(12) United States Patent
Crew et al.

(10) Patent No.: US 11,161,841 B2
(45) Date of Patent: Nov. 2, 2021

(54) MODULATORS OF PROTEOLYSIS AND ASSOCIATED METHODS OF USE

(71) Applicant: Arvinas Operations, Inc., New Haven, CT (US)

(72) Inventors: Andrew P. Crew, Guilford, CT (US); Keith R. Hornberger, Southbury, CT (US); Jing Wang, Milford, CT (US); Hanqing Dong, Madison, CT (US)

(73) Assignee: ARVINAS OPERATIONS, INC., Newhaven, CT (US)

( * ) Notice: Subject to any disclaimer, the term of this patent is extended or adjusted under 35 U.S.C. 154(b) by 0 days.

(21) Appl. No.: 16/375,643

(22) Filed: Apr. 4, 2019

(65) Prior Publication Data

US 2019/0315732 A1 Oct. 17, 2019

Related U.S. Application Data

(60) Provisional application No. 62/652,676, filed on Apr. 4, 2018.

(51) Int. Cl.
| | | |
|---|---|---|
| *C07D 417/14* | (2006.01) | |
| *A61P 35/00* | (2006.01) | |
| *C07D 401/14* | (2006.01) | |
| *C07D 413/14* | (2006.01) | |
| *C07D 471/04* | (2006.01) | |

(52) U.S. Cl.
CPC ............ *C07D 417/14* (2013.01); *A61P 35/00* (2018.01); *C07D 401/14* (2013.01); *C07D 413/14* (2013.01); *C07D 471/04* (2013.01)

(58) Field of Classification Search
CPC .. C07D 417/14; C07D 403/12; C07D 413/14; C07D 471/04; A61P 35/00
USPC ......................................................... 514/264
See application file for complete search history.

(56) References Cited

U.S. PATENT DOCUMENTS

| | | | |
|---|---|---|---|
| 6,306,663 B1 | 10/2001 | Kenten et al. | |
| 6,670,348 B1 | 12/2003 | Rosen et al. | |
| 7,030,141 B2 | 4/2006 | Bigge et al. | |
| 7,041,298 B2 | 5/2006 | Deshaies et al. | |
| 7,208,157 B2 | 4/2007 | Sakamoto et al. | |
| 7,244,851 B2 | 7/2007 | Cohen et al. | |
| 7,345,081 B2 | 3/2008 | Cohen et al. | |
| 7,419,975 B2 | 9/2008 | Palermo et al. | |
| 7,517,906 B2 | 4/2009 | Condon et al. | |
| 7,915,293 B2 | 3/2011 | Ramesh | |
| 9,500,653 B2 | 11/2016 | Crews et al. | |
| 9,632,089 B2 | 4/2017 | Crews et al. | |
| 2006/0128632 A1 | 6/2006 | Sharma et al. | |
| 2008/0051432 A1 | 2/2008 | Zhang | |
| 2008/0214501 A1 | 9/2008 | Pan et al. | |
| 2008/0269140 A1 | 10/2008 | Wang et al. | |
| 2009/0298843 A1 | 12/2009 | Kloog et al. | |
| 2010/0203012 A1 | 8/2010 | Laurent et al. | |
| 2011/0195043 A1 | 8/2011 | Sun et al. | |
| 2012/0270800 A1 | 10/2012 | Verdine et al. | |
| 2014/0235629 A1 | 8/2014 | Bartberger et al. | |
| 2014/0243372 A1 | 8/2014 | Rew | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0239900 A1 | 8/2015 | Li et al. | |
| 2015/0291562 A1 | 10/2015 | Crew et al. | |
| 2015/0344473 A1 | 10/2015 | Du et al. | |
| 2016/0022642 A1 | 1/2016 | Crews et al. | |
| 2016/0045607 A1 | 2/2016 | Crew et al. | |
| 2016/0058872 A1 | 3/2016 | Crew et al. | |
| 2016/0136230 A1 | 5/2016 | Campos et al. | |
| 2016/0214972 A1 | 7/2016 | Jin et al. | |
| 2016/0243247 A1 | 8/2016 | Bradner et al. | |
| 2016/0264627 A1 | 9/2016 | Henning et al. | |

(Continued)

FOREIGN PATENT DOCUMENTS

| | | |
|---|---|---|
| CN | 1844118 A | 10/2006 |
| CN | 103688176 A | 3/2014 |

(Continued)

OTHER PUBLICATIONS

Ahn, et al., "HIF-1alpha peptide derivatives with modifications at the hydroxyproline residue as activators of HIF-1alpha", Bioorg Med Chem Lett. 19(15), 2009, 4403-4405.

Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).

Ashby, M.N. (1998), "CaaX converting enzymes", Current Opinion in Lipidology. 9 (2) 99-102.

(Continued)

*Primary Examiner* — Tracy Vivlemore
*Assistant Examiner* — Ebenezer O Sackey
(74) *Attorney, Agent, or Firm* — Bryan D. Zerhusen, Esq.; Nicholas R. Herrel, Esq.; Cantor Colburn LLP

(57) ABSTRACT

The present disclosure relates to bifunctional compounds, which find utility as modulators of Kirsten rat sarcoma protein (target protein). In particular, the present disclosure is directed to bifunctional compounds, which contain on one end a Von Hippel-Lindau, cereblon, Inhibitors of Apotosis Proteins or mouse double-minute homolog 2 ligand which binds to the respective E3 ubiquitin ligase and on the other end a moiety which binds the target protein, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation, accumulation, and/or overactivation of the target protein are treated or prevented with compounds and compositions of the present disclosure.

22 Claims, 2 Drawing Sheets

(56) References Cited

U.S. PATENT DOCUMENTS

| | | | |
|---|---|---|---|
| 2016/0272639 A1 | 9/2016 | Crew et al. | |
| 2016/0368911 A1 | 12/2016 | Campos et al. | |
| 2017/0008904 A1 | 1/2017 | Crew et al. | |
| 2017/0037004 A1 | 2/2017 | Crew et al. | |
| 2017/0065719 A1* | 3/2017 | Qian .................... | C07D 495/14 |
| 2017/0121321 A1 | 5/2017 | Crews et al. | |
| 2017/0281784 A1 | 10/2017 | Wang et al. | |
| 2017/0307614 A1 | 10/2017 | Crews et al. | |
| 2017/0327469 A1 | 11/2017 | Crew et al. | |
| 2018/0015087 A1 | 1/2018 | Liu et al. | |
| 2018/0072711 A1 | 3/2018 | Crew et al. | |
| 2018/0099940 A1 | 4/2018 | Crew et al. | |
| 2018/0125821 A1 | 5/2018 | Crew et al. | |
| 2018/0147202 A1 | 5/2018 | Crew et al. | |
| 2018/0155322 A1 | 6/2018 | Crew et al. | |
| 2018/0177750 A1 | 6/2018 | Crew et al. | |
| 2018/0179183 A1 | 6/2018 | Crew et al. | |
| 2018/0193470 A1 | 7/2018 | Crew et al. | |
| 2018/0215731 A1 | 8/2018 | Crew et al. | |
| 2018/0228907 A1 | 8/2018 | Crew et al. | |
| 2018/0237418 A1 | 8/2018 | Crew et al. | |
| 2018/0256586 A1 | 9/2018 | Crew et al. | |
| 2018/0319775 A1 | 11/2018 | Li et al. | |
| 2018/0334454 A1 | 11/2018 | Lanman et al. | |

FOREIGN PATENT DOCUMENTS

| | | |
|---|---|---|
| EP | 2985285 | 2/2016 |
| JP | A 2004-525889 | 8/2004 |
| JP | A 2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 2000/066119 | 11/2000 |
| WO | WO 2002/066512 | 8/2002 |
| WO | WO 2002/100845 | 12/2002 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/115289 | 10/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | 2009006567 * | 1/2009 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2012/003281 | 1/2012 |
| WO | WO 2012/007409 | 1/2012 |
| WO | WO 2012/040527 | 3/2012 |
| WO | WO 2012/061683 A2 | 5/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000868 | 1/2015 |
| WO | WO 2015/006524 | 1/2015 |
| WO | WO 2015/097621 | 7/2015 |
| WO | WO 2015/160845 | 10/2015 |
| WO | WO 2016/105518 | 6/2016 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/011590 | 1/2017 |
| WO | WO 2017/024318 A1 | 2/2017 |
| WO | WO 2017/024319 A1 | 2/2017 |
| WO | WO 2017/030814 | 2/2017 |
| WO | WO 2017/046036 | 3/2017 |
| WO | WO 2017/058807 | 4/2017 |
| WO | WO 2017/079267 | 5/2017 |
| WO | WO 2017/161119 | 9/2017 |
| WO | WO 2017/172979 | 10/2017 |
| WO | WO 2017/185036 | 10/2017 |
| WO | WO 2017/197051 | 11/2017 |
| WO | WO 2018/148440 | 8/2018 |
| WO | WO 2018/218070 | 11/2018 |
| WO | WO 2018/218071 | 11/2018 |
| WO | WO 2019/195201 | 10/2019 |

OTHER PUBLICATIONS

Bargagna-Mohan, et al., "Use of PROTACS as molecular probes of angiogenesis", Bioorg Med Chem Left. 15(11) 2005, 2724-2727.

Bondeson DP, et al. (2018) "Lessons in PROTAC Design from Selective Degradation with a Promiscuous Warhead." *Cell Chem Biol* 25(1):78-87 e75.

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule PROTACS", National Chem Biol. 11(8) Aug. 2015, 611-617.

Bos, J. L., "ras oncogenes in human cancer: a review", Cancer Res 49, 4682-4689 (1989).

Buckley, et al., "HaloPROTACS: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and HIF1a", Angew Chem Int Ed Engl.51(46), Nov. 12, 2012, 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

Burslem GM, et al. (2018) "The Advantages of Targeted Protein Degradation Over Inhibition: An RTK Case Study." *Cell Chem Biol* 25(1):67-77 e63.

Burslem, et al., (2017) "Small-Molecule Modulation of Protein Homeostasis." *Chem Rev* 117(17):11269-11301.

Capitosti, S., et al., "Thalidomide analogues demonstrate dual inhibition of both angiogenesis and prostate cancer", Bioorganic & Medicinal Chemistry 12, (2004) 327-336.

Carmony, KC, et al., "PROTAC-Induced Proteolytic Targeting", Methods Mol. Biol., 2012, vol. 832, pp. 627-638.

CAS Registry No. 1004933-70-3, which entered STN on Feb. 21, 2008.

CAS Registry No. 1226974-40-8, indexed in the Registry file on STN CAS Online Jun. 4, 2010.

CAS Registry No. 871986-52-6 entered STN Jan. 16, 2006.

(56) References Cited

OTHER PUBLICATIONS

Chan, et al., (2018) "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds." *J Med Chem* 61(2):504-513.
Chene, P., et al., "Inhibiting the p53-MDM2 interaction: an important target for cancer therapy" Nat. Rev. Cancer (2003), 3, 102-109.
Churcher I (2018) "Protac-Induced Protein Degradation in Drug Discovery: Breaking the Rules or Just Making New Ones?" *J Med Chem* 61(2):444-452.
Cohen, F., et al., "Orally bioavailable antagonists of inhibitor of apoptosis proteins based on an azabicyclooctane scaffold", J. Med. Chem., 52(6), 1723-1730 (2009).
Cohen, F. et al., "Antogonists of inhibitors of apoptosis proteins based on thiazole amide isosteres", Bioorg. Med. Chem. Lett., 20(7), 2229-2233 (2010).
Collins, MA., et al., "Kras as a key oncogene and therapeutic target in pancreatic cancer", Frontiers in Physiol. Jan. 21, 2014; 4:407.
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crew AP, et al. (2018) "Identification and Characterization of Von Hippel-Lindau-Recruiting Proteolysis Targeting Chimeras (PROTACs) of TANK-Binding Kinase 1." *J Med Chem* 61(2):583-598.
Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (2010).
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Kim, K.S., "Discovery of tetrahydroisoquinoline-based bivalent heterodimeric IAP antagonists", Bioorg. Med. Chem. Lett. 24(21), 5022-5029 (2014).
Knickelbein, K., et al., Mutant KRAS as a critical determinant of the therapeutic response of colorectal cancer, Genes Dis. Mar. 2015; 2(1):4-12.
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Kronke, et al, "Lenalidomide Causes Selective Degradation of IKZF1 and IKZF3 in Multiple Myeloma Cells", Science 343, 301-305 (2014).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.

Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in Hlf-1 alpha by pVHL", Nature 417, Jun. 27, 2002, 975-978.
Huang HT, et al. (2018) "A Chemoproteomic Approach to Query the Degradable Kinome Using a Multi-kinase Degrader." *Cell Chem Biol* 25(1):88-99 e86.
Huang, et al., (2016) "Drugging the undruggables: exploring the ubiquitin system for drug development." *Cell Res* 26(4):484-498.
Hughes, et al., (2017) "Molecular recognition of ternary complexes: a new dimension in the structure-guided design of chemical degraders." *Essays Biochem* 61(5):505-516.
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol* 13, 549-555, doi:S1367-5931(09)00107-0 [pii] 10.1016/j.cbpa.2009.08.003 (2009).
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 (2010).
Gadd, M.S., et al., "Structural basis of PROTAC cooperative recognition for selective protein degradation", Nat Chem Biol 13, 514-521 (2017).
Ottis, et al., (2017) "Proteolysis-Targeting Chimeras: Induced Protein Degradation as a Therapeutic Strategy." *ACS Chem Biol* 12(4):892-898.
Pan, Ting, et al., A recombinant chimeric protein specifically induces mutant KRAS degradation and potently inhibits pancreatic tumor growth, Oncotarget, vol. 7, No. 28, pp. 44299-44309.
Perez, HL," Discovery of potent heterodimeric antagonists of inhibitor of apoptosis proteins (IAPs) with sustained antitumor activity", J. Med. Chem. 58(3), 1556-1562 (2015).
Powell, C. E. et al. Chemically Induced Degradation of Anaplastic Lymphoma Kinase (ALK). J. Med. Chem. 61, 4249-4255 (2018).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." *Curr Opin Chem Biol* 39:46-53.

(56) References Cited

OTHER PUBLICATIONS

Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157.
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Luo, J. et al. "A genome-wide RNAi screen identifies multiple synthetic lethal interactions with the Ras oncogene", *Cell* 137, 835-848, doi:S0092-8674(09)00529-7 [pii] 10.1016/j.cell.2009.05.006 (2009).
Mahalingam, D., et al., "Targeting HSP90 for cancer therapy", Br J Cancer 100, 1523-1529 (2009).
Maniaci C, et al. (2017) "Homo-PROTACs: bivalent small-molecule dimerizers of the VHL E3 ubiquitin ligase to induce self-degradation." *Nat Commun* 8(1):830 1-13.
Mannhold, R., et al., "IAP antagonists: promising candidates for cancer therapy", Drug Discov. Today, 15 (5-6), 210-219 (2010).
Martinez-Iacaci, L., et al, "RAS transformation causes sustained activation of epidermal growth factor receptor and elevation of mitogen-activated protein kinase in human mammary epithelial cells", Int. J. Cancer (2000), 88(1), 44-52.
Medline Plus Trusted Health Information for You, www.nlm.nih.gov/medlineplus/cancer.html pp. 1-10, (2007).
Min, Jung-hyun, et al., "Structure of an HIV-1-alpha—pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino-Substituted Thalodomide Analogs: Potent Inhibitors of TNF-α Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.

Ohoka, N. et al. Sniper(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer", Journal of Medicinal Chemistry 2004, 47, 4417-4426.
Ostrem, JM., et al., "Direct small-molecule inhibitors of KRAS: from structural insights to mechanism-based design", Nat Rev Drug Discov. Nov. 2016;15(11):771-785.
Ottis P, et al. (2017) "Assessing Different E3 Ligases for Small Molecule Induced Protein Ubiquitination and Degradation." *ACS Chem Biol* 12(10):2570-2578.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Scharovsky, et al., "Inhibition of ras oncogene: a novel approach to antineoplastic therapy", (2000), Journal of Biomedical Science. 7(4) 292-298.
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stanton, et al., (2018) "Chemically induced proximity in biology and medicine." *Science* 359(6380).
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017 "Compounds containing sulfur Chromophores v. Complex cyanines".
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Sun, B. et al. BET protein proteolysis targeting chimera (PROTAC) exerts potent lethal activity against mantle cell lymphoma cells. Leukemia 32, 343-352 (2018).
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Toure, et al., (2016) "Small-Molecule PROTACS: New Approaches to Protein Degradation." *Angew Chem Int Ed Engl* 55(6):1966-1973.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).

(56) References Cited

OTHER PUBLICATIONS

Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.

Vassilev, et al., "In vivo activation of the p53 pathway by small-molecule antagonists of MDM2", Science 303, Feb. 6, 2004, 844-848.

Vazquez, A. et al., "The genetics of the p53 pathway, apoptosis and cancer therapy", Nat. Rev. Drug. Dis., 7, 979-982 (2008).

Vu, B. et al. "Discovery of RG7112: a small-molecule MDM2 inhibitor in clinical development", ACS Med. Chem. Lett. (2013) 4, 466-469.

Wang J, et al., "Discovery of novel second mitochondrial-derived activator of caspase mimetics as selective inhibitor or apoptosis protein inhibitors", J. Pharmacol. Exp. Ther., 349(2): 319-29 (2014).

Wang, S., et al. "Small-molecule inhibitors of the MDM2-p53 protein-protein interaction (MDM2 inhibitors) in clinical trials for cancer treatment", J. Med. Chem. (2015) 58, 1038-1052.

Wang, S., et al. "Temporal activation of p53 by a specific MDM2 inhibitor is selectively toxic to tumors and leads to complete tumor growth inhabitation", PNAS USA (2008) 105, 3933-3938.

Winter, et al., "Phthalimide Conjugation as a strategy for in vivo target protein degradation", Science, 2015 vol. 348 (6241), pp. 1376-1381 [Pub online: May 21, 2015].

Yao, Z. et al. Tumors with class 3 BRAF mutants are sensitive to the inhibition of activated RAS. Nature 548, 234-238 (2017).

Zengerle, et al., "Selective Small Molecule Induced Degradation of the BET Bromodomain Protein BRD4" ACS Chemical Biology, Jun. 2, 2015, vol. 10, pp. 1770-1777.

Zhang B.et al., "Small-molecule MDM2-p53 inhibitors: recent advances", Future Med. Chem. (2015) 7, 631-645.

Zhang, D. et al., "Targeted Degradation of Proteins by Small Molecules: A Novel Tool for Functional Proteomics," comb Chem. High Throughput Screen., 2004, vol. 7, No. 7, pp. 689-697.

Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem. 6b01816) (2017).

Zeng, M., et al., Potent and Selective Covalent Quinazoline Inhibitors of KRAS G12C, Cell Chemical Biology, 24, 1005-1016.

International Search Report and Written Opinion for PCT/US2019/025878, dated Oct. 15, 2019.

\* cited by examiner

MODULATORS OF PROTEOLYSIS AND ASSOCIATED METHODS OF USE

CROSS-REFERENCE TO RELATED APPLICATION

The present disclosure claims priority to U.S. Provisional Application No. 62/652,676, filed 4 Apr. 2018 and entitled MODULATORS OF PROTEOLYSIS AND ASSOCIATED METHODS OF USE, and the contents of which are incorporated herein by reference in its entirety for all purposes.

INCORPORATION BY REFERENCE

U.S. patent application Ser. No. 15/230,354, filed on Aug. 5, 2016, published as Application Publication No. 2017/0065719, and U.S. patent application Ser. No. 15/206,497 filed 11 Jul. 2016, published as U.S. Patent Application Publication No. 2017/0008904; and U.S. patent application Ser. No. 15/209,648 filed 13 Jul. 2016, published as U.S. Patent Application Publication No. 2017/0037004; and U.S. patent application Ser. No. 15/730,728, filed on Oct. 11, 2017, published as U.S. Patent Application Publication No. 2018/0099940; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639; and U.S. Provisional patent application Ser. No. 15/885,671, filed Jan. 31, 2018, published as U.S. Patent Application Publication No. 2018/0215731 A1; and International Patent Application No. PCT/US2016/023258, filed Mar. 18, 2016, published as International Patent Application Publication No. WO2016/149668, are incorporated herein by reference in their entirety. Furthermore, all references cited herein are incorporated by reference herein in their entirety.

FIELD OF THE INVENTION

The description provides bifunctional compounds comprising a target protein binding moiety and an E3 ubiquitin ligase binding moiety, and associated methods of use. The bifunctional compounds are useful as modulators of targeted ubiquitination, especially with respect to Kirsten ras sarcoma protein (KRas or KRAS), such as mutant or gain-of-function KRas, which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-la, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC 1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apotosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death. However, pro-apoptotic stimuli can result in the release of mitochondrial proteins DIABLO (also known as second mitrochondria-derived activator of caspases or SMAC) and HTRA2 (also known as Omi). Binding of DIABLO and HTRA2 appears to block IAP activity.

SMAC interacts with essentially all known IAPs including XIAP, c-IAP1, c-IAP2, NIL-IAP, Bruce, and survivin. The first four amino acids (AVPI) of mature SMAC bind to a portion of IAPs, which is believed to be essential for blocking the anti-apoptotic effects of IAPs.

Bifunctional compounds such as those that are described in U.S. Patent Application Publications 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

The Kirsten rat sarcoma (KRAS) gene is an oncogene encoding KRas, which is a small GTPase signal transduction protein. Ras proteins associate with the plasma membrane, and act as switches in the transduction of extracellular signals to intracellular response, thereby regulating, e.g., cell division. Numerous activating or gain-of-function mutations of the KRas gene are known, and in fact, KRas is the most frequently mutated gene in cancer. Gain-in-function KRas mutations are found in approximately 30% of all human cancers, including, e.g., pancreatic cancer (>80%), colon cancer (approximately 40-50%), lung cancer (approximately 30-50%), non-small cell lung cancer, biliary tract malignancies, endometrial cancer, cervical cancer, bladder cancer, liver cancer, myeloid leukemia, and breast cancer. These activating mutations impair the ability of KRas to switch between active and inactive states. Key roles for mutant KRas have been established in initiation, maintenance, progression, and metastasis of various cancers, and mutations are frequently correlated with poor prognosis and increased resistance to chemotherapy and biological therapies, including, e.g., therapies that target epidermal growth factor receptor. However, in spite of its key role and high rates prevalence in cancer, there is an absence of effective therapies that directly target this oncogene, leading to it being considered "undruggable."

Thus, an ongoing need exists in the art for effective treatments for disease associated with overexpression, aggregation, and/or overactivation of KRas (e.g., the aggregation of active KRas), such as a gain-of-function KRas mutant (i.e., a KRas having a gain-of-function mutation). However, non-specific effects, and the inability to target and modulate mutant KRas, remain as obstacles to the development of effective treatments. As such, small-molecule therapeutic agents that target KRas and that leverage or potentiate VHL's, cereblon's, MDM2's, and IAPs' substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., pancreatic cancer, colon cancer, colorectal cancer, lung cancer, non-small cell lung cancer, biliary tract malignancies, endometrial cancer, cervical cancer, bladder cancer, liver cancer, myeloid leukemia, and breast cancer.

As such, in one aspect the disclosure provides bifunctional or PROTAC compounds, which comprise an E3 ubiquitin ligase binding moiety (i.e., a ligand for an E3 ubiquitin ligase or "ULM" group), and a moiety that binds a target protein (i.e., a protein/polypeptide targeting ligand or "PTM" group) such that the target protein/polypeptide (e.g., Kirsten rat sarcoma protein (KRas or KRAS) and/or mutant KRas, such as $KRas^{G12C}$) is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double miniute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

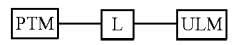

where PTM is a protein/polypeptide targeting moiety, L is a linker, e.g., a bond or a chemical group coupling PTM to ULM, and ULM is a IAP E3 ubiquitin ligase binding moiety (ILM), or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as:

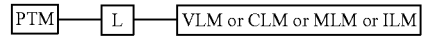

wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety that bind MDM2; and ILM is a IAP binding moiety that binds to IAP.

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other thorugh amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, published as U.S. Patent Application Publication No. 2017/0008904, which as discussed above, is incorporated herein in its entirety. In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation and/or inhibition in a patient or subject, for example, an animal such as a human, and can be used for treating or ameliorating disease states or conditions which are modulated through the degraded/inhibited protein. In certain embodiments, the therapeutic compositions as described herein may be used to effectuate the degradation of proteins of interest for the treatment or amelioration of a disease, e.g., cancer (such as pancreatic cancer, colon cancer, colorectal cancer, lung cancer, or non-small cell lung cancer). In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, the PTM can be coupled to VLM or CLM or MLM or ILM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIG. 2A is a Western blot showing a potent degrader, exemplary compound 399. FIG. 2B is a Western blot showing a less potent degrader, exemplary compound 432. Both compounds covalently modify $KRas^{G12C}$, as seen by the gel shift.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
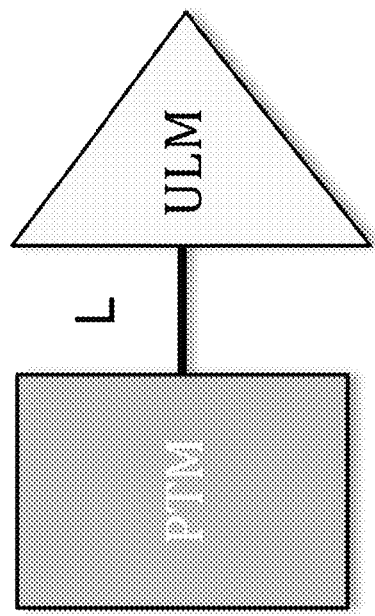
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.
Figure 1B:
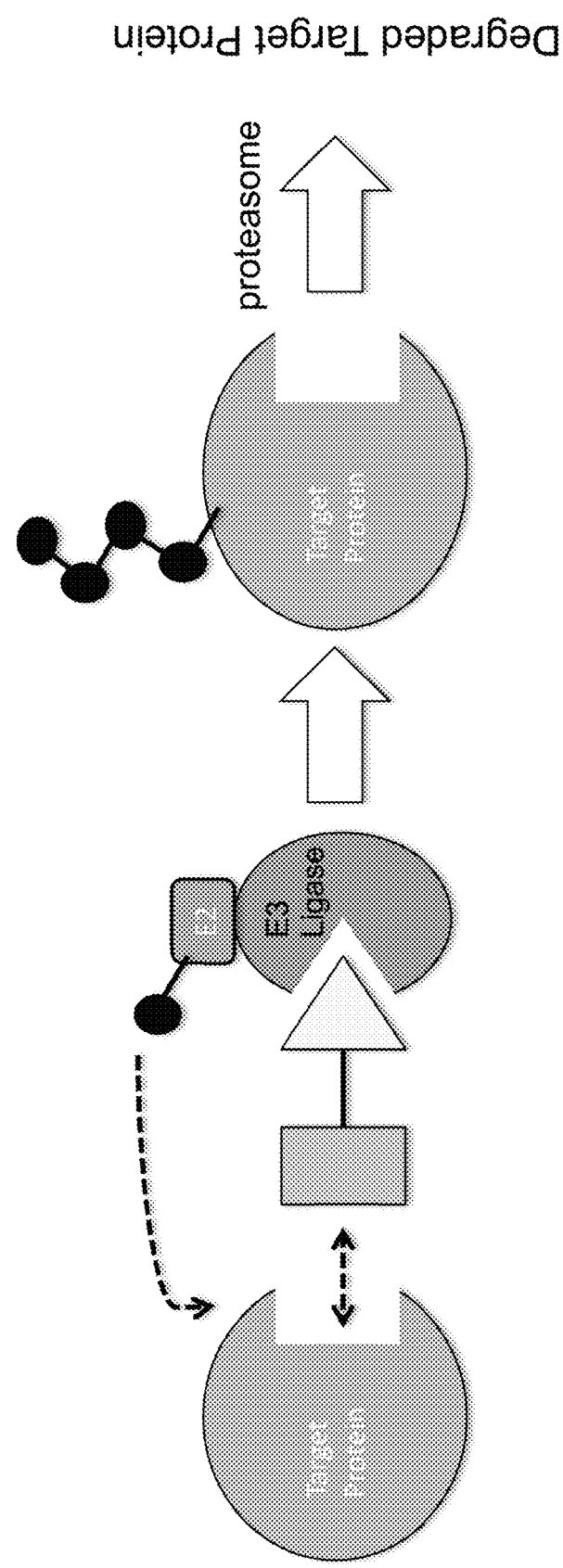

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein, which leads to degradation of the target protein by the proteasome (see FIG. 1). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent, such as a chemotherapy or biological therapy that targets epidermal growth factor receptors (e.g., epidermal growth factor receptor inhibitors, such as at least one of gefitinib, erlotinib, neratinib, lapatinib, cetuximab, vandetanib, necitumamab, osimertinib, or a combination thereof). In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a target protein binding moiety (PTM) via a chemical linker (L) according to the structure:

PTM-L-ULM      (A)

wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

PTM-ILM      (B)

PTM-CLM      (C)

PTM-VLM      (D)

PTM-MLM      (E)

In certain embodiments, the bifunctional compound further comprises a chemical linker ("L"). For example, the bifunctional compound can be depicted as:

PTM-L-ILM      (F)

PTM-L-CLM      (G)

PTM-L-VLM      (H)

PTM-L-MLM      (I)

wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 µM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects or embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ULMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

Exemplary ILMs

AVPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

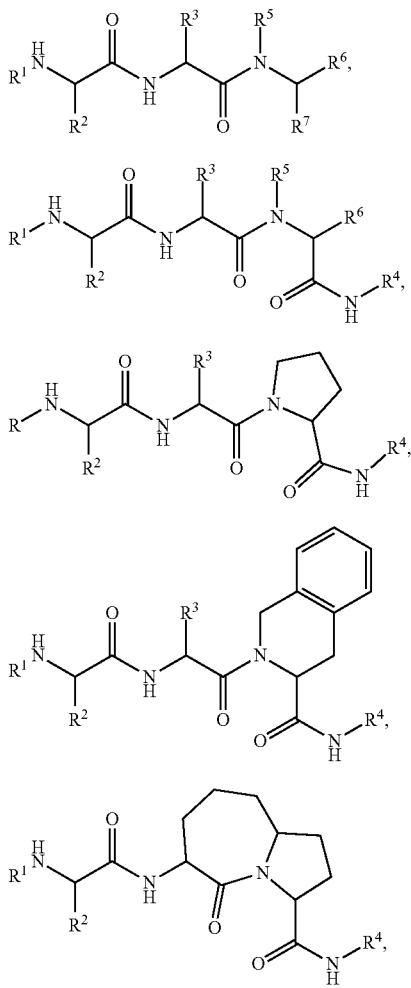

wherein:
- $R^1$ for Formulas (I), (II), (III), (IV), and (V) is selected from H or alkyl;
- $R^2$ for Formulas (I), (II), (III), (IV), and (V) is selected from H or alkyl;
- $R^3$ for Formulas (I), (II), (III), (IV), and (V) is selected from H, alkyl, cycloalkyl and heterocycloalkyl;
- $R^5$ and $R^6$ for Formulas (I), (II), (III), (IV), and (V) are independently selected from H, alkyl, cycloalkyl, heterocycloalkyl, or more preferably, $R^5$ and $R^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;
- $R^3$ and $R^5$ for Formulas (I), (II), (III), (IV), and (V) taken together can form a 5-8-membered ring further optionally fused to 1-2 cycloalkyl, heterocycloalkyl, aryl or heteroaryl rings;
- $R^7$ for Formulas (I), (II), (III), (IV), and (V) is selected from cycloalkyl, cycloalkylalkyl, heterocycloalkyl, heterocycloalkylalkyl, aryl, aryl-C(O)—$R^4$, arylalkyl, heteroaryl, heteroaryl-C(O)—$R^4$, heteroaryl-$R^4$, heteroaryl-naphthalene, heteroarylalkyl, or —C(O)NH—$R^4$, each one further optionally substituted with 1-3 substituents selected from halogen, alkyl, haloalkyl, hydroxyl, alkoxy, cyano, (hetero)cycloalkyl, aryl, (hetero)aryl, —C(O)NH—$R^4$, or C(O)—$R^4$; and
- $R^4$ is selected from alkyl, cycloalkyl, heterocycloalkyl, cycloalkylalkyl, heterocycloalkylalkyl, aryl (e.g., bicyclic aryl), arylalkyl, heteroaryl (e.g., a bicyclic heteroaryl), heteroarylalkyl, further optionally substituted with 1-3 substituents as described above.

As shown above, P1, P2, P3, and P4 of Formula (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

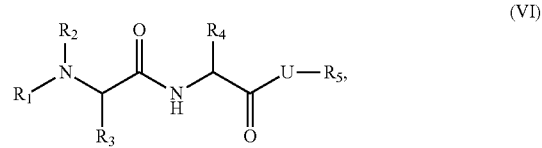

wherein:
- $R_1$ of Formula (VI) is, independently selected from H, $C_1$-$C_4$-alky, $C_1$-$C_4$-alkenyl, $C_1$-$C_4$-alkynyl or $C_3$-$C_{10}$-cycloalkyl which are unsubstituted or substituted;
- $R_2$ of Formula (VI) is, independently selected from H, $C_1$-$C_4$-alkyl, $C_1$-$C_4$-alkenyl, $C_1$-$C_4$-alkynyl or $C_3$-$C_{10}$-cycloalkyl which are unsubstituted or substituted;
- $R_3$ of Formula (VI) is, independently selected from H, —$CF_3$, —$C_2H_5$, $C_1$-$C_4$-alkyl, $C_1$-$C_4$-alkenyl, $C_1$-$C_4$-alkynyl, —$CH_2$—Z or any $R_2$ and $R_3$ together form a heterocyclic ring;
- each Z of Formula (VI) is, independently selected from H, —OH, F, Cl, —CH3, —$CF_3$, —$CH_2Cl$, —$CH_2F$ or —$CH_2OH$;
- $R_4$ of Formula (VI) is, independently selected from $C_1$-$C_{16}$ straight or branched alkyl, $C_1$-$C_{16}$-alkenyl, $C_1$-$C_{16}$-alkynyl, $C_3$-$C_{10}$-cycloalkyl, —$(CH_2)_{0-6}$—$Z_1$, —$(CH_2)_{0-6}$-aryl, and —$(CH_2)_{0-6}$-het, wherein alkyl, cycloalkyl, and phenyl are unsubstituted or substituted;
- $R_5$ of Formula (VI) is, independently selected from H, $C_1$-$C_{10}$-alkyl, aryl, phenyl, $C_{3-7}$-cycloalkyl, —$(CH_2)_{1-6}$—$C_{3-7}$-cycloalkyl, —$C_{1-10}$-alkyl-aryl, —$(CH_2)_{0-6}$—$C_{3-7}$-cycloalkyl-$(CH_2)_{0-6}$-phenyl, —$(CH_2)_{0-4}$—CH[$(CH_2)_{1-4}$-phenyl]$_2$, indanyl, —C(O)—$C_{1-10}$-alkyl, —C(O)—$(CH_2)_{1-6}$—$C_{3-7}$-cycloalkyl, —C(O)—$(CH_2)_{0-6}$-phenyl-$(CH_2)_{0-6}$—C(O)-phenyl, —$(CH_2)_{0-6}$-het, —C(O)—$(CH_2)_{1-6}$-het, or $R_5$ is selected from a residue of an amino acid, wherein the alkyl, cycloalkyl, phenyl, and aryl substituents are unsubstituted or substituted;

$Z_1$ of Formula (VI) is, independently selected from —N($R_{10}$)—C(O)—$C_{1-10}$-alkyl, —N($R_{10}$)—C(O)—($CH_2$)$_{0-6}$—$C_{3-7}$-cycloalkyl, —N($R_{10}$)—C(O)—($CH_2$)$_{0-6}$-phenyl, —N($R_{10}$)—C(O)($CH_2$)$_{1-6}$-het, —C(O)—N($R_{11}$)($R_{12}$), —C(O)—O—$C_{1-10}$-alkyl, —C(O)—O—($CH_2$)$_{1-6}$—$C_{3-7}$-cycloalkyl, —C(O)—O—($CH_2$)$_{0-6}$-phenyl, —C(O)—O—($CH_2$)$_{1-6}$-het, —O—C(O)—$C_{1-10}$-alkyl, —O—C(O)—($CH_2$)$_{1-6}$—$C_{3-7}$-cycloalkyl, —O—C(O)—($CH_2$)$_{0-6}$-phenyl, —O—C(O)—($CH_2$)$_{1-6}$-het, wherein alkyl, cycloalkyl, and phenyl are unsubstituted or substituted;

het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;

$R_{10}$ of Formula (VI) is selected from H, —$CH_3$, —$CF_3$, —$CH_2OH$, or —$CH_2Cl$;

$R_{11}$ and $R_{12}$ of Formula (VI) are independently selected from 1H, $C_{1-4}$-alkyl, $C_{3-7}$-cycloalkyl, —($CH_2$)$_{1-6}$—$C_{3-7}$-cycloakyl, ($CH_2$)$_{0-6}$-phenyl, wherein alkyl, cycloalkyl, and phenyl are unsubstituted or substituted; or $R_{11}$ and $R_{12}$ together with the nitrogen form het, and U of Formula (VI) is, independently, as shown in Formula (VII):

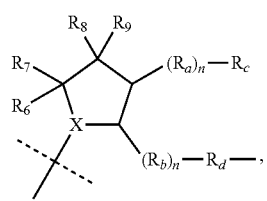

wherein:
each n of Formula (VII) is, independently selected from 0 to 5;

X of Formula (VII) is selected from the group —CH and N;

$R_a$ and $R_b$, of Formula (VII) are independently selected from the group O, S, or N atom or $C_{0-8}$-alkyl wherein one or more of the carbon atoms in the alkyl chain are optionally replaced by a heteroatom selected from O, S, or N, and where each alkyl is, independently, either unsubstituted or substituted;

$R_d$ of Formula (VII) is selected from the group Re-Q-($R_f$)$_p$($R_g$)$_q$, and $Ar_1$-D-$Ar_2$;

$R_c$ of Formula (VII) is selected from the group H or any $R_c$ and $R_d$ together form a cycloalkyl or het; where if $R_c$ and $R_d$ form a cycloalkyl or het, $R_5$ is attached to the formed ring at a C or N atom;

p and q of Formula (VII) are independently selected from 0 or 1;

$R_e$ of Formula (VII) is selected from the group $C_{1-8}$-alkyl and alkylidene, and each Re is either unsubstituted or substituted;

Q is selected from the group N, O, S, S(O), and S(O)$_2$;

$Ar_1$ and $Ar_2$ of Formula (VII) are independently selected from the group of substituted or unsubstituted aryl and het;

$R_f$ and $R_g$ of Formula (VII) are independently selected from H, —$C_{1-10}$-alkyl, $C_{1-10}$-alkylaryl, —OH, —O—$C_{1-10}$-alkyl, —($CH_2$)$_{0-6}$—$C_{3-7}$-cycloalky, —O—($CH_2$)$_{0-6}$-aryl, phenyl, aryl, phenyl-phenyl, —($CH_2$)$_{1-6}$-het, —O—($CH_2$)$_{1-6}$-het, —$OR_3$, —C(O)—$R_{13}$, —C(O)—N($R_{13}$)($R_{14}$), —N($R_{13}$)($R_{14}$), —S—$R_{13}$, —S(O)—$R_{13}$, —S(O)$_2$—$R_{13}$, —S(O)$_2$— $NR_{13}R_{14}$, —$NR_{13}$—S(O)$_2$—$R_{14}$, —S—$C_{1-10}$-alkyl, aryl-$C_{1-4}$-alkyl, or het-$C_{1-4}$-alkyl, wherein alkyl, cycloalkyl het, and aryl are unsubstituted or substituted, —SO$_2$—$C_{1-2}$-alkyl, —SO$_2$—$C_{1-2}$-alkylphenyl, —O—$C_{1-4}$-alkyl, or any $R_g$ and $R_f$ together form a ring selected from het or aryl;

D of Formula (VII) is selected from the group —CO—, —C(O)—$C_{1-7}$-alkylene or arylene, —$CF_2$—, —O—, —S(O)$_r$, where r is 0-2, 1,3-dioxalane, or $C_{1-7}$-alkyl-OH; where alkyl, alkylene, or arylene are unsubstituted or substituted with one or more halogens, OH, —O—$C_{1-6}$-alkyl, —S—$C_{1-6}$-alkyl, or —$CF_3$; or each D is, independently selected from N(R);

Rh is selected from the group H, unsubstituted or substituted $C_{1-7}$-alkyl, aryl, unsubstituted or substituted —O—($C_{1-7}$-cycloalkyl), —C(O)—$C_{1-10}$-alkyl, —C(O)—$C_{0-10}$-alkyl-aryl, —C—O—$C_{01-10}$-alkyl, —C—O—$C_{0-10}$-alkyl-aryl, —SO$_2$—$C_{1-10}$-alkyl, or —SO$_2$—($C_{0-10}$-alkylaryl);

$R_6$, $R_7$, $R_8$, and $R_9$ of Formula (VII) are, independently, selected from the group H, —$C_{1-10}$-alkyl, —$C_{1-10}$-alkoxy, aryl-$C_{1-10}$-alkoxy, —OH, —O—$C_{1-10}$-alkyl, —($CH_2$)$_{0-6}$—$C_{3-7}$-cycloalkyl, —O—($CH_2$)$_{0-6}$-aryl, phenyl, —($CH_2$)$_{1-6}$-het, —O—($CH_2$)$_{1-6}$-het, —$OR_{13}$, —C(O)—$R_{13}$, —C(O)—N($R_{13}$)($R_{14}$), —N($R_{13}$)($R_{14}$), —S—$R_{13}$, —S(O)—$R_{13}$, —S(O)$_2$— $R_{13}$, —S(O)$_2$—$NR_{13}R_{14}$, or —$NR_{13}$—S(O)$_2$—$R_{14}$; wherein each alkyl, cycloalkyl, and aryl is unsubstituted or substituted; and any $R_6$, $R_7$, $R_8$, and $R_9$ optionally together form a ring system;

$R_{13}$ and $R_{14}$ of Formula (VII) are independently selected from the group H, $C_{1-10}$-alkyl, —($CH_2$)$_{0-6}$—$C_{3-7}$-cycloalkyl, —($CH_2$)$_{0-6}$—(CH)$_{0-1}$-(aryl)$_{1-2}$, —C(O)—$C_{1-10}$-alkyl, —C(O)—($CH_2$)$_{1-6}$—$C_{3-7}$-cycloalkyl, —C(O)—O—($CH_2$)$_{0-6}$-aryl, —C(O)—($CH_2$)$_{0-6}$—O-fluorenyl, —C(O)—NH—($CH_2$)$_{0-6}$-aryl, —C(O)—($CH_2$)$_{0-6}$-aryl, —C(O)—($CH_2$)$_{0-6}$-het, —C(S)—$C_{1-10}$-alkyl, —C(S)—($CH_2$)$_{1-6}$—$C_{3-7}$-cycloalkyl, —C(S)—O—($CH_2$)$_{0-6}$-aryl, —C(S)—($CH_2$)$_{0-6}$O-fluorenyl, —C(S)—NH—($CH_2$)$_{0-6}$-aryl, —C(S)—($CH_2$)$_{0-6}$-aryl, or —C(S)—($CH_2$)$_{1-6}$-het, wherein each alkyl, cycloalkyl, and aryl is unsubstituted or substituted; or any $R_{13}$ and $R_{14}$ together with a nitrogen atom form het;

wherein alkyl substituents of $R_{13}$ and $R_{14}$ of Formula (VII) are unsubstituted or substituted and when substituted, are substituted by one or more substituents selected from $C_{1-10}$-alkyl, halogen, OH, —O—$C_{1-6}$-alkyl, —S—$C_{1-6}$-alkyl, and —$CF_3$; and substituted phenyl or aryl of $R_{13}$ and $R_{14}$ are substituted by one or more substituents selected from halogen, hydroxyl. $C_{1-4}$-alkyl, $C_{1-4}$-alkoxy, nitro, —CN, —O—C(O)—$C_{1-4}$-alkyl, and —C(O)—O—$C_{1-4}$-aryl; or a pharmaceutically acceptable salt or hydrate thereof.

In certain embodiments, the compound further comprises an independently selected second ILM attached to the ILM of Formula (VI), or an unnatural mimetic thereof, by way of at least one additional independently selected linker group.

In an embodiment, the second ILM is a derivative of Formula (VI), or an unnatural mimetic thereof. In a certain embodiment, the at least one additional independently selected linker group comprises two additional independently selected linker groups chemically linking the ILM and the second ILM. In an embodiment, the at least one additional linker group for an ILM of the Formula (VI), or an unnatural mimetic thereof, chemically links groups selected from $R_4$ and $R_5$. For example, an ILM of Formula (VI) and a second ILM of Formula (VI), or an unnatural mimetic thereof, can be linked as shown below:

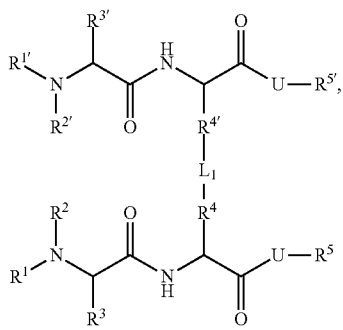
(A)

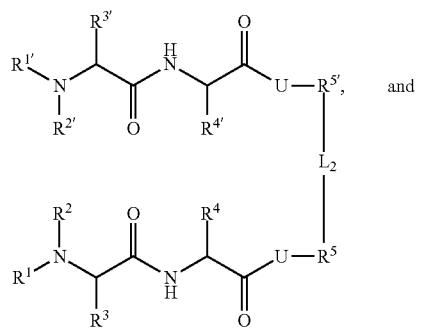
(B)

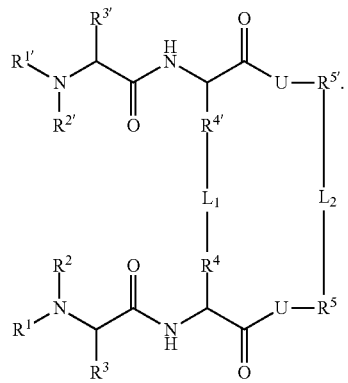
(C)

In certain embodiments, the ILM, the at least one additional independently selected linker group L, and the second ILM has a structure selected from the group consisting of:

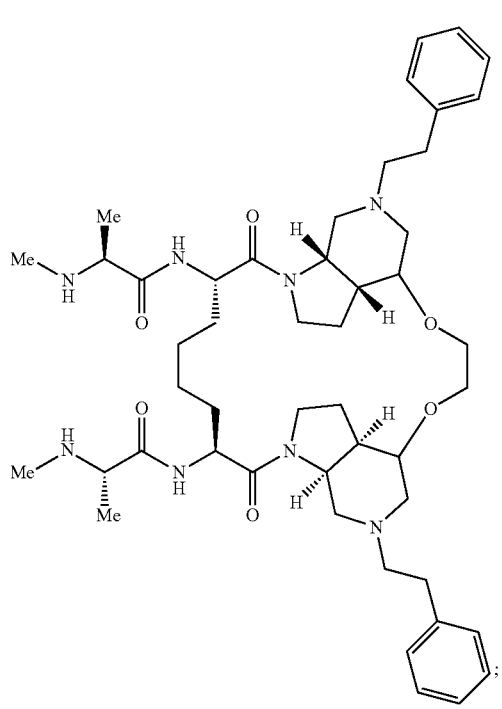
(A)

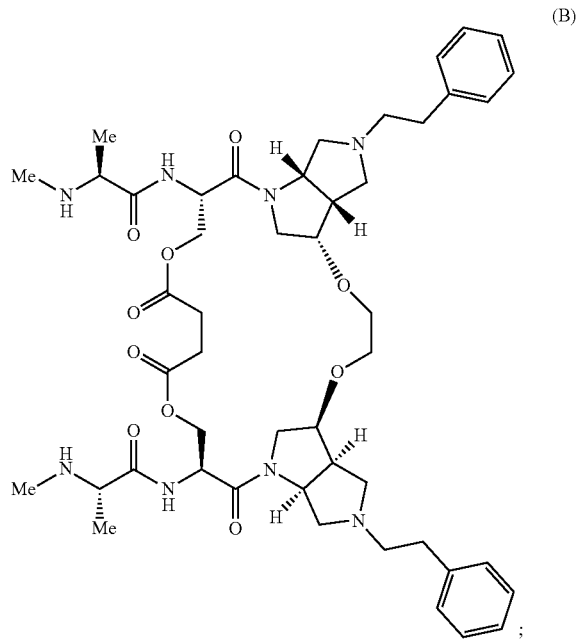
(B)

-continued
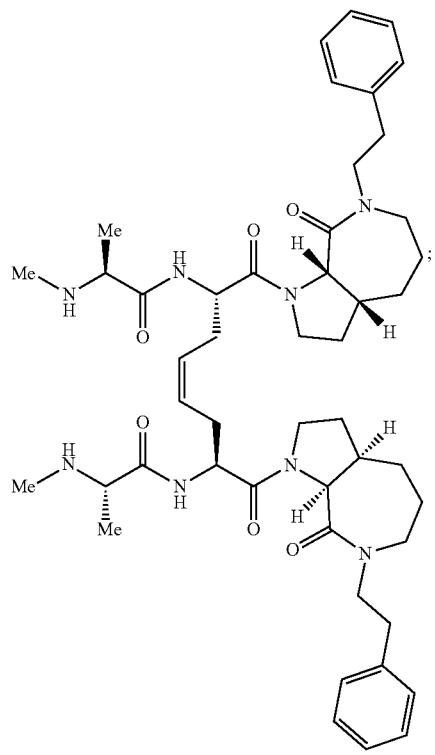
(C)
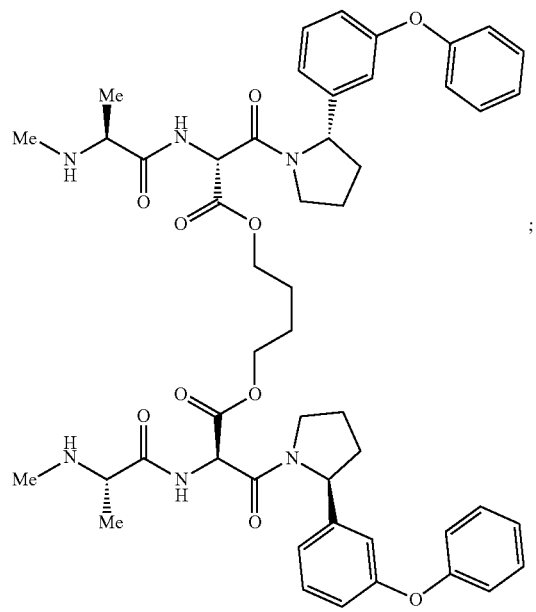
(D)
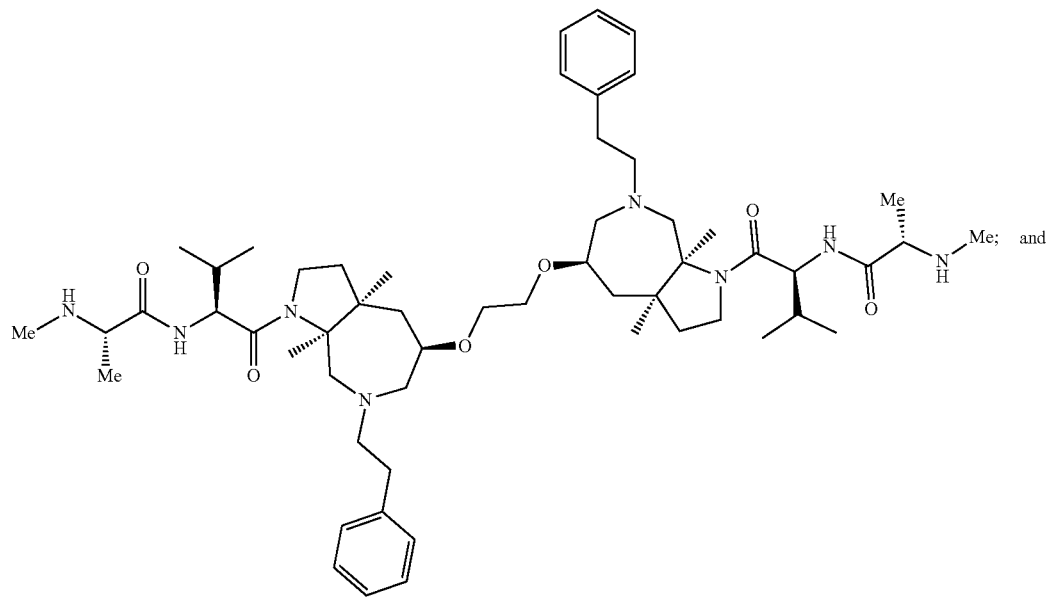
(E)
and (F)

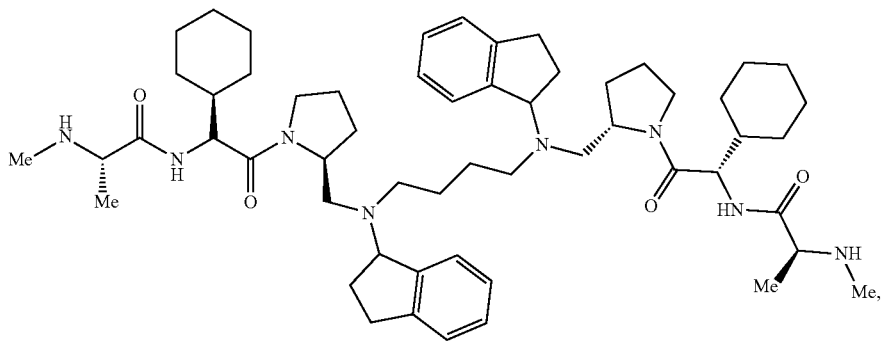

which are derivatives of IAP antagonists described in WO Pub. No. 2008/014236.

In any of the compounds described herein, the ILM can have the structure of Formula (VIII), which is based on the IAP ligrands described in Ndubaku, C., et al. Antagonism of c-IAP and XIAP proteins is required for efficient induction of cell death by small-molecule IAP antagonists, *ACS Chem. Biol.*, 557-566, 4 (7) (2009), or an unnatural mimetic thereof:

(VIII)

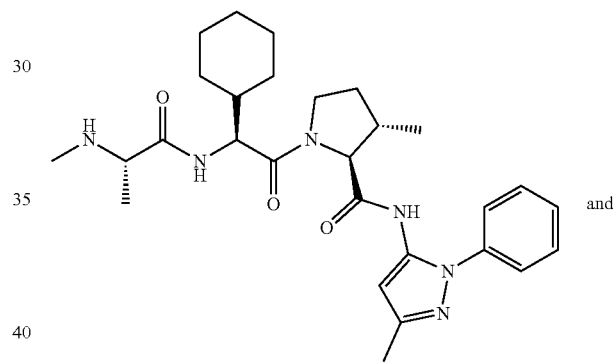

wherein each of A1 and A2 of Formula (VIII) is independently selected from optionally substituted monocyclic, fused rings, aryls and hetoroaryls; and R of Formula (VIII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of

In any of the compounds described herein, the ILM can have the structure of Formula (IX), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

(IX)

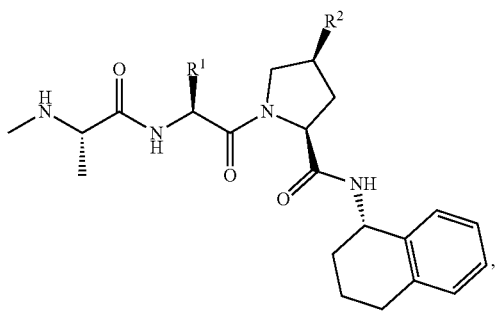

wherein R¹ is selected from alkyl, cycloalkyl and heterocycloalkyl and, most preferably, from isopropyl, tert-butyl, cyclohexyl and tetrahydropyranyl, and R² of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

(X)

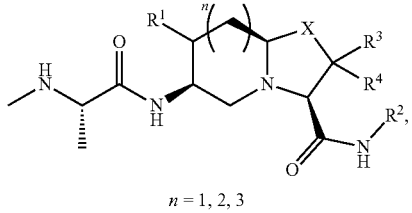

$n = 1, 2, 3$ wherein:
R¹ of Formula (X) is selected from H, —CH$_2$OH, —CH$_2$CH$_2$OH, —CH$_2$NH$_2$, —CH$_2$CH$_2$NH$_2$;
X of Formula (X) is selected from S or CH$_2$;
R² of Formula (X) is selected from:

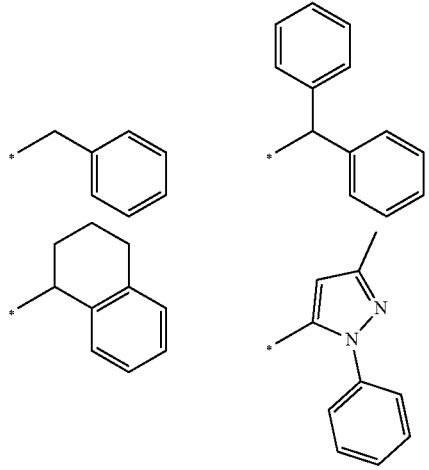

R³ and R⁴ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

(XI)

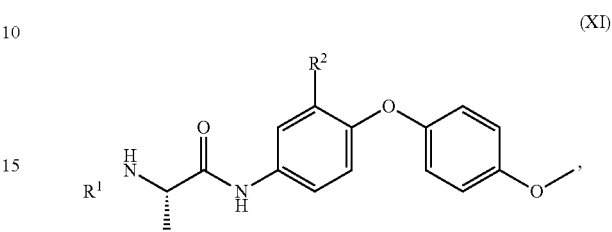

wherein R¹ of Formula (XI) is selected from H or Me, and R² of Formula (XI) is selected from H or

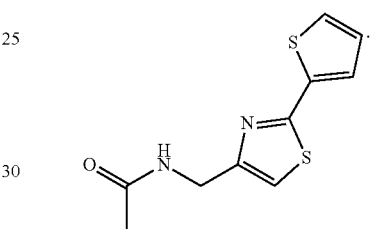

In any of the compounds described herein, the ILM can have the structure of Formula (XII), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

(XII)

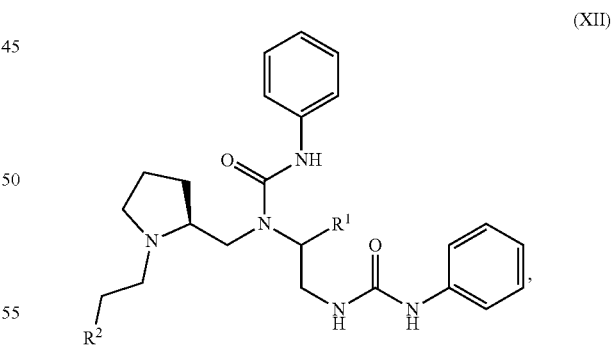

wherein:
R¹ of Formula (XII) is selected from:

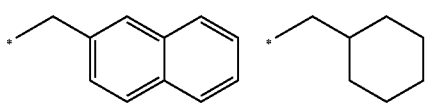

25
-continued
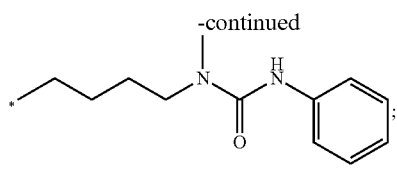
and
R² of Formula (XII) is selected from:
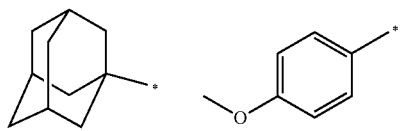
26
-continued
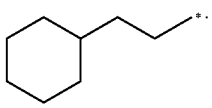
In any of the compounds described herein, the IAP E3 ubiquitin ligase binding moiety is selected from the group consisting of:
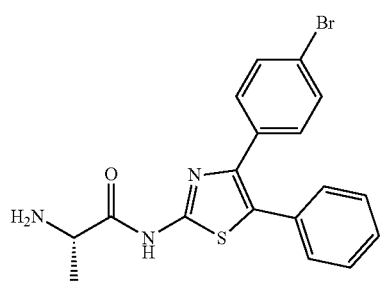
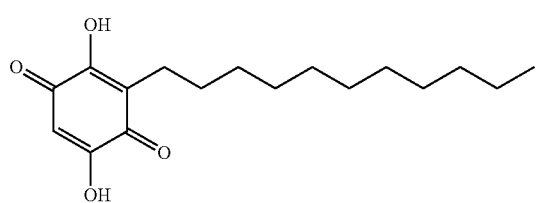
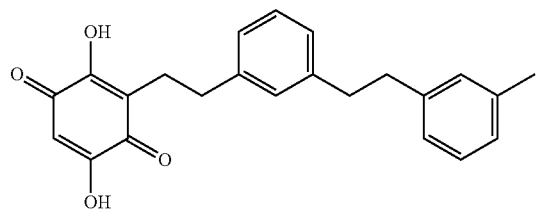
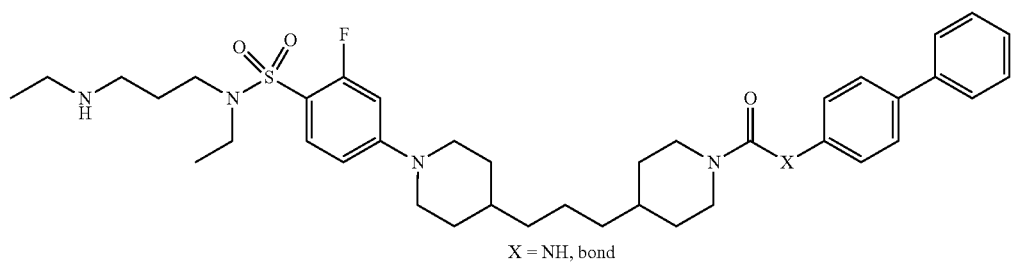
X = NH, bond

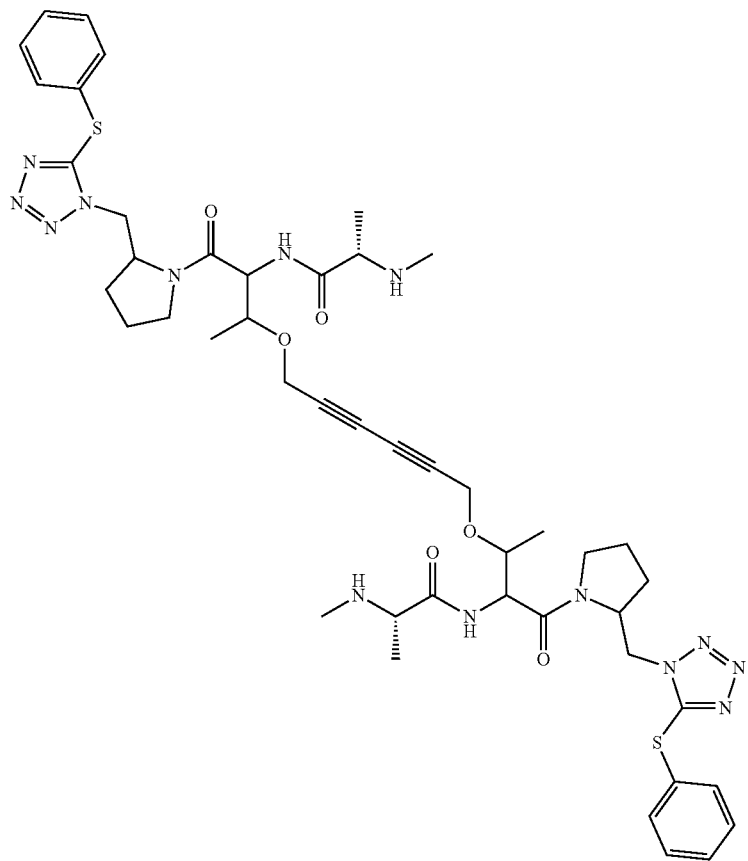
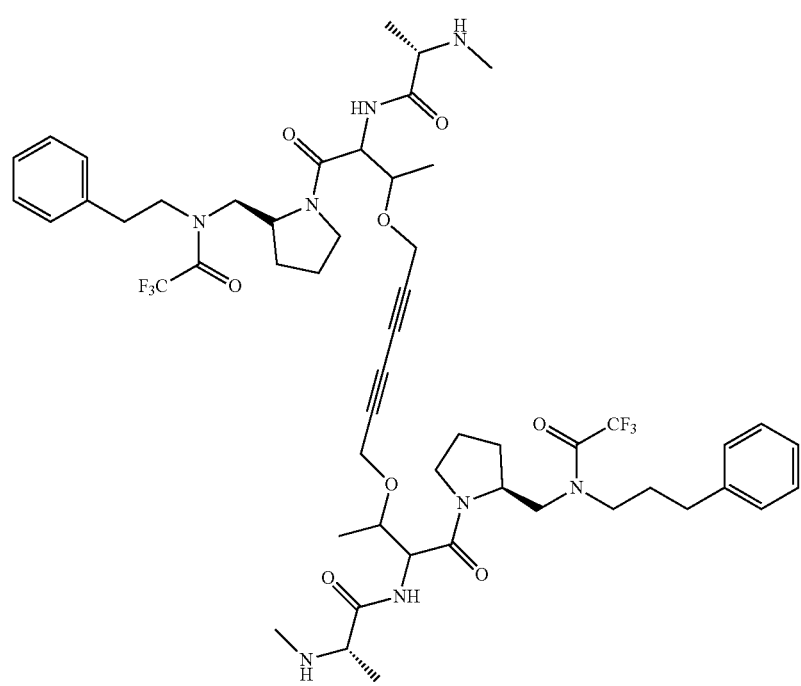

-continued
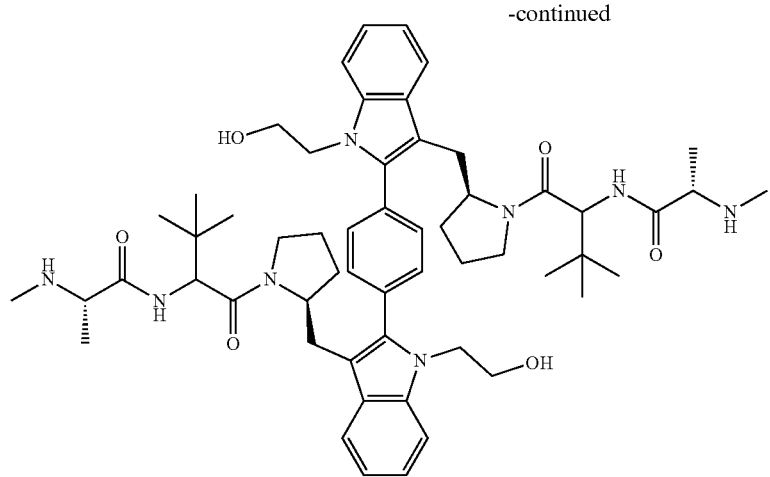
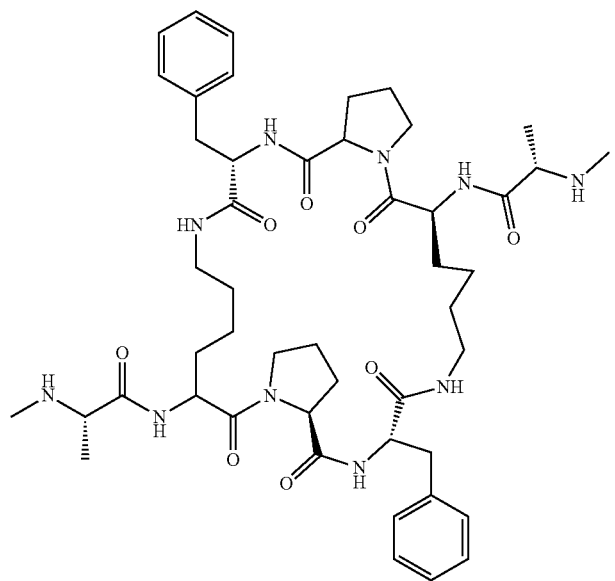
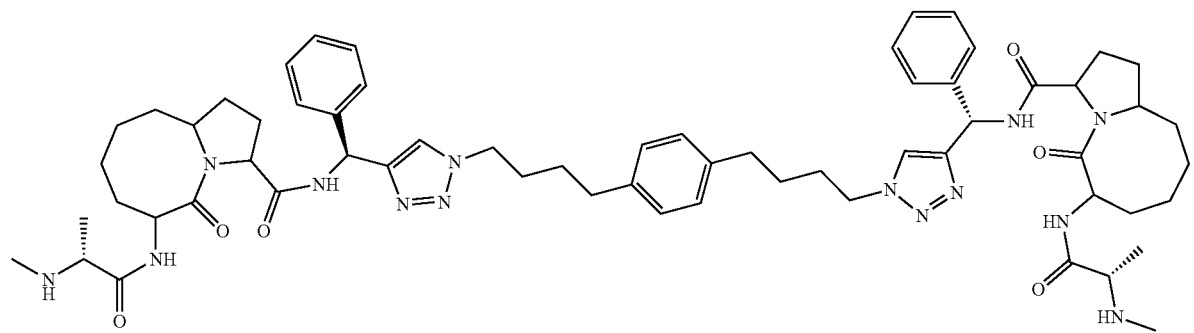

-continued

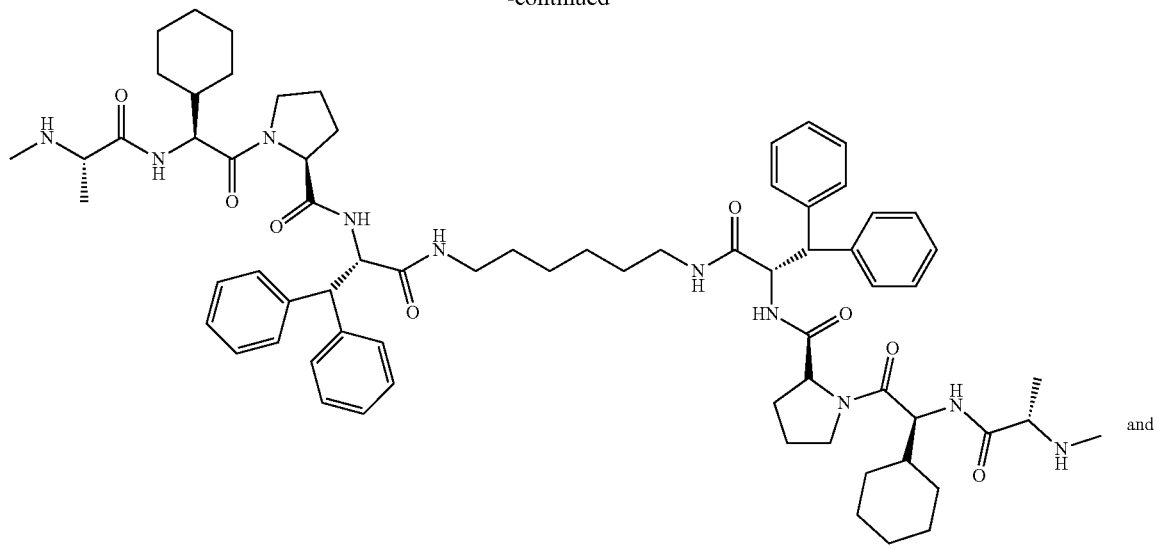

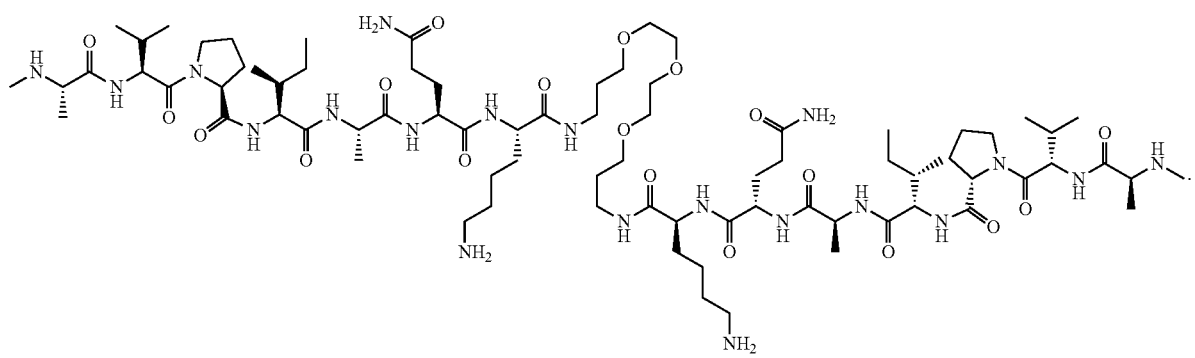

In any of the compounds described herein, the ILM can have the structure of Formula (XIII), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

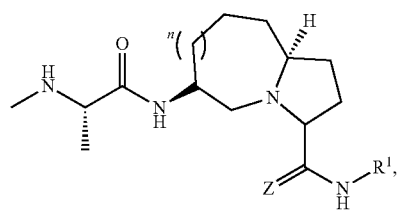

(XIII)

$n = 0, 2$ or, preferably, 1 wherein:

Z of Formula (XIII) is absent or O;

$R^1$ of Formula (XIII) is selected from:

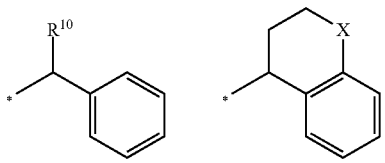

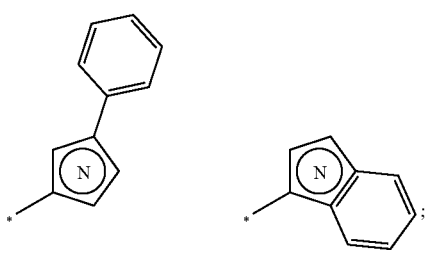

$R^{10}$ of

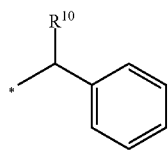

is selected from H, alkyl, or aryl;

X is selected from CH2 and O; and

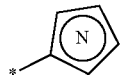

is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

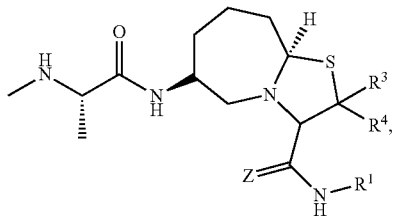

(XIV)

wherein:

Z of Formula (XIV) is absent or O;

$R^3$ and $R^4$ of Formula (XIV) are independently selected from H or Me;

$R^1$ of Formula (XIV) is selected from:

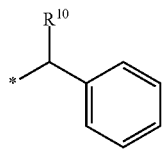 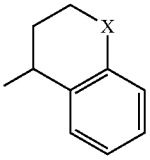

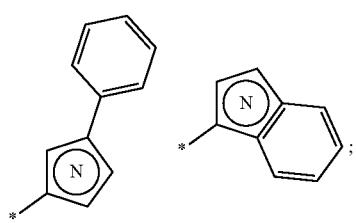
;

$R^{10}$ of

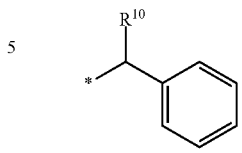

is selected from H, alkyl, or aryl;

X of

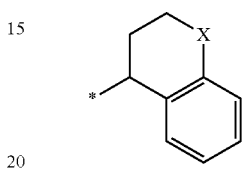

is selected from CH2 and O; and

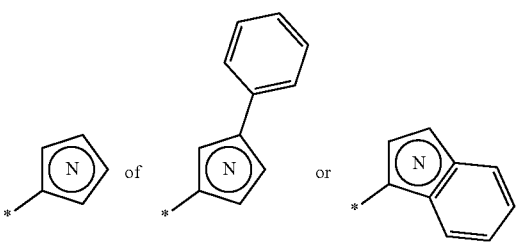

is a nitrogen-containing heteraryl.

In any of the compounds described herein, the ILM is selected from the group consisting of:

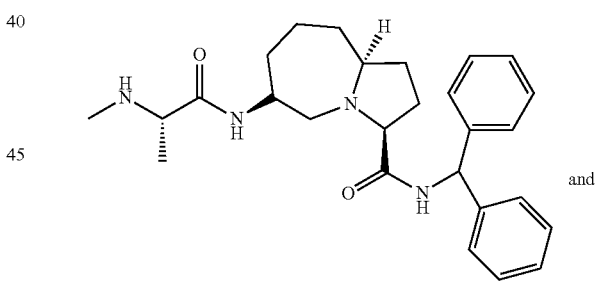 and

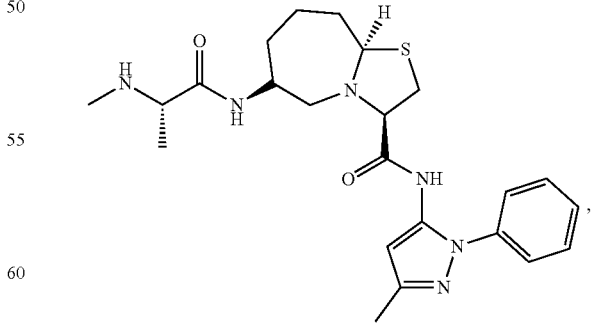, which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

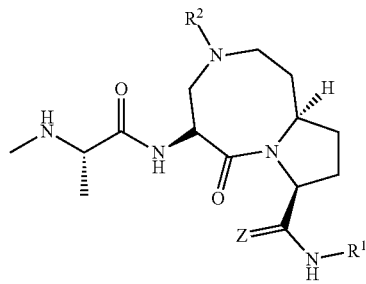
(XV)

wherein:

Z of Formula (XV) is absent or O;

R¹ of Formula (XV) is selected from:

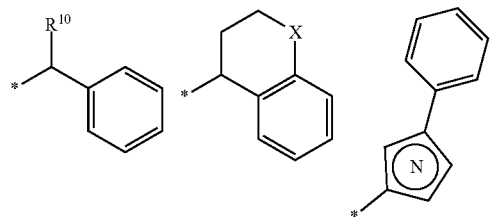

R¹⁰ of

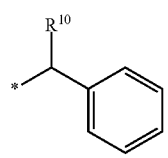

is selected from H, alkyl, or aryl;

X of

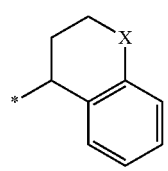

is selected from CH2 and O; and

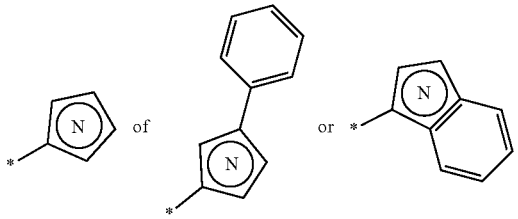

is a nitrogen-containing heteraryl; and

R² of Formula (XV) selected from H, alkyl, or acyl;

In a particular embodiment, the ILM has the following structure:

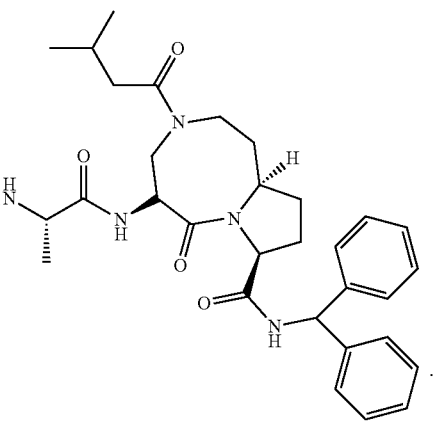

In any of the compounds described herein, the ILM can have the structure of Formula (XVI), which is based on the IAP ligand described in WO Pub. No. 2006/069063, or an unnatural mimetic thereof:

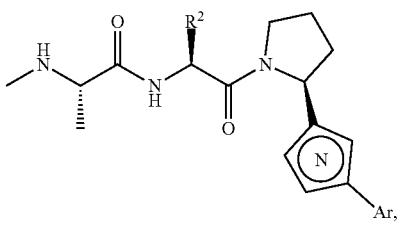
(XVI)

wherein:

R² of Formula (XVI) is selected from alkyl, cycloalkyl and heterocycloalkyl; more preferably, from isopropyl, tert-butyl, cyclohexyl and tetrahydropyranyl, most preferably from cyclohexyl;

of Formula (XVI) is a 5- or 6-membered nitrogen-containing heteroaryl; more preferably, 5-membered nitrogen-containing heteroaryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

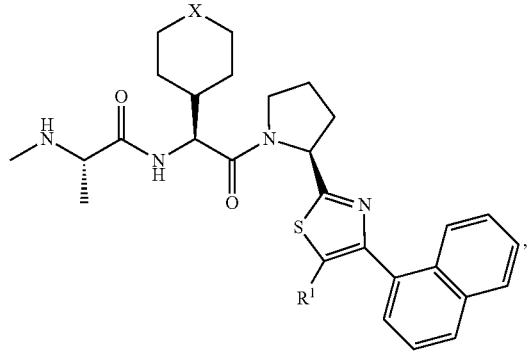
(XVII)

wherein:
$R^1$ of Formula (XVII) is selected from the group halogen (e.g. fluorine), cyano,

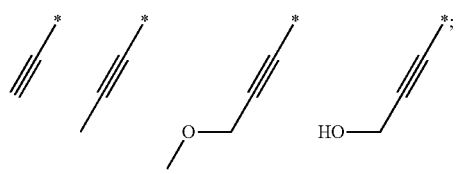

X of Formula (XVII) is selected from the group O or CH2.

In any of the compounds described herein, the ILM can have the structure of Formula (XVIII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

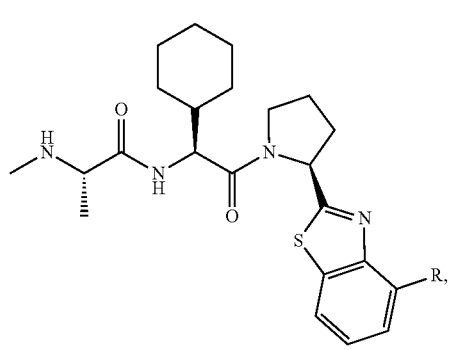
(XVIII)

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., *Antogonists of inhibitors of apoptosis proteins based on thiazole amide isosteres*, Bioorg. Med. Chem. Lett., 20(7), 2229-33 (2010), or an unnatural mimetic thereof:

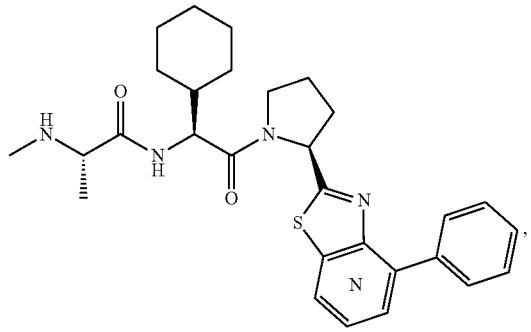
(XIX)

wherein

is a 6-member nitrogen heteroaryl.

In a certain embodiment, the ILM of the composition is selected from the group consisting of:

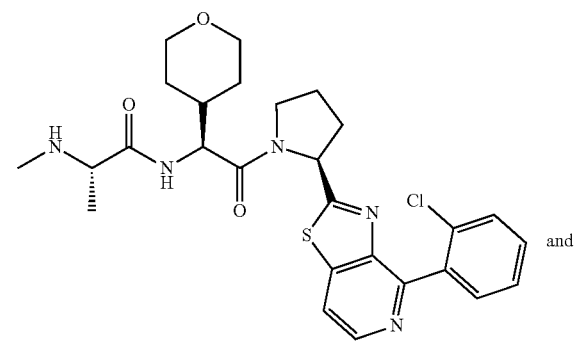
and

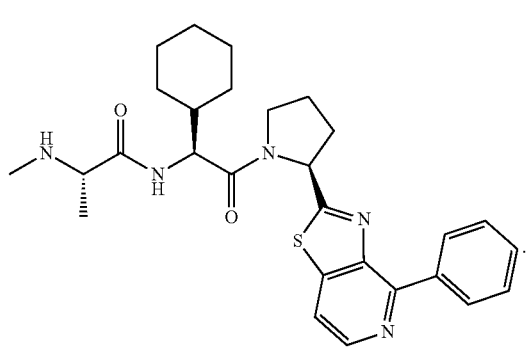

In certain embodiments, the ILM of the composition is selected from the group consisting of:

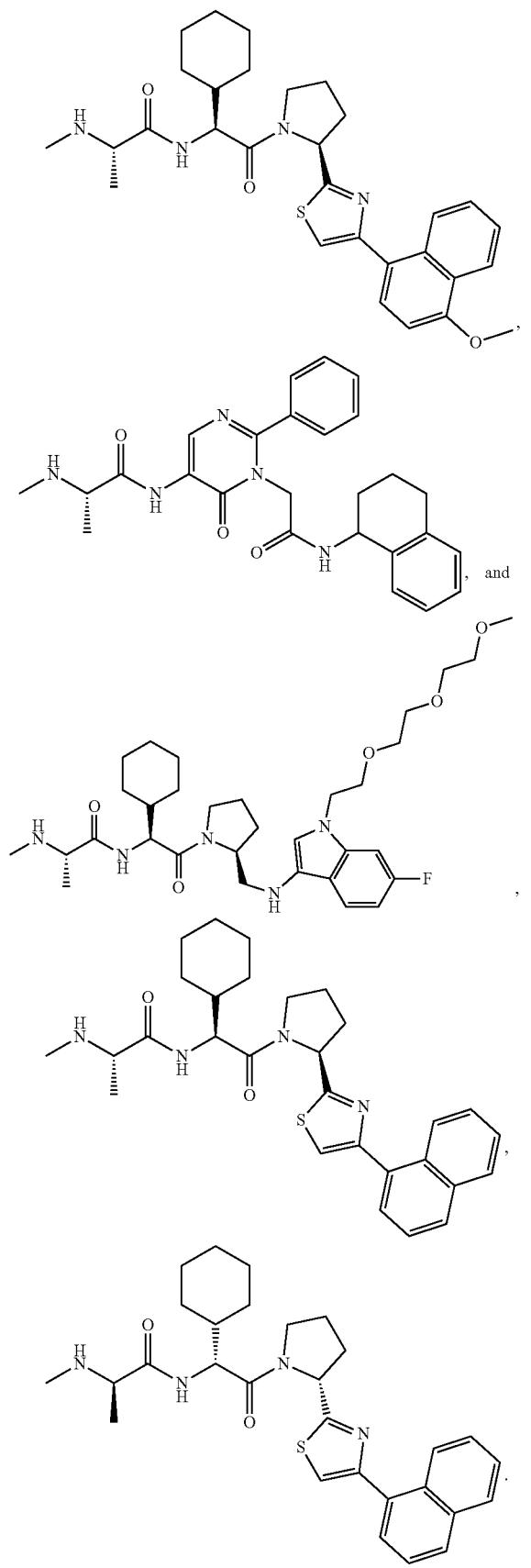

and

In any of the compounds described herein, the ILM can have the structure of Formula (XX), which is based on the IAP ligands described in WO Pub. No. 2007/110347, or an unnatural mimetic thereof:

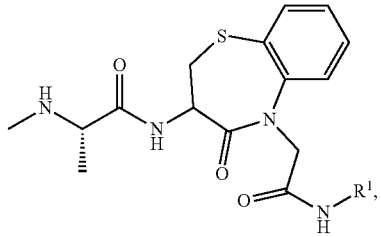

(XX)

wherein X of Formula (XX) is selected from CH$_2$, O, NH, or S.

In any of the compounds described herein, the ILM can have the structure of Formula (XXI), which is based on the IAP ligands described in U.S. Pat. Nos. 7,345,081 and 7,419,975, or an unnatural mimetic thereof:

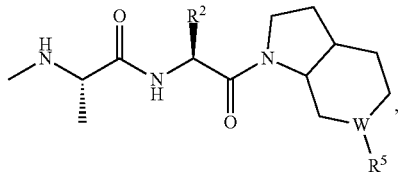

(XXI)

wherein:

R$^2$ of Formula (XXI) is selected from:

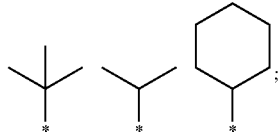

R$^5$ of Formula (XXI) is selected from:

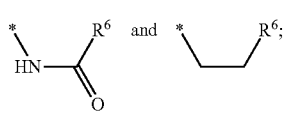

and

W of Formula (XXI) is selected from CH or N; and

R$^6$ of

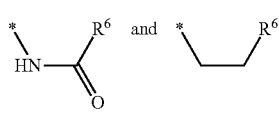

are independently a mono- or bicyclic fused aryl or heteroaryl.

In certain embodiments, the ILM of the compound is selected from the group consisting of:

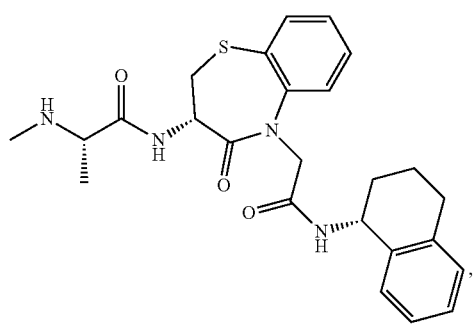
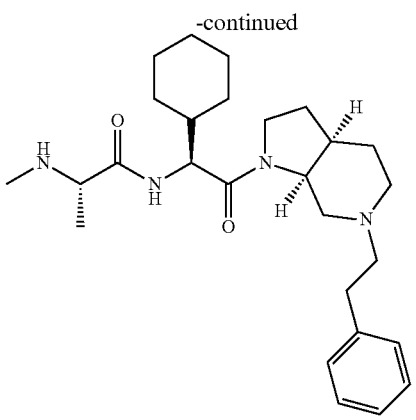
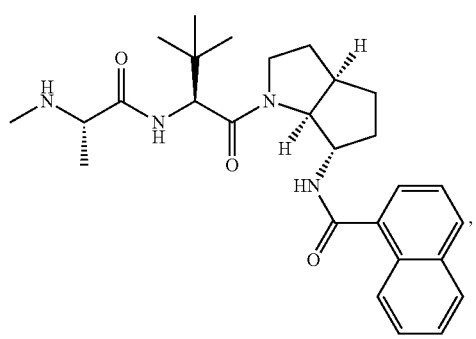
, and
In certain embodiments, the ILM of the compound is selected from the group consisting of:
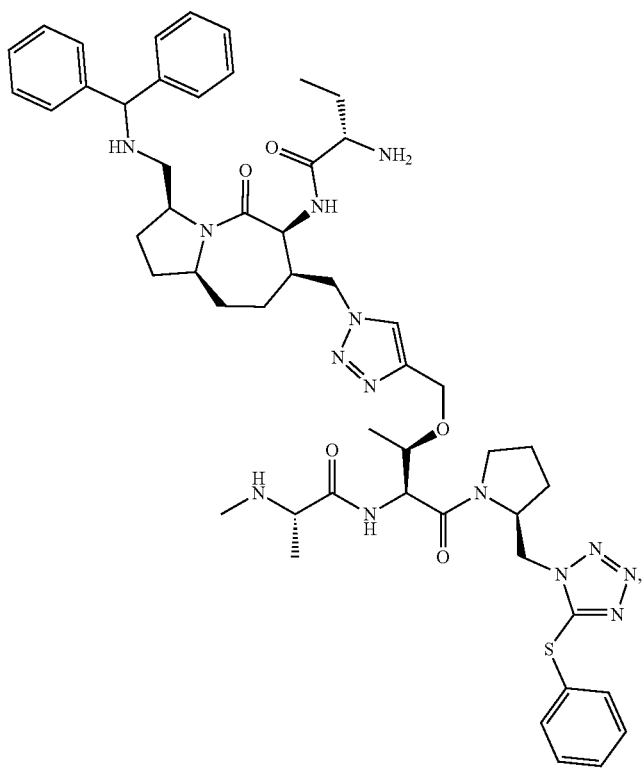

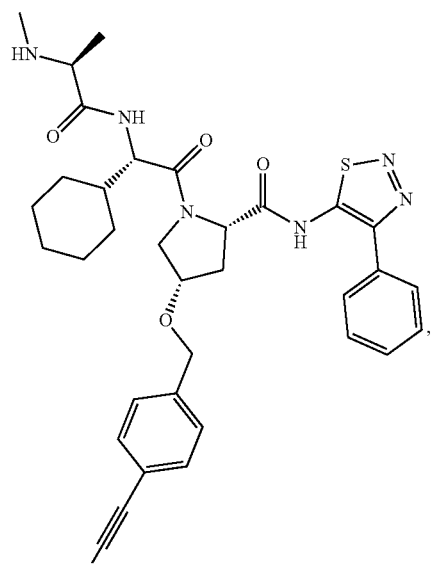
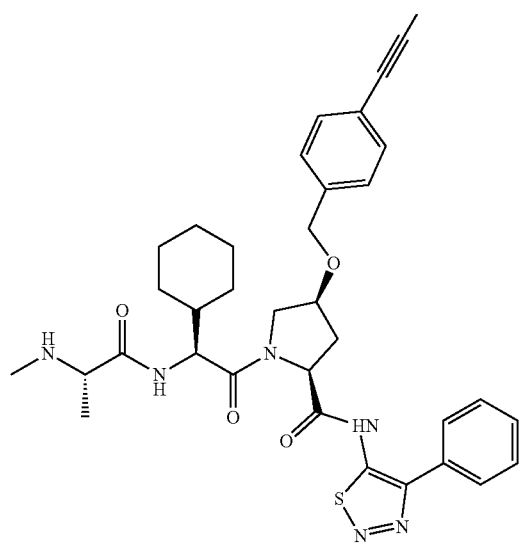
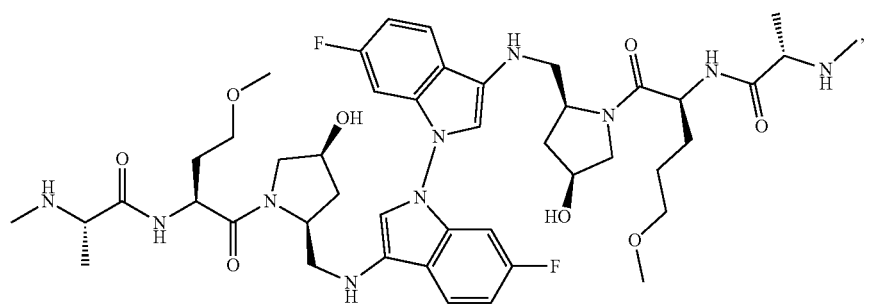

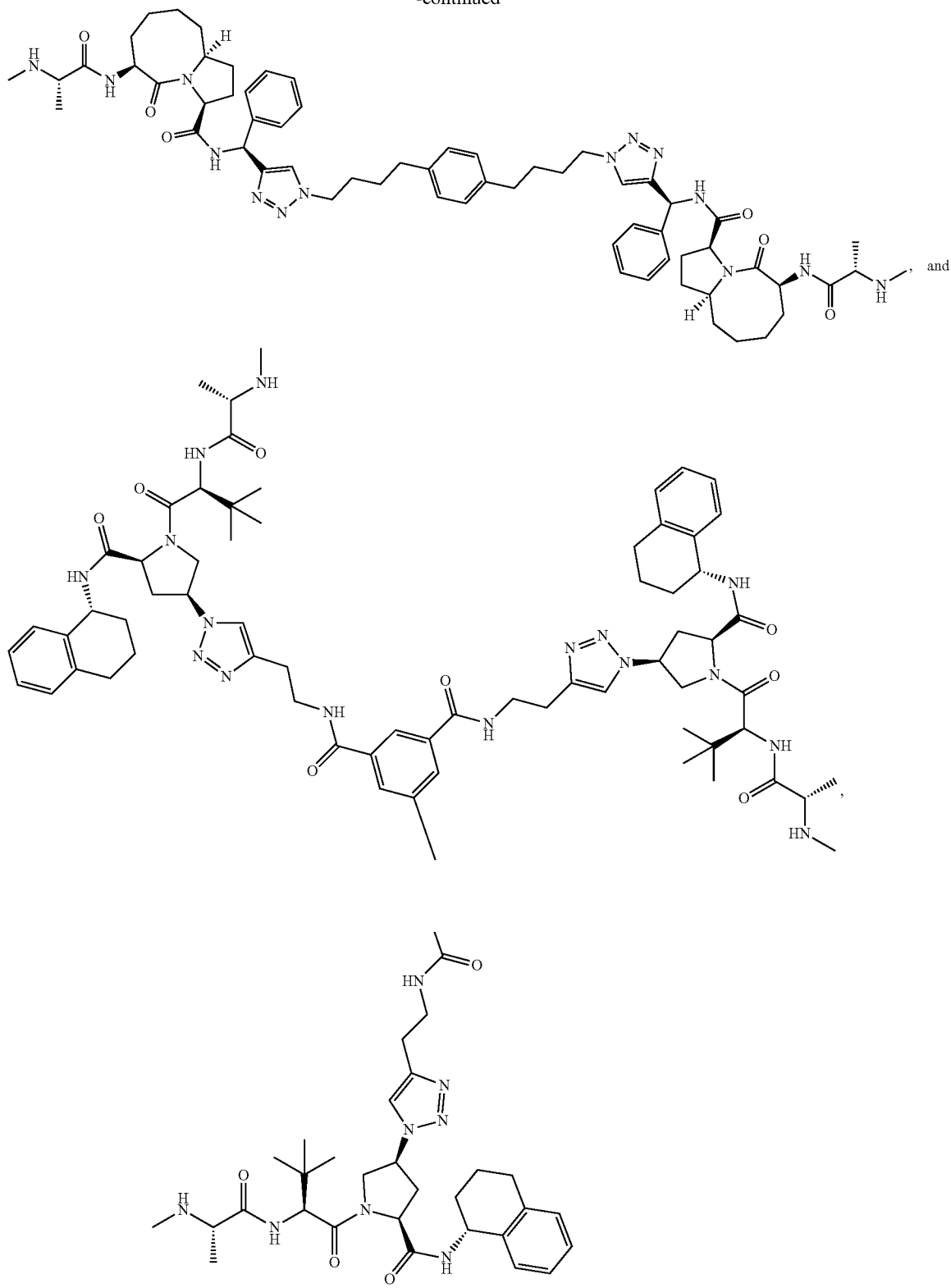

which are described in WO Pub. No. 2009/060292, U.S. Pat. No. 7,517,906, WO Pub. No. 2008/134679, WO Pub. No. 2007/130626, and WO Pub. No. 2008/128121.

In any of the compounds described herein, the ILM can have the structure of Formula (XXII) or (XXIII), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof:

(XXII)

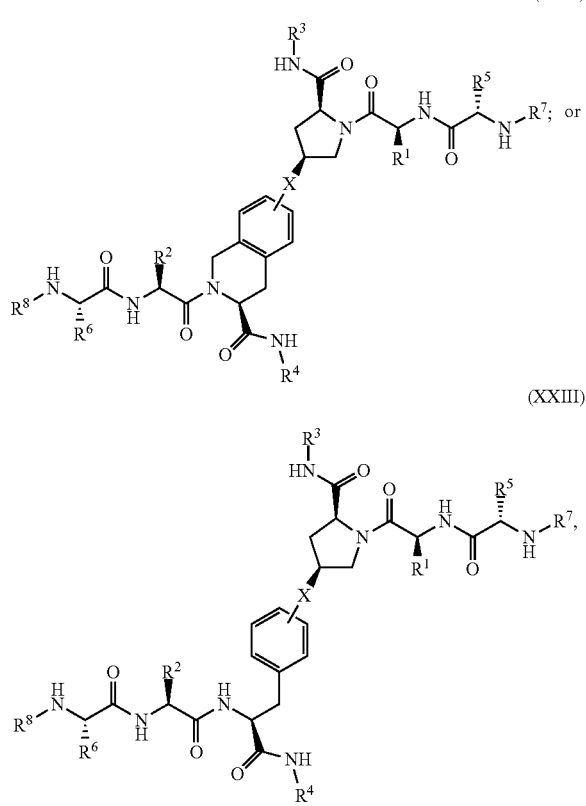

(XXIII)

wherein:
R¹ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;

R² of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;

or alternatively, R¹ and R² of Formula (XXII) or (XXIII) are independently optionally substituted thioalkyl wherein the substituents attached to the S atom of the thioalkyl are optionally substituted alkyl, optionally substituted branched alkyl, optionally substituted heterocyclyl, $-(CH_2)_vCOR^{20}$, $-CH_2CHR^{21}COR^{22}$ or $-CH_2R^{23}$;

wherein:
v is an integer from 1-3;
$R^{20}$ and $R^{22}$ of $-(CH_2)_vCOR^{20}$ and $-CH_2R^{23}$ are independently selected from OH, $NR^{24}R^{25}$ or $OR^{26}$;
$R^{21}$ of $-CH_2CHR^{21}COR^2$ is selected from the group $NR^{24}R^{25}$;
$R^{23}$ of $-CH_2R^{23}$ is selected from optionally substituted aryl or optionally substituted heterocyclyl, where the optional substituents include alkyl and halogen;
$R^{24}$ of $NR^{24}R^{25}$ is selected from hydrogen or optionally substituted alkyl;
$R^{25}$ of $NR^{24}R^{25}$ is selected from hydrogen, optionally substituted alkyl, optionally substituted branched alkyl, optionally substituted arylalkyl, optionally substituted heterocyclyl, $-CH_2(OCH_2CH_2O)_mCH_3$, or a polyamine chain, such as spermine or spermidine;

$R^{26}$ of $OR^{26}$ is selected from optionally substituted alkyl, wherein the optional substituents are OH, halogen or $NH_2$; and m is an integer from 1-8;

$R^3$ and $R^4$ of Formula (XXII) or (XXIII) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXII) or (XXIII) are independently selected from hydrogen, optionally substituted alkyl or optionally substituted cycloalkyl; and X is selected from a bond or a chemical linker group, and/or a pharmaceutically acceptable salt, tautomer or stereoisomer thereof.

In certain embodiments, X is a bond or is selected from the group consisting of:

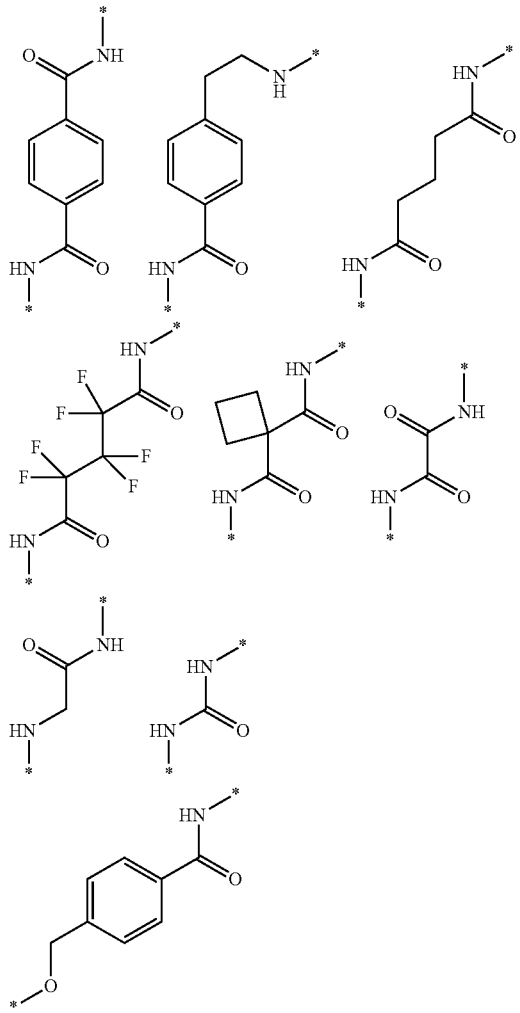

-continued

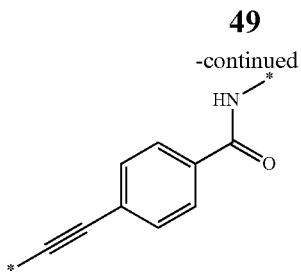

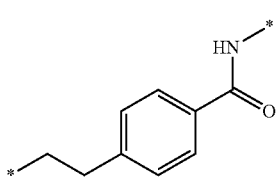

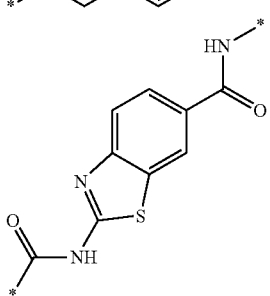

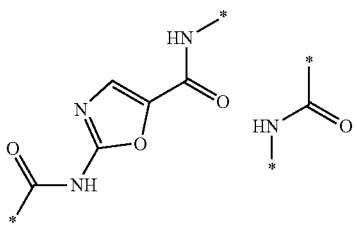

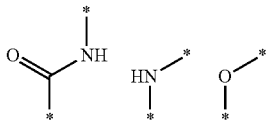

wherein "*" is the point of attachment of a PTM, L or ULM, e.g., an ILM.

In any of the compounds described herein, the ILM can have the structure of Formula (XXIV) or (XXVI), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof, and the chemical linker to linker group L as shown:

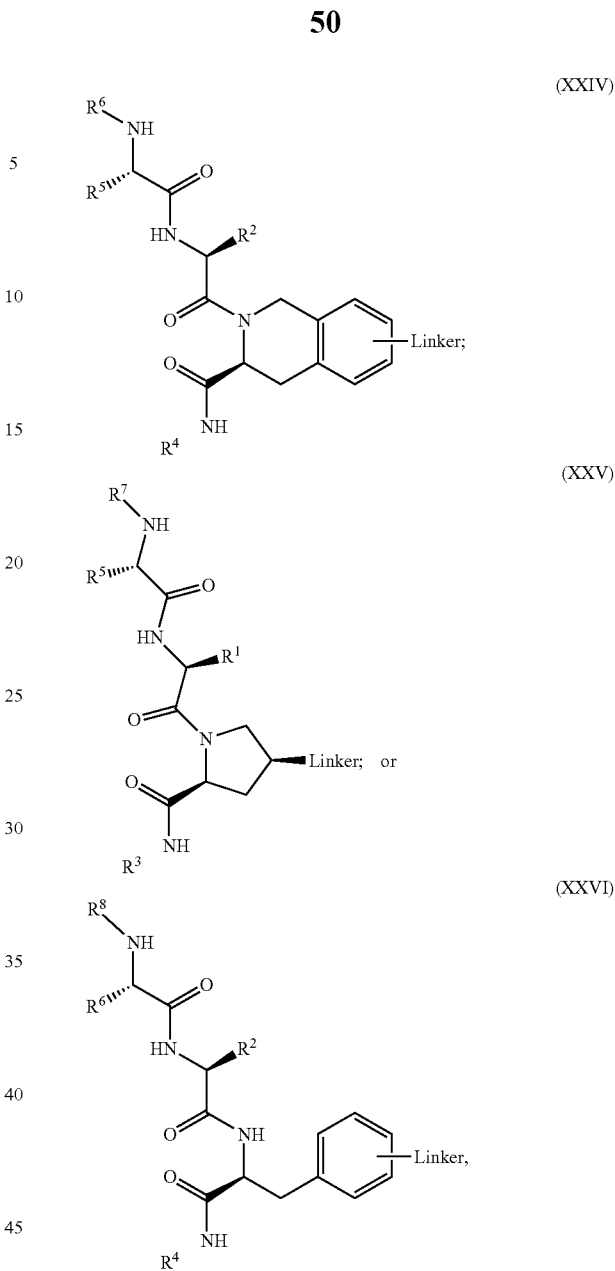

wherein:

$R^1$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

or alternatively, $R^1$ and $R^2$ of Formula (XXIV), (XXV) or (XXVI) are independently selected from optionally substituted thioalkyl wherein the substituents attached to the S atom of the thioalkyl are optionally substituted alkyl, optionally substituted branched alkyl, optionally substituted heterocyclyl, $-(CH_2)_vCOR^{20}$, $-CH_2CHR^{21}COR^{22}$ or $-CH_2R^{23}$ wherein:
v is an integer from 1-3;
R$^{20}$ and R$^{22}$ of —(CH$_2$)$_v$COR$^{20}$ and —CH$_2$R$^{23}$ are independently selected from OH, NR$^{24}$R$^{25}$ or OR$^{26}$;
R$^{21}$ of —CH$_2$CHR$^{21}$COR$^2$ is selected from NR$^{24}$R$^{25}$;
R$^{23}$ of —CH$_2$R$^{23}$ is selected from optionally substituted aryl or optionally substituted heterocyclyl, wherein the optional substituents include alkyl and halogen;
R$^{24}$ of NR$^{24}$R$^{25}$ is selected from hydrogen or optionally substituted alkyl;
R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$_2$O)$_m$CH$_3$, or a polyamine chain, such as spermine or spermidine;
R$^{26}$ of OR$^{26}$ is selected from optionally substituted alkyl, wherein the optional substituents are OH, halogen or NH$_2$; and
m is an integer from 1-8;
R$^3$ and R$^4$ of Formula (XXIV), (XXV) or (XXVI) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;
R$^5$, R$^6$, R$^7$ and R$^8$ of Formula (XXIV), (XXV) or (XXVI) are independently hydrogen, optionally substituted alkyl or optionally substituted cycloalkyl; and/or a pharmaceutically acceptable salt, tautomer or stereoisomer thereof.

In a particular embodiment, the ILM according to Formulas (XXII) through (XXVI):
R$^7$ and R$^8$ are selected from the H or Me;
R$^5$ and R$^6$ are selected from the group comprising:

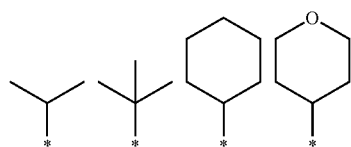

R$^3$ and R$^4$ are selected from the group comprising:

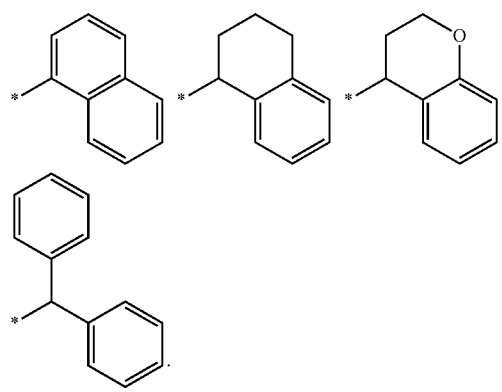

In any of the compounds described herein, the ILM can have the structure of Formula (XXVII) or (XXVII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof:

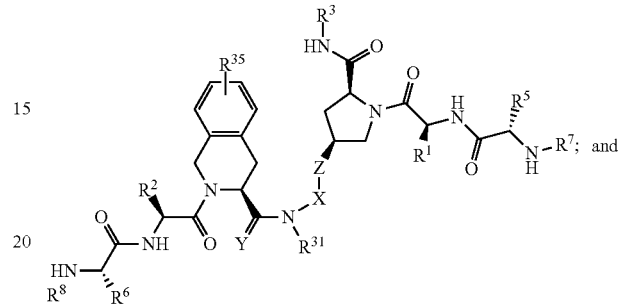

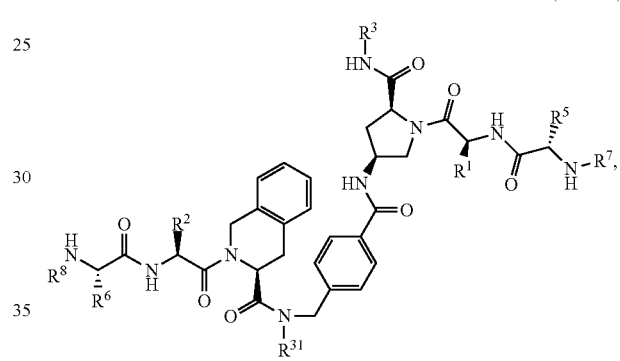

wherein:
R$^{35}$ is 1-2 substituents selected from alkyl, halogen, alkoxy, cyano and haloalkoxy;
R$^1$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;
R$^2$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;
or alternatively,
R$^1$ and R$^2$ of Formula (XXVII) and (XXVIII) are independently selected from an optionally substituted thioalkyl —CR$^{60}$R$^{61}$SR$^{70}$, wherein R$^{60}$ and R$^{61}$ are selected from H or methyl, and R$^{70}$ is selected from an optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$
wherein:
v is an integer from 1-3;
R$^{20}$ and R$^{22}$ of —(CH$_2$)$_v$COR$^{20}$ and —CH$_2$CHR$^{21}$COR$^{22}$ are independently selected from OH, NR$^{24}$R$^{25}$ or OR$^{26}$;
R$^{21}$ of —CH$_2$CHR$^{21}$COR$^{22}$ is selected from NR$^{24}$R$^{25}$;

R²³ of —CH₂R²³ is selected from an optionally substituted aryl or optionally substituted heterocyclyl, where the optional substituents include alkyl and halogen;

R²⁴ of NR²⁴R²⁵ is selected from hydrogen or optionally substituted alkyl;

R²⁵ of NR²⁴R²⁵ is selected from hydrogen, optionally substituted alkyl, optionally substituted branched alkyl, optionally substituted arylalkyl, optionally substituted heterocyclyl, —CH₂CH₂(OCH₂CH₂)$_m$CH₃, or a polyamine chain —[CH₂CH₂(CH₂)$_δ$NH]$_ψ$CH₂CH₂(CH₂)$_{\overline{ω}}$NH₂, such as spermine or spermidine;

wherein δ=0-2, ω=1-3, $\overline{ω}$=0-2;

R²⁶ of OR²⁶ is an optionally substituted alkyl, wherein the optional substituents are OH, halogen or NH₂; and m is an integer from 1-8, R³ and R⁴ of Formula (XXVII) and (XXVIII) are independently selected from an optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R⁵, R⁶, R⁷ and R⁸ of Formula (XXVII) and (XXVIII) are independently selected from hydrogen, optionally substituted alkyl or optionally substituted cycloalkyl;

R³¹ of Formulas (XXVII) and (XXVIII) is selected from alkyl, aryl, arylalkyl, heteroaryl or heteroarylalkyl optionally further substituted, preferably selected form the group consisting of:

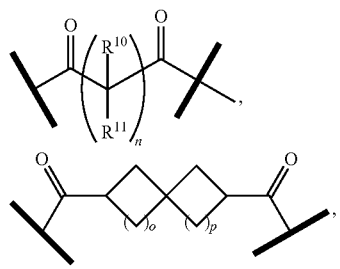

X of Formulas (XXVII) and (XXVIII) is selected from —(CR⁸¹R⁸²)$_m$—, optionally substituted heteroaryl or heterocyclyl,

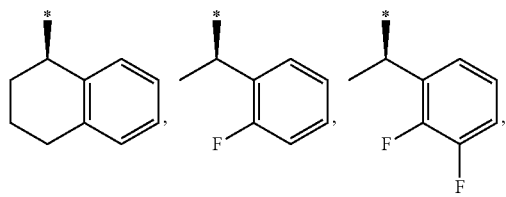

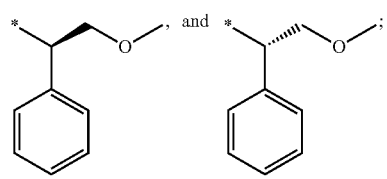

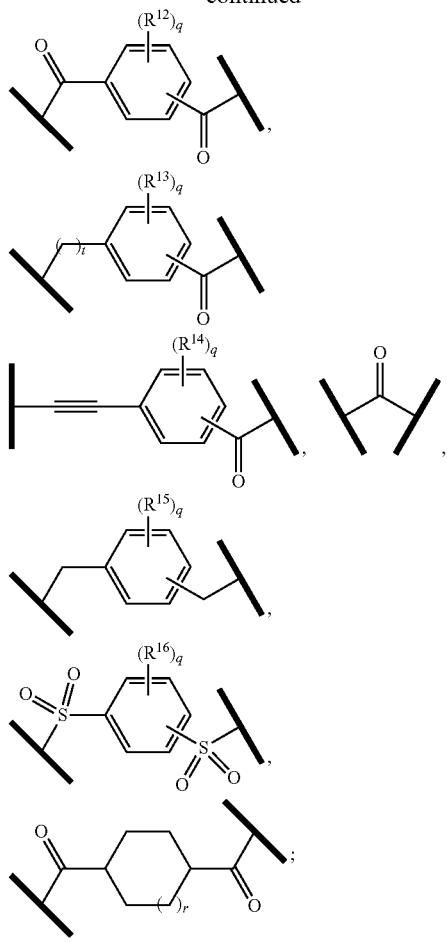

Z of Formulas (XXVII) is selected from C=O, —O—, —NR, —CONH—, —NHCO—, or may be absent;

R⁸¹ and R⁸² of —(CR⁸¹R⁸²)$_m$ are independently selected from hydrogen, halogen, alkyl or cycloalkyl, or R⁸¹ and R⁸² can be taken together to form a carbocyclic ring;

R¹⁰ and R¹¹ of

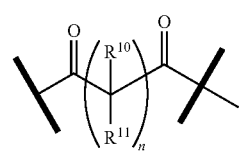

are independently selected from hydrogen, halogen or alkyl;

R¹², R¹³, R¹⁴, R¹⁵ and R¹⁶ of

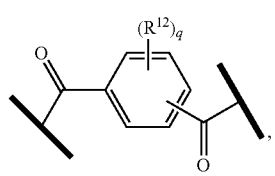

-continued

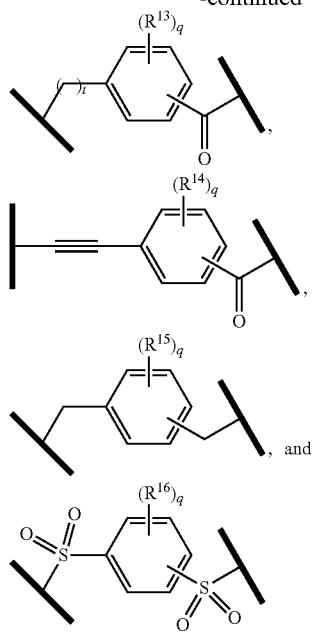

are independently selected from hydrogen, halogen or optionally substituted alkyl or $OR^{17}$;
$R^{17}$ is selected from hydrogen, optionally substituted alkyl or optionally substituted cycloalkyl;
m and n of —$(CR^{21}R^{22})_m$— and

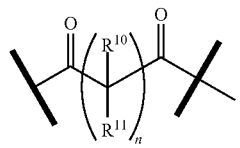

are independently 0, 1, 2, 3, or 4;
o and p of

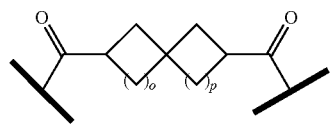

are independently 0, 1, 2 or 3;
q and t of

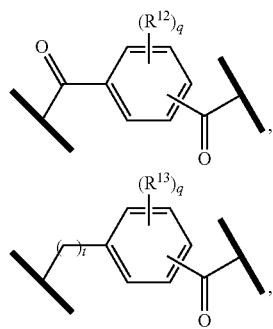

-continued

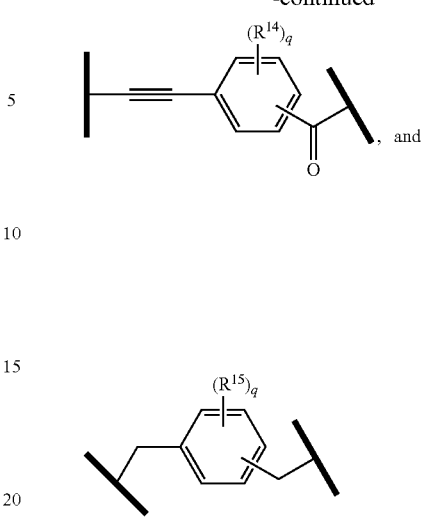

are independently 0, 1, 2, 3, or 4;
r of

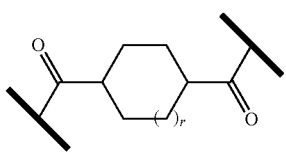

is 0 or 1;
and/or a pharmaceutically acceptable salt, tautomer or stereoisomer thereof.

In any of the compounds described herein, the ILM can have the structure of Formula (XXIX), (XXX), (XXXI), or (XXXII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof, and the chemical linker to linker group L as shown:

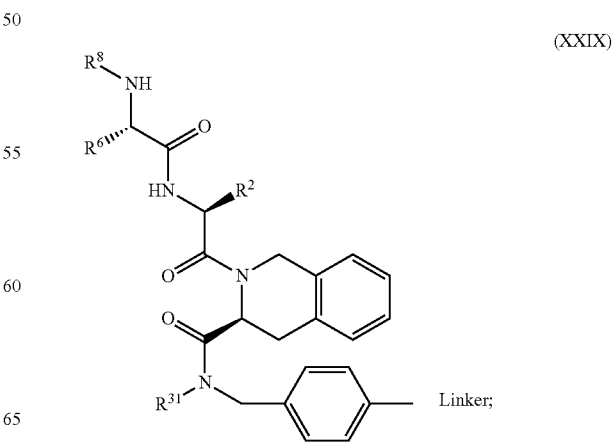

(XXIX)

-continued

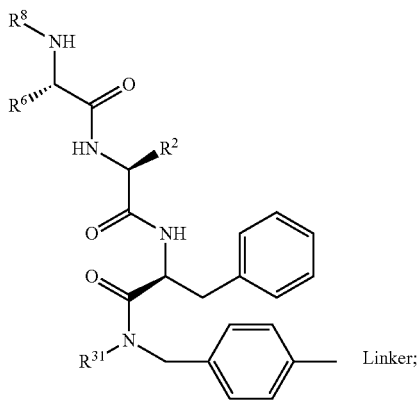

(XXX)

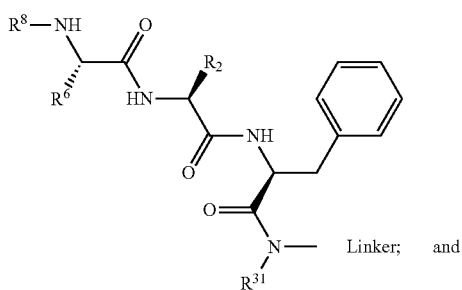

(XXXI)

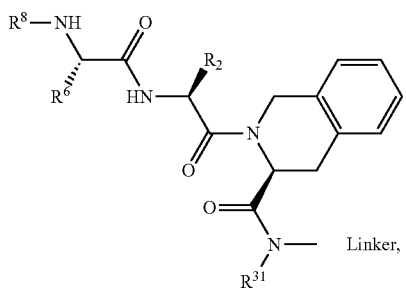

(XXXII)

wherein:

$R^2$ of Formula (XXIX) through (XXXII) is selected from H, an optionally substituted alkyl, optionally substituted cycloalkyl, optionally substituted cycloalkylalkyl, optionally substituted heterocyclyl, optionally substituted arylalkyl or optionally substituted aryl;

or alternatively;

$R^1$ and $R^2$ of Formula (XXVII) and (XXVIII) are independently selected from H, an optionally substituted thioalkyl —$CR^{60}R^{61}SR^{70}$ wherein $R^{60}$ and $R^{61}$ are selected from H or methyl, and $R^{70}$ is an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$;

wherein:

v is an integer from 1-3;

$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;

$R^{21}$ of —$CH_2CHR^{21}COR^{22}$ is selected from $NR^{24}R^{25}$;

$R^{23}$ of —$CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain —$[CH_2CH_2(CH_2)_\delta NH]_\psi CH_2CH_2(CH_2)\overline{\omega}_rNH_2$, such as spermine or spermidine, wherein $\delta=0-2$, $\psi=1-3$, $\overline{\omega}=0-2$;

$R^{26}$ of $OR^{26}$ is an optionally substituted alkyl, wherein the optional substituents are OH, halogen or $NH_2$;

m is an integer from 1-8;

$R^6$ and $R^8$ of Formula (XXIX) through (XXXII) are independently selected from hydrogen, optionally substituted alkyl or optionally substituted cycloalkyl; and $R^{31}$ of Formulas (XXIX) through (XXXII) is selected from alkyl, aryl, arylalkyl, heteroaryl or heteroarylalkyl optionally further substituted, preferably selected form the group consisting of:

In certain embodiments, the ILM of the compound is:

In any of the compounds described herein, the ILM can have the structure of Formula (XXXIII), which are derived from the IAP ligands described in WO Pub. No. 2014/074658 and WO Pub. No. 2013/071035, or an unnatural mimetic thereof:

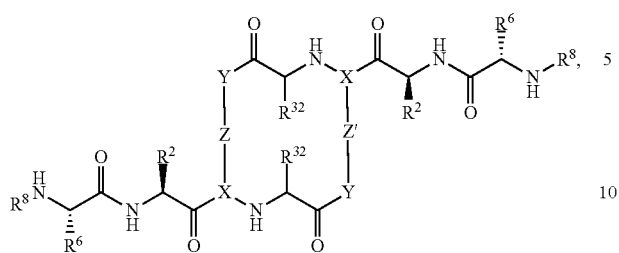

(XXXIII)

wherein:
- $R^2$ of Formula (XXXIII) is selected from H, an optionally substituted alkyl, optionally substituted cycloalkyl, optionally substituted cycloalkylalkyl, optionally substituted heterocyclyl, optionally substituted arylalkyl or optionally substituted aryl;
- $R^6$ and $R^8$ of Formula (XXXIII) are independently selected from hydrogen, optionally substituted alkyl or optionally substituted cycloalkyl;
- $R^{32}$ of Formula (XXXIII) is selected from ($C_1$-$C_4$ alkylene)-$R^{33}$ wherein $R^{33}$ is selected from hydrogen, aryl, heteroaryl or cycloalkyl optionally further substituted;
- X of Formula (XXXIII) is selected from:

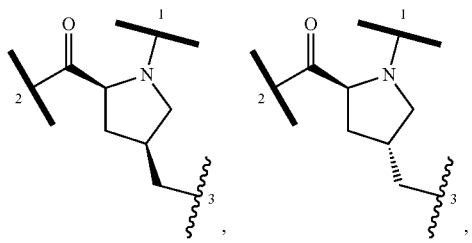

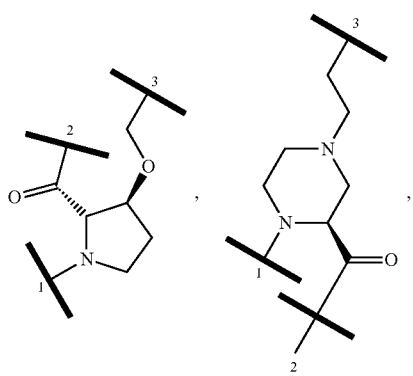

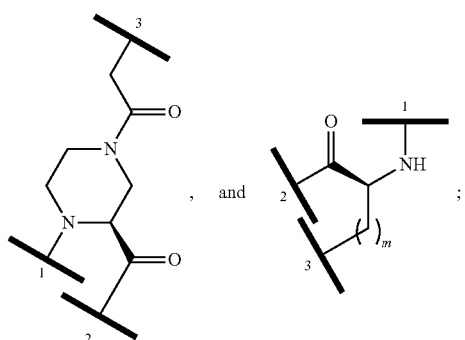

Z and Z' of Formula (XXXIII) are independently selected from:

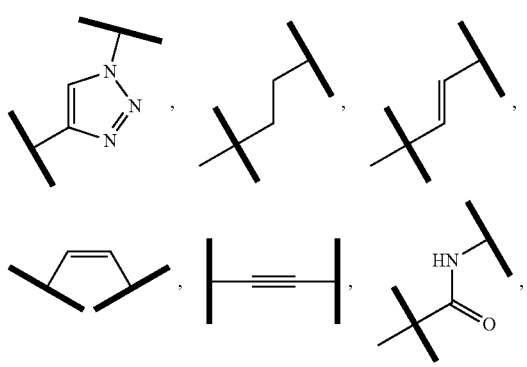

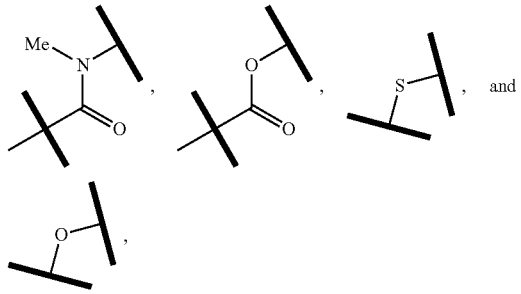

wherein each
represents a point of attachment to the compound, and Z and Z' cannot both be
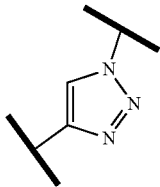
in any given compound;
Y of Formula (XXXIII) is selected from:
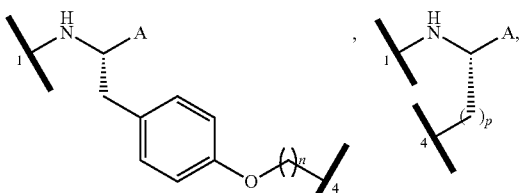
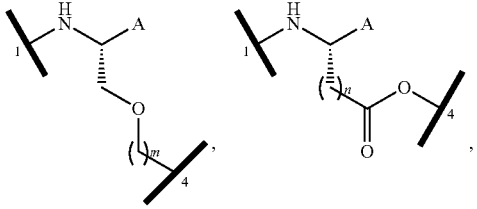
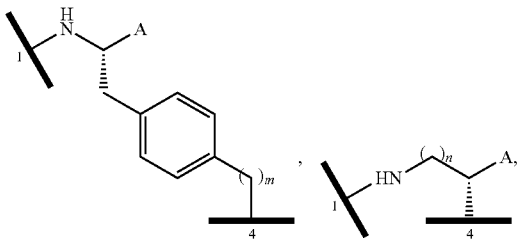
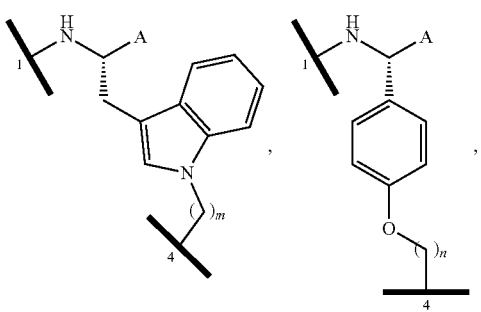, and
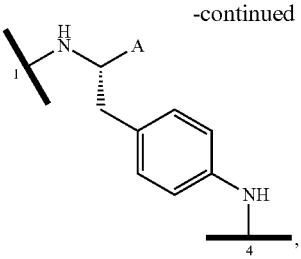
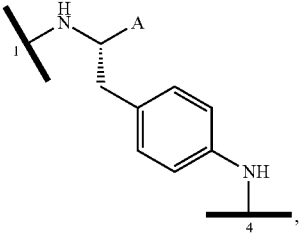
wherein Z and Z' of Formula (XXXIII) are the same and Z is
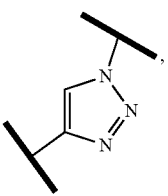,
wherein each
represents a point of attachment to the compound, X is selected from:
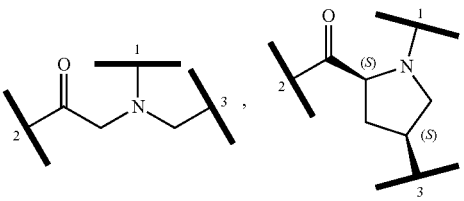
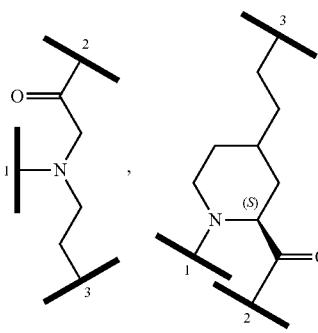
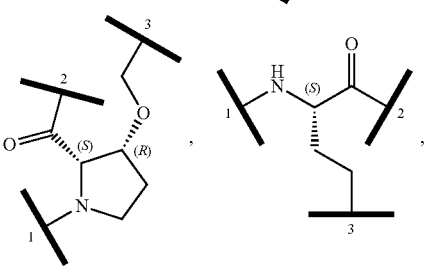

-continued
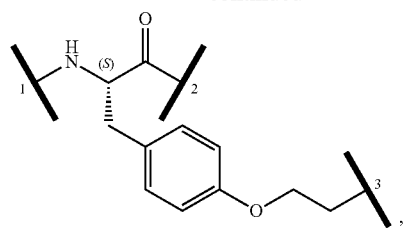
,
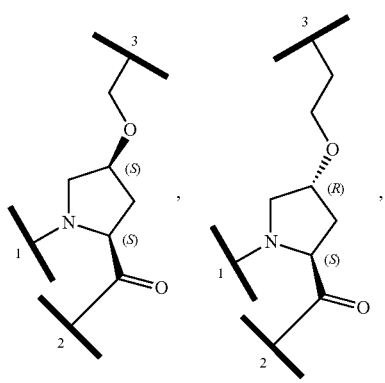
,
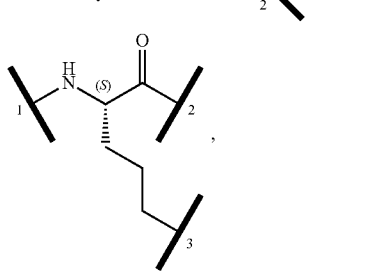
,
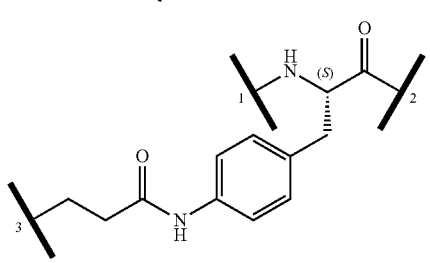
,
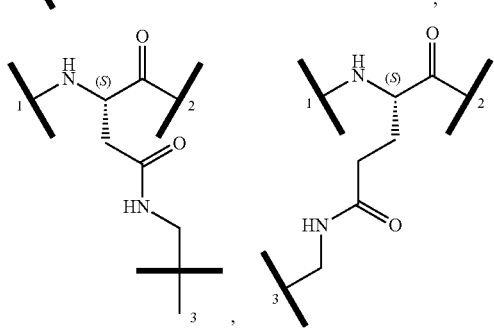
,
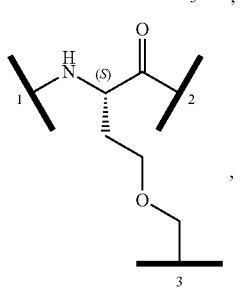
,
-continued
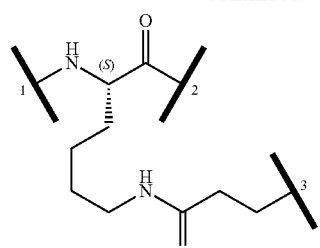
,
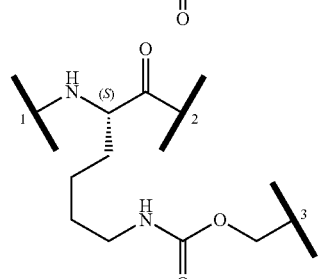
,
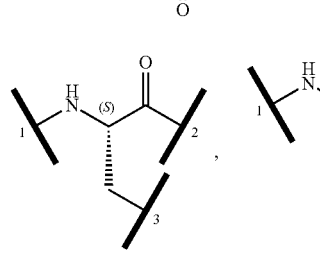
,
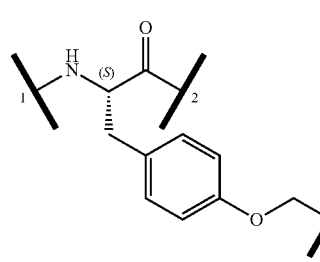
, and
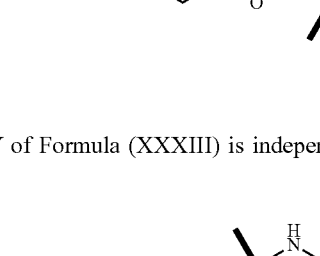
and
Y of Formula (XXXIII) is independently selected from:
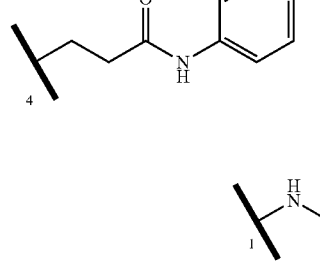
,
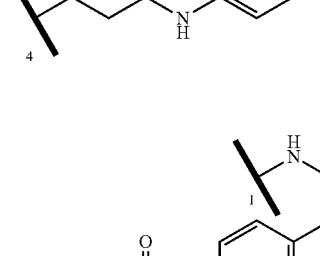
, -continued
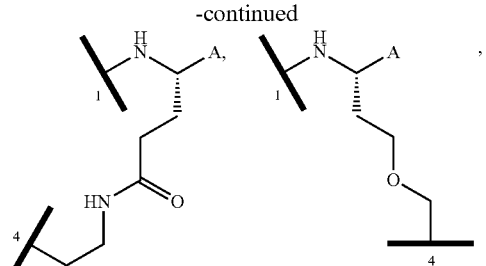
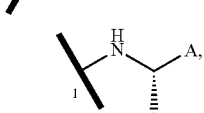
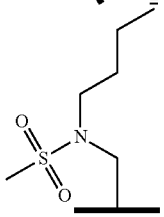
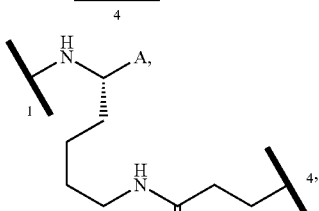
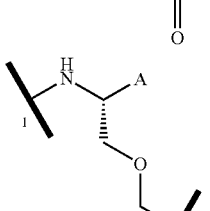
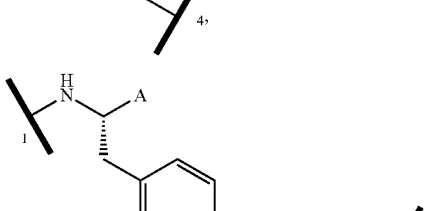
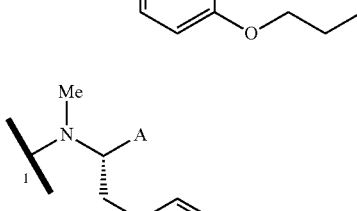
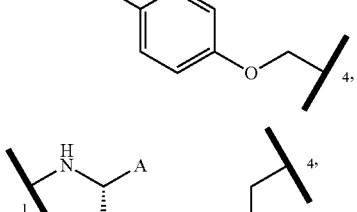
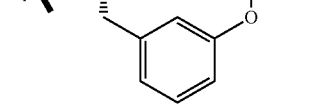
-continued
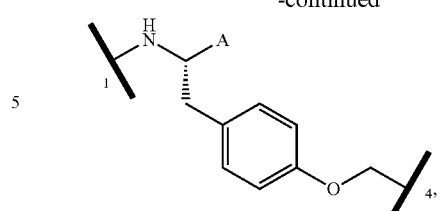
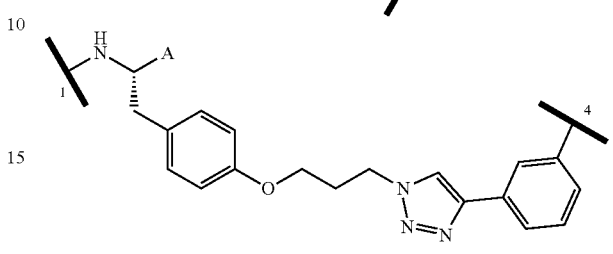
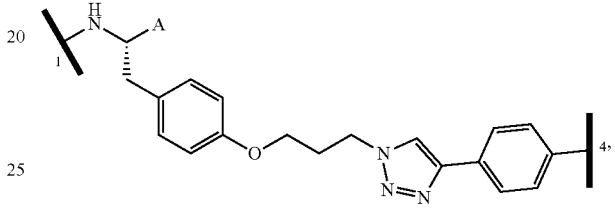
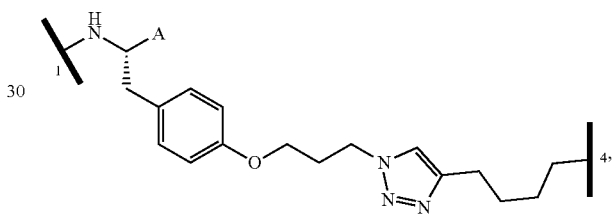
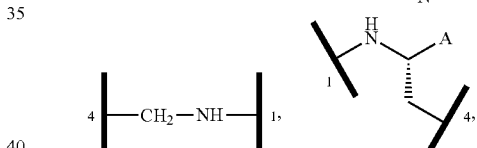
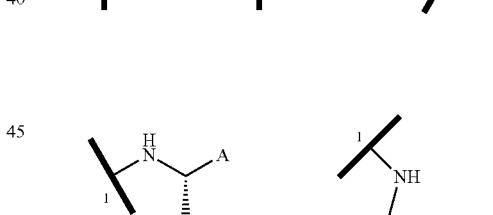
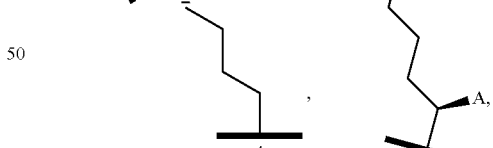
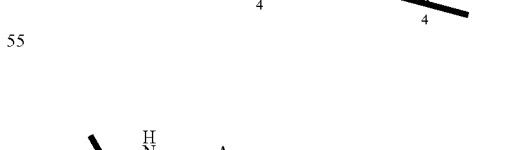
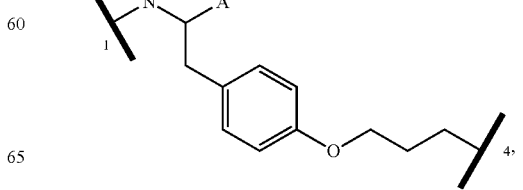

-continued

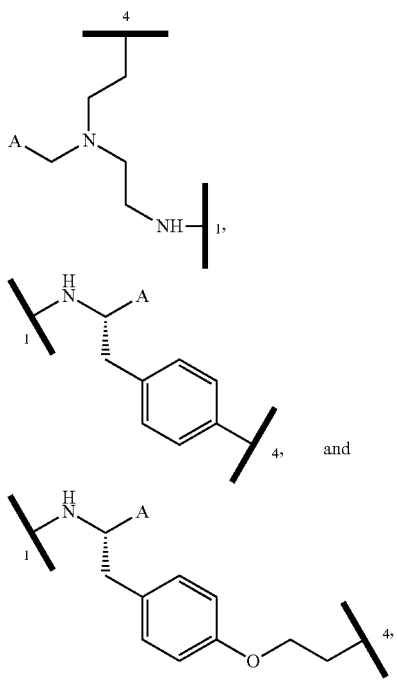

wherein:

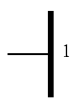

represents a point of attachment to a —C=O portion of the compound;


represents a point of attachment to a —NH portion of the compound;

i represents a first point of attachment to Z;

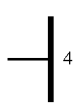

represents a second point of attachment to Z;
m is an integer from 0-3;
n is an integer from 1-3;
p is an integer from 0-4; and
A is —C(O)$R^3$;

$R^3$ is selected from —C(O)$R^3$ is OH, NHCN, NHSO$_2$$R^{10}$, NHO$R^{11}$ or N($R^{12}$)($R^{13}$);

$R^{10}$ and $F^{11}$ of NHSO$_2$$R^{10}$ and NHO$R^{11}$ are independently selected from hydrogen, optionally substituted —C$_1$-C$_4$ alkyl, cycloalkyl, aryl, heteroaryl, heterocyclyl or heterocycloalkyl;

$R^{12}$ and $R^{13}$ of N($R^{12}$)($R^{13}$) are independently selected from hydrogen, —C$_1$-C$_4$ alkyl, —(C$_1$-C$_4$) alkylene)-NH—(C$_1$-C$_4$ alkyl), and —(C$_1$-C$_4$ alkylene)-O—(C$_1$-C$_4$ hydroxyalkyl), or $R^{12}$ and $R^{13}$ taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXIV) or (XXXV), which are derived from the IAP ligands described in WO Pub. No. 2014/047024, or an unnatural mimetic thereof:

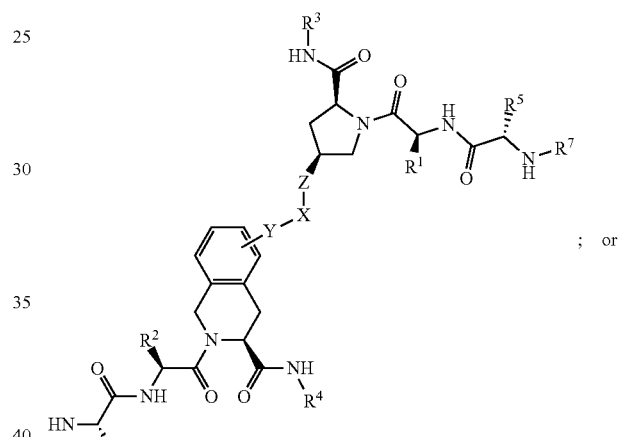

(XXXIV)

; or

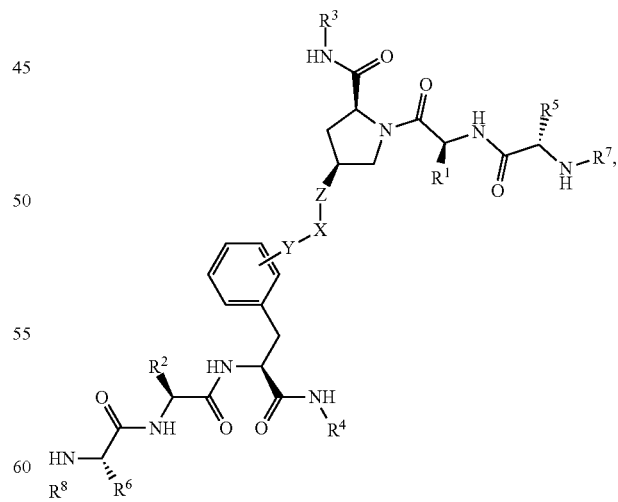

(XXXV)

wherein:

X of Formula (XXXIV) or (XXXV) is absent or a group selected from —(C$R^{10}$$R^{11}$)$_m$—, optionally substituted heteroaryl or optionally substituted heterocyclyl,

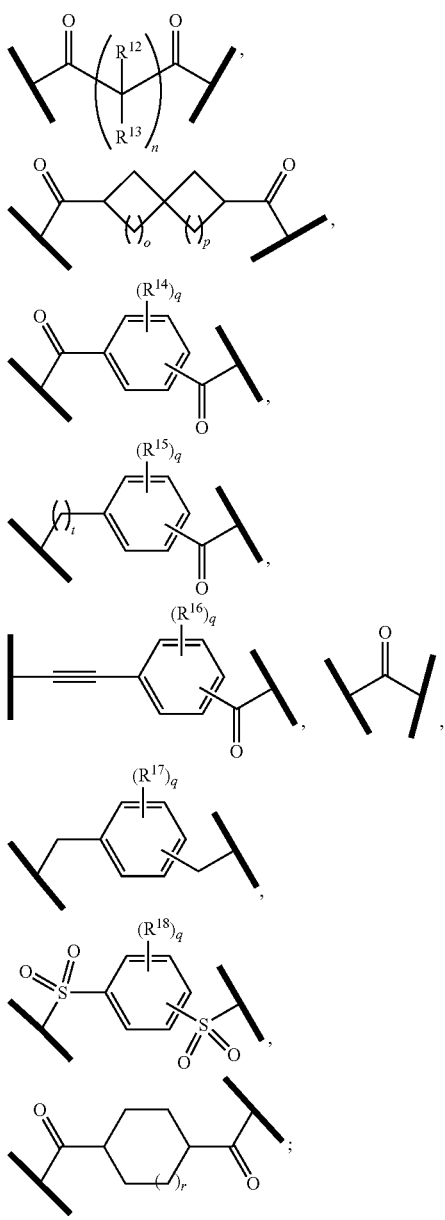

Y and Z of Formula (XXXIV) or (XXXV) are independently selected from C=O, —O—, —NR$^9$—, —CONH—, —NHCO— or may be absent;

R$^1$ and R$^2$ of Formula (XXXIV) or (XXXV) are independently selected from an optionally substituted alkyl, optionally substituted cycloalkyl, optionally substituted cycloalkylalkyl, optionally substituted arylalkyl, optionally substituted aryl, or R$^1$ and R$^2$ of Formula (XXXIV) or (XXXV) are independently selected from optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$; wherein v is an integer from 1-3;

R$^{20}$ and R$^{22}$ of —(CH$_2$)$_v$COR$^{20}$ and —CH$_2$CHR$^{21}$COR$^{22}$ are independently selected from OH, NR$^{24}$R$^{25}$ or OR$^{26}$;

R$^{21}$ of —CH$_2$CHR$^{21}$COR$^{22}$ is selected from NR$^{24}$R$^{25}$;

R$^{23}$ of —CH$_2$R$^{23}$ are selected from an optionally substituted aryl or optionally substituted heterocyclyl, where the optional substituents include alkyl and halogen;

R$^{24}$ of NR$^{24}$R$^{25}$ is selected from hydrogen or optionally substituted alkyl;

R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$^{20}$)mCH3, or a polyamine chain;

R$^{26}$ is an optionally substituted alkyl, wherein the optional substituents are OH, halogen or NH$_2$;

m of —(CR$^{10}$R$^{11}$)$_m$— is an integer from 1-8;

R$^3$ and R$^4$ of Formula (XXXIV) or (XXXV) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R$^5$, R$^6$, R$^7$ and R$^8$ of Formula (XXXIV) or (XXXV) are independently selected from hydrogen, optionally substituted alkyl or optionally substituted cycloalkyl;

R$^{10}$ and R$^{11}$ of —(CR$^{10}$R$^{11}$)$_m$— are independently selected from hydrogen, halogen or optionally substituted alkyl;

R$^{12}$ and R$^{13}$ of

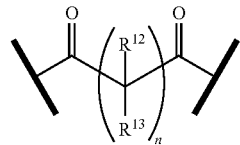

are independently selected from hydrogen, halogen or optionally substituted alkyl, or R$^{12}$ and R$^{13}$ can be taken together to form a carbocyclic ring;

R$^{14}$, R$^{15}$, R$^{16}$, R$^{17}$ and R$^{18}$ of

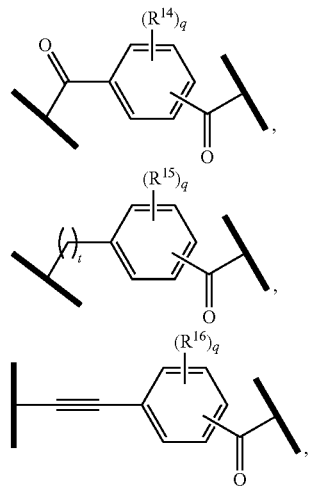

-continued

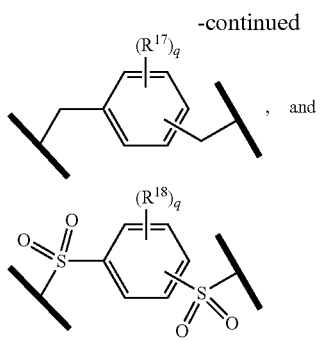
and are independently selected from hydrogen, halogen, optionally substituted alkyl or $OR^{19}$;
$R^{19}$ of $OR^{19}$ is selected from hydrogen, optionally substituted alkyl or optionally substituted cycloalkyl;
m and n of $-(CR^{10}R^{11})_m$ are independently 0, 1, 2, 3, or 4;
o and p of $-(CR^{10}R^{11})_m$ are independently 0, 1, 2 or 3;
q of $-(CR^{10}R^{11})_m$ is 0, 1, 2, 3, or 4; r is 0 or 1;
t of $-(CR^{10}R^{11})_m$ is 1, 2, or 3; and/or a pharmaceutically acceptable salt, tautomer or stereoisomer thereof.

In any of the compounds described herein, the ILM can have the structure of Formula (XXXVI), which are derived from the IAP ligands described in WO Pub. No. 2014/025759, or an unnatural mimetic thereof:

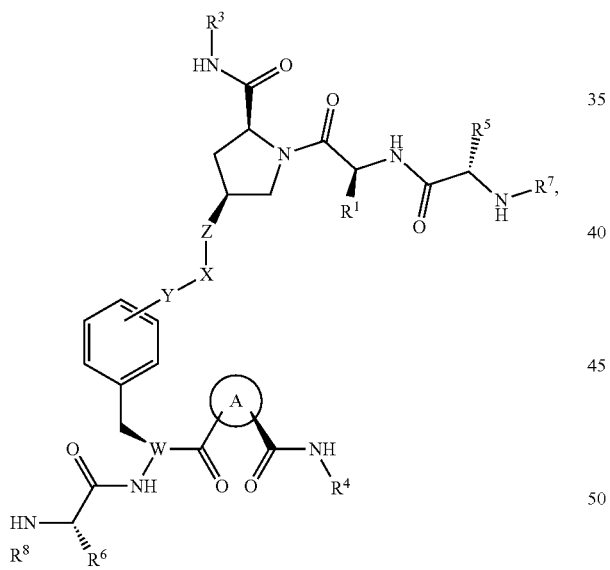
(XXXVI)

where:
A of Formula (XXXVI) is selected from:

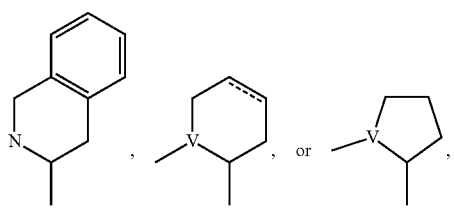

where the dotted line represents an optional double bond;
X of Formula (XXXVI) is selected from: $-(CR^{21}R^{22})_m-$,

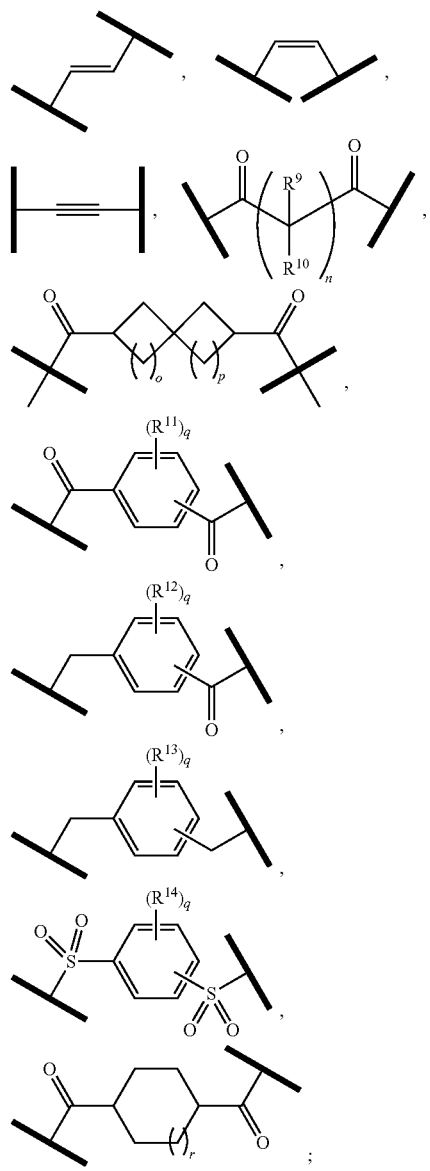

Y and Z of Formula (XXXVI) are independently selected from $-O-$, $-NR^6-$ or are absent;
V of Formula (XXXVI) is selected from $-N-$ or $-CH-$;
W of Formula (XXXVI) is selected from $-CH-$ or $-N-$;
$R^1$ of Formula (XXXVI) is selected from an optionally substituted alkyl, optionally substituted cycloalkyl, optionally substituted cycloalkylalkyl, optionally substituted arylalkyl or optionally substituted aryl;
$R^3$ and $R^4$ of Formula (XXXVI) are independently selected from optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

$R^5$, $R^6$, $R^7$ and $R^8$ of Formula (XXIV), (XXV) or (XXVI) are independently selected from hydrogen, optionally substituted alkyl or optionally substituted cycloalkyl, or preferably methyl;

$R^9$ and $R^{10}$ of

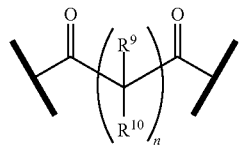

are independently selected from hydrogen, halogen or optionally substituted alkyl, or $R^9$ and $R^{10}$ can be taken together to form a ring;

$R^{11}$, $R^{12}$, $R^{13}$ and $R^{14}$ of

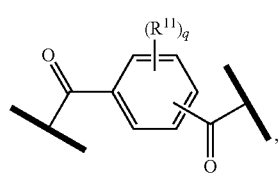

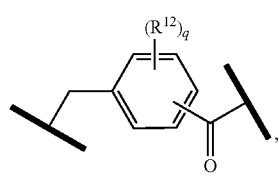

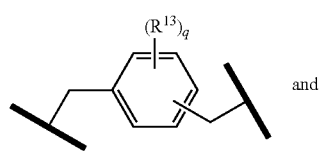

and

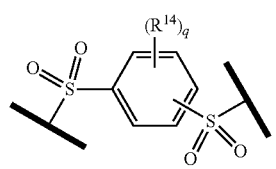

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

m and n of —$(CR^{21}R^{22})_m$— and

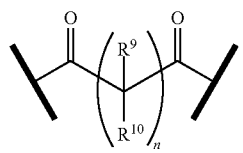

$R^{10}$ are independently selected from 0, 1, 2, 3, or 4;

o and p of

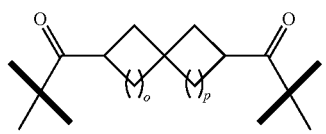

and are independently selected from 0, 1, 2 or 3;

q of

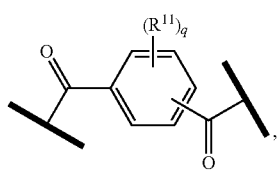

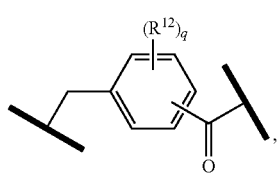

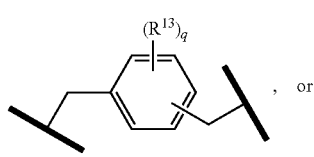

, or

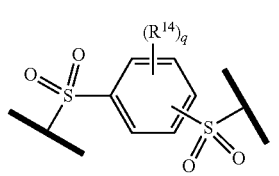

is selected from 0, 1, 2, 3, or 4;

r of

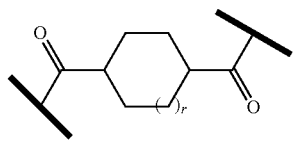

is selected from 0 or 1, and/or or a pharmaceutically acceptable salt, tautomer or stereoisomer thereof.

In any of the compounds described herein, the ILM can have the structure of Formula (XXXVII) or (XXXVIII), which are derived from the IAP ligands described in WO Pub. No. 2014/011712, or an unnatural mimetic thereof:

(XXXVII)

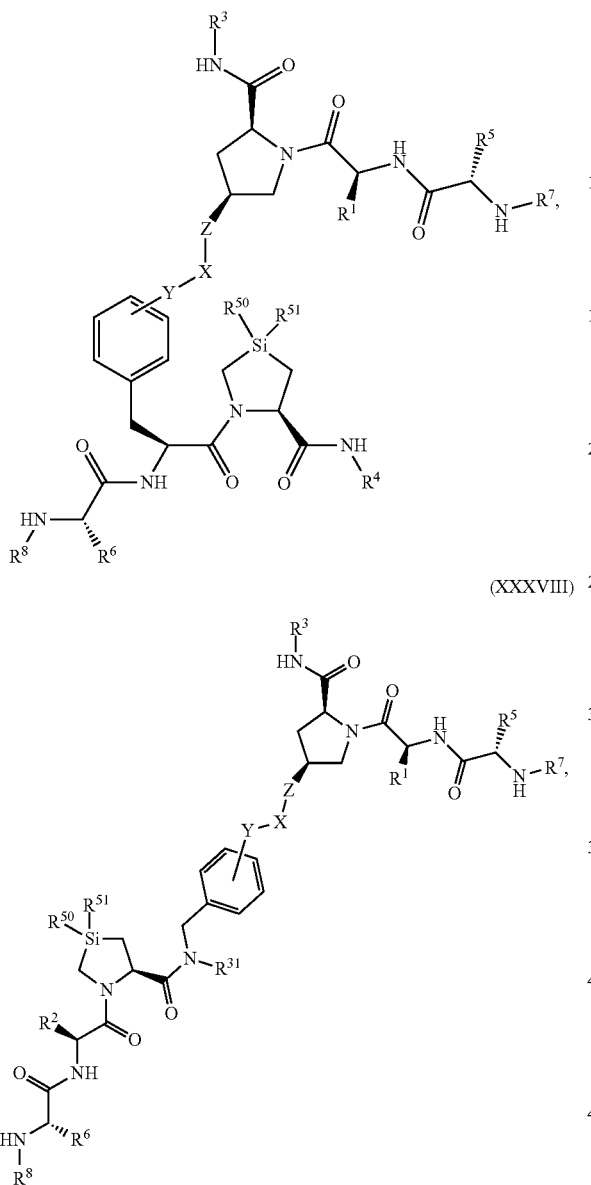

(XXXVIII)

wherein:

X of Formulas (XXXVII) and (XXXVIII) is —(CR$^{16}$R$^{17}$)$_m$—,

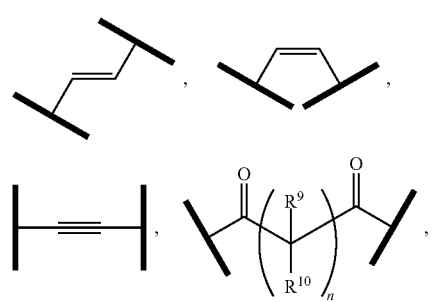

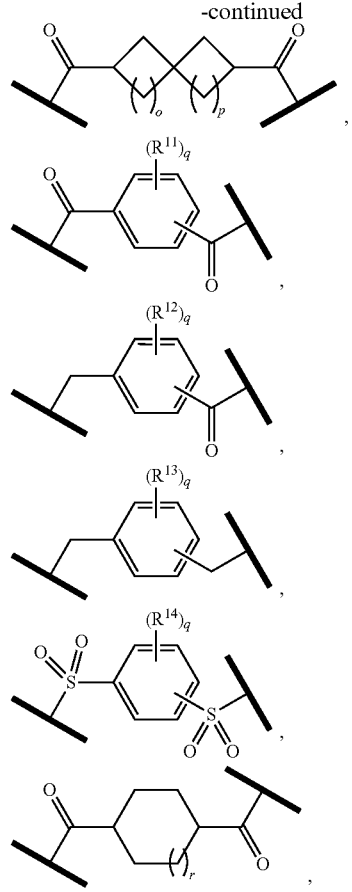

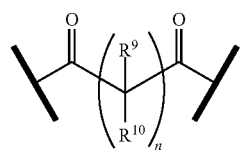

or absent;

Y and Z of Formula (XXXVII) and (XXXVIII) are independently selected from —O—, C═O, NR$^6$ or are absent;

R$^1$ and R$^2$ of Formula (XXXVII) and (XXXVIII) are selected from optionally substituted alkyl, optionally substituted cycloalkyl, optionally substituted alkylaryl or optionally substituted aryl;

R$^3$ and R$^4$ of Formula (XXXVII) and (XXXVIII) are independently selected from optionally substituted alkyl, optionally substituted cycloalkyl, optionally substituted cycloalkylalkyl, optionally substituted arylalkyl or optionally substituted aryl;

R$^5$ and R$^6$ of Formula (XXXVII) and (XXXVIII) are independently selected from optionally substituted alkyl or optionally substituted cycloalkyl;

R$^7$ and R$^8$ of Formula (XXXVII) and (XXXVIII) are independently selected from hydrogen, optionally substituted alkyl or optionally substituted cycloalkyl, or preferably methyl;

R$^9$ and R$^{10}$ of are independently selected from hydrogen, optionally substituted alkyl, or R$^9$ and R$^{10}$ may be taken together to form a ring;

$R^{11}$ to $R^{14}$ of

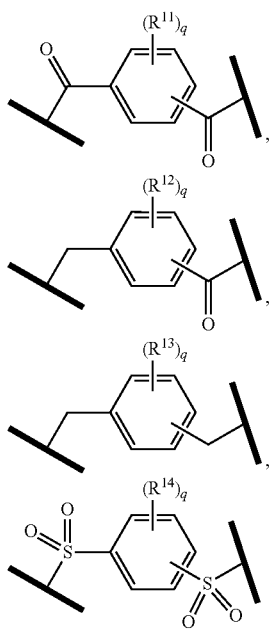

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

$R^{16}$ and $R^{17}$ of $-(CR^{16}R^{17})_m-$ are independently selected from hydrogen, halogen or optionally substituted alkyl;

$R^{50}$ and $R^{51}$ of Formula (XXXVII) and (XXXVIII) are independently selected from optionally substituted alkyl, or $R^{50}$ and $R^{51}$ are taken together to form a ring;

m and n of $-(CR^{16}R^{17})_m-$ and

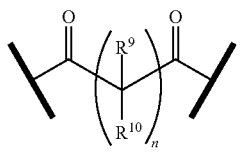

are independently an integer from 0-4;

o and p of

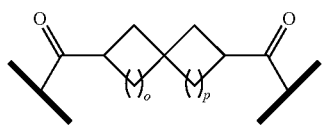

are independently an integer from 0-3;

q of

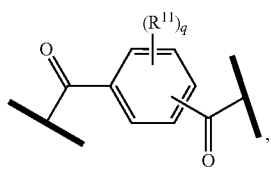

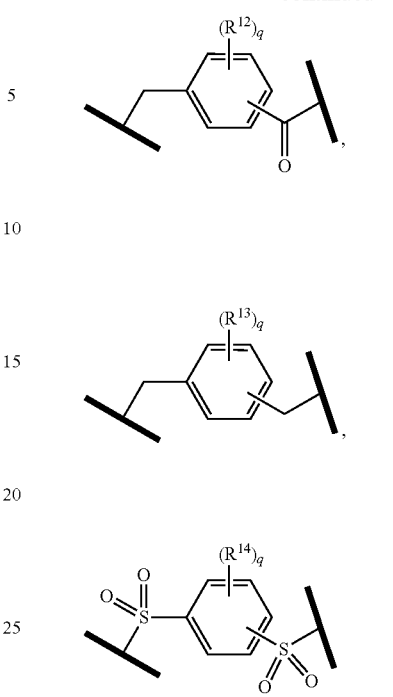

is an integer from 0-4; and r of

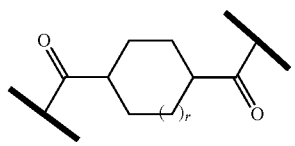

is an integer from 0-1;

or a pharmaceutically acceptable salt, tautomer or stereoisomer thereof.

In an embodiment, $R^1$ and $R^2$ of the ILM of Formula (XXXVII) or (XXXVIII) are t-butyl and $R^3$ and $R^4$ of the ILM of Formula (XXXVII) or (XXXVIII) are tetrahydronaphtalene.

In any of the compounds described herein, the ILM can have the structure of Formula (XXXIX) or (XL), which are derived from the IAP ligands described in WO Pub. No. 2013/071039, or an unnatural mimetic thereof:

(XXXIX)

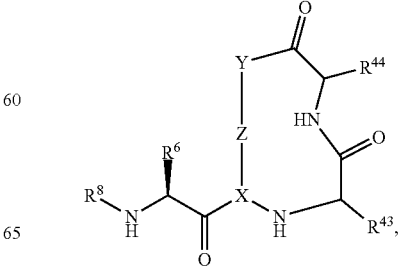

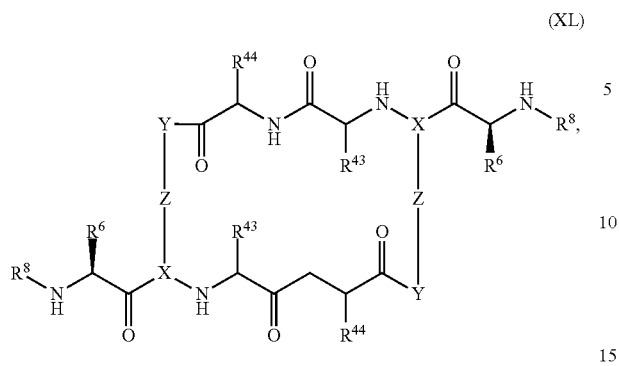

(XL)

wherein:

R[43] and R[44] of Formulas (XXXIX) and (XL) are independently selected from hydrogen, alkyl, aryl, arylalkyl, heteroaryl, heteroarylalkyl, cycloalkyl, cycloalkylalkyl further optionally substituted, and R[6] and R[8] of Formula (XXXIX) and (XL) are independently selected from hydrogen, optionally substituted alkyl or optionally substituted cycloalkyl.

each X of Formulas (XXXIX) and (XL) is independently selected from:

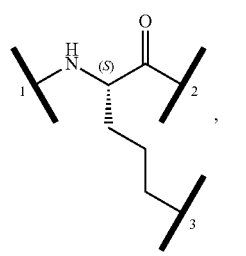

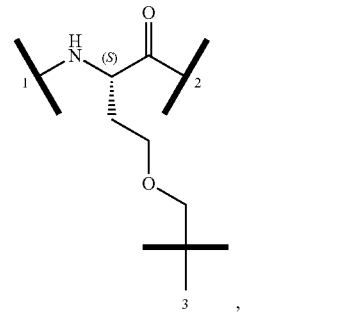

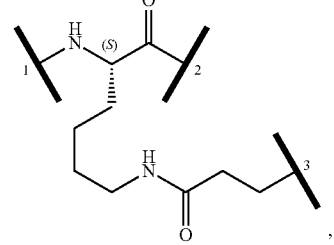

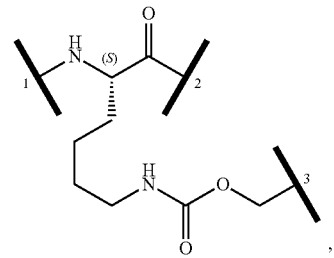

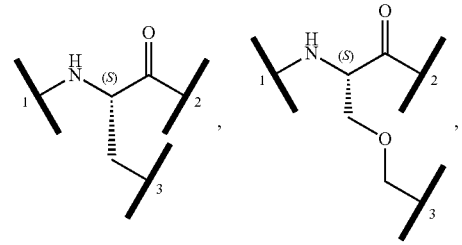

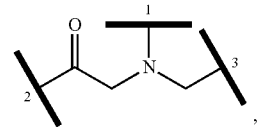

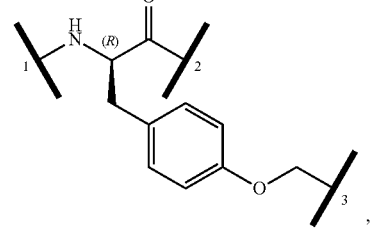

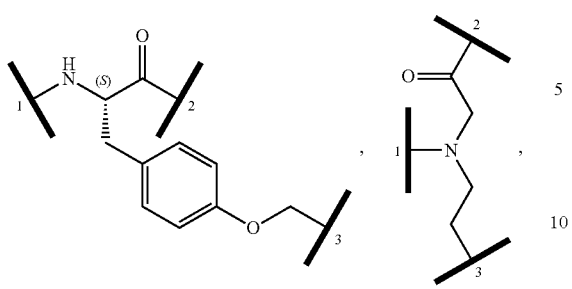
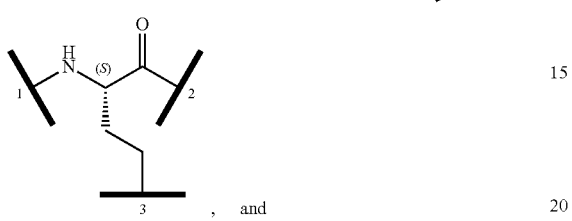
, and
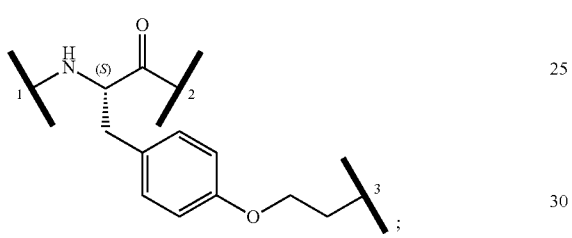
each Z of Formulas (XXXIX) and (XL) is selected from
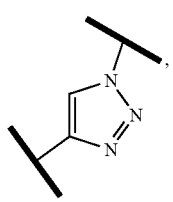
wherein each
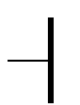
represents a point of attachment to the compound; and each Y is selected from:
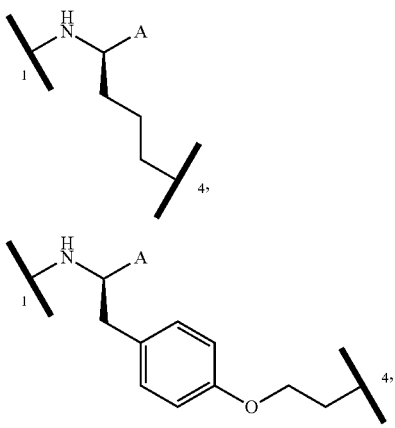
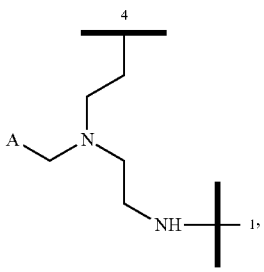
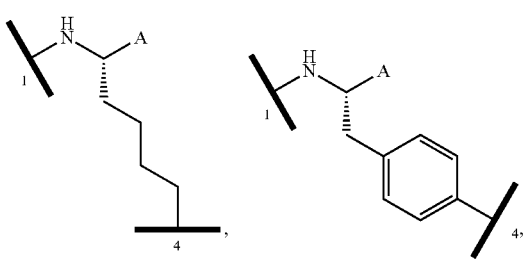
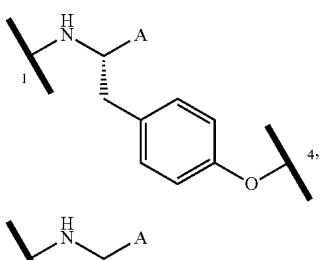
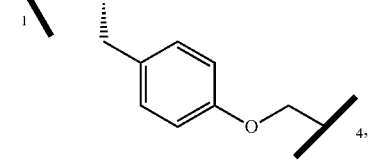
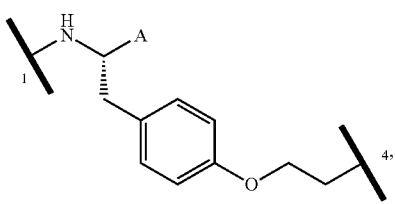

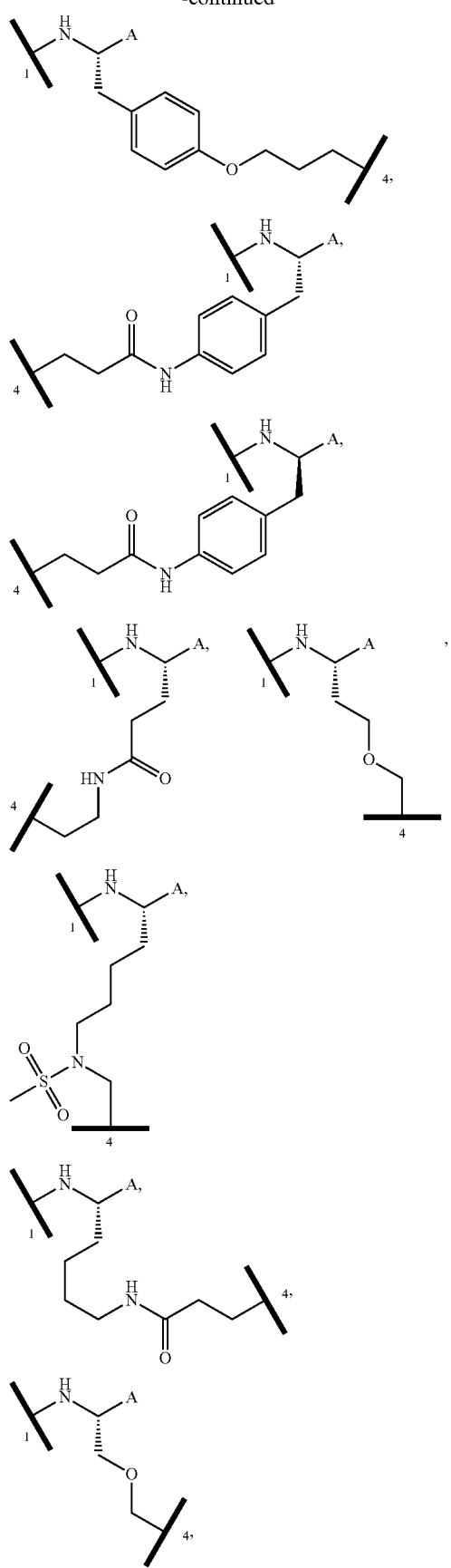
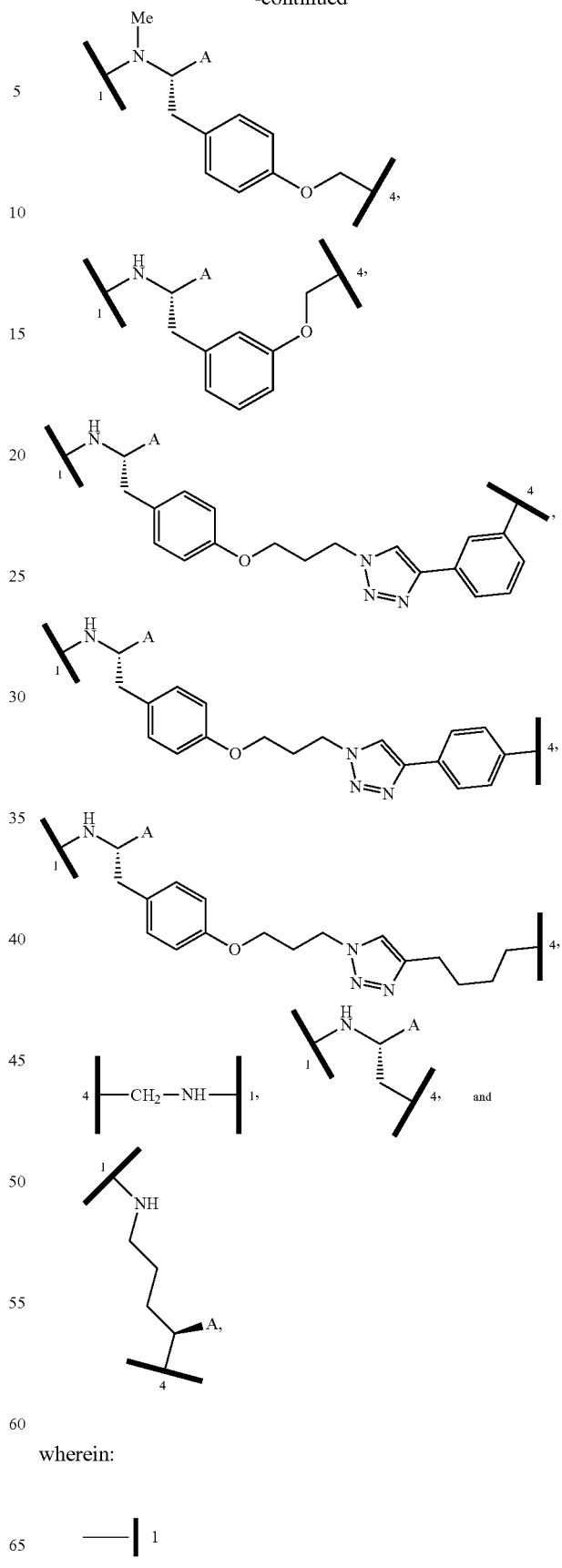
wherein:

represents a point of attachment to a —C═O portion of the compound;

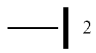

represents a point of attachment to an amino portion of the compound;

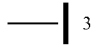

represents a first point of attachment to Z;

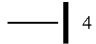

represents a second point of attachment to Z; and
A is selected from —C(O)R$^3$ or

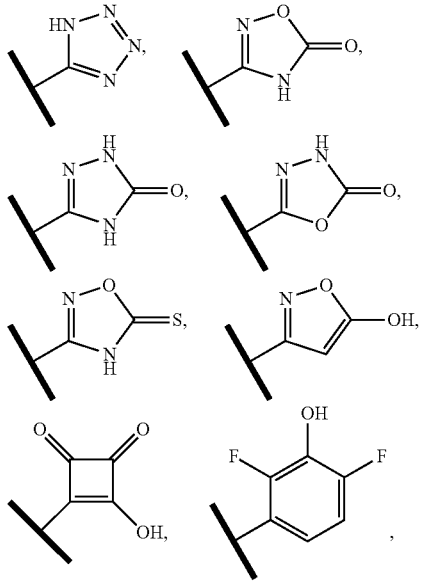

or a tautomeric form of any of the foregoing, wherein:
R$^3$ of —C(O)R$^3$ is selected from OH, NHCN, NHSO$_2$R$^{10}$, NHOR$^{11}$ or N(R$^{12}$)(R$^{13}$);
R$^{10}$ and R$^{11}$ of NHSO$_2$R$^{10}$ and NHOR$^{11}$ are independently selected from —C$_1$-C$_4$ alkyl, cycloalkyl, aryl, heteroaryl, or heterocycloalkyl, any of which are optionally substituted, and hydrogen;
each of R$^{12}$ and R$^{13}$ of N(R$^{12}$)(R$^{13}$) are independently selected from hydrogen, —C$_1$-C$_4$ alkyl, —(C$_1$-C$_4$ alkylene)-NH—(C$_1$-C$_4$ alkyl), benzyl, —(C$_1$-C$_4$ alkylene)-C(O)OH, —(C$_1$-C$_4$ alkylene)-C(O)CH$_3$, —CH(benzyl)-COOH, —C$_1$-C$_4$ alkoxy, and —(C$_1$-C$_4$ alkylene)-O—(C$_1$-C$_4$ hydroxyalkyl); or R$^{12}$ and R$^{13}$ of N(R$^{12}$)(R$^{13}$) are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XLI), which are derived from the IAP ligands described in WO Pub. No. 2013/071039, or an unnatural mimetic thereof:

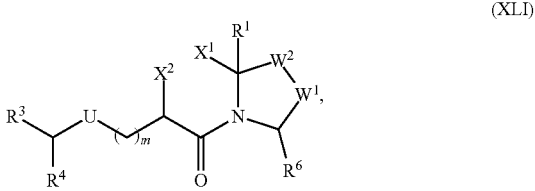

wherein:
W$^1$ of Formula (XLI) is selected from O, S, N—R$^A$, or C(R$^{8a}$)(R$^{8b}$);
W$^2$ of Formula (XLI) is selected from O, S, N—R$^A$, or C(R$^{8c}$)(R$^{8d}$); provided that W$^1$ and W$^2$ are not both O, or both S;
R$^1$ of Formula (XLI) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);
when X$^1$ is selected from O, N—R$^A$, S, S(O), or S(O)$_2$, then X$^2$ is C(R$^{2a}$R$^{2b}$);
or:
X$^1$ of Formula (XLI) is selected from CR$^{2c}$R$^{2d}$ and X$^2$ is CR$^{2a}$R$^{2b}$, and R$^{2c}$ and R$^{2a}$ together form a bond;
or:
X$^1$ and X$^2$ of Formula (XLI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;
or:
X$^1$ of Formula (XLI) is selected from CH$_2$ and X$^2$ is C═O, C═C(R$^c$)$_2$, or C═NR$^c$; where each R$^c$ is independently selected from H, —CN, —OH, alkoxy, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
R$^A$ of N—R$^A$ is selected from H, C$_1$-C$_6$alkyl, —C(═O)C$_1$-C$_2$alkyl, substituted or unsubstituted aryl, or substituted or unsubstituted heteroaryl;
R$^{2a}$, R$^{2b}$, R$^{2c}$, R$^{2d}$ of CR$^{2c}$R$^{2d}$ and CR$^{2a}$R$^{2b}$ are independently selected from H, substituted or unsubstituted C$_1$-C$_6$alkyl, substituted or unsubstituted C$_1$-C$_6$heteroalkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ of $NR^D R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLI) is selected from 0, 1 or 2;

—U— of Formula (XLI) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ of Formula (XLI) is selected from C1-$C_3$alkyl, or C1-$C_3$fluoroalkyl;

$R^4$ of Formula (XLI) is selected from —$NHR^5$, —$N(R^5)_2$, —$N+(R^5)_3$ or —$OR^5$; each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLI) together with the atoms to which they are attached form a substituted or unsubstituted 5-7 membered ring;

or:

$R^3$ of Formula (XLI) is bonded to a nitrogen atom of U to form a substituted or unsubstituted 5-7 membered ring;

$R^6$ of Formula (XLI) is selected from —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of C($R^{8a}$)($R^{8b}$) and C($R^{8c}$)($R^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, $C_1$-$C_4$fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLII), which are derived from the IAP ligands described in WO Pub. No. 2013/071039, or an unnatural mimetic thereof:

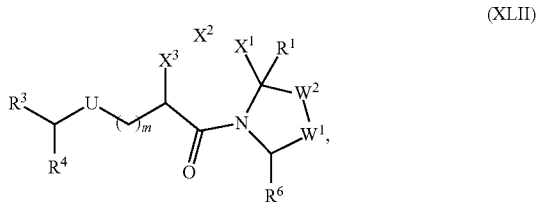

(XLII)

wherein:
W$^1$ of Formula (XLII) is O, S, N—R$^A$, or C(R$^{8a}$)(R$^{8b}$);
W$^2$ of Formula (XLII) is O, S, N—R$^A$, or C(R$^{8c}$)(R$^{8d}$); provided that W$^1$ and W$^2$ are not both O, or both S;
R$^1$ of Formula (XLII) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);
when X$^1$ of Formula (XLII) is N—R$^A$, then X$^2$ is C=O, or CR$^{2c}$R$^{2d}$, and X$^3$ is CR$^{2a}$R$^{2b}$;
or:
when X$^1$ of Formula (XLII) is selected from S, S(O), or S(O)$_2$, then X$^2$ is CR$^{2c}$R$^{2d}$, and X$^3$ is CR$^{2a}$R$^{2b}$;
or:
when X$^1$ of Formula (XLII) is O, then X$^2$ is CR$^{2c}$R$^{2d}$ and N—R$^A$ and X$^3$ is CR$^{2a}$R$^{2b}$; or:
when X$^1$ of Formula (XLII) is CH$_3$, then X$^2$ is selected from O, N—R$^A$, S, S(O), or S(O)$_2$, and X$^3$ is CR$^{2a}$R$^{2b}$;
when X$^1$ of Formula (XLII) is CR$^{2e}$R$^{2f}$ and X2 is CR$^{2c}$R$^{2d}$, and R$^{2e}$ and R$^{2c}$ together form a bond, and X$^3$ of Formula (VLII) is CR$^{2a}$R$^{2b}$;
or:
X$^1$ and X$^3$ of Formula (XLII) are both CH$_2$ and X$^2$ of Formula (XLII) is C=O, C=C(R$^C$)2, or C=NR$^C$; where each R$^C$ is independently selected from H, —CN, —OH, alkoxy, substituted or unsubstituted C1-C6alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
or:
X$^1$ and X$^2$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^3$ is CR$^{2a}$R$^{2b}$;
or:
X$^2$ and X$^3$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^1$ of Formula (VLII) is CR$^{2e}$R$^{2f}$;
R$^A$ of N—R$^A$ is selected from H, C$_1$-C$_6$alkyl, —C(=O) C$_1$-C$_2$alkyl, substituted or unsubstituted aryl, or substituted or unsubstituted heteroaryl;
R$^{2a}$, R$^{2b}$, R$^{2c}$, R$^{2d}$, R$^{2e}$, and R$^{2f}$ of CR$^{2c}$R$^{2d}$, CR$^{2a}$R$^{2b}$ and CR$^{2e}$R$^{2f}$ are independently selected from H, substituted or unsubstituted C$_1$-C$_6$alkyl, substituted or unsubstituted C$_1$-C$_6$heteroalkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl) and —C(=O)R$^B$;
R$^B$ of —C(=O)R$^B$ is selected from substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl), or —NR$^D$R$^E$;
R$^D$ and R$^E$ of NR$^D$R$^E$ are independently selected from H, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
m of Formula (XLII) is selected from 0, 1 or 2;
—U— of Formula (XLII) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
R$^3$ of Formula (XLII) is selected from C1-C$_3$alkyl, or C1-C$_3$fluoroalkyl;
R$^4$ of Formula (XLII) is selected from —NHR$^5$, —N(R$^5$)$_2$, —N+(R$^5$)$_3$ or —OR$^5$; each R$^5$ of —NHR$^5$, —N(R$^5$)$_2$, —N+(R$^5$)$_3$ and —OR$^5$ is independently selected from H, C$_1$-C$_3$alkyl, C$_1$-C$_3$haloalkyl, C$_1$-C$_3$heteroalkyl and —C$_1$-C$_3$alkyl-(C3-C$_5$cycloalkyl);
or:
R$^3$ and R$^5$ of Formula (XLII) together with the atoms to which they are attached form a substituted or unsubstituted 5-7 membered ring;
or:
R$^3$ of Formula (XLII) is bonded to a nitrogen atom of U to form a substituted or unsubstituted 5-7 membered ring;
R$^6$ of Formula (XLII) is selected from —NHC(=O)R$^7$, —C(=O)NHR$^7$, —NHS(=O)2R$^7$, —S(=O)$_2$NHR$^7$; —NHC(=O)NHR$^7$, —NHS(=O)$_2$NHR$^7$, —(C$_1$-C$_3$alkyl)-NHC(=O)R$^7$, —(C$_1$-C$_3$alkyl)-C(=O)NHR$^7$, —(C1-C3alkyl)-NHS(=O)$_2$R$^7$, —(C1-C3alkyl)-S(=O)$_2$NHR$^7$; —(C$_1$-C$_3$alkyl)-NHC(=O)NHR$^7$, —(C$_1$-C$_3$alkyl)-NHS(=O)$_2$NHR$^7$, substituted or unsubstituted C$_2$-C$_{10}$heterocycloalkyl, or substituted or unsubstituted heteroaryl;

each R⁷ of —NHC(=O)R⁷, —C(=O)NHR⁷, —NHS(=O)2R⁷, —S(=O)₂NHR⁷; —NHC(=O)NHR⁷, —NHS(=O)₂NHR⁷, —(C₁-C₃alkyl)-NHC(=O)R⁷, —(C₁-C₃alkyl)-C(=O)NHR⁷, —(C₁-C₃alkyl)-NHS(=O)2R⁷, —(C₁-C₃alkyl)-S(=O)2NHR⁷; —(C₁-C₃alkyl)-NHC(=O)NHR⁷, —(C₁-C₃alkyl)-NHS(=O)2NHR⁷ is independently selected from C₁-C₆alkyl, C₁-C₆haloalkyl, C₁-C₆heteroalkyl, a substituted or unsubstituted C3-C10cycloalkyl, a substituted or unsubstituted C₂-C₁₀heterocycloalkyl, a substituted or unsubstituted aryl, a substituted or unsubstituted heteroaryl, —C₁-C₆alkyl-(substituted or unsubstituted C₃-C₁₀cycloalkyl), —C₁-C₆alkyl-(substituted or unsubstituted C2-C10heterocycloalkyl, —C1-C6alkyl-(substituted or unsubstituted aryl), —C₁-C₆alkyl-(substituted or unsubstituted heteroaryl), —(CH2)p-CH(substituted or unsubstituted aryl)2, —(CH₂)ₚ—CH(substituted or unsubstituted heteroaryl)2, —(CH₂)ₚ—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of R⁷ is selected from 0, 1 or 2;

$R^{8a}$, $R^{8b}$, $R^{8c}$, and $R^{8d}$ of $C(R^{8a})(R^{8b})$ and $C(R^{8C})(R^{8d})$ are independently selected from H, C₁-C₆alkyl, C₁-C₆fluoroalkyl, C₁-C₆ alkoxy, C₁-C₆heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 R⁹; and each R⁹ of $R^{8a}$, $R^{8b}$, $R^{8c}$ and $R^{8d}$ is independently selected from halogen, —OH, —SH, (C=O), CN, C₁-C₄alkyl, C1-C4fluoroalkyl, C₁-C₄ alkoxy, C₁-C₄ fluoroalkoxy, —NH₂, —NH(C₁-C₄alkyl), —NH(C₁-C₄alkyl)₂, —C(=O)OH, —C(=O)NH₂, —C(=O)C₁-C₃alkyl, —S(=O)₂CH₃, —NH(C₁-C₄alkyl)-OH, —NH(C₁-C₄alkyl)-O—(C—C₄alkyl), —O(C₁-C₄alkyl)-NH2; —O(C₁-C₄alkyl)-NH—(C₁-C₄alkyl), and —O(C₁-C₄alkyl)-N—(C₁-C₄alkyl)₂, or two R⁹ together with the atoms to which they are attached form a methylene dioxy or ethylene dioxy ring substituted or unsubstituted with halogen, —OH, or C₁-C₃alkyl.

In any of the compounds described herein, the ILM can have the structure of Formula (XLIII), which is derived from the IAP ligands described in WO Pub. No. 2013/071039, or an unnatural mimetic thereof:

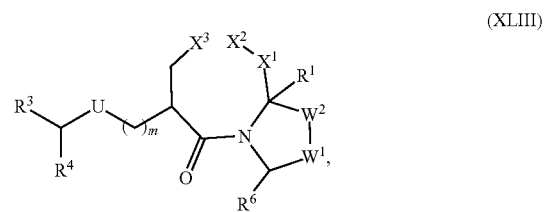

(XLIII)

wherein:

W¹ of Formula (XLIII) is selected from O, S, N—$R^A$, or $C(R^{8a})(R^{8b})$;

W² of Formula (XLIII) is selected from O, S, N—$R^A$, or $C(R^{8C})(R^{8d})$; provided that W¹ and W² are not both O, or both S;

R¹ of Formula (XLIII) is selected from H, C₁-C₆alkyl, C₃-C₆cycloalkyl, —C₁-C₆alkyl-(substituted or unsubstituted C₃-C₆cycloalkyl), substituted or unsubstituted aryl, substituted or unsubstituted heteroaryl, —C₁-C₆alkyl-(substituted or unsubstituted aryl), or —C₁-C₆alkyl-(substituted or unsubstituted heteroaryl);

when X¹ of Formula (XLIII) is selected from N—$R^A$, S, S(O), or S(O)₂, then X² of Formula (XLIII) is $CR^{2C}R^{2d}$, and X³ of Formula (XLIII) is $CR^{2a}R^{2b}$;

or:

when X¹ of Formula (XLIII) is O, then X² of Formula (XLIII) is selected from O, N—$R^A$, S, S(O), or S(O)₂, and X³ of Formula (XLIII) is $CR^{2a}R^{2b}$;

or:

when X¹ of Formula (XLIII) is $CR^{2e}R^{2f}$ and X² of Formula (XLIII) is $CR^{2c}R^{2d}$, and $R^{2e}$ and $R^{2c}$ together form a bond, and X³ of Formula (XLIII) is $CR^{2a}R^{2b}$;

or:

X¹ and X² of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X³ of Formula (XLIII) is $CR^{2a}R^{2b}$;

or:

X² and X³ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X¹ of Formula (VLII) is $CR^{2e}R^{2f}$;

$R^A$ of N—$R^A$ is H, C₁-C₆alkyl, —C(=O)C₁-C₂alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —$C(=O)R^B$;

$R^B$ of —$C(=O)R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLIII) is 0, 1 or 2;

—U— of Formula (XLIII) is —$NHC(=O)$—, —$C(=O)NH$—, —$NHS(=O)_2$—, —$S(=O)_2NH$—, —$NHC(=O)NH$—, —$NH(C=O)O$—, —$O(C=O)NH$—, or —$NHS(=O)_2NH$—;

$R^3$ of Formula (XLIII) is $C_1$-$C_3$alkyl, or $C_1$-$C_3$fluoroalkyl;

$R^4$ of Formula (XLIII) is —$NHR^5$, —$N(R^5)_2$, —$N+(R^5)_3$ or —$OR^5$; each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-(C3-$C_5$cycloalkyl);

or:

$R^3$ and $R^5$ of Formula (XLIII) together with the atoms to which they are attached form a substituted or unsubstituted 5-7 membered ring;

or:

$R^3$ of Formula (XLIII) is bonded to a nitrogen atom of U to form a substituted or unsubstituted 5-7 membered ring;

$R^6$ of Formula (XLIII) is selected from —$NHC(=O)R^7$, —$C(=O)NHR^7$, —$NHS(=O)2R^7$, —$S(=O)_2NHR^7$; —$NHC(=O)NHR^7$, —$NHS(=O)_2NHR^7$, —$(C_1$-$C_3$alkyl)-$NHC(=O)R^7$, —$(C_1$-$C_3$alkyl)-$C(=O)NHR^7$, —(C1-C3alkyl)-$NHS(=O)_2R^7$, —(C1-C3alkyl)-$S(=O)_2NHR^7$; —$(C_1$-$C_3$alkyl)-$NHC(=O)NHR^7$, —$(C_1$-$C_3$alkyl)-$NHS(=O)_2NHR^7$, substituted or unsubstituted $C_2$-$C_{10}$heterocycloalkyl, or substituted or unsubstituted heteroaryl;

each $R^7$ of —$NHC(=O)R^7$, —$C(=O)NHR^7$, —$NHS(=O)_2R^7$, —$S(=O)_2NHR^7$; —$NHC(=O)NHR^7$, $NHS(=O)_2NHR^7$, —$(C_1$-$C_3$alkyl)-$NHC(=O)R^7$, —$(C_1$-$C_3$alkyl)-$C(=O)NHR^7$, —$(C_1$-$C_3$alkyl)-$NHS(=O)_2R^7$, —$(C_1$-$C_3$alkyl)-$S(=O)_2NHR^7$; —$(C_1$-$C_3$alkyl)-$NHC(=O)NHR^7$, —$(C_1$-$C_3$alkyl)-$NHS(=O)2NHR^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —$(CH_2)_p$—CH(substituted or unsubstituted heteroaryl)2, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, $C_1$-$C_4$fluoroalkyl, $C_1$-$C_4$ alkoxy, $C_1$-$C_4$ fluoroalkoxy, —$NH_2$, —$NH(C_1$-$C_4$alkyl), —$NH(C_1$-$C_4$alkyl)_2$, —$C(=O)OH$, —$C(=O)NH_2$, —$C(=O)C_1$-$C_3$alkyl, —$S(=O)_2CH_3$, —$NH(C_1$-$C_4$alkyl)-OH, —$NH(C_1$-$C_4$alkyl)-O—(C=C4alkyl), —$O(C_1$-$C_4$alkyl)-NH2; —$O(C_1$-$C_4$alkyl)-NH—$(C_1$-$C_4$alkyl), and —$O(C_1$-$C_4$alkyl)-N—$(C_1$-$C_4$alkyl)_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIV), which is derived from the IAP ligands described in WO Pub. No. 2013/071039, or an unnatural mimetic thereof:

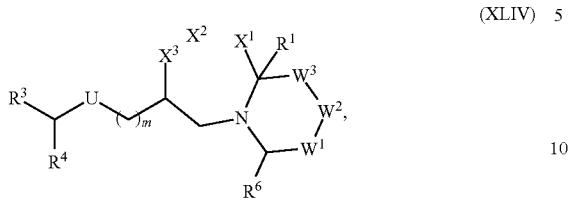

(XLIV)

wherein:
- $W^1$ of Formula (XLIV) is selected from O, S, N—$R^A$, or $C(R^{8a})(R^{8b})$;
- $W^2$ of Formula (XLIV) is selected from O, S, N—$R^A$, or $C(R^{8c})(R^{8d})$; provided that $W^1$ and $W^2$ are not both O, or both S;
- $W^3$ of Formula (XLIV) is selected from O, S, N—$R^A$, or $C(R^{8e})(R^{8f})$, providing that the ring comprising $W^1$, $W^2$, and $W^3$ does not comprise two adjacent oxygen atoms or sulfer atoms;
- $R^1$ of Formula (XLIV) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
- when $X^1$ of Formula (XLIV) is O, then $X^2$ of Formula (XLIV) is selected from $CR^{2c}R^{2d}$ and N—$R^A$, and $X^3$ of Formula (XLIV) is $CR^{2a}R^{2b}$;

or:
- when $X^1$ of Formula (XLIV) is $CH_2$, then $X^2$ of Formula (XLIV) is selected from O, N—$R^A$, S, S(O), or $S(O)_2$, and $X^3$ of Formula (XLIV) is $CR^{2a}R^{2b}$;

or:
- when $X^1$ of Formula (XLIV) is $CR^{2e}R^{2f}$ and $X^2$ of Formula (XLIV) is $CR^{2c}R^{2d}$, and $R^{2e}$ and $R^{2c}$ together form a bond, and $X^3$ of Formula (VLIV) is $CR^{2a}R^{2b}$;

or:
- $X^1$ and $X^3$ of Formula (XLIV) are both $CH_2$ and $X^2$ of Formula (XLII) is C=O, C=C($R^C$)2, or C=$NR^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:
- $X^1$ and $X^2$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIV) is $CR^{2a}R^{2b}$;

or:
- $X^2$ and $X^3$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLIV) is $CR^{2e}R^{2f}$;
- $R^A$ of N—$R^A$ is selected from H, $C_1$-$C_6$alkyl, —C(=O) $C_1$-$C_2$alkyl, substituted or unsubstituted aryl, or substituted or unsubstituted heteroaryl;
- $R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted C2-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
- $R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
- $R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
- m of Formula (XLIV) is selected from 0, 1 or 2;
- —U— of Formula (XLIV) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
- $R^3$ of Formula (XLIV) is selected from $C_1$-$C_3$alkyl, or $C_1$-$C_3$fluoroalkyl;
- $R^4$ of Formula (XLIV) is selected from —$NHR^5$, —N($R^5$)$_2$, —N+($R^5$)$_3$ or —$OR^5$;
- each $R^5$ of —$NHR^5$, —N($R^5$)$_2$, —N+($R^5$)$_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-(C3-$C_5$cycloalkyl);

or:
- $R^3$ and $R^5$ of Formula (XLIV) together with the atoms to which they are attached form a substituted or unsubstituted 5-7 membered ring;

or:
- $R^3$ of Formula (XLIII) is bonded to a nitrogen atom of U to form a substituted or unsubstituted 5-7 membered ring;
- $R^6$ of Formula (XLIII) is selected from —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are as defined above, and $R^{8b}$ and $R^{8c}$ together form a bond;

or:

$R^{8a}$, $R^{8b}$, $R^{8d}$, and $R^{8f}$ of C($R^{8a}$)($R^{8b}$), C($R^{8c}$)($R^{8d}$) and C($R^{8e}$)($R^{8f}$) are as defined above, and $R^{8c}$ and $R^{8e}$ together form a bond;

or:

$R^{8a}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ of C($R^{8a}$)($R^{8b}$), C($R^{8c}$)($R^{8d}$) and C($R^{8e}$)($R^{8f}$) are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$, and $R^{8f}$ of C($R^{8c}$)($R^{8d}$) and C($R^{8e}$)($R^{8f}$) are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$, and $R^{8f}$ of C($R^{8a}$)($R^{8b}$) and C($R^{8e}$)($R^{8f}$) are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ of C($R^{8a}$)($R^{8b}$) and C($R^{8c}$)($R^{8d}$) are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

or:

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$, $R^{8d}$, $R^{8e}$, and $R^{8f}$ is independently selected from halogen, —OH, —SH, (C=O), CN, $C_1$-$C_4$alkyl, $C_1$-$C_4$fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLV), (XLVI) or (XLVII), which is derived from the IAP ligands described in Vamos, M., et al., *Expedient synthesis of highly potent antagonists of inhibitor of apoptosis proteins (IAPs) with unique selectivity for ML-IAP*, ACS Chem. Biol., 8(4), 725-32 (2013), or an unnatural mimetic thereof:

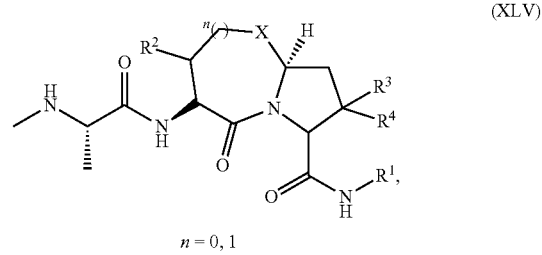

(XLV)

$n = 0, 1$

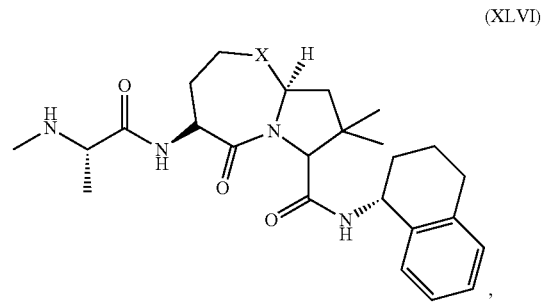

(XLVI)

-continued (XLVII)

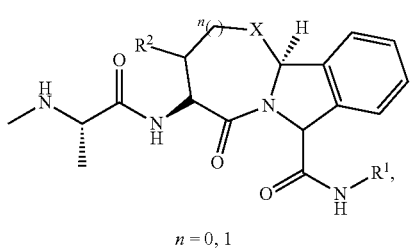

$n = 0, 1$

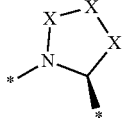

is a 5-member heterocycle selected from:

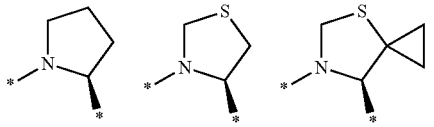

wherein:

R², R³ and R⁴ of Formula (XLV) are independently selected from H or ME;

X of Formula (XLV) is independently selected from O or S; and

R¹ of Formula (XLV) is selected from:

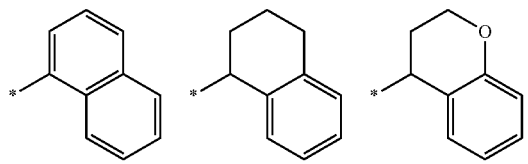

In a particular embodiment, the

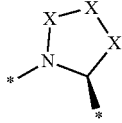

of Formula XLVIII) is

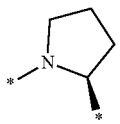 [SMILES: *[C@@H]1CCCN1*]

In a particular embodiment, the ILM has a structure and attached to a linker group L as shown below:

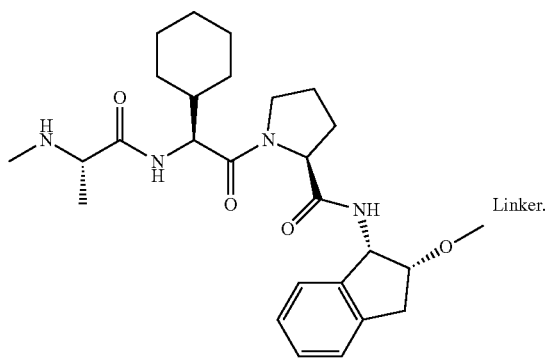

In a particular embodiment, the ILM has a structure according to Formula (XLVIII):

(XLVIII)

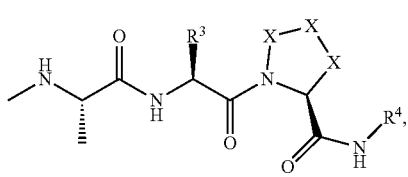

wherein R³ and R⁴ of Formula (XLVIII) are independently selected from H or ME;

In a particular embodiment, the ILM has a structure according to Formula (XLIX), (L), or (LI):

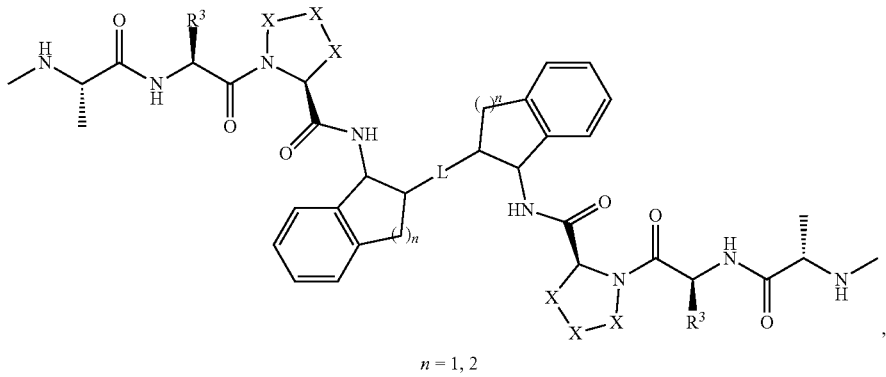
(XLIX)
n = 1, 2
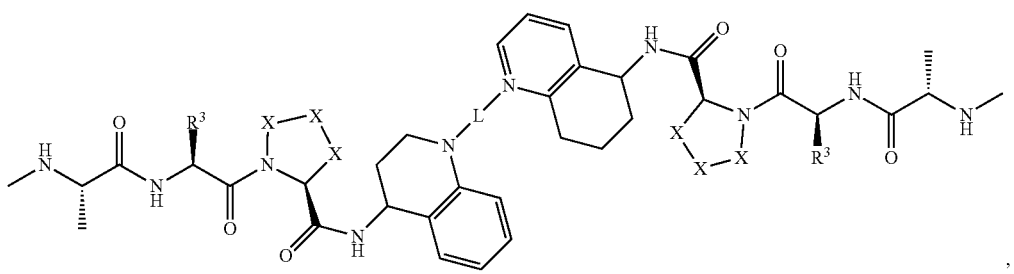
(L)
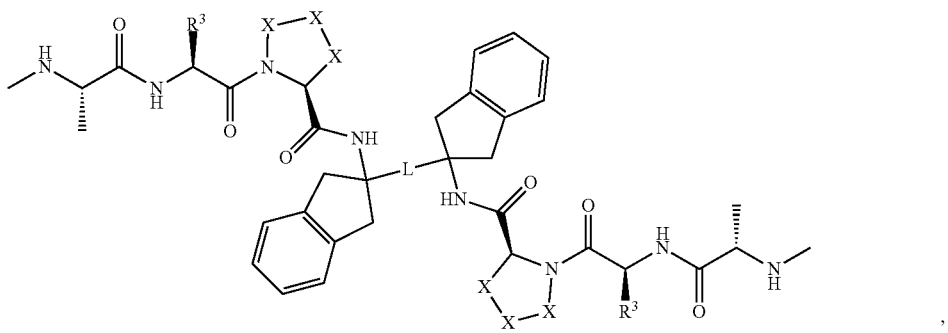
(LI)
wherein:
R³ of Formula (XLIX), (L) or (LI) are independently selected from H or ME;
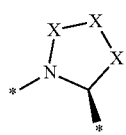
is a 5-member heteocycle selected from:
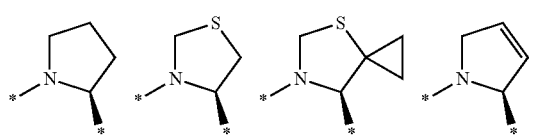
-continued
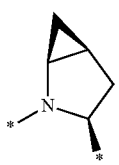
and
L of Formula (XLIX), (L) or (LI) is selected from:

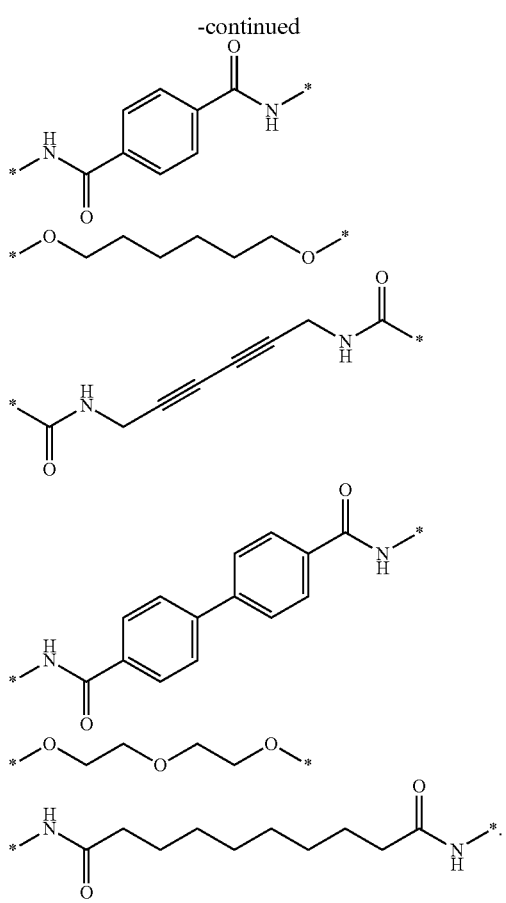

In a particular embodiment L of Formula (XLIX), (L), or (LI)

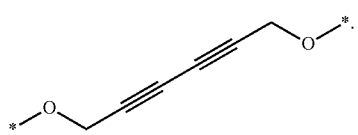

In a particular embodiment, the ILM has a structure according to Formula (LII):

In a particular embodiment, the ILM has a structure according to Formula (LII) is chemically linked to the linker group L in the area denoted with

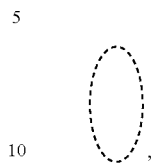

and as shown below:

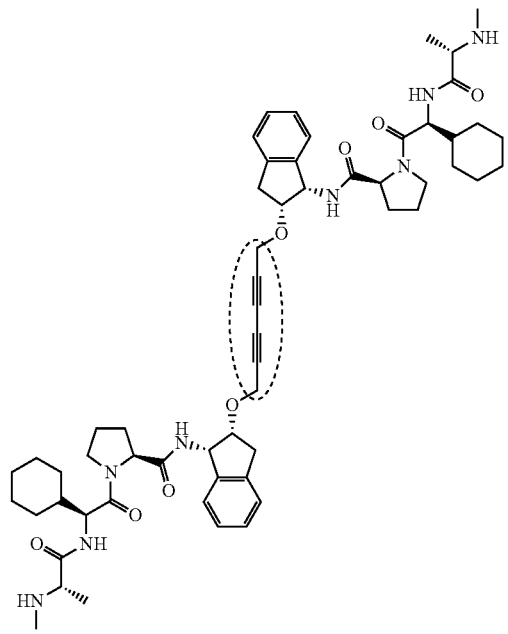

In any of the compounds described herein, the ILM can have the structure of Formula (LIII) or (LIV), which is based on the IAP ligands described in Hennessy, E J, et al., *Discovery of aminopiperidine-based Smac mimetics as IAP antagonists*, Bioorg. Med. Chem. Lett., 22(4), 1960-4 (2012), or an unnatural mimetic thereof:

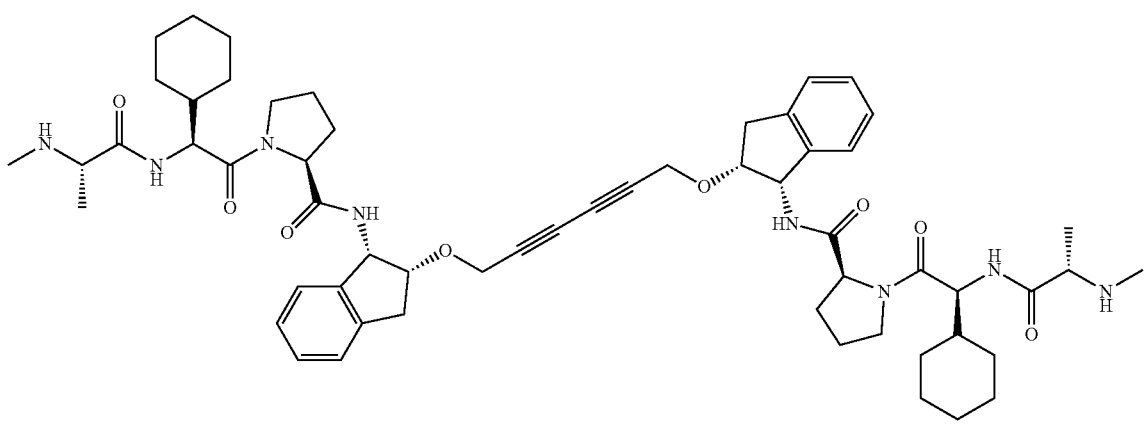

(LIII)

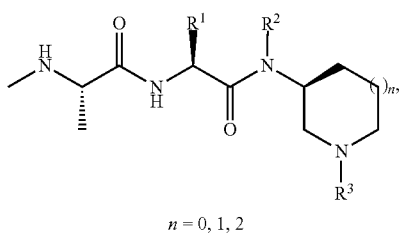

$n = 0, 1, 2$ (LIV)

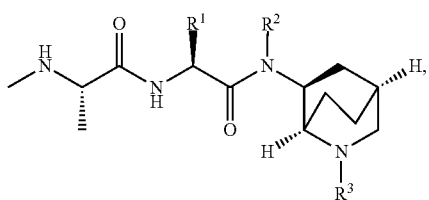

wherein:

R¹ of Formulas (LIII) and (LIV) is selected from:

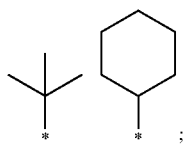

R² of Formulas (LIII) and (LIV) is selected from H or Me;
R³ of Formulas (LIII) and (LIV) is selected from:

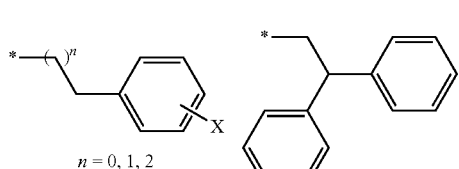

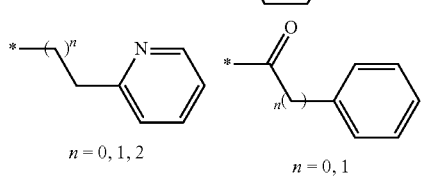

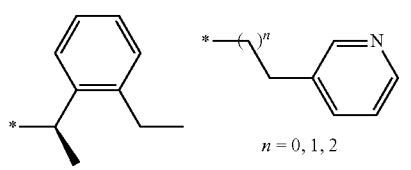

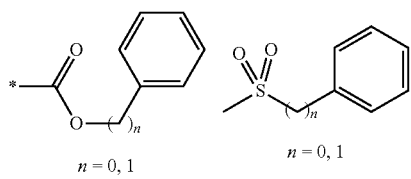

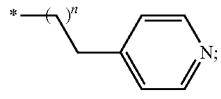

$n = 0, 1, 2$

X of is selected from H, halogen, methyl, methoxy, hydroxy, nitro or trifluoromethyl.

In any of the compounds described herein, the ILM can have the structure of and be chemically linked to the linker as shown in Formula (LV) or (LVI), or an unnatural mimetic thereof:

(LV)

(LVI)

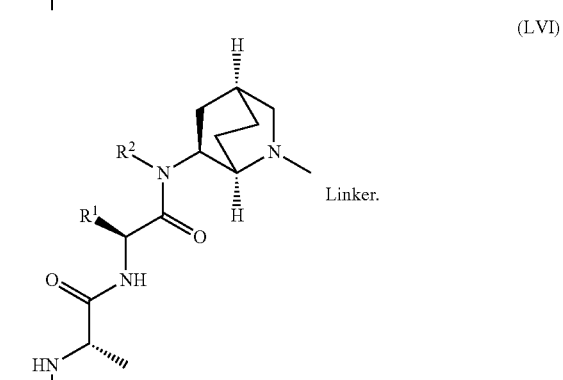

In any of the compounds described herein, the ILM can have the structure of Formula (LVII), which is based on the IAP ligands described in Cohen, F, et al., *Orally bioavailable antagonists of inhibitor of apoptosis proteins based on an azabicyclooctane scaffold*, J. Med. Chem., 52(6), 1723-30 (2009), or an unnatural mimetic thereof:

(LVII)

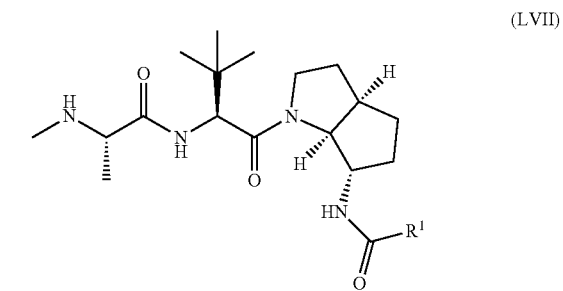

wherein:
R1 of Formulas (LVII) is selected from:

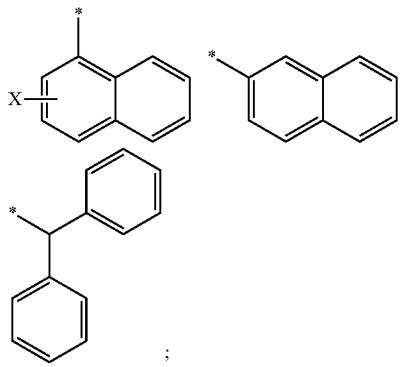

X of

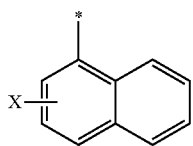

is selected from H, fluoro, methyl or methoxy.

In a particular embodiment, the ILM is represented by the following structure:

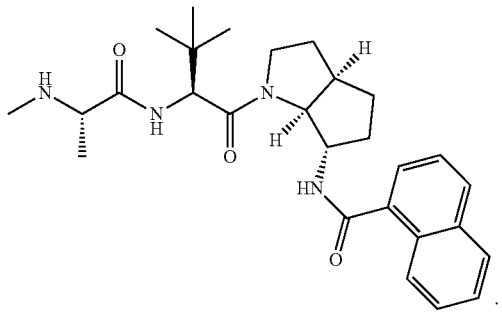 [SMILES: CN[C@@H](C)C(=O)N[C@H](C(=O)N1CC[C@H]2CC[C@H](NC(=O)c3cccc4ccccc34)[C@H]21)C(C)(C)C]

In a particular embodiment, the ILM is selected from the group consisting of, and which the chemical link between the ILM and linker group L is shown:

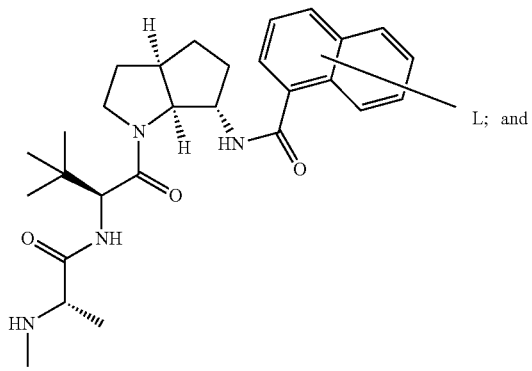

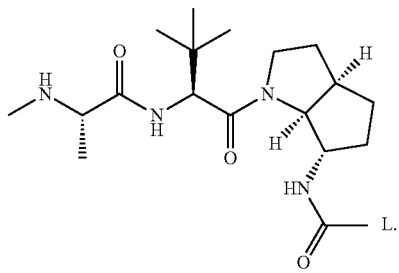

In any of the compounds described herein, the ILM is selected from the group consisting of the structures below, which are based on the IAP ligands described in Asano, M, et al., *Design, sterioselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

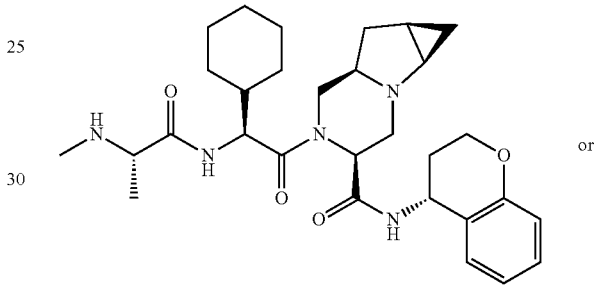

or

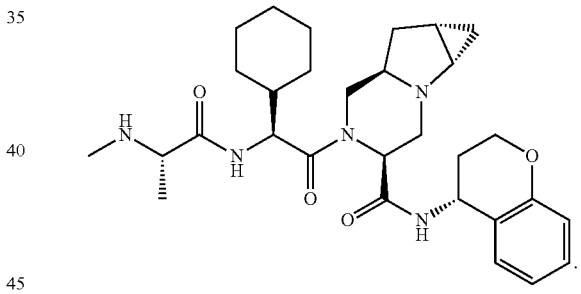

In a particular embodiment, the ILM is selected from the group consisting of, and which the chemical link between the ILM and linker group L is shown:

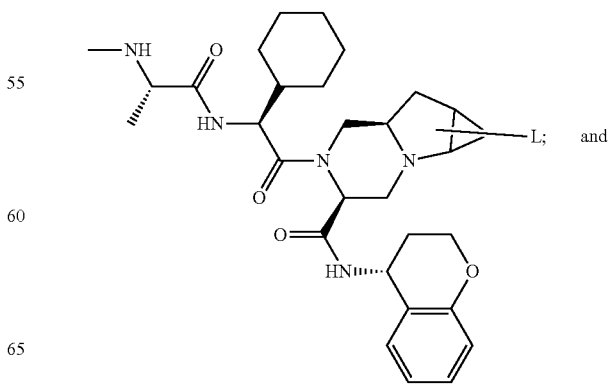

and

-continued

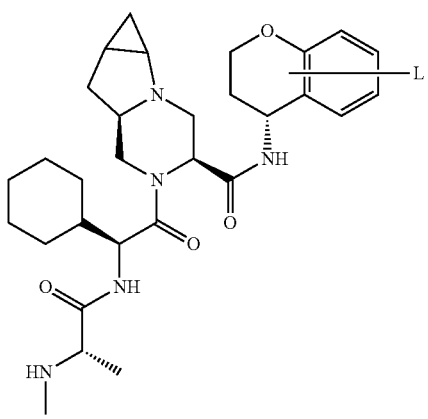

In any of the compounds described herein, the ILM can have the structure of Formula (LVIII), which is based on the IAP ligands described in Asano, M, et al., *Design, sterioselective synthesis, and biological evaluation of novel tricyclic compounds as inhibitor of apoptosis proteins (IAP) antagonists*, Bioorg. Med. Chem., 21(18): 5725-37 (2013), or an unnatural mimetic thereof:

(LVIII)

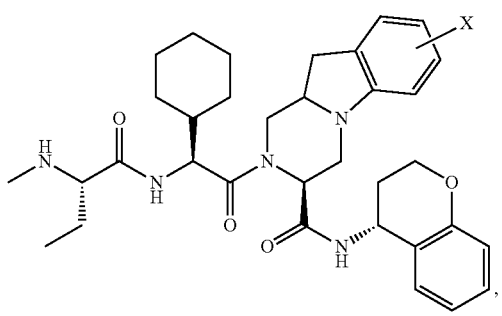

wherein X of Formula (LVIII) is one or two substituents independently selected from H, halogen or cyano.

In any of the compounds described herein, the ILM can have the structure of and be chemically linked to the linker group L as shown in Formula (LIX) or (LX), or an unnatural mimetic thereof:

(LIX)

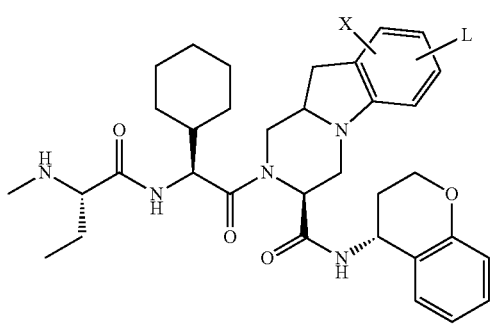

or

-continued (LX)

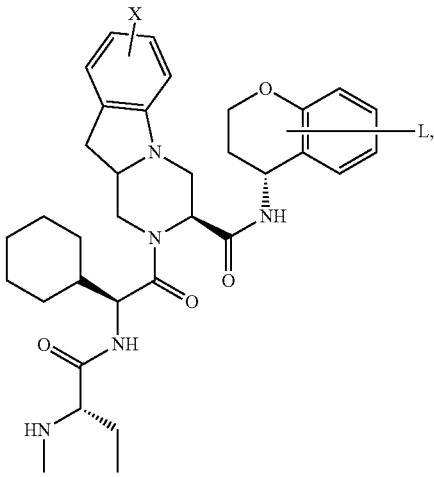

wherein X of Formula (LIX) and (LX) is one or two substituents independently selected from H, halogen or cyano, and; and L of Formulas (LIX) and (LX) is a linker group as described herein.

In any of the compounds described herein, the ILM can have the structure of Formula (LXI), which is based on the IAP ligands described in Ardecky, R J, et al., *Design, sysnthesis and evaluation of inhibitor of apoptosis (IAP) antagonists that are highly selective for the BIR2 domain of XIAP*, Bioorg. Med. Chem., 23(14): 4253-7 (2013), or an unnatural mimetic thereof:

(LXI)

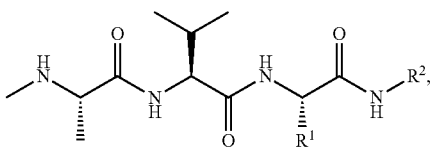

wherein:

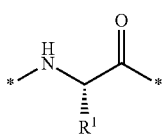

of Formula (LXI) is a natural or unnatural amino acid; and $R^2$ of Formula (LXI) is selected from:

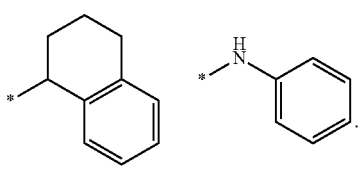

In any of the compounds described herein, the ILM can have the structure of and be chemically linked to the linker group L as shown in Formula (LXII) or (LLXIII), or an unnatural mimetic thereof:

(LXII)

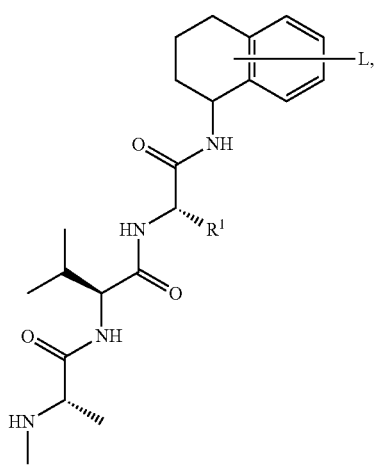

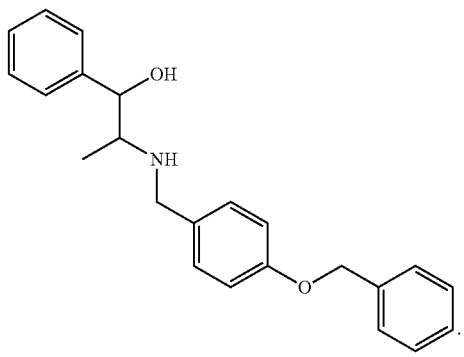

(LXIII)

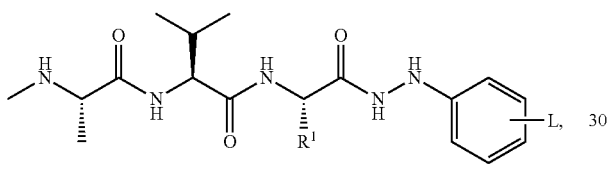

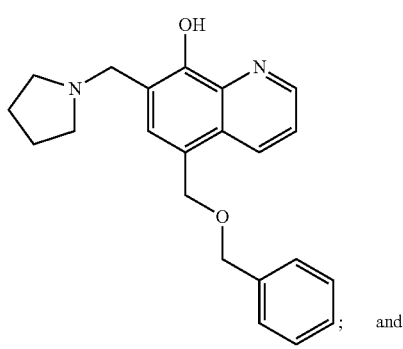

of Formula (LXI) is a natural or unnatural amino acid; and L of Formula (LXI) is a linker group as described herein.

In any of the compounds described herein, the ILM can have the structure selected from the group consisting of, which is based on the IAP ligands described in Wang, J, et al., *Discovery of novel second mitochondrial-derived activator of caspase mimetics as selective inhibitor or apoptosis protein inhibitors*, J. Pharmacol. Exp. Ther., 349(2): 319-29 (2014), or an unnatural mimetic thereof:

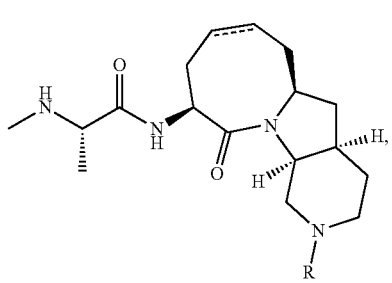

In any of the compounds described herein, the ILM has a structure according to Formula (LXIX), which is based on the IAP ligands described in Hird, A W, et al., *Structure-based design and synthesis of tricyclic IAP (Inhibitors of Apoptosis Proteins) inhibitors*, Bioorg. Med. Chem. Lett., 24(7): 1820-4 (2014), or an unnatural mimetic thereof:

(LXIX)

wherein R of Formula LIX is selected from the group consisting of:

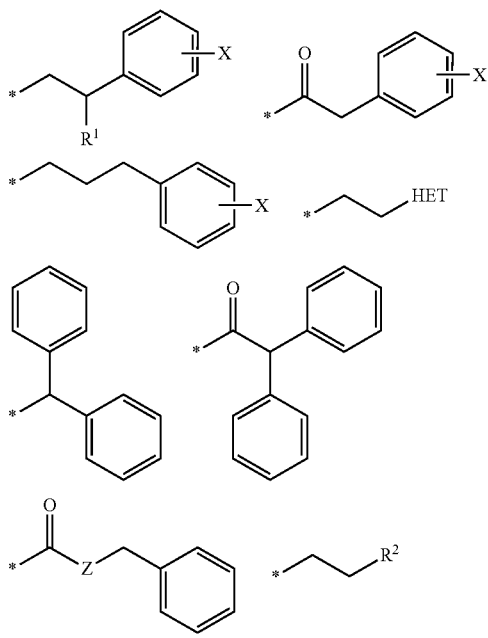

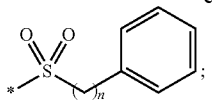

R1 of

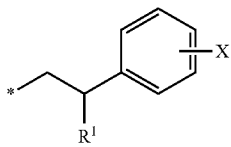

is selected from H or Me;
R2 of

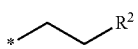

is selected from alkyl or cycloalkyl;
X of

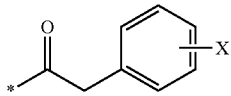 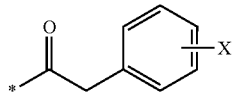

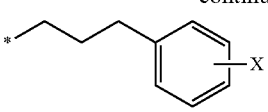

is 1-2 substitutents independently selected from halogen, hydroxy, methoxy, nitro and trifluoromethyl Z of

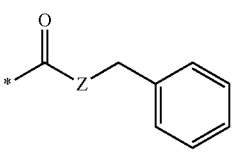

is O or NH;
HET of

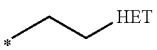

is mono- or fused bicyclic heteroaryl; and
--- of Formula (LIX) is an optional double bond.

In a particular embodiment, the ILM of the compound has a chemical structure as represented by:

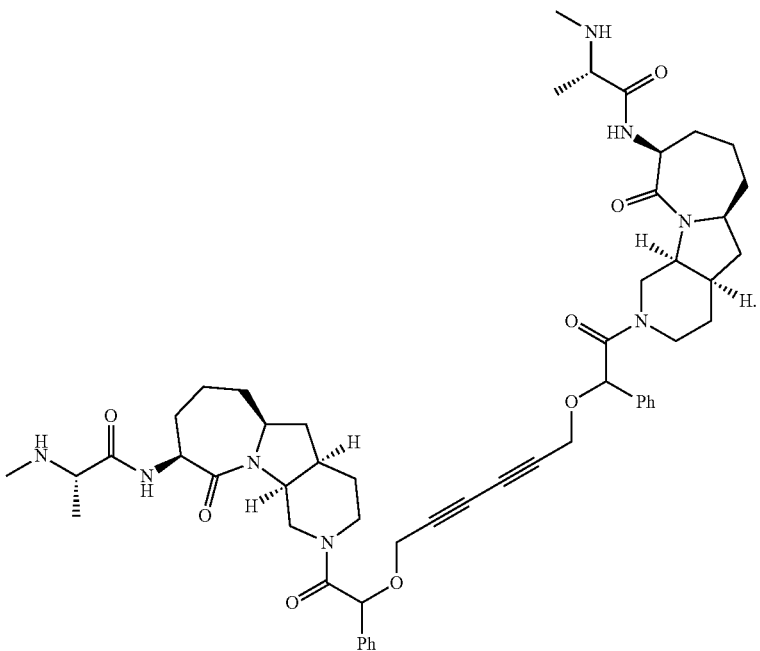

In a particular embodiment, the ILM of the compound has a chemical structure selected from the group consisting of:
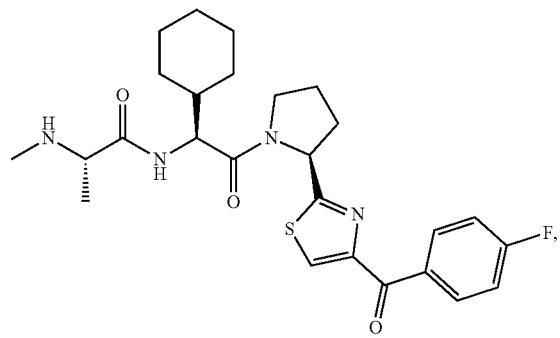
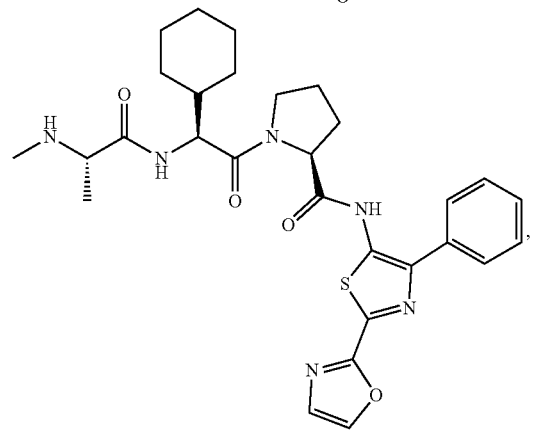
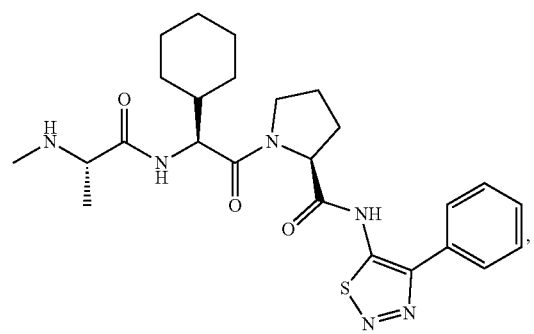
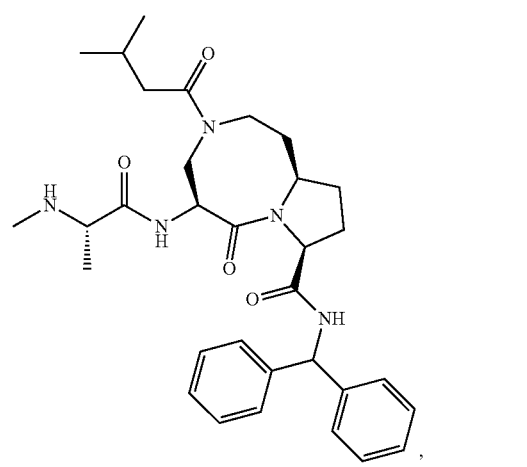
-continued
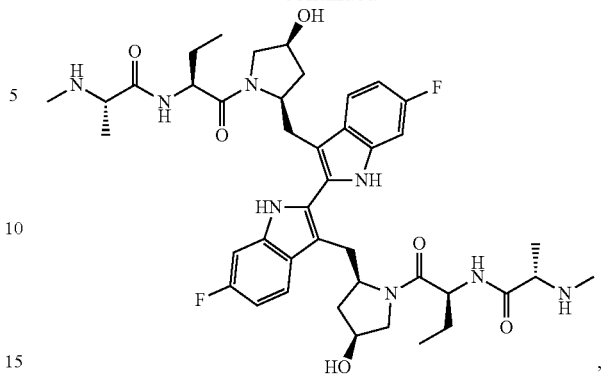
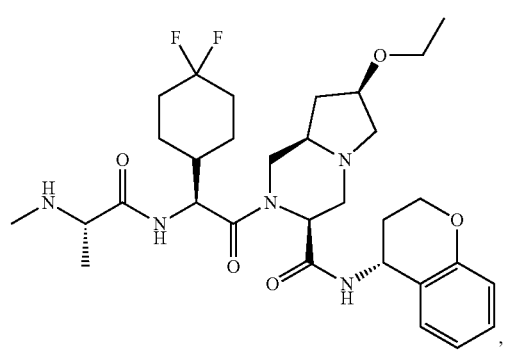
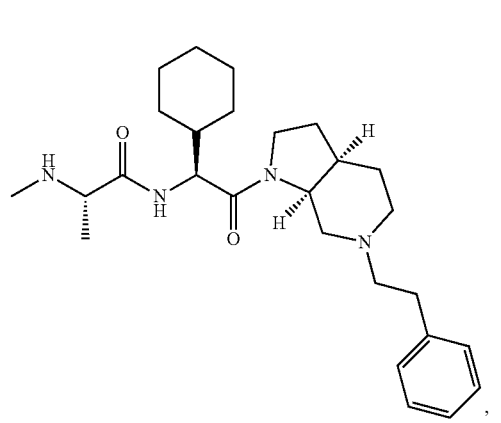
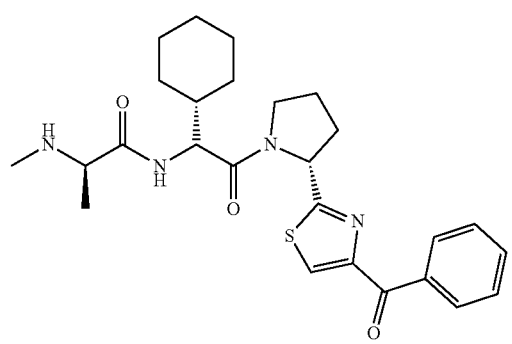

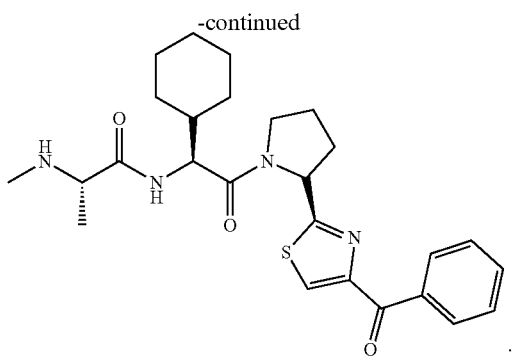

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C1$-$C_6$ alkyl amine or a $C1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$ or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—NR$_1$R$_2$ or —N(R$_1$)—C(O)—O—R$_1$, nitro, cyano and amine (especially including a $C_1$-$C_6$ alkylene-NR$_1$R$_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, $C_1$-$C_6$ alkyl, —(CH$_2$)$_n$O—(C$_1$-$C_6$ alkyl), —(CH$_2$)$_n$C(O)—(C$_1$-$C_6$ alkyl), —(CH$_2$)$_n$OC(O)—(C$_1$-$C_6$ alkyl), —(CH$_2$)$_n$C(O)O—(C$_1$-$C_6$ alkyl), —(CH$_2$)$_n$NHC(O)—R$_1$, —(CH$_2$)$_n$C(O)—NR$_1$R$_2$, —(OCH$_2$)$_n$OH, —(CH$_2$O)$_n$COOH, $C_1$-$C_6$ alkyl, —(OCH$_2$)$_n$O—(C$_1$-$C_6$ alkyl), —(CH$_2$O)$_n$C(O)—(C$_1$-$C_6$ alkyl), —(OCH$_2$)$_n$NHC(O)—R$_1$, —(CH$_2$O)$_n$C(O)—NR$_1$R$_2$, —S(O)$_2$—R$_S$, —S(O)—R$_S$ (R$_S$ is $C_1$-$C_6$ alkyl or a —(CH$_2$)$_m$—NR$_1$R$_2$ group), NO$_2$, CN or halogen (F, Cl, Br, I, preferably F or Cl), depending on the context of the use of the substituent. R$_1$ and R$_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—NR$_1$R$_2$ group where R$_1$ and R$_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —(CH$_2$)$_n$OH, —(CH$_2$)$_n$—O—(C$_1$-$C_6$)alkyl, —(CH$_2$)$_n$—O—(CH$_2$)$_n$—(C$_1$-$C_6$)alkyl, —(CH$_2$)$_n$—C(O)(C$_0$-$C_6$) alkyl, —(CH$_2$)$_n$—C(O)O(C$_0$-$C_6$) alkyl, —(CH$_2$)$_n$—OC(O)(C$_0$-$C_6$)alkyl, amine, mono- or di-(C$_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably connected/attached to a PTM group, including a ULM group, via a linker group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3, or 4-pyridine) or a group according to the chemical structure:

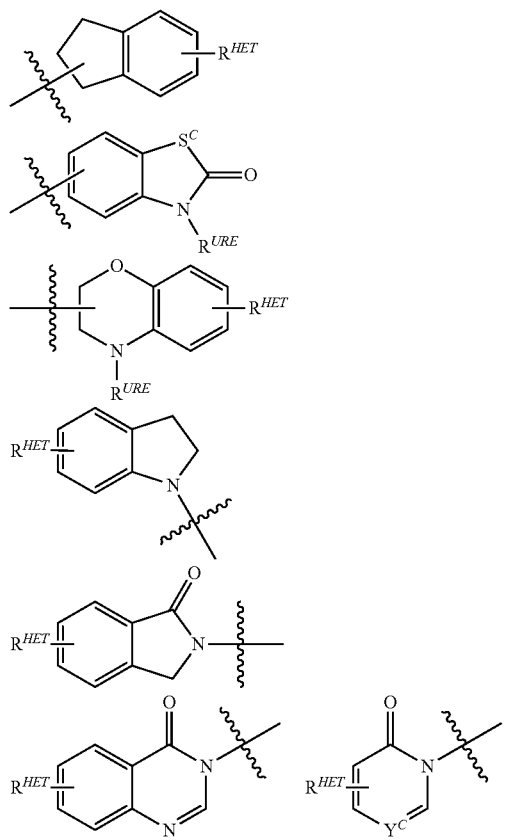

wherein:
S$^c$ is CHR$^{SS}$, NR$^{URE}$, or O;
R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);
R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
Y$^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO— heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

In any of the embodiments described herein, the W, X, Y, Z, G, G', R, R', R", Q1-Q4, A, and Rn can independently be covalently coupled to a linker and/or a linker to which is attached one or more PTM, ULM, ILM or ILM' groups.

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

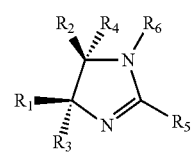

Formula (A-1)

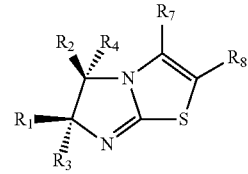

Formula (A-2)

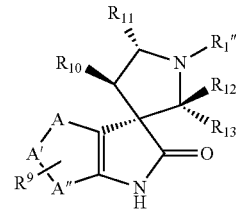

Formula (A-3)

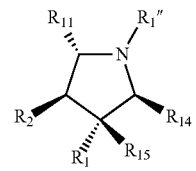

Formula (A-4)

-continued

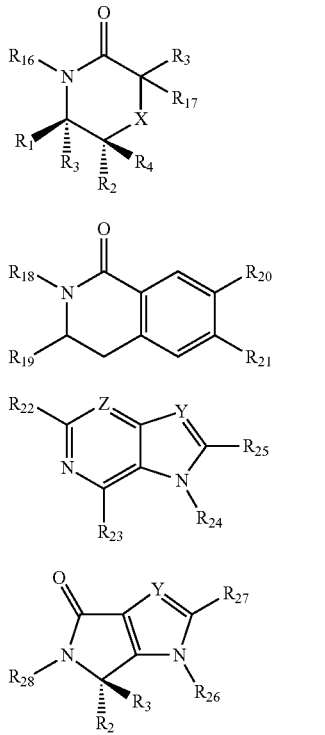

Formula (A-5)

Formula (A-6)

Formula (A-7)

Formula (A-8)

wherein above Formula (A-1) through Formula (A-8),
X of Formula (A-1) through Formula (A-8) is selected from the group consisting of carbon, oxygen, sulfur, sulfoxide, sulfone, and N—$R^a$;
  $R^a$ is independently H or an alkyl group with carbon number 1 to 6;
Y and Z of Formula (A-1) through Formula (A-8) are independently carbon or nitrogen;
A, A' and A" of Formula (A-1) through Formula (A-8) are independently selected from C, N, O or S, can also be one or two atoms forming a fused bicyclic ring, or a 6,5- and 5,5-fused aromatic bicyclic group;
$R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:
  halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;
$R_3$, $R_4$ of Formula (A-1) through Formula (A-8) are independently selected from the group consisting of H, methyl and C1 to C6 alkyl;
$R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:
  halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);
$R_6$ of Formula (A-1) through Formula (A-8) is H or —C(=O)$R^b$, wherein
  $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-$R^c$-1-piperidinyl, wherein
  $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein
  $R^d$ of Formula (A-1) through Formula (A-8) is selected from the group consisting of alkoxy, alkyl sulfone, alkyl sulfoxide, N-substituted carboxamide, —NHC(O)-alkyl, —NH—SO$_2$-alkyl, aryl, substituted aryl, heteroaryl, substituted heteroaryl;
$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;
$R_8$ of Formula (A-1) through Formula (A-8) is selected from the group consisting of —$R^e$C(O)—$R^f$, —$R^e$-alkoxy, —$R^e$-aryl, —$R^e$-heteroaryl, and —$R^e$—C(O)—$R^f$—C(O)—$R^g$, wherein:
  $R^e$ of Formula (A-1) through Formula (A-8) is an alkylene with 1 to 6 carbons, or a bond;
  $R^f$ of Formula (A-1) through Formula (A-8) is a substituted 4- to 7-membered heterocycle;
  $R^g$ of Formula (A-1) through Formula (A-8) is selected from the group consisting of aryl, hetero aryl, substituted aryl or heteroaryl, and 4- to 7-membered heterocycle;
$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;
$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;
$R_{11}$ of Formula (A-1) through Formula (A-8) is —C(O)—N($R^h$)($R^i$), wherein $R^h$ and $R^i$ are selected from groups consisting of the following:

H; optionally substituted linear or branched C1 to C6 alkyl; alkoxy substituted alkyl; mono- and di-hydroxy substituted alkyl (e.g., a C3 to C6), sulfone substituted alkyl; optionally substituted aryl; optionally substituted heteraryl; mono-, bis- or tri-substituted aryl or heteroaryl; phenyl-4-carboxylic acid; substituted phenyl-4-carboxylic acid, alkyl carboxylic acid; optionally substituted heteroaryl carboxylic acid; alkyl carboxylic acid; fluorine substituted alkyl carboxylic acid; optionally substituted cycloalky, 3-hydroxycyclobutane, 4-hydroxycyclohehexane, aryl substituted cycloalkyl; heteroaryl substituted cycloalkyl; or Rh and Ri taken together form a ring;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one $CH_2$ replaced by S(=O), —S, or —S(=O)$_2$, alkyl or cycloalkyl with terminal $CH_3$ replaced by S(=O)$_2$N(alkyl)(alkyl), —C(=O)N(alkyl)(alkyl), —N(alkyl)S(=O)$_2$(alkyl), —C(=O)$_2$(alkyl), —O(alkyl), C1-6 alkyl or alkyl-cycloalkyl with hydron replaced by hydroxyl group, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated $C_{1-6}$ alkyl, $C_{1-6}$ alkyl containing thioether, ether, sulfone, sulfoxide, fluorine substituted ether or cyano group;

$R_{17}$ of Formula (A-1) through Formula (A-8) is selected from the group consisting of $(CH_2)_nC(O)NR^kR^l$, wherein $R^k$ and $R^l$ are independently selected from H, C1-6 alkyl, hydrxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ of Formula (A-1) through Formula (A-8) is selected from the group consisting of aryl, heteroaryl, bicyclic heteroaryl, and these aryl or hetroaryl groups can be substituted with halogen, C1-6 alkyl, C1-6 cycloalkyl, $CF_3$, F, CN, alkyne, alkyl sulfone, the halogen substitution can be mon- bis- or tri-substituted;

$R_{20}$ and $R_{21}$ of Formula (A-1) through Formula (A-8) are independently selected from C1-6 alkyl, C1-6 cycloalkyl, C1-6 alkoxy, hydoxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with $C_{1-6}$ alkyl, alkoxy, fluorine-substituted alkyl, CN, and alkylsulfone;

$R_{23}$ of Formula (A-1) through Formula (A-8) is selected from aryl, heteroaryl, —O-aryl, —O— heteroaryl, —O-alkyl, —O-alkyl-cycloalkyl, —NH-alkyl, —NH-alkyl-cycloalkyl, —N(H)-aryl, —N(H)-heteroaryl, —N(alkyl)-aryl, —N(alkyl)-heteroaryl, the aryl or heteroaryl groups can be substituted with halogen, C1-6 alkyl, hydoxylated C1-6 alkyl, cycloalkyl, fluorine-substituted C1-6 alkyl, CN, alkoxy, alkyl sulfone, amide and sulfonamide;

$R_{24}$ of Formula (A-1) through Formula (A-8) is selected from the group consisting of —CH2-(C1-6 alkyl), —CH2-cycloalkyl, —CH2-aryl, CH2-heteroaryl, where alkyl, cycloalkyl, aryl and heteroaryl can be substituted with halogen, alkoxy, hydoxylated alkyl, cyano-substituted alkyl, cycloalyl and substituted cycloalkyl;

$R_{25}$ of Formula (A-1) through Formula (A-8) is selected from the group consisting of C1-6 alkyl, $C_{1-6}$ alkyl-cycloalkyl, alkoxy-substituted alkyl, hydroxylated alkyl, aryl, heteroaryl, substituted aryl or heteroaryl, 5, 6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—S(O)$_2$-alkyl, and —S(O)$_2$-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1''}$ of Formula (A-1) through Formula (A-8) is selected from the group consisting of H, alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^g$ of Formula (A-1) through Formula (A-8) are substituted pyrrolidine, substituted piperidine, substituted piperizine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where 'L' is a connector (i.e. a linker group), and "PTM" is a ligand binding to a target protein.

In certain embodiments, the description provides a bifunctional molecule comprising a structure selected from the group consisting of:

Formula (A-9)
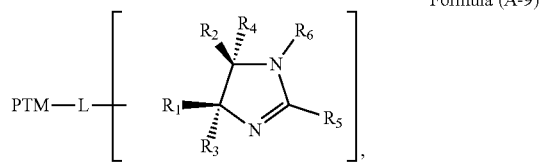

Formula (A-10)
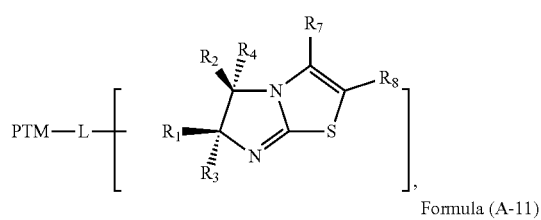

Formula (A-11)
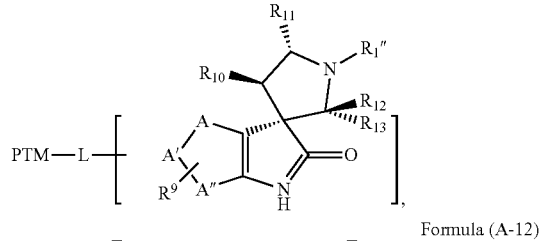

Formula (A-12)
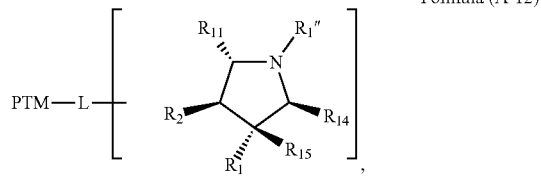

Formula (A-13)
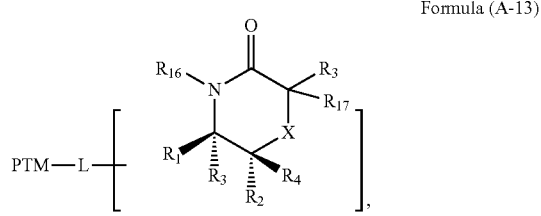

Formula (A-14)
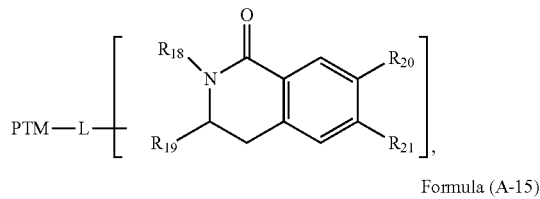

Formula (A-15)

, and

Formula (A-16)
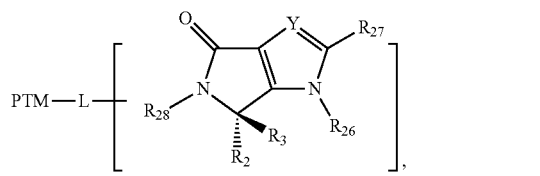
, wherein X, $R^a$, Y, Z, A, A', A", $R_1$, $R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R^{27}$, $R_{28}$, and $R_{1''}$ are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

A-1-1
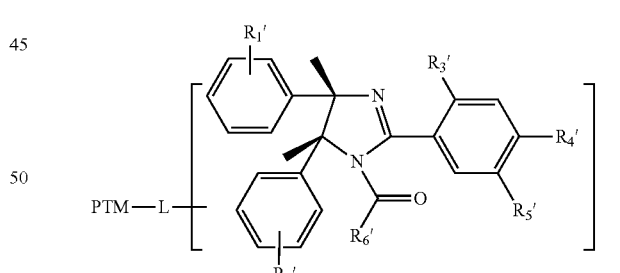

A-1-2
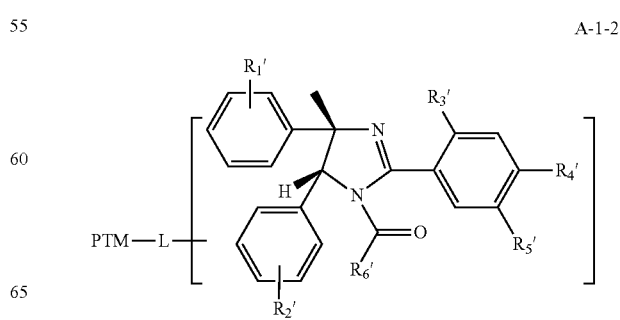

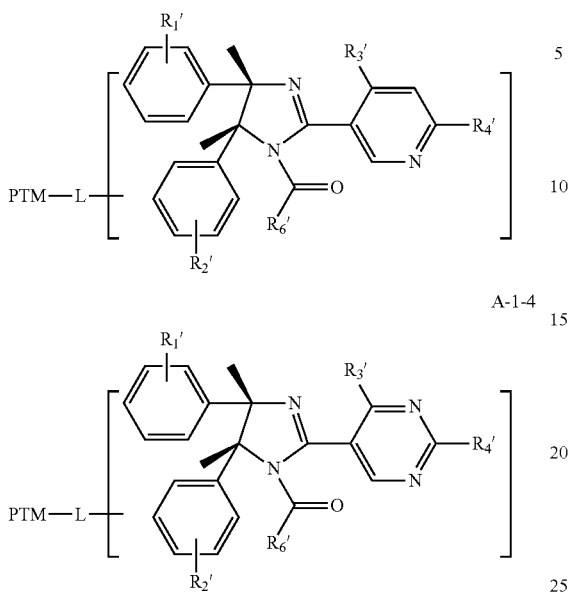

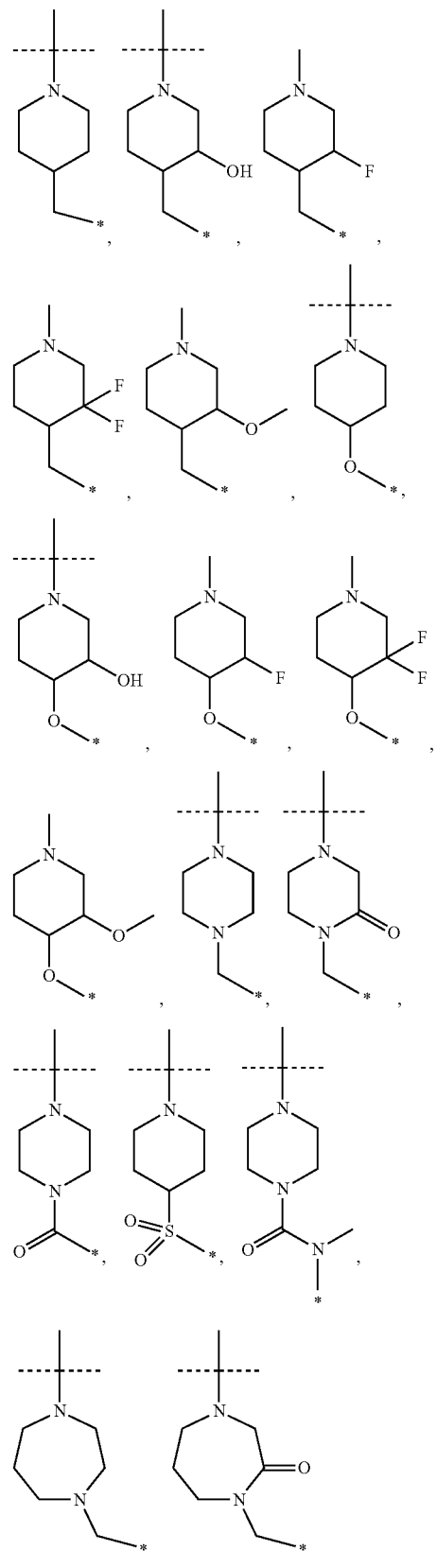

wherein:
- R1' and R2' of Formulas A-1-1 through A-1-4 (i.e., A-1-1, A-1-2, A-1-3, and A-1-4) are independently selected from the group consisting of F, Cl, Br, I, acetylene, CN, $CF_3$ and $NO_2$;
- R3' is selected from the group consisting of —$OCH_3$, —$OCH_2CH_3$, —$OCH_2CH_2F$, —$OCH_2CH_2OCH_3$, and —$OCH(CH_3)_2$;
- R4' of Formulas A-1-1 through A-1-4 is selected from the group consisting of H, halogen, —$CH_3$, —$CF_3$, —$OCH_3$, —$C(CH_3)_3$, —$CH(CH_3)_2$, -cyclopropyl, —CN, —$C(CH_3)_2OH$, —$C(CH_3)_2OCH_2CH_3$, —$C(CH_3)_2CH_2OH$, —$C(CH_3)_2CH_2OCH_2CH_3$, —$C(CH_3)_2CH_2OCH_2CH_2OH$, —$C(CH_3)_2CH_2OCH_2CH_3$, —$C(CH_3)_2CN$, —$C(CH_3)_2C(O)CH_3$, —$C(CH_3)_2C(O)NHCH_3$, —$C(CH_3)_2C(O)N(CH_3)_2$, —$SCH_3$, —$SCH_2CH_3$, —$S(O)_2CH_3$, —$S(O_2)CH_2CH_3$, —$NHC(CH_3)_3$, —$N(CH_3)_2$, pyrrolidinyl, and 4-morpholinyl;
- R5' of Formulas A-1-1 through A-1-4 is selected from the group consisting of halogen, -cyclopropyl, —$S(O)_2CH_3$, —$S(O)_2CH_2CH_3$, 1-pyrrolidinyl, —$NH_2$, —$N(CH_3)_2$, and —$NHC(CH_3)_3$; and
- R6' of Formulas A-1-1 through A-1-4 is selected from the structures presented below where the linker connection point is indicated as "*".
- Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 through A-1-4 is at least one of R4' or R6' or both.

In certain embodiments, R6' of Formulas A-1-1 through A-1-4 is independently selected from the group consisting of H, -continued

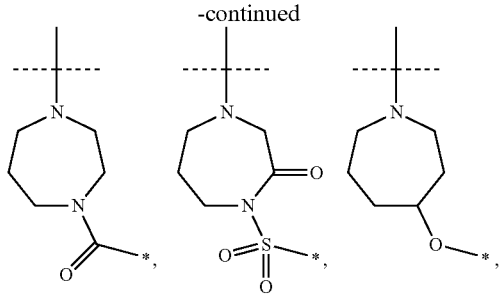

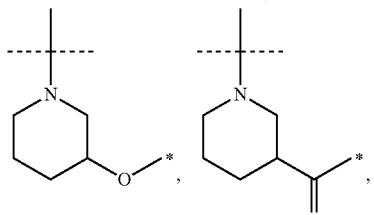

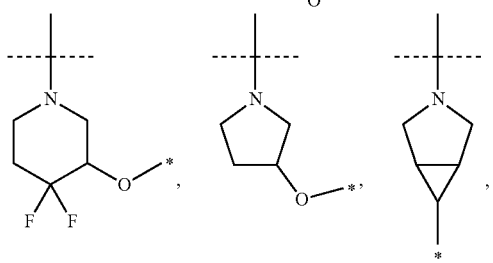

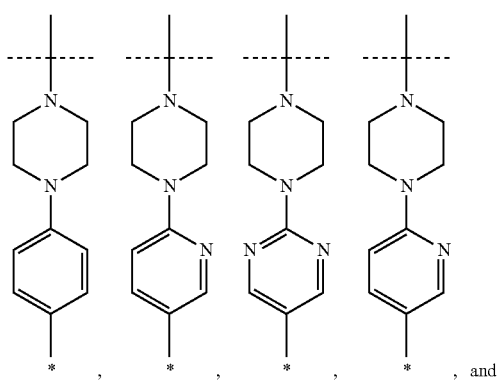

, and

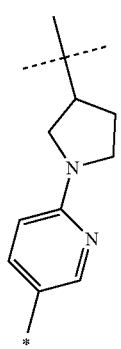

wherein "*" indicates the point of attachment of the linker.

In certain embodiments, the linker of Formula A-4-1 through A-4-6 is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

A-4-1

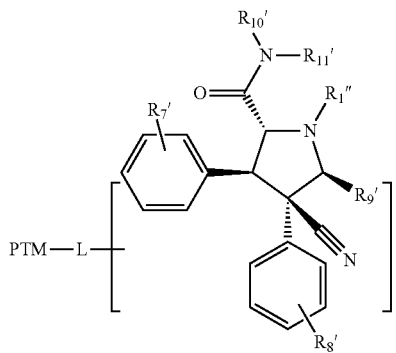

A-4-2

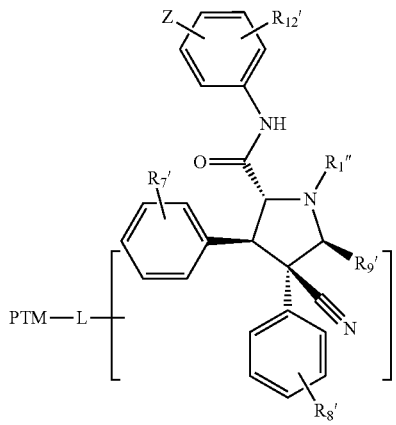

A-4-3

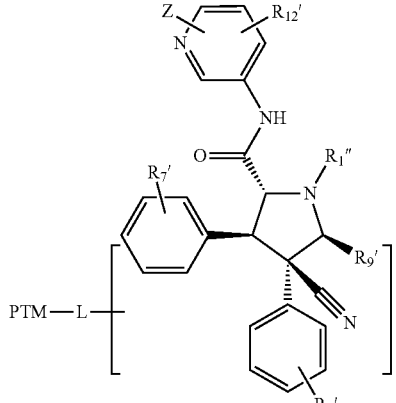

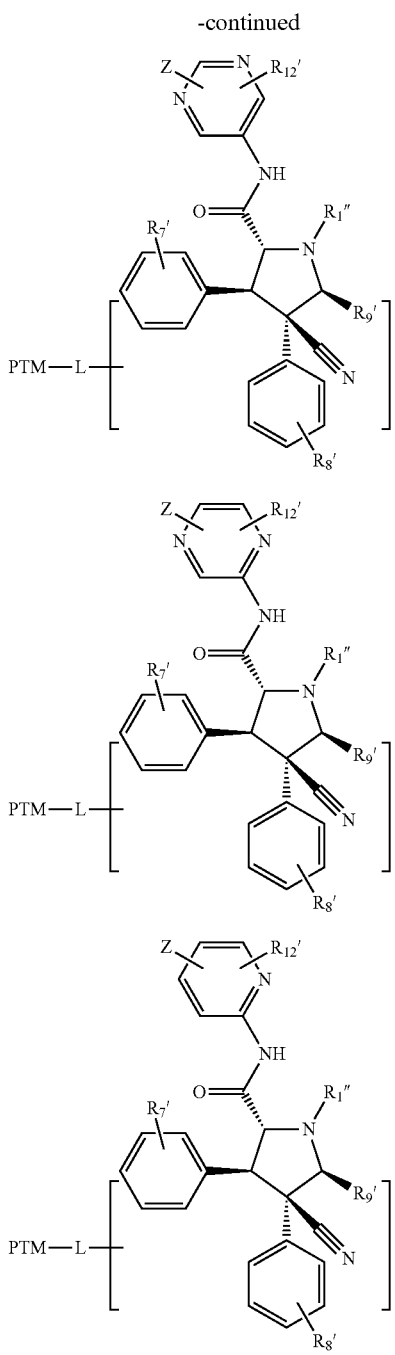

substituted aryl, hetero aryl, substituted heteroaryl, cycloalkyl, substituted cycloalkyl, alkenyl, and substituted cycloalkenyl;

Z of Formula A-4-1 through A-4-6 is selected from the group consisting of H, —OCH$_3$, —OCH$_2$CH$_3$, and halogen;

R10' and R11' of Formula A-4-1 through A-4-6 are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH)$_n$—CONR'R", (CH$_2$)$_n$—OR', (CH$_2$)$_n$—SR', (CH$_2$)$_n$—SOR', (CH$_2$)$_n$—CH(OH)—R', (CH$_2$)$_n$—COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_n$—(CH$_2$)$_n$—NR'COR", (CH$_2$CH$_2$O)$_m$(CH$_2$)$_n$—NR'SO$_2$R", (CH$_2$CH$_2$O)$_m$(CH$_2$)$_n$—COOH, (CH$_2$CH$_2$O)$_m$(CH$_2$)$_n$—COOR', (CH$_2$CH$_2$O)$_m$(CH$_2$)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—(CH$_2$CH$_2$O)$_m$(CH$_2$)$_n$R', (CH$_2$)p-(CH$_2$CH$_2$O)$_m$—(CH$_2$)$_n$—OH, (CH$_2$)$_p$—(CH$_2$CH$_2$O)$_m$—(CH$_2$)n-OR', (CH$_2$)$_p$—(CH$_2$CH$_2$O)$_m$—(CH$_2$)$_n$—NR'R", (CH$_2$)$_p$—(CH$_2$CH$_2$O)$_m$—(CH$_2$)$_n$—NR'COR", (CH$_2$)$_p$—(CH$_2$CH$_2$O)$_m$—(CH$_2$)$_n$—NR'SO$_2$R", (CH2)$_p$—(CH$_2$CH$_2$O)$_m$—(CH$_2$)$_n$—COOH, (CH$_2$)$_p$—(CH$_2$CH$_2$)$_m$—(CH$_2$)$_n$—COOR', (CH$_2$)$_p$—(CH$_2$CH$_2$O)$_m$—(CH$_2$)$_n$—CONR'R", (CH$_2$)$_p$—(CH$_2$CH$_2$O)$_m$—(CH$_2$)$_n$—SO$_2$R', (CH2)$_p$—(CH$_2$CH$_2$O)$_m$—(CH$_2$)$_n$—COR', (CH$_2$)$_p$—(CH$_2$CH$_2$O)$_m$—(CH$_2$)$_n$—SONR'R", (CH$_2$)$_p$—(CH$_2$CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), N(alkyl)$_2$, oxo, carboxy, clcloalkyl and heteroaryl;

m, n, and p are independently 0 to 6;

R12' of Formula A-4-1 through A-4-6 is selected from the group consisting of —O-(alkyl), —O-(alkyl)-akoxy, —C(O)-(alkyl), —C(OH)-alkyl-alkoxy, —C(O)—NH-(alkyl), —C(O)—N-(alkyl)$_2$, —S(O)-(alkyl), S(O)$_2$-(alkyl), —C(O)-(cyclic amine), and —O-aryl-(alkyl), —O-aryl-(alkoxy);

R1" of Formula A-4-1 through A-4-6 is selected from the group consisting of H, alkyl, aryl substituted alkyl, aloxy substituted alkyl, cycloalkyl, ary-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11", R12", or R1".

The method used to design chimeric molecules as presented in A-1-1 through A-1-4, A-4-1 through A-4-6 can be applied to MLM with formula A-2, A-3, A-5, A-6, A-7 and A-8, wherein the solvent exposed area in the MLM can be connected to linker "L" which will be attached to target protein ligand "PTM", to construct PROTACs.

wherein:
R7' of Formula A-4-1 through A-4-6 (i.e., A-4-1, A-4-2, A-4-3, A-4-4, A-4-5, and A-4-6) is one or more (e.g., 1, 2, 3, 4) halogens;
R8' of Formula A-4-1 through A-4-6 is one or more groups (e.g., 1, 2, 3, or 4 groups) selected from the group consisting of H, —F, —Cl, —Br, —I, —CN, —NO$_2$, ethylnyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted;
R9' of Formula A-4-1 through A-4-6 is selected from the group consisting of alkyl, substituted alkyl, alkenyl, substituted alkenyl, alkynyl, substituted alkynyl, aryl, In any aspect or embodiment described herein, the MLM is selected from:

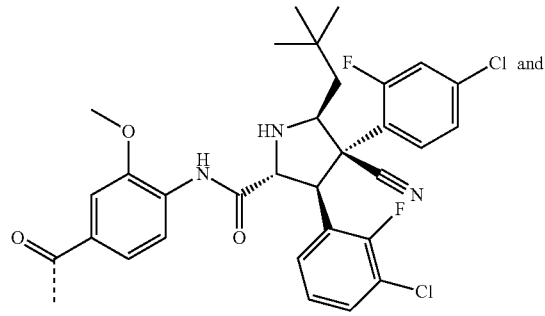

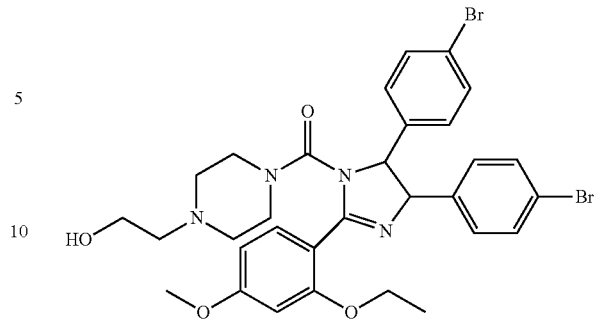

(derivatized where a linker group L or a -(L-MLM) group is attached, for example, at the methoxy group or hydroxyl group);

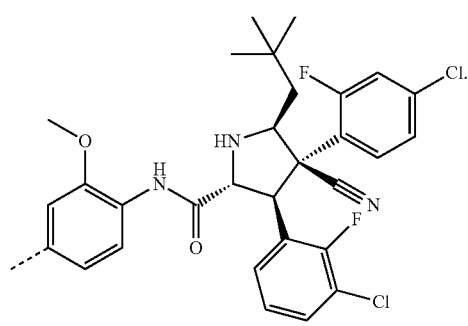

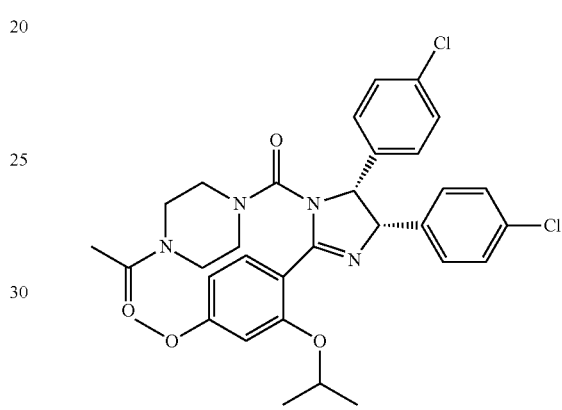

Exemplary MDM2 binding moieties include, but not limited, the following:

1. The HDM2/MDM2 inhibitors identified in Vassilev, et al., In vivo activation of the p53 pathway by small-molecule antagonists of MDM2, *SCIENCE* vol: 303, pag: 844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

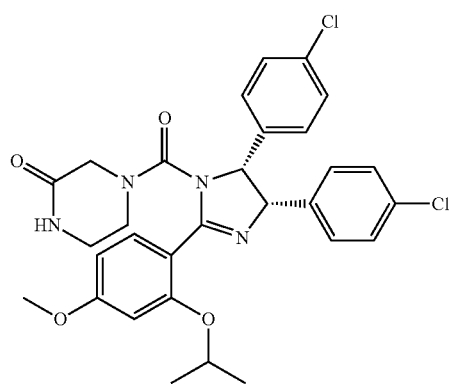 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM) group is attached, for example, at the methoxy group or as a hydroxyl group);

(derivatized where a linker group L or a -(L-MLM) group is attached, for example, via the methoxy group or as a hydroxyl group); and 2. Trans-4-Iodo-4'-Boranyl-Chalcone

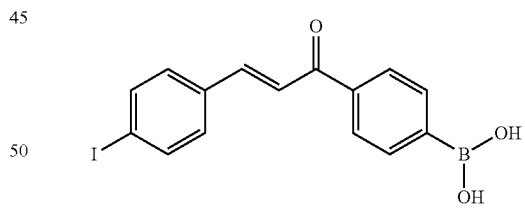

(derivatized where a linker group L or a linker group L or a-(L-MLM) group is attached, for example, via a hydroxy group).

Exemplary CLMs

Neo-Imide Compounds

In one aspect the description provides compounds useful for binding and/or inhibiting cereblon. In certain embodiments, the compound is selected from the group consisting of chemical structures:

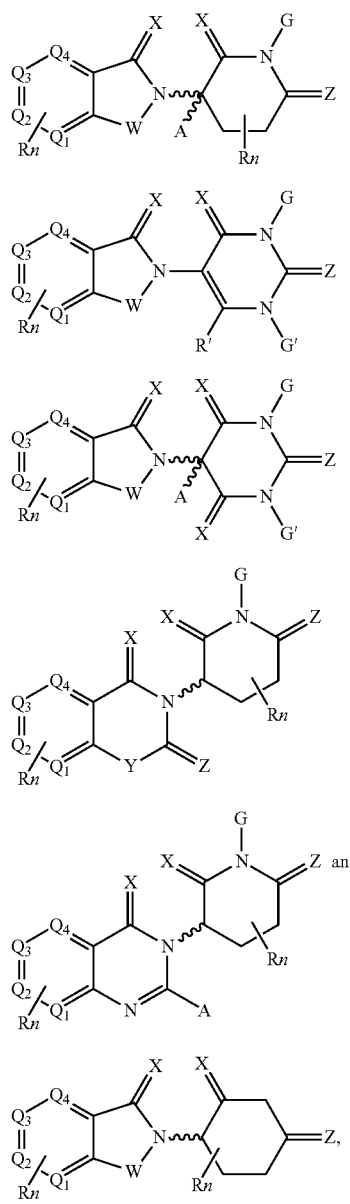

wherein:
- W of Formulas (a) through (f) is independently selected from the group $CH_2$, CHR, C=O, $SO_2$, NH, and N-alkyl;
- X of Formulas (a) through (f) is independently selected from the group O, S and $H_2$;
- Y of Formulas (a) through (f) is independently selected from the group $CH_2$, —C=CR', NH, N-alkyl, N-aryl, N-hetaryl, N-cycloalkyl, N-heterocyclyl, O, and S;
- Z of Formulas (a) through (f) is independently selected from the group O, and S or $H_2$ except that both X and Z cannot be $H_2$;
- G and G' of Formulas (a) through (f) are independently selected from the group H, optionally substituted linear or branched alkyl, OH, R'OCOOR, R'OCONRR", CH2-heterocyclyl optionally substituted with R', and benzyl optionally substituted with R';
- Q1-Q4 of Formulas (a) through (f) represent a carbon C substituted with a group independently selected from R', N or N-oxide;
- A of Formulas (a) through (f) is independently selected from the group H, optionally substituted linear or branched alkyl, cycloalkyl, Cl and F;
- R of Formulas (a) through (f) comprises, but is not limited to: —CONR'R", —OR', —NR'R", —SR', —$SO_2$R', —$SO_2$NR'R", —CR'R"—, —CR'NR'R"—, (—CR'O)$_n$R", -aryl, -hetaryl, -optionally substituted linear or branched alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$
- R' and R" of Formulas (a) through (f) are independently selected from a bond, H, alkyl, cycloalkyl, aryl, heteroaryl, heterocyclic, —C(=O)R, heterocyclyl, each of which is optionally substituted;
- n' of Formulas (a) through (f) is an integer from 1-10 (e.g. 1-4, 1, 2, 3, 4, 5, 6, 7, 8, 9, or 10);
- ⁓ of Formulas (a) through (f) represents a bond that may be stereospecific ((R) or (S)) or non-stereospecific; and
- $R_n$ of Formulas (a) through (f) comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy.

Exemplary CLMs

In any of the compounds described herein, the CLM comprises a chemical structure selected from the group:

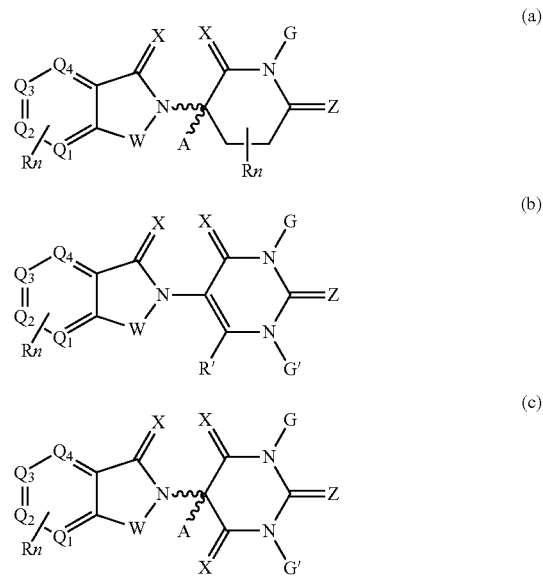

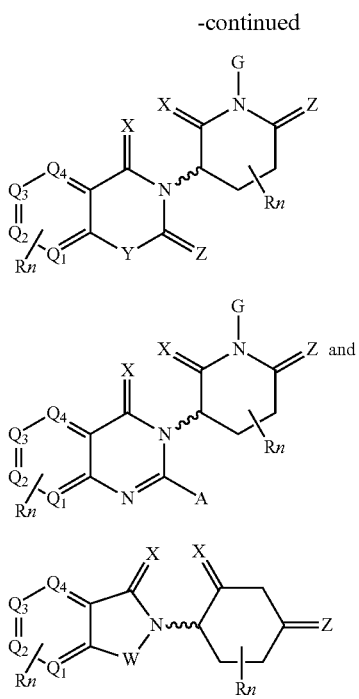

n of Formulas (a) through (f) is an integer from 1-10 (e.g., 1-4, 1, 2, 3, 4, 5, 6, 7, 8, 9, or 10);

∿∿∿ of Formulas (a) through (f) represents a bond that may be stereospecific ((R) or (S)) or non-stereospecific; and Rn of Formulas (a) through (f) comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, and optionally, one of which is modified to be covalently joined to a PTM, a chemical linker group (L), a ULM, CLM (or CLM') or combination thereof.

In certain embodiments described herein, the CLM or ULM comprises a chemical structure selected from the group:

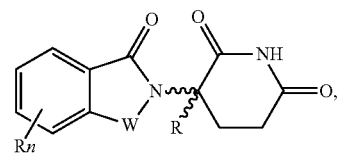

Formula (g)

wherein:

W of Formulas (a) through (f) is independently selected from the group $CH_2$, CHR, C=O, $SO_2$, NH, and N-alkyl;

X of Formulas (a) through (f) is independently selected from the group O, S and H2;

Y of Formulas (a) through (f) is independently selected from the group $CH_2$, —C=CR', NH, N-alkyl, N-aryl, N-hetaryl, N-cycloalkyl, N-heterocyclyl, O, and S;

Z of Formulas (a) through (f) is independently selected from the group O, and S or H2 except that both X and Z cannot be H2;

G and G' of Formulas (a) through (f) are independently selected from the group H, optionally substituted linear or branched alkyl, OH, R'OCOOR, R'OCONRR", $CH_2$-heterocyclyl optionally substituted with R', and benzyl optionally substituted with R';

Q1-Q4 of Formulas (a) through (f) represent a carbon C substituted with a group independently selected from R', N or N-oxide;

A of Formulas (a) through (f) is independently selected from the group H, alkyl (linear, branched, optionally substituted), cycloalkyl, Cl and F;

R of Formulas (a) through (f) comprises, but is not limited to: —CONR'R", —OR', —NR'R", —SR', —SO2R', —SO2NR'R", —CR'R"—, —CR'NR'R"—, (—CR'O)$_n$R", -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF3

R' and R" of Formulas (a) through (f) are independently selected from a bond, H, alkyl, cycloalkyl, aryl, heteroaryl, heterocyclic, —C(=O)R, heterocyclyl, each of which is optionally substituted;

wherein:

W of Formula (g) is independently selected from the group $CH_2$, C=O, NH, and N-alkyl;

R of Formula (g) is independently selected from a H, methyl, or optionally substituted linear or branched alkyl (e.g., optionally substituted linear or branched C1-C6 alkyl);

∿∿∿ of Formula (g) represents a bond that may be stereospecific ((R) or (S)) or non-stereospecific; and Rn of Formula (g) comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, and optionally, one of which is modified to be covalently joined to a PTM, a chemical linker group (L), a ULM, CLM (or CLM') or combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

In any of the aspects or embodiments described herein, Rn comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, and optionally, one of which is modified to be covalently joined to a PTM, a chemical linker group (L), a ULM, CLM (or CLM') or combination thereof.

In any of the aspects or embodiments described herein, Rn comprises from 1 to 4 functional groups or atoms, for example, O, OH, N, C1-C6 alkyl, C1-C6 alkoxy, amine, amide, or carboxy, and optionally, one of which is modified to be covalently joined to a PTM, a chemical linker group (L), a ULM, CLM (or CLM') or combination thereof.

More specifically, non-limiting examples of CLMs include those shown below as well as those "hybrid" molecules that arise from the combination of 1 or more of the different features shown in the molecules below.
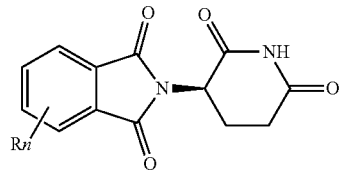
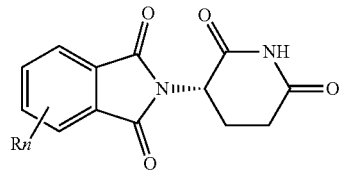
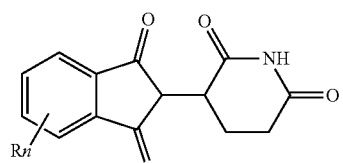
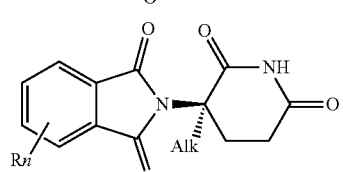
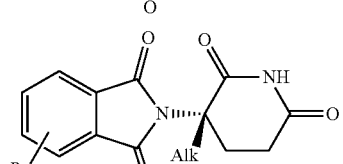
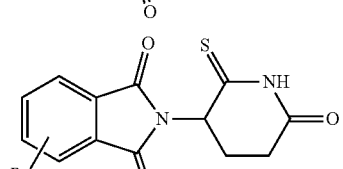
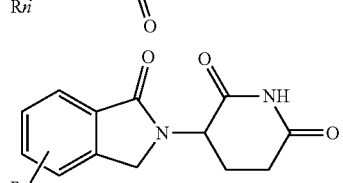
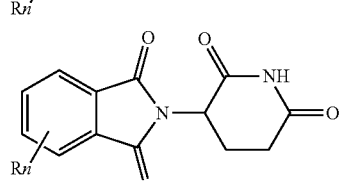
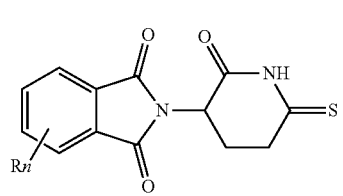
-continued
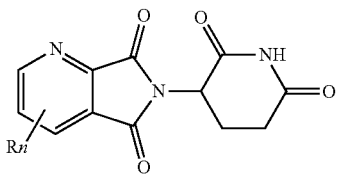
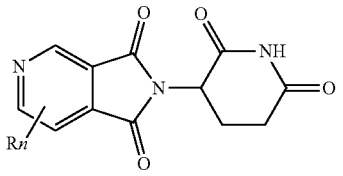
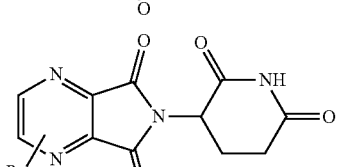
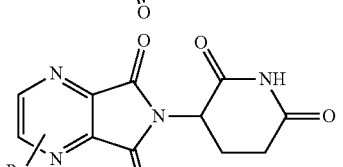
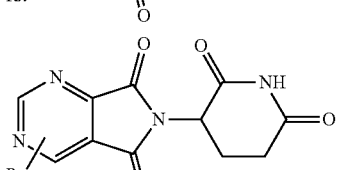
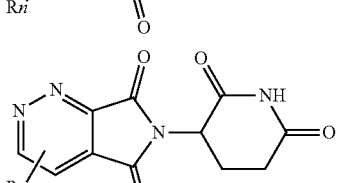
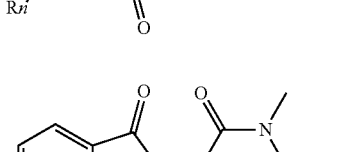

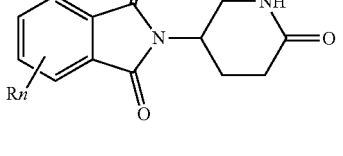
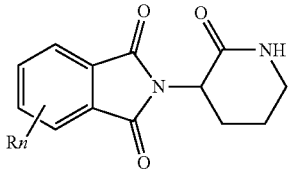

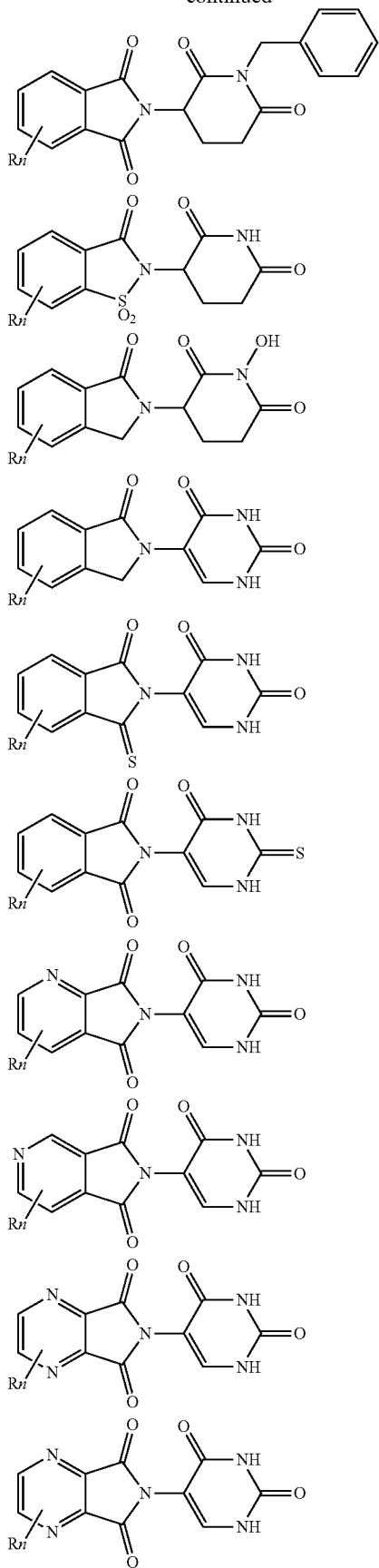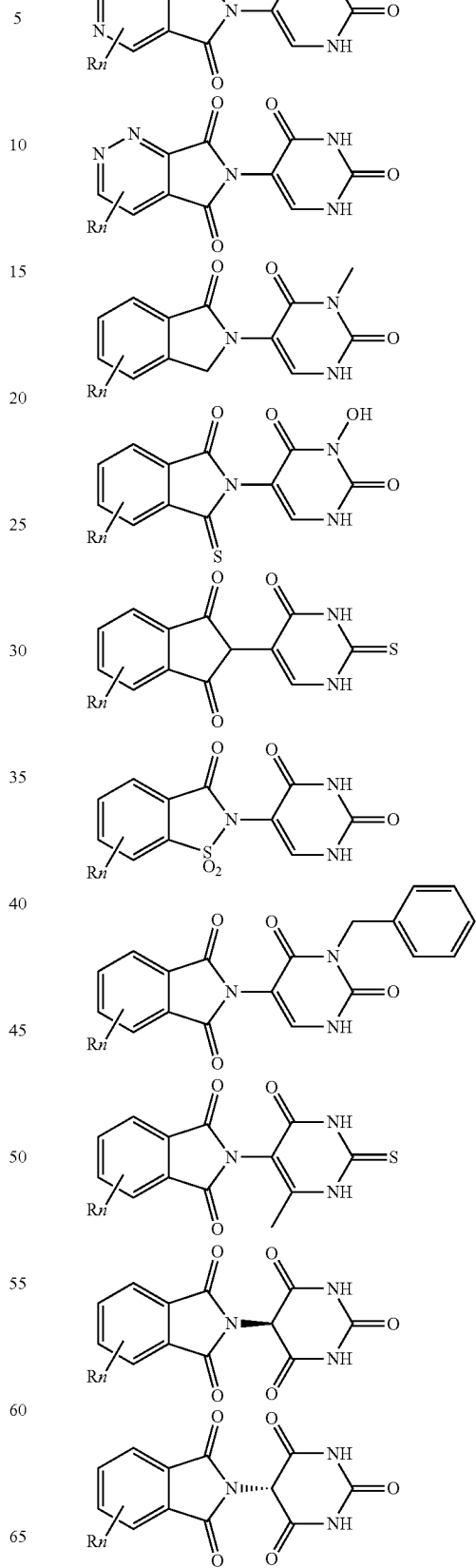

147
-continued
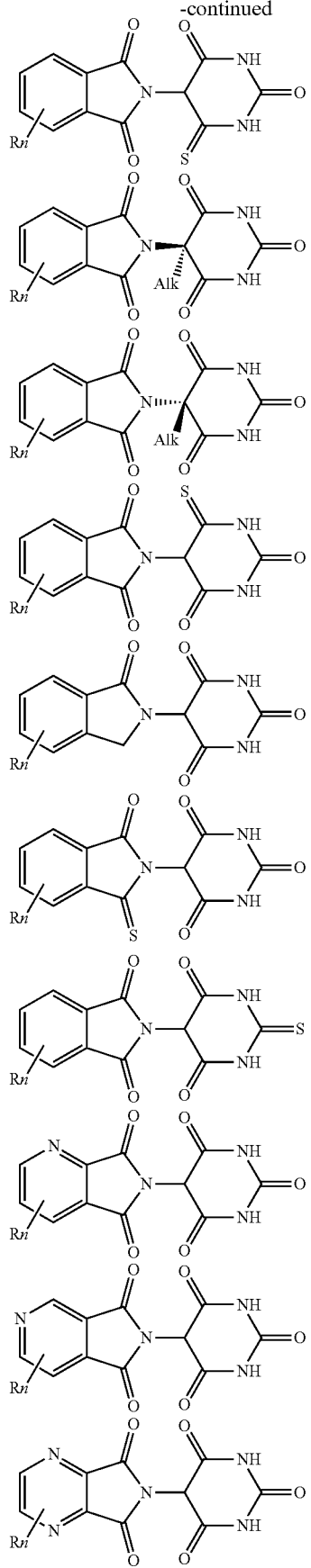
148
-continued
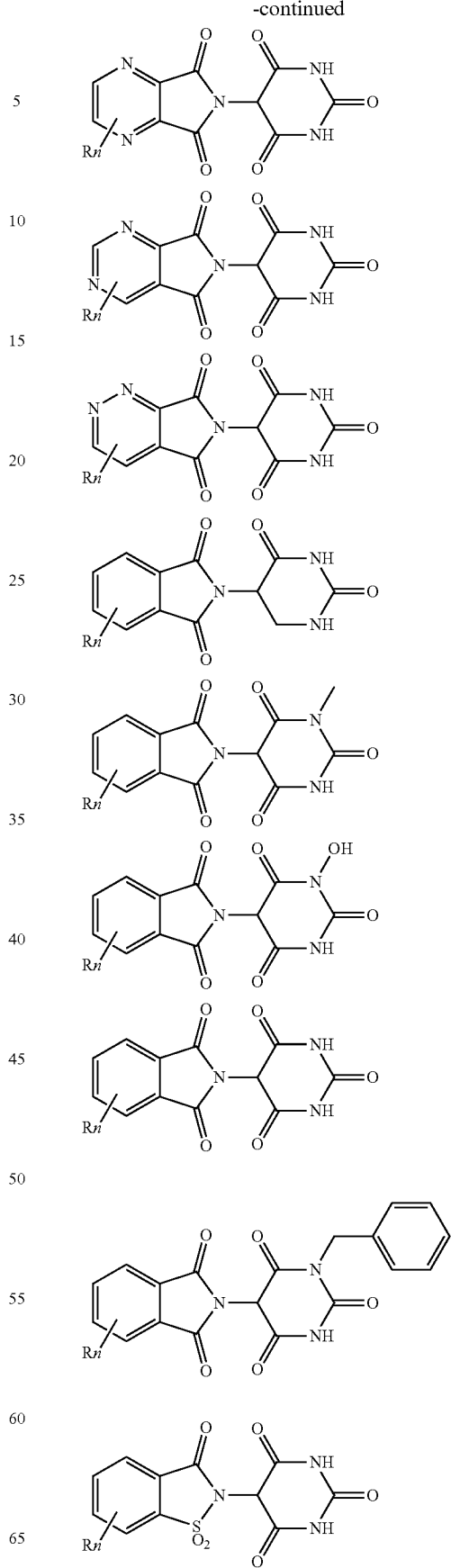

149
-continued
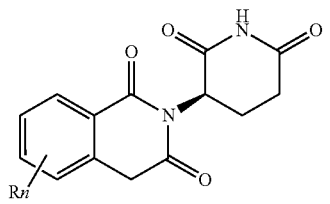
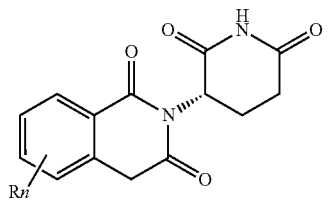
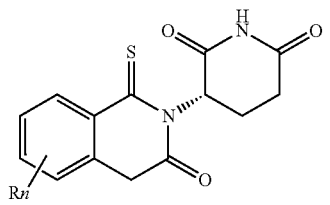
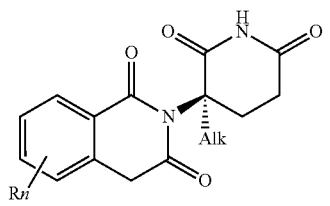
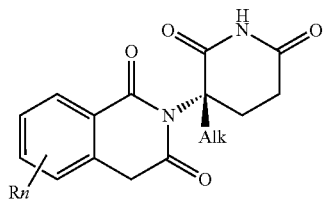
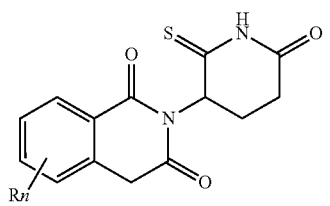
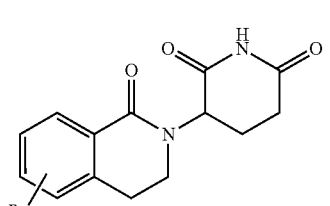
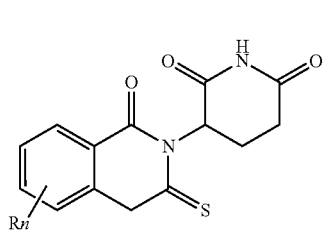
150
-continued
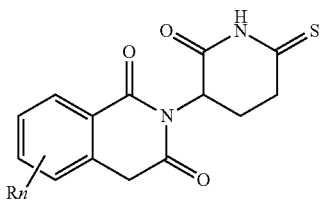
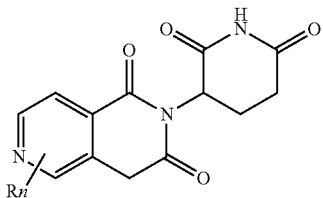
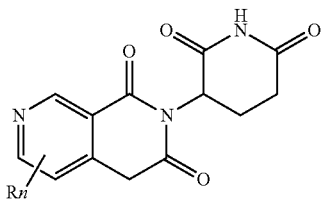
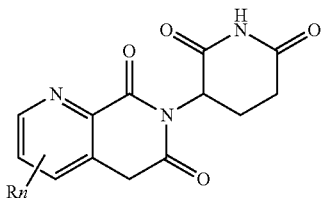
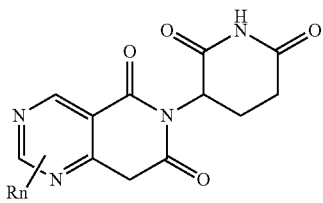
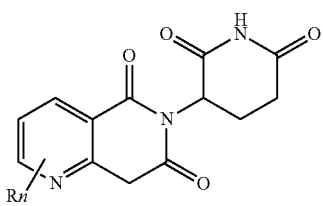
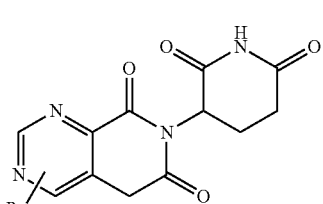
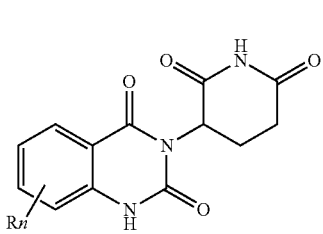

151
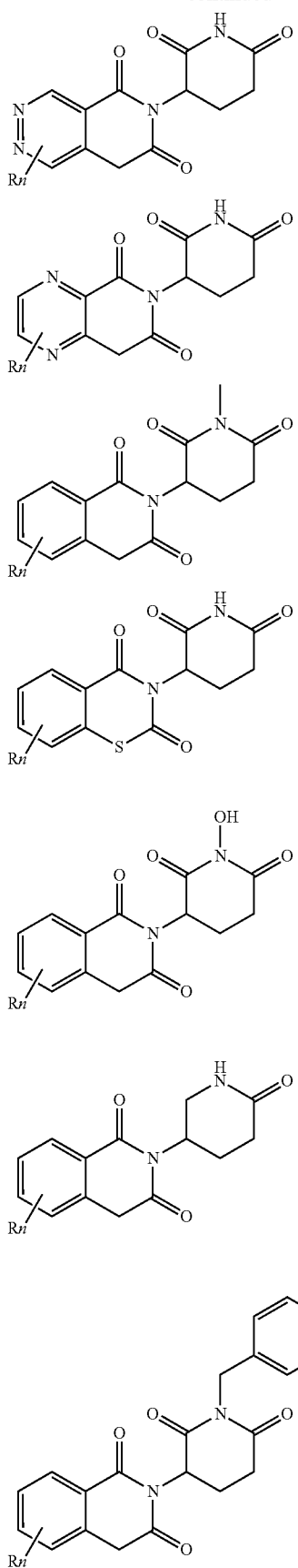
152
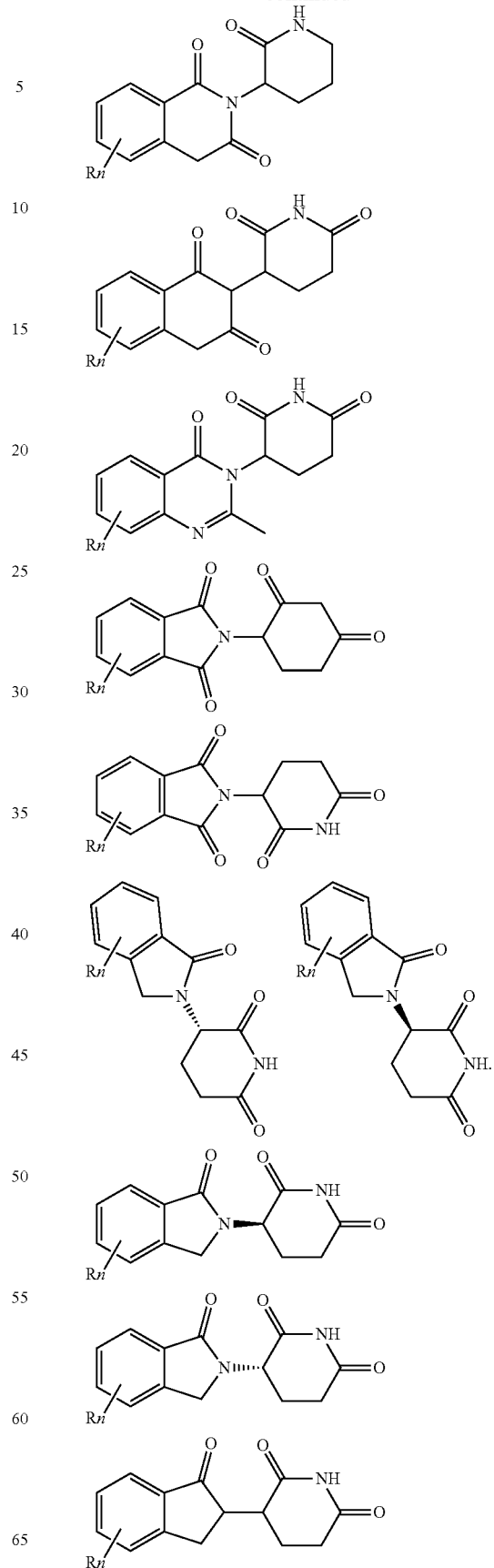

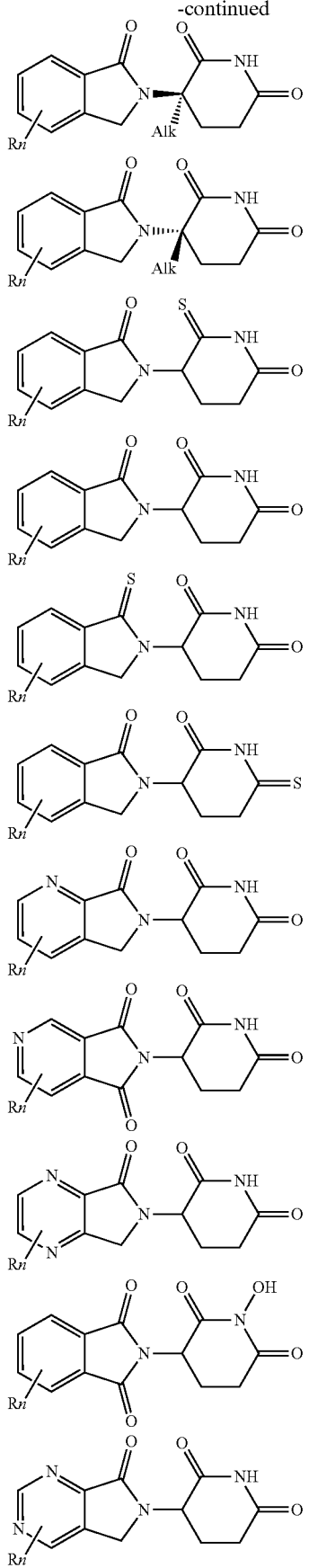
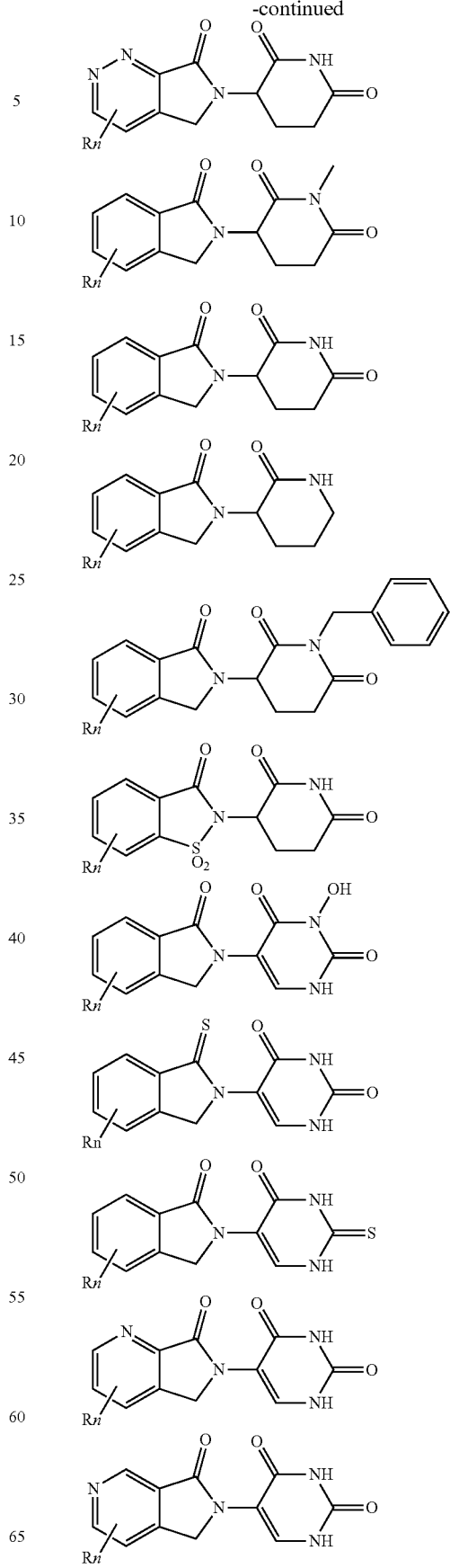

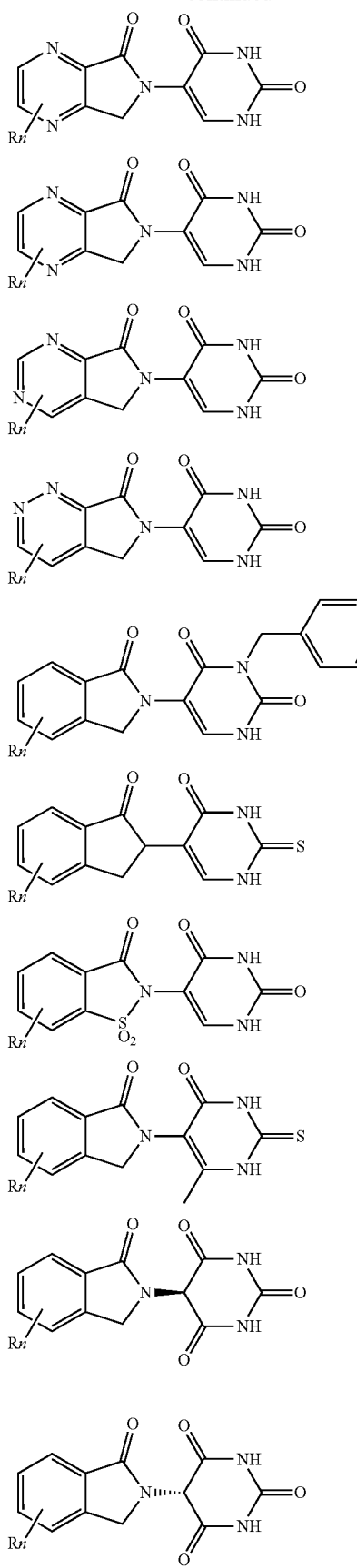
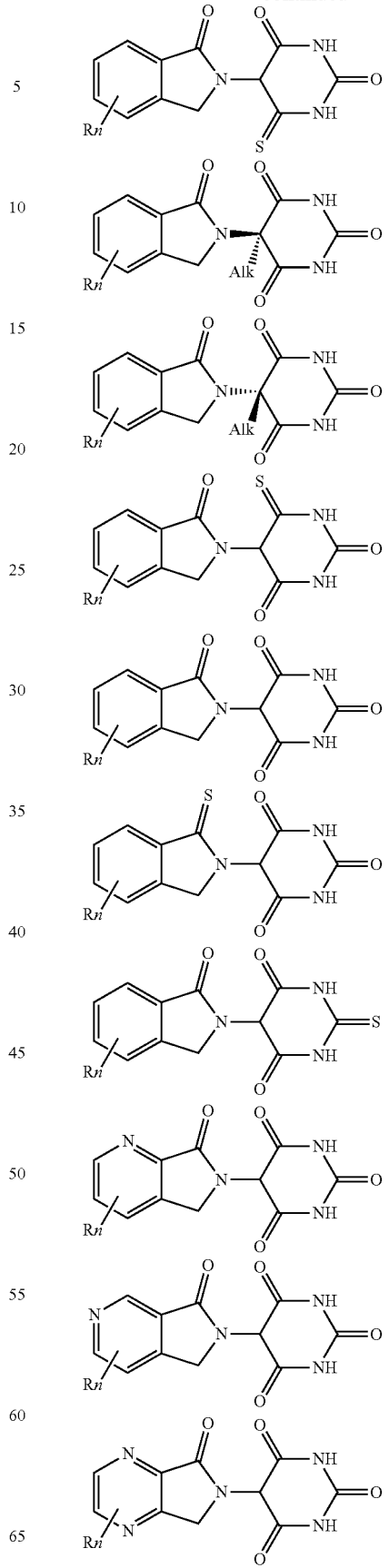

157
-continued
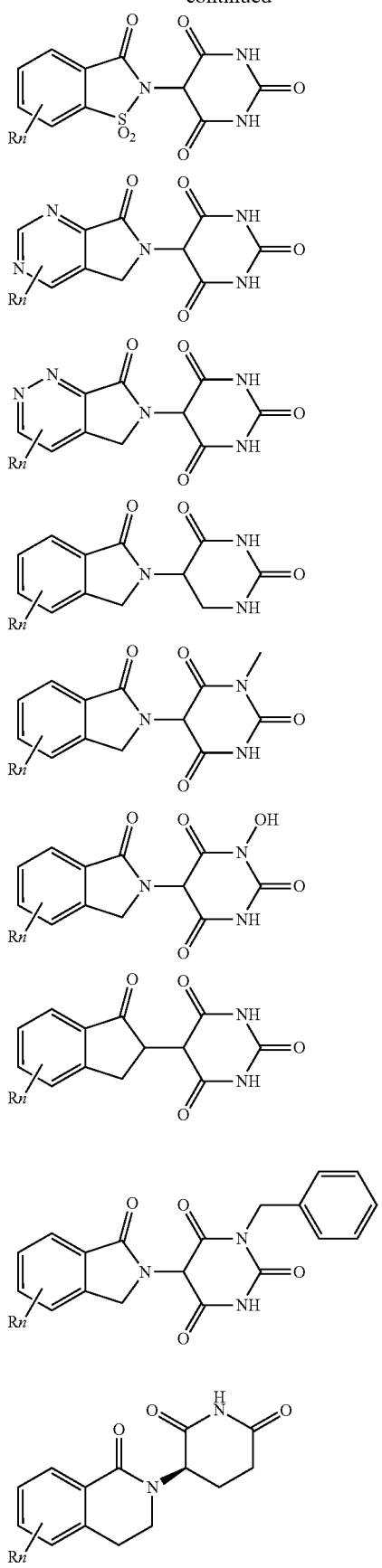
158
-continued
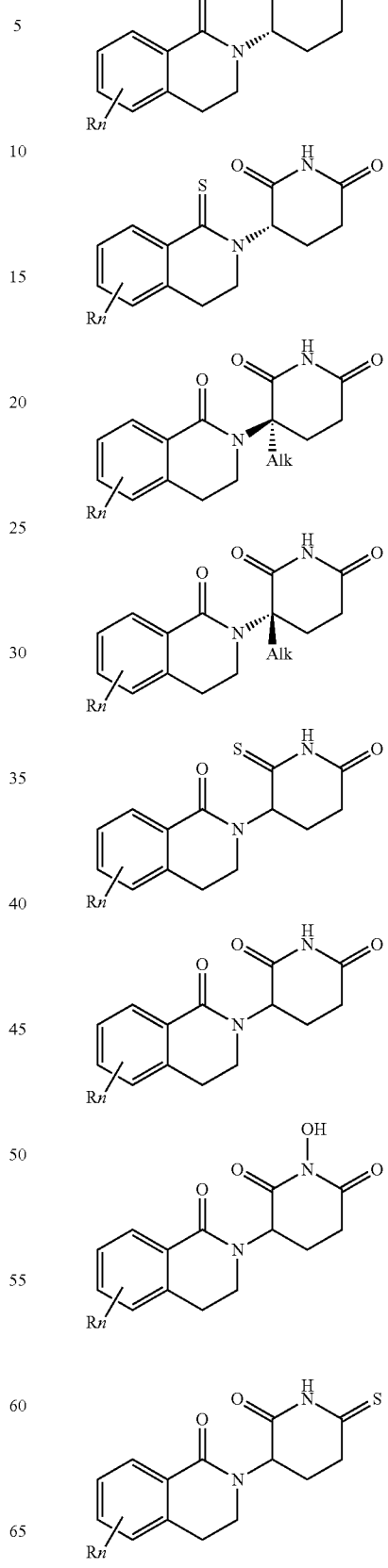

-continued
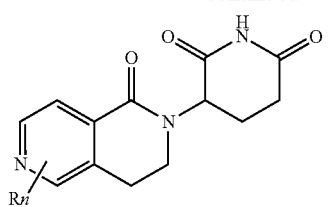
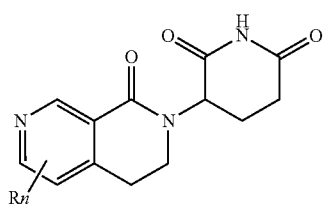
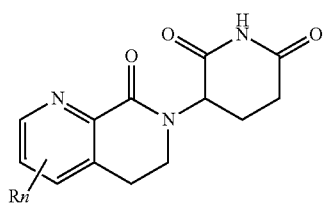
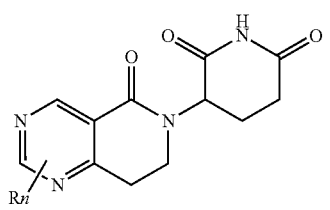
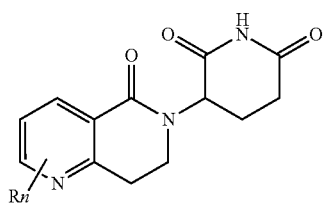
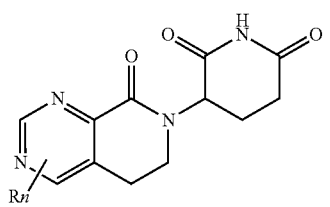
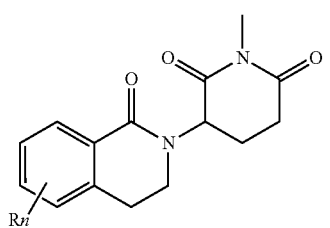
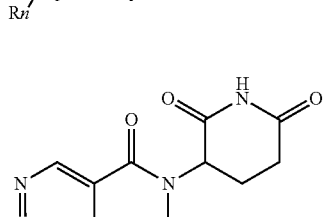
-continued
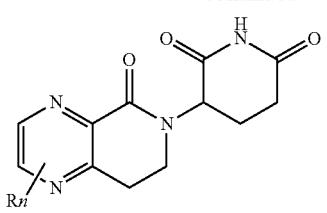
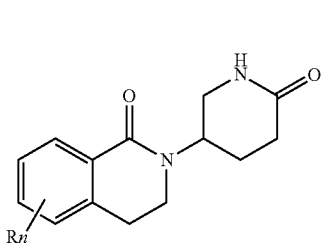
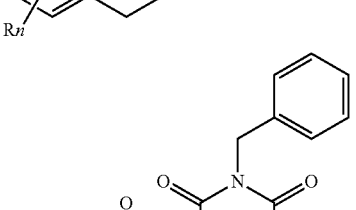
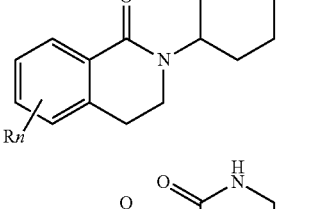
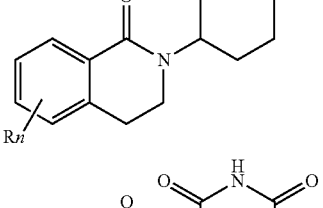
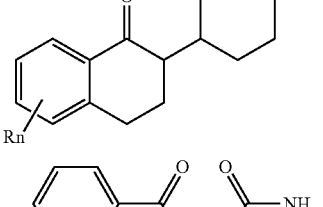
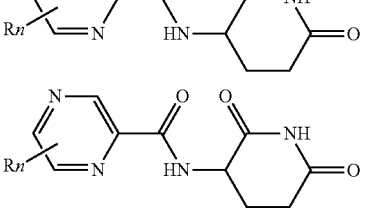
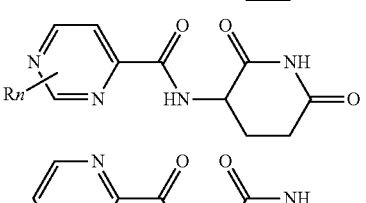

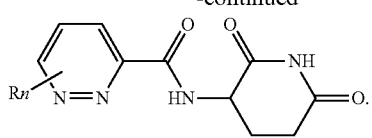
In any of the compounds described herein, the CLM comprises a chemical structure selected from the group:
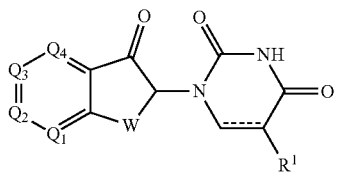
(h)
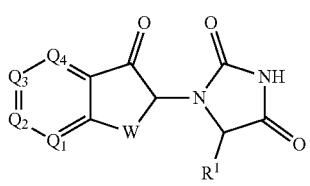
(i)
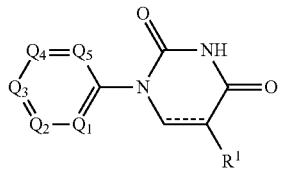
(j)
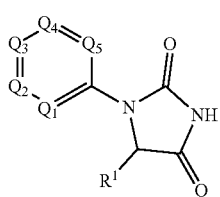
(k)
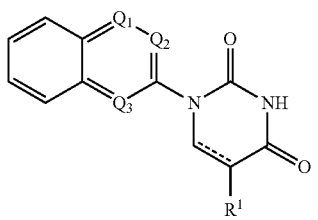
(l)
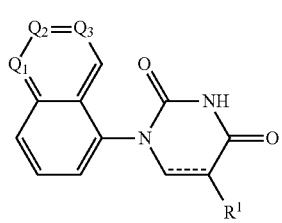
(m)
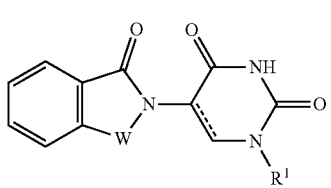
(n)
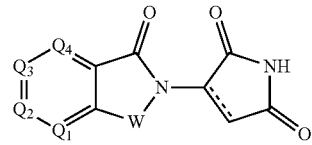
(o)
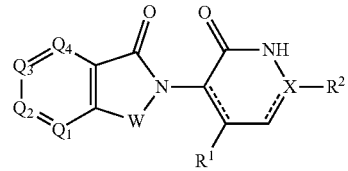
(p)
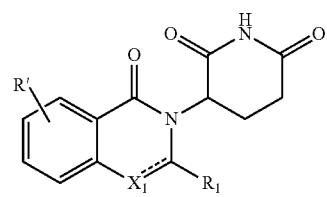
(q)
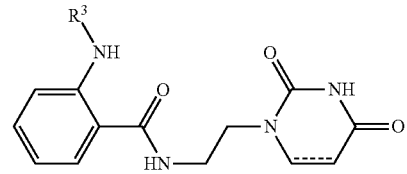
(r)
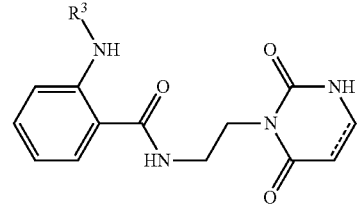
(s)
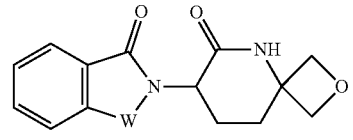
(t)
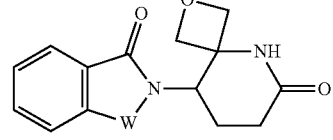
(u)
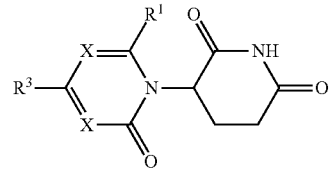
(v)
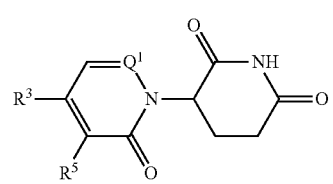
(w)

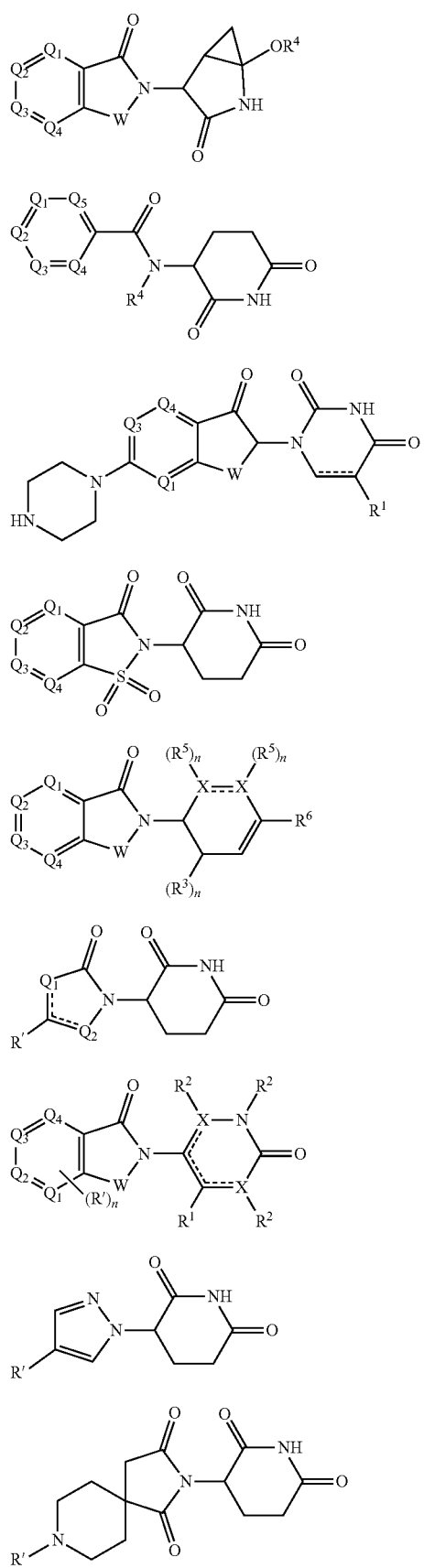
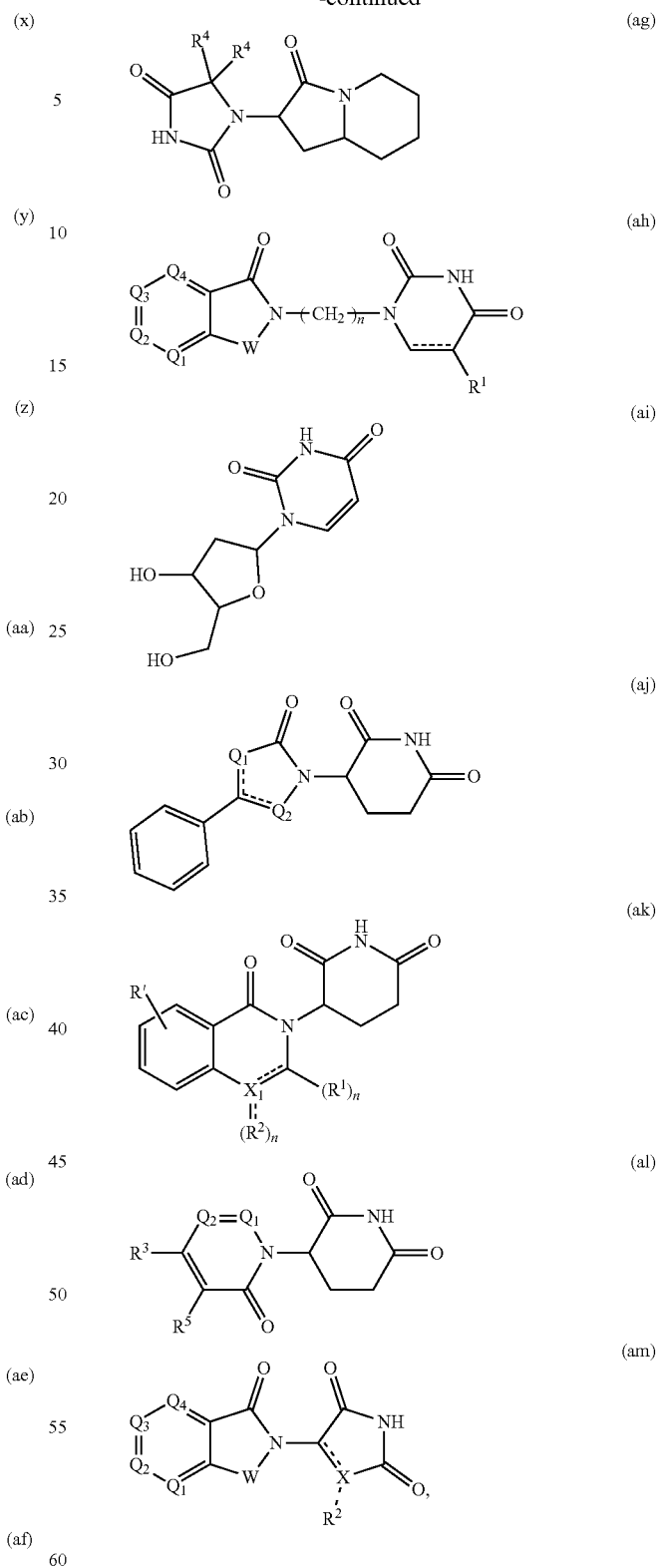
wherein:
W is independently selected from $CH_2$, CHR, C=O, $SO_2$, NH, and N-alkyl;
$Q_1$, $Q_2$, $Q_3$, $Q_4$, $Q_5$ are each independently represent a carbon C or N substituted with a group independently selected from R', N or N-oxide;

$R^1$ is selected from absent, H, OH, CN, C1-C3 alkyl, C=O;
$R^2$ is selected from the group absent, H, OH, CN, $C_1$-$C_3$ alkyl, $CHF_2$, $CF_3$, CHO, C(=O)$NH_2$;
$R^3$ is selected from H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);
$R^4$ is selected from H, alkyl, substituted alkyl;
$R^5$ and $R^6$ are each independently H, halogen, C(=O)R', CN, OH, $CF_3$;
X is C, CH, C=O, or N;
$X_1$ is C=O, N, CH, or $CH_2$;
R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(=O)$OR^2$, optionally substituted phenyl;
n is 0-4;
⫽ is a single or double bond; and
the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$.

In any of the embodiments described herein, the W, X, $R^1$, $R^2$, $R^3$, $R^4$, R', $Q_1$, $Q_2$, $Q_3$, $Q_4$, and $Q_5$ can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

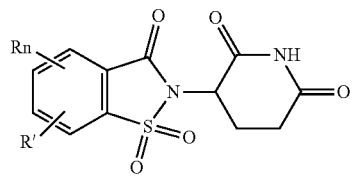

(an)

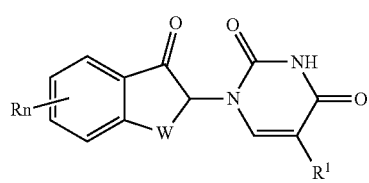

(ao)

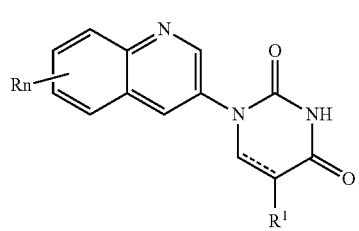

(ap)

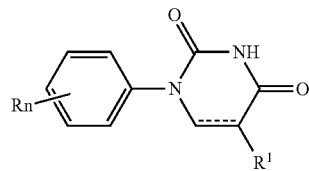

(aq)

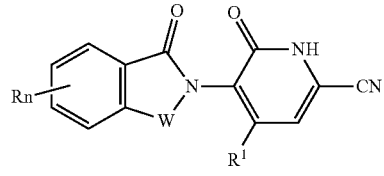

(ar)

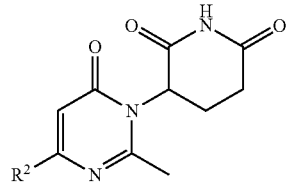

(as)

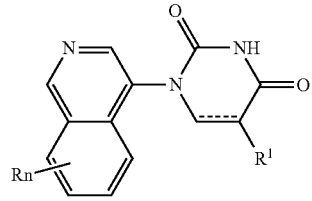

(at)

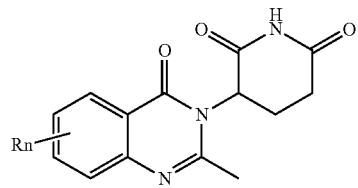

(au)

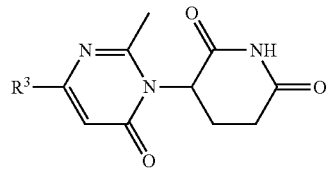

(av)

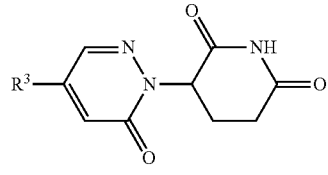

(aw)

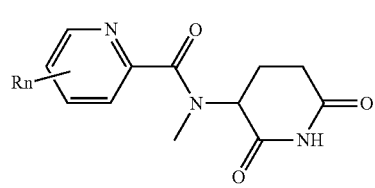

(ax)

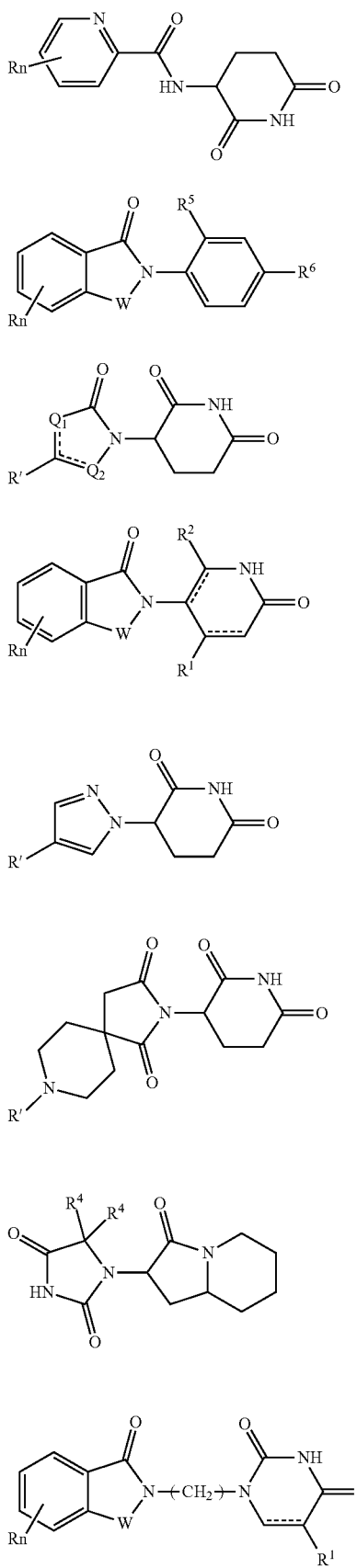

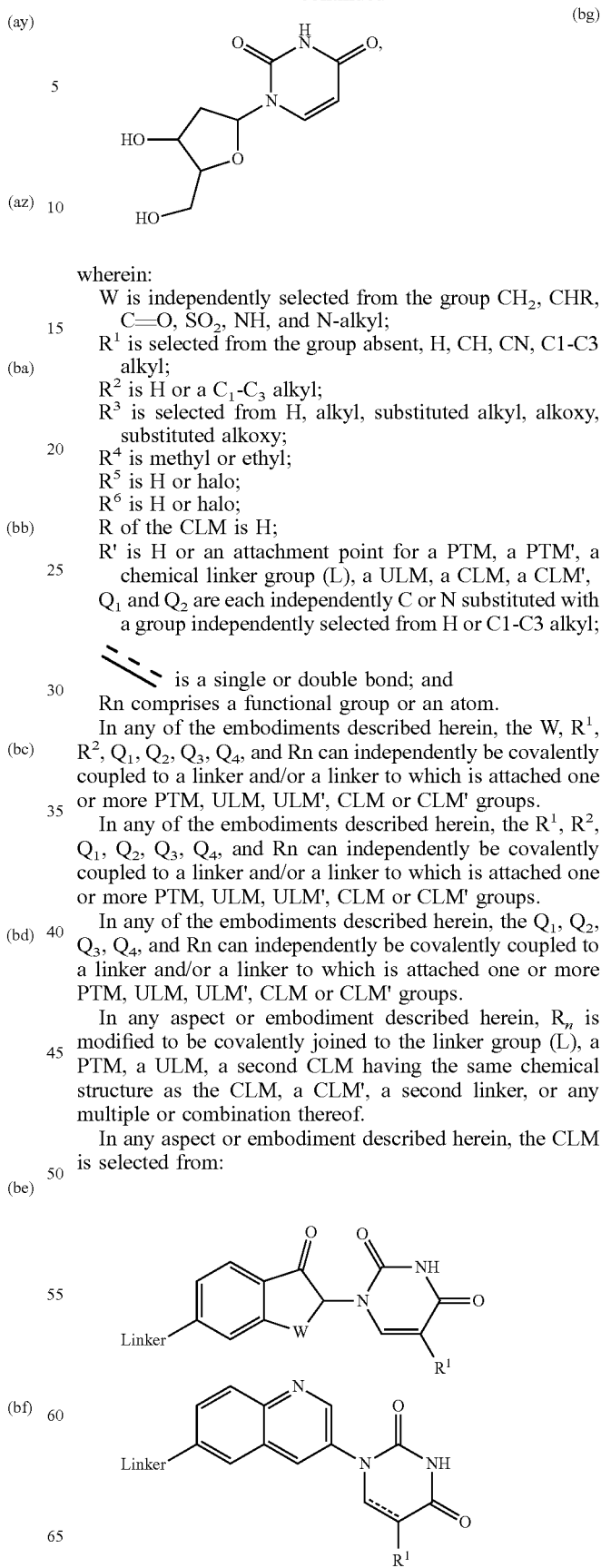

wherein:
W is independently selected from the group CH$_2$, CHR, C=O, SO$_2$, NH, and N-alkyl;
R$^1$ is selected from the group absent, H, CH, CN, C1-C3 alkyl;
R$^2$ is H or a C$_1$-C$_3$ alkyl;
R$^3$ is selected from H, alkyl, substituted alkyl, alkoxy, substituted alkoxy;
R$^4$ is methyl or ethyl;
R$^5$ is H or halo;
R$^6$ is H or halo;
R of the CLM is H;
R' is H or an attachment point for a PTM, a PTM', a chemical linker group (L), a ULM, a CLM, a CLM',
Q$_1$ and Q$_2$ are each independently C or N substituted with a group independently selected from H or C1-C3 alkyl;

is a single or double bond; and
Rn comprises a functional group or an atom.

In any of the embodiments described herein, the W, R$^1$, R$^2$, Q$_1$, Q$_2$, Q$_3$, Q$_4$, and Rn can independently be covalently coupled to a linker and/or a linker to which is attached one or more PTM, ULM, ULM', CLM or CLM' groups.

In any of the embodiments described herein, the R$^1$, R$^2$, Q$_1$, Q$_2$, Q$_3$, Q$_4$, and Rn can independently be covalently coupled to a linker and/or a linker to which is attached one or more PTM, ULM, ULM', CLM or CLM' groups.

In any of the embodiments described herein, the Q$_1$, Q$_2$, Q$_3$, Q$_4$, and Rn can independently be covalently coupled to a linker and/or a linker to which is attached one or more PTM, ULM, ULM', CLM or CLM' groups.

In any aspect or embodiment described herein, R$_n$ is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

169
-continued
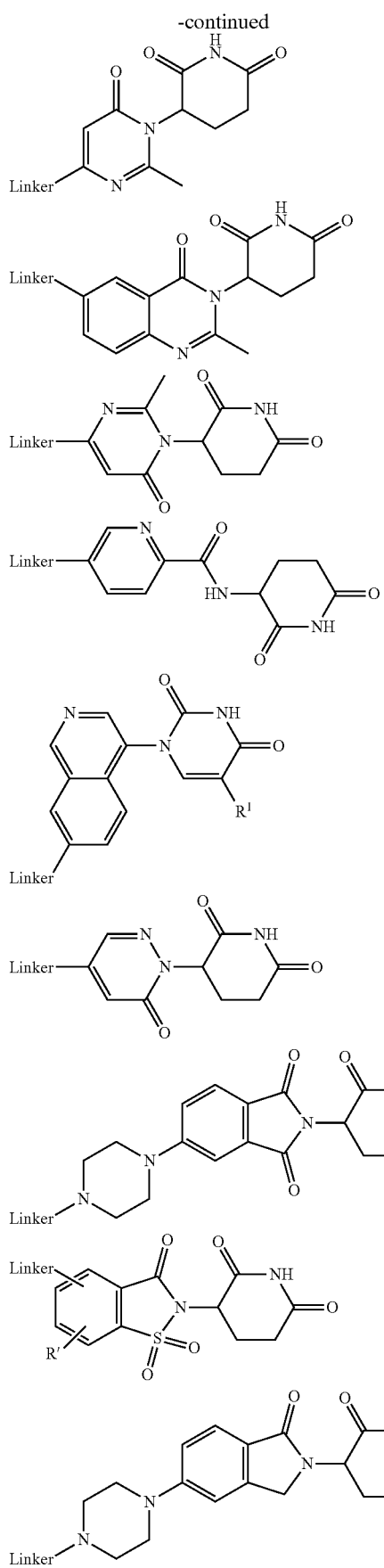
170
-continued
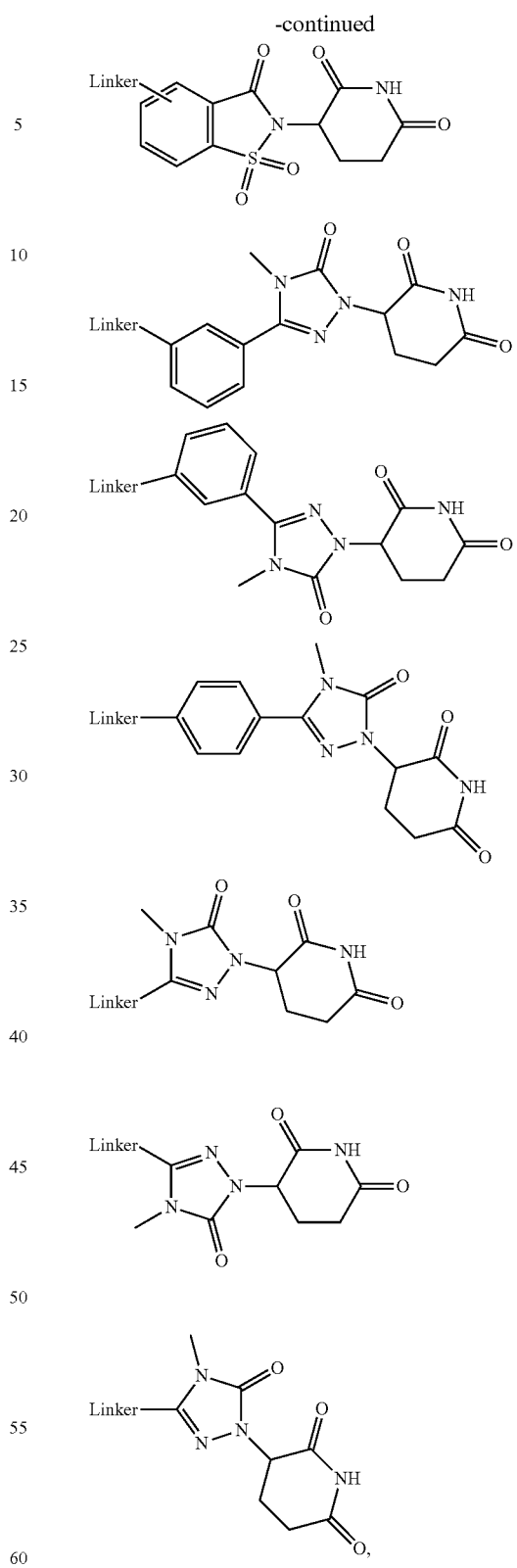
wherein R' is a halogen and $R^1$ is as described in any aspect or embodiment described herein.
In certain cases, "CLM" can be imides that bind to cereblon E3 ligase. These imides and linker attachment point can be, but not limited to, the following structures:

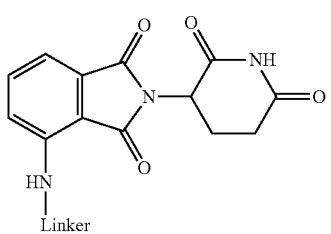
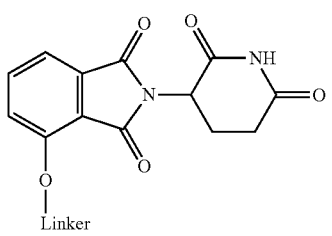
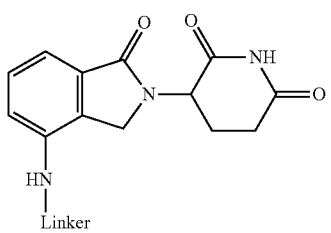
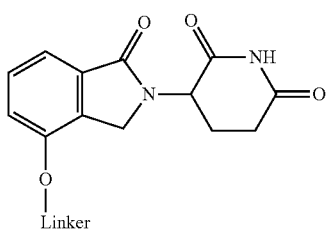
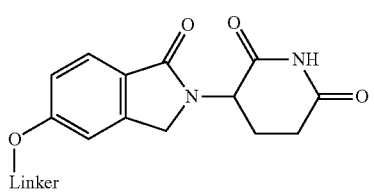
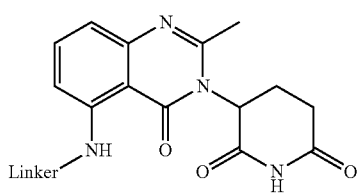
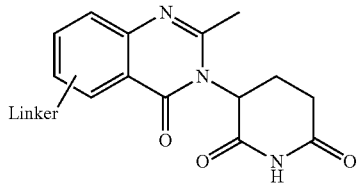
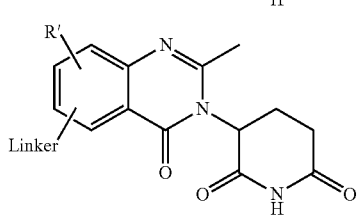

-continued

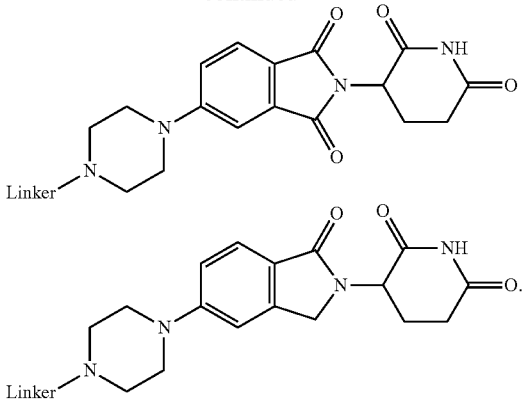

Exemplary VLMs

In certain embodiments of the compounds as described herein, ULM is VLM and comprises a chemical structure selected from the group ULM-a:

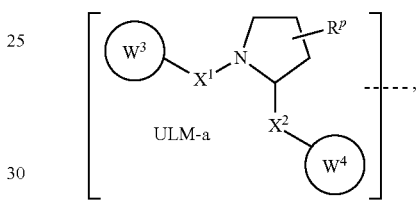

wherein:
  a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;
  $X^1$, $X^2$ of Formula ULM-a are each independently selected from the group of a bond, O, $NR^{Y3}$, $CR^{Y3}R^{Y4}$, C=O, C=S, SO, and $SO_2$;
  $R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3 $R^P$ groups);
  $R^P$ of Formula ULM-a is 0, 1, 2, or 3 groups, each independently selected from the group H, halo, —OH, $C_{1-3}$ alkyl, C=O;
  $W^3$ of Formula ULM-a is selected from the group of an optionally substituted T, an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted T-biheteroaryl, an optionally substituted -T-heterocyclyl, an optionally substituted -T-bi heterocyclyl, an optionally substituted —$NR^1$-T-Aryl, an optionally substituted —$NR^1$-T-Heteroaryl or an optionally substituted —$NR^1$-T-Heterocycle;
  $X^3$ of Formula ULM-a is C=O, $R^1$, $R^{1a}$, $R^{1b}$;
  each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;

T of Formula ULM-a is selected from the group of an optionally substituted alkyl, —(CH$_2$)$_n$— group, wherein each one of the methylene groups is optionally substituted with one or two substituents selected from the group of halogen, methyl, a linear or branched C$_1$-C$_6$ alkyl group optionally substituted by 1 or more halogen, C(O) NR$^1$R$^{1a}$, or NR$^1$R$^{1a}$ or R$^1$ and R$^{1a}$ are joined to form an optionally substituted heterocyclyl, or —OH groups or an amino acid side chain optionally substituted;

W$^4$ of Formula ULM-a is an optionally substituted —NR1-T-Aryl wherein the aryl group may be optionally substituted with an optionally substituted 5-6 membered heteroaryl, an optionally substituted —NR1-T-Heteroaryl group or an optionally substituted —NR1-T-Heterocycle, where —NR1 is covalently bonded to X$^2$ and R$^1$ is H or CH$_3$, preferably H; and n is 0 to 6, often 0, 1, 2, or 3, preferably 0 or 1.

In any of the embodiments described herein, T is selected from the group of an optionally substituted alkyl, —(CH$_2$)$_n$— group, wherein each one of the methylene groups is optionally substituted with one or two substituents selected from the group of halogen, methyl, optionally substituted alkoxy, a linear or branched C$_1$-C$_6$ alkyl group optionally substituted by 1 or more halogen, C(O) NR$^1$R$^{1a}$, or NR$^1$R$^{1a}$ or R$^1$ and R$^{1a}$ are joined to form an optionally substituted heterocycle, or —OH groups or an amino acid side chain optionally substituted; and n is 0 to 6, often 0, 1, 2, or 3, preferably 0 or 1.

In certain embodiments, W$^4$ of Formula ULM-a is

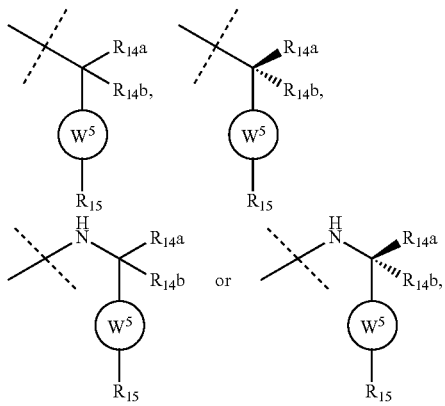

wherein W$^5$ is an optionally substituted phenyl or an optionally substituted 5-10 membered heteroaryl (e.g., optionally substituted with one or more [such as 1, 2, 3, 4, or 5]halo, CN, optionally substituted alkyl, optionally substituted haloalkyl, optionally substituted alkoxy, hydroxy, or optionally substituted haloalkoxy), and R$_{14a}$, R$_{14b}$, are each independently selected from the group of H, haloalkyl, or optionally substituted alkyl.

In any of the embodiments, W$^5$ of Formula ULM-a is selected from the group of an optionally substituted phenyl or an optionally substituted 5-10 membered heteroaryl (e.g., W$^5$ is optionally substituted with one or more [such as 1, 2, 3, 4, or 5]halo, CN, optionally substituted alkyl, optionally substituted haloalkyl, optionally substituted alkoxy, hydroxy, or optionally substituted haloalkoxy), and R$_{15}$ of Formula ULM-a is selected from the group of H, halogen, CN, OH, NO$_2$, NR$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14a}$SO$_2$R$_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

In additional embodiments, W$^4$ substituents for use in the present disclosure also include specifically (and without limitation to the specific compound disclosed) the W$^4$ substituents which are found in the identified compounds disclosed herein. Each of these W$^4$ substituents may be used in conjunction with any number of W$^3$ substituents which are also disclosed herein.

In certain additional embodiments, ULM-a, is optionally substituted by 0-3 R$^p$ groups in the pyrrolidine moiety. Each R$^p$ is independently H, halo, —OH, C1-3alkyl, C═O.

In any of the embodiments described herein, the W$^3$, W$^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

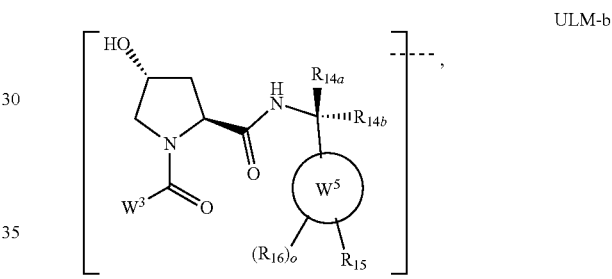

wherein:

W$^3$ of Formula ULM-b is selected from the group of an optionally substituted aryl, optionally substituted heteroaryl, or

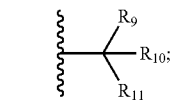

R$_9$ and R$_{10}$ of Formula ULM-b are independently hydrogen, optionally substituted alkyl, optionally substituted cycloalkyl, optionally substituted hydroxyalkyl, optionally substituted heteroaryl, or haloalkyl, or R$_9$, R$_{10}$, and the carbon atom to which they are attached form an optionally substituted cycloalkyl;

R$_{11}$ of Formula ULM-b is selected from the group of an optionally substituted heterocyclic, optionally substituted alkoxy, optionally substituted heteroaryl, optionally substituted aryl,

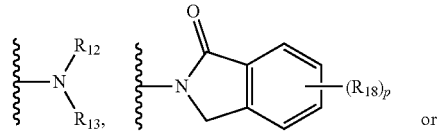

or

-continued

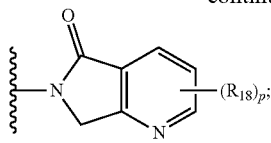

R$_{12}$ of Formula ULM-b is selected from the group of H or optionally substituted alkyl;

R$_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

R$_{14a}$, R$_{14b}$ of Formula ULM-b, are each independently selected from the group of H, haloalkyl, or optionally substituted alkyl;

W$^5$ of Formula ULM-b is selected from the group of an optionally substituted phenyl or an optionally substituted 5-10 membered heteroaryl (e.g., W$^5$ is optionally substituted with one or more [such as 1, 2, 3, 4, or 5]halo, CN, optionally substituted alkyl, optionally substituted haloalkyl, optionally substituted alkoxy, hydroxy, or optionally substituted haloalkoxy), R$_{15}$ of Formula ULM-b is selected from the group of H, halogen, CN, OH, NO$_2$, NR$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14a}$SO$_2$R$_{14b}$, optionally substituted alkyl, optionally substituted haloalkyl, optionally substituted haloalkoxy; aryl, heteroaryl, cycloalkyl, or cycloheteroalkyl (each optionally substituted);

each R$_{16}$ of Formula ULM-b is independently selected from the group of halo, CN, optionally substituted alkyl, optionally substituted haloalkyl, optionally substituted alkoxy, hydroxy, or optionally substituted haloalkoxy;

o of Formula ULM-b is 0, 1, 2, 3, or 4;

R$_{18}$ of Formula ULM-b is independently selected from the group of H, halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, R$_{15}$ of Formula ULM-b is

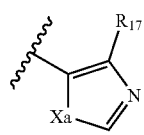

wherein R$_{17}$ is H, halo, optionally substituted C$_{3-6}$cycloalkyl, optionally substituted C$_{1-6}$alkyl, optionally substituted C$_{1-6}$alkenyl, and C$_{1-6}$haloalkyl; and Xa is S or O.

In certain embodiments, R$_{17}$ of Formula ULM-b is selected from the group methyl, ethyl, isopropyl, and cyclopropyl.

In certain additional embodiments, R$_{15}$ of Formula ULM-b is selected from the group consisting of:

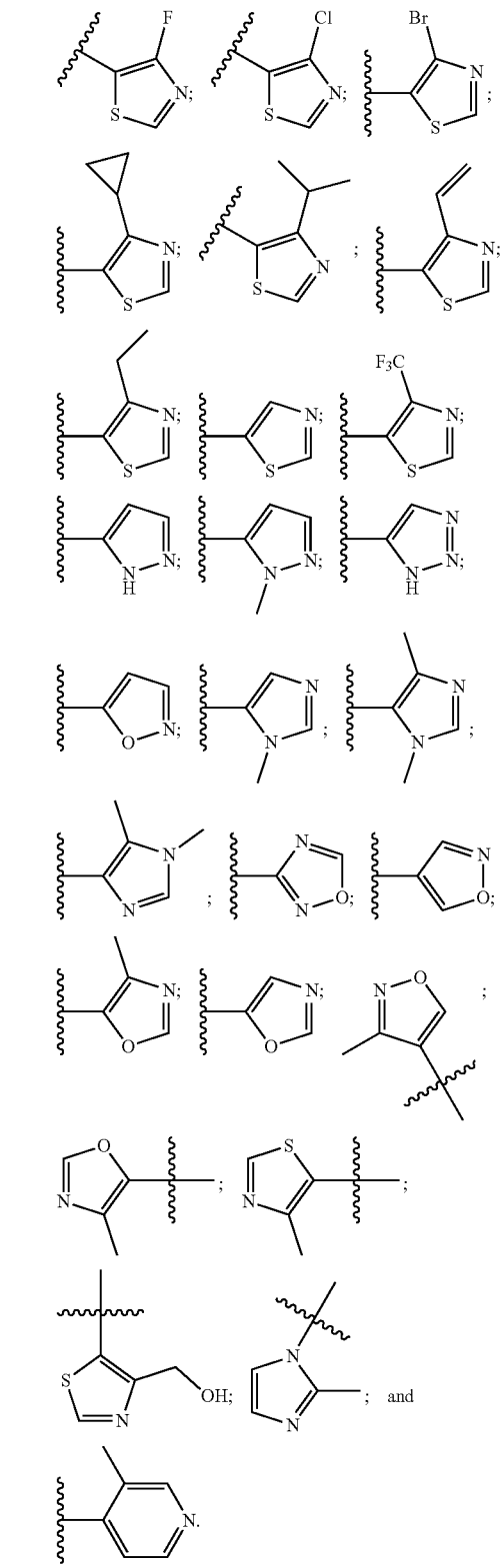

In certain embodiments, R$_{11}$ of Formula ULM-b is selected from the group consisting of:

In certain embodiments, ULM has a chemical structure selected from the group of:

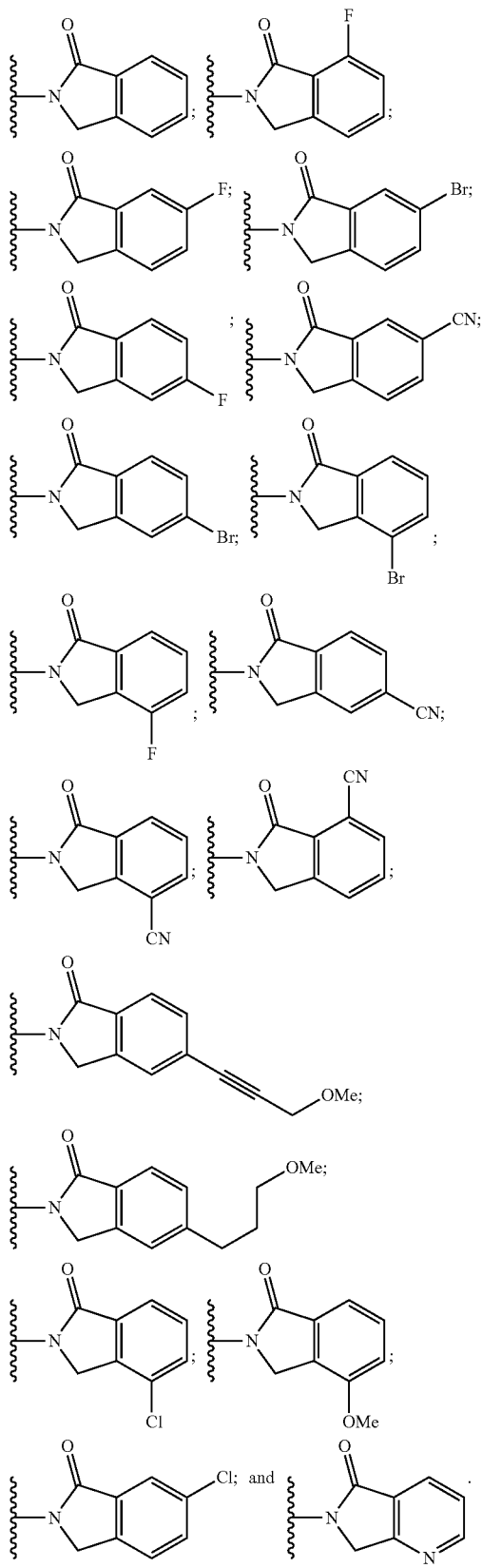

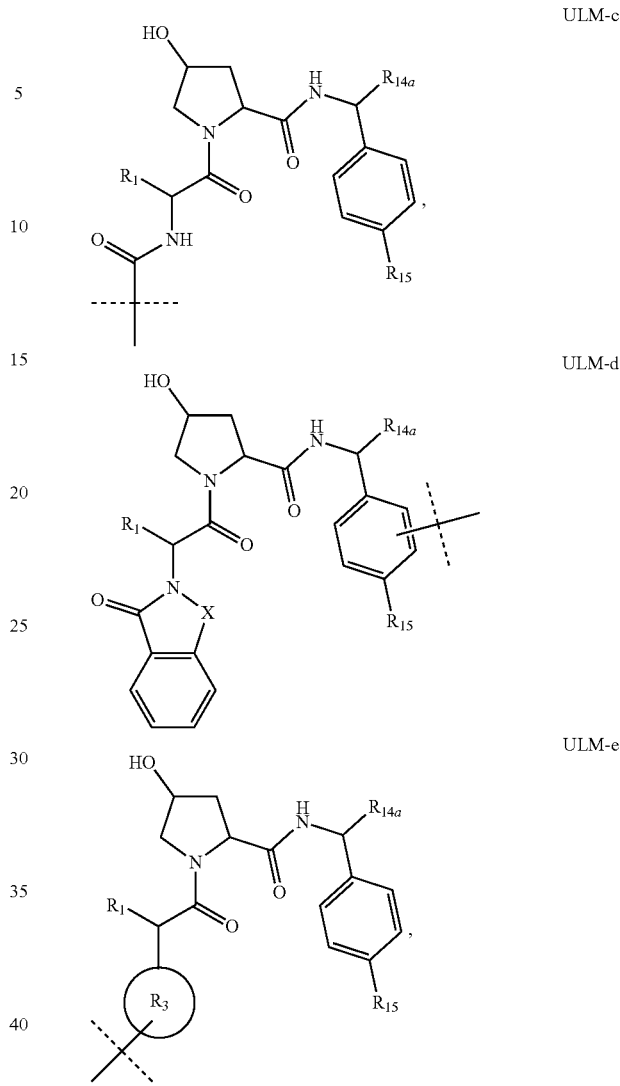

wherein:

R₁ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, OH, $NO_2$, optionally substituted heteroaryl, optionally substituted aryl; optionally substituted alkyl, optionally substituted haloalkyl, optionally substituted optionally substituted haloalkoxy, optionally substituted cycloalkyl, or optionally substituted cycloheteroalkyl;

X of Formulas ULM-c, ULM-d, and ULM-e is C, $CH_2$, or C=O

R₃ of Formulas ULM-c, ULM-d, and ULM-e is absent or an optionally substituted 5 or 6 membered heteroaryl; and the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

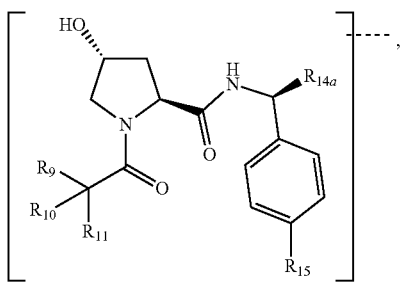

ULM-f wherein:
  $R_{14a}$ of Formula ULM-f is H, haloalkyl, optionally substituted alkyl, methyl, fluoromethyl, hydroxymethyl, ethyl, isopropyl, or cyclopropyl;
  $R_9$ of Formula ULM-f is H;
  $R_{10}$ of Formula ULM-f is H, ethyl, isopropyl, tert-butyl, sec-butyl, cyclopropyl, cyclobutyl, cyclopentyl, or cyclohexyl;
  $R_{11}$ of Formula ULM-f is or optionally substituted heteroaryl;
  p of Formula ULM-f is 0, 1, 2, 3, or 4;
  each $R_{18}$ of Formula ULM-f is independently halo, optionally substituted alkoxy, cyano, optionally substituted alkyl, haloalkyl, haloalkoxy or a linker;
  $R_{12}$ of Formula ULM-f is H, C=O;
  $R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl,
  $R_{15}$ of Formula ULM-f is selected from the group consisting of H, halogen, Cl, CN, OH, $NO_2$, optionally substituted haloalkyl, optionally substituted heteroaryl, optionally substituted aryl;

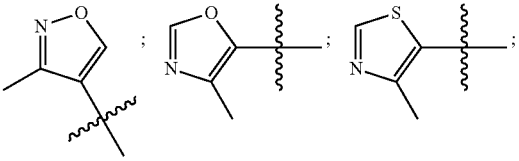

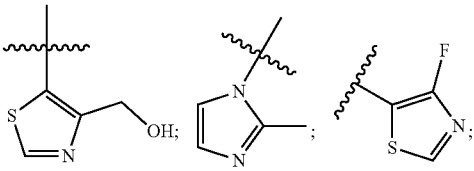

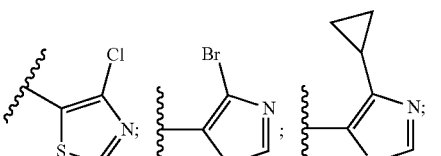

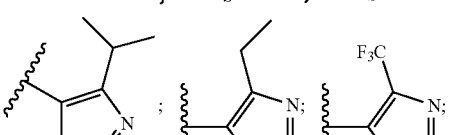

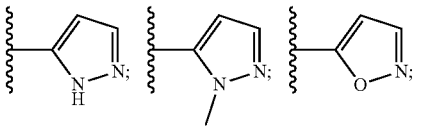

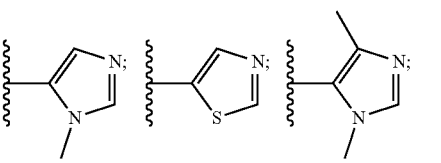

and
  wherein the dashed line of Formula ULM-f indicates the site of attachment of at least one PTM, another ULM (ULM') or a chemical linker moiety coupling at least one PTM or a ULM' or both to ULM.

In certain embodiments, the ULM is selected from the following structures:

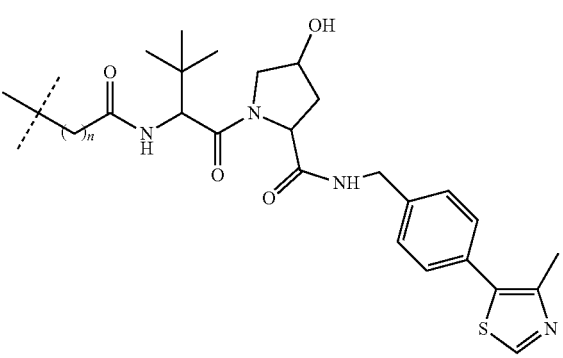

ULM-a2
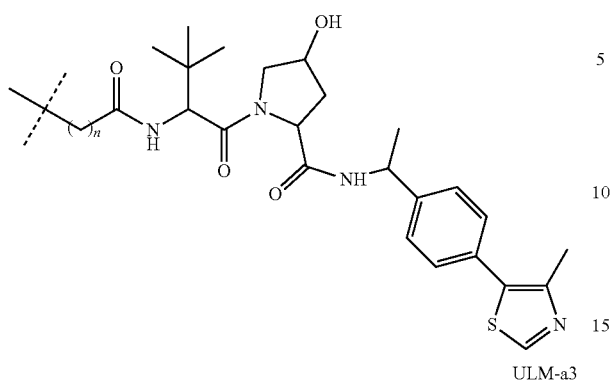
ULM-a6
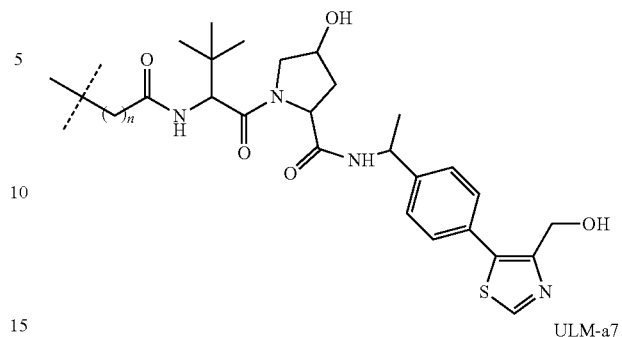
ULM-a3
ULM-a7
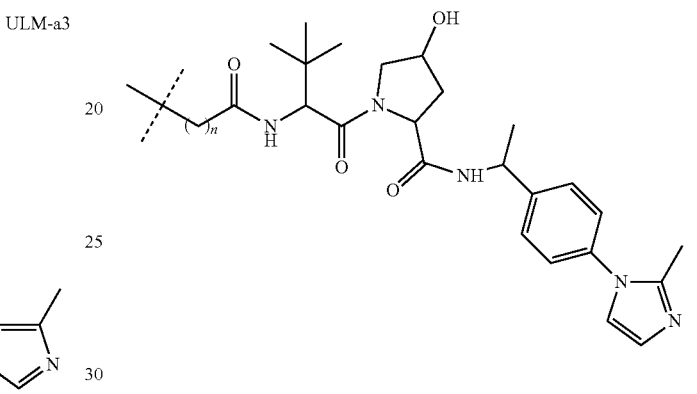
ULM-a4
ULM-a8
ULM-a5
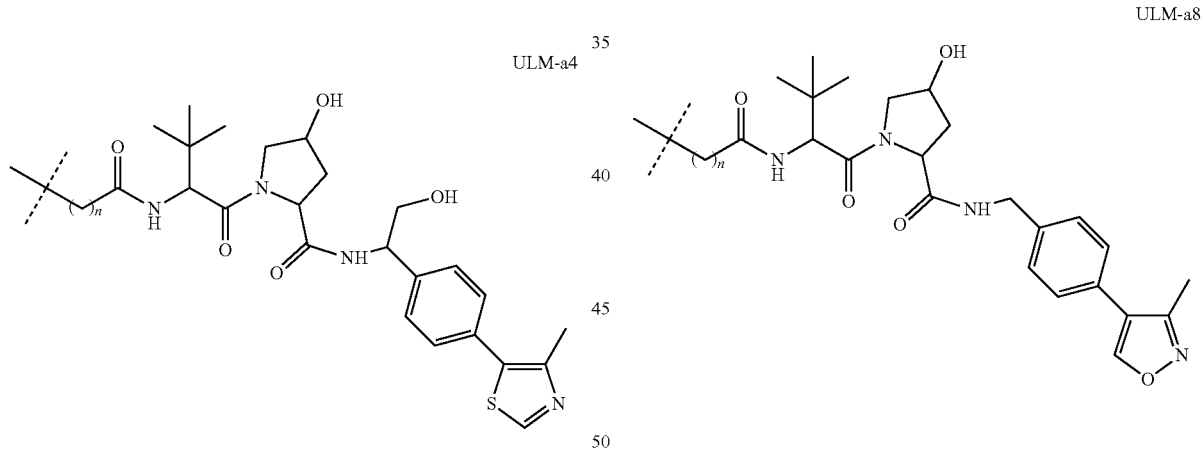
ULM-a9

ULM-a10
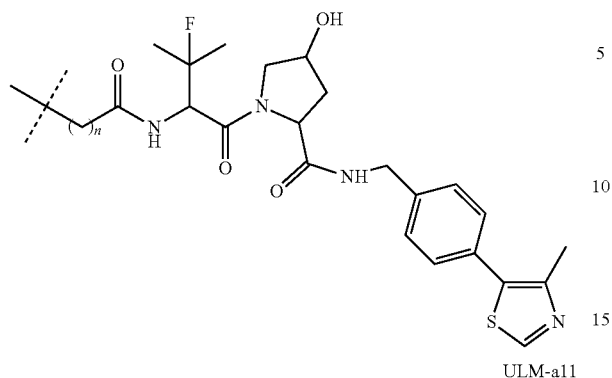
ULM-a11
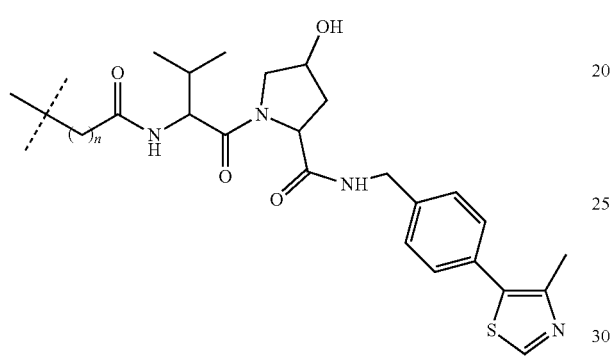
ULM-a12
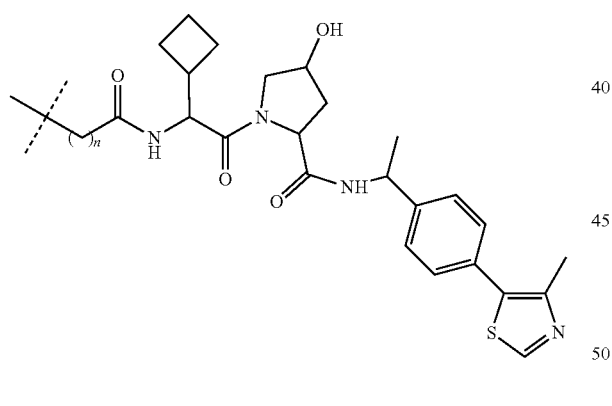
ULM-a13
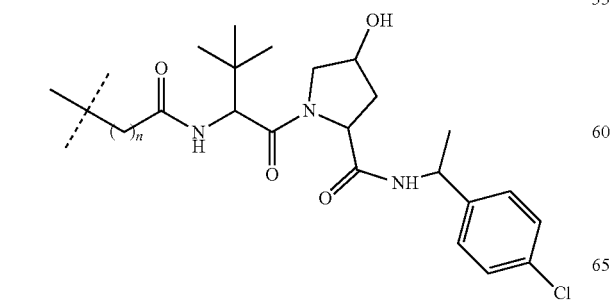
ULM-a14
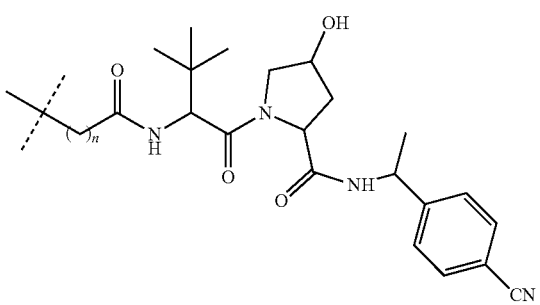
ULM-a15
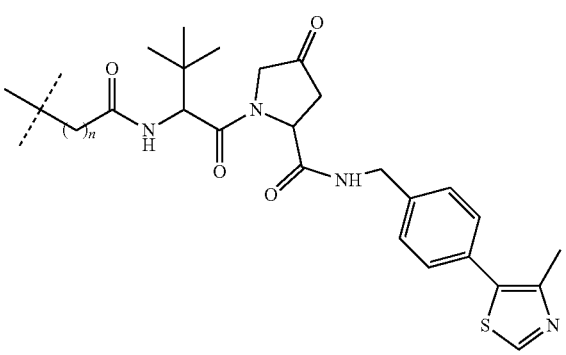
wherein n is 0 or 1.
In certain embodiments, the ULM is selected from the following structures:
ULM-b1
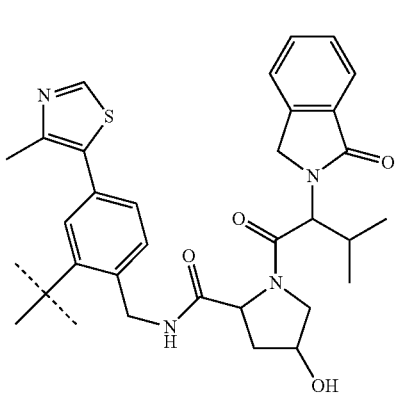
ULM-b2
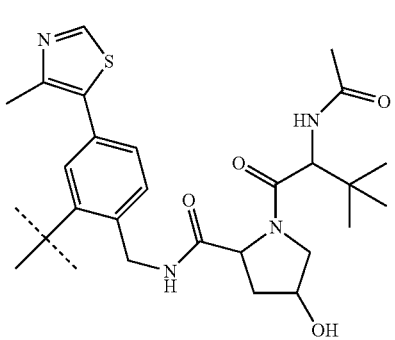

ULM-b3
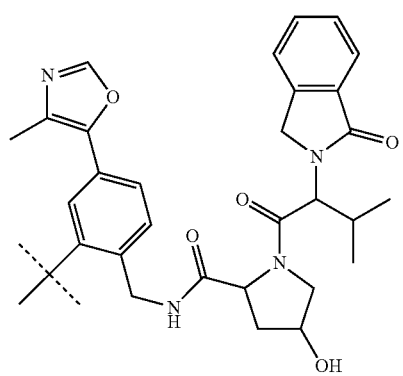
ULM-b7
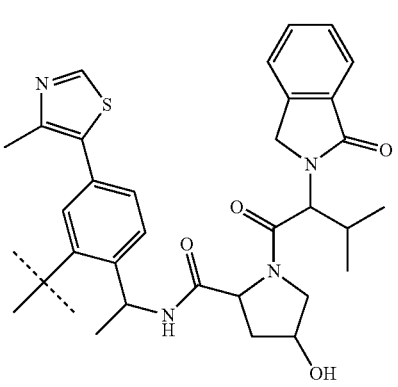
ULM-b4
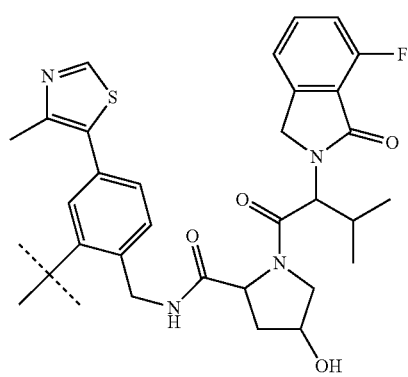
ULM-b8
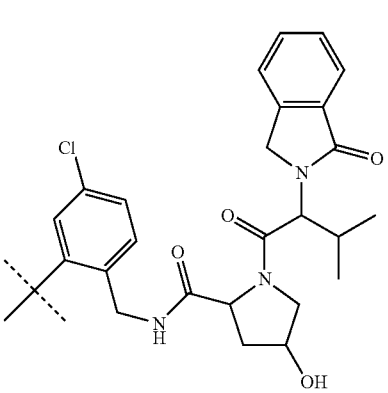
ULM-b5
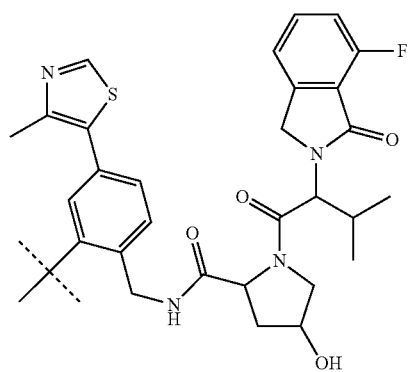
ULM-b9
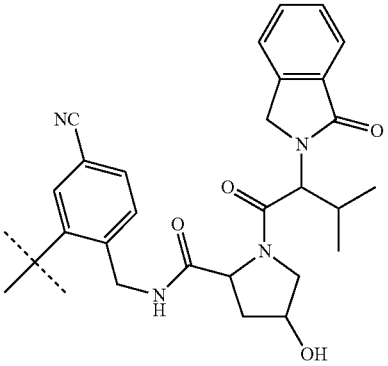
ULM-b6
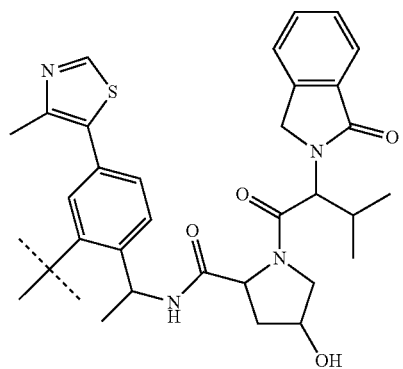
ULM-b10
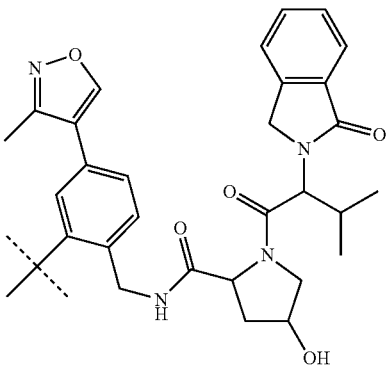

-continued
ULM-b11
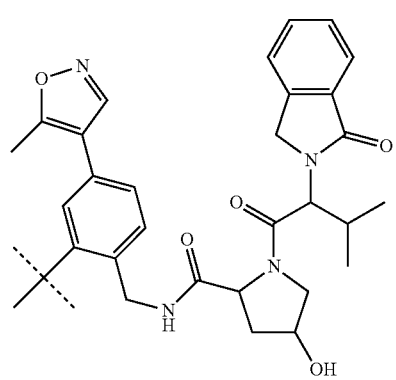
ULM-b12
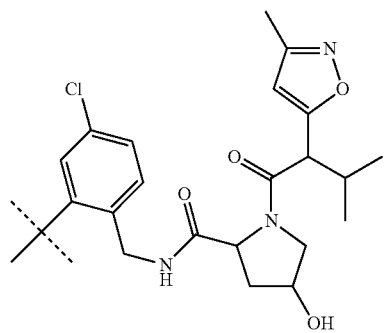
ULM-c1
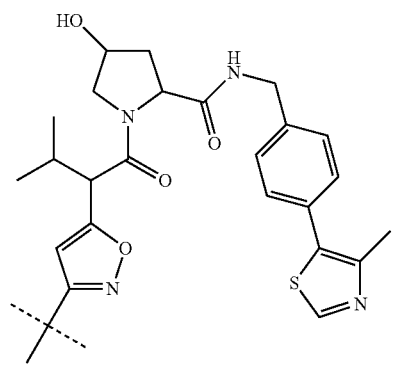
ULM-c2
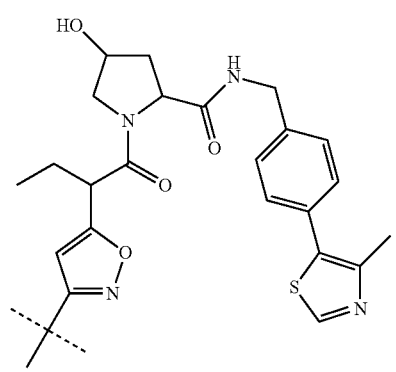
ULM-c3
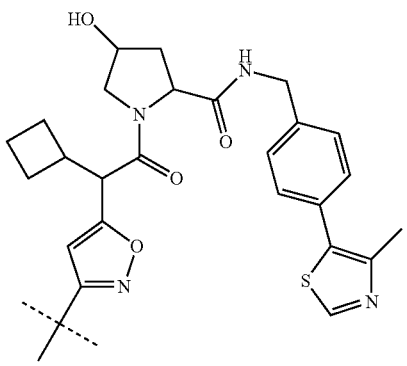
ULM-c4

ULM-c5

ULM-c6
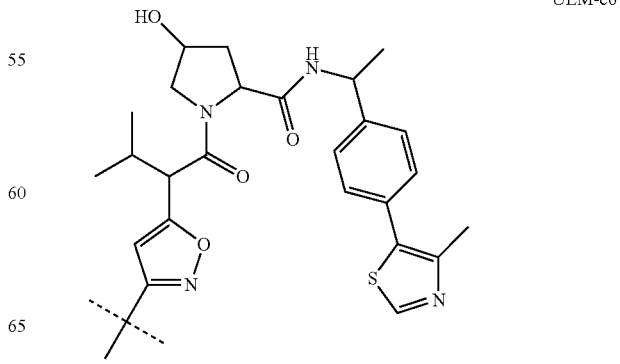

ULM-c7
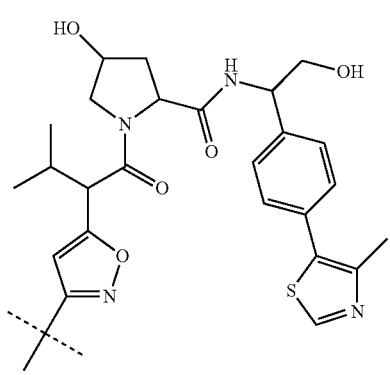
ULM-c8
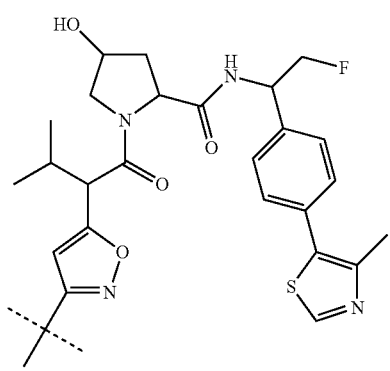
ULM-c9
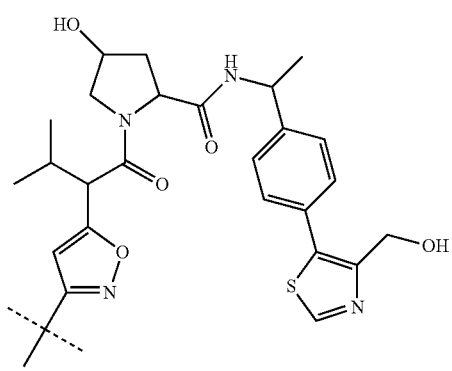
ULM-c10
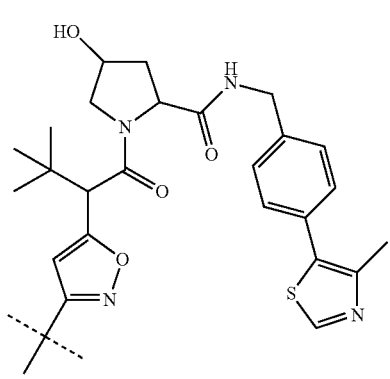
ULM-c11
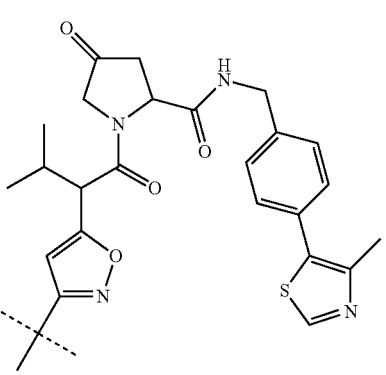
ULM-c12
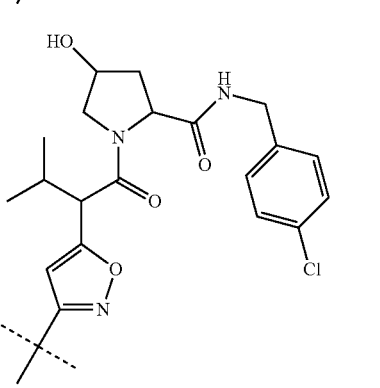
ULM-c13
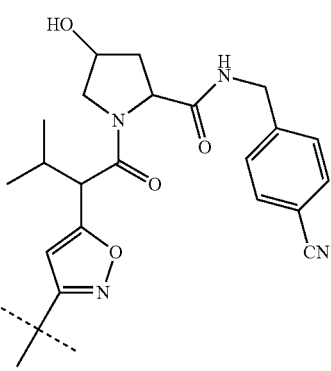
ULM-c14
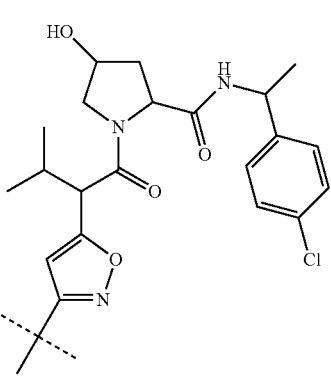

ULM-c15
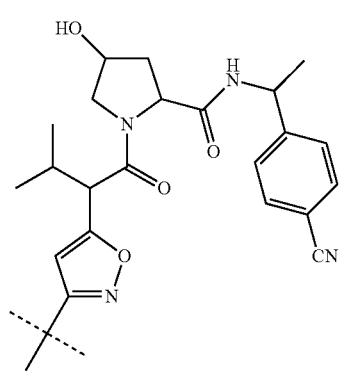
ULM-d4
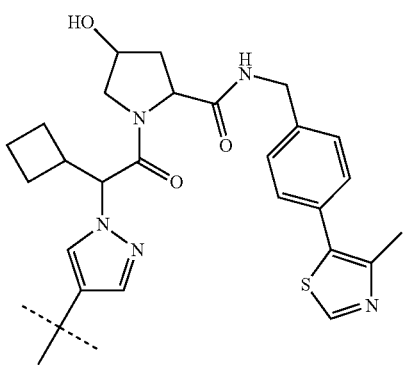
ULM-d1
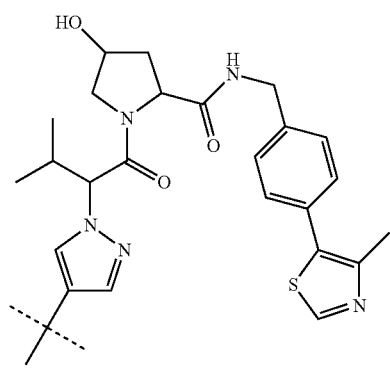
ULM-d5
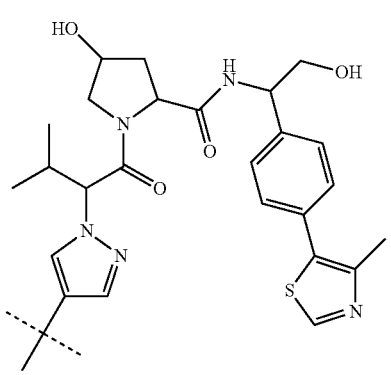
ULM-d2
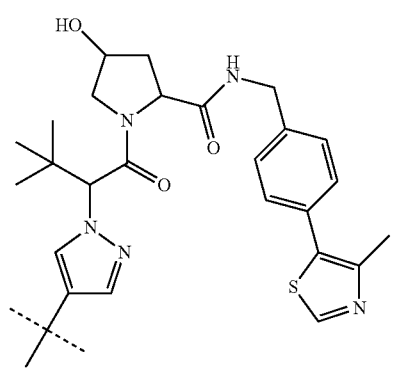
ULM-d6
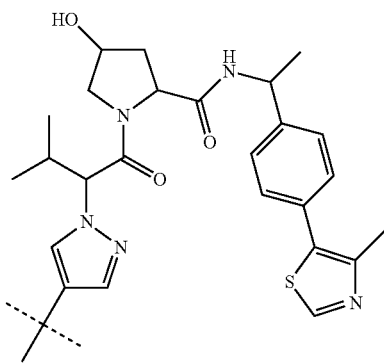
ULM-d3
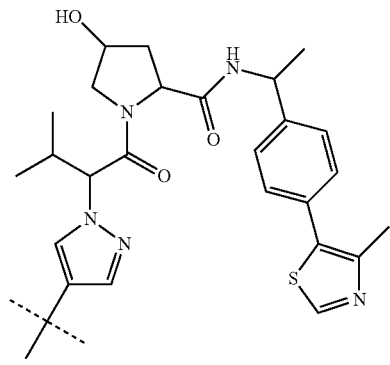
ULM-d7
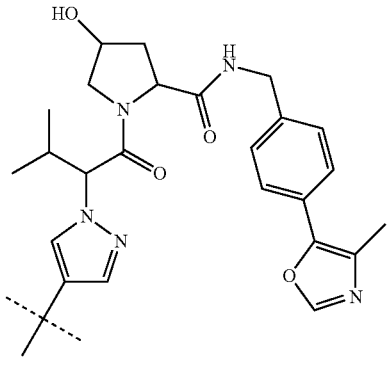

-continued

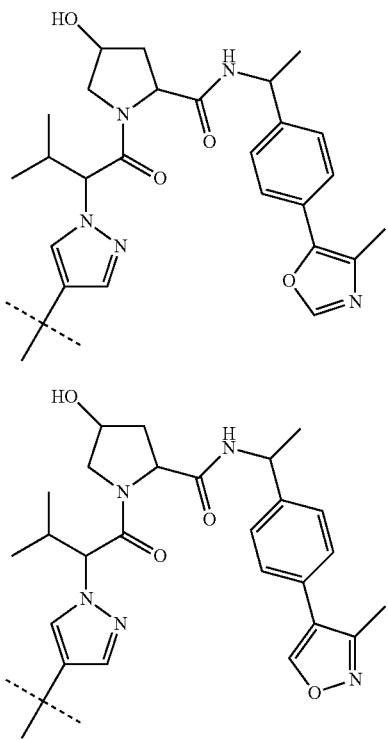

ULM-d8

ULM-d9 wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

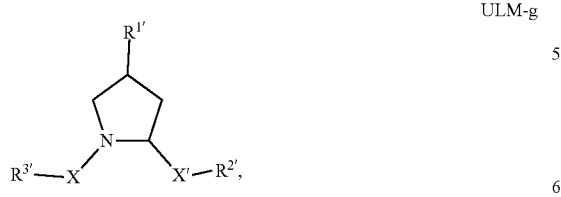

ULM-g or a pharmaceutically acceptable salt thereof, wherein:
$R^1$ of ULM-g is an optionally substituted $C_1$-$C_6$ alkyl group, an optionally substituted —$(CH_2)_n$OH, an optionally substituted —$(CH_2)_n$SH, an optionally substituted $(CH_2)_n$—O—($C_1$-$C_6$)alkyl group, an optionally substituted $(CH_2)_n$—WCOCW—($C_0$-$C_6$)alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—(C1-$C_6$ alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—($C_1$-$C_6$ alkyl), an optionally substituted —$(CH_2)_n$C(O)—O—($C_1$-$C_6$ alkyl), an optionally substituted —$(CH_2O)_n$COOH, an optionally substituted —$(OCH_2)_n$O—($C_1$-$C_6$ alkyl), an optionally substituted —$(CH_2O)_n$C(O)—($C_1$-$C_6$ alkyl), an optionally substituted —$(OCH_2)_n$NHC(O)—$R_1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—($C_1$-$C_6$ alkyl), an optionally substituted —$(CH_2CH_2O)_n$C(O)—($C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a —$(CH_2)_m NR_1R_2$ group;

X and X' of ULM-g are each independently C=O, C=S, —S(O), $S(O)_2$, (preferably X and X' are both C=O);

$R^{2'}$ of ULM-g is an optionally substituted —$(CH2)_n$—(C=O)_u(NR_1)_v(SO_2)_w$alkyl group, an optionally substituted —$(CH_2)_n$—(C=O)_u(NR_1)_v(SO_2)_w$—$NR_{1N}R_{2N}$ group, an optionally substituted —$(CH_2)_n$—(C=O)_u(NR_1)_v(SO_2)_w$-Aryl, an optionally substituted —$(CH_2)_n$—(C=O)_u(NR_1)_v(SO_2)_w$-Heteroaryl, an optionally substituted —$(CH_2)$—(C=O)_v NR_1(SO_2)_w$-Heterocycle, an optionally substituted —$NR^1$—$(CH_2)_n$—C(O)_u(NR_1)_v(SO_2)_w$-alkyl, an optionally substituted —$NR^1$—$(CH_2)$—C(O)_u(NR_1)_v(SO_2)_w$—$NR_{1N}R_{2N}$, an optionally substituted —$NR^1$—$(CH_2)_n$—C(O)_u(NR_1)_v(SO_2)_w$—$NR_1C(O)R_{1N}$, an optionally substituted —$NR^1$—$(CH_2)_n$—(C=O)_u(NR_1)_v(SO_2)_w$-Aryl, an optionally substituted —$NR^1$—$(CH_2)_n$-Aryl-Heteroaryl, an optionally substituted —$NR_1$—$(CH_2)_n$—(C=O)_u(NR_1)_v(SO_2)_w$-Heteroaryl or an optionally substituted —$NR^1$—$(CH_2)$—(C=O)_v NR_1(SO_2)_w$-Heterocycle, an optionally substituted —$X^{R2'}$-alkyl group; an optionally substituted —$X^{R2'}$-Aryl group; an optionally substituted —$X^{R2'}$-Heteroaryl group; an optionally substituted —$X^{R2'}$-Heterocycle group; an optionally substituted;

$R^{3'}$ of ULM-g is an optionally substituted alkyl, an optionally substituted —$(CH_2)_n$—(O)_u(NR_1)_v(SO_2)_w$-alkyl, an optionally substituted —$(CH_2)_n$—C(O)_u(NR_1)_v(SO_2)_w$—$NR_{1N}R_{2N}$, an optionally substituted —$(CH_2)_n$—C(O)_u(NR_1)_v(SO_2)_w$—$NR_1C(O)R_{1N}$, an optionally substituted —$(CH_2)_n$—C(O)_u(NR_1)_v(SO_2)_w$—C(O)NR_1R_2$, an optionally substituted —$(CH_2)_n$—C(O)_u(NR_1)_v(SO_2)_w$-Aryl, an optionally substituted —$(CH_2)_n$—C(O)_u(NR_1)_v(SO_2)_w$-Heteroaryl, an optionally substituted —$(CH_2)$—C(O)_u(NR_1)_v(SO_2)_w$-Heterocycle, an optionally substituted —$NR^1$—$(CH_2)_n$—C(O)_u(NR_1)_v(SO_2)_w$-alkyl, an optionally substituted —$NR^1$—$(CH_2)_n$—C(O)_u(NR_1)_v $(SO_2)_w$— $NR_{1N}R_{2N}$, an optionally substituted —$NR^1$—$(CH_2)_n$—$C(O)_u(NR_1)_v(SO_2)_w$—$NR_1C(O)$ $R_{1N}$, an optionally substituted —$NR^1$—$(CH_2)_n$ —$C(O)_u(NR_1)_v(SO_2)_w$-Aryl, an optionally substituted —$NR^1$—$(CH_2)$—$C(O)_u(NR_1)_v(SO_2)_w$-Heteroaryl, an optionally substituted —$NR^1$—$(CH_2)_n$—$C(O)_u(NR_1)_v$ $(SO_2)_w$-Heterocycle, an optionally substituted —O— $(CH_2)_n$—$(C=O)_u(NR_1)_v(SO_2)_w$-alkyl, an optionally substituted —O—$(CH_2)$n-$(C=O)_u(NR_1)_v(SO_2)_w$— $NR_{1N}R_{2N}$, an optionally substituted —O—$(CH_2)$n- $(C=O)_u(NR_1)_v(SO_2)_w$—$NR_1C(O)R_{1N}$, an optionally substituted —O—$(CH_2)$n-$(C=O)_u(NR_1)_v(SO_2)_w$- Aryl, an optionally substituted —O—$(CH_2)_n$ —$(C=O)_u(NR_1)_v(SO_2)_w$-Heteroaryl or an optionally substituted —O—$(CH_2)$—$(C=O)_u(NR_1)_v(SO_2)_w$-Heterocycle; —$(CH_2)_n$—$(V)_{n'}$—$(CH_2)_n$—$(V)_{n'}$-alkyl group, an optionally substituted —$(CH_2)_n$—$(V)_{n'}$— $(CH_2)_n$—$(V)_{n'}$-Aryl group, an optionally substituted —$(CH_2)_n$—$(V)_{n'}$—$(CH_2)_n$—$(V)_{n'}$-Heteroaryl group, an optionally substituted —$(CH_2)_n$—$(V)_{n'}$—$(CH_2)_n$— $(V)_{n'}$-Heterocycle group, an optionally substituted —$(CH_2)_n$—$N(R_{1'})(C=O)_{m'}$—$(V)_{n'}$-alkyl group, an optionally substituted —$(CH_2)_n$—$N(R_{1'})(C=O)_{m'}$— $(V)_{n'}$-Aryl group, an optionally substituted —$(CH_2)_n$— $N(R_{1'})(C=O)_{m'}$—$(V)_{n'}$-Heteroaryl group, an optionally substituted —$(CH_2)_n$—$N(R_{1'})(C=O)_{m'}$—$(V)_{n'}$- Heterocycle group, an optionally substituted —$X^{R3'}$- alkyl group; an optionally substituted —$X^{R3'}$-Aryl group; an optionally substituted —$X^{R3'}$-Heteroaryl group; an optionally substituted —$X^{R3'}$-Heterocycle group;

$R_{1N}$ and $R_{2N}$ of ULM-g are each independently H, $C_1$-$C_6$ alkyl which is optionally substituted with one or two hydroxyl groups and up to three halogen groups or an optionally substituted —$(CH_2)_n$-Aryl, —$(CH_2)_n$-Heteroaryl or —$(CH_2)_n$-Heterocycle group;

V of ULM-g is O, S or $NR_1$;

$R_1$ of ULM-g is the same as above;

$R^1$ and $R_{1'}$ of ULM-g are each independently H or a $C_1$-$C_3$ alkyl group;

$X^{R2'}$ and $X^{R3'}$ of ULM-g are each independently an optionally substituted —$(CH_2)_n$—, —$(CH_2)_n$—CH $(X_v)$=$CH(X_v)$-(cis or trans), —$(CH_2)_n$—CH=CH—, —$(CH_2CH_2O)_n$— or a $C_3$-$C_6$ cycloalkyl group, where $X_v$ is H, a halo or a $C_1$-$C_3$ alkyl group which is optionally substituted;

each m of ULM-g is independently 0, 1, 2, 3, 4, 5, 6;
each m' of ULM-g is independently 0 or 1;
each n of ULM-g is independently 0, 1, 2, 3, 4, 5, 6;
each n' of ULM-g is independently 0 or 1;
each u of ULM-g is independently 0 or 1;
each v of ULM-g is independently 0 or 1;
each w of ULM-g is independently 0 or 1; and any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

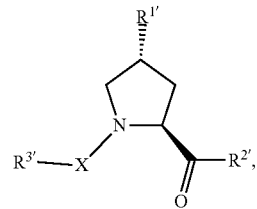

ULM-h wherein:
each of $R^{1'}$, $R^{2'}$ and $R^{3'}$ of ULM-h are the same as above and X is C=O, C=S, —S(O) group or a $S(O)_2$ group, more preferably a C=O group, and
any one or more of $R^{1'}$, $R^{2'}$ and $R^{3'}$ of ULM-h are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or
a pharmaceutically acceptable salt, enantiomer, diastereomer, solvate or polymorph thereof.

In any of the aspects or embodiments described herein, the ULM, and when present, ULM', are each independently according to the chemical structure:

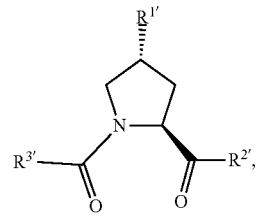

ULM-i wherein:
any one or more of $R^{1'}$, $R^{2'}$ and $R^{3'}$ of ULM-I are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or
a pharmaceutically acceptable salt, enantiomer, diastereomer, solvate or polymorph thereof.

In further preferred aspects of the disclosure, $R^{1'}$ of ULM-g through ULM-i is preferably a hydroxyl group or a group which may be metabolized to a hydroxyl or carboxylic group, such that the compound represents a prodrug form of an active compound. Exemplary preferred $R^{1'}$ groups include, for example, —$(CH_2)_n$OH, $(CH_2)_n$—O— $(C_1$-$C_6)$alkyl group, —$(CH_2)_n$COOH, —$(CH_2O)_n$H, an optionally substituted —$(CH_2)_n$OC(O)—$(C_1$-$C_6$ alkyl), or an optionally substituted —$(CH_2)_n$C(O)—O—$(C_1$-$C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a $S(O)_2$ group, more preferably a C=O group;

R[2'] of ULM-g through ULM-i is preferably an optionally substituted —NR[1]-T-Aryl (e.g., an optionally substituted NH-T-aryl or an optionally substituted N(CH$_3$)-T-aryl), an optionally substituted —NR[1]-T-Heteroaryl group (e.g., an optionally substituted NH-T-heteroaryl or an optionally substituted N(CH$_3$)-T-heteroaryl), or an optionally substituted —NR[1]-T-heterocylcl (e.g., an optionally substituted NH-T-heterocylcl or an optionally substituted N(CH$_3$)-T-heterocylcl), where R[1] is H or CH$_3$, preferably H and T is an optionally substituted —(CH$_2$)$_n$— group, wherein each one of the methylene groups may be optionally substituted with one or two substituents, preferably selected from halogen, an amino acid sidechain as otherwise described herein or a C$_1$-C$_3$ alkyl group, preferably one or two methyl groups, which may be optionally substituted; and n is 0 to 6, often 0, 1, 2 or 3, preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, all of which groups are optionally substituted.

Preferred Aryl groups for R[2'] of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

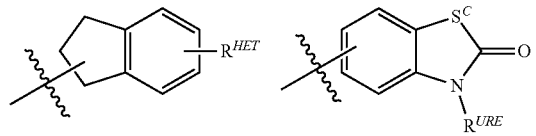

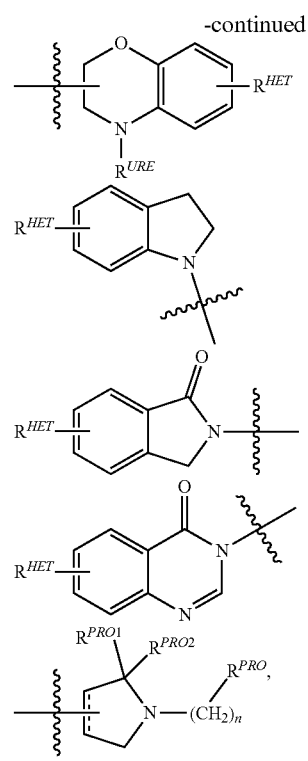

wherein:
S$^C$ of ULM-g through ULM-i is CHR$^{SS}$, NR$^{URE}$, or O;
R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$alkyl) (preferably substituted with one or two hydroxyl groups or up to three halo groups);
R$^{URE}$ of ULM-g through ULM-i is H, a C$_1$-C$_6$ alkyl (preferably H or C$_1$-C$_3$ alkyl) or a —C(O)(C$_1$-C$_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);
R$^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrrolidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group; and each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally attached to a PTM group (including a ULM' group) via a linker group.

In certain preferred aspects,

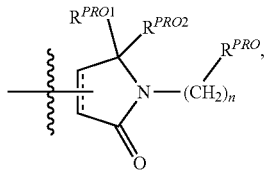

of ULM-g through ULM-i is a

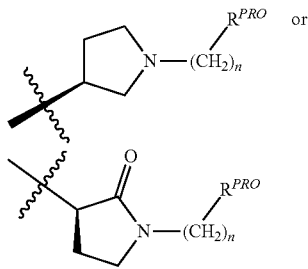

group, where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3-, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

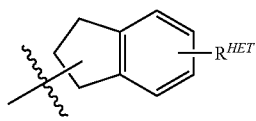

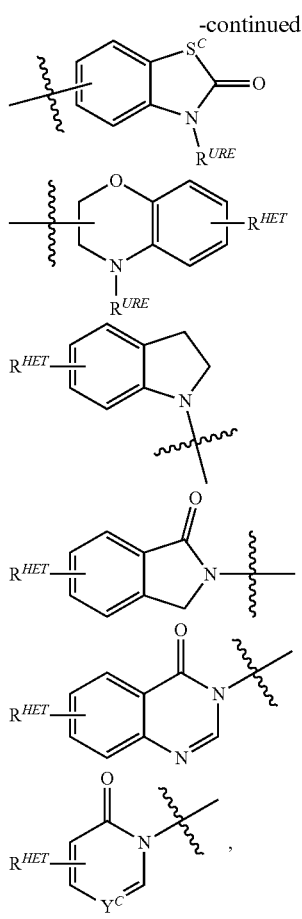

wherein:

$S^C$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocylclgroups for $R^{2'}$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

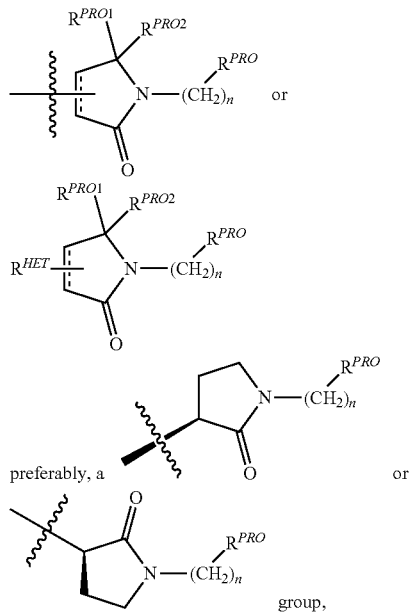

preferably, a group, wherein:
$R^{PRO}$ of ULM-g through ULM-i is H, optionally substituted $C_1$-$C_6$ alkyl or an optionally substituted aryl, heteroaryl or heterocyclyl group;
$R^{PRO1}$ and $R^{PRO2}$ of ULM-g through ULM-i are each independently H, an optionally substituted $C_1$-$C_3$ alkyl group or together form a keto group and
each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted-T-Heteroaryl, an optionally substituted -T-heterocyclyl, an optionally substituted-$NR^1$-T-Aryl (e.g., an optionally substituted NH-T-aryl, an optionally substituted N(CH3)-T-aryl, or an optionally substituted N($C_1$-$C_3$ alkyl)-T-aryl), an optionally substituted —$NR^1$-T-Heteroaryl (e.g., an optionally substituted NH-T-heteroaryl, an optionally substituted N(CH3)-T-heteroaryl, or an optionally substituted N($C_1$-$C_3$ alkyl)-T-heteroaryl), or an optionally substituted-$NR^1$-T-heterocyclyl (e.g., an optionally substituted NH-T-heterocyclyl, an optionally substituted N($CH_3$)-T-heterocyclyl, or an optionally substituted N($C_1$-$C_3$ alkyl)-T-heterocyclyl), where $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a $C_1$-$C_6$ alkyl group, an optionally substituted aryl, heteroaryl or heterocycle group or a —$(CH_2)_m NR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3-, or 4-pyridine) or a group according to the chemical structure:

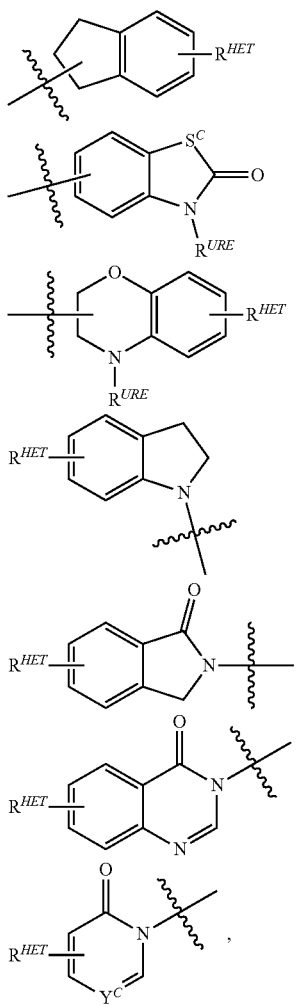

wherein:
S$^c$ of ULM-g through ULM-i is CHR$^{SS}$, NR$^{URE}$, or O;
R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl); R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);
R$^{URE}$ of ULM-g through ULM-i is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
Y$^C$ of ULM-g through ULM-i is N or C—R$^{YC}$, where R$^{YC}$C is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl). Each of said heteroaryl groups may be optionally connected/attached to a PTM group (including a ULM' group) via a linker group.

Preferred heterocycle groups for R$^{3'}$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

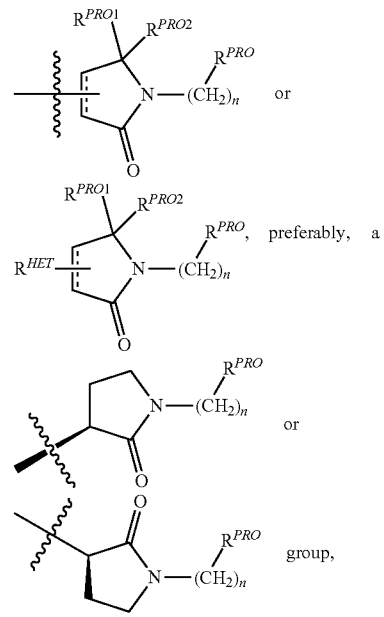

wherein:
R$^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ of ULM-g through ULM-i are each independently H, an optionally substituted C$_1$-C$_3$ alkyl group or together form a keto group, and each n of ULM-g through ULM-i is 0, 1, 2, 3, 4, 5, or 6 (preferably 0 or 1), wherein each of said Heteocycle groups may be optionally connected/attached to a PTM group (including a ULM' group) via a linker group.

Preferred R$^{3'}$ substituents of ULM-g through ULM-i also include specifically (and without limitation to the specific compound disclosed) the R$^{3'}$ substituents which are found in the identified compounds disclosed herein (which includes the specific compounds which are disclosed in the present specification, and the figures which are attached hereto). Each of these R$^{3'}$ substituents may be used in conjunction with any number of R$^{2'}$ substituents, which are also disclosed herein.

In certain alternative preferred embodiments, R$^{2'}$ of ULM-g through ULM-i is an optionally substituted —NR$_1$—X$^{R2'}$-alkyl group, —NR$_1$—X$^{R2'}$-Aryl group; an optionally substituted —NR$_1$—X$^{R2'}$-HET, an optionally substituted —NR$_1$—X$^{R2'}$-Aryl-HET or an optionally substituted —NR$_1$—X$^{R2'}$-HET-Aryl,
wherein:
R$_1$ of ULM-g through ULM-i is H or a C$_1$-C$_3$ alkyl group (preferably H);
X$^{R2'}$ of ULM-g through ULM-i is an optionally substituted —CH$_2$)$_n$—, —CH$_2$)$_n$—CH(X$_v$)=CH(X$_v$)-(cis or trans), —(CH$_2$)$_n$—CH=CH—, —(CH$_2$CH$_2$O)$_n$— or a C$_3$-C$_6$ cycloalkyl group; and
X$_v$ of ULM-g through ULM-i is H, a halo or a C$_1$-C$_3$ alkyl group which is optionally substituted with one or two hydroxyl groups or up to three halogen groups;
Alkyl of ULM-g through ULM-i is an optionally substituted C1-C$_{10}$ alkyl (preferably a C$_1$-C$_6$ alkyl) group (in certain preferred embodiments, the alkyl group is end-capped with a halo group, often a Cl or Br);
Aryl of ULM-g through ULM-i is an optionally substituted phenyl or naphthyl group (preferably, a phenyl group); and
HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a C$_1$-C$_3$ alkyl group, preferably methyl or a halo group, preferably F or Cl) or a group according to the chemical structure:

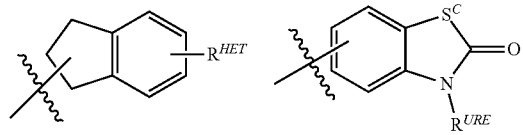

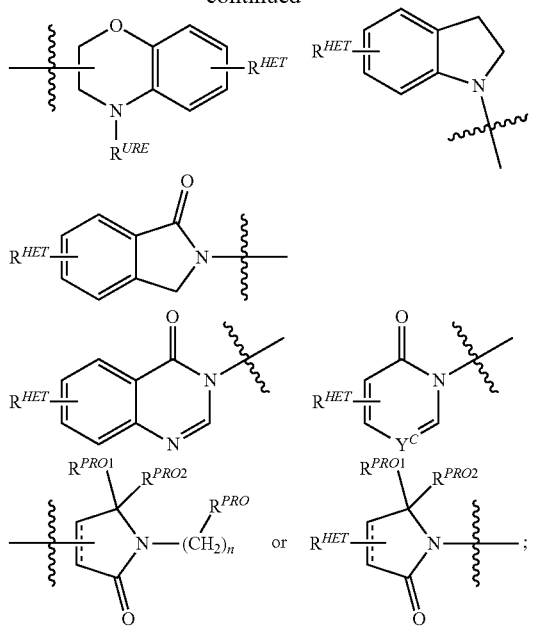

S$^c$ of ULM-g through ULM-i is CHR$^{SS}$, NR$^{URE}$, or O;
R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);
R$^{URE}$ of ULM-g through ULM-i is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
Y$^C$ of ULM-g through ULM-i is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected/attached to a PTM group (including a ULM' group) via a linker group.

In certain alternative preferred embodiments of the present disclosure, $R^{3'}$ of ULM-g through ULM-i is an optionally substituted —(CH2)$_n$—(V)$_{n'}$—(CH$_2$)$_n$—(V)$_{n'}$—$R^{S3'}$ group, an optionally substituted -(CH$_2$)$_n$—N(R$_{1'}$)(C=O)$_{m'}$—(V)$_{n'}$—$R^{S3'}$ group, an optionally substituted —$X^{R3'}$-alkyl group, an optionally substituted —$X^{R3'}$-Aryl group; an optionally substituted —$X^{R3'}$-HET group, an optionally substituted —$X^{R3'}$-Aryl-HET group or an optionally substituted —$X^{R3'}$-HET-Aryl group, wherein:
$R^{S3'}$ is an optionally substituted alkyl group ($C_1$-$C_{10}$, preferably $C_1$-$C_6$ alkyl), an optionally substituted Aryl group or a HET group;
$R_{1'}$ is H or a $C_1$-$C_3$ alkyl group (preferably H);
V is O, S or $NR_{1'}$;
$X^{R3'}$ is —(CH$_2$)$_n$—, —(CH$_2$CH$_2$O)$_n$—, —(CH$_2$)$_n$—CH(X$_v$)=CH(X$_v$)-(cis or trans), —CH$_2$)$_n$—CH≡CH—, or a $C_3$-$C_6$ cycloalkyl group, all optionally substituted;
$X_v$ is H, a halo or a $C_1$-$C_3$ alkyl group which is optionally substituted with one or two hydroxyl groups or up to three halogen groups;
Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);
Aryl is an optionally substituted phenyl or napthyl group (preferably, a phenyl group); and
HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

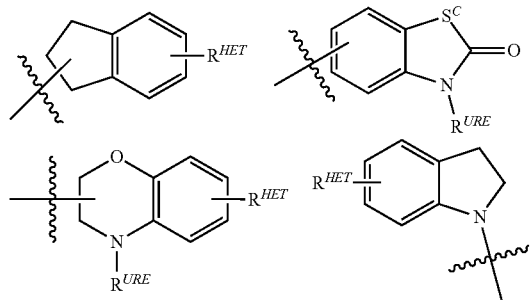

-continued

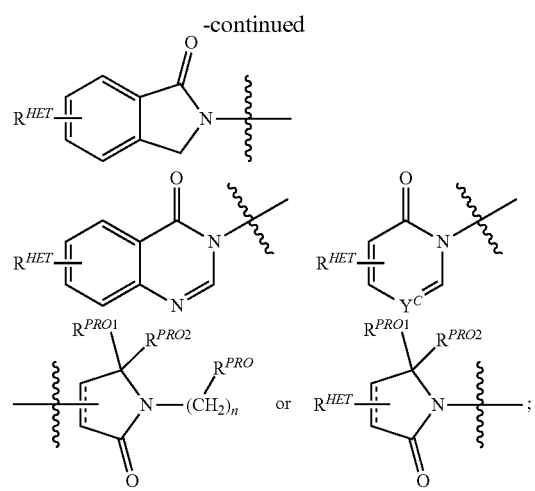

$S^c$ of ULM-g through ULM-i is $CHR^{SS}$, $NR^{URE}$, or O;
$R^{HET}$ of ULM-g through ULM-i is H, CN, NO$_2$, halo (preferably Cl or F), optionally substituted $C_1$-$C_6$ alkyl (preferably substituted with one or two hydroxyl groups or up to three halo groups (e.g. CF$_3$), optionally substituted O($C_1$-$C_6$ alkyl) (preferably substituted with one or two hydroxyl groups or up to three halo groups) or an optionally substituted acetylenic group —C≡C—R$_a$ where R$_a$ is H or a $C_1$-$C_6$ alkyl group (preferably $C_1$-$C_3$ alkyl);
$R^{SS}$ of ULM-g through ULM-i is H, CN, NO$_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
$Y^C$ of ULM-g through ULM-i is N or C—$R^{YC}$, where $R^{YC}$ is H, OH, CN, NO$_2$, halo (preferably Cl or F), optionally substituted $C_1$-$C_6$ alkyl (preferably substituted with one or two hydroxyl groups or up to three halo groups (e.g. CF$_3$), optionally substituted O($C_1$-$C_6$ alkyl) (preferably substituted with one or two hydroxyl groups or up to three halo groups) or an optionally substituted acetylenic group —C≡C—R$_a$ where R$_a$ is H or a $C_1$-$C_6$ alkyl group (preferably $C_1$-$C_3$ alkyl);
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected/attached to a PTM group (including a ULM' group) via a linker.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$-HET, wherein:
said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_nO(C_1$-$C_6)$alkyl, amine, mono- or di-$(C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—$(C_1$-$C_6)$alkyl, —$(CH_2)_n$—O—$(CH_2)_n$—$(C_1$-$C_6)$alkyl, —$(CH_2)_n$—C(O)$(C_0$-$C_6)$ alkyl, —$(CH_2)_n$—C(O)O$(C_0$-$C_6)$alkyl, —$(CH_2)_n$—OC(O)$(C_0$-$C_6)$alkyl, amine, mono- or di-$(C_1$-$C_6$ alkyl) amine wherein the alkyl group on the amine is optionally substituted with 1 or 2 hydroxyl groups or up to three halo (preferably F, Cl) groups, CN, NO$_2$, an optionally substituted —$(CH_2)_n$—(V)$_{m'}$—CH$_2)_n$—(V)$_{m'}$—(C$_1$-$C_6)$alkyl group, a —(V)$_{m'}$—(CH$_2$CH$_2$O)$_n$—$R^{PEG}$ group where V is O, S or NR$_1$', R$_1$, is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

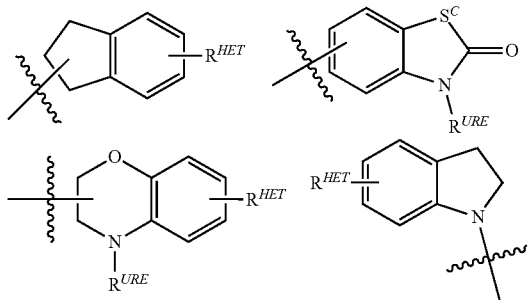

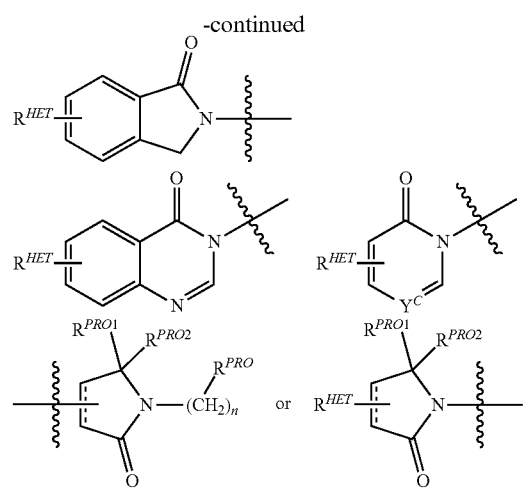

$S^c$ of ULM-g through ULM-i is CHR$^{SS}$, NR$^{URE}$, or O;

$R^{HET}$ of ULM-g through ULM-i is H, CN, NO$_2$, halo (preferably Cl or F), optionally substituted $C_1$-$C_6$ alkyl (preferably substituted with one or two hydroxyl groups or up to three halo groups (e.g. CF$_3$), optionally substituted O($C_1$-$C_6$ alkyl) (preferably substituted with one or two hydroxyl groups or up to three halo groups) or an optionally substituted acetylenic group —C≡C—R$_a$ where R$_a$ is H or a $C_1$-$C_6$ alkyl group (preferably $C_1$-$C_3$ alkyl);

$R^{SS}$ of ULM-g through ULM-i is H, CN, NO$_2$, halo (preferably F or Cl), optionally substituted $C_1$-$C_6$ alkyl (preferably substituted with one or two hydroxyl groups or up to three halo groups), optionally substituted O—$(C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—R$^{YC}$, where R$^{YC}$ is H, OH, CN, NO$_2$, halo (preferably Cl or F), optionally substituted $C_1$-$C_6$ alkyl (preferably substituted with one or two hydroxyl groups or up to three halo groups (e.g. CF$_3$), optionally substituted O($C_1$-$C_6$ alkyl) (preferably substituted with one or two hydroxyl groups or up to three halo groups) or an optionally substituted acetylenic group —C≡C—R$_a$ where R$_a$ is H or a $C_1$-$C_6$ alkyl group (preferably C1-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

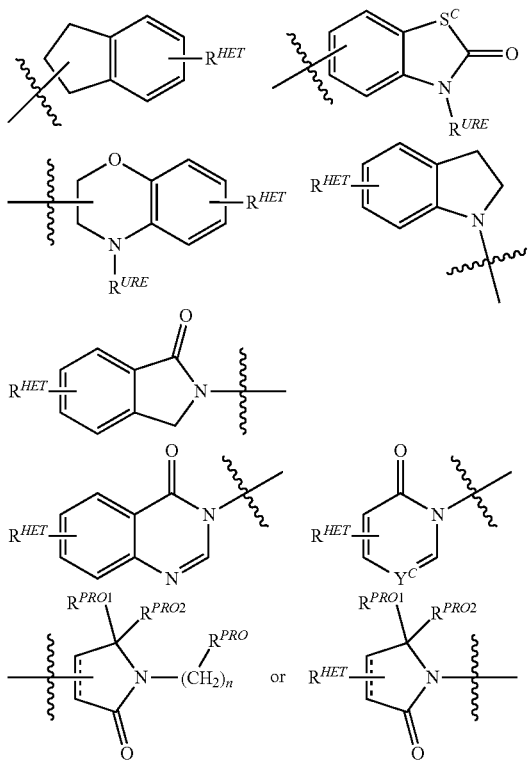

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected/attached to a PTM group (including a ULM' group) via a linker group.

In still additional embodiments, preferred compounds include those according to the chemical structure:

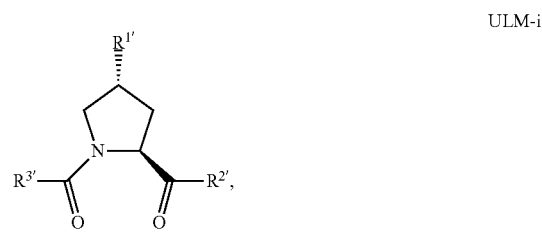

ULM-i wherein:

$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^{3'}$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —$(CH_2)_n OCH_3$ group where n is 1 or 2 (preferably 2), or a

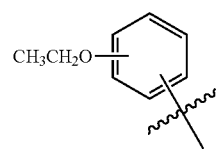

group (the ethyl ether group is preferably meta-substituted on the phenyl moiety), a morpholino group (linked to the carbonyl at the 2- or 3-position;
$R^{3P2}$ of ULM-i is a

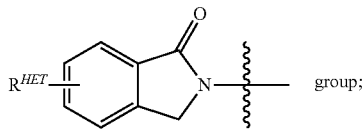 group;

Aryl of ULM-i is phenyl;
HET of ULM-i is an optionally substituted thiazole or isothiazole; and
$R^{HET}$ of ULM-i is H or a halo group (preferably H);
or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

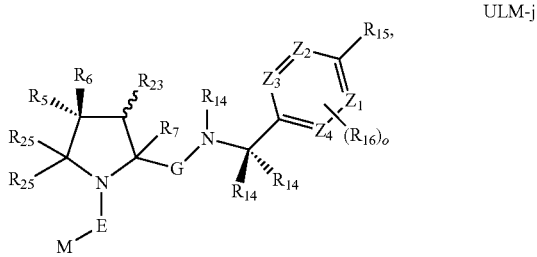 ULM-j wherein:
each $R_5$ and $R_6$ of ULM-j is independently OH, SH, or optionally substituted alkyl or $R_5$, $R_6$, and the carbon atom to which they are attached form a carbonyl;
$R_7$ of ULM-j is H or optionally substituted alkyl;
E of ULM-j is a bond, C=O, or C=S;
G of ULM-j is a bond, optionally substituted alkyl, —COOH or C=J;
J of ULM-j is O or N—$R_8$;
$R_8$ of ULM-j is H, CN, optionally substituted alkyl or optionally substituted alkoxy;
M of ULM-j is optionally substituted aryl, optionally substituted heteroaryl, optionally substituted heterocyclic or

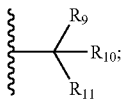

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;
$R_{11}$ of ULM-j is optionally substituted heterocyclic, optionally substituted alkoxy, optionally substituted heteroaryl, optionally substituted aryl, or

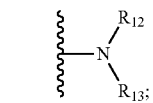

$R_{12}$ of ULM-j is H or optionally substituted alkyl;
$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate,
each $R_{14}$ of ULM-j is independently H, haloalkyl, optionally substituted cycloalkyl, optionally substituted alkyl or optionally substituted heterocycloalkyl;
$R_{15}$ of ULM-j is H, CN, optionally substituted heteroaryl, haloalkyl, optionally substituted aryl, optionally substituted alkoxy, or optionally substituted heterocyclyl;
each $R_{16}$ of ULM-j is independently halo, optionally substituted alkyl, optionally substituted haloalkyl, CN, or optionally substituted haloalkoxy;
each $R_{25}$ of ULM-j is independently H or optionally substituted alkyl; or both $R_{25}$ groups can be taken together to form an oxo or optionally substituted cycloalkyl group;
$R_{23}$ of ULM-j is H or OH;
$Z_1$, $Z_2$, $Z_3$, and $Z_4$ of ULM-j are independently C or N; and
o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

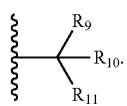

In certain embodiments, wherein E of ULM-j is C=O, $R_{11}$ is optionally substituted heterocyclic or

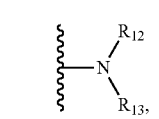

and M is

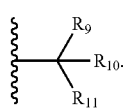

In certain embodiments, wherein E of ULM-j is C=O, M is

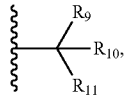

and R₁₁ is

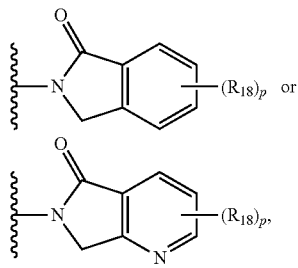

each R₁₈ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

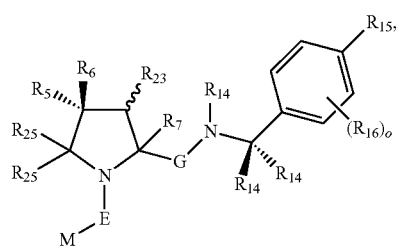

ULM-k wherein:
G of ULM-k is C=J, J is O;
R₇ of ULM-k is H;
each R₁₄ of ULM-k is H;
o of ULM-k is 0;
R₁₅ of ULM-k is

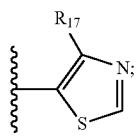

and
R₁₇ of ULM-k is H, halo, optionally substituted cycloalkyl, optionally substituted alkyl, optionally substituted alkenyl, and haloalkyl.

In other instances, R₁₇ of ULM-k is alkyl (e.g., methyl) or cycloalkyl (e.g., cyclopropyl).

In other embodiments, ULM and where present, ULM', are each independently a group according to the chemical structure:

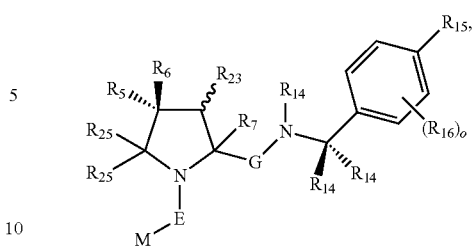

wherein:
G of ULM-k is C=J, J is O;
R₇ of ULM-k is H;
each R₁₄ of ULM-k is H;
o of ULM-k is 0; and
R₁₅ of ULM-k is selected from the group consisting of:

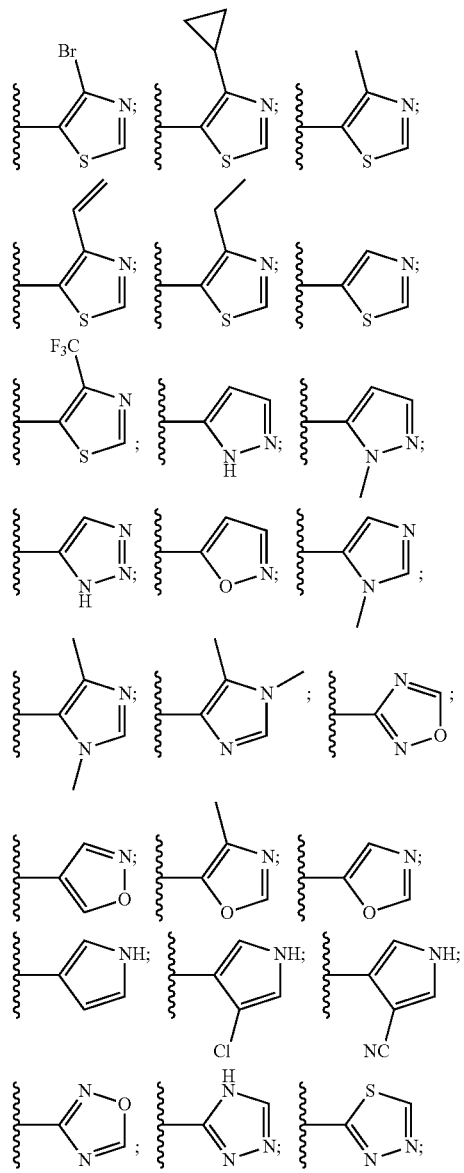

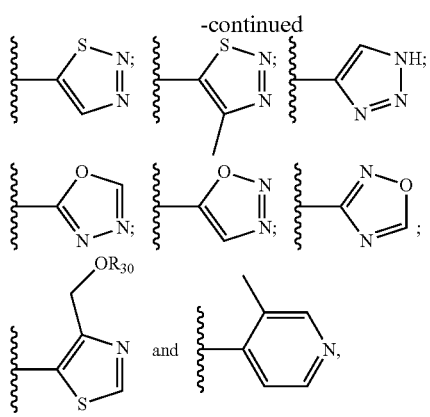
wherein R₃₀ of ULM-k is H or an optionally substituted alkyl.
In other embodiments, ULM and where present, ULM', are each independently a group according to the chemical structure:
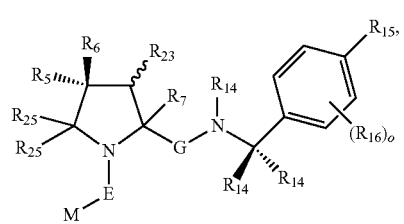
ULM-k
wherein:
E of ULM-k is C=O;
M of ULM-k is
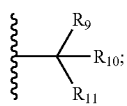
and
R₁₁ of ULM-k is selected from the group consisting of:
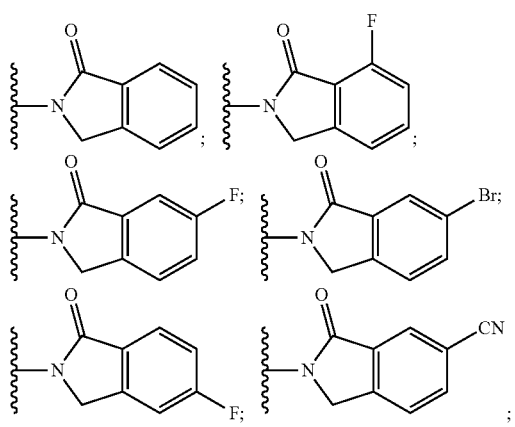
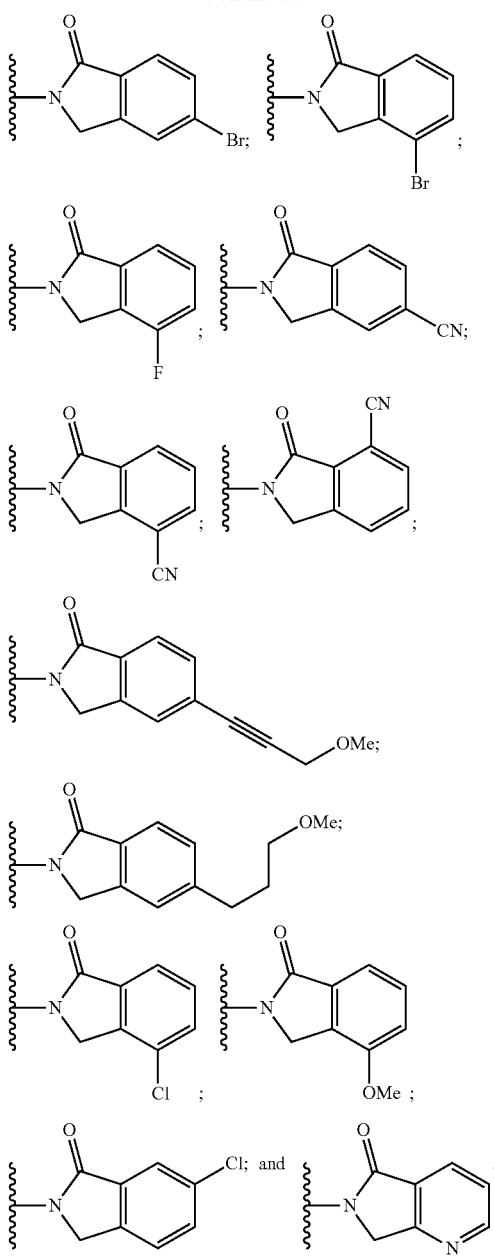
In still other embodiments, a compound of the chemical structure,
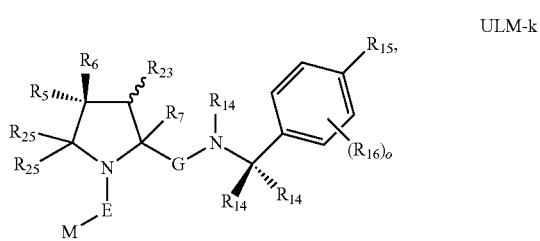
ULM-k wherein E of ULM-k is C=O;
R$_{11}$ of ULM-k is

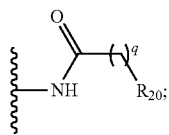

and
M of ULM-k is

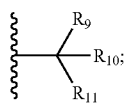

q of ULM-k is 1 or 2;
R$_{20}$ of ULM-k is H, optionally substituted alkyl, optionally substituted cycloalkyl, optionally substituted aryl, or

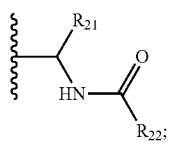

R$_{21}$ of ULM-k is H or optionally substituted alkyl; and
R$_{22}$ of ULM-k is H, optionally substituted alkyl, optionally substituted alkoxy, or haloalkyl.

In any embodiment described herein, R$_{11}$ of ULM-j or ULM-k is selected from the group consisting of:

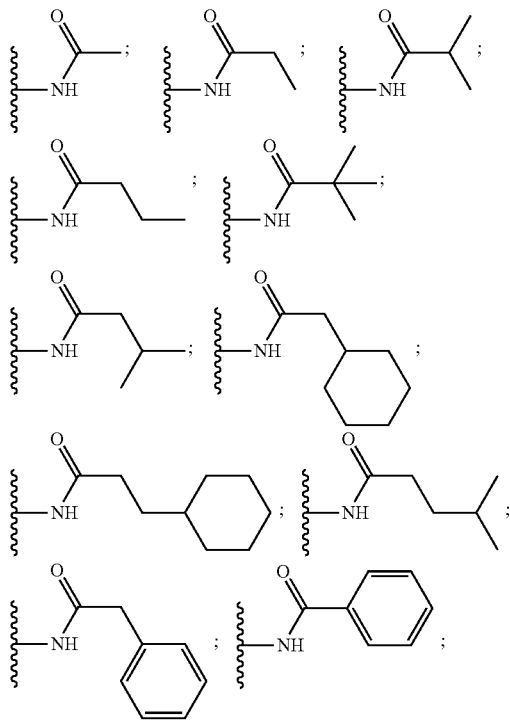

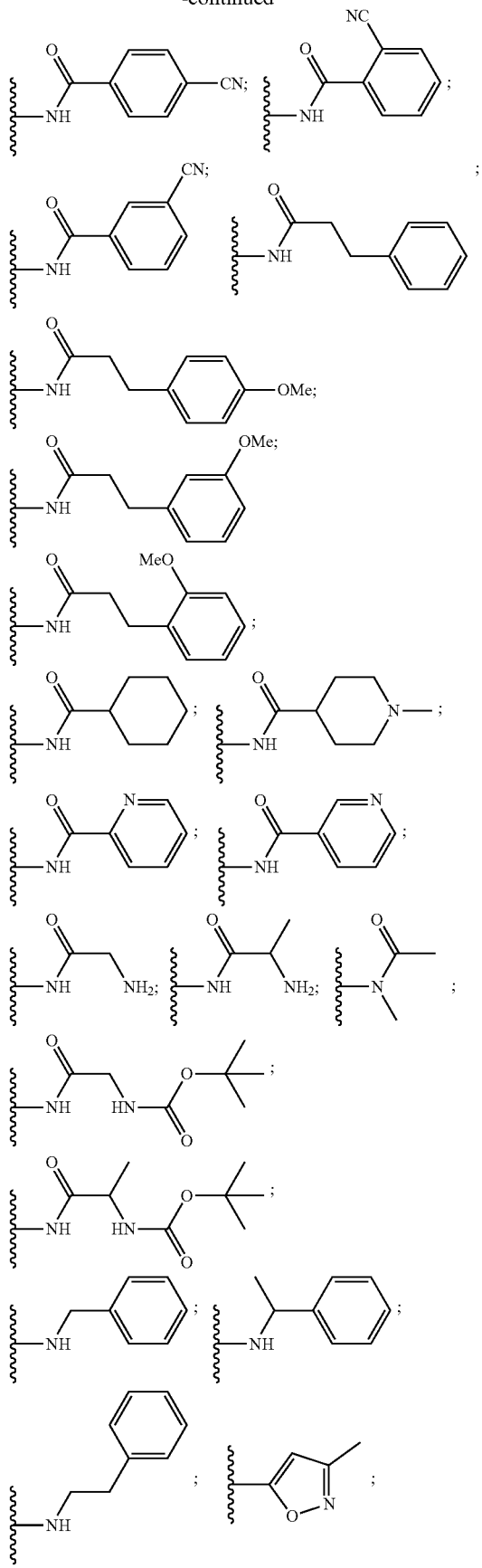

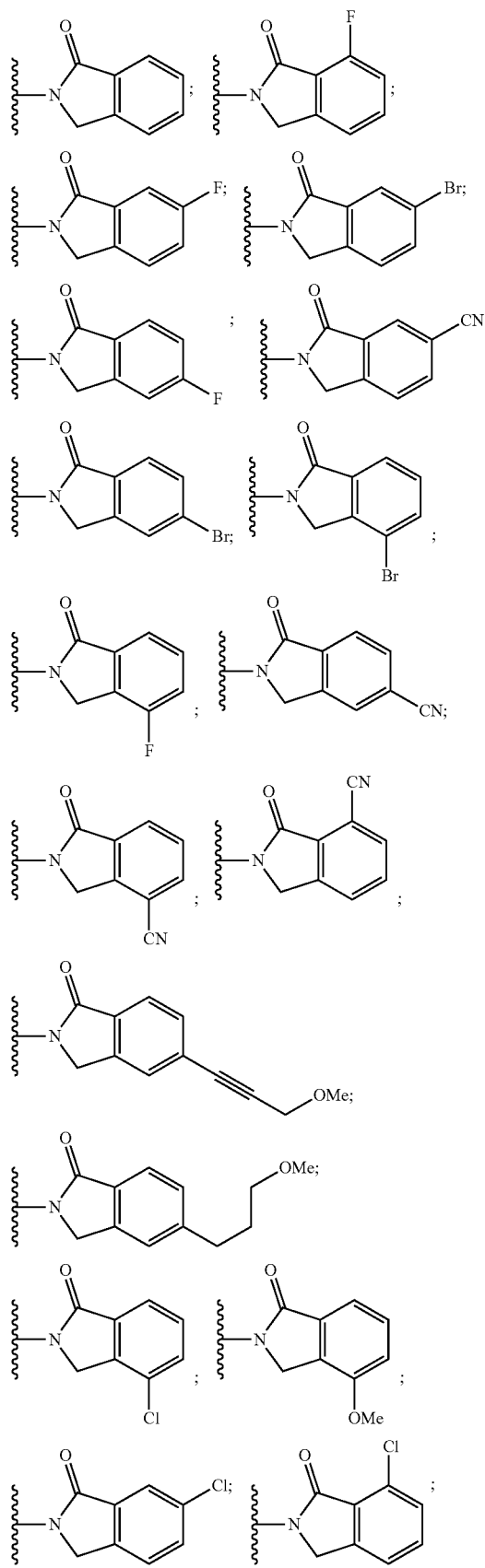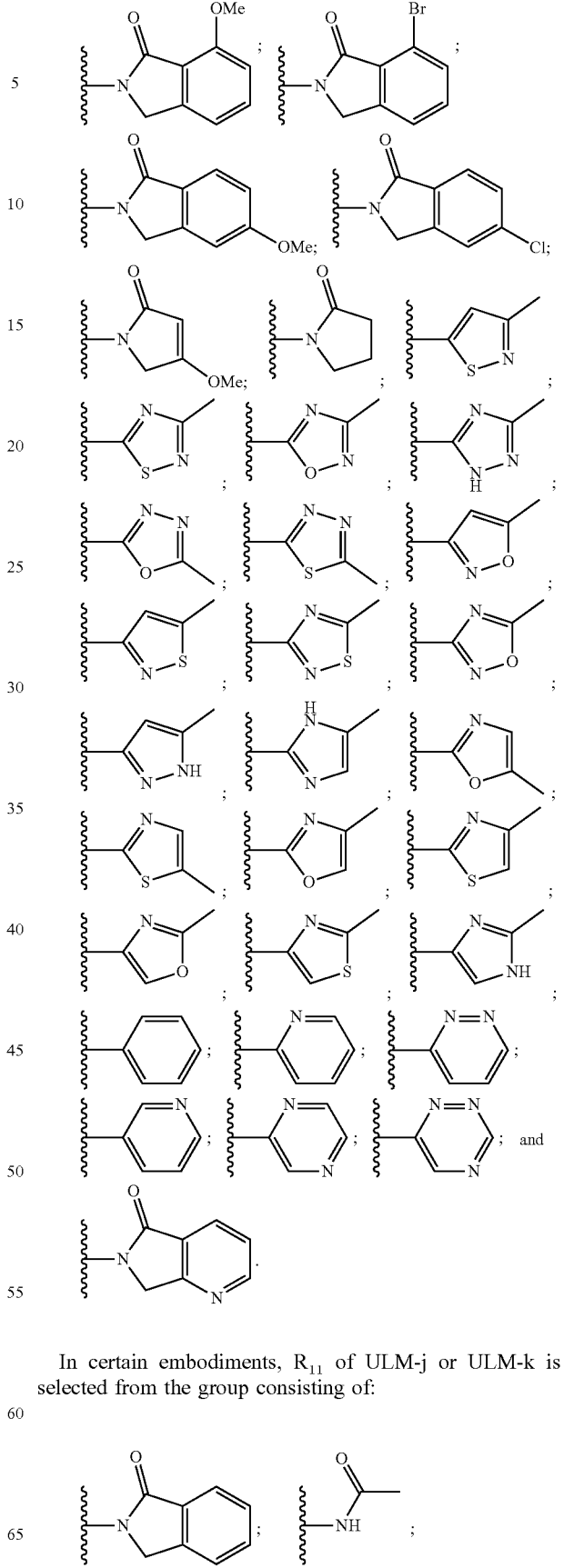
In certain embodiments, $R_{11}$ of ULM-j or ULM-k is selected from the group consisting of:

223
-continued
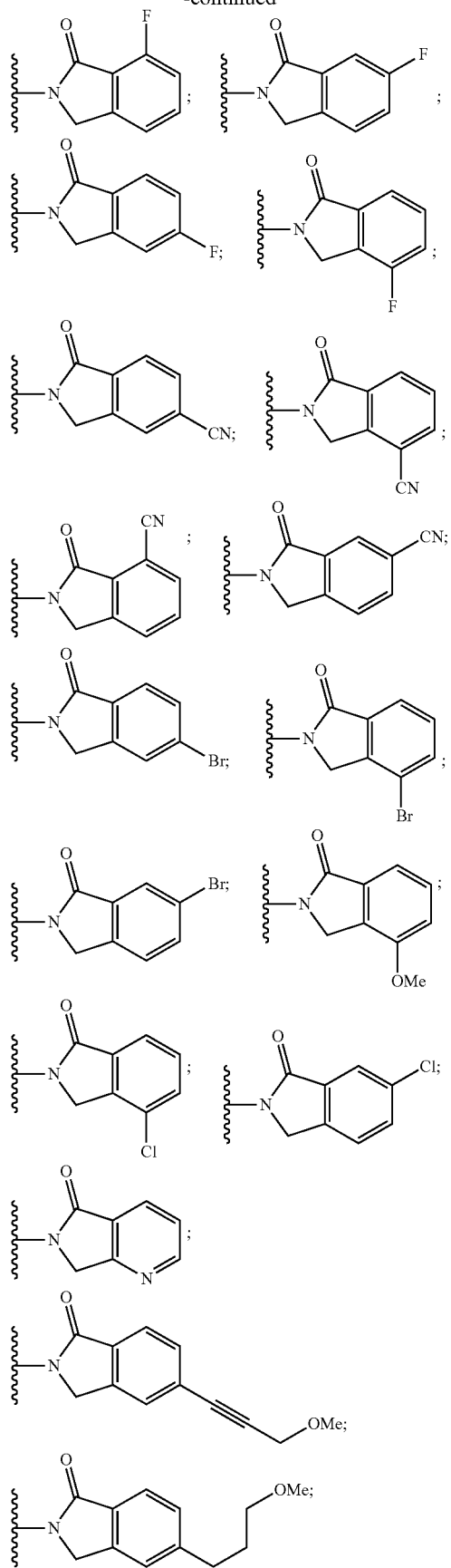
224
-continued
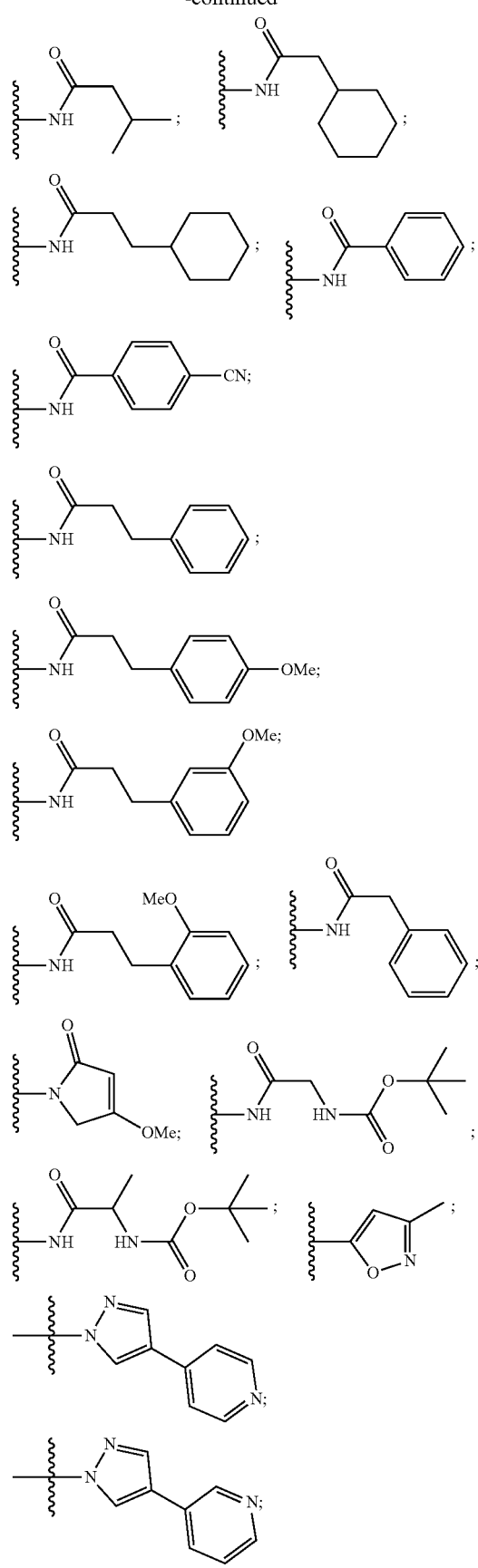

-continued

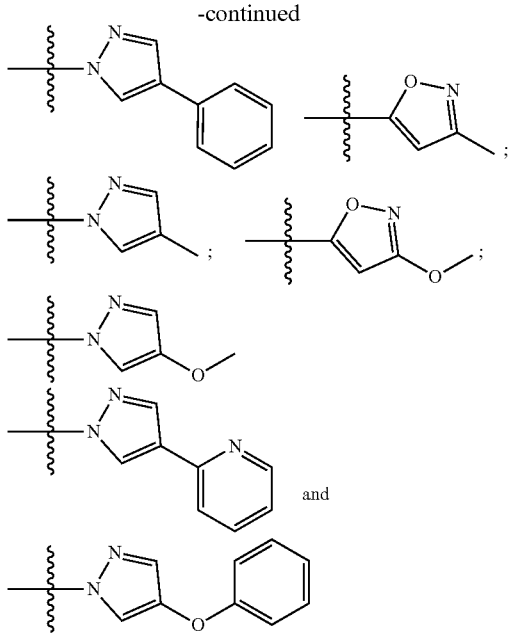

In certain embodiments, ULM (or when present ULM') is a group according to the chemical structure:

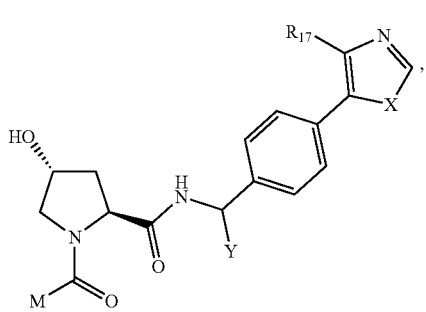
ULM-1 wherein:
X of ULM-1 is O or S;
Y of ULM-1 is H, methyl or ethyl;
$R_{17}$ of ULM-1 is H, methyl, ethyl, hydoxymethyl or cyclopropyl;
M of ULM-1 is optionally substituted aryl, optionally substituted heteroaryl, or

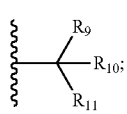

$R_9$ of ULM-1 is H;
$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;
R11 of ULM-1 is optionally substituted heteroaromatic, optionally substituted heterocyclic, optionally substituted aryl or

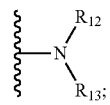

$R_{12}$ of ULM-1 is H or optionally substituted alkyl; and
$R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

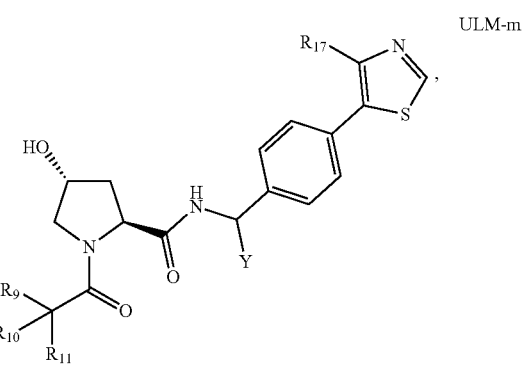
ULM-m wherein:
Y of ULM-m is H, methyl or ethyl
$R_9$ of ULM-m is H;
$R_{10}$ is isopropyl, tert-butyl, sec-butyl, cyclopentyl, or cyclohexyl;
$R_{11}$ of ULM-m is optionally substituted amide, optionally substituted isoindolinone, optionally substituted isooxazole, optionally substituted heterocycles.

In other preferred embodiments of the disclosure, ULM and where present, ULM', are each independently a group according to the chemical structure:

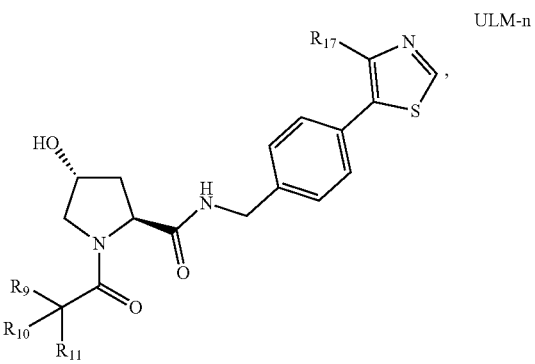
ULM-n wherein:
$R_{17}$ of ULM-n is methyl, ethyl, or cyclopropyl; and
$R_9$, $R_{10}$, and $R_{11}$ of ULM-n are as defined above. In other instances, $R_9$ is H; and $R_{10}$ of ULM-n is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

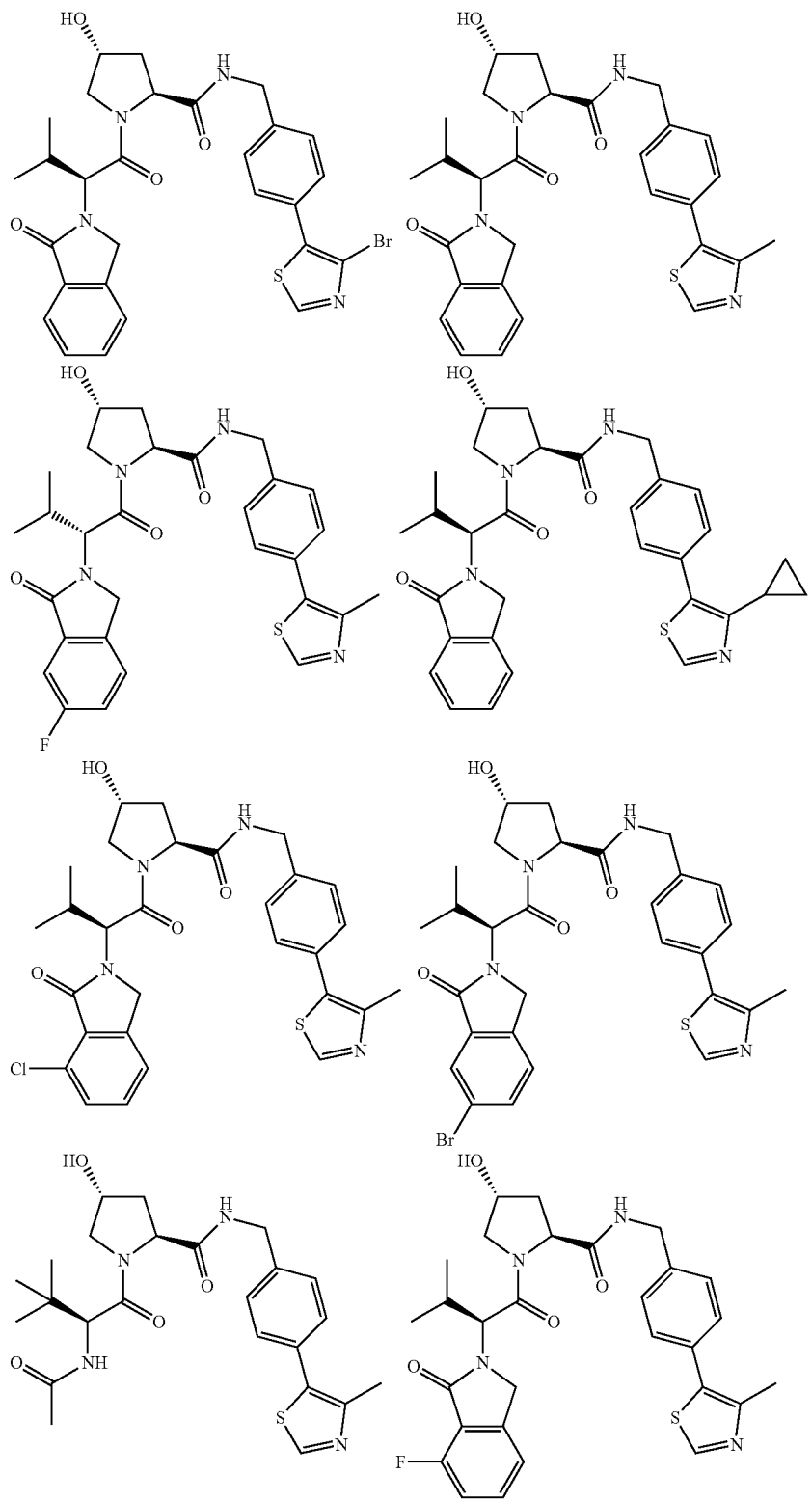

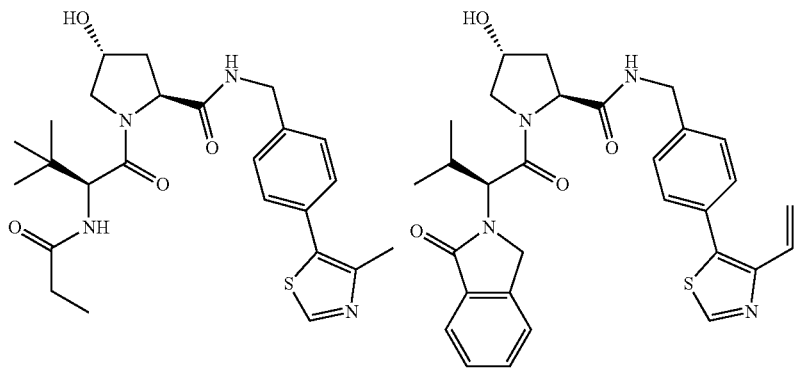
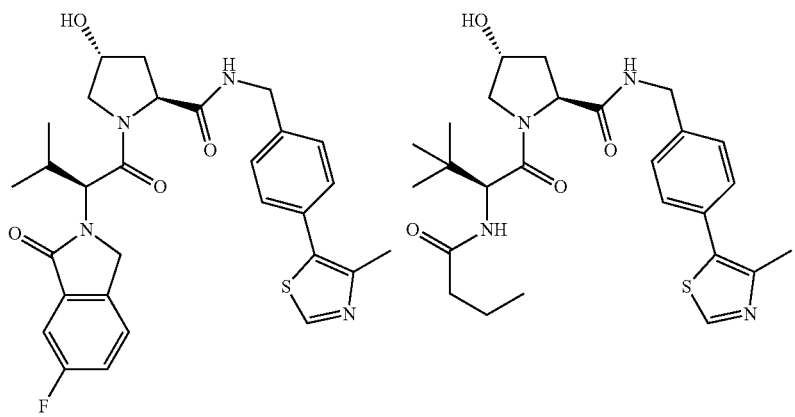
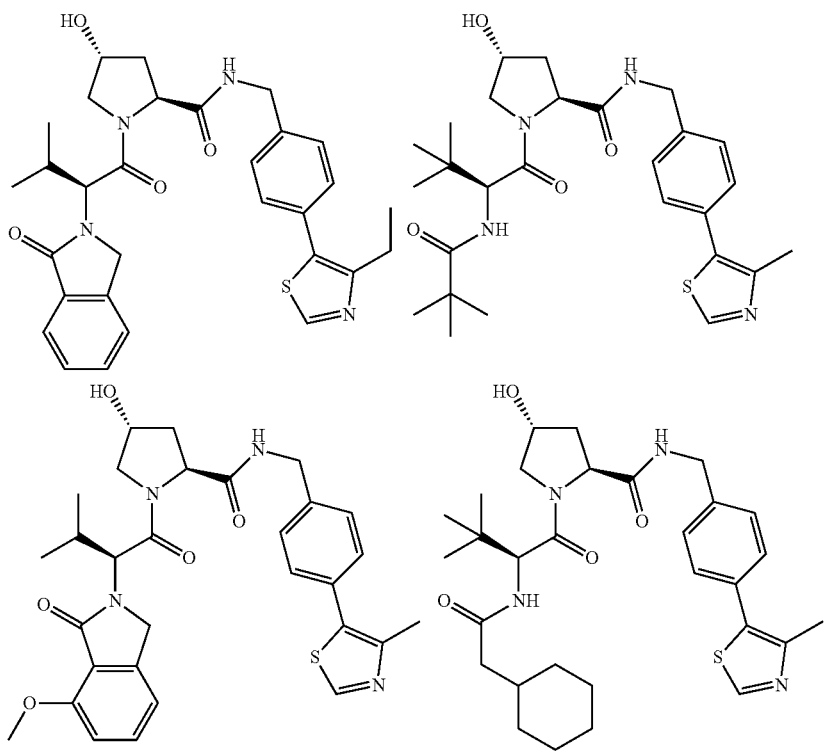

-continued
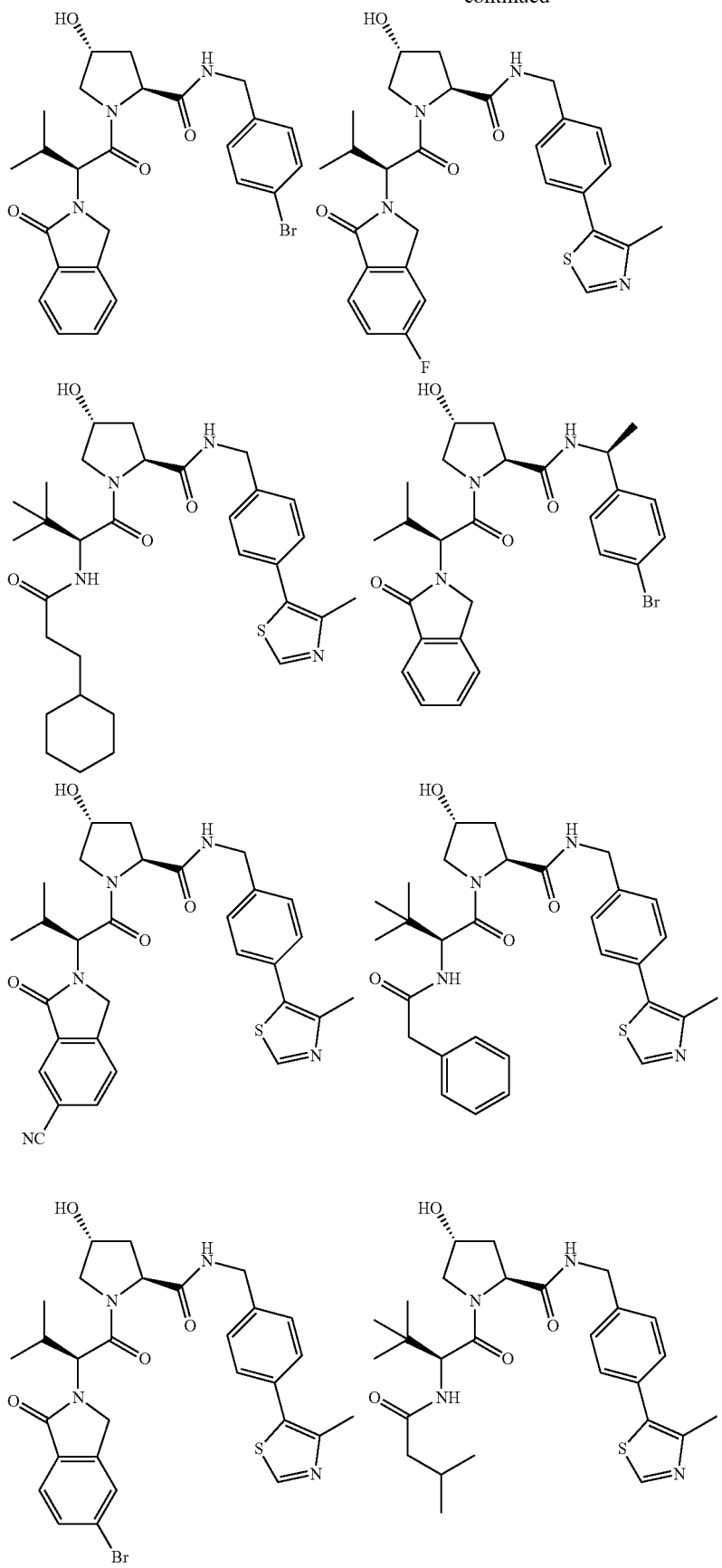

-continued
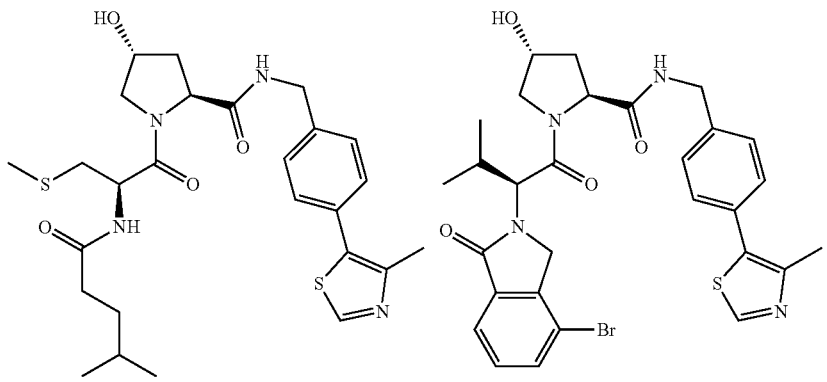
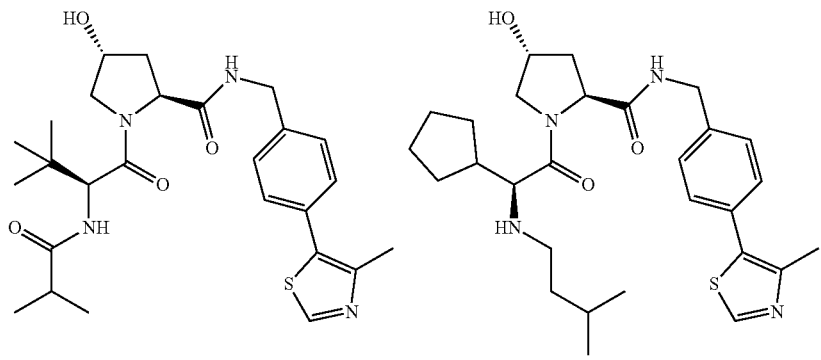
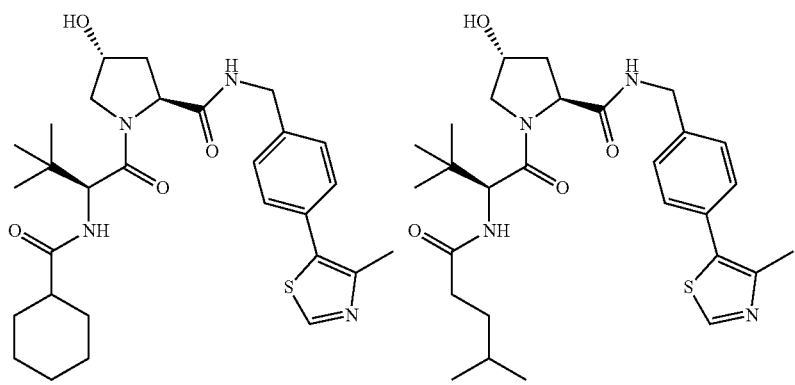
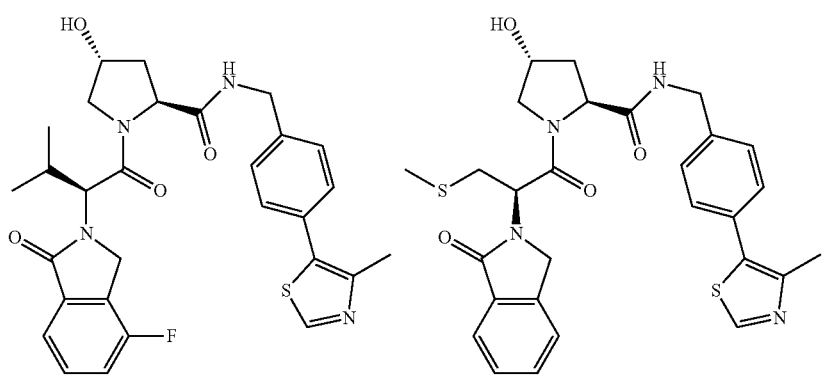

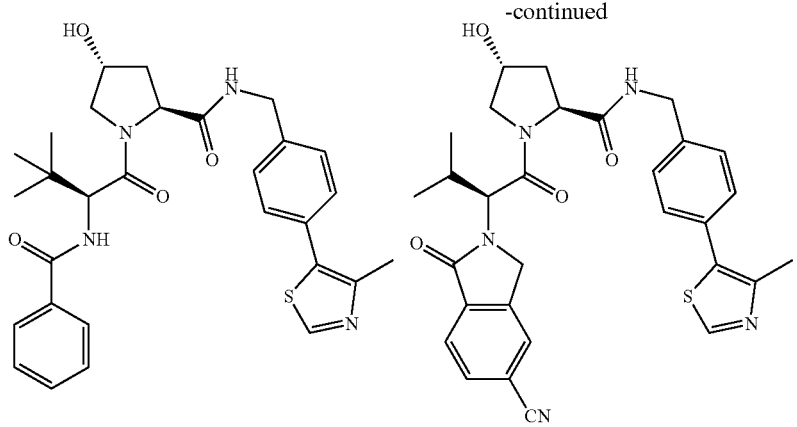
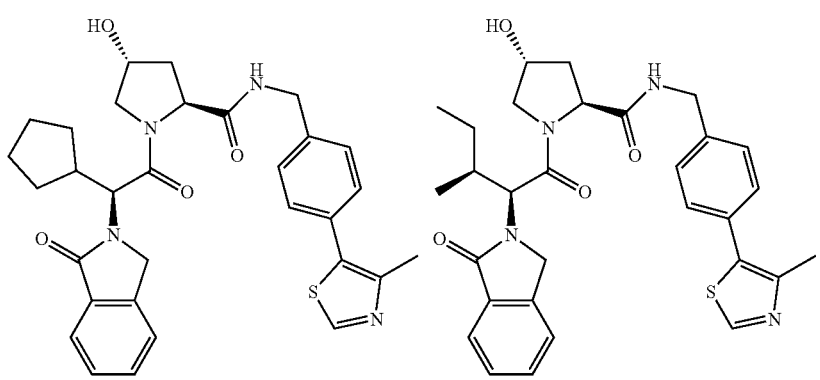
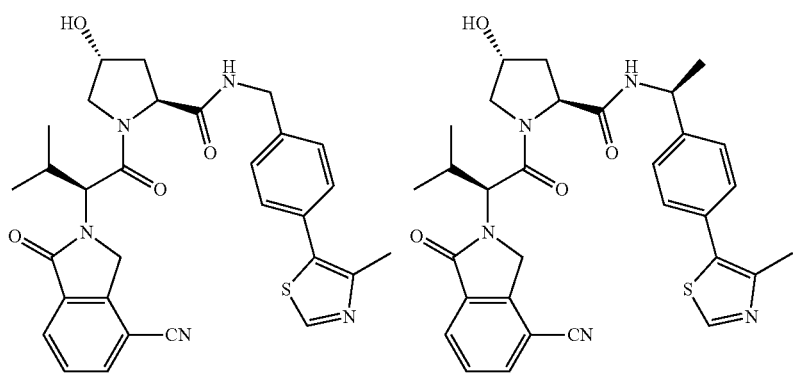
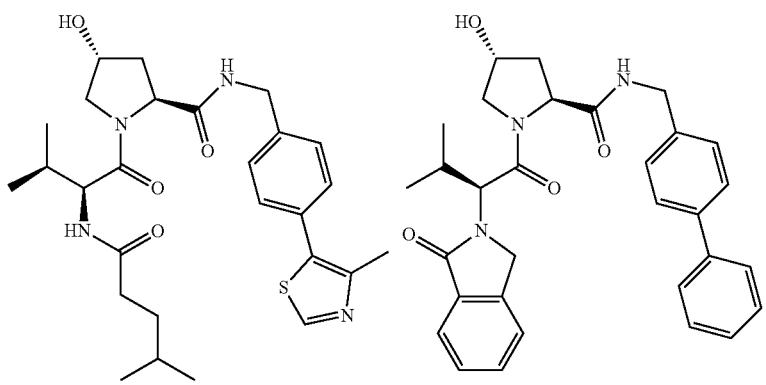

-continued
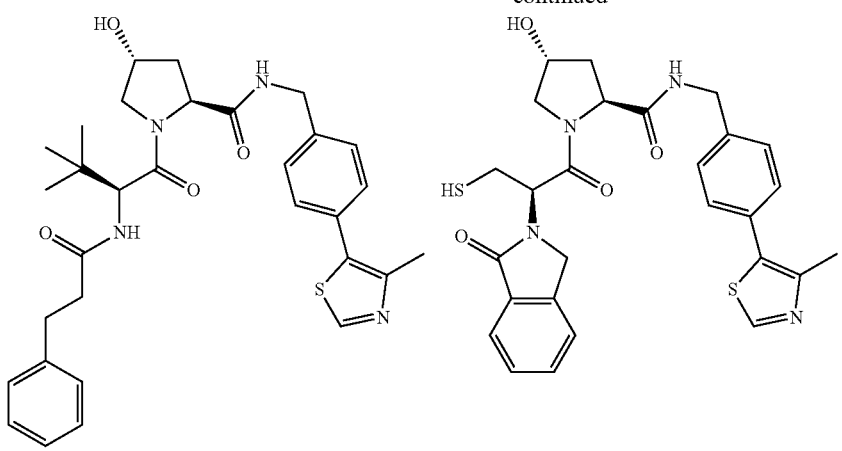
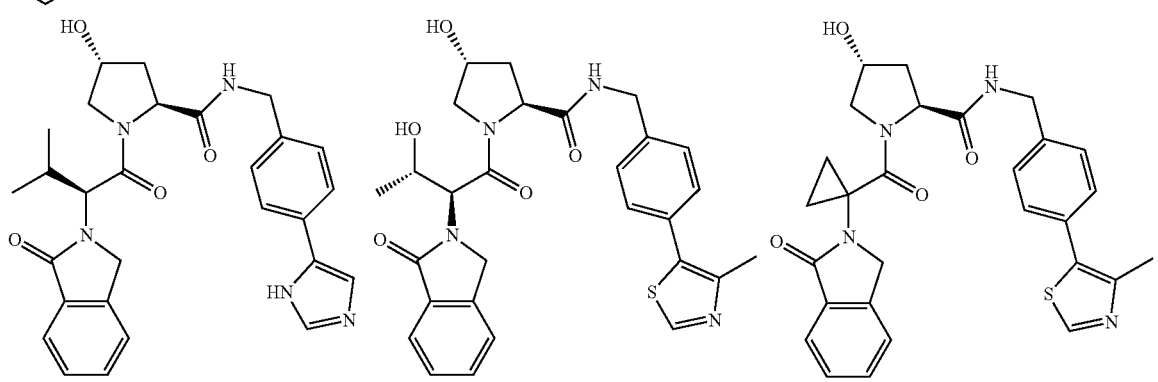
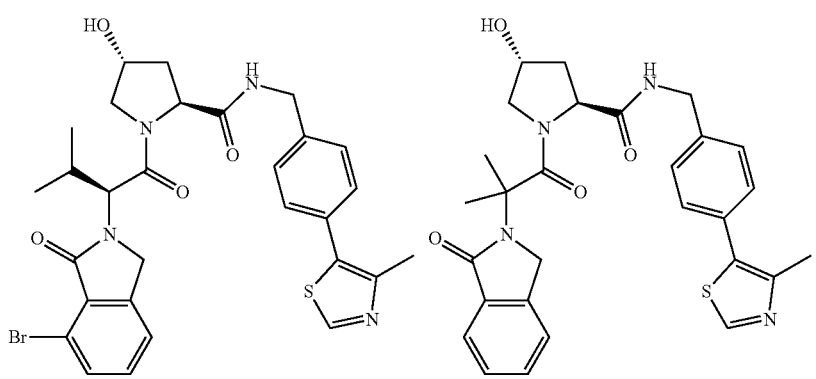
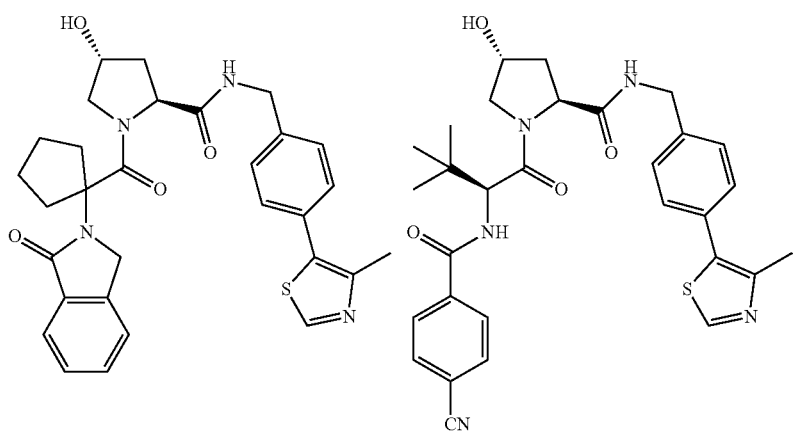

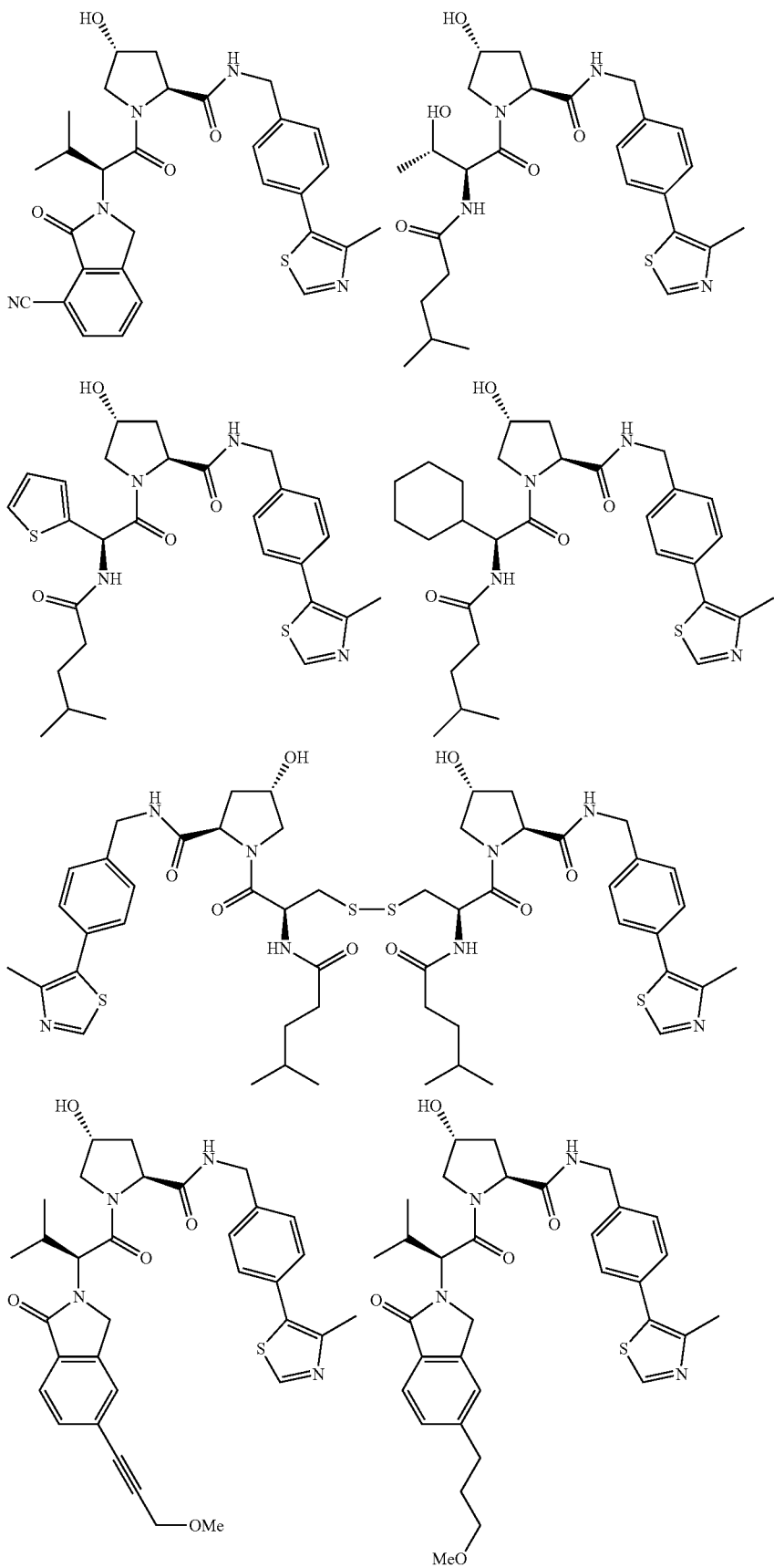

-continued
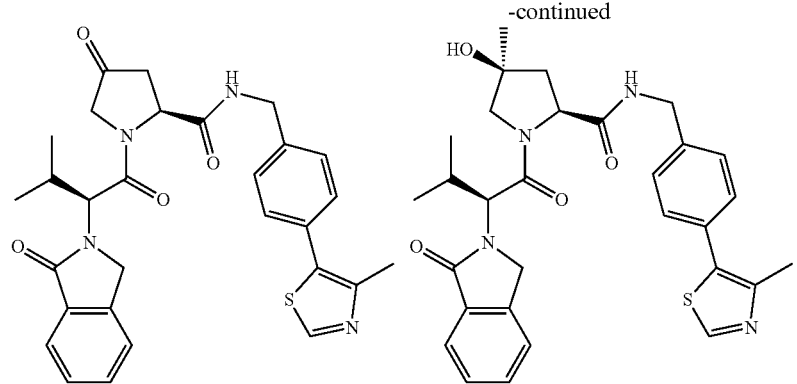
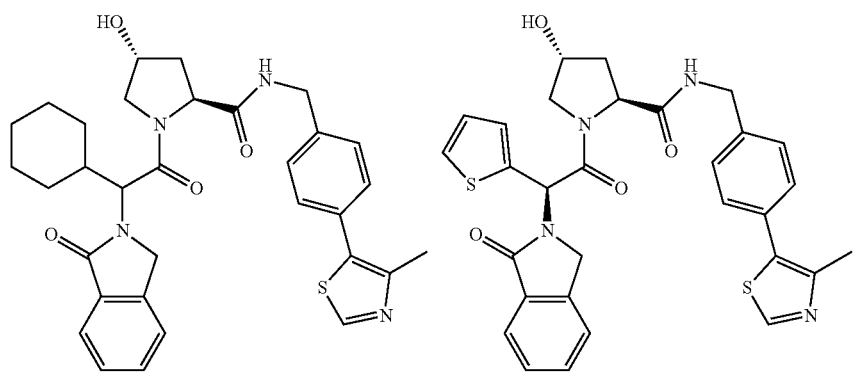
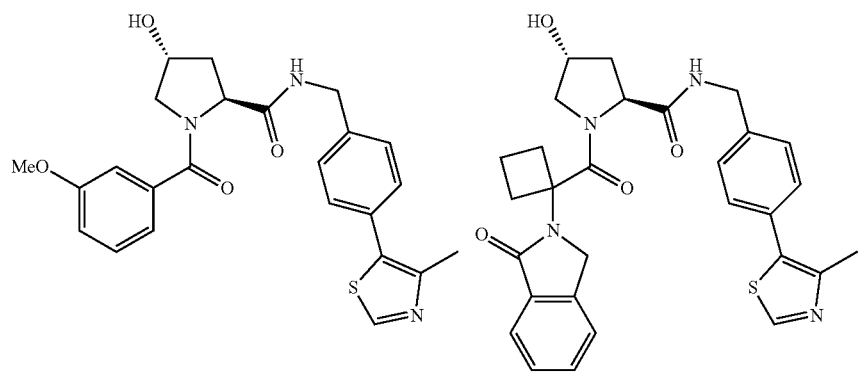
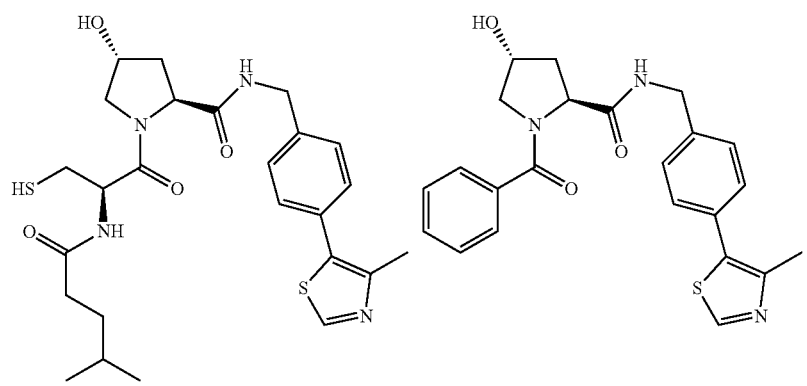

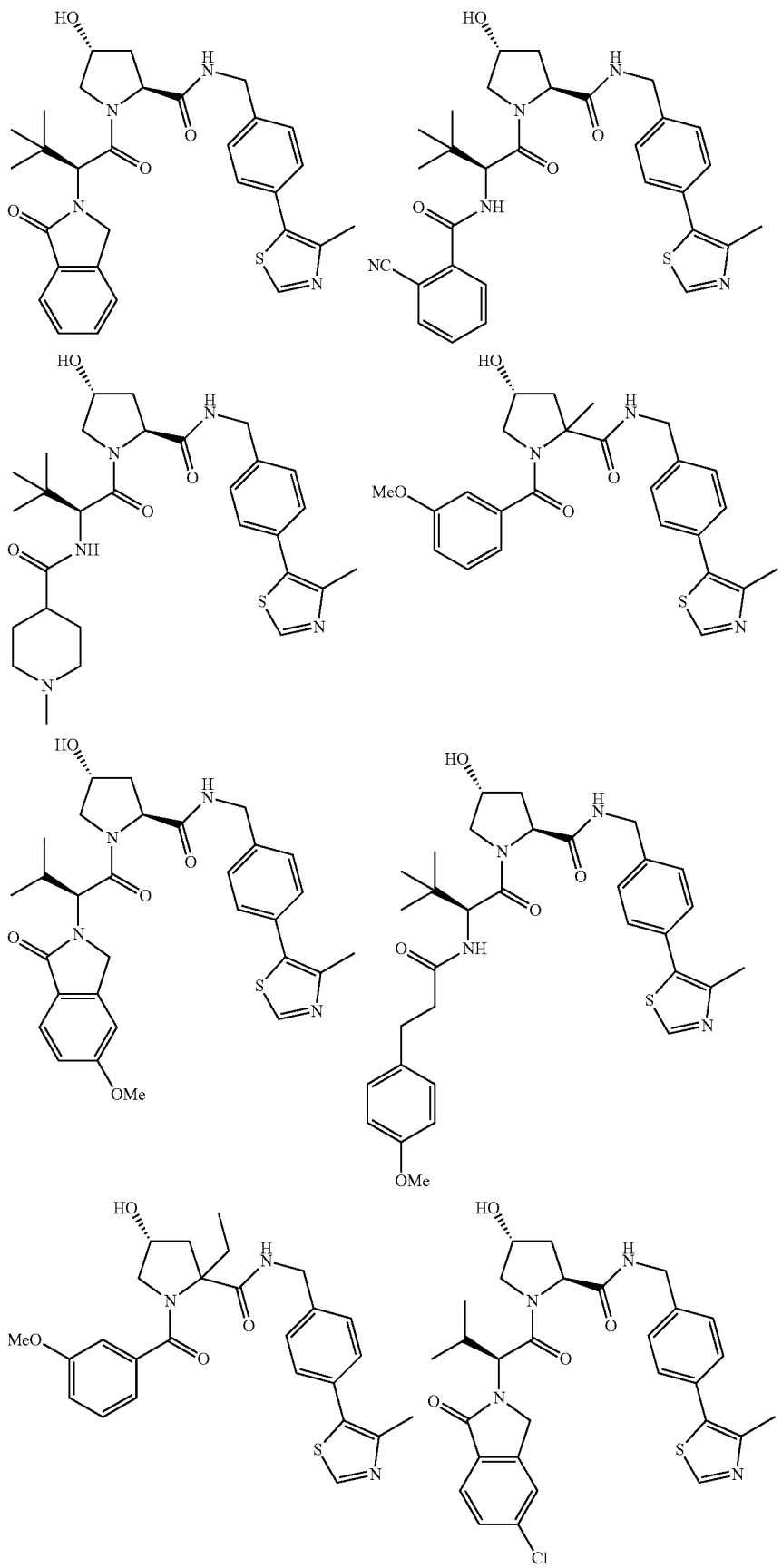

245 246
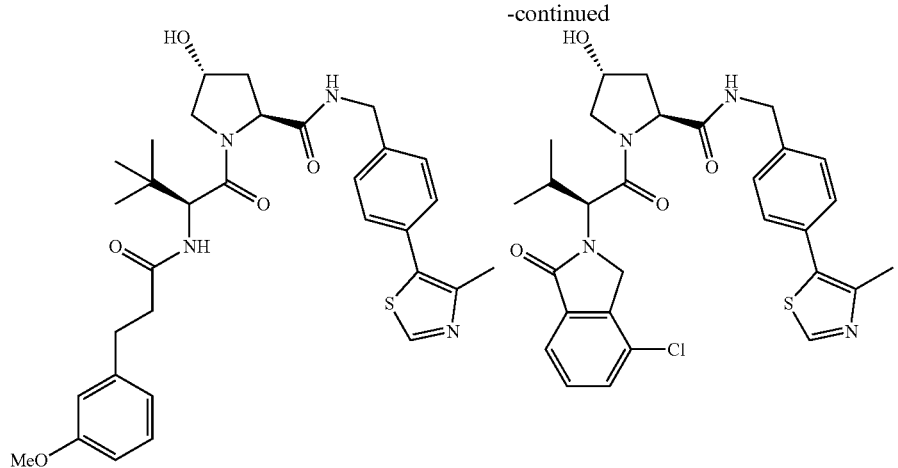
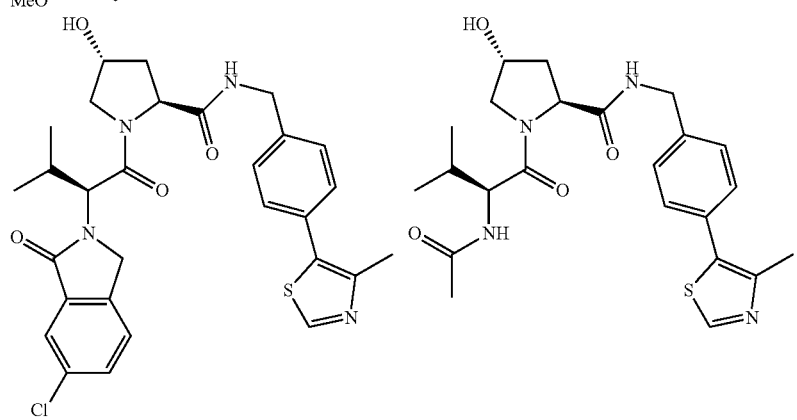
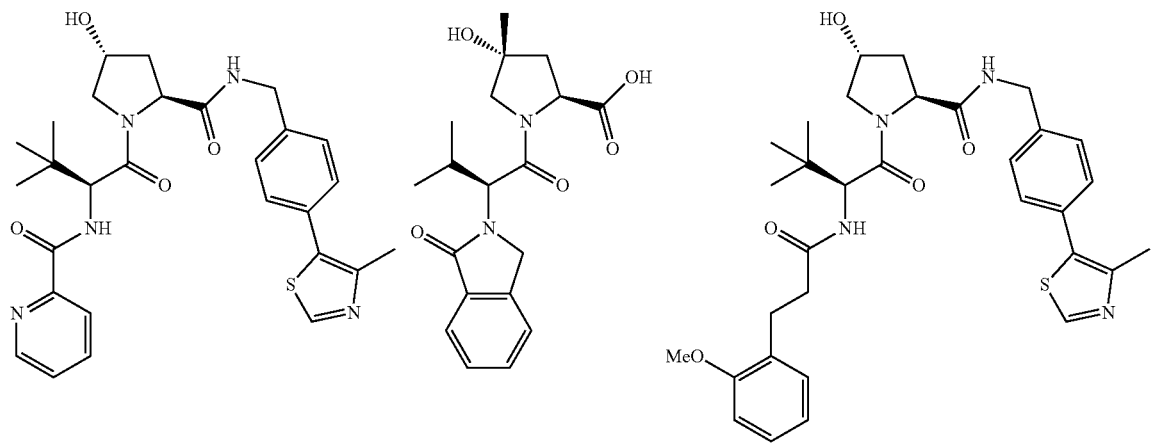
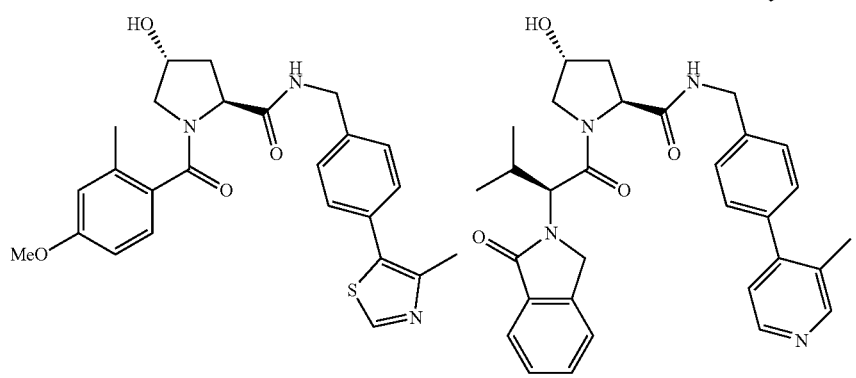

247
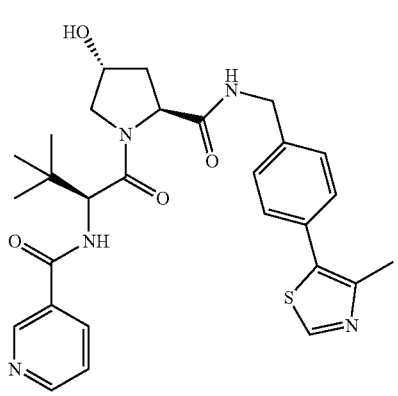
248
-continued
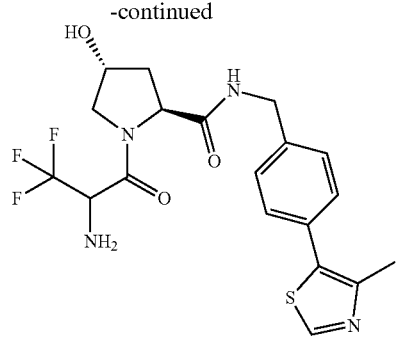
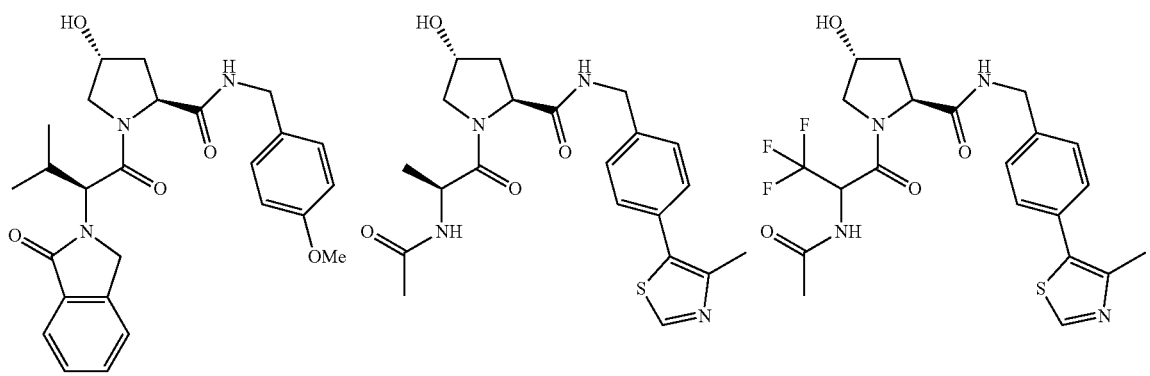
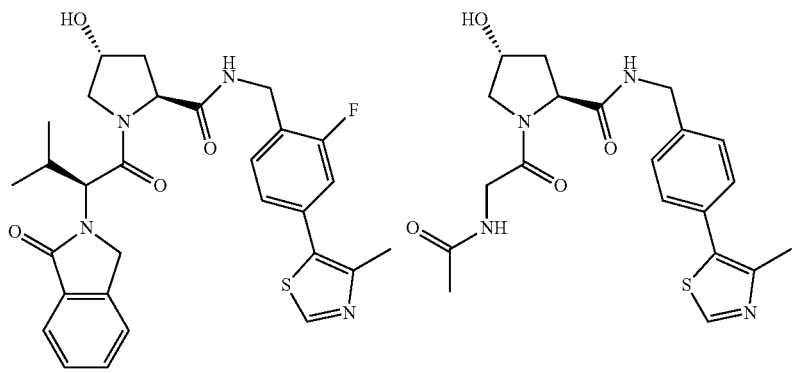
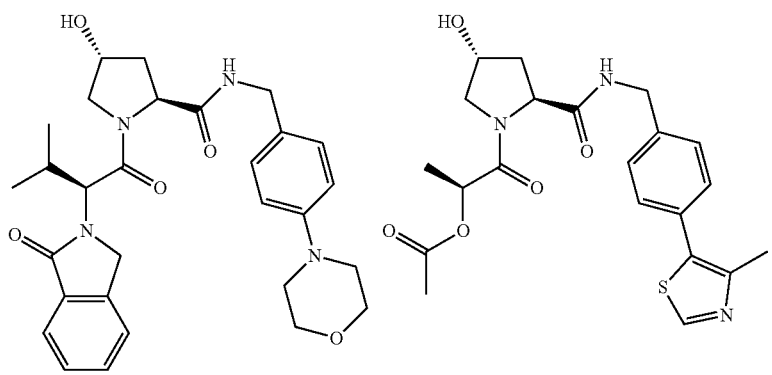

249
-continued
250
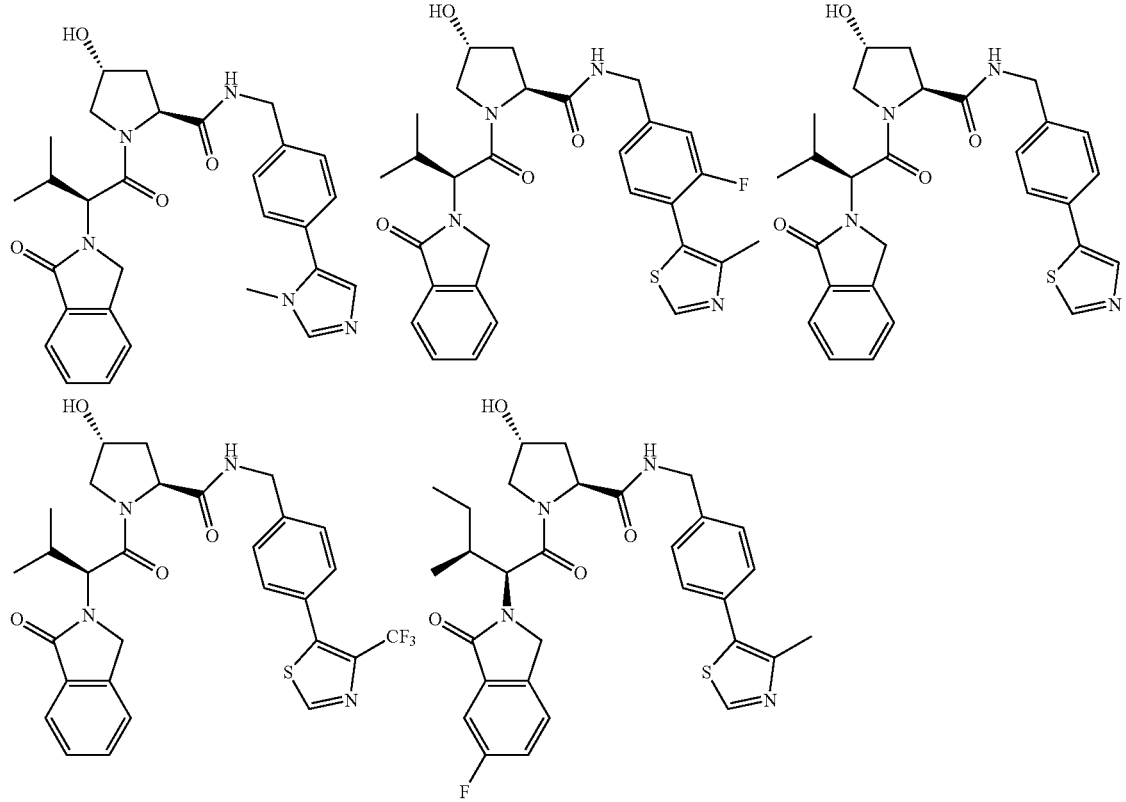
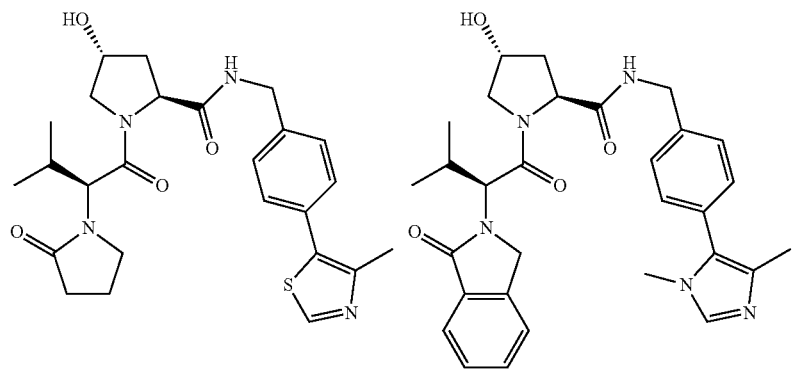
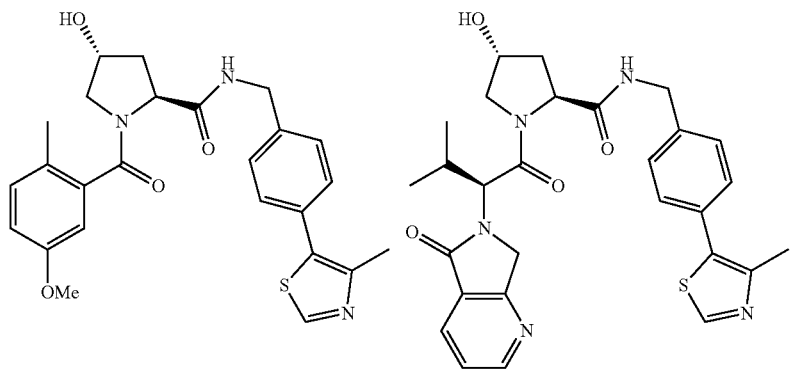

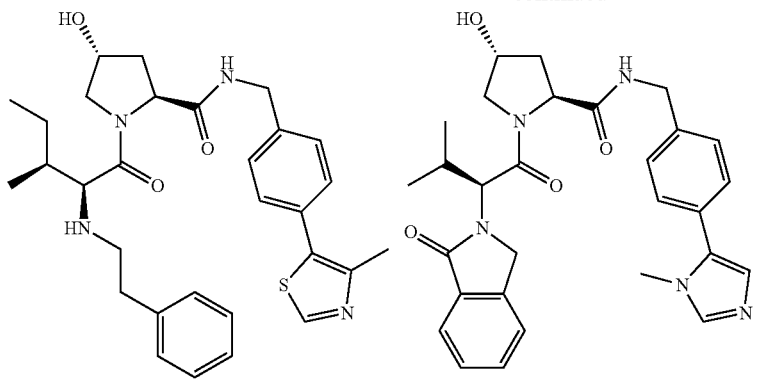
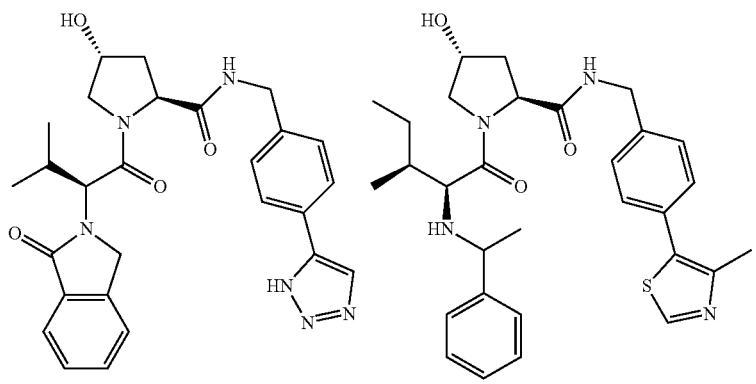
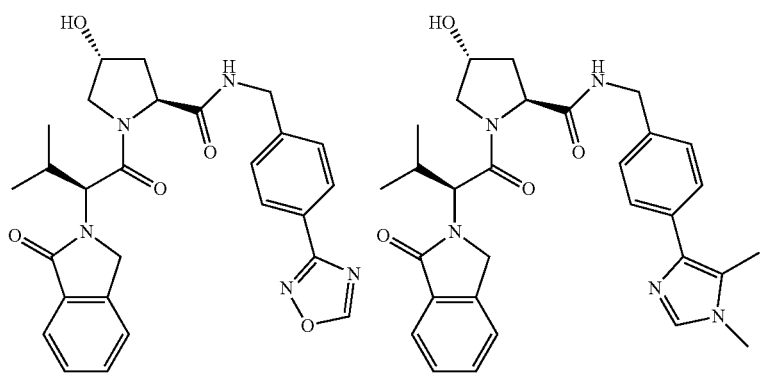
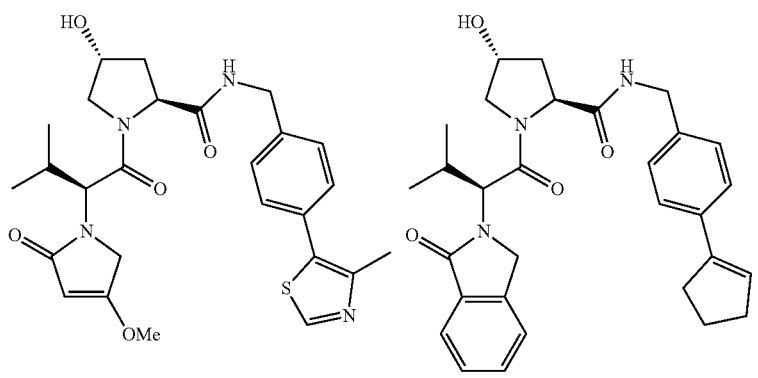

-continued
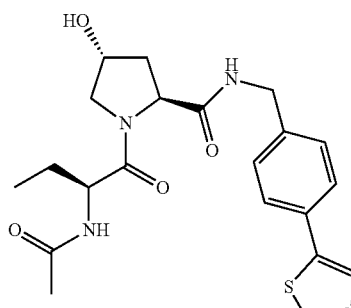
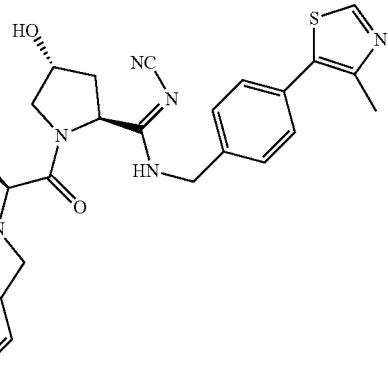
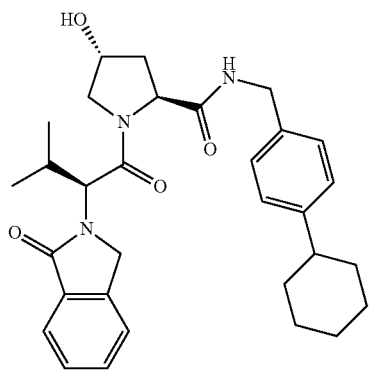
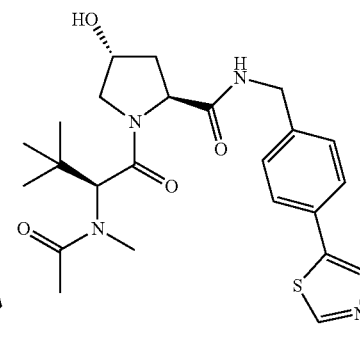
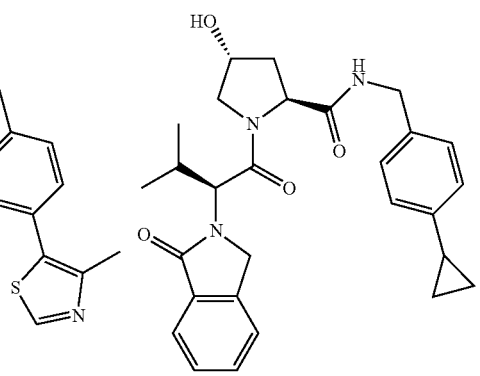
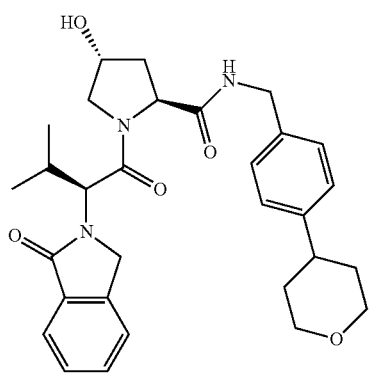
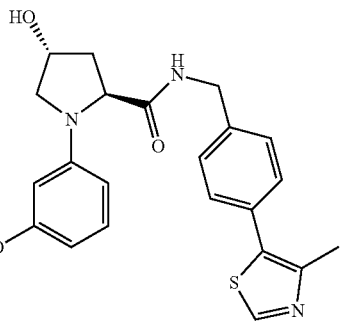
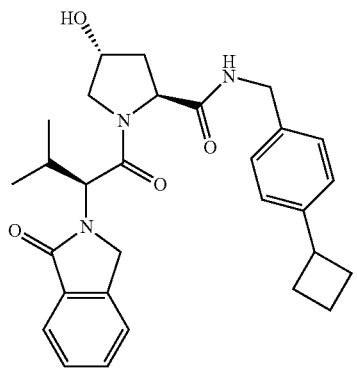
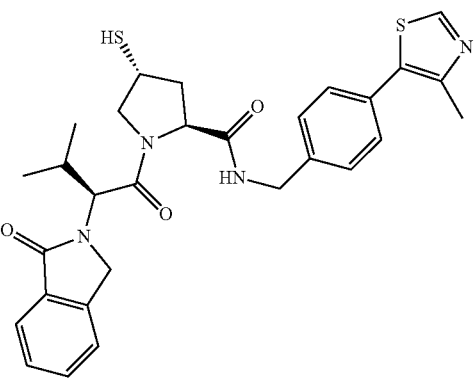

-continued
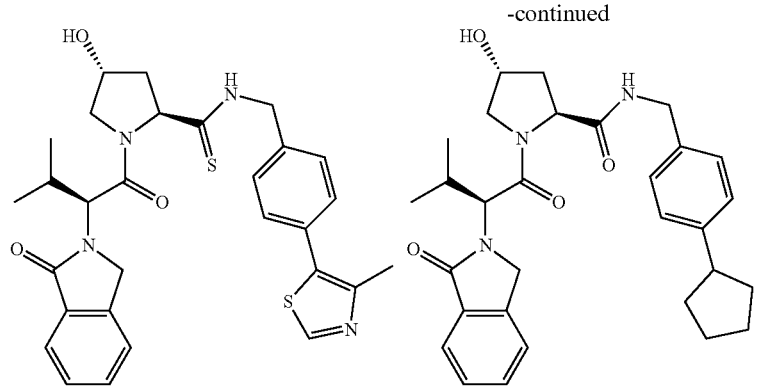
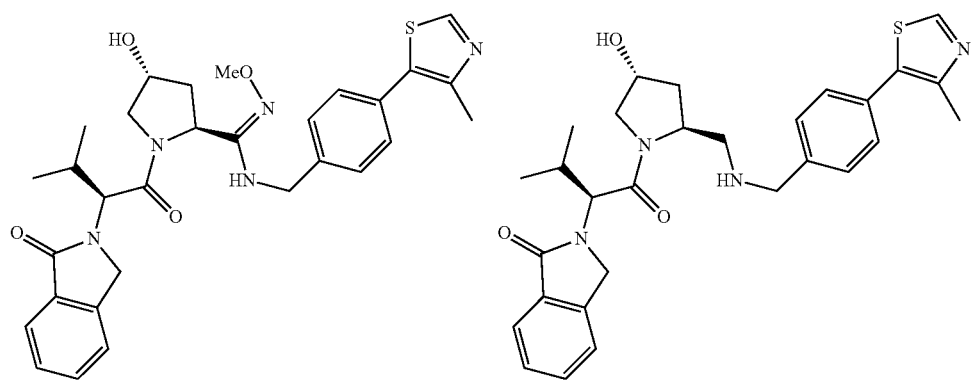
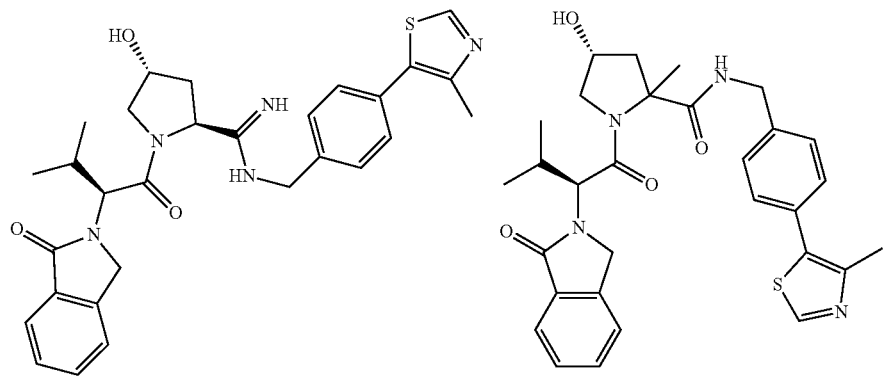
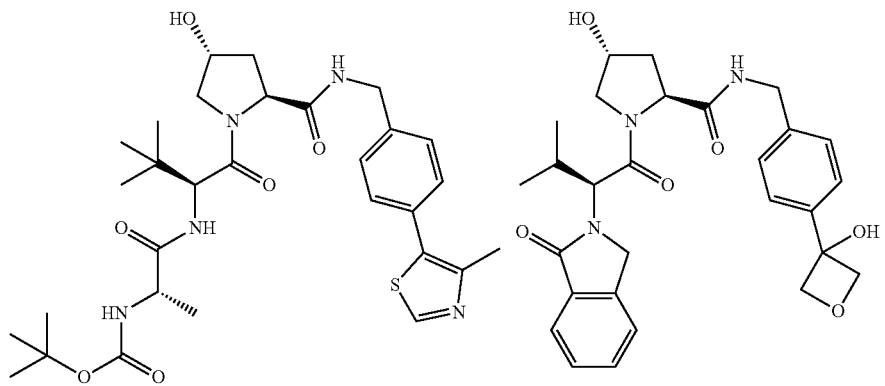

-continued
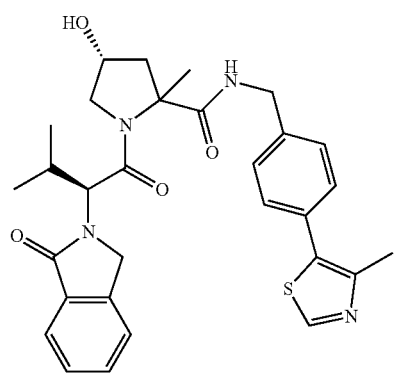
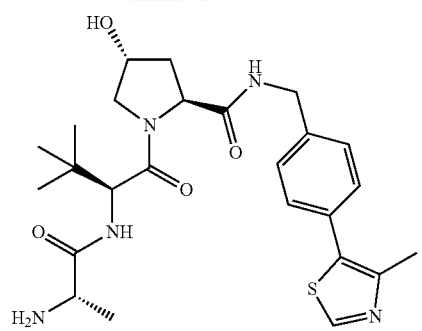
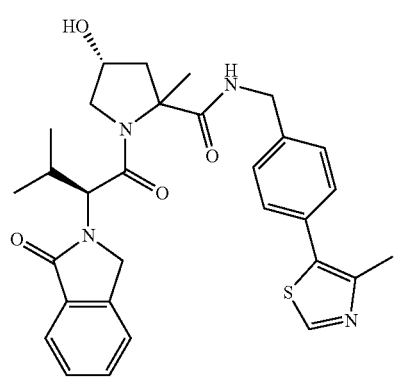
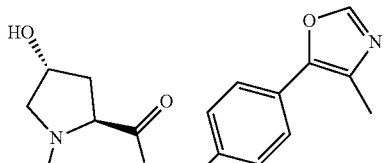
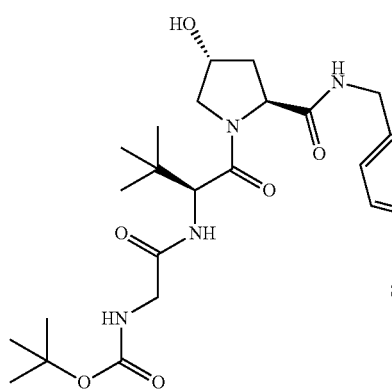
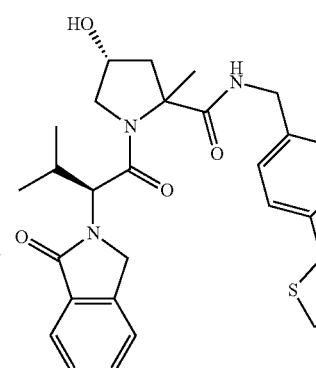
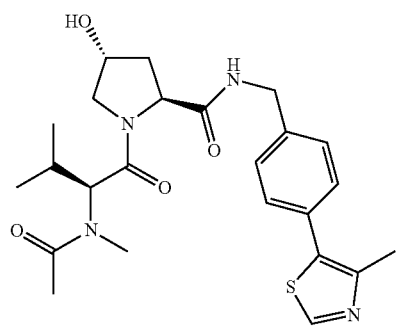
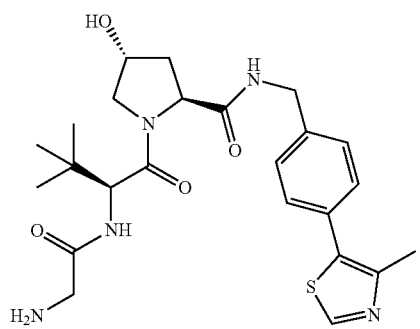

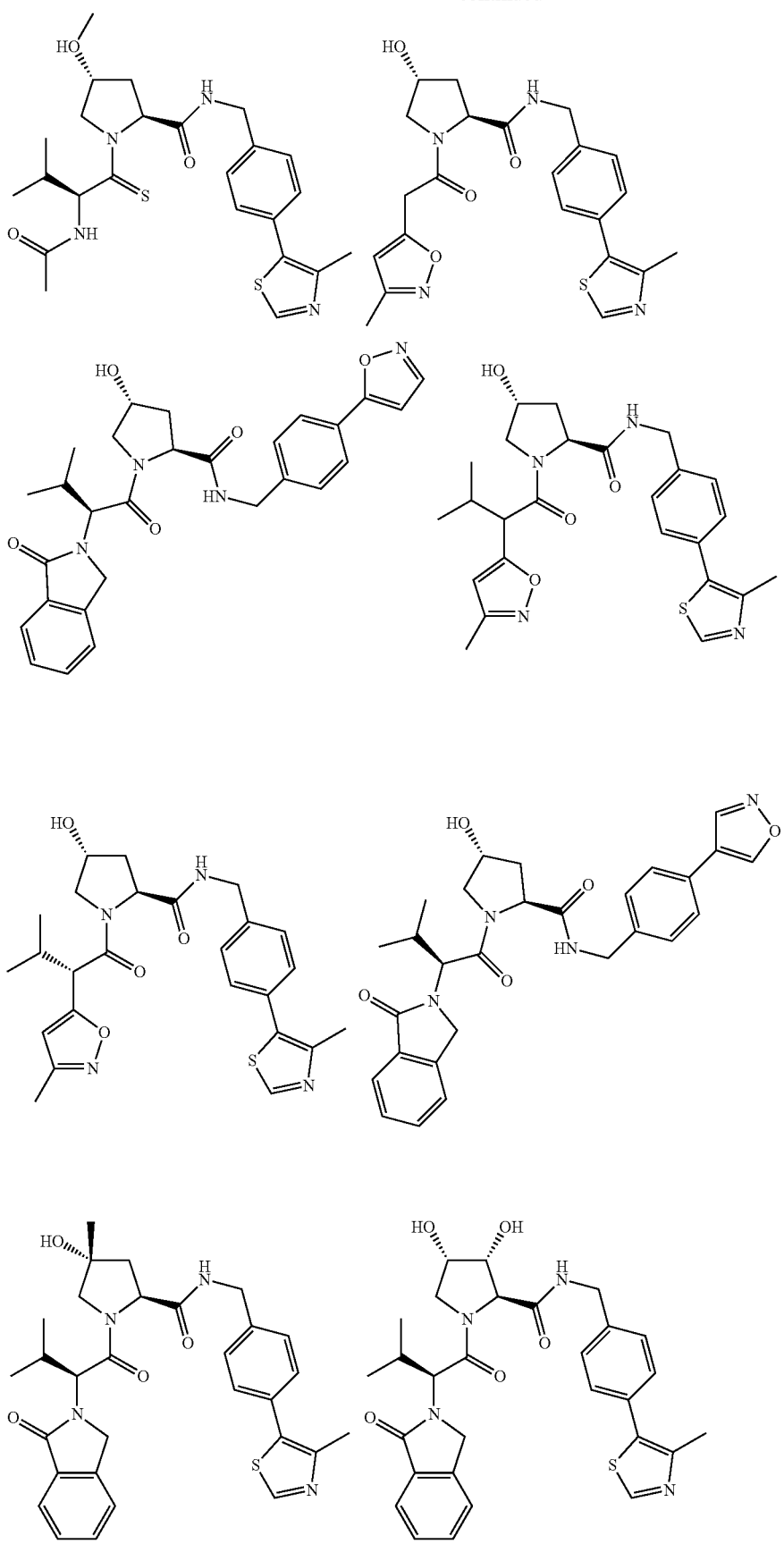

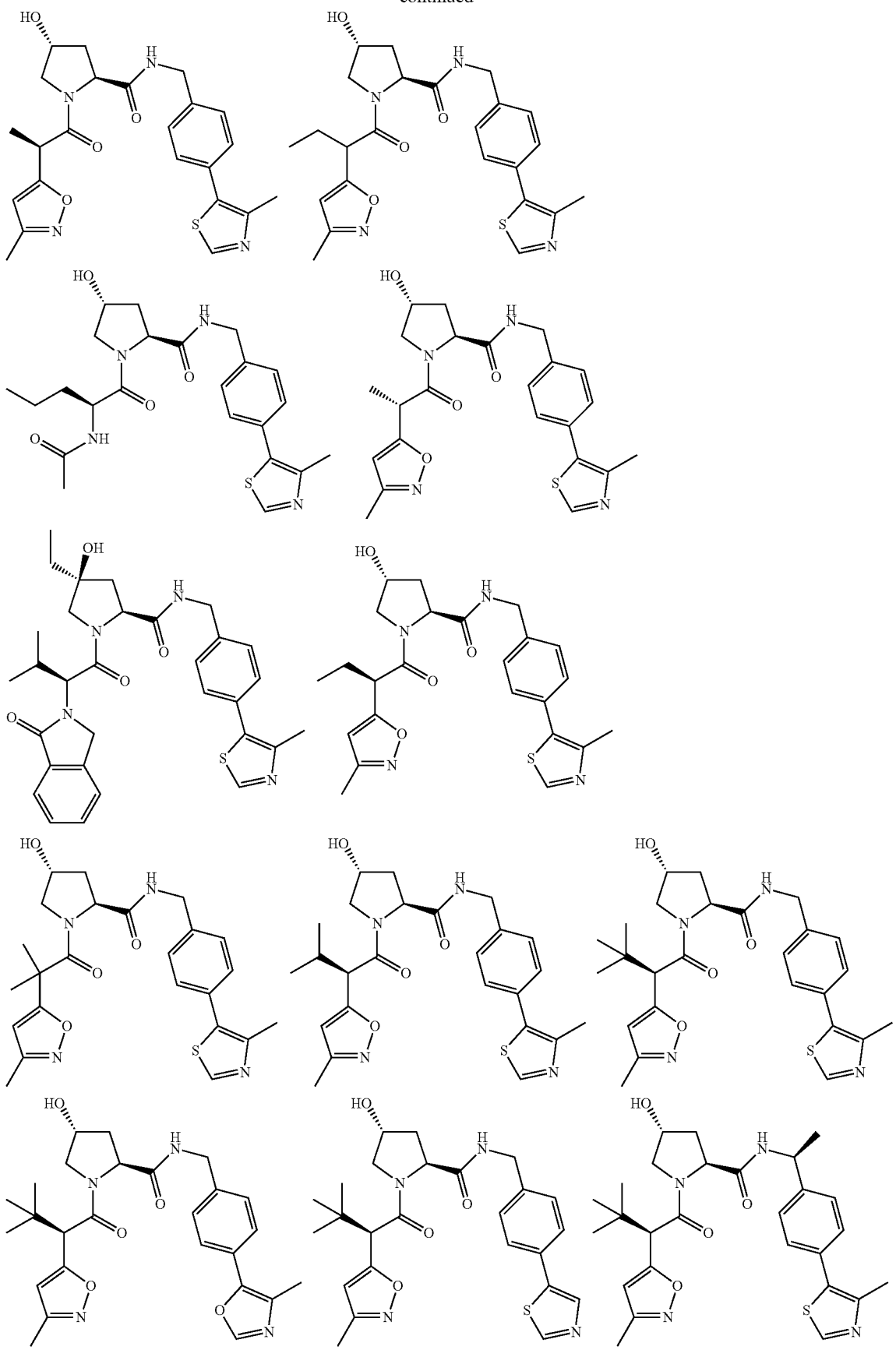

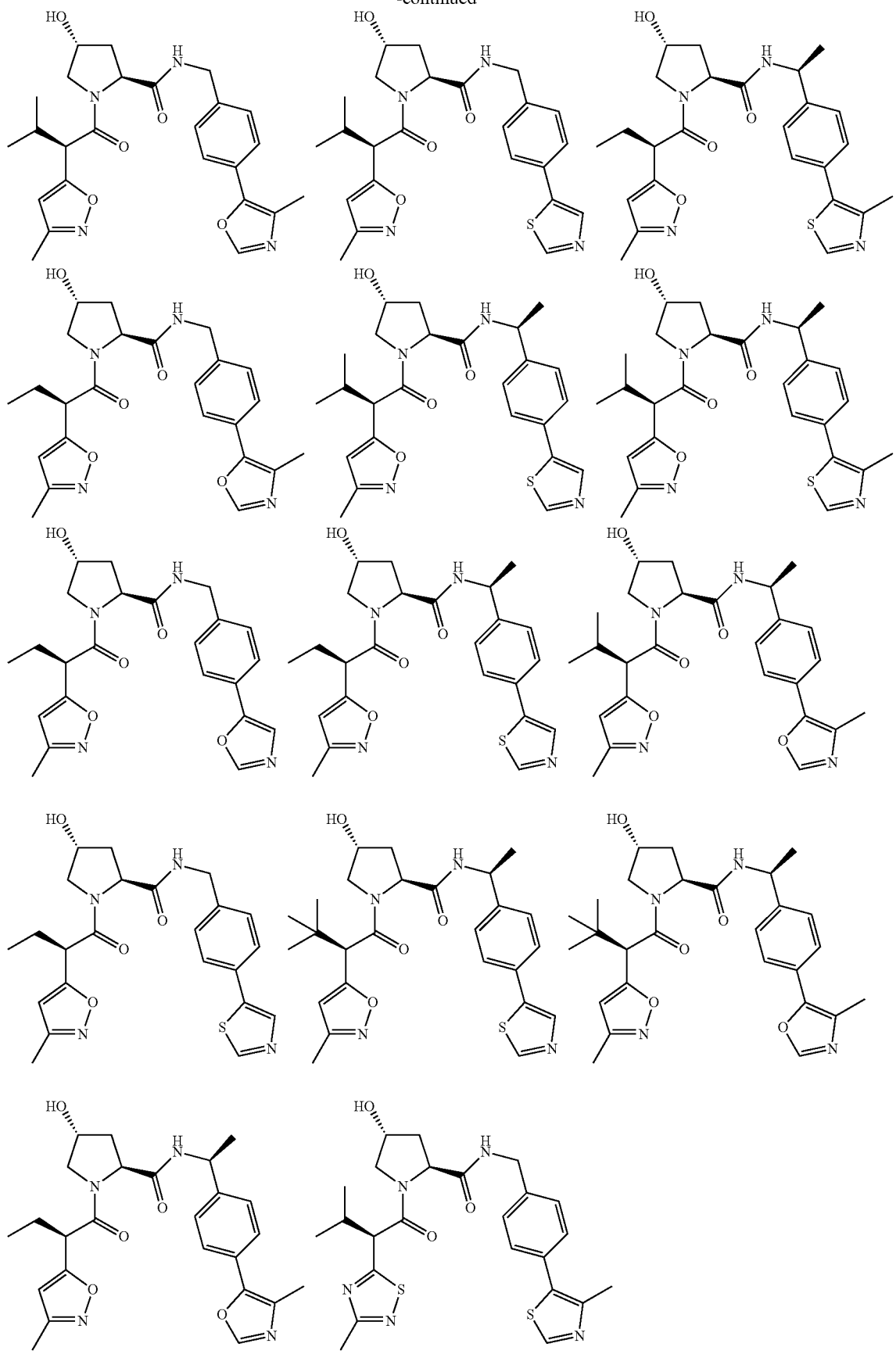

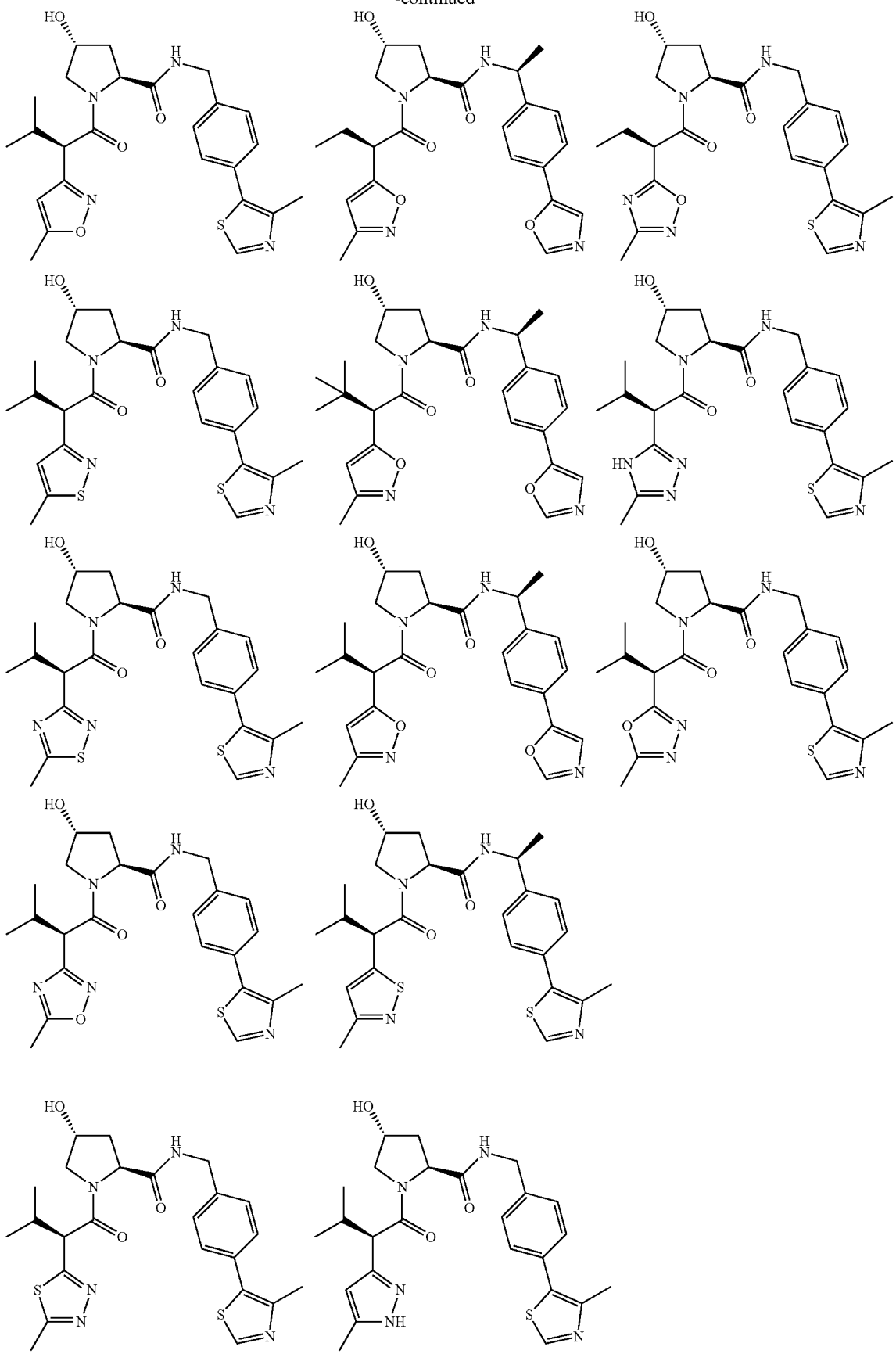

-continued
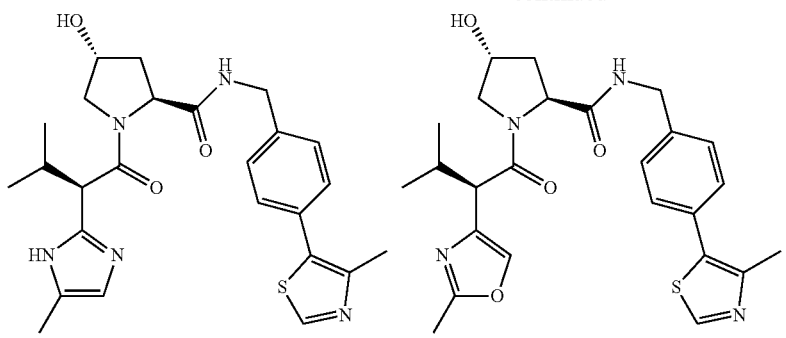
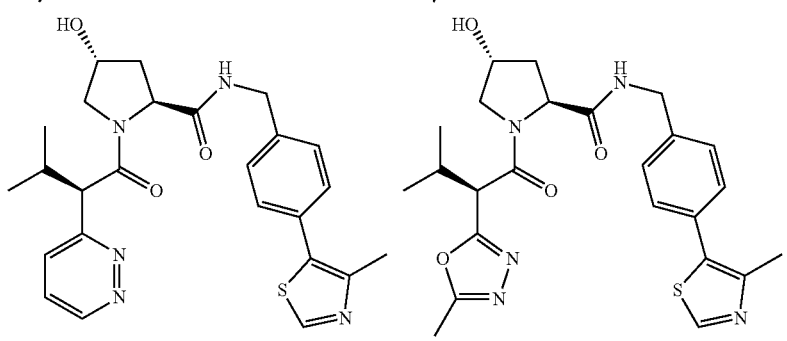
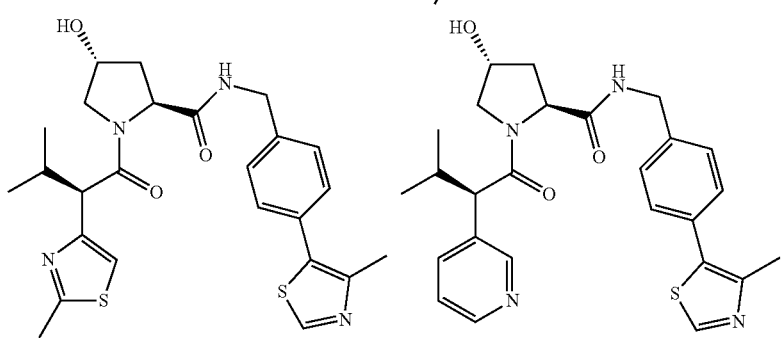
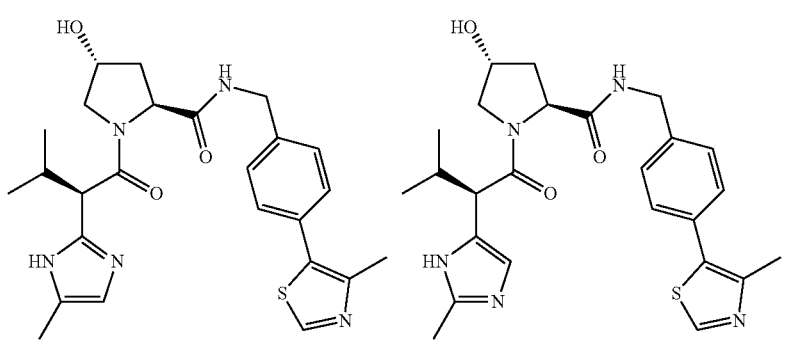
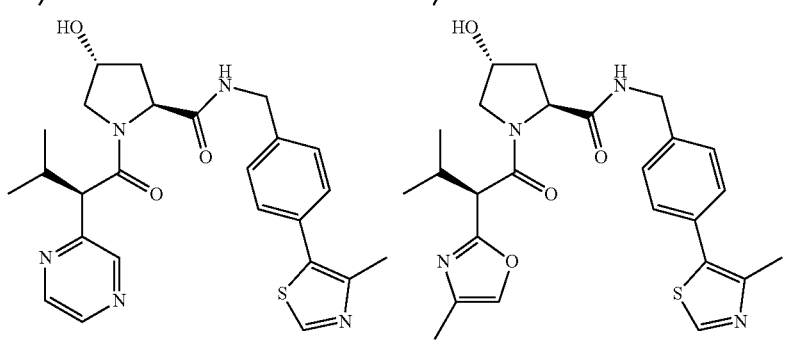

-continued
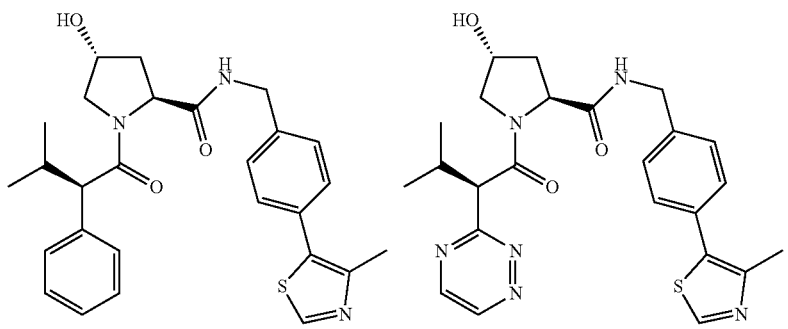
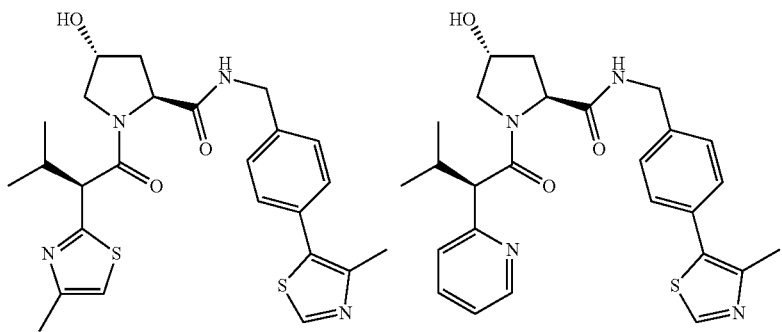
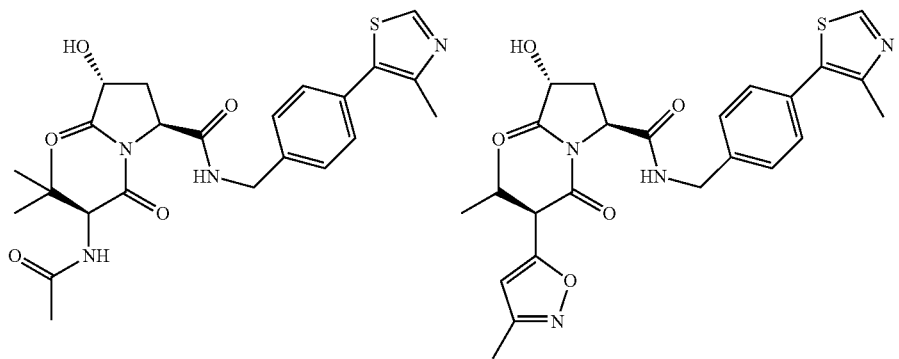
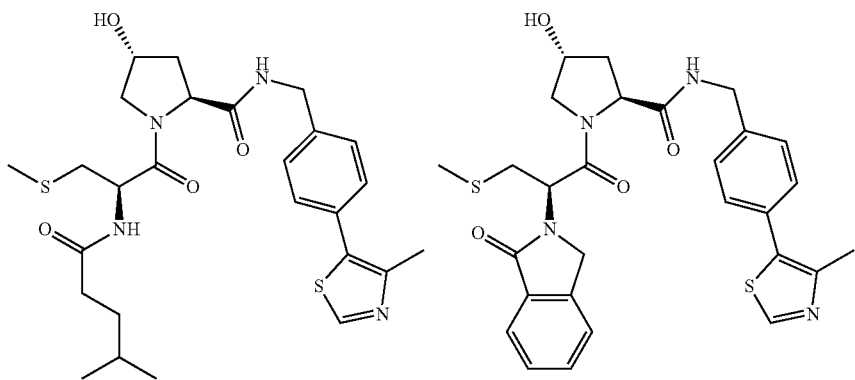

-continued
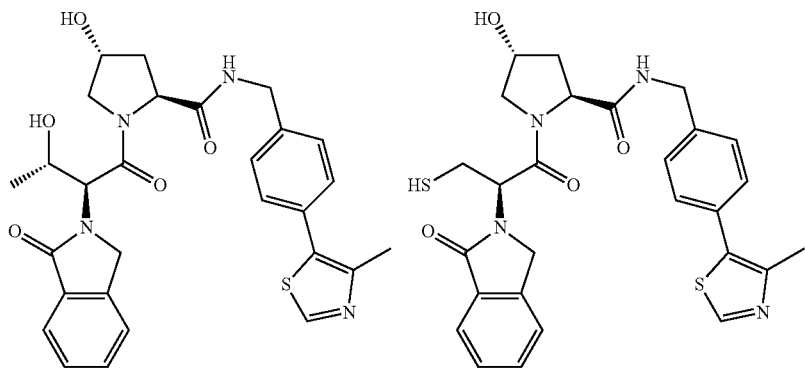
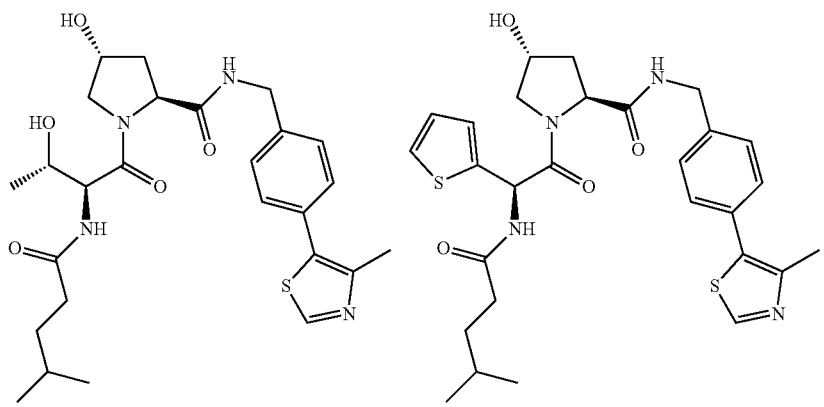
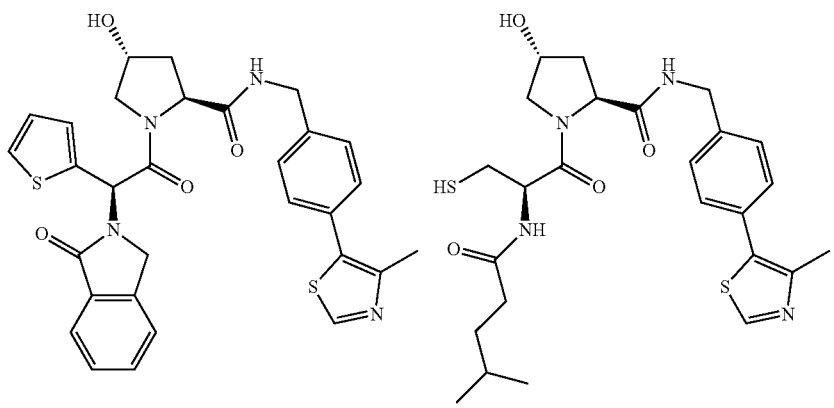
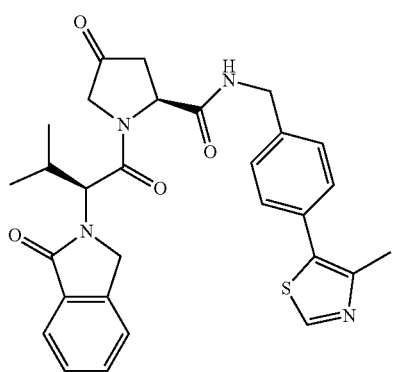

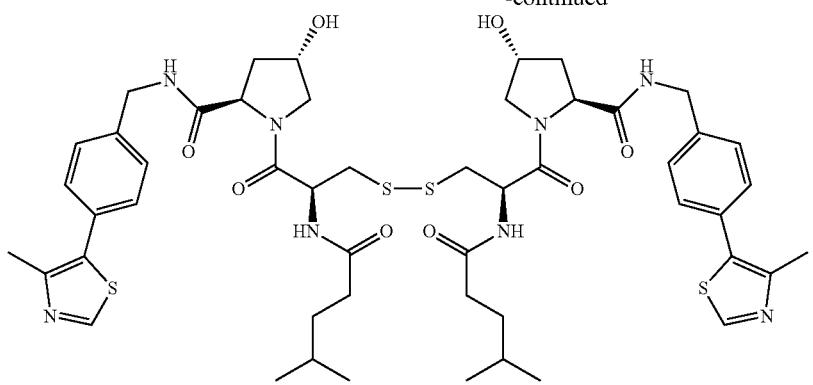
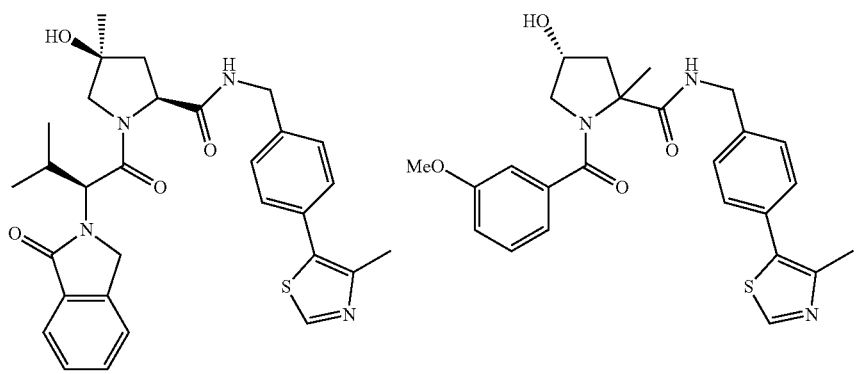
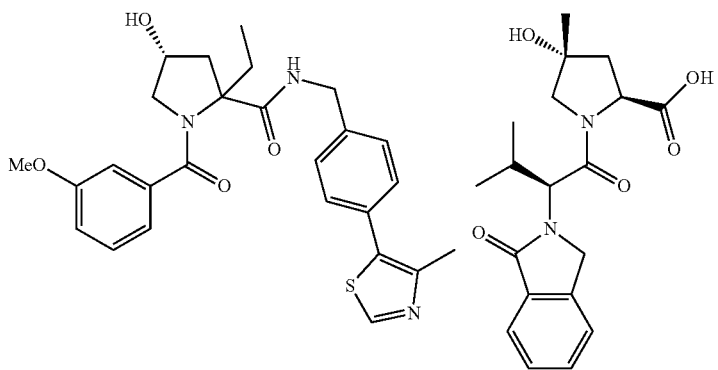
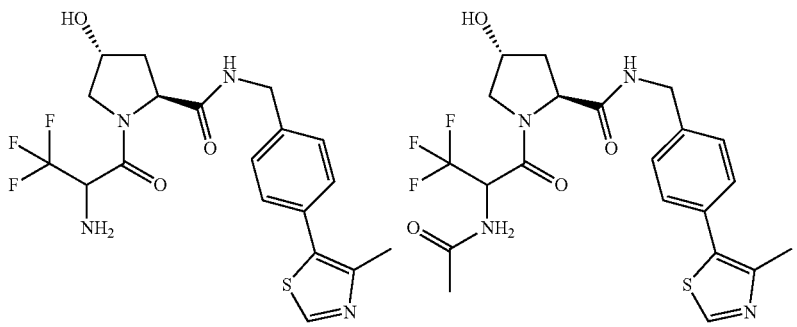

-continued
275
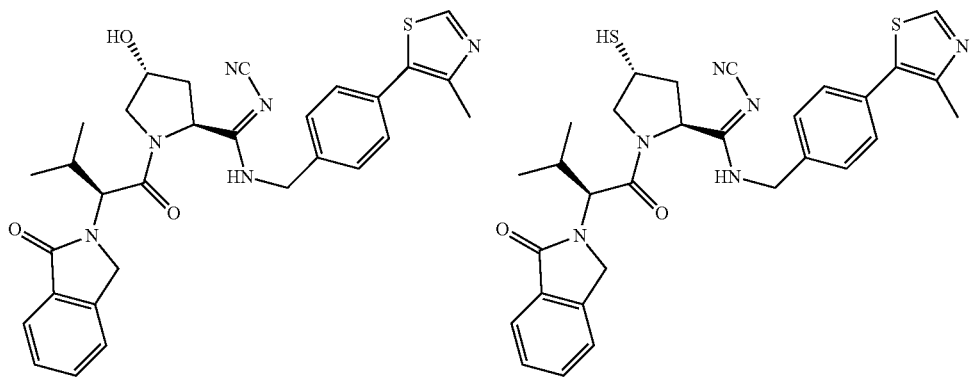
276
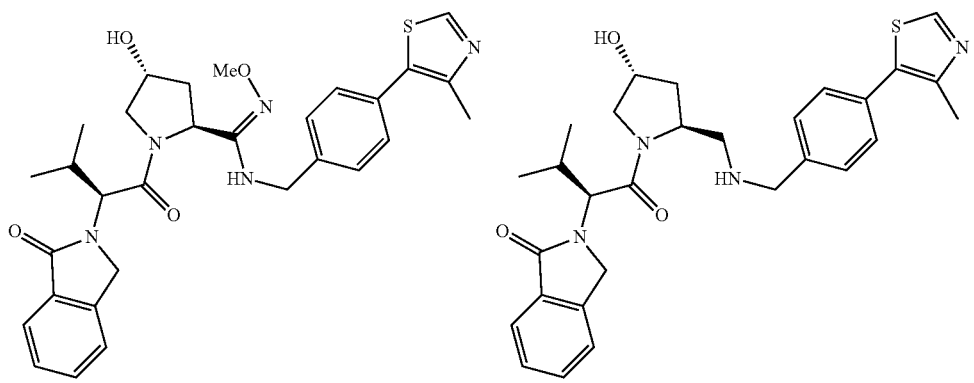
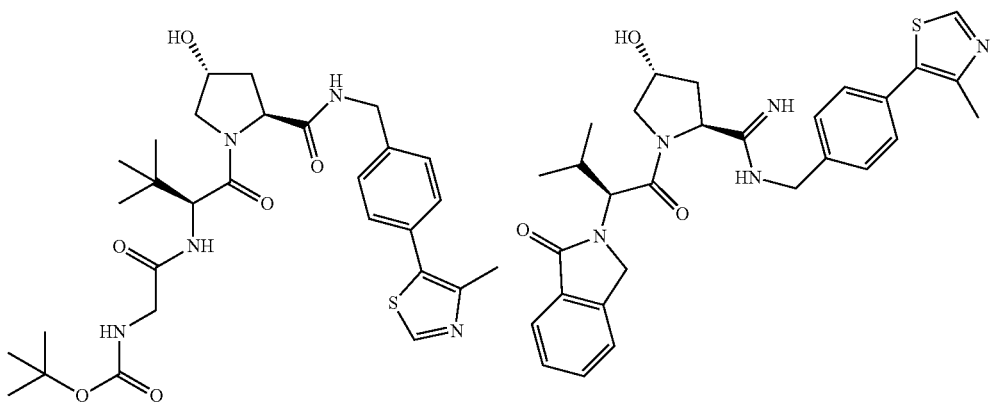
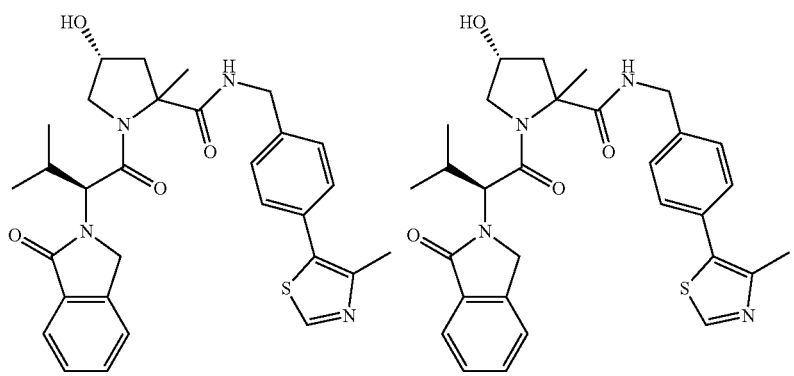

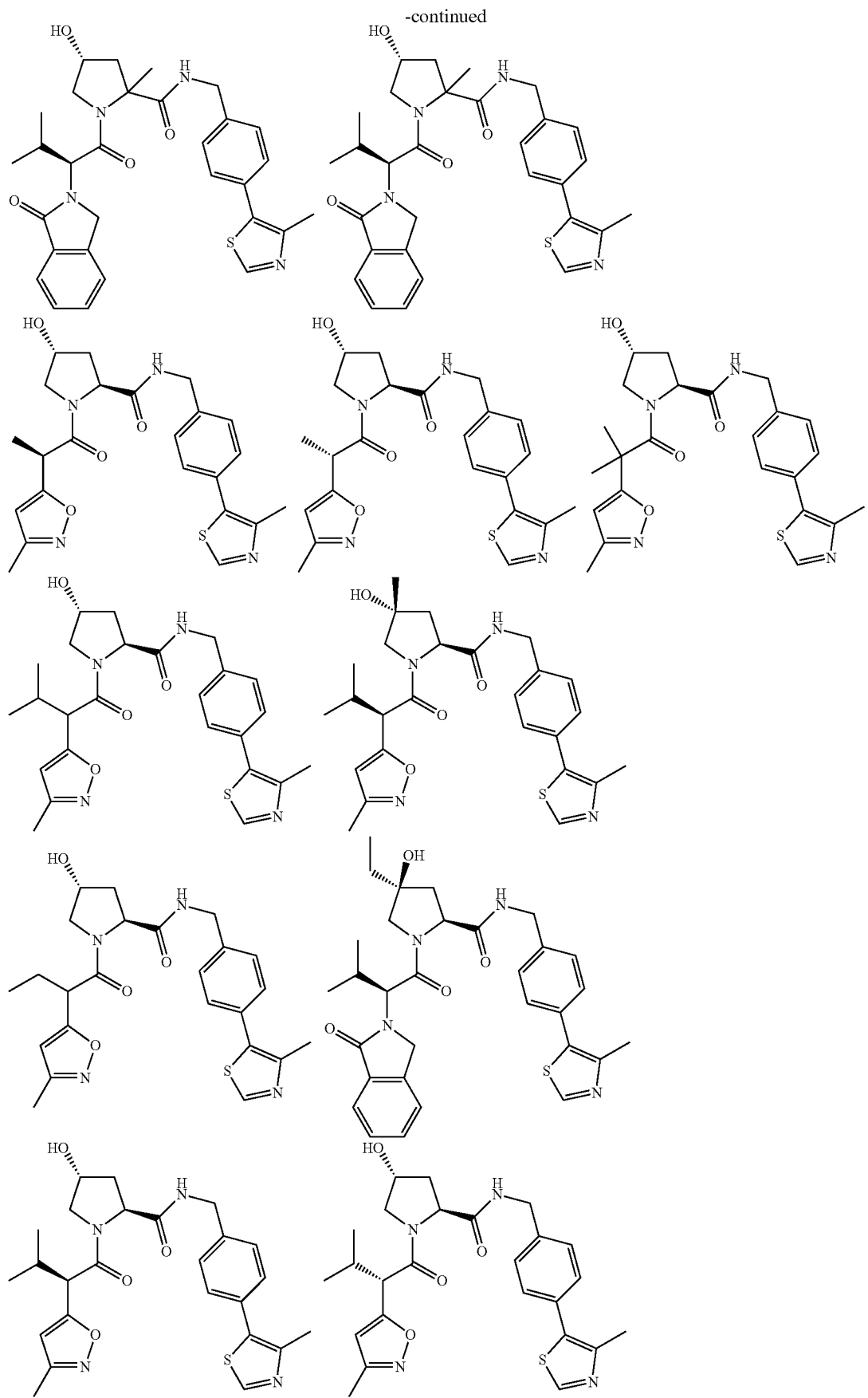

-continued
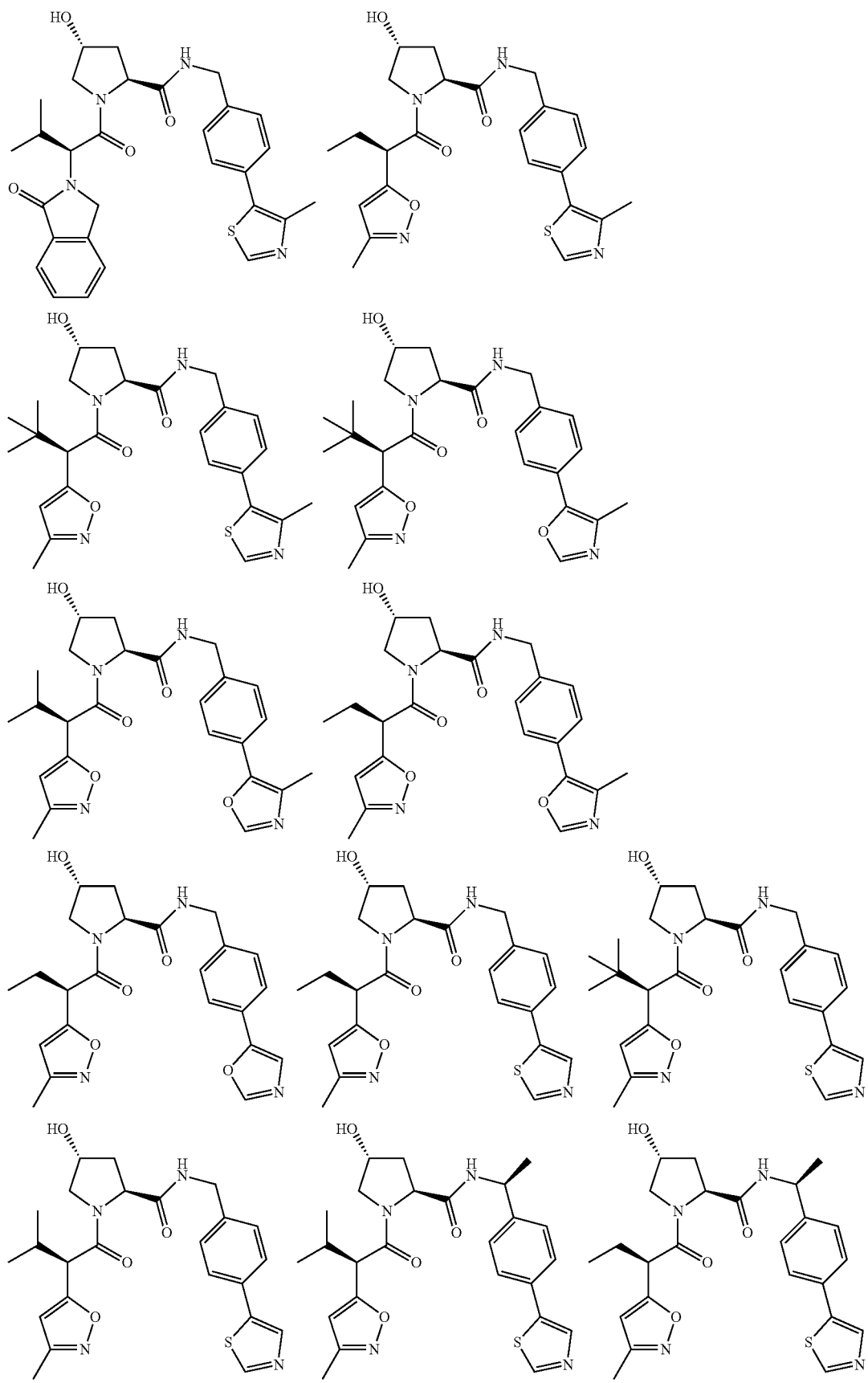

281 282
-continued
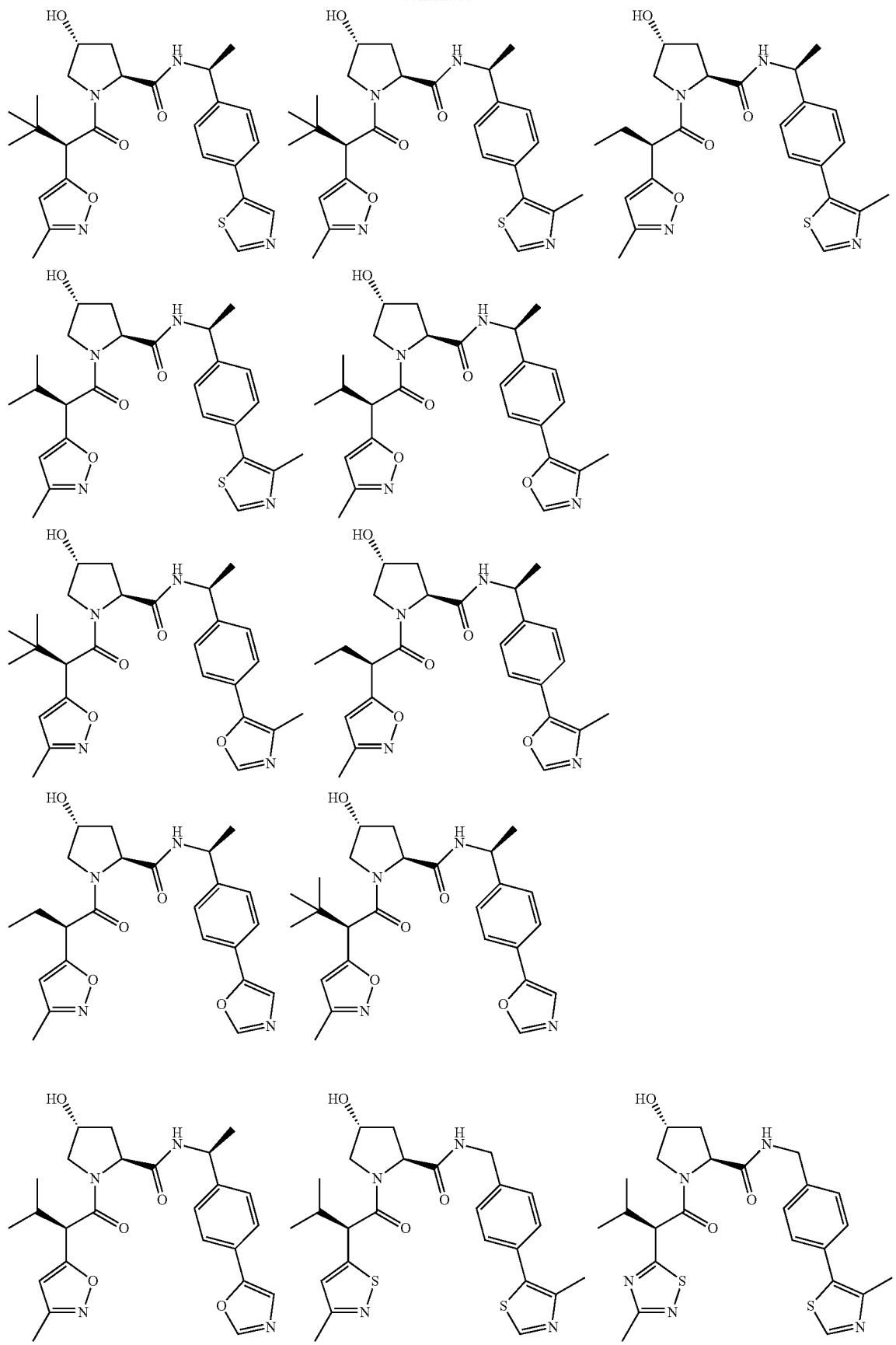

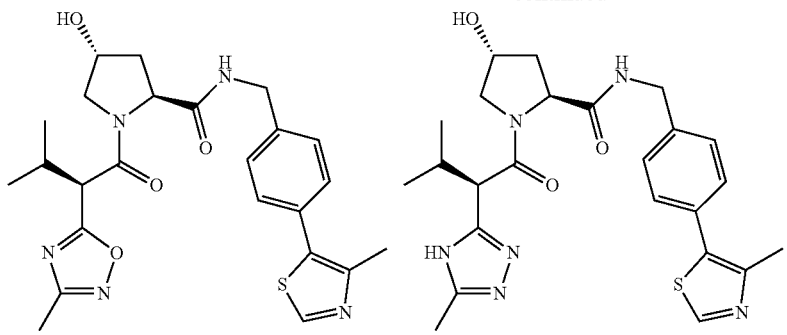
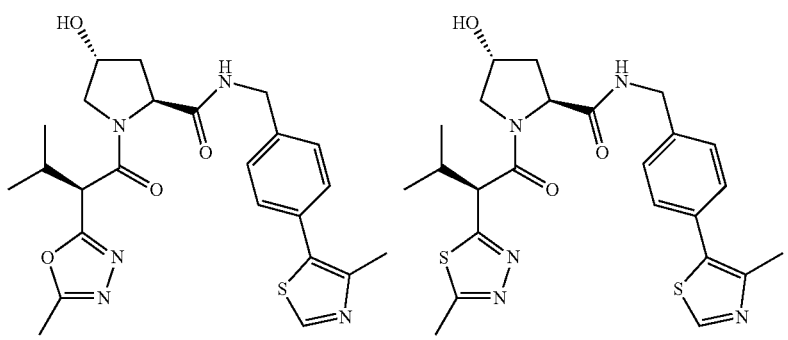
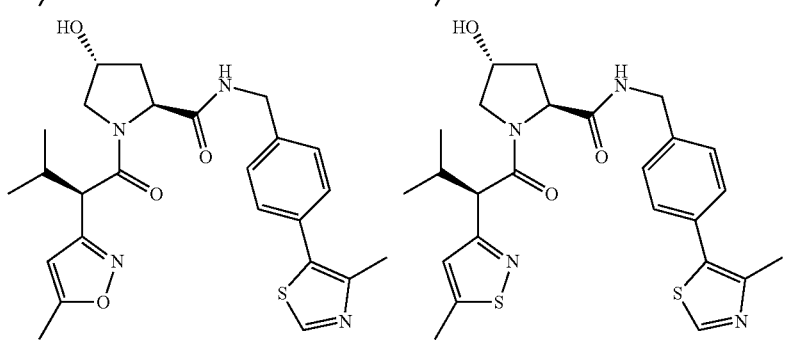
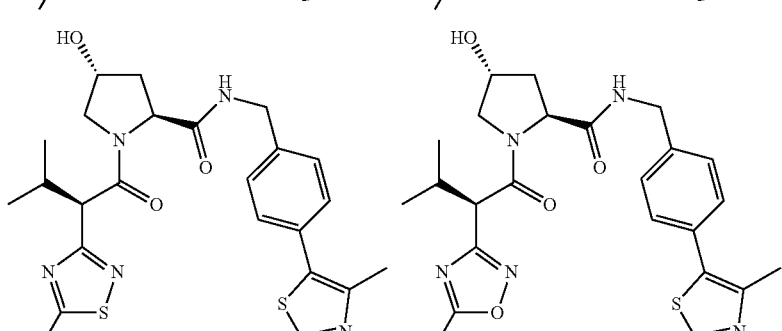
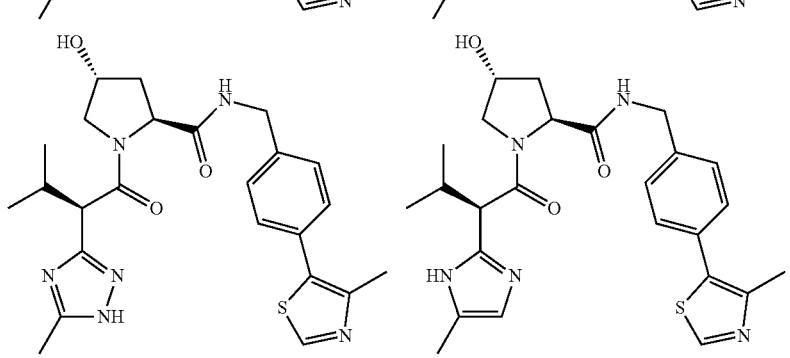

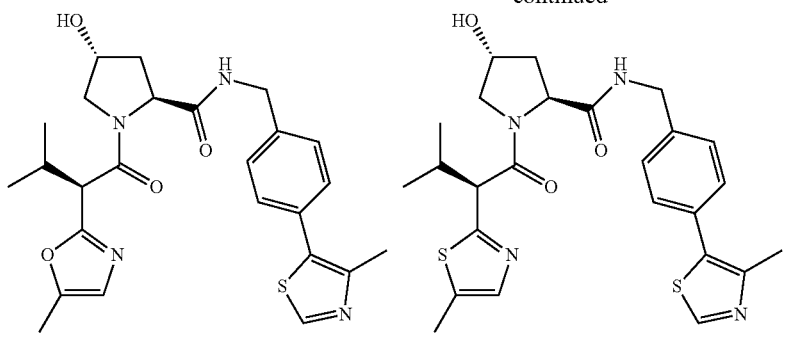
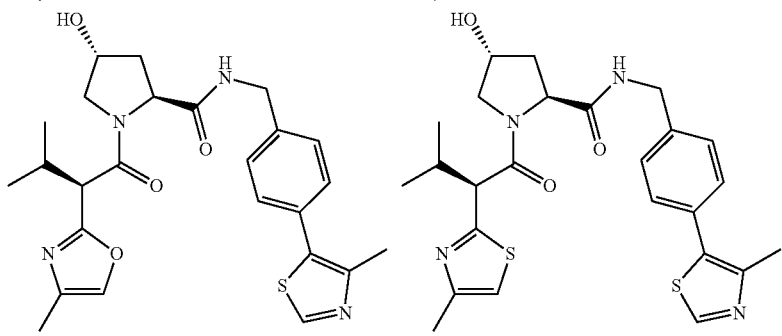
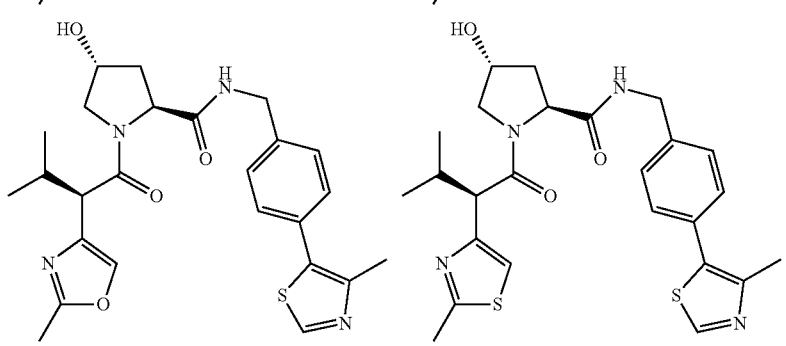
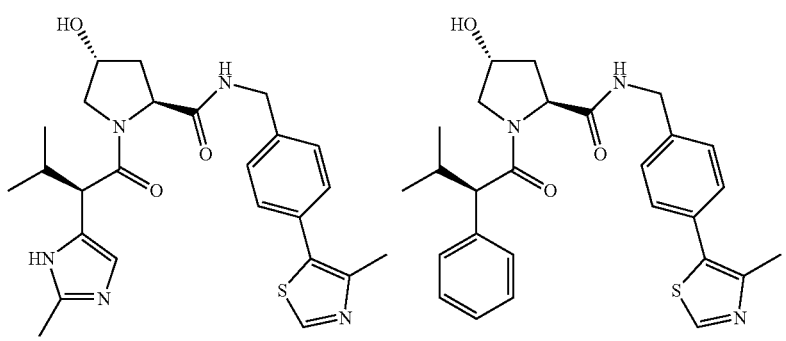
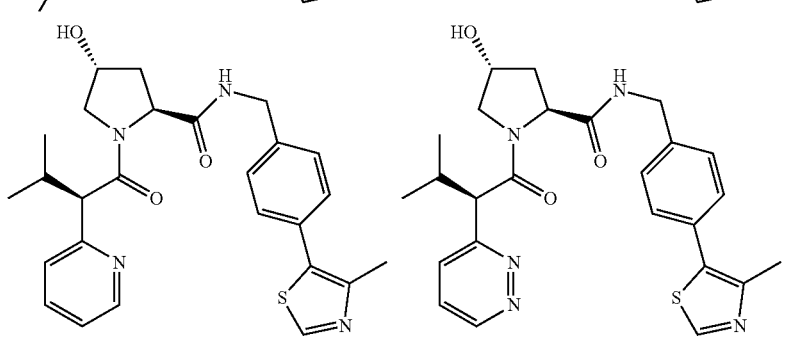

287                                    288
-continued
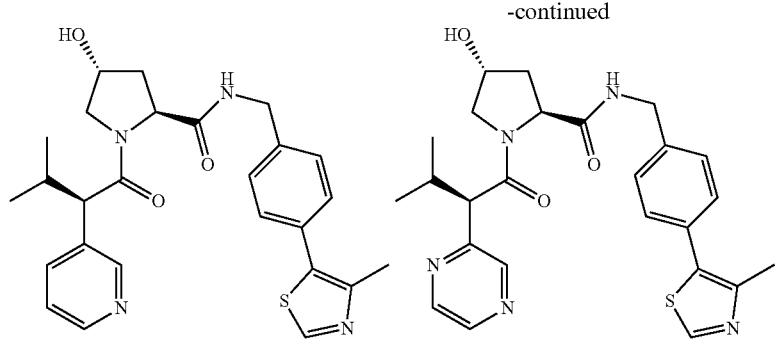
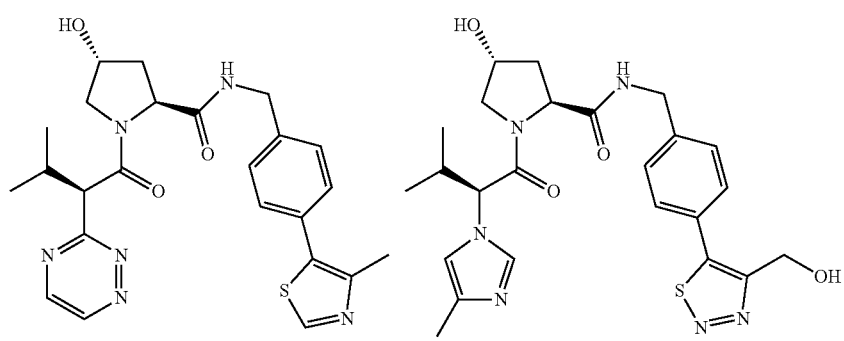
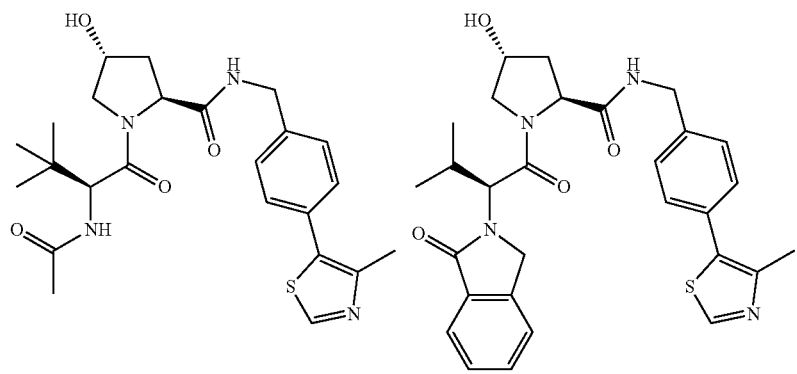
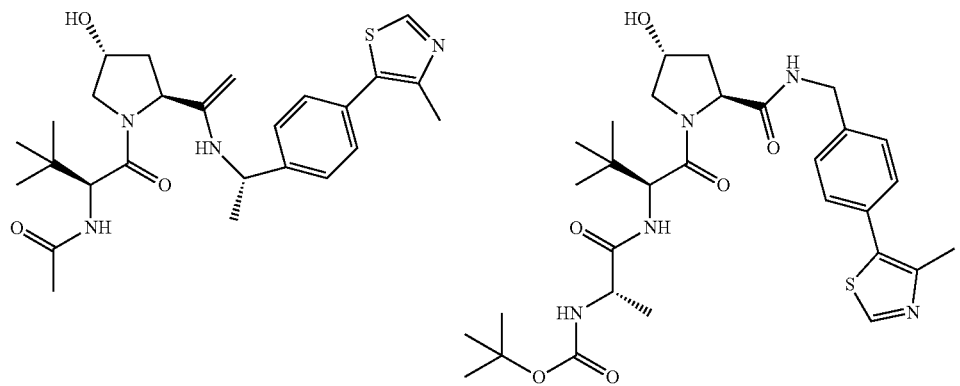

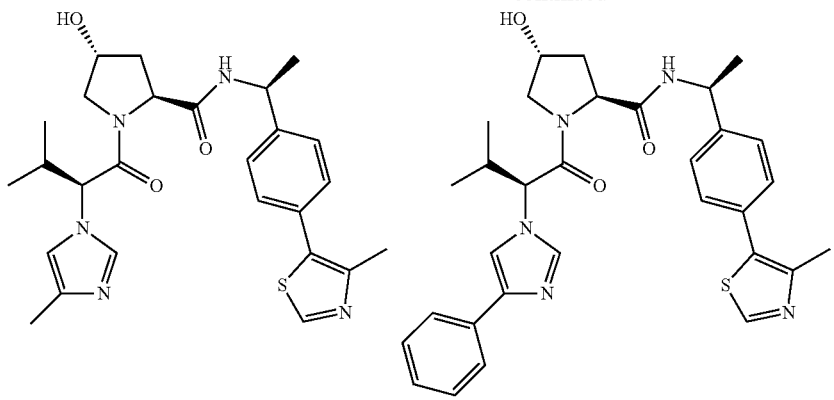
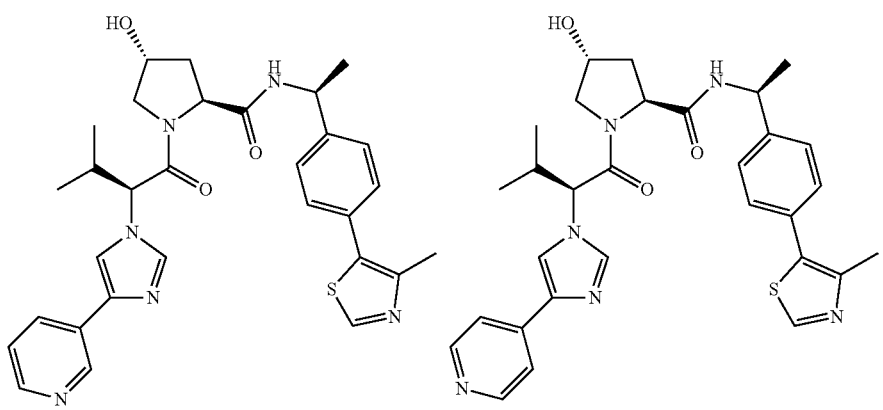
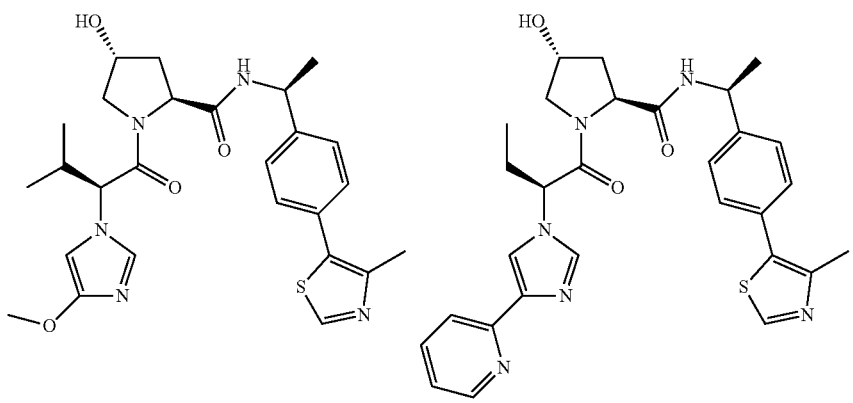
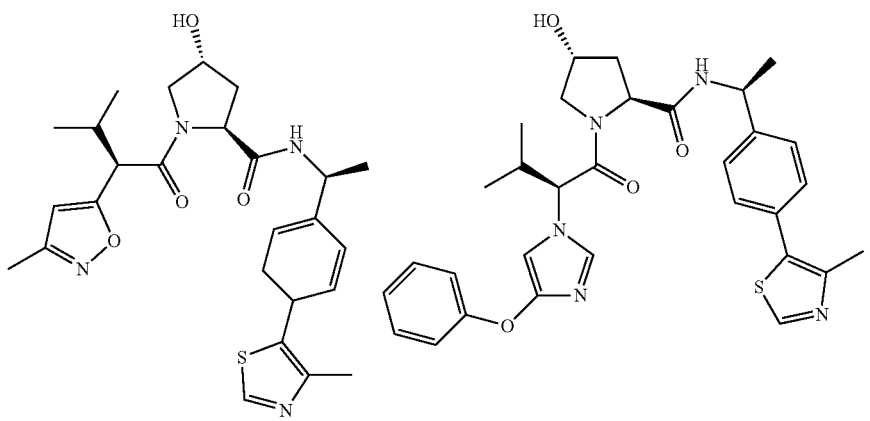

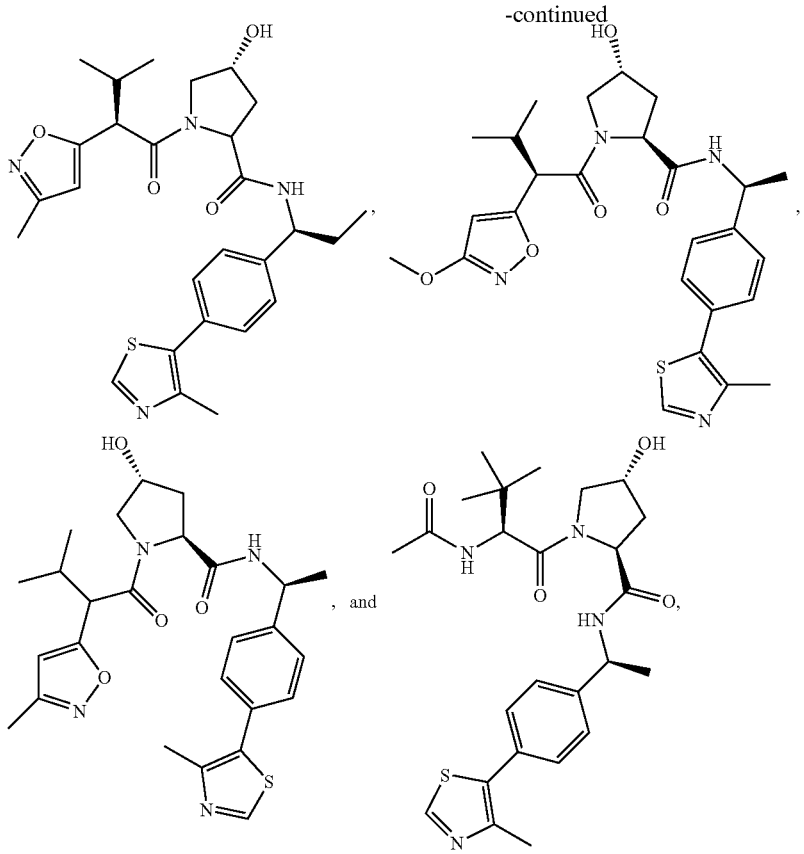

wherein the VLM may be connected to a PTM via a linker, as described herein, at any appropriate location, including, e.g., an aryl, heteroary, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., $-A^L{}_1 \ldots (A^L)_q-$ or $-(A^L)_q-$), wherein $A^L{}_1$ is a group coupled to PTM, and $(A^L)_q$ is a group coupled to ULM.

In any aspect or embodiment described herein, the linker group L is a bond or a chemical linker group represented by the formula $-(A^L)_q-$, wherein $A^L$ is a chemical moiety and q is an integer from 1-100, and wherein $A^L$ is covalently bound to the PTM and the ULM, and provides for sufficient binding of the PTM to the protein target and the ULM to an E3 ubiquitin ligase to result in target protein ubiquitination.

In certain embodiments, the linker group L is $-(A^L)_q-$, wherein:

$(A^L)_q$ is a group which is connected to at least one of a ULM (such as a CLM or a VLM), PTM moiety, or a combination thereof;

q of the linker is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^4$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC-C_{1-8}$alkyl, CCH, $CH=CH(C_{1-8}alkyl)$, $C(C_{1-8}alkyl)=CH(C_{1-8}alkyl)$, $C(C_{1-8}alkyl)=C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl) SO_2N(C_{1-8}alkyl)_2$, $NH SO_2NH(C_{1-8}alkyl)$, $NH SO_2N(C_{1-8}alkyl)_2$, $NH SO_2NH_2$.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is connected to ULM, and $A^L_1$ and $(A^L)_q$ are connected via structural units of the linker (L).

In certain embodiments, e.g., where q of the linker is 2, $(A^L)_q$ is a group which is connected to $A^L_1$ and to a ULM.

In certain embodiments, e.g., where q of the linker is 1, the structure of the linker group L is -$A^L_1$-, and $A^L_1$ is a group which is connected to a ULM moiety and a PTM moiety.

In certain embodiments, the unit $A^L$ of linker (L) comprises a group represented by a general structure selected from the group consisting of:
—NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(hetero cycloalkyl)-, —NR(CH$_2$CH$_2$O)$_n$-(lower alkyl)-O—CH$_2$—, —NR(CH$_2$CH$_2$O)$_n$-(hetero cycloalkyl)-O—CH$_2$—, —NR(CH$_2$CH$_2$O)$_n$-Aryl-O—CH$_2$—, NR(CH$_2$CH$_2$O)$_n$-(hetero aryl)-O—CH$_2$—, —NR(CH$_2$CH$_2$O)$_n$-(cyclo alkyl)-O-(hetero aryl)-O—CH$_2$—, —NR(CH$_2$CH$_2$O)$_n$-(cyclo alkyl)-O-Aryl-O—CH$_2$—, —NR(CH$_2$CH$_2$O)$_n$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)l-, —NR(CH$_2$CH$_2$)$_n$-(cycloalkyl)-O-(heterocyclyl)-CH$_2$, —NR(CH$_2$CH$_2$)$_n$-(heterocyclyl)-(heterocyclyl)-CH$_2$, —N(R1R2)-(heterocyclyl)-CH$_2$; where n of the linker can be 0 to 10;

R of the linker can be H, lower alkyl;

R1 and R2 of the linker can form a ring with the connecting N.

In any aspect or embodiment described herein, the unit $A^L$ of linker (L) comprises a group selected from:

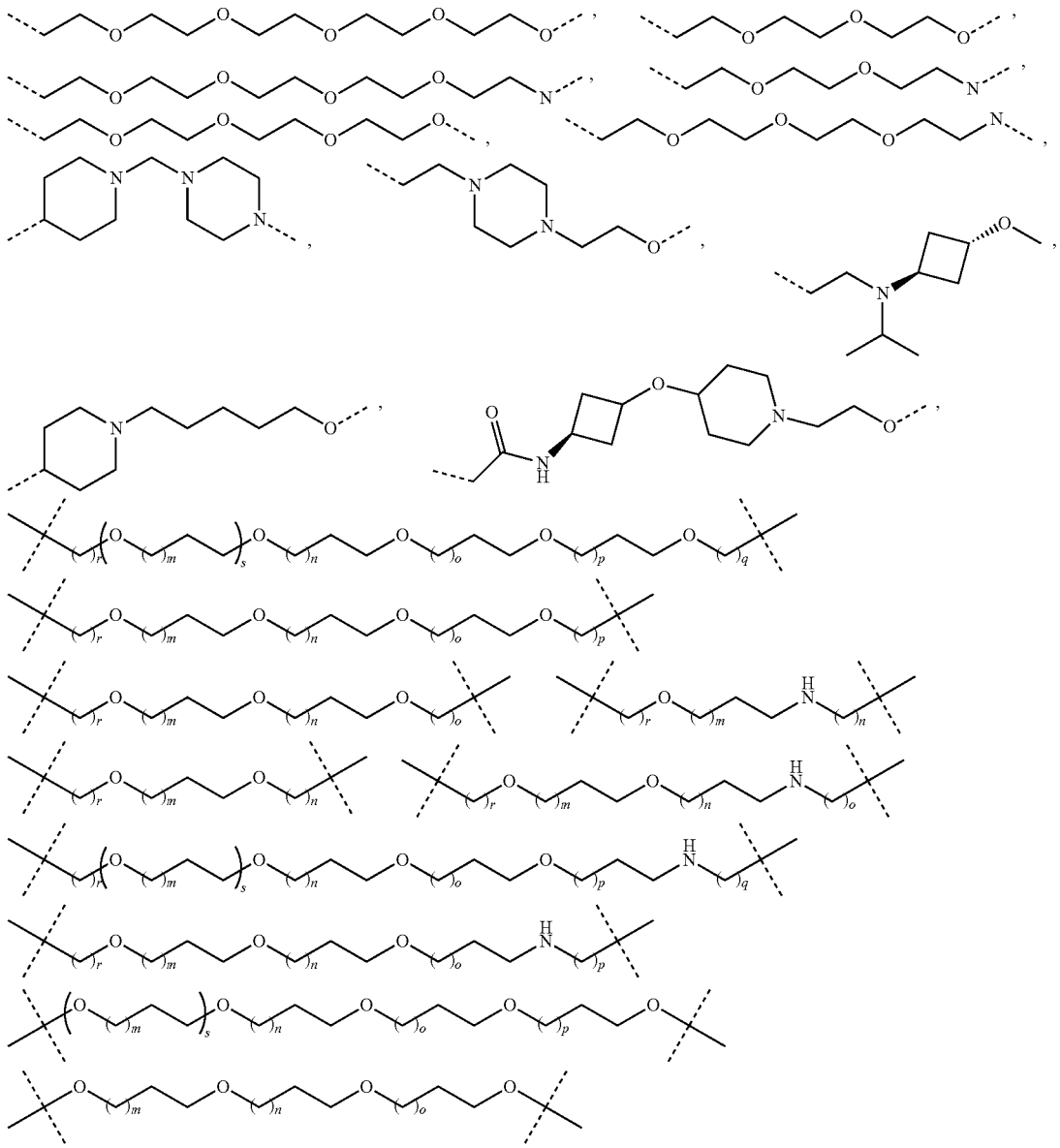

-continued
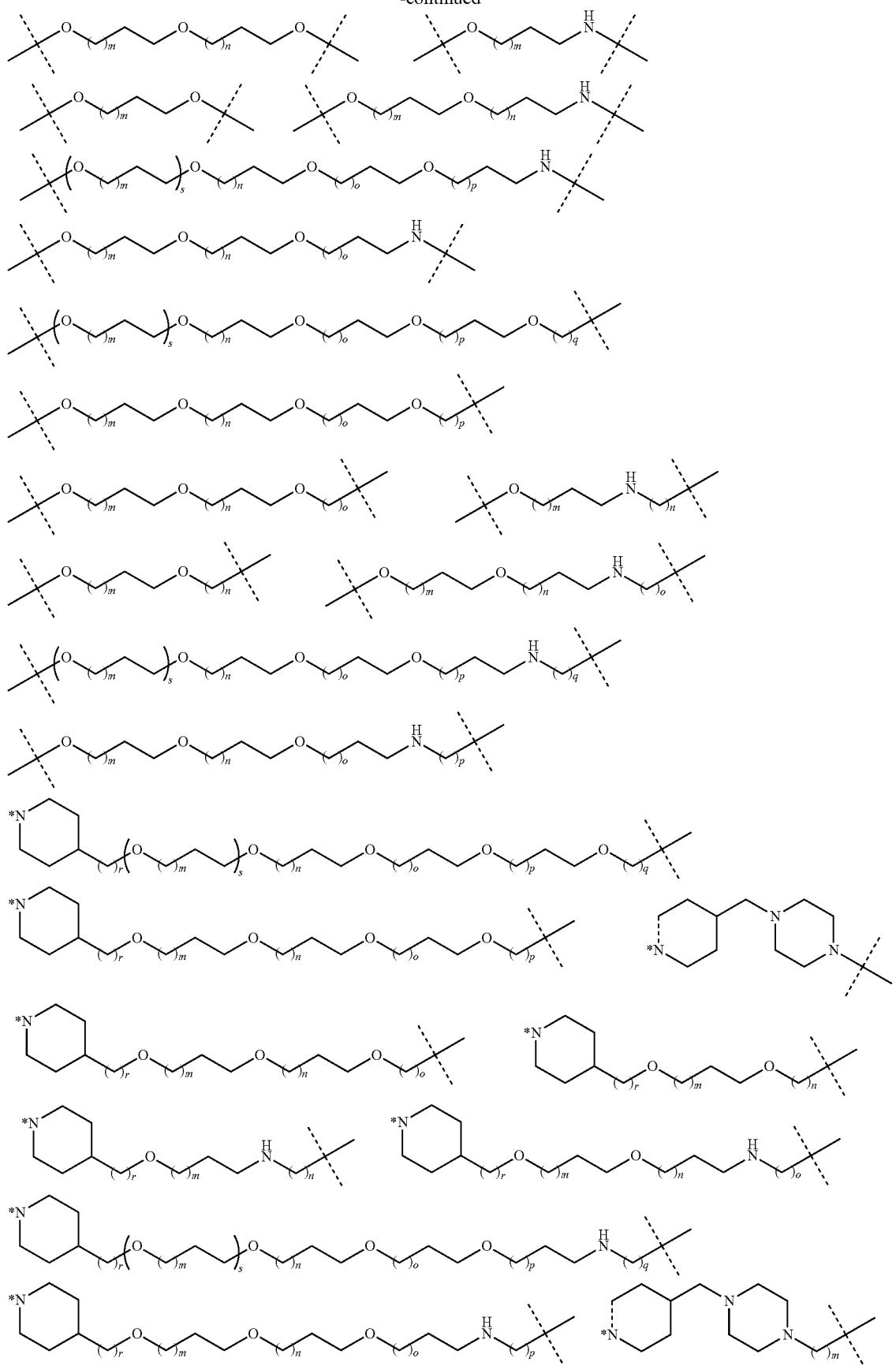

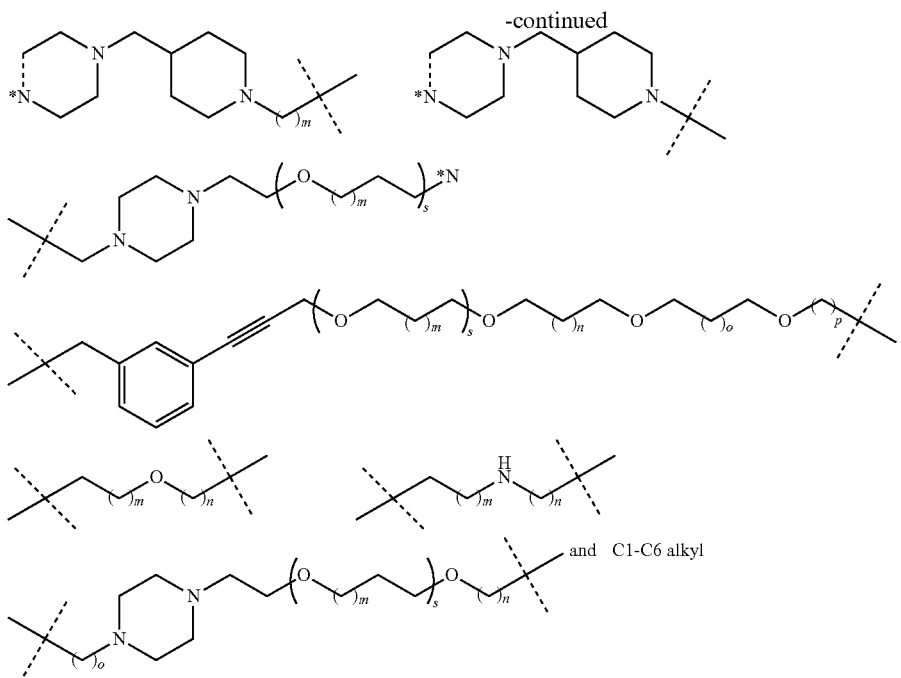
wherein:
*N of the heterocycloalkyl is shared with the PTM; and each m, n, o, p, q, r, and s are independently selected from 0, 1, 2, 3, 4, 5, 6, 7, 8, 9, 10, 11, 12, 13, 14, 15, 16, 17, 18, 19, or 20.
In certain embodiments, the unit $A^L$ of linker (L) comprises a group represented by a general structure selected from the group consisting of:
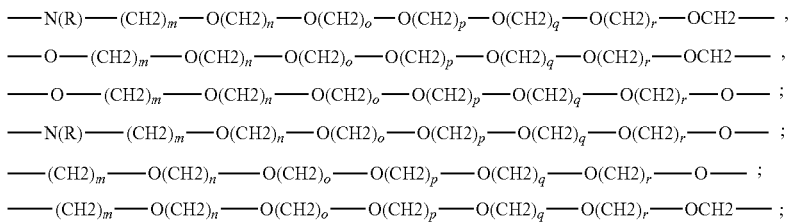
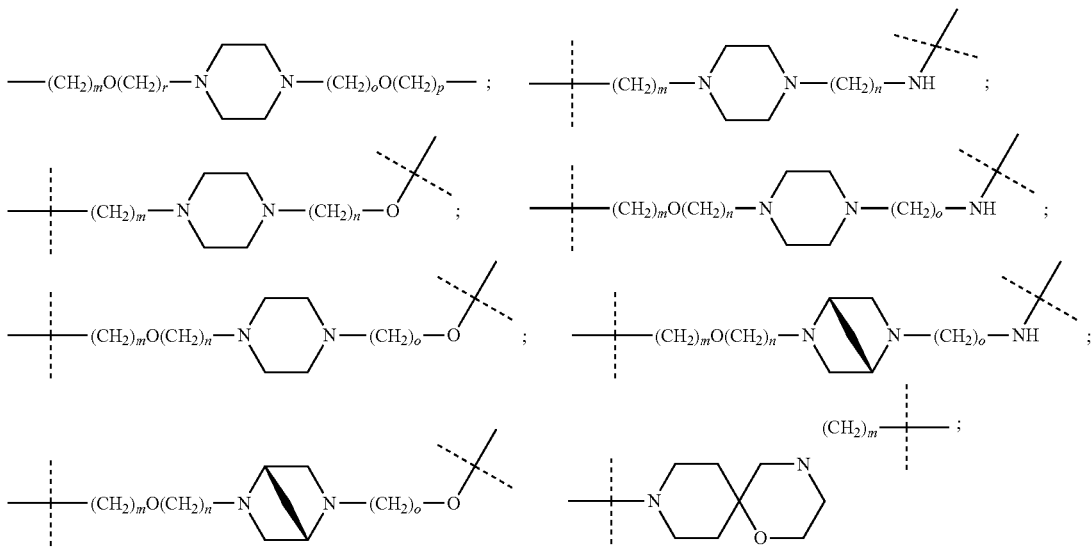

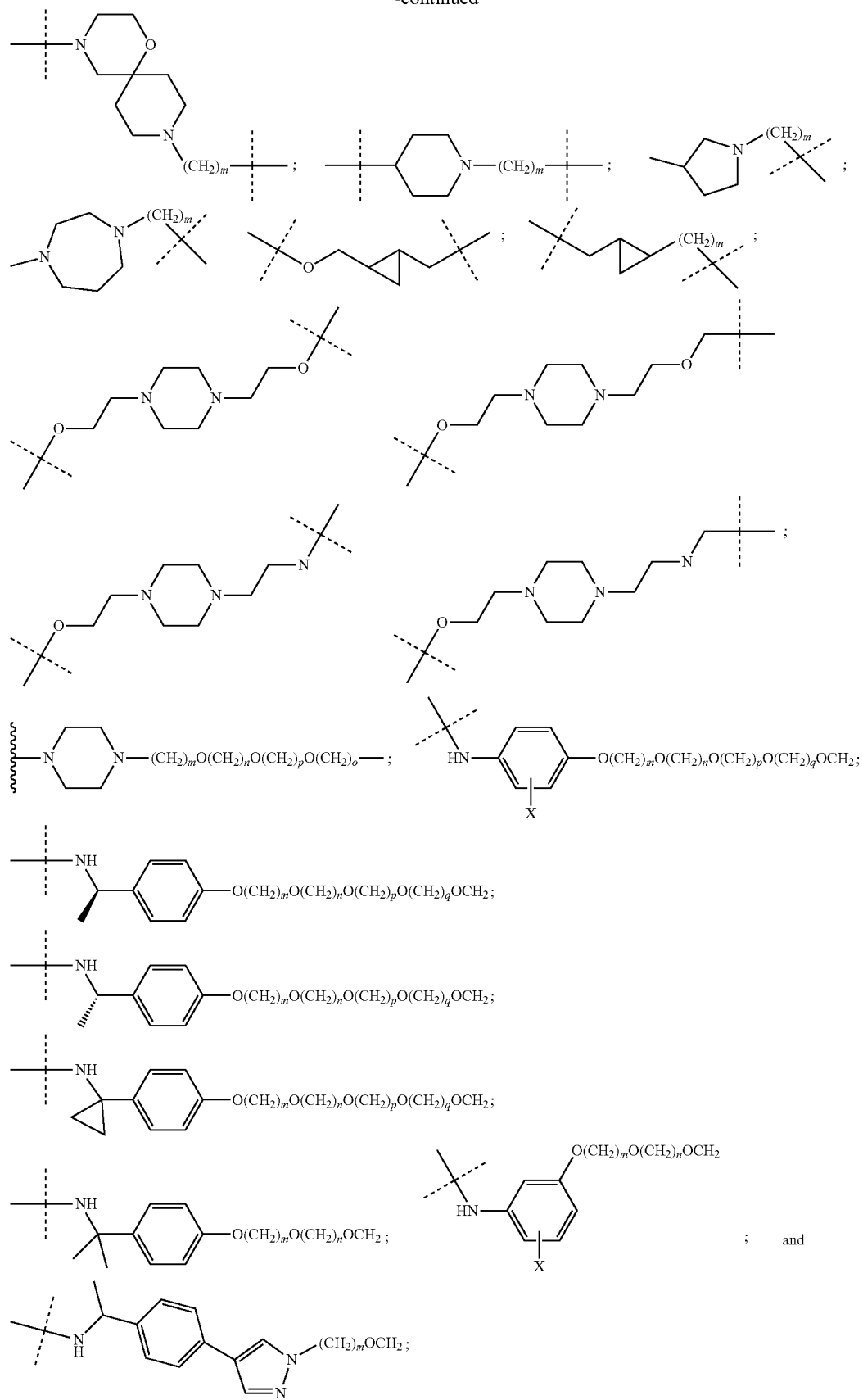

wherein
m, n, o, p, q, and r of the linker are independently 0, 1, 2, 3, 4, 5, 6, 7, 8, 9, 10, 11, 12, 13, 14, 15, 16, 17, 18, 19, 20;
when the number is zero, there is no N—O or O—O bond
R of the linker is H, methyl and ethyl;
X of the linker is H and F
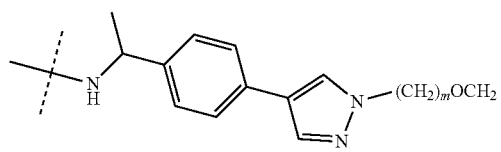
where m of the linker can be 2, 3, 4, 5
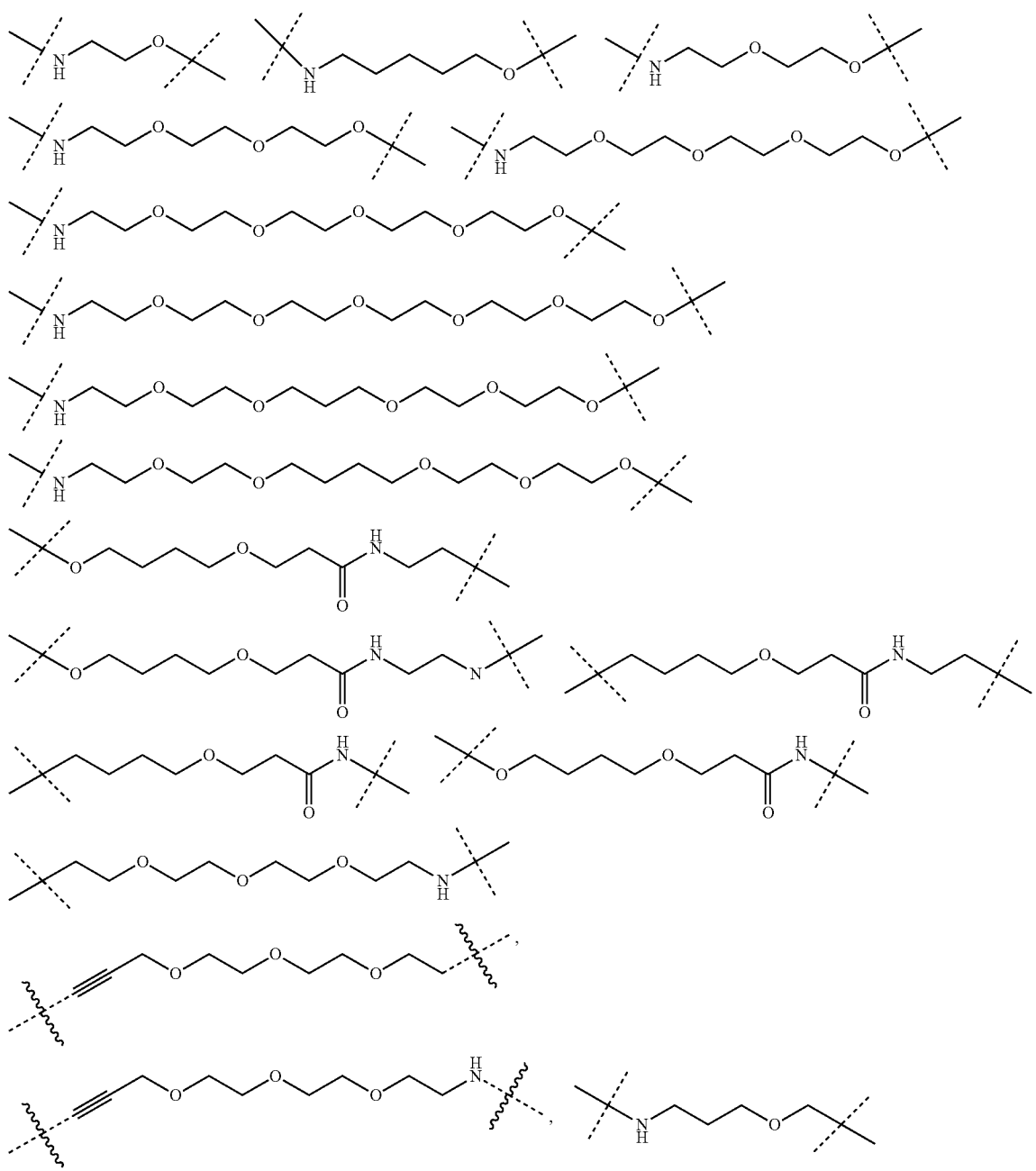

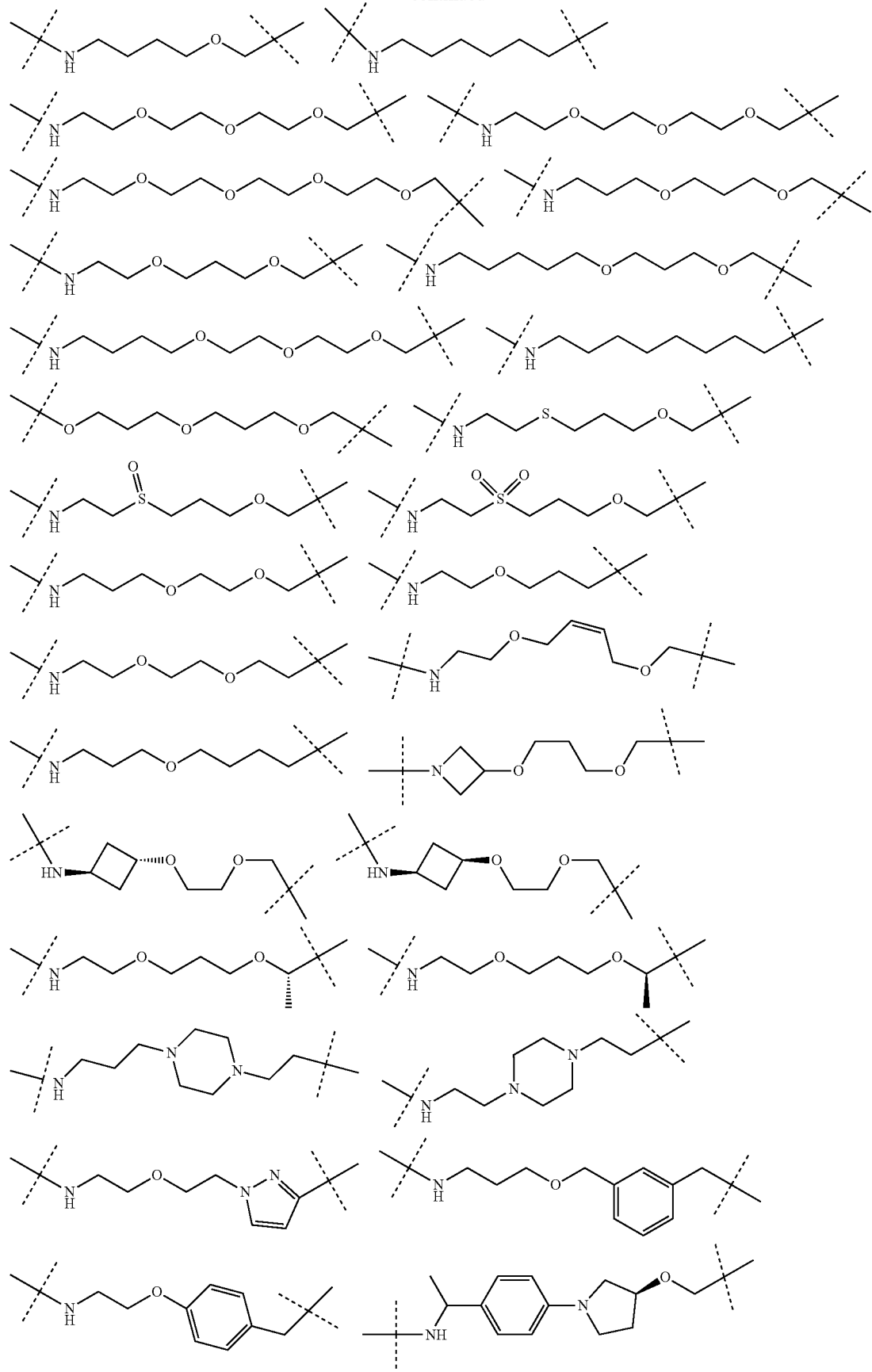

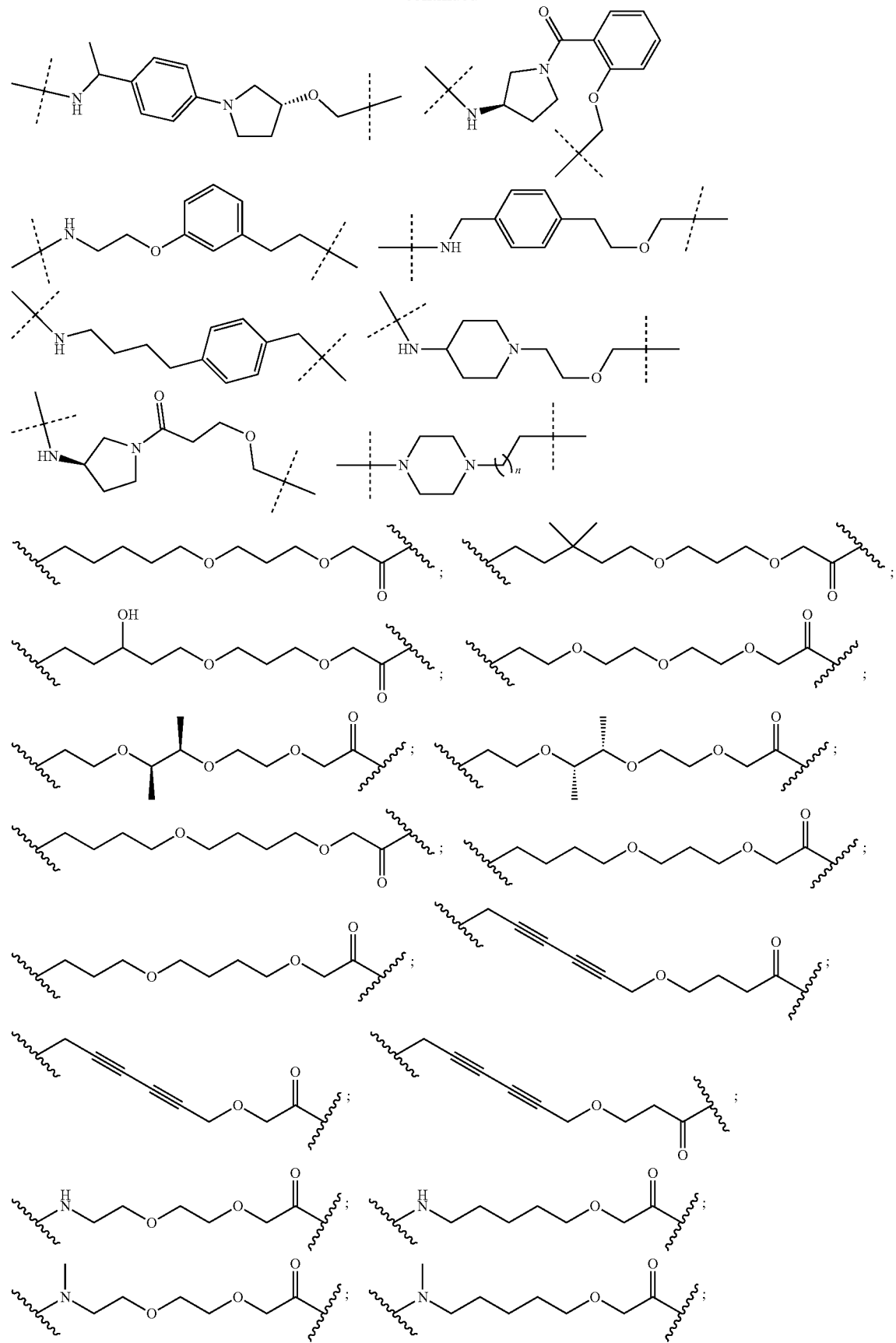

-continued
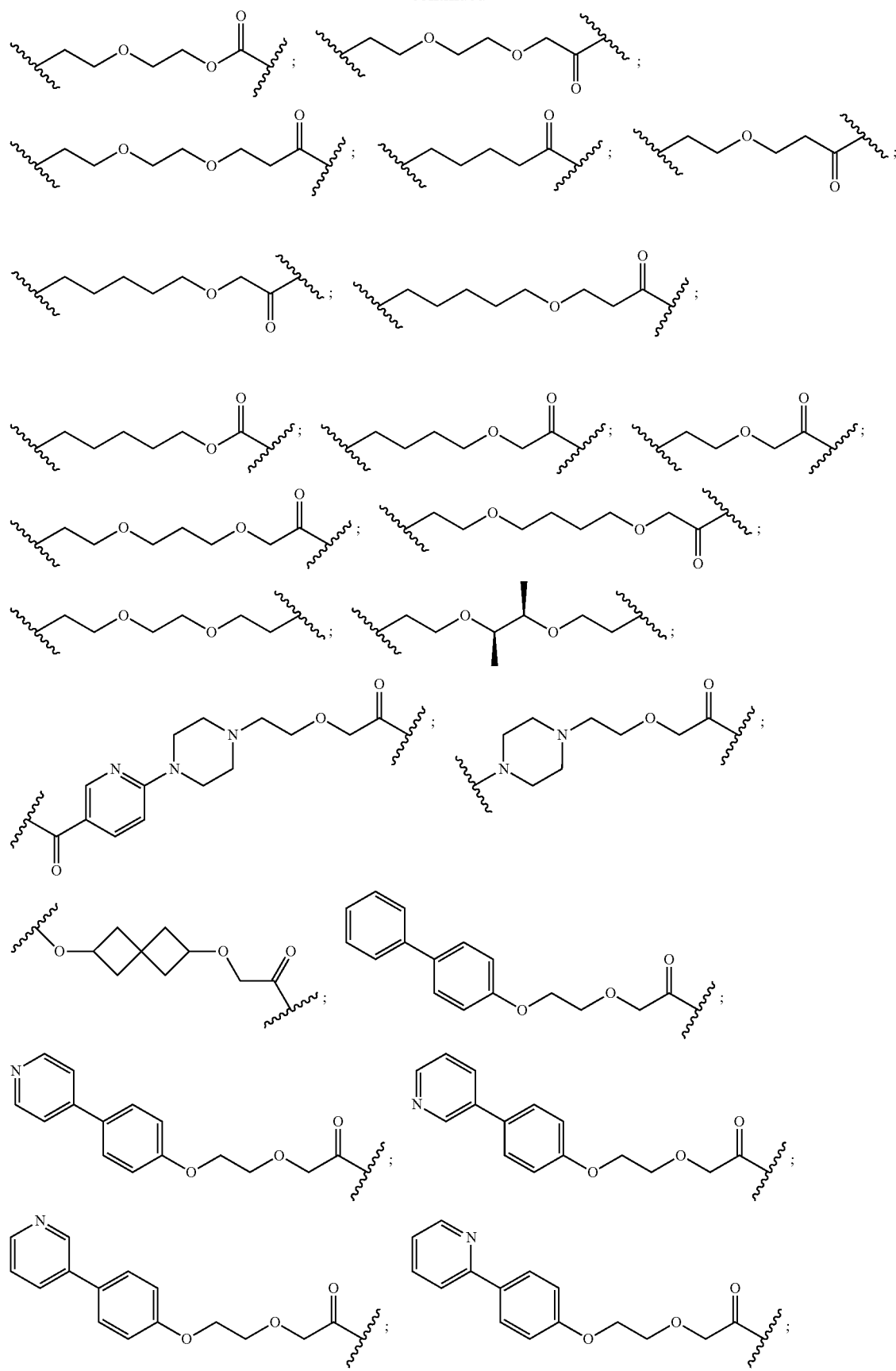

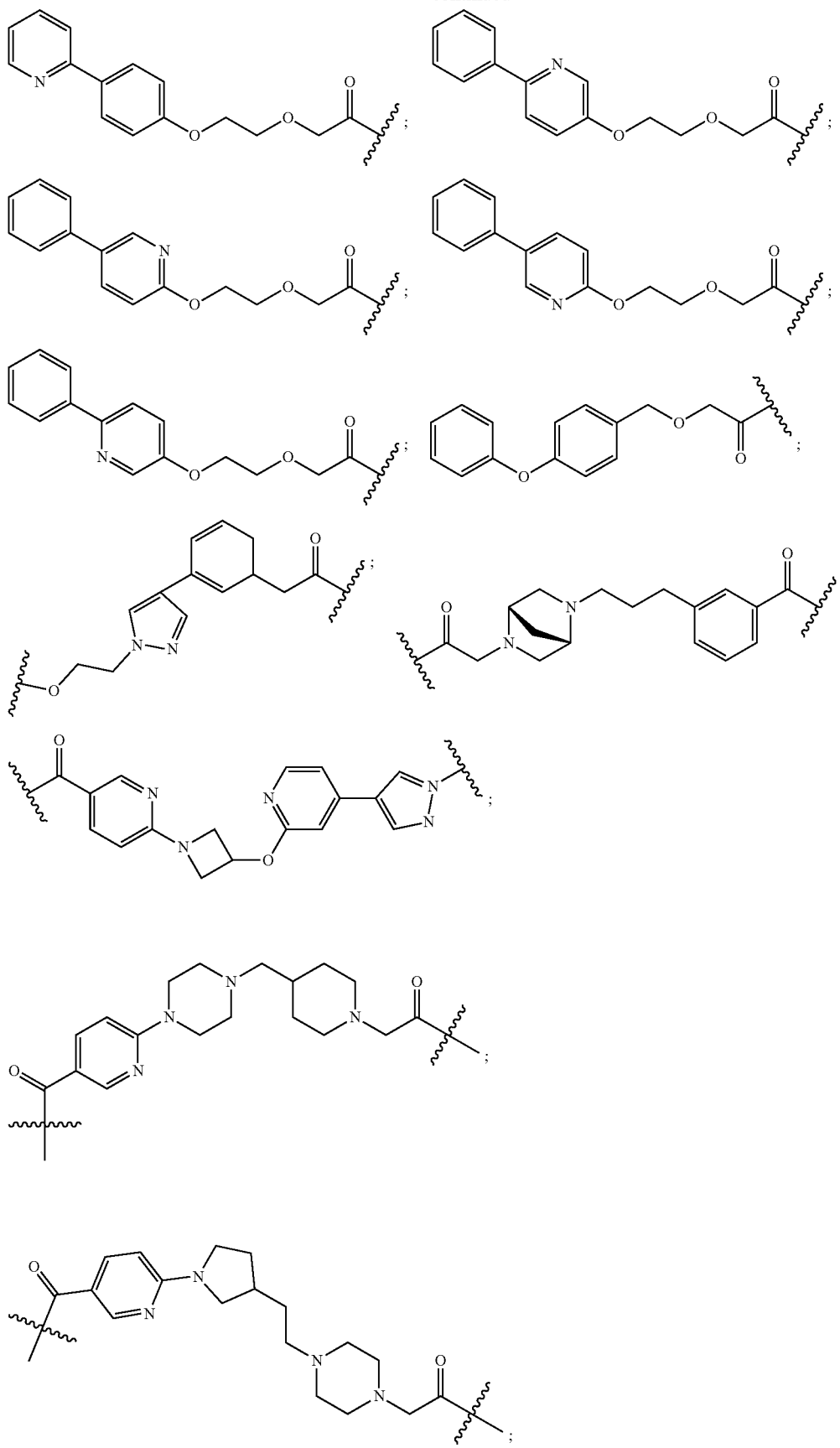

-continued
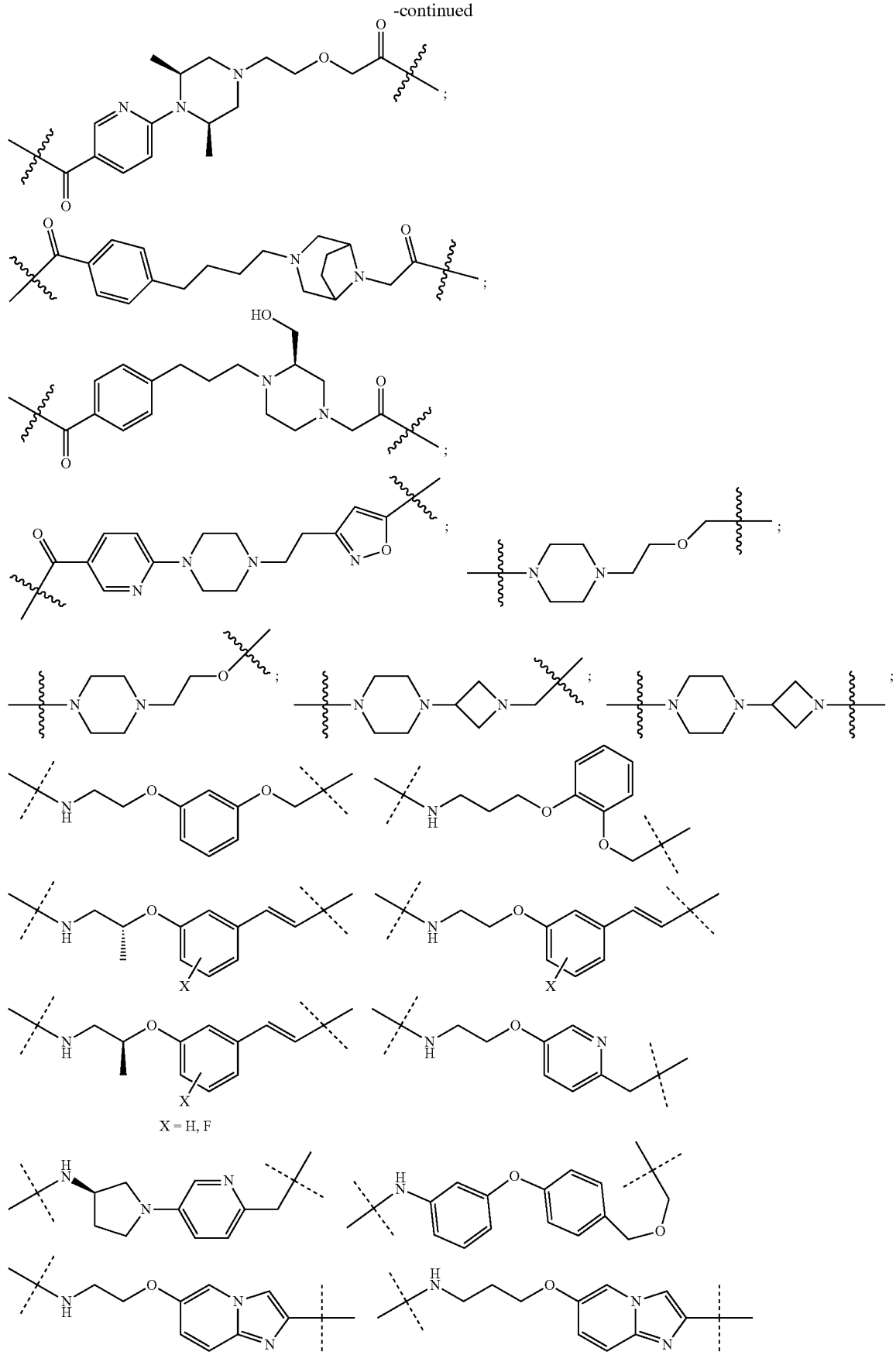
X = H, F

-continued
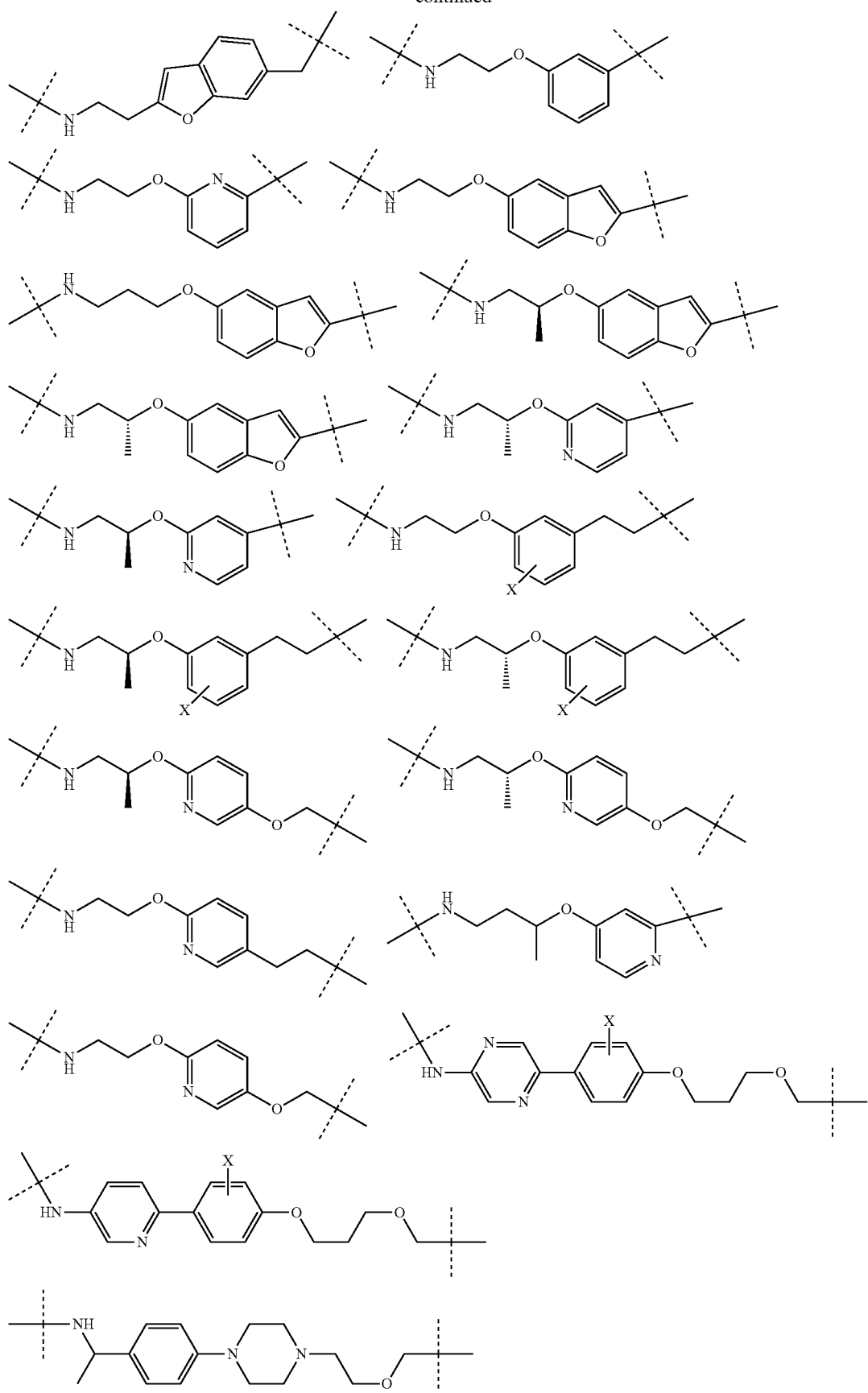

-continued
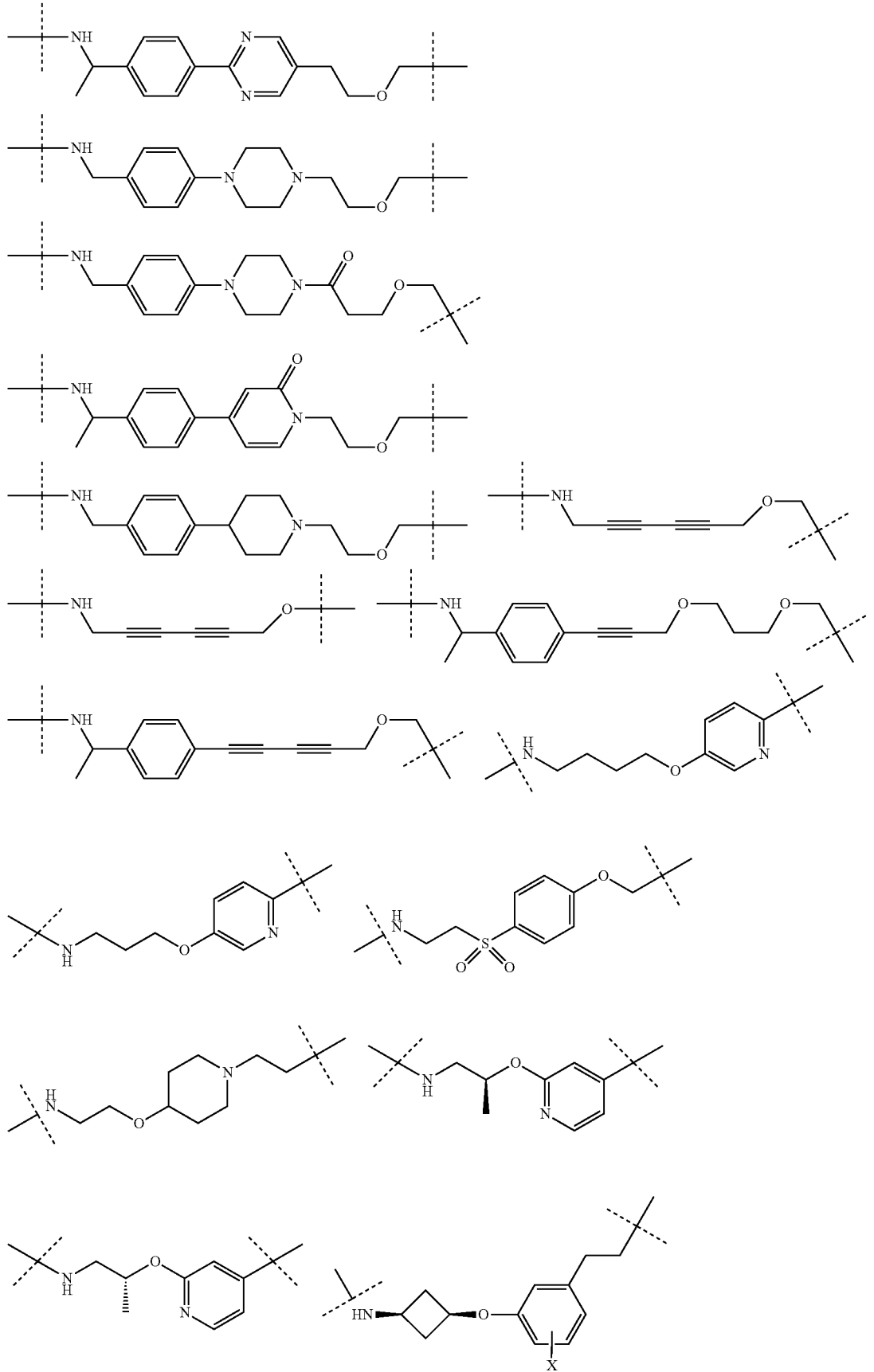

-continued
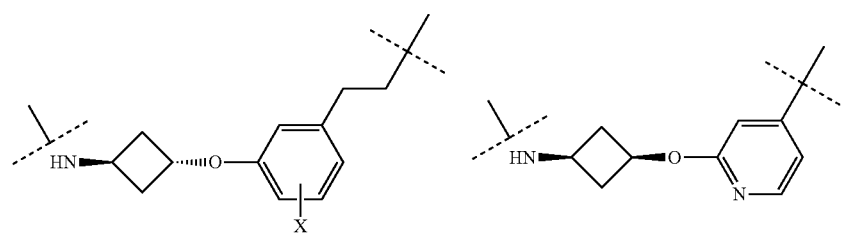
X = H, F
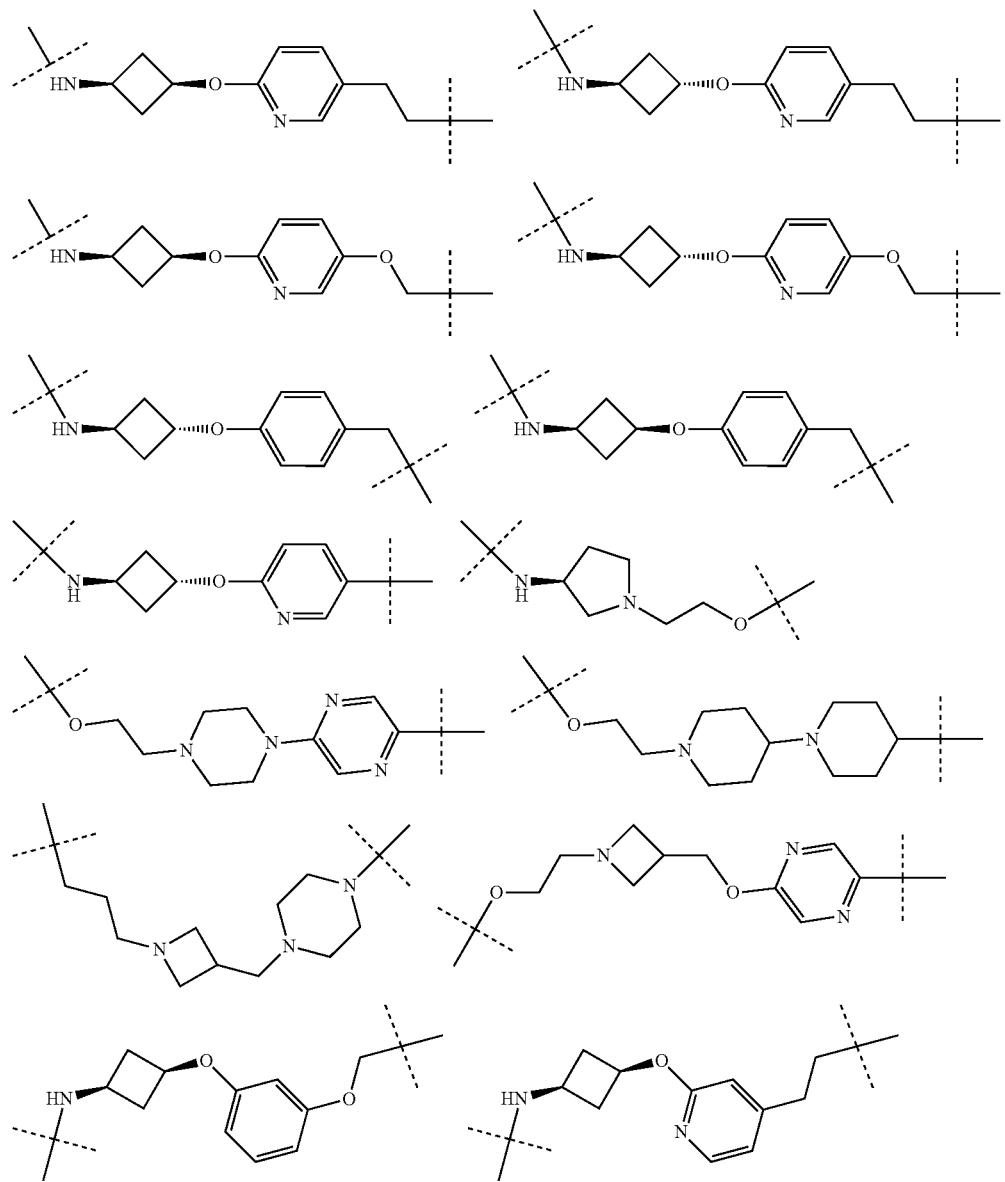
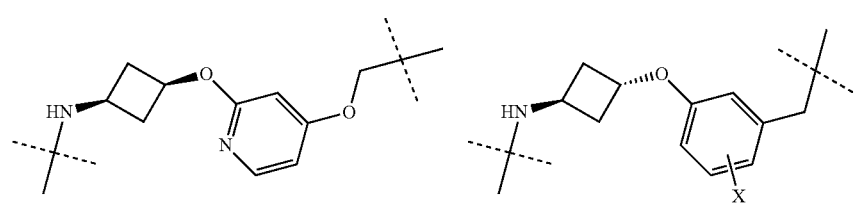

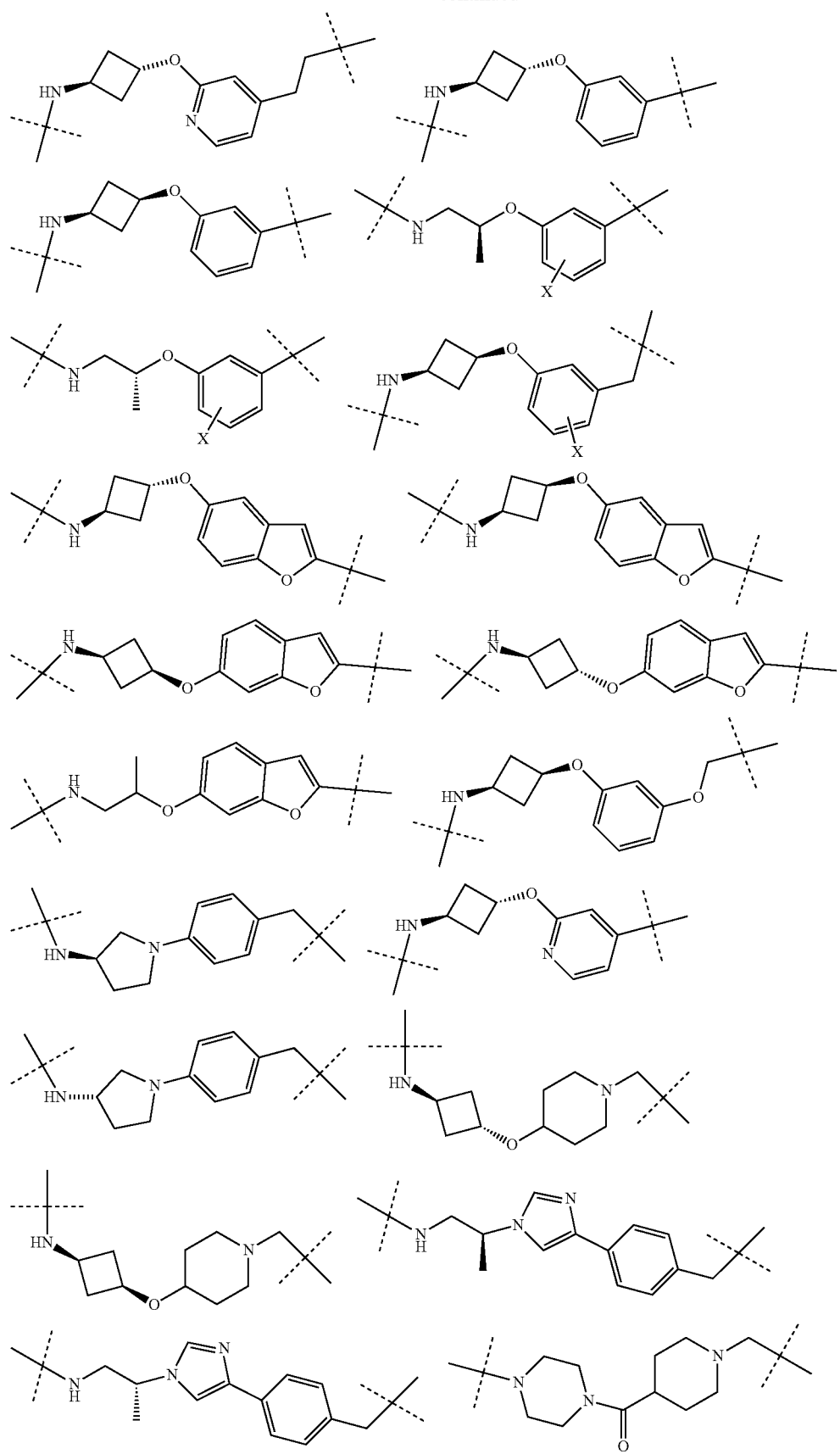

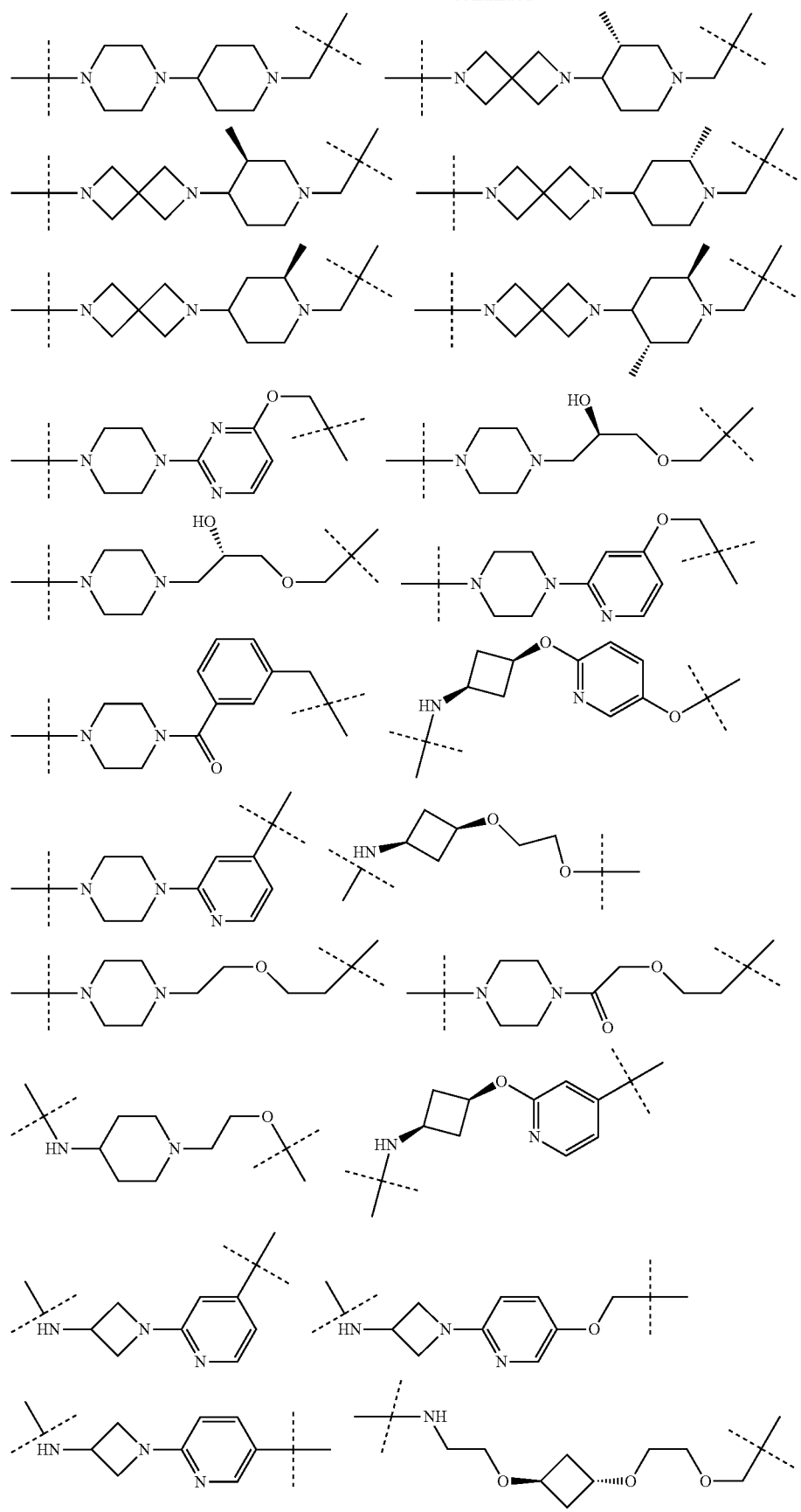

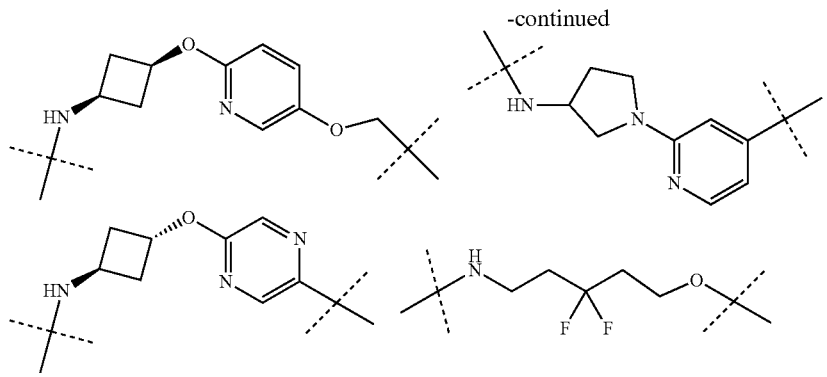
where each n and m of the linker can independently be 0, 1, 2, 3, 4, 5, 6.
In any aspect or embodiment described herein, the unit $A^L$ of linker (L) is selected from the group consisting of:
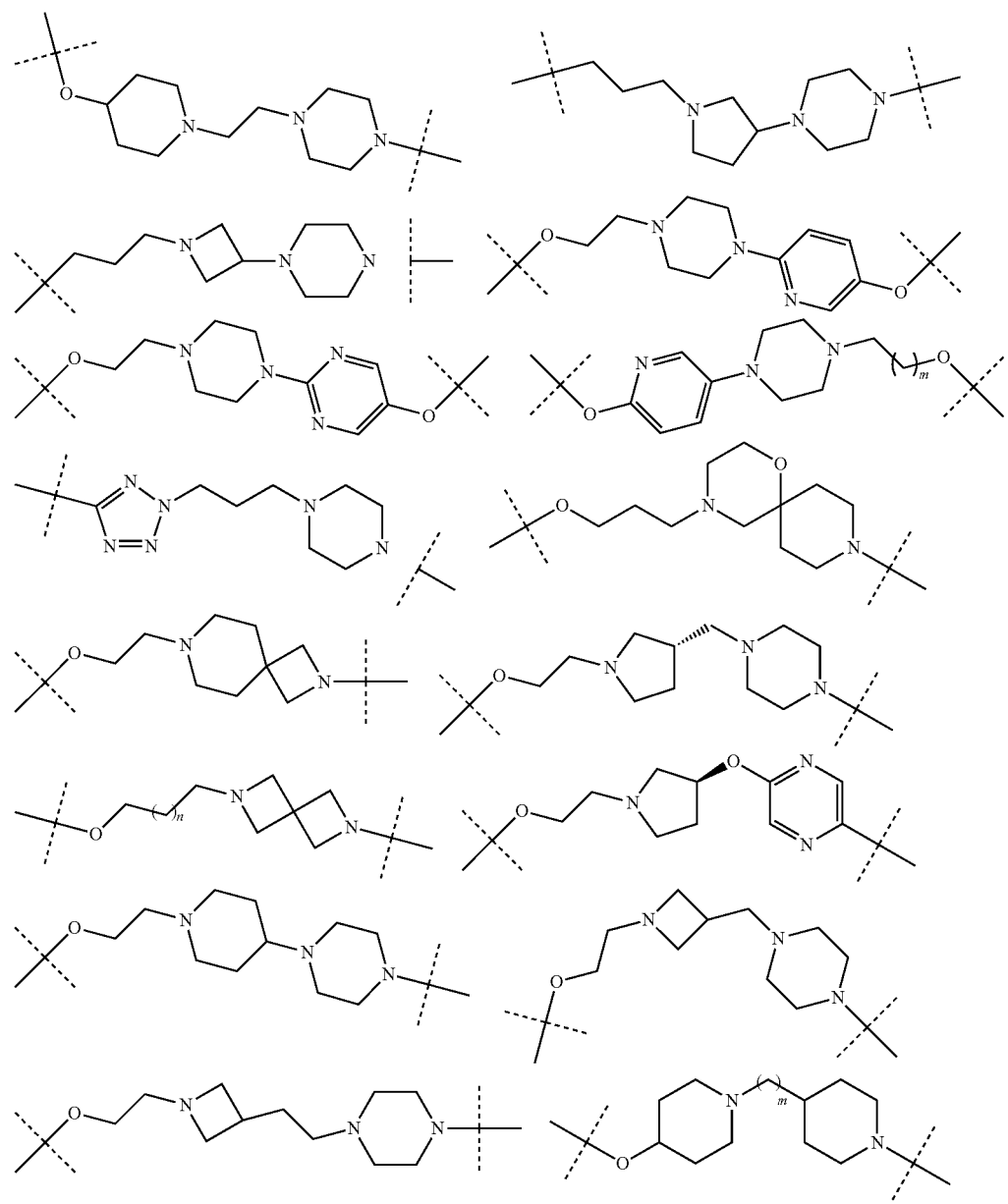

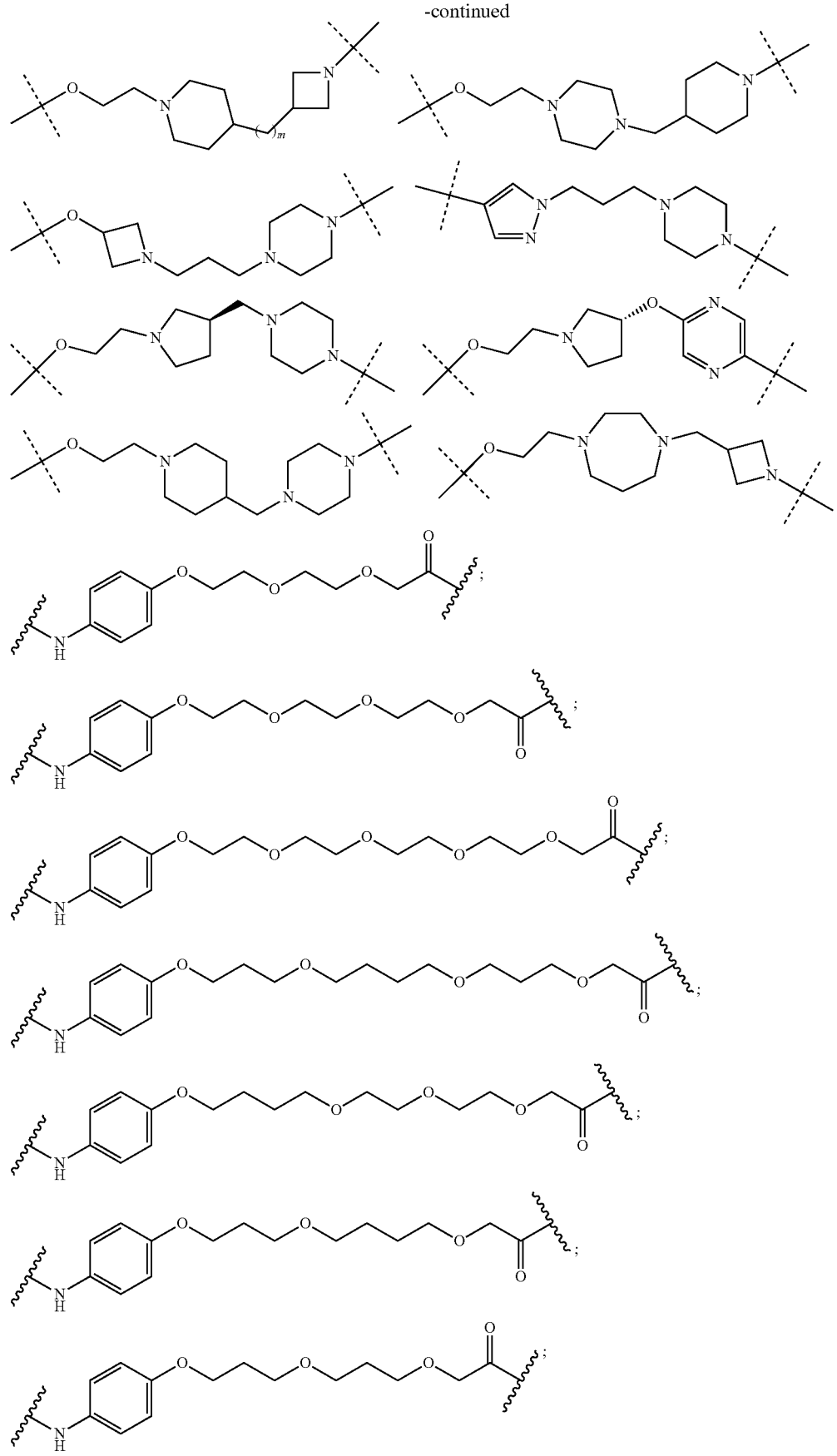

-continued
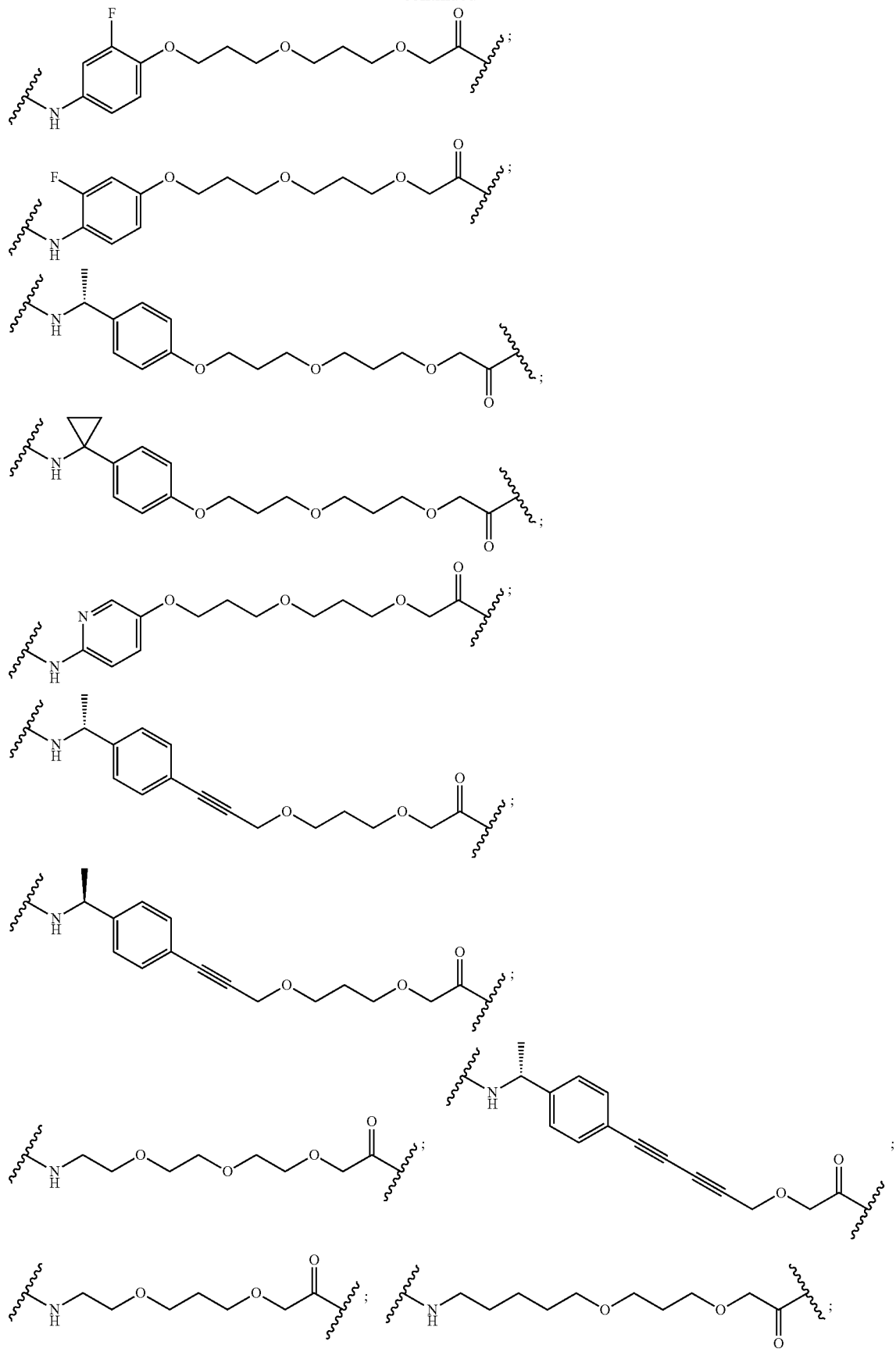

-continued
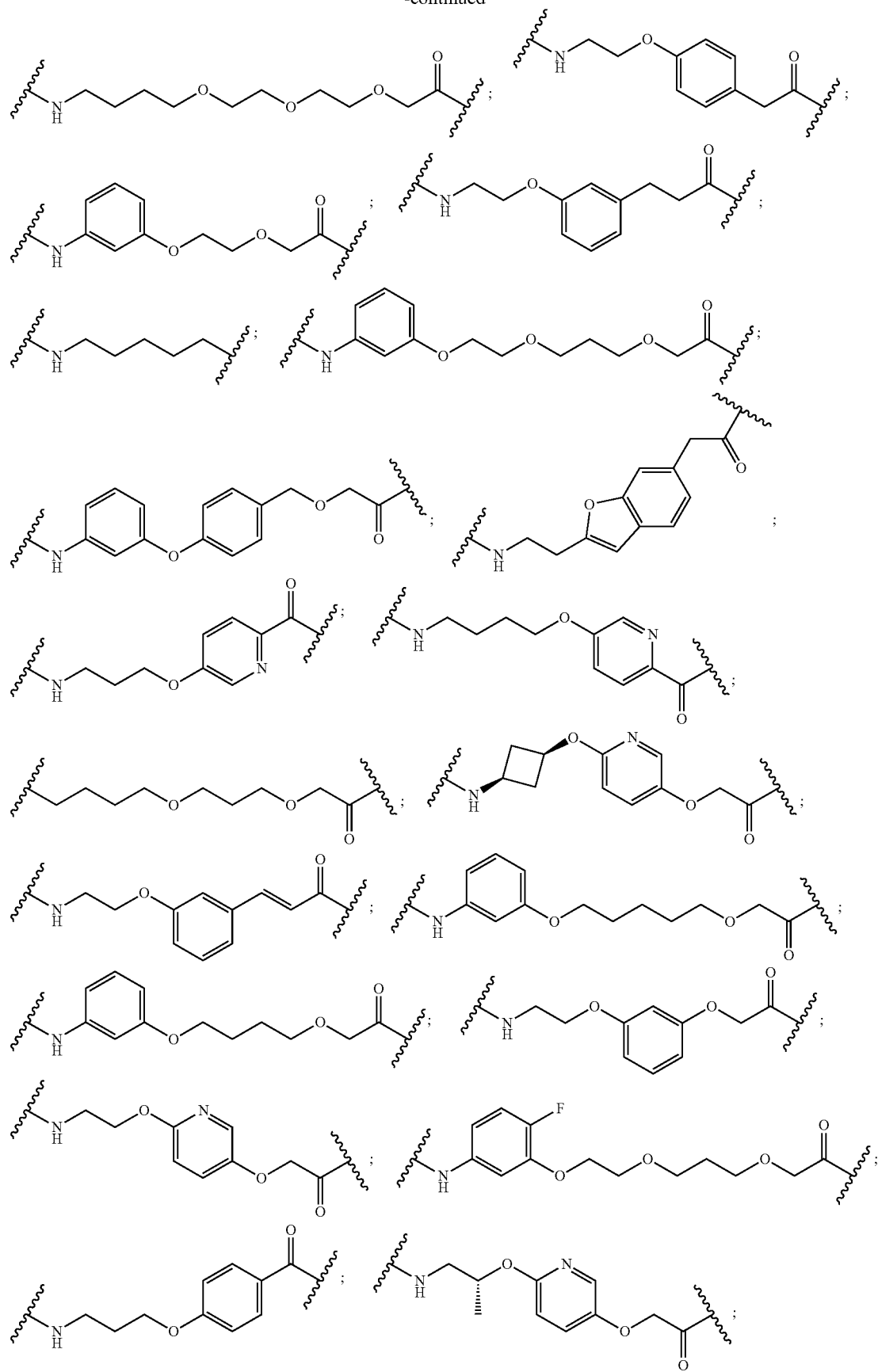

331 332
-continued
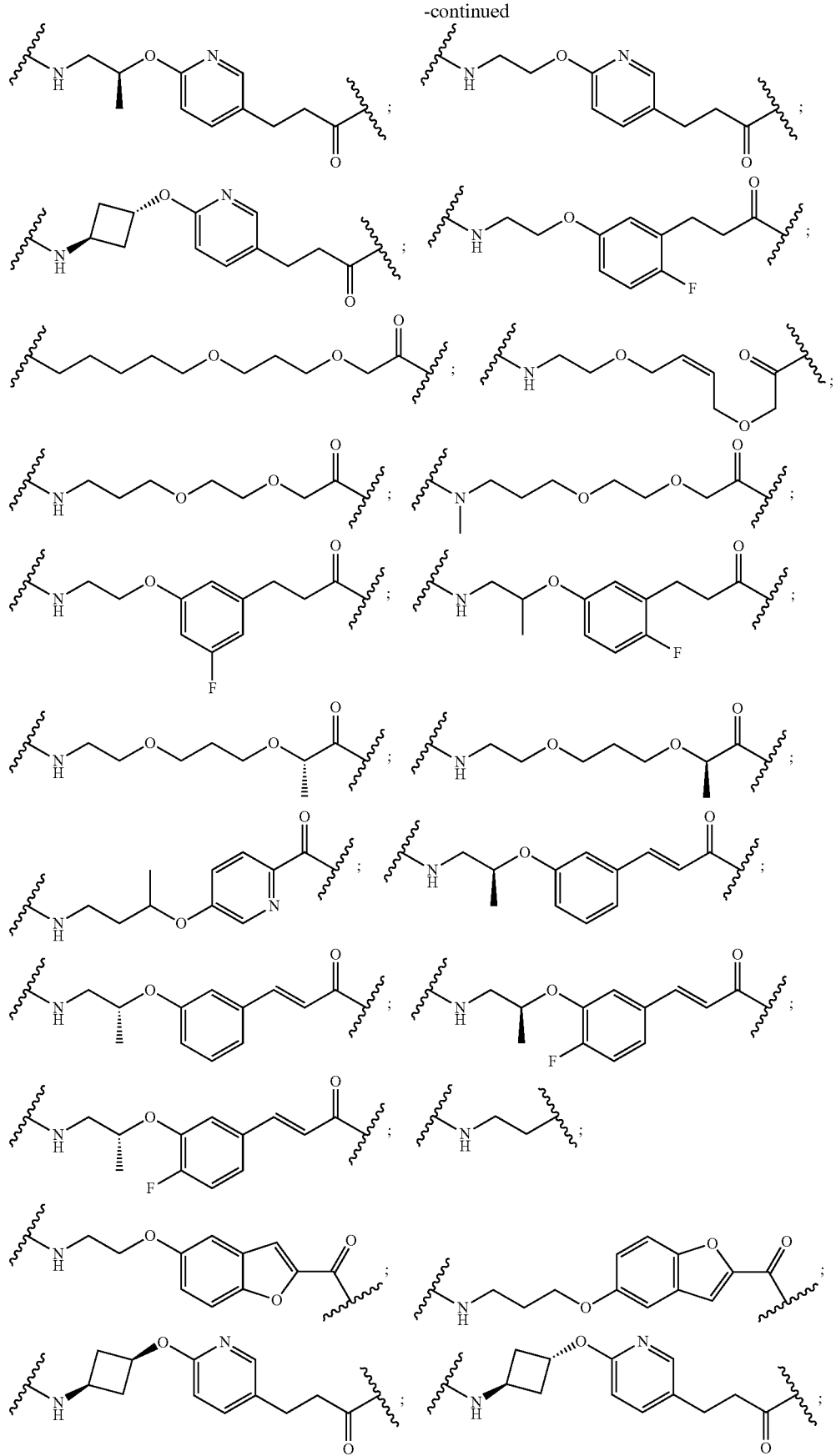

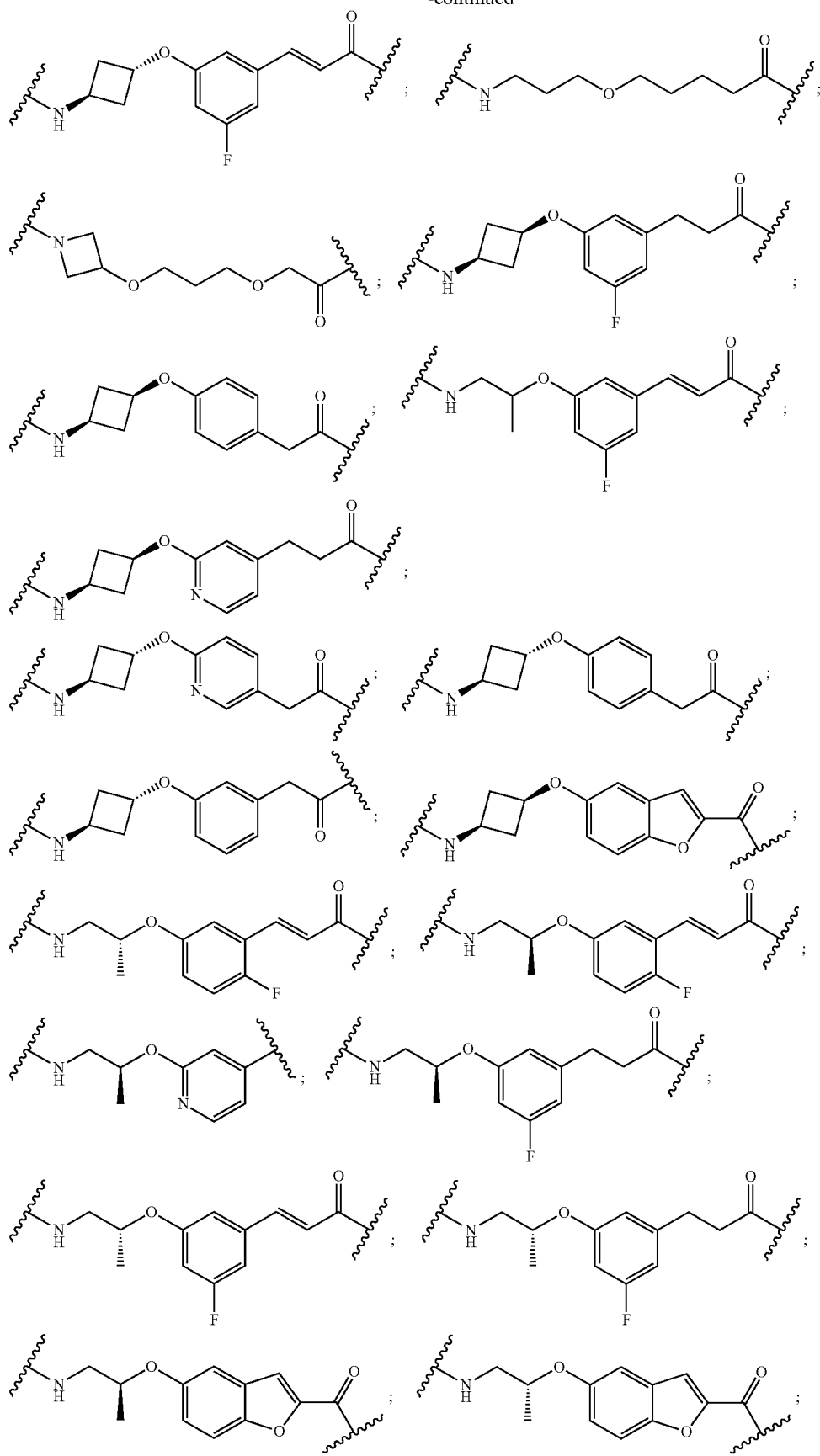

-continued
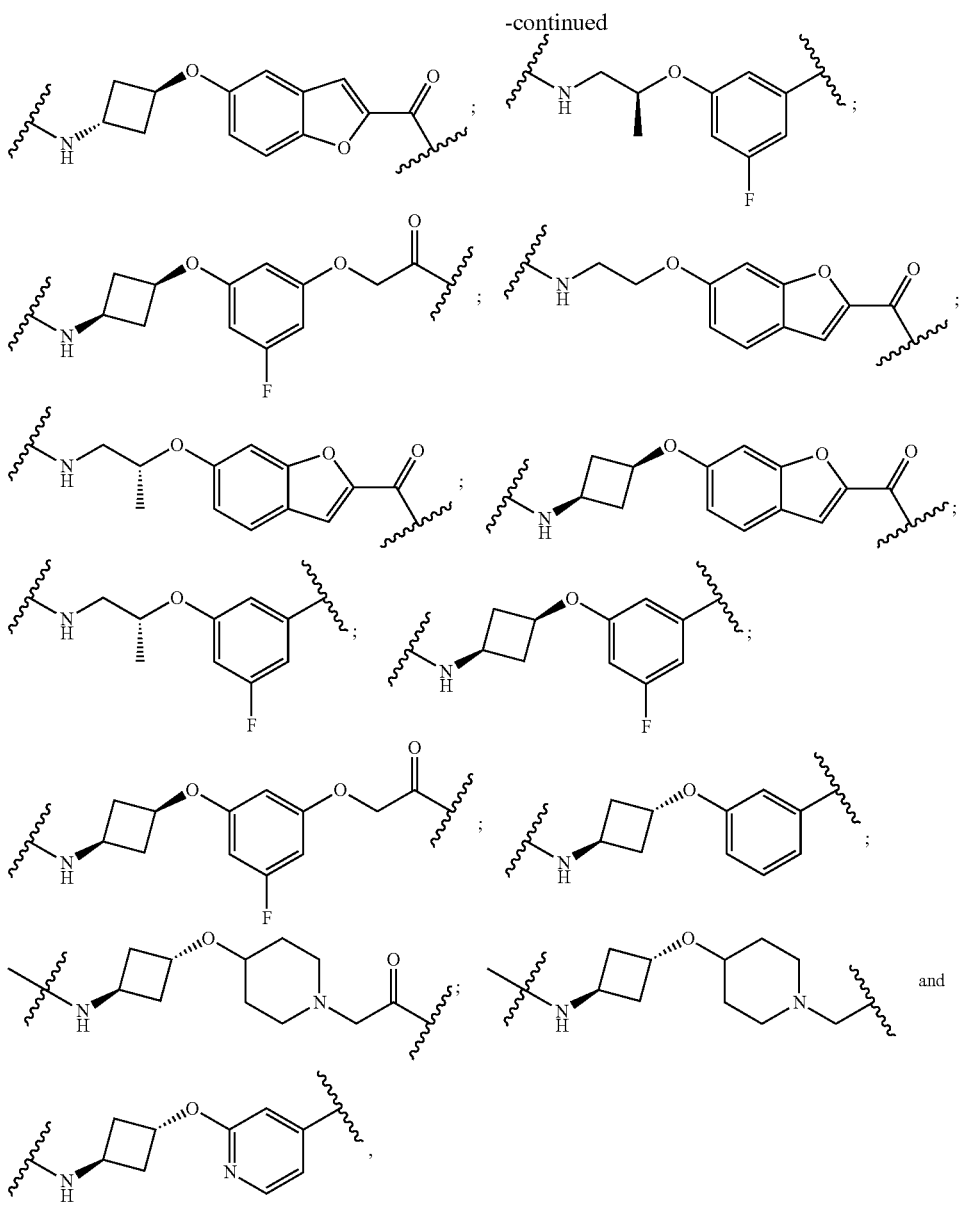
wherein each m and n is independently selected from 0, 1, 2, 3, 4, 5, or 6.
In any aspect or embodiment described herein, the unit $A^L$ of linker (L) is selected from the group consisting of:
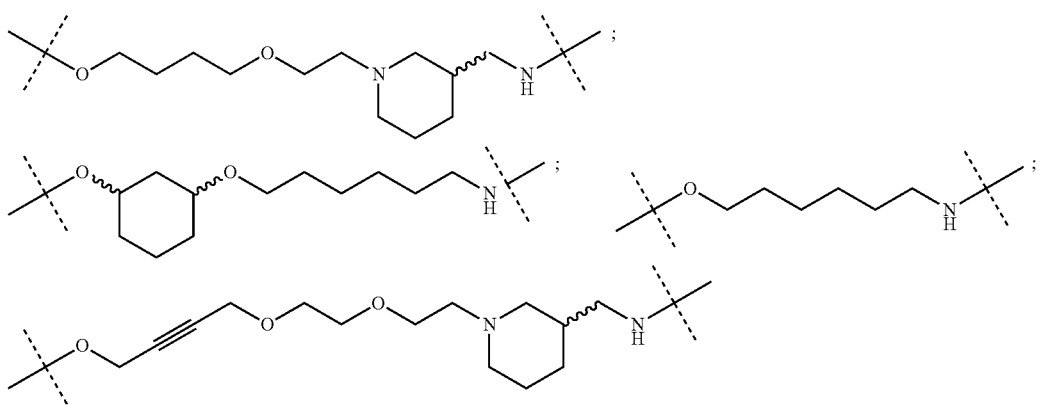

-continued
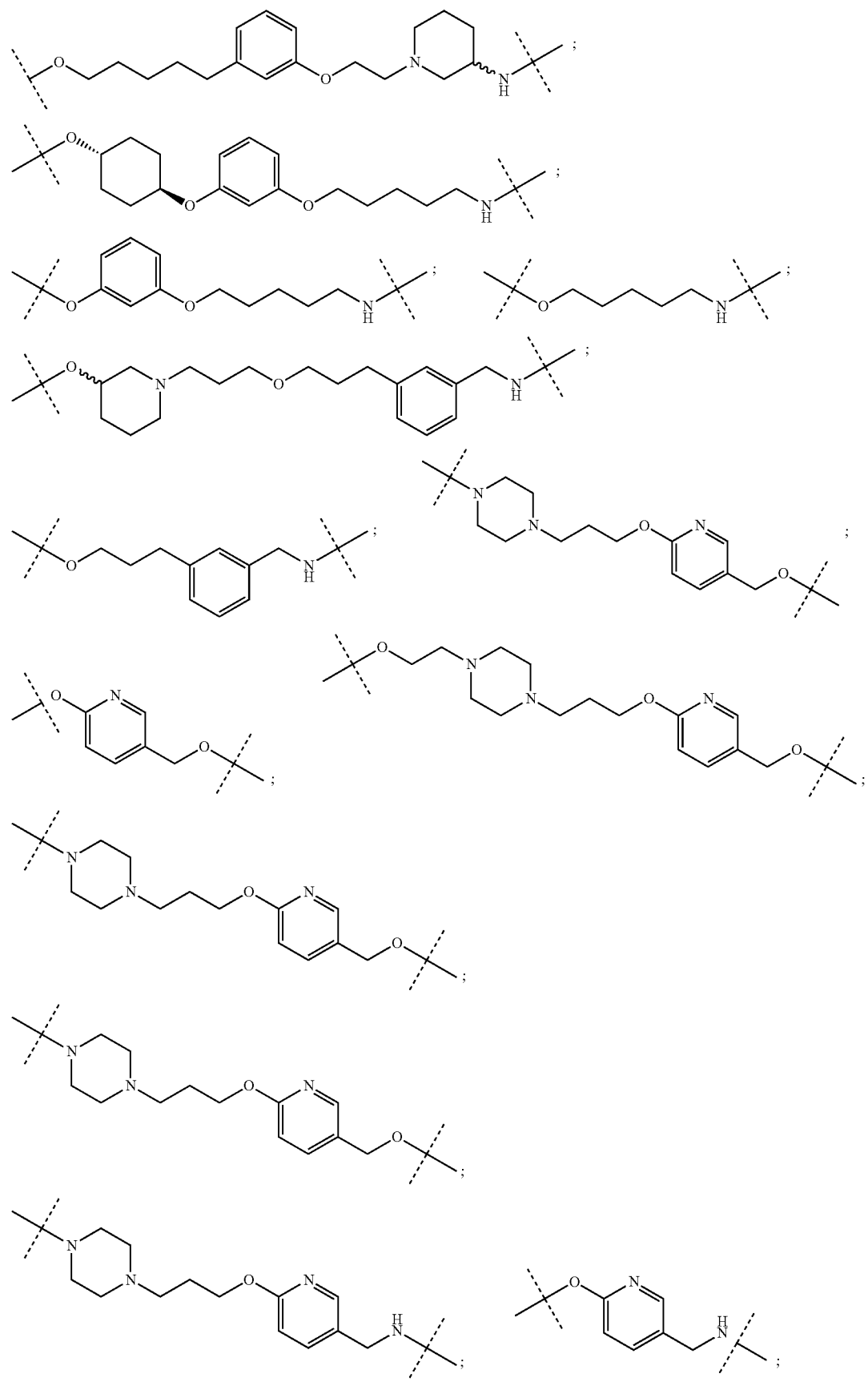

-continued
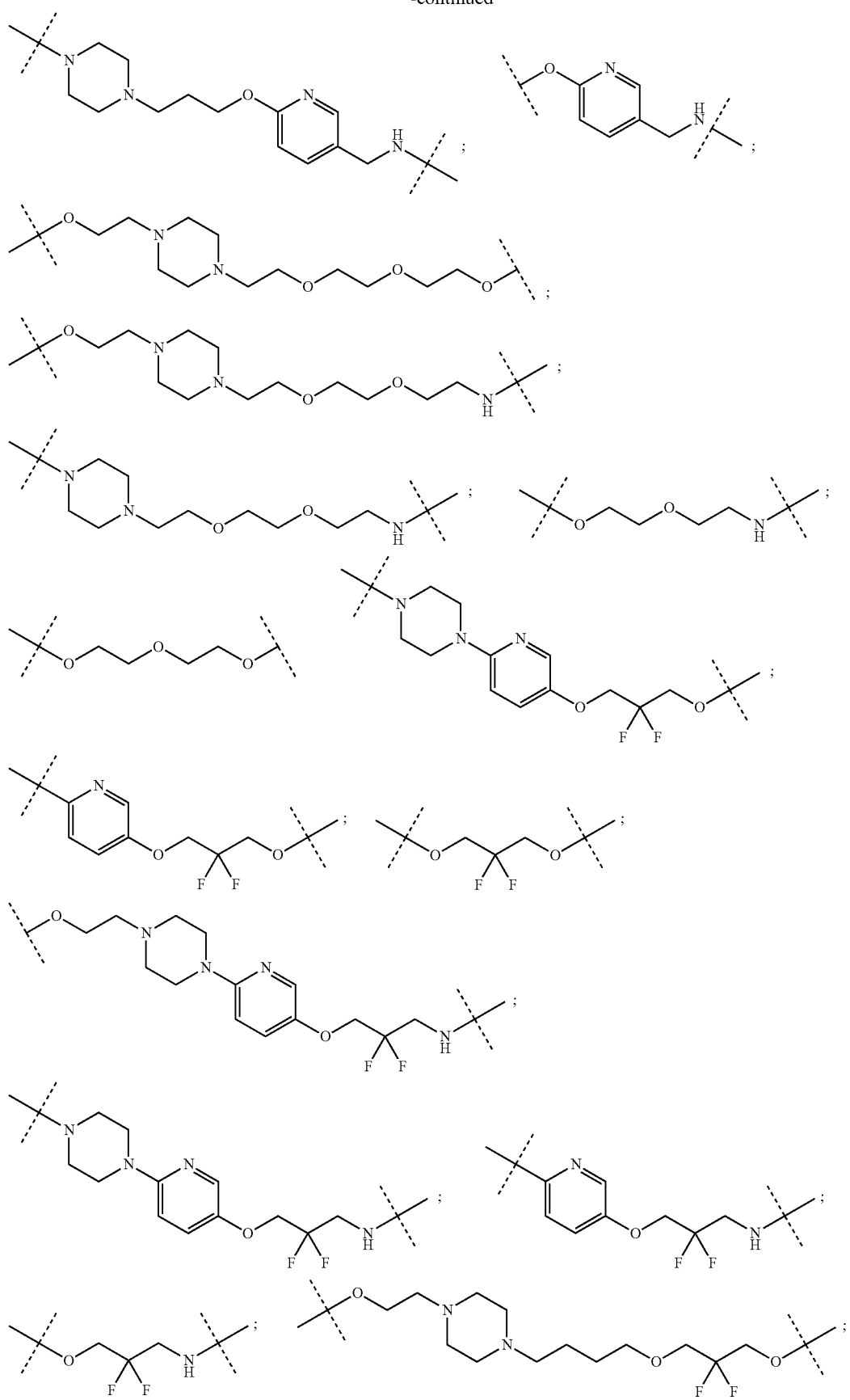

341 342
-continued
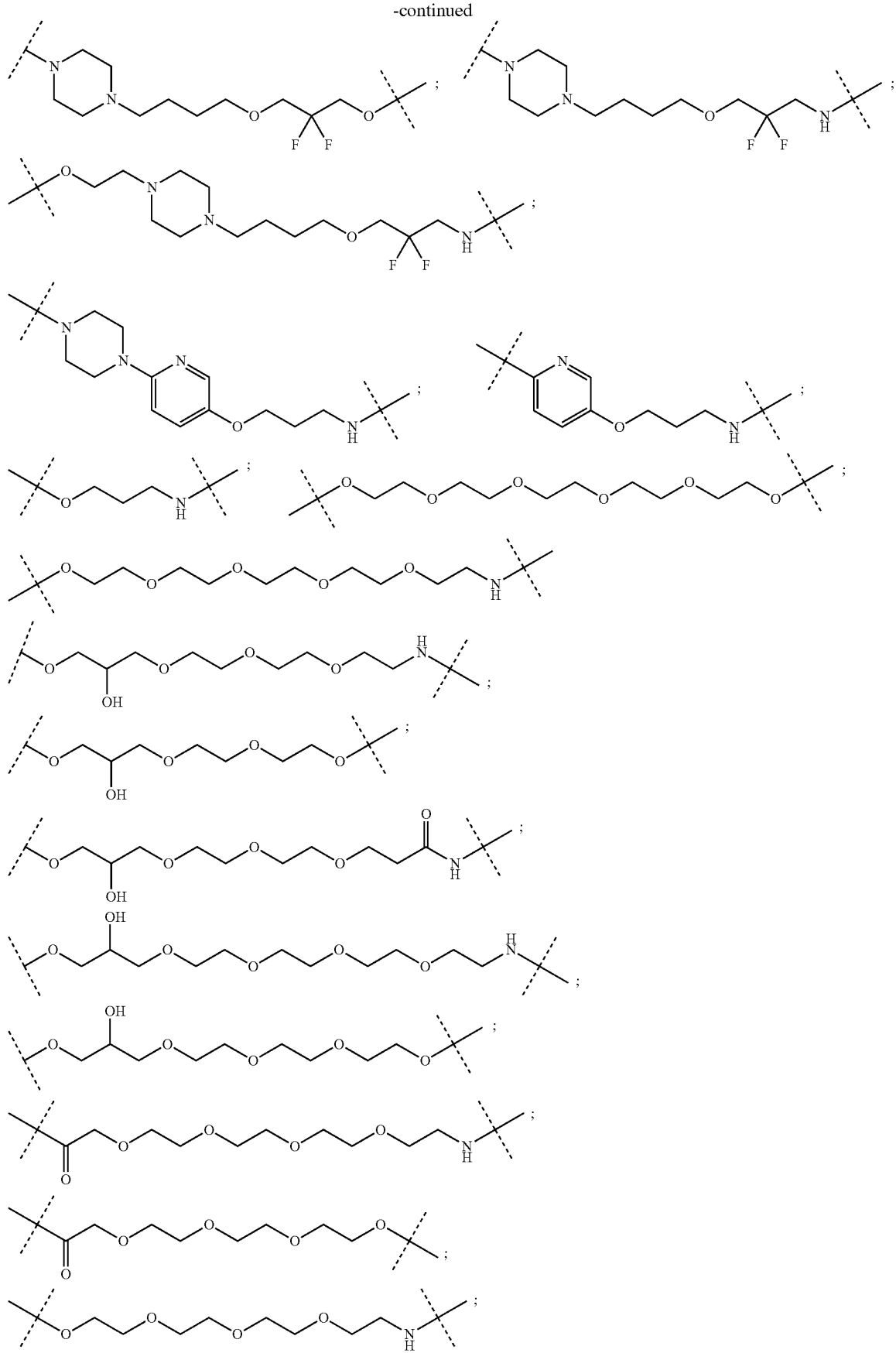

343
-continued
344
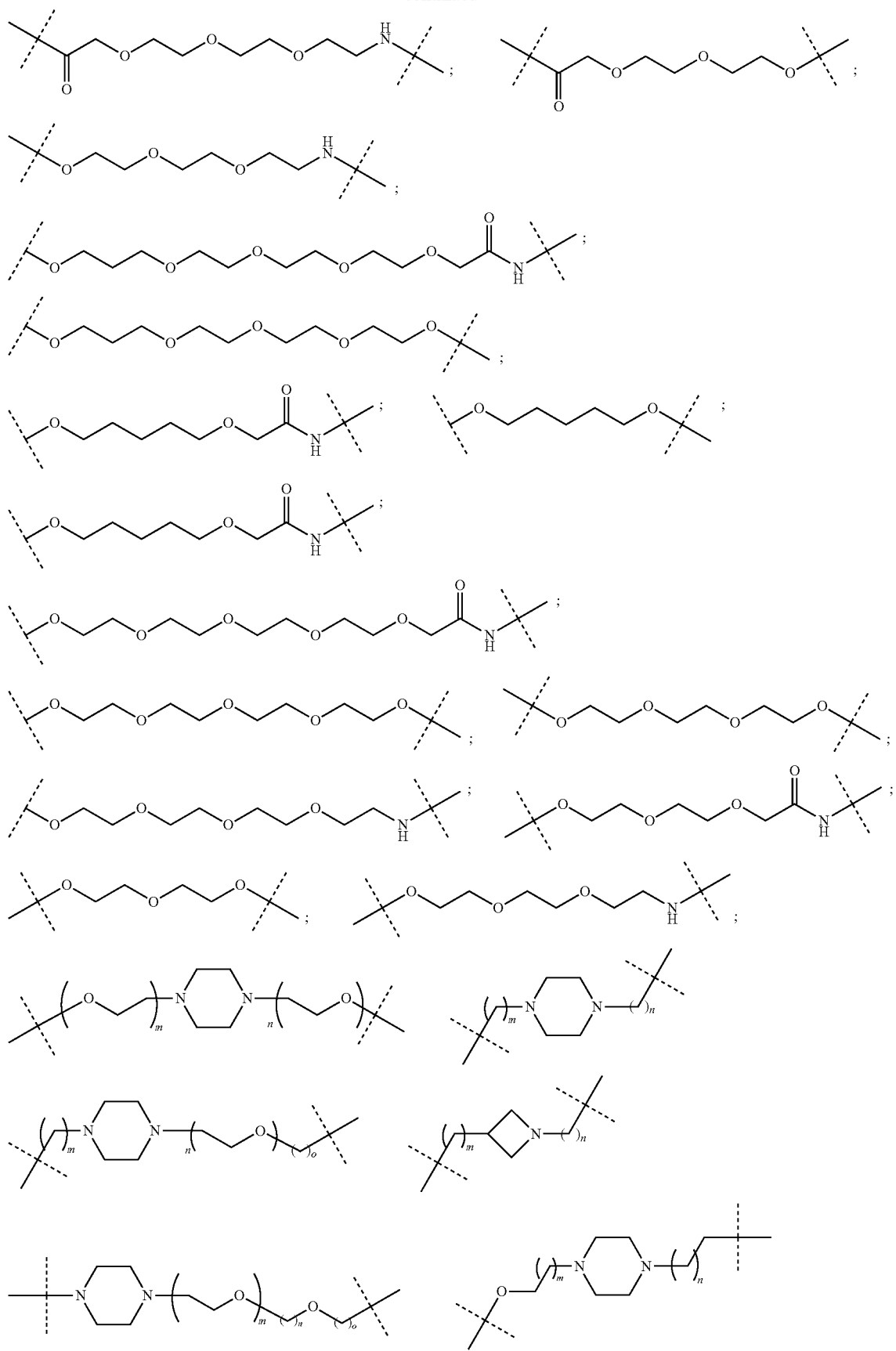

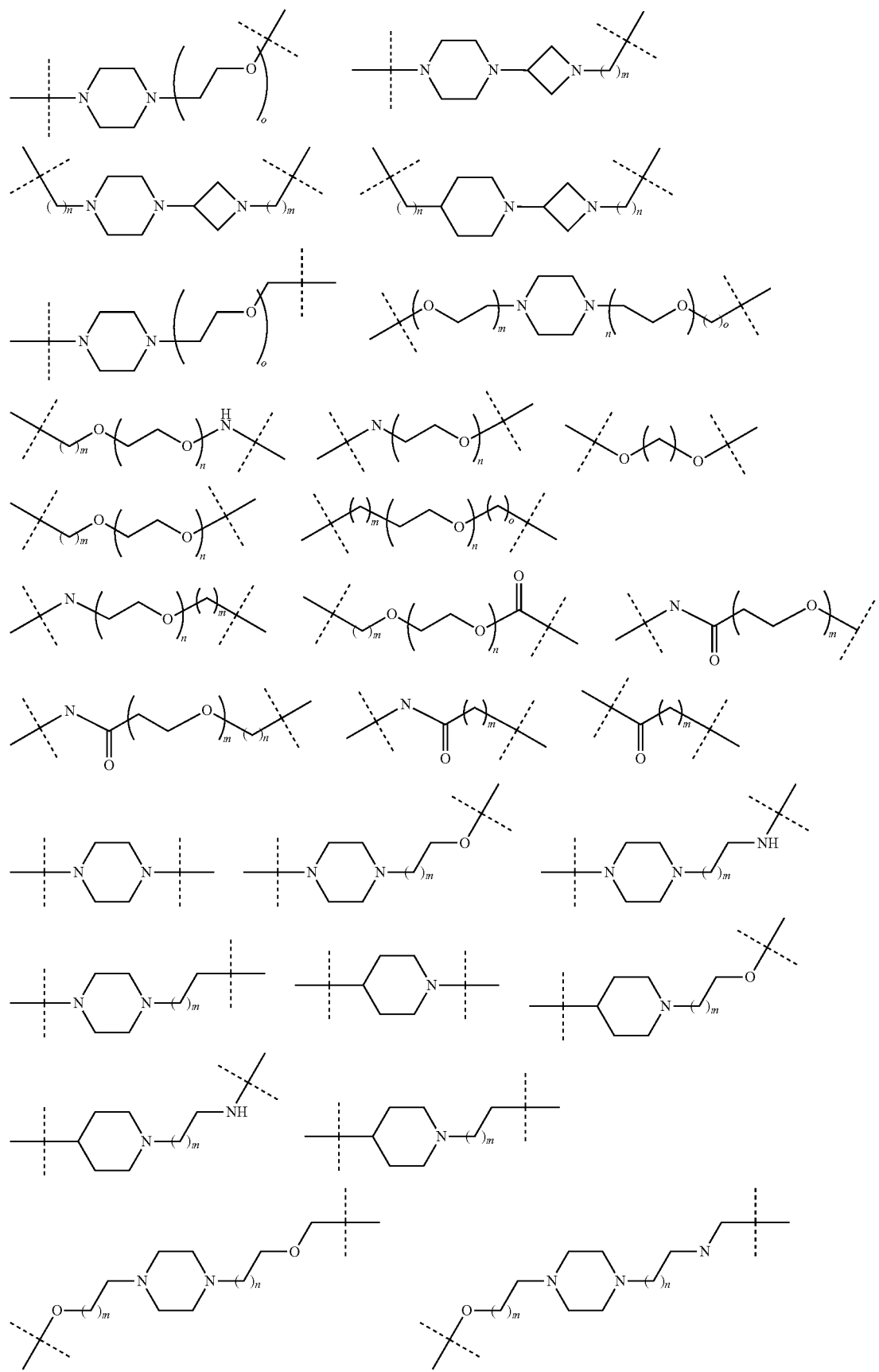

347 348
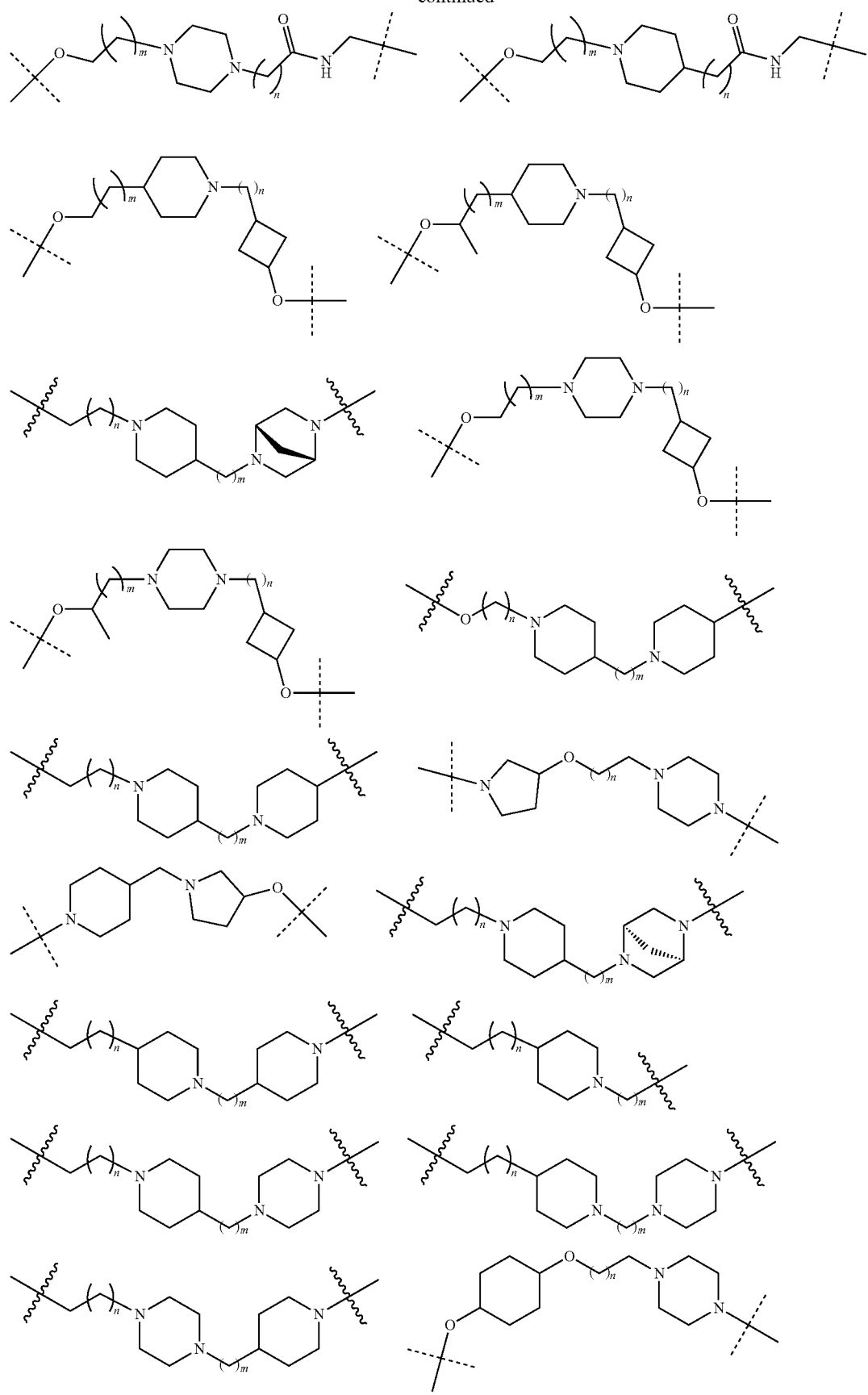

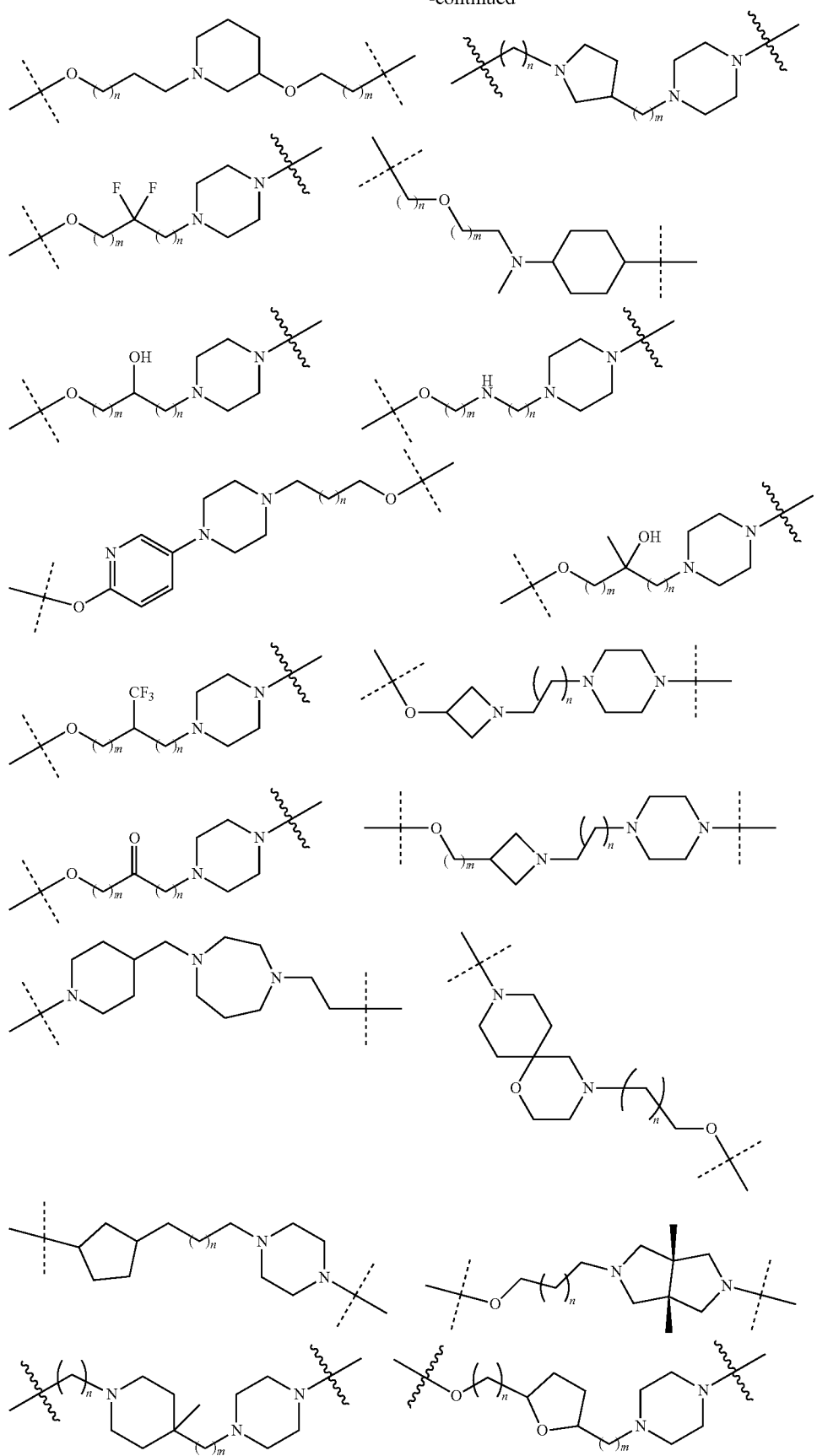

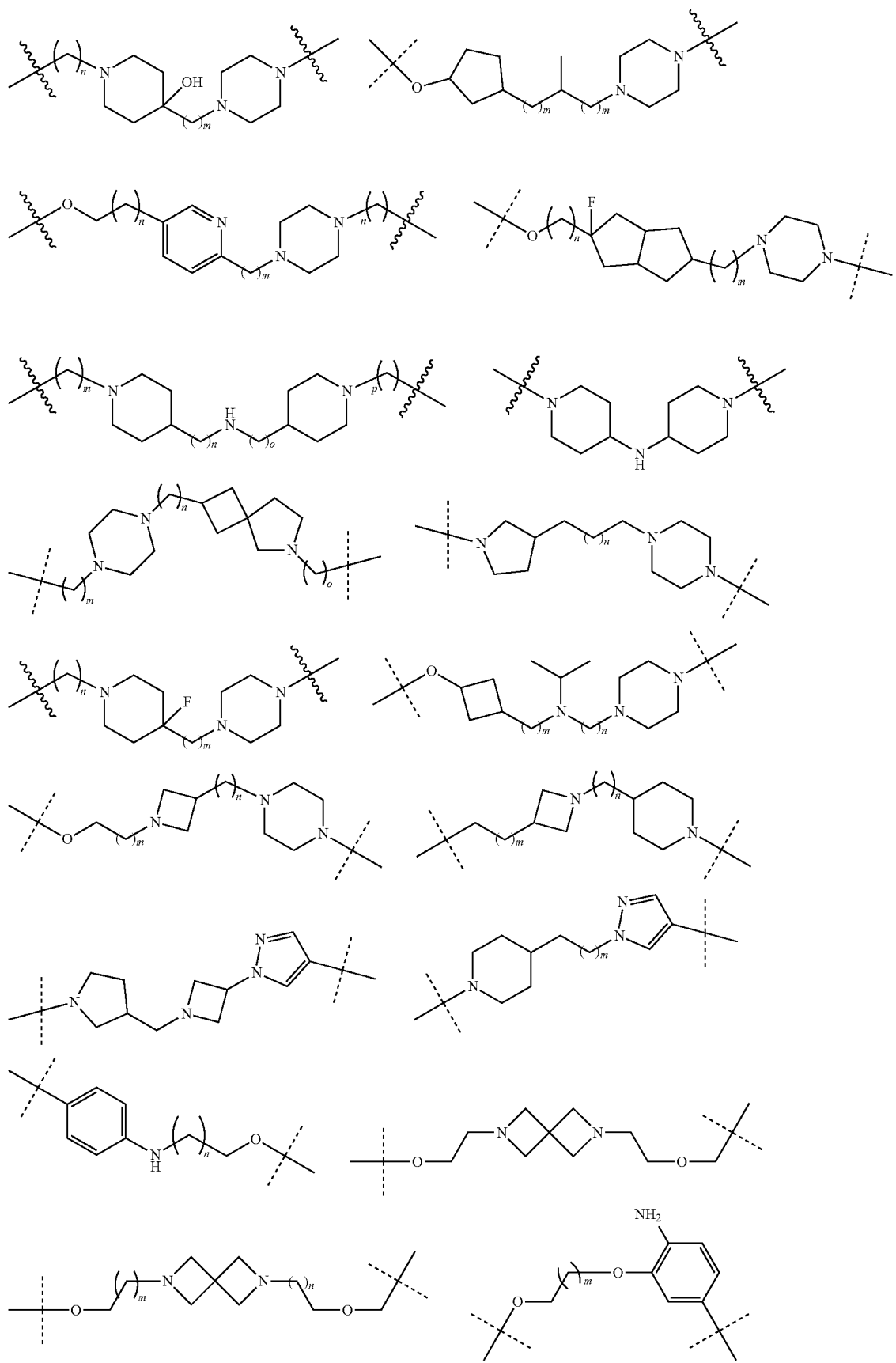

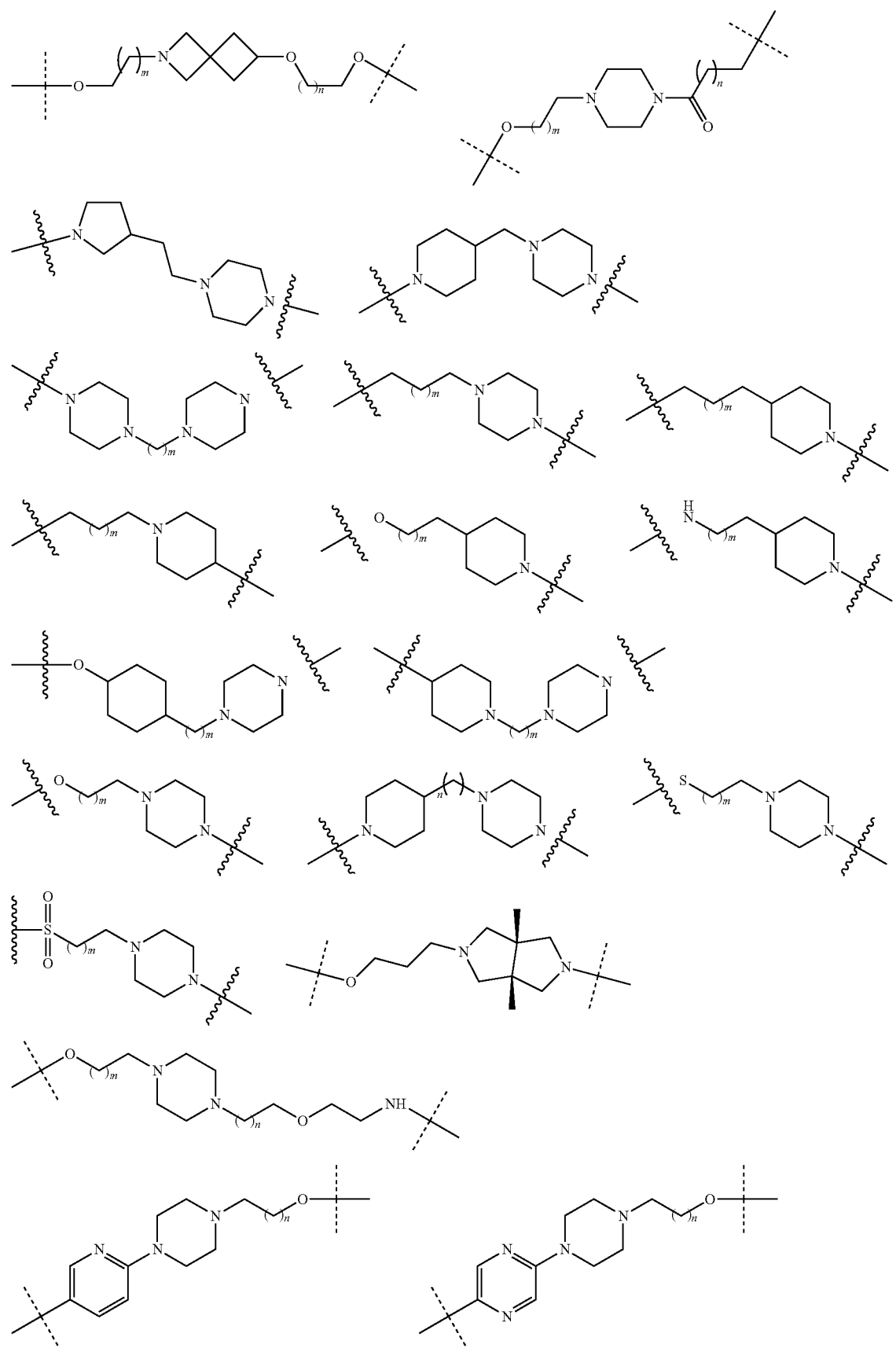

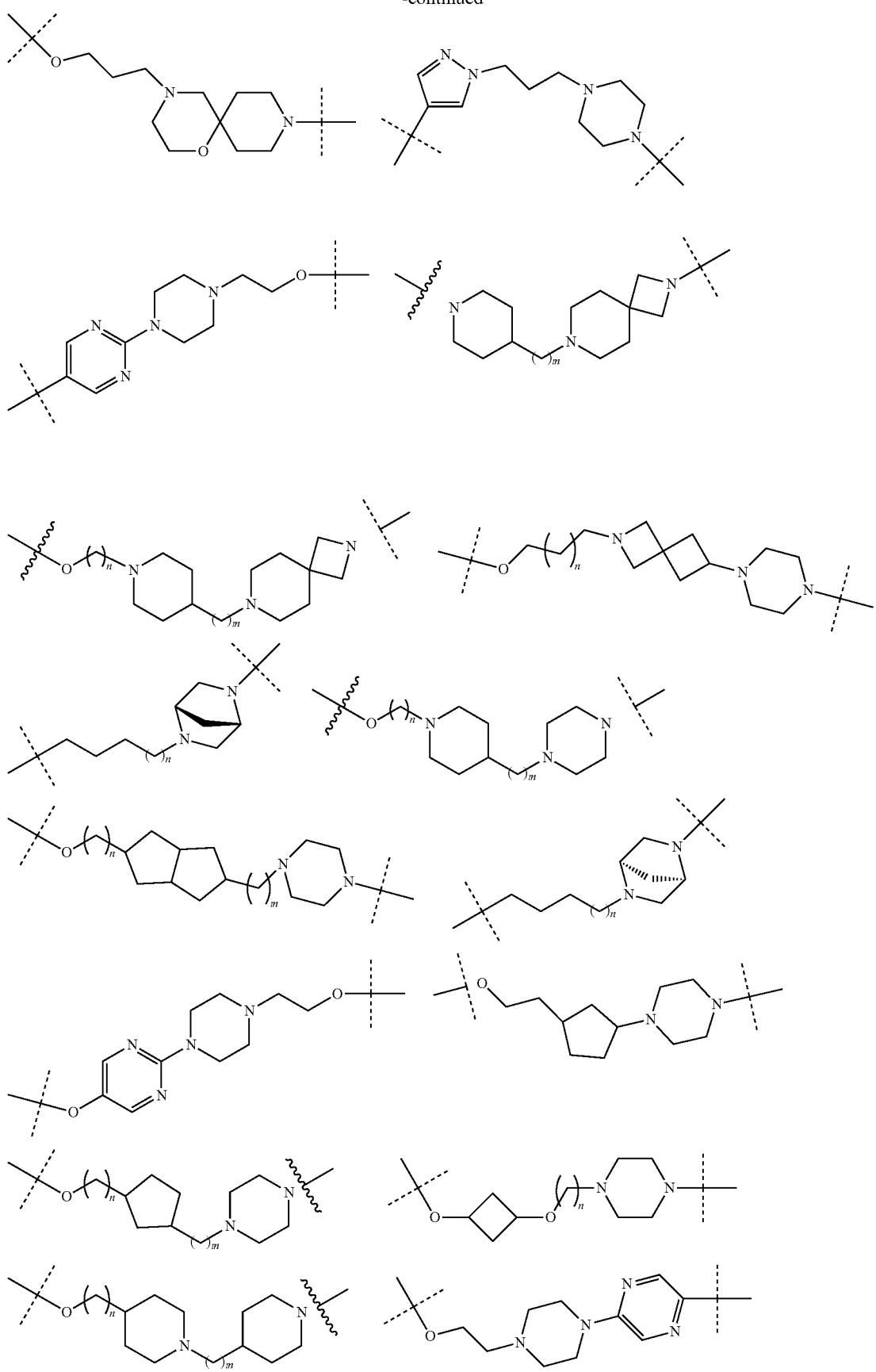

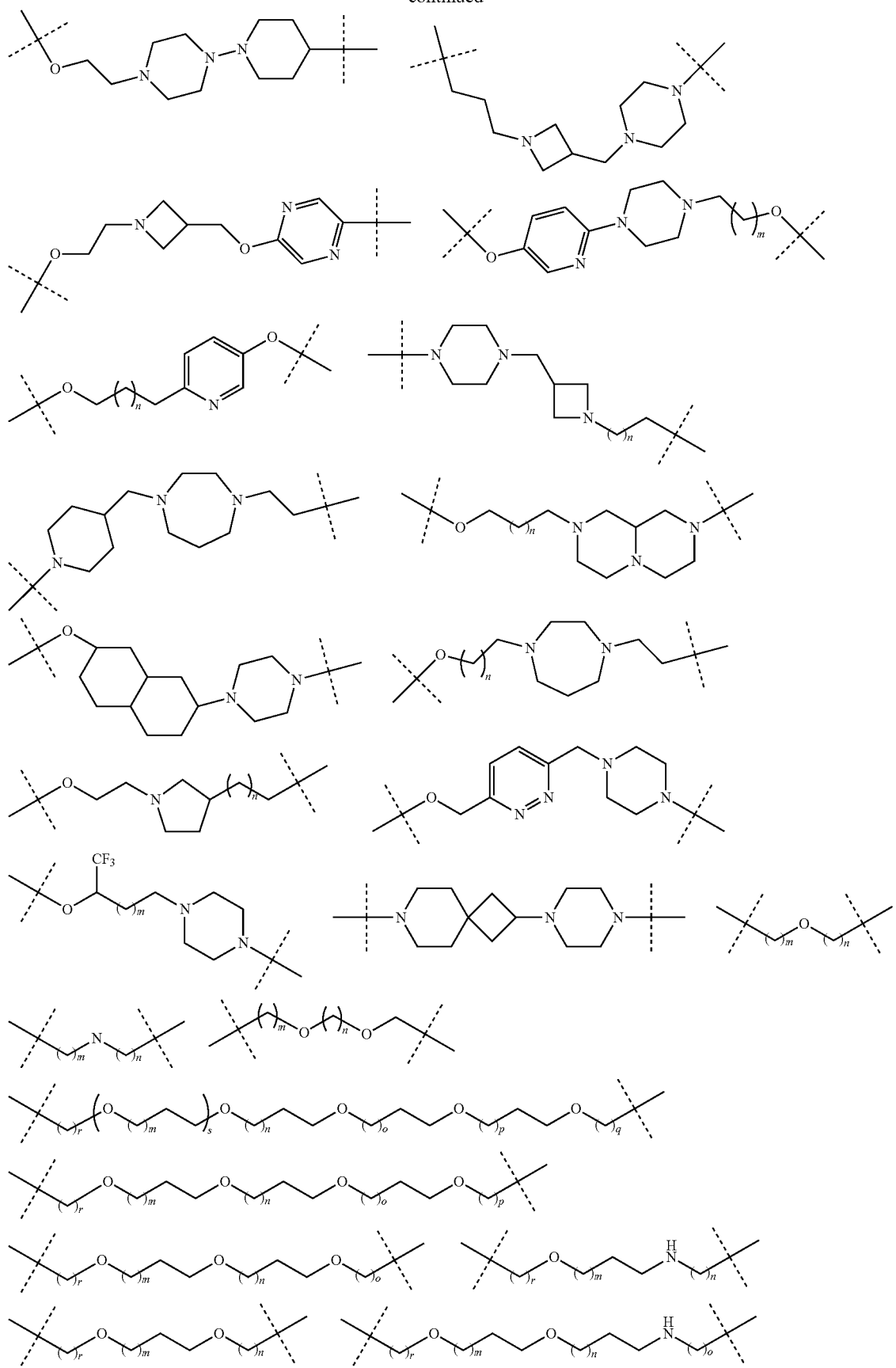

-continued
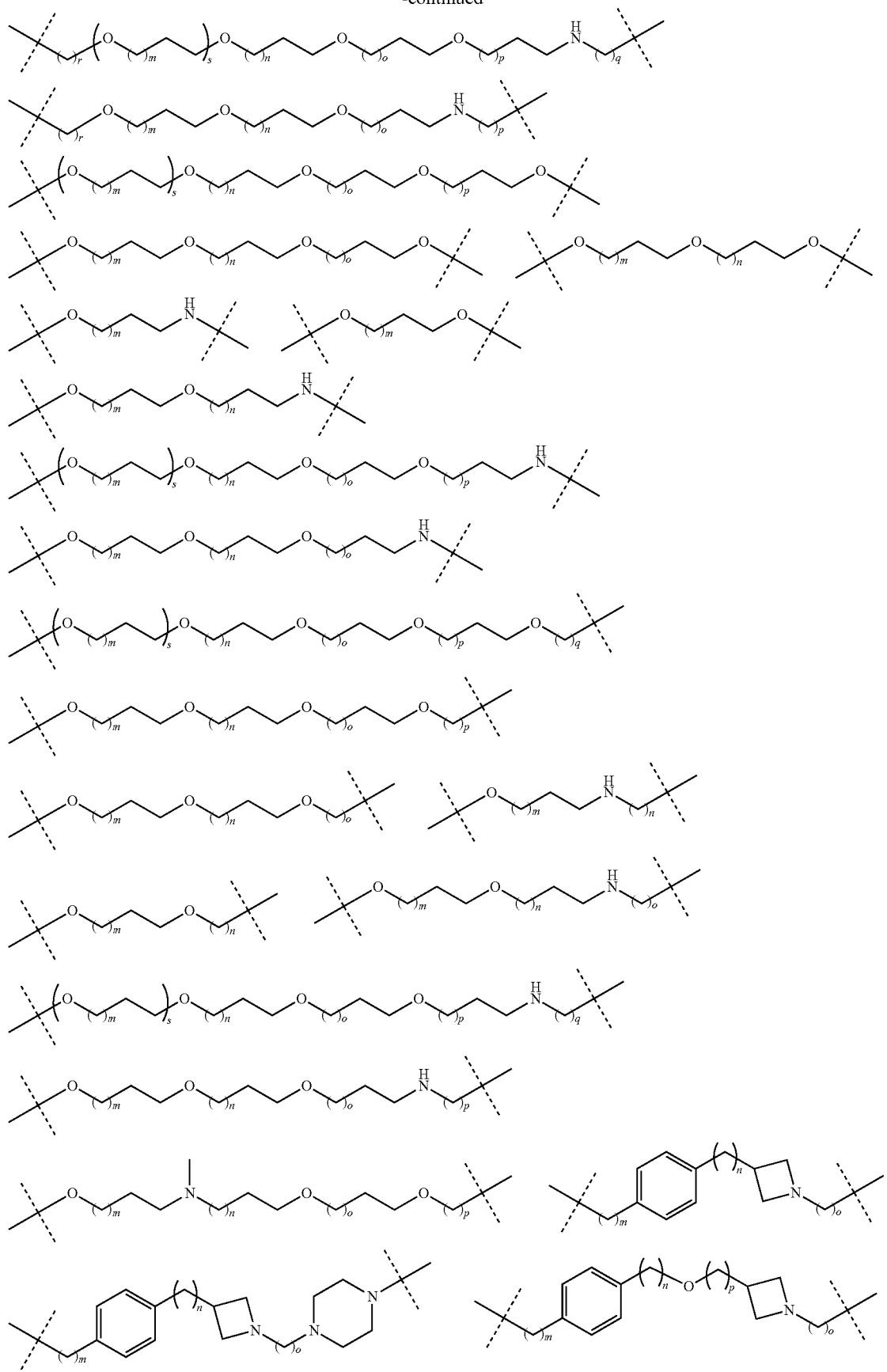

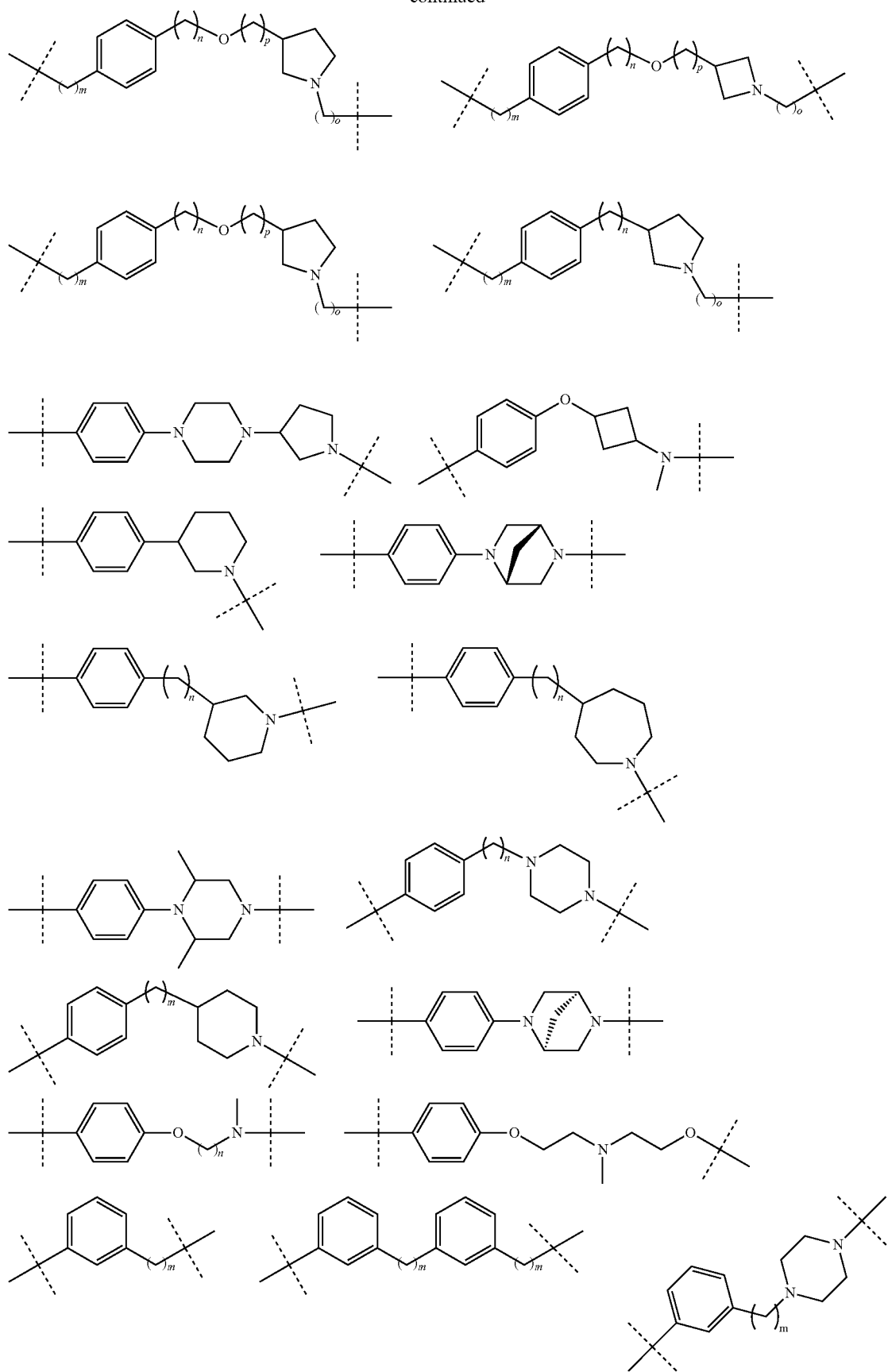

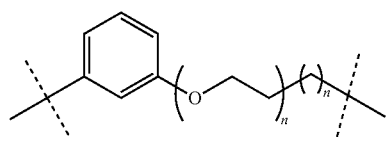
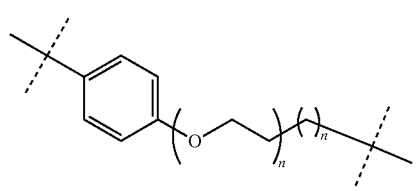
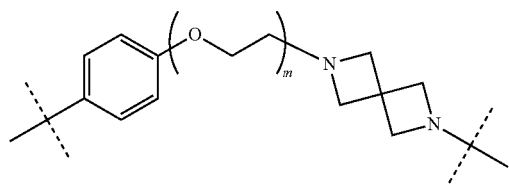
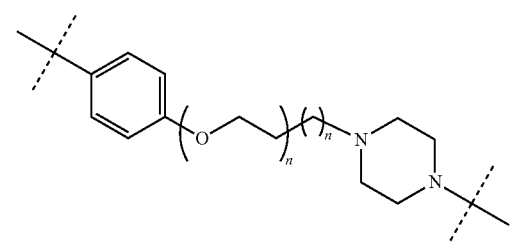
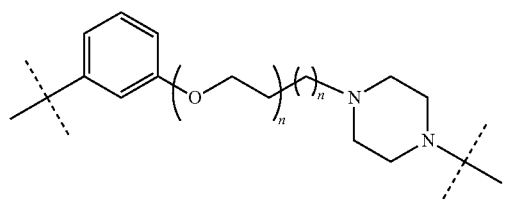
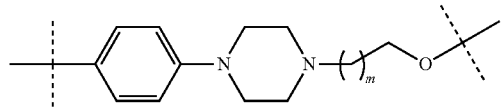
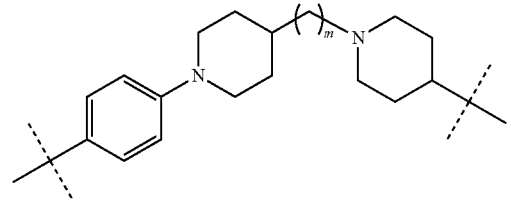
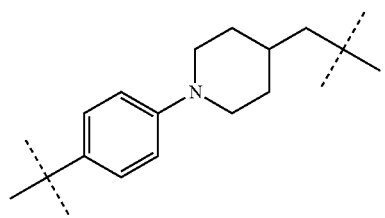
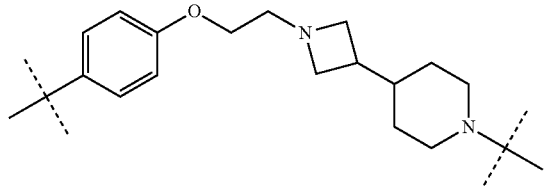
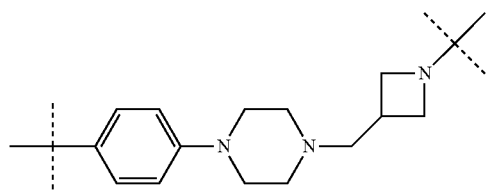
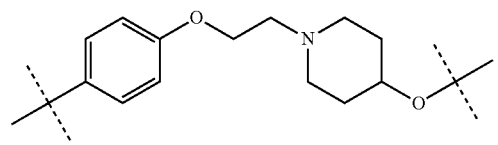
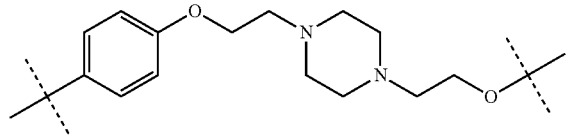
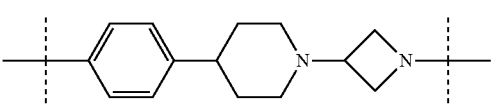
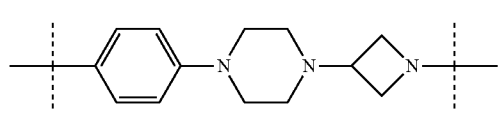
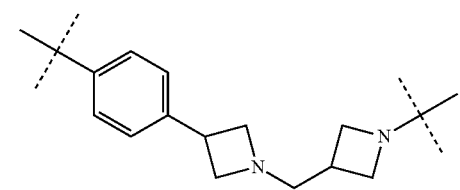

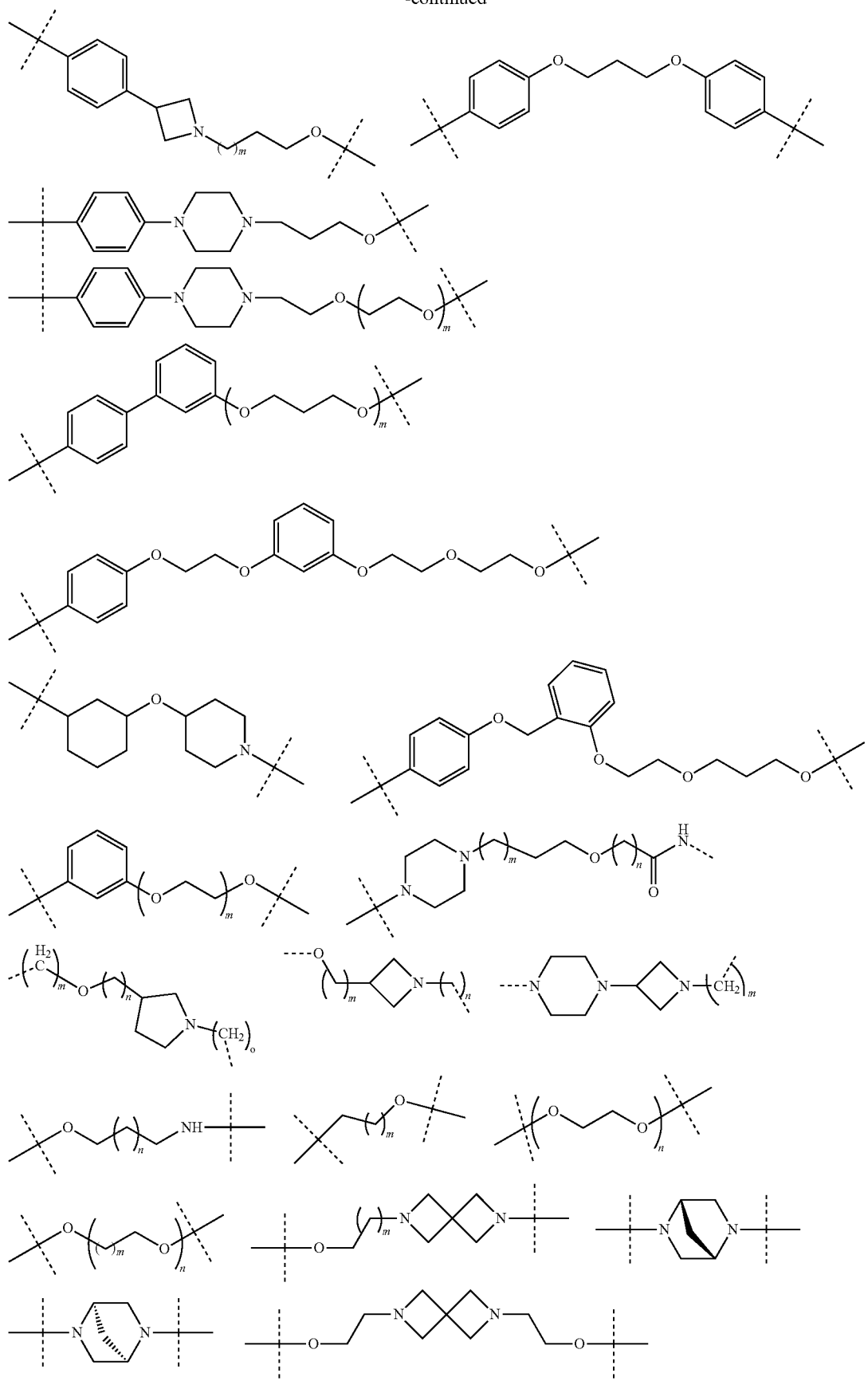

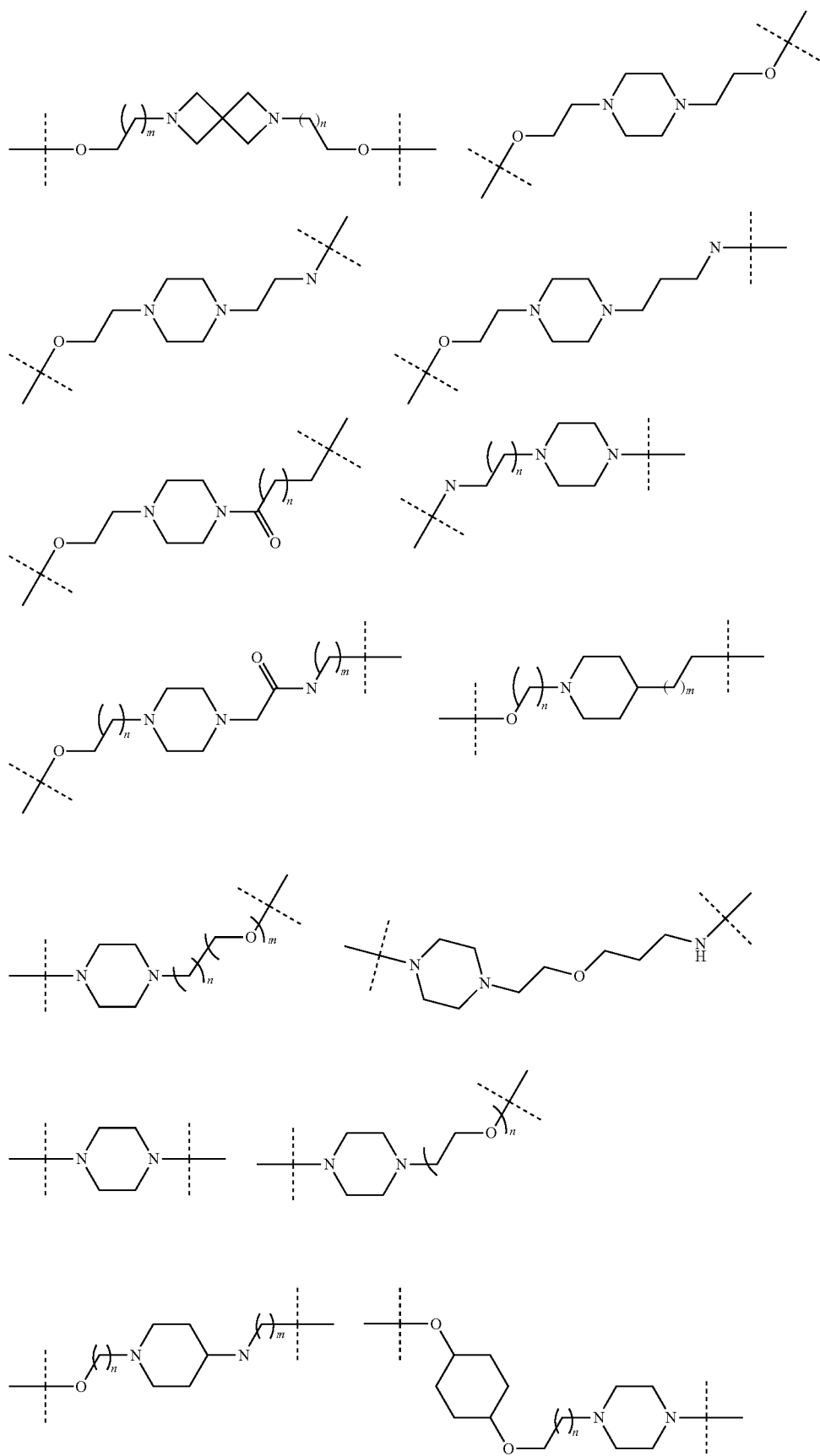

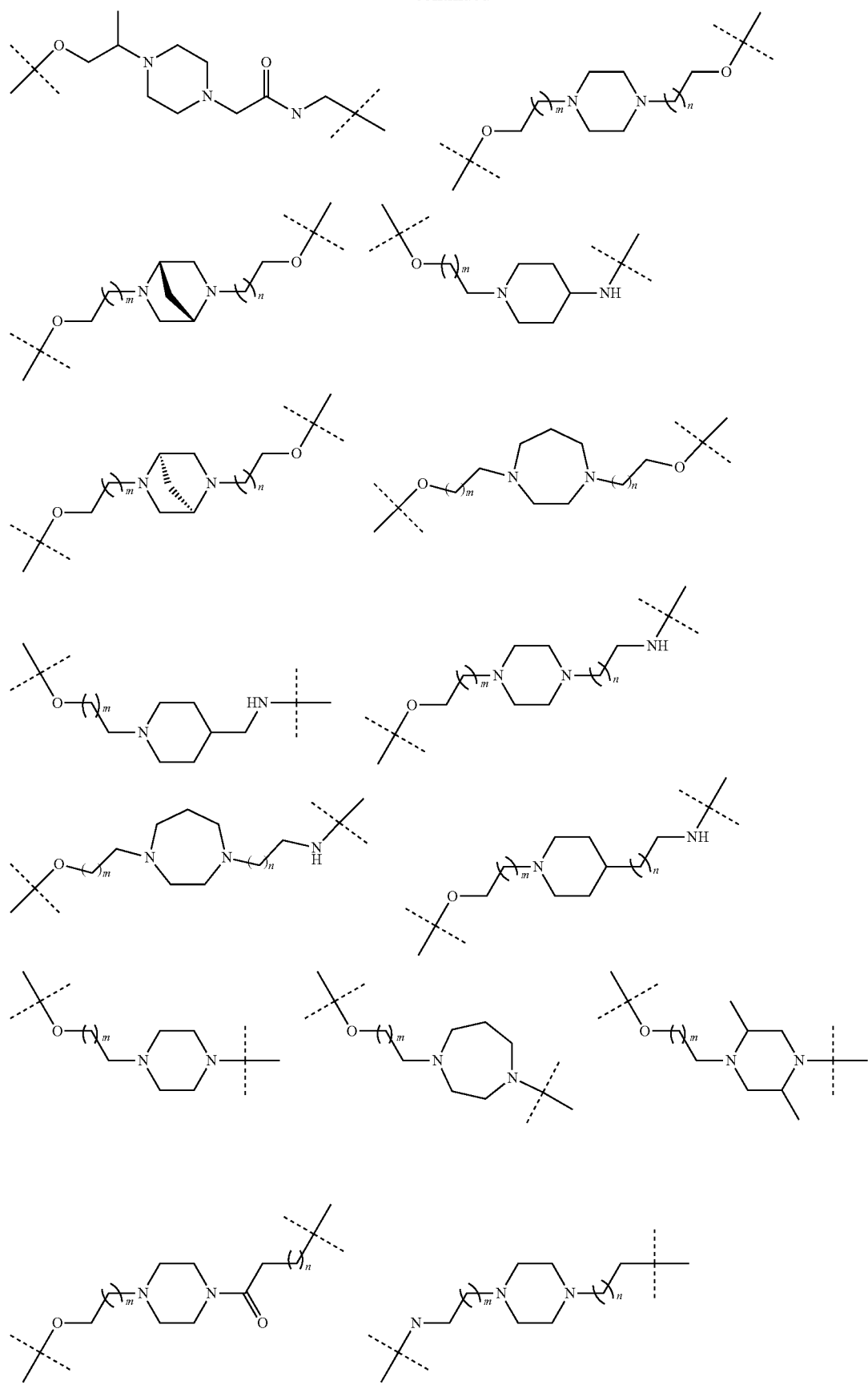

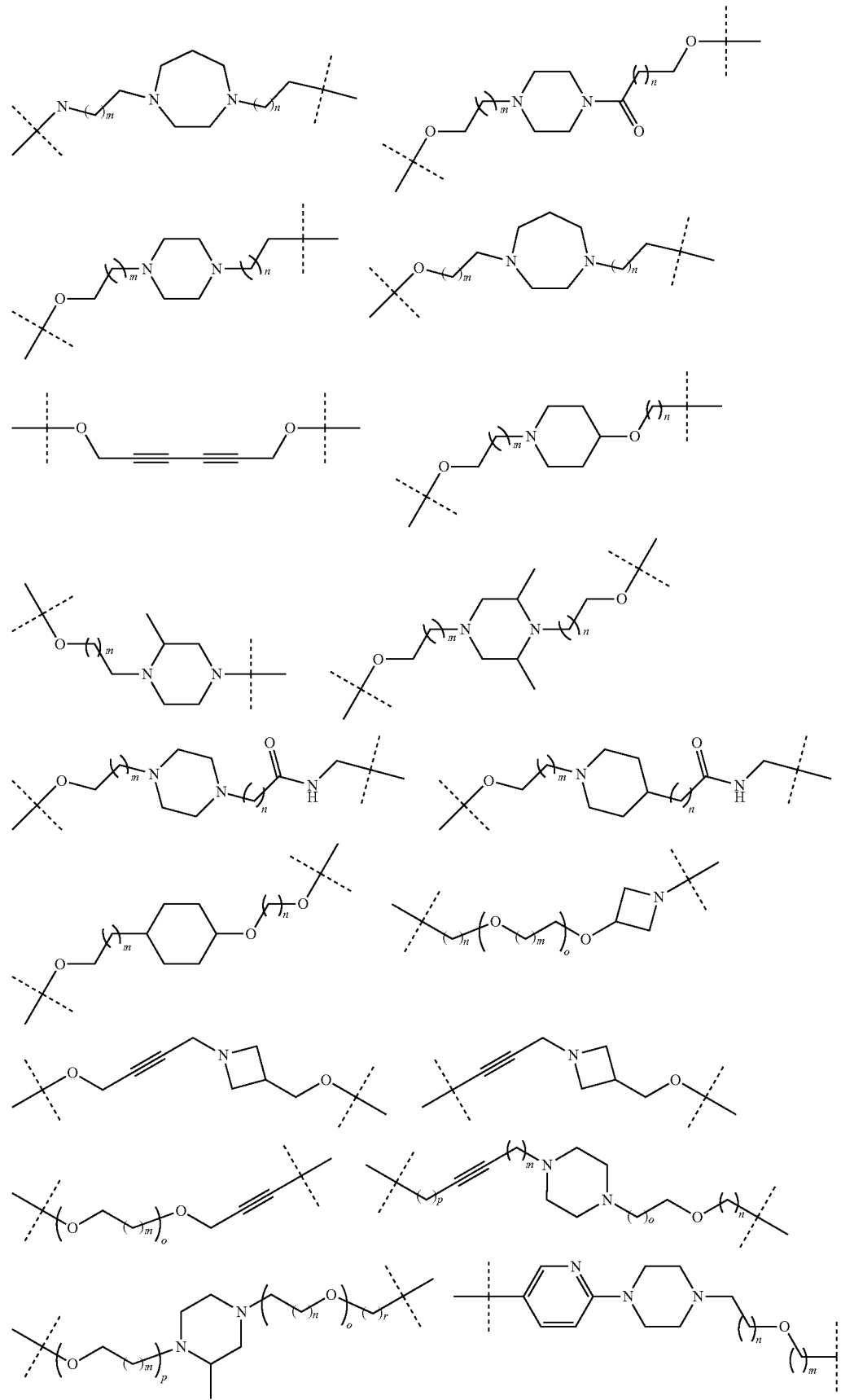

-continued
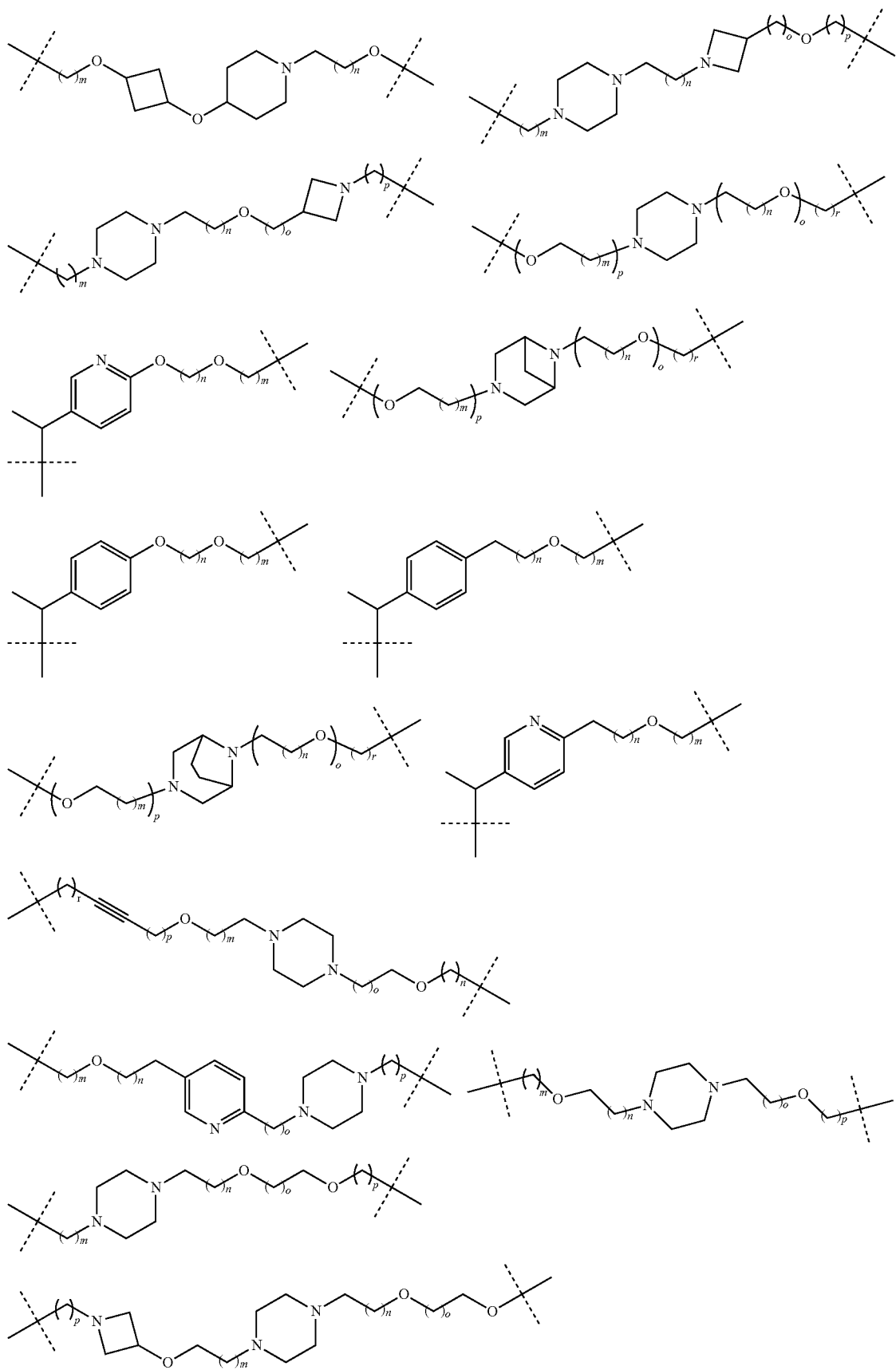

-continued
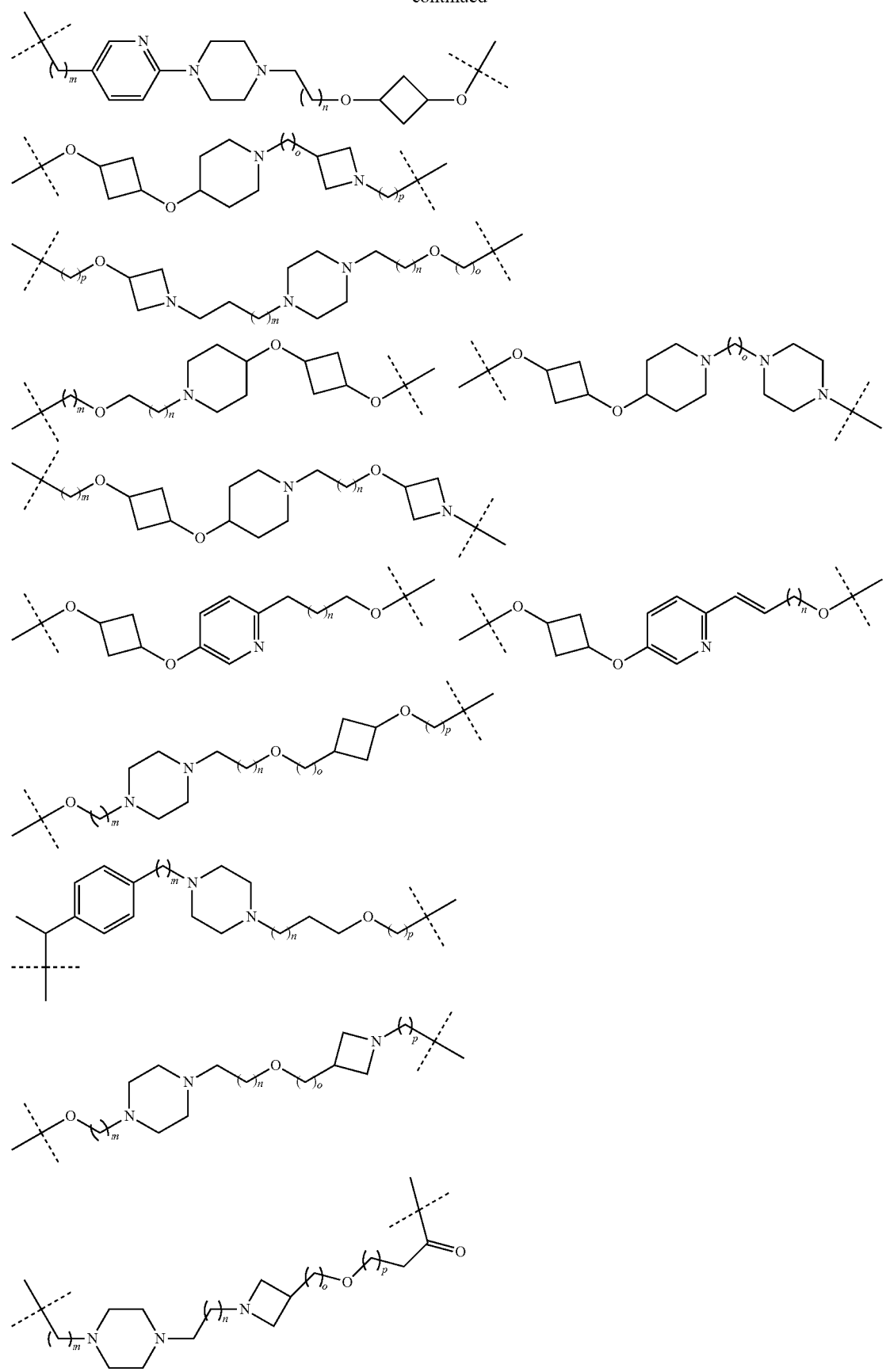

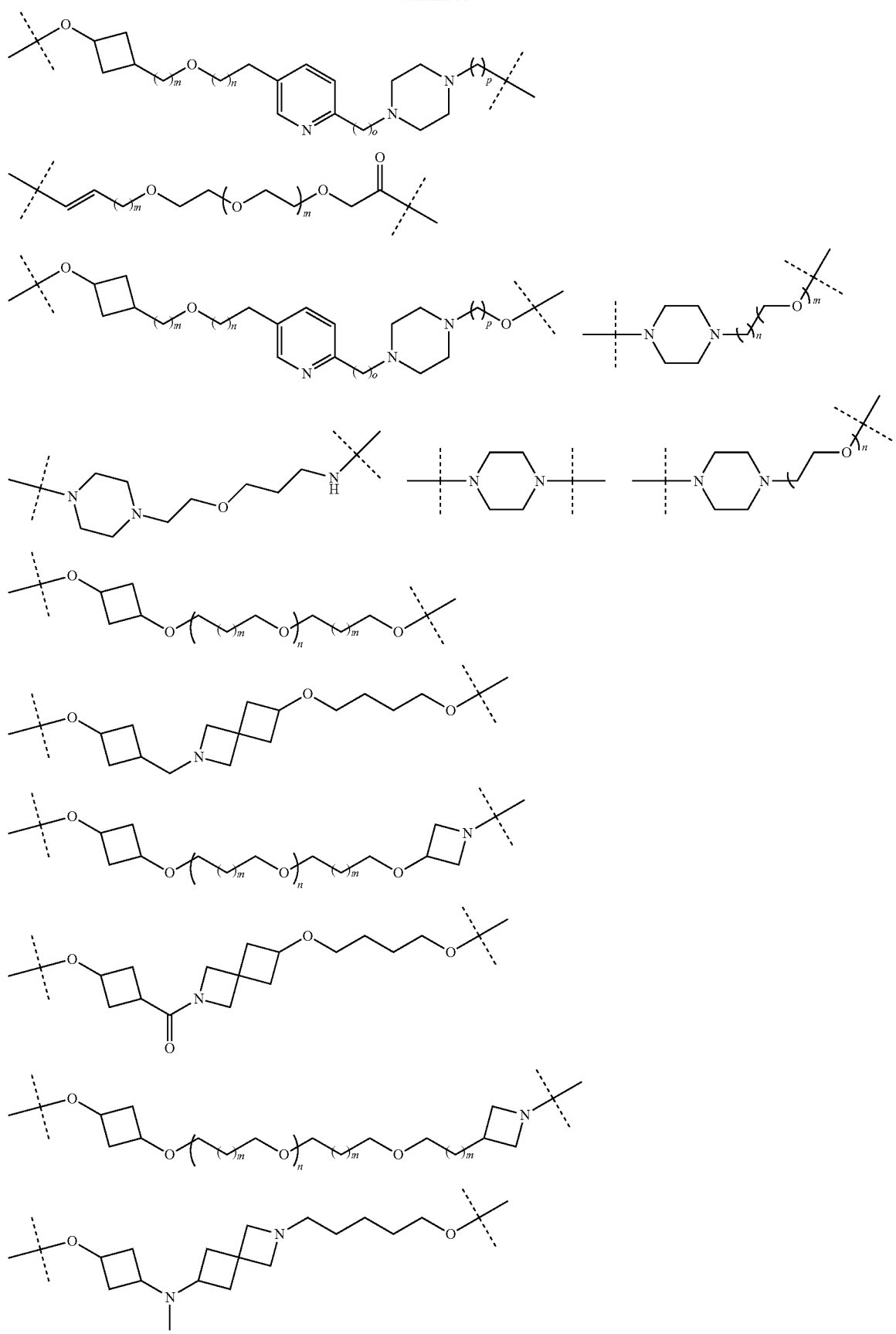

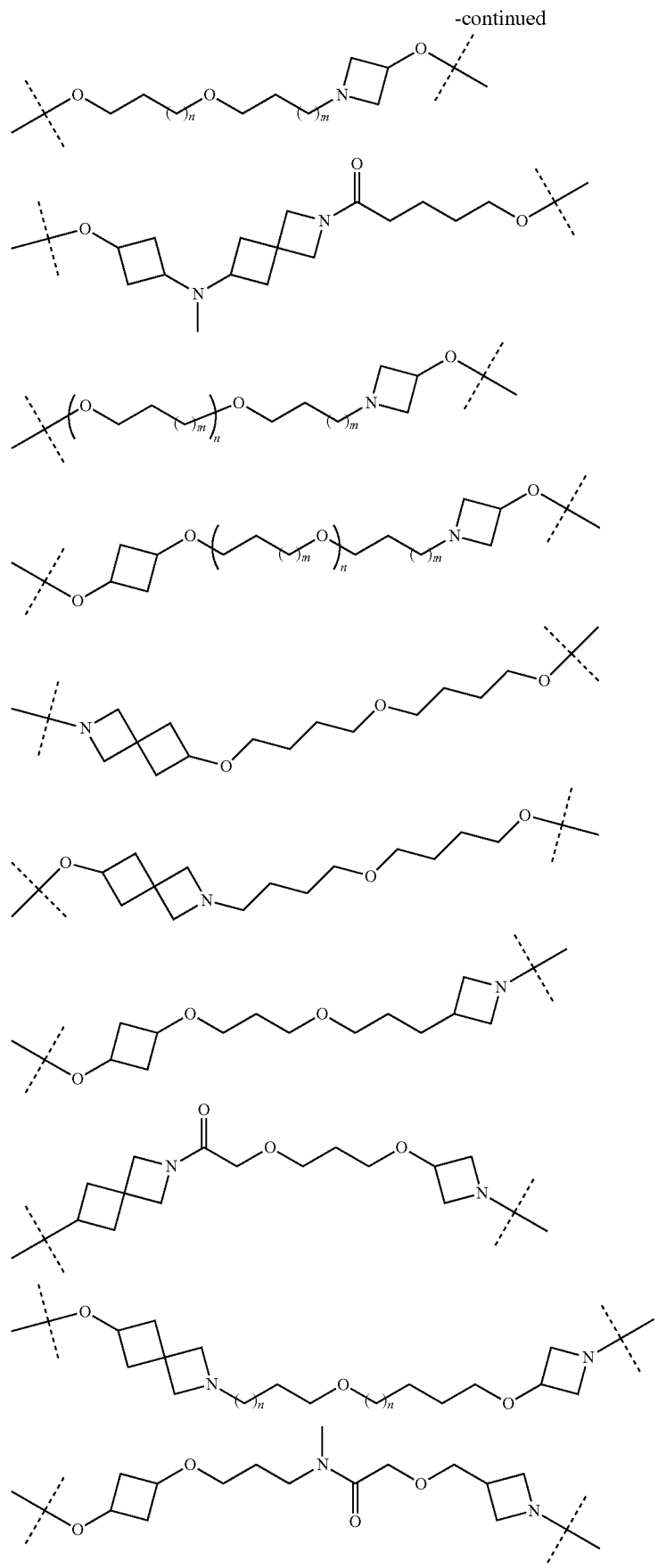

-continued
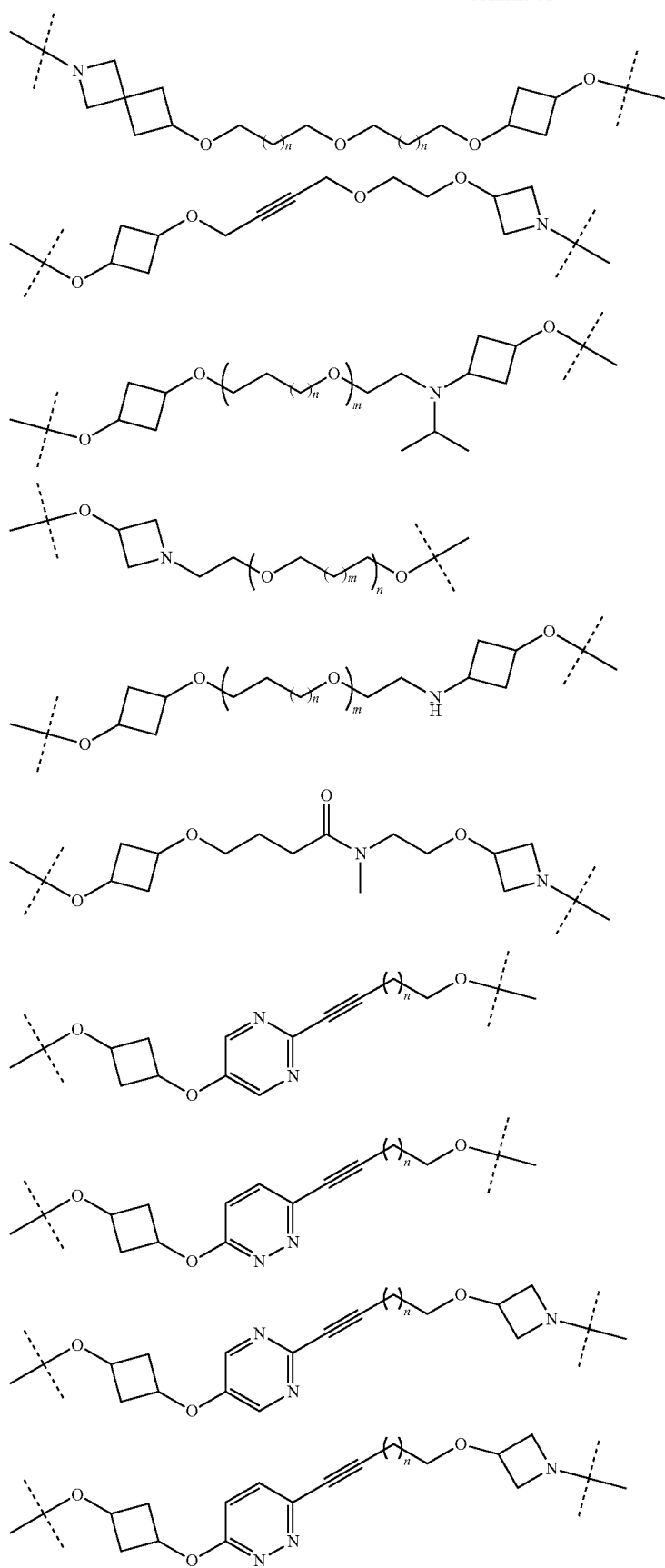

-continued
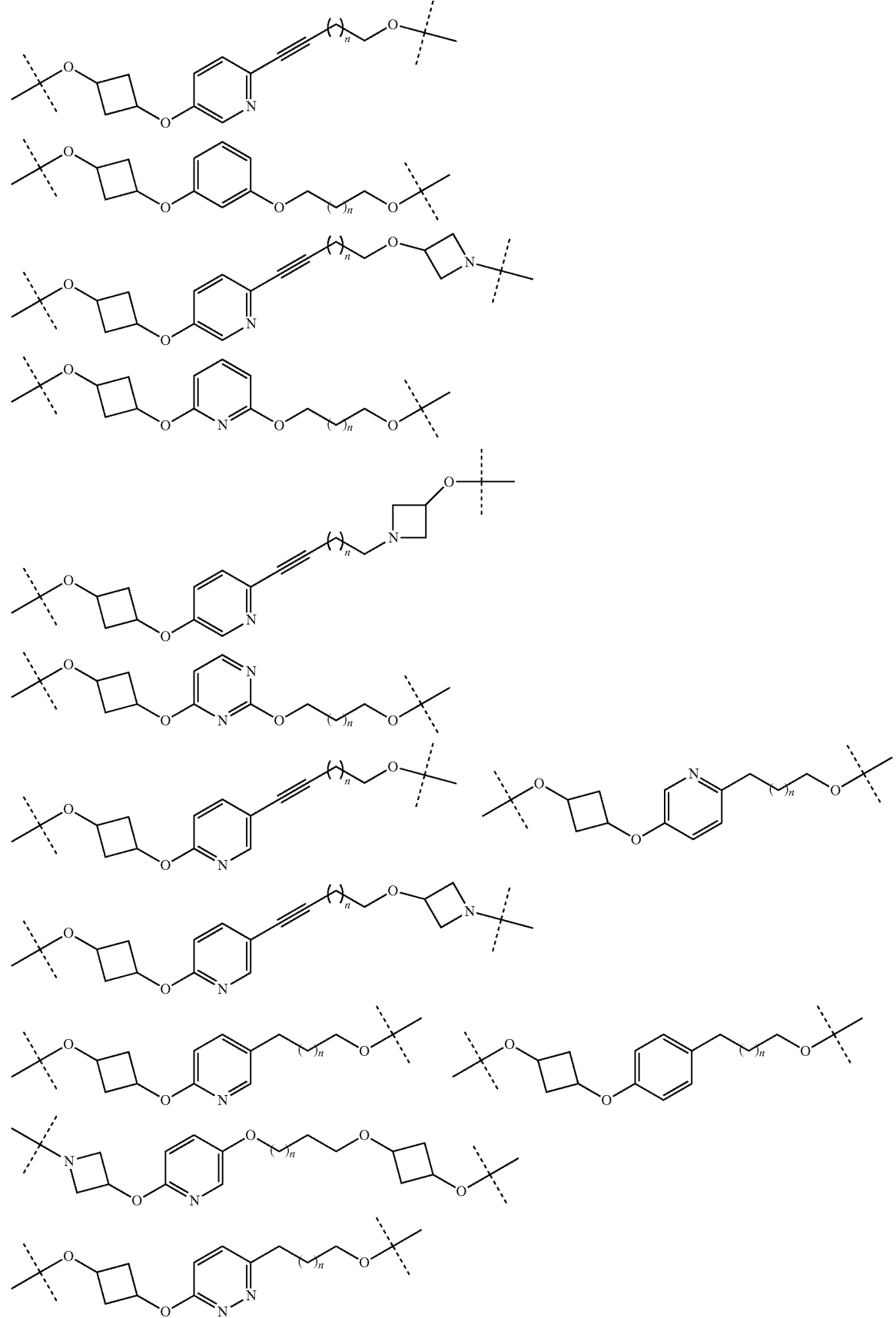

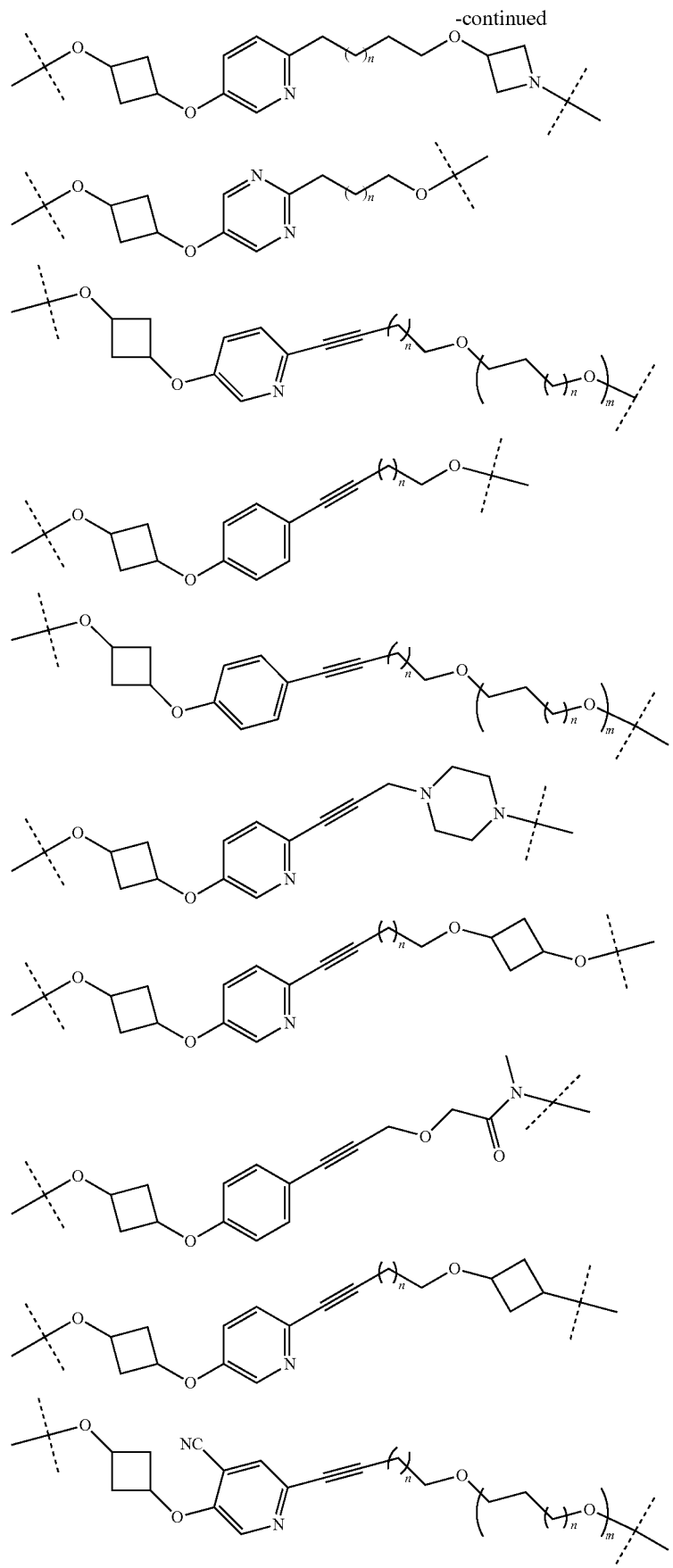

-continued
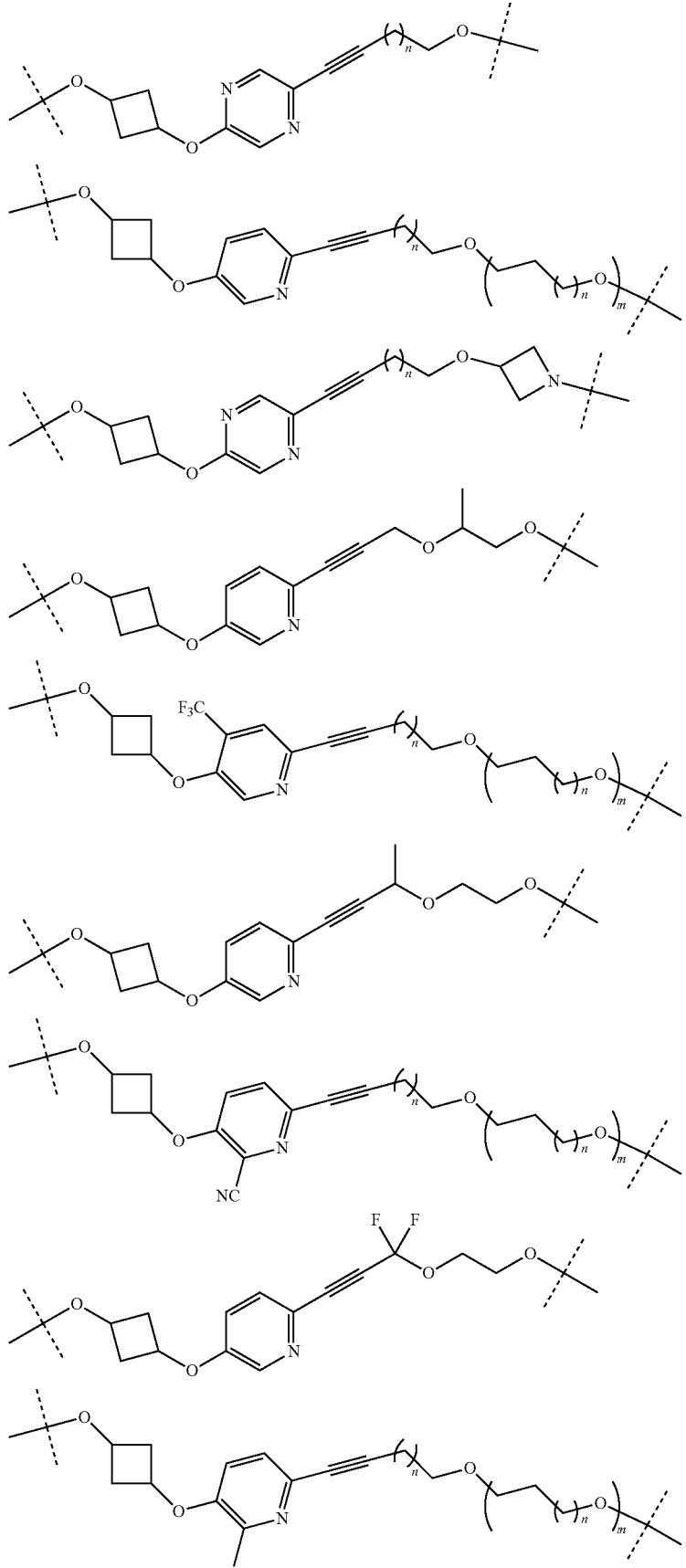

-continued
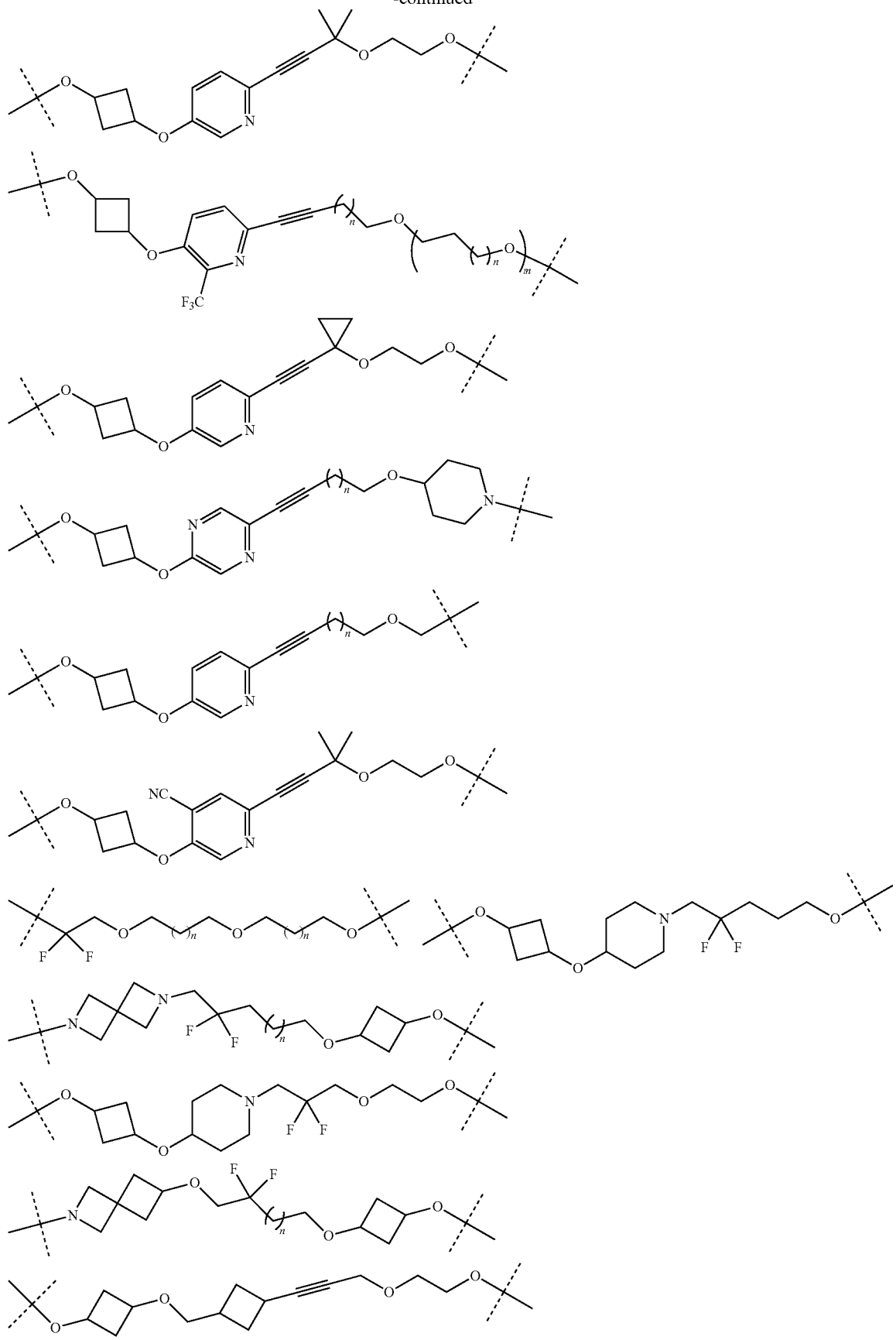

-continued
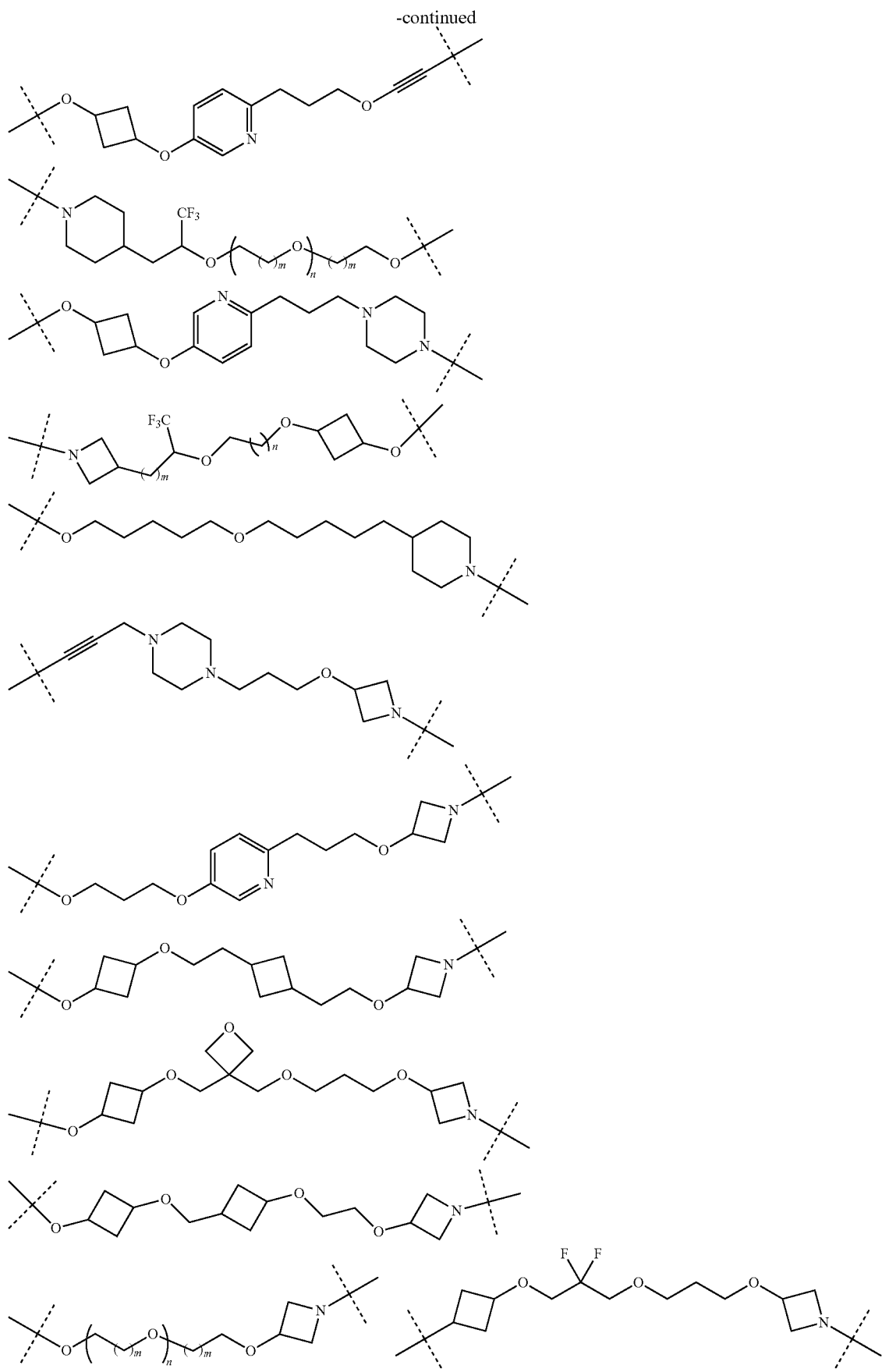

-continued
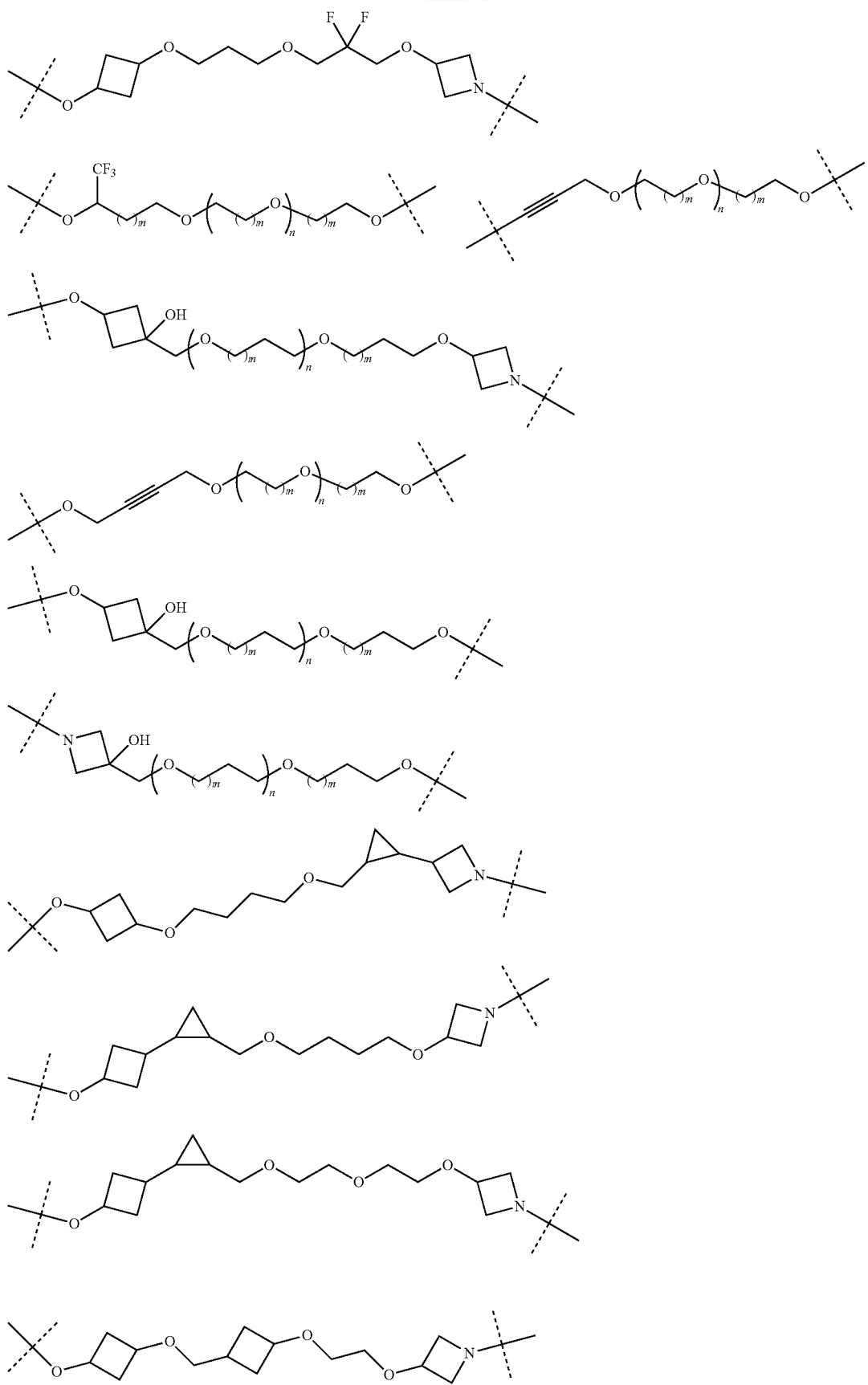

-continued
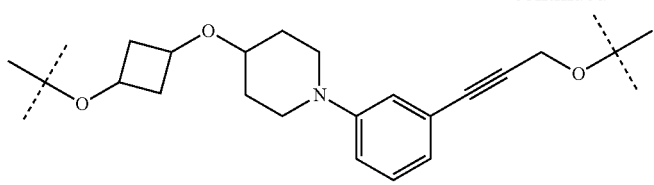
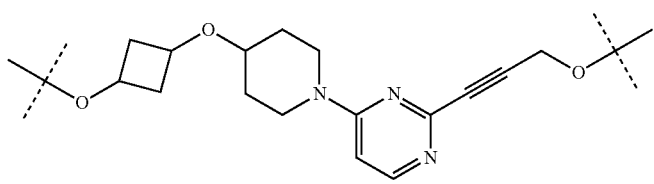
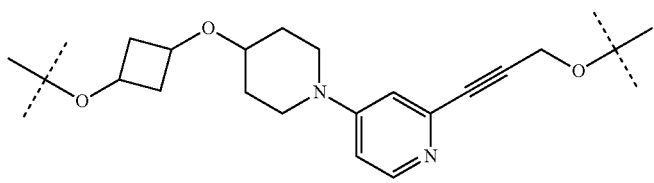
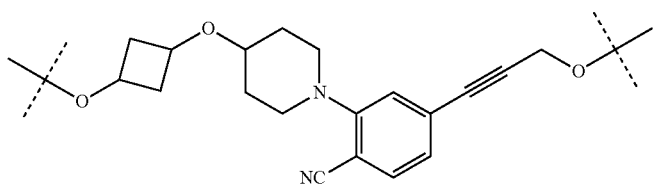
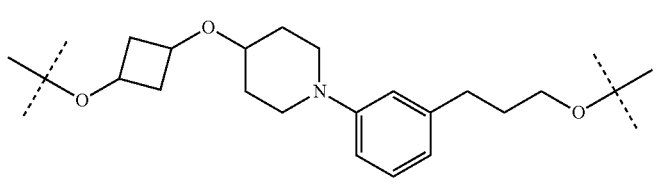
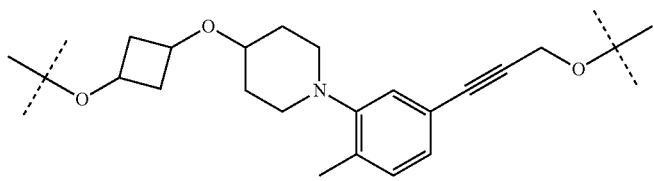
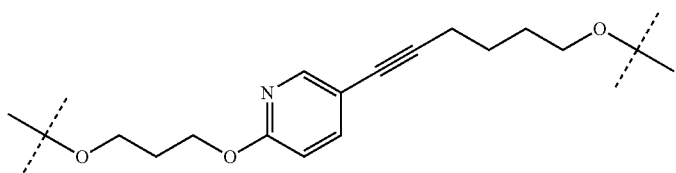
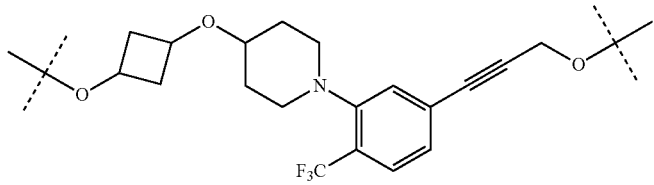
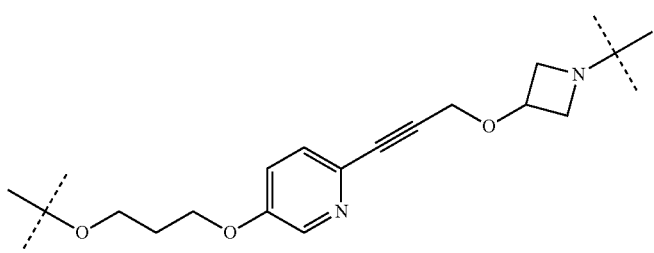

-continued
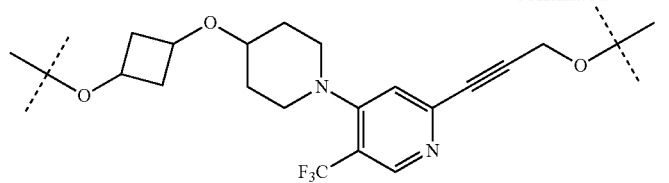
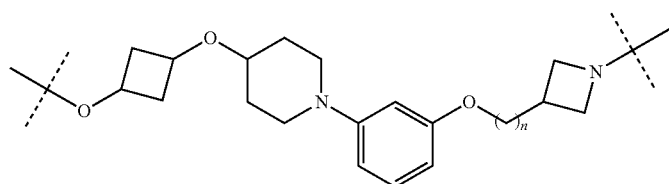
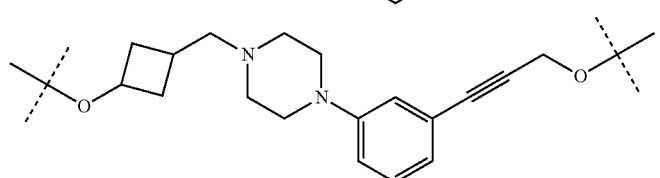
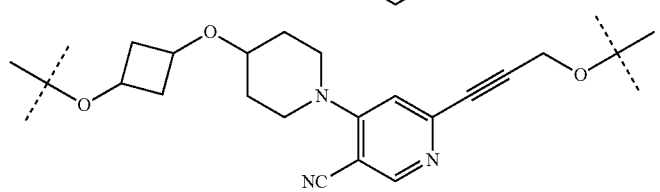
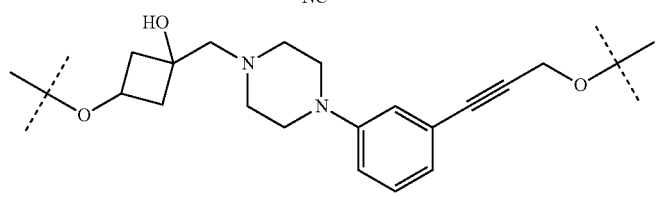
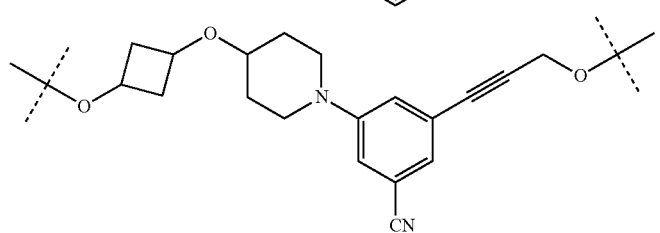
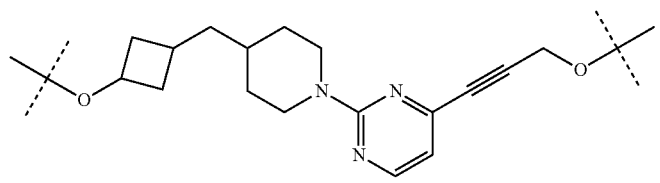
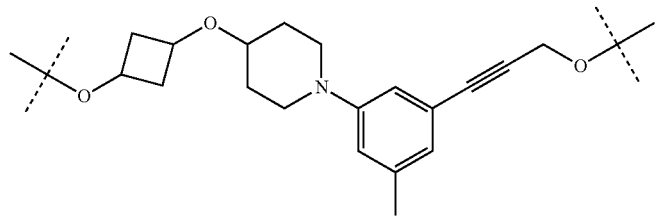
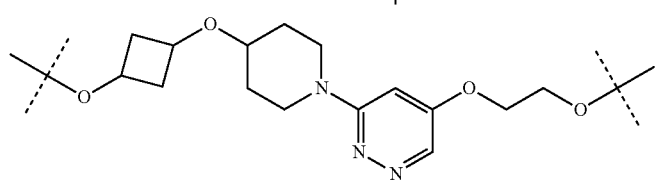

-continued
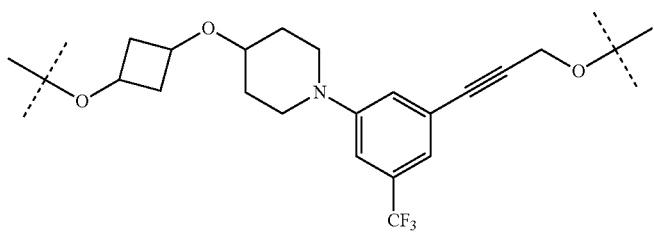
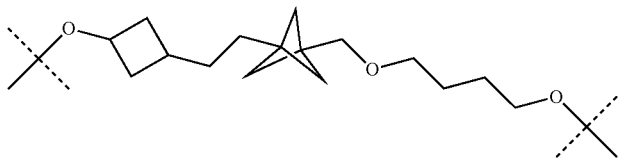
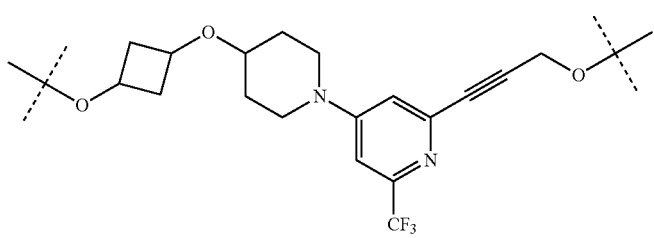
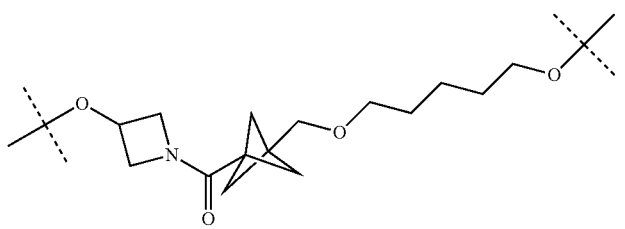
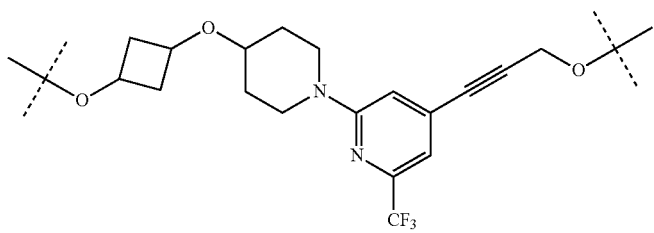
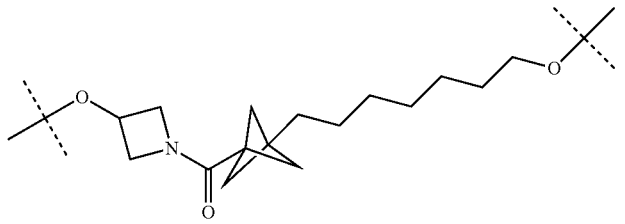
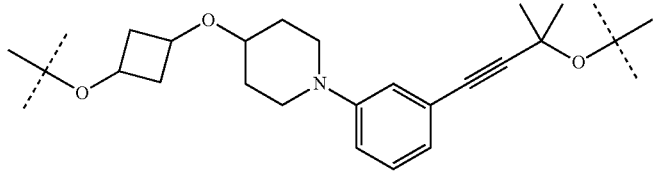
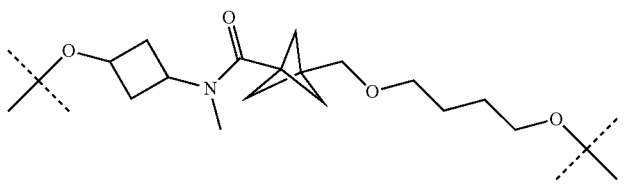

-continued
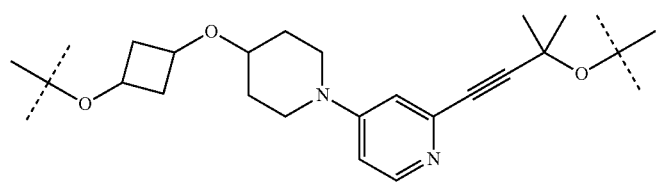
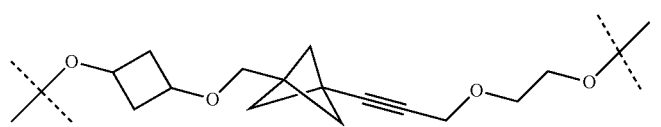
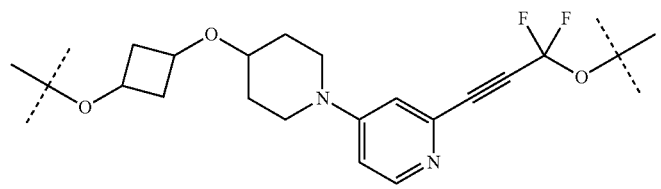
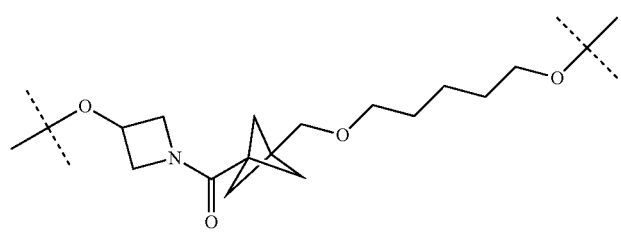
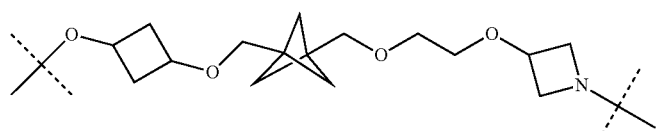
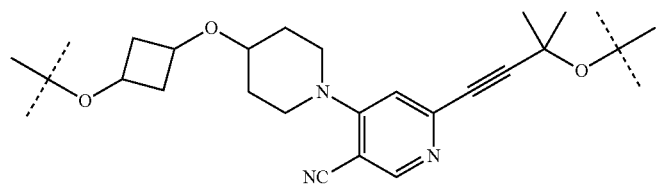
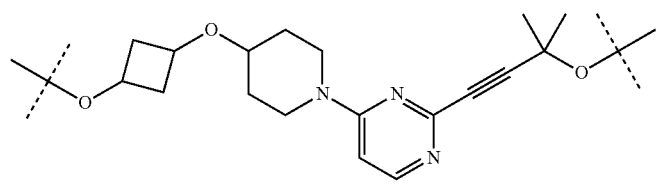
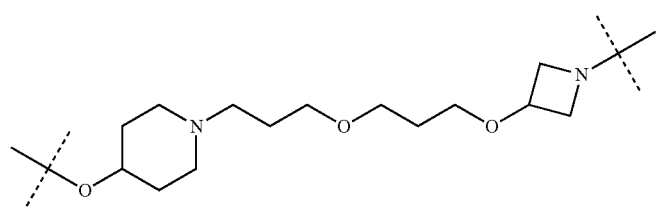
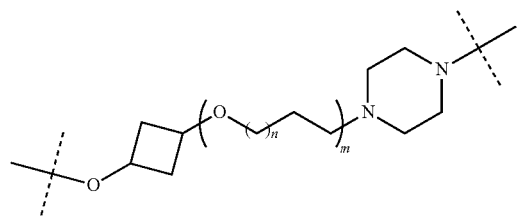

-continued
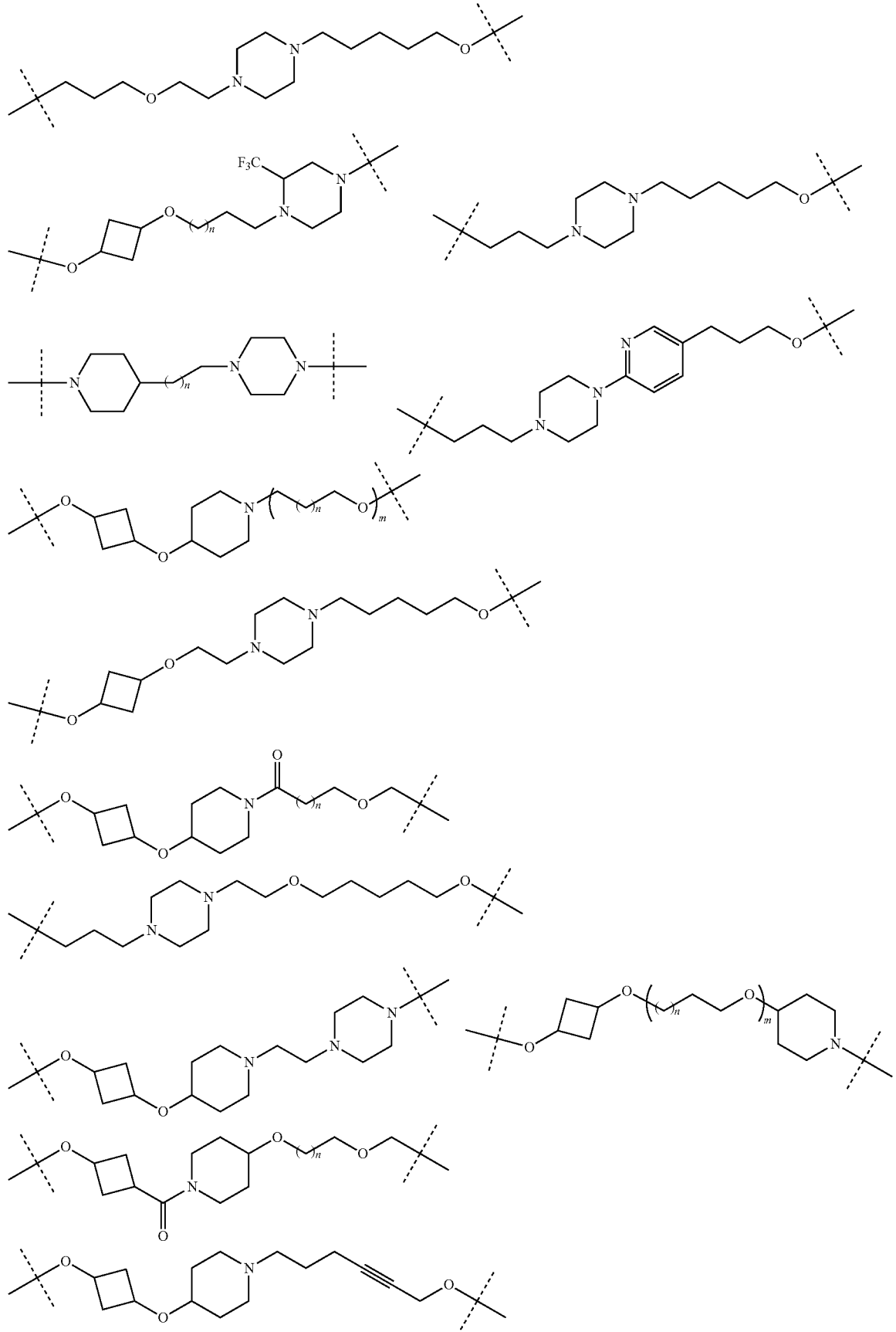

-continued
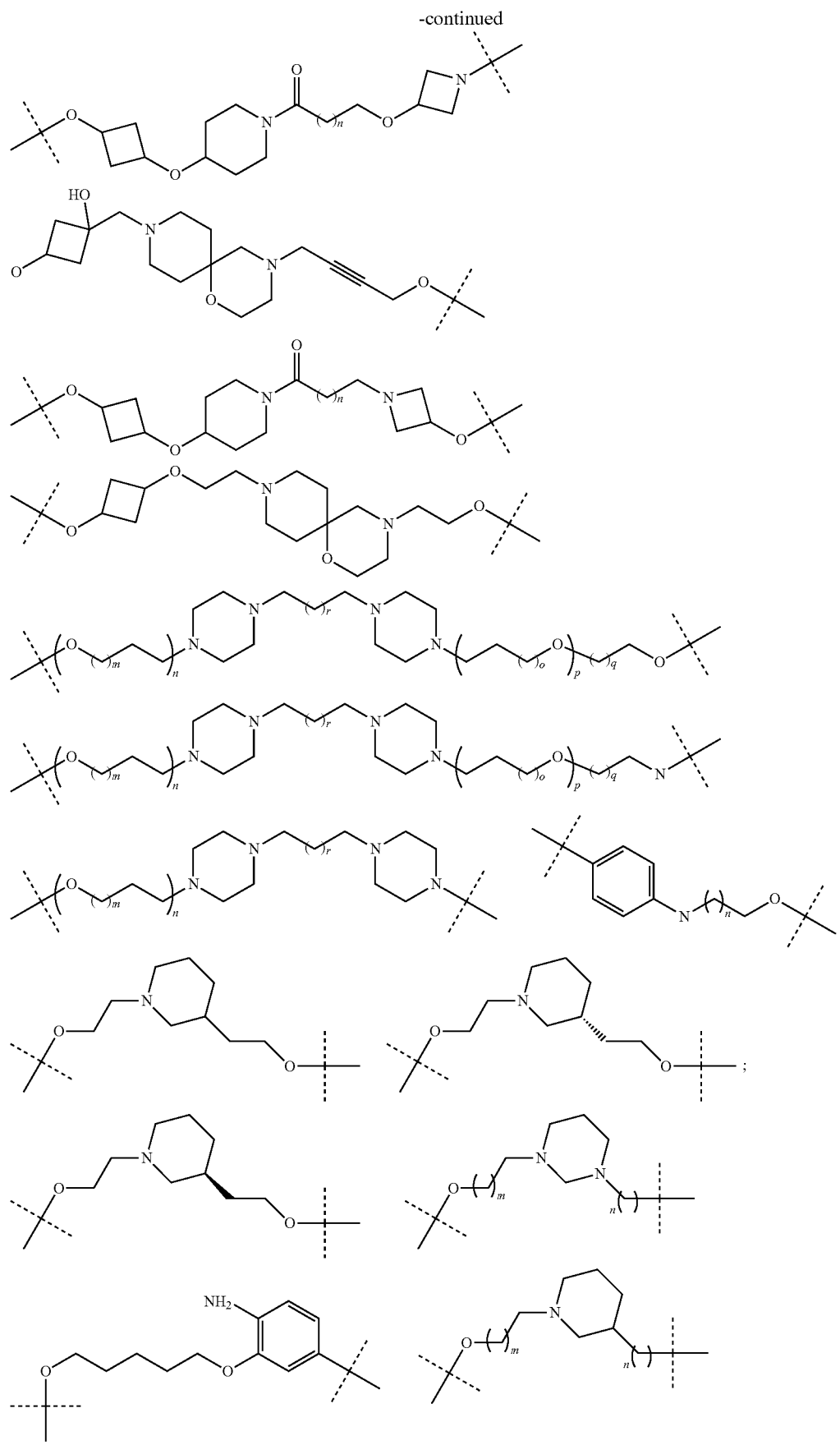

-continued
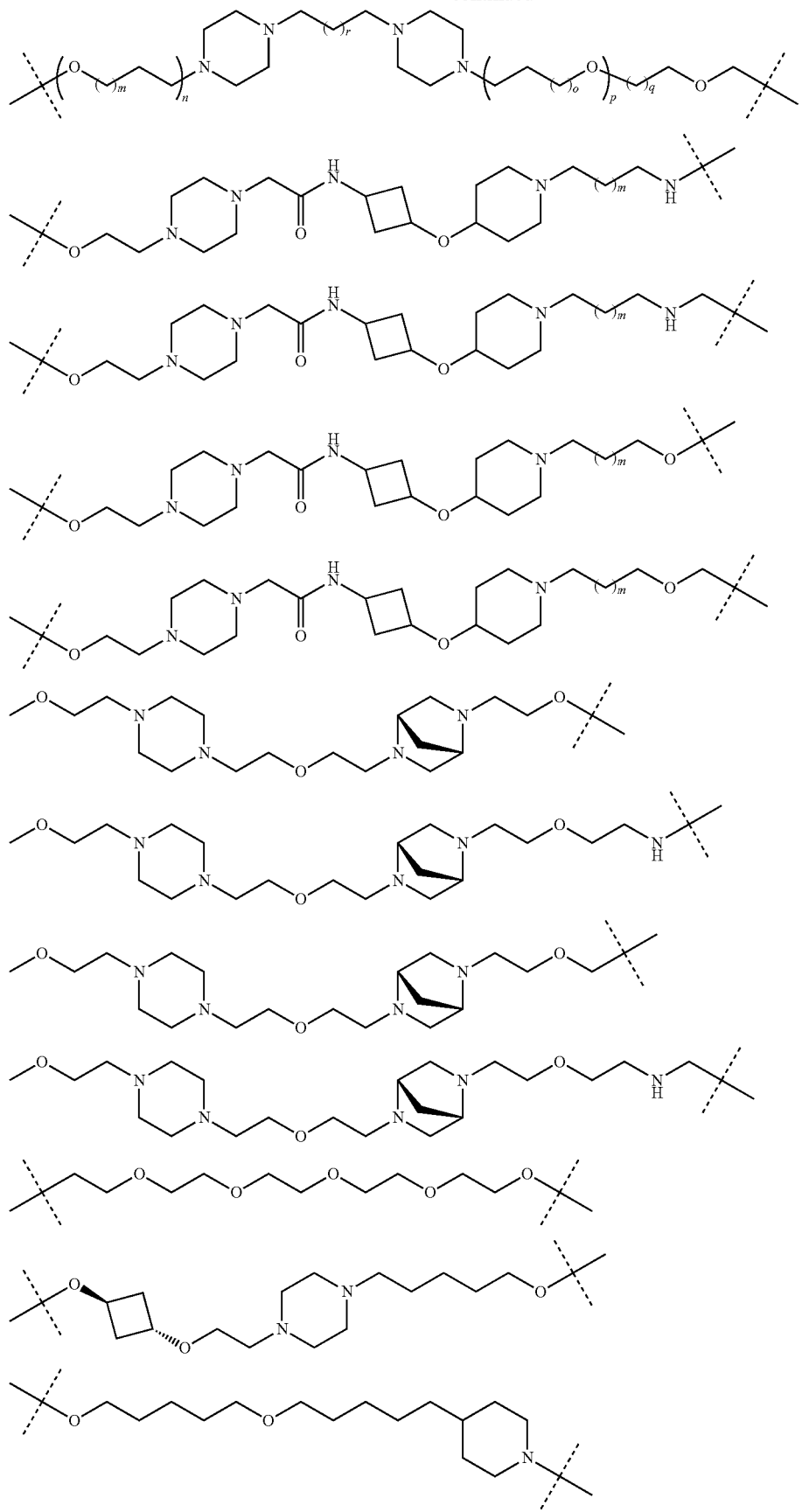

-continued
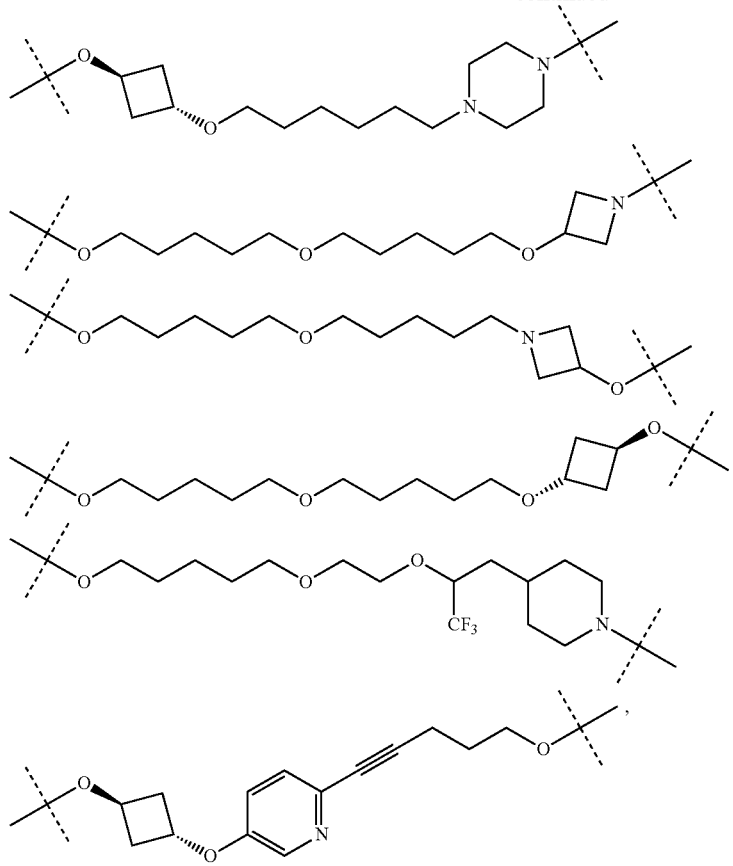
wherein each m, n, o, p, q, r, and s is independently 0, 1, 2, 3, 4, 5, 6, 7, 8, 9, 10, 11, 12, 13, 14, 15, 16, 17, 18, 19, or 20.
In any aspect or embodiment described herein, the unit $A^L$ of linker (L) is selected from the group consisting of:
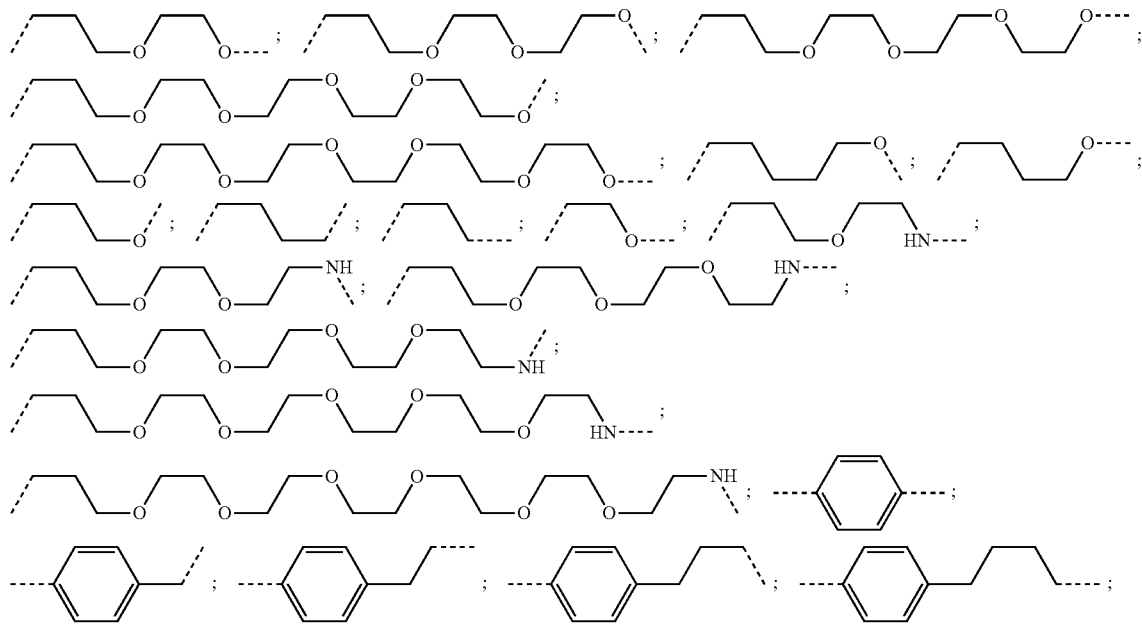

411
-continued
412
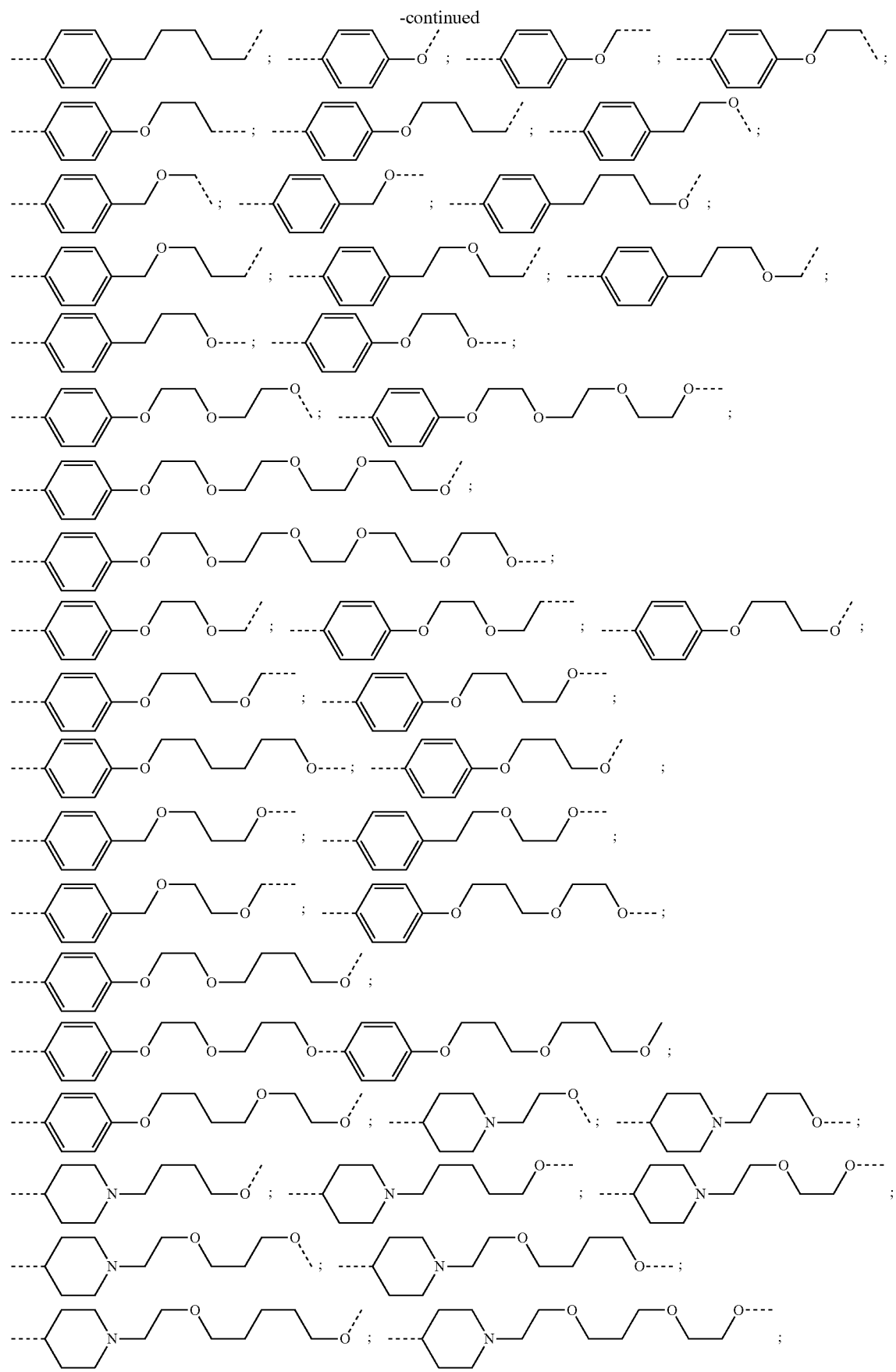

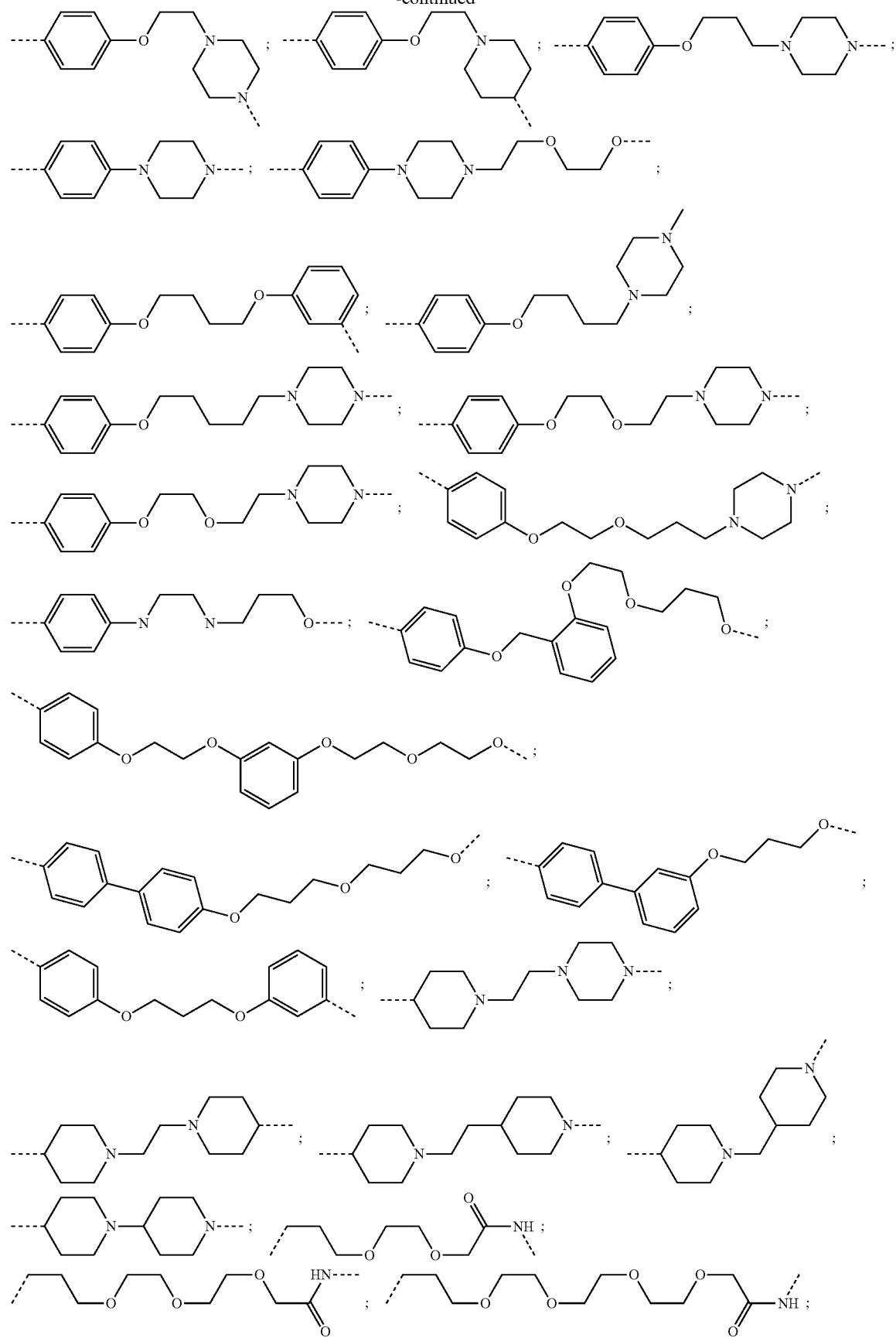

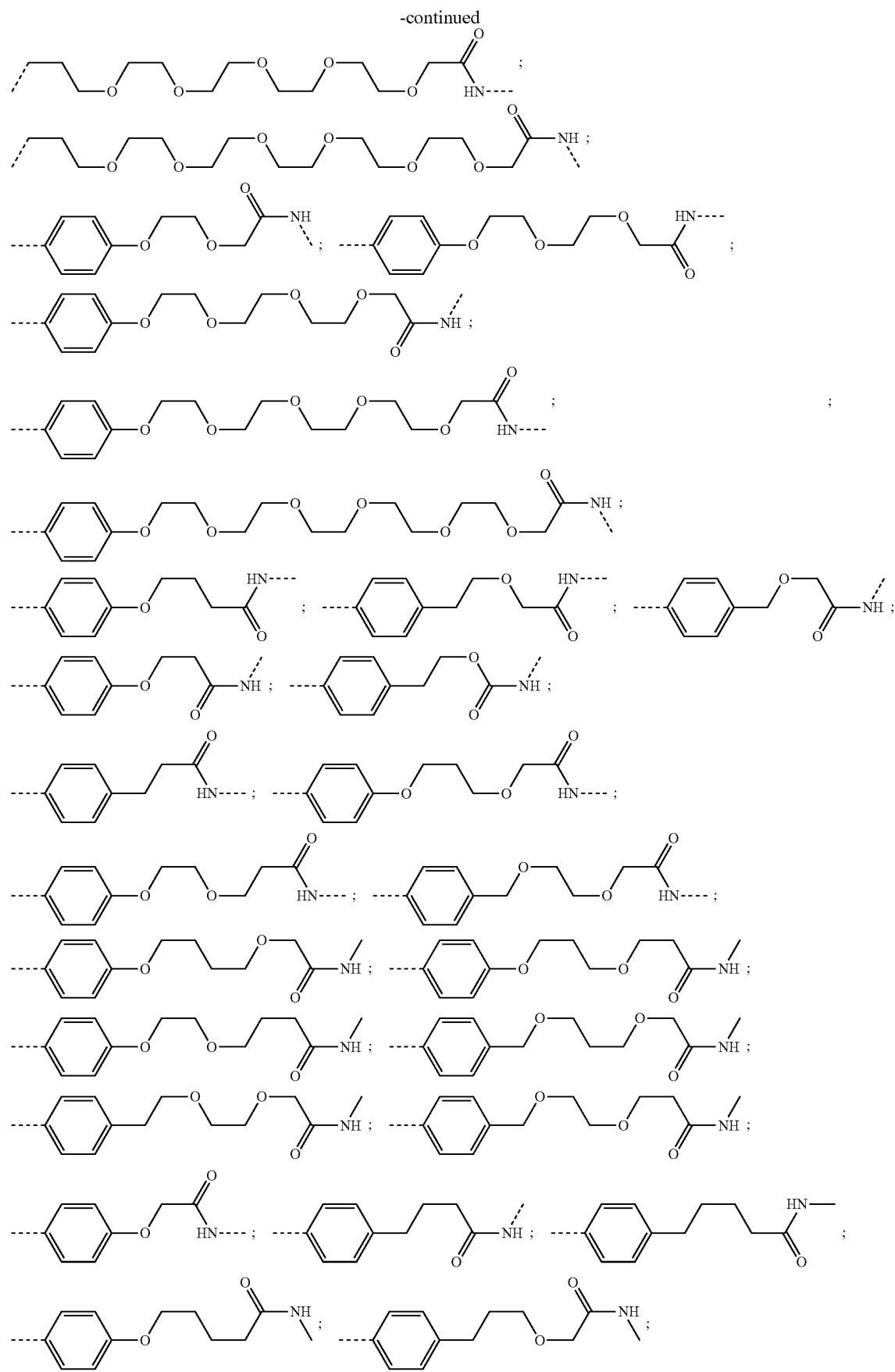

417 418
-continued
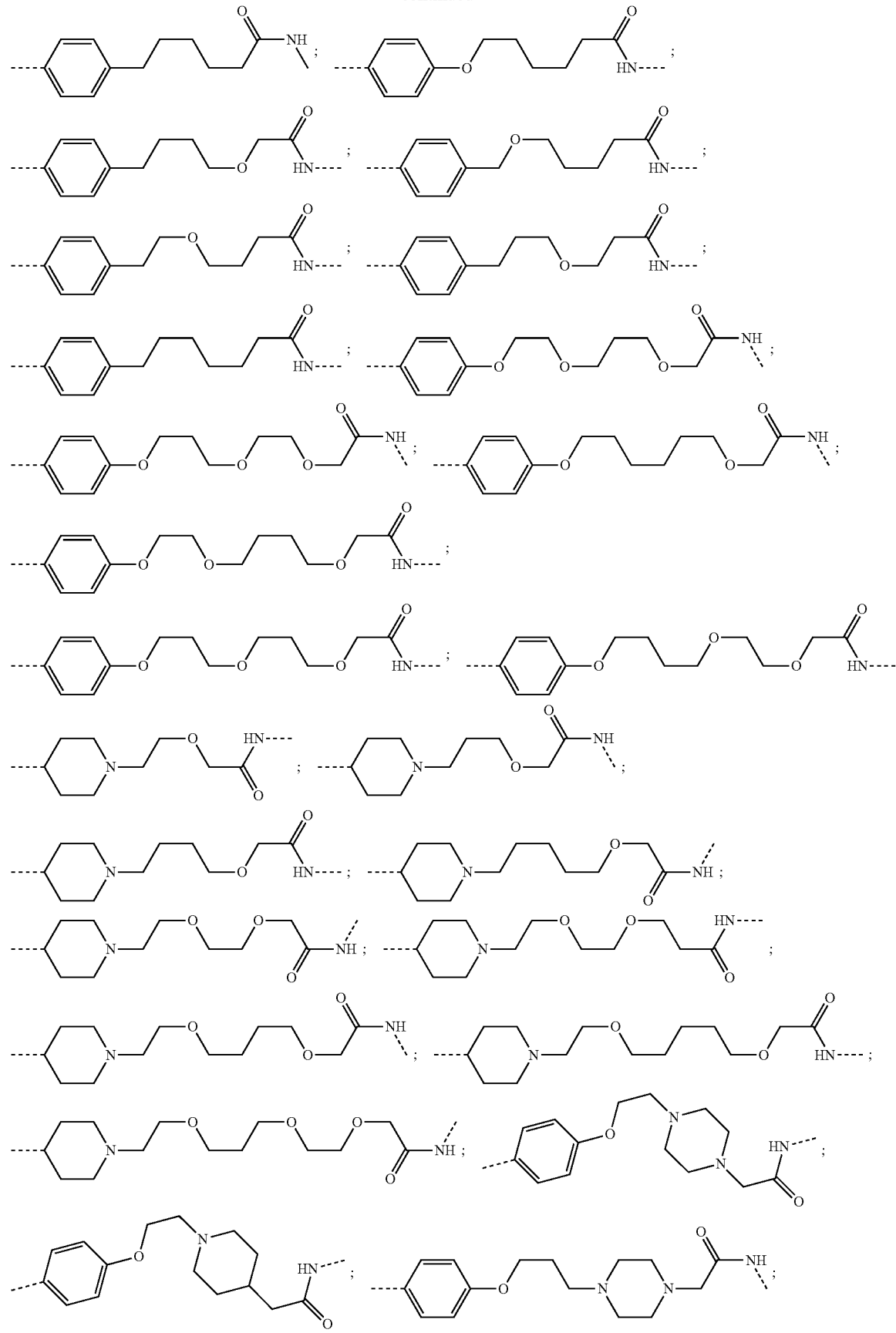

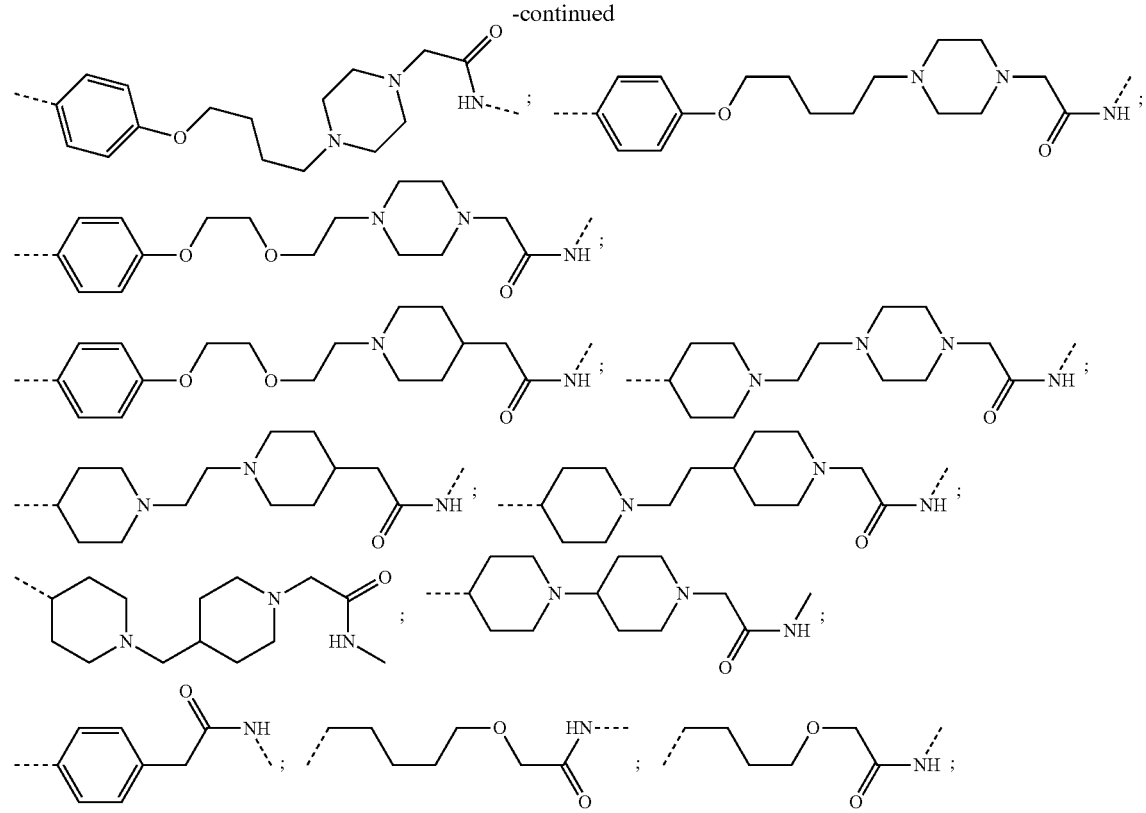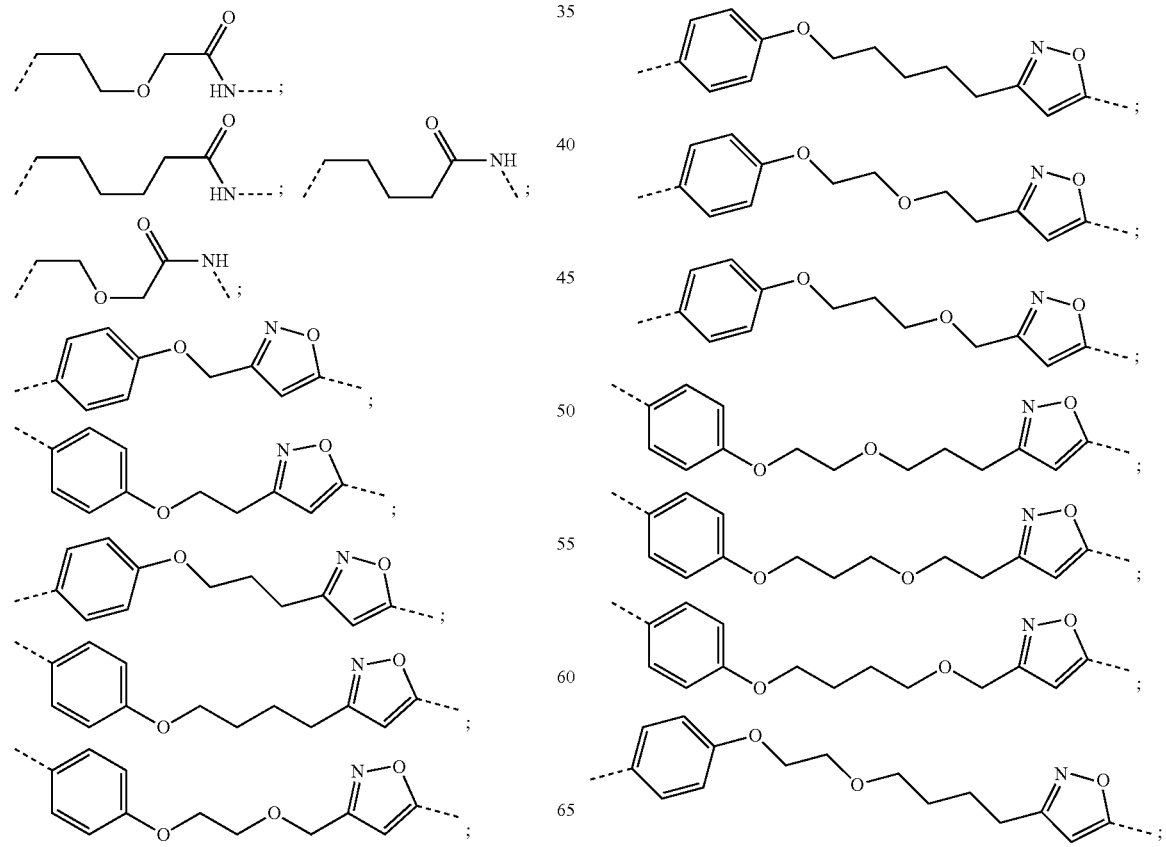

421
-continued
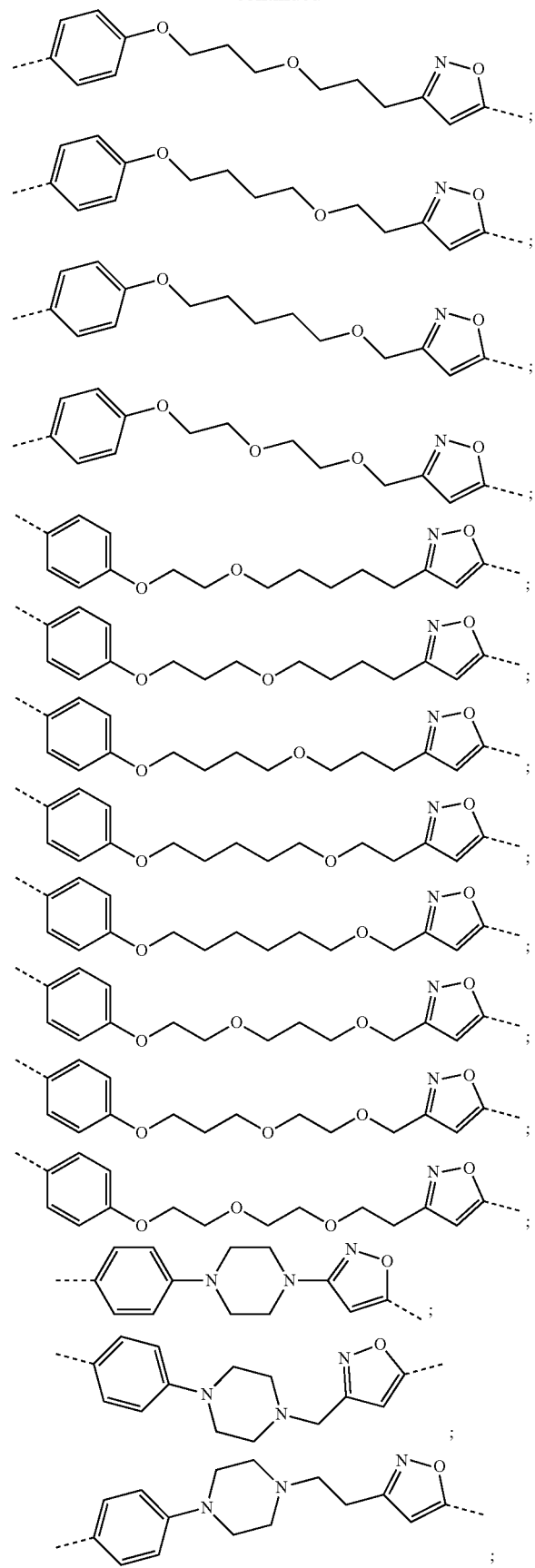
422
-continued
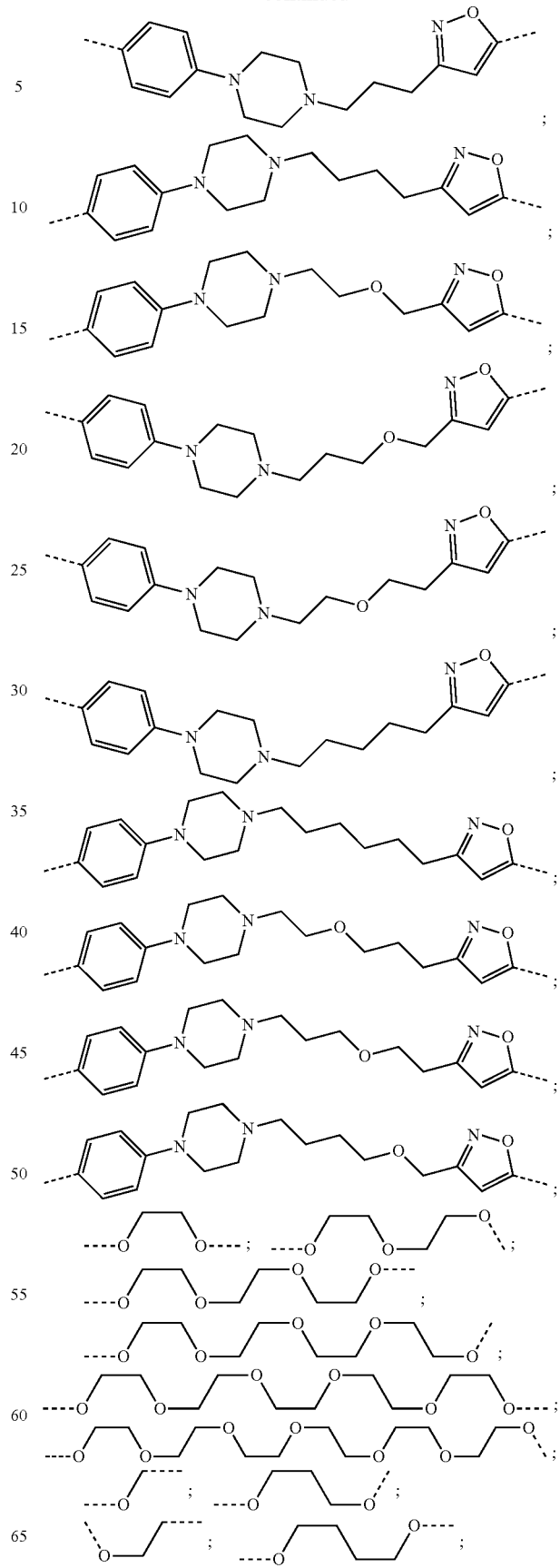

423

-continued

424

-continued

425
-continued
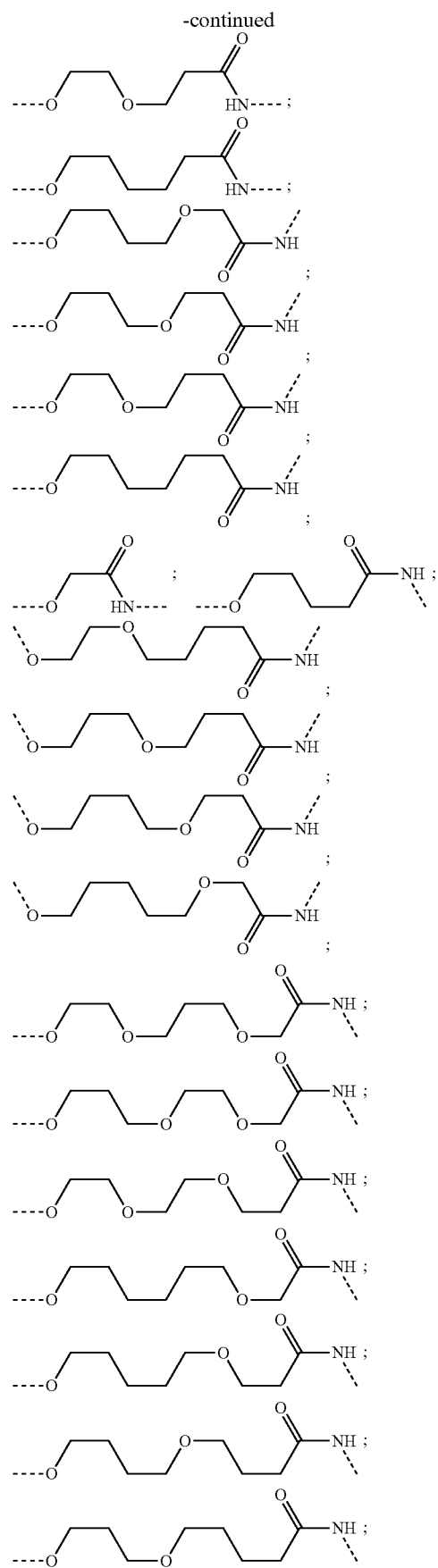
426
-continued
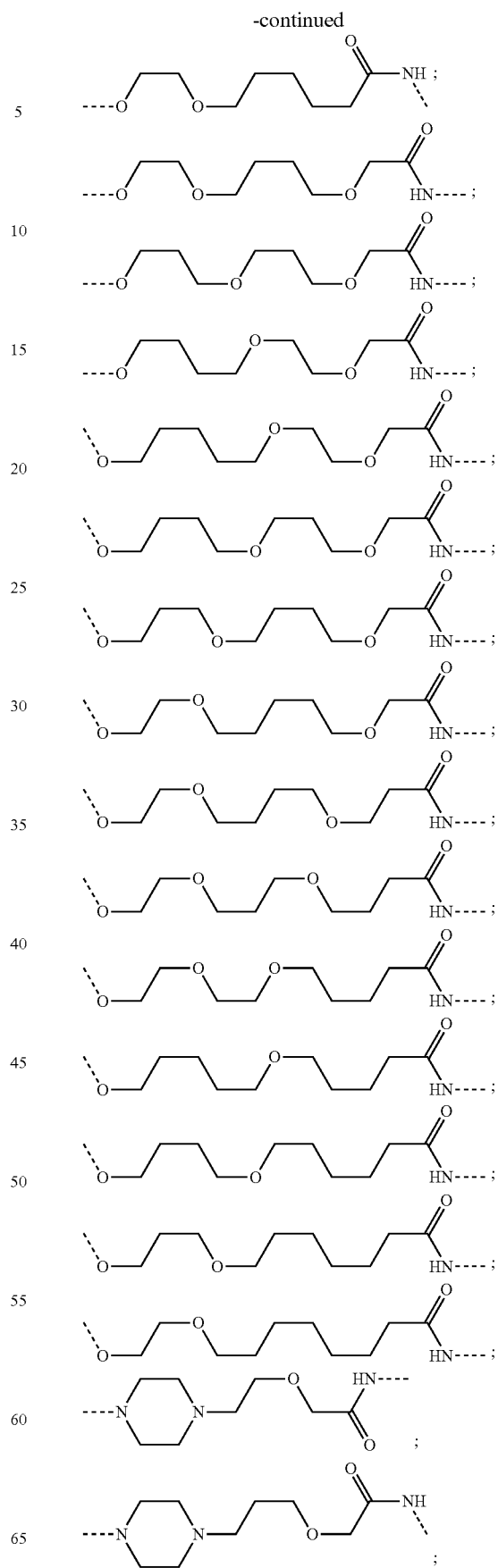

427
-continued
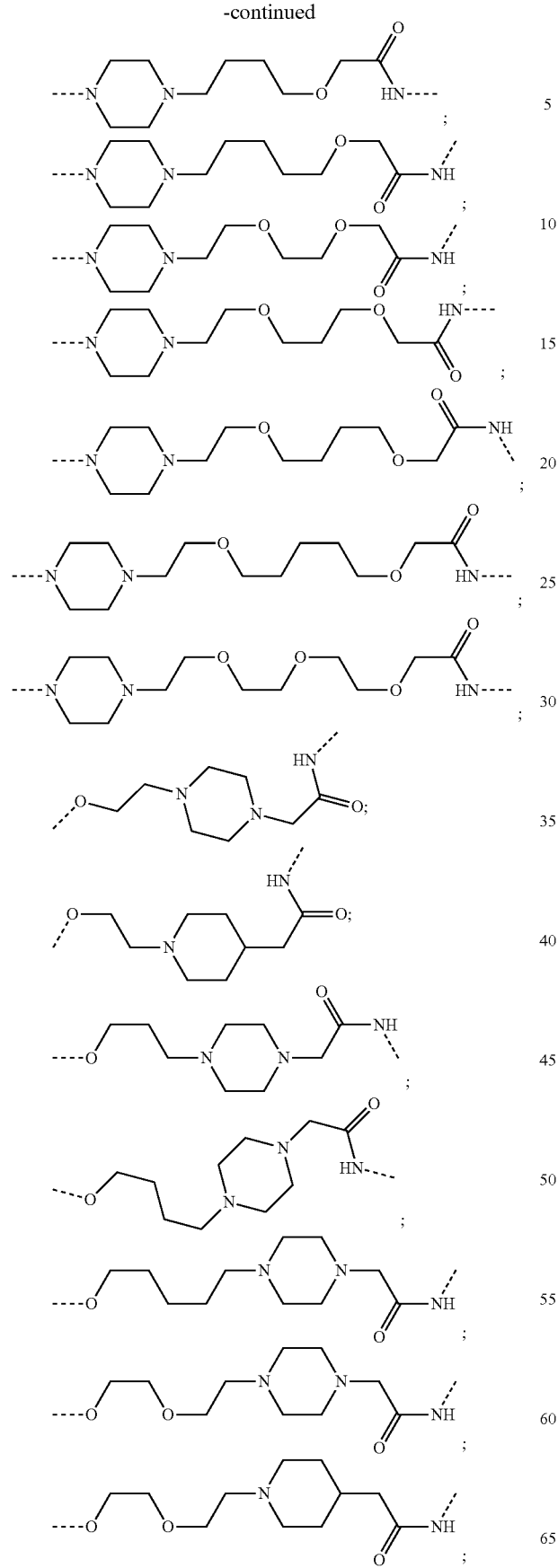
428
-continued
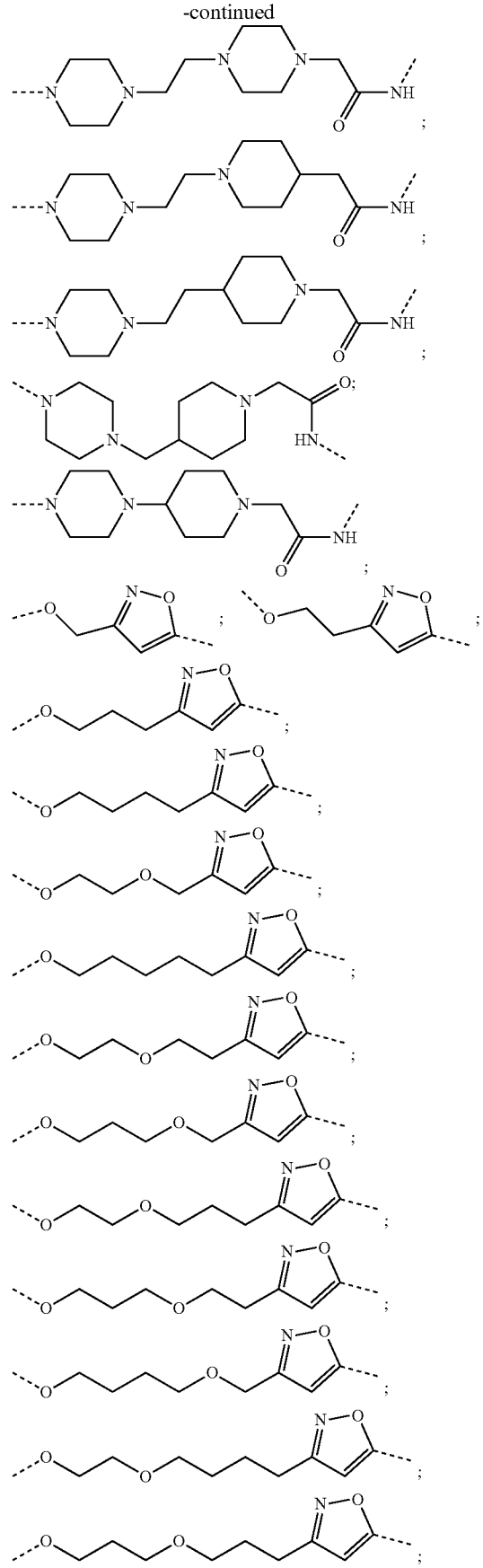

-continued

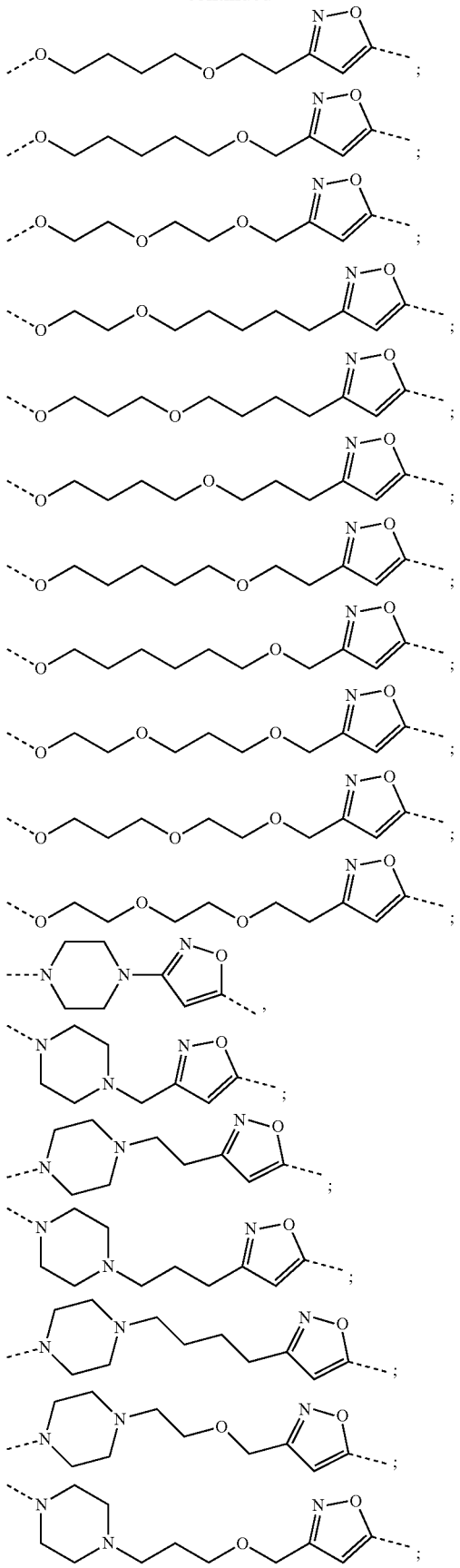

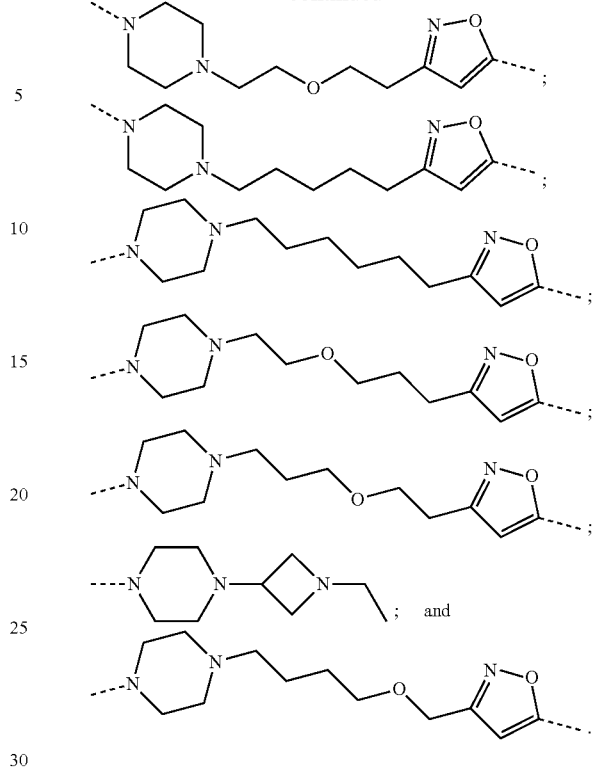

In additional embodiments, the linker (L) comprises a structure selected from, but not limited to the structure shown below, where a dashed line indicates the attachment point to the PTM or ULM moieties:

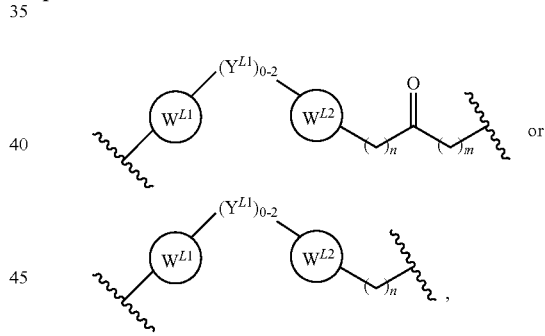

wherein:
$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, optionally substituted linear or branched $C_1$-$C_6$ alkyl, optionally substituted linear or branched $C_1$-$C_6$ alkoxy, or 2 $R^Q$ groups taken together with the atom they are attached to, form a 4-8 membered ring system containing 0-4 heteroatoms;
$Y^{L1}$ is each independently a bond, optionally substituted linear or branched $C_1$-$C_6$ alkyl, and optionally one or more C atoms are replaced with O; or optionally substituted linear or branched $C_1$-$C_6$ alkoxy;
n and m are independently 0-10; and indicates the attachment point to the PTM or ULM moieties.

In additional embodiments, the linker (L) comprises a structure selected from, but not limited to the structure shown below, where a dashed line indicates the attachment point to the PTM or ULM moieties:

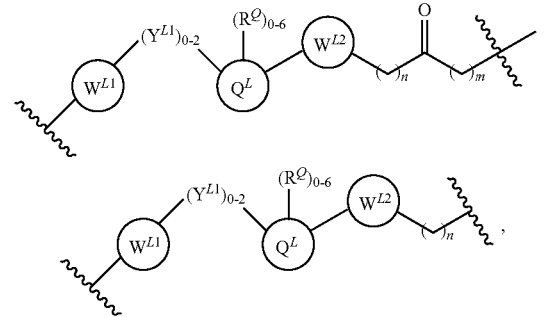

wherein:
- $W^{L1}$ and $W^{L2}$ are each independently absent, aryl, heteroaryl, cyclic, heterocyclic, $C_{1-6}$ alkyl and optionally one or more C atoms are replaced with O or N, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;
- $Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$ alkyl (linear, branched, optionally substituted) and optionally one or more C atoms are replaced with O; optionally substituted linear or branched $C_1$-$C_6$ alkoxy, 3-6 membered alicyclic or aromatic ring with 0-4 heteroatoms;
- $Q^L$ is a 3-6 membered alicyclic or aromatic ring with 0-4 heteroatoms, optionally bridged, optionally substituted with 0-6 $R^Q$, each $R^Q$ is independently H, optionally substituted linear or branched $C_{1-6}$ alkyl (e.g., optionally substituted by 1 or more halo or $C_{1-6}$ alkoxyl), or 2 $R^Q$ groups taken together with the atom they are attached to, form a 3-8 membered ring system containing 0-2 heteroatoms;
- $R^{YL1}$, $R^{YL2}$ are each independently H, OH, optionally substituted linear or branched $C_{1-6}$ alkyl (e.g., optionally substituted by 1 or more halo or $C_{1-6}$ alkoxyl), or $R^1$, $R^2$ together with the atom they are attached to, form a 3-8 membered ring system containing 0-2 heteroatoms;
- n and m are independently 0-10; and ⧹ indicates the attachment point to the PTM or ULM moieties.

In additional embodiments, the linker group is optionally substituted (poly)ethyleneglycol having between 1 and about 100 ethylene glycol units (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, etc., ethylene glycol units), between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein each carbon is optionally substituted with a heteroatom selected from N, S, P, or Si atoms that has an appropriate number of hydrogens, substitutions, or both to complete valency, with the proviso that there is no heteroatom-heteroatom bonding (e.g., no heteroatoms are covalently linked or adjacently located).

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency. For example, in any aspect or embodiment described herein, the linker (L) has a chemical structure selected from:

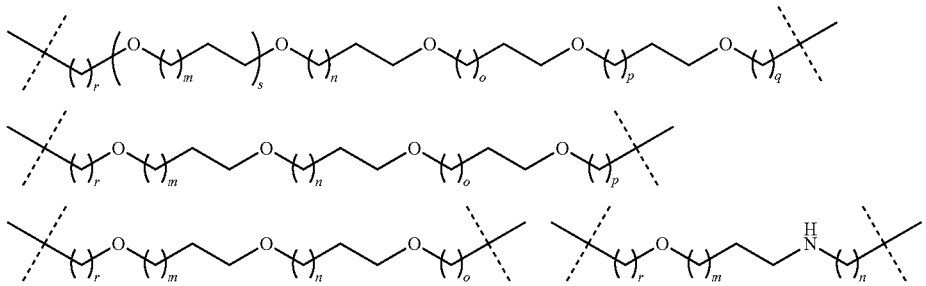

-continued

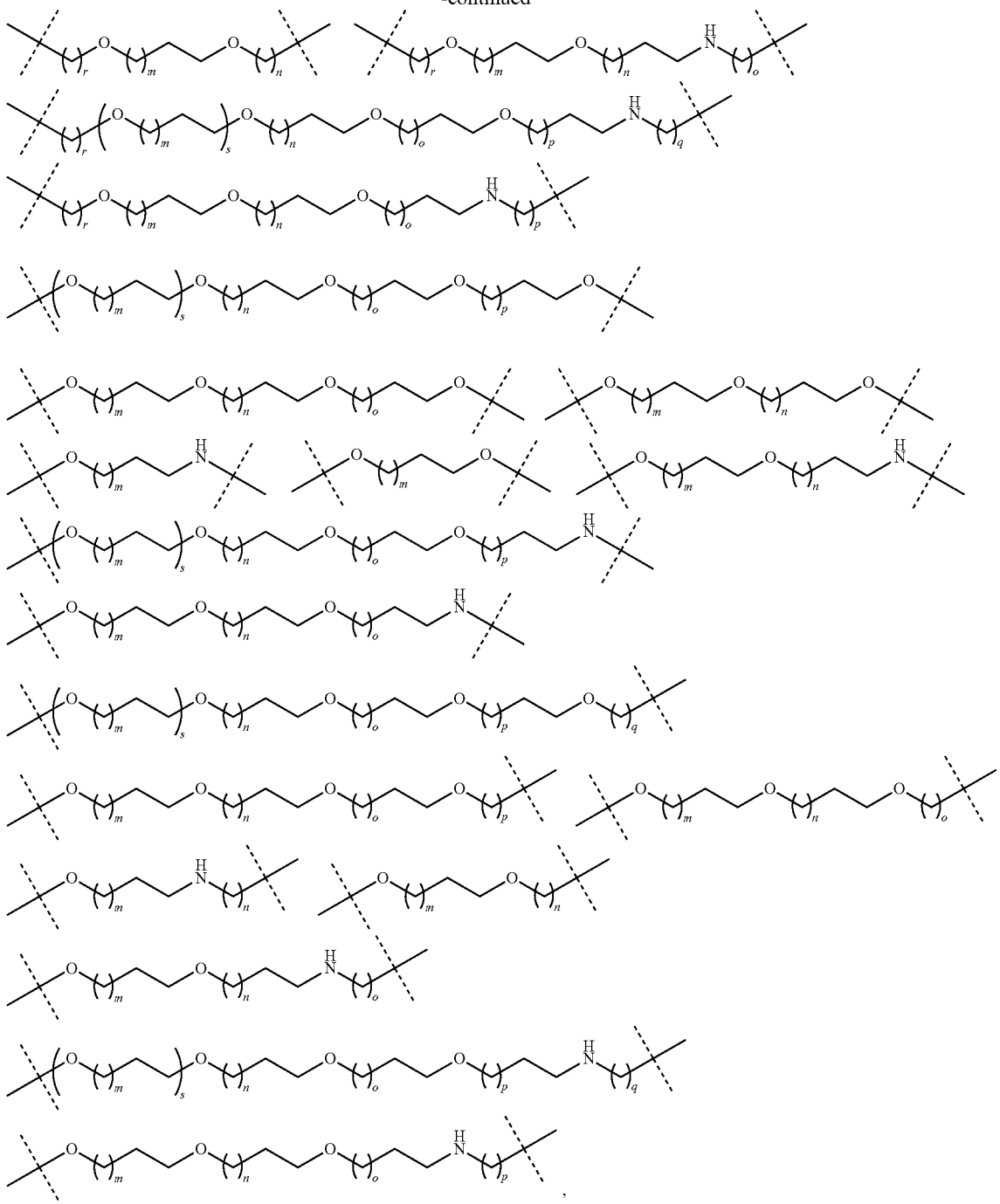

wherein carbon or oxygen may be substituted with a heteroatom selected from N, S, P, or Si atoms with an appropriate number of hydrogens to complete valency, and m, n, o, p, q, r, and s are independently selected from 0, 1, 2, 3, 4, 5, 6, 7, 8, 9, 10, 11, 12, 13, 14, 15, 16, 17, 18, 19, and 20.

In another embodiment, the present disclosure is directed to a compound which comprises a PTM group as described above, which binds to a target protein or polypeptide (e.g., Kirsten rat sarcoma protein (KRas or KRAS) and/or a gain-of-function KRas mutant), which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

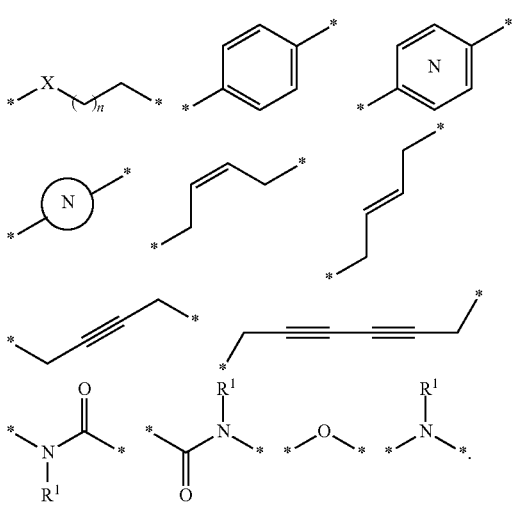

The X is selected from the group consisting of O, N, S, S(O) and SO$_2$; n is integer from 1 to 5;
R$^{L1}$ is hydrogen or alkyl,

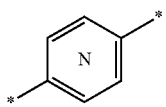

is a mono- or bicyclic aryl or heteroaryl optionally substituted with 1-3 substituents selected from alkyl, halogen, haloalkyl, hydroxy, alkoxy or cyano;

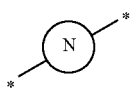

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: KRas inhibitors, Hsp90 inhibitors, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest, such as KRas and/or mutant KRas, including gain-of-function KRas mutant(s), such as KRas$^{G12C}$. These binding moieties are linked to the ubiquitin ligase binding moiety preferably through a linker in order to present a target protein (to which the protein target moiety is bound), such as KRas and/or gain-of-function KRas mutant(s), in proximity to the ubiquitin ligase for ubiquitination and degradation.

The present disclosure may be used to treat a number of disease states and/or conditions, including any disease state and/or condition in which proteins are dysregulated and where a patient would benefit from the degradation and/or inhibition of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer (including, e.g., pancreatic cancer, colon cancer, lung cancer, non-small cell lung cancer, or a combination thereof). In certain additional embodiments, the disease includes or is pancreatic cancer, colon cancer, colorectal cancer, lung cancer, non-small cell lung cancer, biliary tract malignancies, endometrial cancer, cervical cancer, bladder cancer, liver cancer, myeloid leukemia, breast cancer, or a combination thereof.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer (including, e.g., pancreatic cancer, colon cancer, colorectal cancer, lung cancer, non-small cell lung cancer, biliary tract malignancies, endometrial cancer, cervical cancer, bladder cancer, liver cancer, myeloid leukemia, breast cancer, or a combination thereof), by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. For example, in any aspect or embodiment described herein, the PTM is a small molecule comprising a KRas protein targeting moiety. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. For example, in any aspect or embodiment described herein, the PTM is a KRas protein binding moiety.

These various protein targets, such as KRas protein, may be used in screens that identify compound moieties that bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include KRas inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of the small molecule target proteins. Exemplary protein target moieties according to the present disclosure include, KRas inhibitors, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest.

In any aspect or embodiment described herein, the PTM is a KRas protein binding/targeting moiety, e.g., a small molecule comprising a KRas protein binding/targeting moiety. In any aspect or embodiment described herein, the PTM binds mutant KRas, e.g. gain-of-function mutant KRas (such as $KRas^{G12C}$). In any aspect or embodiment described herein, the PTM has a chemical structure represented by:

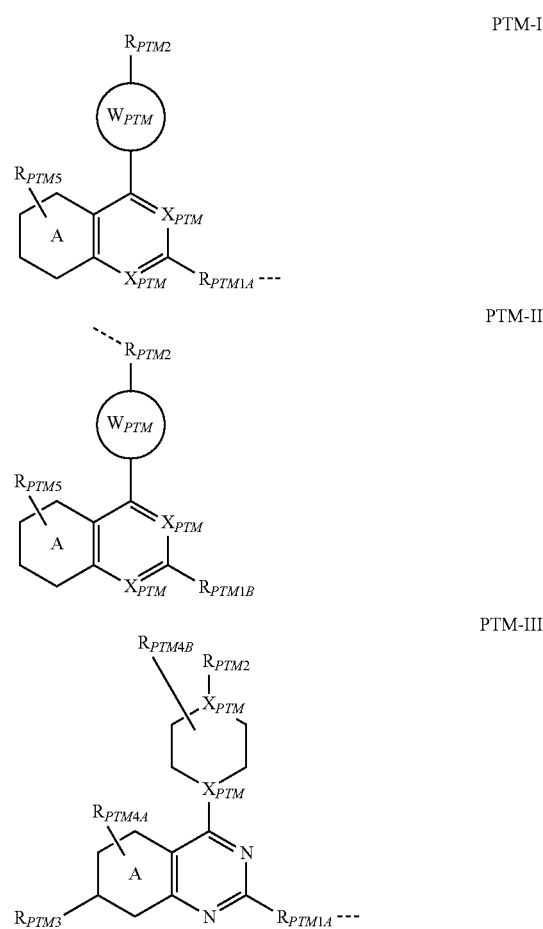

PTM-IV

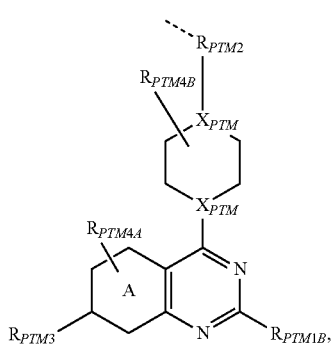

wherein:

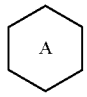

is an aryl, heteroaryl, cycloalkyl, or heterocycloalkyl;
$X_{PTM}$ is C or N;
$W_{PTM}$ is chosen from the group consisting of optionally substituted C3-C6 cycloalkyl, and optionally substituted C3-C6 heteroalkyl, optionally substituted C3-C6 heterocycloalkyl optionally substituted aryl (e.g., optionally substituted C5-C7 aryl), optionally substituted heteroaryl (e.g., optionally substituted $C_5$-$C_7$ heteroaryl);
$R_{PTM1A}$ is $NR_{PTM9}R_{PTM10}$, $OR_{PTM9}R_{PTM10}$, H, optionally substituted alkyl, optionally substituted alkoxy, optionally substituted C3-C6 cycloalkyl, optionally substituted O—(C3-C6 cycloalkyl), optionally substituted C3-C6 heteroalkyl, optionally substituted —O—C1-4 alkyl-C3-6cycloalkyl, optionally substituted O—(C3-C6 heteroalkyl), optionally substituted O—$C_{1-4}$ alkyl-$C_{3-6}$ heteroalkyl, optionally substituted O—$C_{1-4}$ alkyl-$C_{3-6}$ heterocycloalkyl, optionally substituted aryl (e.g., optionally substituted C5-C7 aryl), optionally substituted O-aryl (e.g., optionally substituted O—(C5-C7 aryl)), optionally substituted heteroaryl (e.g., optionally substituted C5-C7 heteroaryl), optionally substituted O-heteroaryl (e.g., optionally substituted O—(C5-C7 heteroaryl)), optionally substituted

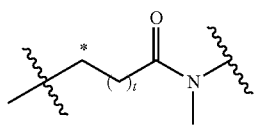

(e.g., optionally substituted with at least one alkyl, such as the * carbon may be optionally substituted with an alkyl), optionally substituted

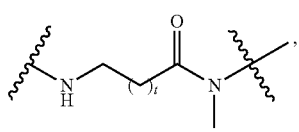

optionally substituted

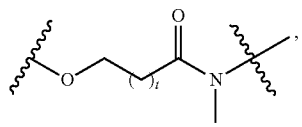

optionally substituted

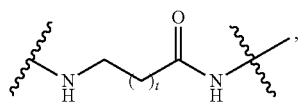

optionally substituted

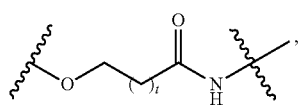

optionally substituted

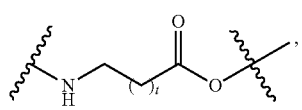

optionally substituted

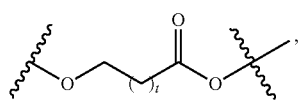

optionally substituted

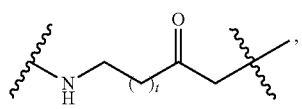

optionally substituted

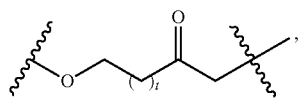

optionally substituted

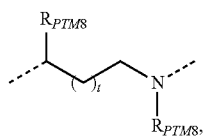

optionally substituted

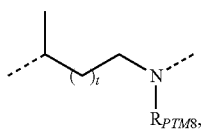

optionally substituted

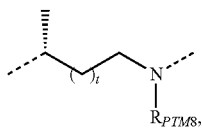

optionally substituted

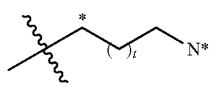

(e.g., optionally substituted with at least one alkyl, such as the * carbon may be optionally substituted with an alkyl), optionally substituted

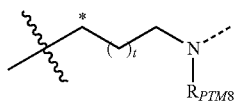

(e.g., optionally substituted with at least one alkyl, such as the * carbon may be optionally substituted with an alkyl), optionally substituted

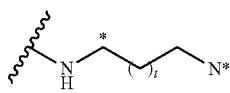

(e.g., optionally substituted with at least one alkyl, such as the * carbon may be optionally substituted with an alkyl), optionally substituted

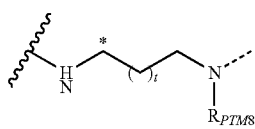

(e.g., optionally substituted with at least one alkyl, such as the * carbon may be optionally substituted with an alkyl), optionally substituted

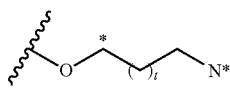

(e.g., optionally substituted with at least one alkyl, such as the * carbon may be optionally substituted with an alkyl), optionally substituted

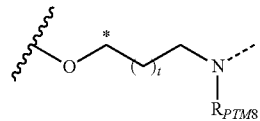

(e.g., optionally substituted with at least one alkyl, such as the * carbon may be optionally substituted with an alkyl), wherein N* is a N atom of a heterocycloalkyl (e.g., a C4-C8 heterocycloalkyl) of the linker (L);

$R_{PTM1B}$ is $NR_{PTM9}R_{PTM10}$, $OR_{PTM9}R_{PTM10}$, H, optionally substituted alkyl, optionally substituted O-alkyl, optionally substituted C3-C6 cycloalkyl, optionally substituted O—(C3-C6 cycloalkyl), optionally substituted —O—$C_{1-4}$ alkyl-$C_{3-6}$cycloalkyl, optionally substituted C3-C6 heteroalkyl, optionally substituted O—(C3-C6 heteroalkyl), optionally substituted O—$C_{1-4}$ alkyl-$C_{3-6}$ heteroalkyl, optionally substituted aryl (e.g., optionally substituted C5-C7 aryl), optionally substituted O-aryl (e.g., optionally substituted O—(C5-C7 aryl)), optionally substituted heteroaryl (e.g., optionally substituted $C_5$-$C_7$ heteroaryl), optionally substituted O-heteroaryl (e.g., optionally substituted O(C5-C7 heteroaryl)), optionally substituted

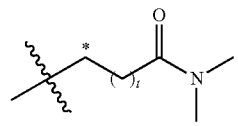

(e.g., optionally substituted with at least one alkyl, such as the * carbon may be optionally substituted with an alkyl), optionally substituted

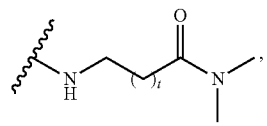

optionally substituted

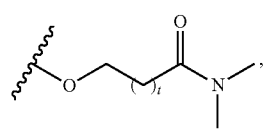

optionally substituted

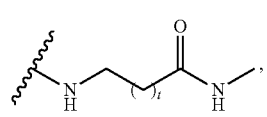

optionally substituted

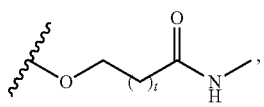

optionally substituted

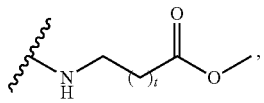

optionally substituted

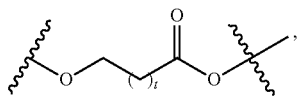

optionally substituted

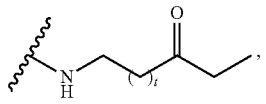

optionally substituted

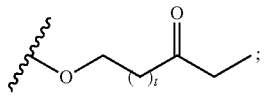

$R_{PTM9}$ and $R_{PTM10}$ are each independently H, optionally substituted C1-C6 alkyl, optionally substituted aliphatic amine, optionally substituted aliphatic amide;

$R_{PTM2}$ is H, (C=O)$R_{PTM2'}$, optionally substituted linear or branched alkyl;

$R_{PTM2'}$ is optionally substituted linear or branched alkyl, optionally substituted alkene, —N($R_{PTM8}$)$_2$, or —C(OH)$_2$;

$R_{PTM3}$ is alkyl, alkoxy, phenyl, or napthalene, each independently substituted with OH, H, halogen;

$R_{PTM4A}$ is OH, H, halogen, optionally substituted linear or branched $C_1$-$C_6$ alkyl;

$R_{PTM4B}$ is OH, H, halogen, optionally substituted linear or branched $C_1$-$C_6$ alkyl;

$R_{PTM5}$ is chosen from the group consisting of optionally substituted aryl, optionally substituted biaryl, optionally substituted heteroaryl, optionally substituted biheteroaryl, optionally substituted C3-C6 cycloalkyl, optionally substituted C3-C6 cycloheteroalkyl, halogen, H, optionally substituted linear or branched alkyl (e.g., optionally substituted linear or branched C1-C6 alkyl), OH, and alkoxy;

$R_{PTM8}$ is a H or an alkyl (e.g., a C1 alkyl, a C2 alkyl, a C3 alkyl, or a C4 alkyl);

t is 0, 1, 2, 3, 4, 5, 6 (such as 0, 1, 2, 3); and the ⸺ indicates the site of attachment of at least one of a linker, ULM, ULM', CLM, CLM', VLM, VLM', ILM, ILM', MLM, MLM', or a combination thereof.

In any aspect or embodiment described herein, the PTM has a chemical structure represented by:

PTM-Va

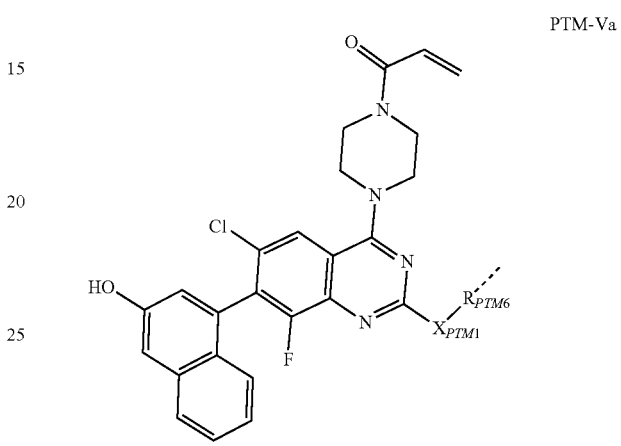

PTM-Vb

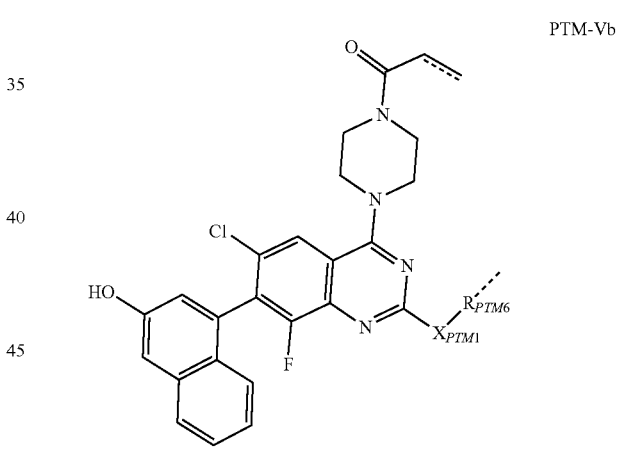

PTM-VI

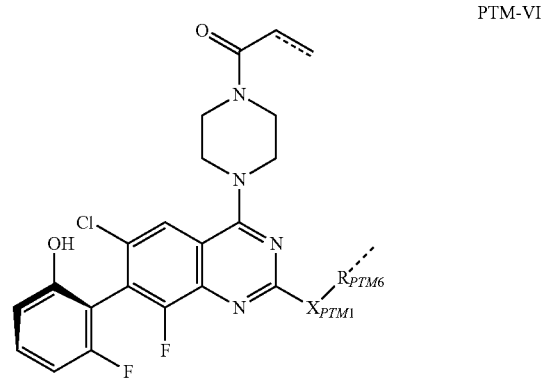

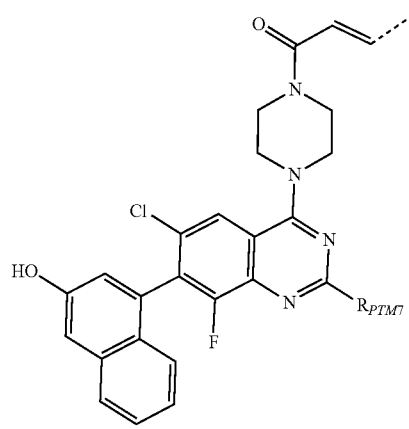
PTM-VIIa
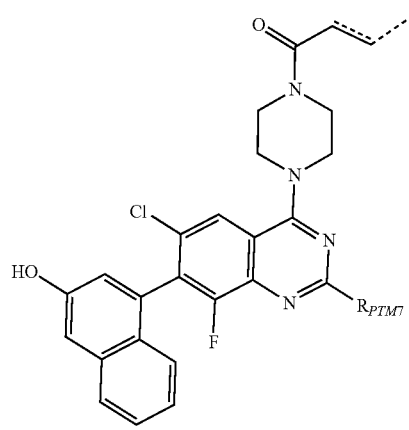
PTM-VIIb
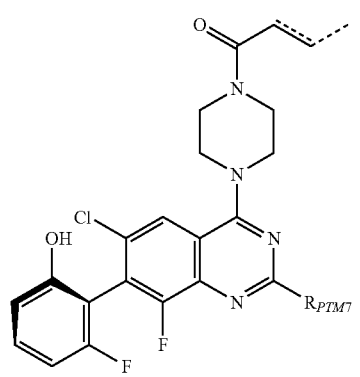
PTM-VIII
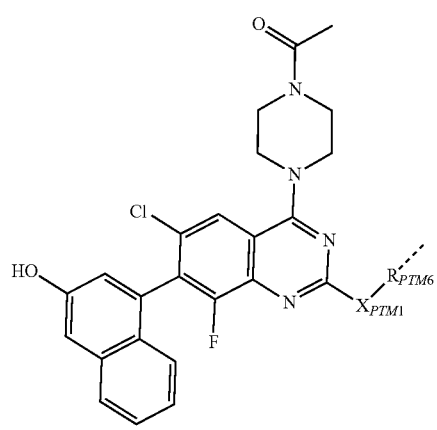
PTM-IXa
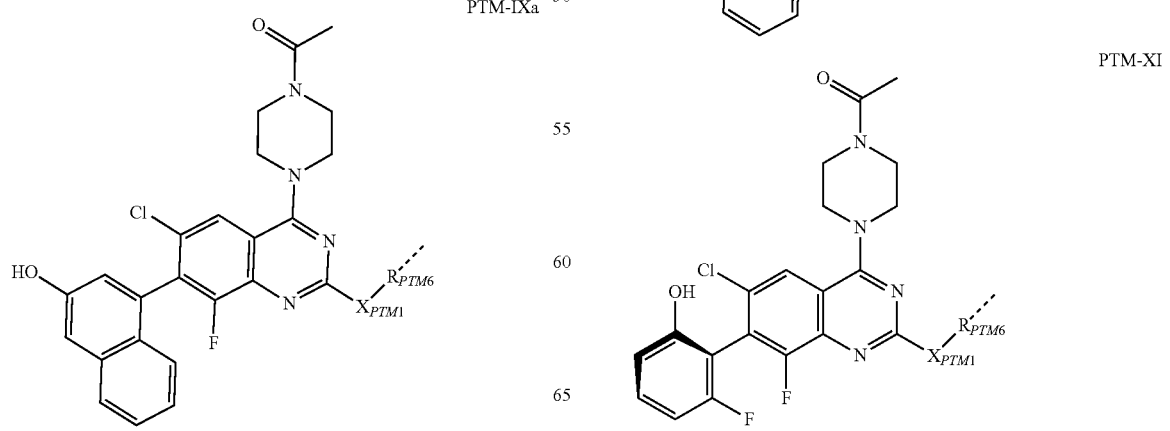
PTMI-Xb
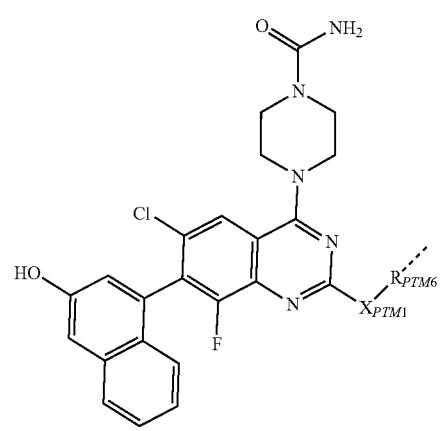
PTM-Xa
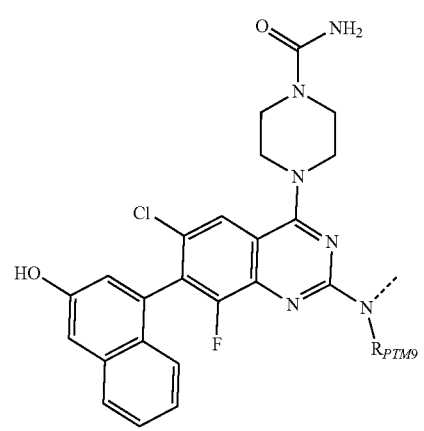
PTM-Xb
PTM-XI 447
-continued
PTM-XII
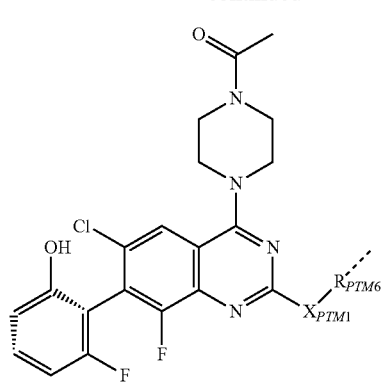
PTM-XIII
PTM-XIV
PTM-XV
448
-continued
PTM-XVI
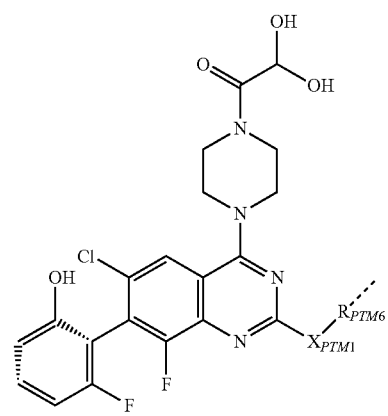
PTM-XVIIa
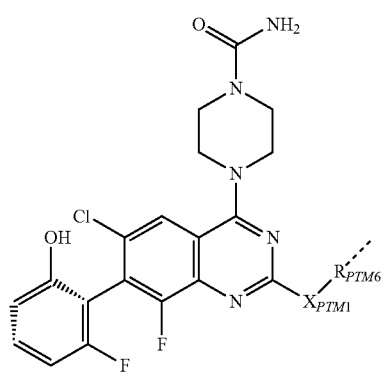
PTM-XVIIb
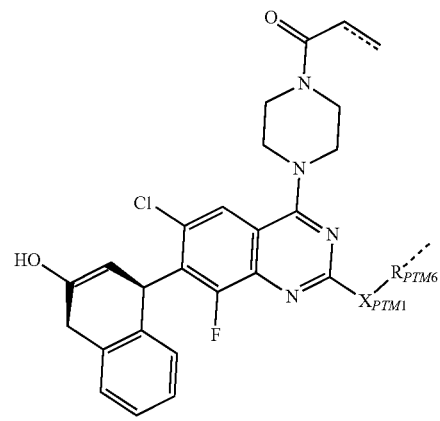
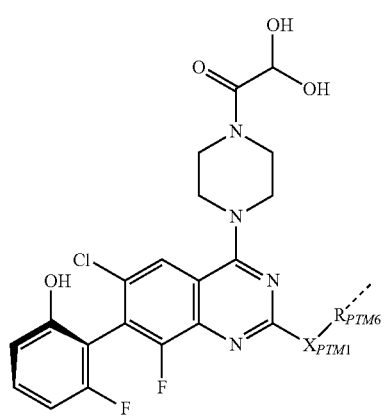

-continued
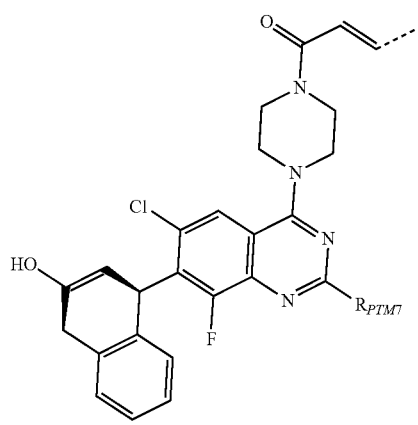
PTM-XVIII
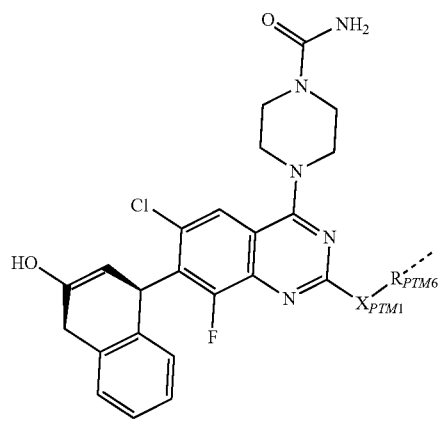
PTM-XVI
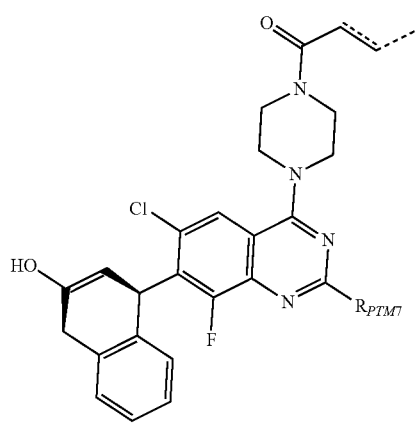
PTM-XIV
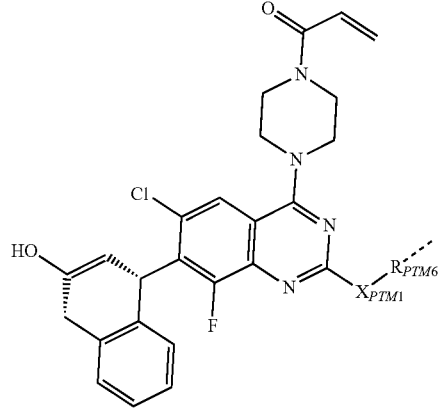
PTM-XVIIa
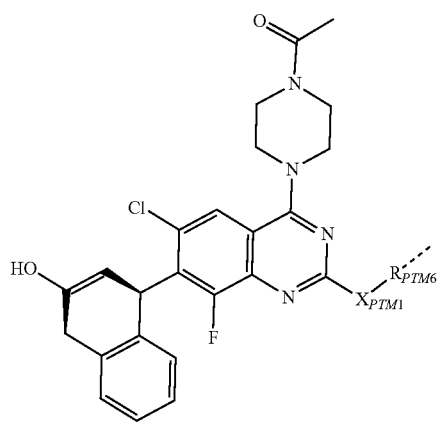
PTM-XV
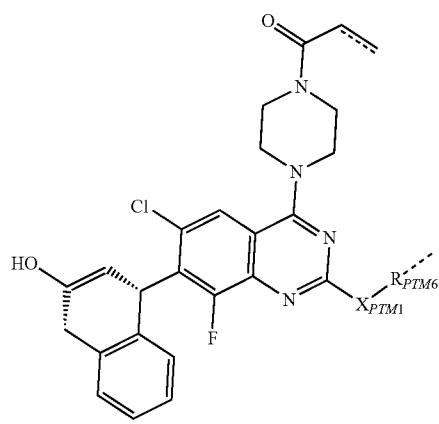
PTMXVIIb PTM-XVIII
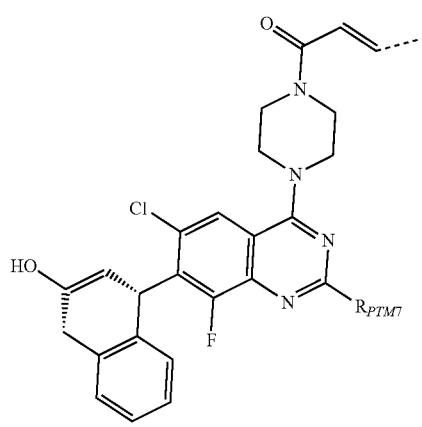
PTM-XIX
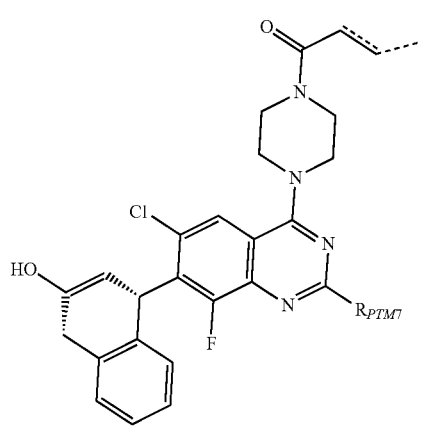
PTM-XX
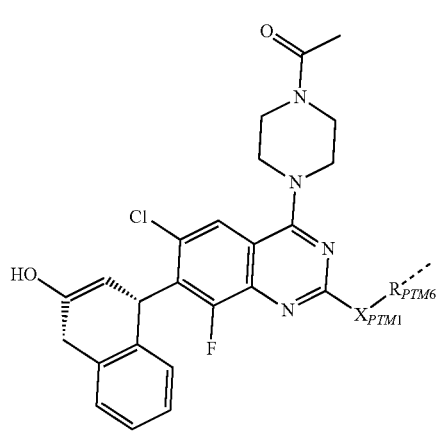
PTM-XXI
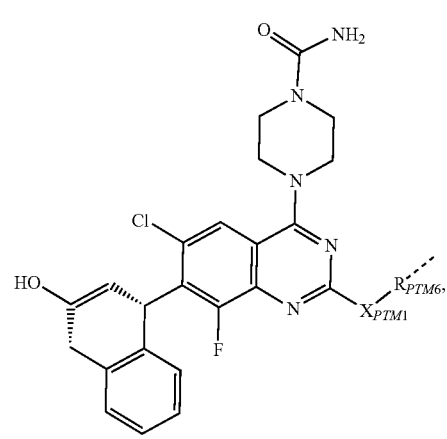
wherein:
$X_{PTM1}$ is NH or O;
$R_{PTM6}$ is aryl, heteroaryl,
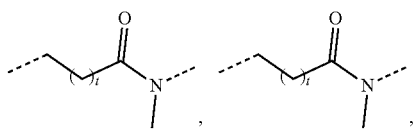
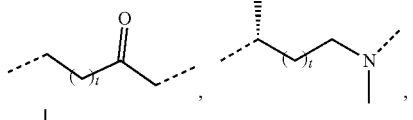
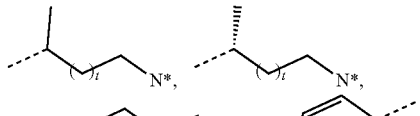
wherein N* is a N atom of a heterocycloalkyl (e.g., a C4-C8 heterocycloalkyl) of the linker (L);
$R_{PTM7}$ is H, aryl, O-aryl, heteroaryl, O-heteroaryl,
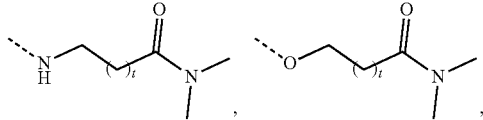

-continued

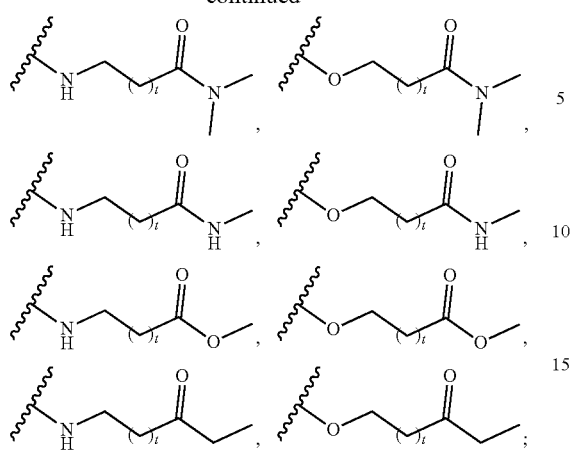

t is 0, 1, 2, 3, 4, 5, 6 (e.g., 1, 2, or 3);

$R_{PTM9}$ is H, optionally substituted C1-C6 alkyl, optionally substituted aliphatic amine, optionally substituted aliphatic amide, or optionally substituted

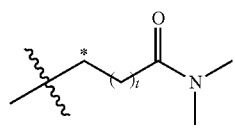

(e.g., optionally substituted with at least one alkyl, such as the * carbon may be optionally substituted with an alkyl);

the ⋮⋮ can be a single bond or a double bond; and the ⋰ indicates the site of attachment of at least one of a linker, ULM, ULM', CLM, CLM', VLM, VLM', ILM, ILM', MLM, MLM', or a combination thereof.

In any aspect or embodiment described herein, the PTM is selected from:

PTM-1

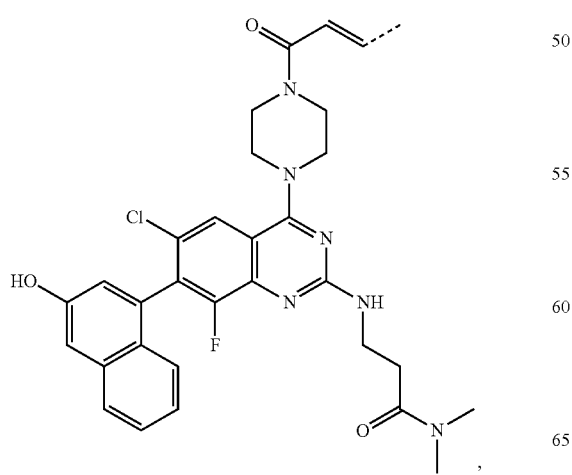

-continued

PTM-2

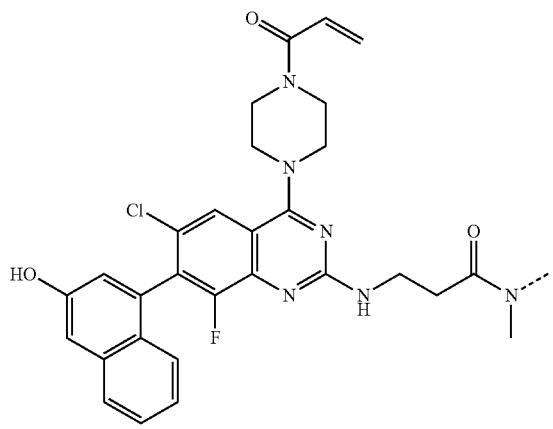

PTM-3

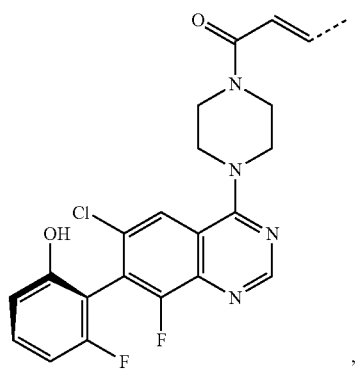

PTM-4

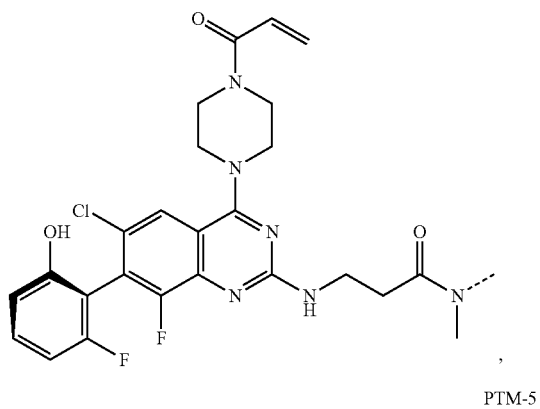

PTM-5

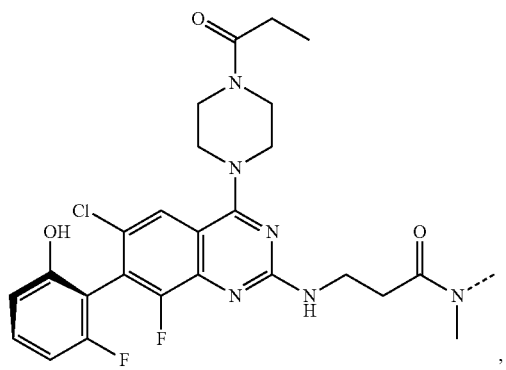

PTM-6
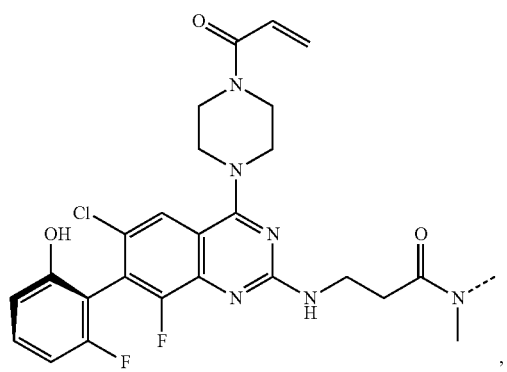
PTM-7
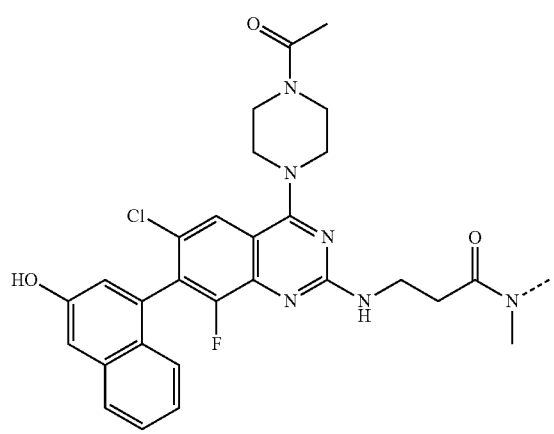
PTM-8
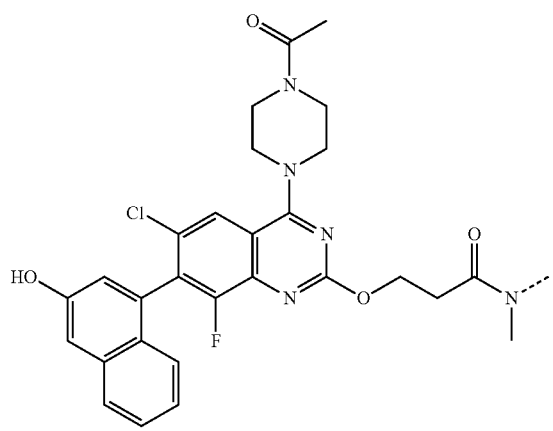
PTM-9
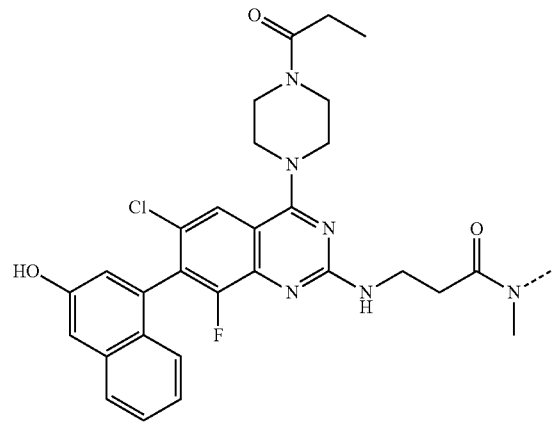
PTM-10
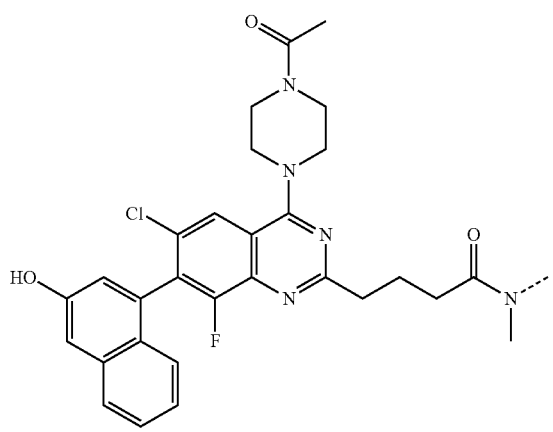
PTM-11
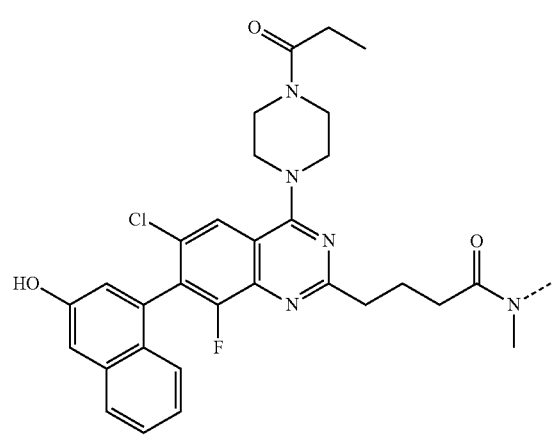

PTM-12
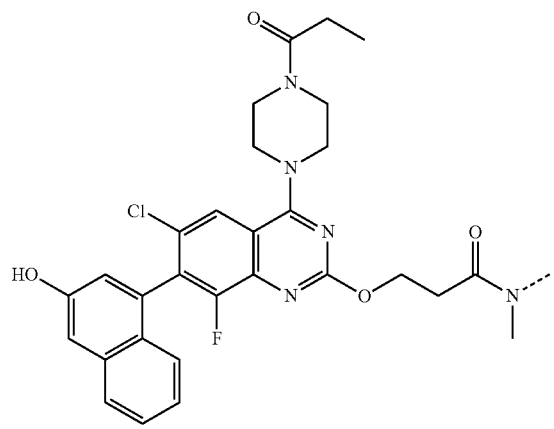
PTM-13
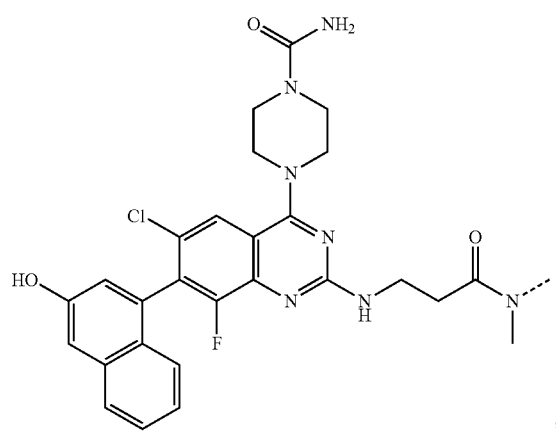
PTM-14
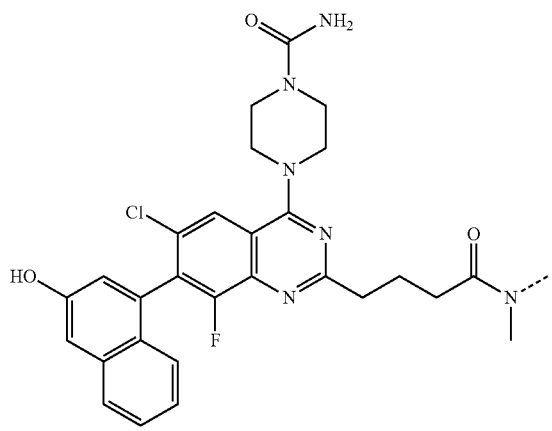
PTM-15
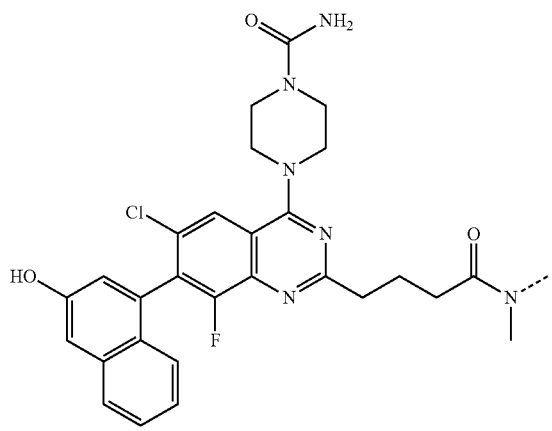
PTM-16
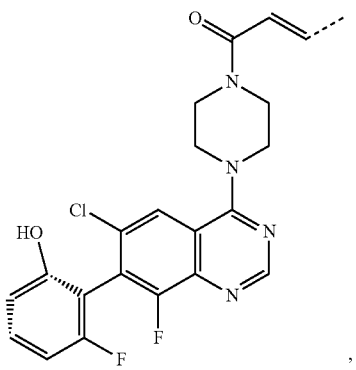
PTM-17
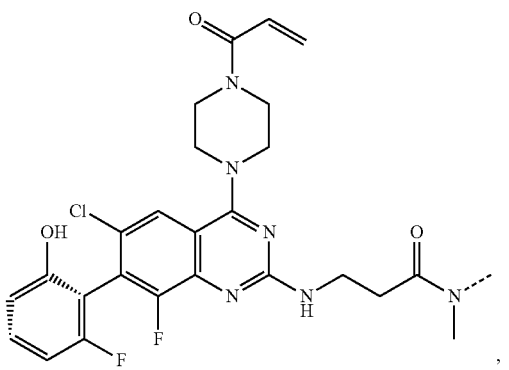
PTM-18
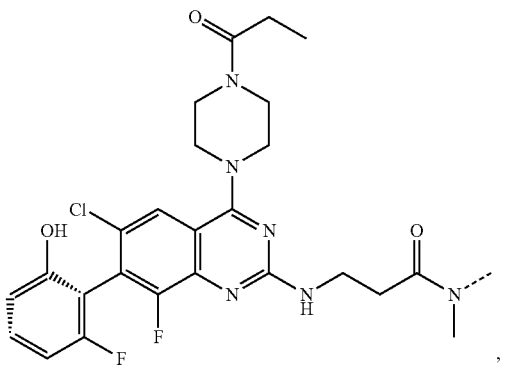

PTM-19
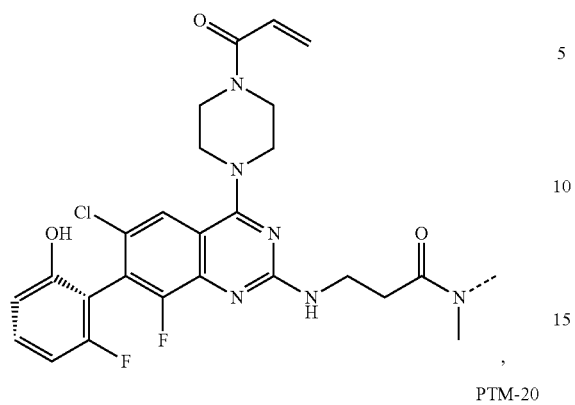
PTM-20
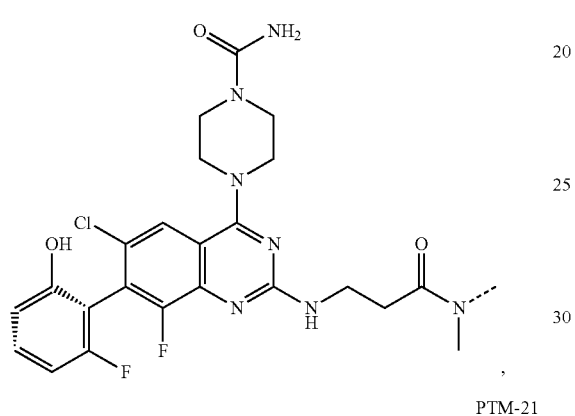
PTM-21
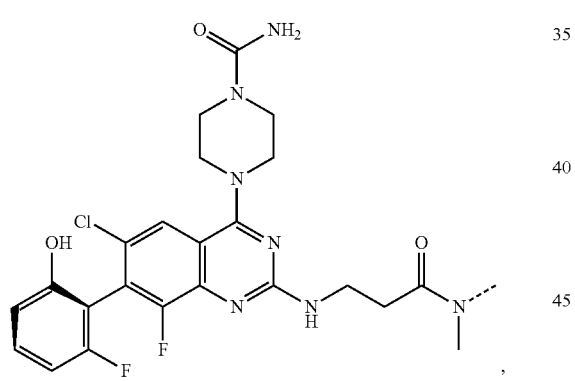
PTM-22
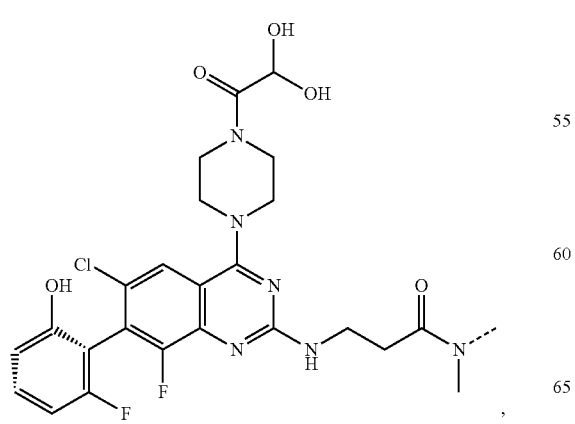
PTM-23
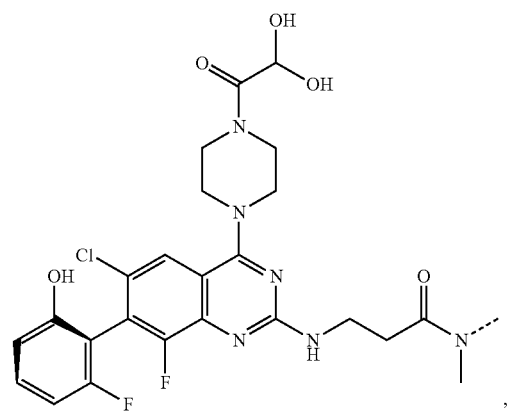
PTM-23
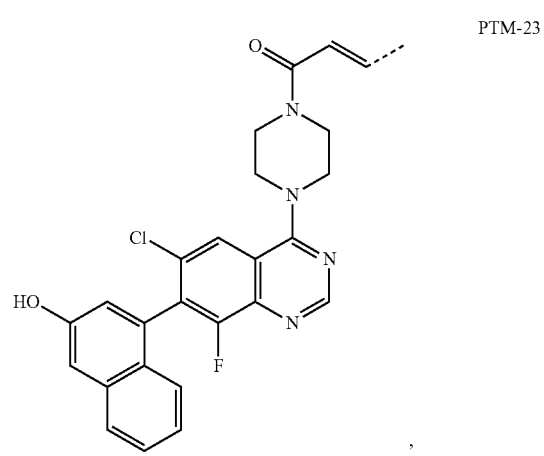
PTM-24

PTM-25
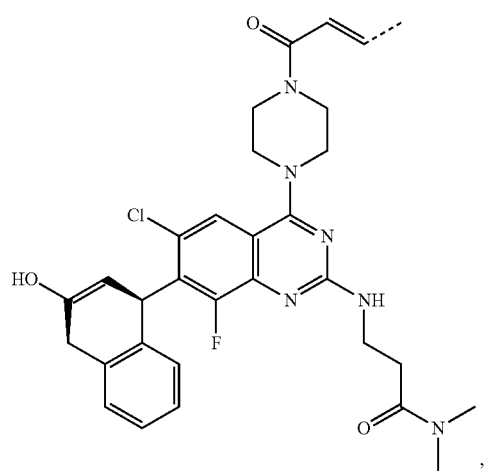
PTM-26
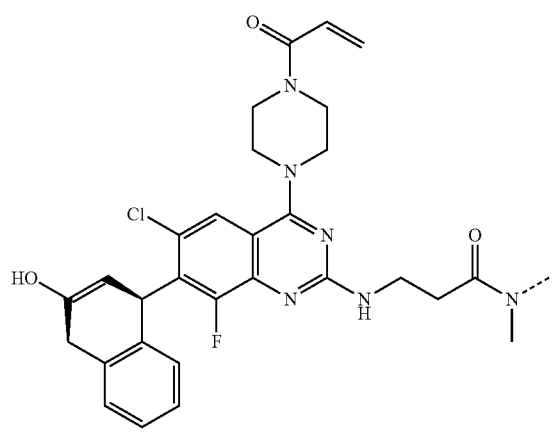
PTM-27
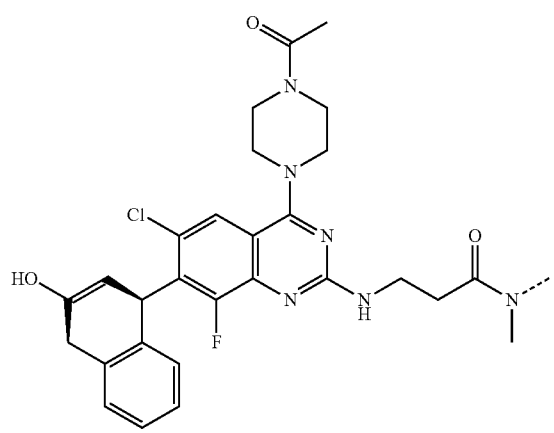
PTM-28
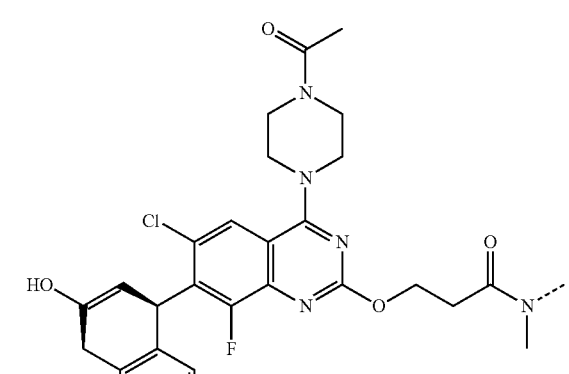
PTM-29
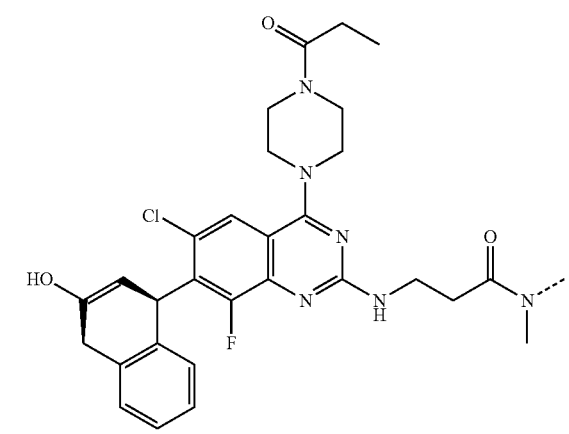
PTM-32
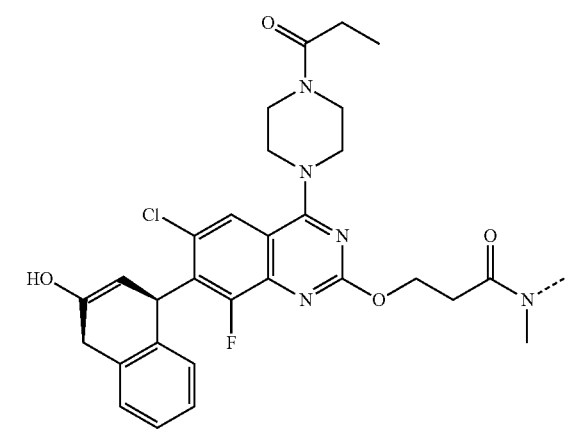

-continued
PTM-33
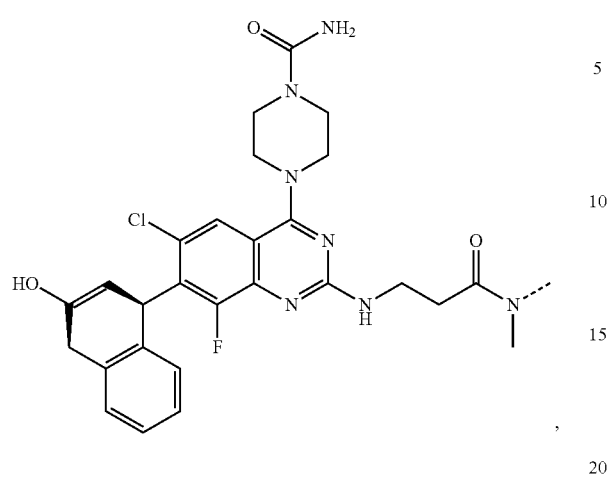
PTM-36
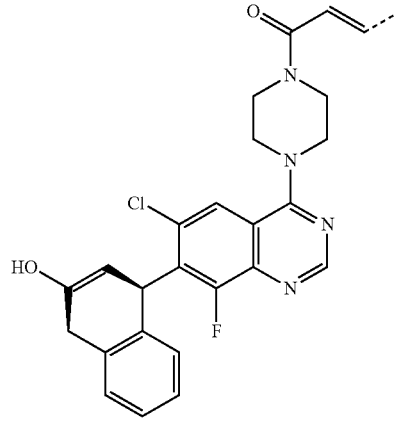
PTM-34
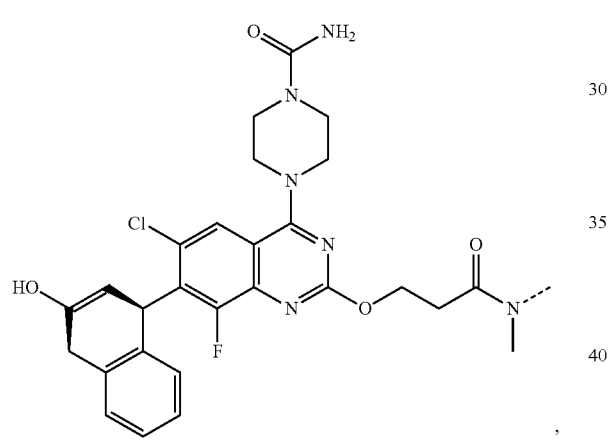
PTM-37
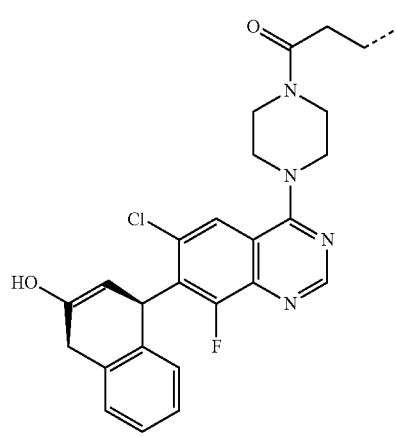
PTM-35
PTM-38
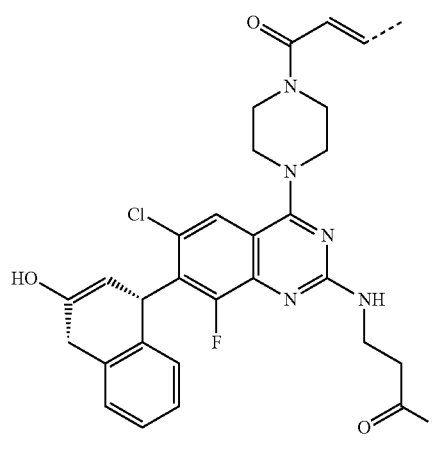

-continued
PTM-39
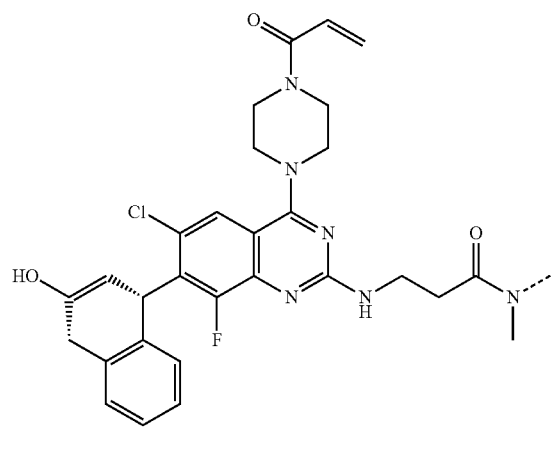
PTM-42
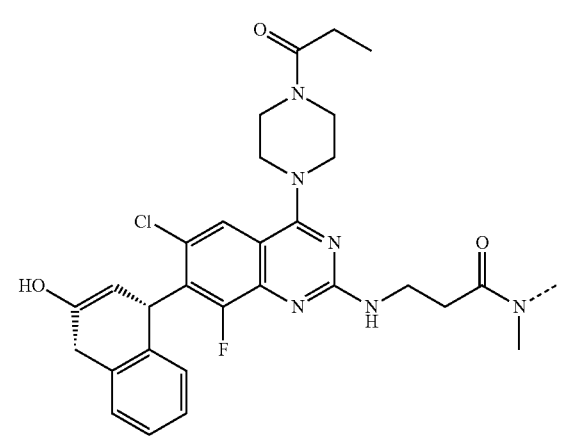
,
PTM-40
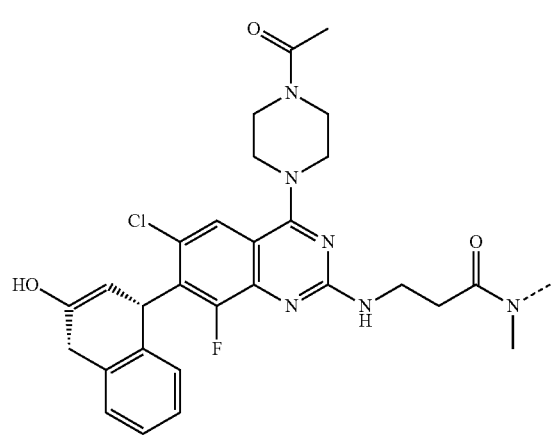
PTM-43
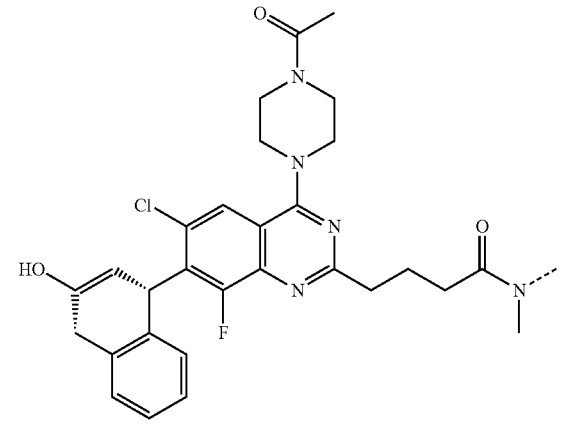
,
PTM-41
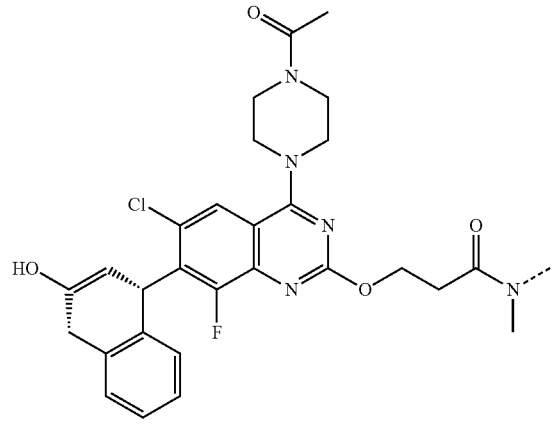
PTM-44
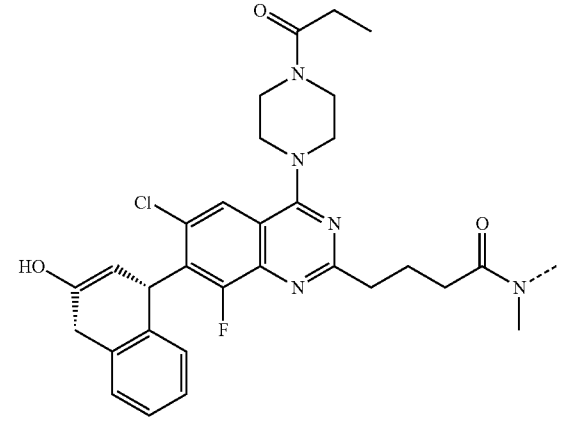
, PTM-45
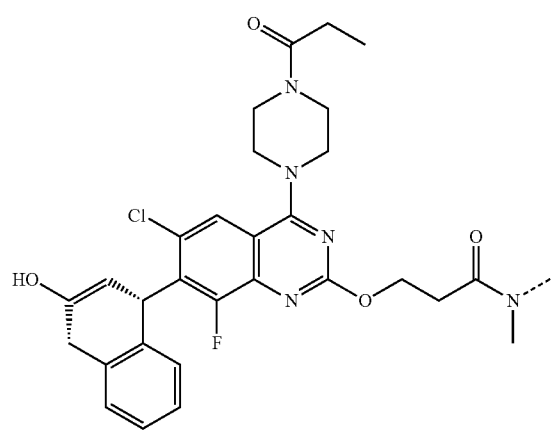
PTM-46
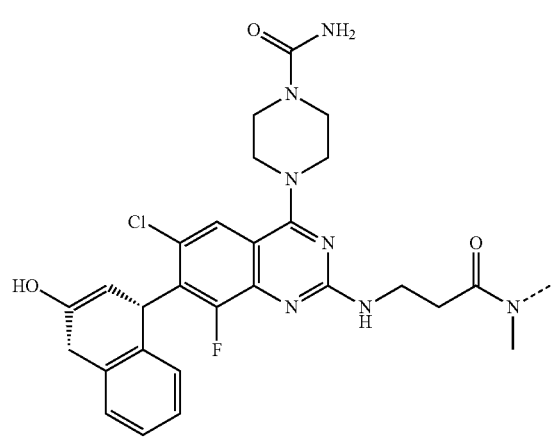
PTM-47
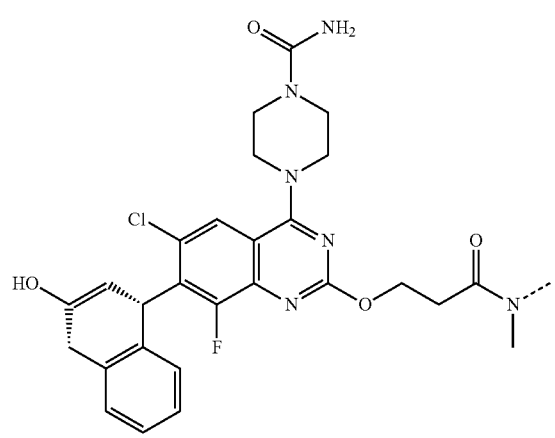
PTM-48
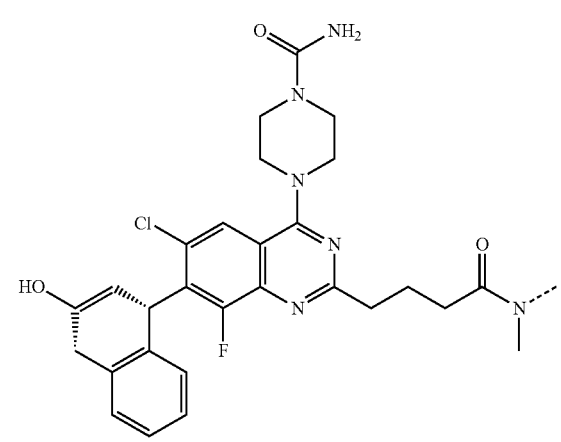
PTM-49
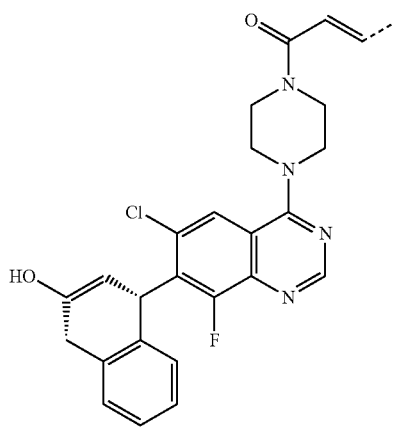
PTM-50
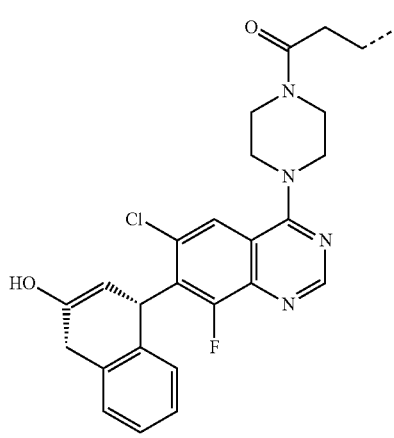

PTM-51
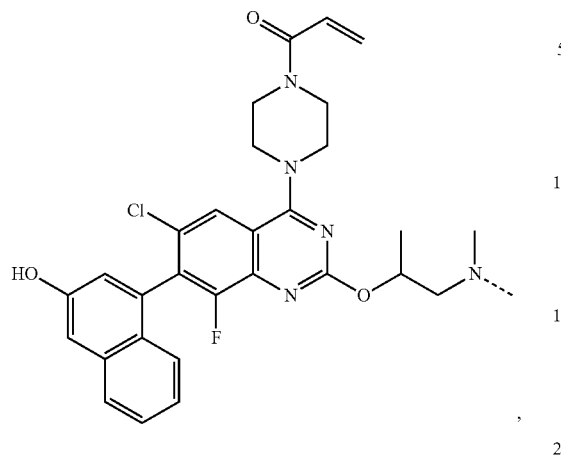
PTM-52
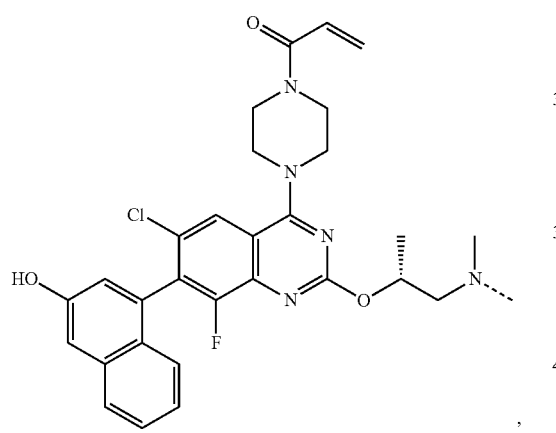
PTM-53
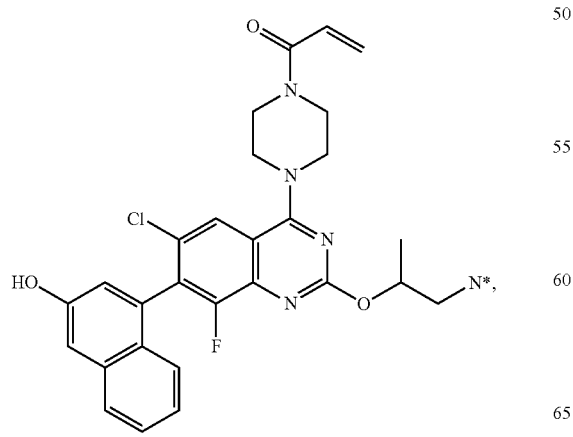
PTM-54
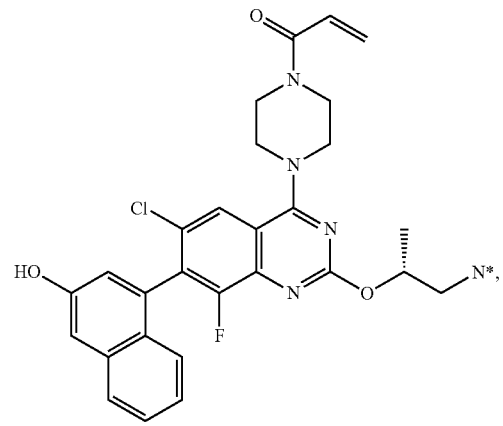
PTM-55
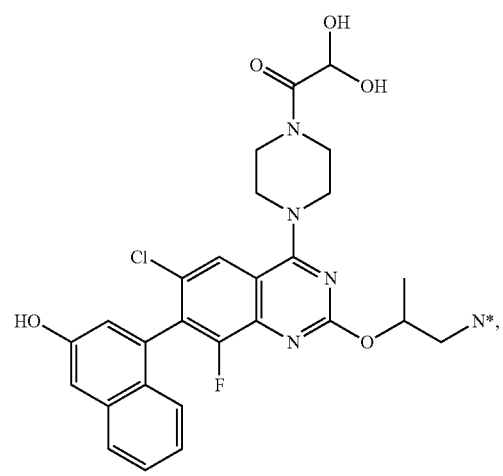
PTM-56
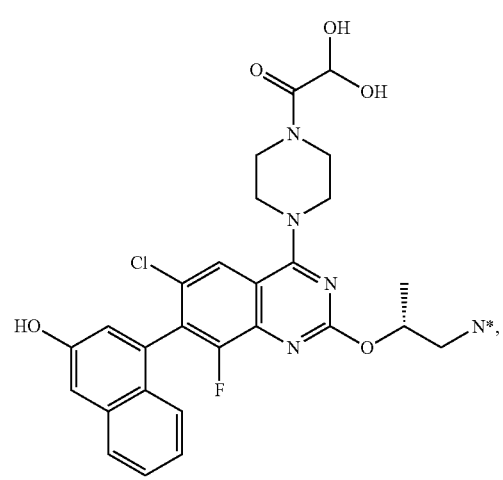

PTM-57
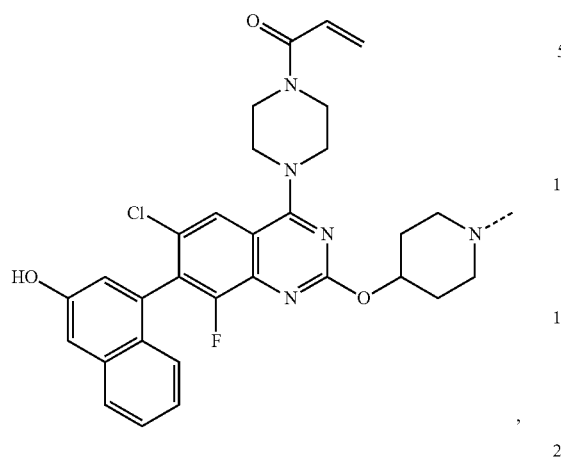
PTM-58
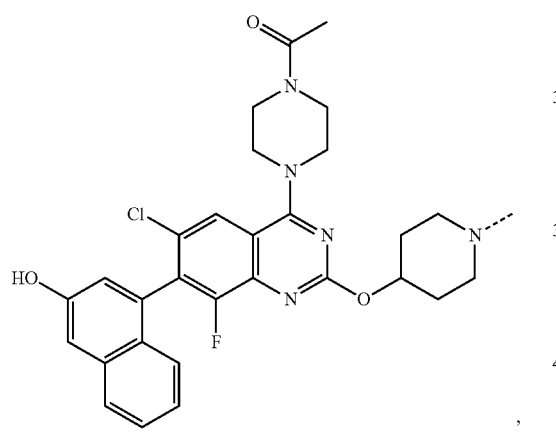
PTM-59
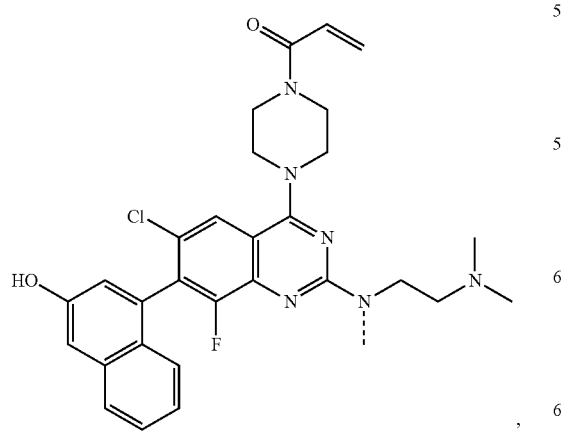
PTM-60
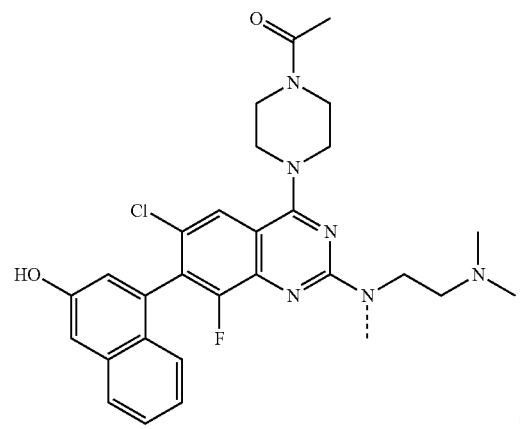
PTM-61
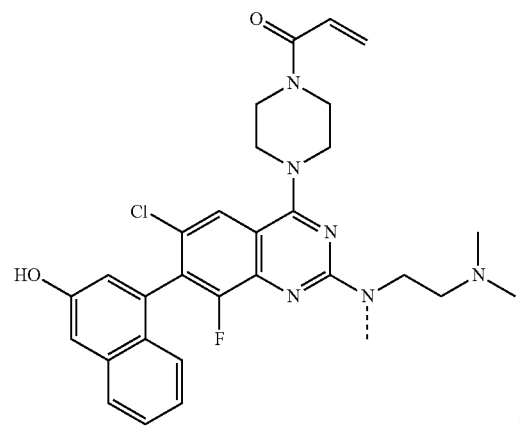
PTM-62
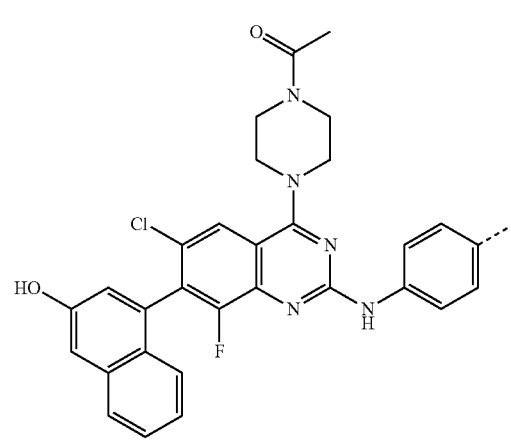

PTM-63
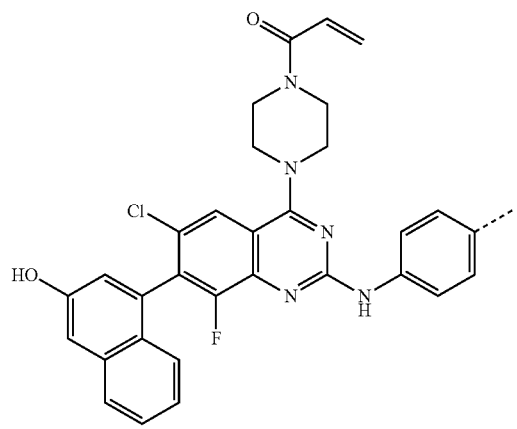
PTM-64
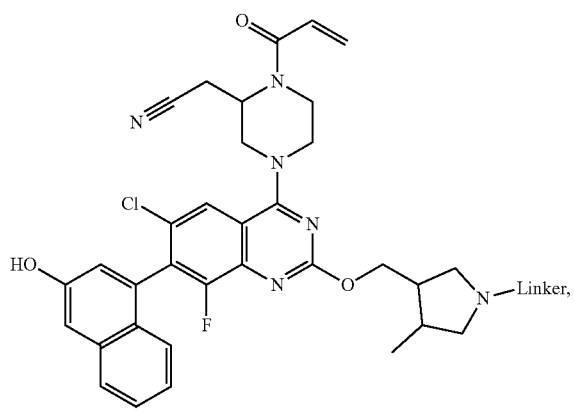
PTM-65
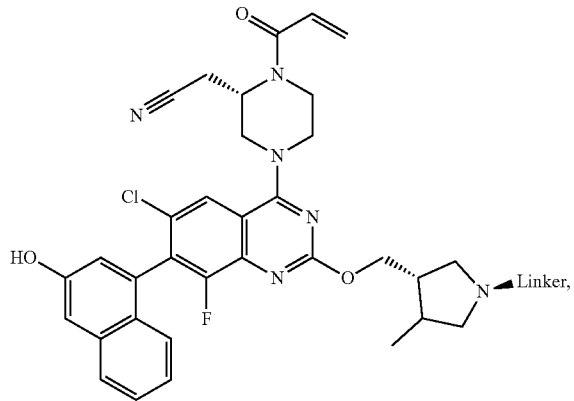
PTM-66
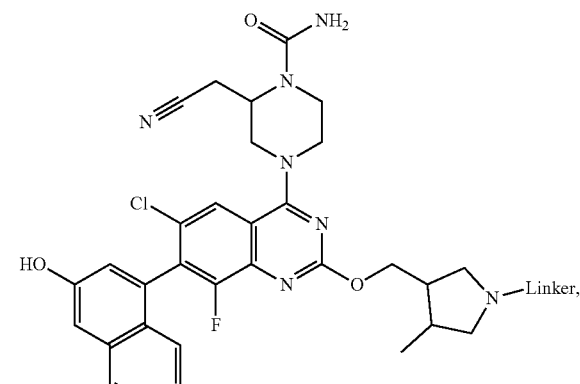
PTM-67
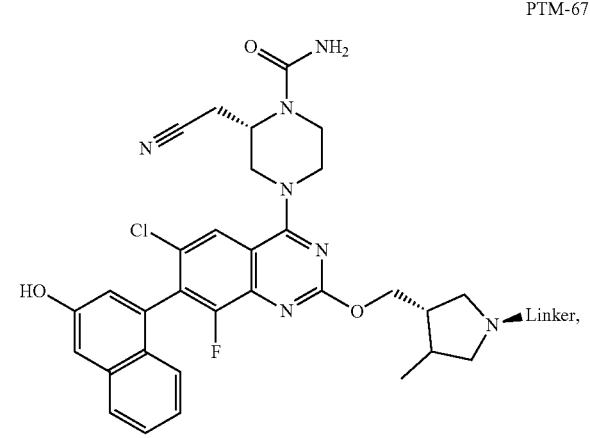
PTM-68
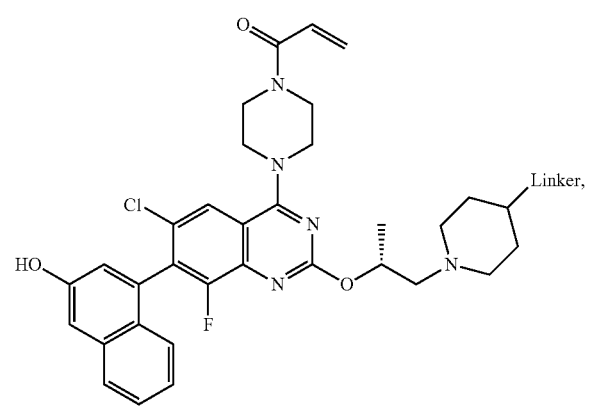

PTM-69
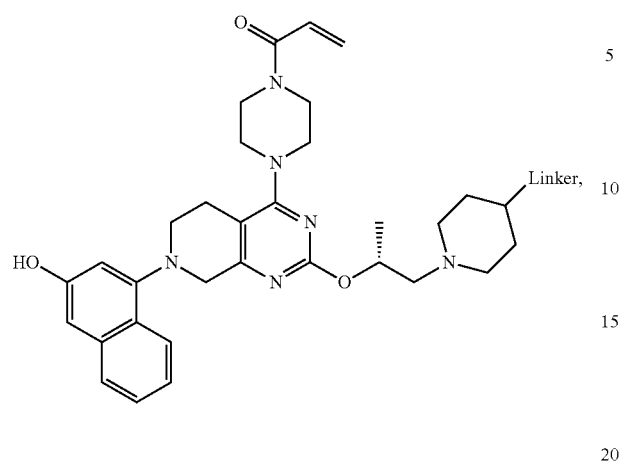
PTM-72
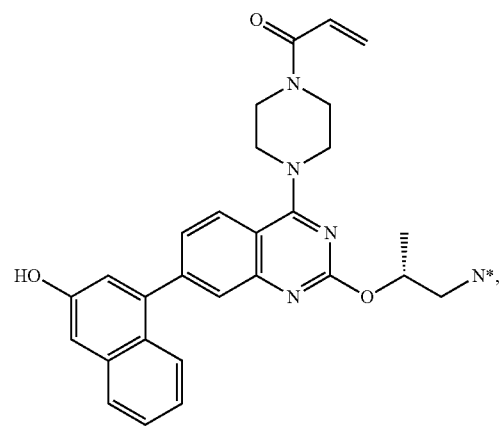
PTM-70
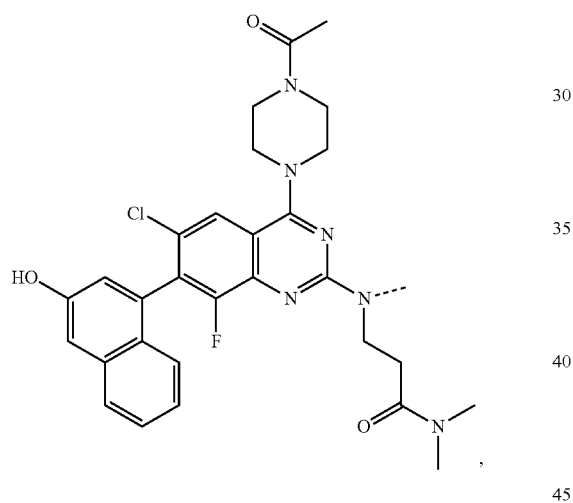
PTM-73
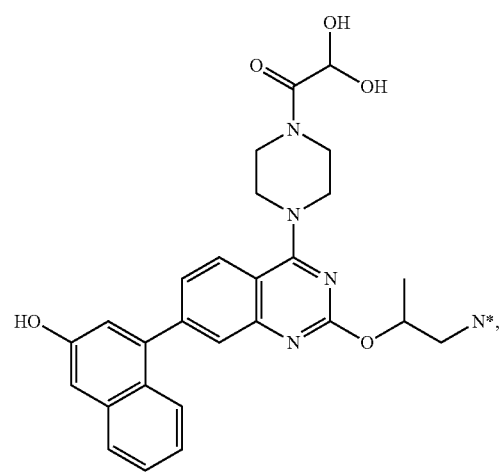
PTM-71
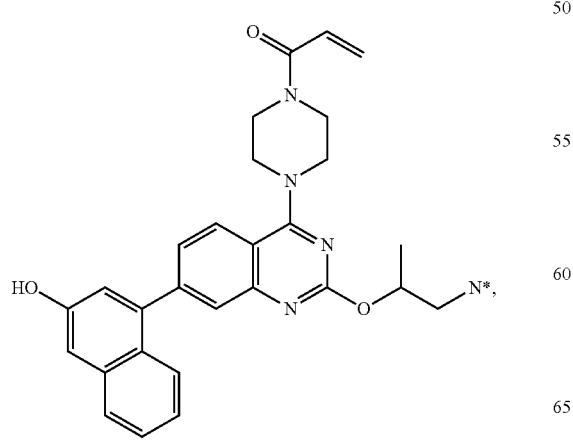
PTM-74
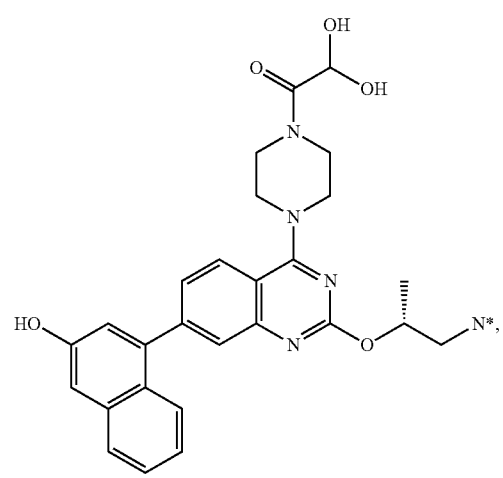

PTM-74
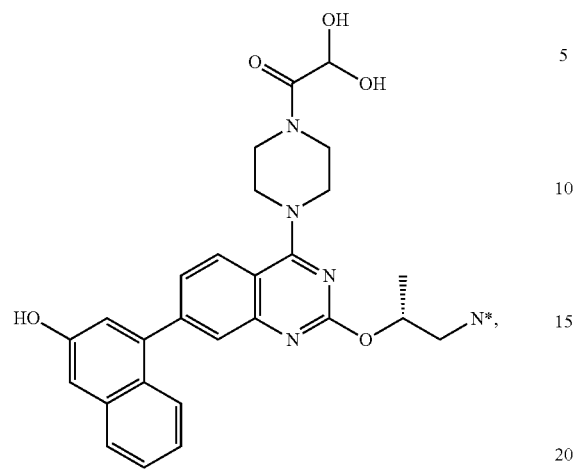
PTM-75

PTM-76
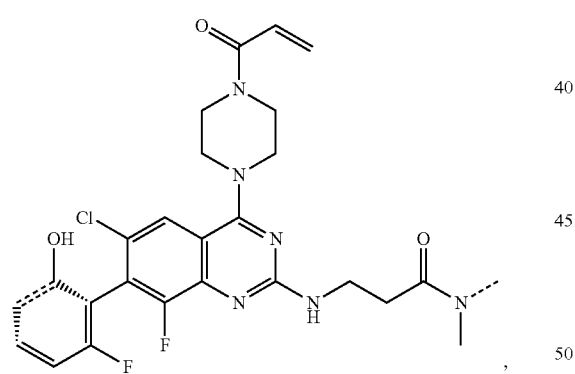
PTM-77
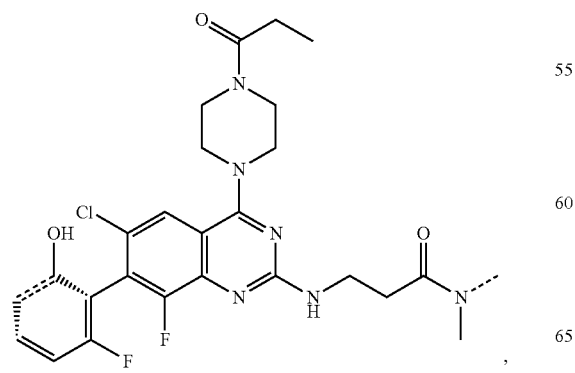
PTM-78
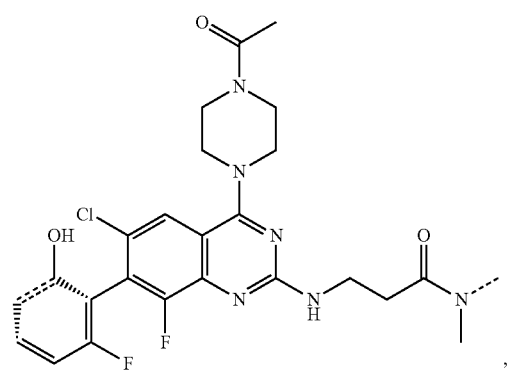
PTM-79
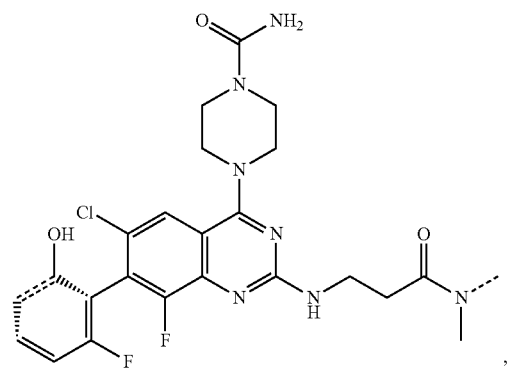
PTM-80
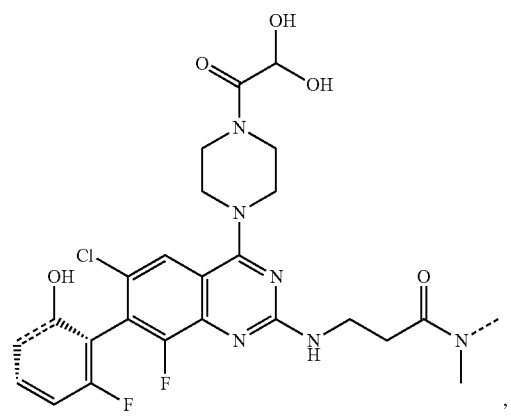

PTM-81
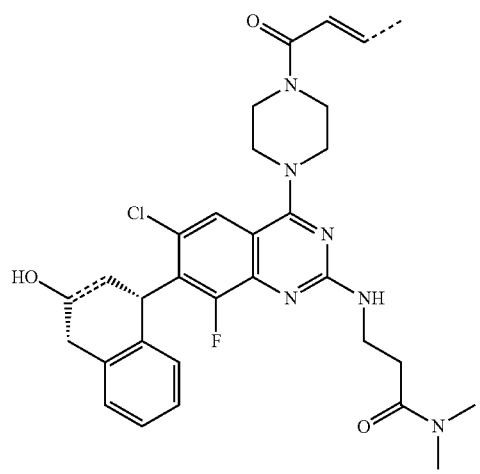
PTM-84
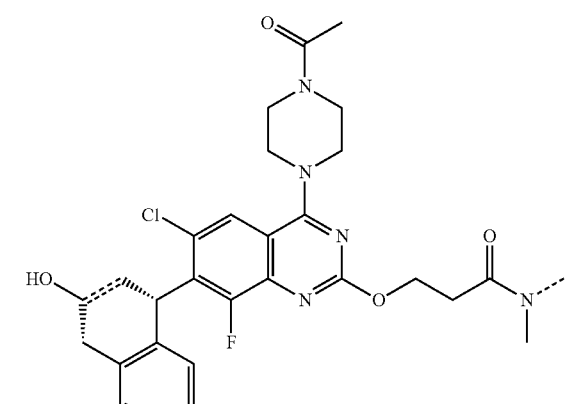
PTM-82
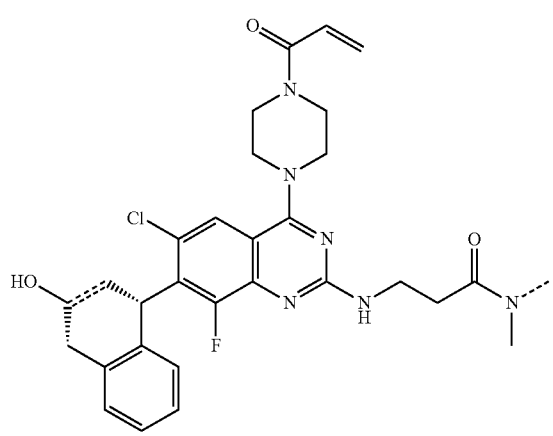
PTM-85
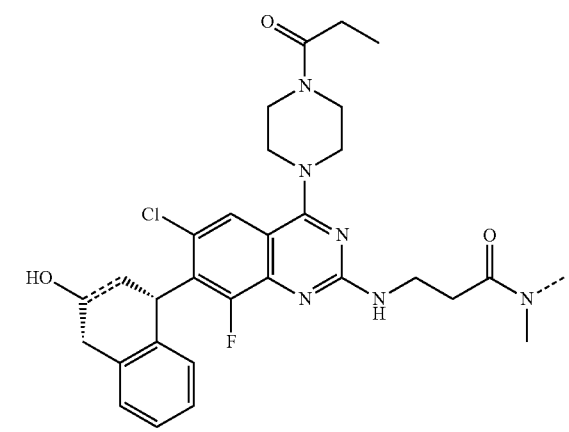
PTM-83
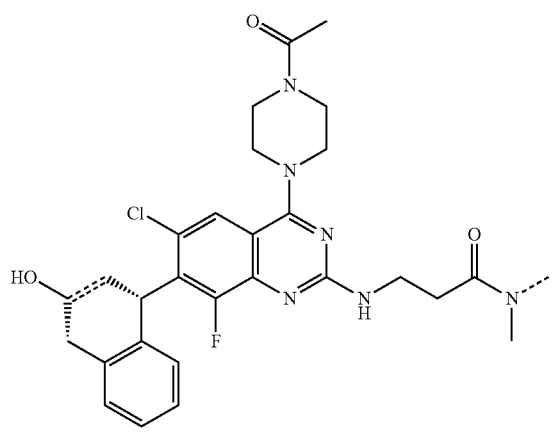
PTM-86
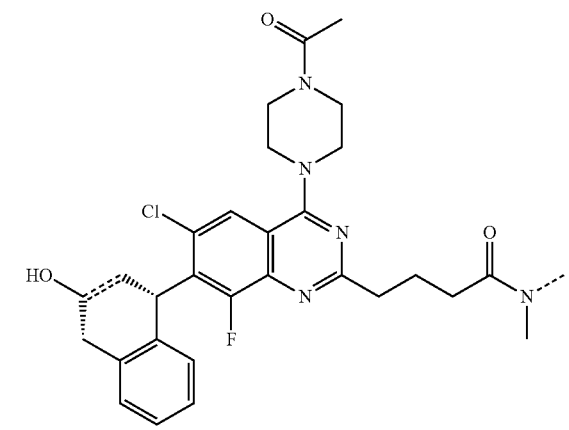

PTM-87
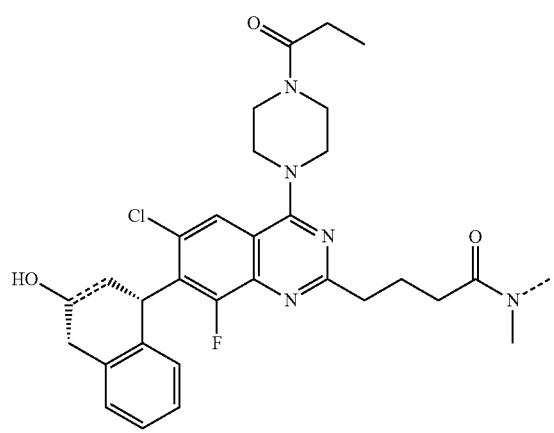
PTM-88
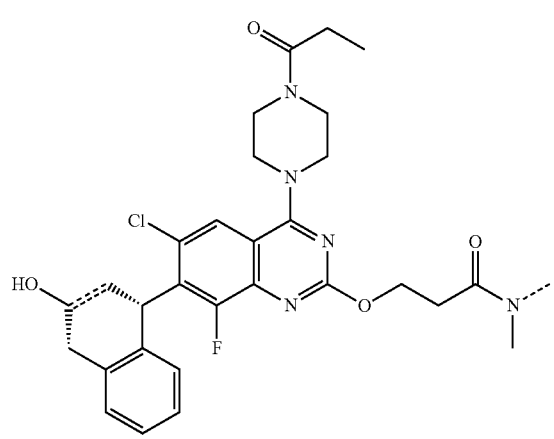
PTM-89
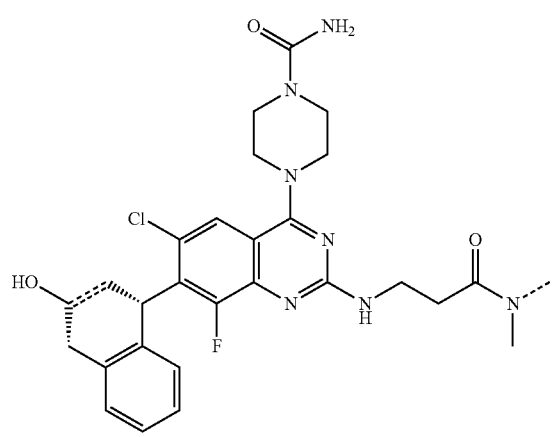
PTM-90
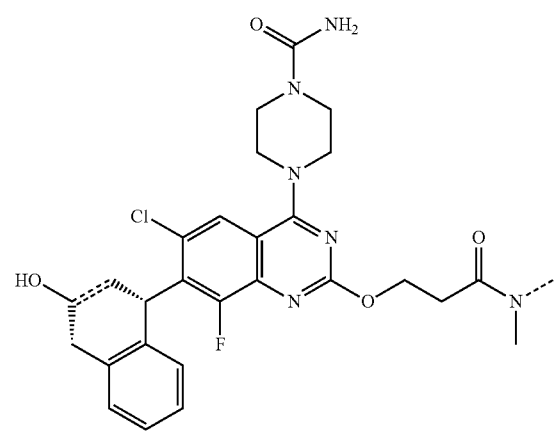
PTM-91
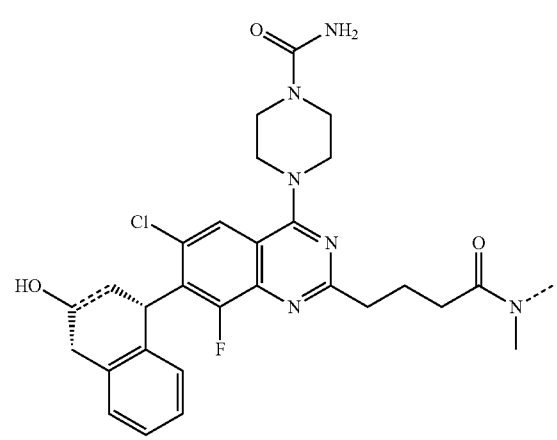
PTM-92
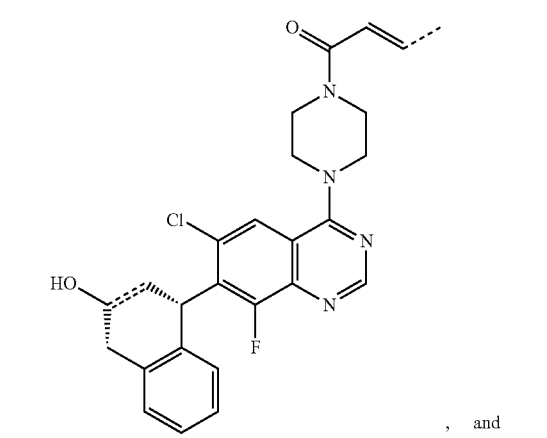
, and

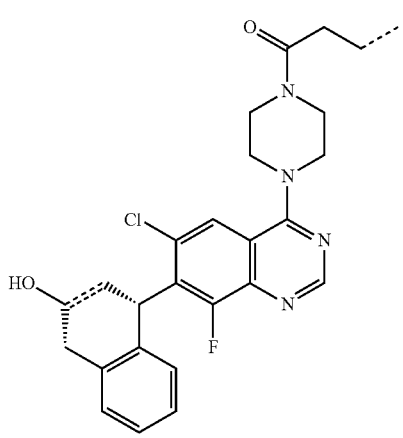

PTM-93

In any aspect or embodiment described herein, the PTM is: (i) a PTM selected from a compound of Tables 4, 6, 8, 10, and 12; or (ii) a PTM of Table 1.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, including epidermal growth factor receptor inhibitors, EPO and darbapoietin alfa, among others. In certain preferred aspects of the disclosure, one or more compounds according to the present disclosure are coadministered with another bioactive agent, such as an anti-cancer agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer (e.g., at least one of pancreatic cancer, colon cancer, colorectal cancer, lung cancer, non-small cell lung cancer, biliary tract malignancies, endometrial cancer, cervical cancer, bladder cancer, liver cancer, myeloid leukemia, breast cancer, or combinations thereof), which may be treated using compounds according to the present disclosure are set forth hereinabove.

The description provides therapeutic compositions as described herein for effectuating the degradation of proteins of interest for the treatment or amelioration of a disease, e.g., cancer (such as pancreatic cancer, colon cancer, colorectal cancer, lung cancer, non-small cell lung cancer, biliary tract malignancies, endometrial cancer, cervical cancer, bladder cancer, liver cancer, myeloid leukemia, or breast cancer). In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. In any aspect or embodiment described herein, the disease or disorder is a cancer or neoplasia selected from pancreatic cancer, colon cancer, colorectal cancer, lung cancer, non-small cell lung cancer, biliary tract malignancies, endometrial cancer, cervical cancer, bladder cancer, liver cancer, myeloid leukemia, or breast cancer (e.g., a cancer or neoplasia selected from pancreatic cancer, colon cancer, lung cancer, or non-small cell lung cancer). Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, non-small cell lung cancer, biliary tract malignancies, endometrial cancer, myeloid leukemia, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatinib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In any aspect or embodiment described herein, the bioactive agent or additional anti-cancer agent is a chemotherapy or biological therapy that targets epidermal growth factor receptors (e.g., an epidermal growth factor receptor inhibitor, such as at least one of gefitinib, erlotinib, neratinib, lapatinib, cetuximab, vandetanib, necitumamab, osimertinib, or a combination thereof).

The term "anti-HIV agent" or "additional anti-HIV agent" includes, for example, nucleoside reverse transcriptase inhibitors (NRTI), other non-nucleoeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddl (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-

6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT C1, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl(pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Abbreviations:
DIEA or DIPEA: diisopropylethylamine
DMF: N,N-dimethylformamide
DMSO: Dimethyl sulfoxide
EDCI: 1-ethyl-3-(3-dimethylaminopropyl)carbodiimide
HOBt: hydroxybenzotriazole Exemplary Synthesis of Intermediates Exemplary syntheses of intermediates which may be used for synthesis of compounds of the invention are described in Schemes A through I.

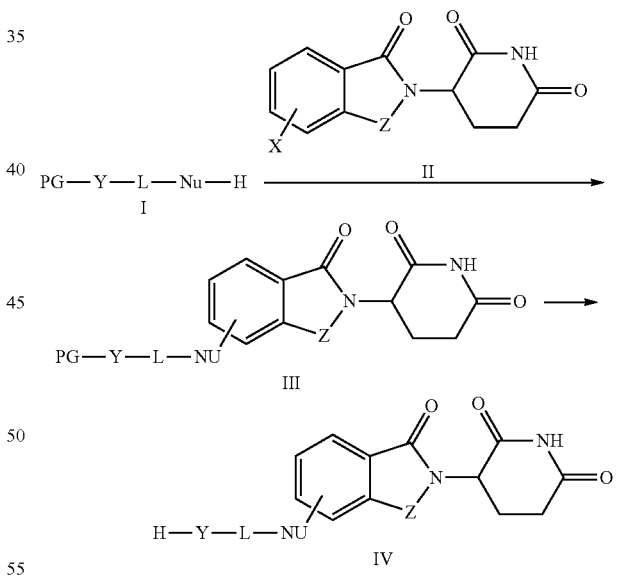

Scheme A.

A compound of formula I, which is commercially available or readily prepared using standard reaction techniques known to one skilled in the art, may be reacted with a compound of formula II under conditions suitable for a nucleophilic aromatic substitution reaction, e.g. using a suitable base such as diisopropylethylamine in a suitable solvent such as N,N-dimethylpyrrolidone. Herein, Y is a primary or secondary amine, which may be optionally substituted or cyclized into a 4- to 8-membered heterocyclic ring, or is carboxylate; PG is H or a suitable optional protecting group, including but not limited to t-butoxycarbonyl when Y is a primary or secondary amine or t-butyl when Y is carboxylate; L is an optional linker; Nu is a suitable nucleophilic group such as O or a primary or secondary amine, which may be optionally substituted or cyclized into a 4- to 8-membered heterocyclic ring; X is a suitable leaving group such as fluoride or chloride; and Z is $CH_2$ or C=O. In cases where III contains an optional protecting group PG, PG may be removed under suitable conditions, e.g. hydrochloric acid in 1,4-dioxane when PG-Y is t-butoxycarbonylamino, or trifluoroacetic acid in dichloromethane when PG-Y is t-butyl-carboxylate, to afford a compound of formula IV. In cases where PG is H, it is understood that III and IV are identical structures.

Scheme B.

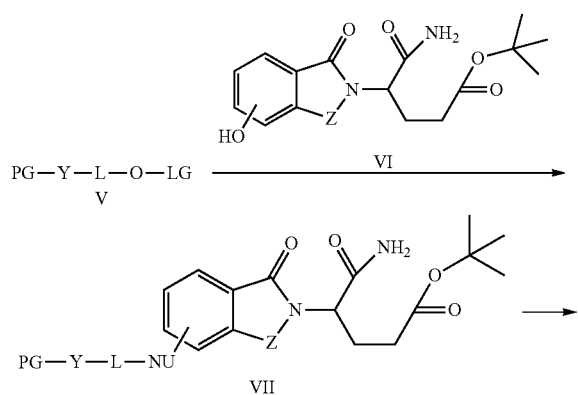

Alternatively, a compound of formula V, which is commercially available or readily prepared using standard reaction techniques known to one skilled in the art, may be reacted with a compound of formula VI to prepare a compound of formula VII. Herein PG, Y, and L are as defined in Scheme A; Z is $CH_2$, and Nu is O. LG may be a suitable leaving group such as tosylate, bromide, or iodide, in which case the reaction conditions are those for nucleophilic substitution, e.g. employing a suitable base such as potassium carbonate and a suitable solvent such as N,N-dimethylformamide. Alternatively, LG may be H, in which case the reaction conditions are those for a Mitsunobu reaction, e.g. triphenylphosphine and diisopropylazodicarboxylate. A compound of formula VII may then be converted to a compound of formula IV using conditions suitable for an imide ring closure and concomitant removal of PG as necessary, e.g. p-toluenesulfonic acid or benzenesulfonic acid in acetonitrile at 80° C.

Scheme C.

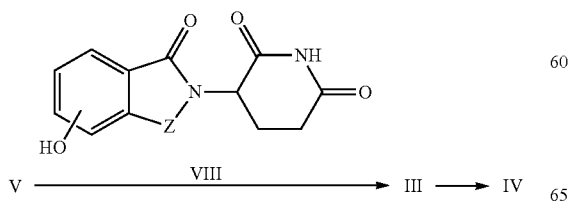

Alternatively, a compound of formula V, may be reacted with a compound of formula VIII to prepare a compound of formula III. Herein Z is C=O, and all other groups are as defined in Scheme B. LG may be a suitable leaving group such as tosylate, in which case the reaction conditions are those for nucleophilic substitution, e.g. employing a suitable base such as potassium carbonate and a suitable solvent such as N,N-dimethylformamide. A compound of formula III may then be converted to a compound of formula IV using conditions as described in Scheme A. Compounds of formula IV may be further converted to additional compounds of formula IV, e.g. via functional group manipulation in the linker L, using techniques known to one skilled in the art. For example, if L contains an alkene, such alkene may be reduced under hydrogenation conditions, e.g. $H_2$, palladium on carbon in methanol, to afford the corresponding alkane.

Scheme D.

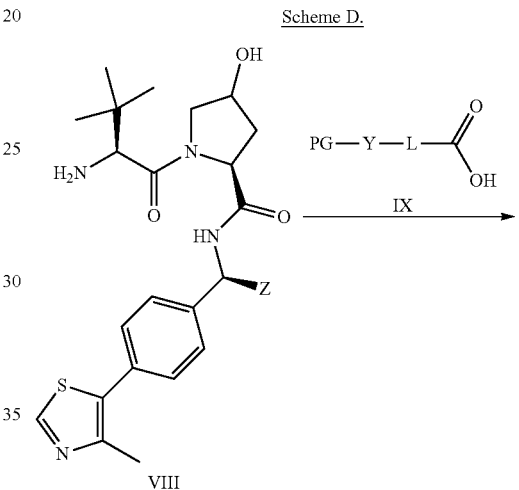

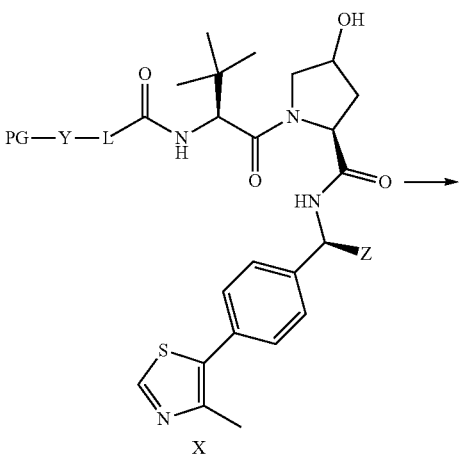

497
-continued

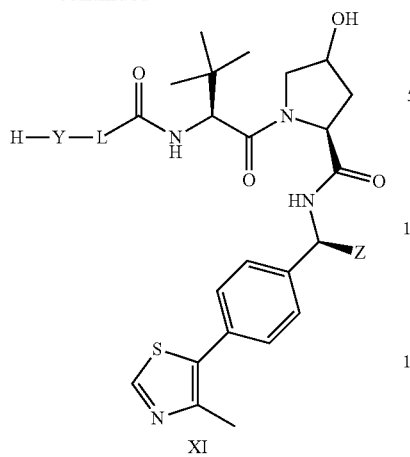

XI

A compound of formula VIII may be reacted with a compound of formula IX to produce compounds of formula X under amide formation conditions, e.g. hydroxybenzotriazole, 1-ethyl-3-(3-dimethylaminopropyl)carbodiimide, and diisopropylethylamine in N,N-dimethylformamide or 1-[bis(dimethylamino)methylene]-1H-1,2,3-triazolo[4,5-b]pyridinium 3-oxid hexafluorophosphate and diisopropylethylamine or triethylamine in dichloromethane. Herein Z is an optional substituent, e.g. H, methyl, or hydroxymethyl, Y is a primary or secondary amine, which may be optionally substituted or cyclized into a 4- to 8-membered heterocyclic ring, or is carboxylate; PG is a suitable optional protecting group, including but not limited to t-butoxycarbonyl when Y is a primary or secondary amine or methyl when Y is carboxylate; and L is an optional linker. A compound of formula X may then be converted to a compound of formula XI by removal of PG under suitable conditions, e.g. hydrochloric acid in 1,4-dioxane or dichloromethane when PG-Y is t-butoxycarbonylamino, or sodium hydroxide or lithium hydroxide in water mixed with tetrahydrofuran and/or methanol or hydrochloric acid in 1,4-dioxane when PG-Y is methyl carboxylate.

Scheme E.

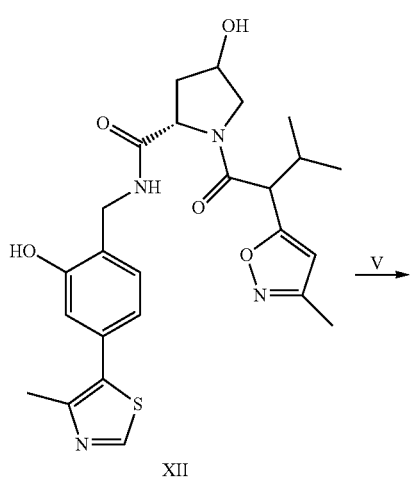

XII

498
-continued

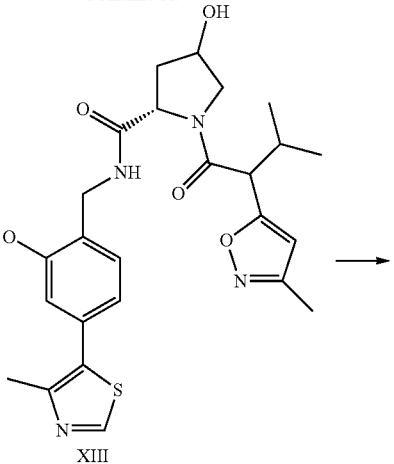

XIII

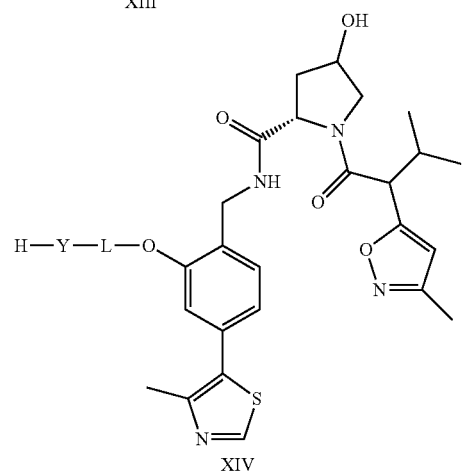

XIV

A compound of formula XII may be reacted with a compound of formula V to prepare a compound of formula XIII. Herein LG may be a suitable leaving group such as tosylate, bromide, or iodide; L is an optional linker; Y is a primary or secondary amine, which may be optionally substituted or cyclized into a 4- to 8-membered heterocyclic ring, or is carboxylate; PG is H or a suitable optional protecting group, including but not limited to t-butoxycarbonyl when Y is a primary or secondary amine or t-butyl when Y is carboxylate; or alternatively PG-Y together are LG', a suitable leaving group which may be the same or different from LG. The reaction conditions for the preparation of a compound of formula XIII are those for nucleophilic substitution, e.g. employing a suitable base such as potassium carbonate and a suitable solvent such as N,N-dimethylformamide at a temperature such as 80° C. PG may be removed under suitable conditions, e.g. hydrochloric acid in 1,4-dioxane when PG-Y is t-butoxycarbonylamino, or trifluoroacetic acid in dichloromethane when PG-Y is t-butyl-carboxylate; or alternatively when PG-Y are together LG' they may be treated with a nucleophile, e.g. a primary amine in ethanol, in which case Y in XIV becomes a secondary amine, to afford a compound of formula XIV. In cases where PG is H, it is understood that XIII and XIV are identical structures. As needed, mixtures of enantiomers or diastereomers of any compounds XIII or XIV may be resolved into their constituent enantiomers or diastereomers using techniques known to one skilled in the art, including but not limited to preparative high performance liquid chromatography or preparative supercritical fluid chromatography.

Scheme F.

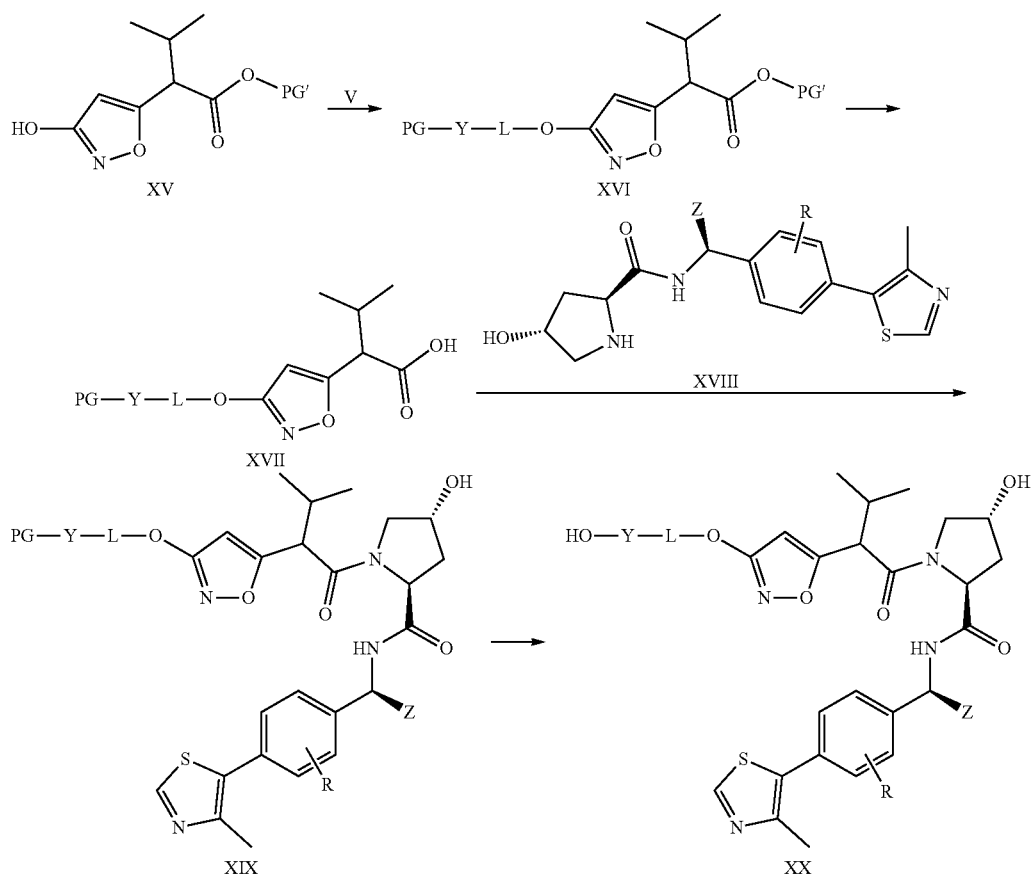

A compound of formula XV may be reacted with a compound V (readily prepared using standard reaction techniques known to one skilled in the art) to prepare a compound of formula XVI under nucleophilic substitution conditions, e.g. using a suitable base such as potassium carbonate in a suitable solvent such as N,N-dimethylformamide. Herein, PG, Y, L, and LG in compound V are as defined in Scheme B; and PG' represents a suitable ester protecting group, e.g. methyl, ethyl, or t-butyl. Compounds of formula XVI may be converted to a compound of formula XVIII by treatment with a reagent suitable for the removal of PG', e.g. sodium hydroxide or lithium hydroxide in methanol and water when PG' is methyl or ethyl or trifluoroacetic acid with PG' is t-butyl. Compound XVII may be reacted with a compound of formula XVIII, wherein Z is an optional substituent, e.g. H, methyl, or hydroxymethyl and R is an optional substituent, to produce compounds of formula XIX under amide formation conditions, e.g. 1-hydroxybenzotriazole, N-(3-dimethylaminopropyl)-N'-ethylcarbodiimide, diisopropylethylamine, N,N-dimethylformamide. A compound of formula XIX may be converted to a compound of formula XX by removal of PG under suitable conditions, e.g. hydrochloric acid in 1,4-dioxane when PG-Y is t-butoxycarbonylamino, or trifluoroacetic acid in dichloromethane when PG-Y is t-butyl-carboxylate; or alternatively when PG-Y are together a suitable leaving group which may be the same or different from LG they may be treated with a nucleophile, e.g. a primary amine in ethanol, in which case Y in XX becomes a secondary amine. In cases where PG is H, it is understood that XIX and XX are identical structures. As needed, mixtures of enantiomers or diastereomers of any compounds XVI, XVII, XIX, or XX may be resolved into their constituent enantiomers or diasteromers using techniques known to one skilled in the art, including but not limited to preparative high performance liquid chromatography or preparative supercritical fluid chromatography.

Scheme G.

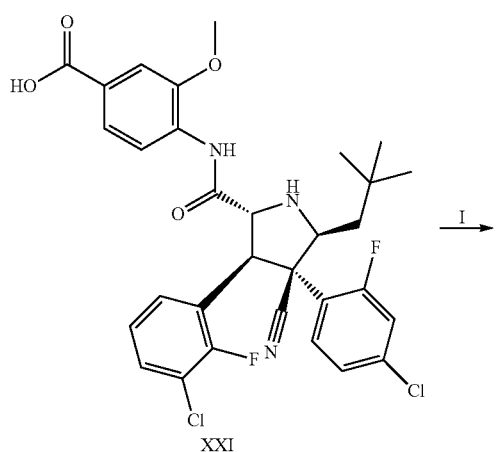

-continued

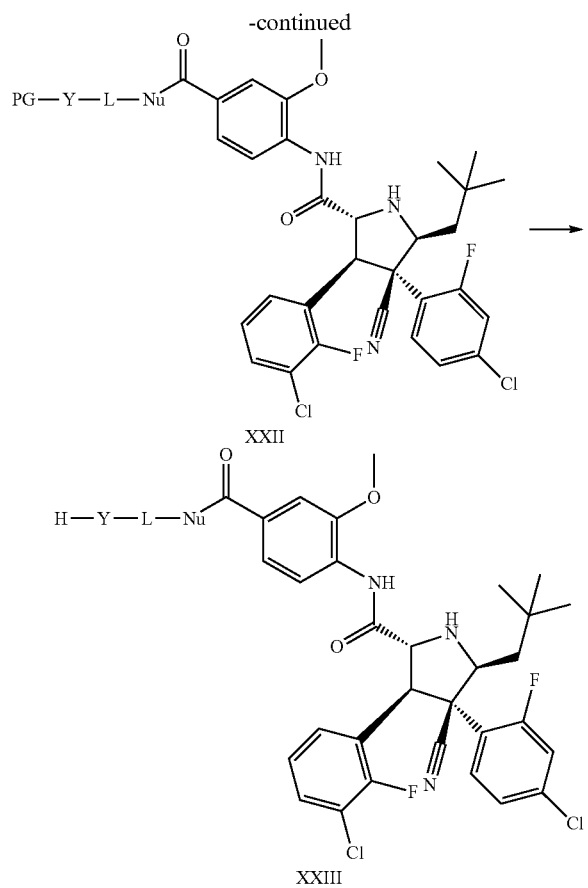

XXII

XXIII

A compound of formula XXI may be reacted with a compound of formula I under conditions suitable an amide coupling, e.g. 1-[bis(dimethylamino)methylene]-1H-1,2,3-triazolo[4,5-b]pyridinium 3-oxid hexafluorophosphate and diisopropylethylamine in N,N-dimethylformamide, to afford a compound of formula XXII. Herein Y is a primary or secondary amine, which may be optionally substituted or cyclized into a 4- to 8-membered heterocyclic ring; PG is H or a suitable optional protecting group, including but not limited to t-butoxycarbonyl; L is an optional linker; and Nu is a primary or secondary amine, which may be optionally substituted or cyclized into a 4- to 8-membered heterocyclic ring. In cases where XXII contains an optional protecting group PG, PG may be removed under suitable conditions, e.g. hydrochloric acid in 1,4-dioxane when PG-Y is t-butoxycarbonylamino, to afford a compound of formula XXIII. In cases where PG is H, it is understood that XXII and XXIII are identical structures.

Scheme H.

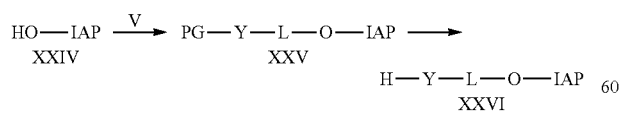

A compound of formula XXIV may be reacted with a compound of formula V to prepare a compound of formula XXV. Herein LG may be a suitable leaving group such as tosylate, bromide, or iodide; L is an optional linker; Y is a primary or secondary amine, which may be optionally substituted or cyclized into a 4- to 8-membered heterocyclic ring and PG is H or a suitable optional protecting group, including but not limited to benzyloxycarbonyl or 2-(trimethylsilyl)ethoxycarbonyl; or alternatively PG-Y together are LG', a suitable leaving group which may be the same or different from LG; and IAP is either:

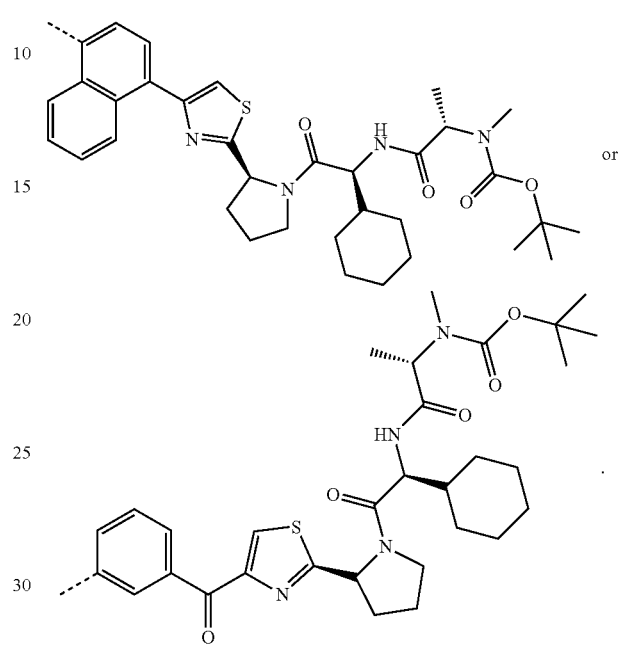

or

The reaction conditions are those for nucleophilic substitution, e.g. employing a suitable base such as potassium carbonate and a suitable solvent such as N,N-dimethylformamide or acetonitrile at a temperature such as 70-80° C. PG may be removed under suitable conditions to afford a compound of formula XXVI, e.g. hydrogen, palladium on carbon when PG-Y is benzyloxycarbonylamino, or tetra-n-butylammonium fluoride in tetrahydrofuran when PG-Y is 2-(trimethylsilyl)ethoxycarbonylamino; or alternatively when PG-Y are together LG' they may be treated with a nucleophile, e.g. a primary amine in ethanol at 60° C., in which case Y in XXVI becomes a secondary amine. In cases where PG is H, it is understood that XXV and XXVI are identical structures.

Scheme I.

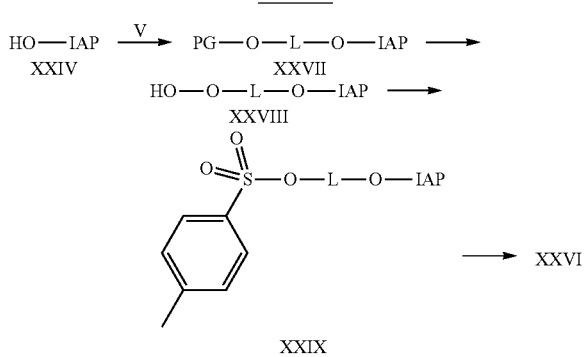

Alternatively, a compound of formula XXIV as defined in Scheme H, may be reacted with a different compound of formula V wherein PG is a suitable protecting group, such as tetrahydropyranyl, Y is O, L is an optional linker, and LG is a suitable leaving group such as tosylate, bromide, or iodide, under conditions of a nucleophilic substitution, e.g. potassium carbonate and potassium iodide in N,N-dimethylformamide at 70° C., to afford a compound of formula XXVII. The compound of formula XXVII may be deprotected, e.g. with pyridinium p-toluenesulfonate in methanol, to afford a compound XXVIII. A compound of formula XXVIII may be converted to a compound of formula XXIX by treatment with e.g. p-toluenesulfonyl chloride, triethylamine, N,N-dimethylaminopyridine in dichloromethane. Finally, a compound of formula XXIX may be treated with a nucleophile, e.g. a primary amine in ethanol at 60° C., converting it to a compound of formula XXVI as described in Scheme H.

General Synthetic Schemes:

Compounds of the invention may be synthesized as shown in Schemes 1 through 19, making use of the intermediate structures described in Schemes A through I.

independently substituted with OH, H, and/or halogen; $R_2$ is an optionally substituted alkyl amide, alkenyl amide, urea, or a suitable protecting group such as t-butoxycarbonyl; $R_3$ is an optional substituent; L' is an optional linker; W is a carboxylic acid; Y is a primary or secondary amine, which may be optionally substituted or cyclized into a 4- to 8-membered heterocyclic ring; and L, Nu, and Z are as defined in one of Schemes A, B, or C.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XXXI under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine.

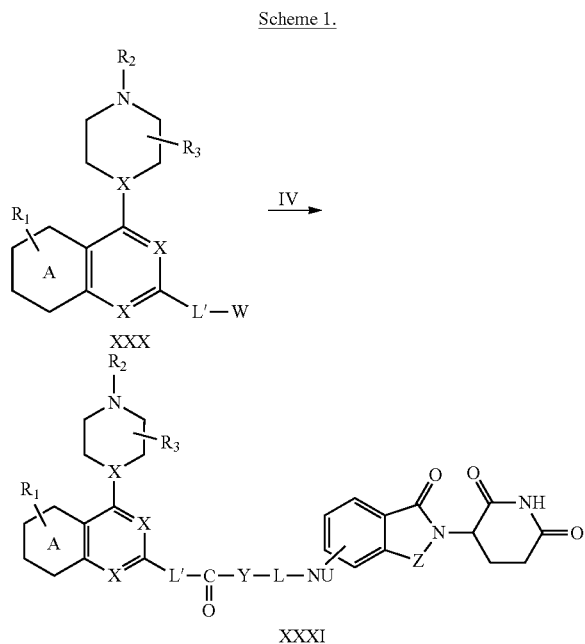

A compound of formula XXX may be reacted with a compound of formula IV under amide coupling conditions, e.g. 1-[bis(dimethylamino)methylene]-1H-1,2,3-triazolo[4,5-b]pyridinium 3-oxid hexafluorophosphate and diisopropylethylamine in N,N-dimethylformamide or 1-hydroxybenzotriazole and N-(3-dimethylaminopropyl)-N'-ethylcarbodiimide, diisopropylethylamine in N,N-dimethylformamide to afford a compound of formula XXXI.

Herein,

is an aryl, heteroaryl, cycloalkyl, or heterocycloalkyl; each X is independently CH or N; $R_1$ is one or more independent alkyl, alkoxy, phenyl, or napthalene, each of which may be A compound of formula XXX may also be reacted with a compound of formula IV under amide coupling conditions, e.g. 1-[bis(dimethylamino)methylene]-1H-1,2,3-triazolo[4,5-b]pyridinium 3-oxid hexafluorophosphate and triethylamine in N,N-dimethylformamide to form a compound of formula XXXII.

Herein, $R_2$ is H; L'-W together are H or form an optional substitution;

,

X, $R_1$, $R_3$ are as defined in Scheme 1; Y is a carboxylic acid; and L, Nu, and Z are as defined in one of Schemes A, B, or C.

Scheme 3.

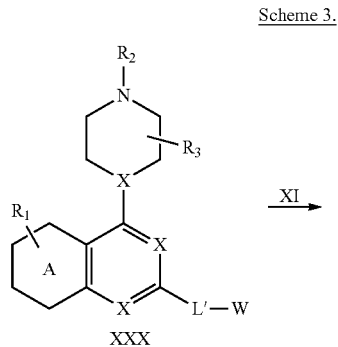

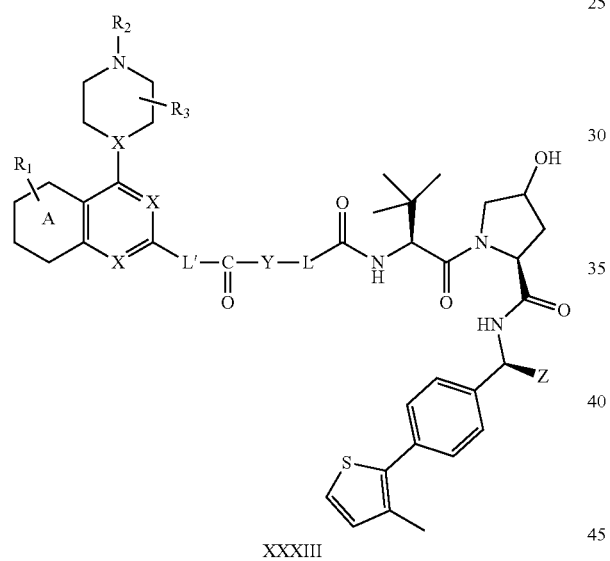

A compound of formula XXX may also be reacted with a compound of formula XI under amide coupling conditions, e.g. 1-[bis(dimethylamino)methylene]-1H-1,2,3-triazolo[4,5-b]pyridinium 3-oxid hexafluorophosphate and diisopropylethylamine in N,N-dimethylformamide afford a compound of formula XXXIII.

Herein,

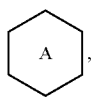

X, $R_1$, $R_2$, $R_3$, L', and W are as defined in Scheme 1; Y is a primary or secondary amine, which may be optionally substituted or cyclized into a 4- to 8-membered heterocyclic ring; and L and Z are as defined in Scheme D.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XXXIII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

Scheme 4.

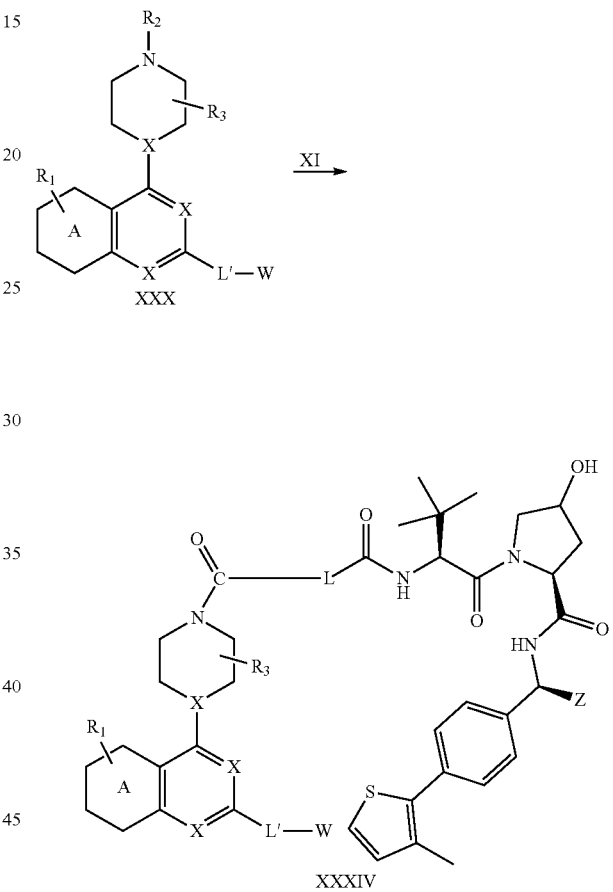

A compound of formula XXX may also be reacted with a compound of formula XI under amide coupling conditions, e.g. 1-[bis(dimethylamino)methylene]-1H-1,2,3-triazolo[4,5-b]pyridinium 3-oxid hexafluorophosphate and triethylamine in N,N-dimethylformamide to form a compound of formula XXXIV.

Herein, $R_2$ is H; L'-W together are H or form an optional substitution;

X, $R_1$, $R_3$ are as defined in Scheme 1; Y is a carboxylic acid; and L and Z are as defined in Scheme D.

Scheme 5.

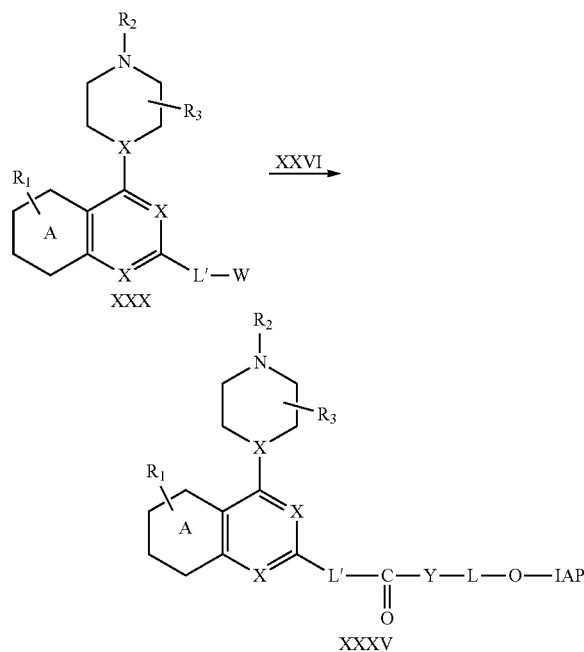

A compound of formula XXX may also be reacted with a compound of formula XXVI under amide coupling conditions, e.g. 1-[bis(dimethylamino)methylene]-1H-1,2,3-triazolo[4,5-b]pyridinium 3-oxid hexafluorophosphate and diisopropylethylamine in N,N-dimethylformamide afford a compound of formula XXXV.

Herein,

X, $R_1$, $R_2$, $R_3$, L', and W are as defined in Scheme 1; Y is a primary or secondary amine, which may be optionally substituted or cyclized into a 4- to 8-membered heterocyclic ring; and L and IAP are as defined in one of Schemes H or I.

The t-butoxycarbonyl group contained in the structure of IAP may then be removed under suitable conditions, for example hydrochloric acid in 1,4-dioxane or tifluoroacetic acid in dichloromethane, to afford different compounds of formula XXXV where the structure of IAP is either:

Scheme 6.

A compound of formula XXX may also be reacted with a compound of formula XXIII under amide coupling conditions, e.g. 1-[bis(dimethylamino)methylene]-1H-1,2,3-triazolo[4,5-b]pyridinium 3-oxid hexafluorophosphate and diisopropylethylamine in N,N-dimethylformamide afford a compound of formula XXXVI.

Herein,

X, $R_1$, $R_2$, $R_3$, L', and W are as defined in Scheme 1; Y is a primary or secondary amine, which may be optionally substituted or cyclized into a 4- to 8-membered heterocyclic ring; and L and Nu are as defined in Scheme G.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XXXVI under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

converted to a different compound of formula XXXVII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature. As needed, mixtures of enantiomers or diastereomers of any compounds XXXVII may be resolved into their constituent enantiomers or diastereomers using techniques known to one skilled in the art, including but not limited to preparative high performance liquid chromatography or preparative supercritical fluid chromatography.

Scheme 7.

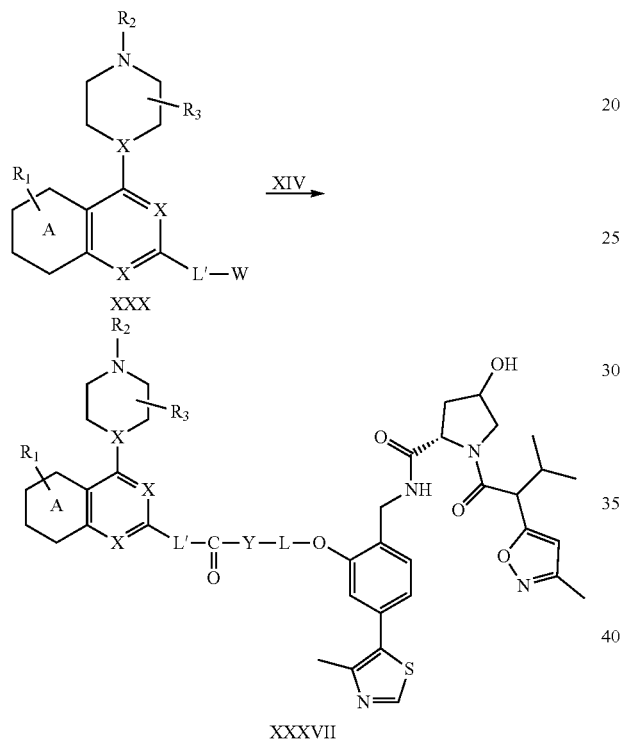

Scheme 8.

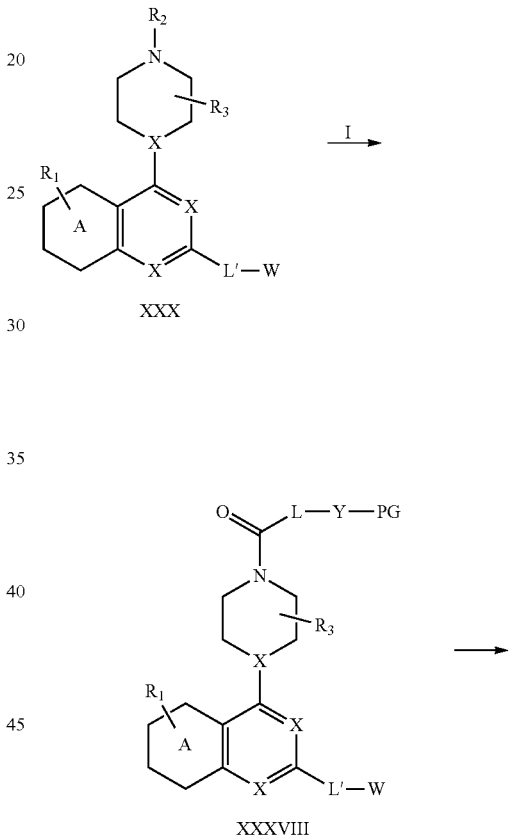

A compound of formula XXX may also be reacted with a compound of formula XIV under amide coupling conditions, e.g. hydroxybenzoltriazole, 1-ethyl-3-(3-dimethylaminopropyl)carbodiimide, and diisopropylethylamine in N,N-dimethylformamide to afford a compound of formula XXXVII.

Herein,

X, $R_1$, $R_2$, $R_3$, L', and W are as defined in Scheme 1; Y is a primary or secondary amine, which may be optionally substituted or cyclized into a 4- to 8-membered heterocyclic ring; and L is as defined in Scheme E.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be

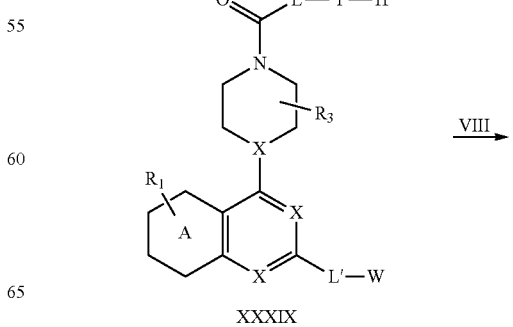

-continued

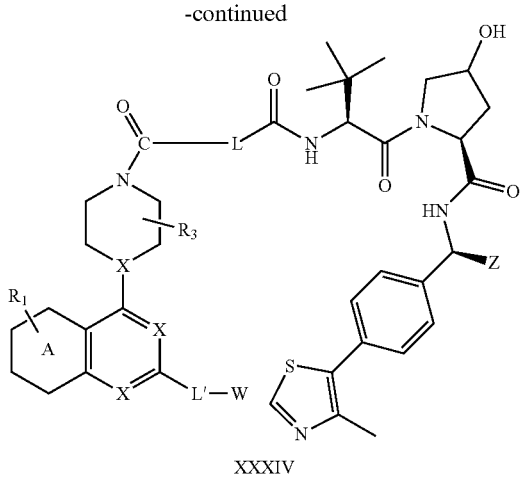

XXXIV

A compound of formula XXX may also be reacted with a compound of formula I under amide coupling conditions, e.g. 1-[bis(dimethylamino)methylene]-1H-1,2,3-triazolo[4,5-b]pyridinium 3-oxid hexafluorophosphate and triethylamine in N,N-dimethylformamide to form a compound of formula XXXIV.

Herein, $R^2$ is H; L'-W together are H or form an optional substitution;

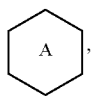

X, $R_1$, $R_3$ are as defined in Scheme 1; Nu-H is a primary or secondary amine; L is an optional linker; Y is carboxylate, and PG is a suitable carboxylic acid protecting group including but not limited to methyl or ethyl. A compound of formula XXXVIII may then be converted to a compound of formula XXXIX under conditions suitable for the removal of PG, for example lithium hydroxide in water and a mixture of methanol and/or tetrahydrofuran when PG is methyl or ethyl. Finally, a compound of formula XXXIX may be reacted with a compound of formula VIII under conditions suitable for amide formation, e.g. hydroxybenzoltriazole, 1-ethyl-3-(3-dimethylaminopropyl)carbodiimide, and diisopropylethylamine in N,N-dimethylformamide, to afford a compound of formula XXXIV. Herein Z is as defined in Scheme D.

Scheme 9.

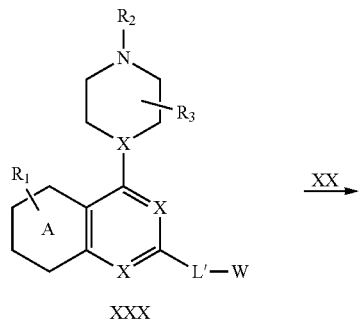

-continued

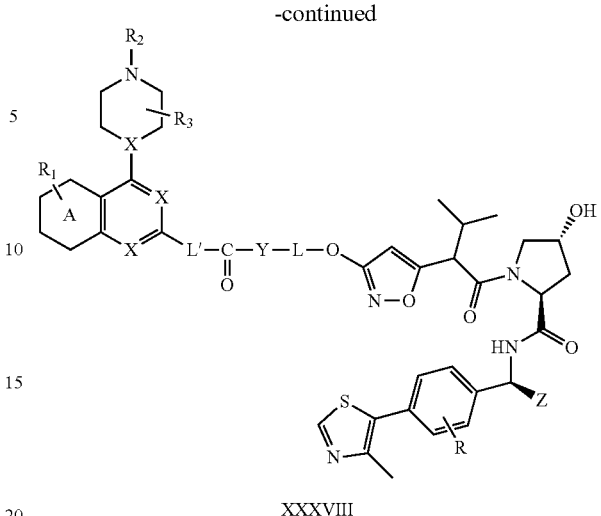

XXXVIII

A compound of formula XXX may also be reacted with a compound of formula XX under amide coupling conditions, e.g. 1-[bis(dimethylamino)methylene]-1H-1,2,3-triazolo[4,5-b]pyridinium 3-oxid hexafluorophosphate and diisopropylethylamine in N,N-dimethylformamide afford a compound of formula XXXVIII.

Herein,

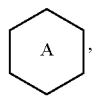

X, $R_1$, $R_2$, $R_3$, L', and W are as defined in Scheme 1; Y is a primary or secondary amine, which may be optionally substituted or cyclized into a 4- to 8-membered heterocyclic ring; and L, Z, and R are as defined in Scheme F.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XXXVIII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature. As needed, mixtures of enantiomers or diastereomers of any compounds XXXVIII may be resolved into their constituent enantiomers or diastereomers using techniques known to one skilled in the art, including but not limited to preparative high performance liquid chromatography or preparative supercritical fluid chromatography.

Scheme 10.

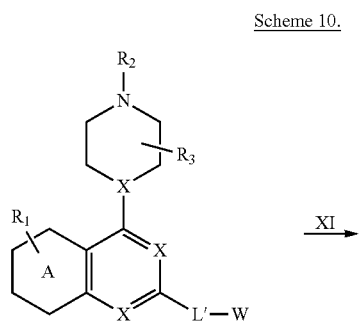

XXX

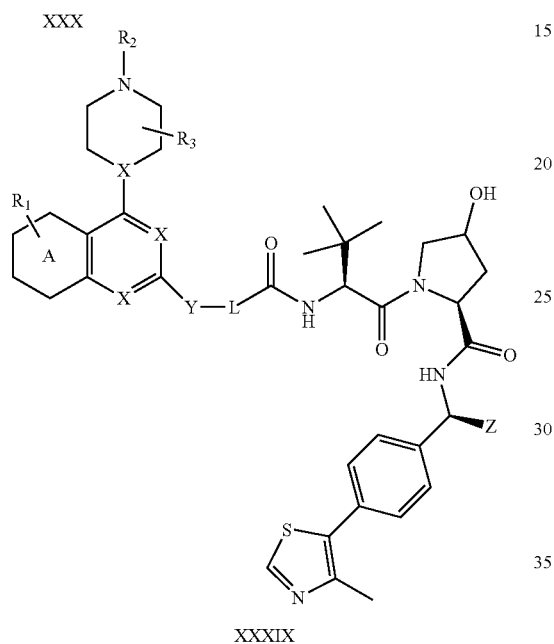

XXXIX

A compound of formula XXX may also be reacted with a compound of formula XI under conditions for a nucleophilic aromatic substitution reaction, e.g. diisopropylethylamine in isopropanol at 115° C. with microwave heating, to afford a compound of formula XXXIX.

Herein,

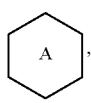

X, $R_1$, $R_2$, and $R_3$ are as defined in Scheme 1; L' is absent; W is a suitable leaving group such as fluoride or chloride; Y is a primary or secondary amine, which may be optionally substituted or cyclized into a 4- to 8-membered heterocyclic ring; and L and Z are as defined in Scheme D. In cases where $R_1$ is an aryl or heteroaryl chloride, bromide, or iodide, a compound of formula XXXIX may be further transformed to a different compound of formula XXXIX, e.g. by reaction under Suzuki coupling conditions with an aryl boronic acid or ester, with catalytic (2-dicyclohexylphosphino-2',4',6'-triisopropyl-1,1'-biphenyl)[2-(2'-amino-1,1'-biphenyl)]palladium(II) methanesulfonate, potassium phosphate in water and tetrahydrofuran at 60° C. In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XXXIX under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

Scheme 11.

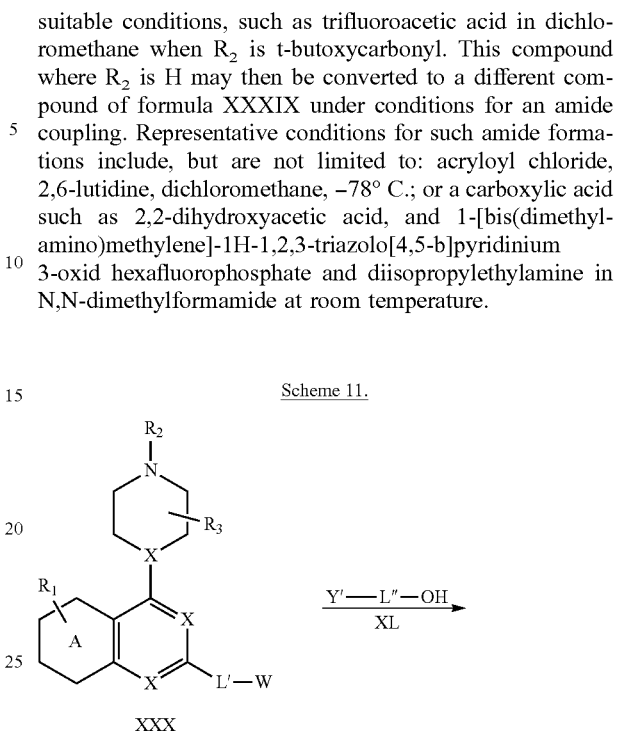

XXX

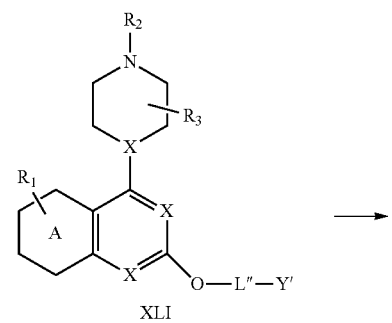

XLI

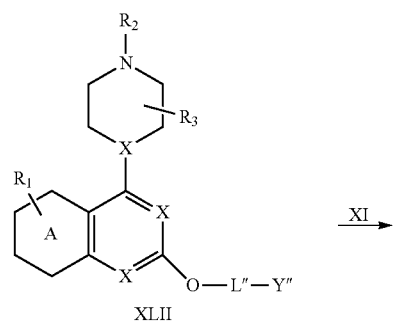

XLII

-continued

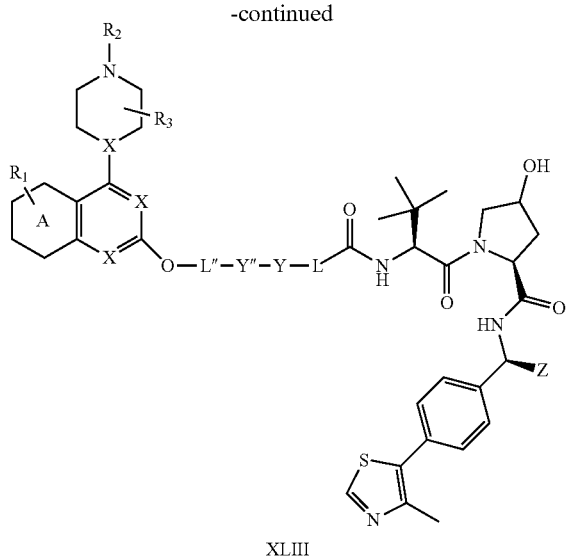

XLIII

A compound of formula XXX may also be reacted with a compound of formula XL under conditions for a nucleophilic aromatic substitution reaction, e.g. sodium hydride in N,N-dimethylformamide at room temperature, to afford a compound of formula XLI.

Herein,

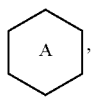,

X, $R_1$, $R_2$, and $R_3$ are as defined in Scheme 1; L' is absent; W is a suitable leaving group such as fluoride or chloride; L" is a linker; and Y' is either is either $CH_2OH$ or a terminal, suitably protected (e.g. t-butoxycarbonyl) primary or secondary amine, which may be optionally substituted or cyclized into a 4- to 8-membered heterocyclic ring.

In cases of XLI where Y' is $CH_2OH$, it may be converted to its corresponding aldehyde under oxidative conditions, for example Swern or Dess-Martin oxidation, to afford a compound XLII wherein Y" is CHO. In cases of XLI where Y' is a terminal, suitably protected primary or secondary amine, it may be converted to the corresponding deprotected amine using suitable conditions, for example trifluoroacetic acid in dichloromethane at room temperature when the protecting group is t-butoxycarbonyl, to afford a compound XLII wherein Y" is the amine of Y' without its protecting group. A compound of formula XLII may then be treated with a compound of formula XI under reductive amination conditions, for example sodium triacetoxyborohydride and triethylamine in dichloromethane or sodium cyanoborohydride, sodium acetate, and acetic acid in dichloromethane and methanol, to afford a compound of formula XLIII. Herein, L and Z are as defined in Scheme D. In cases where Y" in XLII is CHO, Y in XI is a primary or secondary amine, which may be optionally substituted or cyclized into a 4- to 8-membered heterocyclic ring; and Y" in XLIII becomes $CH_2$. In cases where Y" in XLII is a primary or secondary amine, which may be optionally substituted or cyclized into a 4- to 8-membered heterocyclic ring, Y in XI is CHO; and Y in XLIII becomes $CH_2$.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XLIII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

Scheme 12.

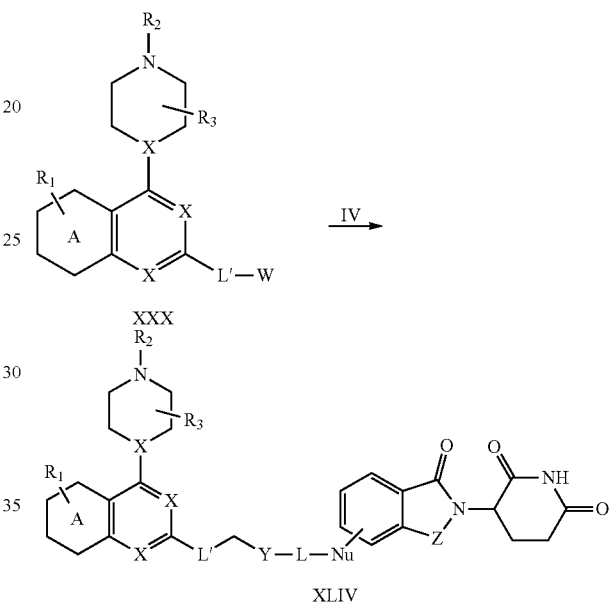

XLIV

A compound of formula XXX may be reacted with a compound of formula IV under reductive amination conditions, for example sodium triacetoxyborohydride and triethylamine in dichloromethane or sodium cyanoborohydride, sodium acetate, and acetic acid in dichloromethane and methanol to afford a compound of formula XXXI.

Herein,

, $R_1$, $R_2$, $R_3$, and L' are as defined in Scheme 1; W is CHO; Y is a primary or secondary amine, which may be optionally substituted or cyclized into a 4- to 8-membered heterocyclic ring; and Nu, L, and Z are as defined in one of Schemes A, B, or C.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XLIV under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine.

Scheme 13.

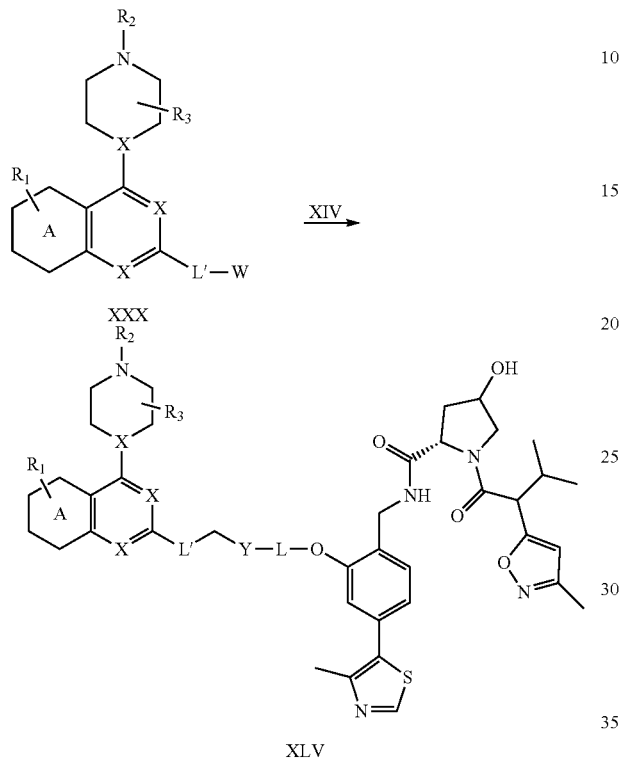

XXX

XLV

A compound of formula XXX may also be reacted with a compound of formula XIV under reductive amination conditions, for example sodium triacetoxyborohydride and triethylamine in dichloromethane or sodium cyanoborohydride, sodium acetate, and acetic acid in dichloromethane and methanol to afford a compound of formula XLV.

Herein,

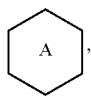

X, $R_1$, $R_2$, $R_3$, and L' are as defined in Scheme 1; W is CHO; Y is a primary or secondary amine, which may be optionally substituted or cyclized into a 4- to 8-membered heterocyclic ring; and L is as defined in Scheme E.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XLV under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature. As needed, mixtures of enantiomers or diastereomers of any compounds XLV may be resolved into their constituent enantiomers or diastereomers using techniques known to one skilled in the art, including but not limited to preparative high performance liquid chromatography or preparative supercritical fluid chromatography.

Scheme 14.

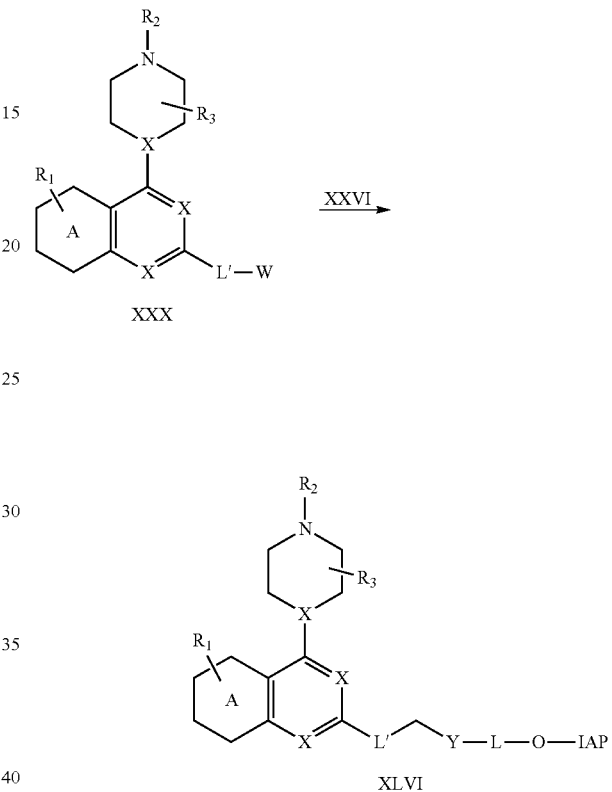

XXX

XLVI

A compound of formula XXX may also be reacted with a compound of formula XXVI under reductive amination conditions, for example sodium triacetoxyborohydride and triethylamine in dichloromethane or sodium cyanoborohydride, sodium acetate, and acetic acid in dichloromethane and methanol to afford a compound of formula XLVI.

Herein,

X, $R_1$, $R_2$, $R_3$, and L' are as defined in Scheme 1; W is CHO; Y is a primary or secondary amine, which may be optionally substituted or cyclized into a 4- to 8-membered heterocyclic ring; and L and IAP are as defined in one of Schemes H or I.

The t-butoxycarbonyl group contained in the structure of IAP may then be removed under suitable conditions, for example hydrochloric acid in 1,4-dioxane or tifluoroacetic acid in dichloromethane, to afford different compounds of formula XLVI where the structure of IAP is either:

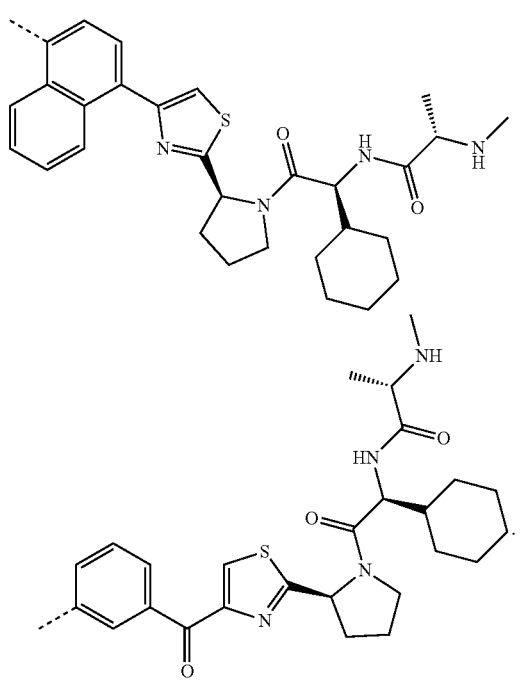

or

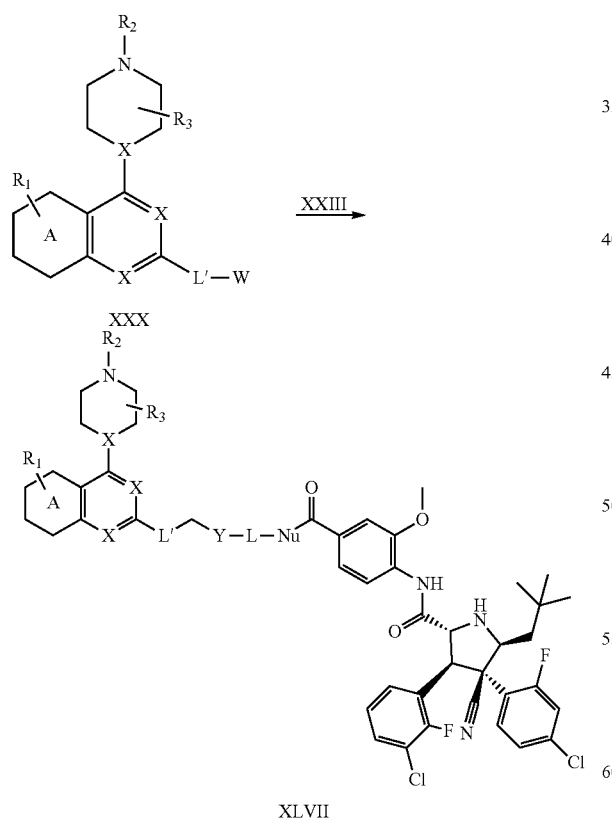

Scheme 15.

A compound of formula XXX may also be reacted with a compound of formula XXIII under reductive amination conditions, for example sodium triacetoxyborohydride and triethylamine in dichloromethane or sodium cyanoborohy-dride, sodium acetate, and acetic acid in dichloromethane and methanol to afford a compound of formula XLVII.

Herein,

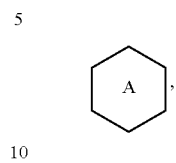

X, $R_1$, $R_2$, $R_3$, and L' are as defined in Scheme 1; W is CHO; Y is a primary or secondary amine, which may be optionally substituted or cyclized into a 4- to 8-membered heterocyclic ring; and L and Nu are as defined in Scheme G.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula XXXVII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

Scheme 16.

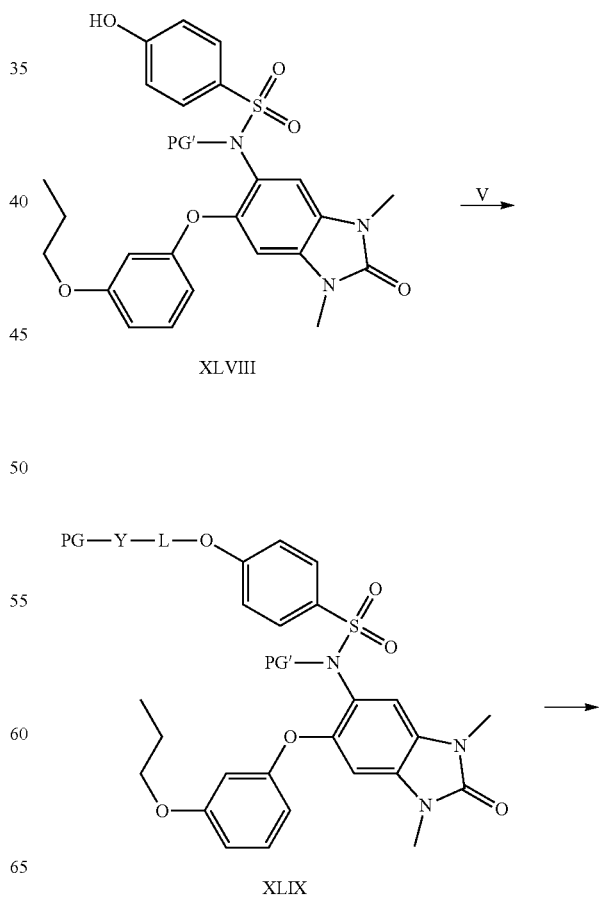

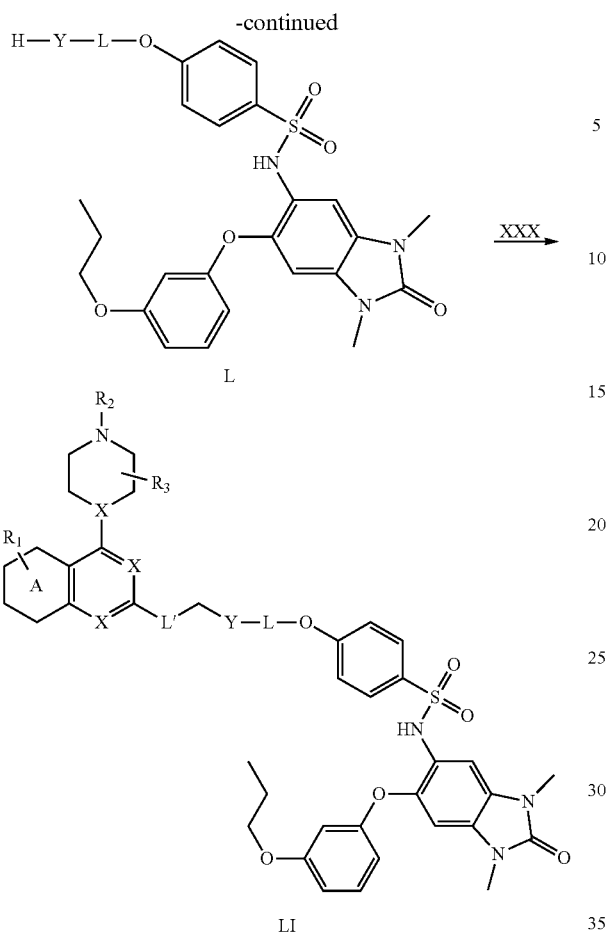

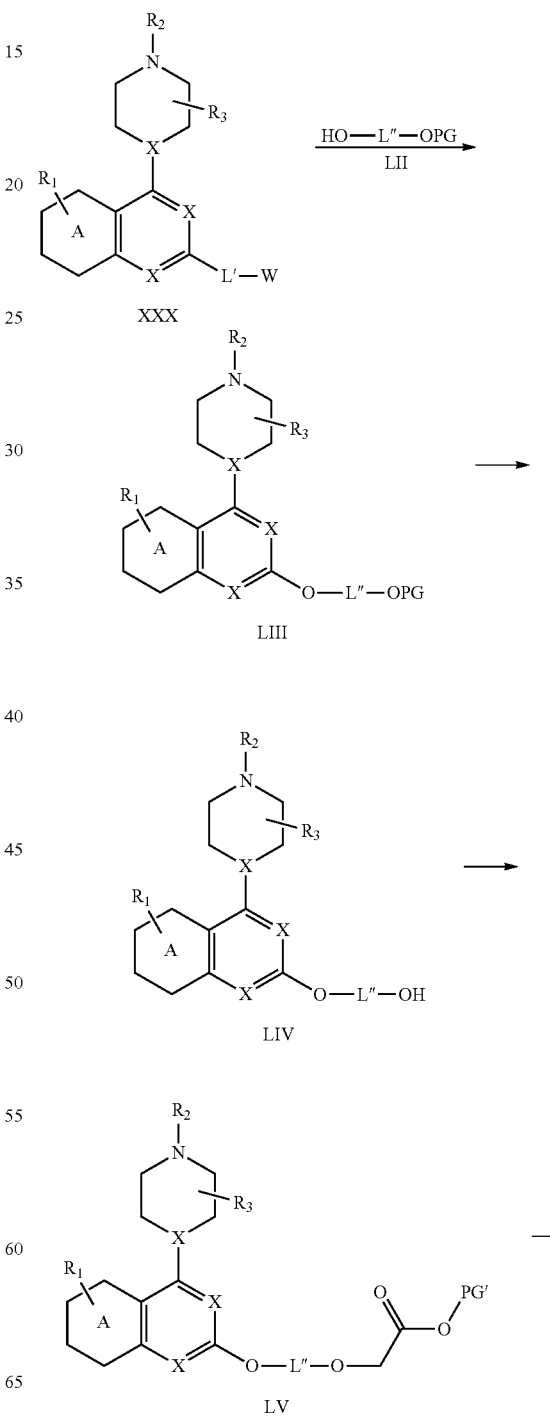

Scheme 17.

carbonyl. This compound where $R_2$ is H may then be converted to a different compound of formula LI under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

A compound of formula XLVIII may be reacted with a compound of formula V to prepare a compound of formula XLIX. Herein LG may be a suitable leaving group such as tosylate, bromide, or iodide; L is an optional linker; Y is a primary or secondary amine, which may be optionally substituted or cyclized into a 4- to 8-membered heterocyclic ring; PG is a suitable protecting group, including but not limited to t-butoxycarbonyl; and PG' is a suitable protecting group, including but not limited to 2-(trimethylsilyl)ethoxy]methyl. PG and PG' may then be removed simultaneously, using suitable conditions, such as hydrochloric acid in 1,4-dioxane, to afford a compound of formula L. A compound of formula L may then be reacted with a compound of formula XXX under reductive amination conditions, for example sodium triacetoxyborohydride and triethylamine in dichloromethane or sodium cyanoborohydride, sodium acetate, and acetic acid in dichloromethane and methanol to afford a compound of formula LI.

Herein,

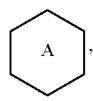

X, $R_1$, $R_2$, $R_3$, and L' are as defined in Scheme 1; and W is CHO. In cases where $R_2$ is a protecting group, the protecting group may be removed with suitable conditions, such as trifluoroacetic acid in dichloromethane when $R_2$ is t-butoxy-

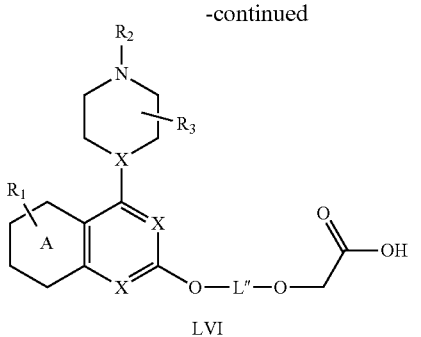

LVI

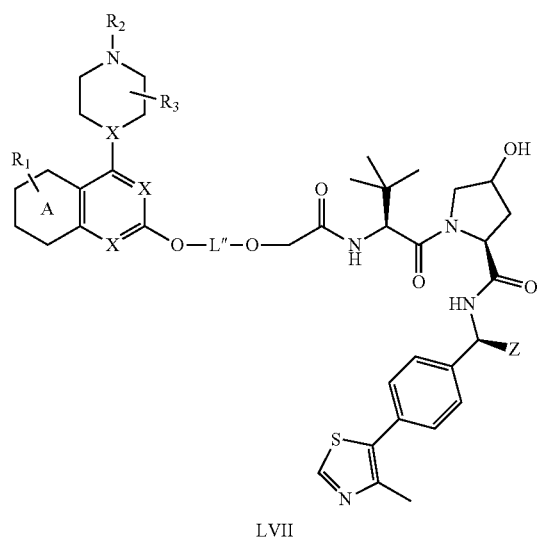

LVII

A compound of formula XXX may also be reacted with a compound of formula LII under conditions for a nucleophilic aromatic substitution reaction, e.g. sodium hydride in tetrahydrofuran at 20 to 50° C., to afford a compound of formula LIII. Herein, X and $R_3$ are as defined in Scheme 1;

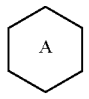

is an optionally substituted aliphatic cyclic amine; $R_1$ is a suitable protecting group on the amine group of

for example t-butoxycarbonyl; $R_2$ is a suitable protecting group, for example benzyloxycarbonyl; L' is absent; W is a suitable leaving group such as fluoride or chloride; L" is a linker; and PG is a suitable alcohol protecting group, for example tetrahydropyranyl. A compound of formula LIII may be transformed to a compound of formula LIV under conditions suitable for the removal of certain protecting groups, for example trifluoroacetic acid in dichloromethane when $R_1$ is t-butoxycarbonyl and PG is tetrahydropyranyl; in this case, $R_1$ of LIV becomes H. Such a compound of formula LIV may be transformed into a different compound of general formula LIV using conditions known to one skilled in the art. For example, by taking the compound LIV where $R_1$ is H and treating it with an aryl halide under conditions suitable for a Hartwig-Buchwald amination, e.g. (2-dicyclohexylphosphino-2',6'-diisopropoxy-1,1'-biphenyl)[2-(2'-amino-1,1'-biphenyl)]palladium(II) methanesulfonate and cesium carbonate in 1,4-dioxane at 90° C., a compound of formula LIV is obtained wherein $R_1$ is e.g. phenyl, napthalene, or heteroaryl, which may be independently multiply substituted with OH, CN, alkyl, and/or halogen. Further transformations of a compound LIV into a different compound LIV may be derived, for example, by changing the identity of the group $R_2$. For example, in the case where $R_2$ is benzyloxycarbonyl, it may be treated with e.g. $H_2$, palladium on carbon in methanol to afford the compound LIV where $R_2$ is H. This compound of formula LIV where $R_2$ is H may be transformed e.g. by treatment with di-t-butyldicarbonate and triethylamine in dichloromethane to another compound of formula LIV where $R_2$ is t-butoxycarbonyl; or e.g. by treatment with isocyanatotrimethylsilane and triethylamine in tetrahydrofuran to another compound of formula LIV where $R_2$ is $C(O)NH_2$. A suitably substituted compound of formula LIV may be converted to a compound of formula LV, wherein PG is a suitable protecting group such as ethyl, by treatment with a reagent such as ethyl diazoacetate and a catalyst such as rhodium (II) acetate in dichloromethane. A compound of formula LV may be transformed to a compound of formula LVI using conditions suitable for ester hydrolysis, such as lithium hydroxide in water and tetrahydrofuran. Finally, a compound of formula LVI may be reacted with a compound of formula VIII under conditions suitable for amine coupling, e.g. N-(3-dimethylaminopropyl)-N'-ethylcarbodiimide hydrochloride, 1-hydroxybenzotriazole, and diisopropylethylamine in N,N-dimethylformamide to afford a compound of formula LVII. Herein Z is an optional substituent, e.g. H, methyl, or hydroxymethyl.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula LVII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature. Alternatively this compound where $R_2$ is H may then be converted to a different compound of formula LVII under conditions for a urea formation. Representative conditions for such amide formations include, but are not limited to isocyanatotrimethylsilane and triethylamine in N,N-dimethylformamide at room temperature.

Scheme 18.

LIV → 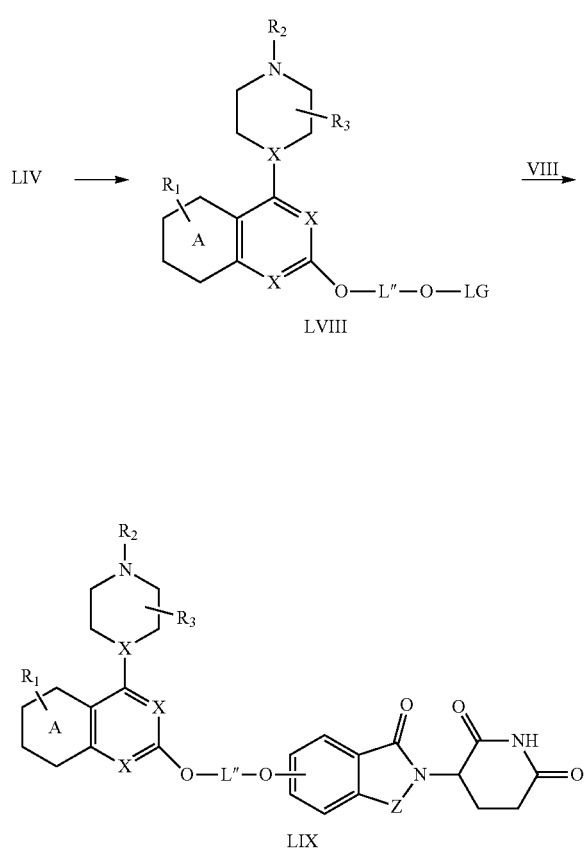

Alternatively, a compound of formula LIV may be converted into a compound of formula LVIII by treatment with a suitable reagent such as p-toluenesulfonyl chloride, triethylamine, and N,N-dimethylaminopyridine in dichloromethane.

Herein

$R_1$, $R_2$, $R_3$, and L" are as defined for LIV in Scheme 17; and LG is e.g. p-toluenesulfonate. A compound of formula LVIII may then be reacted with a compound of formula VIII under conditions suitable for nucleophilic substitution, e.g. potassium carbonate in N,N-dimethylformamide at 50° C. to afford a compound of formula LIX. Herein Z is C=O.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula LIX under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature. Alternatively this compound where $R_2$ is H may then be converted to a different compound of formula LIX under conditions for a urea formation. Representative conditions for such urea formations include, but are not limited to isocyanatotrimethylsilane and triethylamine in N,N-dimethylformamide at room temperature.

Scheme 19.

LVIII $\xrightarrow{XII}$

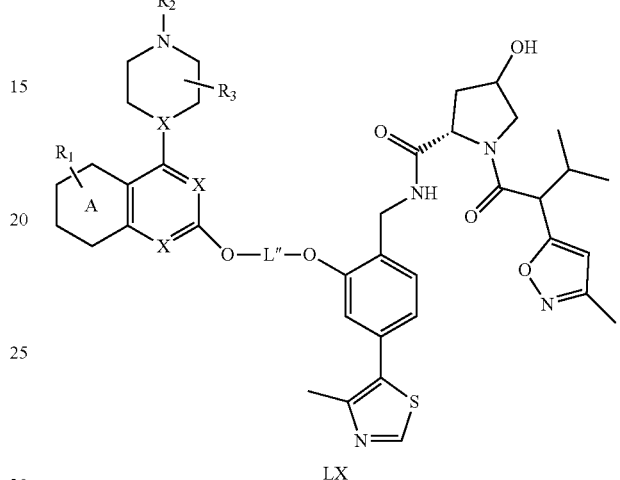

Alternatively, a compound of formula LVIII may be converted to a compound of formula LX by treatment with a compound of formula XII under conditions suitable for an alkylation reaction, for example potassium carbonate in N,N-dimethylformamide at 80° C.

Herein

$R_1$, $R_2$, $R_3$, and L" are as defined for LIV in Scheme 17.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula LX under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature. Alternatively this compound where $R_2$ is H may then be converted to a different compound of formula LX under conditions for a urea formation. Representative conditions for such urea formations include, but are not limited to isocyanatotrimethylsilane and triethylamine in N,N-dimethylformamide at room temperature.

Scheme 20.

Scheme 21.

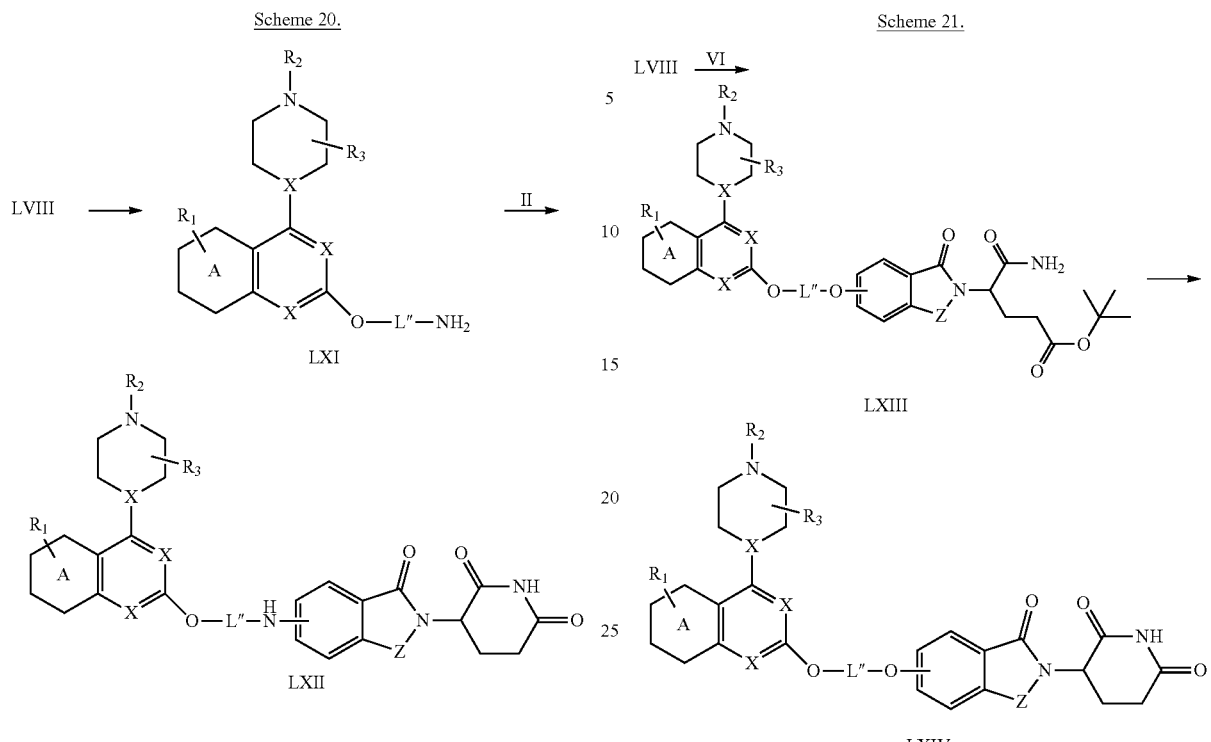

Alternatively, a compound of formula LVIII may be converted to a compound of formula LXI by treatment with an ammonia equivalent such as phthalimide potassium salt in N,N-dimethylformamide at 80° C. followed by treatment with e.g. hydrazine hydrate in ethanol at 70° C.

Herein

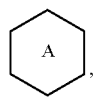, $R_1$, $R_2$, $R_3$, and L" are as defined for LIV in Scheme 17.

A compound of formula LXI may then be reacted with a compound of formula II under conditions suitable for nucleophilic aromatic substitution, e.g. diisopropylethylamine in dimethylsulfoxide at 90° C., to afford a compound of formula LXII. Herein Z is C=O.

In cases where $R_2$ is a protecting group, the protecting group may be removed with suitable conditions, such as trifluoroacetic acid in dichloromethane when $R_2$ is t-butoxycarbonyl. This compound where $R_2$ is H may then be converted to a different compound of formula LXII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature. Alternatively this compound where $R_2$ is H may then be converted to a different compound of formula LXII under conditions for a urea formation. Representative conditions for such urea formations include, but are not limited to isocyanatotrimethylsilane and triethylamine in N,N-dimethylformamide at room temperature.

Alternatively, a compound of formula LVIII may be reacted with a compound of formula VI to prepare a compound of formula LXIII under conditions suitable for nucleophilic substitution, e.g. potassium carbonate in N,N-dimethylformamide at 80° C.

Herein

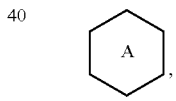, $R_1$, $R_2$, $R_3$, and L" are as defined for LIV in Scheme 17; and Z is $CH_2$.

A compound of formula LXIII may then be treated with a reagent to effect imide ring closure and concomitant removal of $R_2$ in cases where $R_2$ is t-butoxycarbonyl, e.g. benzenesulfonic acid in acetonitrile at reflux. In cases where $R_2$ is t-butoxycarbonyl in LVIII, $R_2$ thus becomes H in LXIV. This compound LXIV where $R_2$ is H may then be converted to a different compound of formula LXIV under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature. Alternatively this compound where $R_2$ is H may then be converted to a different compound of formula LXIV under conditions for a urea formation. Representative conditions for such urea formations include, but are not limited to isocyanatotrimethylsilane and triethylamine in N,N-dimethylformamide at room temperature.

Scheme 22.

LVIII $\xrightarrow{XXIV}$

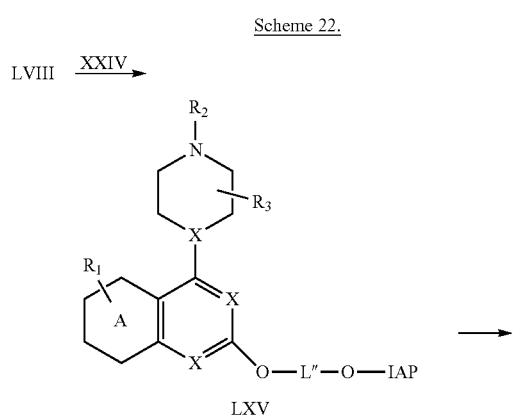

LXV

→

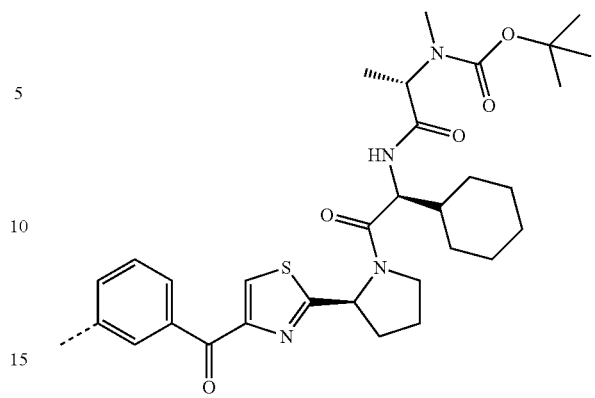

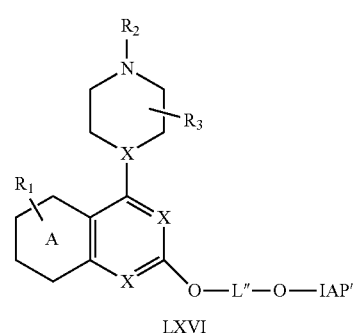

LXVI

Alternatively, a compound of formula LVIII may be converted to a compound of formula LXV by treatment with a compound of formula XXIV under conditions suitable for an alkylation reaction, for example potassium carbonate in acetonitrile at 80° C.

Herein

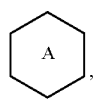

$R_1$, $R_2$, $R_3$, and L" are as defined for LIV in Scheme 17; and IAP is either:

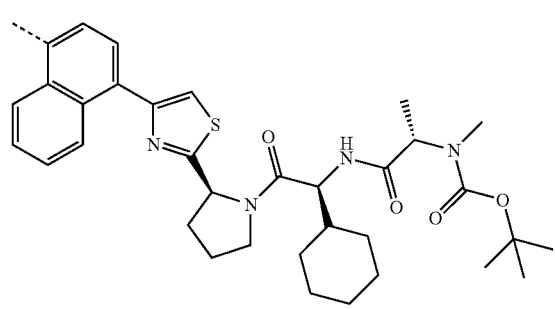

In cases where $R_2$ is a protecting group, the protecting group may be removed with suitable conditions, such as $H_2$, palladium on carbon in methanol when $R_2$ is benzyloxycarbonyl. This compound where $R_2$ is H may then be converted to a different compound of formula LXVI under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

A compound of formula LXV may subsequently be converted to a compound of formula LXVI by treatment with reagents suitable for the removal of a t-butoxycarbonyl protecting group, for example trifluoroacetic acid in dichloromethane. Herein IAP' is either:

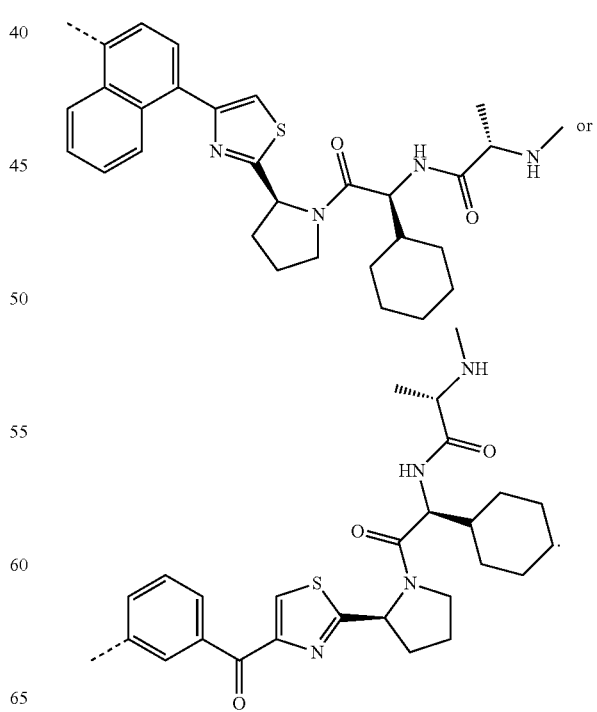

Scheme 23.

LXI $\xrightarrow{XXI}$

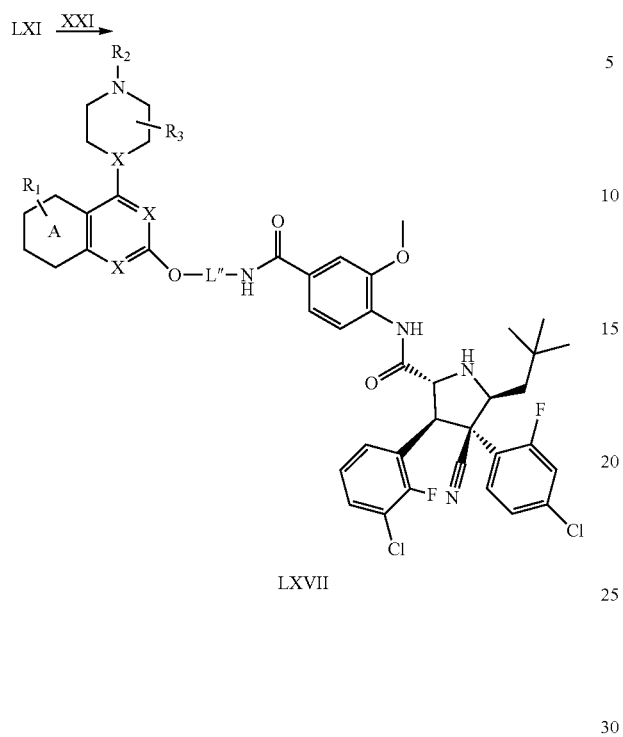

LXVII

A compound of formula LXI may alternatively be reacted with a compound of formula XXI under amide coupling conditions, e.g. N-(3-dimethylaminopropyl)-N'-ethylcarbodiimide hydrochloride, 1-hydroxybenzotriazole, and diisopropylethylamine in N,N-dimethylformamide to afford a compound of formula LXVII.

Herein

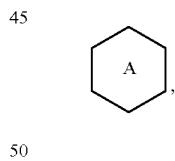

$R_1$, $R_2$, $R_3$, and L" are as defined for LIV in Scheme 17.

In cases where $R_2$ is a protecting group, the protecting group may be removed with suitable conditions, such as $H_2$, palladium on carbon in methanol when $R_2$ is benzyloxycarbonyl. This compound where $R_2$ is H may then be converted to a different compound of formula LXVII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

Scheme 24.

LVIII $\xrightarrow{XLVIII}$

LXVIII

Alternatively, a compound of formula LVIII may be converted to a compound of formula LXVIII by treatment with a compound of formula XLVIII under conditions suitable for an alkylation reaction, for example potassium carbonate in acetonitrile at 80° C.

Herein $R_1$, $R_2$, $R_3$, and L" are as defined for LIV in Scheme 17; and PG' is as defined in Scheme 16. In cases where $R_2$ is a protecting group, the protecting group may be removed with suitable conditions, such as hydrogen chloride in 1,4-dioxane; in cases where PG' is 2-(trimethylsilyl)ethoxymethyl, PG' becomes H under these conditions. This compound where PG' and $R_2$ are H may then be converted to a different compound of formula LXVIII under conditions for an amide coupling. Representative conditions for such amide formations include, but are not limited to: acryloyl chloride, 2,6-lutidine, dichloromethane, −78° C.; or a carboxylic acid such as 2,2-dihydroxyacetic acid, and 1-[bis(dimethylamino)methylene]-1H-1,2,3-triazolo[4,5-b]pyridinium 3-oxid hexafluorophosphate and diisopropylethylamine in N,N-dimethylformamide at room temperature.

General Synthetic Scheme 1.
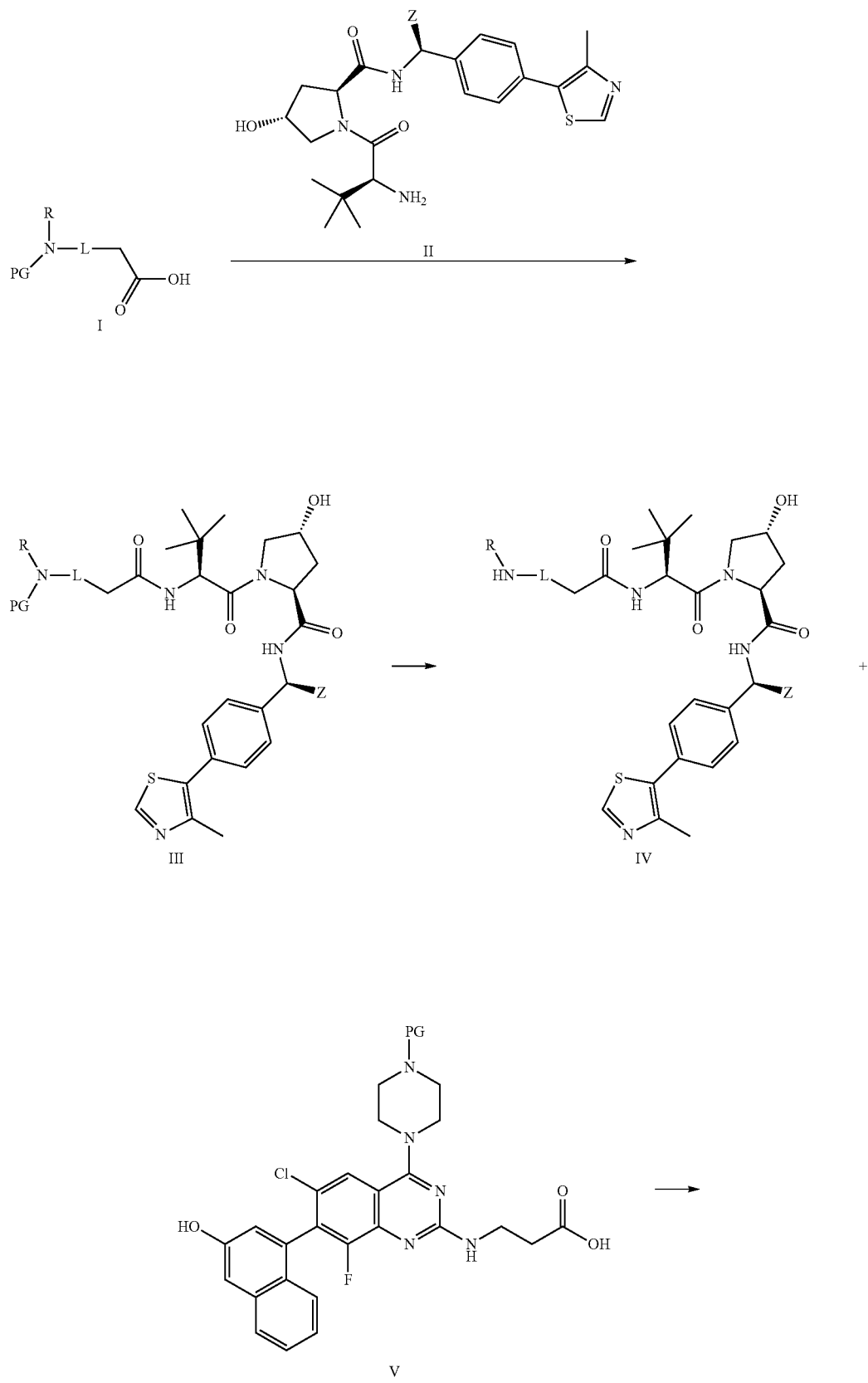

-continued
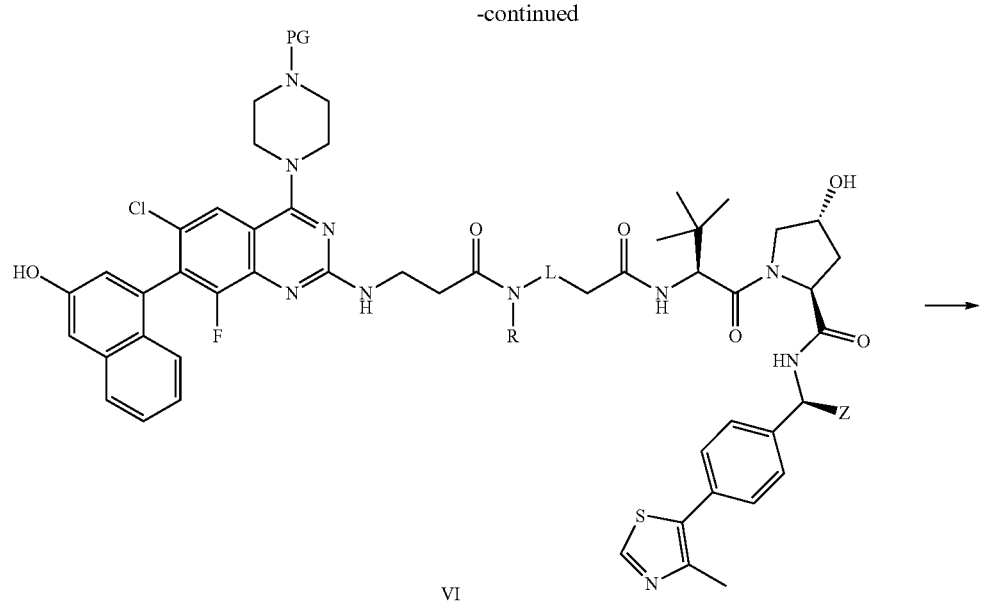
VI
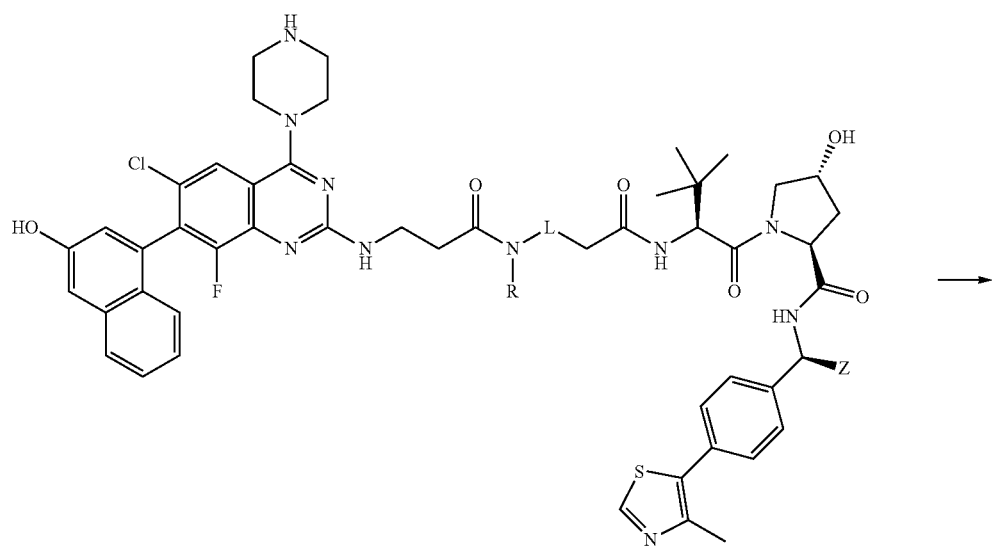
VII

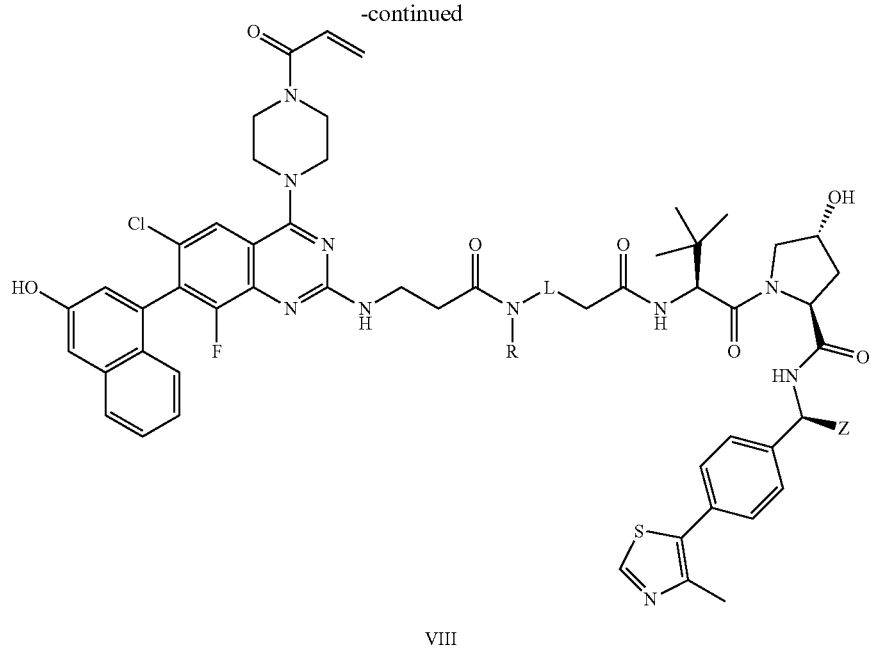

VIII

A compound of formula I (commercially available or readily prepared using standard reaction techniques known to one skilled in the art) may be reacted with a compound II under amide formation conditions, e.g. HOBt, EDCI, with a suitable base such as DIEA and a suitable solvent such as DMF to produce a compound of formula III. PG is a suitable protecting group, e.g. tert-butoxycarbonyl, R is H or an optional substituent, e.g. methyl, and Z is an optional substituent, e.g. H, methyl, or hydroxymethyl. A compound of formula III may be converted to a compound of formula IV using conditions suitable for the removal of a protecting group, e.g. hydrogen chloride in 1,4-dioxane in dichloromethane when PG is tert-butoxycarbonyl. A compound of formula IV may then be reacted with a compound of formula V under amide coupling conditions, e.g. analogous to those used for the conversion of I and II to III, to produce a compound of formula VI. Compounds VI may then be converted to compounds VII under suitable protecting group removal conditions, e.g. trifluoroacetic acid in dichloromethane. The compound VII may be converted to a compound of formula VIII under amide formation conditions, e.g. acryloyl chloride, 2,6-lutidine, dichloromethane.

General Synthetic Scheme 2.

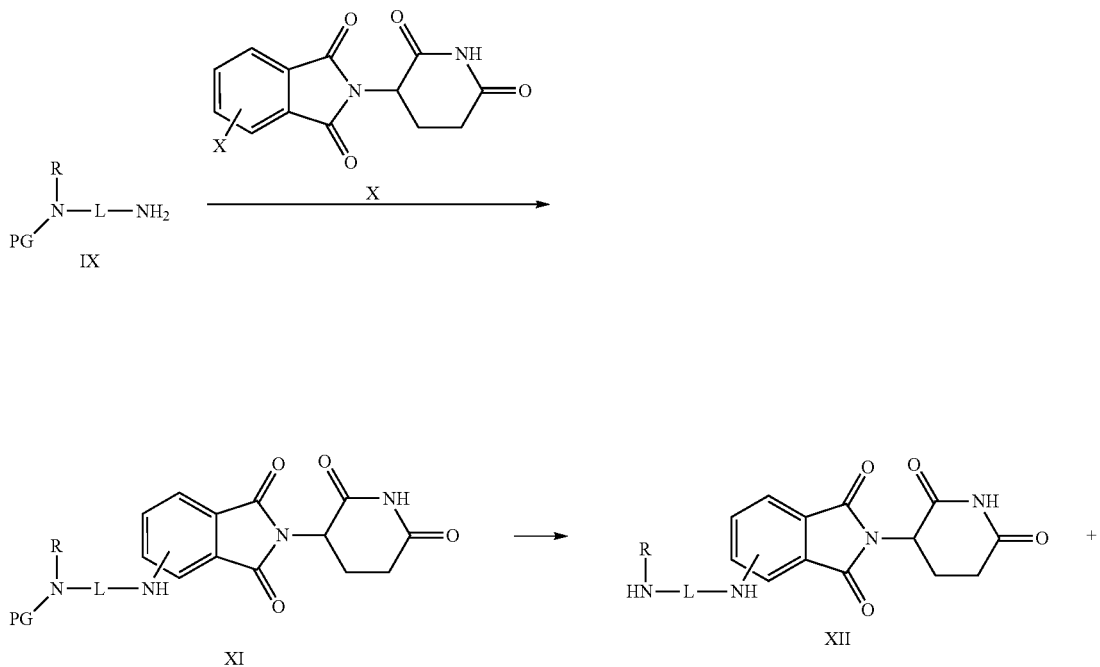

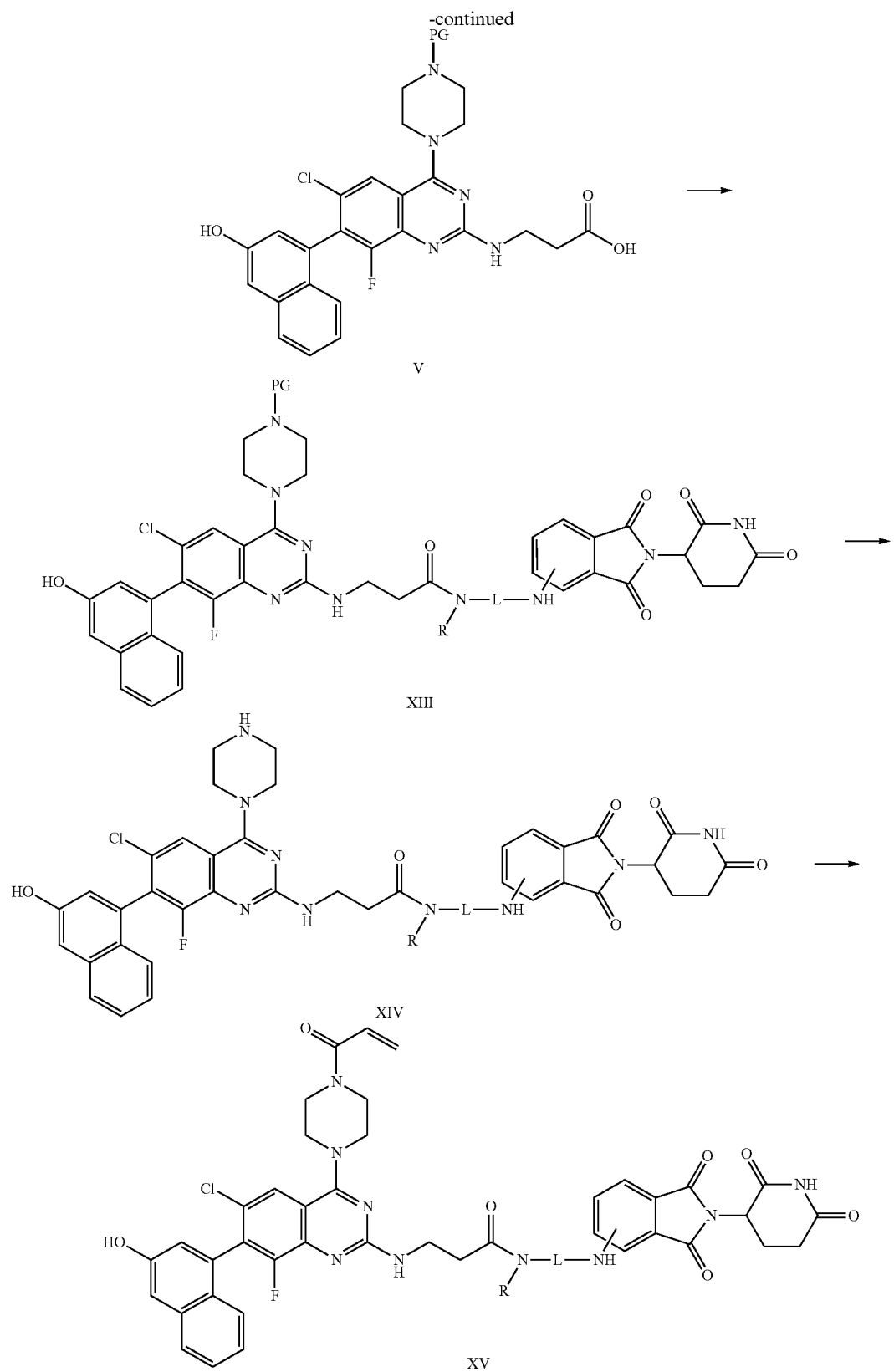
A compound of formula IX may be reacted with a compound of formula X to provide compounds of formula XI, wherein X is a suitable leaving group such as fluorine or chlorine, PG is a suitable protecting group, e.g. tert-butoxycarbonyl, R is H or an optional substituent, e.g. methyl, and reaction conditions are those for a nucleophilic aromatic substitution, e.g. DIEA, DMSO, 80° C. A compound of formula XI may be converted to a compound of formula XII using conditions suitable for the removal of a protecting group, e.g. hydrogen chloride in 1,4-dioxane in dichloromethane when PG is tert-butoxycarbonyl. A compound of formula XI may then be reacted with a compound of formula V under amide coupling conditions, e.g. HOBt, EDCI, with a suitable base such as DIEA and a suitable solvent such as DMF, to produce a compound of formula XIII. Compound XIII may then be converted to compound XIV under suitable protecting group removal conditions, e.g. trifluoroacetic acid in dichloromethane. The compound XIV may be converted to a compound of formula XV under amide formation conditions, e.g. acryloyl chloride, 2,6-lutidine, dichloromethane.

Exemplary Synthesis of 2-(2,6-dioxopiperidin-3-yl)-5-hydroxyisoindoline-1,3-dione Step 1: Preparation of 2-(2,6-dioxopiperidin-3-yl)-5-hydroxyisoindoline-1,3-dione

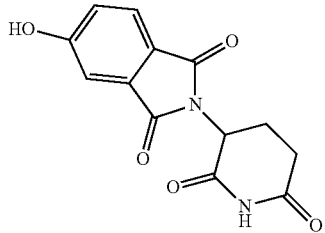 [SMILES: O=C1CCC(N2C(=O)c3ccc(O)cc3C2=O)C(=O)N1]

A solution of 3-aminopiperidine-2,6-dione (4.1 g, 24.7 mmol, 1.50 eq, HCl salt) in acetic acid (45 mL) was charged with sodium acetate (4.1 g, 49.4 mmol, 3.00 eq), then the mixture was stirred at 25° C. for 1 hour. Then 4-hydroxyphthalic acid (3.0 g, 16.5 mmol, 1.00 eq) was added into the mixture and heated to 120° C., stirred for additional 11 hours. The mixture was concentrated and then poured into water (20 mL), and then filtered. The crude product was purified by column chromatography (dichloromethane:methanol=50:1 to 10:1) to afford 2-(2,6-dioxo-3-piperidyl)-5-hydroxy-isoindoline-1,3-dione (3.9 g, 14.3 mmol, 86% yield) as a colorless solid. LC/MS (ESI) m/z: 275 [M+1]$^+$; $^1$H-NMR (400 MHz, CDCl$_3$) δ 11.19-10.94 (m, 2H), 7.75 (d, J=8.0 Hz, 1H), 7.20-7.08 (m, 2H), 5.08 (dd, J=5.2, 12.8 Hz, 1H), 3.34 (br s, 1H), 2.95-2.81 (m, 1H), 2.64-2.55 (m, 1H), 2.08-1.98 (m, 1H).

Exemplary Synthesis of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride Step 1: Preparation of tert-butyl (S)-(1-(4-bromophenyl)ethyl)carbamate

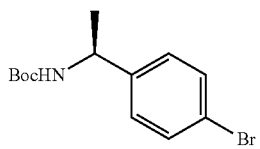 [SMILES: C[C@H](NC(=O)OC(C)(C)C)c1ccc(Br)cc1]

Into a 250-mL round-bottom flask, was placed (1S)-1-(4-bromophenyl)ethan-1-amine (10.0 g, 49.98 mmol, 1.00 equiv) in dichloromethane (100 mL), triethylamine (10.0 g, 99.01 mmol, 2.00 equiv), di-tert-butyl dicarbonate (13.0 g, 59.63 mmol, 1.20 equiv). The resulting solution was stirred for 2 hours at room temperature. The resulting mixture was concentrated under vacuum. The residue was applied onto a silica gel column with ethyl acetate/petroleum ether (1:10). This resulted in 15.0 g of tert-butyl N-[(1S)-1-(4-bromophenyl)ethyl]carbamate as a white solid.

Step 2: Preparation of tert-butyl (S)-(1-(4-(4-methylthiazol-5-yl)phenyl)ethyl)carbamate

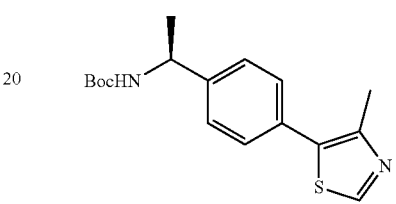

Into a 250-mL round-bottom flask purged and maintained with an inert atmosphere of nitrogen, was placed a solution of tert-butyl N-[(1S)-1-(4-bromophenyl)ethyl]carbamate (15.0 g, 49.97 mmol, 1.00 equiv) in N,N-Dimethylacetamide (100 mL), 4-methyl-1,3-thiazole (9.9 g, 99.84 mmol, 2.00 equiv), potassium acetate (9.8 g, 99.86 mmol, 2.00 equiv), palladium(II) acetate (112.5 mg, 0.50 mmol, 0.01 equiv). The resulting solution was stirred for 2 hours at 120° C. The reaction mixture was quenched by the addition of water (500 mL). The resulting solution was extracted with ethyl acetate (200 mL×3) and the organic layers combined and concentrated under vacuum. The residue was applied onto a silica gel column with ethyl acetate/petroleum ether (1:5). This resulted in 7.5 g (47%) of tert-butyl N-[(1S)-1-[4-(4-methyl-1,3-thiazol-5-yl)phenyl]ethyl]carbamate as a white solid. LC/MS (ESI) m/z: 319.13 [M+Na]$^+$.

Step 3: Preparation of (S)-1-(4-(4-methylthiazol-5-yl)phenyl)ethan-1-amine hydrochloride

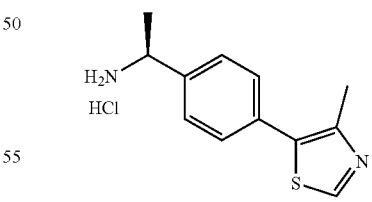

Into a 100-mL round-bottom flask, was placed a solution of tert-butyl N-[(1S)-1-[4-(4-methyl-1,3-thiazol-5-yl)phenyl]ethyl]carbamate (7.5 g, 23.55 mmol, 1.00 equiv) in methanol (20 mL), hydrogen chloride (gas) was bubbled in at room temperature. The resulting solution was stirred for 2 hours at room temperature. The resulting mixture was concentrated under vacuum. This resulted in 4.4 g (86%) of (1S)-1-[4-(4-methyl-1,3-thiazol-5-yl)phenyl]ethan-1-amine as a white solid.

Step 4: Preparation of tert-butyl (2S,4R)-4-hydroxy-2-(((S)-1-(4-(4-methylthiazol-5-yl)phenyl)ethyl)carbamoyl)pyrrolidine-1-carboxylate

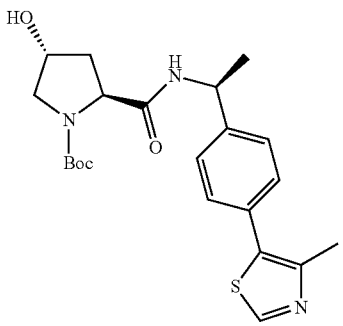 [SMILES: Cc1ncsc1-c1ccc([C@H](C)NC(=O)[C@@H]2C[C@@H](O)CN2C(=O)OC(C)(C)C)cc1]

Into a 100-mL round-bottom flask, was placed (2S,4R)-1-[(tert-butoxy)carbonyl]-4-hydroxypyrrolidine-2-carboxylic acid (4.7 g, 20.32 mmol, 1.00 equiv) in N,N-dimethylformamide (20 mL), N-ethyl-N-isopropylpropan-2-amine (7.8 g, 60.35 mmol, 3.00 equiv), o-(7-Azabenzotriazol-1-yl)-N,N,N',N'-te-tramethyluronium hexafluorophosphate (11.5 g, 30.26 mmol, 1.50 equiv), (1S)-1-[4-(4-methyl-1,3-thiazol-5-yl)phenyl]ethan-1-amine (4.4 g, 20.15 mmol, 1.00 equiv). The resulting solution was stirred for 12 hours at room temperature. The reaction mixture was quenched by the addition of water (20 mL). The resulting solution was extracted with ethyl acetate (100 mL×3) and the organic layers combined and dried in an oven under reduced pressure, concentrated under vacuum. The residue was applied onto a silica gel column with ethyl acetate/petroleum ether (1:1). This resulted in 5.0 g (57%) of tert-butyl (2S,4R)-4-hydroxy-2-[[(1S)-1-[4-(4-methyl-1,3-thiazol-5-yl)phenyl]ethyl]carbamoyl]pyrrolidine-1-carboxylate as a yellow solid. LC/MS (ESI) m/z: 432.15 [M+1]⁺.

Step 5: Preparation of (2S,4R)-4-hydroxy-N—((S)-1-(4-(4-methylthiazol-5-yl)phenyl)ethyl)pyrrolidine-2-carboxamide hydrochloride

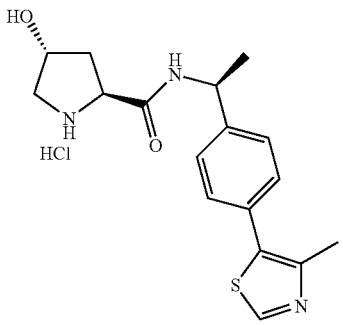 [SMILES: Cc1ncsc1-c1ccc([C@H](C)NC(=O)[C@@H]2C[C@@H](O)CN2)cc1 ; Cl]

Into a 500-mL round-bottom flask, was placed a solution of tert-butyl (2S,4R)-4-hydroxy-2-[[(1S)-1-[4-(4-methyl-1,3-thiazol-5-yl)phenyl]ethyl]carbamoyl]pyrrolidine-1-carboxylate (5.0 g, 11.59 mmol, 1.00 equiv) in methanol (200 mL), then hydrogen chloride (gas) was bubbled into the reaction mixture for 2 hours at room temperature. The resulting mixture was concentrated under vacuum. This resulted in 3.2 g (83%) of (2S,4R)-4-hydroxy-N-[(1S)-1-[4-(4-methyl-1,3-thiazol-5-yl)phenyl]ethyl]pyrrolidine-2-carboxamide as a red solid.

Step 6: Preparation of tert-butyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate

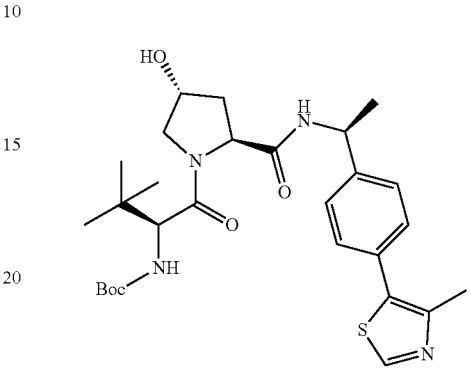

Into a 25-mL round-bottom flask, was placed (2S)-2-[(tert-butoxy)carbonyl]amino-3,3-dimethylbutanoic acid (2.0 g, 8.65 mmol, 0.99 equiv) in N,N-dimethylformamide (30 mL). N-ethyl-N-isopropylpropan-2-amine (3.4 g, 3.00 equiv), o-(7-Azabenazotriazol-1-yl)-N,N,N',N'-te-tramethyluronium hexafluorophosphate (5.0 g, 1.50 equiv), (2S,4R)-4-hydroxy-N-[(1S)-1-[4-(4-methyl-1,3-thiazol-5-yl)phenyl]ethyl]pyrrolidine-2-carboxamide hydrochloride (3.2 g, 8.70 mmol, 1.00 equiv). The resulting solution was stirred for 12 hours at room temperature. The resulting solution was extracted with ethyl acetate (60 mL×3) and washed with water (100 mL×2). The organic layers combined and dried, concentrated under vacuum. The residue was applied onto a silica gel column with ethyl acetate/petroleum ether (1:3). This resulted in 4.0 g (84%) of tert-butyl N-[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate as a yellow solid. LC/MS (ESI) m/z: 545.30 [M+1]⁺.

Step 7: Preparation of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride

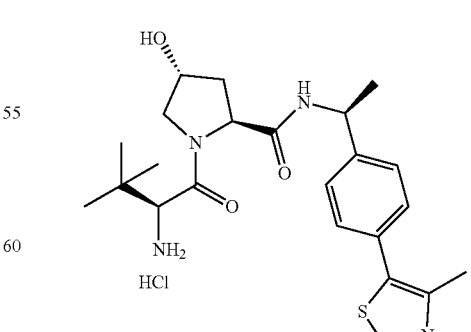

Into a 100-mL round-bottom flask, was placed a solution of tert-butyl N-[(2S)-1-[(2S,4R)-4-hydroxy-2-[[(1S)-1-[4-

(4-methyl-1,3-thiazol-5-yl)phenyl]ethyl]carbamoyl]pyrrolidin-1-yl]-3,3-dimethyl-1-oxobutan-2-yl]carbamate (4.0 g, 7.34 mmol, 1.00 equiv) in methanol (30 mL), then hydrogen chloride (gas) was bubbled into the reaction mixture for 2 hours at room temperature. The resulting mixture was concentrated under vacuum. This resulted in 3.5 g of (2S,4R)-1-[(2S)-2-amino-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride as a yellow solid. LC/MS (ESI) m/z: 445.05 [M+1]$^+$; $^1$H-NMR (400 MHz, DMSO-d$_6$) δ 8.99 (s, 1H), 8.57-8.55 (d, J=7.8 Hz, 1H), 8.01 (b, 3H), 7.46-7.43 (d, J=8.4 Hz, 2H), 7.39-7.37 (d, J=8.4 Hz, 2H), 4.98-4.90 (m, 1H), 4.57-4.51 (m, 1H), 4.34 (b, 1H), 3.94-3.92 (m, 1H), 3.69-3.66 (m, 1H), 3.53-3.49 (m, 1H), 2.52 (s, 3H), 2.10-2.07 (m, 1H), 1.83-1.81 (m, 1H), 1.40-1.30 (m, 3H), 1.03 (s, 9H).

Exemplary Synthesis of 3-((4-(4-acetylpiperazin-1-yl)-6-chloro-8-fluoro-7-(3-hydroxynaphthalen-1-yl) quinazolin-2-yl)amino)propanoic acid Step 1: Preparation of 2-amino-4-bromo-5-chloro-3-fluorobenzoic acid

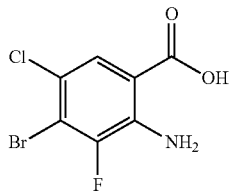 [SMILES: Nc1c(C(=O)O)cc(Cl)c(Br)c1F]

To a solution of 2-amino-4-bromo-3-fluorobenzoic acid (9.0 g, 38.5 mmol) in N,N-dimethylformamide (180 mL) was added N-Chlorosuccinimide (6.2 g, 46.2 mmol) and stirred at 70° C. overnight. After cooling to room temperature, the reaction mixture was poured into water (100 mL). The precipitate was collected through filtration, and the filter cake was washed with water and dried in vacuo to afford 2-amino-4-bromo-5-chloro-3-fluorobenzoic acid (9.0 g, 87%) as a yellow solid. LC/MS (ESI) m/z: 268.0 [M+1]$^+$; $^1$H-NMR (400 MHz, DMSO-d$_6$) δ 6.90 (br, 2H), 7.69 (d, J=2.0 Hz, 1H).

Step 2: Preparation of 7-bromo-6-chloro-8-fluoro-quinazoline-2,4(1H,3H)-dione

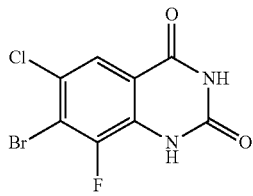

A mixture 2-amino-4-bromo-5-chloro-3-fluorobenzoic acid (2.0 g, 7.5 mmol) and urea (2.2 g, 37.3 mmol) was mixed uniformly at room temperature and stirred at 240° C. for 2 hours. After cooling to 100° C., water (30 mL) was added to and the resulting mixture was stirred at 100° C. for 30 minutes. The precipitate was collected through filtration, and the filter cake was washed with boiling water three times and dried in vacuo to afford 7-bromo-6-chloro-8-fluoroquinazoline-2,4(1H,3H)-dione (2.1 g, 95%) as a yellow solid. LC/MS (ESI) m/z: 293.6 [M+1]$^+$; $^1$H-NMR (400 MHz, DMSO-d$_6$) δ 7.82 (d, J=1.6 Hz, 1H), 11.65 (br, 2H).

Step 3: Preparation of 7-bromo-2,4,6-trichloro-8-fluoroquinazoline

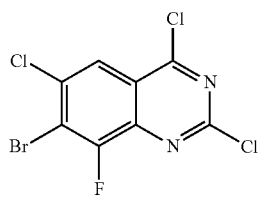 [SMILES: Fc1c(Br)c(Cl)cc2c(Cl)nc(Cl)nc12]

To a suspension of 7-bromo-6-chloro-8-fluoroquinazoline-2,4(1H,3H)-dione (500 mg, 1.7 mmol) in phosphorus oxychloride (7.5 mL) was added N-ethyl-N-isopropylpropan-2-amine (550 mg, 4.3 mmol) and refluxed overnight. The volatiles were evaporated under reduced pressure to give a residue which was purified by silica gel flash chromatography (2% ethyl acetate in hexane) to afford 7-bromo-2,4,6-trichloro-8-fluoroquinazoline (400 mg, 71%) as a yellow solid. $^1$H-NMR (400 MHz, CDCl$_3$) δ 8.21 (d, J=2.0 Hz, 1H).

Step 4: Preparation of tert-butyl 4-(7-bromo-2,6-dichloro-8-fluoroquinazolin-4-yl)piperazine-1-carboxylate

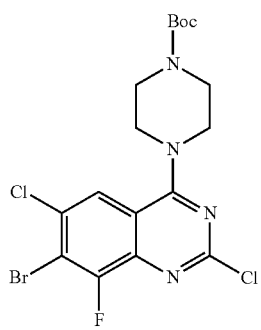 [SMILES: CC(C)(C)OC(=O)N1CCN(c2nc(Cl)nc3c(F)c(Br)c(Cl)cc23)CC1]

To a solution of 7-bromo-2,4,6-trichloro-8-fluoroquinazoline (400 mg, 1.2 mmol) and triethylamine (364 mg, 3.6 mmol) in 1,4-dioxane (6 mL) was added tert-butyl piperazine-1-carboxylate (236 mg, 1.27 mmol) at room temperature and stirred at 50° C. for 30 minutes. The reaction mixture was quenched with water (15 mL) and extracted with dichloromethane (10 mL×2). The combined organic layers were washed with brine (10 ml), dried over anhydrous sodium sulfate, and concentrated under reduced pressure to give a residue which was purified by silica gel flash chromatography (eluted with 3%-30% ethyl acetate in hexane) to afford tert-butyl 4-(7-bromo-2,6-dichloro-8-fluoroquinazolin-4-yl)piperazine-1-carboxylate (520 mg, 90%) as a yellow solid. LC/MS (ESI) m/z: 479.0/481.0 [M+1]$^+$; $^1$H-NMR (400 MHz, CDCl$_3$) δ 1.50 (s, 9H), 3.69-3.62 (m, 4H), 3.94-3.85 (m, 4H), 7.77 (d, J=2.0 Hz, 1H).

Step 5: Preparation of tert-butyl 4-(7-bromo-6-chloro-2-((3-ethoxy-3-oxopropyl)amino)-8-fluoro-quinazolin-4-yl)piperazine-1-carboxylate

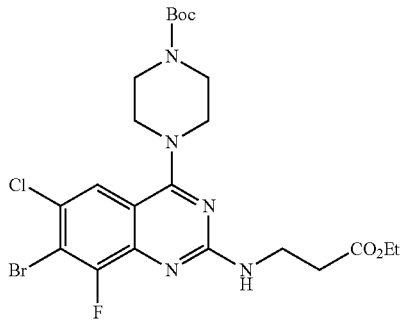 [SMILES: CCOC(=O)CCNc1nc(N2CCN(C(=O)OC(C)(C)C)CC2)c2cc(Cl)c(Br)c(F)c2n1]

To a solution of tert-butyl 4-(7-bromo-2,6-dichloro-8-fluoroquinazolin-4-yl) piperazine-1-carboxylate (100 mg, 0.2 mmol) in isopropanol (3 mL) were added ethyl 3-aminopropanoate hydrochloride (91.8 mg, 0.6 mmol) and N-ethyl-N-isopropylpropan-2-amine (78 mg, 0.6 mmol) and refluxed for 20 hours. The reaction mixture was partitioned between ethyl acetate (20 ml) and water (10 ml). The organic layer was collected, and the aqueous layer was extracted with ethyl acetate (15 ml×2). The combined organic layers were washed with brine (10 ml), dried over anhydrous sodium sulfate, and concentrated under reduced pressure to give a residue which was purified by silica gel flash chromatography (eluted with 10%-50% ethyl acetate in hexane) to afford tert-butyl 4-(7-bromo-6-chloro-2-((3-ethoxy-3-oxopropyl)amino)-8-fluoroquin azolin-4-yl) piperazine-1-carboxylate (95 mg, 81%) as a colorless oil. $^1$H-NMR (400 MHz, CDCl$_3$) δ 1.27 (t, J=7.2 Hz, 3H), 1.49 (s, 9H), 2.60-2.70 (m, 2H), 3.55-3.70 (m, 8H), 3.84-3.75 (m, 2H), 4.16 (q, J=7.2 Hz, 2H), 5.67 (br, 1H), 7.57 (d, J=2.0 Hz, 1H).

Step 6: Preparation of tert-butyl 4-(6-chloro-2-((3-ethoxy-3-oxopropyl)amino)-8-fluoro-7-(3-(methoxymethoxy)naphthalen-1-yl)quinazolin-4-yl) piperazine-1-carboxylate

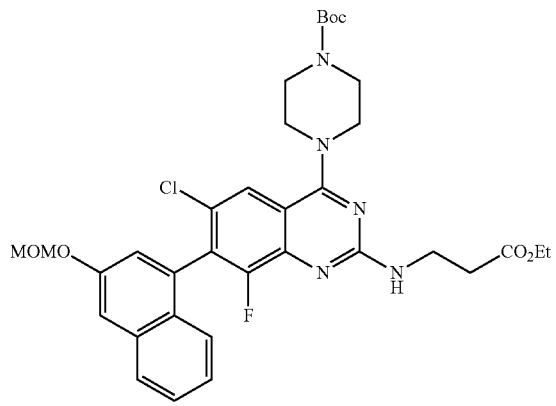

To a solution of tert-butyl 4-(7-bromo-6-chloro-2-((3-ethoxy-3-oxopropyl)amino)-8-fluoroquinazolin-4-yl)piperazine-1-carboxylate (820 mg, 1.46 mmol) in 1,4-dioxane (16.5 mL) and water (4 mL) were added 2-(3-(methoxymethoxy)naphthalene-1-yl)-4,4,5,5-tetramethyl-1,3,2-dioxaborolane (550 mg, 1.75 mmol), sodium carbonate (387 mg, 3.65 mmol) and 1,1'-Bis(diphenylphosphino)ferrocene palladium(II)dichloride (110 mg, 0.15 mmol) at room temperature under nitrogen atmosphere; the mixture was degassed with nitrogen three times. The resulting mixture was refluxed for 2 hours. The reaction mixture was partitioned between ethyl acetate (30 ml) and water (20 ml); the organic layer was collected and the aqueous layer was extracted with ethyl acetate (20 ml×2). The combined organic layers were washed with brine (40 ml), dried over anhydrous sodium sulfate, and concentrated under reduced pressure to give a crude residue which was purified by silica gel flash chromatography (eluted with 10-33% ethyl acetate in hexane) to afford tert-butyl 4-(6-chloro-2-((3-ethoxy-3-oxopropyl)amino)-8-fluoro-7-(3-(methoxy methoxy)naphthalen-1-yl)quinazolin-4-yl)piperazine-1-carboxylate (940 mg, 78%) as a white foam. LC/MS (ESI) m/z: 668.4 [M+1]$^+$; $^1$H-NMR (400 MHz, CDCl$_3$) δ 1.26 (t, J=7.2 Hz, 3H), 1.51 (s, 9H), 2.67 (t, J=6.0 Hz, 2H), 3.55 (s, 3H), 3.62-3.75 (m, 8H), 3.79-3.83 (m, 2H), 4.16 (q, J=7.2 Hz, 2H), 5.38-5.29 (m, 2H), 5.57-5.65 (m, 1H), 7.19 (d, J=2.4 Hz, 1H), 7.30-7.26 (m, 1H), 7.37 (d, J=8.4 Hz, 1H), 7.49-7.42 (m, 1H), 7.52 (d, J=2.4 Hz, 1H), 7.66 (d, J=1.4 Hz, 1H), 7.82 (d, J=8.2 Hz, 1H).

Step 7: Preparation of ethyl 3-((6-chloro-8-fluoro-7-(3-hydroxynaphthalen-1-yl)-4-(piperazin-1-yl)quinazolin-2-yl)amino)propanoate hydrochloride

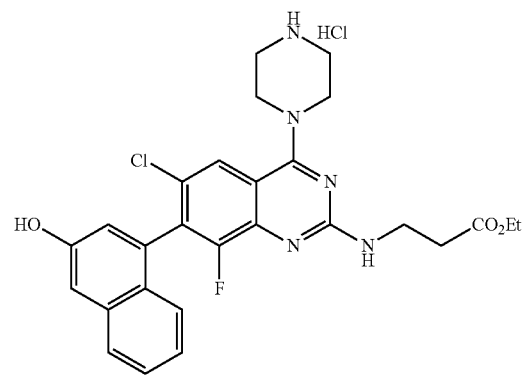 [SMILES: CCOC(=O)CCNc1nc(N2CCNCC2)c2cc(Cl)c(-c3cc(O)cc4ccccc34)c(F)c2n1 ; Cl]

To a solution of tert-butyl 4-(6-chloro-2-((3-ethoxy-3-oxopropyl)amino)-8-fluoro-7-(3-(methoxymethoxy)naphthalen-1-yl)quinazolin-4-yl)piperazine-1-carboxylate (940 mg, 1.4 mmol) in ethanol (10 mL) was added hydrogen chloride in dioxane (10 mL, 4 M) at room temperature and stirred overnight. The volatiles were evaporated under reduced pressure to give ethyl 3-((6-chloro-8-fluoro-7-(3-hydroxynaphthalen-1-yl)-4-(piperazin-1-yl) quinazolin-2-yl)amino)propanoate hydrochloride (1.4 mmol). LC/MS (ESI) m/z: 524.4 [M+1]$^+$.

Step 8: Preparation of ethyl 3-((7-(3-acetoxynaphthalen-1-yl)-4-(4-acetylpiperazin-1-yl)-6-chloro-8-fluoroquinazolin-2-yl)amino)propanoate

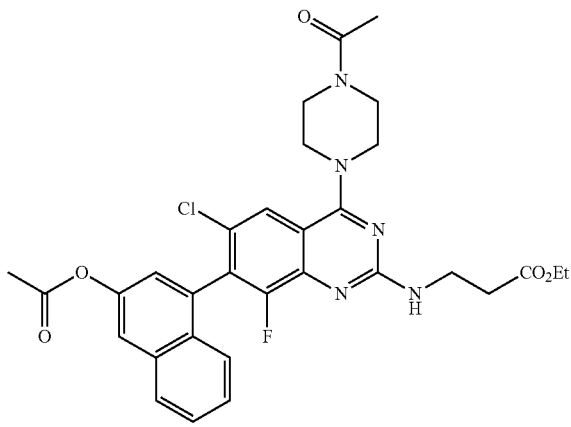 [SMILES: CCOC(=O)CCNc1nc(N2CCN(C(C)=O)CC2)c2cc(Cl)c(-c3cc(OC(C)=O)cc4ccccc34)c(F)c2n1]

To a suspension of ethyl 3-((6-chloro-8-fluoro-7-(3-hydroxynaphthalen-1-yl)-4-(piperazin-1-yl)quinazolin-2-yl)amino)propanoate hydrochloride (1.4 mmol) in dichloromethane (30 mL) were added triethylamine (850 mg, 8.4 mmol) and acetyl chloride (328 mg, 4.2 mmol) at room temperature and stirred 1 hour. The reaction mixture was concentrated in vacuo to give residue which was purified by silica gel column (eluted with 2% methanol in dichloromethane) to afford ethyl 3-((7-(3-acetoxynaphthalen-1-yl)-4-(4-acetylpiperazin-1-yl)-6-chloro-8-fluoroquinazolin-2-yl)amino)propanoate (735 mg, two steps yield 86%) as light yellow oil. LC/MS (ESI) m/z: 608.7 [M+1]$^+$; $^1$H-NMR (400 MHz, CDCl$_3$) δ 1.26 (t, J=7.2 Hz, 3H), 2.18 (s, 3H), 2.36 (s, 3H), 2.67 (t, J=6.0 Hz, 2H), 3.66-3.88 (m, 10H), 4.17 (q, J=7.2 Hz, 2H), 5.64 (t, J=5.2 Hz, 1H), 7.23 (d, J=2.4 Hz, 1H), 7.43-7.36 (m, 1H), 7.45 (d, J=8.2 Hz, 1H), 7.49-7.53 (m, 1H), 7.66 (d, J=1.6 Hz, 1H), 7.73 (d, J=2.2 Hz, 1H), 7.89 (d, J=8.2 Hz, 1H).

Step 9: Preparation of 3-((4-(4-acetylpiperazin-1-yl)-6-chloro-8-fluoro-7-(3-hydroxynaphthalen-1-yl)quinazolin-2-yl)amino)propanoic acid

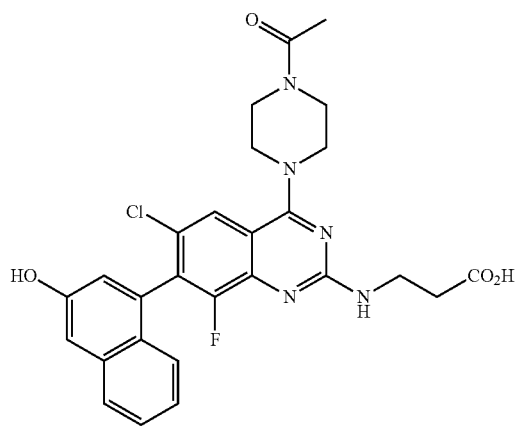 [SMILES: CC(=O)N1CCN(c2nc(NCCC(=O)O)nc3c(F)c(-c4cc(O)cc5ccccc45)c(Cl)cc23)CC1]

To a solution of ethyl 3-((7-(3-acetoxynaphthalen-1-yl)-4-(4-acetylpiperazin-1-yl)-6-chloro-8-fluoroquinazolin-2-yl)amino)propanoate (735 mg, 1.2 mmol) in tetrahydrofuran (6 ml)-water (2 ml) was added lithium hydroxide monohydrate (241 mg, 6.0 mmol) at room temperature and stirred for 2 hours. The mixture solution was cooled to room temperature, acidified with diluted hydrochloride acid (3N) till pH 3-4, and extracted with dichloromethane (10 ml×2). The organic layers were combined, washed with brine (10 ml), dried over sodium sulfate and concentrated under reduced pressure to afford 3-((4-(4-acetylpiperazin-1-yl)-6-chloro-8-fluoro-7-(3-hydroxynaphthalen-1-yl)quinazolin-2-yl)amino)propanoic acid as a white solid (470 mg, 78%). LC/MS (ESI) m/z: 538.3 [M+1]$^+$; $^1$H-NMR (400 MHz, DMSO-d$_6$) δ 2.07 (s, 3H), 2.55-2.65 (m, 2H), 3.45-3.85 (m, 8H), 4.19-3.88 (m, 2H), 7.07 (s, 1H), 7.17-7.35 (m, 3H), 7.53-7.38 (m, 1H), 7.70-8.10 (m, 2H), 10.22-9.94 (m, 1H), 12.33 (br, 1H).

Exemplary Synthesis of 3-((4-(4-acryloylpiperazin-1-yl)-6-chloro-8-fluoro-7-(3-hydroxynaphthalen-1-yl)quinazolin-2-yl)amino)propanoic acid

Step 1: Preparation of ethyl 3-((4-(4-acryloylpiperazin-1-yl)-6-chloro-8-fluoro-7-(3-hydroxynaphthalen-1-yl)quinazolin-2-yl)amino)propanoate

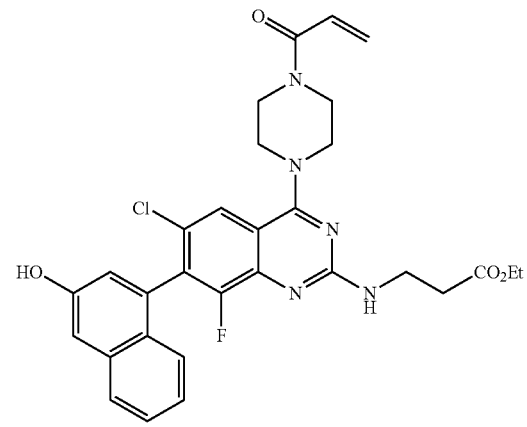 [SMILES: C=CC(=O)N1CCN(c2nc(NCCC(=O)OCC)nc3c(F)c(-c4cc(O)cc5ccccc45)c(Cl)cc23)CC1]

To a solution of ethyl 3-((6-chloro-8-fluoro-7-(3-hydroxynaphthalen-1-yl)-4-(piperazin-1-yl)quinazolin-2-yl)amino)propanoate hydrochloride (630 mg, 1.12 mmol) and triethylamine (341 mg, 3.36 mmol) in dichloromethane (5 ml) was added acryloyl chloride (166 mg, 1.68 mmol) at 0° C., stirred at room temperature for 1 hour. The mixture was quenched with water (20 ml) at 0° C., and extracted with dichloromethane (20 ml). The organic layer was collected, washed with brine (20 ml), dried over anhydrous sodium sulfate, and concentrated under reduced pressure to give a crude residue which was purified by silica gel flash chromatography (eluted with 2-5% methanol in dichloromethane) to afford ethyl 3-((4-(4-acryloylpiperazin-1-yl)-6-chloro-8-fluoro-7-(3-hydroxynaphthalen-1-yl)quinazolin-2-yl)amino)propanoate (425 mg, 66%) as off-white solid.

Step 2: Preparation of 3-((4-(4-acryloylpiperazin-1-yl)-6-chloro-8-fluoro-7-(3-hydroxynaphthalen-1-yl)quinazolin-2-yl)amino)propanoic acid

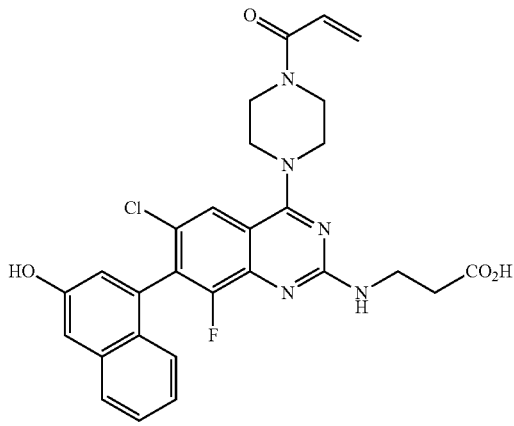

A mixture of ethyl3-((4-(4-carbamoylpiperazin-1-yl)-6-chloro-8-fluoro-7-(3-hydroxynaphthalen-1-yl)quinazolin-2-yl)amino)propanoate ethyl 3-((4-(4-acryloylpiperazin-1-yl)-6-chloro-8-fluoro-7-(3-hydroxynaphthalen-1-yl)quinazolin-2-yl)amino)propanoate (425 mg, 0.75 mmol) and lithium hydroxide monohydrate (63 mg, 1.5 mmol) in tetrahydrofuran (4 ml)-water (1 ml)-methanol (1 ml) was stirred at room temperature for 1 hour. The reaction mixture was acidified with diluted hydrochloride acid (1N) to pH 6-7, and extracted with dichloromethane (10 ml×3). The combined organic layers were dried over sodium sulfate and concentrated under reduced pressure to afford 3-((4-(4-carbamoylpiperazin-1-yl)-6-chloro-8-fluoro-7-(3-hydroxynaphthalen-1-yl)quinazolin-2-yl)amino)propanoic acid (400 mg, 99%) as light yellow solid. LC/MS (ESI) m/z: 550.1 [M+1]$^+$.

Exemplary Synthesis of 2,2,5-trimethyl-4-oxo-3,8,11-trioxa-5-azatridecan-13-yl 4-methylbenzenesulfonate

Step 1: Preparation of 2-(2-(2-hydroxyethoxy)ethoxy)ethyl 4-methylbenzenesulfonate

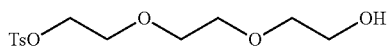 [SMILES: Cc1ccc(S(=O)(=O)OCCOCCOCCO)cc1]

To a mixture of 2-[2-(2-hydroxyethoxy)ethoxy]ethanol (5.00 g, 33.29 mmol, 1.00 eq) and 4-methylbenzenesulfonyl chloride (1.59 g, 8.32 mmol, 0.25 eq) in dichloromethane (50 mL) was added triethylamine (1.68 g, 16.65 mmol, 2.3 mL, 0.5 eq) in one portion at 25° C. under nitrogen. The mixture was stirred at 25° C. for 12 hours. The mixture was washed with brine (30 mL×2), dried with anhydrous sodium sulfate, filtered and concentrated in vacuum. The residue was purified by silica gel chromatography (Petroleum ether/Ethyl acetate=1/1 to 0:1) to afford 2-[2-(2-hydroxyethoxy)ethoxy]ethyl 4-methylbenzenesulfonate (1.72 g, 5.65 mmol, 17% yield) as a colorless oil. LC/MS (ESI) m/z: 327.0 [M+23]$^+$; $^1$H-NMR (400 MHz, CDCl$_3$) δ 7.81 (d, J=8.3 Hz, 2H), 7.35 (d, J=8.0 Hz, 2H), 4.22-4.15 (m, 2H), 3.79-3.67 (m, 4H), 3.67-3.56 (m, 6H), 2.46 (s, 3H).

Step 2: Preparation of 2-(2-(2-(methylamino)ethoxy)ethoxy)ethan-1-ol

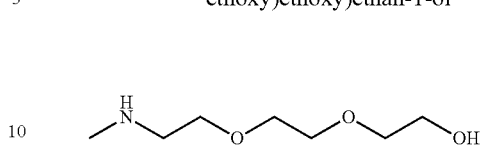

Methanamine (41.27 g, 398.65 mmol, 50 mL, 30% in ethanol, 24.27 eq) was added to 2-[2-(2-hydroxyethoxy)ethoxy]ethyl 4-methylbenzenesulfonate (5 g, 16.43 mmol, 1 eq). The mixture was stirred at 80° C. for 12 hours. The mixture was cooled to 20° C. and concentrated in vacuum. 2-[2-[2-(methylamino)ethoxy]ethoxy]ethanol (2.68 g, 16.43 mmol) was obtained as a colorless oil.

Step 3: Preparation of tert-butyl (2-(2-(2-hydroxyethoxy)ethoxy)ethyl)(methyl)carbamate

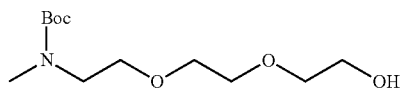 [SMILES: CN(CCOCCOCCO)C(=O)OC(C)(C)C]

To a solution of 2-[2-[2-(methylamino)ethoxy]ethoxy]ethanol (2.68 g, 16.43 mmol, 1 eq) and di-tert-butyl dicarbonate (4.30 g, 19.70 mmol, 4.5 mL, 1.2 eq) in dichloromethane (20 mL) was added triethylamine (3.32 g, 32.84 mmol, 4.5 mL, 2 eq). The mixture was stirred at 20° C. for 12 hours. The mixture was quenched by the addition of water (20 mL) and the aqueous phase was extracted with ethyl acetate (20 mL×3). The combined organic phase was washed with brine (20 mL), dried with anhydrous sodium sulfate, filtered and concentrated in vacuum. The residue was purified by silica gel chromatography (petroleum ether/ethyl acetate=3/1 to 1/3) to give tert-butyl N-[2-[2-(2-hydroxyethoxy)ethoxy]ethyl]-N-methyl-carbamate (3.2 g, 12.15 mmol, 74% yield) as a colorless oil. $^1$H-NMR (400 MHz, CDCl$_3$) δ 3.70-3.80 (m, 2H), 3.54-3.70 (m, 8H), 3.41 (br s, 2H), 2.92 (s, 3H), 1.46 (s, 9H).

Step 4: Preparation of 2,2,5-trimethyl-4-oxo-3,8,11-trioxa-5-azatridecan-13-yl 4-methylbenzenesulfonate

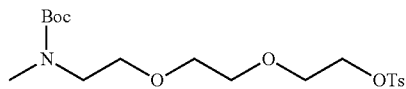 [SMILES: Cc1ccc(S(=O)(=O)OCCOCCOCCN(C)C(=O)OC(C)(C)C)cc1]

To a solution of tert-butyl N-[2-[2-(2-hydroxyethoxy)ethoxy]ethyl]-N-methyl-carbamate (600 mg, 2.28 mmol, 1 eq) and triethylamine (461 mg, 4.56 mmol, 0.6 mL, 2 eq) in dichloromethane (5 mL) was added p-toluenesulfonyl chloride (651 mg, 3.42 mmol, 1.5 eq). The mixture was stirred at 20° C. for 12 hours. The mixture was diluted with water (20 mL). The aqueous phase was extracted with ethyl acetate (20 mL×3). The combined organic phase was washed with brine (20 mL), dried with anhydrous sodium sulfate, filtered and concentrated in vacuum. The residue was purified by silica gel chromatography (petroleum ether/ethyl acetate=10/1 to 3/1) to give 2-[2-[2-[tert-butoxycarbonyl (methyl)amino]ethoxy]ethoxy]ethyl 4-methylbenzenesulfonate (750 mg, 1.80 mmol, 79% yield) as a colorless oil. LC/MS (ESI) m/z: 440.1 [M+23]⁺; ¹H-NMR (400 MHz, CDCl₃) δ 7.81 (d, J=8.0 Hz, 2H), 7.35 (d, J=8.0 Hz, 2H), 4.19-4.15 (m, 2H), 3.70 (t, J=4.8 Hz, 2H), 3.61-3.51 (m, 6H), 3.38 (br s, 2H), 2.90 (s, 3H), 2.46 (s, 3H), 1.45 (s, 9H).

Exemplary Synthesis of 2-(2,6-dioxopiperidin-3-yl)-4-fluoroisoindoline-1,3-dione Step 1: Preparation of 2-(2,6-dioxopiperidin-3-yl)-4-fluoroisoindoline-1,3-dione

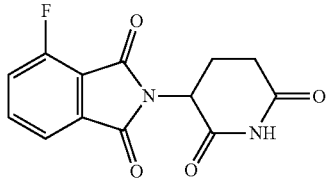 [SMILES: O=C1CCC(N2C(=O)c3cccc(F)c3C2=O)C(=O)N1]

To a mixture of 3-aminopiperidine-2,6-dione (10.90 g, 66.22 mmol, 1.1 eq, hydrochloride) and 4-fluoroisobenzofuran-1,3-dione (10 g, 60.20 mmol, 1 eq) in acetic acid (150 mL) was added potassium acetate (18.32 g, 186.63 mmol, 3.1 eq) in one portion at 100° C. under nitrogen. The mixture was stirred at 100° C. for 16 hours. The mixture was cooled to 20° C. and concentrated under reduced pressure at 55° C. The residue was triturated with Ethyl acetate (100 mL) and water (30 mL), the cake was collected under reduced pressure and dried under high vacuo. Compound 2-(2,6-dioxo-3-piperidyl)-4-fluoro-isoindoline-1,3-dione (8.9 g, 32.22 mmol, 53% yield) was obtained as a black solid. ¹H-NMR (400 MHz, DMSO-d₆) δ 11.15 (br s, 1H), 7.95 (dt, J=4.6, 7.9 Hz, 1H), 7.82-7.70 (m, 2H), 5.17 (dd, J=5.3, 12.9 Hz, 1H), 2.99-2.81 (m, 1H), 2.66-2.52 (m, 2H), 2.13-2.02 (m, 1H).

Exemplary Synthesis of (S)-3-((4-(4-(tert-butoxycarbonyl)piperazin-1-yl)-6-chloro-8-fluoro-7-(2-fluoro-6-hydroxyphenyl)quinazolin-2-yl)amino)propanoic acid Step 1: Preparation of 3-fluoro-2-(4,4,5,5-tetramethyl-1,3,2-dioxaborolan-2-yl)phenol

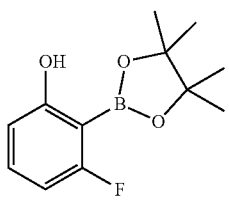 [SMILES: CC1(C)OB(c2c(O)cccc2F)OC1(C)C]

To a solution of (2-fluoro-6-methoxy-phenyl)boronic acid (10 g, 58.84 mmol, 1.0 eq) in dichloromethane (100 mL) was added boron tribromide (44 g, 176.52 mmol, 3.0 eq) at 0° C. Then the mixture was stirred at 0° C. for 0.5 hour. The mixture was diluted with ice water (100 mL) at 0° C., extracted with ethyl acetate (200 mL×3), washed with brine (200 mL), dried over anhydrous sodium sulfate, filtered and then concentrated. The residue in tetrahydrofuran (100 mL) was added 2,3-dimethylbutane-2,3-diol (13.91 g, 117.68 mmol, 2 eq). Then the mixture was stirred at 20° C. for 12 hours. Then the mixture was concentrated. The residue was purified by column chromatography silica (petroleum ether). 3-fluoro-2-(4,4,5,5-tetramethyl-1,3,2-dioxaborolan-2-yl)phenol (6 g, 25.20 mmol, 42% yield) was obtained as a white solid. ¹H-NMR (400 MHz, CDCl₃) δ 8.37 (s, 1H), 7.36-7.28 (m, 1H), 6.69 (d, J=8.4 Hz, 1H), 6.57 (t, J=8.8 Hz, 1H), 1.40 (s, 12H).

Step 2: Preparation of tert-butyl 4-(7-bromo-6-chloro-8-fluoro-2-((3-methoxy-3-oxopropyl)amino)quinazolin-4-yl)piperazine-1-carboxylate

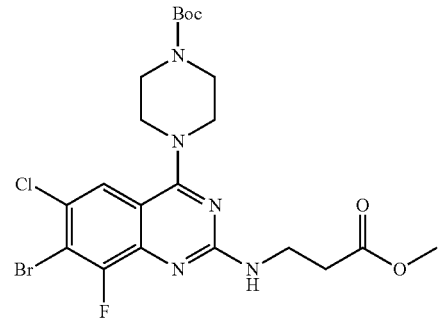 [SMILES: COC(=O)CCNc1nc(N2CCN(C(=O)OC(C)(C)C)CC2)c2cc(Cl)c(Br)c(F)c2n1]

To a mixture of methyl 3-aminopropanoate (16.57 g, 118.71 mmol, 3 eq, hydrochloride) and tert-butyl 4-(7-bromo-2,6-dichloro-8-fluoro-quinazolin-4-yl)piperazine-1-carboxylate (19 g, 39.57 mmol, 1 eq) in isopropanol (600 mL) was added N,N-diisopropylethylamine (25.57 g, 197.85 mmol, 34.46 mL, 5 eq) in one portion at 20° C. under nitrogen. The mixture was stirred at 95° C. for 12 hours. The mixture was cooled to 20° C. and concentrated under reduced pressure at 45° C. The residue was purified by silica gel chromatography (petroleum ether/ethyl acetate=10/1, 3/1) to afford tert-butyl4-[7-bromo-6-chloro-8-fluoro-2-[(3-methoxy-3-oxo-propyl)amino]quinazolin-4-yl]piperazine-1-carboxylate (10.6 g, 19.38 mmol, 49% yield) as yellow solid. ¹H-NMR (400 MHz, DMSO-d₆) δ 7.75 (s, 1H), 7.65-7.32 (m, 1H), 3.64-3.52 (m, 10H), 3.34 (s, 3H), 2.66 (br d, J=9.2 Hz, 2H), 1.43 (s, 9H).

Step 3: Preparation of tert-butyl 4-(6-chloro-8-fluoro-7-(2-fluoro-6-hydroxyphenyl)-2-((3-methoxy-3-oxopropyl)amino)quinazolin-4-yl)piperazine-1-carboxylate

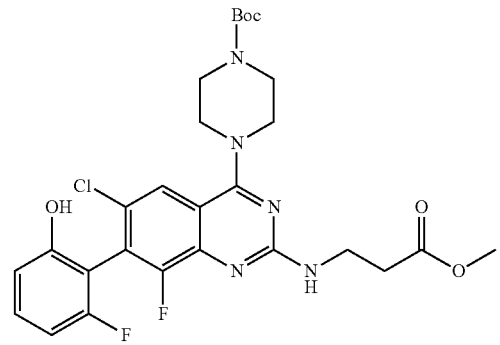 [SMILES: COC(=O)CCNc1nc(N2CCN(C(=O)OC(C)(C)C)CC2)c2cc(Cl)c(-c3c(O)cccc3F)c(F)c2n1]

To a solution of tert-butyl 4-[7-bromo-6-chloro-8-fluoro-2-[(3-methoxy-3-oxo-propyl)amino]quinazolin-4-yl]piperazine-1-carboxylate (6.8 g, 12.44 mmol, 1 eq) and 3-fluoro-2-(4,4,5,5-tetramethyl-1,3,2-dioxaborolan-2-yl)phenol (7.43 g, 31.21 mmol, 2.51 eq) in toluene (140 mL) was added [2-(2-aminophenyl)phenyl]-chloro-palladium; dicyclohexyl-[2-(2,6-dimethoxyphenyl)phenyl]phosphane (448 mg, 0.62 mmol, 0.05 eq) and potassium phosphate (1.5 M, 24.87 mL, 3 eq). The reaction mixture was degassed and charged with nitrogen for three times and then stirred at 75° C. for 30 hours. Ethyl acetate (80 mL) and water (100 mL) were added and the mixture was separated. The organic layer was dried over sodium sulfate and then concentrated under vacuum to get the residue. The residue was purified by silica gel flash chromatography (0-100% ethyl acetate in petroleum ether) to get tert-butyl 4-[6-chloro-8-fluoro-7-(2-fluoro-6-hydroxy-phenyl)-2-[(3-methoxy-3-oxo-propyl)amino]quinazolin-4-yl]piperazine-1-carboxylate (4.2 g, 6.90 mmol, 55% yield, 95% purity) as a yellow solid. LC/MS (ESI) m/z: 578.2 [M+1]+.

Step 4: Preparation of tert-butyl (S)-4-(6-chloro-8-fluoro-7-(2-fluoro-6-hydroxyphenyl)-2-((3-methoxy-3-oxopropyl)amino)quinazolin-4-yl)piperazine-1-carboxylate and tert-butyl (R)-4-(6-chloro-8-fluoro-7-(2-fluoro-6-hydroxyphenyl)-2-((3-methoxy-3-oxopropyl)amino)quinazolin-4-yl)piperazine-1-carboxylate

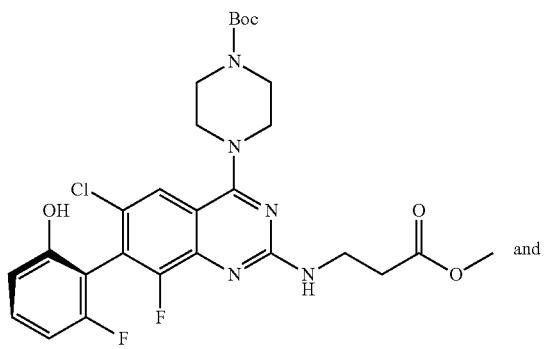

and

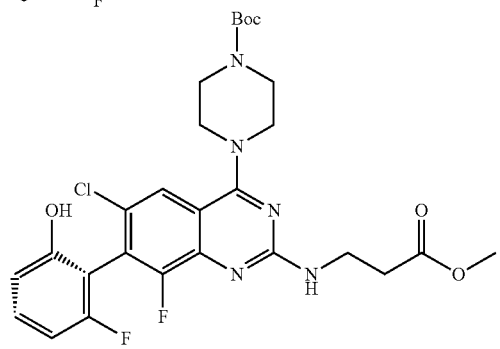

Tert-butyl 4-[6-chloro-8-fluoro-7-(2-fluoro-6-hydroxyphenyl)-2-[(3-methoxy-3-oxo-propyl)amino]quinazolin-4-yl]piperazine-1-carboxylate (5 g, 8.65 mmol, 1 eq) was separated by SFC. Tert-butyl (S)-4-(6-chloro-8-fluoro-7-(2-fluoro-6-hydroxyphenyl)-2-((3-methoxy-3-oxopropyl)amino)quinazolin-4-yl)piperazine-1-carboxylate (2.38 g, 3.85 mmol, 89% yield, 93% purity) was obtained as a yellow solid. Tert-butyl (R)-4-(6-chloro-8-fluoro-7-(2-fluoro-6-hydroxyphenyl)-2-((3-methoxy-3-oxopropyl)amino)quinazolin-4-yl)piperazine-1-carboxylate (2.5 g, 4.15 mmol, 96% yield, 96% purity) was obtained as a yellow solid.

Step 5: Preparation of tert-butyl (S)-3-((4-(4-(tert-butoxycarbonyl)piperazin-1-yl)-6-chloro-8-fluoro-7-(2-fluoro-6-hydroxyphenyl)quinazolin-2-yl)amino)propanoic acid

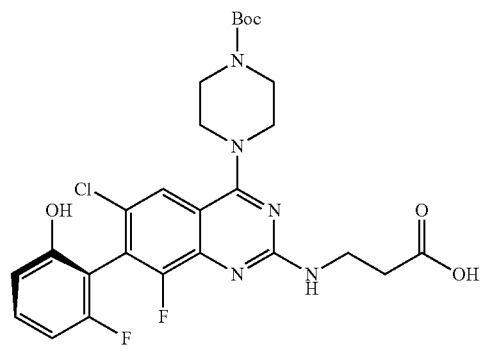

To a solution of tert-butyl 4-[6-chloro-8-fluoro-7-(2-fluoro-6-hydroxy-phenyl)-2-[(3-methoxy-3-oxo-propyl)amino]quinazolin-4-yl]piperazine-1-carboxylate (2.38 g, 3.83 mmol, 1 eq) in mixture of tetrahydrofuran (12 mL) and methanol (12 mL) was added water (12 mL) and lithium hydroxide monohydrate (450 mg, 10.73 mmol, 2.80 eq). The reaction mixture was stirred at 20° C. for 16 hours. The pH of the water layer was adjusted to 6 with the addition of 1 N hydrochloric acid. The resulting mixture was extracted with ethyl acetate (70 mL×2). The organic layer was dried over sodium sulfate and then concentrated under vacuum to get (S)-3-((4-(4-(tert-butoxycarbonyl)piperazin-1-yl)-6-chloro-8-fluoro-7-(2-fluoro-6-hydroxyphenyl)quinazolin-2-yl)amino)propanoic acid (2.02 g, 3.58 mmol, 93% yield) as a yellow solid.

Exemplary Synthesis of (R)-3-((4-(4-(tert-butoxycarbonyl)piperazin-1-yl)-6-chloro-8-fluoro-7-(2-fluoro-6-hydroxyphenyl)quinazolin-2-yl)amino)propanoic acid Step 1: Preparation of (R)-3-((4-(4-(tert-butoxycarbonyl)piperazin-1-yl)-6-chloro-8-fluoro-7-(2-fluoro-6-hydroxyphenyl)quinazolin-2-yl)amino)propanoic acid

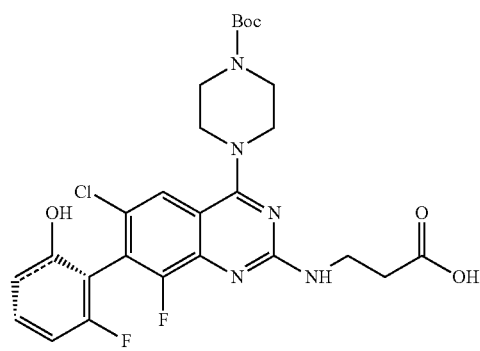

To a solution of tert-butyl 4-[6-chloro-8-fluoro-7-(2-fluoro-6-hydroxy-phenyl)-2-[(3-methoxy-3-oxo-propyl)amino]quinazolin-4-yl]piperazine-1-carboxylate (2.5 g, 4.15 mmol, 1 eq) in a mixture of tetrahydrofuran (12 mL) and methanol (12 mL) were added water (12 mL) and lithium hydroxide monohydrate (488 mg, 11.63 mmol, 2.80 eq). The reaction mixture was stirred at 20° C. for 16 hours. The pH of the mixture was adjusted to 6 with the addition of 1 N hydrochloric acid. The resulting mixture was extracted with ethyl acetate (80 mL×2). The organic layer was dried over sodium sulfate and then concentrated under vacuum to get (R)-3-((4-(4-(tert-butoxycarbonyl)piperazin-1-yl)-6-chloro-8-fluoro-7-(2-fluoro-6-hydroxyphenyl)quinazolin-2-yl)amino)propanoic acid (2.24 g, 3.97 mmol, 95% yield) as a yellow solid.

Exemplary Synthesis of (S)-3-((4-(4-acryloylpiperazin-1-yl)-6-chloro-8-fluoro-7-(2-fluoro-6-hydroxyphenyl)quinazolin-2-yl)amino)propanoic acid Step 1: Preparation of (S)-3-((6-chloro-8-fluoro-7-(2-fluoro-6-hydroxyphenyl)-4-(piperazin-1-yl)quinazolin-2-yl)amino)propanoic acid

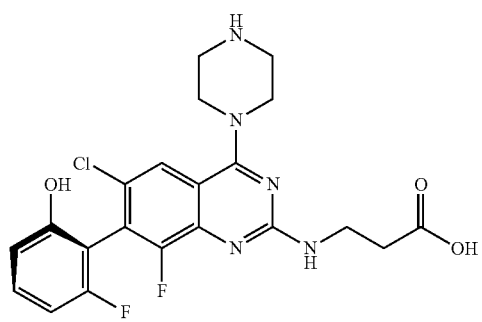

To a solution of (S)-3-((4-(4-(tert-butoxycarbonyl)piperazin-1-yl)-6-chloro-8-fluoro-7-(2-fluoro-6-hydroxyphenyl)quinazolin-2-yl)amino)propanoic acid (1.0 g, 1.77 mmol, 1 eq) in dioxane (10 mL) was added hydrogen chloride/dioxane (4 M, 30.00 mL, 67.68 eq). The mixture was stirred at 25° C. for 1 hour. The reaction mixture was concentrated under reduced pressure to give the product (S)-3-((6-chloro-8-fluoro-7-(2-fluoro-6-hydroxyphenyl)-4-(piperazin-1-yl)quinazolin-2-yl)amino)propanoic acid (0.88 g, 1.76 mmol, 99% yield, hydrochloride) as a white solid. LC/MS (ESI) m/z: 464.0 [M+1]$^+$.

Step 2: Preparation of (S)-3-((4-(4-acryloylpiperazin-1-yl)-6-chloro-8-fluoro-7-(2-fluoro-6-hydroxyphenyl)quinazolin-2-yl)amino)propanoic acid

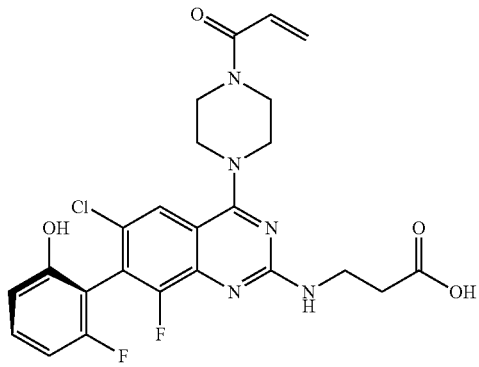

To a solution of (S)-3-((6-chloro-8-fluoro-7-(2-fluoro-6-hydroxyphenyl)-4-(piperazin-1-yl)quinazolin-2-yl)amino)propanoic acid (0.88 g, 1.76 mmol, 1 eq, hydrochloride) and saturated sodium bicarbonate solution (20 mL) in tetrahydrofuran (20 mL) was added acryloyl chloride (159 mg, 1.76 mmol, 143.24 uL, 9.98e-1 eq). The mixture was stirred at 0° C. for 0.5 hour. The reaction mixture was concentrated under reduced pressure to remove solvent to give a residue. The residue was purified by prep-HPLC. Compound (S)-3-((4-(4-acryloylpiperazin-1-yl)-6-chloro-8-fluoro-7-(2-fluoro-6-hydroxyphenyl)quinazolin-2-yl)amino)propanoic acid (0.52 g, 1.00 mmol, 57% yield) was obtained as a white solid. $^1$H-NMR (400 MHz, CD$_3$OD) δ 7.77 (s, 1H), 7.33-7.25 (m, 1H), 6.86-6.66 (m, 3H), 6.26 (dd, J=2.0, 16.8 Hz, 1H), 5.80 (dd, J=2.0, 10.8 Hz, 1H), 3.88 (br s, 8H), 3.74 (br t, J=6.4 Hz, 2H), 2.63 (t, J=6.4 Hz, 2H).

Exemplary Synthesis of (S)-3-((4-(4-carbamoylpiperazin-1-yl)-6-chloro-8-fluoro-7-(2-fluoro-6-hydroxyphenyl)quinazolin-2-yl)amino)propanoic acid Step 1: Preparation of methyl (S)-3-((6-chloro-8-fluoro-7-(2-fluoro-6-hydroxyphenyl)-4-(piperazin-1-yl)quinazolin-2-yl)amino)propanoate hydrochloride

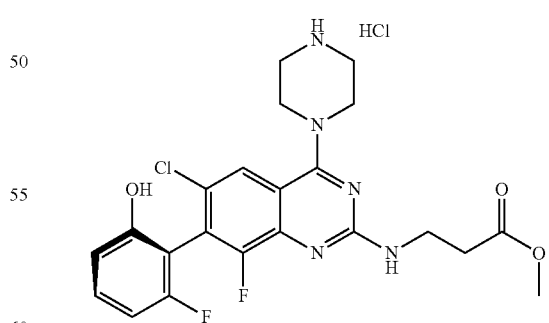

To a solution of 3-[[4-(4-tert-butoxycarbonylpiperazin-1-yl)-6-chloro-8-fluoro-7-(2-fluoro-6-hydroxy-phenyl)quinazolin-2-yl]amino]propanoic acid (1.5 g, 2.66 mmol, 1 eq) in methanol (5 mL) was added hydrochloric acid in methanol (4 M, 10 mL). The mixture was stirred at 50° C. for 2 hours. The reaction mixture was concentrated under reduced pressure to give compound methyl 3-[[6-chloro-8-fluoro-7-(2-fluoro-6-hydroxy-phenyl)-4-piperazin-1-yl-quinazolin-2-yl]amino]propanoate (1.35 g, hydrochloride) as a yellow solid. LC/MS (ESI) m/z: 478.2 [M+1]$^+$; $^1$H-NMR (400 MHz, DMSO-d$_6$) δ 10.63 (brs, 1H), 9.92 (brs, 2H), 8.77-8.43 (m, 1H), 8.08 (s, 1H), 7.38 (q, J=8.0 Hz, 1H), 6.94 (d, J=8.4 Hz, 1H), 6.87-6.72 (m, 1H), 4.42-4.15 (m, 4H), 3.86-3.51 (m, 5H), 3.36-3.26 (m, 4H), 2.71-2.55 (m, 2H).

Step 2: Preparation of methyl (S)-3-((4-(4-carbamoylpiperazin-1-yl)-6-chloro-8-fluoro-7-(2-fluoro-6-hydroxyphenyl)quinazolin-2-yl)amino)propanoate

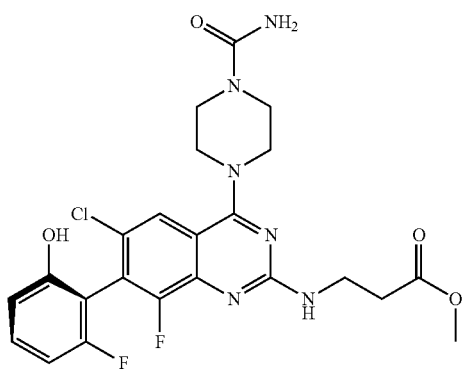

To a solution of methyl 3-[[6-chloro-8-fluoro-7-(2-fluoro-6-hydroxy-phenyl)-4-piperazin-1-yl-quinazolin-2-yl]amino]propanoate (1.35 g, 2.62 mmol, 1 eq, hydrochloride) and triethylamine (266 mg, 2.62 mmol, 1 eq) in N,N-dimethylformamide (10 mL) and tetrahydrofuran (5 mL) was added isocyanato(trimethyl)silane (302 mg, 2.62 mmol, 1 eq). The mixture was stirred at 20° C. for 0.5 hour. The reaction mixture was concentrated under reduced pressure to give compound methyl 3-[[4-(4-carbamoylpiperazin-1-yl)-6-chloro-8-fluoro-7-(2-fluoro-6-hydroxy-phenyl)quinazolin-2-yl]amino]propanoate (1.37 g) as a yellow oil. LC/MS (ESI) m/z: 521.2 [M+1]$^+$.

Step 3: Preparation of (S)-3-((4-(4-carbamoylpiperazin-1-yl)-6-chloro-8-fluoro-7-(2-fluoro-6-hydroxyphenyl)quinazolin-2-yl)amino)propanoic acid

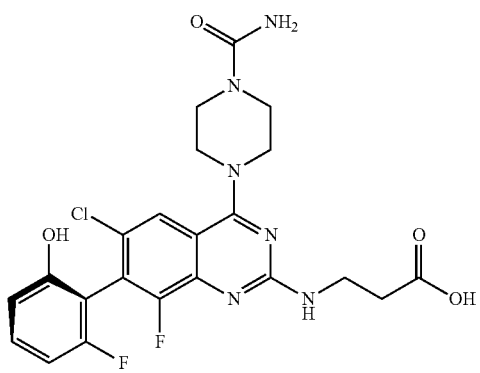

To a solution of methyl 3-[[4-(4-carbamoylpiperazin-1-yl)-6-chloro-8-fluoro-7-(2-fluoro-6-hydroxy-phenyl)quinazolin-2-yl]amino]propanoate (1.37 g, 2.63 mmol, 1 eq) in tetrahydrofuran (10 mL) and water (3 mL) was added lithium hydroxide monohydrate (276 mg, 6.57 mmol, 2.5 eq). The mixture was stirred at 20° C. for 0.5 hour. The reaction mixture was concentrated under reduced pressure to give a residue. The residue was diluted with water (10 mL), acidified to pH=3 with hydrochloric acid (1 M), some precipitate was formed while the addition of hydrochloric acid. The resulting mixture was filtered and the filter cake was evaporated to dryness under reduced pressure to give compound 3-[[4-(4-carbamoylpiperazin-1-yl)-6-chloro-8-fluoro-7-(2-fluoro-6-hydroxy-phenyl)quinazolin-2-yl]amino]propanoic acid (1.2 g, 2.37 mmol, 90% yield) as a yellow solid. LC/MS (ESI) m/z: 507.2 [M+1]$^+$; $^1$H-NMR (400 MHz, DMSO-d$_6$) δ 12.41 (brs, 1H), 10.57-10.08 (m, 1H), 8.19-7.94 (m, 1H), 7.93-7.64 (m, 1H), 7.44-7.26 (m, 1H), 6.98-6.73 (m, 2H), 6.11 (brs, 2H), 4.19-3.91 (m, 2H), 3.77-3.46 (m, 4H), 3.43-3.36 (m, 4H), 2.58 (t, J=6.4 Hz, 2H).

Exemplary Synthesis of 4-(6-chloro-8-fluoro-4-(piperazin-1-yl)quinazolin-7-yl)naphthalen-2-ol hydrochloride Step 1: Preparation of 7-bromo-6-chloro-8-fluoroquinazolin-4(3H)-one

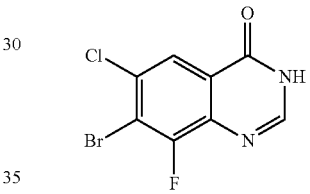

A mixture of 2-amino-4-bromo-5-chloro-3-fluorobenzoic acid (1.5 g, 5.58 mmol) and formimidamide acetate (2.3 g, 22.35 mmol) in ethanol (30 ml) was stirred at reflux for 24 hours. The mixture was concentrated and the residue was partitioned with water (20 ml) and ethyl acetate (20 ml). The organic layer was washed with brine (10 ml), dried over sodium sulfate and concentrated under reduced pressure to afford 7-bromo-6-chloro-8-fluoroquinazolin-4(3H)-one (1.2 g, 77%) as light yellow solid.

Step 2: Preparation of 7-bromo-4,6-dichloro-8-fluoroquinazoline

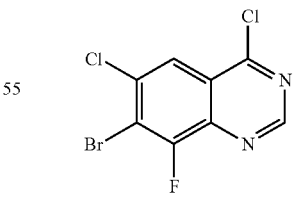

To a solution of 7-bromo-6-chloro-8-fluoroquinazolin-4 (3H)-one (1.2 g, 4.3 mmol) in sulfurous dichloride (16 ml) was added N,N-dimethylformamide (1 ml) at room temperature. The mixture was stirred at reflux for 16 hours. The mixture was concentrated and the residue was dissolved in dichloromethane (20 ml). The organic layer was poured into ice water (20 ml), washed with aqueous solution of sodium bicarbonate (1N, 10 ml) and brine (10 ml), dried over sodium sulfate and concentrated under reduced pressure to give a crude residue which was purified by silica gel flash chromatography (eluted with 5% ethyl acetate in hexane) to afford 7-bromo-4,6-dichloro-8-fluoroquinazoline (1.07 g, 83%) as yellow solid.

Step 3: Preparation of tert-butyl 4-(7-bromo-6-chloro-8-fluoroquinazolin-4-yl)piperazine-1-carboxylate

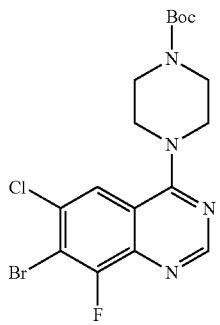 [SMILES: CC(C)(C)OC(=O)N1CCN(c2ncnc3c(F)c(Br)c(Cl)cc23)CC1]

A mixture of 7-bromo-4,6-dichloro-8-fluoroquinazoline (1.07 g, 3.61 mmol), tert-butyl piperazine-1-carboxylate (674 mg, 3.61 mmol) and triethylamine (1.1 g, 10.85 mmol) in 1,4-dioxane (11 ml) was stirred at 50° C. for 30 minutes. The reaction mixture was concentrated and the residue was partitioned between ethyl acetate (15 ml) and water (20 ml). The organic layer was collected, washed with brine (10 ml), dried over anhydrous sodium sulfate, and concentrated under reduced pressure to give a crude residue which was purified by silica gel flash chromatography (eluted with 20-25% ethyl acetate in hexane) to afford tert-butyl 4-(7-bromo-6-chloro-8-fluoroquinazolin-4-yl)piperazine-1-carboxylate (1 g, 62%) as white solid. $^1$H-NMR (400 MHz, CDCl$_3$) δ 1.50 (s, 9H), 3.65, 3.80 (two singles, 8H), 7.79 (s, 1H), 8.77 (s, 1H).

Step 4: Preparation of tert-butyl 4-(6-chloro-8-fluoro-7-(3-(methoxymethoxy)naphthalen-1-yl)quinazolin-4-yl)piperazine-1-carboxylate

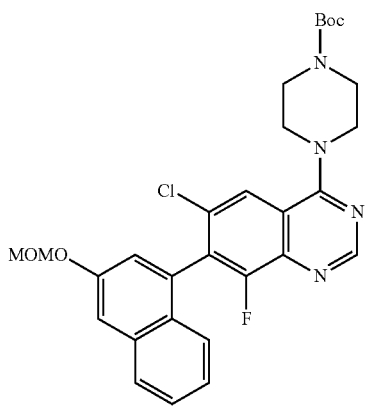

To a suspension of tert-butyl 4-(7-bromo-6-chloro-8-fluoroquinazolin-4-yl)piperazine-1-carboxylate (1 g, 2.24 mmol), 2-(3-(methoxymethoxy)naphthalen-1-yl)-4,4,5,5-tetramethyl-1,3,2-dioxaborolane (705 mg, 2.24 mmol) and potassium carbonate (624 mg, 4.48 mmol) in dioxane (8 ml)-water (2 ml) was added tetrakis(triphenylphosphine)palladium(0) (520 mg, 0.45 mmol) at room temperature under nitrogen atmosphere; the mixture was degassed and refilled with nitrogen three times. The resulting mixture was refluxed for 12 hours. The mixture was concentrated and the residue was partitioned with water (10 ml) and ethyl acetate (10 ml). The organic layer was collected, washed with brine (10 ml), dried over anhydrous sodium sulfate, and concentrated under reduced pressure to give a crude residue which was purified by silica gel flash chromatography (eluted with 18-33% ethyl acetate in hexane) to afford tert-butyl4-(6-chloro-8-fluoro-7-(3-(methoxymethoxy)naphthalen-1-yl)quinazolin-4-yl)piperazine-1-carboxylate (420 mg, 34%) as light yellow solid. LC/MS (ESI) m/z: 553.20 [M+1]$^+$.

Step 5: Preparation of 4-(6-chloro-8-fluoro-4-(piperazin-1-yl)quinazolin-7-yl)naphthalen-2-ol hydrochloride

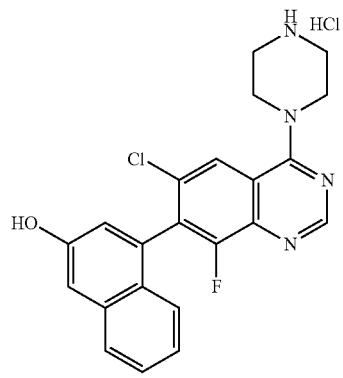 [SMILES: Cl ; Oc1cc(-c2c(Cl)cc3c(N4CCNCC4)ncnc3c2F)c2ccccc2c1]

To a solution of tert-butyl4-(6-chloro-8-fluoro-7-(3-(methoxymethoxy)naphthalen-1-yl)quinazolin-4-yl)piperazine-1-carboxylate (200 mg, 0.36 mmol) in methanol (2 ml) was added dioxane hydrochloric acid solution (2 ml) at room temperature. The mixture was stirred at room temperature for 1 hour. The mixture was concentrated and the solid was washed with ethyl acetate (5 ml). The solid was collected and dried to afford 4-(6-chloro-8-fluoro-4-(piperazin-1-yl)quinazolin-7-yl)naphthalen-2-ol hydrochloride (190 mg). LC/MS (ESI) m/z: 409.10 [M+1]$^+$.

Exemplary Synthesis of (2S,4R)-1-((S)-15-(tert-butyl)-13-oxo-5,8,11-trioxa-2,14-diazahexadecan-16-oyl)-4-hydroxy-N—((S)-1-(4-(4-methylthiazol-5-yl)phenyl)ethyl)pyrrolidine-2-carboxamide Step 1: Preparation of tert-butyl 2,2,5-trimethyl-4-oxo-3,8,11,14-tetraoxa-5-azahexadecan-16-oate

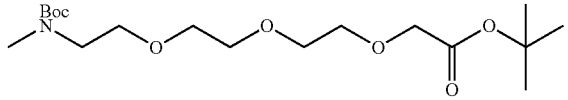 [SMILES: CN(CCOCCOCCOCC(=O)OC(C)(C)C)C(=O)OC(C)(C)C]

To a solution of tert-butyl (2-(2-(2-hydroxyethoxy)ethoxy)ethyl)(methyl)carbamate (600 mg, 2.28 mmol), tetrabutyl ammonium chloride (635 mg, 2.38 mmol), tert-butyl 2-bromoacetate (445 mg, 2.28 mmol) and sodium hydroxide (12 ml, 35% in water)dichloromethane (12 ml) was stirred at room temperature for 4 hours. The organic phase was collected, and the aqueous layer was extracted with dichloromethane(10 ml×2). The combined organic layers were washed with brine (20 ml), dried over anhydrous sodium sulfate, and concentrated under reduced pressure to give a residue which was purified by silica gel flash chromatography(eluted with 10-20% ethyl acetate in cyclohexane) to afford tert-butyl 2,2,5-trimethyl-4-oxo-3,8,11,14-tetraoxa-5-azahexadecan-16-oate (300 mg, 35%) as colorless oil. $^1$H-NMR (400 MHz, CDCl$_3$) δ 1.45, 1.47 (two singles, 18H), 2.91 (s, 3H), 3.32-3.46 (m, 2H), 3.58-3.73 (m, 10H), 4.02 (s, 2H).

Step 2: Preparation of 2,2,5-trimethyl-4-oxo-3,8,11,14-tetraoxa-5-azahexadecan-16-oic acid

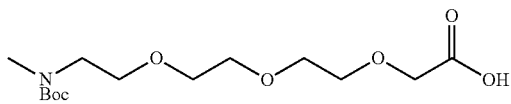 [SMILES: CN(CCOCCOCCOCC(=O)O)C(=O)OC(C)(C)C]

A mixture of tert-butyl 2,2,5-trimethyl-4-oxo-3,8,11,14-tetraoxa-5-azahexadecan-16-oate (100 mg, 0.26 mmol) and lithium hydroxide monohydrate (23 mg, 0.53 mmol) in tetrahydrofuran (1 ml)-water (0.5 ml)-methanol (0.5 ml) was stirred at room temperature for 1 hour. The mixture was concentrated and the residue was acidified with aqueous hydrochloride acid (1N) till pH 4-5, and extracted with dichloromethane (10 ml). The organic layer was washed with brine (5 ml), dried over sodium sulfate and concentrated under reduced pressure to afford 2,2,5-trimethyl-4-oxo-3,8,11,14-tetraoxa-5-azahexadecan-16-oic acid (77 mg, 90%) as colorless oil.

Step 3: Preparation of tert-butyl ((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)(methyl)carbamate

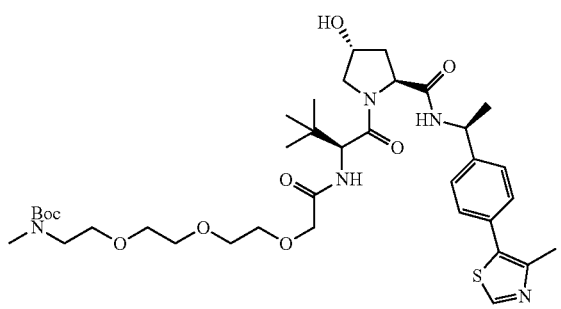

To a solution of 2,2,5-trimethyl-4-oxo-3,8,11,14-tetraoxa-5-azahexadecan-16-oic acid (77 mg, 0.24 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (115 mg, 0.24 mmol) and N-ethyl-N-isopropylpropan-2-amine (124 mg, 0.96 mmol) in dry N,N-dimethylformamide (2 ml) was added HATU (2-(7-Aza-1H-benzotriazole-1-yl)-1,1,3,3-tetramethyluronium hexafluorophosphate) (182 mg, 0.48 mmol) at 0° C., the resulting mixture was allowed to warm to room temperature and stirred at room temperature for 10 minutes. The mixture was partitioned between ethyl acetate (20 ml) and water (20 ml). The organic layer was collected, washed with brine (20 ml), dried over anhydrous sodium sulfate, and concentrated under reduced pressure to give a crude residue which was purified by silica gel flash column chromatography (eluted with 5% methanol in dichloromethane) to afford tert-butyl ((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)(methyl)carbamate (140 mg, 78%) as light yellow oil. LC/MS (ESI) m/z: 748.40 [M+1]$^+$.

Step 4: Preparation of (2S,4R)-1-((S)-15-(tert-butyl)-13-oxo-5,8,11-trioxa-2,14-diazahexadecan-16-oyl)-4-hydroxy-N—((S)-1-(4-(4-methylthiazol-5-yl)phenyl)ethyl)pyrrolidine-2-carboxamide

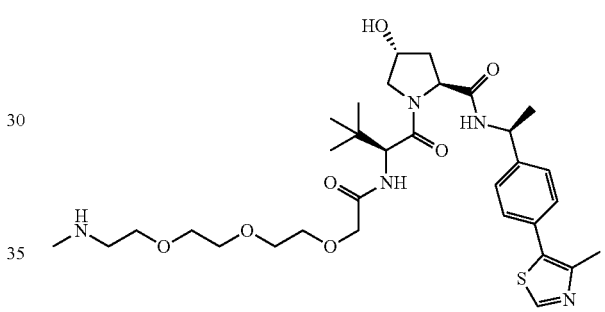

To a solution of tert-butyl ((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)(methyl)carbamate (70 mg, 0.093 mmol) in dichloromethane (1 ml) was added 2,2,2-trifluoroacetic acid (0.5 ml) at room temperature. The mixture was stirred at room temperature for 1 hour. The mixture was concentrated under reduced pressure to afford (2S,4R)-1-((S)-15-(tert-butyl)-13-oxo-5,8,11-trioxa-2,14-diazahexadecan-16-oyl)-4-hydroxy-N—((S)-1-(4-(4-methylthiazol-5-yl)phenyl)ethyl)pyrrolidine-2-carboxamide (70 mg) as light yellow oil.

Exemplary Synthesis of (2S,4R)-1-((S)-18-(tert-butyl)-16-oxo-5,8,11,14-tetraoxa-2,17-diazanonadecan-19-oyl)-4-hydroxy-N—((S)-1-(4-(4-methylthiazol-5-yl)phenyl)ethyl)pyrrolidine-2-carboxamide Step 1: Preparation of 2-(2-(2-(2-hydroxyethoxy)ethoxy)ethoxy)ethyl 4-methylbenzenesulfonate

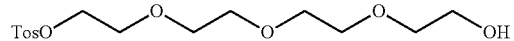

To a mixture of 2-[2-[2-(2-hydroxyethoxy)ethoxy]ethoxy]ethanol (5 g, 25.74 mmol, 4.4 mL, 1 eq) and 4-methylbenzenesulfonyl chloride (1.23 g, 6.44 mmol, 0.25 eq) in dichloromethane (50 mL) was added triethylamine (1.30 g, 12.87 mmol, 1.8 mL, 0.5 eq) in one portion at 25° C. under nitrogen. The mixture was stirred at 25° C. for 12 hours. The mixture was washed with brine (30 mL×2), dried with anhydrous sodium sulfate, filtered and concentrated in vacuum. The residue was purified by silica gel chromatography (Petroleum ether/Ethyl acetate=1/1 to 0/1) to afford 2-[2-[2-(2-hydroxyethoxy)ethoxy]ethoxy]ethyl 4-methylbenzenesulfonate (1.98 g, 5.68 mmol, 22% yield) as colorless oil. LC/MS (ESI) m/z: 371.0 [M+23]+; 1H-NMR (400 MHz, CDCl3) δ 7.82 (d, J=8.3 Hz, 2H), 7.36 (d, J=8.2 Hz, 2H), 4.21-4.11 (m, 2H), 3.75-3.61 (m, 14H), 2.47 (s, 3H).

Step 2: Preparation of 5,8,11-trioxa-2-azatridecan-13-ol

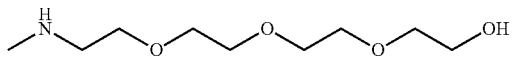

A solution of 2-[2-[2-(2-hydroxyethoxy)ethoxy]ethoxy] ethyl 4-methylbenzenesulfonate (6 g, 17.22 mmol, 1 eq) in methanamine (16.21 g, 172.21 mmol, 33% purity, 10 eq) was stirred at 80° C. for 16 hours. The reaction mixture was concentrated in vacuum to give a residue. 2-[2-[2-[2-(methylamino)ethoxy]ethoxy]ethoxy]ethanol (4.6 g) was obtained as a light yellow oil. 1H-NMR (400 MHz, CDCl3) δ 7.77 (d, J=8.2 Hz, 2H), 7.17 (d, J=7.9 Hz, 2H), 3.84-3.71 (m, 4H), 3.69-3.60 (m, 10H), 3.21-3.09 (m, 2H), 2.82-2.63 (m, 3H).

Step 3: Preparation of tert-butyl (2-(2-(2-(2-hydroxyethoxy)ethoxy)ethoxy)ethyl)(methyl)carbamate

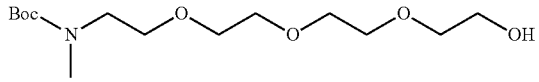 [SMILES: CN(CCOCCOCCOCCO)C(=O)OC(C)(C)C]

To a solution of 2-[2-[2-[2-(methylamino)ethoxy]ethoxy] ethoxy]ethanol (3.86 g, 18.62 mmol, 1 eq) in dichloromethane (30 mL) was added di-tert-butyl dicarbonate (4.88 g, 22.35 mmol, 5.13 mL, 1.2 eq) at 0° C., then stirred at 15° C. for 16 hours. Triethylamine (3.77 g, 37.25 mmol, 5.18 mL, 2 eq) was added and then stirred at 15° C. for 12 hours. The reaction mixture was concentrated in vacuum to give a residue. The residue was purified by silica gel column chromatography (Petroleum ether/Ethyl acetate=5/1 to 1/3) to give tert-butyl N-[2-[2-[2-(2-hydroxyethoxy)ethoxy] ethoxy]ethyl]-N-methyl-carbamate (5.74 g) was obtained as a light yellow oil. 1H-NMR (400 MHz, CDCl3) δ 3.75-3.47 (m, 14H), 3.38 (br s, 2H), 2.90 (s, 3H), 1.44 (s, 9H).

Step 4: Preparation of ethyl 2,2,5-trimethyl-4-oxo-3,8,11,14,17-pentaoxa-5-azanonadecan-19-oate

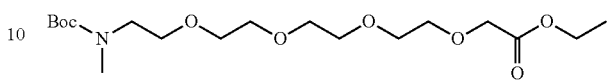

To a mixture of tert-butyl N-[2-[2-[2-(2-hydroxyethoxy) ethoxy]ethoxy]ethyl]-N-methyl-carbamate (1 g, 3.25 mmol, 1 eq) and diacetoxyrhodium (143 mg, 0.32 mmol, 0.1 eq) in dichloromethane (20 mL) was added ethyl 2-diazoacetate (2.47 g, 19.50 mmol, 2.27 mL, 90% purity, 6 eq) in three portions dropwise at −5 to 0° C. Then the reaction mixture was stirred at 10° C. for 16 hours. Acetic acid (0.4 mL) was added to the reaction mixture. Then the reaction mixture was extracted with dichloromethane (30 mL×3), and concentrated under vacuum to give a residue. The residue was purified by silica gel column chromatography (petroleum ether/ethyl acetate=20/1 to 1/3). ethyl 2-[2-[2-[2-[2-[tert-butoxycarbonyl(methyl)amino]ethoxy]ethoxy]ethoxy] ethoxy]acetate (600 mg, 1.52 mmol, 46% yield) was obtained as a green oil. 1H-NMR (400 MHz, CDCl3) δ 4.21 (q, J=7.2 Hz, 2H), 4.15 (s, 2H), 3.75-3.67 (m, 4H), 3.66 (s, 4H), 3.64-3.51 (m, 6H), 3.39 (br s, 2H), 2.91 (s, 3H), 1.50-1.39 (m, 9H), 1.31-1.26 (m, 3H).

Step 5: Preparation of 2,2,5-trimethyl-4-oxo-3,8,11,14,17-pentaoxa-5-azanonadecan-19-oic acid

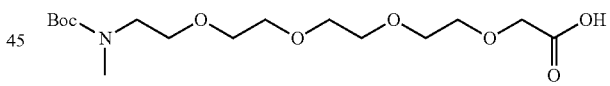

To a solution of ethyl 2-[2-[2-[2-[2-[tert-butoxycarbonyl (methyl)amino]ethoxy]ethoxy]ethoxy]ethoxy]acetate (600 mg, 1.52 mmol, 1 eq) in tetrahydrofuran (5 mL), water (5 mL) and methanol (5 mL) was added lithium hydroxide monohydrate (365 mg, 15.25 mmol, 10 eq), then the mixture was stirred at 15° C. for 4 hours. 1 M hydrogen chloride aqueous solution was added to the mixture until pH 3.0-4.0, then extracted with dichloromethane (30 mL×3), then the combined organic layers were washed with brine (10 mL), dried with anhydrous sodium sulfate, filtered and concentrated under reduced pressure. 2-[2-[2-[2-[2-[tert-butoxycarbonyl(methyl)amino]ethoxy]ethoxy]ethoxy]ethoxy]acetic acid (473 mg, 1.29 mmol, 84% yield) was obtained as a colorless oil. 1H-NMR (400 MHz, CDCl3) δ 4.16 (s, 2H), 3.80-3.74 (m, 2H), 3.73-3.57 (m, 12H), 3.41 (br s, 2H), 2.92 (s, 3H), 1.46 (s, 9H).

Step 6: Preparation of tert-butyl ((S)-16-((2S,4R)-4-hydroxy-2-(((S)-1-(4-(4-methylthiazol-5-yl)phenyl)ethyl)carbamoyl)pyrrolidine-1-carbonyl)-17,17-dimethyl-14-oxo-3,6,9,12-tetraoxa-15-azaoctadecyl)(methyl)carbamate

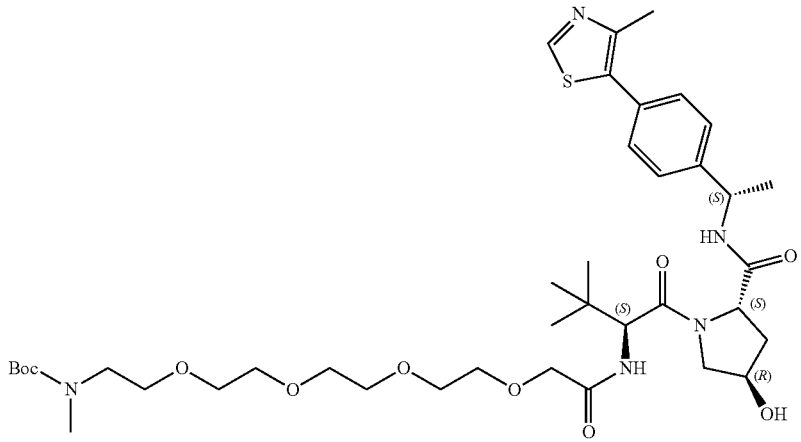

To a solution of 2-[2-[2-[2-[2-[tert-butoxycarbonyl(methyl)amino]ethoxy]ethoxy]ethoxy]ethoxy]acetic acid (250 mg, 0.68 mmol, 1 eq), (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (304 mg, 0.68 mmol, 1 eq) and N,N-diisopropylethylamine (265 mg, 2.05 mmol, 0.36 mL, 3 eq) in N,N-dimethylformamide (5 mL) was added hydroxybenzotriazole (111 mg, 0.82 umol, 1.2 eq) and 3-(ethyliminomethyleneamino)-N,N-dimethyl-propan-1-amine; hydrochloride (157 mg, 0.82 mmol, 1.2 eq) sequentially at 0° C., then stirred at 15° C. for 12 hours. The reaction mixture was poured into water (30 mL) and then extracted with ethyl acetate (20 mL×3). The combined organic phase was washed with brine (10 mL), dried with anhydrous sodium sulfate, filtered and concentrated in vacuum. The residue was purified by prep-TLC (dichloromethane/methanol=10/1). tert-butyl N-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl]-N-methyl-carbamate (405 mg, 0.51 mmol, 74% yield) was obtained as a colorless oil. $^1$H-NMR (400 MHz, DMSO-d$_6$) δ 8.98 (s, 1H), 8.43 (d, J=7.7 Hz, 1H), 7.46-7.41 (m, 2H), 7.37 (d, J=8.2 Hz, 3H), 5.12 (d, J=3.5 Hz, 1H), 4.91 (q, J=6.9 Hz, 1H), 4.54 (d, J=9.7 Hz, 1H), 4.44 (t, J=8.2 Hz, 1H), 4.28 (br s, 1H), 3.63-3.47 (m, 15H), 3.30-3.26 (m, 2H), 3.17 (s, 3H), 2.80 (br d, J=4.4 Hz, 3H), 2.45 (s, 3H), 1.77 (ddd, J=4.5, 8.5, 12.9 Hz, 1H), 1.43-1.35 (m, 12H), 0.94 (s, 9H).

Step 7: Preparation of tert-butyl (2S,4R)-1-((S)-8-(tert-butyl)-16-oxo-5,8,11,14-tetraoxa-2,17-diazanonadecan-19-oyl)-4-hydroxy-N—((S)-1-(4-(4-methylthiazol-5-yl)phenyl)ethyl)pyrrolidine-2-carboxamide

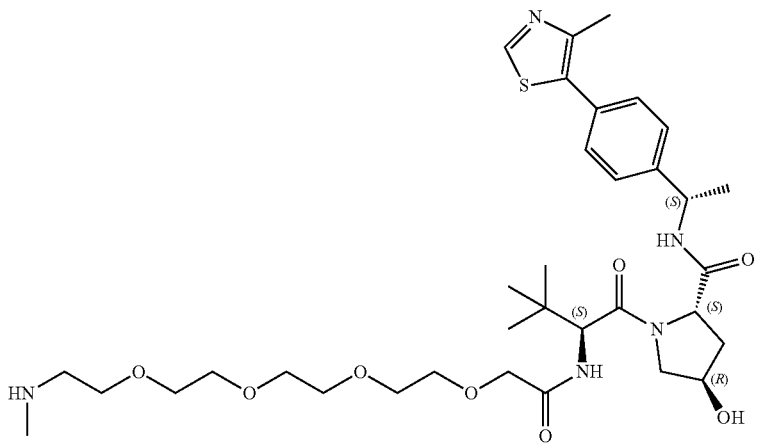

To a solution of tert-butyl N-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl]-N-methyl-carbamate (120 mg, 0.15 mmol, 1 eq) in dichloromethane (4 mL) was added hydrochloride/dioxane (4 M, 4 mL, 105.60 eq), then stirred at 15° C. for 2 hours. The reaction mixture was concentrated in vacuum to give (2S,4R)-1-[(2S)-3,3-dimethyl-2-[[2-[2-[2-[2-[2-(methylamino)ethoxy]ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (120 mg, hydrochloride) was obtained as a colorless oil.

Exemplary Synthesis of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride Step 1: Preparation of 4-(4-methylthiazol-5-yl)benzonitrile

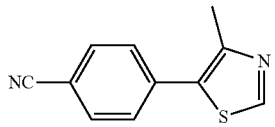

Into a 1-L round-bottom flask purged and maintained with an inert atmosphere of nitrogen, was placed a solution of 4-bromobenzonitrile (20 g, 109.88 mmol, 1.00 equiv) in DMA (250 mL), 4-methyl-1,3-thiazole (21.88 g, 220.67 mmol, 2.00 equiv), Pd(OAc)$_2$ (743 mg, 3.31 mmol, 0.03 equiv) and KOAc (21.66 g, 220.71 mmol, 2.00 equiv). The resulting solution was stirred for 5 hours at 150° C. The reaction mixture was cooled with a water/ice bath and diluted with 1 L of water. The resulting solution was extracted with 3×300 mL of ethyl acetate. The combined organic layers were washed with 3×300 mL of water and 1×300 mL of brine, then dried over anhydrous sodium sulfate and concentrated under vacuum. The residue was purified on combi-flash with ethyl acetate/petroleum ether (1:100-1:5). This resulted in 20 g (91%) of 4-(4-methyl-1,3-thiazol-5-yl)benzonitrile as a beige solid.

Step 2: Preparation of (4-(4-methylthiazol-5-yl)phenyl)methanamine

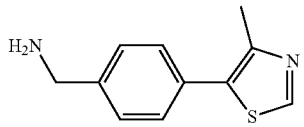

Into a 3-L 3-necked round-bottom flask purged and maintained with an inert atmosphere of nitrogen, was placed 4-(4-methyl-1,3-thiazol-5-yl)benzonitrile (35 g, 174.77 mmol, 1.00 equiv) in tetrahydrofuran (1000 mL). This was followed by the addition of LiAlH$_4$ (20 g, 526.32 mmol, 3.00 equiv) in portions at 0° C. in 10 minutes. The resulting solution was stirred for 3 hours at 60° C. in an oil bath. The reaction was cooled to 0° C. with a water/ice bath, then quenched by the addition of 20 mL of water, 20 mL of NaOH (15%) and 60 mL of water. The resulting solution was diluted with 200 mL of ethyl acetate. The solids were filtered out. The filtrate was dried over anhydrous sodium sulfate and concentrated under vacuum. The residue was applied onto a silica gel column with dichloromethane/methanol (10:1). This resulted in 20 g (56%) of [4-(4-methyl-1,3-thiazol-5-yl)phenyl]methanamine as yellow oil.

Step 3: Preparation of tert-butyl (2S,4R)-4-hydroxy-2-((4-(4-methylthiazol-5-yl)benzyl)carbamoyl)pyrrolidine-1-carboxylate

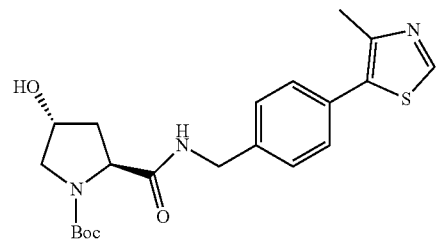 [SMILES: Cc1ncsc1-c1ccc(CNC(=O)[C@@H]2C[C@@H](O)CN2C(=O)OC(C)(C)C)cc1]

Into a 50-mL round-bottom flask, was placed (2S,4R)-1-[(tert-butoxy)carbonyl]-4-hydroxypyrrolidine-2-carboxylic acid (2.7 g, 11.68 mmol, 1.20 equiv) in N,N-dimethylformamide (30 mL), DIEA (2.52 g, 19.50 mmol, 1.20 equiv), HATU (4.47 g, 11.76 mmol, 1.20 equiv), [4-(4-methyl-1,3-thiazol-5-yl)phenyl]methanamine (2 g, 9.79 mmol, 1.00 equiv). The resulting solution was stirred overnight at 25° C. The reaction was then quenched by the addition of 20 mL of water and extracted with 3×20 mL of ethyl acetate. The organic layers combined, dried over anhydrous sodium sulfate and concentrated under vacuum. The residue was applied onto a silica gel column with dichloromethane/methanol (20:1). This resulted in 1 g (24%) of tert-butyl (2S,4R)-4-hydroxy-2-([[4-(4-methyl-1,3-thiazol-5-yl)phenyl]methyl]carbamoyl)pyrrolidine-1-carboxylate as a yellow solid.

Step 4: Preparation of (2S,4R)-4-hydroxy-N-(4-(4-methylthiazol-5-yl)benzyl)pyrrolidine-2-carboxamide hydrochloride

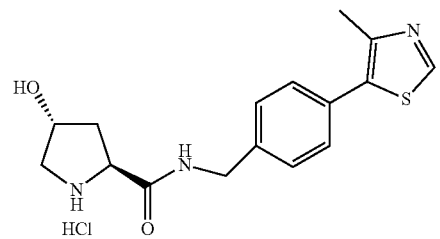 [SMILES: Cc1ncsc1-c1ccc(CNC(=O)[C@@H]2C[C@@H](O)CN2)cc1 ; Cl]

Into a 1000-mL round-bottom flask, was placed tert-butyl (2S,4R)-4-hydroxy-2-([[4-(4-methyl-1,3-thiazol-5-yl)phenyl]methyl]carbamoyl)pyrrolidine-1-carboxylate (45 g, 107.78 mmol, 1.00 equiv), a solution of hydrogen chloride (13.44 L) in dioxane (300 mL). The resulting solution was stirred for 2 hours at 20° C. The solids were collected by filtration. This resulted in 37.3 g (98%) of (2S,4R)-4-hydroxy-N-[[4-(4-methyl-1,3-thiazol-5-yl)phenyl]methyl]pyrrolidine-2-carboxamide hydrochloride as a yellow solid.

Step 5: Preparation of tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl) carbamate

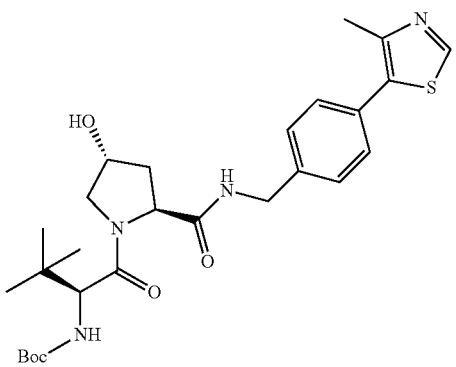 [SMILES: Cc1ncsc1-c1ccc(CNC(=O)[C@@H]2C[C@@H](O)CN2C(=O)[C@@H](NC(=O)OC(C)(C)C)C(C)(C)C)cc1]

Into a 1000-mL round-bottom flask, was placed (2S)-2-[[(tert-butoxy)carbonyl]amino]-3,3-dimethylbutanoic acid (15.73 g, 68.01 mmol, 1.20 equiv) in N,N-dimethylformamide (500 mL), DIEA (29.2 g, 225.94 mmol, 4.00 equiv), HATU (25.9 g, 68.12 mmol, 1.20 equiv) and (2S,4R)-2-amino-5-chloro-4-hydroxy-N-[[4-(4-methyl-1,3-thiazol-5-yl)phenyl]methyl]pentanamide (20 g, 56.52 mmol, 1.00 equiv). The resulting solution was stirred 16 hours at 20° C. The reaction was then quenched by the addition of 200 mL of water and extracted with 3×100 mL of ethyl acetate. The combined organic layers were dried over anhydrous sodium sulfate and concentrated under vacuum. The residue was applied onto a silica gel column with ethyl acetate/petroleum ether (2:1). This resulted in 15.2 g (51%) of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate as a yellow solid.

Step 6: Preparation of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride

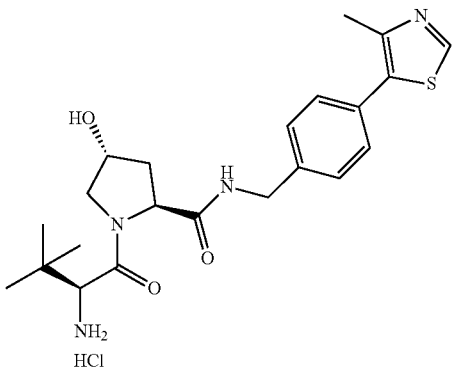 [SMILES: Cc1ncsc1-c1ccc(CNC(=O)[C@@H]2C[C@@H](O)CN2C(=O)[C@@H](N)C(C)(C)C)cc1 ; Cl]

Into a 500-mL round-bottom flask, was placed tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate (12 g, 22.61 mmol, 1.00 equiv) in dioxane (20 mL) and a solution of hydrogen chloride (3.584 L) in dioxane (80 mL). The resulting solution was stirred for 2 hours at 25° C. The solids were collected by filtration. This resulted in 5.1 g (48%) of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride as a yellow solid. LC/MS (ESI) m/z: 431 [M+1]$^+$; $^1$H-NMR (400 MHz, CD$_3$OD) δ 9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H).

Exemplary Synthesis of 1-(4-(azetidin-3-yl)piperazin-1-yl)-2-((4-chloro-2-hydroxy-5-(1-methylcyclopropyl)phenyl)amino)ethan-1-one hydrochloride

Step 1: Preparation of N-(4-chloro-2-methoxy-5-(1-methylcyclopropyl)phenyl)acetamide

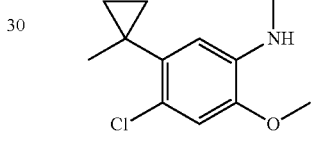

N-(4-chloro-2-methoxy-5-(1-methylcyclopropyl)phenyl)acetamide was prepared followed the procedure outlined in patent U.S. Patent Application Publication No. 2014/288045 A1, which is incorporated herein by reference in its entirety.

Step 2: Preparation of N-(4-chloro-2-hydroxy-5-(1-methylcyclopropyl)phenyl)acetamide

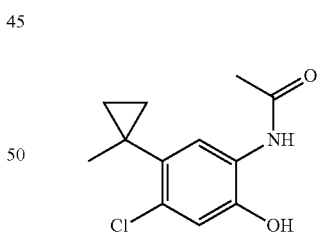

To a solution of N-(4-chloro-2-methoxy-5-(1-methylcyclopropyl)phenyl)acetamide (2.0 g, 7.88 mmol, 1.0 equiv) in EtSH (20 mL) was added AlCl$_3$ (10.5 g, 78.8 mmol, 1.0 eq) at 20° C. After stirring for 20 hours, the mixture was quenched with ice water. The pH was adjusted to ~9 with aq. NaHCO$_3$, and the mixture was extracted with EtOAc. The combined organic layers were washed with brine, dried over Na$_2$SO$_4$ and concentrated in vacuo. The residue was purified by column chromatography on silica gel with PE:EtOAc (1:1) to afford the desired product N-(4-chloro-2-hydroxy-5-(1-methylcyclopropyl)phenyl)acetamide (1.2 g, yield: 63.6%) as a yellow solid. LC/MS (ESI) m/z: 241.1 [M+1]$^+$.

Step 3: Preparation of 2-amino-5-chloro-4-(1-methylcyclopropyl)phenol

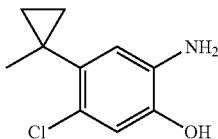

A solution of N-(4-chloro-2-hydroxy-5-(1-methylcyclopropyl)phenyl)acetamide (0.4 g, 2.51 mmol, 1.0 equiv) in EtOH/con.HCl (27.5 mL, 10/1, v/v) was stirred at 100° C. for 5 hours. After cooling to room temperature, the mixture was removed in vacuo to afford desired product 2-amino-5-chloro-4-(1-methylcyclopropyl)phenol (0.4 g, yield 100%) as a brown solid. LC/MS (ESI) m/z: 198.1 [M+1]$^+$.

Step 4: Preparation of ethyl (4-chloro-2-hydroxy-5-(1-methylcyclopropyl)phenyl)glycinate

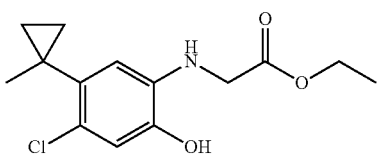 [SMILES: CCOC(=O)CNc1cc(C2(C)CC2)c(Cl)cc1O]

To a solution of 2-amino-5-chloro-4-(1-methylcyclopropyl)phenol (0.4 g, 2.0 mmol, 1.0 equiv) in MeOH (20 mL) were added AcOH (3 drops) and ethyl glyoxalate (306 mg, 3.0 mmol, 50% in toluene) at 20° C. After stirring for 2 hours, NaBH$_3$CN (378 mg, 6.0 mmol) was added. The resulting solution was stirred at 50° C. for 20 hours. Then the reaction was poured into ethyl acetate and aqueous solution. The organic phase was dried over Na$_2$SO$_4$, filtered and concentrated. The residue was purified by column chromatography on silica gel with PE:EtOAc (10:1) to give ethyl (4-chloro-2-hydroxy-5-(1-methylcyclopropyl)phenyl)glycinate (0.4 g, yield: 70.5%) as a yellow oil. LC/MS (ESI) m/z: 284.1 [M+1]$^+$.

Step 5: Preparation of (4-chloro-2-hydroxy-5-(1-methylcyclopropyl)phenyl)glycine

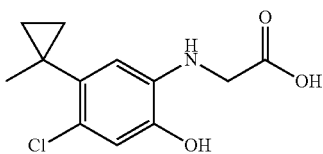 [SMILES: CC1(c2cc(NCC(=O)O)c(O)cc2Cl)CC1]

To a solution of ethyl (4-chloro-2-hydroxy-5-(1-methylcyclopropyl)phenyl)glycinate (0.4 g, 1.48 mmol, 1.0 equiv) in THF/H$_2$O (16 Ml, 3/1, v/v) was added LiOH (620 mg, 14.8 mmol) at 25° C. After stirring for 1 hour, the pH was adjusted to ~2 with 1M HCl. The mixture was taken up with EtOAc. The organic phase was dried over Na$_2$SO$_4$, filtered and concentrated to give (4-chloro-2-hydroxy-5-(1-methylcyclopropyl)phenyl)glycine (0.18 g) as a brown oil.

$^1$H-NMR (400 MHz, CD$_3$OD) δ 6.66 (s, 1H), 6.25 (s, 1H), 5.38 (q, J=6.4 Hz, 1H), 3.86 (s, 2H), 1.90 (s, 3H), 1.72 (dd, J=6.8 Hz, 3H).

Step 6: Preparation of benzyl 4-(1-(tert-butoxycarbonyl)azetidin-3-yl)piperazine-1-carboxylate

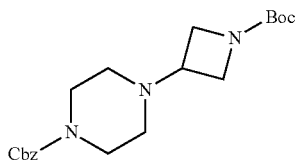 [SMILES: CC(C)(C)OC(=O)N1CC(N2CCN(C(=O)OCc3ccccc3)CC2)C1]

To a solution of benzyl piperazine-1-carboxylate (10 g, 45.4 mmol) and tert-butyl 3-oxoazetidine-1-carboxylate (8.5 g, 49.6 mmol) in MeOH (200 mL) was added AcOH (3 mL). After stirred at 25° C. for 1 hour, NaBH$_3$CN (8.5 g, 136.2 mmol) was added to the mixture and the resulting mixture was stirred at 25° C. for 16 hours. The mixture was quenched with aq. NaHCO$_3$ and extracted with EtOAc. The organic layer was washed with brine, dried over Na$_2$SO4 and concentrated. The residue was purified by column chromatography on silica gel with PE:EtOAc (5:1) to give benzyl 4-(1-(tert-butoxycarbonyl)azetidin-3-yl)piperazine-1-carboxylate (12.6 g, yield: 75%) as a white solid. $^1$H-NMR (400 MHz, CDCl$_3$) δ 7.38-7.30 (m, 5H), 5.13 (s, 2H), 4.17-4.09 (m, 2H), 3.94-3.90 (m, 2H), 3.59-3.52 (m, 4H), 3.09-3.04 (m, 1H), 2.30 (s, 4H), 1.43 (s, 9H).

Step 7: Preparation of tert-butyl 3-(piperazin-1-yl)azetidine-1-carboxylate

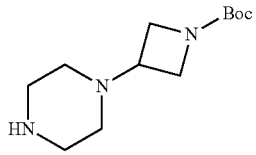

To a solution of benzyl 4-(1-(tert-butoxycarbonyl)azetidin-3-yl)piperazine-1-carboxylate (1.7 g, 4.53 mmol) in methanol (50 mL) was added Pd/C (0.5 g, 10%). The resulting mixture was stirred under H$_2$ at 25° C. for 20 h. The mixture was filtered, evaporated under reduced pressure to afford tert-butyl 3-(piperazin-1-yl)azetidine-1-carboxylate (950 mg, yield: 87%) as a colorless oil.

Step 8: Preparation of tert-butyl 3-(4-((4-chloro-2-hydroxy-5-(1-methylcyclopropyl)phenyl)glycyl)piperazin-1-yl)azetidine-1-carboxylate

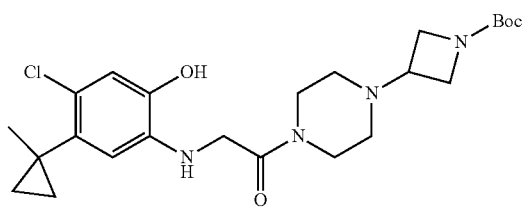 [SMILES: CC(C)(C)OC(=O)N1CC(N2CCN(C(=O)CNc3cc(C4(C)CC4)c(Cl)cc3O)CC2)C1]

To a solution of tert-butyl 3-(piperazin-1-yl)azetidine-1-carboxylate (250 mg, 1.03 mmol) were added DIEA (530 mg, 4.1 mmol), (4-chloro-2-hydroxy-5-(1-methylcyclopropyl)phenyl)glycine (290 mg, 1.13 mmol) and PyBOP (1.07 g, 2.06 mmol). The mixture was stirred at 20° C. for 1 hour. The mixture was quenched with water and extracted with EtOAc. The organic layer was washed with brine, dried over Na$_2$SO$_4$ and concentrated. The residue was purified by column chromatography on silica gel with DCM:MeOH (50:1-20:1) to give tert-butyl 3-(4-((4-chloro-2-hydroxy-5-(1-methylcyclopropyl)phenyl)glycyl)piperazin-1-yl)azetidine-1-carboxylate (210 mg, yield: 43%) as a brown oil. LC/MS (ESI) m/z: 479.2 [M+1]$^+$; $^1$H-NMR (400 MHz, CDCl$_3$) δ 6.84-6.79 (m, 1H), 6.43 (s, 1H), 3.96-3.88 (m, 4H), 3.82-3.79 (m, 2H), 3.71 (s, 2H), 3.48 (d, J=4.0 Hz, 2H), 3.11-3.08 (m, 1H), 2.36 (d, J=4.0 Hz, 4H), 1.93 (s, 2H), 1.82-1.73 (m, 3H), 1.41 (s, 9H), 1.26-1.23 (m. 2H).

Step 9: Preparation of 1-(4-(azetidin-3-yl)piperazin-1-yl)-2-((4-chloro-2-hydroxy-5-(1-methylcyclopropyl)phenyl)amino)ethan-1-one hydrochloride

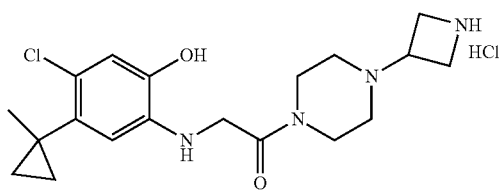 [SMILES: CC1(c2cc(NCC(=O)N3CCN(C4CNC4)CC3)c(O)cc2Cl)CC1 ; Cl]

A solution of tert-butyl 3-(4-((4-chloro-2-hydroxy-5-(1-methylcyclopropyl)phenyl)glycyl)piperazin-1-yl)azetidine-1-carboxylate (210 mg, 0.44 mmol) in in dioxane (2 mL) and HCl (6M in dioxane, 1 mL). The resulting mixture was stirred at 20° C. for 0.5 h. The mixture was concentrated to give 1-(4-(azetidin-3-yl)piperazin-1-yl)-2-((4-chloro-2-hydroxy-5-(1-methylcyclopropyl)phenyl)amino)ethan-1-one hydrochloride (120 mg, yield: 66%) as a white solid. LC/MS (ESI) m/z: 379.2 [M+1]$^+$.

Exemplary Synthesis of tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate Step 1: Preparation of tert-butyl (S)-2-carbamoylpyrrolidine-1-carboxylate

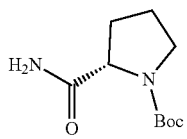

To a mixture of (tert-butoxycarbonyl)-L-proline (20.3 g, 94.20 mmol) and triethylamine (16 ml) in tetrahydrofuran (80 ml) was added a solution of methyl 2-chloroacetate (30.0 g, 245.9 mmol) in tetrahydrofuran (40 ml) was at −10° C. After stirring for 30 minutes, to the reaction mixture was added ammonium hydroxide (30 ml) at −10° C. The resulting mixture was stirred at room temperature overnight. The volatiles were evaporated under reduced pressure to a residue which was taken up with ethyl acetate (100 ml), wash with aqueous solution of sodium bicarbonate (sat 40 ml), then brine (40 ml), dried over anhydrous sodium sulfate, and concentrated under reduced pressure to give a tert-butyl (S)-2-carbamoylpyrrolidine-1-carboxylate (22.0 g) as colorless oil.

Step 2: Preparation of tert-butyl (S)-2-carbamothioylpyrrolidine-1-carboxylate

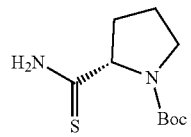 [SMILES: CC(C)(C)OC(=O)N1CCC[C@H]1C(N)=S]

A mixture of (S)-2-carbamoylpyrrolidine-1-carboxylate (22.0 g) in tetrahydrofuran (80 ml) and Lawesson reagent (41.8 g, 103.40 mmol) was stirred at 70° C. for 2 hours. The mixture was partitioned between ethyl acetate (400 ml) and water (400 ml). The organic layer was collected, washed with brine (300 ml), dried over anhydrous sodium sulfate, and concentrated under reduced pressure to afford a crude residue which was purified by silica gel flash chromatography (eluted with 20% ethyl acetate in hexane) to afford tert-butyl (S)-2-carbamothioylpyrrolidine-1-carboxylate (8.3 g, 38% yield) as white solid. LC/MS (ESI) m/z: 231.0 [M+1]$^+$.

Step 3: Preparation of ethyl (S)-2-(1-(tert-butoxycarbonyl)pyrrolidin-2-yl)thiazole-4-carboxylate

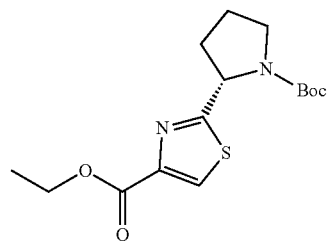 [SMILES: CCOC(=O)c1csc([C@@H]2CCCN2C(=O)OC(C)(C)C)n1]

A mixture of tert-butyl (S)-2-carbamothioylpyrrolidine-1-carboxylate (8.3 g, 40.4 mmol) and ethyl 3-bromo-2-oxopropanoate (13.8 g, 56.6 mmol) in ethanol (80 ml) was stirred at 60° C. for 2 hours. The volatiles were evaporated under reduced pressure to give a crude residue, which was taken up in saturated aqueous solution of sodium bicarbonate (10.6 g, 100 mmol in 80 ml water)-tetrahydrofuran (80 mL). To the resulting mixture was added di-tert-butyl dicarbonate (8.81 g, 40.4 mmol), and stirred at room temperature for 2 hours. The volatiles were evaporated under reduced pressure, and the resulting aqueous solution was extracted with ethyl acetate (300 ml). The organic layer was collected, washed with brine (150 ml), dried over anhydrous sodium sulfate, and concentrated under reduced pressure to give a crude residue which was purified by silica gel flash chromatography (eluted with 20% ethyl acetate in hexane) to afford ethyl (S)-2-(1-(tert-butoxycarbonyl)pyrrolidin-2-yl)thiazole-4-carboxylate (6.8 g, 52% yield) as colorless oil. LC/MS (ESI) m/z: 327.0 [M+1]$^+$.

Step 4: Preparation of (S)-2-(1-(tert-butoxycarbonyl)pyrrolidin-2-yl)thiazole-4-carboxylic acid

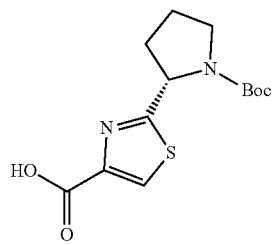

A mixture of ethyl (S)-2-(1-(tert-butoxycarbonyl)pyrrolidin-2-yl)thiazole-4-carboxylate (6.8 g, 20.90 mmol) and sodium hydroxide (1.67 g, 41.8 mmol) in methanol (30 ml)-water (30 ml) was stirred at room temperature for 1 hour. The volatiles were evaporated under reduced pressure. The resulting aqueous solution was acidified with aqueous hydrochloride acid (1N) to pH to 3-4, and extracted ethyl acetate (60 ml). The organic layer was collected, washed with brine (20 ml), dried over anhydrous sodium sulfate, and concentrated under reduced pressure to afford (S)-2-(1-(tert-butoxycarbonyl)pyrrolidin-2-yl)thiazole-4-carboxylic acid (4.5 g, 72% yield) as white solid. LC/MS (ESI) m/z: 299.0 [M+1]$^+$.

Step 5: Preparation of tert-butyl (S)-2-(4-(methoxy(methyl)carbamoyl)thiazol-2-yl)pyrrolidine-1-carboxylate

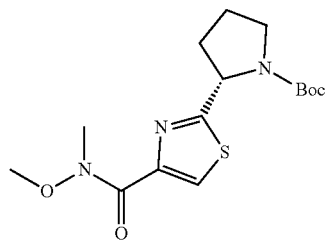 [SMILES: CON(C)C(=O)c1csc([C@@H]2CCCN2C(=O)OC(C)(C)C)n1]

To a mixture of (S)-2-(1-(tert-butoxycarbonyl)pyrrolidin-2-yl)thiazole-4-carboxylic acid (3.88 g, 15.10 mmol), N,O-dimethylhydroxylamine hydrochloride (1.53 g, 15.60 mmol) and N-ethyl-N-isopropylpropan-2-amine (5.03 g, 39.0 mmol) in N,N-dimethylformamide (20 ml) were added 1-Ethyl-3-(3-dimethylaminopropyl)carbodiimide hydrochloride (3.25 g, 16.90 mmol) and 1-Hydroxybenzotriazole (2.11 g, 15.60 mmol) at 0° C., the resulting mixture was allowed to warm to room temperature and stirred at room temperature for 12 hours. The mixture was partitioned between ethyl acetate (200 ml) and water (100 ml). The organic layer was collected, washed with water (100 ml×2) then brine (100 ml), dried over anhydrous sodium sulfate, and concentrated under reduced pressure to afford a crude residue which was purified by silica gel flash chromatography (eluted with 20% ethyl acetate in hexane) to afford tert-butyl (S)-2-(4-(methoxy(methyl)carbamoyl)thiazol-2-yl)pyrrolidine-1-carboxylate (3.46 g, 78% yield) as colorless oil. LC/MS (ESI) m/z: 342.0 [M+1]$^+$.

Step 6: Preparation of tert-butyl (S)-2-(4-(3-methoxybenzoyl)thiazol-2-yl)pyrrolidine-1-carboxylate

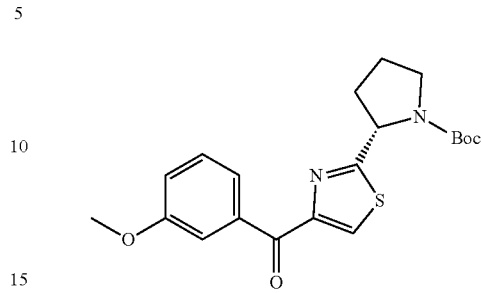

To a mixture of tert-butyl (S)-2-(4-(methoxy(methyl)carbamoyl)thiazol-2-yl)pyrrolidine-1-carboxylate (3.3 g, 9.46 mmol) in anhydrous tetrahydrofuran (30 ml) as added (3-methoxyphenyl)magnesium bromide (28.4 ml, 28.40 mmol) was dropped at −40° C., the mixture was stirred at −40° C. for 1 hour. The mixture was quenched with ammonium chloride solution (100 ml) at −0° C. The resulting mixture was extracted with ethyl acetate (30 ml×3). The organic layers were collected, washed with brine (80 ml), dried over anhydrous sodium sulfate, and concentrated under reduced pressure to give a crude residue which was purified silica gel flash chromatography (eluted with 20% ethyl acetate in hexane) to afford (S)-tert-butyl 2-(4-(3-methoxybenzoyl)thiazol-2-yl)pyrrolidine-1-carboxylate (3.49 g, 95% yield) as colorless oil. LC/MS (ESI) m/z: 389.1 [M+1]$^+$.

Step 7: Preparation of (S)-(3-hydroxyphenyl)(2-(pyrrolidin-2-yl)thiazol-4-yl)methanone

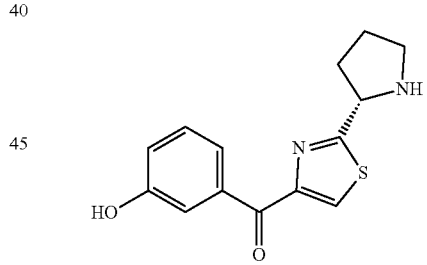

To a mixture of tert-butyl (S)-2-(4-(methoxy(methyl)carbamoyl)thiazol-2-yl)pyrrolidine-1-carboxylate (3.49 g, 8.99 mmol) in dichloromethane (20 ml), a solution of tribromo borane (4.2 ml) in dichloromethane (10 ml) was added at −45° C., the mixture was stirred at −45° C. for 1 hour. The mixture was quenched with methanol (1 ml) at −78° C. After warmed to room temperature, the resulting mixture was partitioned between dichloromethane (30 ml) and water (30 ml). The organic layer was collected, washed with brine (15 ml), dried over anhydrous sodium sulfate, and concentrated under reduced pressure to give a crude residue which was purified silica gel flash chromatography (eluted with 5% methanol in dichloromethane) to afford (S)-tert-butyl 2-(4-(3-methoxybenzoyl)thiazol-2-yl)pyrrolidine-1-carboxylate (1.25 g, 51% yield) as colorless oil. LC/MS (ESI) m/z: 275.1 [M+1]$^+$.

Step 8: Preparation of tert-butyl ((S)-1-cyclohexyl-2-((S)-2-(4-(3-hydroxybenzoyl)thiazol-2-yl)pyrrolidin-1-yl)-2-oxoethyl)carbamate

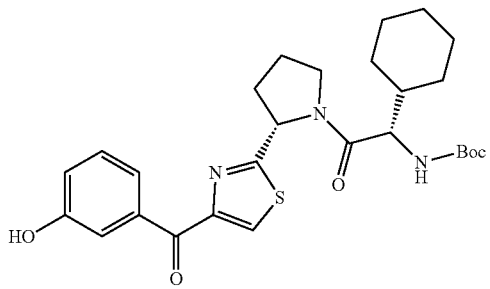 [SMILES: CC(C)(C)OC(=O)N[C@H](C(=O)N1CCC[C@H]1c1nc(C(=O)c2cccc(O)c2)cs1)C1CCCCC1]

To a mixture of (S)-tert-butyl 2-(4-(3-methoxybenzoyl)thiazol-2-yl)pyrrolidine-1-carboxylate (1.20 g, 4.38 mmol), (S)-2-((tert-butoxycarbonyl)amino)-2-cyclohexylacetic acid (2.81 g, 10.95 mmol) and N-ethyl-N-isopropylpropan-2-amine (5.65 g, 43.80 mmol) in N,N-dimethylformamide (10 ml) were added 1-Ethyl-3-(3-dimethylaminopropyl)carbodiimide hydrochloride (2.52 g, 13.14 mmol), 1-Hydroxybenzotriazole (1.77 g, 13.14 mmol) at 0° C., the resulting mixture was allowed to warm to room temperature and stirred at room temperature for 1 hour. The mixture was partitioned between ethyl acetate (30 ml) and water (30 ml). The organic layer was collected, washed with brine (15 ml), dried over anhydrous sodium sulfate, and concentrated under reduced pressure to give a crude residue which was taken up in methanol, potassium carbonate (1.51 g, 10.95 mmol) was added, the mixture was stirred at room temperature for 2 hours. The mixture was filtered and concentrated under reduced pressure to give a crude residue which was purified silica gel flash chromatography (eluted with 20% ethyl acetate in hexane) to afford to afford tert-butyl ((S)-1-cyclohexyl-2-((S)-2-(4-(3-hydroxybenzoyl)thiazol-2-yl)pyrrolidin-1-yl)-2-oxoethyl)carbamate (1.35 g, 60% yield) as colorless oil. LC/MS (ESI) m/z: 514.2 $[M+1]^+$.

Step 9: Preparation of (S)-2-amino-2-cyclohexyl-1-((S)-2-(4-(3-hydroxybenzoyl)thiazol-2-yl)pyrrolidin-1-yl)ethan-1-one

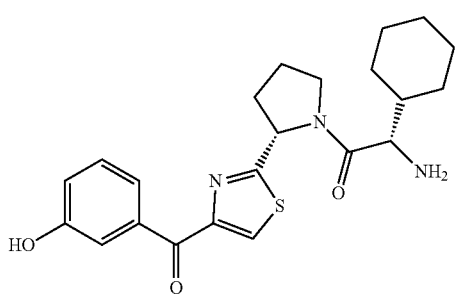 [SMILES: N[C@H](C(=O)N1CCC[C@H]1c1nc(C(=O)c2cccc(O)c2)cs1)C1CCCCC1]

To a mixture of tert-butyl ((S)-1-cyclohexyl-2-((S)-2-(4-(3-hydroxybenzoyl)thiazol-2-yl) pyrrolidin-1-yl)-2-oxoethyl)carbamate (1.34 g, 2.61 mmol) in dichloromethane (5 ml), 1 M hydrochloride in dioxane (1.0 ml) was added, the mixture was stirred at room temperature for 1.5 hours. The volatiles were evaporated under reduced pressure to give a residue which was basified with saturated aqueous solution of sodium bicarbonate, extracted with dichloromethane (20 ml×2). The organic layers were collected, washed with brine (15 ml), dried over anhydrous sodium sulfate, and concentrated under reduced pressure to afford a (S)-2-amino-2-cyclohexyl-1-((S)-2-(4-(3-hydroxybenzoyl)thiazol-2-yl)pyrrolidin-1-yl)ethanone (980 mg) as light yellow oil. LC/MS (ESI) m/z: 414.1 $[M+1]^+$.

Step 10: Preparation of tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate

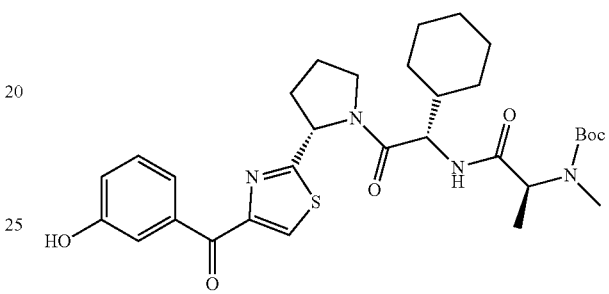

To a mixture of (S)-2-amino-2-cyclohexyl-1-((S)-2-(4-(3-hydroxybenzoyl)thiazol-2-yl) pyrrolidin-1-yl)ethanone (980 mg, 2.37 mmol) in dichloromethane (10 ml), N-ethyl-N-isopropylpropan-2-amine (5.03 g, 39.0 mmol) were added a solution of tert-butyl (S)-(1-(2,5-dioxopyrrolidin-1-yl)-1-oxopropan-2-yl)(methyl)carbamate (673 mg, 2.37 mmol) in dichloromethane (10 ml) at room temperature. The resulting mixture was stirred for 1 hour. The mixture was diluted with dichloromethane (30 ml) and washed with water (30 ml), dried over anhydrous sodium sulfate, and concentrated under reduced pressure to give a crude residue which was purified by silica gel flash chromatography (eluted with 20% ethyl acetate in hexane) to afford tert-butyl ((S)-1-(((S)-1-cyclohexyl-2-((S)-2-(4-(3-hydroxybenzoyl)thiazol-2-yl) pyrrolidin-1-yl)-2-oxoethyl)amino)-1-oxopropan-2-yl) (methyl)carbamate (895 mg, 62% yield) as white solid. LC/MS (ESI) m/z: 599.1 $[M+1]^+$.

Exemplary Synthesis of tert-butyl ((S)-1-(((S)-1-cyclohexyl-2-((S)-2-(4-(4-hydroxynaphthalen-1-yl)thiazol-2-yl)pyrrolidin-1-yl)-2-oxoethyl)amino)-1-oxopropan-2-yl)(methyl)carbamate Step 1: Preparation of methyl (S)-2-((S)-2-((tert-butoxycarbonyl)(methyl)amino)propanamido)-2-cyclohexylacetate

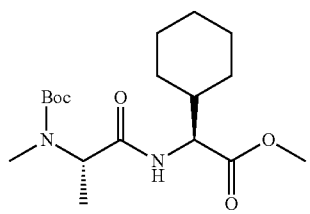

To a mixture of methyl (2S)-2-amino-2-cyclohexyl-acetate (1.60 g, 7.70 mmol, 1.00 eq, hydrogen chloride) and (2S)-2-[tert-butoxycarbonyl(methyl)amino]propanoic acid (1.57 g, 7.70 mmol, 1.00 eq) in dichloromethane (20 mL) was added O-(7-azabenzotriazole-1-yl)-N,N,N',N'-tetramethyluronium hexafluorophosphate (4.39 g, 11.56 mmol, 1.50 eq) and triethylamine (2.34 g, 23.11 mmol, 3.22 mL, 3.00 eq) in one portion. The mixture was stirred at 30° C. for 12 hours. The reaction mixture was washed with water (50 mL×2) and the organic phase was concentrated in vacuum. The residue was purified by column chromatography (Petroleum ether/Ethyl acetate=5/1) to give compound methyl (2S)-2-[[(2S)-2-[tert-butoxycarbonyl(methyl)amino]propanoyl]amino]-2-cyclohexyl-acetate (2.40 g, 6.73 mmol, 87% yield) as a white solid. LC/MS (ESI) m/z: 357.2 [M+1]⁺.

Step 2: Preparation of (S)-2-((S)-2-((tert-butoxycarbonyl)(methyl)amino)propanamido)-2-cyclohexylacetic acid

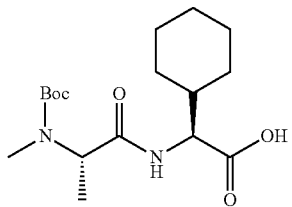 [SMILES: C[C@@H](C(=O)N[C@H](C(=O)O)C1CCCCC1)N(C)C(=O)OC(C)(C)C]

To a mixture of methyl (2S)-2-[[(2S)-2-[tert-butoxycarbonyl(methyl)amino]propanoyl]amino]-2-cyclohexyl-acetate (2.40 g, 6.73 mmol, 1.00 eq) in Tetrahydrofuran (15 mL) was added a mixture of lithium hydroxide (0.42 g, 10.10 mmol, 1.50 eq) in water (5 mL) in portions at 0° C. under Nitrogen. The mixture was stirred at 20° C. for 1 hour. The mixture was diluted with water (50 mL), extracted with ethyl acetate (50 mL×2). The water phase was adjusted pH to about 5 with hydrogen chloride solution (1 M). Then it was extracted with ethyl acetate (40 mL×3). The combined organic layer was washed with water (80 mL×2) and brine (80 mL×2), dried over anhydrous sodium sulfate, filtered and concentrated under reduced pressure to give the product. Compound (2S)-2-[[(2S)-2-[tert-butoxycarbonyl(methyl)amino]propanoyl]amino]-2-cyclohexyl-acetic acid (2.20 g, 6.42 mmol, 95% yield) was obtained as a white solid. LC/MS (ESI) m/z: 287.1 [M−55]⁺; ¹H-NMR (400 MHz, CDCl₃) δ 7.01-6.55 (m, 1H), 4.74 (br s, 1H), 4.52 (br dd, J=5.0, 8.3 Hz, 1H), 2.81 (d, J=3.3 Hz, 3H), 1.95-1.81 (m, 1H), 1.79-1.59 (m, 4H), 1.49 (s, 8H), 1.40-1.18 (m, 5H), 1.16-0.96 (m, 3H).

Step 3: Preparation of 1-(4-fluoronaphthalen-1-yl)ethan-1-one

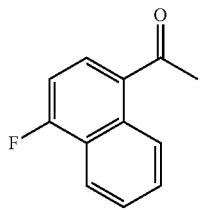

A mixture of 1-fluoronaphthalene (5.00 g, 34.21 mmol, 4.42 mL, 1.00 eq) and aluminum chloride (6.84 g, 51.31 mmol, 2.80 mL, 1.50 eq) in dichloromethane (50 mL) was added acetyl chloride (3.22 g, 41.05 mmol, 2.93 mL, 1.20 eq) in dichloromethane (10 mL) at 0° C. The mixture was stirred at 0° C. for 0.5 hour. Then the mixture was stirred at 20° C. for 4 hours. The mixture was pouring into water (60 mL), It was extracted with dichloromethane (50 mL×2). The combined organic layer was washed with water (80 mL×2) and brine (80 mL×2), dried over anhydrous sodium sulfate, filtered and concentrated under reduced pressure to give a residue. The residue was purified by column chromatography (petroleum ether/Ethyl acetate=1/0 to 20/1) to give compound 1-(4-fluoro-1-naphthyl) ethanone (5.40 g, 28.69 mmol, 84% yield) as a colorless oil. ¹H-NMR (400 MHz, CDCl₃) δ 8.94-8.86 (m, 1H), 8.17 (d, J=8.3 Hz, 1H), 7.98 (dd, J=5.4, 8.1 Hz, 1H), 7.71-7.65 (m, 1H), 7.64-7.58 (m, 1H), 7.16 (dd, J=8.1, 9.7 Hz, 1H), 2.84-2.67 (m, 3H).

Step 4: Preparation of 1-(4-(benzyloxy)naphthalen-1-yl)ethan-1-one

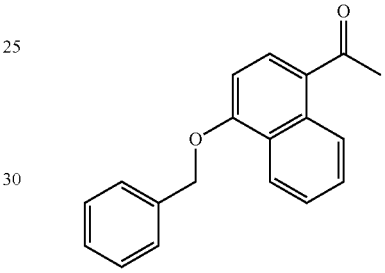

A mixture of phenylmethanol (4.48 g, 41.45 mmol, 4.31 mL, 1.50 eq) in dimethylformamide (60 mL) was added potassium tert-butoxide (4.65 g, 41.45 mmol, 1.50 eq) The mixture was stirred at 20° C. for 0.5 hour. Then 1-(4-fluoro-1-naphthyl) ethanone (5.20 g, 27.63 mmol, 1.00 eq) was added to the mixture. The mixture was stirred at 20° C. for 2 hours. The mixture was diluted with water (200 mL), extracted with ethyl acetate (100 mL×2). The combined organic layer was washed with water (100 mL×2) and brine (100 mL×2), dried over anhydrous sodium sulfate, filtered and concentrated under reduced pressure to give a residue. The residue was purified by column chromatography (petroleum ether/ethyl acetate=30/1 to 10/1) to give compound 1-(4-benzyloxy-1-naphthyl) ethanone (7.64 g, 22.80 mmol, 83% yield) as a white solid.

Step 5: Preparation of 1-(4-(benzyloxy)naphthalen-1-yl)-2-bromoethan-1-one

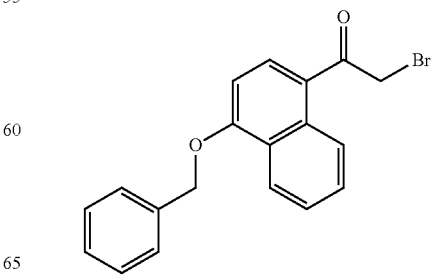

To a mixture of 1-(4-benzyloxy-1-naphthyl) ethanone (5.00 g, 18.09 mmol, 1.00 eq) in dichloromethane (300 mL) was added liquid bromine (2.89 g, 18.09 mmol, 932.78 uL, 1.00 eq) in portions at 20° C. under $N_2$. The mixture was stirred for 2 hours. The reaction mixture was quenched by addition of sat. sodium thiosulfate (50 mL) and the organic phase was concentrated in vacuum. The residue was purified by column chromatography (Petroleum ether/Ethyl acetate=30/1) to give compound 1-(4-benzyloxy-1-naphthyl)-2-bromo-ethanone (4.50 g, 12.67 mmol, 70% yield) as a white solid. LC/MS (ESI) m/z: 354.9 [M+1]$^+$.

Step 6: Preparation of tert-butyl (S)-2-(4-(4-(benzyloxy)naphthalen-1-yl)thiazol-2-yl)pyrrolidine-1-carboxylate

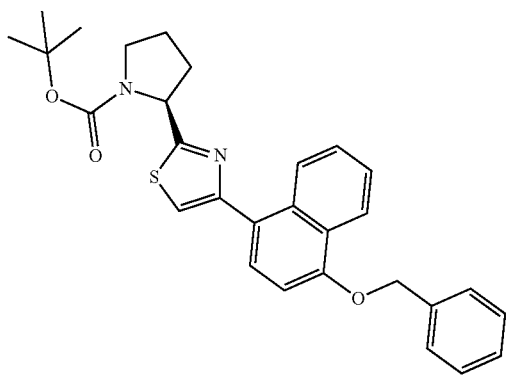 [SMILES: CC(C)(C)OC(=O)N1CCC[C@H]1c1nc(-c2ccc(OCc3ccccc3)c3ccccc23)cs1]

To a mixture of 1-(4-benzyloxy-1-naphthyl)-2-bromo-ethanone (3.90 g, 10.98 mmol, 1.00 eq) and tert-butyl (2S)-2-carbamothioylpyrrolidine-1-carboxylate (3.79 g, 16.47 mmol, 1.50 eq) in ethyl alcohol (80 mL) was added Pyridine (0.87 g, 10.98 mmol, 886.16 uL, 1.00 eq) under Nitrogen. The mixture was heated to 80° C. and stirred for 1 hour. The reaction mixture was concentrated in vacuum. The residue was purified by column chromatography (Petroleum ether/Ethyl acetate=5/1) to give compound tert-butyl (2S)-2-[4-(4-benzyloxy-1-naphthyl)thiazol-2-yl]pyrrolidine-1-carboxylate (5.30 g, 10.89 mmol, 99% yield) as a white solid. LC/MS (ESI) m/z: 487.3 [M+1]$^+$; $^1$H-NMR (400 MHz, CDCl$_3$) δ 8.49-8.37 (m, 1H), 8.35-8.31 (m, 1H), 8.23 (br s, 1H), 7.61-7.48 (m, 5H), 7.47-7.33 (m, 3H), 7.27 (s, 1H), 7.26 (br s, 1H), 6.93 (d, J=7.9 Hz, 1H), 5.32 (s, 2H), 3.77-3.42 (m, 2H), 2.48-2.25 (m, 2H), 2.14-1.94 (m, 3H), 1.57-1.34 (m, 9H).

Step 7: Preparation of (S)-4-(4-(benzyloxy)naphthalen-1-yl)-2-(pyrrolidin-2-yl)thiazole

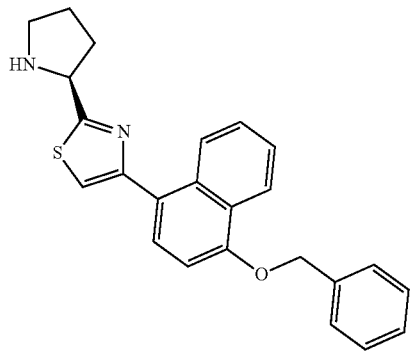 [SMILES: c1ccc(COc2ccc(-c3csc([C@@H]4CCCN4)n3)c3ccccc23)cc1]

To a mixture of tert-butyl (2S)-2-[4-(4-benzyloxy-1-naphthyl)thiazol-2-yl]pyrrolidine-1-carboxylate (2.00 g, 4.11 mmol, 1.00 eq) in Dichloromethane (36 mL) was added trifluoroacetic acid (18.12 g, 158.89 mmol, 11.76 mL, 38.66 eq) in one portion under $N_2$. The mixture was stirred at 30° C. for 1 hour. The reaction mixture was concentrated in vacuum. Compound 4-(4-benzyloxy-1-naphthyl)-2-[(2S)-pyrrolidin-2-yl]thiazole (2.06 g, trifluoroacetic acid) was obtained as a white solid. LC/MS (ESI) m/z: 387.2 [M+1]$^+$.

Step 8: Preparation of tert-butyl ((S)-1-(((S)-2-((S)-2-(4-(4-(benzyloxy)naphthalen-1-yl)thiazol-2-yl)pyrrolidin-1-yl)-1-cyclohexyl-2-oxoethyl)amino)-1-oxopropan-2-yl)(methyl)carbamate

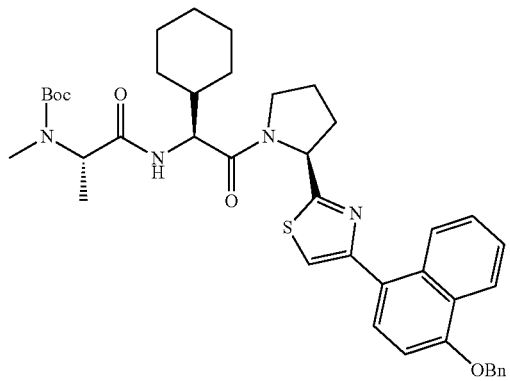 [SMILES: C[C@@H](C(=O)N[C@H](C(=O)N1CCC[C@H]1c1nc(-c2ccc(OCc3ccccc3)c3ccccc23)cs1)C1CCCCC1)N(C)C(=O)OC(C)(C)C]

To a mixture of (2S)-2-[[(2S)-2-[tert-butoxycarbonyl (methyl)amino]propanoyl]amino]-2-cyclohexyl-acetic acid (1.15 g, 3.36 mmol, 1 eq) 4-(4-benzyloxy-1-naphthyl)-2-[(2S)-pyrrolidin-2-yl]thiazole (2.02 g, 4.03 mmol, 1.2 eq, trifluoroacetic acid) and 4-methylmorpholine (1.36 g, 13.43 mmol, 1.48 mL, 4 eq) in tetrahydrofuran (40 mL) and dimethyl formamide (4 mL) was added 4-(4,6-dimethoxy-1,3,5-triazin-2-yl)-4-methyl-morpholin-4-ium; chloride; hydrate (1.98 g, 6.72 mmol, 2 eq). The mixture was stirred at 20° C. for 12 hours. The reaction mixture was quenched by addition water (30 mL) and extracted with ethyl acetate (30 mL×3), then the organic phase was concentrated in vacuum. The residue was purified by column chromatography (Petroleum ether/Ethyl acetate=5/1) to give compound tert-butyl N-[(1S)-2-[[(1S)-2-[(2S)-2-[4-(4-benzyloxy-1- naphthyl)thiazol-2-yl]pyrrolidin-1-yl]-1-cyclohexyl-2-oxo-ethyl]amino]-1-methyl-2-oxo-ethyl]-N-methyl-carbamate (0.80 g, 1.09 mmol, 33% yield, 97% purity) as a white solid. LC/MS (ESI) m/z: 711.3 [M+1]$^+$; $^1$H-NMR (400 MHz, CDCl$_3$) δ 8.46-8.39 (m, 1H), 8.25-8.18 (m, 1H), 8.03 (s, 1H), 7.59-7.49 (m, 5H), 7.47-7.34 (m, 3H), 7.25 (s, 1H), 6.92 (d, J=8.1 Hz, 1H), 5.70-5.61 (m, 1H), 4.79-4.59 (m, 2H), 3.96-3.78 (m, 2H), 2.97 (s, 2H), 2.89 (s, 2H), 2.82 (s, 3H), 2.47 (br s, 1H), 2.37-2.16 (m, 2H), 2.05 (s, 2H), 1.88-1.54 (m, 17H), 1.50 (s, 9H), 1.53-1.45 (m, 1H), 1.35 (d, J=7.1 Hz, 3H), 1.30-0.93 (m, 9H).

To a mixture of tert-butyl N-[(1S)-2-[[(1S)-2-[(2S)-2-[4-(4-benzyloxy-1-naphthyl)thiazol-2-yl]pyrrolidin-1-yl]-1-cyclohexyl-2-oxo-ethyl]amino]-1-methyl-2-oxo-ethyl]-N-methyl-carbamate (0.50 g, 0.70 mmol, 1.00 eq) in Methyl alcohol (10 mL) was added Hydroxide palladium (0.36 g, 2.53 mmol, 3.60 eq) and Hydrogen (0.01 g, 0.70 mmol, 1.00 eq) in one portion under Nitrogen. The mixture was stirred at 20° C. for 16 hours. The reaction mixture was filtered and the filtrate was concentrated in vacuum. Compound tert-butyl N-[(1S)-2-[[(1S)-1-cyclohexyl-2-[(2S)-2-[4-(4-hydroxy-1-naphthyl)thiazol-2-yl]pyrrolidin-1-yl]-2-oxo-ethyl]amino]-1-methyl-2-oxo-ethyl]-N-methyl-carbamate (0.3 g, 0.48 mmol, 69% yield) was obtained as a white solid. LC/MS (ESI) m/z: 621.3 [M+1]$^+$.

Step 9: Preparation of tert-butyl ((S)-1-(((S)-1-cyclohexyl-2-((S)-2-(4-(4-hydroxynaphthalen-1-yl)thiazol-2-yl)pyrrolidin-1-yl)-2-oxoethyl)amino)-1-oxopropan-2-yl)(methyl)carbamate Exemplary Synthesis of tert-butyl ((S)-1-(((S)-1-cyclohexyl-2-((S)-2-(4-(4-(2-(2-(2-(methylamino)ethoxy)ethoxy)ethoxy)naphthalen-1-yl)thiazol-2-yl)pyrrolidin-1-yl)-2-oxoethyl)amino)-1-oxopropan-2-yl)(methyl)carbamate

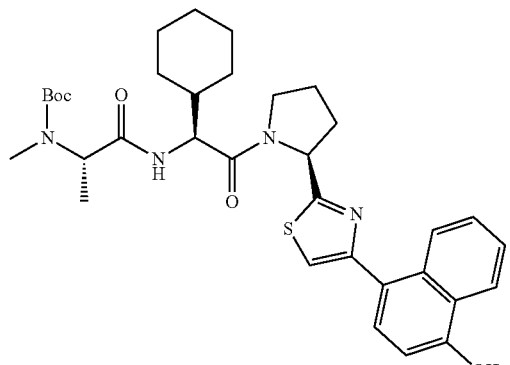

Step 1: Preparation of tert-butyl ((S)-1-(((S)-2-((S)-2-(4-(4-(2-(2-(2-bromoethoxy)ethoxy)ethoxy)naphthalen-1-yl)thiazol-2-yl)pyrrolidin-1-yl)-1-cyclohexyl-2-oxoethyl)amino)-1-oxopropan-2-yl)(methyl)carbamate

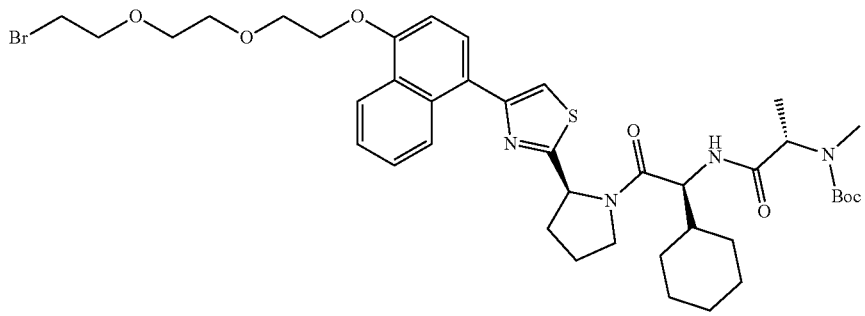 [SMILES: C[C@@H](C(=O)N[C@H](C(=O)N1CCC[C@H]1c1nc(-c2ccc(OCCOCCOCCBr)c3ccccc23)cs1)C1CCCCC1)N(C)C(=O)OC(C)(C)C]

To a mixture of tert-butyl N-[(1S)-2-[[(1S)-1-cyclohexyl-2-[(2S)-2-[4-(4-hydroxy-1-naphthyl)thiazol-2-yl]pyrrolidin-1-yl]-2-oxo-ethyl]amino]-1-methyl-2-oxo-ethyl]-N-methyl-carbamate (0.30 g, 0.48 mmol, 1.00 eq) and 1,2-bis(2-bromoethoxy)ethane (0.27 g, 0.97 mmol, 2.00 eq) in acetonitrile (12 mL) was added potassium carbonate (0.23 g, 1.69 mmol, 3.50 eq) under Nitrogen. The mixture was heated to 80° C. and stirred for 12 hours. The reaction mixture was washed with water (10 mL) and extracted with ethyl acetate (20 mL), then the organic phase was concentrated in vacuum. The residue was purified by column chromatography (Petroleum ether/Ethyl acetate=1/1) to give compound tert-butyl N-[(1S)-2-[[(1S)-2-[(2S)-2-[4-[4-[2-[2-(2-bromoethoxy)ethoxy]ethoxy]-1-naphthyl]thiazol-2-yl]pyrrolidin-1-yl]-1-cyclohexyl-2-oxo-ethyl]amino]-1-methyl-2-oxo-ethyl]-N-methyl-carbamate (0.15 g, 0.18 mmol, 38% yield) as a white solid. LC/MS (ESI) m/z: 817.3 [M+1]$^+$.

Step 2: Preparation of tert-butyl ((S)-1-(((S)-1-cyclohexyl-2-((S)-2-(4-(4-(2-(2-(2-(methylamino)ethoxy)ethoxy)ethoxy)naphthalen-1-yl)thiazol-2-yl)pyrrolidin-1-yl)-2-oxoethyl)amino)-1-oxopropan-2-yl)(methyl)carbamate A mixture of tert-butyl N-[(1S)-2-[[(1S)-2-[(2S)-2-[4-[4-[2-[2-(2-bromoethoxy)ethoxy]ethoxy]-1-naphthyl]thiazol-2-yl]pyrrolidin-1-yl]-1-cyclohexyl-2-oxo-ethyl]amino]-1-methyl-2-oxo-ethyl]-N-methyl-carbamate (0.14 g, 0.17 mmol, 1.00 eq) and methylamine/ethyl alcohol (10 mL) was heated to 60° C. and stirred for 12 hours. The reaction mixture was concentrated in vacuum. Compound tert-butyl N-[(1S)-2-[[(1S)-1-cyclohexyl-2-[(2S)-2-[4-[4-[2-[2-[2-(methylamino)ethoxy]ethoxy]ethoxy]-1-naphthyl]thiazol-2-yl]pyrrolidin-1-yl]-2-oxo-ethyl]amino]-1-methyl-2-oxo-ethyl]-N-methyl-carbamate (0.13 g) was obtained as a white solid. LC/MS (ESI) m/z: 766.4 [M+1]$^+$.

Exemplary Synthesis of tert-butyl (2-(2-(2-aminoethoxy)ethoxy)ethyl)(methyl)carbamate Step 1: Preparation of tert-butyl (2-(2-(2-(1,3-dioxoisoindolin-2-yl)ethoxy)ethoxy)ethyl)(methyl)carbamate

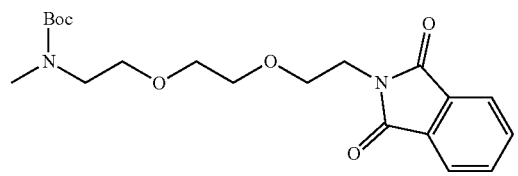

To a solution of 2-[2-[2-[tert-butoxycarbonyl(methyl)amino]ethoxy]ethoxy]ethyl 4-methylbenzenesulfonate (400 mg, 0.96 mmol, 1 eq) in N,N-dimethylformamide (10 mL) was added (1,3-dioxoisoindolin-2-yl)potassium (213 mg,

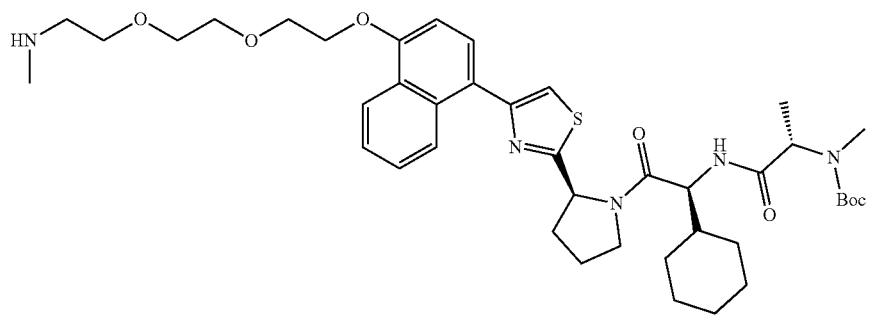 [SMILES: CNCCOCCOCCOc1ccc(-c2csc([C@@H]3CCCN3C(=O)[C@@H](NC(=O)[C@H](C)N(C)C(=O)OC(C)(C)C)C3CCCCC3)n2)c2ccccc12]

1.15 mmol, 1.2 eq). The mixture was stirred at 50° C. for 12 hours. The mixture was diluted with water (20 mL) and the aqueous phase was extracted with ethyl acetate (20 mL×3). The combined organic phase was washed with brine (20 mL), dried with anhydrous sodium sulfate, filtered and concentrated in vacuum. The residue was purified by prep-TLC (petroleum ether/ethyl acetate=3/1) to give tert-butyl N-[2-[2-[2-(1,3-dioxoisoindolin-2-yl)ethoxy]ethoxy]ethyl]-N-methyl-carbamate (300 mg, 0.76 mmol, 79% yield) as a colorless oil. LC/MS (ESI) m/z: 415.1 [M+23].

Step 2: Preparation of tert-butyl (2-(2-(2-aminoethoxy)ethoxy)ethyl)(methyl)carbamate

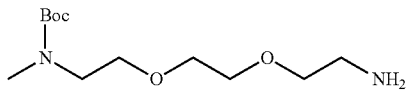 [SMILES: CN(CCOCCOCCN)C(=O)OC(C)(C)C]

To a solution of tert-butyl N-[2-[2-[2-(1,3-dioxoisoindolin-2-yl)ethoxy]ethoxy]ethyl]-N-methyl-carbamate (300 mg, 0.76 mmol, 1 eq) in ethanol (5 mL) was added hydrazine hydrate (382 mg, 7.64 mmol, 0.4 mL, 10 eq). The mixture was stirred at 80° C. for 12 hours. The mixture was diluted with water (20 mL) and the aqueous phase was extracted with dichloromethane (20 mL×3). The combined organic phase was washed with brine (20 mL), dried with anhydrous sodium sulfate, filtered and concentrated in vacuum. The residue was purified by prep-TLC (dichloromethane/methanol=5/2) to give tert-butyl N-[2-[2-(2-aminoethoxy)ethoxy]ethyl]-N-methyl-carbamate (120 mg, 0.46 mmol, 59% yield) as a colorless oil. $^1$H-NMR (400 MHz, CDCl$_3$) δ 3.66-3.56 (m, 6H), 3.55-3.49 (m, 2H), 3.40 (br s, 2H), 2.99-2.79 (m, 5H), 1.74 (br s, 3H), 1.46 (s, 9H).

Exemplary Synthesis of (2R,3S,4R,5S)-3-(3-chloro-2-fluorophenyl)-4-(4-chloro-2-fluorophenyl)-4-cyano-N-(2-methoxy-4-((2-(2-(2-(methylamino)ethoxy)ethoxy)ethyl)carbamoyl)phenyl)-5-neopentylpyrrolidine-2-carboxamide Step 1: Preparation of (Z)-3-(3-chloro-2-fluorophenyl)-2-(4-chloro-2-fluorophenyl)acrylonitrile

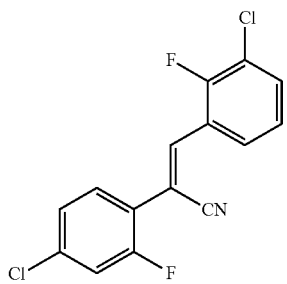 [SMILES: N#C/C(=C\c1cccc(Cl)c1F)c1ccc(Cl)cc1F]

To a mixture of 3-chloro-2-fluoro-benzaldehyde (13.7 g, 86.68 mmol, 1.05 eq) and 2-(4-chloro-2-fluoro-phenyl)acetonitrile (14 g, 82.56 mmol, 1 eq) in methanol (200 mL) was added the solution of sodium methoxide (13.4 g, 247.67 mmol, 3 eq) in methanol (40 mL) dropwise at 0° C. under nitrogen atmosphere. The product begins to precipitate during the addition. The suspension was stirred at 45° C. for 5 hours. The solid was filtered and washed with water (200 mL) and methanol (50 mL) and then was dried in vacuum to give (Z)-3-(3-chloro-2-fluoro-phenyl)-2-(4-chloro-2-fluorophenyl)prop-2-enenitrile (24 g, 77.39 mmol, 93% yield) as a white solid. $^1$H-NMR (400 MHz, CDCl$_3$) δ 8.20-8.10 (m, 1H), 7.81 (s, 1H), 7.64-7.49 (m, 2H), 7.33-7.20 (m, 3H).

Step 2: Preparation of ethyl 4-(2-(((benzyloxy)carbonyl)amino)acetamido)-3-methoxybenzoate

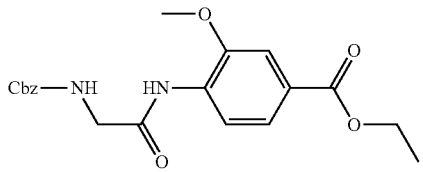

To a mixture of 2-(benzyloxycarbonylamino)acetic acid (5.9 g, 28.17 mmol, 1.1 eq) and ethyl 4-amino-3-methoxybenzoate (5 g, 25.61 mmol, 1 eq) in tetrahydrofuran (50 mL) was added O-(7-azabenzotriazol-1-yl)-N,N,N,N-tetramethyluronium hexafluorophosphate (11.7 g, 30.74 mmol, 1.2 eq) and N,N-diisopropylethylamine (6.6 g, 51.23 mmol, 8.9 mL, 2 eq) at 0° C. under nitrogen. The mixture was warmed to 20° C. and stirred for 12 hours. The mixture was diluted with water (100 mL) and extracted with ethyl acetate (100 mL×3). The combined organic phase was washed with brine (200 mL×2), dried with anhydrous sodium sulfate, filtered and concentrated in vacuum. The residue was purified by silica gel chromatography (petroleum ether/ethyl acetate=10/1, 3/1 to 1/1) to give ethyl 4-[[2-(benzyloxycarbonylamino)acetyl]amino]-3-methoxy-benzoate (9 g, 23.29 mmol, 91% yield) as a yellow oil. $^1$H-NMR (400 MHz, CDCl$_3$) δ 8.41 (br d, J=8.4 Hz, 2H), 7.68 (br d, J=8.4 Hz, 1H), 7.53 (s, 1H), 7.42-7.28 (m, 5H), 5.61 (br s, 1H), 5.18 (s, 2H), 4.42-4.32 (m, 2H), 4.11-4.01 (m, 2H), 3.88 (s, 3H), 1.40 (t, J=7.2 Hz, 3H).

Step 3: Preparation of ethyl 4-(2-aminoacetamido)-3-methoxybenzoate

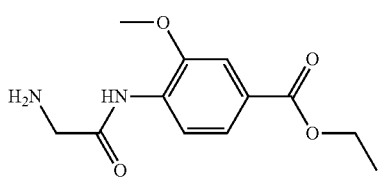 [SMILES: CCOC(=O)c1ccc(NC(=O)CN)c(OC)c1]

To a solution of ethyl 4-[[2-(benzyloxycarbonylamino)acetyl]amino]-3-methoxy-benzoate (8.8 g, 22.77 mmol, 1 eq) in ethanol (100 mL) was added palladium on activated carbon catalyst (1 g, 10% purity) under nitrogen atmosphere. The suspension was degassed under vacuum and purged with hydrogen several times. The mixture was stirred under hydrogen (15 psi) at 50° C. for 24 hours. Then the mixture was stirred under hydrogen (50 psi) at 50° C. for 5 hours. The reaction mixture was filtered and the filtrate was concentrated. The crude product was purified by silica gel chromatography (petroleum ether/ethyl acetate=10/1, 3/1 to 1/1) to give ethyl 4-[(2-aminoacetyl)amino]-3-methoxy-benzoate (3.2 g, 12.69 mmol, 56% yield) as a yellow oil. $^1$H-NMR (400 MHz, CDCl$_3$) δ 10.00 (br s, 1H), 8.53 (d, J=8.4 Hz, 1H), 7.71 (dd, J=1.6, 8.4 Hz, 1H), 7.57 (d, J=1.6 Hz, 1H), 4.38 (q, J=7.2 Hz, 2H), 3.97 (s, 3H), 3.53 (s, 2H), 1.40 (t, J=7.2 Hz, 3H).

Step 4: Preparation of ethyl (E)-4-(2-((3,3-dimethylbutylidene)amino)acetamido)-3-methoxybenzoate

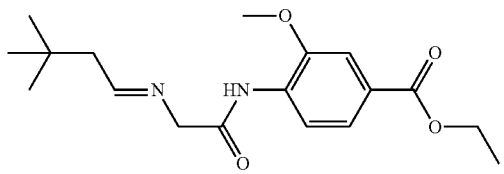 [SMILES: CCOC(=O)c1ccc(NC(=O)C/N=C/CC(C)(C)C)c(OC)c1]

To a mixture of ethyl 4-[(2-aminoacetyl)amino]-3-methoxy-benzoate (3.2 g, 12.69 mmol, 1 eq) and 3,3-dimethylbutanal (1.3 g, 12.94 mmol, 1.6 mL, 1.02 eq) in dichloromethane (50 mL) was added magnesium sulfate (3.0 g, 25.37 mmol, 2 eq) at 20° C. The mixture was stirred for 20 hours. The mixture was filtered and the filtrate was concentrated in vacuum to give ethyl 4-[[2-[(E)-3,3-dimethylbutylideneamino]acetyl]amino]-3-methoxy-benzoate (4.24 g, 12.68 mmol, 100% yield) as a yellow oil. $^1$H-NMR (400 MHz, CDCl$_3$) δ 9.45 (br s, 1H), 8.53 (d, J=8.4 Hz, 1H), 7.89-7.82 (m, 1H), 7.72-7.68 (m, 1H), 7.58-7.53 (m, 1H), 4.39-4.34 (m, 2H), 4.25-4.20 (m, 2H), 3.94 (s, 3H), 2.30-2.27 (m, 2H), 1.42-1.38 (m, 3H), 1.04 (s, 9H).

Step 5: Preparation of ethyl 4-((2R,3S,4R,5R)-3-(3-chloro-2-fluorophenyl)-4-(4-chloro-2-fluorophenyl)-4-cyano-5-neopentylpyrrolidine-2-carboxamido)-3-methoxybenzoate

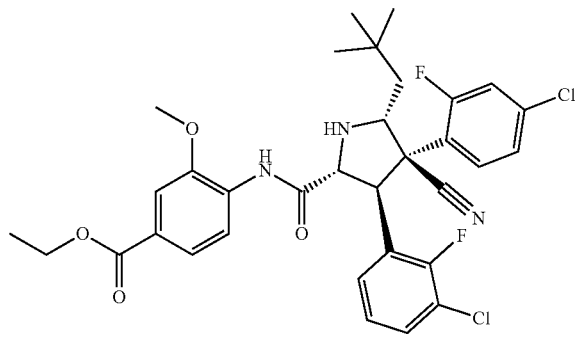 [SMILES: CCOC(=O)c1ccc(NC(=O)[C@@H]2N[C@H](CC(C)(C)C)[C@](C#N)(c3ccc(Cl)cc3F)[C@H]2c2cccc(Cl)c2F)c(OC)c1]

To a solution of [1-(2-diphenylphosphanyl-1-naphthyl)-2-naphthyl]-diphenyl-phosphane (530 mg, 0.85 mmol, 0.12 eq) in 2-methyltetrahydrofuran (10 mL) was added acetoxy-copper (95 mg, 0.78 mmol, 0.11 eq). The mixture was stirred at 20° C. for 30 minutes. Ethyl 4-[[2-[(E)-3,3-dimethylbutylideneamino]acetyl]amino]-3-methoxy-benzoate (2.6 g, 7.80 mmol, 1.1 eq) and (Z)-3-(3-chloro-2-fluoro-phenyl)-2-(4-chloro-2-fluoro-phenyl)prop-2-enenitrile (2.2 g, 7.09 mmol, 1 eq) in 2-methyltetrahydrofuran (100 mL) was added at 20° C. under nitrogen atmosphere. Then triethylamine (717 mg, 7.09 mmol, 1.0 mL, 1 eq) was added. The mixture was stirred at 20° C. for 36 hours. The mixture was diluted with water (100 mL) and extracted with ethyl acetate (100 mL×3). The combined organic phase was washed with brine (100 mL×2), dried with anhydrous sodium sulfate, filtered and concentrated in vacuum. The residue was purified by silica gel chromatography (petroleum ether/ethyl acetate=10/1 to 5/1) to give ethyl 4-[[(2R,3S,4R,5R)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoate (3 g, 4.65 mmol, 65% yield) as a yellow solid.

Step 6: Preparation of 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid

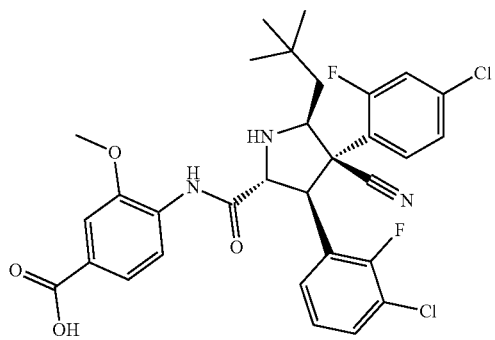 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

To a mixture of ethyl 4-[[(2R,3S,4R,5R)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoate (3.0 g, 4.65 mmol, 1 eq) in water (5 mL), tetrahydrofuran (5 mL) and methanol (5 mL) was added sodium hydroxide (937 mg, 23.44 mmol, 5.04 eq) at 20° C. The mixture was stirred at 20° C. for 12 hours. The mixture was then heated to 50° C. and stirred for another 12 hours. The mixture was diluted with water (20 mL) and acidified with 1N hydrochloride acid until pH=5. The product begins to precipitate during the addition. The solid was filtered and dried in vacuum to give the crude product. The solid was triturated with acetonitrile (100 mL) to give 4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoic acid (1.2 g, 1.91 mmol, 41% yield, 98% ee, 95% de, 98% purity) as a white solid. $^1$H-NMR (400 MHz, CD$_3$OD) δ 8.38 (d, J=8.4 Hz, 1H), 7.76-7.70 (m, 1H), 7.69-7.62 (m, 2H), 7.44-7.30 (m, 3H), 7.28-7.19 (m, 2H), 4.79-4.76 (m, 1H), 4.64 (d, J=8.0 Hz, 1H), 4.16-4.04 (m, 2H), 3.98 (s, 3H), 1.76-1.66 (m, 1H), 1.36 (br d, J=14.0 Hz, 1H), 1.04 (s, 9H).

Step 7: Preparation of tert-butyl (2-(2-(2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzamido)ethoxy)ethoxy)ethyl)(methyl)carbamate

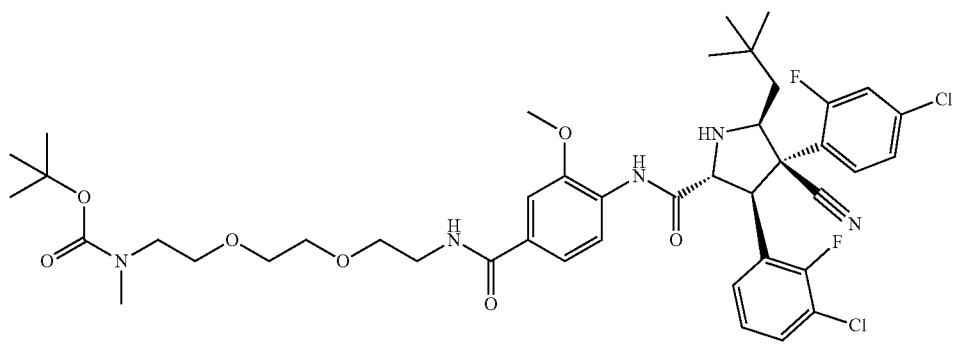 [SMILES: COc1cc(C(=O)NCCOCCOCCN(C)C(=O)OC(C)(C)C)ccc1NC(=O)[C@@H]1N[C@@H](CC(C)(C)C)[C@](C#N)(c2ccc(Cl)cc2F)[C@H]1c1cccc(Cl)c1F]

To the mixture of 4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoic acid (200 mg, 0.32 mmol, 1 eq) and tert-butyl N-[2-[2-(2-aminoethoxy)ethoxy]ethyl]-N-methyl-carbamate (85 mg, 0.32 mmol, 1 eq) in N,N-dimethylformamide (8 mL) was added 1-hydroxybenzotriazole (65 mg, 0.48 mmol, 1.5 eq), N-(3-dimethylaminopropyl)-N-ethyl-carbodiimide hydrochloride (93 mg, 0.48 mmol, 1.5 eq) and N,N-diisopropylethylamine (125 mg, 0.97 mmol, 0.17 mL, 3 eq). The mixture was stirred at 20° C. for 12 hours. The mixture was quenched with water (25 mL). Then it was extracted with ethyl acetate (25 mL×3). The combined organic layer was washed with water (35 mL×2) and brine (35 mL×2), dried over anhydrous sodium sulfate, filtered and concentrated under reduced pressure to give a residue. The residue was purified by prep-TLC (dichloromethane:methanol=10:1). tert-butyl N-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethyl]-N-methyl-carbamate (230 mg, 0.26 mmol, 82% yield) was obtained as a light yellow solid. LC/MS (ESI) m/z: 860.4 [M+1]$^+$.

Step 8: Preparation of (2R,3S,4R,5S)-3-(3-chloro-2-fluorophenyl)-4-(4-chloro-2-fluorophenyl)-4-cyano-N-(2-methoxy-4-((2-(2-(2-(methylamino)ethoxy)ethoxy)ethyl)carbamoyl)phenyl)-5-neopentylpyrrolidine-2-carboxamide

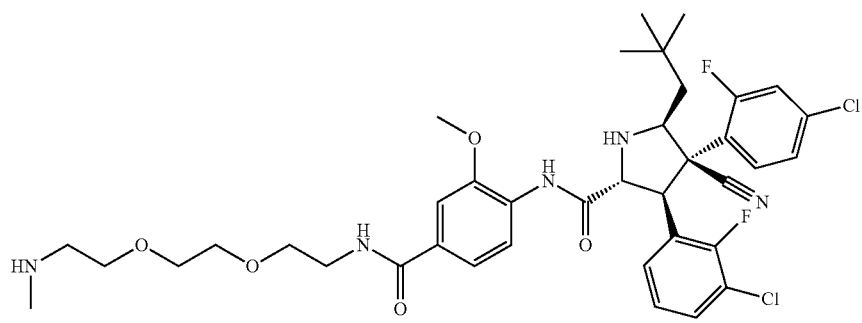 [SMILES: CNCCOCCOCCNC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

To the mixture of tert-butyl N-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethyl]-N-methyl-carbamate (230 mg, 0.26 mmol, 1 eq) in dichloromethane (8 mL) was added trifluoroacetic acid (2.00 mL). The mixture was stirred at 20° C. for 0.5 hour. The mixture was concentrated under reduced pressure to give the product. (2R,3S,4R,5S)-3-(3-chloro-2-fluoro-phenyl)-4-(4-chloro-2-fluoro-phenyl)-4-cyano-5-(2,2-dimethylpropyl)-N-[2-methoxy-4-[2-[2-[2-(methylamino)ethoxy]ethoxy]ethylcarbamoyl]phenyl]pyrrolidine-2-carboxamide (230 mg, trifluoroacetate) was obtained as a light yellow oil. LC/MS (ESI) m/z: 760.3 [M+1]$^+$.

Exemplary Synthesis of (2S,4R)-4-hydroxy-N-(2-hydroxy-4-(4-methylthiazol-5-yl)benzyl)-1-(3-methyl-2-(3-methylisoxazol-5-yl)butanoyl)pyrrolidine-2-carboxamide Step 1: Preparation of 2-(3-methylisoxazol-5-yl)acetic acid

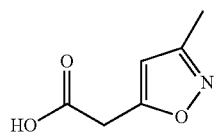

To a solution of 3,5-dimethylisoxazole (15 g, 154.46 mmol, 15 mL, 1 eq) in tetrahydrofuran (150 mL) was added n-butyllithium (2.5 M, 77 mL, 1.25 eq) dropwise at −78° C. under nitrogen, the mixture was stirred at −55° C. for 30 minutes, and then carbon dioxide was bubbled into the mixture for 30 minutes, the mixture was stirred at 25° C. for 1 hour. The mixture was quenched by saturated ammonium chloride solution (50 mL) the mixture was extracted with ethyl acetate (50 mL). The aqueous phase was adjusted with aqueous hydrochloric acid solution (2 M) until pH=2, the mixture was extracted with ethyl acetate (50 mL, three times), the organic phase was dried by anhydrous sodium sulfate, filtered and the filtrate was concentrated to give 2-(3-methylisoxazol-5-yl)acetic acid (10 g, 70.86 mmol, 46% yield) as a brown solid. $^1$H-NMR (400 MHz, DMSO-d$_6$) δ 12.74 (br s, 1H), 6.24 (s, 1H), 3.83 (s, 2H), 2.20 (s, 3H).

Step 2: Preparation of methyl 2-(3-methylisoxazol-5-yl)acetate

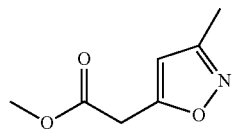

To a solution of 2-(3-methylisoxazol-5-yl)acetic acid (10 g, 70.86 mmol, 1 eq) in methanol (100 mL) was added thionyl chloride (12.65 g, 106.29 mmol, 7.71 mL, 1.5 eq) at 0° C., and the mixture was stirred at 50° C. for 4 hours. The mixture was concentrated to give crude product. This crude was diluted with ethyl acetate (200 mL) and washed by water (200 mL), and then saturated sodium bicarbonate aqueous solution (50 mL) and then brine (50 mL), the organic phase was dried by anhydrous, filtered and the filtrate was condensed to give methyl 2-(3-methylisoxazol-5-yl)acetate (10 g, 64.45 mmol, 91% yield) as a brown oil. $^1$H-NMR (400 MHz, CDCl$_3$) δ 6.11 (s, 1H), 3.80 (s, 2H), 3.76 (s, 3H), 2.30 (s, 3H).

Step 3: Preparation of methyl 3-methyl-2-(3-methylisoxazol-5-yl)butanoate

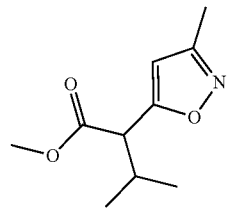

To a solution of methyl 2-(3-methylisoxazol-5-yl)acetate (10 g, 64.45 mmol, 1 eq) in tetrahydrofuran (100 mL) was added sodium hydride (3.87 g, 96.68 mmol, 60% purity, 1.5 eq) at 0° C. and then 2-iodopropane (13.15 g, 77.34 mmol, 7.74 mL, 1.2 eq) was added at 0° C., the mixture was stirred at 25° C. for 2 hours. Additional 2-iodopropane (2.55 g, 15.00 mmol, 1.5 mL) was added and the mixture was stirred at 25° C. for 10 hours. The mixture was quenched by aqueous hydrochloric acid solution (1 M, 300 mL) and the mixture was extracted with ethyl acetate (200 mL, three times), the organic phase was dried by anhydrous sodium sulfate, filtered and the filtrate was concentrated to give methyl 3-methyl-2-(3-methylisoxazol-5-yl)butanoate (13 g) as a brown oil.

Step 4: Preparation of 3-methyl-2-(3-methylisoxazol-5-yl)butanoic acid

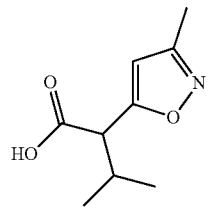

To a solution of methyl 3-methyl-2-(3-methylisoxazol-5-yl)butanoate (12.7 g, 64.39 mmol, 1 eq) in methanol (90 mL) and water (60 mL) was added sodium hydroxide (12.88 g, 321.96 mmol, 5 eq), the mixture was stirred at 25° C. for 2 hours. The mixture was concentrated to removed methanol, and then the residue was diluted with water (200 mL) and extracted with ethyl acetate (200 mL), the aqueous phase was adjusted by aqueous hydrochloric acid solution (2 M) until pH=3, and then the mixture was extracted with dichloromethane (200 mL, three times), the organic phase was dried by anhydrous sodium sulfate, filtered and the filtrate was concentrated to give crude product as a brown oil, this crude was purified by flash prep-HPLC, the fraction of acetonitrile was removed and the residue was extracted with dichloromethane (300 mL×5), the organic phase was dried by anhydrous sodium sulfate, filtered and the filtrate was concentrated to give product 3-methyl-2-(3-methylisoxazol-5-yl)butanoic acid (7.5 g, 40.94 mmol, 63% yield) as white solid. ¹H-NMR (400 MHz, DMSO-d₆) δ 6.26 (s, 1H), 3.58 (d, J=8.7 Hz, 1H), 2.33-2.23 (m, 1H), 2.21 (s, 3H), 0.95 (d, J=6.7 Hz, 3H), 0.82 (d, J=6.8 Hz, 3H).

Step 5: Preparation of 2-hydroxy-4-(4-methylthiazol-5-yl)benzonitrile

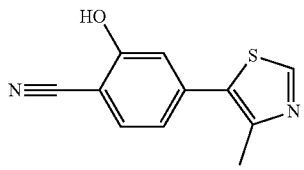

To a solution of 4-bromo-2-hydroxy-benzonitrile (15 g, 75.75 mmol, 1 eq) and 4-methylthiazole (20.28 g, 204.53 mmol, 19 mL, 2.7 eq) in N-methyl pyrrolidone (150 mL) was added potassium acetate (22.30 g, 227.25 mmol, 3 eq) and palladium acetate (1.70 g, 7.58 mmol, 0.1 eq)), the mixture stirred at 110° C. under nitrogen for 6 hours. The mixture was quenched with water (500 mL), the aqueous phase was extracted with ethyl acetate (300 mL×3). The combined organic phase was washed with brine (200 mL, twice), dried with anhydrous sodium sulfate, filtered and concentrated under vacuum and then methyl tertiary butyl ether (500 mL) was added to the mixture and the organic phase was washed with water (100 mL) and brine (100 mL, twice). The residue was purified by silica gel column chromatography (petroleum ether/ethyl acetate=3/1 to 1/1). Compound 2-hydroxy-4-(4-methylthiazol-5-yl)benzonitrile (11 g, 50.87 mmol, 67% yield) was obtained as a yellow solid.

Step 6: Preparation of 2-(aminomethyl)-5-(4-methylthiazol-5-yl)phenol

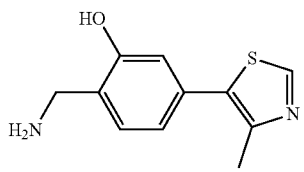

To a solution of 2-hydroxy-4-(4-methylthiazol-5-yl)benzonitrile (11 g, 50.87 mmol, 1 eq) in tetrahydrofuran (150 mL) was added lithium aluminum hydride (7.72 g, 203.46 mmol, 4 eq) at 0° C., the mixture was stirred at 50° C. for 3 hours. The mixture was quenched by water (8 mL) at 0° C., and then 15% sodium hydroxide aqueous solution (8 mL) and then water (8 mL), anhydrous sodium sulfate (30 g) was added, the mixture was stirred at 25° C. for 30 minutes, filtered and the solid was added dichloromethane/methanol (4/1, 50 mL), the mixture was stirred at 25° C. for 1 hours, filtered and the filtrate combined was concentrated to give 2-(aminomethyl)-5-(4-methylthiazol-5-yl)phenol (7 g, 31.78 mmol, 62% yield) as a brown solid. ¹H-NMR (400 MHz, DMSO-d₆) δ 8.82 (s, 1H), 6.90 (d, J=7.5 Hz, 1H), 6.52 (d, J=1.6 Hz, 1H), 6.25 (dd, J=1.7, 7.5 Hz, 1H), 3.59 (s, 2H), 2.41 (s, 3H).

Step 7: Preparation of tert-butyl (2S,4R)-4-hydroxy-2-((2-hydroxy-4-(4-methylthiazol-5-yl)benzyl)carbamoyl)pyrrolidine-1-carboxylate

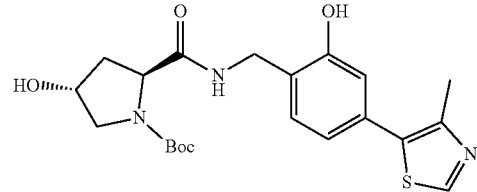 [SMILES: Cc1ncsc1-c1ccc(CNC(=O)[C@@H]2C[C@@H](O)CN2C(=O)OC(C)(C)C)c(O)c1]

To a solution of 2-(aminomethyl)-5-(4-methylthiazol-5-yl)phenol (7 g, 31.78 mmol, 1 eq) and (2S,4R)-1-tert-butoxycarbonyl-4-hydroxy-pyrrolidine-2-carboxylic acid (7.35 g, 31.78 mmol, 1 eq) in dimethylformamide (70 mL) was added diisopropylethylamine (12.32 g, 95.33 mmol, 16.60 mL, 3 eq) and then HATU (13.29 g, 34.95 mmol, 1.1 eq), the mixture was stirred at 25° C. for 2 hours. Additional (2S,4R)-1-tert-butoxycarbonyl-4-hydroxy-pyrrolidine-2-carboxylic acid (7.35 g, 31.78 mmol, 1 eq) and HATU (12.08 g, 31.78 mmol, 1 eq) was added, the mixture was stirred at 25° C. for 5 hours. The mixture was diluted with water (300 mL) and extracted with ethyl acetate (300 mL, twice), the organic phase was dried by anhydrous sodium sulfate, filtered and the filtrate was concentrated to give crude product as a brown oil, this crude was dissolved in tetrahydrofuran/water (2/1, 150 mL) and lithium hydroxide (3 g) was added, the mixture was stirred at 25° C. for 1 hour. The mixture was diluted with water (300 mL) and adjusted with aqueous hydrochloric acid solution (0.5 M) until pH=7, the mixture was extracted with ethyl acetate (300 mL, twice), the organic phase was dried by anhydrous sodium sulfate, filtered and filtrate was concentrated to give crude product, this crude product was purified by silica gel chromatography (2-10% methnol in dichloromethane) to give tert-butyl (2S,4R)-4-hydroxy-2-[[2-hydroxy-4-(4-methylthiazol-5-yl)phenyl]methylcarbamoyl]pyrrolidine-1-carboxylate (6.9 g, 15.92 mmol, 50% yield) as a yellow oil. LC/MS (ESI) m/z: 434.1 [M+1].

Step 8: Preparation of (2S,4R)-4-hydroxy-N-(2-hydroxy-4-(4-methylthiazol-5-yl)benzyl)pyrrolidine-2-carboxamide

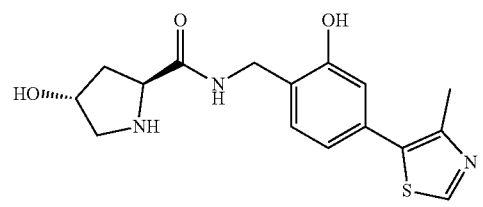 [SMILES: Cc1ncsc1-c1ccc(CNC(=O)[C@@H]2C[C@@H](O)CN2)c(O)c1]

To a solution of tert-butyl (2S,4R)-4-hydroxy-2-[[2-hydroxy-4-(4-methylthiazol-5-yl)phenyl]methylcarbamoyl] pyrrolidine-1-carboxylate (6.9 g, 15.92 mmol, 1 eq) in methanol (30 mL) was added hydrochloric/dioxane (4 M, 30 mL, 7.54 eq), the mixture was stirred at 25° C. for 20 minutes. The mixture was concentrated to give product as a yellow solid, this crude product was triturated by ethyl acetate and petroleum ether (1:1, 20 mL), the mixture was filtered and the solid was dried by rotary evaporator to give product (2S,4R)-4-hydroxy-N-[[2-hydroxy-4-(4-methylthiazol-5-yl)phenyl]methyl]pyrrolidine-2-carboxamide (4.83 g, 13.06 mmol, 82% yield, hydrochloric acid) as a yellow solid. $^1$H-NMR (400 MHz, DMSO-$d_6$) δ 10.03 (br s, 1H), 9.11-8.95 (m, 2H), 8.66 (br s, 1H), 7.20 (d, J=7.9 Hz, 1H), 7.04 (d, J=1.3 Hz, 1H), 6.90 (dd, J=1.7, 7.8 Hz, 1H), 4.44 (br s, 1H), 4.40-4.26 (m, 3H), 3.41-3.27 (m, 1H), 3.13-3.02 (m, 1H), 2.46 (s, 3H), 2.33 (br dd, J=7.5, 12.7 Hz, 1H), 1.96-1.85 (m, 1H), 1.33-1.24 (m, 1H).

Step 9: Preparation of (2S,4R)-4-hydroxy-N-(2-hydroxy-4-(4-methylthiazol-5-yl)benzyl)-1-(3-methyl-2-(3-methylisoxazol-5-yl)butanoyl)pyrrolidine-2-carboxamide

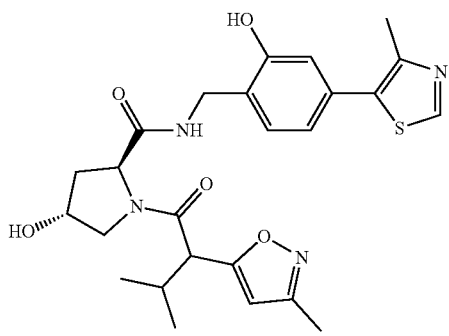 [SMILES: Cc1cc(C(C(=O)N2C[C@H](O)C[C@H]2C(=O)NCc2ccc(-c3scnc3C)cc2O)C(C)C)on1]

To a solution of (2S,4R)-4-hydroxy-N-[[2-hydroxy-4-(4-methylthiazol-5-yl)phenyl]methyl]pyrrolidine-2-carboxamide (4.83 g, 13.06 mmol, 1 eq, hydrochloride) in dimethylformamide (60 mL) was added diisopropylethylamine (5.06 g, 39.18 mmol, 6.82 mL, 3 eq), and then 3-methyl-2-(3-methylisoxazol-5-yl)butanoic acid (2.39 g, 13.06 mmol, 1 eq) and HATU (5.46 g, 14.36 mmol, 1.1 eq) was added, the mixture was stirred at 25° C. for 2 hours. The mixture was diluted with water (200 mL) and extracted with ethyl acetate (300 mL, twice), the organic phase was dried by anhydrous sodium sulfate, filtered and the filtrate was concentrated to give crude product. This crude product was purified by prep-HPLC, the fraction of acetonitrile was removed, and the residue was extracted with dichloromethane (300 mL×5), the organic phase was dried by anhydrous sodium sulfate, filtered and the filtrate was concentrated to give product (2S,4R)-4-hydroxy-N-[[2-hydroxy-4-(4-methylthiazol-5-yl)phenyl]methyl]-1-[3-methyl-2-(3-methylisoxazol-5-yl)butanoyl]pyrrolidine-2-carboxamide (4.0 g, 8.02 mmol, 61% yield) as a white solid. $^1$H-NMR (400 MHz, CD$_3$OD) δ 8.85 (s, 1H), 7.39-7.23 (m, 1H), 6.98-6.86 (m, 2H), 6.31-6.06 (m, 1H), 4.65-4.28 (m, 4H), 3.94-3.48 (m, 3H), 2.52-2.45 (m, 3H), 2.42-2.31 (m, 1H), 2.26-2.15 (m, 4H), 2.13-2.03 (m, 1H), 1.08-1.01 (m, 3H), 0.92-0.81 (m, 3H).

Exemplary Synthesis of 2-(2-((tert-butoxycarbonyl)(methyl)amino)ethoxy)ethyl 4-methylbenzenesulfonate Step 1: Preparation of 2-(2-hydroxyethoxy)ethyl 4-methylbenzenesulfonate

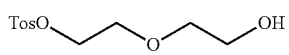

To a solution of 2-(2-hydroxyethoxy)ethanol (55.66 g, 524.53 mmol, 49.70 mL, 2 eq) in tetrahydrofuran (500 mL) was added sodium hydride (6.29 g, 157.27 mmol, 60% purity, 0.6 eq) at 0° C. and stirred for 0.5 hour under nitrogen. Then the mixture was added p-toluenesulfonyl chloride (50 g, 262.26 mmol, 1 eq), warmed to 25° C. and stirred for 6 hours. The mixture was poured into saturated ammonium chloride solution (200 mL) and stirred for 15 minutes. The aqueous phase was extracted with ethyl acetate (200 mL×2). The combined organic phase was washed with brine (200 mL), dried with anhydrous anhydrous sodium sulfate, filtered and concentrated in vacuum. The residue was purified by silica gel chromatography (Petroleum ether/Ethyl acetate=10/1 to 1/1) to afford 2-(2-hydroxyethoxy)ethyl 4-methylbenzenesulfonate (35 g, 134.46 mmol, 51% yield) as a yellow oil. LC/MS (ESI) m/z: 261.0 [M+1]$^+$; $^1$H-NMR (400 MHz, CDCl$_3$) δ 7.76-7.72 (m, 2H), 7.28 (d, J=8.0 Hz, 2H), 4.15-4.02 (m, 2H), 3.66-3.55 (m, 4H), 3.49-3.44 (m, 2H), 2.38 (s, 3H).

Step 2: Preparation of 2-(2-(methylamino)ethoxy)ethan-1-ol

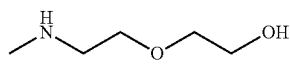

A mixture of 2-(2-hydroxyethoxy)ethyl 4-methylbenzenesulfonate (3 g, 11.52 mmol, 1 eq) in methanamine (11.93 g, 115.25 mmol, 10 eq) was degassed and purged with nitrogen for 3 times, and then the mixture was stirred at 85° C. for 16 hours under nitrogen. The reaction mixture was concentrated under reduced pressure to give a residue. Compound 2-[2-(methylamino)ethoxy]ethanol (1.37 g, 11.50 mmol, 99% yield) was obtained as a yellow oil. $^1$H-NMR (400 MHz, CDCl$_3$) δ 3.72-3.47 (m, 8H), 2.67-2.63 (m, 3H).

Step 3: Preparation of tert-butyl (2-(2-hydroxyethoxy)ethyl)(methyl)carbamate

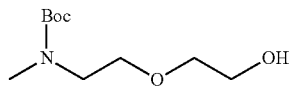

A mixture of 2-[2-(methylamino)ethoxy]ethanol (1.37 g, 11.50 mmol, 1 eq) and di-tert-butyl dicarbonate (3.01 g, 13.80 mmol, 3.17 mL, 1.2 eq) in dichloromethane (20 mL) was degassed and purged with nitrogen for 3 times, and then the mixture was stirred at 25° C. for 16 hours under nitrogen. The reaction mixture was quenched by addition water 200 mL, and extracted with ethyl acetate (300 mL×3). The combined organic layers were washed with brine (100 mL×3), dried over anhydrous sodium sulfate, filtered and concentrated under reduced pressure to give a residue. The residue was purified by column chromatography (Petroleum ether/Ethyl acetate=50/1 to 5/1). Compound tert-butyl N-[2-(2-hydroxyethoxy)ethyl]-N-methyl-carbamate (1.7 g, 7.75 mmol, 67% yield) was obtained as a yellow oil. $^1$H-NMR (400 MHz, CDCl$_3$) δ 3.77-3.68 (m, 2H), 3.66-3.55 (m, 4H), 3.42 (br s, 2H), 2.92 (s, 3H), 1.48-1.25 (m, 9H).

Step 4: Preparation of 2-(2-((tert-butoxycarbonyl)(methyl)amino)ethoxy)ethyl 4-methylbenzenesulfonate

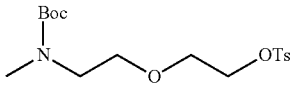 [SMILES: Cc1ccc(S(=O)(=O)OCCOCCN(C)C(=O)OC(C)(C)C)cc1]

A mixture of tert-butyl N-[2-(2-hydroxyethoxy)ethyl]-N-methyl-carbamate (1.1 g, 5.02 mmol, 1 eq), p-toluenesulfonyl chloride (1.91 g, 10.03 mmol, 2 eq), and triethylamine (1.52 g, 15.05 mmol, 2.09 mL, 3 eq) in dichloromethane (20 mL) was degassed and purged with nitrogen for 3 times, and then the mixture was stirred at 25° C. for 12 hours under nitrogen. The reaction mixture was quenched by addition water 200 mL, and extracted with ethyl acetate (300 mL×3). The combined organic layers were washed with brine (100 mL×3), dried over anhydrous sodium sulfate, filtered and concentrated under reduced pressure to give a residue. The residue was purified by column chromatography (Petroleum ether/Ethyl acetate=30/1 to 10/1). Compound 2-[2-[tert-butoxycarbonyl(methyl)amino]ethoxy]ethyl 4-methylbenzenesulfonate (1.6 g, 4.28 mmol, 85% yield) was obtained as a colorless oil. $^1$H-NMR (400 MHz, CDCl$_3$) δ 7.73 (d, J=8.4 Hz, 2H), 7.28 (d, J=8.0 Hz, 2H), 4.12-4.01 (m, 2H), 3.60-3.52 (m, 2H), 3.45 (br s, 2H), 3.25 (br s, 2H), 2.78 (s, 3H), 2.38 (s, 3H), 1.37 (s, 9H).

Exemplary Synthesis of tert-butyl (2-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)carbamate and tert-butyl (2-(2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)carbamate

Step 1: Preparation of tert-butyl (2-(2-(2-(((2S,4R)-4-hydroxy-1-(3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)carbamate A mixture of 2-[2-[tert-butoxycarbonyl(methyl)amino]ethoxy]ethyl 4-methylbenzenesulfonate (70 mg, 0.18 mmol, 1 eq), (2S,4R)-4-hydroxy-N-[[2-hydroxy-4-(4-methylthiazol-5-yl)phenyl]methyl]-1-[3-methyl-2-(3-methylisoxazol-5-yl)butanoyl]pyrrolidine-2-carboxamide (93 mg, 0.18 mmol, 1 eq) and potassium carbonate (51 mg, 0.37 mmol, 2 eq) in N,N-dimethylformamide (2 mL) was degassed and purged with nitrogen for 3 times, and then the mixture was stirred at 80° C. for 4 hours under nitrogen. The reaction mixture was quenched by the addition of water (10 mL) and extracted with ethyl acetate (20 mL×3). The combined organic layers were washed with brine (10 mL×3), dried over anhydrous sodium sulfate, filtered and concentrated under reduced pressure to give a residue. The residue was purified by prep-TLC (9% methanol in dichloromethane) to give the compound tert-butyl N-[2-[2-[2-[[[(2S,4R)-4-hydroxy-1-[3-methyl-2-(3-methylisoxazol-5-yl)butanoyl]pyrrolidine-2-carbonyl]amino]methyl]-5-(4-methylthiazol-5-yl)phenoxy]ethoxy]ethyl]-N-methyl-carbamate (100 mg, 0.14 mmol, 76% yield) as a yellow oil. LC/MS (ESI) m/z: 722.4 [M+23]$^+$.

Step 2: Preparation of tert-butyl (2-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)carbamate and tert-butyl (2-(2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)carbamate

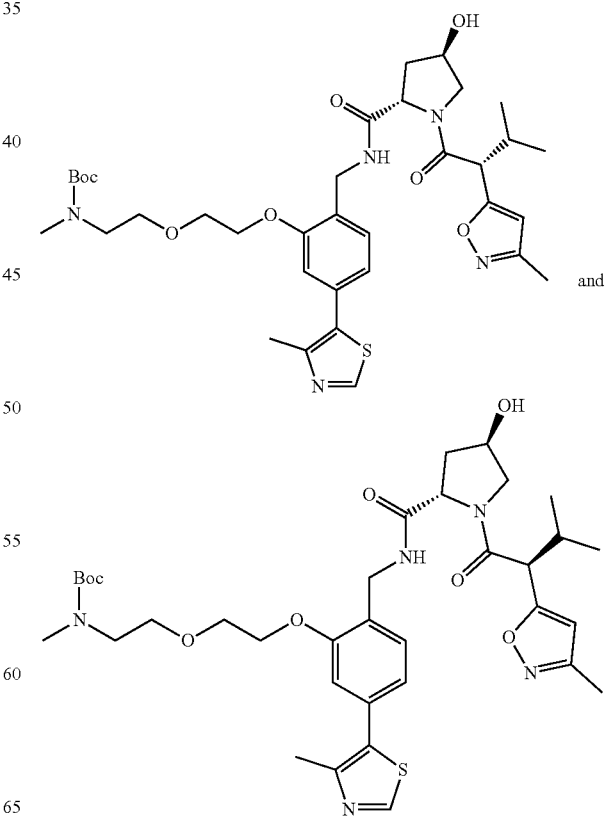

and

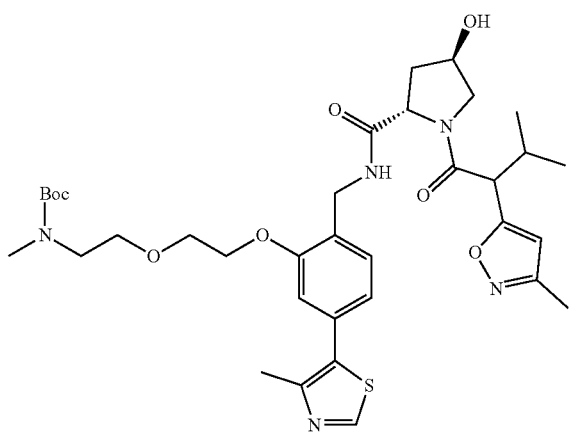

Tert-butyl N-[2-[2-[2-[[[(2S,4R)-4-hydroxy-1-[3-methyl-2-(3-methylisoxazol-5-yl)butanoyl]pyrrolidine-2-carbonyl]amino]methyl]-5-(4-methylthiazol-5-yl)phenoxy]ethoxy]ethyl]-N-methyl-carbamate (250 mg, 0.35 mmol, 1 eq) was purified by prep-SFC. Compounds tert-butyl (2-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)carbamate (90 mg, 0.12 mmol, 33% yield, 94% purity) and tert-butyl (2-(2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)carbamate (90 mg, 0.12 mmol, 35% yield, 99% purity) were obtained as colorless oils.

Exemplary Synthesis of methyl 2-(3-hydroxyisoxazol-5-yl)-3-methylbutanoate

Step 1: Preparation of methyl 3-(benzyloxy)isoxazole-5-carboxylate

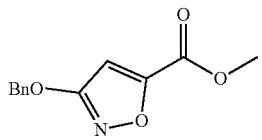 [SMILES: COC(=O)c1cc(OCc2ccccc2)no1]

To a solution of methyl 3-hydroxyisoxazole-5-carboxylate (7.20 g, 50.31 mmol, 1.00 eq) in acetone (150 mL) was added potassium carbonate (13.91 g, 100.62 mmol, 2.00 eq). The mixture was heated to 80° C. for 1 hour, then (bromomethyl) benzene (10.33 g, 60.37 mmol, 1.20 eq) was added. The resulting mixture was stirred at 80° C. for another 3 hours. The solid was filtered off and the filtrated was concentrated in vacuum. The residue was further purified by silica gel column chromatography (Petroleum ether:Ethyl acetate=15:1 to 10:1) to afford methyl 3-benzyloxy-isoxazole-5-carboxylate (9.50 g, 40.73 mmol, 81% yield) as a colorless oil. The oil was solidified after standing at 15° C. for 15 hr. LC/MS (ESI) m/z: 256.0 [M+23]$^+$; $^1$H-NMR (400 MHz, CDCl$_3$) δ 7.49-7.41 (m, 5H), 6.60 (s, 1H), 5.34 (s, 2H), 3.97 (s, 3H).

Step 2: Preparation of (3-(benzyloxy)isoxazol-5-yl)methanol

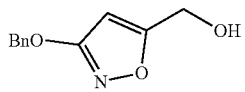

To a solution of methyl 3-benzyloxyisoxazole-5-carboxylate (2.33 g, 9.99 mmol, 1.00 eq) in methanol (50 mL) was added sodium borohydride (756 mg, 19.98 mmol, 2.00 eq) in portions. The resulting mixture was stirred at 15° C. for 3 hours. The mixture was poured into hydrochloric acid (0.2 M, 200 mL), and then extracted with ethyl acetate (150 mL×2). The combined organic layers were washed with saturated brine (200 mL×2), dried over anhydrous sodium sulfate, filtered and concentrated in vacuum to afford (3-benzyloxyisoxazol-5-yl)methanol (1.85 g, 9.02 mmol, 90% yield) as colorless oil. LC/MS (ESI) m/z: 206.0 [M+1].

Step 3: Preparation of 2-(3-(benzyloxy)isoxazol-5-yl)acetonitrile

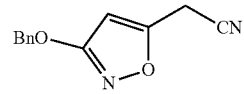 [SMILES: N#CCc1cc(OCc2ccccc2)no1]

To a solution of cyanic bromide (334 mg, 3.15 mmol, 1.05 eq) and triphenylphosphine (787 mg, 3.00 mmol, 1.00 eq) in dichloromethane (10 mL) was added a solution of (3-benzyloxyisoxazol-5-yl)methanol (616 mg, 3.00 mmol, 1.00 eq) in dichloromethane (10 mL). The mixture was stirred at 15° C. for 1 hour, then 2,3,4,6,7,8,9,10-octahydropyrimido[1,2-a]azepine (480 mg, 3.15 mmol, 1.05 eq) was added at 0° C. The resulting mixture was stirred at 0-15° C. for another 14 hours. The solvent was concentrated in vacuum. The residue was further purified by silica gel column chromatography (Petroleum ether:Ethyl acetate=5:1 to 4:1) to afford 2-(3-benzyloxyisoxazol-5-yl)acetonitrile (320 mg, 1.49 mmol, 50% yield) as a colorless oil. LC/MS (ESI) m/z: 215.0 [M+1]$^+$; $^1$H-NMR (400 MHz, CDCl$_3$) δ 7.48-7.41 (m, 5H), 6.06 (s, 1H), 5.30 (s, 2H), 3.82 (s, 2H).

Step 4: Preparation of 2-(3-(benzyloxy)isoxazol-5-yl)-3-methylbutanenitrile

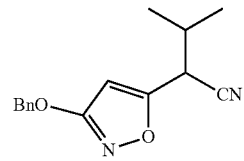 [SMILES: CC(C)C(C#N)c1cc(OCc2ccccc2)no1]

To a solution of 2-(3-benzyloxyisoxazol-5-yl)acetonitrile (214 mg, 1.00 mmol, 1.00 eq) in N,N-dimethylformamide (3 mL) was added potassium carbonate (138 mg, 1.00 mmol, 1.00 eq). The mixture was stirred at 15° C. for half an hour, then 2-iodopropane (170 mg, 1.00 mmol, 1.00 eq) was added. The resulting mixture was stirred at 15° C. for another 2.5 hr. Then potassium; 2-methylpropan-2-olate (90 mg, 0.8 mmol, 0.80 eq) was added to the mixture, the mixture was stirred at 15° C. for another 12 hours. The mixture was poured into hydrochloric acid (0.2 M, 30 mL), then extracted with ethyl acetate (30 mL×2). The combined organic layers were dried over anhydrous sodium sulfate, filtered and concentrated in vacuum. The residue was purified by silica gel column chromatography (Petroleum ether:Ethyl acetate=10:1 to 8:1) to afford 2-(3-benzyloxyisoxazol-5-yl)-3-methyl-butanenitrile (150 mg, 0.56 mmol, 59% yield) as a colorless oil. $^1$H-NMR (400 MHz, CDCl$_3$) δ 7.48-7.41 (m, 5H), 6.04 (s, 1H), 5.28 (s, 2H), 3.85 (d, J=5.6 Hz, 1H), 2.42-2.37 (m, 1H), 1.18 (d, J=6.8 Hz, 3H), 1.10 (d, J=6.8 Hz, 3H).

Step 5: Preparation of 2-(3-hydroxyisoxazol-5-yl)-3-methylbutanoic acid

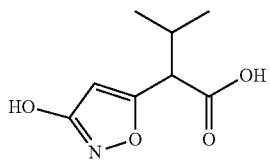

To a solution of 2-(3-benzyloxyisoxazol-5-yl)-3-methyl-butanenitrile (3.40 g, 13.27 mmol, 1.00 eq) in dioxane (30 mL) was added hydrochloric acid (11.8 M, 120 mL). The mixture was heated to 100° C. and stirred at 100° C. for 15 hr. The mixture was cooled to 15° C., and then extracted with ethyl acetate (150 mL×3). The combined organic layers were dried over anhydrous sodium sulfate, filtered and concentrated in vacuum. The crude product was further purified by prep-HPLC to afford 2-(3-hydroxyisoxazol-5-yl)-3-methyl-butanoic acid (230 mg, 1.19 mmol, 9% yield) as a yellow solid. LC/MS (ESI) m/z: 186.1 [M+1]$^+$.

Step 6: Preparation of methyl 2-(3-hydroxyisoxazol-5-yl)-3-methylbutanoate

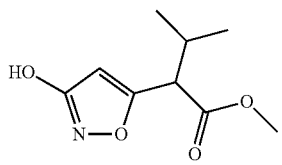

To a solution of 2-(3-hydroxyisoxazol-5-yl)-3-methyl-butanoic acid (1 g, 5.40 mmol, 1 eq) in methanol (10 mL) was added thionyl chloride (2.57 g, 21 mmol, 1.57 mL, 4 eq) at 0° C. The reaction mixture was stirred at 70° C. for 3 hours. The reaction mixture was concentrated under reduced pressure. The residue was diluted with water (50 ml) and extracted with ethyl acetate (30 mL×3). The combined organic layers were washed with brine (80 mL×2), dried over anhydrous sodium sulfate, filtered and concentrated under reduced pressure. Methyl 2-(3-hydroxyisoxazol-5-yl)-3-methyl-butanoate (1 g, 5.02 mmol, 92% yield) was obtained as a yellow oil. LC/MS (ESI) m/z: 200.1 [M+1]$^+$.

Exemplary Synthesis of (2S,4R)-4-hydroxy-N—((S)-1-(2-methoxy-4-(4-methylthiazol-5-yl)phenyl)ethyl)pyrrolidine-2-carboxamide hydrochloride

Step 1: Preparation of 1-(4-bromo-2-methoxyphenyl)ethan-1-one

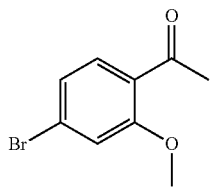

To a solution of 1-(4-bromo-2-hydroxy-phenyl)ethanone (10 g, 46.50 mmol, 1.0 eq) in dimethyl formamide (50 mL) was added potassium carbonate (9.64 g, 69.75 mmol, 1.5 eq). Then iodomethane (13.20 g, 93.00 mmol, 2.0 eq) was added into the mixture at 0° C. Then the mixture was stirred at 20° C. for 12 hours. The mixture was diluted with water (200 mL), extracted with ethyl acetate (100 ml×3), washed with brine (50 mL×2), dried over anhydrous sodium sulfate, filtered and then concentrated. 1-(4-bromo-2-methoxy-phenyl)ethanone (10.5 g, 45.84 mmol, 98% yield) was obtained as a yellow solid. LC/MS (ESI) m/z: 230.9 [M+1]$^+$; $^1$H-NMR (400 MHz, CDCl$_3$) δ 7.63 (d, J=8.4 Hz, 1H), 7.18-7.11 (m, 2H), 3.93 (s, 3H), 2.60 (s, 3H).

Step 2: Preparation of (R,E)-N-(1-(4-bromo-2-methoxyphenyl)ethylidene)-2-methylpropane-2-sulfinamide

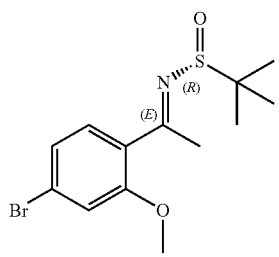

To a solution of 1-(4-bromo-2-methoxy-phenyl)ethanone (10 g, 43.65 mmol, 1.18 eq) in tetrahydrofuran (50 mL) was added Tetraethyl titanate (16.94 g, 74.26 mmol, 2.0 eq). Then 2-methylpropane-2-sulfinamide (4.5 g, 37.13 mmol, 1.0 eq) was added into the mixture and purged with N$_2$ (3 times). Then the mixture was stirred at 70° C. for 12 hours. The mixture was quenched with water (100 mL), diluted with water (200 mL), filtered and then extracted with ethyl acetate (200 ml×3), washed with brine (200 mL), dried over anhydrous sodium sulfate, filtered and then concentrated. The residue was purified by column chromatography silica (petroleum ether: ethyl acetate=20:1 to 3:1). (NE)-N-[1-(4-bromo-2-methoxy-phenyl)ethylidene]-2-methyl-propane-2-sulfinamide (9 g, 27.09 mmol, 73% yield) was obtained as a yellow oil. $^1$H-NMR (400 MHz, CDCl$_3$) δ 7.35 (d, J=8.0 Hz, 1H), 7.13 (dd, J=1.2, 8.0 Hz, 1H), 7.09 (s, 1H), 3.88 (s, 3H), 2.70 (s, 3H), 1.35-1.28 (m, 9H).

Step 3: Preparation of (R)—N—((S)-1-(4-bromo-2-methoxyphenyl)ethyl)-2-methylpropane-2-sulfinamide

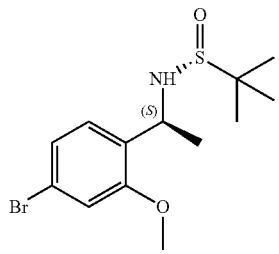

To a solution of (NE)-N-[1-(4-bromo-2-methoxy-phenyl)ethylidene]-2-methyl-propane-2-sulfinamide (9 g, 27.09 mmol, 1.0 eq) in tetrahydrofuran (90 mL) was added L-selectride (1 M, 81.26 mL, 3.0 eq) at 0° C. Then the mixture was stirred at 20° C. for 2 hours. The mixture was quenched with water (100 mL), diluted with water (20 mL), extracted with ethyl acetate (300 mL×3), washed with brine (200 mL), dried over anhydrous sodium sulfate, filtered and then concentrated. The residue was purified by column chromatography silica (petroleum ether:ethyl acetate=20:1 to 1:1). N-[(1S)-1-(4-bromo-2-methoxy-phenyl)ethyl]-2-methyl-propane-2-sulfinamide (5.5 g, 16.45 mmol, 60% yield) was obtained as a yellow oil. $^1$H-NMR (400 MHz, CDCl$_3$) δ 7.20-7.16 (m, 1H), 7.12-7.07 (m, 1H), 7.02 (d, J=2.0 Hz, 1H), 4.90-4.82 (m, 1H), 3.86 (s, 3H), 3.50 (d, J=5.2 Hz, 1H), 1.52 (d, J=6.8 Hz, 3H), 1.21 (s, 9H).

Step 4: Preparation of (R)—N—((S)-1-(2-methoxy-4-(4,4,5,5-tetramethyl-1,3,2-dioxaborolan-2-yl)phenyl)ethyl)-2-methylpropane-2-sulfinamide

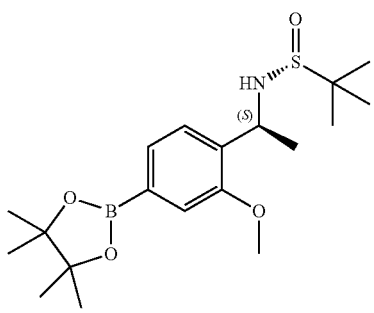

To a solution of N-[(1S)-1-(4-bromo-2-methoxy-phenyl)ethyl]-2-methyl-propane-2-sulfinamide (4.7 g, 14.06 mmol, 1.0 eq) and 4,4,5,5-tetramethyl-2-(4,4,5,5-tetramethyl-1,3,2-dioxaborolan-2-yl)-1,3,2-dioxaborolane (5.36 g, 21.09 mmol, 1.5 eq) in dioxane (12 mL) was added [1,1'-bis(diphenylphosphino)ferrocene]dichloropalladium(ii) (1.03 g, 1.41 mmol, 0.1 eq) and potassium acetate (2.76 g, 28.12 mmol, 2.0 eq). Then the mixture was purged with N$_2$ (3 times). Then the mixture was stirred at 90° C. for 5 hours. The mixture was diluted with water (20 mL), filtered and then extracted with ethyl acetate (50 mL×3), washed with brine (30 mL), dried over anhydrous sodium sulfate, filtered and then concentrated. The residue was purified by column chromatography silica (petroleum ether:ethyl acetate=10:1 to 1:1). N-[(1S)-1-[2-methoxy-4-(4,4,5,5-tetramethyl-1,3,2-dioxaborolan-2-yl)phenyl]ethyl]-2-methyl-propane-2-sulfinamide (4.5 g, 11.80 mmol, 84% yield) was obtained as a yellow oil. $^1$H-NMR (400 MHz, CDCl$_3$) δ 7.42 (d, J=8.0 Hz, 1H), 7.32-7.28 (m, 2H), 4.90 (m, J=6.4 Hz, 1H), 3.91 (s, 3H), 3.73-3.67 (m, 1H), 1.55 (d, J=6.8 Hz, 3H), 1.36 (s, 12H), 1.19 (s, 9H).

Step 5: Preparation of (R)—N—((S)-1-(2-methoxy-4-(4-methylthiazol-5-yl)phenyl)ethyl)-2-methylpropane-2-sulfinamide

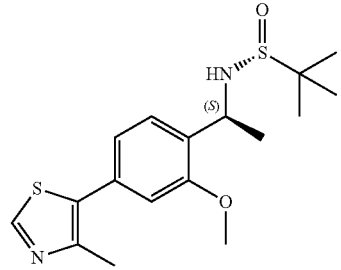

To a solution of N-[(1S)-1-[2-methoxy-4-(4,4,5,5-tetramethyl-1,3,2-dioxaborolan-2-yl) phenyl]ethyl]-2-methyl-propane-2-sulfinamide (4.71 g, 12.36 mmol, 1.0 eq) and 5-bromo-4-methyl-thiazole (2.2 g, 12.36 mmol, 1.0 eq) in dioxane (8 mL) and water (2 mL) was added sodium bicarbonate (2.08 g, 24.72 mmol, 2.0 eq) and [1,1'-bis(diphenylphosphino)ferrocene]dichloropalladium(ii) (904 mg, 1.24 mmol, 0.1 eq). Then the mixture was purged with N$_2$ (3 times). Then the mixture was stirred at 90° C. for 5 hours. The mixture was diluted with water (20 mL), filtered, extracted with ethyl acetate (30 mL×3), washed with brine (30 mL), dried over anhydrous sodium sulfate, filtered and then concentrated. The residue was purified by column chromatography silica (dichloromethane:methanol=100:1 to 10:1). N-[(1S)-1-[2-methoxy-4-(4-methylthiazol-5-yl)phenyl]ethyl]-2-methyl-propane-2-sulfinamide (3.9 g, 11.06 mmol, 89% yield) was obtained as a light yellow oil. $^1$H-NMR (400 MHz, CDCl$_3$) δ 8.69 (s, 1H), 7.34 (d, J=8.0 Hz, 1H), 7.03 (d, J=8.0 Hz, 1H), 6.92 (s, 1H), 4.92 (m, J=6.4 Hz, 1H), 3.89 (s, 3H), 3.58 (d, J=5.6 Hz, 1H), 2.56 (s, 3H), 1.57 (d, J=6.8 Hz, 3H), 1.22 (s, 9H).

Step 6: Preparation of (S)-1-(2-methoxy-4-(4-methylthiazol-5-yl)phenyl)ethan-1-amine hydrochloride

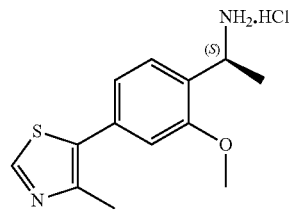

To a solution of N-[(1S)-1-[2-methoxy-4-(4-methylthiazol-5-yl)phenyl]ethyl]-2-methyl-propane-2-sulfinamide (3.6 g, 10.21 mmol, 1.0 eq) in dichloromethane (20 mL) was added hydrochloric/dioxane (4 M, 18.46 mL, 7.23 eq). Then the mixture was stirred at 20° C. for 1 hour. The mixture was concentrated. (1S)-1-[2-methoxy-4-(4-methylthiazol-5-yl)phenyl]ethanamine (3.8 g, HCl) was obtained as a yellow solid.

Step 7: Preparation of tert-butyl (2S,4R)-4-hydroxy-2-(((S)-1-(2-methoxy-4-(4-methylthiazol-5-yl)phenyl)ethyl)carbamoyl)pyrrolidine-1-carboxylate

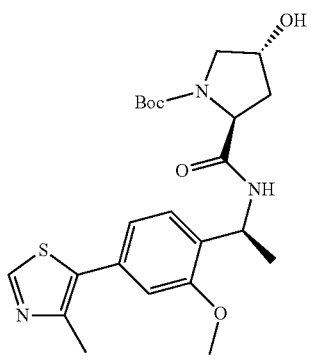 [SMILES: COc1cc(-c2scnc2C)ccc1[C@H](C)NC(=O)[C@@H]1C[C@@H](O)CN1C(=O)OC(C)(C)C]

To a solution of (1S)-1-[2-methoxy-4-(4-methylthiazol-5-yl)phenyl]ethanamine (800 mg, 2.25 mmol, 1.0 eq, HCl) in dimethyl formamide (10 mL) was added diisopropylethylamine (871 mg, 6.74 mmol, 1.17 mL, 3.0 eq). Then the mixture was stirred at 20° C. for 10 minutes. (2S,4R)-1-tert-butoxycarbonyl-4-hydroxy-pyrrolidine-2-carboxylic acid (519 mg, 2.25 mmol, 1.0 eq) and 1-hydroxybenzotriazole (364 mg, 2.70 mmol, 1.2 eq) was added into the mixture and stirred at 20° C. for 10 minutes. Then 1-(3-dimethylaminopropyl)-3-ethylcarbodiimide hydrochloride (517 mg, 2.70 mmol, 1.2 eq) was added into the mixture and stirred at 20° C. for 40 minutes. The mixture was diluted with water (30 mL), extracted with ethyl acetate (30 mL×3), washed with brine (30 mL), dried over anhydrous sodium sulfate, filtered and then concentrated. The residue was purified by column chromatography silica (dichloromethane:methanol=100:1 to 20:1). tert-butyl(2S,4R)-4-hydroxy-2-[[(1S)-1-[2-methoxy-4-(4-methylthiazol-5-yl)phenyl]ethyl]carbamoyl]pyrrolidine-1-carboxylate (850 mg, 1.84 mmol, 82% yield) was obtained as a yellow solid. $^1$H-NMR (400 MHz, CDCl$_3$) δ 8.69 (s, 1H), 7.28 (s, 1H), 7.00 (dd, J=1.6, 7.6 Hz, 1H), 6.93 (s, 1H), 5.34-5.21 (m, 1H), 4.59-4.26 (m, 2H), 3.91 (s, 3H), 3.81-3.53 (m, 2H), 2.54 (s, 3H), 2.51-2.38 (m, 1H), 2.22-1.94 (m, 1H), 1.57-1.18 (m, 13H).

Step 8: Preparation of (2S,4R)-4-hydroxy-N—((S)-1-(2-methoxy-4-(4-methylthiazol-5-yl)phenyl)ethyl)pyrrolidine-2-carboxamide hydrochloride

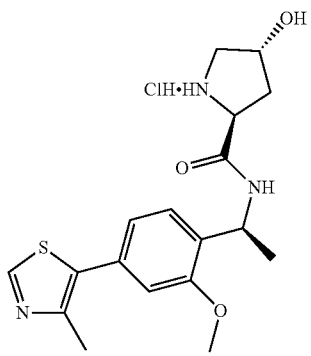

To a solution of tert-butyl (2S,4R)-4-hydroxy-2-[[(1S)-1-[2-methoxy-4-(4-methylthiazol-5-yl)phenyl]ethyl]carbamoyl]pyrrolidine-1-carboxylate (850 mg, 1.84 mmol, 1.0 eq) in dichloromethane (10 mL) was added hydrochloric acid (gas)/dioxane (4 M, 10 mL). Then the mixture was stirred at 20° C. for 1 hour. The mixture was concentrated. (2S,4R)-4-hydroxy-N-[(1S)-1-[2-methoxy-4-(4-methylthiazol-5-yl)phenyl]ethyl]pyrrolidine-2-carboxamide (700 mg, 1.76 mmol, 95% yield, HCl) was obtained as a yellow solid.

Exemplary Synthesis of tert-butyl (2-(2-(2-((5-((S)-1-((2S,4R)-4-hydroxy-2-(((S)-1-(2-methoxy-4-(4-methylthiazol-5-yl)phenyl)ethyl)carbamoyl)pyrrolidin-1-yl)-3-methyl-1-oxobutan-2-yl)isoxazol-3-yl)oxy)ethoxy)ethoxy)ethyl)(methyl)carbamate and tert-butyl (2-(2-(2-((5-((R)-1-((2S,4R)-4-hydroxy-2-(((S)-1-(2-methoxy-4-(4-methylthiazol-5-yl)phenyl)ethyl)carbamoyl)pyrrolidin-1-yl)-3-methyl-1-oxobutan-2-yl)isoxazol-3-yl)oxy)ethoxy)ethoxy)ethyl)(methyl)carbamate Step 1: Preparation of methyl 3-methyl-2-(3-((2,2,5-trimethyl-4-oxo-3,8,11-trioxa-5-azatridecan-13-yl)oxy)isoxazol-5-yl)butanoate

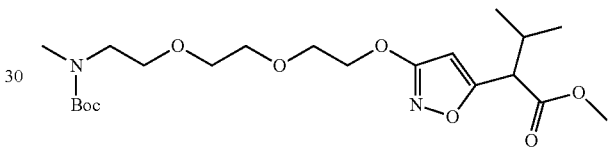

To a solution of methyl 2-(3-hydroxyisoxazol-5-yl)-3-methyl-butanoate (500 mg, 2.51 mmol, 1.0 eq) and 2-[2-[2-[tert-butoxycarbonyl(methyl)amino]ethoxy]ethoxy]ethyl4-methylbenzenesulfonate (1.05 g, 2.51 mmol, 1.0 eq) in dimethylformamide (10 mL) was added potassium carbonate (1.04 g, 7.53 mmol, 3.0 eq). Then the mixture was stirred at 70° C. for 48 hours. The mixture was diluted with water (50 mL), extracted with ethyl acetate (50 mL×3), washed with brine (50 mL), dried over anhydrous sodium sulfate, filtered and then concentrated. The residue was purified by column chromatography silica (petroleum ether:ethyl acetate=10:1 to 1:1). methyl 2-[3-[2-[2-[2-[tert-butoxycarbonyl(methyl)amino]ethoxy]ethoxy]ethoxy]isoxazol-5-yl]-3-methyl-butanoate (650 mg, 1.46 mmol, 58% yield) was obtained as a yellow oil. $^1$H-NMR (400 MHz, CDCl$_3$) δ 5.93 (s, 1H), 4.44-4.37 (m, 2H), 3.88-3.83 (m, 2H), 3.74 (s, 3H), 3.72-3.60 (m, 6H), 3.50 (d, J=8.8 Hz, 1H), 3.41 (br s, 2H), 2.92 (s, 3H), 2.37 (m, J=6.8, 8.8 Hz, 1H), 1.47 (s, 9H), 1.01 (d, J=6.8 Hz, 3H), 0.93 (d, J=6.8 Hz, 3H).

Step 2: Preparation of 3-methyl-2-(3-((2,2,5-trimethyl-4-oxo-3,8,11-trioxa-5-azatridecan-13-yl)oxy)isoxazol-5-yl)butanoic acid

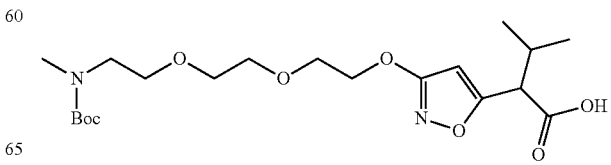

To a solution of methyl 2-[3-[2-[2-[2-[tert-butoxycarbonyl(methyl)amino]ethoxy]ethoxy]ethoxy]isoxazol-5-yl]-3-methyl-butanoate (630 mg, 1.42 mmol, 1.0 eq) in methanol (4 mL) and water (2 mL) was added lithium hydroxide monohydrate (594 mg, 14.17 mmol, 10.0 eq). Then the mixture was stirred at 20° C. for 2 hours. The mixture was quenched with aqueous hydrochloric (4M, 3 mL), extracted with ethyl acetate (30 mL×3), washed with brine (20 mL×2), dried over anhydrous sodium sulfate, filtered and then concentrated. 2-[3-[2-[2-[2-[tert-butoxycarbonyl(methyl)amino]ethoxy]ethoxy]ethoxy]isoxazol-5-yl]-3-methyl-butanoic acid (600 mg, 1.39 mmol, 98% yield) was obtained as a yellow oil.

Step 3: Preparation of tert-butyl (2-(2-(2-((5-(1-((2S,4R)-4-hydroxy-2-(((S)-1-(2-methoxy-4-(4-methylthiazol-5-yl)phenyl)ethyl)carbamoyl)pyrrolidin-1-yl)-3-methyl-1-oxobutan-2-yl)isoxazol-3-yl)oxy)ethoxy)ethoxy)ethyl)(methyl)carbamate

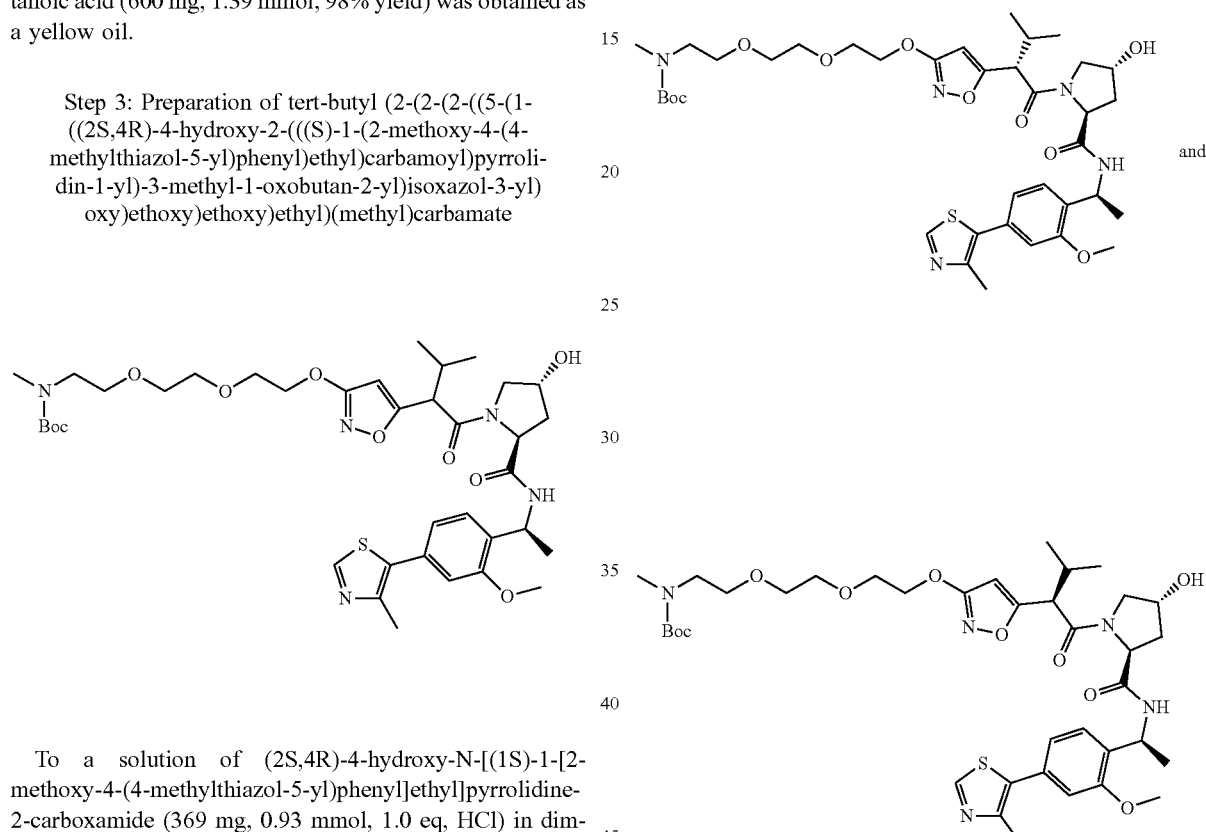

To a solution of (2S,4R)-4-hydroxy-N-[(1S)-1-[2-methoxy-4-(4-methylthiazol-5-yl)phenyl]ethyl]pyrrolidine-2-carboxamide (369 mg, 0.93 mmol, 1.0 eq, HCl) in dimethylformamide (5 mL) was added diisopropylethylamine (360 mg, 2.79 mmol, 3.0 eq). Then the mixture was stirred at 20° C. for 10 min. 2-[3-[2-[2-[2-[tert-butoxycarbonyl(methyl)amino]ethoxy]ethoxy]ethoxy]isoxazol-5-yl]-3-methyl-butanoic acid (400 mg, 0.93 mmol, 1.0 eq) and 1-hydroxybenzotriazole (251 mg, 1.86 mmol, 2.0 eq) were added into the mixture and stirred at 20° C. for 10 minutes. Then 1-(3-dimethylaminopropyl)-3-ethylcarbodiimide hydrochloride (356 mg, 1.86 mmol, 2.0 eq) was added into the mixture and stirred at 20° C. for 40 minutes. The mixture was diluted with water (30 mL), extracted with ethyl acetate (30 mL×2), washed with brine (30 mL), dried over anhydrous sodium sulfate, filtered and then concentrated. The residue was purified by prep-thin layer chromatography (dichloromethane:methanol=10:1). tert-butyl N-[2-[2-[2-[5-[1-[(2S,4R)-4-hydroxy-2-[[(1S)-1-[2-methoxy-4-(4-methylthiazol-5-yl)phenyl]ethyl]carbamoyl]pyrrolidine-1-carbonyl]-2-methyl-propyl]isoxazol-3-yl]oxyethoxy]ethoxy]ethyl]-N-methyl-carbamate (490 mg, 0.63 mmol, 67% yield, 99% purity) was obtained as a white solid.

Step 4: Preparation of tert-butyl (2-(2-(2-((5-((S)-1-((2S,4R)-4-hydroxy-2-(((S)-1-(2-methoxy-4-(4-methylthiazol-5-yl)phenyl)ethyl)carbamoyl)pyrrolidin-1-yl)-3-methyl-1-oxobutan-2-yl)isoxazol-3-yl)oxy)ethoxy)ethoxy)ethyl)(methyl)carbamate and tert-butyl (2-(2-(2-((5-((R)-1-((2S,4R)-4-hydroxy-2-(((S)-1-(2-methoxy-4-(4-methylthiazol-5-yl)phenyl)ethyl)carbamoyl)pyrrolidin-1-yl)-3-methyl-1-oxobutan-2-yl)isoxazol-3-yl)oxy)ethoxy)ethoxy)ethyl)(methyl)carbamate

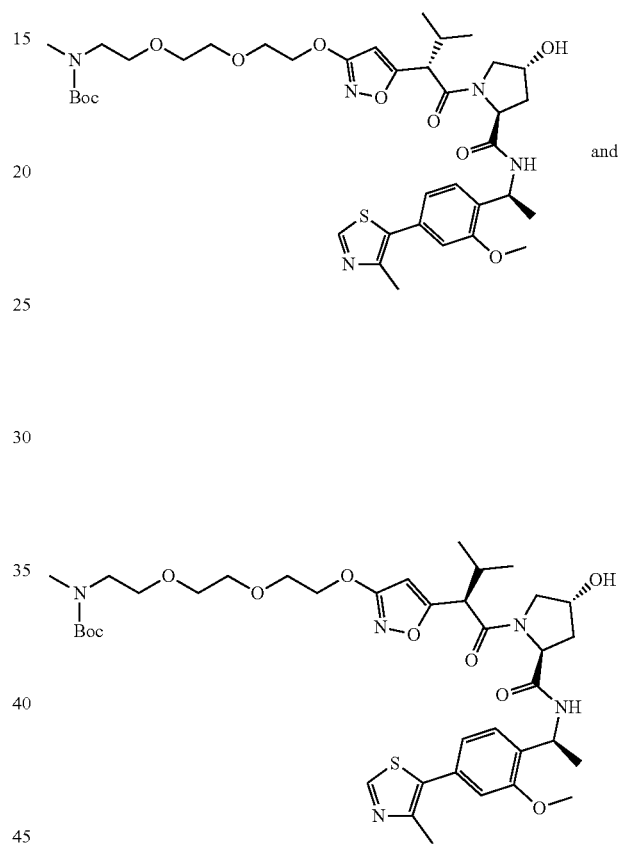

Tert-butyl N-[2-[2-[2-[5-[1-[(2S,4R)-4-hydroxy-2-[[(1S)-1-[12-methoxy-4-(4-methylthiazol-5-yl)phenyl]ethyl]carbamoyl]pyrrolidine-1-carbonyl]-2-methyl-propyl]isoxazol-3-yl]oxyethoxy]ethoxy]ethyl]-N-methyl-carbamate (490 mg, 0.63 mmol, 1.0 eq) was separated by SFC. The organic layers were concentrated. tert-butyl (2-(2-(2-((5-((S)-1-((2S,4R)-4-hydroxy-2-(((S)-1-(2-methoxy-4-(4-methylthiazol-5-yl)phenyl)ethyl)carbamoyl)pyrrolidin-1-yl)-3-methyl-1-oxobutan-2-yl)isoxazol-3-yl)oxy)ethoxy)ethoxy)ethyl)(methyl)carbamate (190 mg, 0.24 mmol, 95% yield, 98% purity) was obtained as a white solid. tert-butyl (2-(2-(2-((5-((R)-1-((2S,4R)-4-hydroxy-2-(((S)-1-(2-methoxy-4-(4-methylthiazol-5-yl)phenyl)ethyl)carbamoyl)pyrrolidin-1-yl)-3-methyl-1-oxobutan-2-yl)isoxazol-3-yl)oxy)ethoxy)ethoxy)ethyl)(methyl)carbamate (250 mg, 0.32 mmol, 84% yield, 99% purity) was obtained as a white solid.

Exemplary Synthesis of 4-(4,4,5,5-tetramethyl-1,3,2-dioxaborolan-2-yl)naphthalen-2-ol Step 1: Preparation of 4-(4,4,5,5-tetramethyl-1,3,2-dioxaborolan-2-yl)naphthalen-2-ol

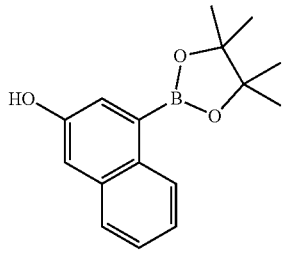 [SMILES: CC1(C)OB(c2cc(O)cc3ccccc23)OC1(C)C]

To a solution of 4-bromonaphthalen-2-ol (220 mg, 0.99 mmol, 1 eq) and 4,4,5,5-tetramethyl-2-(4,4,5,5-tetramethyl-1,3,2-dioxaborolan-2-yl)-1,3,2-dioxaborolane (326 mg, 1.28 mmol, 1.3 eq) in dimethylformamide (20 mL) was added [1,1'-bis(diphenylphosphino)ferrocene]dichloropalladium (II).dichloromethane (80 mg, 0.1 mmol, 0.1 eq) and potassium acetate (242 mg, 2.47 mmol, 2.5 eq), and then the mixture was stirred at 90° C. under nitrogen for 5 hours. The mixture was diluted with water (50 mL) and extracted with ethyl acetate (50 mL), the organic phase was dried by anhydrous, filtered and the filtrate was condensed to give crude product. This crude product was purified by silica gel column chromatography (10-33.3% ethyl acetate in petroleum ether) to give the product 400 mg as a white solid, this product was further purified by prep-TLC (50% ethyl acetate in petroleum ether) to give 4-(4,4,5,5-tetramethyl-1,3,2-dioxaborolan-2-yl)naphthalen-2-ol (180 mg, 0.67 mmol, 67% yield) as a white solid. $^1$H-NMR (400 MHz, CDCl$_3$) δ 8.67 (d, J=8.2 Hz, 1H), 7.72-7.66 (m, 2H), 7.46-7.35 (m, 2H), 7.28-7.27 (m, 1H), 4.95 (s, 1H), 1.43 (s, 12H).

Exemplary Synthesis of tert-butyl 4-(6-chloro-8-fluoro-7-(3-hydroxynaphthalen-1-yl)-2-(((R)-1-oxopropan-2-yl)oxy)quinazolin-4-yl)piperazine-1-carboxylate Step 1: Preparation of methyl (R)-2-(benzyloxy)propanoae

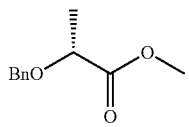

To solution of (2R)-2-benzyloxypropanoic acid (20.00 g, 110.99 mmol, 1.00 eq) in methanol (150 mL) was cooled to 0° C., then sulfurous dichloride (39.61 g, 332.96 mmol, 24.2 mL, 3.00 eq) was added dropwise. The mixture was then stirred at 50° C. for 4 hours. The reaction mixture concentrated under reduced pressure to give a residue. The residue was diluted with saturated sodium bicarbonate solution (200 mL), then extracted with ethyl acetate (200 mL×2). The combined organic layers were dried over anhydrous sodium sulfate, filtered and concentrated under reduced pressure to give the product, methyl (2R)-2-benzyloxypropanoate (21.96 g) as a yellow oil. LC/MS (ESI) m/z: 217.1 [M+23]$^+$; $^1$H-NMR (400 MHz, CDCl$_3$) δ 7.40-7.27 (m, 5H), 4.70 (d, J=11.6 Hz, 1H), 4.46 (d, J=11.6 Hz, 1H), 4.08 (q, J=6.8 Hz, 1H), 3.77 (s, 3H), 1.45 (d, J=6.8 Hz, 3H).

Step 2: Preparation of (R)-2-(benzyloxy)propanal

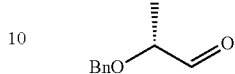

A solution of methyl (2R)-2-benzyloxypropanoate (20.96 g, 107.92 mmol, 1.00 eq) in dichloromethane (200 mL) was cooled to −78° C., then diisobutylaluminum hydride (1 M, 110 mL, 1.00 eq) was added in dropwise. The mixture was then stirred at −78° C. for 1 hour. The reaction mixture was quenched with hydrochloric acid (1 M, 10 mL), filtered through celite. The filtrate was diluted with water (100 mL), then extracted with dichloromethane (100 mL×2). The combined organic layers were dried over anhydrous sodium sulfate, filtered and concentrated under reduced pressure to give a residue. Compound (2R)-2-benzyloxypropanal (15.70 g) was obtained as a colorless oil. LC/MS (ESI) m/z: 181.1 [M+17]$^+$; $^1$H-NMR (400 MHz, CDCl$_3$) δ 9.68 (d, J=1.6 Hz, 1H), 7.42-7.33 (m, 5H), 4.68-4.60 (m, 2H), 3.95-3.86 (m, 1H), 1.34 (d, J=6.8 Hz, 3H).

Step 3: Preparation of (R)-(((1,1-dimethoxypropan-2-yl)oxy)methyl)benzene

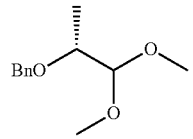

To a solution of (2R)-2-benzyloxypropanal (14.70 g, 89.52 mmol, 1 eq) in trimethoxymethane (71.15 g, 670.46 mmol, 73.5 mL, 7.49 eq) was added 4-methylbenzenesulfonic acid; pyridine (450 mg, 1.79 mmol, 0.02 eq). The mixture was stirred at 25° C. for 2 hours. The reaction mixture was diluted with water (100 mL), then extracted with ethyl acetate (100 mL×2). The combined organic layers were dried over anhydrous sodium sulfate, filtered and concentrated under reduced pressure to give a residue. The residue was purified by silica gel column chromatography (petroleum ether/ethyl acetate=25/1 to 20/1) to give desired product. Compound [(1R)-2,2-dimethoxy-1-methyl-ethoxy]methylbenzene (16.70 g, 79.42 mmol, 89% yield, 100% purity) was obtained as a colorless oil. LC/MS (ESI) m/z: 233.1 [M+23]$^+$; $^1$H-NMR (400 MHz, CDCl$_3$) δ 7.39-7.27 (m, 5H), 4.68-4.61 (m, 2H), 4.22 (d, J=5.2 Hz, 1H), 3.62-3.53 (m, 1H), 3.44 (d, J=4.0 Hz, 6H), 1.20 (d, J=6.4 Hz, 3H).

Step 4: Preparation of (R)-1,1-dimethoxypropan-2-ol

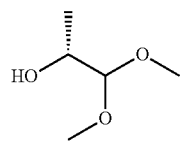

To a solution of [(1R)-2,2-dimethoxy-1-methyl-ethoxy]methylbenzene (9.00 g, 42.80 mmol, 1.00 eq) in methanol (80 mL) was added palladium on activated carbon (500 mg, 5% purity) and palladium hydroxide (500 mg, 5% purity) under nitrogen gas. The suspension was degassed under vacuum and purged with hydrogen gas several times. The mixture was stirred under hydrogen gas (15 psi) at 60° C. for 8 hours. The reaction mixture was filtered through celite and concentrated under reduced pressure to give a residue. Compound (2R)-1,1-dimethoxypropan-2-ol (4.1 g) was obtained as a colorless oil. $^1$H-NMR (400 MHz, CDCl$_3$) δ 4.08 (d, J=6.4 Hz, 1H), 3.81-3.73 (m, 1H), 3.45 (d, J=4.0 Hz, 6H), 1.20 (d, J=6.4 Hz, 3H).

Step 5: Preparation of tert-butyl (R)-4-(7-bromo-6-chloro-2-((1,1-dimethoxypropan-2-yl)oxy)-8-fluoro-quinazolin-4-yl)piperazine-1-carboxylate

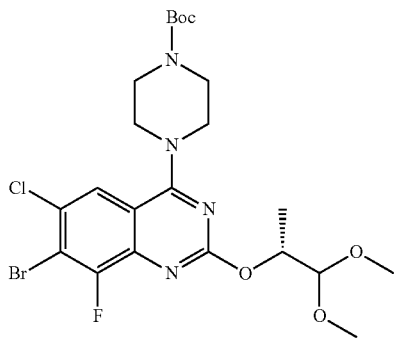 [SMILES: COC(OC)[C@@H](C)Oc1nc(N2CCN(C(=O)OC(C)(C)C)CC2)c2cc(Cl)c(Br)c(F)c2n1]

Tert-butyl 4-(7-bromo-2,6-dichloro-8-fluoro-quinazolin-4-yl)piperazine-1-carboxylate (300 mg, 0.62 mmol, 1 eq), (2R)-1,1-dimethoxypropan-2-ol (150.13 mg, 1.25 mmol, 2 eq), potassium carbonate (259 mg, 1.87 mmol, 3 eq) and 1,4-diazabicyclo[2.2.2]octane (7 mg, 62.48 umol, 0.1 eq) were taken up into a microwave tube in acetonitrile (10 mL). The sealed tube was heated at 100° C. for 2 hours under microwave. The reaction mixture was filtered and the filtrate was concentrated under vacuum to get the residue. The residue was purified by silica gel column chromatography (0-15% ethyl acetate in petroleum ether) to get tert-butyl 4-[7-bromo-6-chloro-2-[(1R)-2,2-dimethoxy-1-methyl-ethoxy]-8-fluoro-quinazolin-4-yl]piperazine-1-carboxylate (706 mg, 1.10 mmol, 22% yield, 87% purity) as a yellow solid. LC/MS (ESI) m/z: 565.1 [M+1]$^+$.

Step 6: Preparation of tert-butyl 4-(6-chloro-2-(((R)-1,1-dimethoxypropan-2-yl)oxy)-8-fluoro-7-(3-hydroxynaphthalen-1-yl)quinazolin-4-yl)piperazine-1-carboxylate

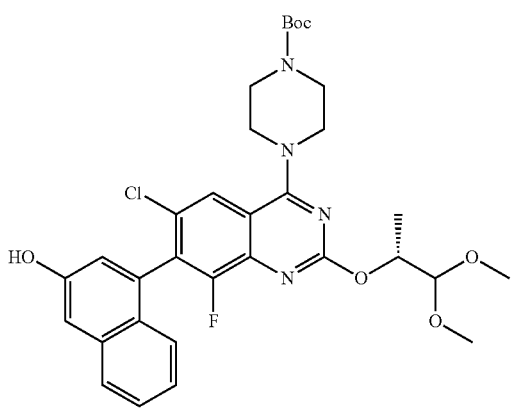 [SMILES: COC(OC)[C@@H](C)Oc1nc(N2CCN(C(=O)OC(C)(C)C)CC2)c2cc(Cl)c(-c3cc(O)cc4ccccc34)c(F)c2n1]

To a solution of tert-butyl 4-[7-bromo-6-chloro-2-[(1R)-2,2-dimethoxy-1-methyl-ethoxy]-8-fluoro-quinazolin-4-yl]piperazine-1-carboxylate (608 mg, 1.08 mmol, 1 eq), 4-(4,4,5,5-tetramethyl-1,3,2-dioxaborolan-2-yl)naphthalen-2-ol (379 mg, 1.40 mmol, 1.3 eq) in tetrahydrofuran (15 mL) was added potassium phosphate (1.5 M, 2.16 mL, 3 eq) and (2-dicyclohexylphosphino-2',4',6'-triisopropyl-1,1'-biphenyl) [2-(2'-amino-1,1'-biphenyl)]palladium(ii) methanesulfonate (91 mg, 0.11 mmol, 0.1 eq). The reaction mixture was degassed and charged with nitrogen for 3 times and then heated to 65° C. for 16 hours. Ethyl acetate (30 mL) was added and the mixture was washed with water (30 mL). The organic layer was dried over sodium sulfate and then concentrated under vacuum to get the residue. The residue was purified by flash silica gel chromatography (0-60% ethyl acetate in petroleum ether) to get the crude product (600 mg). This crude product was purified by semi-preparative reverse phase HPLC. The collected fractions were concentrated under vacuum to remove most of the acetonitrile. The pH of the mixture was adjusted to 8 with saturated aqueous sodium bicarbonate and then extracted with ethyl acetate (50 mL×2). The combined organic layer was dried over sodium sulfate and then concentrated under vacuum to get tert-butyl 4-[6-chloro-2-[(1R)-2,2-dimethoxy-1-methyl-ethoxy]-8-fluoro-7-(3-hydroxy-1-naphthyl)quinazolin-4-yl]piperazine-1-carboxylate (400 mg) as a light yellow solid. LC/MS (ESI) m/z: 627.2 [M+1]$^+$.

Step 7: Preparation of (2R)-2-((6-chloro-8-fluoro-7-(3-hydroxynaphthalen-1-yl)-4-(piperazin-1-yl)quinazolin-2-yl)oxy)propanal

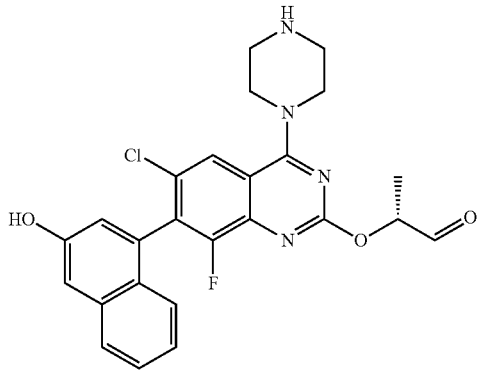 [SMILES: C[C@H](C=O)Oc1nc(N2CCNCC2)c2cc(Cl)c(-c3cc(O)cc4ccccc34)c(F)c2n1]

To a solution of tert-butyl 4-[6-chloro-2-[(1R)-2,2-dimethoxy-1-methyl-ethoxy]-8-fluoro-7-(3-hydroxy-1-naphthyl)quinazolin-4-yl]piperazine-1-carboxylate (400 mg, 0.64 mmol, 1 eq) in dioxane (20 mL) was added hydrochloric acid (12 M, 2.00 mL, 37.63 eq). The reaction mixture was stirred at 25° C. for 1 hour. The reaction mixture was concentrated under vacuum to get (2R)-2-[6-chloro-8-fluoro-7-(3-hydroxy-1-naphthyl)-4-piperazin-1-yl-quinazolin-2-yl]oxypropanal (330 mg, hydrochloride) as a light yellow gum. LC/MS (ESI) m/z: 481.1 [M+1]$^+$.

Step 8: Preparation of tert-butyl 4-(6-chloro-8-fluoro-7-(3-hydroxynaphthalen-1-yl)-2-(((R)-1-oxopropan-2-yl)oxy)quinazolin-4-yl)piperazine-1-carboxylate

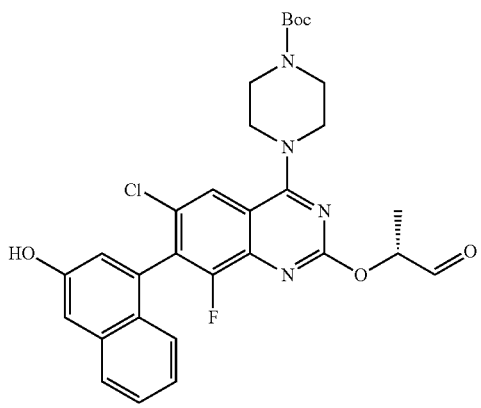 [SMILES: C[C@H](C=O)Oc1nc(N2CCN(C(=O)OC(C)(C)C)CC2)c2cc(Cl)c(-c3cc(O)cc4ccccc34)c(F)c2n1]

A mixture of (2R)-2-[6-chloro-8-fluoro-7-(3-hydroxy-1-naphthyl)-4-piperazin-1-yl-quinazolin-2-yl]oxypropanal (330 mg, 0.64 mmol, 1 eq, hydrochloride) and di-tert-butyl dicarbonate (278.41 mg, 1.28 mmol, 2 eq) in tetrahydrofuran (20 mL) was cooled to 0° C. Then saturated aqueous sodium sulfate (322 mg, 3.83 mmol, 6 mL, 6 eq) was added. The reaction mixture was stirred at 25° C. for 2 hours. Ethyl acetate (30 mL) and water (20 mL) were added and the mixture was separated. The organic layer was dried over sodium sulfate and then concentrated under vacuum to get the residue. The residue was purified by silica gel column chromatography with dichloromethane (50 mL) then ethyl acetate (40 mL) to get tert-butyl 4-[6-chloro-8-fluoro-7-(3-hydroxy-1-naphthyl)-2-[(1R)-1-methyl-2-oxo-ethoxy]quinazolin-4-yl]piperazine-1-carboxylate (380 mg) as a light yellow solid. LC/MS (ESI) m/z: 581.2 [M+1]$^+$; $^1$H-NMR (400 MHz, CDCl$_3$) δ 9.71 (dd, J=1.8, 3.4 Hz, 1H), 7.80 (d, J=1.1 Hz, 1H), 7.76 (d, J=8.3 Hz, 1H), 7.44 (dt, J=1.5, 7.3 Hz, 1H), 7.33-7.27 (m, 2H), 7.27-7.22 (m, 1H), 7.10 (d, J=2.4 Hz, 1H), 6.32-5.88 (m, 1H), 5.30-5.22 (m, 1H), 3.99-3.77 (m, 4H), 3.74-3.61 (m, 4H), 1.59-1.54 (m, 3H), 1.52 (s, 9H).

Exemplary Synthesis of tert-butyl 4-(2-(tosyloxy)ethoxy)piperidine-1-carboxylate

Step 1: Preparation of 2-(benzyloxy)ethyl 4-methylbenzenesulfonate

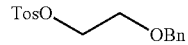

To a solution of 2-benzyloxyethanol (50 g, 328.54 mmol, 46.73 mL, 1 eq) and potassium hydroxide (22.12 g, 394.24 mmol, 1.2 eq) in tetrahydrofuran (200 mL) was added toluenesulfonyl chloride (56.37 g, 295.68 mmol, 0.9 eq). The mixture was stirred at 25° C. for 1 hour. Ethyl acetate (1000 mL) was added, then the reaction was filtered, then the filtrate was washed by brine (200 mL), dried with anhydrous sodium sulfate, filtered and concentrated in vacuum. The residue was purified by flash silica gel chromatography (Petroleum ether:Ethyl acetate=5:1 to 3:1). Compound 2-benzyloxyethyl 4-methylbenzenesulfonate (75 g, 243.82 mmol, 74% yield, 99% purity) was obtained as a yellow oil. $^1$H-NMR (400 MHz, CDCl$_3$) δ 7.85-7.79 (m, 2H), 7.38-7.31 (m, 4H), 7.30-7.26 (m, 2H), 7.31 (s, 1H), 4.51 (s, 2H), 4.26-4.19 (m, 2H), 3.73-3.65 (m, 2H), 2.50-2.40 (m, 3H).

Step 2: Preparation of tert-butyl 4-(2-(benzyloxy)ethoxy)piperidine-1-carboxylate

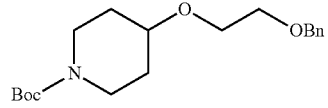 [SMILES: CC(C)(C)OC(=O)N1CCC(OCCOCc2ccccc2)CC1]

To a solution of tert-butyl 4-hydroxypiperidine-1-carboxylate (10.35 g, 51.41 mmol, 1.05 eq) in N,N-dimethylformamide (150 mL) was added sodium cyanide (2.15 g, 53.86 mmol, 60% purity, 1.1 eq) at 0° C. stirred at 0.5 hour, 2-benzyloxyethyl 4-methylbenzenesulfonate (15 g, 48.96 mmol, 1 eq) was added. The mixture was stirred at 25° C. for 1 hour. Ammonium chloride solution (200 mL) was added, and then the aqueous phase was extracted with ethyl acetate (200 mL*3). The combined organic phase was washed with brine (100 mL*2), dried with anhydrous sodium sulfate, filtered and concentrated in vacuum. The residue was purified by flash silica gel chromatography (Petroleum ether:Ethyl acetate=10:1 to 4:1). Compound tert-butyl 4-(2-benzyloxyethoxy)piperidine-1-carboxylate (14.5 g) was obtained as a colorless oil. LC/MS (ESI) m/z: 236.1 [M–100]$^+$; $^1$H-NMR (400 MHz, CDCl$_3$) δ 7.41-7.30 (m, 5H), 4.60 (s, 2H), 3.80 (br d, J=9.9 Hz, 2H), 3.71-3.62

(m, 4H), 3.55-3.46 (m, 1H), 3.08 (ddd, J=3.5, 9.5, 13.3 Hz, 2H), 1.86 (br d, J=7.9 Hz, 2H), 1.60-1.50 (m, 2H), 1.47 (s, 9H).

Step 3: Preparation of tert-butyl 4-(2-hydroxyethoxy)piperidine-1-carboxylate

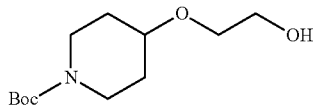 [SMILES: CC(C)(C)OC(=O)N1CCC(OCCO)CC1]

To a solution of tert-butyl 4-(2-benzyloxyethoxy)piperidine-1-carboxylate (5 g, 14.91 mmol, 1 eq) in methanol (40 mL) was added palladium on activated carbon (0.5 g, 10% purity) under nitrogen. The suspension was degassed under vacuum and purged with $H_2$ several times. The mixture was stirred under hydrogen (15 psi) at 25° C. for 12 hours. The reaction mixture was filtered and concentrated under vacuum. Compound tert-butyl 4-(2-hydroxyethoxy)piperidine-1-carboxylate (3 g, 12.23 mmol, 82% yield) was obtained as a colorless oil. $^1$H-NMR (400 MHz, CDCl$_3$) δ 3.86-3.72 (m, 4H), 3.66-3.58 (m, 2H), 3.56-3.45 (m, 1H), 3.16-3.07 (m, 2H), 2.15-2.05 (m, 1H), 1.96-1.78 (m, 2H), 1.59-1.49 (m, 2H), 1.47 (s, 9H).

Step 4: Preparation of tert-butyl 4-(2-(tosyloxy)ethoxy)piperidine-1-carboxylate

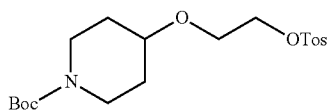

To a mixture of tert-butyl 4-(2-hydroxyethoxy)piperidine-1-carboxylate (7.4 g, 30.17 mmol, 1 eq) and triethylamine (9.16 g, 90.50 mmol, 12.60 mL, 3 eq) in dichloromethane (70 mL) was added toluenesulfonyl chloride (8.63 g, 45.25 mmol, 1.5 eq) at 0° C. The mixture was stirred at 25° C. for 12 hours. The reaction mixture was concentrated under vacuum. The residue was purified by flash silica gel chromatography (Petroleum ether:Ethyl acetate=4:1 to 1:1). Compound tert-butyl 4-[2-(p-tolylsulfonyloxy)ethoxy]piperidine-1-carboxylate (8.7 g, 21.78 mmol, 72% yield) as a yellow oil was obtained. $^1$H-NMR (400 MHz, CDCl$_3$) δ 7.80 (d, J=8.3 Hz, 2H), 7.34 (d, J=8.1 Hz, 2H), 4.18-4.13 (m, 2H), 3.76-3.70 (m, 2H), 3.67-3.60 (m, 4H), 3.47-3.39 (m, 1H), 3.14-3.01 (m, 2H), 2.46-2.43 (m, 3H), 1.90-1.78 (m, 2H), 1.45 (s, 9H).

Exemplary Synthesis of tert-butyl 4-(2-(2-(2-(1,3-dioxoisoindolin-2-yl)ethoxy)ethoxy)ethoxy)piperidine-1-carboxylate Step 1: Preparation of 2-(2-(2-(benzyloxy)ethoxy)ethoxy)ethyl 4-methylbenzenesulfonate

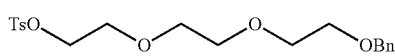 [SMILES: Cc1ccc(S(=O)(=O)OCCOCCOCCOCc2ccccc2)cc1]

To a solution of 2-[2-(2-benzyloxyethoxy)ethoxy]ethanol (18.2 g, 75.74 mmol, 1 eq) and potassium hydroxide (12.75 g, 227.22 mmol, 3 eq) in tetrahydrofuran (100 mL) was stirred at 25° C. for 0.5 hour, then p-toluenesulfonyl chloride (28.88 g, 151.48 mmol, 2 eq) was added and stirred at 25° C. for 1 hour. The reaction mixture was quenched by water (100 mL) at 25° C., and extracted with Ethyl acetate (200 mL*3). The combined organic layers were washed with brine (150 mL*2), dried over sodium sulfate, filtered and concentrated under reduced pressure to give a residue. The residue was purified by flash silica gel chromatography (0-10% ethyl aetate in petroleum ether). Compound 2-[2-(2-benzyloxyethoxy)ethoxy]ethyl 4-methylbenzenesulfonate (20 g, 50.70 mmol, 66.9% yield) was obtained as a colorless oil.

Step 2: Preparation of tert-butyl 4-(2-(2-(2-(benzyloxy)ethoxy)ethoxy)ethoxy)piperidine-1-carboxylate

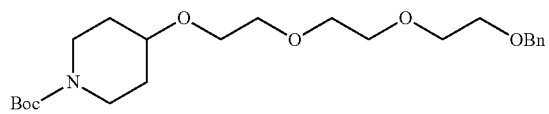 [SMILES: CC(C)(C)OC(=O)N1CCC(OCCOCCOCCOCc2ccccc2)CC1]

To the mixture of tert-butyl 4-hydroxypiperidine-1-carboxylate (8.42 g, 41.83 mmol, 1.1 eq) in N,N-dimethylformamide (150 mL) was added sodium hydride (1.75 g, 43.73 mmol, 60% in mineral oil, 1.15 eq) at 0° C. Then it was stirred at 25° C. for 0.5 hour. Then 2-[2-(2-benzyloxyethoxy)ethoxy]ethyl 4-methylbenzenesulfonate (15 g, 38.02 mmol, 1 eq) was added to the mixture. The mixture was stirred at 25° C. for 2 hours. The mixture was quenched with saturated ammonium chloride solution (350 mL). Then it was extracted with ethyl acetate (150 mL×3). The combined organic layer was washed with water (200 mL×2) and brine (200 mL×2), dried over anhydrous sodium sulfate, filtered and concentrated under reduced pressure to give a residue. The residue was purified by gel silica chromatography (petroleum ether:ethyl acetate=10:1 to 3:1). Compound tert-butyl 4-[2-[2-(2-benzyloxyethoxy)ethoxy]ethoxy]piperidine-1-carboxylate (11.8 g, 27.86 mmol, 73.27% yield) was obtained as a colorless oil. LC/MS (ESI) m/z: 324.1 [M−99]; $^1$H-NMR (400 MHz, CDCl$_3$) δ 7.35-7.28 (m, 5H), 4.57-4.56 (m, 2H), 3.84-3.75 (m, 2H), 3.69-3.63 (m, 12H), 3.50-3.45 (m, 1H), 3.07-3.02 (m, 2H), 1.83-1.81 (m, 2H), 1.53-1.45 (m, 11H).

Step 3: Preparation of tert-butyl 4-(2-(2-(2-hydroxyethoxy)ethoxy)ethoxy)piperidine-1-carboxylate

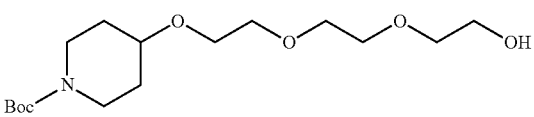

To the mixture of tert-butyl 4-[2-[2-(2-benzyloxyethoxy)ethoxy]ethoxy]piperidine-1-carboxylate (11.8 g, 27.86 mmol, 1 eq) in methanol (100 mL) was added palladium on activated carbon catalyst (800 mg, 10% purity). The mixture was degassed and refilled with hydrogen for 3 times. Then it was stirred at 25° C. for 12 hours under hydrogen atmosphere (50 psi). The reaction mixture was warmed to 60° C. The mixture was stirred at 60° C. for another 12 hours under hydrogen atmosphere (50 psi). The mixture was filtered. The filtrate was concentrated under reduced pressure to give the product, tert-butyl 4-[2-[2-(2-hydroxyethoxy)ethoxy]ethoxy]piperidine-1-carboxylate (9 g) as a colorless oil. ¹H-NMR (400 MHz, CDCl₃) δ 3.82-3.60 (m, 14H), 3.50-3.47 (m, 1H), 3.06-3.02 (m, 2H), 1.85-1.82 (m, 2H), 1.53-1.44 (m, 11H).

Step 4: Preparation of tert-butyl 4-(2-(2-(2-(tosyloxy)ethoxy)ethoxy)ethoxy)piperidine-1-carboxylate

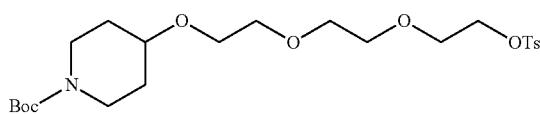

To the mixture of tert-butyl 4-[2-[2-(2-hydroxyethoxy)ethoxy]ethoxy]piperidine-1-carboxylate (7 g, 20.99 mmol, 1 eq) and potassium hydroxide (1.53 g, 27.29 mmol, 1.3 eq) in tetrahydrofuran (70 mL) was added p-toluenesulfonyl chloride (4.80 g, 25.19 mmol, 1.2 eq). The mixture was stirred at 25° C. for 1 hour. The mixture was diluted with ice water (100 mL). Then it was extracted with ethyl acetate (100 mL×3). The combined organic layer was washed with brine (150 mL×2), dried over anhydrous sodium sulfate, filtered and concentrated under reduced pressure to give a residue. The residue was purified by silica gel chromatography (petroleum ether:ethyl acetate=10:1 to 1:2). Compound tert-butyl 4-[2-[2-[2-(p-tolylsulfonyloxy)ethoxy]ethoxy]ethoxy]piperidine-1-carboxylate (7.5 g, 15.38 mmol, 73.26% yield) was obtained as a colorless oil. ¹H-NMR (400 MHz, CDCl₃) δ 7.78 (d, J=8.4 Hz, 2H), 7.33 (d, J=8.4 Hz, 2H), 4.14 (t, J=4.8 Hz, 2H), 3.82-3.75 (m, 2H), 3.69-3.66 (m, 2H), 3.59-3.57 (m, 8H), 3.45-3.35 (m, 1H), 3.05-3.00 (m, 2H), 2.43 (s, 3H), 1.81-1.80 (m, 2H), 1.50-1.44 (m, 11H).

Step 5: Preparation of tert-butyl 4-(2-(2-(2-(1,3-dioxoisoindolin-2-yl)ethoxy)ethoxy)ethoxy)piperidine-1-carboxylate

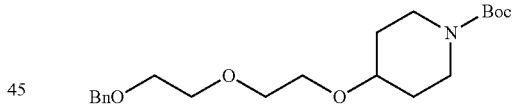

To the mixture of tert-butyl 4-[2-[2-[2-(p-tolylsulfonyloxy)ethoxy]ethoxy]ethoxy]piperidine-1-carboxylate (3.5 g, 7.18 mmol, 1 eq) in N,N-dimethylformamide (30 mL) was added (1,3-dioxoisoindolin-2-yl)potassium (1.60 g, 8.61 mmol, 1.2 eq). The mixture was stirred at 80° C. for 2 hours. The mixture was diluted with water (100 mL). Then it was extracted with ethyl acetate (50 mL×3). The combined organic layer was washed with water (80 mL×2) and brine (80 mL×2), dried over anhydrous sodium sulfate, filtered and concentrated under reduced pressure to give a residue. The residue was purified by gel silica chromatography (petroleum ether:ethyl acetate=3:1 to 1:1). Compound tert-butyl 4-[2-[2-[2-(1,3-dioxoisoindolin-2-yl)ethoxy]ethoxy]ethoxy]piperidine-1-carboxylate (2.31 g, 4.99 mmol, 69% yield) was obtained as a colorless oil. LC/MS (ESI) m/z: 363.1 [M−100]⁺.

Exemplary Synthesis of tert-butyl 4-(2-(2-(tosyloxy)ethoxy)ethoxy)piperidine-1-carboxylate Step 1: Preparation of 2-(2-(benzyloxy)ethoxy)ethyl 4-methylbenzenesulfonate

To a solution of 2-(2-benzyloxyethoxy)ethanol (50 g, 254.79 mmol, 1 eq) and potassium hydroxide (17.15 g, 305.74 mmol, 1.2 eq) in tetrahydrofuran (200 mL) was added paratoluensulfonyl chloride (48.57 g, 254.79 mmol, 1 eq). The mixture was stirred at 25° C. for 1 hour. Ice-water (500 mL) and ethyl acetate (500 mL) was added, the aqueous phase was extracted with ethyl acetate (300 mL*3). The combined organic phase was washed with brine (200 mL), dried with anhydrous sodium sulfate, filtered and concentrated in vacuum. The residue was purified by flash silica gel chromatography (Petroleum ether:Ethyl acetate=5:1 to 3:1). Compound 2-(2-benzyloxyethoxy)ethyl 4-methylbenzenesulfonate (70 g, 199.76 mmol, 78% yield) was obtained as a yellow oil. ¹H-NMR (400 MHz, CDCl₃) δ 7.85-7.75 (m, 2H), 7.38-7.28 (m, 7H), 4.54 (s, 2H), 4.23-4.13 (m, 2H), 3.72-3.69 (m, 2H), 3.64-3.60 (m, 2H), 3.59-3.55 (m, 2H), 2.44 (s, 3H).

Step 2: Preparation of tert-butyl 4-(2-(2-(benzyloxy)ethoxy)ethoxy)piperidine-1-carboxylate To a mixture of tert-butyl 4-hydroxypiperidine-1-carboxylate (12.27 g, 60.97 mmol, 1.07 eq) in N,N-dimethylformamide (200 mL) was added sodium hydride (2.55 g, 63.75 mmol, 60% purity, 1.12 eq) at 0° C. stirred for 0.5 hour. Then 2-(2-benzyloxyethoxy)ethyl 4-methylbenzenesulfonate (20 g, 57.07 mmol, 1 eq) was added, the mixture was stirred at 25° C. for 1 hour. Ammonium chloride solution (200 mL) was added, then the aqueous phase was extracted with ethyl acetate (200 mL*3). The combined organic phase was washed with brine (100 mL*2), dried with anhydrous sodium sulfate, filtered and concentrated in vacuum. The residue was purified by flash silica gel chromatography (Petroleum ether:Ethyl acetate=5:1 to 3:1). Compound tert-butyl 4-[2-(2-benzyloxyethoxy)ethoxy]piperidine-1-carboxylate (16.2 g) as a yellow oil was obtained. ¹H-NMR (400 MHz, CDCl₃) δ 7.38-7.33 (m, 4H), 7.32-7.28 (m, 1H), 4.58 (s, 2H), 4.15-4.08 (m, 1H), 3.77 (d, J=13.0 Hz, 2H), 3.72-3.66 (m, 2H), 3.66-3.63 (m, 5H), 3.61-3.42 (m, 1H), 3.05 (ddd, J=3.4, 9.5, 13.3 Hz, 2H), 1.83 (d, J=7.1 Hz, 2H), 1.52 (tdd, J=4.5, 8.7, 13.0 Hz, 2H), 1.46 (s, 9H).

Step 3: Preparation of tert-butyl 4-(2-(2-hydroxyethoxy)ethoxy)piperidine-1-carboxylate

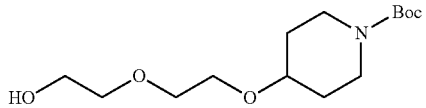 [SMILES: CC(C)(C)OC(=O)N1CCC(OCCOCCO)CC1]

To a solution of tert-butyl 4-[2-(2-benzyloxyethoxy)ethoxy]piperidine-1-carboxylate (16.2 g, 42.69 mmol, 1 eq) in methanol (100 mL) was added palladium on carbon (1.5 g, 42.69 mmol, 4.27 mL, 10% purity, 1 eq) under nitrogen. The suspension was degassed under vacuum and purged with hydrogen several times. The mixture was stirred under hydrogen (50 psi) at 25° C. for 60 hours. The reaction mixture was filtered and concentrated under reduced pressure to give a residue. Compound tert-butyl 4-[2-(2-hydroxyethoxy)ethoxy]piperidine-1-carboxylate (6.7 g, 23.15 mmol, 54% yield) was obtained as a yellow oil. $^{1}$H-NMR (400 MHz, CD$_{3}$OD) δ 3.79-3.71 (m, 2H), 3.70-3.61 (m, 7H), 3.59-3.55 (m, 3H), 3.21-3.06 (m, 2H), 1.91-1.81 (m, 2H), 1.51-1.42 (m, 12H).

Step 4: Preparation of tert-butyl 4-(2-(2-(tosyloxy)ethoxy)ethoxy)piperidine-1-carboxylate

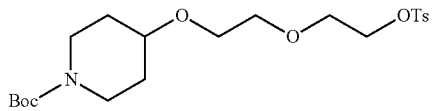

To a solution of tert-butyl 4-[2-(2-hydroxyethoxy)ethoxy]piperidine-1-carboxylate (6.5 g, 22.46 mmol, 1 eq) in dichloromethane (65 mL) was added triethylamine (6.82 g, 67.39 mmol, 9.38 mL, 3 eq), then p-toluenesulfonyl chloride (6.42 g, 33.69 mmol, 1.5 eq) was added to the mixture, the mixture was stirred at 25° C. for 16 hours. The reaction was concentrated under reduced pressure to give a residue. The residue was purified by flash silica gel chromatography (0-25% Ethyl acetate/Petroleum ether). tert-butyl 4-[2-[2-(p-tolylsulfonyloxy)ethoxy]ethoxy]piperidine-1-carboxylate (7.4 g, 16.68 mmol, 74% yield) was obtained as a colorless oil. $^{1}$H-NMR (400 MHz, CD$_{3}$OD) δ 7.81-7.76 (m, 2H), 7.46-7.41 (m, 2H), 4.81 (s, 3H), 3.74-3.64 (m, 4H), 3.58-3.49 (m, 6H), 3.11 (t, J=9.6 Hz, 2H), 2.47-2.45 (m, 1H), 1.86-1.76 (m, 2H), 1.46 (s, 9H), 1.48-1.37 (m, 2H).

Exemplary Synthesis of N-(1,3-dimethyl-2-oxo-6-(3-propoxyphenoxy)-2,3-dihydro-1H-benzo[d]imidazol-5-yl)-4-hydroxy-N-((2-(trimethylsilyl)ethoxy)methyl)benzenesulfonamide

Step 1: Preparation of sodium 4-(benzyloxy)benzenesulfonate

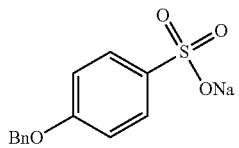

To a solution of 4-hydroxybenzenesulfonic acid (17.50 g, 100.47 mmol, 1 eq) inpropan-2-ol (280 mL) was added (bromomethyl)benzene (36.86 g, 215.54 mmol, 25.6 mL, 2.15 eq), sodium hydroxide (2 M, 100 mL, 1.99 eq) and dropwise (bromomethyl)benzene (36.86 g, 215.54 mmol, 25.6 mL, 2.15 eq). The mixture was stirred at 70° C. for 20 hours. The mixture was concentrated to give solid, the solid were washed with water (50 mL), filtered and concentrated under reduced pressure to give the product (4-benzyloxyphenyl)sulfonyloxysodium (19.00 g, 66.37 mmol, 66% yield) as a white solid. $^{1}$H-NMR (400 MHz, DMSO-d$_{6}$) δ 7.52 (d, J=8.8 Hz, 2H), 7.46-7.32 (m, 5H), 6.94 (d, J=8.8 Hz, 2H), 5.12 (s, 2H).

Step 2: Preparation of 4-(benzyloxy)benzenesulfonyl chloride

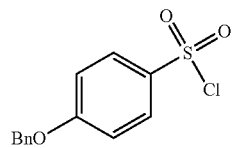

To a solution of (4-benzyloxyphenyl)sulfonyloxysodium (19.00 g, 66.37 mmol, 1.00 eq) in sulfurous dichloride (80 mL) was added N,N-dimethylformamide (475 mg, 6.50 mmol, 0.5 mL, 0.98 eq). The mixture was stirred at 70° C. for 4 hour. The mixture was concentrated to give a crude product, and this material was dissolved with ethyl acetate (50 mL) and washed by water (150 mL) followed by three washes with saturated sodium bicaarbonate and brine, filtered and the filtrate was condensed to give a white solid. Compound 4-benzyloxybenzenesulfonyl chloride (16.50 g, 58.36 mmol, 88% yield) was obtained as a white solid. $^{1}$H-NMR (400 MHz, CDCl$_{3}$) δ 8.00 (dd, J=2.0, 6.8 Hz, 2H), 7.46-7.40 (m, 5H), 7.15 (dd, J=2.0, 6.8 Hz, 2H), 5.21 (s, 2H).

Step 3: Preparation of 4-(benzyloxy)-N-(1,3-dimethyl-2-oxo-6-(3-propoxyphenoxy)-2,3-dihydro-1H-benzo[d]imidazol-5-yl)benzenesulfonamide

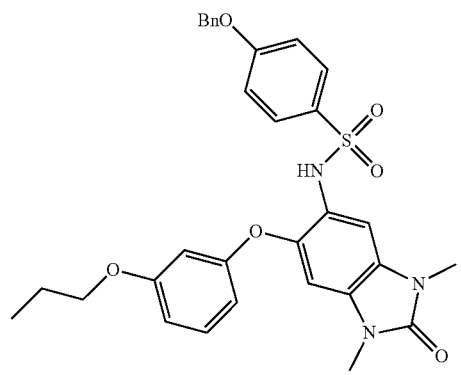 [SMILES: CCCOc1cccc(Oc2cc3c(cc2NS(=O)(=O)c2ccc(OCc4ccccc4)cc2)n(C)c(=O)n3C)c1]

To a solution of 5-amino-1,3-dimethyl-6-(3-propoxyphenoxy)benzimidazol-2-one (3.00 g, 9.16 mmol, 1.00 eq) and triethylamine (1.39 g, 13.75 mmol, 2.0 mL, 1.50 eq) in dichloromethane (30 mL) was added dropwise a solution of 4-benzyloxybenzenesulfonyl chloride (2.60 g, 9.16 mmol, 1.00 eq) in dichloromethane (10 mL) at 0° C. The mixture was stirred at 20° C. for 12 hours. The mixture was added water (20 mL), then extracted with ethyl acetate (50 mL×3), the organic layers were washed with salt water, then dried over sodium sulfate, filtered and concentrated under reduced pressure to give a residue. The residue was purified by prep-HPLC. The compound 4-benzyloxy-N-[1,3-dimethyl-2-oxo-6-(3-propoxyphenoxy) benzimidazol-5-yl]benzenesulfonamide (2.30 g, 4.01 mmol, 44% yield) was obtained as a yellow solid. LC/MS (ESI) m/z: 574.2 [M+1]⁺.

Step 4: Preparation of 4-(benzyloxy)-N-(1,3-dimethyl-2-oxo-6-(3-propoxyphenoxy)-2,3-dihydro-1H-benzo[d]imidazol-5-yl)-N-((2-(trimethylsilyl)ethoxy)methyl)benzenesulfonamide

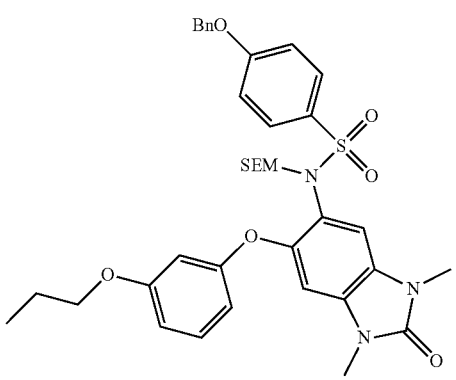 [SMILES: CCCOc1cccc(Oc2cc3c(cc2N(COCC[Si](C)(C)C)S(=O)(=O)c2ccc(OCc4ccccc4)cc2)n(C)c(=O)n3C)c1]

To a solution of 4-benzyloxy-N-[1,3-dimethyl-2-oxo-6-(3-propoxyphenoxy) benzimidazol-5-yl]benzenesulfonamide (2.30 g, 4.01 mmol, 1.00 eq) in tetrahydrofuran (30 mL) was added sodium hydride (208 mg, 5.21 mmol, 60% purity, 1.30 eq) at 0° C. for 30 minutes, then the trimethylsilyi ethoxymethyl choloride (870 mg, 5.21 mmol, 1.30 eq) was added dropwise. The reaction was stirred at 25° C. for 12 hours. The mixture was added water (50 mL), then extracted with ethyl acetate (50 mL×3), the organic layers were washed with water, then dried over sodium sulfate, filtered and concentrated under reduced pressure to give a residue. The residue was purified by silica gel (petroleum ether/ethyl acetate, 10/1-1/1). The compound 4-benzyloxy-N-[1,3-dimethyl-2-oxo-6-(3-propoxyphenoxy)benzimidazol-5-yl]-N-(2-trimethylsilylethoxymethyl)benzenesulfonamide (2.70 g, 3.84 mmol, 96% yield) was obtained as a yellow solid. LC/MS (ESI) m/z: 704.2 [M+1]⁺.

Step 5: Preparation of N-(1,3-dimethyl-2-oxo-6-(3-propoxyphenoxy)-2,3-dihydro-1H-benzo[d]imidazol-5-yl)-4-hydroxy-N-((2-(trimethylsilyl)ethoxy)methyl)benzenesulfonamide

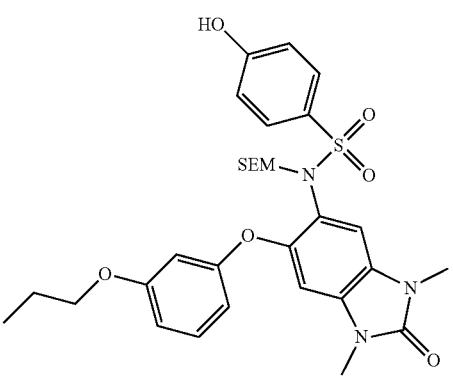 [SMILES: CCCOc1cccc(Oc2cc3c(cc2N(COCC[Si](C)(C)C)S(=O)(=O)c2ccc(O)cc2)n(C)c(=O)n3C)c1]

A mixture of 4-benzyloxy-N-[1,3-dimethyl-2-oxo-6-(3-propoxyphenoxy)benzimidazol-5-yl]-N-(2-trimethylsilylethoxymethyl)benzenesulfonamide (2.70 g, 3.84 mmol, 1.00 eq), Palladium on activated carbon (3.84 mmol, 10% purity, 1.00 eq) in methanol (30 mL) was degassed and purged with nitrogen gas for 3 times, and then the mixture was stirred at 25° C. for under hydrogen gas atmosphere for 3 hours. The mixture was filtered through a celite pad, and the filtrate was concentrated to give the product. The compound N-[1,3-dimethyl-2-oxo-6-(3-propoxyphenoxy) benzimidazol-5-yl]-4-hydroxy-N-(2-trimethylsilylethoxymethyl)benzenesulfonamide (2.30 g, 3.75 mmol, 98% yield) was obtained as white solid. LC/MS (ESI) m/z: 636.3 [M+23]⁺.

Exemplary Synthesis of tert-butyl (S)-2-(cyanomethyl)-4-(2-(((2S,4R)-4-(2-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate and tert-butyl (S)-2-(cyanomethyl)-4-(2-(((2S,4R)-4-(2-(2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate Step 1: Preparation of tert-butyl (2S,4R)-2-(((tert-butyldimethylsilyl)oxy)methyl)-4-hydroxypyrrolidine-1-carboxylate

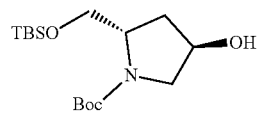 [SMILES: CC(C)(C)OC(=O)N1C[C@H](O)C[C@H]1CO[Si](C)(C)C(C)(C)C]

To a solution of tert-butyl (2S,4R)-4-hydroxy-2-(hydroxymethyl)pyrrolidine-1-carboxylate (25 g, 115.07 mmol, 1 eq) in dichloromethane (400 mL) was added triethylamine (23.29 g, 230.14 mmol, 32.03 mL, 2 eq) and N,N-dimethylpyridin-4-amine (1.41 g, 11.51 mmol, 0.1 eq), and then tert-butyldimethylsilyl chloride (18.21 g, 120.82 mmol, 1.05 eq) was added at 0° C., the mixture was stirred at 25° C. for 48 hours. Evaporate the solution on a water bath under reduced pressure using a rotary evaporator. This crude product was purified by silica gel column chromatography (EA:PE=0:1 to 1:5) to give compound tert-butyl (2S,4R)-2-[[tert-butyl(dimethyl)silyl]oxymethyl]-4-hydroxy-pyrrolidine-1-carboxylate (40 g) as a colorless oil. $^1$H-NMR (400 MHz, CD$_3$OD) δ 4.45 (s, 1H), 4.00-3.91 (m, 1H), 3.56-3.53 (m, 2H), 3.40 (s, 2H), 2.23-2.15 (m, 2H), 2.00-1.90 (m, 1H), 1.45 (s, 9H), 0.89 (s, 9H), 0.01 (s, 6H).

Step 2: Preparation of tert-butyl (2S,4R)-2-(((tert-butyldimethylsilyl)oxy)methyl)-4-(2-(2-((tetrahydro-2H-pyran-2-yl)oxy)ethoxy)ethoxy)pyrrolidine-1-carboxylate

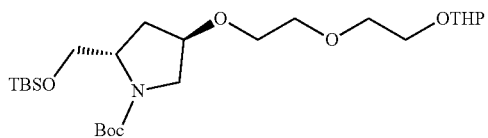

To a solution of tert-butyl (2S,4R)-2-[[tert-butyl(dimethyl)silyl]oxymethyl]-4-hydroxy-pyrrolidine-1-carboxylate (40 g, 120.66 mmol, 1 eq) in tetrahydrofuran (500 mL) was added sodium hydride (7.24 g, 180.98 mmol, 60% in mineral oil, 1.5 eq) at 0° C. The reaction mixture was stirred at 25° C. for 1 hour. Then 2-(2-tetrahydropyran-2-yloxyethoxy)ethyl 4-methylbenzenesulfonate (45.71 g, 132.72 mmol, 1.1 eq) was added and the reaction mixture was stirred at 25° C. for another 12 hours. The reaction mixture was quenched by saturated aqueous ammonium chloride (200 mL), then extracted by ethyl acetate (100 mL×3). The organic layers were combined and evaporated under vacuum to get the residue. The residue was purified through silica gel column chromatography (Petroleum ether/Ethyl acetate=1/0 to 2/1) to get the product. Tert-butyl (2S,4R)-2-[[tert-butyl(dimethyl)silyl]oxymeth-yl]-4-[2-(2-tetrahydropyran-2-yloxyethoxy)ethoxy]pyrrolidine-1-carboxylate (40.8 g, 83.79 mmol, 68% yield) was obtained as a light yellow oil. $^1$H-NMR (400 MHz, CDCl$_3$) δ 4.65-4.64 (m, 1H), 3.90-3.85 (m, 4H), 3.70-3.39 (m, 12H), 2.23-2.13 (m, 1H), 2.10-1.92 (m, 1H), 1.91-1.49 (m, 6H), 1.45 (s, 9H), 0.88 (s, 9H), 0.03 (s, 6H).

Step 3: Preparation of tert-butyl (2S,4R)-2-(hydroxymethyl)-4-(2-(2-((tetrahydro-2H-pyran-2-yl)oxy)ethoxy)ethoxy)pyrrolidine-1-carboxylate

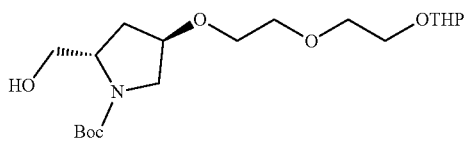

To a solution of tert-butyl (2S,4R)-2-[[tert-butyl(dimethyl)silyl]oxymethyl]-4-[2-(2-tetrahydr-opyran-2-yloxyethoxy)ethoxy]pyrrolidine-1-carboxylate (10.8 g, 21.44 mmol, 1 eq) in tetrahydrofuran (125 mL) was added tetrabutylammonium fluoride (1 M, 23.6 mL, 1.1 eq) at 25° C. The mixture was stirred at 25° C. for 12 hours. The solvent was removed under vacuum to get the residue. The residue was purified through silica gel column chromatography (Petroleum ether/Ethyl acetate=10/1 to 1/1). The product tert-butyl (2S,4R)-2-(hydroxymethyl)-4-[2-(2-tetrahydropyran-2-yloxyethoxy)ethoxy]pyrrolidine-1-carboxylate (6.35 g, 16.30 mmol, 76% yield) was obtained as a light yellow oil.

Step 4: Preparation of ((2S,4R)-1-methyl-4-(2-(2-((tetrahydro-2H-pyran-2-yl)oxy)ethoxy)ethoxy)pyrrolidin-2-yl)methanol

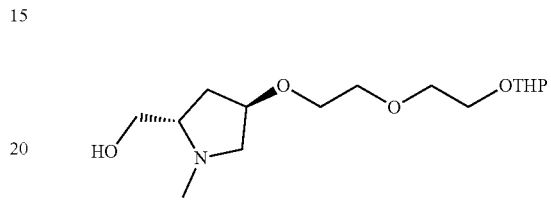

To a solution of tert-butyl (2S,4R)-2-(hydroxymethyl)-4-[2-(2-tetrahydropyran-2-yloxyethox-y)ethoxy]pyrrolidine-1-carboxylate (20 g, 51.35 mmol, 1 eq) in tetrahydrofuran (350 mL) was added lithium aluminum hydride (4.87 g, 128.38 mmol, 2.5 eq) at 25° C. The mixture was stirred at 60° C. for 16 hours. The reaction mixture was quenched by water (10 mL) before celite (20 g) was added. The mixture was filtered and the filtrate was collected, then evaporated under vacuum to get [(2S,4R)-1-methyl-4-[2-(2-tetrahydropyran-2-yloxyethoxy)ethoxy]pyrrolidin-2-yl]methanol (14 g) as a light yellow oil. $^1$H-NMR (400 MHz, CDCl$_3$) δ 4.64-4.63 (m, 1H), 4.01-3.97 (m, 1H), 3.87-3.85 (m, 2H), 3.70-3.46 (m, 9H), 3.40-3.38 (m, 2H), 2.63-2.61 (m, 1H), 2.40-2.36 (m, 1H), 2.33 (s, 3H), 2.13-2.02 (m, 1H), 1.88-1.43 (m, 8H).

Step 5: Preparation of tert-butyl 4-((S)-4-((benzyloxy)carbonyl)-3-(cyanomethyl)piperazin-1-yl)-2-(((2S,4R)-1-methyl-4-(2-(2-((tetrahydro-2H-pyran-2-yl)oxy)ethoxy)ethoxy)pyrrolidin-2-yl)methoxy)-5,8-dihydropyrido[3,4-d]pyrimidine-7(6H)-carboxylate

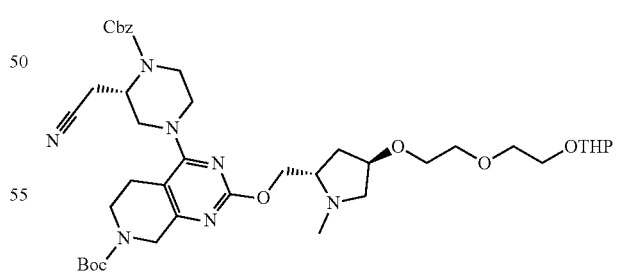

To a solution of [(2S,4R)-1-methyl-4-[2-(2-tetrahydropyran-2-yloxyethoxy)ethoxy]pyrrolidin-2-yl]methanol (6.22 g, 20.49 mmol, 1.2 eq) and tert-butyl 4-[(3S)-4-benzyloxycarbonyl-3-(cyanomethyl)piperazin-1-yl]-2-chloro-6,8-dihydro-5H-pyrido[3,4-d]pyrimidine-7-carboxylate (9 g, 17.08 mmol, 1 eq) in dioxane (180 mL) was added methanesulfonato(2-dicyclohexyl-phosphino-2',6'-di-1-propoxy-1,1'-biphenyl)(2'-amino-1,1'-biphenyl-2-yl)palladium(II)

(1.43 g, 1.71 mmol, 0.1 eq) and cesium carbonate (16.69 g, 51.23 mmol, 3 eq) under nitrogen. The reaction mixture was stirred at 90° C. for 6 hours under nitrogen. The solvent was removed under vacuum to get the crude product. The crude product was purified by silica gel column chromatography (Ethyl acetate) to get the product. The product tert-butyl 4-[(3S)-4-benzyloxycarbonyl-3-(cyanomethyl)piperazin-1-yl]-2-[[(2S,4R)-1-methyl-4-[2-(2-tetrahydropyran-2-yloxyethoxy)ethoxy]pyrrolidin-2-yl]methoxy]-6,8-dihydro-5H-pyrido[3,4-d]pyrimidine-7-carboxylate (7.4 g, 6.63 mmol, 39% yield, 71% purity) was obtained as a brown solid. LC/MS (ESI) m/z: 794.5 [M+1]$^+$.

Step 6: Preparation of benzyl (S)-2-(cyanomethyl)-4-(2-(((2S,4R)-4-(2-(2-hydroxyethoxy)ethoxy)-1-methylpyrrolidin-2-yl)methoxy)-5,6,7,8-tetrahydro-pyrido[3,4-d]pyrimidin-4-yl)piperazine-1-carboxylate

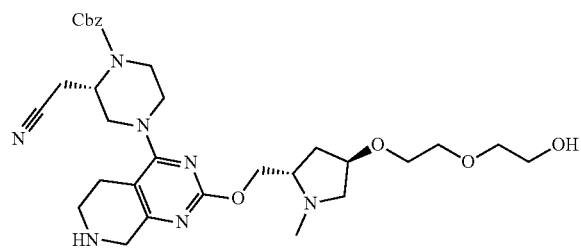 [SMILES: CN1C[C@H](OCCOCCO)C[C@H]1COc1nc2c(c(N3CCN(C(=O)OCc4ccccc4)[C@@H](CC#N)C3)n1)CCNC2]

To a solution of tert-butyl 4-[(3S)-4-benzyloxycarbonyl-3-(cyanomethyl)piperazin-1-yl]-2-[[(2S,4R)-1-methyl-4-[2-(2-tetrahydropyran-2-yloxyethoxy)ethoxy]pyrrolidin-2-yl]methoxy]-6,8-dihydro-5H-pyrido[3,4-d]pyrimidine-7-carboxylate (7 g, 8.82 mmol, 1 eq) in dichloromethane (100 mL) was added trifluoroacetic acid (25.13 g, 220.42 mmol, 16.3 mL, 25 eq). The mixture was stirred at 25° C. for 2 hours. The reaction mixture was quenched by saturated aqueous sodium bicarbonate solution (100 mL), then extracted by dichloromethane (30 mL×3). The combined organic layers were evaporated under vacuum to remove the solvent to get the crude product. The crude product was purified by Prep-HPLC. The product benzyl (2S)-2-(cyanomethyl)-4-[2-[[(2S,4R)-4-[2-(2-hydroxyethoxy)ethoxy]-1-methyl-pyrrolidin-2-yl]methoxy]-5,6,7,8-tetrahy-dro-pyrido[3,4-d]pyrimidin-4-yl]piperazine-1-carboxylate (2.76 g, 4.13 mmol, 47% yield, 91% purity) was obtained as a light yellow solid. LC/MS (ESI) m/z: 610.4 [M+1]$^+$; $^1$H-NMR (400 MHz, CDCl$_3$) δ 7.40-7.37 (m, 5H), 5.19 (s, 2H), 4.65 (s, 1H), 4.37 (dd, J=11.2 Hz, J=4.4 Hz, 1H), 4.18-2.58 (m, 26H), 2.46 (s, 3H), 2.38 (dd, J=9.6 Hz, J=6.0 Hz, 1H), 2.01-1.95 (m, 3H).

Step 7: Preparation of benzyl (S)-2-(cyanomethyl)-4-(2-(((2S,4R)-4-(2-(2-hydroxyethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

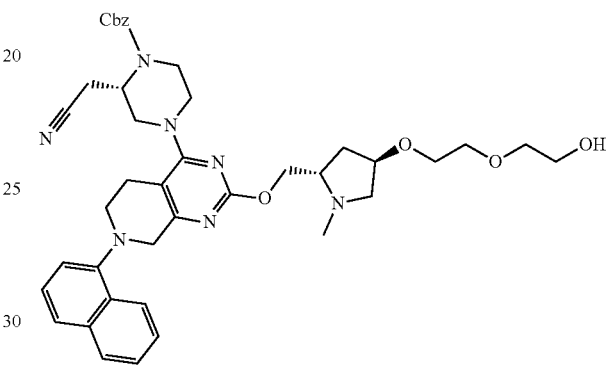

To a solution of benzyl (2S)-2-(cyanomethyl)-4-[2-[[(2S,4R)-4-[2-(2-hydroxyethoxy)ethoxy]-1-methyl-pyrrolidin-2-yl]methoxy]-5,6,7,8-tetrahydropyrido[3,4-d]pyrimidin-4-yl]piperazine-1-carboxylate (2.2 g, 3.61 mmol, 1 eq) and 1-bromonaphthalene (1.34 g, 6.49 mmol, 0.9 mL, 1.8 eq) in dioxane (50 mL) was added methanesulfonato(2-dicyclohexylphosphino-2',6'-di-i-propoxy-1,1'-biphenyl)(2'-amino-1,1'-biphenyl-2-yl)palladium(II) (301.8 mg, 0.36 mmol, 0.1 eq) and cesium carbonate (3.53 g, 10.82 mmol, 3 eq) in nitrogen. The mixture was stirred at 90° C. for 12 hours in nitrogen. The reaction mixture was quenched by water (50 mL) and extracted by ethyl acetate (40 mL×3). The organic layers were combined and evaporated under vacuum to get the residue. The residue was purified through silica gel column chromatography (Dichloromethane/Methanol=10/1) to get the product. The product benzyl (2S)-2-(cyanomethyl)-4-[2-[[(2S,4R)-4-[2-(2-hydroxyethoxy)ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (1.15 g, 1.39 mmol, 38% yield, 89% purity) was obtained as a yellow oil. LC/MS (ESI) m/z: 736.3 [M+1]$^+$; $^1$H-NMR (400 MHz, CDCl$_3$) δ 8.22-8.20 (m, 1H), 7.87-7.85 (m, 1H), 7.62 (d, J=8.0 Hz, 1H), 7.51-7.36 (m, 8H), 7.15 (d, J=6.8 Hz, 1H), 5.21 (s, 2H), 4.70 (s, 1H), 4.38-4.10 (m, 8H), 3.76-3.31 (m, 14H), 3.10-2.72 (m, 6H), 2.47 (s, 3H), 2.39-2.35 (m, 1H), 2.14-2.08 (m, 1H), 2.03-1.96 (m, 1H).

Step 8: Preparation of 2-((S)-4-(2-(((2S,4R)-4-(2-(2-hydroxyethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

Step 9: Preparation of tert-butyl (S)-2-(cyanomethyl)-4-(2-(((2S,4R)-4-(2-(2-hydroxyethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

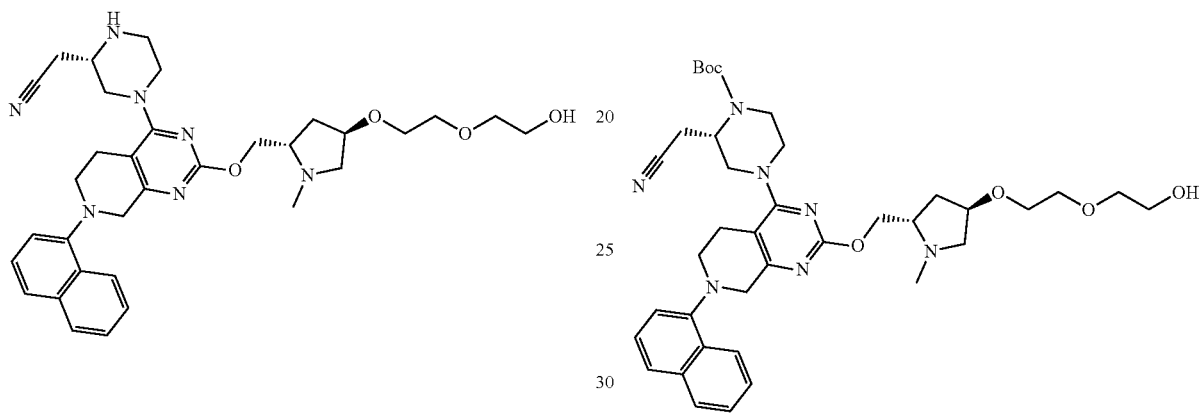

To a solution of benzyl (2S)-2-(cyanomethyl)-4-[2-[[(2S,4R)-4-[2-(2-hydroxyethoxy)ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (1.38 g, 1.88 mmol, 1 eq) and ammonium hydroxide (1.82 g, 12.98 mmol, 2 mL, 25% purity, 6.92 eq) in methanol (60 mL) and tetrahydrofuran (3 mL) was added palladium on activated carbon catalyst (200 mg, 10% purity). The mixture was degassed and charged with hydrogen, then stirred at 25° C. with hydrogen (15 psi) for 12 hours. The reaction mixture was added tetrahydrofuran (40 mL) and filtered. The organic solvent was removed under vacuum to get 2-[(2S)-4-[2-[[(2S,4R)-4-[2-(2-hydroxyethoxy)ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (1.1 g) as a light yellow solid. LC/MS (ESI) m/z: 602.3 [M+1]⁺; ¹H-NMR (400 MHz, CDCl₃) δ 8.23-8.21 (m, 1H), 7.87-7.85 (m, 1H), 7.62 (d, J=8.4 Hz, 1H), 7.51-7.49 (m, 2H), 7.43 (t, J=8.4 Hz, 1H), 7.15-7.13 (m, 1H), 4.41-4.39 (m, 1H), 4.26 (s, 2H), 4.22 (dd, J=11.2 Hz, J=6.4 Hz, 1H), 4.03 (d, J=12.0 Hz, 1H), 3.88 (d, J=12.0 Hz, 1H), 3.76-3.72 (m, 3H), 3.67-3.54 (m, 6H), 3.45-2.85 (m, 12H), 2.57-2.55 (m, 2H), 2.47 (s, 3H), 2.39 (dd, J=9.6 Hz, J=6.0 Hz, 1H), 2.11-1.84 (m, 2H).

To a solution of 2-[(2S)-4-[2-[[(2S,4R)-4-[2-(2-hydroxyethoxy)ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (800 mg, 1.33 mmol, 1 eq) in tetrahydrofuran (30 mL) and water (30 mL) was added sodium bicarbonate (223.4 mg, 2.66 mmol, 0.1 mL, 2 eq) and di-tert-butyl dicarbonate (1.45 g, 6.65 mmol, 1.5 mL, 5 eq). The mixture was stirred at 25° C. for 6 hours. The reaction mixture was quenched by adding water (20 mL), then extracted by ethyl acetate (30 mL×3). The organic phase was washed with brine (30 mL×2), evaporated under vacuum to get the crude product. The crude product was purified through silica gel column chromatography (Dichloromethane/Methanol=10/1). The product tert-butyl (2S)-2-(cyano-methyl)-4-[2-[[(2S,4R)-4-[2-(2-hydroxyethoxy)ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (670 mg, 0.95 mmol, 72% yield) was obtained as a light yellow solid. LC/MS (ESI) m/z: 702.4 [M+1]⁺; ¹H-NMR (400 MHz, CDCl₃) δ 8.23-8.20 (m, 1H), 7.87-7.85 (m, 1H), 7.62 (d, J=8.4 Hz, 1H), 7.51-7.49 (m, 2H), 7.43 (t, J=8.4 Hz, 1H), 7.15-7.14 (m, 1H), 4.63 (s, 1H), 4.41-4.39 (m, 1H), 4.26-4.22 (m, 3H), 4.12 (d, J=12.0 Hz, 1H), 3.75-3.31 (m, 14H), 3.10-2.76 (m, 6H), 2.48 (s, 3H), 2.40 (dd, J=9.6 Hz, J=6.0 Hz, 1H), 2.37-2.05 (m, 2H), 1.52 (s, 9H).

Step 10: Preparation of tert-butyl (S)-2-(cyanomethyl)-4-(2-(((2S,4R)-1-methyl-4-(2-(2-(tosyloxy)ethoxy)ethoxy)pyrrolidin-2-yl)methoxy)-7-(naphthalen-1-yl)-5,6,7,8-tetrahydropyrido[3,4-d]pyrimidin-4-yl)piperazine-1-carboxylate

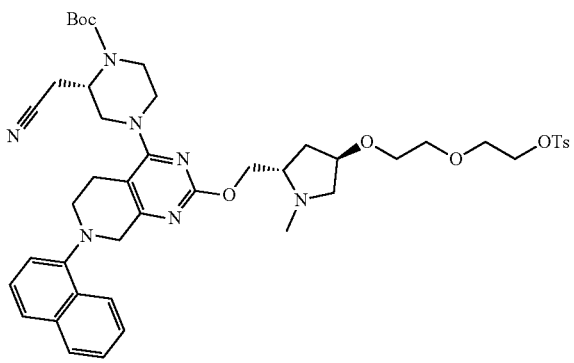 [SMILES: Cc1ccc(S(=O)(=O)OCCOCCO[C@@H]2C[C@@H](COc3nc4c(c(N5CCN(C(=O)OC(C)(C)C)[C@@H](CC#N)C5)n3)CCN(c3cccc5ccccc35)C4)N(C)C2)cc1]

To a solution of tert-butyl (2S)-2-(cyanomethyl)-4-[2-[[(2S,4R)-4-[2-(2-hydroxyethoxy)ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (300 mg, 0.43 mmol, 1 eq) in dichloromethane (5 mL) was added triethylamine (129.8 mg, 1.28 mmol, 0.2 mL, 3 eq), p-toluenesulfonyl chloride (163 mg, 0.85 mmol, 2 eq) and dimethylaminopyridine (10.4 mg, 0.09 mmol, 0.2 eq). The mixture was stirred at 25° C. for 12 hours. The solvent was removed under vacuum to get a residue. The residue was purified by prep-TLC (silicon dioxide, Dichloromethane/Methanol=10/1). The product tert-butyl (2S)-2-(cyanomethyl)-4-[2-[[(2S,4R)-1-methyl-4-[2-[2-(p-tolylsulfonyloxy)ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (233 mg, 0.27 mmol, 64% yield) was obtained as a light yellow solid. $^1$H-NMR (400 MHz, CDCl$_3$) δ 8.22-8.20 (m, 1H), 7.87-7.85 (m, 1H), 7.81-7.75 (m, 2H), 7.62 (d, J=8.0 Hz, 1H), 7.51-7.49 (m, 2H), 7.43 (t, J=8.0 Hz, 1H), 7.35 (d, J=8.0 Hz, 2H), 7.15-7.12 (m, 1H), 4.63 (s, 1H), 4.43-4.39 (m, 1H), 4.27-3.93 (m, 8H), 3.72-3.27 (m, 12H), 3.07-2.75 (m, 6H), 2.49 (s, 3H), 2.45 (s, 3H), 2.41-2.36 (m, 1H), 2.09-1.98 (m, 2H), 1.52 (s, 9H).

Step 11: Preparation of tert-butyl (S)-2-(cyanomethyl)-4-(2-(((2S,4R)-4-(2-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate and tert-butyl (S)-2-(cyanomethyl)-4-(2-(((2S,4R)-4-(2-(2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

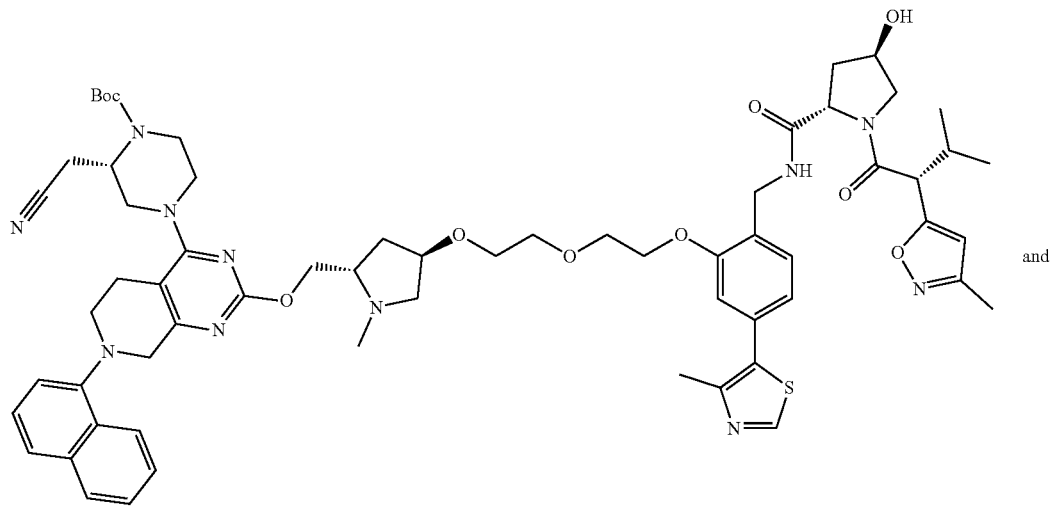

and

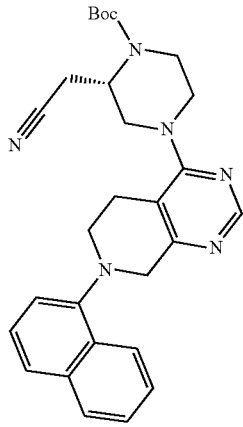
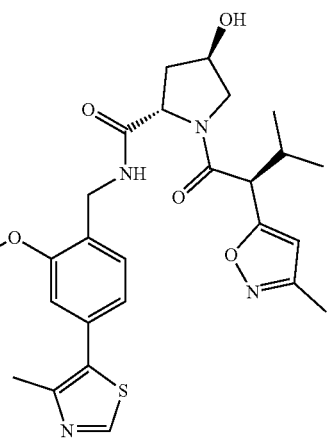

To a solution of tert-butyl (2S)-2-(cyanomethyl)-4-[2-[[(2S,4R)-1-methyl-4-[2-[²-(p-tolyl-sulfonyloxy)ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (250 mg, 0.29 mmol, 1 eq) and (2S,4R)-4-hydroxy-N-[[2-hydroxy-4-(4-methylthiazol-5-yl)phenyl]methyl]-1-[3-methyl-2-(3-methylisoxazol-5-yl)butanoyl]pyrrolidine-2-carboxamide (152.9 mg, 0.31 mmol, 1.05 eq) in acetonitrile (8 mL) was added cesium carbonate (190.3 mg, 0.58 mmol, 2 eq). The mixture was stirred at 80° C. for 14 hours. The mixture was extracted by ethyl acetate (30 mL×3) after water (30 mL) was added. The combined organic phases were evaporated under vacuum to get a residue. The residue was purified by Prep-TLC (silicon dioxide, Dichloromethane/Methanol=10/1). The product containing the two isomers (255 mg) was obtained as a yellow solid. Then the product was further purified through SFC. The product tert-butyl (2S)-2-(cyanomethyl)-4-[2-[[(2S,4R)-4-[2-[2-[2-[[[(2S,4R)-4-hydroxy-1-[(2R)-3-methyl-2-(3-methylisoxazol-5-yl)butanoyl]pyrrolidine-2-carbonyl]amino]methyl]-5-(4-methylthiazol-5-yl)phenoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (80 mg, 0.06 mmol, 21% yield, 92% purity) was obtained as a yellow oil. The product tert-butyl (2S)-2-(cyanomethyl)-4-[2-[[(2S,4R)-4-[2-[2-[2-[[[(2S,4R)-4-hydroxy-1-[(2S)-3-methyl-2-(3-methylisoxazol-5-yl)butanoyl]pyrrolidine-2-carbonyl]amino]methyl]-5-(4-methylthiazol-5-yl)phenoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (120 mg, 0.096 mmol, 33% yield, 95% purity) was obtained as a light yellow solid. LC/MS (ESI) m/z: 1182.7 [M+1]⁺.

Exemplary Synthesis of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate Step 1: Preparation of 1-benzyl 4-(tert-butyl) (R)-2-(hydroxymethyl)piperazine-1,4-dicarboxylate

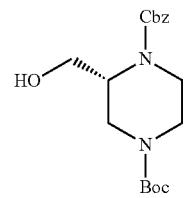

To a solution of tert-butyl (3R)-3-(hydroxymethyl)piperazine-1-carboxylate (5.00 g, 23.12 mmol, 1.00 eq) in ethyl acetate (50 mL) and water (50 mL) was added sodium bicarbonate (5.83 g, 69.00 mmol, 3.00 eq) in one portion, then benzyl carbonochloridate (5.94 g, 35.00 mmol, 1.51 eq) was added to the solution slowly with stirring at 0° C. for 30 minutes. The resulted solution was stirred at 10° C. for 5 hours. The organic layer was separated from the reaction solution, and washed with water (10 mL). The aqueous phase was extracted with ethyl acetate (100 mL). The organic layer was collected and combined, washed with water (30 mL×3) brine (30 mL), dried over sodium sulfate, concentrated under reduced pressure to give a yellow liquid. The yellow liquid was purified by silica gel column chromatography (Petroleum ether/Ethyl acetate=3/1 to 1/1) to obtained compound O1-benzyl-O4-tert-butyl (2R)-2-(hydroxymethyl)piperazine-1,4-dicarboxylate (8.00 g, 22.83 mmol, 99% yield) as colorless liquid. ¹H-NMR (400 MHz, CDCl₃) δ 7.33-7.24 (m, 5H), 5.08 (s, 2H), 4.18 (br s, 1H), 3.87 (br s, 2H), 3.57 (br s, 2H), 3.12-2.78 (m, 2H), 1.97 (s, 2H), 1.60-1.57 (m, 1H), 1.40 (s, 9H).

Step 2: Preparation of 1-benzyl 4-(tert-butyl) (R)-2-(((methylsulfonyl)oxy)methyl)piperazine-1,4-dicarboxylate

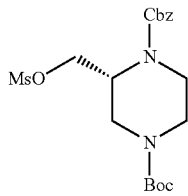

To a solution of O 1-benzyl-04-tert-butyl (2R)-2-(hydroxymethyl)piperazine-1,4-dicarboxylate (6.31 g, 18.01 mmol, 1.00 eq) in dichloromethane (100 mL) was added triethylamine (5.47 g, 54.00 mmol, 3.00 eq) in one portion. Then methylsulfonyl chloride (3.09 g, 27.00 mmol, 1.50 eq) was added to the solution. The resulted solution was stirred at 25° C. for 2 hours. The solution was concentrated under reduced pressure to give a compound O1-benzyl 04-tert-butyl (2R)-2-(methylsulfonyloxymethyl)piperazine-1,4-dicarboxylate (6.66 g) as yellow liquid.

Step 3: Preparation of 1-benzyl 4-(tert-butyl) (S)-2-(cyanomethyl)piperazine-1,4-dicarboxylate

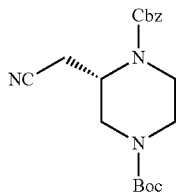 [SMILES: CC(C)(C)OC(=O)N1CCN(C(=O)OCc2ccccc2)[C@@H](CC#N)C1]

To a solution of O1-benzyl-04-tert-butyl (2R)-2-(methylsulfonyloxymethyl)piperazine-1,4-dicarboxylate (2.45 g, 5.72 mmol, 1.00 eq) in N,N-dimethylacetamide (10 mL) was added cyanosodium (560 mg, 11.00 mmol, 2.00 eq) in one portion. The solution was stirred at 55° C. for 24 hours. The solution was poured into ethyl acetate (200 mL), the solution was washed with water (50 mL×2). The organic layer was separated and collected, washed with brine (50 mL), concentrated under reduced pressure to give a yellow liquid. The yellow liquid was purified by column chromatography (silicon dioxide, Petroleum ether/Ethyl acetate=10/1 to 4/1) to give compound O1-benzyl-04-tert-butyl (2S)-2-(cyanomethyl)piperazine-1,4-dicarboxylate (1.00 g, 2.00 mmol, 40% yield) was obtained as colorless liquid. LC/MS (ESI) m/z: 304.1 [M−55]+; 1H-NMR (400 MHz, CDCl3) δ 7.39 (s, 5H), 5.19 (s, 2H), 4.58 (br s, 1H), 4.15-3.86 (m, 3H), 3.24-2.48 (m, 5H), 1.51 (s, 9H).

Step 4: Preparation of benzyl (S)-2-(cyanomethyl)piperazine-1-carboxylate

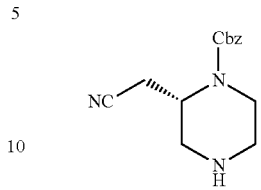

To a solution of O1-benzyl-O4-tert-butyl (2S)-2-(cyanomethyl)piperazine-1,4-dicarboxylate (900 mg, 2.50 mmol, 1.00 eq) in dichloromethane (10 mL) was added trifluoroacetic acid (3.08 g, 27.00 mmol, 10.79 eq) slowly. The solution was stirred at 10° C. for 2 hours. The solution was concentrated under reduced pressure to give benzyl (2S)-2-(cyanomethyl)piperazine-1-carboxylate (911 mg, 2.44 mmol, 97% yield, trifluoroacetic acid salt) as yellow liquid.

Step 5: Preparation of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate

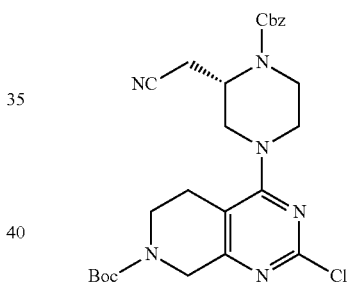

To a solution of benzyl (2S)-2-(cyanomethyl)piperazine-1-carboxylate (646 mg, 2.49 mmol, 1.00 eq, trifluoroacetic acid salt) and Diisopropylethylamine (1.29 g, 9.96 mmol, 4.00 eq) in dimethylsulfoxide (20 mL) was added tert-butyl 2,4-dichloro-5,6-dihydropyrido[3,4-d]pyrimidine-7(8H)-carboxylate (758 mg, 2.49 mmol, 1.00 eq) in one portion. The resulted solution was stirred at 50° C. for 9 hours. The reaction solution was diluted with ethyl acetate (200 mL) and water (100 mL). The organic layer was separated and collected, washed with water (50 mL×2) and brine (50 mL), dried over anhydrous sodium sulfate, concentrated under reduced pressure to give a yellow liquid. The yellow liquid was purified by column chromatography (silicon dioxide, Petroleum ether/Ethyl acetate=10/1 to 1/1) to obtained tert-butyl 4-[(3S)-4-benzyloxycarbonyl-3-(cyanomethyl) piperazin-1-yl]-2-chloro-6,8-dihydro-5H-pyrido[3,4-d]pyrimidine-7-carboxylate (1.10 g, 2.09 mmol, 84% yield) as yellow liquid. LC/MS (ESI) m/z: 527.1 [M+1]+; 1H-NMR (400 MHz, CDCl3) δ 7.46-7.32 (m, 5H), 5.26-5.14 (m, 2H), 4.67 (d, J=17.6 Hz, 2H), 4.51-4.42 (m, 1H), 4.21-4.05 (m, 2H), 3.93-3.75 (m, 2H), 3.40 (d, J=10.8 Hz, 2H), 3.12 (dt, J=3.2, 12.4 Hz, 1H), 2.97-2.51 (m, 3H), 1.61 (s, 2H), 1.50 (s, 9H).

Exemplary Synthesis of tert-butyl (S)-2-(cyanomethyl)-4-(2-(((2S,4R)-1-methyl-4-(2-(2-(2-(tosyloxy)ethoxy)ethoxy)ethoxy)pyrrolidin-2-yl)methoxy)-7-(naphthalen-1-yl)-5,6,7,8-tetrahydropyrido[3,4-d]pyrimidin-4-yl)piperazine-1-carboxylate Step 1: Preparation of tert-butyl (2S,4R)-2-(((tert-butyldimethylsilyl)oxy)methyl)-4-(2-(2-(2-((tetrahydro-2H-pyran-2-yl)oxy)ethoxy)ethoxy)ethoxy)pyrrolidine-1-carboxylate

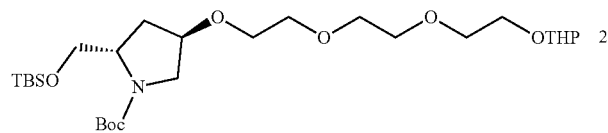

To a mixture of tert-butyl (2S,4R)-2-[[tert-butyl(dimethyl)silyl]oxymethyl]-4-hydroxy-pyrrolidine-1-carboxylate (15 g, 45.25 mmol, 1.1 eq) in tetrahydrofuran (30 mL) was added sodium hydride (3.29 g, 82.37 mmol, 60% purity, 2 eq) at 25° C. stirred for 1 h, then 2-[2-(2-tetrahydropyran-2-yloxyethoxy)ethoxy]ethyl 4-methylbenzenesulfonate (15.98 g, 41.13 mmol, 1 eq) was added, the mixture was stirred at 25° C. for 12 hours. The residue was poured into ice-water (100 mL) and stirred for 0.5 minutes. The aqueous phase was extracted with ethyl acetate (70 mL×3). The combined organic phase was washed with brine (50 mL), dried with anhydrous sodium sulfate, filtered and concentrated in vacuum. The residue was purified by silica gel chromatography (Petroleum ether:Ethyl acetate=5:1 to 2:1). Compound tert-butyl (2S,4R)-2-[[tert-butyl(dimethyl) silyl]oxymethyl]-4-[2-[2-(2-tetrahydropyran-2-yloxyethoxy)ethoxy]ethoxy]pyrrolidine-1-carboxylate (18.2 g, 33.22 mmol, 81% yield) was obtained as a colorless oil. $^1$H-NMR (400 MHz, CDCl$_3$) δ 4.63 (t, J=3.4 Hz, 1H), 4.51-4.14 (m, 1H), 4.03-3.78 (m, 4H), 3.69-3.66 (m, 6H), 3.65-3.55 (m, 6H), 3.54-3.47 (m, 2H), 3.44-3.38 (m, 1H), 2.27-2.13 (m, 1H), 2.00-1.78 (m, 2H), 1.77-1.65 (m, 2H), 1.60 (br d, J=8.2 Hz, 2H), 1.45 (br s, 9H), 1.22-1.17 (m, 1H), 0.87 (s, 9H), 0.02 (br s, 6H).

Step 2: Preparation of tert-butyl (2S,4R)-2-(hydroxymethyl)-4-(2-(2-(2-((tetrahydro-2H-pyran-2-yl)oxy)ethoxy)ethoxy)ethoxy)pyrrolidine-1-carboxylate

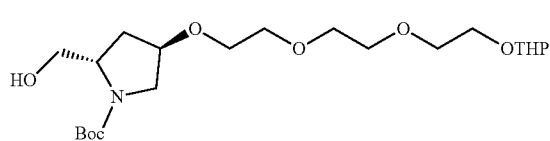

To a mixture of tert-butyl (2S,4R)-2-[[tert-butyl(dimethyl)silyl]oxymethyl]-4-[2-[2-(2-tetrahydropyran-2-yloxyethoxy)ethoxy]ethoxy]pyrrolidine-1-carboxylate (18.2 g, 33.22 mmol, 1 eq) in tetrahydrofuran (80 mL) was added tetrabutylammonium (1 M, 33.22 mL, 1 eq) at 20° C. The reaction mixture was stirred at 20° C. for 2 hours. The reaction mixture was concentrated under vacuum to get the residue. The residue was purified by silica gel column chromatography (Petroleum ether:Ethyl acetate=5:1 to 1:1) to get tert-butyl (2S,4R)-2-(hydroxymethyl)-4-[2-[2-(2-tetrahydropyran-2-yloxyethoxy)ethoxy]ethoxy]pyrrolidine-1-carboxylate (9 g, 20.76 mmol, 62% yield) as a yellow oil. $^1$H-NMR (400 MHz, CDCl$_3$) δ 4.66-4.62 (m, 1H), 4.39 (br s, 1H), 4.03 (br s, 1H), 3.92-3.82 (m, 2H), 3.75-3.70 (m, 1H), 3.70-3.68 (m, 2H), 3.67 (d, J=2.0 Hz, 4H), 3.64-3.61 (m, 2H), 3.60-3.54 (m, 4H), 3.54-3.44 (m, 2H), 3.44-3.37 (m, 1H), 2.20-2.10 (m, 1H), 1.89-1.79 (m, 1H), 1.78-1.66 (m, 2H), 1.64-1.57 (m, 2H), 1.53 (br d, J=6.6 Hz, 2H), 1.47 (s, 1H).

Step 3: Preparation of ((2S,4R)-1-methyl-4-(2-(2-(2-((tetrahydro-2H-pyran-2-yl)oxy)ethoxy)ethoxy)ethoxy)pyrrolidin-2-yl)methanol

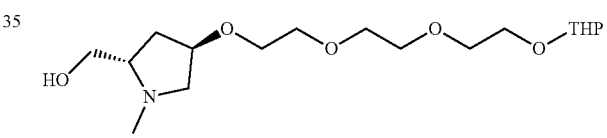

To a mixture of tert-butyl (2S,4R)-2-(hydroxymethyl)-4-[2-[2-(2-tetrahydropyran-2-yloxyethoxy)ethoxy]ethoxy]pyrrolidine-1-carboxylate (9 g, 20.76 mmol, 1 eq) in tetrahydrofuran (150 mL) was added lithium aluminium hydride (3.94 g, 103.80 mmol, 5 eq), then the reaction mixture was stirred at 70° C. for 12 hours. The mixture was cooled to 25° C. Tetrahydrofuran (200 mL) was added, water (5 mL) was added slowly, then the mixture was filtered and concentrated under vacuum. The crude product was purified by silica gel chromatography (Petroleum ether:Ethyl acetate=3:1 to 0:1), then (Tetrahydrofuran:Methanol=10:1) with 0.1% ammonium hydroxide to get [(2S,4R)-1-methyl-4-[2-[2-(2-tetrahydropyran-2-yloxyethoxy)ethoxy]ethoxy]pyrrolidin-2-yl]methanol (5.2 g, 14.97 mmol, 72% yield) as a colorless oil. $^1$H-NMR (400 MHz, CDCl$_3$) δ 4.67-4.60 (m, 1H), 4.42-4.34 (m, 1H), 4.04-3.96 (m, 1H), 3.91-3.74 (m, 2H), 3.72-3.64 (m, 7H), 3.64-3.54 (m, 4H), 3.54-3.47 (m, 1H), 3.43-3.36 (m, 2H), 2.77-2.61 (m, 1H), 2.42-2.36 (m, 2H), 2.35-2.32 (m, 3H), 2.29-2.05 (m, 2H), 1.94-1.67 (m, 4H), 1.65-1.55 (m, 2H).

Step 4: Preparation of tert-butyl 4-((S)-4-((benzyloxy)carbonyl)-3-(cyanomethyl)piperazin-1-yl)-2-(((2S,4R)-1-methyl-4-(2-(2-(2-((tetrahydro-2H-pyran-2-yl)oxy)ethoxy)ethoxy)ethoxy)pyrrolidin-2-yl)methoxy)-5,8-dihydropyrido[3,4-d]pyrimidine-7(6H)-carboxylate

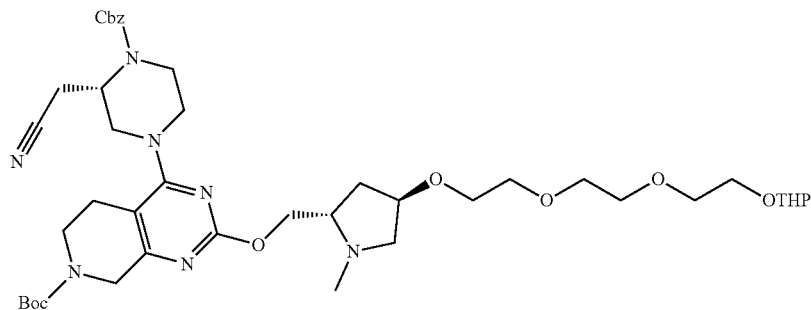

To a solution of tert-butyl 4-[(3S)-4-benzyloxycarbonyl-3-(cyanomethyl)piperazin-1-yl]-2-chloro-6,8-dihydro-5H-pyrido[3,4-d]pyrimidine-7-carboxylate (1.7 g, 3.23 mmol, 1 eq) and [(2S,4R)-1-methyl-4-[2-[2-(2-tetrahydropyran-2-yloxyethoxy)ethoxy]ethoxy]pyrrolidin-2-yl]methanol (1.40 g, 4.03 mmol, 1.25 eq) in dioxane (20 mL) was added Methanesulfonato(2-dicyclohexylphosphino-2,6-di-i-propoxy-1,1-biphenyl)(2-amino-1,1-biphenyl-2-yl)palladium(ii) (270 mg, 0.32 mmol, 0.1 eq) and cesium carbonate (3.15 g, 9.68 mmol, 3 eq), the mixture was stirred at 90° C. for 2 hours under nitrogen. Water (100 mL) was added. The aqueous phase was extracted with ethyl acetate (150 mL×3). The combined organic phase was washed with brine (50 mL), dried with anhydrous sodium sulfate, filtered and concentrated in vacuum. The residue was purified by silica gel chromatography (Petroleum ether:Ethyl acetate=4:1 to 0:1), and then purified by silica gel chromatography (Dichloromethane:Methanol=10:1) to get the product. Compound tert-butyl 4-[(3S)-4-benzyloxycarbonyl-3-(cyanomethyl)piperazin-1-yl]-2-[[(2S,4R)-1-methyl-4-[2-[2-(2-tetrahydropyran-2-yloxyethoxy)ethoxy]ethoxy]pyrrolidin-2-yl]methoxy]-6,8-dihydro-5H-pyrido[3,4-d]pyrimidine-7-carboxylate (2.3 g) was obtained as a brown oil. LC/MS (ESI) m/z: 838.6 [M+1]⁺.

Step 5: Preparation of benzyl (S)-2-(cyanomethyl)-4-(2-(((2S,4R)-4-(2-(2-(2-hydroxyethoxy)ethoxy)ethoxy)-1-methylpyrrolidin-2-yl)methoxy)-5,6,7,8-tetrahydropyrido[3,4-d]pyrimidin-4-yl)piperazine-1-carboxylate

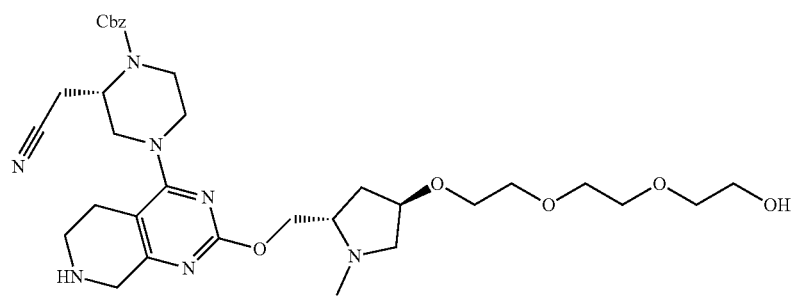 [SMILES: CN1C[C@H](OCCOCCOCCO)C[C@H]1COc1nc2c(c(N3CCN(C(=O)OCc4ccccc4)[C@@H](CC#N)C3)n1)CCNC2]

To a mixture of tert-butyl 4-[(3S)-4-benzyloxycarbonyl-3-(cyanomethyl)piperazin-1-yl]-2-[[(2S,4R)-1-methyl-4-[2-[2-(2-tetrahydropyran-2-yloxyethoxy)ethoxy]ethoxy]pyrrolidin-2-yl]methoxy]-6,8-dihydro-5H-pyrido[3,4-d]pyrimidine-7-carboxylate (2.5 g, 2.98 mmol, 1 eq) in dichloromethane (20 mL) was added trifluoroacetic acid (3.08 g, 27.01 mmol, 2 mL, 9.05 eq), then the reaction mixture was stirred at 20° C. for 5 hours. The residue was poured into saturated potassium carbonate solution and stirred for 0.5 minutes. Then lithium hydrate was added to adjust pH to 12 stirred for 20 minutes, then the aqueous phase was extracted with dichloromethane and methanol (10:1, 50 mL×3), dried with anhydrous sodium sulfate, filtered and concentrated in vacuum. The residue was purified by semi-preparative reverse phase HPLC to get compound benzyl (2S)-2-(cyanomethyl)-4-[2-[[(2S,4R)-4-[2-[2-(2-hydroxyethoxy)ethoxy]ethoxy]-1-methyl-pyrrolidin-2-yl]methoxy]-5,6,7,8-tetrahydropyrido[3,4-d]pyrimidin-4-yl]piperazine-1-carboxylate (1.3 g, 1.99 mmol, 67% yield) as a brown oil. LC/MS (ESI) m/z: 676.3 [M+23]⁺.

Step 6: Preparation of benzyl (S)-2-(cyanomethyl)-4-(2-(((2S,4R)-4-(2-(2-(2-hydroxyethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

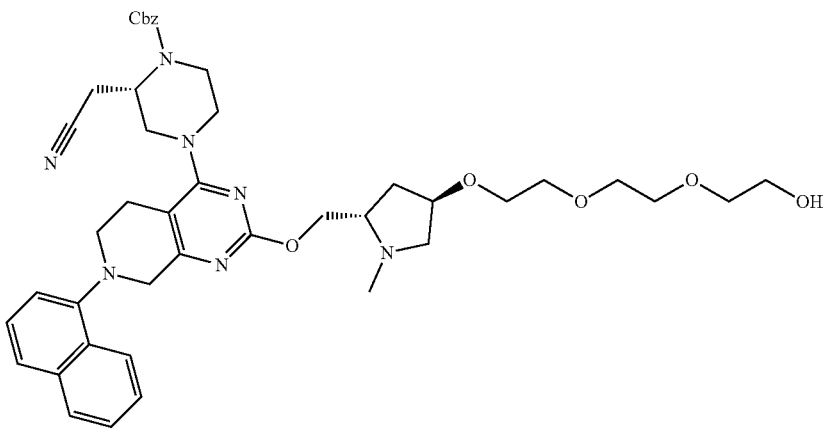

To a solution of benzyl (2S)-2-(cyanomethyl)-4-[2-[[(2S,4R)-4-[2-[2-(2-hydroxyethoxy)ethoxy]ethoxy]-1-methyl-pyrrolidin-2-yl]methoxy]-5,6,7,8-tetrahydropyrido[3,4-d]pyrimidin-4-yl]piperazine-1-carboxylate (1 g, 1.53 mmol, 1 eq) and 1-bromonaphthalene (633 mg, 3.06 mmol, 0.4 mL, 2 eq) in dioxane (10 mL) was added Methanesulfonato(2-dicyclohexylphosphino-2,6-di-i-propoxy-1,1-biphenyl)(2-amino-1,1-biphenyl-2-yl)palladium(ii) (128 mg, 0.15 mmol, 0.1 eq) and cesium carbonate (1.50 g, 4.59 mmol, 3 eq), the mixture was stirred at 90° C. for 8 hours under nitrogen. Water (10 mL) was added. The aqueous phase was extracted with ethyl acetate (15 mL×3). The combined organic phase was washed with brine (10 mL), dried with anhydrous sodium sulfate, filtered and concentrated in vacuum. The residue was purified by flash silica gel chromatography (Dichloromethane:Methanol=50:1 to 10:1) to get benzyl (2S)-2-(cyanomethyl)-4-[2-[[(2S,4R)-4-[2-[2-(2-hydroxyethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (310 mg, 0.40 mmol, 26% yield) as a brown solid. LC/MS (ESI) m/z: 780.5 [M+1]⁺; ¹H-NMR (400 MHz, CDCl₃) δ 8.24-8.15 (m, 1H), 7.90-7.82 (m, 1H), 7.61 (d, J=8.1 Hz, 1H), 7.54-7.46 (m, 2H), 7.46-7.33 (m, 6H), 7.14 (d, J=7.4 Hz, 1H), 5.21 (s, 2H), 4.70 (br s, 1H), 4.39 (br s, 1H), 4.34-4.24 (m, 2H), 4.23-4.15 (m, 2H), 4.06 (br s, 1H), 3.95 (br d, J=11.5 Hz, 1H), 3.76-3.72 (m, 2H), 3.70-3.54 (m, 10H), 3.51-3.41 (m, 2H), 3.32 (br d, J=11.9 Hz, 3H), 3.10-3.01 (m, 1H), 3.00-2.79 (m, 4H), 2.79-2.72 (m, 1H), 2.48 (br s, 3H), 2.39 (br s, 1H), 2.09 (br dd, J=4.3, 7.5 Hz, 1H), 2.02-1.97 (m, 1H), 1.86 (td, J=3.3, 6.6 Hz, 2H), 0.92-0.75 (m, 1H).

Step 7: Preparation of 2-((S)-4-(2-(((2S,4R)-4-(2-(2-(2-hydroxyethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

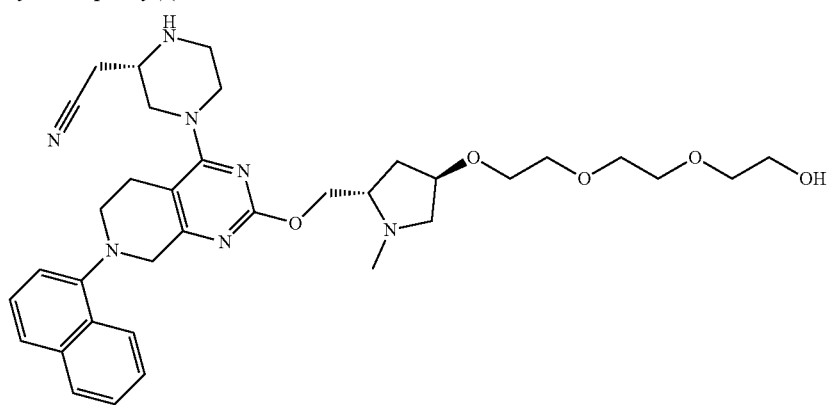

To a solution of benzyl (2S)-2-(cyanomethyl)-4-[2-[[(2S,4R)-4-[2-[2-(2-hydroxyethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (310 mg, 0.40 mmol, 1 eq) in methanol (10 mL) was added palladium/carbon (30 mg, 10% purity) and ammonium hydroxide (273 mg, 2.34 mmol, 0.3 mL, 30% purity, 5.88 eq) under nitrogen. The suspension was degassed under vacuum and purged with hydrogen several times. The mixture was stirred under hydrogen (15 psi) at 20° C. for 5 hours. The mixture was concentrated under vacuum. Compound 2-[(2S)-4-[2-[[(2S,4R)-4-[2-[2-(2-hydroxyethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (180 mg, 0.26 mmol, 67% yield, 95% purity) was obtained as a yellow solid. LC/MS (ESI) m/z: 646.4 [M+1]$^+$.

Step 8: Preparation of tert-butyl (S)-2-(cyanomethyl)-4-(2-(((2S,4R)-4-(2-(2-(2-hydroxyethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

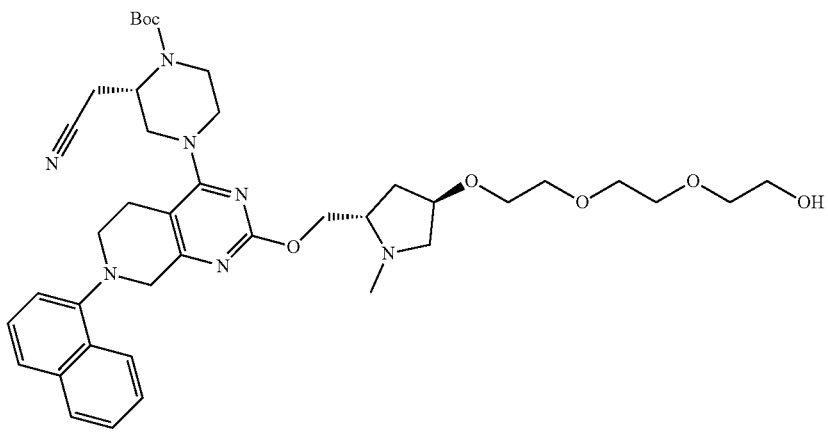 [SMILES: CN1C[C@H](OCCOCCOCCO)C[C@H]1COc1nc2c(c(N3CCN(C(=O)OC(C)(C)C)[C@@H](CC#N)C3)n1)CCN(c1cccc3ccccc13)C2]

To a solution of 2-[(2S)-4-[2-[[(2S,4R)-4-[2-[2-(2-hydroxyethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (150 mg, 0.23 mmol, 1 eq) in dichloromethane (3 mL) was added di-tert-butyl dicarbonate (507 mg, 2.32 mmol, 0.5 mL, 10 eq) and triethylamine (71 mg, 0.70 mmol, 0.1 mL, 3 eq), the reaction mixture was stirred at 25° C. for 12 hours. The mixture was filtered, and concentrated under vacuum. The reaction mixture was purified by prep-TLC (Dichloromethane:Methanol=10:1). Compound tert-butyl (2S)-2-(cyanomethyl)-4-[2-[[(2S,4R)-4-[2-[2-(2-hydroxyethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (130 mg, 0.16 mmol, 71% yield, 95% purity) was obtained as a yellow oil. LC/MS (ESI) m/z: 746.3 [M+1]$^+$.

Step 9: Preparation of tert-butyl (S)-2-(cyanomethyl)-4-(2-(((2S,4R)-1-methyl-4-(2-(2-(2-(tosyloxy)ethoxy)ethoxy)ethoxy)pyrrolidin-2-yl)methoxy)-7-(naphthalen-1-yl)-5,6,7,8-tetrahydropyrido[3,4-d]pyrimidin-4-yl)piperazine-1-carboxylate

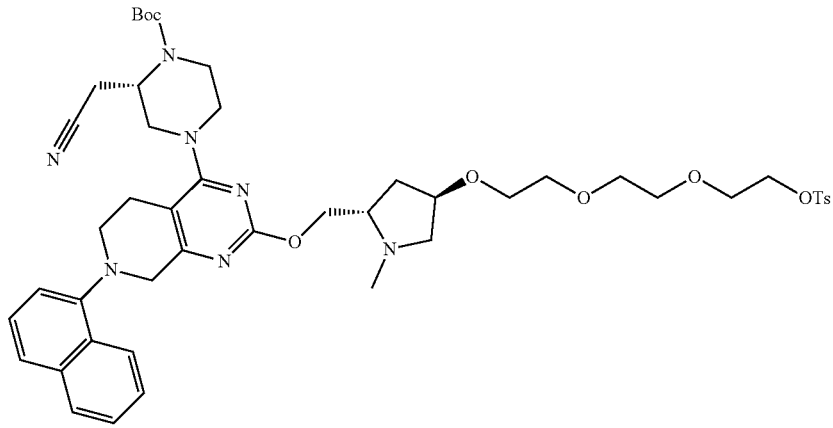 [SMILES: Cc1ccc(S(=O)(=O)OCCOCCOCCO[C@@H]2C[C@@H](COc3nc4c(c(N5CCN(C(=O)OC(C)(C)C)[C@@H](CC#N)C5)n3)CCN(c3cccc5ccccc35)C4)N(C)C2)cc1]

To a solution of tert-butyl(2S)-2-(cyanomethyl)-4-[2-[[(2S,4R)-4-[2-[2-(2-hydroxyethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (130 mg, 0.17 mmol, 1 eq) in dichloromethane (2 mL) was added triethylamine (53 mg, 0.52 mmol, 3 eq) and paratoluensulfonyl chloride (66 mg, 0.35 mmol, 2 eq) and dimethylaminopyridine (4 mg, 0.034 mmol, 0.2 eq), the reaction mixture was stirred at 25° C. for 12 hours. The mixture was filtered, and concentrated under vacuum. The reaction mixture was purified by prep-TLC (Dichloromethane:Methanol=10:1). Compound tert-butyl (2S)-2-(cyanomethyl)-4-[2-[[(2S,4R)-1-methyl-4-[2-[2-[2-(p-tolylsulfonyloxy)ethoxy]ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (100 mg, 0.11 mmol, 61% yield, 95% purity) was obtained as a yellow oil. LC/MS (ESI) m/z: 900.4 [M+1]$^+$.

Exemplary Synthesis of (2S,4R)-1-((S)-18-(tert-butyl)-16-oxo-5,8,11,14-tetraoxa-2,17-diazanonadecan-19-oyl)-4-hydroxy-N—((S)-1-(4-(4-methylthiazol-5-yl)phenyl)ethyl)pyrrolidine-2-carboxamide Step 1: Preparation of tert-butyl ((S)-16-((2S,4R)-4-hydroxy-2-(((S)-1-(4-(4-methylthiazol-5-yl)phenyl)ethyl)carbamoyl)pyrrolidine-1-carbonyl)-17,17-dimethyl-14-oxo-3,6,9,12-tetraoxa-15-azaoctadecyl)(methyl)carbamate

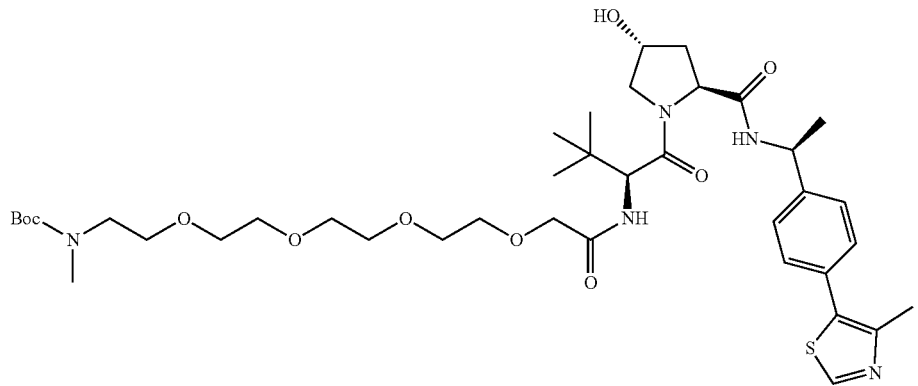 [SMILES: Cc1ncsc1-c1ccc([C@H](C)NC(=O)[C@@H]2C[C@@H](O)CN2C(=O)[C@@H](NC(=O)COCCOCCOCCOCCN(C)C(=O)OC(C)(C)C)C(C)(C)C)cc1]

A mixture of 2-[2-[2-[2-[2-[tert-butoxycarbonyl(methyl)amino]ethoxy]ethoxy]ethoxy]ethoxy]acetic acid (450 mg, 1.23 mmol, 1.00 eq), (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (592 mg, 1.23 mmol, 1.00 eq, hydrochloride), hydroxybenzotriazole (199 mg, 1.48 mmol, 1.20 eq), 1-(3-dimethylaminopropyl)-3-ethylcarbodiimide hydrochloride (283 mg, 1.48 mmol, 1.20 eq) in dichloromethane (10 mL) and diisopropylethylamine (318 mg, 2.46 mmol, 430 uL, 2.00 eq) was degassed and purged with nitrogen for 3 times, and then the mixture was stirred at 20° C. for 12 hours under nitrogen atmosphere. The reaction mixture was diluted with water (30 mL), adjust to pH=2 with hydrochloric acid (1 M), then extracted with ethyl acetate (30 mL×2). The combined organic layers were washed with saturated sodium bicarbonate solution (50 mL×1), dried over sodium sulfate, filtered and concentrated under reduced pressure to give a residue. The residue was purified by silica gel column chromatography (100-90% ethyl acetate in methanol) to give compound tert-butyl N-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl]-N-methyl-carbamate (650 mg, 0.82 mmol, 67% yield) as a colorless oil. LC/MS (ESI) m/z: 792.5 [M+1]$^+$; $^1$H-NMR (400 MHz, CDCl$_3$) δ 8.68 (s, 1H), 7.53-7.29 (m, 6H), 5.17-4.99 (m, 1H), 4.77 (t, J=8.0 Hz, 1H), 4.58-4.47 (m, 2H), 4.25-3.96 (m, 3H), 3.79-3.50 (m, 16H), 3.44-3.32 (m, 2H), 2.91 (s, 3H), 2.65-2.50 (m, 4H), 2.14-2.01 (m, 1H), 1.52-1.42 (m, 12H), 1.08 (s, 9H).

Step 2: Preparation of (2S,4R)-1-((S)-8-(tert-butyl)-16-oxo-5,8,11,14-tetraoxa-2,17-diazanonadecan-19-oyl)-4-hydroxy-N—((S)-1-(4-(4-methylthiazol-5-yl)phenyl)ethyl)pyrrolidine-2-carboxamide

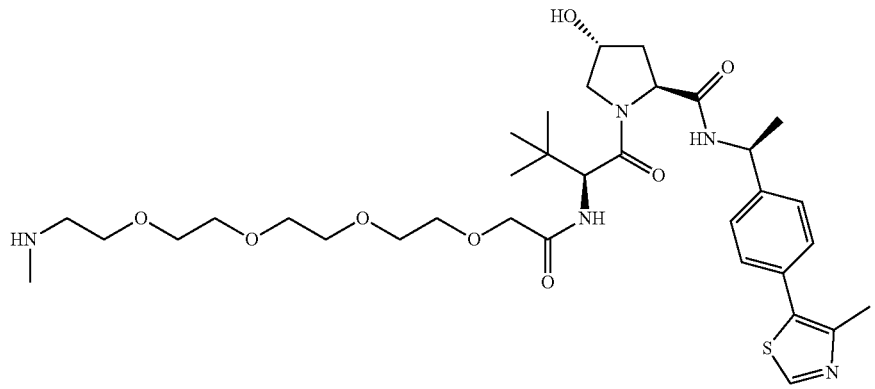 [SMILES: CNCCOCCOCCOCCOCC(=O)N[C@H](C(=O)N1C[C@H](O)C[C@H]1C(=O)N[C@@H](C)c1ccc(-c2scnc2C)cc1)C(C)(C)C]

To a solution of tert-butyl N-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl]-N-methyl-carbamate (650 mg, 0.82 mmol, 1 eq) in dichloromethane (4 mL) was added hydrochloric acid in dioxane (4 M, 3 mL). The mixture was stirred at 20° C. for 0.5 hour. The reaction mixture was concentrated under reduced pressure to give compound (2S,4R)-1-[(2S)-3,3-dimethyl-2-[[2-[2-[2-[2-[2-(methylamino)ethoxy]ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (600 mg, hydrochloride) as a green oil. LC/MS (ESI) m/z: 692.2 [M+I]$^+$.

Exemplary Synthesis of tert-butyl (R)-(2-(2-hydroxyethoxy)-1-(4-(4-methylthiazol-5-yl)phenyl)ethyl)carbamate Step 1: Preparation of tert-butyl (R)-(1-(4-bromophenyl)-2-hydroxyethyl)carbamate

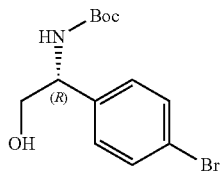

To a solution of (2R)-2-amino-2-(4-bromophenyl)ethanol (5 g, 19.80 mmol, 1 eq, hydrochloride) and triethylamine (6.01 g, 59.40 mmol, 8.27 mL, 3 eq) in dichloromethane (80 mL) was added di-tert-butyl dicarbonate (4.66 g, 21.35 mmol, 4.91 mL, 1.08 eq). The reaction mixture was stirred at 20° C. for 16 hours. The reaction solution was washed with water (100 mL), dried over sodium sulfate and then concentrated under vacuum to get tert-butyl N-[(1R)-1-(4-bromophenyl)-2-hydroxy-ethyl]carbamate (6.07 g, 18.85 mmol, 95% yield, 98% purity) as a white solid. LC/MS (ESI) m/z: 338.1 [M+23]$^+$; $^1$H-NMR (400 MHz, CDCl$_3$) δ 7.50 (d, J=8.4 Hz, 2H), 7.24 (d, J=8.8 Hz, 2H), 4.79 (t, J=5.6 Hz, 1H), 4.48 (br s, 1H), 3.47 (br dd, J=6.0, 10.4 Hz, 2H), 1.36 (s, 9H).

Step 2: Preparation of ethyl (R)-2-(2-(4-bromophenyl)-2-((tert-butoxycarbonyl)amino)ethoxy)acetate

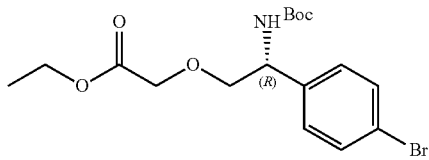

To a solution of tert-butyl N-[(1R)-1-(4-bromophenyl)-2-hydroxy-ethyl]carbamate (4 g, 12.65 mmol, 1 eq) and diacetoxyrhodium (279 mg, 1.27 mmol, 0.1 eq) in dichloromethane (150 mL) was added ethyl 2-diazoacetate (5.41 g, 37.95 mmol, 4.97 mL, 3 eq) dropwise at 0° C. The reaction mixture was stirred at 20° C. for 16 hours. The reaction mixture was concentrated under vacuum to get the residue. The residue was purified by silica gel column chromatography (0-10% ethyl acetate in petroleum ether) to get ethyl 2-[(2R)-2-(4-bromophenyl)-2-(tert-butoxycarbonylamino)ethoxy]acetate (5.1 g) was obtained as a white solid. $^1$H-NMR (400 MHz, CDCl$_3$) δ 7.48-7.43 (m, 2H), 7.24 (d, J=8.4 Hz, 2H), 5.79 (br s, 1H), 4.87-4.62 (m, 1H), 4.25-4.24 (m, 2H), 4.06 (d, J=1.2 Hz, 2H), 3.80-3.73 (m, 1H), 3.69 (br d, J=4.8 Hz, 1H), 1.50-1.36 (m, 9H), 1.30-1.26 (m, 3H).

Step 3: Preparation of ethyl (R)-2-(2-((tert-butoxycarbonyl)amino)-2-(4-(4,4,5,5-tetramethyl-1,3,2-dioxaborolan-2-yl)phenyl)ethoxy)acetate

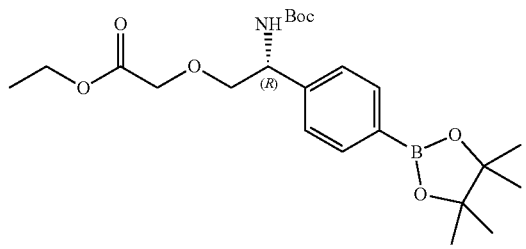

To a solution of ethyl 2-[(2R)-2-(4-bromophenyl)-2-(tert-butoxycarbonylamino)ethoxy]acetate (3 g, 7.46 mmol, 1 eq) and 4,4,4',4',5,5,5',5'-octamethyl-2,2'-bi(1,3,2-dioxaborolane) (2.27 g, 8.95 mmol, 1.2 eq) in dioxane (45 mL) was added dioxane (45 mL) [1,1'-bis(diphenylphosphino)ferrocene]dichloropalladium(ii) (436 mg, 0.60 mmol, 0.08 eq) and potassium acetate (1.46 g, 14.92 mmol, 2 eq). The reaction mixture was degassed and purged with nitrogen for 3 times, and then the mixture was stirred at 90° C. for 16 hours. The reaction mixture was concentrated under vacuum to get the residue. The residue was purified by silica column chromatography (0-30% ethyl acetate in petroleum ether) to get ethyl 2-[(2R)-2-(tert-butoxycarbonylamino)-2-[4-(4,4,5,5-tetramethyl-1,3,2-dioxaborolan-2-yl)phenyl]ethoxy]acetate (3.35 g) as a yellow oil.

Step 4: Preparation of ethyl (R)-2-(2-((tert-butoxycarbonyl)amino)-2-(4-(4-methylthiazol-5-yl)phenyl)ethoxy)acetate

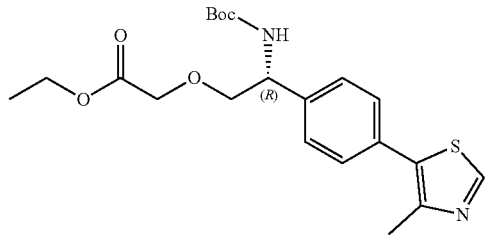

To a solution of ethyl 2-[(2R)-2-(tert-butoxycarbonylamino)-2-[4-(4,4,5,5-tetramethyl-1,3,2-dioxaborolan-2-yl)phenyl]ethoxy]acetate (3.35 g, 7.46 mmol, 1 eq) and 5-bromo-4-methyl-thiazole (2.65 g, 14.91 mmol, 2 eq) in dioxane (60 mL) was added [1,1'-bis(diphenylphosphino)ferrocene]dichloropalladium(ii) (545 mg, 0.75 mmol, 0.1 eq), potassium carbonate (2.06 g, 14.91 mmol, 2 eq) and water (12 mL). The reaction mixture was degassed and purged with nitrogen for 3 times, and then the mixture was stirred at 85° C. for 6 hours. The reaction mixture was concentrated under vacuum to remove most of the solvents. Then water (40 mL) was added and the mixture was extracted with ethyl acetate (40 mL×2). The organic layer was dried over sodium sulfate and then concentrated under vacuum to get the residue. This residue was purified by silica gel flash chromatography (0-100% ethyl acetate in petroleum ether) to get ethyl 2-[(2R)-2-(tert-butoxycarbonylamino)-2-[4-(4-methylthiazol-5-yl)phenyl]ethoxy]acetate (1.6 g, 3.80 mmol, 51% yield) as a light yellow gum. $^1$H-NMR (400 MHz, CDCl$_3$) δ 8.70 (s, 1H), 7.42 (s, 4H), 5.86 (br s, 1H), 4.86 (br s, 1H), 4.25 (q, J=7.2 Hz, 2H), 4.10 (s, 2H), 3.88-3.71 (m, 2H), 2.55 (s, 3H), 1.45 (br s, 9H), 1.31 (t, J=7.2 Hz, 3H).

Step 5: Preparation of tert-butyl (R)-(2-(2-hydroxyethoxy)-1-(4-(4-methylthiazol-5-yl)phenyl)ethyl) carbamate

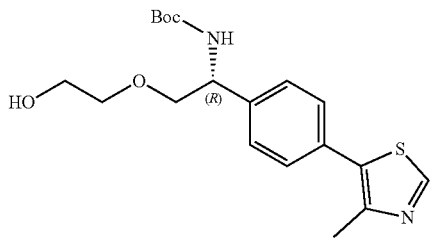

To a suspension of lithium aluminium hydride (131 mg, 3.45 mmol, 1 eq) in tetrahydrofuran (20 mL) was added a solution of ethyl 2-[(2R)-2-(tert-butoxycarbonylamino)-2-[4-(4-methylthiazol-5-yl)phenyl]ethoxy]acetate (1.45 g, 3.45 mmol, 1 eq) in tetrahydrofuran (20 mL) at −5° C. The reaction mixture was stirred at 0° C. for 1 hour. Then lithium aluminium hydride (131 mg, 3.45 mmol, 1 eq) was added and the reaction mixture was stirred at 0° C. for another 1 hour. Water (20 mL) was added and the mixture was extracted with ethyl acetate (30 mL). The organic layer was dried over sodium sulfate and then concentrated under vacuum to get the residue. The residue was purified by silica gel flash chromatography (0-200% ethyl acetate in petroleum ether) to get tert-butyl N-[(1R)-2-(2-hydroxyethoxy)-1-[4-(4-methylthiazol-5-yl)phenyl]ethyl]carbamate (780 mg, 2.06 mmol, 59% yield as a colorless oil. $^1$H-NMR (400 MHz, CDCl$_3$) δ 8.68 (s, 1H), 7.48-7.35 (m, 4H), 5.33 (br d, J=7.6 Hz, 1H), 4.90 (br s, 1H), 3.81-3.76 (m, 1H), 3.76-3.68 (m, 3H), 3.67-3.61 (m, 1H), 3.60-3.53 (m, 1H), 2.54 (s, 3H), 2.16-1.93 (m, 1H), 1.44 (br s, 9H).

Exemplary Synthesis of (2S,4R)-4-hydroxy-1-(3-methyl-2-(3-methylisoxazol-5-yl)butanoyl)pyrrolidine-2-carboxylic acid Step 1: Preparation of 2-(3-methylisoxazol-5-yl)acetic acid

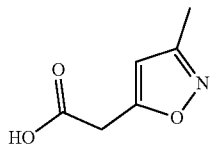

To a solution of 3,5-dimethylisoxazole (15 g, 154.46 mmol, 15 mL, 1 eq) in tetrahydrofuran (150 mL) was added n-butyllithium (2.5 M, 77 mL, 1.25 eq) dropwise at −78° C. under nitrogen, the mixture was stirred at −55° C. for 30 minutes, and then carbon dioxide was bubbled into the mixture for 30 minutes, the mixture was stirred at 25° C. for 1 hour. The reaction was quenched by saturated ammonium chloride solution (50 mL) the mixture was extracted with ethyl acetate (50 mL). The aqueous phase was adjusted with aqueous hydrochloric acid solution (2 M) until pH=2, the mixture was extracted with ethyl acetate (50 mL, three times), the organic phase was dried by anhydrous sodium sulfate, filtered and the filtrate was concentrated to give 2-(3-methylisoxazol-5-yl)acetic acid (10 g, 70.86 mmol, 46% yield) as a brown solid. $^1$H-NMR (400 MHz, DMSO-d$_6$) δ 12.74 (br s, 1H), 6.24 (s, 1H), 3.83 (s, 2H), 2.20 (s, 3H).

Step 2: Preparation of methyl 2-(3-methylisoxazol-5-yl)acetate

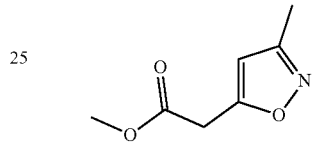

To a solution of 2-(3-methylisoxazol-5-yl)acetic acid (10 g, 70.86 mmol, 1 eq) in methanol (100 mL) was added thionyl chloride (12.65 g, 106.29 mmol, 7.71 mL, 1.5 eq) at 0° C., and the mixture was stirred at 50° C. for 4 hours. The mixture was concentrated to give crude product. This crude product was diluted with ethyl acetate (200 mL) and washed by water (200 mL), and then saturated sodium bicarbonate aqueous solution (50 mL) and then brine (50 mL), the organic phase was dried by anhydrous, filtered and the filtrate was condensed to give methyl 2-(3-methylisoxazol-5-yl)acetate (10 g, 64.45 mmol, 91% yield) as a brown oil. $^1$H-NMR (400 MHz, CDCl$_3$) δ 6.11 (s, 1H), 3.80 (s, 2H), 3.76 (s, 3H), 2.30 (s, 3H).

Step 3: Preparation of methyl 3-methyl-2-(3-methylisoxazol-5-yl)butanoate

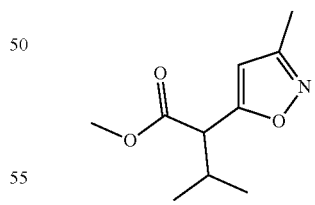

To a solution of methyl 2-(3-methylisoxazol-5-yl)acetate (10 g, 64.45 mmol, 1 eq) in tetrahydrofuran (100 mL) was added sodium hydride (3.87 g, 96.68 mmol, 60% purity, 1.5 eq) at 0° C. and then 2-iodopropane (13.15 g, 77.34 mmol, 7.74 mL, 1.2 eq) was added at 0° C., the mixture was stirred at 25° C. for 2 hours. Additional 2-iodopropane (2.55 g, 15.00 mmol, 1.5 mL) was added, the mixture was stirred at 25° C. for 10 hours. The mixture was quenched by aqueous hydrochloric acid solution (1 M, 300 mL) and the mixture was extracted with ethyl acetate (200 mL, three times), the organic phase was dried by anhydrous sodium sulfate, filtered and the filtrate was concentrated to give methyl 3-methyl-2-(3-methylisoxazol-5-yl)butanoate (13 g) as a brown oil.

Step 4: Preparation of 3-methyl-2-(3-methylisoxazol-5-yl)butanoic acid

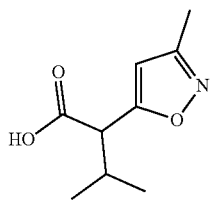

To a solution of methyl 3-methyl-2-(3-methylisoxazol-5-yl)butanoate (12.7 g, 64.39 mmol, 1 eq) in methanol (90 mL) and water (60 mL) was added sodium hydroxide (12.88 g, 321.96 mmol, 5 eq), the mixture was stirred at 25° C. for 2 hours. The mixture was concentrated to give removed methanol, and then the residue was diluted with water (200 mL) and extracted with ethyl acetate (200 mL), the aqueous phase was adjusted by aqueous hydrochloric acid solution (2 M) until pH=3, and then the mixture was extracted with dichloromethane (200 mL, three times), the organic phase was dried by anhydrous sodium sulfate, filtered and the filtrate was concentrated to give crude product as a brown oil, this material was purified by flash prep-HPLC, the fraction of acetonitrile was removed and the residue was extracted with dichloromethane (300 mL×5), the organic phase was dried by anhydrous sodium sulfate, filtered and the filtrate was concentrated to give product 3-methyl-2-(3-methylisoxazol-5-yl)butanoic acid (7.5 g, 40.94 mmol, 63% yield) as white solid. $^1$H-NMR (400 MHz, DMSO-d$_6$) δ 6.26 (s, 1H), 3.58 (d, J=8.7 Hz, 1H), 2.33-2.23 (m, 1H), 2.21 (s, 3H), 0.95 (d, J=6.7 Hz, 3H), 0.82 (d, J=6.8 Hz, 3H).

Step 5: Preparation of methyl (2S,4R)-4-hydroxy-1-(3-methyl-2-(3-methylisoxazol-5-yl)butanoyl)pyrrolidine-2-carboxylate

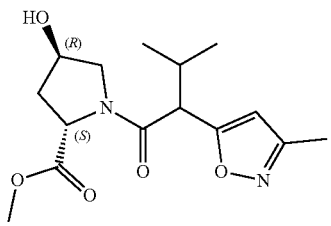

To a solution of methyl (2S,4R)-4-hydroxypyrrolidine-2-carboxylate (1.19 g, 6.55 mmol, 1 eq, hydrochloride), 3-methyl-2-(3-methylisoxazol-5-yl)butanoic acid (1.2 g, 6.55 mmol, 1 eq) and triethylamine (1.99 g, 19.65 mmol, 2.74 mL, 3 eq) in N,N-dimethylformamide (20 mL) was added o-(7-azabenzotriazol-1-yl)-n,n,n',n'-tetramethyluronium hexafluorophosphate (2.74 g, 7.21 mmol, 1.1 eq). The reaction mixture was stirred at 25° C. for 40 minutes. The reaction mixture was dissolved in ethyl acetate (50 mL) and then washed with brine (50 mL). The organic layer was dried over sodium sulfate and then concentrated under vacuum to get the residue (3 g). The residue was purified by prep-HPLC to get methyl (2S,4R)-4-hydroxy-1-[3-methyl-2-(3-methylisoxazol-5-yl)butanoyl]pyrrolidine-2-carboxylate (1.64 g, 5.28 mmol, 80% yield) as light brown gum. LC/MS (ESI) m/z: 311.1 [M+1]$^+$; $^1$H-NMR (400 MHz, DMSO-d$_6$) δ 6.20-6.04 (m, 1H), 4.68-4.50 (m, 2H), 3.89 (dd, J=4.3, 10.8 Hz, 1H), 3.78-3.69 (m, 3H), 3.69-3.57 (m, 2H), 2.47-2.34 (m, 1H), 2.28 (d, J=9.1 Hz, 4H), 2.12-2.09 (m, 1H), 1.12-0.95 (m, 3H), 0.89 (d, J=6.8 Hz, 3H).

Step 6: Preparation of (2S,4R)-4-hydroxy-1-(3-methyl-2-(3-methylisoxazol-5-yl)butanoyl)pyrrolidine-2-carboxylic acid

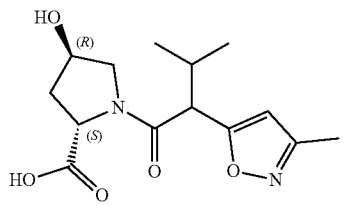

To a solution of methyl (2S,4R)-4-hydroxy-1-[3-methyl-2-(3-methylisoxazol-5-yl)butanoyl]pyrrolidine-2-carboxylate (1.2 g, 3.87 mmol, 1 eq) in tetrahydrofuran (12 mL) was added water (12 mL) and lithium hydroxide monohydrate (487 mg, 11.60 mmol, 3 eq). The reaction mixture was stirred at 25° C. for 2 hours. The pH of the mixture was adjusted to 2 with 1 N hydrochloric acid. The mixture was extracted with ethyl acetate (40 mL×2). The organic layer was dried over sodium sulfate and then concentrated under vacuum to get (2S,4R)-4-hydroxy-1-[3-methyl-2-(3-methylisoxazol-5-yl)butanoyl]pyrrolidine-2-carboxylic acid (1.02 g, 3.44 mmol, 89.02% yield) as a colorless gum. LC/MS (ESI) m/z: 297.1 [M+1]$^+$; $^1$H-NMR (400 MHz, CD$_3$OD) δ 6.23-6.14 (m, 1H), 4.57-4.39 (m, 2H), 3.90-3.67 (m, 2H), 3.66-3.57 (m, 1H), 2.50-2.32 (m, 1H), 2.31-2.21 (m, 4H), 2.13-2.02 (m, 1H), 1.12-0.96 (m, 3H), 0.91-0.78 (m, 3H).

Exemplary Synthesis of tert-butyl ((R)-1-((2S,4R)-4-hydroxy-1-((R)-3-methyl-2-(3-methylisoxazol-5-yl)butanoyl)pyrrolidin-2-yl)-3-(4-(4-methylthiazol-5-yl)phenyl)-1-oxo-5,8,11-trioxa-2-azatridecan-13-yl)(methyl)carbamate and tert-butyl ((3R)-1-((2S,4R)-4-hydroxy-1-(3-methyl-2-(3-methylisoxazol-5-yl)butanoyl)pyrrolidin-2-yl)-3-(4-(4-methylthiazol-5-yl)phenyl)-1-oxo-5,8,11-trioxa-2-azatridecan-13-yl)(methyl)carbamate Step 1: Preparation of 2-(2-((tetrahydro-2H-pyran-2-yl)oxy)ethoxy)ethyl 4-methylbenzenesulfonate

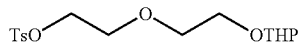

To a solution of 2-(2-hydroxyethoxy)ethyl 4-methylbenzenesulfonate (1 g, 3.84 mmol, 1 eq) in dichloromethane (10 mL) was added 3,4-dihydro-2H-pyran (496 mg, 5.76 mmol, 1.5 eq) and p-toluenesulfonic acid (33 mg, 0.19 mmol, 0.05 eq). The reaction solution was stirred at 20° C. for 2 hours. Triethylamine (0.1 mL) was added and the reaction mixture was concentrated under vacuum to get the residue. This residue was purified by silica gel flash chromatography (0-25% ethyl acetate in petroleum ether) to get the product. 2-(2-tetrahydropyran-2-yloxyethoxy)ethyl 4-methylbenzenesulfonate (1.15 g, 3.34 mmol, 86.91% yield) was obtained as a colorless oil. $^1$H-NMR (400 MHz, DMSO-$d_6$) δ 7.81 (d, J=8.3 Hz, 2H), 7.35 (d, J=8.1 Hz, 2H), 4.62-4.58 (m, 1H), 4.20-4.16 (m, 2H), 3.90-3.77 (m, 2H), 3.74-3.69 (m, 2H), 3.64-3.59 (m, 2H), 3.57-3.46 (m, 2H), 2.46 (s, 3H), 1.88-1.77 (m, 1H), 1.75-1.67 (m, 1H), 1.57-1.48 (m, 4H).

Step 2: Preparation of tert-butyl ((1R)-1-(4-(4-methylthiazol-5-yl)phenyl)-2-(2-(2-(2-((tetrahydro-2H-pyran-2-yl)oxy)ethoxy)ethoxy)ethoxy)ethyl)carbamate

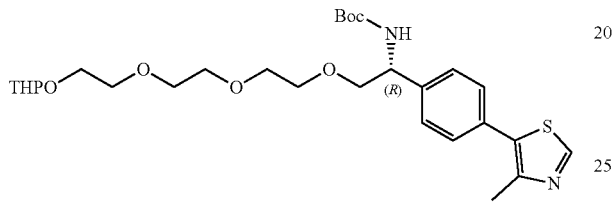

To a solution of tert-butyl N-[(1R)-2-(2-hydroxyethoxy)-1-[4-(4-methylthiazol-5-yl)phenyl]ethyl]carbamate (430 mg, 1.14 mmol, 1 eq) in tetrahydrofuran (4 mL) was added sodium hydrogen (91 mg, 2.28 mmol, 60% purity, 2 eq) at 0° C. The reaction mixture was stirred at 20° C. for 0.5 hour. Then a solution of 2-(2-tetrahydropyran-2-yloxyethoxy) ethyl 4-methylbenzenesulfonate (393 mg, 1.14 mmol, 1 eq) in tetrahydrofuran (6 mL) was added and the reaction mixture was stirred at 55° C. for 12 hours. The mixture was quenched by water (30 mL) and extracted with ethyl acetate (30 mL, three times), the organic phase was dried by anhydrous sodium sulfate, filtered and the filtrate was concentrated to give crude product. This crude product was purified by prep-TLC (dichloromethane:methanol=10:1) to give product, tert-butyl N-[(1R)-1-[4-(4-methylthiazol-5-yl)phenyl]-2-[2-[2-(2-tetrahydropyran-2-yloxyethoxy)ethoxy]ethoxy]ethyl]carbamate (85 mg, 0.12 mmol, 10.8% yield, 79.4% purity) as a brown oil.

Step 3: Preparation of (R)-2-(2-(2-(2-amino-2-(4-(4-methylthiazol-5-yl)phenyl)ethoxy)ethoxy)ethoxy)ethan-1-ol

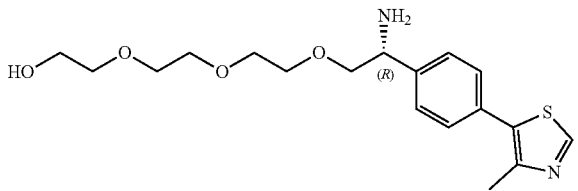

To a solution of tert-butyl N-[(1R)-1-[4-(4-methylthiazol-5-yl)phenyl]-2-[2-[2-(2-tetrahydropyran-2-yloxyethoxy)ethoxy]ethoxy]ethyl]carbamate (84 mg, 0.15 mmol, 1 eq) in dichloromethane (2 mL) was added hydrochloric acid/methanol (4 M, 0.5 mL, 13.11 eq) at 20° C. The reaction mixture was stirred at 20° C. for 3 hours. The reaction mixture was concentrated under vacuum. Compound 2-[2-[2-[(2R)-2-amino-2-[4-(4-methylthiazol-5-yl)phenyl]ethoxy]ethoxy]ethoxy]ethanol (61 mg, 0.15 mmol, 99.3% yield, hydrochloride) was obtained as a yellow oil. LC/MS (ESI) m/z: 367.2 [M+1]$^+$.

Step 4: Preparation of (2S,4R)-4-hydroxy-N—((R)-2-(2-(2-(2-hydroxyethoxy)ethoxy)ethoxy)-1-(4-(4-methylthiazol-5-yl)phenyl)ethyl)-1-(3-methyl-2-(3-methylisoxazol-5-yl)butanoyl)pyrrolidine-2-carboxamide

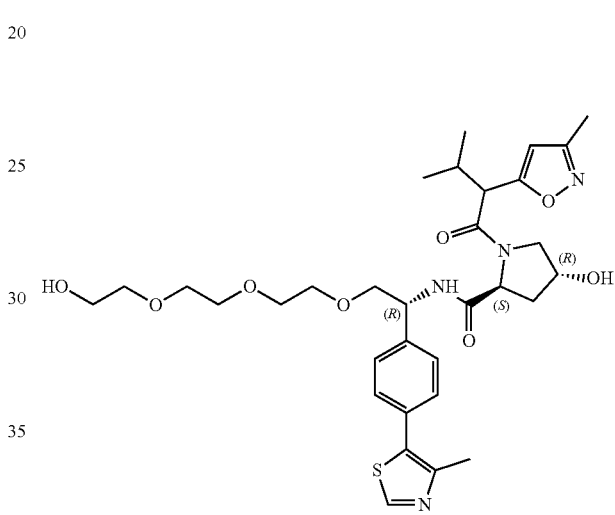

To a solution of 2-[2-[2-[(2R)-2-amino-2-[4-(4-methylthiazol-5-yl)phenyl]ethoxy]ethoxy]ethoxy]ethanol (98 mg, 0.24 mmol, 1 eq, hydrochloride), (2S,4R)-4-hydroxy-1-[3-methyl-2-(3-methylisoxazol-5-yl)butanoyl]pyrrolidine-2-carboxylic acid (76 mg, 0.26 mmol, 1.05 eq), 1-hydroxybenzotriazole (43 mg, 0.32 mmol, 1.3 eq) and N-(3-dimethylaminopropyl)-N-ethylcarbodiimide hydrochloride (61 mg, 0.32 mmol, 1.3 eq) in N,N-dimethylformamide (2 mL) was added diisopropylethylamine (94 mg, 0.73 mmol, 3 eq). The reaction mixture was stirred at 20° C. for 15 hours. The mixture was diluted with water (30 mL) and extracted with dichloromethane (30 mL, twice), the organic phase was dried by anhydrous sodium sulfate, filtered and the filtrate was concentrated to give crude product. This crude product was purified by prep-TLC (dichloromethane:methanol=10:1) to give product. (2S,4R)-4-hydroxy-N-[(1R)-2-[2-[2-(2-hydroxyethoxy)ethoxy]ethoxy]-1-[4-(4-methylthiazol-5-yl)phenyl]ethyl]-1-[3-methyl-2-(3-methylisoxazol-5-yl)butanoyl]pyrrolidine-2-carboxamide totally 180 mg was obtained as a pale yellow oil. LC/MS (ESI) m/z: 645.1 [M+1]$^+$.

Step 5: Preparation of (3R)-1-((2S,4R)-4-hydroxy-1-(3-methyl-2-(3-methylisoxazol-5-yl)butanoyl)pyrrolidin-2-yl)-3-(4-(4-methylthiazol-5-yl)phenyl)-1-oxo-5,8,11-trioxa-2-azatridecan-13-yl 4-methylbenzenesulfonate

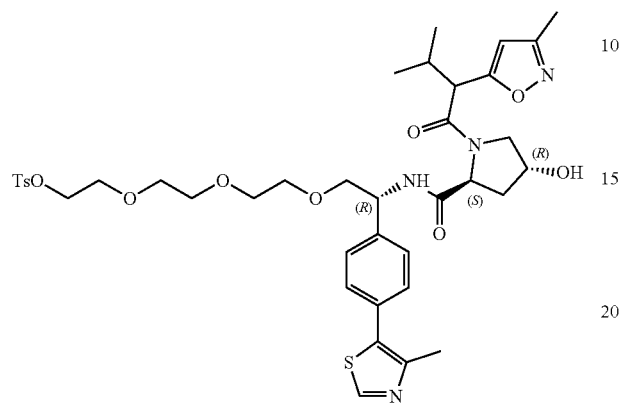

To a solution of (2S,4R)-4-hydroxy-N-[(1R)-2-[2-[2-(2-hydroxyethoxy)ethoxy]ethoxy]-1-[4-(4-methylthiazol-5-yl)phenyl]ethyl]-1-[3-methyl-2-(3-methylisoxazol-5-yl)butanoyl]pyrrolidine-2-carboxamide (100 mg, 0.11 mmol, 1 eq) in dichloromethane (3 mL) was added triethylamine (22 mg, 0.21 mmol, 2 eq), dimethylaminopyridine (1.31 mg, 10.70 umol, 0.1 eq), and then 4-methylbenzene-1-sulfonyl chloride (41 mg, 0.21 mmol, 2 eq), the mixture was stirred at 20° C. for 10 hours. The mixture was concentrated to give crude product. This crude product was purified by prep-TLC (dichloromethane:methanol=10:1) to give product. Compound 2-[2-[2-[(2R)-2-[[(2S,4R)-4-hydroxy-1-[3-methyl-2-(3-methylisoxazol-5-yl)butanoyl]pyrrolidine-2-carbonyl]amino]-2-[4-(4-methylthiazol-5-yl)phenyl]ethoxy]ethoxy]ethyl 4-methylbenzenesulfonate (40 mg, 0.04 mmol, 40.2% yield, 85.9% purity) was obtained as a brown oil. LC/MS (ESI) m/z: 799.0 [M+1]

Step 6: Preparation of (2S,4R)-4-hydroxy-1-(3-methyl-2-(3-methylisoxazol-5-yl)butanoyl)-N—((R)-13-(4-(4-methylthiazol-5-yl)phenyl)-5,8,11-trioxa-2-azatridecan-13-yl)pyrrolidine-2-carboxamide

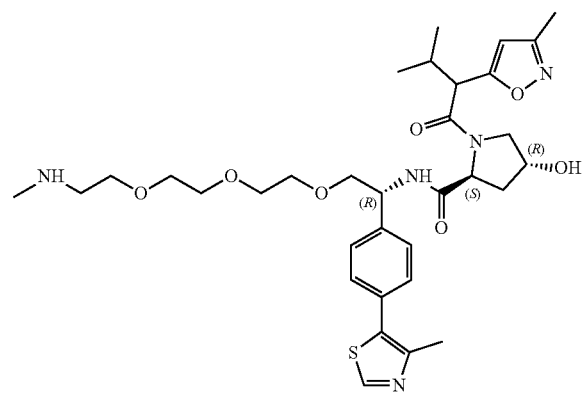

To a solution of 2-[2-[2-[(2R)-2-[[(2S,4R)-4-hydroxy-1-[3-methyl-2-(3-methylisoxazol-5-yl)butanoyl]pyrrolidine-2-carbonyl]amino]-2-[4-(4-methylthiazol-5-yl)phenyl]ethoxy]ethoxy]ethyl 4-methylbenzenesulfonate (100 mg, 0.13 mmol, 1 eq) in methylamine/ethanol (4 mL, 30% purity), the mixture was stirred at 50° C. for 3 hours. The mixture was concentrated to give product (2S,4R)-4-hydroxy-N-[(1R)-2-[2-[2-[2-(methylamino)ethoxy]ethoxy]ethoxy]-1-[4-(4-methylthiazol-5-yl)phenyl]ethyl]-1-[3-methyl-2-(3-methylisoxazol-5-yl)butanoyl]pyrrolidine-2-carboxamide (90 mg) as a pale yellow oil. LC/MS (ESI) m/z: 658.2 [M+1]⁺.

Step 7: Preparation of tert-butyl ((3R)-1-((2S,4R)-4-hydroxy-1-(3-methyl-2-(3-methylisoxazol-5-yl)butanoyl)pyrrolidin-2-yl)-3-(4-(4-methylthiazol-5-yl)phenyl)-1-oxo-5,8,11-trioxa-2-azatridecan-13-yl) (methyl)carbamate

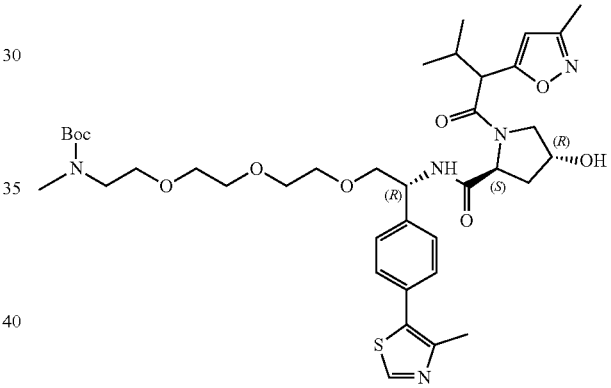

To a solution of (2S,4R)-4-hydroxy-N-[(1R)-2-[2-[2-[2-(methylamino)ethoxy]ethoxy]ethoxy]-1-[4-(4-methylthiazol-5-yl)phenyl]ethyl]-1-[3-methyl-2-(3-methylisoxazol-5-yl)butanoyl]pyrrolidine-2-carboxamide (82 mg, 0.12 mmol, 1 eq) in dichloromethane (3 mL) was added triethylamine (38 mg, 0.37 mmol, 3 eq) and di-tert-butyl dicarbonate (54 mg, 0.25 mmol, 57 uL, 2 eq) was added, the mixture was stirred at 20° C. for 5 hours. The mixture was concentrated to give a crude product. This crude product was purified by prep-TLC (dichloromethane:methanol=10:1) to give tert-butyl N-[2-[2-[2-[(2R)-2-[[(2S,4R)-4-hydroxy-1-[3-methyl-2-(3-methylisoxazol-5-yl)butanoyl]pyrrolidine-2-carbonyl]amino]-2-[4-(4-methylthiazol-5-yl)phenyl]ethoxy]ethoxy]ethyl]-N-methyl-carbamate (75 mg, 98.95 umol, 79.4% yield) as a pale yellow oil. LC/MS (ESI) m/z: 780.1 [M+23]⁺.

Step 8: Preparation of tert-butyl ((R)-1-((2S,4R)-4-hydroxy-1-((R)-3-methyl-2-(3-methylisoxazol-5-yl)butanoyl)pyrrolidin-2-yl)-3-(4-(4-methylthiazol-5-yl)phenyl)-1-oxo-5,8,11-trioxa-2-azatridecan-13-yl)(methyl)carbamate and tert-butyl ((3R)-1-((2S,4R)-4-hydroxy-1-(3-methyl-2-(3-methylisoxazol-5-yl)butanoyl)pyrrolidin-2-yl)-3-(4-(4-methylthiazol-5-yl)phenyl)-1-oxo-5,8,11-trioxa-2-azatridecan-13-yl)(methyl)carbamate

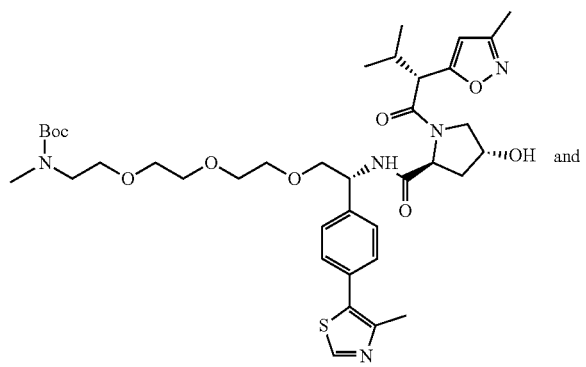

and

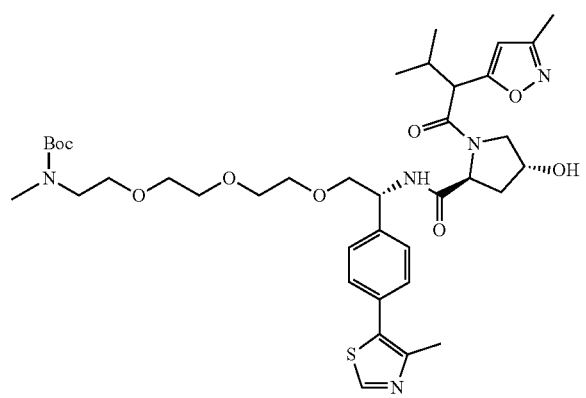

Tert-butyl N-[2-[2-[2-[(2R)-2-[[(2S,4R)-4-hydroxy-1-[3-methyl-2-(3-methylisoxazol-5-yl)butanoyl]pyrrolidine-2-carbonyl]amino]-2-[4-(4-methylthiazol-5-yl)phenyl]ethoxy]ethoxy]ethyl]-N-methyl-carbamate (75 mg, 0.10 mmol, 1 eq) was purified by SFC. Compound tert-butyl N-[2-[2-[2-[(2R)-2-[[(2S,4R)-4-hydroxy-1-[(2R)-3-methyl-2-(3-methylisoxazol-5-yl)butanoyl]pyrrolidine-2-carbonyl]amino]-2-[4-(4-methylthiazol-5-yl)phenyl]ethoxy]ethoxy]ethoxy]ethyl]-N-methyl-carbamate (30 mg, 35.50 umol, 35.9% yield, 89.7% purity) and tert-butyl N-[2-[2-[2-[(2R)-2-[[(2S,4R)-4-hydroxy-1-[(2S)-3-methyl-2-(3-methylisoxazol-5-yl)butanoyl]pyrrolidine-2-carbonyl]amino]-2-[4-(4-methylthiazol-5-yl)phenyl]ethoxy]ethoxy]ethoxy]ethyl]-N-methyl-carbamate (28 mg, 34.36 umol, 34.7% yield, 93% purity) were obtained as colorless oils.

Exemplary Synthesis of 3-((4-(4-acetylpiperazin-1-yl)-6-chloro-8-fluoro-7-(3-hydroxynaphthalen-1-yl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide (Exemplary Compound 13)

Step 1: Preparation of tert-butyl (2-(2-(2-((2-(2,6-dioxopiperidin-3-yl)-1,3-dioxoisoindolin-5-yl)oxy)ethoxy)ethoxy)ethyl)(methyl)carbamate

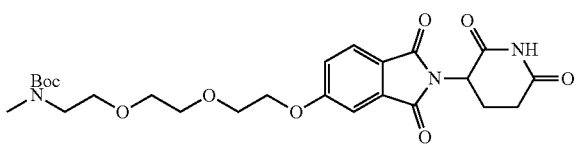 [SMILES: CN(CCOCCOCCOc1ccc2c(c1)C(=O)N(C1CCC(=O)NC1=O)C2=O)C(=O)OC(C)(C)C]

To a stirred solution of 2,2,5-trimethyl-4-oxo-3,8,11-trioxa-5-azatridecan-13-yl 4-methylbenzenesulfonate (370 mg, 0.73 mmol), 2-(2,6-dioxopiperidin-3-yl)-5-hydroxyisoindoline-1,3-dione (200 mg, 0.73 mmol) and potassium carbonate (200 mg, 1.5 mmol) in N,N-dimethylformamide (10 mL). The resulting mixture was stirred at 60° C. overnight. The reaction mixture was portioned between water (20 mL) and ethyl acetate (15 mL). The organic layer was collected, washed with water (20 mL), dried over anhydrous sodium sulfate, and concentrated under reduced pressure to afford a crude residue which was purified by pre-TLC (eluted with 8% methanol in dichloromethane) to afford tert-butyl(2-(2-(2-((2-(2,6-dioxopiperidin-3-yl)-1,3-dioxoisoindolin-5-yl)oxy)ethoxy)ethoxy)ethyl)(methyl)carbamate (180 mg, 47%). LC/MS (ESI) m/z: 520.5 [M+1]$^+$; $^1$H-NMR (400 MHz, CDCl$_3$) δ 1.45 (s, 9H), 2.13-2.17 (m, 1H), 2.73-2.93 (m, 6H), 3.40 (s, 2H), 3.60-3.65 (m, 4H), 3.71-3.73 (m, 2H), 3.91 (t, J=4.4 Hz, 2H), 4.25 (t, J=3.6 Hz, 3H), 4.96 (dd, J=5.2 Hz, J=12.0 Hz, 1H), 7.23 (dd, J=2.0 Hz, J=8.0 Hz, 1H), 7.36 (d, J=2.0 Hz, 1H), 7.78 (d, J=8.4 Hz, 1H), 8.09 (s, 1H).

Step 2: Preparation of 2-(2,6-dioxopiperidin-3-yl)-5-(2-(2-(2-(methylamino)ethoxy)ethoxy)ethoxy)isoindoline-1,3-dione hydrochloride

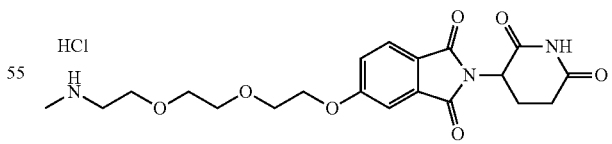

A solution of tert-butyl(2-(2-(2-((2-(2,6-dioxopiperidin-3-yl)-1,3-dioxoisoindolin-5-yl)oxy)ethoxy)ethoxy)ethyl)(methyl)carbamate (90 mg, 0.17 mmol) in 4M hydrogen chloride in dioxane (3 mL) was stirred at room temperature for 1 hour. The volatiles were removed under reduced pressure to give 2-(2,6-dioxopiperidin-3-yl)-5-(2-(2-(2-(methylamino)ethoxy)ethoxy)ethoxy)isoindoline-1,3-dione hydrochloride as HCl salt.

Step 3: Preparation of 3-((4-(4-acetylpiperazin-1-yl)-6-chloro-8-fluoro-7-(3-hydroxynaphthalen-1-yl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide

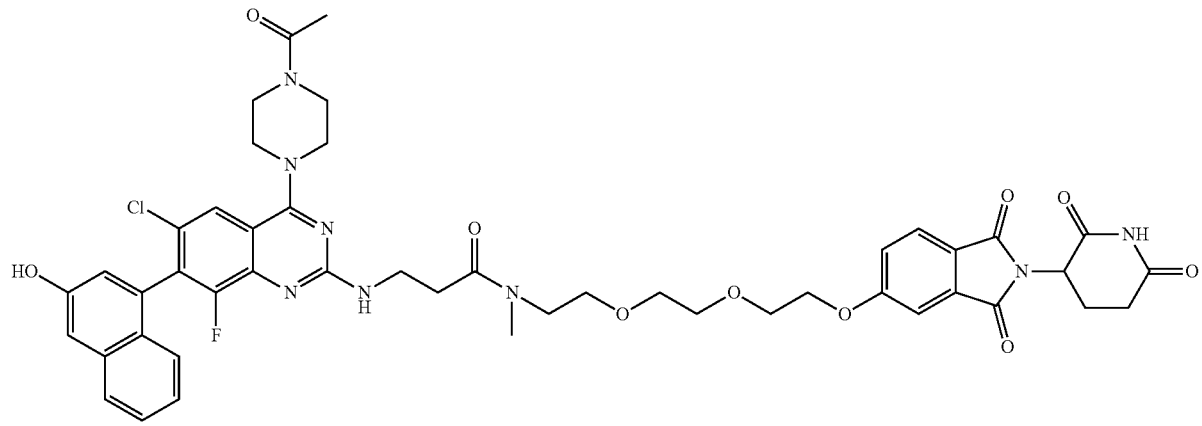 [SMILES: CC(=O)N1CCN(c2nc(NCCC(=O)N(C)CCOCCOCCOc3ccc4c(c3)C(=O)N(C3CCC(=O)NC3=O)C4=O)nc3c(F)c(-c4cc(O)cc5ccccc45)c(Cl)cc23)CC1]

To a stirred solution of 2-(2,6-dioxopiperidin-3-yl)-5-(2-(2-(2-(methylamino)ethoxy)ethoxy)ethoxy)isoindoline-1,3-dione hydrochloride (0.17 mmol), 3-((4-(4-acetylpiperazin-1-yl)-6-chloro-8-fluoro-7-(3-hydroxynaphthalen-1-yl)quinazolin-2-yl)amino)propanoic acid (50 mg, 0.09 mmol) in N,N-dimethylformamide (5 mL) was added N-ethyl-N-isopropylpropan-2-amine (36 mg, 0.28 mmol) and (2-(7-Aza-1H-benzotriazole-1-yl)-1,1,3,3-tetramethyluronium hexafluorophosphate) (71 mg, 0.19 mmol) at 0° C. The resulting mixture was stirred at room temperature for 24 hours. The reaction mixture was partitioned between ethyl acetate (20 ml) and water (20 ml). The organic layer was collected, washed with water (20 mL), dried over anhydrous sodium sulfate, and concentrated under reduced pressure to afford a crude residue which was purified by pre-TLC to afford 3-((4-(4-acetylpiperazin-1-yl)-6-chloro-8-fluoro-7-(3-hydroxynaphthalen-1-yl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide (50 mg, 57%) as white solid. LC/MS (ESI) m/z: 941.0 [M+1]$^+$; $^1$H-NMR (400 MHz, DMSO-d$_6$) δ 2.01-2.07 (m, 4H), 2.54-2.75 (m, 4H), 2.87-2.99 (m, 4H), 3.47-3.77 (m, 16H), 4.18-4.28 (m, 6H), 5.09-5.14 (m, 1H), 7.07-7.08 (m, 1H), 7.22-7.27 (m, 2H), 7.32-7.36 (m, 2H), 7.43-7.48 (m, 2H), 7.80-7.84 (m, 2H), 8.04-8.09 (m, 2H), 11.12 (s, 1H).

Exemplary Synthesis of 3-((4-(4-acetylpiperazin-1-yl)-6-chloro-8-fluoro-7-(3-hydroxynaphthalen-1-yl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide (Exemplary Compound 111)

Step 1: Preparation of tert-butyl (2-(2-(2-((2-(2,6-dioxopiperidin-3-yl)-1,3-dioxoisoindolin-4-yl)amino)ethoxy)ethoxy)ethyl)(methyl)carbamate

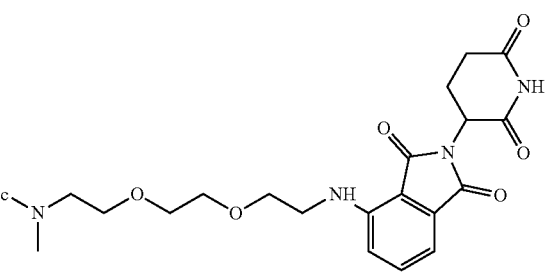

To a solution of 2-(2,6-dioxo-3-piperidyl)-4-fluoro-isoindoline-1,3-dione (151 mg, 0.55 mmol, 1.2 eq) and tert-butyl N-[2-[2-(2-aminoethoxy)ethoxy]ethyl]-N-methyl-carbamate (120 mg, 0.46 mmol, 1 eq) in dimethylsulfoxide (5 mL) was added N,N-diisopropylethylamine (77 mg, 0.60 mmol, 0.1 mL, 1.3 eq). The mixture was stirred at 80° C. for 12 hours. The mixture was diluted with water (20 mL) and the aqueous phase was extracted with ethyl acetate (20 mL×3). The combined organic phase was washed with brine (20 mL), dried with anhydrous sodium sulfate, filtered and concentrated in vacuum. The residue was purified by prep-TLC (petroleum ether/ethyl acetate=1/1) to give tert-butyl N-[2-[2-[2-[[2-(2,6-dioxo-3-piperidyl)-1,3-dioxo-isoindolin-4-yl]amino]ethoxy]ethoxy]ethyl]-N-methyl-carbamate (100 mg, 0.19 mmol, 40% yield, 96% purity) as a yellow solid. LC/MS (ESI) m/z: 541.1 [M+23]$^+$.

Hydrochloride in dioxane solution (4 M, 10 mL, 207.42 eq) was added to tert-butyl N-[2-[2-[2-[[2-(2,6-dioxo-3-piperidyl)-1,3-dioxo-isoindolin-4-yl]amino]ethoxy]ethoxy]ethyl]-N-methyl-carbamate (100 mg, 0.19 mmol, 1 eq) and the mixture was stirred at 20° C. for 12 h. The mixture was concentrated in vacuum to give 2-(2,6-dioxo-3-piperidyl)-4-[2-[2-[2-(methylamino)ethoxy]ethoxy]ethylamino]isoindoline-1,3-dione (110 mg, hydrochloride) as a colorless oil.

Step 2: Preparation of 2-(2,6-dioxopiperidin-3-yl)-4-((2-(2-(2-(methylamino)ethoxy)ethoxy)ethyl)amino)isoindoline-1,3-dione

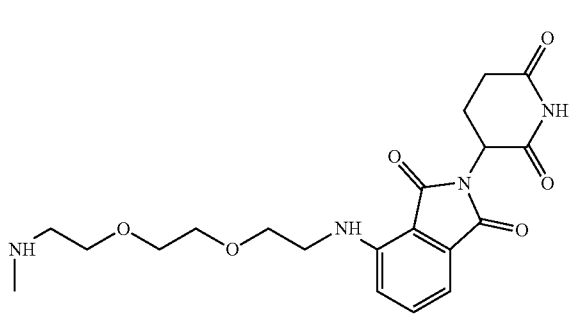 [SMILES: CNCCOCCOCCNc1cccc2c1C(=O)N(C1CCC(=O)NC1=O)C2=O]

Step 3: Preparation of tert-butyl 4-((7S)-6-chloro-2-((3-((2-(2-(2-((2-(2,6-dioxopiperidin-3-yl)-1,3-dioxoisoindolin-4-yl)amino)ethoxy)ethoxy)ethyl)(methyl)amino)-3-oxopropyl)amino)-8-fluoro-7-(2-fluoro-6-hydroxyphenyl)quinazolin-4-yl)piperazine-1-carboxylate

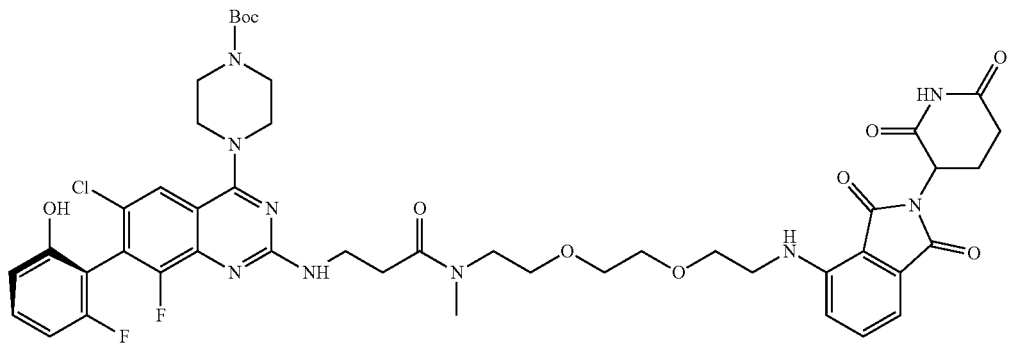

To the mixture of 2-(2,6-dioxo-3-piperidyl)-4-[2-[2-[2-(methylamino)ethoxy]ethoxy]ethylamino]isoindoline-1,3-dione (120 mg, 0.22 mmol, 1 eq, trifluoroacetate) and 3-[[4-(4-tert-butoxycarbonylpiperazin-1-yl)-6-chloro-8-fluoro-7-(2-fluoro-6-hydroxy-phenyl)quinazolin-2-yl]amino]propanoic acid (127 mg, 0.22 mmol, 1 eq) in N,N-dimethylformamide (5 mL) was added 1-hydroxybenzotriazole (60 mg, 0.45 mmol, 2 eq), N-(3-dimethylaminopropyl)-N-ethylcarbodiimide hydrochloride (86 mg, 0.45 mmol, 2 eq) and N,N-diisopropylethylamine (145 mg, 1.13 mmol, 0.20 mL, 5 eq). The mixture was stirred at 25° C. for 12 hours. The mixture was diluted with water (20 mL), extracted with ethyl acetate (20 mL×3). The combined organic layer was washed with water (30 mL×2), and brine (30 mL×2), dried over anhydrous sodium sulfate, filtered and concentrated under reduced pressure to give a residue. The residue was purified by prep-Thin-layer chromatography (dichloromethane:methanol=10:1) to obtain tert-butyl 4-[6-chloro-2-[[3-[2-[2-[2-[[2-(2,6-dioxo-3-piperidyl)-1,3-dioxo-isoindolin-4-yl]amino]ethoxy]ethoxy]ethyl-methyl-amino]-3-oxo-propyl]amino]-8-fluoro-7-(2-fluoro-6-hydroxy-phenyl)quinazolin-4-yl]piperazine-1-carboxylate (150 mg, 0.15 mmol, 69% yield) as a light yellow solid. LC/MS (ESI) m/z: 964.4 [M+1]$^+$.

Step 4: Preparation of 3-(((S)-6-chloro-8-fluoro-7-(2-fluoro-6-hydroxyphenyl)-4-(piperazin-1-yl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide

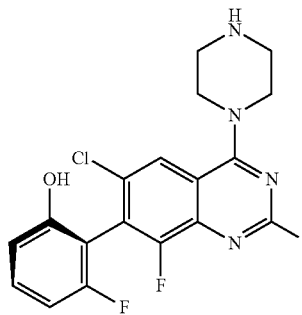 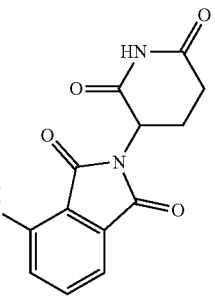

To the mixture of tert-butyl 4-[6-chloro-2-[[3-[2-[2-[2-[[2-(2,6-dioxo-3-piperidyl)-1,3-dioxo-isoindolin-4-yl]amino]ethoxy]ethoxy]ethyl-methyl-amino]-3-oxo-propyl]amino]-8-fluoro-7-(2-fluoro-6-hydroxy-phenyl)quinazolin-4-yl]piperazine-1-carboxylate (150 mg, 0.15 mmol, 1 eq) in dichloromethane (4 mL) was added trifluoroacetic acid (1 mL). The mixture was stirred at 25° C. for 1 hour. The mixture was concentrated under reduced pressure to give 3-[[6-chloro-8-fluoro-7-(2-fluoro-6-hydroxy-phenyl)-4-piperazin-1-yl-quinazolin-2-yl]amino]-N-[2-[2-[2-[[2-(2,6-dioxo-3-piperidyl)-1,3-dioxo-isoindolin-4-yl]amino]ethoxy]ethoxy]ethyl]-N-methyl-propanamide (150 mg, trifluoroacetate) as a green oil. LC/MS (ESI) m/z: 864.3 [M+1].

Step 5: Preparation of 3-(((S)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide

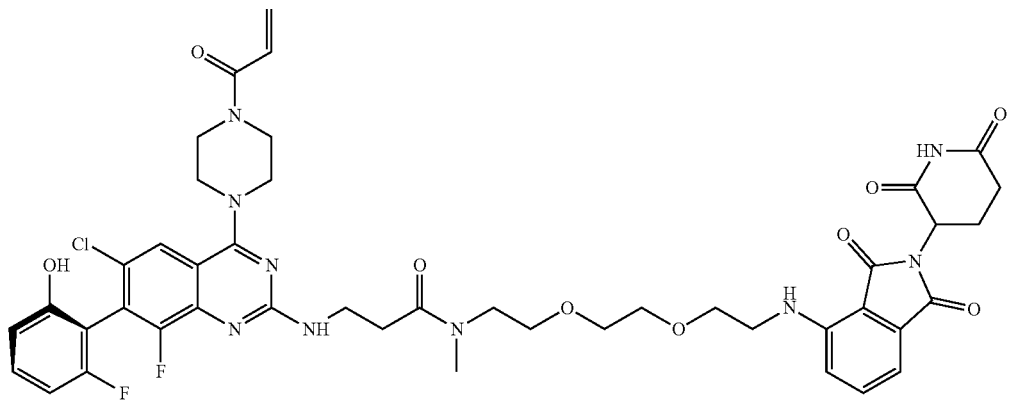

To the mixture of 3-[[6-chloro-8-fluoro-7-(2-fluoro-6-hydroxy-phenyl)-4-piperazin-1-yl-quinazolin-2-yl]amino]-N-[2-[2-[2-[[2-(2,6-dioxo-3-piperidyl)-1,3-dioxo-isoindolin-4-yl]amino]ethoxy]ethoxy]ethyl]-N-methyl-propanamide (75 mg, 0.08 mmol, 1 eq, trifluoroacetate) and 2,6-lutidine (82 mg, 0.77 mmol, 0.09 mL, 10 eq) in dichloromethane (20 mL) was added prop-2-enoyl chloride (7 mg, 0.08 mmol, 0.006 mL, 1 eq) in dichloromethane (5 mL) at −78° C. The mixture was stirred at −78° C. for 30 minutes under nitrogen atmosphere. The mixture was quenched with water (20 mL). Then it was extracted with dichloromethane (20 mL×2). The combined organic layer was washed with water (20 mL×2) and brine (20 mL×2), dried over anhydrous sodium sulfate, filtered and concentrated under reduced pressure to give a residue. The residue was purified by semi-preparative reverse phase HPLC. 3-[[6-chloro-8-fluoro-7-(2-fluoro-6-hydroxy-phenyl)-4-(4-prop-2-enoylpiperazin-1-yl)quinazolin-2-yl]amino]-N-[2-[2-[2-[[2-(2,6-dioxo-3-piperidyl)-1,3-dioxo-isoindolin-4-yl]amino]ethoxy]ethoxy]ethyl]-N-methyl-propanamide (36.9 mg, 0.04 mmol, 51% yield, 99% purity) was obtained as a yellow solid. LC/MS (ESI) m/z: 918.3 [M+1]$^+$; $^1$H-NMR (400 MHz, DMSO-d$_6$) δ 11.09 (s, 1H), 10.47 (s, 1H), 8.10-8.00 (m, 1H), 7.94-7.77 (m, 1H), 7.55-7.51 (m, 1H), 7.39-7.37 (m, 1H), 7.11-7.00 (m, 2H), 6.87-6.74 (m, 3H), 6.59-6.56 (m, 1H), 6.18 (d, J=16.8 Hz, 1H), 5.75 (d, J=9.6 Hz, 1H), 5.04 (dd, J=4.8, 13.2 Hz, 1H), 4.25-4.13 (m, 3H), 3.85-3.68 (m, 17H), 2.95-2.84 (m, 4H), 2.70-2.59 (m, 6H), 2.02-1.99 (m, 1H).

Exemplary Synthesis of 3-(((R)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide (Exemplary Compound 112)

Step 1: Preparation of tert-butyl 4-((7R)-6-chloro-2-((3-((2-(2-(2-((2-(2,6-dioxopiperidin-3-yl)-1,3-dioxoisoindolin-4-yl)amino)ethoxy)ethoxy)ethyl)(methyl)amino)-3-oxopropyl)amino)-8-fluoro-7-(2-fluoro-6-hydroxyphenyl)quinazolin-4-yl)piperazine-1-carboxylate

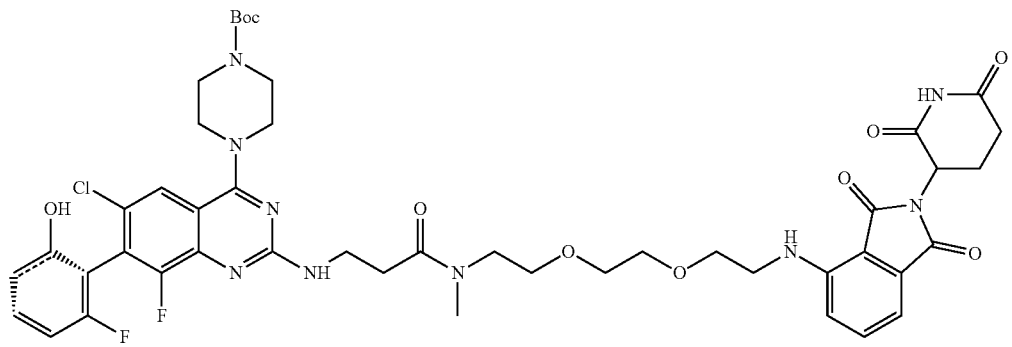

To the mixture of 2-(2,6-dioxo-3-piperidyl)-4-[2-[2-[2-(methylamino)ethoxy]ethoxy]ethylamino]isoindoline-1,3-dione (120 mg, 0.22 mmol, 1 eq, trifluoroacetate) and 3-[[4-(4-tert-butoxycarbonylpiperazin-1-yl)-6-chloro-8-fluoro-7-(2-fluoro-6-hydroxy-phenyl)quinazolin-2-yl]amino]propanoic acid (127 mg, 0.22 mmol, 1 eq) in N,N-dimethylformamide (5 mL) was added 1-hydroxybenzotriazole (60 mg, 0.45 mmol, 2 eq), N-(3-dimethylaminopropyl)-N-ethylcarbodiimide hydrochloride (86 mg, 0.45 mmol, 2 eq) and N,N-diisopropylethylamine (145 mg, 1.13 mmol, 0.2 mL, 5 eq). The mixture was stirred at 25° C. for 4 hours. The mixture was diluted with water (20 mL). Then it was extracted with ethyl acetate (20 mL×3). The combined organic layer was washed with water (30 mL×2) and brine (30 mL×2), dried over anhydrous sodium sulfate, filtered and concentrated under reduced pressure to give a residue. The residue was purified by prep-Thin-layer chromatography (dichloromethane:methanol=10:1). tert-butyl 4-[6-chloro-2-[[3-[2-[2-[2-[[2-(2,6-dioxo-3-piperidyl)-1,3-dioxo-isoindolin-4-yl]amino]ethoxy]ethoxy]ethyl-methyl-amino]-3-oxo-propyl]amino]-8-fluoro-7-(2-fluoro-6-hydroxy-phenyl)quinazolin-4-yl]piperazine-1-carboxylate (160 mg, 0.16 mmol, 73% yield) was obtained as a light yellow oil. LC/MS (ESI) m/z: 964.4 [M+1]$^+$.

Step 2: Preparation of 3-(((R)-6-chloro-8-fluoro-7-(2-fluoro-6-hydroxyphenyl)-4-(piperazin-1-yl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide

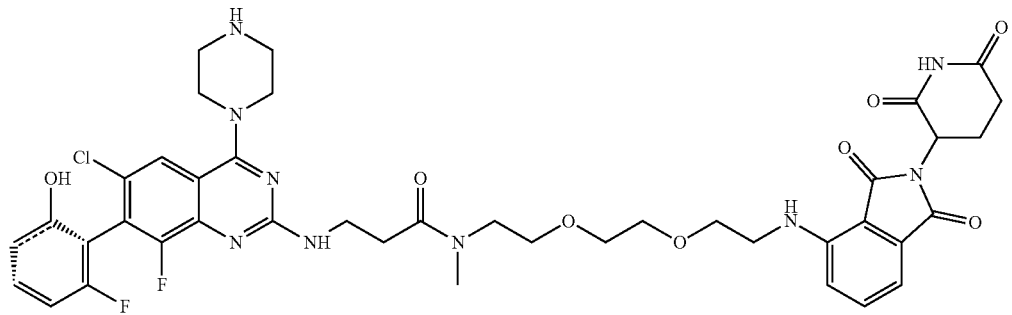

To the mixture of tert-butyl 4-[6-chloro-2-[[3-[2-[2-[2-[[2-(2,6-dioxo-3-piperidyl)-1,3-dioxo-isoindolin-4-yl]amino]ethoxy]ethoxy]ethyl-methyl-amino]-3-oxo-propyl]amino]-8-fluoro-7-(2-fluoro-6-hydroxy-phenyl)quinazolin-4-yl]piperazine-1-carboxylate (160 mg, 0.16 mmol, 1 eq) in dichloromethane (4 mL) was added trifluoroacetic acid (1 mL). The mixture was stirred at 25° C. for 1 hour. The mixture was concentrated under reduced pressure to give 3-[[6-chloro-8-fluoro-7-(2-fluoro-6-hydroxy-phenyl)-4-piperazin-1-yl-quinazolin-2-yl]amino]-N-[2-[2-[2-[[2-(2,6-dioxo-3-piperidyl)-1,3-dioxo-isoindolin-4-yl]amino]ethoxy]ethoxy]ethyl]-N-methyl-propanamide (160 mg, trifluoroacetate) as a green oil. LC/MS (ESI) m/z: 864.3 [M+1]$^+$.

Step 3: Preparation of 3-(((R)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide

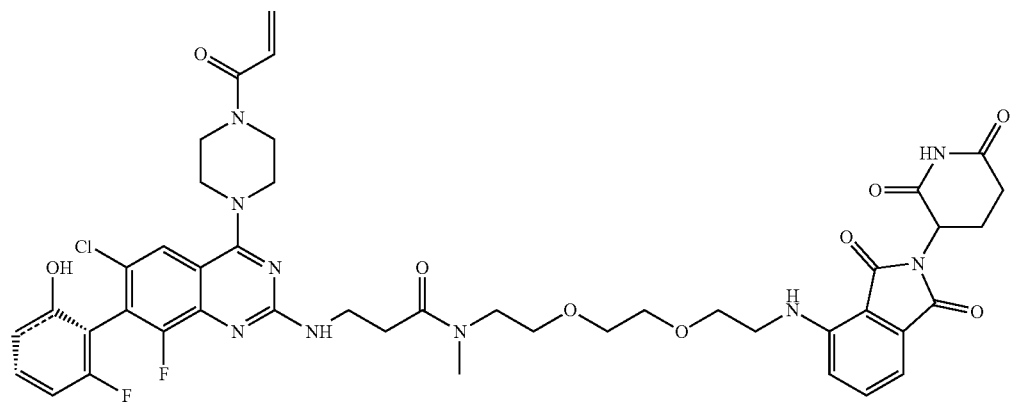

To the mixture of 3-[[6-chloro-8-fluoro-7-(2-fluoro-6-hydroxy-phenyl)-4-piperazin-1-yl-quinazolin-2-yl]amino]-N-[2-[2-[2-[[2-(2,6-dioxo-3-piperidyl)-1,3-dioxo-isoindolin-4-yl]amino]ethoxy]ethoxy]ethyl]-N-methyl-propanamide (80 mg, 0.08 mmol, 1 eq, trifluoroacetate) and 2,6-lutidine (87 mg, 0.81 mmol, 0.09 mL, 10 eq) in dichloromethane (20 mL) was added prop-2-enoyl chloride (7 mg, 0.08 mmol, 0.006 mL, 1 eq) in dichloromethane (5 mL) at −78° C. The mixture was stirred at −78° C. for 30 minutes under nitrogen atmosphere. The mixture was quenched with water (20 mL). Then it was extracted with dichloromethane (20 mL×2). The combined organic layer was washed with water (20 mL×2) and brine (20 mL×2), dried over anhydrous sodium sulfate, filtered and concentrated under reduced pressure to give a residue. The residue was purified by semi-preparative reverse phase HPLC. 3-[[6-chloro-8-fluoro-7-(2-fluoro-6-hydroxy-phenyl)-4-(4-prop-2-enoylpiperazin-1-yl)quinazolin-2-yl]amino]-N-[2-[2-[2-[[2-(2,6-dioxo-3-piperidyl)-1,3-dioxo-isoindolin-4-yl]amino]ethoxy]ethoxy]ethyl]-N-methyl-propanamide (45.3 mg, 0.04 mmol, 59% yield, 99% purity) was obtained as a yellow solid. LC/MS (ESI) m/z: 918.3 [M+1]$^+$; $^1$H-NMR (400 MHz, DMSO-d$_6$) δ 11.09 (s, 1H), 10.49 (s, 1H), 8.02-8.00 (m, 1H), 7.95-7.80 (m, 1H), 7.55-7.51 (m, 1H), 7.40-7.38 (m, 1H), 7.12-7.01 (m, 2H), 6.88-6.74 (m, 3H), 6.55-6.50 (m, 1H), 6.18 (d, J=16.8 Hz, 1H), 5.75 (d, J=9.6 Hz, 1H), 5.04 (dd, J=4.8, 13.6 Hz, 1H), 4.20-4.11 (m, 3H), 3.86-3.68 (m, 17H), 2.95-2.84 (m, 4H), 2.71-2.55 (m, 6H), 2.02-2.00 (m, 1H).

Exemplary Synthesis of (E)-5-(2-(2-((5-(4-(6-chloro-8-fluoro-7-(3-hydroxynaphthalen-1-yl)quinazolin-4-yl)piperazin-1-yl)-5-oxopent-3-en-1-yl)oxy)ethoxy)ethoxy)-2-(2,6-dioxopiperidin-3-yl)isoindoline-1,3-dione (Exemplary Compound 169)

Step 1: Preparation of 2-(2-(3-(benzyloxy)propoxy)ethoxy)ethan-1-ol

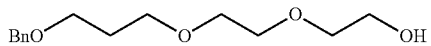 [SMILES: OCCOCCOCCCOCc1ccccc1]

To a solution of 2,2'-oxydiethanol (8 g, 74.9 mmol) in dry N,N-dimethylformamide (20 ml) was added sodium hydride (60% in mineral oil) (1.5 g, 37.4 mmol) at 0° C. The mixture was stirred at 50° C. for 1 hour. Then 3-(benzyloxy)propyl 4-methylbenzenesulfonate (4 g, 12.5 mmol) was added at 50° C. and the mixture was stirred at 70° C. for 12 hours. The mixture was cooled to room temperature and partitioned with ethyl acetate (100 ml) and water (200 ml). The organic layer was collected, washed with brine (50 ml), dried over anhydrous sodium sulfate, and concentrated under reduced pressure to give a crude residue which was purified by silica gel flash chromatography (eluted with 33-50% ethyl acetate in hexane to 2% methanol in dichloromethane) to afford 2-(2-(3-(benzyloxy)propoxy)ethoxy)ethanol (1.94 g, 61%) as yellow oil.

Step 2: Preparation of 2-(2-(2-(3-(benzyloxy)propoxy)ethoxy)ethoxy)tetrahydro-2H-pyran

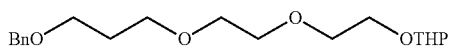

A mixture of 2-(2-(3-(benzyloxy)propoxy)ethoxy)ethanol (1.94 g, 7.63 mmol), 3,4-dihydro-2H-pyran (1.28 g, 15.25 mmol), pyridin-1-ium 4-methylbenzenesulfonate (960 mg, 3.81 mmol) and N,N-dimethylpyridin-4-amine (93 mg, 0.76 mmol) in dichloromethane (20 ml) was stirred at refluxed for 5 hours. The mixture was concentrated and the residue was partitioned with water (30 ml) and ethyl acetate (20 ml). The organic layer was collected, washed with brine (20 ml), dried over anhydrous sodium sulfate, and concentrated under reduced pressure to give a crude residue which was purified by silica gel flash chromatography (eluted with 18-25% ethyl acetate in hexane) to afford 2-(2-(2-(3-(benzyloxy)propoxy)ethoxy)ethoxy)tetrahydro-2H-pyran (2.4 g, 88%) as colorless oil. $^1$H-NMR (400 MHz, CDCl$_3$) δ 1.48-1.64 (m, 4H), 1.68-1.75 (m, 1H), 1.79-1.85 (m, 1H), 1.87-1.93 (m, 2H), 3.47-3.53 (m, 1H), 3.55-3.69 (m, 11H), 3.84-3.90 (m, 2H), 4.50 (s, 2H), 4.63 (t, J=3.6 Hz, 1H), 7.27-7.36 (m, 5H).

Step 3: Preparation of 3-(2-(2-((tetrahydro-2H-pyran-2-yl)oxy)ethoxy)ethoxy)propan-1-ol

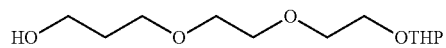

A mixture of 2-(2-(2-(3-(benzyloxy)propoxy)ethoxy)ethoxy)tetrahydro-2H-pyran (2.4 g, 7.09 mmol) and Palladium on carbon (10%, 240 mg) in methanol (30 ml) was stirred at room temperature for 1 hour under hydrogen atmosphere (hydrogen balloon). Palladium on carbon was removed through filtration and washed with methanol (10 ml). The combined filtrate was concentrated under reduced pressure to afford 3-(2-(2-((tetrahydro-2H-pyran-2-yl)oxy)ethoxy)ethoxy)propan-1-ol (1.53 g, 92%) as grey oil.

Step 4: Preparation of 3-(2-(2-((tetrahydro-2H-pyran-2-yl)oxy)ethoxy)ethoxy)propanal

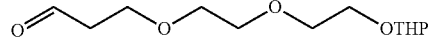

A mixture of 3-(2-(2-((tetrahydro-2H-pyran-2-yl)oxy)ethoxy)ethoxy)propan-1-ol (1.53 g, 6.16 mmol) and Dess-Martin periodinane (5.2 g, 12.32 mmol) in dichloromethane (15 ml) was stirred at room temperature for 1 hour. The mixture was concentrated and the residue was washed with hexane (10 ml). The mixture was filtered and the filtrate was concentrated under reduced pressure to afford 3-(2-(2-((tetrahydro-2H-pyran-2-yl)oxy)ethoxy)ethoxy)propanal (1.3 g, 85%) as colorless oil.

Step 5: Preparation of tert-butyl (E)-5-(2-(2-((tetrahydro-2H-pyran-2-yl)oxy)ethoxy)ethoxy)pent-2-enoate

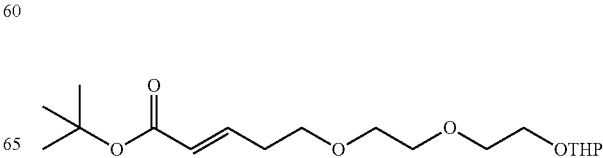

A mixture of 3-(2-(2-((tetrahydro-2H-pyran-2-yl)oxy)ethoxy)ethoxy)propanal (600 mg, 2.44 mmol) and tert-butyl 2-(triphenylphosphoranylidene)acetate (918 mg, 2.44 mmol) in dichloromethane (6 ml) was stirred at room temperature for 2 hours. The mixture was concentrated and the residue was purified by silica gel flash chromatography (eluted with 13-20% ethyl acetate in hexane) to afford(E)-tert-butyl 5-(2-(2-((tetrahydro-2H-pyran-2-yl)oxy)ethoxy)ethoxy)pent-2-enoate (420 mg, 50%) as colorless oil. $^1$H-NMR (400 MHz, CDCl$_3$) δ 1.48 (s, 9H), 1.50-1.62 (m, 4H), 1.69-1.76 (m, 1H), 1.79-1.87 (m, 1H), 2.44-2.49 (m, 2H), 3.48-3.53 (m, 1H), 3.57-3.70 (m, 9H), 3.84-3.90 (m, 2H), 4.63 (t, J=3.6 Hz, 1H), 5.78-5.82 (m, 1H), 6.81-6.88 (m, 1H).

Step 6: Preparation of tert-butyl (E)-5-(2-(2-hydroxyethoxy)ethoxy)pent-2-enoate

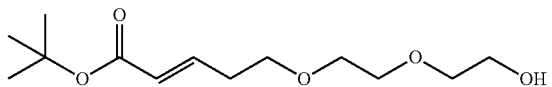 [SMILES: CC(C)(C)OC(=O)/C=C/CCOCCOCCO]

A mixture of (E)-tert-butyl 5-(2-(2-((tetrahydro-2H-pyran-2-yl)oxy)ethoxy)ethoxy)pent-2-enoate (420 mg, 1.22 mmol) and pyridin-1-ium 4-methylbenzenesulfonate (154 mg, 0.61 mmol) in methanol (5 ml) was stirred at 50° C. for 6 hours. The mixture was concentrated and the residue was partitioned with water (20 ml) and ethyl acetate (10 ml). The organic layer was collected, washed with brine (10 ml), dried over anhydrous sodium sulfate, and concentrated under reduced pressure to afford (E)-tert-butyl5-(2-(2-hydroxyethoxy)ethoxy)pent-2-enoate (275 mg, 86%) as colorless oil.

Step 7: Preparation of tert-butyl (E)-5-(2-(2-(tosyloxy)ethoxy)ethoxy)pent-2-enoate

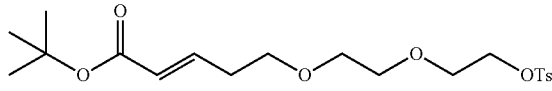 [SMILES: Cc1ccc(S(=O)(=O)OCCOCCOCC/C=C/C(=O)OC(C)(C)C)cc1]

To a solution of (E)-tert-butyl 5-(2-(2-hydroxyethoxy)ethoxy)pent-2-enoate (275 mg, 1.05 mmol), triethylamine (215 mg, 2.1 mmol) and N, N-dimethylpyridin-4-amine (13 mg, 0.1 mmol) in dichloromethane (3 ml) was added 4-toluenesulfonyl chloride (212 mg, 1.1 mmol) at 0° C. The mixture was stirred at room temperature for 3 hours. The mixture was diluted with dichloromethane (20 ml), washed with water (10 ml), brine (20 ml), dried over anhydrous sodium sulfate and concentrated under reduced pressure to give a crude residue which was purified by silica gel flash chromatography (eluted with 18-25% ethyl acetate in hexane) to afford (E)-tert-butyl 5-(2-(2-(tosyloxy)ethoxy)ethoxy)pent-2-enoate (240 mg, 55%) as colorless oil. $^1$H-NMR (400 MHz, CDCl$_3$) δ 1.47 (s, 9H), 2.41-2.47 (m, 5H), 3.52-3.59 (m, 6H), 3.68-3.70 (m, 2H), 4.15-4.18 (m, 2H), 5.77-5.81 (m, 1H), 6.81-6.84 (m, 1H), 7.34 (d, J=8.0 Hz, 2H), 7.80 (d, J=8.4 Hz, 2H).

Step 8: Preparation of tert-butyl (E)-5-(2-(2-((2-(2,6-dioxopiperidin-3-yl)-1,3-dioxoisoindolin-5-yl)oxy)ethoxy)ethoxy)pent-2-enoate

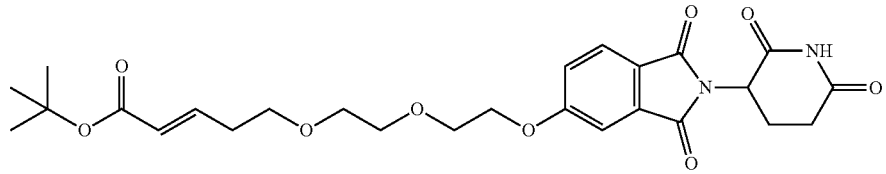 [SMILES: CC(C)(C)OC(=O)/C=C/CCOCCOCCOc1ccc2c(c1)C(=O)N(C1CCC(=O)NC1=O)C2=O]

A mixture of (E)-tert-butyl 5-(2-(2-(tosyloxy)ethoxy)ethoxy)pent-2-enoate (240 mg, 0.58 mmol), 2-(2,6-dioxopiperidin-3-yl)-5-hydroxyisoindoline-1,3-dione (159 mg, 0.58 mmol) and potassium carbonate (160 mg, 1.16 mmol) in dry N,N-dimethylformamide (3 ml) was stirred at 50° C. for 16 hours. The mixture was partitioned between ethyl acetate (20 ml) and water (30 ml). The organic layer was collected, washed with brine (20 ml), dried over anhydrous sodium sulfate, and concentrated under reduced pressure to give a crude residue which was purified by silica gel flash chromatography (eluted with 1-2% methanol in dichloromethane) to afford (E)-tert-butyl 5-(2-(2-((2-(2,6-dioxopiperidin-3-yl)-1,3-dioxoisoindolin-5-yl)oxy)ethoxy)ethoxy)pent-2-enoate (200 mg, 67%) as colorless oil. LC/MS (ESI) m/z: 517.40 [M+1]$^+$.

Step 9: Preparation of (E)-5-(2-(2-((2-(2,6-dioxopiperidin-3-yl)-1,3-dioxoisoindolin-5-yl)oxy)ethoxy)ethoxy)pent-2-enoic acid

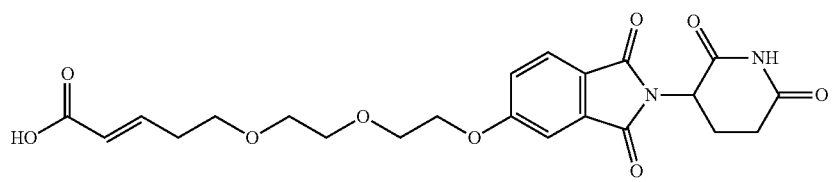 [SMILES: O=C(O)/C=C/CCOCCOCCOc1ccc2c(c1)C(=O)N(C1CCC(=O)NC1=O)C2=O]

To a solution of (E)-tert-butyl 5-(2-(2-((2-(2,6-dioxopiperidin-3-yl)-1,3-dioxoisoindolin-5-yl)oxy)ethoxy)ethoxy)pent-2-enoate (100 mg, 0.19 mmol) in dichloromethane (2 ml) was added 2,2,2-trifluoroacetic acid (0.5 ml) at room temperature. The mixture was stirred at room temperature for 30 minutes. The mixture was concentrated and the residue was purified by pre-TLC (10% methanol in dichloromethane) to afford (E)-5-(2-(2-((2-(2,6-dioxopiperidin-3-yl)-1,3-dioxoisoindolin-5-yl)oxy)ethoxy)ethoxy)pent-2-enoic acid (64 mg, 72%) as colorless oil. LC/MS (ESI) m/z: 461.10 [M+1]$^+$.

Step 10: Preparation of (E)-5-(2-(2-((5-(4-(6-chloro-8-fluoro-7-(3-hydroxynaphthalen-1-yl)quinazolin-4-yl)piperazin-1-yl)-5-oxopent-3-en-1-yl)oxy)ethoxy)ethoxy)-2-(2,6-dioxopiperidin-3-yl)isoindoline-1,3-dione

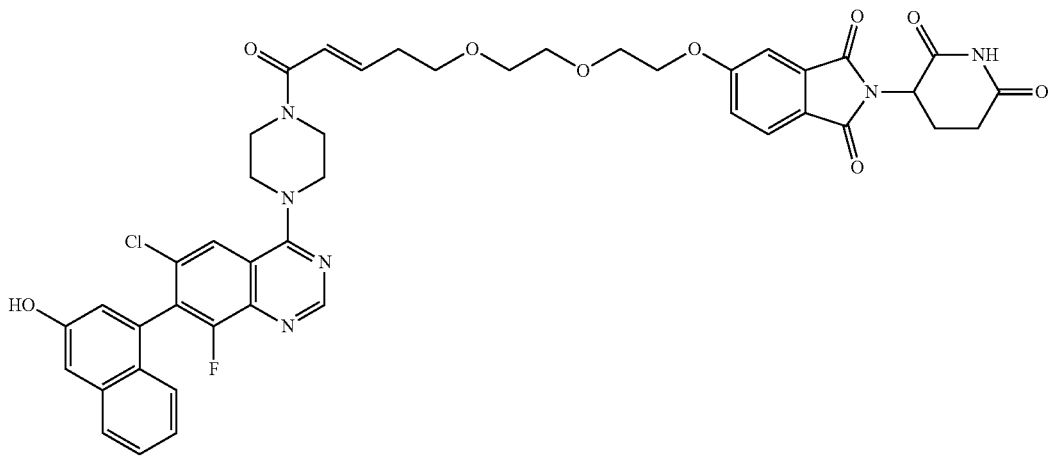 [SMILES: O=C1CCC(N2C(=O)c3ccc(OCCOCCOCC/C=C/C(=O)N4CCN(c5ncnc6c(F)c(-c7cc(O)cc8ccccc78)c(Cl)cc56)CC4)cc3C2=O)C(=O)N1]

To a solution of (E)-5-(2-(2-((2-(2,6-dioxopiperidin-3-yl)-1,3-dioxoisoindolin-5-yl)oxy)ethoxy)ethoxy)pent-2-enoic acid (42 mg, 0.09 mmol), 4-(6-chloro-8-fluoro-4-(piperazin-1-yl)quinazolin-7-yl)naphthalen-2-ol (40 mg, 0.1 mmol) and N-ethyl-N-isopropylpropan-2-amine (47 mg, 0.36 mmol) in dry N,N-dimethylformamide (1 ml) was added HATU (2-(7-Aza-1H-benzotriazole-1-yl)-1,1,3,3-tetramethyluronium hexafluorophosphate) (69 mg, 0.18 mmol) at 0° C., the resulting mixture was allowed to warm to room temperature and stirred at room temperature for 15 minutes. The mixture was partitioned between ethyl acetate (10 ml) and water (10 ml). The organic layer was collected, washed with brine (20 ml), dried over anhydrous sodium sulfate, and concentrated under reduced pressure to give a crude residue which was purified by HPLC to afford (E)-5-(2-(2-((5-(4-(6-chloro-8-fluoro-7-(3-hydroxynaphthalen-1-yl)quinazolin-4-yl)piperazin-1-yl)-5-oxopent-3-en-1-yl)oxy)ethoxy)ethoxy)-2-(2,6-dioxopiperidin-3-yl)isoindoline-1,3-dione (22 mg, 28%) as white solid. LC/MS (ESI) m/z: 851.20 [M+1]$^+$; $^1$H-NMR (400 MHz, DMSO-d$_6$) δ 2.37-2.48 (m, 3H), 2.54-2.65 (m, 2H), 2.83-2.93 (m, 1H), 3.54-3.94 (m, 16H), 4.25-4.40 (m, 2H), 5.09-5.13 (m, 1H), 6.53-6.58 (m, 1H), 6.70-6.77 (m, 1H), 7.11-7.46 (m, 7H), 7.82 (d, J=8.0 Hz, 2H), 8.08 (s, 1H), 8.71 (s, 1H), 10.06 (s, 1H), 11.10 (s, 1H).

Exemplary Synthesis of 4-(6-chloro-8-fluoro-2-(((S)-17-((2S,4R)-4-hydroxy-2-(((S)-1-(4-(4-methylthiazol-5-yl)phenyl)ethyl)carbamoyl)pyrrolidine-1-carbonyl)-4,18,18-trimethyl-3,15-dioxo-77,10,3-trioxa-4,16-diazanonadecyl)amino)-7-(3-hydroxynaphthalen-1-yl)quinazolin-4-yl)piperazine-1-carboxamide (Exemplary Compound 183)

Step 1: Preparation of tert-butyl 4-(6-chloro-8-fluoro-7-(3-hydroxynaphthalen-1-yl)-2-((3-methoxy-3-oxopropyl)amino)quinazolin-4-yl)piperazine-1-carboxylate

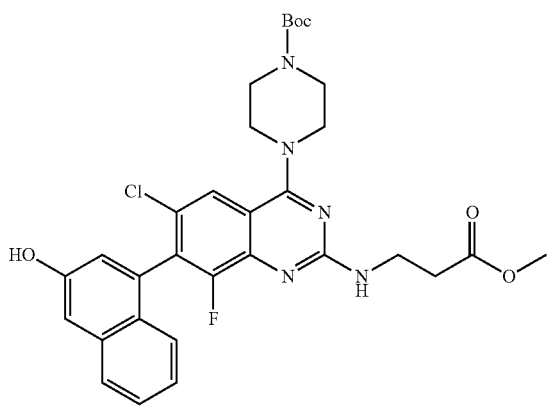 [SMILES: COC(=O)CCNc1nc(N2CCN(C(=O)OC(C)(C)C)CC2)c2cc(Cl)c(-c3cc(O)cc4ccccc34)c(F)c2n1]

A mixture of tert-butyl 4-[7-bromo-6-chloro-8-fluoro-2-[(3-methoxy-3-oxo-propyl)amino]quinazolin-4-yl]piperazine-1-carboxylate (1.00 g, 1.83 mmol, 1 eq), 4-(4,4,5,5-tetramethyl-1,3,2-dioxaborolan-2-yl)naphthalen-2-ol (593 mg, 2.19 mmol, 1.2 eq), potassium phosphate (1.5 M, 3.7 mL, 3 eq) and [2-(2-aminophenyl)phenyl]palladium(1+); dicyclohexyl-[2-(2,4,6-triisopropylphenyl)phenyl]phosphane; methanesulfonate (155 mg, 0.18 mmol, 0.1 eq) in tetrahydrofuran (10 mL) was degassed and purged with nitrogen gas for 3 times, and then the mixture was stirred at 65° C. for 12 hours under nitrogen gas atmosphere. The reaction mixture was diluted with water (50 mL), then extracted with ethyl acetate (50 mL×2). The combined organic layers were washed with brine (100 mL×1), dried over anhydrous sodium sulfate, filtered and concentrated under reduced pressure to give a residue. The residue was purified by silica gel column chromatography (petroleum ether/ethyl acetate=5/1 to 1/1) to give compound tert-butyl 4-[6-chloro-8-fluoro-7-(3-hydroxy-1-naphthyl)-2-[(3-methoxy-3-oxo-propyl)amino]quinazolin-4-yl]piperazine-1-carboxylate (780 mg, 1.28 mmol, 70% yield) as a brown solid. $^1$H-NMR (400 MHz, CDCl$_3$) δ 7.73 (d, J=8.4 Hz, 1H), 7.64 (d, J=1.6 Hz, 1H), 7.40 (t, J=7.6 Hz, 1H), 7.34-7.28 (m, 2H), 7.24-7.17 (m, 1H), 7.12 (d, J=2.0 Hz, 1H), 5.86 (brs, 1H), 3.90-3.72 (m, 6H), 3.71-3.60 (m, 7H), 2.69 (t, J=6.4 Hz, 2H), 1.52 (s, 9H).

Step 2: Preparation of methyl 3-((6-chloro-8-fluoro-7-(3-hydroxynaphthalen-1-yl)-4-(piperazin-1-yl)quinazolin-2-yl)amino)propanoate

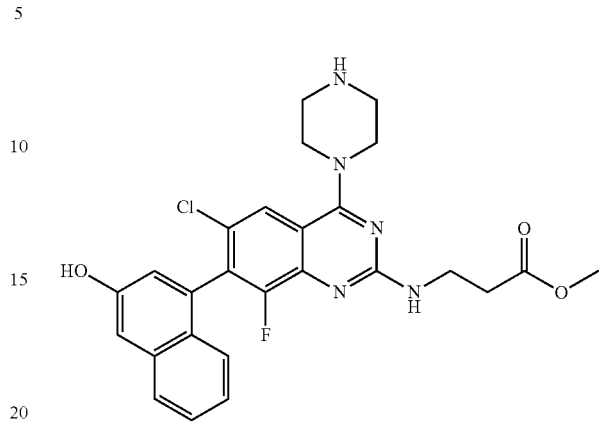

To a solution of tert-butyl 4-[6-chloro-8-fluoro-7-(3-hydroxy-1-naphthyl)-2-[(3-methoxy-3-oxo-propyl)amino]quinazolin-4-yl]piperazine-1-carboxylate (780 mg, 1.28 mmol, 1 eq) in dichloromethane (5 mL) was added hydrochloric acid in dioxane (4 M, 5 mL). The mixture was stirred at 25° C. for 15 minutes. The reaction mixture was concentrated under reduced pressure to give compound methyl 3-[[6-chloro-8-fluoro-7-(3-hydroxy-1-naphthyl)-4-piperazin-1-yl-quinazolin-2-yl]amino]propanoate (700 mg, hydrochloride) as a yellow solid. LC/MS (ESI) m/z: 510.2 [M+1]$^+$.

Step 3: Preparation of methyl 3-((4-(4-carbamoylpiperazin-1-yl)-6-chloro-8-fluoro-7-(3-hydroxynaphthalen-1-yl)quinazolin-2-yl)amino)propanoate

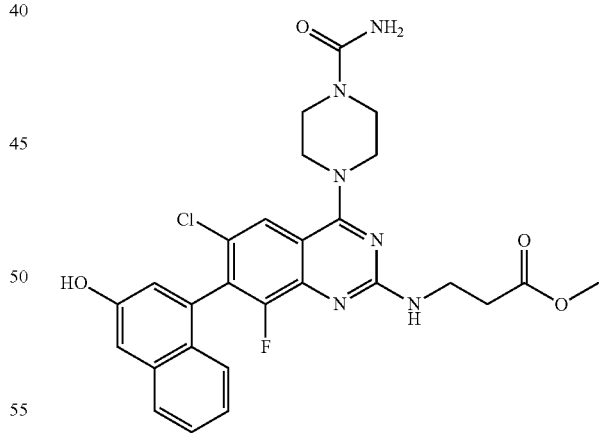

To a solution of methyl 3-[[6-chloro-8-fluoro-7-(3-hydroxy-1-naphthyl)-4-piperazin-1-yl-quinazolin-2-yl]amino]propanoate (650 mg, 1.19 mmol, 1 eq, hydrochloride) and triethylamine (361 mg, 3.57 mmol, 0.5 mL, 3 eq) in dichloromethane (10 mL) was added a solution of isocyanato(trimethyl)silane (178 mg, 1.55 mmol, 1.3 eq) in dichloromethane (1.5 mL). The mixture was stirred at 20° C. for 0.5 hour. The reaction mixture was concentrated under reduced pressure to give compound methyl 3-[[4-(4-carbamoylpiperazin-1-yl)-6-chloro-8-fluoro-7-(3-hydroxy-1-naphthyl) quinazolin-2-yl]amino]propanoate (700 mg) as a yellow solid. LC/MS (ESI) m/z: 553.2 [M+1]⁺.

Step 4: Preparation of 3-((4-(4-carbamoylpiperazin-1-yl)-6-chloro-8-fluoro-7-(3-hydroxynaphthalen-1-yl)quinazolin-2-yl)amino)propanoic acid

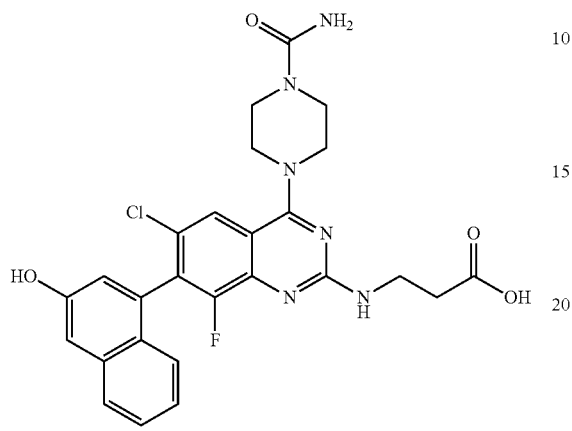

To a solution of methyl 3-[[4-(4-carbamoylpiperazin-1-yl)-6-chloro-8-fluoro-7-(3-hydroxy-1-naphthyl)quinazolin-2-yl]amino]propanoate (700 mg, 1.27 mmol, 1 eq) in tetrahydrofuran (10 mL) and water (1 mL) was added lithium hydroxide monohydrate (133 mg, 3.16 mmol, 2.5 eq). The mixture was stirred at 20° C. for 0.5 hour. The reaction mixture was concentrated under reduced pressure to remove tetrahydrofuran. The residue was acidified to pH=3 with hydrochloric acid (1 M), some precipitate was formed while the addition of hydrochloric acid. The resulting mixture was filtered and the filter cake was evaporated to dryness to give compound 3-[[4-(4-carbamoylpiperazin-1-yl)-6-chloro-8-fluoro-7-(3-hydroxy-1-naphthyl)quinazolin-2-yl]amino] propanoic acid (640 mg, 1.19 mmol, 94% yield) as a brown solid. LC/MS (ESI) m/z: 539.1 [M+1]⁺.

Step 5: Preparation of 4-(6-chloro-8-fluoro-2-(((S)-17-((2S,4R)-4-hydroxy-2-(((S)-1-(4-(4-methylthiazol-5-yl)phenyl)ethyl)carbamoyl)pyrrolidine-1-carbonyl)-4,18,18-trimethyl-3,15-dioxo-7,10,13-trioxa-4,16-diazanonadecyl)amino)-7-(3-hydroxynaphthalen-1-yl)quinazolin-4-yl)piperazine-1-carboxamide

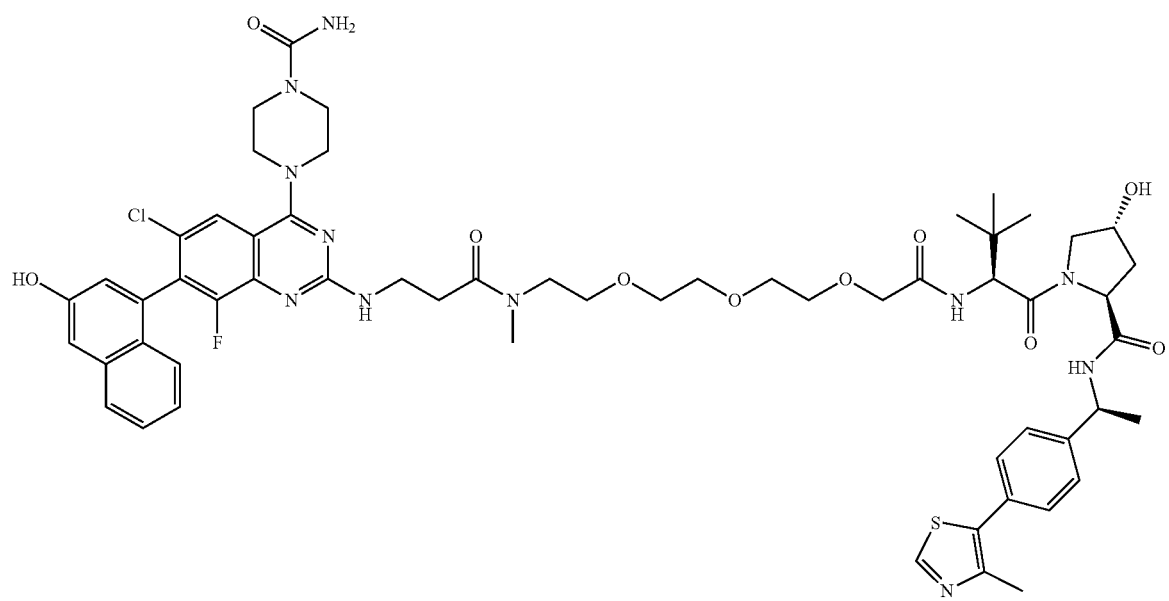 [SMILES: Cc1ncsc1-c1ccc([C@H](C)NC(=O)[C@@H]2C[C@@H](O)CN2C(=O)[C@@H](NC(=O)COCCOCCOCCN(C)C(=O)CCNc2nc(N3CCN(C(N)=O)CC3)c3cc(Cl)c(-c4cc(O)cc5ccccc45)c(F)c3n2)C(C)(C)C)cc1]

To a solution of (2S,4R)-1-((S)-15-(tert-butyl)-13-oxo-5,8,11-trioxa-2,14-diazahexadecan-16-oyl)-4-hydroxy-N—((S)-1-(4-(4-methylthiazol-5-yl)phenyl)ethyl)pyrrolidine-2-carboxamide (70 mg, 0.93 mmol), 3-((4-(4-carbamoylpiperazin-1-yl)-6-chloro-8-fluoro-7-(3-hydroxynaphthalen-1-yl)quinazolin-2-yl)amino)propanoic acid (40 mg, 0.074 mmol) and N-ethyl-N-isopropylpropan-2-amine (48 mg, 0.37 mmol) in dry N,N-dimethylformamide (1 ml) was added HATU (2-(7-Aza-1H-benzotriazole-1-yl)-1,1,3,3-tetramethyluronium hexafluorophosphate) (72 mg, 0.18 mmol) at 0° C., the resulting mixture was allowed to warm to room temperature and stirred at room temperature for 10 minutes. The mixture was partitioned between ethyl acetate (10 ml) and water (10 ml). The organic layer was collected, washed with brine (10 ml), dried over anhydrous sodium sulfate, and concentrated under reduced pressure to give a crude residue which was purified by pre-TLC (10% methanol in dichloromethane) to afford 4-(6-chloro-8-fluoro-2-(((S)-17-((2S,4R)-4-hydroxy-2-(((S)-1-(4-(4-methylthiazol-5-yl)phenyl)ethyl)carbamoyl)pyrrolidine-1-carbonyl)-4,18,18-trimethyl-3,15-dioxo-7,10,13-trioxa-4,16-diazanonadecyl)amino)-7-(3-hydroxynaphthalen-1-yl)quinazolin-4-yl)piperazine-1-carboxamide (40 mg, 36% two steps) as light yellow solid. LC/MS (ESI) m/z: 1190.40 [M+23]⁺; ¹H-NMR (400 MHz, DMSO-d₆) δ 0.92 (s, 9H), 1.17-1.26 (m, 3H), 1.31-1.39 (m, 3H), 1.74-1.81 (m, 1H), 1.99-2.07 (m, 1H), 2.45 (s, 3H), 2.57-2.70 (m, 2H), 2.74-2.92 (m, 2H), 3.01 (s, 1H), 3.39-3.62 (m, 20H), 3.86-3.98 (m, 2H), 4.22-4.34 (m, 1H), 4.42-4.58 (m, 2H), 4.84-4.94 (m, 2H), 5.12 (s, 1H), 6.08 (s, 2H), 7.04-7.43 (m, 11H), 7.73-7.86 (m, 2H), 8.42 (d, J=7.6 Hz, 1H), 8.97 (s, 1H), 9.97 (s, 1H).

Exemplary Synthesis of (2S,4R)-1-((2S)-21-((4-(4-acryloylpiperazin-1-yl)-6-chloro-8-fluoro-7-(3-hydroxynaphthalen-1-yl)quinazolin-2-yl)amino)-2-(tert-butyl)-18-methyl-4,19-dioxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide (Exemplary Compound 194)

Step 1: Preparation of 3-((4-(4-(tert-butoxycarbonyl)piperazin-1-yl)-6-chloro-8-fluoro-7-(3-hydroxynaphthalen-1-yl)quinazolin-2-yl)amino)propanoic acid

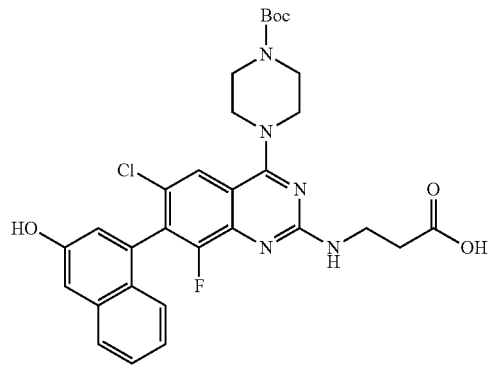 [SMILES: CC(C)(C)OC(=O)N1CCN(c2nc(NCCC(=O)O)nc3c(F)c(-c4cc(O)cc5ccccc45)c(Cl)cc23)CC1]

A solution of tert-butyl 4-[6-chloro-8-fluoro-7-(3-hydroxy-1-naphthyl)-2-[(3-methoxy-3-oxo-propyl)amino]quinazolin-4-yl]piperazine-1-carboxylate (7.02 g, 11.51 mmol, 1 eq) in tetrahydrofuran (25 mL), methanol (25 mL) and water (50 mL) was added lithium hydroxide monohydrate (4.83 g, 115.07 mmol, 10 eq), the mixture was stirred at 15° C. for 2 hours. The mixture was poured into water (10 mL), the pH was adjusted to 3 with 1M hydrochloric acid. The aqueous phase was extracted with ethyl acetate (150 mL×3). The combined organic phase was washed with brine (20 mL×2), dried with anhydrous sodium sulfate, filtered and concentrated under vacuum. Compound 3-[[4-(4-tert-butoxycarbonylpiperazin-1-yl)-6-chloro-8-fluoro-7-(3-hydroxy-1-naphthyl)quinazolin-2-yl]amino]propanoic acid (6.96 g) was obtained as a yellow solid. LC/MS (ESI) m/z: 596.3 [M+1]⁺; ¹H-NMR (400 MHz, DMSO-d₆) δ 12.19 (br s, 1H), 10.06 (s, 1H), 7.85-7.75 (m, 2H), 7.62-7.35 (m, 2H), 7.28 (d, J=2.2 Hz, 1H), 7.23 (d, J=3.7 Hz, 2H), 7.07 (d, J=2.2 Hz, 1H), 3.80-3.47 (m, 10H), 2.56 (br s, 2H), 1.45 (s, 9H).

Step 2: Preparation of tert-butyl 4-(6-chloro-8-fluoro-2-(((S)-20-((2S,4R)-4-hydroxy-2-(((S)-1-(4-(4-methylthiazol-5-yl)phenyl)ethyl)carbamoyl)pyrrolidine-1-carbonyl)-4,21,21-trimethyl-3,18-dioxo-7,10,13,16-tetraoxa-4,19-diazadocosyl)amino)-7-(3-hydroxynaphthalen-1-yl)quinazolin-4-yl)piperazine-1-carboxylate

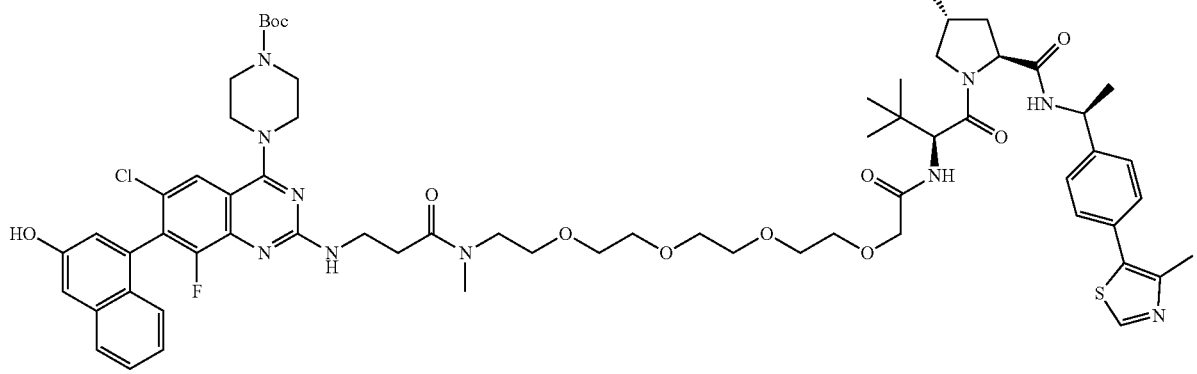

To a solution of (2S,4R)-1-[(2S)-3,3-dimethyl-2-[[2-[2-[2-[2-[2-(methylamino)ethoxy]ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (130 mg, 0.18 mmol, 1 eq, hydrochloride), 3-[[4-(4-tert-butoxycarbonylpiperazin-1-yl)-6-chloro-8-fluoro-7-(3-hydroxy-1-naphthyl)quinazolin-2-yl]amino]propanoic acid (106 mg, 0.18 mmol, 1 eq) and N,N-diisopropylethylamine (69 mg, 0.54 mmol, 0.09 mL, 3 eq) in N,N-dimethylformamide (3 mL) was added 1-hydroxybenzotriazole (29 mg, 0.21 mmol, 1.2 eq) and 1-(3-dimethylaminopropyl)-3-ethylcarbodiimide hydrochloride (41 mg, 0.21 mmol, 1.2 eq) sequentially at 0° C., then stirred at 20° C. for 2 hours. The reaction mixture was quenched with water 30 mL and then extracted with ethyl acetate (20 mL×3). The combined organic phase was washed with brine (10 mL), dried with anhydrous sodium sulfate, filtered and concentrated in vacuum to give a residue. The residue was purified by prep-TLC (dichloromethane/methanol=10/1). tert-butyl 4-[6-chloro-8-fluoro-2-[[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino]-3-oxo-propyl]amino]-7-(3-hydroxy-1-naphthyl)quinazolin-4-yl]piperazine-1-carboxylate (123 mg, 0.09 mmol, 50% yield, 92% purity) was obtained as an off-white solid. LC/MS (ESI) m/z: 635.6 [M/2+1]⁺.

Step 3: Preparation of (2S,4R)-1-((2S)-2-(tert-butyl)-21-((6-chloro-8-fluoro-7-(3-hydroxynaphthalen-1-yl)-4-(piperazin-1-yl)quinazolin-2-yl)amino)-18-methyl-4,19-dioxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide

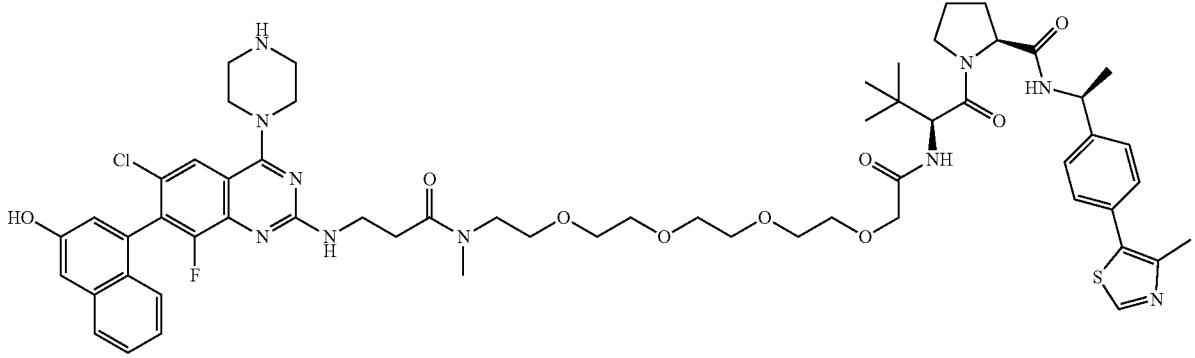

To a solution of tert-butyl 4-[6-chloro-8-fluoro-2-[[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino]-3-oxo-propyl]amino]-7-(3-hydroxy-1-naphthyl)quinazolin-4-yl]piperazine-1-carboxylate (170 mg, 0.13 mmol, 1 eq) in dichloromethane (5 mL) was added trifluoroacetic acid (770 mg, 6.75 mmol, 0.5 mL, 50.45 eq), then stirred at 20° C. for 2 hours. The reaction mixture was concentrated to give a residue. (2S,4R)-1-[(2S)-2-[[2-[2-[2-[2-[2-[3-[[6-chloro-8-fluoro-7-(3-hydroxy-1-naphthyl)-4-piperazin-1-yl-quinazolin-2-yl]amino]propanoyl-methyl-amino]ethoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (170 mg, 0.13 mmol, 98% yield, trifluoroacetic acid) was obtained as a yellow solid.

Step 4: Preparation of (2S,4R)-1-((2S)-21-((4-(4-acryloylpiperazin-1-yl)-6-chloro-8-fluoro-7-(3-hydroxynaphthalen-1-yl)quinazolin-2-yl)amino)-2-(tert-butyl)-18-methyl-4,19-dioxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide

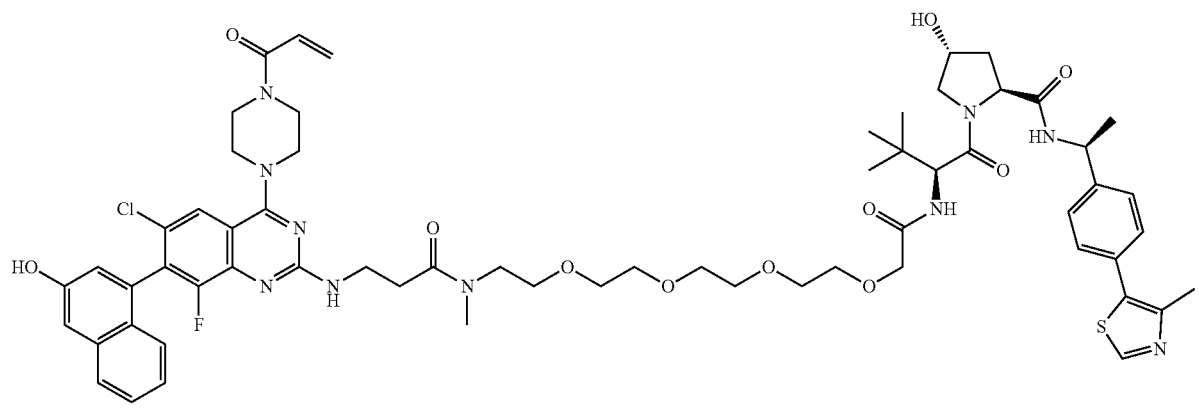 [SMILES: C=CC(=O)N1CCN(c2nc(NCCC(=O)N(C)CCOCCOCCOCCOCC(=O)N[C@H](C(=O)N3C[C@H](O)C[C@H]3C(=O)N[C@@H](C)c3ccc(-c4scnc4C)cc3)C(C)(C)C)nc3c(F)c(-c4cc(O)cc5ccccc45)c(Cl)cc23)CC1]

To a solution of (2S,4R)-1-[(2S)-2-[[2-[2-[2-[2-[2-[3-[[6-chloro-8-fluoro-7-(3-hydroxy-1-naphthyl)-4-piperazin-1-yl-quinazolin-2-yl]amino]propanoyl-methyl-amino]ethoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (170 mg, 0.13 mmol, 1 eq, trifluoroacetic acid) and 2,6-dimethylpyridine (142 mg, 1.32 mmol, 0.15 mL, 10 eq) in dichloromethane (15 mL) was added a solution of prop-2-enoyl chloride (12 mg, 0.13 mmol, 0.01 mL, 1 eq) in dichloromethane(10 mL) at −65° C., then stirred at this temperature for 10 minutes. The reaction mixture was quenched with water 10 mL and then extracted with dichloromethane (10 mL×3). The combined organic phase was washed with brine (10 mL), dried with anhydrous sodium sulfate, filtered and concentrated in vacuum to give a residue. The residue was purified by semi-preparative reverse phase HPLC to yield (2S,4R)-1-[(2S)-2-[[2-[2-[2-[2-[2-[3-[[6-chloro-8-fluoro-7-(3-hydroxy-1-naphthyl)-4-(4-prop-2-enoylpiperazin-1-yl)quinazolin-2-yl]amino]propanoyl-methyl-amino]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (38 mg, 0.03 mmol, 22% yield, 98% purity, formate) as an off-white solid. LC/MS (ESI) m/z: 612.3 [M/2+1]$^+$; $^1$H-NMR (400 MHz, DMSO-d$_6$) δ 10.02 (br s, 1H), 8.98 (s, 1H), 8.45 (br d, J=7.7 Hz, 1H), 8.17 (s, 1H), 7.84-7.76 (m, 2H), 7.49-7.33 (m, 6H), 7.28-7.10 (m, 4H), 7.03 (d, J=2.2 Hz, 1H), 6.85 (dd, J=10.5, 16.7 Hz, 1H), 6.26-6.11 (m, 1H), 5.81-5.67 (m, 1H), 5.14 (br s, 1H), 4.89 (br t, J=7.2 Hz, 1H), 4.53 (d, J=9.5 Hz, 1H), 4.43 (t, J=8.0 Hz, 1H), 4.27 (br s, 1H), 3.99-3.88 (m, 2H), 3.86-3.65 (m, 7H), 3.62-3.60 (m, 1H), 3.61-3.40 (m, 21H), 3.03-2.77 (m, 1H), 3.03-2.77 (m, 1H), 3.03-2.77 (m, 1H), 2.61 (br s, 1H), 2.44 (s, 3H), 2.10-1.98 (m, 1H), 1.81-1.70 (m, 1H), 1.48-1.31 (m, 3H), 0.96-0.88 (m, 1H), 0.92 (s, 8H).

Exemplary Synthesis of (2S,4R)-1-((S)-18-((4-(4-acryloylpiperazin-1-yl)-6-chloro-8-fluoro-7-((R)-2-fluoro-6-hydroxyphenyl)quinazolin-2-yl)amino)-2-(tert-butyl)-15-methyl-4,16-dioxo-6,9,12-trioxa-3,15-diazaoctadecanoyl)-4-hydroxy-N—((S)—(4-(4-methylthiazol-5-yl)phenyl)ethyl)pyrrolidine-2-carboxamide (Exemplary Compound 210)

Step 1: Preparation of tert-butyl 4-(6-chloro-8-fluoro-7-((R)-2-fluoro-6-hydroxyphenyl)-2-(((S)-17-((2S,4R)-4-hydroxy-2-(((S)-1-(4-(4-methylthiazol-5-yl)phenyl)ethyl)carbamoyl)pyrrolidine-1-carbonyl)-4,18,18-trimethyl-3,15-dioxo-7,10,13-trioxa-4,16-diazanonadecyl)amino)quinazolin-4-yl)piperazine-1-carboxylate

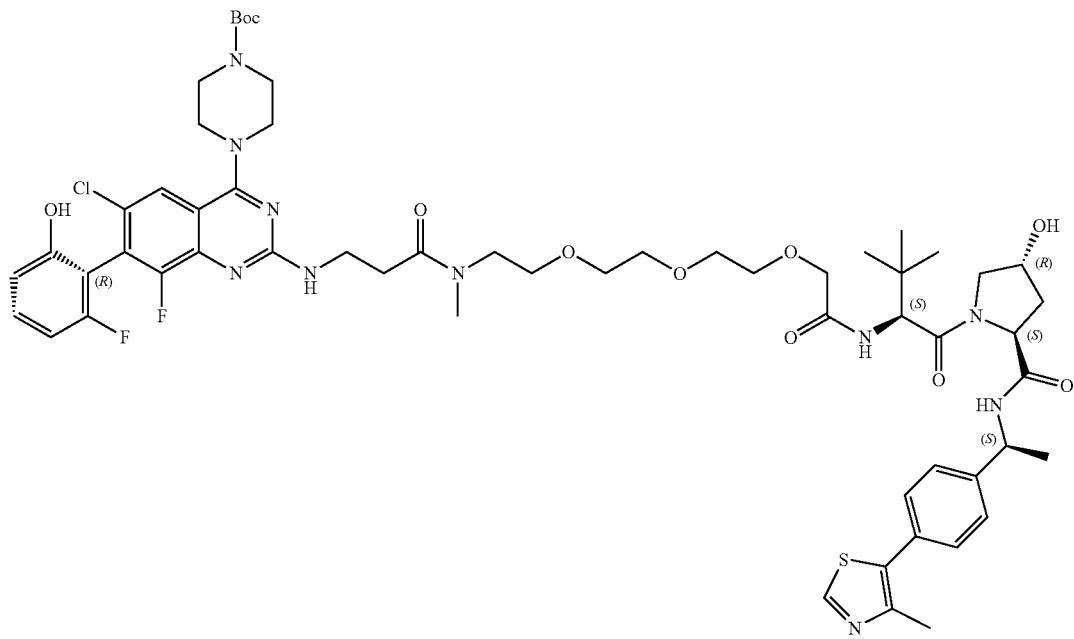

To a mixture of (2S,4R)-1-[(2S)-3,3-dimethyl-2-[[2-[2-[2-[2-(methylamino)ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (146 mg, 0.21 mmol, 1.2 eq, hydrochloride) and 3-[[4-(4-tert-butoxycarbonylpiperazin-1-yl)-6-chloro-8-fluoro-7-(2-fluoro-6-hydroxy-phenyl)quinazolin-2-yl]amino]propanoic acid (100 mg, 0.18 mmol, 1 eq) in N,N-dimethylformamide (8 mL) was added 1-hydroxybenzotriazole (36 mg, 0.27 mmol, 1.5 eq), 1-(3-dimethylaminopropyl)-3-ethylcarbodiimide hydrochloride (51 mg, 0.27 mmol, 1.5 eq) and N,N-diisopropylethylamine (69 mg, 0.53 mmol, 0.1 mL, 3 eq). The mixture was stirred at 15° C. for 16 hours. The reaction mixture was quenched by water (20 mL) and then diluted with dichloromethane (50 mL) and extracted with dichloromethane (50 mL×2). The combined organic layers were washed with brine (30 mL), dried over, filtered and concentrated under reduced pressure to give a residue. The residue was purified by prep-TLC (dichloromethane:methanol=10:1) to give tert-butyl-4-[6-chloro-8-fluoro-7-(2-fluoro-6-hydroxy-phenyl)-2-[[3-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethyl-methyl-amino]-3-oxo-propyl]amino]quinazolin-4-yl]piperazine-1-carboxylate (150 mg, 0.13 mmol, 71% yield) as a yellow oil. LC/MS (ESI) m/z: 1193.2 [M+1]⁺.

Step 2: Preparation of (2S,4R)-1-((S)-2-(tert-butyl)-18-((6-chloro-8-fluoro-7-((R)-2-fluoro-6-hydroxyphenyl)-4-(piperazin-1-yl)quinazolin-2-yl)amino)-15-methyl-4,16-dioxo-6,9,12-trioxa-3,15-diazaoctadecanoyl)-4-hydroxy-N—((S)-1-(4-(4-methylthiazol-5-yl)phenyl)ethyl)pyrrolidine-2-carboxamide

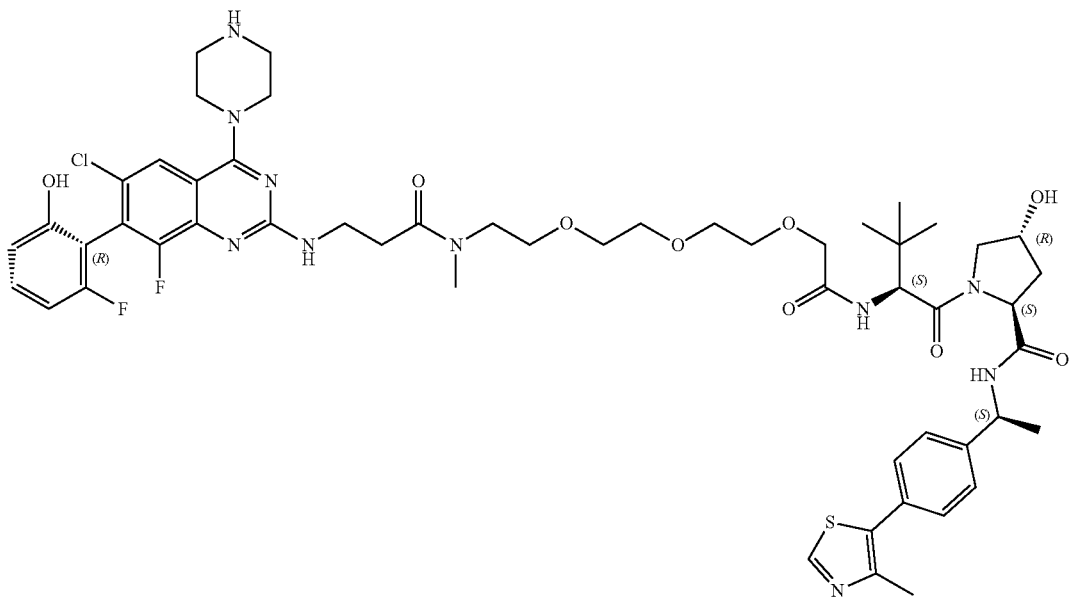

To a solution of tert-butyl-4-[6-chloro-8-fluoro-7-(2-fluoro-6-hydroxy-phenyl)-2-[[3-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethyl-methyl-amino]-3-oxo-propyl]amino]quinazolin-4-yl]piperazine-1-carboxylate (150 mg, 0.13 mmol, 1 eq) in dichloromethane (8 mL) was added trifluoroacetic acid (3.08 g, 26.97 mmol, 2.00 mL, 215 eq). The mixture was stirred at 15° C. for 20 minutes. The mixture was concentrated to give (2S,4R)-1-[(2S)-2-[[2-[2-[2-[2-[3-[[6-chloro-8-fluoro-7-(2-fluoro-6-hydroxy-phenyl)-4-piperazin-1-yl-quinazolin-2-yl]amino]propanoyl-methyl-amino]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (150 mg, 0.12 mmol, 99% yield, trifluoroacetate) as a yellow oil. LC/MS (ESI) m/z: 1093.1 [M+1].

Step 3: Preparation of (2S,4R)-1-((S)-18-((4-(4-acryloylpiperazin-1-yl)-6-chloro-8-fluoro-7-((R)-2-fluoro-6-hydroxyphenyl)quinazolin-2-yl)amino)-2-(tert-butyl)-15-methyl-4,16-dioxo-6,9,12-trioxa-3,15-diazaoctadecanoyl)-4-hydroxy-N—((S)-1-(4-(4-methylthiazol-5-yl)phenyl)ethyl)pyrrolidine-2-carboxamide

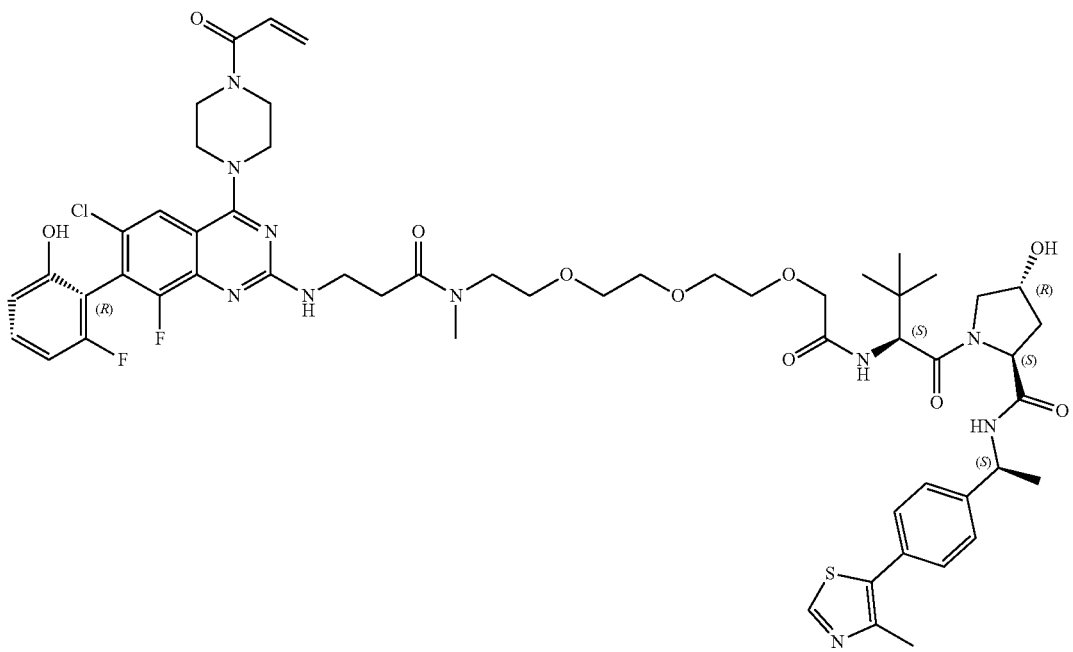

To a solution of (2S,4R)-1-[(2S)-2-[[2-[2-[2-[2-[3-[[6-chloro-8-fluoro-7-(2-fluoro-6-hydroxy-phenyl)-4-piperazin-1-yl-quinazolin-2-yl]amino]propanoyl-methyl-amino]ethoxy]ethoxy]ethoxy]acetyl]amino]-3,3-dimethyl-butanoyl]-4-hydroxy-N—[(S)-1-[4-(4-methylthiazol-5-yl)phenyl]ethyl]pyrrolidine-2-carboxamide (76 mg, 0.06 mmol, 1 eq, trifluoroacetate) and 2,6-lutidine (67 mg, 0.63 mmol, 10 eq) in dichloromethane (10 mL) was added prop-2-enoyl chloride (5 mg, 0.06 mmol, 0.9 eq) dropwise at −70° C. for 10 minutes. The reaction mixture was quenched by water (20 mL) and then diluted with dichloromethane (50 mL) and extracted with dichloromethane (50 mL×2). The combined organic layers were washed with brine (30 mL), dried over, filtered and concentrated under reduced pressure to give a residue. The residue was purified by semi-preparative reverse phase HPLC to give (2S,4R)-1-[(2S)-2-[[2-[2-[2-[2-[3-[[6-chloro-8-fluoro-7-(2-fluoro-6-hydroxy-phenyl)-4-(4-prop-2-enoylpiperazin-1-yl)quinazolin-2-yl]amino]propanoyl-methyl-amino]ethoxy]thoxy]ethoxy]acetyl]amino]-3,3-dimethyl-butanoyl]-4-hydroxy-N-[(1S)—[4-(4-methylthiazol-5-yl)phenyl]ethyl] pyrrolidine-2-carboxamide (30 mg, 0.03 mmol, 42% yield, 100% purity) as a white solid. LC/MS (ESI) m/z: 1147.3 [M+I]$^+$; $^1$H-NMR (400 MHz, DMSO-d$_6$) δ 10.22 (br s, 1H), 8.98 (s, 1H), 8.45 (br d, J=7.8 Hz, 1H), 7.72 (s, 1H), 7.55-6.99 (m, 7H), 6.92-6.68 (m, 3H), 6.17 (dd, J=2.4, 16.7 Hz, 1H), 5.79-5.63 (m, 1H), 5.14 (br s, 1H), 4.89 (br t, J=6.4 Hz, 1H), 4.54 (d, J=9.4 Hz, 1H), 4.44 (t, J=8.0 Hz, 1H), 4.28 (br s, 1H), 3.99-3.90 (m, 2H), 3.80-3.49 (m, 24H), 3.06-2.82 (m, 3H), 2.75-2.58 (m, 2H), 2.45 (s, 3H), 2.04 (br d, J=8.0 Hz, 1H), 1.81-1.72 (m, 1H), 1.48-1.32 (m, 3H), 0.93 (br d, J=2.4 Hz, 9H).

Exemplary Synthesis of (2S,4R)-1-((S)-21-(((S)-4-(4-acryloylpiperazin-1-yl)-6-chloro-8-fluoro-7-(2-fluoro-6-hydroxyphenyl)quinazolin-2-yl)amino)-2-(tert-butyl)-18-methyl-4,19-dioxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide (Exemplary Compound 211)

Step 1: Preparation of tert-butyl 4-((S)-6-chloro-8-fluoro-7-(2-fluoro-6-hydroxyphenyl)-2-(((S)-20-((2S,4R)-4-hydroxy-2-(((S)-1-(4-(4-methylthiazol-5-yl)phenyl)ethyl)carbamoyl)pyrrolidine-1-carbonyl)-4,21,21-trimethyl-3,18-dioxo-7,10,13,16-tetraoxa-4,19-diazadocosyl)amino)quinazolin-4-yl)piperazine-1-carboxylate

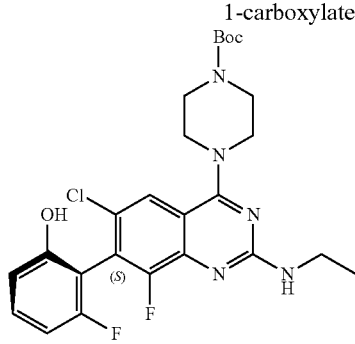
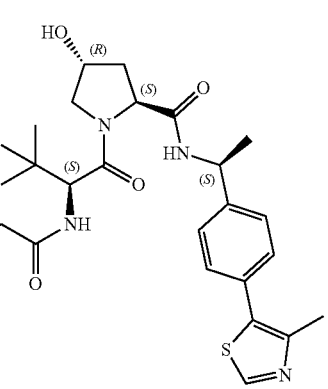

A mixture of (2S,4R)-1-[(2S)-3,3-dimethyl-2-[[2-[2-[2-[2-[2-(methylamino)ethoxy]ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (150 mg, 0.20 mmol, 1 eq, hydrochloride) and 3-[[4-(4-tert-butoxycarbonylpiperazin-1-yl)-6-chloro-8-fluoro-7-(2-fluoro-6-hydroxy-phenyl)quinazolin-2-yl]amino]propanoic acid (129 mg, 0.20 mmol, 1 eq) in N,N-dimethylformamide (8 mL) was added 1-hydroxybenzotriazole (41 mg, 0.30 mmol, 1.5 eq), N-(3-dimethylaminopropyl)-N-ethylcarbodiimide hydrochloride (59 mg, 0.30 mmol, 1.5 eq) and N,N-diisopropylethylamine (79 mg, 0.61 mmol, 0.10 mL, 3 eq). The mixture was stirred at 20° C. for 12 hours. The mixture was diluted with water (25 mL). Then it was extracted with ethyl acetate (20 mL×3). The combined organic layer was washed with water (30 mL×2) and brine (30 mL×2), dried over anhydrous sodium sulfate, filtered and concentrated under reduced pressure to give a residue. The residue was purified by prep-TLC (dichloromethane:methanol=10:1). Compound tert-butyl 4-[6-chloro-8-fluoro-7-(2-fluoro-6-hydroxy-phenyl)-2-[[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino]-3-oxo-propyl]amino]quinazolin-4-yl]piperazine-1-carboxylate (150 mg, 0.12 mmol, 58% yield) was obtained as a light yellow oil. LC/MS (ESI) m/z: 1237.6 [M+1]⁺.

Step 2: Preparation of (2S,4R)-1-((S)-2-(tert-butyl)-21-(((S)-6-chloro-8-fluoro-7-(2-fluoro-6-hydroxyphenyl)-4-(piperazin-1-yl)quinazolin-2-yl)amino)-18-methyl-4,19-dioxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide

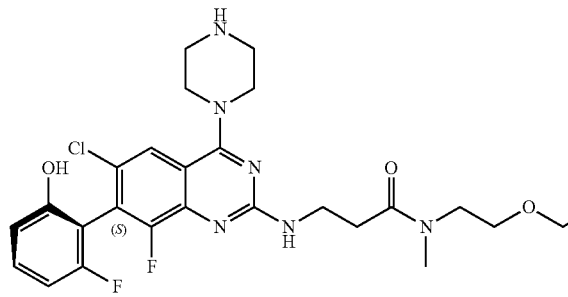
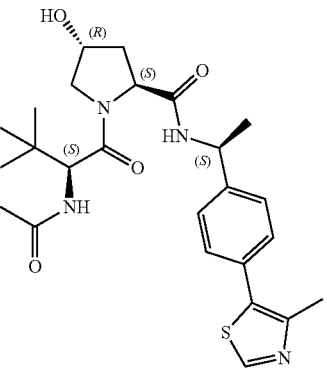

To a mixture of tert-butyl 4-[6-chloro-8-fluoro-7-(2-fluoro-6-hydroxy-phenyl)-2-[[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethyl-methyl-amino]-3-oxo-propyl]amino]quinazolin-4-yl]piperazine-1-carboxylate (150 mg, 0.12 mmol, 1 eq) in dichloromethane (4 mL) was added trifluoroacetic acid (1 mL). The mixture was stirred at 20° C. for 1 hour. The mixture was concentrated under reduced pressure to give (2S,4R)-1-[(2S)-2-[[2-[2-[2-[2-[2-[3-[[6-chloro-8-fluoro-7-(2-fluoro-6-hydroxy-phenyl)-4-piperazin-1-yl-quinazolin-2-yl]amino]propanoyl-methyl-amino]ethoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (150 mg, trifluoroacetate) as a light yellow oil. LC/MS (ESI) m/z: 1237.6 [M+I]⁺.

Step 3: Preparation of (2S,4R)-1-((S)-21-(((S)-4-(4-acryloylpiperazin-1-yl)-6-chloro-8-fluoro-7-(2-fluoro-6-hydroxyphenyl)quinazolin-2-yl)amino)-2-(tert-butyl)-18-methyl-4,19-dioxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide

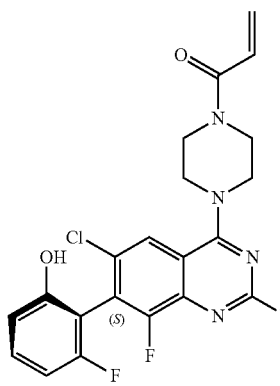
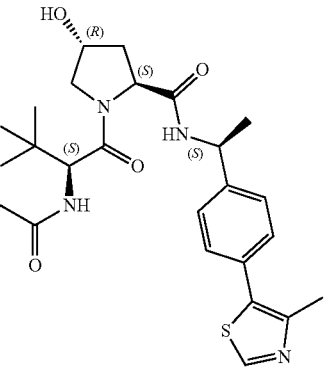

To the mixture of (2S,4R)-1-[(2S)-2-[[2-[2-[2-[2-[2-[3-[[6-chloro-8-fluoro-7-(2-fluoro-6-hydroxy-phenyl)-4-piperazin-1-yl-quinazolin-2-yl]amino]propanoyl-methyl-amino]ethoxy]ethoxy]ethoxy]ethoxy]acetyl]amino]-3,3-dimethyl-butanoyl]-4-hydroxy-N— [(S)-1-[4-(4-methylthiazol-5-yl)phenyl]ethyl]pyrrolidine-2-carboxamide (75 mg, 0.06 mmol, 1 eq, trifluoroacetate) and 2,6-lutidine (64 mg, 0.60 mmol, 0.07 mL, 10 eq) in dichloromethane (20 mL) was added prop-2-enoyl chloride (5 mg, 0.06 mmol, 1 eq) in dichloromethane (5 mL) drop-wise at −75° C. under nitrogen atmosphere. Then it was stirred at −75° C. for 20 minutes. The mixture was quenched with water (20 mL). Then it was extracted with dichloromethane (20 mL×3). The combined organic layer was washed with brine (30 mL×2), dried over anhydrous sodium sulfate, filtered and concentrated under reduced pressure to give a residue. The residue was purified by semi-preparative reverse phase HPLC. (2S,4R)-1-[(2S)-2-[[2-[2-[2-[2-[2-[3-[[6-chloro-8-fluoro-7-(2-fluoro-6-hydroxy-phenyl)-4-(4-prop-2-enoylpiperazin-1-yl)quinazolin-2-yl]amino]propanoyl-methyl-amino]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (29.8 mg, 0.02 mmol, 39% yield, 98% purity, formate) was obtained as a white solid. LC/MS (ESI) m/z: 1213.3 [M+23]⁺; ¹H-NMR (400 MHz, CD₃OD) δ 8.87 (s, 1H), 8.27 (s, 1H), 7.77 (s, 1H), 7.43-7.35 (m, 4H), 7.32-7.27 (m, 1H), 6.84-6.68 (m, 3H), 6.29-6.24 (m, 1H), 5.81-5.78 (m, 1H), 5.01-4.98 (m, 1H), 4.69-4.66 (m, 1H), 4.60-4.55 (m, 1H), 4.11-3.98 (m, 2H), 3.90-3.82 (m, 7H), 3.75-3.72 (m, 4H), 3.66-3.51 (m, 17H), 3.15 (s, 1H), 2.96-2.94 (m, 2H), 2.86-2.83 (m, 1H), 2.78-2.74 (m, 1H), 2.47 (s, 3H), 2.23-2.17 (m, 1H), 2.01-1.92 (m, 1H), 1.56-1.48 (m, 3H), 1.03-1.02 (m, 9H).

Exemplary Synthesis of (2S,4R)-1-((2S)-2-(tert-butyl)-14-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide (Exemplary Compound 246)

Step 1: Preparation of tert-butyl 4-((11-oxo-3,6,9,12-tetraoxatetradecyl)oxy)piperidine-1-carboxylate

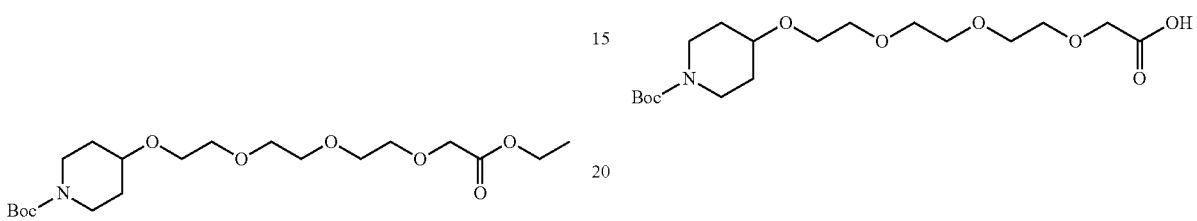

A solution of tert-butyl 4-(2-(2-(2-hydroxyethoxy)ethoxy)ethoxy)piperidine-1-carboxylate (1.38 g, 4.14 mmol, 1.00 eq) and dirhodium(II) tetraacetate (183 mg, 0.41 mmol, 0.10 eq) in dichloromethane (15 mL) was cooled to 0° C., then ethyl 2-diazoacetate (2.83 g, 24.84 mmol, 6.00 eq) was added dropwise. Then the mixture was stirred at 20° C. for 8 hours. The reaction mixture was diluted with water (20 mL), then extracted with ethyl acetate (20 mL×2). The combined organic layers were dried over anhydrous sodium sulfate, filtered and concentrated under reduced pressure to give a residue. The residue was purified by silica gel column chromatography (petroleum ether/ethyl acetate=5/1 to 1/1) to give desired product. Compound tert-butyl 4-((11-oxo-3,6,9,12-tetraoxatetradecyl)oxy)piperidine-1-carboxylate (1.36 g, 3.24 mmol, 78% yield) was obtained as a yellow oil. LC/MS (ESI) m/z: 320.0 [M−99]⁺; ¹H-NMR (400 MHz, CDCl₃) δ 4.21 (q, J=7.2 Hz, 2H), 4.15 (s, 2H), 3.74-3.62 (m, 14H), 3.49-3.46 (m, 1H), 3.08-3.05 (m, 2H), 1.83 (d, J=8.8 Hz, 2H), 1.53-1.49 (m, 2H), 1.45 (s, 9H), 1.29 (t, J=7.2 Hz, 3H).

Step 2: Preparation of 2-(2-(2-(2-((1-(tert-butoxycarbonyl)piperidin-4-yl)oxy)ethoxy)ethoxy)ethoxy)acetic acid To a solution of tert-butyl 4-((11-oxo-3,6,9,12-tetraoxatetradecyl)oxy)piperidine-1-carboxylate (600 mg, 1.43 mmol, 1.00 eq) in a mixture of tetrahydrofuran (5 mL) and water (2 mL) was added lithium hydroxide hydrate (150 mg, 3.58 mmol, 2.50 eq). The mixture was stirred at 20° C. for 0.5 hour. The reaction mixture was concentrated under reduced pressure to give a residue. The residue was acidified to pH=3 with hydrochloric acid (1 M), then extracted with ethyl acetate (20 mL×2). The combined organic layers were dried over anhydrous sodium sulfate, filtered and concentrated under reduced pressure to give a residue. Compound 2-(2-(2-(2-((1-(tert-butoxycarbonyl)piperidin-4-yl)oxy)ethoxy) ethoxy)ethoxy)acetic acid (550 mg) was obtained as a colorless oil. ¹H-NMR (400 MHz, CDCl₃) δ 4.15 (s, 2H), 3.82-3.63 (m, 14H), 3.56-3.44 (m, 1H), 3.11-2.95 (m, 2H), 1.91-1.80 (m, 2H), 1.58-1.48 (m, 2H), 1.45 (s, 9H).

Step 3: Preparation of tert-butyl 4-(((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)oxy)piperidine-1-carboxylate

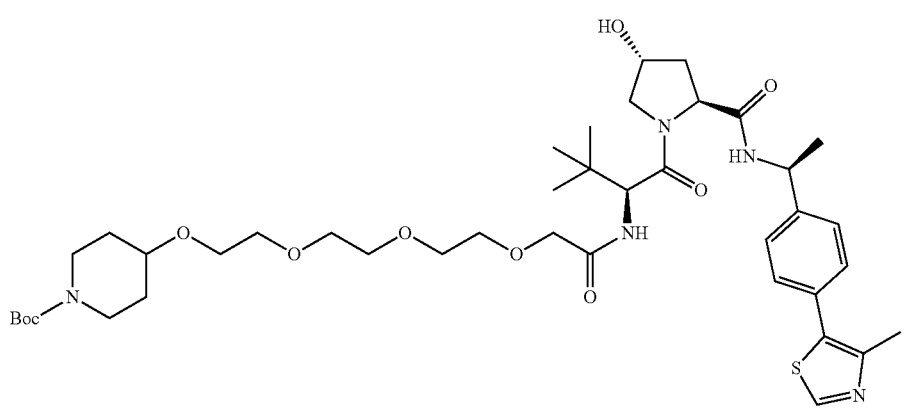 [SMILES: Cc1ncsc1-c1ccc([C@H](C)NC(=O)[C@@H]2C[C@@H](O)CN2C(=O)[C@@H](NC(=O)COCCOCCOCCOC2CCN(C(=O)OC(C)(C)C)CC2)C(C)(C)C)cc1]

To a solution of 2-(2-(2-(2-((1-(tert-butoxycarbonyl)piperidin-4-yl)oxy)ethoxy) ethoxy)ethoxy)acetic acid (250 mg, 0.64 mmol, 1.00 eq) and (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (369 mg, 0.77 mmol, 1.20 eq, hydrochloride salt) in dichloromethane (10 mL) were added 1-(3-dimethylaminopropyl)-3-ethylcarbodiimide hydrochloride (184 mg, 0.96 mmol, 1.50 eq) and hydroxybenzotriazole (129 mg, 0.96 mmol, 1.50 eq) and diisopropylethylamine (248 mg, 1.92 mmol, 3.00 eq). The reaction mixture was stirred at 25° C. for 10 hours. The reaction mixture was diluted with water (20 mL), acidified to pH=3 with hydrochloric acid (1 M), then extracted with dichloromethane (20 mL×2). The combined organic layers were washed with saturated sodium bicarbonate solution (20 mL), dried over sodium sulfate, filtered and concentrated. The residue was purified by silica gel column chromatography (ethyl acetate/methanol=1/0 to 10/1) to give desired product. Compound tert-butyl 4-(((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)oxy)piperidine-1-carboxylate (427 mg, 0.52 mmol, 82% yield) was obtained as colorless oil. LC/MS (ESI) m/z: 818.4 [M+1]$^+$; $^1$H-NMR (400 MHz, CDCl$_3$) δ 8.68 (s, 1H), 7.52-7.31 (m, 6H), 5.30 (s, 1H), 5.16-5.02 (m, 1H), 4.75 (t, J=7.6 Hz, 1H), 4.59-4.46 (m, 2H), 4.15-4.09 (m, 1H), 3.87-3.55 (m, 15H), 3.52-3.43 (m, 1H), 3.28 (s, 1H), 3.12-2.98 (m, 2H), 2.61-2.49 (m, 4H), 2.11-2.05 (m, 1H), 1.89-1.78 (m, 5H), 1.51-1.42 (m, 12H), 1.07 (s, 9H).

Step 4: Preparation of (2S,4R)-1-((S)-2-(tert-butyl)-4-oxo-14-(piperidin-4-yloxy)-6,9,12-trioxa-3-azatetradecanoyl)-4-hydroxy-N—((S)-1-(4-(4-methylthiazol-5-yl)phenyl)ethyl)pyrrolidine-2-carboxamide

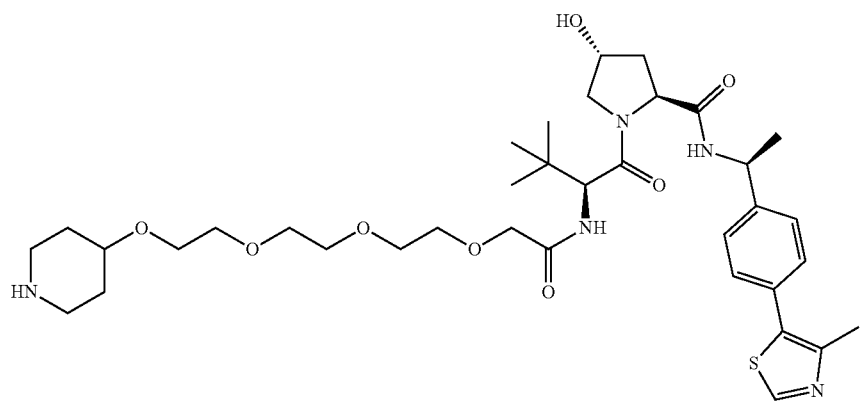 [SMILES: Cc1ncsc1-c1ccc([C@H](C)NC(=O)[C@@H]2C[C@@H](O)CN2C(=O)[C@@H](NC(=O)COCCOCCOCCOC2CCNCC2)C(C)(C)C)cc1]

To a solution of tert-butyl 4-(((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)oxy)piperidine-1-carboxylate (427 mg, 0.52 mmol, 1.00 eq) in dichloromethane (2 mL) was added hydrogen chloride/dioxane (4.0 M, 3.0 mL, 22.99 eq). The mixture was stirred at 25° C. for 0.5 hour. The reaction mixture was concentrated under reduced pressure to give a residue. Compound (2S,4R)-1-((S)-2-(tert-butyl)-4-oxo-14-(piperidin-4-yloxy)-6,9,12-trioxa-3-azatetradecan-1-oyl)-4-hydroxy-N—((S)-1-(4-(4-methylthiazol-5-yl)phenyl)ethyl)pyrrolidine-2-carboxamide (400 mg, hydrochloride salt) was obtained as a white solid. LC/MS (ESI) m/z: 718.4 [M+1]$^+$.

Step 5: Preparation of tert-butyl 4-(6-chloro-8-fluoro-2-(((R)-1-(4-(((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)oxy)piperidin-1-yl)propan-2-yl)oxy)-7-(3-hydroxynaphthalen-1-yl)quinazolin-4-yl)piperazine-1-carboxylate

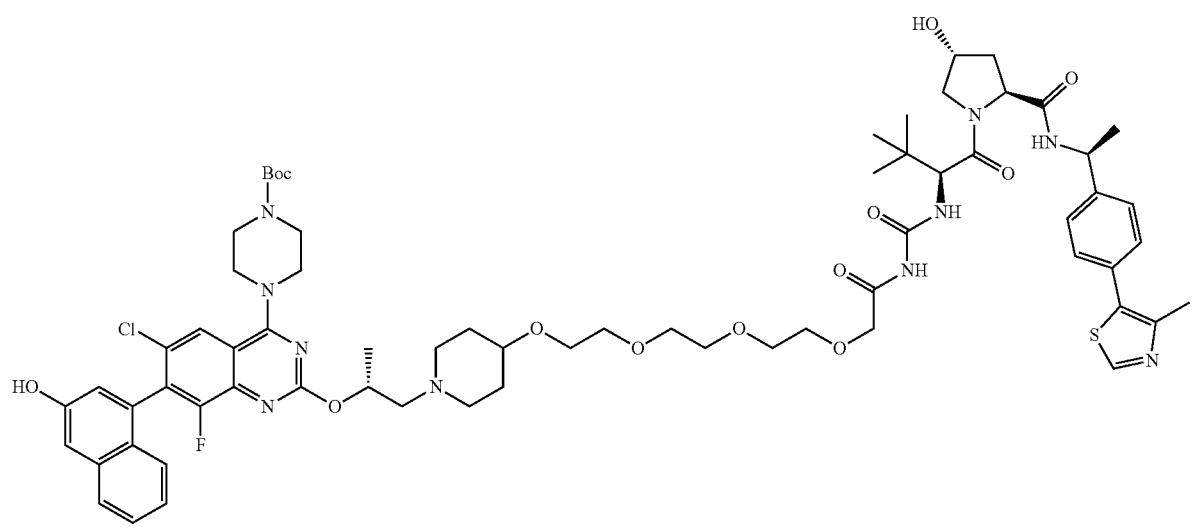 [SMILES: Cc1ncsc1-c1ccc([C@H](C)NC(=O)[C@@H]2C[C@@H](O)CN2C(=O)[C@@H](NC(=O)NC(=O)COCCOCCOCCOC2CCN(C[C@@H](C)Oc3nc(N4CCN(C(=O)OC(C)(C)C)CC4)c4cc(Cl)c(-c5cc(O)cc6ccccc56)c(F)c4n3)CC2)C(C)(C)C)cc1]

To a mixture of (2S,4R)-1-[(2S)-3,3-dimethyl-2-[[2-[2-[2-[2-(4-piperidyloxy)ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (78 mg, 0.1 mmol, 1.2 eq, hydrochloride) in methanol (2 mL) was added sodium sulfate (28 mg, 0.34 mmol, 4 eq). The reaction mixture was stirred at 25° C. for 20 minutes. A solution of tert-butyl 4-[6-chloro-8-fluoro-7-(3-hydroxy-1-naphthyl)-2-[(1R)-1-methyl-2-oxo-ethoxy]quinazolin-4-yl]piperazine-1-carboxylate (50 mg, 0.09 mmol, 1 eq) in dichloromethane (2 mL) was added, follow by acetic acid (10 mg, 0.17 mmol, 2 eq). The reaction mixture was cooled to 0° C. and sodium cyanoborohydride (16 mg, 0.26 mmol, 3 eq) was added. The reaction mixture was stirred at 25° C. for 4 hours. Methanol (2 mL) was added to get the reaction mixture as a clear solution. The solution was purified by prep-TLC (10% methanol in dichloromethane) to get tert-butyl 4-[6-chloro-8-fluoro-2-[(1R)-2-[4-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]-1-piperidyl]-1-methyl-ethoxy]-7-(3-hydroxy-1-naphthyl)quinazolin-4-yl]piperazine-1-carboxylate (45 mg, 0.03 mmol, 38% yield, 94% purity) as a colorless gum. LC/MS (ESI) m/z: 1281.6 [M+1]$^+$.

Step 6: Preparation of (2S,4R)-1-((2S)-2-(tert-butyl)-14-((1-((2R)-2-((6-chloro-8-fluoro-7-(3-hydroxynaphthalen-1-yl)-4-(piperazin-1-yl)quinazolin-2-yl)oxy)propyl)piperidin-4-yl)oxy)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide

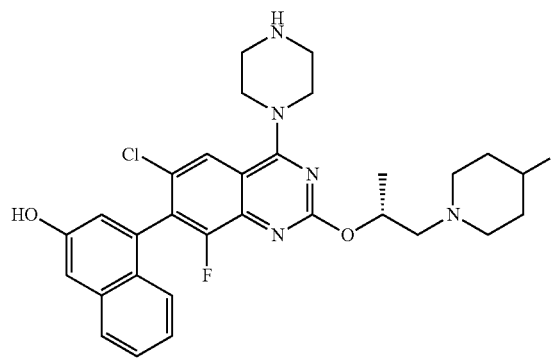
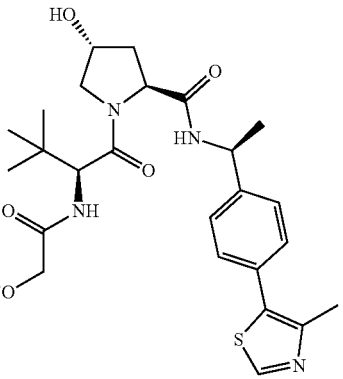

To a solution of tert-butyl 4-[6-chloro-8-fluoro-2-[(1R)-2-[4-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]-1-piperidyl]ethoxy]-1-methyl-ethoxy]-7-(3-hydroxy-1-naphthyl)quinazolin-4-yl]piperazine-1-carboxylate (45 mg, 0.03 mmol, 1 eq) in dichloromethane (2 mL) was added trifluoroacetic acid (308 mg, 2.70 mmol, 0.2 mL, 77.01 eq). The reaction mixture was stirred at 25° C. for 1 hour. The reaction solution was concentrated under vacuum to get (2S,4R)-1-[(2S)-2-[[2-[2-[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (45 mg, 0.03 m mol, 98% yield, trifluoroacetate) as a colorless gum.

Step 7: Preparation of (2S,4R)-1-((2S)-2-(tert-butyl)-14-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide

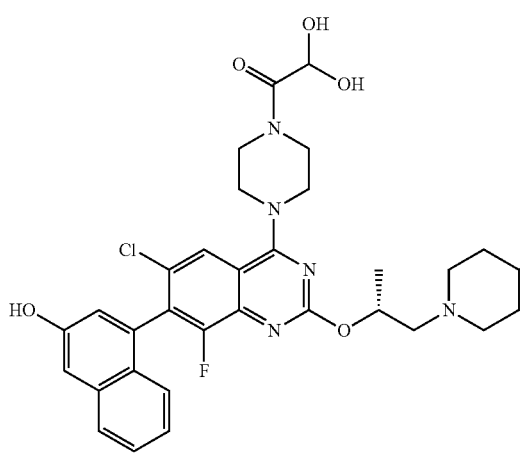
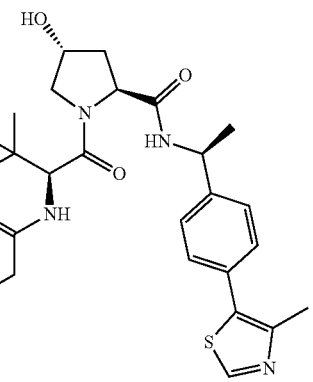

To the mixture of (2S,4R)-1-[(2S)-2-[[2-[2-[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (85 mg, 0.07 mmol, 1 eq, hydrochloride) and 2,2-dihydroxyacetic acid (65 mg, 0.7 mmol, 10 eq) in N,N-dimethylformamide (3 mL) was added O-(7-Azabenzotriazol-1-yl)-N,N,N',N'-tetramethyluronium exafluorophosphate (80 mg, 0.21 mmol, 3 eq) and N,N-diisopropylethylamine (90 mg, 0.7 mmol, 0.1 mL, 10 eq). The mixture was stirred at 25° C. for 12 hours. The mixture was filtered. The filtrate was purified by prep-HPLC. Compound (2S,4R)-1-[(2S)-2-[[2-[2-[2-[2-[[1-[(2R)-2-[6-chloro-4-[4-(2,2-dihydroxyacetyl)piperazin-1-yl]-8-fluoro-7-(3-hydroxy-1-naphthyl)quinazolin-2-yl]oxypropyl]-4-piperidyl]oxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (17.5 mg, 0.01 mmol, 19% yield, 97.8% purity, formate) was obtained as a white solid. LC/MS (ESI) m/z: 1256.4 [M+1]$^+$; $^1$H-NMR (400 MHz, DMSO-d$_6$) δ 10.04 (s, 1H), 8.97 (s, 1H), 8.43-8.41 (d, J=8.0 Hz, 1H), 8.18 (s, 1H), 8.00 (s, 1H), 7.81-7.79 (d, J=8.0 Hz, 1H), 7.58-7.26 (m, 7H), 7.24-7.14 (m, 2H), 7.09-7.01 (m, 1H), 6.43-6.30 (m, 1H), 5.52-5.03 (m, 2H), 4.95-4.80 (m, 1H), 4.71-4.34 (m, 2H), 4.27 (s, 1H), 4.00-3.78 (m, 8H), 3.75-3.66 (m, 2H), 3.63-3.49 (m, 12H), 3.23-3.18 (m, 3H), 2.90-2.74 (m, 2H), 2.44 (s, 4H), 2.18-1.98 (m, 5H), 1.81-1.66 (m, 3H), 1.40-1.18 (m, 8H), 0.92 (s, 9H).

Exemplary Synthesis of (2S,4R)-1-((S)-2-((E)-19-(3-(4-((4-chloro-2-hydroxy-5-(1-methylcyclopropyl)phenyl)glycyl)piperazin-1-yl)azetidin-1-yl)-19-oxo-3,6,9,12,15-pentaoxanonadec-17-enamido)-3,3-dimethylbutanoyl)-4-hydroxy-N-(4-(4-methylthiazol-5-yl)benzyl)pyrrolidine-2-carboxamide (Exemplary Compound 251)

Step 1: Preparation of tert-butyl 17-hydroxy-3,6,9,12,15-pentaoxaheptadecanoate

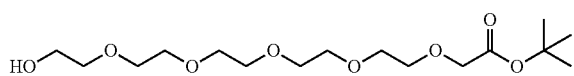 [SMILES: CC(C)(C)OC(=O)COCCOCCOCCOCCOCCO]

To a cold and stirred solution of 3,6,9,12-tetraoxatetradecane-1,14-diol (3 eq) in anhydrous N,N-dimethylformamide was added sodium hydride (60%, 1.2 eq) in portions at 0° C. under nitrogen atmosphere. The reaction mixture was allowed to warm to rt and stirred at room temperature for 1 hour, then re-cooled to 0° C., tert-butyl 2-bromoacetate (1 eq) was added in portions, the resulting mixture was allowed to warm up to room temperature and stirred at room temperature for 2 hours. The reaction was carefully quenched with water under ice-water cooling and extracted with methylene dichloride. The combined organic phase was washed with brine, dried over anhydrous magnesium sulfate and evaporated to dryness under reduced pressure. The crude product was purified by silica gel chromatography (eluent 1-6% methanol in methylene dichloride) to afford the desired product, Tert-butyl 17-hydroxy-3,6,9,12,15-pentaoxaheptadecan-1-oate as light yellow oil, yield 29%. $^1$H-NMR (400 MHz, CDCl$_3$) δ 1.48 (s, 9H), 3.60-3.73 (m, 20H), 4.02 (s, 2H).

Step 2: Preparation of tert-butyl 17-oxo-3,6,9,12,15-pentaoxaheptadecanoate

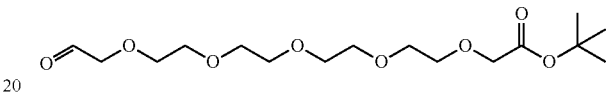

To a solution of tert-butyl 17-hydroxy-3,6,9,12,15-pentaoxaheptadecanoate (1 g, 3.52 mmol) in CH$_3$CN (30 mL) was added IBX (1.4 g, 4.87 mmol). The solution was stirred and heated to reflux for 5 hours under N$_2$. The reaction mixture was cooled to room temperature, and then filtered through Celite. The filtrate was concentrated under reduced pressure. The residue was purified by silica gel column chromatography (PE/EA=5/1 to EA) to afford the title compound (875 mg, 2.5 mmol, 71% yield).

Step 2: Preparation of 1-(tert-butyl) 19-methyl (E)-3,6,9,12,15-pentaoxanonadec-17-enedioate

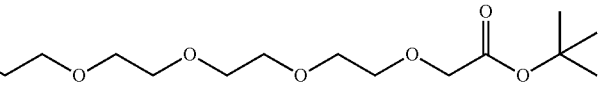

To a solution of tert-butyl 17-oxo-3,6,9,12,15-pentaoxaheptadecanoate (875 mg, 2.5 mmol) and methyl 2-(dimethoxyphosphoryl)acetate (844 mg, 4.64 mmol) in THF (10 mL) was added DBU (1.1 g, 6.96 mmol). The solution was stirred at room temperature for 5 hours under N$_2$. The reaction mixture was quenched with water (20 mL). The organic phase was washed with brine. The organic layer was dried over Na$_2$SO$_4$, filtered and concentrated under reduced pressure. The residue was purified by silica gel column chromatography (PE/EA from 30/1 to 1/1) to afford the title compound (224 mg, 0.55 mmol, 22% yield).

Step 3: Preparation of (E)-3-oxo-2,7,10,13,16,19-hexaoxahenicos-4-en-21-oic acid

To a solution of 1-(tert-butyl) 19-methyl (E)-3,6,9,12,15-pentaoxanonadec-17-enedioate (224 mg, 0.55 mmol) in DCM (5 mL) was added TFA (1 mL). The mixture was stirred at room temperature for 1 hour. The solution was concentrated under reduced pressure to afford the product (E)-3-oxo-2,7,10,13,16,19-hexaoxahenicos-4-en-21-oic acid (240 mg).

Step 4: Preparation of methyl (S,E)-3-((2S,4R)-4-hydroxy-2-((4-(4-methylthiazol-5-yl)benzyl)carbamoyl)pyrrolidine-1-carbonyl)-2,2-dimethyl-5-oxo-7,10,13,16,19-pentaoxa-4-azatricos-21-en-23-oate

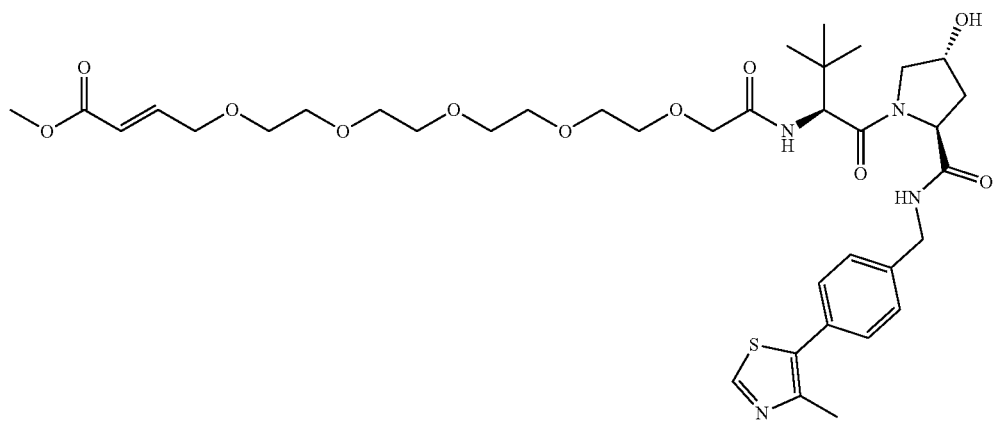 [SMILES: COC(=O)/C=C/COCCOCCOCCOCCOCC(=O)N[C@H](C(=O)N1C[C@H](O)C[C@H]1C(=O)NCc1ccc(-c2scnc2C)cc1)C(C)(C)C]

To a solution of (E)-3-oxo-2,7,10,13,16,19-hexaoxahenicos-4-en-21-oic acid (240 mg) in DCM (10 mL) was added (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (257 mg, 0.55 mmol), TEA (154 mg, 1.52 mmol) and HATU (289 mg, 0.76 mmol). The mixture was stirred at room temperature for 1 hour. Then it was quenched with $H_2O$ (10 mL). The mixture was extracted with DCM. The combined organic layers were washed with brine. The organic phase was dried over $Na_2SO_4$, filtered and concentrated under reduced pressure. The residue was purified by silica gel column chromatography (DCM/MeOH=from 50/1 to 20/1) to afford methyl (S,E)-3-((2S,4R)-4-hydroxy-2-((4-(4-methylthiazol-5-yl)benzyl)carbamoyl)pyrrolidine-1-carbonyl)-2,2-dimethyl-5-oxo-7,10,13,16,19-pentaoxa-4-azatricos-21-en-23-oate (206 mg, 0.27 mmol).

Step 5: Preparation of methyl (S,E)-3-((2S,4R)-4-hydroxy-2-((4-(4-methylthiazol-5-yl)benzyl)carbamoyl)pyrrolidine-1-carbonyl)-2,2-dimethyl-5-oxo-7,10,13,16,19-pentaoxa-4-azatricos-21-en-23-oic acid

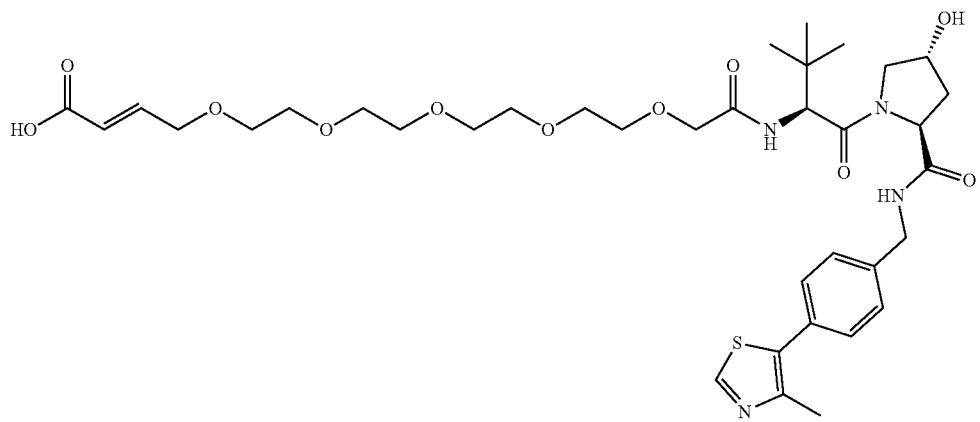 [SMILES: Cc1ncsc1-c1ccc(CNC(=O)[C@@H]2C[C@@H](O)CN2C(=O)[C@@H](NC(=O)COCCOCCOCCOCCOC/C=C/C(=O)O)C(C)(C)C)cc1]

To a solution of methyl (S,E)-3-((2S,4R)-4-hydroxy-2-((4-(4-methylthiazol-5-yl)benzyl)carbamoyl)pyrrolidine-1-carbonyl)-2,2-dimethyl-5-oxo-7,10,13,16,19-pentaoxa-4-azatricos-21-en-23-oate (206 mg, 0.27 mmol) in THF/water (5 mL/5 mL) was added NaOH (33 mg, 0.81 mmol). The mixture was stirred at room temperature for 1 hour. The pH of the mixture was adjusted to 9 with aq.HCl (1 M). The mixture was concentrated under reduced pressure to afford methyl (S,E)-3-((2S,4R)-4-hydroxy-2-((4-(4-methylthiazol-5-yl)benzyl)carbamoyl)pyrrolidine-1-carbonyl)-2,2-dimethyl-5-oxo-7,10,13,16,19-pentaoxa-4-azatricos-21-en-23-oic acid (220 mg).

Step 6: Preparation of (2S,4R)-1-((S)-2-((E)-19-(3-(4-((4-chloro-2-hydroxy-5-(1-methylcyclopropyl)phenyl)glycyl)piperazin-1-yl)azetidin-1-yl)-19-oxo-3,6,9,12,15-pentaoxanonadec-17-enamido)-3,3-dimethylbutanoyl)-4-hydroxy-N-(4-(4-methylthiazol-5-yl)benzyl)pyrrolidine-2-carboxamide

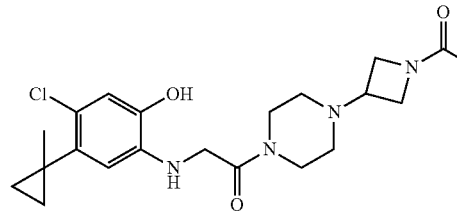

To a solution of methyl (S,E)-3-((2S,4R)-4-hydroxy-2-((4-(4-methylthiazol-5-yl)benzyl)carbamoyl)pyrrolidine-1-carbonyl)-2,2-dimethyl-5-oxo-7,10,13,16,19-pentaoxa-4-azatricos-21-en-23-oic acid (220 mg) in DMF (5 mL) were added 1-(4-(azetidin-3-yl)piperazin-1-yl)-2-((4-chloro-2-hydroxy-5-(1-methylcyclopropyl)phenyl)amino)ethan-1-one hydrochloride (116 mg, 0.28 mmol), TEA (84 mg, 0.84 mmol) and HATU (160 mg, 0.42 mmol) subsequently. The resulting mixture was stirred at room temperature for 30 minutes. It was quenched with $H_2O$ (10 mL) and extracted with Ethyl Acetate. The combined organic layers were washed with brine. The organic phase was dried over $Na_2SO_4$, filtered and concentrated under reduced pressure. The residue was purified by prep-HPLC to afford (2S,4R)-1-((S)-2-((E)-19-(3-(4-((4-chloro-2-hydroxy-5-(1-methylcyclopropyl)phenyl)glycyl)piperazin-1-yl)azetidin-1-yl)-19-oxo-3,6,9,12,15-pentaoxanonadec-17-enamido)-3,3-dimethylbutanoyl)-4-hydroxy-N-(4-(4-methylthiazol-5-yl)benzyl)pyrrolidine-2-carboxamide (15.5 mg, 0.014 mmol). $^1$H-NMR (400 MHz, $CD_3OD$) δ 8.87 (s, 1H), 8.25-8.26 (m, 1H), 7.41-7.47 (m, 4H), 6.78-6.84 (m, 1H), 6.65 (s, 1H), 6.36 (s, 1H), 6.23-6.29 (m, 1H), 5.36-5.41 (m, 1H), 4.69-4.71 (m, 1H), 4.50-4.59 (m, 3H), 4.29-4.38 (m, 2H), 4.18-4.20 (m, 2H), 4.05-4.14 (m, 4H), 3.96 (s, 2H), 3.78-3.91 (m, 3H), 3.60-3.70 (m, 20H), 3.24 (br, 1H), 2.48 (s, 3H), 2.37-2.45 (m, 4H), 2.20-2.25 (m, 1H), 2.05-2.12 (m, 1H), 1.90 (s, 3H), 1.71-1.72 (m, 3H), 1.04 (s, 9H).

Exemplary Synthesis of (2S,4R)-1-((2S)-2-(2-((5-(4-(6-chloro-2-((3-(dimethylamino)-3-oxopropyl)amino)-8-fluoro-7-(3-hydroxynaphthalen-1-yl)quinazolin-4-yl)piperazin-1-yl)-5-oxopentyl)oxy)acetamido)-3,3-dimethylbutanoyl)-4-hydroxy-N—((S)-1-(4-(4-methylthiazol-5-yl)phenyl)ethyl)pyrrolidine-2-carboxamide (Exemplary Compound 254)

Step 1: Preparation of tert-butyl 17-hydroxy-3,6,9,12,15-pentaoxaheptadecanoate

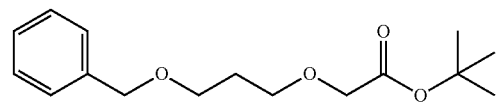 [SMILES: CC(C)(C)OC(=O)COCCCOCc1ccccc1]

Sodium hydroxide (10.67 g, 266.67 mmol, 11.08 eq) was dissolved in water (16 mL) and then added to a solution of 3-benzyloxypropan-1-ol (4 g, 24.07 mmol, 3.81 mL, 1 eq), tetra-n-butylammonium chloride (7.02 g, 25.27 mmol, 7.06 mL, 1.05 eq) in dichloromethane (20 mL). Then tert-butyl 2-bromoacetate (18.78 g, 96.26 mmol, 14.22 mL, 4 eq) was added. The resulting mixture was stirred at 20° C. for 16 hours. Water (80 mL) was added and the organic phase was separated. The aqueous was further extracted with dichloromethane (200 mL×2). The combined organic phase was washed with brine (80 mL×2), dried and concentrated. The residue was purified by silica gel chromatography (Petroleum ether/Ethyl acetate=I/O to 5/1) to give tert-butyl 2-(3-benzyloxypropoxy)acetate (1.0 g, 3.21 mmol, 13% yield, 90% purity) as a colorless oil and tert-butyl 2-(3-benzyloxypropoxy)acetate (6 g, 14.98 mmol, 62% yield, 70% purity) as a yellow oil.

Step 2: Preparation of tert-butyl 2-(3-hydroxypropoxy)acetate

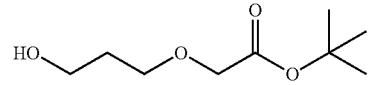

To a solution of tert-butyl 2-(3-benzyloxypropoxy)acetate (6 g, 14.98 mmol, 1 eq) in ethanol (10 mL) was added palladium on activated carbon catalyst (0.5 g 10% purity) and the mixture was degassed with hydrogen. The mixture was stirred at 15° C. for 16 hours under 15 PSI. The mixture was then stirred at 40° C. for 2 hours under 50 PSI. The mixture was filtered. The residue was purified by silica gel chromatography (Petroleum ether/Ethyl acetate=5/1 to 1/1) to give tert-butyl 2-(3-hydroxypropoxy)acetate (1.1 g, 5.78 mmol, 39% yield) as a colorless liquid. $^1$H-NMR (400 MHz, DMSO-$d_6$) δ 4.36 (t, J=5.2 Hz, 1H), 3.92 (s, 2H), 3.53-3.38 (m, 4H), 1.73-1.54 (m, 2H), 1.50-1.38 (s, 9H).

Step 3: Preparation of tert-butyl 2-(3-oxopropoxy)acetate

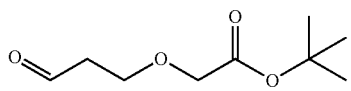

To a mixture of oxalyl chloride (1.20 g, 9.45 mmol, 0.83 mL, 3 eq) in dichloromethane (8 mL) was dropwised added dimethyl sulfoxide (984 mg, 12.60 mmol, 0.98 mL, 4 eq) in dichloromethane (4 mL) at −70° C. and stirred for 0.5 h at −70° C. tert-butyl 2-(3-hydroxypropoxy)acetate (600 mg, 3.15 mmol, 1 eq) in dichloromethane (4 mL) was added dropwise and stirred for −70° C. for 0.5 hour. Triethylamine (2.55 g, 25.20 mmol, 3.51 mL, 8 eq) was added dropwise to the reaction mixture. Then the reaction mixture was stirred at −70° C. for 1 hour and 20° C. for 1 hour. The reaction mixture was quenched by saturated ammonium chloride (20 mL), and then diluted with dichloromethane (50 mL) and extracted with dichloromethane (50 mL×2). The combined organic layers were washed with brine (30 mL), dried over, filtered and concentrated under reduced pressure to give tert-butyl 2-(3-oxopropoxy)acetate (500 mg, 2.66 mmol, 84.33% yield) as a yellow oil. $^1$H-NMR (400 MHz, DMSO-$d_6$) δ 9.67 (t, J=2.0 Hz, 1H), 8.75 (s, 1H), 4.05-3.91 (m, 2H), 3.78 (t, J=6.0 Hz, 2H), 2.62 (dt, J=2.0, 6.0 Hz, 2H), 1.45-1.42 (s, 9H).

Step 4: Preparation of methyl (E)-5-(2-(tert-butoxy)-2-oxoethoxy)pent-2-enoate

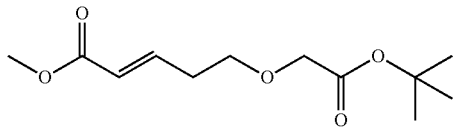 [SMILES: COC(=O)/C=C/CCOCC(=O)OC(C)(C)C]

To a solution of tert-butyl 2-(3-oxopropoxy)acetate (500 mg, 2.66 mmol, 1 eq) in dichloromethane (20 mL) was added methyl 2-(triphenyl-phosphanylidene)acetate (889 mg, 2.66 mmol, 1 eq). The mixture was stirred at 15° C. for 16 hours. The mixture was concentrated as a residue. The residue was purified by silica gel chromatography (Petroleum ether/Ethyl acetate=10/1 to 3/1) to give methyl (E)-5-(2-tert-butoxy-2-oxo-ethoxy)pent-2-enoate (350 mg, 1.43 mmol, 54% yield) as a yellow oil. $^1$H-NMR (400 MHz, DMSO-$d_6$) δ 6.91 (td, J=6.8, 15.6 Hz, 1H), 5.97 (td, J=1.6, 15.6 Hz, 1H), 4.06-3.89 (m, 2H), 3.65 (s, 3H), 3.60-3.50 (m, 2H), 2.45 (dq, J=1.6, 6.4 Hz, 2H), 1.43 (s, 9H).

Step 5: Preparation of (E)-2-((5-methoxy-5-oxo-pent-3-en-1-yl)oxy)acetic acid

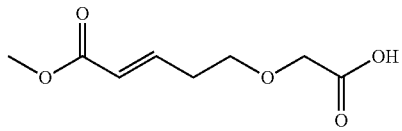

To a solution of methyl (E)-5-(2-tert-butoxy-2-oxo-ethoxy)pent-2-enoate (300 mg, 1.23 mmol, 1 eq) in dichloromethane (8 mL) was added trifluoroacetic acid (3.08 g, 27.01 mmol, 2 mL, 22 eq). The mixture was stirred at 15° C. for 1 hour. The mixture was concentrated to give 2-[(E)-5-methoxy-5-oxo-pent-3-enoxy]acetic acid (370 mg, 1.22 mmol, 99% yield, trifluoroacetate) as a yellow oil.

Step 6: Preparation of 2-((5-methoxy-5-oxopentyl)oxy)acetic acid

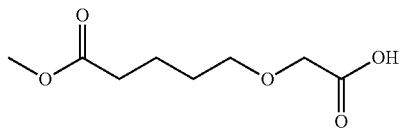

To a solution of 2-[(E)-5-methoxy-5-oxo-pent-3-enoxy] acetic acid (100 mg, 0.53 mmol, 1 eq) in methanol (5 mL) was added Palladium on activated carbon catalyst (0.05 g 10% purity) and the mixture was degassed with hydrogen. The whole mixture was stirred at 15° C. for 16 hours under 15 psi. The mixture was filtrated to get the filtrate. The filtrate was concentrated to give 2-(5-methoxy-5-oxo-pentoxy)acetic acid (140 mg) as a yellow oil.

Step 7: Preparation of methyl 5-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)pentanoate

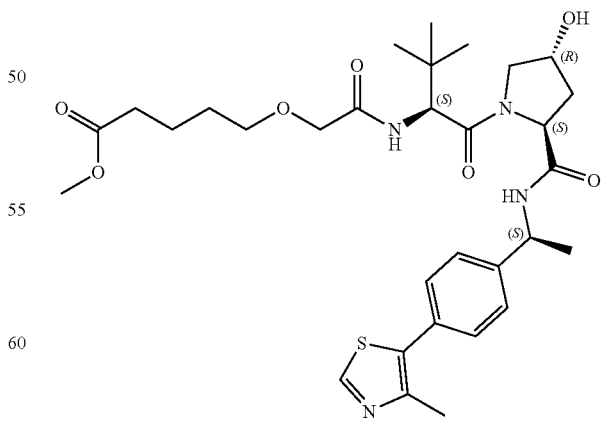

To a mixture of 2-(5-methoxy-5-oxo-pentoxy)acetic acid (140 mg, 0.74 mmol, 1 eq) and (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (327 mg, 0.74 mmol, 1 eq) in N,N-dimethylformamide (8 mL) was added N,N-diisopropylethylamine (285 mg, 2.21 mmol, 0.38 mL, 3 eq), 1-hydroxybenzotriazole (119 mg, 0.88 mmol, 1.2 eq) and 3-(ethyliminomethyleneamino)-N,N-dimethyl-propan-1-amine; hydrochloride (169 mg, 0.88 mmol, 1.2 eq). The mixture was stirred at 15° C. for 2 hours. The mixture was quenched by water (20 mL), the aqueous phase was extracted with ethyl acetate (50 mL×2). The combined organic phase was washed with brine (30 mL), dried with anhydrous sodium sulfate, filtered and concentrated under vacuum. The residue was purified by semi-preparative reverse phase HPLC to give methyl 5-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]pentanoate (120 mg, 0.19 mmol, 26% yield) as a colorless oil. LC/MS (ESI) m/z: 617.5 [M+1]$^+$.

Step 8: Preparation of 5-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)pentanoic acid

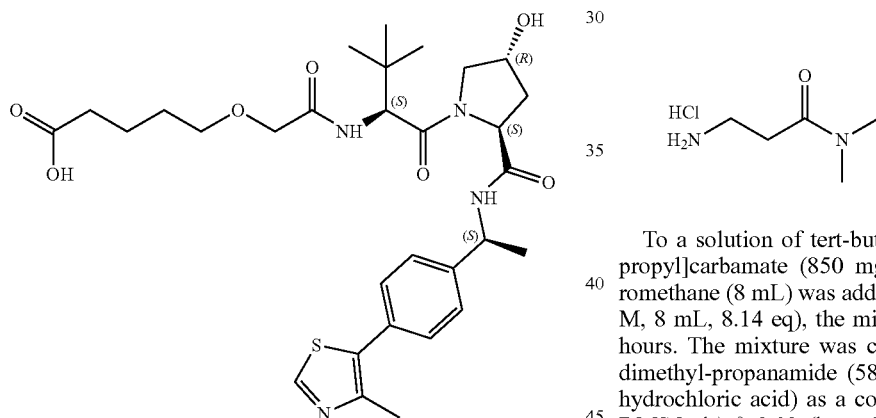

To a solution of methyl 5-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]pentanoate (120 mg, 0.19 mmol, 1 eq) in tetrahydrofuran (3 mL), methanol (3 mL) and water (3 mL) was added lithium hydroxide monohydrate (251 mg, 5.98 mmol, 30.74 eq). The mixture was stirred at 0° C. for 3 hours. The pH of the mixture was adjusted to 5 by hydrochloric acid (1 M) and the aqueous phase was extracted with ethyl acetate (150 mL). The combined organic phase was washed with brine (30 mL), dried with anhydrous sodium sulfate, filtered and concentrated under vacuum to give 5-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]pentanoic acid (100 mg, 0.16 mmol, 85% yield) as a yellow oil.

Step 9: Preparation of tert-butyl (3-(dimethylamino)-3-oxopropyl)carbamate

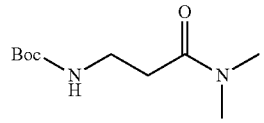

To a solution of 2-cyano-N,N-dimethyl-acetamide (500 mg, 4.46 mmol, 1 eq) in ethyl alcohol (10 mL) was added Raney-Ni (100 mg, 1.17 mmol) and then ammonium hydroxide (1.82 g, 17.14 mmol, 2 mL, 33% purity, 3.84 eq), di-tert-butyl dicarbonate (1.46 g, 6.69 mmol, 1.54 mL, 1.5 eq), the mixture was stirred at 25° C. for 10 hours under hydrogen (15 psi). The mixture was filtered and the filtrate was condensed to give crude product. The crude product was purified by silica gel column chromatography (20-100% ethyl acetate in petroleum ether) to give product tert-butyl N-[3-(dimethylamino)-3-oxo-propyl]carbamate (850 mg, 3.93 mmol, 88% yield) as a colorless oil. $^1$H-NMR (400 MHz, CDCl$_3$) δ 5.43-5.27 (m, 1H), 3.41 (q, J=5.6 Hz, 2H), 2.98 (s, 3H), 2.95 (s, 3H), 2.50 (t, J=5.6 Hz, 2H), 1.42 (s, 9H).

Step 10: Preparation of 3-amino-N,N-dimethylpropanamide hydrochloride

To a solution of tert-butyl N-[3-(dimethylamino)-3-oxopropyl]carbamate (850 mg, 3.93 mmol, 1 eq) in dichloromethane (8 mL) was added hydrochloric acid/methanol (4 M, 8 mL, 8.14 eq), the mixture was stirred at 25° C. for 2 hours. The mixture was condensed to give 3-amino-N,N-dimethyl-propanamide (580 mg, 3.80 mmol, 96.7% yield, hydrochloric acid) as a colorless oil. $^1$H-NMR (400 MHz, DMSO-d$_6$) δ 8.02 (br s, 3H), 2.98-2.90 (m, 5H), 2.83 (s, 3H), 2.68 (t, J=6.7 Hz, 2H).

Step 11: Preparation of tert-butyl 4-(7-bromo-6-chloro-2-((3-(dimethylamino)-3-oxopropyl)amino)-8-fluoroquinazolin-4-yl)piperazine-1-carboxylate

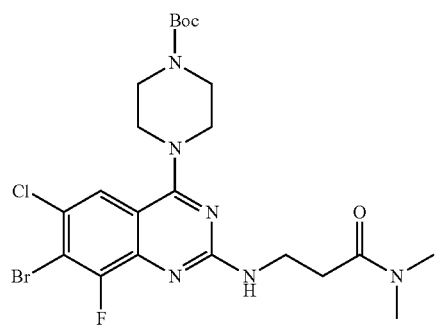 [SMILES: CN(C)C(=O)CCNc1nc(N2CCN(C(=O)OC(C)(C)C)CC2)c2cc(Cl)c(Br)c(F)c2n1]

To a solution of 3-amino-N,N-dimethyl-propanamide (650 mg, 4.26 mmol, 2.38 eq, hydrochloride) in isopropanol (10 mL) was added diisopropylethylamine (810 mg, 6.27 mmol, 1.1 mL, 3.5 eq), and then tert-butyl 4-(7-bromo-2,6-dichloro-8-fluoro-quinazolin-4-yl)piperazine-1-carboxylate (860 mg, 1.79 mmol, 1 eq) was added, the mixture was stirred at 95° C. for 12 hours. The mixture was condensed to give a residue, this residue was dissolved in ethyl acetate (100 mL) and washed by water (100 mL), the organic phase was dried by anhydrous, filter and the filtrate was condensed to give crude product. This crude product was purified by silica gel column chromatography (ethyl acetate/petroleum ether/dichloromethane=5/1/1, 3/1/1, 2/1/1, 1/1/1) to give tert-butyl 4-[7-bromo-6-chloro-2-[[3-(dimethylamino)-3-oxo-propyl]amino]-8-fluoro-quinazolin-4-yl]piperazine-1-carboxylate (750 mg, 1.34 mmol, 74% yield) as a brown solid. $^{1}$H-NMR (400 MHz, CDCl$_3$) δ 7.56 (d, J=1.9 Hz, 1H), 5.92 (br t, J=6.2 Hz, 1H), 3.84 (q, J=6.2 Hz, 2H), 3.61 (br s, 8H), 3.03 (s, 3H), 2.97 (s, 3H), 2.67 (br s, 2H), 1.50 (s, 9H).

Step 12: Preparation of tert-butyl 4-(6-chloro-2-((3-(dimethylamino)-3-oxopropyl)amino)-8-fluoro-7-(3-hydroxynaphthalen-1-yl)quinazolin-4-yl)piperazine-1-carboxylate

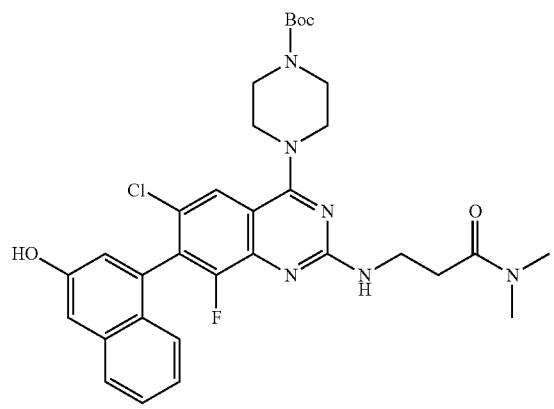 [SMILES: CN(C)C(=O)CCNc1nc(N2CCN(C(=O)OC(C)(C)C)CC2)c2cc(Cl)c(-c3cc(O)cc4ccccc34)c(F)c2n1]

To a solution of tert-butyl 4-[7-bromo-6-chloro-2-[[3-(dimethylamino)-3-oxo-propyl]amino]-8-fluoro-quinazolin-4-yl]piperazine-1-carboxylate (332 mg, 0.59 mmol, 1 eq) and 4-(4,4,5,5-tetramethyl-1,3,2-dioxaborolan-2-yl)naphthalen-2-ol (160 mg, 0.59 mmol, 1 eq) in dioxane (8 mL) and water (2 mL) was added sodium carbonate (188 mg, 1.78 mmol, 3 eq), tetrakis[triphenylphosphine]palladium(0) (68 mg, 0.06 mmol, 0.1 eq), the mixture was stirred at 90° C. under nitrogen for 5 hours. The reaction mixture was charged with tetrakis[triphenylphosphine]palladium(0) (34.22 mg, 0.029 mmol, 0.05 eq) and stirred at 90° C. under nitrogen for 3 hours. The mixture was diluted with water (50 mL) and extracted with ethyl acetate (50 mL, twice), the organic phase was dried by anhydrous sodium sulfate, filtered and the filtrate was condensed to give crude product. This crude product was purified by prep-TLC (dichloromethane/ethyl acetate=1/1) to give tert-butyl 4-[6-chloro-2-[[3-(dimethylamino)-3-oxo-propyl]amino]-8-fluoro-7-(3-hydroxy-1-naphthyl)quinazolin-4-yl]piperazine-1-carboxylate (100 mg, 0.16 mmol, 26.6% yield, 98.2% purity) as a brown solid. LC/MS (ESI) m/z: 623.1 [M+1]$^+$.

Step 13: Preparation of 3-((6-chloro-8-fluoro-7-(3-hydroxynaphthalen-1-yl)-4-(piperazin-1-yl)quinazolin-2-yl)amino)-N,N-dimethylpropanamide

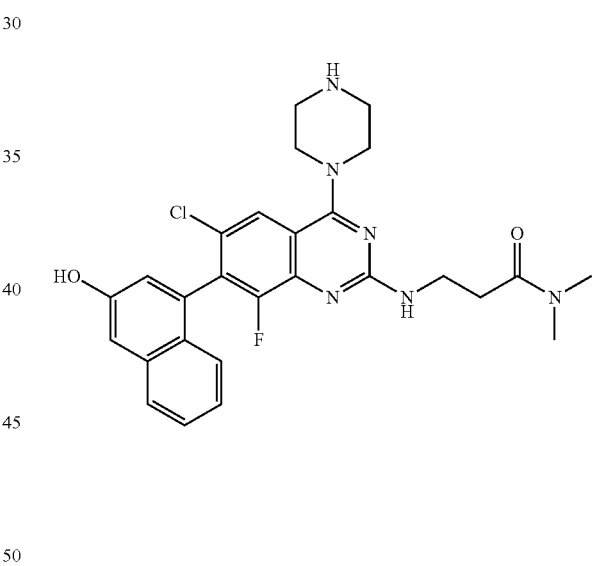

To a solution of tert-butyl 4-[6-chloro-2-[[3-(dimethylamino)-3-oxo-propyl]amino]-8-fluoro-7-(3-hydroxy-1-naphthyl)quinazolin-4-yl]piperazine-1-carboxylate (100 mg, 0.16 mmol, 1 eq) in dichloromethane (8 mL) was added trifluoroacetic acid (3.08 g, 27.01 mmol, 2 mL, 168.32 eq), the mixture was stirred at 25° C. for 1 hour. The mixture was concentrated to give a crude product. This crude product was diluted with saturated sodium bicarbonate aqueous solution (20 mL) and extract with ethyl acetate (20 mL, three times), the organic phase was dried by anhydrous sodium sulfate, filtered and the filtrate was condensed to give 3-[[6-chloro-8-fluoro-7-(3-hydroxy-1-naphthyl)-4-piperazin-1-yl-quinazolin-2-yl]amino]-N,N-dimethyl-propanamide (95 mg) as a brown solid. LC/MS (ESI) m/z: 523.1 [M+1]$^+$.

Step 14: Preparation of (2S,4R)-1-((2S)-2-(2-((5-(4-(6-chloro-2-((3-(dimethylamino)-3-oxopropyl)amino)-8-fluoro-7-(3-hydroxynaphthalen-1-yl)quinazolin-4-yl)piperazin-1-yl)-5-oxopentyl)oxy)acetamido)-3,3-dimethylbutanoyl)-4-hydroxy-N—((S)-1-(4-(4-methylthiazol-5-yl)phenyl)ethyl)pyrrolidine-2-carboxamide

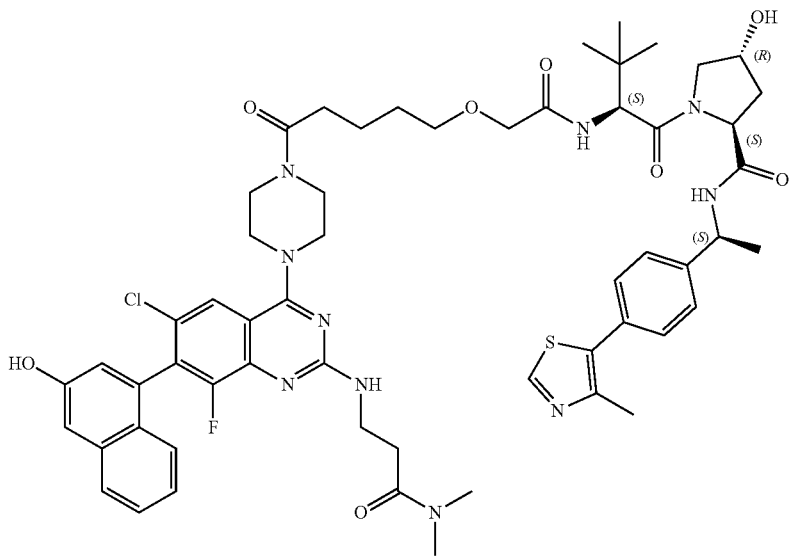

To a mixture of 5-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]pentanoic acid (100 mg, 0.17 mmol, 1 eq) and 3-[[6-chloro-8-fluoro-7-(3-hydroxy-1-naphthyl)-4-piperazin-1-yl-quinazolin-2-yl]amino]-N,N-dimethyl-propanamide (106 mg, 0.17 mmol, 1 eq, trifluoroacetate) in N,N-dimethylformamide (4 mL) was added N,N-diisopropylethylamine (64 mg, 0.50 mmol, 3 eq), 3-(ethyliminomethyleneamino)-N,N-dimethyl-propan-1-amine; hydrochloride (38 mg, 0.20 mmol, 1.2 eq) and 1-hydroxybenzotriazole (27 mg, 0.20 mmol, 1.2 eq). The mixture was stirred at 15° C. for 3 hours. The reaction mixture was quenched by water (20 mL), and then diluted with dichloromethane (50 mL) and extracted with dichloromethane (50 mL×2). The combined organic layers were washed with brine (30 mL), dried over sodium sulfate, filtered and concentrated under reduced pressure to give a residue. The residue was purified by semi-preparative reverse phase HPLC to give (2S,4R)-1-[(2S)-2-[[2-[5-[4-[6-chloro-2-[[3-(dimethylamino)-3-oxo-propyl]amino]-8-fluoro-7-(3-hydroxy-1-naphthyl)quinazolin-4-yl]piperazin-1-yl]-5-oxo-pentoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (9 mg, 0.01 mmol, 4.6% yield, 95% purity) as a white solid. LC/MS (ESI) m/z: 554.4 [M/2+1]+; 1H-NMR (400 MHz, DMSO-d6) δ 10.78-9.66 (s, 1H), 9.09-8.87 (s, 1H), 8.45 (d, J=7.6 Hz, 1H), 8.38 (s, 1H), 7.80 (br d, J=6.0 Hz, 2H), 7.43 (br d, J=8.0 Hz, 3H), 7.38-7.31 (m, 3H), 7.27 (d, J=2.0 Hz, 1H), 7.25-7.10 (m, 3H), 7.05 (d, J=2.4 Hz, 1H), 5.15 (br s, 1H), 4.89 (br t, J=7.2 Hz, 1H), 4.55 (d, J=9.4 Hz, 1H), 4.46 (t, J=8.0 Hz, 1H), 4.29 (br s, 1H), 3.97-3.89 (m, 2H), 3.71 (br s, 5H), 3.59 (br s, 3H), 3.52 (br s, 5H), 2.98 (s, 3H), 2.80 (br s, 3H), 2.61 (br t, J=6.8 Hz, 2H), 2.47-2.40 (m, 6H), 2.12-2.01 (m, 1H), 1.81-1.72 (m, 1H), 1.62 (br s, 4H), 1.49-1.35 (m, 3H), 0.94 (s, 9H).

Exemplary Synthesis of 3-((4-(4-acryloylpiperazin-1-yl)-6-chloro-8-fluoro-7-(3-hydroxynaphthalen-1-yl)quinazolin-2-yl)amino)-N-(2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)-N-methylpropanamide (Exemplary compound 257)

Step 1: Preparation of 2-(trimethylsilyl)ethyl (2-(2-(2-hydroxyethoxy)ethoxy)ethyl)(methyl)carbamate

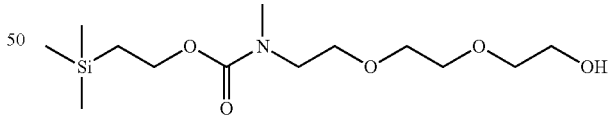

To a stirred solution of 2-(2-(2-(methylamino)ethoxy)ethoxy)ethan-1-ol (1.8 g, 0.005 mol) and triethylamine (1.01 g, 0.01 mol) in dichloromethane (30 mL), was added 4-nitrophenyl (2-(trimethylsilyl)ethyl) carbonate (3.1 g, 0.02 mol) at 0° C. The resulting mixture was stirred at room temperature overnight. The reaction mixture was diluted with dichloromethane (20 mL), washed with water and brine (30 mL), dried over anhydrous sodium sulfate, and concentrated under reduced pressure to afford a crude residue which was purified by silica gel flash chromatography (eluted with 20-30% ethyl acetate in hexane) to afford 2-(trimethylsilyl)ethyl (2-(2-(2-hydroxyethoxy)ethoxy)ethyl)(methyl)carbamate (560 mg, 42%) as colorless oil.

Step 2: Preparation of 2,2,7-trimethyl-6-oxo-5,10,13-trioxa-7-aza-2-silapentadecan-15-yl 4-methylbenzenesulfonate

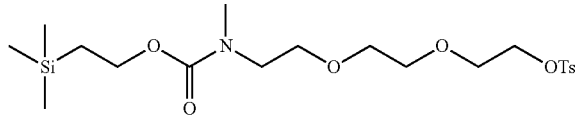 [SMILES: Cc1ccc(S(=O)(=O)OCCOCCOCCN(C)C(=O)OCC[Si](C)(C)C)cc1]

To a stirred solution of 2-(trimethylsilyl)ethyl (2-(2-(2-hydroxyethoxy)ethoxy)ethyl)(methyl)carbamate (560 mg, 1.43 mmol), triethylamine (436 mg, 4.3 mmol) and N,N-dimethylpyridin-4-amine (17 mg, 0.14 mmol) in dichloromethane (10 mL) was added 4-toluenesulfonyl chloride (820 mg, 4.3 mmol) at 0° C. The resulting mixture was stirred at room temperature for 2 hours. The reaction mixture was concentrated under reduced pressure to afford a crude residue which was purified by silica gel flash chromatography (eluted with 20-40% ethyl acetate in hexane) to afford 2,2,7-trimethyl-6-oxo-5,10,13-trioxa-7-aza-2-silapentadecan-15-yl 4-methylbenzenesulfonate (300 mg, 45%) as white solid.

Step 3: Preparation of tert-butyl ((S)-1-(((S)-1-cyclohexyl-2-oxo-2-((S)-2-(4-(3-((2,2,7-trimethyl-6-oxo-5,10,13-trioxa-7-aza-2-silapentadecan-15-yl)oxy)benzoyl)thiazol-2-yl)pyrrolidin-1-yl)ethyl)amino)-1-oxopropan-2-yl)(methyl)carbamate

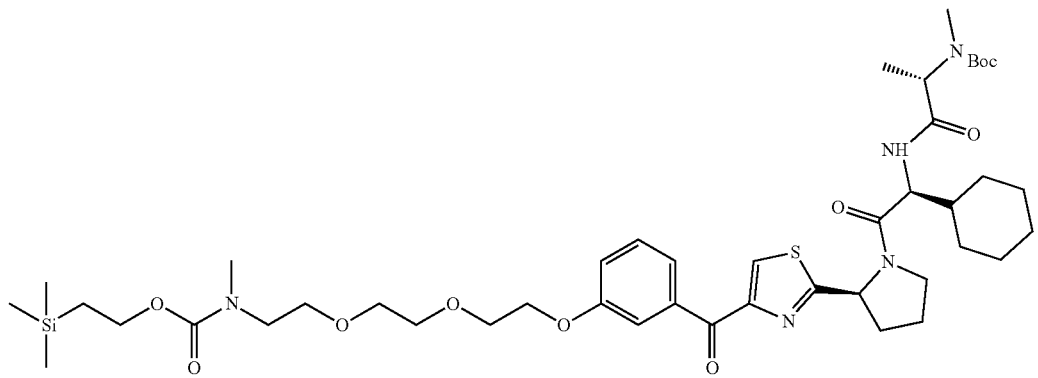 [SMILES: CN[C@@H](C)C(=O)N[C@H](C(=O)N1CCC[C@H]1c1nc(C(=O)c2cccc(OCCOCCOCCN(C)C(=O)OCC[Si](C)(C)C)c2)cs1)C1CCCCC1]

To a stirred solution of 2,2,7-trimethyl-6-oxo-5,10,13-trioxa-7-aza-2-silapentadecan-15-yl 4-methylbenzenesulfonate (115 mg, 0.24 mmol) and potassium carbonate (103 mg, 0.74 mmol) in N,N-dimethylformamide (5 mL) was added tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (100 mg, 0.16 mmol). The resulting mixture was stirred at 50° C. overnight. The reaction mixture was partitioned between ethyl acetate (20 ml) and water (10 ml). The organic layer was collected, and the aqueous layer was extracted with ethyl acetate (15 ml×2). The combined organic layers were washed with brine (10 ml), dried over anhydrous sodium sulfate, and concentrated under reduced pressure to give a residue which was purified by silica gel flash chromatography with (eluted with 3-5% methanol in dichloromethane) to afford tert-butyl ((S)-1-(((S)-1-cyclohexyl-2-oxo-2-((S)-2-(4-(3-((2,2,7-trimethyl-6-oxo-5,10,13-trioxa-7-aza-2-silapentadecan-15-yl)oxy)benzoyl)thiazol-2-yl)pyrrolidin-1-yl)ethyl)amino)-1-oxopropan-2-yl)(methyl)carbamate (120 mg, 49%) as white solid.

Step 4: Preparation of tert-butyl ((S)-1-(((S)-1-cyclohexyl-2-((S)-2-(4-(3-(2-(2-(2-(methylamino)ethoxy)ethoxy)ethoxy)benzoyl)thiazol-2-yl)pyrrolidin-1-yl)-2-oxoethyl)amino)-1-oxopropan-2-yl)(methyl)carbamate

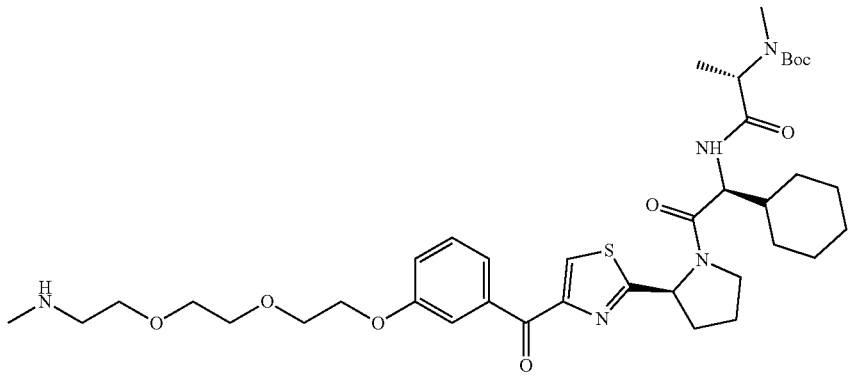 [SMILES: CNCCOCCOCCOc1cccc(C(=O)c2csc([C@@H]3CCCN3C(=O)[C@@H](NC(=O)[C@H](C)NC)C3CCCCC3)n2)c1]

To a stirred solution of tert-butyl ((S)-1-(((S)-1-cyclohexyl-2-oxo-2-((S)-2-(4-(3-((2,2,7-trimethyl-6-oxo-5,10,13-trioxa-7-aza-2-silapentadecan-15-yl)oxy)benzoyl)thiazol-2-yl)pyrrolidin-1-yl)ethyl)amino)-1-oxopropan-2-yl)(methyl)carbamate (120 mg, 0.13 mmol) in tetrahydrofuran (5 mL) was added tetrabutylammonium fluoride (80 mg, 0.30 mmol). The resulting mixture was stirred at room temperature for 4 hours. The reaction mixture was partitioned between ethyl acetate (20 ml) and water (10 ml). The organic layer was collected, and the aqueous layer was extracted with ethyl acetate (15 ml×2). The combined organic layers were washed with brine (10 ml), dried over anhydrous sodium sulfate, and concentrated under reduced pressure to give a residue which was purified by silica gel flash chromatography (eluted with 3-5% methanol in dichloromethane) to afford tert-butyl ((S)-1-(((S)-1-cyclohexyl-2-((S)-2-(4-(3-(2-(2-(2-(methylamino)ethoxy)ethoxy)ethoxy)benzoyl)thiazol-2-yl)pyrrolidin-1-yl)-2-oxoethyl)amino)-1-oxopropan-2-yl)(methyl)carbamate (130 mg, 80%) as white solid.

Step 5: Preparation of tert-butyl ((2S)-1-(((1S)-2-((2S)-2-(4-(3-(2-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)ethoxy)benzoyl)thiazol-2-yl)pyrrolidin-1-yl)-1-cyclohexyl-2-oxoethyl)amino)-1-oxopropan-2-yl)(methyl)carbamate

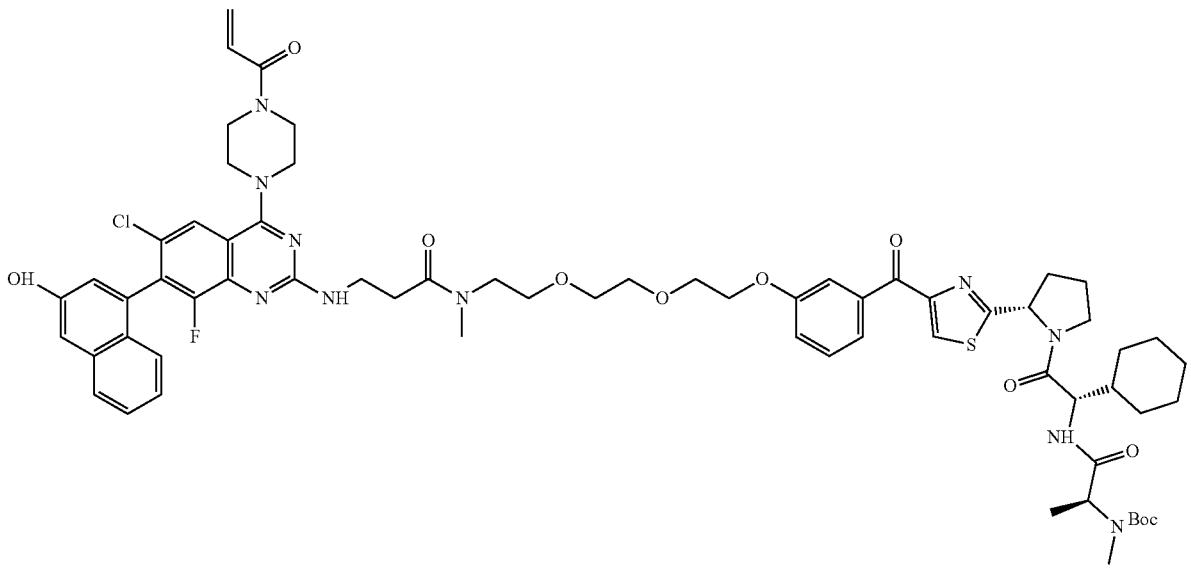 [SMILES: C=CC(=O)N1CCN(c2nc(NCCC(=O)N(C)CCOCCOCCOc3cccc(C(=O)c4csc([C@@H]5CCCN5C(=O)[C@@H](NC(=O)[C@H](C)NC)C5CCCCC5)n4)c3)nc3c(F)c(-c4cc(O)cc5ccccc45)c(Cl)cc23)CC1]

To a stirred solution of tert-butyl ((S)-1-(((S)-1-cyclohexyl-2-((S)-2-(4-(3-(2-(2-(2-(methylamino)ethoxy)ethoxy)ethoxy)benzoyl)thiazol-2-yl)pyrrolidin-1-yl)-2-oxoethyl)amino)-1-oxopropan-2-yl)(methyl)carbamate (130 mg, 0.14 mmol), (2-(7-Aza-1H-benzotriazole-1-yl)-1,1,3,3-tetramethyluronium hexafluorophosphate) (96 mg, 0.23 mmol) and N-ethyl-N-isopropylpropan-2-amine (49 mg, 0.37 mmol) in N,N-dimethylformamide (5 mL) was added 3-((4-(4-acryloylpiperazin-1-yl)-6-chloro-8-fluoro-7-(3-hydroxynaphthalen-1-yl)quinazolin-2-yl)amino)propanoic acid (70 mg, 0.12 mmol). The resulting mixture was stirred at room temperature for 1 hour. The reaction mixture was partitioned between ethyl acetate (20 ml) and water (10 ml). The organic layer was collected, and the aqueous layer was extracted with ethyl acetate (15 ml×2). The combined organic layers were washed with brine (10 ml), dried over anhydrous sodium sulfate, and concentrated under reduced pressure to give a residue which was purified by pre-TLC (eluted with 10% methanol in dichloromethane) to afford tert-butyl ((S)-1-(((S)-2-((S)-2-(4-(3-(2-(2-(2-(3-((4-(4-acryloylpiperazin-1-yl)-6-chloro-8-fluoro-7-((E)-3-hydroxy-1-(o-tolyl)prop-1-en-1-yl)quinazolin-2-yl)amino)-N-methylpropanamido)ethoxy)ethoxy)ethoxy)benzoyl)thiazol-2-yl)pyrrolidin-1-yl)-1-cyclohexyl-2-oxoethyl)amino)-1-oxopropan-2-yl)(methyl)carbamate (80 mg, 49%) as white solid.

Step 6: Preparation of 3-((4-(4-acryloylpiperazin-1-yl)-6-chloro-8-fluoro-7-(3-hydroxynaphthalen-1-yl)quinazolin-2-yl)amino)-N-(2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)-N-methylpropanamide

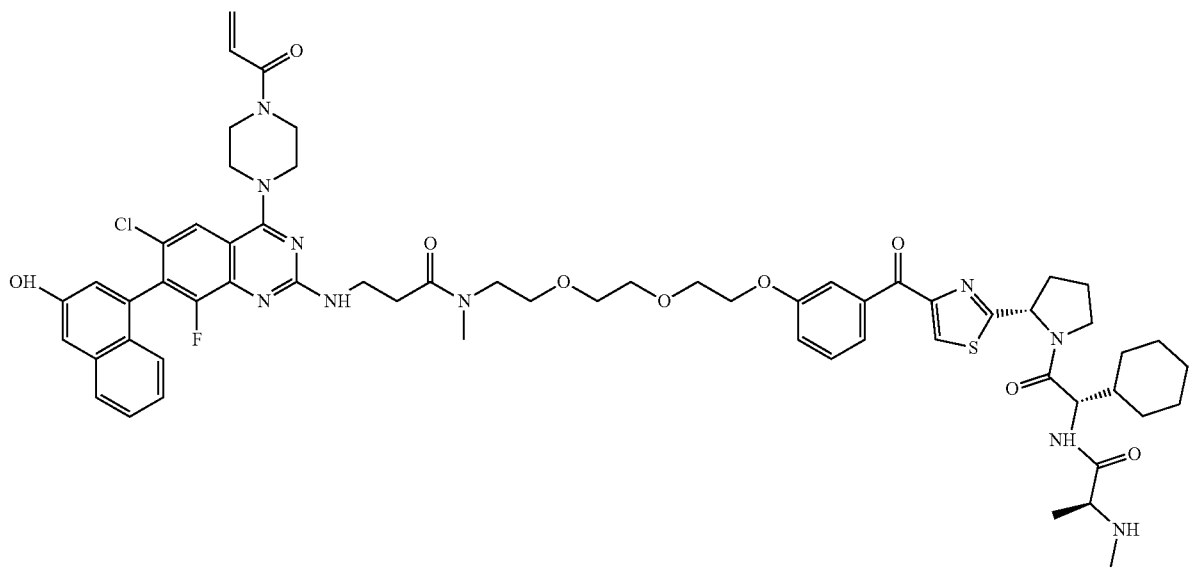 [SMILES: C=CC(=O)N1CCN(c2nc(NCCC(=O)N(C)CCOCCOCCOc3cccc(C(=O)c4csc([C@@H]5CCCN5C(=O)[C@@H](NC(=O)[C@H](C)NC)C5CCCCC5)n4)c3)nc3c(F)c(-c4cc(O)cc5ccccc45)c(Cl)cc23)CC1]

A solution of tert-butyl ((S)-1-(((S)-2-((S)-2-(4-(3-(2-(2-(2-(3-((4-(4-acryloylpiperazin-1-yl)-6-chloro-8-fluoro-7-((E)-3-hydroxy-1-(o-tolyl)prop-1-en-1-yl)quinazolin-2-yl)amino)-N-methylpropanamido)ethoxy)ethoxy)ethoxy)benzoyl)thiazol-2-yl)pyrrolidin-1-yl)-1-cyclohexyl-2-oxoethyl)amino)-1-oxopropan-2-yl)(methyl)carbamate (80 mg, 0.062 mmol) in 4M hydrogen chloride in dioxane (2 mL) was stirred at room temperature for 20 minutes. The volatiles were evaporated under reduced pressure to give a residue which was taken up in aqueous sodium bicarbonate (1N, 10 mL) and extracted with dichloromethane (20 ml). The combined organic layer was collected, dried over anhydrous sodium sulfate, and concentrated under reduced pressure to afford a crude residue which was purified by pre-TLC (eluted with 10% methanol in chloromethane) to afford 3-((4-(4-acryloylpiperazin-1-yl)-6-chloro-8-fluoro-7-(3-hydroxynaphthalen-1-yl)quinazolin-2-yl)amino)-N-(2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)-N-methylpropanamide (60 mg, 82%) as white solid. LC/MS (ESI) m/z: 1175.5 [M+1]$^+$; $^1$H-NMR (400 MHz, DMSO-d$_6$) δ 0.86 (s, 1H), 1.06 (s, 6H), 1.16-1.28 (m, 5H), 1.62 (d, J=1.2 Hz, 6H), 2.01 (s, 2H), 2.19 (s, 1H), 2.32 (s, 3H), 2.63 (d, J=25.4 Hz, 2H), 2.80 (s, 1H), 2.99 (s, 1H), 3.38-3.60 (m, 11H), 3.61-3.91 (m, 12H), 4.12 (dd, J=1.4, 0.8 Hz, 2H), 4.47 (s, 1H), 5.32-5.43 (m, 1H), 5.73 (d, J=10.4 Hz, 1H), 6.16 (d, J=16.8 Hz, 1H), 6.76-6.89 (m, 1H), 7.05 (d, J=1.9 Hz, 1H), 7.18-7.29 (m, 4H), 7.42 (s, 2H), 7.58-7.66 (m, 2H), 7.78 (s, 2H), 8.38-8.26 (m, 1H), 8.47 (s, 1H), 10.01 (s, 1H).

Exemplary Synthesis of 3-((4-(4-acryloylpiperazin-1-yl)-6-chloro-8-fluoro-7-((S)-2-fluoro-6-hydroxyphenyl)quinazolin-2-yl)amino)-N-(2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)-N-methylpropanamide (Exemplary Compound 277)

Step 1: Preparation of tert-butyl ((S)-1-(((S)-2-((S)-2-(4-(4-(2-(2-(2-(3-((4-(4-acryloylpiperazin-1-yl)-6-chloro-8-fluoro-7-((S)-2-fluoro-6-hydroxyphenyl)quinazolin-2-yl)amino)-N-methylpropanamido)ethoxy)ethoxy)ethoxy)naphthalen-1-yl)thiazol-2-yl)pyrrolidin-1-yl)-1-cyclohexyl-2-oxoethyl)amino)-1-oxopropan-2-yl)(methyl)carbamate

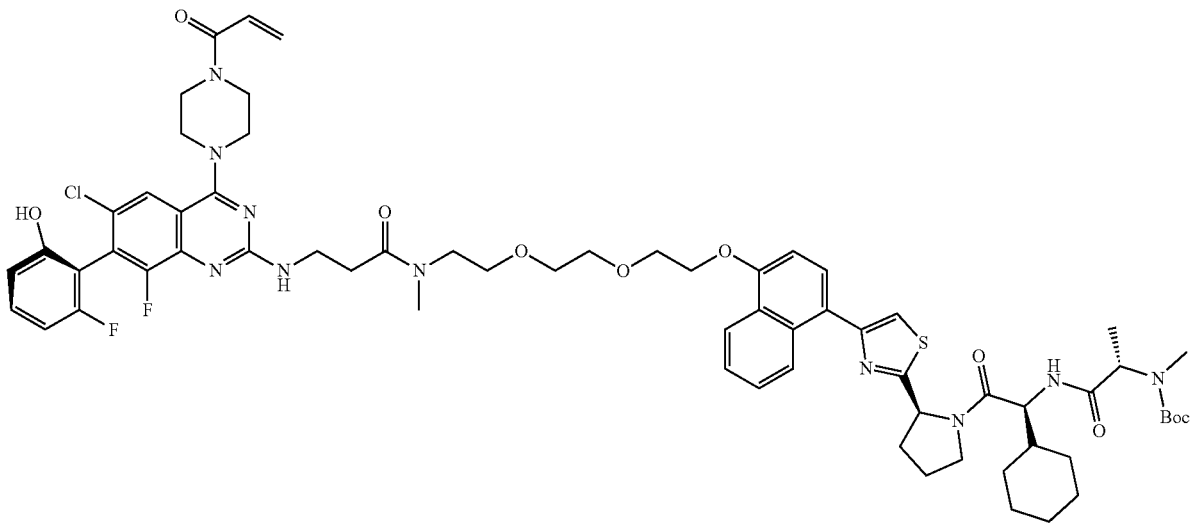

To a mixture of 3-[[6-chloro-8-fluoro-7-(2-fluoro-6-hydroxy-phenyl)-4-(4-prop-2-enoylpiperazin-1-yl)quinazolin-2-yl]amino]propanoic acid (50 mg, 96.54 umol, 1 eq) and tert-butyl N-[(1S)-2-[[(1S)-1-cyclohexyl-2-[(2S)-2-[4-[4-[2-[2-[2-(methylamino)ethoxy]ethoxy]ethoxy]-1-naphthyl]thiazol-2-yl]pyrrolidin-1-yl]-2-oxo-ethyl]amino]-1-methyl-2-oxo-ethyl]-N-methyl-carbamate (78.39 mg, 102.34 umol, 1.06 eq) in Dimethylformamide (5 mL) was added Diisopropylethylamine (49.91 mg, 386.17 umol, 67.26 uL, 4 eq), Hydroxybenzotriazole (26.09 mg, 193.08 umol, 2 eq) and N-(3-dimethylaminopropyl)-N'-ethylcarbodiimide (37.01 mg, 193.08 umol, 2 eq) in one portion. The mixture was stirred at 20° C. for 12 hours. The reaction mixture was washed with water (50 mL) and extracted with ethyl acetate (30 mL×3), then the organic phase was concentrated in vacuum. The residue was purified by prep-HPLC to give compound tert-butyl N-[(1S)-2-[[(1S)-2-[(2S)-2-[4-[4-[2-[2-[3-[[6-chloro-8-fluoro-7-(2-fluoro-6-hydroxy-phenyl)-4-(4-prop-2-enoylpiperazin-1-yl)quinazolin-2-yl]amino]propanoyl-methyl-amino]ethoxy]ethoxy]-1-naphthyl]thiazol-2-yl]pyrrolidin-1-yl]-1-cyclohexyl-2-oxo-ethyl]amino]-1-methyl-2-oxo-ethyl]-N-methyl-carbamate (60 mg, 47.40 umol, 49% yield) as a white solid. LC/MS (ESI) m/z: 633.3 [M/2+1]+.

Step 2: Preparation of 3-((4-(4-acryloylpiperazin-1-yl)-6-chloro-8-fluoro-7-((S)-2-fluoro-6-hydroxyphenyl)quinazolin-2-yl)amino)-N-(2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)-N-methylpropanamide

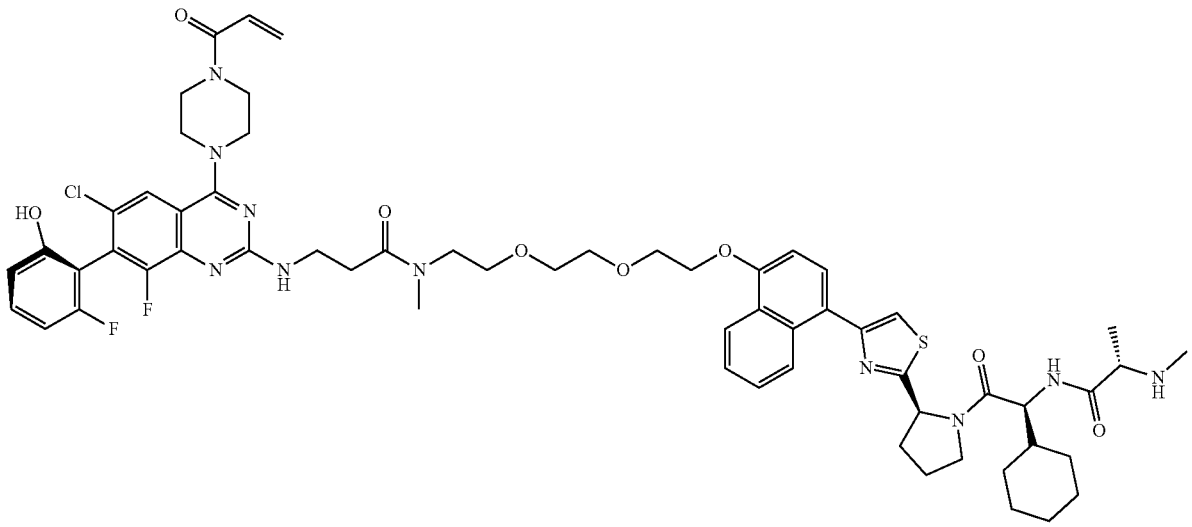

To a mixture of tert-butyl N-[(1S)-2-[[(1S)-2-[(2S)-2-[4-[4-[2-[2-[2-[3-[[6-chloro-8-fluoro-7-(2-fluoro-6-hydroxy-phenyl)-4-(4-prop-2-enoylpiperazin-1-yl)quinazolin-2-yl]amino]propanoyl-methyl-amino]ethoxy]ethoxy]ethoxy]-1-naphthyl]thiazol-2-yl]pyrrolidin-1-yl]-1-cyclohexyl-2-oxo-ethyl]amino]-1-methyl-2-oxo-ethyl]-N-methyl-carbamate (60 mg, 47.40 umol, 1 eq) in dichloromethane (5 mL) was added Trifluoroacetic Acid (770.00 mg, 6.75 mmol, 0.5 mL, 142.48 eq) in one portion. The mixture was stirred at 20° C. for 1 hour. The reaction mixture was concentrated under reduced pressure to remove solvent to give a residue. The residue was purified by prep-HPLC to give compound (2S)—N-[(1S)-2-[(2S)-2-[4-[4-[2-[2-[2-[3-[[6-chloro-8-fluoro-7-(2-fluoro-6-hydroxy-phenyl)-4-(4-prop-2-enoylpiperazin-1-yl)quinazolin-2-yl]amino]propanoyl-methyl-amino]ethoxy]ethoxy]ethoxy]-1-naphthyl]thiazol-2-yl]pyrrolidin-1-yl]-1-cyclohexyl-2-oxo-ethyl]-2-(methylamino)propanamide (23.4 mg, 18.10 umol, 38% yield, 99% purity, Trifluoroacetic Acid) as a white solid. LC/MS (ESI) m/z: 583.3 [M/2+1]+; $^{1}$H-NMR (400 MHz, CD$_{3}$OD) δ 8.25 (br d, J=7.3 Hz, 1H), 8.14-8.01 (m, 1H), 7.85-7.63 (m, 1H), 7.52-7.32 (m, 5H), 6.91-6.66 (m, 4H), 6.30 (br d, J=16.4 Hz, 1H), 5.83 (br d, J=10.3 Hz, 1H), 5.51 (br d, J=7.2 Hz, 1H), 4.67-4.58 (m, 1H), 4.28 (br s, 2H), 4.16-3.51 (m, 26H), 3.16-3.03 (m, 1H), 2.97 (s, 2H), 2.86 (br s, 1H), 2.75-2.65 (m, 3H), 2.46-2.07 (m, 4H), 1.95-1.61 (m, 6H), 1.51 (d, J=7.0 Hz, 3H), 1.31-1.06 (m, 5H).

Exemplary Synthesis of 4-(6-chloro-2-((3-((2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)(methyl)amino)-3-oxopropyl)amino)-8-fluoro-7-((S)-2-fluoro-6-hydroxyphenyl)quinazolin-4-yl)piperazine-1-carboxamide (Exemplary Compound 287)

Step 1: Preparation of tert-butyl ((S)-1-(((S)-2-((S)-2-(4-(4-(2-(2-(2-(3-((4-(4-carbamoylpiperazin-1-yl)-6-chloro-8-fluoro-7-((S)-2-fluoro-6-hydroxyphenyl)quinazolin-2-yl)amino)-N-methylpropanamido)ethoxy)ethoxy)ethoxy)naphthalen-1-yl)thiazol-2-yl)pyrrolidin-1-yl)-1-cyclohexyl-2-oxoethyl)amino)-1-oxopropan-2-yl)(methyl)carbamate

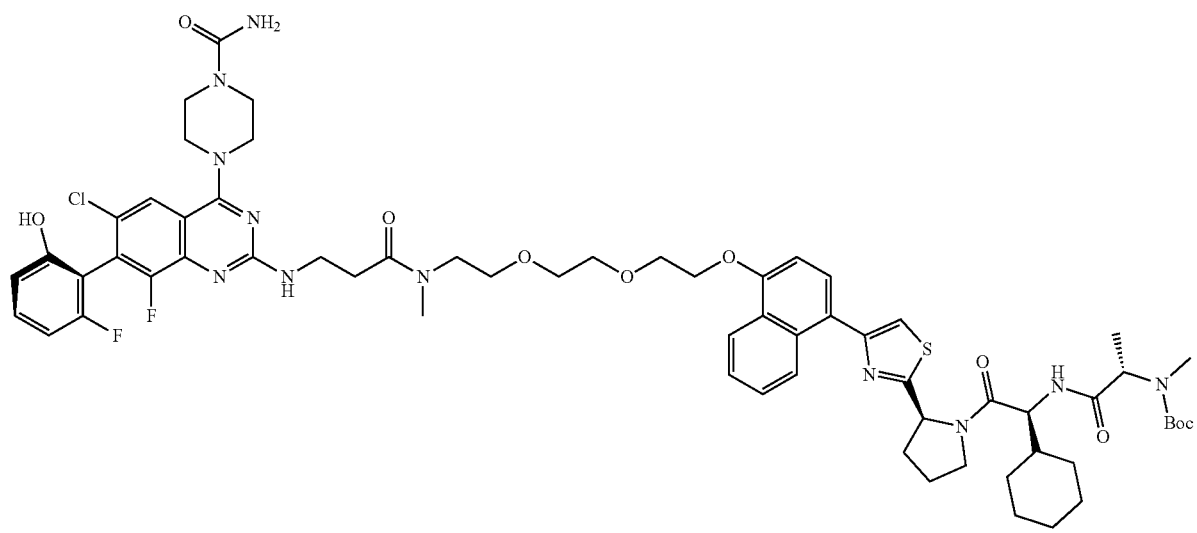

To a mixture of tert-butyl ((S)-1-(((S)-1-cyclohexyl-2-((S)-2-(4-(4-(2-(2-(2-(methylamino)ethoxy)ethoxy)ethoxy)naphthalen-1-yl)thiazol-2-yl)pyrrolidin-1-yl)-2-oxoethyl)amino)-1-oxopropan-2-yl)(methyl)carbamate (60.45 mg, 78.91 umol, 1 eq), (S)-3-((4-(4-carbamoylpiperazin-1-yl)-6-chloro-8-fluoro-7-(2-fluoro-6-hydroxyphenyl)quinazolin-2-yl)amino)propanoic acid (40 mg, 78.91 umol, 1 eq) and N-ethyl-N-isopropylpropan-2-amine (40.80 mg, 315.65 umol, 54.98 uL, 4 eq) in dimethylformamide (5 mL) was added hydroxybenzotriazole (21.33 mg, 157.83 umol, 2.0 eq) and N-(3-dimethylaminopropyl)-N'-ethylcarbodiimide hydrochloride (30.26 mg, 157.83 umol, 2 eq) in one portion. The mixture was stirred at 20° C. for 12 hours. The reaction mixture was washed with water (50 mL) and extracted with ethyl acetate (30 mL×3), then the organic phase was concentrated in vacuum. The residue was purified by prep-Thin layer chromatography (silicon dioxide, Ethyl acetate:Methanol=40:1). Compound tert-butyl ((S)-1-(((S)-2-((S)-2-(4-(4-(2-(2-(2-(3-((4-(4-carbamoylpiperazin-1-yl)-6-chloro-8-fluoro-7-((S)-2-fluoro-6-hydroxyphenyl)quinazolin-2-yl)amino)-N-methylpropanamido)ethoxy)ethoxy)ethoxy)naphthalen-1-yl)thiazol-2-yl)pyrrolidin-1-yl)-1-cyclohexyl-2-oxoethyl)amino)-1-oxopropan-2-yl)(methyl)carbamate (60 mg, 40.16 umol, 51% yield, 84% purity) was obtained as a white solid. LC/MS (ESI) m/z: 1254.8 [M+1]$^+$.

Step 2: Preparation of 4-(6-chloro-2-((3-((2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)(methyl)amino)-3-oxopropyl)amino)-8-fluoro-7-((S)-2-fluoro-6-hydroxyphenyl)quinazolin-4-yl)piperazine-1-carboxamide

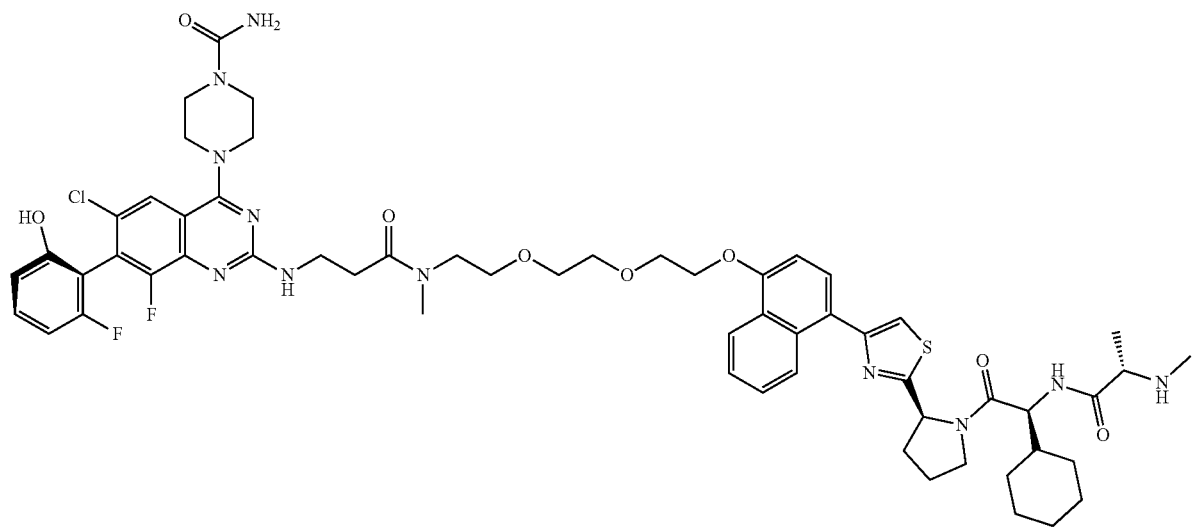

To a solution of tert-butyl ((S)-1-(((S)-2-((S)-2-(4-(4-(2-(2-(2-(3-((4-(4-carbamoylpiperazin-1-yl)-6-chloro-8-fluoro-7-((S)-2-fluoro-6-hydroxyphenyl)quinazolin-2-yl)amino)-N-methylpropanamido)ethoxy)ethoxy)ethoxy)naphthalen-1-yl)thiazol-2-yl)pyrrolidin-1-yl)-1-cyclohexyl-2-oxoethyl)amino)-1-oxopropan-2-yl)(methyl)carbamate (50 mg, 39.84 umol, 1 eq) in dichloromethane (2 mL) was added trifluoroacetic acid (1.54 g, 13.51 mmol, 1000 uL, 338.97 eq). The mixture was stirred at 25° C. for 2 hours. The reaction mixture was concentrated under reduced pressure to give a residue. The residue was purified by prep-HPLC. Compound 4-(6-chloro-2-((3-((2-(2-(2-((4-(2-((S)-1-((S)-2-cyclohexyl-2-((S)-2-(methylamino)propanamido) acetyl)pyrrolidin-2-yl)thiazol-4-yl)naphthalen-1-yl)oxy)ethoxy)ethoxy)ethyl)(methyl)amino)-3-oxopropyl)amino)-8-fluoro-7-((S)-2-fluoro-6-hydroxyphenyl)quinazolin-4-yl)piperazine-1-carboxamide (8.7 mg, 6.58 umol, 16% yield, 96% purity, trifluoroacetic acid) was obtained as a yellow solid. LC/MS (ESI) m/z: 1176.5 [M+23]$^+$; $^1$H-NMR (400 MHz, CD$_3$OD) δ 8.27 (br d, J=8.0 Hz, 1H), 8.09 (d, J=8.4 Hz, 1H), 7.81-7.67 (m, 1H), 7.50-7.37 (m, 5H), 6.88-6.76 (m, 3H), 5.55 (br d, J=8.0 Hz, 1H), 4.65 (d, J=6.8 Hz, 1H), 4.31 (br s, 2H), 4.06-3.58 (m, 25H), 2.99 (s, 2H), 2.89 (br s, 1H), 2.70 (s, 3H), 2.47 (br s, 1H), 2.29 (br d, J=6.4 Hz, 2H), 2.17 (br s, 1H), 1.96-1.62 (m, 7H), 1.53 (d, J=6.8 Hz, 3H), 1.37-1.10 (m, 6H).

Exemplary Synthesis of (2R,3S,4R,5S)—N-(4-((2-(2-(2-(3-(((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide (Exemplary Compound 302)

Step 1: Preparation of tert-butyl 4-(6-chloro-2-((1-(4-(((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-11-methyl-1,12-dioxo-5,8-dioxa-2,11-diazatetradecan-14-yl)amino)-8-fluoro-7-(3-hydroxynaphthalen-1-yl)quinazolin-4-yl)piperazine-1-carboxylate

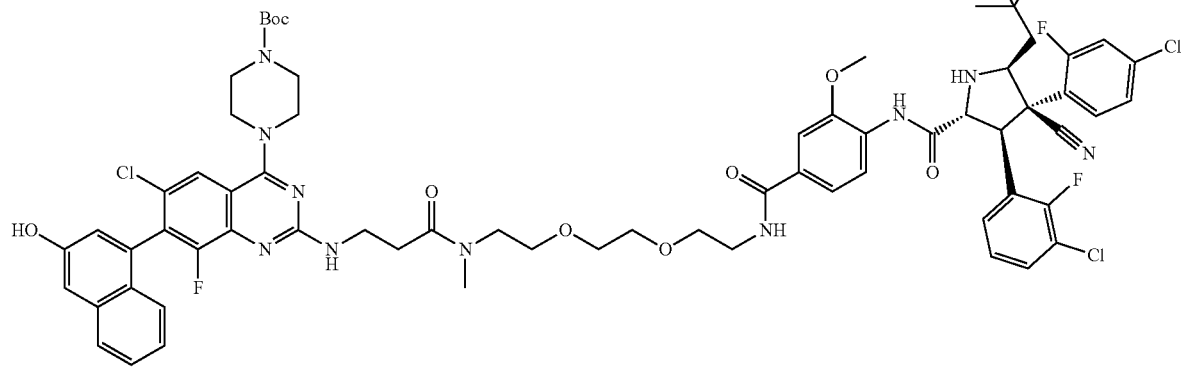

To the mixture of (2R,3S,4R,5S)-3-(3-chloro-2-fluoro-phenyl)-4-(4-chloro-2-fluoro-phenyl)-4-cyano-5-(2,2-dimethylpropyl)-N-[2-methoxy-4-[2-[2-[2-(methylamino)ethoxy]ethoxy]ethylcarbamoyl]phenyl]pyrrolidine-2-carboxamide (140 mg, 0.16 mmol, 1 eq, trifluoroacetate) and 3-[[4-(4-tert-butoxycarbonylpiperazin-1-yl)-6-chloro-8-fluoro-7-(3-hydroxy-1-naphthyl)quinazolin-2-yl]amino] propanoic acid (95 mg, 0.16 mmol, 1 eq) in N,N-dimethylformamide (8 mL) was added 1-hydroxybenzotriazole (32 mg, 0.24 mmol, 1.5 eq), N-(3-dimethylaminopropyl)-N-ethylcarbodiimide hydrochloride (46 mg, 0.24 mmol, 1.5 eq) and N,N-diisopropylethylamine (103 mg, 0.80 mmol, 0.14 mL, 5 eq). The mixture was stirred at 20° C. for 15 hours. The mixture was diluted with water (25 mL), extracted with ethyl acetate (25 mL×3). The combined organic layer was washed with water (30 mL×2) and brine (30 mL×2), dried over anhydrous sodium sulfate, filtered and concentrated under reduced pressure to give a residue. The residue was purified by prep-Thin-layer chromatography (dichloromethane:methanol=10:1). tert-butyl 4-[6-chloro-2-[[3-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl) pyrrolidine-2-carbonyl]amino]-3-methoxy-benzoyl]amino] ethoxy]ethoxy]ethyl-methyl-amino]-3-oxo-propyl]amino]-8-fluoro-7-(3-hydroxy-1-naphthyl)quinazolin-4-yl] piperazine-1-carboxylate (150 mg, 0.11 mmol, 70% yield) was obtained as a light yellow solid. LC/MS (ESI) m/z: 1339.4 [M+1]$^+$.

Step 2: Preparation of (2R,3S,4R,5S)-3-(3-chloro-2-fluorophenyl)-4-(4-chloro-2-fluorophenyl)-N-(4-((2-(2-(2-(3-((6-chloro-8-fluoro-7-(3-hydroxynaphthalen-1-yl)-4-(piperazin-1-yl)quinazolin-2-yl)amino)-N-methylpropanamido)ethoxy)ethoxy)ethyl)carbamoyl)-2-methoxyphenyl)-4-cyano-5-neopentylpyrrolidine-2-carboxamide

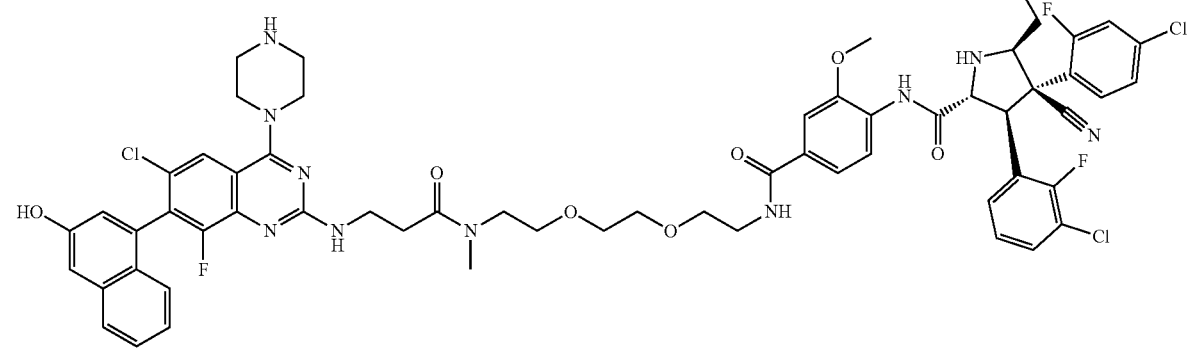

To the mixture of tert-butyl 4-[6-chloro-2-[[3-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethyl-methyl-amino]-3-oxo-propyl]amino]-8-fluoro-7-(3-hydroxy-1-naphthyl)quinazolin-4-yl]piperazine-1-carboxylate (150 mg, 0.11 mmol, 1 eq) in dichloromethane (5 mL) was added trifluoroacetic acid (1 mL). The mixture was stirred at 20° C. for 0.5 hour. The mixture was concentrated under reduced pressure to give the product. (2R,3S,4R,5S)—N-[4-[2-[2-[2-[3-[[6-chloro-8-fluoro-7-(3-hydroxy-1-naphthyl)-4-piperazin-1-yl-quinazolin-2-yl]amino]propanoyl-methyl-amino]ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (150 mg, trifluoroacetate) was obtained as a light yellow oil. LC/MS (ESI) m/z: 1239.4 [M+1]$^+$.

Step 3: Preparation of (2R,3S,4R,5S)—N-(4-((2-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide

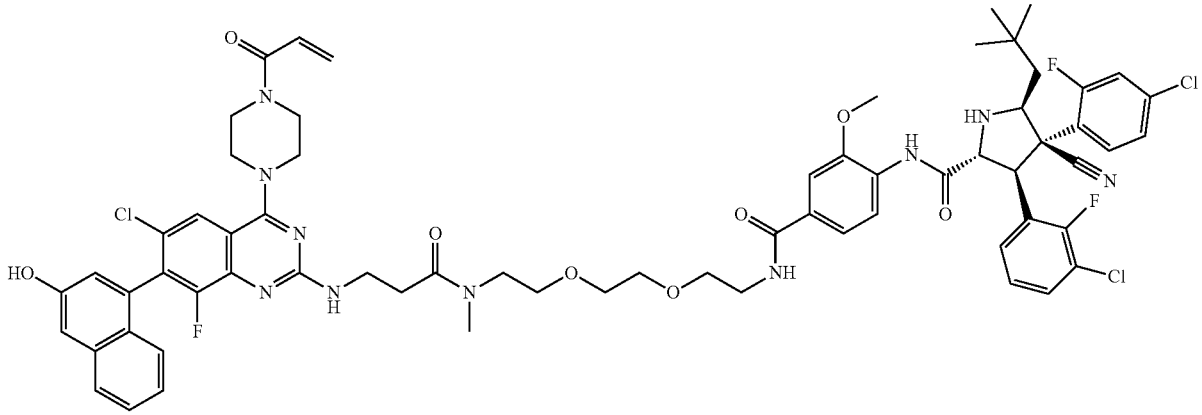 [SMILES: C=CC(=O)N1CCN(c2nc(NCCC(=O)N(C)CCOCCOCCNC(=O)c3ccc(NC(=O)[C@@H]4N[C@@H](CC(C)(C)C)[C@](C#N)(c5ccc(Cl)cc5F)[C@H]4c4cccc(Cl)c4F)c(OC)c3)nc3c(F)c(-c4cc(O)cc5ccccc45)c(Cl)cc23)CC1]

To the mixture of (2R,3S,4R,5S)—N-[4-[2-[2-[2-[3-[[6-chloro-8-fluoro-7-(3-hydroxy-1-naphthyl)-4-piperazin-1-yl-quinazolin-2-yl]amino]propanoyl-methyl-amino]ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (150 mg, 0.11 mmol, 1 eq, trifluoroacetate) and 2,6-lutidine (118 mg, 1.11 mmol, 0.13 mL, 10 eq) in dichloromethane (20 mL) was added prop-2-enoyl chloride (10 mg, 0.11 mmol, 0.009 mL, 1 eq) in dichloromethane (2 mL) at −78° C. under nitrogen atmosphere. The mixture was stirred at −78° C. for 0.5 hour. The mixture was quenched with water (20 mL). It was extracted with dichloromethane (20 mL×2). The combined organic layer was washed with brine (20 mL×2), dried over anhydrous sodium sulfate, filtered and concentrated under reduced pressure to give a residue. The residue was purified by prep-HPLC. (2R,3S,4R,5S)—N-[4-[2-[2-[2-[3-[[6-chloro-8-fluoro-7-(3-hydroxy-1-naphthyl)-4-(4-prop-2-enoylpiperazin-1-yl)quinazolin-2-yl]amino]propanoyl-methyl-amino]ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (40.1 mg, 0.03 mmol, 27% yield, 97% purity) was obtained as an off-white solid. LC/MS (ESI) m/z: 1293.3 [M+1]$^+$; $^1$H-NMR (400 MHz, DMSO-d$_6$) δ 10.39 (s, 1H), 9.99 (s, 1H), 8.45-8.42 (m, 1H), 8.30-8.29 (m, 2H), 7.79-7.77 (m, 2H), 7.74-7.71 (m, 1H), 7.58-7.48 (m, 5H), 7.41-7.34 (m, 4H), 7.26 (s, 1H), 7.25-7.21 (m, 2H), 7.04 (s, 1H), 6.86-6.80 (m, 1H), 6.18-6.14 (m, 1H), 5.73-5.71 (m, 1H), 4.59 (s, 2H), 4.27-4.41 (m, 1H), 3.97-3.90 (m, 4H), 3.80-3.71 (m, 10H), 3.52-3.45 (m, 12H), 2.98-2.79 (m, 3H), 2.62-2.60 (m, 1H), 1.66-1.60 (m, 1H), 1.28-1.24 (m, 1H), 0.96 (s, 9H).

Exemplary Synthesis of (2R,3S,4R,5S)—N-(4-((2-(2-(2-(3-((4-(4-acetylpiperazin-1-yl)-6-chloro-8-fluoro-7-((S)-2-fluoro-6-hydroxyphenyl)quinazolin-2-yl)amino)-N-methylpropanamido)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide (Exemplary compound 319)

Step 1: Preparation of tert-butyl 4-(6-chloro-2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-11-methyl-1,12-dioxo-5,8-dioxa-2,11-diazatetradecan-14-yl)amino)-8-fluoro-7-((S)-2-fluoro-6-hydroxyphenyl)quinazolin-4-yl)piperazine-1-carboxylate

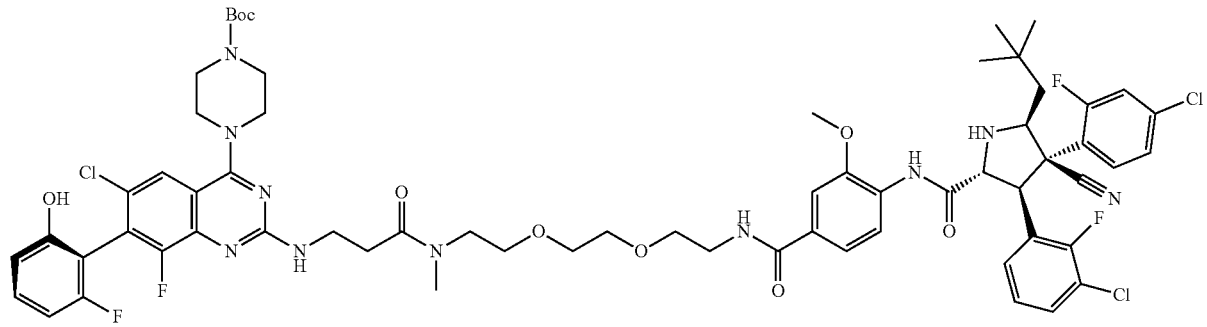

To the mixture of (2R,3S,4R,5S)-3-(3-chloro-2-fluorophenyl)-4-(4-chloro-2-fluoro-phenyl)-4-cyano-5-(2,2-dimethylpropyl)-N-[2-methoxy-4-[2-[2-[2-(methylamino)ethoxy]ethoxy]ethylcarbamoyl]phenyl]pyrrolidine-2-carboxamide (175 mg, 0.2 mmol, 1 eq, trifluoroacetate) and 4-[4-(4-tert-butoxycarbonylpiperazin-1-yl)-6-chloro-8-fluoro-7-(2-fluoro-6-hydroxy-phenyl)quinazolin-2-yl]butanoic acid (112 mg, 0.2 mmol, 1 eq) in N,N-dimethylformamide (8 mL) was added 1-hydroxybenzotriazole (54 mg, 0.40 mmol, 2 eq), N-(3-dimethylaminopropyl)-N-ethylcarbodiimide hydrochloride (76 mg, 0.40 mmol, 2 eq) and N,N-diisopropylethylamine (129 mg, 1.00 mmol, 0.17 mL, 5 eq). The mixture was stirred at 25° C. for 12 hours. The mixture was diluted with water (25 mL). Then it was extracted with ethyl acetate (25 mL×3). The combined organic layer was washed with water (30 mL×2) and brine (30 mL×2), dried over anhydrous sodium sulfate, filtered and concentrated under reduced pressure to give a residue. The residue was purified by prep-Thin-layer chromatography (dichloromethane:methanol=10:1). Compound tert-butyl 4-[6-chloro-2-[[3-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethyl-methyl-amino]-3-oxo-propyl]amino]-8-fluoro-7-(2-fluoro-6-hydroxy-phenyl)quinazolin-4-yl]piperazine-1-carboxylate (180 mg, 0.14 mmol, 68% yield) was obtained as a light yellow solid. LC/MS (ESI) m/z: 1307.4 [M+1]$^+$.

Step 2: Preparation of (2R,3S,4R,5S)-3-(3-chloro-2-fluorophenyl)-4-(4-chloro-2-fluorophenyl)-N-(4-((2-(2-(2-(3-((6-chloro-8-fluoro-7-((S)-2-fluoro-6-hydroxyphenyl)-4-(piperazin-1-yl)quinazolin-2-yl)amino)-N-methylpropanamido)ethoxy)ethoxy)ethyl)carbamoyl)-2-methoxyphenyl)-4-cyano-5-neopentylpyrrolidine-2-carboxamide

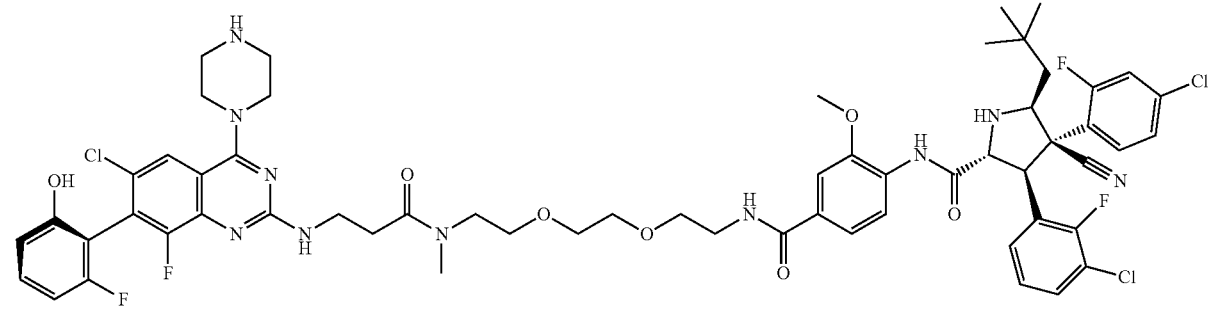

To the mixture of tert-butyl 4-[6-chloro-2-[[3-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethyl-methyl-amino]-3-oxo-propyl]amino]-8-fluoro-7-(2-fluoro-6-hydroxy-phenyl)quinazolin-4-yl]piperazine-1-carboxylate (180 mg, 0.14 mmol, 1 eq) in dichloromethane (5 mL) was added trifluoroacetic acid (1 mL). The mixture was stirred at 25° C. for 0.5 hour. The mixture was concentrated under reduced pressure to give the product. (2R,3S,4R,5S)—N-[4-[2-[2-[2-[3-[[6-chloro-8-fluoro-7-(2-fluoro-6-hydroxy-phenyl)-4-piperazin-1-yl-quinazolin-2-yl]amino]propanoyl-methyl-amino]ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (180 mg, trifluoroacetate) was obtained as a light yellow oil. LC/MS (ESI) m/z: 1207.3 [M+1]⁺.

Step 3: Preparation of (2R,3S,4R,5S)—N-(4-((2-(2-(2-(3-((4-(4-acetylpiperazin-1-yl)-6-chloro-8-fluoro-7-((S)-2-fluoro-6-hydroxyphenyl)quinazolin-2-yl)amino)-N-methylpropanamido)ethoxy)ethoxy)ethyl)carbamoyl)-2-methoxyphenyl)-3-(3-chloro-2-fluorophenyl)-4-(4-chloro-2-fluoro-phenyl)-4-cyano-5-neopentylpyrrolidine-2-carboxamide

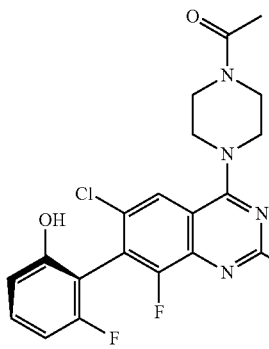
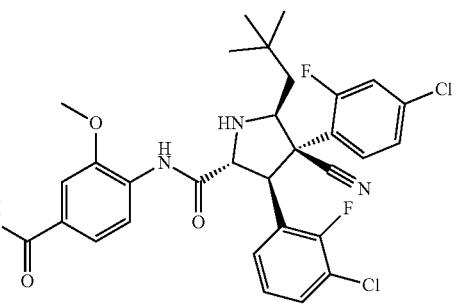

To the mixture of (2R,3S,4R,5S)—N-[4-[2-[2-[2-[3-[[6-chloro-8-fluoro-7-(2-fluoro-6-hydroxy-phenyl)-4-piperazin-1-yl-quinazolin-2-yl]amino]propanoyl-methyl-amino]ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (90 mg, 0.07 mmol, 1 eq, trifluoroacetate) and 2,6-lutidine (73 mg, 0.68 mmol, 0.08 mL, 10 eq) in dichloromethane (20 mL) was added acetyl chloride (5 mg, 0.07 mmol, 0.004 mL, 1 eq) in dichloromethane (5 mL) at −78° C. under nitrogen atmosphere. The mixture was stirred at −78° C. for 20 minutes. The mixture was quenched with water (20 mL). Then it was extracted with dichloromethane (20 mL×2). The combined organic layer was washed with brine (30 mL×2), dried over anhydrous sodium sulfate, filtered and concentrated under reduced pressure to give a residue. The residue was purified by prep-HPLC. Compound (2R,3S,4R,5S)—N-[4-[2-[2-[2-[3-[[4-(4-acetylpiperazin-1-yl)-6-chloro-8-fluoro-7-(2-fluoro-6-hydroxy-phenyl)quinazolin-2-yl]amino]propanoyl-methyl-amino]ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (51.1 mg, 0.04 mmol, 59% yield, 99% purity) was obtained as a white solid. LC/MS (ESI) m/z: 1249.3 [M+1]⁺; ¹H-NMR (400 MHz, DMSO-$d_6$) δ 10.49-10.39 (m, 2H), 8.48-8.44 (m, 1H), 8.31 (dd, J=2.0, 8.4 Hz, 1H), 8.02-8.01 (m, 2H), 7.74-7.71 (m, 1H), 7.58-7.45 (m, 4H), 7.38-7.33 (m, 4H), 6.88-6.79 (m, 2H), 4.58 (s, 2H), 4.16-4.12 (m, 3H), 3.96-3.90 (m, 7H), 3.55-3.37 (m, 17H), 2.96-2.84 (m, 3H), 2.71-2.65 (m, 2H), 2.04-2.03 (m, 3H), 1.67-1.61 (m, 1H), 1.28-1.24 (m, 1H), 0.96 (s, 9H).

Exemplary Synthesis of (2R,3S,4R,5S)—N-(4-((2-(2-(2-(3-(((4-(4-acetylpiperazin-1-yl)-6-chloro-8-fluoro-7-((R)-2-fluoro-6-hydroxyphenyl)quinazolin-2-yl)amino)-N-methylpropanamido)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide (Exemplary Compound 320)

Step 1: Preparation of tert-butyl 4-(6-chloro-2-((1-(4-(((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-11-methyl-1,12-dioxo-5,8-dioxa-2,11-diazatetradecan-14-yl)amino)-8-fluoro-7-((R)-2-fluoro-6-hydroxyphenyl)quinazolin-4-yl)piperazine-1-carboxylate

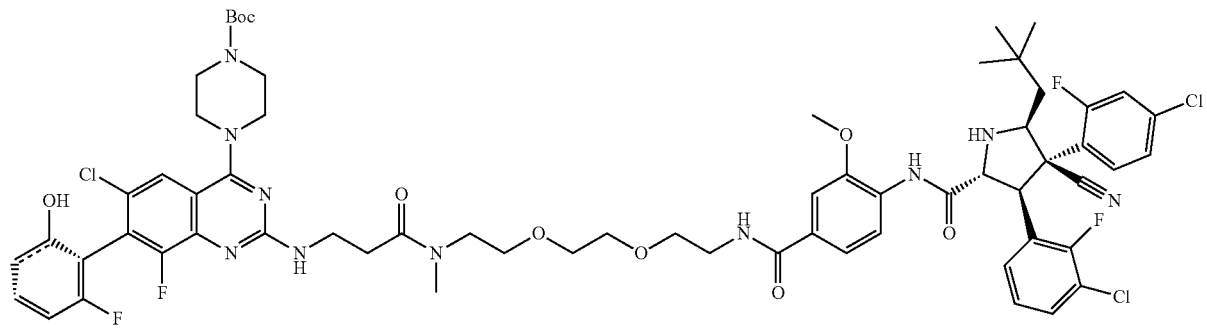

To the mixture of (2R,3S,4R,5S)-3-(3-chloro-2-fluorophenyl)-4-(4-chloro-2-fluoro-phenyl)-4-cyano-5-(2,2-dimethylpropyl)-N-[2-methoxy-4-[2-[2-[2-(methylamino)ethoxy]ethoxy]ethylcarbamoyl]phenyl]pyrrolidine-2-carboxamide (175 mg, 0.20 mmol, 1 eq, trifluoroacetate) and 4-[4-(4-tert-butoxycarbonylpiperazin-1-yl)-6-chloro-8-fluoro-7-(2-fluoro-6-hydroxy-phenyl)quinazolin-2-yl]butanoic acid (112 mg, 0.20 mmol, 1 eq) in N,N-dimethylformamide (8 mL) was added 1-hydroxybenzotriazole (54 mg, 0.40 umol, 2 eq), N-(3-dimethylaminopropyl)-N-ethylcarbodiimide hydrochloride (76 mg, 0.40 mmol, 2 eq) and N,N-diisopropylethylamine (129 mg, 1.00 mmol, 0.17 mL, 5 eq). The mixture was stirred at 25° C. for 12 hours. The mixture was diluted with water (20 mL). Then it was extracted with ethyl acetate (20 mL×3). The combined organic layer was washed with water (30 mL×2) and brine (30 mL×2), dried over anhydrous sodium sulfate, filtered and concentrated under reduced pressure to give a residue. The residue was purified by prep-Thin-layer chromatography (dichloromethane:methanol=10:1) Compound tert-butyl 4-[6-chloro-2-[[3-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethyl-methyl-amino]-3-oxo-propyl]amino]-8-fluoro-7-(2-fluoro-6-hydroxy-phenyl)quinazolin-4-yl]piperazine-1-carboxylate (140 mg, 0.11 mmol, 53% yield) was obtained as a light yellow solid. LC/MS (ESI) m/z: 1307.4 [M+1]+.

Step 2: Preparation of (2R,3S,4R,5S)-3-(3-chloro-2-fluorophenyl)-4-(4-chloro-2-fluorophenyl)-N-(4-((2-(2-(2-(3-(((6-chloro-8-fluoro-7-((R)-2-fluoro-6-hydroxyphenyl)-4-(piperazin-1-yl)quinazolin-2-yl)amino)-N-methylpropanamido)ethoxy)ethoxy)ethyl)carbamoyl)-2-methoxyphenyl)-4-cyano-5-neopentylpyrrolidine-2-carboxamide

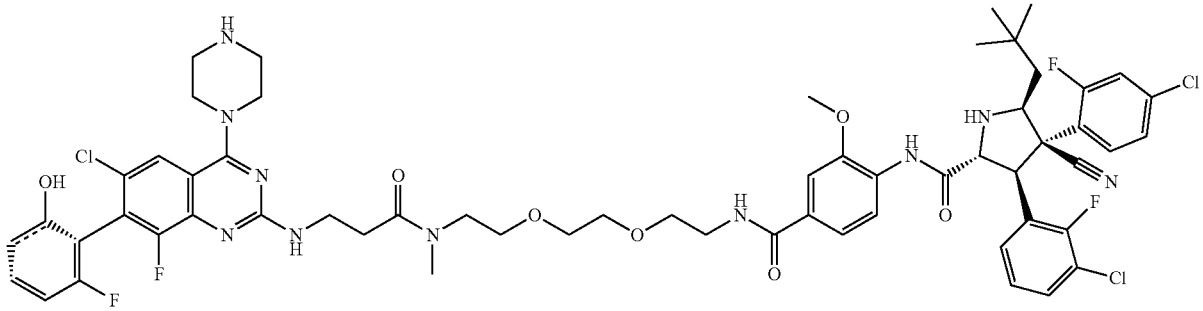

To the mixture of tert-butyl 4-[6-chloro-2-[[3-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethyl-methyl-amino]-3-oxo-propyl]amino]-8-fluoro-7-(2-fluoro-6-hydroxy-phenyl)quinazolin-4-yl]piperazine-1-carboxylate (140 mg, 0.11 mmol, 1 eq) in dichloromethane (5 mL) was added trifluoroacetic acid (1 mL). The mixture was stirred at 25° C. for 0.5 hour. The mixture was concentrated under reduced pressure to give the product. (2R,3S,4R,5S)—N-[4-[2-[2-[2-[3-[[6-chloro-8-fluoro-7-(2-fluoro-6-hydroxy-phenyl)-4-piperazin-1-yl-quinazolin-2-yl]amino]propanoyl-methyl-amino]ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (140 mg, trifluoroacetate) was obtained as a light yellow oil. LC/MS (ESI) m/z: 1207.4 [M+1]⁺.

Step 3: Preparation of (2R,3S,4R,5S)—N-(4-((2-(2-(2-(3-((4-(4-acetylpiperazin-1-yl)-6-chloro-8-fluoro-7-((R)-2-fluoro-6-hydroxyphenyl)quinazolin-2-yl)amino)-N-methylpropanamido)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (70 mg, 0.05 mmol, 1 eq, trifluoroacetate) and 2,6-lutidine (56 mg, 0.53 mmol, 0.06 mL, 10 eq) in dichloromethane (20 mL) was added acetyl chloride (4 mg, 0.05 mmol, 0.004 mL, 1 eq) in dichloromethane (5 mL) at −78° C. under nitrogen atmosphere. The mixture was stirred at −78° C. for 20 minutes. The mixture was quenched with water (20 mL). Then it was extracted with dichloromethane (20 mL×2). The combined organic layer was washed with brine (30 mL×2), dried over anhydrous sodium sulfate, filtered and concentrated under reduced pressure to give a residue. The residue was purified by prep-HPLC. Compound (2R,3S,4R,5S)—N-[4-[2-[2-[2-[3-[[4-(4-acetylpiperazin-1-yl)-6-chloro-8-fluoro-7-(2-fluoro-6-hydroxy-phenyl)quinazolin-2-yl]amino]propanoyl-methyl-amino]ethoxy]ethoxy]ethylcarbamoyl]-2-methoxy-phenyl]-3-(3-chloro-2-fluoro-phenyl)-4-(4-chloro-2-fluoro-phenyl)-4-cyano-5-(2,2-dimethylpropyl)pyrrolidine-2-carboxamide (30.1 mg, 0.02 mmol, 45% yield, 99% purity) was obtained as a white solid. LC/MS (ESI) m/z: 1249.4 [M+1]⁺; ¹H-NMR (400 MHz, DMSO-d₆) δ 10.50-10.39 (m, 2H), 8.47-8.45 (m, 1H), 8.31 (dd, J=2.0, 8.4 Hz, 1H), 8.02-8.00 (m, 2H), 7.74-7.71 (m, 1H), 7.58-7.46 (m, 4H), 7.40-7.32 (m, 4H), 6.88-6.79 (m, 2H), 4.58 (s, 2H), 4.16-4.12 (m, 3H), 3.93-3.90 (m, 7H),

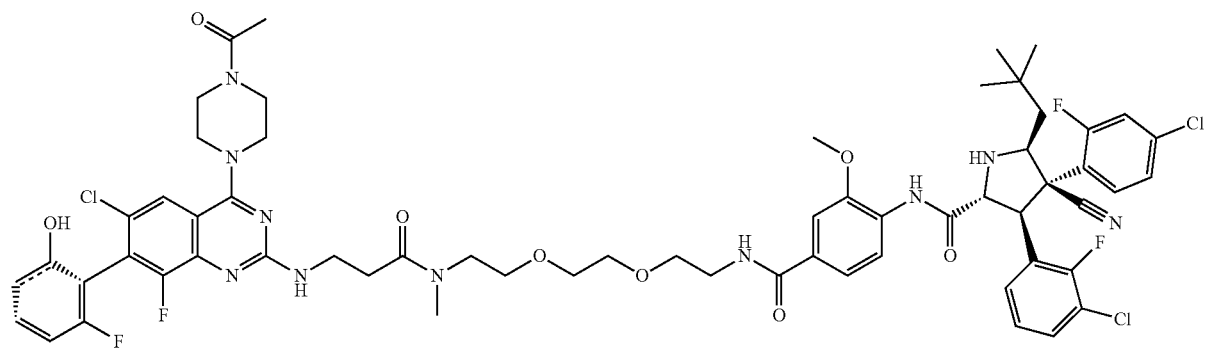

To the mixture of (2R,3S,4R,5S)—N-[4-[2-[2-[2-[3-[[6-chloro-8-fluoro-7-(2-fluoro-6-hydroxy-phenyl)-4-piperazin-1-yl-quinazolin-2-yl]amino]propanoyl-methyl-amino]

3.54-3.37 (m, 17H), 2.96-2.84 (m, 3H), 2.71-2.65 (m, 2H), 2.04-2.03 (m, 3H), 1.67-1.61 (m, 1H), 1.28-1.24 (m, 1H), 0.96 (s, 9H).

Exemplary Synthesis of (2S,4R)—N-(2-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide (Exemplary Compound 339)

Step 1: Preparation of (2S,4R)-4-hydroxy-1-((R)-3-methyl-2-(3-methylisoxazol-5-yl)butanoyl)-N-(2-(2-(2-(methylamino)ethoxy)ethoxy)-4-(4-methylthiazol-5-yl)benzyl)pyrrolidine-2-carboxamide A mixture of tert-butyl N-[2-[2-[2-[[[(2S,4R)-4-hydroxy-1-[(2R)-3-methyl-2-(3-methylisoxazol-5-yl)butanoyl]pyrrolidine-2-carbonyl]amino]methyl]-5-(4-methylthiazol-5-yl)phenoxy]ethoxy]ethyl]-N-methyl-carbamate (90 mg, 0.12 mmol, 1 eq) in hydrochloric acid/dioxane (4 M, 10 mL, 311 eq) was degassed and purged with nitrogen for 3 times, and then the mixture was stirred at 25° C. for 0.5 hour under nitrogen. The reaction mixture was concentrated under reduced pressure to give a residue. Compound (2S,4R)-4-hydroxy-N-[[2-[2-[2-(methylamino)ethoxy]ethoxy]-4-(4-methylthiazol-5-yl)phenyl]methyl]-1-[(2R)-3-methyl-2-(3-methylisoxazol-5-yl)butanoyl]pyrrolidine-2-carboxamide (75 mg, 0.11 mmol, 91% yield, hydrochloride) was obtained as a colorless oil. LC/MS (ESI) m/z: 600.4 [M+1]$^+$.

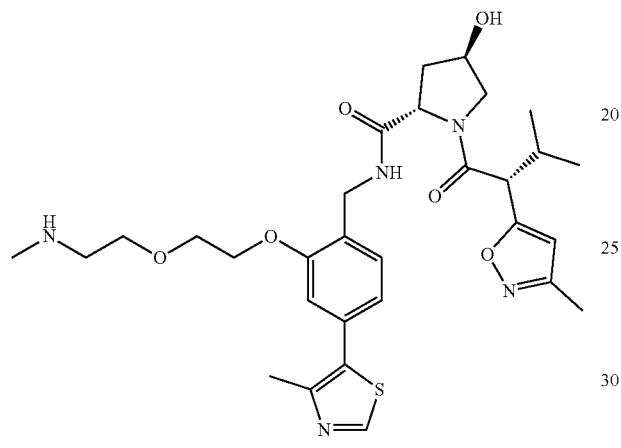

Step 2: Preparation of tert-butyl 4-(6-chloro-8-fluoro-2-((3-((2-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)amino)-3-oxopropyl)amino)-7-(3-hydroxynaphthalen-1-yl)quinazolin-4-yl)piperazine-1-carboxylate

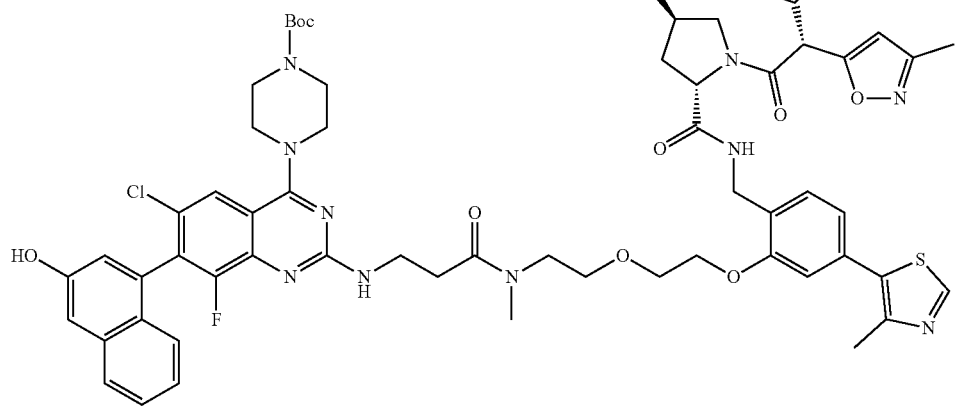

A mixture of (2S,4R)-4-hydroxy-N-[[2-[2-[2-(methylamino)ethoxy]ethoxy]-4-(4-methylthiazol-5-yl)phenyl]methyl]-1-[(2R)-3-methyl-2-(3-methylisoxazol-5-yl)butanoyl]pyrrolidine-2-carboxamide (75 mg, 0.11 mmol, 1 eq, hydrochloride), 3-[[4-(4-tert-butoxycarbonylpiperazin-1-yl)-6-chloro-8-fluoro-7-(3-hydroxy-1-naphthyl)quinazolin-2-yl]amino]propanoic acid (70 mg, 0.11 mmol, 1 eq), 1-hydroxybenzotriazole (23 mg, 0.17 mmol, 1.5 eq), 1-(3-dimethylaminopropyl)-3-ethylcarbodiimide hydrochloride (33 mg, 0.17 mmol, 1.5 eq) and N,N-diisopropylethylamine (61 mg, 0.47 mmol, 4 eq) in N,N-dimethylformamide (1 mL) was degassed and purged with nitrogen for 3 times, and then the mixture was stirred at 25° C. for 12 hours under nitrogen. The reaction mixture was quenched by addition water 10 mL, and extracted with ethyl acetate (20 mL×3). The combined organic layers were washed with brine (O1 mL×3), dried over sodium sulfate, filtered and concentrated under reduced pressure to give a residue. The residue was purified by prep-TLC (9% methanol in dichloromethane). tert-butyl 4-[6-chloro-8-fluoro-2-[[3-[2-[2-[2-[[[(2S,4R)-4-hydroxy-1-[(2R)-3-methyl-2-(3-methylisoxazol-5-yl)butanoyl]pyrrolidine-2-carbonyl]amino]methyl]-5-(4-methylthiazol-5-yl)phenoxy]ethoxy]ethyl-methyl-amino]-3-oxopropyl]amino]-7-(3-hydroxy-1-naphthyl)quinazolin-4-yl]piperazine-1-carboxylate (75 mg, 0.06 mmol, 50% yield, 93% purity) was obtained as a yellow oil. LC/MS (ESI) m/z: 590.1 [M/2+1]⁺.

Step 3: Preparation of (2S,4R)—N-(2-(2-(2-(3-((6-chloro-8-fluoro-7-(3-hydroxynaphthalen-1-yl)-4-(piperazin-1-yl)quinazolin-2-yl)amino)-N-methylpropanamido)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide

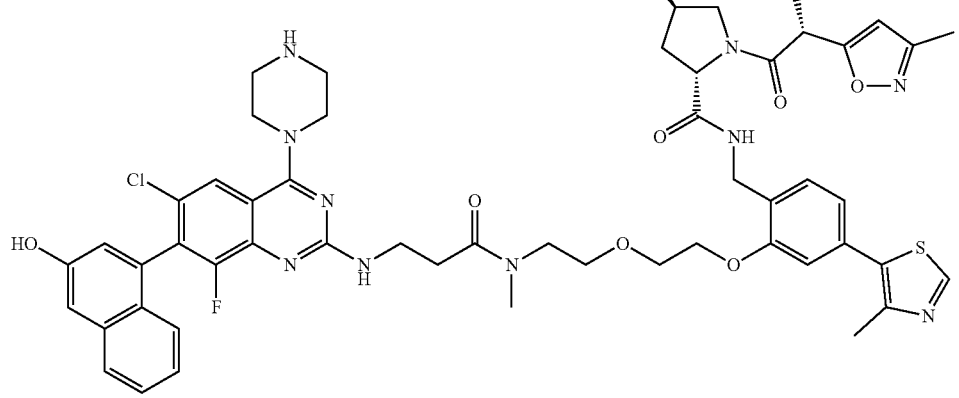

A mixture of tert-butyl 4-[6-chloro-8-fluoro-2-[[3-[2-[2-[2-[[[(2S,4R)-4-hydroxy-1-[(2R)-3-methyl-2-(3-methylisoxazol-5-yl)butanoyl]pyrrolidine-2-carbonyl]amino]methyl]-5-(4-methylthiazol-5-yl)phenoxy]ethoxy]ethyl-methyl-amino]-3-oxo-propyl]amino]-7-(3-hydroxy-1-naphthyl)quinazolin-4-yl]piperazine-1-carboxylate (80 mg, 0.06 mmol, 1 eq) and trifluoroacetic acid (821 mg, 7.20 mmol, 106.05 eq) in dichloromethane (5 mL) was degassed and purged with nitrogen for 3 times, and then the mixture was stirred at 25° C. for 1 hour under nitrogen. The reaction mixture was concentrated under reduced pressure to give (2S,4R)—N-[[2-[2-[2-[3-[[6-chloro-8-fluoro-7-(3-hydroxy-1-naphthyl)-4-piperazin-1-yl-quinazolin-2-yl]amino]propanoyl-methyl-amino]ethoxy]ethoxy]-4-(4-methylthiazol-5-yl)phenyl]methyl]-4-hydroxy-1-[(2R)-3-methyl-2-(3-methylisoxazol-5-yl)butanoyl]pyrrolidine-2-carboxamide (75 mg, 0.06 mmol, 92% yield, trifluoroacetate) as a yellow oil.

Step 4: Preparation of (2S,4R)—N-(2-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide

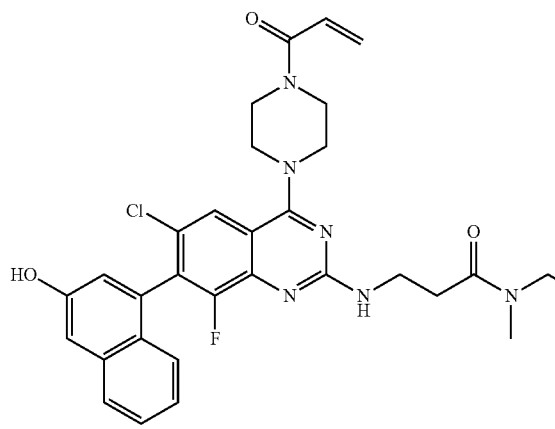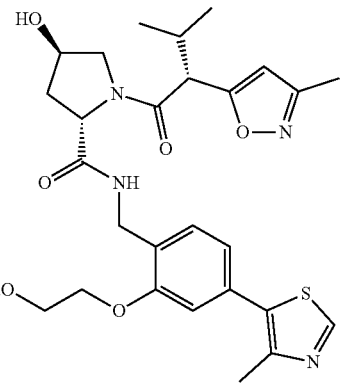

To a solution of (2S,4R)—N-[[2-[2-[2-[3-[[6-chloro-8-fluoro-7-(3-hydroxy-1-naphthyl)-4-piperazin-1-yl-quinazolin-2-yl]amino]propanoyl-methyl-amino]ethoxy]ethoxy]-4-(4-methylthiazol-5-yl)phenyl]methyl]-4-hydroxy-1-[(2R)-3-methyl-2-(3-methylisoxazol-5-yl)butanoyl]pyrrolidine-2-carboxamide (75 mg, 0.06 mmol, 1 eq, trifluoroacetate) and 2,6-lutidine (67 mg, 0.62 mmol, 0.073 mL, 10 eq) in dichloromethane (20 mL) was added a solution of prop-2-enoyl chloride (6 mg, 0.06 mmol, 0.05 mL, 1 eq) in dichloromethane (1 mL) drop-wise at −78° C. under nitrogen. The reaction solution was stirred at −78° C. for 0.5 hour. The reaction mixture was quenched by addition water 10 mL, and extracted with ethyl acetate (20 mL×3). The combined organic layers were washed with brine (O1 mL×3), dried over sodium sulfate, filtered and concentrated under reduced pressure to give a residue. The residue was purified by semi-preparative reverse phase HPLC. Compound 2S,4R)—N-[[2-[2-[2-[3-[[6-chloro-8-fluoro-7-(3-hydroxy-1-naphthyl)-4-(4-prop-2-enoylpiperazin-1-yl)quinazolin-2-yl]amino]propanoyl-methyl-amino]ethoxy]ethoxy]-4-(4-methylthiazol-5-yl)phenyl]methyl]-4-hydroxy-1-[(2R)-3-methyl-2-(3-methylisoxazol-5-yl)butanoyl]pyrrolidine-2-carboxamide (45 mg, 0.04 mol, 62% yield, 99% purity) was obtained as a white solid. LC/MS (ESI) m/z: 566.5 [M/2+1]$^+$; $^1$H-NMR (400 MHz, DMSO-d$_6$) δ 9.98 (br s, 1H), 8.97 (s, 1H), 8.30-8.21 (m, 1H), 7.79 (br d, J=7.9 Hz, 2H), 7.52-7.34 (m, 1H), 7.32-6.94 (m, 8H), 6.89-6.79 (m, 1H), 6.24-6.14 (m, 2H), 5.74 (br d, J=10.6 Hz, 1H), 5.11 (br s, 1H), 4.55-4.15 (m, 6H), 3.93-3.76 (m, 11H), 3.66-3.49 (m, 6H), 3.03-2.70 (m, 4H), 2.65-2.55 (m, 4H), 2.47-2.39 (m, 3H), 2.30-2.03 (m, 1H), 2.15-2.12 (m, 2H), 2.07-2.00 (m, 1H), 1.91 (br dd, J=5.1, 7.6 Hz, 1H), 0.97 (d, J=6.6 Hz, 2H), 0.80 (d, J=6.7 Hz, 2H), 0.68 (br d, J=6.5 Hz, 1H), 0.56 (br d, J=6.4 Hz, 1H).

Exemplary Synthesis of (2S,4R)—N-(2-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide (Exemplary Compound 340)

Step 1: Preparation of (2S,4R)-4-hydroxy-1-((S)-3-methyl-2-(3-methylisoxazol-5-yl)butanoyl)-N-(2-(2-(2-(methylamino)ethoxy)ethoxy)-4-(4-methylthiazol-5-yl)benzyl)pyrrolidine-2-carboxamide

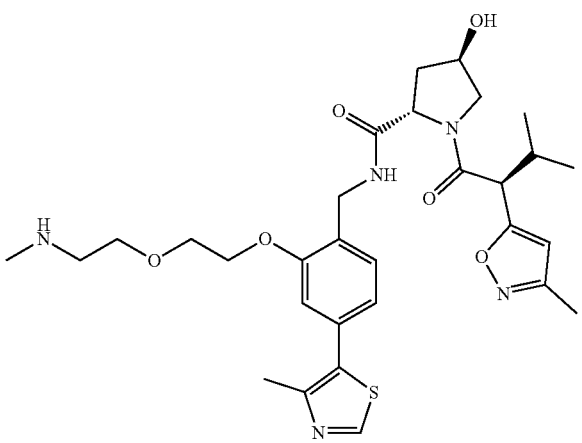

A mixture of tert-butyl N-[2-[2-[2-[[[(2S,4R)-4-hydroxy-1-[(2S)-3-methyl-2-(3-methylisoxazol-5-yl)butanoyl]pyrrolidine-2-carbonyl]amino]methyl]-5-(4-methylthiazol-5-yl)phenoxy]ethoxy]ethyl]-N-methyl-carbamate (90 mg, 0.12 mmol, 1 eq) in hydrochloric acid/dioxane (4 M, 10 mL, 311 eq) was degassed and purged with nitrogen for 3 times, and then the mixture was stirred at 25° C. for 0.5 hour under nitrogen. The reaction mixture was concentrated under reduced pressure to give a residue. Compound (2S,4R)-4-hydroxy-N-[[2-[2-[2-(methylamino)ethoxy]ethoxy]-4-(4-methylthiazol-5-yl)phenyl]methyl]-1-[(2S)-3-methyl-2-(3-methylisoxazol-5-yl)butanoyl]pyrrolidine-2-carboxamide (75 mg, 0.11 mmol, 91% yield, hydrochloride) was obtained as a colorless oil. LC/MS (ESI) m/z: 600.4 [M+1]$^+$.

Step 2: Preparation of tert-butyl 4-(6-chloro-8-fluoro-2-((3-((2-(2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)amino)-3-oxopropyl)amino)-7-(3-hydroxynaphthalen-1-yl)quinazolin-4-yl)piperazine-1-carboxylate

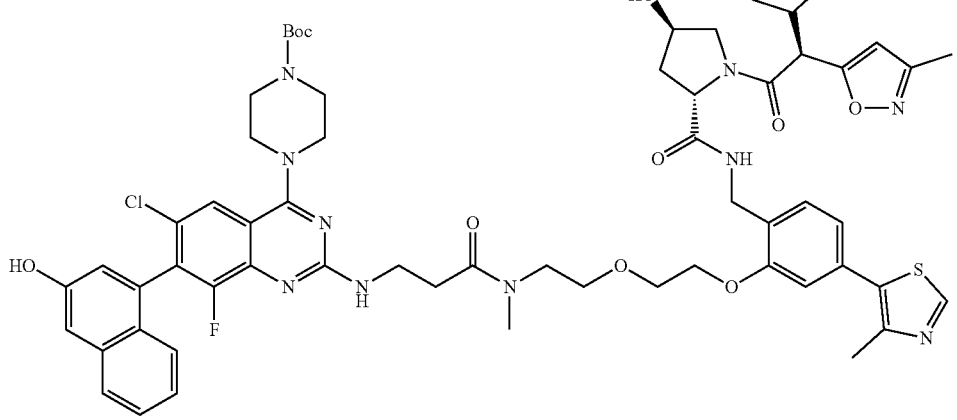

A mixture of (2S,4R)-4-hydroxy-N-[[2-[2-[2-(methylamino)ethoxy]ethoxy]-4-(4-methylthiazol-5-yl)phenyl]methyl]-1-[(2S)-3-methyl-2-(3-methylisoxazol-5-yl)butanoyl]pyrrolidine-2-carboxamide (75 mg, 0.11 mmol, 1 eq, hydrochloride), 3-[[4-(4-tert-butoxycarbonylpiperazin-1-yl)-6-chloro-8-fluoro-7-(3-hydroxy-1-naphthyl)quinazolin-2-yl]amino]propanoic acid (70 mg, 0.11 mmol, 1 eq), 1-hydroxybenzotriazole (23 mg, 0.17 mmol, 1.5 eq), 1-(3-dimethylaminopropyl)-3-ethylcarbodiimide hydrochloride (33 mg, 0.17 mmol, 1.5 eq) and N,N-diisopropylethylamine (61 mg, 0.47 mmol, 4 eq) in N,N-dimethylformamide (1 mL) was degassed and purged with nitrogen for 3 times, and then the mixture was stirred at 25° C. for 12 hours under nitrogen. The reaction mixture was quenched by addition water 10 mL, and extracted with ethyl acetate (20 mL×3). The combined organic layers were washed with brine (10 mL×3), dried over sodium sulfate, filtered and concentrated under reduced pressure to give a residue. The residue was purified by prep-TLC (9% methanol in dichloromethane). tert-butyl 4-[6-chloro-8-fluoro-2-[[3-[2-[2-[2-[[[(2S,4R)-4-hydroxy-1-[(2S)-3-methyl-2-(3-methylisoxazol-5-yl)butanoyl]pyrrolidine-2-carbonyl]amino]methyl]-5-(4-methylthiazol-5-yl)phenoxy]ethoxy]ethyl-methyl-amino]-3-oxopropyl]amino]-7-(3-hydroxy-1-naphthyl)quinazolin-4-yl]piperazine-1-carboxylate (75 mg, 0.06 mmol, 50% yield, 93% purity) was obtained as a yellow oil. LC/MS (ESI) m/z: 590.4 [M/2+1]$^+$.

Step 3: Preparation of (2S,4R)—N-(2-(2-(2-(3-((6-chloro-8-fluoro-7-(3-hydroxynaphthalen-1-yl)-4-(piperazin-1-yl)quinazolin-2-yl)amino)-N-methylpropanamido)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide

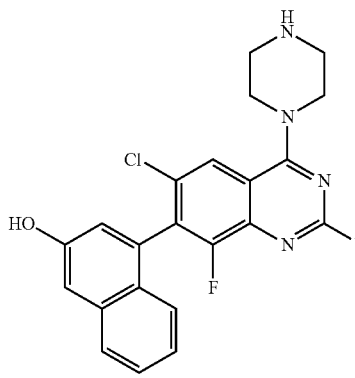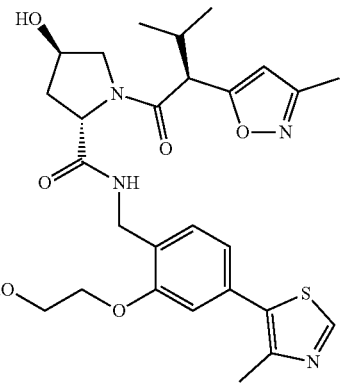

A mixture of tert-butyl 4-[6-chloro-8-fluoro-2-[[3-[2-[2-[2-[[[(2S,4R)-4-hydroxy-1-[(2S)-3-methyl-2-(3-methyl-isoxazol-5-yl)butanoyl]pyrrolidine-2-carbonyl]amino]methyl]-5-(4-methylthiazol-5-yl)phenoxy]ethoxy]ethyl-methyl-amino]-3-oxo-propyl]amino]-7-(3-hydroxy-1-naphthyl)quinazolin-4-yl]piperazine-1-carboxylate (80 mg, 0.06 mmol, 1 eq) and trifluoroacetic acid (821 mg, 7.20 mmol, 106.05 eq) in dichloromethane (5 mL) was degassed and purged with nitrogen for 3 times, and then the mixture was stirred at 25° C. for 1 hour under nitrogen. The reaction mixture was concentrated under reduced pressure to give a residue. Compound (2S,4R)—N-[[2-[2-[2-[3-[[6-chloro-8-fluoro-7-(3-hydroxy-1-naphthyl)-4-piperazin-1-yl-quinazolin-2-yl]amino]propanoyl-methyl-amino]ethoxy]ethoxy]-4-(4-methylthiazol-5-yl)phenyl]methyl]-4-hydroxy-1-[(2S)-3-methyl-2-(3-methylisoxazol-5-yl)butanoyl]pyrrolidine-2-carboxamide (75 mg, 0.06 mmol, 92% yield, trifluoroacetate) was obtained as a yellow oil.

Step 4: Preparation of (2S,4R)—N-(2-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide

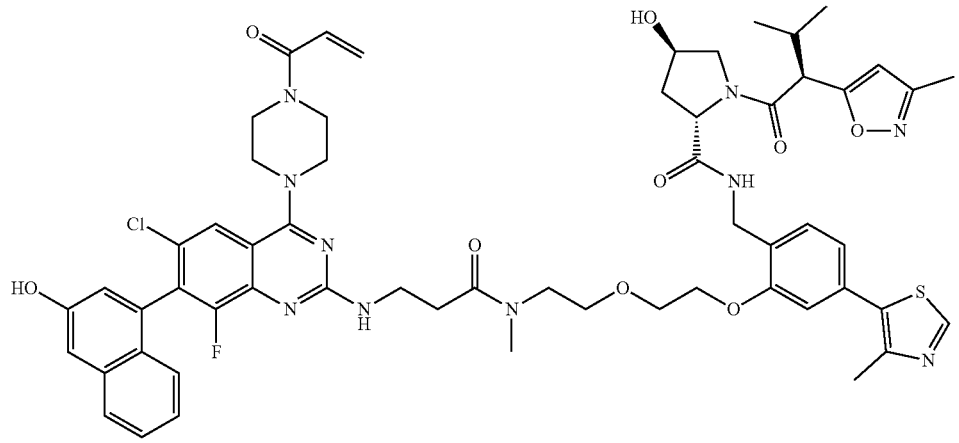 [SMILES: C=CC(=O)N1CCN(c2nc(NCCC(=O)N(C)CCOCCOc3cc(-c4scnc4C)ccc3CNC(=O)[C@@H]3C[C@@H](O)CN3C(=O)[C@H](c3cc(C)no3)C(C)C)nc3c(F)c(-c4cc(O)cc5ccccc45)c(Cl)cc23)CC1]

To a solution of (2S,4R)—N-[[2-[2-[2-[3-[[6-chloro-8-fluoro-7-(3-hydroxy-1-naphthyl)-4-piperazin-1-yl-quinazolin-2-yl]amino]propanoyl-methyl-amino]ethoxy]ethoxy]-4-(4-methylthiazol-5-yl)phenyl]methyl]-4-hydroxy-1-[(2S)-3-methyl-2-(3-methylisoxazol-5-yl)butanoyl]pyrrolidine-2-carboxamide (75 mg, 0.06 mmol, 1 eq, trifluoroacetate) and 2,6-lutidine (67 mg, 0.62 mmol, 73 uL, 10 eq) in dichloromethane (20 mL) was added a solution of prop-2-enoyl chloride (6 mg, 0.06 mmol, 5.13 uL, 1 eq) in dichloromethane (1 mL) drop-wise at −78° C. under nitrogen. The reaction solution was stirred at −78° C. for 0.5 hour. The reaction mixture was quenched by addition water 10 mL, and extracted with ethyl acetate (20 mL×3). The combined organic layers were washed with brine (10 mL×3), dried over sodium sulfate, filtered and concentrated under reduced pressure to give a residue. The residue was purified by semi-preparative reverse phase HPLC. 2S,4R)—N-[[2-[2-[2-[3-[[6-chloro-8-fluoro-7-(3-hydroxy-1-naphthyl)-4-(4-prop-2-enoylpiperazin-1-yl)quinazolin-2-yl]amino]propanoyl-methyl-amino] ethoxy]ethoxy]-4-(4-methylthiazol-5-yl)phenyl]methyl]-4-hydroxy-1-[(2S)-3-methyl-2-(3-methylisoxazol-5-yl)butanoyl]pyrrolidine-2-carboxamide (33.7 mg, 0.03 mmol, 47% yield, 99% purity) was obtained as a white solid. LC/MS (ESI) m/z: 566.3 [M/2+1]$^+$; $^1$H-NMR (400 MHz, DMSO-d$_6$) δ 10.01 (br s, 1H), 8.97 (s, 1H), 8.33 (br s, 1H), 7.79 (br d, J=6.0 Hz, 2H), 7.46-7.38 (m, 1H), 7.34 (br d, J=7.8 Hz, 1H), 7.29-7.17 (m, 4H), 7.11-6.95 (m, 3H), 6.84 (br dd, J=10.5, 16.7 Hz, 1H), 6.24-6.14 (m, 2H), 5.74 (br d, J=10.6 Hz, 1H), 5.08 (br s, 1H), 4.48-4.12 (m, 6H), 3.88-3.72 (m, 12H), 3.60-3.50 (m, 5H), 3.22-2.83 (m, 4H), 2.71-2.57 (m, 3H), 2.47-2.41 (m, 3H), 2.30-2.27 (m, 1H), 2.25-2.19 (m, 2H), 2.15-2.09 (m, 1H), 2.07-1.99 (m, 1H), 1.97-1.84 (m, 1H), 0.99-0.88 (m, 3H), 0.81-0.72 (m, 3H).

Exemplary Synthesis of (2S,4R)-1-((2S,E)-2-(tert-butyl)-17-(4-(6-chloro-8-fluoro-7-(3-hydroxynaphthalen-1-yl)quinazolin-4-yl)piperazin-1-yl)-4,17-dioxo-6,9,12-trioxa-3-azaheptadec-15-enoyl)-4-hydroxy-N—((S)-1-(4-(4-methylthiazol-5-yl)phenyl)ethyl)pyrrolidine-2-carboxamide (Exemplary Compound 374)

Step 1: Preparation of 2-(2-(3-(benzyloxy)propoxy)ethoxy)ethan-1-ol

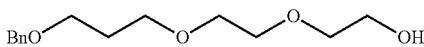

To the mixture of 2-[2-[2-(3-benzyloxypropoxy)ethoxy]ethoxy]tetrahydropyran (6.3 g, 18.61 mmol, 1 eq) in methanol (70 mL) was added para-toluenesulfonic acid (641 mg, 3.72 mmol, 0.2 eq). The mixture was stirred at 20° C. for 12 hours. The mixture was concentrated under reduced pressure to give a residue. The residue was purified by silica gel chromatography (petroleum ether:ethyl acetate=4:1 to 1:1). Compound 2-[2-(3-benzyloxypropoxy)ethoxy]ethanol (3.9 g, 15.33 mmol, 82% yield) was obtained as a colorless oil. $^1$H-NMR (400 MHz, CDCl$_3$) δ 7.35-7.28 (m, 5H), 4.51 (s, 2H), 3.72-3.71 (m, 2H), 3.62-3.60 (m, 2H), 3.59-3.56, (m, 6H), 1.94-1.86 (m, 2H).

Step 2: Preparation of ethyl 1-phenyl-2,6,9,12-tetraoxatetradecan-14-oate

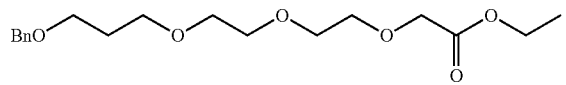 [SMILES: CCOC(=O)COCCOCCOCCCOCc1ccccc1]

To the mixture of 2-[2-(3-benzyloxypropoxy)ethoxy]ethanol (4.5 g, 17.69 mmol, 1 eq) and rhodium acetate (391 mg, 0.88 mmol, 0.05 eq) in dichloromethane (50 mL) was added ethyl 2-diazoacetate (12.11 g, 106.16 mmol, 6 eq) in dichloromethane (10 mL) drop-wise at 0° C. under nitrogen atmosphere. The mixture was stirred at 20° C. for 12 hours under nitrogen atmosphere. The mixture was quenched with acetic acid (1 mL). Then it was washed with brine (40 mL×3), dried over anhydrous sodium sulfate, filtered and concentrated under reduced pressure to give a residue. The residue was purified by silica gel chromatography (petroleum ether:ethyl acetate=5:1 to 3:1). Compound ethyl 2-[2-[2-(3-benzyloxypropoxy)ethoxy]ethoxy]acetate (3.6 g, 10.58 mmol, 59% yield) was obtained as a light yellow oil. $^1$H-NMR (400 MHz, CDCl$_3$) δ 7.34-7.27 (m, 5H), 4.51 (s, 2H), 4.22-4.20 (m, 2H), 4.14 (s, 2H), 3.78-3.70 (m, 4H), 3.59-3.58 (m, 2H), 3.57-3.56 (m, 6H), 1.93-1.85 (m, 2H), 1.30-1.28 (m, 3H).

Step 3: Preparation of ethyl 2-(2-(2-(3-hydroxypropoxy)ethoxy)ethoxy)acetate

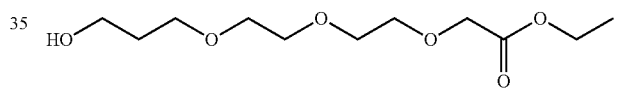

To the mixture of ethyl 2-[2-[2-(3-benzyloxypropoxy)ethoxy]ethoxy]acetate (3.6 g, 10.58 mmol, 1 eq) in ethanol (40 mL) was added palladium on activated carbon catalyst (0.4 g, 10% purity) under nitrogen atmosphere. The mixture was degassed and refilled with hydrogen for 3 times. The mixture was stirred at 50° C. for 12 hours under hydrogen atmosphere (50 psi). The mixture was filtered and concentrated under reduced pressure to give the product. Ethyl 2-[2-[2-(3-hydroxypropoxy)ethoxy]ethoxy]acetate (2.7 g) was obtained as a brown oil. $^1$H-NMR (400 MHz, CDCl$_3$) δ 4.19-4.11 (m, 2H), 3.74 (s, 2H), 3.72-3.69 (m, 4H), 3.65-3.60 (m, 8H), 1.82-1.86 (m, 2H), 1.25 (t, J=7.2 Hz, 3H).

Step 4: Preparation of ethyl 2-(2-(2-(3-oxopropoxy)ethoxy)ethoxy)acetate

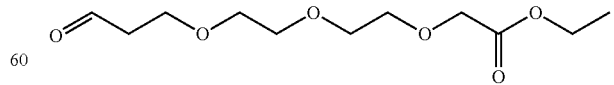

To the mixture of ethyl 2-[2-[2-(3-hydroxypropoxy)ethoxy]ethoxy]acetate (2.7 g, 10.79 mmol, 1 eq) in dichloromethane (30 mL) was added Dess-Martin Periodinane (6.86 g, 16.18 mmol, 5.01 mL, 1.5 eq) at 0° C. The mixture was stirred at 20° C. for 0.5 hour. The mixture was filtered.

The filtrate was washed with saturated sodium dicarbonate solution (30 mL×2) and brine (30 mL×2), dried over anhydrous sodium sulfate, filtered and concentrated under pressure to give a residue. The residue was purified by silica gel chromatography (petroleum ether:ethyl acetate=3:1 to 1:1). Compound ethyl 2-[2-[2-(3-oxopropoxy)ethoxy]ethoxy]acetate (2.5 g, 10.07 mmol, 93% yield) was obtained as a colorless oil. $^1$H-NMR (400 MHz, CDCl$_3$) δ 9.77 (s, 1H), 4.20-4.18 (m, 2H), 4.12 (s, 2H), 3.82-3.79 (m, 2H), 3.71-3.69 (m, 4H), 3.67-3.61 (m, 4H), 2.66 (t, J=6.0 Hz, 2H), 1.25 (t, J=3.6 Hz, 3H).

Step 5: Preparation of tert-butyl (E)-5-(2-(2-(2-ethoxy-2-oxoethoxy)ethoxy)ethoxy)pent-2-enoate

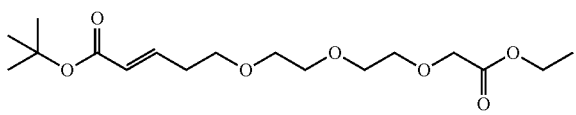 [SMILES: CCOC(=O)COCCOCCOCC/C=C/C(=O)OC(C)(C)C]

A mixture of ethyl 2-[2-[2-(3-oxopropoxy)ethoxy]ethoxy]acetate (2.5 g, 10.07 mmol, 1 eq) and tert-butyl 2-(triphenyl-phosphanylidene)acetate (3.79 g, 10.07 mmol, 1 eq) in dichloromethane (25 mL) was stirred at 20° C. for 12 hours. The mixture was concentrated under reduced pressure to give a residue. The residue was purified by silica gel chromatography (petroleum ether:ethyl acetate=6:1 to 4:1). Compound tert-butyl (E)-5-[2-[2-(2-ethoxy-2-oxoethoxy)ethoxy]ethoxy]pent-2-enoate (2.48 g, 7.16 mmol, 71% yield) was obtained as a colorless oil. $^1$H-NMR (400 MHz, CDCl$_3$) δ 6.88-6.80 (m, 1H), 5.82-5.78 (m, 1H), 4.26-4.23 (m, 2H), 4.21 (s, 2H), 3.73-3.71 (m, 4H), 3.64-3.60 (m, 2H), 3.59-3.56 (m, 4H), 2.49-2.44 (m, 2H), 1.47 (s, 9H), 1.30-1.26 (m, 3H).

Step 6: Preparation of (E)-4-oxo-3,6,9,12-tetraoxaheptadec-15-en-17-oic acid

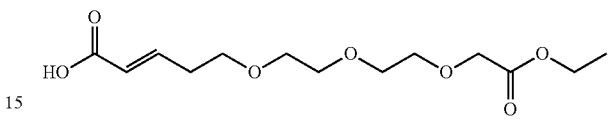

To the mixture of tert-butyl (E)-5-[2-[2-(2-ethoxy-2-oxo-ethoxy)ethoxy]ethoxy]pent-2-enoate (1.0 g, 2.89 mmol, 1 eq) in dichloromethane (15 mL) was added trifluoroacetic acid (3.00 mL). The mixture was stirred at 20° C. for 1 hour. The mixture was concentrated under reduced pressure to give the product. (E)-5-[2-[2-(2-ethoxy-2-oxo-ethoxy)ethoxy]ethoxy]pent-2-enoic acid (1.4 g) was obtained as a colorless oil. $^1$H-NMR (400 MHz, CDCl$_3$) δ 7.18-7.11 (m, 1H), 5.96-5.92 (m, 1H), 4.25-4.23 (m, 2H), 4.16 (s, 2H), 3.74-3.69 (m, 6H), 3.67-3.64 (m, 4H), 2.58-2.53 (m, 2H), 1.29 (t, J=7.2 Hz, 3H).

Step 7: Preparation of ethyl (E)-2-(2-(2-((5-(4-(6-chloro-8-fluoro-7-(3-hydroxynaphthalen-1-yl)quinazolin-4-yl)piperazin-1-yl)-5-oxopent-3-en-1-yl)oxy)ethoxy)ethoxy)acetate

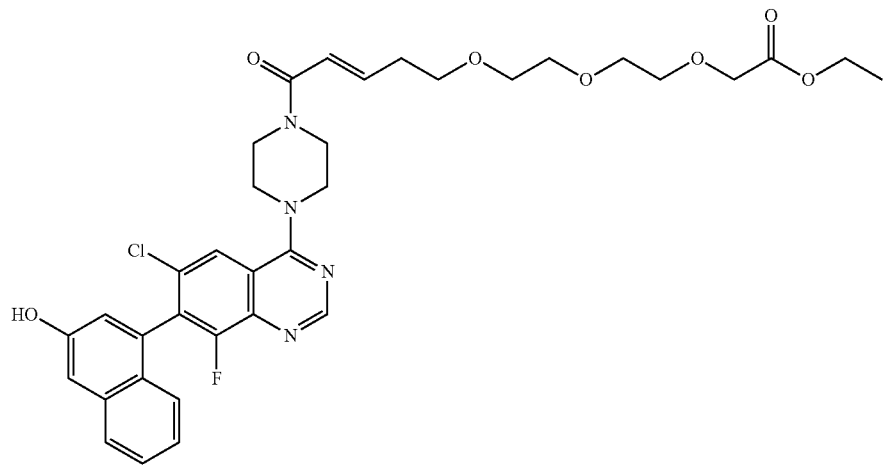 [SMILES: CCOC(=O)COCCOCCOCC/C=C/C(=O)N1CCN(c2ncnc3c(F)c(-c4cc(O)cc5ccccc45)c(Cl)cc23)CC1]

To the mixture of (E)-5-[2-[2-(2-ethoxy-2-oxo-ethoxy)ethoxy]ethoxy]pent-2-enoic acid (150 mg, 0.38 mmol, 1 eq) and 4-(6-chloro-8-fluoro-4-piperazin-1-yl-quinazolin-7-yl)naphthalen-2-ol (202 mg, 0.45 mmol, 1.17 eq, hydrochloride) in N,N-dimethylformamide (8 mL) was added 1-hydroxybenzotriazole (78 mg, 0.58 mmol, 1.5 eq), N-(3-dimethylaminopropyl)-N-ethylcarbodiimide hydrochloride (111 mg, 0.58 mmol, 1.5 eq) and N,N-diisopropylethylamin (250 mg, 1.94 mmol, 0.33 mL, 5 eq). The mixture was stirred at 20° C. for 12 hours. The mixture was diluted with water (30 mL), extracted with ethyl acetate (25 mL×3). The combined organic layer was washed with water (30 mL×2) and brine (30 mL×2), dried over anhydrous sodium sulfate, filtered and concentrated under reduced pressure to give a residue. The residue was purified by prep.TLC (dichloromethane:methanol=10:1). ethyl 2-[2-[2-[(E)-5-[4-[6-chloro-8-fluoro-7-(3-hydroxy-1-naphthyl)quinazolin-4-yl]piperazin-1-yl]-5-oxo-pent-3-enoxy]ethoxy]ethoxy]acetate (120 mg, 0.17 mmol, 45% yield) was obtained as a yellow oil. LC/MS (ESI) m/z: 681.3 [M+1]⁺.

Step 8: Preparation of (E)-2-(2-(2-((5-(4-(6-chloro-8-fluoro-7-(3-hydroxynaphthalen-1-yl)quinazolin-4-yl)piperazin-1-yl)-5-oxopent-3-en-1-yl)oxy)ethoxy)ethoxy)acetic acid

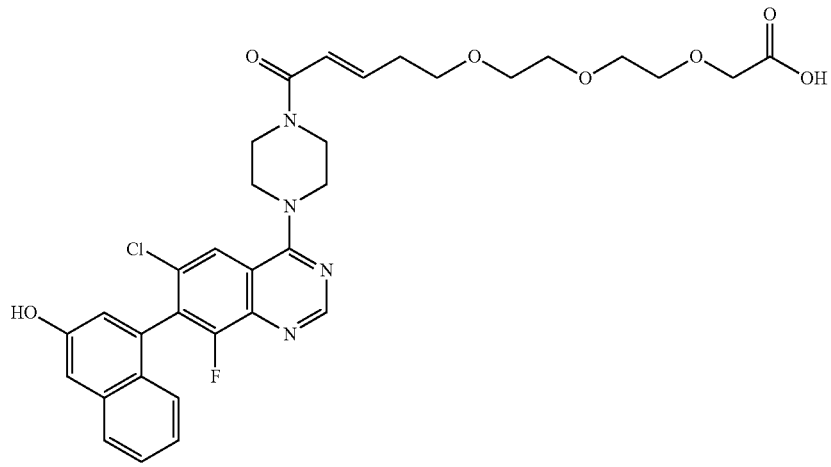 [SMILES: O=C(O)COCCOCCOCC/C=C/C(=O)N1CCN(c2ncnc3c(F)c(-c4cc(O)cc5ccccc45)c(Cl)cc23)CC1]

To the mixture of ethyl 2-[2-[2-[(E)-5-[4-[6-chloro-8-fluoro-7-(3-hydroxy-1-naphthyl)quinazolin-4-yl]piperazin-1-yl]-5-oxo-pent-3-enoxy]ethoxy]ethoxy]acetate (120 mg, 0.17 mmol, 1 eq) in tetrahydrofuran (5 mL) was added lithium hydroxide monohydrate (22 mg, 0.52 mmol, 3 eq) in water (1 mL). The mixture was stirred at 0° C. for 20 minutes. The mixture was diluted with water (10 mL), extracted with ethyl acetate (15 mL×2). Then the water phase was adjusted pH to about 5 with hydrogen chloride solution (1 M). The mixture was extracted with ethyl acetate (10 mL×3). The combined organic layer was washed with brine (20 mL×2), dried over anhydrous sodium sulfate, filtered and concentrated under reduced pressure to give the product. Compound 2-[2-[2-[(E)-5-[4-[6-chloro-8-fluoro-7-(3-hydroxy-1-naphthyl)quinazolin-4-yl]piperazin-1-yl]-5-oxo-pent-3-enoxy]ethoxy]ethoxy]acetic acid (110 mg) was obtained as a light yellow oil. LC/MS (ESI) m/z: 653.3 [M+1]⁺.

Step 9: Preparation of (2S,4R)-1-((2S,E)-2-(tert-butyl)-17-(4-(6-chloro-8-fluoro-7-(3-hydroxynaphthalen-1-yl)quinazolin-4-yl)piperazin-1-yl)-4,17-dioxo-6,9,12-trioxa-3-azaheptadec-15-enoyl)-4-hydroxy-N—((S)-1-(4-(4-methylthiazol-5-yl)phenyl)ethyl)pyrrolidine-2-carboxamide

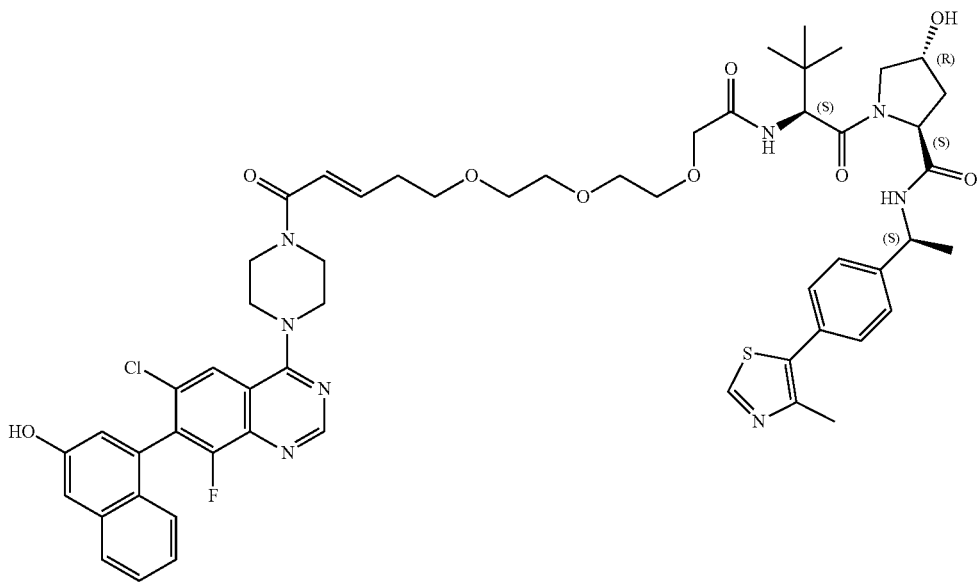

To the mixture of 2-[2-[2-[(E)-5-[4-[6-chloro-8-fluoro-7-(3-hydroxy-1-naphthyl)quinazolin-4-yl]piperazin-1-yl]-5-oxo-pent-3-enoxy]ethoxy]ethoxy]acetic acid (110 mg, 0.17 mmol, 1 eq) and (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (81 mg, 0.17 mmol, 1 eq, hydrochloride) in N,N-dimethylformamide (3 mL) was added 1-hydroxybenzotriazole (34 mg, 0.25 mmol, 1.5 eq), N-(3-dimethylaminopropyl)-N-ethylcarbodiimide hydrochloride (48 mg, 0.25 mmol, 1.5 eq) and N,N-diisopropylethylamine (65 mg, 0.50 mmol, 0.09 mL, 3 eq). The mixture was stirred at 20° C. for 12 hours. The mixture was diluted with water (15 mL), extracted with ethyl acetate (15 mL×3). The combined organic layer was washed with water (20 mL×2), and brine (20 mL×2), dried over anhydrous sodium sulfate, filtered and concentrated under reduced pressure to give a residue. The residue was purified by prep.TLC (dichloromethane:methanol=10:1) to give a residue. The residue was purified by semi-preparative reverse phase HPLC. (2S,4R)-1-[(2S)-2-[[2-[2-[2-[(E)-5-[4-[6-chloro-8-fluoro-7-(3-hydroxy-1-naphthyl)quinazolin-4-yl]piperazin-1-yl]-5-oxo-pent-3-enoxy]ethoxy]ethoxy]acetyl]amino]-3,3-dimethyl-butanoyl]-4-hydroxy-N—[(S)-1-[4-(4-methylthiazol-5-yl)phenyl]ethyl]pyrrolidine-2-carboxamide (50.8 mg, 0.04 mmol, 27% yield, 99% purity) was obtained as a white solid. LC/MS (ESI) m/z: 1195.4 [M+1]$^+$; $^1$H-NMR (400 MHz, CD$_3$OD) δ 8.84 (s, 1H), 8.66 (s, 1H), 8.08 (d, J=1.2 Hz, 1H), 7.75 (d, J=8.4 Hz, 1H), 7.42-7.38 (m, 5H), 7.27 (d, J=2.4 Hz, 1H), 7.25-7.20 (m, 2H), 7.06 (s, 1H), 6.90-6.86 (m, 1H), 6.58-6.54 (m, 1H), 5.02-4.98 (m, 1H), 4.56-4.54 (m, 1H), 4.42 (s, 1H), 4.05-4.03 (m, 6H), 3.89-3.71 (m, 5H), 3.69-3.64 (m, 12H), 2.56-2.51 (m, 2H), 2.45 (s, 3H), 2.18-2.16 (m, 1H), 1.99-1.95 (m, 1H), 1.50-1.46 (m, 3H), 1.04 (s, 9H).

Exemplary Synthesis of (2S,4R)-1-((2S)-2-(3-(2-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)ethoxy)isoxazol-5-yl)-3-methylbutanoyl)-4-hydroxy-N—((S)-1-(2-methoxy-4-(4-methylthiazol-5-yl)phenyl)ethyl)pyrrolidine-2-carboxamide (Exemplary Compound 386)

Step 1: Preparation of (2S,4R)-4-hydroxy-N—((S)-1-(2-methoxy-4-(4-methylthiazol-5-yl)phenyl)ethyl)-1-((S)-3-methyl-2-(3-(2-(2-(2-(methylamino)ethoxy)ethoxy)ethoxy)isoxazol-5-yl)butanoyl)pyrrolidine-2-carboxamide hydrochloride

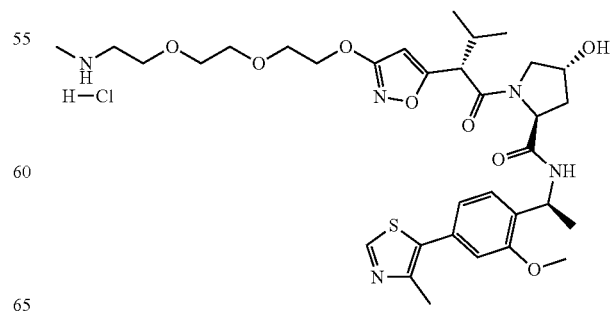

To a solution of tert-butyl N-[2-[2-[2-[5-[(1S)-1-[(2S,4R)-4-hydroxy-2-[[(1S)-1-[2-methoxy-4-(4-methylthiazol-5-yl)phenyl]ethyl]carbamoyl]pyrrolidine-1-carbonyl]-2-methyl-propyl]isoxazol-3-yl]oxyethoxy]ethoxy]ethyl]-N-methyl-carbamate (100 mg, 0.13 mmol, 1.0 eq) in dichloromethane (2 mL) was added hydrochloric/dioxane (4 M, 2 mL, 61.91 eq). The reaction mixture was stirred at 20° C. for 1 hour. The reaction mixture was concentrated under reduced pressure to give a residue. The desired compound (2S,4R)-4-hydroxy-N-[(1S)-1-[2-methoxy-4-(4-methylthiazol-5-yl)phenyl]ethyl]-1-[(2S)-3-methyl-2-[3-[2-[2-[2-(methylamino)ethoxy]ethoxy]ethoxy]isoxazol-5-yl]butanoyl]pyrrolidine-2-carboxamide (90 mg, HCl) was obtained as colorless oil.

Step 2: Preparation of (2S,4R)-1-((2S)-2-(3-(2-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)ethoxy)isoxazol-5-yl)-3-methylbutanoyl)-4-hydroxy-N—((S)-1-(2-methoxy-4-(4-methylthiazol-5-yl)phenyl)ethyl)pyrrolidine-2-carboxamide To a solution of (2S,4R)-4-hydroxy-N-[(1S)-1-[2-methoxy-4-(4-methylthiazol-5-yl)phenyl]ethyl]-1-[(2S)-3-methyl-2-[3-[2-[2-[2-(methylamino)ethoxy]ethoxy]ethoxy]isoxazol-5-yl]butanoyl]pyrrolidine-2-carboxamide (90 mg, 0.13 mmol, 1.0 eq, HCl) in dimethyl formamide (3 mL) was added diisopropylethylamine (50 mg, 0.4 mmol, 3.0 eq). The mixture was stirred at 20° C. for 10 minutes. Then 3-[[4-(4-acetylpiperazin-1-yl)-6-chloro-8-fluoro-7-(3-hydroxy-1-naphthyl)quinazolin-2-yl]amino]propanoic acid (68 mg, 0.13 mmol, 1.0 eq) and 1-hydroxybenzotriazole (34 mg, 0.25 mmol, 2.0 eq) were added into the mixture and stirred at 20° C. for 10 minutes. 1-(3-dimethylaminopropyl)-3-ethylcarbodiimide hydrochloride (48 mg, 0.25 mmol, 2.0 eq) was added into the mixture and stirred at 20° C. for 40 minutes. The mixture was diluted with water (2 mL), extracted with dichloromethane (20 mL), and then concentrated. The residue was purified by semi-preparative reverse phase. (2S,4R)-1-[(2S)-2-[3-[2-[2-[2-[3-[[4-(4-acetylpiperazin-1-yl)-6-chloro-8-fluoro-7-(3-hydroxy-1-naphthyl)quinazolin-2-yl]amino]propanoyl-methyl-amino]ethoxy]ethoxy]ethoxy]isoxazol-5-yl]-3-methyl-butanoyl]-4-hydroxy-N-[(1S)-1-[2-methoxy-4-(4-methylthiazol-5-yl)phenyl]ethyl]pyrrolidine-2-carboxamide (26 mg, 0.021 mmol, 17% yield, 100% purity) was obtained as an off-white solid. LC/MS (ESI) m/z: 1193.3 [M+1]$^+$; $^1$H-NMR (400 MHz, DMSO-d$_6$) δ 9.01-8.96 (m, 1H), 8.29 (d, J=7.2 Hz, 1H), 7.81-7.73 (m, 2H), 7.41 (br s, 1H), 7.28-6.96 (m, 9H), 6.08 (d, J=5.2 Hz, 1H), 5.12 (t, J=7.2 Hz, 1H), 4.46-4.09 (m, 4H), 3.90-3.80 (m, 4H), 3.78-3.61 (m, 12H), 3.50 (d, J=18.8 Hz, 10H), 3.04-2.96 (m, 2H), 2.80 (br s, 2H), 2.25 (d, J=6.4 Hz, 2H), 2.10-1.96 (m, 5H), 1.78 (d, J=6.8 Hz, 1H), 1.38 (d, J=6.8 Hz, 1H), 1.26 (d, J=6.8 Hz, 3H), 1.00-0.72 (m, 8H).

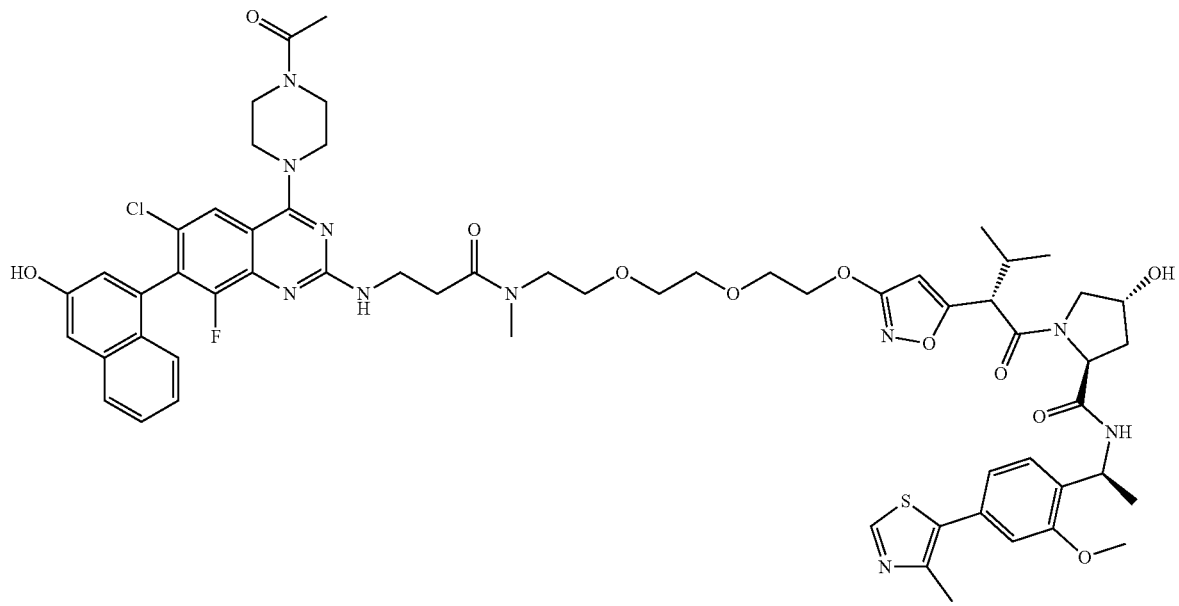 [SMILES: COc1cc(-c2scnc2C)ccc1[C@H](C)NC(=O)[C@@H]1C[C@@H](O)CN1C(=O)[C@H](c1cc(OCCOCCOCCN(C)C(=O)CCNc2nc(N3CCN(C(C)=O)CC3)c3cc(Cl)c(-c4cc(O)cc5ccccc45)c(F)c3n2)no1)C(C)C]

Exemplary Synthesis of (2S,4R)-1-((2R)-2-(3-(2-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)ethoxy)isoxazol-5-yl)-3-methylbutanoyl)-4-hydroxy-N—((S)-1-(2-methoxy-4-(4-methylthiazol-5-yl)phenyl)ethyl)pyrrolidine-2-carboxamide (Exemplary Compound 387)

Step 1: Preparation of (2S,4R)-4-hydroxy-N—((S)-1-(2-methoxy-4-(4-methylthiazol-5-yl)phenyl)ethyl)-1-((R)-3-methyl-2-(3-(2-(2-(2-(methylamino)ethoxy)ethoxy)ethoxy)isoxazol-5-yl)butanoyl)pyrrolidine-2-carboxamide hydrochloride

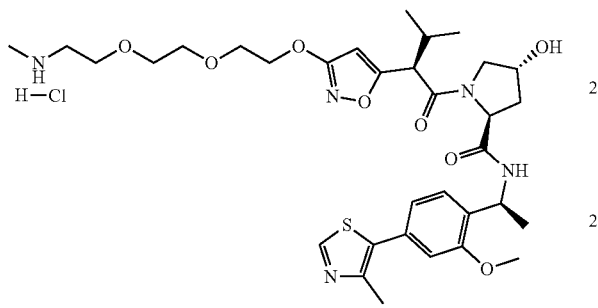

To a solution of tert-butyl N-[2-[2-[2-[5-[(1R)-1-[(2S,4R)-4-hydroxy-2-[[(1S)-1-[2-methoxy-4-(4-methylthiazol-5-yl)phenyl]ethyl]carbamoyl]pyrrolidine-1-carbonyl]-2-methyl-propyl]isoxazol-3-yl]oxyethoxy]ethoxy]ethyl]-N-methyl-carbamate (100 mg, 0.13 mmol, 1.0 eq) in dichloromethane (2 mL) was added hydrochloric/dioxane (4 M, 2 mL, 61.91 eq). The reaction mixture was stirred at 20° C. for 1 hour. The reaction mixture was concentrated under reduced pressure to give a residue. The desired compound (2S,4R)-4-hydroxy-N-[(1S)-1-[2-methoxy-4-(4-methylthiazol-5-yl)phenyl]ethyl]-1-[(2R)-3-methyl-2-[3-[2-[2-[2-(methylamino)ethoxy]ethoxy]ethoxy]isoxazol-5-yl]butanoyl]pyrrolidine-2-carboxamide (90 mg, HCl) was obtained as colorless oil.

Step 2: Preparation of (2S,4R)-1-((2R)-2-(3-(2-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)ethoxy)isoxazol-5-yl)-3-methylbutanoyl)-4-hydroxy-N—((S)-1-(2-methoxy-4-(4-methylthiazol-5-yl)phenyl)ethyl)pyrrolidine-2-carboxamide

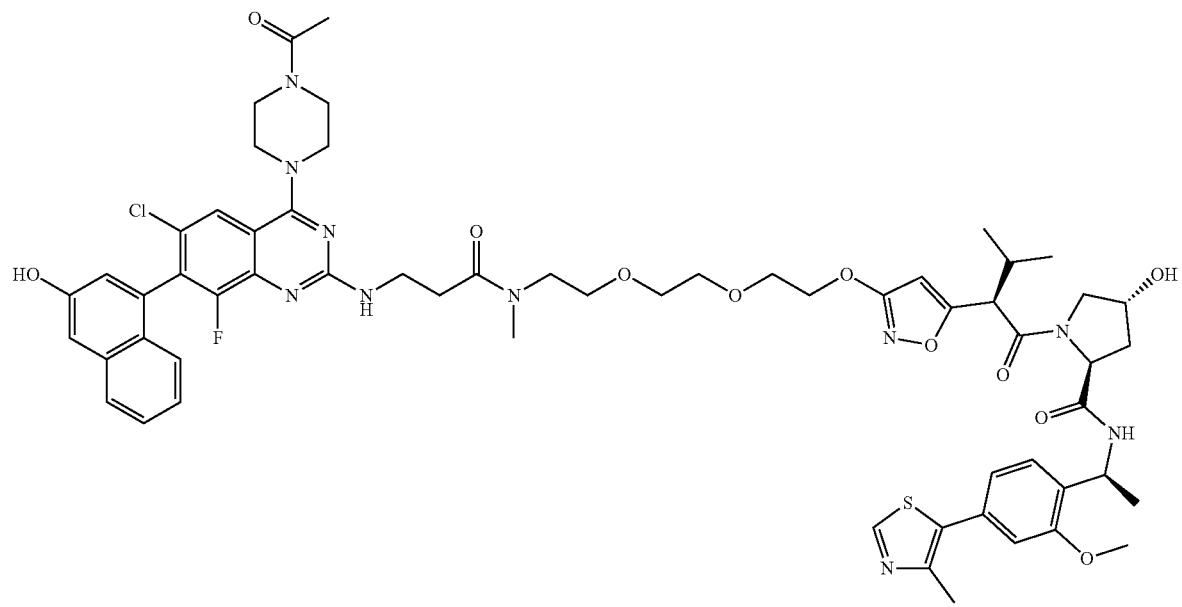 [SMILES: COc1cc(-c2scnc2C)ccc1[C@H](C)NC(=O)[C@@H]1C[C@@H](O)CN1C(=O)[C@@H](c1cc(OCCOCCOCCN(C)C(=O)CCNc2nc(N3CCN(C(C)=O)CC3)c3cc(Cl)c(-c4cc(O)cc5ccccc45)c(F)c3n2)no1)C(C)C]

To a solution of (2S,4R)-4-hydroxy-N-[(1S)-1-[2-methoxy-4-(4-methylthiazol-5-yl)phenyl]ethyl]-1-[(2R)-3-methyl-2-[3-[2-[2-[2-(methylamino)ethoxy]ethoxy]ethoxy]isoxazol-5-yl]butanoyl]pyrrolidine-2-carboxamide (90 mg, 0.13 mmol, 1.0 eq, HCl) in dimethyl formamide (3 mL) was added diisopropylethylamine (50 mg, 0.4 mmol, 3.0 eq). The mixture was stirred at 20° C. for 10 minutes. Then 3-[[4-(4-acetylpiperazin-1-yl)-6-chloro-8-fluoro-7-(3-hydroxy-1-naphthyl)quinazolin-2-yl]amino]propanoic acid (71 mg, 0.13 mmol, 1.0 eq) and 1-hydroxybenzotriazole (36.10 mg, 0.26 mmol, 2.0 eq) were added into the mixture and stirred at 20° C. for 10 minutes. 1-(3-dimethylaminopropyl)-3-ethylcarbodiimide hydrochloride (51 mg, 0.26 mmol, 2.0 eq) was added into the mixture and stirred at 20° C. for 40 minutes. The mixture was diluted with water (2 mL), extracted with dichloromethane (20 mL), then concentrated. The residue was purified by semi-preparative reverse phase. (2S,4R)-1-[(2R)-2-[3-[2-[2-[2-[3-[[4-(4-acetylpiperazin-1-yl)-6-chloro-8-fluoro-7-(3-hydroxy-1-naphthyl)quinazolin-2-yl]amino]propanoyl-methyl-amino]ethoxy]ethoxy]ethoxy]isoxazol-5-yl]-3-methyl-butanoyl]-4-hydroxy-N-[(1S)-1-[2-methoxy-4-(4-methylthiazol-5-yl)phenyl]ethyl]pyrrolidine-2-carboxamide (45 mg, 0.035 mmol, 26% yield, 95% purity) was obtained as an off-white solid. LC/MS (ESI) m/z: 1193.3 [M+1]$^+$; $^1$H-NMR (400 MHz, DMSO-d$_6$) δ 9.01-8.96 (m, 1H), 8.29 (d, J=7.2 Hz, 1H), 7.81-7.73 (m, 2H), 7.41 (br s, 1H), 7.28-6.96 (m, 9H), 6.08 (d, J=5.2 Hz, 1H), 5.12 (t, J=7.2 Hz, 1H), 4.46-4.09 (m, 4H), 3.90-3.80 (m, 4H), 3.78-3.61 (m, 12H), 3.50 (d, J=18.8 Hz, 10H), 3.04-2.96 (m, 2H), 2.80 (br s, 2H), 2.25 (d, J=6.4 Hz, 2H), 2.10-1.96 (m, 5H), 1.78 (d, J=6.8 Hz, 1H), 1.38 (d, J=6.8 Hz, 1H), 1.26 (d, J=6.8 Hz, 3H), 1.00-0.72 (m, 8H).

Exemplary Synthesis of (2S,4R)-1-((2S)-21-((4-(4-acryloylpiperazin-1-yl)-6-chloro-8-fluoro-7-(3-hydroxynaphthalen-1-yl)quinazolin-2-yl)amino)-2-(tert-butyl)-18-methyl-4-oxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide (Exemplary Compound 396)

Step 1: Preparation of tert-butyl ((S)-20-((2S,4R)-4-hydroxy-2-(((S)-1-(4-(4-methylthiazol-5-yl)phenyl)ethyl)carbamoyl)pyrrolidine-1-carbonyl)-4,21,21-trimethyl-18-oxo-7,10,13,16-tetraoxa-4,19-diazadocosyl)carbamate

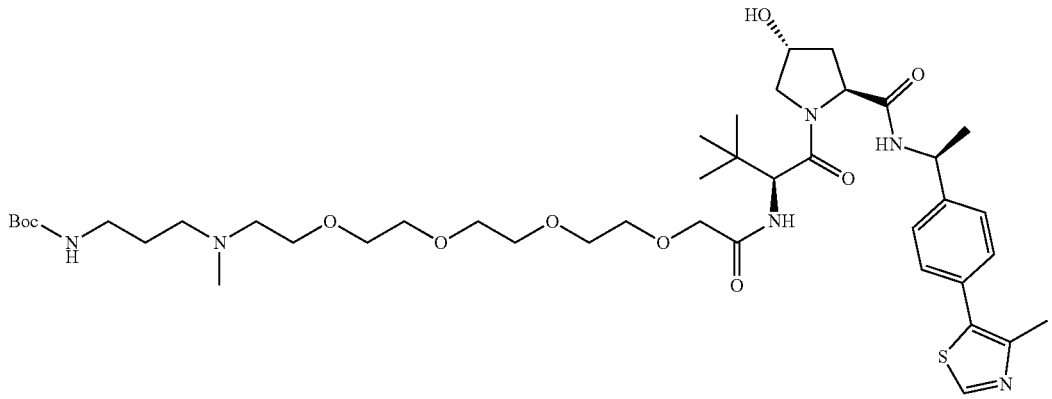 [SMILES: Cc1ncsc1-c1ccc([C@H](C)NC(=O)[C@@H]2C[C@@H](O)CN2C(=O)[C@@H](NC(=O)COCCOCCOCCOCCN(C)CCCNC(=O)OC(C)(C)C)C(C)(C)C)cc1]

(2S,4R)-1-[(2S)-3,3-dimethyl-2-[[2-[2-[2-[2-[2-(methylamino)ethoxy]ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (260 mg, 0.36 mmol, 1.00 eq, hydrochloride), tert-butyl N-(3-bromopropyl) carbamate (170 mg, 0.71 mmol, 2.00 eq) and diisopropylethylamine (93 mg, 0.71 mmol, 2.00 eq) were taken up into a microwave tube in isopropanol (3 mL). The sealed tube was heated at 110° C. for 2 hours under microwave. The reaction mixture was concentrated under reduced pressure to give a residue. The residue was purified by prep-TLC (silica gel plate, 13% dichloromethane in methanol) to give compound tert-butyl N-[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino]propyl]carbamate (140 mg, 0.16 mmol, 46% yield) as a colorless oil. LC/MS (ESI) m/z: 849.5 [M+1]$^+$.

Step 2: Preparation of (2S,4R)-1-((S)-21-amino-2-(tert-butyl)-18-methyl-4-oxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide

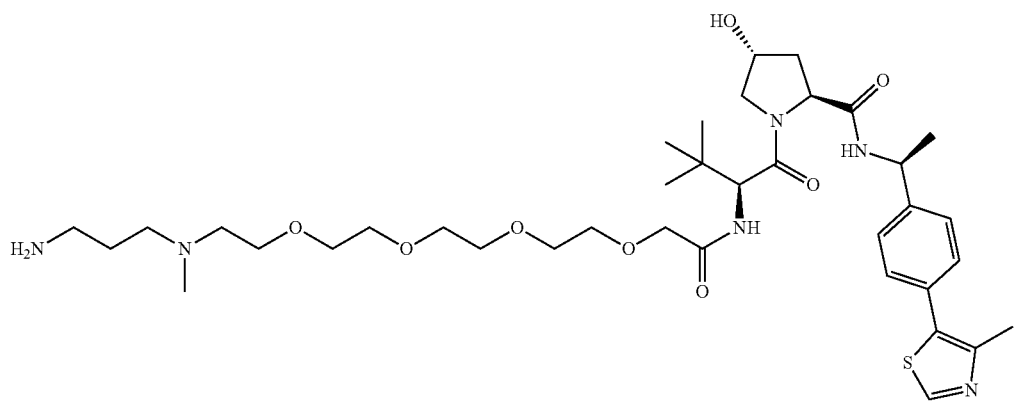 [SMILES: Cc1ncsc1-c1ccc([C@H](C)NC(=O)[C@@H]2C[C@@H](O)CN2C(=O)[C@@H](NC(=O)COCCOCCOCCOCCN(C)CCCN)C(C)(C)C)cc1]

To a solution of tert-butyl N-[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethyl-methyl-amino]propyl]carbamate (140 mg, 0.16 mmol, 1.00 eq) in dichloromethane (3 mL) was added hydrochloric acid in dioxane (4 M, 4 mL). The mixture was stirred at 15° C. for 0.5 hour. The reaction mixture was concentrated under reduced pressure to give compound (2S,4R)-1-[(2S)-2-[[2-[2-[2-[2-[3-aminopropyl (methyl)amino]ethoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl] pyrrolidine-2-carboxamide (130 mg, hydrochloride) as a colorless oil. LC/MS (ESI) m/z: 749.4 [M+1]⁺.

Step 3: Preparation of tert-butyl 4-(7-bromo-6-chloro-8-fluoro-2-(((S)-20-((2S,4R)-4-hydroxy-2-(((S)-1-(4-(4-methylthiazol-5-yl)phenyl)ethyl)carbamoyl)pyrrolidine-1-carbonyl)-4,21,21-trimethyl-18-oxo-7,10,13,16-tetraoxa-4,19-diazadocosyl) amino)quinazolin-4-yl)piperazine-1-carboxylate

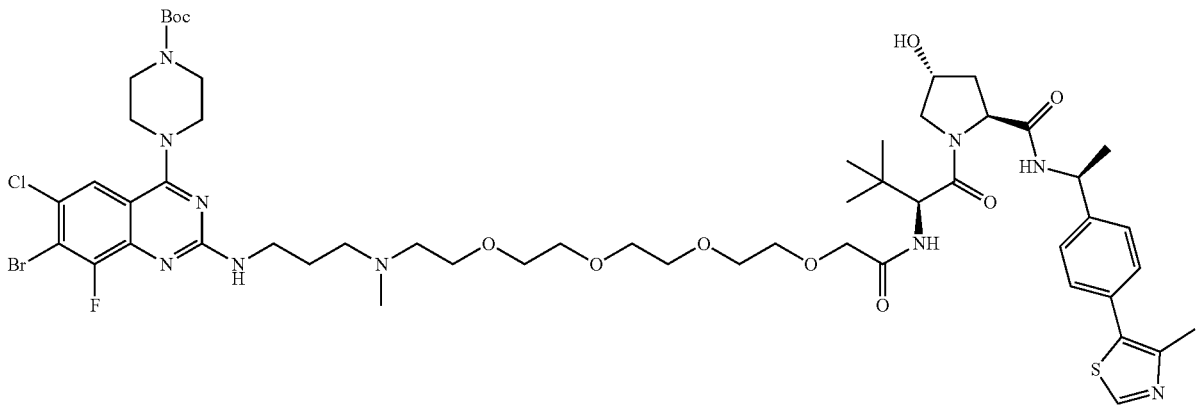 [SMILES: Cc1ncsc1-c1ccc([C@H](C)NC(=O)[C@@H]2C[C@@H](O)CN2C(=O)[C@@H](NC(=O)COCCOCCOCCOCCN(C)CCCNc2nc(N3CCN(C(=O)OC(C)(C)C)CC3)c3cc(Cl)c(Br)c(F)c3n2)C(C)(C)C)cc1]

(2S,4R)-1-[(2S)-2-[[2-[2-[2-[2-[2-[3-aminopropyl (methyl)amino]ethoxy]ethoxy]ethoxy]ethoxy]acetyl] amino]-3,3-dimethyl-butanoyl]-4-hydroxy-N-[(1S)-1-[4-(4-methylthiazol-5-yl)phenyl]ethyl]pyrrolidine-2-carboxamide (130 mg, 0.16 mmol, 1.00 eq, hydrochloride), tert-butyl 4-(7-bromo-2,6-dichloro-8-fluoro-quinazolin-4-yl)piperazine-1-carboxylate (88 mg, 0.18 mmol, 1.15 eq) and diisopropylethylamine (71 mg, 0.55 mmol, 0.10 mL, 3.46 eq) were taken up into a microwave tube in isopropanol (5 mL). The sealed tube was heated at 115° C. for 3 hours under microwave. The reaction mixture was concentrated under reduced pressure to give a residue. The residue was purified by preparative thin layer chromatography (silica gel plate, 13% dichloromethane in methanol) to give compound tert-butyl4-[7-bromo-6-chloro-8-fluoro-2-[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino]propylamino]quinazolin-4-yl] piperazine-1-carboxylate (120 mg, 0.1 mmol, 64% yield, 100% purity) as a colorless oil. LC/MS (ESI) m/z: 597.5 [M/2+1]⁺.

Step 4: Preparation of tert-butyl 4-(6-chloro-8-fluoro-2-(((S)-20-((2S,4R)-4-hydroxy-2-(((S)-1-(4-(4-methylthiazol-5-yl)phenyl)ethyl)carbamoyl)pyrrolidine-1-carbonyl)-4,21,21-trimethyl-18-oxo-7,10,13,16-tetraoxa-4,19-diazadocosyl)amino)-7-(3-hydroxynaphthalen-1-yl)quinazolin-4-yl)piperazine-1-carboxylate

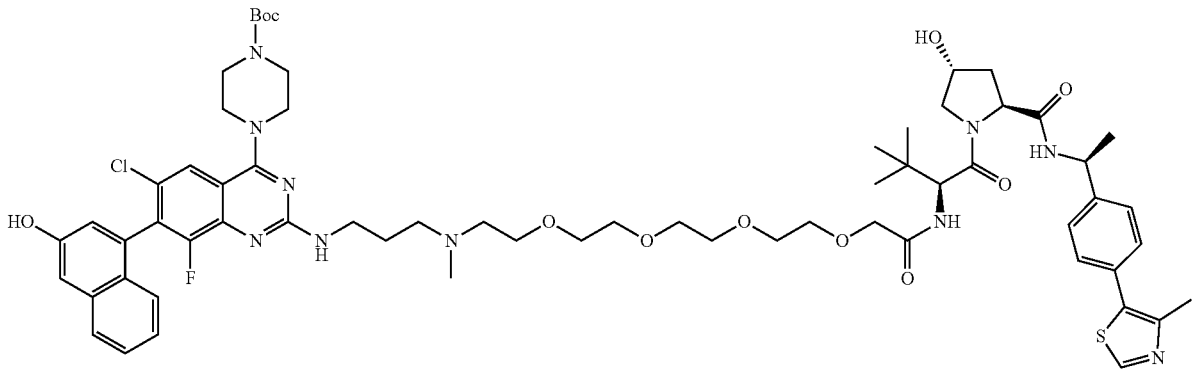 [SMILES: Cc1ncsc1-c1ccc([C@H](C)NC(=O)[C@@H]2C[C@@H](O)CN2C(=O)[C@@H](NC(=O)COCCOCCOCCOCCN(C)CCCNc2nc(N3CCN(C(=O)OC(C)(C)C)CC3)c3cc(Cl)c(-c4cc(O)cc5ccccc45)c(F)c3n2)C(C)(C)C)cc1]

A mixture of tert-butyl4-[7-bromo-6-chloro-8-fluoro-2-[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino] propylamino]quinazolin-4-yl]piperazine-1-carboxylate (120 mg, 0.10 mmol, 1.00 eq), 4-(4,4,5,5-tetramethyl-1,3,2-dioxaborolan-2-yl)naphthalen-2-ol (54 mg, 0.20 mmol, 2.00 eq), [2-(2-aminophenyl)phenyl]palladium(1+); dicyclohexyl-[2-(2,4,6-triisopropylphenyl)phenyl]phosphane; methanesulfonate (9 mg, 0.01 mmol, 0.10 eq) and potassium phosphate (1.5 M in H₂O, 0.20 mL, 3.00 eq) in tetrahydrofuran (5 mL) was degassed and purged with nitrogen for 3 times, and then the mixture was stirred at 60° C. for 12 hours under nitrogen atmosphere. The reaction mixture was concentrated under reduced pressure to give a residue. The residue was purified by preparative thin layer chromatography (silica gel plate, 13% dichloromethane in methanol) to give compound tert-butyl4-[6-chloro-8-fluoro-2-[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy] ethoxy]ethoxy]ethoxy]ethyl-methyl-amino]propylamino]-7-(3-hydroxy-1-naphthyl)quinazolin-4-yl]piperazine-1-carboxylate (100 mg, 0.08 mmol, 79% yield) as a yellow solid. LC/MS (ESI) m/z: 1255.8 [M+I]⁺.

Step 5: Preparation of (2S,4R)-1-((2S)-2-(tert-butyl)-21-((6-chloro-8-fluoro-7-(3-hydroxynaphthalen-1-yl)-4-(piperazin-1-yl)quinazolin-2-yl)amino)-18-methyl-4-oxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide

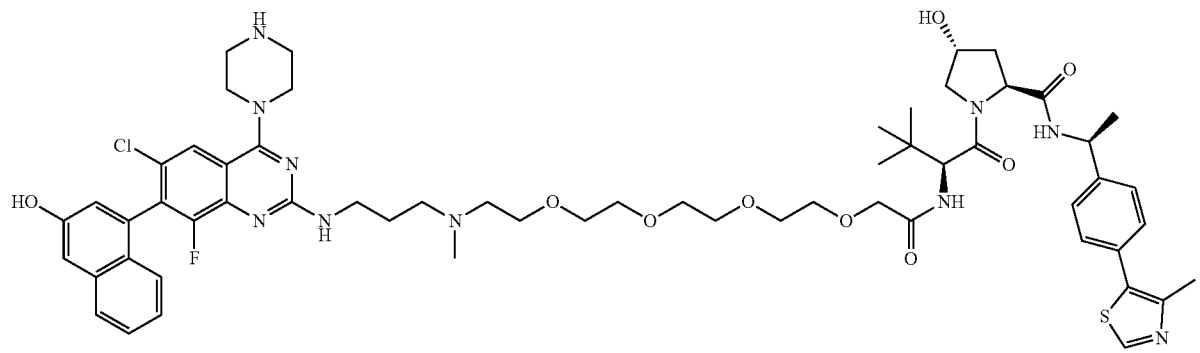 [SMILES: Cc1ncsc1-c1ccc([C@H](C)NC(=O)[C@@H]2C[C@@H](O)CN2C(=O)[C@@H](NC(=O)COCCOCCOCCOCCN(C)CCCNc2nc(N3CCNCC3)c3cc(Cl)c(-c4cc(O)cc5ccccc45)c(F)c3n2)C(C)(C)C)cc1]

To a solution of tert-butyl 4-[6-chloro-8-fluoro-2-[3-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino]propylamino]-7-(3-hydroxy-1-naphthyl)quinazolin-4-yl]piperazine-1-carboxylate (100 mg, 0.08 mmol, 1.00 eq) in dichloromethane (5 mL) was added hydrochloric acid in dioxane (4 M, 3 mL). The resulting mixture was stirred at 20° C. for 0.5 hour. The reaction mixture was concentrated under reduced pressure to give compound (2S,4R)-1-[(2S)-2-[[2-[2-[2-[2-[2-[3-[[6-chloro-8-fluoro-7-(3-hydroxy-1-naphthyl)-4-piperazin-1-yl-quinazolin-2-yl]amino]propyl-methyl-amino]ethoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (95 mg, hydrochloride) as a yellow solid. LC/MS (ESI) m/z: 1155.7 [M+1]$^+$.

Step 6: Preparation of (2S,4R)-1-((2S)-21-((4-(4-acryloylpiperazin-1-yl)-6-chloro-8-fluoro-7-(3-hydroxynaphthalen-1-yl)quinazolin-2-yl)amino)-2-(tert-butyl)-18-methyl-4-oxo-6,9,12,15-tetraoxa-3,18-diazahenicosanoyl)-4-hydroxy-N—((S)-1-(4-(4-methylthiazol-5-yl)phenyl)ethyl)pyrrolidine-2-carboxamide

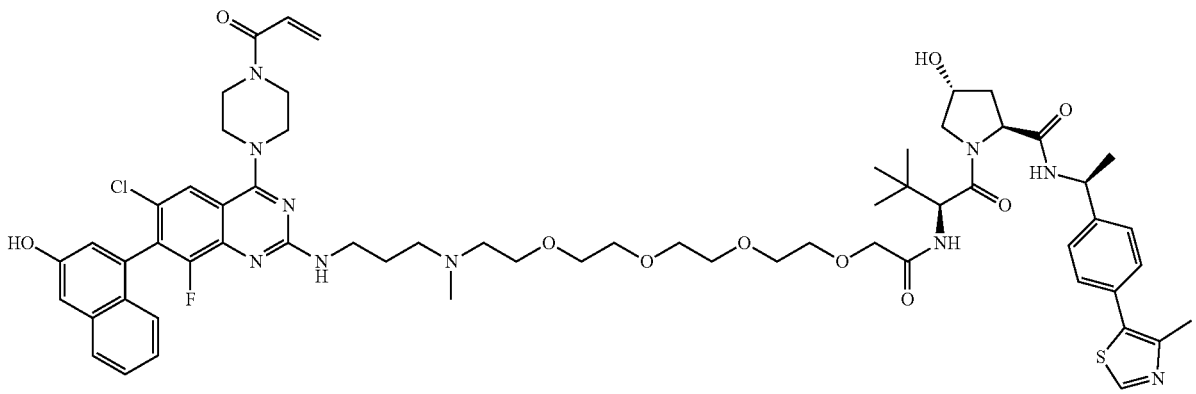 [SMILES: C=CC(=O)N1CCN(c2nc(NCCCN(C)CCOCCOCCOCCOCC(=O)N[C@H](C(=O)N3C[C@H](O)C[C@H]3C(=O)N[C@@H](C)c3ccc(-c4scnc4C)cc3)C(C)(C)C)nc3c(F)c(-c4cc(O)cc5ccccc45)c(Cl)cc23)CC1]

A solution of (2S,4R)-1-[(2S)-2-[[2-[2-[2-[2-[2-[3-[[6-chloro-8-fluoro-7-(3-hydroxy-1-naphthyl)-4-piperazin-1-yl-quinazolin-2-yl]amino]propyl-methyl-amino]ethoxy]ethoxy]ethoxy]ethoxy]acetyl]amino]-3,3-dimethyl-butanoyl]-4-hydroxy-N—[(S)-1-[4-(4-methylthiazol-5-yl)phenyl]ethyl]pyrrolidine-2-carboxamide (95 mg, 0.08 mmol, 1.00 eq, hydrochloride) and 2,6-lutidine (124 mg, 1.16 mmol, 0.14 mL, 15.00 eq) in dichloromethane (5 mL) was cooled to −78° C. Then prop-2-enoyl chloride (7.00 mg, 0.08 mmol, 1.00 eq) in dichloromethane (1 mL) was added. The resulting mixture was stirred at −78° C. for 0.5 hour. The reaction mixture was quenched with saturated sodium bicarbonate solution (20 mL), then extracted with dichloromethane (20 mL×2). The combined organic layers were washed with brine (20 mL×1), dried over anhydrous sodium sulfate, filtered and concentrated under reduced pressure to give a residue. The residue was purified by semi-preparative reverse phase HPLC to give compound (2S,4R)-1-[(2S)-2-[[2-[2-[2-[2-[2-[3-[[6-chloro-8-fluoro-7-(3-hydroxy-1-naphthyl)-4-(4-prop-2-enoylpiperazin-1-yl)quinazolin-2-yl]amino]propyl-methyl-amino]ethoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (31 mg, 0.02 mmol, 30% yield, 98% purity, trifluoroacetic acid salt) as a yellow solid. LC/MS (ESI) m/z: 1209.4 [M+1]$^+$; $^1$H-NMR (400 MHz, DMSO-d$_6$) δ 9.58 (brs, 1H), 8.98 (s, 1H), 8.82-8.56 (m, 1H), 8.41 (d, J=8.0 Hz, 1H), 8.08 (brs, 1H), 7.82 (d, J=8.8 Hz, 1H), 7.59-7.18 (m, 9H), 7.07 (s, 1H), 6.82 (dd, J=11.2, 16.4 Hz, 1H), 6.20 (d, J=16.4 Hz, 1H), 5.77 (d, J=11.2 Hz, 1H), 4.96-4.85 (m, 2H), 4.54 (d, J=9.6 Hz, 1H), 4.43 (t, J=8.0 Hz, 1H), 4.28 (s, 1H), 4.24-4.07 (m, 3H), 3.97-3.66 (m, 9H), 3.63-3.09 (m, 20H), 2.81 (s, 3H), 2.45 (s, 3H), 2.21-1.91 (m, 3H), 1.90-1.70 (m, 1H), 1.50-1.31 (m, 3H), 0.93 (s, 9H).

Exemplary Synthesis of (2S,4R)-1-((2S)-2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide (Exemplary Compound 398)

Step 1: Preparation of tert-butyl 4-(2-(2-ethoxy-2-oxoethoxy)ethoxy)piperidine-1-carboxylate

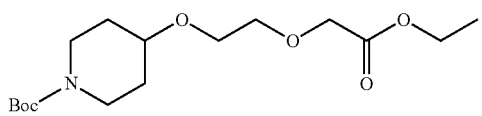 [SMILES: CCOC(=O)COCCOC1CCN(C(=O)OC(C)(C)C)CC1]

To a solution of tert-butyl 4-(2-hydroxyethoxy)piperidine-1-carboxylate (2 g, 8.15 mmol, 1 eq) in dichloromethane (20 mL) was added diacetoxyrhodium (90 mg, 0.41 mmol, 0.05 eq). ethyl 2-diazoacetate (2.79 g, 24.46 mmol, 3 eq) was added at 0° C., the mixture was stirred at 25° C. for 12 hours. The reaction mixture was concentrated under vacuum. The crude product was purified by flash silica gel chromatography (Petroleum ether:Ethyl acetate=9:1 to 3:1). Compound tert-butyl 4-[2-(2-ethoxy-2-oxo-ethoxy)ethoxy]piperidine-1-carboxylate (1.7 g, 5.13 mmol, 63% yield) as a colorless oil was obtained. $^1$H-NMR (400 MHz, CDCl$_3$) δ 4.22 (q, J=7.1 Hz, 2H), 4.16 (s, 2H), 3.83-3.71 (m, 4H), 3.70-3.63 (m, 2H), 3.50 (tt, J=3.9, 8.2 Hz, 1H), 3.07 (ddd, J=3.4, 9.5, 13.3 Hz, 2H), 1.89-1.79 (m, 2H), 1.58-1.48 (m, 2H), 1.46 (s, 9H), 1.32-1.27 (m, 3H).

Step 2: Preparation of 2-(2-((1-(tert-butoxycarbonyl)piperidin-4-yl)oxy)ethoxy)acetic acid

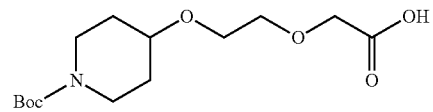 [SMILES: CC(C)(C)OC(=O)N1CCC(OCCOCC(=O)O)CC1]

To a solution of tert-butyl 4-[2-(2-ethoxy-2-oxo-ethoxy)ethoxy]piperidine-1-carboxylate (1.6 g, 4.83 mmol, 1 eq) in methanol (3 mL) and tetrahydrofuran (3 mL) and water (3 mL) was added lithium hydroxide monohydrate (405 mg, 9.66 mmol, 2 eq). The mixture was stirred at 25° C. for 1 hour. Water 10 mL was added. The mixture was adjusted pH to 3-4 by 1M hydrochloric acid, and then the aqueous phase was extracted with dichloromethane and methanol (10:1, 30 mL×3). The combined organic phase was dried with anhydrous sodium sulfate, filtered and concentrated in vacuum. Compound 2-[2-[(1-tert-butoxycarbonyl-4-piperidyl)oxy]ethoxy]acetic acid (1.2 g, 3.96 mmol, 82% yield) as a yellow solid was obtained.

Step 3: Preparation of tert-butyl 4-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)piperidine-1-carboxylate

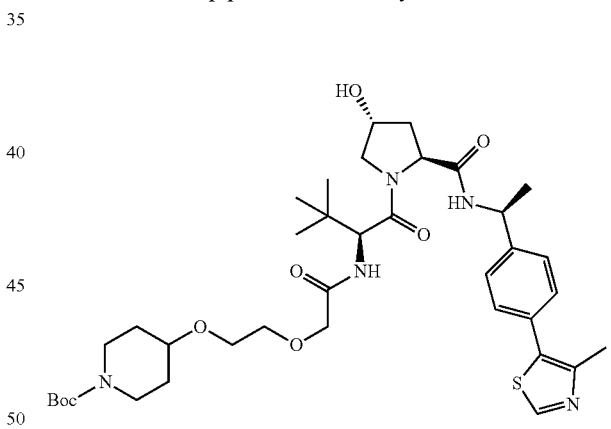

To a solution of 2-[2-[(1-tert-butoxycarbonyl-4-piperidyl)oxy]ethoxy]acetic acid (410 mg, 1.35 mmol, 1 eq) and (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (600 mg, 1.35 mmol, 1 eq) in N,N-dimethylformamide (10 mL) was added hydroxybenzotriazole (274 mg, 2.03 mmol, 1.50 eq) and 1-(3-dimethylaminopropyl)-3-ethylcarbodiimide hydrochloride (389 mg, 2.03 mmol, 1.50 eq) and N,N-diisopropylethylamine (593 mg, 4.59 mmol, 0.8 mL, 3.40 eq). The mixture was stirred at 25° C. for 12 hours. Water (50 mL) was added, the aqueous phase was extracted with ethyl acetate (40 mL×3). The combined organic phase was washed with brine (20 mL), dried with anhydrous sodium sulfate, filtered and concentrated in vacuum. The residue was purified by silica gel chromatography (Dichloromethane:Methanol=1:0 to 20:1). Compound tert-butyl 4-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]piperidine-1-carboxylate (690 mg, 0.95 mmol, 70% yield) was obtained as a yellow oil. LC/MS (ESI) m/z: 730.4 [M+1]$^+$.

Step 4: Preparation of (2S,4R)-1-((S)-3,3-dimethyl-2-(2-(2-(piperidin-4-yloxy)ethoxy)acetamido)butanoyl)-4-hydroxy-N—((S)-1-(4-(4-methylthiazol-5-yl)phenyl)ethyl)pyrrolidine-2-carboxamide

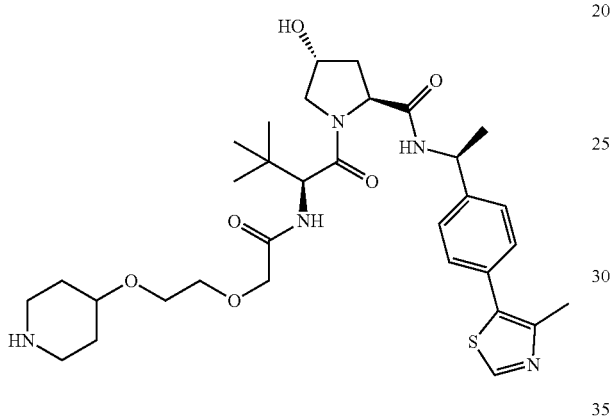

A mixture of tert-butyl 4-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]piperidine-1-carboxylate (690 mg, 0.95 mmol, 1.00 eq) in hydrochloric acid/dioxane (4.0 M, 15 mL, 63.47 eq) was stirred at 20° C. for 1.0 hour. The solvent was removed under reduced pressure. The residue was diluted with methanol (10 mL) and acetonitrile (30 mL), the solvent was removed again and dried in vacuum. A suspension of (2S,4R)-1-[(2S)-3,3-dimethyl-2-[[2-[2-(4-piperidyloxy)ethoxy]acetyl]amino]butanoyl]-4-hydroxy-N-[(1S)-1-[4-(4-methylthiazol-5-yl)phenyl]ethyl]pyrrolidine-2-carboxamide (470 mg, 705.42 umol, 1 eq, hydrochloride) and potassium carbonate (975 mg, 7.05 mmol, 10.00 eq) in a mixture of dichloromethane (8 mL) and acetonitrile (16 mL) was stirred at 25° C. for 1.5 hours. The suspension was filtered through a celite pad and washed with dichloromethane (15 mL), the filtrate was concentrated and dried in vacuum. Compound (2S,4R)-1-[(2S)-3,3-dimethyl-2-[[2-[2-(4-piperidyloxy)ethoxy]acetyl]amino]butanoyl]-4-hydroxy-N-[(1S)-1-[4-(4-methylthiazol-5-yl)phenyl]ethyl]pyrrolidine-2-carboxamide (295 mg, 0.47 mmol, 66% yield) was obtained as a pale yellow solid.

Step 5: Preparation of tert-butyl 4-(6-chloro-8-fluoro-2-(((R)-1-(4-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)piperidin-1-yl)propan-2-yl)oxy)-7-(3-hydroxynaphthalen-1-yl)quinazolin-4-yl)piperazine-1-carboxylate

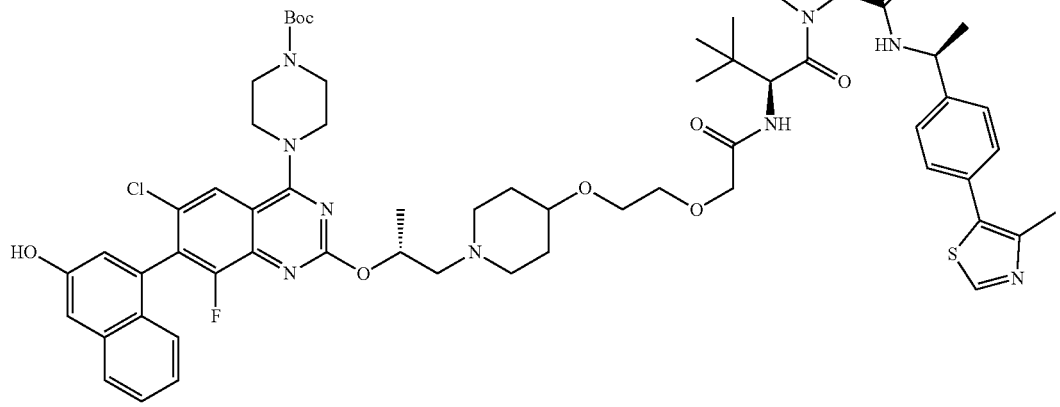

781

To a solution of tert-butyl 4-[6-chloro-8-fluoro-7-(3-hydroxy-1-naphthyl)-2-[(1R)-1-methyl-2-oxo-ethoxy]quinazolin-4-yl]piperazine-1-carboxylate (60 mg, 0.10 mmol, 1 eq) and (2S,4R)-1-[(2S)-3,3-dimethyl-2-[[2-[2-(4-piperidyloxy)ethoxy]acetyl]amino]butanoyl]-4-hydroxy-N-[(1S)-1-[4-(4-methylthiazol-5-yl)phenyl]ethyl]pyrrolidine-2-carboxamide (78 mg, 0.12 mmol, 1.2 eq) in methanol (1 mL) and dichloromethane (2 mL) was added acetic acid (12 mg, 0.20 mmol, 2 eq), then sodium cyanoborohydride (19 mg, 0.31 mmol, 3 eq) was added at 0° C. The mixture was stirred at 25° C. for 3 hours. The mixture was concentrated under vacuum. The mixture was purified by prep-TLC (Dichloromethane:Methanol=10:1) to get a product. Compound tert-butyl 4-[6-chloro-8-fluoro-2-[(1R)-2-[4-[2-[2-[[(1S)-1-

782

[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]-1-piperidyl]-1-methyl-ethoxy]-7-(3-hydroxy-1-naphthyl)quinazolin-4-yl]piperazine-1-carboxylate (63 mg) was obtained as a yellow solid. LC/MS (ESI) m/z: 1194.2 [M+1]$^+$.

Step 6: Preparation of (2S,4R)-1-((2S)-2-(2-(2-((1-((2R)-2-((6-chloro-8-fluoro-7-(3-hydroxynaphthalen-1-yl)-4-(piperazin-1-yl)quinazolin-2-yl)oxy)propyl)piperidin-4-yl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide

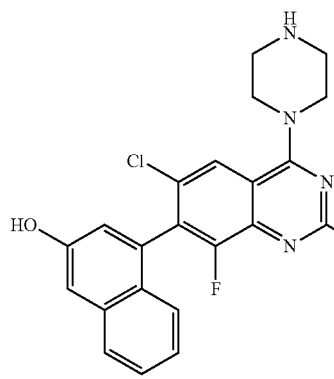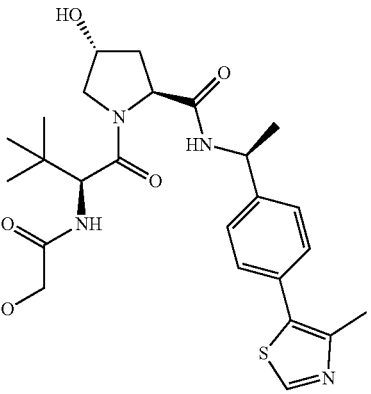

To a solution of tert-butyl 4-[6-chloro-8-fluoro-2-[(1R)-2-[4-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]-1-piperidyl]-1-methyl-ethoxy]-7-(3-hydroxy-1-naphthyl)quinazolin-4-yl]piperazine-1-carboxylate (61 mg, 0.05 mmol, 1 eq) in dichloromethane (2 mL) was added trifluoroacetic acid (770 mg, 6.75 mmol, 0.5 mL, 132.28 eq). The mixture was stirred at 25° C. for 0.5 hour. The mixture was concentrated under vacuum. Compound (2S,4R)-1-[(2S)-2-[[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (61 mg, 0.05 mmol, 99% yield, trifluoroacetate) was obtained as a yellow oil.

Step 7: Preparation of (2S,4R)-1-((2S)-2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide

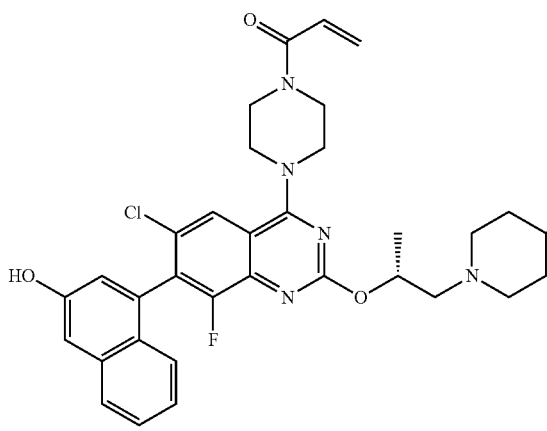
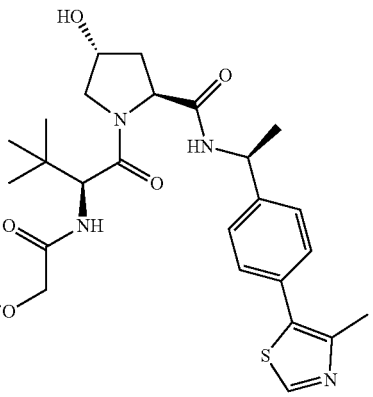

To a solution of (2S,4R)-1-[(2S)-2-[[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]acetyl]amino]-3,3-dimethyl-butanoyl]-4-hydroxy-N-[(1S)—[4-(4-methylthiazol-5-yl)phenyl]ethyl]pyrrolidine-2-carboxamide (61 mg, 0.05 mmol, 1 eq, trifluoroacetate) in dichloromethane (2 mL) was added 2,6-lutidine (54 mg, 0.50 mmol, 10 eq), then prop-2-enoyl chloride (4 mg, 0.045 mmol, 0.9 eq) in dichloromethane (4 mL) was added at −65° C. The mixture was stirred at −65° C. for 10 minutes. Water (10 mL) was added. The aqueous phase was extracted with dichloromethane (15 mL*3). The combined organic phase was concentrated in vacuum. The residue was purified by semi-preparative reverse phase HPLC. Then the collected fraction was concentrated to remove most of the acetonitrile. The solution was lyophilized. Compound (2S,4R)-1-[(2S)-2-[[2-[2-[[1-[(2R)-2-[6-chloro-8-fluoro-7-(3-hydroxy-1-naphthyl)-4-(4-prop-2-enoylpiperazin-1-yl)quinazolin-2-yl]oxypropyl]-4-piperidyl]oxy]ethoxy]acetyl]amino]-3,3-dimethyl-butanoyl]-4-hydroxy-N-[(1S)—[4-(4-methylthiazol-5-yl)phenyl]ethyl]pyrrolidine-2-carboxamide (19 mg, 0.02 mmol, 31% yield, 99% purity, formate) as a white solid was obtained. LC/MS (ESI) m/z: 574.8 [M/2+1]$^+$; $^1$H-NMR (400 MHz, DMSO-d$_6$) δ 10.13-9.89 (m, 1H), 8.98 (s, 1H), 8.41 (br d, J=7.1 Hz, 1H), 8.26 (s, 1H), 8.00 (s, 1H), 7.80 (d, J=9.2 Hz, 1H), 7.42 (br d, J=7.0 Hz, 3H), 7.39-7.26 (m, 4H), 7.21 (br d, J=8.3 Hz, 2H), 7.06 (br d, J=5.4 Hz, 1H), 6.83 (dd, J=10.6, 16.9 Hz, 1H), 6.18 (br d, J=16.9 Hz, 1H), 5.74 (br d, J=10.6 Hz, 1H), 5.38 (br s, 1H), 5.12 (br s, 1H), 4.88 (br d, J=6.1 Hz, 1H), 4.52 (d, J=9.9 Hz, 1H), 4.43 (t, J=8.5 Hz, 1H), 4.27 (br s, 1H), 3.92 (br d, J=8.4 Hz, 6H), 3.85 (br s, 2H), 3.78 (br s, 2H), 3.54 (br d, J=14.1 Hz, 6H), 3.46-3.40 (m, 3H), 2.77 (br s, 2H), 2.61 (br s, 1H), 2.45 (s, 3H), 2.39 (br s, 1H), 2.15 (br s, 2H), 2.02 (br d, J=8.6 Hz, 1H), 1.77 (br s, 3H), 1.35 (br d, J=6.5 Hz, 3H), 1.30 (br d, J=6.1 Hz, 3H), 0.90 (br s, 9H).

Exemplary Synthesis of (2S,4R)-1-((2S)-2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide (Exemplary Compound 399)

Step 1: Preparation of tert-butyl 4-(2-(2-(2-ethoxy-2-oxoethoxy)ethoxy)ethoxy)piperidine-1-carboxylate

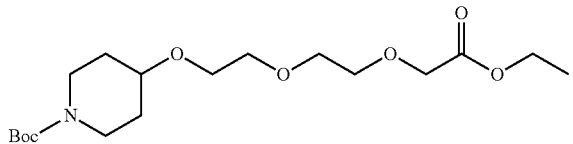 [SMILES: CCOC(=O)COCCOCCOC1CCN(C(=O)OC(C)(C)C)CC1]

To a solution of tert-butyl 4-[2-(2-hydroxyethoxy)ethoxy]piperidine-1-carboxylate (1 g, 3.46 mmol, 1 eq) in dichloromethane (30 mL) was added diacetoxyrhodium (38 mg, 0.17 mmol, 0.05 eq) in one portion at 0° C. under nitrogen, then ethyl 2-diazoacetate (2.37 g, 20.73 mmol, 6 eq) was added and stirred at 25° C. for 16 hours. The mixture was quenched by acetic acid (4 mL) slowly and was added water (20 mL). The aqueous phase was extracted with dichloromethane (15 mL×3). The combined organic phase was washed with brine (20 mL×3), dried with anhydrous sodium sulfate, filtered and concentrated under vacuum. The residue was purified by column chromatography (SiO$_2$, Petroleum ether/Ethyl acetate=30/1 to 10:1). Compound tert-butyl 4-[2-[2-(2-ethoxy-2-oxo-ethoxy)ethoxy]ethoxy]piperidine- 1-carboxylate (700 mg, 1.86 mmol, 54% yield) was obtained as a colorless oil. $^1$H-NMR (400 MHz, CD$_3$OD) δ 4.22-4.16 (m, 4H), 3.71-3.67 (m, 10H), 3.60-3.56 (m, 1H), 3.31-3.13 (m, 2H), 1.81-1.61 (m, 2H), 1.50-1.47 (m, 2H), 1.47 (s, 9H), 1.27 (t, J=7.2 Hz, 3H).

Step 2: Preparation of 2-(2-(2-((1-(tert-butoxycarbonyl)piperidin-4-yl)oxy)ethoxy)ethoxy)acetic acid

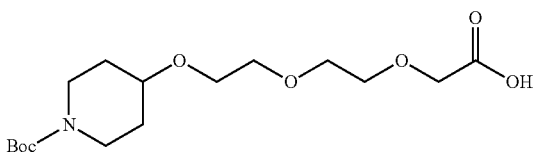 [SMILES: CC(C)(C)OC(=O)N1CCC(OCCOCCOCC(=O)O)CC1]

To a solution of tert-butyl 4-[2-[2-(2-ethoxy-2-oxo-ethoxy)ethoxy]ethoxy]piperidine-1-carboxylate (700 mg, 1.86 mmol, 1 eq) in tetrahydrofuran (2 mL), methanol (2 mL) and water (2 mL) was added lithium hydroxide monohydrate (235 mg, 5.59 mmol, 3 eq), the mixture was stirred at 25° C. for 1 hour. Hydrochloric acid solution (1 M) was added to the mixture to adjust pH about 3-4. The reaction mixture was quenched by water (30 mL), and extracted with ethyl acetate (20 mL×2), the combined organic layers were washed with brine (30 mL), dried over sodium sulfate, filtered and concentrated under reduced pressure to give a residue. Compound 2-[2-[2-[(1-tert-butoxycarbonyl-4-piperidyl)oxy]ethoxy]ethoxy]acetic acid (460 mg, 1.32 mmol, 71% yield) was obtained as a colorless oil.

Step 3: Preparation of tert-butyl 4-(2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)ethoxy)piperidine-1-carboxylate

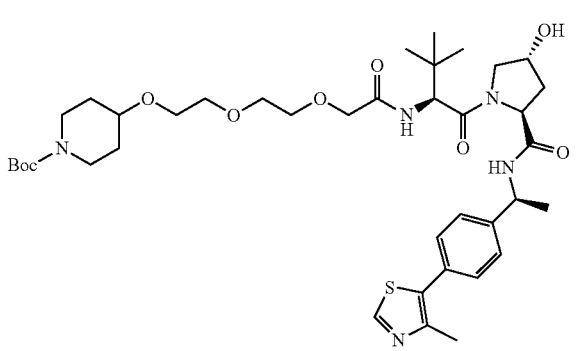 [SMILES: Cc1ncsc1-c1ccc([C@H](C)NC(=O)[C@@H]2C[C@@H](O)CN2C(=O)[C@@H](NC(=O)COCCOCCOC2CCN(C(=O)OC(C)(C)C)CC2)C(C)(C)C)cc1]

To a solution of (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (600 mg, 1.35 mmol, 1 eq) in N,N-dimethylformamide (10 mL) was added 2-[2-[2-[(1-tert-butoxycarbonyl-4-piperidyl)oxy]ethoxy] ethoxy]acetic acid (469 mg, 1.35 mmol, 1 eq), 1-hydroxy-benzotriazol (274 mg, 2.02 mmol, 1.5 eq), 1-(3-dimethyl-aminopropyl)-3-ethylcarbodiimide hydrochloride (388 mg, 2.02 mmol, 1.5 eq) and N,N-diisopropylethylamine (593 mg, 4.59 mmol, 3.4 eq), the mixture was stirred at 25° C. for 16 hours. The reaction mixture was quenched by water (50 mL), and extracted with ethyl acetate (30 mL×2), the combined organic layers were washed with brine (50 mL), dried over sodium sulfate, filtered and concentrated under reduced pressure to give a residue. The residue was purified by column chromatography (SiO$_2$, dichloromethane:methanol=50:1 to 5:1). The residue was further purified by semi-preparative reverse phase HPLC. Compound tert-butyl 4-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy] ethoxy]ethoxy]piperidine-1-carboxylate (777 mg, 1.00 mmol, 74% yield) was obtained as a colorless oil. LC/MS (ESI) m/z: 774.4 [M+1]$^+$.

Step 4: Preparation of (2S,4R)-1-((S)-3,3-dimethyl-2-(2-(2-(2-(piperidin-4-yloxy)ethoxy)ethoxy)acetamido)butanoyl)-4-hydroxy-N—((S)-1-(4-(4-methylthiazol-5-yl)phenyl)ethyl)pyrrolidine-2-carboxamide

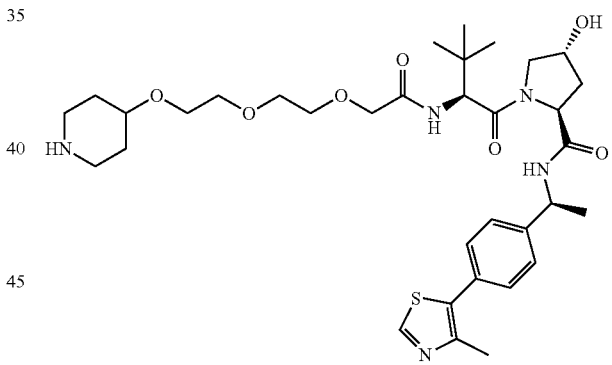

To a solution of tert-butyl 4-[2-[2-[2-[[(1S)-1-[(2S,4R)-4-hydroxy-2-[[(1S)-1-[4-(4-methylthiazol-5-yl)phenyl] ethyl]carbamoyl]pyrrolidine-1-carbonyl]-2,2-dimethyl-propyl]amino]-2-oxo-ethoxy]ethoxy]ethoxy]piperidine-1-carboxylate (80 mg, 0.10 mmol, 1 eq) in dichloromethane (2 mL) was added hydrochloric acid/dioxane (4 M, 0.8 mL, 30.96 eq). The reaction mixture was stirred at 25° C. for 1 hour. The reaction mixture was concentrated under vacuum to get (2S,4R)-1-[(2S)-3,3-dimethyl-2-[[2-[2-[2-(4-piperidyloxy)ethoxy]ethoxy]acetyl]amino]butanoyl]-4-hydroxy-N-[(1S)-1-[4-(4-methylthiazol-5-yl)phenyl]ethyl] pyrrolidine-2-carboxamide (73 mg, 0.10 mmol, 99% yield, hydrochloride) as a light yellow solid.

Step 5: Preparation of tert-butyl 4-(6-chloro-8-fluoro-2-(((R)-1-(4-(2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)ethoxy)piperidin-1-yl)propan-2-yl)oxy)-7-(3-hydroxynaphthalen-1-yl)quinazolin-4-yl)piperazine-1-carboxylate

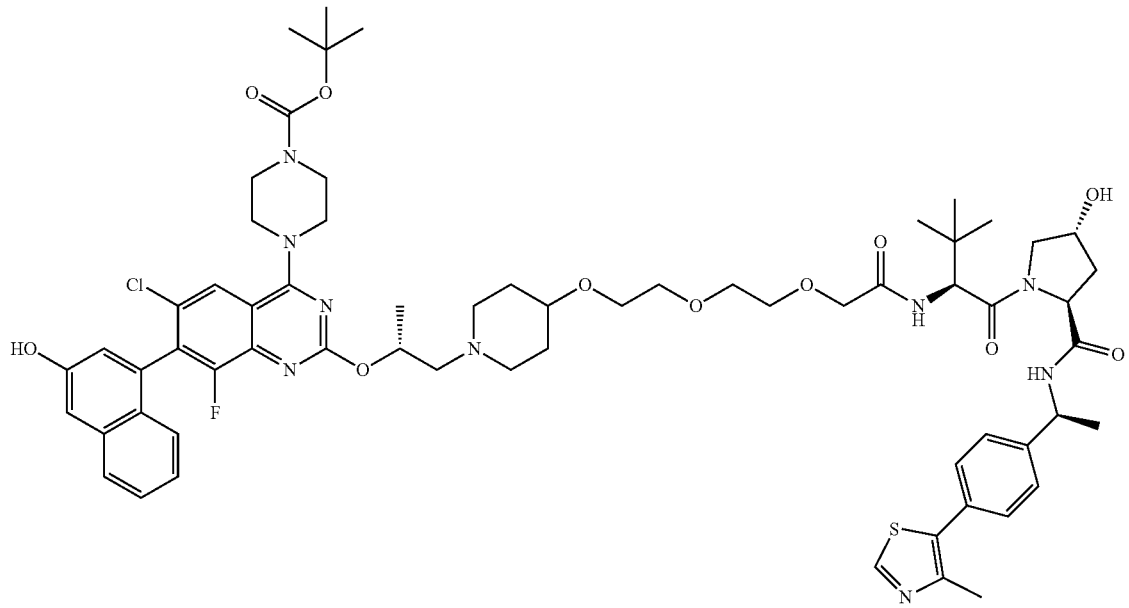 [SMILES: Cc1ncsc1-c1ccc([C@H](C)NC(=O)[C@@H]2C[C@@H](O)CN2C(=O)[C@@H](NC(=O)COCCOCCOC2CCN(C[C@@H](C)Oc3nc(N4CCN(C(=O)OC(C)(C)C)CC4)c4cc(Cl)c(-c5cc(O)cc6ccccc56)c(F)c4n3)CC2)C(C)(C)C)cc1]

To a mixture of (2S,4R)-1-[(2S)-3,3-dimethyl-2-[[2-[2-[2-(4-piperidyloxy)ethoxy]ethoxy]acetyl]amino]butanoyl]-4-hydroxy-N-[(1S)-1-[4-(4-methylthiazol-5-yl)phenyl]ethyl]pyrrolidine-2-carboxamide (73 mg, 0.10 mmol, 1 eq, hydrochloric) in methanol (1 mL) was added sodium acetic (25 mg, 0.31 mmol, 3 eq). The reaction mixture was stirred at 25° C. for 20 minutes. A solution of tert-butyl 4-[6-chloro-8-fluoro-7-(3-hydroxy-1-naphthyl)-2-[(1R)-1-methyl-2-oxo-ethoxy]quinazolin-4-yl]piperazine-1-carboxylate (60 mg, 0.10 mmol, 1 eq) in dichloromethane (2 mL) was added, follow by acetic acid (12 mg, 0.21 mmol, 2 eq). The reaction mixture was cooled to 0° C. and sodium cyanoborohydride (6 mg, 0.41 mmol, 4 eq) was added. The reaction mixture was stirred at 25° C. for 14 hours. Dichloromethane (20 mL) and water (20 mL) were added and the mixture was separated. The organic layer was dried over sodium sulfate and then concentrated under vacuum to get the residue. The residue was purified by prep-TLC (10% methanol in dichloromethane) to get the tert-butyl 4-[6-chloro-8-fluoro-2-[(1R)-2-[4-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]-1-piperidyl]-1-methyl-ethoxy]-7-(3-hydroxy-1-naphthyl)quinazolin-4-yl]piperazine-1-carboxylate (63 mg, 0.05 mmol, 46% yield, 94% purity) as a colorless gum. LC/MS (ESI) m/z: 1238.6 [M+1]$^+$.

Step 6: Preparation of (2S,4R)-1-((2S)-2-(2-(2-(2-((1-((2R)-2-((6-chloro-8-fluoro-7-(3-hydroxynaphthalen-1-yl)-4-(piperazin-1-yl)quinazolin-2-yl)oxy)propyl)piperidin-4-yl)oxy)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide

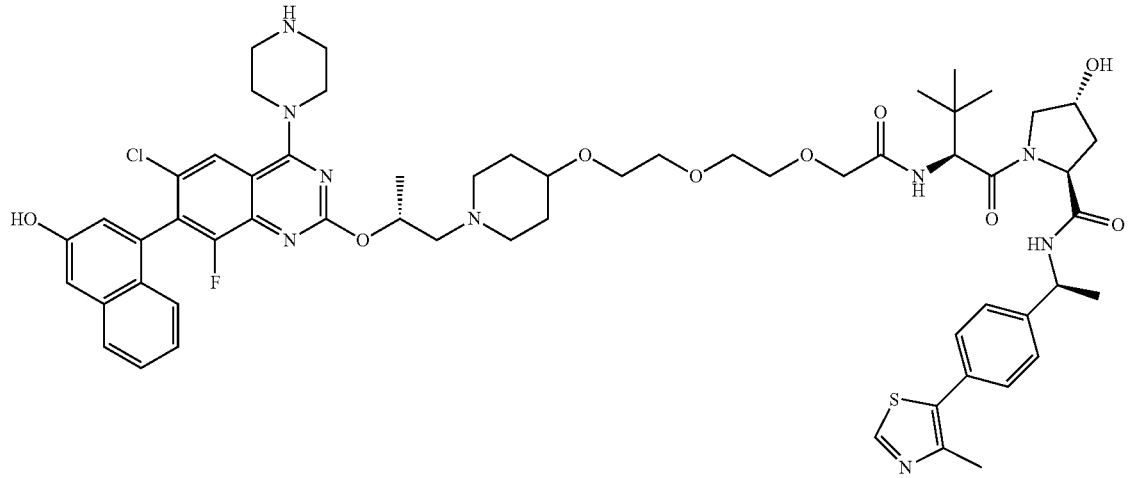 [SMILES: Cc1ncsc1-c1ccc([C@H](C)NC(=O)[C@@H]2C[C@@H](O)CN2C(=O)[C@@H](NC(=O)COCCOCCOC2CCN(C[C@@H](C)Oc3nc(N4CCNCC4)c4cc(Cl)c(-c5cc(O)cc6ccccc56)c(F)c4n3)CC2)C(C)(C)C)cc1]

To a solution of tert-butyl 4-[6-chloro-8-fluoro-2-[(1R)-2-[4-[2-[2-[2-[[(1S)-1-[(2S,4R)-4-hydroxy-2-[[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]-1-piperidyl]-1-methyl-ethoxy]-7-(3-hydroxy-1-naphthyl)quinazolin-4-yl]piperazine-1-carboxylate (63 mg, 0.05 mmol, 1 eq) in dichloromethane (5 mL) was added trifluoroacetic acid (7.70 g, 67.53 mmol, 5 mL, 1327.98 eq). The reaction mixture was stirred at 25° C. for 1 hour. The reaction mixture was concentrated under vacuum to get (2S,4R)-1-[(2S)-2-[[2-[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (63.7 mg, 0.05 mmol, 100% yield, trifluoroacetate) was obtained as a light yellow gum.

Step 7: Preparation of (2S,4R)-1-((2S)-2-(2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide

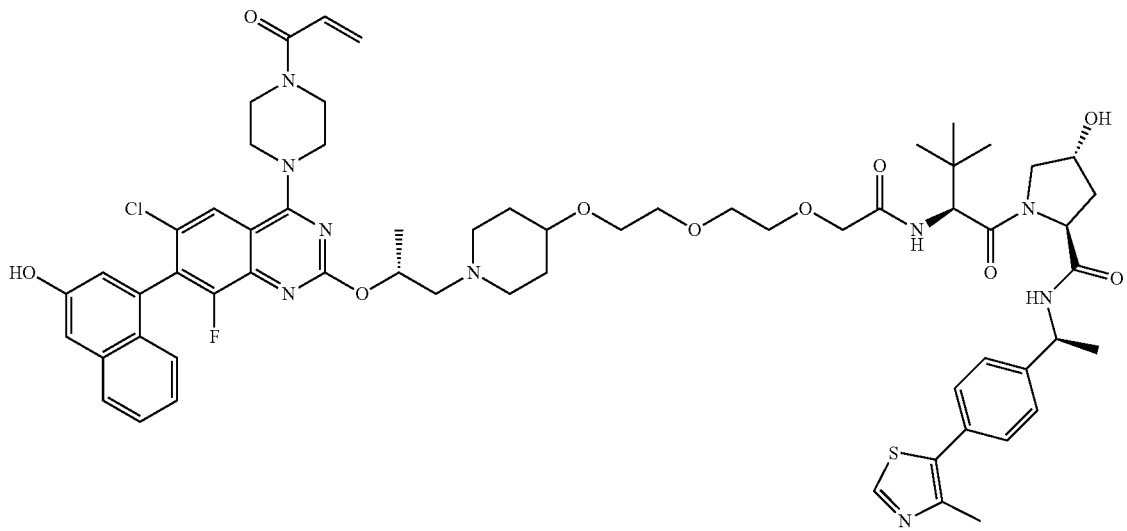 [SMILES: C=CC(=O)N1CCN(c2nc(O[C@H](C)CN3CCC(OCCOCCOCC(=O)N[C@H](C(=O)N4C[C@H](O)C[C@H]4C(=O)N[C@@H](C)c4ccc(-c5scnc5C)cc4)C(C)(C)C)CC3)nc3c(F)c(-c4cc(O)cc5ccccc45)c(Cl)cc23)CC1]

To a solution of (2S,4R)-1-[(2S)-2-[[2-[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (63 mg, 0.05 mmol, 1 eq, trifluoroacetate) in N,N-dimethylformamide (1 mL) and dichloromethane (5 mL) was added 2,6-lutidine (184 mg, 1.72 mmol, 0.2 mL, 34.15 eq). The reaction mixture was cooled to −65° C. and then a solution of prop-2-enoyl chloride (4 mg, 0.05 mmol, 0.9 eq) in dichloromethane (0.36 mL). The reaction mixture was stirred at −65° C. for 10 minutes. Dichloromethane (30 mL) and water (15 mL) were added and the mixture was separated. The organic layer was dried over sodium sulfate and then concentrated under vacuum to get the residue. This residue was purified by semi-preparative reverse phase HPLC. The collected fractions were concentrated under vacuum to remove most of the acetonitrile and then lyophilized. (2S,4R)-1-[(2S)-2-[[2-[2-[2-[[1-[(2R)-2-[6-chloro-8-fluoro-7-(3-hydroxy-1-naphthyl)-4-(4-prop-2-enoylpiperazin-1-yl)quinazolin-2-yl]oxypropyl]-4-piperidyl]oxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (14.5 mg, 0.01 mmol, 21% yield, 98% purity, trifluoroacetate) was obtained as a white solid. LC/MS (ESI) m/z: 1192.5 [M+1]$^+$; $^1$H-NMR (400 MHz, DMSO-$d_6$) δ 10.06 (br d, J=11.9 Hz, 1H), 9.26 (br s, 1H), 8.98 (s, 1H), 8.40 (d, J=7.7 Hz, 1H), 8.07 (s, 1H), 7.82 (d, J=8.2 Hz, 1H), 7.48-7.33 (m, 6H), 7.30 (d, J=2.2 Hz, 1H), 7.27-7.15 (m, 2H), 7.06 (dd, J=2.3, 9.0 Hz, 1H), 6.83 (dd, J=10.6, 16.6 Hz, 1H), 6.19 (dd, J=2.2, 16.6 Hz, 1H), 5.80-5.72 (m, 1H), 5.64 (br s, 1H), 4.89 (br s, 1H), 4.54 (br d, J=9.8 Hz, 1H), 4.42 (br t, J=8.0 Hz, 1H), 4.28 (br s, 1H), 3.96 (br d, J=7.3 Hz, 6H), 3.93-3.90 (m, 4H), 3.86 (br s, 5H), 3.81 (br s, 6H), 3.62-3.51 (m, 10H), 3.43-3.29 (m, 1H), 3.17 (br s, 2H), 2.45 (s, 3H), 2.12-1.86 (m, 3H), 1.77 (br s, 1H), 1.47-1.33 (m, 6H), 0.92 (s, 9H).

Exemplary Synthesis of (2S,4R)-1-((2S)-2-(2-(4-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)methyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Exemplary Compound 403)

Step 1: Preparation of tert-butyl 4-((4-(2-ethoxy-2-oxoethyl)piperazin-1-yl)methyl)piperidine-1-carboxylate

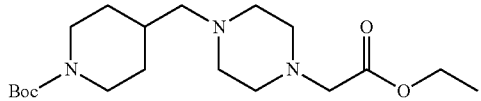 [SMILES: CCOC(=O)CN1CCN(CC2CCN(C(=O)OC(C)(C)C)CC2)CC1]

To the mixture of ethyl 2-piperazin-1-ylacetate (1 g, 4.79 mmol, 1 eq, hydrochloride) in methanol (20 mL) and dichloromethane (20 mL) was added sodium acetate (1.18 g, 14.38 mmol, 3 eq). The mixture was stirred at 25° C. for 10 minutes. Then tert-butyl 4-formylpiperidine-1-carboxylate (1.02 g, 4.79 mmol, 1 eq) and acetic acid (576 mg, 9.58 mmol, 0.6 mL, 2 eq) was added under stirring at 25° C. for 10 minutes. Then sodium cyanoborohydride (603 mg, 9.58 mmol, 2 eq) was added at 0° C. Then the reaction mixture was stirred at 25° C. for 12 hours. Then the mixture was diluted with water (30 mL). Then the mixture was extracted by ethyl acetate (30 mL×3). The combined organic layers were washed with water (50 mL×2) and brine (50 mL×2), dried over anhydrous sodium sulfate, filtered and concentrated under vacuum to give a residue. The residue was purified by silica gel chromatography (Petroleum ether: Ethyl acetate=7:3 to 0:1). Product tert-butyl 4-[[4-(2-ethoxy-2-oxo-ethyl)piperazin-1-yl]methyl]piperidine-1-carboxylate (1.7 g, 4.60 mmol, 96% yield) was obtained as a colorless oil. LC/MS (ESI) m/z: 370.3 [M+1]$^+$; $^1$H-NMR (400 MHz, CDCl$_3$) δ 4.24-4.18 (m, 2H), 3.31 (s, 2H), 3.18-2.97 (m, 4H), 2.97-2.90 (m, 4H), 2.77-2.67 (m, 4H), 2.09 (s, 2H), 1.94-1.85 (m, 1H), 1.84-1.74 (m, 2H), 1.46 (s, 9H), 1.31-1.28 (m, 3H), 1.23-1.14 (m, 2H).

Step 2: Preparation of 2-(4-((1-(tert-butoxycarbonyl)piperidin-4-yl)methyl)piperazin-1-yl)acetic acid

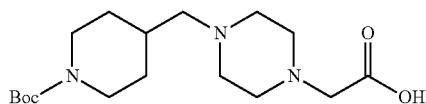 [SMILES: CC(C)(C)OC(=O)N1CCC(CN2CCN(CC(=O)O)CC2)CC1]

To the mixture of tert-butyl 4-[[4-(2-ethoxy-2-oxo-ethyl)piperazin-1-yl]methyl]piperidine-1-carboxylate (200 mg, 0.54 mmol, 1 eq) in tetrahydrofuran (2 mL), methanol (1 mL) and water (2 mL) was added lithium hydroxide monohydrate (68 mg, 1.62 mmol, 3 eq). The mixture was stirred at 25° C. for 1 hour. The mixture was acidified with diluted hydrochloride acid (1 M) to PH=6-7. Then the mixture was concentrated under vacuum to give a residue. Product 2-[4-[(1-tert-butoxycarbonyl-4-piperidyl)methyl]piperazin-1-yl]acetic acid (180 mg) was obtained as a pink solid.

Step 3: Preparation of tert-butyl 4-((4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)methyl)piperidine-1-carboxylate

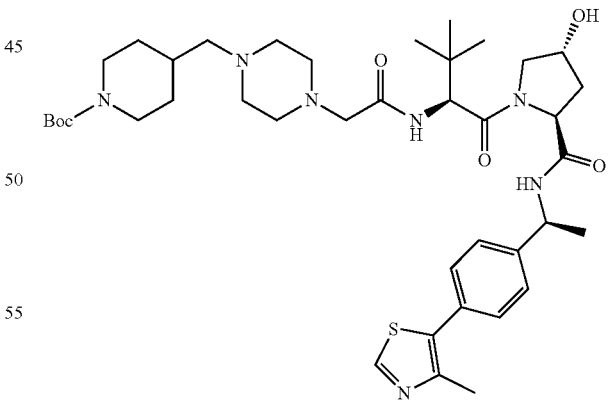

To the mixture of 2-[4-[(1-tert-butoxycarbonyl-4-piperidyl)methyl]piperazin-1-yl]acetic acid (115 mg, 0.34 mmol, 1 eq) and (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (150 mg, 0.34 mmol, 1 eq, hydrochloride) in N,N-dimethylformamide (5 mL) was added 1-hydroxybenzotriazole (91 mg, 0.68 mmol, 2 eq), N-(3-dimethylaminopropyl)-N-ethylcarbodiimide hydrochloride (130 mg, 0.68 mmol, 2 eq) and N,N-diisopropylethylamine (218 mg, 1.69 mmol, 0.3 mL, 5 eq). The mixture was stirred at 25° C. for 12 hours. The mixture was diluted with water (30 mL). Then the mixture was extracted by ethyl acetate (30 mL×3). The combined organic layers were washed with water (50 mL×2) and brine (50 mL×2), dried over anhydrous sodium sulfate, filtered and concentrated under vacuum to give a residue. The residue was purified by prep-TLC (dichloromethane:methanol=10:1). Compound tert-butyl 4-[[4-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]piperazin-1-yl]methyl]piperidine-1-carboxylate (70 mg) was obtained as a colorless oil. LC/MS (ESI) m/z: 768.5 [M+1]⁺.

Step 4: Preparation of (2S,4R)-1-((S)-3,3-dimethyl-2-(2-(4-(piperidin-4-ylmethyl)piperazin-1-yl)acetamido)butanoyl)-4-hydroxy-N—((S)-1-(4-(4-methylthiazol-5-yl)phenyl)ethyl)pyrrolidine-2-carboxamide To the mixture of tert-butyl 4-[[4-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]piperazin-1-yl]methyl]piperidine-1-carboxylate (70 mg, 0.09 mmol, 1 eq) in dichloromethane (5 mL) was added hydrogen chloride/dioxane (4 M, 5 mL). The mixture was stirred at 25° C. for 30 minutes. Then the mixture was concentrated under vacuum to give a residue. Product (2S,4R)-1-[(2S)-3,3-dimethyl-2-[[2-[4-(4-piperidylmethyl)piperazin-1-yl]acetyl]amino]butanoyl]-4-hydroxy-N-[(1S)-1-[4-(4-methylthiazol-5-yl)phenyl]ethyl]pyrrolidine-2-carboxamide (64 mg, hydrochloride) was obtained as a white solid. LC/MS (ESI) m/z: 668.5 [M+1]⁺.

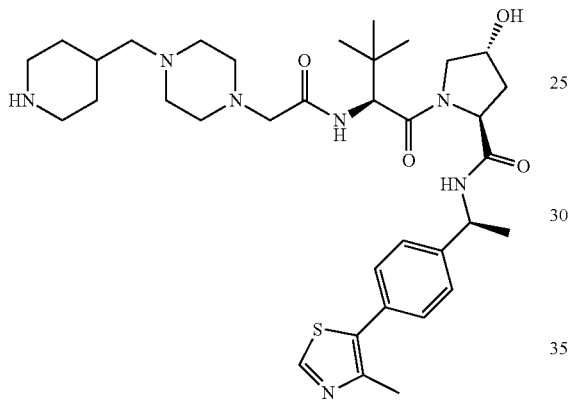

Step 5: Preparation of tert-butyl 4-(6-chloro-8-fluoro-2-(((R)-1-(4-((4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)methyl)piperidin-1-yl)propan-2-yl)oxy)-7-(3-hydroxynaphthalen-1-yl)quinazolin-4-yl)piperazine-1-carboxylate

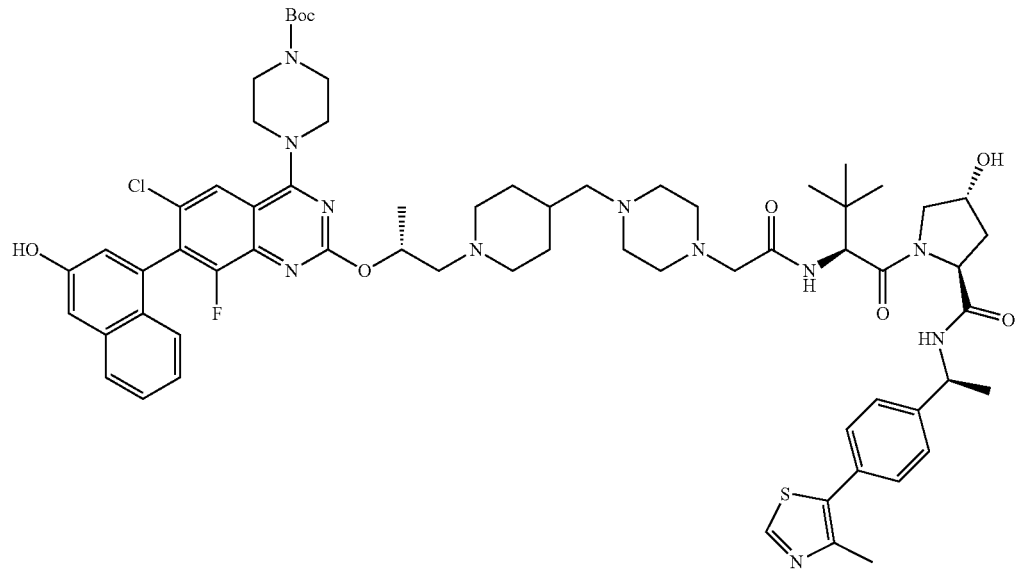 [SMILES: Cc1ncsc1-c1ccc([C@H](C)NC(=O)[C@@H]2C[C@@H](O)CN2C(=O)[C@@H](NC(=O)CN2CCN(CC3CCN(C[C@@H](C)Oc4nc(N5CCN(C(=O)OC(C)(C)C)CC5)c5cc(Cl)c(-c6cc(O)cc7ccccc67)c(F)c5n4)CC3)CC2)C(C)(C)C)cc1]

To the mixture of (2S,4R)-1-[(2S)-3,3-dimethyl-2-[[2-[4-(4-piperidylmethyl)piperazin-1-yl]acetyl]amino]butanoyl]-4-hydroxy-N-[(1S)-1-[4-(4-methylthiazol-5-yl)phenyl]ethyl]pyrrolidine-2-carboxamide (64 mg, 0.09 mmol, 1 eq, hydrochloride) in dichloromethane (3 mL) and methanol (3 mL) was added sodium acetate (23 mg, 0.27 mmol, 3 eq). The mixture was stirred at 25° C. for 10 minutes. Then tert-butyl 4-[6-chloro-8-fluoro-7-(3-hydroxy-1-naphthyl)-2-[(1R)-1-methyl-2-oxo-ethoxy]quinazolin-4-yl]piperazine-1-carboxylate (53 mg, 0.09 mmol, 1 eq) and acetic acid (11 mg, 0.18 mmol, 2 eq) was added under stirring at 25° C. for 10 minutes. Then sodium cyanoborohydride (18 mg, 0.27 mmol, 3 eq) was added at 0° C. Then the reaction mixture was stirred at 25° C. for 12 hours. The mixture was concentrated under vacuum to give a residue. The residue was purified by prep-TLC (dichloromethane:methanol=10:1).

Product tert-butyl 4-[6-chloro-8-fluoro-2-[(1R)-2-[4-[[4-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]piperazin-1-yl]methyl]-1-piperidyl]-1-methyl-ethoxy]-7-(3-hydroxy-1-naphthyl)quinazolin-4-yl]piperazine-1-carboxylate (40 mg, 0.03 mmol, 36% yield) was obtained as a white solid. LC/MS (ESI) m/z: 617.4 [M/2+1]$^+$.

Step 6: Preparation of (2S,4R)-1-((2S)-2-(2-(4-((1-((2R)-2-((6-chloro-8-fluoro-7-(3-hydroxynaphthalen-1-yl)-4-(piperazin-1-yl)quinazolin-2-yl)oxy)propyl)piperidin-4-yl)methyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide

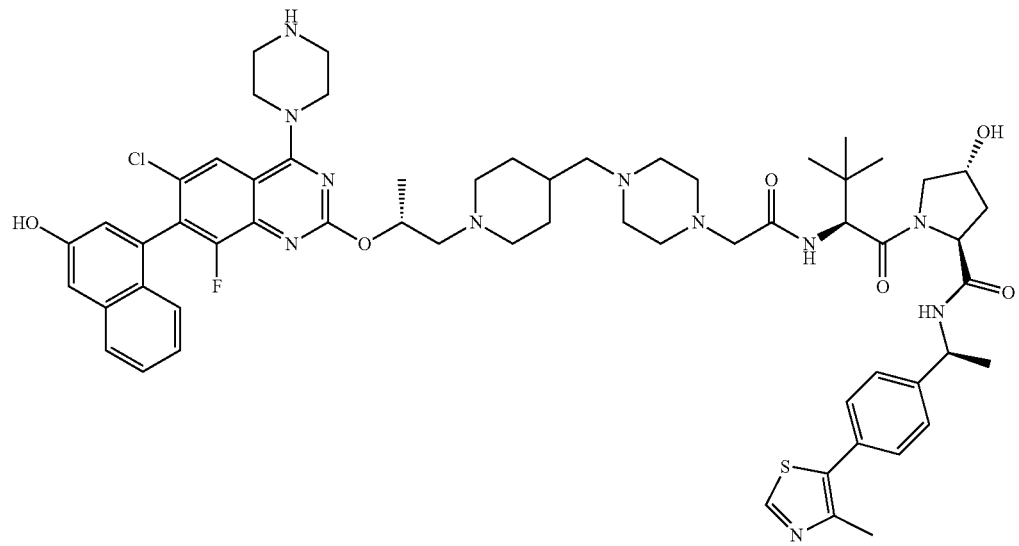 [SMILES: Cc1ncsc1-c1ccc([C@H](C)NC(=O)[C@@H]2C[C@@H](O)CN2C(=O)[C@@H](NC(=O)CN2CCN(CC3CCN(C[C@@H](C)Oc4nc(N5CCNCC5)c5cc(Cl)c(-c6cc(O)cc7ccccc67)c(F)c5n4)CC3)CC2)C(C)(C)C)cc1]

To the mixture of tert-butyl 4-[6-chloro-8-fluoro-2-[(1R)-2-[4-[[4-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]piperazin-1-yl]methyl]-1-piperidyl]-1-methyl-ethoxy]-7-(3-hydroxy-1-naphthyl)quinazolin-4-yl]piperazine-1-carboxylate (40 mg, 0.03 mmol, 1 eq) in dichloromethane (5 mL) was added trifluoroacetic acid (3.08 g, 2 mL). The mixture was stirred at 25° C. for 30 minutes. The mixture was concentrated under vacuum to give a residue. (2S,4R)-1-[(2S)-2-[[2-[4-[[1-[(2R)-2-[6-chloro-8-fluoro-7-(3-hydroxy-1-naphthyl)-4-piperazin-1-yl-quinazolin-2-yl]oxy-propyl]-4-piperidyl]methyl]piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (40 mg, trifluoroacetates) was obtained as a white solid.

Step 7: Preparation of (2S,4R)-1-((2S)-2-(2-(4-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)methyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide

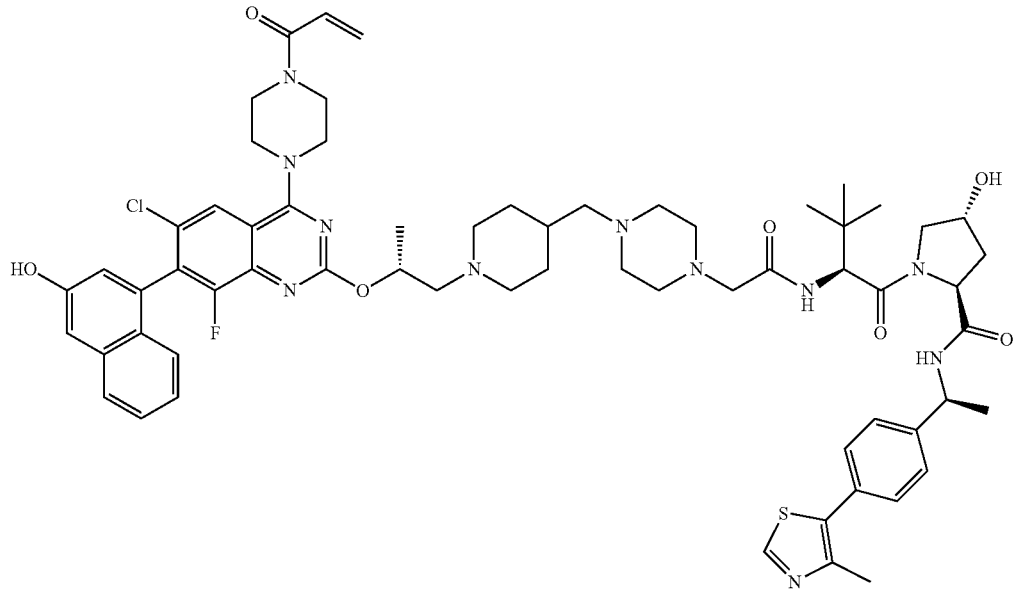 [SMILES: C=CC(=O)N1CCN(c2nc(O[C@H](C)CN3CCC(CN4CCN(CC(=O)N[C@H](C(=O)N5C[C@H](O)C[C@H]5C(=O)N[C@@H](C)c5ccc(-c6scnc6C)cc5)C(C)(C)C)CC4)CC3)nc3c(F)c(-c4cc(O)cc5ccccc45)c(Cl)cc23)CC1]

To the mixture of (2S,4R)-1-[(2S)-2-[[2-[4-[[1-[(2R)-2-[6-chloro-8-fluoro-7-(3-hydroxy-1-naphthyl)-4-piperazin-1-yl-quinazolin-2-yl]oxypropyl]-4-piperidyl]methyl]piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (40 mg, 0.03 mmol, 1 eq, trifluoroacetates) in dichloromethane (20 mL) was added 2,6-lutidine (35 mg, 0.32 mmol, 0.04 mL, 10 eq). Then prop-2-enoyl chloride (3 mg, 0.03 mL, 0.9 eq) in dichloromethane (5 mL) was added at −78° C. under nitrogen atmosphere. Then the mixture was stirred at −78° C. for 15 minutes under nitrogen atmosphere. The mixture was diluted with water (25 mL). Then it was extracted with dichloromethane (20 mL×3). The combined organic layers were washed with brine (30 mL×2), dried over anhydrous sodium sulfate, filtered and concentrated under vacuum to give a residue. The residue was purified by prep-HPLC. Compound (2S,4R)-1-[(2S)-2-[[2-[4-[[1-[(2R)-2-[6-chloro-8-fluoro-7-(3-hydroxy-1-naphthyl)-4-(4-prop-2-enoylpiperazin-1-yl)quinazolin-2-yl]oxypropyl]-4-piperidyl]methyl]piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (5.8 mg, 0.005 mmol, 14.7% yield, 100% purity, formate) was obtained as a white solid. LC/MS (ESI) m/z: 593.8 [M/2+1]⁺; ¹H-NMR (400 MHz, DMSO-$d_6$) δ 8.96 (s, 1H), 8.44-8.42 (d, J=8.0 Hz, 1H), 8.28 (s, 2H), 8.00 (s, 1H), 7.80-7.78 (d, J=8.0 Hz, 1H), 7.70-7.66 (d, J=16.0 Hz, 1H), 7.46-7.39 (m, 3H), 7.38-7.31 (m, 2H), 7.28-7.27 (d, J=4.0 Hz, 1H), 7.26-7.15 (m, 2H), 7.10-7.03 (m, 1H), 6.88-6.77 (m, 1H), 6.22-6.13 (m, 1H), 5.78-5.71 (m, 1H), 5.45-5.36 (m, 1H), 4.92-4.81 (m, 1H), 4.50-4.32 (m, 3H), 4.26 (s, 1H), 3.99-3.69 (m, 14H), 3.11-2.79 (m, 5H), 2.44 (s, 7H), 2.11-1.85 (m, 6H), 1.79-1.69 (m, 1H), 1.59-1.49 (m, 2H), 1.41-1.26 (m, 7H), 0.90 (s, 12H).

Exemplary Synthesis of (2S,4R)-1-((2S)-2-(2-(4-((4-((2R)-2-((4-(4-acryloylpiperazin-1-yl)-6-chloro-8-fluoro-7-(3-hydroxynaphthalen-1-yl)quinazolin-2-yl)oxy)propyl)piperazin-1-yl)methyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Exemplary Compound 404)

Step 1: Preparation of tert-butyl 4-((1-((benzyloxy)carbonyl)piperidin-4-yl)methyl)piperazine-1-carboxylate

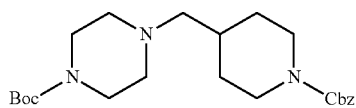 [SMILES: CC(C)(C)OC(=O)N1CCN(CC2CCN(C(=O)OCc3ccccc3)CC2)CC1]

To a solution of tert-butyl 4-[2-(2-hydroxyethoxy)ethoxy]piperidine-1-carboxylate (1 g, 3.46 mmol, 1 eq) in hydrochloride/methanol (4 M, 3 mL, 3.47 eq), the mixture was stirred at 25° C. for 1 hour. The mixture was filtered and concentrated under reduced pressure to give a residue. Compound 2-[2-(4-piperidyloxy)ethoxy]ethanol (600 mg, hydrochloride) was obtained as a white solid.

Step 2: Preparation of tert-butyl 4-(piperidin-4-ylmethyl)piperazine-1-carboxylate

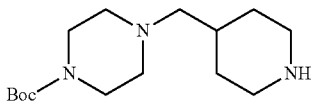 [SMILES: CC(C)(C)OC(=O)N1CCN(CC2CCNCC2)CC1]

To a solution of tert-butyl 4-[(1-benzyloxycarbonyl-4-piperidyl)methyl]piperazine-1-carboxylate (910 mg, 2.18 mmol, 1 eq) in methanol (15 mL) was added palladium on activated carbon catalyst (500 mg, 10% purity), The suspension was degassed under vacuum and purged with hydrogen several times. The palladium on activated carbon catalyst (100 mg, 0.07 mmol, 10% purity, 3.27e-2 eq) in methanol (15 mL) was added to the mixture and stirred under hydrogen (4 mg, 2.18 mmol, 1 eq) (50 psi) at 25° C. for 16 hours. The reaction mixture was filtered and the filter was concentrated. Compound tert-butyl 4-(4-piperidylmethyl)piperazine-1-carboxylate (1.8 g) was obtained as a colorless gum. LC/MS (ESI) m/z: 284.1 [M+1].

Step 3: Preparation of tert-butyl 4-((1-(2-ethoxy-2-oxoethyl)piperidin-4-yl)methyl)piperazine-1-carboxylate

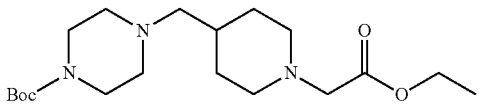 [SMILES: CCOC(=O)CN1CCC(CN2CCN(C(=O)OC(C)(C)C)CC2)CC1]

To a solution of tert-butyl 4-(4-piperidylmethyl)piperazine-1-carboxylate (650 mg, 2.29 mmol, 1 eq) and ethyl 2-bromoacetate (460 mg, 2.75 mmol, 0.3 mL, 1.2 eq) in acetonitrile (10 mL) was added potassium carbonate (951 mg, 6.88 mmol, 3 eq), the mixture was stirred at 80° C. for 16 hours. The reaction mixture was quenched by water (30 mL), and extracted with ethyl acetate (20 mL×2), the combined organic layers were washed with brine (30 mL), dried over sodium sulfate, filtered and concentrated under reduced pressure to give a residue. The residue was purified by silica gel chromatography (petroleum ether:ethyl acetate=10:1 to 0:1). Compound tert-butyl 4-[[1-(2-ethoxy-2-oxo-ethyl)-4-piperidyl]methyl]piperazine-1-carboxylate (537 mg, 1.45 mmol, 63% yield) was obtained as a yellow oil. $^1$H-NMR (400 MHz, CDCl$_3$) δ 4.16 (q, J=7.2 Hz, 2H), 3.38 (d, J=4.8 Hz, 2H), 3.20 (s, 2H), 2.94 (d, J=11.6 Hz, 2H), 2.36-2.27 (m, 4H), 2.21-2.11 (m, 4H), 1.73 (d, J=12.8 Hz, 2H), 1.43 (s, 9H), 1.26-1.22 (m, 8H).

Step 4: Preparation of 2-(4-((4-(tert-butoxycarbonyl)piperazin-1-yl)methyl)piperidin-1-yl)acetic acid

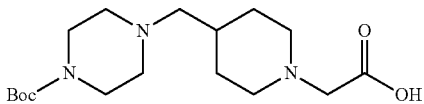 [SMILES: CC(C)(C)OC(=O)N1CCN(CC2CCN(CC(=O)O)CC2)CC1]

To a solution of tert-butyl 4-[[1-(2-ethoxy-2-oxo-ethyl)-4-piperidyl]methyl]piperazine-1-carboxylate (567 mg, 1.53 mmol, 1 eq) in water (5 mL), methanol (5 mL) and tetrahydrofuran (5 mL) was added lithium hydroxide monohydrate (322 mg, 7.67 mmol, 5 eq), the mixture was stirred at 25° C. for 2 hours. The mixture was poured into the hydrochloric acid solution (1 M) to adjust pH about 6-7. The reaction mixture was extracted with (chloroform:isopropanol=5:1) (200 mL×2), the combined organic layers were dried over sodium sulfate, filtered and concentrated under reduced pressure to give a residue. Compound 2-[4-[(4-tert-butoxycarbonylpiperazin-1-yl)methyl]-1-piperidyl]acetic acid (332 mg, 0.97 mmol, 63% yield) was obtained as a yellow solid. $^1$H-NMR (400 MHz, CD$_3$OD) δ 3.57 (s, 2H), 3.42 (s, 4H), 2.38 (t, J=5.2 Hz, 4H), 2.26 (d, J=7.2 Hz, 2H), 2.02 (d, J=14.4 Hz, 2H), 1.56-1.42 (m, 11H), 1.15 (d, J=6.0 Hz, 5H).

Step 5: Preparation of tert-butyl 4-((1-(2-(((S)-1-((2S,4R)-4-hydroxy-2-((((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperidin-4-yl)methyl)piperazine-1-carboxylate

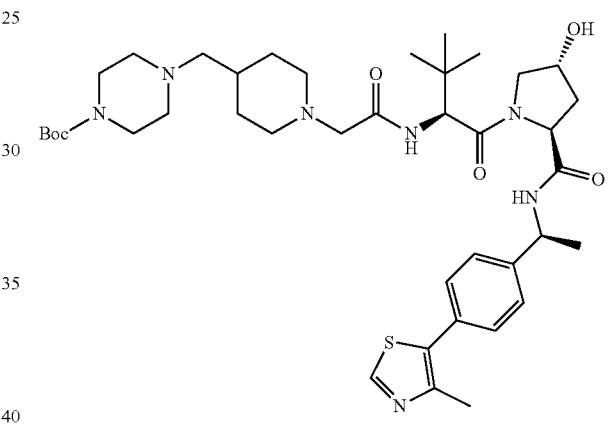

To a solution of 2-[4-[(4-tert-butoxycarbonylpiperazin-1-yl)methyl]-1-piperidyl]acetic acid (115 mg, 0.3 mmol, 1.08 eq) in N,N-dimethylformamide (5 mL) was added (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (150 mg, 0.3 mmol, 1 eq, hydrochloride), 1-(3-dimethylaminopropyl)-3-ethylcarbodiimide hydrochloride (90 mg, 0.47 mmol, 1.5 eq), 1-hydroxybenzotriazole (63 mg, 0.47 mmol, 1.5 eq), N,N-diisopropylethylamine (161 mg, 1.25 mmol, 0.2 mL, 4 eq), the mixture was stirred at 25° C. for 2 hours. The reaction mixture was quenched by water (30 mL), and extracted with ethyl acetate (50 mL×2), the combined organic layers were washed with brine (30 mL), dried over sodium sulfate, filtered and concentrated under reduced pressure to give a residue. The residue was purified by prep-TLC (dichloromethane:methanol=10:1). Compound tert-butyl 4-[[1-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]-4-piperidyl]methyl]piperazine-1-carboxylate (140 mg, 0.18 mmol, 57% yield, 98% purity) was obtained as a colorless solid. LC/MS (ESI) m/z: 768.05 [M+1]$^+$; $^1$H-NMR (400 MHz, CD$_3$OD) δ 8.88 (s, 1H), 7.47-7.38 (m, 4H), 5.01 (q, J=7.2 Hz, 1H), 4.65-4.44 (m, 4H), 3.90-3.83 (m, 1H), 3.80-3.69 (m, 1H), 3.42 (s, 3H), 3.35 (s, 4H), 3.03 (d, J=4.4 Hz, 2H), 2.93-2.84 (m, 2H), 2.48 (s, 3H), 2.37 (t, J=4.8 Hz, 4H), 2.25-2.20 (m, 4H), 2.02-1.91 (m, 1H), 1.80 (t, J=13.6 Hz, 2H), 1.60-1.50 (m, 4H), 1.45 (s, 9H), 1.33-1.22 (m, 2H), 1.06-1.02 (m, 9H).

Step 6: Preparation of (2S,4R)-1-((S)-3,3-dimethyl-2-(2-(4-(piperazin-1-ylmethyl)piperidin-1-yl)acetamido)butanoyl)-4-hydroxy-N—((S)-1-(4-(4-methylthiazol-5-yl)phenyl)ethyl)pyrrolidine-2-carboxamide

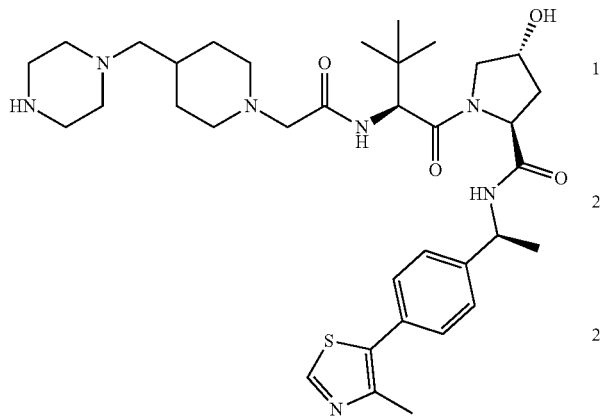

To a solution of tert-butyl 4-[[1-[2-[[(1S)-1-[(2S,4R)-4-hydroxy-2-[[(1S)-1-[4-(4-methylthia-zol-5-yl)phenyl]ethyl]

carbamoyl]pyrrolidine-1-carbonyl]-2,2-dimethyl-propyl]amino]-2-oxo-ethyl]-4-piperidyl]methyl]piperazine-1-carboxylate (140 mg, 0.18 mmol, 1 eq) in hydrochloric acid/methanol (4 M, 5 mL, 109.72 eq), the mixture was stirred at 25° C. for 1 hour. The mixture was concentrated under reduced pressure to give a residue. Compound (2S, 4R)-1-[(2S)-3,3-dimethyl-2-[[2-[4-(piperazin-1-ylmethyl)-1-piperidyl]acetyl]amino]butanoyl]-4-hydroxy-N-[(1S)-1-[4-(4-methylthiazol-5-yl)phenyl]ethyl]pyrrolidine-2-carboxamide (120 mg, 0.17 mmol, 93% yield, hydrochloride) was obtained as a colorless oil. LC/MS (ESI) m/z: 668.5 [M+1]$^+$.

Step 7: Preparation of tert-butyl 4-(6-chloro-8-fluoro-2-(((R)-1-(4-((1-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperidin-4-yl)methyl)piperazin-1-yl)propan-2-yl)oxy)-7-(3-hydroxynaphthalen-1-yl)quinazolin-4-yl)piperazine-1-carboxylate

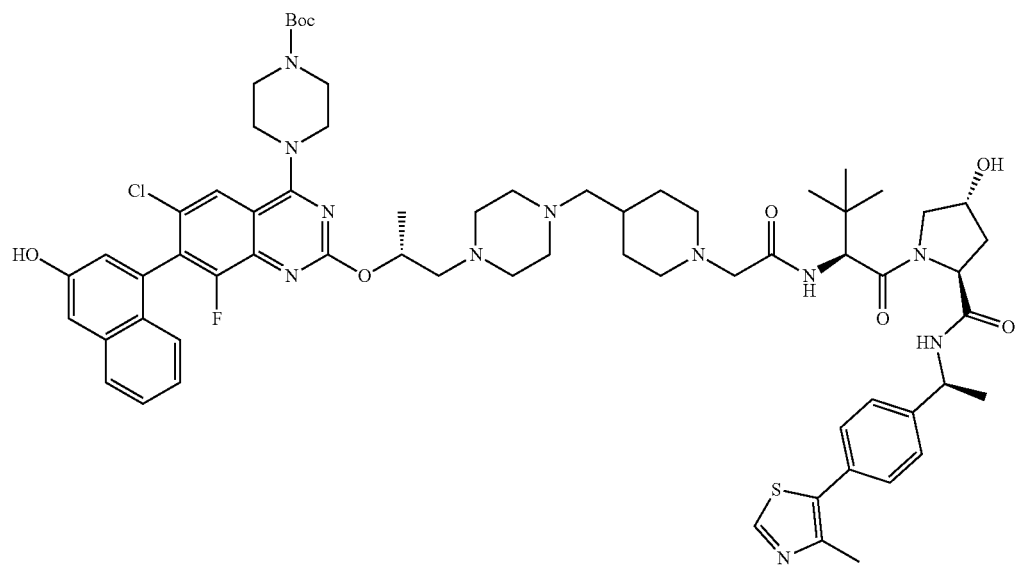 [SMILES: Cc1ncsc1-c1ccc([C@H](C)NC(=O)[C@@H]2C[C@@H](O)CN2C(=O)[C@@H](NC(=O)CN2CCC(CN3CCN(C[C@@H](C)Oc4nc(N5CCN(C(=O)OC(C)(C)C)CC5)c5cc(Cl)c(-c6cc(O)cc7ccccc67)c(F)c5n4)CC3)CC2)C(C)(C)C)cc1]

To a solution of (2S,4R)-1-[(2S)-3,3-dimethyl-2-[[2-[4-(piperazin-1-ylmethyl)-1-piperidyl]acetyl]amino]butanoyl]-4-hydroxy-N-[(1S)-1-[4-(4-methylthiazol-5-yl)phenyl]ethyl]pyrrolidine-2-carboxamide (73 mg, 0.1 mmol, 1 eq, hydrochloride) in methanol (3 mL) was added sodium acetate (25 mg, 0.3 mmol, 3 eq), the mixture was stirred at 25° C. for 0.5 h. Then tert-butyl 4-[6-chloro-8-fluoro-7-(3-hydroxy-1-naphthyl)-2-[(1R)-1-methyl-2-oxo-ethoxy]quinazolin-4-yl]piperazine-1-carboxylate (60 mg, 0.1 mmol, 1 eq) in dichloromethane (3 mL) was added. Acetic acid (6 mg, 0.1 mmol, 0.006 mL, 1 eq) followed by sodium cyanoborohydride (19 mg, 0.3 mmol, 3 eq) were added to the reaction at 0° C. for 0.5 hour. The mixture was stirred at 25° C. for 11 hours. The mixture was concentrated under reduced pressure to give a residue. The residue was purified by prep-TLC (dichloromethane:methanol=10:1). Compound tert-butyl 4-[6-chloro-8-fluoro-2-[(1R)-2-[4-[[1-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]-4-piperidyl]methyl]piperazin-1-yl]-1-methyl-ethoxy]-7-(3-hydroxy-1-naphthyl)quinazolin-4-yl]piperazine-1-carboxylate (72 mg, 0.06 mmol, 55% yield, 97% purity) was obtained as a colorless oil. LC/MS (ESI) m/z: 617.4 [M/2+1]$^+$.

Step 8: Preparation of (2S,4R)-1-((2S)-2-(2-(4-((4-((2R)-2-((6-chloro-8-fluoro-7-(3-hydroxynaphthalen-1-yl)-4-(piperazin-1-yl)quinazolin-2-yl)oxy)propyl)piperazin-1-yl)methyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide

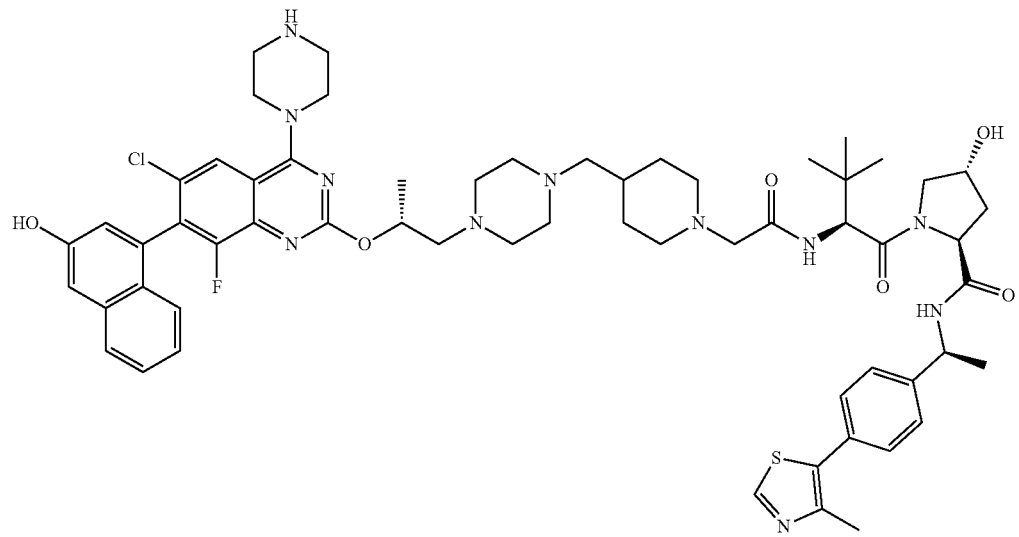 [SMILES: Cc1ncsc1-c1ccc([C@H](C)NC(=O)[C@@H]2C[C@@H](O)CN2C(=O)[C@@H](NC(=O)CN2CCC(CN3CCN(C[C@@H](C)Oc4nc(N5CCNCC5)c5cc(Cl)c(-c6cc(O)cc7ccccc67)c(F)c5n4)CC3)CC2)C(C)(C)C)cc1]

To a solution of tert-butyl 4-[6-chloro-8-fluoro-2-[(1R)-2-[4-[[1-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]-4-piperidyl]methyl]piperazin-1-yl]-1-methyl-ethoxy]-7-(3-hydroxy-1-naphthyl)quinazolin-4-yl]piperazine-1-carboxylate (72 mg, 0.06 mmol, 1 eq) in dichloromethane (10 mL) was added trifluoroacetic acid (1.54 g, 13.51 mmol, 1 mL, 231.28 eq), the mixture was stirred at 25° C. for 1 hour. The mixture was concentrated under reduced pressure to give a residue. Compound (2S,4R)-1-[(2S)-2-[[2-[4-[[4-[(2R)-2-[6-chloro-8-fluoro-7-(3-hydroxy-1-naphthyl)-4-piperazin-1-yl-quinazolin-2-yl]oxypropyl]piperazin-1-yl]methyl]-1-piperidyl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (72 mg, 0.06 mmol, 99% yield, trifluoroacetate) was obtained as a yellow oil. LC/MS (ESI) m/z: 567.4 [M/2+1]$^+$.

Step 9: Preparation of (2S,4R)-1-((2S)-2-(2-(4-((4-((2R)-2-((4-(4-acryloylpiperazin-1-yl)-6-chloro-8-fluoro-7-(3-hydroxynaphthalen-1-yl)quinazolin-2-yl)oxy)propyl)piperazin-1-yl)methyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide To a solution of (2S,4R)-1-[(2S)-2-[[2-[4-[[4-[(2R)-2-[6-chloro-8-fluoro-7-(3-hydroxy-1-naphthyl)-4-piperazin-1-yl-quinazolin-2-yl]oxypropyl]piperazin-1-yl]methyl]-1-piperidyl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (72 mg, 0.06 mmol, 1 eq, trifluoroacetate) in N,N-dimethylformamide (1 mL) was added 2,6-lutidine (248 mg, 2.31 mmol, 0.3 mL, 40 eq), the mixture was cooled to −78° C., and then prop-2-enoyl chloride (4.70 mg, 0.05 mmol, 0.004 mL, 0.9 eq) in dichloromethane (5 mL) was added drop wise, the mixture was stirred at −78° C. for 30 minutes. The mixture was concentrated under reduced pressure to give a residue. The residue was purified by semi-preparative reverse phase HPLC. Compound (2S,4R)-1-[(2S)-2-[[2-[4-[[4-[(2R)-2-[6-chloro-8-fluoro-7-(3-hydroxy-1-naphthyl)-4-(4-prop-2-enoylpiperazin-1-yl)quinazolin-2-yl]oxypropyl]piperazin-1-yl]methyl]-1-piperidyl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (9.9 mg, 0.008 mmol, 14% yield, 96% purity) was obtained as a white solid. LC/MS (ESI) m/z: 594.8 [M/2+1]$^+$; $^1$H-NMR (400 MHz, DMSO-d$_6$) δ 8.98 (s, 1H), 8.45 (d, J=7.7 Hz, 1H), 8.25 (s, 2H), 8.01 (s, 1H), 7.81 (d, J=8.2 Hz, 1H), 7.73 (d, J=9.7 Hz, 1H), 7.43 (d, J=8.2 Hz, 3H), 7.36 (d, J=8.4 Hz, 2H), 7.29 (d, J=2.2 Hz, 1H), 7.24-7.18 (m, 2H), 7.06 (dd, J=2.3, 8.5 Hz, 1H), 6.84

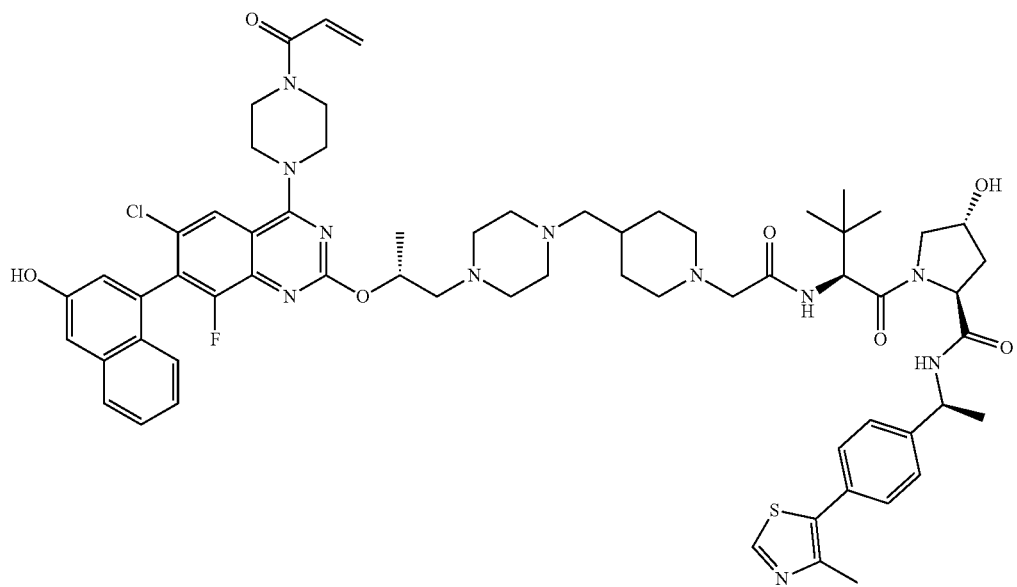 [SMILES: C=CC(=O)N1CCN(c2nc(O[C@H](C)CN3CCN(CC4CCN(CC(=O)N[C@H](C(=O)N5C[C@H](O)C[C@H]5C(=O)N[C@@H](C)c5ccc(-c6scnc6C)cc5)C(C)(C)C)CC4)CC3)nc3c(F)c(-c4cc(O)cc5ccccc45)c(Cl)cc23)CC1]

(dd, J=10.5, 16.7 Hz, 1H), 6.18 (dd, J=2.1, 16.6 Hz, 1H), 5.79-5.72 (m, 1H), 5.45-5.38 (m, 1H), 4.88 (t, J=7.2 Hz, 1H), 4.51-4.39 (m, 2H), 4.27 (s, 1H), 3.95-3.73 (m, 8H), 2.99 (d, J=14.9 Hz, 1H), 2.87-2.71 (m, 4H), 2.69-2.58 (m, 3H), 2.45 (s, 3H), 2.40 (s, 2H), 2.21 (s, 4H), 2.08-2.02 (m, 6H), 1.79-1.58 (m, 4H), 1.45-1.29 (m, 8H), 1.07 (s, 2H), 0.92 (s, 9H).

Exemplary Synthesis of (2S,4R)-1-((S)-20-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-2-(tert-butyl)-4-oxo-6,9,12,15,18-pentaoxa-3-azaicosanoyl)-4-hydroxy-N—((S)-1-(4-(4-methylthiazol-5-yl)phenyl)ethyl)pyrrolidine-2-carboxamide (Exemplary Compound 410)

Step 1: Preparation of 2,4-dibromonaphthalen-1-amine

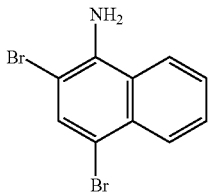 [SMILES: Nc1c(Br)cc(Br)c2ccccc12]

To a solution of dibromine (25.67 g, 160.63 mmol, 8.3 mL, 2.30 eq) in acetic acid (75 mL) was added dropwise a solution of naphthalen-1-amine (10.00 g, 69.84 mmol, 9.8 mL, 1.00 eq) in acetic acid (50 mL) at 5° C. for 30 minutes. After the addition was completed, acetic acid (50 mL) was diluted. The reaction mixture was heated to 70° C. for 30 min. The suspension was filtered and washed with acetic acid (100 mL), the filter cake was suspend in 20% aqueous of sodium hydroxide (120 mL), the mixture was stirred for 20 minutes and extracted with ethyl acetate (100 mL×2), the combined organic phase was washed with sat. brine (150 mL), dried over sodium sulfate, filtered and concentrated. The residue was purified by silica gel column chromatography (Petroleum ether/Ethyl acetate=30/1-1/1). The eluting solution was concentrated and treated with a mixture of ethyl acetate and petroleum ether (50 mL, V/V=1/10), the suspension was filtered and washed with petroleum ether (50 mL), the filter cake was dried in vacuum. Compound 2,4-dibromonaphthalen-1-amine (10.20 g, 33.89 mmol, 49% yield) was obtained as a gray solid. $^1$H-NMR (400 MHz, CDCl$_3$) δ 8.18 (d, J=8.4 Hz, 1H), 7.81-7.90 (m, 2H), 7.62-7.53 (m, 2H), 4.63 (brs, 2H).

Step 2: Preparation of 4-bromo-2-hydroxynaphthalene-1-diazonium

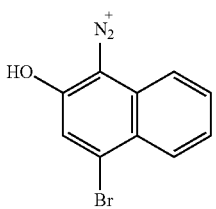

To a solution of 2,4-dibromonaphthalen-1-amine (10.20 g, 33.89 mmol, 1.00 eq) in a mixture of acetic acid (100 mL) and propionic acid (17 mL) was added sodium nitrite (2.69 g, 38.97 mmol, 1.15 eq) at 5-8° C. in portions over a period of 15 minutes. The reaction mixture was stirred at 5-8° C. for 45 minutes. The mixture was poured into ice-water (660 mL) under stirring, the slurry was filtered and washed with water (100 mL), the filtered cake was air dried. Compound 4-bromo-2-hydroxynaphthalene-1-diazonium (8.20 g, 32.79 mmol, 97% yield) was obtained as a pale yellow solid.

Step 3: Preparation of 4-bromonaphthalen-2-ol

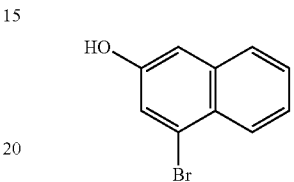

To a solution of 4-bromo-2-hydroxy-naphthalene-1-diazonium (8.20 g, 32.79 mmol, 1.00 eq) in ethanol (170 mL) was added sodium tetrahydroborate (2.84 g, 75.07 mmol, 2.29 eq) in portions over a period of 10 minutes at 10° C. The mixture was stirred at 20° C. for 80 minutes. The solution was adjusted to pH-6 with hydrochloride solution (1.0M, 80 mL), the organic phase was removed under reduced pressure and diluted with water (150 mL), the mixture was extracted with ethyl acetate (150 mL×2), the combined organic phase was dried with sodium sulfate, filtered and concentrated. The residue was purified by silica gel column chromatography (Petroleum ether/Ethyl acetate=50/1 to 5/1). Compound 4-bromonaphthalen-2-ol (2.70 g, 12.10 mmol, 37% yield) was obtained as a purple solid. $^1$H-NMR (400 MHz, CDCl$_3$) δ 8.15 (d, J=8.0 Hz, 1H), 7.66 (d, J=7.6 Hz, 1H), 7.49-7.41 (m, 3H), 7.15 (d, J=2.0 Hz, 1H), 5.42 (s, 1H).

Step 4: Preparation of 1-bromo-3-(methoxymethoxy)naphthalene

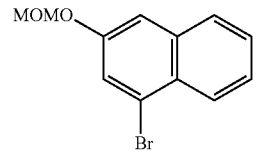

To a solution of 4-bromonaphthalen-2-ol (2.70 g, 12.10 mmol, 1.00 eq) and potassium carbonate (5.02 g, 36.31 mmol, 3.00 eq) in N,N-dimethylformamide (20.0 mL) was added dropwise chloro(methoxy)methane (1.49 g, 18.51 mmol, 1.4 mL, 1.53 eq) at 0° C. The mixture was stirred at 20° C. for 12 hours. The mixture was diluted with water (100 mL) and extracted with ethyl acetate (50 mL×2), the combined organic phase was washed with saturated brine (40 mL×2), dried over sodium sulfate, filtered and concentrated. The crude product was purified by Semi-preparative reverse phase HPLC, the eluting solution was removed under reduced pressure and dried in vacuum. Compound 1-bromo-3-(methoxymethoxy) naphthalene (1.40 g, 5.24 mmol, 43% yield) was obtained as a pale red oil. $^1$H-NMR (400 MHz, CDCl₃) δ 8.18-8.15 (m, 1H), 7.78-7.13 (m, 1H), 7.59 (d, J=2.4 Hz, 1H), 7.53-7.45 (m, 2H), 7.41 (d, J=2.0 Hz, 1H), 5.30 (s, 2H), 3.54 (s, 3H).

Step 5: Preparation of 7-benzyl-5,6,7,8-tetrahydro-pyrido[3,4-d]pyrimidine-2,4-diol

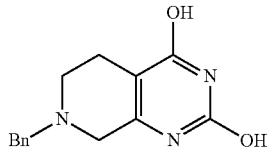

Sodium (11.64 g, 506.31 mmol, 4.43 eq) was added into ethanol (500 mL) in portions over a period of 30 minutes at 0° C. and stirred at 20° C. for another 30 minutes. And then ethyl 1-benzyl-3-oxopiperidine-4-carboxylate (34.00 g, 114.18 mmol, 1.00 eq, hydrochloride salt) and urea (20.57 g, 342.54 mmol, 3.00 eq) were added the upper solution, the reaction mixture was stirred at 90° C. for 12 hours. The mixture was adjusted to pH-7 with hydrochloride solution (1.0 M) and most of organic phase was removed under reduced pressure. The suspension was filtered and washed with water (40 mL), the filter cake was dried in vacuum. Compound 7-benzyl-5,6,7,8-tetrahydropyrido[3,4-d]pyrimidine-2,4-diol (18.10 g, 70.35 mmol, 62% yield) was obtained as a white solid. LC/MS (ESI) m/z: 258.1 [M+1]⁺; ¹H-NMR (400 MHz, DMSO-d₆) δ 10.93 (s, 1H), 10.61 (s, 1H), 7.37-7.27 (m, 5H), 3.62 (s, 2H), 3.13 (s, 2H), 2.61 (t, J=5.6 Hz, 2H), 2.23 (t, J=5.2 Hz, 2H).

Step 6: Preparation of 7-benzyl-2,4-dichloro-5,6,7,8-tetrahydropyrido[3,4-d]pyrimidine

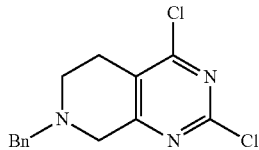 [SMILES: Clc1nc(Cl)c2c(n1)CN(Cc1ccccc1)CC2]

To a solution of 7-benzyl-6,8-dihydro-5H-pyrido[3,4-d]pyrimidine-2,4-diol (18.10 g, 70.35 mmol, 1.00 eq) in phosphoryl trichloride (165.00 g, 1.08 mol, 100 mL, 15.30 eq) was slowly added diisopropylethylamine (27.28 g, 211.05 mmol, 36.8 mL, 3.00 eq). The mixture was stirred at 110° C. for 12 hours. The solvent was evaporated under reduced pressure and diluted with dichloromethane (150 mL), the suspension was slowly poured into ice-bath and adjusted to pH~7 with saturated sodium hydrogen carbonate solution (100 mL), the organic phase was separated and the aqueous was extracted with dichloromethane (150 mL×3), the combined organic phase was dried over sodium sulfate, filtered and concentrated. (phosphoryl trichloride was slowly poured into water under stirring and adjusted to pH~7 with saturated sodium hydrogen carbonate solution). The residue was purified by silica gel column chromatography (Petroleum ether/Ethyl acetate=10/1 to 5/1). Compound 7-benzyl-2,4-dichloro-5,6,7,8-tetrahydropyrido[3,4-d]pyrimidine (6.70 g, 22.78 mmol, 32% yield) was obtained as a pale red solid. pyrimidine-2,4-diol (18.10 g, 70.35 mmol, 62% yield) was obtained as a white solid. LC/MS (ESI) m/z: 294.0 [M+1]⁺; ¹H-NMR (400 MHz, CDCl₃) δ 7.36-7.28 (m, 5H), 3.74 (s, 2H), 3.67 (s, 2H), 2.85 (s, 4H).

Step 7: Preparation of tert-butyl 4-(7-benzyl-2-chloro-5,6,7,8-tetrahydropyrido[3,4-d]pyrimidin-4-yl)piperazine-1-carboxylate

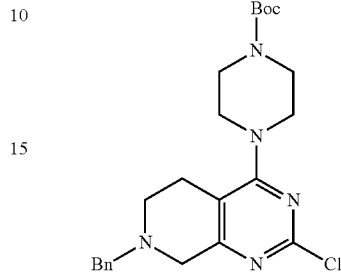

To a solution of 7-benzyl-2,4-dichloro-5,6,7,8-tetrahydropyrido[3,4-d]pyrimidine (28.50 g, 96.88 mmol, 1.00 eq) and tert-butyl piperazine-1-carboxylate (18.95 g, 101.72 mmol, 1.05 eq) in (methylsulfinyl)methane (200 mL) was added diisopropylethylamine (25.04 g, 193.76 mmol, 33.8 mL, 2.00 eq). The mixture was stirred at 55° C. for 3 hours. The mixture was diluted with water (500 mL) and ethyl acetate (60 mL), the suspension was stirred for 10 minutes and the aqueous phase was separated, the organic layer was filtered, the filter cake was washed with ethyl acetate (40 mL), petroleum ether (60 mL) and dried in vacuum, about 38 g of the product as a white solid was obtained, the aqueous was extracted with ethyl acetate (150 mL×2). The combined organic phase and the upper filtrate were washed with water (300 mL), sat. brine (300 mL×2), dried over sodium sulfate, filtered and concentrated. The crude product was purified by silica gel column chromatography (Petroleum ether/Ethyl acetate=10/1 to 3/1) to give about 3.2 g of the product as a white solid. Compound tert-butyl 4-(7-benzyl-2-chloro-6,8-dihydro-5H-pyrido[3,4-d]pyrimidin-4-yl)piperazine-1-carboxylate (41.20 g, 92.80 mmol, 96% yield) was obtained as a white solid. LC/MS (ESI) m/z: 444.1 [M+1]⁺; ¹H-NMR (400 MHz, CDCl₃) δ 7.36-7.29 (m, 5H), 3.70 (s, 2H), 3.62 (s, 2H), 3.54-3.49 (m, 8H), 2.68 (s, 4H), 1.50 (s, 9H).

Step 8: Preparation of tert-butyl (R)-4-(7-benzyl-2-((1,1-dimethoxypropan-2-yl)oxy)-5,6,7,8-tetrahydropyrido[3,4-d]pyrimidin-4-yl)piperazine-1-carboxylate

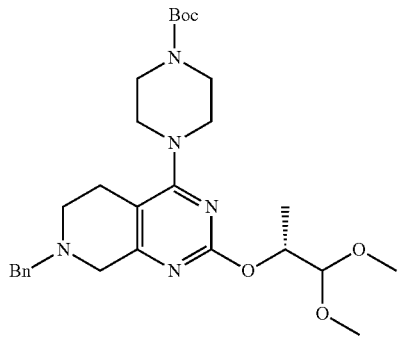 [SMILES: COC(OC)[C@@H](C)Oc1nc2c(c(N3CCN(C(=O)OC(C)(C)C)CC3)n1)CCN(Cc1ccccc1)C2]

811

To a solution of tert-butyl 4-(7-benzyl-2-chloro-6,8-dihydro-5H-pyrido[3,4-d]pyrimidin-4-yl)piperazine-1-carboxylate (10.00 g, 22.52 mmol, 1.00 eq) and (R)-1,1-dimethoxypropan-2-ol (4.06 g, 33.79 mmol, 1.50 eq) in toluene (120 mL) were added tris(dibenzylideneacetone) dipalladium(0) (1.24 g, 1.35 mmol, 0.06 eq), (R)-(+)-2,2'-bis(diphenylphosphino)-1,1'-binaphthalene (1.40 g, 2.25 mmol, 0.10 eq) and sodium 2-methylpropan-2-olate (5.41 g, 56.31 mmol, 2.50 eq). The reaction mixture was degassed with nitrogen gas and stirred at 100° C. for 4 hours. The solvent was removed under reduced pressure. The residue was purified by silica gel column chromatography (17-50% ethyl acetate in petroleum ether). Compound tert-butyl 4-[7-benzyl-2-[(1R)-2,2-dimethoxy-1-methyl-ethoxy]-6,8-dihydro-5H-pyrido[3,4-d]pyrimidin-4-yl]piperazine-1-carboxylate (4.90 g, 9.29 mmol, 41% yield) was obtained as a green solid. LC/MS (ESI) m/z: 528.4 [M+1]+.

Step 9: Preparation of tert-butyl (R)-4-(2-((1,1-dimethoxypropan-2-yl)oxy)-5,6,7,8-tetrahydropyrido[3,4-d]pyrimidin-4-yl)piperazine-1-carboxylate

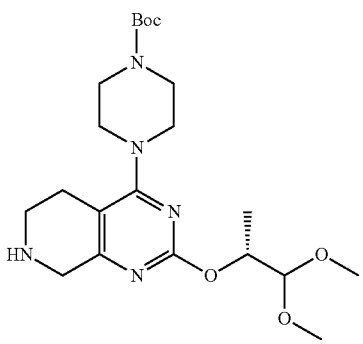 [SMILES: COC(OC)[C@@H](C)Oc1nc2c(c(N3CCN(C(=O)OC(C)(C)C)CC3)n1)CCNC2]

To a solution of tert-butyl 4-[7-benzyl-2-[(1R)-2,2-dimethoxy-1-methyl-ethoxy]-6,8-dihydro-5H-pyrido[3,4-d]pyrimidin-4-yl]piperazine-1-carboxylate (4.90 g, 9.29 mmol, 1.00 eq) in a mixture of methanol (90 mL) and tetrahydrofuran (15 mL) were added ammonia hydroxide (9.04 mmol, 92.86 mmol, 9.9 mL, 36% purity, 10.00 eq) and palladium on activated carbon (10%, 1.00 g) under nitrogen gas. The suspension was degassed under vacuum and purged with hydrogen gas several times. The mixture was stirred under hydrogen gas (50 psi) at 50° C. for 64 hours. The suspension was filtered through a celite pad and washed with methanol (30 mL), the filtrate was concentrated and dried in vacuum. Compound tert-butyl 4-[2-[(1R)-2,2-dimethoxy-1-methyl-ethoxy]-5,6,7,8-tetrahydropyrido[3,4-d]pyrimidin-4-yl]piperazine-1-carboxylate (3.54 g, 8.09 mmol, 87% yield) was obtained as a yellow gum. LC/MS (ESI) m/z: 438.2 [M+1]+.

Step 10: Preparation of tert-butyl (R)-4-(2-((1,1-dimethoxypropan-2-yl)oxy)-7-(3-(methoxymethoxy)naphthalen-1-yl)-5,6,7,8-tetrahydropyrido[3,4-d]pyrimidin-4-yl)piperazine-1-carboxylate

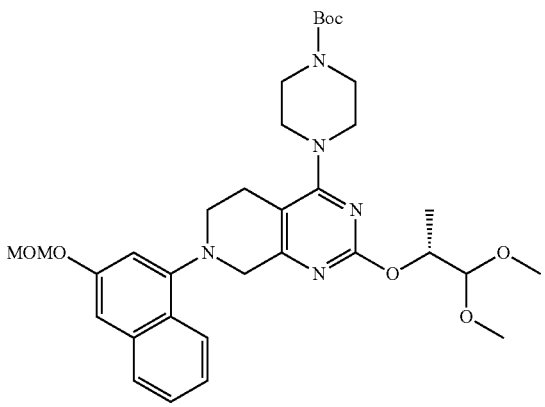

To a mixture of tert-butyl 4-[2-[(1R)-2,2-dimethoxy-1-methyl-ethoxy]-5,6,7,8-tetrahydropyrido[3,4-d]pyrimidin-4-yl]piperazine-1-carboxylate (3.54 g, 8.09 mmol, 1.00 eq) and 1-bromo-3-(methoxymethoxy)naphthalene (2.27 g, 8.50 mmol, 1.05 eq) in dioxane (45 mL) were added RuPhos-Pd-G3 (338 mg, 0.40 mmol, 0.05 eq), dicyclohexyl-(2',6'-diisopropoxy-[1,1'-biphenyl]-2-yl)phosphine (388 mg, 0.81 mmol, 0.10 eq) and cesium carbonate (6.59 g, 20.23 mmol, 2.50 eq). The reaction mixture was degassed with nitrogen gas and stirred at 100° C. for 5 hours. The solvent was removed under reduced pressure. The residue was purified by silica gel column chromatography (Petroleum ether/Ethyl acetate=5/1-3/1). Compound tert-butyl 4-[2-[(1R)-2,2-dimethoxy-1-methyl-ethoxy]-7-[3-(methoxymethoxy)-1-naphthyl]-6,8-dihydro-5H-pyrido[3,4-d]pyrimidin-4-yl]piperazine-1-carboxylate (3.90 g, 6.25 mmol, 77% yield) was obtained as a pale red solid. LC/MS (ESI) m/z: 624.4 [M+1]+; 1H-NMR (400 MHz, CDCl3) δ 8.11 (d, J=8.4 Hz, 1H), 7.76 (d, J=8.0 Hz, 1H), 7.46 (t, J=7.2 Hz, 1H), 7.38 (t, J=8.4 Hz, 1H), 7.17 (d, J=1.6 Hz, 1H), 6.89 (d, J=2.0 Hz, 1H), 5.31 (s, 2H), 5.28-5.21 (m, 1H), 4.48 (d, J=6.0 Hz, 1H), 4.25 (s, 2H), 3.59-3.43 (m, 17H), 3.37 (s, 2H), 2.88 (s, 2H), 1.51 (s, 9H), 1.37 (d, J=6.4 Hz, 3H).

Step 11: Preparation of (R)-2-((7-(3-hydroxynaphthalen-1-yl)-4-(piperazin-1-yl)-5,6,7,8-tetrahydropyrido[3,4-d]pyrimidin-2-yl)oxy)propanal

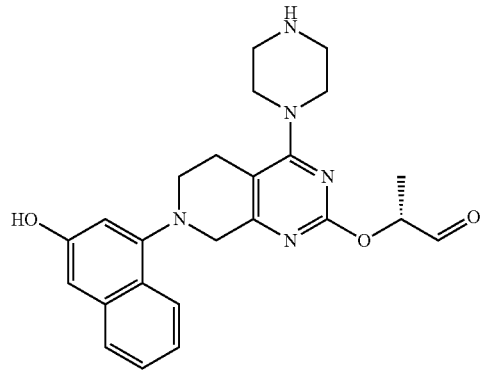 [SMILES: C[C@H](C=O)Oc1nc2c(c(N3CCNCC3)n1)CCN(c1cc(O)cc3ccccc13)C2]

To a solution of tert-butyl 4-[2-[(1R)-2,2-dimethoxy-1-methyl-ethoxy]-7-[3-(methoxymethoxy)-1-naphthyl]-6,8-dihydro-5H-pyrido[3,4-d]pyrimidin-4-yl]piperazine-1-carboxylate (1.90 g, 3.05 mmol, 1.00 eq) in dichloromethane (10 mL) was added hydrochloride/Dioxane (4.0 M, 20 mL, 26.26 eq). The reaction mixture was stirred at 20° C. for 4.0 hours. The suspension was filtered and washed with ethyl acetate (15 mL) and petroleum ether (15 mL), the filter cake was dried in vacuum. Compound (2R)-2-[[7-(3-hydroxy-1-naphthyl)-4-piperazin-1-yl-6,8-dihydro-5H-pyrido[3,4-d]pyrimidin-2-yl]oxy]propanal (800 mg, 1.70 mmol, 56% yield, hydrochloride salt) were obtained as a pale yellow solid. LC/MS (ESI) m/z: 434.1 [M+1]$^+$.

Step 12: Preparation of (R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propanal

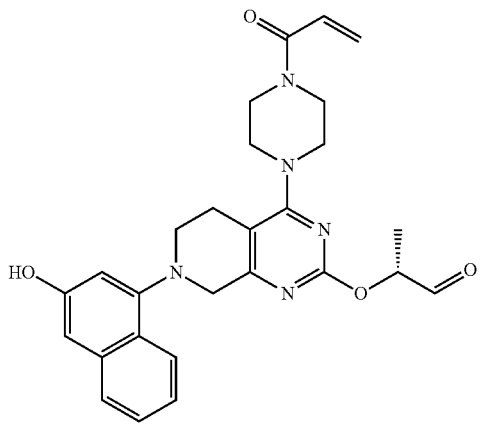 [SMILES: C=CC(=O)N1CCN(c2nc(O[C@H](C)C=O)nc3c2CCN(c2cc(O)cc4ccccc24)C3)CC1]

To a solution of (2R)-2-[[7-(3-hydroxy-1-naphthyl)-4-piperazin-1-yl-6,8-dihydro-5H-pyrido[3,4-d]pyrimidin-2-yl]oxy]propanal (400 mg, 0.85 mmol, 1.00 eq, hydrochloride salt) in a mixture of dichloromethane (155 mL) and N,N-dimethylformamide (4 mL) was added a solution of prop-2-enoyl chloride (85 mg, 0.94 mmol, 1.10 eq) in dichloromethane (5 mL). And then 2,6-lutidine (2.74 g, 25.53 mmol, 30.00 eq) was added dropwise at −78° C. for 30 minutes. The reaction mixture was stirred at −78° C. for 1.0 hour. The solvent was removed under reduced pressure and then evaporated the high boiling point solvent in vacuum. The residue was purified by silica gel column chromatography (Petroleum ether/Ethyl acetate=3/1 to 1/1, ethyl acetate/methanol=20/1-10/1). The product (2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propanal (700 mg) was obtained as a pale red solid. LC/MS (ESI) m/z: 488.1 [M+1]$^+$; $^1$H-NMR (400 MHz, CDCl$_3$) δ 9.94 (s, 1H), 8.01 (d, J=8.8 Hz, 2H), 7.49-7.24 (m, 3H), 6.87-6.77 (m, 1H), 6.18 (d, J=16.8 Hz, 2H), 5.76 (d, J=6.4 Hz, 1H), 5.21-5.05 (m, 1H), 4.60-4.46 (m, 2H), 4.05-3.95 (m, 4H), 3.83-3.74 (m, 8H), 1.50 (t, J=6.4 Hz, 3H).

Step 13: Preparation of 14-hydroxy-3,6,9,12-tetraoxatetradecyl 4-methylbenzenesulfonate

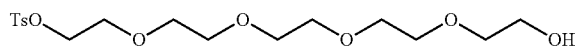 [SMILES: Cc1ccc(S(=O)(=O)OCCOCCOCCOCCOCCO)cc1]

To a solution of 2-[2-[2-[2-(2-hydroxyethoxy)ethoxy]ethoxy]ethoxy]ethanol (15 g, 62.95 mmol, 13.27 mL, 2 eq) in tetrahydrofuran (150 mL) was added sodium hydride (1.26 g, 31.48 mmol, 60% purity, 1 eq) at 0° C. The mixture was stirred at 0° C. for 0.5 hour. Then p-toluenesulfonyl chloride (6.00 g, 31.48 mmol, 1 eq) was added, the mixture was stirred at 25° C. for 2 hours. The mixture was poured into saturated ammonium chloride aqueous solution (100 mL), the water layer was extracted with ethyl acetate (80 mL×2). Then the organic phase was dried over anhydrous sodium sulfate, filtered and the filtrate was condensed to get the residue. The residue was purified by silica gel column chromatography (petroleum ether/ethyl acetate=3/1 to dichloromathane/methanol=10/1) to get 2-[2-[2-[2-(2-hydroxyethoxy)ethoxy]ethoxy]ethoxy]ethyl 4-methylbenzenesulfonate (8.62 g, 21.96 mmol, 69% yield) as a light yellow oil.

Step 14: Preparation of 14-((tetrahydro-2H-pyran-2-yl)oxy)-3,6,9,12-tetraoxatetradecyl 4-methylbenzenesulfonate

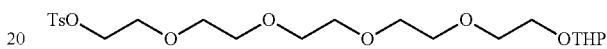

To a solution of 2-[2-[2-[2-(2-hydroxyethoxy)ethoxy]ethoxy]ethoxy]ethyl 4-methylbenzenesulfonate (13 g, 33.12 mmol, 1 eq) in dichloromethane (100 mL) was added pyridine 4-methylbenzenesulfonate (416 mg, 1.66 mmol, 0.05 eq) and 3,4-dihydro-2H-pyran (3.34 g, 39.75 mmol, 3.63 mL, 1.2 eq) at 0° C. Then the mixture was stirred at 25° C. for 16 hours. The mixture was filtrated to get the filtrate. The filtrate was quenched by water (300 mL) and then diluted with dichloromethane (500 mL) and extracted with dichloromethane (500 mL×2). The combined organic layers were washed with brine (300 mL), dried over, filtered and concentrated under reduced pressure to give a residue. The residue was purified by chromatography on silica gel (petroleum ether/ethyl acetate=3:1) to afford 2-[2-[2-[2-(2-tetrahydropyran-2-yloxyethoxy)ethoxy]ethoxy]ethoxy]ethyl 4-methylbenzenesulfonate (12.5 g, 26.23 mmol) as yellow oil.

Step 15: Preparation of tert-butyl 4-((14-((tetrahydro-2H-pyran-2-yl)oxy)-3,6,9,12-tetraoxatetradecyl)oxy)piperidine-1-carboxylate

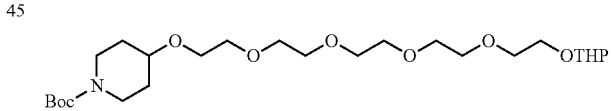

To a mixture of tert-butyl 4-hydroxypiperidine-1-carboxylate (6.33 g, 31.47 mmol, 1.2 eq) in tetrahydrofuran (500 mL) was added sodium hydrogen (1.26 g, 31.47 mmol, 60% purity, 1.2 eq) at 0° C. in portions. The mixture was stirred at 0° C. for 1 hour. Then to the mixture was added a solution of 2-[2-[2-[2-(2-tetrahydropyran-2-yloxyethoxy)ethoxy]ethoxy]ethoxy]ethyl 4-methylbenzenesulfonate (12.5 g, 26.23 mmol, 1 eq) in tetrahydrofuran (50 mL) dropwise. The mixture was stirred at 25° C. for 12 hours. The residue was poured into saturated sodium bicarbonate (300 mL). The mixture was extracted with ethyl acetate (100 mL×3). The organic layer was combined, dried over anhydrous sodium sulfate and filtered. The filtrate was concentrated. The residue was purified by chromatography on silica gel (petroleum ether/ethyl acetat=3:1). Tert-butyl 4-[2-[2-[2-[2-(2-tetrahydropyran-2-yloxyethoxy)ethoxy]ethoxy]ethoxy]ethoxy]piperidine-1-carboxylate was obtained (13.3 g) as yellow oil.

Step 16: Preparation of tert-butyl 4-((14-hydroxy-3,6,9,12-tetraoxatetradecyl)oxy)piperidine-1-carboxylate

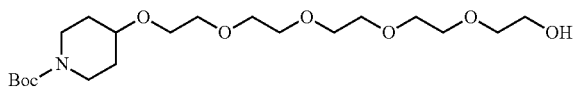 [SMILES: CC(C)(C)OC(=O)N1CCC(OCCOCCOCCOCCOCCO)CC1]

To a solution of tert-butyl 4-[2-[2-[2-[2-(2-tetrahydropyran-2-yloxyethoxy)ethoxy]ethoxy]ethoxy]piperidine-1-carboxylate (13.3 g, 26.30 mmol, 1 eq) in ethyl alcohol (50 mL) was added pyridine 4-methylbenzenesulfonate (661 mg, 2.63 mmol, 0.1 eq). The mixture was stirred at 60° C. for 12 hours. The reaction mixture was filtered and concentrated under reduced pressure to give a residue. The residue was purified by column chromatography (Petroleum ether:Ethyl acetate=5:1 to 0:1). Tert-butyl 4-[2-[2-[2-[2-(2-hydroxyethoxy)ethoxy]ethoxy]ethoxy]ethoxy]piperidine-1-carboxylate (7.2 g, 17.08 mmol, 65% yield) was obtained as a colorless oil.

Step 17: Preparation of tert-butyl 4-((17-oxo-3,6,9,12,15,18-hexaoxaicosyl)oxy)piperidine-1-carboxylate

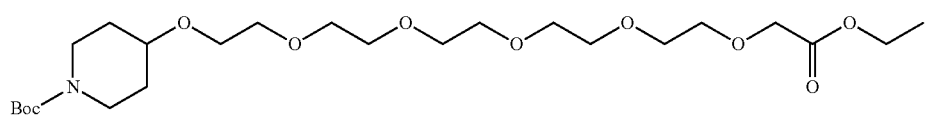 [SMILES: CCOC(=O)COCCOCCOCCOCCOCCOC1CCN(C(=O)OC(C)(C)C)CC1]

To a solution of tert-butyl 4-[2-[2-[2-[2-(2-hydroxyethoxy)ethoxy]ethoxy]ethoxy]ethoxy]piperidine-1-carboxylate (400 mg, 0.95 mmol, 1 eq) in tetrahydrofuran (20 mL) was added sodium hydride (46 mg, 1.14 mmol, 60% purity, 1.2 eq) in one portion at 0° C. under nitrogen. The mixture was stirred at 0° C. for 0.5 hour. Then was added and ethyl 2-bromoacetate (190 mg, 1.14 mmol, 1.2 eq) at 0° C. The mixture was stirred at 25° C. for 11.5 hours. To the reaction mixture was added water (30 mL) and the mixture was extracted with ethyl acetate (30 mL×3). The combined organic phase was washed with brine (20 mL), dried over anhydrous sodium sulfate, filtered and concentrated in vacuum. The residue was purified by column chromatography (SiO$_2$, petroleum ether/ethyl acetate=5/1 to 1/1). Compound tert-butyl 4-[2-[2-[2-[2-[2-(2-ethoxy-2-oxo-ethoxy)ethoxy]ethoxy]ethoxy]ethoxy]piperidine-1-carboxylate (250 mg, 0.49 mmol, 51% yield) was obtained as a white oil.

Step 18: Preparation of 17-((1-(tert-butoxycarbonyl)piperidin-4-yl)oxy)-3,6,9,12,15-pentaoxaheptadecanoic acid

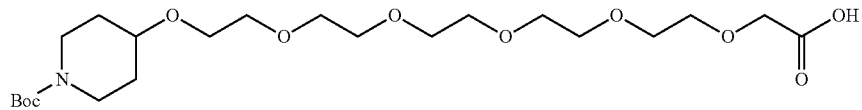 [SMILES: CC(C)(C)OC(=O)N1CCC(OCCOCCOCCOCCOCCOCC(=O)O)CC1]

To a solution of tert-butyl-4-[2-[2-[2-[2-[2-(2-ethoxy-2-oxo-ethoxy)ethoxy]ethoxy]ethoxy]ethoxy]ethoxy]piperidine-1-carboxylate (250 mg, 492.50 umol, 1 eq) in tetrahydrofuran (5 mL) and water (5 mL) was added lithium hydrate (59 mg, 2.46 mmol, 5 eq). The mixture was stirred at 25° C. for 12 hours. The reaction mixture was charged with 1 M hydrochloric acid to adjust pH=5, and extracted with ethyl acetate 20 mL (20 mL*3). The combined organic layers were dried over sodium sulfate, filtered and concentrated under reduced pressure to give compound 2-[2-[2-[2-[2-[2-[(1-tert-butoxycarbonyl-4-piperidyl)oxy]ethoxy]ethoxy]ethoxy]ethoxy]ethoxy]acetic acid (200 mg) as a yellow oil.

Step 19: Preparation of tert-butyl 4-(((S)-19-((2S,4R)-4-hydroxy-2-(((S)-1-(4-(4-methylthiazol-5-yl)phenyl)ethyl)carbamoyl)pyrrolidine-1-carbonyl)-20,20-dimethyl-17-oxo-3,6,9,12,15-pentaoxa-18-azahenicosyl)oxy)piperidine-1-carboxylate

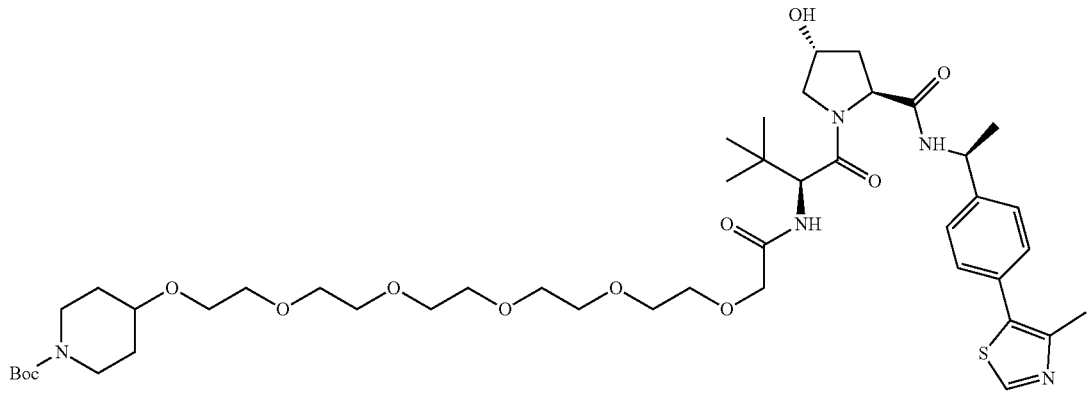 [SMILES: Cc1ncsc1-c1ccc([C@H](C)NC(=O)[C@@H]2C[C@@H](O)CN2C(=O)[C@@H](NC(=O)COCCOCCOCCOCCOCCOC2CCN(C(=O)OC(C)(C)C)CC2)C(C)(C)C)cc1]

A mixture of 2-[2-[2-[2-[2-[2-[(1-tert-butoxycarbonyl-4-piperidyl)oxy]ethoxy]ethoxy]ethoxy]ethoxy]ethoxy]acetic acid (500 mg, 1.04 mmol, 1 eq), (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (464 mg, 1.04 mmol, 1 eq), 1-hydroxybenzotriazol (211 mg, 1.56 mmol, 1.5 eq), 1-(3-dimethylaminopropyl)-3-ethylcarbodiimide hydrochloride (300 mg, 1.56 mmol, 1.5 eq) and N,N-diisopropylethylamine (539 mg, 4.17 mmol, 4 eq) in N,N-dimethylformamide (10 mL) was degassed and purged with nitrogen for 3 times, and then the mixture was stirred at 25° C. for 12 hours under $N_2$ atmosphere. To the reaction mixture was added water (50 mL) and the mixture was extracted with ethyl acetate (30 mL×3). The combined organic phase was washed with brine (20 mL), dried over anhydrous sodium sulfate, filtered and concentrated in vacuum. The crude product was purified by semi-preparative reverse phase HPLC to yield compound tert-butyl 4-[2-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxoethoxy]ethoxy]ethoxy]ethoxy]ethoxy]piperidine-1-carboxylate (700 mg, 0.77 mmol, 74% yield) as a colorless oil.

Step 20: Preparation of (2S,4R)-1-((S)-2-(tert-butyl)-4-oxo-20-(piperidin-4-yloxy)-6,9,12,15,18-pentaoxa-3-azaicosanoyl)-4-hydroxy-N—((S)-1-(4-(4-methylthiazol-5-yl)phenyl)ethyl)pyrrolidine-2-carboxamide

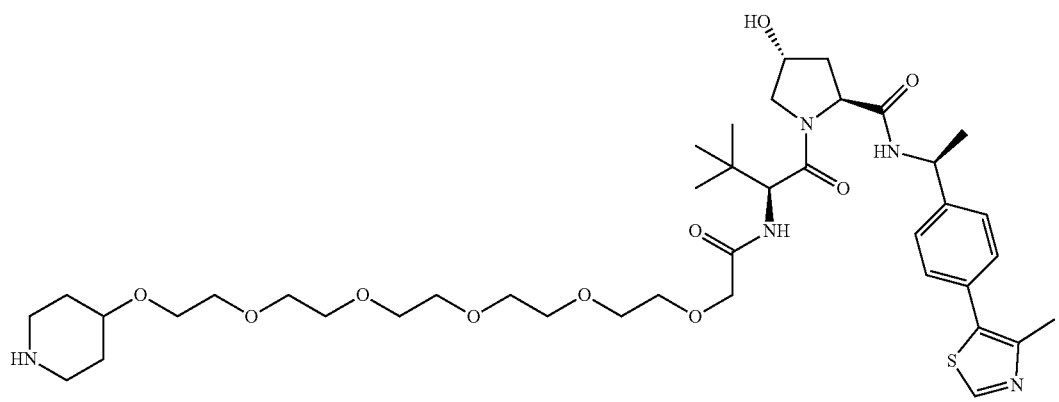 [SMILES: Cc1ncsc1-c1ccc([C@H](C)NC(=O)[C@@H]2C[C@@H](O)CN2C(=O)[C@@H](NC(=O)COCCOCCOCCOCCOCCOC2CCNCC2)C(C)(C)C)cc1]

To a solution tert-butyl 4-[2-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethoxy]piperidine-1-carboxylate (100 mg, 0.11 mmol, 1 eq) in dichloromethane (2 mL) was added hydrochloric acid/dioxane (4 M, 1 mL, 36.25 eq). The reaction mixture stirred at 25° C. for 1 hours. The mixture was concentrated under vacuum to get (2S,4R)-1-[(2S)-3,3-dimethyl-2-[[2-[2-[2-[2-[2-[2-(4-piperidyloxy)ethoxy]ethoxy]ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (93 mg, hydrochloride) as a colorless gum.

Step 21: Preparation of (2S,4R)-1-((S)-20-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-2-(tert-butyl)-4-oxo-6,9,12,15,18-pentaoxa-3-azaicosanoyl)-4-hydroxy-N—((S)-1-(4-(4-methylthiazol-5-yl)phenyl)ethyl)pyrrolidine-2-carboxamide

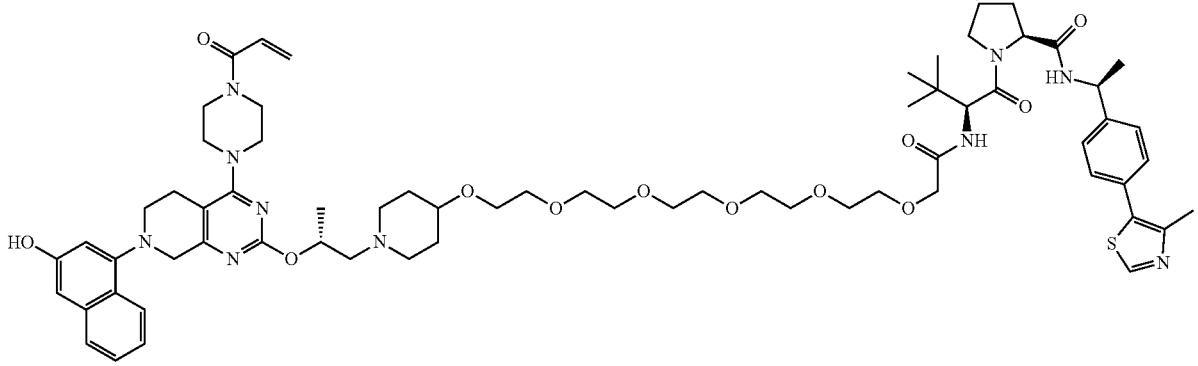

To a mixture of (R)-2-((4-(4-acryloylpiperazin-1-yl)-7-(3-hydroxy naphthalen-1-yl)-5,6,7,8-tetrahydropyrido[3,4-d]pyrimidin-2-yl)oxy)propanal (40 mg, 0.08 mmol, 1.00 eq) and (2S,4R)-1-((S)-2-(tert-butyl)-4-oxo-20-(piperidin-4-yloxy)-6,9,12,15,18-pentaoxa-3-azaicosan-1-oyl)-4-hydroxy-N—((S)-1-(4-(4-methylthiazol-5-yl)phenyl)ethyl)pyrrolidine-2-carboxamide (71 mg, 0.08 mmol, 1.00 eq, hydrochloride salt) in a mixture of 1,2-dichloroethane (1.0 mL) and methanol (1.0 mL) was added sodium acetate (135 mg, 1.64 mmol, 20.00 eq) for about 30 mins. And then sodium cyanoborohydride (16 mg, 0.25 mmol, 3.00 eq) was added at 0° C. The mixture was allowed to warm to 20° C. for 1.5 hours. The suspension was filtered and washed with dichloromethane (7 mL), the filtrate was concentrated and dried in vacuum. The residue was purified by prep-TLC (dichloromethane:methanol=15:1). The product was further purified by Semi-preparative reserve phase HPLC. The eluting solution was lyophilized in vacuum. The product was further purified by Semi-preparative reserve phase HPLC. The eluting solution was lyophilized in vacuum. Compound (2S,4R)-1-((S)-20-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-2-(tert-butyl)-4-oxo-6,9,12,15,18-pentaoxa-3-azaicosan-1-oyl)-4-hydroxy-N—((S)-1-(4-(4-methylthiazol-5-yl)

phenyl)ethyl)pyrrolidine-2-carboxamide (7.1 mg, 0.005 mmol, 7% yield, 97% purity) was obtained as a pink solid. LC/MS (ESI) m/z: 1299.7 [M+23]$^+$; $^1$H-NMR (400 MHz, CDCl$_3$) δ 8.60 (s, 1H), 7.94 (d, J=8.4 Hz, 1H), 7.55 (d, J=7.6 Hz, 1H), 7.48 (d, J=8.0 Hz, 1H), 7.34-7.21 (m, 7H), 6.82 (s, 1H), 6.71 (s, 1H), 6.51 (dd, J=10.8, 16.8 Hz, 1H), 6.26 (d, J=16.8 Hz, 1H), 5.68 (d, J=10.8 Hz, 1H), 5.35-5.22 (m, 1H), 5.04-4.98 (m, 1H), 4.68 (t, J=8.0 Hz, 1H), 4.53 (d, J=8.8 Hz, 1H), 4.44 (s, 1H), 4.10 (s, 2H), 4.01-3.89 (m, 3H), 3.75-3.35 (m, 30H), 3.30-3.15 (m, 2H), 2.88-2.78 (m, 2H), 2.75-2.65 (m, 2H), 2.44 (s, 3H), 2.41-2.33 (m, 2H), 2.27-2.15 (m, 2H), 2.08-2.00 (m, 1H), 1.96-1.86 (m, 3H), 1.56-1.44 (m, 3H), 1.40 (d, J=6.8 Hz, 3H), 1.26 (d, J=6.0 Hz, 3H), 0.99 (s, 9H).

Exemplary Synthesis of 5-(2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)ethoxy)-2-(2,6-dioxopiperidin-3-yl)isoindoline-1,3-dione
(Exemplary compound 428)

Step 1: Preparation of tert-butyl 4-(2-(2-(2-((2-(2,6-dioxopiperidin-3-yl)-1,3-dioxoisoindolin-5-yl)oxy)ethoxy)ethoxy)ethoxy)piperidine-1-carboxylate

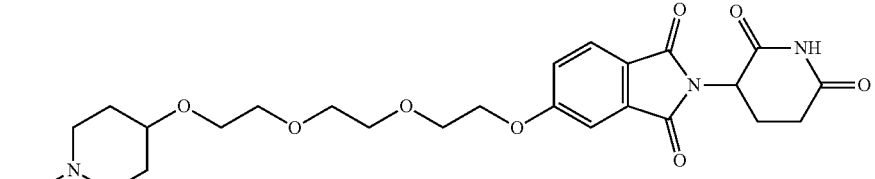

To the mixture of tert-butyl 4-[2-[2-[2-(p-tolylsulfonyloxy)ethoxy]ethoxy]ethoxy]piperidine-1-carboxylate (800 mg, 1.64 mmol, 1 eq) and 2-(2,6-dioxo-3-piperidyl)-5-hydroxy-isoindoline-1,3-dione (449 mg, 1.64 mmol, 1 eq) in N,N-dimethylformamide (10 mL) was added potassium carbonate (566 mg, 4.10 mmol, 2.5 eq) and potassium iodide (27 mg, 0.16 mmol, 0.1 eq). The mixture was stirred at 50° C. for 12 hours. The mixture was poured into hydrochloric acid solution (30 mL, 1 M). Then it was extracted with ethyl acetate (30 mL×3). The combined organic layer was washed with water (50 mL×2), and brine (50 mL×2), dried over anhydrous sodium sulfate, filtered and concentrated under reduced pressure to give a residue. The residue was purified by silica gel chromatography (petroleum ether:ethyl acetate=3:1 to 1:2) to give a product. The product was further purified by prep-HPLC. Compound tert-butyl 4-[2-[2-[2-[2-(2,6-dioxo-3-piperidyl)-1,3-dioxo-isoindolin-5-yl]oxyethoxy]ethoxy]ethoxy]piperidine-1-carboxylate (330 mg, 0.56 mmol, 34% yield) was obtained as a white solid. LC/MS (ESI) m/z: 490.1 [M−100]$^+$; $^1$H-NMR (400 MHz, CD$_3$OD) δ 7.81 (d, J=8.4 Hz, 1H), 7.44 (d, J=2.0 Hz, 1H), 7.36-7.33 (m, 1H), 5.13-5.11 (m, 1H), 4.58 (s, 1H), 4.32-4.30 (m, 1H), 3.72-3.70 (m, 3H), 3.68-3.65 (m, 2H), 3.62-3.58 (s, 4H), 3.56-3.52 (m, 3H), 3.14-3.02 (m, 2H), 2.78-2.77 (m, 1H), 2.74-2.73 (m, 2H), 2.06-2.12 (m, 1H), 1.84-1.80 (m, 2H), 1.47-1.46 (m, 2H), 1.44 (s, 9H).

Step 2: Preparation of 2-(2,6-dioxopiperidin-3-yl)-5-(2-(2-(2-(piperidin-4-yloxy)ethoxy)ethoxy)ethoxy)isoindoline-1,3-dione

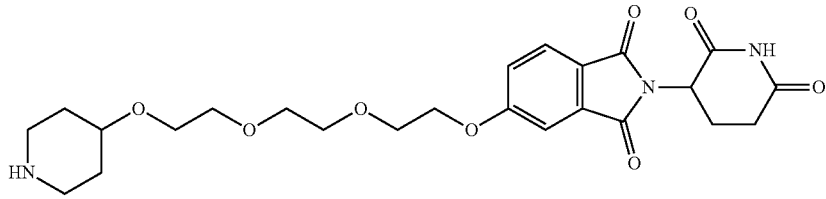 [SMILES: O=C1CCC(N2C(=O)c3ccc(OCCOCCOCCOC4CCNCC4)cc3C2=O)C(=O)N1]

To the mixture of tert-butyl 4-[2-[2-[2-[2-(2,6-dioxo-3-piperidyl)-1,3-dioxo-isoindolin-5-yl]oxyethoxy]ethoxy]ethoxy]piperidine-1-carboxylate (330 mg, 0.55 mmol, 1 eq) in dichloromethane (5 mL) was added hydrochloric acid/dioxane (4 M, 5 mL). The mixture was stirred at 25° C. for 1 hour. The mixture was concentrated under vacuum to give the product 2-(2,6-dioxo-3-piperidyl)-5-[2-[2-[2-(4-piperidyloxy)ethoxy]ethoxy]ethoxy]isoindoline-1,3-dione (290 mg, 0.55 mmol, 98% yield, hydrochloride) as a yellow oil. LC/MS (ESI) m/z: 490.3 [M+1]+.

Step 3: Preparation of tert-butyl 4-(6-chloro-2-(((2R)-1-(4-(2-(2-(2-((2-(2,6-dioxopiperidin-3-yl)-1,3-dioxoisoindolin-5-yl)oxy)ethoxy)ethoxy)ethoxy)piperidin-1-yl)propan-2-yl)oxy)-8-fluoro-7-(3-hydroxynaphthalen-1-yl)quinazolin-4-yl)piperazine-1-carboxylate

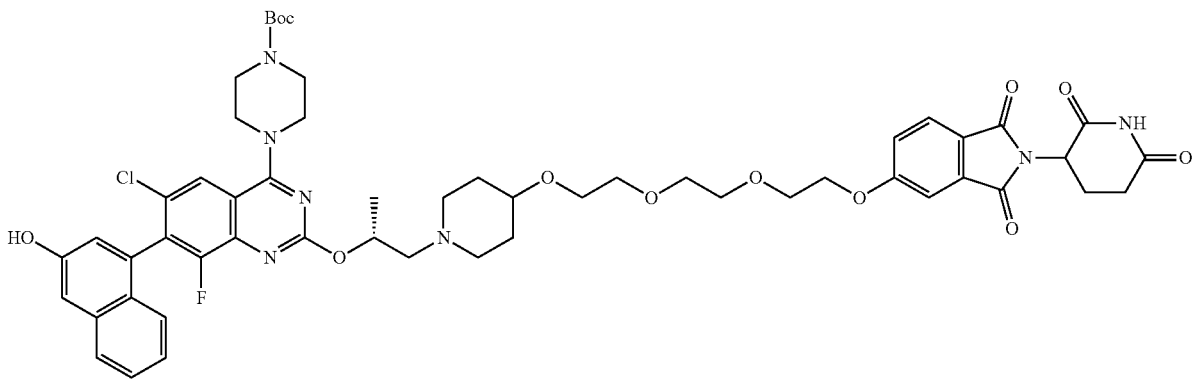 [SMILES: C[C@H](CN1CCC(OCCOCCOCCOc2ccc3c(c2)C(=O)N(C2CCC(=O)NC2=O)C3=O)CC1)Oc1nc(N2CCN(C(=O)OC(C)(C)C)CC2)c2cc(Cl)c(-c3cc(O)cc4ccccc34)c(F)c2n1]

To the mixture of 2-(2,6-dioxo-3-piperidyl)-5-[2-[2-[2-(4-piperidyloxy)ethoxy]ethoxy]ethoxy]isoindoline-1,3-dione (54 mg, 0.10 mmol, 1 eq, hydrochloride) in dichloromethane (3 mL) and methanol (3 mL) was added sodium acetate (25 mg, 0.30 mmol, 3 eq). The mixture was stirred at 25° C. for 10 minutes. Then tert-butyl 4-[6-chloro-8-fluoro-7-(3-hydroxy-1-naphthyl)-2-[(1R)-1-methyl-2-oxo-ethoxy]quinazolin-4-yl]piperazine-1-carboxylate (60 mg, 0.10 mmol, 1 eq) and acetic acid (12 mg, 0.20 mmol, 0.01 mL, 2 eq) was added under stirring at 25° C. for 10 minutes. Then sodium cyanoborohydride (19 mg, 0.30 mmol, 3 eq) was added at 0° C. Then the reaction mixture was stirred at 25° C. for 12 hours. The mixture was concentrated under vacuum to give a residue. The residue was purified by prep-TLC (dichloromethane:methanol=10:1). Compound tert-butyl4-[6-chloro-2-[(1R)-2-[4-[2-[2-[2-[2-(2,6-dioxo-3-piperidyl)-1,3-dioxo-isoindolin-5-yl]oxyethoxy]ethoxy]ethoxy]-1-piperidyl]-1-methyl-ethoxy]-8-fluoro-7-(3-hydroxy-1-naphthyl)quinazolin-4-yl]piperazine-1-carboxylate (60 mg, 0.056 mmol, 55.10% yield) was obtained as a colorless oil. LC/MS (ESI) m/z: 1054.6 [M+1]+.

Step 4: Preparation of 5-(2-(2-(2-((1-((2R)-2-((6-chloro-8-fluoro-7-(3-hydroxynaphthalen-1-yl)-4-(piperazin-1-yl)quinazolin-2-yl)oxy)propyl)piperidin-4-yl)oxy)ethoxy)ethoxy)ethoxy)-2-(2,6-dioxopiperidin-3-yl)isoindoline-1,3-dione

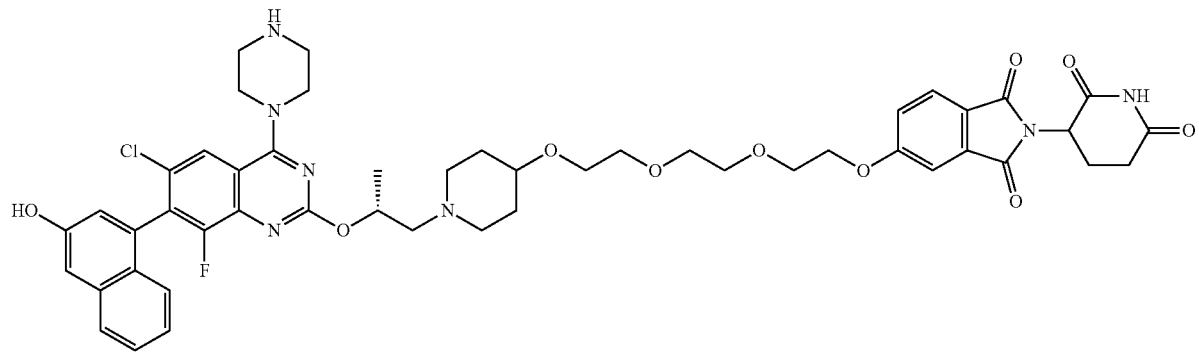 [SMILES: C[C@H](CN1CCC(OCCOCCOCCOc2ccc3c(c2)C(=O)N(C2CCC(=O)NC2=O)C3=O)CC1)Oc1nc(N2CCNCC2)c2cc(Cl)c(-c3cc(O)cc4ccccc34)c(F)c2n1]

To the mixture of tert-butyl 4-[6-chloro-2-[(1R)-2-[4-[2-[2-[2-[2-(2,6-dioxo-3-piperidyl)-1,3-dioxo-isoindolin-5-yl]oxyethoxy]ethoxy]ethoxy]-1-piperidyl]-1-methyl-ethoxy]-8-fluoro-7-(3-hydroxy-1-naphthyl)quinazolin-4-yl]piperazine-1-carboxylate (60 mg, 0.056 mmol, 1 eq) in dichloromethane (5 mL) was added trifluoroacetic acid (3.08 g, 27.01 mmol, 2 mL, 474 eq). The mixture was stirred at 25° C. for 30 minutes. Then the mixture was concentrated to give the product 5-[2-[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]ethoxy]ethoxy]-2-(2,6-dioxo-3-piperidyl)isoindoline-1,3-dione (60 mg, trifluoroacetate) as colorless oil. LC/MS (ESI) m/z: 954.4 [M+1]$^+$.

Step 5: Preparation of 5-(2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)ethoxy)-2-(2,6-dioxopiperidin-3-yl)isoindoline-1,3-dione

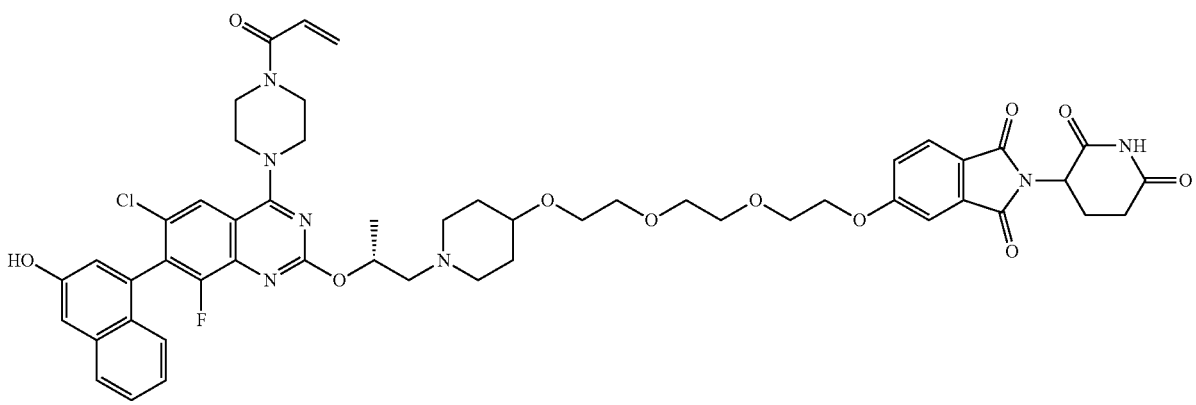 [SMILES: C=CC(=O)N1CCN(c2nc(O[C@H](C)CN3CCC(OCCOCCOCCOc4ccc5c(c4)C(=O)N(C4CCC(=O)NC4=O)C5=O)CC3)nc3c(F)c(-c4cc(O)cc5ccccc45)c(Cl)cc23)CC1]

To the mixture of 5-[2-[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]ethoxy]ethoxy]-2-(2,6-dioxo-3-piperidyl)isoindoline-1,3-dione (60 mg, 0.056 mmol, 1 eq, trifluoroacetate) in dichloromethane (20 mL) was added 2,6-lutidine (0.06 mL, 10 eq). Then prop-2-enoyl chloride (4 mg, 0.050 mmol, 0.004 mL, 0.9 eq) in dichloromethane (5 mL) was added to the mixture at −78° C. under nitrogen atmosphere. The mixture was stirred at −78° C. for 30 minutes under nitrogen atmosphere. Then the mixture was quenched with water (20 mL). It was extracted with dichloromethane (20 mL×3) and washed with brine (20 mL×2), dried over anhydrous sodium sulfate, filtered and concentrated under vacuum to give a residue. The residue was purified by prep-HPLC. Compound 5-[2-[2-[2-[[1-[(2R)-2-[6-chloro-8-fluoro-7-(3-hydroxy-1-naphthyl)-4-(4-prop-2-enoylpiperazin-1-yl)quinazolin-2-yl]oxypropyl]-4-piperidyl]oxy]ethoxy]ethoxy]ethoxy]-2-(2,6-dioxo-3-piperidyl)isoindoline-1,3-dione (5.6 mg, 0.0052 mmol, 9.27% yield, 98% purity, formate) was obtained as a white solid. LC/MS (ESI) m/z: 504.8 [M/2+1]$^+$; $^1$H-NMR (400 MHz, DMSO-d$_6$) δ 11.10 (s, 1H), 8.31 (s, 2H), 7.99 (s, 1H), 7.80-7.78 (d, J=8.0 Hz, 2H), 7.47-7.40 (m, 2H), 7.36-7.30 (m, 1H), 7.28 (s, 1H), 7.23-7.20 (m, 1H), 7.08-7.04 (m, 1H), 6.88-6.77 (m, 1H), 6.25-6.13 (m, 1H), 5.83-5.67 (m, 2H), 5.43-5.31 (m, 1H), 5.13-5.06 (m, 1H), 4.29-4.24 (m, 2H), 3.94-3.72 (m, 12H), 3.58-3.52 (m, 7H), 3.24-3.13 (m, 2H), 2.94-2.71 (m, 3H), 2.64-2.55 (m, 2H), 2.41-2.34 (m, 1H), 2.21-1.91 (m, 4H), 1.78-1.62 (m, 2H), 1.30-1.27 (m, 3H), 1.24-1.17 (m, 1H).

Exemplary Synthesis of 5-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)-2-(2,6-dioxopiperidin-3-yl)isoindoline-1,3-dione (Exemplary Compound 434)

Step 1: Preparation of tert-butyl 4-(2-(2-((2-(2,6-dioxopiperidin-3-yl)-1,3-dioxoisoindolin-5-yl)oxy)ethoxy)ethoxy)piperidine-1-carboxylate

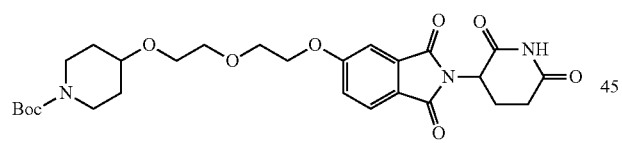

To a solution of tert-butyl 4-[2-[2-(p-tolylsulfonyloxy)ethoxy]ethoxy]piperidine-1-carboxylate (500 mg, 1.13 mmol, 1 eq) in N,N-dimethylformamide (10 mL) was added 2-(2,6-dioxo-3-piperidyl)-5-hydroxy-isoindoline-1,3-dione (309 mg, 1.13 mmol, 1 eq), potassium iodide (19 mg, 0.11 mmol, 0.1 eq) and potassium iodide (390 mg, 2.82 mmol, 2.5 eq), the mixture was stirred at 50° C. for 16 hours. The mixture was poured into hydrochloric acid solution (1 M) to adjust pH about 3-4, and the reaction mixture was extracted with ethyl acetate (50 mL). The combined organic layers were washed with brine (30 mL×2), dried over sodium sulfate, filtered and concentrated under reduced pressure to give a residue. The residue was purified by prep-TLC (dichloromethane:methanol=10:1). The residue was purified by semi-preparative reverse phase HPLC. Tert-butyl 4-[2-[2-[2-(2,6-dioxo-3-piperidyl)-1,3-dioxo-isoindolin-5-yl]oxyethoxy]ethoxy]piperidine-1-carboxylate (234 mg, 0.42 mmol, 38% yield) was obtained as a white solid. LC/MS (ESI) m/z: 568.3 [M+23]$^+$.

Step 2: Preparation of 2-(2,6-dioxopiperidin-3-yl)-5-(2-(2-(piperidin-4-yloxy)ethoxy)ethoxy)isoindoline-1,3-dione

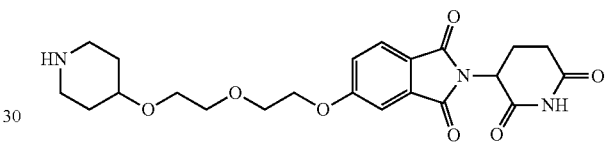

To a solution of tert-butyl 4-[2-[2-[2-(2,6-dioxo-3-piperidyl)-1,3-dioxo-isoindolin-5-yl]oxyethoxy]ethoxy]piperidine-1-carboxylate (330 mg, 0.60 mmol, 1 eq) in dichloromethane (4 mL) was added hydrochloric acid/dioxane (4 M, 4 mL, 26.45 eq), the mixture was stirred at 25° C. for 2 hours. The mixture was concentrated under reduced pressure to give a residue. Compound 2-(2,6-dioxo-3-piperidyl)-5-[2-[2-(4-piperidyloxy)ethoxy]ethoxy]isoindoline-1,3-dione (260 mg, 0.54 mmol, 89% yield, hydrochloride) was obtained as a colorless oil. LC/MS (ESI) m/z: 446.1 [M+1]$^+$.

Step 3: Preparation of tert-butyl 4-(6-chloro-2-(((2R)-1-(4-(2-(2-((2-(2,6-dioxopiperidin-3-yl)-1,3-dioxoisoindolin-5-yl)oxy)ethoxy)ethoxy)piperidin-1-yl)propan-2-yl)oxy)-8-fluoro-7-(3-hydroxynaphthalen-1-yl)quinazolin-4-yl)piperazine-1-carboxylate

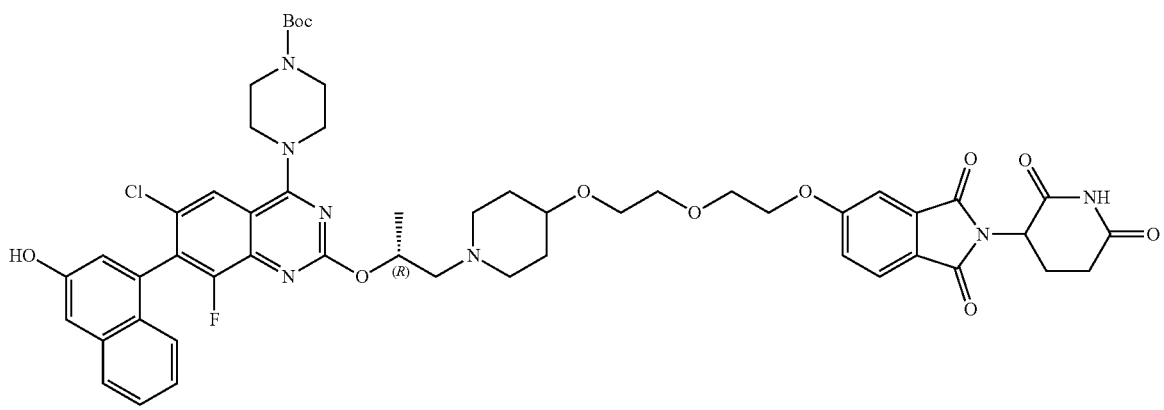

To a solution of 2-(2,6-dioxo-3-piperidyl)-5-[2-[2-(4-piperidyloxy)ethoxy]ethoxy]isoindoline-1,3-dione (86 mg, 0.19 mmol, 1.4 eq, hydrochloride) in methanol (3 mL) was added sodium acetate (34 mg, 0.41 mmol, 3 eq), the mixture was stirred at 25° C. for 0.5 h. Then tert-butyl 4-[6-chloro-8-fluoro-7-(3-hydroxy-1-naphthyl)-2-[(1R)-1-methyl-2-oxo-ethoxy]quinazolin-4-yl]piperazine-1-carboxylate (80 mg, 0.14 mmol, 1 eq) in dichloromethane (3 mL) was added. Acetic acid (8 mg, 0.14 mmol, 1 eq) and sodium cyanoborohydride (26 mg, 0.41 mmol, 3 eq) were added to the reaction at 0° C. for 0.5 hour, the mixture was stirred at 25° C. for 11 hours. The reaction was concentrated under reduced pressure to give a residue. The residue was purified by prep-TLC (dichloromethane:methanol=10:1). Compound tert-butyl 4-[6-chloro-2-[(1R)-2-[4-[2-[2-[2-(2,6-dioxo-3-piperidyl)-1,3-dioxo-isoindolin-5-yl]oxyethoxy]ethoxy]-1-piperidyl]-1-methyl-ethoxy]-8-fluoro-7-(3-hydroxy-1-naphthyl)quinazolin-4-yl]piperazine-1-carboxylate (43 mg, 0.04 mmol, 28% yield, 90% purity) was obtained as a colorless oil. LC/MS (ESI) m/z: 1011.9 [M+1]$^+$.

Step 4: Preparation of 5-(2-(2-((1-((2R)-2-((6-chloro-8-fluoro-7-(3-hydroxynaphthalen-1-yl)-4-(piperazin-1-yl)quinazolin-2-yl)oxy)propyl)piperidin-4-yl)oxy)ethoxy)ethoxy)-2-(2,6-dioxopiperidin-3-yl)isoindoline-1,3-dione

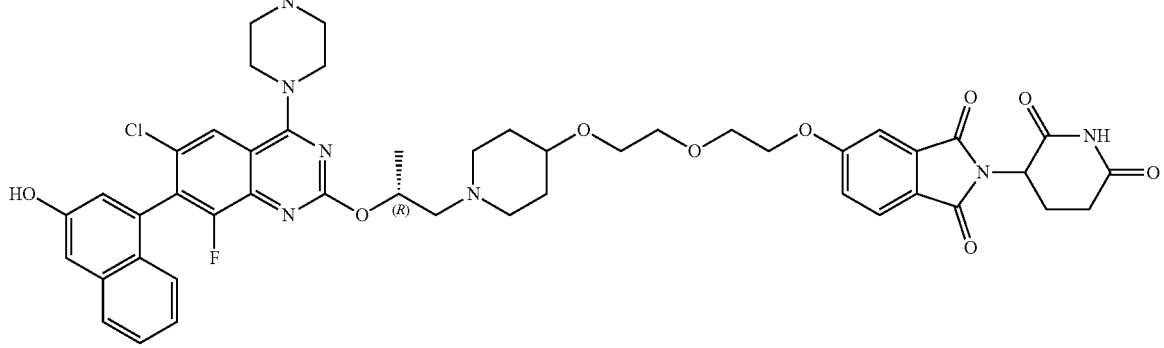

To a solution of tert-butyl 4-[6-chloro-2-[(1R)-2-[4-[2-[2-[2-(2,6-dioxo-3-piperidyl)-1,3-dioxo-isoindolin-5-yl]oxyethoxy]ethoxy]-1-piperidyl]-1-methyl-ethoxy]-8-fluoro-7-(3-hydroxy-1-naphthyl)quinazolin-4-yl]piperazine-1-carboxylate (43 mg, 0.04 mmol, 1 eq) in dichloromethane (3 mL) was added hydrochloric acid/dioxane (4 M, 3 mL, 282 eq), the mixture was stirred at 25° C. for 1 hour. The mixture was concentrated under reduced pressure to give a residue. Compound 5-[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]ethoxy]-2-(2,6-dioxo-3-piperidyl)isoindoline-1,3-dione (38 mg, 0.04 mol, 98% yield) was obtained as a colorless oil.

Step 5: Preparation of 5-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)-2-(2,6-dioxopiperidin-3-yl)isoindoline-1,3-dione

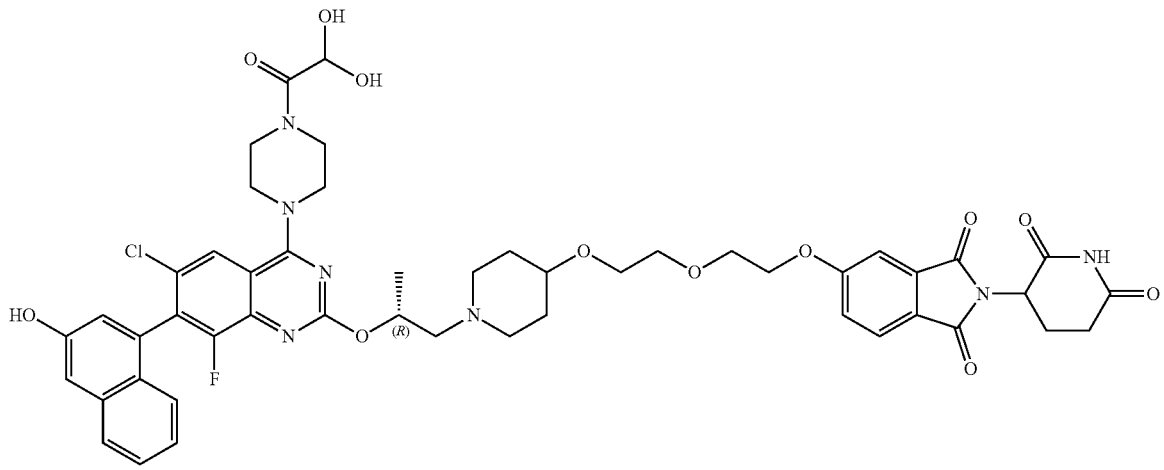

To a solution of 2,2-dihydroxyacetic acid (37 mg, 0.4 mmol, 10 eq), 5-[2-[2-[[1-[(2R)-2-[6-chloro-8-fluoro-7-(3-hydroxy-1-naphthyl)-4-piperazin-1-yl-quinazolin-2-yl]oxypropyl]-4-piperidyl]oxy]ethoxy]ethoxy]-2-(2,6-dioxo-3-piperidyl)isoindoline-1,3-dione (38 mg, 0.04 mmol, 1 eq, hydrochloride) and o-(7-azabenzotriazol-1-yl)-n,n,n',n'-tetramethyluronium hexafluorophosphate (61 mg, 0.16 mmol, 4 eq) was added diisopropylethylamine (16 mg, 0.12 mmol, 0.02 mL, 3 eq) in N,N-dimethylformamide (2 mL), the mixture was stirred at 25° C. for 16 hours. The reaction mixture was quenched by water (30 mL), and extracted with ethyl acetate (20 mL×2), the combined organic layers were washed with brine (30 mL), dried over sodium sulfate, filtered and concentrated under reduced pressure to give a residue. The residue was purified by semi-preparative reverse phase HPLC. Compound 5-[2-[2-[[1-[(2R)-2-[6-chloro-4-[4-(2,2-dihydroxyacetyl)piperazin-1-yl]-8-fluoro-7-(3-hydroxy-1-naphthyl)quinazolin-2-yl]oxypropyl]-4-piperidyl]oxy]ethoxy]ethoxy]-2-(2,6-dioxo-3-piperidyl)isoindoline-1,3-dione (7.4 mg, 0.007 mmol, 18% yield, 96% purity) was obtained as a white solid. LC/MS (ESI) m/z: 984.3 [M+1]$^+$; $^1$H-NMR (400 MHz, DMSO-d$_6$) δ 11.08 (s, 1H), 10.01 (s, 1H), 8.13 (s, 1H), 8.00 (s, 1H), 7.79 (d, J=8.3 Hz, 1H), 7.46-7.38 (m, 2H), 7.34-7.30 (m, 1H), 7.27 (s, 1H), 7.23-7.14 (m, 2H), 7.05 (dd, J=2.4, 5.8 Hz, 1H), 6.36 (d, J=7.3 Hz, 1H), 5.42-5.34 (m, 1H), 5.09 (dd, J=5.4, 12.8 Hz, 1H), 4.27 (s, 2H), 3.92-3.80 (m, 5H), 3.78-3.69 (m, 4H), 3.54 (d, J=2.6 Hz, 3H), 3.48 (dd, J=5.1, 10.9 Hz, 4H), 2.93-2.81 (m, 3H), 2.63-2.51 (m, 5H), 2.23 (s, 2H), 2.08-1.99 (m, 1H), 1.73 (s, 2H), 1.37-1.24 (m, 5H).

Exemplary Synthesis of (2S,4R)—N-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide (Exemplary Compound 436)

Step 1: Preparation of tert-butyl 4-(2-(2-(((2S,4R)-4-hydroxy-1-(3-methyl-2-(3-methylisoxazol-5-yl)butanoyl)pyrrolidine-2-carboxamido)methyl)-5-(4-methylthiazol-5-yl)phenoxy)ethoxy)piperidine-1-carboxylate

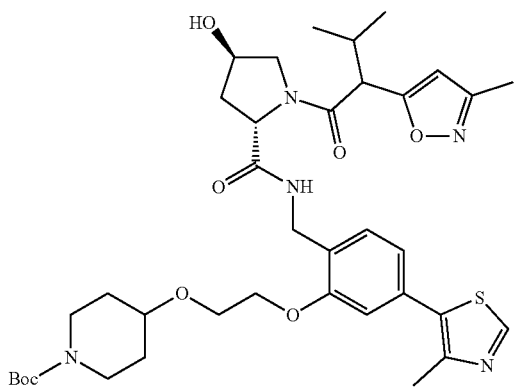 [SMILES: Cc1cc(C(C(=O)N2C[C@H](O)C[C@H]2C(=O)NCc2ccc(-c3scnc3C)cc2OCCOC2CCN(C(=O)OC(C)(C)C)CC2)C(C)C)on1]

To a solution of tert-butyl 4-[2-(p-tolylsulfonyloxy)ethoxy]piperidine-1-carboxylate (361 mg, 0.90 mmol, 1.5 eq) and (2S,4R)-4-hydroxy-N-[[2-hydroxy-4-(4-methylthiazol-5-yl)phenyl]methyl]-1-[3-methyl-2-(3-methylisoxazol-5-yl)butanoyl]pyrrolidine-2-carboxamide (300 mg, 0.60 mmol, 1 eq) in acetonitrile (6 mL) was added potassium carbonate (166. mg, 1.20 mmol, 2 eq). The mixture was stirred at 80° C. for 12 hours. Water (30 mL) was added. The aqueous phase was extracted with ethyl acetate (30 mL×2). The combined organic phase was dried with anhydrous sodium sulfate, filtered and concentrated in vacuum to get the crude product. The crude product was purified by semi-preparative reverse phase HPLC. Compound tert-butyl 4-[2-[2-[[[(2S,4R)-4-hydroxy-1-[3-methyl-2-(3-methylisoxazol-5-yl)butanoyl]pyrrolidine-2-carbonyl]amino]methyl]-5-(4-methylthiazol-5-yl)phenoxy]ethoxy]piperidine-1-carboxylate (320 mg, 0.44 mmol, 73% yield) as a white solid was obtained. LC/MS (ESI) m/z: 626.2 [M−100]$^+$.

Step 2: Preparation of tert-butyl 4-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)piperidine-1-carboxylate

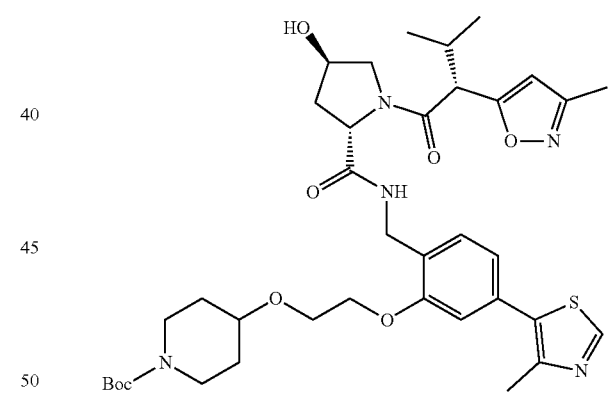

Tert-butyl 4-[2-[2-[[[(2S,4R)-4-hydroxy-1-[3-methyl-2-(3-methylisoxazol-5-yl)butanoyl]pyrrolidine-2-carbonyl]amino]methyl]-5-(4-methylthiazol-5-yl)phenoxy]ethoxy]piperidine-1-carboxylate (320 mg, 0.44 mmol, 1 eq) was separated by chiral SFC. The mixture was concentrated under reduced pressure to afford the product. Compound tert-butyl 4-[2-[2-[[[(2S,4R)-4-hydroxy-1-[(2R)-3-methyl-2-(3-methylisoxazol-5-yl)butanoyl]pyrrolidine-2-carbonyl]amino]methyl]-5-(4-methylthiazol-5-yl)phenoxy]ethoxy]piperidine-1-carboxylate (140 mg, 0.19 mmol, 85% yield, 97% purity) was obtained as a colorless oil.

833

Step 3: Preparation of (2S,4R)-4-hydroxy-1-((R)-3-methyl-2-(3-methylisoxazol-5-yl)butanoyl)-N-(4-(4-methylthiazol-5-yl)-2-(2-(piperidin-4-yloxy)ethoxy)benzyl)pyrrolidine-2-carboxamide

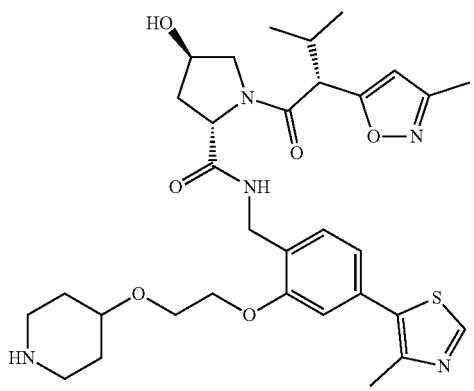 [SMILES: Cc1cc([C@H](C(=O)N2C[C@H](O)C[C@H]2C(=O)NCc2ccc(-c3scnc3C)cc2OCCOC2CCNCC2)C(C)C)on1]

834

To a solution of tert-butyl 4-[2-[2-[[[(2S,4R)-4-hydroxy-1-[(2R)-3-methyl-2-(3-methylisoxazol-5-yl)butanoyl]pyrrolidine-2-carbonyl]amino]methyl]-5-(4-methylthiazol-5-yl)phenoxy]ethoxy]piperidine-1-carboxylate (140 mg, 0.19 mmol, 1 eq) in dichloromethane (3 mL) was added hydrochloric acid/dioxane (4 M, 3 mL, 62.22 eq), the mixture was stirred at 25° C. for 2 hours. The mixture was concentrated under reduced pressure to give a residue. Compound (2S,4R)-4-hydroxy-1-[(2R)-3-methyl-2-(3-methylisoxazol-5-yl)butanoyl]-N-[[4-(4-methylthiazol-5-yl)-2-[2-(4-piperidyloxy)ethoxy]phenyl]methyl]pyrrolidine-2-carboxamide (120 mg, 0.18 mmol, 94% yield, hydrochloride) was obtained as a colorless oil. LC/MS (ESI) m/z: 626.2 [M+1]$^+$.

Step 4: Preparation of (2S,4R)—N-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide

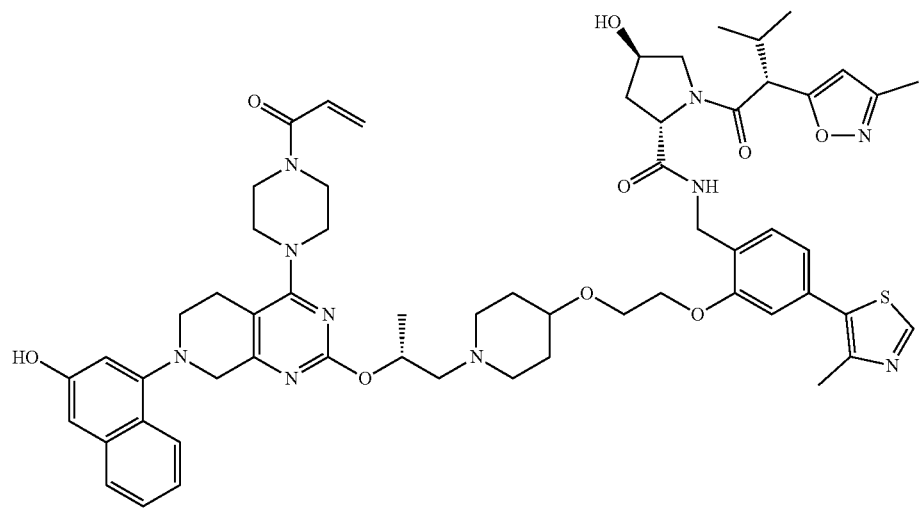 [SMILES: C=CC(=O)N1CCN(c2nc(O[C@H](C)CN3CCC(OCCOc4cc(-c5scnc5C)ccc4CNC(=O)[C@@H]4C[C@@H](O)CN4C(=O)[C@@H](c4cc(C)no4)C(C)C)CC3)nc3c2CCN(c2cc(O)cc4ccccc24)C3)CC1]

To a mixture of (2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propanal (50 mg, 0.10 mmol, 1 eq) in dichloromethane (3 mL) and methanol (1 mL) was added sodium acetate (8 mg, 0.1 mmol, 1 eq) stirred at 25° C. for 15 minutes, then acetic acid (6 mg, 0.1 mmol, 1 eq) and (2S,4R)-4-hydroxy-1-[(2R)-3-methyl-2-(3-methylisoxazol-5-yl)butanoyl]-N-[[4-(4-methylthiazol-5-yl)-2-[2-(4-piperidyloxy)ethoxy]phenyl]methyl]pyrrolidine-2-carboxamide (64 mg, 0.1 mmol, 1 eq, hydrochloride) was added stirred at 0° C. for 15 min, then borane; 2-methylpyridine (44 mg, 0.41 mmol, 4 eq) was added at 0° C., then the reaction mixture was stirred at 25° C. for 12 hours. The mixture was concentrated under reduced pressure to give a residue. The residue was purified by semi-preparative reverse phase HPLC. Compound (2S,4R)-4-hydroxy-N-[[2-[2-[[1-[(2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propyl]-4-piperidyl]oxy]ethoxy]-4-(4-methylthiazol-5-yl)phenyl]methyl]-1-[(2R)-3-methyl-2-(3-methylisoxazol-5-yl)butanoyl]pyrrolidine-2-carboxamide (12.4 mg, 0.01 mmol, 10% yield, 95% purity) was obtained as a pink solid. LC/MS (ESI) m/z: 1097.5 [M+1]$^+$; $^1$H-NMR (400 MHz, DMSO-d$_6$) δ 9.66 (s, 1H), 8.97 (s, 1H), 8.28 (s, 1H), 8.00 (d, J=7.7 Hz, 1H), 7.66 (d, J=8.8 Hz, 1H), 7.37 (d, J=6.6 Hz, 1H), 7.26 (s, 1H), 7.04-6.95 (m, 2H), 6.87-6.76 (m, 3H), 6.21-6.12 (m, 2H), 5.72 (d, J=12.3 Hz, 1H), 5.20 (s, 1H), 4.35-4.04 (m, 8H), 3.85-3.63 (m, 8H), 3.51 (s, 14H), 2.90-2.73 (m, 2H), 2.27-2.09 (m, 9H), 2.04-1.77 (m, 5H), 1.40 (s, 2H), 1.25 (d, J=6.1 Hz, 3H), 0.96 (d, J=6.6 Hz, 2H), 0.79 (d, J=6.6 Hz, 2H), 0.69 (d, J=6.2 Hz, 1H), 0.57 (d, J=6.7 Hz, 1H).

Exemplary Synthesis of (S)—N—((S)-2-((S)-2-(4-(4-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)naphthalen-1-yl)thiazol-2-yl)pyrrolidin-1-yl)-1-cyclohexyl-2-oxoethyl)-2-(methylamino)propanamide (Exemplary Compound 447)

Step 1: Preparation of 2-(2-(2-(piperidin-4-yloxy)ethoxy)ethoxy)ethan-1-ol

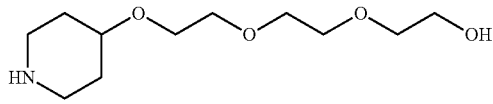 [SMILES: OCCOCCOCCOC1CCNCC1]

To the mixture of tert-butyl 4-[2-[2-(2-hydroxyethoxy)ethoxy]ethoxy]piperidine-1-carboxylate (950 mg, 2.85 mmol, 1 eq) in dichloromethane (15 mL) was added hydrogen chloride/methanol (4 M, 0.7 mL, 1 eq). The mixture was stirred at 25° C. for 1 hour. The mixture was concentrated under vacuum to give the product 2-[2-[2-(4-piperidyloxy)ethoxy]ethoxy]ethanol (760 mg, 2.82 mmol, 99% yield, hydrochloride) as a yellow oil. $^1$H-NMR (400 MHz, DMSO-d$_6$) δ 9.43-8.89 (m, 2H), 3.60-3.51 (m, 2H), 3.49-3.32 (m, 7H), 3.14 (s, 3H), 3.12-2.99 (m, 2H), 2.95-2.80 (m, 2H), 2.43-2.21 (m, 1H), 2.00-1.82 (m, 2H), 1.74-1.54 (m, 2H).

Step 2: Preparation of benzyl 4-(2-(2-(2-hydroxyethoxy)ethoxy)ethoxy)piperidine-1-carboxylate

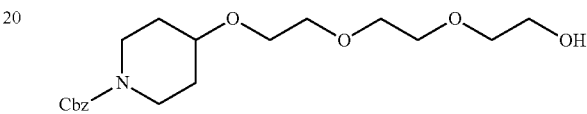

To the mixture of 2-[2-[2-(4-piperidyloxy)ethoxy]ethoxy]ethanol (760 mg, 2.82 mmol, 1 eq, hydrochloride) in water (5 mL) and tetrahydrofuran (10 mL) was added sodium hydrogencarbonate (710 mg, 8.45 mmol, 3 eq). The mixture was stirred at 25° C. for 30 minutes. Then benzyl chloroformate (720 mg, 4.23 mmol, 0.6 mL, 1.5 eq) was added in the mixture. The mixture was stirred at 25° C. for 12 hours. Then the mixture was diluted with water (30 mL). Then the mixture was extracted with ethyl acetate (30 mL×3). The combined organic layers were washed with water (50 mL×2) and brine (50 mL×2), dried over anhydrous sodium sulfate, filtered and concentrated under vacuum to give the product benzyl 4-[2-[2-(2-hydroxyethoxy)ethoxy]ethoxy]piperidine-1-carboxylate (770 mg, 2.10 mmol) as a colorless oil. LC/MS (ESI) m/z: 390.2 [M+23]$^+$.

Step 3: Preparation of benzyl 4-(2-(2-(2-(tosyloxy)ethoxy)ethoxy)ethoxy)piperidine-1-carboxylate

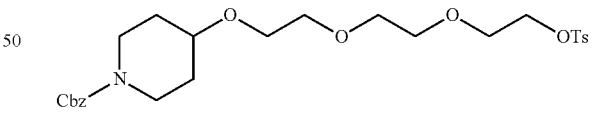

To the mixture of benzyl 4-[2-[2-(2-hydroxyethoxy)ethoxy]ethoxy]piperidine-1-carboxylate (770 mg, 2.10 mmol, 1 eq) in dichloromethane (15 mL) was added p-toluenesulfonyl chloride (479 mg, 2.51 mmol, 1.2 eq) and triethylamine (424 mg, 4.19 mmol, 0.5 mL, 2 eq). The mixture was stirred at 25° C. for 12 hours. Then the mixture was concentrated under vacuum to give a residue. The residue was purified by silica gel chromatography (Petroleum ether:Ethyl acetate=10:1 to 1:1). Benzyl 4-[2-[2-[2-(p-tolylsulfonyloxy)ethoxy]ethoxy]ethoxy]piperidine-1-carboxylate (100 mg, 0.19 mmol, 10% yield) was obtained as a colorless oil. LC/MS (ESI) m/z: 544.3 [M+23]$^+$.

Step 4: Preparation of benzyl 4-(2-(2-(2-((4-(2-((S)-1-((S)-2-((S)-2-((tert-butoxycarbonyl)(methyl)amino)propanamido)-2-cyclohexylacetyl)pyrrolidin-2-yl)thiazol-4-yl)naphthalen-1-yl)oxy)ethoxy)ethoxy)ethoxy)piperidine-1-carboxylate

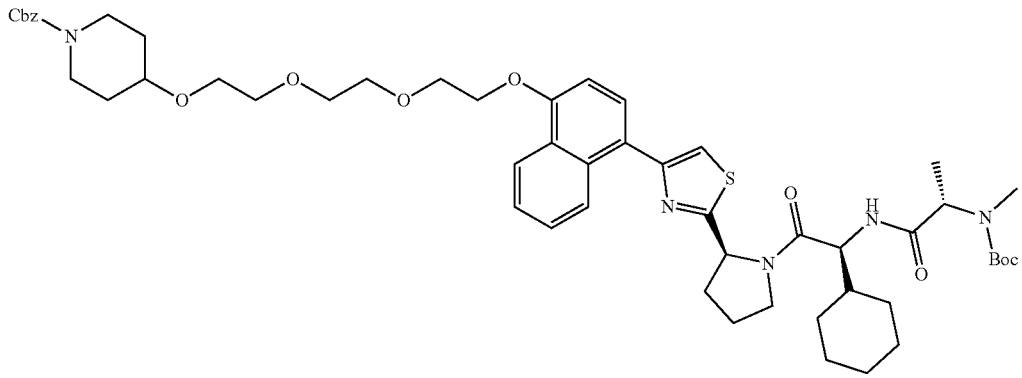 [SMILES: C[C@@H](C(=O)N[C@H](C(=O)N1CCC[C@H]1c1nc(-c2ccc(OCCOCCOCCOC3CCN(C(=O)OCc4ccccc4)CC3)c3ccccc23)cs1)C1CCCCC1)N(C)C(=O)OC(C)(C)C]

To the mixture of benzyl 4-[2-[2-[2-(p-tolylsulfonyloxy)ethoxy]ethoxy]ethoxy]piperidine-1-carboxylate (100 mg, 0.19 mmol, 1 eq) and tert-butyl N-[(1S)-2-[[(1S)-1-cyclohexyl-2-[(2S)-2-[4-(4-hydroxy-1-naphthyl)thiazol-2-yl]pyrrolidin-1-yl]-2-oxo-ethyl]amino]-1-methyl-2-oxo-ethyl]-N-methyl-carbamate (119 mg, 0.19 mmol, 1 eq) in acetonitrile (5 mL) was added potassium carbonate (52 mg, 0.38 mmol, 2 eq). The mixture was stirred at 90° C. for 12 hours. The mixture was diluted with water (30 mL). Then the mixture was extracted by ethyl acetate (30 mL×3). The combined organic layers were washed with water (50 mL×2) and brine (50 mL×2), dried over anhydrous sodium sulfate, filtered and concentrated under vacuum to give a residue. The residue was purified by prep-TLC (ethyl acetate). Compound benzyl 4-[2-[2-[2-[[4-[2-[(2S)-1-[(2S)-2-[[(2S)-2-[tert-butoxycarbonyl(methyl)amino]propanoyl]amino]-2-cyclohexyl-acetyl]pyrrolidin-2-yl]thiazol-4-yl]-1-naphthyl]oxy]ethoxy]ethoxy]ethoxy]piperidine-1-carboxylate (120 mg) was obtained as a green oil. LC/MS (ESI) m/z: 970.6 [M+1]$^+$.

Step 5: Preparation of tert-butyl ((S)-1-(((S)-1-cyclohexyl-2-oxo-2-((S)-2-(4-(4-(2-(2-(2-(piperidin-4-yloxy)ethoxy)ethoxy)ethoxy)naphthalen-1-yl)thiazol-2-yl)pyrrolidin-1-yl)ethyl)amino)-1-oxopropan-2-yl)(methyl)carbamate

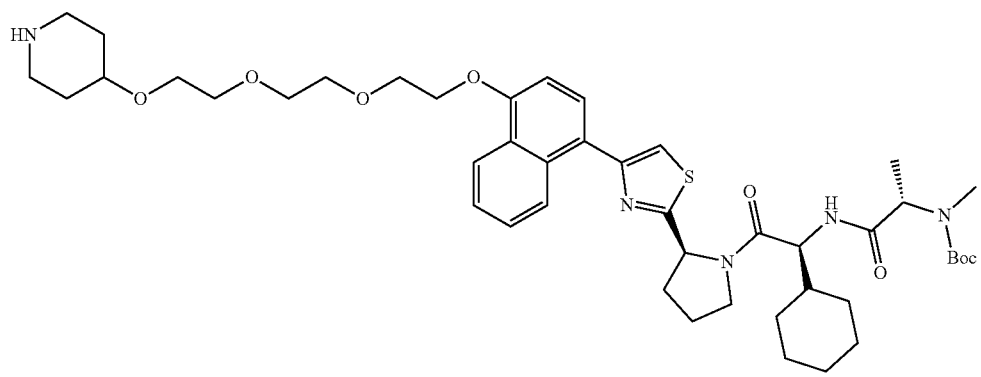 [SMILES: C[C@@H](C(=O)N[C@H](C(=O)N1CCC[C@H]1c1nc(-c2ccc(OCCOCCOCCOC3CCNCC3)c3ccccc23)cs1)C1CCCCC1)N(C)C(=O)OC(C)(C)C]

To the mixture of benzyl 4-[2-[2-[2-[[4-[2-[(2S)-1-[(2S)-2-[[(2S)-2-[tert-butoxycarbonyl(methyl)amino]propanoyl]amino]-2-cyclohexyl-acetyl]pyrrolidin-2-yl]thiazol-4-yl]-1-naphthyl]oxy]ethoxy]ethoxy]ethoxy]piperidine-1-carboxylate (120 mg, 0.12 mmol, 1 eq) in trifluoroethanol (10 mL) was added palladium on activated carbon catalyst (30 mg, 10% purity) under nitrogen atmosphere. The mixture was degassed and refilled with hydrogen for 3 times. Then it was stirred at 25° C. for 2 hours. The mixture was filtered and concentrated under reduced pressure to give a residue. The residue was purified by prep-HPLC. Compound tert-butyl N-[(1S)-2-[[(1S)-1-cyclohexyl-2-oxo-2-[(2S)-2-[4-[4-[2-[2-[2-(4-piperidyloxy)ethoxy]ethoxy]ethoxy]-1-naphthyl]thiazol-2-yl]pyrrolidin-1-yl]ethyl]amino]-1-methyl-2-oxo-ethyl]-N-methyl-carbamate (35 mg, 0.04 mmol, 32% yield, formate) was obtained as a white solid. LC/MS (ESI) m/z: 836.6 [M+1]$^+$.

Step 6: Preparation of tert-butyl ((S)-1-(((S)-2-((S)-2-(4-(4-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)naphthalen-1-yl)thiazol-2-yl)pyrrolidin-1-yl)-1-cyclohexyl-2-oxoethyl)amino)-1-oxopropan-2-yl)(methyl)carbamate

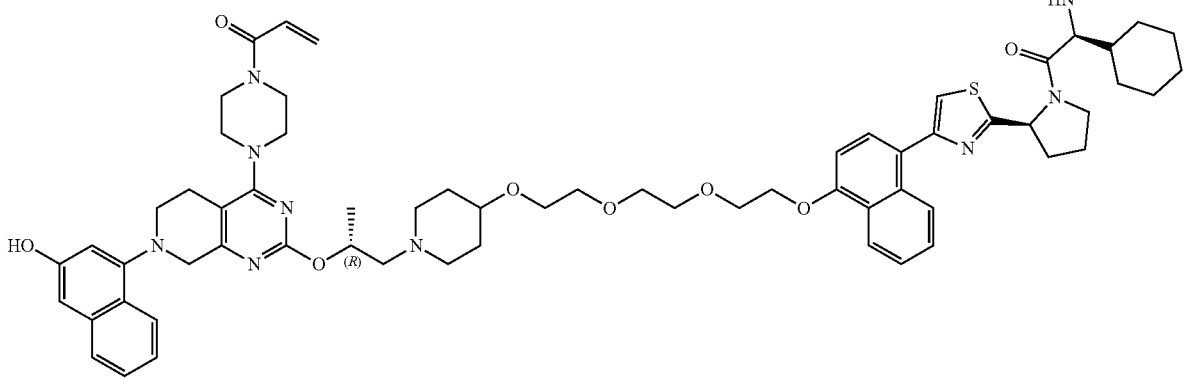

To the mixture of tert-butyl N-[(1S)-2-[[(1S)-1-cyclohexyl-2-oxo-2-[(2S)-2-[4-[4-[2-[2-[2-(4-piperidyloxy)ethoxy]ethoxy]ethoxy]-1-naphthyl]thiazol-2-yl]pyrrolidin-1-yl]ethyl]amino]-1-methyl-2-oxo-ethyl]-N-methyl-carbamate (45 mg, 0.05 mmol, 1 eq, formate) in methanol (2 mL) and dichloromethane (2 mL) was added sodium acetate (12 mg, 0.15 mmol, 3 eq). Then borane; 2-methylpyridine complex (27 mg, 0.25 mmol, 5 eq) was added to the mixture under stirring. Then the mixture was stirred at 25° C. for 20 minutes. Then acetic acid (6 mg, 0.10 mmol, 2 eq) and (2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propanal (24 mg, 0.05 mmol, 1 eq) was added at 0° C. Then the reaction mixture was stirred at 25° C. for 12 hours. Then the mixture was concentrated under vacuum to give a residue. The residue was purified by prep-TLC (dichloromethane:methanol=9:1). Tert-butyl N-[(1S)-2-[[(1S)-1-cyclohexyl-2-[(2S)-2-[4-[4-[2-[2-[2-[[1-[(2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propyl]-4-piperidyl]oxy]ethoxy]ethoxy]ethoxy]-1-naphthyl]thiazol-2-yl]pyrrolidin-1-yl]-2-oxo-ethyl]amino]-1-methyl-2-oxo-ethyl]-N-methyl-carbamate (26 mg, 0.02 mmol, 39% yield) was obtained as a pink oil. LC/MS (ESI) m/z: 1307.5 [M+1]$^+$.

Step 7: Preparation of (S)—N—((S)-2-((S)-2-(4-(4-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)naphthalen-1-yl)thiazol-2-yl)pyrrolidin-1-yl)-1-cyclohexyl-2-oxoethyl)-2-(methylamino)propanamide

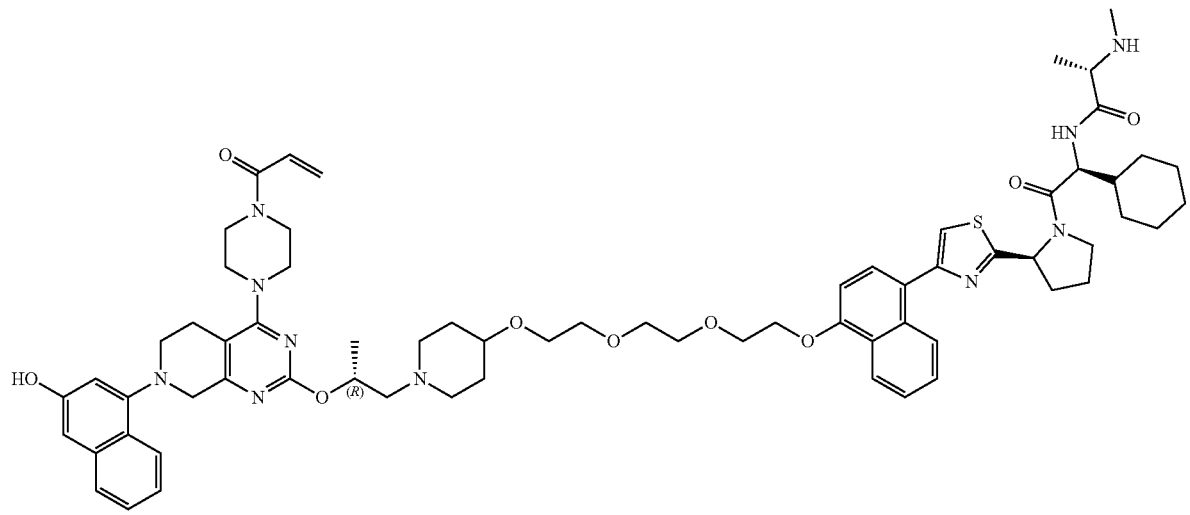

To the mixture of tert-butyl N-[(1S)-2-[[(1S)-1-cyclohexyl-2-[(2S)-2-[4-[4-[2-[2-[2-[[1-[(2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propyl]-4-piperidyl]oxy]ethoxy]ethoxy]ethoxy]-1-naphthyl]thiazol-2-yl]pyrrolidin-1-yl]-2-oxo-ethyl]amino]-1-methyl-2-oxo-ethyl]-N-methyl-carbamate (26 mg, 0.02 mmol, 1 eq) in dichloromethane (2.5 mL) was added trifluoroacetic acid (3.38 mmol, 0.25 mL). The mixture was stirred at 25° C. for 30 minutes. Then the mixture was adjusted to PH=7-8 with sodium hydrogencarbonate solution, then the mixture was filtered. The filtrate was purified by prep-HPLC. Compound (2S)—N-[(1S)-1-cyclohexyl-2-[(2S)-2-[4-[4-[2-[2-[2-[[1-[(2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propyl]-4-piperidyl]oxy]ethoxy]ethoxy]ethoxy]-1-naphthyl]thiazol-2-yl]pyrrolidin-1-yl]-2-oxo-ethyl]-2-(methylamino)propanamide (12.4 mg, 0.01 mmol, 48% yield, 95% purity, formate) was obtained as a pink solid. LC/MS (ESI) m/z: 604.4 [M/2+1]$^+$; $^1$H-NMR (400 MHz, DMSO-d$_6$) δ 8.29-8.20 (m, 4H), 8.07-7.96 (m, 2H), 7.71-7.62 (m, 2H), 7.59-7.57 (d, J=8.0 Hz, 1H), 7.56-7.49 (m, 2H), 7.42-7.35 (m, 1H), 7.30-7.20 (m, 1H), 7.03-7.01 (d, J=8.0 Hz, 1H), 6.88-6.74 (m, 3H), 6.19-6.10 (m, 1H), 5.75-5.68 (m, 1H), 5.48-5.39 (m, 1H), 5.23-5.11 (m, 1H), 4.55-4.47 (m, 1H), 4.34-4.27 (m, 2H), 4.05 (s, 2H), 3.93-3.88 (m, 2H), 3.82-3.77 (m, 2H), 3.73-3.62 (m, 8H), 3.58-3.55 (m, 3H), 3.26-3.17 (m, 6H), 3.14-3.05 (m, 2H), 2.92-2.83 (m, 2H), 2.79-2.68 (m, 2H), 2.31-2.24 (m, 2H), 2.23-2.17 (m, 4H), 2.14-1.99 (m, 5H), 1.88-1.47 (m, 10H), 1.39-1.28 (m, 2H), 1.23-1.21 (d, J=8.0 Hz, 3H), 1.16-0.94 (m, 9H).

Exemplary Synthesis of (S)—N—((S)-2-((S)-2-(4-(4-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)naphthalen-1-yl)thiazol-2-yl)pyrrolidin-1-yl)-1-cyclohexyl-2-oxoethyl)-2-(methylamino)propanamide (Exemplary Compound 446)

Step 1: Preparation of 2-(2-(piperidin-4-yloxy)ethoxy)ethan-1-ol

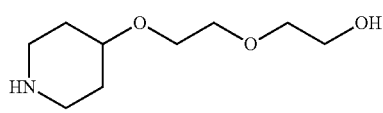 [SMILES: OCCOCCOC1CCNCC1]

To a solution of tert-butyl 4-[2-(2-hydroxyethoxy)ethoxy]piperidine-1-carboxylate (1 g, 3.46 mmol, 1 eq) in hydrochloride/methanol (4 M, 3 mL, 3.47 eq), the mixture was stirred at 25° C. for 1 hour. The mixture was filtered and concentrated under reduced pressure to give the product 2-[2-(4-piperidyloxy)ethoxy]ethanol (600 mg, hydrochloride) as a white solid.

Step 2: Preparation of benzyl 4-(2-(2-hydroxy-ethoxy)ethoxy)piperidine-1-carboxylate

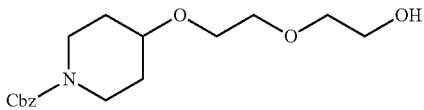 [SMILES: O=C(OCc1ccccc1)N1CCC(OCCOCCO)CC1]

To a solution of 2-[2-(4-piperidyloxy)ethoxy]ethanol (600 mg, 3.17 mmol, 1 eq) in dichloromethane (6 mL) was added benzyl carbonochloridate (568 mg, 3.33 mmol, 0.5 mL, 1.05 eq) and triethylamine (481 mg, 4.76 mmol, 0.7 mL, 1.5 eq), the mixture was stirred at 25° C. for 2 hours. The reaction mixture was extracted with dichloromethane (20 mL×2) and hydrochloric acid solution (1 M) (30 mL). The combined organic layers were washed with brine (50 mL), dried over sodium sulfate, concentrated under reduced pressure to give the product benzyl 4-[2-(2-hydroxyethoxy)ethoxy]piperidine-1-carboxylate (625 mg) as a colorless oil. LC/MS (ESI) m/z: 324.2 [M+1]$^+$.

Step 3: Preparation of benzyl 4-(2-(2-(tosyloxy)ethoxy)ethoxy)piperidine-1-carboxylate

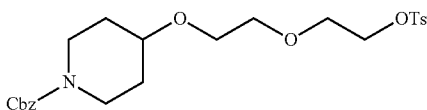 [SMILES: Cc1ccc(S(=O)(=O)OCCOCCOC2CCN(C(=O)OCc3ccccc3)CC2)cc1]

To a solution of benzyl 4-[2-(2-hydroxyethoxy)ethoxy]piperidine-1-carboxylate (625 mg, 1.93 mmol, 1 eq) in dichloromethane (10 mL) was added triethylamine (587 mg, 5.80 mmol, 0.8 mL, 3 eq), then p-toluenesulfonyl chloride (553 mg, 2.90 mmol, 1.5 eq) was added to the mixture, the mixture was stirred at 25° C. for 16 hours. The reaction mixture was quenched by water (30 mL), and extracted with dichloromethane (50 mL×2), the combined organic layers were washed with brine (30 mL), dried over sodium sulfate, filtered and concentrated under reduced pressure to give a residue. The residue was purified by column chromatography (petroleum ether:ethyl acetate=30:1 to 1:1). Compound benzyl 4-[2-[2-(p-tolylsulfonyloxy)ethoxy]ethoxy]piperidine-1-carboxylate (650 mg, 1.36 mmol, 70% yield) was obtained as a colorless oil. $^1$H-NMR (400 MHz, CD$_3$OD) δ 7.82-7.76 (m, 2H), 7.42 (d, J=8.0 Hz, 2H), 7.38-7.28 (m, 5H), 5.11 (s, 2H), 4.17-4.13 (m, 2H), 3.79-3.69 (m, 2H), 3.68-3.61 (m, 2H), 3.58-3.49 (m, 5H), 3.22 (s, 2H), 2.47-2.40 (m, 3H), 1.87-1.77 (m, 2H), 1.47 (tdd, J=4.4, 8.4, 12.8 Hz, 2H).

Step 4: Preparation of benzyl 4-(2-(2-((4-(2-((S)-1-((S)-2-((S)-2-((tert-butoxycarbonyl)(methyl)amino)propanamido)-2-cyclohexylacetyl)pyrrolidin-2-yl)thiazol-4-yl)naphthalen-1-yl)oxy)ethoxy)ethoxy)piperidine-1-carboxylate

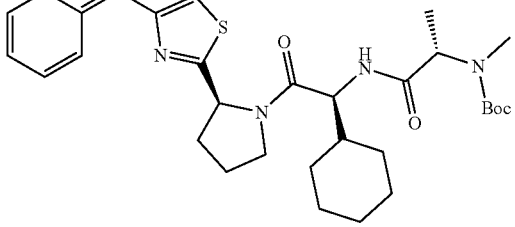

To a solution of benzyl 4-[2-[2-(p-tolylsulfonyloxy)ethoxy]ethoxy]piperidine-1-carboxylate (231 mg, 0.48 mmol, 1 eq), tert-butyl N-[(1S)-2-[[(1S)-1-cyclohexyl-2-[(2S)-2-[4-(4-hydroxy-1-naphthyl)thiazol-2-yl]pyrrolidin-1-yl]-2-oxo-ethyl]amino]-1-methyl-2-oxo-ethyl]-N-methyl-carbamate (300 mg, 0.48 mmol, 1 eq) in acetonitrile (5 mL) was added potassium carbonate (167 mg, 1.21 mmol, 2.5 eq), the mixture was stirred at 80° C. for 6 hours. The mixture was filtered and concentrated under reduced pressure to give a residue. The residue was purified by prep-TLC (dichloromethane:methanol=10:1). Compound benzyl 4-[2-[2-[[4-[2-[(2S)-1-[(2S)-2-[[(2S)-2-[tert-butoxycarbonyl(methyl)amino]propanoyl]amino]-2-cyclohexyl-acetyl]pyrrolidin-2-yl]thiazol-4-yl]-1-naphthyl]oxy]ethoxy]ethoxy]piperidine-1-carboxylate (400 mg, 0.36 mmol, 74% yield, 83% purity) was obtained as a yellow oil. LC/MS (ESI) m/z: 926.5 [M+1]$^+$.

Step 5: Preparation of tert-butyl ((S)-1-(((S)-1-cyclohexyl-2-oxo-2-((S)-2-(4-(4-(2-(2-(piperidin-4-yloxy)ethoxy)ethoxy)naphthalen-1-yl)thiazol-2-yl)pyrrolidin-1-yl)ethyl)amino)-1-oxopropan-2-yl)(methyl)carbamate

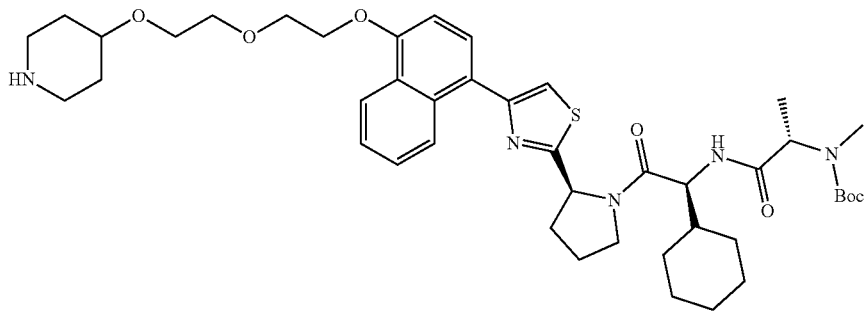 [SMILES: C[C@@H](C(=O)N[C@H](C(=O)N1CCC[C@H]1c1nc(-c2ccc(OCCOCCOC3CCNCC3)c3ccccc23)cs1)C1CCCCC1)N(C)C(=O)OC(C)(C)C]

To a solution of benzyl 4-[2-[2-[[4-[2-[(2S)-1-[(2S)-2-[[(2S)-2-[tert-butoxycarbonyl(methyl)amino]propanoyl]amino]-2-cyclohexyl-acetyl]pyrrolidin-2-yl]thiazol-4-yl]-1-naphthyl]oxy]ethoxy]ethoxy]piperidine-1-carboxylate (350 mg, 0.38 mmol, 1 eq) in trifluoroethanol (20 mL) was added palladium on activated carbon catalyst (100 mg, 0.38 mmol, 10% purity, 1 eq) under nitrogen. The suspension was degassed under vacuum and purged with hydrogen several times. The mixture was stirred under hydrogen (15 psi) at 25° C. for 2 hours. The mixture was filtered and concentrated under reduced pressure to give a residue. The residue was purified by semi-preparative reverse phase HPLC. Compound tert-butyl N-[(1S)-2-[[(1S)-1-cyclohexyl-2-oxo-2-[(2S)-2-[4-[4-[2-[2-(4-piperidyloxy)ethoxy]ethoxy]-1-naphthyl]thiazol-2-yl]pyrrolidin-1-yl]ethyl]amino]-1-methyl-2-oxo-ethyl]-N-methyl-carbamate (111 mg, 0.14 mmol, 37% yield) was obtained as a colorless oil.

Step 6: Preparation of tert-butyl ((S)-1-(((S)-2-((S)-2-(4-(4-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)naphthalen-1-yl)thiazol-2-yl)pyrrolidin-1-yl)-1-cyclohexyl-2-oxoethyl)amino)-1-oxopropan-2-yl)(methyl)carbamate

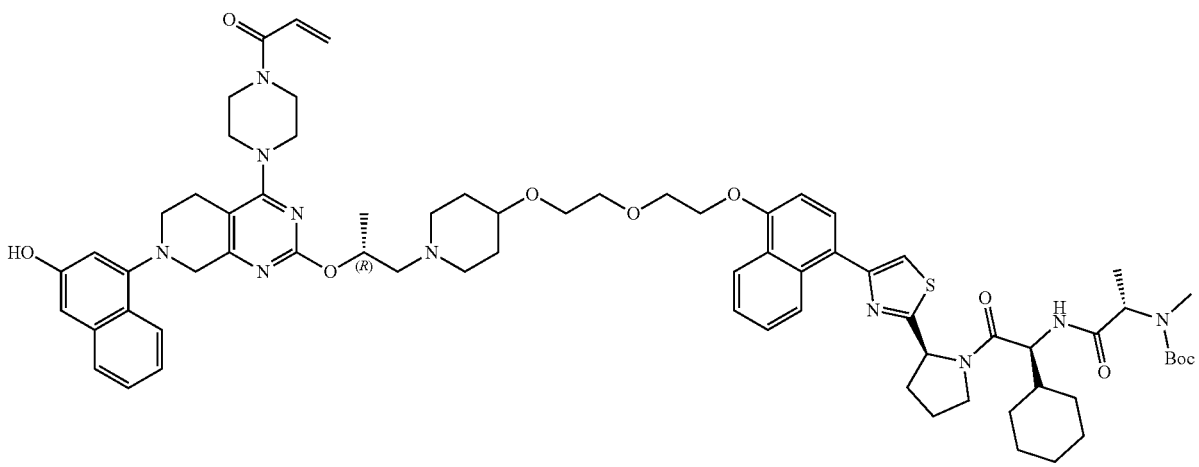

847

To a solution of tert-butyl N-[(1S)-2-[[(1S)-1-cyclohexyl-2-oxo-2-[(2S)-2-[4-[4-[2-[2-(4-piperidyloxy)ethoxy]ethoxy]-1-naphthyl]thiazol-2-yl]pyrrolidin-1-yl]ethyl]amino]-1-methyl-2-oxo-ethyl]-N-methyl-carbamate (81 mg, 0.1 mmol, 1 eq) in methanol (3 mL) was added sodium acetate (17 mg, 0.21 mmol, 2 eq), then borane; 2-methylpyridine (44 mg, 0.41 mmol, 4 eq) in dichloromethane (1 mL) was added at 0° C. for 0.5 hour. (2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propanal (50 mg, 0.1 mmol, 1 eq) and acetic acid (0.62 mg, 0.01 mmol, 0.1 eq) was added the mixture was stirred at 25° C. for 11.5 hours. The mixture was concentrated under reduced pressure to give a residue. The residue was purified by prep-TLC (dichloromethane:methanol=10:1). Compound tert-butyl

848

N-[(1S)-2-[[(1S)-1-cyclohexyl-2-[(2S)-2-[4-[4-[2-[2-[[1-[(2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propyl]-4-piperidyl]oxy]ethoxy]ethoxy]-1-naphthyl]thiazol-2-yl]pyrrolidin-1-yl]-2-oxo-ethyl]amino]-1-methyl-2-oxo-ethyl]-N-methyl-carbamate (60 mg, 0.05 mmol, 46% yield) was obtained as a colorless oil.

Step 7: Preparation of (S)—N—((S)-2-((S)-2-(4-(4-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)naphthalen-1-yl)thiazol-2-yl)pyrrolidin-1-yl)-1-cyclohexyl-2-oxoethyl)-2-(methylamino)propanamide

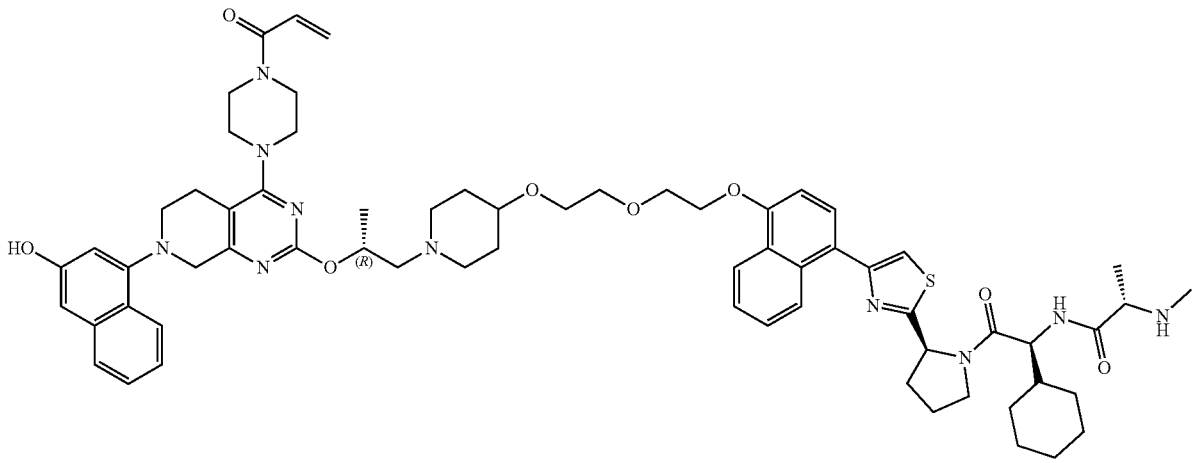

To a solution of tert-butyl N-[(1S)-2-[[(1S)-1-cyclohexyl-2-[(2S)-2-[4-[4-[2-[2-[[1-[(2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propyl]-4-piperidyl]oxy]ethoxy]ethoxy]-1-naphthyl]thiazol-2-yl]pyrrolidin-1-yl]-2-oxo-ethyl]amino]-1-methyl-2-oxo-ethyl]-N-methyl-carbamate (60 mg, 0.05 mol, 1 eq) in dichloromethane (2 mL) was added trifluoroacetic acid (308 mg, 2.70 mmol, 0.2 mL, 56.89 eq), the mixture was stirred at 25° C. for 10 minutes. The reaction was poured into the aqueous sodium bicarbonate solution and the pH was adjusted to about 7-8. The reaction mixture was quenched by water (30 mL), and extracted with ethyl acetate (20 mL×2), the combined organic layers were washed with brine (30 mL), dried over sodium sulfate, filtered and concentrated under reduced pressure to give a residue. The residue was purified by semi-preparative reverse phase HPLC. Compound (2S)—N-[(1S)-1-cyclohexyl-2-[(2S)-2-[4-[4-[2-[2-[[1-[(2R)-2-[[7-(3-hydroxy-1-naphthyl)-4-(4-prop-2-enoylpiperazin-1-yl)-6,8-dihydro-5H-pyrido[3,4-d]pyrimidin-2-yl]oxy]propyl]-4-piperidyl]oxy]ethoxy]ethoxy]-1-naphthyl]thiazol-2-yl]pyrrolidin-1-yl]-2-oxo-ethyl]-2-(methylamino)propanamide (6.6 mg, 0.01 mmol, 11% yield, 95% purity) was obtained as a pink solid. LC/MS (ESI) m/z: 1185.6 [M+23]$^+$; $^1$H-NMR (400 MHz, DMSO-d$_6$) δ 8.33 (s, 1H), 8.28-8.21 (m, 2H), 8.04-7.90 (m, 2H), 7.71-7.63 (m, 2H), 7.60-7.48 (m, 3H), 7.38 (t, J=7.4 Hz, 1H), 7.26 (t, J=7.2 Hz, 1H), 7.02 (d, J=8.1 Hz, 1H), 6.86-6.75 (m, 3H), 6.14 (dd, J=2.4, 16.7 Hz, 1H), 5.71 (d, J=12.7 Hz, 1H), 5.42 (d, J=5.6 Hz, 1H), 5.24-5.14 (m, 1H), 4.57-4.48 (m, 1H), 4.31 (s, 2H), 4.05 (s, 2H), 3.91 (s, 2H), 3.80 (t, J=7.1 Hz, 2H), 3.71-3.63 (m, 6H), 3.56 (d, J=5.4 Hz, 3H), 2.99 (q, J=7.1 Hz, 3H), 2.88 (s, 2H), 2.75-2.65 (m, 3H), 2.35-2.14 (m, 10H), 2.12-2.02 (m, 4H), 1.81-1.53 (m, 10H), 1.36 (s, 2H), 1.23 (d, J=6.1 Hz, 3H), 1.13-1.02 (m, 7H).

Exemplary Synthesis of (2S,4R)-1-((S)-2-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide (Exemplary Compound 500)

Step 1: Preparation of tert-butyl (S)-2-(cyanomethyl)-4-(2-(((2S,4R)-4-(2-(2-(2-ethoxy-2-oxoethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

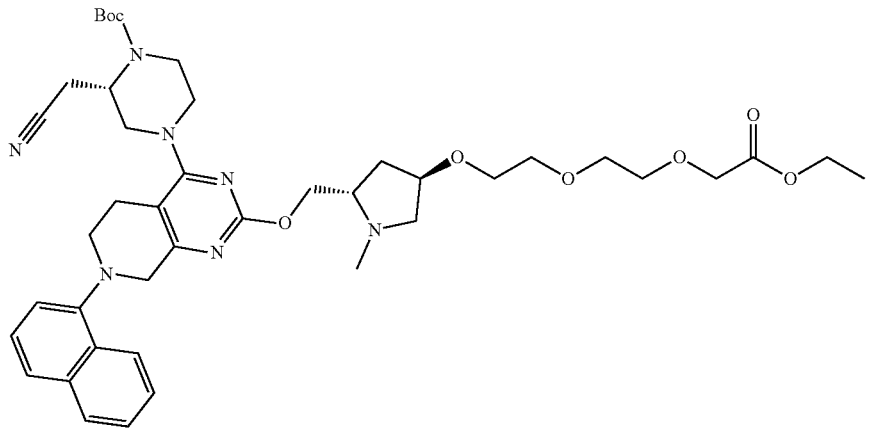 [SMILES: CCOC(=O)COCCOCCO[C@@H]1C[C@@H](COc2nc3c(c(N4CCN(C(=O)OC(C)(C)C)[C@@H](CC#N)C4)n2)CCN(c2cccc4ccccc24)C3)N(C)C1]

To a mixture of tert-butyl (2S)-2-(cyanomethyl)-4-[2-[[(2S,4R)-4-[2-(2-hydroxyethoxy)ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (300 mg, 0.43 mmol, 1 eq) in dichloromethane (10 mL) was added rhodium(ii)acetatedimer (9 mg, 0.042 mmol, 0.1 eq), then ethyl 2-diazoacetate (146 mg, 1.28 mmol, 3 eq) was added at 0° C., then the reaction mixture was stirred at 25° C. for 12 hours. The reaction mixture was concentrated under vacuum. The residue was purified by prep-TLC (Dichloromethane:Methanol=10:1) to get compound tert-butyl (2S)-2-(cyanomethyl)-4-[2-[[(2S,4R)-4-[2-[2-(2-ethoxy-2-oxoethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (111 mg, 0.14 mmol, 33% yield) as a yellow oil. LC/MS (ESI) m/z: 788.3 [M+1]$^+$.

Step 2: Preparation of 2-(2-(2-(((3R,5S)-5-(((4-((S)-4-(tert-butoxycarbonyl)-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)acetic acid

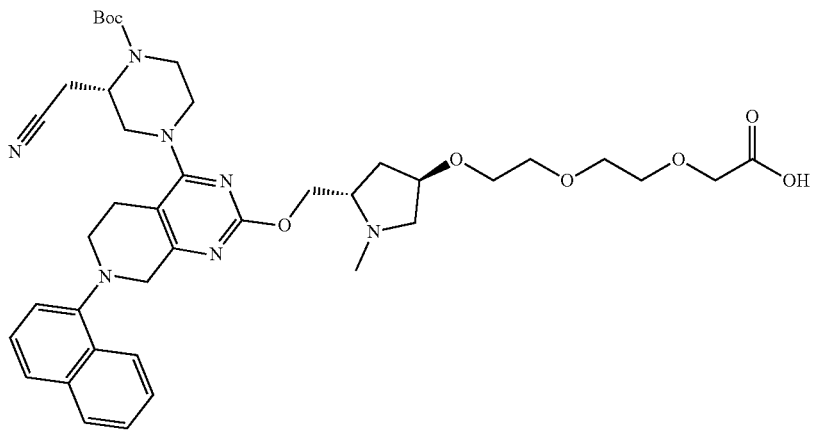 [SMILES: CN1C[C@H](OCCOCCOCC(=O)O)C[C@H]1COc1nc2c(c(N3CCN(C(=O)OC(C)(C)C)[C@@H](CC#N)C3)n1)CCN(c1cccc3ccccc13)C2]

To a mixture of tert-butyl (2S)-2-(cyanomethyl)-4-[2-[[(2S,4R)-4-[2-[2-(2-ethoxy-2-oxo-ethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (110 mg, 0.14 mmol, 1 eq) in water (1 mL) and tetrahydrofuran (1 mL) and methanol (1 mL) was added lithiumhydroxidemonohydrate (126 mg, 3 mmol, 21.49 eq), then the reaction mixture was stirred at 25° C. for 2 hours. Tetrahydrofuran (5 mL) and waster (5 mL) was added, then the reaction mixture was adjust pH to 2-3, the aqueous phase was extracted with dichloromethane and methanol (10:1) (20 mL×4), dried with anhydrous sodium sulfate, filtered and concentrated in vacuum to get compound 2-[2-[2-[(3R,5S)-5-[[4-[(3S)-4-tert-butoxycarbonyl-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]acetic acid (131 mg) as a yellow oil.

Step 3: Preparation of tert-butyl (S)-2-(cyanomethyl)-4-(2-(((2S,4R)-4-(2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

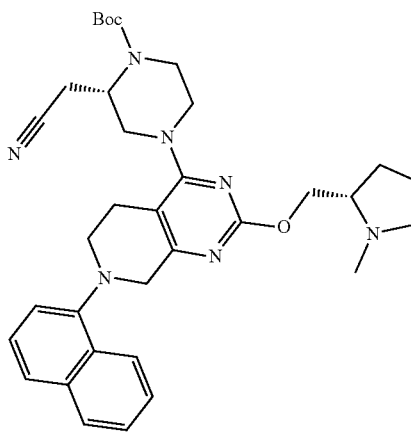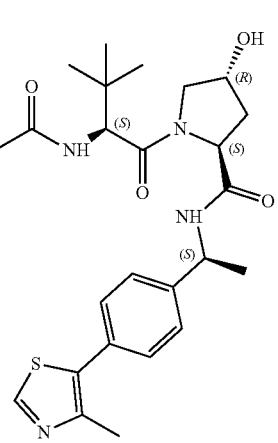

To a mixture of (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (134 mg, 0.28 mmol, 2 eq, hydrochloride) and 2-[2-[2-[(3R,5S)-5-[[4-[(3S)-4-tert-butoxycarbonyl-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]acetic acid (106 mg, 0.14 mmol, 1 eq) in N-methyl-2-pyrrolidone (4 mL) was added 1-hydroxybenzotriazole (28 mg, 0.21 mmol, 1.5 eq), 1-(3-dimethylaminopropyl)-3-ethylcarbodiimide (40 mg, 0.21 mmol, 1.5 eq), N,N-diisopropylethylamine (108 mg, 0.84 mmol, 0.1 mL, 6 eq), then the reaction mixture was stirred at 20° C. for 12 hours. The residue was poured into ice-water (20 mL). The aqueous phase was extracted with ethyl acetate (20 mL*3). The combined organic phase was washed with brine (20 mL), dried with anhydrous sodium sulfate, filtered and concentrated in vacuum. The residue was purified by prep-TLC (Dichloromethane:Methanol=10:1) to get compound tert-butyl (2S)-2-(cyanomethyl)-4-[2-[[(2S,4R)-4-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (90 mg) as a yellow oil. LC/MS (ESI) m/z: 594.0 [M/2+1]$^+$.

Step 4: Preparation of (2S,4R)-1-((S)-2-(2-(2-(2-(((3R,5S)-5-(((4-((S)-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide

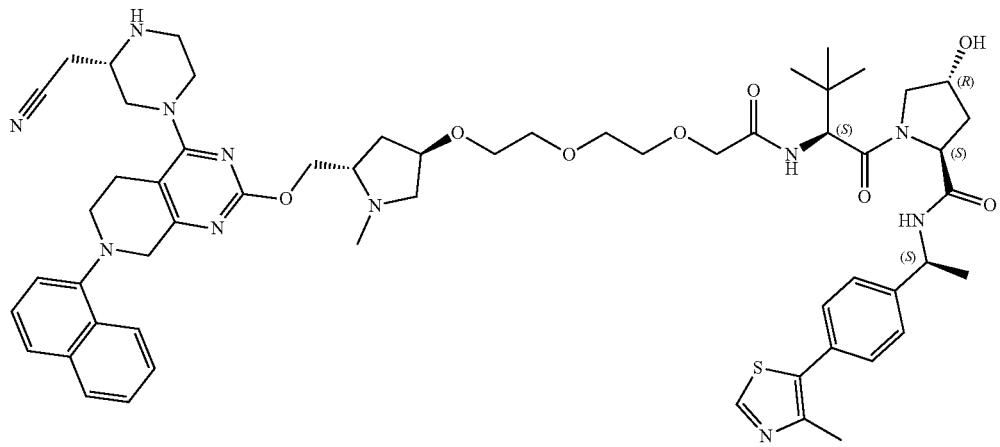

To a solution of tert-butyl (2S)-2-(cyanomethyl)-4-[2-[[(2S,4R)-4-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (35 mg, 0.030 mmol, 1 eq) in dichloromethane (3 mL) was added trifluoroacetic acid (462 mg, 4.05 mmol, 0.3 mL, 137.35 eq). The mixture was stirred at 15° C. for 20 minutes. The reaction mixture was concentrated under vacuum to get compound (2S,4R)-1-[(2S)-2-[[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (35 mg, 0.030 mmol, 99% yield, trifluoroacetate) as a yellow oil. LC/MS (ESI) m/z: 1086.7 [M+1]$^+$.

Step 5: Preparation of (2S,4R)-1-((S)-2-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide

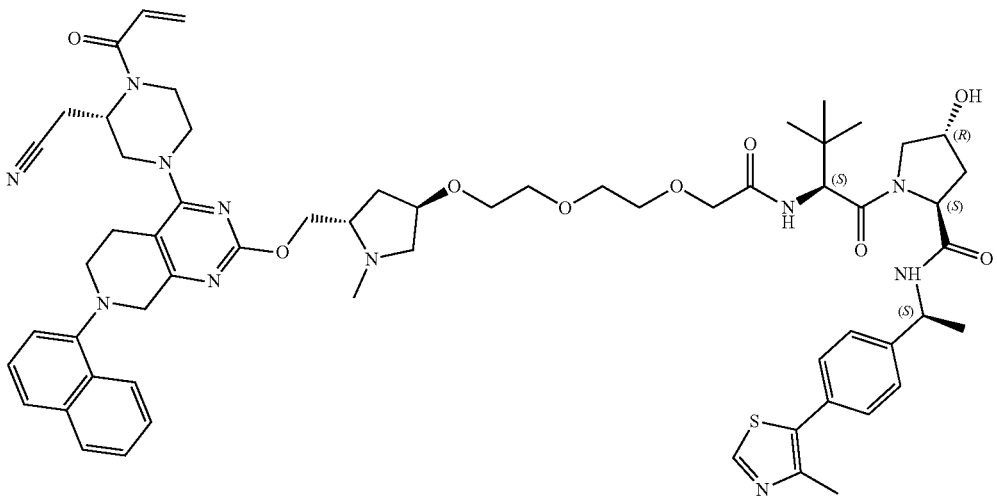

To a mixture of (2S,4R)-1-[(2S)-2-[[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (30 mg, 0.025 mmol, 1 eq, trifluoroacetate) in dichloromethane (5 mL) was added 2,6-lutidine (27 mg, 0.25 mmol, 10 eq), then prop-2-enoyl chloride (2 mg, 0.022 mmol, 0.9 eq) in dichloromethane (1.8 mL) was added at −65° C., then the reaction mixture was stirred at −65° C. for 10 minutes. Water (10 mL) and stirred for 0.5 minutes. The aqueous phase was extracted with dichloromethane (20 mL×2) and concentrated in vacuum. The residue was purified by semi-preparative reverse phase HPLC, then the collected fraction was concentrated to remove most of the acetonitrile. The solution was lyophilized to get compound (2S,4R)-1-[(2S)-2-[[2-[2-[2-[(3R,5S)-5-[[4-[(3S)-3-(cyanomethyl)-4-prop-2-enoyl-piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (9.1 mg, 0.007 mmol, 30% yield, 97% purity, formate) as a white solid. LC/MS (ESI) m/z: 570.8 [M/2+1]$^+$; $^1$H-NMR (400 MHz, DMSO-d$_6$) δ 8.98 (s, 1H), 8.44 (br d, J=7.6 Hz, 1H), 8.30 (s, 1H), 8.22-8.14 (m, 1H), 7.97-7.88 (m, 1H), 7.64 (d, J=8.2 Hz, 1H), 7.59-7.49 (m, 2H), 7.48-7.39 (m, 3H), 7.38-7.33 (m, 2H), 7.22 (d, J=7.2 Hz, 1H), 6.88 (br s, 1H), 6.20 (br d, J=17.4 Hz, 1H), 5.78 (br d, J=11.6 Hz, 1H), 5.06-4.63 (m, 2H), 4.55 (br d, J=9.5 Hz, 1H), 4.45 (br t, J=8.1 Hz, 1H), 4.34-4.22 (m, 2H), 4.17-4.09 (m, 3H), 4.08-3.98 (m, 3H), 3.98-3.91 (m, 2H), 3.61 (br d, J=3.1 Hz, 2H), 3.58 (br d, J=3.9 Hz, 4H), 3.56-3.53 (m, 1H), 3.54 (br s, 2H), 3.53-3.48 (m, 4H), 3.29 (br dd, J=6.2, 9.5 Hz, 2H), 3.24-3.17 (m, 2H), 3.07-2.90 (m, 4H), 2.78-2.63 (m, 2H), 2.45 (s, 3H), 2.34 (s, 3H), 2.19 (br dd, J=6.0, 9.4 Hz, 1H), 2.10-2.00 (m, 1H), 1.92-1.72 (m, 3H), 1.37 (br d, J=7.0 Hz, 3H), 0.94 (s, 9H).

Exemplary Synthesis of 2-((2S)-1-acryloyl-4-(2-(((2S,4R)-4-(2-(2-(2-((2-(2,6-dioxopiperidin-3-yl)-1,3-dioxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (Exemplary Compound 504)

Step 1: Preparation of tert-butyl (2S)-2-(cyanomethyl)-4-(2-(((2S,4R)-4-(2-(2-(2-((2-(2,6-dioxopiperidin-3-yl)-1,3-dioxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

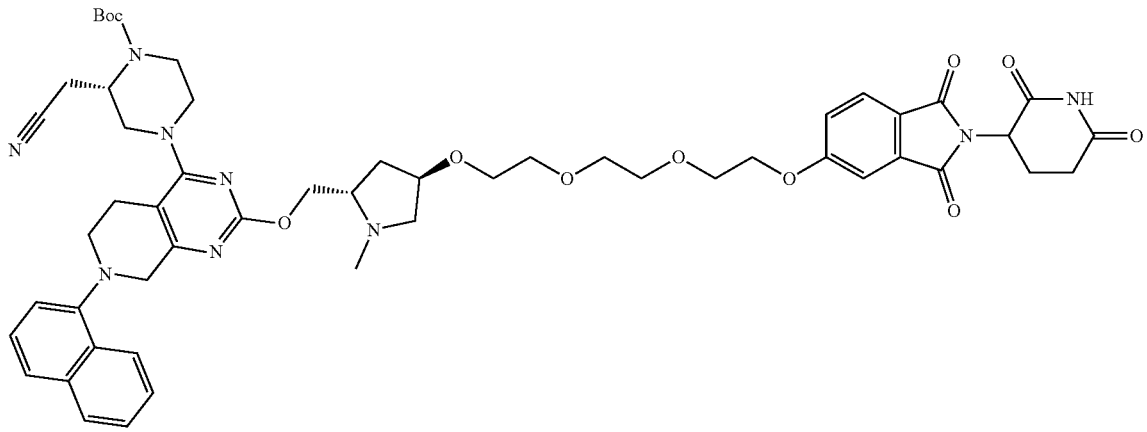 [SMILES: CN1C[C@H](OCCOCCOCCOc2ccc3c(c2)C(=O)N(C2CCC(=O)NC2=O)C3=O)C[C@H]1COc1nc2c(c(N3CCN(C(=O)OC(C)(C)C)[C@@H](CC#N)C3)n1)CCN(c1cccc3ccccc13)C2]

To a mixture of tert-butyl (2S)-2-(cyanomethyl)-4-[2-[[[(2S,4R)-1-methyl-4-[2-[2-[2-(p-tolylsulfonyloxy)ethoxy]ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (100 mg, 0.11 mmol, 1 eq) and 2-(2,6-dioxo-3-piperidyl)-5-hydroxy-isoindoline-1,3-dione (152 mg, 0.56 mmol, 5 eq) in N,N-dimethylformamide (4 mL) was added potassium carbonate (46 mg, 0.33 mmol, 3 eq), then the reaction mixture was stirred at 50° C. for 12 hours. The residue was poured into 0.1 M hydrochloric acid (30 mL). The aqueous phase was extracted with ethyl acetate (50 mL×4), dried with anhydrous sodium sulfate, filtered and concentrated in vacuum. The residue was purified by prep-TLC (Petroleum ether:Ethyl acetate=0:1). Compound tert-butyl (2S)-2-(cyanomethyl)-4-[2-[[[(2S,4R)-4-[2-[2-[2-[2-(2,6-dioxo-3-piperidyl)-1,3-dioxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (70 mg, 0.07 mmol, 63% yield) was obtained as a yellow oil. LC/MS (ESI) m/z: 1002.6 [M+1].

Step 2: Preparation of 2-((2S)-4-(2-(((2S,4R)-4-(2-(2-(2-((2-(2,6-dioxopiperidin-3-yl)-1,3-dioxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

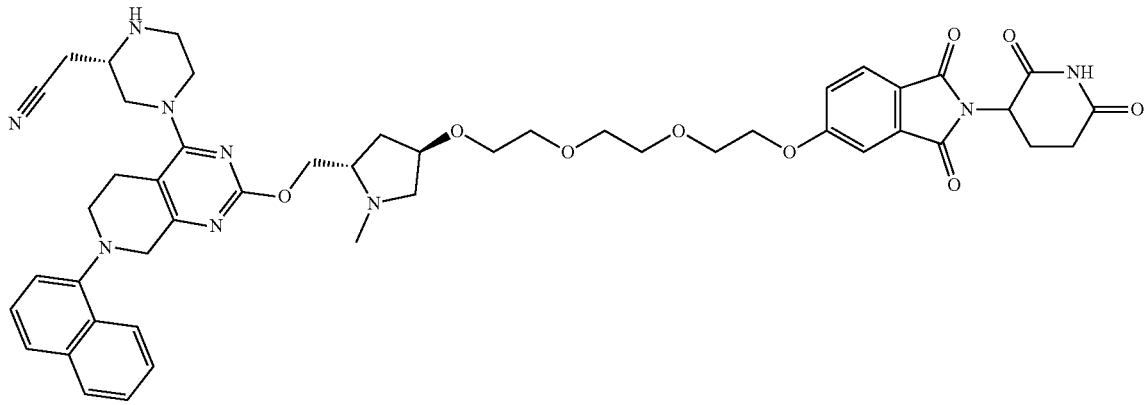 [SMILES: CN1C[C@H](OCCOCCOCCOc2ccc3c(c2)C(=O)N(C2CCC(=O)NC2=O)C3=O)C[C@H]1COc1nc2c(c(N3CCN[C@@H](CC#N)C3)n1)CCN(c1cccc3ccccc13)C2]

To a mixture of tert-butyl (2S)-2-(cyanomethyl)-4-[2-[[(2S,4R)-4-[2-[2-[2-[2-(2,6-dioxo-3-piperidyl)-1,3-dioxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (35 mg, 0.035 mmol, 1 eq) in dichloromethane (5 mL) was added trifluoroacetic acid (1.54 g, 13.51 mmol, 1 mL, 386.70 eq), then the reaction mixture was stirred at 20° C. for 1 hour. The reaction mixture was concentrated under vacuum. Compound 2-[(2S)-4-[2-[[(2S,4R)-4-[2-[2-[2-[2-(2,6-dioxo-3-piperidyl)-1,3-dioxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (35 mg, 0.034 mmol, 99% yield, trifluoroacetate) was obtained as a yellow oil.

Step 3: Preparation of 2-((2S)-1-acryloyl-4-(2-(((2S,4R)-4-(2-(2-(2-((2-(2,6-dioxopiperidin-3-yl)-1,3-dioxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

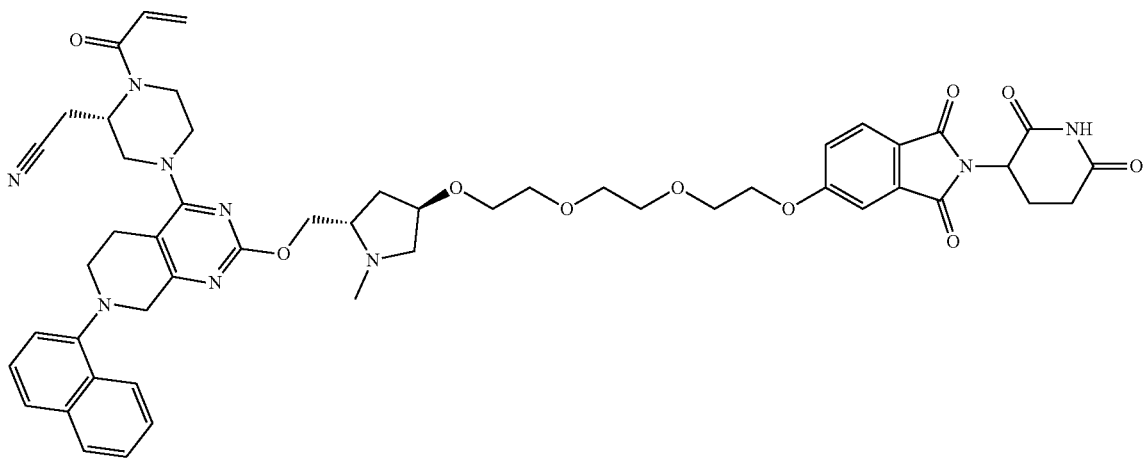 [SMILES: C=CC(=O)N1CCN(c2nc(OC[C@@H]3C[C@@H](OCCOCCOCCOc4ccc5c(c4)C(=O)N(C4CCC(=O)NC4=O)C5=O)CN3C)nc3c2CCN(c2cccc4ccccc24)C3)C[C@@H]1CC#N]

To a mixture of 2-[(2S)-4-[2-[[(2S,4R)-4-[2-[2-[2-[2-(2,6-dioxo-3-piperidyl)-1,3-dioxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (35 mg, 0.034 mmol, 1 eq, trifluoroacetate) in dichloromethane (4 mL) was added 2,6-lutidine (37 mg, 0.34 mmol, 10 eq), then prop-2-enoyl chloride (3 mg, 0.03 mmol, 0.85 eq) in dichloromethane (2 mL) was added at −65° C. for 10 minutes. Water (10 mL) and stirred for 0.5 minute. The aqueous phase was extracted with dichloromethane (20 mL×2), then concentrated in vacuum. The residue was purified by semi-preparative reverse phase HPLC. Compound 2-[(2S)-4-[2-[[(2S,4R)-4-[2-[2-[2-[2-(2,6-dioxo-3-piperidyl)-1,3-dioxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (6.2 mg, 0.006 mmol, 18% yield, 95% purity) was obtained as an off-white solid. LC/MS (ESI) m/z: 956.5 [M+1]$^+$; $^1$H-NMR (400 MHz, DMSO-d$_6$) δ 11.10 (br s, 1H), 8.37-8.06 (m, 2H), 7.96-7.77 (m, 2H), 7.63 (br s, 1H), 7.58-7.42 (m, 4H), 7.36 (br s, 1H), 7.22 (br s, 1H), 6.86 (br s, 1H), 6.19 (br d, J=17.0 Hz, 1H), 5.78 (brd, J=8.8 Hz, 1H), 5.11 (brd, J=7.9 Hz, 1H), 5.03-4.71 (m, 1H), 4.41 (br s, 1H), 4.34-4.23 (m, 3H), 4.13 (br s, 4H), 4.02 (br d, J=12.3 Hz, 4H), 3.78 (br s, 4H), 3.59 (br s, 2H), 3.54 (br s, 2H), 3.49 (br s, 4H), 3.30-3.16 (m, 1H), 3.06-2.86 (m, 6H), 2.67 (br s, 1H), 2.32 (br s, 3H), 2.16 (br s, 1H), 2.04 (br s, 1H), 1.85 (br s, 3H).

Exemplary Synthesis of (2S,4R)—N-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide (Exemplary Compound 506)

Step 1: Preparation of (2S,4R)—N-(2-(2-(2-(((3R,5S)-5-(((4-((S)-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide

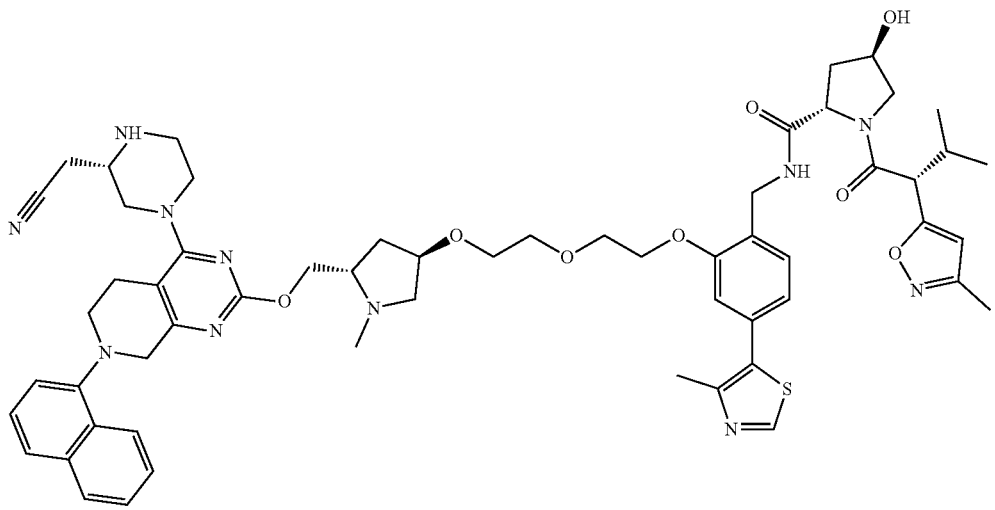 [SMILES: Cc1cc([C@H](C(=O)N2C[C@H](O)C[C@H]2C(=O)NCc2ccc(-c3scnc3C)cc2OCCOCCO[C@@H]2C[C@@H](COc3nc4c(c(N5CCN[C@@H](CC#N)C5)n3)CCN(c3cccc5ccccc35)C4)N(C)C2)C(C)C)on1]

To a solution of tert-butyl (2S)-2-(cyanomethyl)-4-[2-[[(2S,4R)-4-[2-[2-[2-[[[(2S,4R)-4-hydroxy-1-[(2R)-3-methyl-2-(3-methylisoxazol-5-yl)butanoyl]pyrrolidine-2-carbonyl]amino]methyl]-5-(4-methylthiazol-5-yl)phenoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (80 mg, 0.067 mmol, 1 eq) in dichloromethane (8 mL) was added trifluoroacetic acid (3.08 g, 27.0 mmol, 2.0 mL, 400 eq). The mixture was stirred at 20° C. for 2 hours. The reaction mixture was evaporated under vacuum to get the product, (2S,4R)—N-[[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]-4-(4-methylthiazol-5-yl)phenyl]methyl]-4-hydroxy-1-[(2R)-3-methyl-2-(3-methylisoxazol-5-yl)butanoyl]pyrrolidine-2-carboxamide (73 mg) as a yellow oil.

Step 2: Preparation of (2S,4R)—N-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide

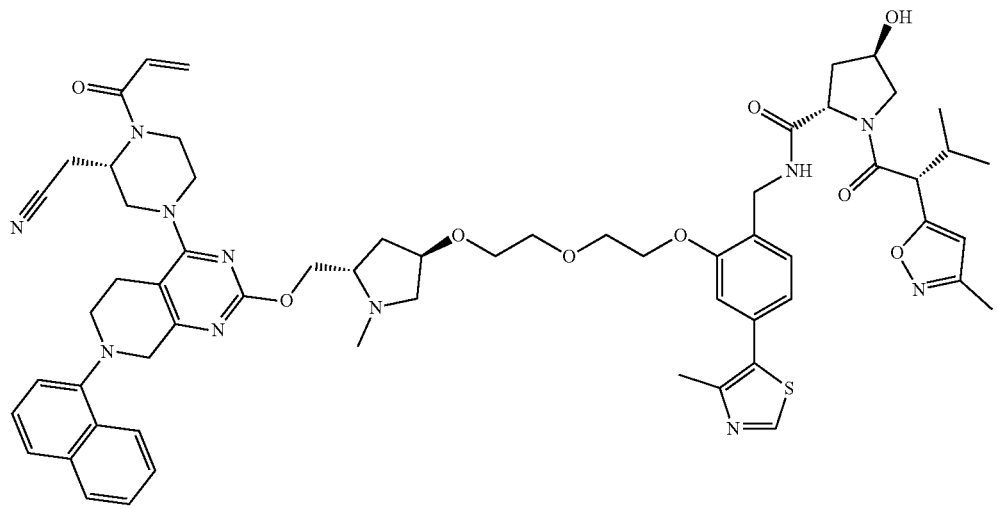 [SMILES: C=CC(=O)N1CCN(c2nc(OC[C@@H]3C[C@@H](OCCOCCOc4cc(-c5scnc5C)ccc4CNC(=O)[C@@H]4C[C@@H](O)CN4C(=O)[C@@H](c4cc(C)no4)C(C)C)CN3C)nc3c2CCN(c2cccc4ccccc24)C3)C[C@@H]1CC#N]

To a solution of (2S,4R)—N-[[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]-4-(4-methylthiazol-5-yl)phenyl]methyl]-4-hydroxy-1-[(2R)-3-methyl-2-(3-methylisoxazol-5-yl)butanoyl]pyrrolidine-2-carboxamide (73 mg, 0.067 mmol, 1 eq) and 2,6-Lutidine (230 mg, 2.15 mmol, 32 eq) in the mixed solvent of dichloromethane (8 mL) and N,N-dimethylformamide (1 mL) was added prop-2-enoyl chloride (6.1 mg, 0.067 mmol, 1 eq) in dichloromethane (0.2 mL) in nitrogen. The mixture was stirred at −65° C. for 10 minutes. The reaction mixture was quenched by water (10 mL) before warmed to 25° C., then extracted by dichloromethane (20 mL×3). The combined organic layers were combined and evaporated under vacuum to get a residue. The residue was purified through Prep-HPLC. The product (2S,4R)—N-[[2-[2-[2-[(3R,5S)-5-[[4-[(3S)-3-(cyanomethyl)-4-prop-2-enoyl-piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]-4-(4-methylthiazol-5-yl)phenyl]methyl]-4-hydroxy-1-[(2R)-3-methyl-2-(3-methylisoxazol-5-yl)butanoyl]pyrrolidine-2-carboxamide (44.1 mg, 0.034 mmol, 50% yield, 96% purity, trifluoroacetate) was obtained as a light yellow solid. LC/MS (ESI) m/z: 1136.3 [M+1]$^+$; $^1$H-NMR (400 MHz, DMSO-d$_6$) δ 8.98 (s, 1H), 8.33-8.30 (m, 1H), 8.19-8.17 (m, 1H), 7.95-7.92 (m, 1H), 7.65 (d, J=8.0 Hz, 1H), 7.55-7.53 (m, 2H), 7.47 (t, J=7.6 Hz, 1H), 7.32-7.21 (m, 2H), 7.08-6.97 (m, 2H), 6.87 (s, 1H), 6.22-6.18 (m, 2H), 5.81-5.78 (m, 1H), 5.00-4.76 (m, 1H), 4.62-4.59 (m, 1H), 4.48-4.41 (m, 3H), 4.33-4.08 (m, 12H), 3.98-3.88 (m, 1H), 3.85 (d, J=8.4 Hz, 1H), 3.83-3.71 (m, 3H), 3.65-3.59 (m, 6H), 3.55-3.44 (m, 1H), 3.41-3.33 (m, 1H), 3.31-3.14 (m, 4H), 3.08-3.29 (m, 7H), 2.46-2.44 (m, 3H), 2.37-2.23 (m, 2H), 2.21-2.13 (m, 3H), 2.08-1.86 (m, 2H), 1.00-0.55 (m, 6H).

Exemplary Synthesis of (2S,4R)—N-(2-(2-(2-(((3R, 5S)-5-(((4-((S)-4-acryloyl-3-(cyanomethyl)piper-azin-1-yl)-7-(naphthalen-1-yl)-5,6,7,8-tetrahydro-pyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide (Exemplary Compound 507)

Step 1: Preparation of (2S,4R)—N-(2-(2-(2-(((3R, 5S)-5-(((4-((S)-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide

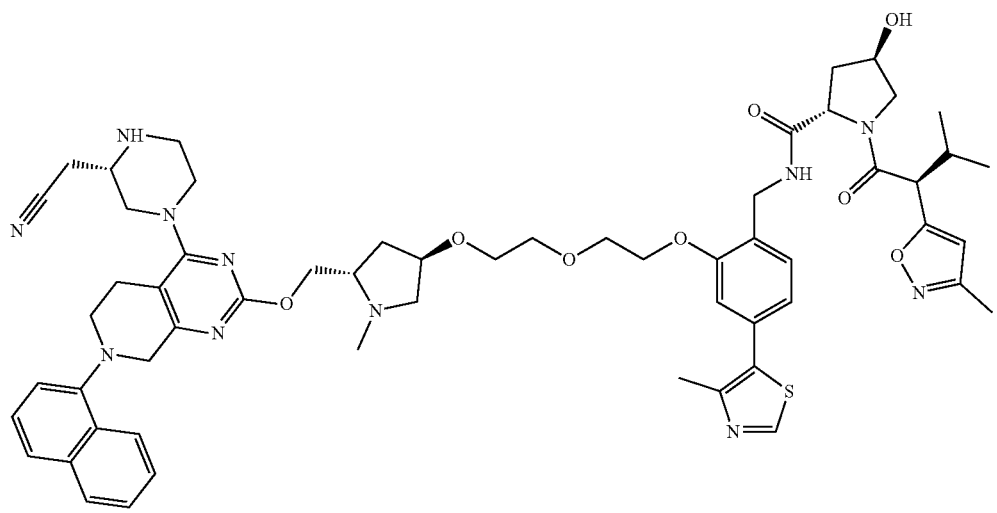 [SMILES: Cc1cc([C@@H](C(=O)N2C[C@H](O)C[C@H]2C(=O)NCc2ccc(-c3scnc3C)cc2OCCOCCO[C@@H]2C[C@@H](COc3nc4c(c(N5CCN[C@@H](CC#N)C5)n3)CCN(c3cccc5ccccc35)C4)N(C)C2)C(C)C)on1]

To a solution of tert-butyl (2S)-2-(cyanomethyl)-4-[2-[[[(2S,4R)-4-[2-[2-[2-[[[(2S,4R)-4-hydroxy-1-[(2S)-3-methyl-2-(3-methylisoxazol-5-yl)butanoyl]pyrrolidine-2-carbonyl]amino]methyl]-5-(4-methylthiazol-5-yl)phenoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (60 mg, 0.051 mmol, 1 eq) in dichloromethane (6 mL) was added trifluoroacetic acid (2.31 g, 20.26 mmol, 1.5 mL, 400 eq). The mixture was stirred at 20° C. for 2 hours. The mixture was evaporated under vacuum to get the product (2S,4R)—N-[[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]-4-(4-methylthiazol-5-yl)phenyl]methyl]-4-hydroxy-1-[(2S)-3-methyl-2-(3-methylisoxazol-5-yl)butanoyl]pyrrolidine-2-carboxamide (50 mg) as a light yellow oil.

Step 2: Preparation of (2S,4R)—N-(2-(2-(2-(((3R, 5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-1-((S)-3-methyl-2-(3-methylisoxazol-5-yl)butanoyl) pyrrolidine-2-carboxamide

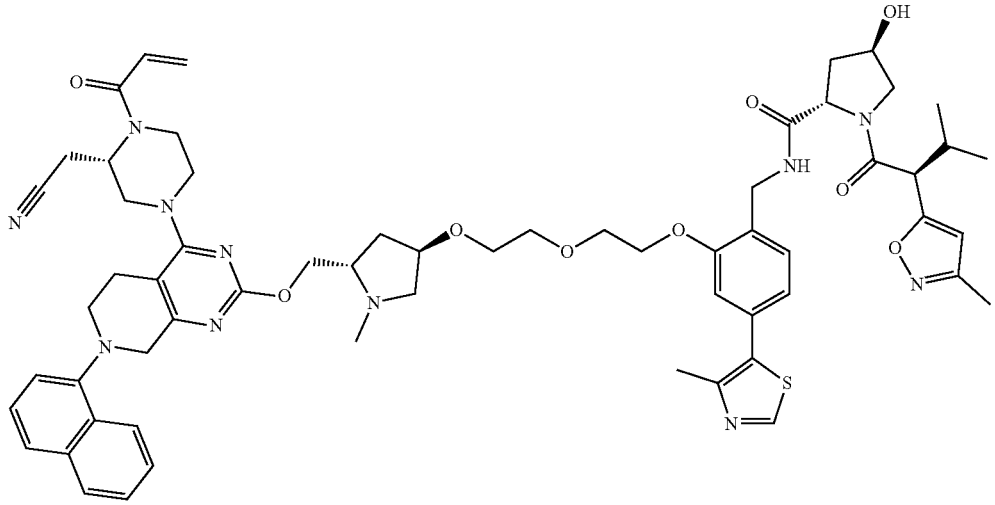 [SMILES: C=CC(=O)N1CCN(c2nc(OC[C@@H]3C[C@@H](OCCOCCOc4cc(-c5scnc5C)ccc4CNC(=O)[C@@H]4C[C@@H](O)CN4C(=O)[C@H](c4cc(C)no4)C(C)C)CN3C)nc3c2CCN(c2cccc4ccccc24)C3)C[C@@H]1CC#N]

To a solution of (2S,4R)—N-[[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]-4-(4-methylthiazol-5-yl)phenyl]methyl]-4-hydroxy-1-[(2S)-3-methyl-2-(3-methylisoxazol-5-yl)butanoyl]pyrrolidine-2-carboxamide (50 mg, 0.046 mmol, 1 eq) and 2,6-Lutidine (184 mg, 1.72 mmol, 0.2 mL, 37 eq) in the mixed solvent of dichloromethane (4 mL) and N,N-dimethylformamide (0.5 mL) was added prop-2-enoyl chloride (3.7 mg, 0.042 mmol, 0.9 eq) in dichloromethane (0.2 mL) in nitrogen. The mixture was stirred at −65° C. for 10 minutes. The mixture was quenched by water (10 mL) and extracted by dichloromethane (20 mL×3). The organic layers were combined and evaporated under vacuum to get a residue (50 mg). The residue was purified through Prep-HPLC. The product (2S,4R)—N-[[2-[2-[2-[(3R,5S)-5-[[4-[(3S)-3-(cyanomethyl)-4-prop-2-enoyl-piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]-4-(4-methylthiazol-5-yl) phenyl]methyl]-4-hydroxy-1-[(2S)-3-methyl-2-(3-methylisoxazol-5-yl)butanoyl]pyrrolidine-2-carboxamide (28.5 mg, 0.024 mmol, 52% yield, 96% purity, trifluoroacetate) was obtained as an off-white solid. LC/MS (ESI) m/z: 1136.3 [M+1]$^+$; $^1$H-NMR (400 MHz, DMSO-$d_6$) δ 8.99 (s, 1H), 8.65-8.37 (m, 1H), 8.20-8.17 (m, 1H), 7.95-7.93 (m, 1H), 7.67 (d, J=8.0 Hz, 1H), 7.56-7.54 (m, 2H), 7.47 (t, J=7.6 Hz, 1H), 7.36 (d, J=7.6 Hz, 1H), 7.24-7.22 (m, 1H), 7.06-7.00 (m, 2H), 6.88 (s, 1H), 6.23-6.18 (m, 2H), 5.81-5.78 (m, 1H), 4.99-4.78 (m, 1H), 4.63-4.59 (m, 1H), 4.48-4.17 (m, 12H), 4.10-4.07 (m, 3H), 3.96-3.92 (m, 1H), 3.82-3.73 (m, 5H), 3.67-3.55 (m, 5H), 3.46-3.37 (m, 2H), 3.30-3.17 (m, 4H), 3.00-2.97 (m, 7H), 2.48-2.44 (m, 3H), 2.39-2.22 (m, 2H), 2.21-2.13 (m, 3H), 2.09-1.88 (m, 2H), 0.97-0.93 (m, 3H), 0.79-0.76 (m, 3H).

Exemplary Synthesis of 2-((2S)-1-acryloyl-4-(2-(((2S,4R)-4-(2-(2-(2-(2-((2-(2,6-dioxopiperidin-3-yl)-1,3-dioxoisoindolin-4-yl)amino)ethoxy)ethoxy) ethoxy)ethoxy)-1-methylpyrrolidin-2-yl)methoxy)-7-(naphthalen-1-yl)-5,6,7,8-tetrahydropyrido[3,4-d] pyrimidin-4-yl)piperazin-2-yl)acetonitrile (Exemplary Compound 518)

Step 1: Preparation of tert-butyl (2S,4R)-2-(((tert-butyldimethylsilyl)oxy)methyl)-4-(2-(2-(2-(2-((tetrahydro-2H-pyran-2-yl)oxy)ethoxy)ethoxy)ethoxy) ethoxy)pyrrolidine-1-carboxylate

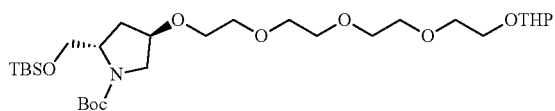

To a solution of tert-butyl (2S,4R)-2-[[tert-butyl(dimethyl)silyl]oxymethyl]-4-hydroxy-pyrrolidine-1-carboxylate (6 g, 18.10 mmol, 1 eq) in dry tetrahydrofuran (80 mL) (dried by sodium and redistilled) was added sodium hydrogen (1.45 g, 36.20 mmol, 60% purity, 2 eq) at 20° C. The reaction mixture was stirred at 20° C. for 30 minutes. Then a solution of 2-[2-[2-(2-tetrahydropyran-2-yloxyethoxy) ethoxy]ethoxy]ethyl 4-methylbenzenesulfonate (8.3 g, 19.19 mmol, 1.06 eq) in tetrahydrofuran (40 mL) was added and the reaction mixture was stirred at 50° C. for another 14 hours. Ethyl acetate (40 mL) was added and the mixture was washed with saturated aqueous ammonium chloride (40 mL). The organic layer was dried over sodium sulfate and then concentrated under vacuum to get the residue. The residue was purified by flash chromatography (silica gel, 0-100% ethyl acetate in petroleum ether) to get tert-butyl (2S,4R)-2-[[tert-butyl(dimethyl) silyl]oxymethyl]-4-[2-[2-[2-(2-tetrahydropyran-2-yloxyethoxy)ethoxy]ethoxy]ethoxy]pyrrolidine-1-carboxylate (3.7 g, 6.25 mmol, 34% yield) as a light yellow oil. $^1$H-NMR (400 MHz, CDCl$_3$) δ 4.67-4.62 (m, 1H), 4.26-4.08 (m, 1H), 3.98 (br s, 1H), 3.90-3.84 (m, 2H), 3.71-3.65 (m, 11H), 3.65-3.61 (m, 3H), 3.61-3.48 (m, 5H), 3.45-3.37 (m, 1H), 2.19 (td, J=5.4, 12.9 Hz, 1H), 2.09-1.94 (m, 1H), 1.89-1.69 (m, 2H), 1.62 (br d, J=4.0 Hz, 1H), 1.66-1.60 (m, 1H), 1.58-1.49 (m, 3H), 1.46 (s, 9H), 1.30-1.24 (m, 1H), 0.88 (s, 9H), 0.07--0.03 (m, 6H).

Step 2: Preparation of tert-butyl (2S,4R)-2-(hydroxymethyl)-4-(2-(2-(2-(2-((tetrahydro-2H-pyran-2-yl)oxy)ethoxy)ethoxy)ethoxy)ethoxy)pyrrolidine-1-carboxylate

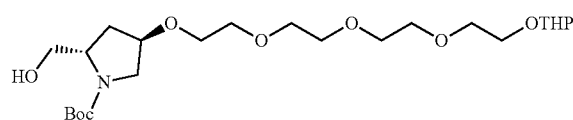

To a solution of tert-butyl (2S,4R)-2-[[tert-butyl(dimethyl)silyl]oxymethyl]-4-[2-[2-[2-(2-tetrahydropyran-2-yloxyethoxy)ethoxy]ethoxy]ethoxy]pyrrolidine-1-carboxylate (3.7 g, 6.25 mmol, 1 eq) in tetrahydrofuran (40 mL) was added tetrabutylammonium fluoride (1 M, 6.25 mL, 1 eq) at 20° C. The reaction mixture was stirred at 20° C. for 6 hour. The reaction mixture was concentrated under vacuum to get the residue. The residue was purified by silica gel column chromatography (30% ethyl acetate in petroleum ether to 100% ethyl acetate) to get tert-butyl (2S,4R)-2-(hydroxymethyl)-4-[2-[2-[2-(2-tetrahydropyran-2-yloxyethoxy)ethoxy]ethoxy]ethoxy]pyrrolidine-1-carboxylate (2.9 g, 6.07 mmol, 97% yield) as a colorless oil. $^1$H-NMR (400 MHz, CDCl$_3$) δ 4.91 (br d, J=8.4 Hz, 1H), 4.67-4.61 (m, 1H), 4.13-3.97 (m, 2H), 3.92-3.84 (m, 2H), 3.71-3.62 (m, 13H), 3.61-3.54 (m, 4H), 3.54-3.48 (m, 1H), 3.41 (br dd, J=4.5, 11.9 Hz, 1H), 2.20-2.11 (m, 1H), 1.89-1.79 (m, 1H), 1.77-1.69 (m, 1H), 1.56 (br s, 1H), 1.64-1.51 (m, 4H), 1.47 (s, 9H).

Step 3: Preparation of ((2S,4R)-1-methyl-4-(2-(2-(2-(2-((tetrahydro-2H-pyran-2-yl)oxy)ethoxy)ethoxy)ethoxy)ethoxy)pyrrolidin-2-yl)methanol

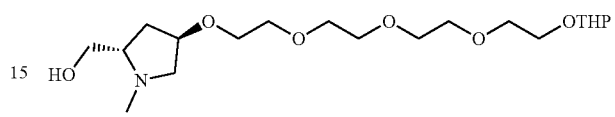

To a solution of tert-butyl (2S,4R)-2-(hydroxymethyl)-4-[2-[2-[2-(2-tetrahydropyran-2-yloxyethoxy)ethoxy]ethoxy]ethoxy]pyrrolidine-1-carboxylate (9.8 g, 20.52 mmol, 1 eq) in tetrahydrofuran (70 mL) was added lithium aluminum hydride (2.34 g, 61.56 mmol, 3 eq) at 20° C. The reaction mixture was stirred at 60° C. for 14 hours. The reaction mixture was cooled to 10° C. and tetrahydrofuran (300 mL) was added. Ice-water (2 mL) was added slowly to quench the reaction with stirring. Datomite (30 g) was added into the suspension and stirred at 20° C. for 10 minutes. The mixture was filtered and filter cake was washed with tetrahydrofuran (50 mL×3). The filtrate was concentrated under vacuum to [(2S,4R)-1-methyl-4-[2-[2-[2-(2-tetrahydropyran-2-yloxyethoxy)ethoxy]ethoxy]ethoxy]pyrrolidin-2-yl]methanol (6.5 g, 16.60 mmol, 80% yield) as a colorless oil. $^1$H-NMR (400 MHz, CDCl$_3$) δ 4.68-4.60 (m, 1H), 4.06-3.96 (m, 1H), 3.92-3.83 (m, 2H), 3.71-3.61 (m, 14H), 3.61-3.54 (m, 2H), 3.54-3.47 (m, 1H), 3.44-3.36 (m, 2H), 2.69-2.59 (m, 1H), 2.39 (dd, J=6.2, 9.7 Hz, 1H), 2.34 (s, 3H), 2.09 (td, J=8.0, 13.4 Hz, 1H), 1.94-1.80 (m, 2H), 1.77-1.68 (m, 1H), 1.66-1.57 (m, 3H), 1.51 (br d, J=3.3 Hz, 1H).

Step 4: Preparation of tert-butyl 4-((S)-4-((benzyloxy)carbonyl)-3-(cyanomethyl)piperazin-1-yl)-2-(((2S,4R)-1-methyl-4-(2-(2-(2-(2-((tetrahydro-2H-pyran-2-yl)oxy)ethoxy)ethoxy)ethoxy)ethoxy)pyrrolidin-2-yl)methoxy)-5,8-dihydropyrido[3,4-d]pyrimidine-7(6H)-carboxylate

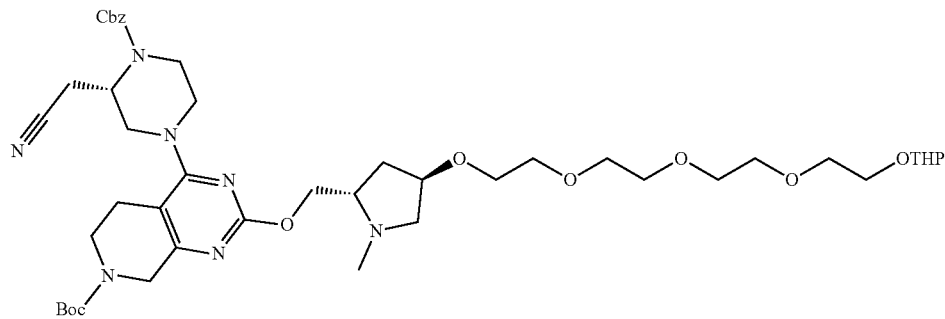

To a solution of [(2S,4R)-1-methyl-4-[2-[2-[2-(2-tetrahydropyran-2-yloxyethoxy)ethoxy]ethoxy]ethoxy]pyrrolidin-2-yl]methanol (1.37 g, 3.50 mmol, 1.32 eq), tert-butyl 4-[(3S)-4-benzyloxycarbonyl-3-(cyanomethyl)piperazin-1-yl]-2-chloro-6,8-dihydro-5H-pyrido[3,4-d]pyrimidine-7-carboxylate (1.4 g, 2.66 mmol, 1 eq) in dioxane (35 mL) were added cesium carbonate (2.60 g, 7.97 mmol, 3 eq) and methanesulfonato(2-dicyclohexylphosphino-2,6-di-i-propoxy-1,1-biphenyl)(2-amino-1,1-biphenyl-2-yl)palladium(ii) (222 mg, 0.26 mmol, 0.1 eq). The reaction mixture was degassed and charged with nitrogen for 3 times and then stirred at 90° C. for 2 hours. Ethyl acetate (50 mL) and saturated aqueous ammonium chloride (30 mL) were added and the mixture was separated. The water layer was extracted with ethyl acetate (40 mL). The combined organic layer was dried over sodium sulfate and then concentrated under vacuum to get the residue. The residue was purified by silica gel column chromatography (50% ethyl acetate in petroleum ether to 100% ethyl acetate then 5% methanol in tetrahydrofuran) to get tert-butyl 4-[(3S)-4-benzyloxycarbonyl-3-(cyanomethyl)piperazin-1-yl]-2-[[(2S,4R)-1-methyl-4-[2-[2-[2-(2-tetrahydropyran-2-yloxyethoxy)ethoxy]ethoxy]ethoxy]pyrrolidin-2-yl]methoxy]-6,8-dihydro-5H-pyrido[3,4-d]pyrimidine-7-carboxylate (1.6 g, 1.81 mmol, 68% yield) as a light brown gum.

Step 5: Preparation of benzyl (S)-2-(cyanomethyl)-4-(2-(((2S,4R)-4-(2-(2-(2-(2-hydroxyethoxy)ethoxy)ethoxy)ethoxy)-1-methylpyrrolidin-2-yl)methoxy)-5,6,7,8-tetrahydropyrido[3,4-d]pyrimidin-4-yl)piperazine-1-carboxylate

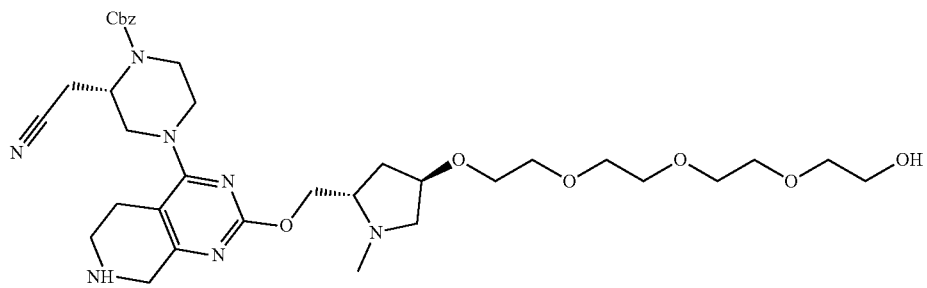 [SMILES: CN1C[C@H](OCCOCCOCCOCCO)C[C@H]1COc1nc2c(c(N3CCN(C(=O)OCc4ccccc4)[C@@H](CC#N)C3)n1)CCNC2]

To a solution of tert-butyl 4-[(3S)-4-benzyloxycarbonyl-3-(cyanomethyl)piperazin-1-yl]-2-[[(2S,4R)-1-methyl-4-[2-[2-[2-(2-tetrahydropyran-2-yloxyethoxy)ethoxy]ethoxy]ethoxy]pyrrolidin-2-yl]methoxy]-6,8-dihydro-5H-pyrido[3,4-d]pyrimidine-7-carboxylate (1.2 g, 1.36 mmol, 1 eq) in dichloromethane (15 mL) was added trifluoroacetic acid (4.62 g, 40.52 mmol, 3.00 mL, 29.78 eq). The reaction mixture was stirred at 20° C. for 2 hours. The reaction solution was poured added into saturated solution of the sodium bicarbonate (30 mL) was added and the pH of the mixture was adjusted to 7 with triethylamine and then concentrated under vacuum to get the residue. This product was dissolved in tetrahydrofuran (8 mL) and then stirred with 1 N sodium hydroxide (5 mL) for 10 minutes. Then water (30 mL) and the mixture was extracted with dichloromethane (25 mL×2). The organic layer was dried over sodium sulfate and then concentrated under vacuum to get the crude product. The crude product was purified by prep-HPLC to get benzyl (2S)-2-(cyanomethyl)-4-[2-[[(2S,4R)-4-[2-[2-[2-(2-hydroxyethoxy)ethoxy]ethoxy]ethoxy]-1-methyl-pyrrolidin-2-yl]methoxy]-5,6,7,8-tetrahydro-pyrido[3,4-d]pyrimidin-4-yl]piperazine-1-carboxylate (660 mg, 0.95 mmol, 69% yield) as a colorless gum. LC/MS (ESI) m/z: 698.4 [M+1]$^+$.

Step 6: Preparation of benzyl (S)-2-(cyanomethyl)-4-(2-(((2S,4R)-4-(2-(2-(2-(2-hydroxyethoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

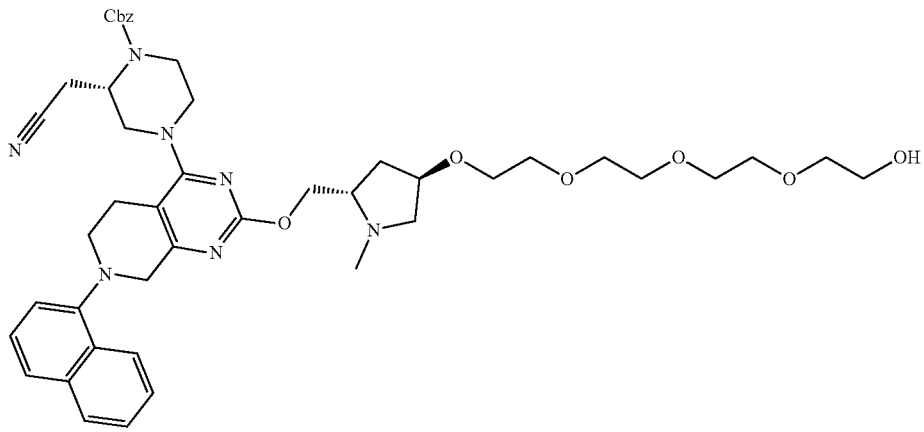 [SMILES: CN1C[C@H](OCCOCCOCCOCCO)C[C@H]1COc1nc2c(c(N3CCN(C(=O)OCc4ccccc4)[C@@H](CC#N)C3)n1)CCN(c1cccc3ccccc13)C2]

A mixture of benzyl (2S)-2-(cyanomethyl)-4-[2-[[(2S,4R)-4-[2-[2-[2-(2-hydroxyethoxy)ethoxy]ethoxy]ethoxy]-1-methyl-pyrrolidin-2-yl]methoxy]-5,6,7,8-tetrahydro-pyrido[3,4-d]pyrimidin-4-yl]piperazine-1-carboxylate (1.6 g, 2.29 mmol, 1 eq), 1-bromonaphthalene (950 mg, 4.59 mmol, 0.64 mL, 2 eq), methanesulfonato(2-dicyclohexylphosphino-2,6-di-i-propoxy-1,1-biphenyl)(2-amino-1,1-biphenyl-2-yl)palladium(ii) (192 mg, 0.23 mmol, 0.1 eq) and cesium carbonate (2.24 g, 6.88 mmol, 3 eq) was added dioxane (30 mL). The reaction mixture was degassed and charged with nitrogen for three times and then stirred at 90° C. for 14 hours. The reaction mixture was concentrated under vacuum to get the residue. Saturated aqueous ammonium chloride (40 mL) and water (20 mL) were added and the mixture was extracted with ethyl acetate (40 mL×2). The organic layer was dried over sodium sulfate and then concentrated under vacuum to get the residue. The product was purified by silica gel column chromatography (30-100% ethyl acetate in petroleum ether then 5% methanol in tetrahydrofuran) to get benzyl (2S)-2-(cyanomethyl)-4-[2-[[(2S,4R)-4-[2-[2-[2-(2-hydroxyethoxy)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (1.05 g, 1.03 mmol, 45% yield, 81% purity) as a light brown gum. LC/MS (ESI) m/z: 824.3 [M+1]$^+$.

Step 7: Preparation of tert-butyl (S)-2-(cyanomethyl)-4-(2-(((2S,4R)-4-(2-(2-(2-(2-hydroxyethoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

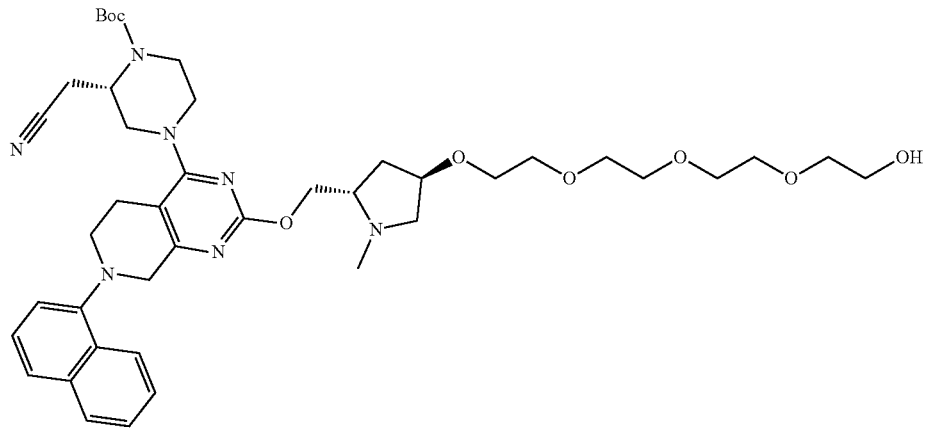 [SMILES: CN1C[C@H](OCCOCCOCCOCCO)C[C@H]1COc1nc2c(c(N3CCN(C(=O)OC(C)(C)C)[C@@H](CC#N)C3)n1)CCN(c1cccc3ccccc13)C2]

To a solution of benzyl (2S)-2-(cyanomethyl)-4-[2-[[(2S,4R)-4-[2-[2-[2-(2-hydroxyethoxy)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (1.17 g, 1.42 mmol, 1 eq), ammonium hydroxide (1.82 g, 17.14 mmol, 2 mL, 33% purity, 12.07 eq) in methanol (30 mL) was added palladium on carbon (150 mg, 5% purity). The reaction mixture was degassed and charged with hydrogen for three times and then stirred at 20° C. with (15 psi) for 4 hours. Then the reaction mixture was stirred at 20° C. with (15 psi) for another 2 h. The reaction mixture was filtered and the filtrate was concentrated under vacuum to get 2-[(2S)-4-[2-[[(2S,4R)-4-[2-[2-[2-(2-hydroxyethoxy)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (980 mg) as a colorless gum. To a solution of 2-[(2S)-4-[2-[[(2S,4R)-4-[2-[2-[2-(2-hydroxyethoxy)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (980 mg, 1.42 mmol, 1 eq) in dichloromethane (20 mL) was added triethylamine (431 mg, 4.26 mmol, 3 eq) and di-tert-butyl dicarbonate (1.55 g, 7.10 mmol, 1.63 mL, 5 eq). The reaction mixture was stirred at 15° C. with for 14 hours. The reaction mixture was filtered and the filtrate was concentrated under vacuum to get the residue. The residue was purified by silica gel (0-5% methanol in dichloromethane) to get tert-butyl (2S)-2-(cyanomethyl)-4-[2-[[(2S,4R)-4-[2-[2-[2-(2-hydroxyethoxy)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (1 g) as a colorless gum. LC/MS (ESI) m/z: 690.3 [M+1]$^+$.

Step 8: Preparation of tert-butyl (S)-2-(cyanomethyl)-4-(2-(((2S,4R)-1-methyl-4-(2-(2-(2-(2-(tosyloxy)ethoxy)ethoxy)ethoxy)ethoxy)pyrrolidin-2-yl)methoxy)-7-(naphthalen-1-yl)-5,6,7,8-tetrahydropyrido[3,4-d]pyrimidin-4-yl)piperazine-1-carboxylate

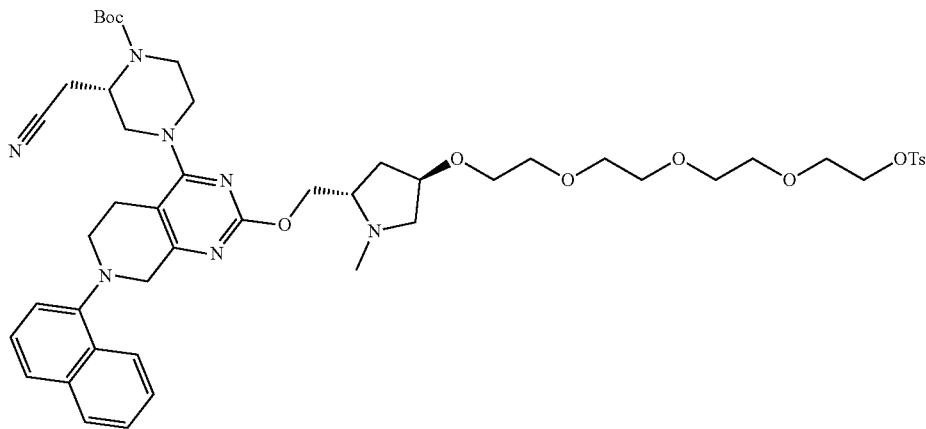 [SMILES: Cc1ccc(S(=O)(=O)OCCOCCOCCOCCO[C@@H]2C[C@@H](COc3nc4c(c(N5CCN(C(=O)OC(C)(C)C)[C@@H](CC#N)C5)n3)CCN(c3cccc5ccccc35)C4)N(C)C2)cc1]

To a solution of tert-butyl (2S)-2-(cyanomethyl)-4-[2-[[(2S,4R)-4-[2-[2-[2-(2-hydroxyethoxy)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (500 mg, 0.63 mmol, 1 eq) in dichloromethane (8 mL) was added 4-methylbenzene-1-sulfonyl chloride (241 mg, 1.27 mmol, 2 eq), triethylamine (192 mg, 1.90 mmol, 3 eq) and N,N-dimethylpyridin-4-amine (15 mg, 0.13 mmol, 0.2 eq). The reaction mixture was stirred at 25° C. with for 14 hours. The reaction mixture was filtered and the filtrate was concentrated under vacuum to get the residue. The residue was purified by prep-TLC (10% methanol in dichloromethane) to get tert-butyl (2S)-2-(cyanomethyl)-4-[2-[[(2S,4R)-1-methyl-4-[2-[2-[2-[$^2$-(p-tolylsulfonyloxy)ethoxy]ethoxy]ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (400 mg, 0.42 mmol, 66% yield) as a colorless gum. LC/MS (ESI) m/z: 944.3 [M+1]$^+$.

Step 9: Preparation of tert-butyl (S)-2-(cyanomethyl)-4-(2-(((2S,4R)-4-(2-(2-(2-(2-(1,3-dioxoisoindolin-2-yl)ethoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

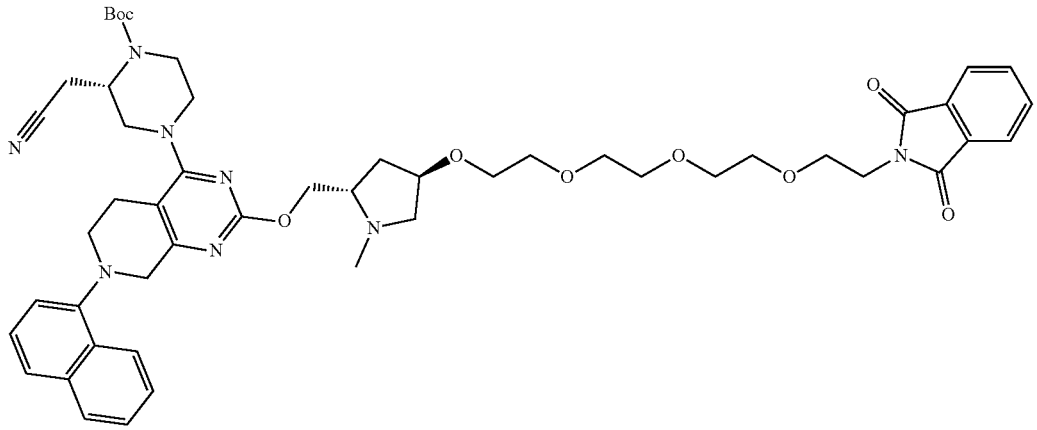 [SMILES: CN1C[C@H](OCCOCCOCCOCCN2C(=O)c3ccccc3C2=O)C[C@H]1COc1nc2c(c(N3CCN(C(=O)OC(C)(C)C)[C@@H](CC#N)C3)n1)CCN(c1cccc3ccccc13)C2]

A mixture of tert-butyl (2S)-2-(cyanomethyl)-4-[2-[[(2S,4R)-1-methyl-4-[2-[2-[2-[2-(ptolylsulfonyloxy)ethoxy]ethoxy]ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (200 mg, 0.21 mmol, 1 eq) and(1,3-dioxoisoindolin-2-yl)potassium (78 mg, 0.42 mmol, 2 eq) in N,N-dimethylformamide (4 mL) was stirred at 80° C. for 2 hours. Ethyl acetate (40 mL) was added and the mixture was washed with water (30 mL). The organic layer was dried over sodium sulfate and then concentrated under vacuum to get the residue. The residue was purified by prep-TLC (10% methanol in dichloromethane) to get tert-butyl (2S)-2-(cyanomethyl)-4-[2-[[(2S,4R)-4-[2-[2-[2-[2-(1,3-dioxo-3a,7a-dihydroisoindol-2-yl)ethoxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (140 mg, 0.15 mmol, 72% yield) as a colorless gum. LC/MS (ESI) m/z: 919.4 [M+1]$^+$.

Step 10: Preparation of tert-butyl (S)-4-(2-(((2S,4R)-4-(2-(2-(2-(2-aminoethoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate

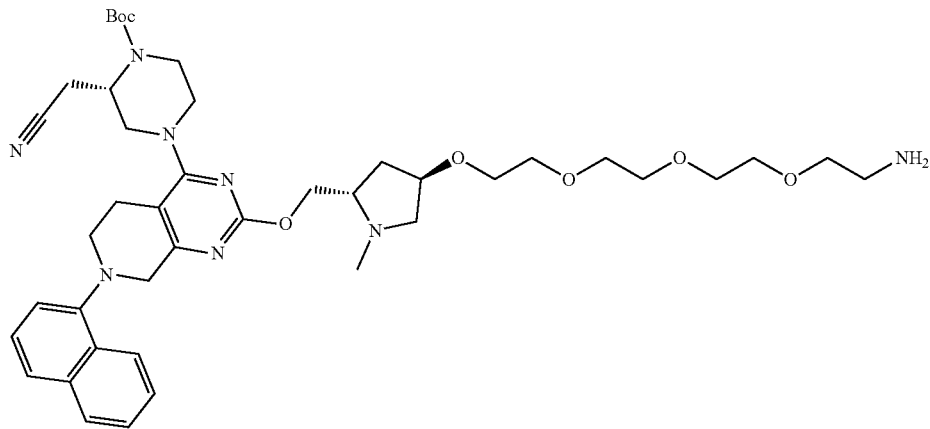 [SMILES: CN1C[C@H](OCCOCCOCCOCCN)C[C@H]1COc1nc2c(c(N3CCN(C(=O)OC(C)(C)C)[C@@H](CC#N)C3)n1)CCN(c1cccc3ccccc13)C2]

To a mixture of tert-butyl (2S)-2-(cyanomethyl)-4-[2-[[(2S,4R)-4-[2-[2-[2-[2-(1,3-dioxo-3a,7a-dihydroisoindol-2-yl)ethoxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (140 mg, 0.15 mmol, 1 eq) in ethanol (2 mL) was added hydrazine hydrate (155 mg, 3.04 mmol, 0.2 mL, 98% purity, 20 eq). The reaction mixture was stirred at 70° C. for 5 hours. The reaction mixture was filtered and the solid was washed with ethanol (30 mL). The filtrate was concentrated under vacuum to get tert-butyl (2S)-4-[2-[[(2S,4R)-4-[2-[2-[2-(2-aminoethoxy)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (140 mg) as a colorless gum.

Step 11: Preparation of tert-butyl (2S)-2-(cyanomethyl)-4-(2-(((2S,4R)-4-(2-(2-(2-(2-((2-(2,6-dioxopiperidin-3-yl)-1,3-dioxoisoindolin-4-yl)amino)ethoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

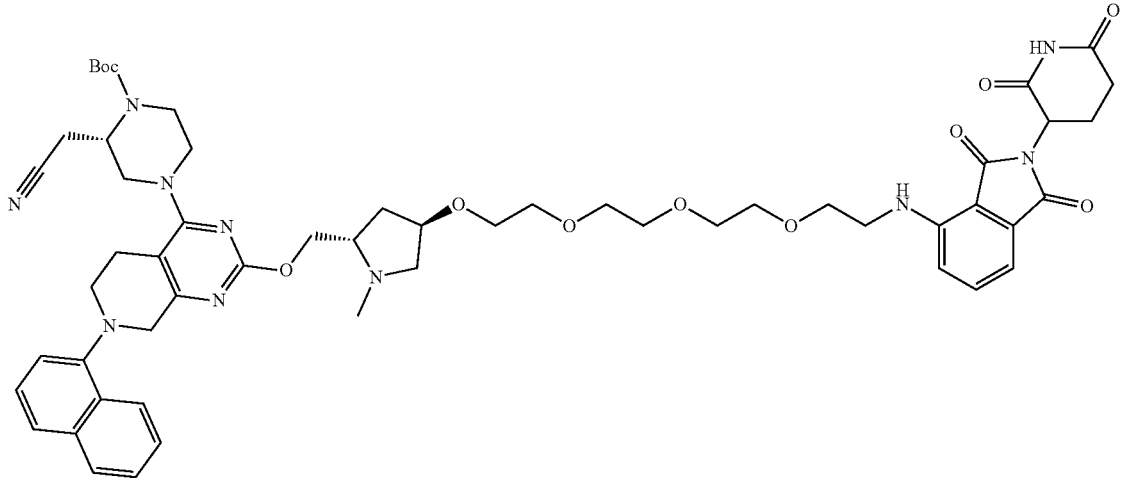 [SMILES: CN1C[C@H](OCCOCCOCCOCCNc2cccc3c2C(=O)N(C2CCC(=O)NC2=O)C3=O)C[C@H]1COc1nc2c(c(N3CCN(C(=O)OC(C)(C)C)[C@@H](CC#N)C3)n1)CCN(c1cccc3ccccc13)C2]

A mixture of tert-butyl (2S)-4-[2-[[(2S,4R)-4-[2-[2-[2-(2-aminoethoxy)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (70 mg, 0.088 mmol, 1 eq), 2-(2,6-dioxo-3-piperidyl)-4-fluoro-isoindoline-1,3-dione (49 mg, 0.18 mmol, 2 eq) and N,N-diisopropylethylamine (46 mg, 0.35 mmol, 4 eq) in dimethyl sulfoxide (2 mL) was heated 90° C. for 3 hours. The reaction mixture was poured into water (25 mL) and then extracted with ethyl acetate (20 mL). The organic layer was washed with brine (20 mL) dried over sodium sulfate and then concentrated under vacuum to get the residue. The residue was purified by prep-TLC (10% methanol in dichloromethane) to get tert-butyl (2S)-2-(cyanomethyl)-4-[2-[[(2S,4R)-4-[2-[2-[2-[2-[[2-(2,6-dioxo-3-piperidyl)-1,3-dioxo-isoindolin-4-yl]amino]ethoxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (25 mg, 0.021 mmol, 24% yield, 88% purity) was obtained as a yellow solid. LC/MS (ESI) m/z: 1045.6 [M+1].

Step 12: Preparation of 2-((2S)-4-(2-(((2S,4R)-4-(2-(2-(2-(2-((2-(2,4-dioxocyclohexyl)-1,3-dioxoisoindolin-4-yl)amino)ethoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

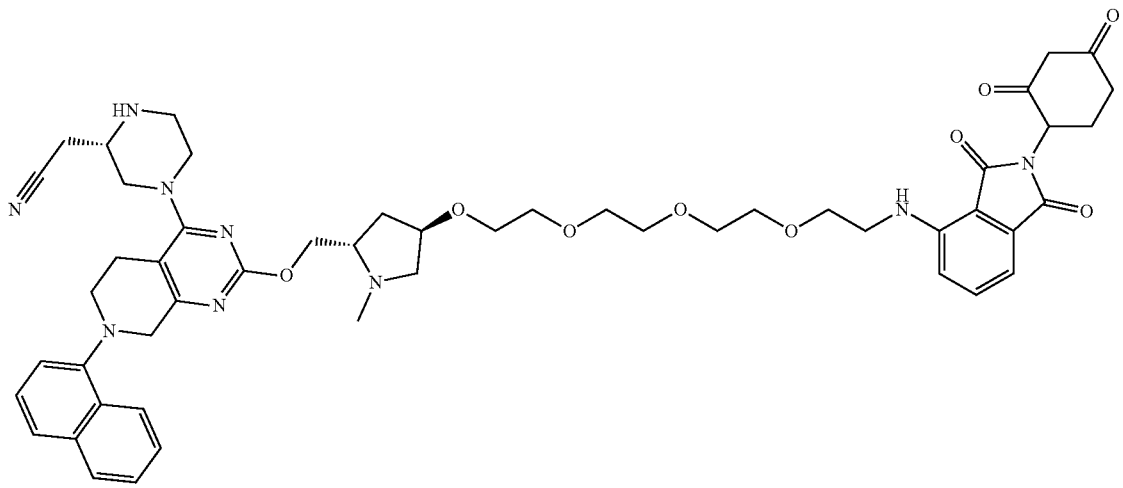 [SMILES: CN1C[C@H](OCCOCCOCCOCCNc2cccc3c2C(=O)N(C2CCC(=O)CC2=O)C3=O)C[C@H]1COc1nc2c(c(N3CCN[C@@H](CC#N)C3)n1)CCN(c1cccc3ccccc13)C2]

To a solution of tert-butyl (2S)-2-(cyanomethyl)-4-[2-[[(2S,4R)-4-[2-[2-[2-[2-[[2-(2,6-dioxo-3-piperidyl)-1,3-dioxo-isoindolin-4-yl]amino]ethoxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (30 mg, 0.028 mmol, 1 eq) in dichloromethane (5 mL) was added trifluoroacetic acid (1.54 g, 13.51 mmol, 1 mL, 470.55 eq). The mixture was stirred at 20° C. for 1 hour. The reaction mixture was concentrated under vacuum to get compound 2-[(2S)-4-[2-[[(2S,4R)-4-[2-[2-[2-[2-[[2-(2,6-dioxo-3-piperidyl)-1,3-dioxo-isoindolin-4-yl]amino] ethoxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (30 mg, 0.028 mmol, 99% yield, trifluoroacetate) as a yellow oil.

Step 13: Preparation of 2-((2S)-1-acryloyl-4-(2-(((2S,4R)-4-(2-(2-(2-(2-((2-(2,6-dioxopiperidin-3-yl)-1,3-dioxoisoindolin-4-yl)amino)ethoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

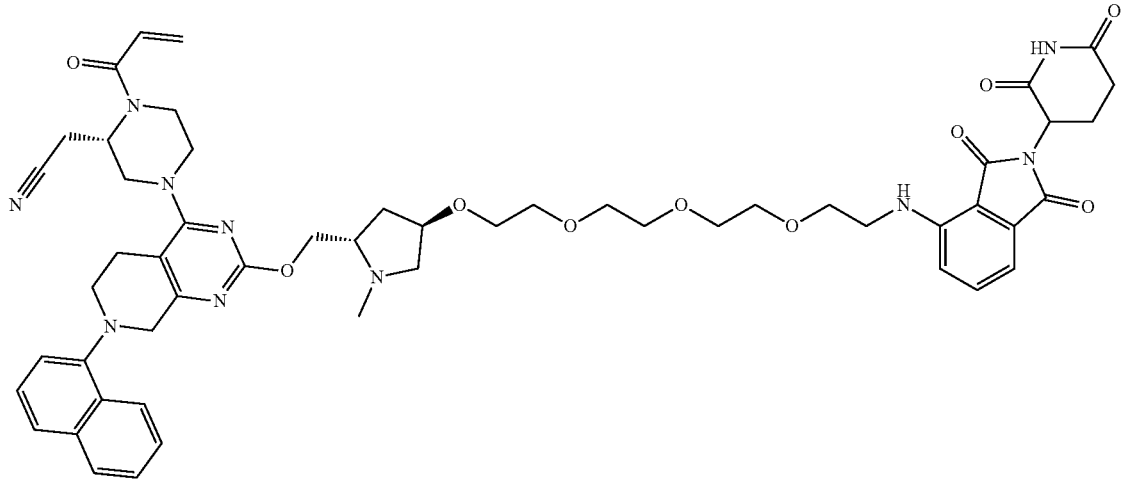 [SMILES: C=CC(=O)N1CCN(c2nc(OC[C@@H]3C[C@@H](OCCOCCOCCOCCNc4cccc5c4C(=O)N(C4CCC(=O)NC4=O)C5=O)CN3C)nc3c2CCN(c2cccc4ccccc24)C3)C[C@@H]1CC#N]

To a mixture of 2-[(2S)-4-[2-[[(2S,4R)-4-[2-[2-[2-[2-[[2-(2,6-dioxo-3-piperidyl)-1,3-dioxo-isoindolin-4-yl]amino]ethoxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (30 mg, 0.028 mmol, 1 eq, trifluoroacetate) in dichloromethane (5 mL) was added 2,6-lutidine (30 mg, 0.28 mmol, 10 eq), then prop-2-enoyl chloride (2 mg, 0.025 mmol, 0.9 eq) in dichloromethane (2 mL) was added at −65° C., then the reaction mixture was stirred at −65° C. for 10 minutes. Water (10 mL) and stirred for 0.5 minutes. The aqueous phase was extracted with dichloromethane (20 mL×2) and concentrated in vacuum. The residue was purified by semi-preparative reverse phase HPLC. Compound 2-[(2S)-4-[2-[[(2S,4R)-4-[2-[2-[2-[2-[[2-(2,6-dioxo-3-piperidyl)-1,3-dioxo-isoindolin-4-yl]amino]ethoxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (15.8 mg, 0.015 mmol, 54% yield, 97% purity) was obtained as a yellow solid. LC/MS (ESI) m/z: 999.5 [M+1]+; 1H-NMR (400 MHz, DMSO-d6) δ 11.09 (s, 1H), 8.22-8.16 (m, 1H), 7.97-7.90 (m, 1H), 7.65 (d, J=8.3 Hz, 1H), 7.61-7.51 (m, 3H), 7.47 (t, J=7.8 Hz, 1H), 7.23 (d, J=7.3 Hz, 1H), 7.14 (d, J=8.7 Hz, 1H), 7.04 (d, J=7.0 Hz, 1H), 6.88 (br s, 1H), 6.60 (br t, J=5.7 Hz, 1H), 6.20 (dd, J=2.0, 16.6 Hz, 1H), 5.85-5.75 (m, 1H), 5.05 (dd, J=5.4, 12.9 Hz, 1H), 5.02-4.73 (m, 1H), 4.26 (br dd, J=4.6, 10.9 Hz, 1H), 4.14 (s, 2H), 4.12-4.07 (m, 1H), 4.06-3.94 (m, 3H), 3.62 (br t, J=5.4 Hz, 2H), 3.57-3.53 (m, 4H), 3.52-3.49 (m, 4H), 3.49-3.47 (m, 2H), 3.46 (br s, 2H), 3.43 (br d, J=6.1 Hz, 2H), 3.27 (br dd, J=6.2, 9.5 Hz, 3H), 3.21-3.17 (m, 2H), 3.10-2.83 (m, 4H), 2.75-2.66 (m, 2H), 2.60 (br d, J=2.7 Hz, 4H), 2.35-2.31 (m, 3H), 2.17 (br dd, J=6.0, 9.5 Hz, 1H), 2.07-1.98 (m, 1H), 1.91-1.78 (m, 2H).

Exemplary Synthesis of 2-((2S)-1-acryloyl-4-(2-(((2S,4R)-4-(2-(2-(2-((2-(2,6-dioxopiperidin-3-yl)-1-oxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (Exemplary Compound 521)

Step 1: Preparation of methyl 4-((tert-butyldimethylsilyl)oxy)-2-methylbenzoate

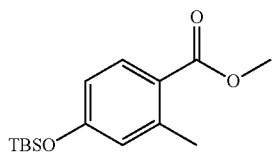 [SMILES: COC(=O)c1ccc(O[Si](C)(C)C(C)(C)C)cc1C]

To a solution of methyl 4-hydroxy-2-methyl-benzoate (5.00 g, 30.09 mmol, 1.00 eq) in dimethylformamide (100 mL) was added imidazole (6.15 g, 90.27 mmol, 3.00 eq). The mixture was stirred at 15° C. for 0.5 h, and then chlorotrimethylsilane (6.80 g, 45.14 mmol, 5.5 mL, 1.50 eq) was added. The resulting mixture was stirred at 15° C. for another 14.5 h. The mixture was poured into saturated brine (300 mL), and then extracted with ethyl acetate (300 mL*2). The combined organic layers were washed with 1 M hydrochloric acid (300 mL*2), brine (300 mL*3), dried over sodium sulfate, filtered and concentrated in vacuum to afford methyl 4-[tert-butyl(dimethyl)silyl]oxy-2-methyl-benzoate (8.00 g, 28.53 mmol, 95% yield) as colorless oil. LC/MS (ESI) m/z: 281.2 [M+1]+.

Step 2: Preparation of methyl 2-(bromomethyl)-4-((tert-butyldimethylsilyl)oxy)benzoate

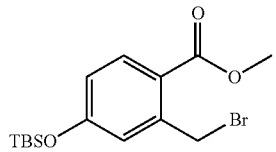 [SMILES: COC(=O)c1ccc(O[Si](C)(C)C(C)(C)C)cc1CBr]

To a solution of methyl 4-[tert-butyl(dimethyl)silyl]oxy-2-methyl-benzoate (3.00 g, 10.70 mmol, 1.00 eq) in carbontetrachloride (40 mL) was added N-bromosuccinimide (2.29 g, 12.84 mmol, 1.20 eq) and 2,2-azobisisobutyronitrile (88 mg, 0.54 mmol, 0.05 eq). The mixture was stirred at 15° C. for 0.5 hour, then heated to 80° C. and stirred at 80° C. for another 2.5 hours. The mixture was poured into water (300 mL), the organic layer was separated. The aqueous layer was extracted with dichloromethane (200 mL*2). The combined organic layers were washed with saturated brine (300 mL*3), dried over sodium sulfate, filtered and concentrated in vacuum to afford methyl 2-(bromomethyl)-4-[tert-butyl(dimethyl)silyl]oxy-benzoate (4.00 g, 8.39 mmol, 78% yield, 75% purity) as a light yellow oil. LC/MS (ESI) m/z: 359.0/361.0 [M+1].

Step 3: Preparation of tert-butyl 5-amino-4-(5-((tert-butyldimethylsilyl)oxy)-1-oxoisoindolin-2-yl)-5-oxopentanoate

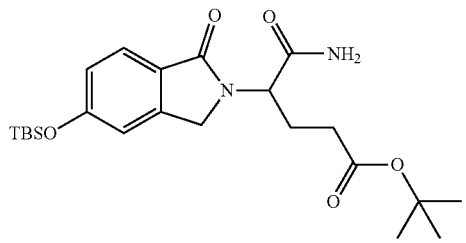 [SMILES: CC(C)(C)OC(=O)CCC(C(N)=O)N1Cc2cc(O[Si](C)(C)C(C)(C)C)ccc2C1=O]

To a mixture of methyl 2-(bromomethyl)-4-[tert-butyl(dimethyl)silyl]oxy-benzoate (9.12 g, 25.38 mmol, 1.00 eq) and diisopropylethylamine (13.12 g, 101.52 mmol, 18 mL, 4.00 eq) in acetonitrile (70 mL) was added tert-butyl 4,5-diamino-5-oxo-pentanoate (5.13 g, 25.38 mmol, 1.00 eq) in one portion at 0° C. under nitrogen atmosphere. The mixture was stirred at 60-80° C. for 16 hours. The mixture was concentrated in vacuum. Then water (50 mL) was added. The aqueous phase was extracted with ethyl acetate (100 mL*3). The combined organic phase was washed with brine (100 mL*2), dried with anhydrous sodium sulfate, filtered and concentrated in vacuum. The residue was purified by silica gel chromatography (Petroleum ether/ethyl acetate=3/1-1/1, then dichloromethane/methanol=10/1). The product tert-butyl 5-amino-4-[5-[tert-butyl (dimethyl)silyl]oxy-1-oxo-isoindolin-2-yl]-5-oxo-pentanoate (3.12 g, 6.68 mmol, 26% yield, 96% purity) was obtained as a colorless oil. LC/MS (ESI) m/z: 449.1 [M+1]+.

Step 4: Preparation of tert-butyl 5-amino-4-(5-hydroxy-1-oxoisoindolin-2-yl)-5-oxopentanoate

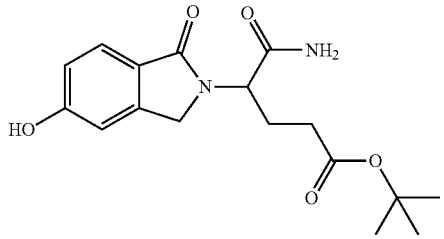 [SMILES: CC(C)(C)OC(=O)CCC(C(N)=O)N1Cc2cc(O)ccc2C1=O]

To a solution of tert-butyl 5-amino-4-[5-[tert-butyl(dimethyl)silyl]oxy-1-oxo-isoindolin-2-yl]-5-oxo-pentanoate (3.12 g, 6.95 mmol, 1.00 eq) in methanol (30 mL) was added tetrabutylammonium fluoride (1 M in tetrahydrofuran, 7 mL, 1.00 eq) in tetrahydrofuran (18 mL). The reaction mixture was stirred at 25° C. for 16 hours. The mixture was concentrated in vacuum. Water (100 mL) was added, the aqueous phase was extracted with dichloromethane (100 mL*2). The combined organic phase was washed with brine (100 mL*3), dried with anhydrous sodium sulfate, filtered and concentrated in vacuum. The residue was purified by flash column chromatography (0-70% ethyl acetate in petroleum ether). The product tert-butyl 5-amino-4-(5-hydroxy-1-oxo-isoindolin-2-yl)-5-oxo-pentanoate (2.50 g, 6.78 mmol, 97% yield, 90% purity) was obtained as a light yellow solid. LC/MS (ESI) m/z: 357.0 [M+23]$^+$.

Step 5: Preparation of tert-butyl (2S)-4-(2-(((2S, 4R)-4-(2-(2-(2-((2-(1-amino-5-(tert-butoxy)-1,5-dioxopentan-2-yl)-1-oxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate

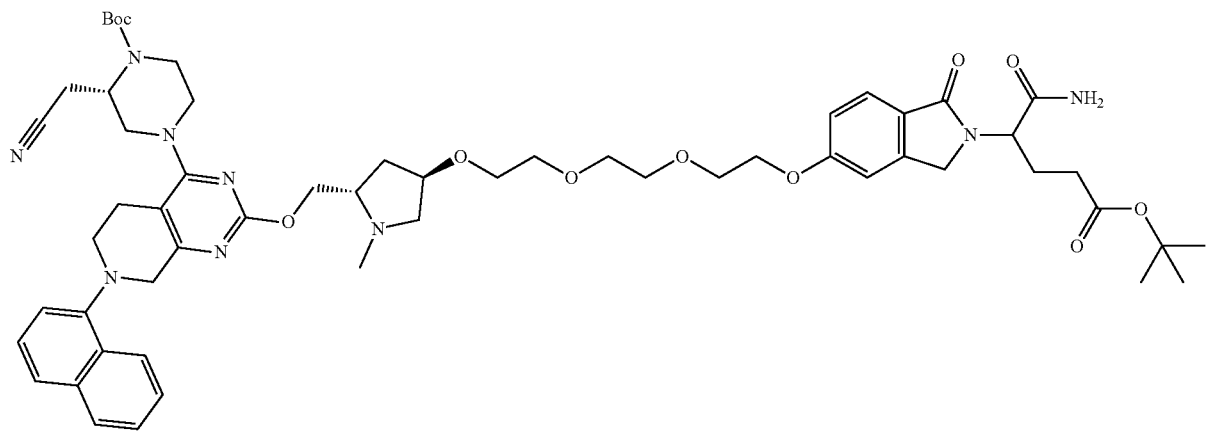 [SMILES: CN1C[C@H](OCCOCCOCCOc2ccc3c(c2)CN(C(CCC(=O)OC(C)(C)C)C(N)=O)C3=O)C[C@H]1COc1nc2c(c(N3CCN(C(=O)OC(C)(C)C)[C@@H](CC#N)C3)n1)CCN(c1cccc3ccccc13)C2]

To a solution of tert-butyl (2S)-2-(cyanomethyl)-4-[2-[[(2S,4R)-1-methyl-4-[2-[2-[2-(p-tolylsulfonyloxy) ethoxy]ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (140 mg, 0.16 mmol, 1 eq) and tert-butyl 5-amino-4-(5-hydroxy-1-oxo-isoindolin-2-yl)-5-oxo-pentanoate (78 mg, 0.23 mmol, 1.5 eq) in acetonitrile (3 mL) was added potassium carbonate (64 mg, 0.47 mmol, 3 eq), the mixture was stirred at 90° C. for 12 hours. The mixture was filtered and the filtrate was concentrated to give crude product, which was purified by prep-TLC (dichloromethane:methanol=10:1) to give tert-butyl (2S)-4-[2-[[(2S,4R)-4-[2-[2-[2-(4-tert-butoxy-1-carbamoyl-4-oxo-butyl)-1-oxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (110 mg, 103.55 umol, 66.6% yield) as a brown oil.

Step 6: Preparation of 2-((2S)-4-(2-(((2S,4R)-4-(2-(2-(2-((2-(2,6-dioxopiperidin-3-yl)-1-oxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

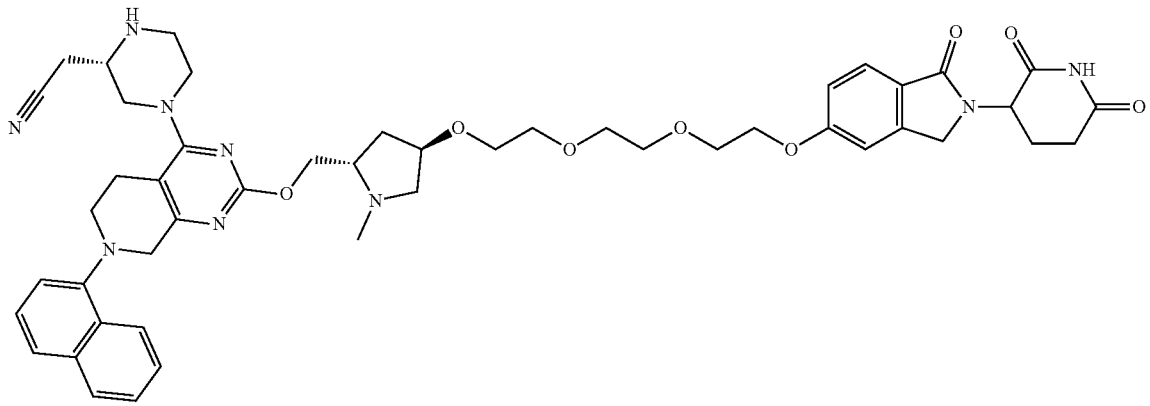 [SMILES: CN1C[C@H](OCCOCCOCCOc2ccc3c(c2)CN(C2CCC(=O)NC2=O)C3=O)C[C@H]1COc1nc2c(c(N3CCN[C@@H](CC#N)C3)n1)CCN(c1cccc3ccccc13)C2]

To a mixture of tert-butyl (2S)-4-[2-[[(2S,4R)-4-[2-[2-[2-[2-(4-tert-butoxy-1-carbamoyl-4-oxo-butyl)-1-oxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (110 mg, 0.1 mmol, 1 eq) in acetonitrile (6 mL) was added benzenesulfonic acid (66 mg, 0.4 mmol, 4 eq) in one portion at 25° C. under nitrogen, the mixture was stirred at 80° C. for 10 hours. The mixture was concentrated in vacuum. The residue was purified by prep-HPLC to afford 2-[(2S)-4-[2-[[(2S,4R)-4-[2-[2-[2-[2-(2,6-dioxo-3-piperidyl)-1-oxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (45 mg, 0.05 mmol, 48% yield) as a yellow oil.

Step 7: Preparation of 2-((2S)-1-acryloyl-4-(2-(((2S,4R)-4-(2-(2-(2-((2-(2,6-dioxopiperidin-3-yl)-1-oxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

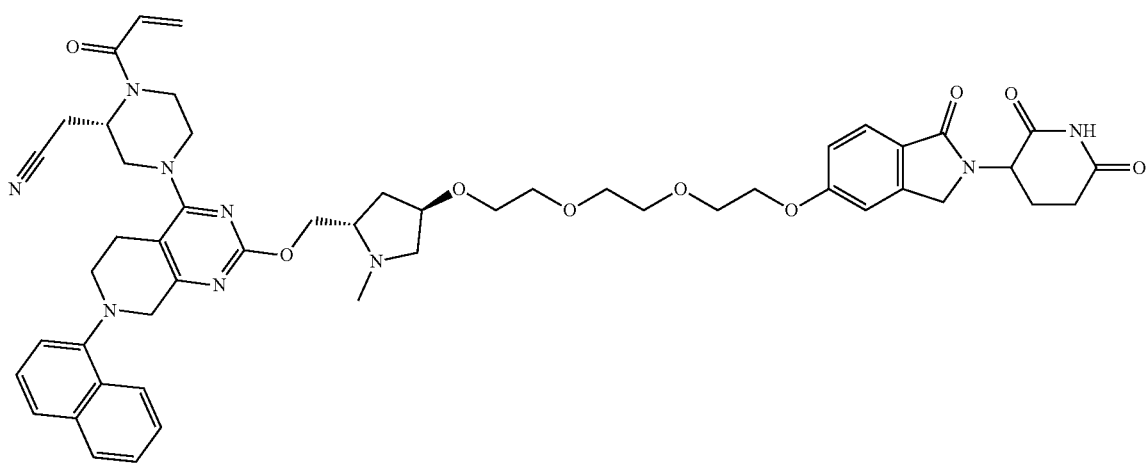 [SMILES: C=CC(=O)N1CCN(c2nc(OC[C@@H]3C[C@@H](OCCOCCOCCOc4ccc5c(c4)CN(C4CCC(=O)NC4=O)C5=O)CN3C)nc3c2CCN(c2cccc4ccccc24)C3)C[C@@H]1CC#N]

To a mixture of 2-[(2S)-4-[2-[[(2S,4R)-4-[2-[2-[2-[2-(2,6-dioxo-3-piperidyl)-1-oxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (45 mg, 0.05 mmol, 1 eq) in dichloromethane (10 mL) was added 2,6-lutidine (54 mg, 0.51 mmol, 10 eq) in one portion at −78° C. under nitrogen, then added prop-2-enoyl chloride (4.1 mg, 0.05 mmol, 0.03 mL, 0.9 eq) in dichloromethane (1 mL) The mixture was stirred at −78° C. for 15 minutes. The mixture was quenched with water (20 mL). The aqueous phase was extracted with ethyl acetate (15 mL×3). The combined organic phase was washed with brine (15 mL), dried with anhydrous sodium sulfate, filtered and concentrated in vacuum. The residue was purified by prep-HPLC to afford 2-[(2S)-4-[2-[[(2S,4R)-4-[2-[2-[2-[2-(2,6-dioxo-3-piperidyl)-1-oxo-isoindolin-5-yl]oxyethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (13 mg, 0.012 mmol, 25% yield, 98% purity, formate) as a white solid. LC/MS (ESI) m/z: 471.8 [M/2+1]$^+$; $^1$H-NMR (400 MHz, DMSO-d$_6$) δ 10.96 (s, 1H), 8.24 (s, 1H), 8.20-8.14 (m, 1H), 7.95-7.89 (m, 1H), 7.66-7.58 (m, 2H), 7.56-7.51 (m, 2H), 7.45-7.3 (m, 1H), 7.25-7.2 (m, 1H), 7.18-7.1 (m, 1H), 7.06-6.9 (m, 1H), 6.88-6.5 (m, 1H), 6.23-6.14 (m, 1H), 5.8-5.5 (m, 1H), 5.06-5.0 (m, 1H), 4.98-4.6 (m, 1H), 4.49-4.32 (m, 2H), 4.27-4.21 (m, 2H), 4.19-4.15 (m, 2H), 4.15-3.93 (m, 8H), 3.79-3.74 (m, 2H), 3.61-3.57 (m, 3H), 3.55-3.53 (m, 3H), 3.51-3.49 (m, 4H), 3.30-3.14 (m, 2H), 3.04-2.84 (m, 4H), 2.75-2.65 (m, 2H), 2.39-2.33 (m, 5H), 2.16-2.1 (m, 1H), 2.00-1.92 (m, 1H), 1.88-1.79 (m, 2H).

Exemplary Synthesis of (S)—N—((S)-2-((S)-2-(4-(4-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethoxy)naphthalen-1-yl)thiazol-2-yl)pyrrolidin-1-yl)-1-cyclohexyl-2-oxoethyl)-2-(methylamino)propanamide (Exemplary Compound 548)

Step 1: Preparation of benzyl (S)-2-(cyanomethyl)-4-(2-(((2S,4R)-1-methyl-4-(2-(2-(2-(tosyloxy)ethoxy)ethoxy)ethoxy)pyrrolidin-2-yl)methoxy)-7-(naphthalen-1-yl)-5,6,7,8-tetrahydropyrido[3,4-d]pyrimidin-4-yl)piperazine-1-carboxylate

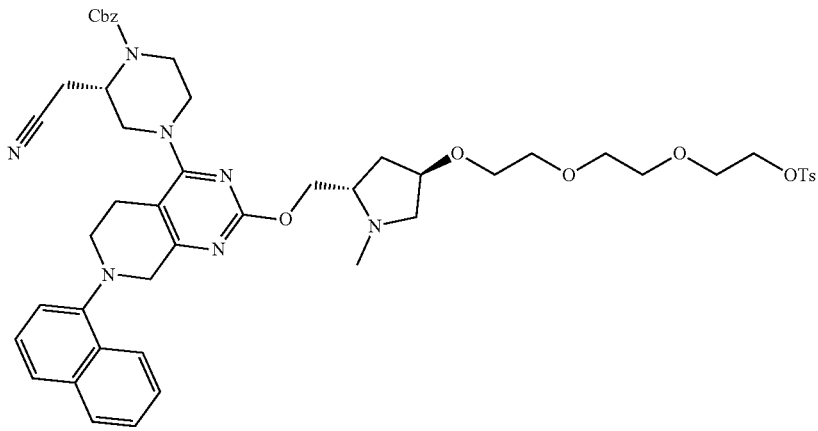 [SMILES: Cc1ccc(S(=O)(=O)OCCOCCOCCO[C@@H]2C[C@@H](COc3nc4c(c(N5CCN(C(=O)OCc6ccccc6)[C@@H](CC#N)C5)n3)CCN(c3cccc5ccccc35)C4)N(C)C2)cc1]

To the mixture of benzyl (2S)-2-(cyanomethyl)-4-[2-[[(2S,4R)-4-[2-[2-(2-hydroxyethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (160 mg, 0.20 mmol, 1 eq) in dichloromethane (2 mL) was added triethylamine (0.1 mL, 3 eq), p-toluenesulfonyl chloride (78 mg, 0.41 mmol, 2 eq) and dimethylaminopyridine (25 mg, 0.20 mmol, 1 eq). Then the reaction mixture was stirred at 15° C. for 12 hours. The reaction mixture was filtered. The filtrate was purified by prep-TLC (Dichloromethane:Methanol=10:1) to get product. Compound benzyl (2S)-2-(cyanomethyl)-4-[2-[[(2S,4R)-1-methyl-4-[2-[2-[2-(ptolylsulfonyloxy)ethoxy]ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (160 mg, 0.17 mmol, 83.5% yield) was obtained as a yellow solid. LC/MS (ESI) m/z: 934.5 [M+1]$^+$.

Step 2: Preparation of benzyl (S)-4-(2-(((2S,4R)-4-(2-(2-(2-((4-(2-((S)-1-((S)-2-((S)-2-((tert-butoxycarbonyl)(methyl)amino)propanamido)-2-cyclohexylacetyl)pyrrolidin-2-yl)thiazol-4-yl)naphthalen-1-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate

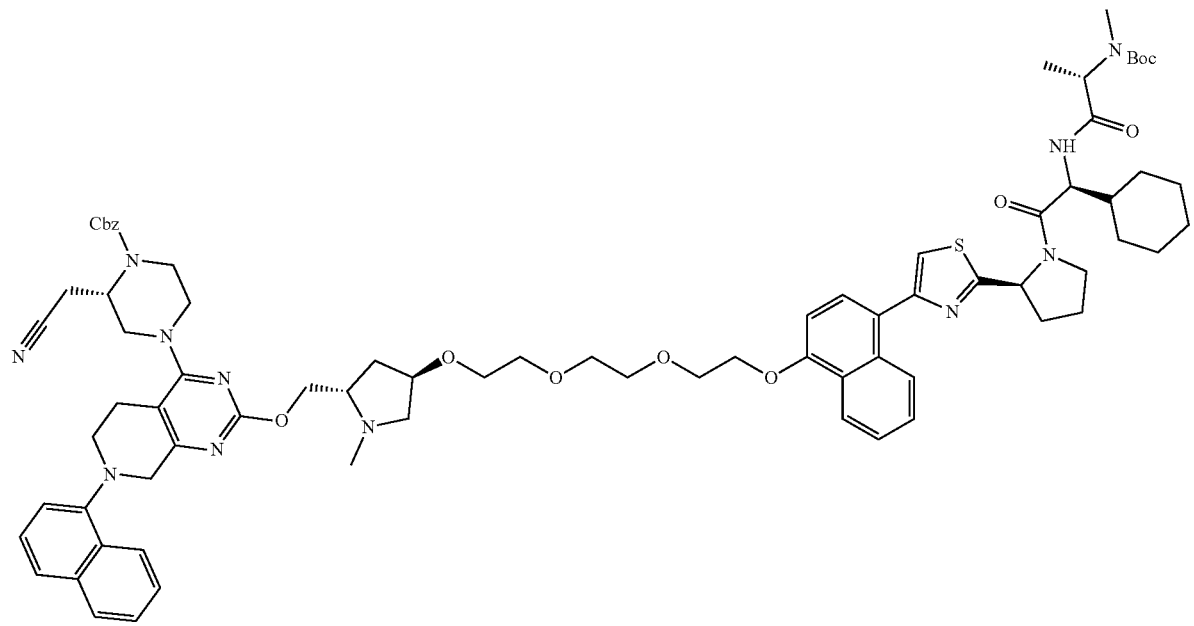 [SMILES: CN[C@@H](C)C(=O)N[C@H](C(=O)N1CCC[C@H]1c1nc(-c2ccc(OCCOCCOCCO[C@@H]3C[C@@H](COc4nc5c(c(N6CCN(C(=O)OCc7ccccc7)[C@@H](CC#N)C6)n4)CCN(c4cccc6ccccc46)C5)N(C)C3)c3ccccc23)cs1)C1CCCCC1]

To the mixture of tert-butyl N-[(1S)-2-[[(1S)-1-cyclohexyl-2-[(2S)-2-[4-(4-hydroxy-1-naphthyl)thiazol-2-yl]pyrrolidin-1-yl]-2-oxo-ethyl]amino]-1-methyl-2-oxo-ethyl]-N-methyl-carbamate (106 mg, 0.17 mmol, 1 eq) and benzyl (2S)-2-(cyanomethyl)-4-[2-[[(2S,4R)-1-methyl-4-[2-[2-[2-(p-tolylsulfonyloxy)ethoxy]ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (160 mg, 0.17 mmol, 1 eq) in acetonitrile (5 mL) was added potassium carbonate (47 mg, 0.34 mmol, 2 eq). The mixture was stirred at 85° C. for 12 hours. The mixture was quenched with water (20 mL). Then the mixture was extracted with dichloromethane (30 mL×3). The combined organic layers were washed with brine, dried over anhydrous sodium sulfate, filtered and concentrated under vacuum to give a residue. The residue was purified by prep-TLC (Dichloromethane:Methanol=10:1). Benzyl (2S)-4-[2-[[(2S,4R)-4-[2-[2-[2-[[4-[2-[(2S)-1-[(2S)-2-[[(2S)-2-[tert-butoxycarbonyl(methyl)amino]propanoyl]amino]-2-cyclohexyl-acetyl]pyrrolidin-2-yl]thiazol-4-yl]-1-naphthyl]oxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (105 mg, 0.07 mmol, 44.3% yield) was obtained as a yellow solid. LC/MS (ESI) m/z: 1383.6 [M+1].

Step 3: Preparation of tert-butyl ((S)-1-(((S)-2-((S)-2-(4-(4-(2-(2-(2-(((3R,5S)-5-(((4-((S)-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethoxy)naphthalen-1-yl)thiazol-2-yl)pyrrolidin-1-yl)-1-cyclohexyl-2-oxoethyl)amino)-1-oxopropan-2-yl)(methyl)carbamate

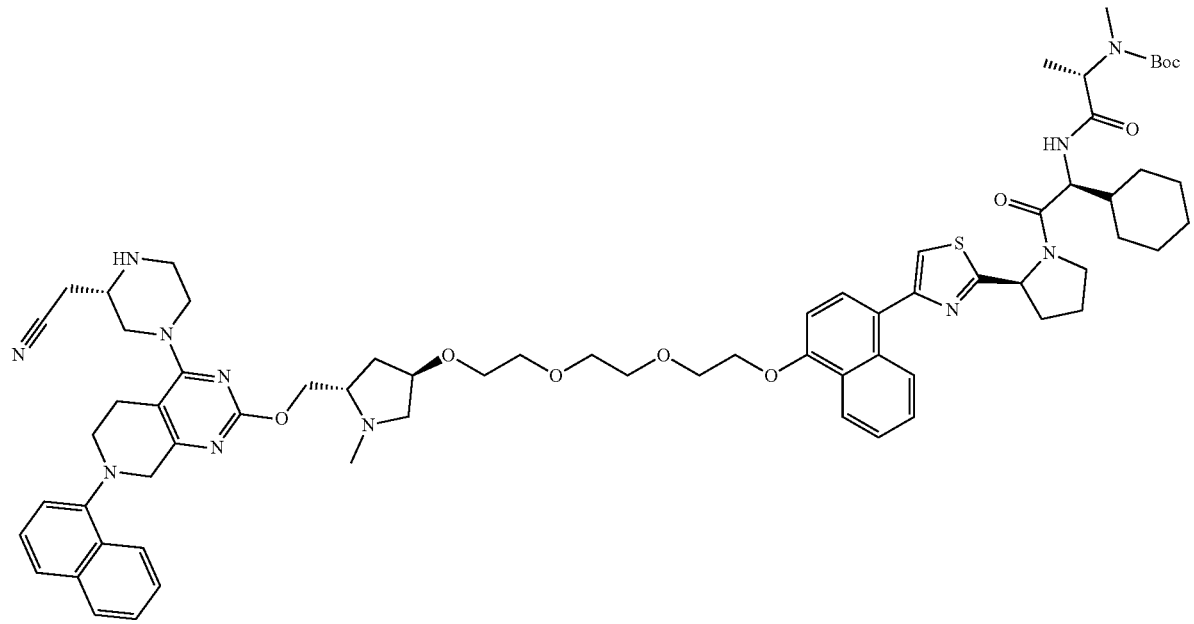 [SMILES: C[C@@H](C(=O)N[C@H](C(=O)N1CCC[C@H]1c1nc(-c2ccc(OCCOCCOCCO[C@@H]3C[C@@H](COc4nc5c(c(N6CCN[C@@H](CC#N)C6)n4)CCN(c4cccc6ccccc46)C5)N(C)C3)c3ccccc23)cs1)C1CCCCC1)N(C)C(=O)OC(C)(C)C]

To the mixture of benzyl (2S)-4-[2-[[(2S,4R)-4-[2-[2-[2-[[4-[2-[(2S)-1-[(2S)-2-[[(2S)-2-[tert-butoxycarbonyl(methyl)amino]propanoyl]amino]-2-cyclohexyl-acetyl]pyrrolidin-2-yl]thiazol-4-yl]-1-naphthyl]oxy]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (105 mg, 0.07 mmol, 1 eq) and ammonium hydroxide (0.2 mL) in tetrahydrofuran (0.5 mL) and methanol (5 mL) was added palladium on activated carbon catalyst (30 mg, 10% purity). The mixture was degassed and charged with hydrogen for three times. Then the mixture was stirred at 25° C. for 12 hours. The mixture was filtered. The filtrate was purified by prep-HPLC. Compound tert-butyl N-[(1S)-2-[[(1S)-2-[(2S)-2-[4-[4-[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]ethoxy]-1-naphthyl]thiazol-2-yl]pyrrolidin-1-yl]-1-cyclohexyl-2-oxo-ethyl]amino]-1-methyl-2-oxo-ethyl]-N-methyl-carbamate (35 mg, 0.03 mmol, 36.9% yield) was obtained as a white solid. LC/MS (ESI) m/z: 1248.8 [M+1]$^+$.

Step 4: Preparation of tert-butyl ((S)-1-(((S)-2-((S)-2-(4-(4-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethoxy)naphthalen-1-yl)thiazol-2-yl)pyrrolidin-1-yl)-11-cyclohexyl-2-oxoethyl)amino)-1-oxopropan-2-yl)(methyl)carbamate

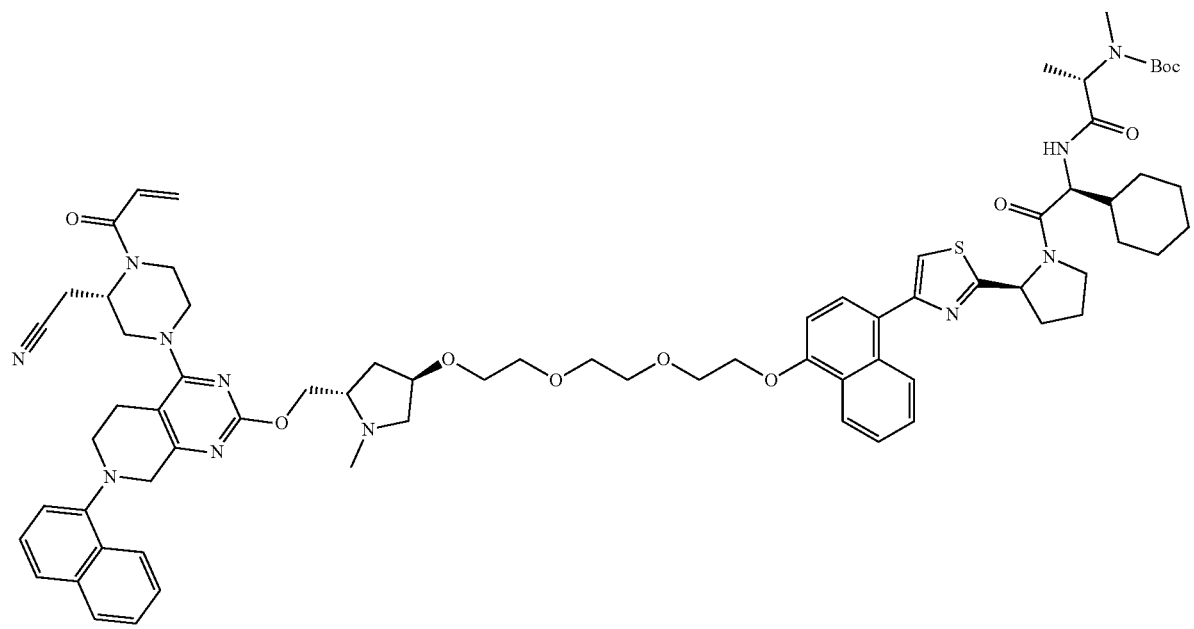 [SMILES: C=CC(=O)N1CCN(c2nc(OC[C@@H]3C[C@@H](OCCOCCOCCOc4ccc(-c5csc([C@@H]6CCCN6C(=O)[C@@H](NC(=O)[C@H](C)N(C)C(=O)OC(C)(C)C)C6CCCCC6)n5)c5ccccc45)CN3C)nc3c2CCN(c2cccc4ccccc24)C3)C[C@@H]1CC#N]

To the mixture of tert-butyl N-[(1S)-2-[[(1S)-2-[(2S)-2-[4-[4-[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]ethoxy]-1-naphthyl]thiazol-2-yl]pyrrolidin-1-yl]-1-cyclohexyl-2-oxo-ethyl]amino]-1-methyl-2-oxo-ethyl]-N-methyl-carbamate (35 mg, 0.03 mmol, 1 eq) in dichloromethane (5 mL) was added 2,6-lutidine (30 mg, 0.28 mmol, 10 eq) and prop-2-enoyl chloride (2 mg, 0.9 eq) at −78° C. Then the mixture was stirred at −78° C. for 30 minutes. The mixture was diluted with water (3 mL). Then the mixture was extracted with ethyl acetate (30 mL×3). The combined organic layers were washed with water (30 mL×2), dried over anhydrous sodium sulfate, filtered and concentrated under vacuum to give a residue. Tert-butyl N-[(1S)-2-[[(1S)-2-[(2S)-2-[4-[4-[2-[2-[2-[(3R,5S)-5-[[4-[(3S)-3-(cyanomethyl)-4-prop-2-enoyl-piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]ethoxy]-1-naphthyl]thiazol-2-yl]pyrrolidin-1-yl]-1-cyclohexyl-2-oxo-ethyl]amino]-1-methyl-2-oxo-ethyl]-N-methyl-carbamate (35 mg) was obtained as a pink oil. LC/MS (ESI) m/z: 1302.9 [M+1]$^+$.

Step 5: Preparation of (S)—N—((S)-2-((S)-2-(4-(4-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethoxy)naphthalen-1-yl)thiazol-2-yl)pyrrolidin-1-yl)-1-cyclohexyl-2-oxoethyl)-2-(methylamino)propanamide

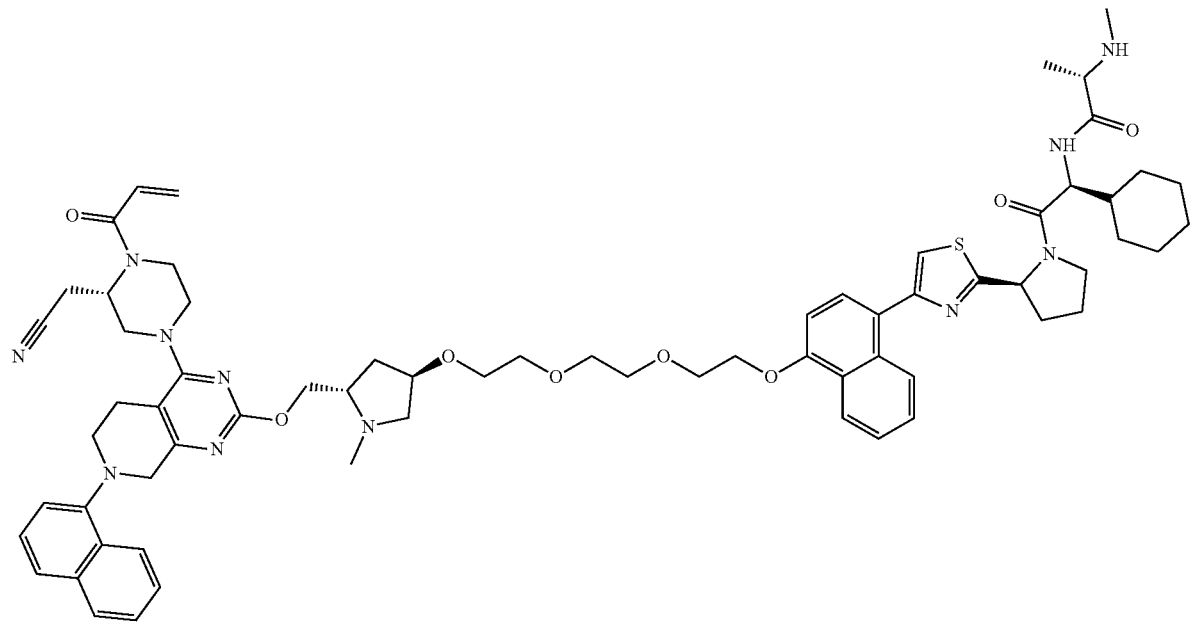 [SMILES: C=CC(=O)N1CCN(c2nc(OC[C@@H]3C[C@@H](OCCOCCOCCOc4ccc(-c5csc([C@@H]6CCCN6C(=O)[C@@H](NC(=O)[C@H](C)NC)C6CCCCC6)n5)c5ccccc45)CN3C)nc3c2CCN(c2cccc4ccccc24)C3)C[C@@H]1CC#N]

To the mixture of tert-butyl N-[(1S)-2-[[(1S)-2-[(2S)-2-[4-[4-[2-[2-[2-[(3R,5S)-5-[[4-[(3S)-3-(cyanomethyl)-4-prop-2-enoyl-piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]ethoxy]-1-naphthyl]thiazol-2-yl]pyrrolidin-1-yl]-1-cyclohexyl-2-oxo-ethyl]amino]-1-methyl-2-oxo-ethyl]-N-methyl-carbamate (35 mg, 0.03 mmol, 1 eq) in dichloromethane (2 mL) was added trifluoroacetic acid (0.2 mL). The mixture was stirred at 25° C. for 30 minutes. The mixture was added into saturated sodium bicarbonate solution drop wise. Then the mixture was extracted with solution (Dichloromethane:Methanol=10:1, 30 mL×2). The combined organic layers were concentrated under vacuum to give a residue. The residue was purified by prep-HPLC. Compound (2S)—N-[(1S)-2-[(2S)-2-[4-[4-[2-[2-[2-[(3R,5S)-5-[[4-[(3S)-3-(cyanomethyl)-4-prop-2-enoyl-piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]ethoxy]-1-naphthyl]thiazol-2-yl]pyrrolidin-1-yl]-1-cyclohexyl-2-oxo-ethyl]-2-(methylamino)propanamide (9.4 mg, 0.007 mmol, 26.3% yield, 98.7% purity, trifluoroacetates) was obtained as a white solid. LC/MS (ESI) m/z: 1203.6 [M+1]$^+$; $^1$H-NMR (400 MHz, DMSO-d$_6$) δ 10.13-9.85 (m, 1H), 8.83-8.70 (m, 2H), 8.28-8.22 (m, 1H), 8.20-8.13 (m, 1H), 7.97-7.90 (m, 1H), 7.73-7.63 (m, 2H), 7.61-7.50 (m, 5H), 7.49-7.43 (m, 1H), 7.21-7.19 (d, J=7.46 Hz, 1H), 7.03-7.01 (d, J=8.0 Hz, 1H), 6.94-6.73 (m, 1H), 6.25-6.12 (m, 1H), 5.82-5.72 (m, 1H), 5.47-5.39 (m, 1H), 5.06-4.91 (m, 1H), 4.81-4.70 (m, 1H), 4.65-4.38 (m, 5H), 4.34-4.29 (m, 2H), 4.27-4.22 (m, 1H), 4.14 (s, 2H), 4.10-4.00 (m, 3H), 3.94-3.67 (m, 12H), 3.63-3.54 (m, 9H), 3.24-3.15 (m, 2H), 3.01-2.93 (m, 5H), 2.89 (s, 1H), 2.73 (s, 1H), 2.28-2.17 (m, 2H), 2.08-1.96 (m, 3H), 1.79-1.64 (m, 4H), 1.62-1.53 (m, 2H), 1.35-1.33 (d, J=6.85 Hz, 3H), 1.24-1.00 (m, 6H).

Exemplary Synthesis of (2R,3S,4R,5S)—N-(4-((2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide (Exemplary Compound 552)

Step 1: Preparation of tert-butyl (S)-2-(cyanomethyl)-4-(2-(((2S,4R)-4-(2-(2-(2-(1,3-dioxoisoindolin-2-yl)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxylate

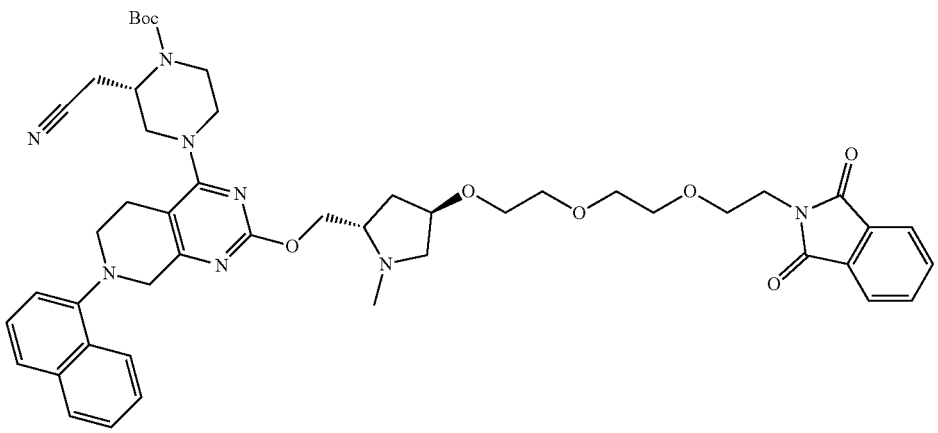 [SMILES: CN1C[C@H](OCCOCCOCCN2C(=O)c3ccccc3C2=O)C[C@H]1COc1nc2c(c(N3CCN(C(=O)OC(C)(C)C)[C@@H](CC#N)C3)n1)CCN(c1cccc3ccccc13)C2]

To a mixture of tert-butyl (2S)-2-(cyanomethyl)-4-[2-[[(2S,4R)-1-methyl-4-[2-[2-[2-(p-tolylsulfonyloxy)ethoxy]ethoxy]ethoxy]pyrrolidin-2-yl]methoxy]-7-(1-naphthyl)-6,8-dihydro-5H-pyrido[3,4-d]pyrimidin-4-yl]piperazine-1-carboxylate (300 mg, 0.33 mmol, 1 eq) in N,N-dimethylformamide (4 mL) was added (1,3-dioxoisoindolin-2-yl)potassium (123 mg, 0.67 mmol, 2 eq), then the reaction mixture was stirred at 80° C. for 2 hours. Water (25 mL) was added, the aqueous phase was extracted with ethyl acetate (25 mL×3). The combined organic phase was washed with brine (25 mL), dried with anhydrous sodium sulfate, filtered and concentrated in vacuum. The residue was purified by silica gel chromatography (Dichloromethane:Methanol=1:0 to 30:1) to get compound tert-butyl (2S)-2-(cyanomethyl)-4-[2-[[(2S,4R)-4-[2-[2-[2-(1,3-dioxoisoindolin-2-yl)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (220 mg, 0.25 mmol, 75% yield) as a yellow solid. LC/MS (ESI) m/z: 875.5 [M+1]+.

Step 2: Preparation of tert-butyl (S)-4-(2-(((2S,4R)-4-(2-(2-(2-aminoethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate

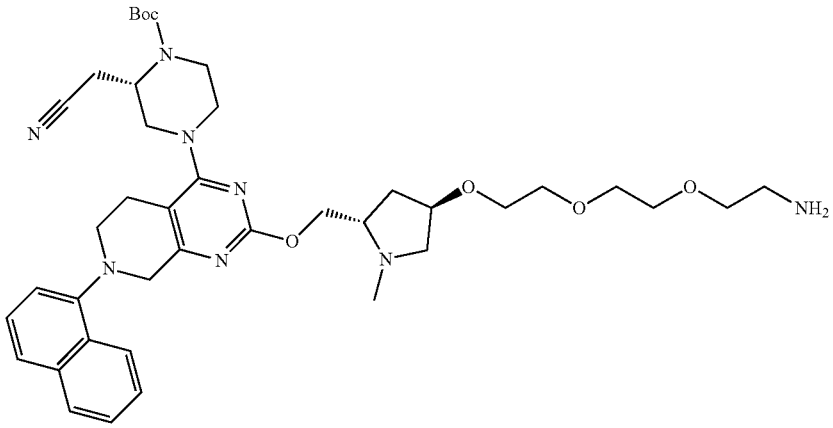 [SMILES: CN1C[C@H](OCCOCCOCCN)C[C@H]1COc1nc2c(c(N3CCN(C(=O)OC(C)(C)C)[C@@H](CC#N)C3)n1)CCN(c1cccc3ccccc13)C2]

To a solution of tert-butyl (2S)-2-(cyanomethyl)-4-[2-[[(2S,4R)-4-[2-[2-[2-(1,3-dioxoisoindolin-2-yl)ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]piperazine-1-carboxylate (150 mg, 0.17 mmol, 1 eq) in ethanol (5 mL) was added hydrazine hydrate (86 mg, 1.71 mmol, 10 eq). The mixture was stirred at 80° C. for 2 hours. The reaction mixture was cooled to 20° C. then ethyl acetate (20 mL) was added, the mixture was filtered and concentrated under vacuum. Compound tert-butyl (2S)-4-[2-[[(2S,4R)-4-[2-[2-(2-aminoethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (141 mg) was obtained as a yellow gum. LC/MS (ESI) m/z: 745.5 [M+1]⁺.

Step 3: Preparation of tert-butyl (S)-4-(2-(((2S,4R)-4-(2-(2-(2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzamido)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate

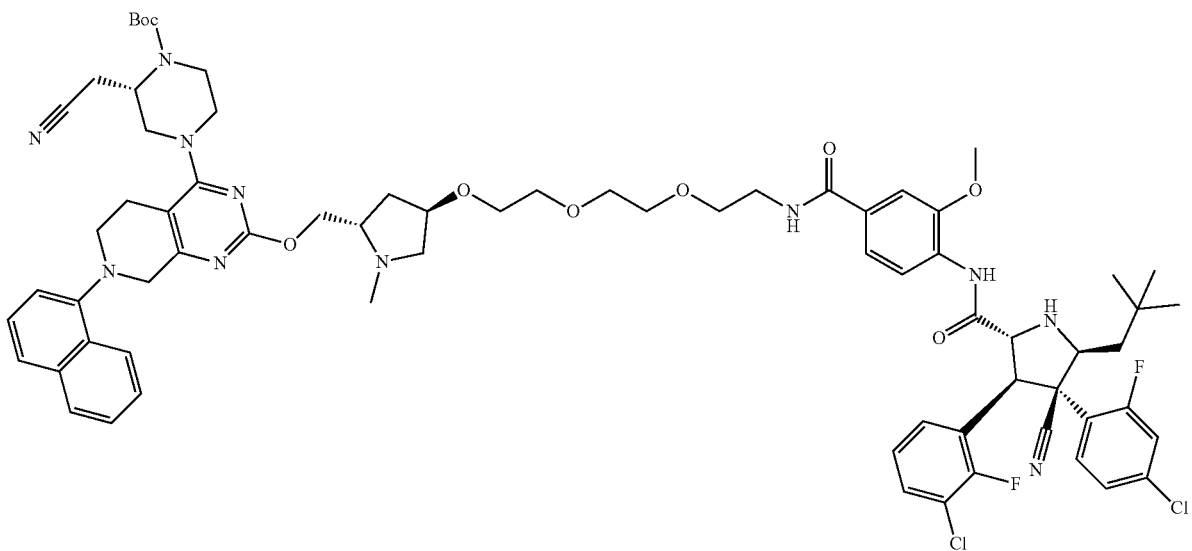 [SMILES: COc1cc(C(=O)NCCOCCOCCO[C@@H]2C[C@@H](COc3nc4c(c(N5CCN(C(=O)OC(C)(C)C)[C@@H](CC#N)C5)n3)CCN(c3cccc5ccccc35)C4)N(C)C2)ccc1NC(=O)[C@@H]1N[C@@H](CC(C)(C)C)[C@](C#N)(c2ccc(Cl)cc2F)[C@H]1c1cccc(Cl)c1F]

903

To a mixture of tert-butyl (2S)-4-[2-[[(2S,4R)-4-[2-[2-(2-aminoethoxy)ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (40 mg, 0.054 mmol, 1.1 eq) and 4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoic acid (30 mg, 0.049 mmol, 1 eq) in N,N-dimethylformamide (1 mL) was added 1-hydroxybenzotriazole (10 mg, 0.073 mmol, 1.5 eq) and 1-(3-dimethylaminopropyl)-3-ethylcarbodiimide hydrochloride (14 mg, 0.073 mmol, 1.5 eq) and N,N-diisopropylethylamine (19 mg, 0.15 mmol, 3 eq), the reaction mixture was stirred at 25° C. for 12 hours. Water (0.1 mL) was added then the mixture was concentrated under vacuum. The reaction mixture was purified by prep-TLC (Dichloromethane:Methanol=15:1). Compound tert-butyl (2S)-4-[2-[[(2S,4R)-4-[2-

904

[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (30 mg, 0.022 mmol, 46% yield) was obtained as a yellow oil. LC/MS (ESI) m/z: 1343.6 [M+1]$^+$.

Step 4: Preparation of (2R,3S,4R,5S)-3-(3-chloro-2-fluorophenyl)-4-(4-chloro-2-fluorophenyl)-4-cyano-N-(4-((2-(2-(2-(((3R,5S)-5-(((4-((S)-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethyl)carbamoyl)-2-methoxyphenyl)-5-neopentylpyrrolidine-2-carboxamide

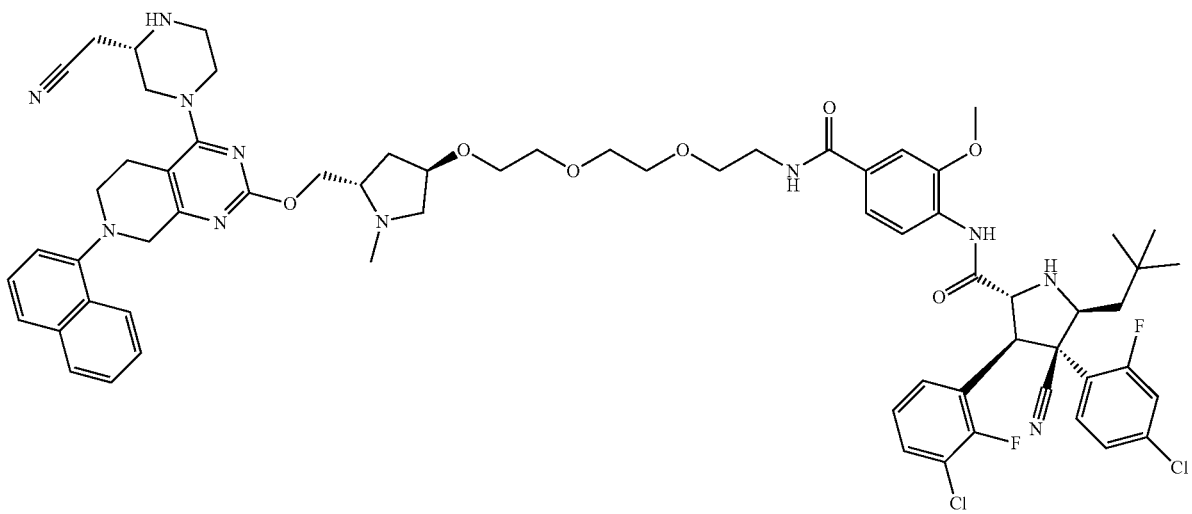 [SMILES: COc1cc(C(=O)NCCOCCOCCO[C@@H]2C[C@@H](COc3nc4c(c(N5CCN[C@@H](CC#N)C5)n3)CCN(c3cccc5ccccc35)C4)N(C)C2)ccc1NC(=O)[C@@H]1N[C@@H](CC(C)(C)C)[C@](C#N)(c2ccc(Cl)cc2F)[C@H]1c1cccc(Cl)c1F]

To a mixture of tert-butyl (2S)-4-[2-[[(2S,4R)-4-[2-[2-[2-[[4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoyl]amino]ethoxy]ethoxy]ethoxy]-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (30 mg, 0.022 mmol, 1 eq) in dichloromethane (5 mL) was added trifluoroacetic acid (1.54 g, 13.51 mmol, 1 mL, 604.79 eq), then the reaction mixture was stirred at 25° C. for 30 minutes. The reaction mixture was concentrated under vacuum. Compound (2R,3S,4R,5S)-3-(3-chloro-2-fluoro-phenyl)-4-(4-chloro-2-fluoro-phenyl)-4-cyano-N-[4-[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]ethylcarbamoyl]-2-methoxy-phenyl]-5-(2,2-dimethylpropyl)pyrrolidine-2-carboxamide (30 mg, 0.022 mmol, 99% yield, trifluoroacetate) was obtained as a yellow oil.

Step 5: Preparation of (2R,3S,4R,5S)—N-(4-((2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide

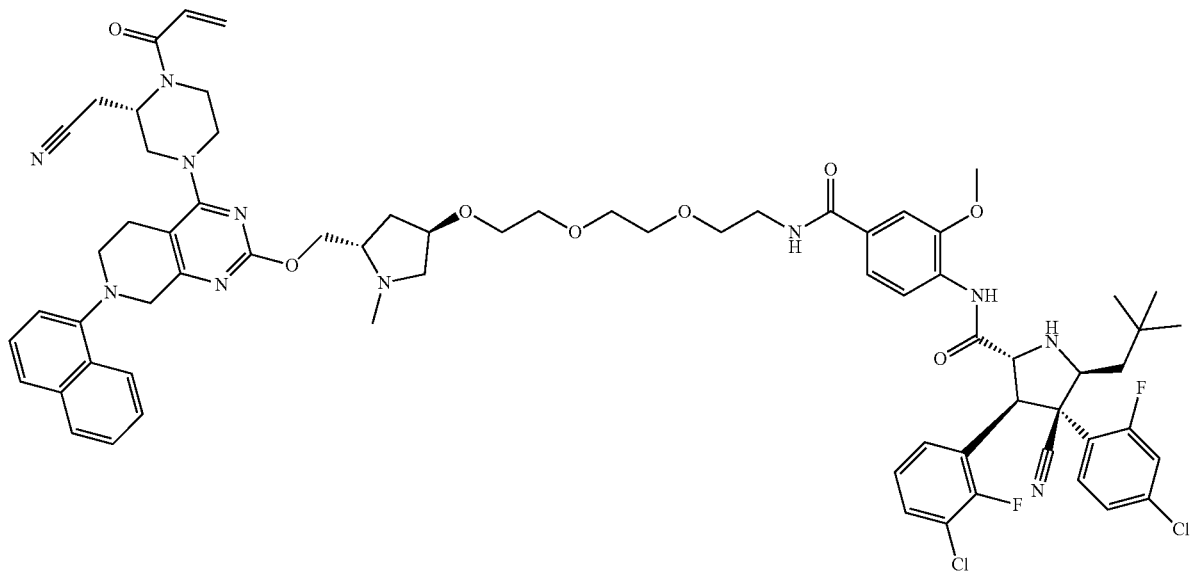 [SMILES: C=CC(=O)N1CCN(c2nc(OC[C@@H]3C[C@@H](OCCOCCOCCNC(=O)c4ccc(NC(=O)[C@@H]5N[C@@H](CC(C)(C)C)[C@](C#N)(c6ccc(Cl)cc6F)[C@H]5c5cccc(Cl)c5F)c(OC)c4)CN3C)nc3c2CCN(c2cccc4ccccc24)C3)C[C@@H]1CC#N]

To a mixture of (2R,3S,4R,5S)-3-(3-chloro-2-fluoro-phenyl)-4-(4-chloro-2-fluoro-phenyl)-4-cyano-N-[4-[2-[2-[2-[(3R,5S)-5-[[4-[(3S)-3-(cyanomethyl)piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]ethylcarbamoyl]-2-methoxy-phenyl]-5-(2,2-dimethylpropyl)pyrrolidine-2-carboxamide (30 mg, 0.022 mmol, 1 eq, trifluoroacetate) in dichloromethane (5 mL) was added 2,6-lutidine (24 mg, 0.22 mmol, 10 eq), then prop-2-enoyl chloride (2 mg, 0.020 mmol, 0.9 eq) was added at −65° C. for 10 minutes. Water (10 mL) and stirred for 0.5 minute. The aqueous phase was extracted with dichloromethane (20 mL×2), and concentrated in vacuum. The residue was purified by semi-preparative reverse phase HPLC. Compound (2R,3S,4R,5S)-3-(3-chloro-2-fluoro-phenyl)-4-(4-chloro-2-fluoro-phenyl)-4-cyano-N-[4-[2-[2-[2-[(3R,5S)-5-[[4-[(3S)-3-(cyanomethyl)-4-prop-2-enoyl-piperazin-1-yl]-7-(1-naphthyl)-6,8-dihydro-5H-pyrido[3,4-d]pyrimidin-2-yl]oxymethyl]-1-methyl-pyrrolidin-3-yl]oxyethoxy]ethoxy]ethylcarbamoyl]-2-methoxy-phenyl]-5-(2,2-dimethylpropyl)pyrrolidine-2-carboxamide (6.0 mg, 0.004 mmol, 20% yield, 99% purity, formate) was obtained as a white solid. LC/MS (ESI) m/z: 640.0 [M/2+1]⁺; ¹H-NMR (400 MHz, DMSO-d₆) δ 10.41 (s, 1H), 8.49 (br t, J=5.5 Hz, 1H), 8.31 (d, J=8.4 Hz, 1H), 8.22 (s, 1H), 8.20-8.14 (m, 1H), 7.96-7.89 (m, 1H), 7.72 (br t, J=6.8 Hz, 1H), 7.64 (d, J=8.3 Hz, 1H), 7.60-7.50 (m, 5H), 7.50-7.43 (m, 2H), 7.41-7.32 (m, 3H), 7.21 (d, J=7.3 Hz, 1H), 6.98-6.74 (m, 1H), 6.25-6.11 (m, 1H), 5.78 (br d, J=12.5 Hz, 1H), 5.06-4.72 (m, 1H), 4.62-4.51 (m, 2H), 4.51-4.28 (m, 2H), 4.24 (br dd, J=4.7, 10.8 Hz, 1H), 4.15-3.93 (m, 8H), 3.91 (s, 3H), 3.55-3.51 (m, 6H), 3.50-3.47 (m, 4H), 3.45-3.43 (m, 4H), 3.25 (br d, J=3.4 Hz, 1H), 3.16 (br s, 1H), 3.06-2.92 (m, 4H), 2.74-2.68 (m, 1H), 2.31 (s, 3H), 2.14 (dd, J=6.1, 9.4 Hz, 1H), 1.91-1.74 (m, 2H), 1.63 (br dd, J=9.9, 14.1 Hz, 1H), 1.31-1.10 (m, 2H), 0.96 (s, 9H).

Exemplary Synthesis of (2S,4R)-1-(4-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide (Exemplary Compound 462)

Step 1: Preparation of 1,2-bis(2-bromoethoxy)ethane

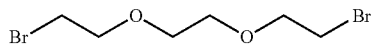

To a solution of 2-[2-[2-(2-hydroxyethoxy)ethoxy]ethoxy]ethanol (20 g, 102.97 mmol, 17.70 mL, 1 eq) and carbon tetrabromide (75.13 g, 226.54 mmol, 2.2 eq) in tetrahydrofuran (200 mL) was added triphenylphosphine (58.07 g, 221.39 mmol, 2.15 eq) dropwise over 30 minutes at 0° C. After the addition, the mixture was stirred at 20° C. for 12 hours. The reaction mixture was concentrated under reduced pressure to remove solvent to give a residue. The residue was purified by silica gel column chromatography (Petroleum ether/Ethyl acetate=50/1 to 20:1). Compound 1-(2-bromoethoxy)-2-[2-(2-bromoethoxy)ethoxy]ethane (30 g, 89.06 mmol, 86% yield, 95% purity) was obtained as a colorless oil.

Step 2: Preparation of 4-(2-(2-bromoethoxy)ethoxy)-2-(3-methylisoxazol-5-yl)butanoic acid

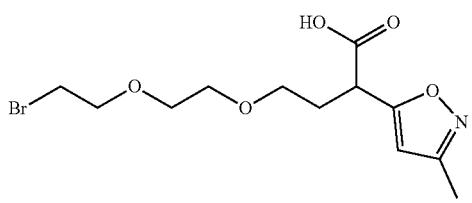 [SMILES: Cc1cc(C(CCOCCOCCBr)C(=O)O)on1]

To a mixture of 2-(3-methylisoxazol-5-yl)acetic acid (4.09 g, 28.99 mmol, 1 eq) in tetrahydrofuran (60 mL) was added n-butyllithium (2.5 M, 28.99 mL, 2.5 eq) drop-wise at −78° C. After the addition, the mixture was stirred at 0° C. for 0.5 hour. Then 1,2-bis(2-bromoethoxy)ethane (16 g, 57.98 mmol, 2 eq) was added drop-wise at −78° C. The mixture was stirred at −78° C. for 1 hour. Then the mixture was allowed to warm to room temperature (25° C.) and stirred at 25° C. for 10.5 hours. The mixture was poured into ice water (100 mL), and then saturated sodium bicarbonate solution was added to basify the solution (pH>8). The solution was extracted with ethyl acetate (100 mL), and the organic layer was discarded. Saturated citric acid solution was added to acidify the water phase (pH=4), and the solution was extracted with ethyl acetate (50 mL×3). The combined organic layers were dried, filtered and concentrated to give a residue. The residue was purified by semi-preparative reverse phase HPLC. Compound 4-[2-(2-bromoethoxy)ethoxy]-2-(3-methylisoxazol-5-yl)butanoic acid (150 mg, 240.94 umol, 0.8% yield, 54% purity) was obtained as a brown gum. LC/MS (ESI) m/z: 336.0 [M+1]⁺.

Step 3: Preparation of (2S,4R)-1-(4-(2-(2-bromoethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide

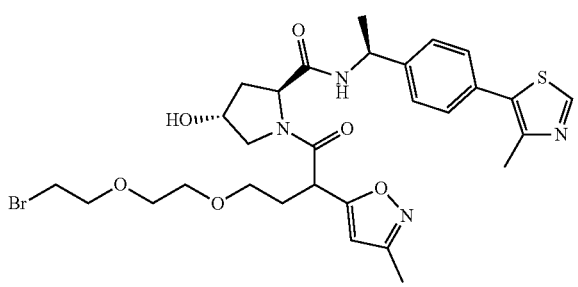 [SMILES: Cc1cc(C(CCOCCOCCBr)C(=O)N2C[C@H](O)C[C@H]2C(=O)N[C@@H](C)c2ccc(-c3scnc3C)cc2)on1]

To a solution of 4-[2-(2-bromoethoxy)ethoxy]-2-(3-methylisoxazol-5-yl)butanoic acid (150 mg, 446.19 umol, 1 eq) and HATU (508.97 mg, 1.34 mmol, 3 eq) in N,N-dimethylformamide (4 mL) was added (2S,4R)-4-hydroxy-N-[(1S)-1-[4-(4-methylthiazol-5-yl)phenyl]ethyl]pyrrolidine-2-carboxamide (147.88 mg, 446.19 umol, 1 eq) and N,N-diisopropylethylamine (230.67 mg, 1.78 mmol, 310.87 uL, 4 eq). The reaction mixture was stirred at 25° C. for 12 hours. The reaction mixture was quenched with water (10 mL) at 0° C., then extracted with ethyl acetate (10 mL×3). The combined organic layers were washed with brine (10 mL×2), dried over anhydrous sodium sulfate, filtered and concentrated to give a residue. The residue was purified by silica gel column chromatography (dichloromethane/methyl alcohol=10/1). Compound (2S,4R)-1-[4-[2-(2-bromoethoxy)ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (0.13 g, 200.12 umol, 44% yield) was obtained as a brown gum. LC/MS (ESI) m/z: 651.1 [M+1]⁺.

Step 4: Preparation of (2S,4R)-4-hydroxy-1-(4-(2-(2-(methylamino)ethoxy)ethoxy)-2-(3-methylisoxazol-5-yl)butanoyl)-N—((S)-1-(4-(4-methylthiazol-5-yl)phenyl)ethyl)pyrrolidine-2-carboxamide

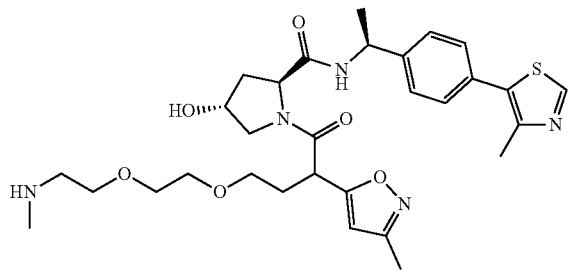 [SMILES: CNCCOCCOCCC(C(=O)N1C[C@H](O)C[C@H]1C(=O)N[C@@H](C)c1ccc(-c2scnc2C)cc1)c1cc(C)no1]

A mixture of (2S,4R)-1-[4-[2-(2-bromoethoxy)ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (0.1 g, 153.94 umol, 1 eq) and methylamine/ethyl alcohol (100.00 mmol, 10 mL, 30% purity) was stirred at 60° C. for 12 hours. The mixture was concentrated to give the product (2S,4R)-4-hydroxy-1-[4-[2-[2-(methylamino)ethoxy]ethoxy]-2-(3-methylisoxazol-5-yl)butanoyl]-N-[(1S)-1-[4-(4-methylthiazol-5-yl)phenyl]ethyl]pyrrolidine-2-carboxamide (90 mg, 150.07 umol, 97% yield) as a yellow solid. LC/MS (ESI) m/z: 600.2 [M+1]⁺.

Step 5: Preparation of (2S,4R)-1-(4-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide

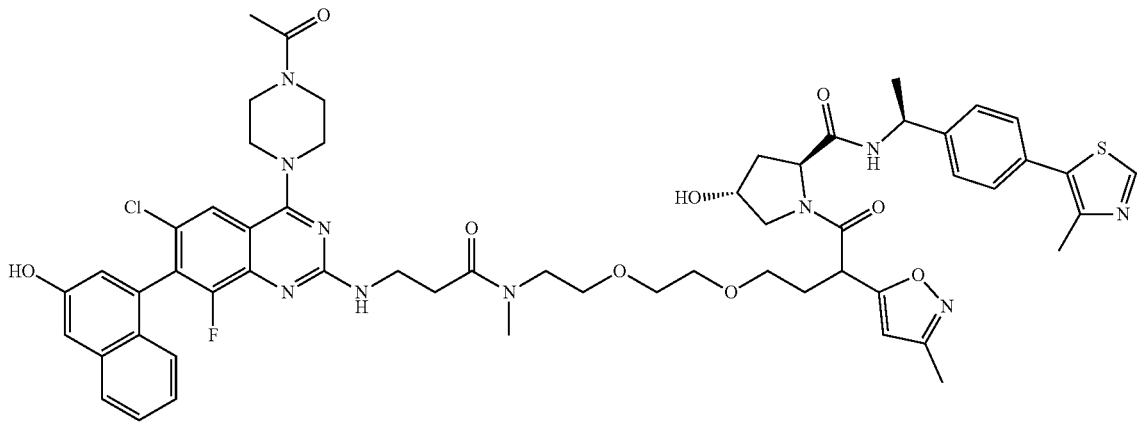 [SMILES: CC(=O)N1CCN(c2nc(NCCC(=O)N(C)CCOCCOCCC(C(=O)N3C[C@H](O)C[C@H]3C(=O)N[C@@H](C)c3ccc(-c4scnc4C)cc3)c3cc(C)no3)nc3c(F)c(-c4cc(O)cc5ccccc45)c(Cl)cc23)CC1]

To a solution of (2S,4R)-4-hydroxy-1-[4-[2-[2-(methylamino)ethoxy]ethoxy]-2-(3-methylisoxazol-5-yl)butanoyl]-N-[(1S)-1-[4-(4-methylthiazol-5-yl)phenyl]ethyl]pyrrolidine-2-carboxamide (90 mg, 150.07 umol, 1 eq) and 3-[[4-(4-acetylpiperazin-1-yl)-6-chloro-8-fluoro-7-(3-hydroxy-1-naphthyl)quinazolin-2-yl]amino]propanoic acid (88.80 mg, 165.07 umol, 1.1 eq) in N,N-dimethylformamide (3 mL) was added 1-hydroxybenzotriazole (40.55 mg, 300.13 umol, 2 eq) and N,N-diisopropylethylamine (77.58 mg, 600.26 umol, 104.55 uL, 4 eq). The mixture was stirred at 25° C. for 0.15 hour. 1-(3-dimethylaminopropyl)-3-ethylcarbodiimide hydrochloride (57.54 mg, 300.13 umol, 2 eq) was added to the mixture. The resulting mixture was stirred at 25° C. for 2 hours. The reaction mixture was quenched with water (15 mL) at 0° C., then extracted with ethyl acetate (10 mL×3). The combined organic layers were washed with brine (15 mL), dried over anhydrous sodium sulfate, filtered and concentrated to give a residue. The residue was purified by semi-preparative reverse phase HPLC. Compound (2S,4R)-1-[4-[2-[2-[3-[[4-(4-acetylpiperazin-1-yl)-6-chloro-8-fluoro-7-(3-hydroxy-1-naphthyl)quinazolin-2-yl]amino]propanoyl-methyl-amino]ethoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (74.7 mg, 66.05 umol, 44% yield, 99% purity) was obtained as a yellow solid. LC/MS (ESI) m/z: 1119.4 [M+1]$^+$; $^1$H-NMR (400 MHz, CD$_3$OD) δ 8.90-8.75 (m, 1H), 7.82-7.65 (m, 2H), 7.45-7.29 (m, 5H), 7.23 (br s, 2H), 7.18-7.09 (m, 1H), 7.03 (br s, 1H), 6.27-6.04 (m, 1H), 5.03-4.93 (m, 1H), 4.61-4.52 (m, 1H), 4.48-4.16 (m, 2H), 3.84-3.41 (m, 21H), 3.31 (br d, J=1.5 Hz, 2H), 3.07 (br d, J=9.5 Hz, 1H), 2.99-2.65 (m, 4H), 2.43 (s, 3H), 2.25-1.91 (m, 10H), 1.46 (br d, J=6.5 Hz, 3H), 1.38-1.19 (m, 2H), 0.88 (br d, J=9.2 Hz, 1H).

Exemplary Synthesis of (2S,4R)-1-(1-((4-(4-acetylpiperazin-1-yl)-6-chloro-8-fluoro-7-(3-hydroxynaphthalen-1-yl)quinazolin-2-yl)amino)-4-methyl-16-(3-methylisoxazol-5-yl)-3-oxo-7,10,13-trioxa-4-azaheptadecan-17-oyl)-4-hydroxy-N—((S)-1-(4-(4-methylthiazol-5-yl)phenyl)ethyl)pyrrolidine-2-carboxamide (Exemplary Compound 463)

Step 1: Preparation of 1-bromo-2-(2-(2-(2-bromoethoxy)ethoxy)ethoxy)ethane

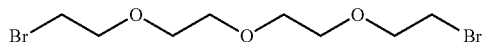 [SMILES: BrCCOCCOCCOCCBr]

To a solution of 2-[2-(2-hydroxyethoxy)ethoxy]ethanol (30 g, 199.77 mmol, 26.79 mL, 1 eq) in tetrahydrofuran (300 mL) was added triphenylphosphine (112.66 g, 429.51 mmol, 2.15 eq) and carbon tetrabromide (145.75 g, 439.49 mmol, 2.2 eq). The mixture was stirred at 20° C. for 12 hours. The reaction mixture was concentrated under reduced pressure to remove solvent. The residue was purified by silica gel column chromatography (Petroleum ether/Ethyl acetate=100/1 to 40/1). Compound 1,2-bis(2-bromoethoxy)ethane (50 g, 173.93 mmol, 87% yield) was obtained as a yellow oil.

Step 2: Preparation of 4-(2-(2-(2-bromoethoxy)ethoxy)ethoxy)-2-(3-methylisoxazol-5-yl)butanoic acid

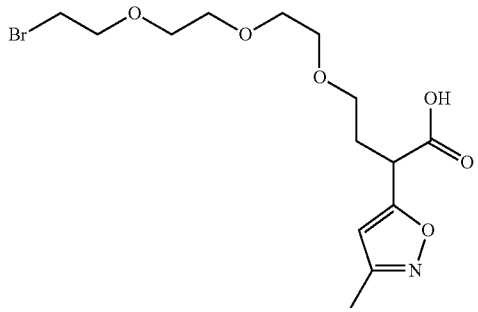 [SMILES: Cc1cc(C(CCOCCOCCOCCBr)C(=O)O)on1]

To a mixture of 2-(3-methylisoxazol-5-yl)acetic acid (1.8 g, 12.75 mmol, 1 eq) in tetrahydrofuran (20 mL) was added n-butyllithium (2.5 M, 12.75 mL, 2.5 eq) drop-wise at −78° C. After the addition, the mixture was stirred at 0° C. for 0.5 hour. Then 1-(2-bromoethoxy)-2-[2-(2-bromoethoxy)ethoxy]ethane (8.16 g, 25.51 mmol, 2 eq) was added dropwise at −78° C. The mixture was stirred at −78° C. for 1 hour. Then the mixture was allowed to warm to room temperature (25° C.) and stirred at 25° C. for 10.5 hours. The mixture was poured into ice water (50 mL), and then saturated sodium bicarbonate solution was added to basify the solution (pH>8). The solution was extracted with ethyl acetate (30 mL), and the organic layer was discarded. Saturated citric acid solution was added to acidify the water phase (pH=4), and the solution was extracted with ethyl acetate (30 mL×3). The combined organic layers were dried, filtered and concentrated to give a residue. The residue was purified by HPLC. Compound 4-[2-[2-(2-bromoethoxy)ethoxy]ethoxy]-2-(3-methylisoxazol-5-yl)butanoic acid (0.15 g, 394.50 umol, 3% yield) was obtained as a brown gum. LC/MS (ESI) m/z: 380.1 [M+1]$^+$.

Step 3: Preparation of (2S,4R)-1-(4-(2-(2-(2-bromoethoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide

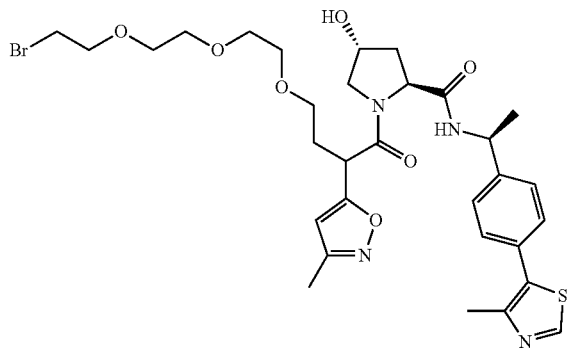 [SMILES: Cc1cc(C(CCOCCOCCOCCBr)C(=O)N2C[C@H](O)C[C@H]2C(=O)N[C@@H](C)c2ccc(-c3scnc3C)cc2)on1]

To a solution of 4-[2-[2-(2-bromoethoxy)ethoxy]ethoxy]-2-(3-methylisoxazol-5-yl)butanoic acid (0.12 g, 315.60 umol, 1 eq) and HATU (360.00 mg, 946.79 umol, 3 eq) in N,N-dimethylformamide (4 mL) was added (2S,4R)-4-hydroxy-N-[(1S)-1l-[4-(4-methylthiazol-5-yl)phenyl]ethyl]pyrrolidine-2-carboxamide (104.60 mg, 315.60 umol, 1 eq) and N,N-diisopropylethylamine (163.16 mg, 1.26 mmol, 219.89 uL, 4 eq). The reaction mixture was stirred at 25° C. for 12 hours. The reaction mixture was quenched with water (10 mL) at 0° C., then extracted with ethyl acetate (10 mL×3). The combined organic layers were washed with brine (10 mL), dried over anhydrous sodium sulfate, filtered and concentrated to give a residue. The residue was purified by silica gel column chromatography (dichloromethane/methyl alcohol=10/1). Compound (2S,4R)-1-[4-[2-[2-(2-bromoethoxy)ethoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (0.13 g, 187.42 umol, 59% yield) was obtained as a brown gum. LC/MS (ESI) m/z: 695.2 [M+1]$^+$.

Step 4: Preparation of (2S,4R)-4-hydroxy-1-(14-(3-methylisoxazol-5-yl)-5,8,11-trioxa-2-azapentadecan-15-oyl)-N—((S)-1-(4-(4-methylthiazol-5-yl)phenyl)ethyl)pyrrolidine-2-carboxamide

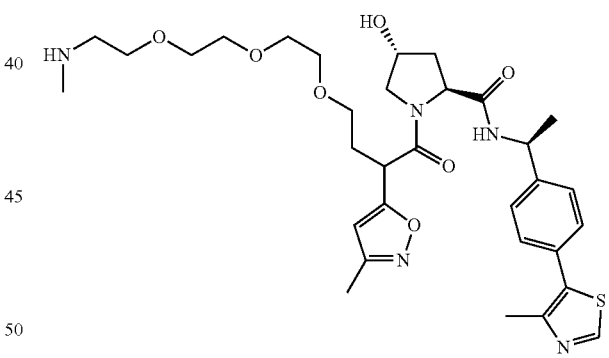

A mixture of (2S,4R)-1-[4-[2-[2-(2-bromoethoxy)ethoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (0.1 g, 144.17 umol, 1 eq) and methylamine/ethyl alcohol (144.17 umol, 10 mL, 30% purity, 1 eq) was stirred at 60° C. for 12 hours. The reaction was concentrated to give the product, (2S,4R)-4-hydroxy-1-[4-[2-[2-[2-(methylamino)ethoxy]ethoxy]ethoxy]-2-(3-methylisoxazol-5-yl)butanoyl]-N-[(1S)-1-[4-(4-methylthiazol-5-yl)phenyl]ethyl]pyrrolidine-2-carboxamide (80 mg, 124.26 umol, 86% yield) as a yellow solid. LC/MS (ESI) m/z: 644.3 [M+1]$^+$.

Step 5: Preparation of (2S,4R)-1-(1-((4-(4-acetylpiperazin-1-yl)-6-chloro-8-fluoro-7-(3-hydroxynaphthalen-1-yl)quinazolin-2-yl)amino)-4-methyl-16-(3-methylisoxazol-5-yl)-3-oxo-7,10,13-trioxa-4-azaheptadecan-17-oyl)-4-hydroxy-N—((S)-1-(4-(4-methylthiazol-5-yl)phenyl)ethyl)pyrrolidine-2-carboxamide

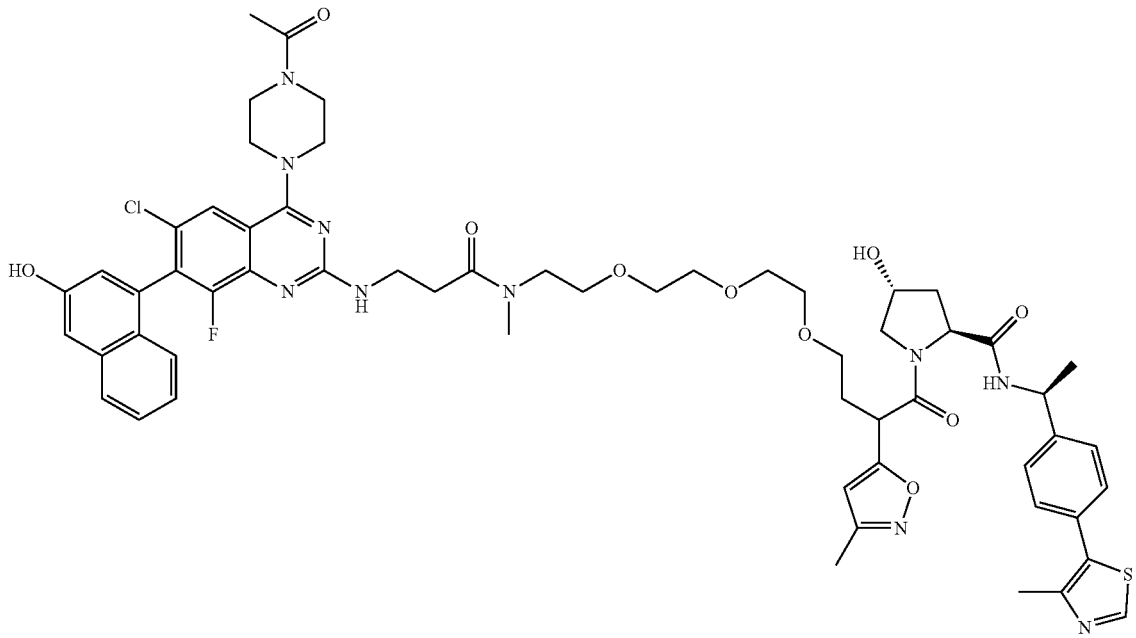 [SMILES: CC(=O)N1CCN(c2nc(NCCC(=O)N(C)CCOCCOCCOCCC(C(=O)N3C[C@H](O)C[C@H]3C(=O)N[C@@H](C)c3ccc(-c4scnc4C)cc3)c3cc(C)no3)nc3c(F)c(-c4cc(O)cc5ccccc45)c(Cl)cc23)CC1]

To solution of (2S,4R)-4-hydroxy-1-[4-[2-[2-[2-(methylamino)ethoxy]ethoxy]ethoxy]-2-(3-methylisoxazol-5-yl)butanoyl]-N-[(1S)-1-[4-(4-methylthiazol-5-yl)phenyl]ethyl]pyrrolidine-2-carboxamide (80 mg, 124.26 umol, 1 eq) and 3-[[4-(4-acetylpiperazin-1-yl)-6-chloro-8-fluoro-7-(3-hydroxy-1-naphthyl)quinazolin-2-yl]amino]propanoic acid (73.54 mg, 136.69 umol, 1.1 eq) in N,N-dimethylformamide (3 mL) was added 1-hydroxybenzotriazole (33.58 mg, 248.53 umol, 2 eq) and N,N-diisopropylethylamine (64.24 mg, 497.05 umol, 86.58 uL, 4 eq). The mixture was stirred at 25° C. for 0.15 hour. 1-(3-dimethylaminopropyl)-3-ethylcarbodiimide hydrochloride (47.64 mg, 248.53 umol, 2 eq) was added to the mixture. The resulting mixture was stirred at 25° C. for 2 hours. The reaction mixture was quenched with water (15 mL) at 0° C., then extracted with ethyl acetate (10 mL×3). The combined organic layers were washed with brine (15 mL), dried over anhydrous sodium sulfate, filtered and concentrated to give a residue. The residue was purified by semi-preparative reverse phase HPLC. Compound (2S,4R)-1-[4-[2-[2-[2-[3-[[4-(4-acetylpiperazin-1-yl)-6-chloro-8-fluoro-7-(3-hydroxy-1-naphthyl)quinazolin-2-yl]amino]propanoyl-methyl-amino]ethoxy]ethoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (62.4 mg, 53.08 umol, 42% yield, 99% purity) was obtained as a yellow solid. LC/MS (ESI) m/z: 1163.3 [M+1]$^+$; $^1$H-NMR (400 MHz, CD$_3$OD) δ 8.90-8.83 (m, 1H), 7.78-7.70 (m, 2H), 7.41-7.35 (m, 5H), 7.23 (br s, 2H), 7.20-7.11 (m, 1H), 7.03 (br s, 1H), 6.23-6.13 (m, 1H), 5.00 (td, J=7.0, 18.7 Hz, 1H), 4.61-4.54 (m, 1H), 4.48-4.27 (m, 2H), 3.75 (br d, J=16.5 Hz, 8H), 3.58-3.51 (m, 8H), 3.10 (br d, J=7.6 Hz, 1H), 2.91 (br d, J=7.0 Hz, 2H), 2.83-2.70 (m, 2H), 2.65 (s, 1H), 2.45 (d, J=2.4 Hz, 3H), 2.24-2.10 (m, 10H), 1.47 (br dd, J=3.1, 6.5 Hz, 3H), 1.28 (s, 1H), 0.88 (br d, J=8.9 Hz, 1H).

Exemplary Synthesis of (2S,4R)-1-((2S)-20-((4-(4-acryloylpiperazin-1-yl)-6-chloro-8-fluoro-7-(3-hydroxynaphthalen-1-yl)quinazolin-2-yl)oxy)-2-(tert-butyl)-18-methyl-4-oxo-6,9,12,15-tetraoxa-3,18-diazaicosanoyl)-4-hydroxy-N—((S)-1-(4-(4-methylthiazol-5-yl)phenyl)ethyl)pyrrolidine-2-carboxamide (Exemplary Compound 473)

Step 1: Preparation of tert-butyl 4-(7-bromo-6-chloro-8-fluoro-2-(2-hydroxyethoxy)quinazolin-4-yl)piperazine-1-carboxylate

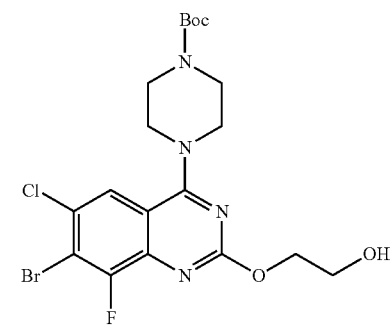 [SMILES: CC(C)(C)OC(=O)N1CCN(c2nc(OCCO)nc3c(F)c(Br)c(Cl)cc23)CC1]

To a solution of ethylene glycol (1.29 g, 20.83 mmol, 1.2 mL, 5 eq) in N,N-dimethylformamide (10 mL) was added sodium hydride (200 mg, 5.00 mmol, 60% in mineral oil, 1.2 eq) at 0° C., the mixture was stirred at 0° C. for 30 minutes, and then tert-butyl 4-(7-bromo-2,6-dichloro-8-fluoro-quinazolin-4-yl)piperazine-1-carboxylate (2 g, 4.17 mmol, 1 eq) in N,N-dimethylformamide (2 mL) was added at 0° C., the mixture was stirred at 20° C. for 1 hour. The mixture was quenched by water (100 mL) and extracted with ethyl acetate (100 mL, twice), the organic phase was dried by anhydrous sodium sulfate, filtered and the filtrate was concentrated to give crude product. This crude product was purified by flash (ethyl acetate:petroleum ether=0:1 to 1:1) to give compound tert-butyl 4-[7-bromo-6-chloro-8-fluoro-2-(2-hydroxyethoxy)quinazolin-4-yl]piperazine-1-carboxylate (1.15 g, 2.09 mmol, 50% yield, 92% purity) as a pale yellow solid. LC/MS (ESI) m/z: 506.9 [M+1]$^+$; $^1$H-NMR (400 MHz, CDCl$_3$) δ 7.72 (d, J=2.0 Hz, 1H), 4.66-4.54 (m, 2H), 4.04-3.97 (m, 2H), 3.86-3.76 (m, 4H), 3.69-3.60 (m, 4H), 1.50 (s, 9H).

Step 2: Preparation of tert-butyl 4-(7-bromo-6-chloro-8-fluoro-2-(((S)-19-((2S,4R)-4-hydroxy-2-(((S)-1-(4-(4-methylthiazol-5-yl)phenyl)ethyl)carbamoyl)pyrrolidine-1-carbonyl)-3,20,20-trimethyl-17-oxo-6,9,12,15-tetraoxa-3,18-diazahenicosyl)oxy)quinazolin-4-yl)piperazine-1-carboxylate

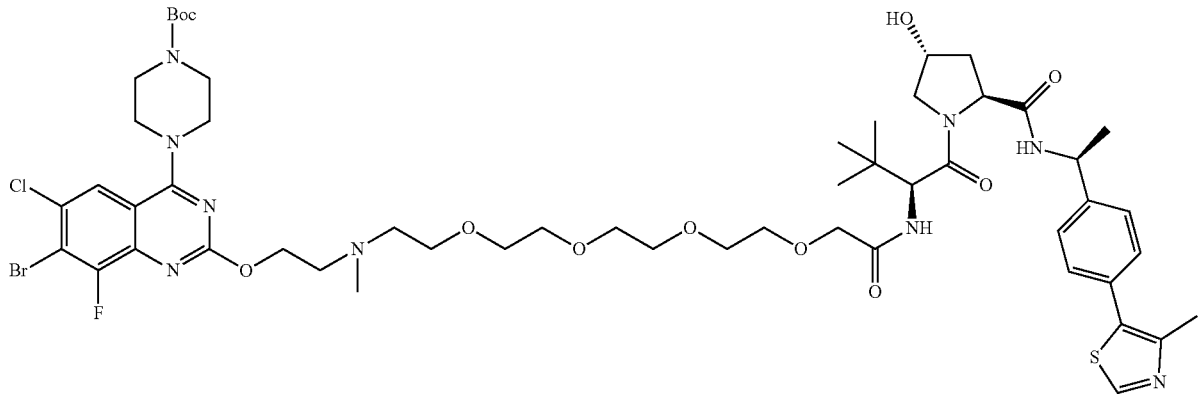 [SMILES: Cc1ncsc1-c1ccc([C@H](C)NC(=O)[C@@H]2C[C@@H](O)CN2C(=O)[C@@H](NC(=O)COCCOCCOCCOCCN(C)CCOc2nc(N3CCN(C(=O)OC(C)(C)C)CC3)c3cc(Cl)c(Br)c(F)c3n2)C(C)(C)C)cc1]

To a solution tert-butyl 4-[7-bromo-6-chloro-8-fluoro-2-(2-hydroxyethoxy) quinazolin-4-yl]piperazine-1-carboxylate (200 mg, 0.40 mmol, 1 eq) in dichloromethane (3 mL) and dimethylsulfoxide (1.00 g, 12.80 mmol, 1 mL, 32.37 eq) was added triethylamine (200 mg, 1.98 mmol, 5 eq) and then Pyridine sulfur trioxide (189 mg, 1.19 mmol, 3 eq), the mixture was stirred at 20° C. for 10 hours. The mixture was charged with (2S,4R)-1-[(2S)-3,3-dimethyl-2-[[2-[2-[2-[2-[2-(methylamino)ethoxy]ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (371 mg, 0.54 mmol, 0.9 eq), triethylamine (121 mg, 1.19 mmol, 2 eq), dichloromethane (4 mL) and dimethylsulfoxide (5 mL) at 20° C. under nitrogen. The mixture was stirred at 20° C. for 30 minutes. Then sodium triacetoxyborohydride (631 mg, 2.98 mmol, 5 eq) was added. The mixture was stirred at 20° C. for 1 hour. The mixture was concentrated in vacuum. The reaction mixture was purified by semi-preparative reverse phase HPLC to give compound tert-butyl 4-[7-bromo-6-chloro-8-fluoro-2-[2-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxoethoxy]ethoxy]ethoxy]ethoxy]ethyl-methylamino]ethoxy]quinazolin-4-yl]piperazine-1-carboxylate (250 mg, 0.20 mmol, 34% yield, formate) as a white solid. LC/MS (ESI) m/z: 590.5 [M/2+1]$^+$.

Step 3: Preparation of tert-butyl 4-(6-chloro-8-fluoro-2-(((S)-19-((2S,4R)-4-hydroxy-2-(((S)-1-(4-(4-methylthiazol-5-yl)phenyl)ethyl)carbamoyl)pyrrolidine-1-carbonyl)-3,20,20-trimethyl-17-oxo-6,9,12,15-tetraoxa-3,18-diazahenicosyl)oxy)-7-(3-hydroxynaphthalen-1-yl)quinazolin-4-yl)piperazine-1-carboxylate

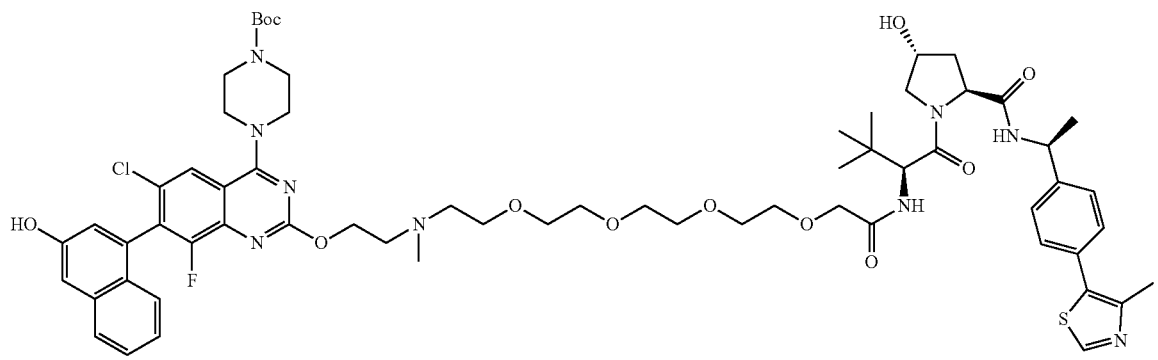 [SMILES: Cc1ncsc1-c1ccc([C@H](C)NC(=O)[C@@H]2C[C@@H](O)CN2C(=O)[C@@H](NC(=O)COCCOCCOCCOCCN(C)CCOc2nc(N3CCN(C(=O)OC(C)(C)C)CC3)c3cc(Cl)c(-c4cc(O)cc5ccccc45)c(F)c3n2)C(C)(C)C)cc1]

A mixture of tert-butyl 4-[7-bromo-6-chloro-8-fluoro-2-[2-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino]ethoxy]quinazolin-4-yl]piperazine-1-carboxylate (50 mg, 0.04 mmol, 1 eq), 4-(4,4,5,5-tetramethyl-1,3,2-dioxaborolan-2-yl)naphthalen-2-ol (17 mg, 0.06 mmol, 1.5 eq), [2-(2-aminophenyl)phenyl]palladium(1+); dicyclohexyl-[2-(2,4,6-triisopropylphenyl)phenyl]phosphane; methanesulfonate (4 mg, 0.004 mmol, 0.1 eq) and potassium phosphate (1.5 M in H$_2$O, 0.08 mL, 3.0 eq) in tetrahydrofuran (3 mL) was degassed and purged with nitrogen (3 times), and then the mixture was stirred at 65° C. for 12 hours under nitrogen atmosphere. The reaction mixture was concentrated under reduced pressure to give a residue. The residue was purified by preparative thin layer chromatography (silica gel plate, dichloromethane/methanol=7/1) to give compound tert-butyl 4-[6-chloro-8-fluoro-2-[2-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]ethyl-methyl-amino]ethoxy]-7-(3-hydroxy-1-naphthyl)quinazolin-4-yl]piperazine-1-carboxylate (40 mg, 0.03 mmol, 76% yield) as a yellow solid. LC/MS (ESI) m/z: 1244.0 [M+I]$^+$.

Step 4: Preparation of (2S,4R)-1-((2S)-2-(tert-butyl)-20-((6-chloro-8-fluoro-7-(3-hydroxynaphthalen-1-yl)-4-(piperazin-1-yl)quinazolin-2-yl)oxy)-18-methyl-4-oxo-6,9,12,15-tetraoxa-3,18-diazaicosanoyl)-4-hydroxy-N—((S)-1-(4-(4-methylthiazol-5-yl)phenyl)ethyl)pyrrolidine-2-carboxamide

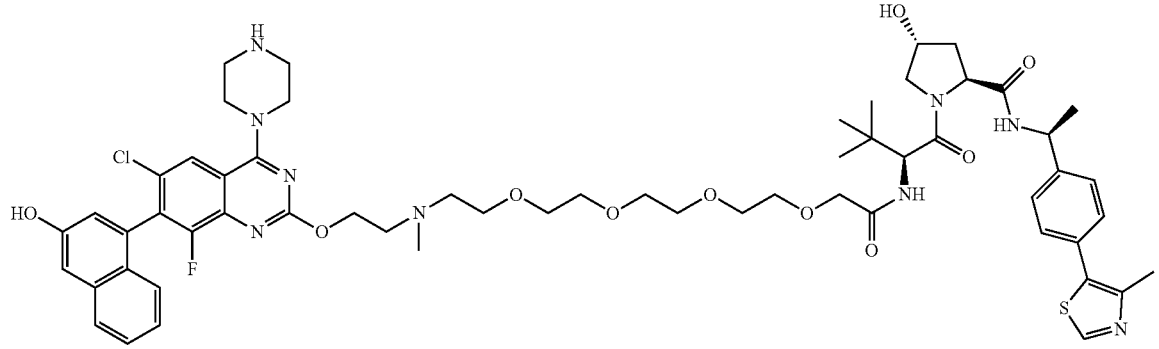 [SMILES: Cc1ncsc1-c1ccc([C@H](C)NC(=O)[C@@H]2C[C@@H](O)CN2C(=O)[C@@H](NC(=O)COCCOCCOCCOCCN(C)CCOc2nc(N3CCNCC3)c3cc(Cl)c(-c4cc(O)cc5ccccc45)c(F)c3n2)C(C)(C)C)cc1]

919

To a solution of tert-butyl 4-[6-chloro-8-fluoro-2-[2-[2-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethyl-methyl-amino]ethoxy]-7-(3-hydroxy-1-naphthyl)quinazolin-4-yl]piperazine-1-carboxylate (40 mg, 0.03 mmol, 1 eq) in dichloromethane (5 mL) was added hydrochloric acid HCl in dioxane (4 M, 3 mL). The mixture was stirred at 20° C. for 0.5 hour. The reaction mixture was concentrated under reduced pressure to give compound (2S,4R)-1-[(2S)-2-[[2-[2-[2-[2-[2-[2-[6-chloro-8-fluoro-7-(3-hydroxy-1-naphthyl)-4-piperazin-1-yl-quinazolin-2-yl]oxyethyl-methyl-amino]ethoxy]ethoxy]

920 ethoxy]ethoxy]acetyl]amino]-3,3-dimethyl-butanoyl]-4-hydroxy-N—[(S)-1-[4-(4-methylthiazol-5-yl)phenyl]ethyl]pyrrolidine-2-carboxamide (40 mg, hydrochloride) as a yellow solid. LC/MS (ESI) m/z: 1143.6 [M+1]$^+$.

Step 5: Preparation of (2S,4R)-1-((2S)-20-((4-(4-acryloylpiperazin-1-yl)-6-chloro-8-fluoro-7-(3-hydroxynaphthalen-1-yl)quinazolin-2-yl)oxy)-2-(tert-butyl)-18-methyl-4-oxo-6,9,12,15-tetraoxa-3,18-diazaicosanoyl)-4-hydroxy-N—((S)-1-(4-(4-methylthiazol-5-yl)phenyl)ethyl)pyrrolidine-2-carboxamide

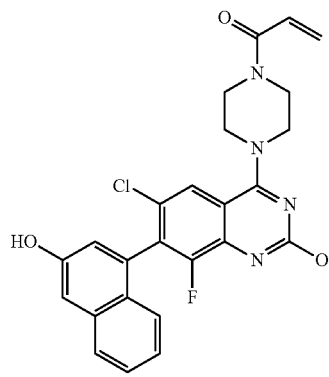
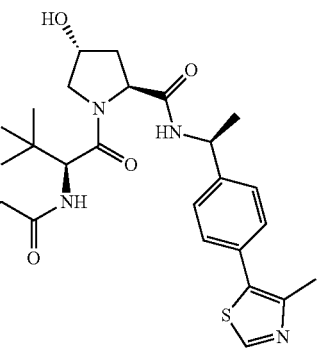

A mixture of (2S,4R)-1-[(2S)-2-[[2-[2-[2-[2-[2-[2-[6-chloro-8-fluoro-7-(3-hydroxy-1-naphthyl)-4-piperazin-1-yl-quinazolin-2-yl]oxyethyl-methyl-amino]ethoxy]ethoxy]ethoxy]ethoxy]acetyl]amino]-3,3-dimethyl-butanoyl]-4-hydroxy-N— [(S)-1-[4-(4-methylthiazol-5-yl)phenyl]ethyl]pyrrolidine-2-carboxamide (40 mg, 0.033 mmol, 1 eq, hydrochloride) and 2,6-lutidine (106 mg, 0.99 mmol, 30 eq) in dichloromethane (5 mL) was cooled to −78° C., then prop-2-enoyl chloride (3 mg, 0.033 mmol, 1 eq) in dichloromethane (1 mL) was added in. The mixture was stirred at −78° C. for 0.5 hour. The reaction mixture was quenched with saturated sodium bicarbonate solution (20 mL), then extracted with dichloromethane (20 mL×2). The combined organic layers were washed with brine (20 mL×1), dried over anhydrous sodium sulfate, filtered and concentrated under reduced pressure to give a residue. The residue was purified by semi-preparative reverse phase HPLC to give compound (2S,4R)-1-[(2S)-2-[[2-[2-[2-[2-[2-[2-[6-chloro-8-fluoro-7-(3-hydroxy-1-naphthyl)-4-(4-prop-2-enoylpiperazin-1-yl)quinazolin-2-yl]oxyethyl-methyl-amino]ethoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (25.6 mg, 0.019 mmol, 56% yield, 95% purity, trifluoroacetic acid salt) as a yellow solid. LC/MS (ESI) m/z: 589.9 [M/2+1]$^+$; $^1$H-NMR (400 MHz, CD$_3$OD) δ 9.01-8.89 (m, 1H), 8.17-8.05 (m, 1H), 7.76 (d, J=8.4 Hz, 1H), 7.58-7.38 (m, 5H), 7.28 (d, J=2.4 Hz, 1H), 7.25-7.16 (m, 2H), 7.05 (d, J=2.4 Hz, 1H), 6.89-6.73 (m, 1H), 6.36-6.23 (m, 1H), 5.86-5.75 (m, 1H), 5.04-4.94 (m, 1H), 4.82-4.75 (m, 1H), 4.69-4.63 (m, 1H), 4.58-4.51 (m, 1H), 4.46-4.31 (m, 1H), 4.16-4.06 (m, 4H), 4.05-3.99 (m, 2H), 3.98-3.89 (m, 4H), 3.88-3.80 (m, 3H), 3.80-3.39 (m, 18H), 3.11-2.99 (m, 3H), 2.51-2.42 (m, 3H), 2.40-2.13 (m, 1H), 2.03-1.90 (m, 1H), 1.60-1.43 (m, 3H), 1.07-0.96 (m, 9H).

921

Exemplary Synthesis of (2S,4R)-1-((2S)-2-(2-(4-(2-(2-(4-((4-(4-acryloylpiperazin-1-yl)-6-chloro-8-fluoro-7-(3-hydroxynaphthalen-1-yl)quinazolin-2-yl)oxy)piperidin-1-yl)ethoxy)ethyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Exemplary Compound 475)

Step 1: Preparation of 2-(2,2-diethoxyethoxy)ethan-1-ol

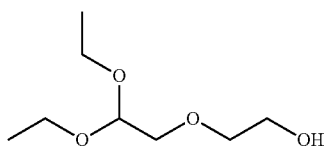

A three neck flask having a content volume of 100 mL equipped with a thermometer, a stirring device and a reflux condenser was charged with ethylene glycol (9.45 g, 152.23 mmol, 8.5 mL, 2 eq). The flask was cooled on an ice bath. Potassium hydroxide (6.41 g, 114.17 mmol, 1.5 eq) was added between 0-50° C. slowly. Then 2-bromo-1,1-diethoxy-ethane (15 g, 76.12 mmol, 11.45 mL, 1 eq) was added and the reaction mixture was heated to 110° C. for 20 hours. The reaction mixture was cooled to 20° C. then water (30 mL) was added. The pH of the mixture was adjusted to 8 with the addition of 1 N hydrochloric acid. Then the mixture was extracted with ethyl acetate (50 mL×5). The organic layer was dried over sodium sulfate and then concentrated under vacuum to get the residue. The residue was purified by silica gel column chromatography (5-80% ethyl acetate in petroleum ether) to get 2-(2,2-diethoxyethoxy)ethanol (3.71 g, 20.82 mmol, 27% yield) as a light yellow oil. $^1$H-NMR (400 MHz, CDCl$_3$) δ 4.65 (t, J=5.2 Hz, 1H), 3.78-3.68 (m, 4H), 3.67-3.62 (m, 2H), 3.62-3.54 (m, 4H), 2.43 (br s, 1H), 1.24 (t, J=7.1 Hz, 6H).

Step 2: Preparation of 2-(2,2-diethoxyethoxy)ethyl 4-methylbenzenesulfonate

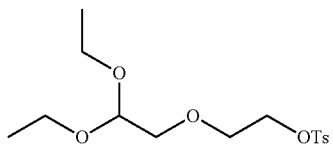 [SMILES: CCOC(COCCOS(=O)(=O)c1ccc(C)cc1)OCC]

To a solution of 2-(2,2-diethoxyethoxy)ethanol (300 mg, 1.68 mmol, 1 eq) in dichloromethane (6 mL) were added triethylamine (511 mg, 5.05 mmol, 0.7 mL, 3 eq) and 4-methylbenzene-1-sulfonyl chloride (481 mg, 2.52 mmol, 1.5 eq). The reaction mixture was stirred at 25° C. for 20 hours. The reaction mixture was concentrated under vacuum to get the residue. The residue was purified by silica gel column chromatography (5-15% ethyl acetate in petroleum ether) to get 2-(2,2-diethoxyethoxy)ethyl 4-methylbenzenesulfonate (404 mg, 1.22 mmol, 72% yield) as a colorless oil.

922

Step 3: Preparation of ethyl 2-(4-(2-(2,2-diethoxyethoxy)ethyl)piperazin-1-yl)acetate

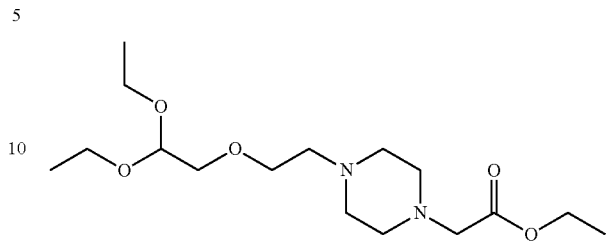

To a solution of ethyl 2-piperazin-1-ylacetate (1.06 g, 5.08 mmol, 1.3 eq, hydrochloric) and 2-(2,2-diethoxyethoxy)ethyl 4-methylbenzenesulfonate (1.3 g, 3.91 mmol, 1 eq) in acetonitrile (10 mL) was added potassium carbonate (1.62 g, 11.76 mmol, 3.01 eq). The mixture was stirred at 80° C. for 12 hours. Water (O1 mL) was added, then the mixture was extracted with ethyl acetate (20 mL×3), the mixture was with anhydrous sodium sulfate, filtered and concentrated in vacuum. The residue was purified by prep-HPLC. Compound ethyl 2-[4-[2-(2,2-diethoxyethoxy)ethyl]piperazin-1-yl]acetate (500 mg, 1.50 mmol, 38% yield) was obtained as a yellow oil. LC/MS (ESI) m/z: 333.6 [M+1]$^+$.

Step 4: Preparation of 2-(4-(2-(2,2-diethoxyethoxy)ethyl)piperazin-1-yl)acetic acid

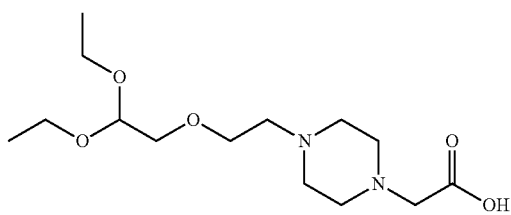 [SMILES: CCOC(COCCN1CCN(CC(=O)O)CC1)OCC]

To a solution of ethyl 2-[4-[2-(2,2-diethoxyethoxy)ethyl]piperazin-1-yl]acetate (400 mg, 1.20 mmol, 1 eq) in a mixture of tetrahydrofuran (4 mL) and methanol (2 mL) were added water (2.5 mL) and Lithium Hydroxide Monohydrate (101 mg, 2.41 mmol, 2 eq). The reaction mixture was stirred at 20° C. for 2 hours. 2 M sulfuric acid was added to adjust the pH of the mixture to 7. Then the mixture was concentrated under vacuum to remove most of the organic solvents and then lyophilized. Methanol (2 mL) and dichloromethane (20 mL) were added. The mixture was filtered and the filtrate was concentrated under vacuum to get 2-[4-[2-(2,2-diethoxyethoxy)ethyl]piperazin-1-yl]acetic acid (320 mg, 1.05 mmol, 87% yield) as a light yellow oil. $^1$H-NMR (400 MHz, CDCl$_3$) δ 4.62 (t, J=5.1 Hz, 1H), 3.74-3.62 (m, 4H), 3.56 (qd, J=7.1, 9.4 Hz, 2H), 3.49 (br s, 3H), 3.33 (br s, 2H), 3.05 (br s, 4H), 2.78 (br s, 4H), 2.67 (br s, 2H), 1.22 (t, J=7.0 Hz, 6H).

Step 5: Preparation of (2S,4R)-1-((S)-2-(2-(4-(2-(2,2-diethoxyethoxy)ethyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide

Step 6: Preparation of (2S,4R)-1-((S)-3,3-dimethyl-2-(2-(4-(2-(2-oxoethoxy)ethyl)piperazin-1-yl)acetamido)butanoyl)-4-hydroxy-N—((S)-1-(4-(4-methylthiazol-5-yl)phenyl)ethyl)pyrrolidine-2-carboxamide

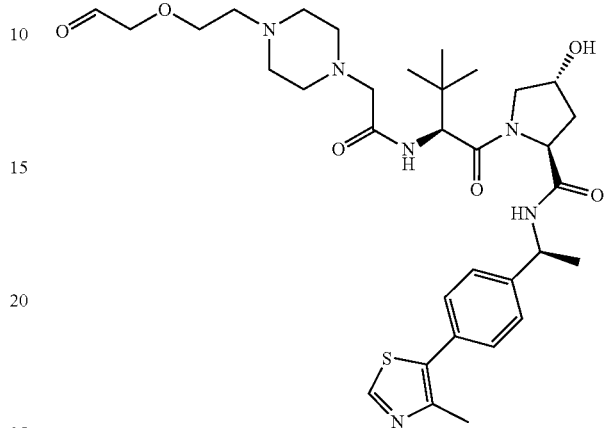

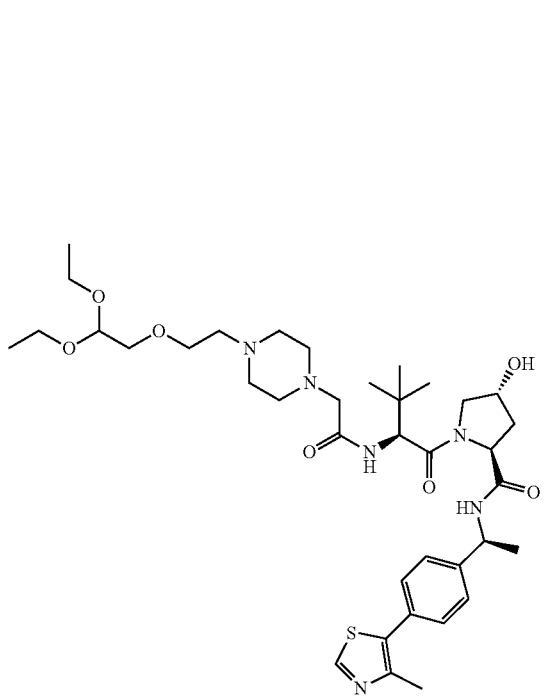 [SMILES: CCOC(COCCN1CCN(CC(=O)N[C@H](C(=O)N2C[C@H](O)C[C@H]2C(=O)N[C@@H](C)c2ccc(-c3scnc3C)cc2)C(C)(C)C)CC1)OCC]

To a solution of (2S,4R)-1-[(2S)-2-[[2-[4-[2-(2,2-diethoxyethoxy)ethyl]piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (100 mg, 0.14 mmol, 1 eq) in tetrahydrofuran (3 mL) was added sulfuric acid (2 M, 0.5 mL, 7.31 eq). The reaction mixture was stirred at 60° C. for 1 hour. Solid sodium sulfate was added into the mixture to adjust the pH to 7. Then tetrahydrofuran (30 mL) and methanol (2 mL) were added and the mixture was dried over sodium sulfate. The solution was concentrated under vacuum to get (2S,4R)-1-[(2S)-3,3-dimethyl-2-[[2-[4-[2-(2-oxoethoxy)ethyl]piperazin-1-yl]acetyl]amino]butanoyl]-4-hydroxy-N-[(1S)-1-[4-(4-methylthiazol-5-yl)phenyl]ethyl]pyrrolidine-2-carboxamide (73 mg) as a colorless gum. LC/MS (ESI) m/z: 679.4 [M+23]$^+$.

Step 7: Preparation of 2-(trimethylsilyl)ethyl 4-hydroxypiperidine-1-carboxylate

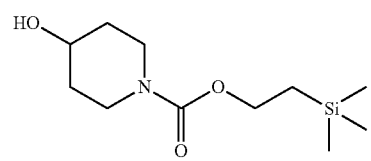 [SMILES: C[Si](C)(C)CCOC(=O)N1CCC(O)CC1]

To a solution of 2-[4-[2-(2,2-diethoxyethoxy)ethyl]piperazin-1-yl]acetic acid (152 mg, 0.50 mmol, 1.2 eq), (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (200 mg, 0.42 mmol, 1 eq, hydrochloride), hydroxybenzotriazole (73 mg, 0.54 mmol, 1.3 eq) and 1-(3-dimethylaminopropyl)-3-ethylcarbodiimide hydrochloride (104 mg, 0.54 mmol, 1.3 eq) in N,N-dimethylformamide (4 mL) was added N,N-diisopropylethylamine (161 mg, 1.25 mmol, 0.22 mL, 3 eq). The reaction mixture was stirred at 20° C. for 4 hours. Then the reaction mixture was stirred at 20° C. for another 14 hours. Water (20 mL) was added and the mixture was extracted with ethyl acetate (20 mL×2). The organic layer was dried over sodium sulfate and then concentrated under vacuum to get the residue. The residue was purified by prep-TLC (10% methanol in dichloromethane) to get (2S,4R)-1-[(2S)-2-[[2-[4-[2-(2,2-diethoxyethoxy)ethyl]piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (192 mg, 0.24 mmol, 58% yield, 92% purity) as a colorless gum. LC/MS (ESI) m/z: 731.5 [M+1]$^+$.

To a solution of piperidin-4-ol (1.17 g, 11.57 mmol, 3 eq) in tetrahydrofuran (10 mL) was added triethylamine (1.17 g, 11.57 mmol, 1.61 mL, 3 eq), (2,5-dioxopyrrolidin-1-yl) 2-trimethylsilylethyl carbonate (1 g, 3.86 mmol, 1 eq) was added to the mixture, the reaction was stirred at 25° C. for 2 h. The reaction mixture was quenched by water (30 mL) and extracted with ethyl acetae (20 mL×2). The combined organic layers were washed with brine (30 mL), dried over sodium sulfate, filtered and concentrated under reduced pressure to give a residue. The residue was purified by column chromatography (SiO$_2$, Petroleum ether/Ethyl acetate=5:1 to 0:1) to give compound 2-trimethylsilylethyl 4-hydroxypiperidine-1-carboxylate (985 mg) as a colorless oil. ¹H-NMR (400 MHz, CD₃OD) δ 4.22-4.16 (m, 4H), 3.71-3.67 (m, 10H), 3.60-3.56 (m, 1H), 3.31-3.13 (m, 1H), 1.81-1.61 (m, 2H), 1.50-1.47 (m, 2H), 1.47 (s, 9H), 1.27 (t, J=7.2 Hz, 3H).

Step 8: Preparation of tert-butyl 4-(7-bromo-6-chloro-8-fluoro-2-((1-((2-(trimethylsilyl)ethoxy)carbonyl)piperidin-4-yl)oxy)quinazolin-4-yl)piperazine-1-carboxylate

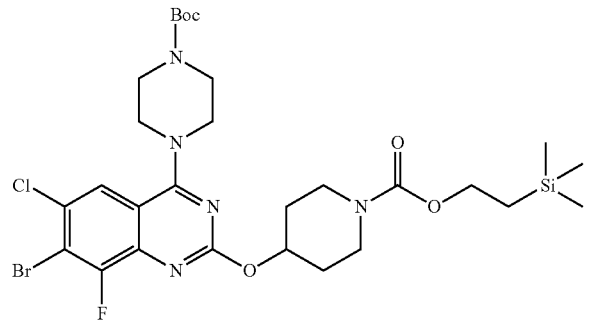 [SMILES: CC(C)(C)OC(=O)N1CCN(c2nc(OC3CCN(C(=O)OCC[Si](C)(C)C)CC3)nc3c(F)c(Br)c(Cl)cc23)CC1]

A mixture of tert-butyl 4-(7-bromo-2,6-dichloro-8-fluoroquinazolin-4-yl)piperazine-1-carboxylate (500 mg, 1.04 mmol, 1 eq), 2-trimethylsilylethyl 4-hydroxypiperidine-1-carboxylate (511 mg, 2.08 mmol, 2 eq, potassium (432 mg, 3.12 mmol, 3 eq) and 1,4-diazabicyclo[2.2.2]octane (12 mg, 0.10 mmol, 0.1 eq) in acetonitrile (25 mL) was heated at 85° C. for 14 hours. The reaction mixture was filtered and the filtrate was concentrated under vacuum to get the residue. The residue was purified by silica gel column chromatography (0-15% ethyl acetate in petroleum ether) to get tert-butyl 4-[7-bromo-6-chloro-8-fluoro-2-[[1-(2-trimethylsilylethoxycarbonyl)-4-piperidyl]oxy]quinazolin-4-yl]piperazine-1-carboxylate (240 mg, 0.35 mmol, 33% yield) as a yellow solid.

Step 9: Preparation of tert-butyl 4-(6-chloro-8-fluoro-7-(3-hydroxynaphthalen-1-yl)-2-((1-((2-(trimethylsilyl)ethoxy)carbonyl)piperidin-4-yl)oxy)quinazolin-4-yl)piperazine-1-carboxylate

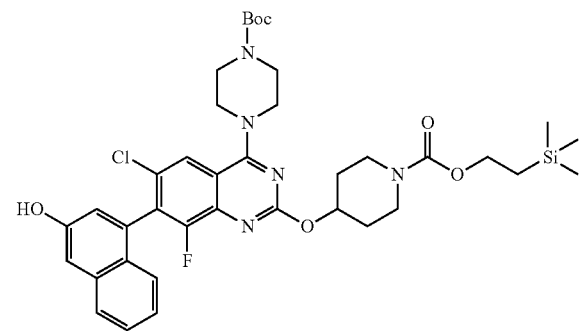 [SMILES: CC(C)(C)OC(=O)N1CCN(c2nc(OC3CCN(C(=O)OCC[Si](C)(C)C)CC3)nc3c(F)c(-c4cc(O)cc5ccccc45)c(Cl)cc23)CC1]

To a solution of tert-butyl 4-[7-bromo-6-chloro-8-fluoro-2-[[1-(2-trimethylsilylethoxycarbonyl)-4-piperidyl]oxy]quinazolin-4-yl]piperazine-1-carboxylate (230 mg, 333.77 umol, 1 eq), 4-(4,4,5,5-tetramethyl-1,3,2-dioxaborolan-2-yl)naphthalen-2-ol (117 mg, 0.43 mmol, 1.3 eq) in tetrahydrofuran (8 mL) was added potassium phosphate (1.5 M, 0.67 mL, 3 eq) and methanesulfonato(2-dicyclohexylphosphino-2,4,6-tri-i-propyl-1,1-biphenyl)(2-amino-1,1-biphenyl-2-yl)palladium(ii) (28 mg, 0.33 mol, 0.1 eq). The reaction mixture was degassed and charged with nitrogen for 3 times and then heated to 65° C. for 16 hours. Ethyl acetate (30 mL) was added and the mixture was washed with water (30 mL). The organic layer was dried over sodium sulfate and then concentrated under vacuum to get the residue. The residue was purified by prep-TLC (60% ethyl acetate in petroleum ether) to get tert-butyl 4-[6-chloro-8-fluoro-7-(3-hydroxy-1-naphthyl)-2-[[1-(2-trimethylsilylethoxycarbonyl)-4-piperidyl]oxy]quinazolin-4-yl]piperazine-1-carboxylate (200 mg) as a light yellow solid. LC/MS (ESI) m/z: 752.1 [M+1]⁺.

Step 10: Preparation of tert-butyl 4-(6-chloro-8-fluoro-7-(3-hydroxynaphthalen-1-yl)-2-(piperidin-4-yloxy)quinazolin-4-yl)piperazine-1-carboxylate

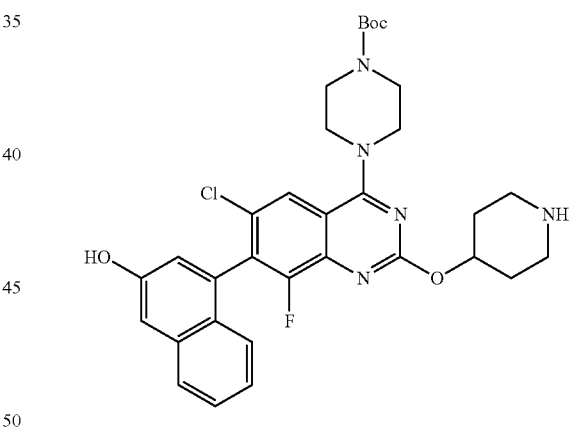

To a solution of tert-butyl 4-[6-chloro-8-fluoro-7-(3-hydroxy-1-naphthyl)-2-[[1-(2-trimethylsilylethoxycarbonyl)-4-piperidyl]oxy]quinazolin-4-yl]piperazine-1-carboxylate (180 mg, 0.24 mmol, 1 eq) in tetrahydrofuran (4 mL) was added tetrabutylammonium fluoride (1 M, 0.26 mL, 1.1 eq). The reaction mixture was heated to 50° C. for 14 hours. The reaction solution was concentrated under vacuum to get the residue. The residue was purified by prep-HPLC to get tert-butyl 4-[6-chloro-8-fluoro-7-(3-hydroxy-1-naphthyl)-2-(4-piperidyloxy)quinazolin-4-yl]piperazine-1-carboxylate (130 mg, 0.18 mmol, 75% yield, trifluoroacetate) as a light yellow solid. LC/MS (ESI) m/z: 608.3 [M+1]⁺.

Step 11: Preparation of tert-butyl 4-(6-chloro-8-fluoro-2-((1-(2-(2-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)ethoxy)ethyl)piperidin-4-yl)oxy)-7-(3-hydroxynaphthalen-1-yl)quinazolin-4-yl)piperazine-1-carboxylate

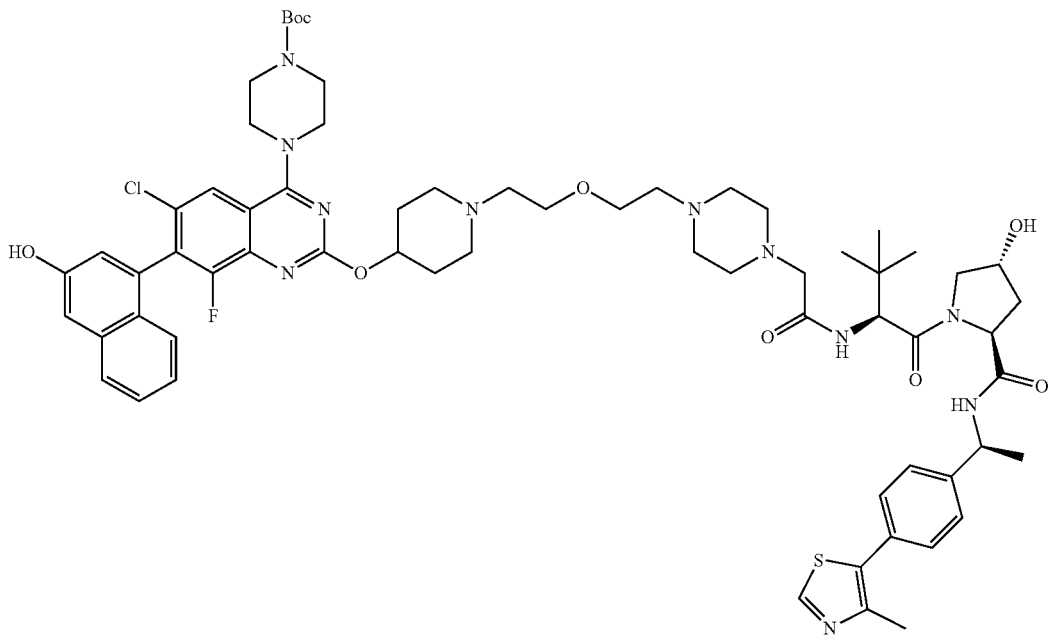 [SMILES: Cc1ncsc1-c1ccc([C@H](C)NC(=O)[C@@H]2C[C@@H](O)CN2C(=O)[C@@H](NC(=O)CN2CCN(CCOCCN3CCC(Oc4nc(N5CCN(C(=O)OC(C)(C)C)CC5)c5cc(Cl)c(-c6cc(O)cc7ccccc67)c(F)c5n4)CC3)CC2)C(C)(C)C)cc1]

To a solution of tert-butyl 4-[6-chloro-8-fluoro-7-(3-hydroxy-1-naphthyl)-2-(4-piperidyloxy)quinazolin-4-yl]piperazine-1-carboxylate (70 mg, 0.1 mmol, 1 eq, trifluoroacetate) in methanol (1 mL) was added sodium acetic (24 mg, 0.29 mmol, 3 eq) at 20° C. The reaction mixture was stirred at 20° C. for 20 minutes. Then acetic acid (12 mg, 0.2 mmol, 2 eq) and a solution of (2S,4R)-1-[(2S)-3,3-dimethyl-2-[[2-[4-[2-(2-oxoethoxy)ethyl]piperazin-1-yl]acetyl]amino]butanoyl]-4-hydroxy-N-[(1S)-1-[4-(4-methylthiazol-5-yl)phenyl]ethyl]pyrrolidine-2-carboxamide (73 mg, 0.11 mmol, 1.15 eq) in dichloromethane (3 mL) were added and the mixture was cooled to 0° C. Sodium cyanoborohydride (9 mg, 0.15 mmol, 1.5 eq) was added and the mixture was stirred at 20° C. for 14 hours. The solution was purified by prep-TLC (8% methanol in dichloromethane) to get tert-butyl 4-[6-chloro-8-fluoro-2-[[1-[2-[2-[4-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]piperazin-1-yl]ethoxy]ethyl]-4-piperidyl]oxy]-7-(3-hydroxy-1-naphthyl)quinazolin-4-yl]piperazine-1-carboxylate (53 mg, 0.04 mmol, 38% yield, 87% purity) as a colorless oil. LC/MS (ESI) m/z: 1238.6 [M+1]$^+$.

Step 12: Preparation of (2S,4R)-1-((2S)-2-(2-(4-(2-(2-(4-((6-chloro-8-fluoro-7-(3-hydroxynaphthalen-1-yl)-4-(piperazin-1-yl)quinazolin-2-yl)oxy)piperidin-1-yl)ethoxy)ethyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide

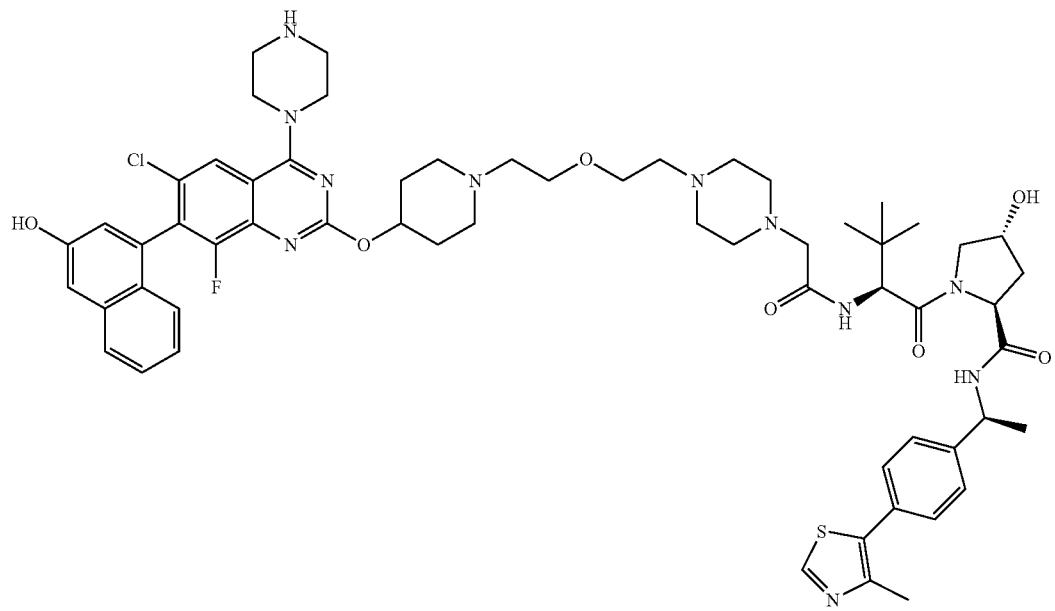 [SMILES: Cc1ncsc1-c1ccc([C@H](C)NC(=O)[C@@H]2C[C@@H](O)CN2C(=O)[C@@H](NC(=O)CN2CCN(CCOCCN3CCC(Oc4nc(N5CCNCC5)c5cc(Cl)c(-c6cc(O)cc7ccccc67)c(F)c5n4)CC3)CC2)C(C)(C)C)cc1]

To a solution of tert-butyl 4-[6-chloro-8-fluoro-2-[[1-[2-[2-[4-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethyl]piperazin-1-yl]ethoxy]ethyl]-4-piperidyl]oxy]-7-(3-hydroxy-1-naphthyl)quinazolin-4-yl]piperazine-1-carboxylate (52 mg, 0.04 mmol, 1 eq) in dichloromethane (3 mL) was added trifluoroacetic acid (0.5 M, 0.08 mL, 1 eq). The mixture was stirred at 15° C. for 1 hour. The reaction mixture was concentrated under vacuum to get (2S,4R)-1-[(2S)-2-[[2-[4-[2-[2-[4-[6-chloro-8-fluoro-7-(3-hydroxy-1-naphthyl)-4-piperazin-1-yl-quinazolin-2-yl]oxy-1-piperidyl]ethoxy]ethyl]piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (52 mg, trifluoroacetate) as a colorless oil.

Step 13: Preparation of (2S,4R)-1-((2S)-2-(2-(4-(2-(2-(4-((4-(4-acryloylpiperazin-1-yl)-6-chloro-8-fluoro-7-(3-hydroxynaphthalen-1-yl)quinazolin-2-yl)oxy)piperidin-1-yl)ethoxy)ethyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide To a solution of (2S,4R)-1-[(2S)-2-[[2-[4-[2-[2-[4-[6-chloro-8-fluoro-7-(3-hydroxy-1-naphthyl)-4-piperazin-1-yl-quinazolin-2-yl]oxy-1-piperidyl]ethoxy]ethyl]piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (52 mg, 41.18 umol, 1 eq, trifluoroacetate) in N,N-dimethylformamide (1 mL) and dichloromethane (5 mL) was added 2,6-lutidine (176 mg, 1.65 mmol, 40 eq). The reaction mixture was cooled to −70° C. Then a solution of prop-2-enoyl chloride (2.61 mg, 0.03 mmol, 0.7 eq) in dichloromethane (0.23 mL) was added and the mixture was stirred at −70° C. for 10 minutes. Dichloromethane (20 mL) and water (15 mL) were added and the mixture was separated. The organic layer was dried over sodium sulfate then concentrated to get the residue. The residue was purified by prep-HPLC to get (2S,4R)-1-[(2S)-2-[[2-[4-[2-[2-[4-[6-chloro-8-fluoro-7-(3-hydroxy-1-naphthyl)-4-(4-prop-2-enoylpiperazin-1-yl)quinazolin-2-yl]oxy-1-piperidyl]ethoxy]ethyl]piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (10.2 mg, 0.008 mmol, 20% yield, 98% purity) as a white solid. LC/MS (ESI) m/z: 1202.6 [M+1]$^+$; $^1$H-NMR (400 MHz, DMSO-d$_6$) δ 8.98 (s, 1H), 8.74-8.38 (m, 1H), 8.27 (s, 2H), 8.00 (s, 1H), 7.80 (d, J=8.3 Hz, 1H), 7.74-7.49 (m, 1H), 7.46-7.39 (m, 3H), 7.38-7.32 (m, 2H), 7.28 (d, J=2.3 Hz, 1H), 7.25-7.16 (m, 2H), 7.06 (d, J=2.3 Hz, 1H), 6.83 (dd, J=10.5, 16.6 Hz, 1H), 6.18 (dd, J=2.3, 16.7 Hz, 1H), 5.78-5.70 (m, 1H), 5.03 (td, J=4.4, 8.3 Hz, 1H), 4.88 (quin, J=7.0 Hz, 1H), 4.53-4.33 (m, 2H), 4.30-4.20 (m, 1H), 3.92 (br d, J=2.5 Hz, 4H), 3.85 (br s, 2H), 3.77 (br s, 2H), 3.60-3.55 (m, 4H), 3.49 (br s, 10H), 3.02 (br d, J=16.1 Hz, 1H), 2.91-2.83 (m, 2H), 2.78 (br s, 2H), 2.47 (br s, 4H), 2.45 (s, 3H), 2.30-2.22 (m, 2H), 2.10-1.95 (m, 3H), 1.80-1.62 (m, 1H), 1.80-1.62 (m, 2H), 1.48-1.33 (m, 3H), 0.90 (s, 8H).

Exemplary Synthesis of (2S,4R)-1-((2S)-14-(4-((4-(4-acryloylpiperazin-1-yl)-6-chloro-8-fluoro-7-(3-hydroxynaphthalen-1-yl)quinazolin-2-yl)amino)phenoxy)-2-(tert-butyl)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide (Exemplary Compound 483)

Step 1: Preparation of 2-(2-(2-((tetrahydro-2H-pyran-2-yl)oxy)ethoxy)ethoxy)ethyl 4-methylbenzenesulfonate

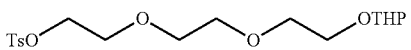

To a solution of 2-(2-(2-hydroxyethoxy)ethoxy)ethyl 4-methylbenzenesulfonate (32.70 g, 107.44 mmol, 1.00 eq) in dichloromethane (300 mL) was added 4-methylbenzenesulfonic acid; pyridine (2.97 g, 11.82 mmol, 0.11 eq), and then 3,4-dihydro-2H-pyran (14.28 g, 169.75 mmol, 15.5 mL, 1.58 eq) was added dropwise at 15° C. The reaction mixture was stirred at 15° C. for 3 hours. The reaction mixture was concentrated under reduced pressure to remove solvent, and then diluted with water (300 mL) and extracted with ethyl acetate (300 mL×2). The combined organic layers were washed with water (300 mL×2), dried over sodium sulfate, filtered and concentrated under reduced pressure to give the product. Compound 2-(2-(2-((tetrahydro-2H-pyran-2-yl)oxy)ethoxy)ethoxy)ethyl 4-methyl benzenesulfonate (37.40 g, 89.92 mmol, 84% yield, 93% purity) was obtained as a white liquid. $^1$H-NMR (400 MHz, CDCl$_3$) δ 7.82 (d, J=8.0 Hz, 2H), 7.36 (d, J=8.4 Hz, 2H), 4.64 (t, J=3.2 Hz, 1H), 4.18 (t, J=4.8 Hz, 2H), 3.73-3.53 (m, 12H), 2.47 (s, 3H), 1.84-1.73 (m, 2H), 1.61-1.52 (m, 4H).

Step 2: Preparation of 2-((1-phenyl-2,6,9,12-tetraoxatetradecan-14-yl)oxy)tetrahydro-2H-pyran

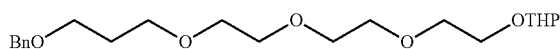

To a solution of 2-(2-(2-((tetrahydro-2H-pyran-2-yl)oxy)ethoxy)ethoxy)ethyl 4-methylbenzenesulfonate (37.00 g, 95.24 mmol, 1.00 eq) in xylene (370 mL) was added potassium hydroxide (6.41 g, 114.29 mmol, 1.20 eq) and 3-(benzyloxy)propan-1-ol (15.83 g, 95.24 mmol, 15.1 mL, 1.00 eq). The mixture was stirred at 130° C. for 3 hours. The reaction mixture was concentrated under reduced pressure to remove solvent. The residue was diluted with ethyl acetate (800 mL). The combined organic layers were washed with water (300 mL×2), dried over sodium sulfate, filtered and concentrated under reduced pressure to give a residue. The residue was purified by flash silica gel chromatography. Compound 2-((1-phenyl-2,6,9,12-tetraoxatetradecan-14-yl)oxy)tetrahydro-2H-pyran (19.00 g, 41.23 mmol, 43% yield, 83% purity) was obtained as a white solid. $^1$H-NMR (400 MHz, CDCl$_3$) δ 7.35-7.28 (m, 5H), 4.64 (t, J=3.6 Hz, 1H), 4.51 (s, 2H), 3.88-3.49 (m, 18H), 2.05-1.26 (m, 8H).

Step 3: Preparation of ethyl 2-(2-(2-(2-(4-nitrophenoxy)ethoxy)ethoxy)ethoxy)acetate

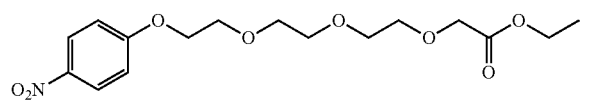 [SMILES: CCOC(=O)COCCOCCOCCOc1ccc(N)cc1]

To a solution of ethyl 2-[2-[2-[2-(p-tolylsulfonyloxy)ethoxy]ethoxy]ethoxy]acetate (3 g, 7.68 mmol, 1 eq) and 4-nitrophenol (1.28 g, 9.22 mmol, 1.2 eq) in dimethyl formamide (10 mL) was added potassium carbonate (2.12 g, 15.37 mmol, 2 eq). The reaction mixture was stirred at 50° C. for 12 hours. The reaction mixture was quenched by addition water (20 mL), and then diluted with water (30 mL), filtered and extracted with ethyl acetate (40 mL×3). The combined organic layers were washed with brine (80 mL), dried over anhydrous sodium sulfate, filtered and concentrated under reduced pressure to give a residue. The residue was purified by prep-HPLC. The desired compound ethyl 2-[2-[2-[2-(4-nitrophenoxy)ethoxy]ethoxy]ethoxy]acetate (1.3 g, 3.64 mmol, 47% yield) was obtained as light yellow oil. LC/MS (ESI) m/z: 835.4 [M+1]$^+$; $^1$H-NMR (400 MHz, CDCl$_3$) δ 8.27-8.15 (m, 2H), 7.04-6.94 (m, 2H), 4.28-4.17 (m, 4H), 4.14 (s, 2H), 3.95-3.87 (m, 2H), 3.79-3.66 (m, 8H), 1.28 (t, J=7.2 Hz, 3H).

Step 4: Preparation of ethyl 2-(2-(2-(2-(4-aminophenoxy)ethoxy)ethoxy)ethoxy)acetate

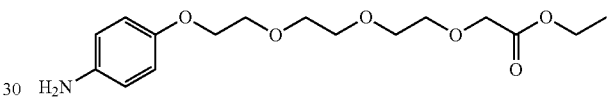

To a solution of ethyl 2-[2-[2-[2-(4-nitrophenoxy)ethoxy]ethoxy]ethoxy]acetate (1.3 g, 3.64 mmol, 1 eq) in ethyl alcohol (10 mL) was added palladium on carbon (500 mg, 10% purity). The reaction mixture was stirred at 40° C. for 12 hours with hydrogen (15 Psi). The reaction mixture was filtered and concentrated under reduced pressure to give the product, compound ethyl 2-[2-[2-[2-(4-aminophenoxy)ethoxy]ethoxy]ethoxy]acetate (1.1 g, 3.36 mmol, 92% yield) as light yellow oil. $^1$H-NMR (400 MHz, CDCl$_3$) δ 6.82-6.73 (m, 2H), 6.69-6.60 (m, 2H), 4.22 (q, J=7.2 Hz, 2H), 4.15 (s, 2H), 4.09-4.03 (m, 2H), 3.86-3.79 (m, 2H), 3.78-3.66 (m, 9H), 1.34-1.21 (m, 4H).

Step 5: Preparation of tert-butyl 4-(7-bromo-6-chloro-8-fluoro-2-((4-((11-oxo-3,6,9,12-tetraoxatetradecyl)oxy)phenyl)amino)quinazolin-4-yl)piperazine-1-carboxylate

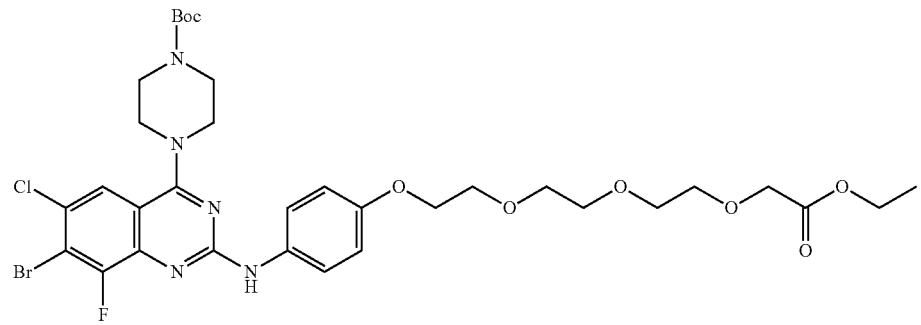 [SMILES: CCOC(=O)COCCOCCOCCOc1ccc(Nc2nc(N3CCN(C(=O)OC(C)(C)C)CC3)c3cc(Cl)c(Br)c(F)c3n2)cc1]

To a solution of ethyl 2-[2-[2-[2-(4-aminophenoxy)ethoxy]ethoxy]ethoxy]acetate (545 mg, 1.67 mmol, 2 eq) and tert-butyl 4-(7-bromo-2,6-dichloro-8-fluoro-quinazolin-4-yl) piperazine-1-carboxylate (400 mg, 0.83 mmol, 1 eq) in isopropanol (10 mL) was added N,N-diisopropylethylamine (431 mg, 3.33 mmol, 4 eq). The reaction mixture was stirred at 95° C. for 12 hours. The reaction mixture was quenched by addition water (20 mL), and then diluted with water (30 mL), filtered and extracted with ethyl acetate (40 mL×3). The combined organic layers were washed with brine (80 mL), dried over anhydrous sodium sulfate, filtered and concentrated under reduced pressure to give a residue. The residue was purified by silica gel chromatography (petroleum ether:ethyl acetate=20:1 to 3:1). The desired compound tert-butyl 4-[7-bromo-6-chloro-2-[4-[2-[2-[2-(2-ethoxy-2-oxo-ethoxy)ethoxy]ethoxy]ethoxy]anilino]-8-fluoro-quinazolin-4-yl]piperazine-1-carboxylate (500 mg, 0.65 mmol, 77% yield) was obtained as yellow solid. LC/MS (ESI) m/z: 772.1 [M+1]$^+$; $^1$H-NMR (400 MHz, CDCl$_3$) δ 7.66-7.51 (m, 3H), 7.08 (s, 1H), 6.92-6.88 (m, 2H), 6.80-6.71 (m, 1H), 6.69-6.59 (m, 1H), 4.27-4.18 (m, 3H), 4.18-4.11 (m, 5H), 4.08-4.04 (m, 1H), 3.89-3.85 (m, 1H), 3.83-3.79 (m, 1H), 3.78-3.60 (m, 13H), 1.54-1.48 (m, 9H), 1.28 (t, J=7.2 Hz, 3H).

Step 6: Preparation of tert-butyl 4-(6-chloro-8-fluoro-7-(3-hydroxynaphthalen-1-yl)-2-((4-((11-oxo-3,6,9,12-tetraoxatetradecyl)oxy)phenyl)amino)quinazolin-4-yl)piperazine-1-carboxylate

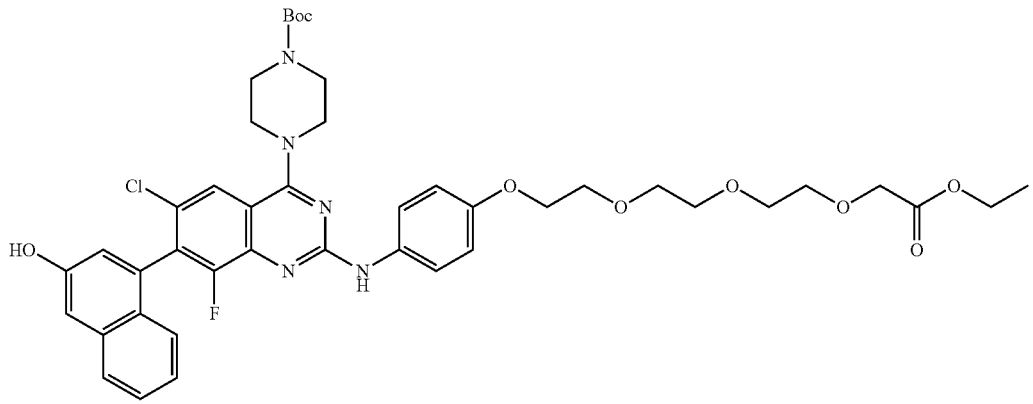 [SMILES: CCOC(=O)COCCOCCOCCOc1ccc(Nc2nc(N3CCN(C(=O)OC(C)(C)C)CC3)c3cc(Cl)c(-c4cc(O)cc5ccccc45)c(F)c3n2)cc1]

To a solution of tert-butyl 4-[7-bromo-6-chloro-2-[4-[2-[2-[2-(2-ethoxy-2-oxo-ethoxy) ethoxy]ethoxy]ethoxy]anilino]-8-fluoro-quinazolin-4-yl]piperazine-1-carboxylate (340 mg, 0.44 mmol, 1 eq) and 4-(4,4,5,5-tetramethyl-1,3,2-dioxaborolan-2-yl)naphthalen-2-ol (143 mg, 0.53 mmol, 1.2 eq) in tetrahydrofuran (10 mL) was added potassium phosphate (1.5 M, 0.9 mL, 3 eq) and [2-(2-aminophenyl)phenyl]palladium(1+); dicyclohexyl-[2-(2,4,6-triisopropyl phenyl)phenyl]phosphane; methanesulfonate (37 mg, 0.04 mmol, 0.1 eq). The reaction mixture was stirred at 60° C. for 12 hours. The reaction mixture was quenched by addition water (10 mL), and then diluted with water (20 mL) and extracted with ethyl acetate (30 mL×3). The combined organic layers were washed with brine (30 mL×2), dried over anhydrous sodium sulfate, filtered and concentrated under reduced pressure to give a residue. The residue was purified by prep-TLC (petroleum ether:ethyl acetate=1:1). The desired compound tert-butyl 4-[6-chloro-2-[4-[2-[2-[2-(2-ethoxy-2-oxo-ethoxy)ethoxy]ethoxy]ethoxy]anilino]-8-fluoro-7-(3-hydroxy-1-naphthyl)quinazolin-4-yl]piperazine-1-carboxylate (122 mg, 0.15 mmol, 33% yield) was obtained as white solid. LC/MS (ESI) m/z: 834.4 [M+1]$^+$; $^1$H-NMR (400 MHz, CDCl$_3$) δ 7.76 (d, J=8.0 Hz, 1H), 7.70 (s, 1H), 7.54 (d, J=7.8 Hz, 2H), 7.43 (t, J=7.6 Hz, 1H), 7.38-7.31 (m, 2H), 7.26-7.20 (m, 2H), 7.15 (s, 1H), 6.90 (d, J=8.8 Hz, 2H), 4.17-4.09 (m, 5H), 3.86 (t, J=4.4 Hz, 2H), 3.80-3.60 (m, 16H), 1.52 (s, 9H), 1.33-1.22 (m, 3H).

Step 7: Preparation of 2-(2-(2-(2-(4-((4-(4-(tert-butoxycarbonyl)piperazin-1-yl)-6-chloro-8-fluoro-7-(3-hydroxynaphthalen-1-yl)quinazolin-2-yl)amino)phenoxy)ethoxy)ethoxy)ethoxy)acetic acid

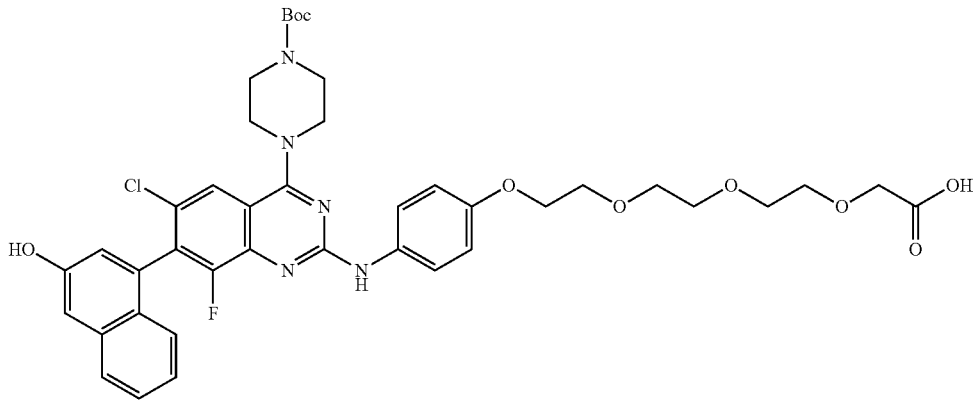 [SMILES: CC(C)(C)OC(=O)N1CCN(c2nc(Nc3ccc(OCCOCCOCCOCC(=O)O)cc3)nc3c(F)c(-c4cc(O)cc5ccccc45)c(Cl)cc23)CC1]

To a solution of tert-butyl 4-[6-chloro-2-[4-[2-[2-[2-(2-ethoxy-2-oxo-ethoxy)ethoxy]ethoxy]ethoxy]anilino]-8-fluoro-7-(3-hydroxy-1-naphthyl)quinazolin-4-yl]piperazine-1-carboxylate (180 mg, 0.21 mmol, 1 eq) in tetrahydrofuran (5 mL) and water (2 mL) was added lithium hydroxide monohydrate (18 mg, 0.43 mmol, 2 eq). The reaction mixture was stirred at 15° C. for 12 hours. The residue was adjust pH=4-5 with 1M hydrogen chloride, then extracted with ethyl acetate (30 mL×2). The combined organic layers were dried over sodium sulfate, filtered and concentrated under reduced pressure to give the product, compound 2-[2-[2-[2-[4-[[4-(4-tert-butoxycarbonylpiperazin-1-yl)-6-chloro-8-fluoro-7-(3-hydroxy-1-naphthyl)quinazolin-2-yl]amino]phenoxy]ethoxy]ethoxy]ethoxy]acetic acid (170 mg, 0.2 mmol, 92% yield, 94% purity) as a yellow solid. LC/MS (ESI) m/z: 806.4 [M+1]$^+$; $^1$H-NMR (400 MHz, CDCl$_3$) δ 7.74 (d, J=7.2 Hz, 1H), 7.66 (s, 1H), 7.60-7.29 (m, 5H), 7.10-6.96 (m, 1H), 6.83 (s, 2H), 4.07 (d, J=6.4 Hz, 2H), 3.88-3.57 (m, 14H), 2.33-2.24 (m, 2H), 1.58-1.40 (m, 9H), 1.01-0.78 (m, 4H).

Step 8: Preparation of tert-butyl 4-(6-chloro-8-fluoro-2-((4-(((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)oxy)phenyl)amino)-7-(3-hydroxynaphthalen-1-yl)quinazolin-4-yl)piperazine-1-carboxylate

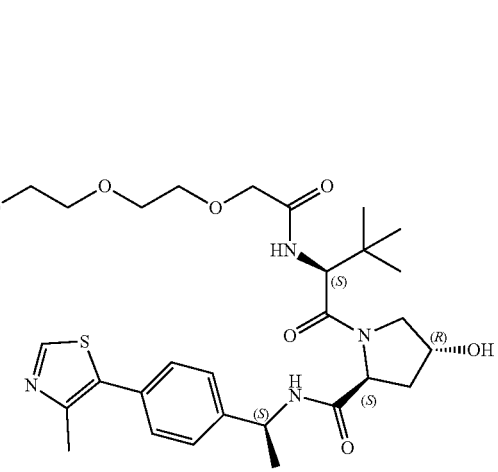

939

To a solution of (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (94 mg, 0.21 mmol, 1 eq) in N,N-dimethylformamide (3 mL) was added N,N-diisopropylethylamine (82 mg, 0.63 mmol, 3 eq) and 2-[2-[2-[2-[4-[[4-(4-tert-butoxycarbonylpiperazin-1-yl)-6-chloro-8-fluoro-7-(3-hydroxy-1-naphthyl)quinazolin-2-yl]amino]phenoxy]ethoxy]ethoxy]ethoxy]acetic acid (170 mg, 0.21 umol, 1 eq), 1-hydroxybenzotriazole (34 mg, 0.25 mmol, 1.2 eq), the reaction mixture was stirred at 15° C. for 0.15 hour, then to the mixture was added 1-(3-dimethylaminopropyl)-3-ethylcarbodiimide (49 mg, 0.25 mmol, 1.2 eq). The reaction mixture was stirred at 15° C. for 0.15 hour. Then heated to 30° C. for 2 hours. The reaction mixture was quenched by addition water (10 mL), and then diluted with water (30 mL), filtered and extracted with ethyl acetate (40 mL×3). The combined organic layers were washed with brine (80 mL), dried over anhydrous sodium sulfate, filtered and concentrated under reduced pressure to give a residue. The residue was purified by prep-TLC (dichloromethane:methanol=10:1). The desired compound tert-butyl 4-[6-chloro-8-fluoro-2-[4-[2-[2-[2-[2-[[(1S)-1-[(2S,4R)-4-hydroxy-2-[[(1S)-1-[4-(4-methylthiazol-5-yl)phenyl]ethyl]

940 carbamoyl]pyrrolidine-1-carbonyl]-2,2-dimethyl-propyl]amino]-2-oxo-ethoxy]ethoxy]ethoxy]ethoxy]anilino]-7-(3-hydroxy-1-naphthyl)quinazolin-4-yl]piperazine-1-carboxylate (180 mg, 0.14 mmol, 65% yield, 94% purity) was obtained as yellow solid. LC/MS (ESI) m/z: 617.2 [M/2+1]⁺; ¹H-NMR (400 MHz, CDCl₃) δ 8.67 (d, J=4.4 Hz, 1H), 7.74 (dd, J=3.2, 8.4 Hz, 1H), 7.69-7.60 (m, 3H), 7.46-7.29 (m, 6H), 7.25-7.09 (m, 2H), 6.92 (d, J=9.2 Hz, 2H), 5.06 (dd, J=6.8, 11.6 Hz, 1H), 4.88-4.75 (m, 1H), 4.59-4.41 (m, 2H), 4.21-4.11 (m, 2H), 4.09-3.98 (m, 2H), 3.96-3.86 (m, 1H), 3.84-3.80 (m, 2H), 3.77-3.55 (m, 16H), 2.49 (d, J=8.8 Hz, 3H), 2.10-1.97 (m, 1H), 1.52 (s, 9H), 1.44 (d, J=6.8 Hz, 3H), 1.30-1.22 (m, 1H), 1.04 (d, J=4.4 Hz, 9H), 0.93-0.79 (m, 1H).

Step 9: Preparation of (2S,4R)-1-((2S)-2-(tert-butyl)-14-(4-((6-chloro-8-fluoro-7-(3-hydroxynaphthalen-1-yl)-4-(piperazin-1-yl)quinazolin-2-yl)amino)phenoxy)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide

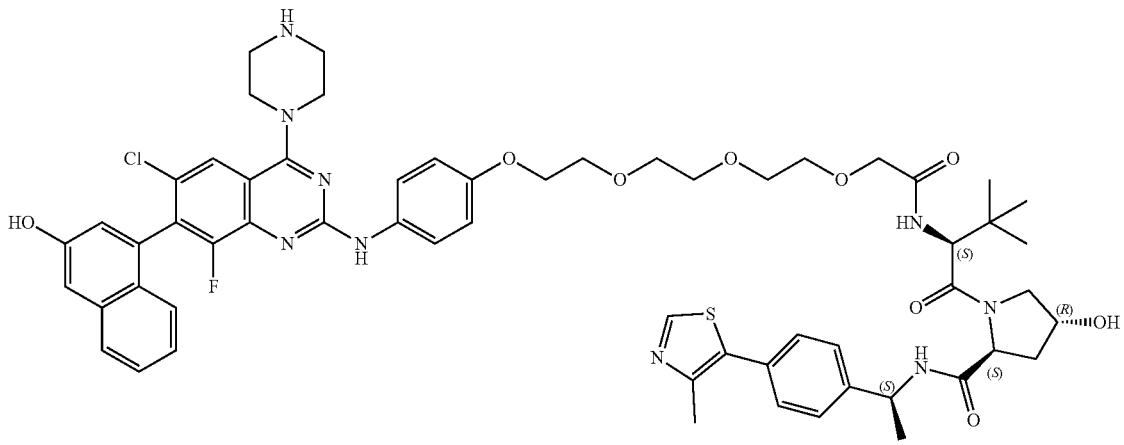

To a solution of tert-butyl 4-[6-chloro-8-fluoro-2-[4-[2-[2-[2-[2-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-2-oxo-ethoxy]ethoxy]ethoxy]ethoxy]anilino]-7-(3-hydroxy-1-naphthyl)quinazolin-4-yl]piperazine-1-carboxylate (180 mg, 0.15 mmol, 1 eq) in dichloromethane (2 mL) was added hydrogen chloride/dioxane (4 M, 2 mL, 55 eq). The reaction mixture was stirred at 15° C. for 0.15 hour. The reaction mixture was concentrated under reduced pressure to give a residue. Acetonitrile was added to the product, then concentrated under reduced pressure to give the product. The desired compound (2S,4R)-1-[(2S)-2-[[2-[2-[2-[2-[4-[[6-chloro-8-fluoro-7-(3-hydroxy-1-naphthyl)-4-piperazin-1-yl-quinazolin-2-yl]amino]phenoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (170 mg, HCl) was obtained as yellow solid. LC/MS (ESI) m/z: 567.3 [M/2+1]⁺.

Step 10: Preparation of (2S,4R)-1-((2S)-14-(4-((4-(4-acryloylpiperazin-1-yl)-6-chloro-8-fluoro-7-(3-hydroxynaphthalen-1-yl)quinazolin-2-yl)amino)phenoxy)-2-(tert-butyl)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide

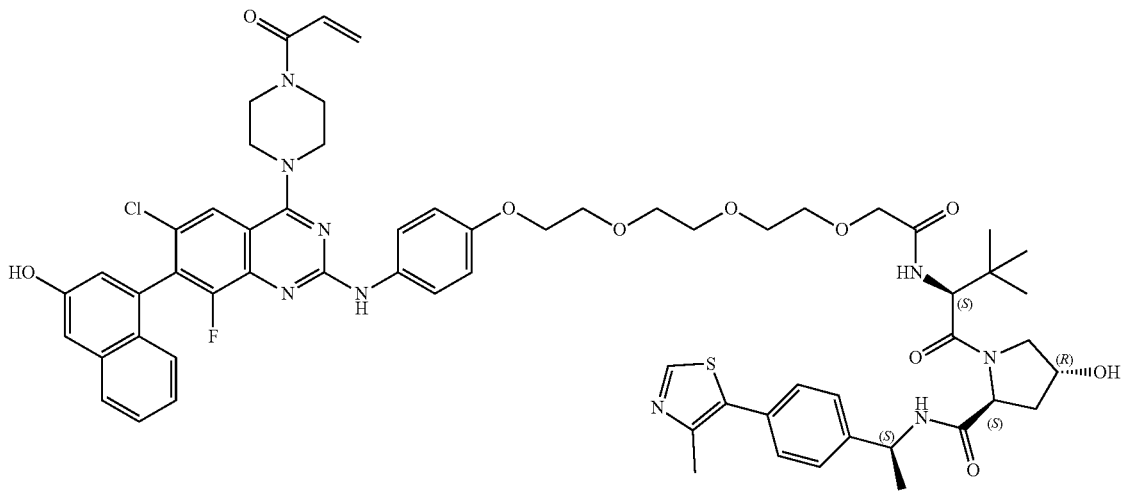

To a solution of (2S,4R)-1-[(2S)-2-[[2-[2-[2-[2-[4-[[6-chloro-8-fluoro-7-(3-hydroxy-1-naphthyl)-4-piperazin-1-yl-quinazolin-2-yl]amino]phenoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (70 mg, 0.06 mmol, 1 eq, HCl) in dichloromethane (5 mL) was added 2,6-lutidine (64 mg, 0.6 mmol, 10 eq). The mixture was stirred at 15° C. for 0.15 hour, then to the mixture was added prop-2-enoyl chloride (5 mg, 0.06 mmol, 1 eq) at −78° C. The reaction mixture was stirred at −78° C. for 0.15 hour. The reaction mixture was quenched by addition water (10 mL), and then diluted with water (20 mL) and extracted with dichloromethane (20 mL×3). The combined organic layers were dried over anhydrous sodium sulfate, filtered and concentrated under reduced pressure to give a residue. The residue was purified by prep-HPLC. The desired compound (2S,4R)-1-[(2S)-2-[[2-[2-[2-[2-[4-[[6-chloro-8-fluoro-7-(3-hydroxy-1-naphthyl)-4-(4-prop-2-enoylpiperazin-1-yl)quinazolin-2-yl]amino]phenoxy]ethoxy]ethoxy]ethoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide (20.3 mg, 0.016 mmol, 26% yield, 94% purity) was obtained as yellow solid. LC/MS (ESI) m/z: 593.9 [M/2+1]$^+$; $^1$H-NMR (400 MHz, DMSO-d$_6$) δ 9.53 (s, 1H), 8.97 (s, 1H), 8.41 (d, J=7.6 Hz, 1H), 8.32-8.25 (m, 1H), 7.92-7.68 (m, 4H), 7.49-7.31 (m, 6H), 7.30-7.19 (m, 3H), 7.08 (d, J=2.1 Hz, 1H), 6.92-6.78 (m, 3H), 6.24-6.10 (m, 1H), 5.80-5.70 (m, 1H), 4.95-4.81 (m, 1H), 4.54 (d, J=9.6 Hz, 1H), 4.44 (t, J=8.0 Hz, 1H), 4.28 (s, 1H), 4.04 (t, J=3.6 Hz, 2H), 3.95 (s, 2H), 3.88-3.69 (m, 9H), 3.66-3.51 (m, 11H), 2.44 (s, 3H), 2.10-1.98 (m, 1H), 1.82-1.71 (m, 1H), 1.44-1.27 (m, 3H), 0.93 (s, 9H).

Exemplary Synthesis of (2S,4R)—N-((1R)-15-((4-(4-acetylpiperazin-1-yl)-6-chloro-8-fluoro-7-(3-hydroxynaphthalen-1-yl)quinazolin-2-yl)amino)-12-methyl-1-(4-(4-methylthiazol-5-yl)phenyl)-13-oxo-3,6,9-trioxa-12-azapentadecyl)-4-hydroxy-1-((R)-3-methyl-2-(3-methylisoxazol-5-yl)butanoyl)pyrrolidine-2-carboxamide (Exemplary Compound 487)

Step 1: Preparation of (2S,4R)-4-hydroxy-1-((R)-3-methyl-2-(3-methylisoxazol-5-yl)butanoyl)-N—((R)-13-(4-(4-methylthiazol-5-yl)phenyl)-5,8,11-trioxa-2-azatridecan-13-yl)pyrrolidine-2-carboxamide

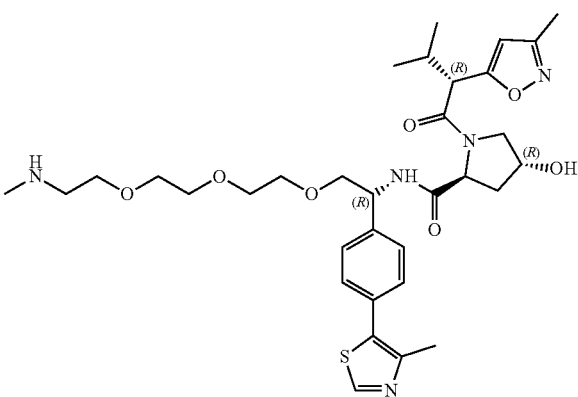

To a solution of tert-butyl N-[2-[2-[2-[(2R)-2-[[(2S,4R)-4-hydroxy-1-[(2R)-3-methyl-2-(3-methylisoxazol-5-yl)butanoyl]pyrrolidine-2-carbonyl]amino]-2-[4-(4-methylthiazol-5-yl)phenyl]ethoxy]ethoxy]ethyl]-N-methyl-carbamate (28 mg, 0.04 mmol, 1 eq) in dichloromethane (1 mL) was added hydrochloric acid/dioxane (4 M, 1 mL, 108.28 eq), the mixture was stirred at 20° C. for 0.5 hour. The mixture was concentrated to give product. Compound (2S,4R)-4-hydroxy-N-[(1R)-2-[2-[2-[2-(methylamino)ethoxy]ethoxy]ethoxy]-1-[4-(4-methylthiazol-5-yl)phenyl]ethyl]-1-[(2R)-3-methyl-2-(3-methylisoxazol-5-yl)butanoyl]pyrrolidine-2-carboxamide was obtained as a pale yellow oil. LC/MS (ESI) m/z: 658.2 [M+1]+.

Step 2: Preparation of (2S,4R)—N-((1R)-15-((4-(4-acetylpiperazin-1-yl)-6-chloro-8-fluoro-7-(3-hydroxynaphthalen-1-yl)quinazolin-2-yl)amino)-12-methyl-1-(4-(4-methylthiazol-5-yl)phenyl)-13-oxo-3,6,9-trioxa-12-azapentadecyl)-4-hydroxy-1-((R)-3-methyl-2-(3-methylisoxazol-5-yl)butanoyl)pyrrolidine-2-carboxamide

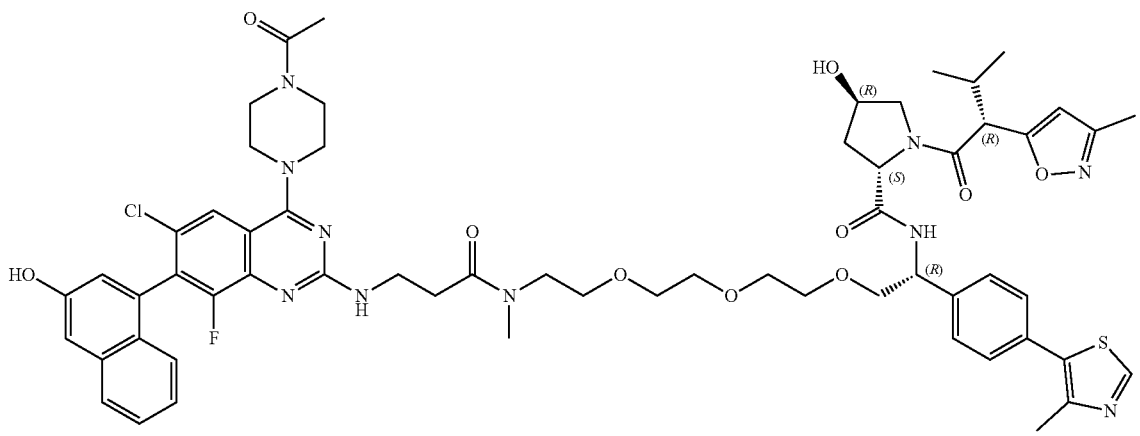

To a solution of (2S,4R)-4-hydroxy-N-[(1R)-2-[2-[2-[2-(methylamino)ethoxy]ethoxy]ethoxy]-1-[4-(4-methylthiazol-5-yl)phenyl]ethyl]-1-[(2R)-3-methyl-2-(3-methylisoxazol-5-yl)butanoyl]pyrrolidine-2-carboxamide (26 mg, 0.04 mmol, 1 eq, hydrochloride), 3-[[4-(4-acetylpiperazin-1-yl)-6-chloro-8-fluoro-7-(3-hydroxy-1-naphthyl)quinazolin-2-yl]amino]propanoic acid (24 mg, 0.04 mmol, 1.2 eq), 1-hydroxybenzotriazole (7 mg, 0.055 mmol, 1.5 eq) and N-(3-dimethylaminopropyl)-N-ethylcarbodiimide hydrochloride (11 mg, 0.055 mmol, 1.5 eq) in N,N-dimethylformamide (1 mL) was added diisopropylethylamine (14 mg, 0.11 mmol, 3 eq). The reaction solution was stirred at 20° C. for 15 hours. The residue was purified by prep-HPLC, the fraction of acetonitrile was removed and the residue was lyophilized to give product. (2S,4R)—N-[(1R)-2-[2-[2-[2-[3-[[4-(4-acetylpiperazin-1-yl)-6-chloro-8-fluoro-7-(3-hydroxy-1-naphthyl)quinazolin-2-yl]amino]propanoyl-methyl-amino]ethoxy]ethoxy]ethoxy]-1-[4-(4-methylthiazol-5-yl)phenyl]ethyl]-4-hydroxy-1-[(2R)-3-methyl-2-(3-methylisoxazol-5-yl)butanoyl]pyrrolidine-2-carboxamide (6.5 mg, 0.005 mmol, 14.7% yield, 97.9% purity) was obtained as a white solid. LC/MS (ESI) m/z: 1177.4 [M+1]+; 1H-NMR (400 MHz, CD3OD) δ 8.90-8.79 (m, 1H), 7.79 (s, 1H), 7.72 (d, J=8.3 Hz, 1H), 7.41-7.29 (m, 5H), 7.25-7.11 (m, 3H), 7.03-6.98 (m, 1H), 6.22-6.16 (m, 1H), 5.06-4.97 (m, 1H), 4.71-4.55 (m, 3H), 4.45-4.29 (m, 1H), 3.81 (br dd, J=8.7, 19.6 Hz, 12H), 3.62-3.48 (m, 12H), 3.14-3.07 (m, 2H), 2.91 (br s, 4H), 2.48-2.33 (m, 4H), 2.24-2.14 (m, 7H), 1.99-1.86 (m, 1H), 1.06-0.91 (m, 3H), 0.87-0.74 (m, 3H).

Exemplary Synthesis of (2S,4R)—N-((1R)-15-((4-(4-acetylpiperazin-1-yl)-6-chloro-8-fluoro-7-(3-hydroxynaphthalen-1-yl)quinazolin-2-yl)amino)-12-methyl-1-(4-(4-methylthiazol-5-yl)phenyl)-13-oxo-3,6,9-trioxa-12-azapentadecyl)-4-hydroxy-1-((S)-3-methyl-2-(3-methylisoxazol-5-yl)butanoyl)pyrrolidine-2-carboxamide (Exemplary Compound 488)

Step 1: Preparation of (2S,4R)-4-hydroxy-1-((S)-3-methyl-2-(3-methylisoxazol-5-yl)butanoyl)-N—((R)-13-(4-(4-methylthiazol-5-yl)phenyl)-5,8,11-trioxa-2-azatridecan-13-yl)pyrrolidine-2-carboxamide To a solution of tert-butyl N-[2-[2-[2-[(2R)-2-[[(2S,4R)-4-hydroxy-1-[(2S)-3-methyl-2-(3-methylisoxazol-5-yl)butanoyl]pyrrolidine-2-carbonyl]amino]-2-[4-(4-methylthiazol-5-yl)phenyl]ethoxy]ethoxy]ethoxy]ethyl]-N-methyl-carbamate (30 mg, 0.04 mmol, 1 eq) in dichloromethane (1 mL) was added hydrochloric acid/dioxane (4 M, 1 mL, 101.06 eq), the mixture was stirred at 20° C. for 0.5 hour. The mixture was concentrated to give product. (2S,4R)-4-hydroxy-N-[(1R)-2-[2-[2-[2-(methylamino)ethoxy]ethoxy]ethoxy]-1-[4-(4-methylthiazol-5-yl)phenyl]ethyl]-1-[(2S)-3-methyl-2-(3-methylisoxazol-5-yl)butanoyl]pyrrolidine-2-carboxamide was obtained as a pale yellow oil. LC/MS (ESI) m/z: 658.2 [M+1]⁺.

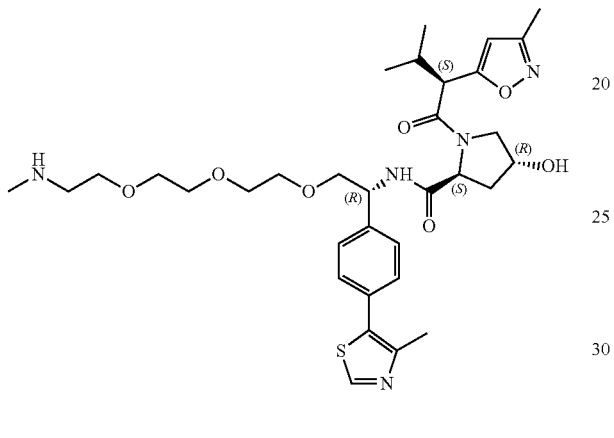

Step 2: Preparation of (2S,4R)—N-((1R)-15-((4-(4-acetylpiperazin-1-yl)-6-chloro-8-fluoro-7-(3-hydroxynaphthalen-1-yl)quinazolin-2-yl)amino)-12-methyl-1-(4-(4-methylthiazol-5-yl)phenyl)-13-oxo-3,6,9-trioxa-12-azapentadecyl)-4-hydroxy-1-((S)-3-methyl-2-(3-methylisoxazol-5-yl)butanoyl) pyrrolidine-2-carboxamide

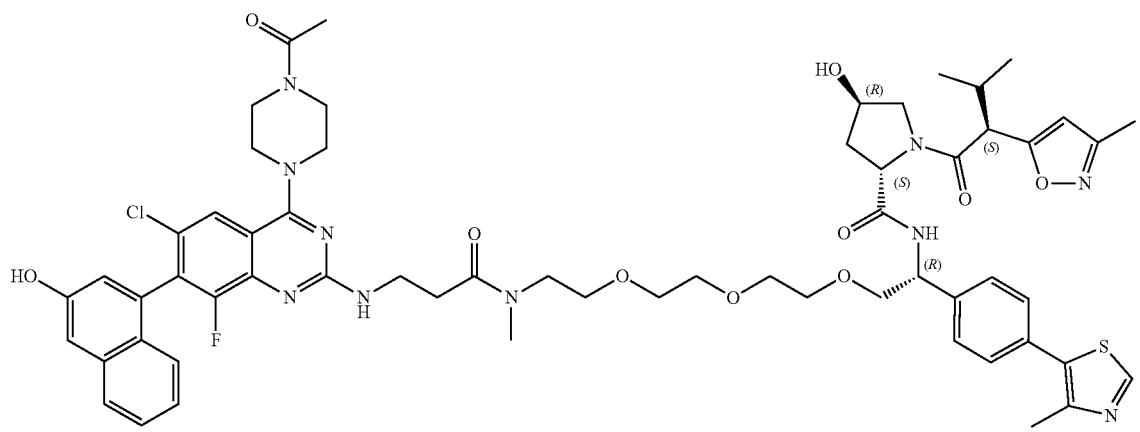

To a solution of (2S,4R)-4-hydroxy-N-[(1R)-2-[2-[2-[2-(methylamino)ethoxy]ethoxy]ethoxy]-1-[4-(4-methylthiazol-5-yl)phenyl]ethyl]-1-[(2S)-3-methyl-2-(3-methylisoxazol-5-yl)butanoyl]pyrrolidine-2-carboxamide (27 mg, 0.04 mmol, 1 eq, hydrochloride), 3-[[4-(4-acetylpiperazin-1-yl)-6-chloro-8-fluoro-7-(3-hydroxy-1-naphthyl)quinazolin-2-yl]amino]propanoic acid (25 mg, 0.046 mmol, 1.2 eq), 1-hydroxybenzotriazole (8 mg, 0.058 mmol, 1.5 eq) and N-(3-dimethylaminopropyl)-N-ethylcarbodiimide hydrochloride (11 mg, 58.33 umol, 1.5 eq) in N,N-dimethylformamide (1 mL) was added diisopropylethylamine (15 mg, 0.12 mmol, 3 eq). The reaction solution was stirred at 20° C. for 15 hours. The residue was purified by prep-HPLC, the fraction of acetonitrile was removed and residue was lyophilized to give product. (2S,4R)—N-[(1R)-2-[2-[2-[2-[3-[[4-(4-acetylpiperazin-1-yl)-6-chloro-8-fluoro-7-(3-hydroxy-1-naphthyl)quinazolin-2-yl]amino]propanoylmethyl-amino]ethoxy]ethoxy]ethoxy]-1-[4-(4-methylthiazol-5-yl)phenyl]ethyl]-4-hydroxy-1-[(2S)-3-methyl-2-(3-methylisoxazol-5-yl)butanoyl]pyrrolidine-2-carboxamide (7.9 mg, 0.006 mmol, 17% yield, 98.7% purity) was obtained as a white solid. LC/MS (ESI) m/z: 1177.4 [M+1]$^+$; $^1$H-NMR (400 MHz, CD$_3$OD) δ 8.84 (d, J=1.2 Hz, 1H), 7.80 (br s, 1H), 7.73 (br d, J=8.6 Hz, 1H), 7.42-7.33 (m, 5H), 7.25-7.13 (m, 3H), 7.03-6.98 (m, 1H), 6.21-6.18 (m, 1H), 5.06 (br s, 1H), 4.69-4.52 (m, 3H), 4.44-4.33 (m, 1H), 3.84-3.71 (m, 12H), 3.62-3.49 (m, 12H), 3.16-3.07 (m, 2H), 2.94-2.70 (m, 4H), 2.45-2.37 (m, 4H), 2.23-2.14 (m, 7H), 2.01-1.88 (m, 1H), 1.04 (d, J=6.5 Hz, 3H), 0.84 (br d, J=6.8 Hz, 3H).

Exemplary Synthesis of (2S,4R)-1-((2S)-2-(3-(4-(2-((4-(4-acetylpiperazin-1-yl)-6-chloro-8-fluoro-7-(3-hydroxynaphthalen-1-yl)quinazolin-2-yl)(3-(dimethylamino)-3-oxopropyl)amino)ethoxy)butoxy)isoxazol-5-yl)-3-methylbutanoyl)-4-hydroxy-N-(4-(4-methylthiazol-5-yl)benzyl)pyrrolidine-2-carboxamide (Exemplary Compound 495)

Step 1: Preparation of ((2-(4-bromobutoxy)ethoxy)methyl)benzene

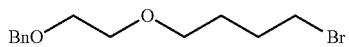

To a solution of 2-benzyloxyethanol (20 g, 131.41 mmol, 18.69 mL, 1 eq) in toluene (150 mL) water (150 mL) was added sodium hydroxide (42.05 g, 1.05 mol, 8 eq) and tetrabutyl ammonium hydrogen sulfate (44.62 g, 131.41 mmol, 1 eq) 1,4-dibromobutane (42.56 g, 197.11 mmol, 23.78 mL, 1.5 eq). The mixture was stirred at 20° C. for 16 hours. Hydrochloric acid (1 N) was added to acidify the water phase (PH=4), and the solution was extracted with ethyl acetate (100 mL×4). The combined organic layers were dried, filtered and concentrate to give a residue. The residue was purified by silica gel column chromatography (Petroleum ether/Ethyl acetate=50/1 to 20/1). Compound 2-(4-bromobutoxy)ethoxymethylbenzene (20 g, 69.64 mmol, 52% yield) was obtained as a colorless oil. $^1$H-NMR (400 MHz, CDCl$_3$) δ 1.70-1.80 (m, 2H), 1.92-2.01 (m, 2H), 3.45 (t, J=6.8 Hz, 2H), 3.52 (t, J=6.4 Hz, 2H), 3.61-3.65 (m, 4H), 4.59 (s, 2H), 7.26-7.32 (m, 1H), 7.36 (d, J=4.8 Hz, 4H).

Step 2: Preparation of methyl 2-(3-(4-(2-(benzyloxy)ethoxy)butoxy)isoxazol-5-yl)-3-methylbutanoate

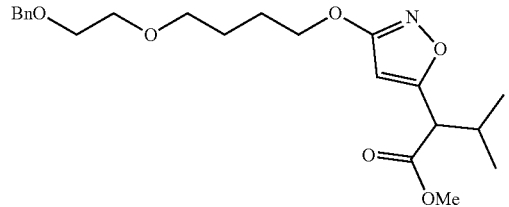 [SMILES: COC(=O)C(c1cc(OCCCCOCCOCc2ccccc2)no1)C(C)C]

A mixture of methyl 2-(3-hydroxyisoxazol-5-yl)-3-methyl-butanoate (3 g, 15.06 mmol, 1 eq), 2-(4-bromobutoxy)ethoxymethylbenzene (4.33 g, 15.06 mmol, 1 eq), potassium carbonate (4.16 g, 30.12 mmol, 2 eq) in N,N-dimethylformamide (40 mL) was degassed and purged with nitrogen (3 times), and then the mixture was stirred at 80° C. for 2 hours under nitrogen atmosphere. The residue was diluted with water (200 mL) and extracted with ethyl acetate (50 mL×3). The combined organic layers were washed with washed with brine (50 mL) and dried over anhydrous sodium sulfate, filtered and concentrated under reduced pressure to give a residue. The residue was purified by silica gel column chromatography (Petroleum ether/Ethyl acetate=10/1 to 1/1). Compound methyl 2-[3-[4-(2-benzyloxyethoxy)butoxy]isoxazol-5-yl]-3-methyl-butanoate (4.2 g, 10.36 mmol, 68% yield) was obtained as a colorless oil. $^1$H-NMR (400 MHz, CD$_3$OD) δ 0.91 (d, J=6.4 Hz, 3H), 0.99 (d, J=6.4 Hz, 3H), 1.67-1.77 (m, 2H), 1.81-1.90 (m, 2H), 2.35 (dquin, J=8.4, 6.4, 6.4, 6.4, 6.4 Hz, 1 H), 3.50-3.59 (m, 3H), 3.60-3.65 (m, 4H), 3.71 (s, 3H), 4.21 (t, J=6.4 Hz, 2H), 4.55 (s, 2H), 6.00 (s, 1H), 7.24-7.31 (m, 1H), 7.32-7.37 (m, 3H).

Step 3: Preparation of methyl 2-(3-(4-(2-hydroxyethoxy)butoxy)isoxazol-5-yl)-3-methylbutanoate

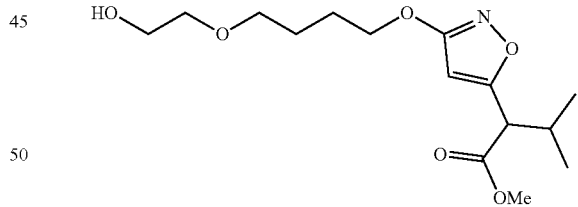

To a solution of methyl 2-[3-[4-(2-benzyloxyethoxy)butoxy]isoxazol-5-yl]-3-methyl-butanoate (4.2 g, 10.36 mmol, 1 eq) in 1,2-dichloroethane (80 mL), water (8 mL) was added dichlorodicyanobenzoquinone (11.76 g, 51.79 mmol, 5 eq). The mixture was stirred at 20° C. for 1 hour. The reaction mixture was quenched by addition saturated sodium bicarbonate solution (150 mL) at 25° C., and then diluted with water (50 mL). The organic phase was separated and extracted with ethyl acetate (50 mL×4). The combined organic layers were washed with brine (20 mL) dried over anhydrous sodium sulfate, filtered and concentrated under reduced pressure to give a residue. The residue was purified by silica gel column chromatography (Petroleum ether/Ethyl acetate=10/1 to 1/1). Compound methyl 2-[3-[4-(2-hydroxyethoxy)butoxy]isoxazol-5-yl]-3-methyl-butanoate (2.7 g, 8.56 mmol, 82% yield) was obtained as a purple liquid. $^1$H-NMR (400 MHz, CD$_3$OD) δ 0.85-0.95 (m, 3H), 0.95-1.04 (m, 3H), 1.66-1.78 (m, 2H), 1.79-1.92 (m, 2H), 2.25-2.43 (m, 1H), 3.46-3.60 (m, 5H), 3.65 (br d, J=3.6 Hz, 2H), 3.72 (br d, J=1.2 Hz, 3H), 4.12-4.28 (m, 2H), 6.00 (s, 1H).

Step 4: Preparation of methyl 2-(3-(4-(2-bromoethoxy)butoxy)isoxazol-5-yl)-3-methylbutanoate

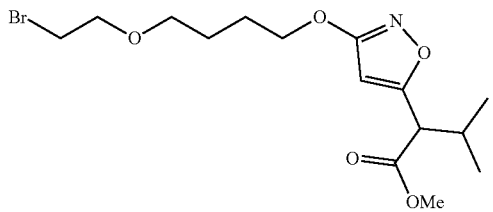 [SMILES: COC(=O)C(c1cc(OCCCCOCCBr)no1)C(C)C]

To a solution of methyl 2-[3-[4-(2-hydroxyethoxy)butoxy]isoxazol-5-yl]-3-methyl-butanoate (2.7 g, 8.56 mmol, 1 eq) in tetrahydrofuran (60 mL) was added carbon tetrabromide (8.52 g, 25.68 mmol, 3 eq), and then triphenylphosphine (6.74 g, 25.68 mmol, 3 eq) in tetrahydrofuran (20 mL) was added dropwise at 0° C. The resulting mixture was stirred at 25° C. for 10 hours. The reaction mixture was concentrated under reduced pressure to remove solvent. The residue was purified by silica gel column chromatography (Petroleum ether/Ethyl acetate=20/1 to 5/1). Compound methyl 2-[3-[4-(2-bromoethoxy)butoxy]isoxazol-5-yl]-3-methyl-butanoate (3.1 g, 8.20 mmol, 95% yield) was obtained as a yellow oil. $^1$H-NMR (400 MHz, CDCl$_3$) δ 0.93 (d, J=6.8 Hz, 3H), 1.00 (d, J=6.4 Hz, 3H), 1.70-1.78 (m, 2H), 1.83-1.91 (m, 2H), 2.30-2.40 (m, 1H), 3.44-3.50 (m, 3H), 3.55 (t, J=6.4 Hz, 2H), 3.73 (s, 3H), 3.73-3.78 (m, 2H), 4.24 (t, J=6.4 Hz, 2H), 5.87 (s, 1H).

Step 5: Preparation of methyl 2-(3-(4-(2-((tert-butoxycarbonyl)(3-(dimethylamino)-3-oxopropyl)amino)ethoxy)butoxy)isoxazol-5-yl)-3-methylbutanoate

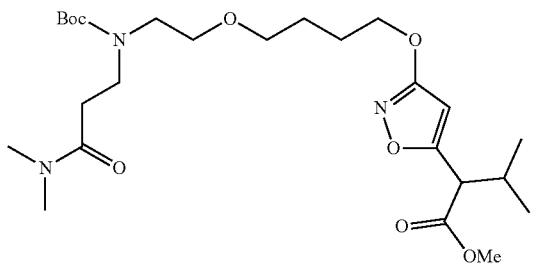 [SMILES: COC(=O)C(c1cc(OCCCCOCCN(CCC(=O)N(C)C)C(=O)OC(C)(C)C)no1)C(C)C]

To a solution of methyl 2-[3-[4-(2-bromoethoxy)butoxy] isoxazol-5-yl]-3-methyl-butanoate (1.5 g, 3.97 mmol, 1 eq) and 3-amino-N,N-dimethyl-propanamide (750 mg, 4.91 mmol, 1.24 eq, hydrochloride) in ethyl alcohol (40 mL) was added N,N-diisopropylethylamine (2.60 g, 20.12 mmol, 3.50 mL, 5.07 eq). The resulting mixture was stirred at 80° C. for 12 hours. The mixture was concentrated to give a residue. Compound methyl 2-[3-[4-[2-[[3-(dimethylamino)-3-oxo-propyl]amino]ethoxy]butoxy]isoxazol-5-yl]-3-methyl-butanoate (1 g) was obtained as a yellow oil. LC/MS (ESI) m/z: 414.3 [M+1]$^+$. To a solution of methyl 2-[3-[4-[2-[[3-(dimethylamino)-3-oxo-propyl]amino]ethoxy]butoxy]isoxazol-5-yl]-3-methyl-butanoate (1 g, 2.42 mmol, 1 eq) and N,N-diisopropylethylamine (1.25 g, 9.67 mmol, 1.68 mL, 4 eq) in dichloromethane (40 mL) was added di-tert-butyl dicarbonate (1.06 g, 4.84 mmol, 1.11 mL, 2 eq) at 0° C. The reaction mixture was stirred at 25° C. for 2 hours. The mixture was poured into ice-water (60 mL) and stirred for 5 minutes. The aqueous phase was extracted with dichloromethane (40 mL×3). The combined organic phase was washed with brine (30 mL), dried with anhydrous sodium sulfate, filtered and concentrated under vacuum. The residue was purified by prep-HPLC. Compound methyl 2-[3-[4-[2-[tert-butoxycarbonyl-[3-(dimethylamino)-3-oxo-propyl]amino]ethoxy]butoxy]isoxazol-5-yl]-3-methyl-butanoate (0.51 g, 992.95 umol, 41% yield) was obtained as a colorless oil. LC/MS (ESI) m/z: 514.2 [M+1].

Step 6: Preparation of 2-(3-(4-(2-((tert-butoxycarbonyl)(3-(dimethylamino)-3-oxopropyl)amino)ethoxy)butoxy)isoxazol-5-yl)-3-methylbutanoic acid

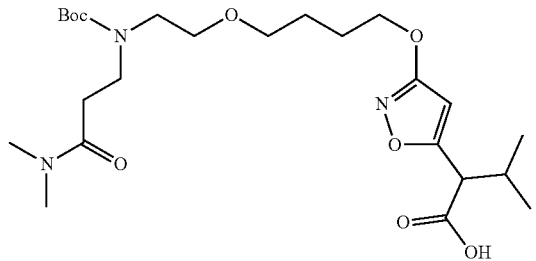 [SMILES: CC(C)C(C(=O)O)c1cc(OCCCCOCCN(CCC(=O)N(C)C)C(=O)OC(C)(C)C)no1]

To a solution of methyl 2-[3-[4-[2-[tert-butoxycarbonyl-[3-(dimethylamino)-3-oxo-propyl]amino]ethoxy]butoxy] isoxazol-5-yl]-3-methyl-butanoate (450 mg, 876.13 umol, 1 eq) in tetrahydrofuran (8 mL) and methyl alcohol (8 mL) and water (8 mL) was added lithium hydroxide monohydrate (110.30 mg, 2.63 mmol, 3 eq). The resulting mixture was stirred at 25° C. for 12 hours. The reaction mixture was adjusted to pH=5 with diluted hydrochloric acid solution (1 N) at 0° C., and extracted with ethyl acetate (30 mL×3). The combined organic layers were washed with brine (10 mL×2), dried over anhydrous sodium sulfate, filtered and concentrated to give the product. Compound 2-[3-[4-[2-[tert-butoxycarbonyl-[3-(dimethylamino)-3-oxo-propyl] amino]ethoxy]butoxy]isoxazol-5-yl]-3-methyl-butanoic acid (450 mg) was obtained as a colorless oil. LC/MS (ESI) m/z: 500.3 [M+1]$^+$.

Step 7: Preparation of tert-butyl (3-(dimethyl-amino)-3-oxopropyl)(2-(4-((5-((S)-1-((2S,4R)-4-hydroxy-2-((4-(4-methylthiazol-5-yl)benzyl)carbam-oyl)pyrrolidin-1-yl)-3-methyl-1-oxobutan-2-yl)isoxazol-3-yl)oxy)butoxy)ethyl)carbamate

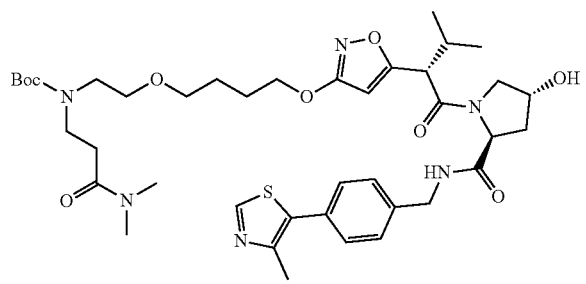 [SMILES: Cc1ncsc1-c1ccc(CNC(=O)[C@@H]2C[C@@H](O)CN2C(=O)[C@H](c2cc(OCCCCOCCN(CCC(=O)N(C)C)C(=O)OC(C)(C)C)no2)C(C)C)cc1]

To a solution of 2-[3-[4-[2-[tert-butoxycarbonyl-[3-(dim-ethylamino)-3-oxo-propyl]amino]ethoxy]butoxy]isoxazol-5-yl]-3-methyl-butanoic acid (400 mg, 800.65 umol, 1 eq) and [dimethylamino(triazolo[4,5-b]pyridin-3-yloxy)methyl-ene]-dimethyl-ammonium; hexafluorophosphate (921 mg, 2.42 mmol, 3.03 eq) in N,N-dimethylformamide (8 mL) was added (2S,4R)-4-hydroxy-N-[[4-(4-methylthiazol-5-yl)phe-nyl]methyl]pyrrolidine-2-carboxamide (255 mg, 803.39 umol, 1 eq) and N,N-diisopropylethylamine (420 mg, 3.25 mmol, 566.04 uL, 4.06 eq). The resulting mixture was stirred at 25° C. for 12 hours. The mixture was poured into ice-water (40 mL) and stirred for 5 minutes. The aqueous phase was extracted with ethyl acetate (30 mL×3). The combined organic phase was washed with brine (15 mL×2), dried with anhydrous sodium sulfate, filtered and concentrated under vacuum. The residue was purified by column chromatography (dichloromethane/methyl alcohol=20/1 to 10/1). Compound tert-butyl N-[3-(dimethylamino)-3-oxo-propyl]-N-[2-[4-[5-[1-[(2S,4R)-4-hydroxy-2-[[4-(4-methyl-thiazol-5-yl)phenyl]methylcarbamoyl]pyrrolidine-1-carbo-nyl]-2-methyl-propyl]isoxazol-3-yl]oxybutoxy]ethyl]carbamate (650 mg, 748.45 umol, 93% yield, 92% purity) was obtained as a off-white solid. LC/MS (ESI) m/z: 799.4 [M+1]⁺.

Step 8: Preparation of tert-butyl (3-(dimethyl-amino)-3-oxopropyl)(2-(4-((5-((S)-1-((2S,4R)-4-hydroxy-2-((4-(4-methylthiazol-5-yl)benzyl)carbam-oyl)pyrrolidin-1-yl)-3-methyl-1-oxobutan-2-yl)isoxazol-3-yl)oxy)butoxy)ethyl)carbamate

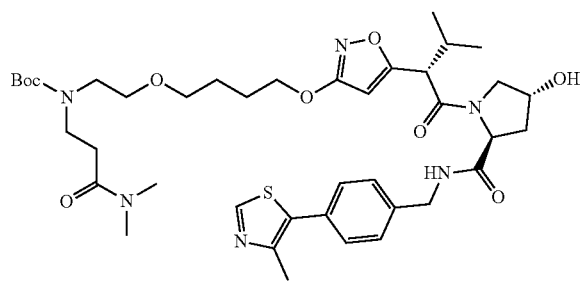 [SMILES: Cc1ncsc1-c1ccc(CNC(=O)[C@@H]2C[C@@H](O)CN2C(=O)[C@H](c2cc(OCCCCOCCN(CCC(=O)N(C)C)C(=O)OC(C)(C)C)no2)C(C)C)cc1]

The tert-butyl N-[3-(dimethylamino)-3-oxo-propyl]-N-[2-[4-[5-[1-[(2S)-4-hydroxy-2-[[4-(4-methylthiazol-5-yl)phenyl]methylcarbamoyl]pyrrolidine-1-carbonyl]-2-methyl-propyl]isoxazol-3-yl]oxybutoxy]ethyl]carbamate (630.00 mg, 788.50 umol, 1 eq) was separated by SFC. The reaction mixture was concentrated under reduced pressure to give a residue. Compound tert-butyl N-[3-(dimethylamino)-3-oxo-propyl]-N-[2-[4-[5-[(1S)-1-[(2S,4R)-4-hydroxy-2-[[4-(4-methylthiazol-5-yl)phenyl]methylcarbamoyl]pyrroli-dine-1-carbonyl]-2-methyl-propyl]isoxazol-3-yl]oxybutoxy]ethyl]carbamate (0.3 g, 364.21 umol, 46% yield, 97% purity) was obtained as a light yellow solid.

Step 9: Preparation of (2S,4R)-1-((S)-2-(3-(4-(2-((3-(dimethylamino)-3-oxopropyl)amino)ethoxy)butoxy)isoxazol-5-yl)-3-methylbutanoyl)-4-hydroxy-N-(4-(4-methylthiazol-5-yl)benzyl)pyrrolidine-2-carboxamide A mixture of tert-butyl N-[3-(dimethylamino)-3-oxo-pro-pyl]-N-[2-[4-[5-[(1S)-1-[(2S,4R)-4-hydroxy-2-[[4-(4-meth-ylthiazol-5-yl)phenyl]methylcarbamoyl]pyrrolidine-1-car-bonyl]-2-methyl-propyl]isoxazol-3-yl]oxybutoxy]ethyl]carbamate (150 mg, 187.74 umol, 1 eq) and hydrochloric/dioxane (4 M, 10 mL) was stirred at 25° C. for 3 hours. The mixture was concentrated to give the product. Compound (2S,4R)-1-[(2S)-2-[3-[4-[2-[[3-(dimethylamino)-3-oxo-pro-pyl]amino]ethoxy]butoxy]isoxazol-5-yl]-3-methyl-bu-tanoyl]-4-hydroxy-N-[[4-(4-methylthiazol-5-yl)phenyl]methyl]pyrrolidine-2-carboxamide (130 mg, 176.79 umol, 94% yield, hydrochloride) was obtained as a light yellow solid. LC/MS (ESI) m/z: 699.3 [M+1]⁺.

Step 10: Preparation of (2S,4R)-1-((2S)-2-(3-(4-(2-((4-(4-acetylpiperazin-1-yl)-6-chloro-8-fluoro-7-(3-hydroxynaphthalen-1-yl)quinazolin-2-yl)(3-(dimethylamino)-3-oxopropyl)amino)ethoxy)butoxy)isoxazol-5-yl)-3-methylbutanoyl)-4-hydroxy-N-(4-(4-methylthiazol-5-yl)benzyl)pyrrolidine-2-carboxamide

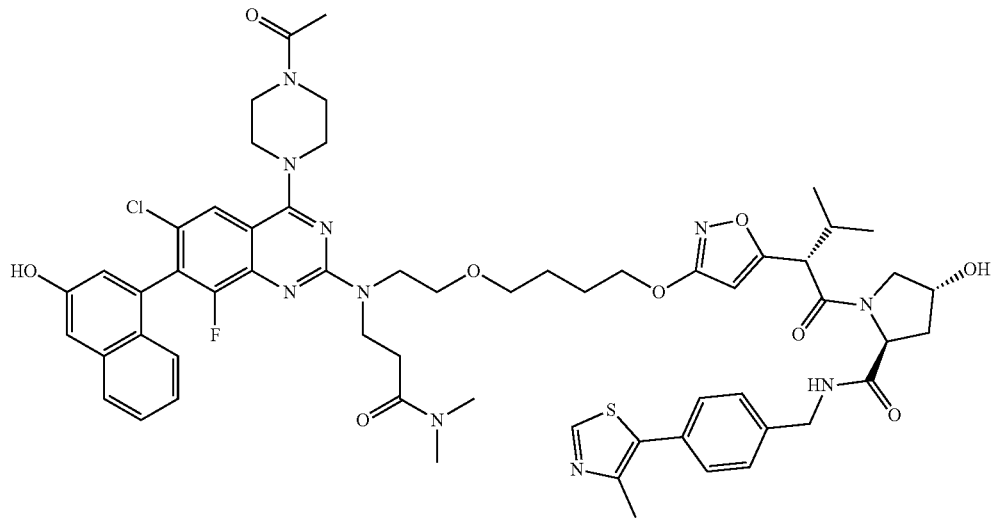 [SMILES: CC(=O)N1CCN(c2nc(N(CCOCCCCOc3cc([C@@H](C(=O)N4C[C@H](O)C[C@H]4C(=O)NCc4ccc(-c5scnc5C)cc4)C(C)C)on3)CCC(=O)N(C)C)nc3c(F)c(-c4cc(O)cc5ccccc45)c(Cl)cc23)CC1]

To a solution of 1-[4-[2,6-dichloro-8-fluoro-7-(3-hydroxy-1-naphthyl)quinazolin-4-yl]piperazin-1-yl]ethanone (40 mg, 82.42 umol, 1 eq) and (2S,4R)-1-[(2S)-2-[3-[4-[2-[[3-(dimethylamino)-3-oxo-propyl]amino]ethoxy]butoxy]isoxazol-5-yl]-3-methyl-butanoyl]-4-hydroxy-N-[[4-(4-methylthiazol-5-yl)phenyl]methyl]pyrrolidine-2-carboxamide (130 mg, 176.79 umol, 2.15 eq, hydrochloride) in dioxane (1 mL) was added N,N-diisopropylethylamine (159.78 mg, 1.24 mmol, 215.33 uL, 15 eq). The mixture was stirred at 100° C. for 10 hours. The mixture was concentrated to give a residue. The residue was purified by semi-preparative reverse phase HPLC. Compound (2S,4R)-1-[(2S)-2-[3-[4-[2-[[4-(4-acetylpiperazin-1-yl)-6-chloro-8-fluoro-7-(3-hydroxy-1-naphthyl)quinazolin-2-yl]-[3-(dimethylamino)-3-oxo-propyl]amino]ethoxy]butoxy]isoxazol-5-yl]-3-methyl-butanoyl]-4-hydroxy-N-[[4-(4-methylthiazol-5-yl)phenyl]methyl]pyrrolidine-2-carboxamide (29.1 mg, 24.09 umol, 29% yield, 95% purity) was obtained as a yellow solid. LC/MS (ESI) m/z: 1169.5 [M+23]$^+$; $^1$H-NMR (400 MHz, CD$_3$OD) δ 0.57-0.65 (m, 1H), 0.76 (d, J=6.4 Hz, 1H), 0.85-0.92 (m, 2H), 1.03 (d, J=6.4 Hz, 2H), 1.54-1.79 (m, 4H), 2.01-2.10 (m, 1H), 2.14 (s, 3H), 2.19-2.27 (m, 1H), 2.27-2.38 (m, 1H), 2.40-2.47 (m, 3H), 2.76-2.93 (m, 5H), 2.99-3.16 (m, 3H), 3.42-3.49 (m, 2H), 3.63-3.81 (m, 12H) 3.84-4.15 (m, 6H), 4.34-4.42 (m, 2H), 4.47 (br s, 1H), 4.54-4.69 (m, 2H), 5.84-5.98 (m, 1H), 6.97-7.05 (m, 1H), 7.10-7.19 (m, 1H), 7.23 (br d, J=2.4 Hz, 2H), 7.30-7.40 (m, 4H), 7.41-7.50 (m, 1H), 7.72 (d, J=8.4 Hz, 1H), 7.75-7.80 (m, 1H), 8.79-8.89 (m, 1H).

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

SPECIFIC EMBODIMENTS OF THE PRESENT DISCLOSURE

The present disclosure encompasses the following specific embodiments. These following embodiments may include all of the features recited in a proceeding embodiment, as specified. Where applicable, the following embodiments may also include the features recited in any proceeding embodiment inclusively or in the alternative (e.g., an eighth embodiment may include the features recited in a first embodiment, as recited, and/or the features of any of the second through seventh embodiments).

In certain embodiments, the description provides the following exemplary KRas bifunctional molecules (exemplary compounds 1-10 of Tables 4 and 5 and 11-249, 254-454, and 458-573 of Tables 6, 8, 10, and 12), including salts, prodrugs, polymorphs, analogs, derivatives, and deuterated forms thereof.

In any aspect or embodiment described herein, the bifunctional compound of the present disclosure includes a PTM from Table 1 (e.g., PTM-1, PTM-2, PTM-3, PTM-4, PTM-5, or PTM-6), a linker from Table 2 (e.g., L-1, L-2, L-3, L-4, L-5, or L-6), and a ULM from Table 3 (e.g., ULM-1, ULM-2, ULM-3, ULM-4, or ULM-5), including salts, prodrugs, polymorphs, analogs, derivatives, and deuterated forms thereof:

TABLE 1

Exemplary PTMs of exemplary PROTACs of the present disclosure

| PTM No. | Chemical Structure |
|---|---|
| PTM-1 | 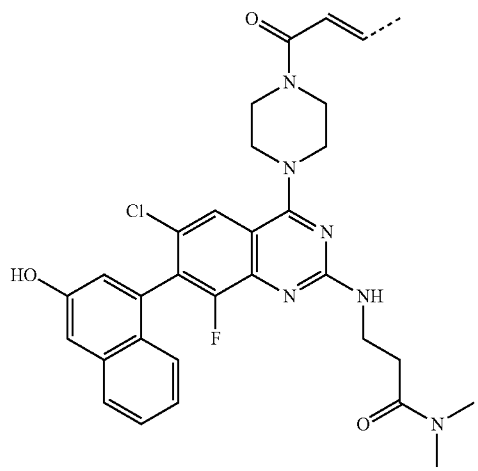 |
| PTM-2 | 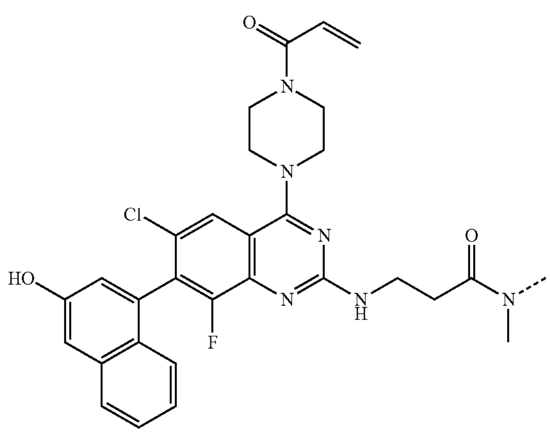 |
| PTM-3 | 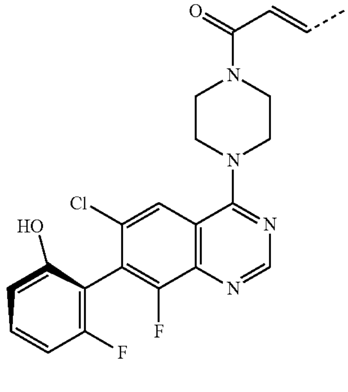 |

TABLE 1-continued
Exemplary PTMs of exemplary PROTACs of the present disclosure
| PTM No. | Chemical Structure |
|---|---|
| PTM-4 | 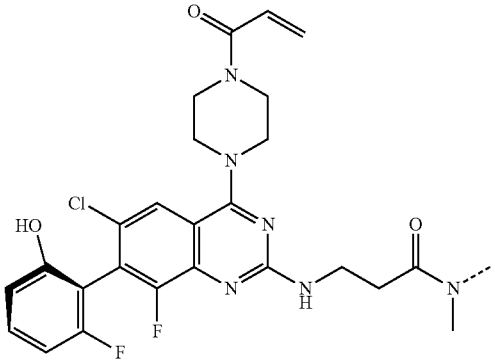 |
| PTM-5 | 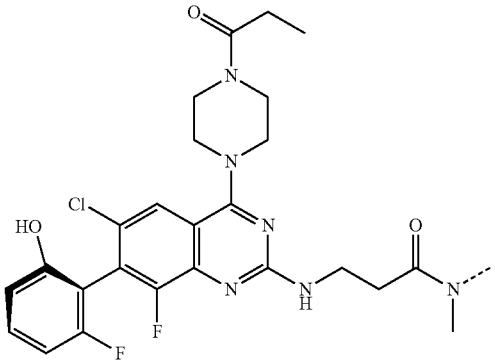 |
| PTM-6 | 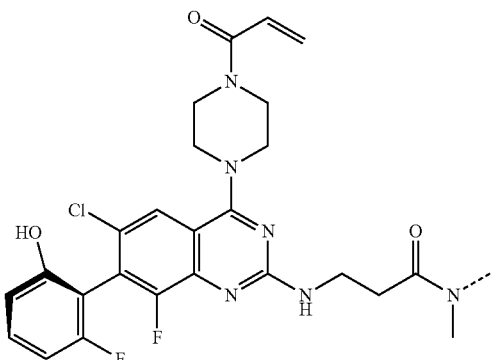 |
| PTM-7 | 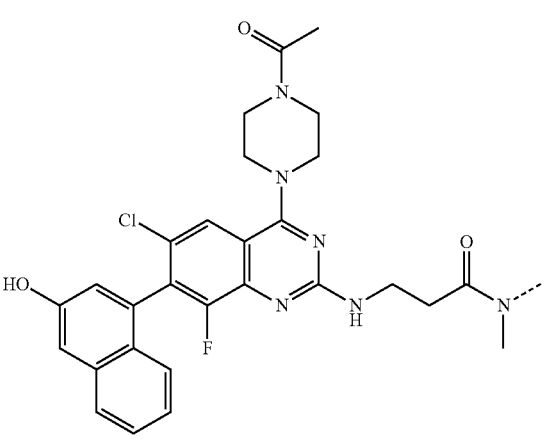 |

TABLE 1-continued

Exemplary PTMs of exemplary PROTACs of the present disclosure

| PTM No. | Chemical Structure |
| --- | --- |
| PTM-8 | 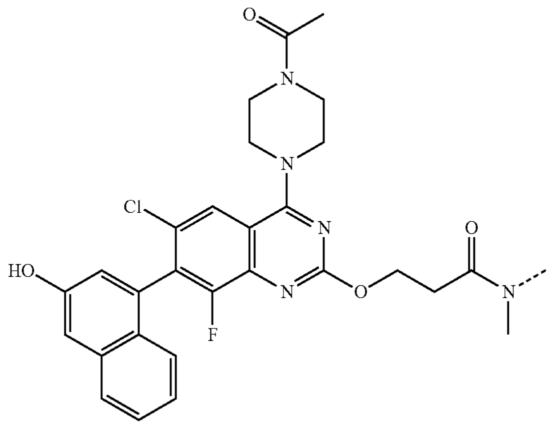 |
| PTM-9 | 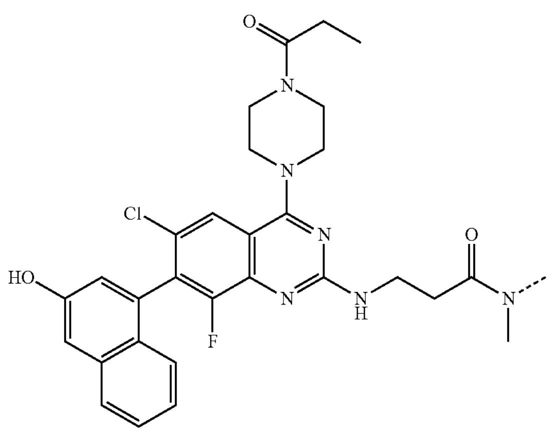 |
| PTM-10 | 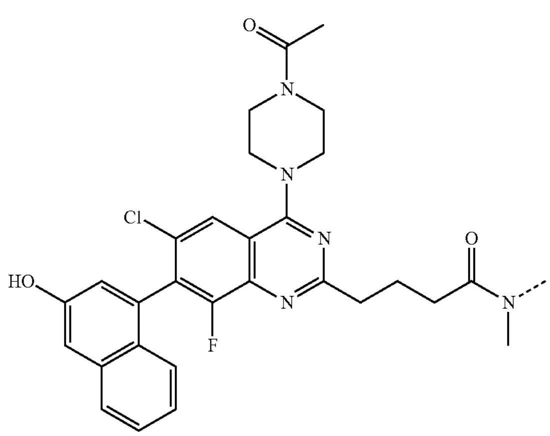 |

TABLE 1-continued
Exemplary PTMs of exemplary PROTACs of the present disclosure
| PTM No. | Chemical Structure |
|---|---|
| PTM-11 | 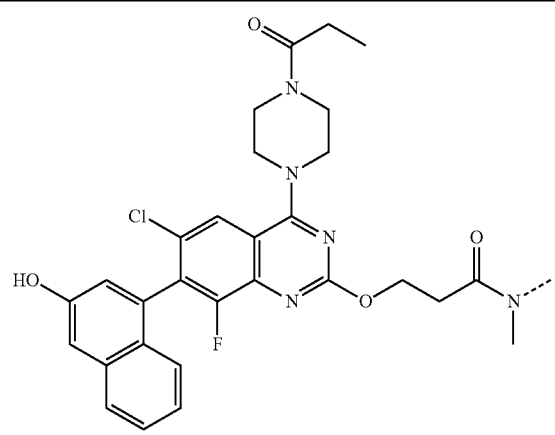 |
| PTM-12 | 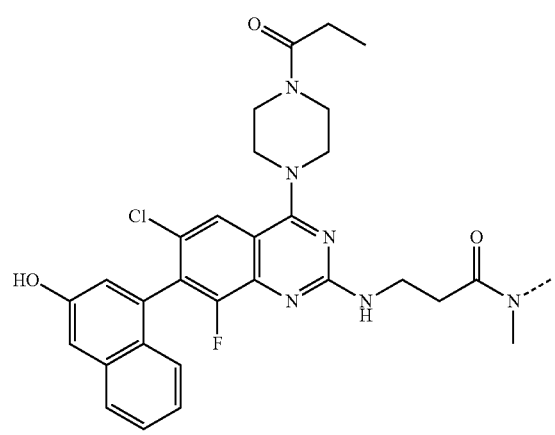 |
TABLE 2
Exemplary linkers of exemplary PROTACs of the present disclosure
| Linker No. | Chemical Structure |
|---|---|
| L-1 | 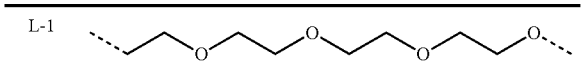 |
| L-2 | 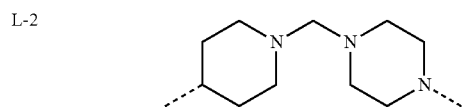 |
| L-3 | 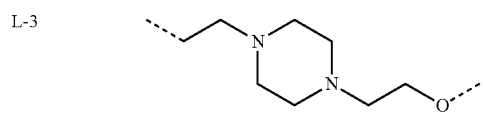 |
| L-4 | 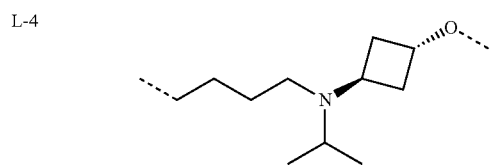 |
TABLE 2-continued
Exemplary linkers of exemplary PROTACs of the present disclosure
| Linker No. | Chemical Structure |
|---|---|
| L-5 | 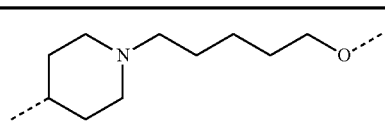 |
| L-6 | 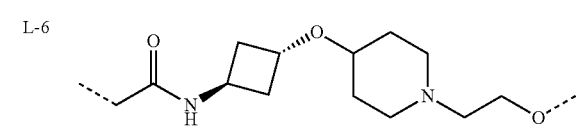 |

TABLE 3

Exemplary ULMs of exemplary PROTACs of the present disclosure

| ULM No. | Chemical Structure |
|---|---|
| ULM-1 | 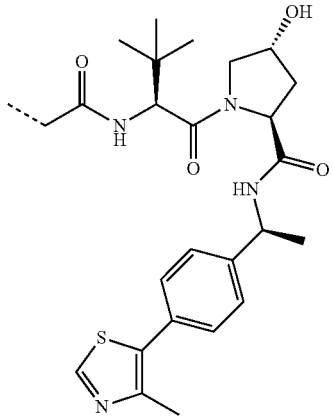 |
| ULM-2 | 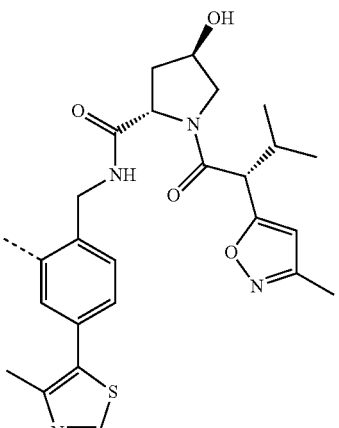 |
| ULM-3 | 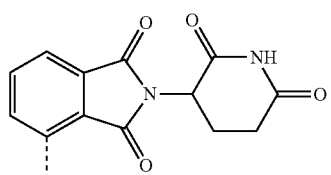 |
| ULM-4 | 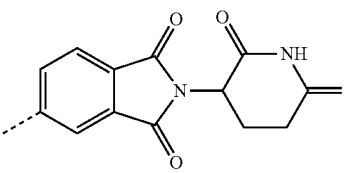 |
| ULM-5 | 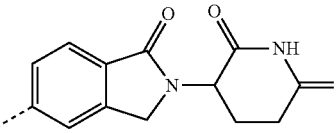 |

In certain exemplary embodiments as described herein, a compound is provided having a linker selected from Table 2 (e.g., L-1, L-2, L-3, L-4, L-5, or L-6) coupled to a PTM from Table 1 (e.g., PTM-1, PTM-2, PTM-3, PTM-4, PTM-5, or PTM-6) and a ULM from Table 3 (e.g., ULM-1, ULM-2, ULM-3, ULM-4, or ULM-5). For example, the PTM of Table 1, the linker of Table 2, and the ULM of Table 3 may be combined in any desired combination, e.g., PTM-1/L-1/ULM-1 or PTM-2/L-1/ULM-1, and so forth thereby forming exemplary compounds of the present disclosure.

An aspect of the present disclosure provides a bifunctional compound having the chemical structure:

ULM-L-PTM, or a pharmaceutically acceptable salt, enantiomer, stereoisomer, solvate, polymorph or prodrug thereof, wherein: the ULM is a small molecule E3 ubiquitin ligase binding moiety that binds an E3 ubiquitin ligase; the PTM is a small molecule comprising a Kirsten rat sarcoma protein (KRas) targeting moiety; and the L is a bond or a chemical linking moiety connecting the ULM and the PTM.

In any aspect or embodiment described herein, the E3 ubiquitin ligase binding moiety that targets an E3 ubiquitin ligase selected from the group consisting of Von Hippel-Lindau (VLM), cereblon (CLM), mouse double-minute homolog 2 (MLM), and IAP (ILM).

In any aspect or embodiment described herein, the PTM is represented by:

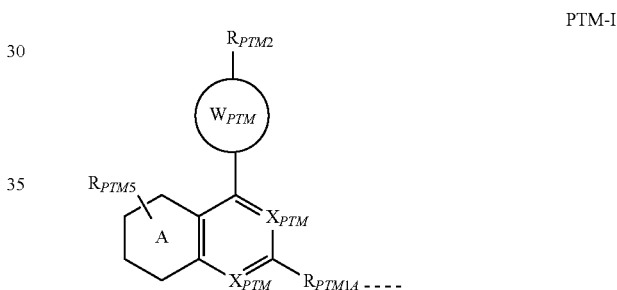

PTM-I

PTM-II

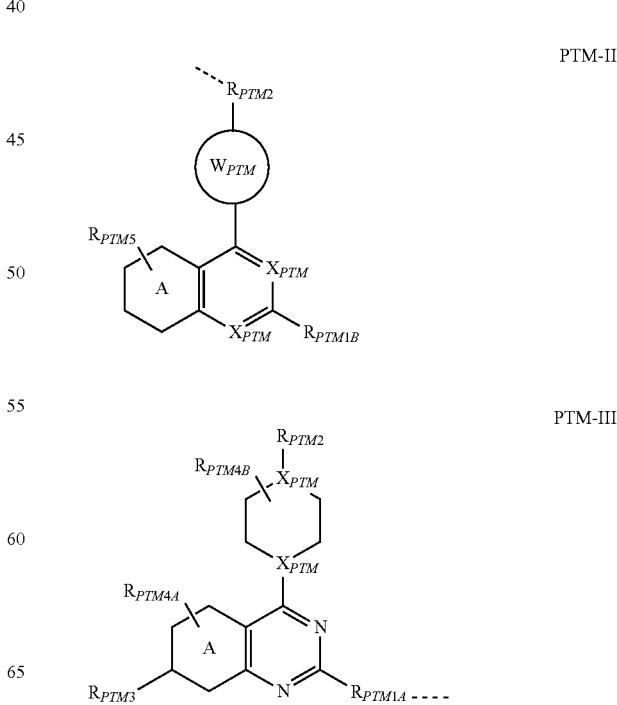

PTM-III

-continued

PTM-IV

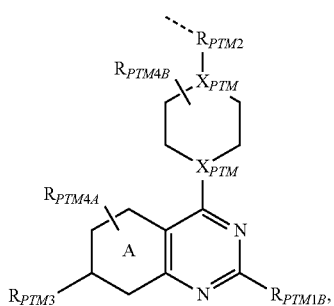

wherein:

is an aryl, heteroaryl, cycloalkyl, or heterocycloalkyl;

$X_{PTM}$ is C or N;

$W_{PTM}$ is chosen from the group consisting of optionally substituted $C_3$-$C_6$ cycloalkyl, and optionally substituted $C_3$-$C_6$ heteroalkyl, optionally substituted $C_3$-$C_6$ heterocycloalkyl, optionally substituted aryl (e.g., optionally substituted $C_5$-$C_7$ aryl), optionally substituted heteroaryl (e.g., optionally substituted $C_5$-$C_7$ heteroaryl);

$R_{PTM1A}$ is $NR_{PTM9}R_{PTM10}$, $OR_{PTM9}R_{PTM10}$, H, optionally substituted alkyl, optionally substituted alkoxy, optionally substituted C3-C6 cycloalkyl, optionally substituted O—(C3-C6 cycloalkyl), optionally substituted —O—$C_{1-4}$ alkyl-$C_{3-6}$cycloalkyl, optionally substituted C3-C6 heteroalkyl, optionally substituted O—(C3-C6 heteroalkyl), optionally substituted O—$C_{1-4}$ alkyl-$C_{3-6}$ heteroalkyl, optionally substituted O—$C_{1-4}$ alkyl-$C_{3-6}$ heterocycloalkyl, optionally substituted aryl (e.g., optionally substituted C5-C7 aryl), optionally substituted O-aryl (e.g., optionally substituted O—(C5-C7 aryl)), optionally substituted heteroaryl (e.g., optionally substituted C5-C7 heteroaryl), optionally substituted O-heteroaryl (e.g., optionally substituted O—(C5-C7 heteroaryl)), optionally substituted

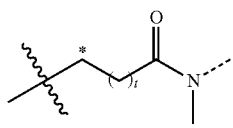

(e.g., optionally substituted with at least one alkyl, such as the * carbon may be optionally substituted with an alkyl), optionally substituted

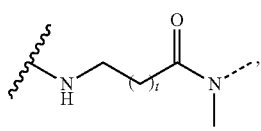

optionally substituted

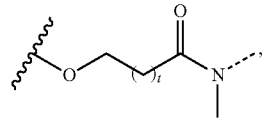

optionally substituted

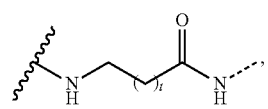

optionally substituted

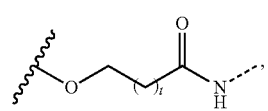

optionally substituted

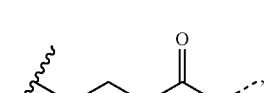

optionally substituted

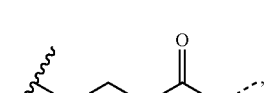

optionally substituted

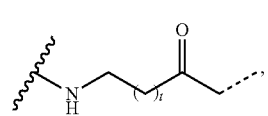

optionally substituted

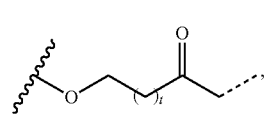

optionally substituted

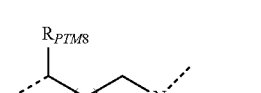

optionally substituted

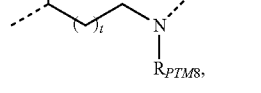

optionally substituted

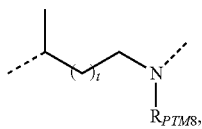

optionally substituted

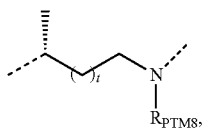

optionally substituted

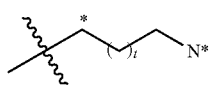

(e.g., optionally substituted with at least one alkyl, such as the * carbon may be optionally substituted with an alkyl), optionally substituted

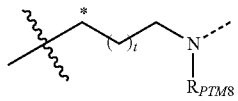

(e.g., optionally substituted with at least one alkyl, such as the * carbon may be optionally substituted with an alkyl), optionally substituted

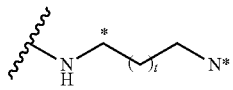

(e.g., optionally substituted with at least one alkyl, such as the * carbon may be optionally substituted with an alkyl), optionally substituted

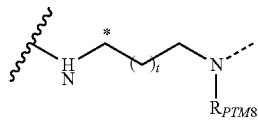

(e.g., optionally substituted with at least one alkyl, such as the * carbon may be optionally substituted with an alkyl), optionally substituted

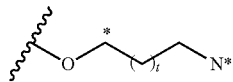

(e.g., optionally substituted with at least one alkyl, such as the * carbon may be optionally substituted with an alkyl), optionally substituted

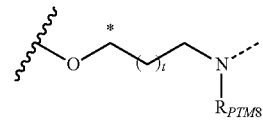

(e.g., optionally substituted with at least one alkyl, such as the * carbon may be optionally substituted with an alkyl), wherein N* is a N atom of a heterocycloalkyl of the linker (L);

$R_{PTM1B}$ is $NR_{PTM9}R_{PTM10}$, $OR_{PTM9}R_{PTM10}$, H, optionally substituted alkyl, optionally substituted O-alkyl, optionally substituted C3-C6 cycloalkyl, optionally substituted O—(C3-C6 cycloalkyl), optionally substituted —O—$C_{1-4}$ alkyl-$C_{3-6}$cycloalkyl, optionally substituted C3-C6 heteroalkyl, optionally substituted O—(C3-C6 heteroalkyl), optionally substituted O—$C_{1-4}$ alkyl-$C_{3-6}$ heteroalkyl, optionally substituted aryl (e.g., optionally substituted C5-C7 aryl), optionally substituted O-aryl (e.g., optionally substituted O—(C5-C7 aryl)), optionally substituted heteroaryl (e.g., optionally substituted C5-C7 heteroaryl), optionally substituted O-heteroaryl (e.g., optionally substituted O(C5-C7 heteroaryl)), optionally substituted

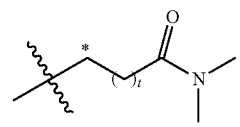

(e.g., optionally substituted with at least one alkyl, such as the * carbon may be optionally substituted with an alkyl), optionally substituted

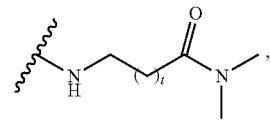

optionally substituted

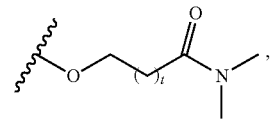

optionally substituted

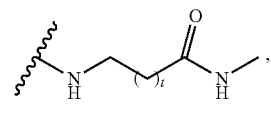

optionally substituted

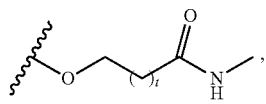

optionally substituted

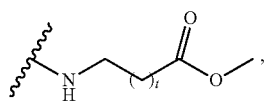

optionally substituted

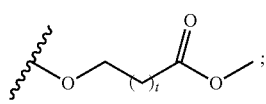

optionally substituted

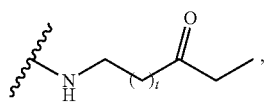

optionally substituted

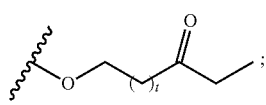

$R_{PTM9}$ and $R_{PTM10}$ are each independently H, optionally substituted C1-C6 alkyl, optionally substituted aliphatic amine, optionally substituted aliphatic amide;

$R_{PTM2}$ is H, (C=O)$R_{PTM2'}$, optionally substituted linear or branched alkyl;

$R_{PTM2'}$ is optionally substituted linear or branched alkyl, optionally substituted alkene, —N($R_{PTM8}$)$_2$, or —C(OH)$_2$;

$R_{PTM3}$ is alkyl, alkoxy, phenyl, or napthalene, each independently substituted with OH, H, halogen;

$R_{PTM4A}$ is OH, H, halogen, optionally substituted linear or branched C1-C6 alkyl;

$R_{PTM4B}$ is OH, H, halogen, optionally substituted linear or branched C1-C6 alkyl;

$R_{PTM5}$ is chosen from the group consisting of optionally substituted aryl, optionally substituted biaryl, optionally substituted heteroaryl, optionally substituted biheteroaryl, optionally substituted C3-C6 cycloalkyl, optionally substituted C3-C6 cycloheteroalkyl, halogen, H, optionally substituted linear or branched alkyl (e.g., optionally substituted linear or branched C1-C6 alkyl), OH, and alkoxy;

$R_{PTM8}$ is a H or an alkyl (e.g., a C1 alkyl, a C2 alkyl, a C3 alkyl, or a C4 alkyl);

t is 0, 1, 2, 3, 4, 5, 6; and the ⟋ indicates the site of attachment of at least one of a linker, ULM, ULM', CLM, CLM', VLM, VLM', ILM, ILM', MLM, MLM', or a combination thereof.

In any aspect or embodiment described herein, the PTM is represented by:

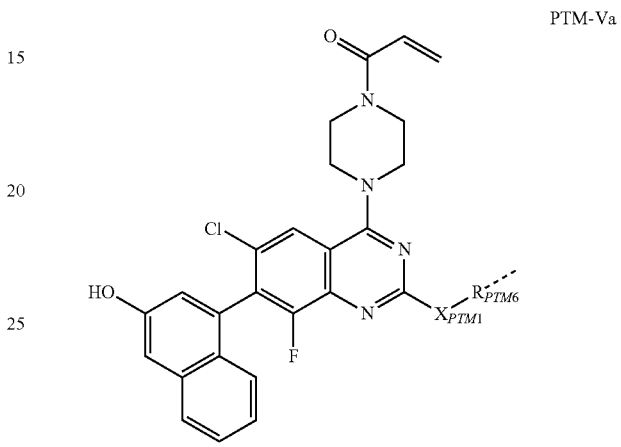

PTM-Va

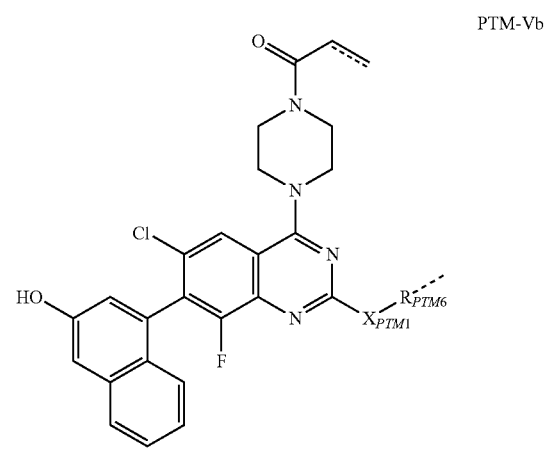

PTM-Vb

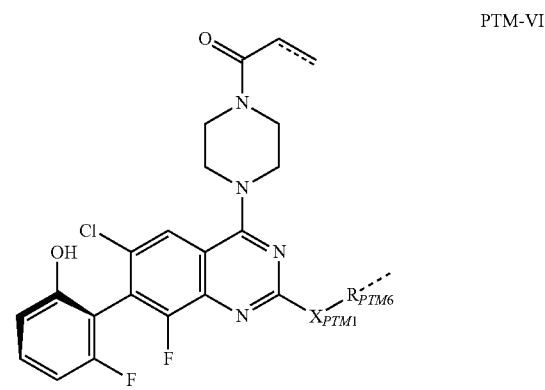

PTM-VI

-continued
PTM-VIIa
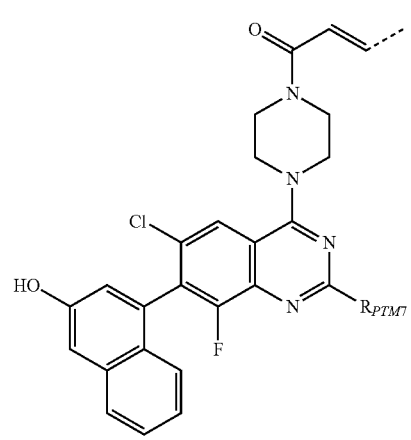
PTM-VIIb
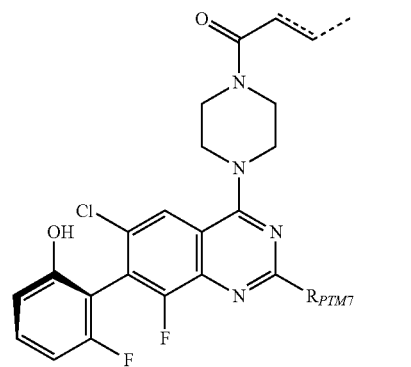
PTM-VIII
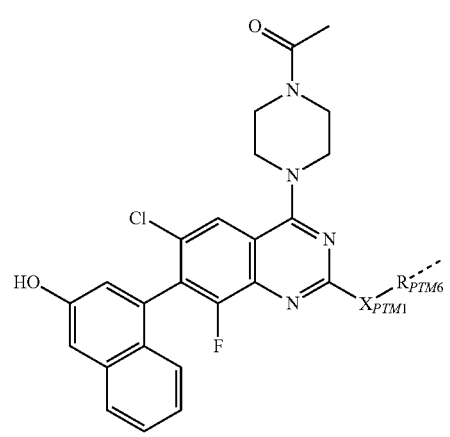
PTM-IXa
-continued
PTM-Xb
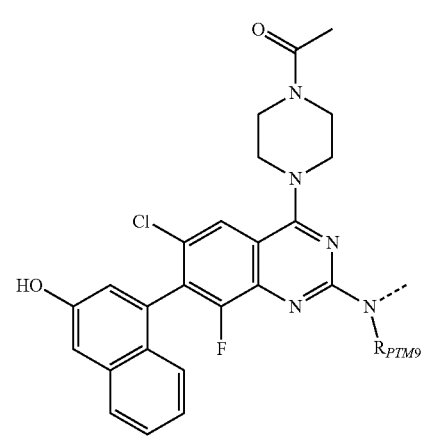
PTM-Xa
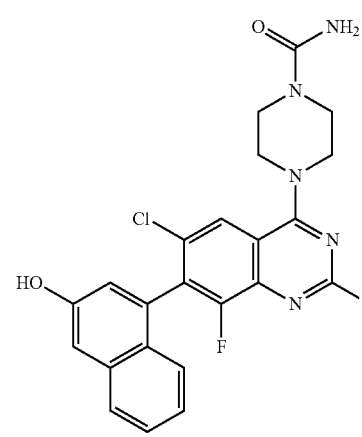
PTM-Xb
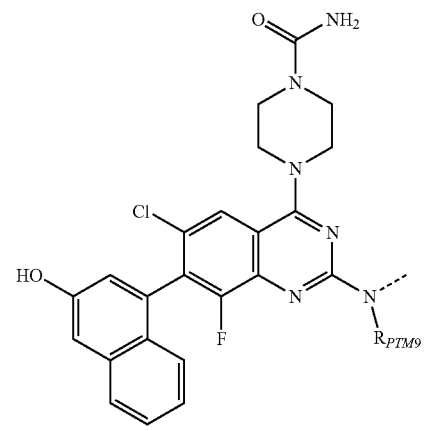
PTM-XI
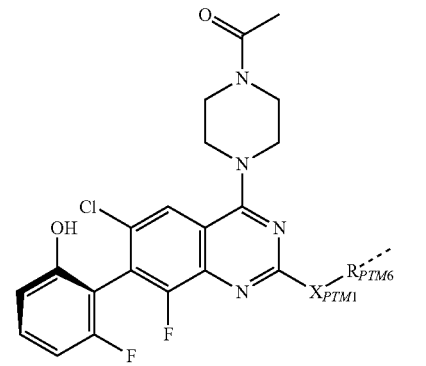

PTM-XII
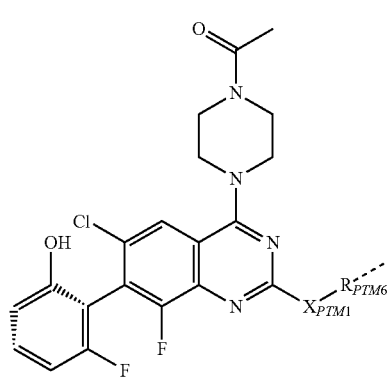
PTM-XVI
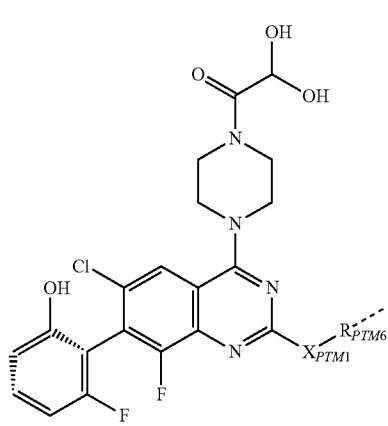
PTM-XIII
PTM-XIV
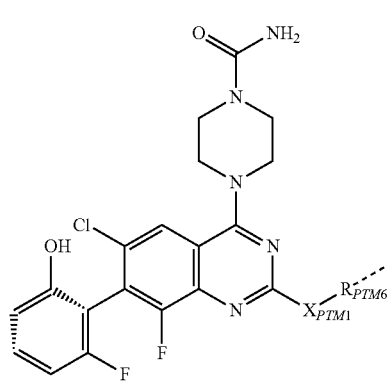
PTM-XVIIa
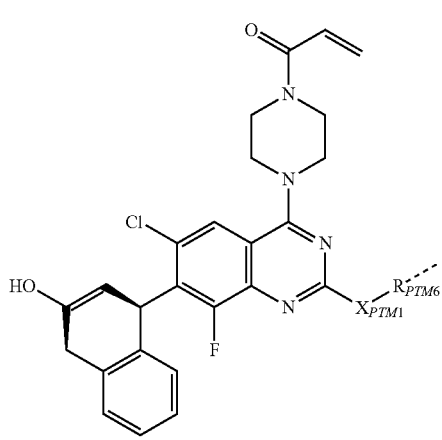
PTM-XV
PTM-XVIIb
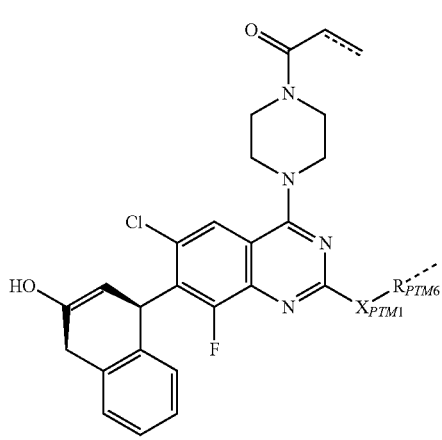

PTM-XVIII
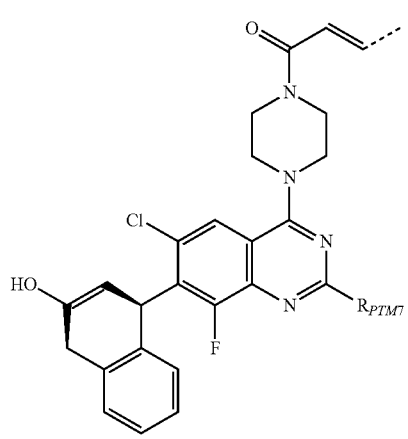
PTM-XIV
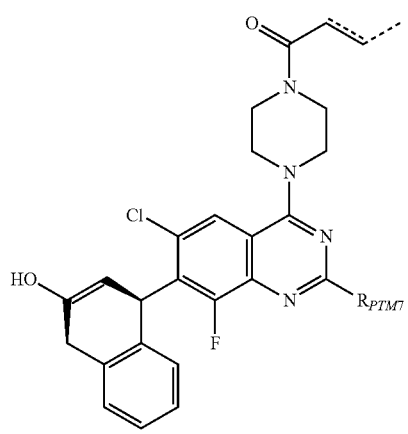
PTM-XV
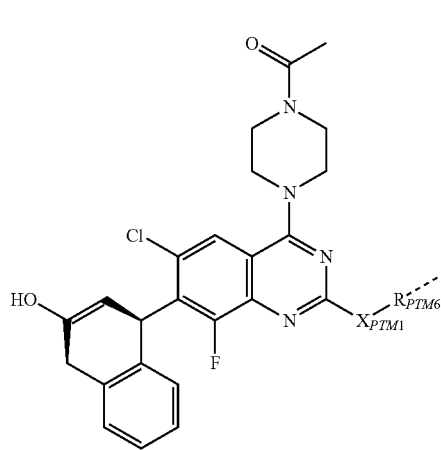
PTM-XVI
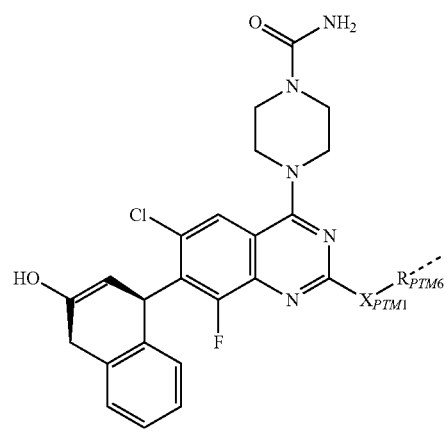
PTM-XVIIa
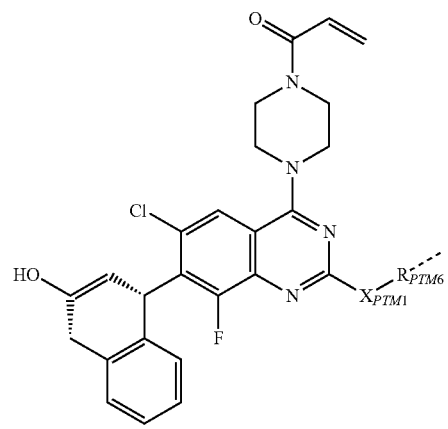
PTM-XVIIb
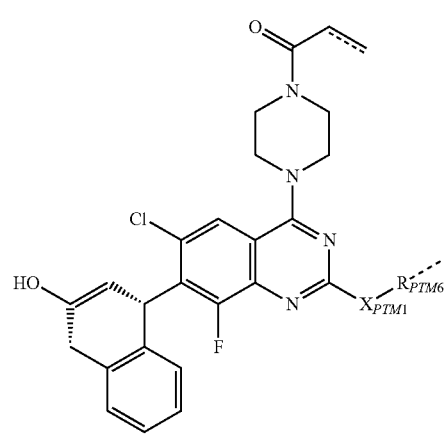

PTM-XVIII
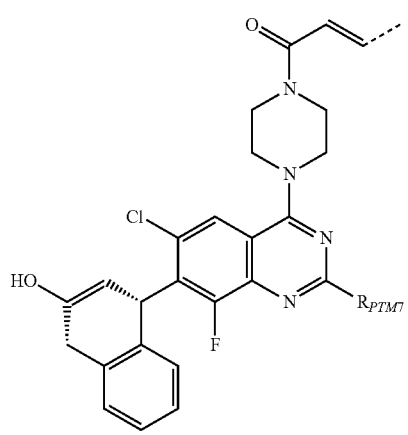
PTM-XIX
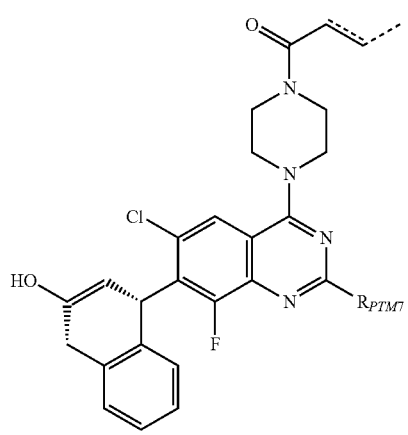
PTM-XX
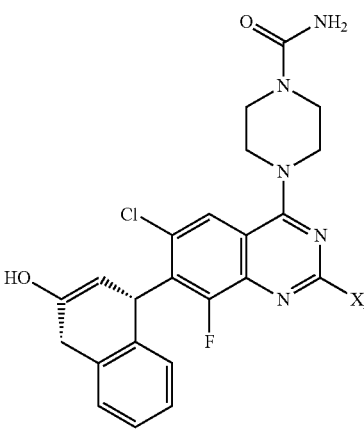
PTM-XXI
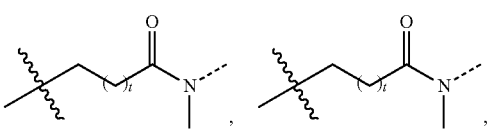
wherein:
$X_{PTM1}$ is NH or O;
$R_{PTM6}$ is aryl, heteroaryl,
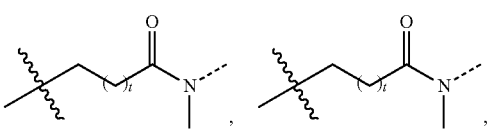
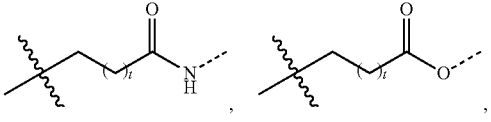
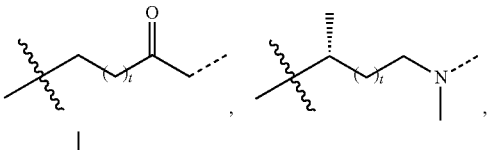
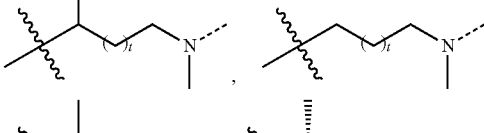
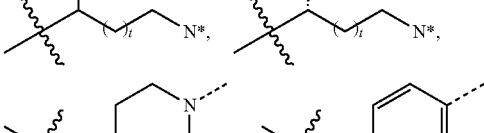
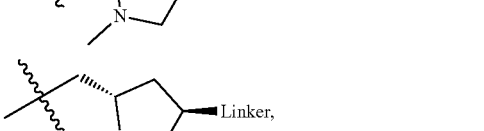
wherein N* a N atom of a heterocycloalkyl (e.g., a C4-C8 heterocycloalkyl) of the linker (L);

R$_{PTM7}$ is H, aryl, O-aryl, heteroaryl, O-heteroaryl,

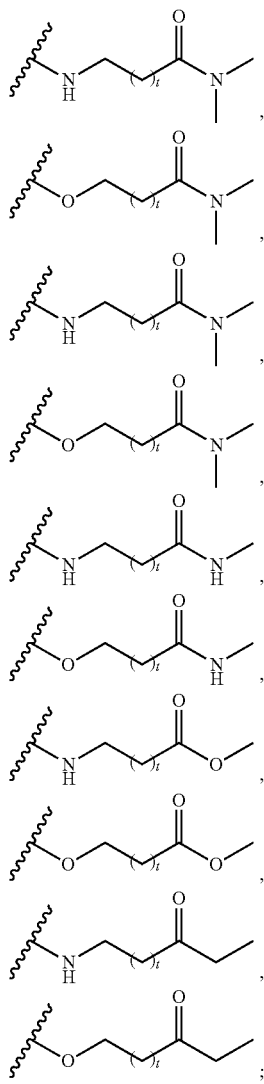

R$_{PTM9}$ is H, optionally substituted C1-C6 alkyl, optionally substituted aliphatic amine, optionally substituted aliphatic amide optionally substituted

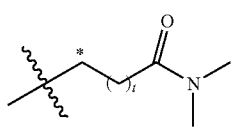

(e.g., optionally substituted with at least one alkyl, such as the * carbon may be optionally substituted with an alkyl);

the ⤢ can be a single bond or a double bond; and the ⤢ indicates the site of attachment of at least one of a linker, ULM, ULM', CLM, CLM', VLM, VLM', ILM, ILM', MLM, MLM', or a combination thereof.

In any aspect or embodiment described herein, the PTM is represented by chemical structure:

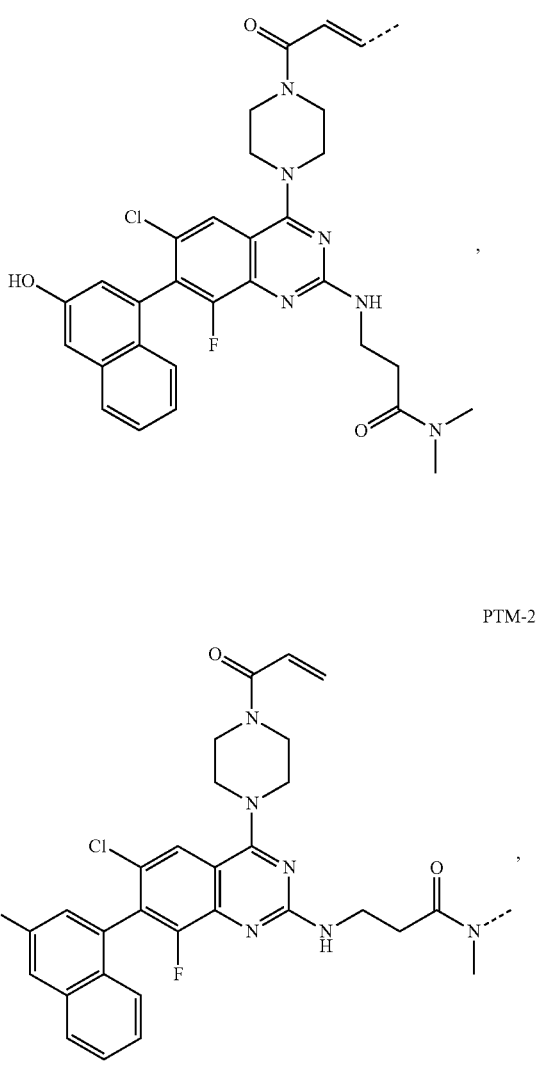

PTM-1

PTM-2

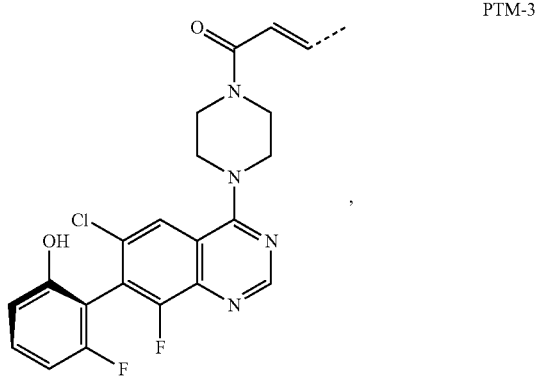

PTM-3

-continued
PTM-4
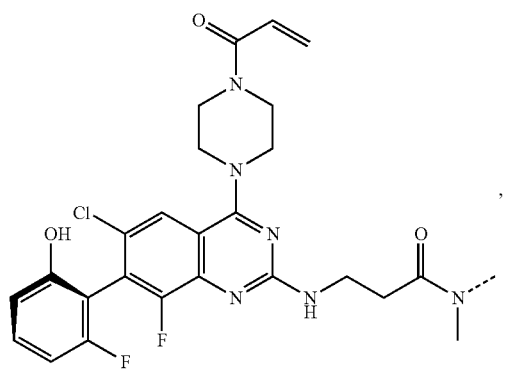
PTM-5
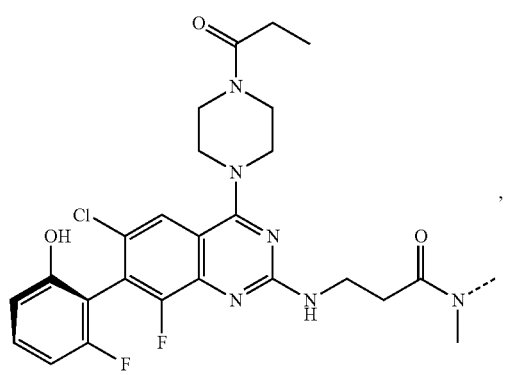
PTM-6
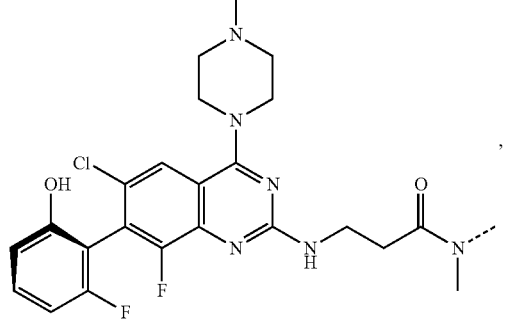
PTM-7
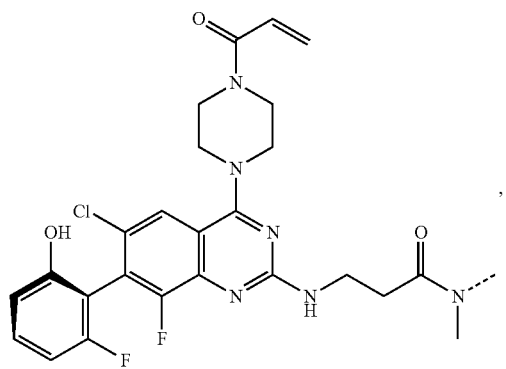
-continued
PTM-8
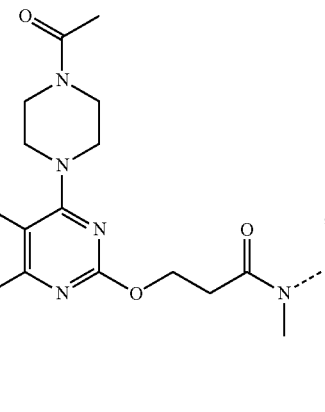
PTM-9
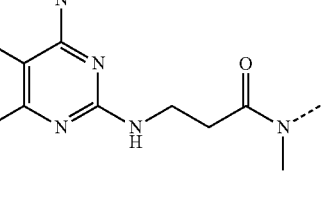
PTM-10

PTM-11
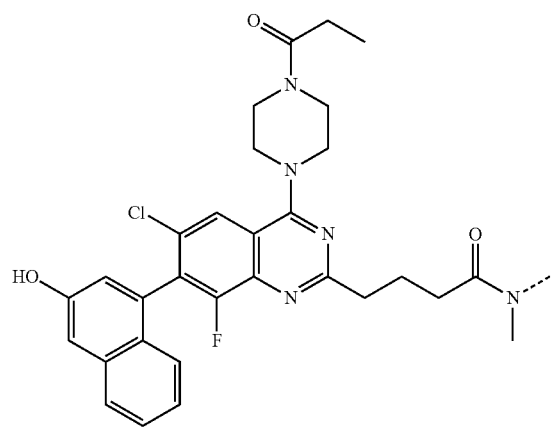
PTM-12
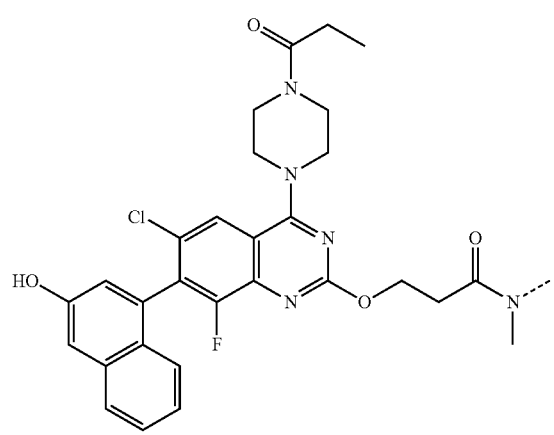
PTM-13
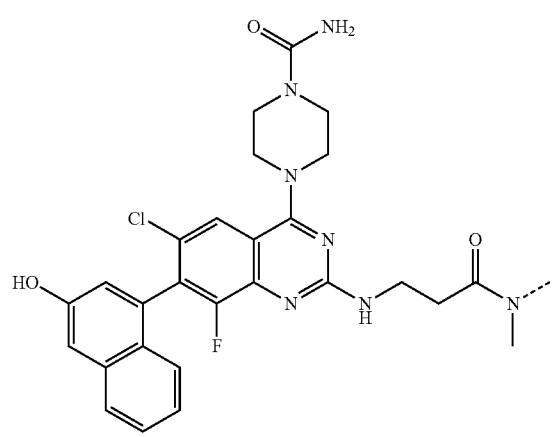
PTM-14
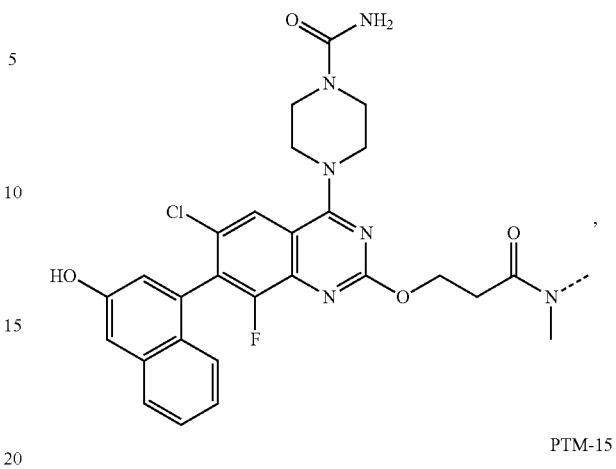
PTM-15
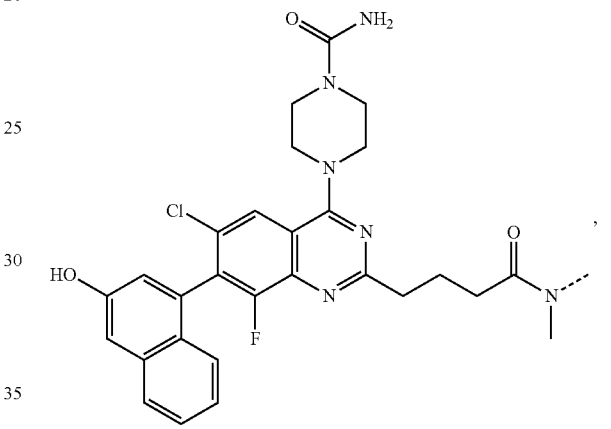
PTM-16
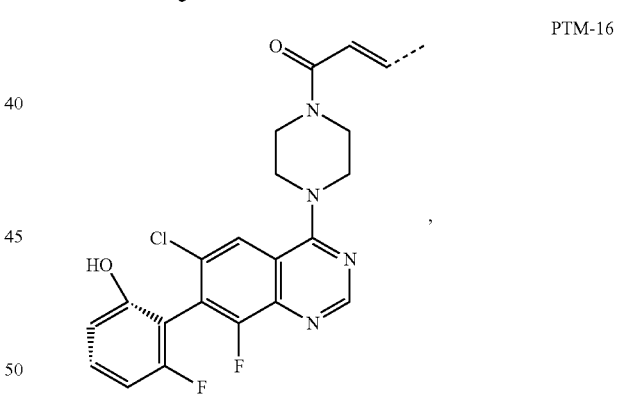
PTM-17
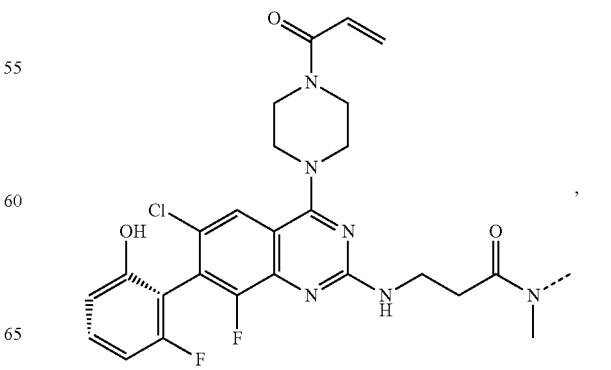

-continued
PTM-18
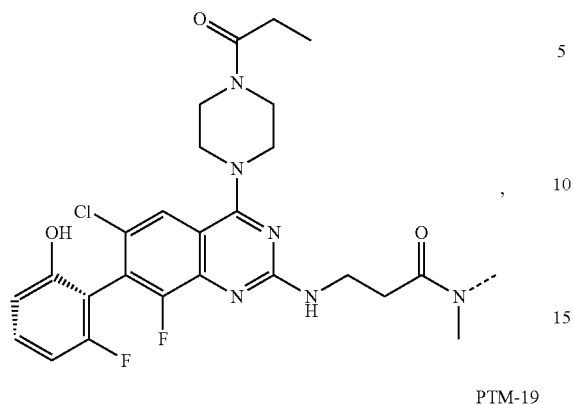
PTM-19
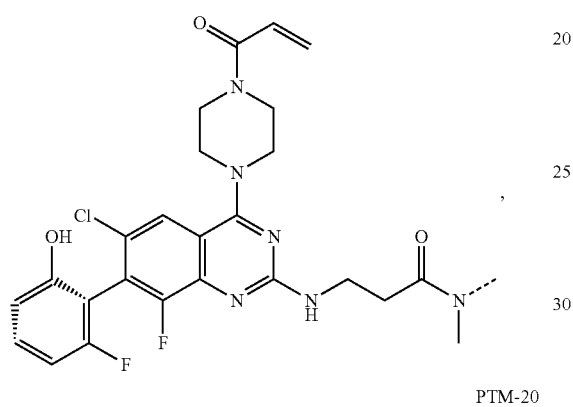
PTM-20
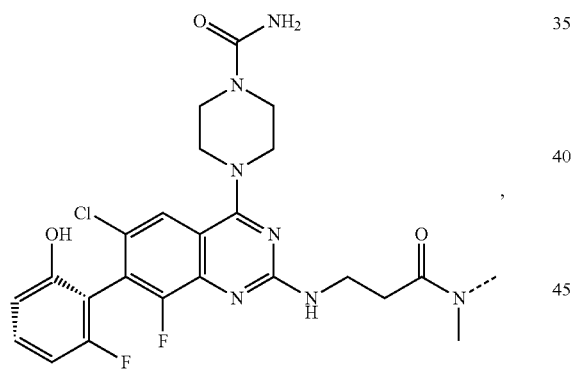
PTM-21
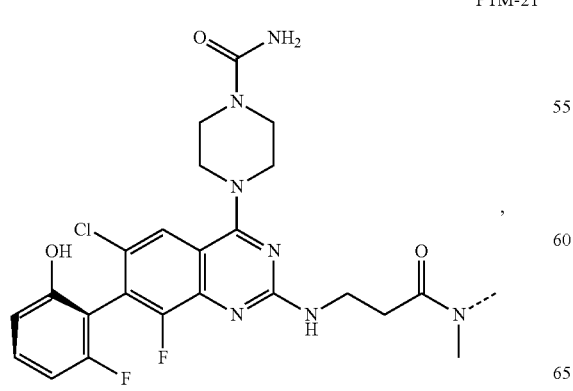
-continued
PTM-22
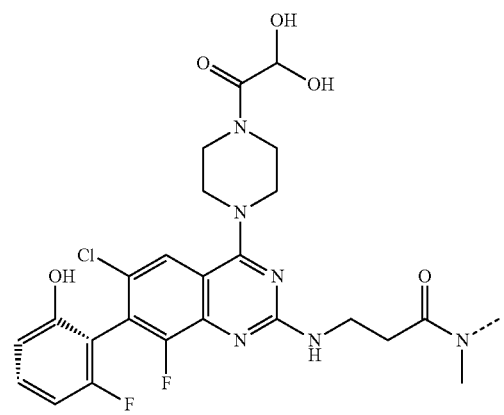
PTM-23
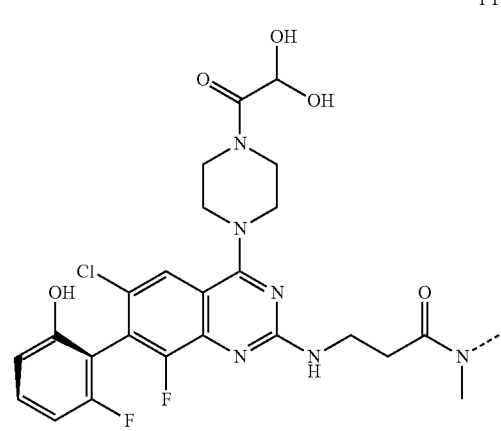
PTM-23
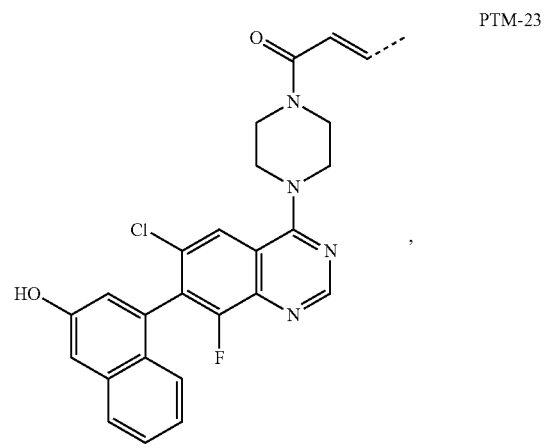

PTM-24
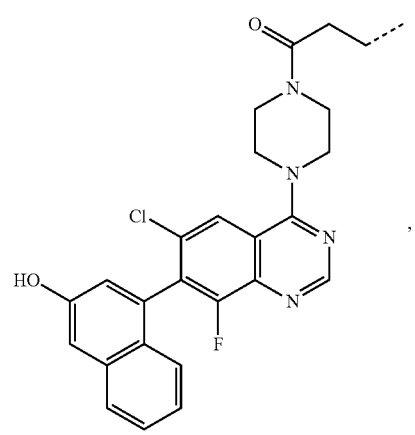
PTM-25
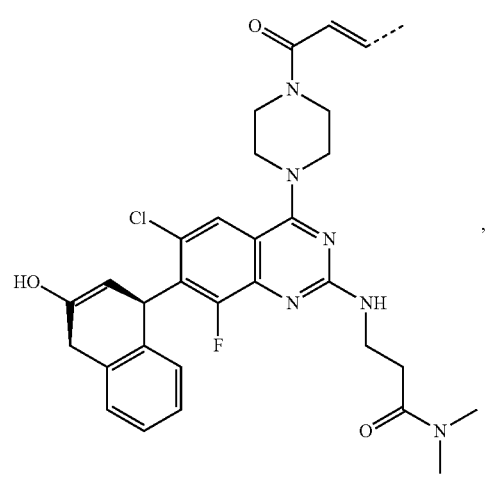
PTM-26
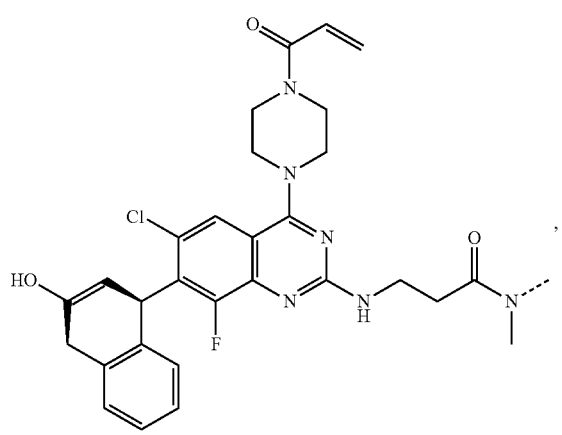
PTM-27
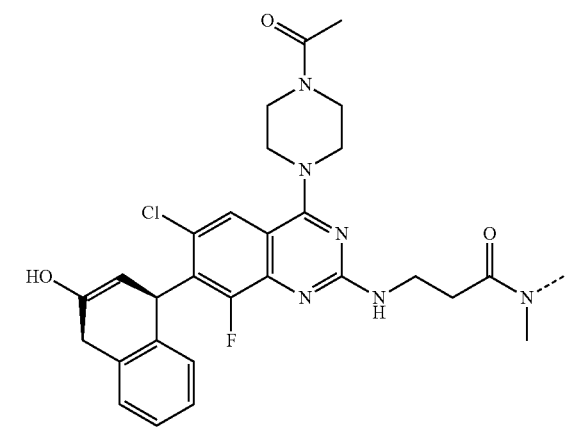
PTM-28
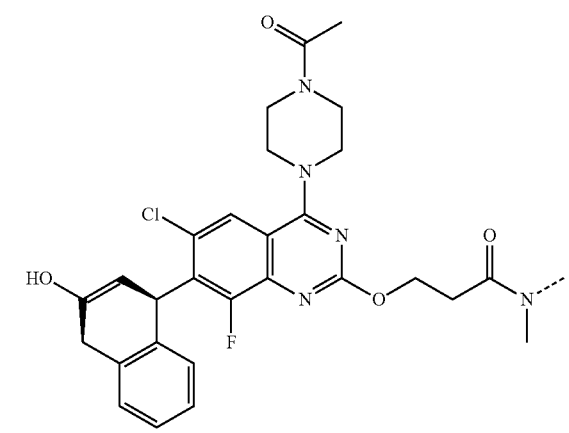
PTM-29
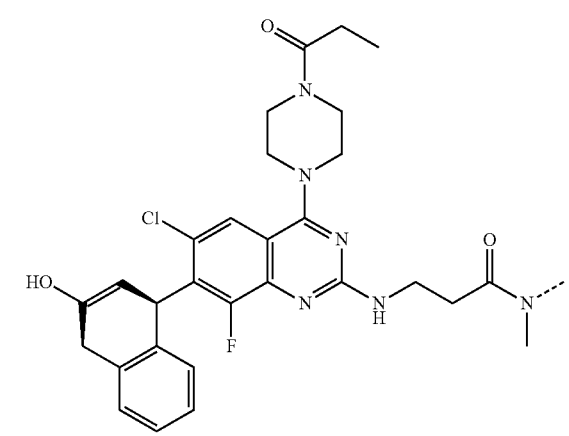

PTM-32
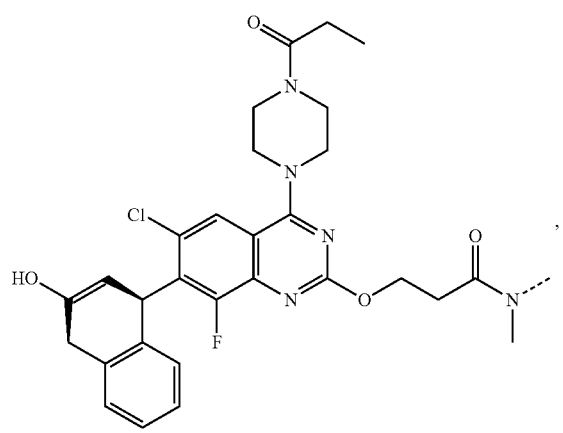
PTM-33
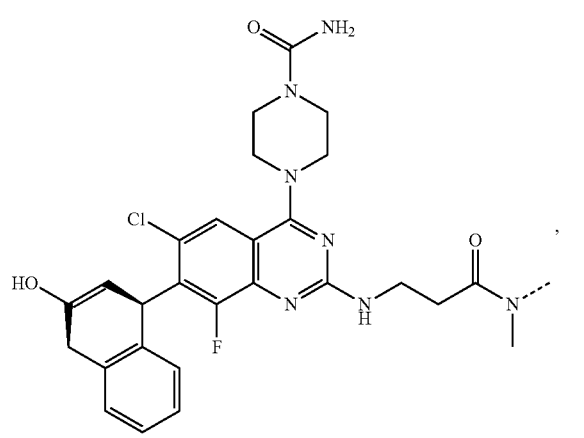
PTM-34
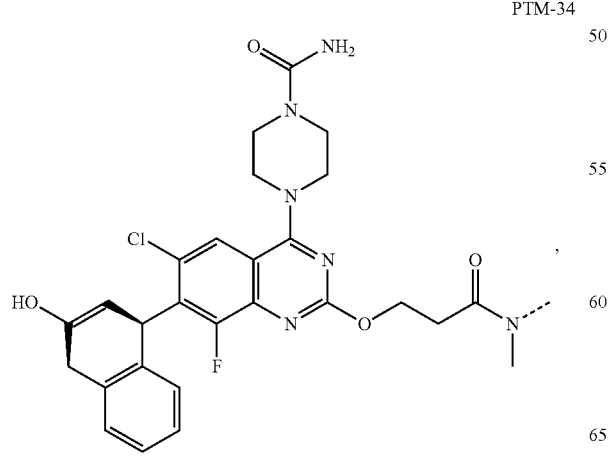
PTM-35
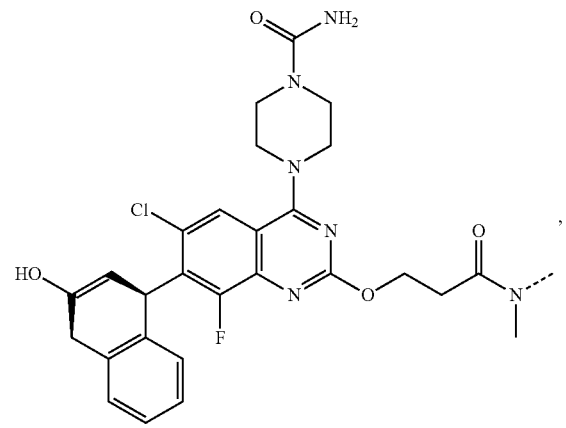
,
PTM-36
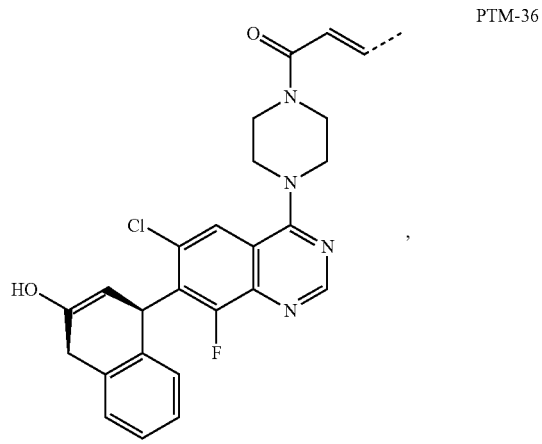
,
PTM-37
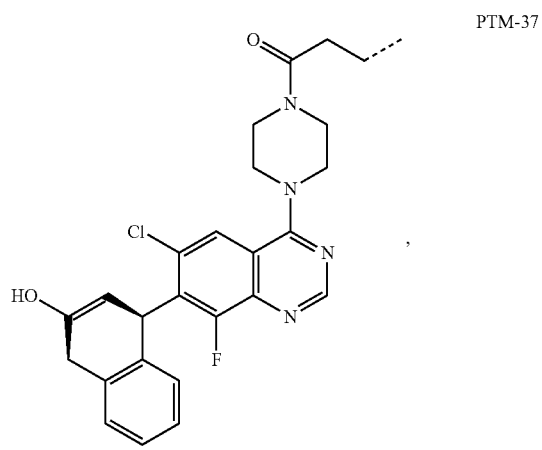

PTM-38
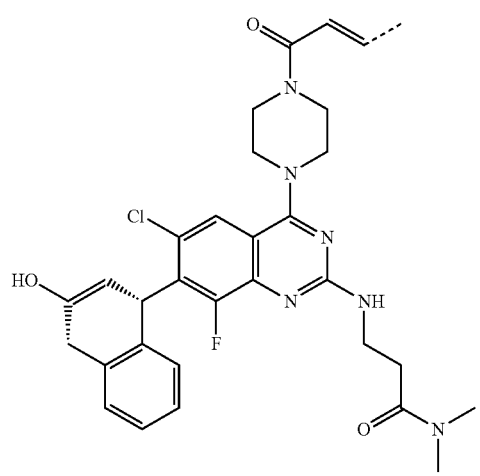
PTM-41
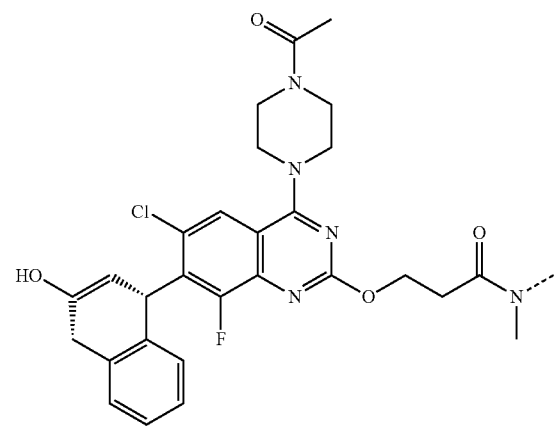
PTM-39
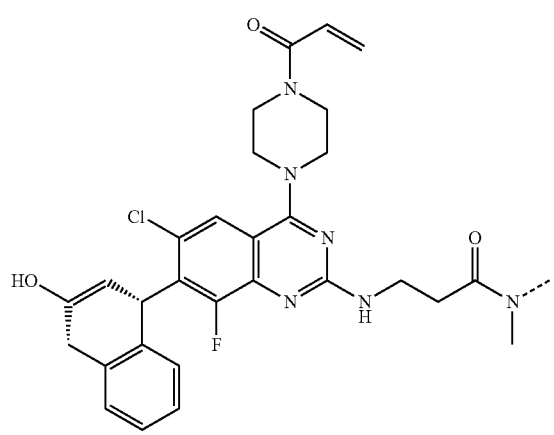
PTM-42
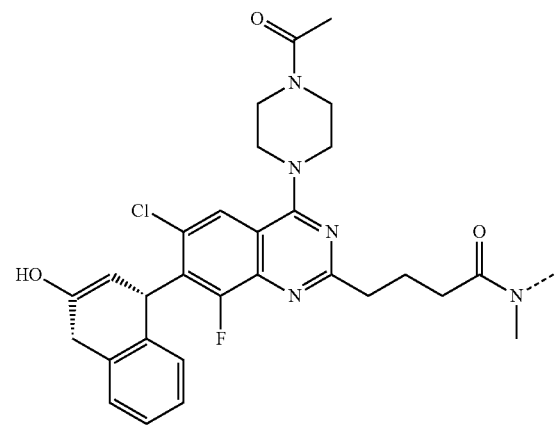
PTM-40
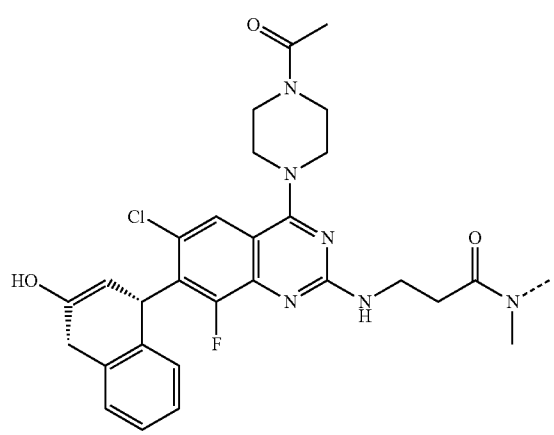
PTM-43

PTM-44
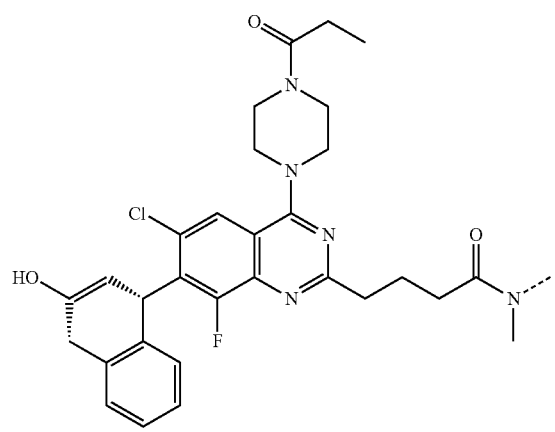
PTM-45
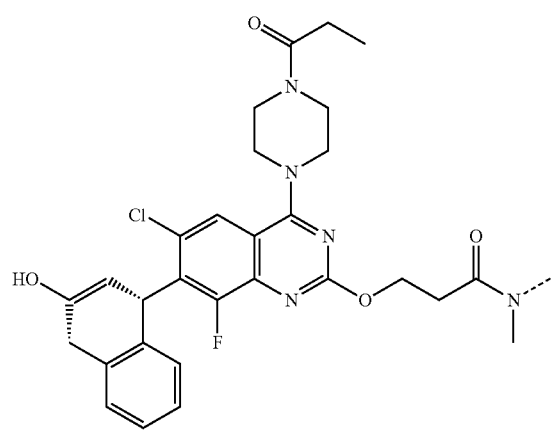
PTM-46
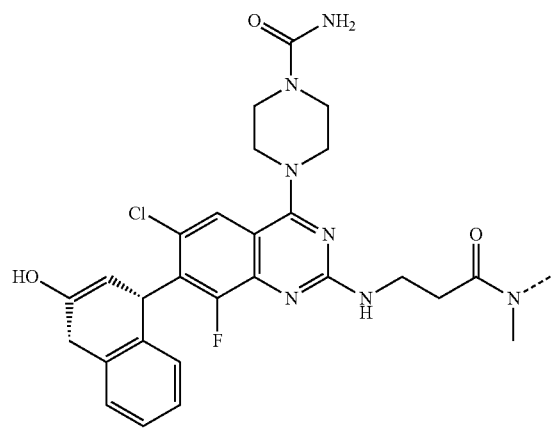
PTM-47
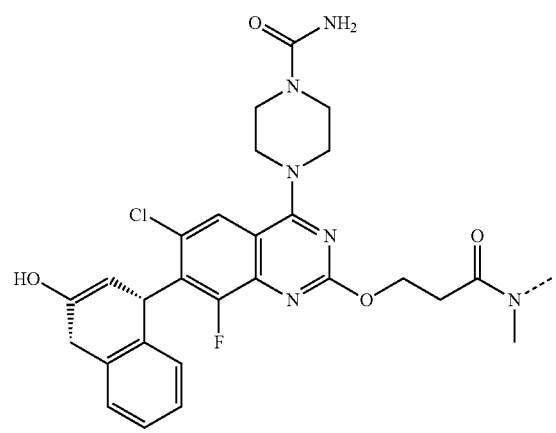
,
PTM-48
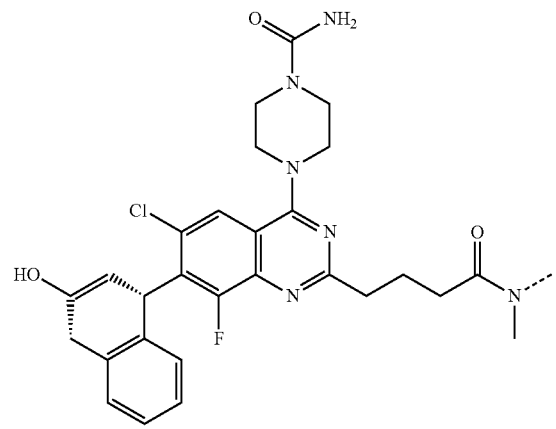
,
PTM-49
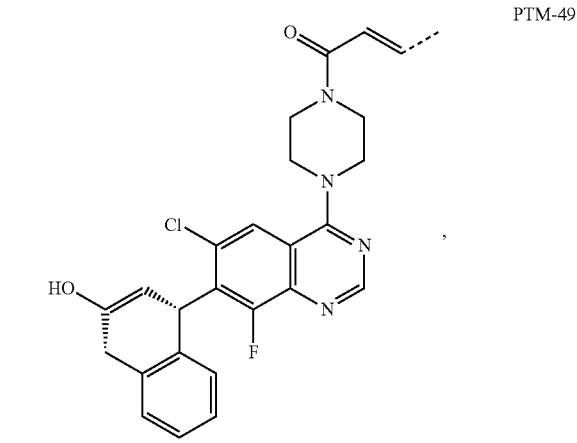
, 995
-continued
996
-continued
PTM-50
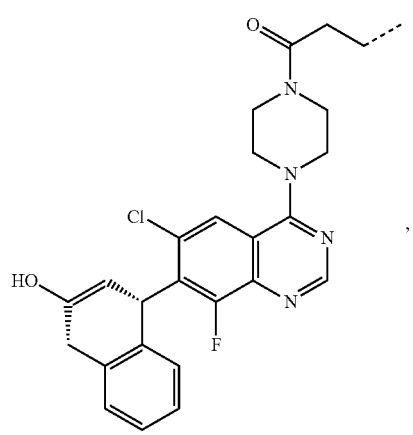
PTM-53
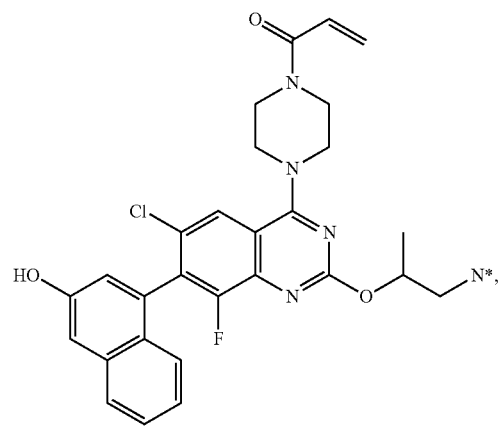
PTM-51
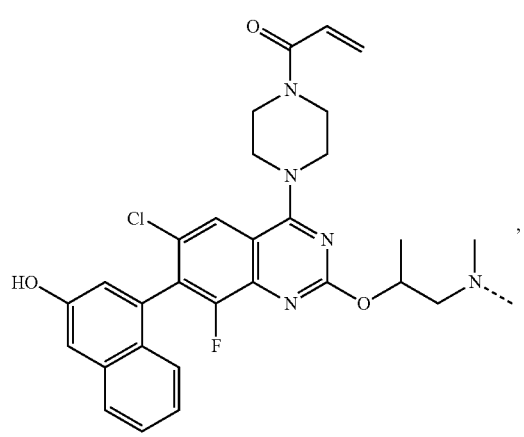
PTM-54
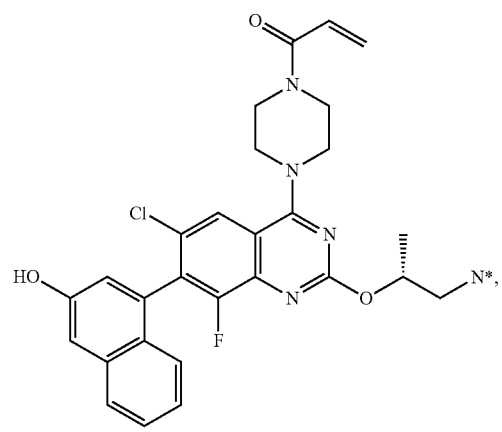
PTM-52
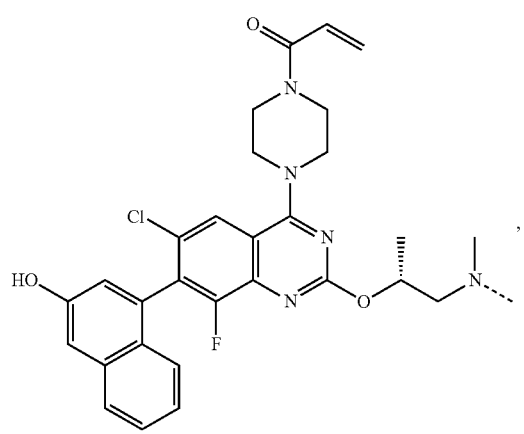
PTM-55
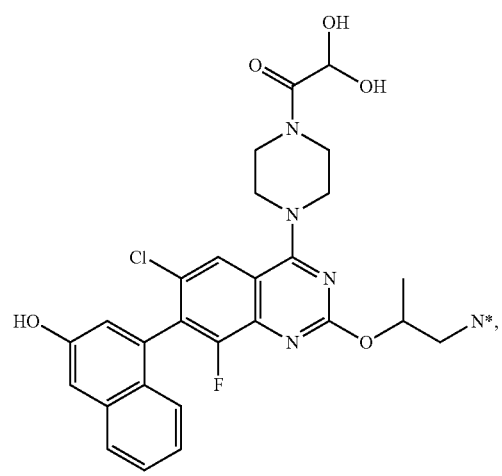

PTM-56
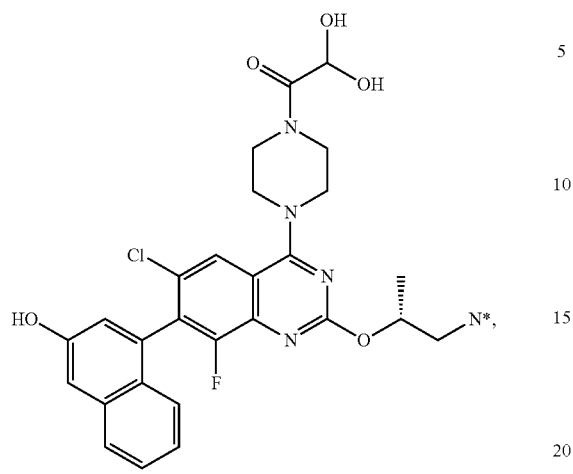
PTM-57
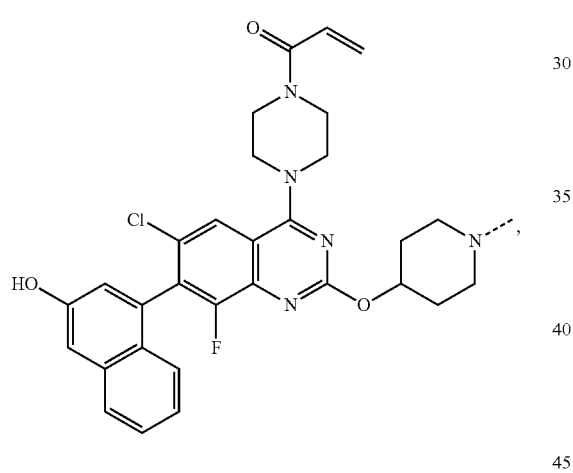
PTM-58
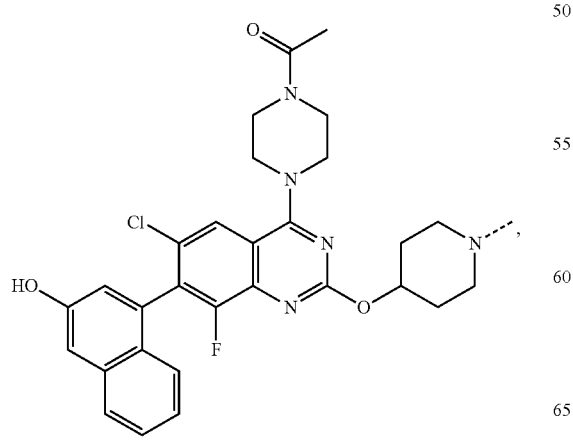
PTM-59
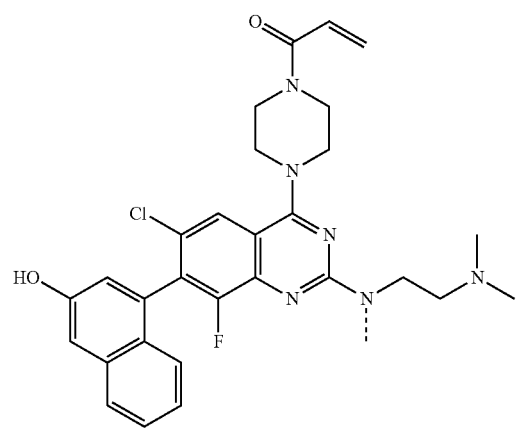
PTM-60
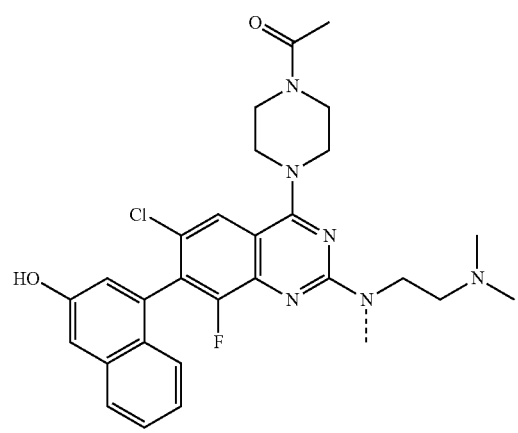
PTM-61
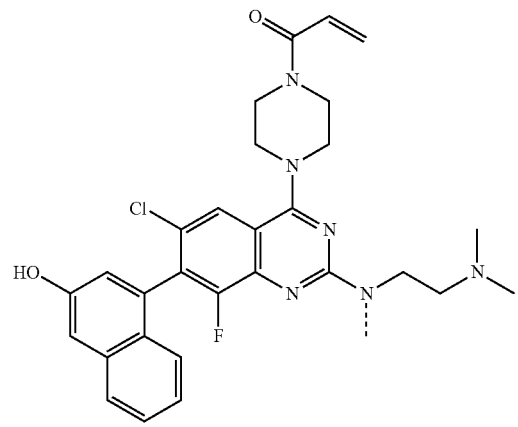

PTM-62
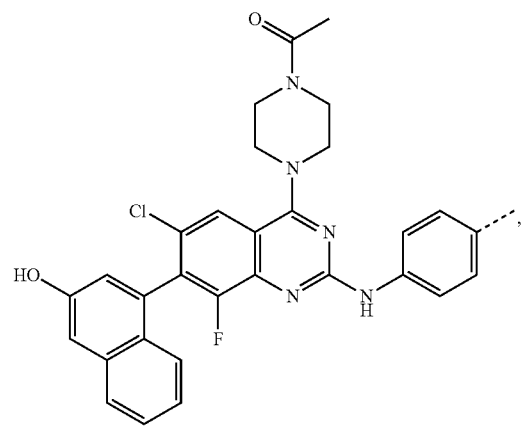
PTM-63
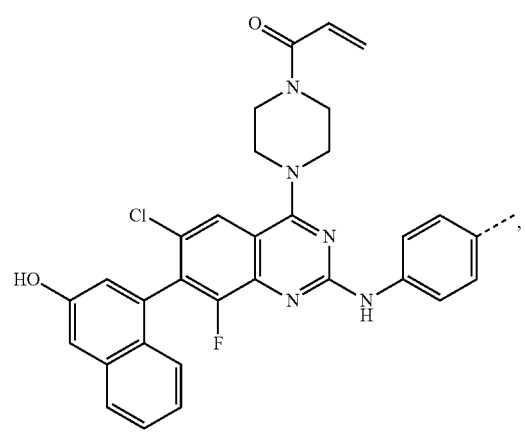
PTM-64
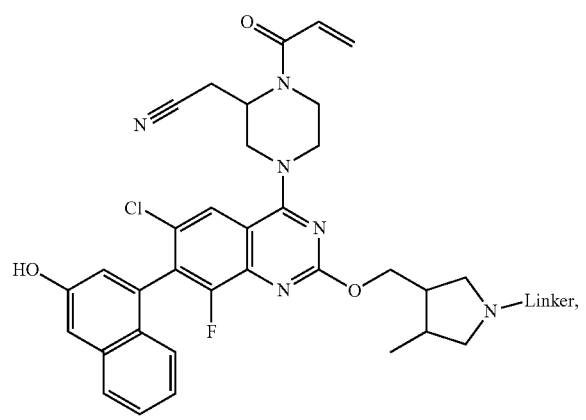
PTM-65
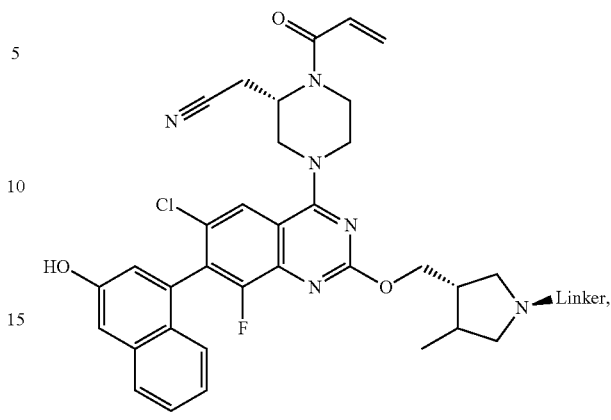
PTM-66
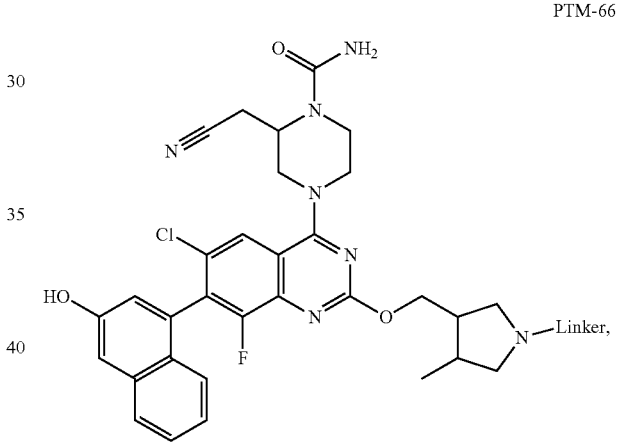
PTM-67
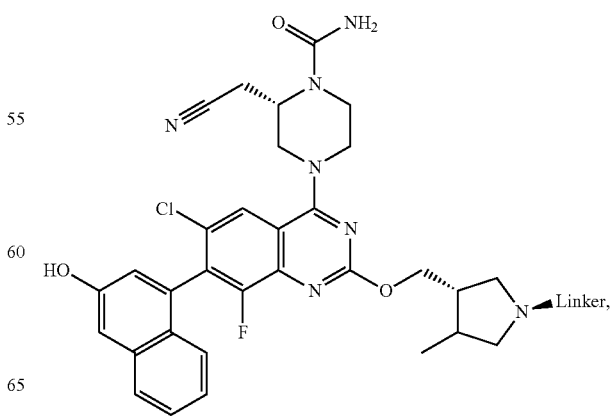

1001
-continued
PTM-68
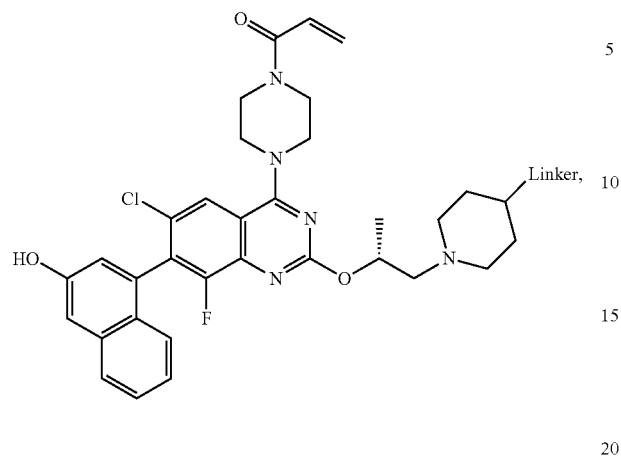
PTM-69
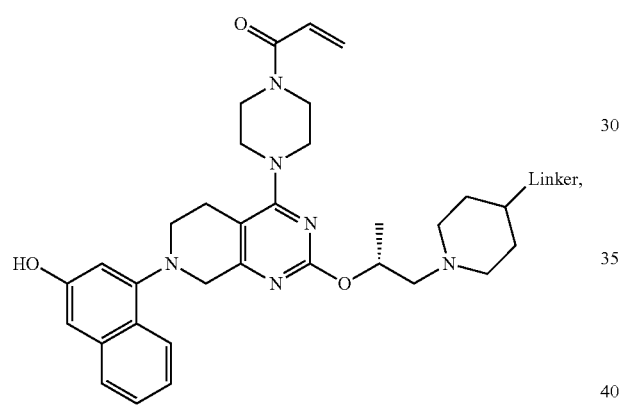
PMT-70
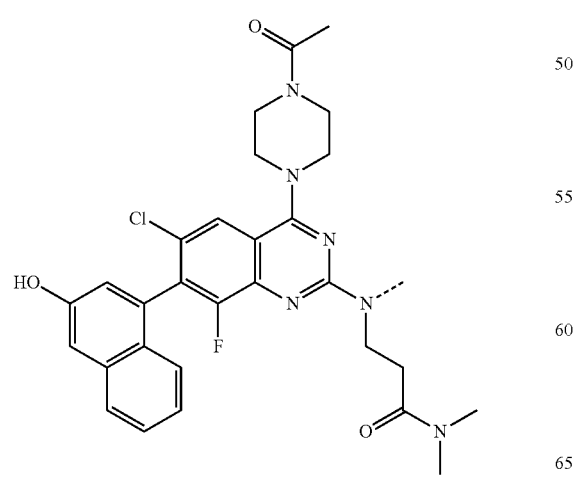
1002
-continued
PTM-71
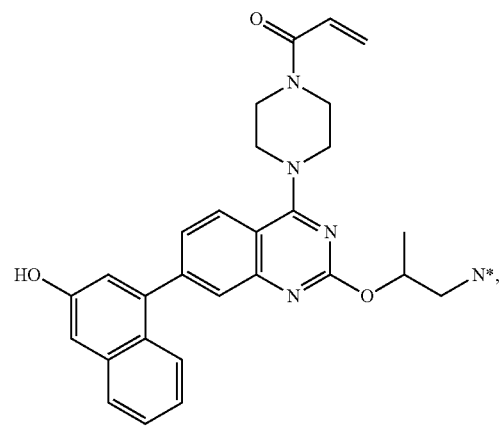
PTM-72
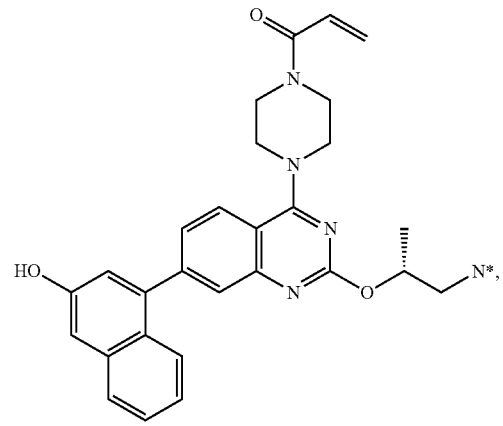
PTM-73
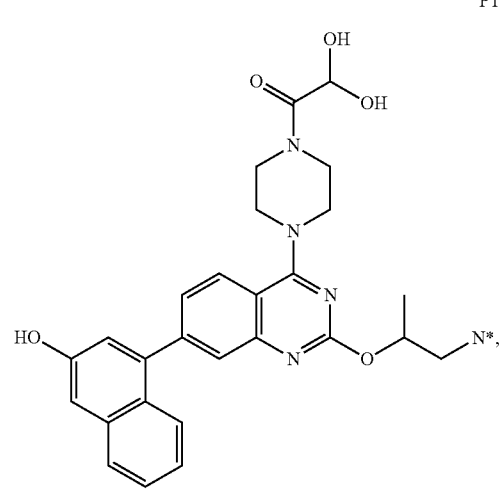

PTM-74
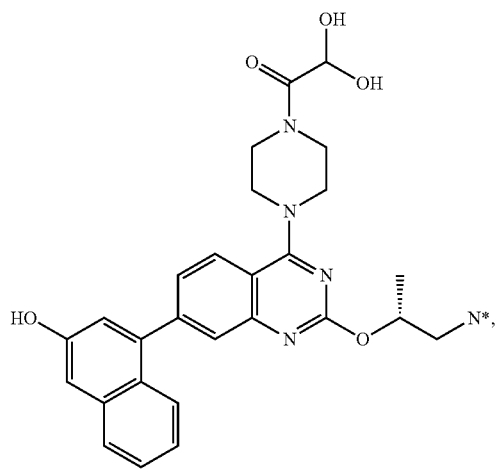
PTM-74
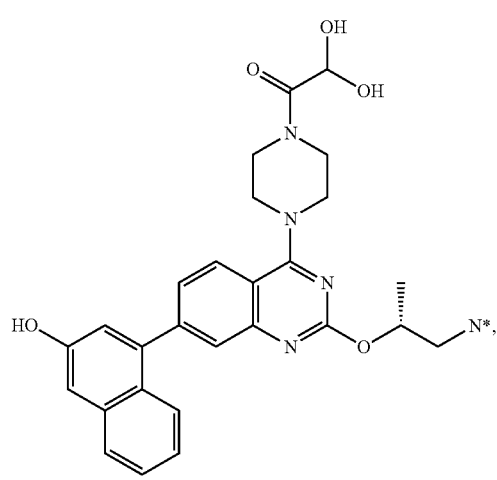
PTM-75
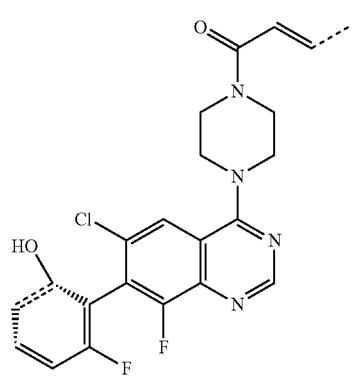
PTM-76
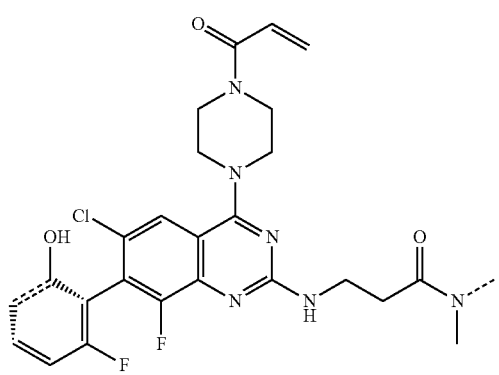
PTM-77
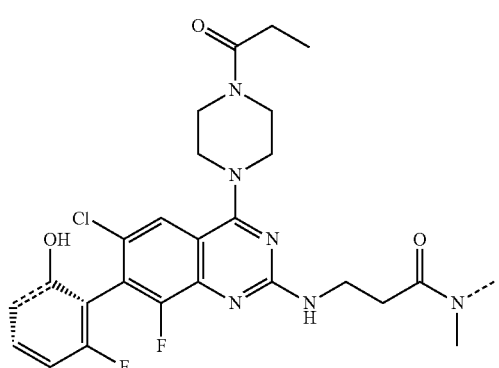
PTM-78
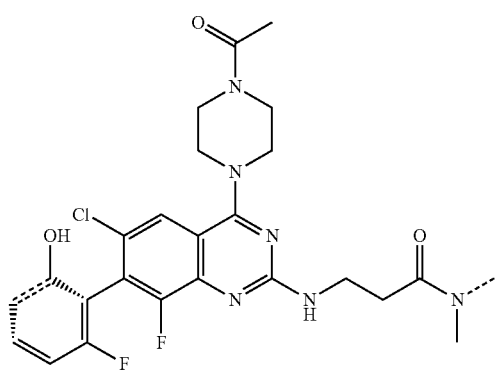
PTM-79

| PTM-80 | PTM-83 |
|---|---|
| 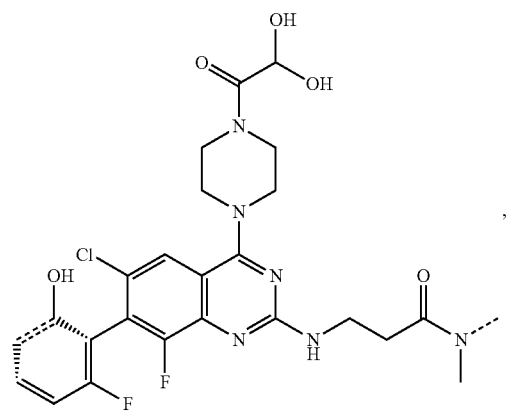 | 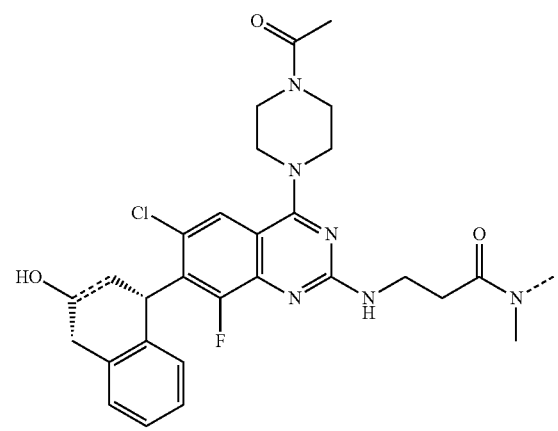 |
| PTM-81 | PTM-84 |
| 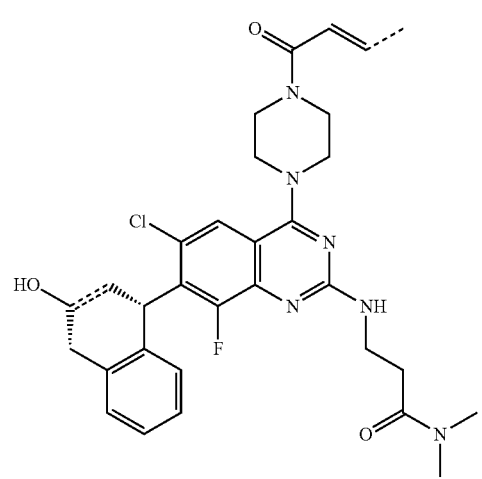 | 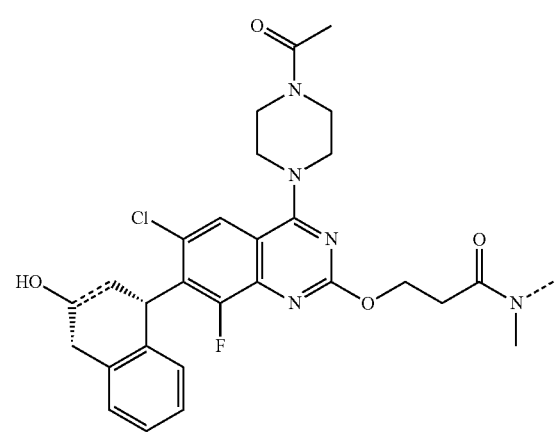 |
| PTM-82 | PTM-85 |
| 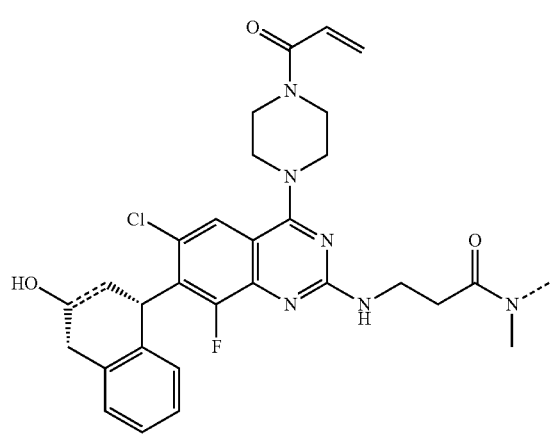 | 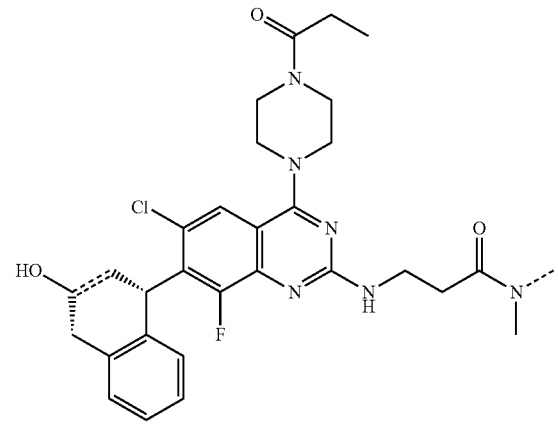 |

1007
-continued
PTM-86
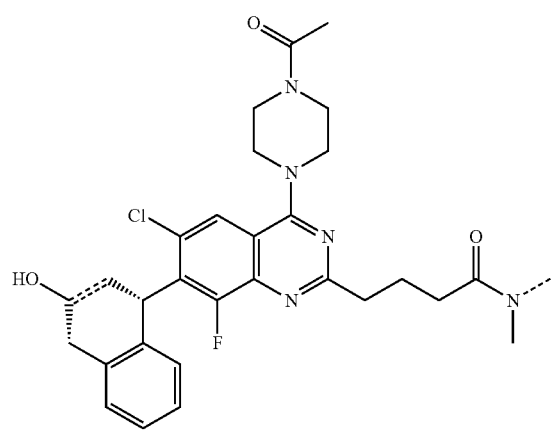
PTM-87
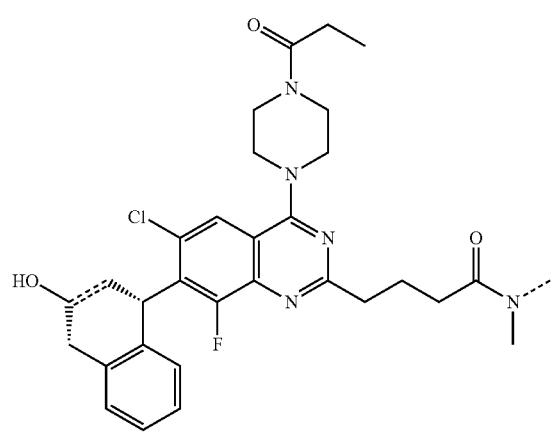
PTM-88
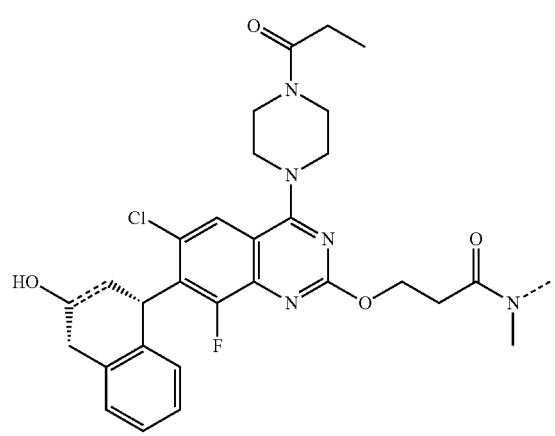
1008
-continued
PTM-89
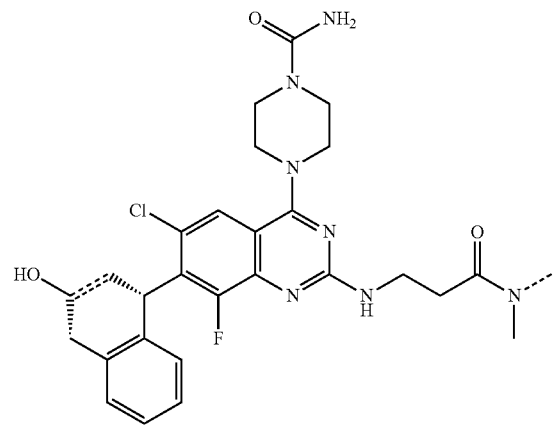
PTM-90
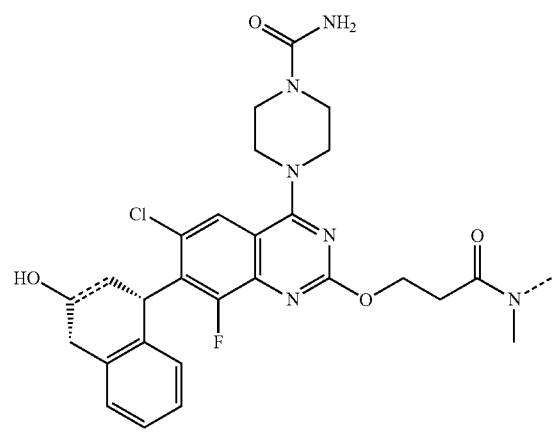
PTM-91
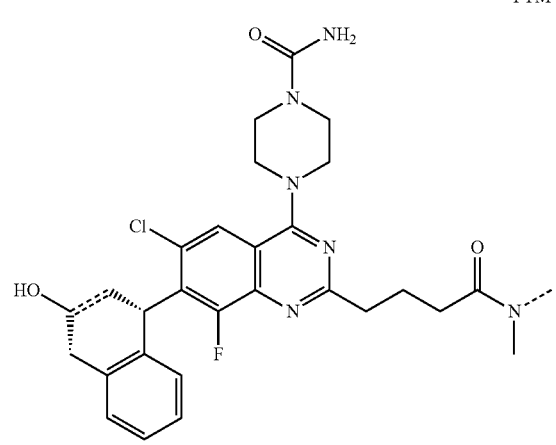

-continued

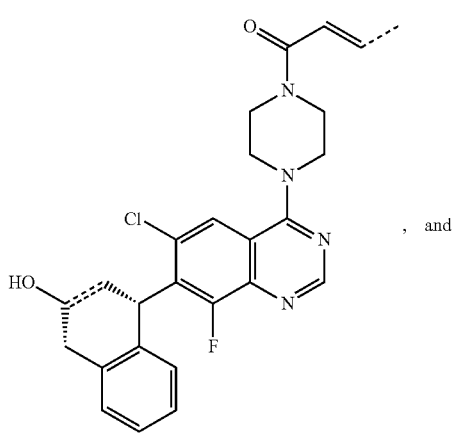
PTM-92

, and

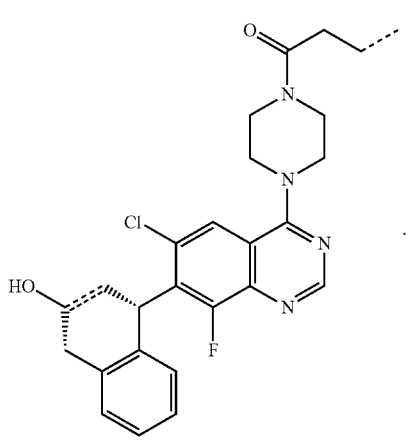
PTM-93

In any aspect or embodiment described herein, ULM is a Von Hippel-Lindau (VHL) ligase-binding moiety (VLM) with a chemical structure represented by:

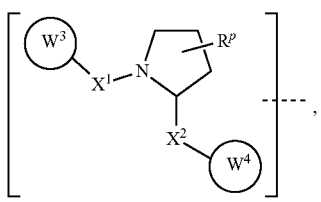

wherein:
X$^1$, X$^2$ are each independently selected from the group of a bond, O, NR$^{Y3}$, CR$^{Y3}$R$^{Y4}$, C=O, C=S, SO, and SO$_2$;
R$^{Y3}$, R$^{Y4}$ are each independently selected from the group of H, linear or branched C$_{1-6}$ alkyl, optionally substituted by 1 or more halo, C$_{1-6}$ alkoxyl optionally substituted by 0-3 R$^P$ groups;
R$^P$ is 0, 1, 2, or 3 groups, each independently selected from the group H, halo, —OH, C$_{1-3}$ alkyl, C=O;
W$^3$ is selected from the group of an optionally substituted T, an optionally substituted -T-N(R$^{1a}$R$^{1b}$)X$^3$, an optionally substituted -T-N(R$^{1a}$R$^{1b}$), an optionally substituted -T-Aryl, an optionally substituted -T-Heteroaryl, an optionally substituted -T-heterocyclyl, an optionally substituted -T-bieterocyclyl, an optionally substituted —NR$^1$-T-Aryl, an optionally substituted —NR$^1$-T-Heteroaryl or an optionally substituted —NR$^1$-T-heterocyclyl;

X$^3$ is C=O, R$^1$, R$^{1a}$, R$^{1b}$;
each of R$^1$, R$^{1a}$, R$^{1b}$ is independently selected from the group consisting of H, linear or branched C$_1$-C$_6$ alkyl group optionally substituted by 1 or more halo or —OH groups, R$^{Y3}$C=O, R$^{Y3}$C=S, R$^{Y3}$SO, R$^{Y3}$SO$_2$, N(R$^{Y3}$R$^{Y4}$)C=O, N(R$^{Y3}$R$^{Y4}$)C=S, N(R$^{Y3}$R$^{Y4}$)SO, and N(R$^{Y3}$R$^{Y4}$)SO$_2$;
T is selected from the group of an optionally substituted alkyl, —(CH$_2$)$_n$— group, wherein each one of the methylene groups is optionally substituted with one or two substituents selected from the group of halogen, methyl, optionally substituted alkoxy, a linear or branched C$_1$-C$_6$ alkyl group optionally substituted by 1 or more halogen, C(O) NR$^1$R$^{1a}$, or NR$^1$R$^{1a}$ or R$^1$ and R$^{1a}$ are joined to form an optionally substituted heterocycle, or —OH groups or an amino acid side chain optionally substituted; and
n is 0 to 6,
W$^4$ is

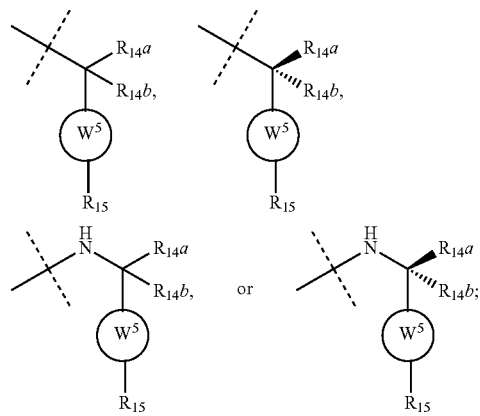

R$_{14a}$, R$_{14b}$, are each independently selected from the group of H, haloalkyl, or optionally substituted alkyl;
W$^5$ is selected from the group of an optionally substituted phenyl or an optionally substitute 5-10 membered heteroaryl (e.g., optionally substituted with one or more [such as 1, 2, 3, 4, or 5]halo, CN, optionally substituted alkyl, optionally substituted haloalkyl, optionally substituted alkoxy, hydroxy, or optionally substituted haloalkoxy),
R$_{15}$ is selected from the group of H, halogen, CN, OH, NO$_2$, NR$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14a}$ SO$_2$R$_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;
and wherein the dashed line indicates the site of attachment of at least one PTM, another ULM (ULM') or a chemical linker moiety coupling at least one PTM or a ULM' or both to ULM.

In any aspect or embodiment described herein, ULM is a Von Hippel-Lindau (VHL) ligase-binding moiety (VLM) with a chemical structure represented by:

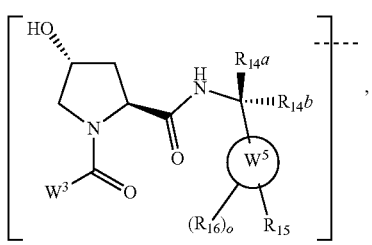

wherein:
W³ is selected from the group of an optionally substituted aryl, optionally substituted heteroaryl, or

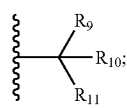

R₉ and R₁₀ are independently hydrogen, optionally substituted alkyl, optionally substituted cycloalkyl, optionally substituted hydroxyalkyl, optionally substituted heteroaryl, or haloalkyl, or R₉, R₁₀, and the carbon atom to which they are attached form an optionally substituted cycloalkyl;
R₁₁ is selected from the group of an optionally substituted heterocyclyl, optionally substituted alkoxy, optionally substituted heteroaryl, optionally substituted aryl,

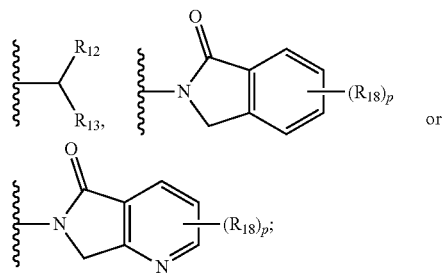

R₁₂ is selected from the group of H or optionally substituted alkyl;
R₁₃ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
R₁₄ₐ, R₁₄ᵦ, are each independently selected from the group of H, haloalkyl, or optionally substituted alkyl;
W⁵ is selected from the group of an optionally substituted phenyl or an optionally substituted 5-10 membered heteroaryl (e.g., optionally substituted with one or more [such as 1, 2, 3, 4, or 5]halo, CN, optionally substituted alkyl, optionally substituted haloalkyl, optionally substituted alkoxy, hydroxy, or optionally substituted haloalkoxy);
R₁₅ is selected from the group of H, halogen, CN, OH, NO₂, NR₁₄ₐR₁₄ᵦ, OR₁₄ₐ, CONR₁₄ₐR₁₄ᵦ, NR₁₄ₐCOR₁₄ᵦ, SO₂NR₁₄ₐR₁₄ᵦ, NR₁₄ₐ SO₂R₁₄ᵦ, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;
each R₁₆ is independently selected from the group of halo, CN, optionally substituted alkyl, optionally substituted haloalkyl, optionally substituted alkoxy, hydroxy, or optionally substituted haloalkoxy;
o is 0, 1, 2, 3, or 4;
R₁₈ is independently selected from the group of halo, optionally substituted alkoxy, cyano, optionally substituted alkyl, haloalkyl, haloalkoxy or a linker; and
p is 0, 1, 2, 3, or 4, and wherein the dashed line indicates the site of attachment of at least one PTM, another ULM (ULM') or a chemical linker moiety coupling at least one PTM or a ULM' or both to ULM.

In any aspect or embodiment described herein, the ULM has a chemical structure selected from the group of:

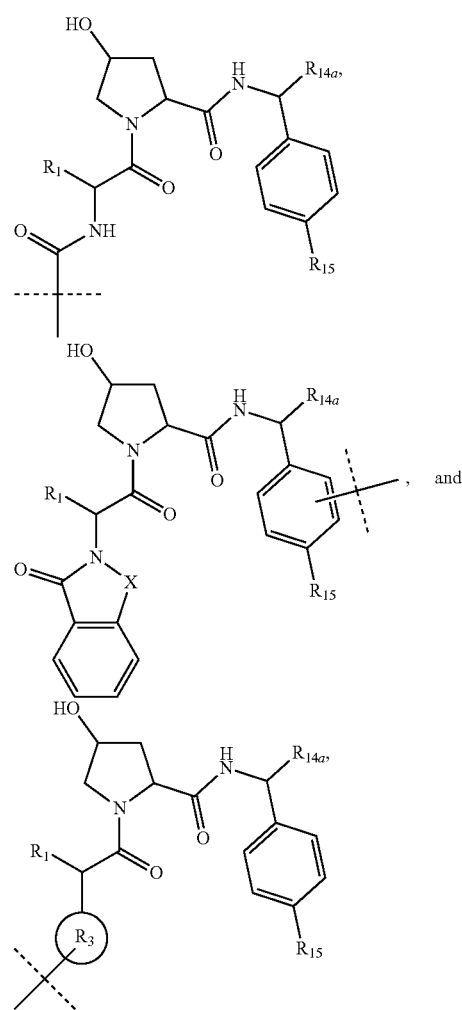

wherein:
R₁ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;
R₁₄ₐ is H, haloalkyl, optionally substituted alkyl, methyl, fluoromethyl, hydroxymethyl, ethyl, isopropyl, or cyclopropyl;

R$_{15}$ is selected from the group consisting of H, halogen, CN, OH, NO$_2$, optionally substituted heteroaryl, optionally substituted aryl, optionally substituted alkyl, optionally substituted haloalkyl, optionally substituted haloalkoxy, optionally substituted cycloalkyl, or optionally substituted cycloheteroalkyl;

X is C, CH$_2$, or C=O

R$_3$ is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to the ULM.

In any aspect or embodiment described herein, the ULM comprises a group according to the chemical structure:

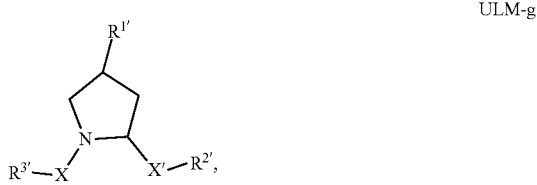

ULM-g wherein:

R$^{1'}$ of ULM-g is an optionally substituted C$_1$-C$_6$ alkyl group, an optionally substituted —(CH$_2$)$_n$OH, an optionally substituted —(CH$_2$)$_n$SH, an optionally substituted (CH$_2$)$_n$—O—(C$_1$-C$_6$)alkyl group, an optionally substituted (CH$_2$)$_n$—WCOCW—(C$_0$-C$_6$)alkyl group containing an epoxide moiety WCOCW where each W is independently H or a C$_1$-C$_3$ alkyl group, an optionally substituted —(CH$_2$)$_n$COOH, an optionally substituted —(CH$_2$)$_n$C(O)—(C$_1$-C$_6$ alkyl), an optionally substituted —(CH$_2$)$_n$NHC(O)—R$_1$, an optionally substituted —(CH$_2$)$_n$C(O)—NR$_1$R$_2$, an optionally substituted —(CH$_2$)$_n$OC(O)—NR$_1$R$_2$, —(CH$_2$O)$_n$H, an optionally substituted —(CH$_2$)$_n$OC(O)—(C$_1$-C$_6$ alkyl), an optionally substituted —(CH$_2$)$_n$C(O)—O—(C$_1$-C$_6$ alkyl), an optionally substituted —(CH$_2$O)$_n$COOH, an optionally substituted —(OCH$_2$)$_n$O—(C$_1$-C$_6$ alkyl), an optionally substituted —(CH$_2$O)$_n$C(O)—(C$_1$-C$_6$ alkyl), an optionally substituted —(OCH$_2$)$_n$NHC(O)—R$_1$, an optionally substituted —(CH$_2$O)$_n$C(O)—NR$_1$R$_2$, —(CH$_2$CH$_2$O)$_n$H, an optionally substituted —(CH$_2$CH$_2$O)$_n$COOH, an optionally substituted —(OCH$_2$CH$_2$)$_n$O—(C$_1$-C$_6$ alkyl), an optionally substituted —(CH$_2$CH$_2$O)$_n$C(O)—(C$_1$-C$_6$ alkyl), an optionally substituted —(OCH$_2$CH$_2$)$_n$NHC(O)—R$_1$, an optionally substituted —(CH$_2$CH$_2$O)$_n$C(O)—NR$_1$R$_2$, an optionally substituted —SO$_2$R$_S$, an optionally substituted S(O)R$_S$, NO$_2$, CN or halogen (F, Cl, Br, I, preferably F or Cl);

R$_1$ and R$_2$ of ULM-g are each independently H or a C$_1$-C$_6$ alkyl group which may be optionally substituted with one or two hydroxyl groups or up to three halogen groups (preferably fluorine);

R$_S$ of ULM-g is a C$_1$-C$_6$ alkyl group, an optionally substituted aryl, heteroaryl or heterocycle group or a —(CH$_2$)$_m$NR$_1$R$_2$ group;

X and X' of ULM-g are each independently C=O, C=S, —S(O), S(O)$_2$, (preferably X and X' are both C=O);

R$^{2'}$ of ULM-g is an optionally substituted —(CH$_2$)$_n$—(C=O)$_u$(NR$_1$)$_v$(SO$_2$)$_w$alkyl group, an optionally substituted —(CH$_2$)$_n$—(C=O)$_u$(NR$_1$)$_v$(SO$_2$)$_w$NR$_{1N}$R$_{2N}$ group, an optionally substituted —(CH$_2$)$_n$—(C=O)$_u$(NR$_1$)$_v$(SO$_2$)$_w$-Aryl, an optionally substituted —(CH$_2$)$_n$—(C=O)$_u$(NR$_1$)$_v$(SO$_2$)$_w$-Heteroaryl, an optionally substituted —(CH$_2$)—(C=O)$_v$NR$_1$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)—C(O)$_u$(NR$_1$)$_v$(SO$_2$)$_w$—NR$_{1N}$R$_{2N}$, an optionally substituted —NR$^1$—(CH$_2$)$_n$—C(O)$_u$(NR$_1$)$_v$(SO$_2$)$_w$—NR$_1$C(O)R$_{1N}$, an optionally substituted —NR$^1$—(CH$_2$)$_n$—(C=O)$_u$(NR$_1$)$_v$(SO$_2$)$_w$-Aryl, an optionally substituted —NR$^1$—(CH$_2$)$_n$-Aryl-heteroaryl, an optionally substituted —NR$^1$—(CH$_2$)—(C=O)$_u$(NR$_1$)$_v$(SO$_2$)$_w$-Heteroaryl or an optionally substituted —NR$^1$—(CH$_2$)$_n$—(C=O)$_v$NR$_1$(SO$_2$)$_w$-Heterocycle, an optionally substituted —X$^{R2'}$-alkyl group; an optionally substituted —X$^{R2'}$-Aryl group; an optionally substituted —X$^{R2'}$-Heteroaryl group; an optionally substituted —X$^{R2'}$-Heterocycle group; an optionally substituted;

R$^{3'}$ of ULM-g is an optionally substituted alkyl, an optionally substituted —(CH$_2$)$_n$—(O)$_u$(NR$_1$)$_v$(SO$_2$)$_w$-alkyl, an optionally substituted —(CH$_2$)—C(O)$_u$(NR$_1$)$_v$(SO$_2$)$_w$—NR$_{1N}$R$_{2N}$, an optionally substituted —(CH$_2$)$_n$—C(O)$_u$(NR$_1$)$_v$(SO$_2$)$_w$—NR$_1$C(O)R$_{1N}$, an optionally substituted —(CH$_2$)$_n$—C(O)$_u$(NR$_1$)$_v$(SO$_2$)$_w$—C(O)NR$_1$R$_2$, an optionally substituted —(CH$_2$)$_n$—C(O)$_u$(NR$_1$)$_v$(SO$_2$)$_w$-Aryl, an optionally substituted —(CH$_2$)$_n$—C(O)$_u$(NR$_1$)$_v$(SO$_2$)$_w$-Heteroaryl, an optionally substituted —(CH$_2$)—C(O)$_u$(NR$_1$)$_v$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)$_n$—C(O)$_u$(NR$_1$)$_v$(SO$_2$)$_w$— NR$_{1N}$R$_{2N}$, an optionally substituted —NR$^1$—(CH$_2$)$_n$—C(O)$_u$(NR$_1$)$_v$(SO$_2$)$_w$—NR$_1$C(O) R$_{1N}$, an optionally substituted —NR$^1$—(CH$_2$)$_n$—C(O)$_u$(NR$_1$)$_v$(SO$_2$)$_w$-Aryl, an optionally substituted —NR$^1$—(CH$_2$)$_n$—C(O)$_u$(NR$_1$)$_v$(SO$_2$)$_w$-Heteroaryl, an optionally substituted —NR$^1$—(CH$_2$)$_n$—C(O)$_u$(NR$_1$)$_v$(SO$_2$)$_w$-Heterocycle, an optionally substituted —O—(CH$_2$)n-(C=O)$_u$(NR$_1$)$_v$(SO$_2$)$_w$-alkyl, an optionally substituted —O—(CH$_2$)n-(C=O)$_u$(NR)$_v$(SO$_2$)$_w$— NR$_{1N}$R$_{2N}$, an optionally substituted —O—(CH$_2$)n-(C=O)$_u$(NR)$_v$(SO$_2$)$_w$—NR$_1$C(O)R$_{1N}$, an optionally substituted —O—(CH$_2$)n-(C=O)$_u$(NR$_1$)$_v$(SO$_2$)$_w$-Aryl, an optionally substituted —O—(CH$_2$)$_n$—(C=O)$_u$(NR$_1$)$_v$(SO$_2$)$_w$-Heteroaryl or an optionally substituted —O—(CH$_2$)$_n$—(C=O)$_u$(NR$_1$)$_v$(SO$_2$)$_w$-Heterocycle; —(CH$_2$)$_n$—(V)$_{n'}$—(CH$_2$)$_n$—(V)$_{n'}$-alkyl group, an optionally substituted —(CH$_2$)$_n$—(V)$_{n'}$—(CH$_2$)$_n$—(V)$_{n'}$-Aryl group, an optionally substituted —(CH$_2$)$_n$—(V)$_{n'}$—(CH$_2$)$_n$—(V)$_{n'}$-Heteroaryl group, an optionally substituted —(CH$_2$)$_n$—(V)$_{n'}$—(CH$_2$)$_n$—(V)$_{n'}$-Heterocycle group, an optionally substituted —(CH$_2$)$_n$—N(R$_{1'}$)(C=O)$_{m'}$—(V)$_{n'}$-alkyl group, an optionally substituted —(CH$_2$)$_n$—N(R$_{1'}$)(C=O)$_{m'}$—(V)$_{n'}$-Aryl group, an optionally substituted —(CH$_2$)$_n$—N(R$_{1'}$)(C=O)$_{m'}$—(V)$_{n'}$-Heteroaryl group, an optionally substituted —(CH$_2$)$_n$—N(R$_{1'}$)(C=O)$_{m'}$—(V)$_{n'}$-Heterocycle group, an optionally substituted —X$^{R3'}$-alkyl group; an optionally substituted —X$^{R3'}$-Aryl group; an optionally substituted —X$^{R3'}$-Heteroaryl group; an optionally substituted —X$^{R3'}$-Heterocycle group; an optionally substituted;

R$_{1N}$ and R$_{2N}$ of ULM-g are each independently H, C$_1$-C$_6$ alkyl which is optionally substituted with one or two hydroxyl groups and up to three halogen groups or an optionally substituted —(CH$_2$)$_n$-Aryl, —(CH$_2$)$_n$-Heteroaryl or —(CH$_2$)$_n$-Heterocycle group;

V of ULM-g is O, S or NR$_1$;

R$_1$ of ULM-g is the same as above;

R$^1$ and R$_{1'}$ of ULM-g are each independently H or a C$_1$-C$_3$ alkyl group;

X$^{R2'}$ and X$^{R3'}$ of ULM-g are each independently an optionally substituted —(CH$_2$)$_n$—, —(CH$_2$)$_n$—CH(X$_v$)=CH(X$_v$)-(cis or trans), —(CH$_2$)$_n$—CH—CH—, —(CH$_2$CH$_2$O)$_n$— or a C$_3$-C$_6$ cycloalkyl group, where X$_v$ is H, a halo or a C$_1$-C$_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of R$^{1'}$, R$^{2'}$, R$^{3'}$, X and X' of ULM-g is optionally modified to be covalently bonded to the PTM group through a linker group when PTM is not ULM', or when PTM is ULM', any one or more of R$^{1'}$, R$^{2'}$, R$^{3'}$, X and X' of each of ULM and ULM' are optionally modified to be covalently bonded to each other directly or through a linker group, or a pharmaceutically acceptable salt, stereoisomer, solvate or polymorph thereof.

In any aspect or embodiment described herein, the ULM is a cereblon E3 ligase-binding moiety (CLM) selected from the group consisting of a thalidomide, lenalidomide, pomalidomide, analogs thereof, isosteres thereof, or derivatives thereof.

In any aspect or embodiment described herein, the CLM has a chemical structure represented by:

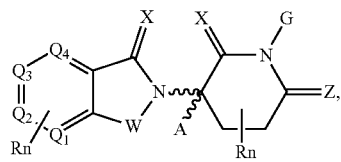

(a)

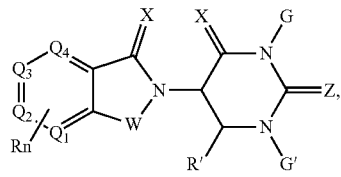

(b)

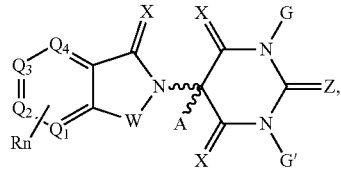

(c)

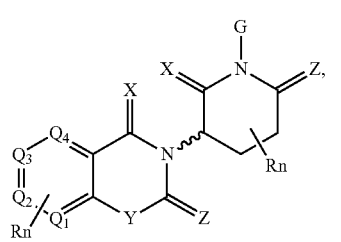

(d)

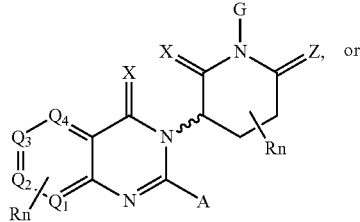

(e)

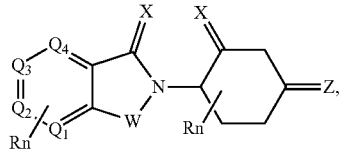

(f)

wherein:

W is selected from the group consisting of CH$_2$, CHR, C=O, SO$_2$, NH, and N-alkyl;

each X is independently selected from the group consisting of O, S, and H$_2$;

Y is selected from the group consisting of CH$_2$, —C=CR', NH, N-alkyl, N-aryl, N-hetaryl, N-cycloalkyl, N-heterocyclyl, O, and S;

Z is selected from the group consisting of O, S, and H$_2$;

G and G' are independently selected from the group consisting of H, optionally substituted linear or branched alkyl, OH, R'OCOOR, R'OCONRR'', CH$_2$-heterocyclyl optionally substituted with R', and benzyl optionally substituted with R';

Q$_1$, Q$_2$, Q$_3$, and Q$_4$ represent a carbon C substituted with a group independently selected from R', N or N-oxide;

A is independently selected from the group H, optionally substituted linear or branched alkyl, cycloalkyl, Cl and F;

R comprises —CONR'R'', —OR', —NR'R'', —SR', —SO$_2$R', —SO$_2$NR'R'', —CR'R''—, —CR'NR'R''—, (—CR'O)$_n$R'', -aryl, -hetaryl, optionally substituted linear or branched alkyl, -cycloalkyl, -heterocyclyl, —P(O)(OR')R'', —P(O)R'R'', —OP(O)(OR')R'', —OP(O)R'R'', —Cl, —F, —Br, —I, —CF$_3$, —CN, —NR'SO$_2$NR'R'', —NR'CONR'R'', —CONR'COR'', —NR'C(=N—CN)NR'R'', —C(=N—CN)NR'R'', —NR'C(=N—CN)R'', —NR'C(=C—NO$_2$)NR'R'', —SO$_2$NR'COR'', —NO$_2$, —CO$_2$R', —C(C=N—OR')R'', —CR'=CR'R'', —CCR', —S(C=O)(C=N—R')R'', —SF$_5$ and —OCF$_3$;

R' and R'' are independently selected from the group consisting of a bond, H, alkyl, cycloalkyl, aryl, heteroaryl, heterocyclic, —C(=O)R, heterocyclyl, each of which is optionally substituted;

∿∿ represents a bond that may be stereospecific ((R) or (S)) or non-stereospecific; and Rn comprises from 1 to 4 functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy; and n is an integer from 1-10, wherein when n is 1, R$_n$ is modified to be covalently joined to the linker group (L), and when n is 2, 3, or 4, then one R$_n$ is modified to be covalently joined to the linker group (L), and any other $R_n$ is optionally modified to be covalently joined to a PTM, a CLM, a second CLM having the same chemical structure as the CLM, a CLM', a second linker, or any multiple or combination thereof.
In any aspect or embodiment described herein, the CLM has a chemical structure represented by:
(h)
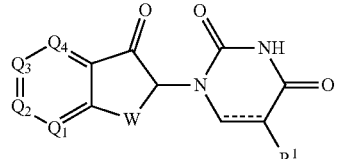
(i)
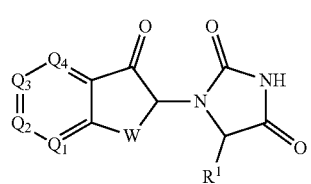
(j)
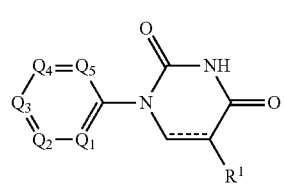
(k)
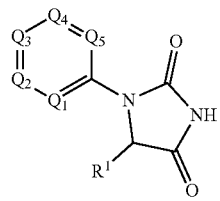
(l)
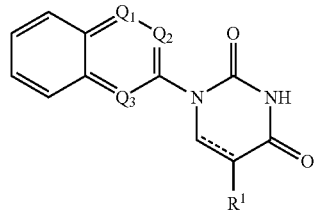
(m)
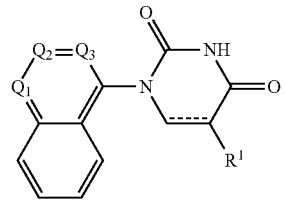
(n)
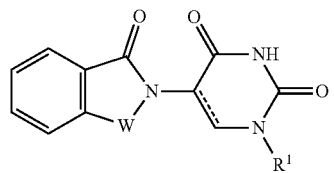
-continued
(o)
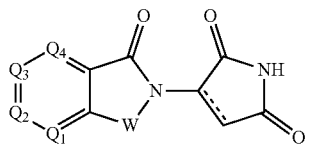
(p)
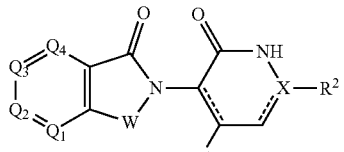
(q)
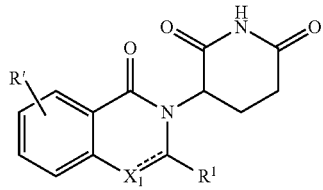
(r)
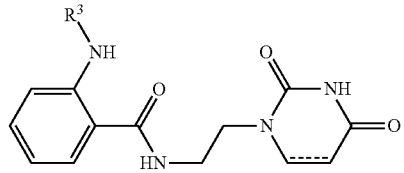
(s)
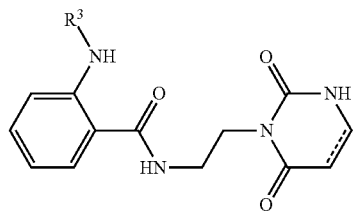
(t)
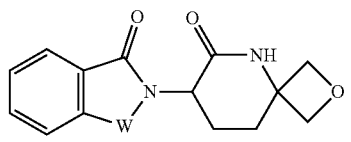
(u)
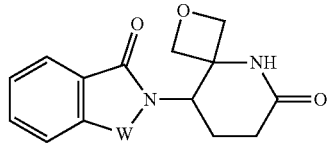
(v)
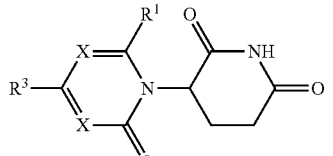
(w)
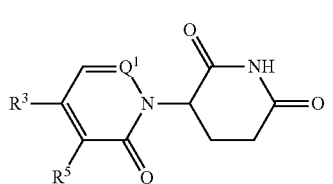

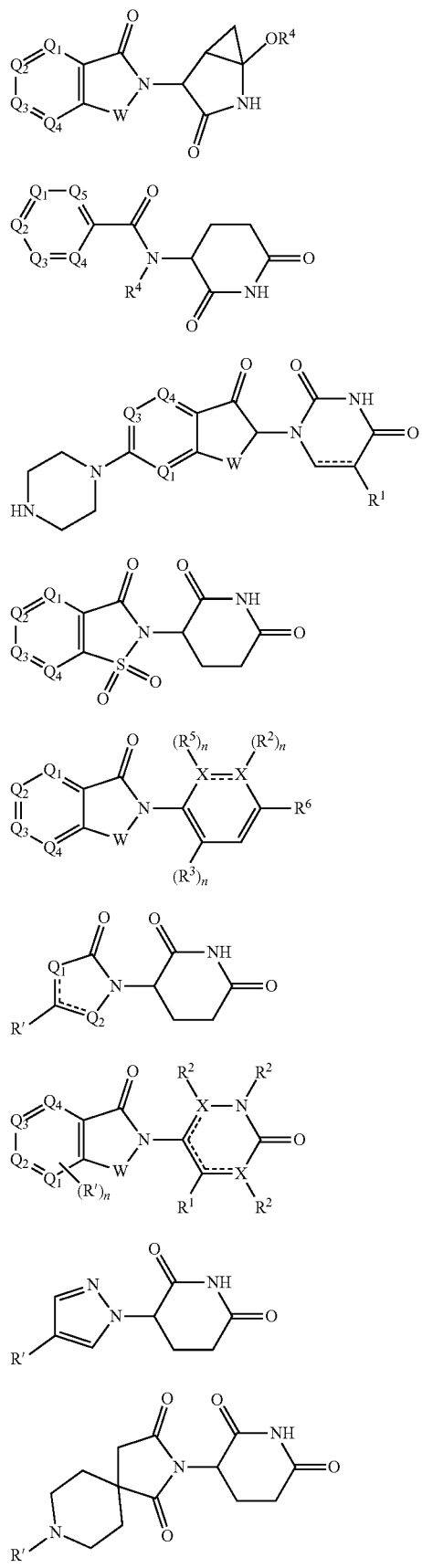
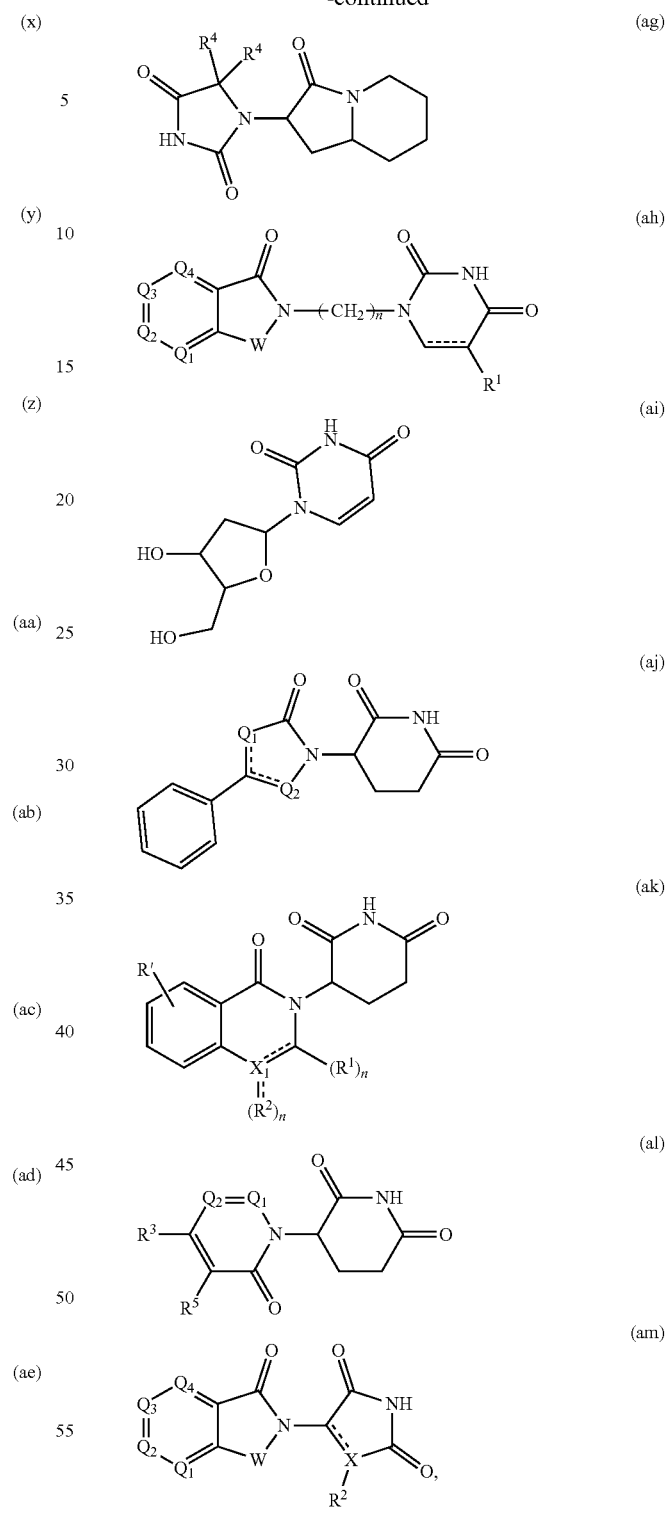
wherein:
W is independently selected from $CH_2$, CHR, C=O, $SO_2$, NH, and N-alkyl;
$Q_1$, $Q_2$, $Q_3$, $Q_4$, $Q_5$ are each independently a carbon C or N substituted with a group independently selected from R', N or N-oxide;
$R^1$ is selected from absent, H, OH, CN, C1-C3 alkyl, C=O;

$R^2$ is selected from the group absent, H, OH, CN, $C_1$-$C_3$ alkyl, $CHF_2$, $CF_3$, CHO, C(=O)$NH_2$;

$R^3$ is selected from H, alkyl (e.g., $C_1$-$C_6$ or $C_1$-$C_3$ alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);

$R^4$ is selected from H, alkyl, substituted alkyl;

$R^5$ and $R^6$ are each independently H, halogen, C(=O)R', CN, OH, $CF_3$;

X is C, CH, C=O, or N;

$X_1$ is C=O, N, CH, or $CH_2$;

R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(=O)$OR^2$, optionally substituted phenyl;

n is 0-4;

⫽ is a single or double bond; and the CLM is covalently joined to a PTM, a chemical linker group (L), a ULM, CLM, CLM', or combinations thereof.

In any aspect or embodiment described herein, the ULM is a (MDM2) binding moiety (MLM) with a chemical moiety selected from the group consisting of a substituted imidazolines, a substituted spiro-indolinones, a substituted pyrrolidines, a substituted piperidinones, a substituted morpholinones, a substituted pyrrolopyrimidines, a substituted imidazolopyridines, a substituted thiazoloimidazoline, a substituted pyrrolopyrrolidinones, and a substituted isoquinolinones.

In any aspect or embodiment described herein, the MLM is selected from:

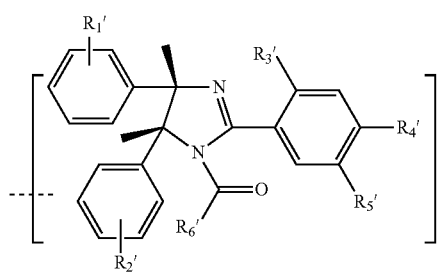

A-1-1

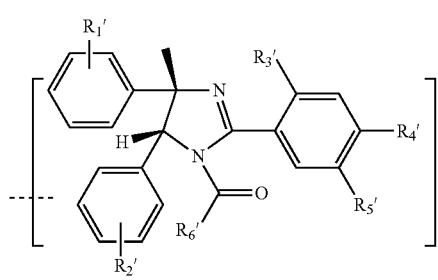

A-1-2

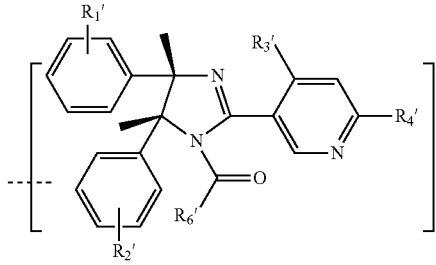

A-1-3

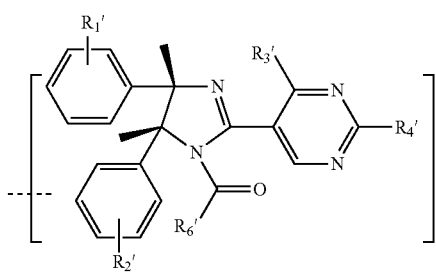

A-1-4

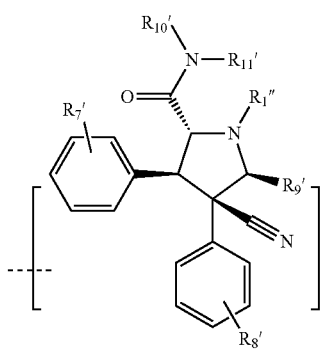

A-4-1

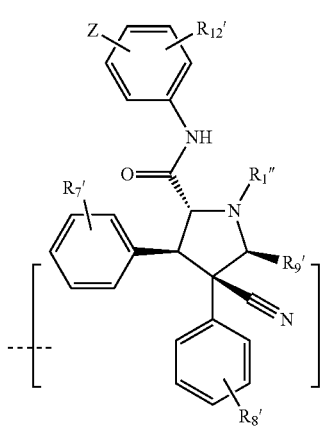

A-4-2

1023
-continued

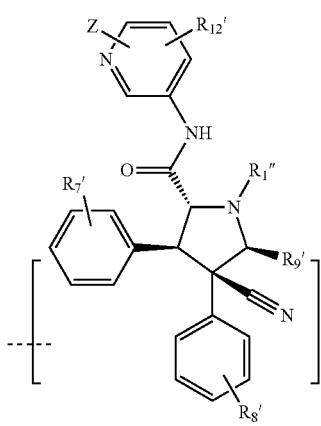
A-4-3

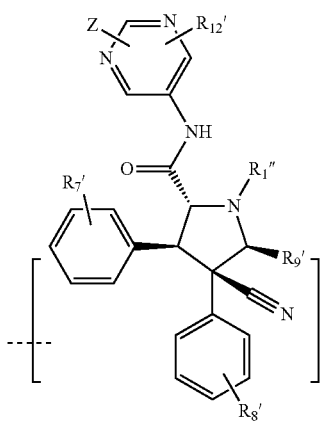
A-4-4

1024
-continued

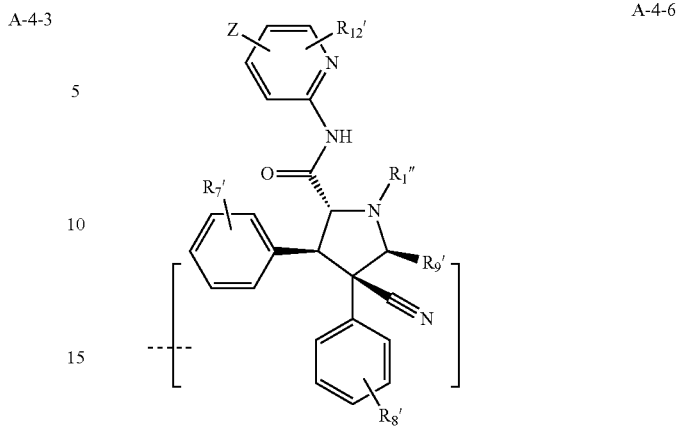
A-4-6 wherein:
R1' and R2' of Formulas A-1-1 through A-1-4 (i.e., A-1-i, A-1-2, A-1-3, and A-1-4) are independently selected from the group consisting of F, Cl, Br, I, acetylene, CN, CF$_3$ and NO$_2$;

R3' is selected from the group consisting of —OCH$_3$, —OCH$_2$CH$_3$, —OCH$_2$CH$_2$F, —OCH$_2$CH$_2$OCH$_3$, and —OCH(CH$_3$)$_2$;

R4' of Formulas A-1-1 through A-1-4 is selected from the group consisting of H, halogen, —CH$_3$, —CF$_3$, —OCH$_3$, —C(CH$_3$)$_3$, —CH(CH$_3$)$_2$, -cyclopropyl, —CN, —C(CH$_3$)$_2$OH, —C(CH$_3$)$_2$OCH$_2$CH$_3$, —C(CH$_3$)$_2$CH$_2$OH, —C(CH$_3$)$_2$CH$_2$OCH$_2$CH$_3$, C(CH$_3$)$_2$CH$_2$OCH$_2$CH$_2$OH, —C(CH$_3$)$_2$CH$_2$OCH$_2$CH$_3$, —C(CH$_3$)$_2$CN, —C(CH$_3$)$_2$C(O)CH$_3$, —C(CH$_3$)$_2$C(O)NHCH$_3$, —C(CH$_3$)$_2$C(O)N(CH$_3$)$_2$, —SCH$_3$, —SCH$_2$CH$_3$, —S(O)$_2$CH$_3$, S(O$_2$)CH$_2$CH$_3$, —NHC(CH$_3$)$_3$, —N(CH$_3$)$_2$, pyrrolidinyl, and 4-morpholinyl;

R5' of Formulas A-1-1 through A-1-4 is selected from the group consisting of halogen, -cyclopropyl, —S(O)$_2$CH$_3$, —S(O)$_2$CH$_2$CH$_3$, 1-pyrrolidinyl, —NH$_2$, —N(CH$_3$)$_2$, and —NHC(CH$_3$)$_3$; and R6' of Formulas A-1-1 through A-1-4 is selected from H,

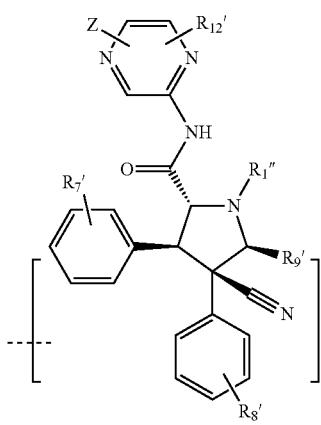
A-4-5

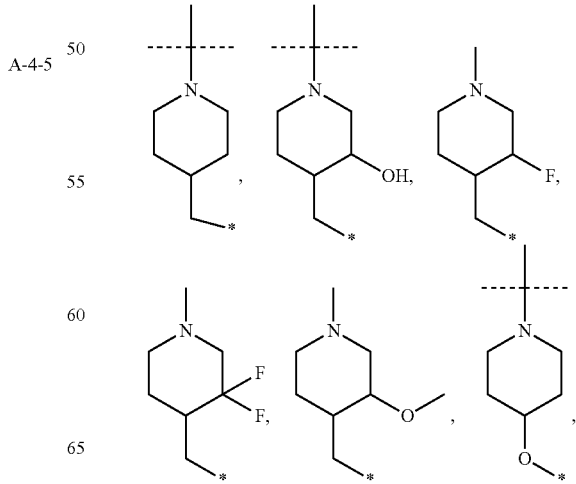

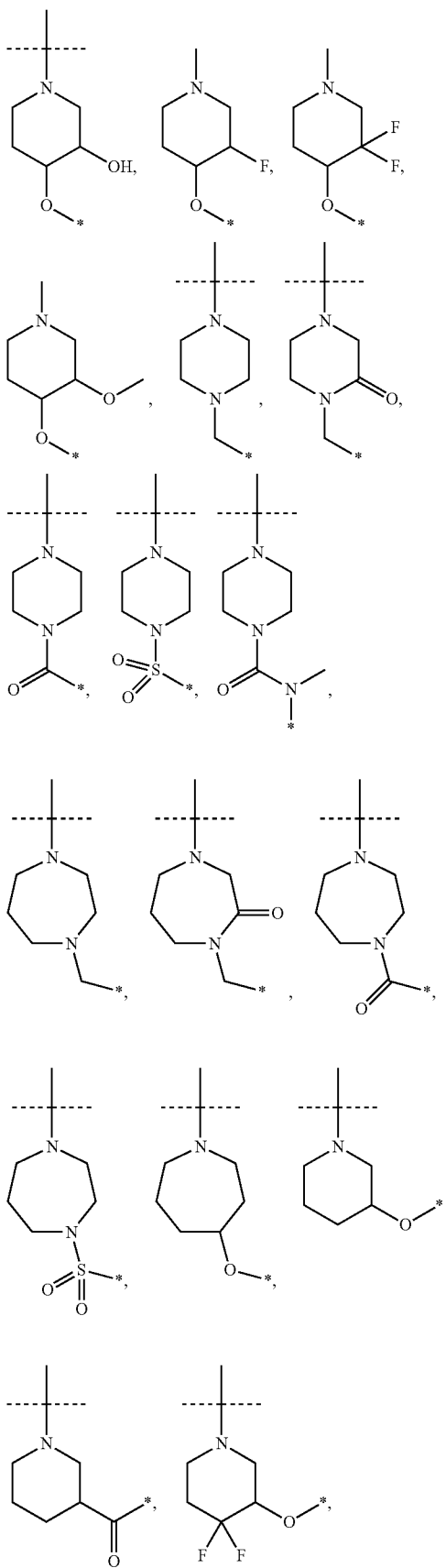
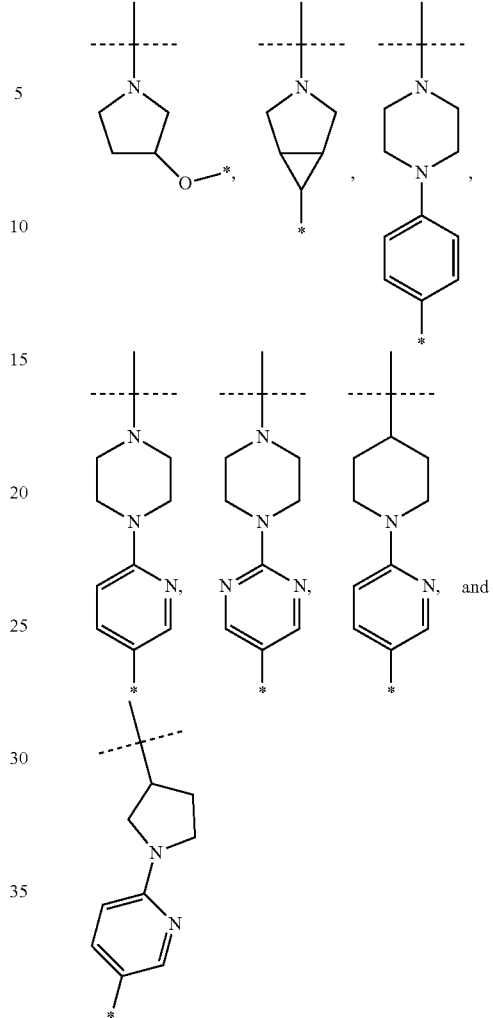

wherein the linker is attached to the "*" of $R^{6'}$ or to the terminal atom of $R^{4'}$;

R7' of Formula A-4-1 through A-4-6 is one or more (e.g., 1, 2, 3, 4) halogens;

R8' of Formula A-4-1 through A-4-6 is one or more groups (e.g., 1, 2, 3, or 4 groups) selected from the group consisting of H, —F, —Cl, —Br, —I, —CN, —NO$_2$, ethylnyl, cyclopropyl, methyl, ethyl, isopropyl, vinyl, methoxy, ethoxy, isopropoxy, —OH, other C$_{1-6}$ alkyl, other C$_{1-6}$ alkenyl, and C$_{1-6}$ alkynyl, mono-, di- or tri-substituted;

R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;

Z of Formula A-4-1 through A-4-6 is selected from the group consisting of H, —OCH$_3$, —OCH$_2$CH$_3$, and halogen;

R10' and R11' of Formula A-4-1 through A-4-6 are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH)$_n$—CONR'R", (CH$_2$)$_n$—OR', (CH$_2$)$_n$—SR', (CH$_2$)$_n$—SOR', (CH$_2$)$_n$—CH(OH)—R', (CH$_2$)$_n$—

COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_m$—(CH$_2$)$_n$—NR'COR", (CH$_2$CH$_2$O)$_m$(CH$_2$)$_n$—NR'SO$_2$R", (CH$_2$CH$_2$O)$_m$(CH$_2$)$_n$—COOH, (CH$_2$CH$_2$O)$_m$(CH$_2$)$_n$—COOR', (CH$_2$CH$_2$O)$_m$—(CH$_2$)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—(CH$_2$CH$_2$O)$_m$—(CH$_2$)$_n$R', (CH$_2$)$_p$—(CH$_2$CH$_2$O)$_m$—(CH$_2$)$_n$—OH, (CH$_2$)$_p$—(CH$_2$CH$_2$O)$_m$—(CH$_2$)$_n$—OR', (CH$_2$)$_p$—(CH$_2$CH$_2$O)$_m$—(CH$_2$)$_n$—NR'R", (CH$_2$)$_p$—(CH$_2$CH$_2$O)$_m$—(CH$_2$)$_n$—NR'COR", (CH$_2$)$_p$—(CH$_2$CH$_2$O)m-(CH$_2$)$_n$—NR'SO$_2$R", (CH$_2$)$_p$—(CH$_2$CH$_2$O)$_m$—(CH$_2$)$_n$—COOH, (CH$_2$)$_p$—(CH$_2$CH$_2$O)$_m$—(CH$_2$)$_n$—COOR', (CH$_2$)$_p$—(CH$_2$CH$_2$O)$_m$—(CH$_2$)$_n$—CONR'R", (CH$_2$)p-(CH$_2$CH$_2$O)$_m$—(CH$_2$)$_n$—SO$_2$R', (CH$_2$)$_p$—(CH$_2$CH$_2$O)$_m$—(CH$_2$)$_n$—COR', (CH$_2$)$_p$—(CH$_2$CH$_2$O)$_m$(CH$_2$)$_n$—SONR'R", (CH$_2$)$_p$—(CH$_2$CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), N(alkyl)$_2$, oxo, carboxy, clcloalkyl and heteroaryl;

m, n, and p are independently 0 to 6;

R12' of Formula A-4-1 through A-4-6 is selected from the group consisting of —O-(alkyl), —O-(alkyl)-akoxy, —C(O)-(alkyl), —C(OH)-alkyl-alkoxy, —C(O)—NH-(alkyl), —C(O)—N-(alkyl)$_2$, —S(O)-(alkyl), S(O)$_2$-(alkyl), —C(O)—(cyclic amine), and —O-aryl-(alkyl), —O-aryl-(alkoxy);

R1" of Formula A-4-1 through A-4-6 is selected from the group consisting of H, alkyl, aryl substituted alkyl, aloxy substituted alkyl, cycloalkyl, ary-substituted cycloalkyl, and alkoxy substituted cycloalkyl; and ∕∕∕ denotes connection to L.

In any aspect or embodiment described herein, the MLM is selected from:

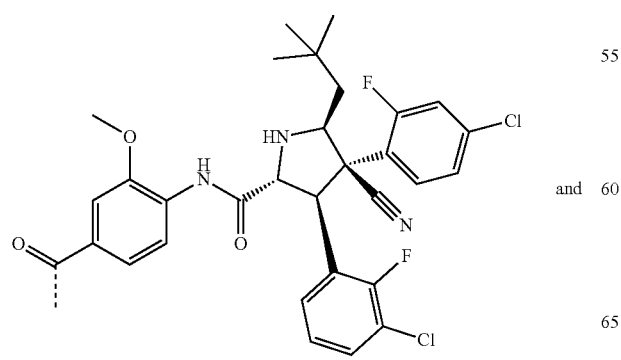

and

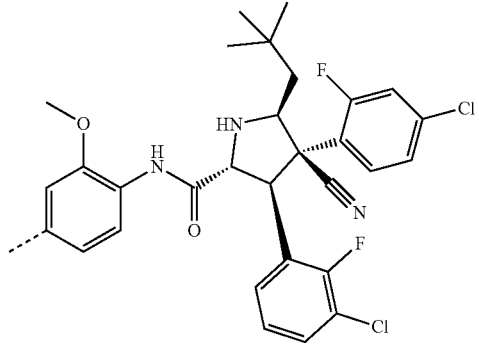

In any aspect or embodiment described herein, the ULM is a IAP E3 ubiquitin ligase binding moiety (ILM) comprising the amino acids alanine (A), valine (V), proline (P), and isoleucine (I) or their unnatural mimetics.

In any aspect or embodiment described herein, the ULM is a IAP E3 ubiquitin ligase binding moiety (ILM) comprising a AVPI tetrapeptide fragment or derivative thereof.

In any aspect or embodiment described herein, the ILM is selected from the group consisting of chemical structures represented by Formulas (I), (II), (III), (IV), and (V):

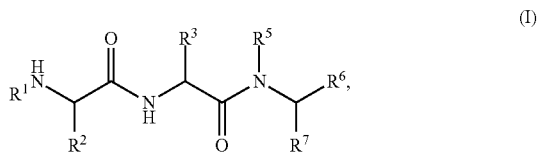
(I)

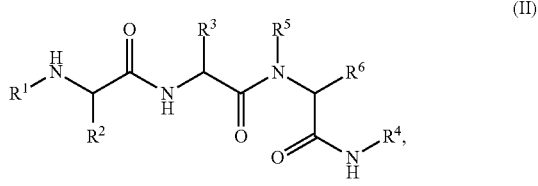
(II)

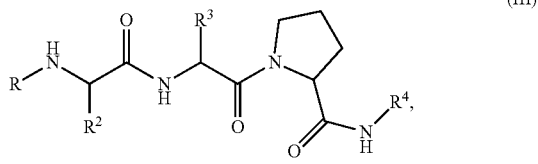
(III)

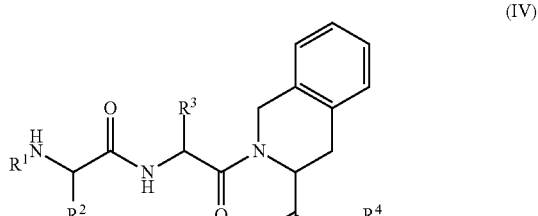
(IV)

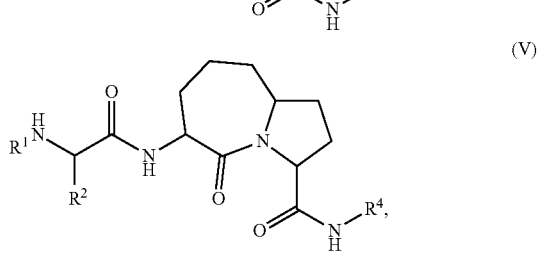
(V)

wherein:
- R¹ for Formulas (I), (II), (III), (IV), and (V) is selected from H or alkyl;
- R² for Formulas (I), (II), (III), (IV), and (V) is selected from H or alkyl;
- R³ for Formulas (I), (II), (III), (IV), and (V) is selected from H, alkyl, cycloalkyl and heterocycloalkyl;
- R⁵ and R⁶ for Formulas (I), (II), (III), (IV), and (V) are independently selected from H, alkyl, cycloalkyl, heterocycloalkyl, or more preferably, R⁵ and R⁶ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;
- R³ and R⁵ for Formulas (I), (II), (III), (IV), and (V) taken together can form a 5-8-membered ring further optionally fused to 1-2 cycloalkyl, heterocycloalkyl, aryl or heteroaryl rings;
- R⁷ for Formulas (I), (II), (III), (IV), and (V) is selected from cycloalkyl, cycloalkylalkyl, heterocycloalkyl, heterocycloalkylalkyl, aryl, aryl-C(O)—R⁴, arylalkyl, heteroaryl, heteroaryl-C(O)—R⁴, heteroaryl-R⁴, heteroaryl-naphthalene, heteroarylalkyl, or —C(O)NH—R⁴, each one further optionally substituted with 1-3 substituents selected from halogen, alkyl, haloalkyl, hydroxyl, alkoxy, cyano, (hetero)cycloalkyl, aryl, (hetero)aryl, —C(O)NH—R⁴, or —C(O)—R⁴; and
- R⁴ is selected from alkyl, cycloalkyl, heterocycloalkyl, cycloalkylalkyl, heterocycloalkylalkyl, aryl or bicyclic aryl, arylalkyl, heteroaryl (e.g., a bicyclic heteroaryl), heteroarylalkyl, further optionally substituted with 1-3 substituents as described above.

In any aspect or embodiment described herein, the ILM is selected from the group consisting of:

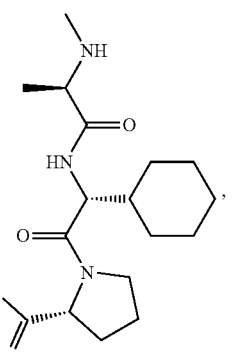

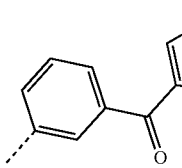

,

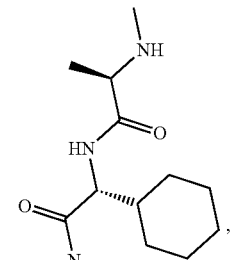

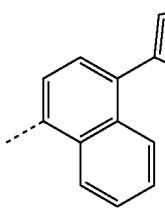

,

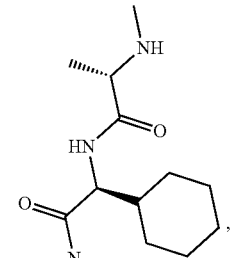

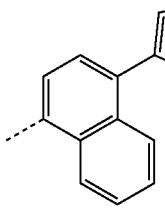

,

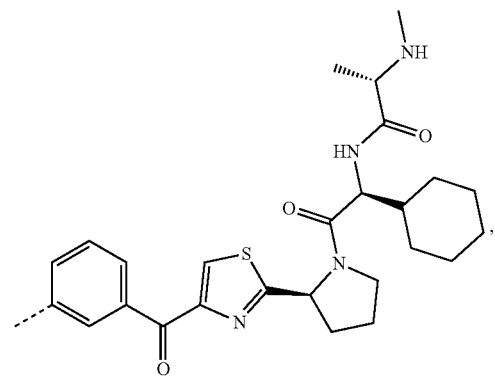

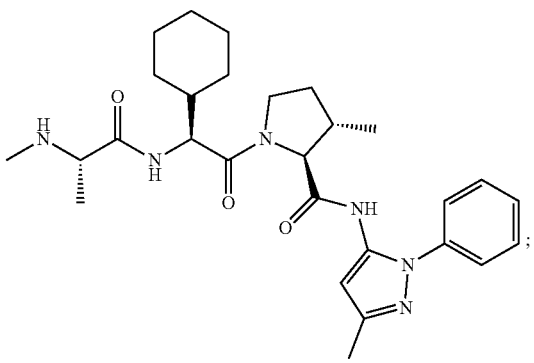

;

1031
-continued
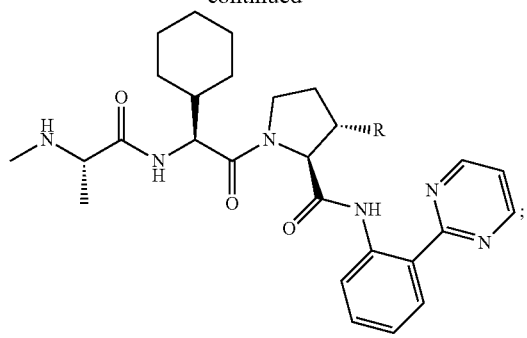
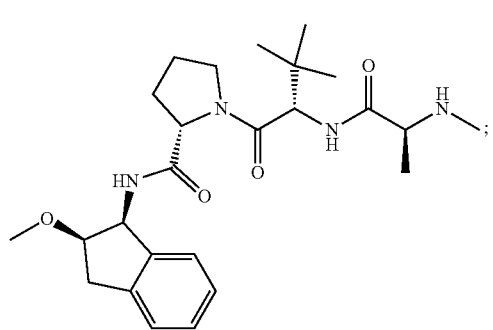
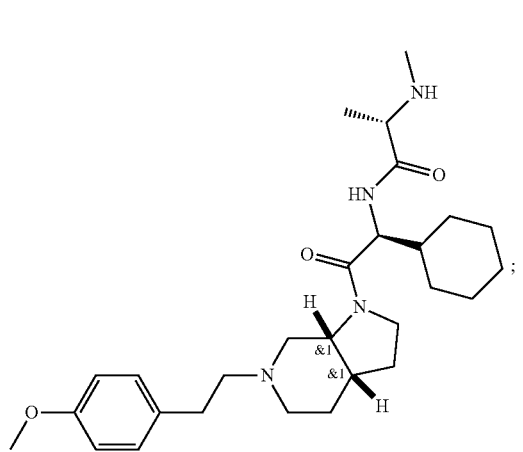
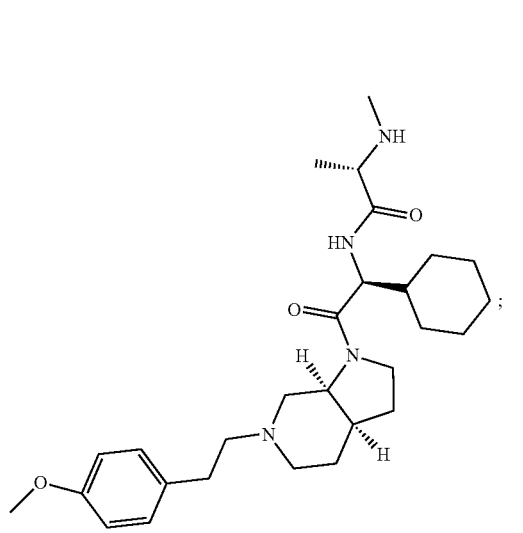
1032
-continued
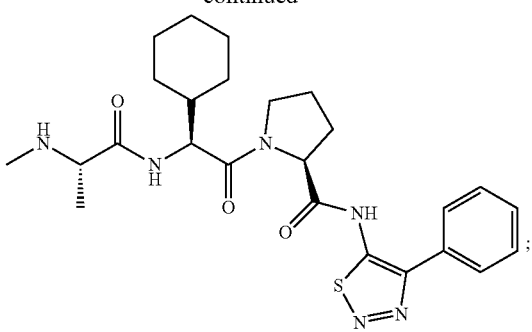
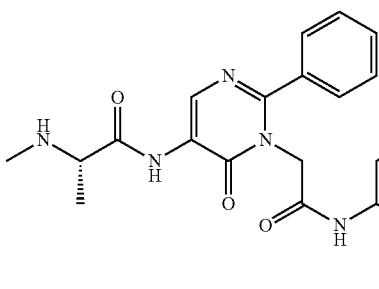
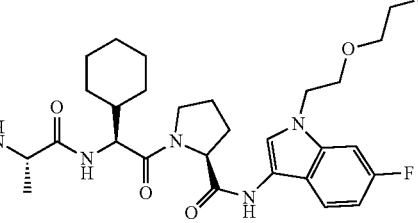
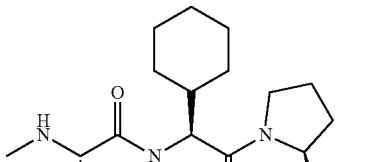
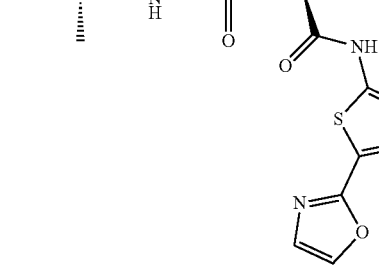
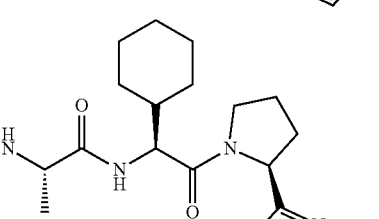
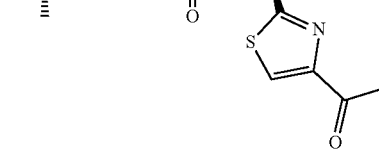

-continued

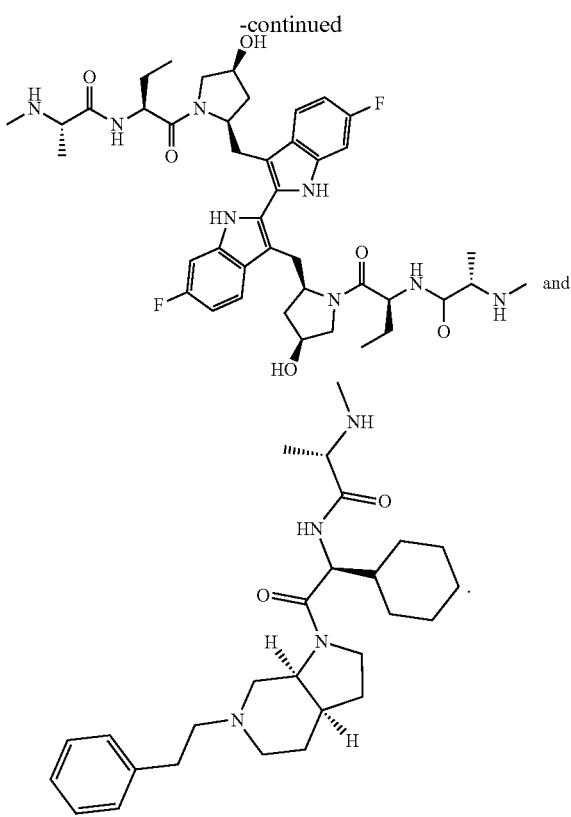

In any aspect or embodiment described herein, the linker (L) comprises a chemical structural unit represented by the formula:

-(A$^L$)$_q$-, wherein:
-(A$^L$)q- is a group which is connected to at least one of ULM, PTM, or both;
q is an integer greater than or equal to 1;
each A$^L$ is independently selected from the group consisting of, a bond, CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L1}$, NR$^{L3}$C (=NCN), NR$^{L3}$C(=CNO$_2$)NR$^{L4}$, C$_{3-11}$cycloalkyl optionally substituted with 0-6 R$^{L1}$ and/or R$^{L2}$groups, C$_{3-11}$heteocyclyl optionally substituted with 0-6 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups; and
R$^{L1}$, R$^{L2}$, R$^{L3}$, RN and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_0$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl) SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In any aspect or embodiment described herein, the linker (L) includes an optionally substituted C$_1$-C$_{50}$ alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, C$_{31}$, C$_{32}$, C$_{33}$, C$_{34}$, C$_{35}$, C$_{36}$, C$_{37}$, C$_{38}$, C$_{39}$, C$_{40}$, C$_{41}$, C$_{42}$, C$_{43}$, C$_{44}$, C$_{45}$, C$_{46}$, C$_{47}$, C$_{48}$, C$_{49}$, or C$_{50}$ alkyl), wherein each carbon is optionally substituted with (1) a heteroatom selected from N, S, P, or Si atoms that has an appropriate number of hydrogens, substitutions, or both to complete valency, (2) an optionally substituted cycloalkyl or bicyclic cycloalkly, (3) an optionally substituted heterocyloalkyl or bicyclic heterocyloalkyl, (4) an optionally substituted aryl bicyclic aryl, or (5) optionally substituted heteroaryl or bicyclic heteroaryl, with the proviso that there is no heteroatom-heteroatom bonding (e.g., no heteroatoms are covalently linked or adjacently located).

In any aspect or embodiment described herein, the unit A$^L$ of linker (L) comprises a group represented by a general structure selected from the group consisting of:

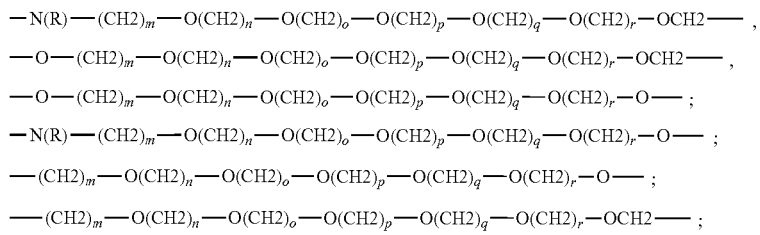

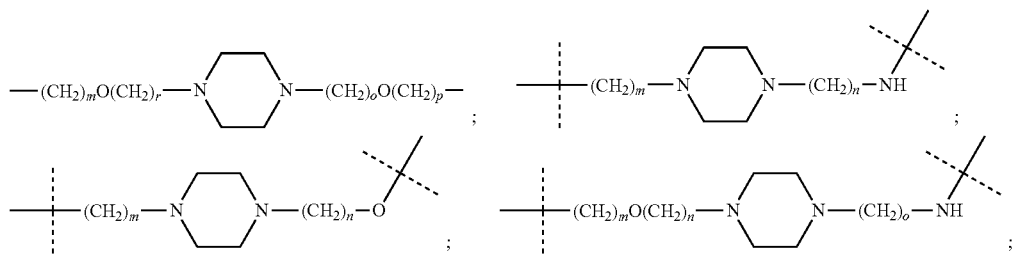

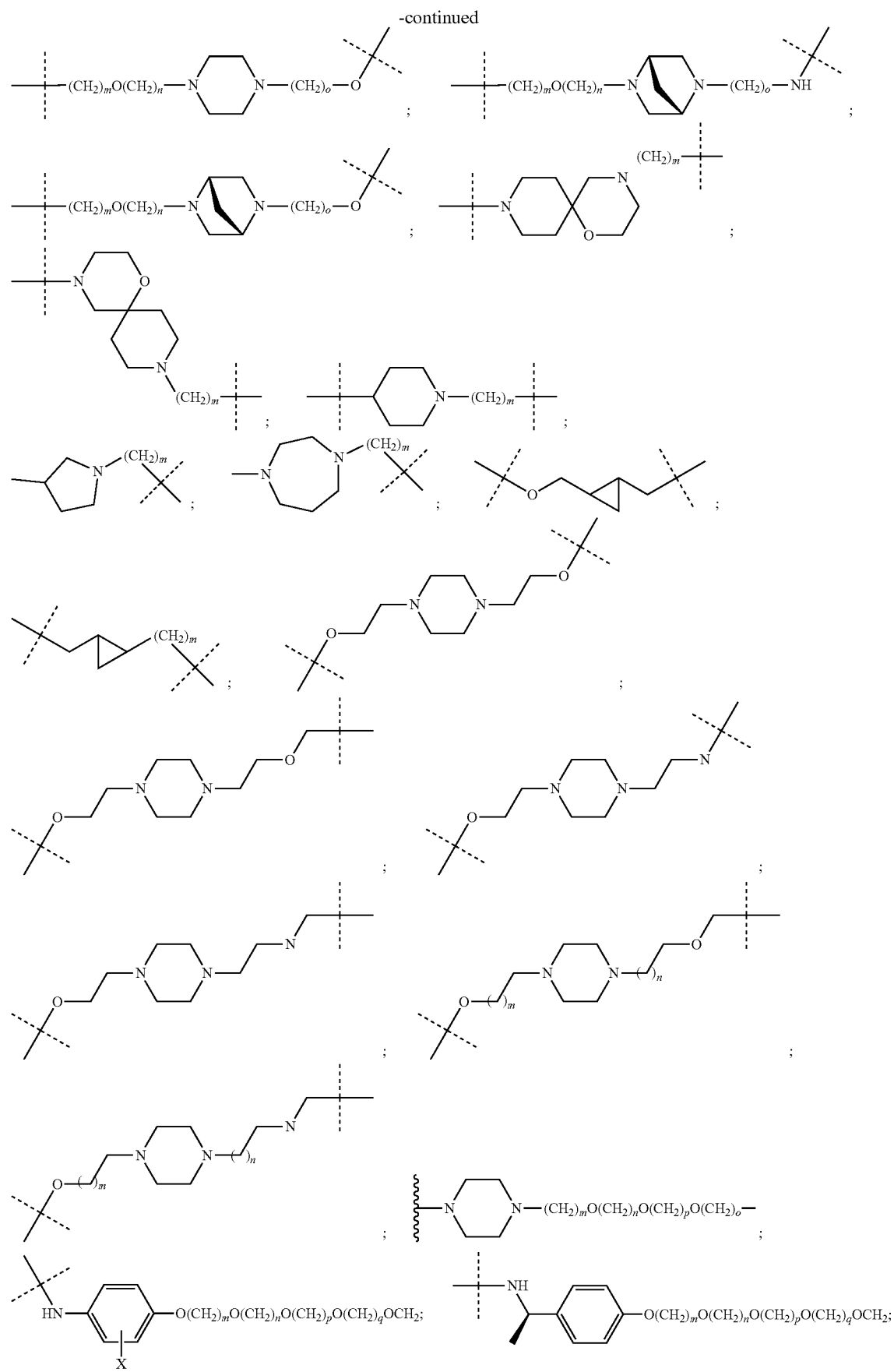

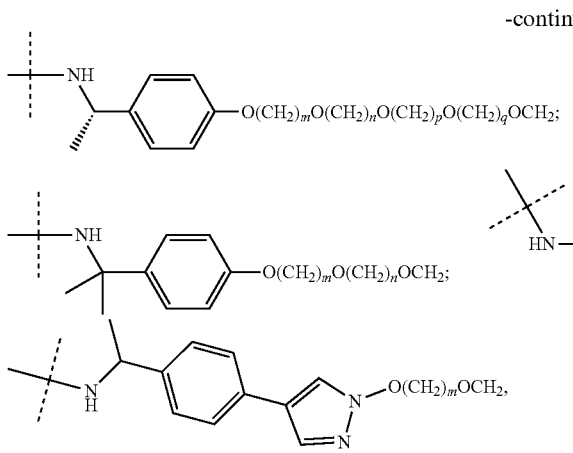
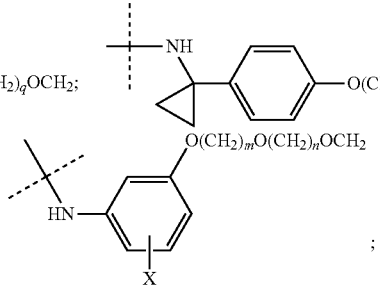
wherein each m, n, o, p, q, and r, is independently 0, 1, 2, 3, 4, 5, 6, 7, 8, 9, 10, 11, 12, 13, 14, 15, 16, 17, 18, 19, or 20, with the proviso that when the number is zero, there is no N—O or O—O bond, R is selected from the group H, methyl and ethyl, and X is selected from the group H and F;
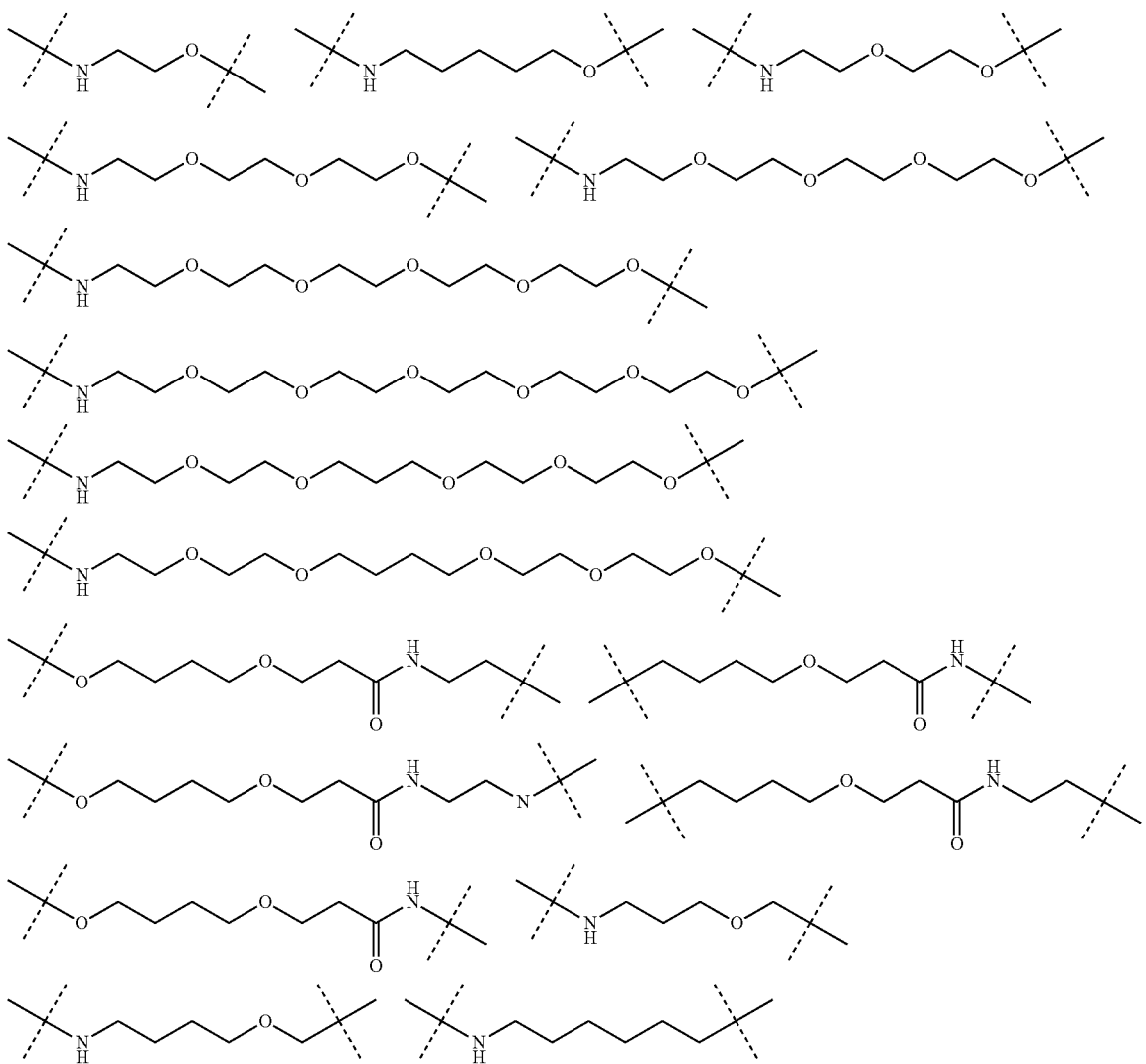

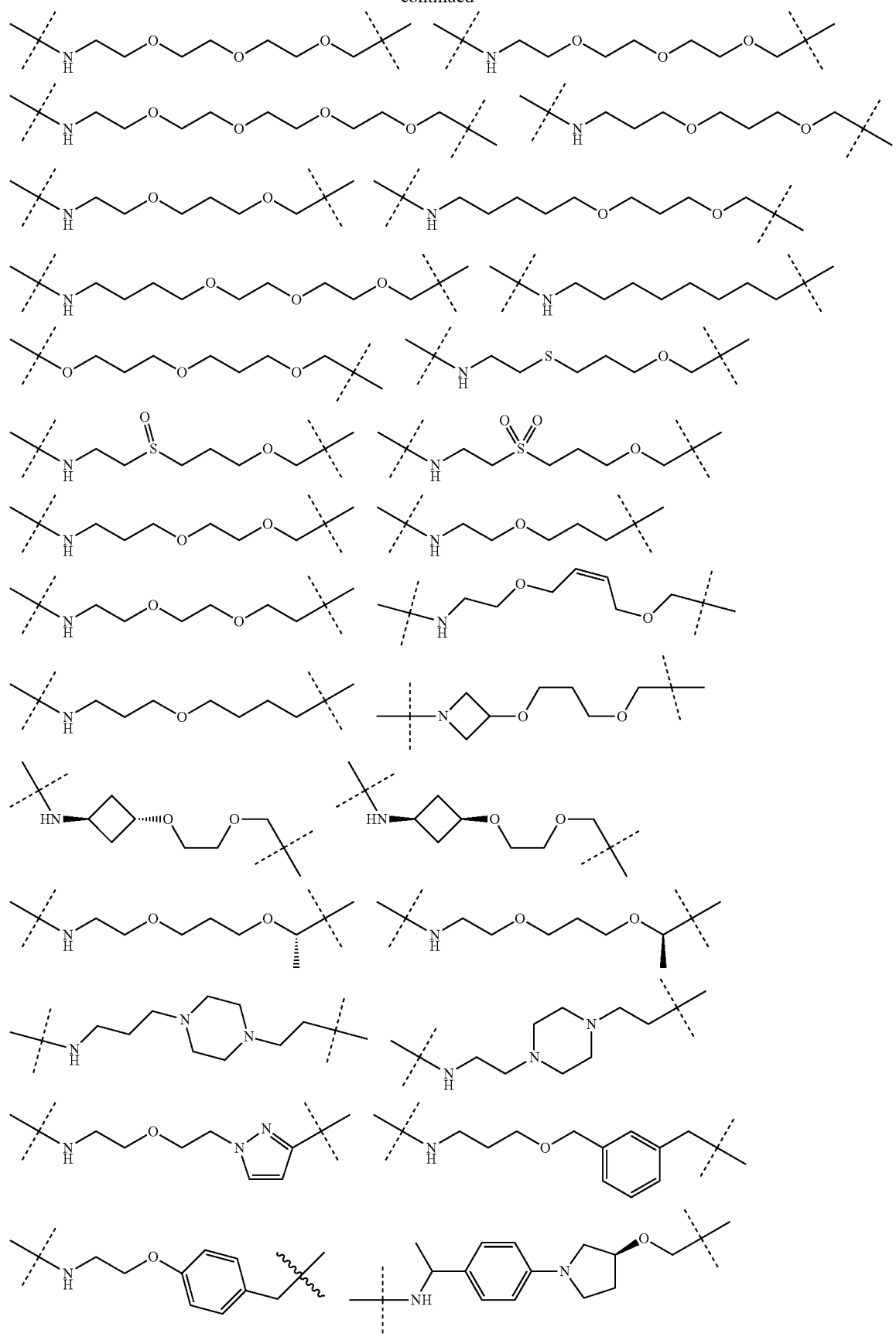

1041 1042
-continued
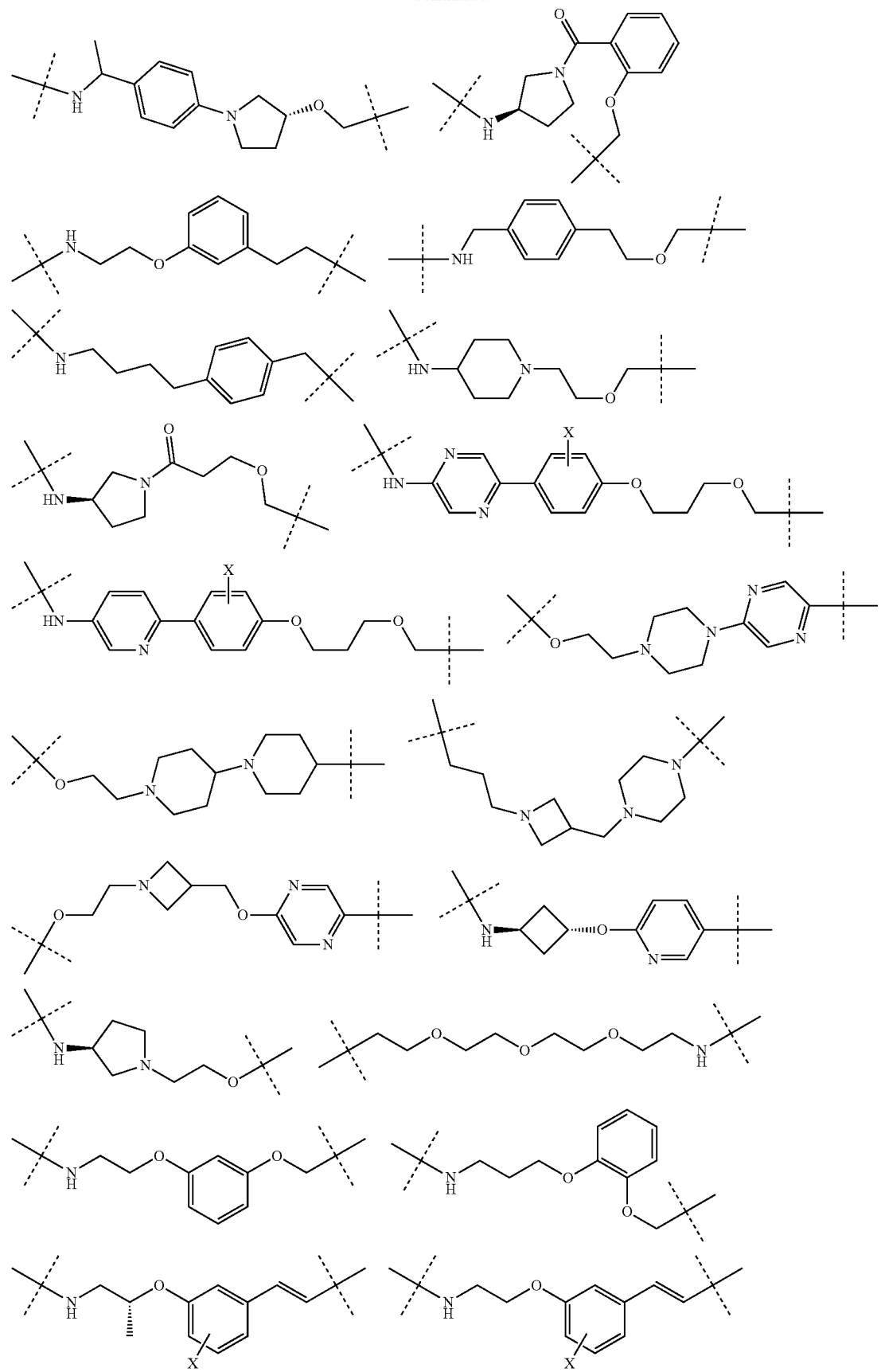

1043 1044
-continued
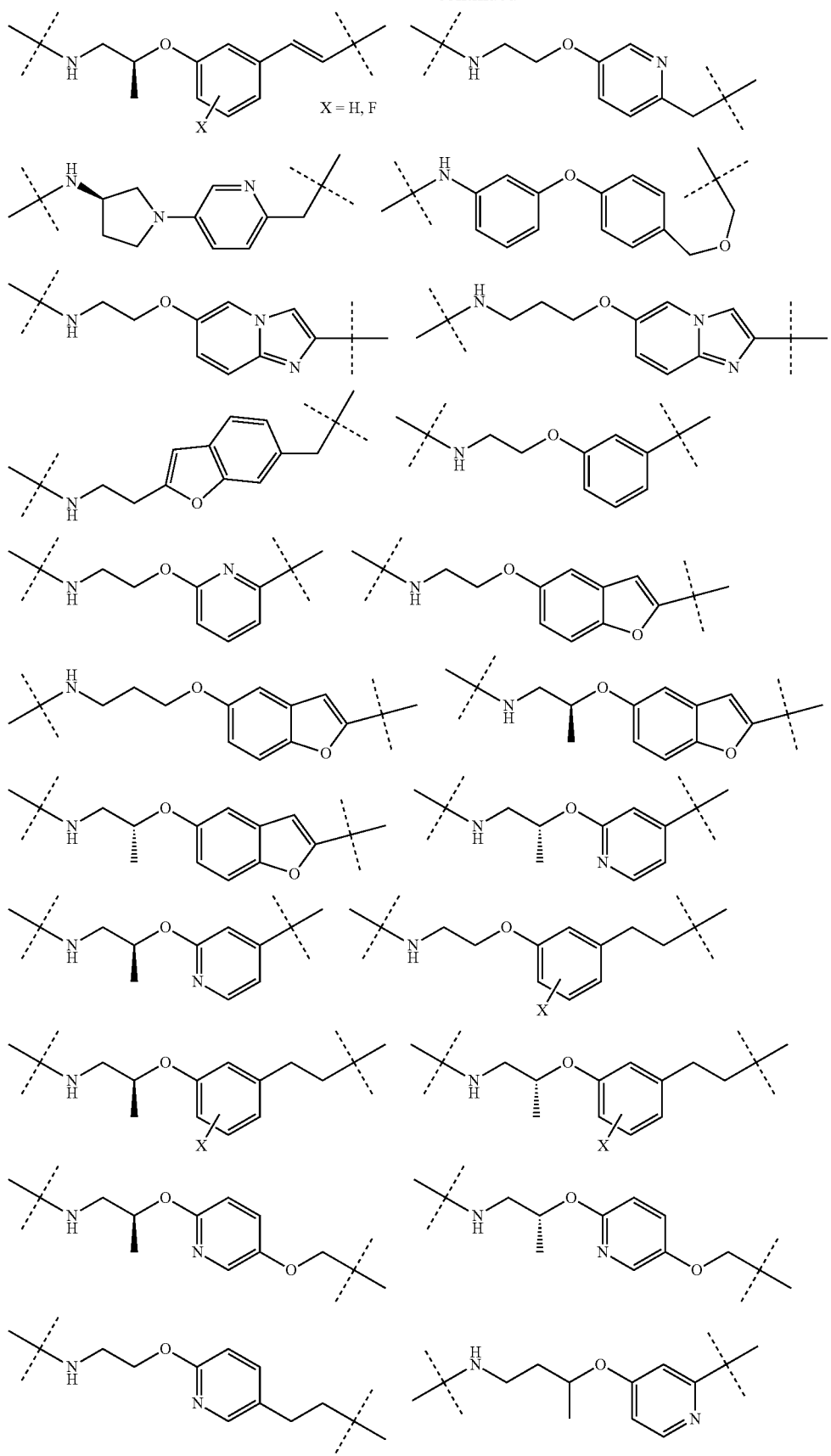

-continued
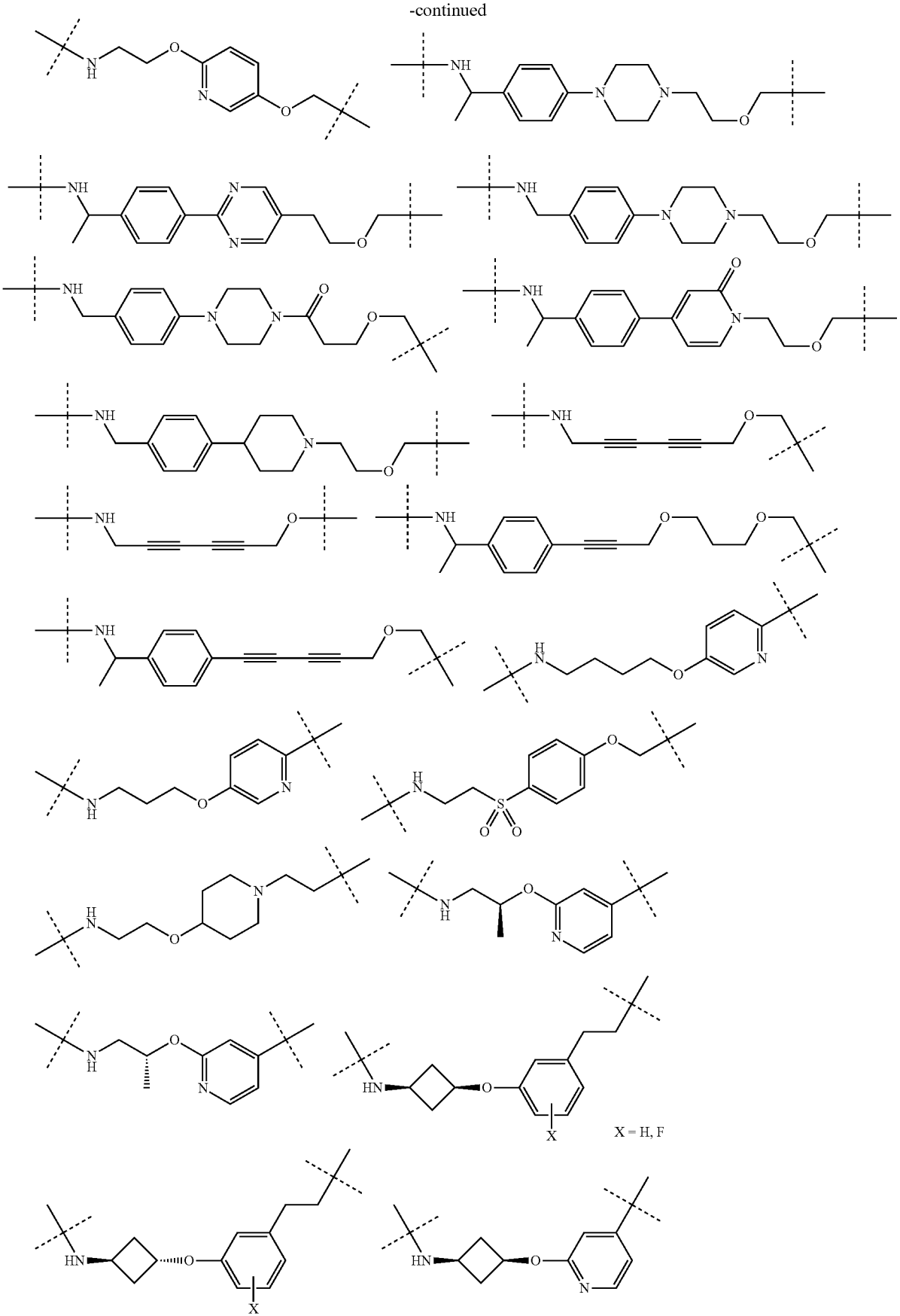

-continued
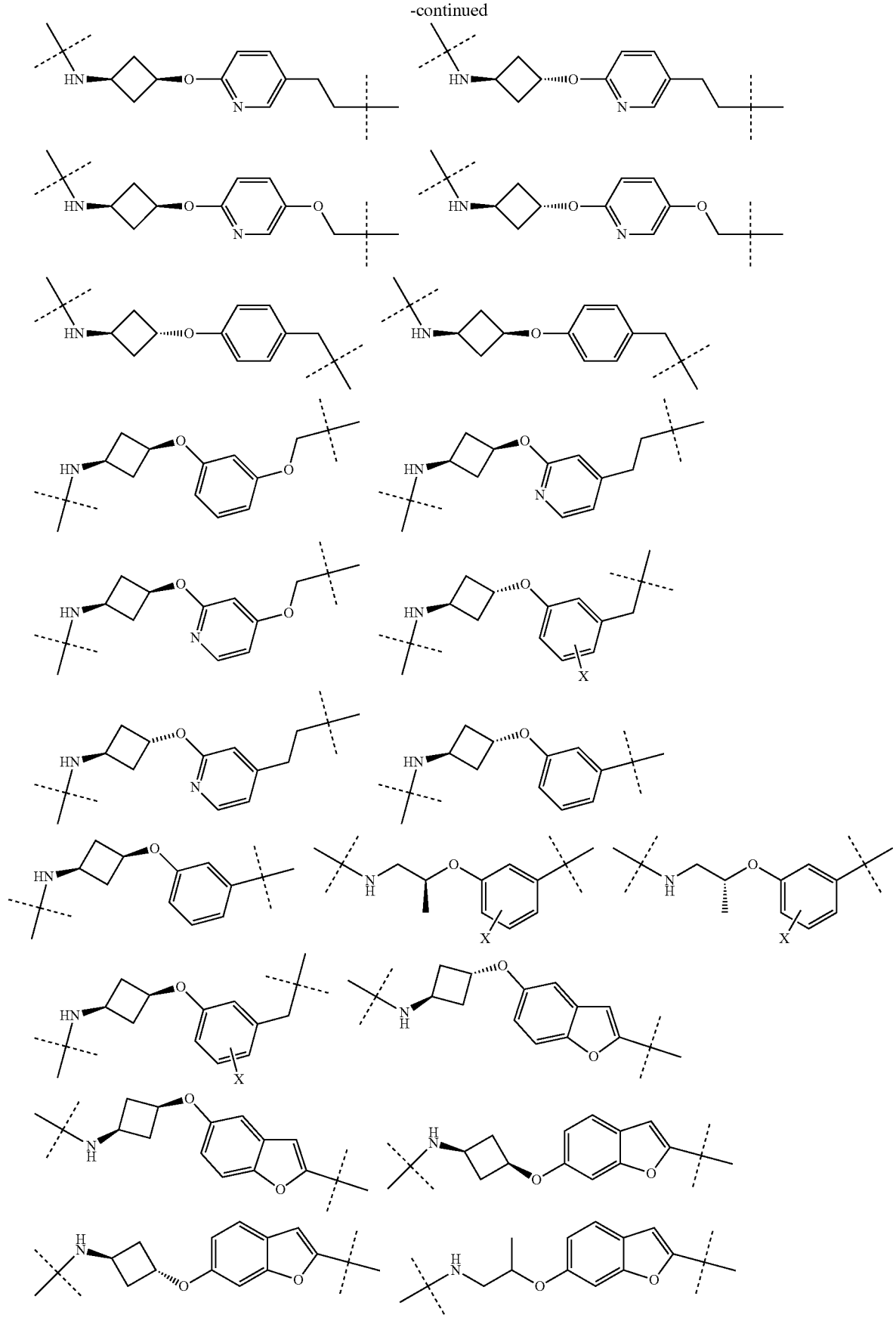

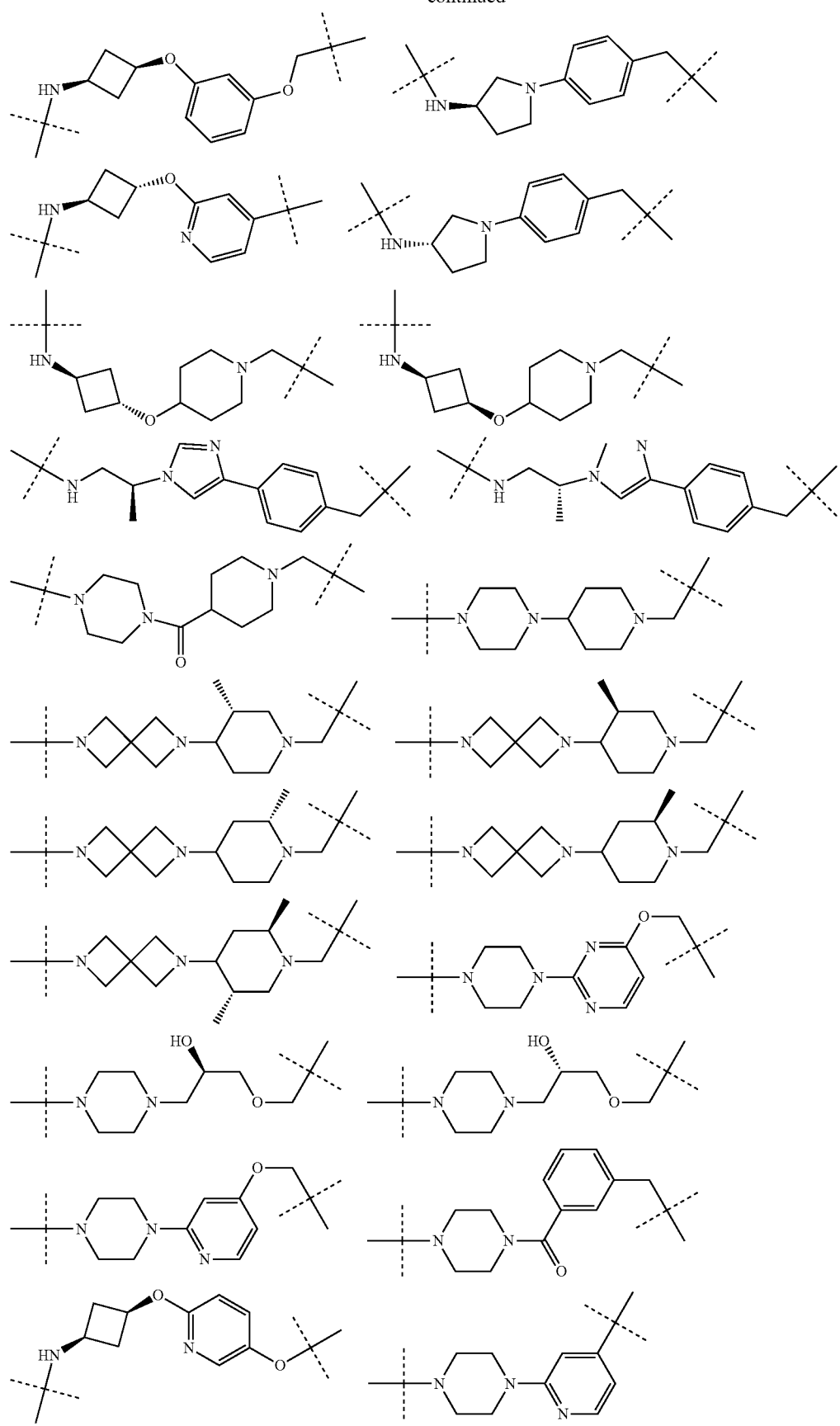

-continued
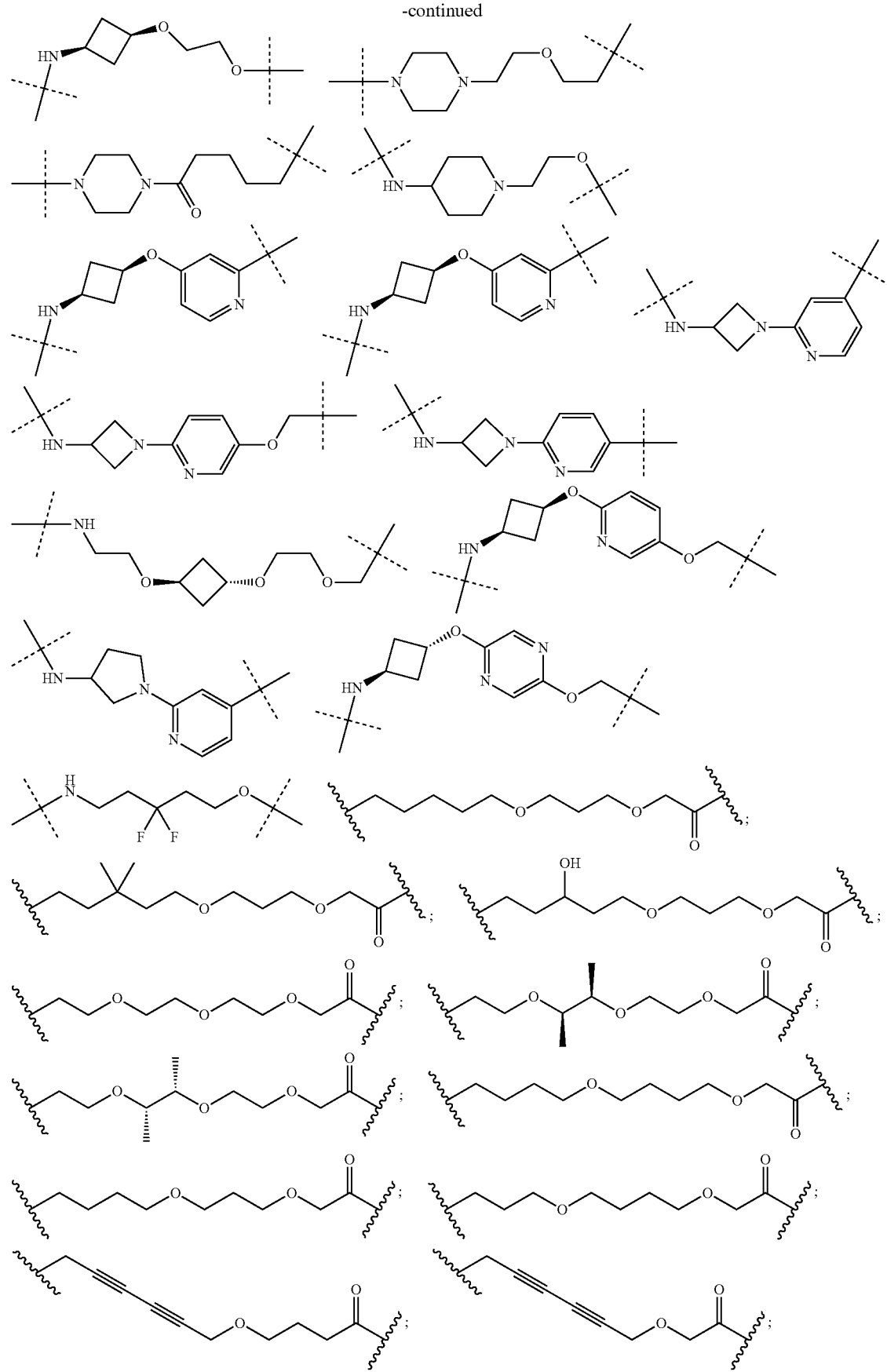

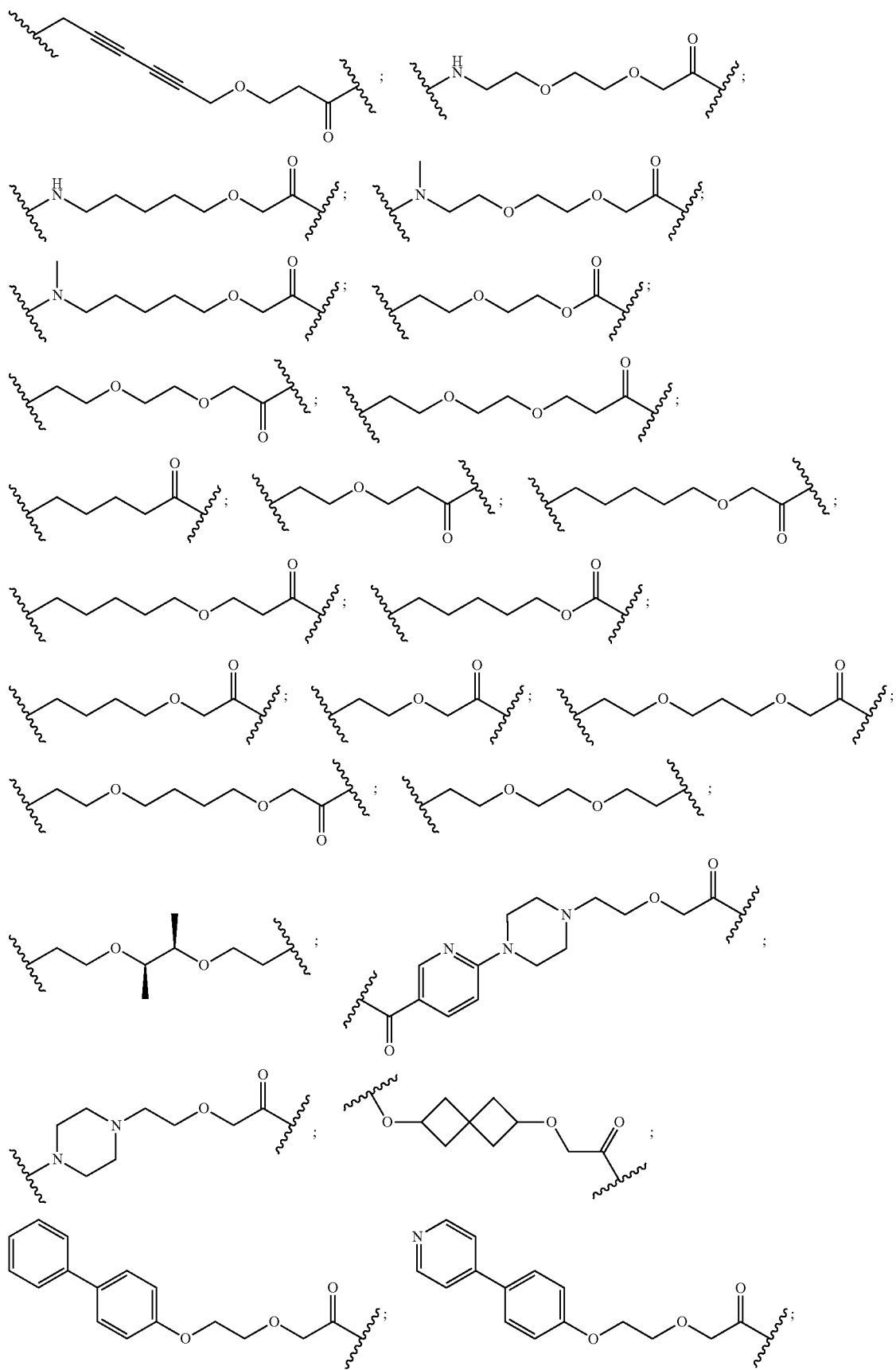

1055
1056
-continued
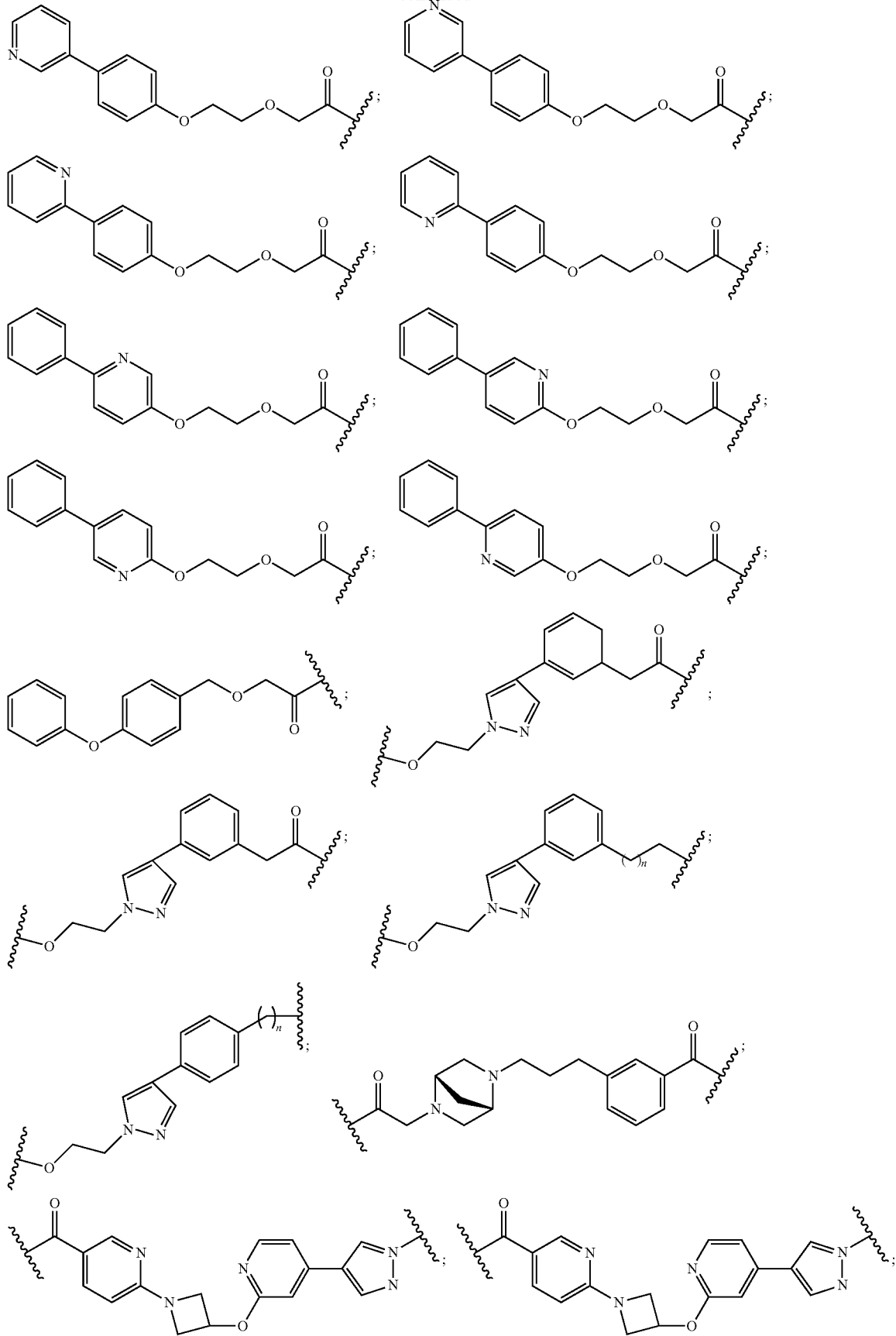

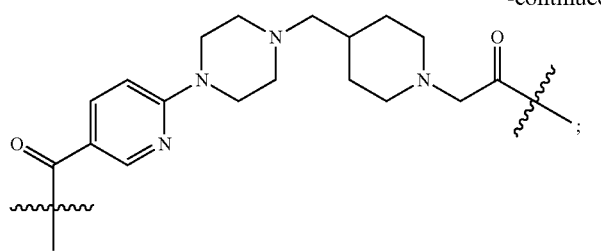
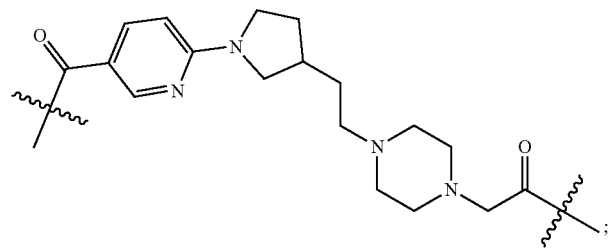
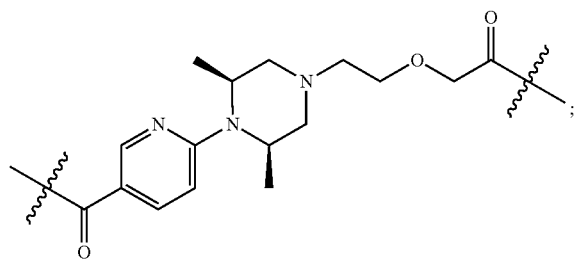
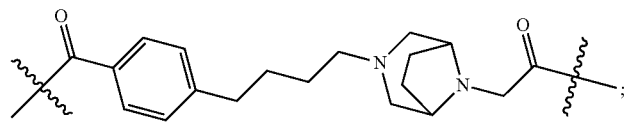
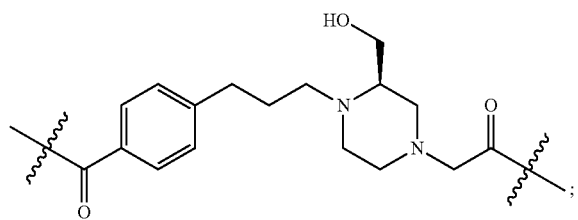
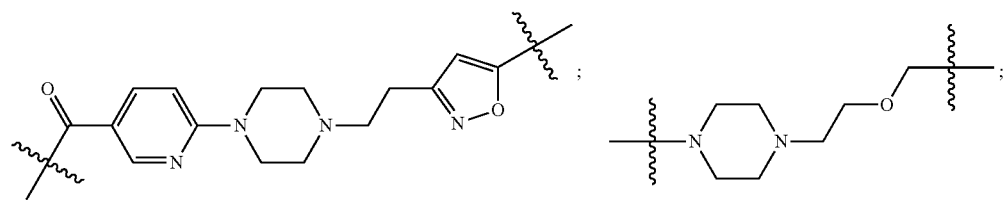
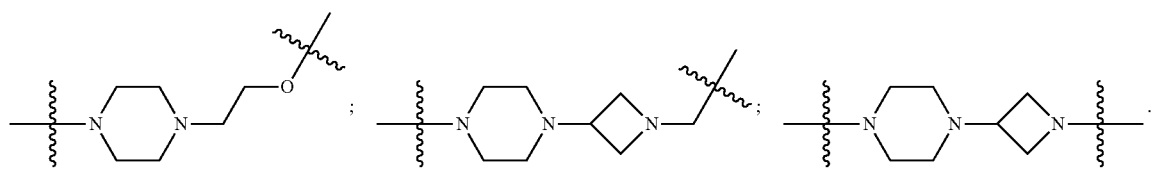

In any aspect or embodiment described herein, the unit $A^L$ of linker (L) is selected from the group consisting of:
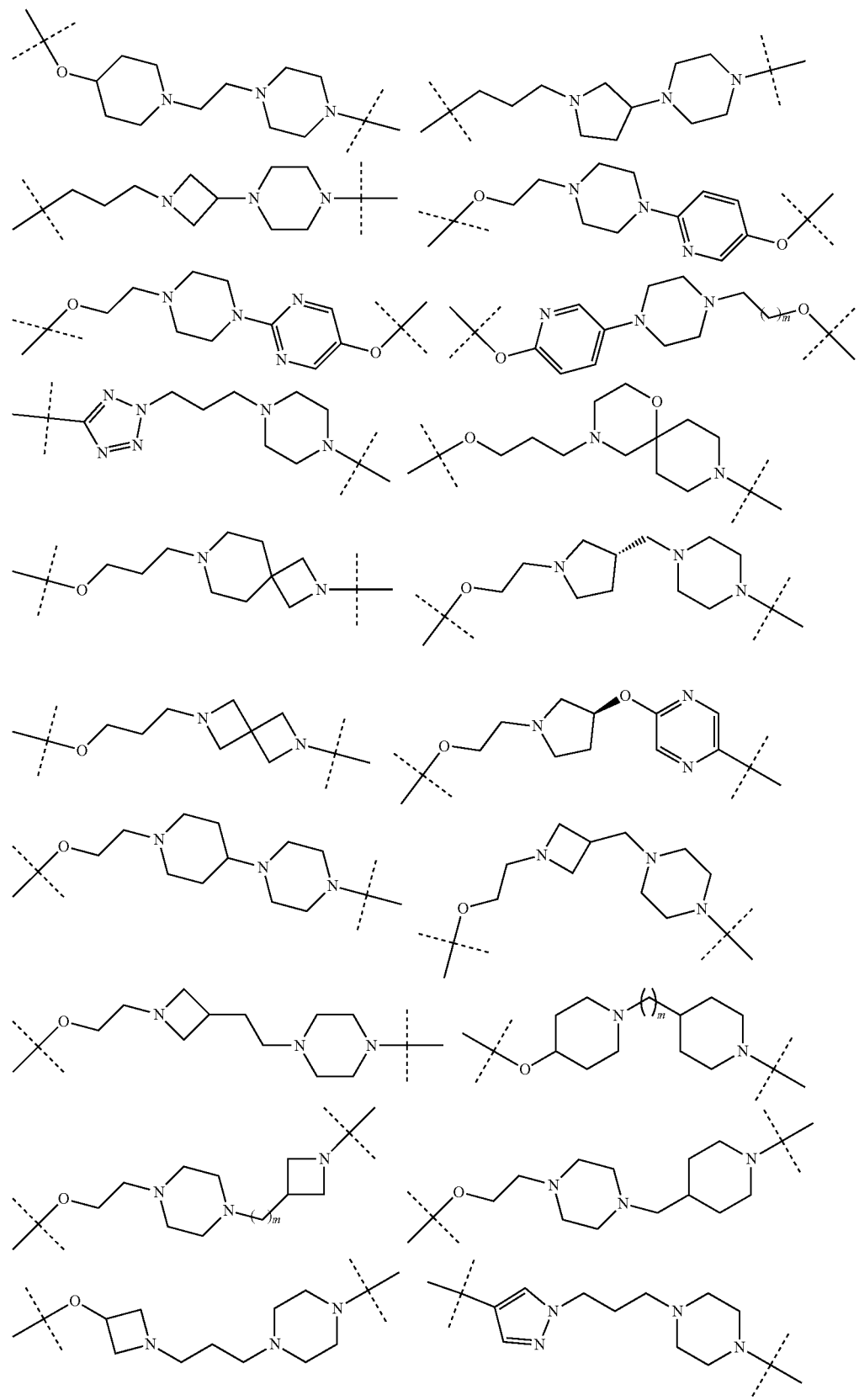

1061 1062
-continued
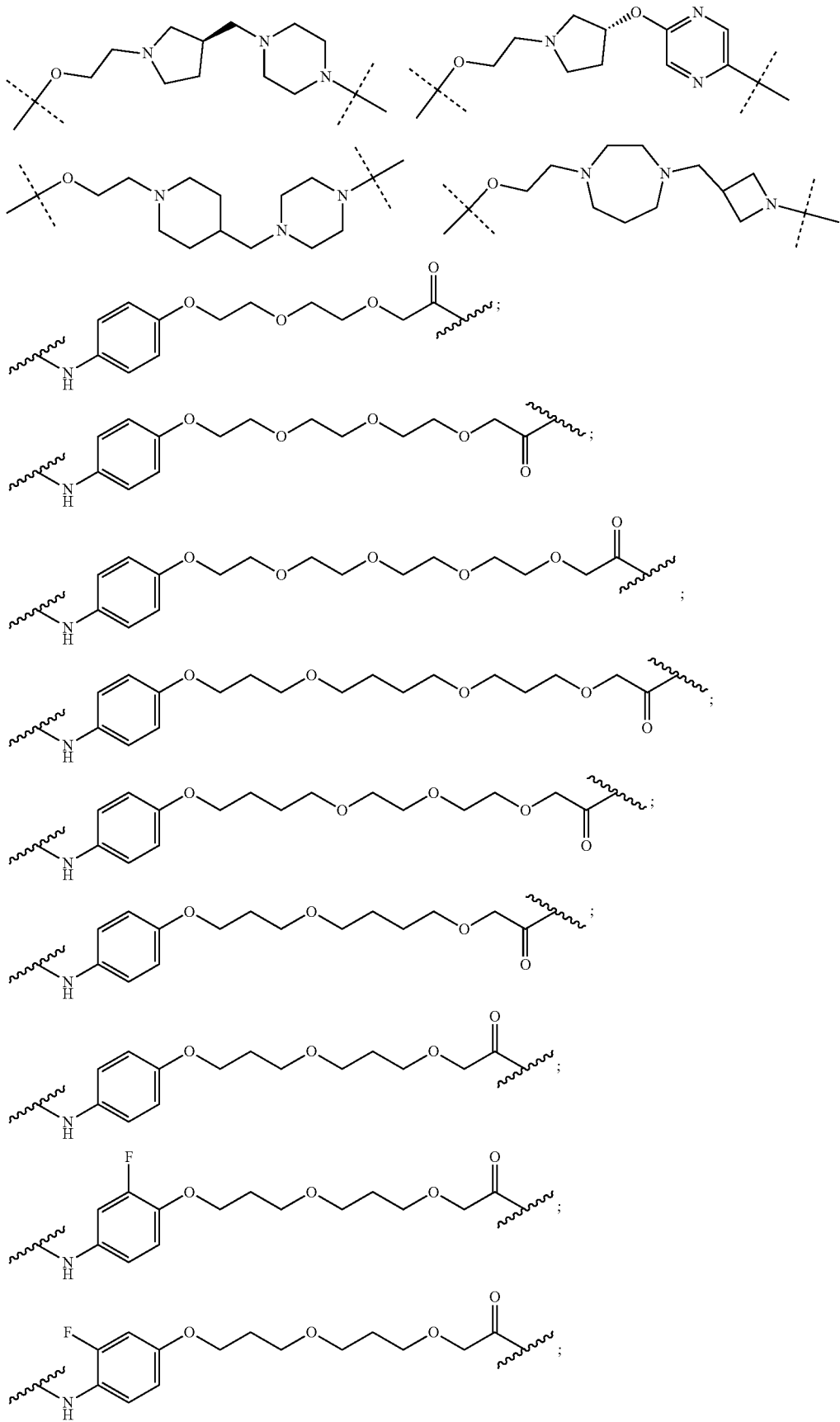

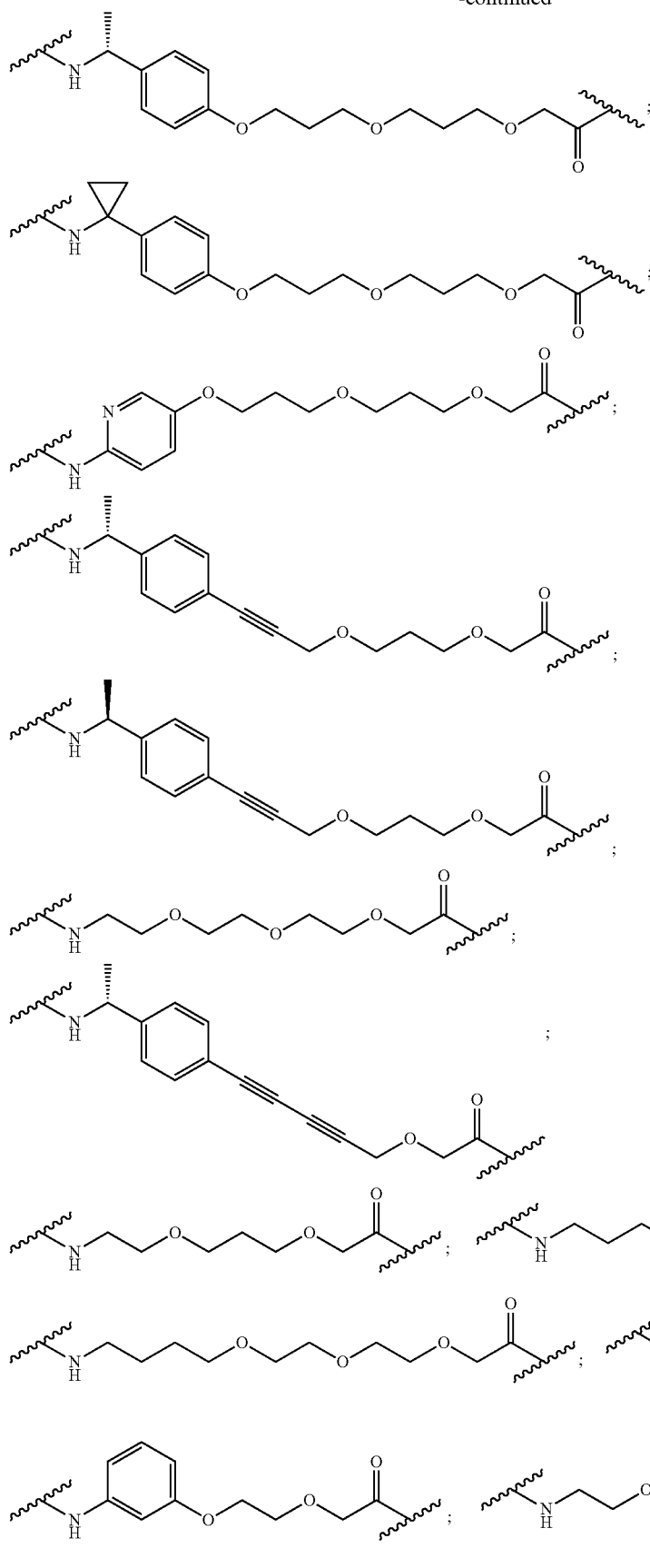

1065 1066
-continued
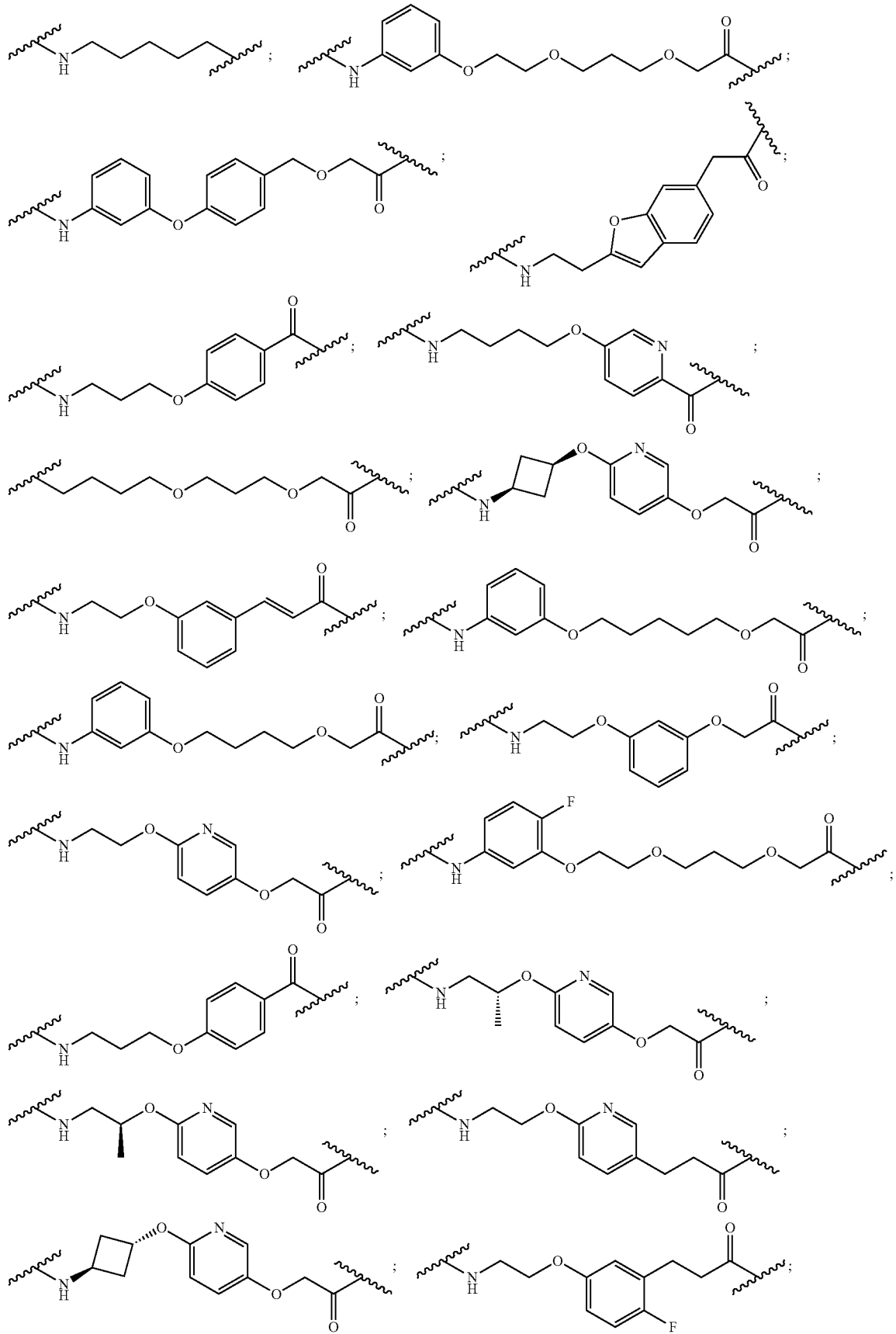

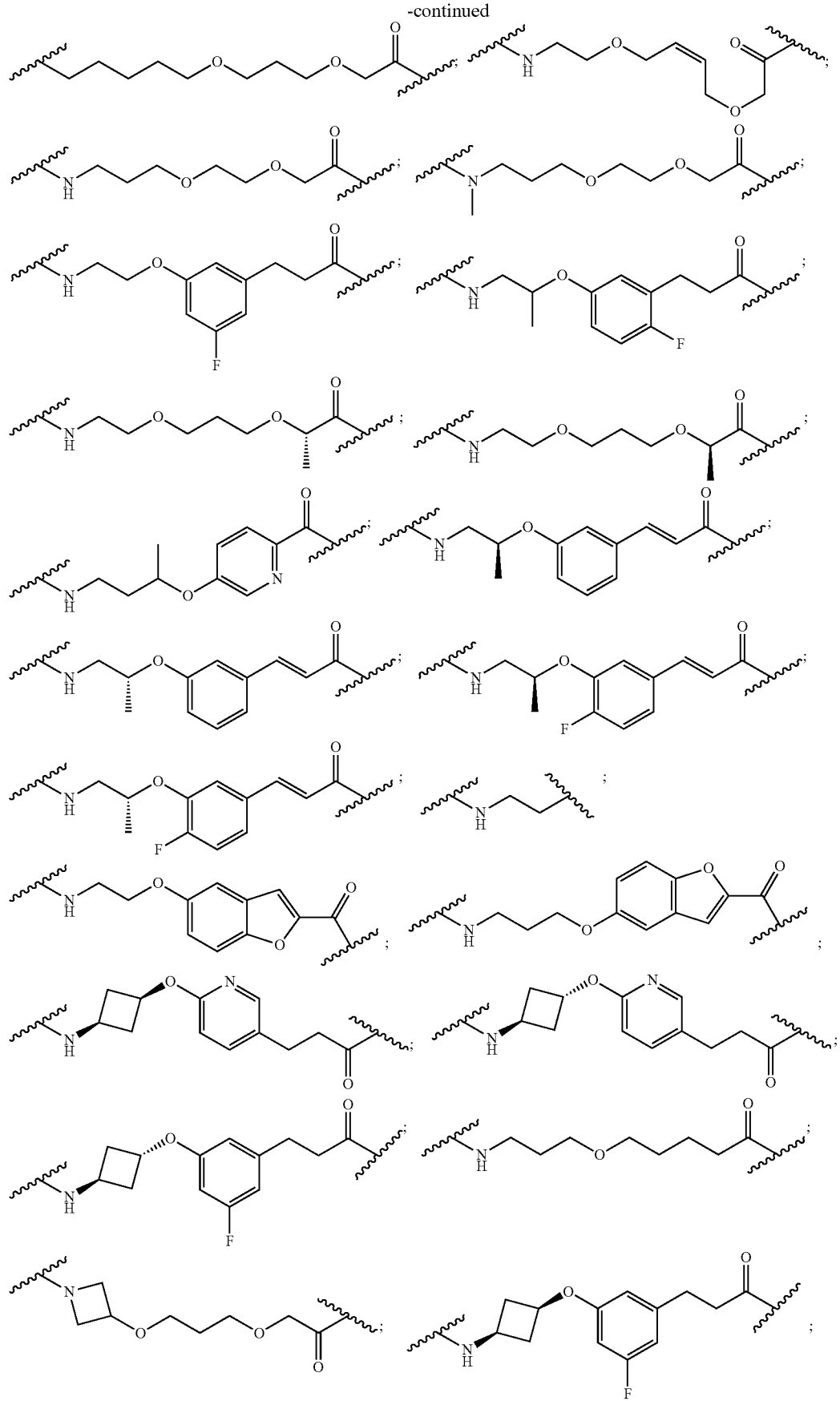

-continued
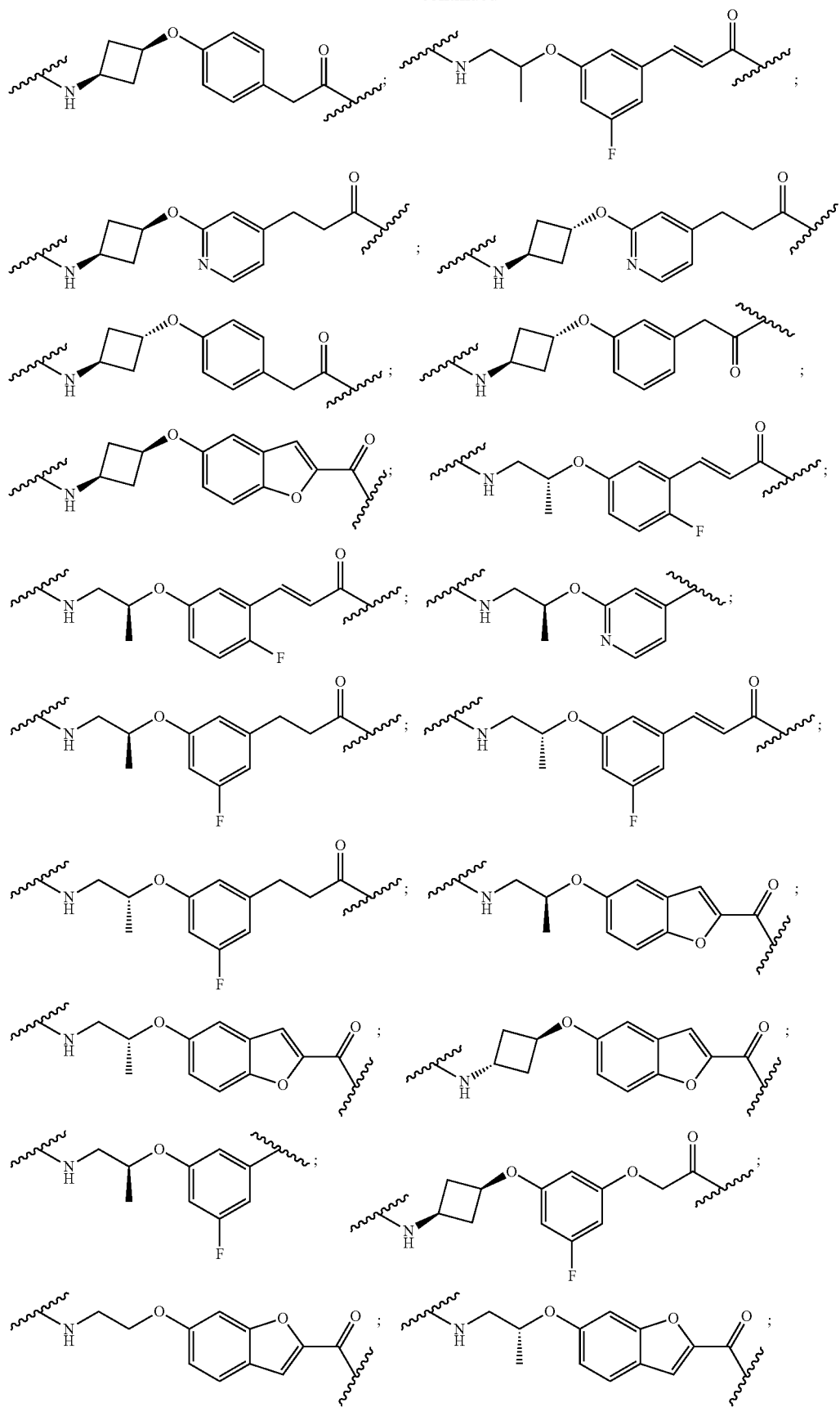

1071
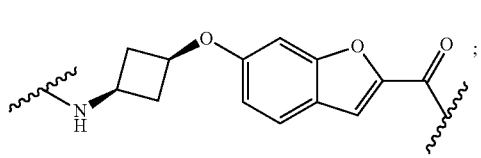
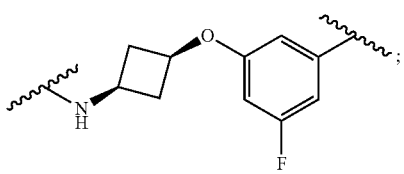
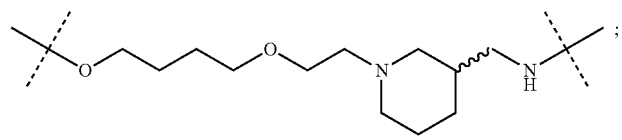
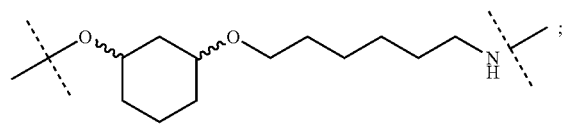 and
1072
-continued
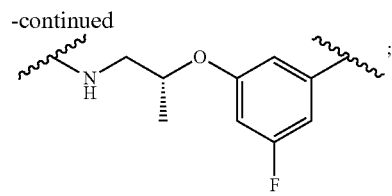
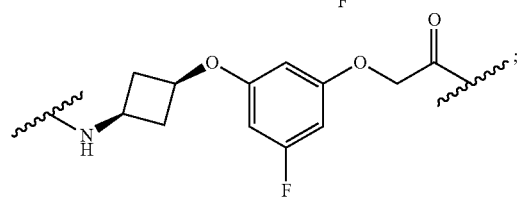
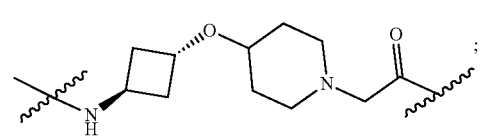
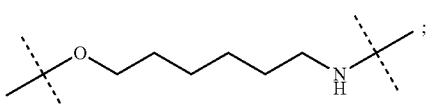
wherein each m and n is independently selected from 0, 1, 2, 3, 4, 5, or 6.
In any aspect or embodiment described herein, the unit $A^L$ of linker (L) is selected from the group consisting of:
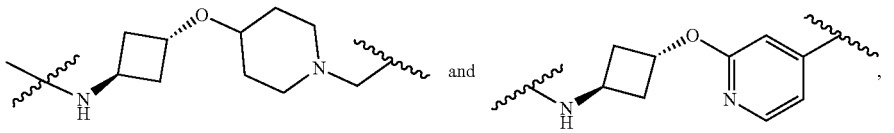
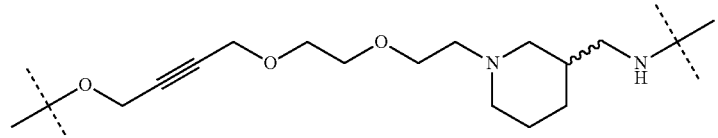
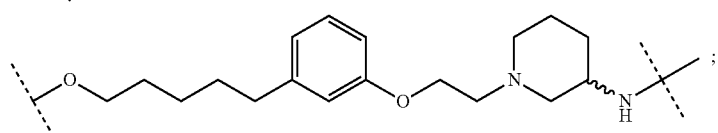
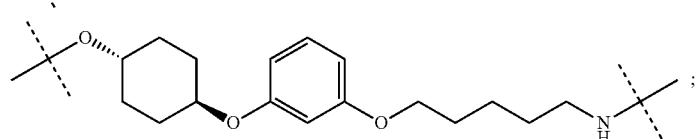
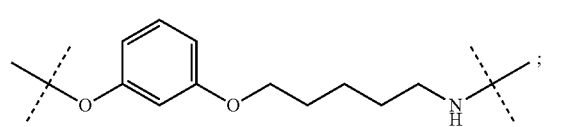  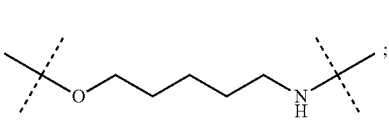
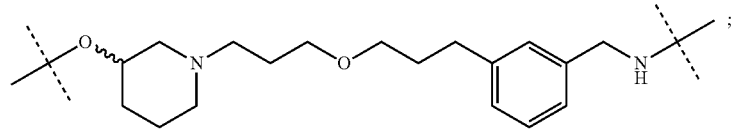

1073
-continued
1074
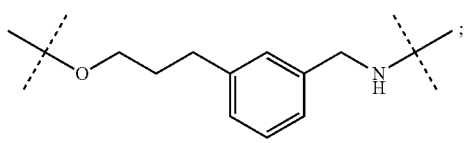
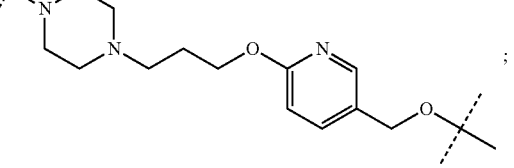
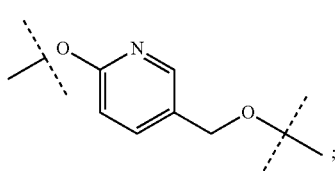
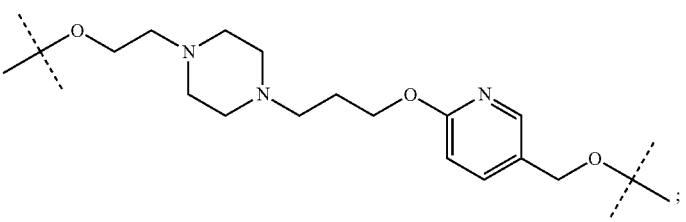
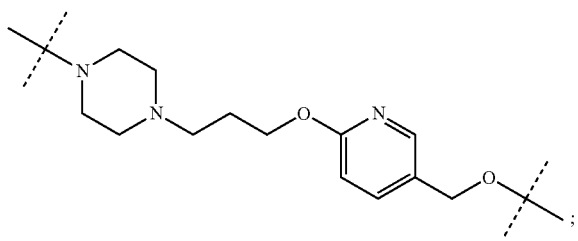
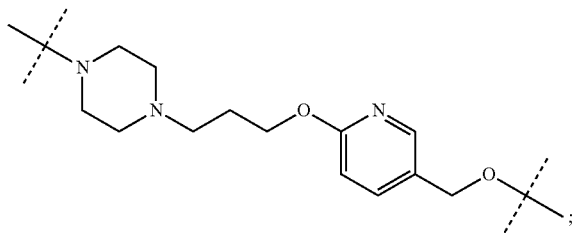
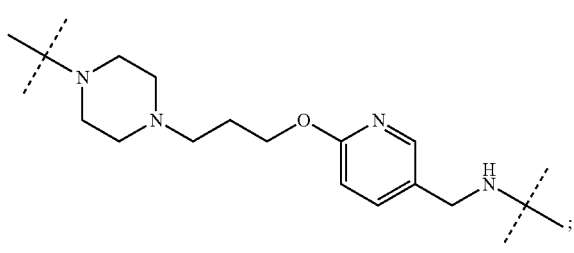
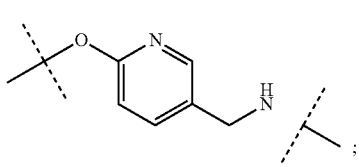
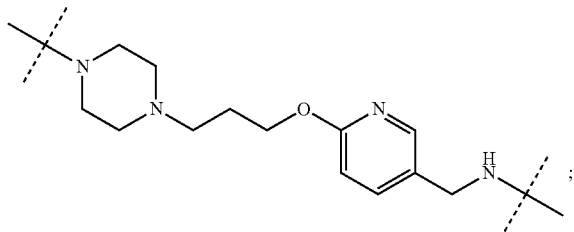
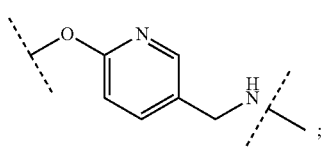
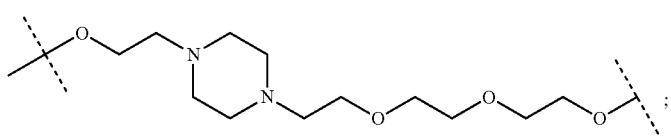
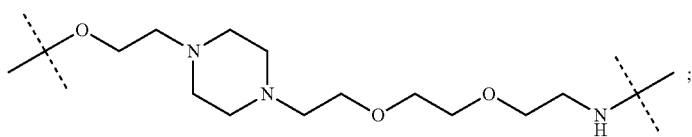

1075           1076
-continued
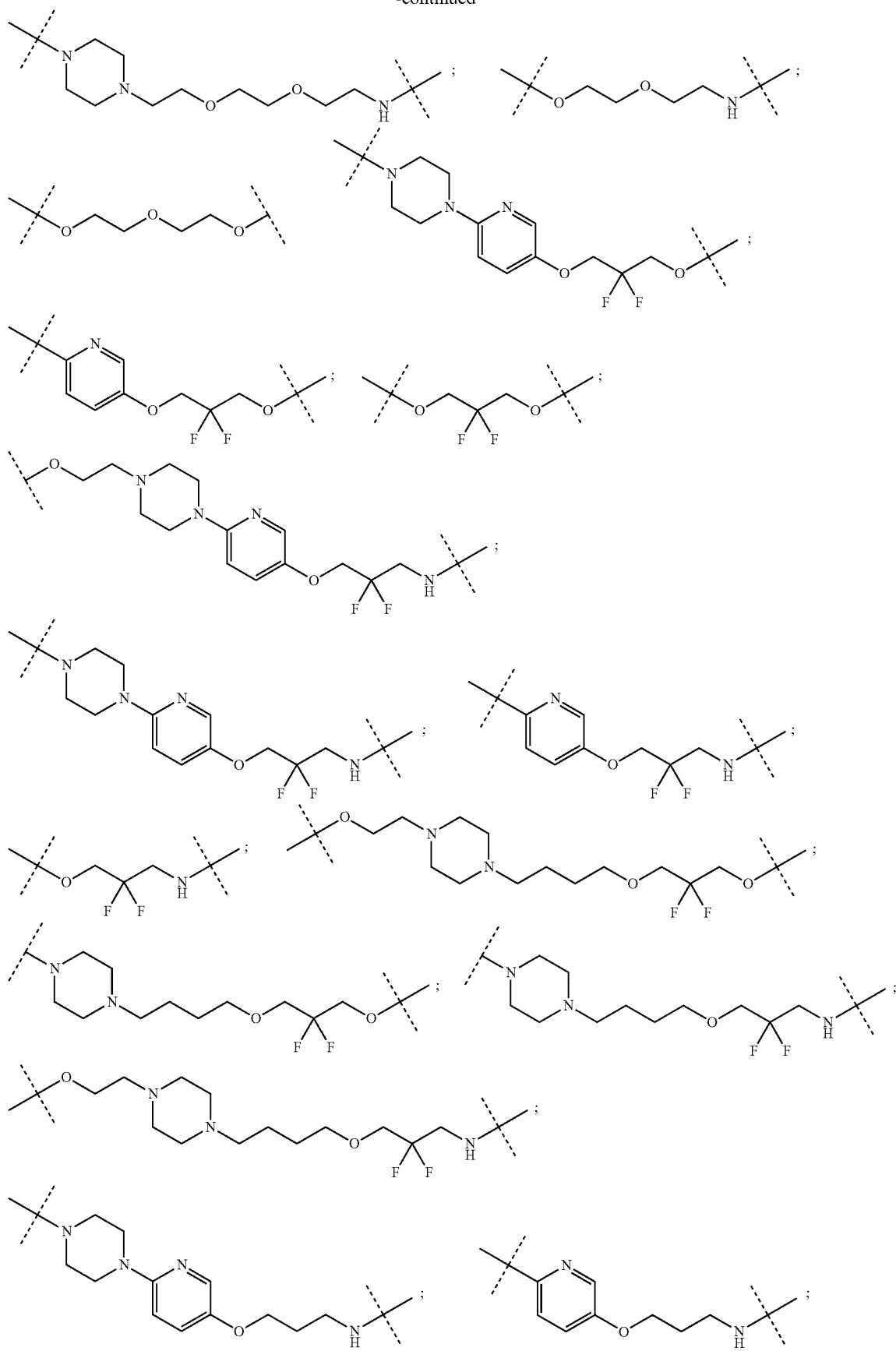

1077 1078
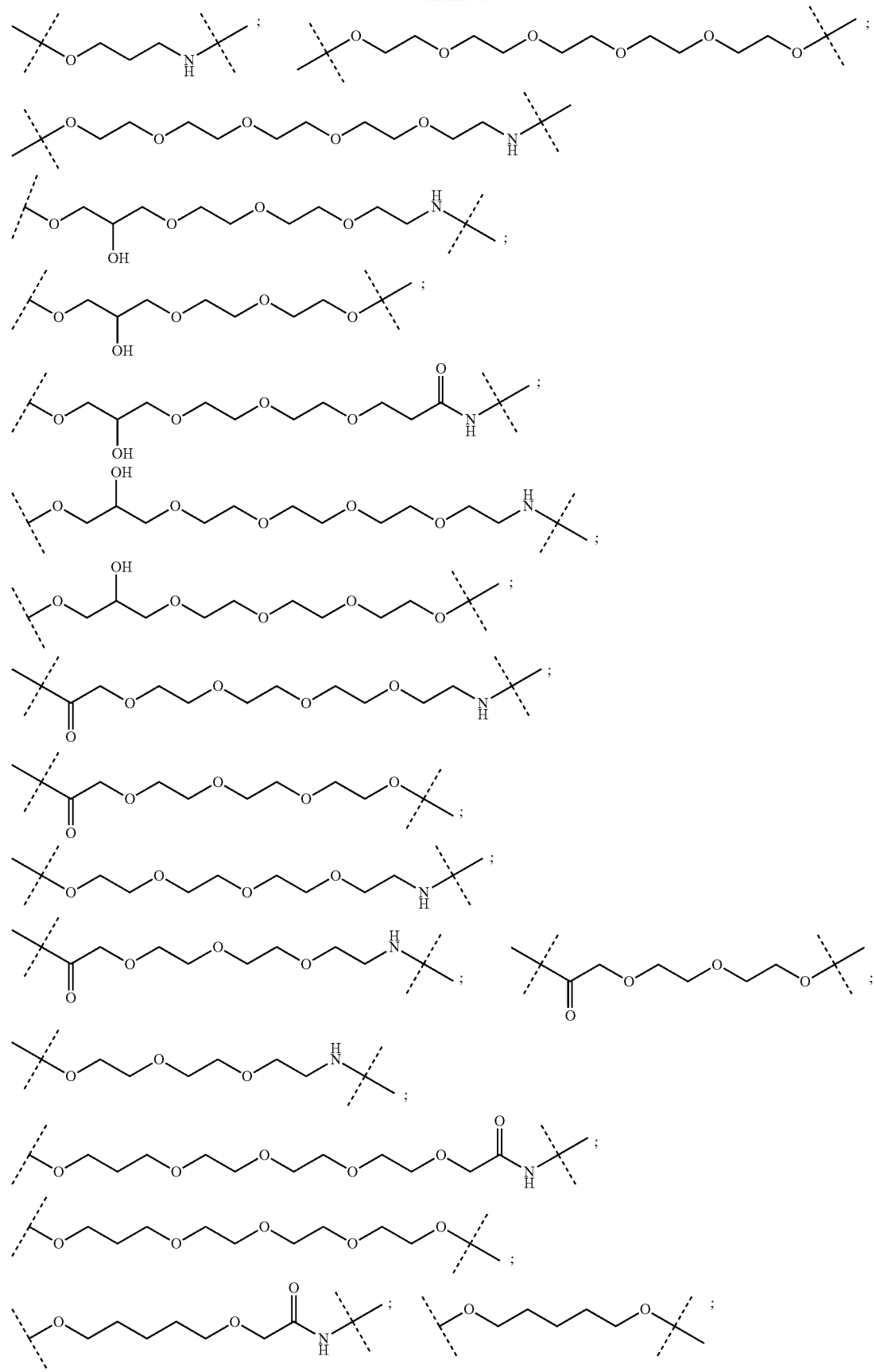

1079    1080
-continued
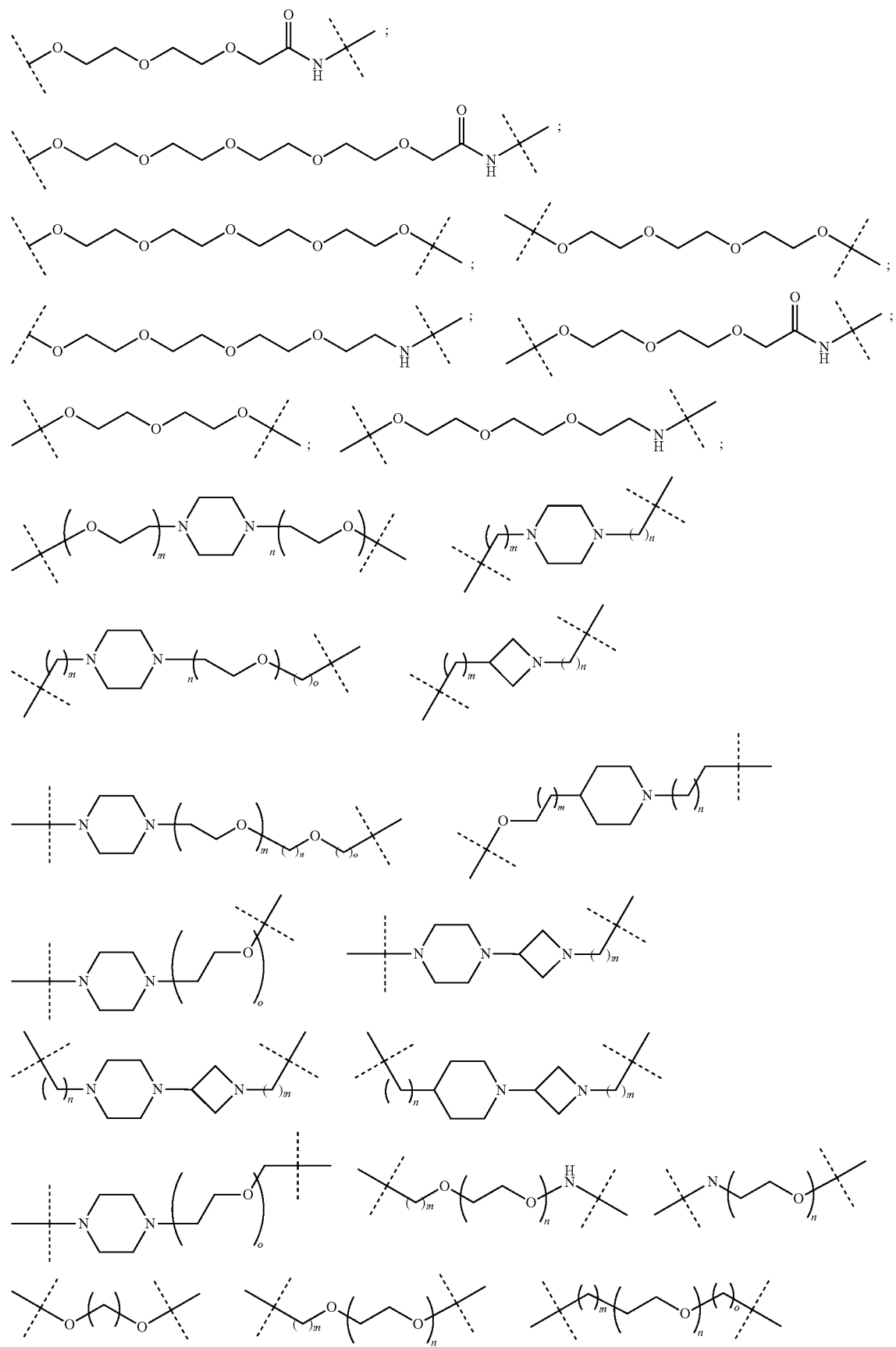

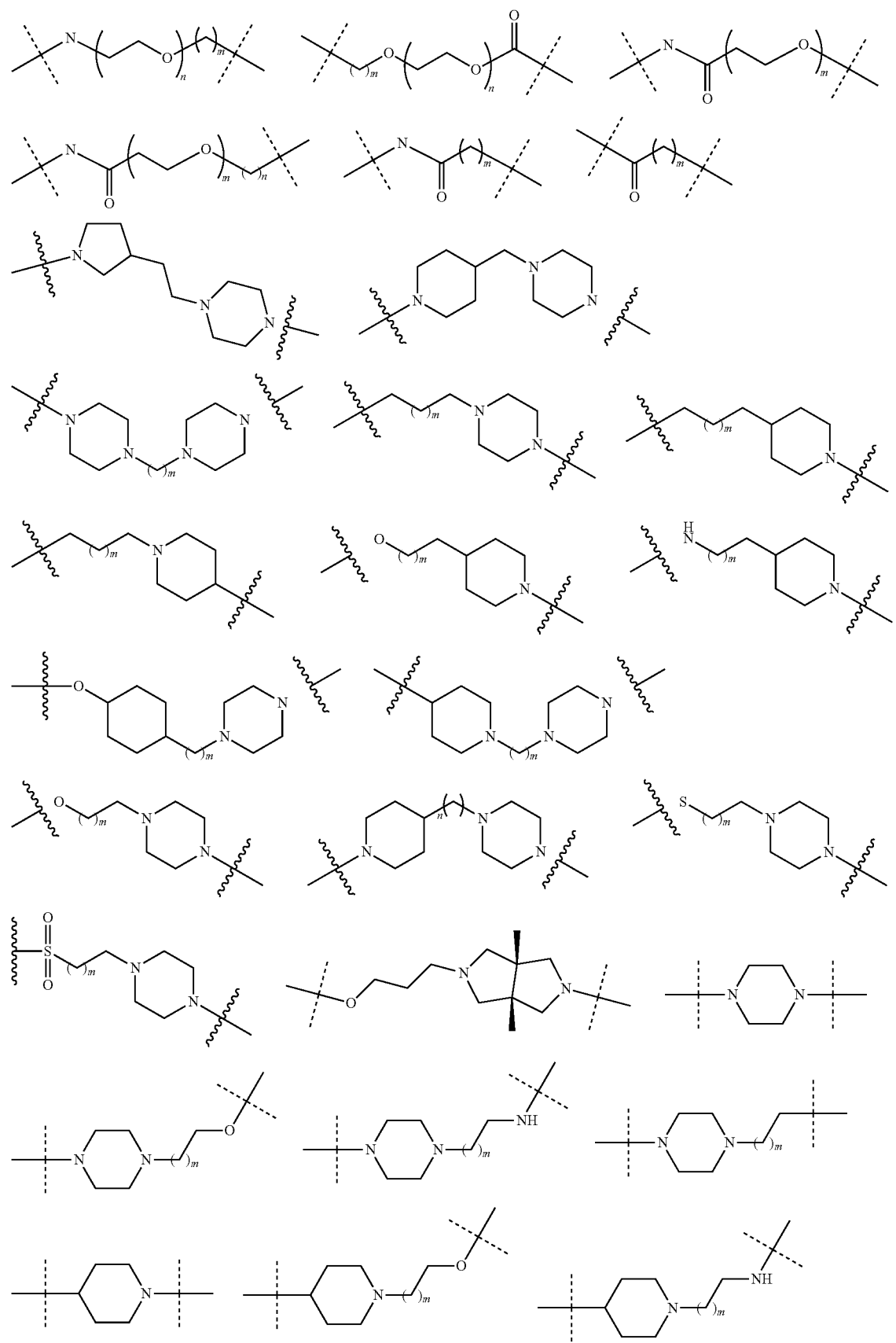

-continued
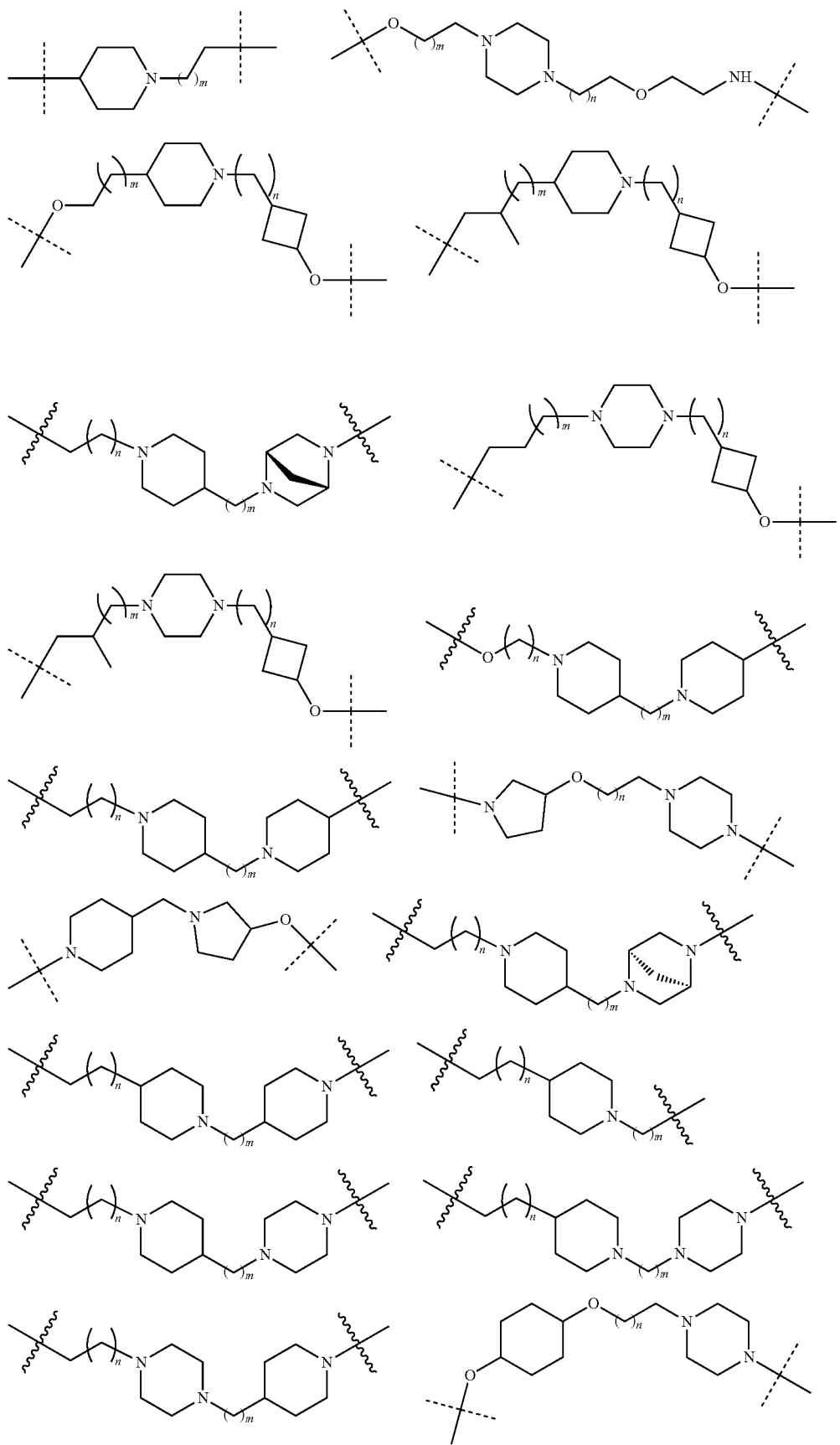

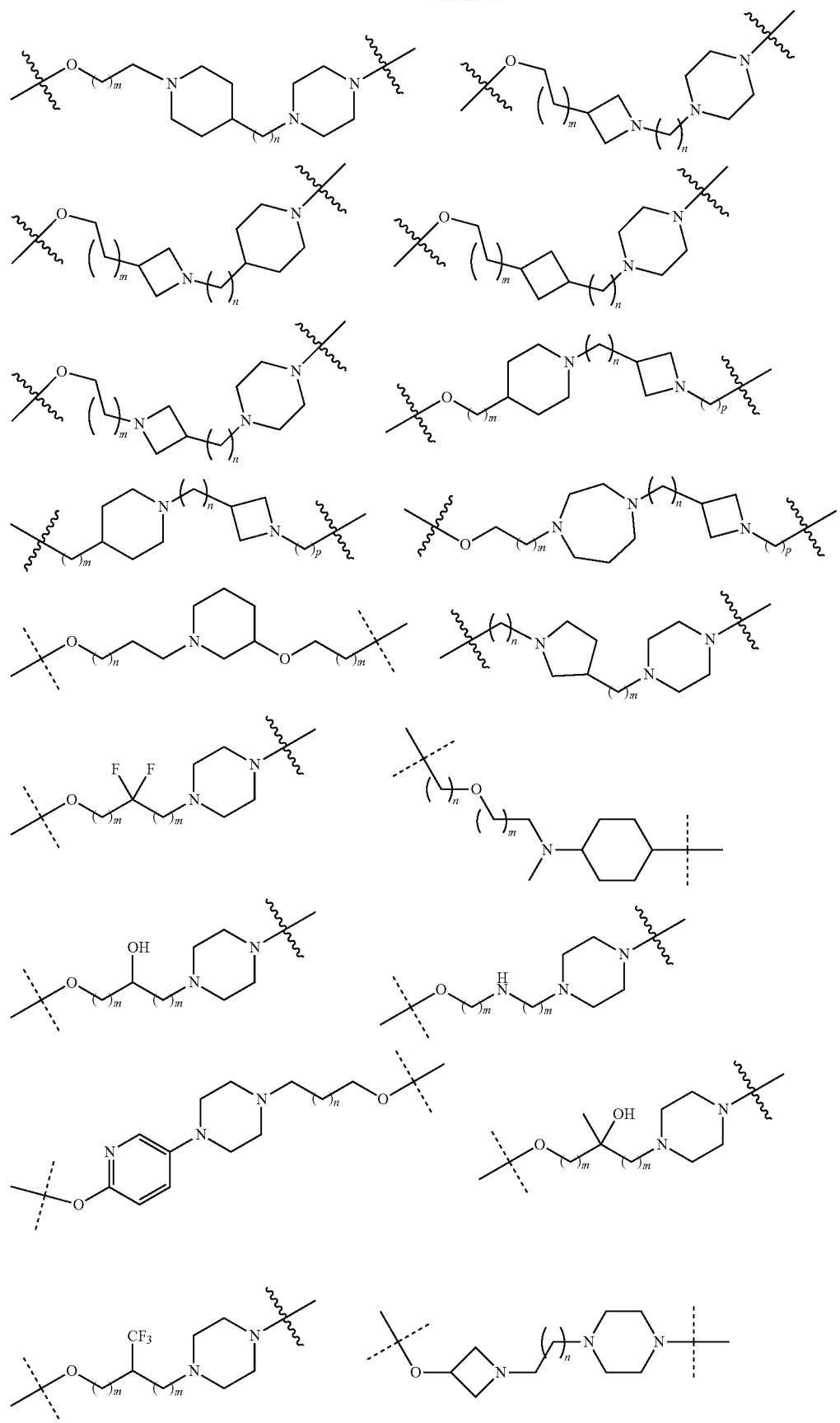

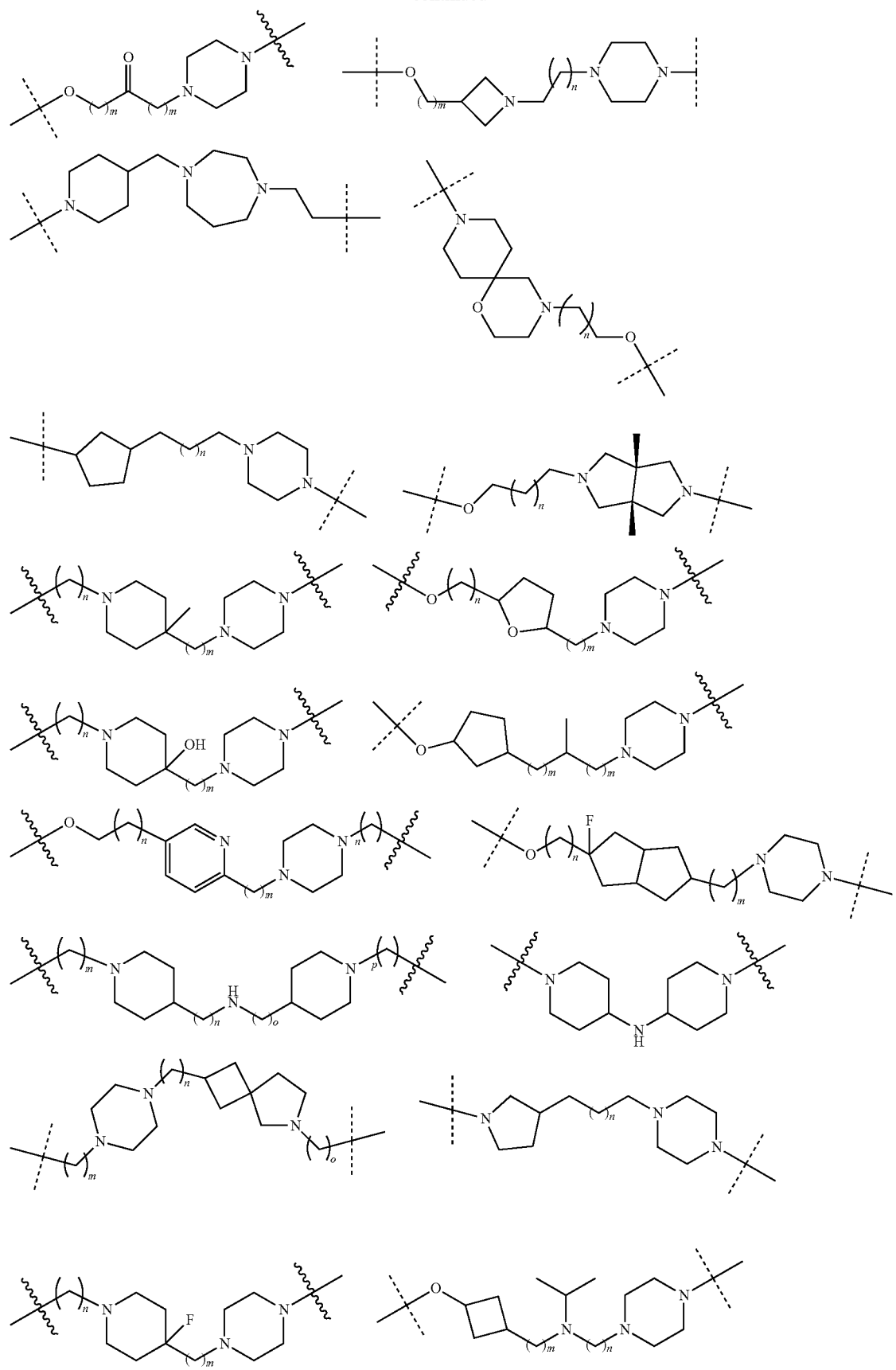

1089 1090
-continued
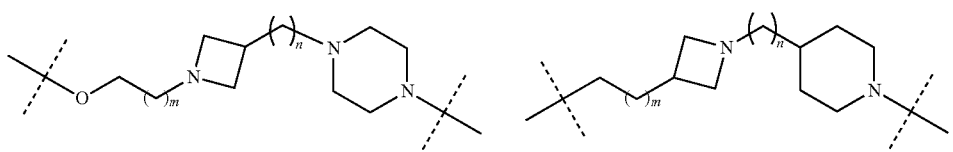
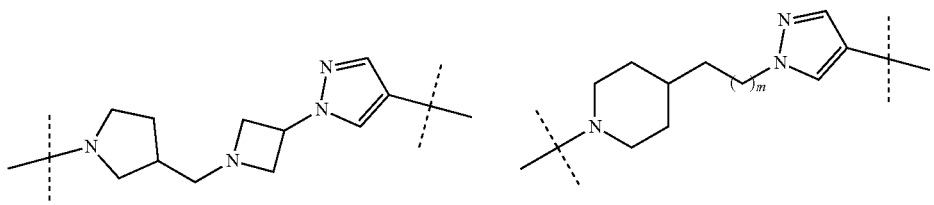
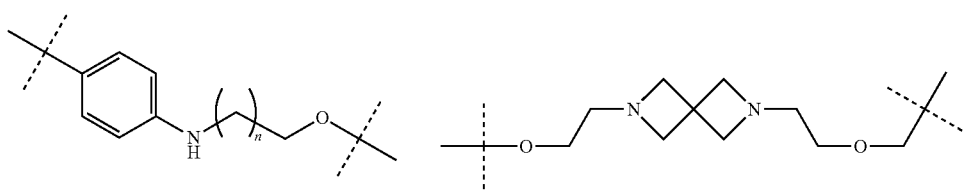
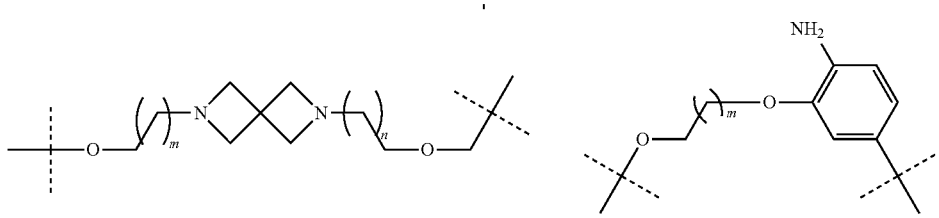
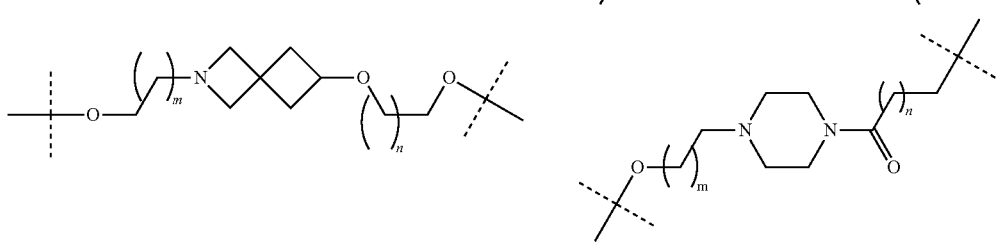
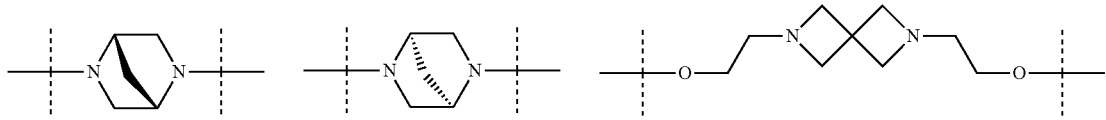
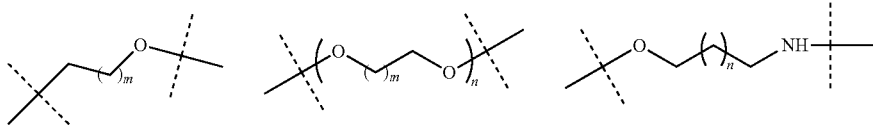
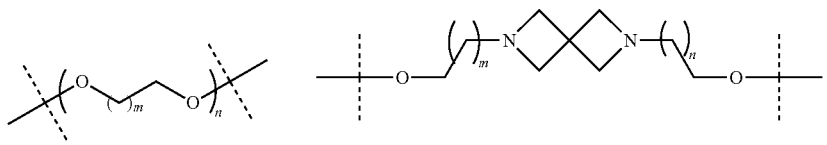
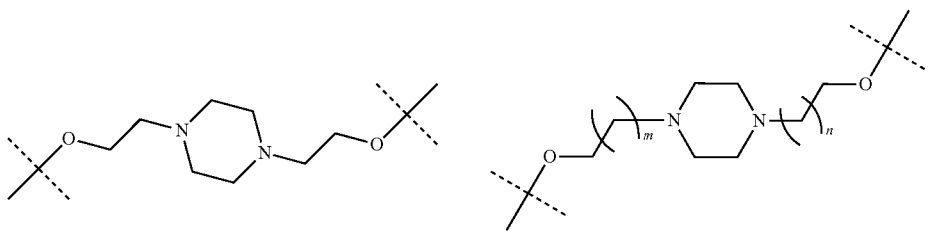

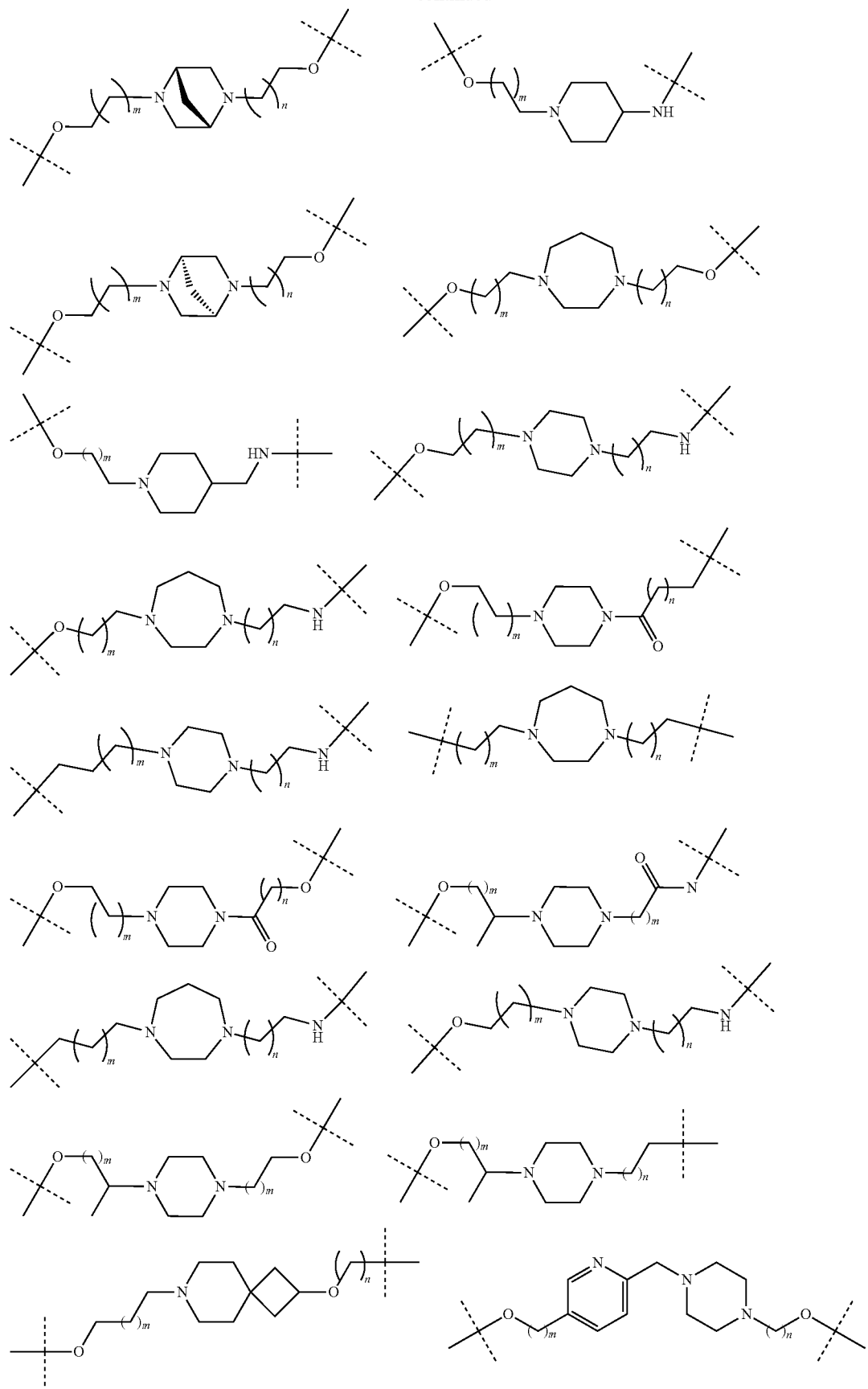

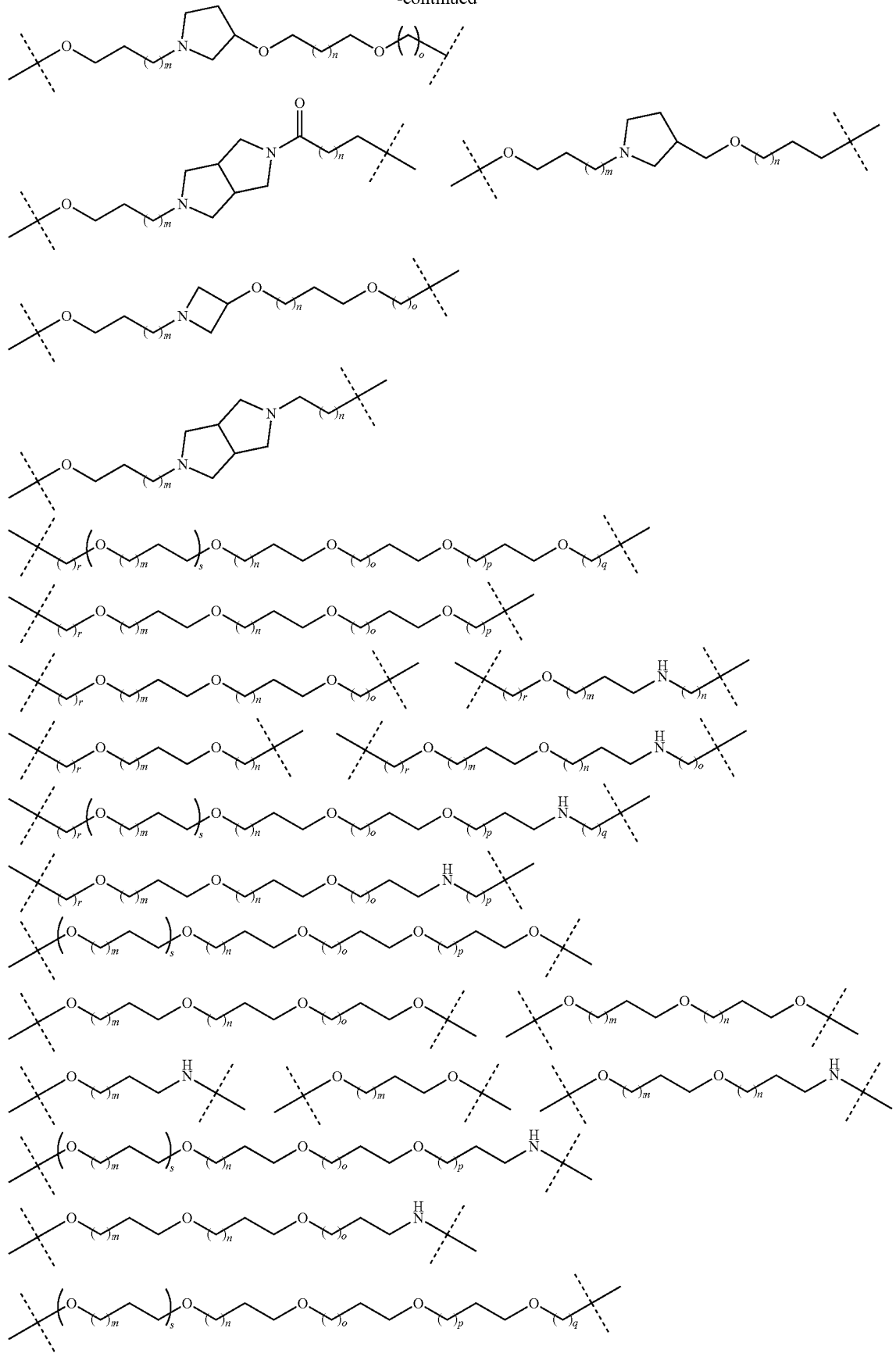

1095
-continued
1096
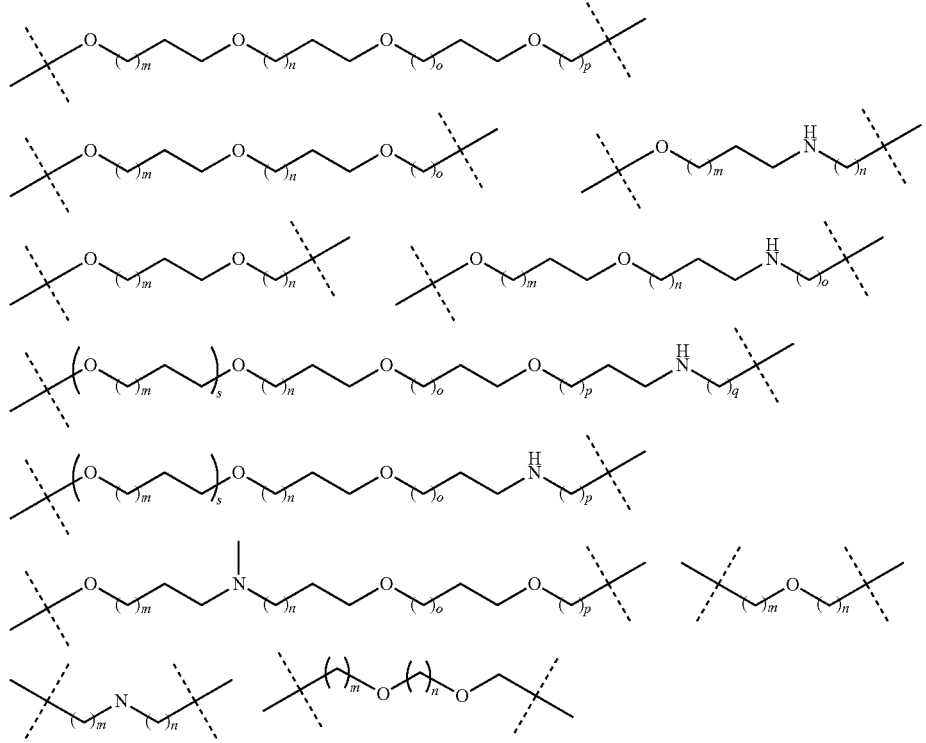
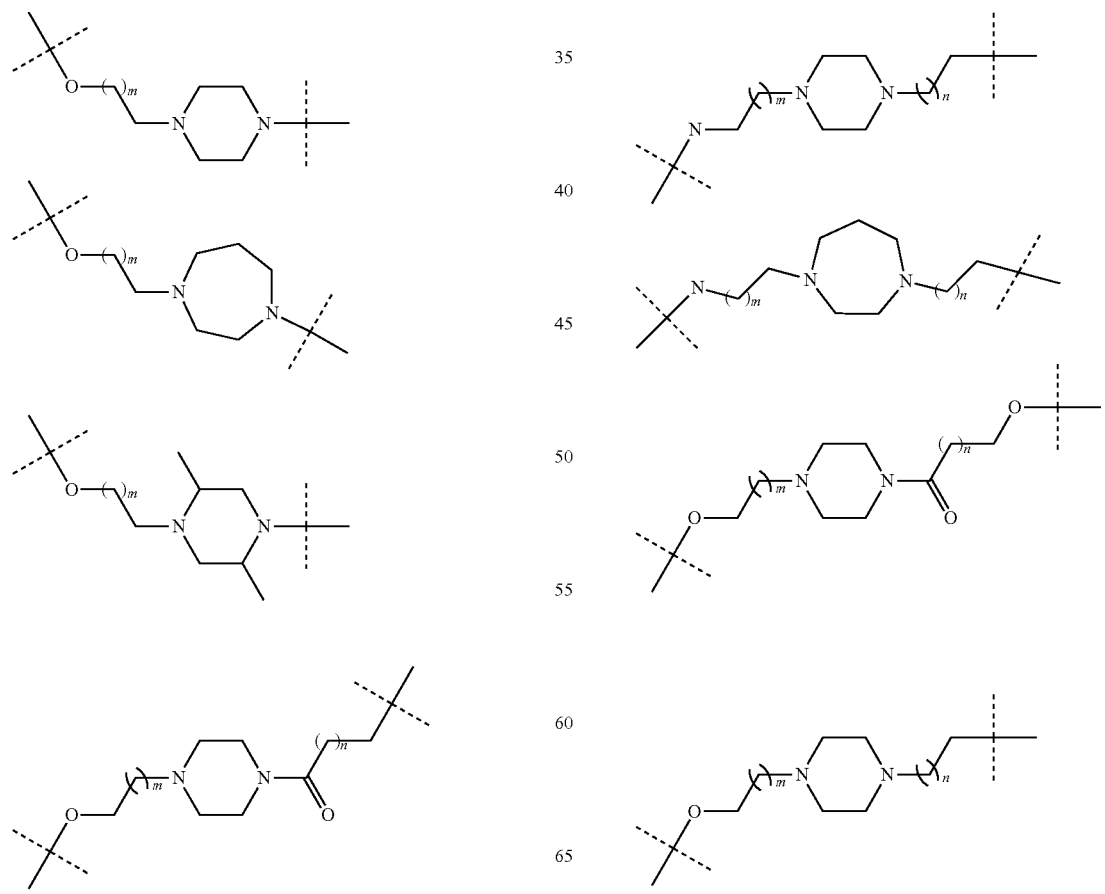

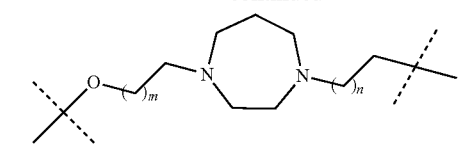
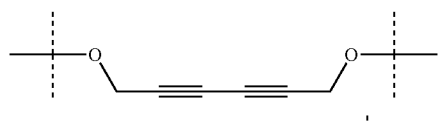
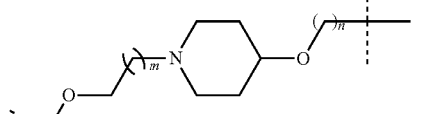
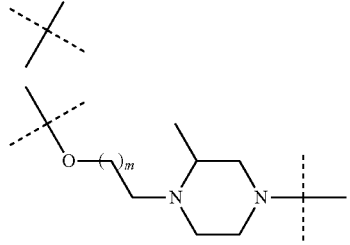
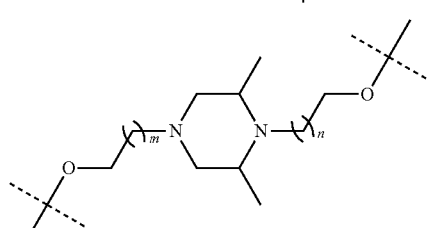
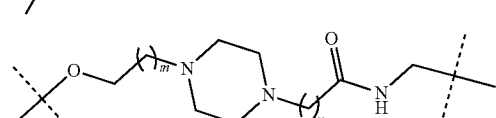
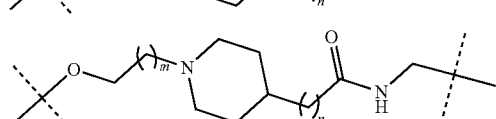
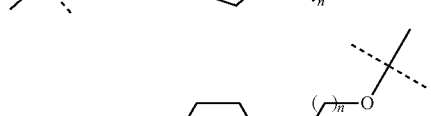
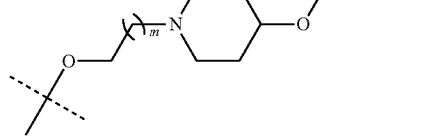
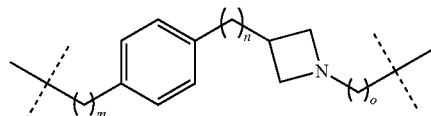
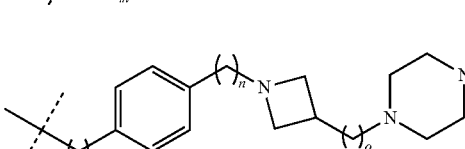
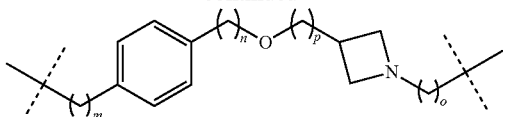
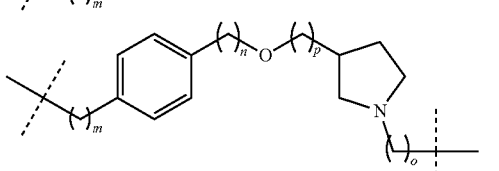
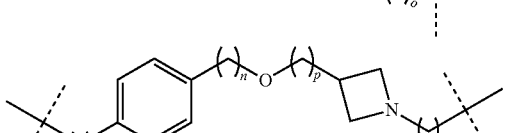
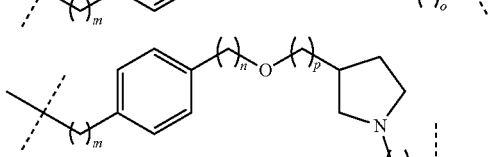
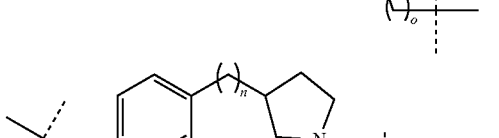
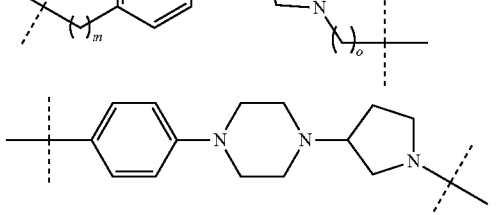
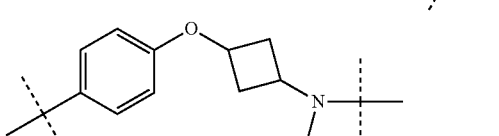
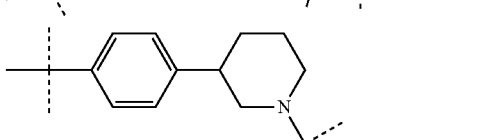
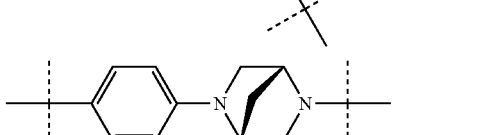
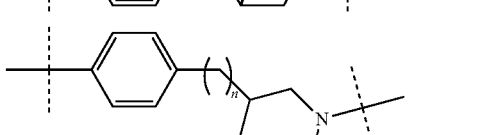
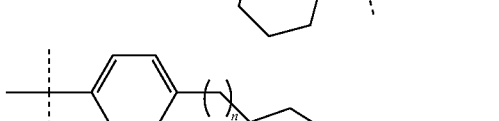
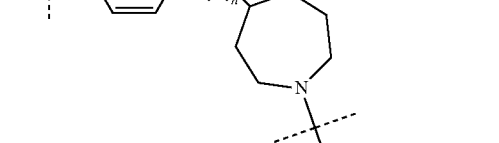

1099
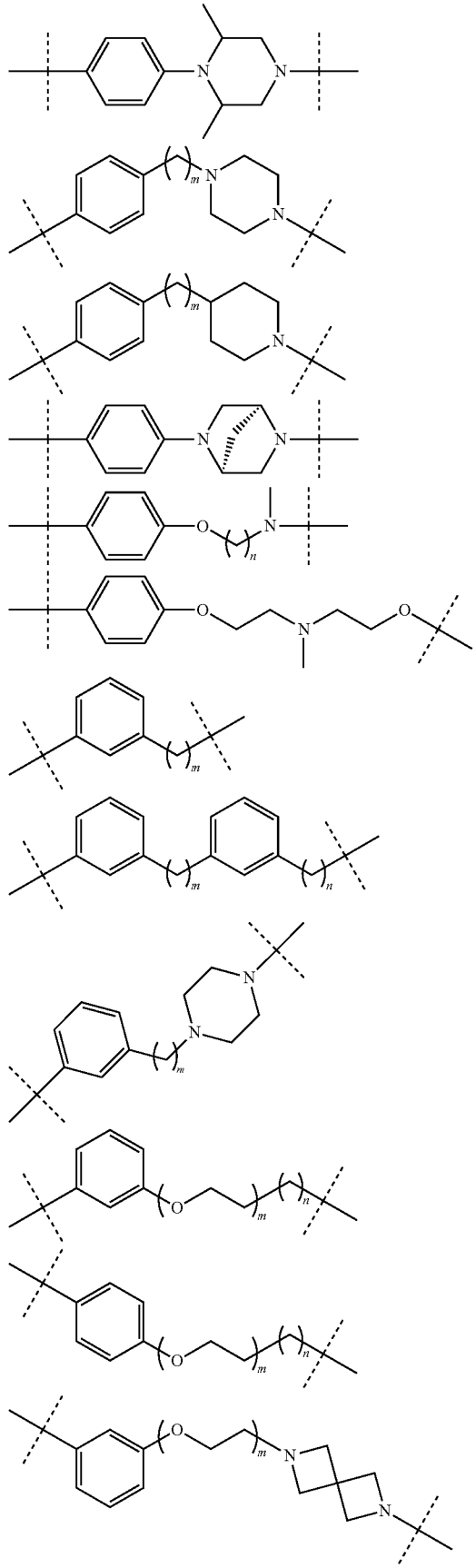
1100
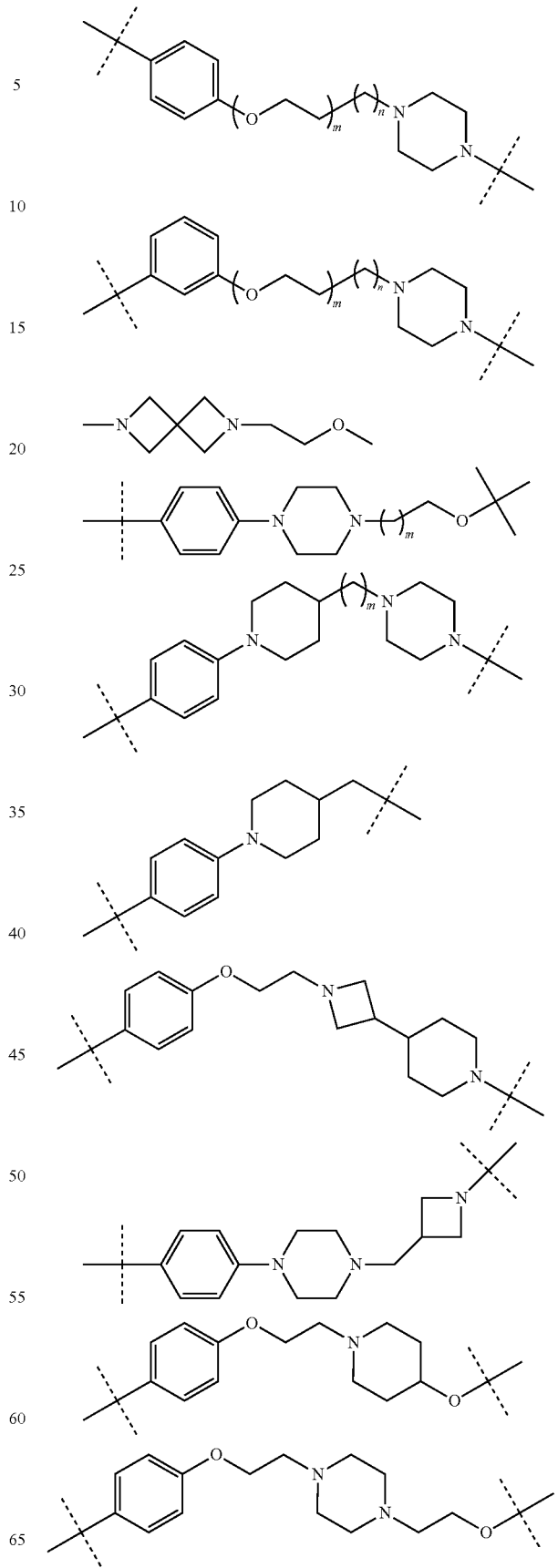

1101
-continued
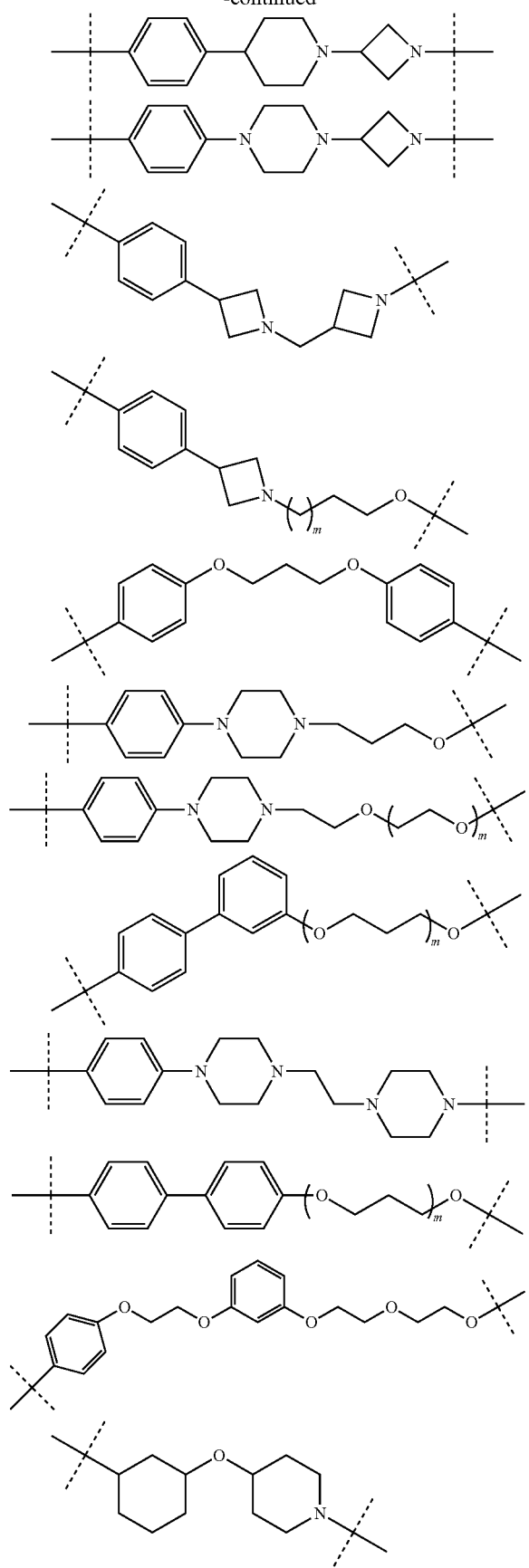
1102
-continued
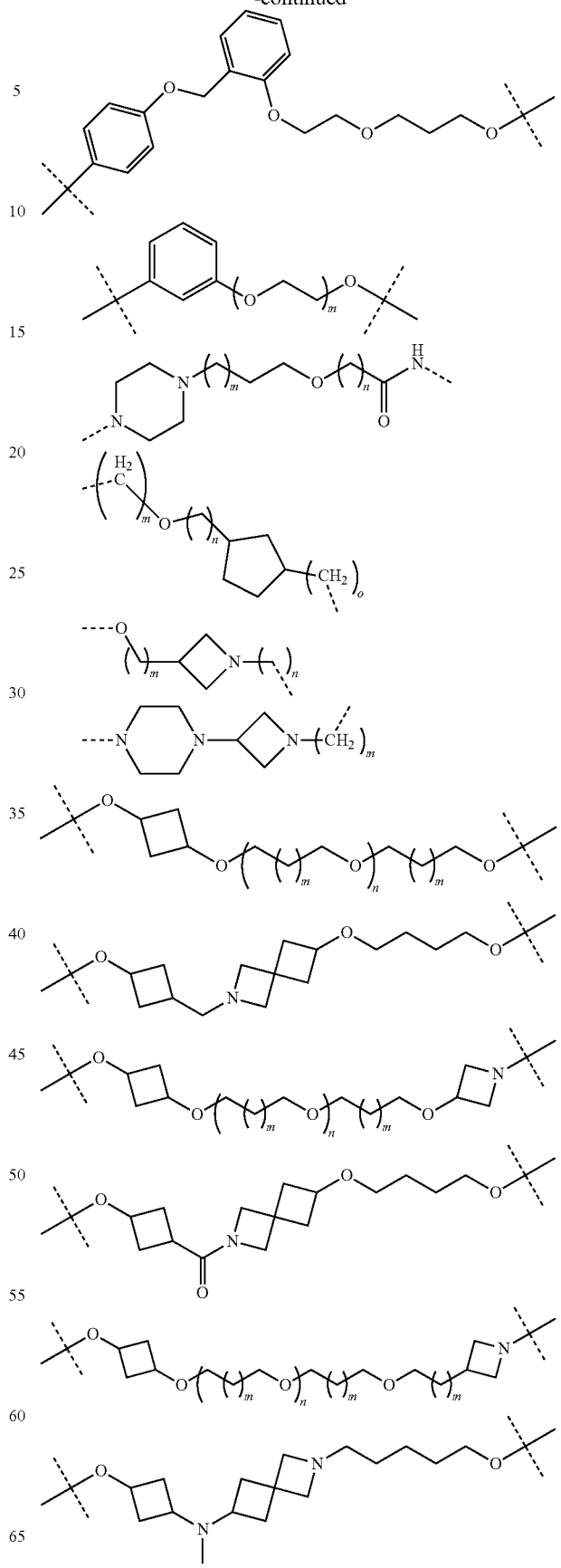

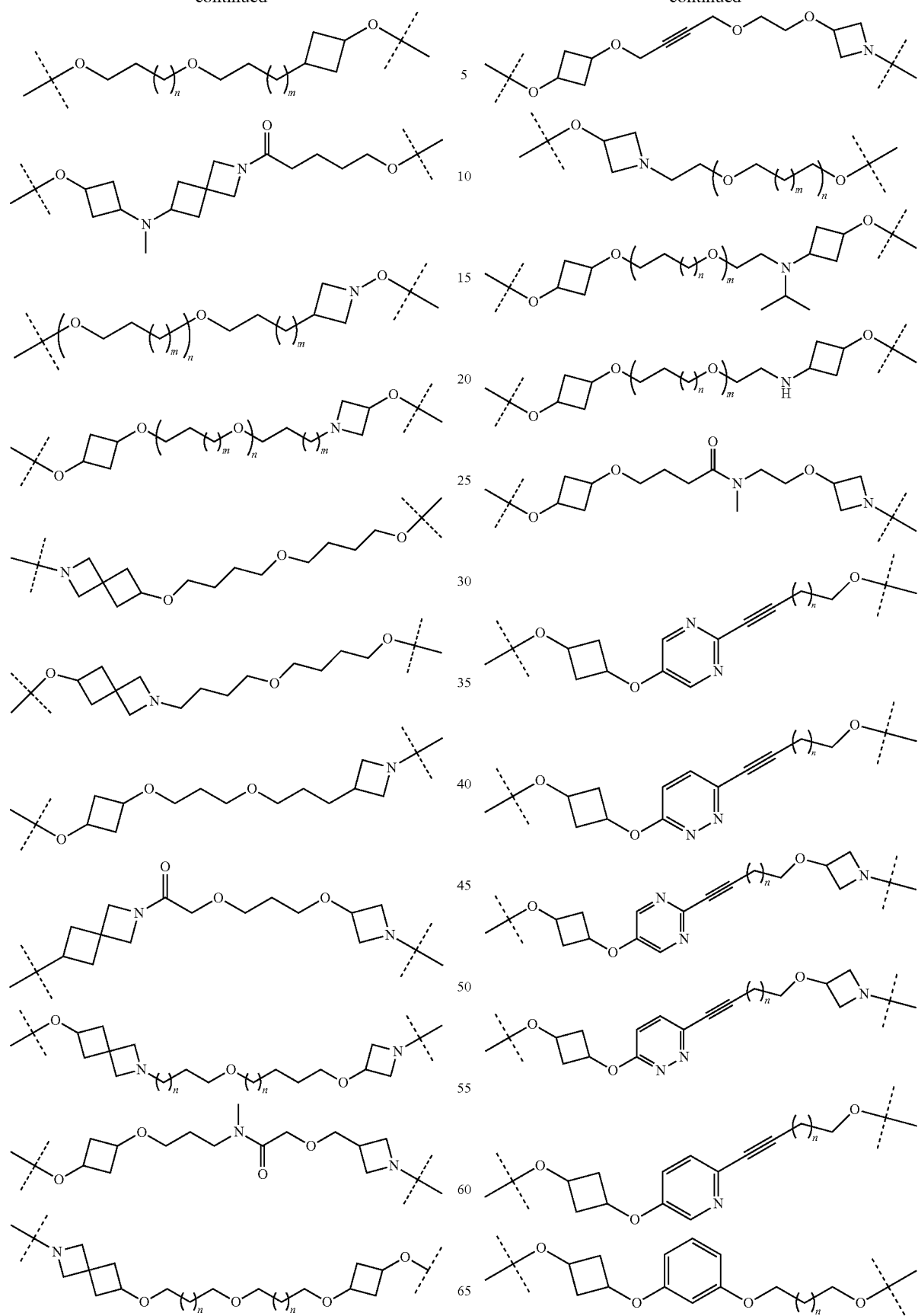

1105
-continued
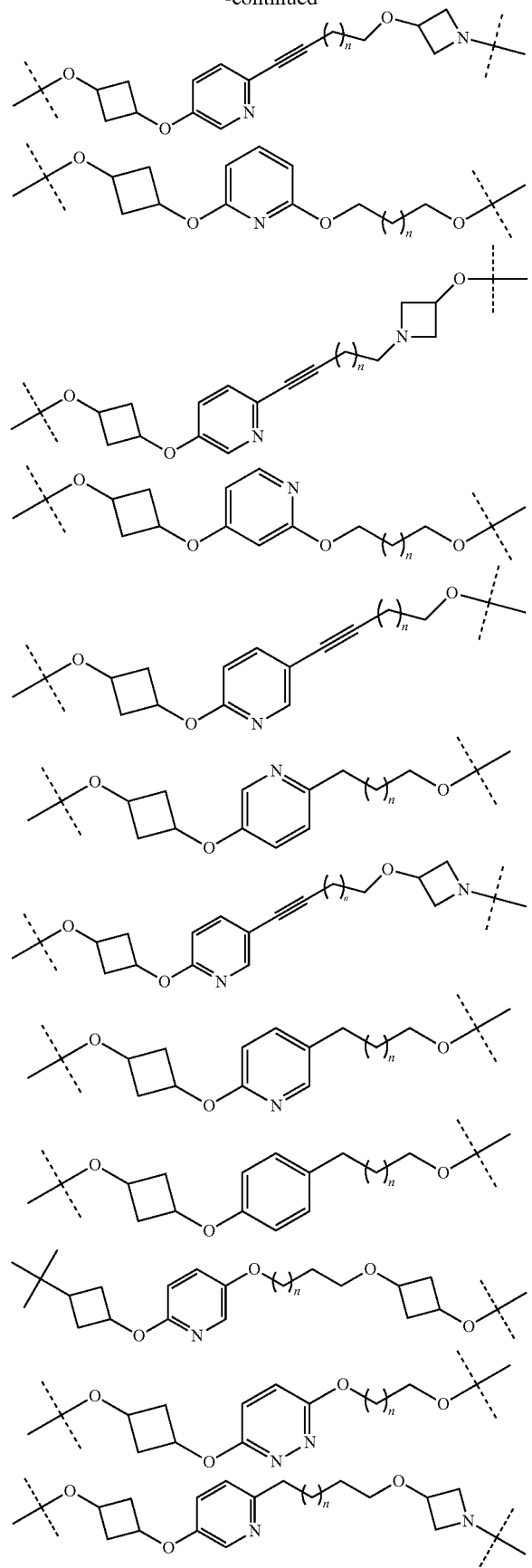
1106
-continued
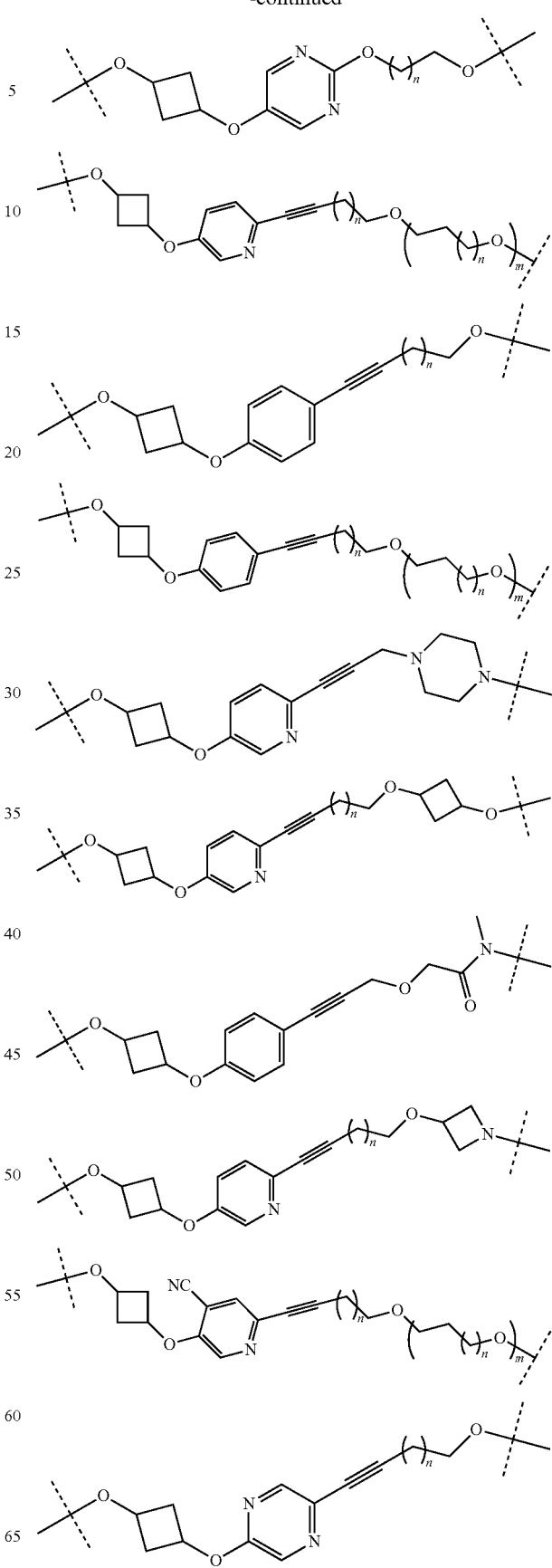

1107
-continued
1108
-continued
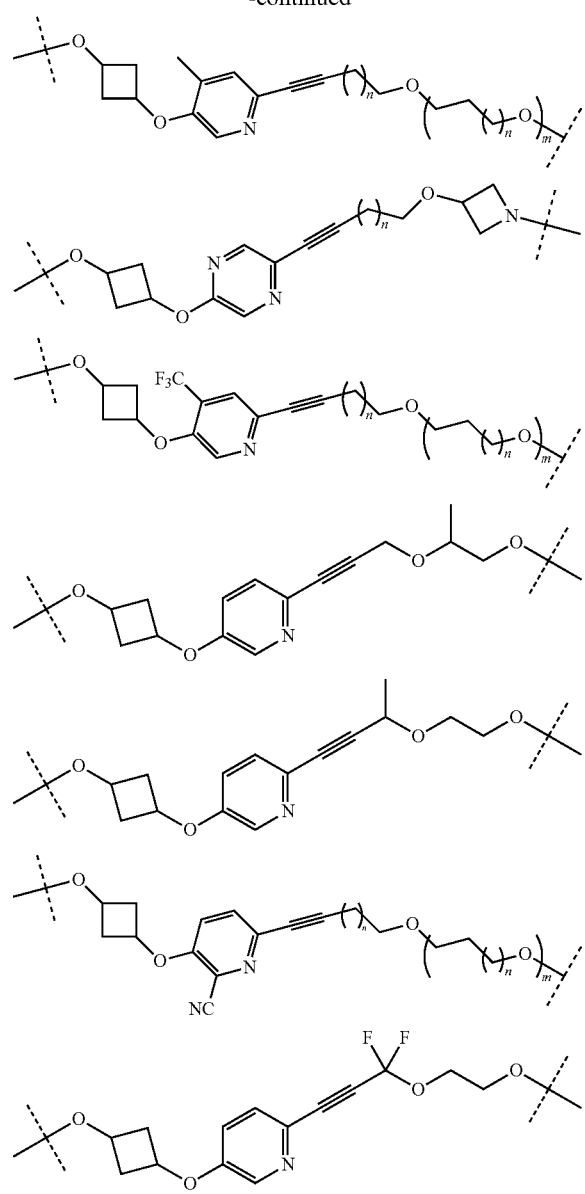
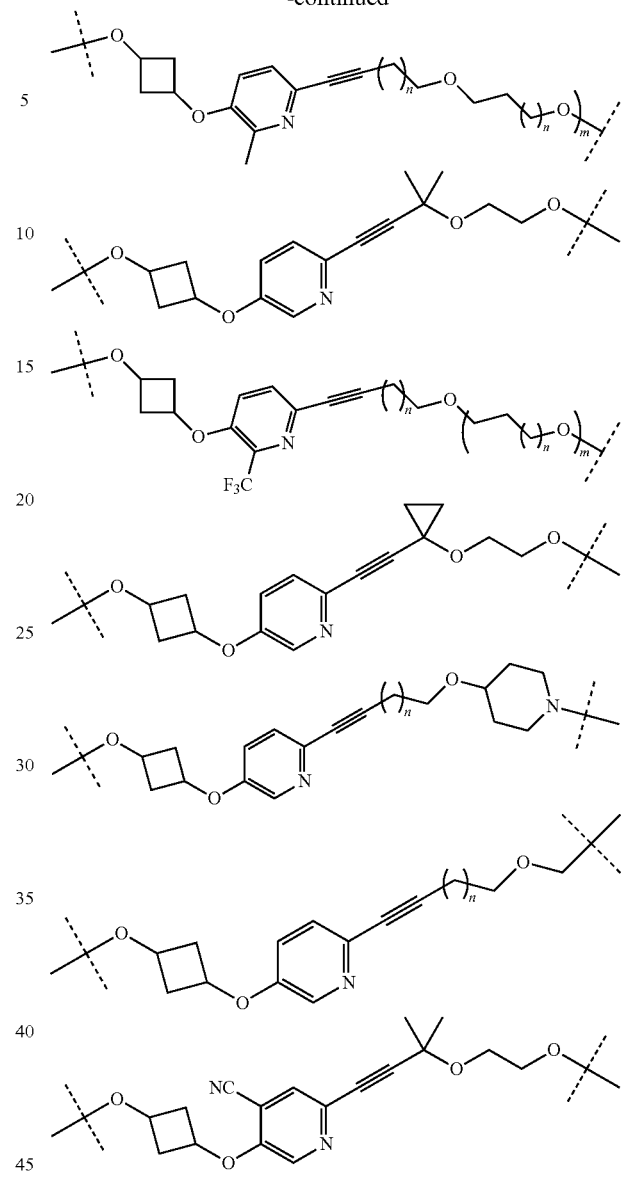
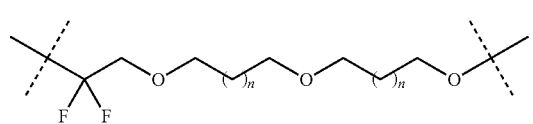
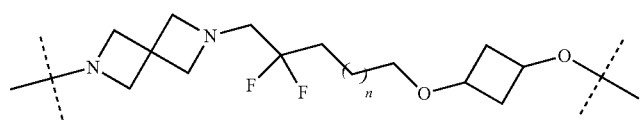
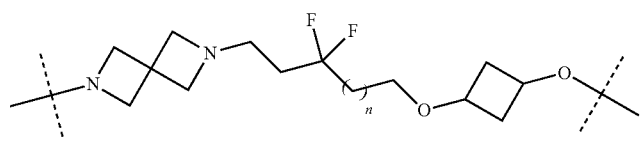

-continued
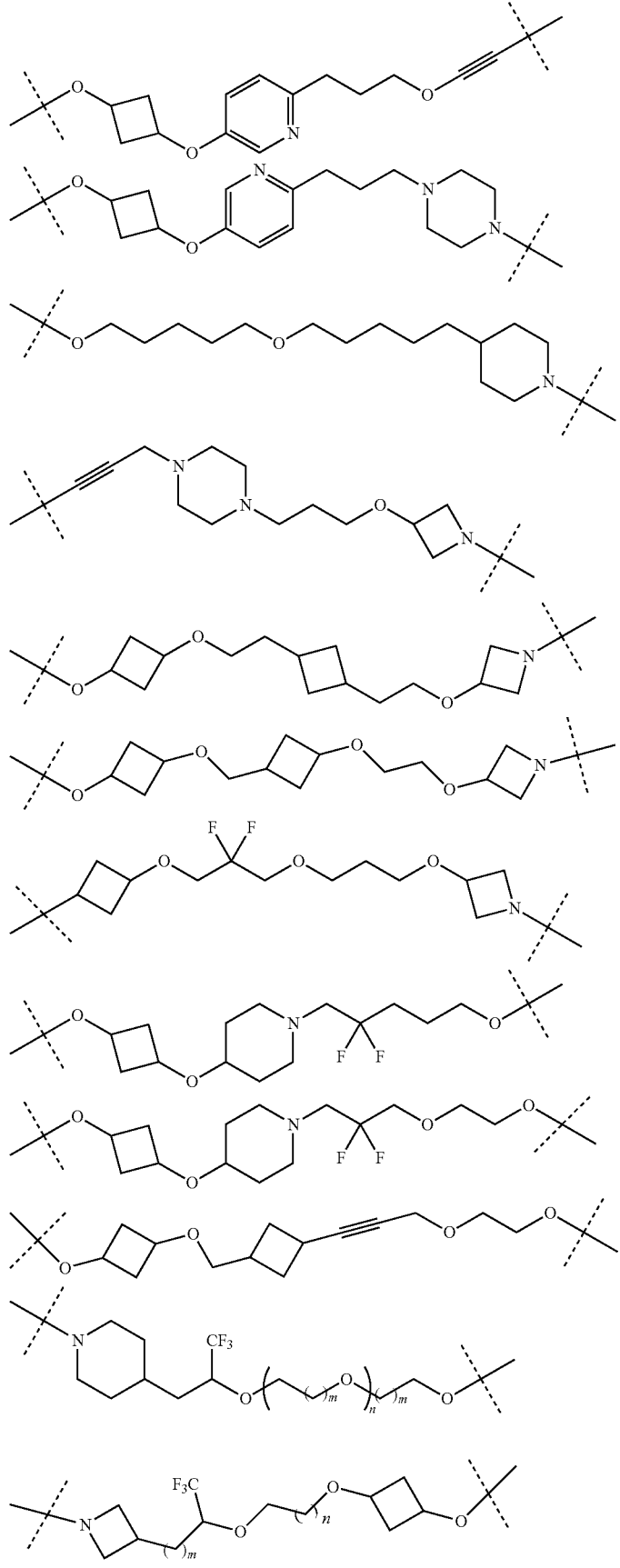

-continued
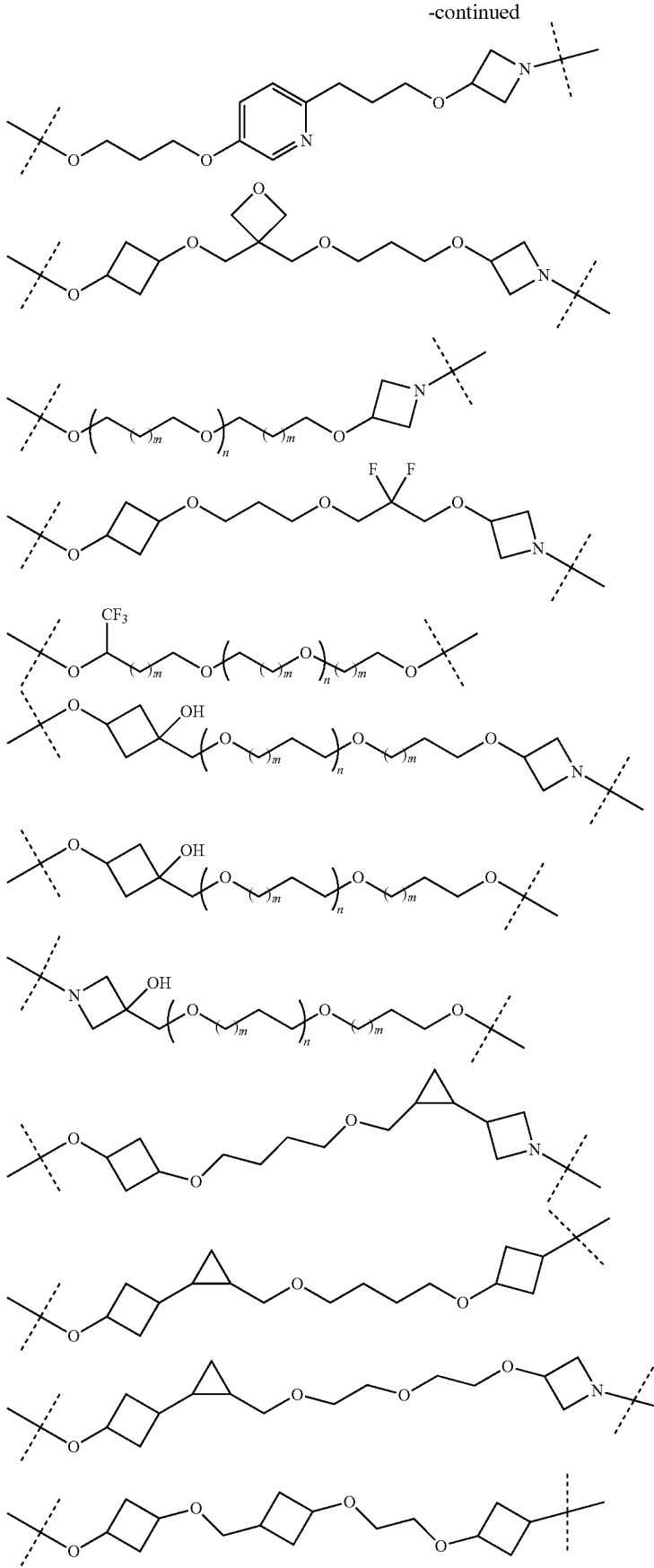

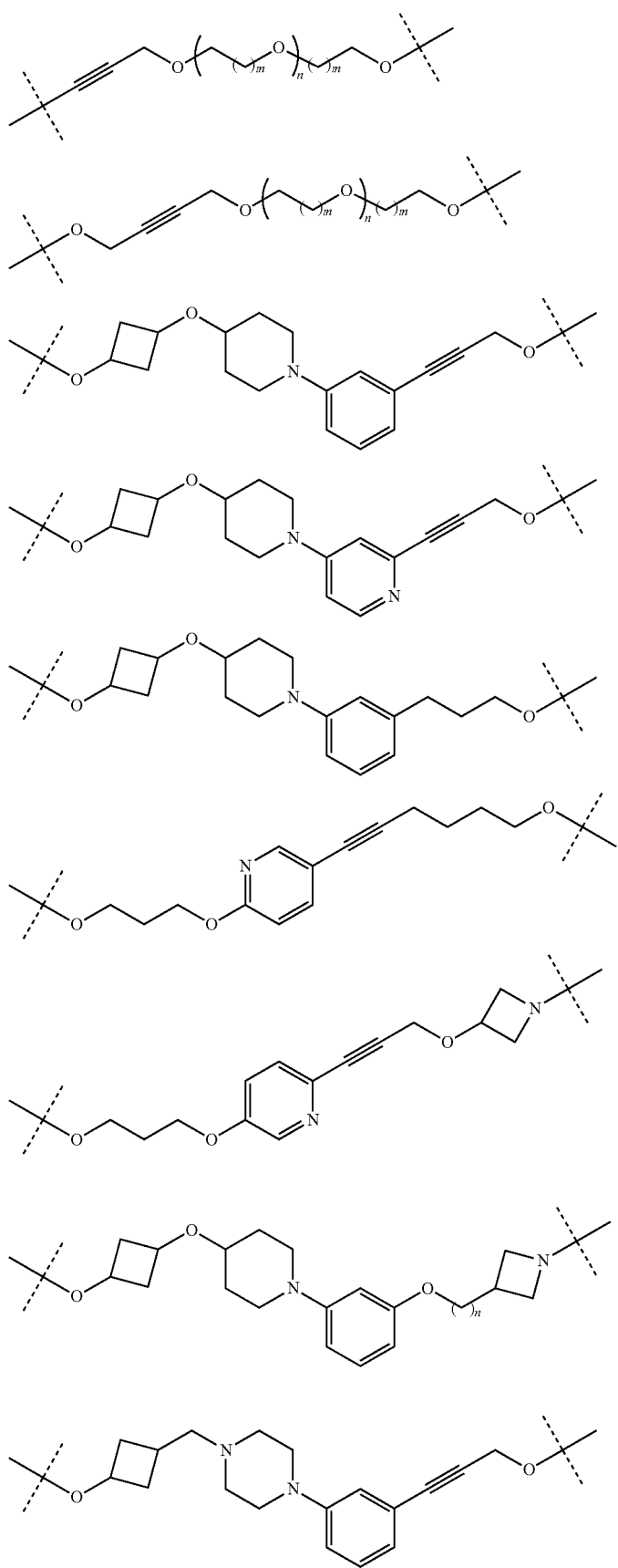

-continued
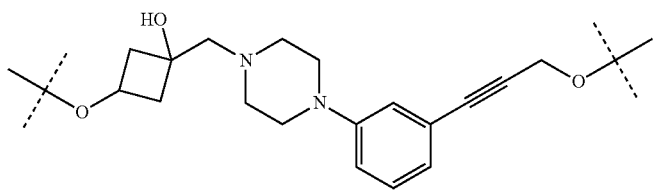
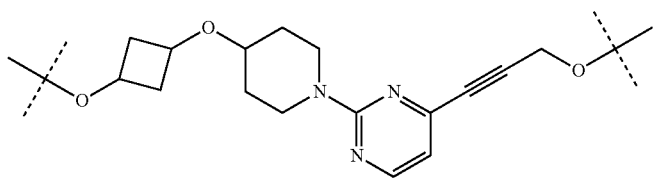
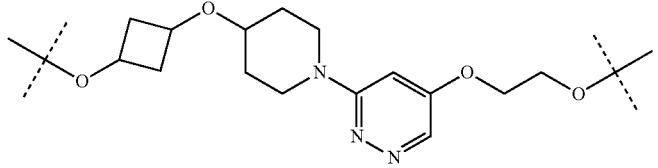
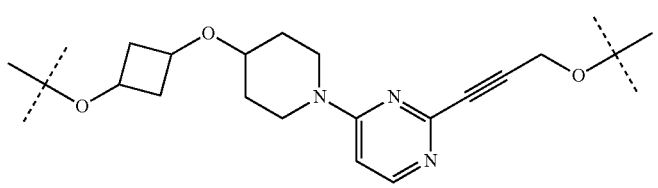
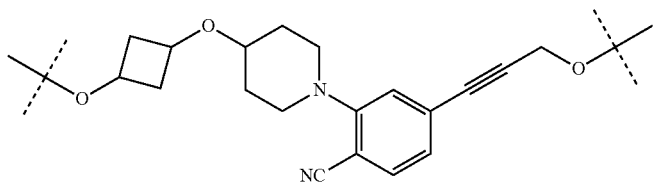
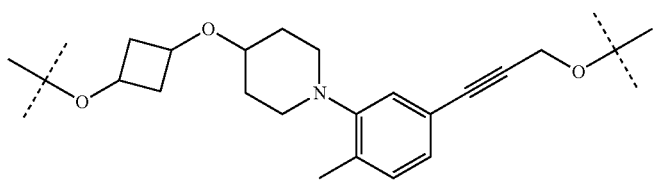
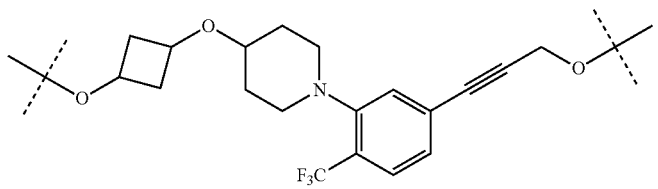
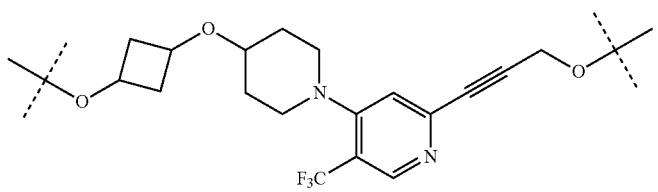
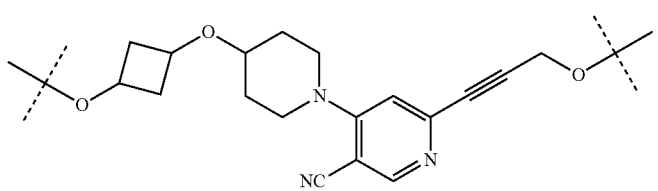

1117                                                                    1118
-continued
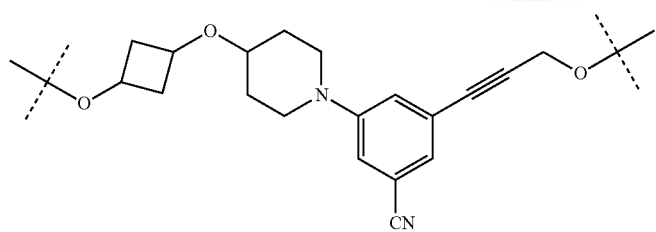
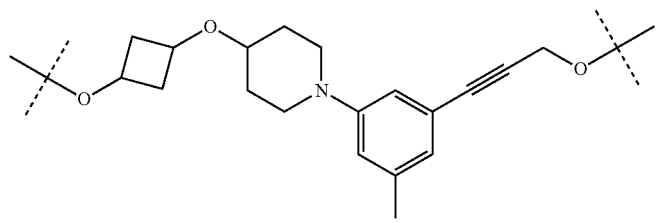
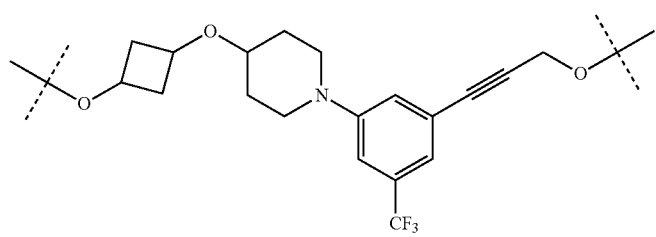
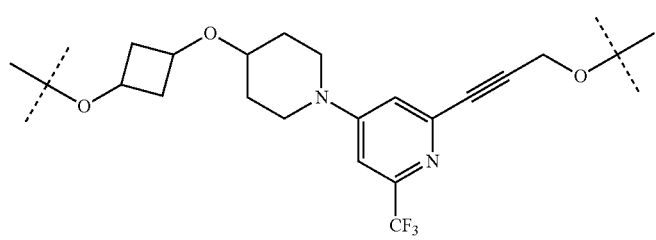
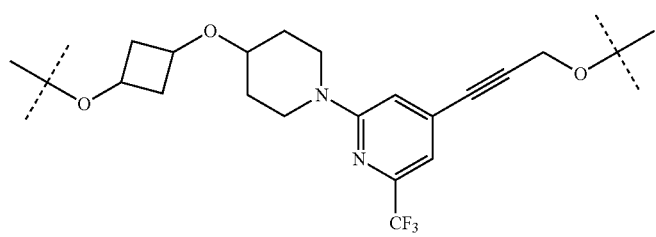
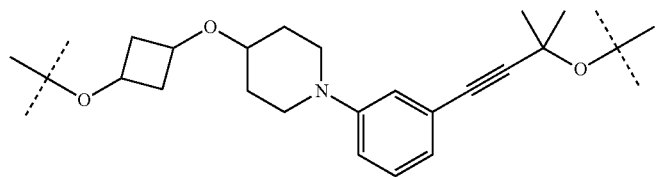
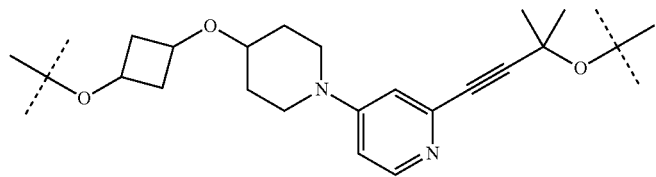
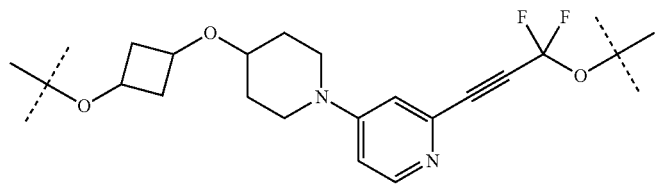

-continued
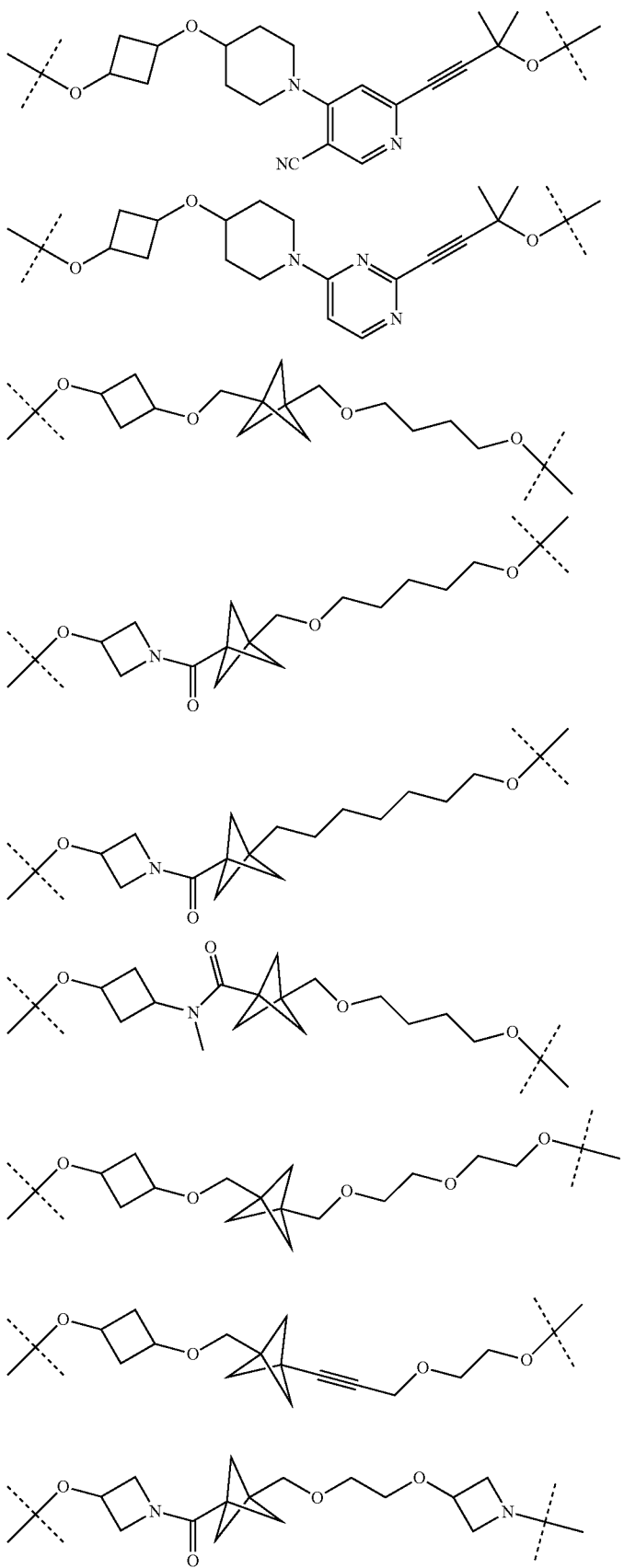

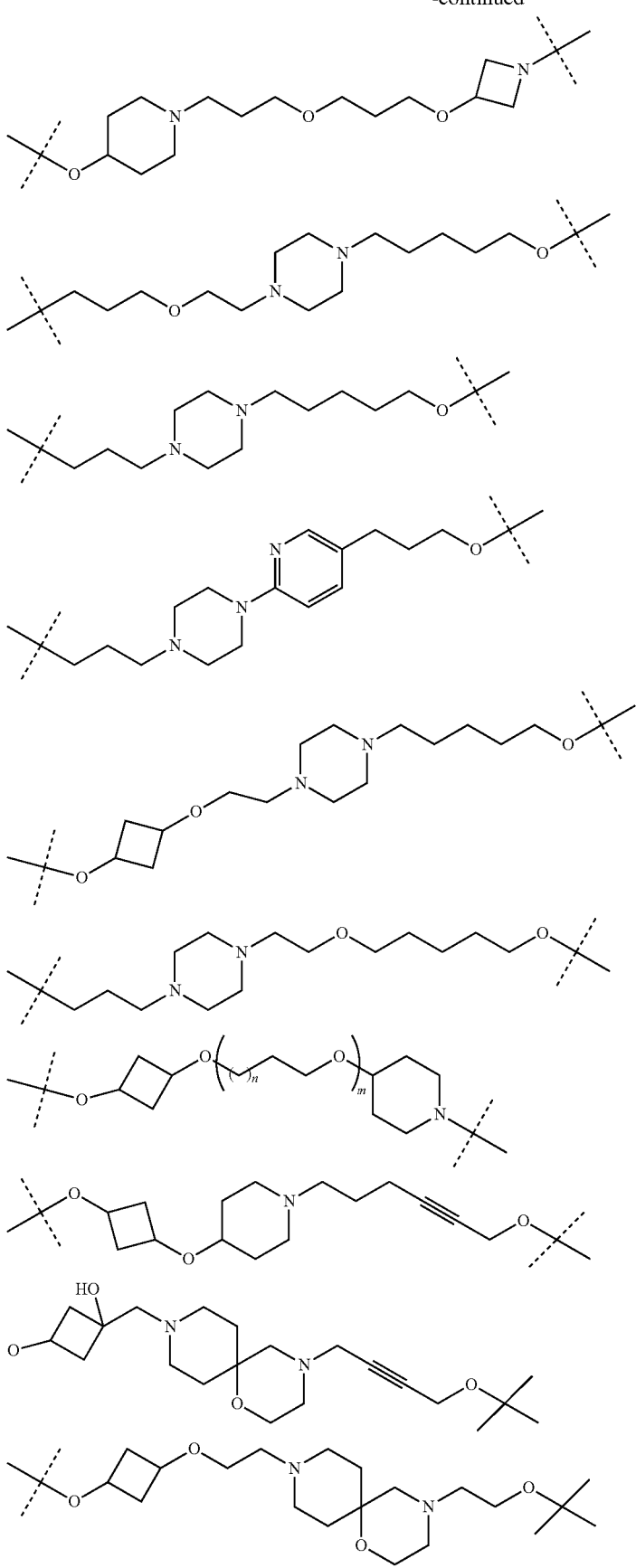

1123 1124
-continued
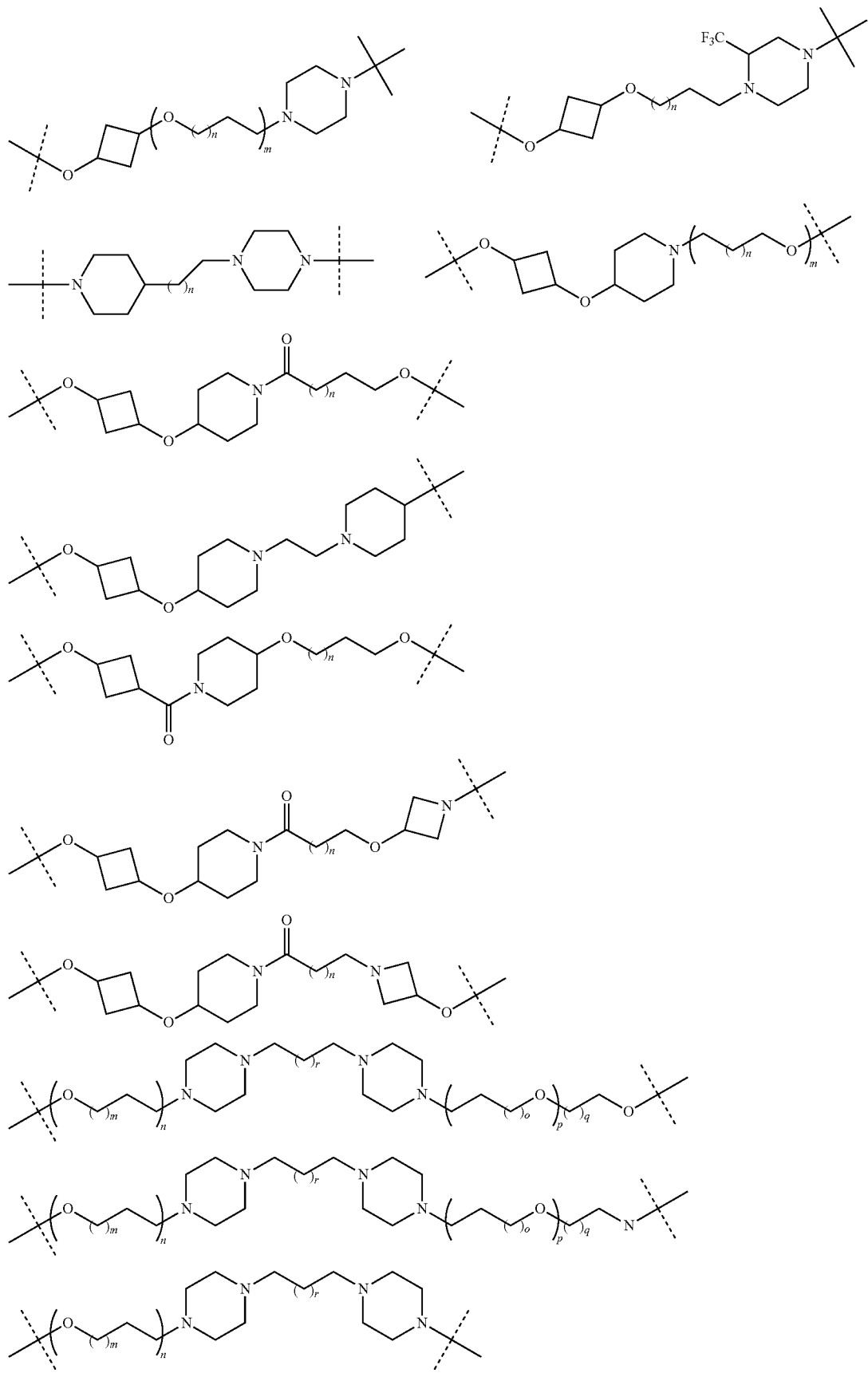

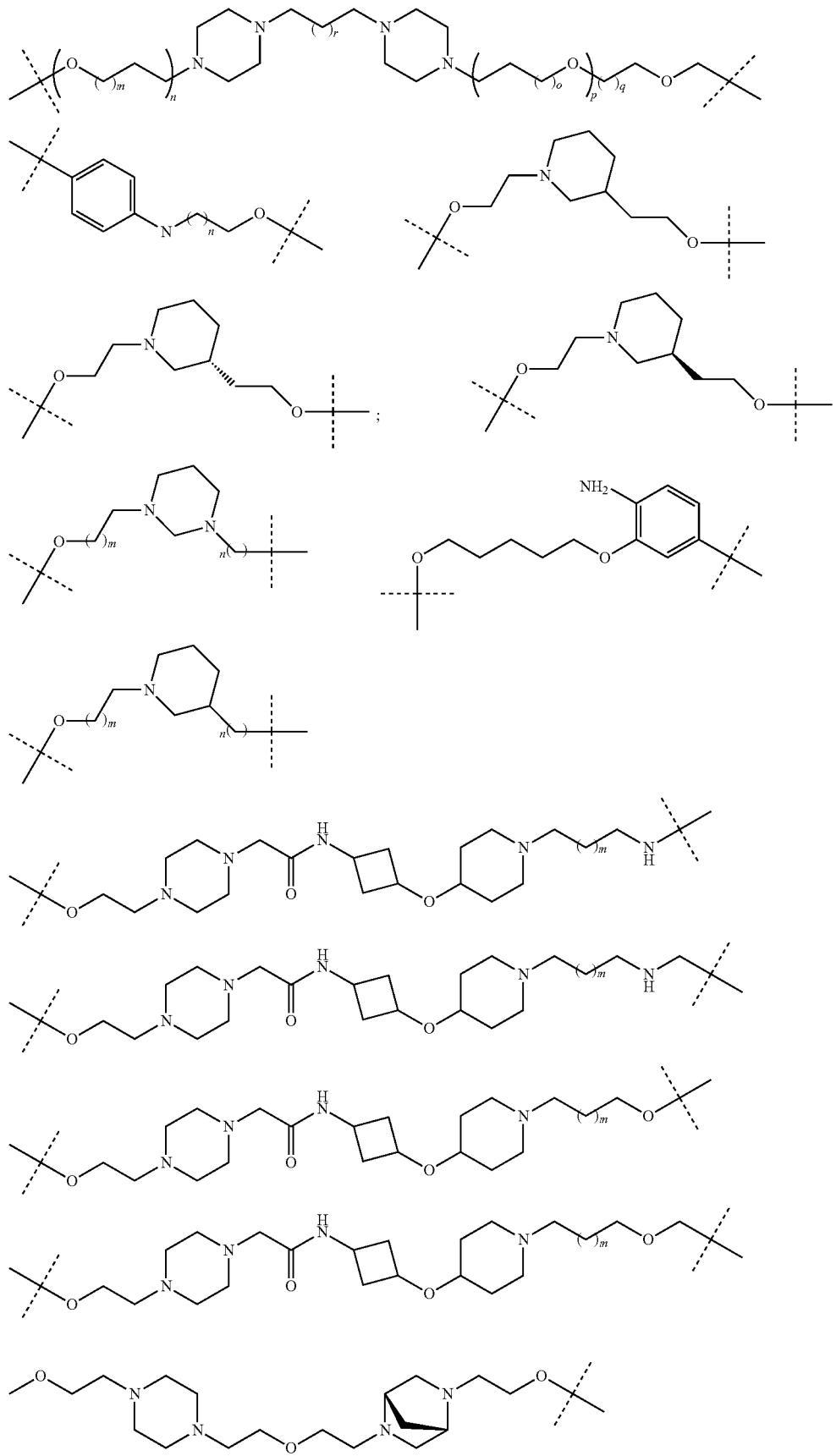

-continued
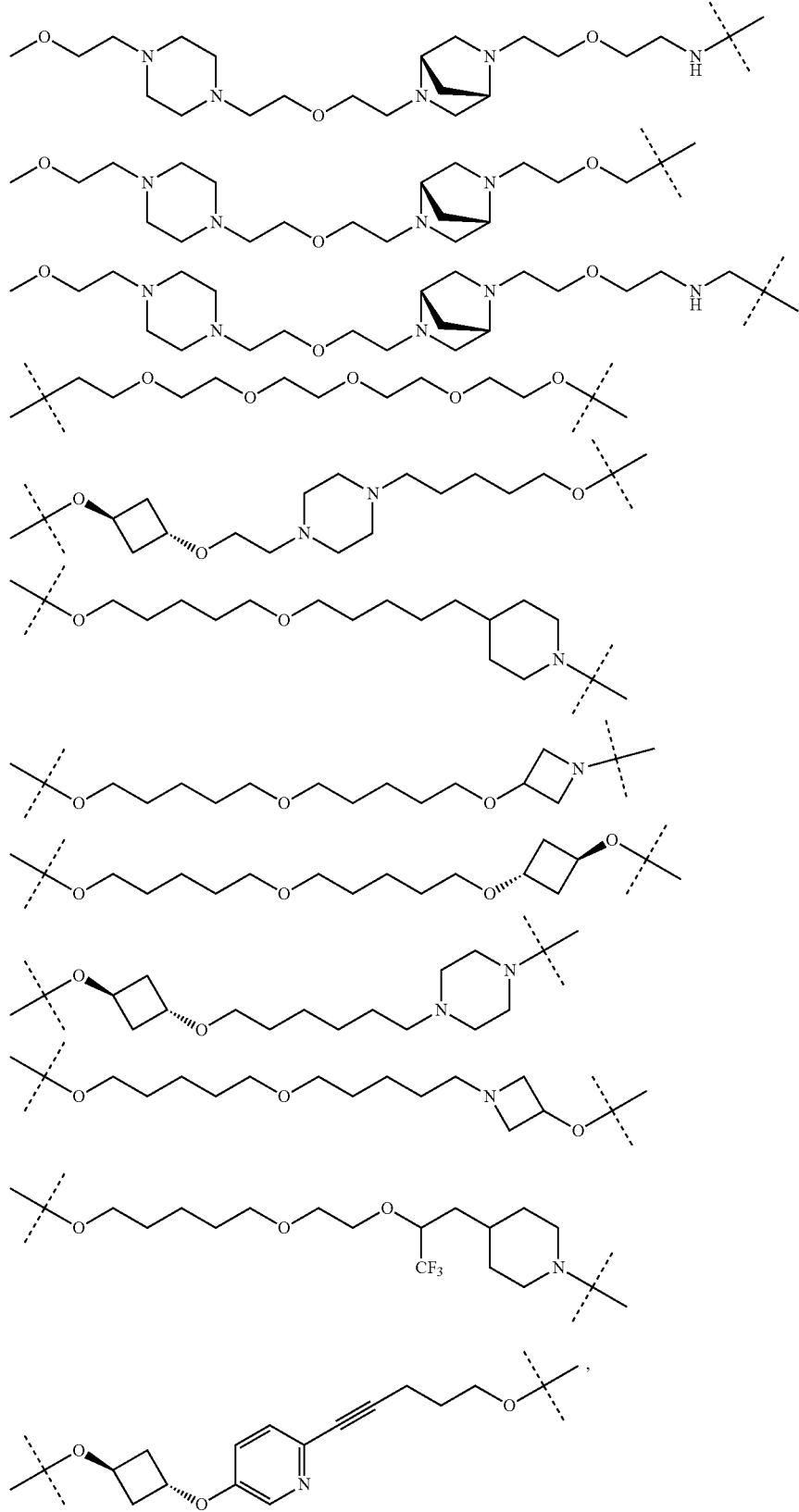
wherein each m, n, o, p, q, r, and s is independently 0, 1, 2,3,4,5,6,7, 8,9, 10, 11, 12, 13, 14, 15, 16, 17, 18, 19, or 20.

In any aspect or embodiment described herein, the unit $A^L$ of linker (L) is selected from:
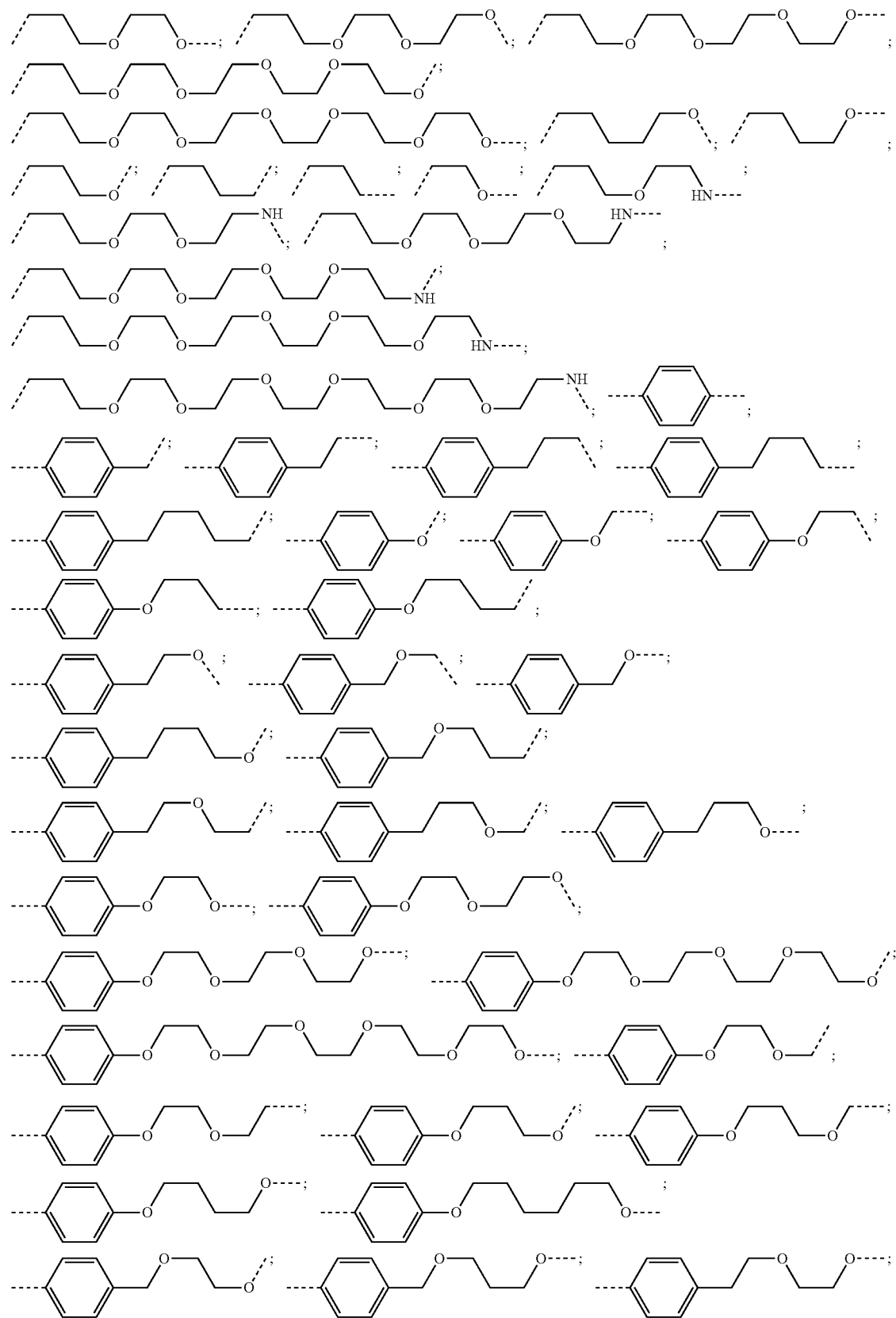

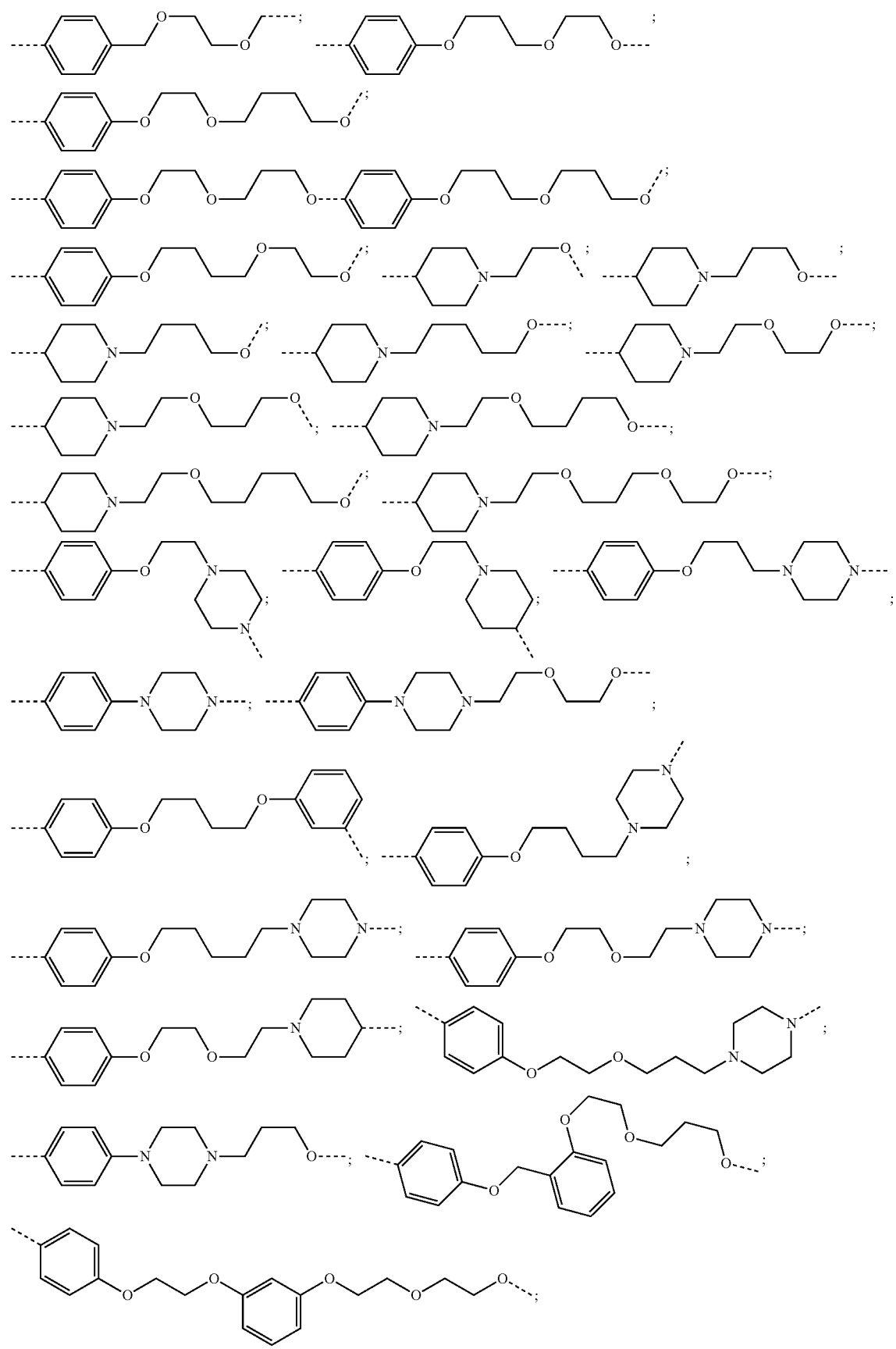

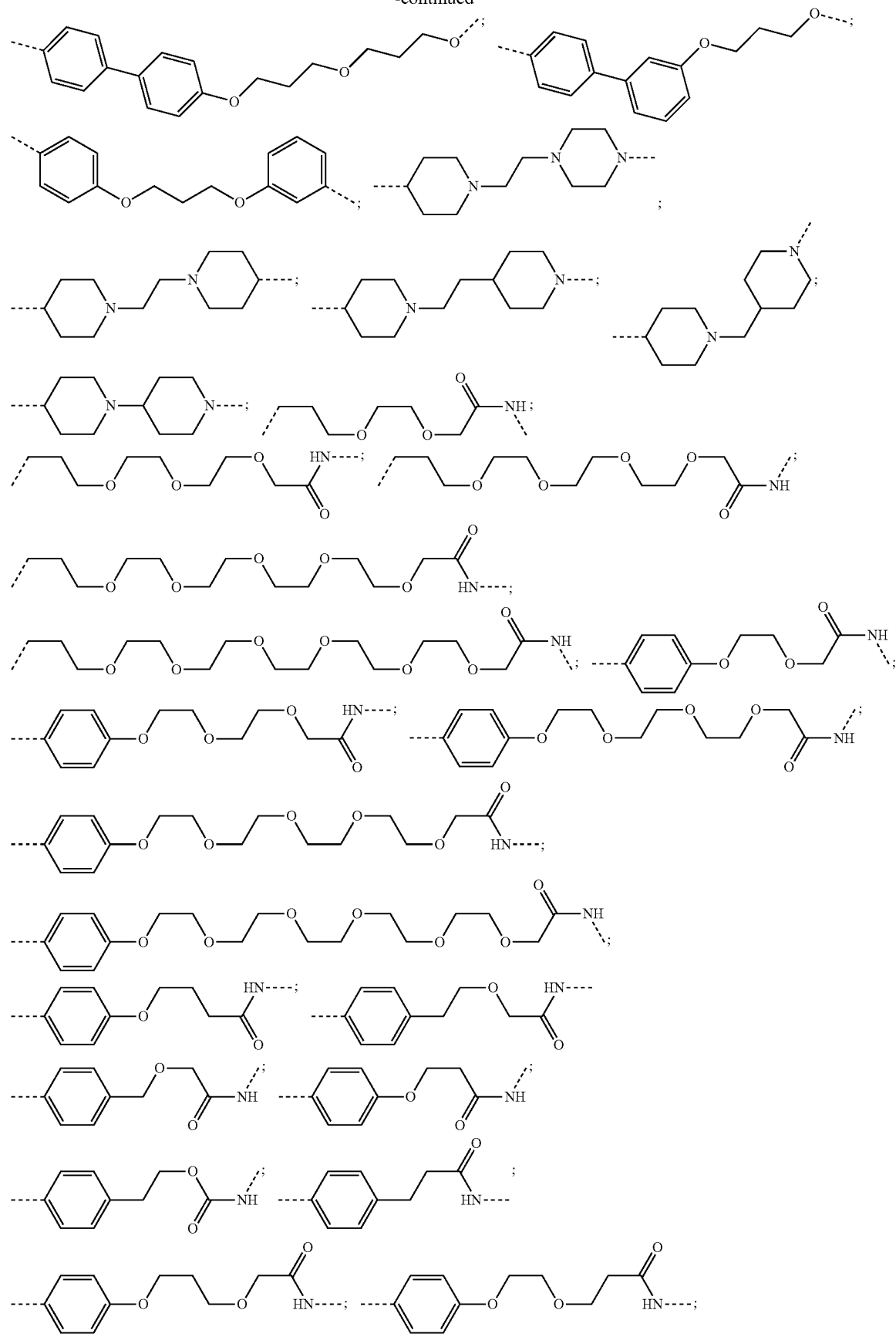

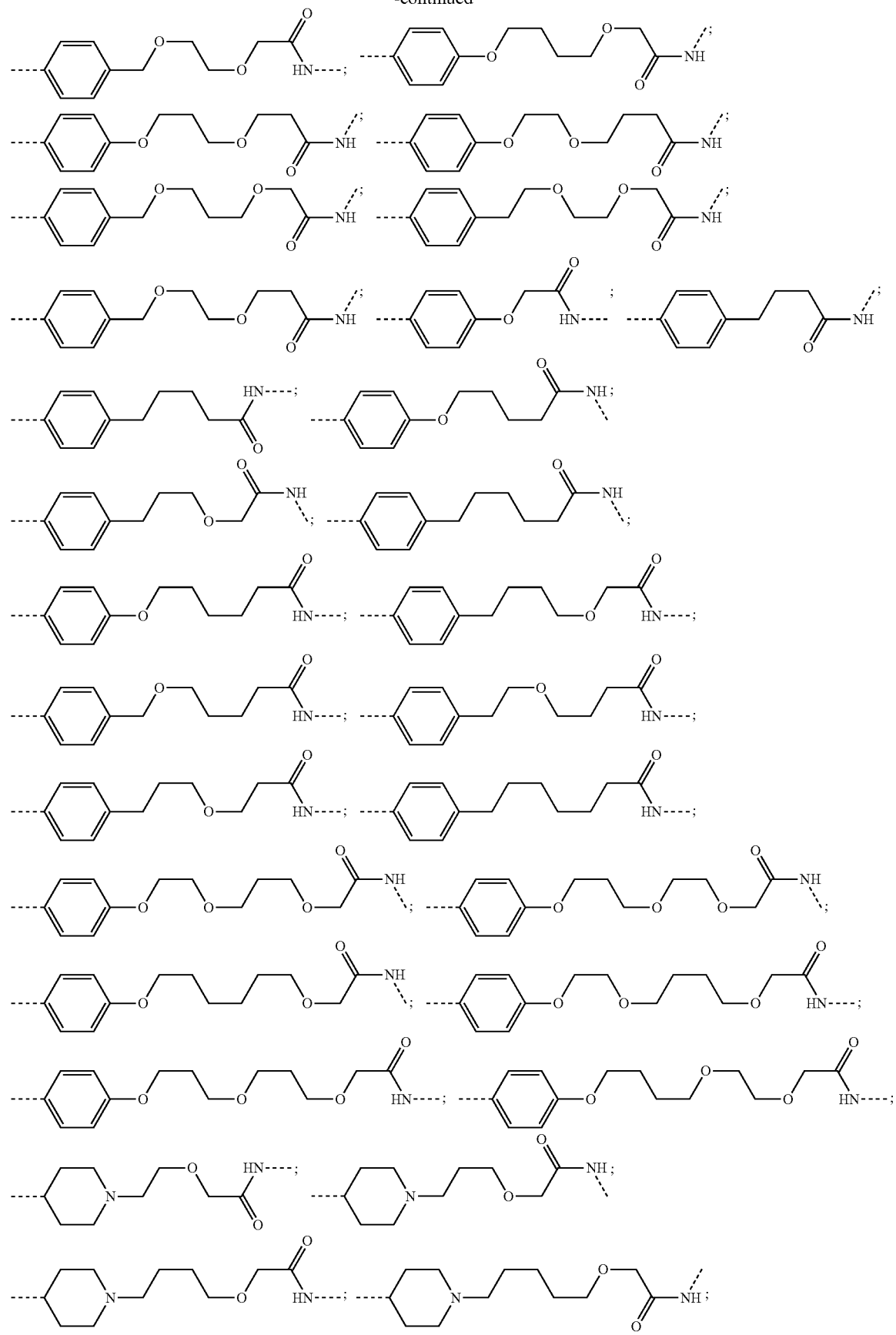

1137
1138
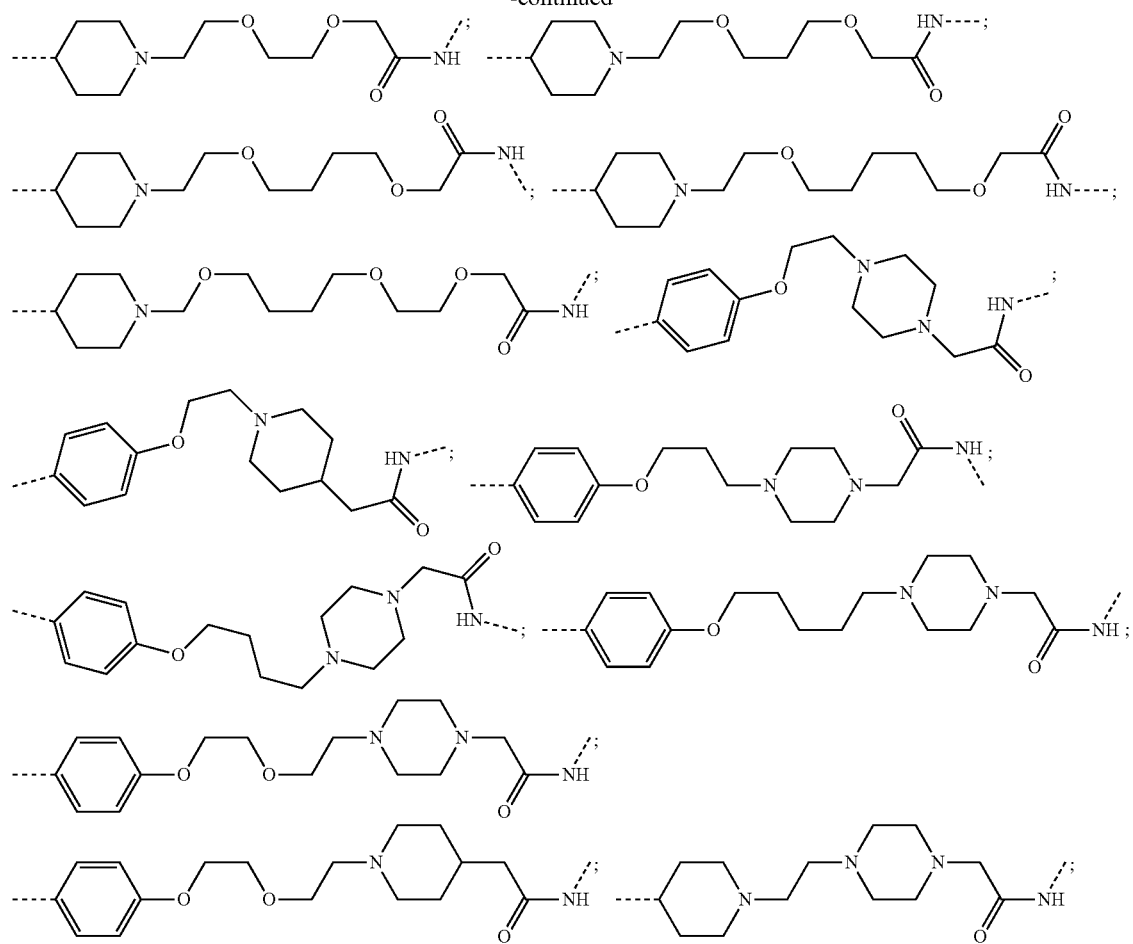
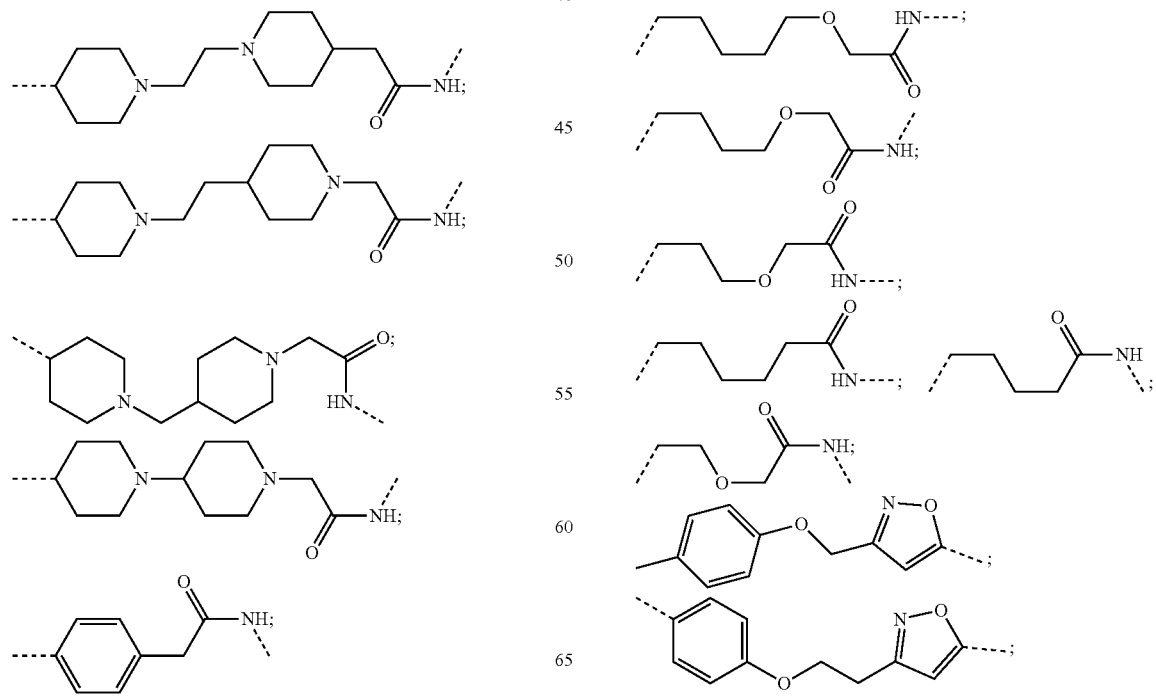

1139
-continued
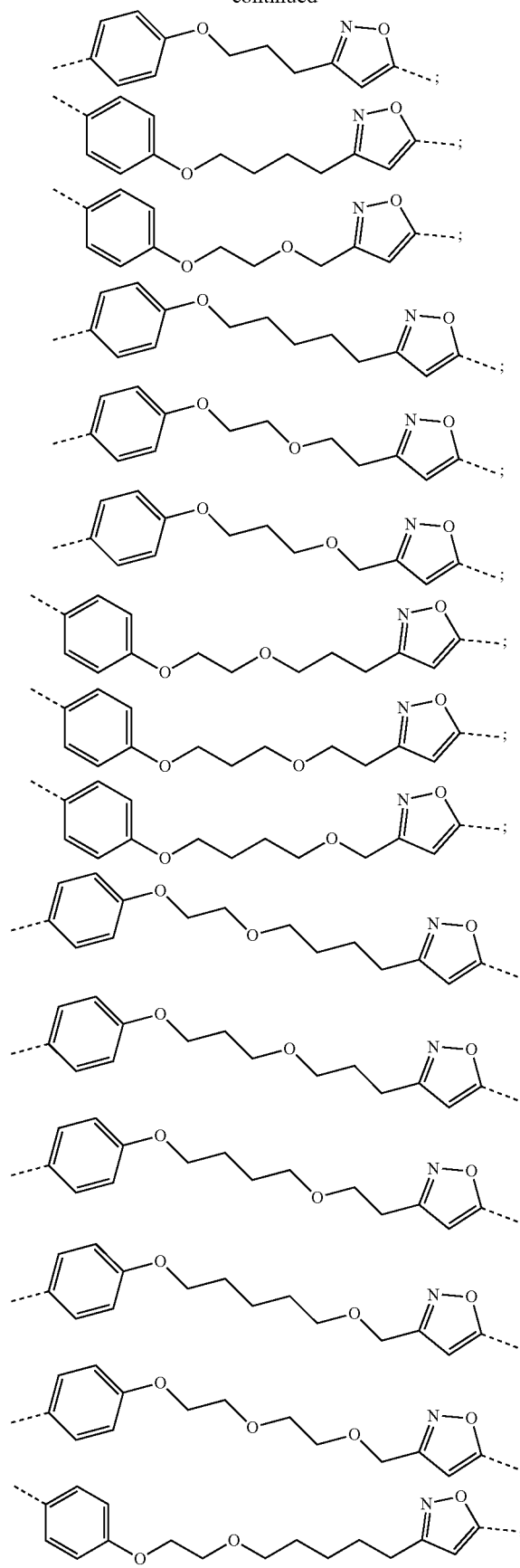
1140
-continued
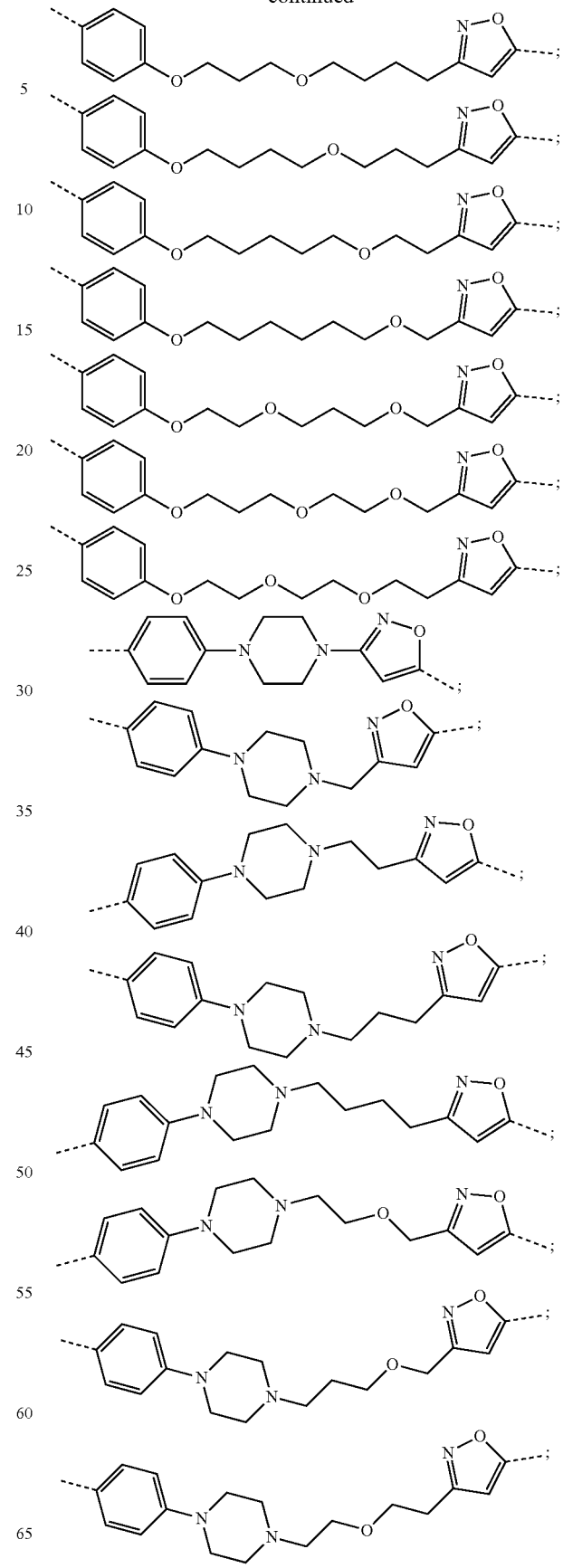

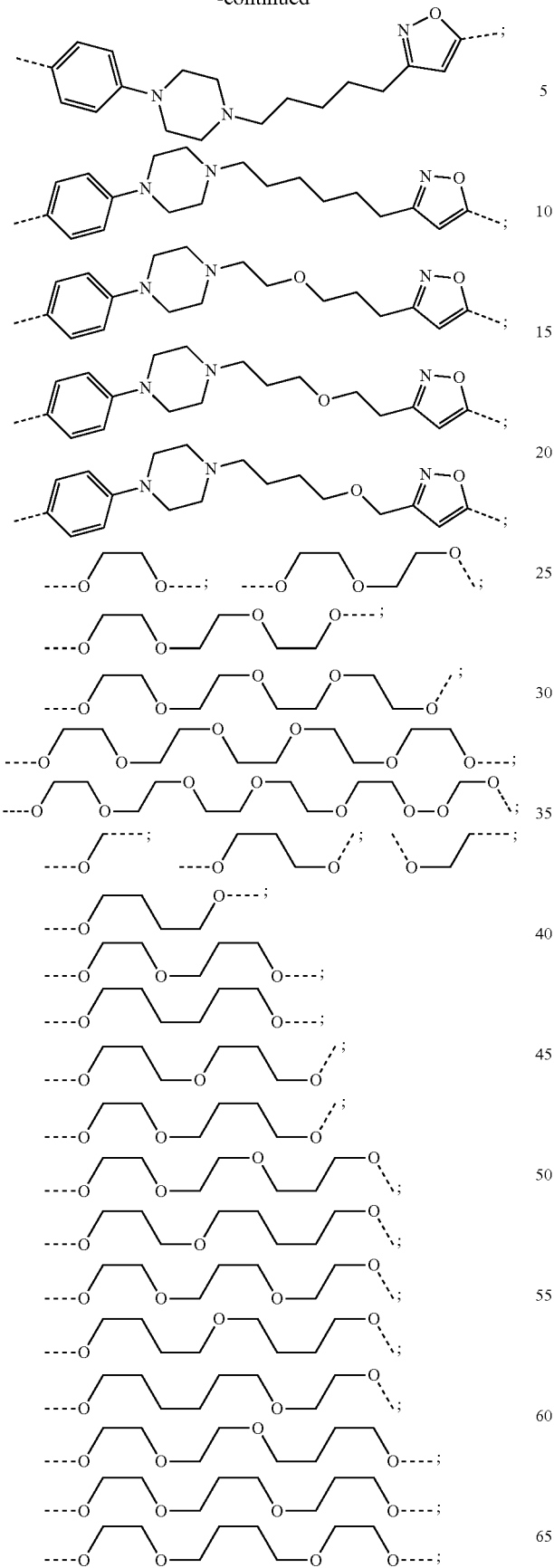
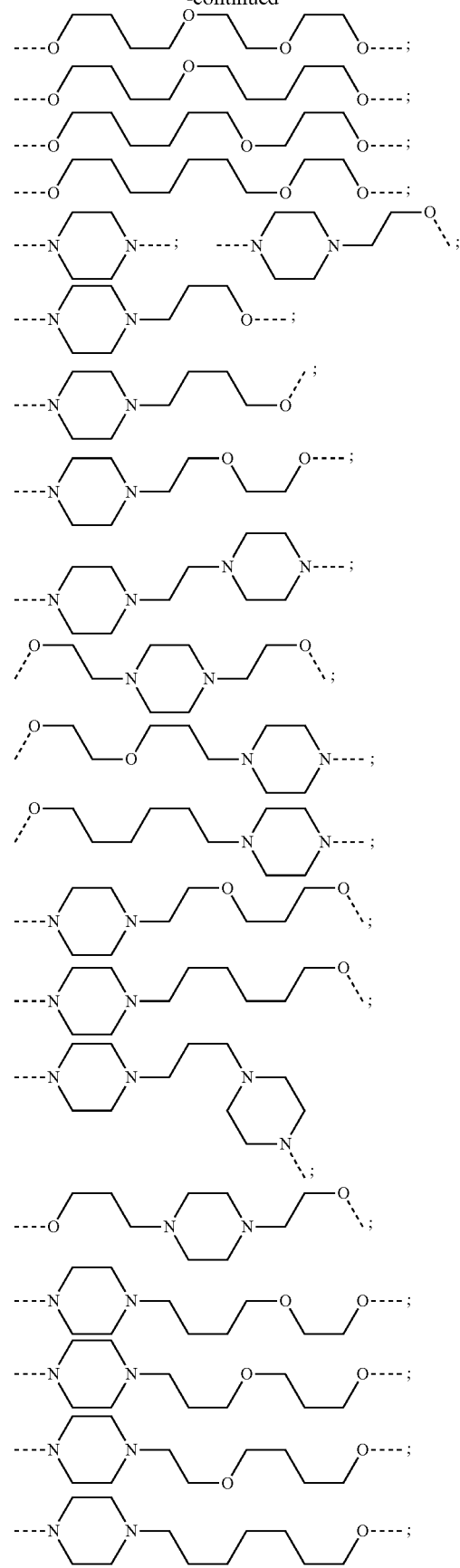

1143
-continued
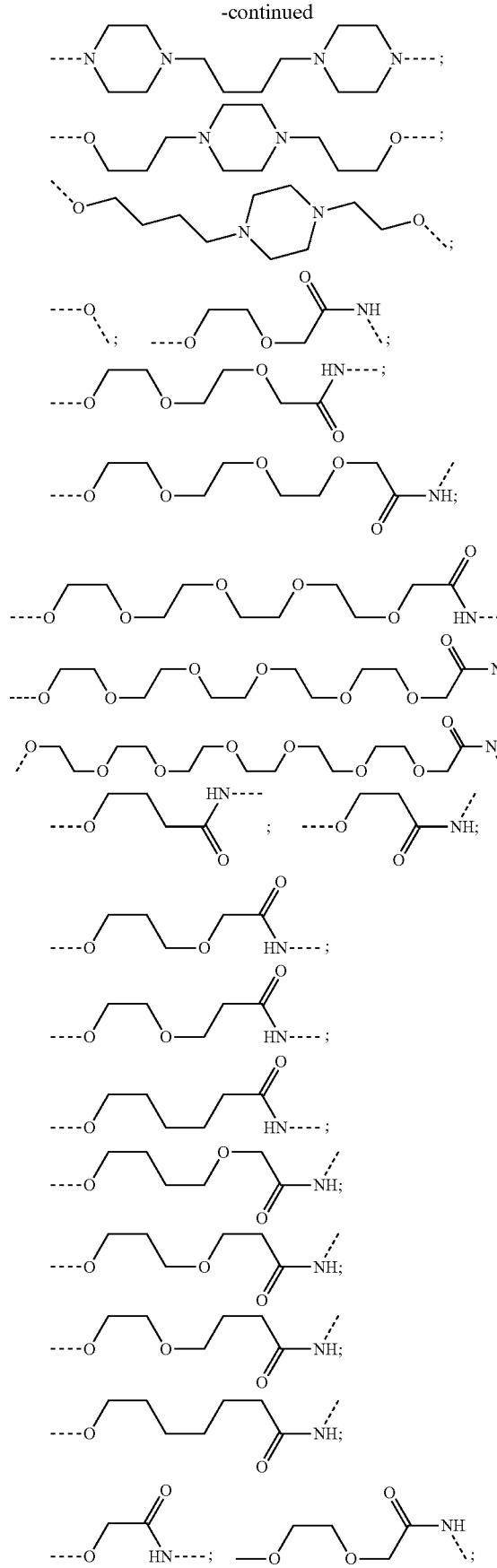
1144
-continued
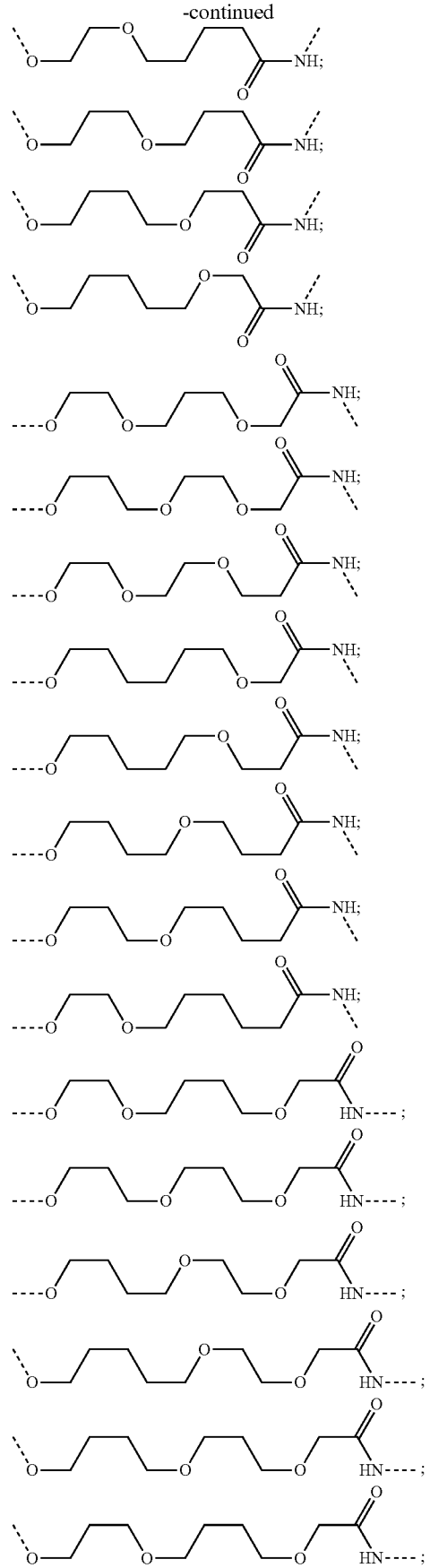

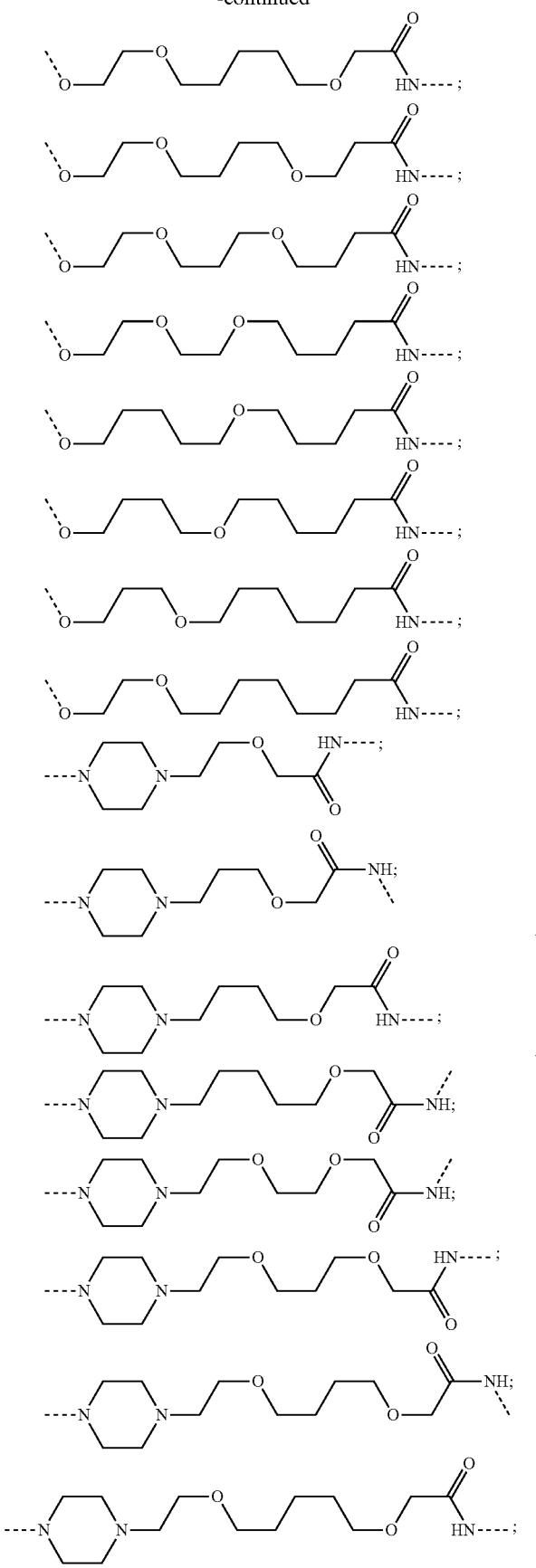
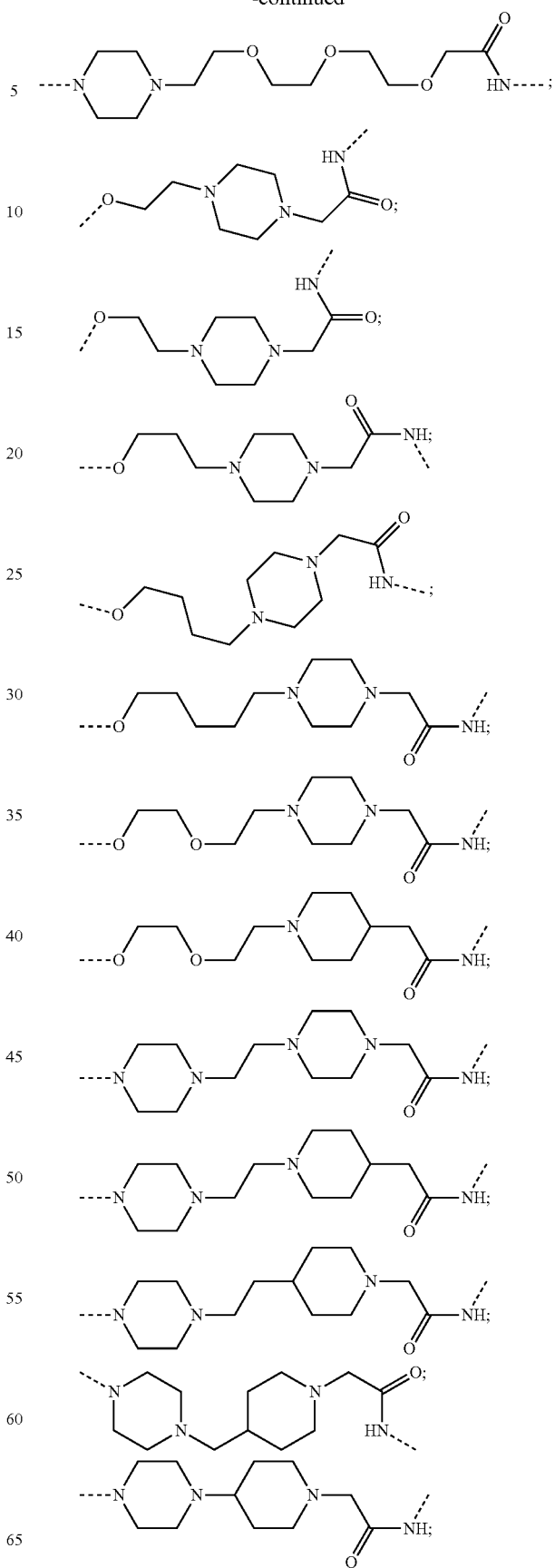

1147
-continued
1148
-continued
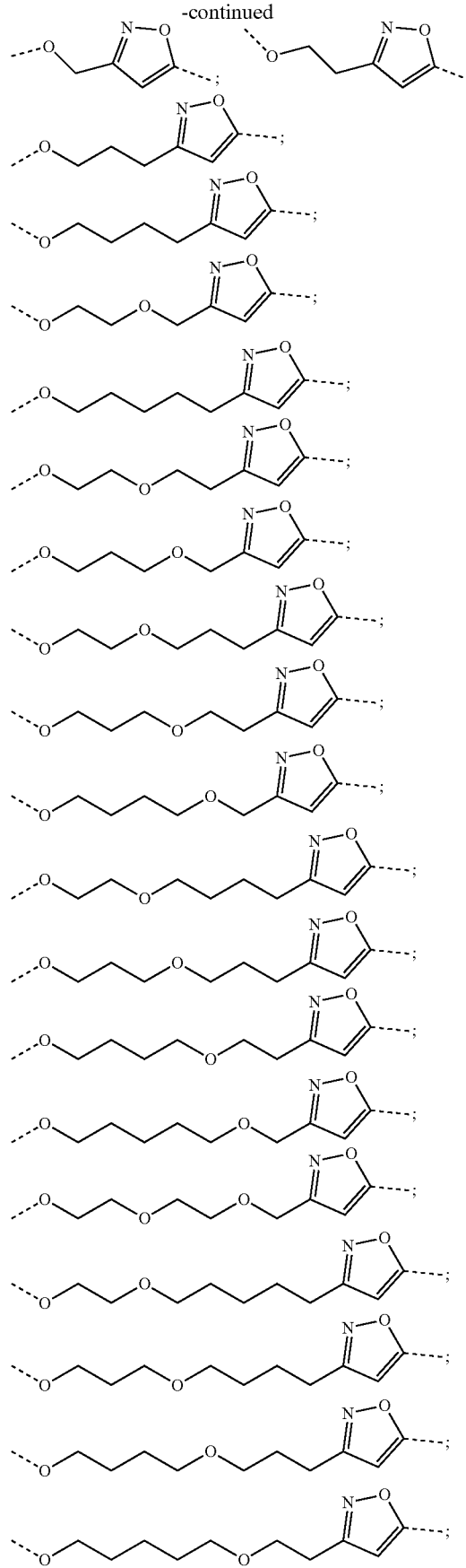
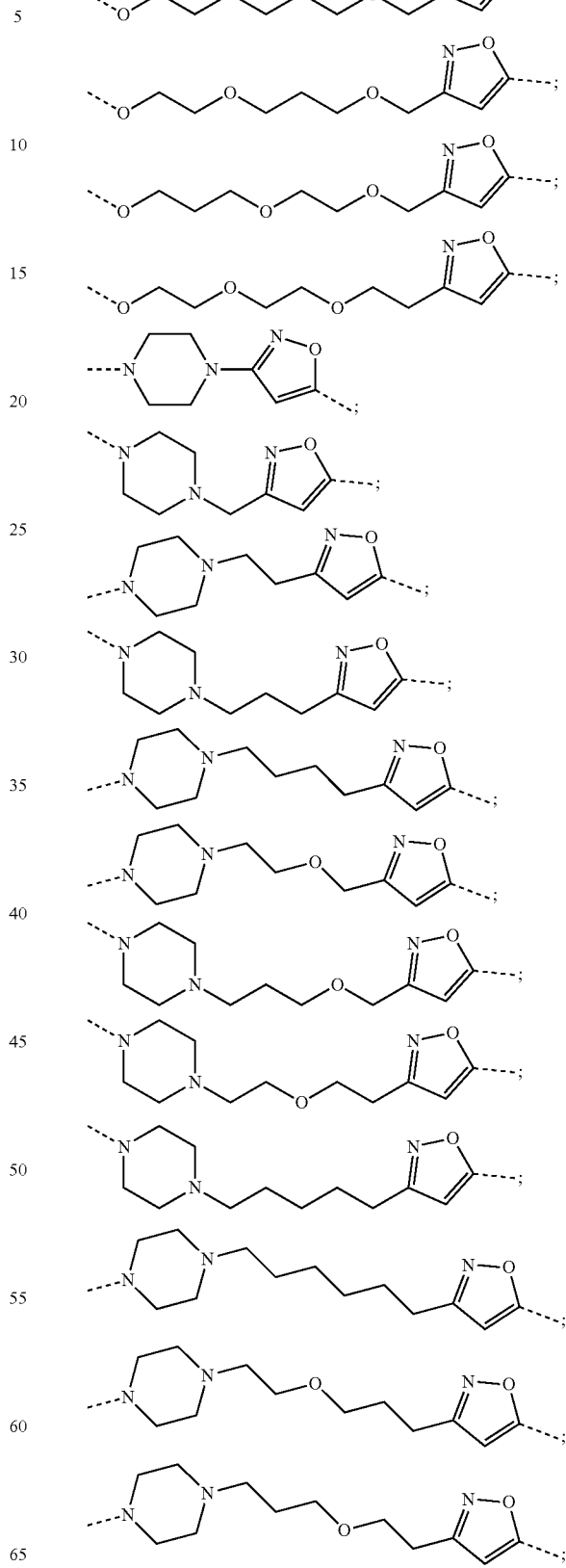

-continued

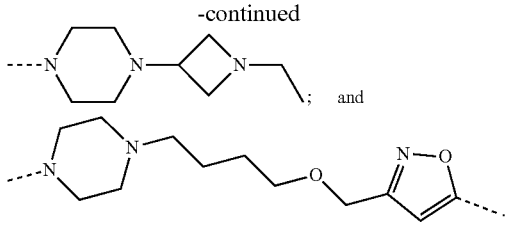
; and

In any aspect or embodiment described herein, the linker (L) is a polyethylenoxy group optionally substituted with aryl or phenyl comprising from 1 to 10 ethylene glycol units.

In any aspect or embodiment described herein, the linker (L) comprises the following chemical structure:

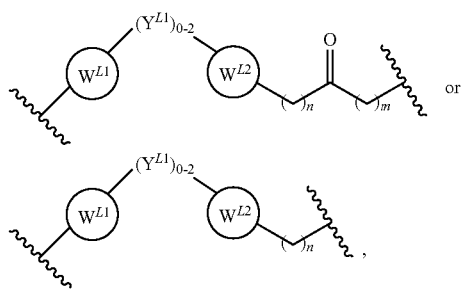

wherein:
- $W^{L1}$ and $W^{L2}$ are each independently absent, a 4-8 membered ring with 0-4 heteroatoms, optionally substituted with RQ, each RQ is independently a H, halo, OH, CN, CF3, optionally substituted linear or branched C1-C6 alkyl, optionally substituted linear or branched C1-C6 alkoxy, or 2 RQ groups taken together with the atom they are attached to, form a 4-8 membered ring system containing 0-4 heteroatoms;
- $Y^{L1}$ is each independently a bond, optionally substituted linear or branched C1-C6 alkyl and optionally one or more C atoms are replaced with O; or optionally substituted linear or branched C1-C6 alkoxy;
- n is 0-10; and

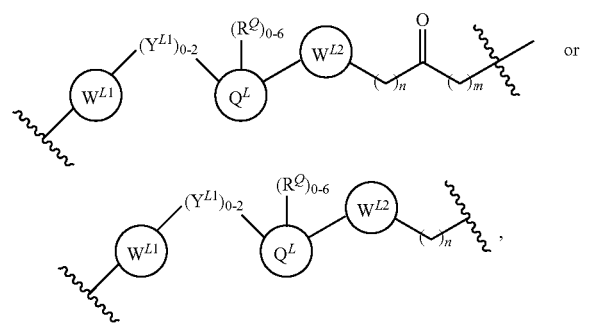 indicates the attachment point to the PTM or ULM moieties.

In any aspect or embodiment described herein, the linker (L) comprises the following chemical structure:

wherein:
- $W^{L1}$ and $W^{L2}$ are each independently absent, aryl, heteroaryl, cyclic, heterocyclic, $C_{1-6}$ alkyl and optionally one or more C atoms are replaced with O or N, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;
- $Y^{L1}$ is each independently a bond, $NR^{YL1}$, O, S, $NR^{YL2}$, $CR^{YL1}R^{YL2}$, C=O, C=S, SO, $SO_2$, optionally substituted linear or branched $C_1$-$C_6$ alkyl and optionally one or more C atoms are replaced with O; optionally substituted linear or branched $C_1$-$C_6$ alkoxy, 3-6 membered alicyclic or aromatic ring with 0-4 heteroatoms;
- $Q^L$ is a 3-6 membered alicyclic or aromatic ring with 0-4 heteroatoms, optionally bridged, optionally substituted with 0-6 $R^Q$, each $R^Q$ is independently H, optionally substituted linear or branched $C_{1-6}$ alkyl (e.g., optionally substituted by 1 or more halo or $C_{1-6}$ alkoxyl), or 2 $R^Q$ groups taken together with the atom they are attached to, form a 3-8 membered ring system containing 0-2 heteroatoms;
- $R^{YL1}$, $R^{YL2}$ are each independently H, OH, optionally substituted linear or branched $C_{1-6}$ alkyl (e.g., optionally substituted by 1 or more halo or $C_{1-6}$ alkoxyl), or $R^1$, $R^2$ together with the atom they are attached to, form a 3-8 membered ring system containing 0-2 heteroatoms;
- n is 0-10; and indicates the attachment point to the PTM or ULM moieties.

In any aspect or embodiment described herein, the unit $A^L$ of linker (L) is selected from the group consisting of:

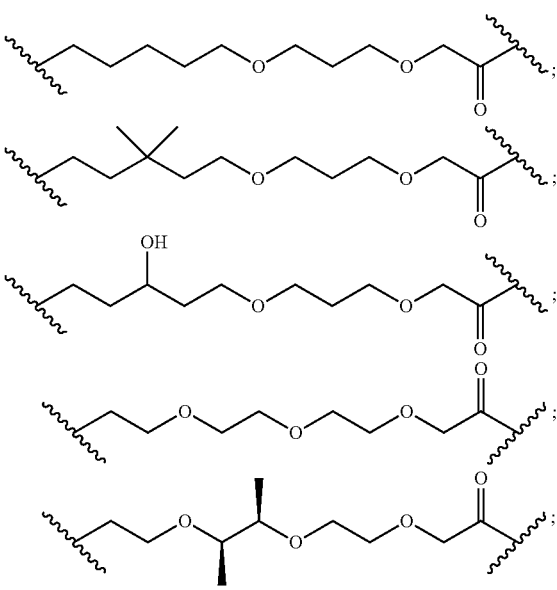

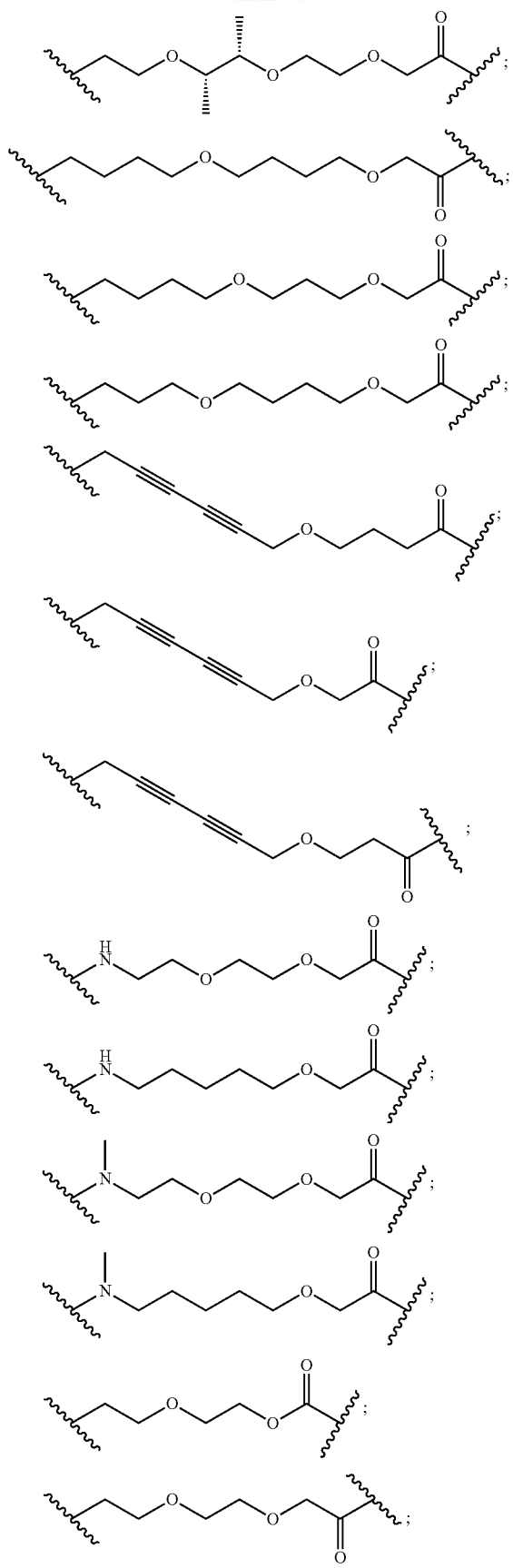
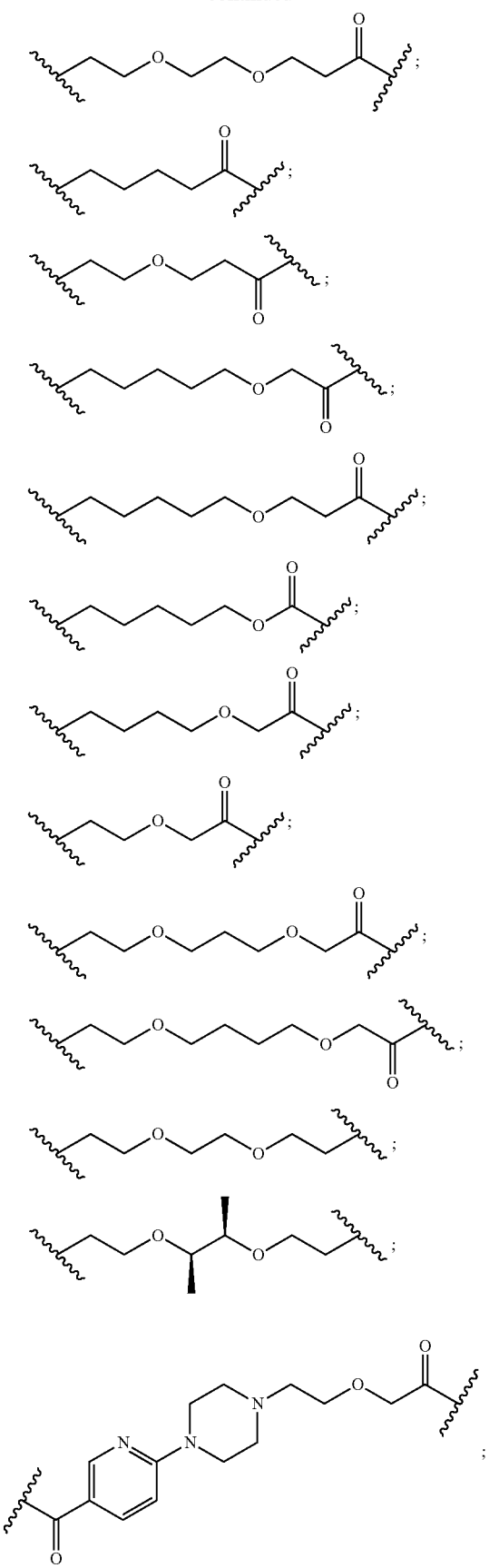

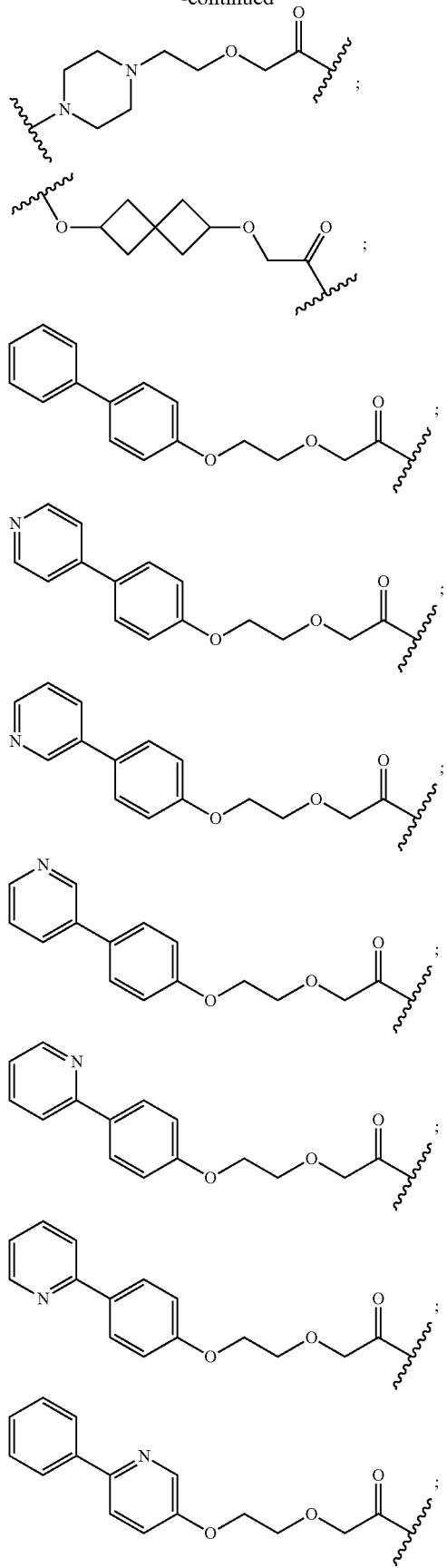
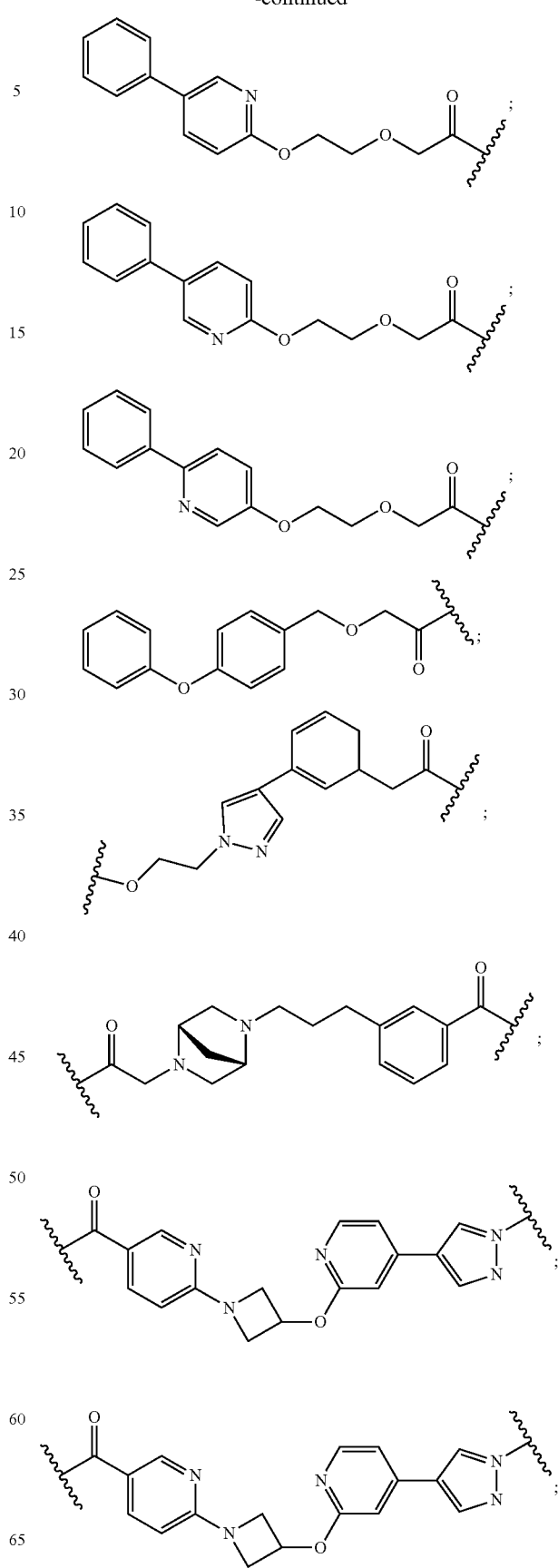

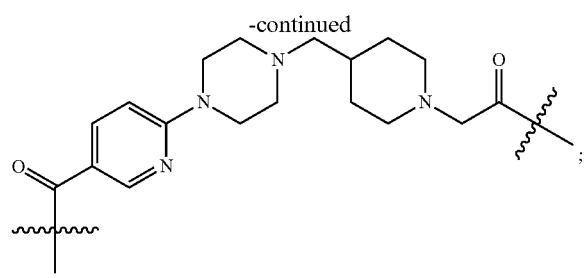
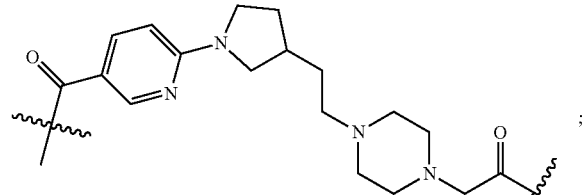
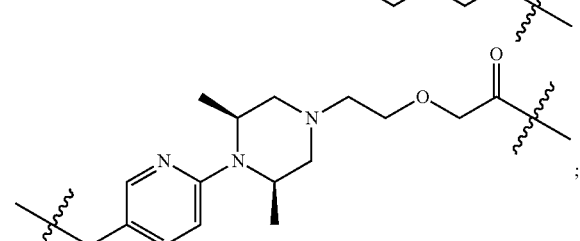
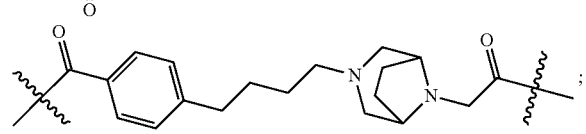
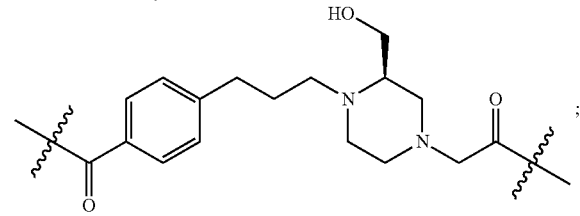
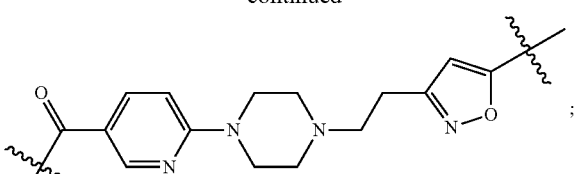
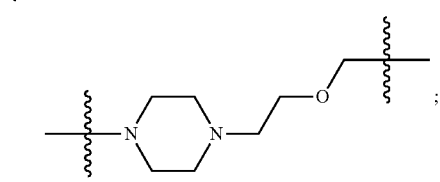
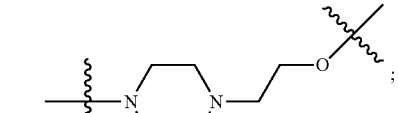
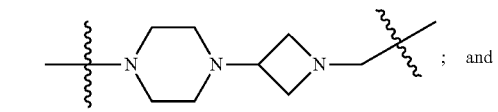
; and
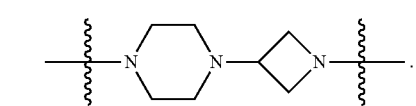
.
In any aspect or embodiment described herein, at least one of:
(a) the PTM is selected from a compound of Tables 4, 6, 8, 10, and 12 or a PTM of Table 1;
(b) the ULM is selected from a compound of Tables 4, 6, 8, 10, and 12 or a ULM of Table 3;
(c) the unit $A^L$ of linker (L) is selected from:
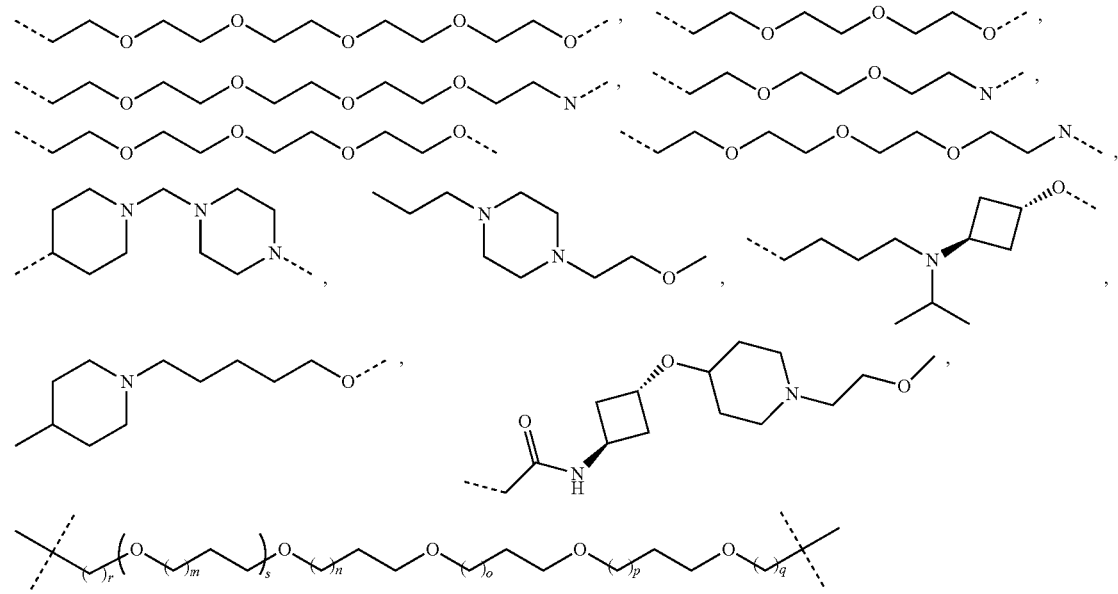

-continued
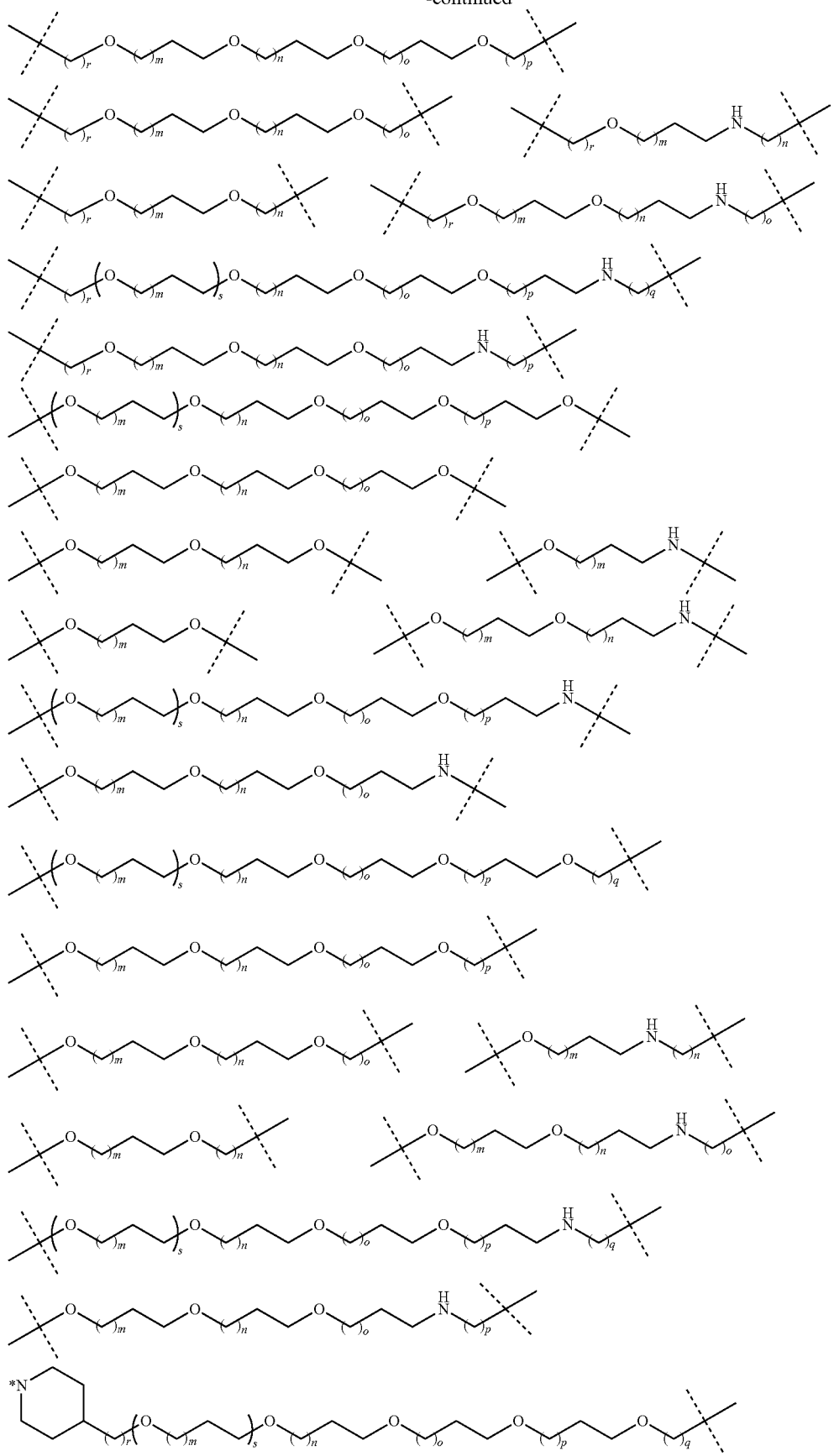

-continued
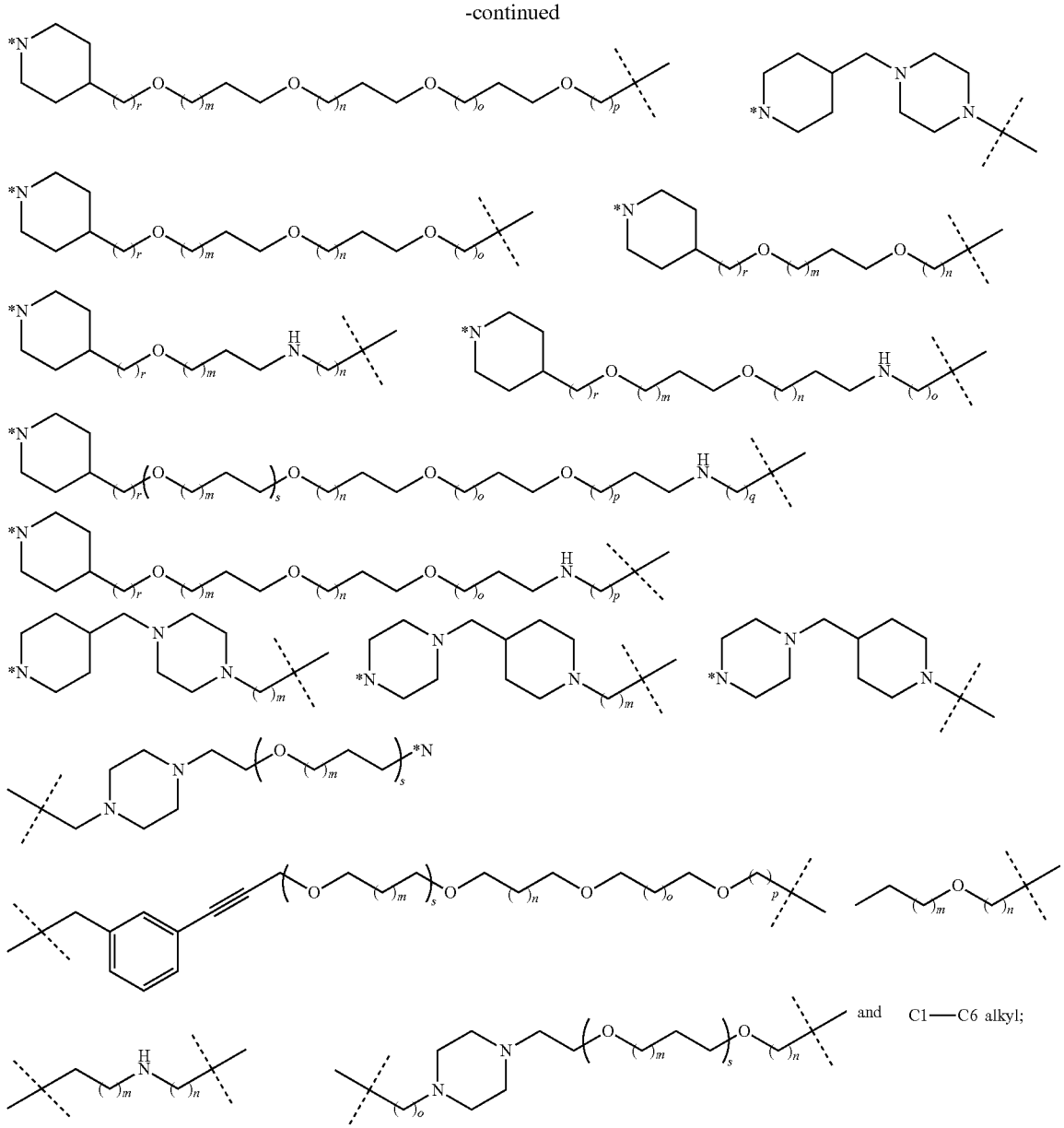
or
(d) combinations thereof,
wherein:
  *N of the heterocycloalkyl is shared with the PTM; and
  each m, n, o, p, q, r, and s are independently selected from 0, 1, 2, 3, 4, 5, 6, 7, 8, 9, or 10.
In any aspect or embodiment described herein, the unit $A^L$ of linker (L) or L is selected from the group consisting of:
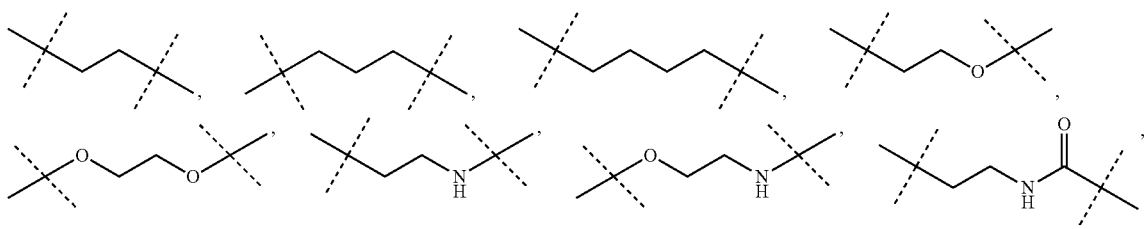

1161  1162
-continued
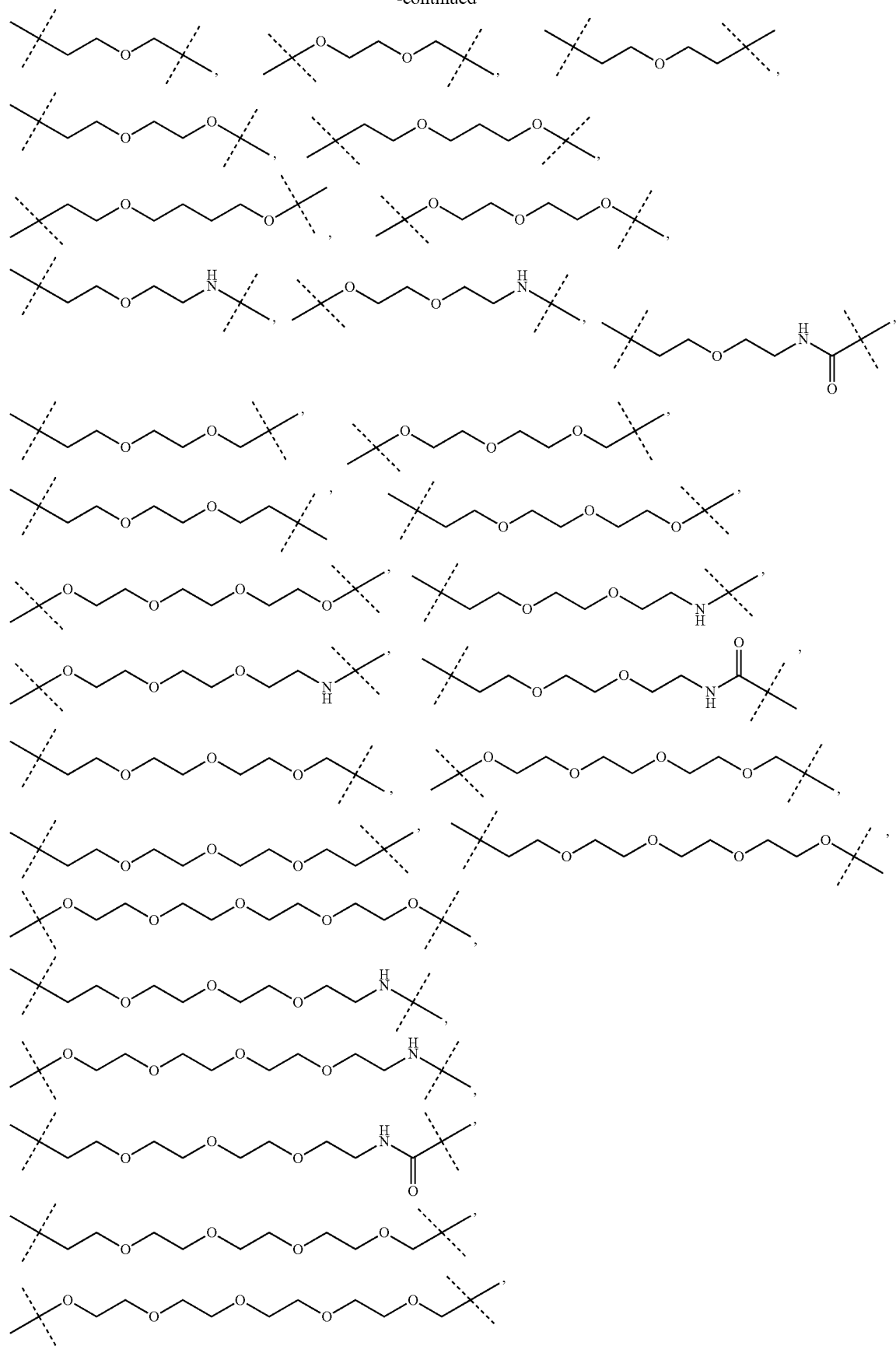

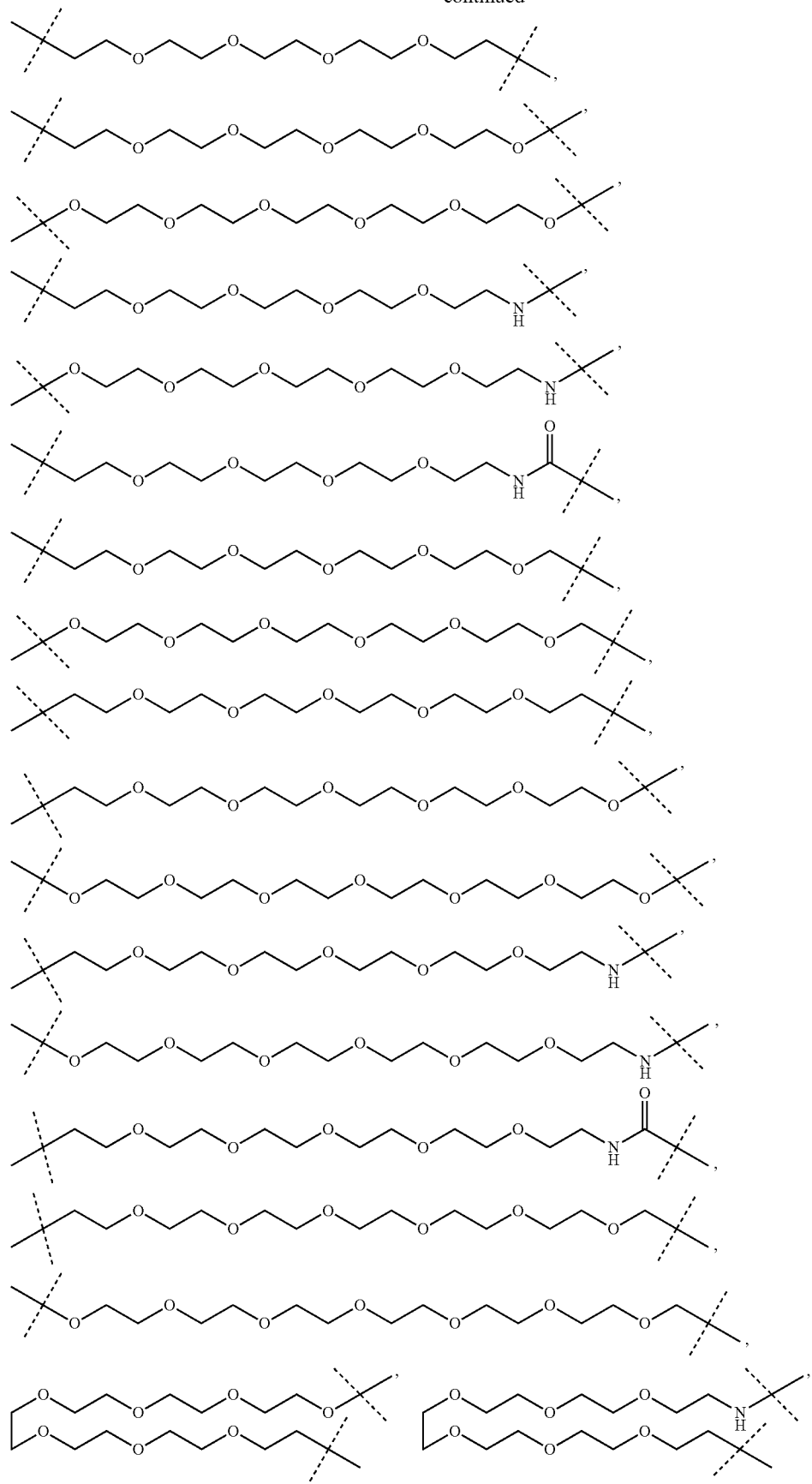

1165                                    1166
-continued
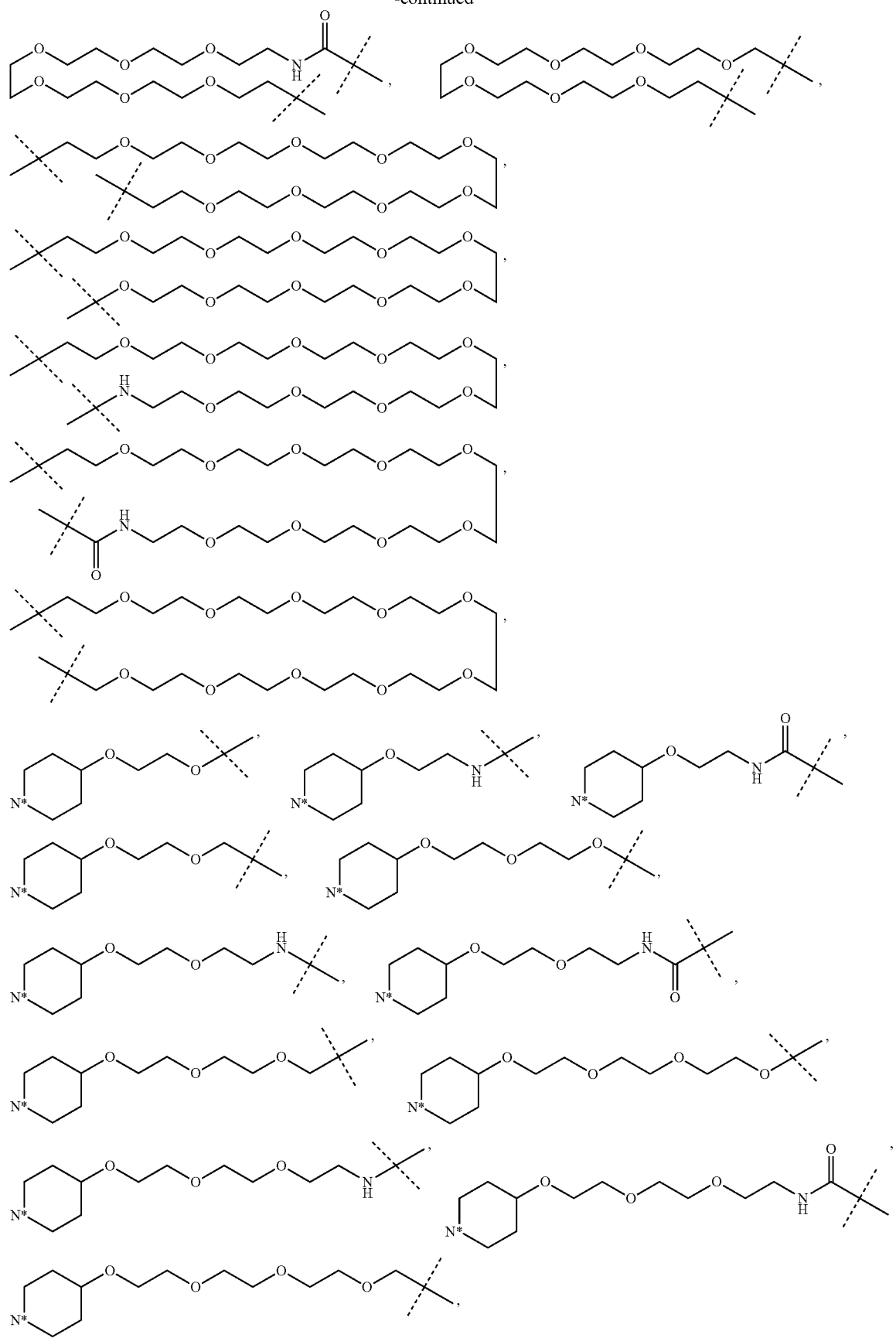

1167
-continued
1168
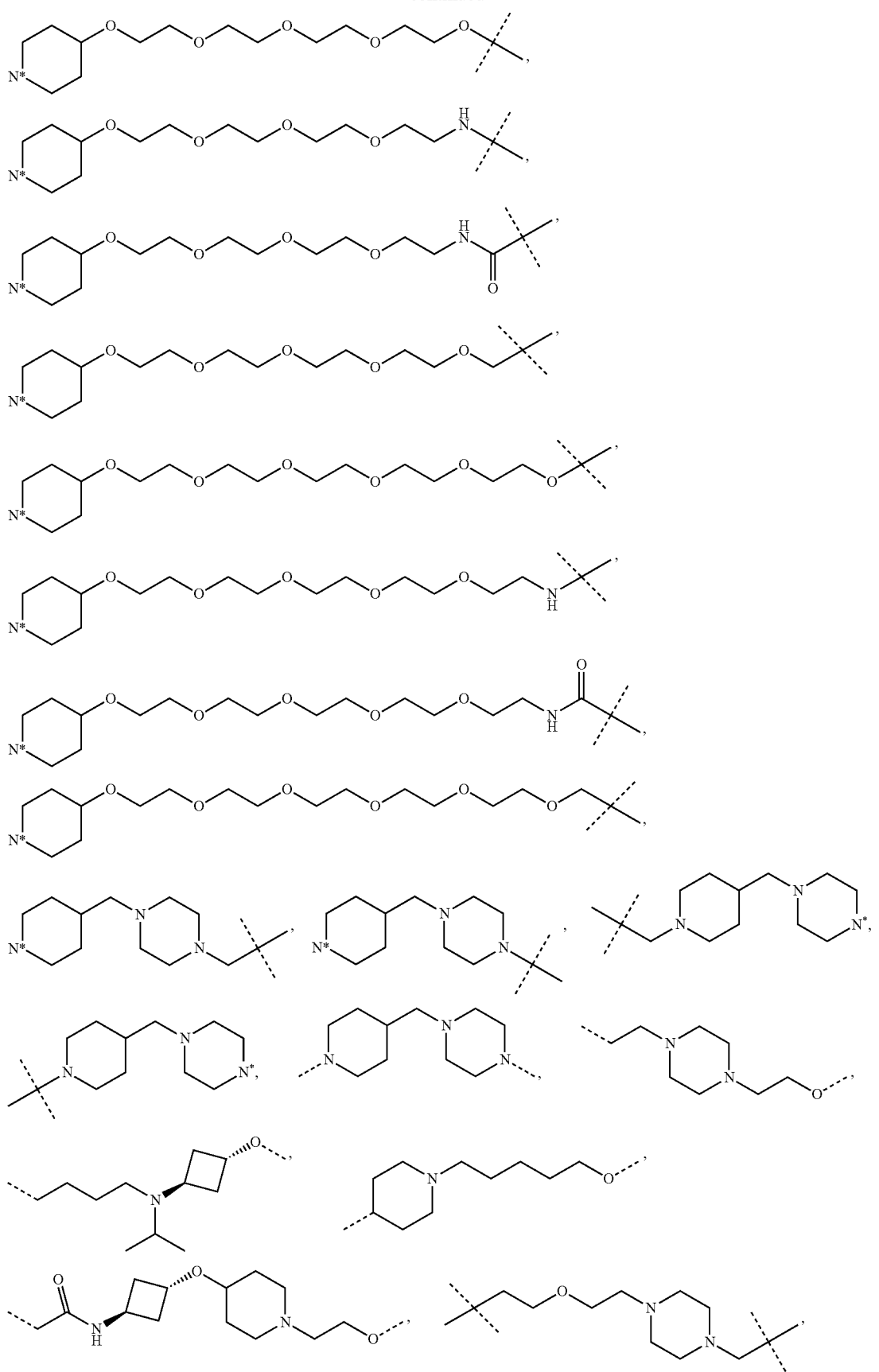

-continued

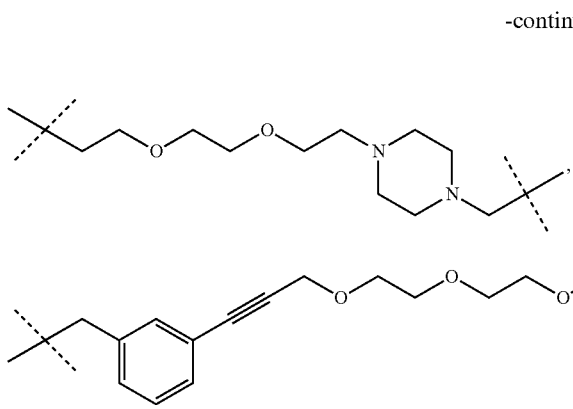

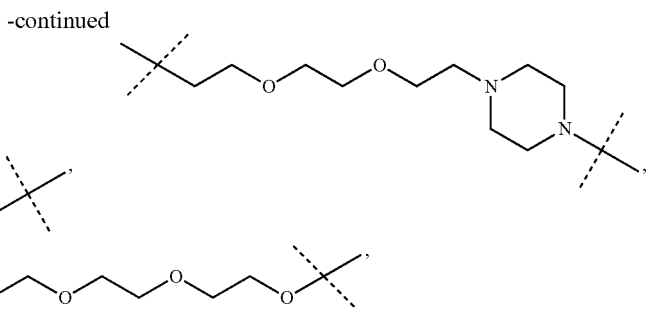

wherein N* of the heterocycloalkyl is shared with the PTM.

In any aspect or embodiment described herein, at least one of:
  the PTM is selected from PTM-1, PTM-2, PTM-3, PTM-4, PTM-5, or PTM-6;
  the linker is selected from L-1, L-2, L-3, L-4, L-5, or L-6;
  the ULM is selected from ULM-1, ULM-2, ULM-3, ULM-4, or ULM-5; or combinations thereof.

In any aspect or embodiment described herein, the compound is selected from the group consisting of: exemplary compounds 1-10.

Another aspect of the present disclosure provides a composition comprising an effective amount of a bifunctional compound of the present disclosure, and a pharmaceutically acceptable carrier.

In any aspect or embodiment described herein, the composition further comprises at least one of additional bioactive agent or another bifunctional compound of the present disclosure.

In any aspect or embodiment described herein, the additional bioactive agent is an anti-cancer agent (e.g., an epidermal growth factor receptor inhibitor).

A further aspect of the present disclosure provides a composition comprising a pharmaceutically acceptable carrier and an effective amount of at least one compound of the presente disclosure for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with at least one of accumulation, aggregation, overactivation, or combinations thereof, of KRas.

In any aspect or embodiment described herein, the disease or disorder is cancer that is associated with the accumulation, aggregation, and/or overactivation of KRas.

In any aspect or embodiment described herein, the disease or disorder is pancreatic cancer, colon cancer, colorectal cancer, lung cancer, non-small cell lung cancer, biliary tract malignancies, endometrial cancer, cervical cancer, bladder cancer, liver cancer, myeloid leukemia, and breast cancer.

In any aspect or embodiment described herein, the disease or disorder is pancreatic cancer, colon cancer, lung cancer, non-small cell lung cancer.

EXAMPLES

Assays and Degradation Data
  Cell Lines, Antibodies, and Reagents.
  NCI-H2030 (CRL-5914) and SW1573 (CRL-2170) cells were purchased from ATCC. Both cell lines are homozygous for the G12C mutation in KRas. NCI-H2030 cells were cultured in RPMI-1640 medium containing 1% penicillin-streptomycin and 10% fetal bovine serum (FBS). SW1573 cells were cultured in DMEM containing 1% penicillin-streptomycin and 10% FBS. The KRas detection antibody (Cat. No. LS-C175665) was purchased from LifeSpan Biosciences and was used at a dilution of 1:2000. GAPDH was detected using an antibody purchased from Cell Signaling Technology (Cat. No. 5174) and was diluted 1:3000. Secondary anti-mouse and anti-rabbit detection antibodies were purchased from Cell Signaling Technology (Cat. Nos. 7076 and 7074, respectively).
  Compound Treatment and Western Blotting of the Data of Table 5.
  H2030 cells in 12-well plates were serum starved for 24 hours, and then treated with 0.3 uM, 1 uM, and 3 uM of the indicated bifunctional compound, for 24 hours. Cells were lysed in a Cell Signaling Technology Cell Lysis Buffer (Cat. No. #9803) supplemented with protease inhibitors, and proteins were separated by SDS-PAGE. KRas was detected by immunoblotting using the LSBio antibody (Cat. No. LS-C175665).
  Compound Treatment and Western Blotting of the Data of Table 14.
  Either NCI-H2030 or SW1573 cells were plated in 12-well plates and allowed to adhere overnight at 37° C. in an incubator containing 5% $CO_2$. The following day, the medium was replaced with the appropriate medium lacking FBS to induce starvation. Cells were returned to the incubator for an additional 24 hours following media exchange. Compounds were then added to the appropriate final concentration (0.3 µM, 1 µM, and 3 µM) in 0.1% DMSO. Cells were treated with VHL-based compounds for 24 hours and all other compounds for 72 hours. Following treatment, cells were lysed in RIPA buffer (Thermo Fisher Cat. No. 89900) containing phosphatase (Thermo Fisher Cat. No. 1861277) and protease (Thermo Fisher Cat. No. 78429) inhibitor cocktails. Lysates were cleared at 13,000 rpm for 15 minutes and supernatants were assayed for total protein concentration using the Pierce BCA assay system (Thermo Fisher Cat. No. 23225). For each sample, 10 µg total protein was resolved on a 12% Bis-Tris gel and then transferred to a nitrocellulose membrane. After blocking in 3% BSA in TBST (Tris-buffered Saline with 0.1% Tween-20) for 1 hour at room temperature, membranes were probed with the primary antibody (LS Bio Cat. No. LS-C175665) overnight at 4° C. After incubation with the secondary antibody, the following day membranes were visualized using the Super-Signal™ West Femto substrate (Thermo Fisher Cat. No. 34095). The KRas signal in each lane was normalized to GAPDH and percent degradation was either estimated as less than 25% by visual inspection (C in Table 13) or quantitated relative to the DMSO control lane using BIO-RAD Image Lab 5.2.1, and all data was plotted using GraphPad PRISM 6.07.

$DC_{50}$ is the half-maximal degradation concentration—i.e., the concentration at which 50% degradation is observed. $D_{Max}$ is the maximum degradation efficacy is achieved—i.e., the maximal degradation observed) degradation data.

Figure 2A:
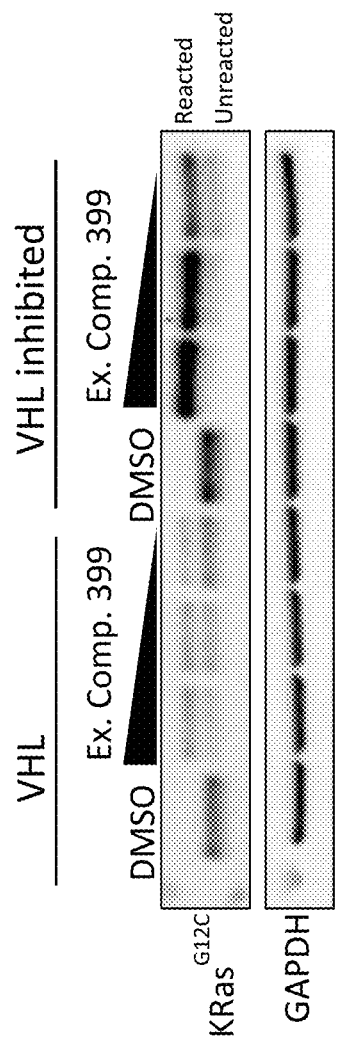
FIGS. 2A and 2B.
Figure 2B:
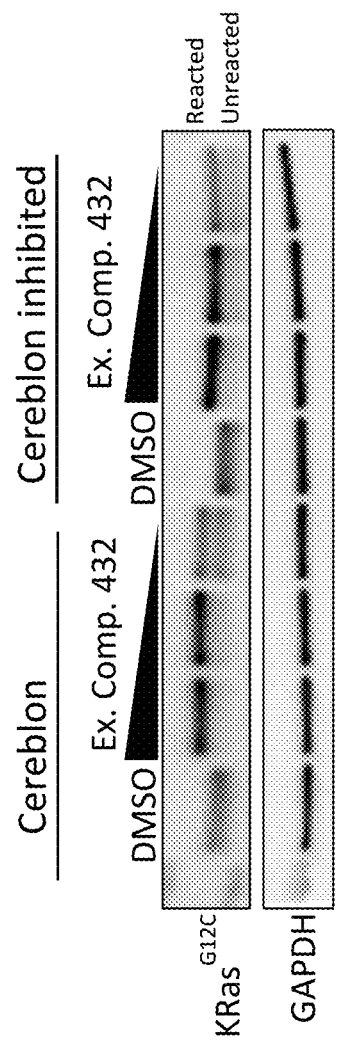

FIGS. 2A and 2B show the result of treating cells with either a bifunctional compound alone or a bifunctional compound and an E3 ubiquitin ligase inhibitor, and then detecting the KRas protein on the gel. The mobility shift of KRas detection on the gel illustrates that the bifunctional compounds covalently modify KRas. The upper band is KRas and the bifunctional compound, while the lower band is KRas alone. FIG. 2A is a representative Western blot of a potent degrader, exemplary compound 399. FIG. 2B is a representative Western blot of a less active degrader, exemplary compound 432. Both compounds covalently modify $KRas^{G12C}$, as seen by the gel shift.

The bifunctional compounds of Tables 4, 6, 8, 10, and 12 demonstrated target protein degradation when tested under the conditions described above. For example, each of the bifunctional compound of Table 4 had a DC50 in the range of 500 nM to 1 uM and a Dmax as shown in Table 5. By way of further example, the bifunctional compounds of Table 6, 8, 10, and 12 degraded KRas, as shown in Table 14. In the tables, "nd" is an indication that the particular parameter, characteristic, etc., was not determined for the particular compound.

TABLE 4

Exemplary Bifunctional Compounds of the Ppresent Disclosure

| Ex. No. | Chemical Structure | Compound Name |
|---|---|---|
| 1 | 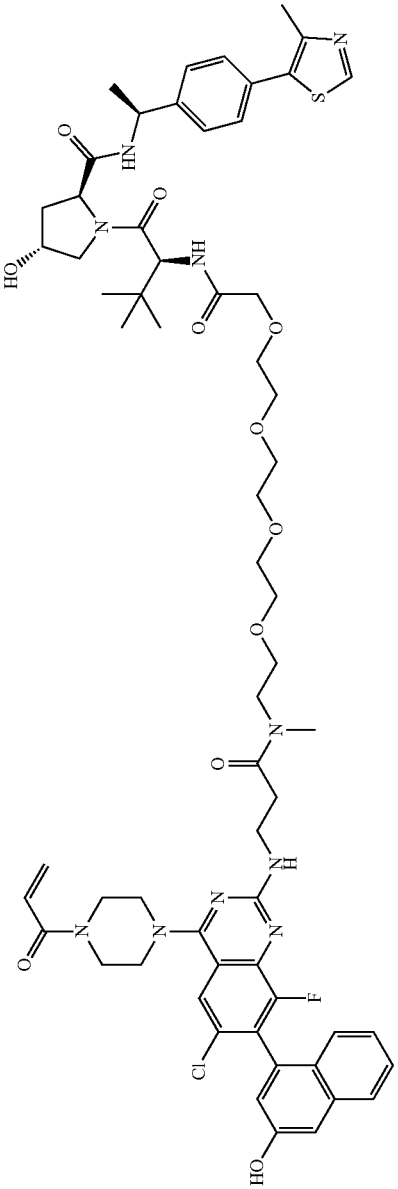 | (2S,4R)-1-((2S)-21-((4-(4-acryloylpiperazin-1-yl)-6-chloro-8-fluoro-7-(3-hydroxynaphthalen-1-yl)quinazolin-2-yl)amino)-2-(tert-butyl)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide |
| 2 | 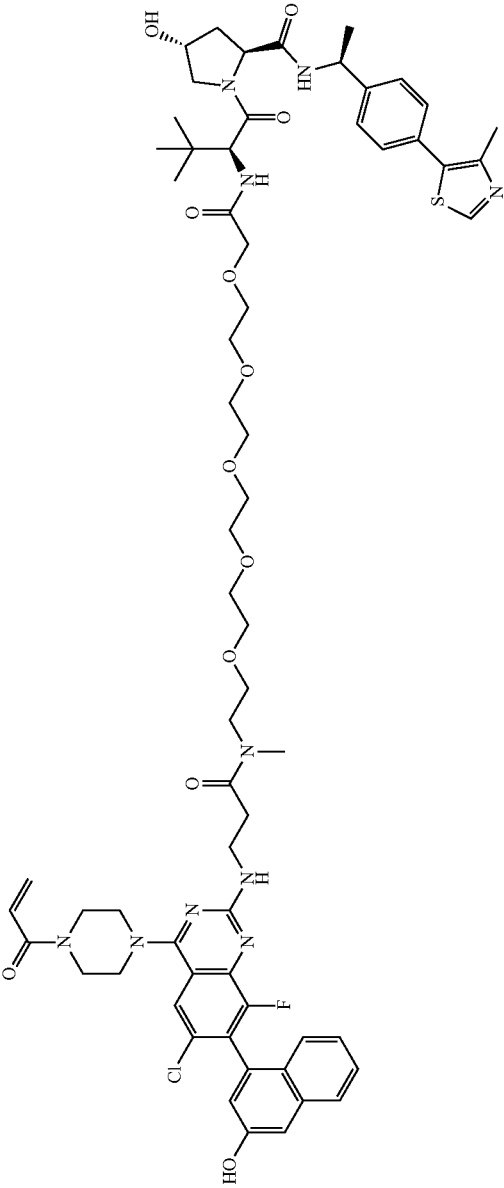 | (2S,4R)-1-((2S)-24-((4-(4-acryloylpiperazin-1-yl)-6-chloro-8-fluoro-7-(3-hydroxynaphthalen-1-yl)quinazolin-2-yl)amino)-2-(tert-butyl)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide |

TABLE 4-continued

Exemplary Bifunctional Compounds of the Present Disclosure

| Ex. No. | Chemical Structure | Compound Name |
|---|---|---|
| 3 | 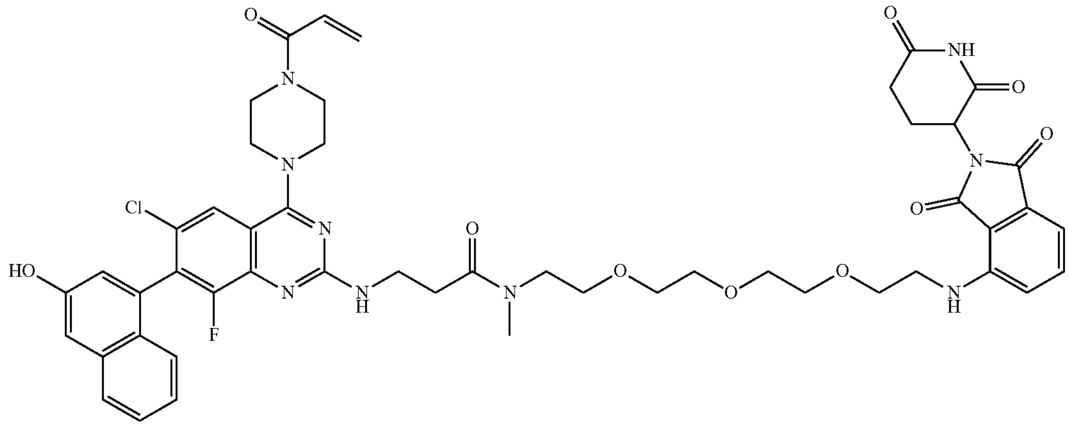 | 3-((4-(4-acryloylpiperazin-1-yl)-6-chloro-8-fluoro-7-(3-hydroxynaphthalen-1-yl)quinazolin-2-yl)amino)-N-(2-(2-(2-(2-((2-(2,6-dioxopiperidin-3-yl)-1,3-dioxoisoindolin-4-yl)amino)ethoxy)ethoxy)ethoxy)ethyl)-N-methylpropanamide |
| 4 | 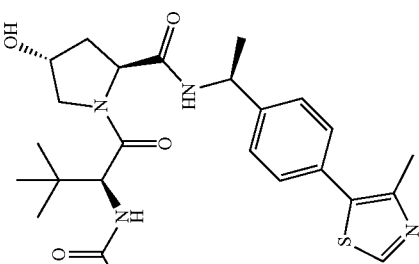 | (2S,4R)-1-((2S)-18-((4-(4-acryloylpiperazin-1-yl)-6-chloro-8-fluoro-7-(3-hydroxynaphthalen-1-yl)quinazolin-2-yl)amino)-2-(tert-butyl)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide |

TABLE 4-continued

Exemplary Bifunctional Compounds of the Ppresent Disclosure

| Ex. No. | Chemical Structure | Compound Name |
|---|---|---|
| 5 | 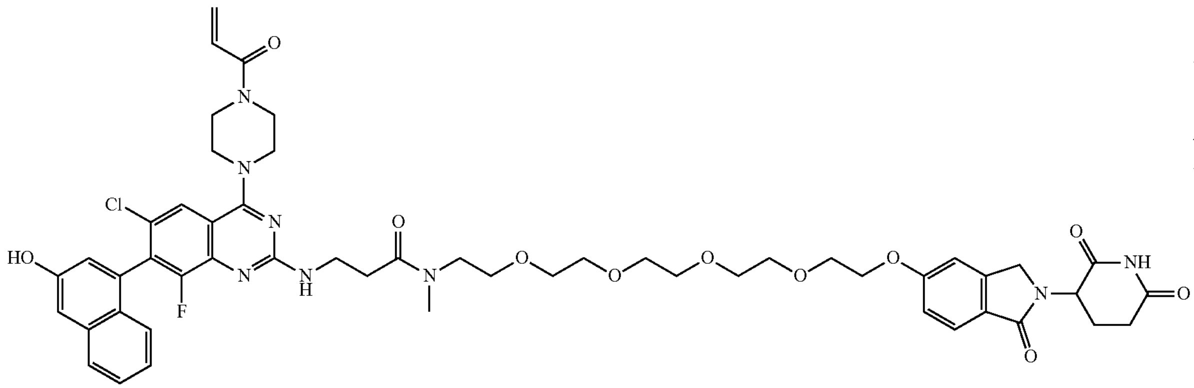 [SMILES: C=CC(=O)N1CCN(c2nc(NCCC(=O)N(C)CCOCCOCCOCCOCCOc3ccc4c(c3)CN(C3CCC(=O)NC3=O)C4=O)nc3c(F)c(-c4cc(O)cc5ccccc45)c(Cl)cc23)CC1] | 3-((4-(4-acryloylpiperazin-1-yl)-6-chloro-8-fluoro-7-(3-hydroxynaphthalen-1-yl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide |
| 6 | 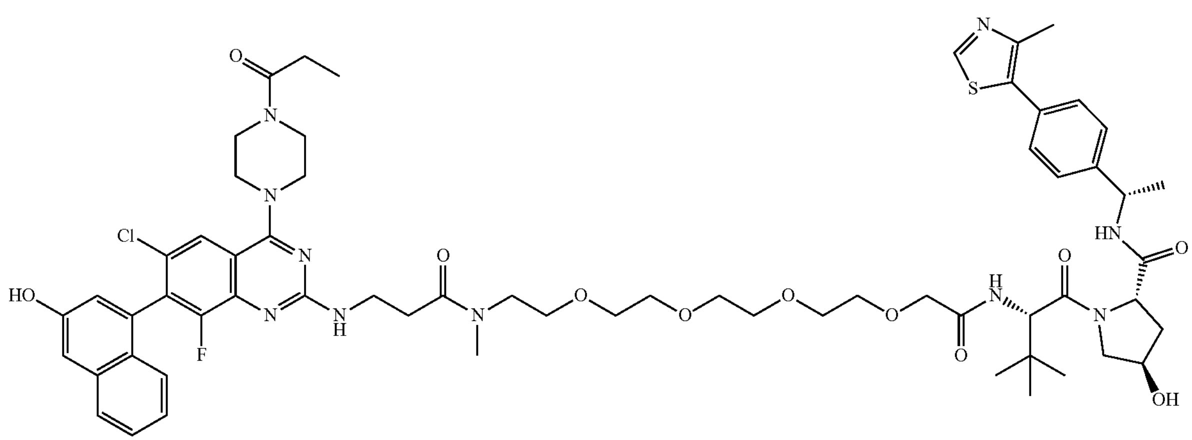 [SMILES: CCC(=O)N1CCN(c2nc(NCCC(=O)N(C)CCOCCOCCOCCOCC(=O)N[C@H](C(=O)N3C[C@H](O)C[C@H]3C(=O)N[C@@H](C)c3ccc(-c4scnc4C)cc3)C(C)(C)C)nc3c(F)c(-c4cc(O)cc5ccccc45)c(Cl)cc23)CC1] | (2S,4R)-1-((2S)-2-(tert-butyl)-21-((6-chloro-8-fluoro-7-(3-hydroxynaphthalen-1-yl)-4-(4-propionylpiperazin-1-yl)quinazolin-2-yl)amino)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide |

TABLE 4-continued

Exemplary Bifunctional Compounds of the Present Disclosure

| Ex. No. | Chemical Structure | Compound Name |
|---|---|---|
| 7 | 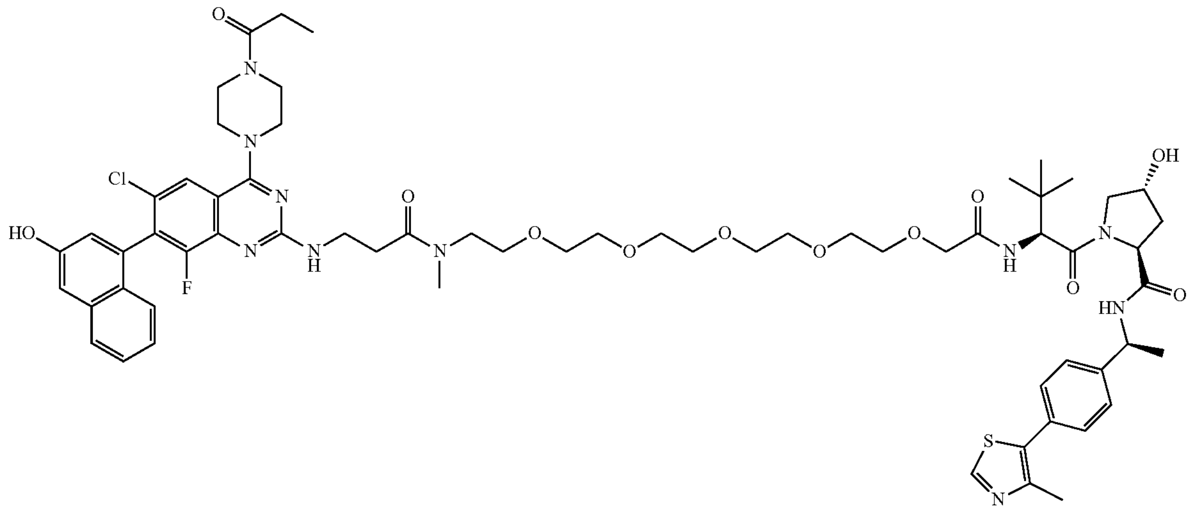 [SMILES: CCC(=O)N1CCN(c2nc(NCCC(=O)N(C)CCOCCOCCOCCOCCOCC(=O)N[C@H](C(=O)N3C[C@H](O)C[C@H]3C(=O)N[C@@H](C)c3ccc(-c4scnc4C)cc3)C(C)(C)C)nc3c(F)c(-c4cc(O)cc5ccccc45)c(Cl)cc23)CC1] | (2S,4R)-1-((2S)-2-(tert-butyl)-24-((6-chloro-8-fluoro-7-(3-hydroxynaphthalen-1-yl)-4-(4-propionylpiperazin-1-yl)quinazolin-2-yl)amino)-21-methyl-4,22-dioxo-6,9,12,15,18-pentaoxa-3,21-diazatetracosanoyl)-4-hydroxy-N-((1S)-1-(4-(4-methyl-5H-114-thiazol-5-yl)phenyl)ethyl)pyrrolidine-2-carboxamide |
| 8 | 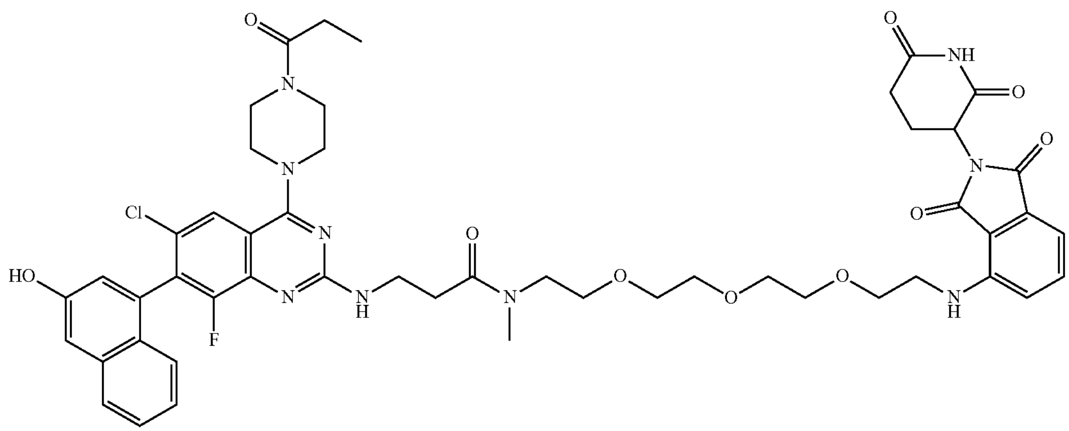 [SMILES: CCC(=O)N1CCN(c2nc(NCCC(=O)N(C)CCOCCOCCOCCNc3cccc4c3C(=O)N(C3CCC(=O)NC3=O)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(2-(2-(2-(2-(2,6-dioxopiperidin-3-yl)-1,3-dioxoisoindolin-4-yl)amino)ethoxy)ethoxy)ethyl)-N-methylpropanamide |

TABLE 4-continued

Exemplary Bifunctional Compounds of the Ppresent Disclosure

| Ex. No. | Chemical Structure | Compound Name |
|---|---|---|
| 9 | 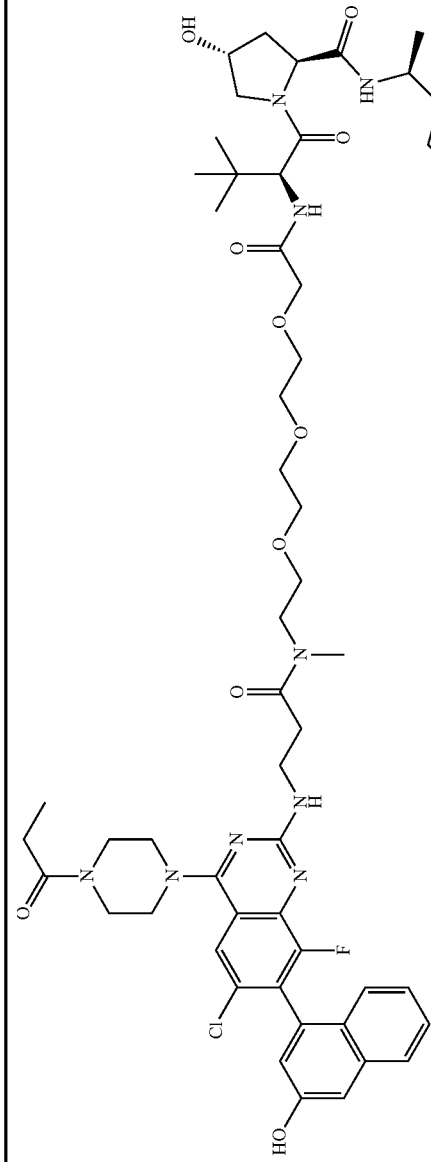 | (2S,4R)-1-((S)-2-(tert-butyl)-18-(((6-chloro-8-fluoro-7-(3-hydroxynaphthalen-1-yl)-4-(4-propionylpiperazin-1-yl)-5H-3,12-quinazolin-2-yl)amino)-15-methyl-4,16-dioxa-3,15-diazaoctadecanoyl)-4-hydroxy-N-((S)-1-(4-(4-methyl-3,12-thiazol-5-yl)phenyl)ethyl)pyrrolidine-2-carboxamide |
| 10 | 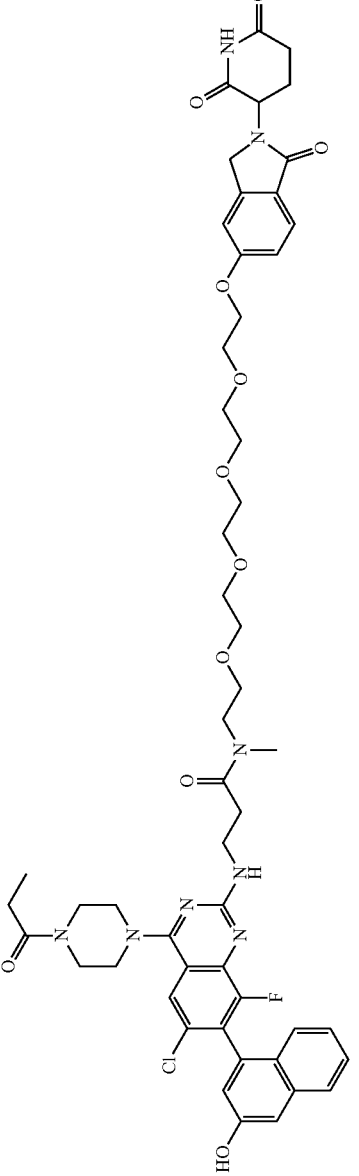 | 3-((6-chloro-8-fluoro-7-(3-hydroxynaphthalen-1-yl)-4-(4-propionylpiperazin-1-yl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide |

TABLE 5

Target Protein Degradation via Exemplary Bifunctional Compounds from Table 4

| Ex. No. | Mol Weight | MH+ | H2030 Degradation at 0.3 uM* | H2030 Degradation at 1 uM* | H2030 Degradation at 3 uM* |
|---|---|---|---|---|---|
| 1 | 1223.84 | 1223.8/1225.8 | C | A | A |
| 2 | 1267.90 | 1267.8/1269.8 | C | A | A |
| 3 | 994.46 | 994.6/996.6 | C | B | B |
| 4 | 1179.79 | 1179.75/1181.75 | C | B | B |
| 5 | 1025.52 | 1025.63/1027.63 | C | B | B |
| 6 | 1225.86 | 1225.81/1227.81 | C | C | C |
| 7 | 1269.91 | 1269.80/1271.80 | C | C | C |
| 8 | 996.48 | 996.62/998.62 | C | C | C |
| 9 | 1181.81 | 1181.80/1183.80 | C | C | C |
| 10 | 1027.53 | 1027.65/1029.65 | C | C | C |

*Percent Degradation: C < 25; 25 ≤ B < 50; A ≥ 50

TABLE 6

Compounds Prepared by Schemes 1 and 2

| Ex. No. | Structure | Compound Name | Synthetic Scheme |
|---|---|---|---|
| 11 | 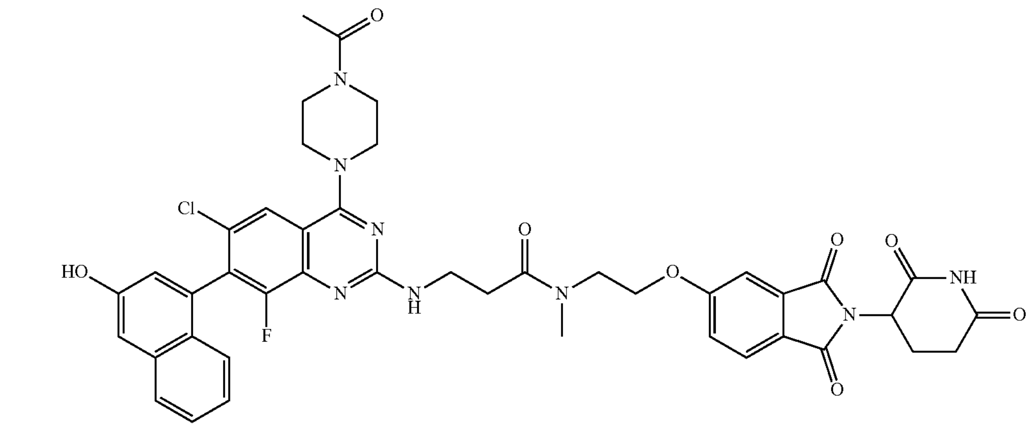 [SMILES: CC(=O)N1CCN(c2nc(NCCC(=O)N(C)CCOc3ccc4c(c3)C(=O)N(C3CCC(=O)NC3=O)C4=O)nc3c(F)c(-c4cc(O)cc5ccccc45)c(Cl)cc23)CC1] | 3-((4-(4-acetylpiperazin-1-yl)-6-chloro-8-fluoro-7-(3-hydroxynaphthalen-1-yl)quinazolin-2-yl)amino)-N-(2-((2-(2,6-dioxopiperidin-3-yl)-1,3-dioxoisoindolin-5-yl)oxy)ethyl)-N-methylpropanamide | 1 |
| 12 | 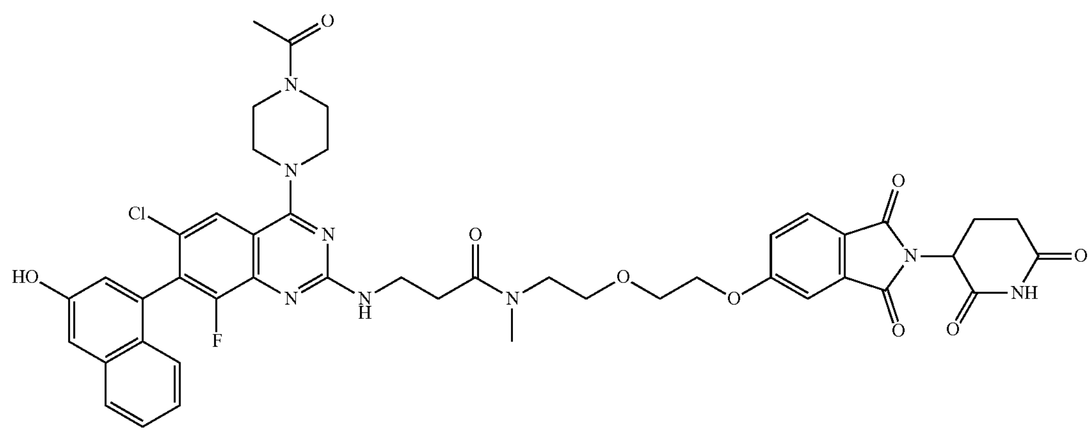 [SMILES: CC(=O)N1CCN(c2nc(NCCC(=O)N(C)CCOCCOc3ccc4c(c3)C(=O)N(C3CCC(=O)NC3=O)C4=O)nc3c(F)c(-c4cc(O)cc5ccccc45)c(Cl)cc23)CC1] | 3-((4-(4-acetylpiperazin-1-yl)-6-chloro-8-fluoro-7-(3-hydroxynaphthalen-1-yl)quinazolin-2-yl)amino)-N-(2-(2-((2-(2,6-dioxopiperidin-3-yl)-1,3-dioxoisoindolin-5-yl)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 13 | 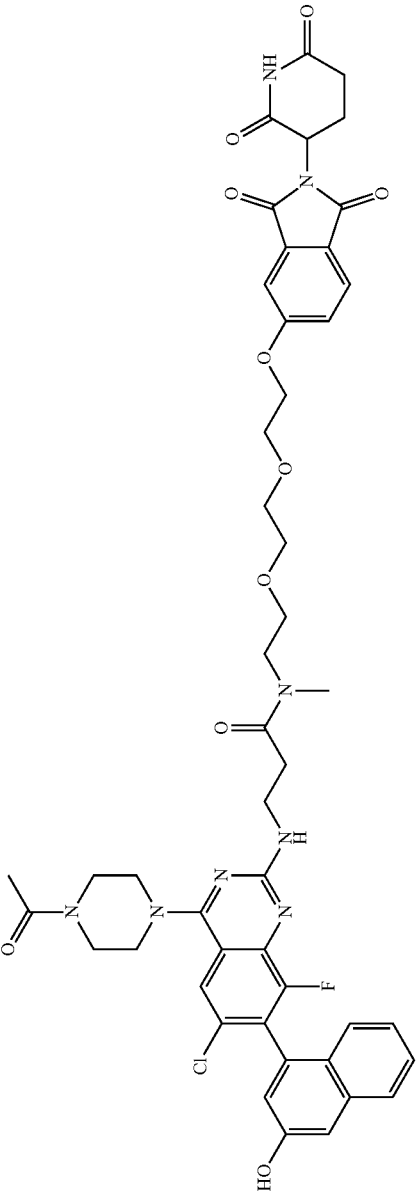 | 3-((4-(4-acetylpiperazin-1-yl)-6-chloro-8-fluoro-7-(3-hydroxynaphthalen-1-yl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |
| 14 | 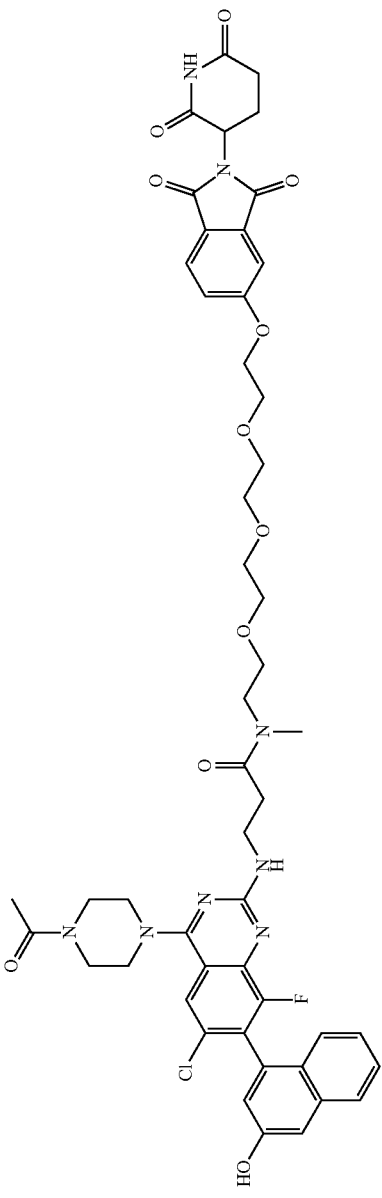 | 3-((4-(4-acetylpiperazin-1-yl)-6-chloro-8-fluoro-7-(3-hydroxynaphthalen-1-yl)quinazolin-2-yl)amino)-N-(2-(2-((2-(2,6-dioxopiperidin-3-yl)-1,3-dioxoisoindolin-5-yl)oxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 15 | 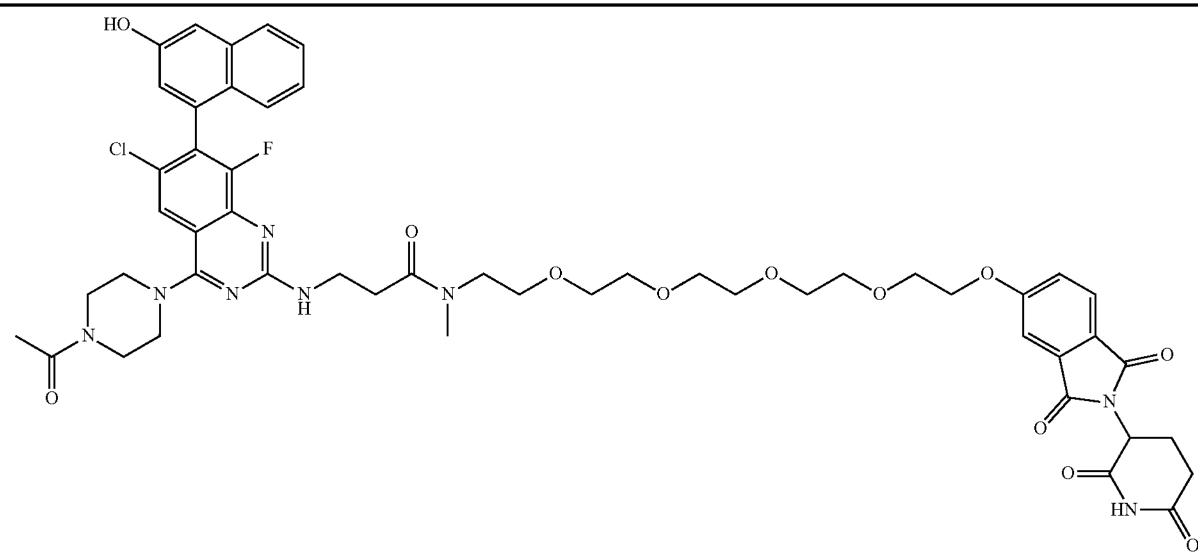 | 3-((4-(4-acetylpiperazin-1-yl)-6-chloro-8-fluoro-7-(3-hydroxynaphthalen-1-yl)quinazolin-2-yl)amino)-N-(2-(2-(2,6-dioxopiperidin-3-yl)-1,3-dioxoisoindolin-5-yl)oxy)-3,6,9,12-tetraoxatetradecyl)-N-methylpropanamide | 1 |
| 16 | 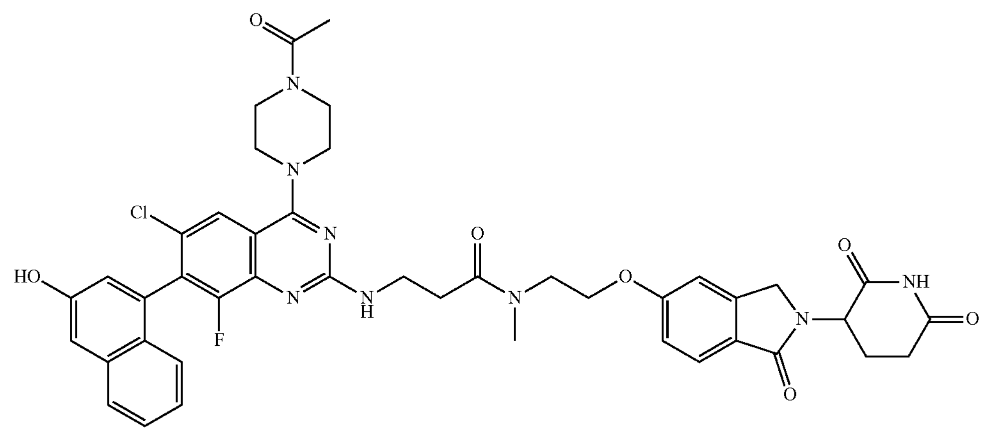 [SMILES: CC(=O)N1CCN(c2nc(NCCC(=O)N(C)CCOc3ccc4c(c3)CN(C3CCC(=O)NC3=O)C4=O)nc3c(F)c(-c4cc(O)cc5ccccc45)c(Cl)cc23)CC1] | 3-((4-(4-acetylpiperazin-1-yl)-6-chloro-8-fluoro-7-(3-hydroxynaphthalen-1-yl)quinazolin-2-yl)amino)-N-(2-((2-(2,6-dioxopiperidin-3-yl)-1-oxoisoindolin-5-yl)oxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 17 | 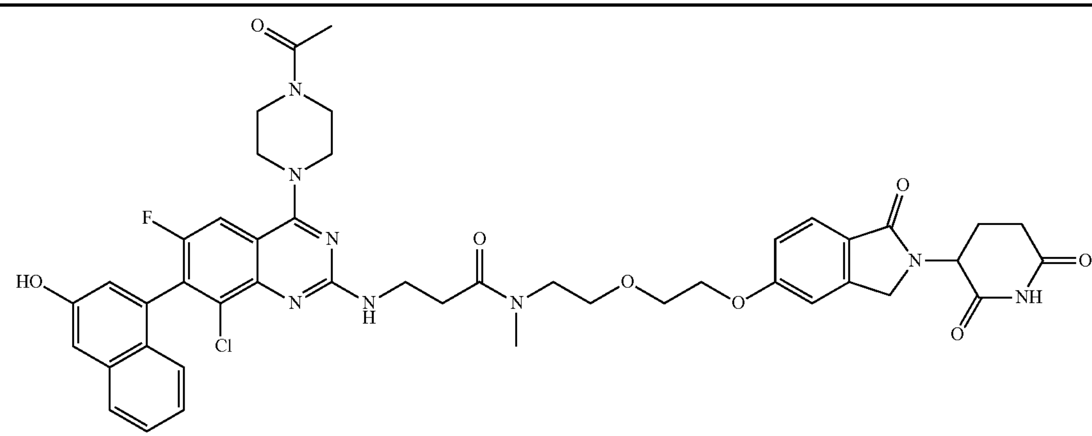 | 3-((4-(4-acetylpiperazin-1-yl)-8-chloro-6-fluoro-7-(3-hydroxynaphthalen-1-yl)quinazolin-2-yl)amino)-N-(2-((2-(2,6-dioxopiperidin-3-yl)-1-oxoisoindolin-5-yl)oxy)ethoxy)ethyl)-N-methylpropanamide | 1 |
| 18 | 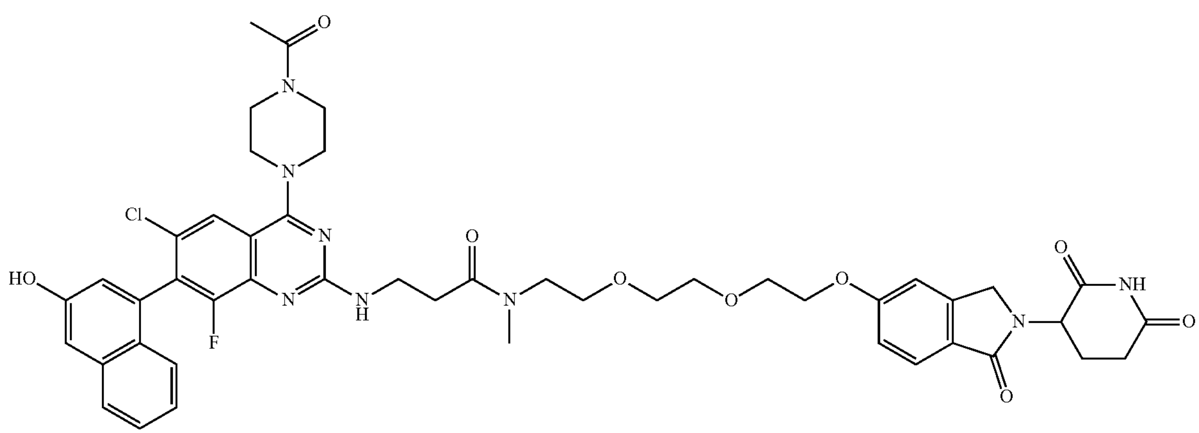 [SMILES: CC(=O)N1CCN(c2nc(NCCC(=O)N(C)CCOCCOCCOc3ccc4c(c3)CN(C3CCC(=O)NC3=O)C4=O)nc3c(F)c(-c4cc(O)cc5ccccc45)c(Cl)cc23)CC1] | 3-((4-(4-acetylpiperazin-1-yl)-6-chloro-8-fluoro-7-(3-hydroxynaphthalen-1-yl)quinazolin-2-yl)amino)-N-(2-(2-((2-(2,6-dioxopiperidin-3-yl)-1-oxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 19 | 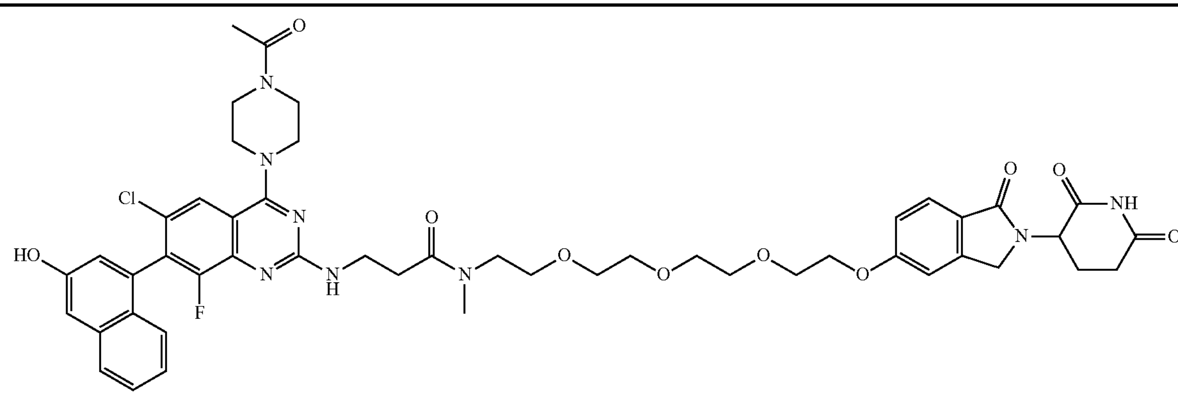 | 3-((4-(4-acetylpiperazin-1-yl)-6-chloro-8-fluoro-7-(3-hydroxynaphthalen-1-yl)quinazolin-2-yl)amino)-N-(2-(2-(2-((2-(2,6-dioxopiperidin-3-yl)-1-oxoisoindolin-5-yl)oxy)ethoxy)ethoxy)ethyl)-N-methylpropanamide | 1 |
| 20 | 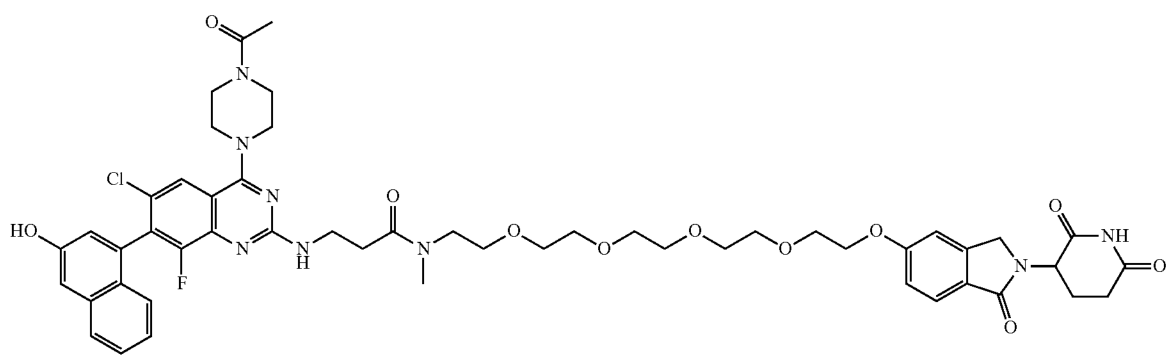 [SMILES: CC(=O)N1CCN(c2nc(NCCC(=O)N(C)CCOCCOCCOCCOCCOc3ccc4c(c3)CN(C3CCC(=O)NC3=O)C4=O)nc3c(F)c(-c4cc(O)cc5ccccc45)c(Cl)cc23)CC1] | 3-((4-(4-acetylpiperazin-1-yl)-6-chloro-8-fluoro-7-(3-hydroxynaphthalen-1-yl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 21 | 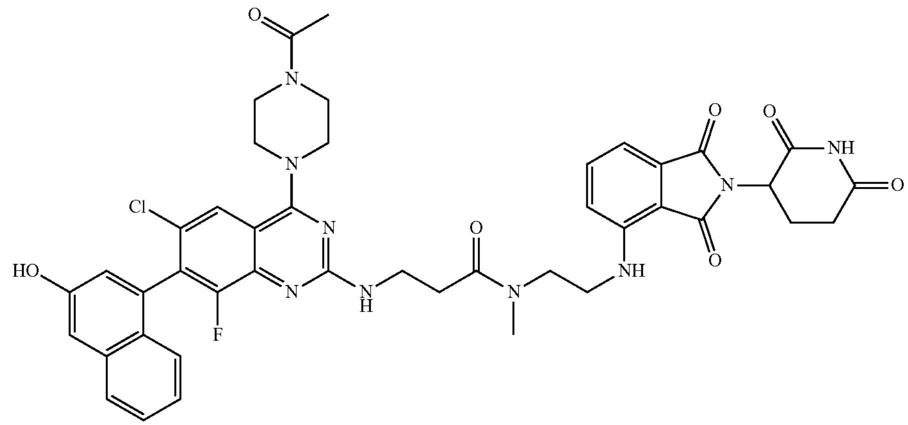 [SMILES: CC(=O)N1CCN(c2nc(NCCC(=O)N(C)CCNc3cccc4c3C(=O)N(C3CCC(=O)NC3=O)C4=O)nc3c(F)c(-c4cc(O)cc5ccccc45)c(Cl)cc23)CC1] | 3-((4-(4-acetylpiperazin-1-yl)-6-chloro-8-fluoro-7-(3-hydroxynaphthalen-1-yl)quinazolin-2-yl)amino)-N-(2-((2-(2,6-dioxopiperidin-3-yl)-1,3-dioxoisoindolin-4-yl)amino)ethyl)-N-methylpropanamide | 1 |
| 22 | 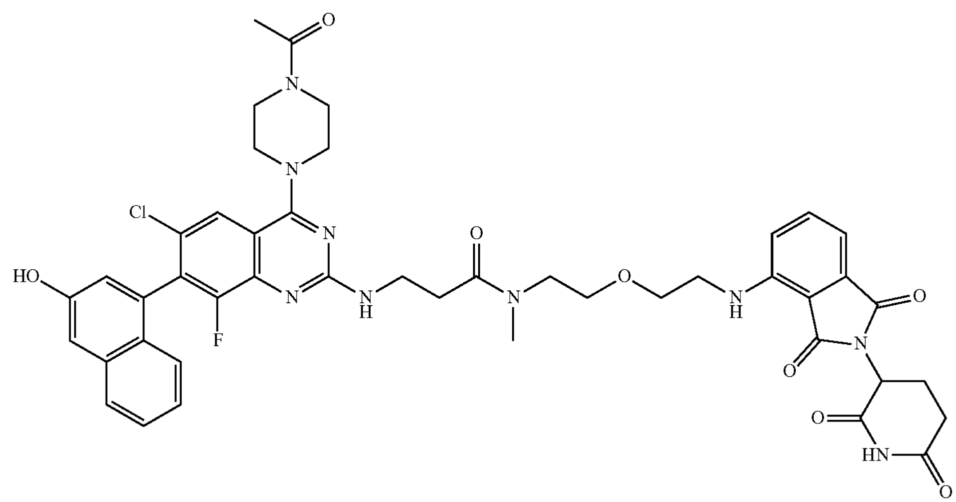 [SMILES: CC(=O)N1CCN(c2nc(NCCC(=O)N(C)CCOCCNc3cccc4c3C(=O)N(C3CCC(=O)NC3=O)C4=O)nc3c(F)c(-c4cc(O)cc5ccccc45)c(Cl)cc23)CC1] | 3-((4-(4-acetylpiperazin-1-yl)-6-chloro-8-fluoro-7-(3-hydroxynaphthalen-1-yl)quinazolin-2-yl)amino)-N-(2-(2-((2-(2,6-dioxopiperidin-3-yl)-1,3-dioxoisoindolin-4-yl)amino)ethoxy)ethyl)-N-methylpropanamide | 1 |

TABLE 6-continued
Compounds Prepared by Schemes 1 and 2
| Ex. No. | Structure | Compound Name | Synthetic Scheme |
|---|---|---|---|
| 23 | 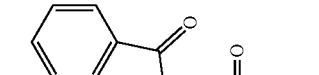 | 3-((4-(4-acetylpiperazin-1-yl)-6-chloro-8-fluoro-7-(3-hydroxynaphthalen-1-yl)quinazolin-2-yl)amino)-N-(2-(2-(2-(2-(2,6-dioxopiperidin-3-yl)-1,3-dioxoisoindolin-4-yl)amino)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 24 | 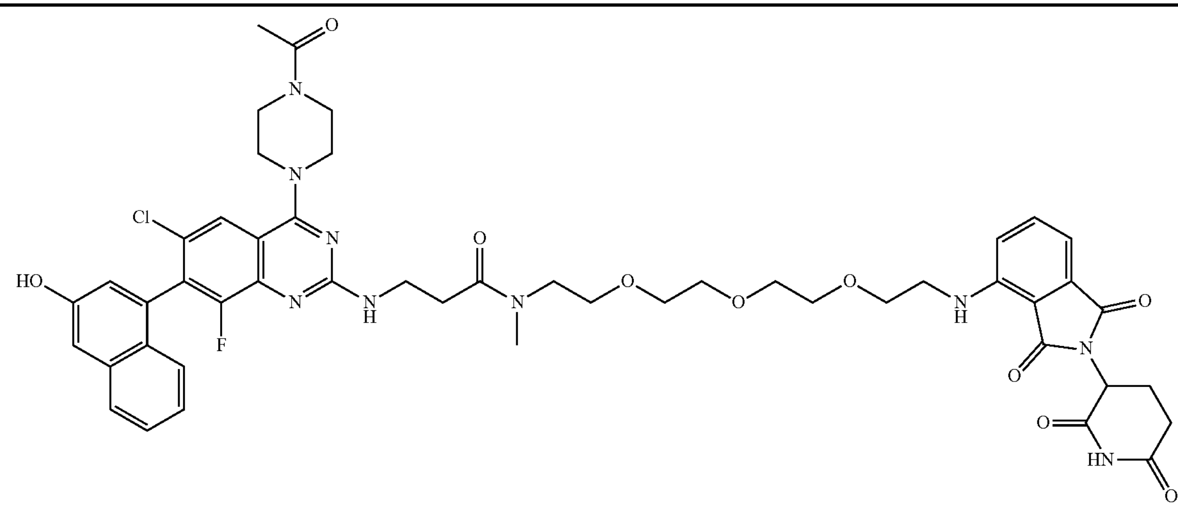 | 3-((4-(4-acetylpiperazin-1-yl)-6-chloro-8-fluoro-7-(3-hydroxynaphthalen-1-yl)quinazolin-2-yl)amino)-N-(2-(2-(2-((2-(2,6-dioxopiperidin-3-yl)-1,3-dioxoisoindolin-4-yl)amino)ethoxy)ethoxy)ethoxy)ethyl)-N-methylpropanamide | 1 |
| 25 | 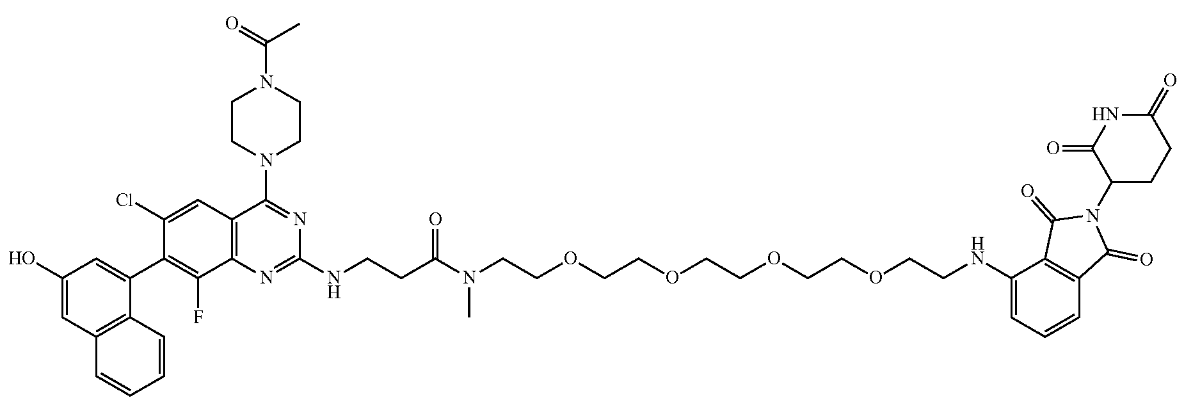 [SMILES: CC(=O)N1CCN(c2nc(NCCC(=O)N(C)CCOCCOCCOCCOCCNc3cccc4c3C(=O)N(C3CCC(=O)NC3=O)C4=O)nc3c(F)c(-c4cc(O)cc5ccccc45)c(Cl)cc23)CC1] | 3-((4-(4-acetylpiperazin-1-yl)-6-chloro-8-fluoro-7-(3-hydroxynaphthalen-1-yl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 26 | 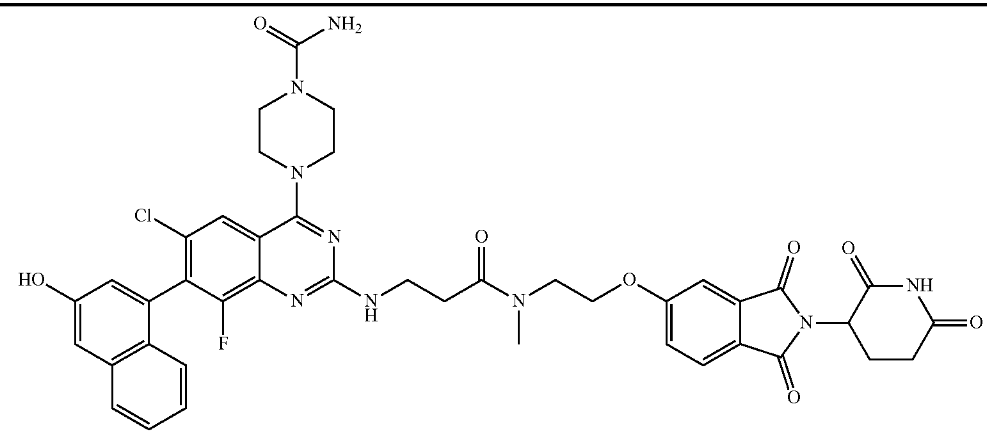 | 4-(6-chloro-2-((3-((2-((2-(2,6-dioxopiperidin-3-yl)-1,3-dioxoisoindolin-5-yl)oxy)ethyl)(methyl)amino)-3-oxopropyl)amino)-8-fluoro-7-(3-hydroxynaphthalen-1-yl)quinazolin-4-yl)piperazine-1-carboxamide | 1 |
| 27 | 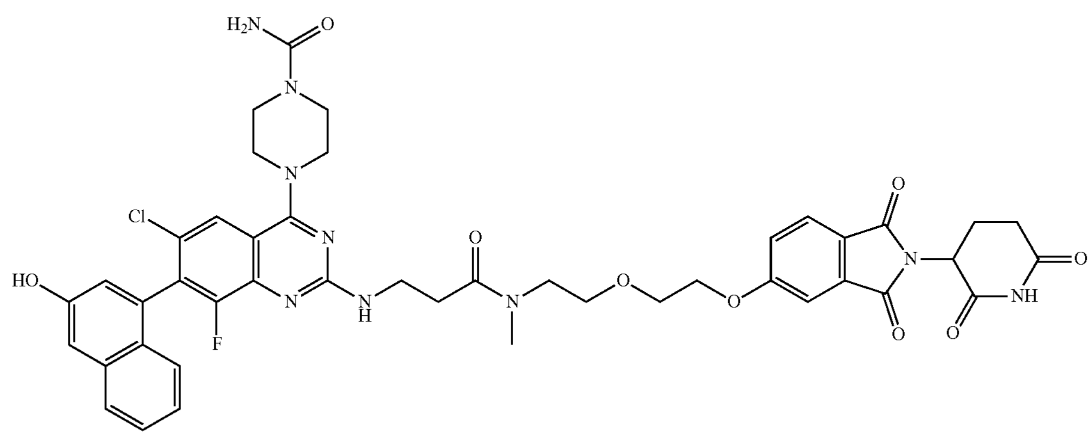 [SMILES: CN(CCOCCOc1ccc2c(c1)C(=O)N(C1CCC(=O)NC1=O)C2=O)C(=O)CCNc1nc(N2CCN(C(N)=O)CC2)c2cc(Cl)c(-c3cc(O)cc4ccccc34)c(F)c2n1] | 4-(6-chloro-2-((3-(3-(2-((2-(2,6-dioxopiperidin-3-yl)-1,3-dioxoisoindolin-5-yl)oxy)ethoxy)ethyl)(methyl)amino)-3-oxopropyl)amino)-8-fluoro-7-(3-hydroxynaphthalen-1-yl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 28 | 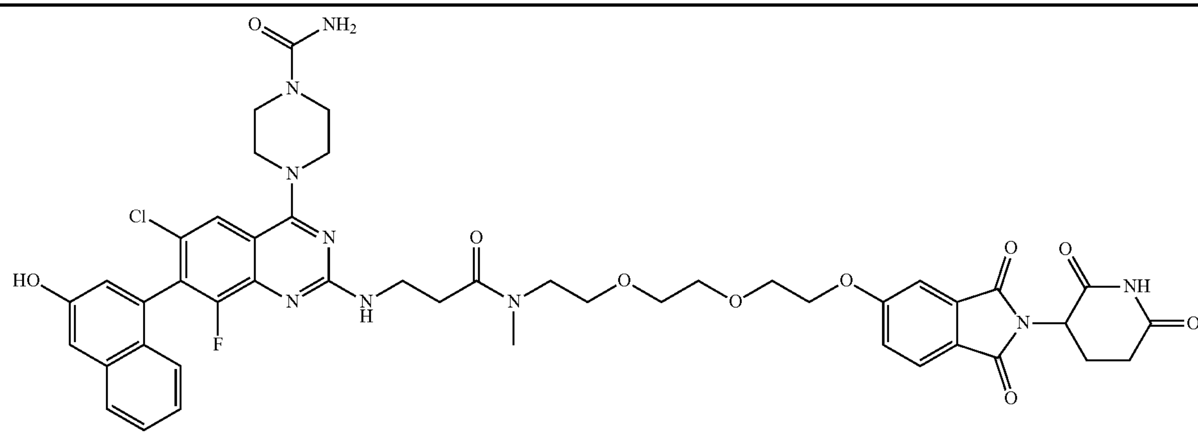 | 4-(6-chloro-2-((3-((2-(2-(2-(2-(2,6-dioxopiperidin-3-yl)-1,3-dioxoisoindolin-5-yl)oxy)ethoxy)ethoxy)ethy)(methyl)amino)-3-oxopropyl)amino)-8-fluoro-7-(3-hydroxynaphthalen-1-yl)quinazolin-4-yl)piperazine-1-carboxamide | 1 |
| 29 | 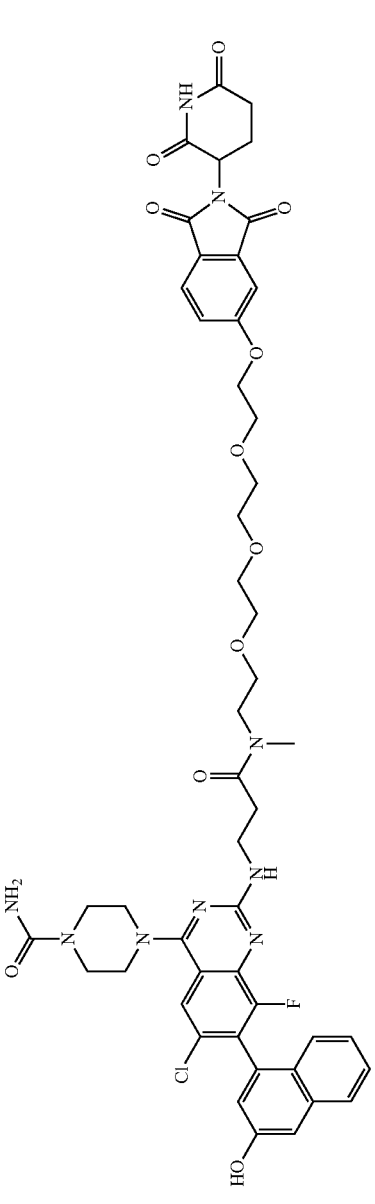 | 4-(6-chloro-2-((1-((2-(2,6-dioxopiperidin-3-yl)-1,3-dioxoisoindolin-5-yl)oxy)-12-methyl-13-oxo-3,6,9-trioxa-12-azapentadecan-15-yl)amino)-8-fluoro-7-(3-hydroxynaphthalen-1-yl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 30 | 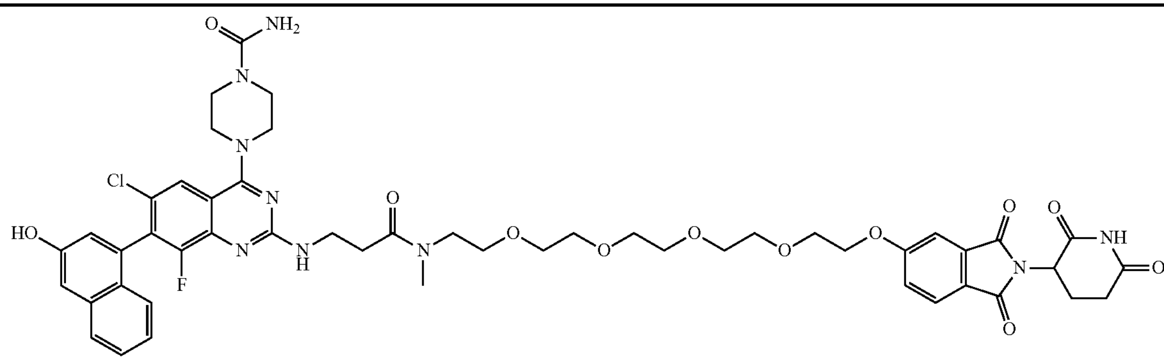 | 4-(6-chloro-2-((1-((2-(2,6-dioxopiperidin-3-yl)-1,3-dioxoisoindolin-5-yl)oxy)-15-methyl-16-oxo-3,6,9,12-tetraoxa-15-azaoctadecan-18-yl)amino)-8-fluoro-7-(3-hydroxynaphthalen-1-yl)quinazolin-4-yl)piperazine-1-carboxamide | 1 |
| 31 | 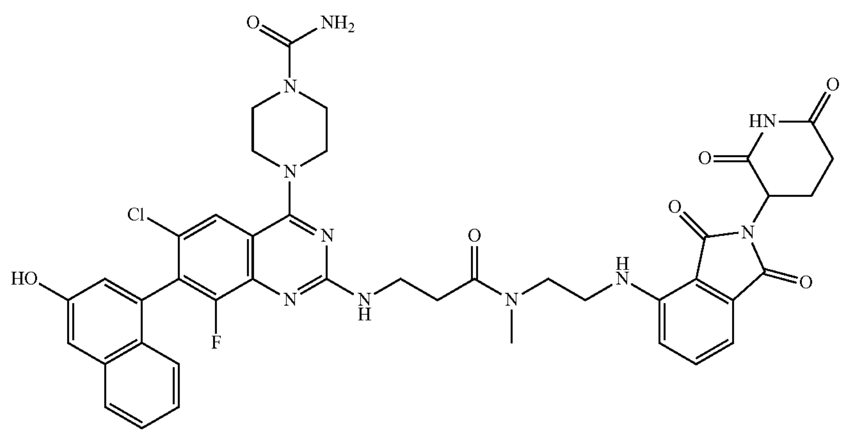 [SMILES: CN(CCNc1cccc2c1C(=O)N(C1CCC(=O)NC1=O)C2=O)C(=O)CCNc1nc(N2CCN(C(N)=O)CC2)c2cc(Cl)c(-c3cc(O)cc4ccccc34)c(F)c2n1] | 4-(6-chloro-2-((3-((2-((2-(2,6-dioxopiperidin-3-yl)-1,3-dioxoisoindolin-4-yl)amino)ethyl)(methyl)amino)-3-oxopropyl)amino)-8-fluoro-7-(3-hydroxynaphthalen-1-yl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 32 | 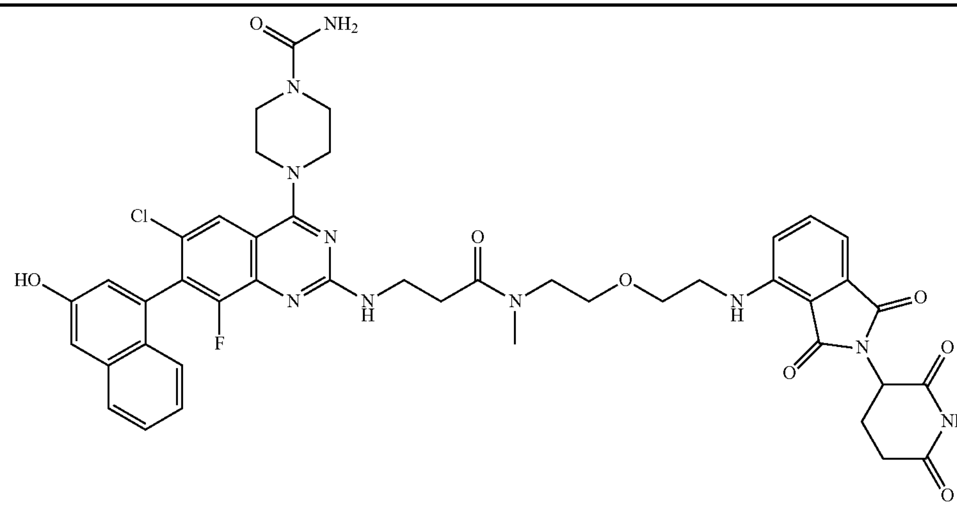 | 4-(6-chloro-2-((3-((2-(2-(2-(2,6-dioxopiperidin-3-yl)-1,3-dioxoisoindolin-4-yl)amino)ethoxy)ethyl)(methyl)amino)-3-oxopropyl)amino)-8-fluoro-7-(3-hydroxynaphthalen-1-yl)quinazolin-4-yl)piperazine-1-carboxamide | 1 |
| 33 | 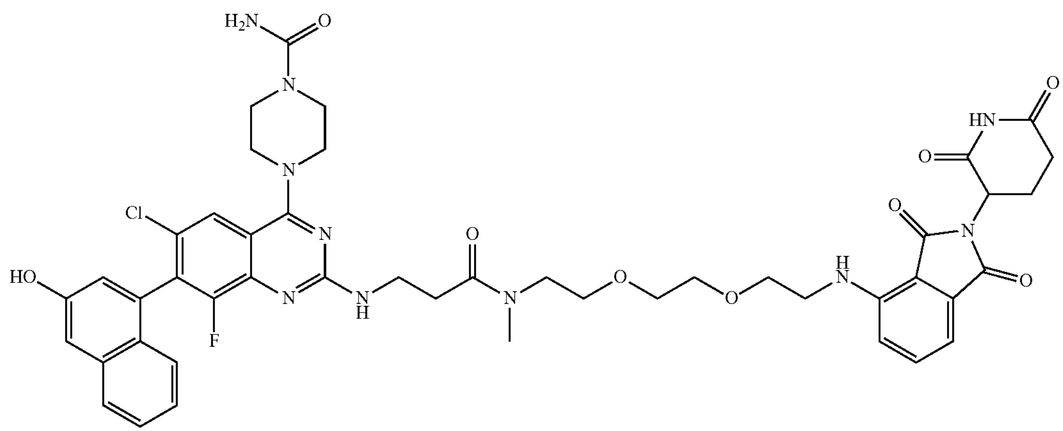 [SMILES: CN(CCOCCOCCNc1cccc2c1C(=O)N(C1CCC(=O)NC1=O)C2=O)C(=O)CCNc1nc(N2CCN(C(N)=O)CC2)c2cc(Cl)c(-c3cc(O)cc4ccccc34)c(F)c2n1] | 4-(6-chloro-2-((3-((2-(2-(2-(2,6-dioxopiperidin-3-yl)-1,3-dioxoisoindolin-4-yl)amino)ethoxy)ethyl)(methyl)amino)-3-oxopropyl)amino)-8-fluoro-7-(3-hydroxynaphthalen-1-yl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 34 | 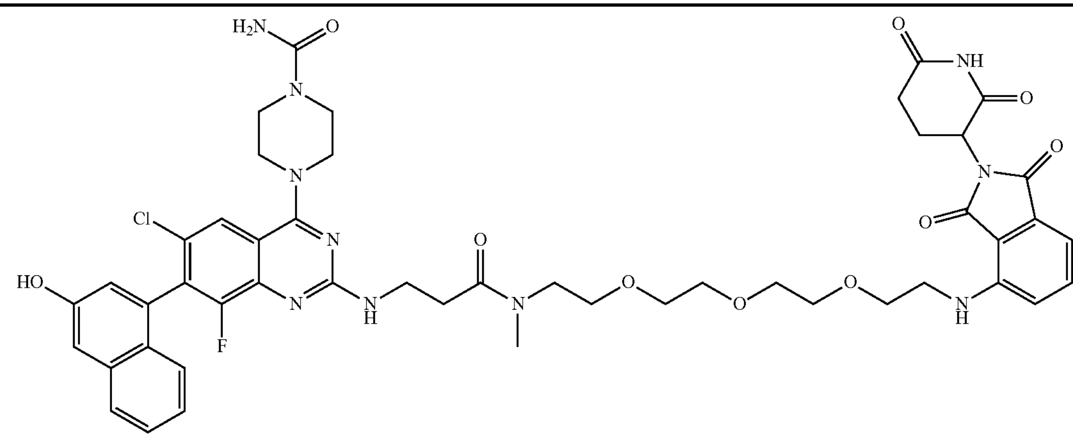 | 4-(6-chloro-2-((1-((2-(2,6-dioxopiperidin-3-yl)-1,3-dioxoisoindolin-4-yl)amino)-12-methyl-13-oxo-3,6,9-trioxa-12-azapentadecan-15-yl)amino)-8-fluoro-7-(3-hydroxynaphthalen-1-yl)quinazolin-4-yl)piperazine-1-carboxamide | 1 |
| 35 | 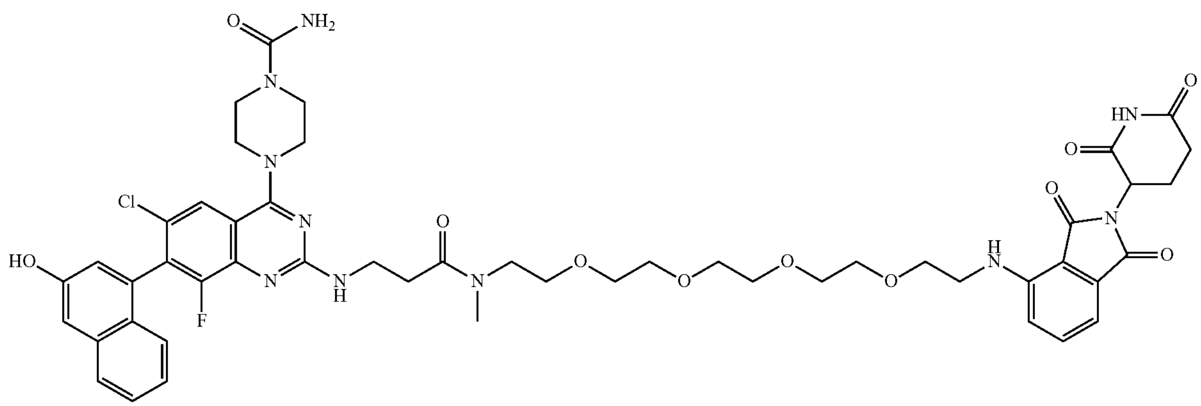 [SMILES: CN(CCOCCOCCOCCOCCNc1cccc2c1C(=O)N(C1CCC(=O)NC1=O)C2=O)C(=O)CCNc1nc(N2CCN(C(N)=O)CC2)c2cc(Cl)c(-c3cc(O)cc4ccccc34)c(F)c2n1] | 4-(6-chloro-2-((1-((2-(2,6-dioxopiperidin-3-yl)-1,3-dioxoisoindolin-4-yl)amino)-15-methyl-16-oxo-3,6,9,12-tetraoxa-15-azaoctadecan-18-yl)amino)-8-fluoro-7-(3-hydroxynaphthalen-1-yl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 36 | 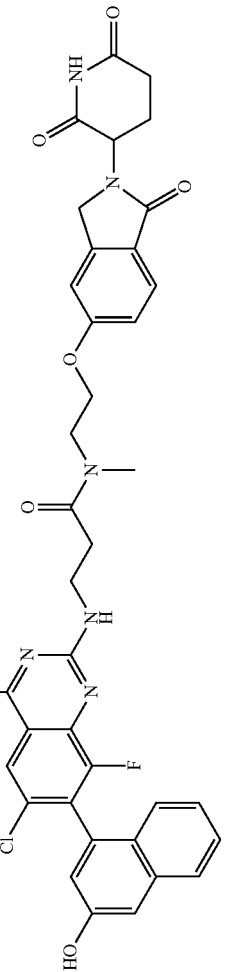 | 4-(6-chloro-2-((3-((2-((2-(2,6-dioxopiperidin-3-yl)-1-oxoisoindolin-5-yl)oxy)ethyl)(methyl)amino)-3-oxopropyl)amino)-8-fluoro-7-(3-hydroxynaphthalen-1-yl)quinazolin-4-yl)piperazine-1-carboxamide | 1 |
| 37 | 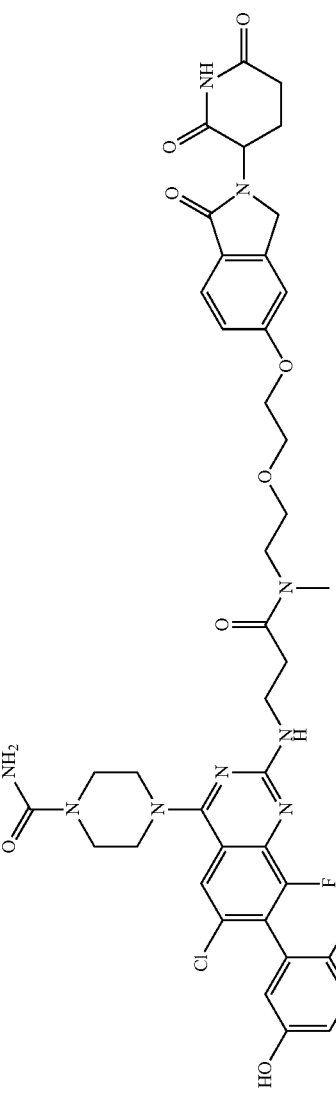 | 4-(6-chloro-2-((3-((2-(2-(2-(2,6-dioxopiperidin-3-yl)-1-oxoisoindolin-5-yl)oxy)ethoxy)ethyl)(methyl)amino)-3-oxopropyl)amino)-8-fluoro-7-(3-hydroxynaphthalen-1-yl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 38 | 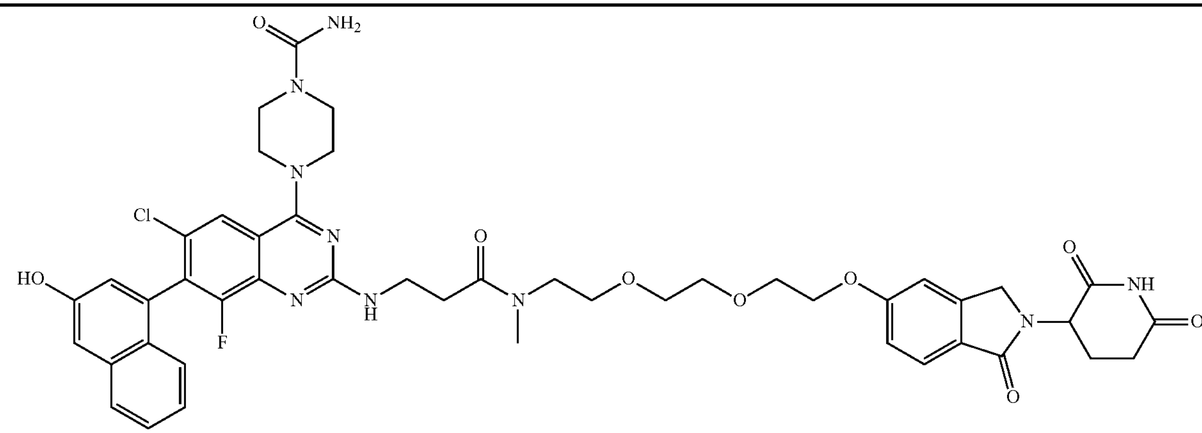 | 4-(6-chloro-2-((3-((2-(2-(2-((2-(2,6-dioxopiperidin-3-yl)-1-oxoisoindolin-5-yl)oxy)ethoxy)ethyl)(methyl)amino)-3-oxopropyl)amino)-8-fluoro-7-(3-hydroxynaphthalen-1-yl)quinazolin-4-yl)piperazine-1-carboxamide | 1 |
| 39 | 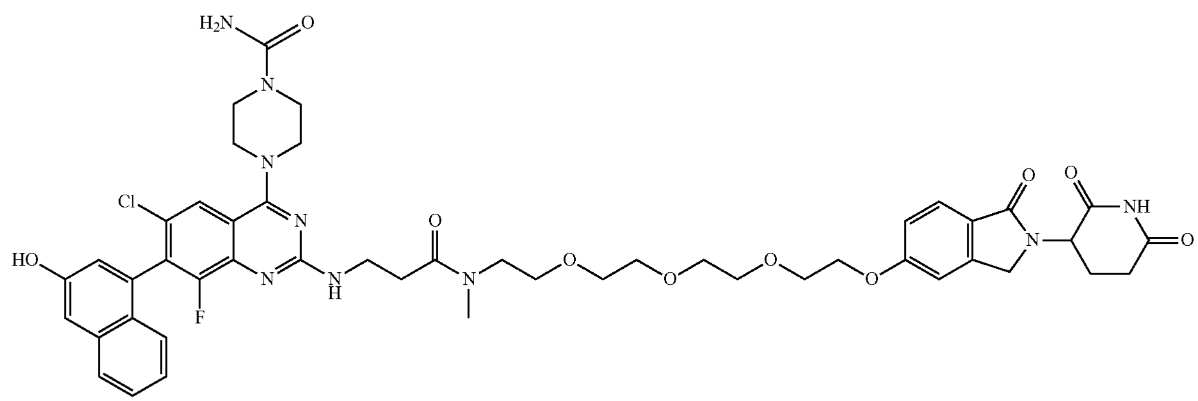 [SMILES: CN(CCOCCOCCOCCOc1ccc2c(c1)CN(C1CCC(=O)NC1=O)C2=O)C(=O)CCNc1nc(N2CCN(C(N)=O)CC2)c2cc(Cl)c(-c3cc(O)cc4ccccc34)c(F)c2n1] | 4-(6-chloro-2-((1-((2-(2,6-dioxopiperidin-3-yl)-1-oxoisoindolin-5-yl)oxy)-12-methyl-13-oxo-3,6,9-trioxa-12-azapentadecan-15-yl)amino)-8-fluoro-7-(3-hydroxynaphthalen-1-yl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 40 | 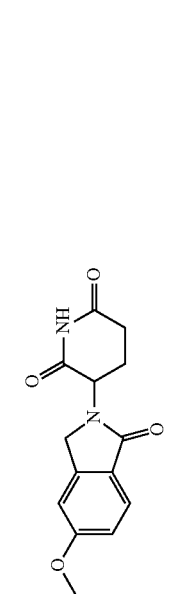 | 4-(6-chloro-2-((1-((2-(2,6-dioxopiperidin-3-yl)-1-oxoisoindolin-5-yl)oxy)-15-methyl-16-oxo-3,6,9,12-tetraoxa-15-azaoctadecan-18-yl)amino)-8-fluoro-7-(3-hydroxynaphthalen-1-yl)quinazolin-4-yl)piperazine-1-carboxamide | 1 |
| 41 | 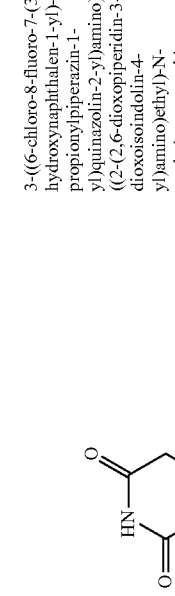 | 3-((6-chloro-8-fluoro-7-(3-hydroxynaphthalen-1-yl)-4-(4-propionylpiperazin-1-yl)quinazolin-2-yl)amino)-N-(2-((2-(2,6-dioxopiperidin-3-yl)-1,3-dioxoisoindolin-4-yl)amino)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 42 | 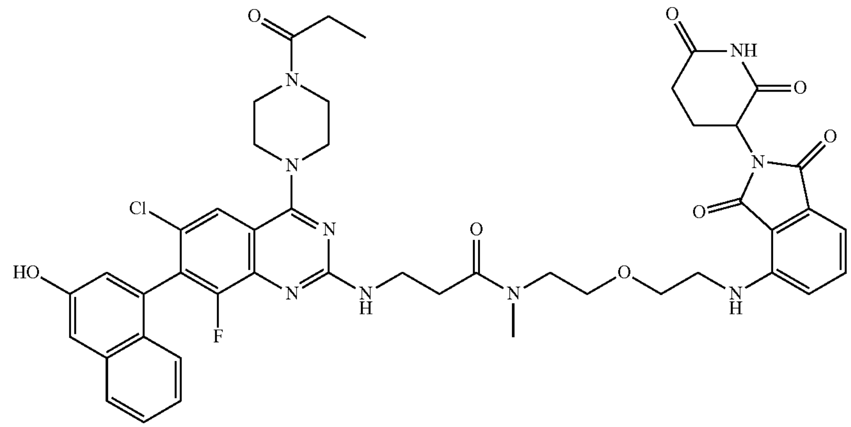 [SMILES: CCC(=O)N1CCN(c2nc(NCCC(=O)N(C)CCOCCNc3cccc4c3C(=O)N(C3CCC(=O)NC3=O)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(2-((2-(2,6-dioxopiperidin-3-yl)-1,3-dioxoisoindolin-4-yl)amino)ethoxy)ethyl)-N-methylpropanamide | 1 |
| 43 | 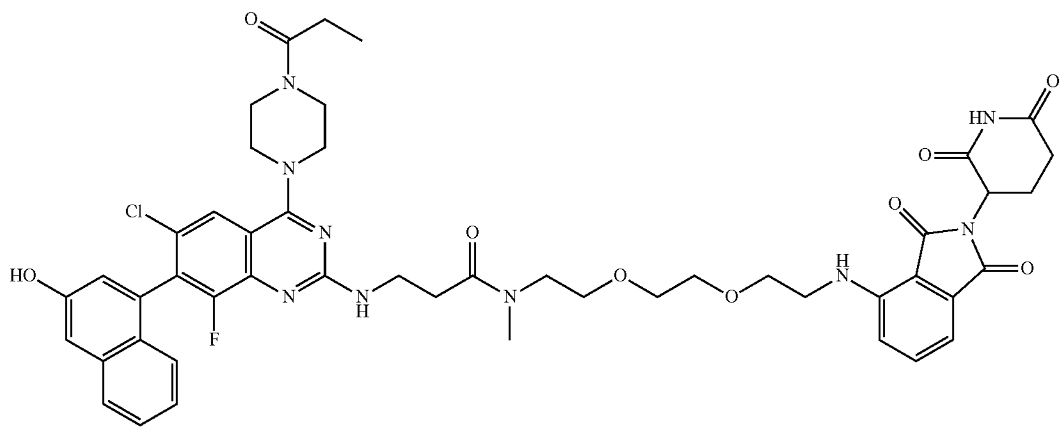 [SMILES: CCC(=O)N1CCN(c2nc(NCCC(=O)N(C)CCOCCOCCNc3cccc4c3C(=O)N(C3CCC(=O)NC3=O)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(2-(2-(2-(2,6-dioxopiperidin-3-yl)-1,3-dioxoisoindolin-4-yl)amino)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 44 | 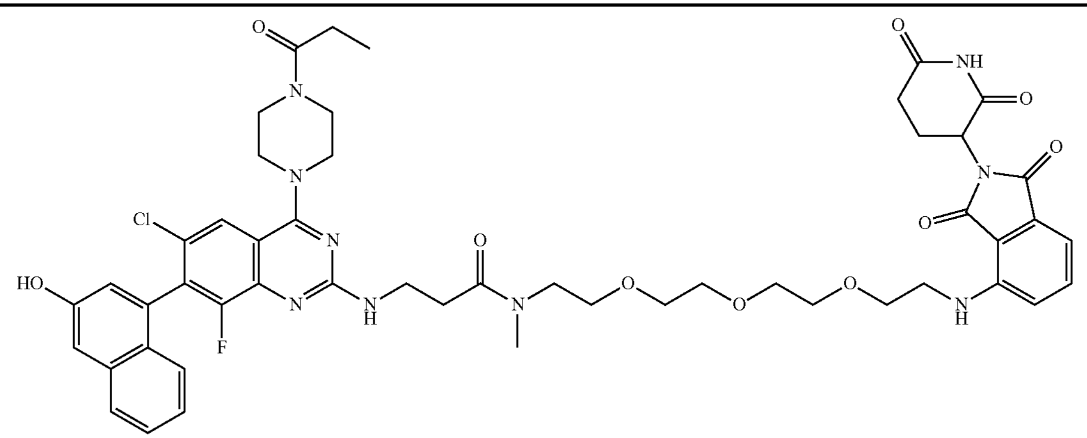 | 3-((6-chloro-8-fluoro-7-(3-hydroxynaphthalen-1-yl)-4-(4-propionylpiperazin-1-yl)quinazolin-2-yl)amino)-N-(2-(2-(2-((2-(2,6-dioxopiperidin-3-yl)-1,3-dioxoisoindolin-4-yl)amino)ethoxy)ethoxy)ethoxy)ethyl)-N-methylpropanamide | 1 |
| 45 | 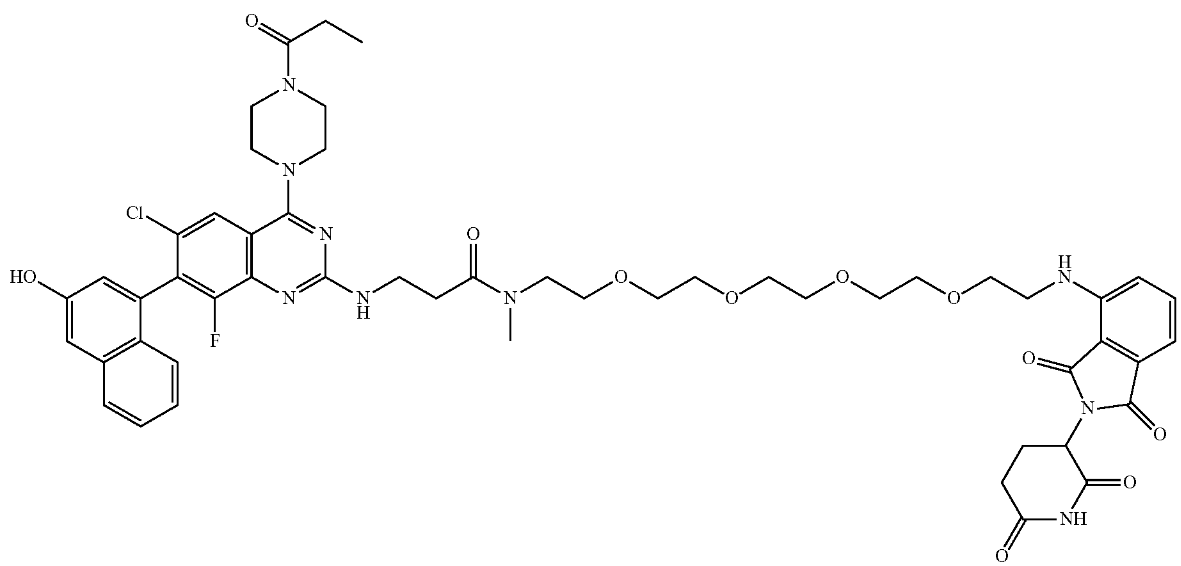 [SMILES: CCC(=O)N1CCN(c2nc(NCCC(=O)N(C)CCOCCOCCOCCOCCNc3cccc4c3C(=O)N(C3CCC(=O)NC3=O)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 46 | 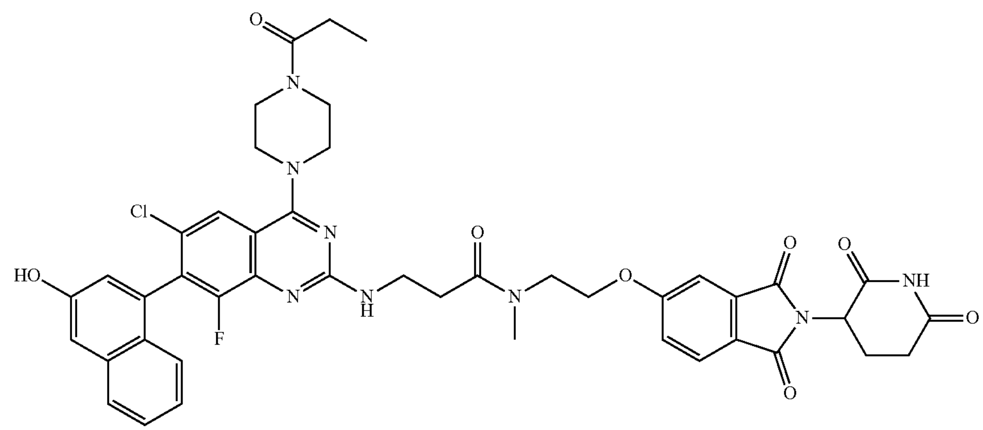 [SMILES: CCC(=O)N1CCN(c2nc(NCCC(=O)N(C)CCOc3ccc4c(c3)C(=O)N(C3CCC(=O)NC3=O)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(2-((2-(2,6-dioxopiperidin-3-yl)-1,3-dioxoisoindolin-5-yl)oxy)ethyl)-N-methylpropanamide | 1 |
| 47 | 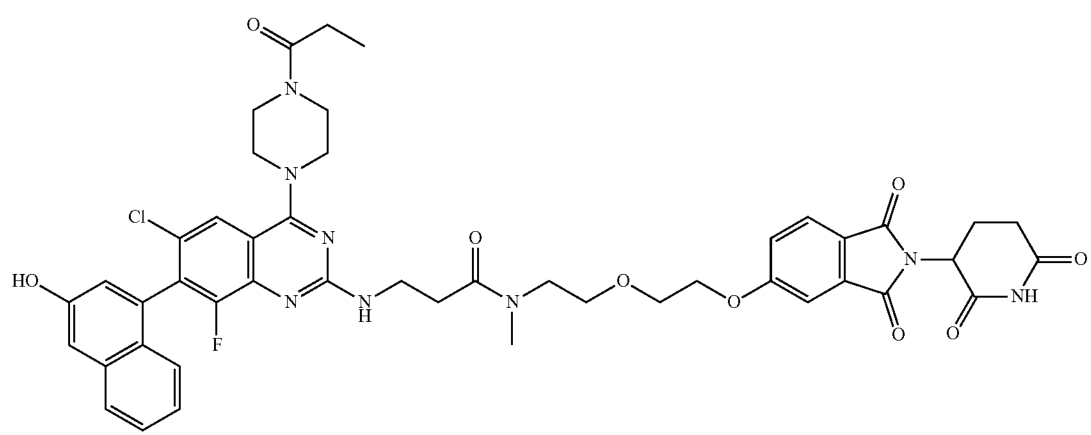 [SMILES: CCC(=O)N1CCN(c2nc(NCCC(=O)N(C)CCOCCOc3ccc4c(c3)C(=O)N(C3CCC(=O)NC3=O)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 48 | 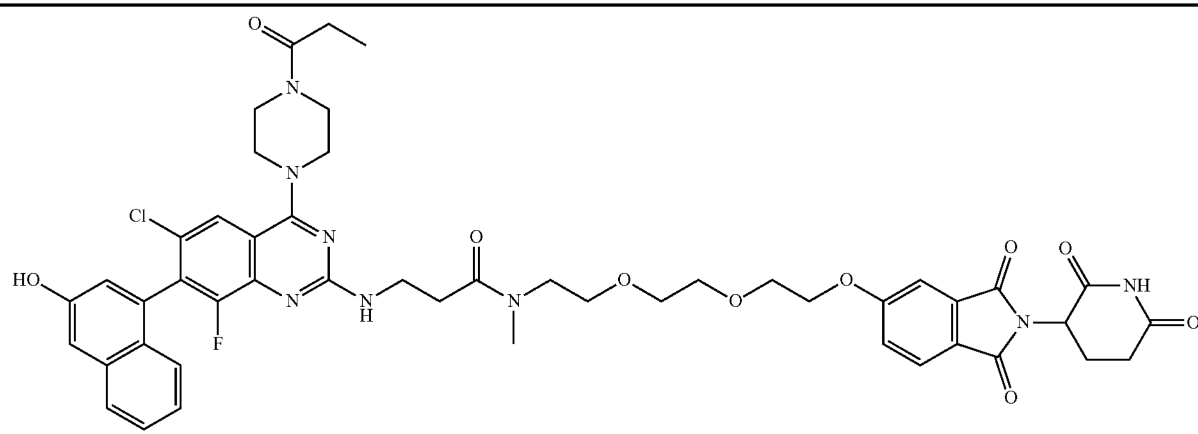 | 3-((6-chloro-8-fluoro-7-(3-hydroxynaphthalen-1-yl)-4-(4-propionylpiperazin-1-yl)quinazolin-2-yl)amino)-N-(2-(2-(2-(2,6-dioxopiperidin-3-yl)-1,3-dioxoisoindolin-5-yl)oxy)ethoxy)ethoxy)ethyl)-N-methylpropanamide | 1 |
| 49 | 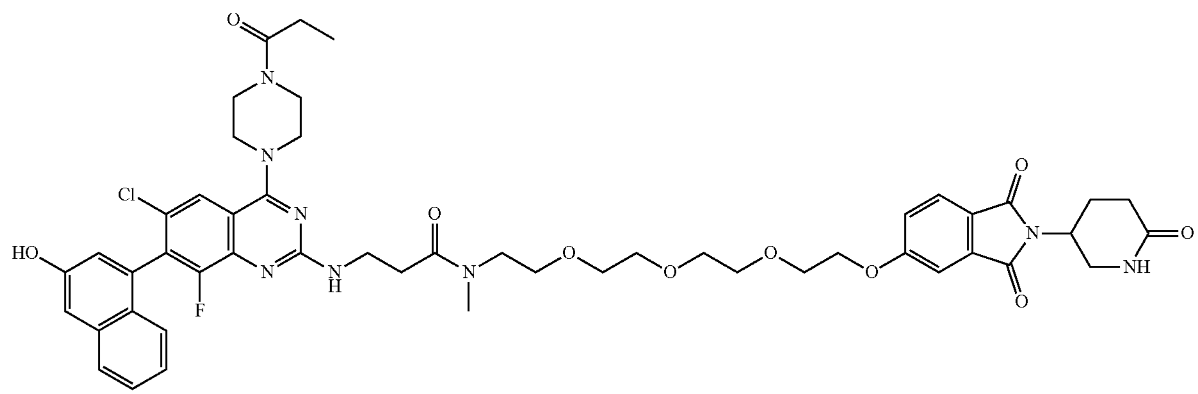 [SMILES: CCC(=O)N1CCN(c2nc(NCCC(=O)N(C)CCOCCOCCOCCOc3ccc4c(c3)C(=O)N(C3CCC(=O)NC3)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(2-(2-((2-(2-(2,6-dioxopiperidin-3-yl)-1,3-dioxoisoindolin-5-yl)oxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 50 | 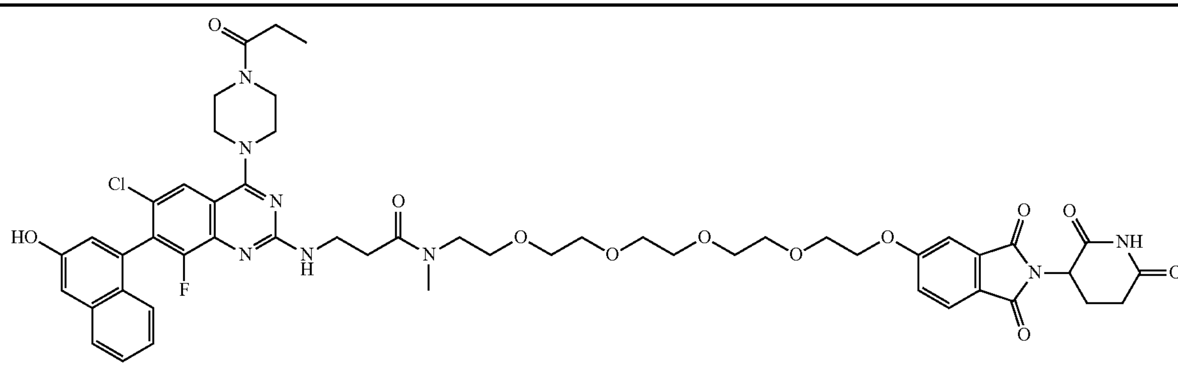 | 3-((6-chloro-8-fluoro-7-(3-hydroxynaphthalen-1-yl)-4-(4-propionylpiperazin-1-yl)quinazolin-2-yl)amino)-N-(14-((2-(2,6-dioxopiperidin-3-yl)-1,3-dioxoisoindolin-5-yl)oxy)-3,6,9,12-tetraoxatetradecyl)-N-methylpropanamide | 1 |
| 51 | 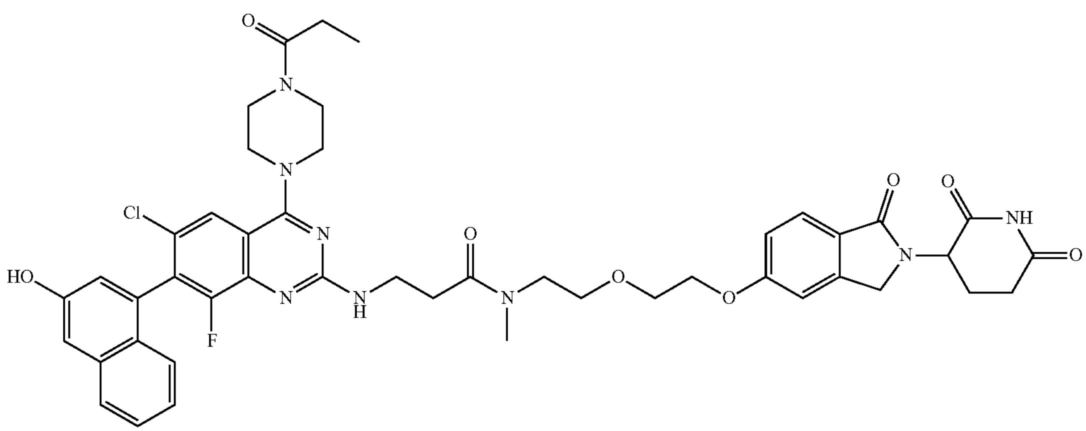 [SMILES: CCC(=O)N1CCN(c2nc(NCCC(=O)N(C)CCOCCOc3ccc4c(c3)CN(C3CCC(=O)NC3=O)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(2-(2-((2-(2,6-dioxopiperidin-3-yl)-1-oxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 52 | 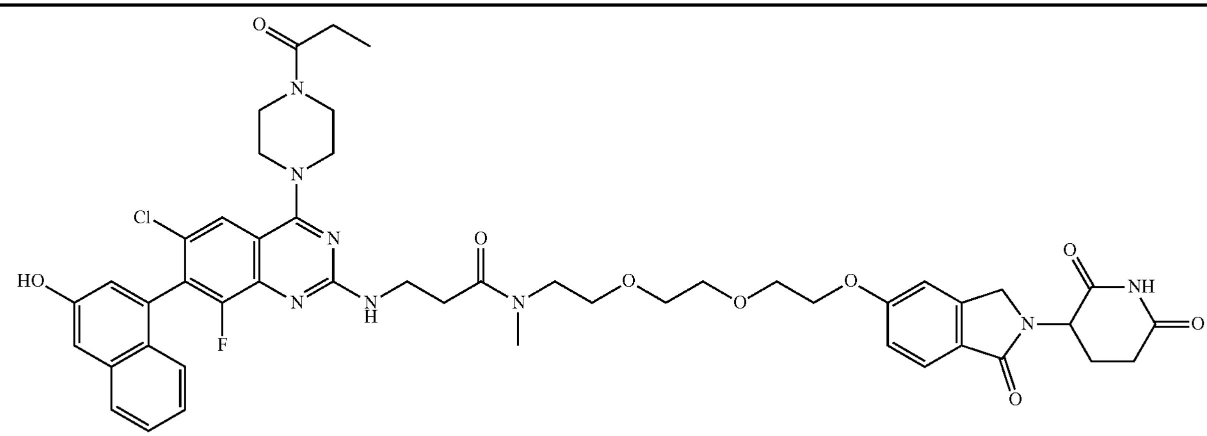 | 3-((6-chloro-8-fluoro-7-(3-hydroxynaphthalen-1-yl)-4-(4-propionylpiperazin-1-yl)quinazolin-2-yl)amino)-N-(2-(2-(2-(2,6-dioxopiperidin-3-yl)-1-oxoisoindolin-5-yl)oxy)ethoxy)ethoxy)ethyl)-N-methylpropanamide | 1 |
| 53 | 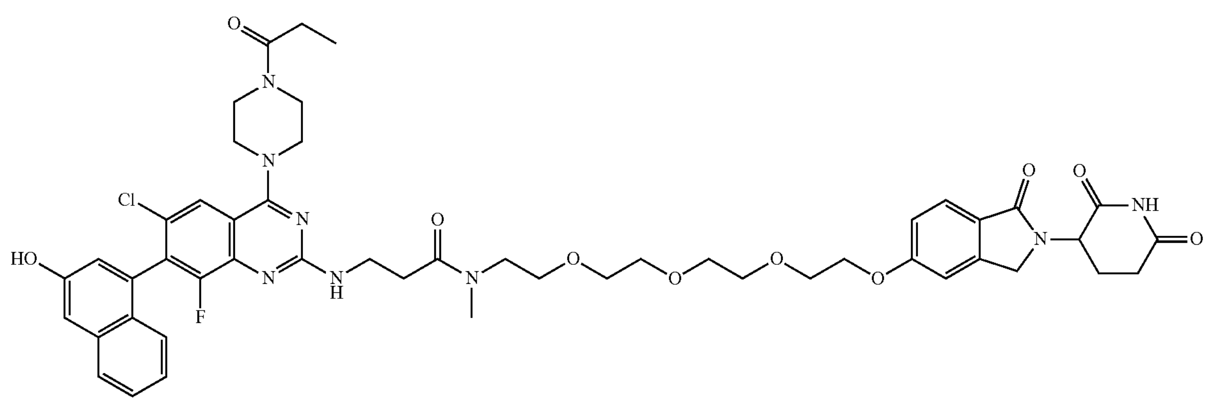 [SMILES: CCC(=O)N1CCN(c2nc(NCCC(=O)N(C)CCOCCOCCOCCOc3ccc4c(c3)CN(C3CCC(=O)NC3=O)C4=O)nc3c(F)c(-c4cc(O)cc5ccccc45)c(Cl)cc23)CC1] | 3-((6-chloro-8-fluoro-7-(3-hydroxynaphthalen-1-yl)-4-(4-propionylpiperazin-1-yl)quinazolin-2-yl)amino)-N-(2-(2-(2-(2-(2,6-dioxopiperidin-3-yl)-1-oxoisoindolin-5-yl)oxy)ethoxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 54 | 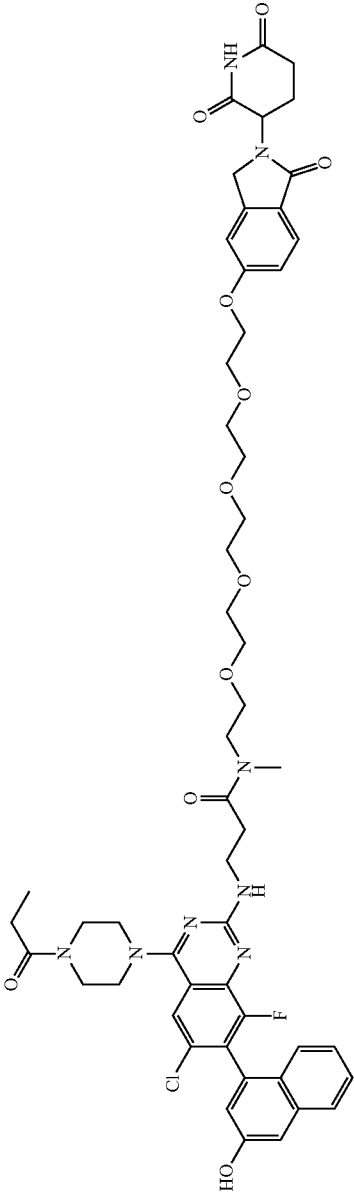 | 3-((6-chloro-8-fluoro-7-(3-hydroxynaphthalen-1-yl)-4-(4-propionylpiperazin-1-yl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide | 1 |
| 55 | 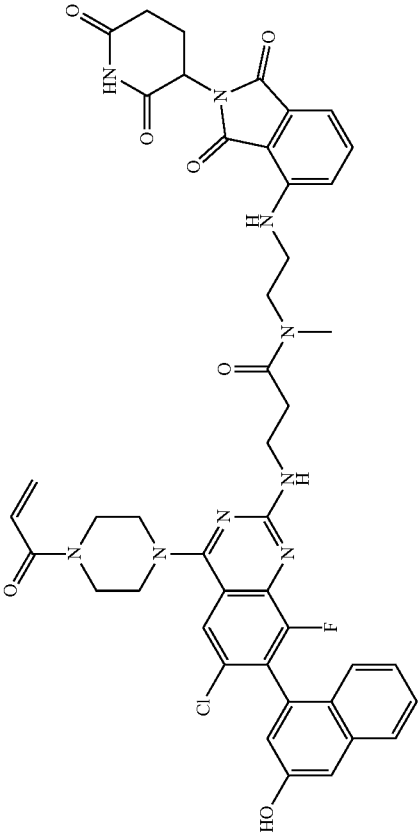 | 3-((4-(4-acryloylpiperazin-1-yl)-6-chloro-8-fluoro-7-(3-hydroxynaphthalen-1-yl)quinazolin-2-yl)amino)-N-(2-((2-(2,6-dioxopiperidin-3-yl)-1,3-dioxoisoindolin-4-yl)amino)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 56 | 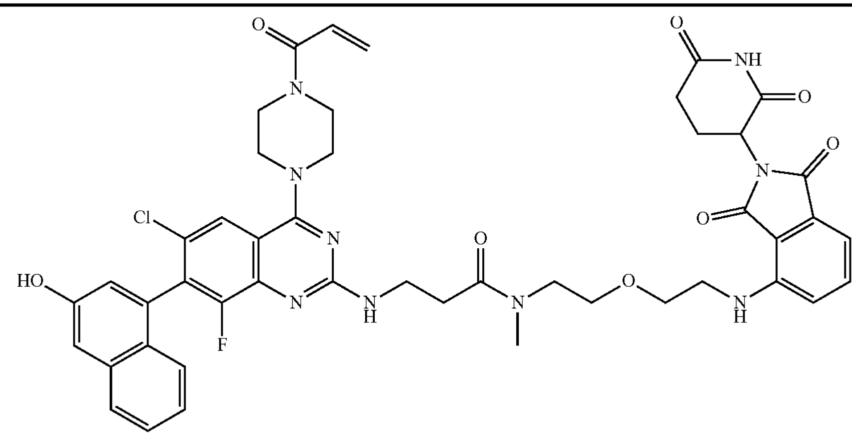 | 3-((4-(4-acryloylpiperazin-1-yl)-6-chloro-8-fluoro-7-(3-hydroxynaphthalen-1-yl)quinazolin-2-yl)amino)-N-(2-((2-(2,6-dioxopiperidin-3-yl)-1,3-dioxoisoindolin-4-yl)amino)ethoxy)ethyl)-N-methylpropanamide | 1 |
| 57 | 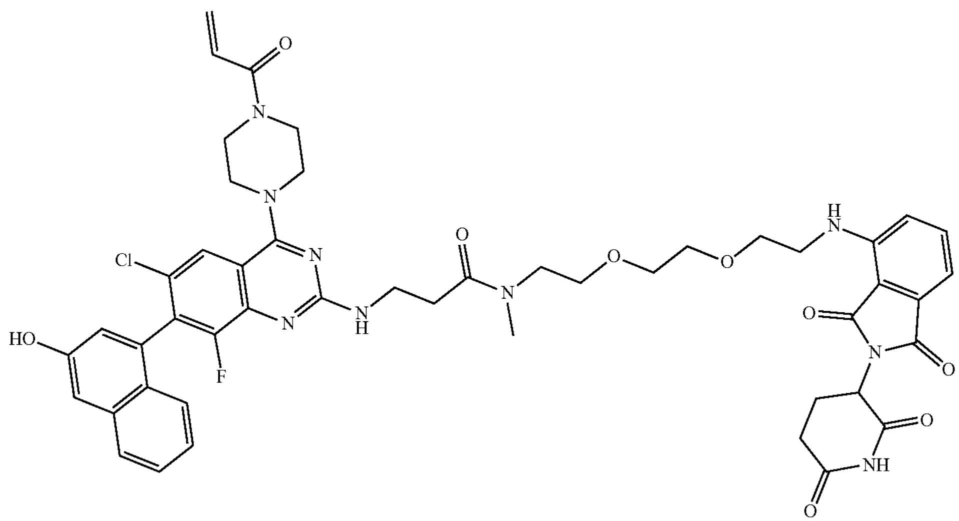 [SMILES: C=CC(=O)N1CCN(c2nc(NCCC(=O)N(C)CCOCCOCCNc3cccc4c3C(=O)N(C3CCC(=O)NC3=O)C4=O)nc3c(F)c(-c4cc(O)cc5ccccc45)c(Cl)cc23)CC1] | 3-((4-(4-acryloylpiperazin-yl)-6-chloro-8-fluoro-7-(3-hydroxynaphthalen-1-yl)quinazolin-2-yl)amino)-N-(2-(2-((2-(2,6-dioxopiperidin-3-yl)-1,3-dioxoisoindolin-4-yl)amino)ethoxy)ethoxy)ethyl)-N-methylpropanamide | 1 |

TABLE 6-continued
Compounds Prepared by Schemes 1 and 2
| Ex. No. | Structure | Compound Name | Synthetic Scheme |
|---|---|---|---|
| 58 | 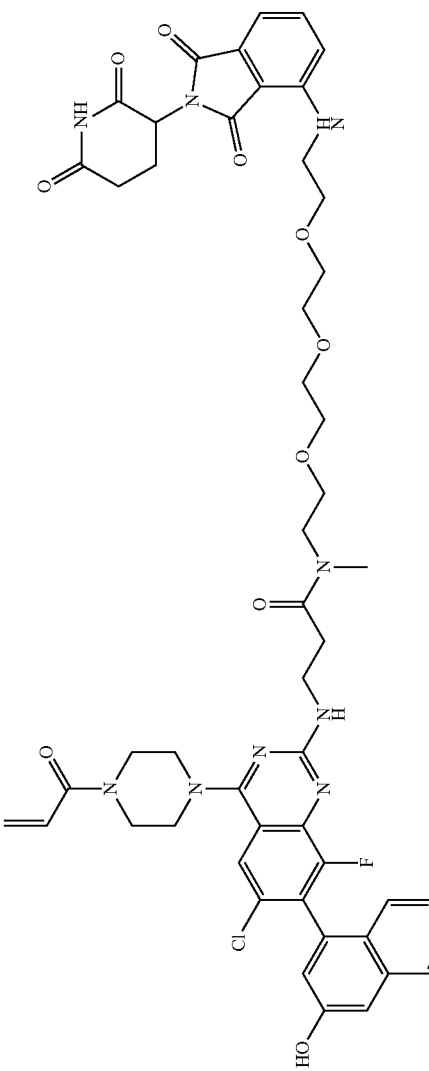 | 3-((4-(4-acryloylpiperazin-1-yl)-6-chloro-8-fluoro-7-(3-hydroxynaphthalen-1-yl)quinazolin-2-yl)amino)-N-(2-(2-(2-((2-(2,6-dioxopiperidin-3-yl)-1,3-dioxoisoindolin-4-yl)amino)ethoxy)ethoxy)ethoxy)ethyl)-N-methylpropanamide | 1 |

TABLE 6-continued
Compounds Prepared by Schemes 1 and 2
| Ex. No. | Structure | Compound Name | Synthetic Scheme |
|---|---|---|---|
| 59 | 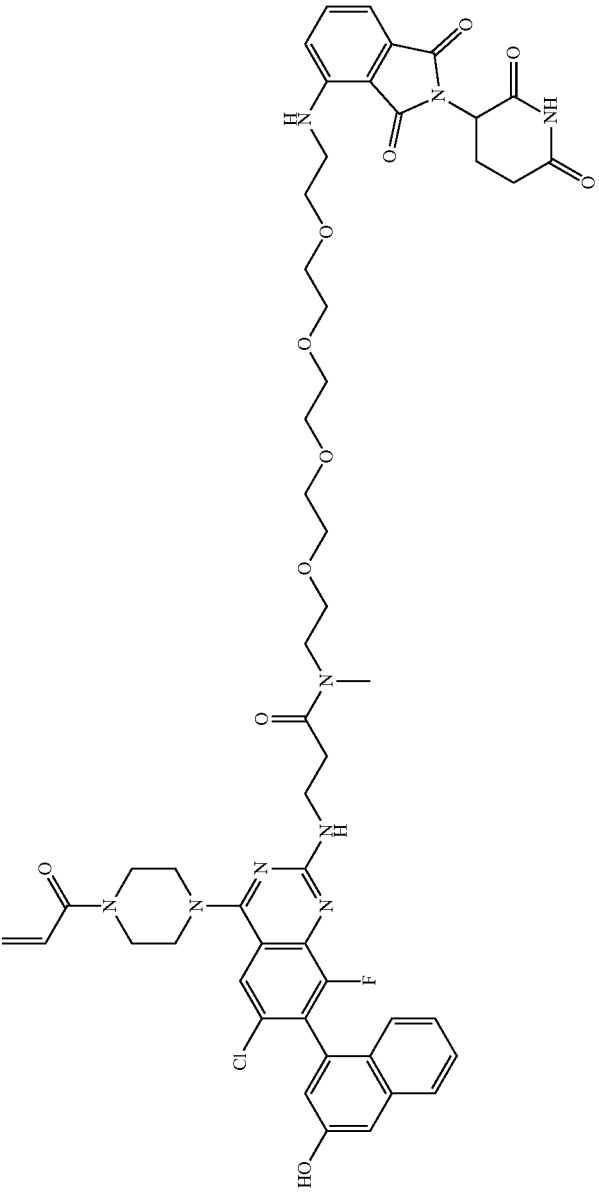 | 3-((4-(4-acryloylpiperazin-1-yl)-6-chloro-8-fluoro-7-(3-hydroxynaphthalen-1-yl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 60 | 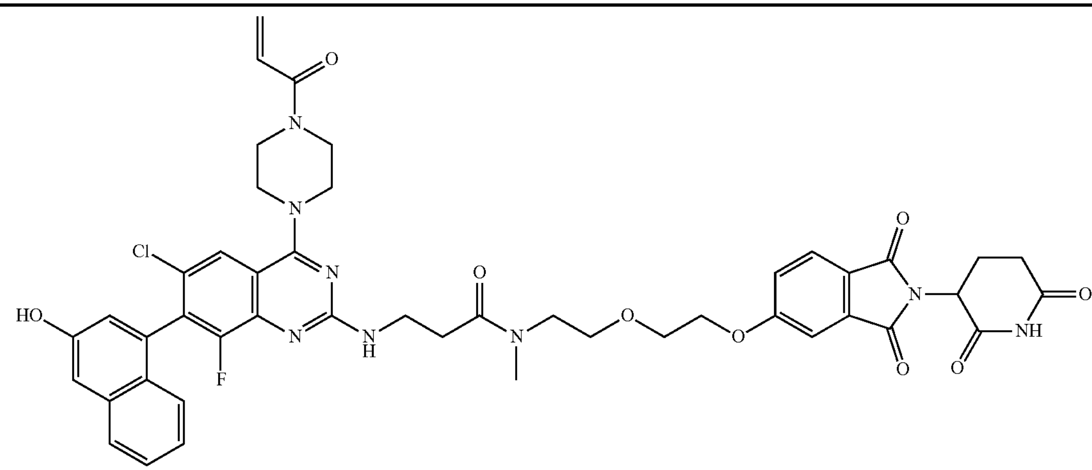 | 3-((4-(4-acryloylpiperazin-1-yl)-6-chloro-8-fluoro-7-(3-hydroxynaphthalen-1-yl)quinazolin-2-yl)amino)-N-(2-((2-(2,6-dioxopiperidin-3-yl)-1,3-dioxoisoindolin-5-yl)oxy)ethoxy)ethyl)-N-methylpropanamide | 1 |
| 61 | 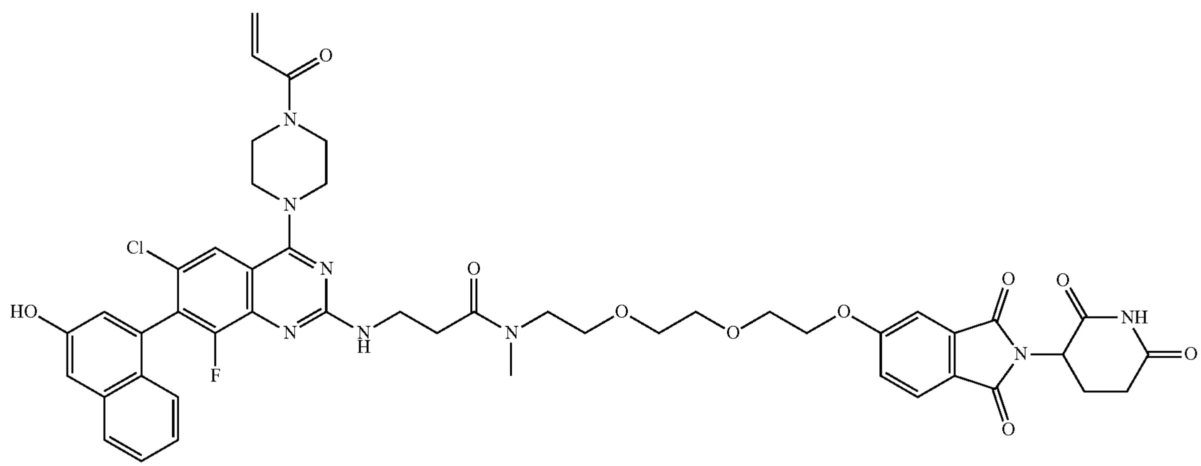 [SMILES: C=CC(=O)N1CCN(c2nc(NCCC(=O)N(C)CCOCCOCCOc3ccc4c(c3)C(=O)N(C3CCC(=O)NC3=O)C4=O)nc3c(F)c(-c4cc(O)cc5ccccc45)c(Cl)cc23)CC1] | 3-((4-(4-acryloylpiperazin-1-yl)-6-chloro-8-fluoro-7-(3-hydroxynaphthalen-1-yl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 62 | 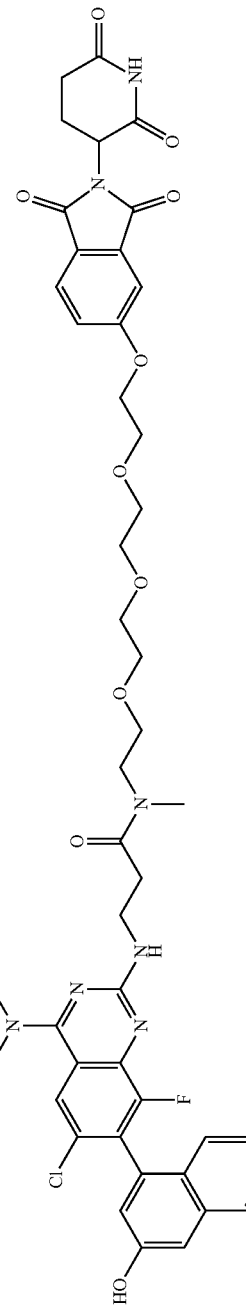 | 3-((4-(4-acryloylpiperazin-1-yl)-6-chloro-8-fluoro-7-(3-hydroxynaphthalen-1-yl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide | 1 |
| 63 | 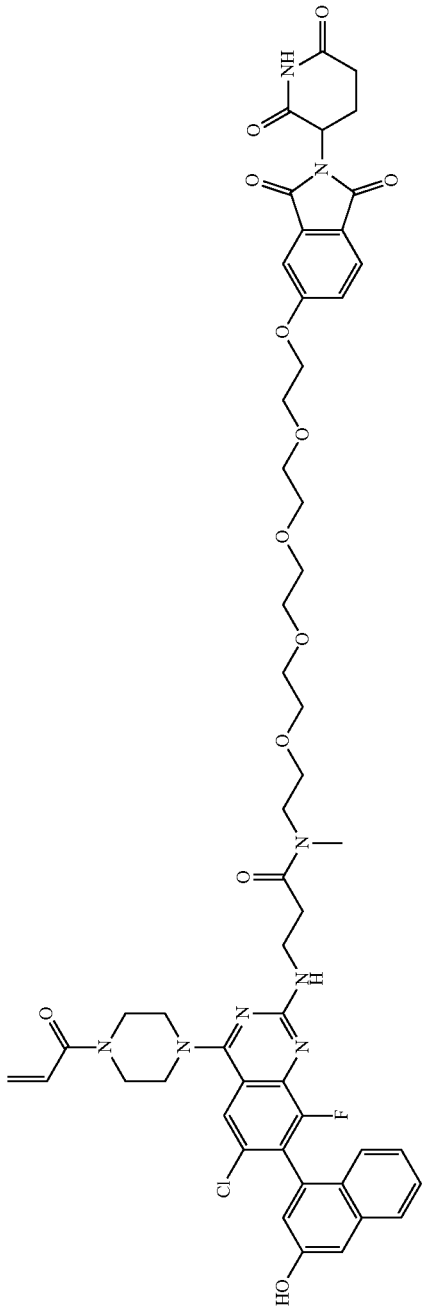 | 3-((4-(4-acryloylpiperazin-1-yl)-6-chloro-8-fluoro-7-(3-hydroxynaphthalen-1-yl)quinazolin-2-yl)amino)-N-(14-((2-(2,6-dioxopiperidin-3-yl)-1,3-dioxoisoindolin-5-yl)oxy)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 64 | 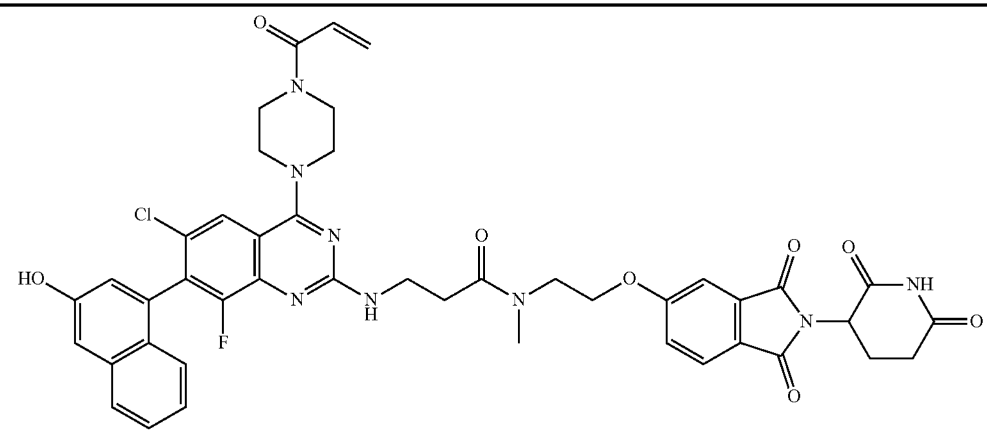 | 3-((4-(4-acryloylpiperazin-1-yl)-6-chloro-8-fluoro-7-(3-hydroxynaphthalen-1-yl)quinazolin-2-yl)amino)-N-(2-((2-(2,6-dioxopiperidin-3-yl)-1-oxoisoindolin-5-yl)oxy)ethyl)-N-methylpropanamide | 1 |
| 65 | 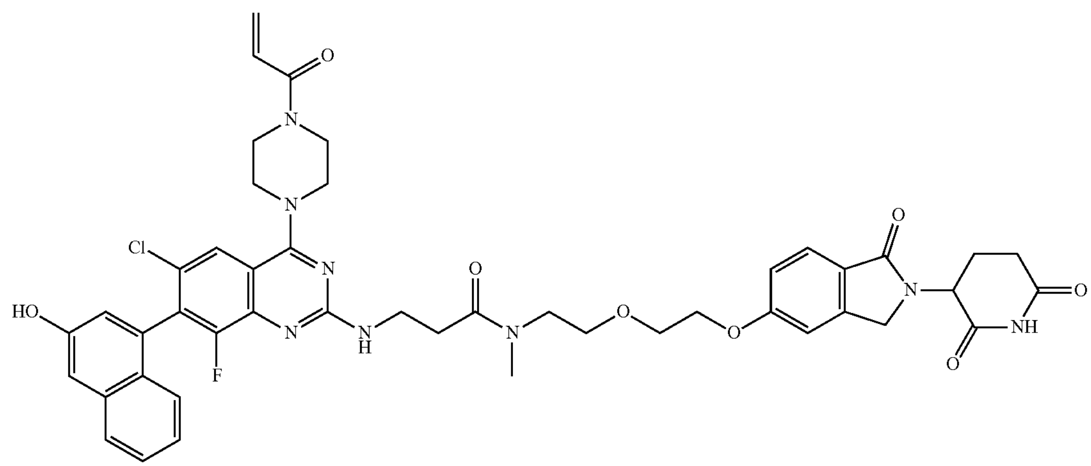 [SMILES: C=CC(=O)N1CCN(c2nc(NCCC(=O)N(C)CCOCCOc3ccc4c(c3)CN(C3CCC(=O)NC3=O)C4=O)nc3c(F)c(-c4cc(O)cc5ccccc45)c(Cl)cc23)CC1] | 3-((4-(4-acryloylpiperazin-1-yl)-6-chloro-8-fluoro-7-(3-hydroxynaphthalen-1-yl)quinazolin-2-yl)amino)-N-(2-(2-((2-(2,6-dioxopiperidin-3-yl)-1-oxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 66 | 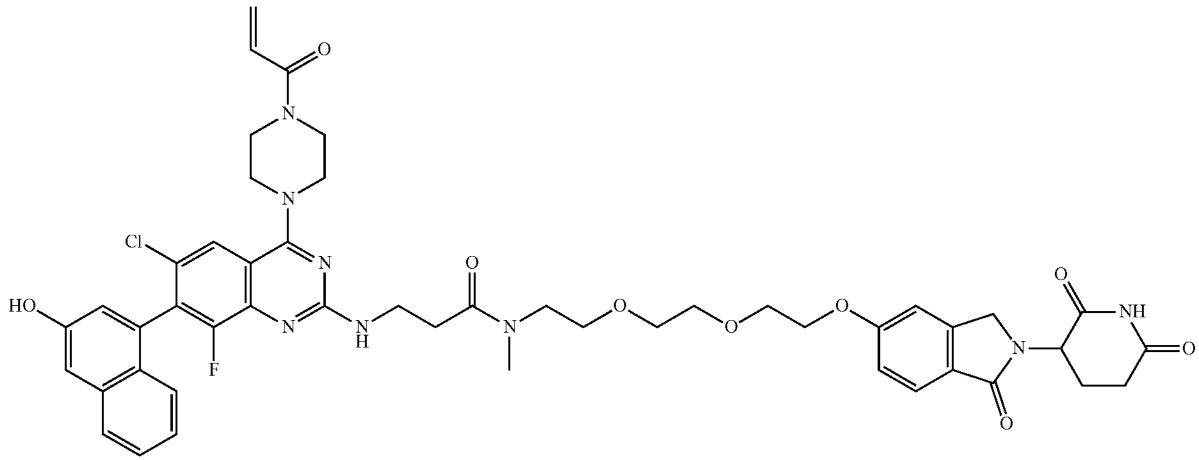 [SMILES: C=CC(=O)N1CCN(c2nc(NCCC(=O)N(C)CCOCCOCCOc3ccc4c(c3)CN(C3CCC(=O)NC3=O)C4=O)nc3c(F)c(-c4cc(O)cc5ccccc45)c(Cl)cc23)CC1] | 3-((4-(4-acryloylpiperazin-1-yl)-6-chloro-8-fluoro-7-(3-hydroxynaphthalen-1-yl)quinazolin-2-yl)amino)-N-(2-(2-(2-(2,6-dioxopiperidin-3-yl)-1-oxoisoindolin-5-yl)oxy)ethoxy)ethoxy)ethyl)-N-methylpropanamide | 1 |
| 67 | 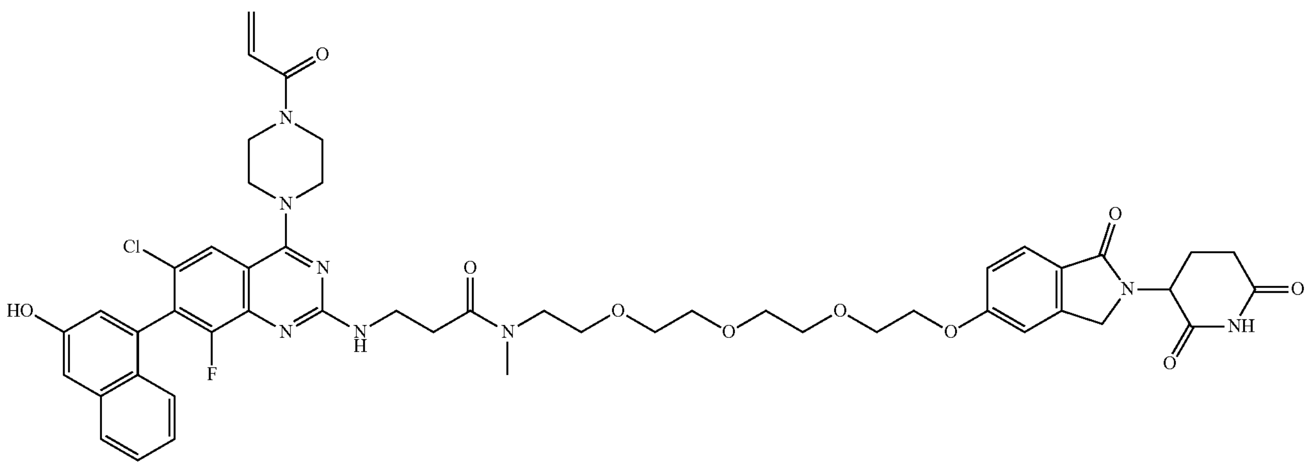 [SMILES: C=CC(=O)N1CCN(c2nc(NCCC(=O)N(C)CCOCCOCCOCCOc3ccc4c(c3)CN(C3CCC(=O)NC3=O)C4=O)nc3c(F)c(-c4cc(O)cc5ccccc45)c(Cl)cc23)CC1] | 3-((4-(4-acryloylpiperazin-1-yl)-6-chloro-8-fluoro-7-(3-hydroxynaphthalen-1-yl)quinazolin-2-yl)amino)-N-(2-(2-((2-(2,6-dioxopiperidin-3-yl)-1-oxoisoindolin-5-yl)oxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 68 | 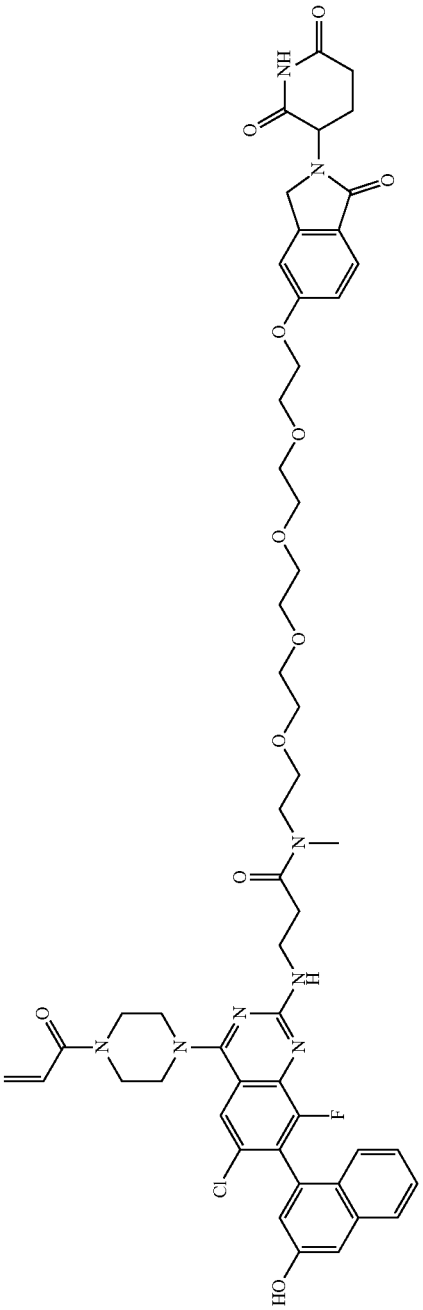 | 3-((4-(4-acryloylpiperazin-1-yl)-6-chloro-8-fluoro-7-(3-hydroxynaphthalen-1-yl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide | 1 |
| 69 | 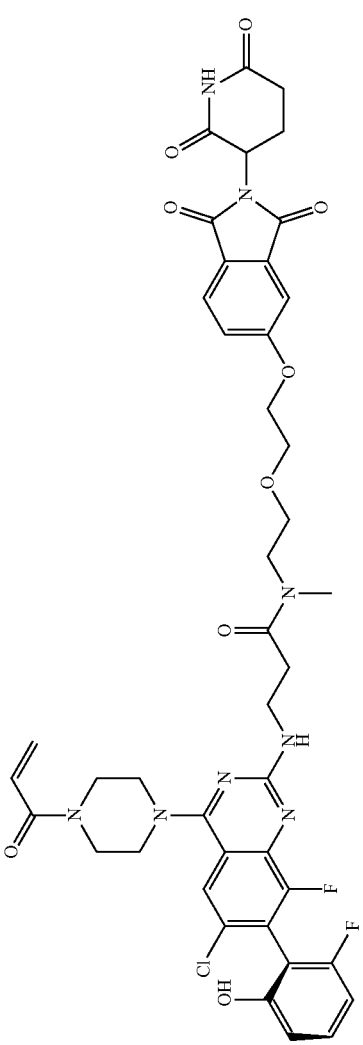 | 3-(((S)-4-(4-acryloylpiperazin-1-yl)-6-chloro-8-fluoro-7-(2-fluoro-6-hydroxyphenyl)quinazolin-2-yl)amino)-N-(2-(2-(2-(2,6-dioxopiperidin-3-yl)-1,3-dioxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 70 | 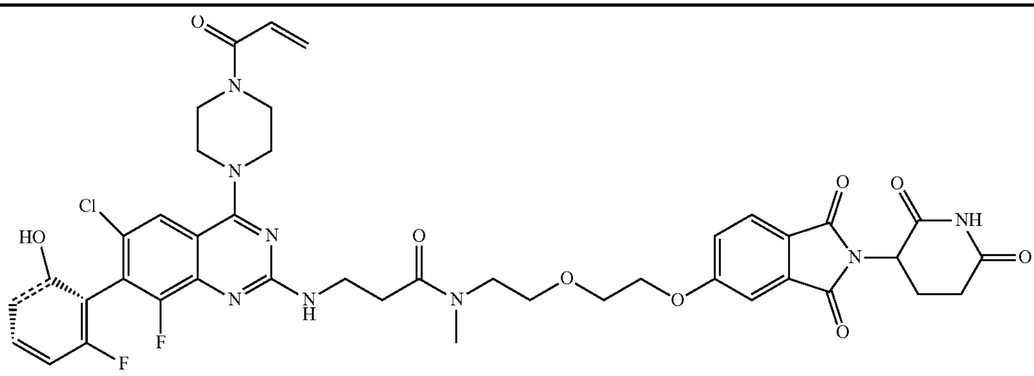 | 3-(((R)-4-(4-acryloylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |
| 71 | 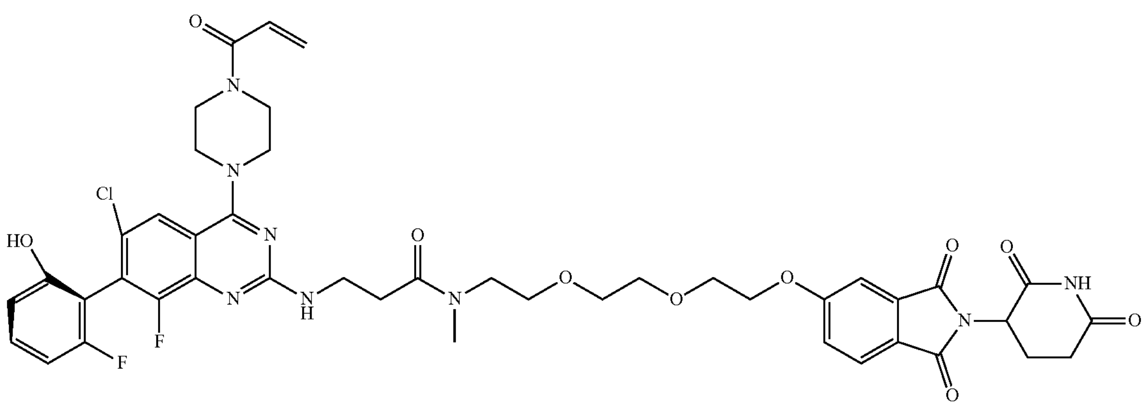 | 3-(((S)-4-(4-acryloylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 72 | 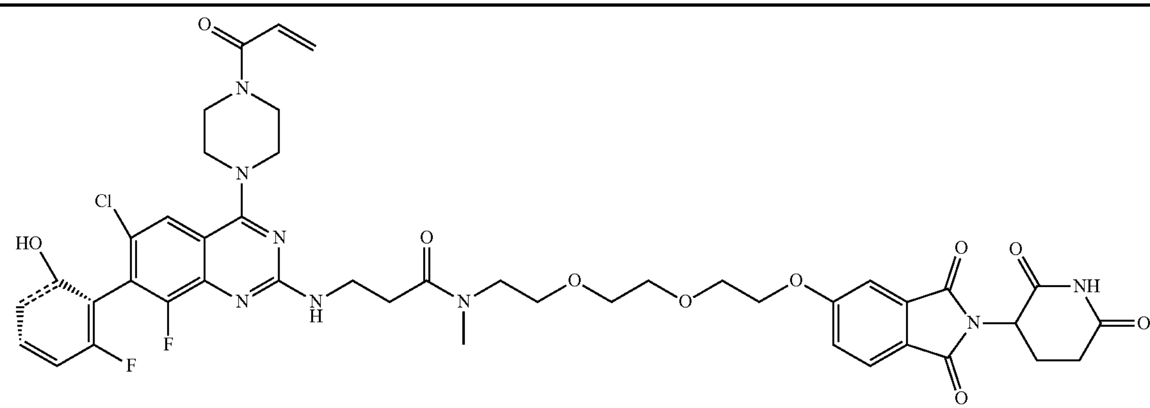 | 3-(((R)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide | 1 |
| 73 | 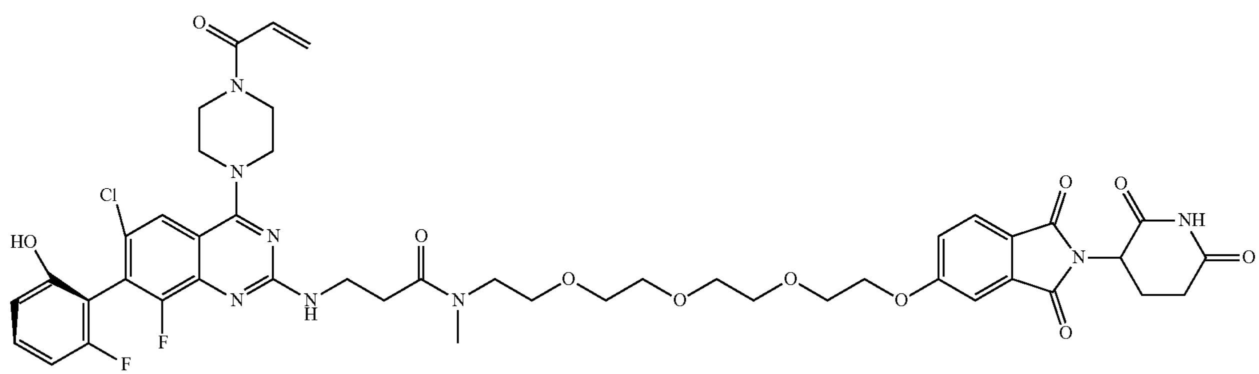 | 3-(((S)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 74 | 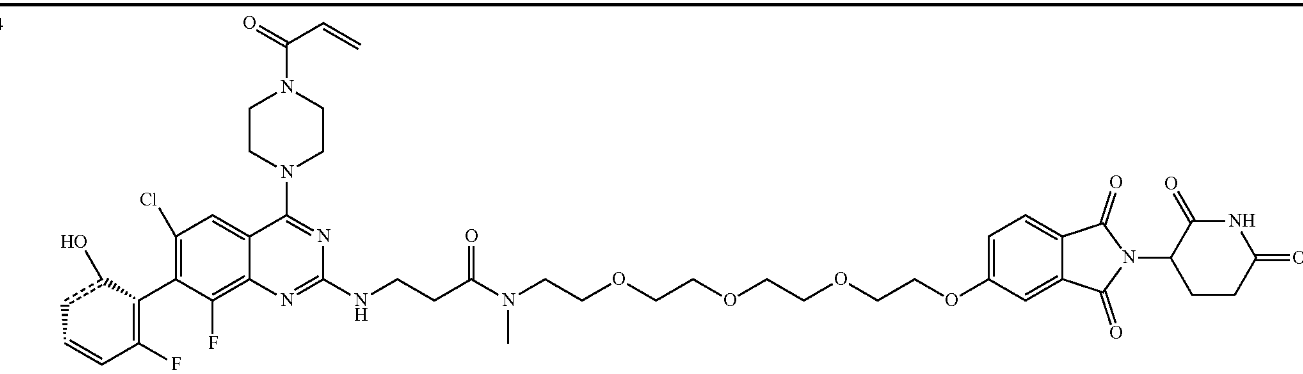 | 3-(((R)-4-(4-acryloylpiperazin-1-yl)-6-chloro-8-fluoro-7-(2-fluoro-6-hydroxyphenyl)quinazolin-2-yl)amino)-N-(2-(2-(2-(2-((2-(2,6-dioxopiperidin-3-yl)-1,3-dioxoisoindolin-5-yl)oxy)ethoxy)ethoxy)ethoxy)ethyl)-N-methylpropanamide | 1 |
| 75 | 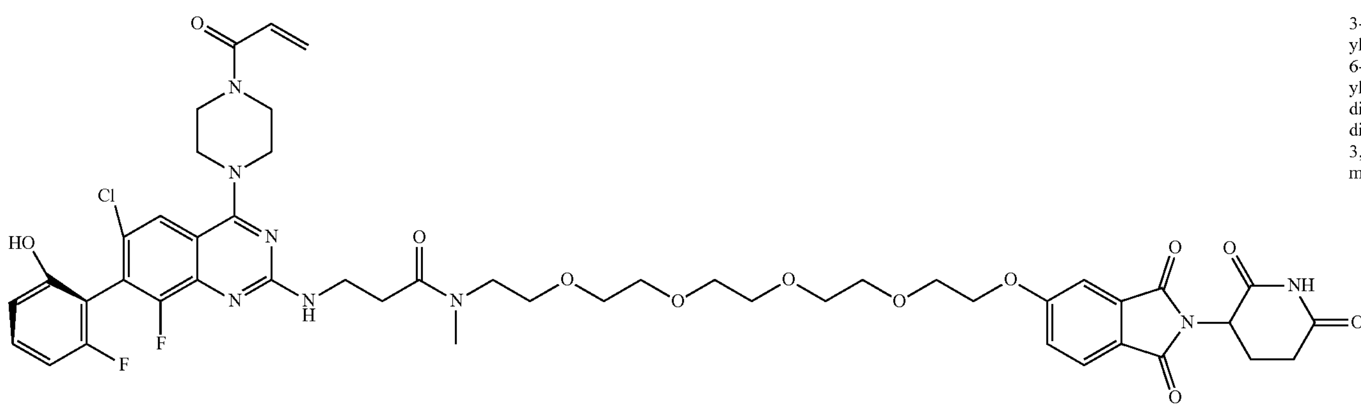 | 3-(((S)-4-(4-acryloylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1,3-dioxoisoindolin-5-yl)oxy)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 76 | 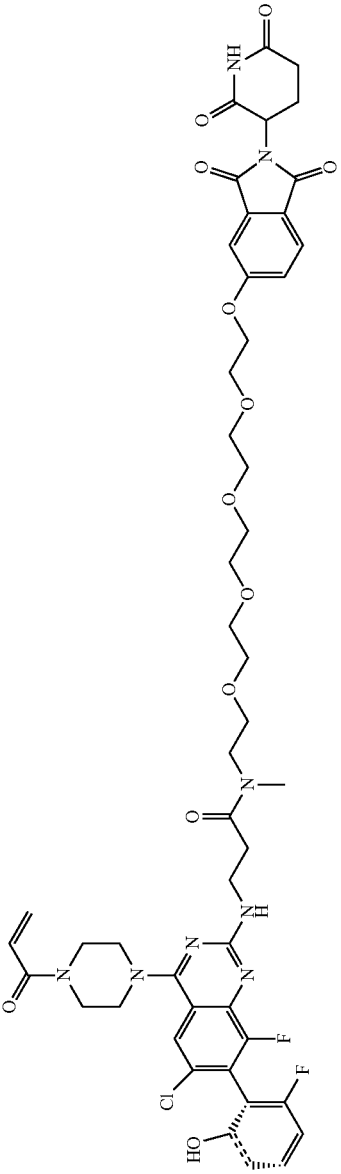 | 3-(((R)-4-(4-acryloylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1,3-dioxoisoindolin-5-yl)oxy)-3,6,9,12-tetraoxatetradecyl)-N-methylpropanamide | 1 |
| 77 | 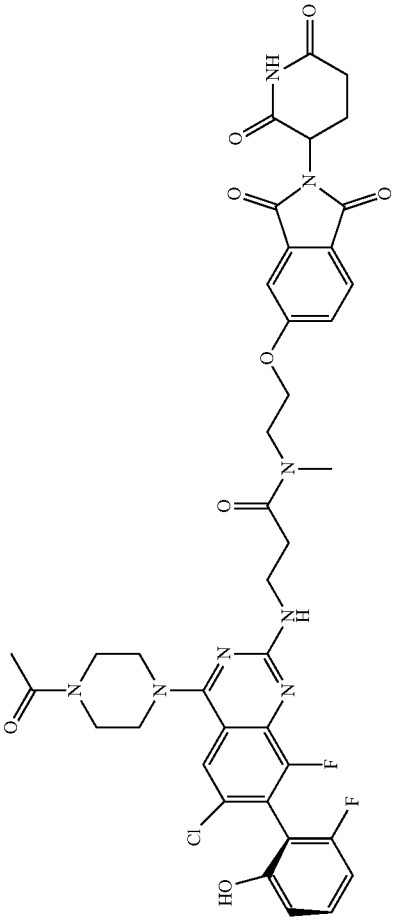 | 3-(((S)-4-(4-acetylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-5-yl)oxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 78 | 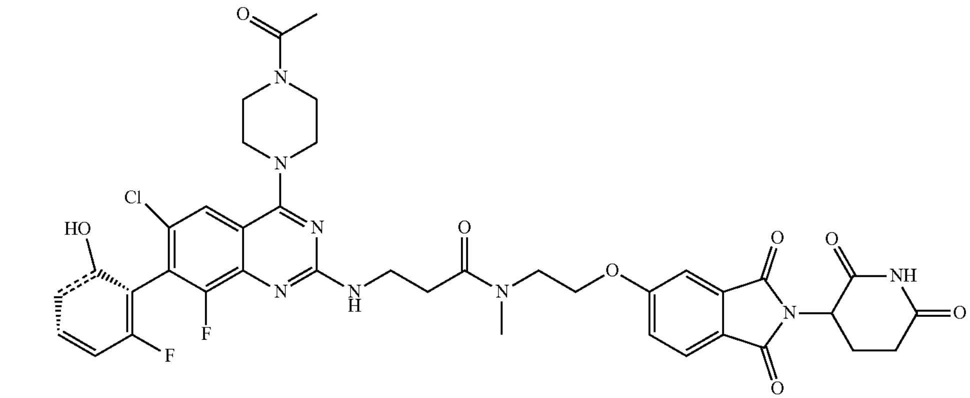 | 3-(((R)-4-(4-acetylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-5-yl)oxy)ethyl)-N-methylpropanamide | 1 |
| 79 | 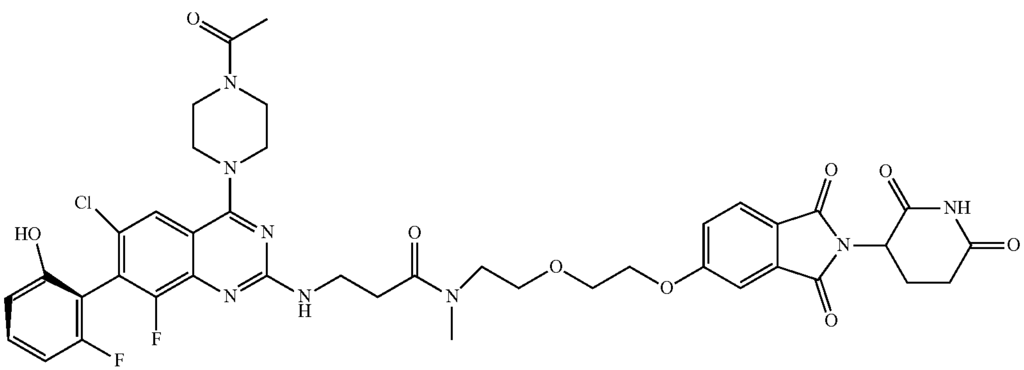 | 3-(((S)-4-(4-acetylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 80 | 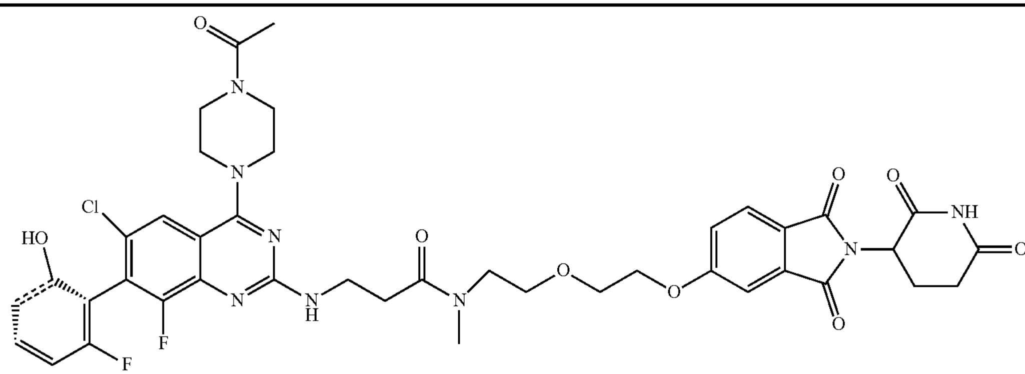 | 3-(((R)-4-(4-acetylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |
| 81 | 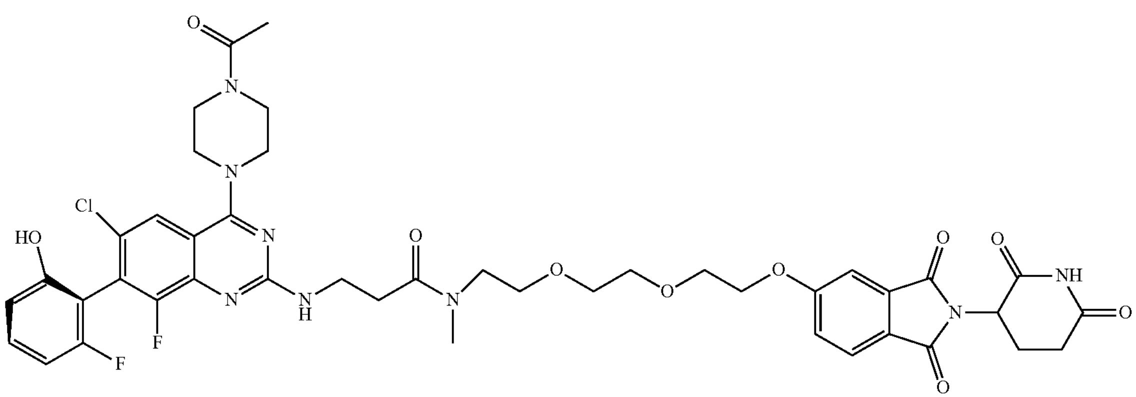 | 3-(((S)-4-(4-acetylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 82 | 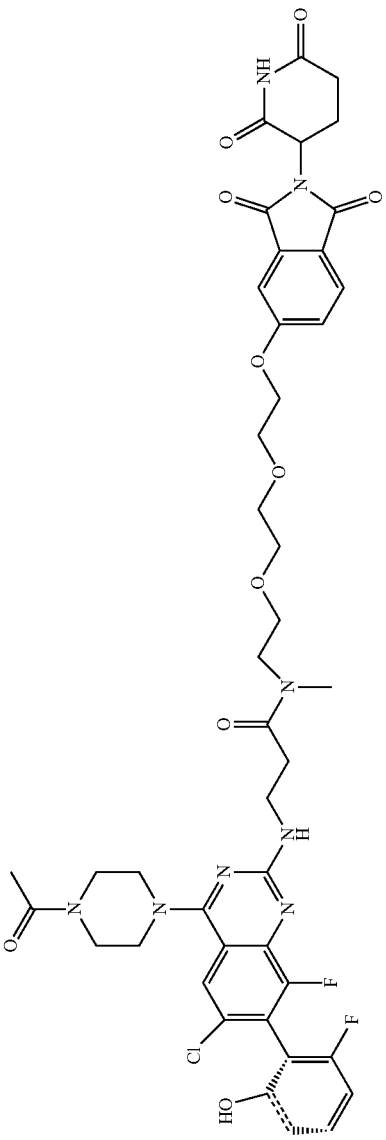 | 3-(((R)-4-(4-acetylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide | 1 |
| 83 | 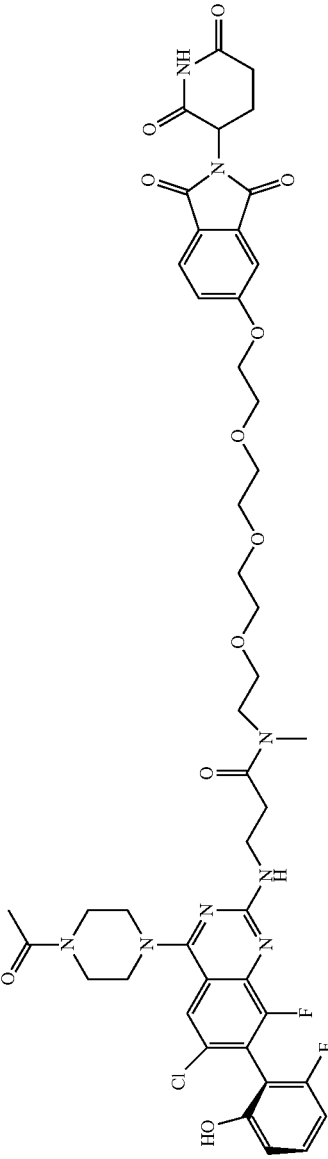 | 3-(((S)-4-(4-acetylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 84 | 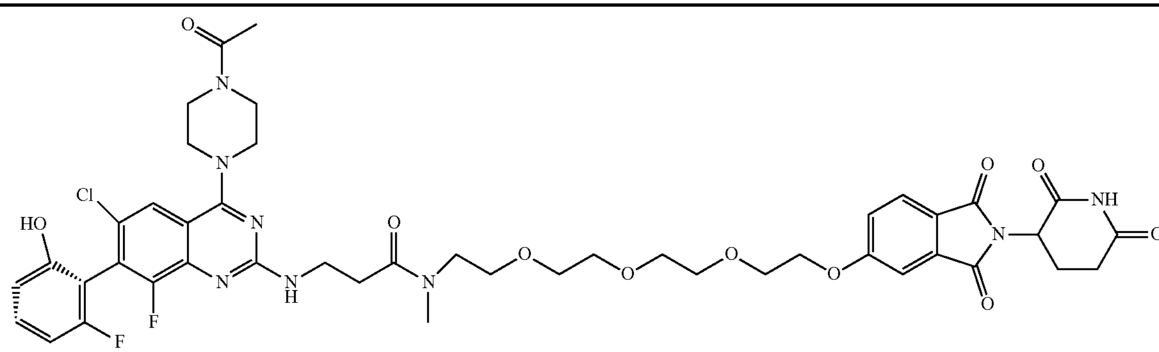 | 3-(((R)-4-(4-acetylpiperazin-1-yl)-6-chloro-8-fluoro-7-(2-fluoro-6-hydroxyphenyl)quinazolin-2-yl)amino)-N-(2-(2-(2-(2-((2-(2,6-dioxopiperidin-3-yl)-1,3-dioxoisoindolin-5-yl)oxy)ethoxy)ethoxy)ethoxy)ethyl)-N-methylpropanamide | 1 |
| 85 | 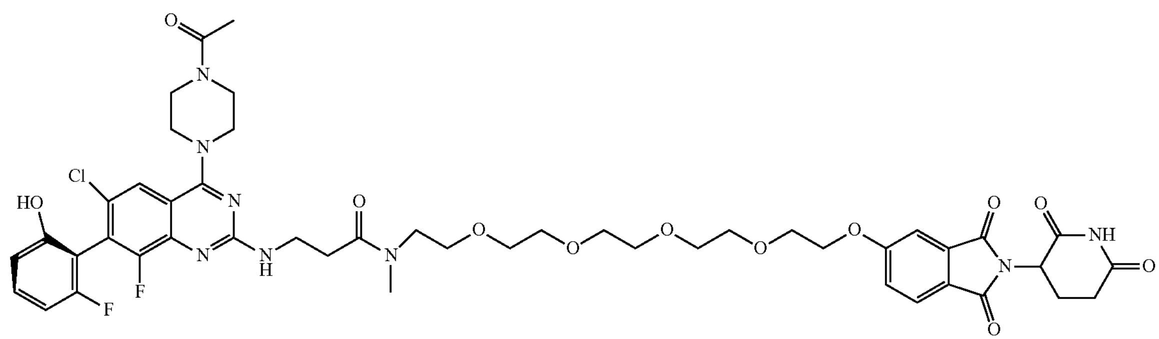 | 3-(((S)-4-(4-acetylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1,3-dioxoisoindolin-5-yl)oxy)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 86 | 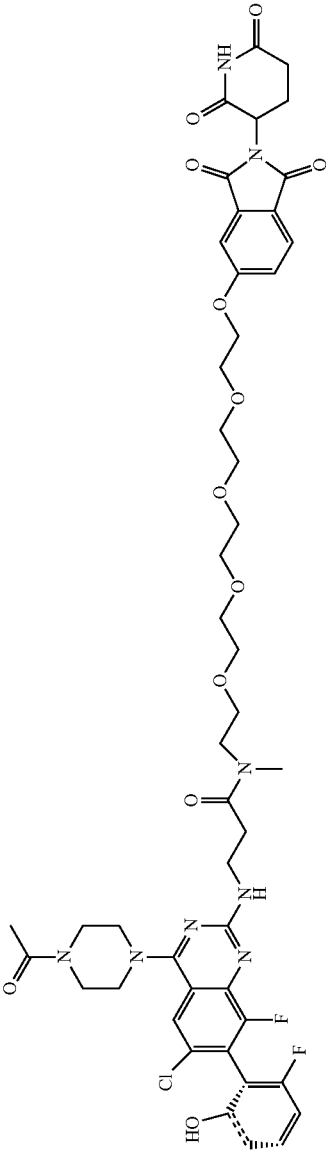 | 3-(((R)-4-(4-acetylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1,3-dioxoisoindolin-5-yl)oxy)-3,6,9,12-tetraoxatetradecyl)-N-methylpropanamide | 1 |
| 87 | 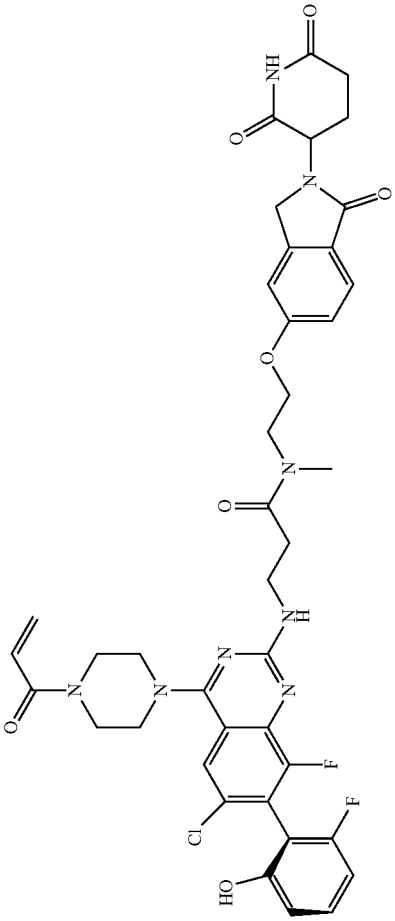 | 3-(((S)-4-(4-acryloylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1-oxoisoindolin-5-yl)oxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 88 | 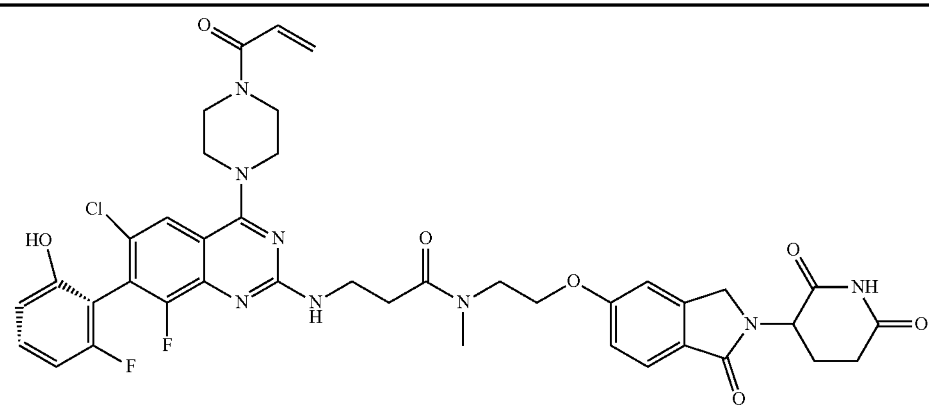 | 3-(((R)-4-(4-acryloylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1-oxoisoindolin-5-yl)oxy)ethyl)-N-methylpropanamide | 1 |
| 89 | 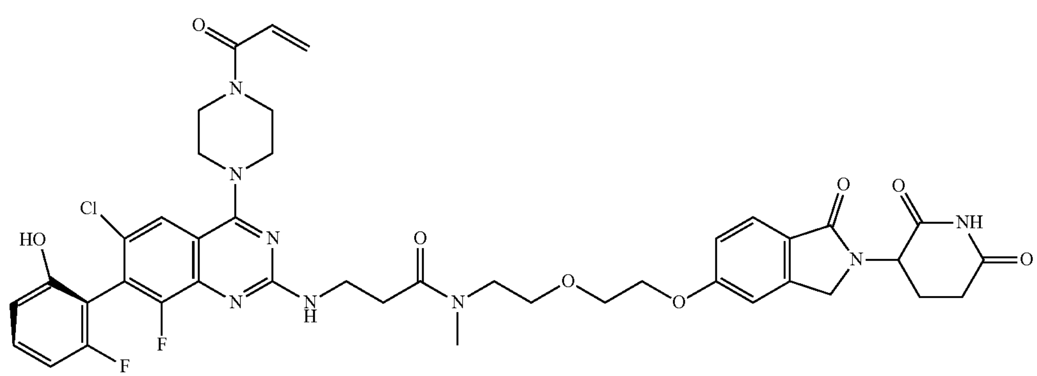 | 3-((4-(4-acryloylpiperazin-1-yl)-6-chloro-8-fluoro-7-((S)-2-fluoro-6-hydroxyphenyl)quinazolin-2-yl)amino)-N-(2-(2-((2-(2,6-dioxopiperidin-3-yl)-1-oxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 90 | 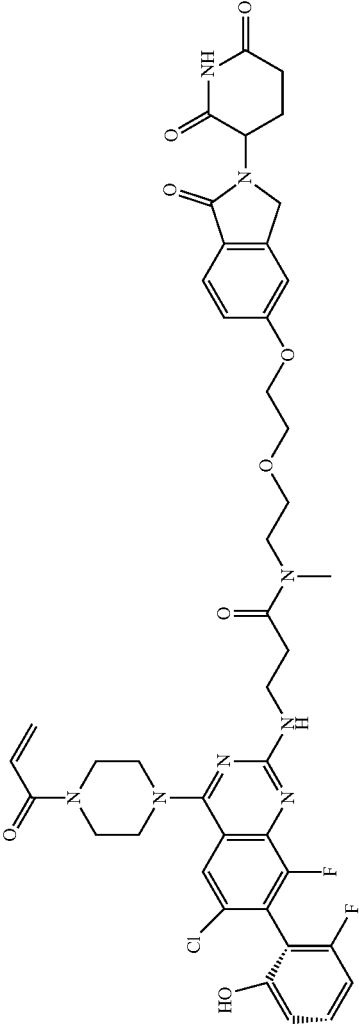 | 3-((4-(4-acryloylpiperazin-1-yl)-6-chloro-8-fluoro-7-((R)-2-fluoro-6-hydroxyphenyl)quinazolin-2-yl)amino)-N-(2-(2-((2-(2,6-dioxopiperidin-3-yl)-1-oxoisoindolin-5-yl)oxy)ethoxy)ethyl)-N-methylpropanamide | 1 |
| 91 | 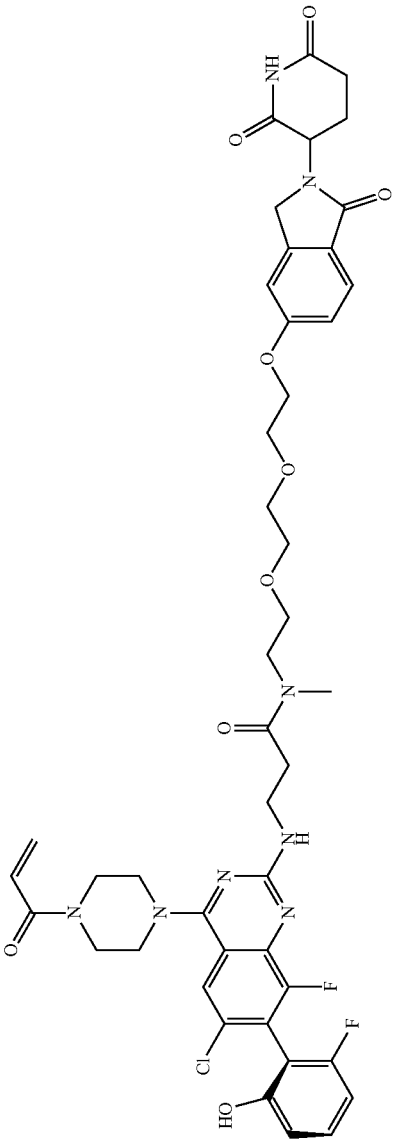 | 3-(((S)-4-(4-acryloylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1-oxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 92 | 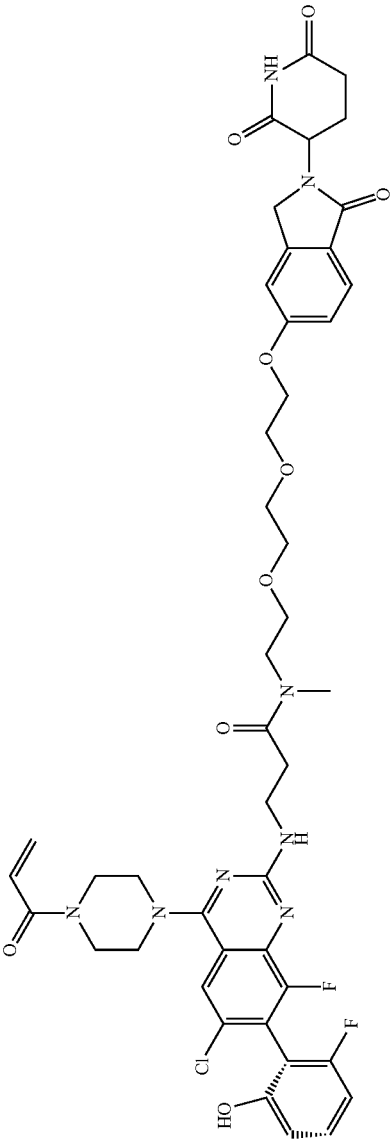 | 3-(((R)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1-oxoisoindolin-5-yl)oxy)ethoxy)ethoxy)ethyl)-N-methylpropanamide | 1 |
| 93 | 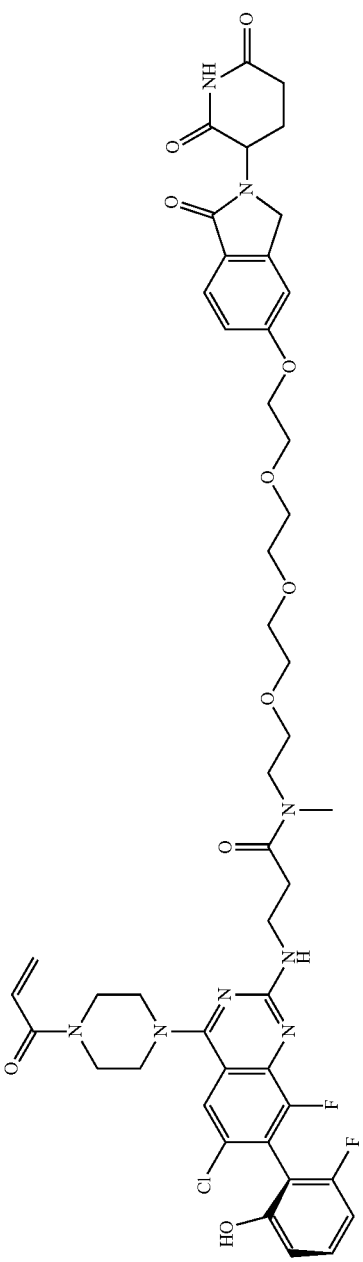 | 3-((4-(4-acryloylpiperazin-1-yl)-6-chloro-8-fluoro-7-((S)-2-fluoro-6-hydroxyphenyl)quinazolin-2-yl)amino)-N-(2-(2-(2-((2-(2,6-dioxopiperidin-3-yl)-1-oxoisoindolin-5-yl)oxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 94 | 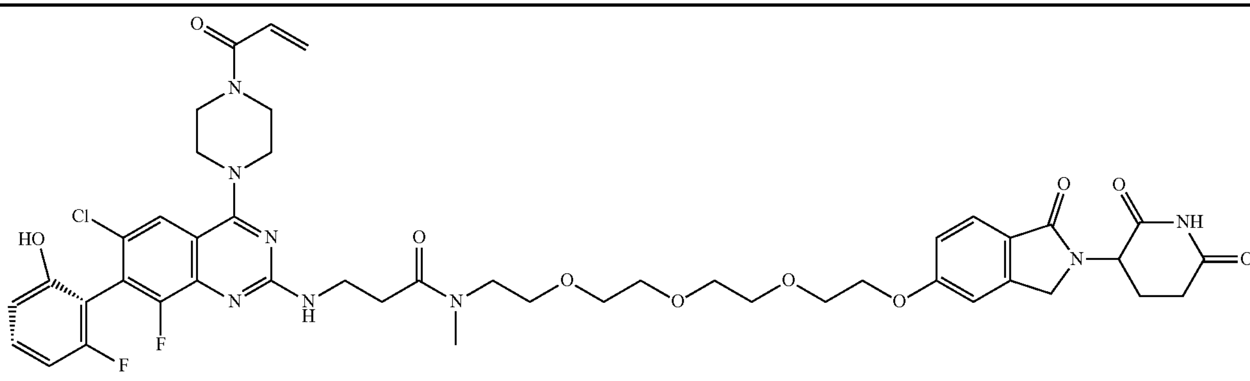 | 3-((4-(4-acryloylpiperazin-1-yl)-6-chloro-8-fluoro-7-((R)-2-fluoro-6-hydroxyphenyl)quinazolin-2-yl)amino)-N-(2-(2-(2-(2-((2-(2,6-dioxopiperidin-3-yl)-1-oxoisoindolin-5-yl)oxy)ethoxy)ethoxy)ethoxy)ethyl)-N-methylpropanamide | 1 |
| 95 | 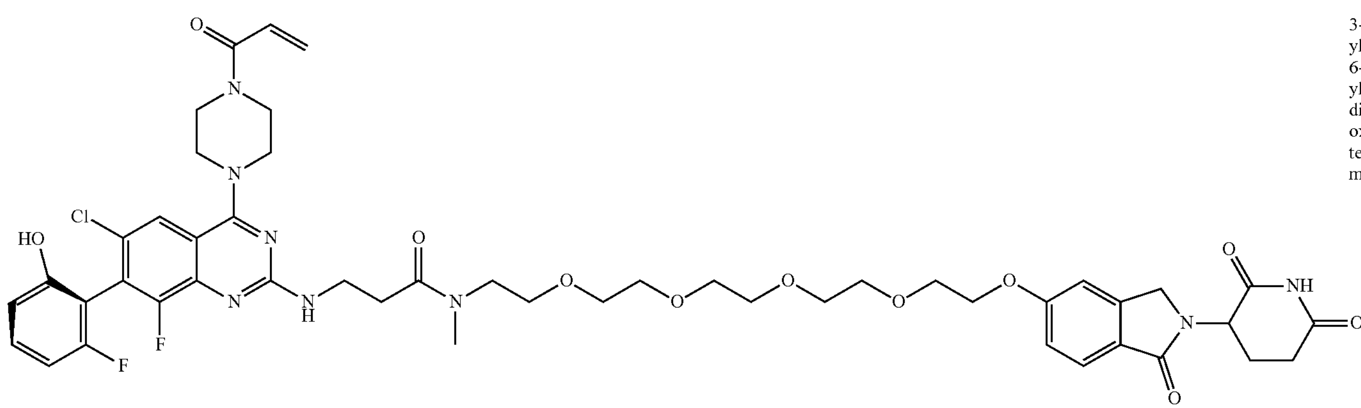 | 3-(((S)-4-(4-acryloylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 96 | 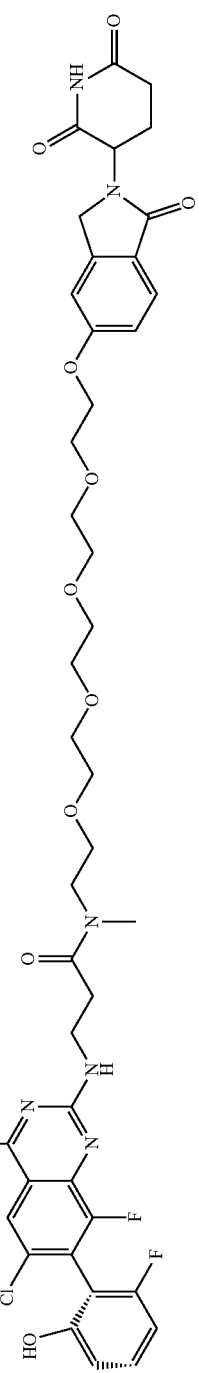 | 3-(((R)-4-(4-acryloylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide | 1 |
| 97 | 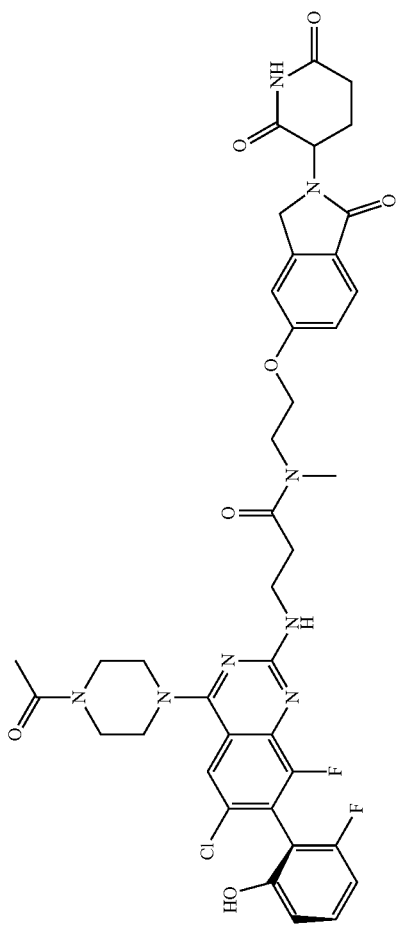 | 3-(((S)-4-(4-acetylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1-oxoisoindolin-5-yl)oxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 98 | 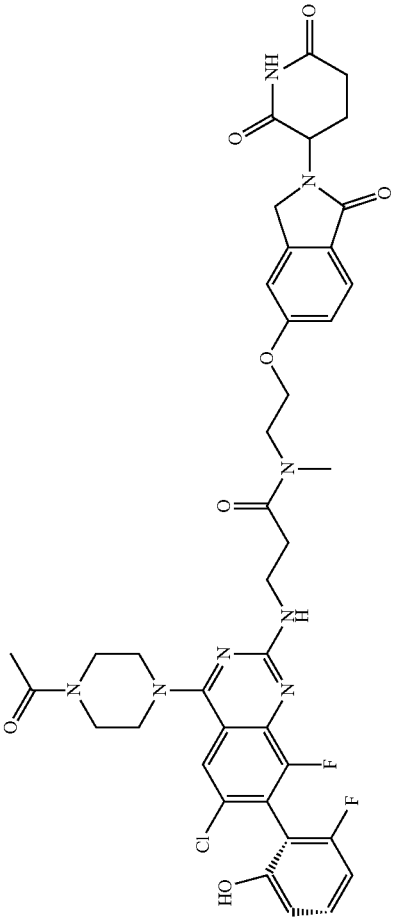 | 3-(((R)-4-(4-acetylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1-oxoisoindolin-5-yl)oxy)ethyl)-N-methylpropanamide | 1 |
| 99 | 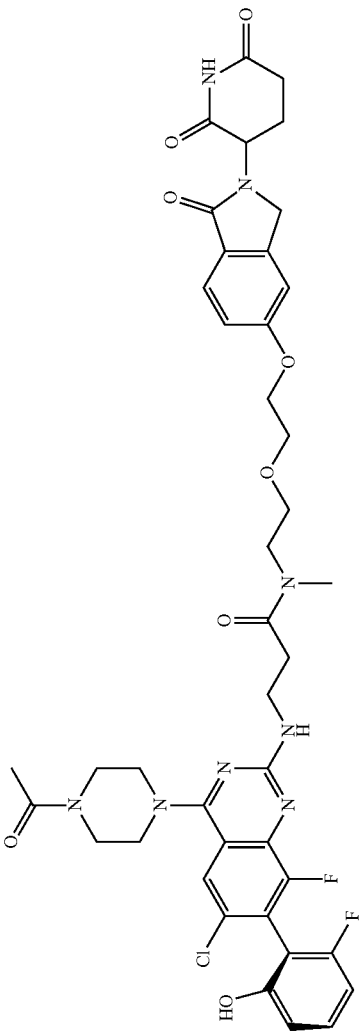 | 3-((4-(4-acetylpiperazin-1-yl)-6-chloro-8-fluoro-7-((S)-2-fluoro-6-hydroxyphenyl)quinazolin-2-yl)amino)-N-(2-(2-((2-(2,6-dioxopiperidin-3-yl)-1-oxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 100 | 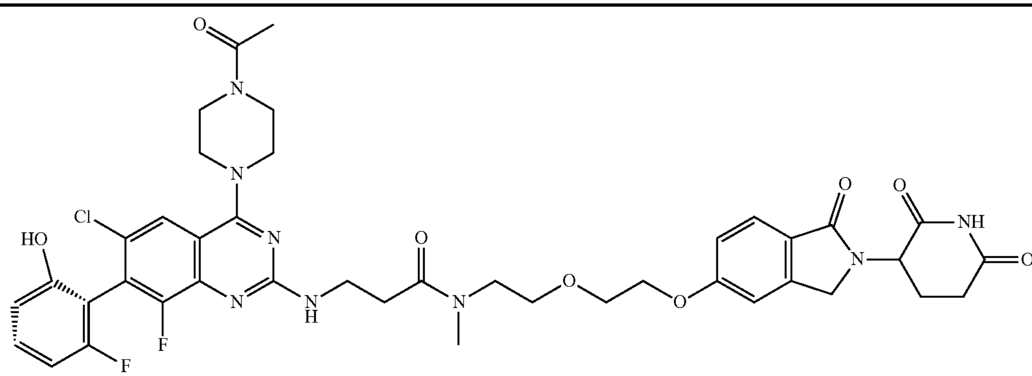 | 3-((4-(4-acetylpiperazin-1-yl)-6-chloro-8-fluoro-7-((R)-2-fluoro-6-hydroxyphenyl)quinazolin-2-yl)amino)-N-(2-((2-(2,6-dioxopiperidin-3-yl)-1-oxoisoindolin-5-yl)oxy)ethoxy)ethyl)-N-methylpropanamide | 1 |
| 101 | 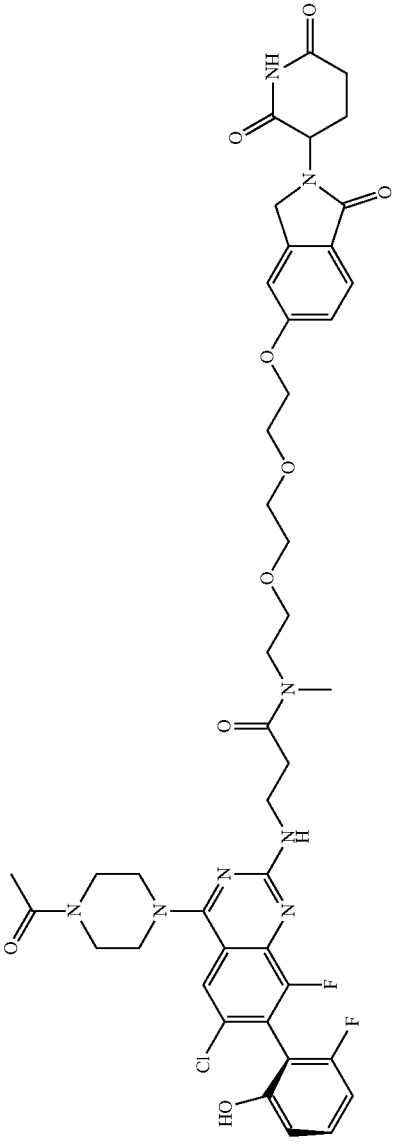 | 3-(((S)-4-(4-acetylpiperazin-1-yl)-6-chloro-8-fluoro-7-(2-fluoro-6-hydroxyphenyl)quinazolin-2-yl)amino)-N-(2-(2-(2-(2,6-dioxopiperidin-3-yl)-1-oxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 102 | 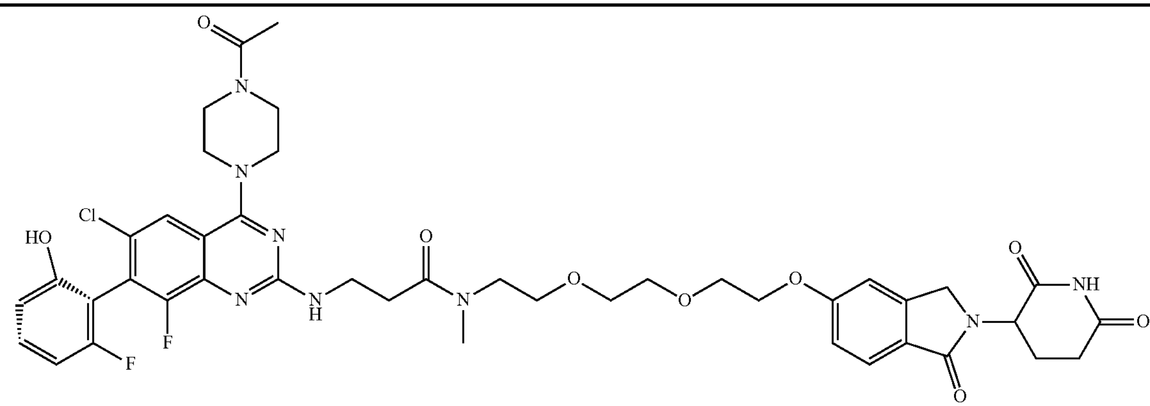 | 3-(((R)-4-(4-acetylpiperazin-1-yl)-6-chloro-8-fluoro-7-(2-fluoro-6-hydroxyphenyl)quinazolin-2-yl)amino)-N-(2-(2-(2-(2-(2,6-dioxopiperidin-3-yl)-1-oxoisoindolin-5-yl)oxy)ethoxy)ethoxy)ethyl)-N-methylpropanamide | 1 |
| 103 | 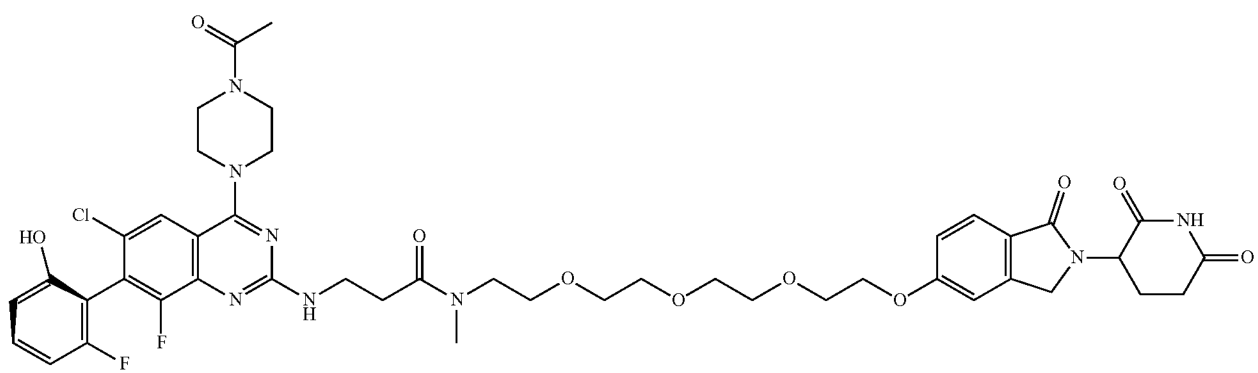 | 3-((4-(4-acetylpiperazin-1-yl)-6-chloro-8-fluoro-7-((S)-2-fluoro-6-hydroxyphenyl)quinazolin-2-yl)amino)-N-(2-(2-(2-(2-((2-(2,6-dioxopiperidin-3-yl)-1-oxoisoindolin-5-yl)oxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 104 | 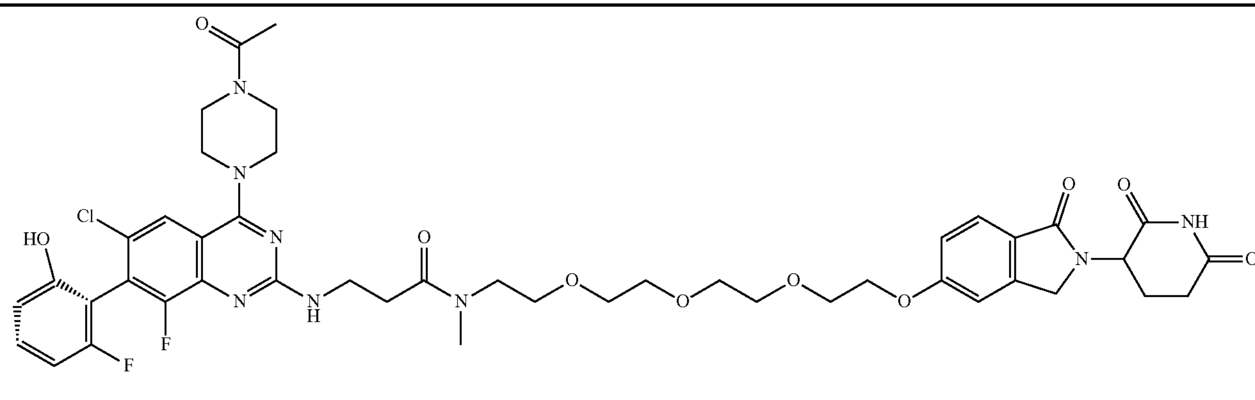 | 3-((4-(4-acetylpiperazin-1-yl)-6-chloro-8-fluoro-7-((R)-2-fluoro-6-hydroxyphenyl)quinazolin-2-yl)amino)-N-(2-(2-(2-(2-((2-(2,6-dioxopiperidin-3-yl)-1-oxoisoindolin-5-yl)oxy)ethoxy)ethoxy)ethoxy)ethyl)-N-methylpropanamide | 1 |
| 105 | 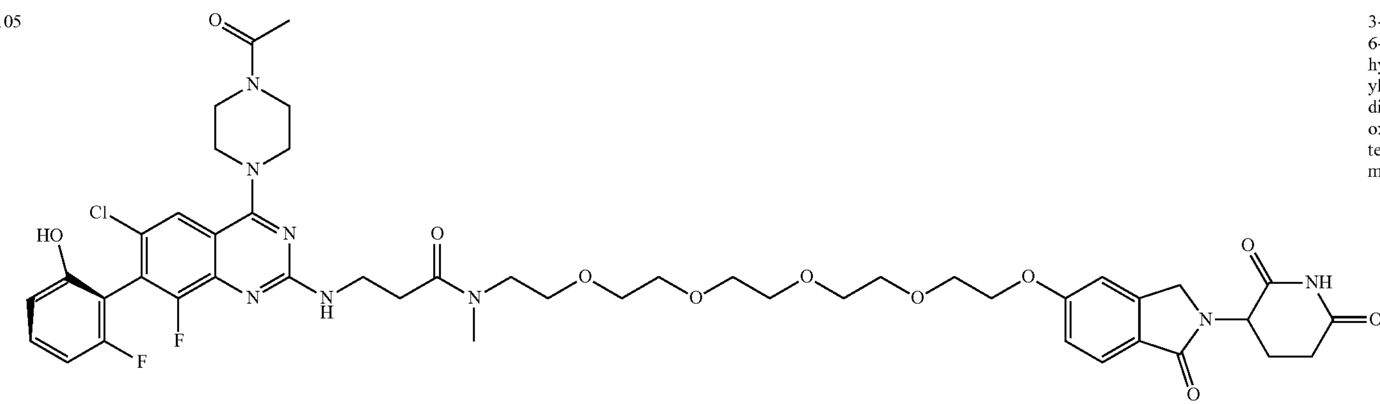 | 3-(((S)-4-(4-acetylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 106 | 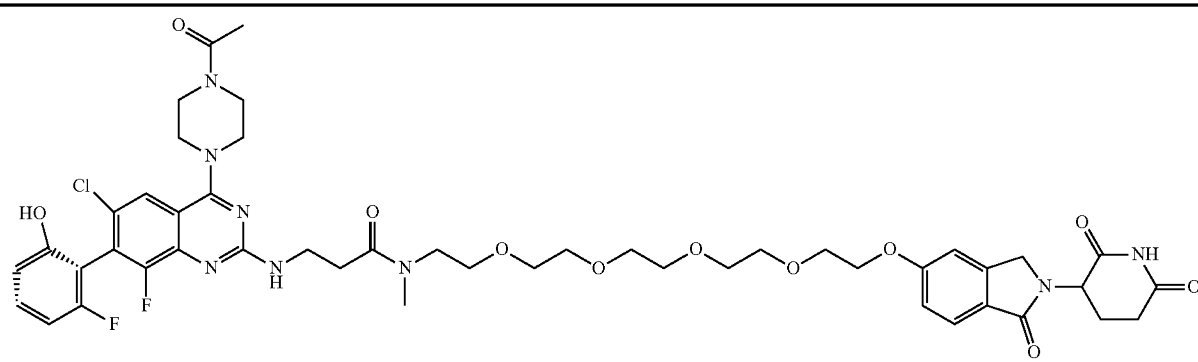 | 3-(((R)-4-(4-acetylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1-oxoisoindolin-5-yl)oxy)-3,6,9,12-tetraoxatetradecyl)-N-methylpropanamide | 1 |
| 107 | 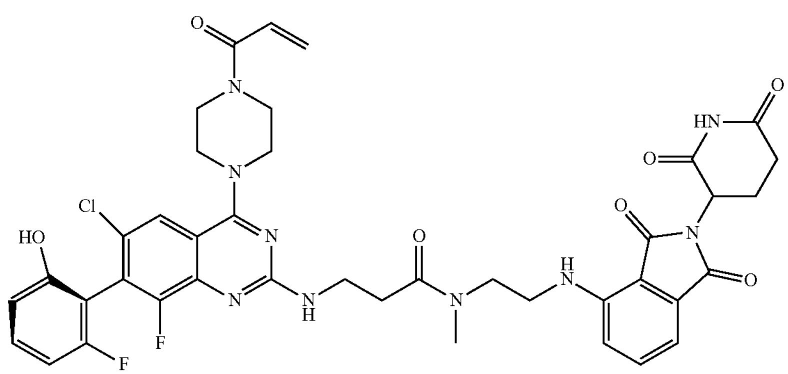 | 3-(((S)-4-(4-acryloylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-4-yl)amino)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 108 | 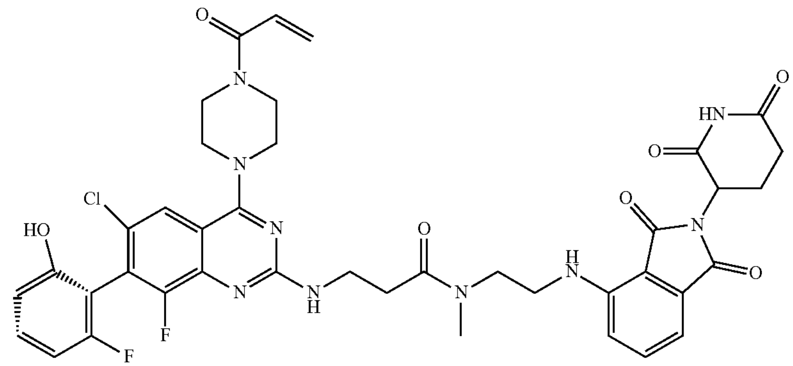 | 3-(((R)-4-(4-acryloylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-4-yl)amino)ethyl)-N-methylpropanamide | 1 |
| 109 | 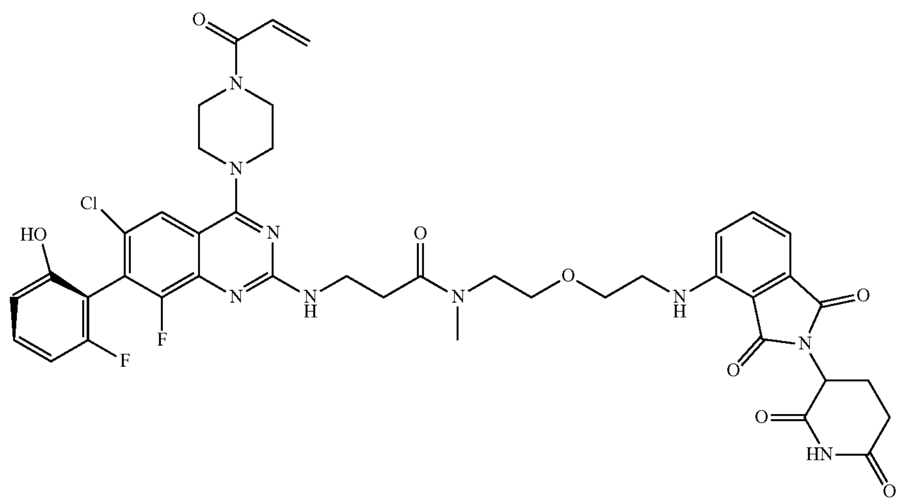 | 3-(((S)-4-(4-acryloylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-4-yl)amino)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 110 | 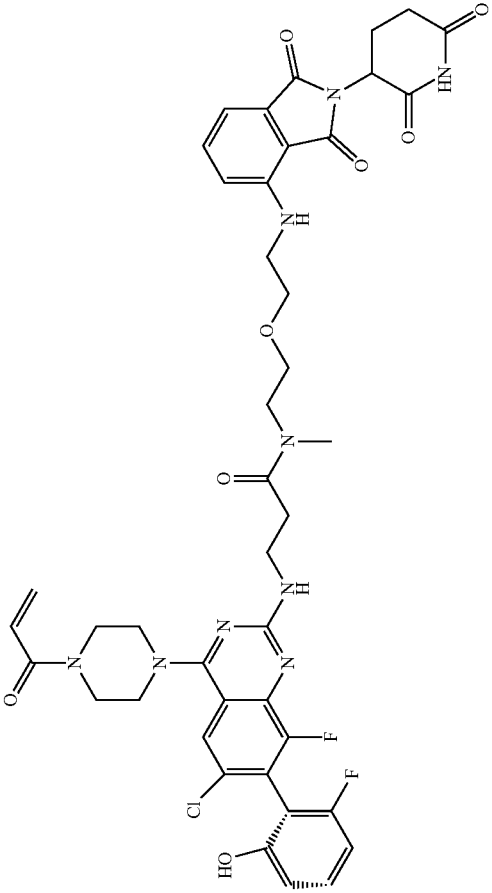 | 3-(((R)-4-(4-acryloylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-4-yl)amino)ethoxy)ethyl)-N-methylpropanamide | 1 |
| 111 | 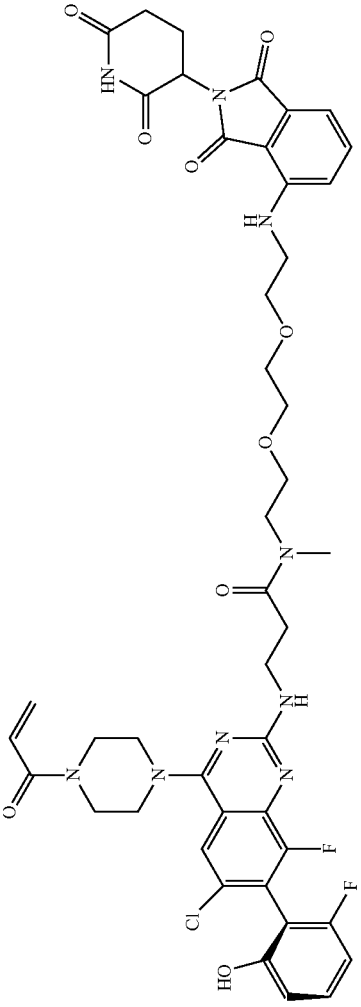 | 3-(((S)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 112 | 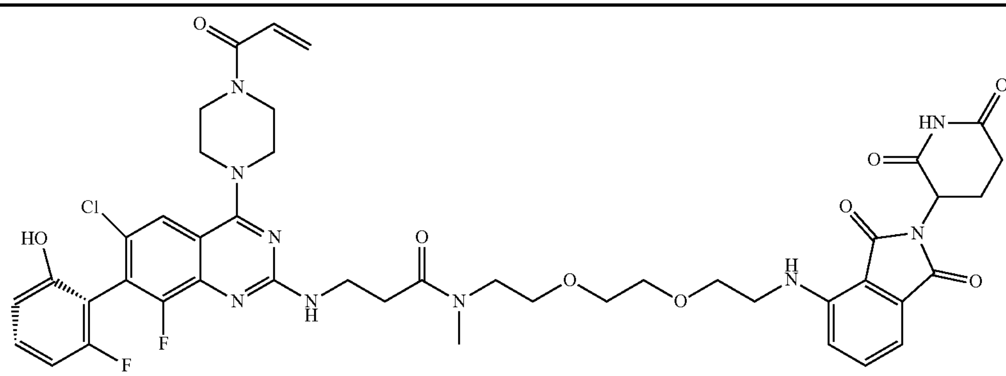 | 3-(((R)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide | 1 |
| 113 | 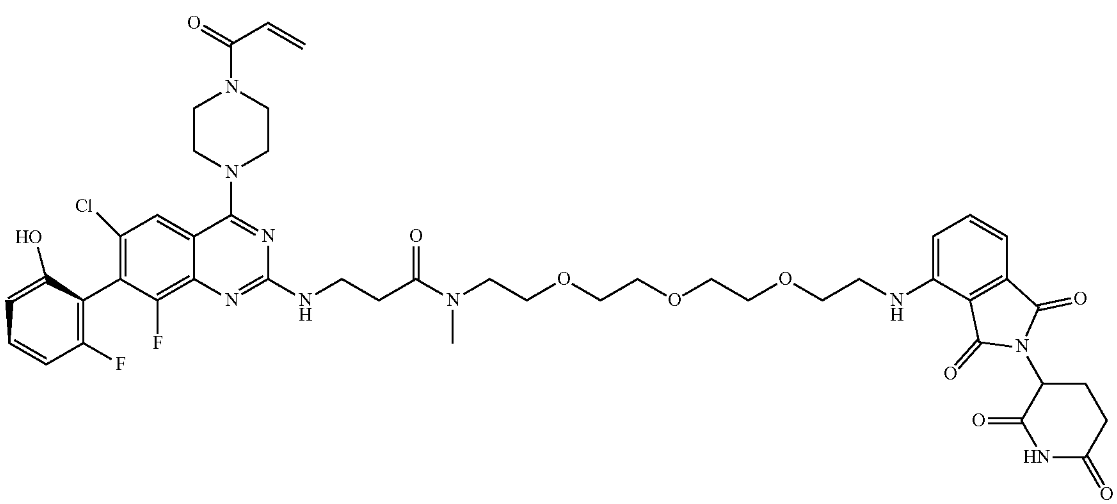 | 3-(((S)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 114 | 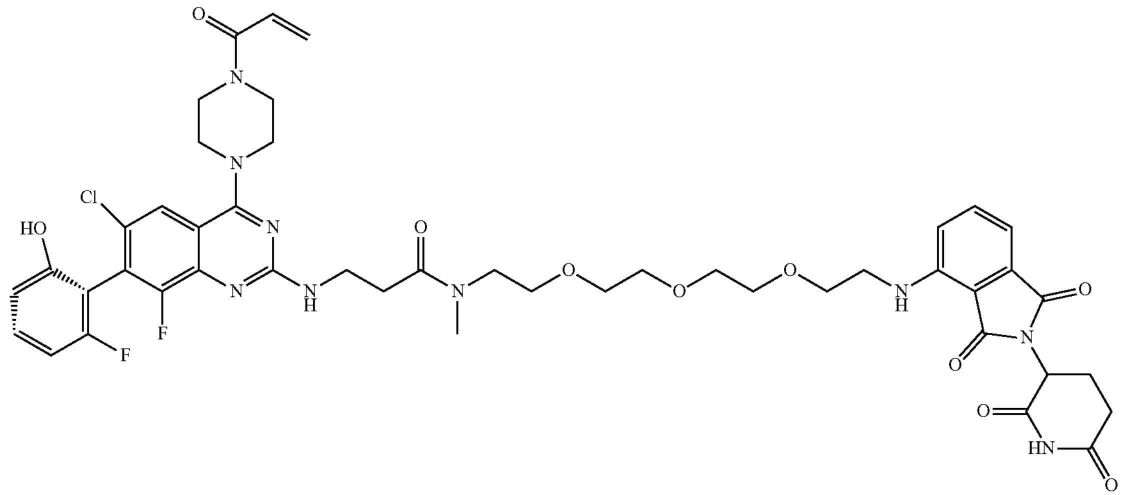 | 3-(((R)-4-(4-acryloylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide | 1 |
| 115 | 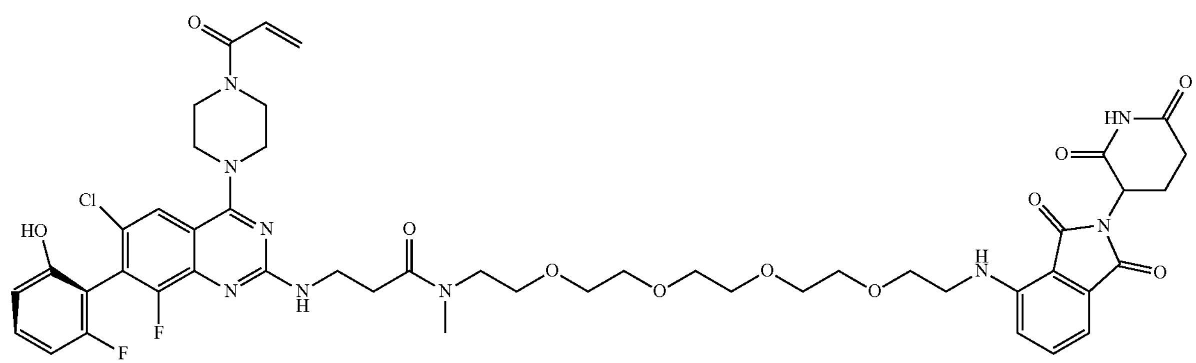 | 3-(((S)-4-(4-acryloylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 116 | 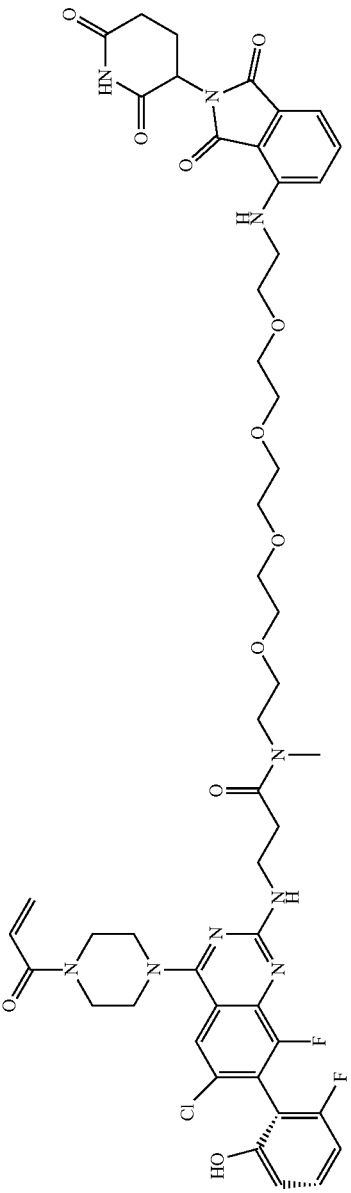 | 3-(((R)-4-(4-acryloylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |
| 117 | 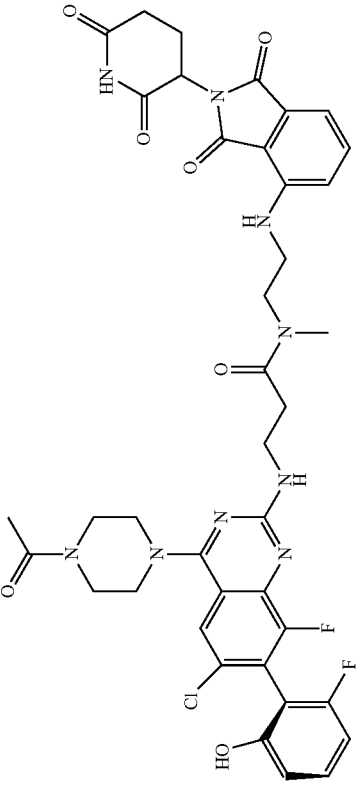 | 3-(((S)-4-(4-acetylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-4-yl)amino)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 118 | 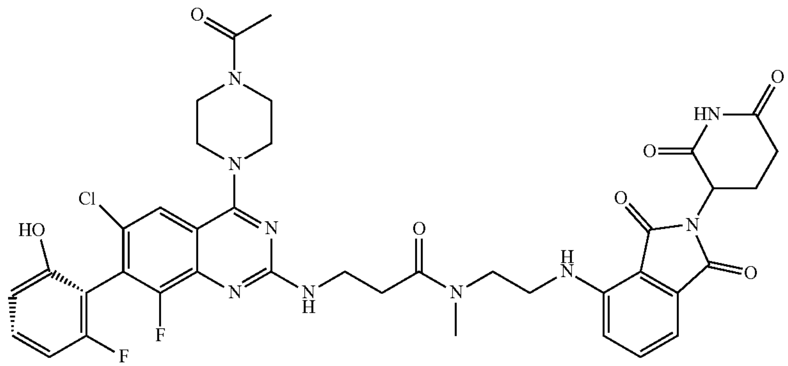 | 3-(((R)-4-(4-acetylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-4-yl)amino)ethyl)-N-methylpropanamide | 1 |
| 119 | 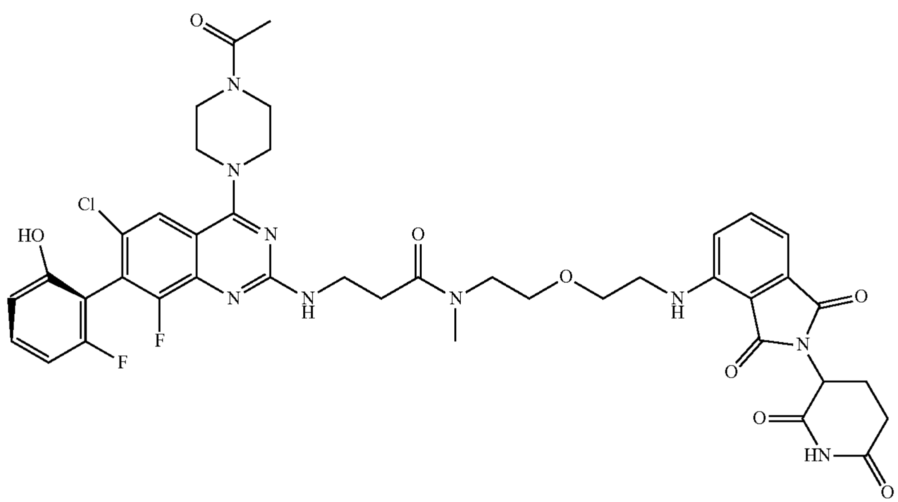 | 3-(((S)-4-(4-acetylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-4-yl)amino)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 120 | 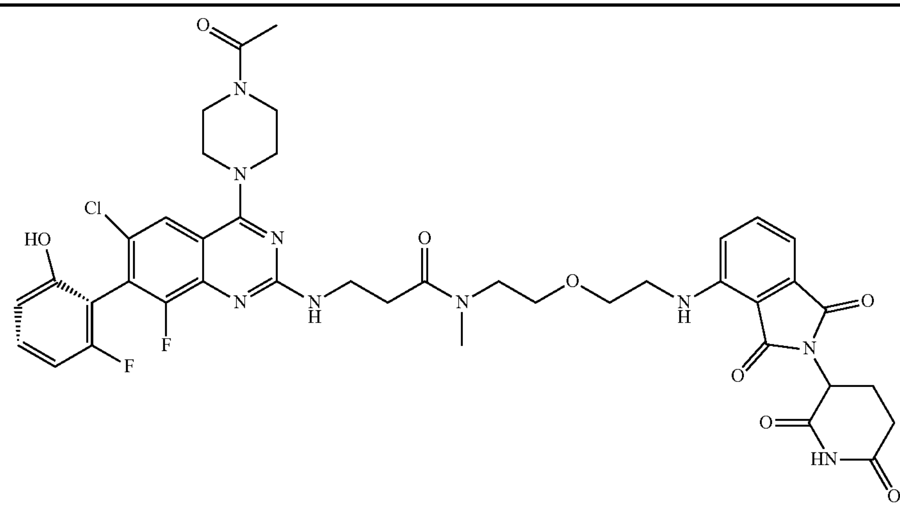 | 3-(((R)-4-(4-acetylpiperazin-1-yl)-6-chloro-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-4-yl)amino)ethoxy)ethyl)-N-methylpropanamide | 1 |
| 121 | 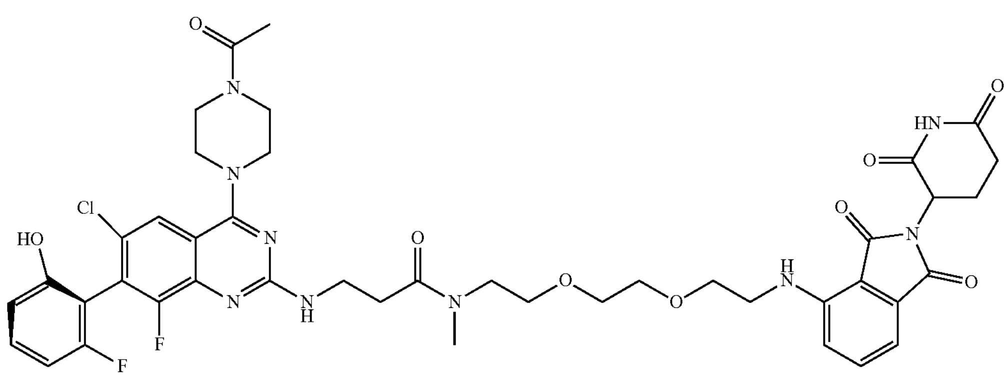 | 3-(((S)-4-(4-acetylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 122 | 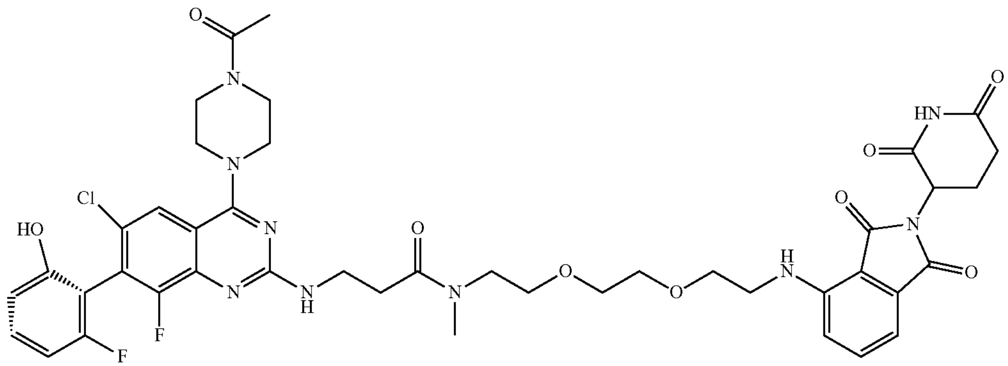 | 3-(((R)-4-(4-acetylpiperazin-1-yl)-6-chloro-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide | 1 |
| 123 | 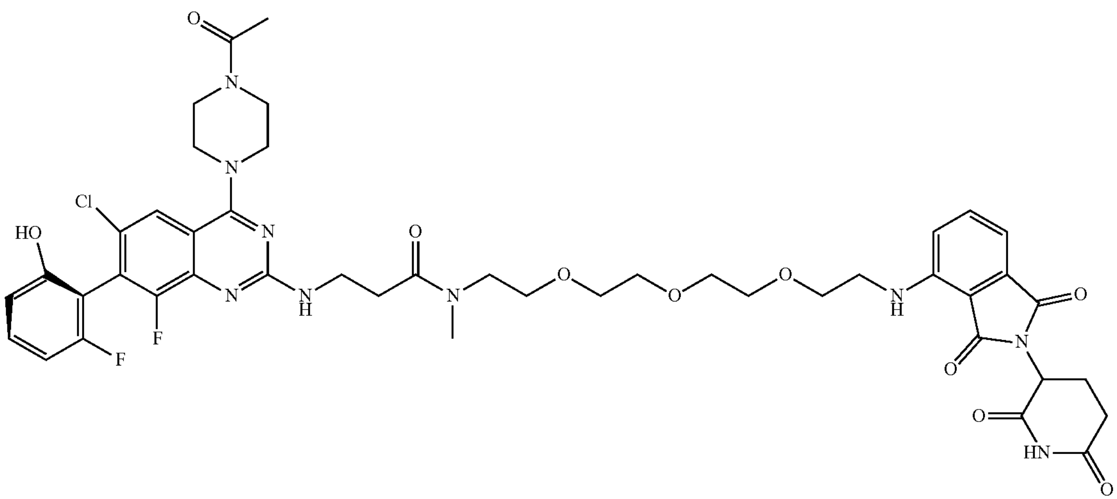 | 3-(((S)-4-(4-acetylpiperazin-1-yl)-6-chloro-8-fluoro-7-(2-fluoro-6-hydroxyphenyl)quinazolin-2-yl)amino)-N-(2-(2-(2-(2-((2-(2,6-dioxopiperidin-3-yl)-1,3-dioxoisoindolin-4-yl)amino)ethoxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 124 | 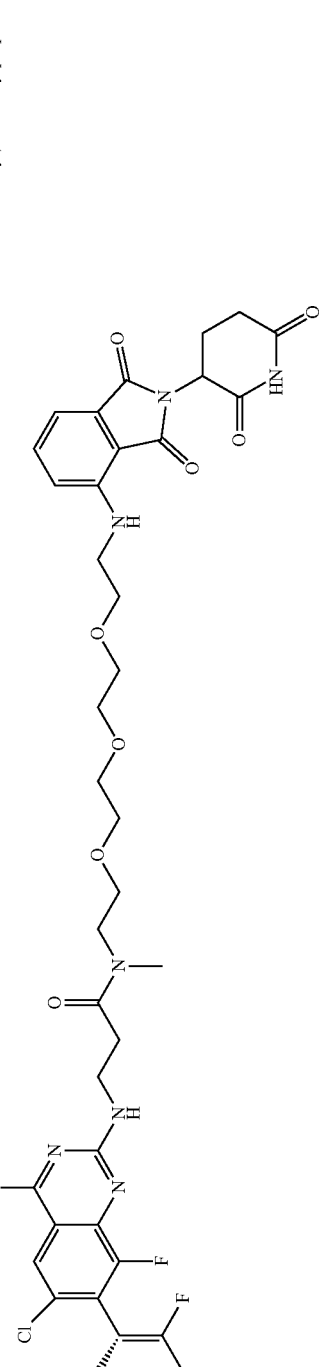 | 3-(((R)-4-(4-acetylpiperazin-1-yl)-6-chloro-8-fluoro-7-(2-fluoro-6-hydroxyphenyl)quinazolin-2-yl)amino)-N-(2-(2-(2-(2-((2-(2,6-dioxopiperidin-3-yl)-1,3-dioxoisoindolin-4-yl)amino)ethoxy)ethoxy)ethoxy)ethyl)-N-methylpropanamide | 1 |
| 125 | 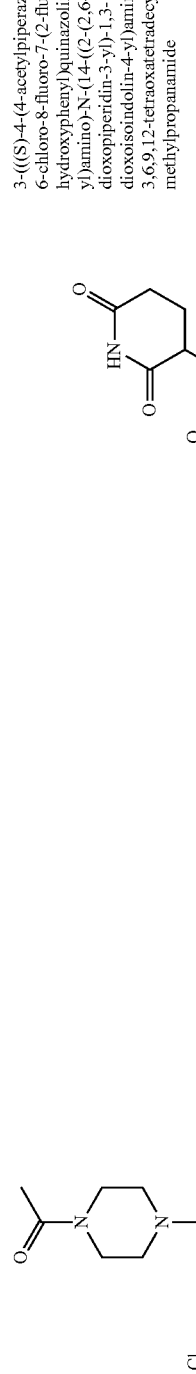 | 3-(((S)-4-(4-acetylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 126 | 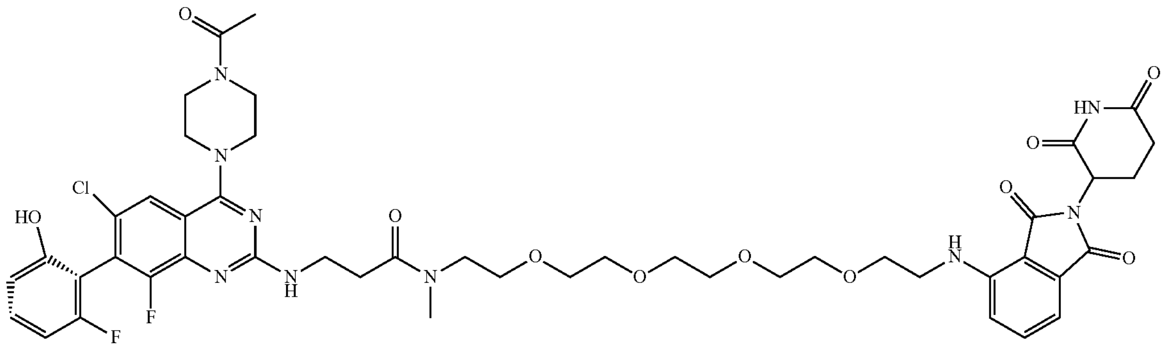 | 3-(((R)-4-(4-acetylpiperazin-1-yl)-6-chloro-8-fluoro-7-(2-fluoro-6-hydroxyphenyl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |
| 127 | 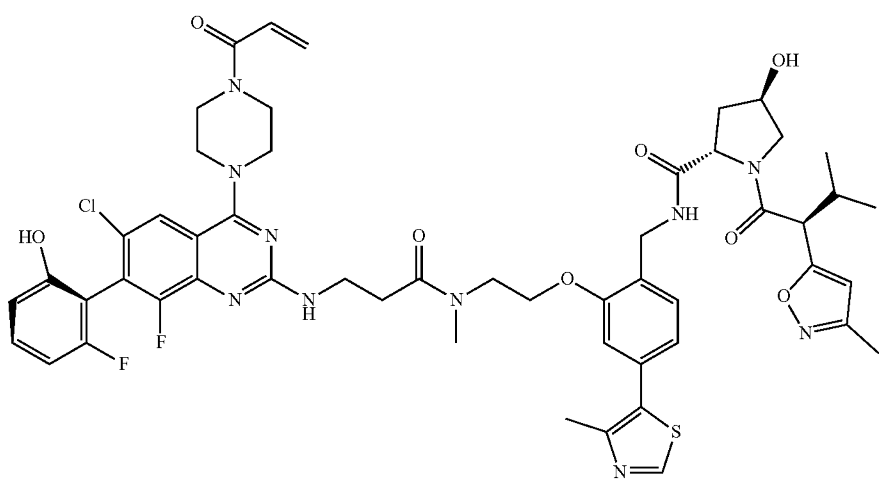 | (2S,4R)-N-(2-(2-(3-(((S)-4-(4-acryloylpiperazin-1-yl)-6-chloro-8-fluoro-7-(2-fluoro-6-hydroxyphenyl)quinazolin-2-yl)amino)-N-methylpropanamido)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 1 |

TABLE 6-continued

Compounds Prepared by Schemes 1 and 2

| Ex. No. | Structure | Compound Name | Synthetic Scheme |
|---|---|---|---|
| 128 | 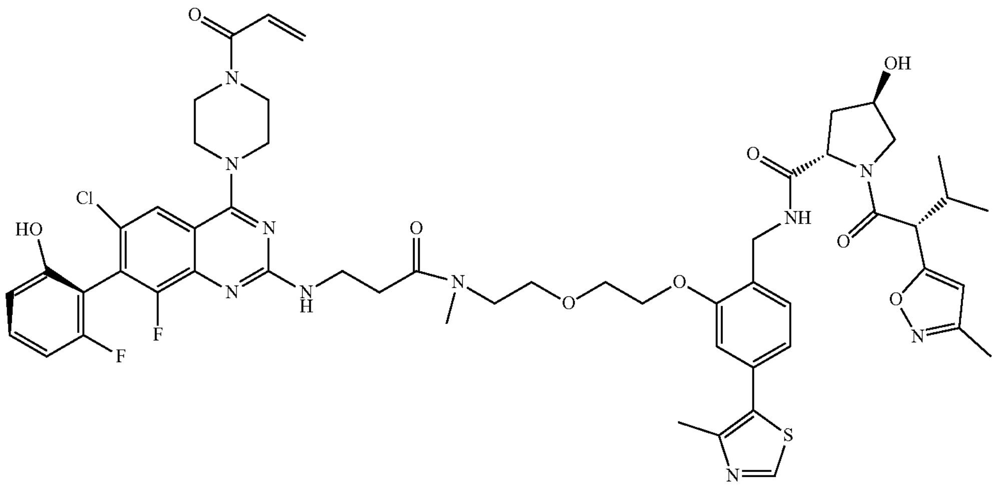 | (2S,4R)-N-(2-(2-(2-(3-(((S)-4-(4-acryloylpiperazin-1-yl)-6-chloro-8-fluoro-7-(2-fluoro-6-hydroxyphenyl)quinazolin-2-yl)amino)-N-methylpropanamido)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 1 |
| 129 | 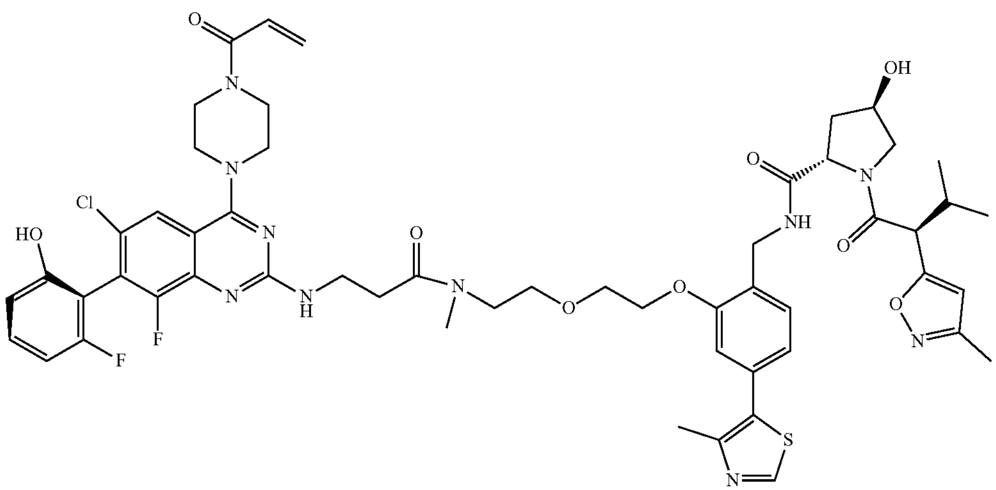 | (2S,4R)-N-(2-(2-(2-(3-(((S)-4-(4-acryloylpiperazin-1-yl)-6-chloro-8-fluoro-7-(2-fluoro-6-hydroxyphenyl)quinazolin-2-yl)amino)-N-methylpropanamido)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 1 |

TABLE 6-continued

Compounds Prepared by Schemes 1 and 2

| Ex. No. | Structure | Compound Name | Synthetic Scheme |
|---|---|---|---|
| 130 | 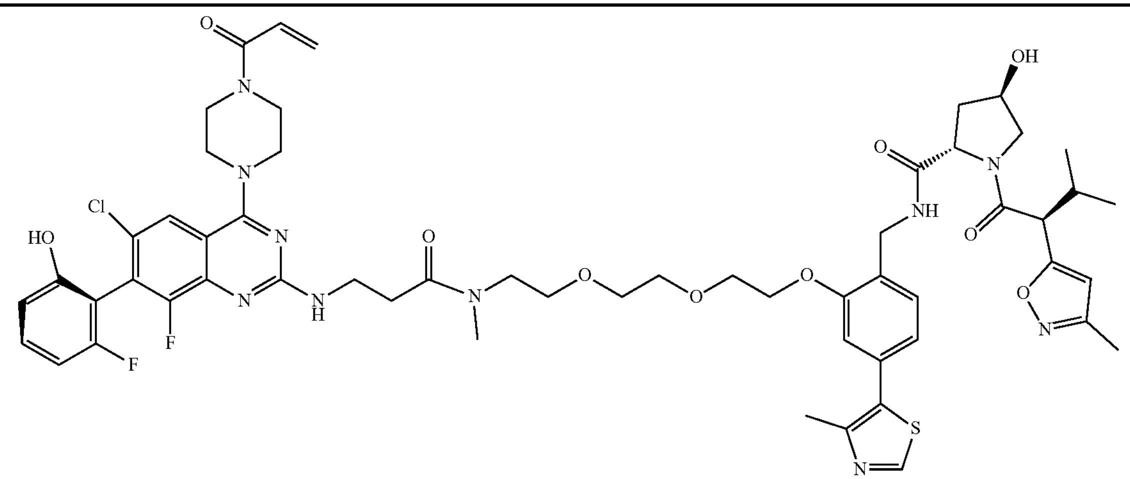 | (2S,4R)-N-(2-(2-(2-(2-(3-(((S)-4-(4-acryloylpiperazin-1-yl)-6-chloro-8-fluoro-7-(2-fluoro-6-hydroxyphenyl)quinazolin-2-yl)amino)-N-methylpropanamido)ethoxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 1 |
| 131 | 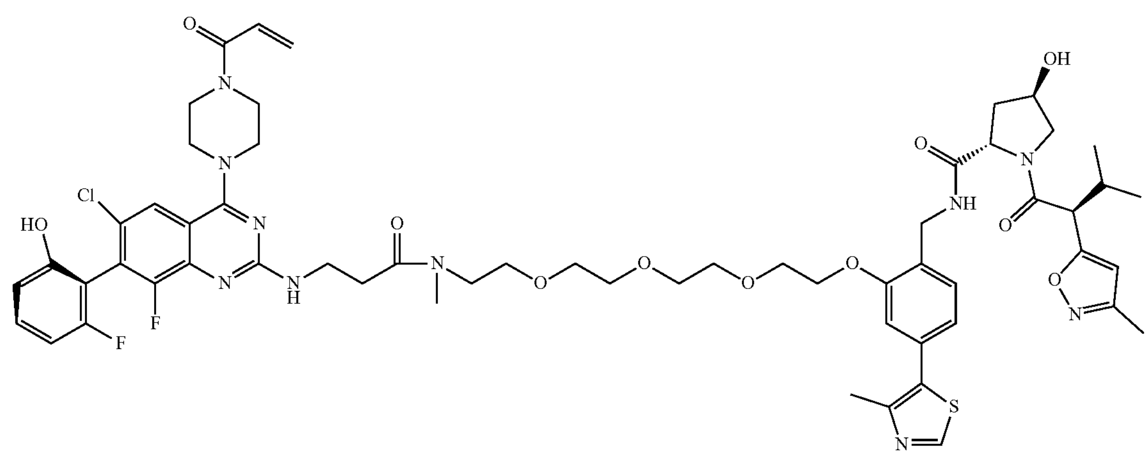 | (2S,4R)-N-(2-((15-(((S)-4-(4-acryloylpiperazin-1-yl)-6-chloro-8-fluoro-7-(2-fluoro-6-hydroxyphenyl)quinazolin-2-yl)amino)-12-methyl-13-oxo-3,6,9-trioxa-12-azapentadecyl)oxy)-4-(4-methylthiazol-5-yl)benzyl)-4-hydroxy-1-((S)-3-methyl-2-(3-methylisoxazol-5-yl)butanoyl)pyrrolidine-2-carboxamide | 1 |

TABLE 6-continued

Compounds Prepared by Schemes 1 and 2

| Ex. No. | Structure | Compound Name | Synthetic Scheme |
|---|---|---|---|
| 132 | 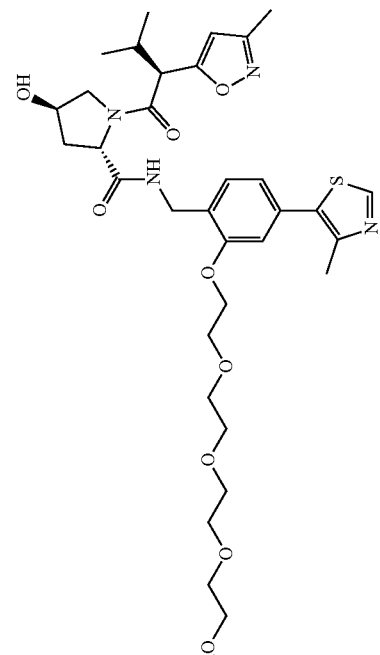 | (2S,4R)-N-(2-((18-(((S)-4-(4-acryloylpiperazin-1-yl)-6-chloro-8-fluoro-7-(2-fluoro-6-hydroxyphenyl)quinazolin-2-yl)amino)-15-methyl-16-oxo-3,6,9,12-tetraoxa-15-azaoctadecyl)oxy)-4-(4-methylthiazol-5-yl)benzyl)-4-hydroxy-1-((S)-3-methyl-2-(3-methylisoxazol-5-yl)butanoyl)pyrrolidine-2-carboxamide | 1 |
| 133 | 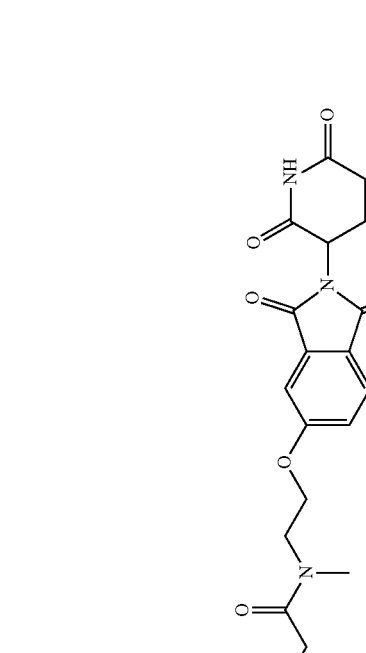 | 4-((7S)-6-chloro-2-((3-((2-((2-(2,6-dioxopiperidin-3-yl)-1,3-dioxoisoindolin-5-yl)oxy)ethyl)(methyl)amino)-3-oxopropyl)amino)-8-fluoro-7-(2-fluoro-6-hydroxyphenyl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 134 | 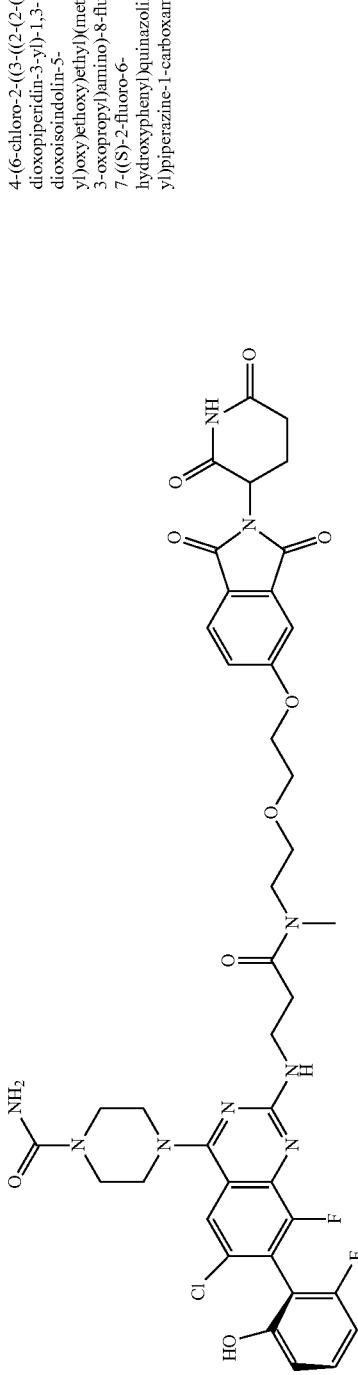 | 4-(6-chloro-2-((3-((2-((2-(2,6-dioxopiperidin-3-yl)-1,3-dioxoisoindolin-5-yl)oxy)ethoxy)ethyl)(methyl)amino)-3-oxopropyl)amino)-8-fluoro-7-((S)-2-fluoro-6-hydroxyphenyl)quinazolin-4-yl)piperazine-1-carboxamide | 1 |
| 135 | 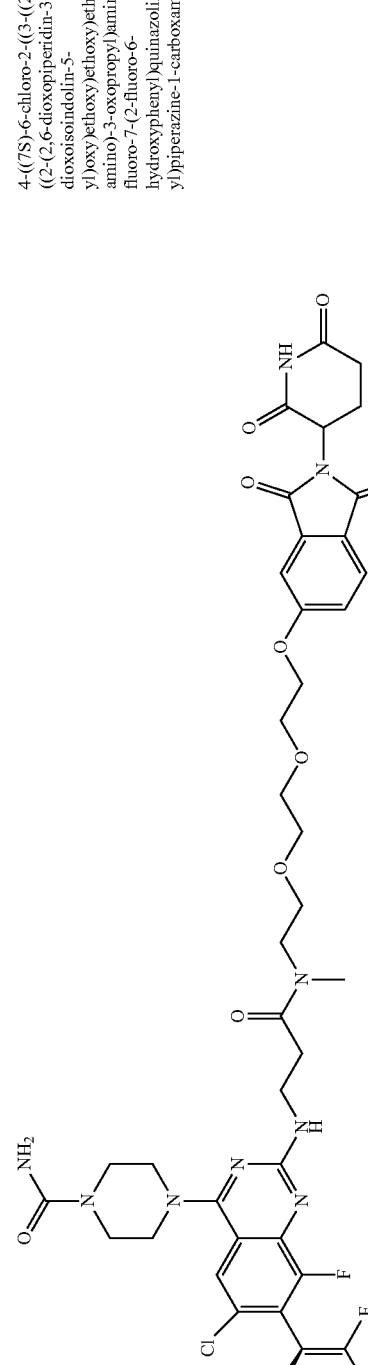 | 4-((7S)-6-chloro-2-((3-((2-(2-(2-((2-(2,6-dioxopiperidin-3-yl)-1,3-dioxoisoindolin-5-yl)oxy)ethoxy)ethoxy)ethyl)(methyl)amino)-3-oxopropyl)amino)-8-fluoro-7-(2-fluoro-6-hydroxyphenyl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 136 | 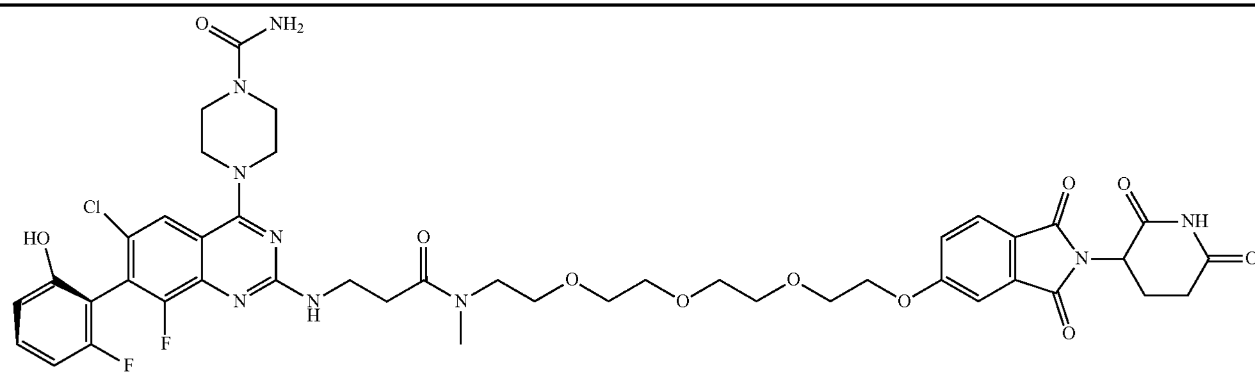 | 4-(6-chloro-2-((1-((2-(2,6-dioxopiperidin-3-yl)-1,3-dioxoisoindolin-5-yl)oxy)-12-methyl-13-oxo-3,6,9-trioxa-12-azapentadecan-15-yl)amino)-8-fluoro-7-((S)-2-fluoro-6-hydroxyphenyl)quinazolin-4-yl)piperazine-1-carboxamide | 1 |
| 137 | 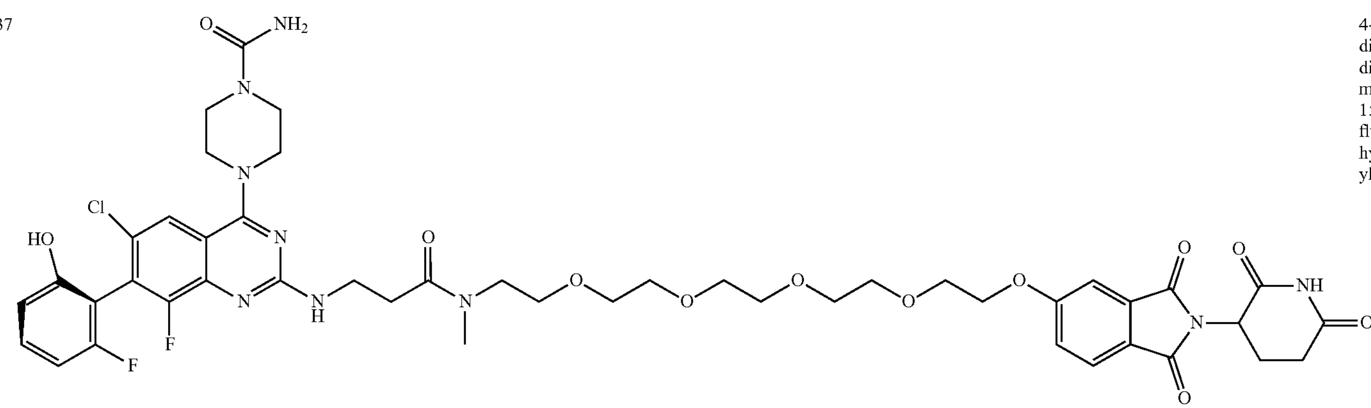 | 4-((7S)-6-chloro-2-((1-((2-(2,6-dioxopiperidin-3-yl)-1,3-dioxoisoindolin-5-yl)oxy)-15-methyl-16-oxo-3,6,9,12-tetraoxa-15-azaoctadecan-18-yl)amino)-8-fluoro-7-(2-fluoro-6-hydroxyphenyl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 138 | 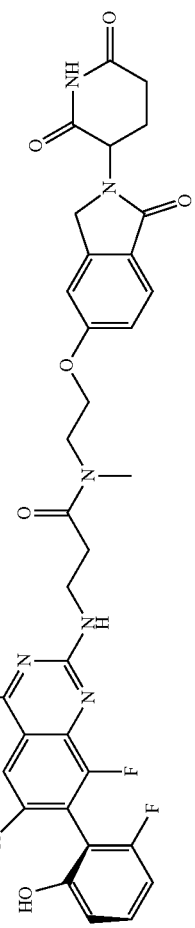 | 4-((7S)-6-chloro-2-((3-((2-((2-(2,6-dioxopiperidin-3-yl)-1-oxoisoindolin-5-yl)oxy)ethyl)(methyl)amino)-3-oxopropyl)amino)-8-fluoro-7-(2-fluoro-6-hydroxyphenyl)quinazolin-4-yl)piperazine-1-carboxamide | 1 |
| 139 | 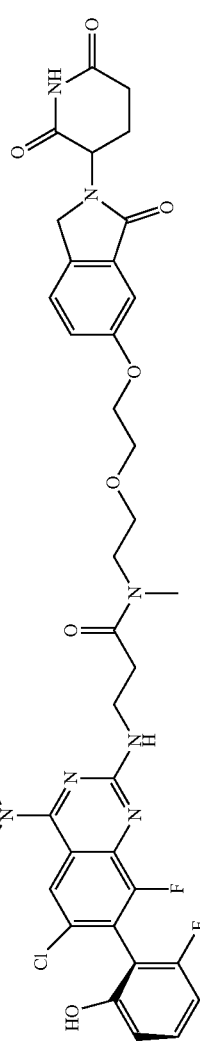 | 4-(6-chloro-2-((3-((2-(2-((2-(2,6-dioxopiperidin-3-yl)-1-oxoisoindolin-5-yl)oxy)ethoxy)ethyl)(methyl)amino)-3-oxopropyl)amino)-8-fluoro-7-((S)-2-fluoro-6-hydroxyphenyl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 140 | 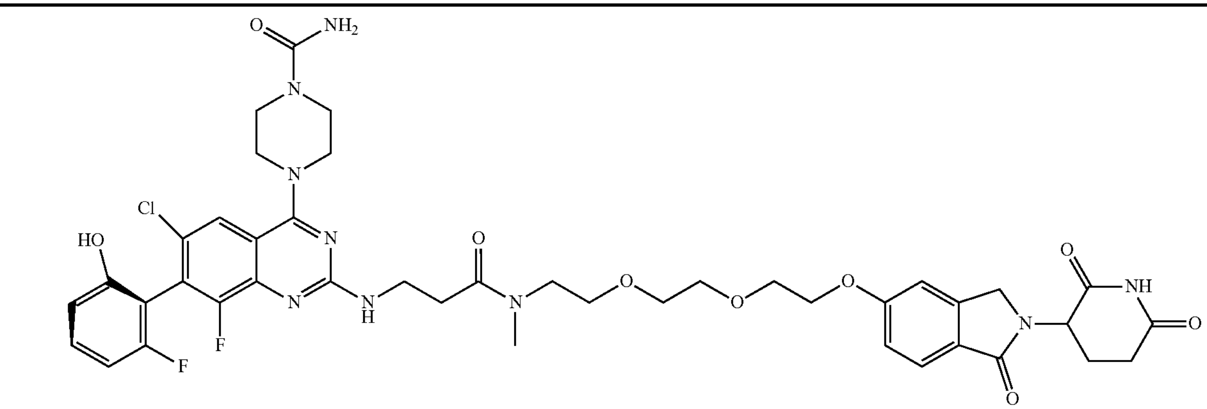 | 4-((7S)-6-chloro-2-((3-((2-(2-(2-((2,6-dioxopiperidin-3-yl)-1-oxoisoindolin-5-yl)oxy)ethoxy)ethoxy)ethyl)(methyl)amino)-3-oxopropyl)amino)-8-fluoro-7-(2-fluoro-6-hydroxyphenyl)quinazolin-4-yl)piperazine-1-carboxamide | 1 |
| 141 | 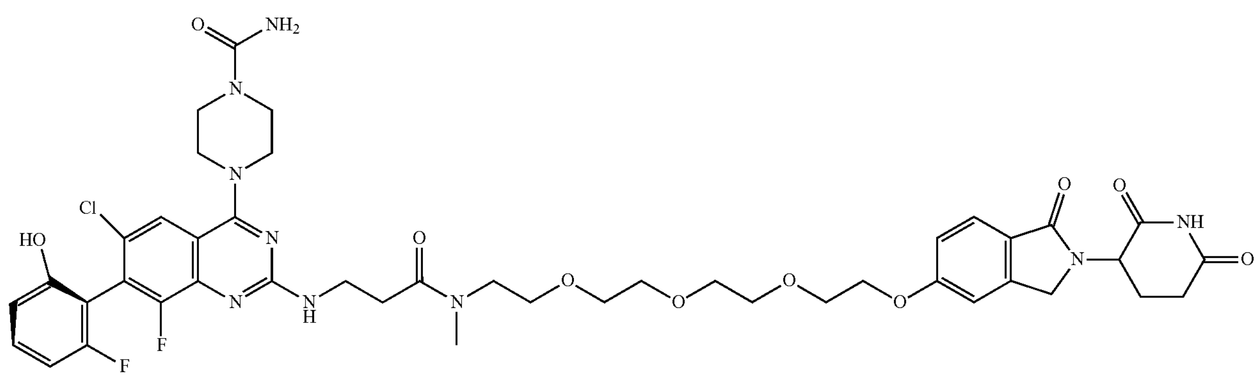 | 4-(6-chloro-2-((1-(2-(2,6-dioxopiperidin-3-yl)-1-oxoisoindolin-5-yl)oxy)-12-methyl-13-oxo-3,6,9-trioxa-12-azapentadecan-15-yl)amino)-8-fluoro-7-((S)-2-fluoro-6-hydroxyphenyl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 142 | 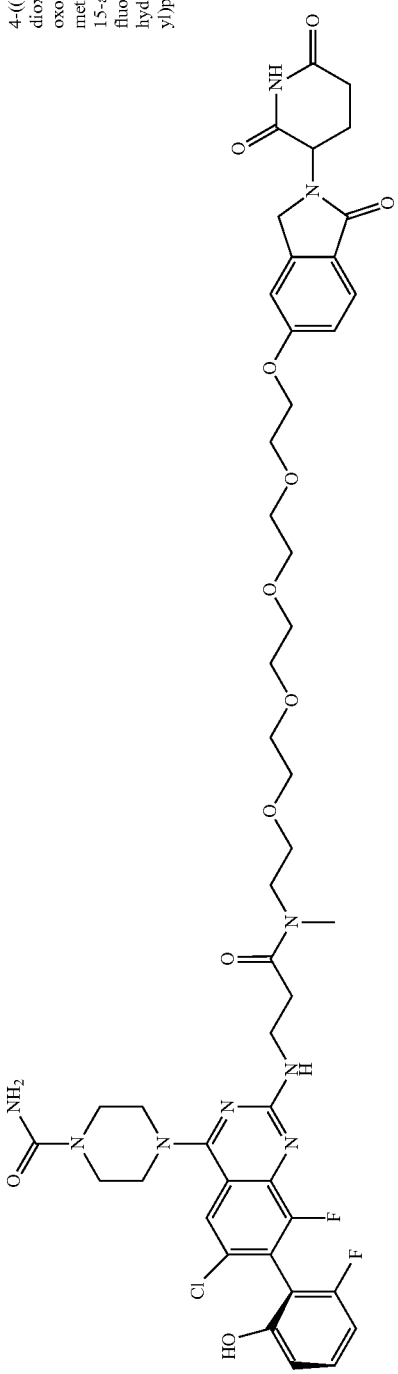 | 4-((7S)-6-chloro-2-((1-((2-(2,6-dioxopiperidin-3-yl)-1-oxoisoindolin-5-yl)oxy)-15-methyl-16-oxo-3,6,9,12-tetraoxa-15-azaoctadecan-18-yl)amino)-8-fluoro-7-(2-fluoro-6-hydroxyphenyl)quinazolin-4-yl)piperazine-1-carboxamide | 1 |
| 143 | 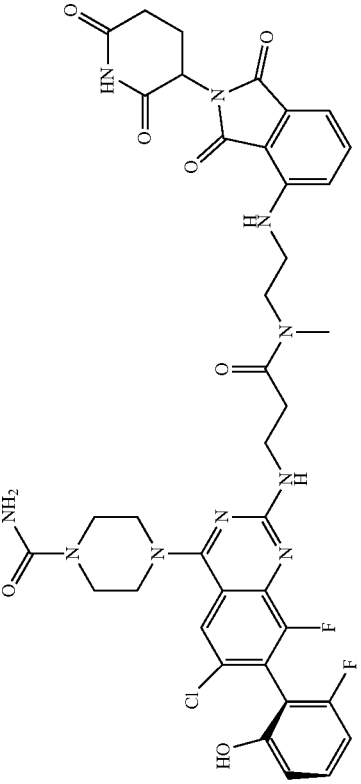 | 4-((7S)-6-chloro-2-((3-((2-(2-(2,6-dioxopiperidin-3-yl)-1,3-dioxoisoindolin-4-yl)amino)ethyl)(methyl)amino)-3-oxopropyl)amino)-8-fluoro-7-(2-fluoro-6-hydroxyphenyl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 144 | 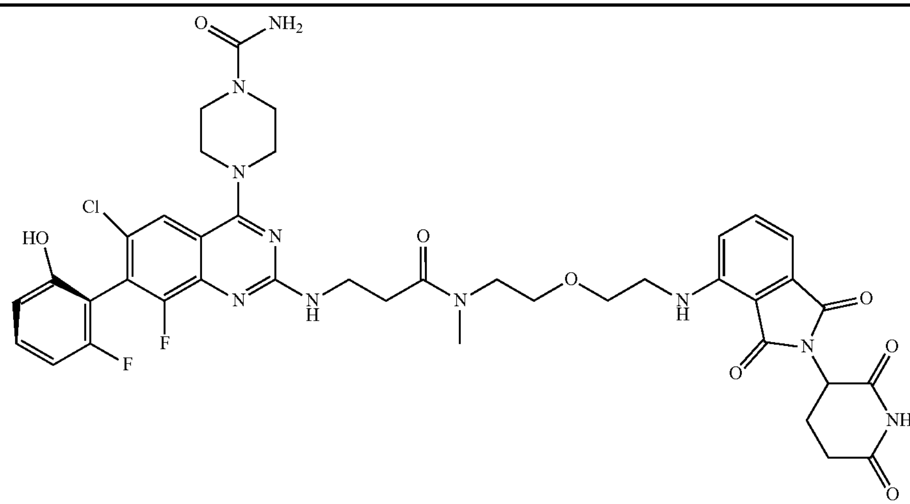 | 4-((7S)-6-chloro-2-((3-((2-(2-((2-(2,6-dioxopiperidin-3-yl)-1,3-dioxoisoindolin-4-yl)amino)ethoxy)ethyl)(methyl)amino)-3-oxopropyl)amino)-8-fluoro-7-(2-fluoro-6-hydroxyphenyl)quinazolin-4-yl)piperazine-1-carboxamide | 1 |
| 145 | 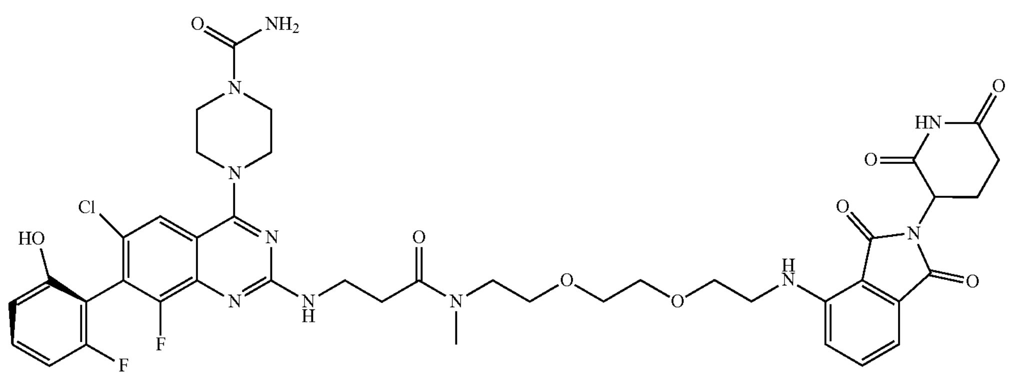 | 4-((7S)-6-chloro-2-((3-(2-(2-(2-((2-(2,6-dioxopiperidin-3-yl)-1,3-dioxoisoindolin-4-yl)amino)ethoxy)ethoxy)ethyl)(methyl)amino)-3-oxopropyl)amino)-8-fluoro-7-(2-fluoro-6-hydroxyphenyl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 146 | 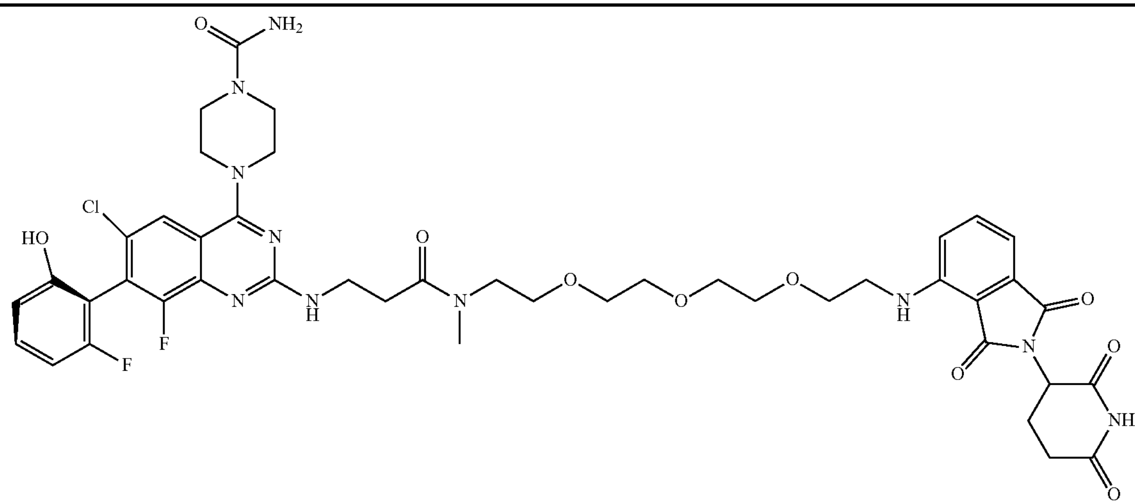 | 4-((7S)-6-chloro-2-((1-((2-(2,6-dioxopiperidin-3-yl)-1,3-dioxoisoindolin-4-yl)amino)-12-methyl-13-oxo-3,6,9-trioxa-12-azapentadecan-15-yl)amino)-8-fluoro-7-(2-fluoro-6-hydroxyphenyl)quinazolin-4-yl)piperazine-1-carboxamide | 1 |
| 147 | 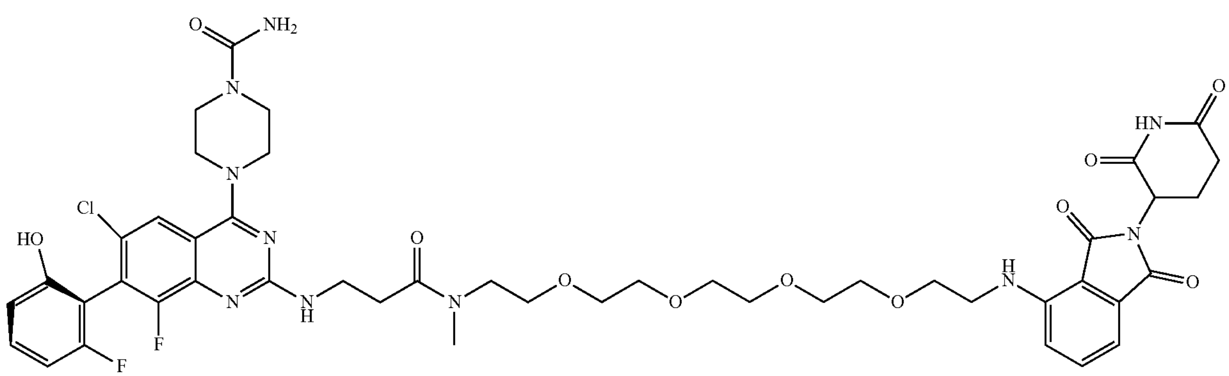 | 4-((7S)-6-chloro-2-((1-((2-(2,6-dioxopiperidin-3-yl)-1,3-dioxoisoindolin-4-yl)amino)-15-methyl-16-oxo-3,6,9,12-tetraoxa-15-azaoctadecan-18-yl)amino)-8-fluoro-7-(2-fluoro-6-hydroxyphenyl)quinazolin-4-yl)piperazine-1-carboxamide | 1 |

TABLE 6-continued

Compounds Prepared by Schemes 1 and 2

| Ex. No. | Structure | Compound Name | Synthetic Scheme |
|---|---|---|---|
| 148 | 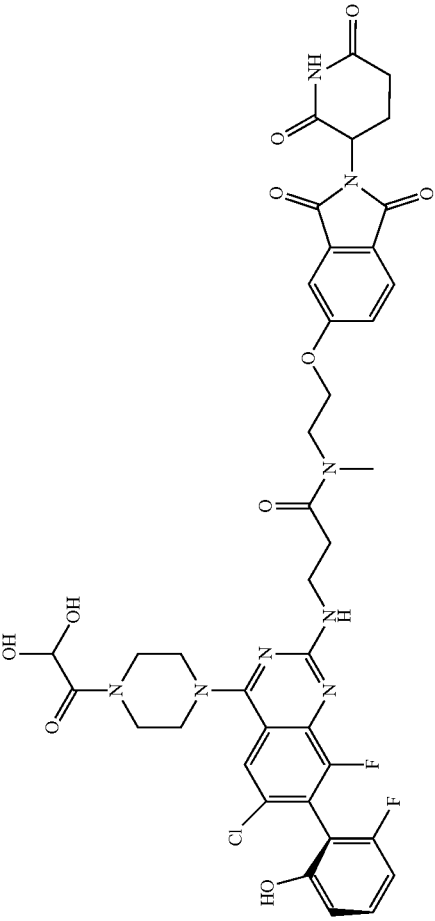 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(2-((2-(2,6-dioxopiperidin-3-yl)-1,3-dioxoisoindolin-5-yl)oxy)ethyl)-N-methylpropanamide | 1 |
| 149 | 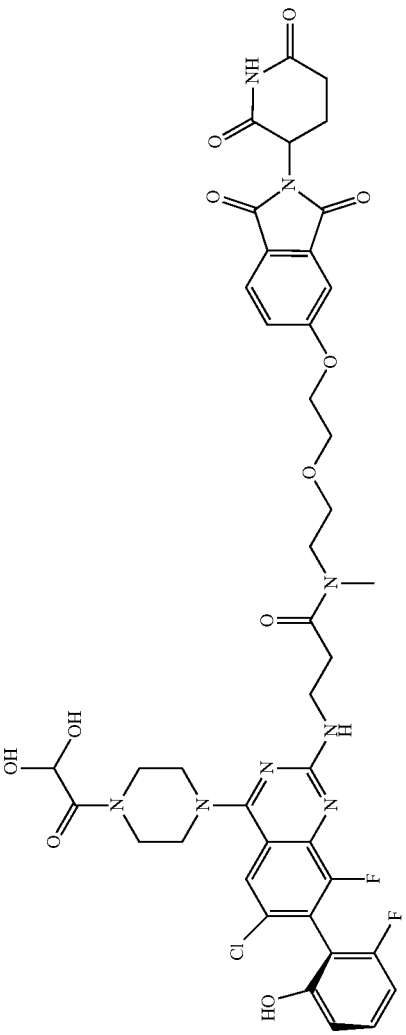 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 150 | 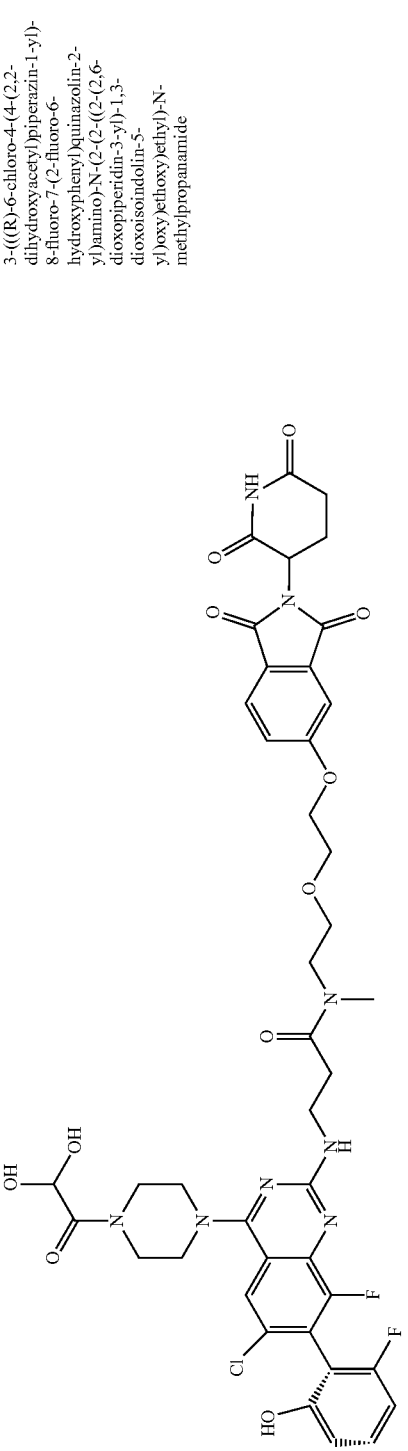 | 3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |
| 151 | 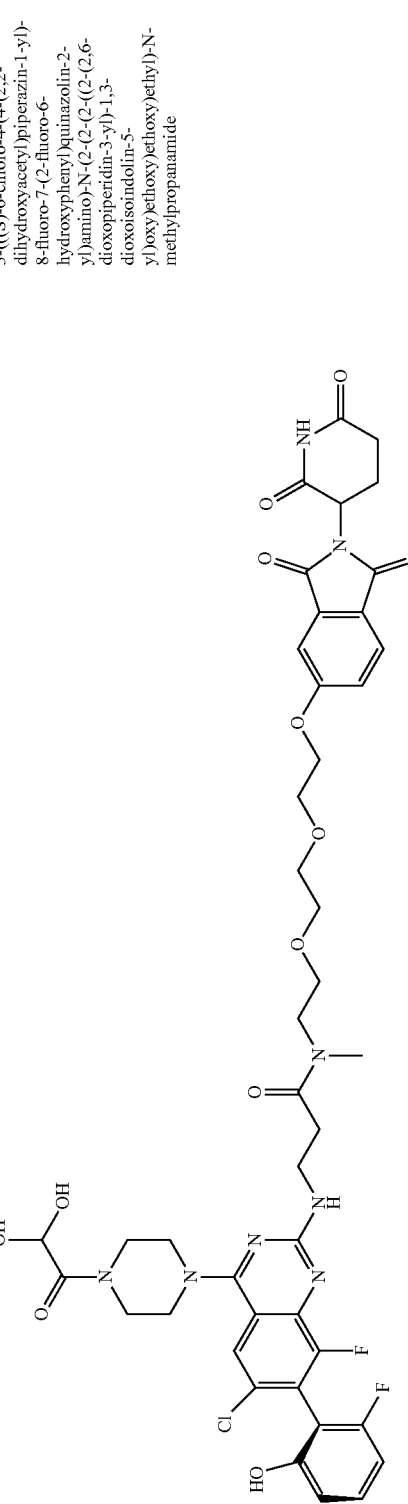 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-5-yl)oxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 152 | 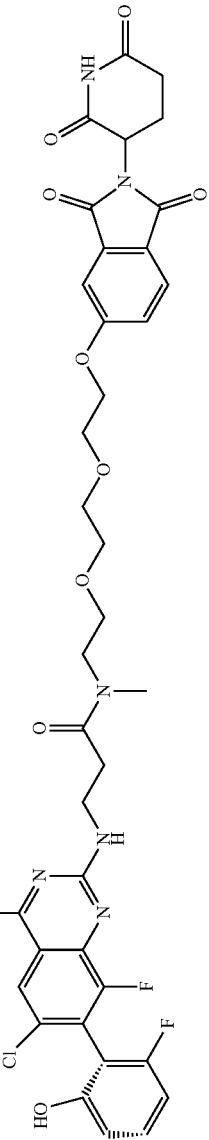 | 3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide | 1 |
| 153 | 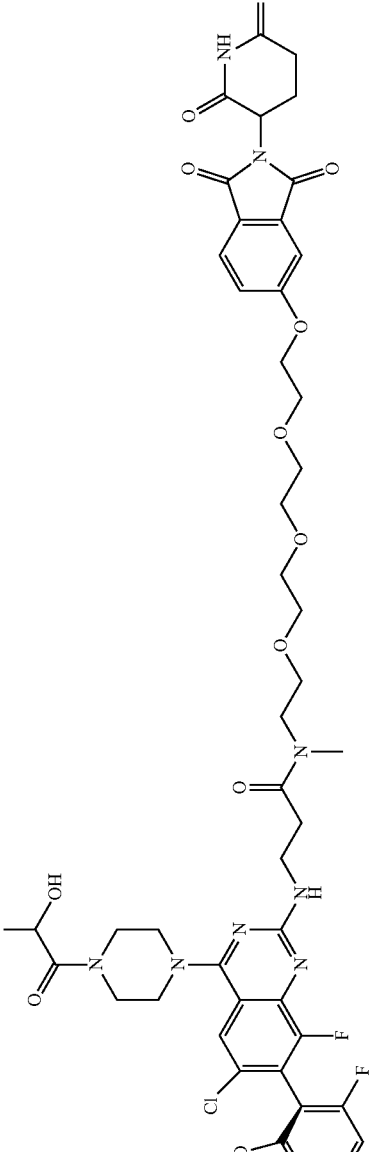 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-5-yl)oxy)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 154 | 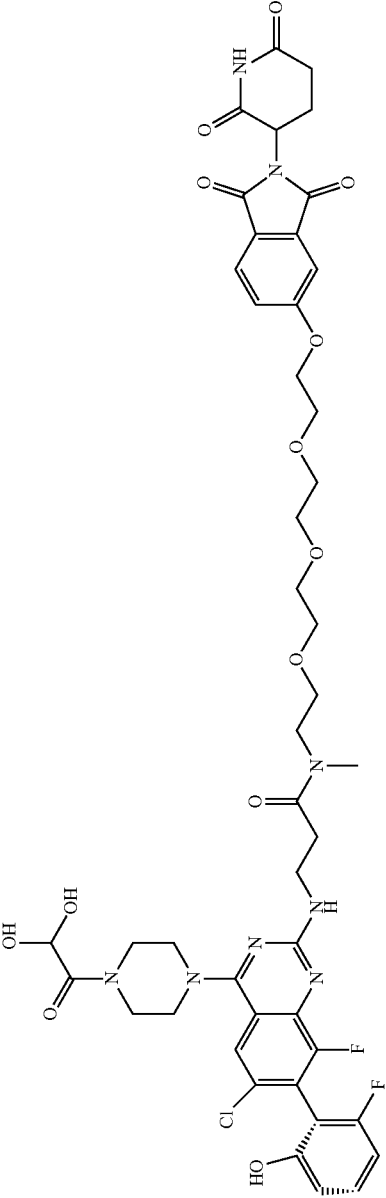 | 3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-(2-(2-((2,6-dioxopiperidin-3-yl)-1,3-dioxoisoindolin-5-yl)oxy)ethoxy)ethoxy)ethoxy)ethyl)-N-methylpropanamide | 1 |
| 155 | 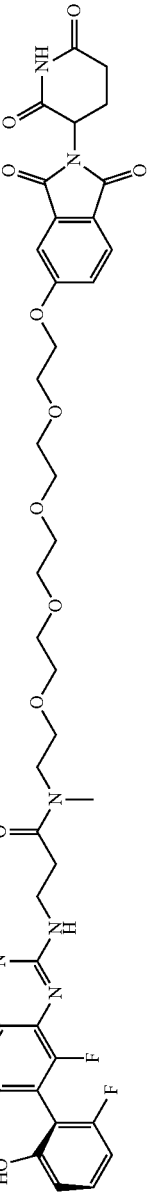 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(14-((2-(2,6-dioxopiperidin-3-yl)-1,3-dioxoisoindolin-5-yl)oxy)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 156 | 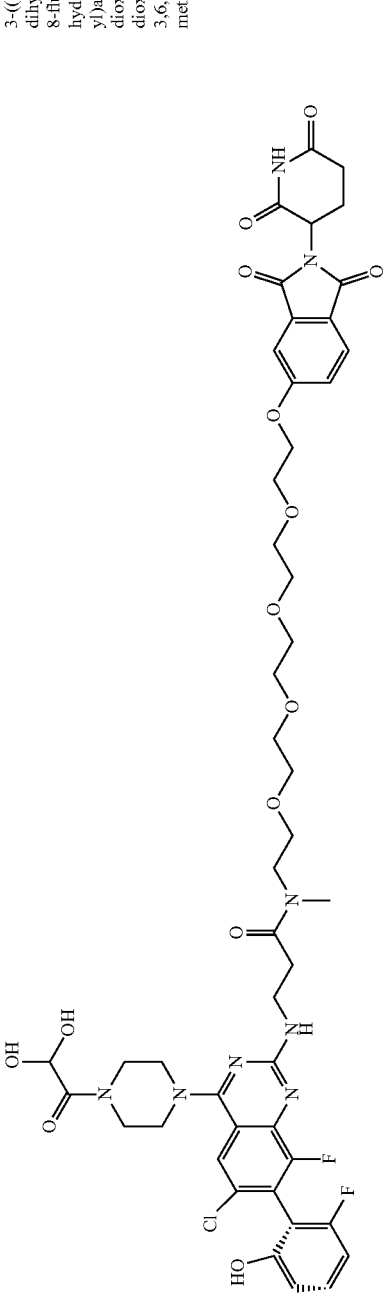 | 3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-(14-((2-(2,6-dioxopiperidin-3-yl)-1,3-dioxoisoindolin-5-yl)oxy)-3,6,9,12-tetraoxatetradecyl)-N-methylpropanamide | 1 |
| 157 | 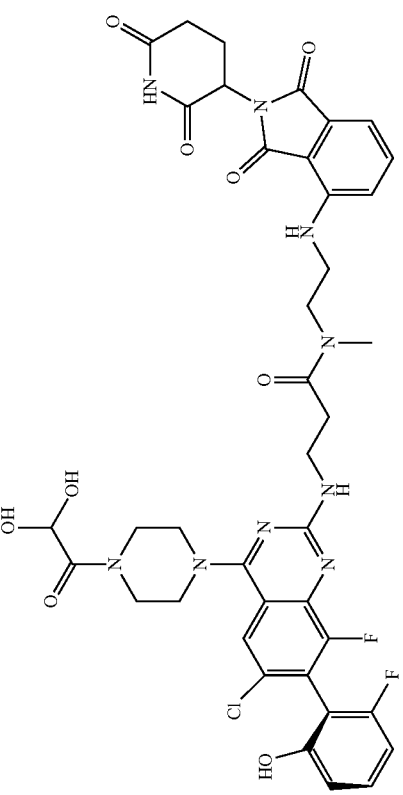 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(2-((2-(2,6-dioxopiperidin-3-yl)-1,3-dioxoisoindolin-4-yl)amino)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 158 | 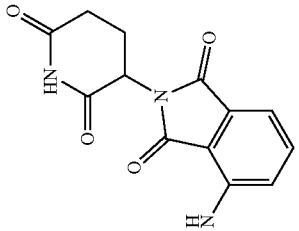 | 3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-(2-((2-(2,6-dioxopiperidin-3-yl)-1,3-dioxoisoindolin-4-yl)amino)ethyl)-N-methylpropanamide | 1 |
| 159 | 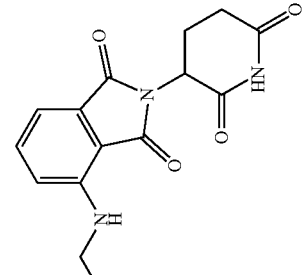 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-4-yl)amino)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 160 | 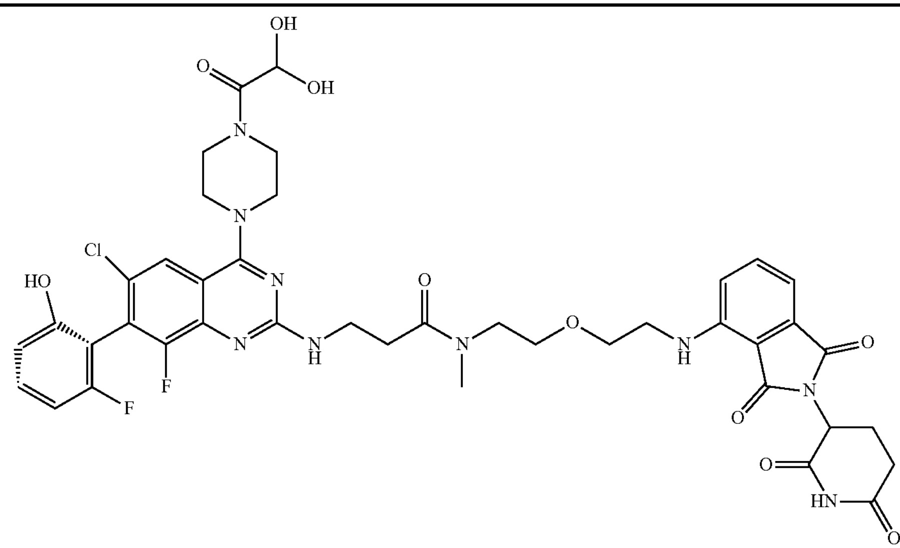 | 3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-4-yl)amino)ethoxy)ethyl)-N-methylpropanamide | 1 |
| 161 | 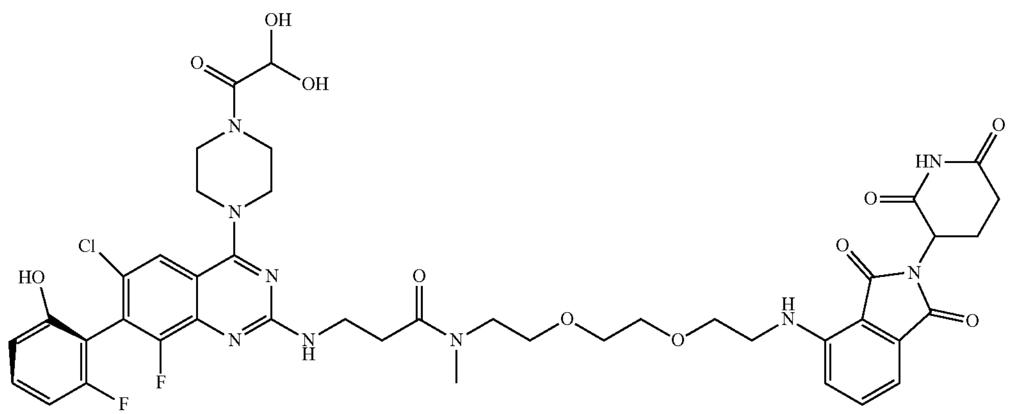 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-((2-(2,6-dioxopiperidin-3-yl)-1,3-dioxoisoindolin-4-yl)amino)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 162 | 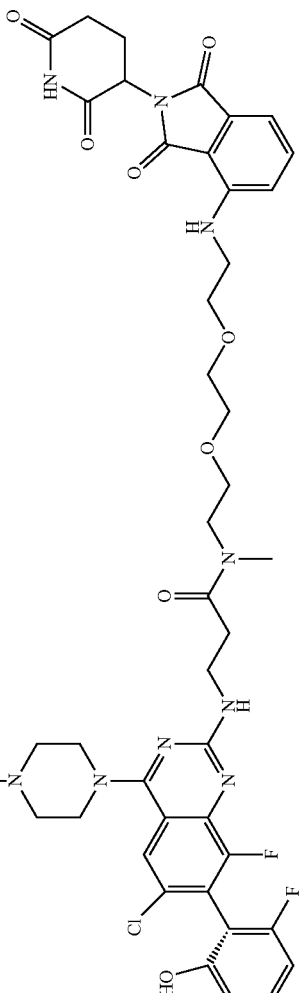 | 3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide | 1 |
| 163 | 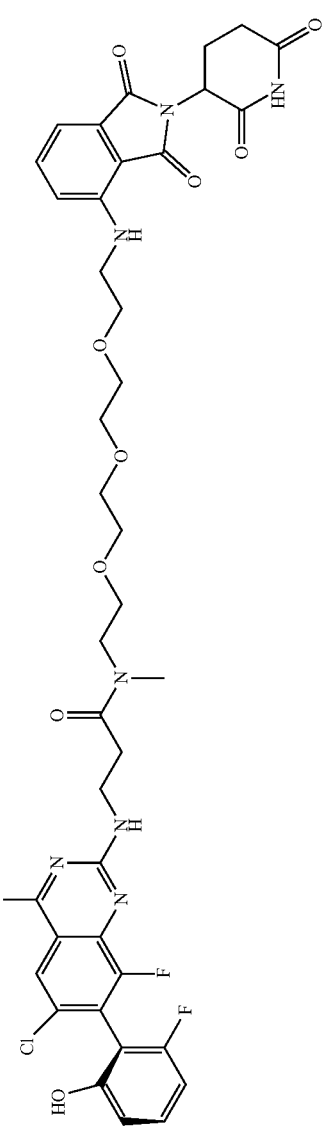 | 3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-(2-((2-(2,6-dioxopiperidin-3-yl)-1,3-dioxoisoindolin-4-yl)amino)ethoxy)ethoxy)ethyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 164 | 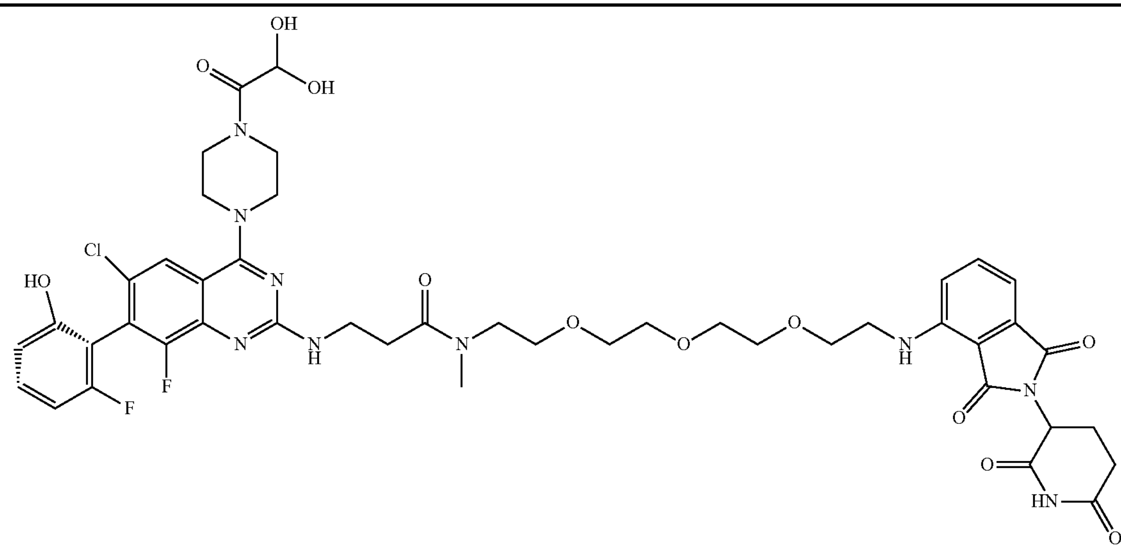 | 3-((R)-6-chloro-4-(4-(2,2-dihydroxyacetyl)piperazin-1-yl)-8-fluoro-7-(2-fluoro-6-hydroxyphenyl)quinazolin-2-yl)amino)-N-(2-(2-(2-(2-((2-(2,6-dioxopiperidin-3-yl)-1,3-dioxoisoindolin-4-yl)amino)ethoxy)ethoxy)ethoxy)ethyl)-N-methylpropanamide | 1 |
| 165 | 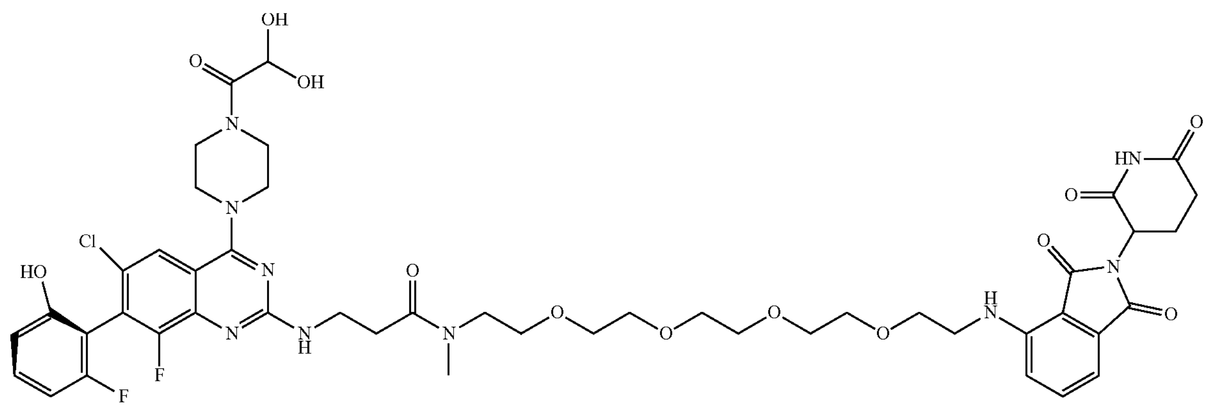 | 3-((S)-6-chloro-4-(4-(2,2-dihydroxyacetyl)piperazin-1-yl)-8-fluoro-7-(2-fluoro-6-hydroxyphenyl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |

TABLE 6-continued

Compounds Prepared by Schemes 1 and 2

| Ex. No. | Structure | Compound Name | Synthetic Scheme |
|---|---|---|---|
| 166 | 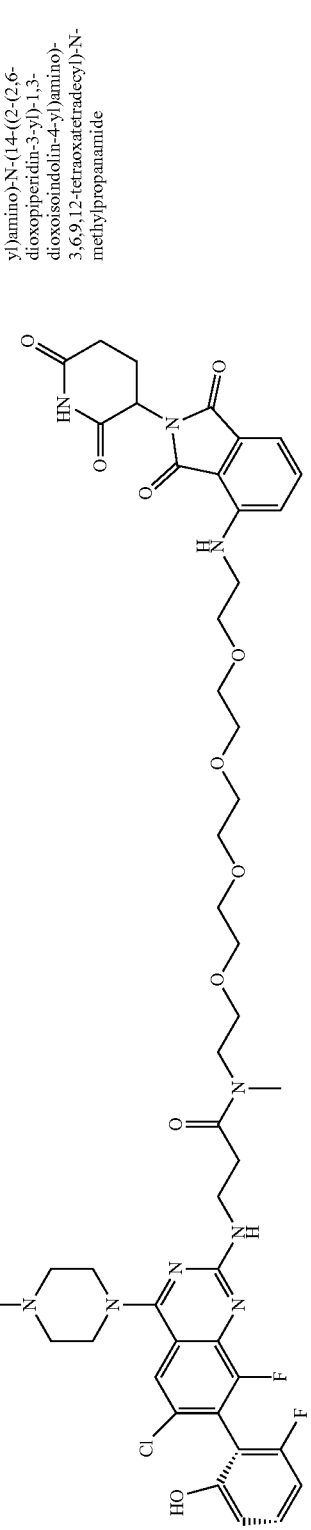 | 3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-(14-((2-(2,6-dioxopiperidin-3-yl)-1,3-dioxoisoindolin-4-yl)amino)-3,6,9,12-tetraoxatetradecyl)-N-methylpropanamide | 1 |
| 167 | 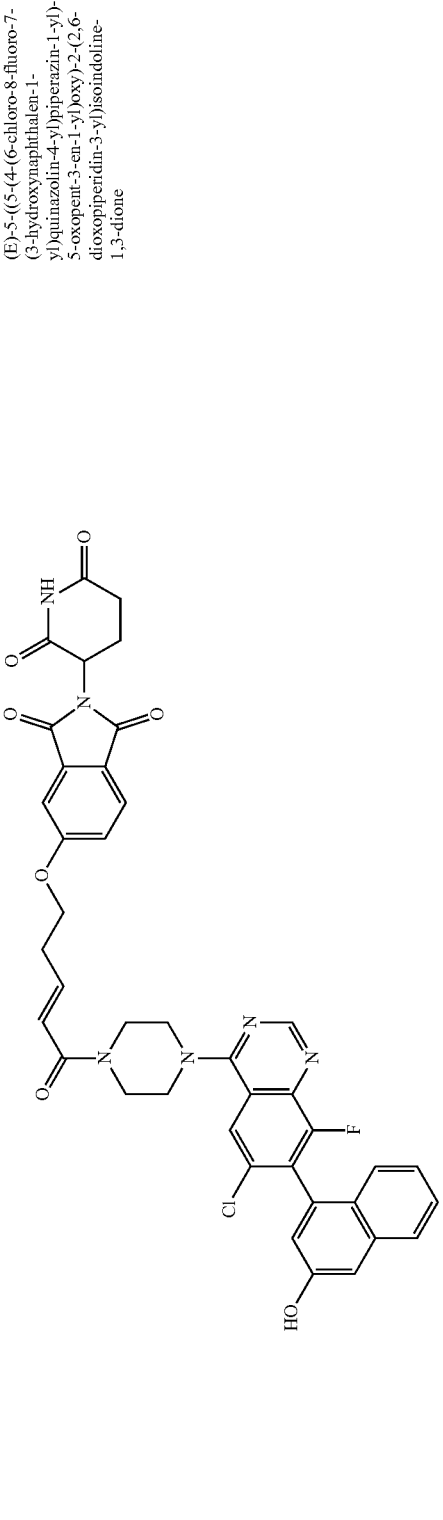 | (E)-5-((5-(4-(6-chloro-8-fluoro-7-(3-hydroxynaphthalen-1-yl)quinazolin-4-yl)piperazin-1-yl)-5-oxopent-3-en-1-yl)oxy)-2-(2,6-dioxopiperidin-3-yl)isoindoline-1,3-dione | 2 |

TABLE 6-continued

Compounds Prepared by Schemes 1 and 2

| Ex. No. | Structure | Compound Name | Synthetic Scheme |
|---|---|---|---|
| 168 | 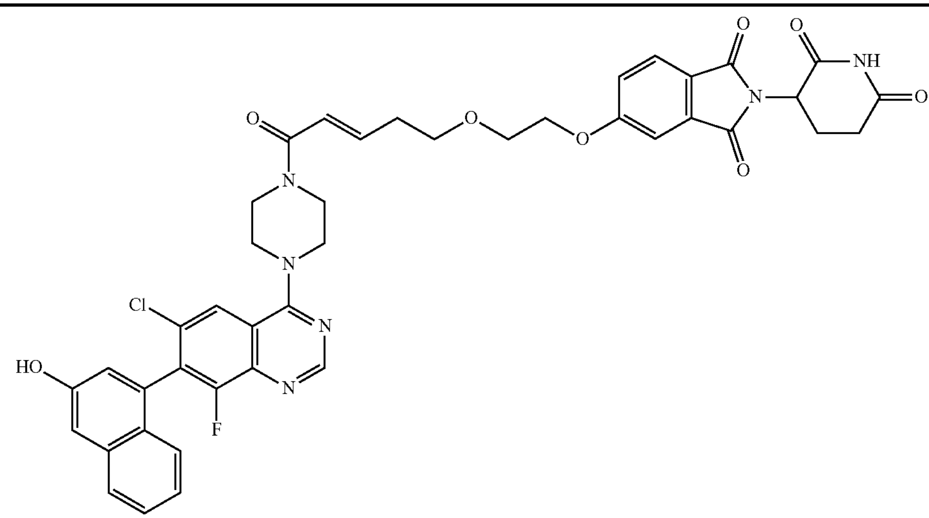 | (E)-5-(2-((5-(4-(6-chloro-8-fluoro-7-(3-hydroxynaphthalen-1-yl)quinazolin-4-yl)piperazin-1-yl)-5-oxopent-3-en-1-yl)oxy)ethoxy)-2-(2,6-dioxopiperidin-3-yl)isoindoline-1,3-dione | 2 |
| 169 | 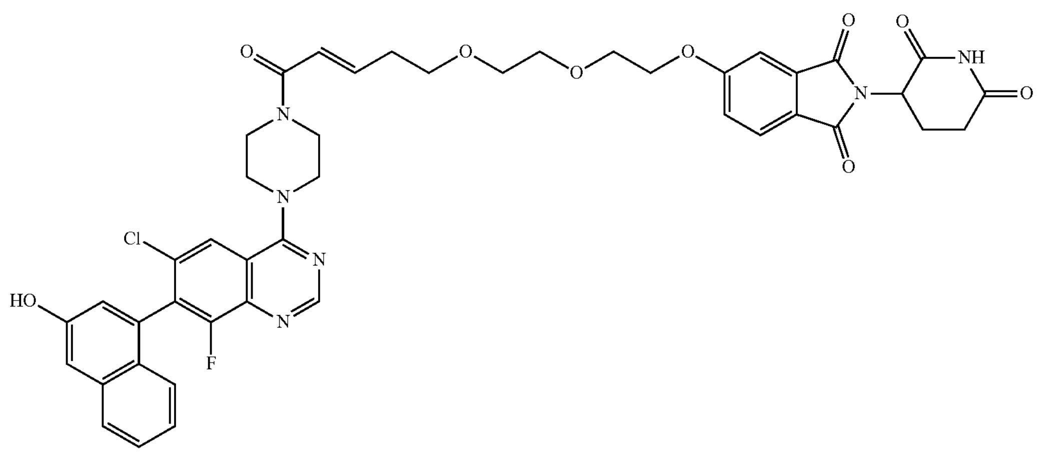 [SMILES: O=C1CCC(N2C(=O)c3ccc(OCCOCCOCC/C=C/C(=O)N4CCN(c5ncnc6c(F)c(-c7cc(O)cc8ccccc78)c(Cl)cc56)CC4)cc3C2=O)C(=O)N1] | (E)-5-(2-(2-((5-(4-(6-chloro-8-fluoro-7-(3-hydroxynaphthalen-1-yl)quinazolin-4-yl)piperazin-1-yl)-5-oxopent-3-en-1-yl)oxy)ethoxy)ethoxy)-2-(2,6-dioxopiperidin-3-yl)isoindoline-1,3-dione | 2 |

TABLE 6-continued

Compounds Prepared by Schemes 1 and 2

| Ex. No. | Structure | Compound Name | Synthetic Scheme |
|---|---|---|---|
| 170 | 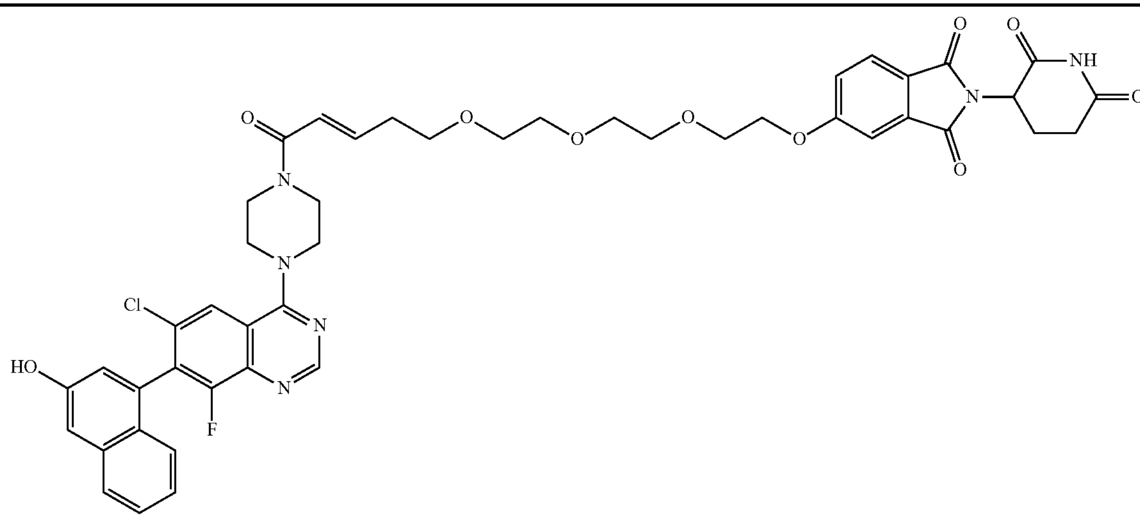 | (E)-5-(2-(2-(2-(2-((5-(4-(6-chloro-8-fluoro-7-(3-hydroxynaphthalen-1-yl)quinazolin-4-yl)piperazin-1-yl)-5-oxopent-3-en-1-yl)oxy)ethoxy)ethoxy)ethoxy)-2-(2,6-dioxopiperidin-3-yl)isoindoline-1,3-dione | 2 |
| 171 | 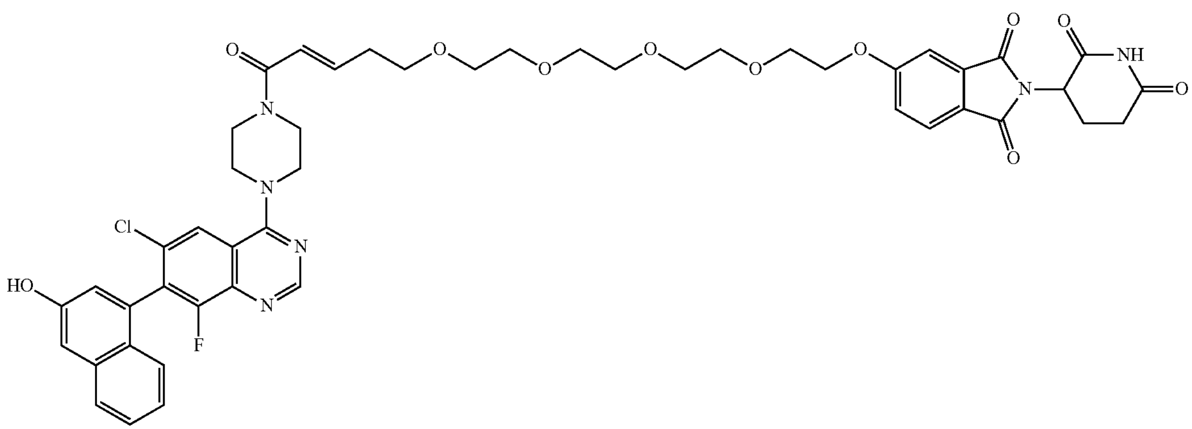 [SMILES: O=C1CCC(N2C(=O)c3ccc(OCCOCCOCCOCCOCC/C=C/C(=O)N4CCN(c5ncnc6c(F)c(-c7cc(O)cc8ccccc78)c(Cl)cc56)CC4)cc3C2=O)C(=O)N1] | (E)-5-((17-(4-(6-chloro-8-fluoro-7-(3-hydroxynaphthalen-1-yl)quinazolin-4-yl)piperazin-1-yl)-17-oxo-3,6,9,12-tetraoxaheptadec-15-en-1-yl)oxy)-2-(2,6-dioxopiperidin-3-yl)isoindoline-1,3-dione | 2 |

TABLE 6-continued

Compounds Prepared by Schemes 1 and 2

| Ex. No. | Compound Name | Structure | Synthetic Scheme |
|---|---|---|---|
| 172 | (E)-3-((6-chloro-4-(4-(5-(2-((2-(2,6-dioxopiperidin-3-yl)-1,3-dioxoisoindolin-5-yl)oxy)ethoxy)pent-2-enoyl)piperazin-1-yl)-8-fluoro-7-(3-hydroxynaphthalen-1-yl)quinazolin-2-yl)amino)-N,N-dimethylpropanamide | 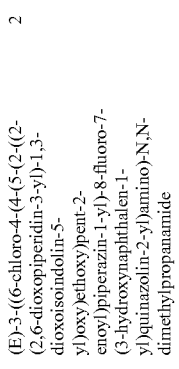 | 2 |
| 173 | (E)-3-((6-chloro-4-(4-(5-(2-(2-((2-(2,6-dioxopiperidin-3-yl)-1,3-dioxoisoindolin-5-yl)oxy)ethoxy)ethoxy)pent-2-enoyl)piperazin-1-yl)-8-fluoro-7-(3-hydroxynaphthalen-1-yl)quinazolin-2-yl)amino)-N,N-dimethylpropanamide | 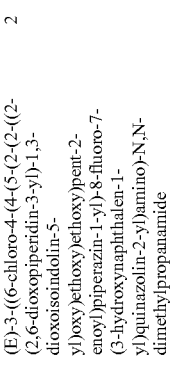 | 2 |

TABLE 6-continued

Compounds Prepared by Schemes 1 and 2

| Ex. No. | Structure | Compound Name | Synthetic Scheme |
|---|---|---|---|
| 174 | 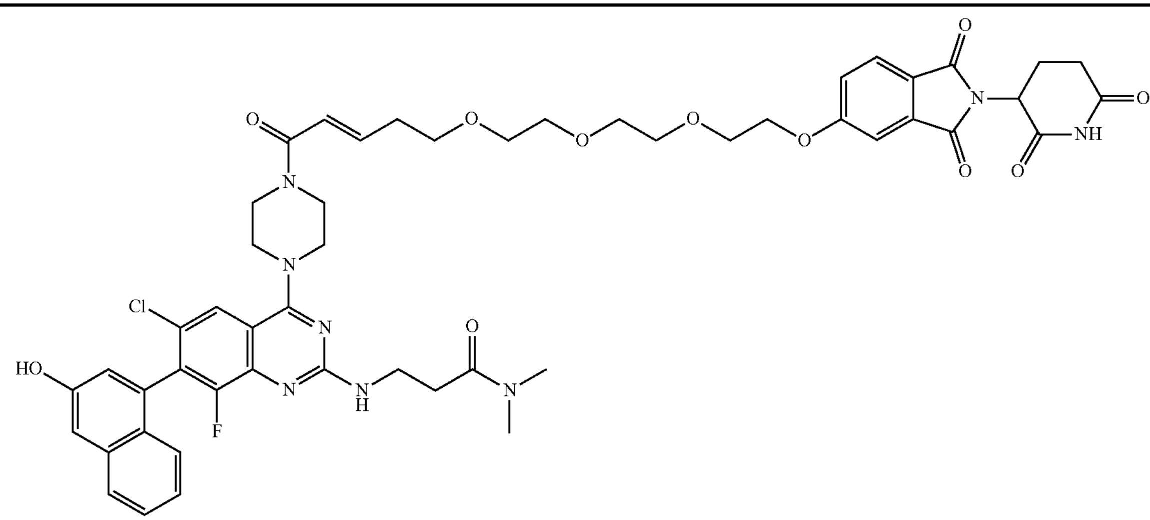 | (E)-3-((6-chloro-4-(4-(5-(2-(2-(2-((2-(2,6-dioxopiperidin-3-yl)-1,3-dioxoisoindolin-5-yl)oxy)ethoxy)ethoxy)ethoxy)pent-2-enoyl)piperazin-1-yl)-8-fluoro-7-(3-hydroxynaphthalen-1-yl)quinazolin-2-yl)amino)-N,N-dimethylpropanamide | 2 |
| 175 | 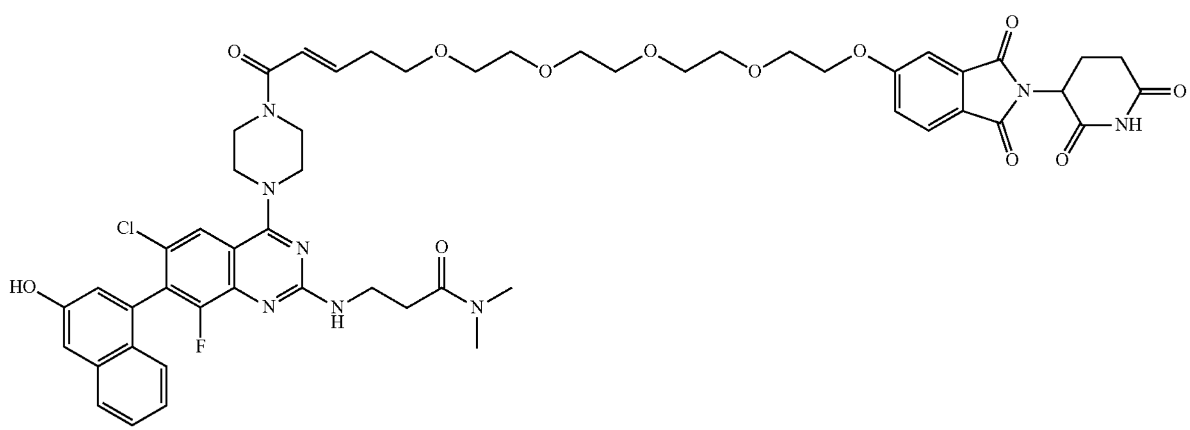 [SMILES: CN(C)C(=O)CCNc1nc(N2CCN(C(=O)/C=C/CCOCCOCCOCCOCCOc3ccc4c(c3)C(=O)N(C3CCC(=O)NC3=O)C4=O)CC2)c2cc(Cl)c(-c3cc(O)cc4ccccc34)c(F)c2n1] | (E)-3-((6-chloro-4-(4-(1-((2-(2,6-dioxopiperidin-3-yl)-1,3-dioxoisoindolin-5-yl)oxy)-3,6,9,12-tetraoxaheptadec-15-en-17-oyl)piperazin-1-yl)-8-fluoro-7-(3-hydroxynaphthalen-1-yl)quinazolin-2-yl)amino)-N,N-dimethylpropanamide | 2 |

TABLE 6-continued

Compounds Prepared by Schemes 1 and 2

| Ex. No. | Structure | Compound Name | Synthetic Scheme |
|---|---|---|---|
| 176 | 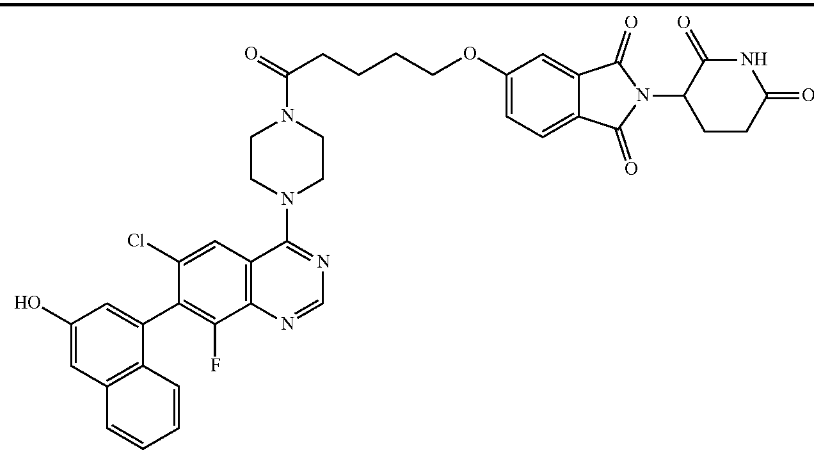 | 5-((5-(4-(6-chloro-8-fluoro-7-(3-hydroxynaphthalen-1-yl)quinazolin-4-yl)piperazin-1-yl)-5-oxopentyl)oxy)-2-(2,6-dioxopiperidin-3-yl)isoindoline-1,3-dione | 2 |
| 177 | 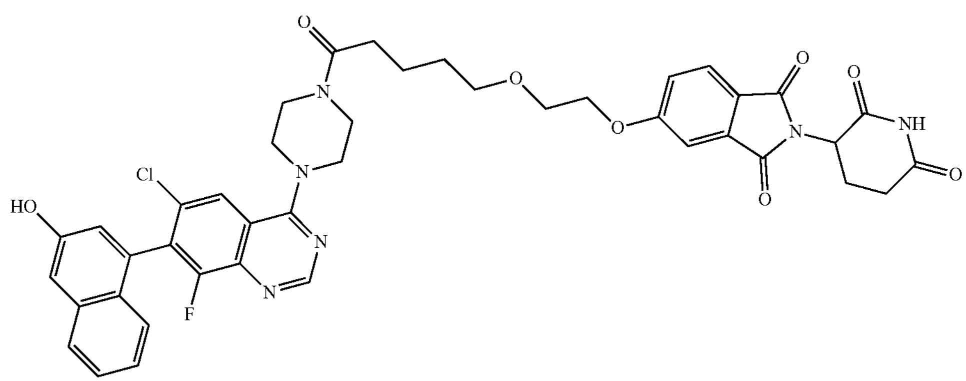 [SMILES: O=C1CCC(N2C(=O)c3ccc(OCCOCCCCC(=O)N4CCN(c5ncnc6c(F)c(-c7cc(O)cc8ccccc78)c(Cl)cc56)CC4)cc3C2=O)C(=O)N1] | 5-(2-((5-(4-(6-chloro-8-fluoro-7-(3-hydroxynaphthalen-1-yl)quinazolin-4-yl)piperazin-1-yl)-5-oxopentyl)oxy)ethoxy)-2-(2,6-dioxopiperidin-3-yl)isoindoline-1,3-dione | 2 |

TABLE 6-continued
Compounds Prepared by Schemes 1 and 2
| Ex. No. | Structure | Compound Name | Synthetic Scheme |
|---|---|---|---|
| 178 | 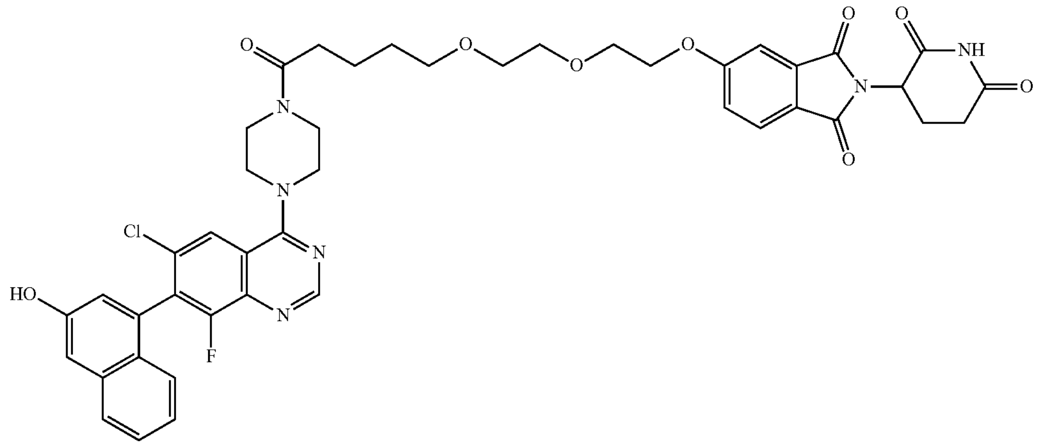 [SMILES: O=C1CCC(N2C(=O)c3ccc(OCCOCCOCCCCC(=O)N4CCN(c5ncnc6c(F)c(-c7cc(O)cc8ccccc78)c(Cl)cc56)CC4)cc3C2=O)C(=O)N1] | 5-(2-(2-((5-(4-(6-chloro-8-fluoro-7-(3-hydroxynaphthalen-1-yl)quinazolin-4-yl)piperazin-1-yl)-5-oxopentyl)oxy)ethoxy)ethoxy)-2-(2,6-dioxopiperidin-3-yl)isoindoline-1,3-dione | 2 |
| 179 | 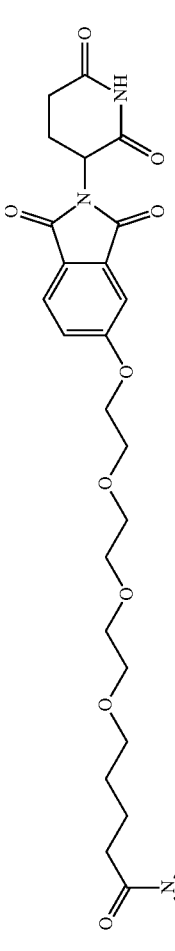 | 5-(2-(2-(2-((5-(4-(6-chloro-8-fluoro-7-(3-hydroxynaphthalen-1-yl)piperazin-1-yl)-5-oxopentyl)oxy)ethoxy)ethoxy)ethoxy)-2-(2,6-dioxopiperidin-3-yl)isoindoline-1,3-dione | 2 |

TABLE 6-continued

Compounds Prepared by Schemes 1 and 2

| Ex. No. | Structure | Compound Name | Synthetic Scheme |
|---|---|---|---|
| 180 | 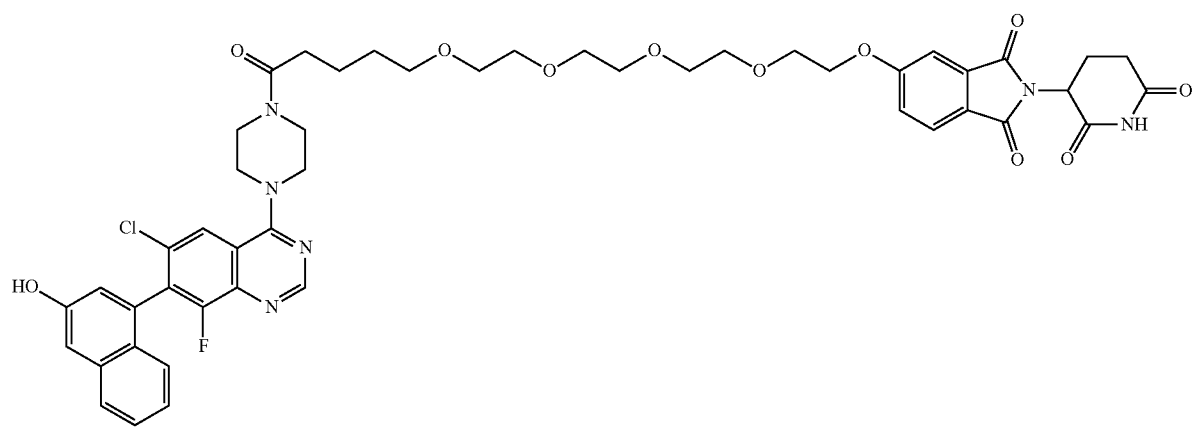 [SMILES: O=C1CCC(N2C(=O)c3ccc(OCCOCCOCCOCCOCCCCC(=O)N4CCN(c5ncnc6c(F)c(-c7cc(O)cc8ccccc78)c(Cl)cc56)CC4)cc3C2=O)C(=O)N1] | 5-((17-(4-(6-chloro-8-fluoro-7-(3-hydroxynaphthalen-1-yl)quinazolin-4-yl)piperazin-1-yl)-17-oxo-3,6,9,12-tetraoxaheptadecyl)oxy)-2-(2,6-dioxopiperidin-3-yl)isoindoline-1,3-dione | 2 |

TABLE 7

Data for Compounds of Table 6

| Ex. No. | MH+ (1) | MH+ (2) | NMR Transcript | Synthetic Scheme | Mol Weight |
|---|---|---|---|---|---|
| 11 | 851.59 | 853.59 | ¹H NMR (400 MHz, DMSO-d₆) δ 1.97-2.05 (m, 4H), 2.56-2.88 (m, 7H), 2.89-3.09 (m, 2H), 3.56-3.79 (m, 11H), 4.26 (s, 2H), 5.09-5.13 (m, 1H), 7.04-7.43 (m, 8H), 7.65-7.77 (m, 3H), 9.97 (s, 1H), 11.08 (s, 1H). | 1 | 851.29 |
| 12 | 895.63 | 897.63 | ¹H NMR (400 MHz, DMSO-d₆) δ 2.01-2.04 (m, 1H), 2.06 (s, 3H), 2.54-2.65 (m, 4H), 2.81-2.88 (m, 3H), 3.02 (s, 1H), 3.47-3.75 (m, 18H), 4.19 (br, 1H), 4.28 (s, 1H), 5.08-5.13 (m, 1H), 7.03-7.04 (m, 1H), 7.21-7.22 (m, 2H), 7.25-7.26 (m, 1H), 7.31-7.33 (m, 1H), 7.42 (s, 2H), 7.78-7.80 (m, 2H), 9.97 (s, 1H), 11.10 (s, 1H). | 1 | 895.34 |
| 13 | 939.66 | 941.67 | ¹H NMR (400 MHz, DMSO-d₆) δ 2.01-2.07 (m, 4H), 2.54-2.75 (m, 4H), 2.87-2.99 (m, 4H), 3.47-3.77 (m, 16H), 4.18-4.28 (m, 6H), 5.09-5.14 (m, 1H), 7.07-7.08 (m, 1H), 7.22-7.27 (m, 2H), 7.32-7.36 (m, 2H), 7.43-7.48 (m, 2H), 7.80-7.84 (m, 2H), 8.04-8.09 (m, 2H), 11.12 (s, 1H). | 1 | 939.40 |
| 14 | 983.7 | 985.7 | ¹H NMR (400 MHz, DMSO-d₆) δ 2.00-2.07 (m, 4H), 2.54-2.74 (m, 4H), 2.86-2.98 (m, 4H), 3.48-3.57 (m, 12H), 3.72-3.77 (m, 8H), 4.18-4.29 (m, 6H), 5.11 (dd, J = 5.2, 12.8 Hz, 1H), 7.08 (s, 1H), 7.24-7.25 (m, 2H), 7.32-7.35 (m, 2H), 7.44-7.48 (m, 2H), 7.80-7.84 (m, 2H), 8.03-8.09 (m, 2H), 11.11 (s, 1H). | 1 | 983.45 |
| 15 | 1027.74 | 1029.74 | ¹H NMR (400 MHz, DMSO-d₆) δ 2.04-2.07 (m, 4H), 2.54-2.99 (m, 9H), 3.48-3.77 (m, 22H), 4.19-4.30 (m, 6H), 5.11 (dd, J = 5.2, 12.8 Hz, 2H), 7.08 (s, 1H), 7.22-7.27 (m, 2H), 7.32-7.36 (m, 2H), 7.44-7.48 (m, 2H), 7.81-7.84 (m, 2H), 8.00-8.10(m, 2H), 11.11 (s, 1H). | 1 | 1027.50 |
| 16 | 837.6 | 839.61 | ¹H NMR (400 MHz, DMSO-d₆) δ 1.23-1.28 (m, 1H), 1.93-1.99 (m, 1H), 2.06 (s, 3H), 2.26-2.46 (m, 2H), 2.53-2.69 (m, 2H), 2.74-2.81 (m, 1H), 2.85-2.91 (m, 2H), 3.10 (s, 1H), 3.51-3.83 (m, 12H), 4.15-4.38 (3, 4H), 5.01-5.11 (m, 2H), 6.90-7.05 (m, 2H), 7.13-7.28 (m, 4H), 7.34-7.67 (m, 3H), 7.74-7.84(m, 2H), 9.98 (s, 1H), 10.92-11.02 (m, 1H). | 1 | 837.31 |
| 17 | 881.65 | 883.65 | ¹H NMR (400 MHz, DMSO-d₆) δ 1.95-2.10 (m, 4H), 2.51-2.92 (m, 7H), 3.09 (s, 2H), 3.50-3.80 (m, 11H), 4.27 (s, 2H), 5.06-5.11 (m, 5H), 7.09-7.44 (m, 8H), 7.55-7.80 (m, 3H), 9.97 (s, 1H), 11.11 (s, 1H). | 1 | 881.36 |
| 18 | 925.68 | 927.68 | ¹H NMR (400 MHz, DMSO-d₆) δ 1.97-2.06 (m, 4H), 2.29-2.41 (m, 1H), 2.56-3.00 (m, 7H), 3.12-3.15 (m, 1H), 3.41-3.72 (m, 18H), 4.06-4.37 (m, 5H), 5.07 (dd, J = 4.8, 12.8 Hz 2H), 6.98-7.12 (m, 3H), 7.22-7.28 (m, 3H), 7.42-7.44 (m, 1H), 7.59 (d, J = 8.4 Hz, 1H), 7.75-7.81 (m, 2H), 10.00 (s, 1H), 10.96 (s, 1H). | 1 | 925.41 |
| 19 | 969.72 | 971.73 | ¹H NMR (400 MHz, DMSO-d₆) δ 1.96-2.06 (m, 4H), 2.29-2.38 (m, 2H), 2.56-2.66 (m, 3H), 2.80-3.00 (m, 4H), 3.42-3.71 (m, 23H), 4.13-4.39 (m, 4H), 5.07 (dd, J = 5.2, 13.2 Hz, 1H), 7.01-7.05 (m, 2H), 7.13-7.27 (m, 5H), 7.41-7.45 (m, 1H), 7.60 (d, J = 8.4 Hz, 1H), 7.79 (d, J = 8.4 Hz, 2H), 9.98 (s, 1H), 10.96 (s, 1H). | 1 | 969.47 |
| 20 | 1013.76 | 1015.76 | ¹H NMR (400 MHz, DMSO-d₆) δ 1.93-2.01 (m, 1H), 2.06 (s, 3H), 2.36 (m, 1H), 2.54-2.70 (m, 3H), 2.80 (s, 1H), 2.88 (s, 1H), 3.00 (s, 1H), 3.36-3.58 (m, 19H), 3.59-3.85 (m, 11H), 4.15 (s, 2H), 4.24 (d, J = 23.0 Hz, 1H), 4.33-4.38 (m, 1H), 5.04-5.08 (m, 1H), 7.03 (d, J = 7.6 Hz, 2H), 7.14 (s, 1H), 7.22 (d, J = 3.6 Hz, 2H), 7.26 (d, J = 2.0 Hz, 1H), 7.39-7.46 (m, 1H), 7.60 (d, J = 8.4 Hz, 1H), 7.79 (d, J = 8.8 Hz, 2H), 9.98 (s, 1H), 10.96 (s, 1H). | 1 | 1013.52 |
| 21 | 850.61 | 852.61 | ¹H NMR (400 MHz, DMSO-d₆) δ 2.00-2.02 (m, 5H), 2.57-2.63 (m, 3H), 2.85 (s, 2H), 3.03 (s, 2H), 3.41-3.59 (m, 7H), 3.67 (s, 7H), 5.02-5.06 (m, 1H), 6.71 (s, 1H), 6.92-7.11 (m, 3H), 7.15-7.24 (m, 3H), 7.26 (s, 1H), 7.40-7.46 (m, 1H),7.57 (s, 1H), 7.74-7.85 (m, 2H), 9.99 (s, 1H) ,11.08 (s, 1H). | 1 | 850.31 |
| 22 | 894.64 | 896.64 | ¹H NMR (400 MHz, DMSO-d₆) δ 1.97-2.01 (m, 1H), 2.06 (s, 3H), 2.59-2.67 (m, 3H), 2.80-2.86 (m, 4H), 3.00 (s, 1H), 3.44-3.67 (m, 19H), 5.01-5.05 (m, 1H), 6.56 (br, 1H), 6.95-6.96 (m, 1H), 7.03-7.04 (m, 1H), 7.10-7.13 (m, 1H), 7.22-7.26 (m, 3H), 7.41-7.44 (m, 1H), 7.53-7.56 (m, 1H), 7.73-7.80 (m, 2H), 9.97 (s, 1H), 11.08 (s, 1H). | 1 | 894.36 |
| 23 | 938.68 | 940.68 | ¹H NMR (400 MHz, DMSO-d₆) δ 1.99-2.06 (m, 4H), 2.55-2.99 (m, 8H), 3.33-3.67 (m, 22H), 5.04 (dd, J = 5.2, 13.2 Hz, 1H), 6.53-6.58 (m, 1H), 7.00-7.11 (m, 3H), 7.19-7.30 (m, 3H), 7.41-7.46 (m, 1H), 7.51-7.55 (m, 1H), 7.75-7.80 (m, 2H), 9.98 (s, 1H), 11.08 (s, 1H). | 1 | 938.41 |
| 24 | 982.72 | 984.72 | ¹H NMR (400 MHz, DMSO-d₆) δ 1.99-2.06 (m, 4H), 2.55-2.99 (m, 8H), 3.33-3.68 (m, 26H), 5.04 (dd, J = 5.2 Hz, J = 12.8 Hz, 1H), 6.56-6.59 (m, 1H), 7.01-7.10 (m, 3H), 7.22-7.27 (m, 3H), 7.41-7.44 (m, 1H), 7.52-7.57 (m, 1H), 7.79-7.81 (m, 2H), 9.99 (s, 1H), 11.09 (s, 1H). | 1 | 982.46 |
| 25 | 1026.76 | 1028.76 | ¹H NMR (400 MHz, DMSO-d₆) δ 2.01-2.06 (m, 4H), 2.54-2.77 (m, 3H), 2.92 (d, J = 5.4 Hz, 4H), 3.46-3.59 (m, 26H), 4.07-4.30 (m, 5H), 5.04 (s, 1H), 6.59 (s, 1H), 7.08 (s, 3H), 7.23 (s, 3H), 7.46 (s, 1H), 7.56 (s, 1H),7.82 (d, J = 8.0 Hz, 1H), 8.08 (s, 2H), 11.08 (s, 1H). | 1 | 1026.52 |
| 26 | 852.59 | 854.59 | ¹H NMR (400 MHz, DMSO-d₆) δ 1.20-1.28 (m, 1H), 1.98-2.07 (m, 1H), 2.54-2.67 (m, 3H), 2.73-2.97 (m, 3H), 3.09-3.17 (m, 2H), 3.46-3.80 (m, 11H), 4.21-4.36 (m, 2H), 5.09-5.13 (m, 1H), 6.07 (s, 1H), 6.99-7.07 (m, 2H), 7.12-7.45 (m, 7H), 7.69-7.80 (m, 3H), 9.97 (s, 1H), 11.10 (s, 1H). | 1 | 852.28 |
| 27 | 896.63 | 898.63 | ¹H NMR (400 MHz, DMSO-d₆) δ 1.97-2.07 (m, 2H), 2.54-2.74 (m, 4H), 2.87 (s, 2H), 3.00 (s, 2H), 3.64-3.78 (m, 13H), 4.12 (s, 3H), 4.30 (s, 2H), 5.08-5.13 (m, 1H), 6.13 (s, 2H), 7.07 (s, 1H), 7.23-7.24 (m, 2H), 7.31-7.36 (m, 2H), 7.41-7.47 (m, 2H), 7.79-7.83 (m, 2H), 8.05-8.07 (m, 1H), 10.11 (s, 1H), 11.11 (s, 1H). | 1 | 896.33 |
| 28 | 940.66 | 942.66 | ¹H NMR (400 MHz, DMSO-d₆) δ 1.99-2.07 (m, 1H), 2.53-2.72 (m, 4H), 2.78-2.90 (m, 2H), 2.92-3.08 (m, 2H), 3.36-3.82 (m, 20H), 4.14-4.32 (m, 2H), 5.06-5.15 (m, 1H), 6.08 (s, 2H),7.04(s, 1H), 7.08-7.34 (m, 5H), 7.37-7.45 (m, 2H), 7.71-7.85 (m, 3H), 9.97 (s, 1H), 11.10 (s, 1H). | 1 | 940.38 |
| 29 | 984.7 | 986.7 | ¹H NMR (400 MHz, DMSO-d₆) δ 2.03-2.06 (m, 1H), 2.55-2.99 (m, 4H), 3.42-3.74 (m, 23H), 4.26 (s, 2H), 5.09-5.13 (m, 1H), 6.09 (s, 2H), 6.98-7.19 (m, 2H), 7.23-7.27 (m, 3H), 7.32-7.34 (m, 1H), 7.42-7.47 (m, 2H), 7.77-7.81 (m, 3H), 9.98 (s, 1H), 11.11 (s, 1H). | 1 | 984.44 |
| 30 | 1028.74 | 1030.74 | ¹H NMR (400 MHz, DMSO-d₆) δ 2.03-2.06 (m, 1H), 2.54-2.68 (m, 3H), 2.81-2.93 (m, 3H), 3.00 (s, 1H), 3.36-3.76 (m, 27H), 4.28 (s, 2H), 5.09-5.14 (m, 1H), 6.09 (s, 2H), 6.99-7.11 (m, 2H), 7.20-7.27 (m, 3H), 7.33-7.35 (m, 1H), 7.41-7.46 (m, 2H), 7.78-7.82 (m, 3H), 9.98 (s, 1H), 11.11 (s, 1H). | 1 | 1028.49 |
| 31 | 851.6 | 853.6 | ¹H NMR (400 MHz, DMSO-d₆) δ 1.91-2.03 (m, 2H), 2.56-2.67 (m, 2H), 2.81-2.91 (m, 2H), 2.98-3.07 (m, 2H), 3.41-3.82 (m, 15H), 5.01-5.06 (m, 1H), 6.08 (s, 2H), 6.64-6.75 (m, 1H), 6.96-7.32 (m, 7H), 7.40-7.45 (m, 1H), 7.55-7.59 (m, 1H), 7.74-7.83 (m, 2H), 9.97 (s, 1H), 11.08 (s, 1H). | 1 | 851.29 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| 32 | 895.65 | 897.65 | ¹H NMR (400 MHz, DMSO-d₆) δ 1.12-1.33 (m, 2H), 1.97-2.03 (m, 1H), 2.52-2.67 (m, 3H), 2.80-3.00 (m, 4H), 3.17 (d, J = 3.6 Hz, 1H), 3.34-3.70 (m, 16H), 5.00-5.05 (m, 1H), 6.08 (s, 2H), 6.50-6.62 (m, 1H), 6.94-7.26 (m, 7H), 7.40-7.56 (m, 2H), 7.72-7.80 (m, 2H), 9.97 (s, 1H), 11.07 (s, 1H). | 1 | 895.35 |
| 33 | 939.67 | 941.67 | ¹H NMR (400 MHz, DMSO-d₆) δ 1.91-2.08 (m, 2H), 2.54-2.68 (m, 3H), 2.72-3.06 (m, 5H), 3.36-3.74 (m, 21H), 4.99-5.07 (m, 1H), 6.08 (s, 2H), 6.50-6.60 (m, 1H), 6.92-7.15 (m, 4H), 7.19-7.29 (m, 3H), 7.39-7.46 (m, 1H), 7.49-7.57 (m, 1H), 7.70-7.83 (m, 2H), 9.98 (s, 1H), 11.08 (s, 1H). | 1 | 939.40 |
| 34 | 983.7 | 984.7 | ¹H NMR (400 MHz, DMSO-d₆) δ 1.98-2.03 (m, 2H), 2.25-2.33 (m, 1H), 2.52-2.99 (m, 8H), 3.00 (s, 1H), 3.37-3.68 (m, 24H), 5.02-5.07 (m, 1H), 6.08 (s, 2H), 6.56-6.58 (m, 1H), 6.97-7.15 (m, 4H), 7.23-7.27 (m, 3H), 7.41-7.44 (m, 1H), 7.52-7.57 (m, 1H), 7.77-7.80 (m, 2H), 9.98 (s, 1H), 11.08 (s, 1H). | 1 | 983.45 |
| 35 | 1027.76 | 1029.76 | ¹H NMR (400 MHz, DMSO-d₆) δ 2.00-2.05 (m, 1H), 2.44-2.45 (m, 1H), 2.52-2.72 (m, 4H), 2.81-2.92 (m, 3H), 3.00 (s, 2H), 3.45-3.62 (m, 29H), 5.02-5.07 (m, 1H), 6.08 (s, 2H), 6.57-6.59 (m, 1H), 7.01-7.04 (m, 2H), 7.10-7.13 (m, 1H), 7.23-7.27 (m, 3H), 7.41-7.45 (m, 1H), 7.53-7.58 (m, 1H), 7.78-7.82 (m, 2H), 9.98 (s, 1H) 11.08 (m, 1H). | 1 | 1027.51 |
| 36 | 838.6 | 840.6 | ¹H NMR (400 MHz, DMSO-d₆) δ 1.93-1.99 (m, 1H), 2.23-2.37 (m, 1H), 2.56-2.67 (m, 2H), 2.76-2.79 (m, 1H), 2.85-2.93 (m, 2H), 3.10 (s, 1H), 3.48-3.79 (m, 13H), 4.15-4.38 (m, 4H), 5.04-5.08 (m, 1H), 6.08 (s, 2H), 7.04-7.27 (m, 7H), 7.40-7.45 (m, 1H), 7.50-7.61 (m, 1H), 7.76-7.83 (m, 2H), 9.98 (s, 1H), 10.95 (s, 1H). | 1 | 838.29 |
| 37 | 882.64 | 884.64 | ¹H NMR (400 MHz, DMSO-d₆) δ 1.94-2.01 (m, 1H), 2.31-2.38 (m, 1H), 2.55-2.70 (m, 3H), 2.76-2.96 (m, 3H), 3.02 (s, 1H), 3.10-3.18 (m, 1H), 3.43-3.79 (m, 15H), 4.06-4.37 (m, 4H), 5.04-5.08 (m, 1H), 6.08 (s, 2H), 7.01-7.27 (m, 7H), 7.41-7.44 (m, 1H), 7.54-7.59 (m, 1H), 7.73-7.85 (m, 2H), 9.99 (s, 1H), 10.95 (s, 1H). | 1 | 882.35 |
| 38 | 926.67 | 928.68 | ¹H NMR (400 MHz, DMSO-d₆) δ 1.94-2.07 (m, 1H), 2.31-2.40 (m, 1H), 2.54-2.70 (m, 3H), 2.80-3.08 (m, 6H), 3.36-3.82 (m, 18H), 4.04-4.40 (m, 4H), 5.06-5.15 (m, 1H), 6.08 (s, 2H), 6.96-7.18 (m, 4H), 7.20-7.31 (m, 3H), 7.39-7.47 (m, 1H), 7.55-7.63 (m, 1H), 7.73-7.85 (m, 2H),10.00 (s, 1H), 10.96 (s, 1H). | 1 | 926.40 |
| 39 | 970.71 | 972.71 | ¹H NMR (400 MHz, DMSO-d₆) δ 1.94-2.03 (m, 2H), 2.30-2.45 (m, 2H), 2.56-3.00 (m, 8H), 3.41-3.72 (m, 21H), 4.13-4.14 (m, 2H), 4.22-4.27 (m, 1H), 4.33-4.39 (m, 1H), 5.04-5.09 (m, 1H), 6.08 (s, 2H), 7.01-7.04 (m, 2H), 7.13 (s, 1H), 7.23-7.27 (m, 3H), 7.41-7.44 (m, 1H), 7.60 (d, J = 8.4 Hz, 1H), 7.77-7.80 (m, 2H), 9.97 (s, 1H), 10.95 (s, 1H). | 1 | 970.45 |
| 40 | 1014.75 | 1016.75 | ¹H NMR (400 MHz, CDCl₃) δ 2.00-2.13 (m, 2H), 2.37-2.48 (m, 1H), 2.65 (s, 1H), 2.73-2.95 (m, 6H), 3.08 (s, 1H), 3.50-3.86 (m, 22H), 4.14-4.43 (m, 8H), 5.07-5.18 (m, 1H), 6.93-7.07 (m, 3H), 7.23-7.31 (m, 3H), 7.42-7.46 (m, 1H), 7.62-7.65 (m, 1H), 7.76-7.78 (m, 1H), 8.05-8.09 (m, 1H). | 1 | 1014.51 |
| 41 | 864.51 | 866.51 | ¹H NMR (400 MHz, DMSO-d₆) δ 11.09 (s, 1H), 10.09-9.91 (m, 1H), 7.85-7.73 (m, 2H), 7.64-7.50 (m, 1H), 7.48-7.40 (m, 1H), 7.34-7.13 (m, 5H), 7.10-6.95 (m, 2H), 6.71 (br s, 1H), 5.14-4.97 (m, 1H), 3.86-3.70 (m, 4H), 3.67-3.38 (m, 8H), 3.33 (s, 3H), 3.07-2.98 (m, 2H), 2.94-2.81 (m, 2H), 2.72-2.56 (m, 3H), 2.43-2.32 (m, 2H), 2.06-1.94 (m, 1H), 1.03 (t, J = 7.3 Hz, 3H). | 1 | 864.33 |
| 42 | 908.55 | 910.55 | ¹H NMR (400 MHz, DMSO-d₆) δ 12.3 (br s, 1H), 11.10 (br d, J = 2.5 Hz, 1H), 10.17 (br s, 1H), 8.10-8.05 (m, 2H), 7.84 (d, J = 8.2 Hz, 1H), 7.65-7.41 (m, 2H), 7.33 (s, 1H), 7.29-7.21 (m, 2H), 7.21-7.08 (m, 2H), 7.01 (dd, J = 3.9, 6.9 Hz, 1H), 6.58 (br s, 1H), 5.05 (br d, J = 7.5 Hz, 1H), 4.20 (br s, 4H),3.86-3.56 (m, 15H), 2.94-2.73 (m, 4H), 2.68-2.56 (m, 3H), 2.43-2.23 (m, 2H), 2.02 (br d, J = 4.9 Hz, 1H), 1.03 (dt, J = 2.4, 7.3 Hz, 3H). | 1 | 908.39 |
| 43 | 952.58 | 954.58 | ¹H NMR (400 MHz, DMSO-d₆) δ 11.10 (br s, 1H), 10.02 (br s, 1H), 7.83-7.71 (m, 2H), 7.59-7.47 (m, 1H), 7.47-7.36 (m, 1H), 7.26 (d, J = 2.4 Hz, 1H), 7.23-7.19 (m, 2H), 7.15-6.96 (m, 4H), 6.66-6.46 (m, 1H), 5.07-5.00 (m, 1H), 3.74-3.37 (m, 23H), 3.00-2.73 (m, 4H), 2.63-2.54 (m, 3H), 2.44-2.35 (m, 2H), 2.08-1.96 (m, 1H), 1.06-0.97 (m, 3H). | 1 | 952.44 |
| 44 | 996.62 | 998.62 | ¹H NMR (400 MHz, DMSO-d₆) δ 12.63 (br s, 1H), 11.10 (br s, 1H), 8.29 (br s, 1H), 8.10 (br d, J = 2.9 Hz, 1H), 7.82 (d, J = 8.3 Hz, 1H), 7.61-7.52 (m, 1H), 7.50-7.41 (m, 1H), 7.33 (d, J = 2.1 Hz, 1H), 7.27-7.20 (m, 2H), 7.16-7.08 (m, 2H), 7.02 (dd, J = 3.4, 7.0 Hz, 1H), 6.80-6.28 (m, 1H), 5.05 (dd, J = 5.1, 12.8 Hz, 1H), 4.20 (br s, 4H), 3.72 (br s, 6H), 3.60 (br s, 2H), 3.56-3.41 (m, 14H), 3.01-2.81 (m, 4H), 2.77-2.63 (m, 2H), 2.57 (br d, J = 17.0 Hz, 2H), 2.43-2.29 (m, 3H), 2.08-1.95 (m, 1H), 1.07-0.96 (m, 3H). | 1 | 996.49 |
| 45 | 1040.65 | 1042.65 | ¹H NMR (400 MHz, DMSO-d₆) δ 11.11 (s, 1H), 10.45-9.40 (m, 1H), 8.19 (s, 1H), 7.83-7.73 (m, 2H), 7.61-7.48 (m, 1H), 7.43 (td, J = 4.0, 8.0 Hz, 1H), 7.35-6.98 (m, 7H), 6.59 (br t, J = 5.2 Hz, 1H), 5.05 (dd, J = 5.2, 12.8 Hz, 1H), 3.90-3.47 (m, 20H), 3.41-3.27 (m, 10H), 3.03-2.78 (m, 4H), 2.72-2.53 (m, 4H), 2.42-2.23 (m, 2H), 2.07-1.95 (m, 1H), 1.09-0.90 (m, 3H). | 1 | 1040.54 |
| 46 | 865.5 | 867.5 | ¹H NMR (400 MHz, CDCl₃) δ 11.11 (s, 1H), 10.16-8.09 (m, 2H), 7.84-7.82 (m, 2H), 7.46-7.06 (m, 7H), 5.12 (dd, J = 5.2, 12.8 Hz, 1H), 4.37-4.20 (m, 5H), 3.77-3.60 (m, 7H), 2.95-2.84 (m, 6H), 2.73-2.56 (m, 4H), 2.41-2.35 (m, 2H), 2.05-2.02 (m, 1H), 1.05-0.95 (m, 3H). | 1 | 865.32 |
| 47 | 909.53 | 911.53 | ¹H NMR (400 MHz, DMSO-d₆) δ 11.12 (s, 1H), 9.99 (s, 1H), 7.83-7.71 (m, 3H), 7.44-7.19 (m, 6H), 7.11 (m, 2H), 5.12 (dd, J = 5.2, 12.9 Hz, 1H), 4.29-4.21 (m, 2H), 3.76-3.50 (m, 16H), 3.38 (s, 3H), 2.95-2.78 (m, 2H), 2.74-2.55 (m, 3H), 2.47-2.29 (m, 2H), 2.10-2.01 (m, 1H), 1.06-0.95 (m, 3H). | 1 | 909.37 |
| 48 | 953.57 | 955.57 | ¹H NMR (400 MHz, DMSO-d₆) δ 11.11 (br s, 1H), 10.07 (br s, 1H), 7.82-7.71 (m, 3H), 7.45-7.36 (m, 2H), 7.33-7.19 (m, 4H), 7.19-7.00 (m, 2H), 5.11 (dd, J = 5.4, 12.8 Hz, 1H), 4.31-4.13 (m, 2H), 3.77-3.40 (m, 21H), 3.02-2.77 (m, 4H), 2.65-2.55 (m, 3H), 2.44-2.34 (m, 2H), 2.16-198 (m, 1H), 1.09-0.97 (m, 3H). | 1 | 953.42 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| 49 | 997.6 | 999.6 | ¹H NMR (400 MHz, DMSO-d₆) δ 12.29 (br s, 1H), 11.12 (s, 1H), 10.14 (br s, 1H), 8.10 (br s, 1H), 8.01 (br s, 1H), 7.90-7.74 (m, 2H), 7.51-7.40 (m, 2H), 7.39-7.30 (m, 2H), 7.28-7.18 (m, 2H), 7.10 (s, 1H), 5.12 (br dd, J = 5.1, 12.5 Hz, 1H), 4.30 (br s, 2H), 4.21 (br s, 3H), 3.76 (br d, J = 11.8 Hz, 7H), 3.63-3.45 (m, 14H), 2.99 (s, 1H), 2.87 (s, 2H), 2.74 (br t, J = 5.6 Hz, 1H), 2.60 (br d, J = 18.3 Hz, 3H), 2.47-2.35 (m, 3H), 2.04 (br d, J = 4.8 Hz, 1H), 1.10-0.97 (m, 3H). | 1 | 997.48 |
| 50 | 1041.63 | 1043.63 | ¹H NMR (400 MHz, DMSO-d₆) δ 11.11 (br s, 1H), 8.21 (s, 1H), 7.86-7.74 (m, 3H), 7.46-7.38 (m, 2H), 7.33 (br dd, J = 2.4, 8.4 Hz, 1H), 7.26 (d, J = 2.4 Hz, 1H), 7.22 (d, J = 3.6 Hz, 2H), 7.04 (s, 2H), 5.11 (dd, J = 5.4, 12.8 Hz, 1H), 4.28 (br s, 2H), 3.90-3.63 (m, 8H), 3.62-3.39 (m, 20H), 3.02-2.79 (m, 4H), 2.68-2.54 (m, 4H), 2.37 (q, J = 7.2 Hz, 2H), 2.10-1.99 (m, 1H), 1.08-0.91 (m, 3H). | 1 | 1041.53 |
| 51 | 895.55 | 897.55 | ¹H NMR (400 MHz, DMSO-d₆) δ 10.96 (s, 1H), 8.23 (s, 1H), 7.80-7.76 (m, 2H), 7.63-7.53 (m, 1H), 7.44-7.41 (m, 1H), 7.29-7.20 (m, 3H), 7.17-7.11 (m, 1H), 7.05-7.02 (m, 2H), 5.09-5.04 (m, 1H), 4.41-4.02 (m, 5H), 3.93-3.84 (m, 1H), 3.84-3.64 (m, 7H), 3.55-3.49 (m, 10H), 3.02 (s, 2H), 2.92-2.79 (m, 3H), 2.71-2.59 (m, 3H), 2.40-2.32 (m, 2H), 2.03-1.92 (m, 1H), 1.05-0.95 (m, 3H). | 1 | 895.39 |
| 52 | 939.59 | 941.59 | ¹H NMR (300 MHz, DMSO-d₆) δ 10.97 (s, 1H), 8.24 (s, 1H), 7.83-7.74 (m, 2H), 7.60 (d, J Hz, 1H), 7.48-7.38 (m, 1H), 7.31-6.96 (m, 7H), 5.07 (dd, J = 5.2, 13.2 Hz, 1H), 4.47-4.00 (m, 5H), 3.85-3.47 (m, 21H), 3.18 (s, 1H), 3.04-2.81 (m, 4H), 2.64-2.55 (m, 2H), 2.43-2.37 (m, 2H), 2.05-1.92 (m, 1H), 1.09-0.93 (m, 3H). | 1 | 939.44 |
| 53 | 983.62 | 985.62 | ¹H NMR (300 MHz, DMSO-d₆) δ 10.97 (s, 1H), 9.98 (s, 1H), 7.83-7.76 (m, 2H), 7.61 (d, J = 8.4 Hz, 1H), 7.47-7.40 (m, 1H), 7.25 (dd, J = 2.8, 18.0 Hz, 3H), 7.18-7.00 (m, 4H), 5.08 (dd, J = 5.2, 13.2 Hz, 1H), 4.45-4.03 (m, 5H), 3.77-3.37 (m, 25H), 3.18 (d, J = 5.2 Hz, 1H), 3.04-2.80 (m, 4H), 2.64-2.55 (m, 2H), 2.44-2.37 (m, 2H), 2.04-1.92 (m, 1H), 1.07-0.98 (m, 3H). | 1 | 983.49 |
| 54 | 1027.65 | 1029.65 | ¹H NMR (400 MHz, DMSO-d₆) δ 10.97 (s, 1H), 10.01 (s, 1H), 7.85-7.74 (m, 2H), 7.60 (d, J = 8.4 Hz, 1H), 7.47-7.38 (m, 1H), 7.26 (s, 1H), 7.22-7.21 (m, 2H), 7.14 (s, 1H), 7.07-6.99 (m, 2H), 5.09-5.04 (m, 1H), 4.42-4.20 (m, 2H), 4.15 (s, 2H), 3.99-3.61 (m, 9H), 3.60-3.39 (m, 19H), 3.06-2.74 (m, 5H), 2.71-2.57 (m, 4H), 2.42-2.29 (m, 3H), 2.05-1.87 (m, 1H), 1.03-0.99 (m, 3H). | 1 | 1027.55 |
| 55 | 862.49 | 864.49 | ¹H NMR (400 MHz, DMSO-d₆) δ 11.08 (s, 1H), 10.00 (s, 1H), 8.18 (s, 1H), 7.80 (br s, 2H), 7.58 (br s, 1H), 7.43 (br dd, J = 4.3, 7.9 Hz, 1H), 7.27 (s, 1H), 7.24-7.12 (m, 3H), 7.11-6.95 (m, 2H), 6.90-6.67 (m, 2H), 6.18 (dd, J = 2.2, 16.4 Hz, 1H), 5.74 (br d, J = 11.9 Hz, 1H), 5.11-4.97 (m, 1H), 3.88-3.64 (m, 8H), 3.42-3.37 (m, 7H), 3.03 (s, 2H), 3.00-2.81 (m, 3H), 2.65-2.57 (m, 2H), 1.98 (br s, 1H). | 1 | 862.32 |
| 56 | 906.53 | 908.53 | ¹H NMR (400 MHz, DMSO-d₆) δ 11.10 (br s, 1H), 8.22 (s, 1H), 7.85-7.73 (m, 2H), 7.61-7.41 (m, 2H), 7.27-7.22 (m, 3H), 7.26-6.97 (m, 4H), 6.85 (br dd, J = 10.5, 16.6 Hz, 1H), 6.59 (br s, 1H), 6.18 (dd, J = 2.0, 16.7 Hz, 1H), 5.74 (br d, J = 12.1 Hz, 1H), 5.10-5.00 (m, 1H), 3.90-3.65 (m, 11H), 3.59-3.52 (m, 8H), 3.05-2.82 (m, 5H), 2.72-2.65 (m, 2H), 2.08-1.95 (m, 1H). | 1 | 906.37 |
| 57 | 950.56 | 952.57 | ¹H NMR (400 MHz, DMSO-d₆) δ 11.07 (s, 1H), 10.00 (br s, 1H), 8.28 (s, 1H), 7.90-7.69 (m, 2H), 7.59-7.38 (m, 2H), 7.30-7.18 (m, 3H), 7.16-6.95 (m, 4H), 6.89-6.76 (m, 1H), 6.63-6.50 (m, 1H), 6.22-6.14 (m, 1H), 5.77-5.72 (m, 1H), 5.08-5.01 (m, 1H), 3.88-3.66 (m, 7H), 3.65-3.40 (m, 17H), 3.03-2.74 (m, 4H), 2.64-2.57 (m, 2H), 2.06-1.98 (m, 1H). | 1 | 950.42 |
| 58 | 994.6 | 996.6 | ¹H NMR (400 MHz, DMSO-d₆) δ 11.09 (s, 1H), 10.01 (br s, 1H), 8.20 (s, 1H), 7.83-7.75 (m, 2H), 7.60-7.49 (m, 1H), 7.47-7.37 (m, 1H), 7.26 (d, J = 2.1 Hz, 1H), 7.22 (br d, J = 3.4 Hz, 2H), 7.16-6.95 (m, 4H), 6.90-6.78 (m, 1H), 6.57 (br s, 1H), 6.17 (br d, J = 17.0 Hz, 1H), 5.73 (br d, J = 10.6 Hz, 1H), 5.04 (br dd, J = 5.1, 12.8 Hz, 1H), 3.88-3.66 (m, 7H), 3.61-3.41 (m, 21H), 3.03-2.74 (m, 4H), 2.60 (br s, 2H), 2.00 (br d, J = 19.4 Hz, 1H). | 1 | 994.48 |
| 59 | 1038.63 | 1040.63 | ¹H NMR (400 MHz, DMSO-d₆) δ 11.11 (br s, 1H), 8.29 (s, 1H), 7.88-7.74 (m, 2H), 7.61-7.53 (m, 1H), 7.48-7.39 (m, 1H), 7.36-7.08 (m, 5H), 7.03 (br d, J = 10.4 Hz, 2H), 6.85 (dd, J = 10.4, 16.3 Hz, 1H), 6.59 (br s, 1H), 6.22-6.13 (m, 1H), 5.74 (br d, J = 11.2 Hz, 1H), 5.05 (dd, J = 5.4, 13.0 Hz, 1H), 3.91-3.66 (m, 7H), 3.64-3.43 (m, 21H), 3.38-3.31 (m, 2H), 3.03-2.80 (m, 4H), 2.63-2.57 (m, 4H), 2.08-1.92 (m, 1H). | 1 | 1038.53 |
| 60 | 907.51 | 909.51 | ¹H NMR (400 MHz, DMSO-d₆) δ 11.13 (br s, 1H), 10.04 (br s, 1H), 7.83-7.70 (m, 3H), 7.46-7.28 (m, 3H), 7.26-7.15 (m, 4H), 7.04 (d, J = 2.2 Hz, 1H), 6.85 (dd, J = 10.3, 16.9 Hz, 1H), 6.18 (dd, J = 2.2, 16.6 Hz, 1H), 5.74 (br d, J = 12.5 Hz, 1H), 5.11 (dd, J = 5.2, 12.9 Hz, 1H), 4.28-4.19 (m, 2H), 3.82-3.62 (m, 11H), 3.59-3.42 (m, 6H), 3.07-2.76 (m, 5H), 2.62-2.56 (m, 2H), 2.09-1.94 (m, 1H). | 1 | 907.35 |
| 61 | 951.54 | 953.54 | ¹H NMR (400 MHz, DMSO-d₆) δ 11.11 (br s, 1H), 10.18 (br s, 1H), 8.44 (s, 1H), 7.82-7.74 (m, 3H), 7.47-7.36 (m, 2H), 7.33-7.08 (m, 5H), 7.06-7.02 (m, 1H), 6.90-6.79 (m, 1H), 6.21-6.13 (m, 1H), 5.76-5.71 (m, 1H), 5.11 (dd, J = 5.6, 12.8 Hz, 1H), 4.30-4.15 (m, 2H), 3.88-3.62 (m, 10H), 3.59-3.44 (m, 12H), 3.05-2.76 (m, 4H), 2.63-2.59 (m, 2H), 2.09-1.99 (m, 1H). | 1 | 951.41 |
| 62 | 995.46 | 997.46 | ¹H NMR (400 MHz, DMSO-d₆) δ 11.09 (s, 1H), 10.06 (br d, J = 9.8 Hz, 1H), 7.85-7.72 (m, 3H), 7.47-7.38 (m, 2H), 7.32 (br dd, J = 2.1, 8.4 Hz, 1H), 7.26 (d, J = 2.3 Hz, 1H), 7.22 (br s, 2H), 7.04 (s, 2H), 6.88-6.75 (m, 1H), 6.17 (dd, J = 1.9, 16.7 Hz, 1H), 5.73 (br d, J = 12.3 Hz, 1H), 5.11 (dd, J = 5.3, 12.9 Hz, 1H), 4.26 (br s, 2H), 4.05-3.68 (m, 10H), 3.60-3.36 (m, 16H), 3.02-2.78 (m, 4H), 2.59 (br d, J = 16.8 Hz, 2H), 2.11-1.98 (m, 1H). | 1 | 995.46 |
| 63 | 1039.61 | 1041.61 | ¹H NMR (400 MHz, DMSO-d₆) δ 11.13 (br s, 1H), 8.31 (s, 1H), 7.89-7.72 (m, 3H), 7.48-7.39 (m, 2H), 7.38-7.08 (m, 5H), 7.05 (s, 1H), 6.85 (dd, J = 10.2, 16.4 Hz, 1H), 6.18 (dd, J = 2.0, 17.0 Hz, 1H), 5.79-5.69 (m, 1H), 5.12 (dd, J = 5.2, 12.8 Hz, 1H), 4.28 (br s, 2H), 3.88-3.65 (m, 9H), 3.56 (br s, 4H), 3.41 (br s, 15H), 3.01-2.80 (m, 4H), 2.59 (br d, J = 16.8 Hz, 4H), 2.10-2.00 (m, 1H). | 1 | 1039.51 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| 64 | 849.39 | 851.39 | $^1$H NMR (400 MHz, DMSO-d$_6$) δ 10.95 (br s, 1H), 8.20 (s, 1H), 7.83-7.77 (m, 2H), 7.64-7.38 (m, 2H), 7.27 (d, J = 2.0 Hz, 1H), 7.25-6.89 (m, 6H), 6.84 (br dd, J = 10.3, 16.8 Hz, 1H), 6.18 (dd, J = 2.4, 16.7 Hz, 1H), 5.78-5.70 (m, 1H), 5.07 (br dd, J = 5.0, 13.1 Hz, 1H), 4.42-4.12 (m, 4H), 3.86-3.64 (m, 10H), 3.57 (br s, 2H), 3.11-2.85 (m, 4H), 2.78 (br t, J = 6.7 Hz, 1H), 2.67-2.55 (m, 2H), 2.45-2.33 (m, 1H), 2.03-1.91 (m, 1H). | 1 | 849.32 |
| 65 | 893.43 | 895.43 | $^1$H NMR (400 MHz, DMSO-d$_6$) δ 10.95 (s, 1H), 8.17 (s, 1H), 7.82-7.74 (m, 2H), 7.57 (br dd, J = 8.8, 12.5 Hz, 1H), 7.47-7.38 (m, 1H), 7.27 (d, J = 2.2 Hz, 1H), 7.25-7.20 (m, 1H), 7.19-6.89 (m, 4H), 6.83 (br dd, J = 10.5, 16.6 Hz, 1H), 6.17 (dd, J = 2.1, 16.8 Hz, 1H), 5.79-5.67 (m, 1H), 5.06 (dd, J = 5.1, 13.1 Hz, 1H), 4.50-3.98 (m, 4H), 3.83-3.67 (m, 10H), 3.54 (br d, J = 4.3 Hz, 6H), 3.02-2.80 (m, 4H), 2.68-2.54 (m, 3H), 2.42-2.26 (m, 1H), 2.02-1.90 (m, 1H). | 1 | 893.37 |
| 66 | 937.57 | 939.57 | $^1$H NMR (400 MHz, DMSO-d$_6$) δ 10.95 (s, 1H), 8.22 (s, 1H), 7.79-7.80 (m, 2H), 7.59-7.57 (m, 1H), 7.26-7.22 (m, 1H), 7.11 (s, 1H), 7.09-7.07 (m, 2H), 7.05-7.01 (m, 3H), 7.00-6.95 (m, 1H), 6.83-6.80 (m, 1H), 6.16 (d, J = 16.8 Hz, 1H), 5.73 (d, J = 10.8 Hz, 1H), 5.08-5.04 (m, 1H), 4.32-4.21 (m, 2H), 4.13-4.02 (m, 2H), 3.81-3.75 (m, 9H), 3.54-3.49 (m, 11H), 3.00-2.80 (m, 4H), 2.66-2.60 (m, 3H), 2.36-2.33 (m, 1H), 2.0-1.98 (m, 1H). | 1 | 937.42 |
| 67 | 981.6 | 983.6 | $^1$H NMR (400 MHz, DMSO-d$_6$) δ 10.97 (s, 1H), 8.19 (s, 1H), 7.82-7.75 (m, 2H), 7.60 (d, J = 8.3 Hz, 1H), 7.47-7.39 (m, 1H), 7.26 (d, J = 2.2 Hz, 1H), 7.22 (br d, J = 3.3 Hz, 2H), 7.20-7.06 (m, 2H), 7.06-6.99 (m, 2H), 6.84 (ddd, J = 2.2, 10.5, 16.6 Hz, 1H), 6.17 (dd, J = 2.0, 16.7 Hz, 1H), 5.78-5.70 (m, 1H), 5.07 (dd, J = 5.0, 13.3 Hz, 1H), 4.41-4.31 (m, 1H), 4.28-4.19 (m, 1H), 4.13 (br s, 2H), 3.90-3.59 (m, 12H), 3.47 (br s, 12H), 3.05-2.75 (m, 4H), 2.68-2.54 (m, 3H), 2.43-2.29 (m, 1H), 2.03-1.89 (m, 1H). | 1 | 981.48 |
| 68 | 1025.63 | 1027.63 | $^1$H NMR (400 MHz, DMSO-d$_6$) δ 10.96 (br s, 1H), 8.30 (s, 1H), 7.86-7.74 (m, 2H), 7.61 (d, J = 8.4 Hz, 1H), 7.48-7.38 (m, 1H), 7.35-6.99 (m, 7H), 6.84 (dd, J = 10.4, 16.4 Hz, 1H), 6.18 (dd, J = 2.4, 16.8 Hz, 1H), 5.80-5.70 (m, 1H), 5.07 (dd, J = 5.2, 13.4 Hz, 1H), 4.42-4.22 (m, 2H), 4.16 (br s, 2H), 4.01-3.66 (m, 9H), 3.56 (br s, 8H), 3.43 (br d, J = 9.2 Hz, 7H), 3.03-2.78 (m, 4H), 2.62-2.57 (m, 5H), 2.44-2.34 (m, 1H), 2.03-1.91 (m, 1H). | 1 | 1025.53 |
| 69 | 875.6 | 877.6 | $^1$H NMR (400 MHz, CD$_3$OD) δ 8.25 (s, 1H), 7.79-7.53 (m, 2H), 7.41-7.16 (m, 3H), 6.88-6.64 (m, 3H), 6.26 (br d, J = 16.8 Hz, 1H). 5.79 (br d, J = 10.4 Hz, 1H), 5.19-5.02 (m, 1H), 4.28-4.05 (m, 3H), 4.01-3.48 (m, 22H), 3.14 (br s, 2H), 2.95 (s, 2H), 2.89-2.66 (m, 6H), 2.17-1.99 (m, 1H). | 1 | 875.28 |
| 70 | 875.6 | 877.6 | $^1$H NMR (400 MHz, CD$_3$OD) δ 8.44 (br s, 1H), 7.76-7.51 (m, 2H), 7.41-6.96 (m, 4H), 6.87-6.62 (m, 4H), 6.25 (br d, J = 16.6 Hz, 1H), 5.78 (br d, J = 10.5 Hz, 1H), 5.17-5.00 (m, 1H), 4.31-4.02 (m, 1H), 3.95-3.52 (m, 15H), 3.14 (br s, 1H), 3.00-2.56 (m, 8H), 2.09 (br d, J = 11.7 Hz, 1H). | 1 | 875.28 |
| 71 | 919.63 | 921.63 | $^1$H NMR (400 MHz, CD$_3$OD) δ 7.76-7.58 (m, 1H), 7.35-7.23 (m, 1H), 7.17 (dd, J = 2.3, 8.4 Hz, 1H), 6.84-6.73 (m, 1H), 6.70 (t, J = 8.7 Hz, 1H), 6.25 (td, J = 1.9, 16.8 Hz, 1H), 5.78 (d, J = 10.8 Hz 1H), 5.12-5.02 (m, 1H), 4.25-4.05 (m, 2H), 3.91-3.50 (m, 22H), 3.13 (br s, 1H), 2.96-2.88 (m, 2H), 2.87-2.80 (m, 2H), 2.78-2.62 (m, 3H), 2.15-2.01 (m, 1H), 2.15-2.01 (m, 1H). | 1 | 919.34 |
| 72 | 919.63 | 921.63 | $^1$H NMR (400 MHz, CD$_3$OD) δ 7.75-7.61 (m, 1H), 7.35-7.22 (m, 1H), 7.17 (dd, J = 2.4, 8.4 Hz, 1H), 6.83-6.74 (m, 1H), 6.70 (t, J = 8.7 Hz, 1H), 6.25 (td, J = 2.0, 16.8 Hz, 1H), 5.83-5.73 (m, 1H), 5.13-5.03 (m, 1H), 4.25-4.06 (m, 2H), 3.92-3.52 (m, 21H), 2.97-2.90 (m, 2H), 2.88-2.65 (m, 5H), 2.16-2.05 (m, 1H). | 1 | 919.34 |
| 73 | 963.67 | 965.67 | $^1$H NMR (400 MHz, METHANOL-d$_4$) δ 7.76-7.68 (m, 2H), 7.37-7.17 (m, 3H), 6.85-6.66 (m, 3H), 6.25 (dd, J = 1.6, 16.4 Hz, 1H), 5.83-5.74 (m, 1H), 5.08 (dd, J = 5.6, 12.4 Hz, 1H), 4.25-4.17 (m, 2H), 3.90-3.50 (m, 23H), 3.13 (br s, 1H), 2.93 (s, 2H), 2.88-2.80 (m, 2H), 2.78-2.61 (m, 3H), 2.17-2.06 (m, 1H). | 1 | 963.39 |
| 74 | 963.67 | 965.67 | $^1$H NMR (400 MHz, METHANOL-d$_4$) δ 7.76-7.69 (m, 2H), 7.37-7.21 (m, 3H), 6.84-6.67 (m, 3H), 6.26 (br d, J = 16.8 Hz, 1H), 5.79 (br d, J = 11.2 Hz, 1H), 5.09 (br dd, J = 5.6, 12.4 Hz, 1H), 4.21 (br s, 2H), 3.92-3.50 (m, 25H), 3.13 (br s, 1H), 2.93 (s, 2H), 2.88-2.66 (m, 6H), 2.17-2.06 (m, 1H). | 1 | 963.39 |
| 75 | 1007.71 | 1009.71 | $^1$H NMR (400 MHz, METHANOL-d$_4$) δ 8.46 (br s, 1H), 7.78-7.69 (m, 2H), 7.40-7.21 (m, 3H), 6.85-6.66 (m, 3H), 6.25 (dd, J = 2.0, 16.8 Hz, 1H), 5.79 (dd, J = 2.0, 10.4 Hz, 1H), 5.09 (dd, J = 5.6, 12.4 Hz, 1H), 4.57 (br s, 3H), 4.27-4.21 (m, 2H), 3.92-3.45 (m, 30H), 3.16-2.92 (m, 3H), 2.89-2.81 (m, 2H), 2.79-2.46 (m, 3H), 2.38-1.98 (m, 2H), 1.37-1.28 (m, 2H). | 1 | 1007.44 |
| 76 | 1007.71 | 1009.71 | $^1$H NMR (400 MHz, METHANOL-d$_4$) δ 8.46 (br s, 1H), 7.77-7.70 (m, 2H), 7.39-7.23 (m, 3H), 6.86-6.66 (m, 3H), 6.25 (dd, J = 1.6, 16.8 Hz, 1H), 5.83-5.75 (m, 1H), 5.09 (dd, J = 5.6, 12.4 Hz, 1H), 4.57 (br s, 5H), 4.28-4.20 (m, 2H), 3.92-3.46 (m, 30H), 3.13 (br s, 1H), 2.93 (s, 2H), 2.88-2.80 (m, 2H), 2.78-2.45 (m, 3H), 2.38-1.98 (m, 2H), 1.34-1.29 (m, 2H). | 1 | 1007.44 |
| 77 | 819.56 | 821.56 | $^1$H NMR (400 MHz, METHANOL-d$_4$) δ 7.72 (br d, J = 8.0 Hz, 2H), 7.40-7.06 (m, 3H), 6.86-6.64 (m, 2H), 5.08 (br dd, J = 4.8, 12.4 Hz, 1H), 4.24 (br s, 2H), 4.00-3.59 (m, 12H), 3.22 (br s, 1H), 3.05-2.64 (m, 7H), 2.19-2.05 (m, 4H). | 1 | 819.22 |
| 78 | 819.56 | 821.56 | $^1$H NMR (400 MHz, METHANOL-d$_4$) δ 7.84-7.53 (m, 2H), 7.40-7.03 (m, 3H), 6.83-6.64 (m, 2H), 5.08 (br dd, J = 4.8, 12.8 Hz, 1H), 4.33-4.11 (m, 2H), 4.02-3.64 (m, 12H), 3.22 (br s, 1H), 3.04-2.62 (m, 7H), 2.18-2.02 (m, 4H). | 1 | 819.22 |
| 79 | 863.59 | 865.59 | $^1$H NMR (400 MHz, CD$_3$OD) δ 8.28 (br s, 1H), 7.78-7.53 (m, 2H), 7.37-7.26 (m, 1H), 7.21 (br d, J = 7.7 Hz, 1H), 6.85-6.65 (m, 3H), 5.13-5.01 (m, 1H), 4.26-4.05 (m, 3H), 3.96-3.48 (m, 22H), 3.14 (br s, 2H), 3.01-2.61 (m, 9H), 2.20-2.02 (m, 5H). | 1 | 863.27 |
| 80 | 863.59 | 865.59 | $^1$H NMR (400 MHz, CD$_3$OD) δ 8.49-8.36 (m, 1H), 8.44 (br s, 1H), 7.72-7.53 (m, 1H), 7.37-7.25 (m, 1H), 7.23-6.98 (m, 1H), 6.82-6.65 (m, 1H), 5.07 (br dd, J = 6.4, 11.9 Hz, 1H), 4.23-4.02 (m, 2H), 3.89-3.52 (m, 17H), 3.14 (br s, 1H), 2.98-2.91 (m, 1H), 2.88-2.66 (m, 5H), 2.15 (d, J = 2.9 Hz, 4H). | 1 | 863.27 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| 81 | 907.63 | 909.63 | ¹H NMR (400 MHz, CD₃OD) δ 8.18 (s, 1H), 7.68 (br d, J = 8.3 Hz, 1H), 7.42-7.10 (m, 3H), 6.82-6.63 (m, 2H), 5.07 (br dd, J = 5.3, 12.7 Hz, 1H), 4.25-4.14 (m, 1H), 3.88-3.51 (m, 20H), 3.19-3.07 (m, 1H), 3.03-2.51 (m, 8H), 2.14 (d, J = 2.9 Hz, 4H). | 1 | 907.33 |
| 82 | 907.63 | 909.63 | ¹H NMR (400 MHz, CD₃OD) δ 8.18 (br s, 1H), 7.70 (br d, J = 8.6 Hz, 1H), 7.37-7.27 (m, 2H) 7.24-7.14 (m, 1H), 7.19 (s, 1H), 6.85-6.64 (m, 2H), 5.07 (br s, 1H), 4.66-4.49 (m, 3H), 4.28-4.07 (m, 1H), 3.86-3.72 (m, 7H), 3.67-3.51 (m, 7H), 3.13 (br s, 1H), 2.94 (s, 10H), 2.15 (br d, J = 3.1 Hz, 4H) | 1 | 907.33 |
| 83 | 951.67 | 953.67 | ¹H NMR (400 MHz, METHANOL-d₄) δ 7.76-7.65 (m, 2H), 7.37-7.18 (m, 3H), 6.76 (d, J = 8.4 Hz, 1H), 6.70 (t, J = 8.8 Hz, 1H), 5.08 (dd, J = 5.2, 12.4 Hz, 1H), 4.26-4.16 (m, 2H), 3.87-3.47 (m, 23H), 3.13 (br s, 1H), 2.96-2.89 (m, 2H), 2.84 (m, 2H), 2.78-2.64 (m, 3H), 2.15 (m, 4H). | 1 | 951.38 |
| 84 | 951.67 | 953.67 | ¹H NMR (400 MHz, METHANOL-d₄) δ 7.71 (br d, J = 8.4 Hz, 1H), 6.76 (d, J = 8.0 Hz. 1H). 6.70 (t, J = 8.8 Hz, 1H), 5.08 (dd, J = 5.6, 12.4 Hz, 1H), 4.24-4.18 (m, 2H), 3.86-3.49 (m, 23H), 3.13 (br s, 1H), 2.96-2.89 (m, 2H), 2.88-2.80 (m, 2H), 2.79-2.62 (m, 3H), 2.15 (m, 4H). | 1 | 951.38 |
| 85 | 995.71 | 997.71 | ¹H NMR (400 MHz, METHANOL-d₄) δ 8.42 (br s, 1H), 7.78-7.68 (m, 2H), 7.39-7.22 (m, 3H), 6.76 (d, J = 8.0 Hz, 1H), 6.70 (t, J = 8.8 Hz, 1H), 5.09 (dd, J = 5.6, 12.4 Hz, 1H), 4.66-4.47 (m, 2H), 4.27-4.21 (m, 2H), 3.87-3.46 (m, 30H), 3.15-2.92 (m, 3H), 2.89-2.80 (m, 2H), 2.78-2.46 (m, 3H), 2.38-1.99 (m, 5H), 1.36-1.28 (m, 2H). | 1 | 995.43 |
| 86 | 995.71 | 997.71 | ¹H NMR (400 MHz, METHANOL-d₄) δ 8.51 (br s, 1H), 7.78-7.68 (m, 2H), 7.40-7.22 (m, 3H), 6.80-6.66 (m, 2H), 5.09 (dd, J = 5.6, 12.4 Hz, 1H), 4.57 (br s, 4H), 4.29-4.21 (m, 2H), 3.88-3.46 (m, 30H), 3.16-2.92 (m, 3H), 2.91-2.80 (m, 2H), 2.79-2.44 (m, 3H), 2.38-1.94 (m, 5H), 1.35-1.28 (m, 2H). | 1 | 995.43 |
| 87 | 817.57 | 819.57 | ¹H NMR (400 MHz, DMSO-d₆) δ 10.96 (s, 1H), 10.46 (br s, 1H), 8.03 (br s, 1H), 7.96-7.72 (m, 1H), 7.68-7.54 (m, 1H), 7.39 (br d, J = 8.3 Hz, 1H), 7.17 (br s, 1H), 7.10-6.96 (m, 1H), 6.84 (br dd, J = 8.4, 19.5 Hz, 3H), 6.17 (br d, J = 17.1 Hz, 1H), 5.85-5.60 (m, 1H), 5.13-4.95 (m, 1H), 4.41-4.10 (m, 8H), 3.86 (br s, 2H), 3.75 (br s, 4H), 3.07 (br s, 1H), 2.98-2.76 (m, 3H), 2.69 (br s, 1H), 2.61 (br s, 4H), 2.41-2.36 (m, 1H), 1.98 (br s, 1H). | 1 | 817.25 |
| 88 | 817.57 | 819.57 | ¹H NMR (400 MHz, DMSO-d₆) δ 10.95 (s, 1H), 10.55-10.16 (m, 1H), 8.02 (br s, 1H), 7.94-7.70 (m, 1H), 7.62 (br d, J = 7.5 Hz, 1H), 7.37 (br s, 1H), 7.17 (br s, 1H), 7.08-6.95 (m, 1H), 6.88-6.69 (m, 3H), 6.17 (br d, J = 16.9 Hz, 1H), 5.75 (br d, J = 10.5 Hz, 1H), 5.06 (br dd, J = 4.6, 12.8 Hz, 1H), 4.41-4.09 (m, 8H), 3.85 (br s, 3H), 3.76 (br s, 4H), 3.07 (br s, 1H), 2.94-2.79 (m, 3H), 2.72-2.68 (m, 1H), 2.58 (br d, J = 18.1 Hz, 4H), 2.37 (m, 1H), 1.97 (br s, 1H). | 1 | 817.25 |
| 89 | 861.62 | 863.62 | ¹H NMR (DMSO-d₆) δ 10.98 (s, 1H), 10.20 (s, 1H), 7.76-7.53 (m, 2H), 7.38-7.28 (m, 1H), 7.18-7.00 (m, 2H), 6.89-6.74 (m, 3H), 6.17 (d, J = 15.6 Hz, 1H), 5.73 (d, J = 12.4 Hz, 1H), 5.07 (dd, J = 4.8, 13.2 Hz, 1H), 4.37-4.07 (m, 4H), 3.96-3.43 (m, 15H), 3.23-2.78 (m, 514), 2.61 (s, 2H), 2.10-1.89 (m, 2H), 1.24 (s, 1H). | 1 | 861.30 |
| 90 | 861.62 | 863.62 | ¹H NMR (DMSO-d₆) δ 10.96 (s, 1H), 10.17 (s, 1H), 7.71 (d, J = 8.4 Hz, 1H), 7.63-7.52 (m, 1H), 7.39-7.27 (m, 1H), 7.25-6.90 (m, 3H), 6.88-6.73 (m, 3H), 6.23-6.11 (m, 1H), 5.80-5.66 (m, 1H), 5.06 (dd, J = 5.2, 13.2 Hz, 1H), 4.39-4.07 (m, 4H), 3.89-3.41 (m, 17H), 3.09-2.80 (m, 4H), 2.65-2.55 (m, 2H), 2.43-2.33 (m, 1H), 2.09-1.93 (m, 1H). | 1 | 861.30 |
| 91 | 905.65 | 907.65 | ¹H NMR (400 MHz, DMSO-d₆) δ 10.95 (s, 1H), 10.37 (s, 1H), 7.70 (d, J = 2.8 Hz, 1H), 7.60-7.58 (m, 1H), 7.34-7.28 (m, 1H), 7.12-6.99 (m, 3H), 6.85-6.74 (m, 3H), 6.17-6.10 (m, 1H), 5.72 (d, J = 11.2 Hz, 1H), 5.06 (dd, J = 5.2, 13.6 Hz, 1H), 4.37-4.21 (m, 2H), 4.15-4.09 (m, 2H), 3.75-3.67 (m, 10H), 3.56-3.51 (m, 10H), 3.01-2.81 (m, 4H), 2.66-2.60 (m, 3H), 2.40-2.32 (m, 1H), 1.98-1.95 (m, 1H). | 1 | 905.35 |
| 92 | 905.65 | 907.65 | ¹H NMR (400 MHz, DMSO-d₆) δ 10.79 (s, 1H), 10.58 (s, 1H), 8.10 (s, 1H), 8.02 (s, 1H), 7.60 (d, J = 7.2 Hz, 1H), 7.39-7.37 (m, 1H), 7.12 (d, J = 7.6 Hz, 1H), 7.01-7.00 (m, 1H), 6.88-6.75 (m, 3H), 6.18 (d, J = 16.4 Hz, 1H), 5.75 (d, J = 10.4 Hz, 1H), 5.07-5.04 (m, 1H), 4.39-4.33 (m, 2H), 4.26-4.16 (m, 6H), 3.87-3.70 (m, 16H), 2.96-2.84 (m, 4H), 2.72-2.58 (m, 3H), 2.41-2.34 (m, 1H), 2.01-1.92 (m, 1H). | 1 | 905.35 |
| 93 | 949.69 | 951.69 | ¹H NMR (400 MHz, DMSO-d₆) δ 10.96 (s, 1H), 10.21 (s, 1H), 7.82-7.53 (m, 2H), 7.37-7.26 (m, 1H), 7.21-6.94 (m, 3H), 6.87-6.72 (m, 3H), 6.28-6.03 (m, 1H), 5.72 (d, J = 11.6 Hz, 1H), 5.06 (dd, J = 5.0, 13.2 Hz, 1H), 4.42-4.20 (m, 2H), 4.13 (d, J = 3.2 Hz, 2H), 3.79-3.43 (m, 24H), 3.08-2.74 (m, 4H), 2.68-2.54 (m, 3H), 2.45-2.32 (m, 1H), 2.09-1.82 (m, 1H). | 1 | 949.41 |
| 94 | 949.69 | 951.69 | ¹H NMR (400 MHz, DMSO-d₆) δ 10.98 (s, 1H), 10.40-10.06 (m, 1H), 7.72 (s, 1H), 7.61 (d, J = 8.4 Hz, 1H), 7.39-6.99 (m, 4H), 6.90-6.72 (m, 3H), 6.17 (d, J = 17.0 Hz, 1H), 5.73 (d, J = 11.0 Hz, 1H), 5.07 (dd, J = 5.0, 13.2 Hz, 1H), 4.44-4.20 (m, 2H), 4.15 (d, J = 3.2 Hz, 2H), 3.86-3.46 (m, 24H), 3.06-2.93 (m, 2H), 2.92-2.80 (m, 2H), 2.68-2.58 (m, 3H), 2.40-2.31 (m, 1H), 2.04-1.92 (m, 1H). | 1 | 949.41 |
| 95 | 993.72 | 995.72 | ¹H NMR (400 MHz, DMSO-d₆) δ 10.97 (s, 1H), 10.68-9.90 (m, 1H), 7.72 (s, 1H), 7.62 (d, J = 8.4 Hz, 1H), 7.39-7.27 (m, 1H), 7.16 (s, 1H), 7.05 (br d, J = 8.4 Hz, 1H), 6.89-6.74 (m, 3H), 6.17 (dd, J = 2.0, 16.4 Hz, 1H), 5.78-5.70 (m, 1H), 5.08 (dd, J = 5.2, 13.2 Hz, 1H), 4.43-4.22 (m, 2H), 4.17 (br s, 2H), 3.82-3.64 (m, 10H), 3.59-3.46 (m, 18H), 3.09-2.76 (m, 4H), 2.70-2.52 (m, 5H), 2.44-2.28 (m, 1H), 2.04-1.93 (m, 1H). | 1 | 993.46 |
| 96 | 993.72 | 995.72 | ¹H NMR (400 MHz, DMSO-d₆) δ 10.97 (s, 1H), 10.27 (br s, 1H), 7.72 (s, 1H), 7.62 (d, J = 8.4 Hz, 1H), 7.38-7.26 (m, 1H), 7.16 (s, 1H), 7.05 (br d, J = 8.8 Hz, 1H), 6.89-6.74 (m, 3H), 6.17 (dd, J = 2.4, 16.8 Hz, 1H), 5.78-5.67 (m, 1H), 5.08 (dd, J = 5.2, 13.2 Hz, 1H), 4.43-4.22 (m, 2H), 4.17 (br s, 2H), 3.82-3.63 (m, 10H), 3.59-3.46 (m, 16H), 3.02-2.80 (m, 4H), 2.70-2.54 (m, 5H), 2.44-2.30 (m, 1H), 2.03-1.92 (m, 1H). | 1 | 993.46 |
| 97 | 805.57 | 807.57 | ¹H NMR (400 MHz, METHANOL-d₄) δ 8.32 (br s, 1H), 7.77-7.54 (m, 2H), 7.35-7.26 (m, 1H), 7.01-6.91 (m, 1H), 6.81-6.75 (m, 1H), 6.74-6.68 (m, 1H), 5.06 (br dd, J = 6.8, 11.9 Hz, 1H), 4.57 (br s, 6H), 4.24-4.07 (m, 3H), 3.79-3.71 (m, 6H), 3.22 (br s, 2H), 3.03 (s, 2H), 2.95-2.82 (m, 2H), 2.81-2.64 (m, 2H), 2.47-2.32 (m, 1H), 2.16-2.08 (m, 4H). | 1 | 805.24 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| 98 | 805.57 | 807.57 | ¹H NMR (400 MHz, METHANOL-d₄) δ 8.31 (br s, 1H), 7.81-7.56 (m, 2H), 7.39-7.27 (m, 1H), 7.05-6.91 (m, 1H), 6.81-6.77 (m, 1H), 6.76-6.71 (m, 1H), 5.08 (br dd, J = 7.2, 12.2 Hz, 1H), 4.59 (br s, 6H), 4.41-4.11 (m, 3H), 3.83-3.69 (m, 6H), 3.24 (m, 2H), 3.05 (s, 2H), 2.97-2.83 (m, 2H), 2.79 (br s, 2H), 2.51-2.35 (m, 1H), 2.19-2.08 (m, 4H). | 1 | 805.24 |
| 99 | 849.61 | 851.61 | ¹H NMR (DMSO-d₆) δ 10.98 (s, 1H), 10.19 (s, 1H), 7.74-7.52 (m, 2H), 7.40-6.71 (m, 6H), 5.07 (dd, J = 5.2, 13.2 Hz, 1H), 4.36-4.08 (m, 4H), 3.92-3.43 (m, 15H), 3.14-2.70 (m, 5H), 2.61 (s, 2H), 2.11-1.90 (m, 5H), 1.24 (s, 1H). | 1 | 849.29 |
| 100 | 849.61 | 851.61 | ¹H NMR (DMSO-d₆) δ 10.96 (s, 1H), 10.17 (s, 1H), 7.70 (d, J = 8.7 Hz, 1H), 7.64-7.52 (m, 1H), 7.37-7.27 (m, 1H), 7.25-6.91 (m, 3H), 6.87-6.72 (m, 2H), 5.06 (dd, J = 5.1, 13.3 Hz, 1H), 4.40-4.06 (m, 4H), 3.80-3.42 (m, 17H), 3.09-2.81 (m, 4H), 2.65-2.55 (m, 2H), 2.39-2.28 (m, 1H), 209-1.95 (m. 4H). | 1 | 849.29 |
| 101 | 893.65 | 895.65 | ¹H NMR (400 MHz, DMSO-d₆) δ 10.97 (s, 1H), 10.53 (s, 1H), 8.01-7.78 (m, 2H), 7.61-7.59 (m, 1H), 7.42-7.36 (m, 1H), 7.14-7.12 (m, 1H),7.03-7.00 (m, 1H), 6.88-6.80 (m, 2H), 5.06 (dd, J = 4.8, 13.2 Hz, 1H), 4.39-4.21 (m, 2H), 4.17-4.13 (m, 5H), 3.77-3.64 (m, 9H), 3.58-3.54 (m, 6H), 2.97-2.86 (m, 5H), 2.74-2.58 (m, 4H), 2.38-2.33 (m, 1H), 2.07-2.04 (m, 3H), 1.98-1.95 (m, 1H). | 1 | 893.34 |
| 102 | 893.65 | 895.65 | ¹H NMR (400 MHz, DMSO-d₆) δ 7.68 (d, J = 3.2 Hz, 1H), 7.59 (d, J = 8.8 Hz, 1H), 7.34-7.28 (m, 1H), 7.12-6.99 (m, 3H), 6.83 (d, J = 8.0 Hz, 1H), 6.78-6.74 (m, 1H), 5.08-5.04 (m, 1H), 4.37-4.21 (m, 2H), 4.14-4.08 (m, 2H), 3.74-3.41 (m, 18H), 3.02-2.81 (m, 5H), 2.66-2.60 (m, 4H), 2.37-2.33 (m, 1H), 2.04-2.03 (m, 3H), 1.98-1.95 (m, 1H). | 1 | 893.34 |
| 103 | 937.68 | 939.68 | ¹H NMR (400 MHz, DMSO-d₆) δ 11.27-10.62 (m, 1H), 10.47-9.91 (m, 1H), 7.70 (s, 1H), 7.61 (d, J = 8.4 Hz, 1H), 7.41-6.97 (m, 4H), 6.91-6.70 (m, 2H), 5.06 (dd, J = 5.0, 13.2 Hz, 1H), 4.41-4.20 (m, 2H), 4.14 (d, J = 4.0 Hz, 2H), 3.78-3.45 (m, 24H), 3.08-2.77 (m, 4H), 2.58 (d, J = 18.6 Hz, 3H), 2.41-2.28 (m, 1H), 2.10-1.91 (m, 4H). | 1 | 937.40 |
| 104 | 937.69 | 939.69 | ¹H NMR (400 MHz, DMSO-d₆) δ 11.14-10.77 (m, 1H), 10.20 (s, 1H), 7.70 (s, 1H), 7.61 (d, J = 8.4 Hz, 1H), 7.35-6.99 (m, 4H), 6.87-6.71 (m, 2H), 5.07 (dd, J = 5.0, 13.0 Hz, 1H), 4.42-4.20 (m, 2H), 4.14 (d, J = 3.2 Hz, 2H), 3.84-3.47 (m, 24H), 3.02 (s, 2H), 2.92-2.74 (m, 1H), 2.92-2.73 (m, 1H), 2.60 (s, 3H), 2.41-2.31 (m, 1H), 2.13-1.92 (m, 4H). | 1 | 937.40 |
| 105 | 981.73 | 983.73 | ¹H NMR (400 MHz, DMSO-d₆) δ 10.97 (br s, 1H), 10.64-9.73 (m, 1H), 8.26 (s, 1H), 7.71 (s, 1H), 7.62 (d, J = 8.4 Hz, 1H), 7.40-7.23 (m, 1H), 7.16 (s, 1H), 7.05 (br d, J = 8.4 Hz, 1H), 6.87-6.73 (m, 2H), 5.08 (dd, J = 5.2, 13.2 Hz, 1H), 4.44-4.21 (m, 2H), 4.17 (br s, 2H), 3.77-3.63 (m, 10H), 3.53-3.46 (m, 16H), 3.05-2.80 (m, 4H), 2.72-2.54 (m, 5H), 2.43-2.30 (m, 1H), 2.05 (s, 3H), 2.01-1.93 (m, 1H). | 1 | 981.45 |
| 106 | 981.72 | 983.72 | ¹H NMR (400 MHz, DMSO-d₆) δ 10.97 (s, 1H), 10.41-10.03 (m, 1H), 8.23 (s, 1H),7.71 (s, 1H), 7.62 (d, J = 8.4 Hz, 1H), 7.32 (q, J = 8.0 Hz, 1H), 7.16 (s, 1H), 7.05 (br d, J = 8.4 Hz, 1H), 6.88-6.74 (m, 2H), 5.07 (dd, J = 5.2, 13.2 Hz, 1H), 4.42-4.23 (m, 2H), 4.17 (br s, 2H), 3.77-3.62 (m, 16H), 3.49 (br s, 10H), 2.92-2.81 (m, 4H), 2.68 (br s, 5H), 2.35 (br d, J = 11.6 Hz, 1H), 2.05 (s, 3H), 1.99 (br s, 1H). | 1 | 981.45 |
| 107 | 830.57 | 832.57 | ¹H NMR (400 MHz, DMSO-d₆) δ 11.07 (s, 1H), 10.18 (br s, 1H), 8.18 (s, 1H), 7.72 (s, 1H), 7.63-7.55 (m, 1H), 7.38-7.27 (m, 1H), 7.24-7.15 (m, 1H), 7.13-6.91 (m, 1H), 6.87-6.65 (m, 4H), 6.23-6.09 (m, 1H), 5.80-5.67 (m, 1H), 5.11-4.95 (m, 1H), 3.88-3.62 (m, 7H), 3.60-3.44 (m, 9H), 3.10-2.80 (m, 4H), 2.65-2.58 (m, 2H), 2.06-1.94 (m, 1H). | 1 | 830.25 |
| 108 | 830.57 | 832.57 | ¹H NMR (400 MHz, DMSO-d₆) δ 11.07 (s, 1H), 10.19 (br s, 1H), 8.17 (s, 1H), 7.72 (s, 1H), 7.63-7.54 (m, 1H), 7.41-7.26 (m, 1H), 7.24-7.15 (m, 1H), 7.14-6.91 (m, 1H), 6.88-6.68 (m, 4H), 6.23-6.09 (m, 1H), 5.80-5.66 (m, 1H), 5.10-4.96 (m, 1H), 3.93-3.61 (m, 7H), 3.60-3.45 (m, 9H), 3.08-2.80 (m, 4H), 2.64-2.57 (m, 2H), 2.07-1.90 (m, 1H). | 1 | 830.25 |
| 109 | 874.61 | 876.61 | ¹H NMR (400 MHz, DMSO-d₆) δ 11.07 (s, 1H), 10.57-9.79 (m, 1H), 8.21 (s, 1H), 7.69 (d, J = 14.1 Hz, 1H), 7.59-7.41 (m, 1H), 7.36-7.27 (m, 1H), 7.12 (d, J = 8.4 Hz, 1H), 6.99 (br t, J = 7.3 Hz, 1H), 6.87-6.73 (m, 3H), 6.62-6.49 (m, 1H), 6.16 (dd, J = 2.0, 16.6 Hz, 1H), 5.80-5.68 (m, 1H), 5.03 (dd, J = 5.3, 12.9 Hz, 1H), 3.82-3.71 (m, 5H), 3.66 (br s, 3H), 3.60-3.49 (m, 8H), 3.05-2.80 (m, 4H), 2.65-2.52 (m, 6H), 2.00 (br d, J = 10.5 Hz, 1H). | 1 | 874.30 |
| 110 | 874.61 | 876.61 | ¹H NMR (400 MHz, DMSO-d₆) δ 11.08 (s, 1H), 10.19 (br s, 1H), 8.21 (s, 1H), 7.70 (br d, J = 13.8 Hz, 1H), 7.59-7.43 (m, 1H), 7.32 (q, J = 7.5 Hz, 1H), 7.13 (br d, J = 9.2 Hz, 1H), 6.99 (br t, J = 7.0 Hz, 1H), 6.88-6.73 (m, 3H), 6.59 (br d, J = 5.9 Hz, 1H), 6.16 (br d, J = 18.6 Hz, 1H), 5.73 (br d, J = 12.7 Hz, 1H), 5.10-4.96 (m, 1H), 3.81-3.66 (m, 8H), 3.60-3.50 (m, 8H), 3.07-2.80 (m, 4H), 2.66-2.54 (m, 6H), 2.01 (br d, J = 10.3 Hz, 1H). | 1 | 874.30 |
| 111 | 918.65 | 920.65 | ¹H NMR (400 MHz, DMSO-d₆) δ 11.09 (s, 1H), 10.47 (s, 1H), 8.10-8.00 (m, 1H), 7.94-7.77 (m, 1H), 7.55-7.51 (m, 1H), 7.39-7.37 (m, 1H), 7.11-7.00 (m, 2H), 6.87-6.74 (m, 3H), 6.59-6.56 (m, 1H), 6.18 (d, J = 16.8 Hz, 1H), 5.75 (d, J = 9.6 Hz, 1H), 5.04 (dd, J = 4.8, 13.2 Hz, 1H), 4.25-4.13 (m, 3H), 3.85-3.68 (m, 17H), 2.95-2.84 (m, 4H), 2.70-2.59 (m, 6H), 2.02-1.99 (m, 1H). | 1 | 918.35 |
| 112 | 918.65 | 920.65 | ¹H NMR (400 MHz, DMSO-d₆) δ 11.09 (s, 1H), 10.49 (s, 1H), 8.02-8.00 (m, 1H), 7.95-7.80 (m, 1H), 7.55-7.51 (m, 1H), 7.40-7.38 (m, 1H), 7.12-7.01 (m, 2H), 6.88-6.74 (m, 3H), 6.55-6.50 (m, 1H), 6.18 (d, J = 16.8 Hz, 1H), 5.75 (d, J = 9.6 Hz, 1H), 5.04 (dd, J = 4.8, 13.6 Hz, 1H), 4.20-4.11 (m, 3H), 3.86-3.68 (m, 17H), 2.95-2.84 (m, 4H), 2.71-2.55 (m, 6H), 2.02-2.00 (m, 1H). | 1 | 918.35 |
| 113 | 962.68 | 964.68 | ¹H NMR (400 MHz, DMSO-d₆) δ 11.09 (s, 1H), 10.45-9.96 (m, 1H), 8.21 (s, 1H), 7.72 (s, 1H), 7.63-7.49 (m, 1H), 7.32 (q, J = 8.0 Hz, 1H), 7.18-7.07 (m, 1H), 7.03 (dd, J = 2.0, 7.2 Hz, 1H), 6.89-6.72 (m, 3H), 6.64-6.53 (m, 1H), 6.23-6.09 (m, 1H), 5.73 (dd, J = 1.6, 12.4 Hz, 1H), 5.05 (dd, J = 4.8, 13.2 Hz, 1H), 3.88-3.66 (m, 8H), 3.62-3.45 (m, 16H), 3.02-2.80 (m, 4H), 2.72-2.52 (m, 614), 2.08-1.97 (m, 1H). | 1 | 962.41 |
| 114 | 962.68 | 964.68 | ¹H NMR (400 MHz, DMSO-d₆) δ 11.09 (s, 1H), 10.17 (br s, 1H), 8.16 (s, 1H), 7.72 (s, 1H), 7.62-7.45 (m, 1H), 7.32 (q, J = 8.0 Hz, 1H), 7.11 (dd, J = 5.2, 8.4 Hz, 1H), 7.03 (dd, J = 1.6, 7.2 Hz, 1H), 6.87-6.73 (m, 3H), 6.58 (br d, J = 4.8 Hz, 1H), 6.17 (br d, J = 16.4 Hz, 1H), 5.73 (br d, J = 10.8 Hz, 1H), 5.05 (dd, J = 5.2, 12.8 Hz, 1H), 3.84-3.64 (m, 8H), 3.61-3.44 (m, 16H), 3.04-2.80 (m, 4H), 2.77-2.52 (m, 6H), 2.07-1.97 (m, 1H). | 1 | 962.41 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| 115 | 1006.72 | 1008.72 | ¹H NMR (400 MHz, DMSO-d₆) δ 11.10(s, 1H), 10.54 (s, 1H), 8.04-7.83 (m, 2H), 7.59-7.52(m, 1H), 7.42-7.36 (m, 1H), 7.14-7.11 (m, 1H), 7.03 (d, J = 7.2 Hz, 1H), 6.89-6.76 (m, 3H), 5.69 (s, 1H), 6.19 (d, J = 17.2 Hz, 1H), 5.76 (d, J = 10.8 Hz, 1H), 5.06 (dd, J = 5.2, 12.8 Hz, 1H), 4.18-3.71 (m, 20H), 3.61-3.51 (m, 8H), 2.97-2.86 (m, 4H), 3.72-2.58 (m, 6H), 2.07-2.01 (m, 1H). | 1 | 1006.46 |
| 116 | 1006.72 | 1008.72 | ¹H NMR (400 MHz, DMSO-d₆) δ 11.09 (s, 1H), 10.54 (s, 1H), 8.03-7.78 (m, 2H), 7.57-7.55 (m, 1H), 7.37-7.32 (m, 1H), 7.14-7.11 (m, 1H), 7.03-7.02 (m, 1H), 6.88-6.80 (m, 3H), 6.55 (s, 1H), 6.18 (d, J = 17.2 Hz, 1H), 5.75 (d, J = 10 Hz, 1H), 5.07-5.04 (m, 1H), 4.18-3.60 (m, 20H), 3.54-3.50 (m, 8H), 2.97-2.85 (m, 4H), 2.71-2.53 (m, 6H), 2.03-2.00 (m, 1H). | 1 | 1006.46 |
| 117 | 818.57 | 820.57 | ¹H NMR (400 MHz, DMSO-d₆) δ 11.08 (s, 1H), 10.48 (br s, 1H), 8.03 (br s, 1H), 7.99-7.75 (m, 1H), 7.66-7.52 (m, 1H), 7.45-7.33 (m, 1H), 7.25-7.13 (m, 1H), 7.08-6.98 (m, 1H), 6.92-6.79 (m, 2H), 6.78-6.67 (m, 1H), 5.11-4.96 (m, 1H), 4.24-4.06 (m, 3H), 3.76-3.58 (m, 12H), 3.08-2.81 (m, 4H), 2.74-2.62 (m, 2H), 2.61-2.54 (m, 1H), 2.10-1.95 (m, 4H). | 1 | 818.24 |
| 118 | 818.57 | 820.57 | ¹H NMR (400 MHz, DMSO-d₆) δ 11.08 (s, 1H), 10.46 (br s, 1H), 8.10-7.75 (m, 2H), 7.65-7.50 (m, 1H), 7.44-7.33 (m, 1H), 7.25-7.12 (m, 1H), 7.08-6.98 (m, 1H), 6.91-6.79 (m, 2H), 6.78-6.67 (m, 1H), 5.10-4.97 (m, 1H), 4.22-4.05 (m, 3H), 3.77-3.56 (m, 12H), 3.07-2.80 (m, 4H), 2.72-2.62 (m, 2H), 2.61-2.54 (m, 1H), 2.09-1.93 (m, 4H). | 1 | 818.24 |
| 119 | 862.6 | 864.6 | ¹H NMR (400 MHz, METHANOL-d₄) δ 8.10-7.82 (m, 1H), 7.46-7.25 (m, 2H), 7.07-6.56 (m, 4H), 5.03 (br s, 1H), 4.35-3.59 (m, 16H), 3.51-3.36 (m, 2H), 3.16-3.06 (m, 3H), 2.92-2.59 (m, 5H), 2.23-2.04 (m, 4H). | 1 | 862.29 |
| 120 | 862.6 | 864.6 | ¹H NMR (400 MHz, DMSO-d₆) δ 11.09 (br s, 1H), 10.72-9.82 (m, 1H), 8.24 (br s, 1H), 7.73-7.64 (m, 1H), 7.61-7.43 (m, 1H), 7.31 (q, J = 7.5 Hz, 1H), 7.24-7.10 (m, 1H), 7.07-6.94 (m, 2H), 6.83 (d, J = 8.2 Hz, 1H), 6.76 (t, J = 8.7 Hz, 1H), 6.65-6.49 (m, 1H), 5.03 (dd, J-= 5.4, 13.0 Hz, 1H), 3.63 (br s, 9H), 3.60-3.51 (m, 10H), 3.05-2.79 (m, 4H), 2.70-2.55 (m, 3H), 2.09-1.96 (m, 4H). | 1 | 862.29 |
| 121 | 906.64 | 908.64 | ¹H NMR (400 MHz, DMSO-d₆) δ 11.10 (s, 1H), 10.50 (s, 1H), 8.01-7.99 (m, 1H), 7.95-7.68 (m, 1H), 7.55-7.51 (m, 1H), 7.39-7.38 (m, 1H), 7.12-7.02 (m, 2¹H), 6.88-6.80 (m, 2H), 6.61-6.56 (m, 1H), 5.07-5.02 (m, 1H), 4.38-4.08 (m, 3H), 3.82-3.59 (m, 17H), 2.95-2.84 (m, 4H), 2.70-2.55 (m, 6H), 2.05-2.00 (m, 4H). | 1 | 906.34 |
| 122 | 906.64 | 908.64 | ¹H NMR (400 MHz, DMSO-d₆) δ 11.08 (s, 1H), 10.44 (s, 1H), 8.04-7.92 (m, 1H), 7.91-7.67 (m, 1H), 7.62-7.48 (m, 1H), 7.44-7.28 (m, 1H), 7.08-7.01 (m, 2H), 6.87-6.82 (m, 2H), 6.61-6.52 (m, 1H), 5.06-5.02 (m, 1H), 4.15-4.08 (m, 3H), 3.75-3.59 (m, 17H), 2.95-2.84 (m, 4H), 2.69-2.60 (m, 6H), 2.05-2.03 (m, 4H). | 1 | 906.34 |
| 123 | 950.68 | 952.68 | ¹H NMR (400 MHz, DMSO-d₆) δ 11.09 (s, 1H), 10.20 (br s, 1H), 8.18 (s, 1H), 7.70 (s, 1H), 7.61-7.48 (m, 1H), 7.32 (q, J = 8.0 Hz, 1H), 7.17-7.06 (m, 1H), 7.03 (dd, J = 1.6, 6.8 Hz, 1H), 6.88-6.73 (m, 2H), 6.62-6.51 (m, 1H), 5.05 (dd, J = 4.8, 13.2 Hz, 1H), 3.74-3.61 (m, 8H), 3.54-3.42 (m, 16H), 3.02-2.80 (m, 4H), 2.71-2.52 (m, 6H), 2.05 (d, J = 2.4 Hz, 3H), 2.02 (br d, J = 7.2 Hz, 1H). | 1 | 950.39 |
| 124 | 950.69 | 952.69 | ¹H NMR (400 MHz, DMSO-d₆) δ 11.09 (s, 1H), 10.16 (br s, 1H), 8.15 (s, 1H), 7.70 (s, 1H), 7.56 (dt, J = 3.6, 7.6 Hz, 1H), 7.32 (q, J = 8.0 Hz, 1H), 7.11 (br dd, J = 5.2, 8.4 Hz, 1H), 7.03 (br d, J = 6.0 Hz, 1H), 6.88-6.73 (m, 2H), 6.58 (br d, J = 4.4 Hz, 1H), 5.05 (dd, J = 4.8, 12.8 Hz, 1H), 3.78-3.61 (m, 8H), 3.57-3.42 (m, 16H), 3.06-2.77 (m, 4H), 2.59 (br d, J = 16.8 Hz, 6H), 2.05 (d, J = 1.6 Hz, 3H), 2.01 (br s, 1H). | 1 | 950.39 |
| 125 | 994.72 | 996.72 | ¹H NMR (400 MHz, DMSO-d₆) δ 11.09 (s, 1H), 10.55 (s, 1H), 8.10 (s, 1H), 8.03 (s, 1H), 7.58-7.54 (m, 1H), 7.41-7.35 (m, 1H), 7.13-7.10 (m, 1H), 7.03-7.01 (m, 1H), 6.89-6.80 (m, 2H), 6.58 (s, 1H), 5.07-5.02 (m, 1H), 4.16-3.19 (m, 12H), 3.73-3.50 (m, 16H), 2.97-2.85 (m, 4H), 2.72-2.53 (m, 6H), 2.07-2.00 (m, 4H). | 1 | 994.45 |
| 126 | 994.72 | 996.72 | ¹H NMR (400 MHz, DMSO-d₆) δ 11.09 (s, 1H), 10.54 (s, 1H), 8.08-8.02 (m, 2H), 7.58-7.54 (m, 1H), 7.41-7.35 (m, 1H), 7.14-7.10 (m, 1H), 7.03-7.02 (m, 1H), 6.88-6.80 (m, 2H), 6.58 (s, 1H), 5.07-5.02 (m, 1H), 4.79-4.12 (m, 9H), 3.73-3.69 (m, 9H), 3.54-3.50 (m, 10H), 2.97-2.85 (m, 4H), 2.72-2.53 (m, 6H), 2.05-2.00 (m, 4H). | 1 | 994.45 |
| 127 | 1055.75 | 1057.75 | ¹H NMR (400 MHz, METHANOL-d₄) δ 8.89-8.81 (m, 1H), 8.32 (br s, 1H), 7.71-7.56 (m, 1H), 7.38-7.26 (m, 2H), 7.02-6.91 (m, 1H), 6.83-6.74 (m, 1H), 6.72-6.65 (m, 1H), 6.30-6.17 (m, 2H), 5.82-5.75 (m, 1H), 4.54-4.11 (m, 7H), 3.92-3.55 (m, 15H), 3.04 (m, 1H), 2.92-2.76 (m, 1H), 2.47-2.34 (m, 4H), 2.25-2.04 (m, 5H), 0.99 (br dd, J = 6.4, 10.0 Hz, 3H), 0.84 (br dd, J = 6.8, 9.6 Hz, 3H). | 1 | 1055.60 |
| 128 | 1099.78 | 1101.78 | ¹H NMR (400 MHz, CD₃OD) δ 8.87-8.80(m, 1H), 8.87-8.80 (m, 1H), 8.39 (br s, 1H), 7.85-7.49 (m, 1H), 7.35-7.18 (m, 2H), 7.02-6.92 (m, 1H), 6.87-6.63 (m, 3H), 6.26 (br d, J = 16.4 Hz, 1H), 6.21-6.17 (m, 1H), 5.79 (br d, J = 11.1 Hz, 1H), 4.47 (br s, 1H), 4.35-4.22 (m, 1H), 4.20-3.97 (m, 1H), 3.94-3.53 (m, 18H), 3.13 (br s, 1H), 3.00-2.91 (m, 2H), 2.89-2.59 (m, 3H), 2.44 (d, J = 7.8 Hz, 4H), 2.28-2.01 (m, 5H), 1.05 (dd, J = 3.9, 6.8 Hz, 2H), 0.87 (d, J = 6.4 Hz, 2H). | 1 | 1099.65 |
| 129 | 1099.79 | 1101.79 | ¹H NMR (400 MHz, CD₃OD) δ 8.88-8.79 (m, 1H), 7.77-7.57 (m, 1H), 7.28 (d, J = 7.0 Hz, 1H), 7.03-6.95 (m, 1H), 6.87-6.64 (m, 3H), 6.30-6.19 (m, 2H), 5.84-5.74 (m, 1H), 4.53-4.31 (m, 3H), 4.23-3.98 (m, 1H), 3.91-3.51 (m, 16H), 3.13 (s, 1H), 3.00-2.91 (m, 1H), 2.95 (s, 5H), 2.52-2.52 (m, 1H), 2.50-2.40 (m, 3H), 2.28-2.19 (m, 3H), 1.02 (dd, J = 2.8, 6.5 Hz, 1H), 0.88-0.78 (m, 1H). | 1 | 1099.65 |
| 130 | 1143.82 | 1145.82 | ¹H NMR (400 MHz, METHANOL-d₄) δ 8.84 (d, J = 2.4 Hz, 1H), 7.69 (br d, J = 8.0 Hz, 1H), 7.38 (dd, J = 4.0, 7.6 Hz, 1H), 7.28 (m, 1H), 6.96 (br dd, J = 8.8, 15.6 Hz, 2H), 6.84-6.73 (m, 2H), 6.69 (t, J = 8.8 Hz, 1H), 6.25 (td, J = 2.4, 16.8 Hz, 1H), 6.20 (s, 1H), 5.81-5.75 (m, 1H), 4.56-4.39 (m, 4H), 4.20-4.13 (m, 1H), 4.05 (br t, J = 6.8 Hz, 1H), 3.91-3.49 (m, 26H), 3.10 (br s, 1H), 2.92 (s, 2H), 2.83 (m, 1H), 2.71 (br t, J = 6.8 Hz, 1H), 2.47-2.36 (m, 4H), 2.27-1.98 (m, 6H), 1.02 (d, J = 6.4 Hz, 3H), 0.84 (d, J = 6.8 Hz, 3H). | 1 | 1143.70 |
| 131 | 1187.85 | 1189.85 | ¹H NMR (400 MHz, METHANOL-d₄) δ 8.84 (s, 1H), 7.73 (br s, 1H), 7.40 (br d, J = 6.8 Hz, 1H), 7.32-7.25 (m, 1H), 7.03-6.98 (m, 2H), 6.84-6.74 (m, 2H), 6.69 (t, J = 8.8 Hz, 1H), 6.25 (br, d, J = 16.8 Hz, 1H), 6.21 (s, 1H), 5.78 (br d, J = 10.4 Hz, 1H), 4.57-4.43 (m, 5H), 4.16 (m, 2H), 3.88- | 1 | 1187.76 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| | | | 3.49 (m, 30H), 3.11 (br s, 1H), 2.92 (s, 2H), 2.82 (m, 1H), 2.74-2.68 (m, 1H), 2.48-2.44 (m, 3H), 2.39 (m, 1H), 2.25-2.02 (m, 6H), 1.02 (br d, J = 6.4 Hz, 3H), 0.84 (d, J = 6.4 Hz, 3H). | | |
| 132 | 1231.89 | 1233.89 | $^1$H NMR (400 MHz, METHANOL-$d_4$) δ 8.85 (s, 1H), 7.74 (br s, 1H), 7.41 (d, J = 7.9 Hz, 1H), 7.35-7.24 (m, 1H), 7.08-6.97 (m, 2H), 6.86-6.74 (m, 2H), 6.69 (t, J = 8.6 Hz, 1H), 6.23-6.18 (m, 2H), 5.78 (br d, J = 10.4 Hz, 1H), 4.63-4.37 (m, 5H), 4.18 (br d, J = 3.7 Hz, 2H), 3.88-3.44 (m, 30H), 3.12 (br s, 1H), 2.92 (s, 2H), 2.82 (br t, J = 6.4 Hz, 1H), 2.72 (br t, J = 6.0 Hz, 1H), 2.51-2.43 (m, 3H), 2.42-2.33 (m, 1H), 2.27-1.99 (m, 5H), 1.02 (d, J = 6.4 Hz, 3H), 0.84 (d, J = 6.8 Hz, 3H). | 1 | 1231.81 |
| 133 | 820.55 | 822.55 | $^1$H NMR (400 MHz, DMSO-$d_6$) δ 11.10 (br s, 1H), 10.76-9.69 (m, 1H), 8.20 (s, 1H), 7.87-7.65 (m, 2H), 7.48-7.39 (m, 1H), 7.38-7.05 (m, 3H), 6.85-6.72 (m, 2H), 6.06 (s, 2H), 5.11 (dd, J = 5.2, 13.0 Hz, 1H), 4.30 (td, J = 5.6, 15.0 Hz, 2H), 3.83-3.54 (m, 1H1), 3.11 (br s, 2H), 2.94-2.76 (m, 4H), 2.67-2.53 (m, 4H), 2.09-1.99 (m, 1H). | 1 | 820.21 |
| 134 | 864.59 | 866.59 | $^1$H NMR (400 MHz, DMSO-$d_6$) δ 11.17 (s, 1H), 10.57 (br s, 1H), 8.16-7.71 (m, 3H), 7.47 (d, J = 6.4 Hz, 3H), 7.03-6.76 (m, 2H), 6.17 (br s, 2H), 5.17 (dd, J = 5.2, 12.8 Hz, 1H), 4.35 (s, 2H), 4.15 (s, 3H), 3.90-3.69 (m, 7H), 3.64 (s, 6H), 3.12-2.62 (m, 8H), 2.24-2.03 (m, 1H). | 1 | 864.26 |
| 135 | 908.62 | 910.63 | $^1$H NMR (400 MHz, DMSO-$d_6$) δ 11.13 (m, 1H), 10.55 (m, 1H), 8.02 (d, J = 4.4 Hz, 1H), 7.84-7.76 (m, 1H), 7.44-7.29 (m, 3H), 6.89-6.80 (m, 2H), 6.14 (brs, 2H), 5.11 (dd, J = 4.4,11.6 Hz, 1H), 4.28 (s, 2H), 4.11 (m, 3H), 3.78-3.53 (m, 16H), 3.03-2.80 (m, 4H), 2.79-2.53 (m, 4H), 2.47-2.27 (m, 1H), 2.08-1.99 (m, 1H). | 1 | 908.31 |
| 136 | 952.66 | 954.66 | $^1$H NMR (400 MHz, DMSO-$d_6$) δ 11.11 (br s, 1H), 8.26 (s,1H), 7.82 (d, J = 8.2 Hz, 1H), 7.69 (s, 1H), 7.43 (d, J = 2.4 Hz, 1H), 7.39-7.28 (m, 2H), 7.27-6.98 (m, 1H), 6.87-6.73 (m, 2H), 6.07 (s, 2H), 5.12 (dd, J = 5.2, 12.8 Hz, 1H), 4.36-4.25 (m, 2H), 3.58 (br s, 14H), 3.44-3.17 (m, 10H), 3.02 1H), 2.96-2.80 (m, 3H), 2.72-2.53 (m, 4H), 2.10-2.01 (m, 1H). | 1 | 952.37 |
| 137 | 996.7 | 998.7 | $^1$H NMR (400 MHz, DMSO-$d_6$) δ 11.12 (s, 1H), 10.21 (s, 1H), 8.17 (s, 1H), 7.82 (d, J = 8.0 Hz, 1H), 7.69 (s, 1H), 7.47-7.41 (m, 1H), 7.39-7.27 (m, 2H), 7.25-6.99 (m, 1H), 6.83 (d, J = 8.4 Hz, 1H), 6.77 (t, J = 8.8 Hz, 1H), 6.08 (s, 2H), 5.12 (dd, J = 5.2, 12.8 Hz, 1H), 4.35-4.22 (m, 2H), 3.78-3.73 (m, 2H), 3.72-3.64 (m, 2H), 3.60-3.53 (m, 7H), 3.51-3.46 (m, 11H), 3.46-3.44 (m, 3H), 3.41-3.40 (m, 2H), 3.06-2.95 (m, 2H), 2.94-2.77 (m, 3H), 2.71-2.51 (m, 4H), 2.09-1.99 (m, 1H). | 1 | 996.42 |
| 138 | 806.56 | 808.56 | $^1$H NMR (400 MHz, METHANOL-$d_4$) δ 8.26 (br s, 1H), 7.81-7.56 (m, 2H), 7.42-7.27 (m, 1H), 7.04-6.92 (m, 1H), 6.79 (br d, J = 10.6 Hz, 1H), 6.76-6.69 (m, 1H), 5.18-5.03 (m, 1H), 4.58 (br s, 3H), 4.40-4.14 (m, 3H), 3.94-3.54 (m, 9H), 3.24 (br s, 2H), 3.05 (s, 2H), 2.96-2.85 (m, 2H), 2.81-2.67 (m, 2H), 2.51-2.29 (m, 1H), 2.20-2.00 (m, 1H). | 1 | 806.22 |
| 139 | 850.61 | 852.61 | $^1$H NMR (400 MHz, DMSO-$d_6$) δ 10.98 (br s, 1H), 10.29 (br s, 1H), 8.23 (s, 1H), 7.74-7.64 (m, 1H), 7.63-7.51 (m, 1H), 7.36-7.26 (m, 1H), 7.26-6.92 (m, 3H), 6.86-6.73 (m, 2H), 6.09 (br s, 2H), 5.06 (dd, J = 5.1, 13.3 Hz, 1H), 4.46-4.03 (m, 5H), 3.73 (br d, J = 3.1 Hz, 4H), 3.64-3.54 (m, 11H), 3.06-2.79 (m, 4H), 2.71-2.54 (m, 3H), 2.42-2.23 (m, 3H), 2.08-1.86 (m, 1H). | 1 | 850.28 |
| 140 | 894.64 | 896.64 | $^1$H NMR (400 MHz, DMSO-$d_6$) δ 10.94 (s, 1H), 10.26 (s, 1H), 8.25 (s, 1H), 7.68-7.67 (m, 1H), 7.69 (d, J = 8.0 Hz, 1H), 7.33-7.27 (m, 1H), 7.12-6.99 (m, 3H), 6.81 (d, J = 8.4 Hz, 1H), 6.75 (t, J = 8.8 Hz, 1H), 6.05 (s, 2H), 5.05 (dd, J = 4.8, 13.2 Hz, 1H), 4.37-4.21 (m, 2H), 4.14-4.08 (m, 2H), 3.75-3.73 (m, 1H), 3.72-3.64 (m, 3H), 3.57-3.55 (m, 6H), 3.46-3.35 (m, 10H), 3.01 (s, 1H), 2.94-2.81 (m, 3H), 2.66-2.53 (m, 3H), 2.41-2.30 (m, 1H), 1.98-1.95 (m, 1H). | 1 | 894.33 |
| 141 | 938.68 | 940.68 | $^1$H NMR (400 MHz, DMSO-$d_6$) δ 11.30-10.73 (m, 1H), 10.47 (br s, 1H), 8.04 (br s, 1H), 7.92 (br s, 1H), 7.62 (d, J = 7.2 Hz, 1H), 7.48-7.28 (m, 1H), 7.16 (br d, J = 6.0 Hz, 1H), 7.09-7.01 (m, 1H), 6.91-6.78 (m, 2H), 6.11 (br s, 2H), 5.07 (dd, J = 5.2, 13.2 Hz, 1H), 4.39-4.24(m, 2H), 4.17 (br d, J = 2.8 Hz, 2H), 4.14-3.74 (m, 10H), 3.60-3.55 (m, 14H), 2.99-2.87 (m, 4H), 2.70-2.65 (m, 3H), 2.36 (br d, J = 4.2 Hz, 1H), 2.03-1.93 (m, 1H). | 1 | 938.38 |
| 142 | 982.72 | 984.72 | $^1$H NMR (400 MHz, DMSO-$d_6$) δ 10.96 (s, 1H), 10.57-10.09 (m, 1H), 8.01 (br s, 1H), 7.79 (br s, 1H), 7.62 (d, J = 8.4 Hz, 1H), 7.39 (br d, J = 7.8 Hz, 1H), 7.16 (br s, 1H), 7.08-7.02 (m, 1H), 6.91-6.76 (m, 2H), 6.11 (br s, 2H), 5.07 (dd, J = 5.2, 13.4 Hz, 1H), 4.43-4.22 (m, 2H), 4.21-4.15 (m, 2H), 4.13-3.58 (m, 10H), 3.51-3.42 (m, 18H), 3.04-2.82 (m, 4H), 2.74-2.68 (m, 3H), 2.41-2.36 (m, 1H), 2.03-1.95 (m, 1H). | 1 | 982.44 |
| 143 | 819.56 | 821.56 | $^1$H NMR (400 MHz, DMSO-$d_6$) δ 11.07 (s, 1H), 10.59-9.88 (m, 1H), 8.18 (s, 1H), 7.70 (s, 1H), 7.62-7.28 (m, 2H), 7.23-6.94 (m, 3H), 6.88-6.67 (m, 3H), 6.06 (s, 2H), 5.16-4.88 (m, 1H), 3.65-3.44 (m, 14H), 3.06-2.80 (m, 4H), 2.66-2.51 (m, 4H), 2.07-1.94 (m, 1H). | 1 | 819.22 |
| 144 | 863.6 | 865.6 | $^1$H NMR (400 MHz, DMSO-$d_6$) δ 11.07 (s, 1H), 10.51-9.98 (m, 1H), 8.16 (s, 1H), 7.67 (br d, J = 13.2 Hz, 1H), 7.59-7.42 (m, 1H), 7.31 (q, J = 7.7 Hz, 1H), 7.19-6.92 (m, 3H), 6.86-6.73 (m, 2H), 6.64-6.48 (m, 1H), 6.05 (s, 2H), 5.03 (dd, J = 5.4, 12.7 Hz, 1H), 3.57 (br d, J = 8.2 Hz, 8H), 3.52-3.44 (m, 10H), 3.04-2.77 (m, 4H), 2.67-2.53 (m, 4H), 2.00 (br d, J = 10.1 Hz, 1H). | 1 | 863.28 |
| 145 | 907.64 | 909.64 | $^1$H NMR (400 MHz, DMSO-$d_6$) δ 11.08 (s, 1H), 10.09 (s, 1H), 8.18 (s, 1H), 7.69 (d, J = 4.0 Hz, 1H), 7.56-7.52 (m, 1H), 7.35-7.29 (m, 1H), 7.10-7.01 (m, 3H), 6.83 (d, J = 8.4 Hz, 1H), 6.79-6.75 (m, 1H), 6.60-6.54 (m, 1H), 6.06 (s, 2H), 5.07-5.02 (m, 1H), 3.62-3.59 (m, 3H), 3.54-3.45 (m, 18H), 3.01-2.81 (m, 5H), 2.67-2.53 (m, 4H), 2.04-2.01 (m, 1H). | 1 | 907.33 |
| 146 | 951.68 | 953.68 | $^1$H NMR (400 MHz, DMSO-$d_6$) δ 11.09 (br s, 1H), 10.71-9.68 (m, 1H), 8.26 (s, 1H), 7.70 (s, 1H), 7.56 (dt, J = 4.0, 7.8 Hz, 1H), 7.32 (q, J = 8.0 Hz, 1H), 7.11 (dd, J = 5.4, 8.8 Hz, 1H), 7.03 (dd, J = 1.6, 7.2 Hz, 1H), 6.90-6.72 (m, 2H), 6.58 (br d, J = 4.4 Hz, 1H), 6.07 (s, 2H), 5.05 (dd, J = 5.2, 12.8 Hz, 1H), 3.70-3.57 (m, 8H), 3.51-3.42 (m, 18H), 3.06-2.76 (m, 4H), 2.74-2.52 (m, 4H), 2.09-1.97 (m, 1H). | 1 | 951.38 |
| 147 | 995.71 | 997.72 | $^1$H NMR (400 MHz, DMSO-$d_6$) δ 11.09 (s, 1H), 10.76-9.47 (m, 1H), 8.23 (s, 1H), 7.70 (s, 1H), 7.62-7.50 (m, 1H), 7.32 (q, J = 8.0 Hz, 1H), 7.13 (dd, J = 4.8, 8.8 Hz, 1H), 7.03 (d, J = 7.2 Hz, 1H), 6.88-6.70 (m, 2H), 6.59 (br t, J = 5.2 Hz, 1H), 6.07 (s, 2H), 5.05 (dd, J = 5.4, 12.8 Hz, 1H), 3.67-3.54 (m, 10H), 3.51-3.43 (m, 16H), 3.06-2.77 (m, 5H), 2.70-2.52 (m, 5H), 2.08-1.98 (m, 1H). | 1 | 995.44 |
| 148 | 851.36 | 853.36 | $^1$H NMR (400 MHz, DMSO-$d_6$) δ 11.11 (s, 1H), 10.19 (br s, 1H), 7.86-7.67 (m, 2H), 7.52-7.05 (m, 4H), 6.89-6.71 (m, 2H), 6.35 (br d, J = 7.2 Hz, 1H), 5.35 (br s, 1H), 5.12 (dd, J = 5.4, 12.7 Hz, | 1 | 851.22 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| | | | 1H), 4.46-4.20 (m, 2H), 3.81-3.42 (m, 13H), 3.18-2.99 (m, 2H), 2.95-2.58 (m, 5H), 2.12-2.02 (m, 1H). | | |
| 149 | 895.6 | 897.6 | $^1$H NMR (400 MHz, DMSO-d$_6$) δ 11.64 (s, 1H), 11.10 (s, 1H), 10.17 (s, 1H), 8.13 (s, 1H), 7.79-7.69 (m, 2H), 7.43-7.28 (m, 3H), 7.24-7.09 (m, 1H), 6.82 (d, J = 8.4 Hz, 1H), 6.79-6.75 (m, 1H), 6.34 (d, J = 6.8 Hz, 1H), 5.41-5.29 (m, 1H), 4.12-4.08 (m, 1H), 4.28-4.23 (m, 2H), 3.90-3.48 (m, 16H), 3.46-3.45 (m, 2H), 3.03-2.82 (m, 4H), 2.61-2.56 (m, 2H), 2.07-2.02 (m, 1H). | 1 | 895.27 |
| 150 | 895.6 | 897.6 | $^1$H NMR (400 MHz, DMSO-d$_6$) δ 11.10(s, 1H), 11.17(s, 1H),9.41 (s, 1H), 8.21 (s, 1H), 7.78-7.68 (m, 2H), 7.43-7.28 (m, 3H), 7.23-7.04 (m, 1H), 6.82 (d, J = 8.0 Hz, 1H), 6.78-6.74 (m, 1H), 6.34 (s, 1H), 5.34 (s, 1H), 5.12-5.07 (m, 1H), 4.28-4.22 (m, 2H), 3.73-3.53 (m, 18H), 3.02-2.81 (m, 4H), 2.60-2.56 (m, 2H), 2.06-2.01 (m, 1H). | 1 | 895.27 |
| 151 | 939.64 | 941.64 | $^1$H NMR (400 MHz, DMSO-d$_6$) δ 11.10(s, 1H), 10.20(s, 1H), 7.80 (d, J = 8.4 Hz, 1H), 7.70 (d, J = 4.4 Hz, 1H), 7.41-7.40 (m, 1H), 7.34-7.29 (m, 2H), 7.18-7.08 (m, 1H), 6.83 (d, J = 8.0 Hz, 1H), 6.76 (t, J = 8.8 Hz, 1H), 6.35 (d, J = 7.2 Hz, 1H), 5.34-5.33 (m, 1H), 5.13-5.08 (m, 1H), 4.27-4.22 (m, 2H), 3.83-3.75 (m, 2H), 3.73-3.60 (m, 7H), 3.58-3.42 (m, 14H), 3.07-2.81 (m, 4H), 2.61-2.57 (m, 2H), 2.05-2.03 (m, 1H). | 1 | 939.32 |
| 152 | 939.64 | 941.64 | $^1$H NMR (400 MHz, DMSO-d$_6$) δ 11.11 (s, 1H), 10.28 (s, 1H), 8.38 (s, 1H), 7.79 (d, J = 8.4 Hz, 1H), 7.70 (d, J = 4.0 Hz, 1H), 7.42-7.39 (m, 1H), 7.34-7.28 (m, 2H), 7.21-7.09 (m, 1H), 6.82 (d, J = 8.4 Hz, 1H), 6.76 (t, J = 8.8 Hz, 1H), 6.37 (d, J = 6.4 Hz, 1H), 5.34 (s, 1H), 5.12-5.08 (m, 1H), 4.27-4.21 (m, 2H), 3.77-3.75 (m, 4H), 3.71-3.65 (m, 5H), 3.58-3.5 (m, 13H), 2.92-2.81 (m, 4H), 2.61-2.60 (m, 2H), 2.07-2.01 (m, 2H). | 1 | 939.32 |
| 153 | 983.67 | 985.67 | $^1$H NMR (400 MHz, DMSO-d$_6$) δ 11.13 (br s, 1H), 10.27 (br s, 1H), 9.42 (s, 1H), 7.81 (d, J = 8.4 Hz, 1H), 7.72 (s, 1H), 7.43 (d, J = 2.0 Hz, 1H), 7.38-7.24 (m, 2H), 7.13 (br s, 1H), 6.86 (d, J = 8.4 Hz, 1H), 6.77 (t, J = 8.8 Hz, 1H), 6.38 (d, J = 7.2 Hz, 1H), 5.35 (br t, J = 6.8 Hz, 1H), 5.12 (dd, J = 5.2, 12.8 Hz, 1H), 4.35-4.21 (m, 2H), 3.90-3.40 (m, 27H), 3.05-2.79 (m, 4H), 2.59 (br d, J = 17.6 Hz, 2H), 2.11-1.98 (m, 1H). | 1 | 983.38 |
| 154 | 983.67 | 985.67 | $^1$H NMR (400 MHz, DMSO-d$_6$) δ 11.37-10.97 (m, 1H), 10.27 (br s, 1H), 9.42 (s, 1H), 7.81 (d, J = 8.4 Hz, 1H), 7.72 (s, 1H), 7.43 (d, J = 2.4 Hz, 1H), 7.39-7.25 (m, 2H), 6.87 (d, J = 8.4 Hz, 1H), 6.76 (t, J = 8.8 Hz, 1H), 6.36 (br d, J = 7.2 Hz, 1H), 5.35 (br t, J = 6.8 Hz, 1H), 5.12 (dd, J = 5.4, 13.2 Hz, 1H), 4.39-4.22 (m, 2H), 4.00-3.39 (m, 27H), 3.05-2.78 (m, 4H), 2.59 (br d, J = 16.8 Hz, 2H), 2.11-1.96 (m, 1H). | 1 | 983.38 |
| 155 | 1027.71 | 1029.71 | $^1$H NMR (400 MHz, DMSO-d$_6$) δ 11.11 (br s, 1H), 10.25 (br s, 1H), 9.42 (s, 1H), 8.37 (br s, 1H), 7.82 (d, J = 8.2 Hz, 1H), 7.72 (s, 1H), 7.44 (s, 1H), 7.38-7.27 (m, 2H), 7.18-6.97 (m, 1H), 6.83 (d, J = 8.3 Hz, 1H), 6.77 (t, J = 8.7 Hz, 1H), 6.35 (br d, J = 3.7 Hz, 1H), 5.35 (br s, 1H), 5.11 (dd, J = 5.3, 12.8 Hz, 1H), 4.29 (br s, 2H), 3.85-3.63 (m, 10H), 3.58-3.45 (m, 16H), 3.02 (br s, 3H), 2.94-2.78 (m, 5H), 2.61 (br s, 2H), 2.07-1.99 (m, 1H). | 1 | 1027.43 |
| 156 | 1027.71 | 1029.71 | $^1$H NMR (400 MHz, DMSO-d$_6$) δ 11.10 (s, 1H), 10.19 (s, 1H), 8.13 (s, 1H), 7.82-7.73 (m, 2H), 7.43-7.29 (m, 2H), 7.17-7.15 (m, 1H), 7.09 (m, 1H), 6.82 (d, J = 8.4 Hz, 1H), 6.77 (t, J = 8.4 Hz, 1H), 6.34 (s, 1H), 5.34 (s, 1H), 5.17-5.09 (m, 1H), 4.28 (s, 1H), 3.87-3.68 (m, 11H), 3.55-3.44 (m, 19H), 3.01-2.81 (m, 5H), 2.61-2.57 (m, 2H), 2.07-2.02 (m, 1H). | 1 | 1027.43 |
| 157 | 850.58 | 852.58 | $^1$H NMR (400 MHz, DMSO-d$_6$) δ 12.73 (s, 1H), 11.09 (s, 1H), 10.19 (s, 1H), 8.13 (s, 1H), 7.73 (s, 1H), 7.59 (s, 1H), 7.39-7.28 (m, 1H), 7.19 (d, J = 7.7 Hz, 1H), 7.08-6.93 (m, 1H), 6.85-6.68 (m, 3H), 6.36 (s, 1H), 5.34 (s, 1H), 5.05 (dd, J = 5.1, 12.7 Hz, 1H), 3.82-3.39 (m, 14H), 3.08-2.79 (m, 4H), 2.67-2.55 (m, 4H), 2.04-1.93 (m, 1H). | 1 | 850.23 |
| 158 | 850.58 | 852.58 | $^1$H NMR (400 MHz, DMSO-d$_6$) δ 11.08 (s, 1H), 10.18 (s, 1H), 8.13 (s, 1H), 7.73 (s, 1H), 7.59 (t, J = 7.4 Hz, 1H), 7.33 (q, J = 8.1 Hz, 1H), 7.19 (d, J = 8.8 Hz, 1H), 7.02 (d, J = 7.0 Hz, 1H), 6.86-6.67 (m, 3H), 6.34 (s, 1H), 5.35 (s, 1H), 5.08-4.98 (m, 1H), 3.85-3.37 (m, 15H), 3.07-2.97 (m, 2H), 2.91-2.79 (m, 2H), 2.65-2.52 (m, 4H), 2.06-1.94 (m, 1H). | 1 | 850.23 |
| 159 | 894.6 | 896.61 | $^1$H NMR (400 MHz, DMSO-d$_6$) δ 11.09 (br s, 1H), 10.62-10.06 (m, 1H), 8.06-7.65 (m, 1H), 7.60-7.46 (m, 1H), 7.39 (br d, J = 7.6 Hz, 1H), 7.19-6.93 (m, 2H), 6.93-6.64 (m, 2H), 6.63-6.15 (m, 2H), 5.67-4.79 (m, 2H), 4.11 (br s, 2H), 3.88 (br s, 3H), 3.72-3.53 (m, 8H), 3.45 (br s, 8H), 3.04-2.78 (m, 4H), 2.69-2.59 (m, 2H), 2.56 (br s, 1H), 2.13-1.92 (m, 1H). | 1 | 894.29 |
| 160 | 894.61 | 896.62 | $^1$H NMR (400 MHz, DMSO-d$_6$) δ 11.09 (br s, 1H), 10.51-10.14 (m, 1H), 8.01-7.67 (m, 1H), 7.63-7.43 (m, 1H), 7.35 (br s, 1H), 7.18-7.04 (m, 1H), 6.99 (br t, J = 3.8 Hz, 1H), 6.89-6.73 (m, 2H), 6.58 (br s, 1H), 6.38 (br s, 1H), 5.39-4.90 (m, 2H), 3.81 (br s, 1H), 3.68 (br s, 4H), 3.56 (br d, J = 17.6 Hz, 8H), 3.45 (br d, J = 4.9 Hz, 8H), 3.04-2.79 (m, 4H), 2.61 (br d, J = 6.8 Hz, 2H), 2.55-2.53 (m, 1H), 2.10-1.91 (m, 1H). | 1 | 894.29 |
| 161 | 938.65 | 940.65 | $^1$H NMR (400 MHz, DMSO-d$_6$) δ 11.08 (s, 1H), 10.18 (s, 1H), 7.72 (s, 1H), 7.55-7.51 (m, 1H), 7.35-7.29 (m, 1H), 7.06-7.00 (m, 2H), 6.84-6.75 (m, 2H), 6.57-6.54 (m, 1H), 6.34 (s, 1H), 5.35 (s, 1H), 5.06-5.02 (m, 1H), 3.80 (s, 2H), 3.76-3.64 (m, 4H), 3.62-3.59 (m, 2H), 3.53-3.46 (m, 10H), 3.42-3.41 (m, 8H), 3.00-2.81 (m, 4H), 2.60-2.56 (m, 2H), 2.03-1.98 (m, 1H). | 1 | 938.34 |
| 162 | 938.65 | 940.65 | $^1$H NMR (400 MHz, DMSO-d$_6$) δ 11.07 (s, 1H), 10.17 (s, 1H), 7.72 (s, 1H), 7.54-7.50 (m, 1H), 7.34-7.29 (m, 1H), 7.05-7.00 (m, 2H), 6.83-6.75 (m, 2H), 6.57-6.54 (m, 1H), 6.34-6.32 (d, J = 6.8 Hz, 1H), 5.34 (s, 1H), 5.06-5.01 (m, 1H), 3.79 (s, 2H), 3.67-3.53 (m, 6H), 3.51-3.42 (m, 18H), 2.99-2.82 (m, 4H), 2.66-2.59 (m, 2H), 2.06-2.00(m, 1H). | 1 | 938.34 |
| 163 | 982.68 | 984.68 | $^1$H NMR (400 MHz, DMSO-d$_6$) δ 12.71 (s, 1H), 11.09 (s, 1H),10.18 (s, 1H), 8.13 (s, 1H), 7.72 (s, 1H), 7.58-7.53 (m, 1H), 7.35-7.29 (m, 1H), 7.12-7.09 (m, 1H), 7.04-7.01 (m, 1H), 6.84-6.75 (m, 2H), 6.58-6.57 (m, 1H), 6.35-6.34 (m, 1H), 5.55-5.52 (m, 1H), 5.07-5.03 (m, 1H), 3.84-3.78 (m, 2H), 3.72-3.64 (m, 5H), 3.63-3.42 (m, 22H), 3.01-2.81 (m, 4H), 2.64-2.58 (m, 2H), 2.03-2.00 (m, 1H). | 1 | 982.39 |
| 164 | 982.68 | 984.68 | $^1$H NMR (400 MHz, DMSO-d$_6$) δ 11.07 (s, 1H), 10.15 (s, 1H), 7.72(s, 1H), 7.59-7.52 (m, 1H), 7.35-7.28 (m, 1H), 7.18-6.95 (m, 3H), 6.9-6.7 (m, 2H), 6.62-6.52 (m, 1H), 6.33-6.32 (d, J = 4.0 Hz, 1H), 5.37-5.31 (m, 1H), 5.08-5.00 (m, 1H), 3.79 (s, 2H), 3.74-3.63 (m, 5H), 3.62-3.37 (m, 22H), 3.01-2.81 (m, 4H), 2.60-2.58 (d, J = 8.0 Hz, 2H), 2.05-1.97 (s, 1H). | 1 | 982.39 |

TABLE 7-continued

Data for Compounds of Table 6

| Ex. No. | MH+ (1) | MH+ (2) | NMR Transcript | Synthetic Scheme | Mol Weight |
|---|---|---|---|---|---|
| 165 | 1026.73 | 1028.73 | $^1$H NMR (400 MHz, DMSO-$d_6$) δ 11.11 (s, 1H), 10.22 (br s, 1H), 7.73 (br s, 1H), 7.61-7.51 (m, 1H), 7.33 (q, J = 7.9 Hz, 1H), 7.12 (br dd, J = 3.1, 8.6 Hz, 1H), 7.03 (d, J = 7.0 Hz, 1H), 6.87-6.74 (m, 2H), 6.59 (br s, 1H), 6.38 (br d, J = 1.1 Hz, 1H), 5.35 (br s, 1H), 5.05 (dd, J = 5.3, 12.7 Hz, 1H), 3.80 (br s, 3H), 3.66 (br d, J = 13.1 Hz, 4H), 3.63-3.55 (m, 4H), 3.54-3.49 (m, 6H), 3.47 (br t, J = 3.5 Hz, 14H), 3.33-3.16 (m, 2H), 3.03-2.82 (m, 4H), 2.61 (br s, 2H), 2.56 (br s, 1H), 2.08-1.96 (m, 1H). | 1 | 1026.45 |
| 166 | 1026.72 | 1028.73 | $^1$H NMR (400 MHz, DMSO-$d_6$) δ 11.10(s, 1H), 10.21 (br s, 1H), 7.72 (br s, 1H), 7.60-7.51 (m, 1H), 7.32 (q, J = 7.9 Hz, 1H), 7.11 (br dd, J = 3.2, 8.6 Hz, 1H), 7.02 (d, J = 7.0 Hz, 1H), 6.86-6.74 (m, 2H), 6.58 (br s, 1H), 6.37 (br s, 1H), 5.60-5.28 (m, 1H), 5.04 (dd, J = 5.3, 13.0 Hz, 1H), 3.79 (br s, 3H), 3.65 (br d, J = 15.5 Hz, 4H), 3.58 (br s, 4H), 3.50 (br dd, J = 5.6, 10.7 Hz, 8H), 3.46 (br t, J = 3.7 Hz, 12H), 3.24 (br d, J = 7.2 Hz, 2H), 3.02-2.80 (m, 4H), 2.60 (br s, 2H), 2.55 (br s, 1H), 2.09-1.94 (m, 1H). | 1 | 1026.45 |
| 167 | 763.5 | 765.5 | $^1$H NMR (400 MHz, DMSO-$d_6$) δ 1.14-1.31 (m, 1H), 2.02-2.08 (m, 1H), 2.58-2.62 (m, 1H), 2.68-2.78 (m, 2H), 2.84-2.93 (m, 1H), 3.73-4.04 (m, 8H), 4.29-4.45 (m, 2H), 5.10-5.14 (m, 1H), 6.66-6.72 (m, 1H), 6.78-6.88 (m, 1H), 7.10-7.52 (m, 7H), 7.81-7.88 (m, 2H), 8.10 (s, 1H), 8.73 (s, 1H), 10.03 (s, 1H), 11.11 (s, 1H). | 2 | 763.18 |
| 168 | 807.54 | 809.54 | $^1$H NMR (400 MHz, DMSO-$d_6$) δ 1.99-2.07 (m, 1H), 2.51-2.57 (m, 4H), 2.84-2.93 (m, 1H), 3.63 (t, J = 6.4 Hz, 2H), 3.71-3.94 (m, 10H), 4.32-4.35 (m, 2H), 5.09-5.14 (m, 1H), 6.56, 6.59 (two singles, 1H), 6.71-6.78 (m, 1H), 7.10-7.47 (m, 7H), 7.81-7.84 (m, 2H), 8.09 (s, 1H), 8.72 (s, 1H), 10.03 (s, 1H), 11.10 (s, 1H). | 2 | 807.23 |
| 169 | 851.58 | 851.58 | $^1$H NMR (400 MHz, DMSO-$d_6$) δ 2.37-2.48 (m, 3H), 2.54-2.65 (m, 2H), 2.83-2.93 (m, 1H), 3.54-3.94 (m, 16H), 4.25-4.40 (m, 2H), 5.09-5.13 (m, 1H), 6.53-6.58 (m, 1H), 6.70-6.77 (m, 1H), 7.11-7.46 (m, 7H), 7.82 (d, J = 8.0 Hz, 2H), 8.08 (s, 1H), 8.71 (s, 1H), 10.06 (s, 1H), 11.10 (s, 1H). | 2 | 851.29 |
| 170 | 895.61 | 897.61 | $^1$H NMR (400 MHz, DMSO-$d_6$) δ 2.00-2.07 (m, 1H), 2.41-2.46 (m, 2H), 2.53-2.61 (m, 2H), 2.84-2.93 (m, 1H), 3.46-3.62 (m, 10H), 3.70-4.01 (m, 10H), 4.28-4.36 (m, 2H), 5.09-5.13 (m, 1H), 6.54, 6.58 (two singles, 1H), 6.69-6.77 (m, 1H), 7.10-7.47 (m, 7H), 7.82 (d, J = 8.4 Hz, 2H), 8.09 (s, 1H), 8.71 (s, 1H), 10.03 (s, 1H), 11.10 (s, 1H). | 2 | 895.34 |
| 171 | 939.65 | 941.65 | $^1$H NMR (400 MHz, DMSO-$d_6$) δ 1.90-2.14 (m, 2H), 2.40-2.46 (m, 2H), 2.54-2.68 (m, 2H), 2.83-2.92 (m, 1H), 3.49-3.55 (m, 11H), 3.58-3.64 (m, 2H), 3.71-3.87 (m, 6H), 3.89-4.01 (m, 4H), 4.27-4.34 (m, 2H), 5.06-5.15 (m, 1H), 6.56-6.60 (m, 1H), 6.67-6.77 (m, 1H), 7.10 (d, J = 1.6 Hz, 1H), 7.16-7.25 (m, 2H), 7.29 (s, 1H), 7.33-7.38 (m, 1H), 7.41-7.47 (m, 2H), 7.78-7.85 (m, 2H), 8.09 (s, 1H), 8.71 (s, 1H), 10.14 (s, 1H), 11.08 (s, 1H). | 2 | 939.39 |
| 172 | 921.66 | 923.66 | $^1$H NMR (400 MHz, DMSO-$d_6$) δ 11.11 (s, 1H), 9.99 (s, 1H), 7.86-7.76 (m, 3H), 7.49-7.35 (m, 3H), 7.26 (d, J = 2.3 Hz, 1H), 7.22 (d, J = 3.5 Hz, 2H), 7.13 (s, 1H), 7.04 (d, J = 2.3 Hz, 1H), 6.78-6.69 (m, 1H), 6.61-6.55 (m, 1H), 5.11 (dd, J = 5.4, 13.0 Hz, 1H), 4.33 (d, J = 4.3 Hz, 2H), 3.81-3.50 (m, 13H), 3.02-2.73 (m, 7H), 2.64-2.53 (m, 3H), 2.47 (s, 4H), 2.11-1.96 (m, 1H). | 2 | 921.38 |
| 173 | 965.7 | 967.7 | $^1$H NMR (400 MHz, CD$_3$OD) δ 8.25 (s, 2H), 7.83-7.81 (m, 1H), 7.77-7.75 (m, 2H), 7.43-7.42 (m, 2H), 7.35-7.34 (m, 1H), 7.27-7.26 (m, 2H), 7.25-7.20 (m, 2H), 7.06-7.05 (m, 1H), 6.88-6.84 (m, 1H), 6.57-6.54 (m, 1H), 5.11-5.05 (m, 1H), 4.34-4.33 (m, 1H), 3.92-3.88 (m, 7H), 3.74-3.73 (m, 5H), 3.68-3.66 (m, 5H), 3.09 (s, 3H), 2.93 (s, 3H), 2.78-2.74 (m, 6H), 2.52-2.47 (m, 2H), 2.12-2.11 (m, 1H). | 2 | 965.43 |
| 174 | 1009.72 | 1011.73 | $^1$H NMR (400 MHz, DMSO-$d_6$) δ 11.12 (s, 1H), 10.16 (s, 1H), 8.24-8.06 (m, 2H), 7.84 (d, J = 8.0 Hz, 2H), 7.49-7.22 (m, 6H), 7.13-7.05 (m, 1H), 6.81-6.69 (m, 1H), 6.56 (d, J = 14.8 Hz, 1H), 5.17-5.09 (m, 1H), 4.32 (s, 2H), 4.22 (s, 4H), 3.78-3.46 (m, 18H), 2.96 (s, 3H), 2.86 (s, 4H), 2.71-2.55 (m, 4H), 2.48-2.42 (m, 2H), 2.09-2.00 (m, 1H). | 2 | 1009.49 |
| 175 | 1053.76 | 1055.76 | $^1$H NMR (400 MHz, CDCl$_3$) δ 11.12 (s, 1H), 10.14 (s, 1H), 8.10 (s, 2H), 7.84 (d, J = 8 Hz, 2H), 7.54-7.22 (m, 6H), 7.07 (s, 1H), 6.84-6.66 (m, 1H), 6.56 (d, J = 14.4 Hz, 1H), 5.18-5.06 (m, 1H), 4.39-4.03 (m, 6H), 3.80-3.39 (m, 22H), 2.96 (s, 3H), 2.86 (s, 4H), 2.72-2.57 (m, 4H), 2.47-2.38 (m, 2H), 2.11-1.98 (m, 1H). | 2 | 1053.54 |
| 176 | 765.52 765.52 | 767.52 767.52 | $^1$H NMR (400 MHz, DMSO-$d_6$) δ 1.68-1.75 (m, 2H), 1.79-1.84 (m, 2H), 2.01-2.08 (m, 1H), 2.46-2.48 (m, 2H), 2.54-2.62 (m, 2H), 2.84-2.94 (m, 1H), 3.68-3.79 (m, 4H), 3.87-4.00 (m, 4H), 4.22 (t, J = 6.2 Hz, 2H), 5.10-5.14 (m, 1H), 7.10-7.45 (m, 7H), 7.83 (t, J = 8.0 Hz, 2H), 8.09 (s, 1H), 8.72 (s, 1H), 10.03 (s, 1H), 11.11 (s, 1H). | 2 | 765.20 |
| 177 | 809.55 809.55 | 811.56 811.55 | $^1$H NMR (400 MHz, DMSO-$d_6$) δ 1.54-1.62 (m, 4H), 2.01-2.07 (m, 1H), 2.36-2.41 (m, 2H), 2.53-2.61 (m, 2H), 2.83-2.93 (m, 1H), 3.46-3.53 (m, 2H), 3.66-3.77 (m, 6H), 3.85-3.98 (m, 4H), 4.32-4.34 (m, 2H), 5.09-5.13 (m, 1H), 7.10-7.47 (m, 7H), 7.82 (d, J = 8.8 Hz, 2H), 8.07 (two singles, 1H), 8.71 (s, 1H), 10.05 (s, 1H), 11.08 (s, 1H). | 2 | 809.25 |
| 178 | 853.59 853.6 | 855.59 855.6 | $^1$H NMR (400 MHz, DMSO-$d_6$) δ 1.48-1.61 (m, 4H), 2.00-2.08 (m, 1H), 2.38 (t, J = 6.8 Hz, 2H), 2.51-2.69 (m, 2H), 2.83-2.93 (m, 1H), 3.40-3.94 (m, 16H), 4.30-4.35 (m, 2H), 5.09-5.13 (m, 1H), 7.10-7.45 (m, 7H), 7.82 (d, J = 8.0 Hz, 2H), 8.08 (s, 1H), 8.71 (s, 1H), 10.03 (s, 1H), 11.10 (s, 1H). | 2 | 853.30 |
| 179 | 897.63 897.63 | 899.63 899.63 | $^1$H NMR (400 MHz, DMSO-$d_6$) δ 1.47-1.62 (m, 4H), 2.01-2.05 (m, 1H), 2.34-2.41 (m, 2H), 2.54-2.67 (m, 2H), 2.84-2.93 (m, 1H), 3.37-3.61 (m, 12H), 3.71-3.95 (m, 8H), 4.28-4.35 (m, 2H), 5.09-5.13 (m, 1H), 7.10-7.45 (m, 7H), 7.82 (d, J = 8.4 Hz, 2H), 8.08 (s, 1H), 8.71 (s, 1H), 10.03 (s, 1H), 11.10(s, 1H). | 2 | 897.35 |
| 180 | 941.68 941.66 | 943.68 943.67 | $^1$H NMR (400 MHz, DMSO-$d_6$) δ 1.50-1.60 (m, 4H), 2.01-2.07 (m, 1H), 2.34-2.42 (m, 2H), 2.54-2.69 (m, 2H), 2.82-2.95 (m, 1H), 3.36-3.42 (m, 2H), 3.44-3.48 (m, 2H), 3.50-3.55 (m, 8H), 3.56-3.62 (m, 2H), 3.65-3.75 (m, 4H), 3.76-3.81 (m, 2H), 3.86-3.98 (m, 4H), 4.26-4.34 (m, 2H), 5.06-5.15 (m, 1H), 7.10 (d, J = 2.4 Hz, 1H), 7.18-7.24 (m, 2H), 7.30 (d, J = 2.0 Hz, 1H), 7.34-7.38 (m, 1H), 7.41-7.48 (m, 2H), 7.78-7.84 (m, 2H), 8.08 (s, 1H), 8.71 (s, 1H), 10.03 (s, 1H), 11.10 (s, 1H). | 2 | 941.41 |

TABLE 8
Compounds Prepared by Schemes 3-6
| Ex. No. | Structure |
|---|---|
| 181 | 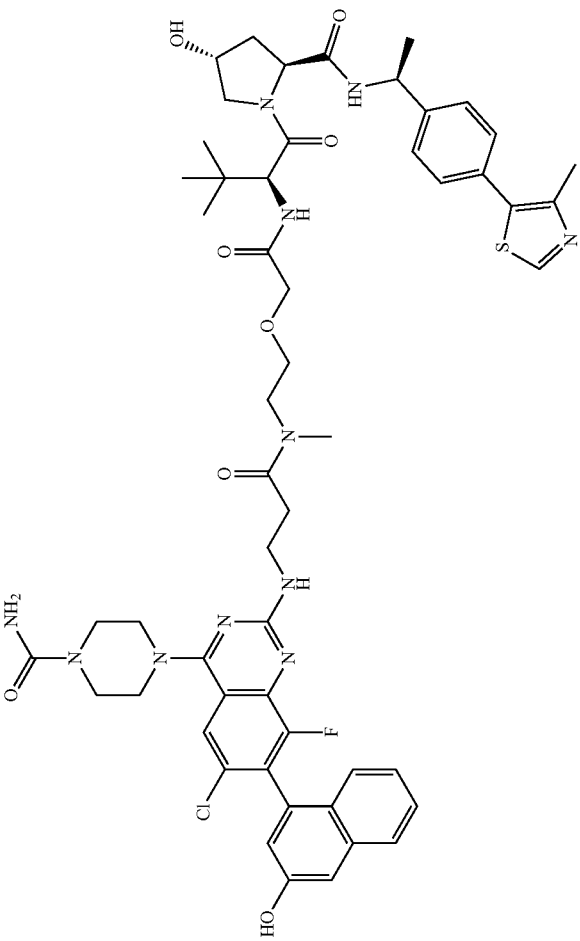 |

TABLE 8-continued
Compounds Prepared by Schemes 3-6
| 1381 | 1382 |
|---|---|
| 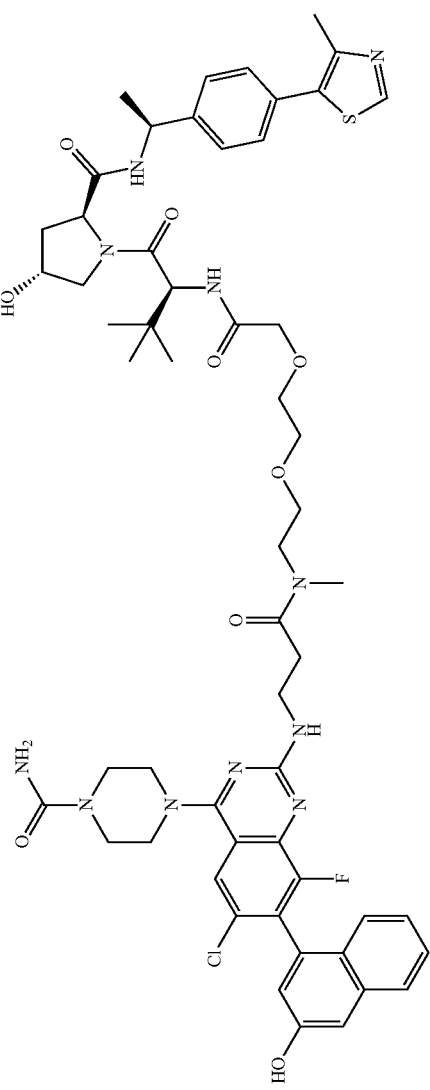 | 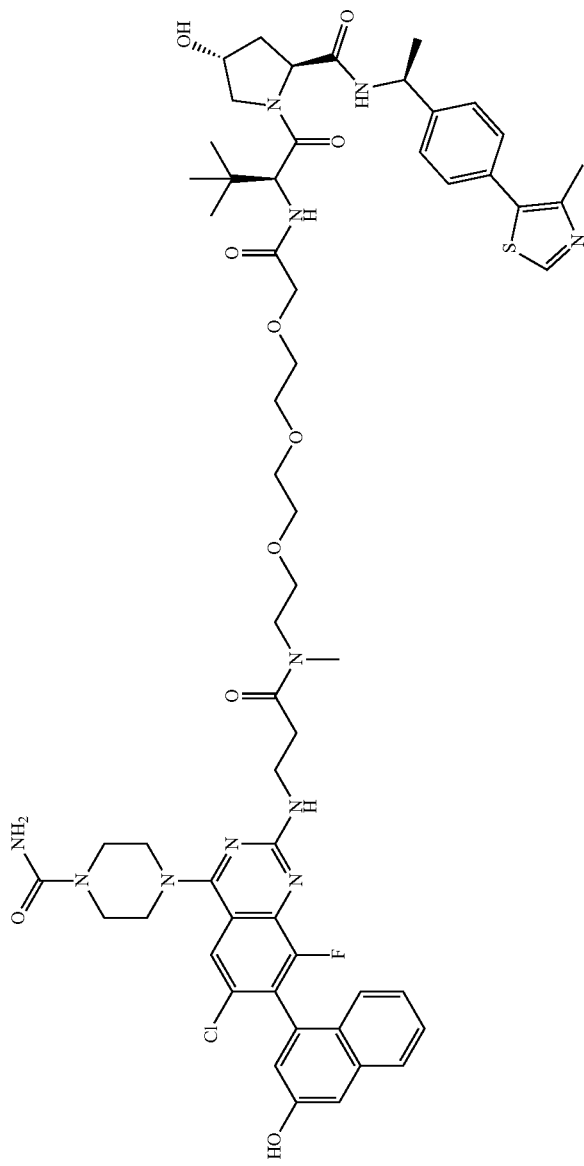 |

TABLE 8-continued
Compounds Prepared by Schemes 3-6
| 1383 | 1384 |
|---|---|
| 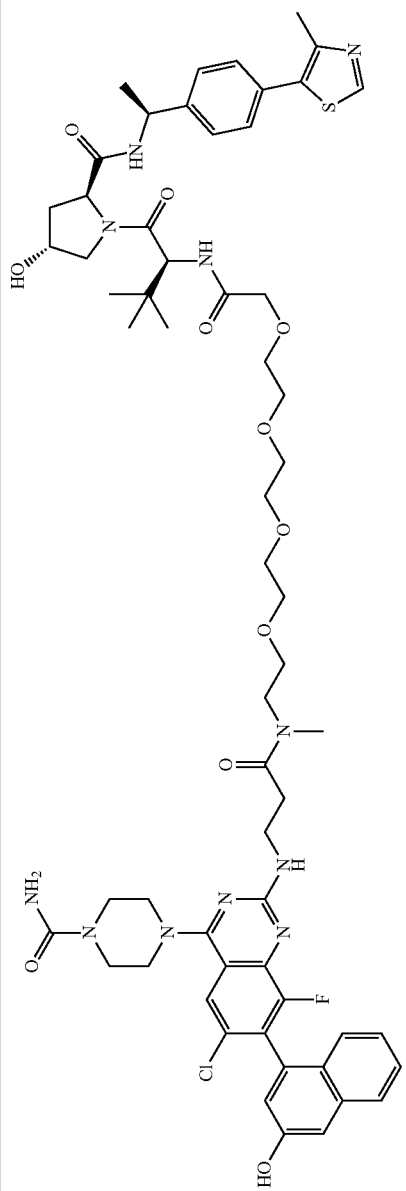 | 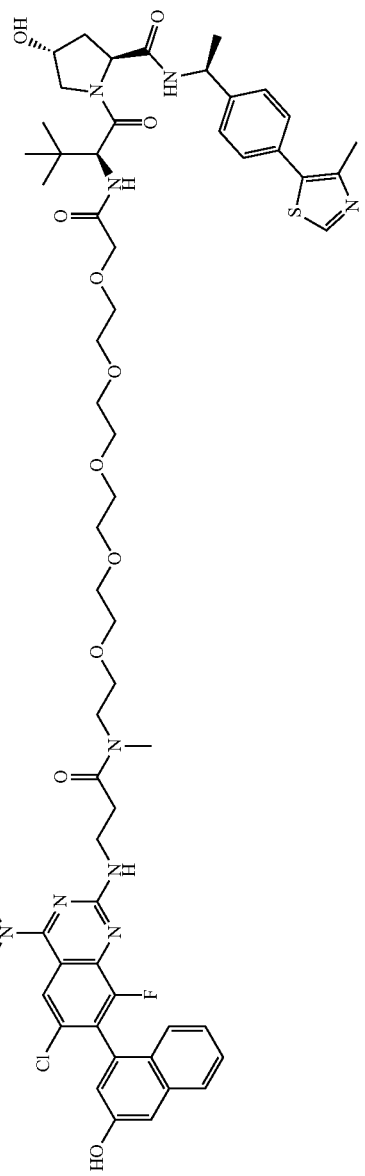 |
| 184 | 185 |

TABLE 8-continued
Compounds Prepared by Schemes 3-6
| 1385 | 1386 |
|---|---|
| 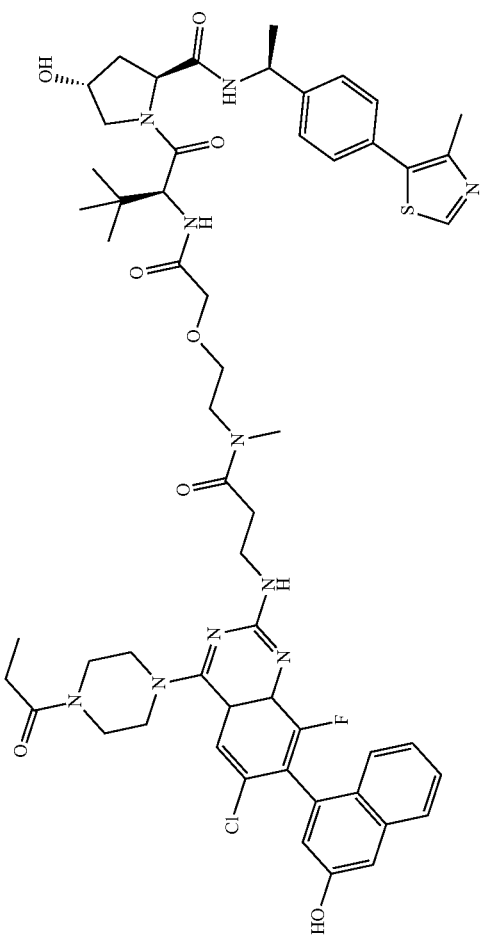 | 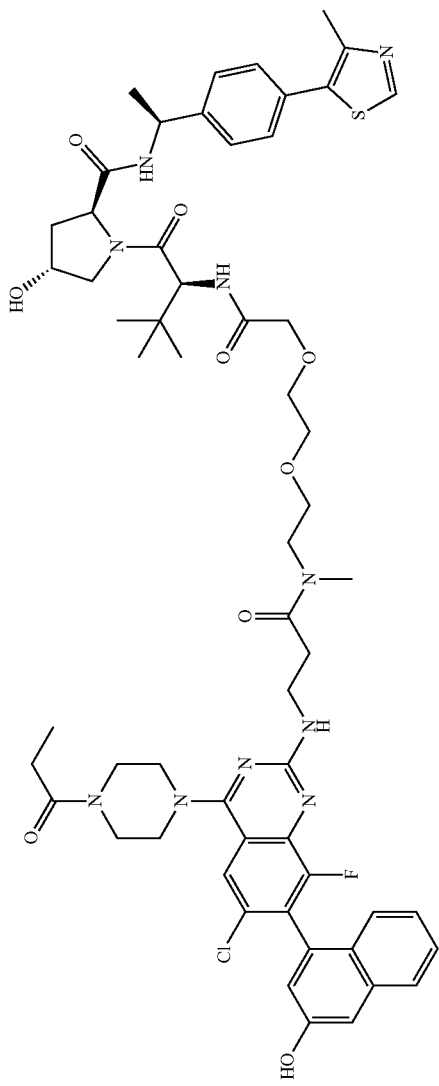 |

TABLE 8-continued
Compounds Prepared by Schemes 3-6
| 1387 | 1388 |
|---|---|
| 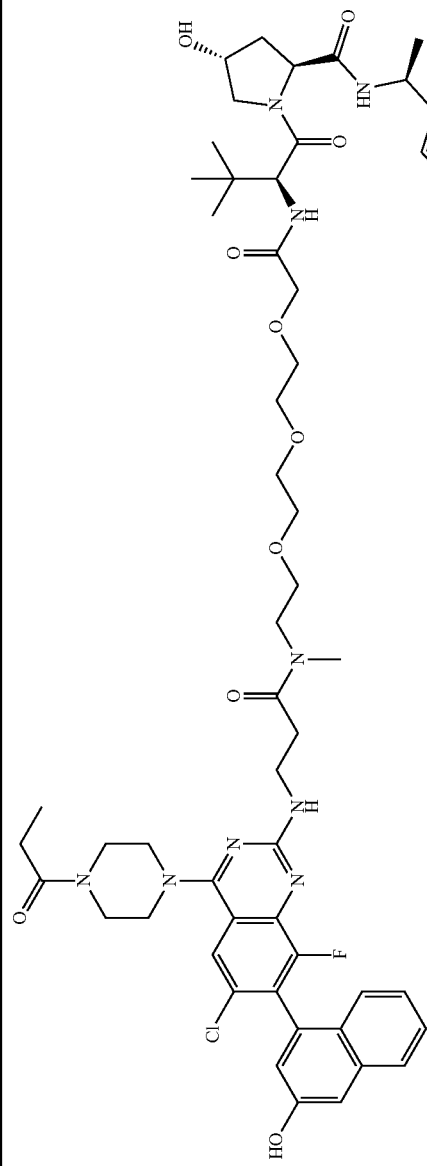 | 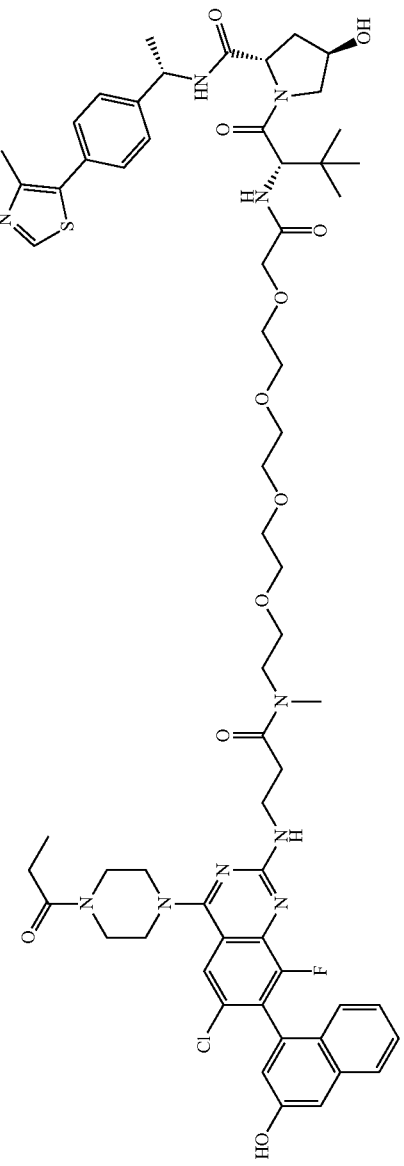 |

TABLE 8-continued
Compounds Prepared by Schemes 3-6
| 1389 | 1390 |
|---|---|
| 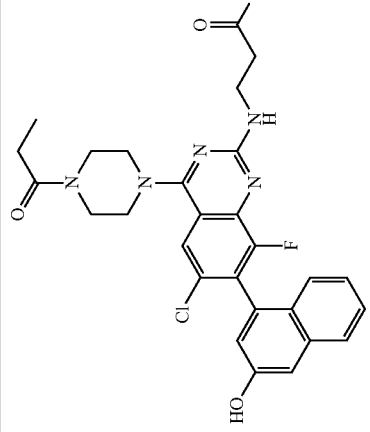 | 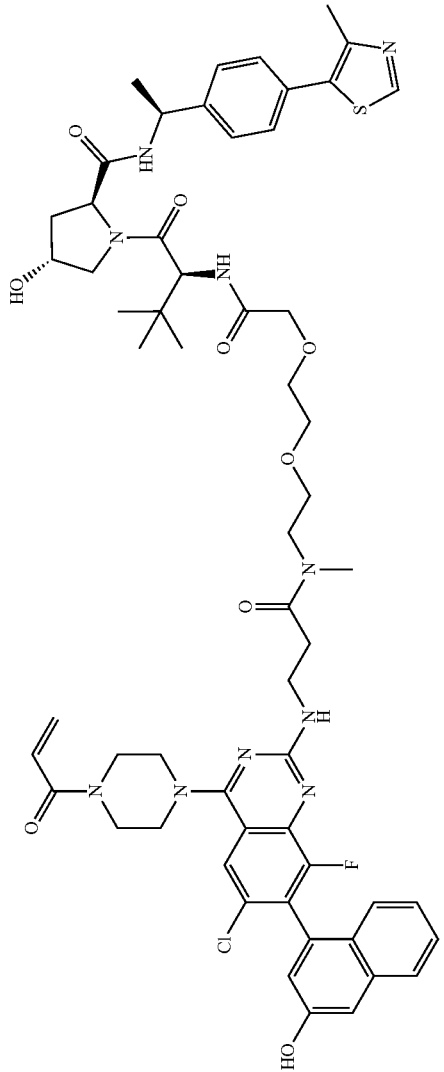 |

TABLE 8-continued
Compounds Prepared by Schemes 3-6
| 1391 | 1392 |
|---|---|
| 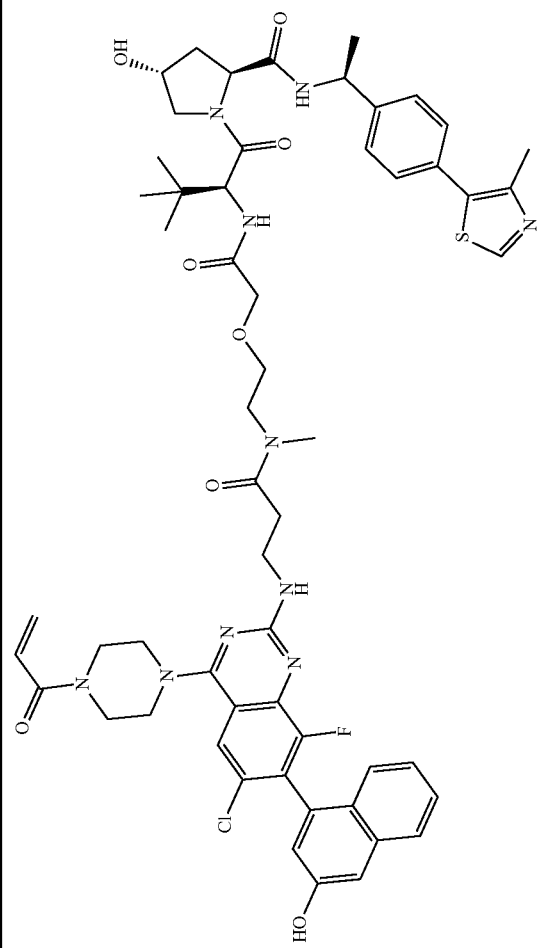 | 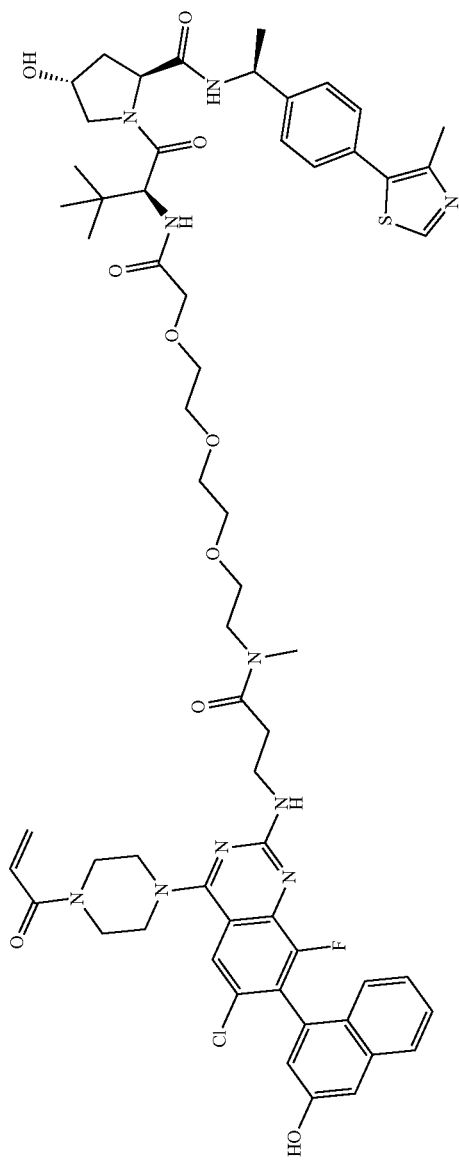 |

TABLE 8-continued
Compounds Prepared by Schemes 3-6
| 1393 | 1394 |
|---|---|
| 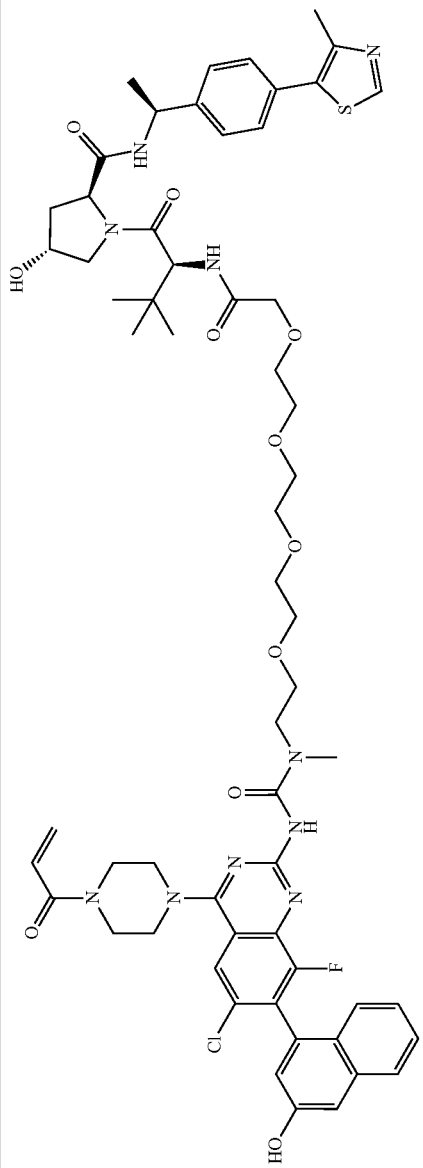 | 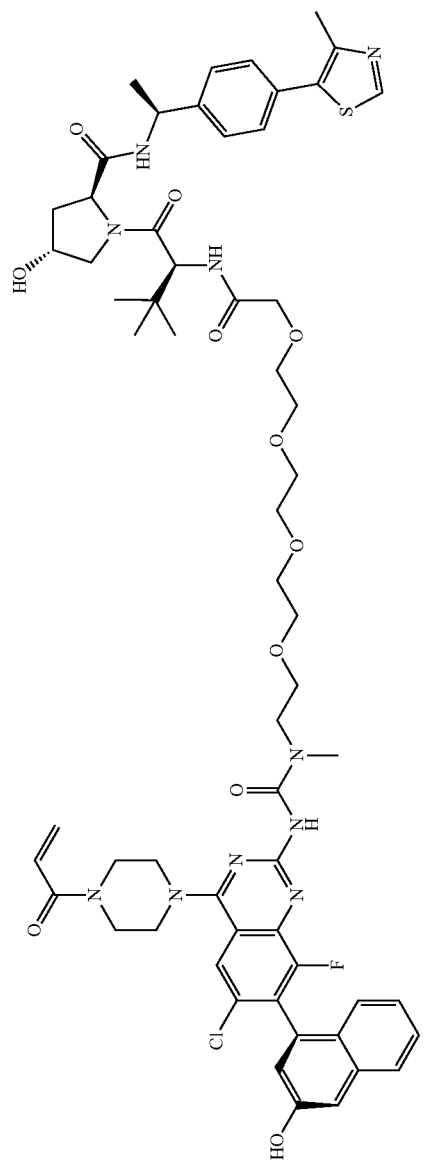 |

TABLE 8-continued
Compounds Prepared by Schemes 3-6
| 1395 | 1396 |
|---|---|
| 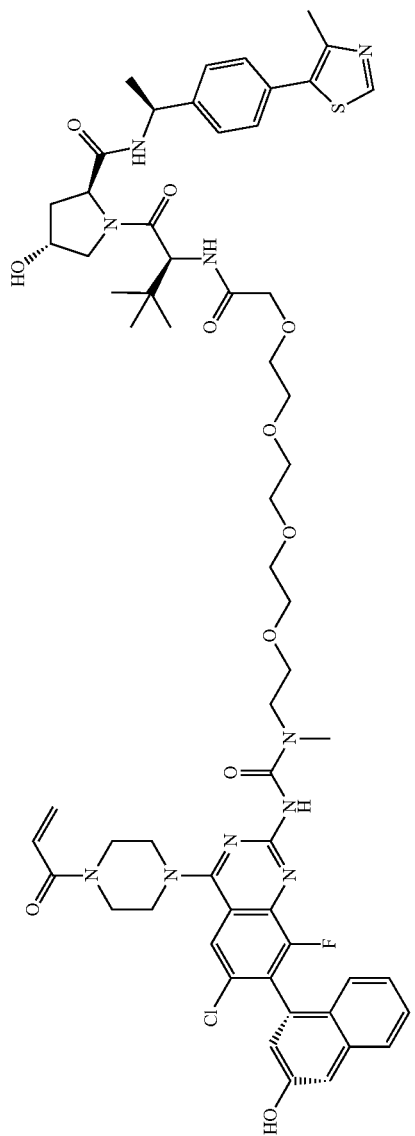 | 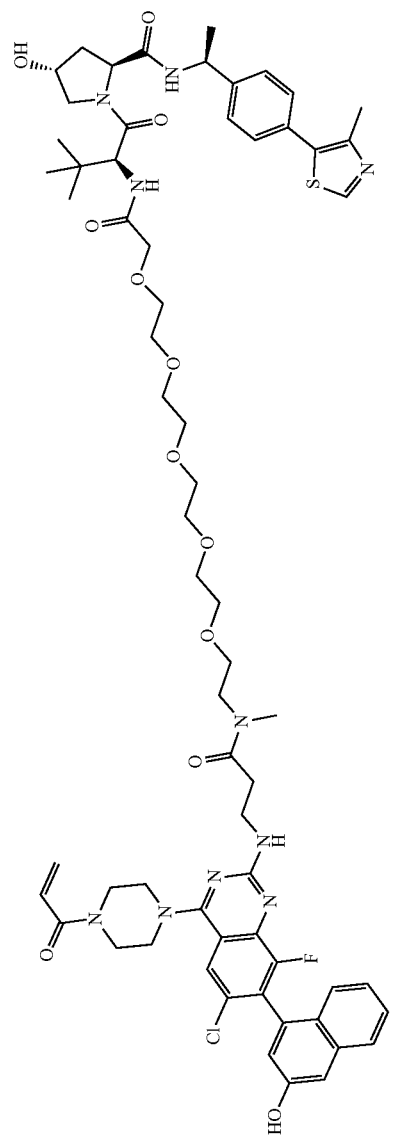 |

TABLE 8-continued
Compounds Prepared by Schemes 3-6
| 1397 | 1398 |
|---|---|
| 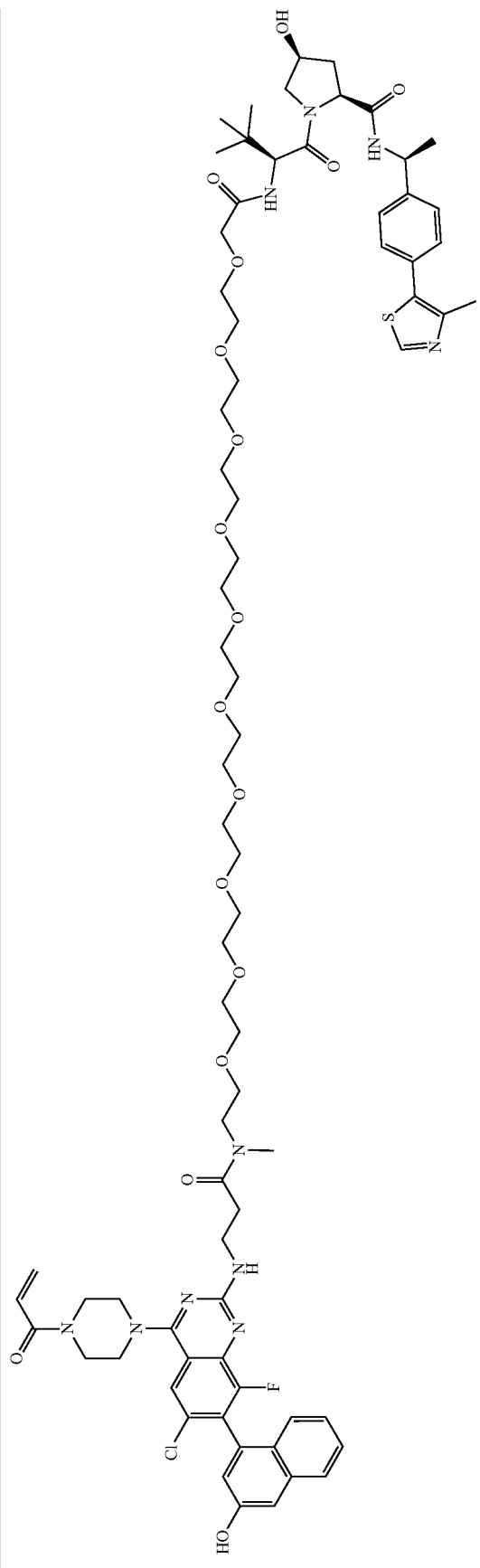 | 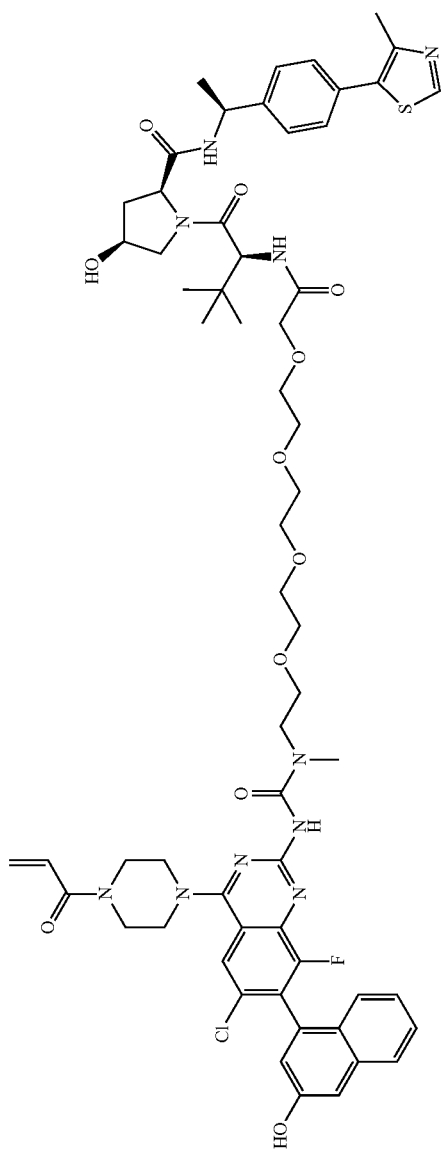 |

TABLE 8-continued
Compounds Prepared by Schemes 3-6
| 1399 | 1400 |
|---|---|
| 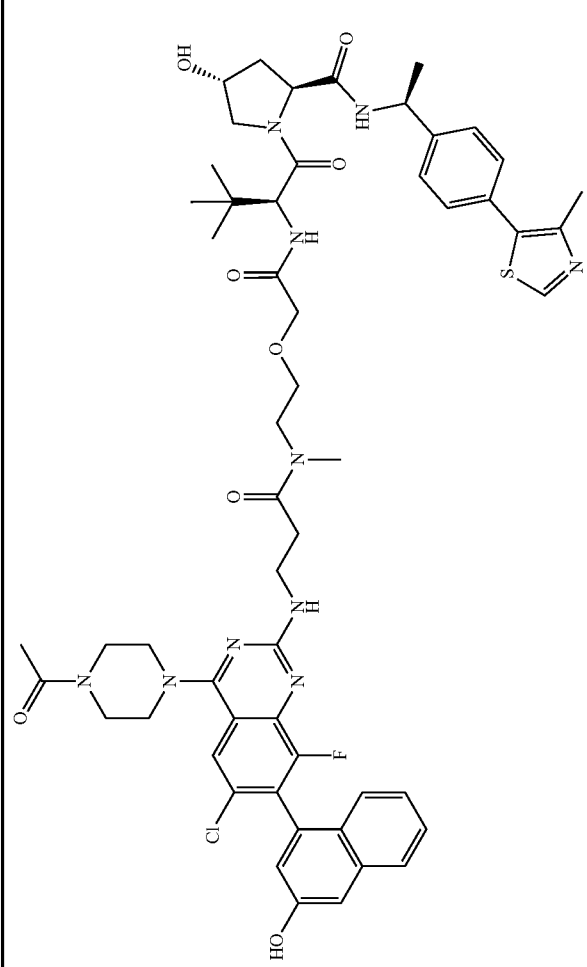 | 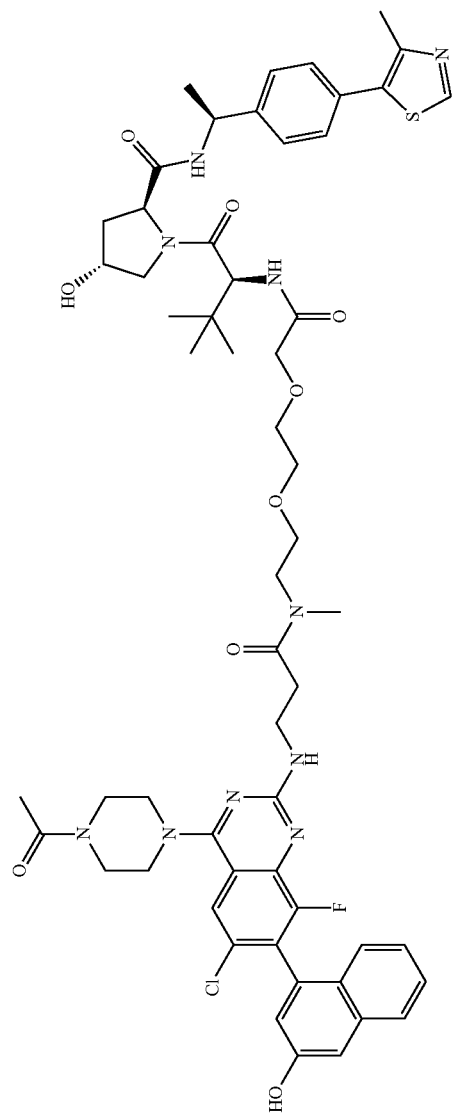 |

TABLE 8-continued
Compounds Prepared by Schemes 3-6
| 1401 | 1402 |
|---|---|
| 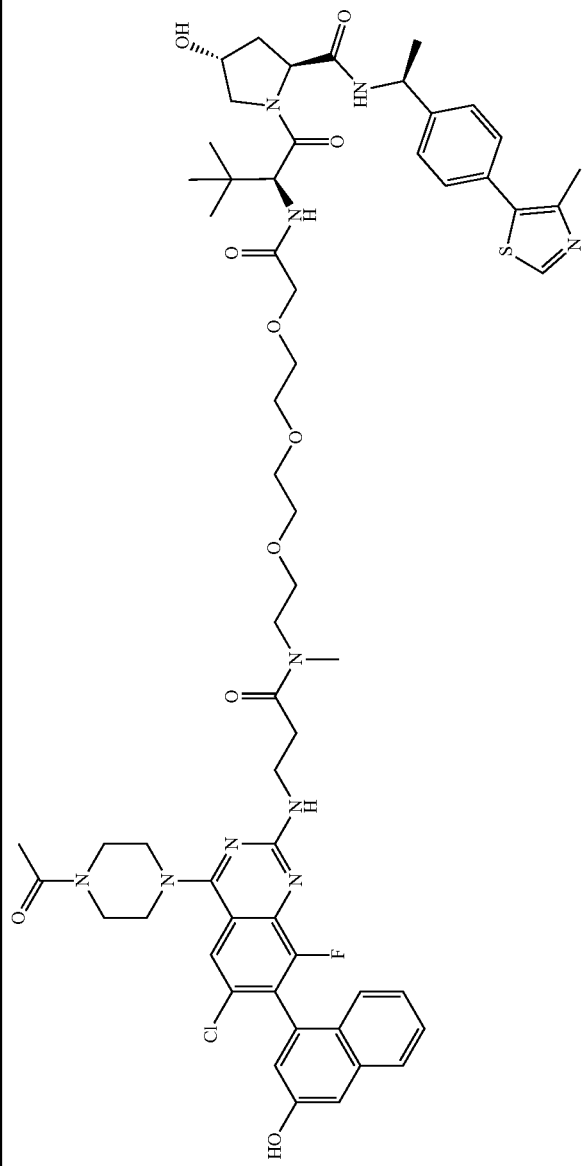 | 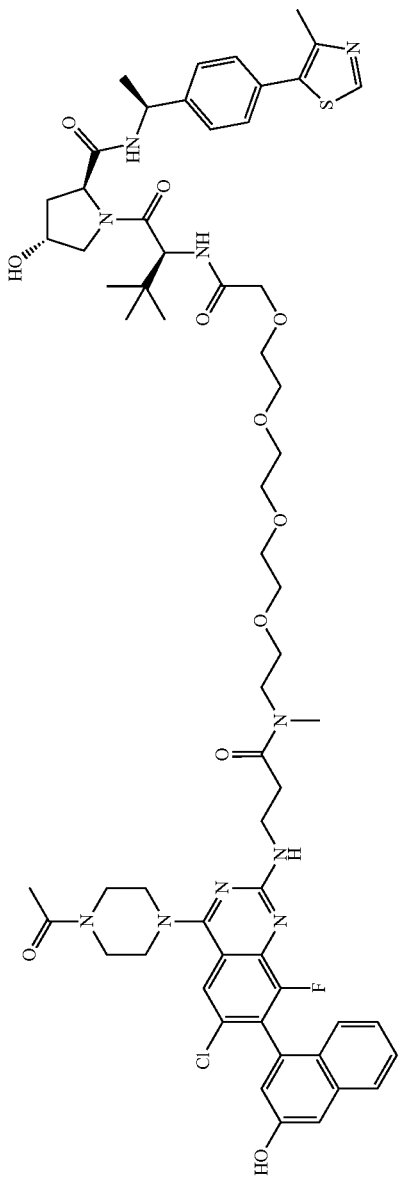 |

TABLE 8-continued
Compounds Prepared by Schemes 3-6
| 1403 | 1404 |
|---|---|
| 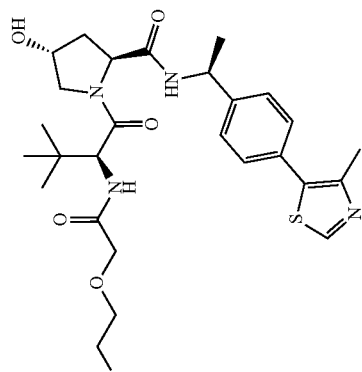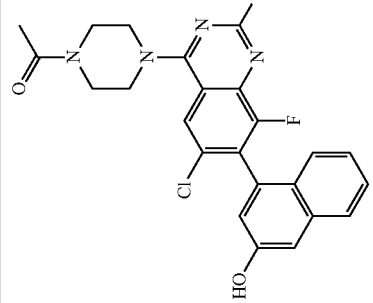 | 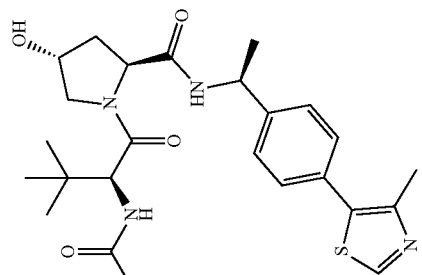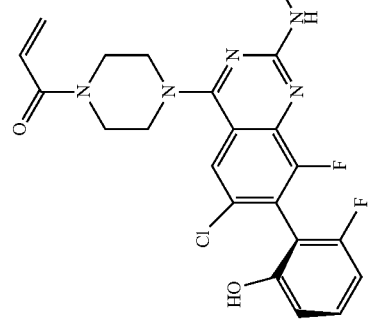 |

TABLE 8-continued
Compounds Prepared by Schemes 3-6
| 1405 | 1406 |
|---|---|
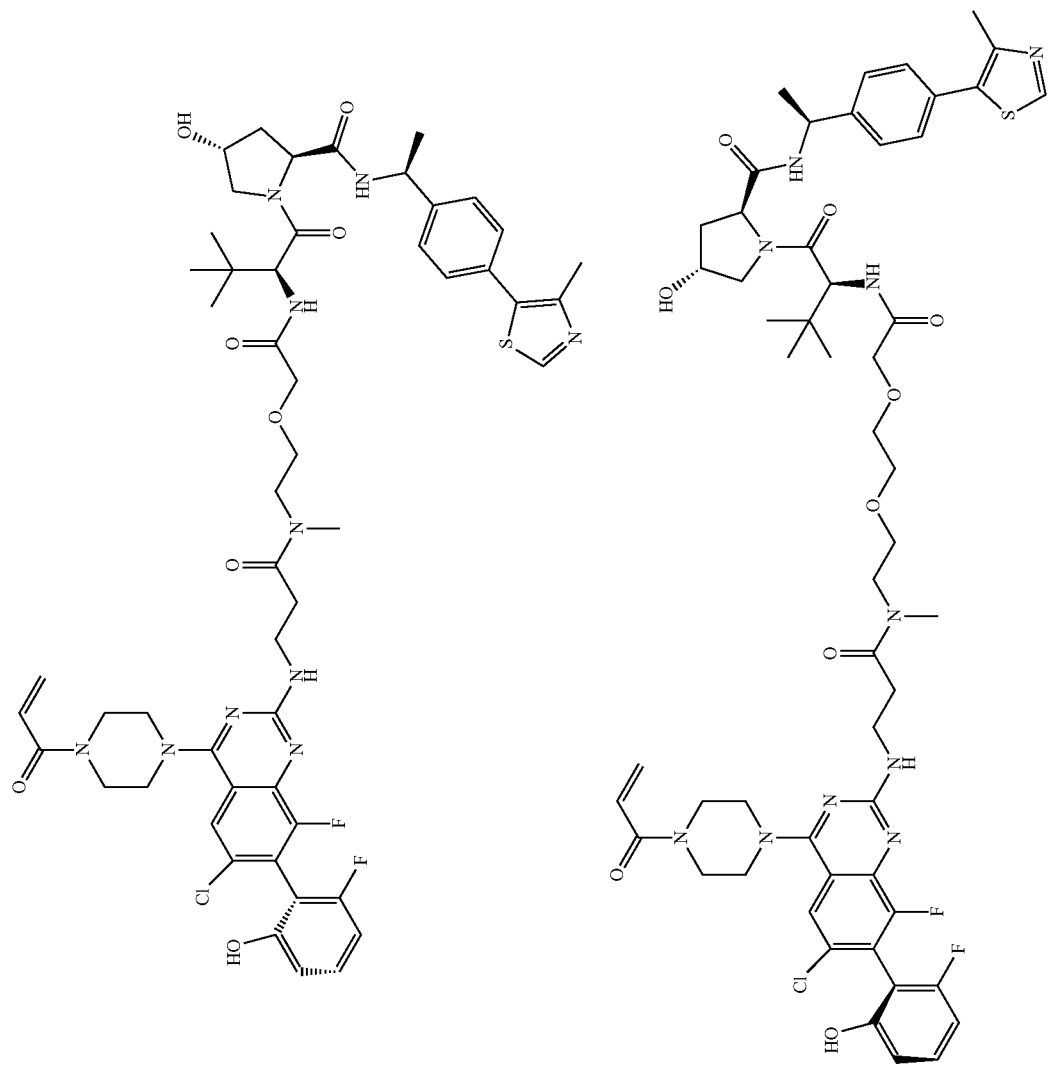

TABLE 8-continued
Compounds Prepared by Schemes 3-6
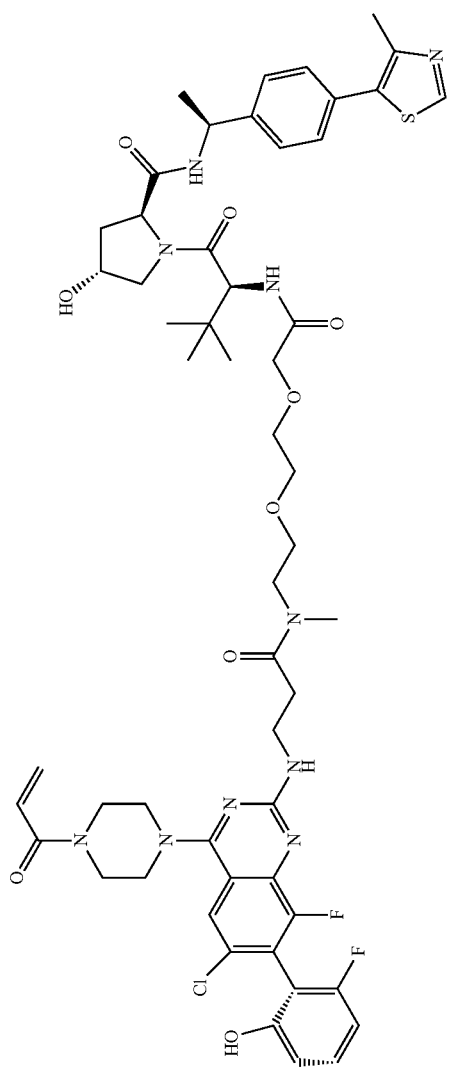

TABLE 8-continued
Compounds Prepared by Schemes 3-6
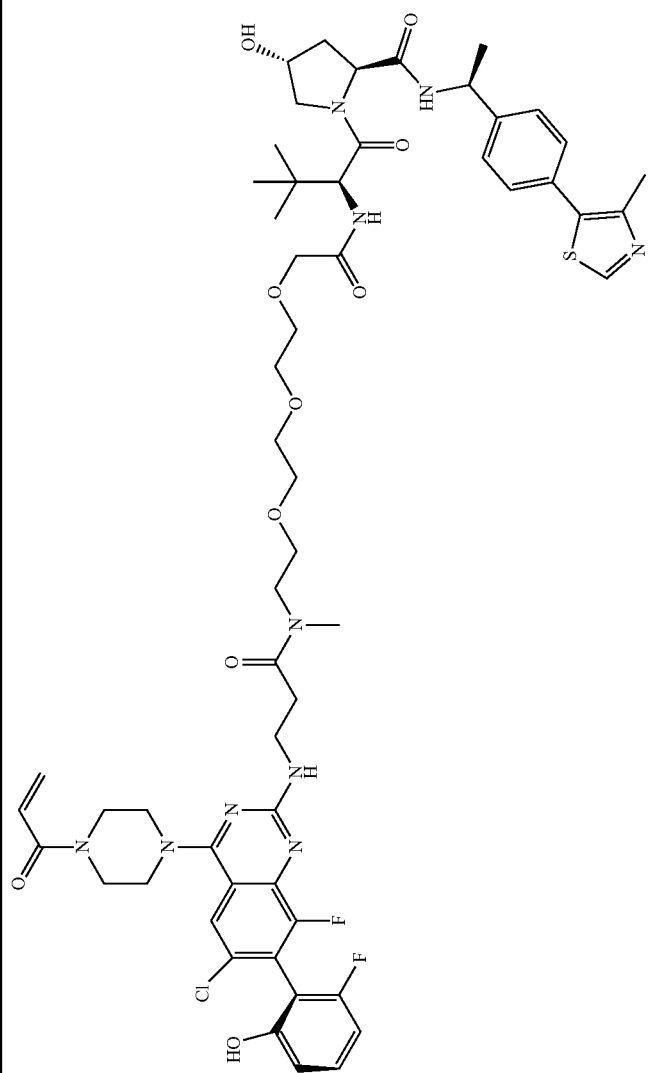

TABLE 8-continued
Compounds Prepared by Schemes 3-6
210
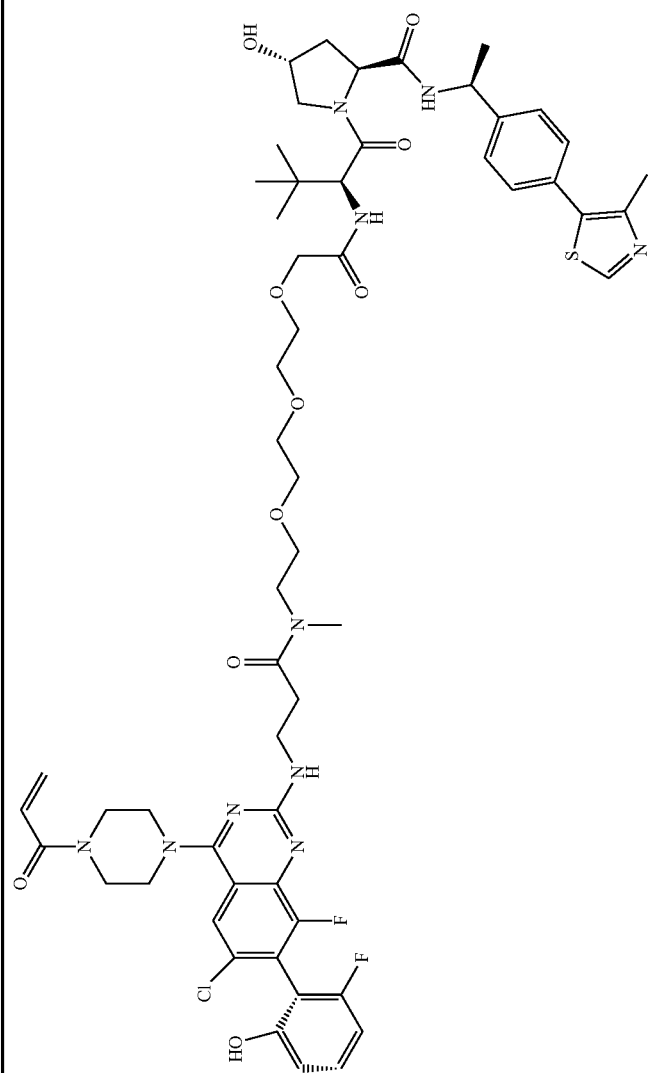

TABLE 8-continued
Compounds Prepared by Schemes 3-6
| 1413 | 1414 |
|---|---|
| 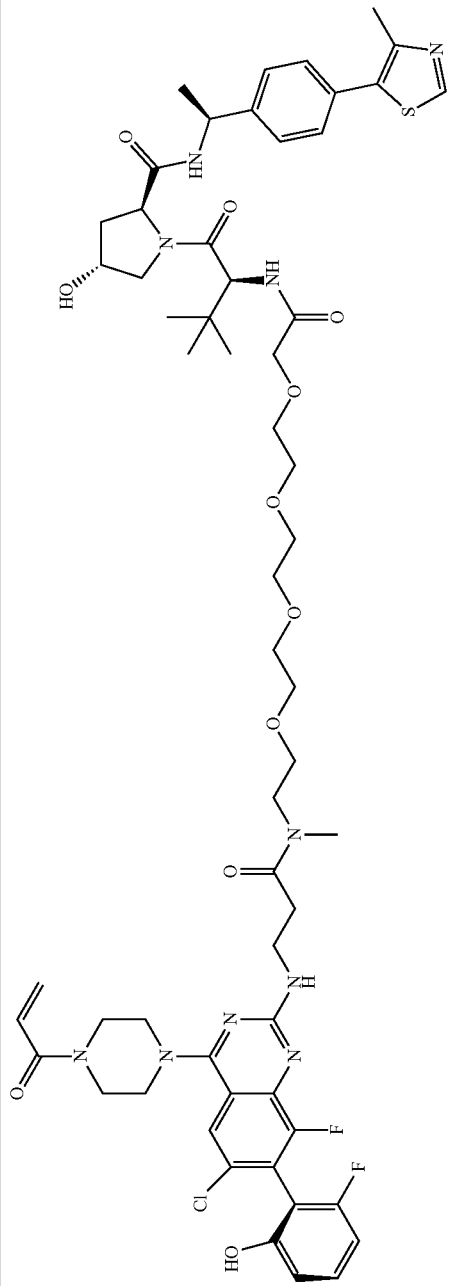 | 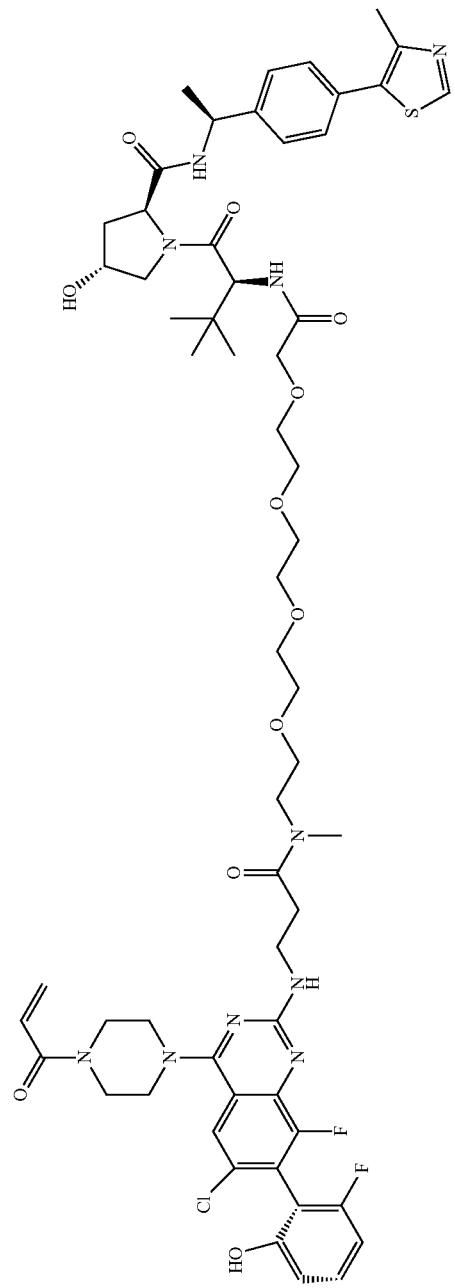 |
| 211 | 212 |

TABLE 8-continued
Compounds Prepared by Schemes 3-6
1415
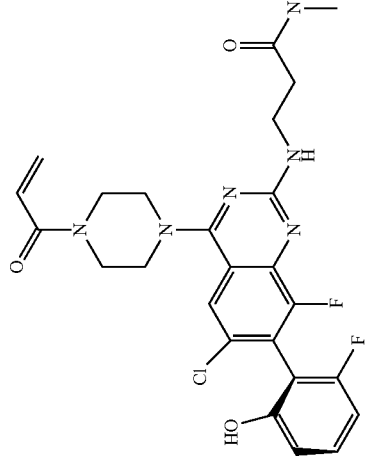
213

TABLE 8-continued
Compounds Prepared by Schemes 3-6
1417
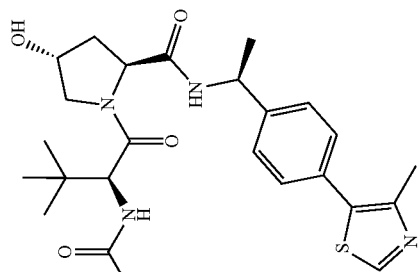

TABLE 8-continued
Compounds Prepared by Schemes 3-6
215
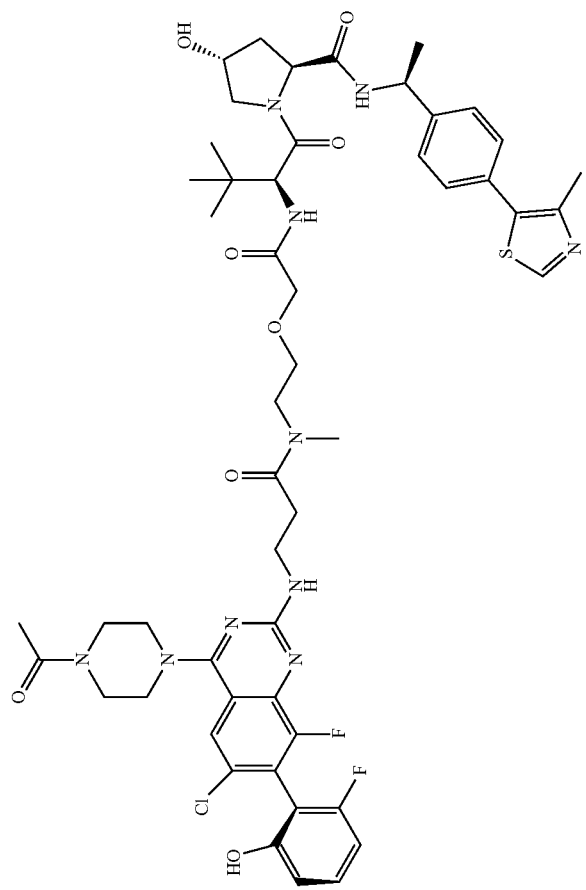

TABLE 8-continued
Compounds Prepared by Schemes 3-6
| 1421 | 1422 |
|---|---|
| 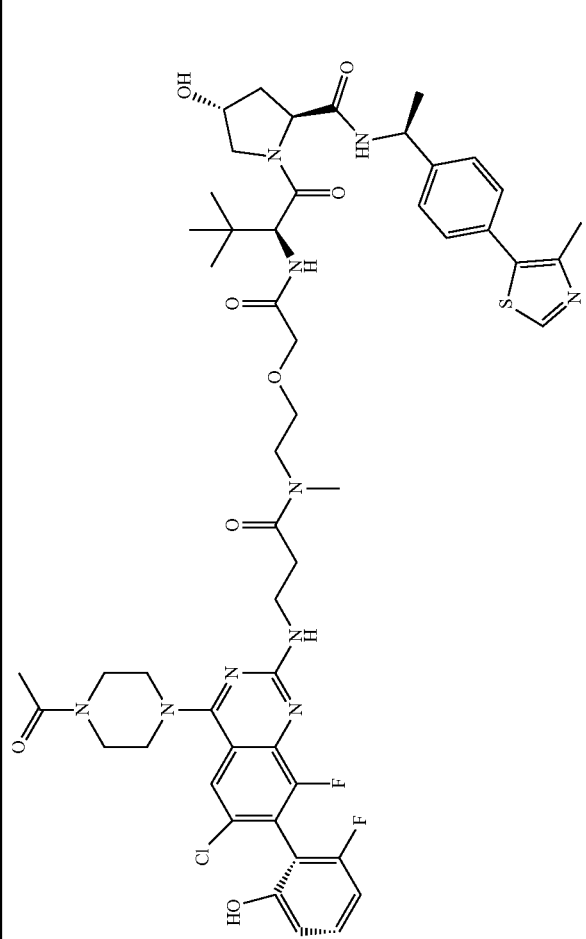 | 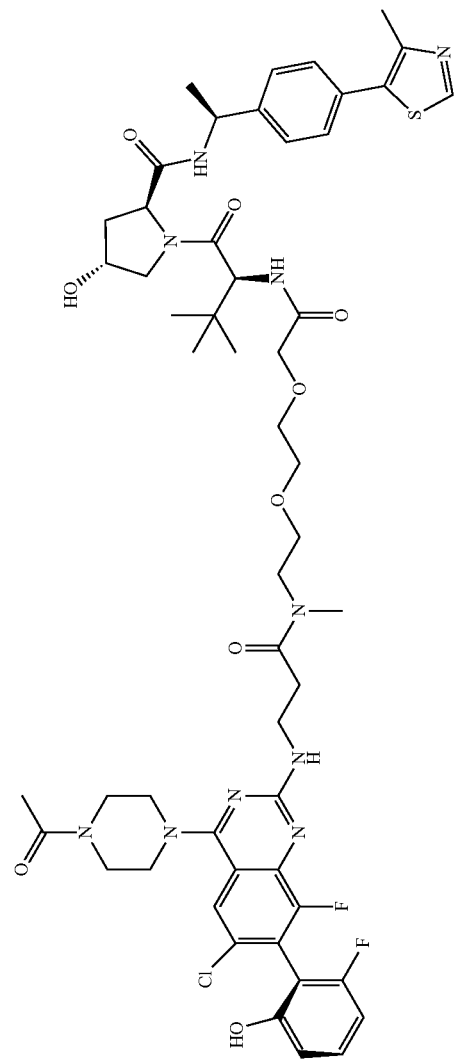 |

TABLE 8-continued
Compounds Prepared by Schemes 3-6
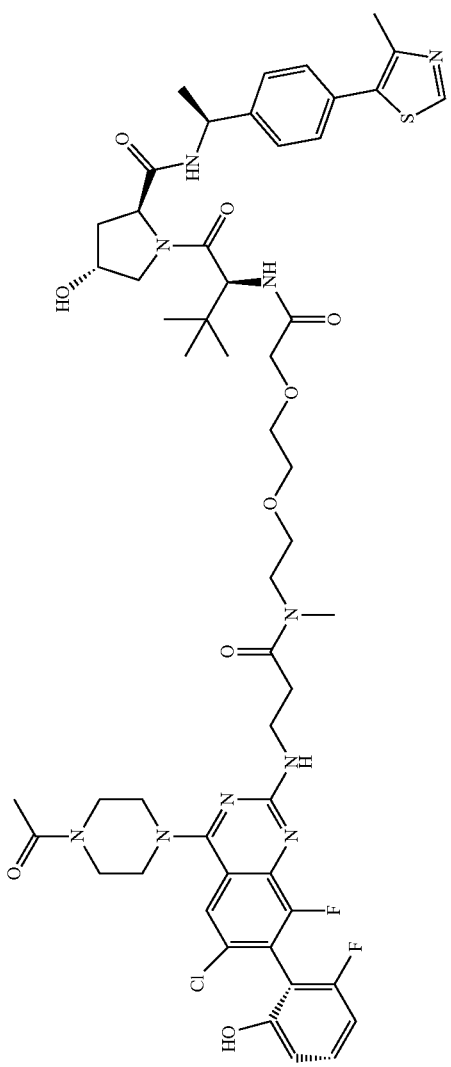

TABLE 8-continued
Compounds Prepared by Schemes 3-6
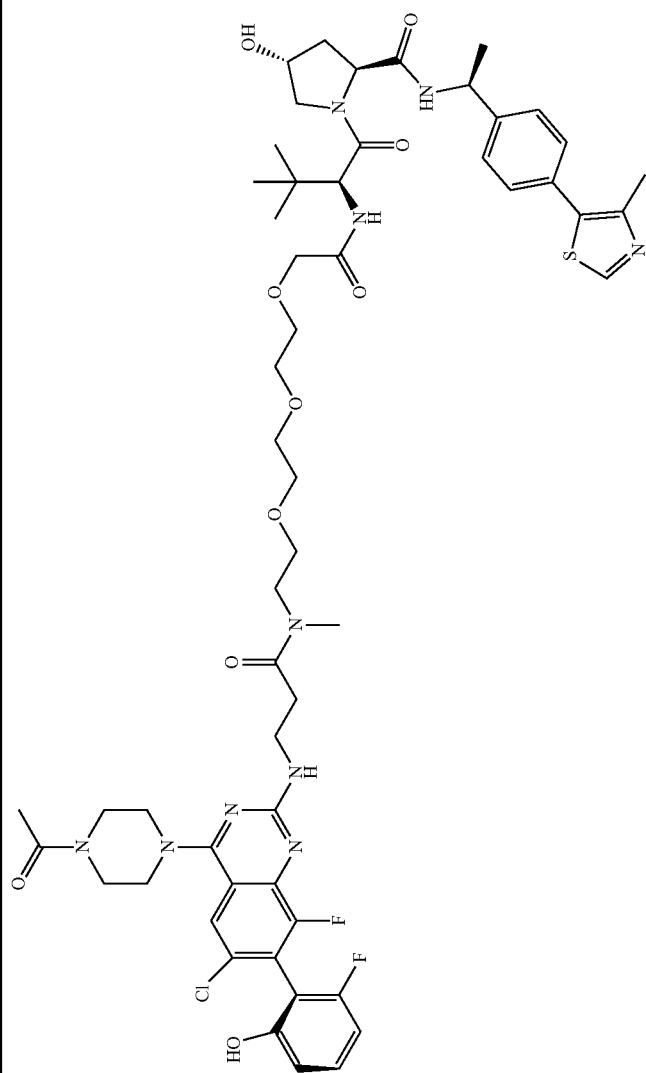

TABLE 8-continued
Compounds Prepared by Schemes 3-6
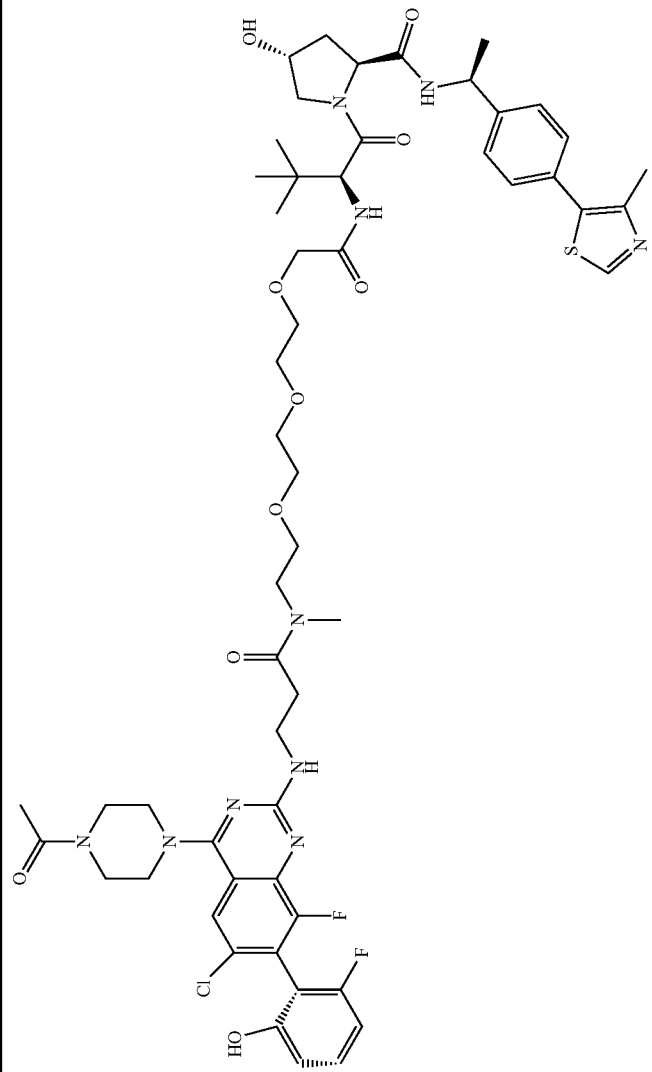

TABLE 8-continued
Compounds Prepared by Schemes 3-6
| 1429 | 1430 |
|---|---|
| 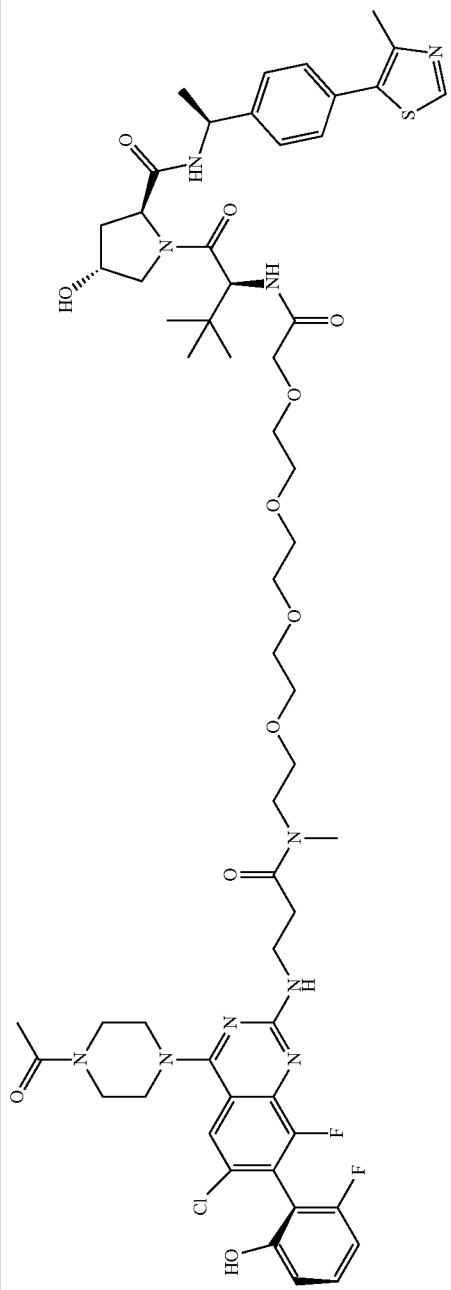 | 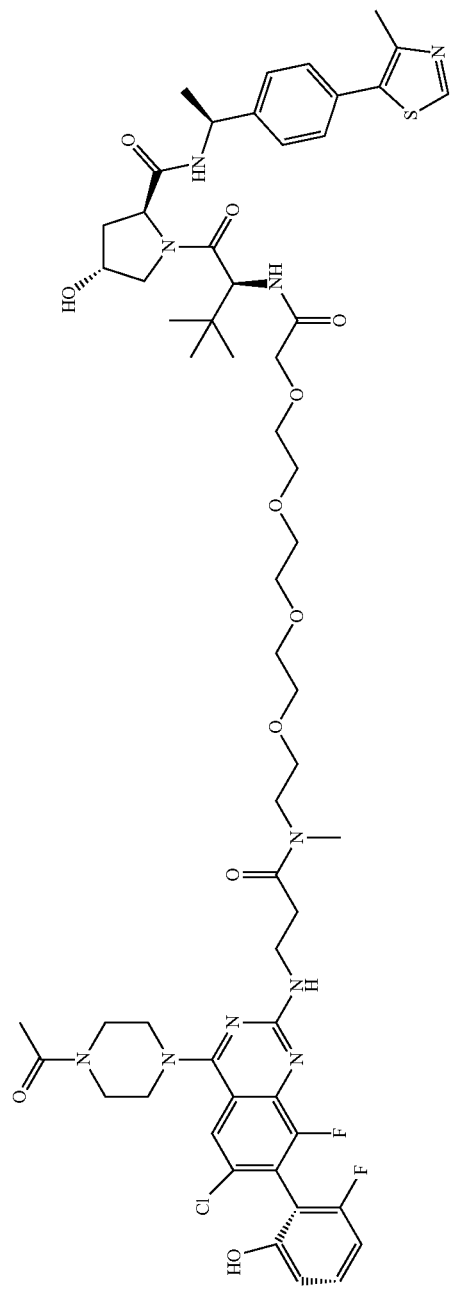 |

TABLE 8-continued
Compounds Prepared by Schemes 3-6
| 223 | 1431 | 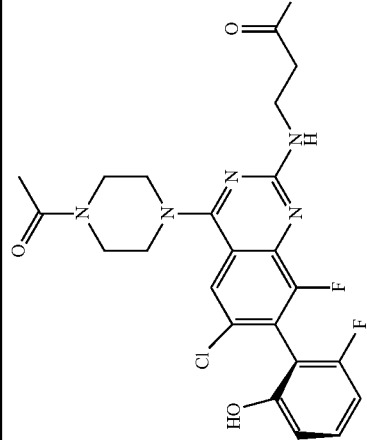 |

TABLE 8-continued
Compounds Prepared by Schemes 3-6
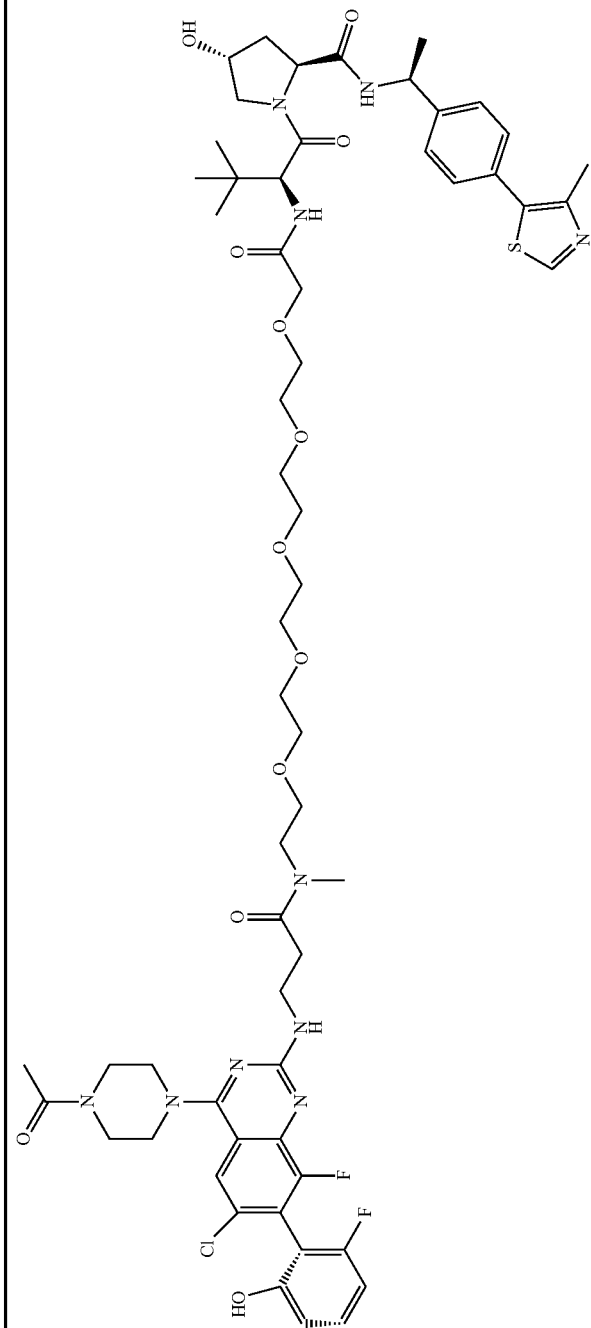
224

TABLE 8-continued
Compounds Prepared by Schemes 3-6
| 225 | 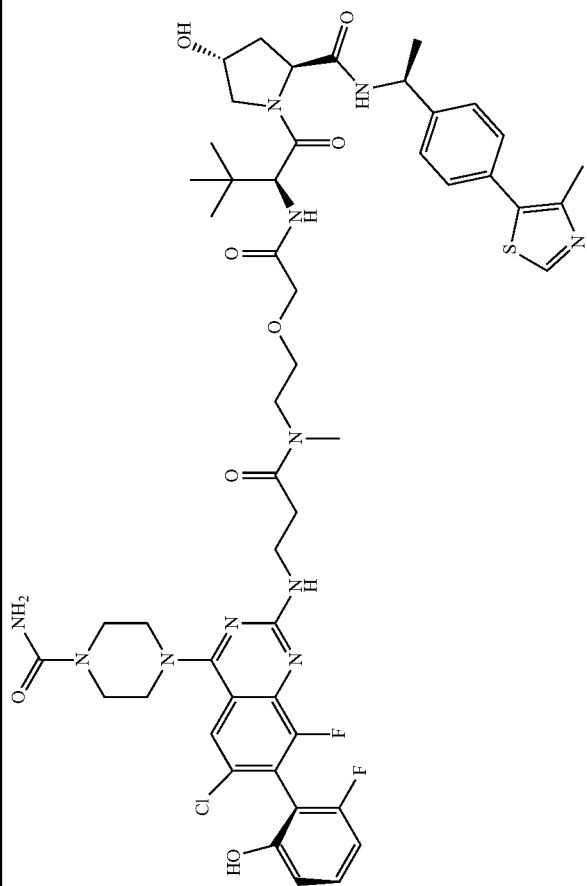 |
|---|---|

TABLE 8-continued
Compounds Prepared by Schemes 3-6
| 1437 | 1438 |
|---|---|
| 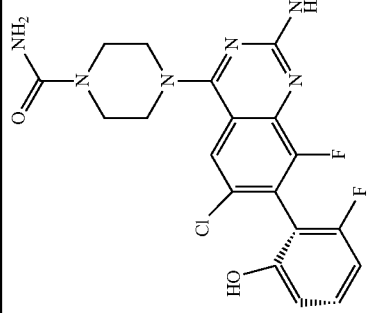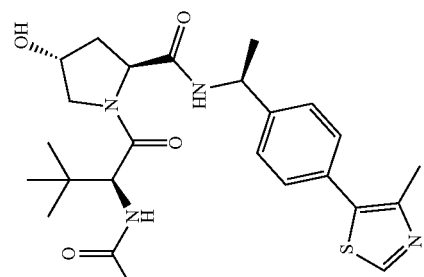 | 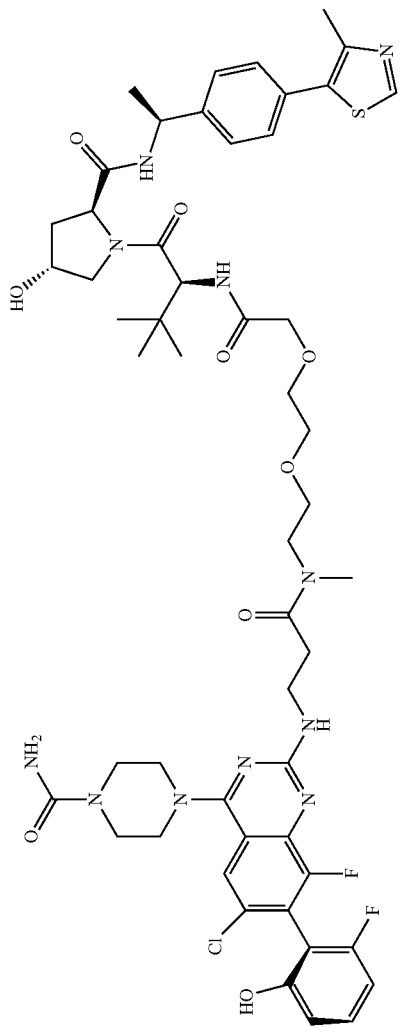 |
| 226 | 227 |

TABLE 8-continued
Compounds Prepared by Schemes 3-6
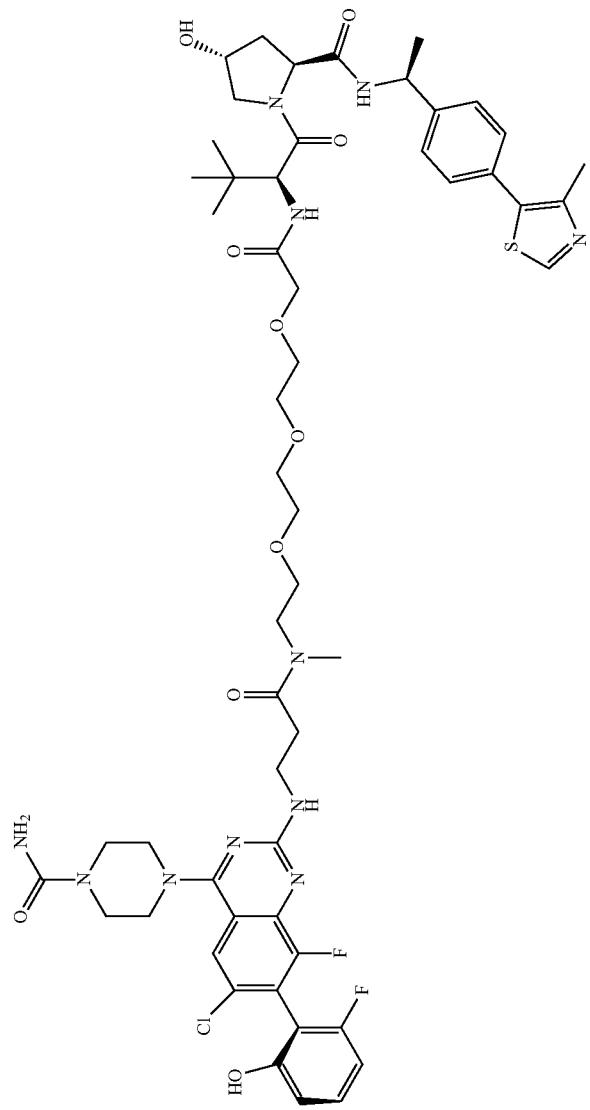

TABLE 8-continued
Compounds Prepared by Schemes 3-6
| 1441 | 1442 |
|---|---|
| 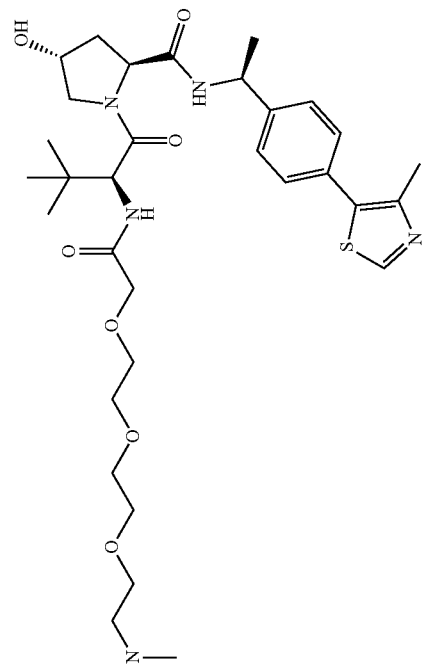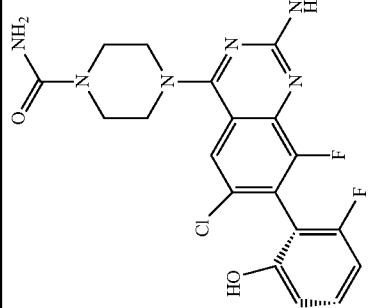 | 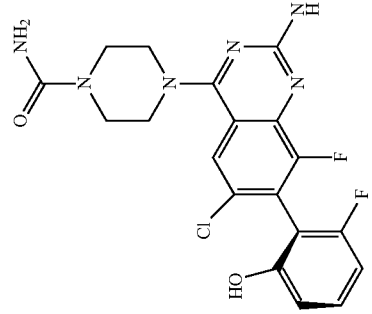 |

TABLE 8-continued
Compounds Prepared by Schemes 3-6
| 1443 | 1444 |
|---|---|
| 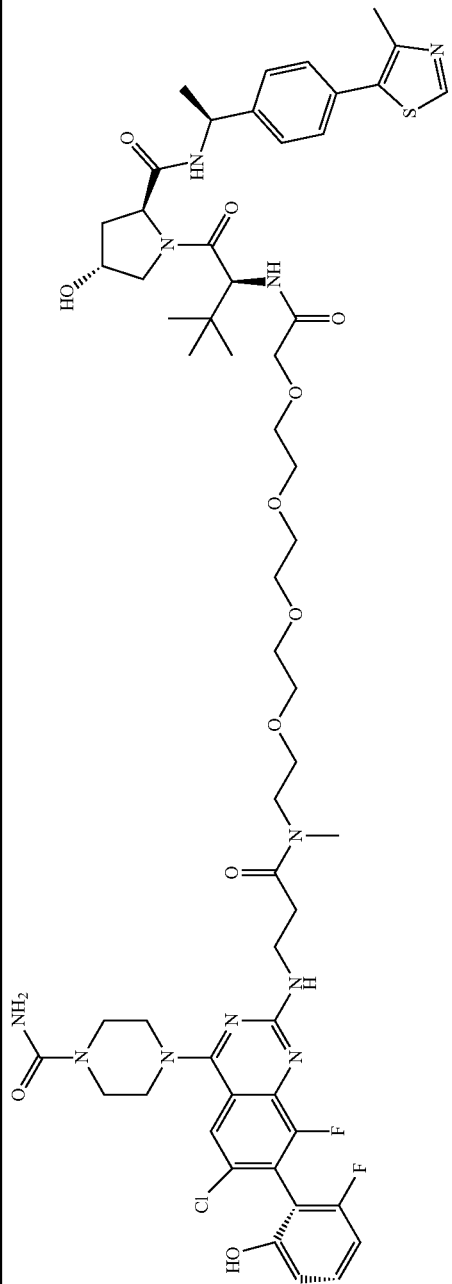 | 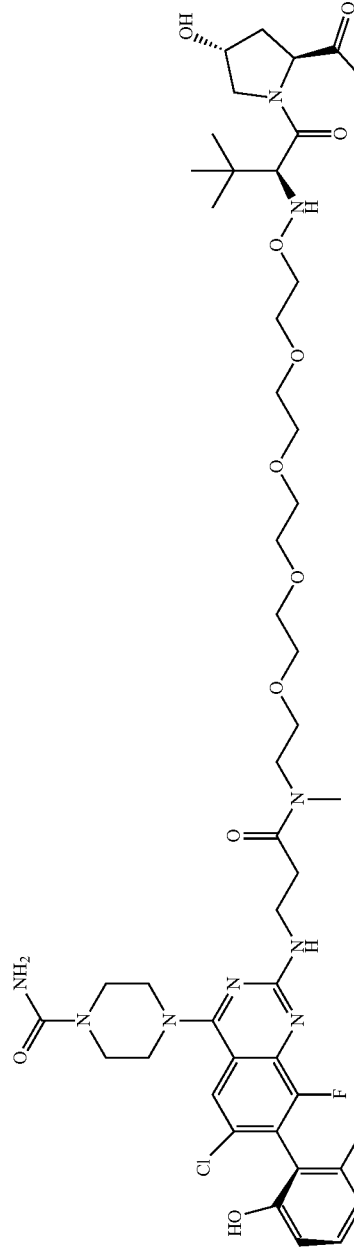 |

TABLE 8-continued
Compounds Prepared by Schemes 3-6
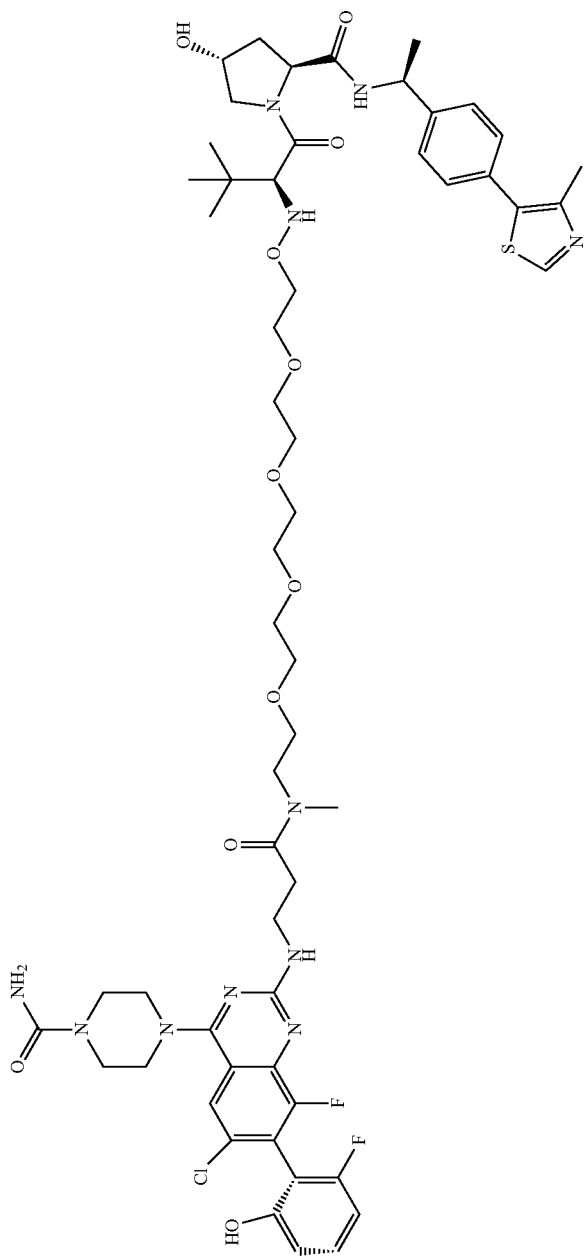

TABLE 8-continued
Compounds Prepared by Schemes 3-6
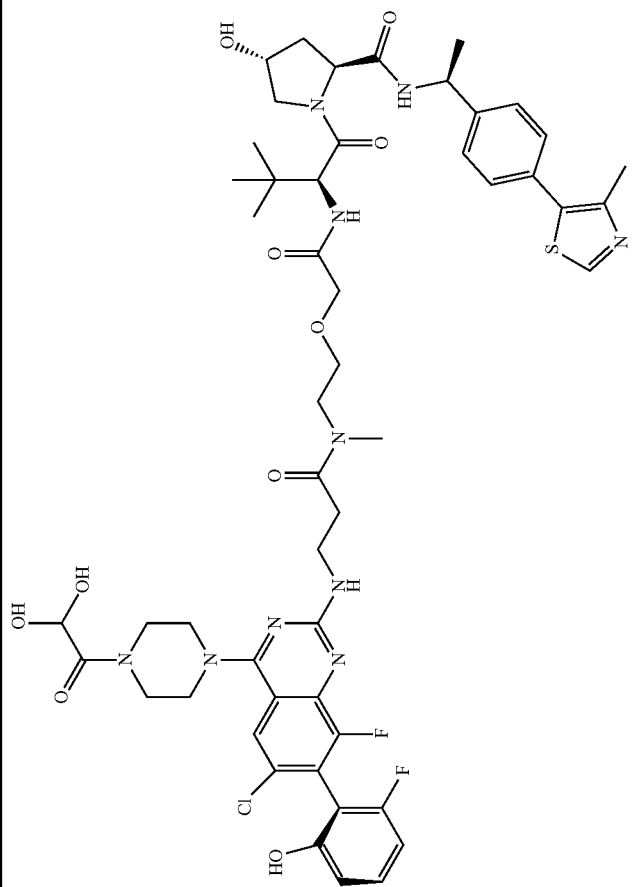
234

TABLE 8-continued
Compounds Prepared by Schemes 3-6
235
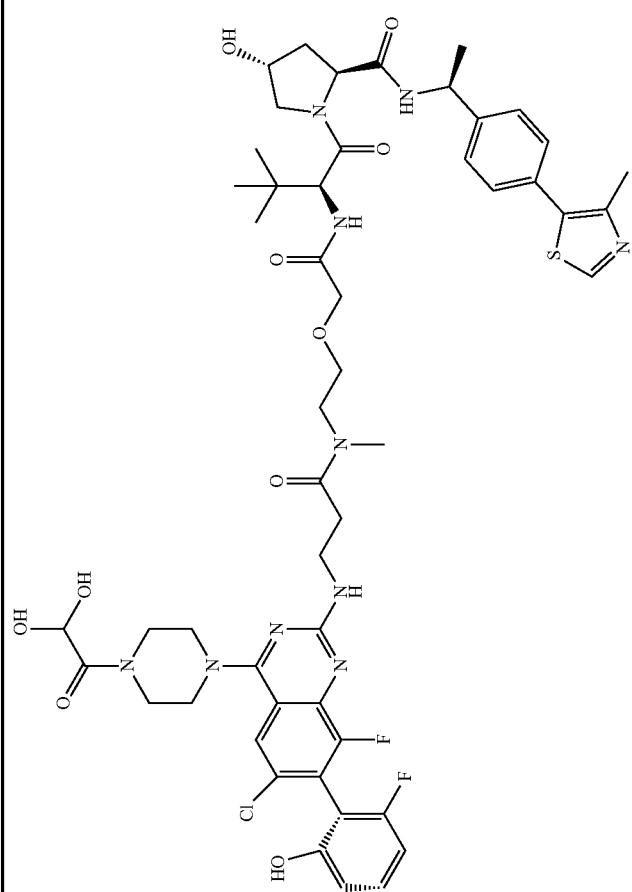

TABLE 8-continued
Compounds Prepared by Schemes 3-6
| 1451 | 1452 |
|---|---|
| 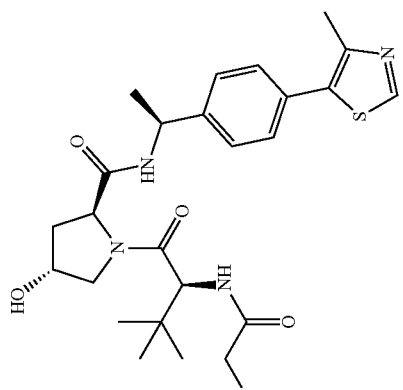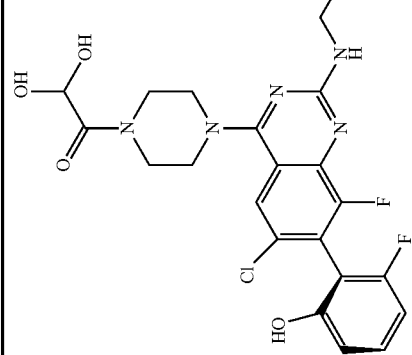 | 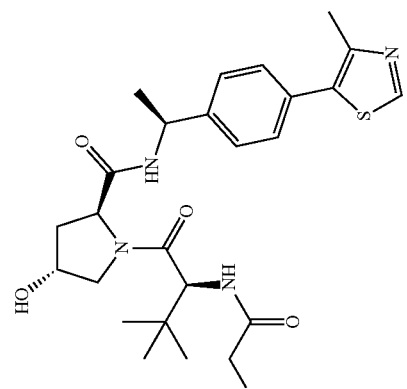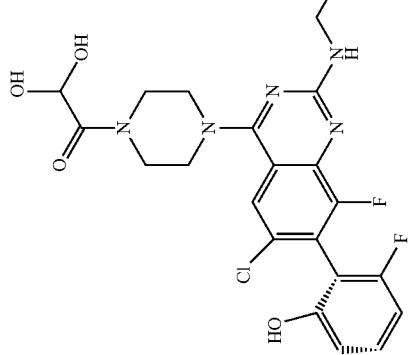 |

TABLE 8-continued
Compounds Prepared by Schemes 3-6
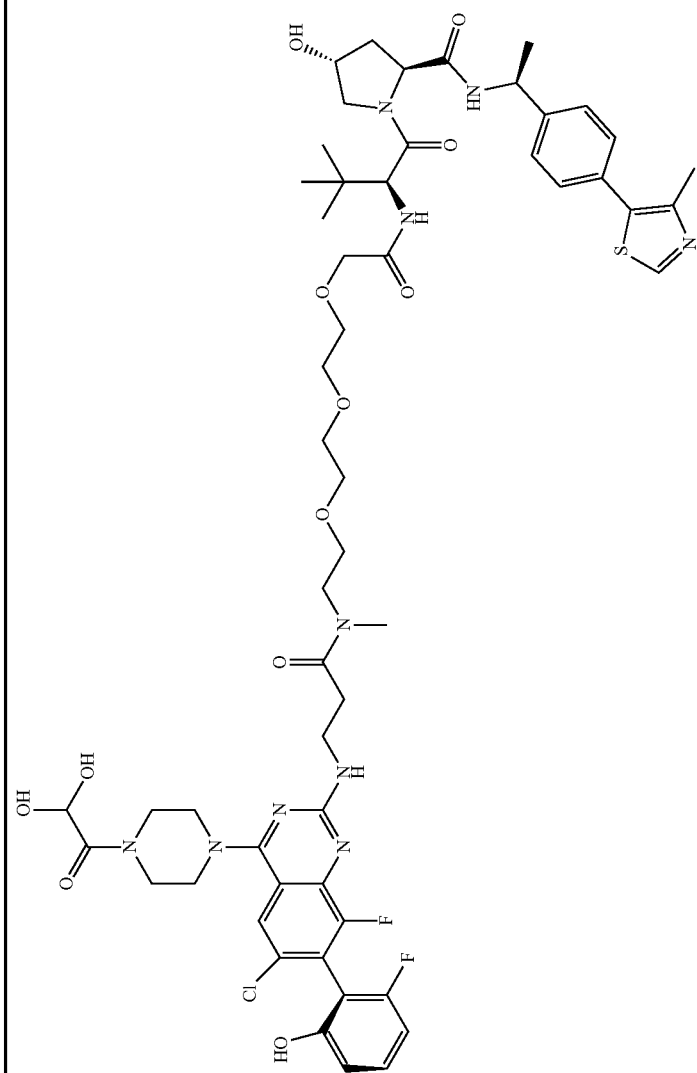
238

TABLE 8-continued
Compounds Prepared by Schemes 3-6
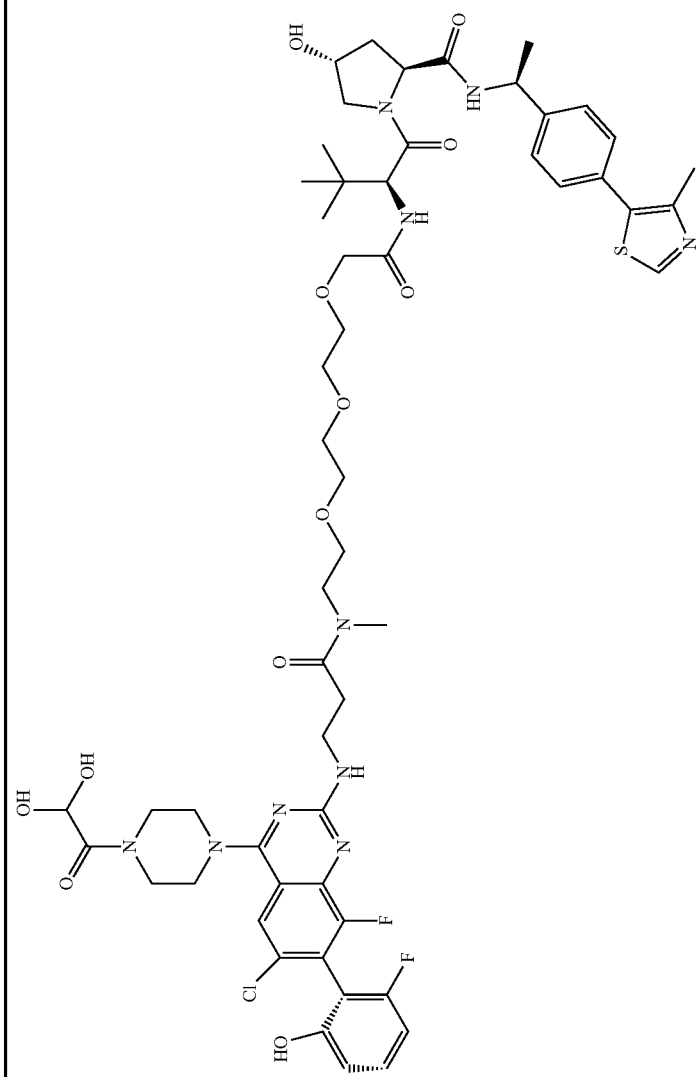
239

TABLE 8-continued
Compounds Prepared by Schemes 3-6
| 1457 | 1458 |
|---|---|
| 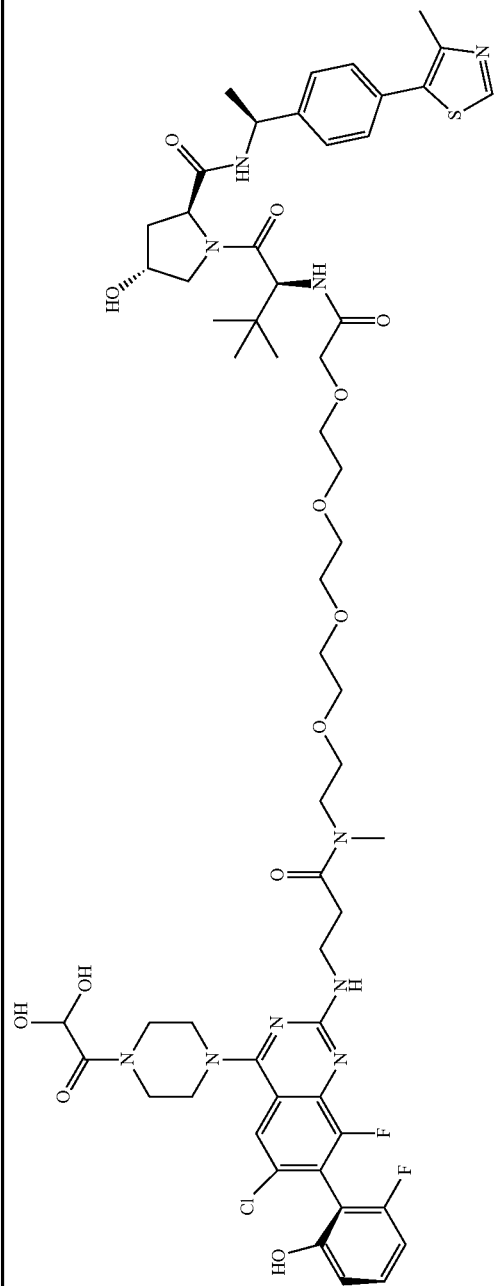 | 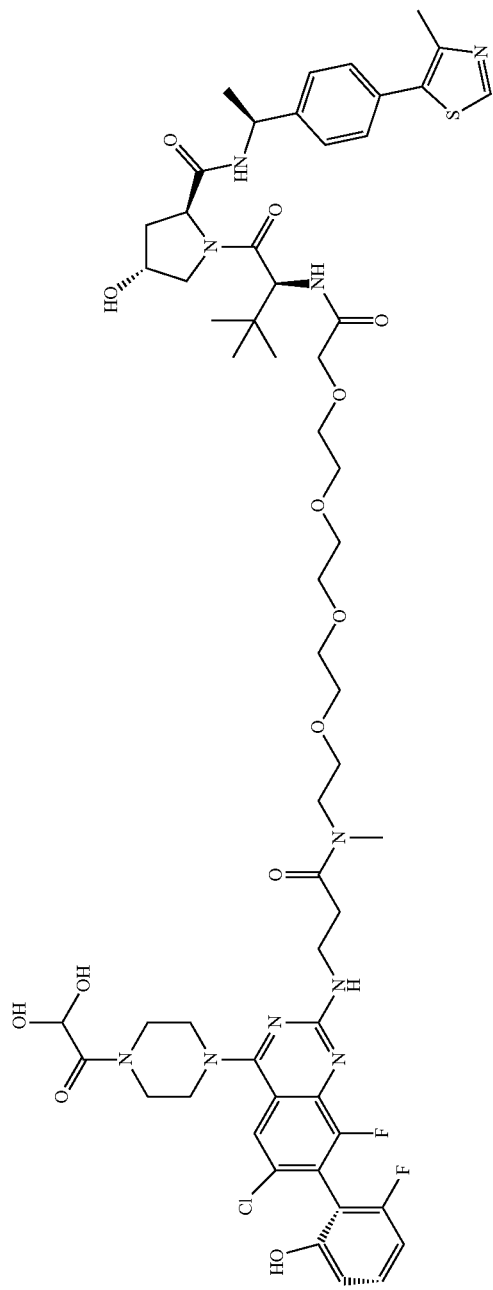 |
| 240 | 241 |

TABLE 8-continued
Compounds Prepared by Schemes 3-6
| 242 | 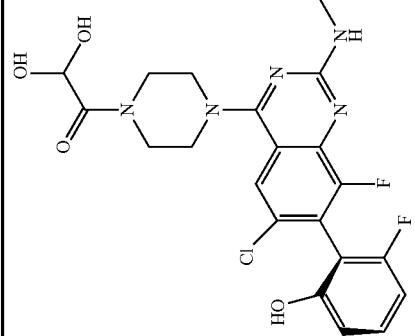 |
|---|---|

TABLE 8-continued
Compounds Prepared by Schemes 3-6
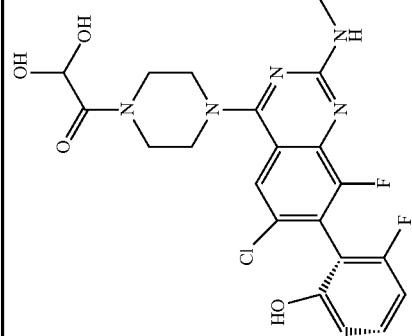
243

TABLE 8-continued
Compounds Prepared by Schemes 3-6
| 1463 | 1464 |
|---|---|
| 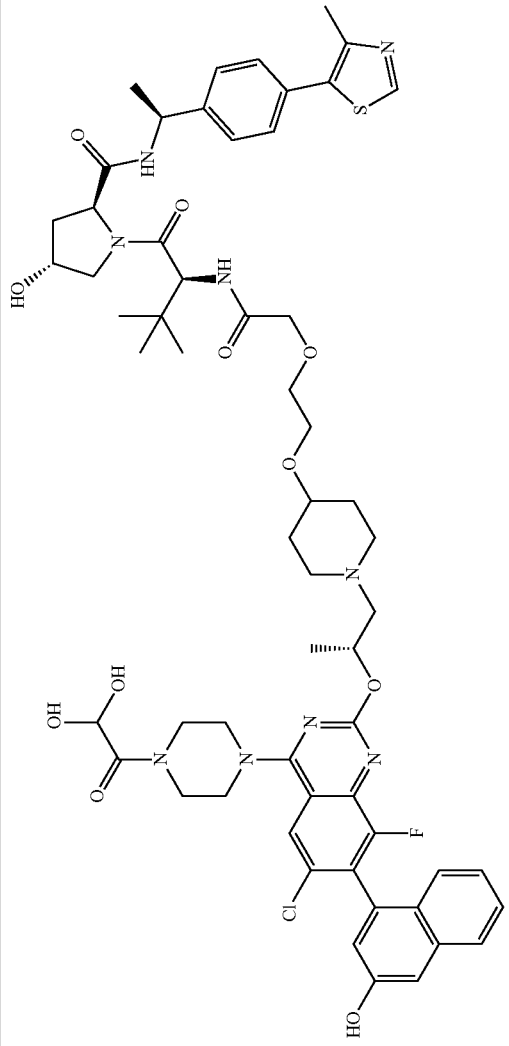 | 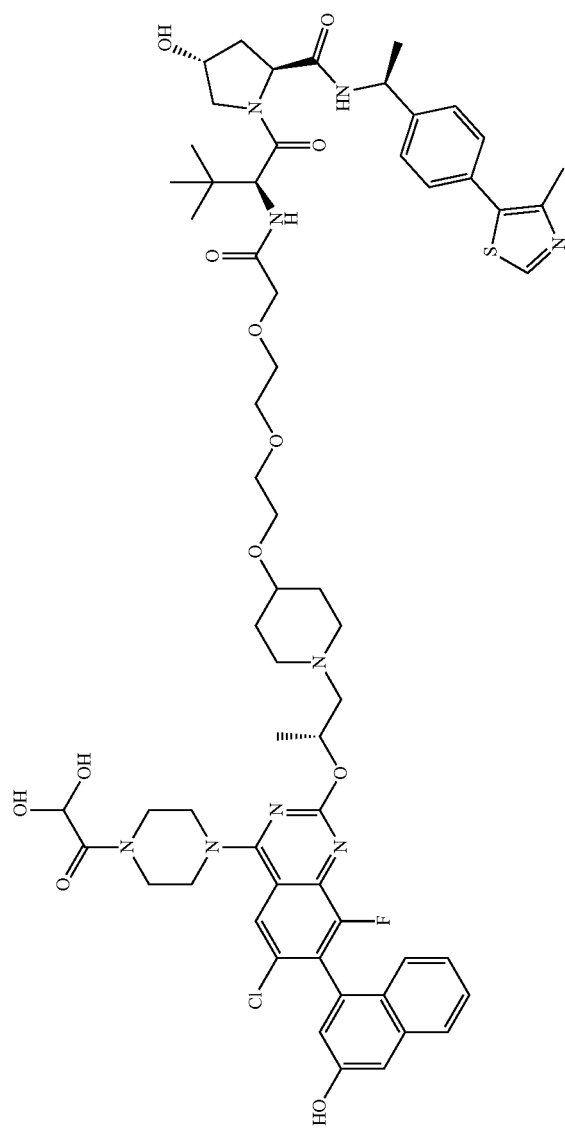 |

TABLE 8-continued
Compounds Prepared by Schemes 3-6
| 1465 | 1466 |
|---|---|
| 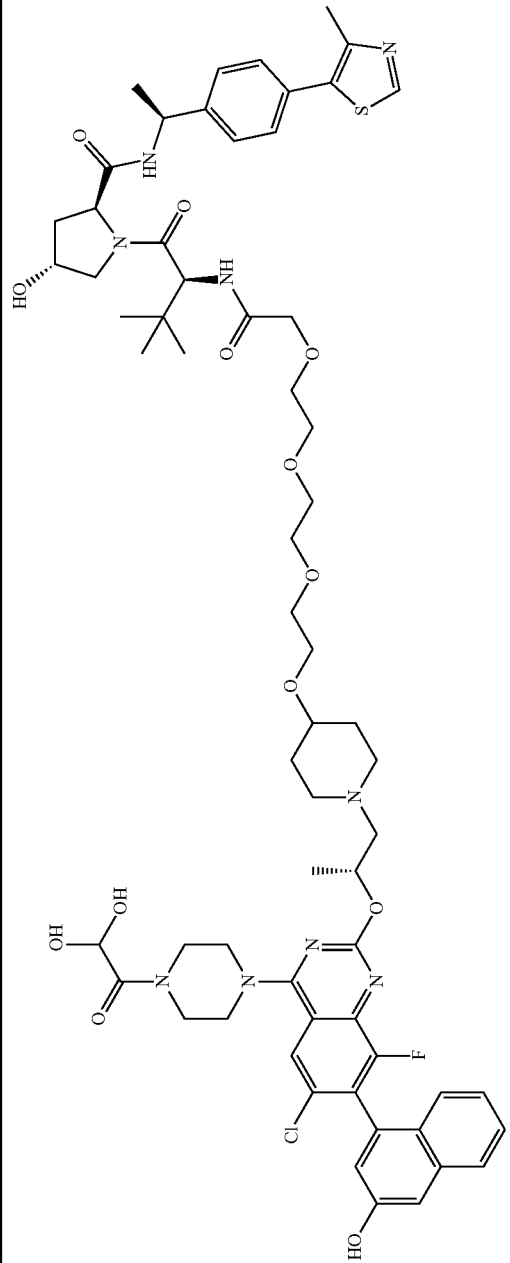 | 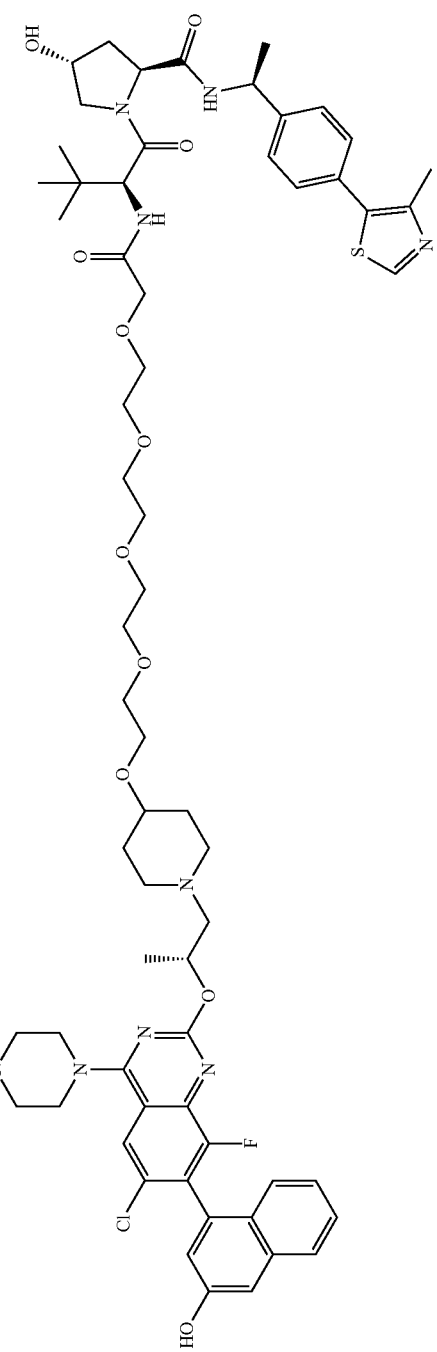 |

TABLE 8-continued
Compounds Prepared by Schemes 3-6
| 1467 | 1468 |
|---|---|
| 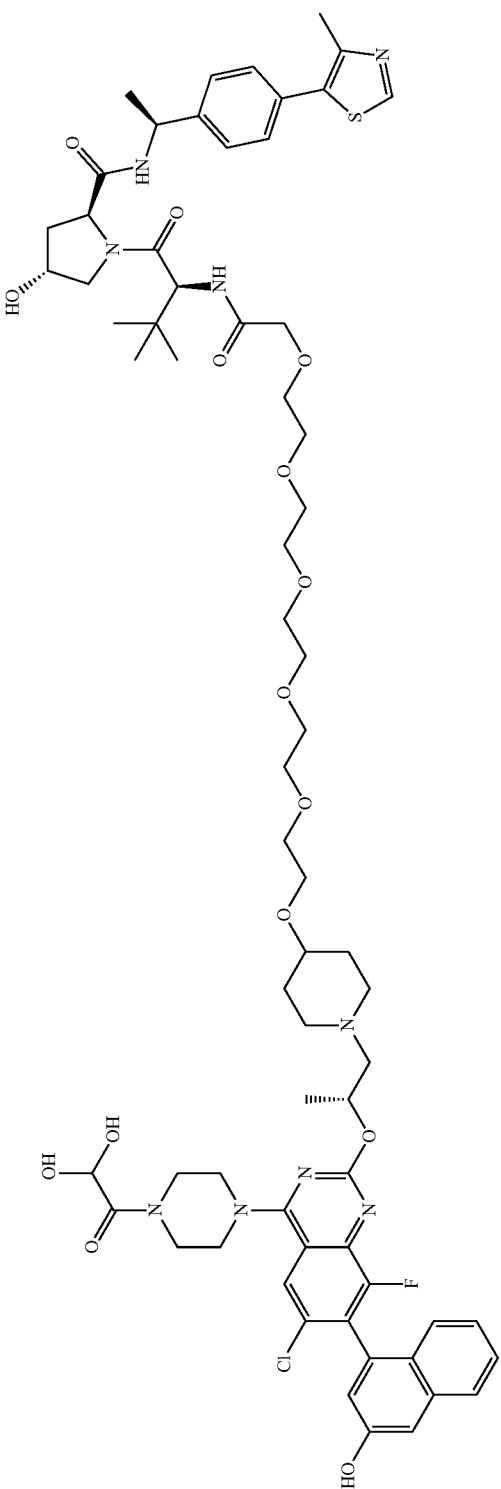 | 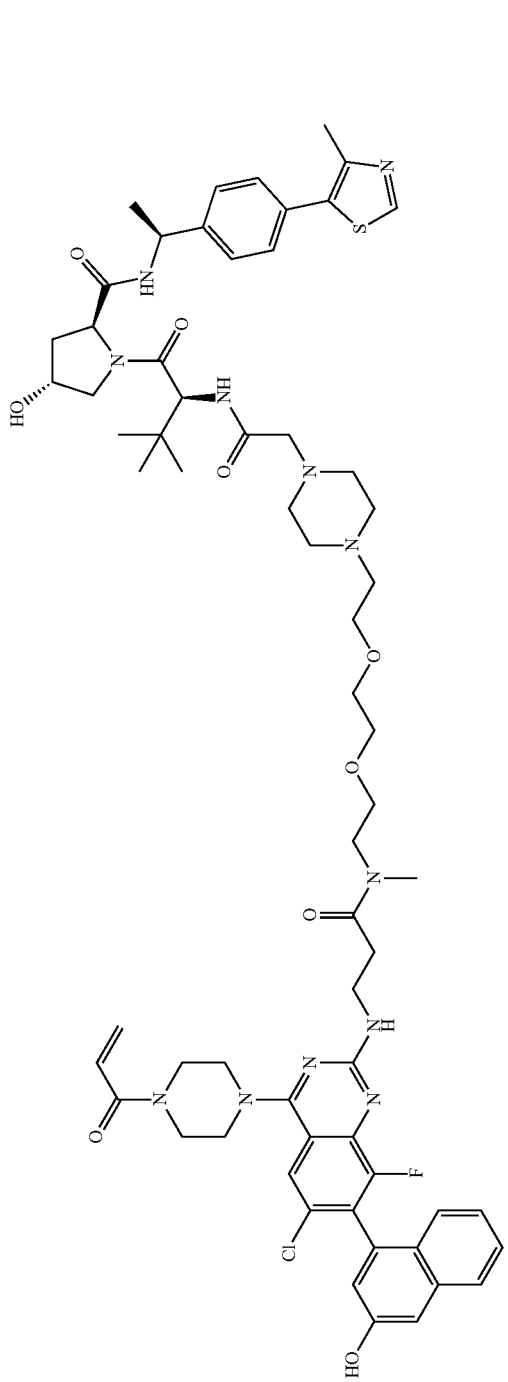 |
| 248 | 249 |

TABLE 8-continued
Compounds Prepared by Schemes 3-6
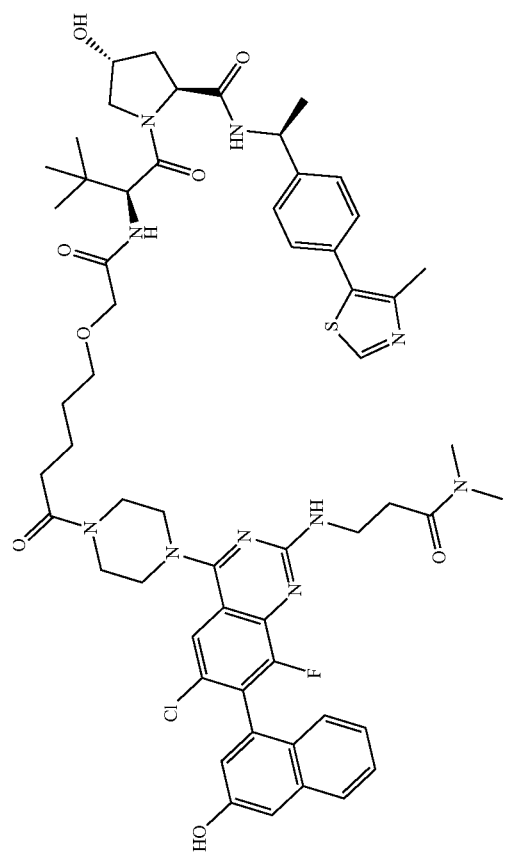

TABLE 8-continued
Compounds Prepared by Schemes 3-6
| 1471 | 1472 |
|---|---|
| 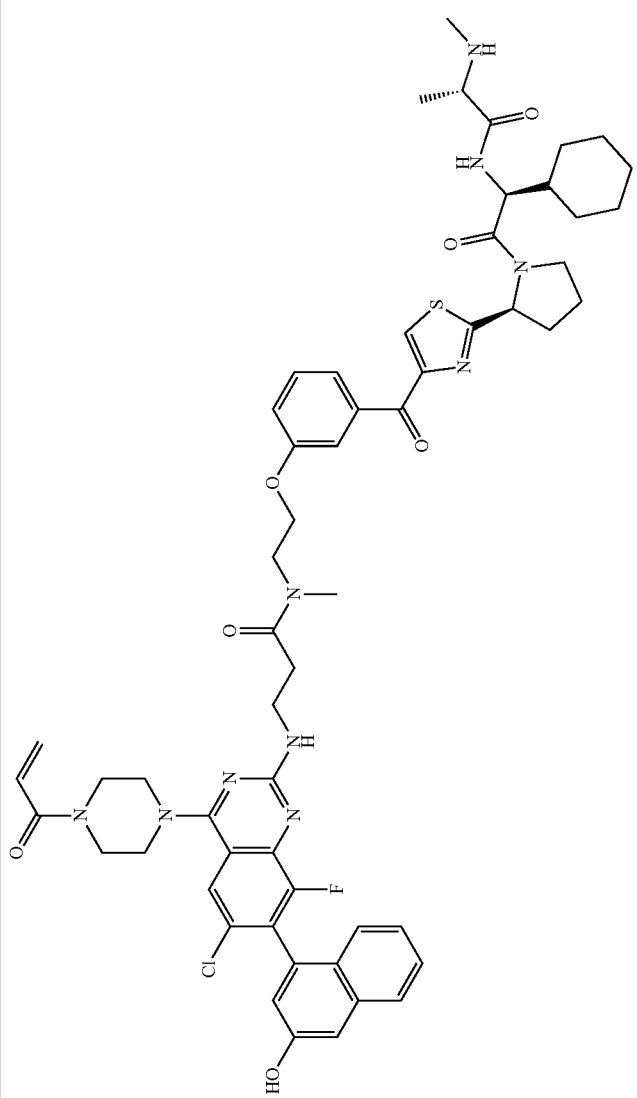 | 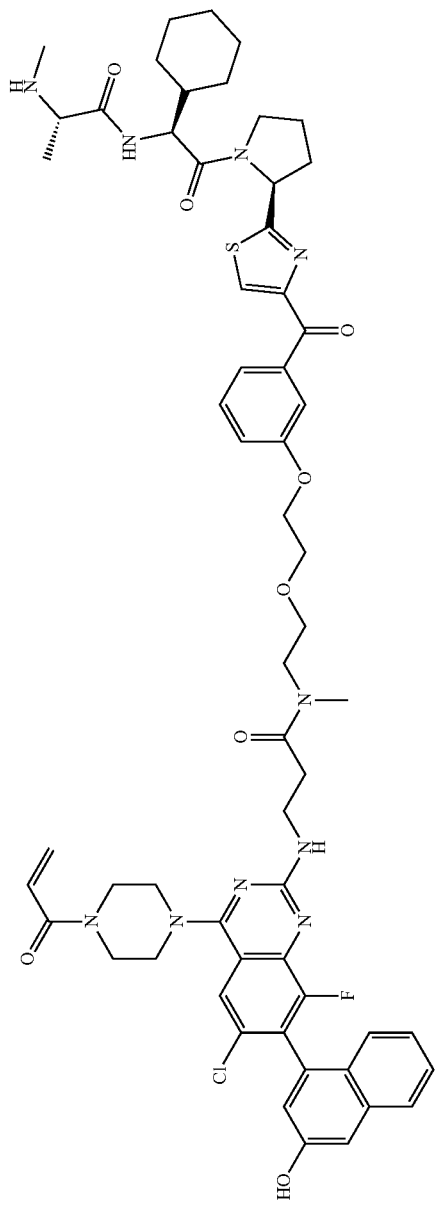 |

TABLE 8-continued
Compounds Prepared by Schemes 3-6
| 1473 | 1474 |
|---|---|
| 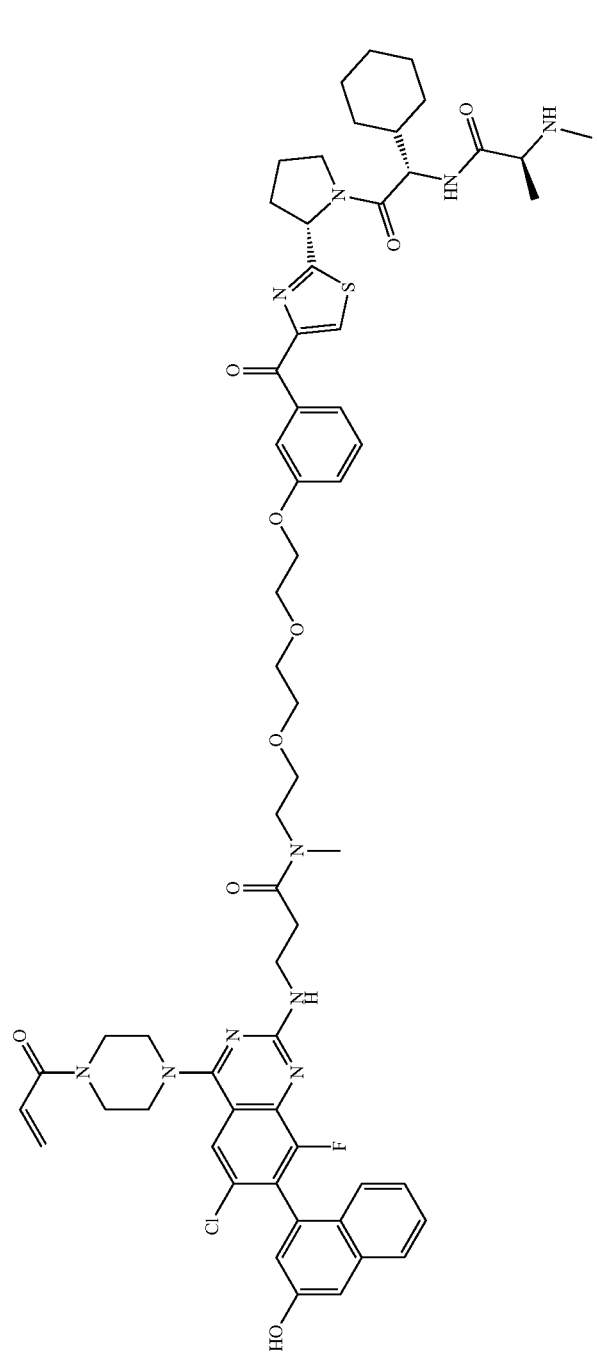 | 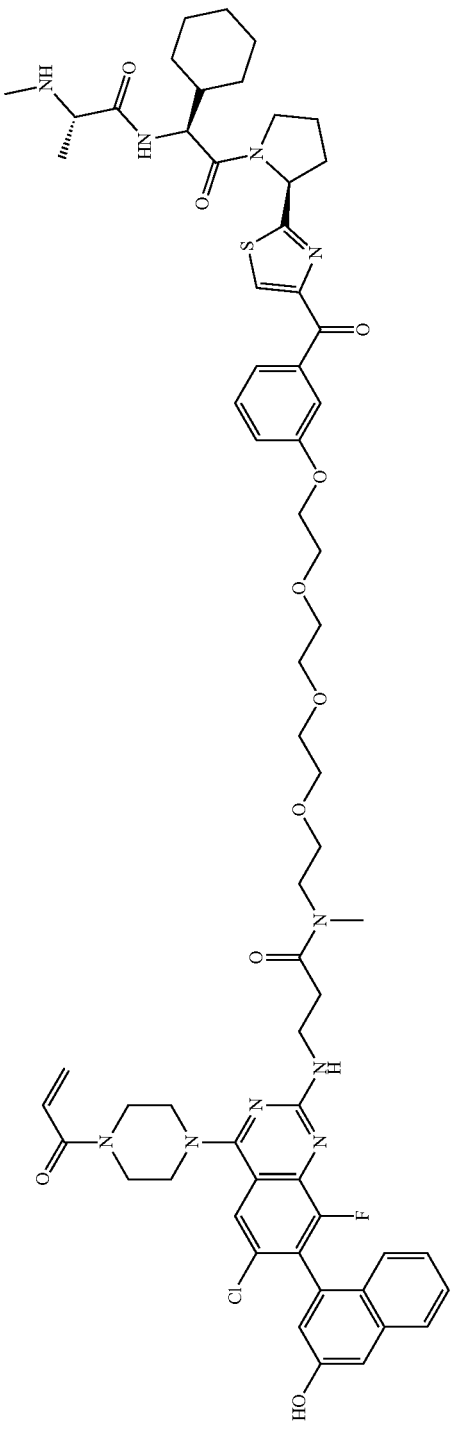 |

TABLE 8-continued
Compounds Prepared by Schemes 3-6
| 259 | 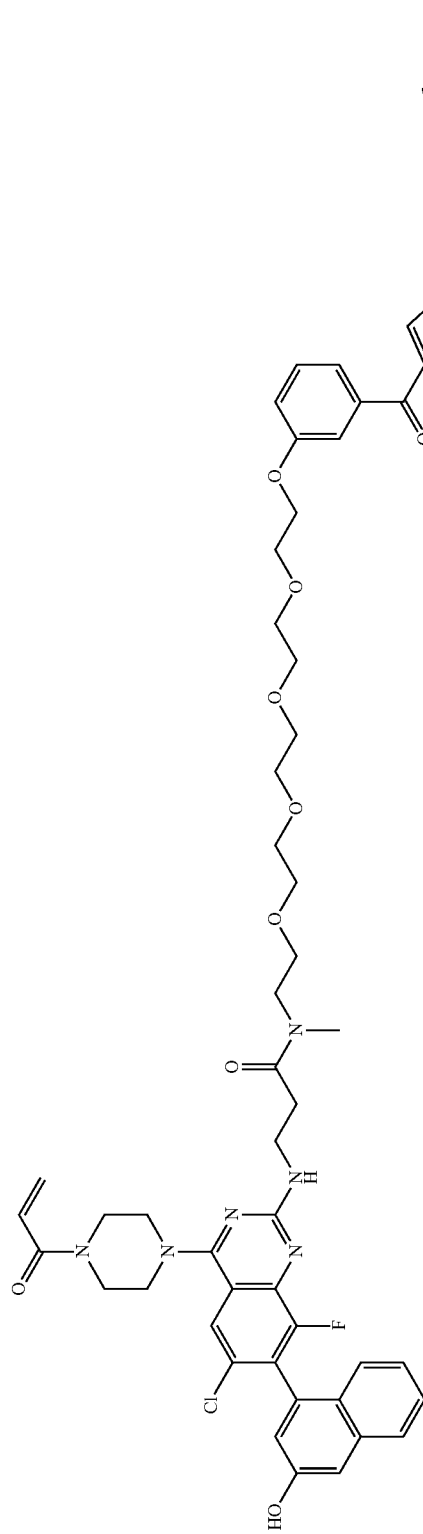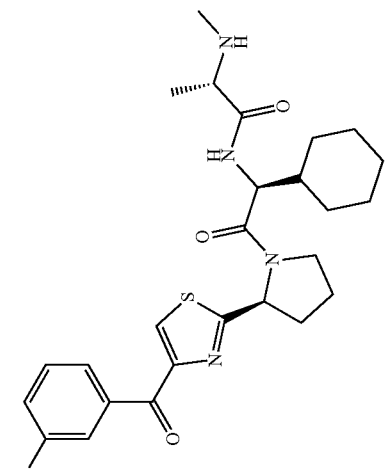 |
|---|---|

TABLE 8-continued
Compounds Prepared by Schemes 3-6
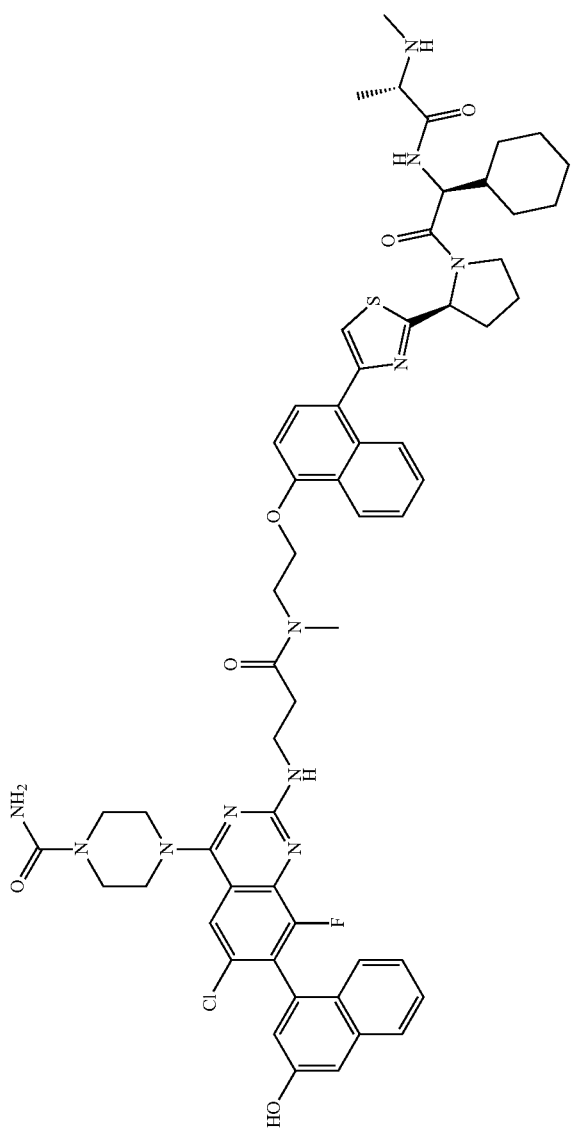
260

TABLE 8-continued
Compounds Prepared by Schemes 3-6
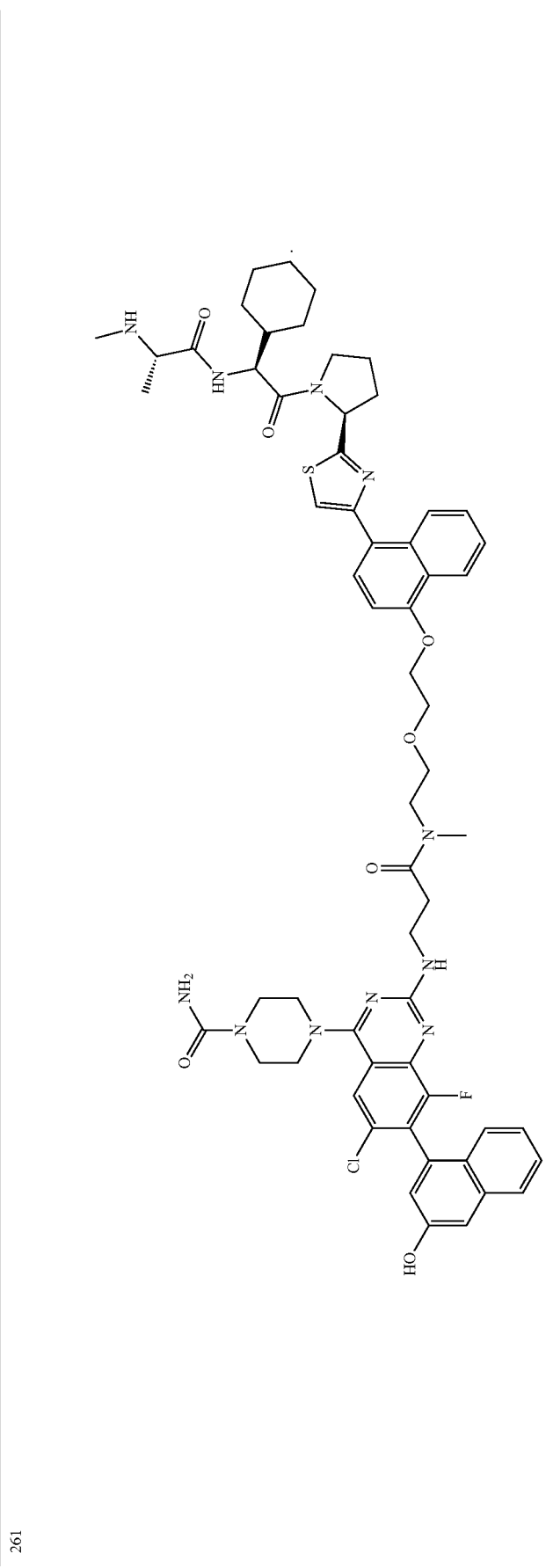

TABLE 8-continued
Compounds Prepared by Schemes 3-6
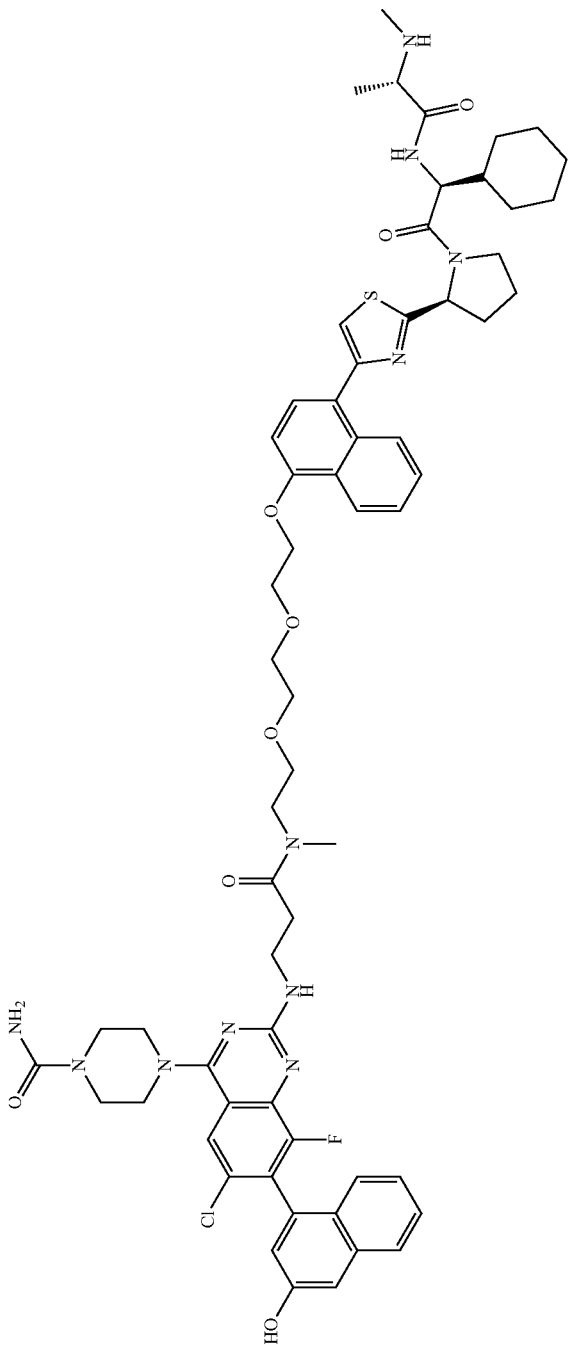

TABLE 8-continued
Compounds Prepared by Schemes 3-6
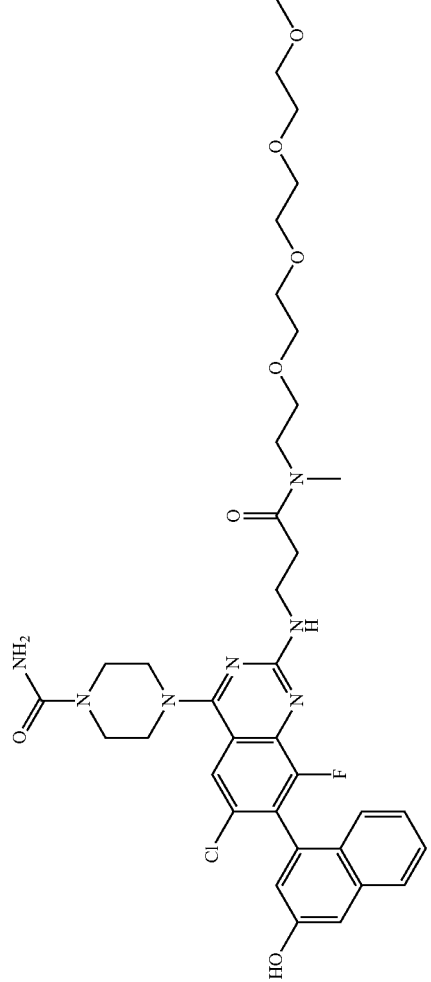

TABLE 8-continued
Compounds Prepared by Schemes 3-6
264
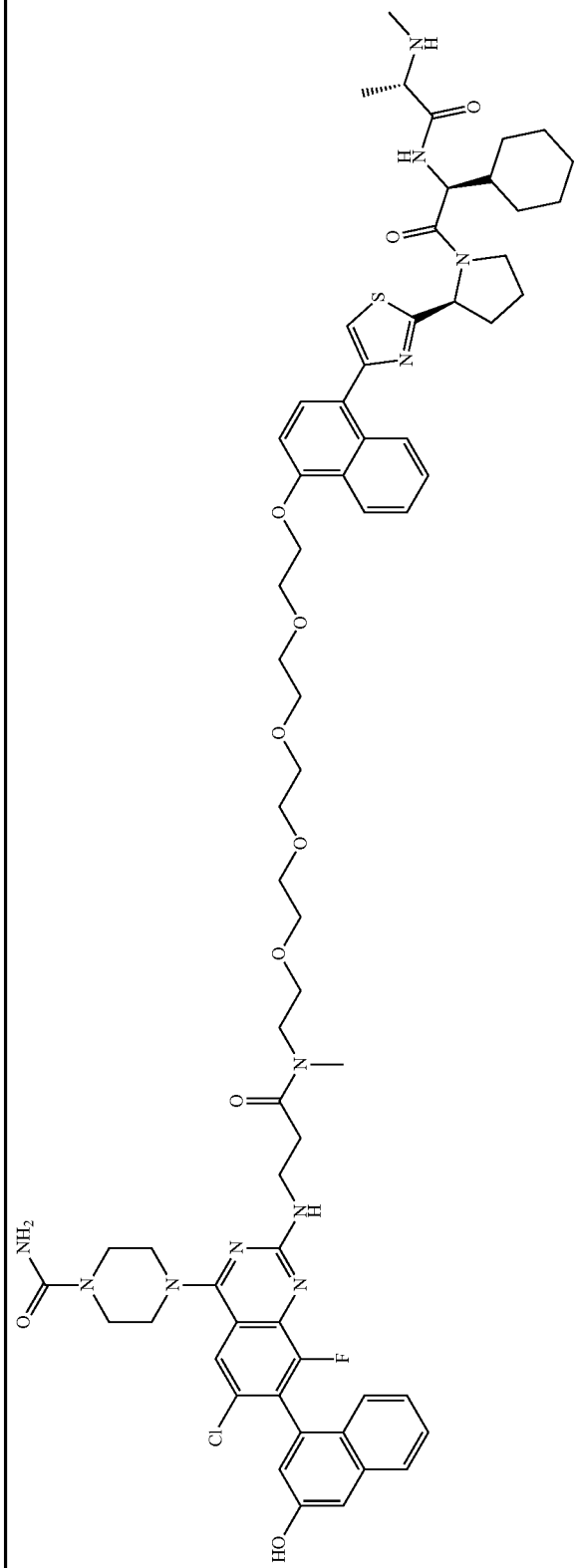

TABLE 8-continued
Compounds Prepared by Schemes 3-6
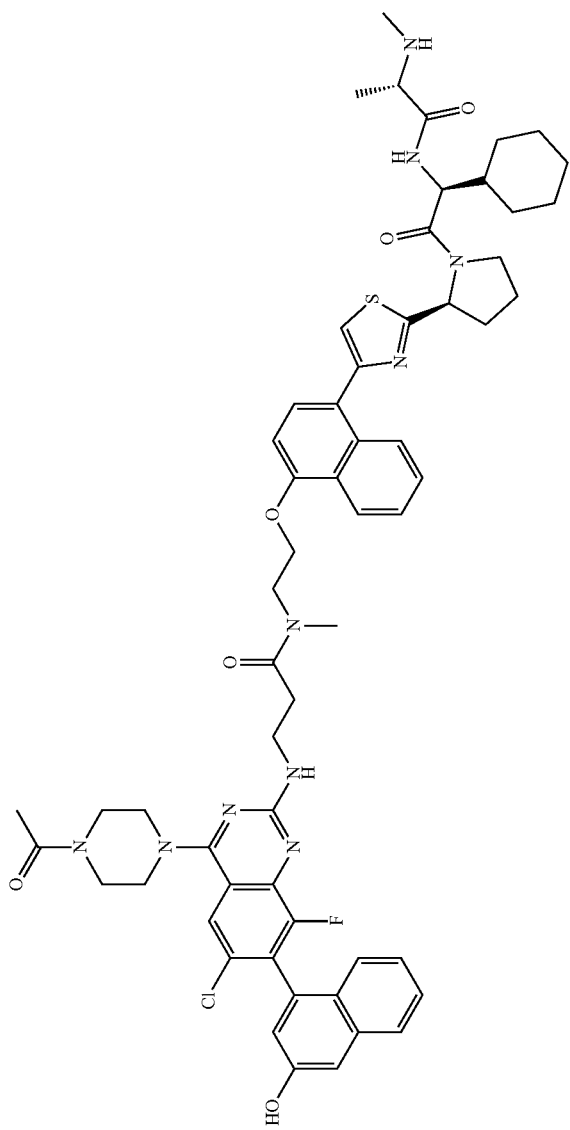

TABLE 8-continued
Compounds Prepared by Schemes 3-6
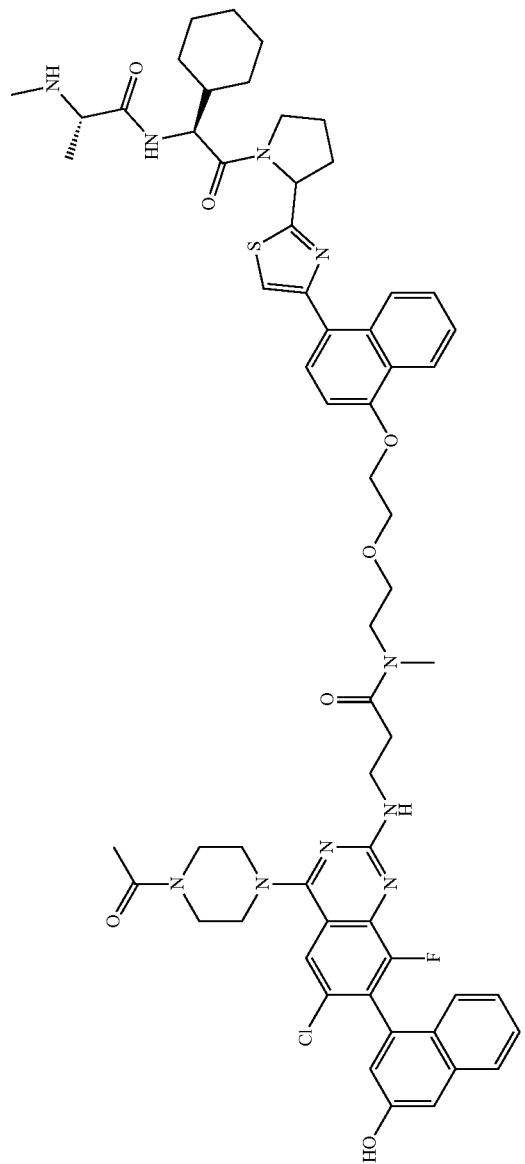

TABLE 8-continued
Compounds Prepared by Schemes 3-6
| 1491 | 1492 |
|---|---|
| 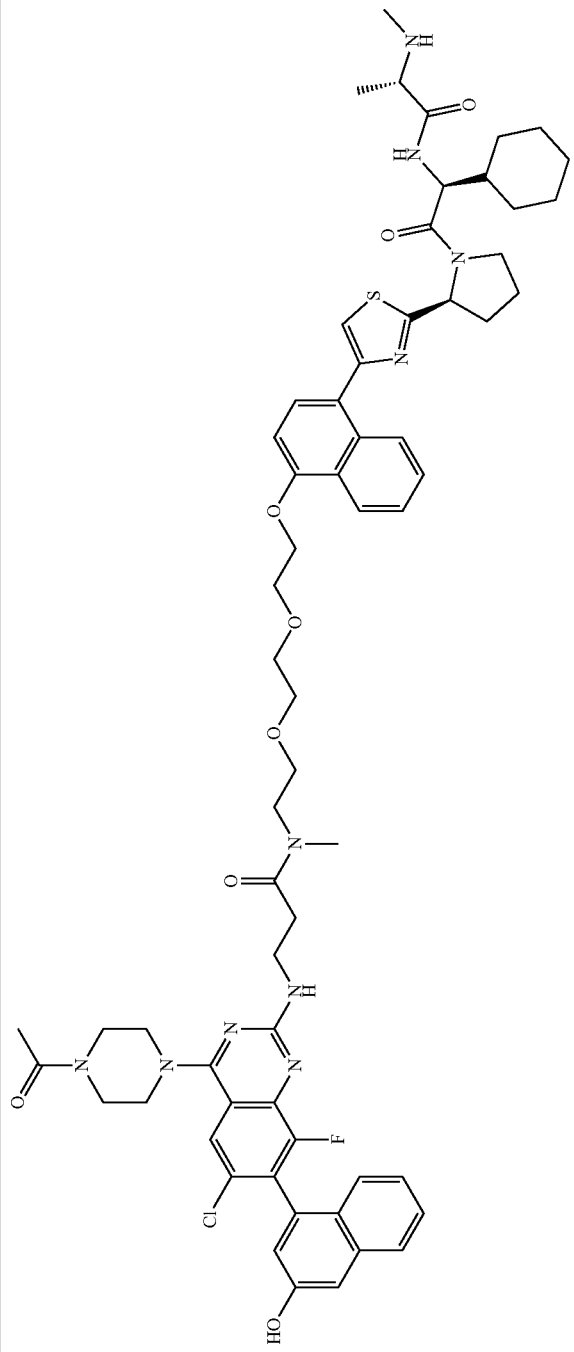 | 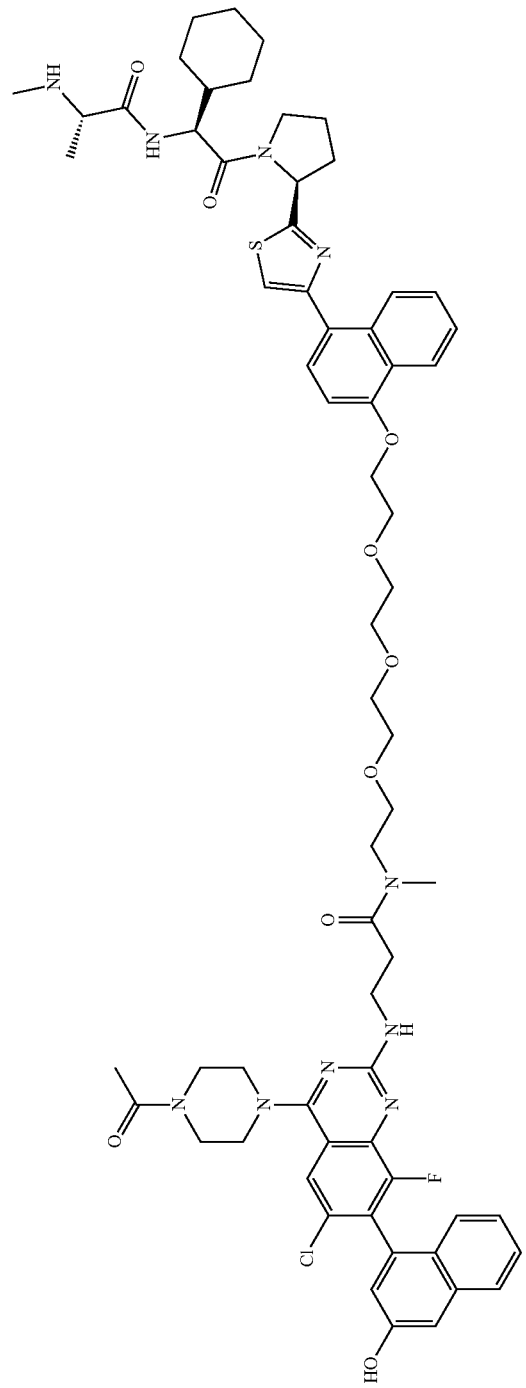 |

TABLE 8-continued
Compounds Prepared by Schemes 3-6
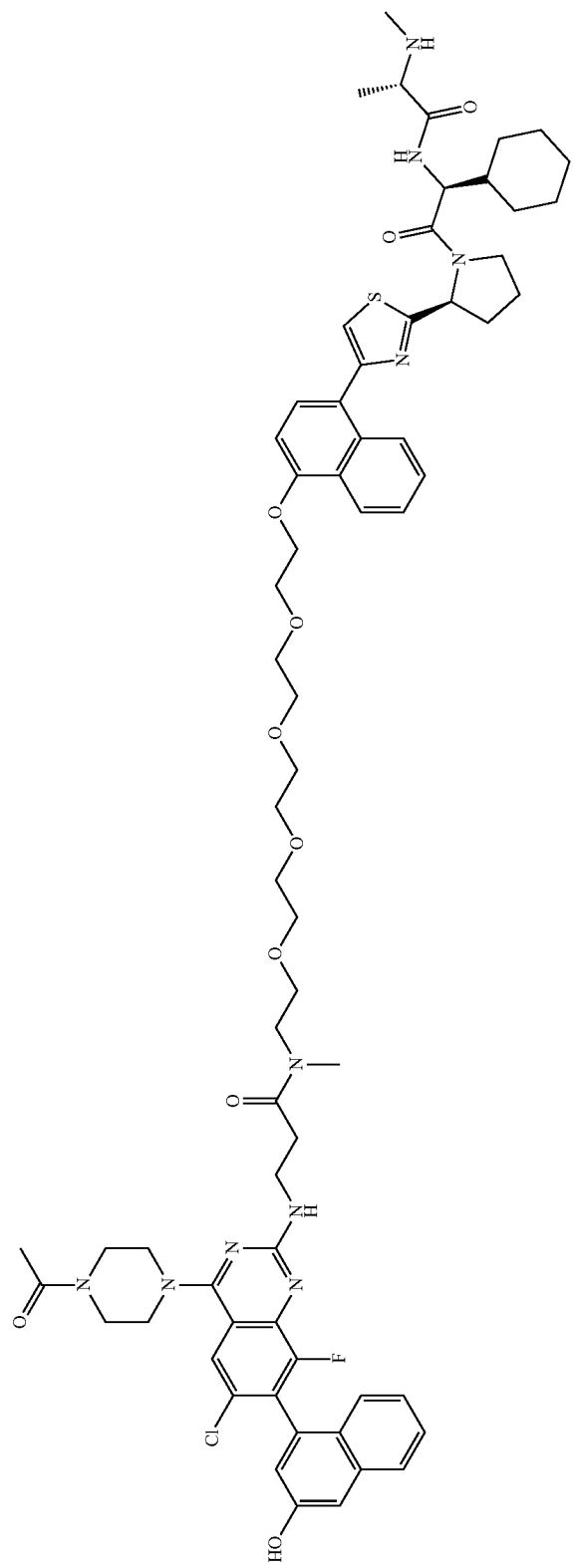

TABLE 8-continued
Compounds Prepared by Schemes 3-6
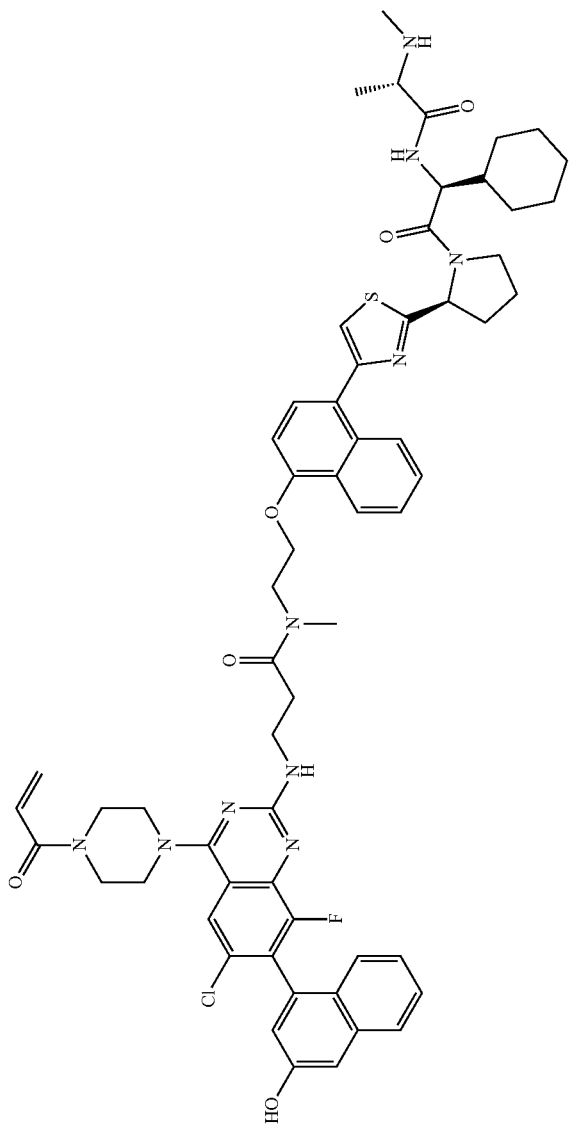

TABLE 8-continued
Compounds Prepared by Schemes 3-6
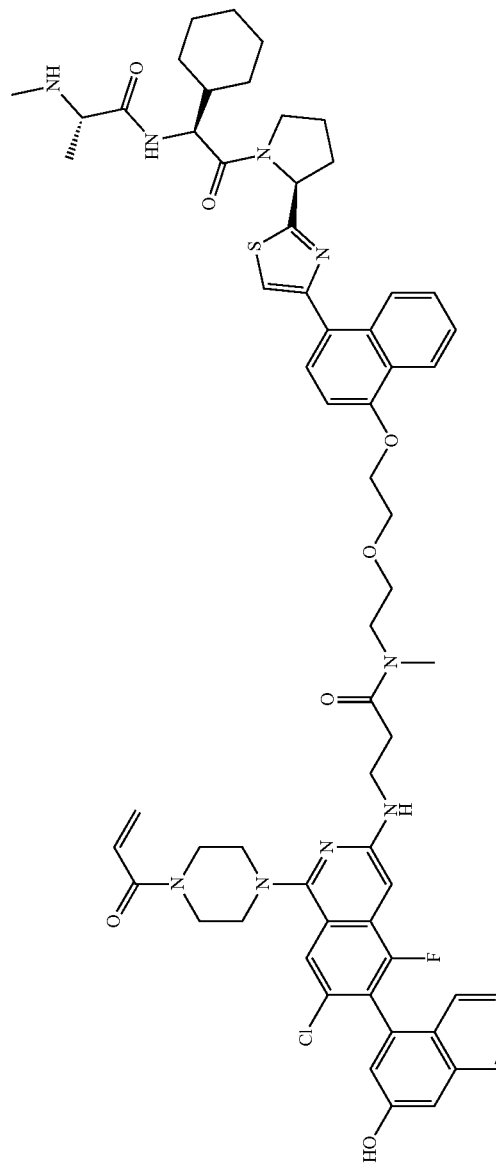

TABLE 8-continued
Compounds Prepared by Schemes 3-6
272
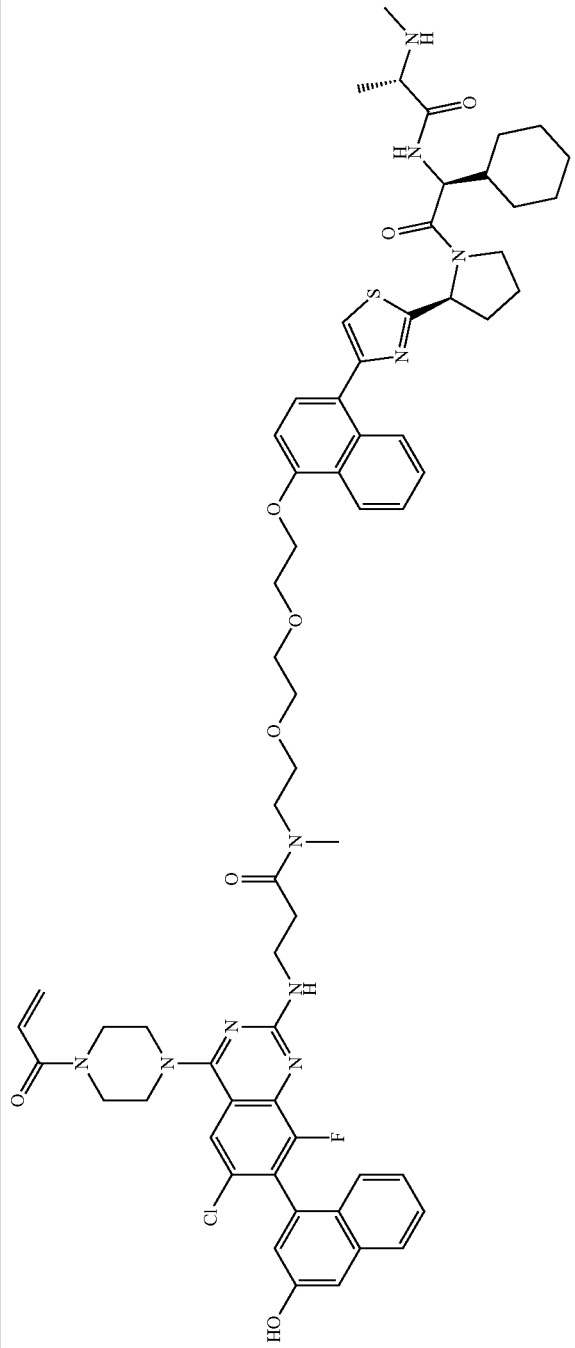

TABLE 8-continued
Compounds Prepared by Schemes 3-6
1501
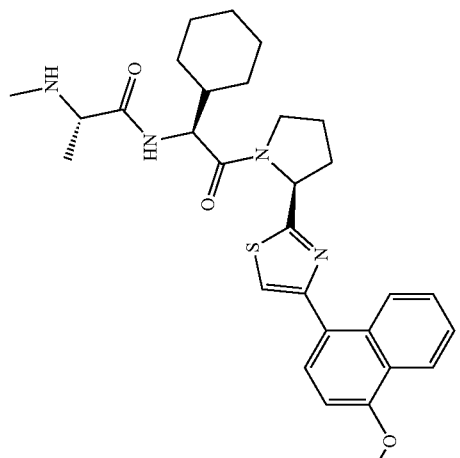
1502
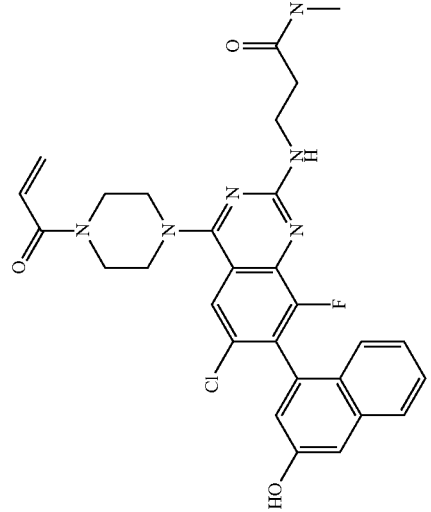

TABLE 8-continued
Compounds Prepared by Schemes 3-6
| 1503 | 1504 |
|---|---|
| 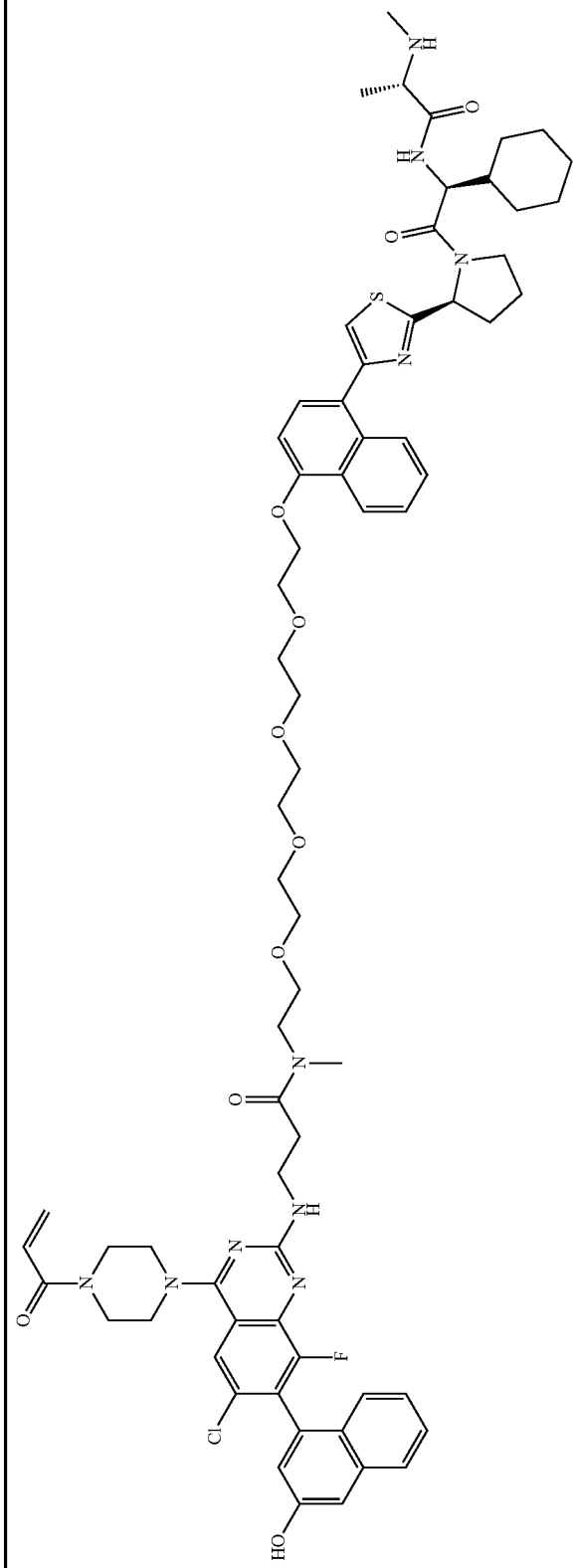 | |

TABLE 8-continued
Compounds Prepared by Schemes 3-6
1505
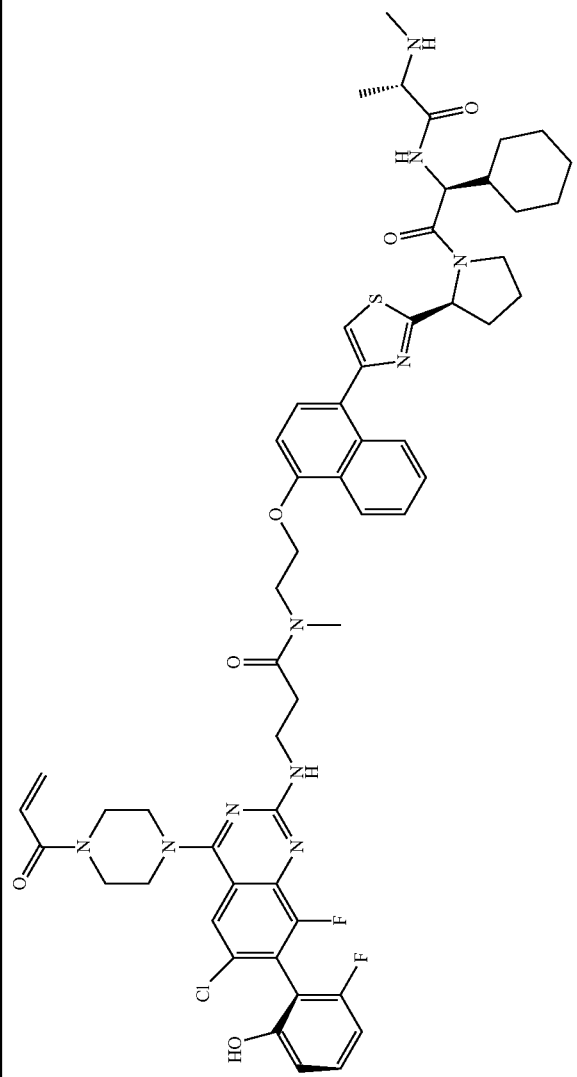
1506
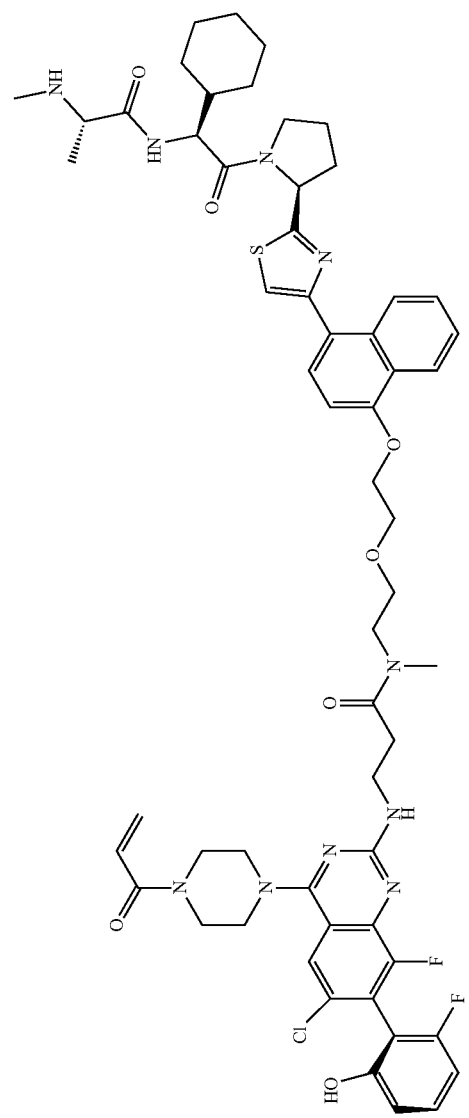

TABLE 8-continued
Compounds Prepared by Schemes 3-6
| 1507 | 1508 |
|---|---|
| 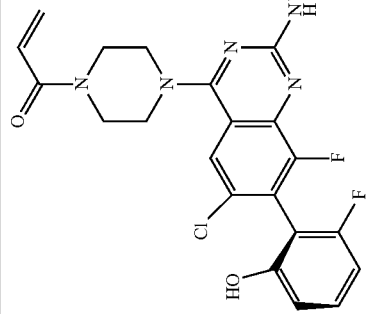 | 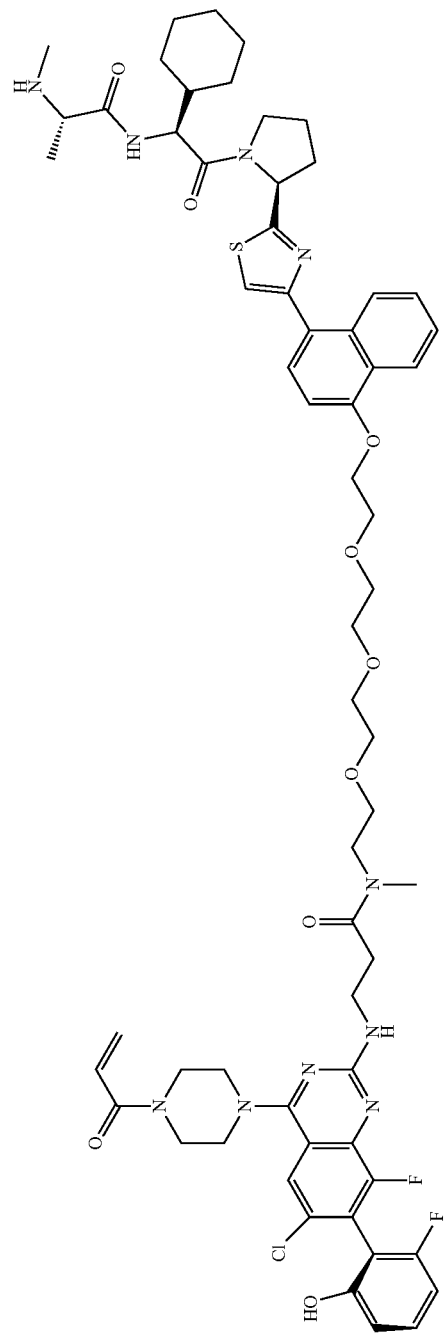 |

TABLE 8-continued
Compounds Prepared by Schemes 3-6
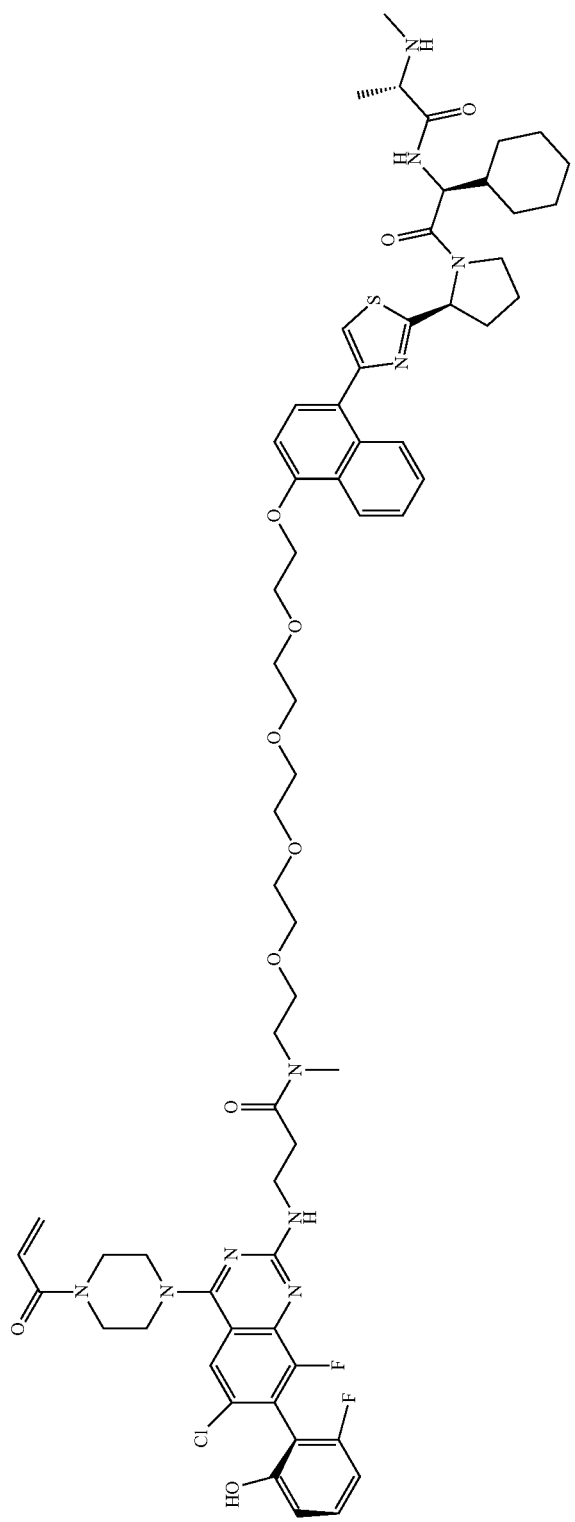
279

TABLE 8-continued
Compounds Prepared by Schemes 3-6
| 1511 | 1512 |
|---|---|
| 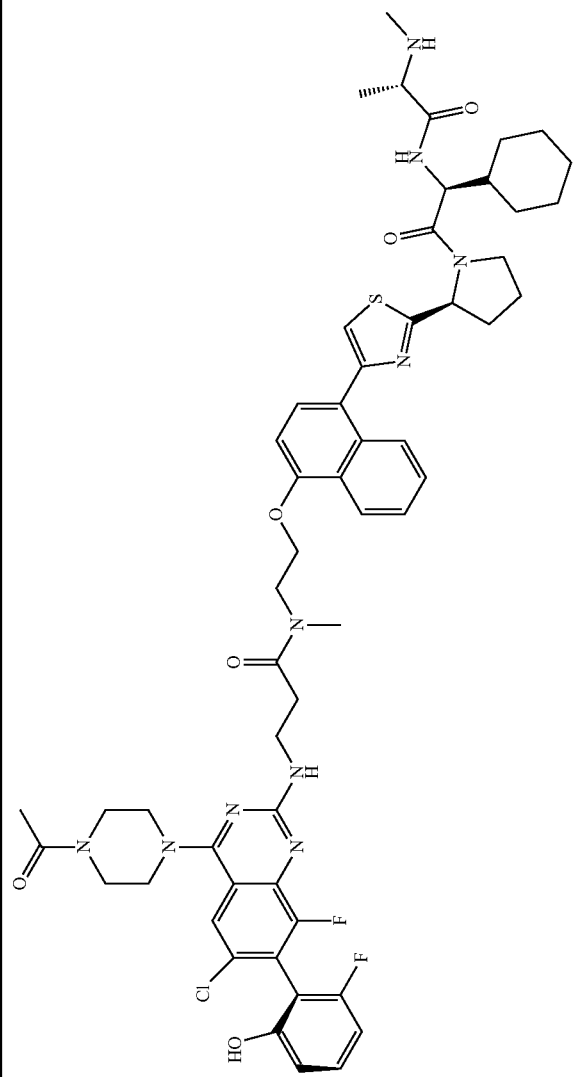 | 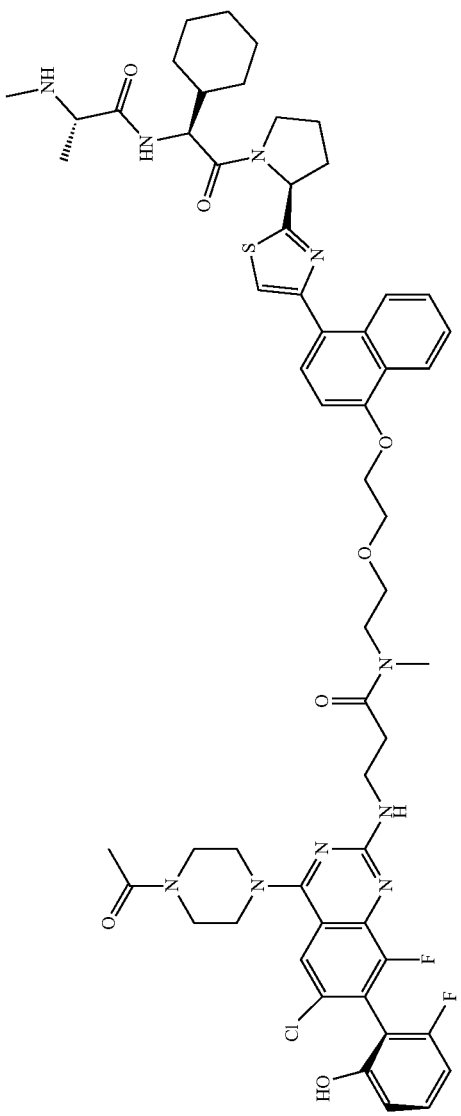 |

TABLE 8-continued
Compounds Prepared by Schemes 3-6
| 1513 | 1514 |
|---|---|
| 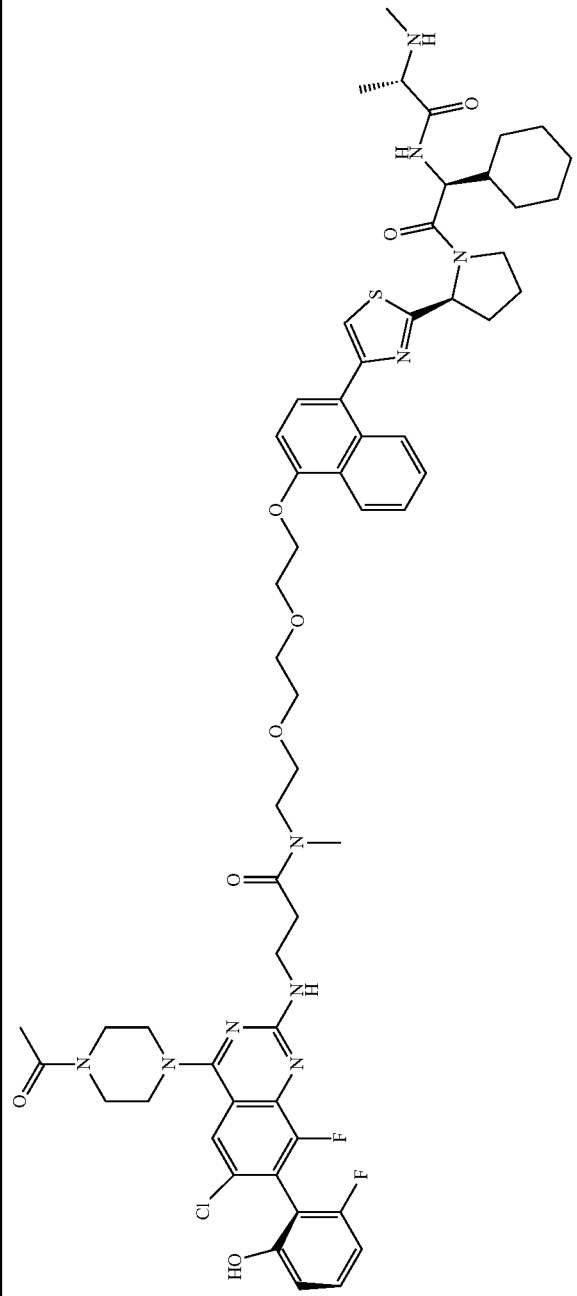 | 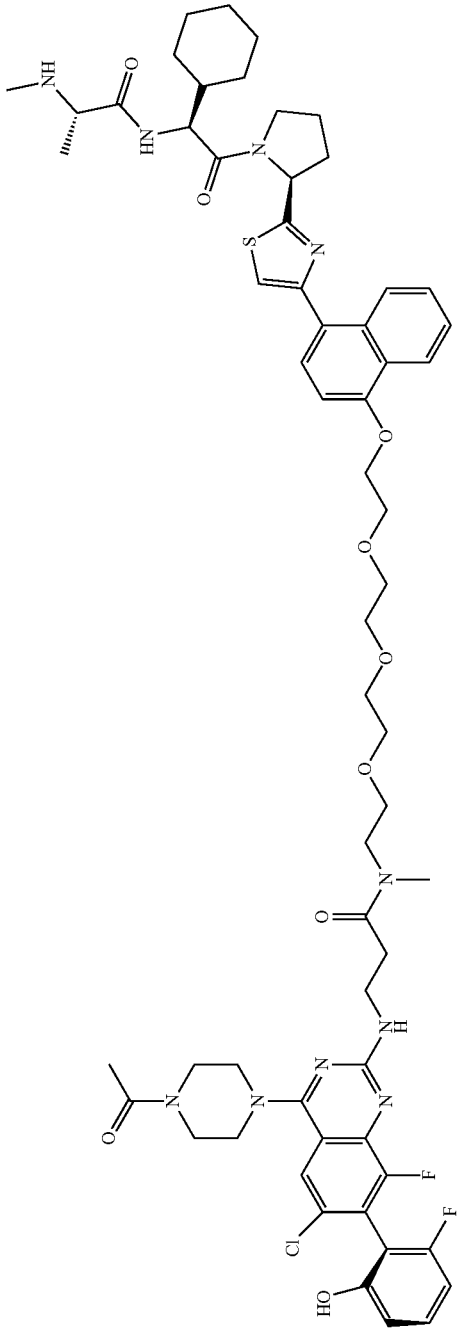 |

TABLE 8-continued
Compounds Prepared by Schemes 3-6
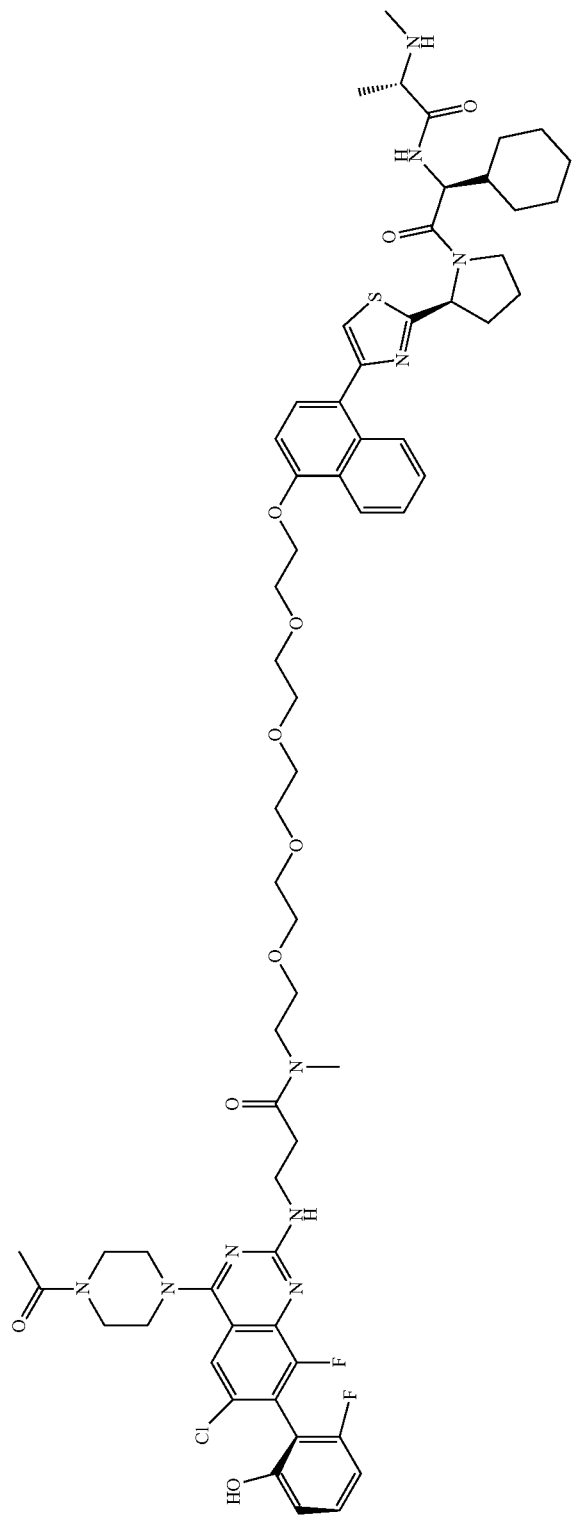

TABLE 8-continued
Compounds Prepared by Schemes 3-6
| 1517 | 1518 |
|---|---|
| 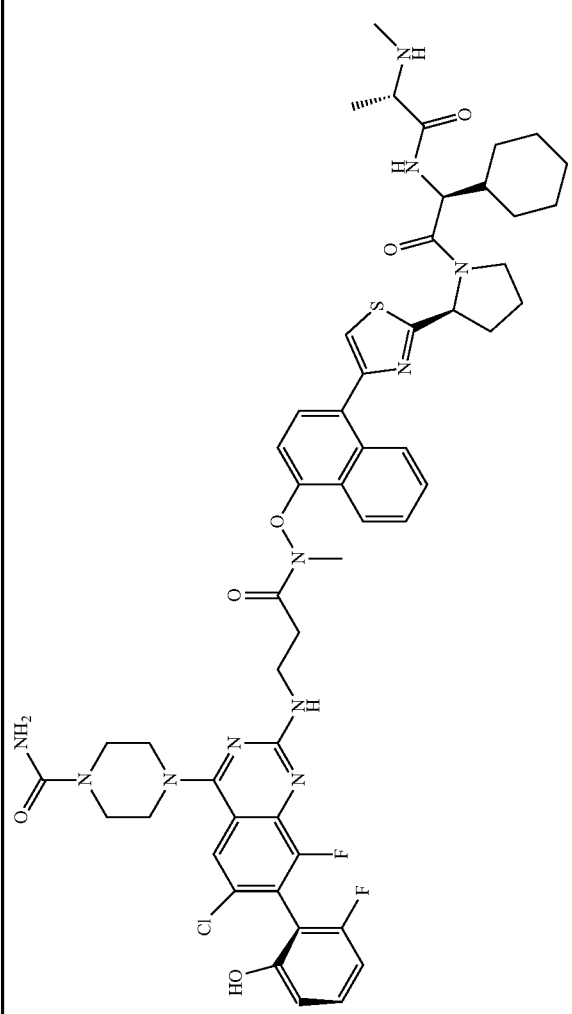 | 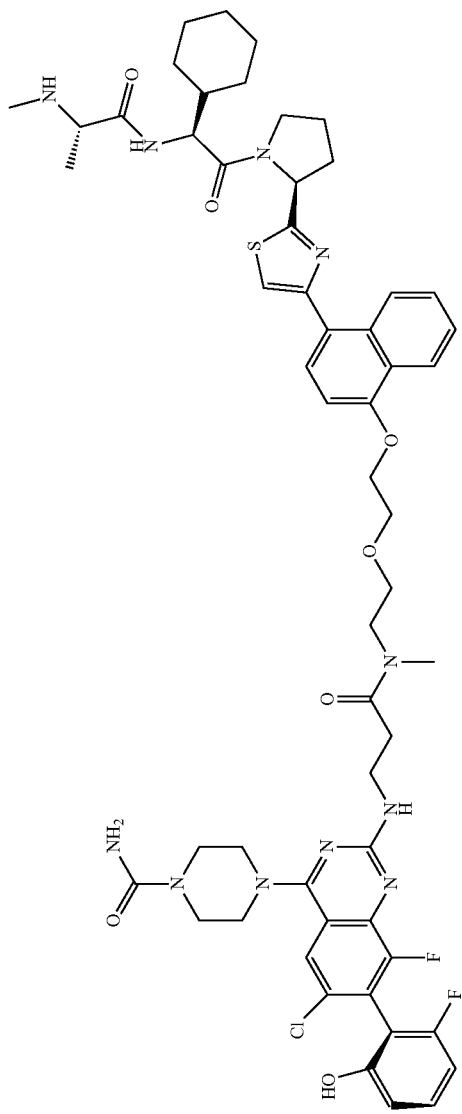 |

TABLE 8-continued
Compounds Prepared by Schemes 3-6
| 1519 | 1520 |
|---|---|
| 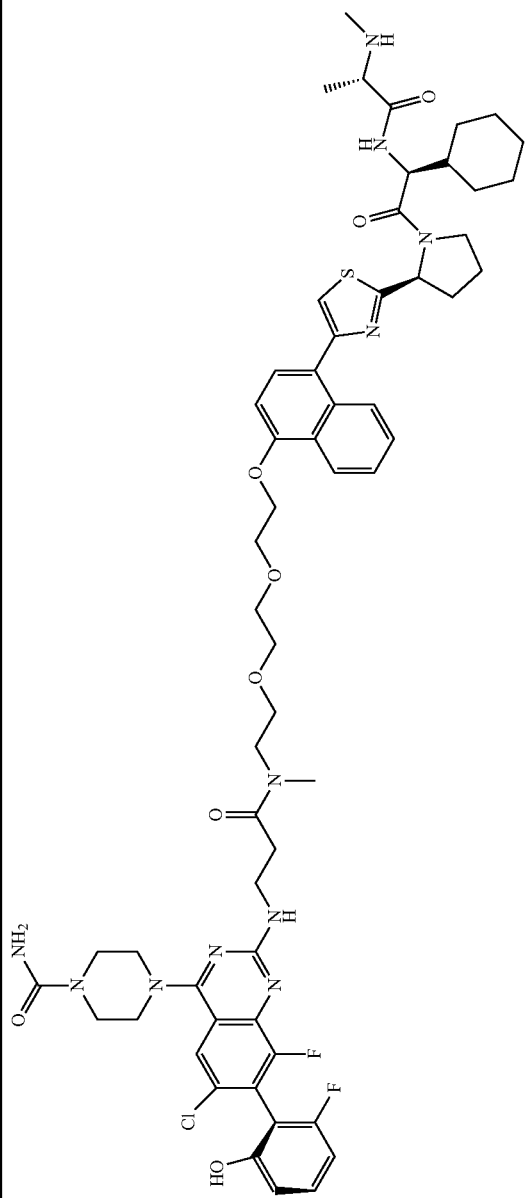 | 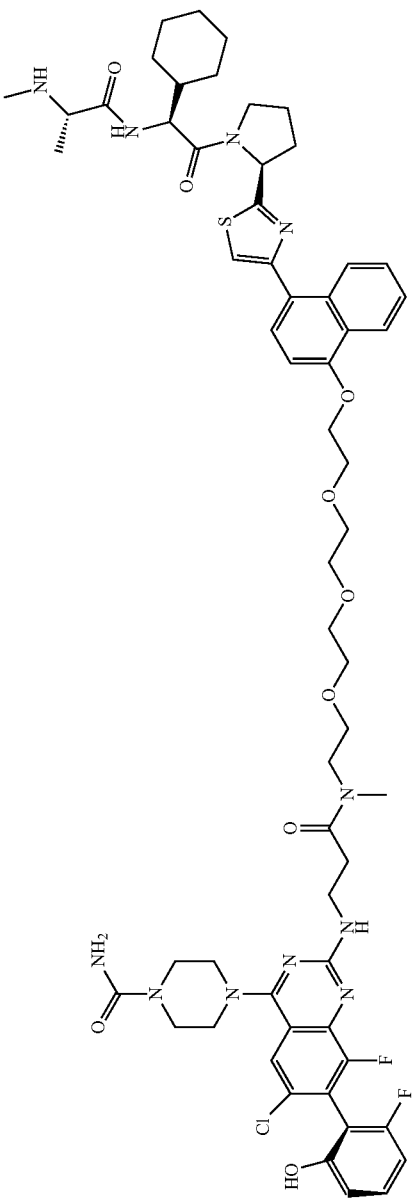 |

TABLE 8-continued
Compounds Prepared by Schemes 3-6
| 1521 | 1522 |
|---|---|
| 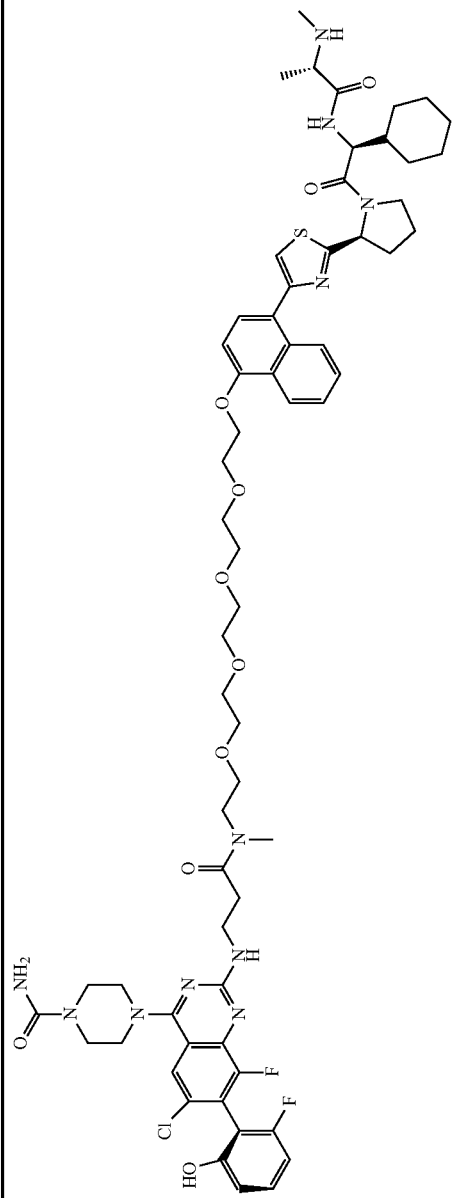 | 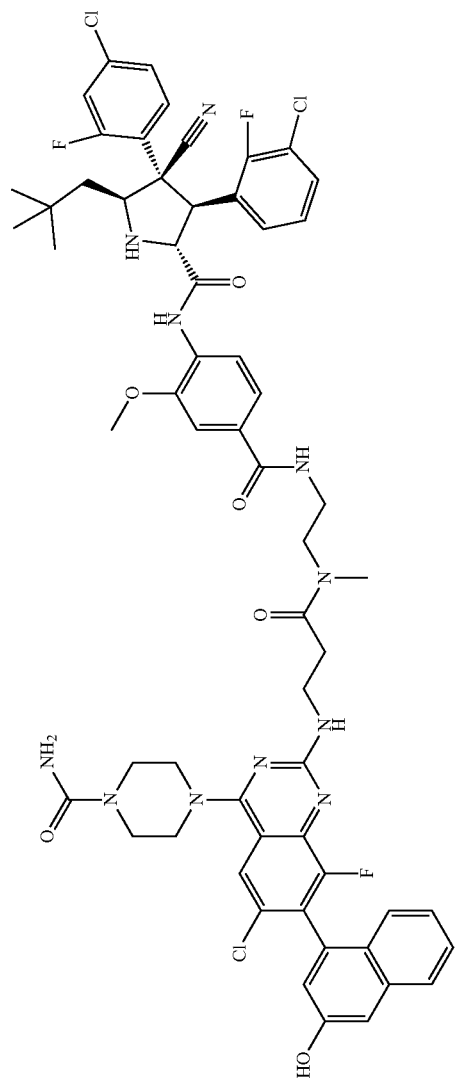 |

TABLE 8-continued
Compounds Prepared by Schemes 3-6
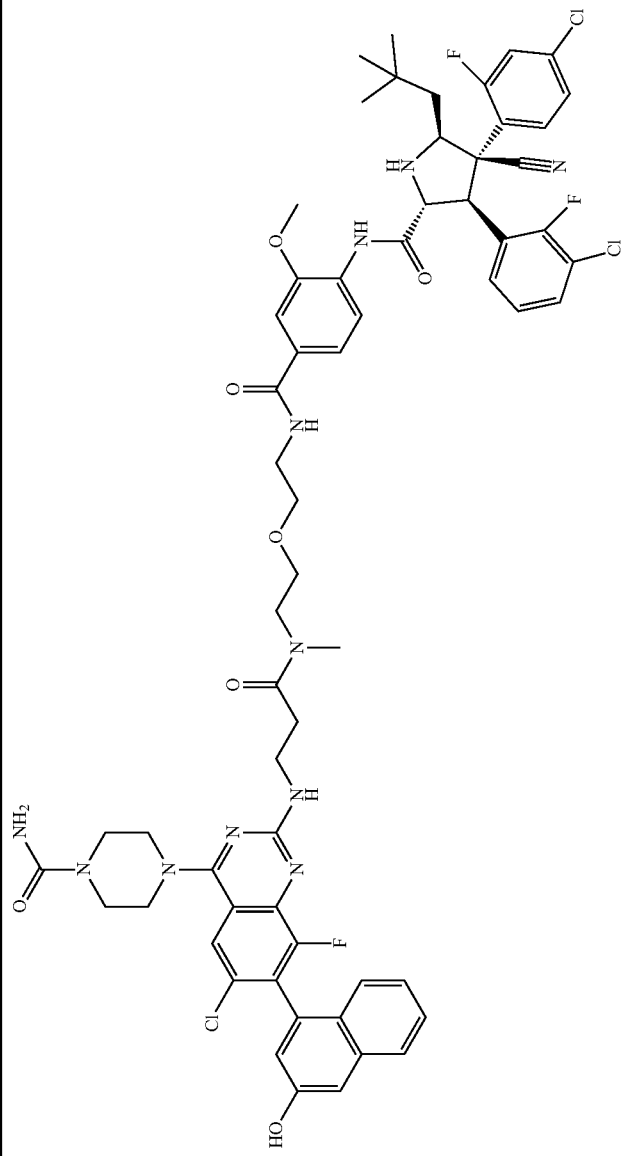
291

TABLE 8-continued
Compounds Prepared by Schemes 3-6
| 1525 | 1526 |
|---|---|
| 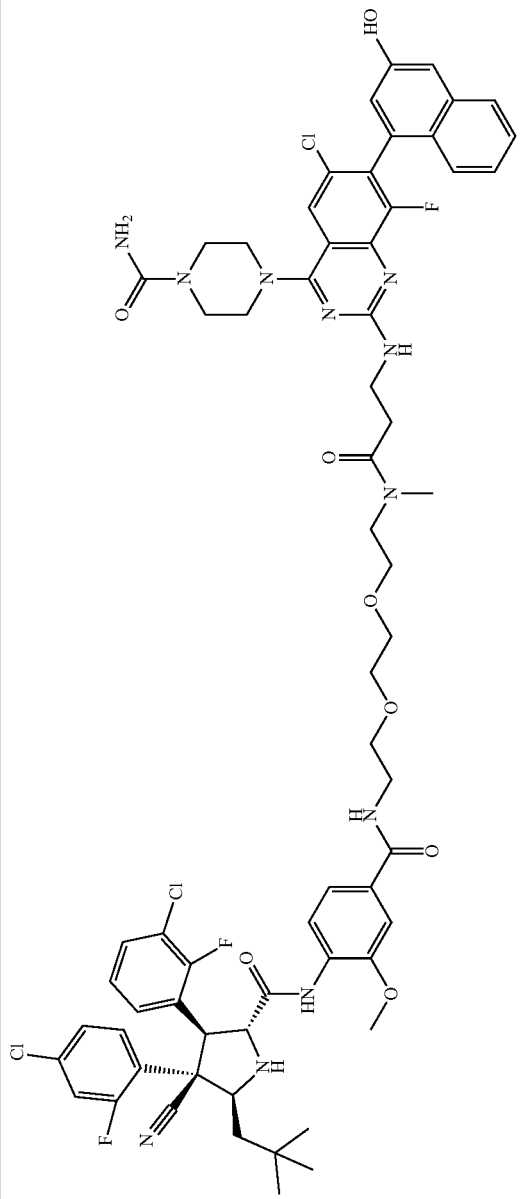 | 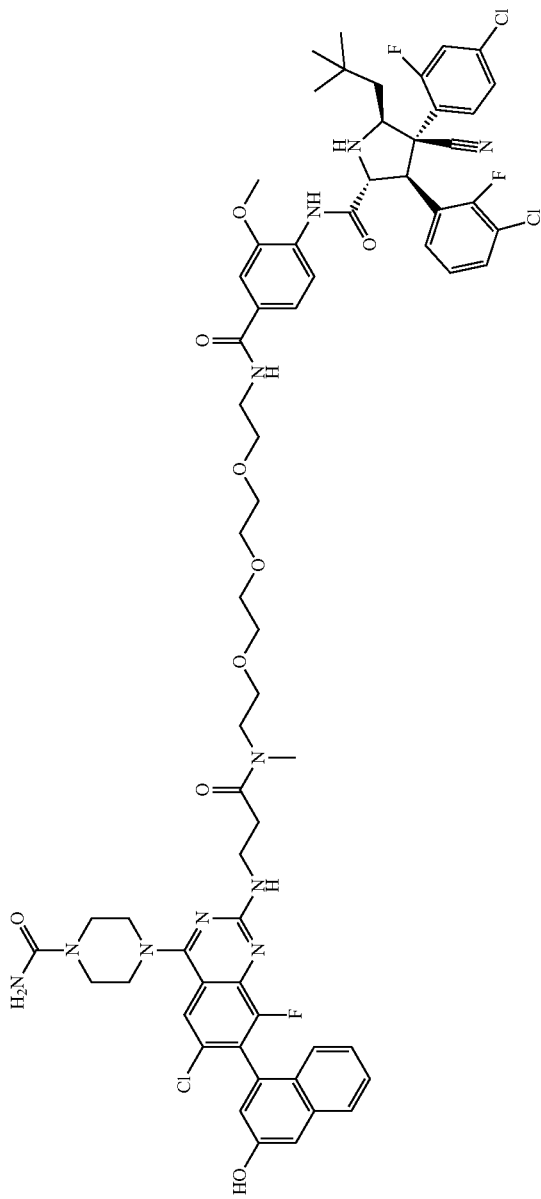 |

TABLE 8-continued
Compounds Prepared by Schemes 3-6
| 1527 | 1528 |
|---|---|
| 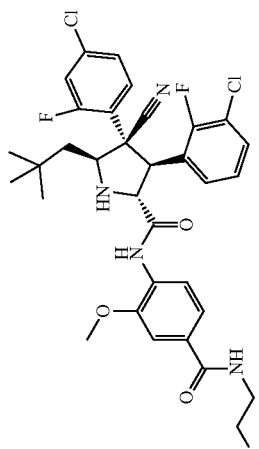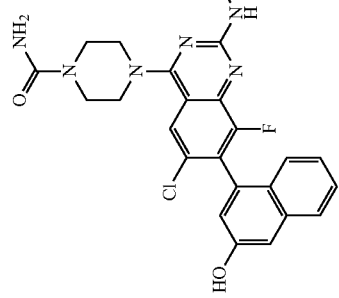 | 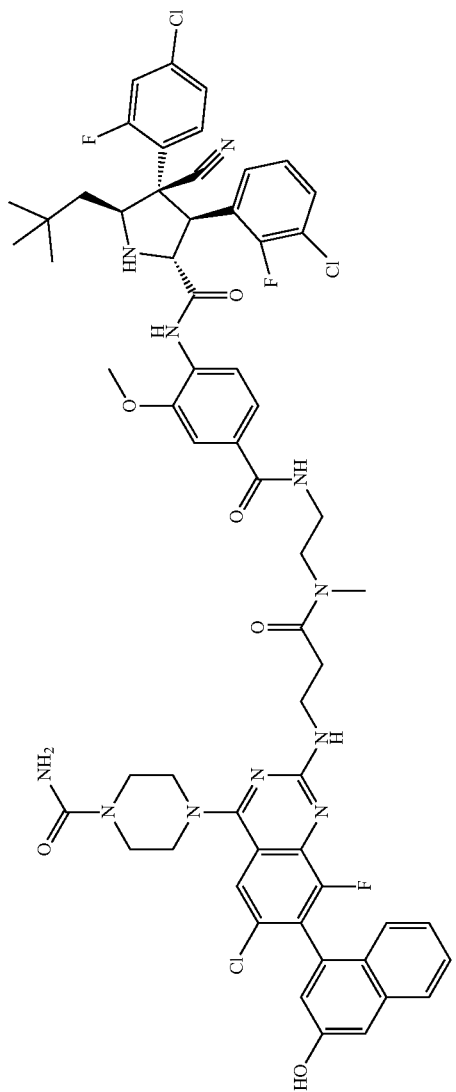 |

TABLE 8-continued
Compounds Prepared by Schemes 3-6
| 1529 | 1530 |
|---|---|
| 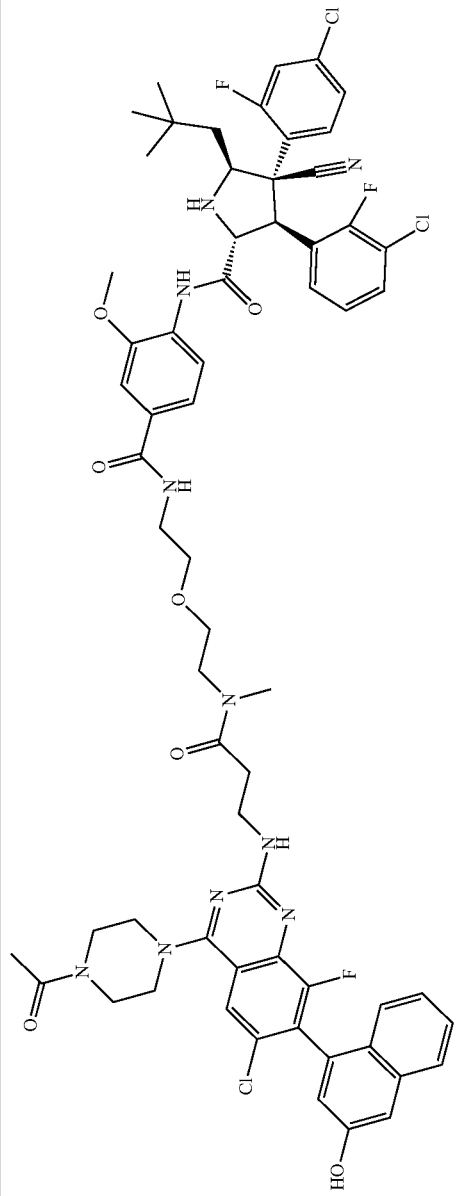 | 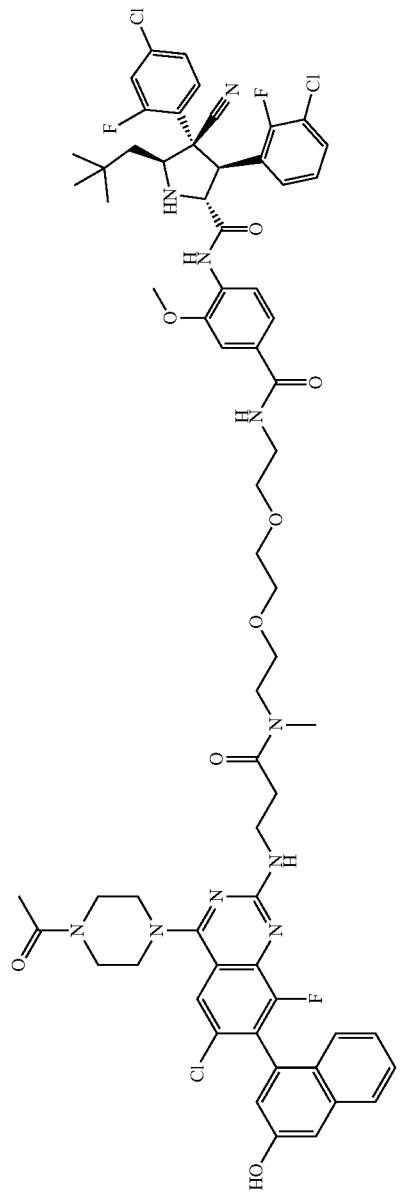 |

TABLE 8-continued
Compounds Prepared by Schemes 3-6
| 1531 | 1532 |
|---|---|
| 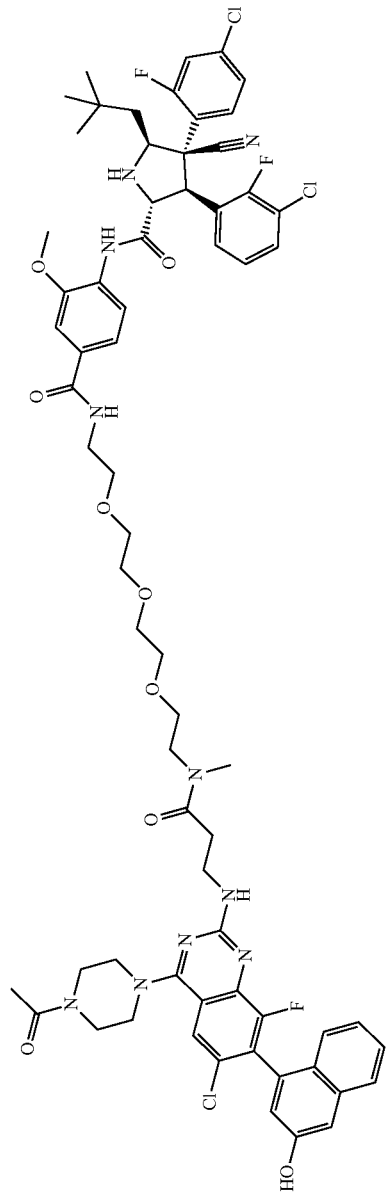 | 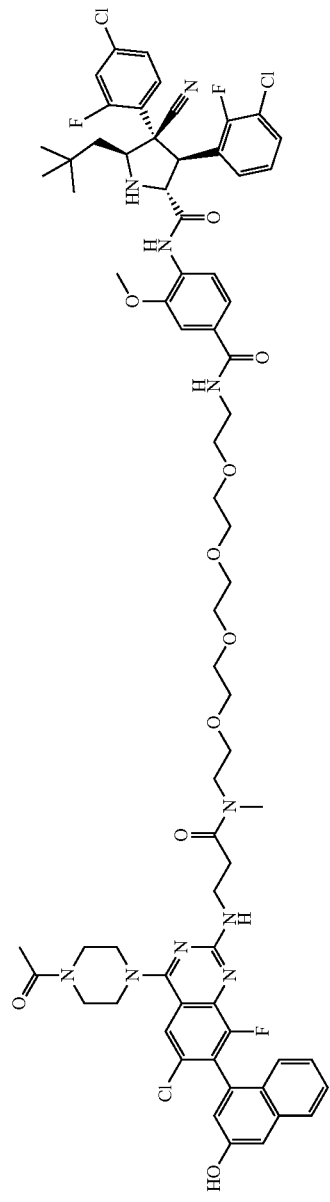 |

TABLE 8-continued
Compounds Prepared by Schemes 3-6
| 1533 | 1534 |
|---|---|
| 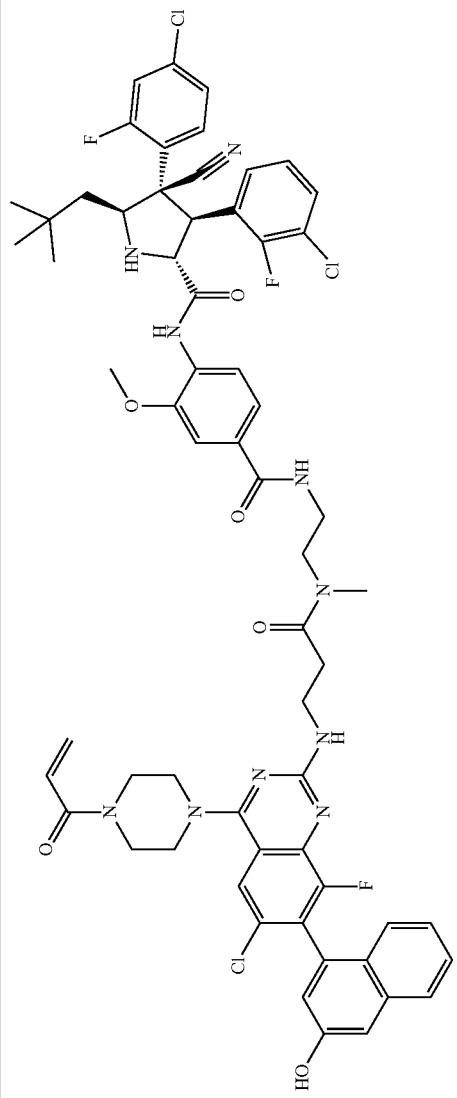 | 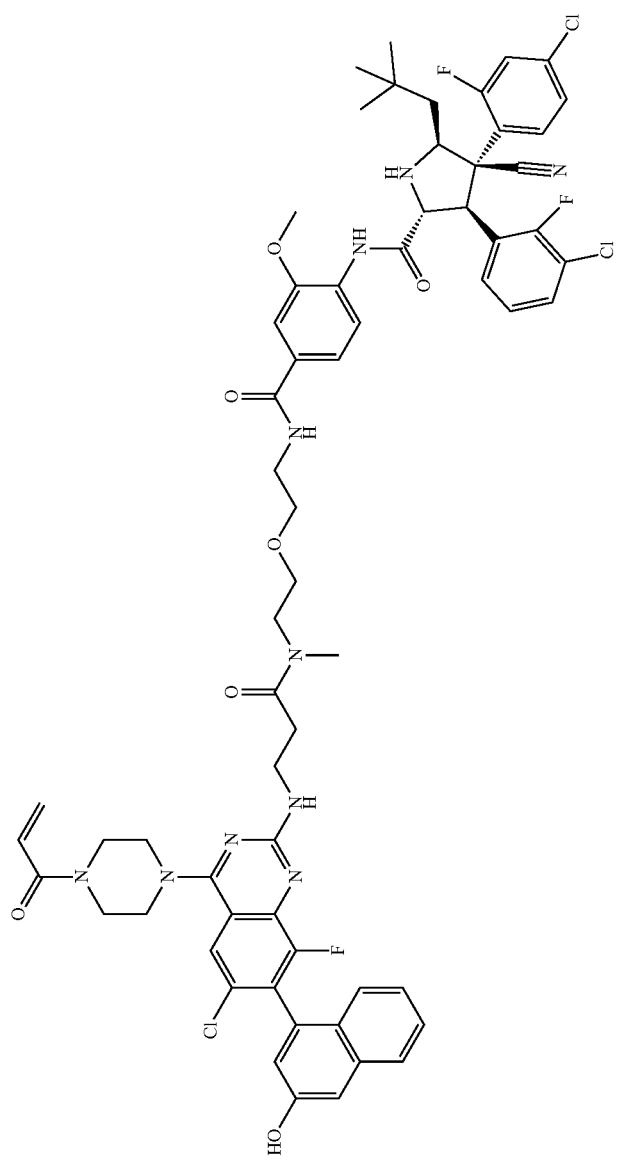 |

TABLE 8-continued
Compounds Prepared by Schemes 3-6
| 1535 | 1536 |
|---|---|
| 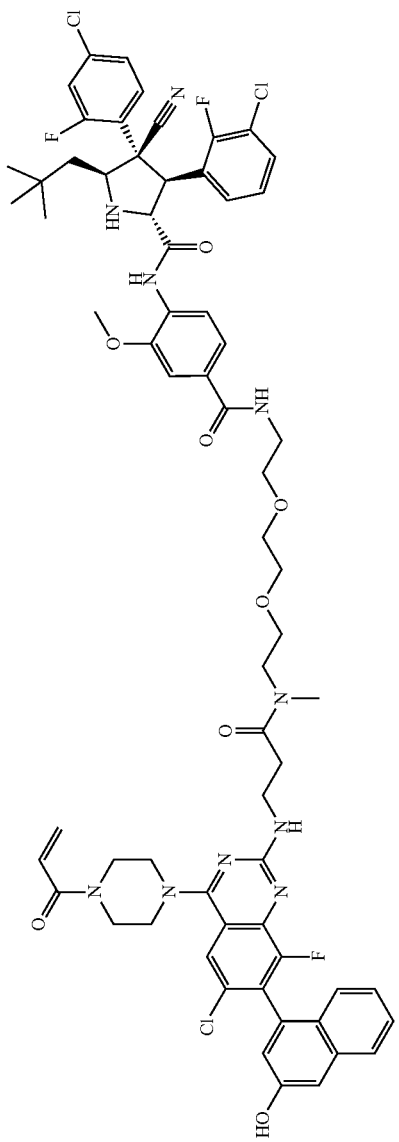 | 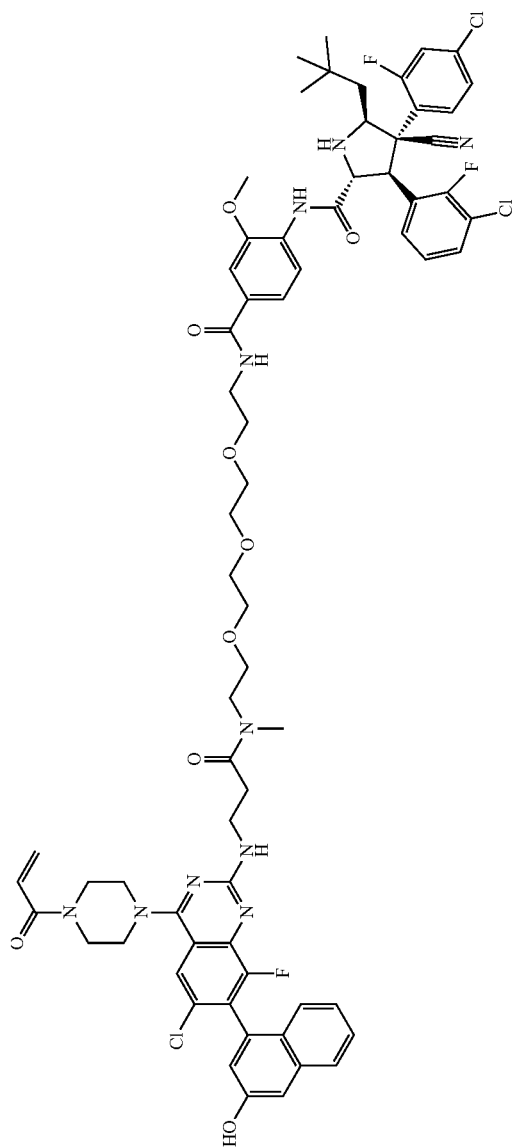 |
| 302 | 303 |

TABLE 8-continued
Compounds Prepared by Schemes 3-6
| 1537 | 1538 |
|---|---|
| 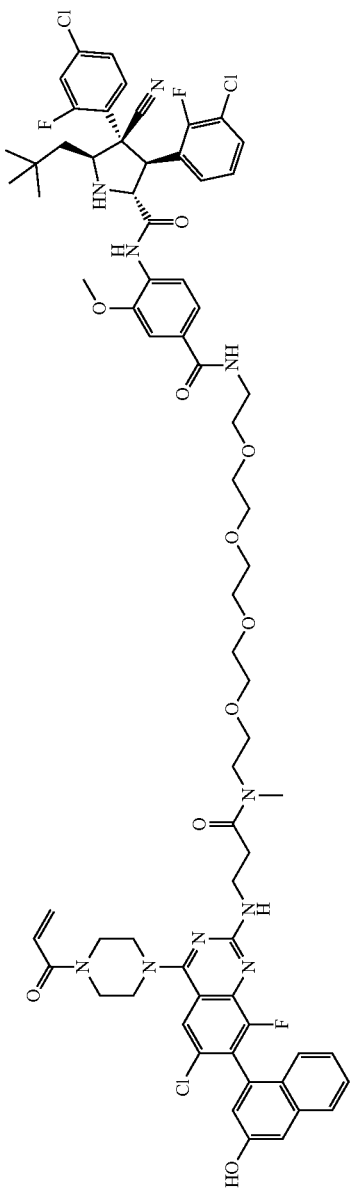 | 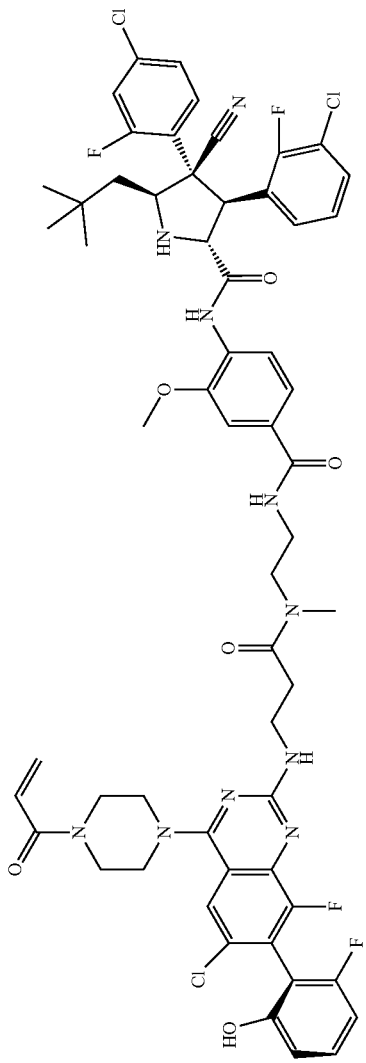 |
| 304 | 305 |

TABLE 8-continued
Compounds Prepared by Schemes 3-6
| 1539 | 1540 |
|---|---|
| 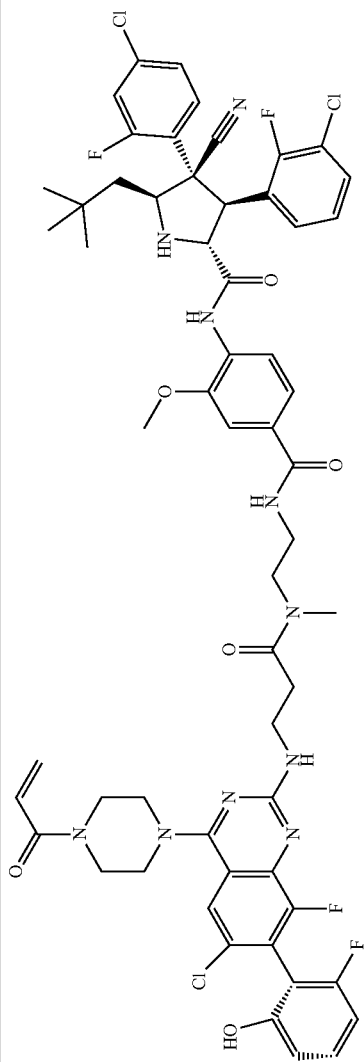 | 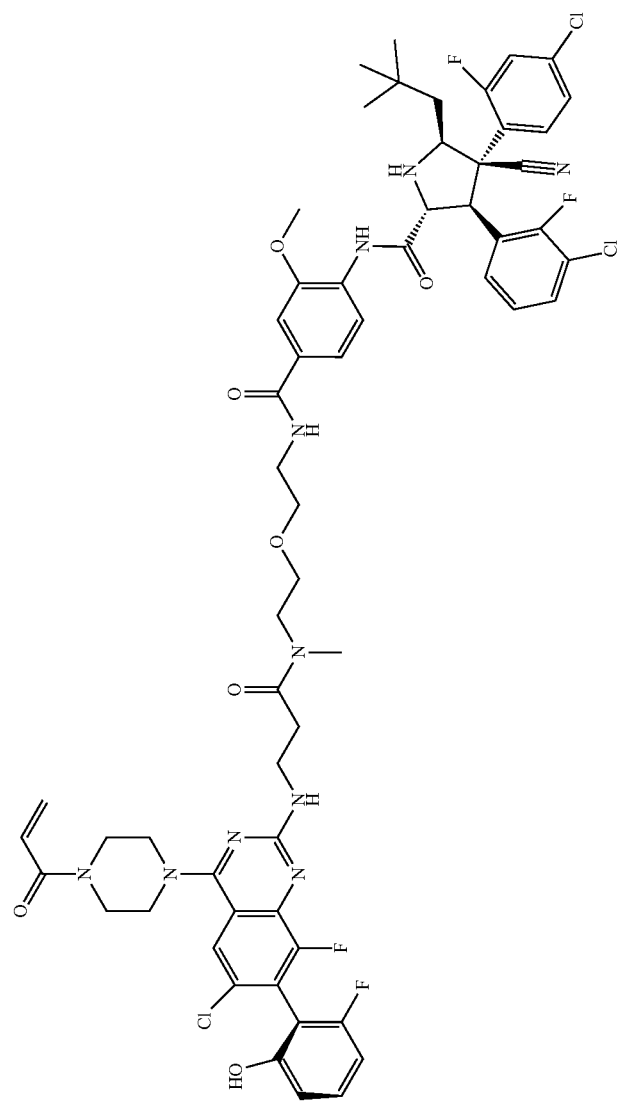 |

TABLE 8-continued
Compounds Prepared by Schemes 3-6
| 1541 | 1542 |
|---|---|
| 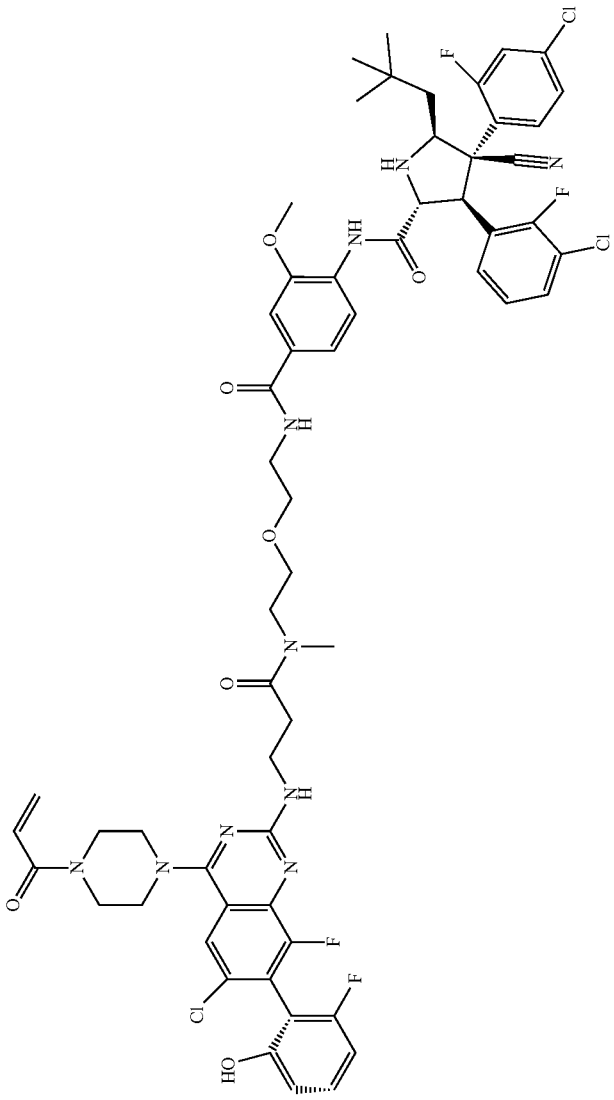 | 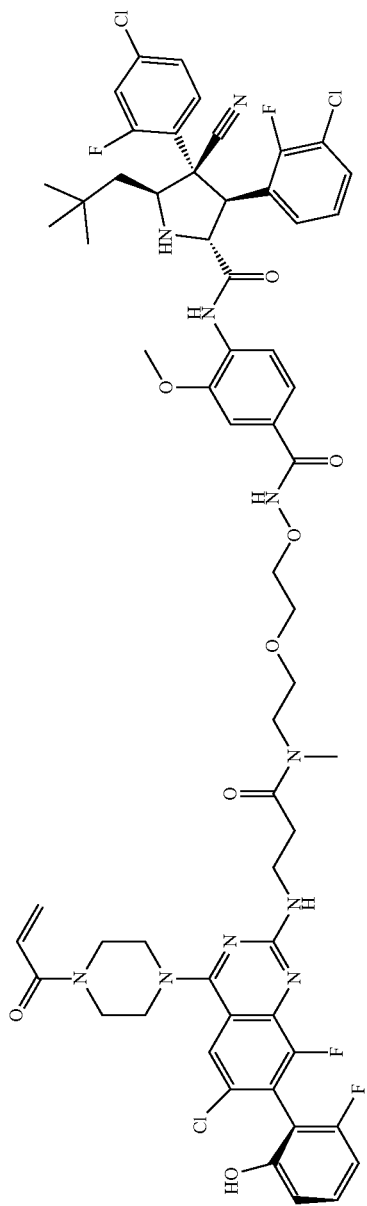 |

TABLE 8-continued
Compounds Prepared by Schemes 3-6
| 1543 | 1544 |
|---|---|
| 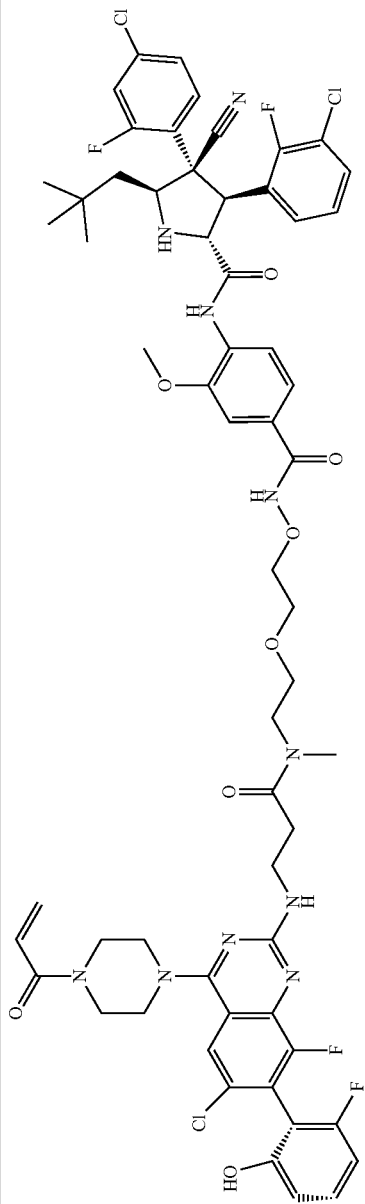 | 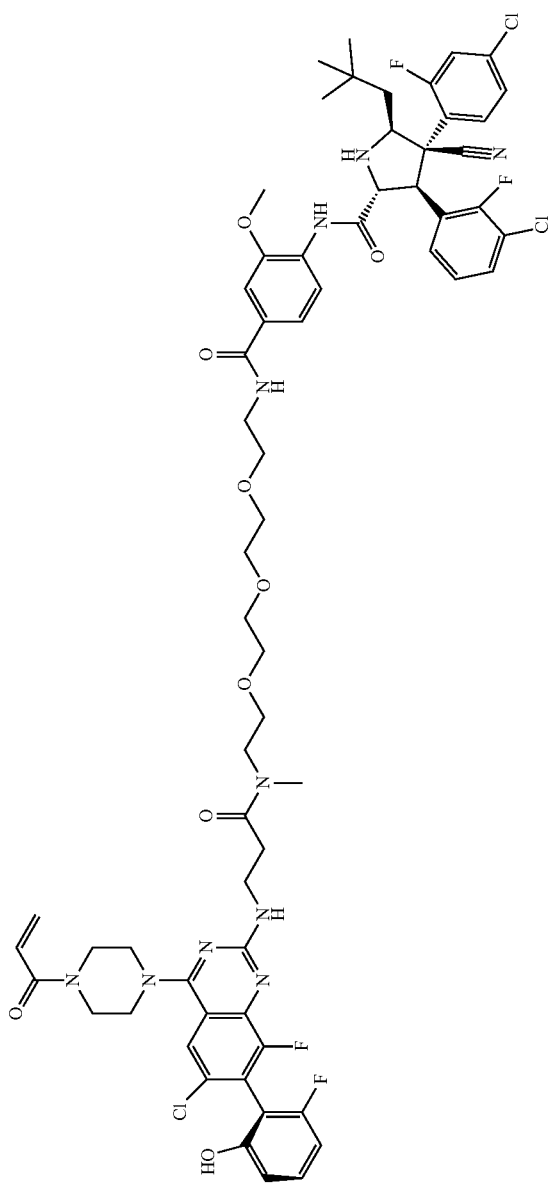 |

TABLE 8-continued
Compounds Prepared by Schemes 3-6
| 1545 | 1546 |
|---|---|
| 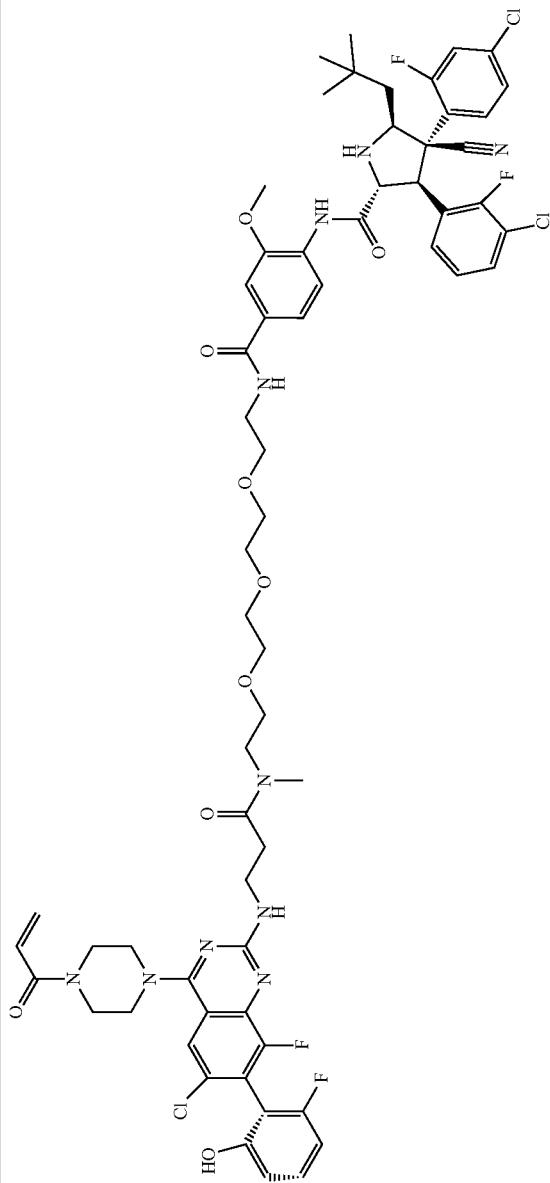 | 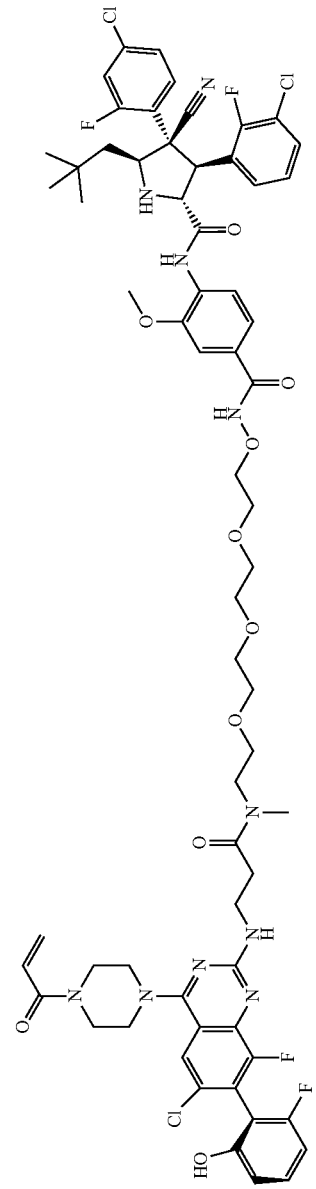 |
| 312 | 313 |

TABLE 8-continued
Compounds Prepared by Schemes 3-6
| 1547 | 1548 |
|---|---|
| 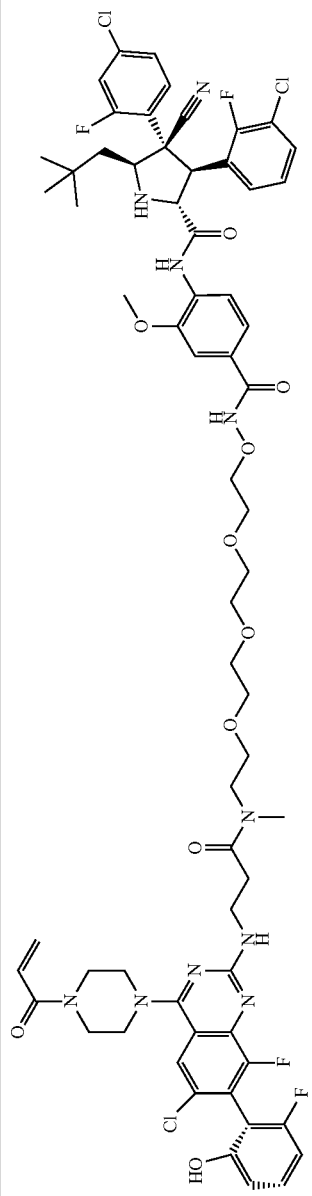 | 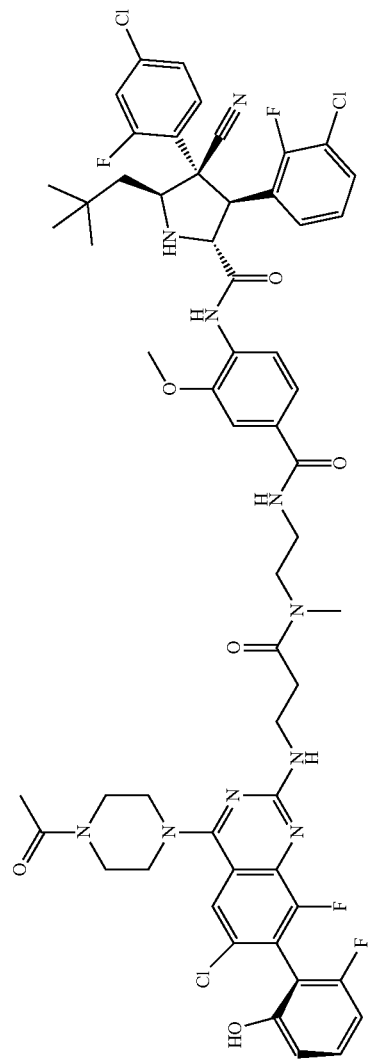 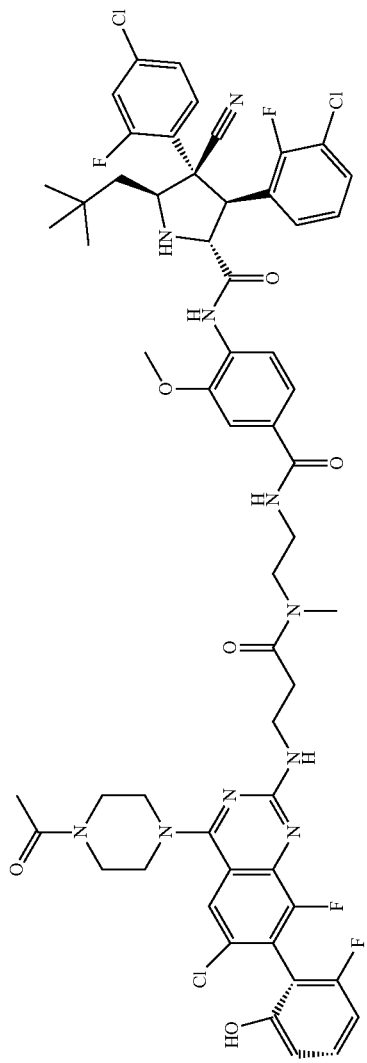 |
| 314 | 315 316 |

TABLE 8-continued
Compounds Prepared by Schemes 3-6
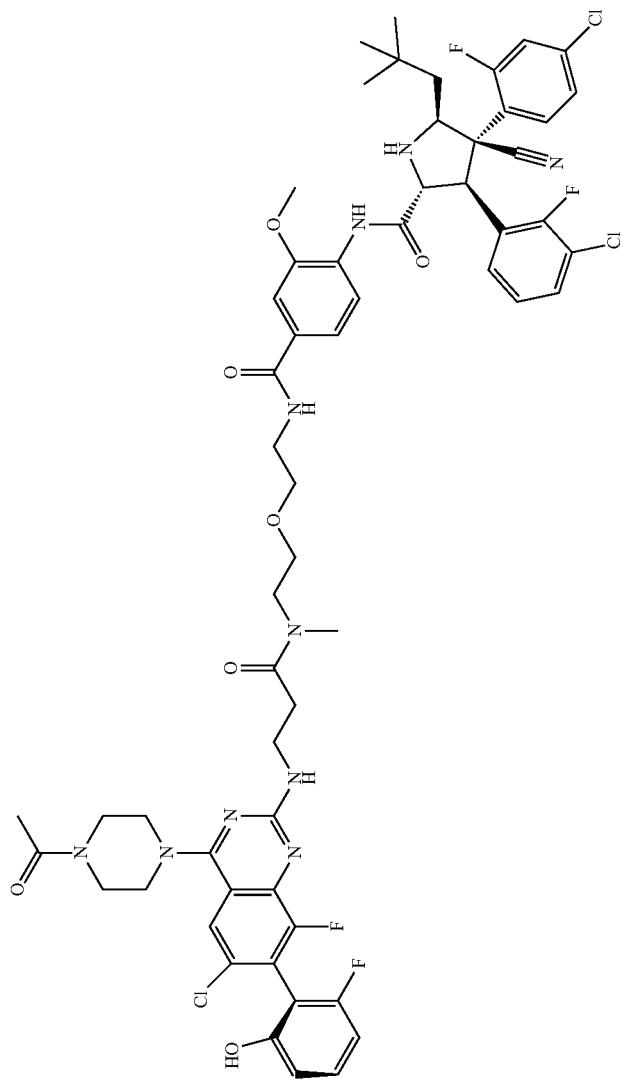

TABLE 8-continued
Compounds Prepared by Schemes 3-6
| 1551 | 1552 |
|---|---|
| 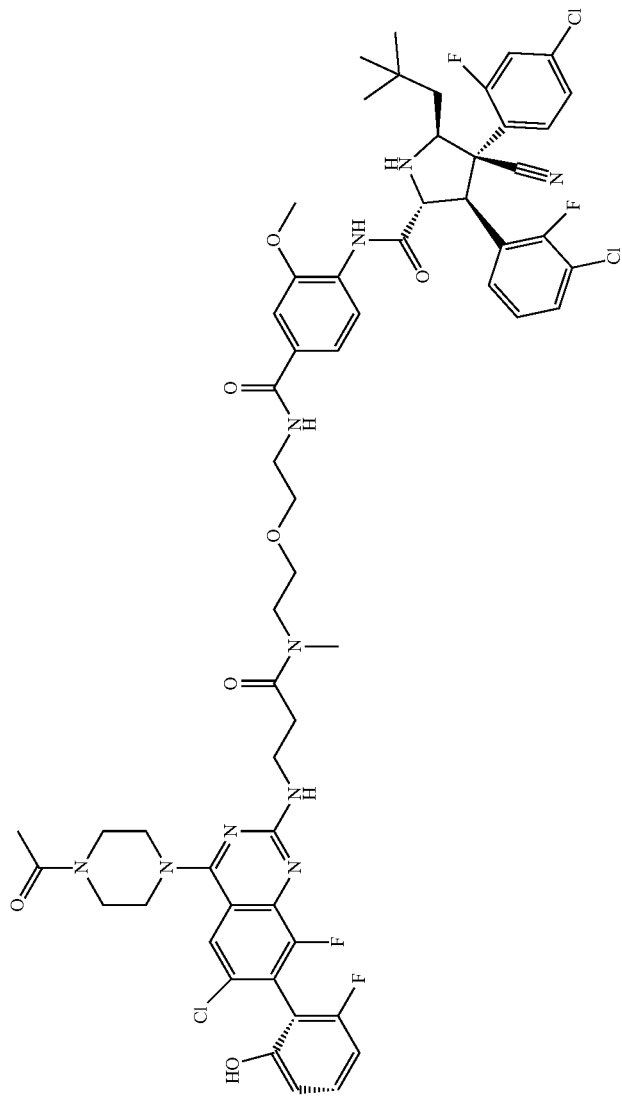 | 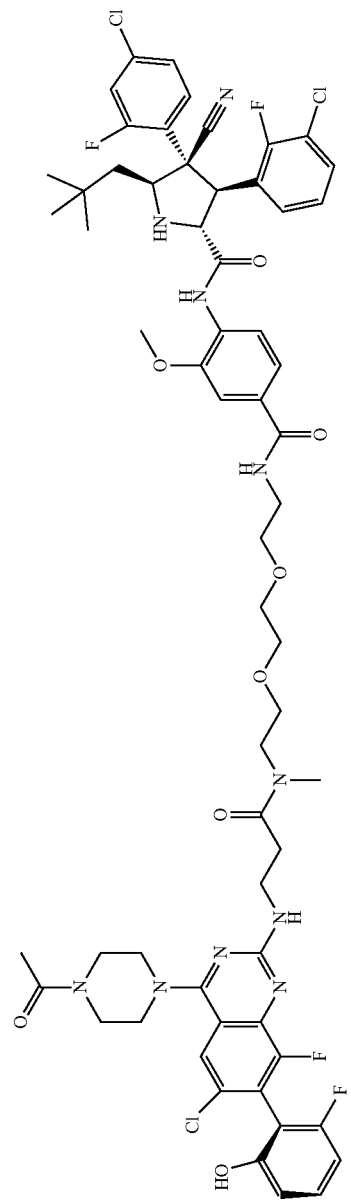 |

TABLE 8-continued
Compounds Prepared by Schemes 3-6
| 1553 | 1554 |
|---|---|
| 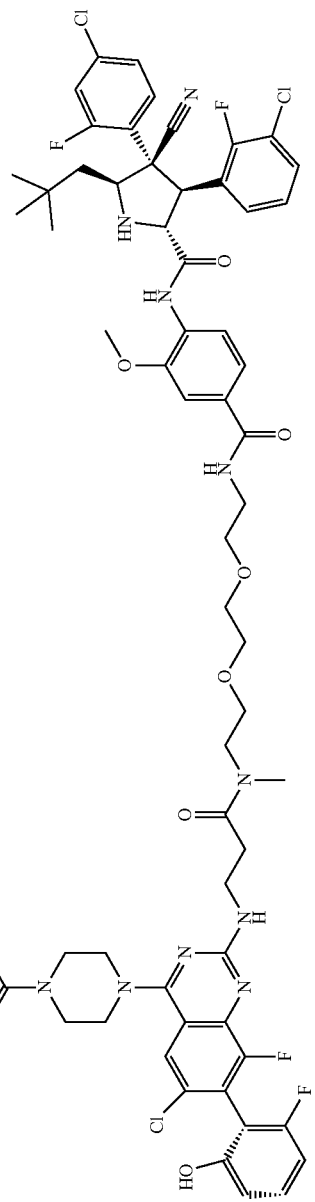 | 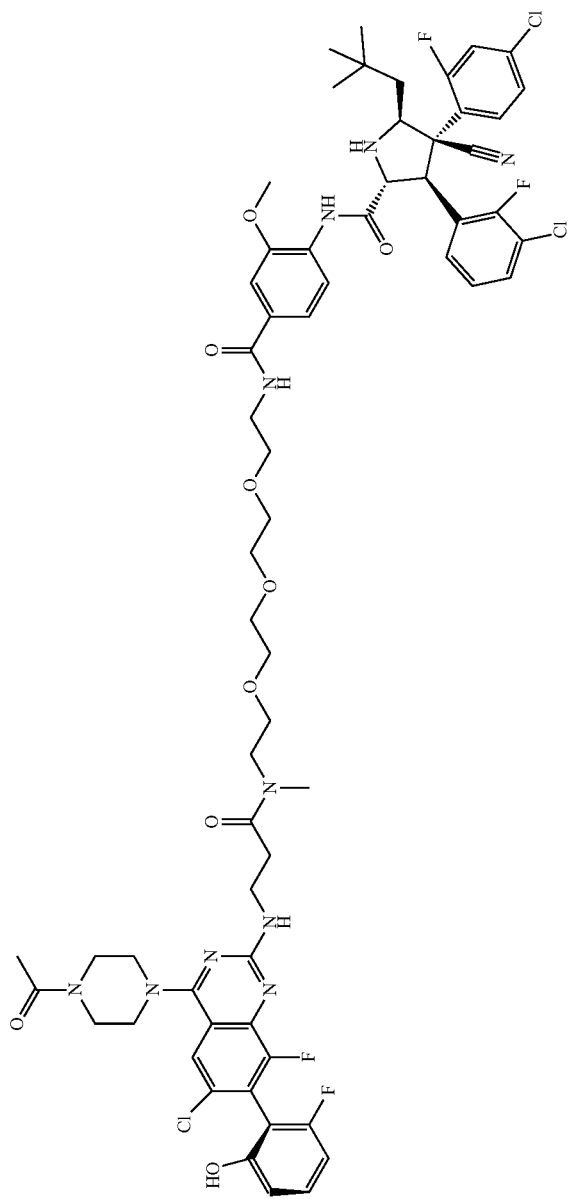 |

TABLE 8-continued
Compounds Prepared by Schemes 3-6
| 1555 | 1556 |
|---|---|
| 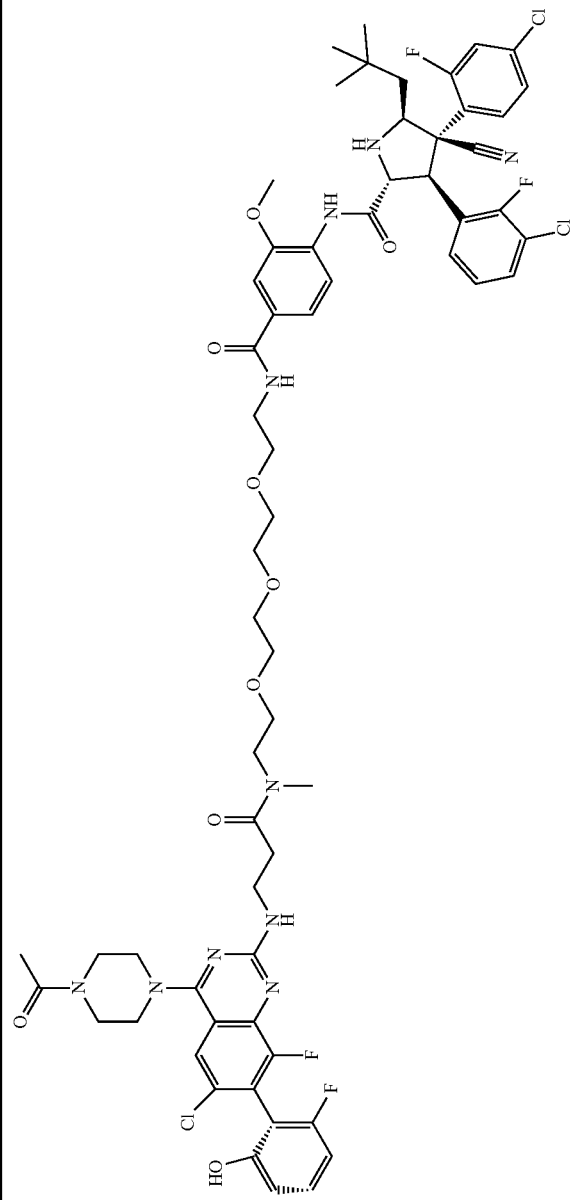 | 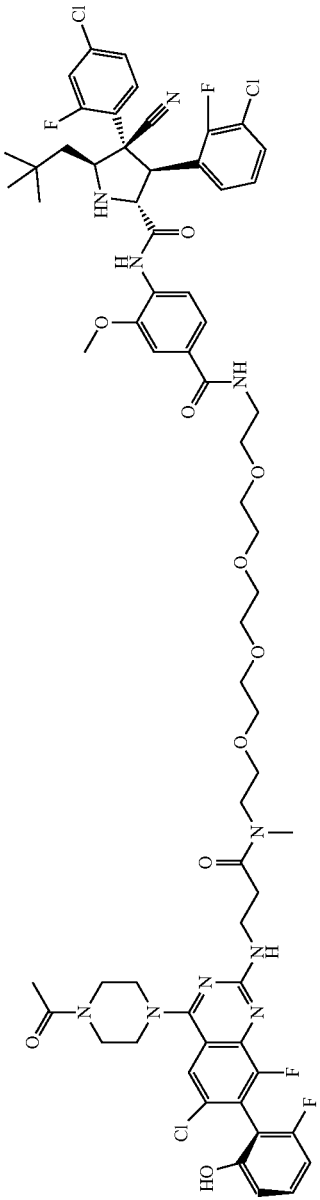 |

TABLE 8-continued
Compounds Prepared by Schemes 3-6
| 1557 | 1558 |
|---|---|
| 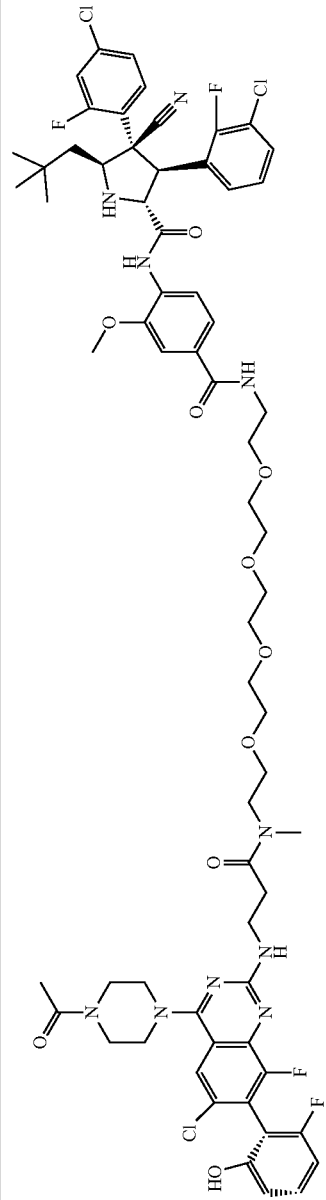 | 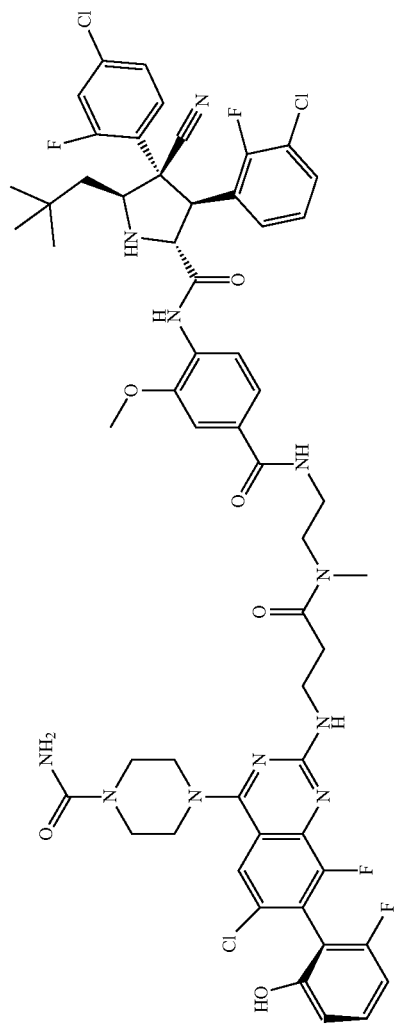 |
| 324 | 325 |

TABLE 8-continued
Compounds Prepared by Schemes 3-6
| 1559 | 1560 |
|---|---|
| 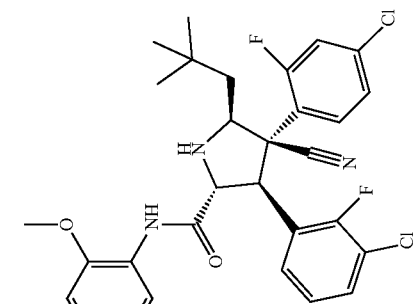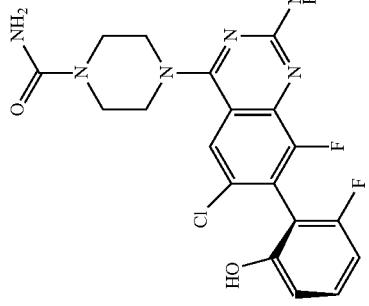 | 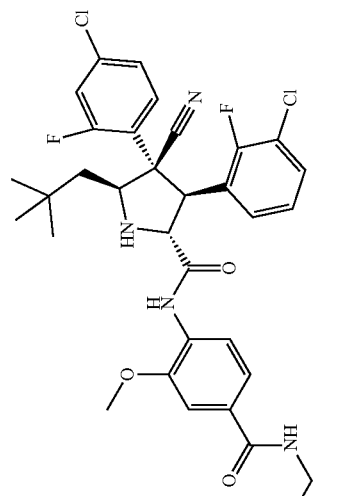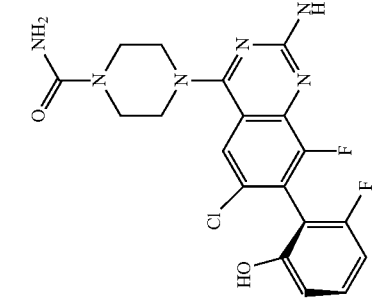 |

TABLE 8-continued

Compounds Prepared by Schemes 3-6

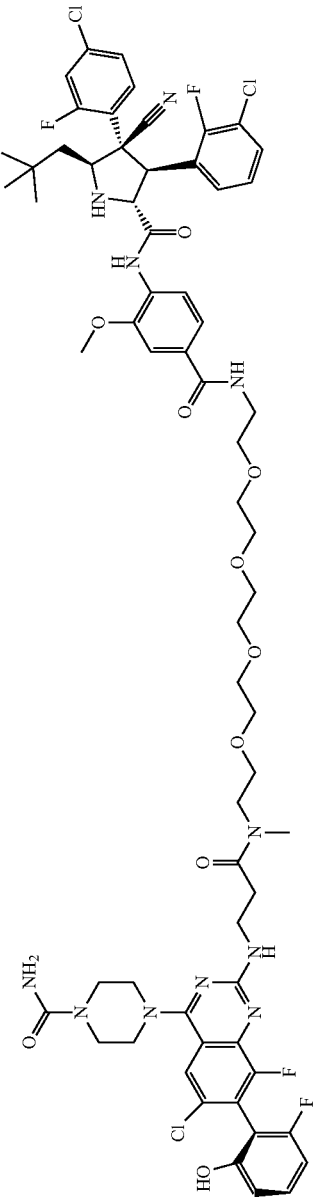

| Ex. No. | Compound Name | Synthetic Scheme |
|---|---|---|
| 181 | 4-(6-chloro-8-fluoro-2-((3-((2-(2-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethyl)(methyl)amino)-3-oxopropyl)amino)-7-(3-hydroxynaphthalen-1-yl)quinazolin-4-yl)piperazine-1-carboxamide | 3 |
| 182 | 4-(6-chloro-8-fluoro-2-(((S)-14-((2S,4R)-4-hydroxy-2-(((S)-1-(4-(4-methylthiazol-5-yl)phenyl)ethyl)carbamoyl)pyrrolidine-1-carbonyl)-4,15,15-trimethyl-3,12-dioxo-7,10-dioxa-4,13-diazahexadecyl)amino)-7-(3-hydroxynaphthalen-1-yl)quinazolin-4-yl)piperazine-1-carboxamide | 3 |
| 183 | 4-(6-chloro-8-fluoro-2-(((S)-17-((2S,4R)-4-hydroxy-2-(((S)-1-(4-(4-methylthiazol-5-yl)phenyl)ethyl)carbamoyl)pyrrolidine-1-carbonyl)-4,18,18-trimethyl-3,15-dioxo-7,10,13-trioxa-4,16-diazanonadecyl)amino)-7-(3-hydroxynaphthalen-1-yl)quinazolin-4-yl)piperazine-1-carboxamide | 3 |

TABLE 8-continued

Compounds Prepared by Schemes 3-6

| # | Name | |
|---|---|---|
| 184 | 4-(6-chloro-8-fluoro-2-(((S)-20-((2S,4R)-4-hydroxy-2-(((S)-1-(4-(4-methylthiazol-5-yl)phenyl)ethyl)carbamoyl)pyrrolidine-1-carbonyl)-4,21,21-trimethyl-3,18-dioxo-7,10,13,16-tetraoxa-4,19-diazadocosyl)amino)-7-(3-hydroxynaphthalen-1-yl)quinazolin-4-yl)piperazine-1-carboxamide | 3 |
| 185 | 4-(6-chloro-8-fluoro-2-(((S)-23-((2S,4R)-4-hydroxy-2-(((S)-1-(4-(4-methylthiazol-5-yl)phenyl)ethyl)carbamoyl)pyrrolidine-1-carbonyl)-4,24,24-trimethyl-3,21-dioxo-7,10,13,16,19-pentaoxa-4,22-diazapentacosyl)amino)-7-(3-hydroxynaphthalen-1-yl)quinazolin-4-yl)piperazine-1-carboxamide | 3 |
| 186 | (2S,4R)-1-((2S)-2-(2-(2-(3-((6-chloro-8-fluoro-7-(3-hydroxynaphthalen-1-yl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 187 | (2S,4R)-1-((2S)-2-(tert-butyl)-15-((6-chloro-8-fluoro-7-(3-hydroxynaphthalen-1-yl)-4-(4-propionylpiperazin-1-yl)quinazolin-2-yl)amino)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |
| 188 | (2S,4R)-1-((2S)-2-(tert-butyl)-18-((6-chloro-8-fluoro-7-(3-hydroxynaphthalen-1-yl)-4-(4-propionylpiperazin-1-yl)quinazolin-2-yl)amino)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 189 | (2S,4R)-1-((2S)-2-(tert-butyl)-21-((6-chloro-8-fluoro-7-(3-hydroxynaphthalen-1-yl)-4-(4-propionylpiperazin-1-yl)quinazolin-2-yl)amino)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 190 | (2S,4R)-1-((2S)-2-(tert-butyl)-24-((6-chloro-8-fluoro-7-(3-hydroxynaphthalen-1-yl)-4-(4-propionylpiperazin-1-yl)quinazolin-2-yl)amino)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 191 | (2S,4R)-1-((2S)-2-(2-(3-((4-acryloylpiperazin-1-yl)-6-chloro-8-fluoro-7-(3-hydroxynaphthalen-1-yl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 192 | (2S,4R)-1-((2S)-15-((4-acryloylpiperazin-1-yl)-6-chloro-8-fluoro-7-(3-hydroxynaphthalen-1-yl)quinazolin-2-yl)amino)-2-(tert-butyl)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |
| 193 | (2S,4R)-1-((2S)-18-((4-acryloylpiperazin-1-yl)-6-chloro-8-fluoro-7-(3-hydroxynaphthalen-1-yl)quinazolin-2-yl)amino)-2-(tert-butyl)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 194 | (2S,4R)-1-((2S)-21-((4-acryloylpiperazin-1-yl)-6-chloro-8-fluoro-7-(3-hydroxynaphthalen-1-yl)quinazolin-2-yl)amino)-2-(tert-butyl)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 195 | (2RS,4SR)-1-((RS)-21-((4-(4-acryloylpiperazin-1-yl)-6-chloro-8-fluoro-7-((RS)-3-hydroxynaphthalen-1-yl)quinazolin-2-yl)amino)-18-methyl-4,19-dioxo-6,9,12,15-tetraoxa-3,18-diazahenicosanoyl)-4-hydroxy-N-((RS)-1-(4-(4-methylthiazol-5-yl)phenyl)ethyl)pyrrolidine-2-carboxamide | 3 |
| 196 | (2RS,4SR)-1-((RS)-21-((4-(4-acryloylpiperazin-1-yl)-6-chloro-8-fluoro-7-((SR)-3-hydroxynaphthalen-1-yl)quinazolin-2-yl)amino)-18-methyl-4,19-dioxo-6,9,12,15-tetraoxa-3,18-diazahenicosanoyl)-4-hydroxy-N-((R)-1-(4-(4-methylthiazol-5-yl)phenyl)ethyl)pyrrolidine-2-carboxamide | 3 |
| 197 | (2S,4R)-1-((2S)-24-((4-(4-acryloylpiperazin-1-yl)-6-chloro-8-fluoro-7-(3-hydroxynaphthalen-1-yl)quinazolin-2-yl)amino)-2-(tert-butyl)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 198 | (2S,4R)-1-((2S)-39-((4-(4-acryloylpiperazin-1-yl)-6-chloro-8-fluoro-7-(3-hydroxynaphthalen-1-yl)quinazolin-2-yl)amino)-2-(tert-butyl)-36-methyl-4,37-dioxo-6,9,12,15,18,21,24,27,30,33-decaoxa-3,36-diazanonatriacontanoyl)-4-hydroxy-N-((S)-1-(4-(4-methylthiazol-5-yl)phenyl)ethyl)pyrrolidine-2-carboxamide | 3 |
| 199 | (2S,4S)-1-((2S)-21-((4-(4-acryloylpiperazin-1-yl)-6-chloro-8-fluoro-7-(3-hydroxynaphthalen-1-yl)quinazolin-2-yl)amino)-2-(tert-butyl)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 200 | (2S,4R)-1-((2S)-2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 201 | (2S,4R)-1-((2S)-15-((4-(4-acetylpiperazin-1-yl)-6-chloro-8-fluoro-7-(3-hydroxynaphthalen-1-yl)quinazolin-2-yl)amino)-2-(tert-butyl)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |
| 202 | (2S,4R)-1-((2S)-18-((4-(4-acetylpiperazin-1-yl)-6-chloro-8-fluoro-7-(3-hydroxynaphthalen-1-yl)quinazolin-2-yl)amino)-2-(tert-butyl)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 203 | (2S,4R)-1-((2S)-21-((4-(4-acetylpiperazin-1-yl)-6-chloro-8-fluoro-7-(3-hydroxynaphthalen-1-yl)quinazolin-2-yl)amino)-2-(tert-butyl)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 204 | (2S,4R)-1-((2S)-24-((4-(4-acetylpiperazin-1-yl)-6-chloro-8-fluoro-7-(3-hydroxynaphthalen-1-yl)quinazolin-2-yl)amino)-2-(tert-butyl)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 205 | (2S,4R)-1-((S)-2-(2-(3-(((S)-4-((4-acryloylpiperazin-1-yl)-6-chloro-8-fluoro-7-(2-fluoro-6-hydroxyphenyl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 206 | (2S,4R)-1-((S)-2-(2-(3-(((R)-4-((4-acryloylpiperazin-1-yl)-6-chloro-8-fluoro-7-(2-fluoro-6-hydroxyphenyl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 207 | (2S,4R)-1-((S)-15-(((S)-4-((4-acryloylpiperazin-1-yl)-6-chloro-8-fluoro-7-(2-fluoro-6-hydroxyphenyl)quinazolin-2-yl)amino)-2-(tert-butyl)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |
| 208 | (2S,4R)-1-((S)-15-(((R)-4-((4-acryloylpiperazin-1-yl)-6-chloro-8-fluoro-7-(2-fluoro-6-hydroxyphenyl)quinazolin-2-yl)amino)-2-(tert-butyl)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |

TABLE 8-continued

Compounds Prepared by Schemes 3-6

| | | |
|---|---|---|
| 209 | (2S,4R)-1-((S)-18-((4-(4-acryloylpiperazin-1-yl)-6-chloro-8-fluoro-7-((S)-2-fluoro-6-hydroxyphenyl)quinazolin-2-yl)amino)-2-(tert-butyl)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 210 | (2S,4R)-1-((S)-18-((4-(4-acryloylpiperazin-1-yl)-6-chloro-8-fluoro-7-((R)-2-fluoro-6-hydroxyphenyl)quinazolin-2-yl)amino)-2-(tert-butyl)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 211 | (2S,4R)-1-((S)-21-((4-(4-acryloylpiperazin-1-yl)-6-chloro-8-fluoro-7-(2-fluoro-6-hydroxyphenyl)quinazolin-2-yl)amino)-2-(tert-butyl)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 212 | (2S,4R)-1-((S)-21-(((R)-4-(4-acryloylpiperazin-1-yl)-6-chloro-8-fluoro-7-(2-fluoro-6-hydroxyphenyl)quinazolin-2-yl)amino)-2-(tert-butyl)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 213 | (2S,4R)-1-((S)-24-(((S)-4-(4-acryloylpiperazin-1-yl)-6-chloro-8-fluoro-7-(2-fluoro-6-hydroxyphenyl)quinazolin-2-yl)amino)-2-(tert-butyl)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 214 | (2S,4R)-1-((S)-24-(((R)-4-(4-acryloylpiperazin-1-yl)-6-chloro-8-fluoro-7-(2-fluoro-6-hydroxyphenyl)quinazolin-2-yl)amino)-2-(tert-butyl)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 215 | (2S,4R)-1-(S)-2-(2-(3-(((S)-4-(4-acetylpiperazin-1-yl)-6-chloro-8-fluoro-7-(2-fluoro-6-hydroxyphenyl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 216 | (2S,4R)-1-((S)-2-(2-(3-(((R)-4-(4-acetylpiperazin-1-yl)-6-chloro-8-fluoro-7-(2-fluoro-6-hydroxyphenyl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 217 | (2S,4R)-1-((S)-15-(((S)-4-(4-acetylpiperazin-1-yl)-6-chloro-8-fluoro-7-(2-fluoro-6-hydroxyphenyl)quinazolin-2-yl)amino)-2-(tert-butyl)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |
| 218 | (2S,4R)-1-((S)-15-(((R)-4-(4-acetylpiperazin-1-yl)-6-chloro-8-fluoro-7-(2-fluoro-6-hydroxyphenyl)quinazolin-2-yl)amino)-2-(tert-butyl)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |
| 219 | (2S,4R)-1-((S)-18-((4-(4-acetylpiperazin-1-yl)-6-chloro-8-fluoro-7-((S)-2-fluoro-6-hydroxyphenyl)quinazolin-2-yl)amino)-2-(tert-butyl)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 220 | (2S,4R)-1-((S)-18-((4-(4-acetylpiperazin-1-yl)-6-chloro-8-fluoro-7-((R)-2-fluoro-6-hydroxyphenyl)quinazolin-2-yl)amino)-2-(tert-butyl)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 221 | (2S,4R)-1-((S)-21-((4-(4-acetylpiperazin-1-yl)-6-chloro-8-fluoro-7-(2-fluoro-6-hydroxyphenyl)quinazolin-2-yl)amino)-2-(tert-butyl)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 222 | (2S,4R)-1-(((R)-4-(4-acetylpiperazin-1-yl)-6-chloro-8-fluoro-7-(2-fluoro-6-hydroxyphenyl)quinazolin-2-yl)amino)-2-(tert-butyl)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 223 | (2S,4R)-1-((S)-24-(((S)-4-(4-acetylpiperazin-1-yl)-6-chloro-8-fluoro-7-(2-fluoro-6-hydroxyphenyl)quinazolin-2-yl)amino)-2-(tert-butyl)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 224 | (2S,4R)-1-((S)-24-(((R)-4-(4-acetylpiperazin-1-yl)-6-chloro-8-fluoro-7-(2-fluoro-6-hydroxyphenyl)quinazolin-2-yl)amino)-2-(tert-butyl)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 225 | 4-((S)-6-chloro-8-fluoro-7-(2-fluoro-6-hydroxyphenyl)-2-(3-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethyl)(methyl)amino)-3-oxopropyl)amino)quinazolin-4-yl)piperazine-1-carboxamide | 3 |
| 226 | 4-((R)-6-chloro-8-fluoro-7-(2-fluoro-6-hydroxyphenyl)-2-(3-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethyl)(methyl)amino)-3-oxopropyl)amino)quinazolin-4-yl)piperazine-1-carboxamide | 3 |
| 227 | 4-((S)-6-chloro-8-fluoro-7-(2-fluoro-6-hydroxyphenyl)-2-(((S)-14-((2S,4R)-4-hydroxy-2-(((S)-1-(4-(4-methylthiazol-5-yl)phenyl)ethyl)carbamoyl)pyrrolidine-1-carbonyl)-4,15,15-trimethyl-3,12-dioxo-7,10-dioxa-4,13-diazahexadecyl)amino)quinazolin-4-yl)piperazine-1-carboxamide | 3 |
| 228 | 4-((S)-6-chloro-8-fluoro-7-(2-fluoro-6-hydroxyphenyl)-2-(((S)-17-((2S,4R)-4-hydroxy-2-(((S)-1-(4-(4-methylthiazol-5-yl)phenyl)ethyl)carbamoyl)pyrrolidine-1-carbonyl)-4,18,18-trimethyl-3,15-dioxo-7,10,13-trioxa-4,16-diazanonadecyl)amino)quinazolin-4-yl)piperazine-1-carboxamide | 3 |
| 229 | 4-((R)-6-chloro-8-fluoro-7-(2-fluoro-6-hydroxyphenyl)-2-(((S)-17-((2S,4R)-4-hydroxy-2-(((S)-1-(4-(4-methylthiazol-5-yl)phenyl)ethyl)carbamoyl)pyrrolidine-1-carbonyl)-4,18,18-trimethyl-3,15-dioxo-7,10,13-trioxa-4,16-diazanonadecyl)amino)quinazolin-4-yl)piperazine-1-carboxamide | 3 |
| 230 | 4-((S)-6-chloro-8-fluoro-7-(2-fluoro-6-hydroxyphenyl)-2-(((S)-20-((2S,4R)-4-hydroxy-2-(((S)-1-(4-(4-methylthiazol-5-yl)phenyl)ethyl)carbamoyl)pyrrolidine-1-carbonyl)-4,21,21-trimethyl-3,18-dioxo-7,10,13,16-tetraoxa-4,19-diazadocosyl)amino)quinazolin-4-yl)piperazine-1-carboxamide | 3 |
| 231 | 4-((R)-6-chloro-8-fluoro-7-(2-fluoro-6-hydroxyphenyl)-2-(((S)-20-((2S,4R)-4-hydroxy-2-(((S)-1-(4-(4-methylthiazol-5-yl)phenyl)ethyl)carbamoyl)pyrrolidine-1-carbonyl)-4,21,21-trimethyl-3,18-dioxo-7,10,13,16-tetraoxa-4,19-diazadocosyl)amino)quinazolin-4-yl)piperazine-1-carboxamide | 3 |
| 232 | 4-((S)-6-chloro-8-fluoro-7-(2-fluoro-6-hydroxyphenyl)-2-(((S)-23-((2S,4R)-4-hydroxy-2-(((S)-1-(4-(4-methylthiazol-5-yl)phenyl)ethyl)carbamoyl)pyrrolidine-1-carbonyl)-4,24,24-trimethyl-3,21-dioxo-7,10,13,16,19-pentaoxa-4,22-diazapentacosyl)amino)quinazolin-4-yl)piperazine-1-carboxamide | 3 |
| 233 | 4-((R)-6-chloro-8-fluoro-7-(2-fluoro-6-hydroxyphenyl)-2-(((S)-23-((2S,4R)-4-hydroxy-2-(((S)-1-(4-(4-methylthiazol-5-yl)phenyl)ethyl)carbamoyl)pyrrolidine-1-carbonyl)-4,24,24-trimethyl-3,21-dioxo-7,10,13,16,19-pentaoxa-4,22-diazapentacosyl)amino)quinazolin-4-yl)piperazine-1-carboxamide | 3 |

TABLE 8-continued

Compounds Prepared by Schemes 3-6

| | | |
|---|---|---|
| 234 | (2S,4R)-1-((S)-2-(2-(2-(3-(((S)-6-chloro-4-(4-(2,2-dihydroxyacetyl)piperazin-1-yl)-8-fluoro-7-(2-fluoro-6-hydroxyphenyl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 235 | (2S,4R)-1-((S)-2-(2-(3-(((R)-6-chloro-4-(4-(2,2-dihydroxyacetyl)piperazin-1-yl)-8-fluoro-7-(2-fluoro-6-hydroxyphenyl)quinazolin-2-yl)amino)-N-methylpropanamido)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 236 | (2S,4R)-1-((S)-2-(tert-butyl)-15-(((S)-6-chloro-4-(4-(2,2-dihydroxyacetyl)piperazin-1-yl)-8-fluoro-7-(2-fluoro-6-hydroxyphenyl)quinazolin-2-yl)amino)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |
| 237 | (2S,4R)-1-((S)-2-(tert-butyl)-15-(((R)-6-chloro-4-(4-(2,2-dihydroxyacetyl)piperazin-1-yl)-8-fluoro-7-(2-fluoro-6-hydroxyphenyl)quinazolin-2-yl)amino)-12-methyl-4,13-dioxo-6,9-dioxa-3,12-diazapentadecanoyl)-4-hydroxy-N-((S)-1-(4-(4-methylthiazol-5-yl)phenyl)ethyl)pyrrolidine-2-carboxamide | 3 |
| 238 | (2S,4R)-1-((S)-2-(tert-butyl)-18-(((S)-6-chloro-4-(4-(2,2-dihydroxyacetyl)piperazin-1-yl)-8-fluoro-7-(2-fluoro-6-hydroxyphenyl)quinazolin-2-yl)amino)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 239 | (2S,4R)-1-((S)-2-(tert-butyl)-18-(((R)-6-chloro-4-(4-(2,2-dihydroxyacetyl)piperazin-1-yl)-8-fluoro-7-(2-fluoro-6-hydroxyphenyl)quinazolin-2-yl)amino)-15-methyl-4,16-dioxo-6,9,12-trioxa-3,15-diazaoctadecanoyl)-4-hydroxy-N-((S)-1-(4-(4-methylthiazol-5-yl)phenyl)ethyl)pyrrolidine-2-carboxamide | 3 |
| 240 | (2S,4R)-1-((S)-2-(tert-butyl)-21-(((S)-6-chloro-4-(4-(2,2-dihydroxyacetyl)piperazin-1-yl)-8-fluoro-7-(2-fluoro-6-hydroxyphenyl)quinazolin-2-yl)amino)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 241 | (2S,4R)-1-((S)-2-(tert-butyl)-21-(((R)-6-chloro-4-(4-(2,2-dihydroxyacetyl)piperazin-1-yl)-8-fluoro-7-(2-fluoro-6-hydroxyphenyl)quinazolin-2-yl)amino)-18-methyl-4,19-dioxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 3 |
| 242 | (2S,4R)-1-((S)-2-(tert-butyl)-24-(((S)-6-chloro-4-(4-(2,2-dihydroxyacetyl)piperazin-1-yl)-8-fluoro-7-(2-fluoro-6-hydroxyphenyl)quinazolin-2-yl)amino)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 243 | (2S,4R)-1-((S)-2-(tert-butyl)-24-(((R)-6-chloro-4-(4-(2,2-dihydroxyacetyl)piperazin-1-yl)-8-fluoro-7-(2-fluoro-6-hydroxyphenyl)quinazolin-2-yl)amino)-21-methyl-4,22-dioxo-6,9,12,15,18-pentaoxa-3,21-diazatetracosanoyl)-4-hydroxy-N-((S)-1-(4-(4-methylthiazol-5-yl)phenyl)ethyl)pyrrolidine-2-carboxamide | 3 |
| 244 | (2S,4R)-1-((1-(2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 245 | (2S,4R)-1-((2S)-2-(2-(2-(1-((2R)-2-(2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 246 | (2S,4R)-1-((2S)-2-(tert-butyl)-14-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | 3 |
| 247 | (2S,4R)-1-((2S)-2-(tert-butyl)-17-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | 3 |
| 248 | (2S,4R)-1-((2S)-2-(tert-butyl)-20-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | 3 |
| 249 | (2S,4R)-1-((2S)-2-(2-(4-(2-(2-(3-((4-acryloylpiperazin-1-yl)-6-chloro-8-fluoro-7-(3-hydroxynaphthalen-1-yl)-6-chloro-7-(3-hydroxynaphthalen-1-yl)quinazolin-2-yl)amino)-N-methylpropanamido)ethoxy)ethyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 3 |
| 254 | (2S,4R)-1-((2S)-2-(2-((5-(4-(6-chloro-2-((3-(dimethylamino)-3-oxopropyl)amino)-8-fluoro-7-(3-hydroxynaphthalen-1-yl)quinazolin-4-yl)piperazin-1-yl)-5-oxopentyl)oxy)acetamido)-3,3-dimethylbutanoyl)-4-hydroxy-N-((S)-1-(4-(4-methylthiazol-5-yl)phenyl)ethyl)-N-methylpropanamide | 4 |
| 255 | 3-((4-(4-acryloylpiperazin-1-yl)-6-chloro-8-fluoro-7-(3-hydroxynaphthalen-1-yl)quinazolin-2-yl)amino)-N-(2-(3-(2-(S)-1-((S)-2-cyclohexyl-2-((S)-2-(methylamino)propanamido)acetyl)pyrrolidin-2-yl)thiazole-4-carbonyl)phenoxy)ethyl)-N-methylpropanamide | 5 |
| 256 | 3-((4-(4-acryloylpiperazin-1-yl)-6-chloro-8-fluoro-7-(3-hydroxynaphthalen-1-yl)quinazolin-2-yl)amino)-N-(2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethyl)-N-methylpropanamide | 5 |
| 257 | 3-((4-(4-acryloylpiperazin-1-yl)-6-chloro-8-fluoro-7-(3-hydroxynaphthalen-1-yl)quinazolin-2-yl)amino)-N-(2-(2-(2-(2-(3-(2-((S)-1-((S)-2-cyclohexyl-2-((S)-2-(methylamino)propan-amido)acetyl)pyrrolidin-2-yl)thiazole-4-carbonyl)phenoxy)ethoxy)ethoxy)ethyl)-N-methylpropanamide | 5 |
| 258 | 3-((4-(4-acryloylpiperazin-1-yl)-6-chloro-8-fluoro-7-(3-hydroxynaphthalen-1-yl)quinazolin-2-yl)amino)-N-(2-(2-(2-(2-(2-(3-(2-((S)-1-((S)-2-cyclohexyl-2-((S)-2-(methylamino)propan-amido)acetyl)pyrrolidin-2-yl)thiazole-4-carbonyl)phenoxy)ethoxy)ethoxy)ethoxy)ethyl)-N-methylpropanamide | 5 |
| 259 | 3-((4-(4-acryloylpiperazin-1-yl)-6-chloro-8-fluoro-7-(3-hydroxynaphthalen-1-yl)quinazolin-2-yl)amino)-N-(14-(3-(2-((S)-1-((S)-2-cyclohexyl-2-((S)-2-(methylamino)propanamido)acetyl)pyrrolidin-2-yl)thiazole-4-carbonyl)phenoxy)-3,6,9,12-tetraoxatetradecyl)-N-methylpropanamide | 5 |
| 260 | 4-(6-chloro-2-(3-((2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethyl)(methyl)amino)-3-oxopropyl)amino)-8-fluoro-7-(3-hydroxynaphthalen-1-yl)quinazolin-4-yl)piperazine-1-carboxamide | 5 |
| 261 | 4-(6-chloro-2-(3-((2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethyl)(methyl)amino)-3-oxopropyl)amino)-8-fluoro-7-(3-hydroxynaphthalen-1-yl)piperazine-1-carboxamide | 5 |
| 262 | 4-(6-chloro-2-(3-((2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)(methyl)amino)-3-oxopropyl)amino)-8-fluoro-7-(3-hydroxynaphthalen-1-yl)quinazolin-4-yl)piperazine-1-carboxamide | 5 |

TABLE 8-continued

Compounds Prepared by Schemes 3-6

| # | Name | |
|---|---|---|
| 263 | 4-(6-chloro-2-((1-((4-(2-((S)-2-cyclohexyl-2-((S)-2-(methylamino)propanamido)acetyl)pyrrolidin-2-yl)thiazol-4-yl)naphthalen-1-yl)oxy)-12-methyl-13-oxo-3,6,9-trioxa-12-azapentadecan-15-yl)amino)-8-fluoro-7-(3-hydroxynaphthalen-1-yl)quinazolin-4-yl)piperazine-1-carboxamide | 5 |
| 264 | 4-(6-chloro-2-((1-((4-(2-((S)-2-cyclohexyl-2-((S)-2-(methylamino)propanamido)acetyl)pyrrolidin-2-yl)thiazol-4-yl)naphthalen-1-yl)oxy)-15-methyl-16-oxo-3,6,9,12-tetraoxa-15-azaoctadecan-18-yl)amino)-8-fluoro-7-(3-hydroxynaphthalen-1-yl)quinazolin-4-yl)piperazine-1-carboxamide | 5 |
| 265 | 3-((4-(4-acetylpiperazin-1-yl)-6-chloro-8-fluoro-7-(3-hydroxynaphthalen-1-yl)quinazolin-2-yl)amino)-N-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethyl)-N-methylpropanamide | 5 |
| 266 | 3-((4-(4-acetylpiperazin-1-yl)-6-chloro-8-fluoro-7-(3-hydroxynaphthalen-1-yl)quinazolin-2-yl)amino)-N-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethyl)-N-methylpropanamide | 5 |
| 267 | 3-((4-(4-acetylpiperazin-1-yl)-6-chloro-8-fluoro-7-(3-hydroxynaphthalen-1-yl)quinazolin-2-yl)amino)-N-(2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)-N-methylpropanamide | 5 |
| 268 | 3-((4-(4-acetylpiperazin-1-yl)-6-chloro-8-fluoro-7-(3-hydroxynaphthalen-1-yl)quinazolin-2-yl)amino)-N-(14-((4-(2-((S)-1-((S)-2-cyclohexyl-2-((S)-2-(methylamino)propanamido)acetyl)pyrrolidin-2-yl)thiazol-4-yl)naphthalen-1-yl)oxy)-3,6,9,12-tetraoxatetradecyl)-N-methylpropanamide | 5 |
| 269 | 3-((4-(4-acetylpiperazin-1-yl)-6-chloro-8-fluoro-7-(3-hydroxynaphthalen-1-yl)quinazolin-2-yl)amino)-N-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethyl)-N-methylpropanamide | 5 |
| 270 | 3-((4-(4-acryloylpiperazin-1-yl)-6-chloro-8-fluoro-7-(3-hydroxynaphthalen-1-yl)quinazolin-2-yl)amino)-N-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethyl)-N-methylpropanamide | 5 |
| 271 | 3-((4-(4-acryloylpiperazin-1-yl)-6-chloro-8-fluoro-7-(3-hydroxynaphthalen-1-yl)quinazolin-2-yl)amino)-N-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethyl)-N-methylpropanamide | 5 |
| 272 | 3-((4-(4-acryloylpiperazin-1-yl)-6-chloro-8-fluoro-7-(3-hydroxynaphthalen-1-yl)quinazolin-2-yl)amino)-N-(2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)-N-methylpropanamide | 5 |
| 273 | 3-((4-(4-acryloylpiperazin-1-yl)-6-chloro-8-fluoro-7-(3-hydroxynaphthalen-1-yl)quinazolin-2-yl)amino)-N-(2-(2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)-N-methylpropanamide | 5 |
| 274 | 3-((4-(4-acryloylpiperazin-1-yl)-6-chloro-8-fluoro-7-(3-hydroxynaphthalen-1-yl)quinazolin-2-yl)amino)-N-(14-((4-(2-((S)-1-((S)-2-cyclohexyl-2-((S)-2-(methylamino)propanamido)acetyl)pyrrolidin-2-yl)thiazol-4-yl)naphthalen-1-yl)oxy)-3,6,9,12-tetraoxatetradecyl)-N-methylpropanamide | 5 |
| 275 | 3-(((S)-4-(4-acryloylpiperazin-1-yl)-6-chloro-8-fluoro-7-(2-hydroxyphenyl)quinazolin-2-yl)amino)-N-(2-(4-(2-((S)-1-((S)-2-cyclohexyl-2-((S)-2-(methylamino)propanamido)acetyl)pyrrolidin-2-yl)thiazol-4-yl)naphthalen-1-yl)oxy)ethyl)-N-methylpropanamide | 5 |
| 276 | 3-((4-(4-acryloylpiperazin-1-yl)-6-chloro-8-fluoro-7-((S)-2-fluoro-6-hydroxyphenyl)quinazolin-2-yl)amino)-N-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethyl)-N-methylpropanamide | 5 |
| 277 | 3-((4-(4-acryloylpiperazin-1-yl)-6-chloro-8-fluoro-7-((S)-2-fluoro-6-hydroxyphenyl)quinazolin-2-yl)amino)-N-(2-(2-(2-((4-(2-((S)-1-((S)-2-cyclohexyl-2-((S)-2-(methylamino)propan-amido)acetyl)pyrrolidin-2-yl)thiazol-4-yl)naphthalen-1-yl)oxy)ethoxy)ethoxy)ethyl)-N-methylpropanamide | 5 |
| 278 | 3-((4-(4-acryloylpiperazin-1-yl)-6-chloro-8-fluoro-7-((S)-2-fluoro-6-hydroxyphenyl)quinazolin-2-yl)amino)-N-(2-(2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)-N-methylpropanamide | 5 |
| 279 | 3-((4-(4-acryloylpiperazin-1-yl)-6-chloro-8-fluoro-7-((S)-2-fluoro-6-hydroxyphenyl)quinazolin-2-yl)amino)-N-(14-((4-(2-((S)-1-((S)-2-cyclohexyl-2-((S)-2-(methylamino)propanamido)acetyl)pyrrolidin-2-yl)thiazol-4-yl)naphthalen-1-yl)oxy)-3,6,9,12-tetraoxatetradecyl)-N-methylpropanamide | 5 |
| 280 | 3-(((S)-4-(4-acryloylpiperazin-1-yl)-6-chloro-8-fluoro-7-(2-fluoro-6-hydroxyphenyl)quinazolin-2-yl)amino)-N-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethyl)-N-methylpropanamide | 5 |
| 281 | 3-((4-(4-acetylpiperazin-1-yl)-6-chloro-8-fluoro-7-((S)-2-fluoro-6-hydroxyphenyl)quinazolin-2-yl)amino)-N-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethyl)-N-methylpropanamide | 5 |
| 282 | 3-((4-(4-acetylpiperazin-1-yl)-6-chloro-8-fluoro-7-((S)-2-fluoro-6-hydroxyphenyl)quinazolin-2-yl)amino)-N-(2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)-N-methylpropanamide | 5 |
| 283 | 3-((4-(4-acetylpiperazin-1-yl)-6-chloro-8-fluoro-7-((S)-2-fluoro-6-hydroxyphenyl)quinazolin-2-yl)amino)-N-(2-(2-(2-(2-((4-(2-((S)-1-((S)-2-cyclohexyl-2-((S)-2-(methylamino)propan-amido)acetyl)pyrrolidin-2-yl)thiazol-4-yl)naphthalen-1-yl)oxy)ethoxy)ethoxy)ethyl)-N-methylpropanamide | 5 |
| 284 | 3-((4-(4-acetylpiperazin-1-yl)-6-chloro-8-fluoro-7-((S)-2-fluoro-6-hydroxyphenyl)quinazolin-2-yl)amino)-N-(14-((4-(2-((S)-1-((S)-2-cyclohexyl-2-((S)-2-(methylamino)propanamido)acetyl)pyrrolidin-2-yl)thiazol-4-yl)naphthalen-1-yl)oxy)-3,6,9,12-tetraoxatetradecyl)-N-methylpropanamide | 5 |
| 285 | 4-(S)-6-chloro-2-(3-((2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethyl)(methyl)amino)-3-oxopropyl)amino)-8-fluoro-7-(2-fluoro-6-hydroxyphenyl)quinazolin-4-yl)piperazine-1-carboxamide | 5 |
| 286 | 4-(6-chloro-2-(3-((2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethyl)(methyl)amino)-3-oxopropyl)amino)-8-fluoro-7-(2-fluoro-6-hydroxyphenyl)quinazolin-4-yl)piperazine-1-carboxamide | 5 |
| 287 | 4-(6-chloro-2-(3-((2-(2-(2-((4-(2-((S)-1-((S)-2-cyclohexyl-2-((S)-2-(methylamino)propanamido)acetyl)pyrrolidin-2-yl)thiazol-4-yl)naphthalen-1-yl)oxy)ethoxy)ethoxy)ethyl)(methyl)amino)-3-oxopropyl)amino)-8-fluoro-7-(2-fluoro-6-hydroxyphenyl)quinazolin-4-yl)piperazine-1-carboxamide | 5 |

TABLE 8-continued

Compounds Prepared by Schemes 3-6

| | | |
|---|---|---|
| 288 | 4-(6-chloro-2-((1-((4-(2-((S)-1-((S)-2-cyclohexyl-2-((S)-2-(methylamino)propanamido)acetyl)pyrrolidin-2-yl)thiazol-4-yl)naphthalen-1-yl)oxy)-12-methyl-13-oxo-3,6,9-trioxa-12-azapentadecan-15-yl)amino)-8-fluoro-7-((S)-2-fluoro-6-hydroxyphenyl)quinazolin-4-yl)piperazine-1-carboxamide | 5 |
| 289 | 4-(6-chloro-2-((1-((4-(2-((S)-1-((S)-2-cyclohexyl-2-((S)-2-(methylamino)propanamido)acetyl)pyrrolidin-2-yl)thiazol-4-yl)naphthalen-1-yl)oxy)-15-methyl-16-oxo-3,6,9,12-tetraoxa-15-azaoctadecan-18-yl)amino)-8-fluoro-7-((S)-2-fluoro-6-hydroxyphenyl)quinazolin-4-yl)piperazine-1-carboxamide | 5 |
| 290 | 4-(6-chloro-2-(3-((2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzamido)ethyl)(methyl)amino)-3-oxopropyl)amino)-8-fluoro-7-(3-hydroxynaphthalen-1-yl)quinazolin-4-yl)piperazine-1-carboxamide | 6 |
| 291 | 4-(6-chloro-2-(3-((2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzamido)ethoxy)ethyl)(methyl)amino)-3-oxopropyl)amino)-8-fluoro-7-(3-hydroxynaphthalen-1-yl)quinazolin-4-yl)piperazine-1-carboxamide | 6 |
| 292 | 4-(6-chloro-2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-11-methyl-1,12-dioxo-5,8-dioxa-2,11-diazatetradecan-14-yl)amino)-8-fluoro-7-(3-hydroxynaphthalen-1-yl)quinazolin-4-yl)piperazine-1-carboxamide | 6 |
| 293 | 4-(6-chloro-2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-14-methyl-1,15-dioxo-5,8,11-trioxa-2,14-diazaheptadecan-17-yl)amino)-8-fluoro-7-(3-hydroxynaphthalen-1-yl)quinazolin-4-yl)piperazine-1-carboxamide | 6 |
| 294 | 4-(6-chloro-2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-17-methyl-1,18-dioxo-5,8,11,14-tetraoxa-2,17-diazaicosan-20-yl)amino)-8-fluoro-7-(3-hydroxynaphthalen-1-yl)quinazolin-4-yl)piperazine-1-carboxamide | 6 |
| 295 | (2R,3S,4R,5S)-N-(4-(2-(3-((4-(4-acetylpiperazin-1-yl)-6-chloro-8-fluoro-7-(3-hydroxynaphthalen-1-yl)quinazolin-2-yl)amino)-N-methylpropanamido)ethyl)carbamoyl)-2-methoxyphenyl)-4-(4-chloro-2-fluorophenyl)-4-cyano-5-neopentylpyrrolidine-2-carboxamide | 6 |
| 296 | (2R,3S,4R,5S)-N-(4-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethyl)carbamoyl)-3-chloro-2-fluorophenyl)-4-(4-chloro-2-fluorophenyl)-4-cyano-5-neopentylpyrrolidine-2-carboxamide | 6 |
| 297 | (2R,3S,4R,5S)-N-(4-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 298 | (2R,3S,4R,5S)-N-(4-((15-((4-acetylpiperazin-1-yl)-6-chloro-8-fluoro-7-(3-hydroxynaphthalen-1-yl)quinazolin-2-yl)amino)-12-methyl-13-oxo-3,6,9-trioxa-12-azapentadecyl)carbamoyl)-3-chloro-2-fluorophenyl)-4-(4-chloro-2-fluorophenyl)-4-cyano-5-neopentylpyrrolidine-2-carboxamide | 6 |
| 299 | (2R,3S,4R,5S)-N-(4-((18-((4-acetylpiperazin-1-yl)-6-chloro-8-fluoro-7-(3-hydroxynaphthalen-1-yl)quinazolin-2-yl)amino)-15-methyl-16-oxo-3,6,9,12-tetraoxa-15-azaoctadecyl)carbamoyl)-2-methoxyphenyl)-4-(4-chloro-2-fluorophenyl)-4-cyano-5-neopentylpyrrolidine-2-carboxamide | 6 |
| 300 | (2R,3S,4R,5S)-N-(4-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 301 | (2R,3S,4R,5S)-N-(4-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethyl)carbamoyl)-2-methoxyphenyl)-4-(4-chloro-2-fluorophenyl)-4-cyano-5-neopentylpyrrolidine-2-carboxamide | 6 |
| 302 | (2R,3S,4R,5S)-N-(4-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)ethyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 303 | (2R,3S,4R,5S)-N-(4-((15-((4-acryloylpiperazin-1-yl)-6-chloro-8-fluoro-7-(3-hydroxynaphthalen-1-yl)quinazolin-2-yl)amino)-12-methyl-13-oxo-3,6,9-trioxa-12-azapentadecyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 304 | (2R,3S,4R,5S)-N-(4-((18-((4-acryloylpiperazin-1-yl)-6-chloro-8-fluoro-7-(3-hydroxynaphthalen-1-yl)quinazolin-2-yl)amino)-15-methyl-16-oxo-3,6,9,12-tetraoxa-15-azaoctadecyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 305 | (2R,3S,4R,5S)-N-(4-(2-(3-((4-(4-acryloylpiperazin-1-yl)-6-chloro-8-fluoro-7-((S)-2-fluoro-6-hydroxyphenyl)quinazolin-2-yl)amino)-N-methylpropanamido)ethyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 306 | (2R,3S,4R,5S)-N-(4-(2-(3-((4-(4-acryloylpiperazin-1-yl)-6-chloro-8-fluoro-7-((R)-2-fluoro-6-hydroxyphenyl)quinazolin-2-yl)amino)-N-methylpropanamido)ethyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 307 | (2R,3S,4R,5S)-N-(4-(2-(3-((4-(4-acryloylpiperazin-1-yl)-6-chloro-8-fluoro-7-((S)-2-fluoro-6-hydroxyphenyl)quinazolin-2-yl)amino)-N-methylpropanamido)ethoxy)ethyl)carbamoyl)-2-methoxyphenyl)-4-(4-chloro-2-fluorophenyl)-4-cyano-5-neopentylpyrrolidine-2-carboxamide | 6 |
| 308 | (2R,3S,4R,5S)-N-(4-(2-(3-((4-(4-acryloylpiperazin-1-yl)-6-chloro-8-fluoro-7-((R)-2-fluoro-6-hydroxyphenyl)quinazolin-2-yl)amino)-N-methylpropanamido)ethoxy)ethyl)carbamoyl)-2-methoxyphenyl)-4-(4-chloro-2-fluorophenyl)-4-cyano-5-neopentylpyrrolidine-2-carboxamide | 6 |
| 309 | (2R,3S,4R,5S)-N-(4-(2-(2-(3-((4-(4-acryloylpiperazin-1-yl)-6-chloro-8-fluoro-7-((S)-2-fluoro-6-hydroxyphenyl)quinazolin-2-yl)amino)-N-methylpropanamido)ethoxy)ethoxy)ethyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 310 | (2R,3S,4R,5S)-N-(4-(2-(2-(3-((4-(4-acryloylpiperazin-1-yl)-6-chloro-8-fluoro-7-((R)-2-fluoro-6-hydroxyphenyl)quinazolin-2-yl)amino)-N-methylpropanamido)ethoxy)ethoxy)ethyl)carbamoyl)-2-methoxyphenyl)-3-chloro-2-fluorophenyl)-4-(4-chloro-2-fluorophenyl)-4-cyano-5-neopentylpyrrolidine-2-carboxamide | 6 |
| 311 | (2R,3S,4R,5S)-N-(4-((15-((4-acryloylpiperazin-1-yl)-6-chloro-8-fluoro-7-((S)-2-fluoro-6-hydroxyphenyl)quinazolin-2-yl)amino)-12-methyl-13-oxo-3,6,9-trioxa-12-azapentadecyl)carbamoyl)-3-chloro-2-fluorophenyl)-4-(4-chloro-2-fluorophenyl)-4-cyano-5-neopentylpyrrolidine-2-carboxamide | 6 |
| 312 | (2R,3S,4R,5S)-N-(4-((15-((4-acryloylpiperazin-1-yl)-6-chloro-8-fluoro-7-((R)-2-fluoro-6-hydroxyphenyl)quinazolin-2-yl)amino)-12-methyl-13-oxo-3,6,9-trioxa-12-azapentadecyl)carbamoyl)-3-chloro-2-fluorophenyl)-4-(4-chloro-2-fluorophenyl)-4-cyano-5-neopentylpyrrolidine-2-carboxamide | 6 |

TABLE 8-continued

Compounds Prepared by Schemes 3-6

| # | Compound | Scheme |
|---|---|---|
| 313 | (2R,3S,4R,5S)-N-(4-((18-((4-(4-acryloylpiperazin-1-yl)-6-chloro-8-fluoro-7-((S)-2-fluoro-6-hydroxyphenyl)quinazolin-2-yl)amino)-15-methyl-16-oxo-3,6,9,12-tetraoxa-15-azaoctadecyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 314 | (2R,3S,4R,5S)-N-(4-((18-((4-(4-acryloylpiperazin-1-yl)-6-chloro-8-fluoro-7-((R)-2-fluoro-6-hydroxyphenyl)quinazolin-2-yl)amino)-15-methyl-16-oxo-3,6,9,12-tetraoxa-15-azaoctadecyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 315 | (2R,3S,4R,5S)-N-(4-((2-(3-((4-(4-acetylpiperazin-1-yl)-6-chloro-8-fluoro-7-((S)-2-fluoro-6-hydroxyphenyl)quinazolin-2-yl)amino)-N-methylpropanamido)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 316 | (2R,3S,4R,5S)-N-(4-((2-(3-((4-(4-acetylpiperazin-1-yl)-6-chloro-8-fluoro-7-((R)-2-fluoro-6-hydroxyphenyl)quinazolin-2-yl)amino)-N-methylpropanamido)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 317 | (2R,3S,4R,5S)-N-(4-((2-(3-((4-(4-acetylpiperazin-1-yl)-6-chloro-8-fluoro-7-((S)-2-fluoro-6-hydroxyphenyl)quinazolin-2-yl)amino)-N-methylpropanamido)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 318 | (2R,3S,4R,5S)-N-(4-((2-(3-((4-(4-acetylpiperazin-1-yl)-6-chloro-8-fluoro-7-((R)-2-fluoro-6-hydroxyphenyl)quinazolin-2-yl)amino)-N-methylpropanamido)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 319 | (2R,3S,4R,5S)-N-(4-((2-(2-(3-((4-(4-acetylpiperazin-1-yl)-6-chloro-8-fluoro-7-((S)-2-fluoro-6-hydroxyphenyl)quinazolin-2-yl)amino)-N-methylpropanamido)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 320 | (2R,3S,4R,5S)-N-(4-((2-(2-(3-((4-(4-acetylpiperazin-1-yl)-6-chloro-8-fluoro-7-((R)-2-fluoro-6-hydroxyphenyl)quinazolin-2-yl)amino)-N-methylpropanamido)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 321 | (2R,3S,4R,5S)-N-(4-((15-((4-(4-acetylpiperazin-1-yl)-6-chloro-8-fluoro-7-((S)-2-fluoro-6-hydroxyphenyl)quinazolin-2-yl)amino)-12-methyl-13-oxo-3,6,9-trioxa-12-azapentadecyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 322 | (2R,3S,4R,5S)-N-(4-((15-((4-(4-acetylpiperazin-1-yl)-6-chloro-8-fluoro-7-((R)-2-fluoro-6-hydroxyphenyl)quinazolin-2-yl)amino)-12-methyl-13-oxo-3,6,9-trioxa-12-azapentadecyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 323 | (2R,3S,4R,5S)-N-(4-((18-((4-(4-acetylpiperazin-1-yl)-6-chloro-8-fluoro-7-((S)-2-fluoro-6-hydroxyphenyl)quinazolin-2-yl)amino)-15-methyl-16-oxo-3,6,9,12-tetraoxa-15-azaoctadecyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 324 | (2R,3S,4R,5S)-N-(4-((18-((4-(4-acetylpiperazin-1-yl)-6-chloro-8-fluoro-7-((R)-2-fluoro-6-hydroxyphenyl)quinazolin-2-yl)amino)-15-methyl-16-oxo-3,6,9,12-tetraoxa-15-azaoctadecyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 6 |
| 325 | 4-(6-chloro-2-(3-((2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzamido)ethyl)(methyl)amino)-3-oxopropyl)amino)-8-fluoro-7-((S)-2-fluoro-6-hydroxyphenyl)quinazolin-4-yl)piperazine-1-carboxamide | 6 |
| 326 | 4-(6-chloro-2-(3-((2-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzamido)ethoxy)ethyl)(methyl)amino)-8-fluoro-7-((S)-2-fluoro-6-hydroxyphenyl)quinazolin-4-yl)piperazine-1-carboxamide | 6 |
| 327 | 4-(6-chloro-2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-11-methyl-1,12-dioxo-5,8-dioxa-2,11-diazatetradecan-14-yl)amino)-8-fluoro-7-((S)-2-fluoro-6-hydroxyphenyl)quinazolin-4-yl)piperazine-1-carboxamide | 6 |
| 328 | 4-(6-chloro-2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-14-methyl-1,15-dioxo-5,8,11-trioxa-2,14-diazaheptadecan-17-yl)amino)-8-fluoro-7-((S)-2-fluoro-6-hydroxyphenyl)quinazolin-4-yl)piperazine-1-carboxamide | 6 |
| 329 | 4-(6-chloro-2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxyphenyl)-17-methyl-1,18-dioxo-5,8,11,14-tetraoxa-2,17-diazaicosan-20-yl)amino)-8-fluoro-7-((S)-2-fluoro-6-hydroxyphenyl)quinazolin-4-yl)piperazine-1-carboxamide | 6 |

US 11,161,841 B2

TABLE 9

Data for Compounds of Table 8

| Ex. No. | MH+ (1) | MH+ (2) | NMR Transcript | Synthetic Scheme | Mol Weight |
|---|---|---|---|---|---|
| 181 | 1080.8 | 1082.8 | $^1$H NMR (400 MHz, DMSO-d$_6$) δ 0.89 (s, 9H), 1.33-1.40 (m, 6H), 1.77 (s, 1H), 1.96-2.07 (m, 1H), 2.45 (s, 3H), 2.68 (m, 2H), 2.85 (s, 1H), 3.06 (s, 1H), 3.42 (s, 1H), 3.49-3.65 (m, 12H), 3.73 (s, 1H), 3.88-3.99 (m, 2H), 4.27 (s, 1H), 4.52 (m, 2H), 4.87 (t, J = 7.0 Hz, 1H), 5.12 (d, J = 3.2 Hz, 1H), 6.09 (s, 2H), 7.01-7.36 (m, 8H), 7.37-7.46 (m, 3H), 7.79 (d, J = 8.4 Hz, 2H), 8.41 (s, 1H), 8.98 (s, 1H), 9.97 (s, 1H). | 3 | 1080.68 |
| 182 | 1124.84 | 1126.84 | $^1$H NMR (400 MHz, DMSO-d$_6$) δ 0.84-0.91 (m, 9H), 1.24 (s, 3H), 1.35 (d, J = 6.8 Hz, 4H), 1.74-1.80 (m, 1H), 2.01-2.06 (m, 1H), 2.45 (s, 3H), 2.61-2.69 (m, 2H), 2.84 (s, 1H), 3.03 (s, 1H), 3.40-3.78 (m, 19H), 3.86-3.94 (m, 2H), 4.21-4.28 (m, 1H), 4.42-4.54 (m, 2H), 4.88-4.91 (m, 1H), 5.13 (s, 1H), 6.09 (s, 1H), 7.04 (s, 1H), 7.22-7.42 (m, 9H), 7.78-7.80 (m, 2H), 8.41-8.43 (m,1H), 8.98 (s, 1H), 9.97 (s, 1H). | 3 | 1124.73 |
| 183 | 1168.88 | 1170.88 | $^1$H NMR (400 MHz, DMSO-d$_6$) δ 0.92 (s, 9H), 1.17-1.26 (m, 3H), 1.31-1.39 (m, 3H), 1.74-1.81 (m, 1H), 1.99-2.07 (m, 1H), 2.45 (s, 3H), 2.57-2.70 (m, 2H), 2.74-2.92 (m, 3H), 3.01 (s, 1H), 3.39-3.62 (m, 20H), 3.86-3.98 (m, 2H), 4.22-4.34 (m, 1H), 4.42-4.58 (m, 2H), 4.84-4.94 (m, 2H), 5.12 (s, 1H), 6.08 (s, 2H), 7.04-7.43 (m, 11H), 7.73-7.86 (m, 2H), 8.42 (d, J = 7.6 Hz, 1H), 8.97 (s, 1H), 9.97 (s, 1H). | 3 | 1168.78 |
| 184 | 1212.91 | 1214.91 | $^1$H NMR (400 MHz, DMSO-d$_6$) δ 0.924 (s, 9H), 1.32-1.48 (m, 3H), 1.72-1.82 (m, 1H), 1.98-2.10 (m, 1H), 2.45 (s, 3H), 2.58-2.71 (m, 2H), 2.75-2.84 (m, 2H), 3.00 (s, 2H), 3.38-3.70 (m, 27H), 3.88-3.98 (m, 2H), 4.24-4.30 (m, 1H), 4.44 (t, J = 8.2 Hz, 1H), 4.54 (d, J = 9.6 Hz, 1H), 4.82-4.94 (m, 1H), 5.12 (brs, 1H), 6.09 (s, 2H), 7.00-7.16 (m, 2H), 7.20-7.30 (m, 3H), 7.32-7.38 (m, 3H), 7.40-7.46 (m, 3H), 7.80 (d, J = 8.4 Hz, 2H), 8.43 (d, J = 7.6 Hz, 1H), 8.98 (s, 1H), 9.99 (s, 1H). | 3 | 1212.83 |
| 185 | 1256.95 | 1258.95 | $^1$H NMR (400 MHz, DMSO-d$_6$) δ 0.93 (s, 9H), 1.37 (d, J = 7.2 Hz, 3H), 1.74-1.80 (m, 1H), 2.02-2.07 (m, 1H), 2.45 (s, 3H), 2.62-2.67 (m, 2H), 2.82(m, 1H), 3.01 (s, 1H), 3.17 (s, 1H), 3.36-3.66 (m, 30H), 3.95 (s, 2H), 4.28 (s, 1H), 4.42-4.46 (m, 1H), 4.53-4.55 (m, 1H),4.88-4.92 (m, 1H), 5.12-5.13 (m, 1H), 6.09 (s, 2H), 7.03-7.05 (m, 2H), 7.16 (s, 1H), 7.22-7.23 (m, 2H), 7.27-7.29 (m, 2H), 7.35-7.37 (m, 3H), 7.42-7.45 (m, 3H), 7.78-7.80 (m, 2H), 8.42-8.44 (m, 1H), 8.98 (s, IH), 9.99 (s, 1H). | 3 | 1256.89 |
| 186 | 1093.71 | 1095.71 | $^1$H NMR (400 MHz, DMSO-d$_6$) δ 8.98 (s, 1H), 8.83-8.34 (m, 1H), 8.21 (s, 1H), 7.84-7.73 (m, 2H), 7.41 (br d, J = 8.2 Hz, 3H), 7.37-7.19 (m, 7H), 7.16-7.00 (m, 2H), 5.12 (br s, 1H), 4.95-4.84 (m, 1H), 4.62-4.41 (m, 2H), 4.28 (br s, 1H), 3.93 (br s, 3H), 3.74-3.53 (m, 10H), 3.07 (s, 2H), 2.86 (s, 2H), 2.79-2.64 (m, 3H), 2.45 (s, 3H), 2.38 (br d, J = 7.4 Hz, 2H), 2.02 (br d, J = 9.5 Hz, 1H), 1.77 (br s, 1H), 1.34 (br t, J = 5.8 Hz, 3H), 1.03 (t, J = 7.4 Hz, 3H), 0.89 (br s, 9H). | 3 | 1093.71 |
| 187 | 1137.74 | 1139.74 | $^1$H NMR (400 MHz, DMSO-d$_6$) δ 10.00 (s, 1H), 8.99 (s, 1H), 8.46 (br s, 1H), 7.83-7.76 (m, 2H), 7.46-7.32 (m, 6H), 7.30-7.19 (m, 3H), 7.12-7.01 (m, 2H), 5.15 (d, J = 3.3 Hz, 1H), 4.89 (br t, J = 7.0 Hz, 1H), 4.54 (br d, J = 9.0 Hz, 1H), 4.44 (br t, J = 8.0 Hz, 1H), 4.28 (br s, 1H), 3.90 (m, 2H), 3.69-3.47 (m, 20H), 3.03-2.76 (m, 3H), 2.74-2.58 (m, 3H), 2.45 (s, 3H), 2.41-2.33 (m, 2H), 2.13-1.97 (m, 1H), 1.83-1.70 (m, 1H), 1.35 (br d, J = 6.9 Hz, 3H), 1.05-0.95 (m, 3H), 0.90 (s, 9H). | 3 | 1137.77 |
| 188 | 1181.8 | 1183.8 | $^1$H NMR, (400 MHz, DMSO-d$_6$) δ 9.99 (s, 1H), 8.99 (s, 1H), 8.42-8.46 (m, 1H), 7.76-7.84 (m, 2H), 7.41-7.46 (m, 3H), 7.34-7.39 (m, 3H), 7.26-7.29 (m, 2H), 7.21-7.24 (m, 2H), 7.03-7.16 (m, 2H), 5.12-5.15 (m, 1H), 4.86-4.94 (m, 1H), 4.52-4.57 (m, 1H), 4.41-4.48 (m, 1H), 4.26-4.31 (m, 1H), 3.91-3.96 (m, 2H), 3.40-3.83 (m, 25H), 2.76-3.06 (m, 3H), 2.59-2.66 (m, 1H), 2.45-3.47 (m, 3H), 2.36-2.42 (m, 2H), 2.00-2.10 (m, 1H), 1.71-1.84 (m, 1H), 1.34-1.48 (m, 3H), 1.03 (t, J = 7.6 Hz, 3H), 0.93 (s, 9H). | 3 | 1181.82 |
| 189 | 1225.81 | 1227.81 | $^1$H NMR (400 MHz, DMSO-d$_6$) δ 10.65-9.52 (m, 1H), 8.98 (s, 1H), 8.43 (br d, J = 7.8 Hz, 1H), 8.24 (s, 1H), 7.86-7.71 (m, 2H), 7.48-7.33 (m, 6H), 7.29-7.00 (m, 5H), 5.33-4.97 (m, 1H), 4.89 (br t, J = 7.1 Hz, 1H), 4.53 (br d, J = 9.7 Hz, 1H), 4.44 (t, J = 8.1 Hz, 1H), 4.28 (br s, 1H), 4.00-3.86 (m, 2H), 3.69 (br s, 8H), 3.61-3.46 (m, 18H), 3.02-2.77 (m, 3H), 2.70-2.58 (m, 2H), 2.43-2.43 (m, 1H), 2.45 (s, 3H), 2.42-2.14 (m, 3H), 2.10-1.94 (m, 1H), 1.84-1.71 (m, 1H), 1.49-1.32 (m, 3H), 1.02 (t, J = 7.3 Hz, 3H), 0.92 (s, 9H). | 3 | 1225.87 |
| 190 | 1269.8 | 1271.8 | $^1$H NMR (400 MHz, DMSO-d$_6$) δ 10.00 (s, 1H), 8.98 (s, 1H), 8.44 (d, J = 7.6 Hz, 1H), 7.88-7.70 (m, 2H), 7.49-7.33 (m, 6H), 7.25 (dd, J = 3.2, 19.6 Hz, 3H), 7.17-6.99 (m, 2H), 5.13 (d, J = 3.6 Hz, 1H), 4.96-4.83 (m, 1H), 4.55 (d, J = 9.6 Hz, 1H), 4.45 (t, J = 8.0 Hz, 1H), 4.33-4.21 (m, 1H), 3.98-3.89 (m, 2H), 3.70 (br s, 6H), 3.63-3.39 (m, 26H), 3.06-2.77 (m, 3H), 2.71-2.57 (m, 2H), 2.46 (s, 3H), 2.42-2.31 (m, 2H), 2.08-1.99 (m, 1H), 1.78 (ddd, J = 4.8, 8.8, 12.9 Hz, 1H), 1.37 (d, J = 6.8 Hz, 3H), 1.03 (t, J = 7.2 Hz, 3H), 0.94 (s, 9H). | 3 | 1269.93 |
| 191 | 1091.69 | 1093.69 | $^1$H NMR (400 MHz, DMSO-d$_6$) δ 8.99 (s, 1H), 8.86-8.40 (m, 1H), 8.29 (s, 1H), 7.79 (br d, J = 7.0 Hz, 2H), 7.47-7.38 (m, 3H), 7.34 (br d, J = 8.1 Hz, 3H), 7.29-7.17 (m, 4H), 7.15-7.01 (m, 2H), 6.85 (dd, J = 10.5, 16.6 Hz, 1H), 6.18 (dd, J = 2.3, 16.7 Hz, 1H), 5.77-5.71 (m, 1H), 4.95-4.85 (m, 1H), 4.62-4.39 (m, 2H), 4.28 (s, 1H), 3.87-3.34 (m, 18H), 3.13-2.83 (m, 4H), 2.67 (br dd, J = 1.8, 3.7 Hz, 2H), 2.47-2.44 (m, 3H), 2.07-1.96(m, 1H), 1.77 (br s, 1H), 1.37-1.30 (m, 3H), 0.99-0.78 (m, 9H). | 3 | 1091.70 |
| 192 | 1135.71 | 1137.72 | $^1$H NMR (400 MHz, DMSO-d$_6$) δ 8.98 (s, 1H), 8.45 (br s, 1H), 8.23 (s, 1H), 7.79 (br d, J 6.2 Hz, 2H), 7.46-7.31 (m, 6H), 7.27 (br d, J = 2.2 Hz, 1H), 7.22 (br d, J = 2.3 Hz, 2H), 7.13 (br s, 1H), 7.04 (d, J = 2.2 Hz, 1H), 6.85 (dd, J = 10.5, 16.6 Hz, 1H), 6.18 (dd, J = 2.2, 16.8 Hz, 1H), 5.77-5.71 (m, 1H), 5.02-4.84 (m, 1H), 4.54 (br d, J = 9.5 Hz, 1H), 4.44 (br t, J = 8.1 Hz, 1H), 4.28 (br s, 1H), 4.03-3.71 (m, 12H), 3.63-3.54 (m, 9H), 3.02-2.84 (m, 3H), 2.70-2.60 (m, 2H), 2.45 (s, 3H), 2.13-2.00 (m, 1H), 1.78-1.75 (m, 1H), 1.48-1.30 (m, 3H), 0.95-0.87 (m, 9H). | 3 | 1135.75 |
| 193 | 1179.75 | 1181.75 | $^1$H NMR (400 MHz, DMSO-d$_6$) δ 10.11 (s, 1H), 8.99 (s, 1H), 8.44 (d, J = 7.6 Hz, 1H), 8.19-7.98 (m, 2H), 7.84 (d, J = 8.8 Hz, 1H), 7.50-7.30 (m, 8H), 7.29-7.20 (m, 2H), 7.09 (d, J = 2.0 Hz, 1H), 6.82 (dd, J = 10.8, 16.4 Hz, 1H), 6.21 (br d, J = 18.4 Hz, 1H), 5.78 (br d, J = 12.4 Hz, 1H), 4.93-4.88 (m, 1H), 4.56 (br s, 1H), 4.47-4.42 (m, 1H), 4.28 (br s, 2H), 3.98- | 3 | 1179.80 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| | | | 3.71 (m, 10H), 3.62-3.49 (m, 14H), 3.04-2.86 (m, 3H), 2.75 (br s, 1H), 2.68 (br d, J = 4.0 Hz, 1H), 2.45 (s, 3H), 2.14-1.98 (m, 1H), 1.83-1.69 (m, 1H), 1.49-1.28 (m, 3H), 0.94 (s, 9H). | | |
| 194 | 1223.8 | 1225.8 | ¹H NMR (400 MHz, DMSO-d₆) δ 10.02 (br s, 1H), 8.98 (s, 1H), 8.45 (br d, J = 7.7 Hz, 1H), 8.17 (s, 1H), 7.84-7.76 (m, 2H), 7.49-7.33 (m, 6H), 7.28-7.10 (m, 4H), 7.03 (d, J = 2.2 Hz, 1H), 6.85 (dd, J = 10.5, 16.7 Hz, 1H), 6.26-6.11 (m, 1H), 5.81-5.67 (m, 1H), 5.14 (br s, 1H), 4.89 (br t, J = 7.2 Hz, 1H), 4.53 (d, J = 9.5 Hz, 1H), 4.43 (t, J = 8.0 Hz, 1H), 4.27 (br s, 1H), 3.99-3.88 (m, 2H), 3.86-3.65 (m, 7H), 3.62-3.60 (m, 1H), 3.61-3.40 (m, 21H), 3.03-2.77 (m, 1H), 3.03-2.77 (m, 1H), 3.03-2.77 (m, 1H), 2.61 (br s, 1H), 2.44 (s, 3H), 2.10-1.98 (m, 1H), 1.81-1.70 (m, 1H), 1.48-1.31 (m, 3H), 0.96-0.88 (m, 1H), 0.92 (s, 8H). | 3 | 1223.86 |
| 195 | 1223.94 | 1225.94 | ¹H NMR (400 MHz, DMSO-d₆) δ 8.98 (s, 1H), 8.44 (d, J = 7.6 Hz, 1H), 8.22 (s, 1H), 7.79 (br d, J = 5.4 Hz, 2H), 7.46-7.40 (m, 3H), 7.36 (br d, J = 7.9 Hz, 3H), 7.27 (d, J = 2.2 Hz, 1H), 7.22 (d, J = 3.7 Hz, 2H), 7.14 (br s, 1H), 7.04 (d, J = 2.0 Hz, 1H), 6.85 (dd, J = 10.5, 16.6 Hz, 1H), 6.20 (s, 1H), 5.78-5.71 (m, 1H), 5.13 (br s, 1H), 4.90 (br t, J = 7.3 Hz, 1H), 4.58-4.38 (m, 2H), 4.28 (br s, 1H), 3.94 (s, 2H), 3.86-3.64 (m, 8H), 3.63-3.47 (m, 20H), 3.01 (s, 2H), 2.82 (br s, 1H), 2.70-2.58 (m, 1H), 2.45 (s, 5H), 2.09-1.99 (m, 1H), 1.77 (s, 1H), 1.36 (br d, J = 5.9 Hz, 3H), 0.92 (s, 10H). | 3 | 1223.86 |
| 196 | 1223.94 | 1225.94 | ¹H NMR (400 MHz, DMSO-d₆) δ 10.00 (s, 1H), 8.98 (s, 1H), 8.43 (d, J = 7.8 Hz, 1H), 8.26 (s, 1H), 7.80 (br d, J = 5.7 Hz, 2H), 7.47-7.40 (m, 3H), 7.36 (br d, J = 8.4 Hz, 3H), 7.27 (d, J = 2.1 Hz, 1H), 7.22 (d, J = 3.7 Hz, 2H), 7.14 (br s, 1H), 7.04 (d, J = 2.2 Hz, 1H), 6.85 (dd, J = 10.5, 16.7 Hz, 1H), 6.18 (dd, J = 2.4, 16.6 Hz, 1H), 5.80-5.69 (m, 1H), 5.14 (br s, 1H), 4.90 (br t, J = 7.0 Hz, 1H), 4.59-4.40 (m, 2H), 4.28 (br s, 1H), 3.94 (s, 2H), 3.91-3.65 (m, 8H), 3.63-3.41 (m, 20H), 3.02-2.82 (m, 3H), 2.62 (br s, 1H), 2.45 (s, 3H), 2.09-1.99 (m, 1H), 1.77 (s, 1H), 1.37 (br d, J = 5.6 Hz, 3H), 0.93 (s, 9H). | 3 | 1223.86 |
| 197 | 1267.8 | 1269.8 | ¹H NMR (400 MHz, DMSO-d₆) δ 8.98 (s, 1H), 8.53-8.36 (m, 2H), 7.84-7.75 (m, 2H), 7.49-7.32 (m, 7H), 7.27 (d, J = 2.4 Hz, 1H), 7.22 (d, J = 3.6 Hz, 2H), 7.05 (d, J = 2.0 Hz, 2H), 6.85 (dd, J = 10.4, 16.4 Hz, 1H), 6.18 (dd, J = 2.0, 16.8 Hz, 1H), 5.77-5.72 (m, 1H), 5.13 (s, 1H), 4.91 (br t, J = 7.2 Hz, 1H), 4.54 (d, J = 9.6 Hz, 1H), 4.45 (t, J = 8.0 Hz, 1H), 4.28 (br s, 1H), 3.95 (s, 2H), 3.86-3.67 (m, 9H), 3.62-3.45 (m, 24H), 3.03-2.78 (m, 3H), 2.62 (br s, 1H), 2.46 (s, 3H), 2.14-1.96 (m, 1H), 1.82-1.71 (m, 1H), 1.37 (d, J = 6.4 Hz, 3H), 0.94 (s, 9H). | 3 | 1267.91 |
| 198 | 1488.15 | 1490.15 | ¹H NMR (400 MHz, DMSO-d₆) δ 8.97 (s, 1H), 8.41 (d, J = 7.7 Hz, 1H), 8.30 (s, 1H), 7.81-7.75 (m, 2H), 7.45-7.39 (m, 3H), 7.38-7.32 (m, 3H), 7.26 (d, J = 2.3 Hz, 1H), 7.21 (d, J = 3.8 Hz, 2H), 7.16-7.00 (m, 2H), 6.83 (dd, J = 10.5, 16.7 Hz, 1H), 6.16 (dd, J = 2.3, 16.8 Hz, 1H), 5.76-5.70 (m, 1H), 4.94-4.85 (m, 114), 4.54 (d, J = 9.5 Hz, 1H), 4.44 (t, J = 8.3 Hz, 1H), 4.28 (br s, 1H), 3.95 (s, 2H), 3.86-3.69 (m, 8H), 3.63-3.52 (m, 14H), 3.50-3.44 (m, 32H), 3.01-2.80 (m, 3H), 2.62 (br d, J = 7.5 Hz, 1H), 2.44 (s, 3H), 2.08-1.99 (m, 1H), 1.77 (ddd, J = 4.5, 8.7, 13.0 Hz, 1H), 1.48-1.34 (m, 3H), 0.93 (s, 9H). | 3 | 1488.18 |
| 199 | 1223.93 | 1225.93 | ¹H NMR (400 MHz, DMSO-d₆) δ 10.01 (br s, 1H), 8.98 (s, 1H), 8.39 (br d, J = 6.2 Hz, 1H), 8.29 (s, 1H), 7.79 (br d, J = 5.0 Hz, 2H), 7.46-7.32 (m, 6H), 7.28-7.07 (m, 4H), 7.03 (s, 1H), 6.84 (dd, J = 10.3, 16.7 Hz, 1H), 6.17 (br d, J = 14.9 Hz, 1H), 5.74 (br d, J = 13.1 Hz, 1H), 5.32 (br s, 1H), 4.91 (br t, J = 6.9 Hz, 1H), 4.49 (br d, J = 9.3 Hz, 1H), 4.37-4.30 (m, 1H), 4.20 (br s, 1H), 3.92 (s, 2H), 3.88-3.64 (m, 11H), 3.60-3.42 (m, 21H), 3.00 (s, 3H), 2.61 (br s, 2H), 1.67-1.56 (m, 1H), 1.36 (br d, J = 7.5 Hz, 3H), 0.97-0.89 (m, 9H). | 3 | 1223.86 |
| 200 | 1079.81 | 1081.81 | ¹H NMR (400 MHz, DMSO-d₆) δ 8.98 (s, 114), 8.41-8.32 (m, 1H), 7.85-7.75 (m, 2H), 7.50-7.04 (m, 11H), 5.11 (s, 1H), 4.97-4.81 (m, 1H), 4.59-4.36 (m, 2H), 4.34-3.90 (m, 4H), 3.80-3.48 (m, 11H), 3.10-3.01 (m, 2H), 2.91-2.81 (m, 2H), 2.76-2.63 (m, 3H), 2.46-2.40 (m, 3H), 2.37-2.28 (m, 1H), 2.12-1.95 (m, 4H), 1.84-1.71 (m, 1H), 1.43-1.24 (m, 3H), 1.03-0.78 (m, 9H). | 3 | 1079.69 |
| 201 | 1123.77 | 1125.77 | ¹H NMR (400 MHz, DMSO-d₆) δ 8.97 (s, 1H), 8.77-8.36 (m, 1H), 7.83-7.73 (m, 2H), 7.48-6.96 (m, 11H), 5.23-5.06 (m, 1H), 4.95-4.81 (m, 1H), 4.71-4.37 (m, 2H), 4.32-4.17 (m, 1H), 3.98-3.84 (m, 2H), 3.78-3.48 (m, 18H), 3.02 (s, 2H), 2.83 (s, 2H), 2.72-2.58 (m, 1H), 2.44 (s, 3H), 2.10-2.01 (m, 4H), 1.84-1.68 (m, 1H), 1.51-1.28 (m, 3H), 0.90 (s, 9H). | 3 | 1123.74 |
| 202 | 1167.88 | 1169.89 | ¹H NMR (400 MHz, DMSO-d₆) δ 8.97 (s, 1H), 8.78-8.39 (m, 1H), 7.84-7.74 (m, 2H), 7.49-7.00 (m, 11H), 4.89 (t, J = 6.4 Hz, 1H), 4.71-4.49 (m, 1H), 4.44 ( t, J = 8.0 Hz, 1H), 4.34-4.19 (m, 1H), 3.99-3.86 (m, 2H), 3.76-3.44 (m, 24H), 3.01 (s, 1H), 2.82 (s, 3H), 2.71-2.58 (m, 2H), 2.44 (s, 3H), 2.10-1.96 (m, 4H), 1.82-1.69 (m, 1H), 1.50-1.29 (m, 3H), 0.91 (s, 9H). | 3 | 1167.79 |
| 203 | 1211.9 | 1213.9 | ¹H NMR (400 MHz, DMSO-d₆) δ 10.00 (s, 1H), 8.97 (s, 1H), 8.76-8.38 (m, 1H), 7.86-7.75 (m, 2H), 7.48-6.99 (m, 11H), 5.13 (d, J = 3.2 Hz, 1H), 5.02-4.84 (m, 1H), 4.53 (d, J = 9.6 Hz, 1H), 4.44 (t, J = 8.4 Hz, 1H), 4.35-4.17 (m, 1H), 3.99-3.89 (m, 2H), 3.78-3.40 (m, 27H), 3.04-2.96 (m, 1H), 2.85-2.78 (m, 1H), 2.71-2.56 (m, 2H), 2.44 (s, 3H), 2.10-1.99 (m, 4H), 1.83-1.70 (m, 1H), 1.51-1.32 (m, 3H), 0.92 (s, 9H). | 3 | 1211.85 |
| 204 | 1255.95 | 1257.95 | ¹H NMR (400 MHz, DMSO-d₆) δ 10.03 (s, 1H), 8.96 (s, 1H), 8.77-8.31 (m, 1H), 7.86-7.72 (m, 2H), 7.49-6.97 (m, 11H), 5.22-5.11 (m, 1H), 4.89 (t, J = 7.2 Hz, 1H), 4.60-4.38 (m, 2H), 4.33-4.18 (m, 2H), 3.98-3.87 (m, 2H), 3.74-3.52 (m, 29H), 3.48-3.48 (m, 1H), 3.00 (s, 1H), 2.80 (s, 2H), 2.71-2.56 (m, 314), 2.44 (s, 314), 2.06 (s, 4H), 1.84-1.69 (m, 1H), 1.49-1.31 (m, 3H), 0.92 (s, 9H). | 3 | 1255.90 |
| 205 | 1059.8 | 1061.8 | ¹H NMR (400 MHz, METHANOL-d₄) δ 10.19 (br s, 1H), 8.98 (s, 1H), 8.42 (br s, 1H), 8.20 (s, 1H), 7.71 (br s, 1H), 7.47-7.00 (m, 7H), 6.87-6.74 (m, 3H), 6.16 (dd, J = 2.3, 16.6 Hz, 1H), 5.76-5.67 (m, 1H), 5.12 (br s, 1H), 4.94-4.82 (m, 1H), 4.57-4.36 (m, 2H), 4.28 (br | 3 | 1059.63 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| | | | s, 1H), 4.02-3.87 (m, 2H), 3.83-3.49 (m, 18H), 3.08 (br s, 1H), 2.87-2.84 (m, 1H), 2.67 (br d, J = 1.7 Hz, 1H), 2.45-2.43 (m, 3H), 2.07-1.97 (m, 1H), 1.76 (br d, J = 4.8 Hz, 1H), 1.49-1.26 (m, 3H), 0.91 (br d, J = 5.5 Hz, 9H). | | |
| 206 | 1059.8 | 1061.8 | ¹H NMR (400 MHz, DMSO-d₆) δ 10.44-9.98 (m, 1H), 8.98 (s, 1H), 8.73-8.43 (m, 1H), 8.23 (s, 1H), 7.71 (br s, 1H), 7.08 (br s, 7H), 6.89-6.73 (m, 3H), 6.16 (dd, J = 2.4, 16.7 Hz, 1H), 5.80-5.63 (m, 1H), 5.24-5.08 (m, 1H), 4.88 (br d, J = 3.4 Hz, 1H), 4.63-4.40 (m, 2H), 4.27 (br s, 1H), 4.01-3.88 (m, 2H), 3.84-3.53 (m, 18H), 3.07 (br s, 1H), 2.86 (s, 1H), 2.74-2.69 (m, 1H), 2.45-2.44 (m, 3H), 2.07-1.98 (m, 1H), 1.83-1.72 (m, 1H), 1.45-1.30 (m, 3H), 0.91 (br d, J = 3.4 Hz, 9H). | 3 | 1059.63 |
| 207 | 1103.8 | 1105.8 | ¹H NMR (400 MHz, MeOD) δ 8.86-8.84 (m, 1H), 8.25 (s, 1H), 7.75-7.71 (m, 1H), 7.41-7.25 (m, 5H), 6.82-6.74 (m, 2H), 6.71-6.66 (m, 1H), 6.25 (dd, J = 2.0, 16.8 Hz, 1H), 5.79 (d, J = 11.6 Hz, 1H), 4.99-4.94 (m, 1H), 4.66 (s, 1H), 4.42-4.33 (m, 1H), 4.04-3.70 (m, 15H), 3.64-3.59 (m, 9H), 3.14 (s, 1H), 2.94 (s, 1H), 2.90-2.82 (m, 1H), 2.78-2.75 (m, 1H), 2.45 (s, 3H), 2.21-2.16 (m, 1H), 1.98-1.91 (m, 1H), 1.54-1.47 (m, 3H), 1.01-0.98 (m, 9H). | 3 | 1103.68 |
| 208 | 1103.8 | 1105.8 | ¹H NMR (400 MHz, MeOD) s 8.93-8.92 (m, 1H), 8.07-8.01 (m, 1H), 7.44-7.25 (m, 5H), 6.82-6.73 (m, 3H), 6.31 (d, J = 16.8 Hz, 1H), 5.83 (d, J = 10.4 Hz, 1H), 5.03-4.96 (m, 1H), 4.68 (s, 1H), 4.59-4.55 (m, 1H), 4.41-4.22 (m, 5H), 3.96-3.80 (m, 9H), 3.73-3.48 (m, 10H), 3.15 (s, 1H), 2.98 (s, 1H), 2.89 (s, 1H), 2.79 (s, 1H), 2.48-2.46 (m, 3H), 2.23 (s, 1H), 2.00-1.92 (m, 1H), 1.57-1.48 (m, 3H), 1.02 (s, 9H). | 3 | 1103.68 |
| 209 | 1147.86 | 1149.86 | ¹H NMR (400 MHz, DMSO-d₆) δ 10.25 (br s, 1H), 8.98 (s, 1H), 8.45 (br d, J = 7.6 Hz, 1H), 7.72 (s, 1H), 7.50-7.02 (m, 7H), 6.94-6.60 (m, 3H), 6.17 (dd, J = 2.0, 16.8 Hz, 1H), 5.84-5.61 (m, 1H), 5.14 (br s, 1H), 4.98-4.82 (m, 1H), 4.59-4.40 (m, 2H), 4.35-4.21 (m, 1H), 3.98-3.87 (m, 2H), 3.79-3.46 (m, 24H), 3.06-2.82 (m, 3H), 2.72-2.57 (m, 2H), 2.46 (s, 3H), 2.08-1.99 (m, 1H), 1.77 (ddd, J = 4.4, 8.8, 12.8 Hz, 1H), 1.48-1.33 (m, 3H), 0.93 (br d, J = 2.4 Hz, 9H). | 3 | 1147.73 |
| 210 | 1147.86 | 1149.86 | ¹H NMR (400 MHz, DMSO-d₆) δ 10.22 (br s, 1H), 8.98 (s, 1H), 8.45 (br d, J = 7.8 Hz, 1H), 7.72 (s, 1H), 7.55-6.99 (m, 7H), 6.92-6.68 (m, 3H), 6.17 (dd, J = 2.4, 16.7 Hz, 1H), 5.79-5.63 (m, 1H), 5.14 (br s, 1H), 4.89 (br t, J = 6.4 Hz, 1H), 4.54 (d, J = 9.4 Hz, 1H), 4.44 (t, J = 8.0 Hz, 1H), 4.28 (br s, 1H), 3.99-3.90 (m, 2H), 3.80-3.49 (m, 24H), 3.06-2.82 (m, 3H), 2.75-2.58 (m, 2H), 2.45 (s, 3H), 2.04 (br d, J = 8.0 Hz, 1H), 1.81-1.72 (m, 1H), 1.48-1.32 (m, 3H), 0.93 (br d, J = 2.4 Hz, 9H). | 3 | 1147.73 |
| 211 | 1191.89 | 1193.89 | ¹H NMR (400 MHz, MeOD) δ 8.87 (s, 1H), 8.27 (s, 1H), 7.77 (s, 1H), 7.43-7.35 (m, 4H), 7.32-7.27 (m, 1H), 6.84-6.68 (m, 3H), 6.29-6.24 (m, 1H), 5.81-5.78 (m, 1H), 5.01-4.98 (m, 1H), 4.69-4.66 (m, 1H), 4.60-4.55 (m, 1H), 4.11-3.98 (m, 2H), 3.90-3.82 (m, 7H), 3.75-3.72 (m, 4H), 3.66-3.51 (m, 17H), 3.15 (s, 1H), 2.96-2.94 (m, 2H), 2.86-2.83 (m, 1H), 2.78-2.74 (m, 1H), 2.47 (s, 3H), 2.23-2.17 (m, 1H), 2.01-1.92 (m, 1H), 1.56-1.48 (m, 3H), 1.03-1.02 (m, 9H). | 3 | 1191.79 |
| 212 | 1191.89 | 1193.89 | ¹H NMR (400 MHz, MeOD) δ 8.86 (m, 1H), 7.75 (m, 1H), 7.42-7.34 (m, 4H), 7.31-7.25 (m, 1H), 6.84-6.74 (m, 2H), 6.71-6.67 (m, 1H), 6.26 (dd, J = 1.6, 16.4 Hz, 1H), 5.79 (dd, J = 1.6, 16.4 Hz, 1H), 4.99-4.96 (m, 1H), 4.68-4.66 (m, 1H), 4.60-4.54 (m, 1H), 4.42-4.36 (m, 1H), 4.08-3.97 (m, 2H), 3.91-3.82 (m, 7H), 3.75-3.71 (m, 4H), 3.65-3.50 (m, 17H), 3.14 (s, 1H), 2.94 (s, 2H), 2.85-2.82 (m, 1H), 2.77-2.73 (m, 1H), 2.46 (s, 3H), 2.22-2.17 (m, 1H), 2.00-1.91 (m, 1H), 1.56-1.47 (m, 3H), 1.02-1.01 (m, 9H). | 3 | 1191.79 |
| 213 | 1235.93 | 1237.94 | ¹H NMR (400 MHz, DMSO-d₆) δ 10.25 (br s, 1H), 8.98 (s, 1H), 8.42 (d, J = 7.6 Hz, 1H), 8.33 (s, 1H), 7.72 (s, 1H), 7.49-7.41 (m, 2H), 7.41-7.28 (m, 4H), 7.16-6.99 (m, 1H), 6.90-6.73 (m, 3H), 6.17 (dd, J = 2.4, 16.8 Hz, 1H), 5.79-5.69 (m, 1H), 5.12 (br s, 1H), 4.96-4.86 (m, 1H), 4.55 (d, J = 9.6 Hz, 1H), 4.45 (t, J = 8.0 Hz, 1H), 4.34-4.23 (m, 1H), 4.00-3.89 (m, 2H), 3.82-3.65 (m, 8H), 3.63-3.44 (m, 25H), 3.07-2.80 (m, 3H), 2.66-2.58 (m, 1H), 2.46 (s, 3H), 2.11-1.98 (m, 1H), 1.84-1.73 (m, 1H), 1.50-1.34 (m, 3H), 0.94 (s, 9H). | 3 | 1235.84 |
| 214 | 1235.93 | 1237.94 | ¹H NMR (400 MHz, DMSO-d₆) δ 10.25 (br s, 1H), 8.98 (s, 1H), 8.43 (d, J = 7.6 Hz, 1H), 8.34 (s, 1H), 7.72 (s, 1H), 7.48-7.42 (m, 2H), 7.41-7.27 (m, 4H), 7.19-7.00 (m, 1H), 6.94-6.70 (m, 3H), 6.17 (dd, J = 2.0, 16.8 Hz, 1H), 5.78-5.66 (m, 1H), 5.12 (br s, 1H), 4.96-4.86 (m, 1H), 4.55 (d, J = 9.6 Hz, 1H), 4.45 (t, J = 8.0 Hz, 1H), 4.32-4.22 (m, 1H), 4.00-3.89 (m, 2H), 3.83-3.64 (m, 8H), 3.63-3.44 (m, 25H), 3.08-2.77 (m, 3H), 2.65-2.57 (m, 1H), 2.46 (s, 3H), 2.09-1.98 (m, 1H), 1.82-1.74 (m, 1H), 1.49-1.34 (m, 3H), 0.94 (s, 9H). | 3 | 1235.84 |
| 215 | 1047.8 | 1049.8 | ¹H NMR (METHANOL-d₄) δ 8.76 (s, 1H), 7.64-7.38 (m, 1H), 7.32-7.09 (m, 5H), 6.71-6.64 (m, 1H), 6.59 (t, J = 8.7 Hz, 1H), 4.97-4.80 (m, 2H), 4.68-4.52 (m, 1H), 4.40-4.23 (m, 1H), 4.00-3.91 (m, 1H), 3.87 (br d, J = 7.9 Hz, 1H), 3.80-3.39 (m, 17H), 3.08 (br s, 1H), 2.87 (s, 2H), 2.73 (br d, J = 6.6 Hz, 1H), 2.38-2.29 (m, 3H), 2.11-1.84 (m, 5H), 1.46-1.34 (m, 3H), 1.02-0.87 (m, 9H). | 3 | 1047.62 |
| 216 | 1047.8 | 1049.8 | ¹H NMR (METHANOL-d₄) δ 8.86 (s, 1H), 7.80-7.50 (m, 1H), 7.45-7.11 (m, 5H), 6.81-6.62 (m, 2H), 5.05-4.89 (m, 211), 4.77-4.62 (m, 1H), 4.46 (br s, 1H), 4.03 (br d, J = 8.6 Hz, 1H), 3.98-3.90 (m, 1H), 3.90-3.50 (m, 17H), 3.24-3.09 (m, 1H), 3.05-2.93 (m, 2H), 2.83 (br d, J = 4.2 Hz, 1H), 2.50-2.38 (m, 3H), 2.26-1.92 (m, 5H), 1.62-1.37 (m, 3H), 0.99 (s, 9H). | 3 | 1047.62 |
| 217 | 1091.8 | 1093.8 | ¹H NMR (400 MHz, MeOD) δ 8.87-8.85 (m, 1H), 7.70-7.67 (m, 1H), 7.39-7.27 (m, 5H), 6.78-6.75 (m, 2H), 6.72-6.67 (m, 1H), 5.01-4.95 (m, 1H), 4.68 (s, 1H), 4.44-4.35 (m, 1H), 3.97- 3.96 (m, 1H), 3.85-3.75 (m, 12H), 3.65-3.60 (m, 10H), 3.17 (s, 1H), 2.95 (s, 2H), 2.79-2.76 (m, 1H), 2.46 (s, 3H), 2.20-2.15 (m, 4H), 2.02-1.94 (m, 1H), 1.54-1.47 (m, 3H), 1.03-1.00 (m, 9H). | 3 | 1091.67 |
| 218 | 1091.8 | 1093.8 | ¹H NMR (400 MHz, DMSO-d₆) δ 10.19(s, 1H), 8.97 (s, 1H), 8.44 (d, J = 6.4 Hz, 1H), 7.69 (s, 1H), 7.43-7.40 (m, 2H), 7.37-7.27 (m, 4H),7.17-7.05 (m, 1H), 6.83 (d, J = 8.4 Hz, | 3 | 1091.67 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| | | | 1H), 6.76 (t, J = 8.8 Hz, 1H), 5.14 (s, 1H), 4.91-4.86 (m, 1H), 4.53 (t, J = 9.6 Hz, 1H), 4.45-4.41 (m, 1H), 4.27 (s, 1H), 3.94-3.89 (m, 2H), 3.75-3.50 (m, 21H), 3.02 (s, 1H), 2.94 (s, 1H), 2.66-2.61 (m, 2H), 2.44 (s, 3H), 2.06-2.01 (m, 4H), 1.79-1.72 (m, 1H), 1.45-1.33(m, 3H), 0.91-0.90 (m, 9H). | | |
| 219 | 1135.86 | 1137.86 | $^1$H NMR (400 MHz, DMSO-$d_6$) δ 10.28 (br s, 1H), 8.99 (s, 1H), 8.45 (d, J = 7.6 Hz, 1H), 7.71 (s, 1H), 7.47-7.26 (m, 6H), 7.22-6.98 (m, 1H), 6.87-6.70 (m, 2H), 5.14 (br s, 1H), 4.90 (br t, J = 6.4 Hz, 1H), 4.54 (d, J = 9.6 Hz, 1H), 4.44 (t, J = 8.4 Hz, 1H), 4.31-4.21 (m, 1H), 3.99-3.87 (m, 2H), 3.64-3.43 (m, 24H), 3.08-2.81 (m, 3H), 2.72-2.58 (m, 2H), 2.46 (s, 3H), 2.09-2.01 (m, 4H), 1.82-1.70 (m, 1H), 1.48-1.34 (m, 3H), 0.93 (br d, J = 2.4 Hz, 9H). | 3 | 1135.72 |
| 220 | 1135.86 | 1137.86 | $^1$H NMR (400 MHz, DMSO-$d_6$) δ 10.23 (br s, 1H), 8.98 (s, 1H), 8.45 (d, J = 7.6 Hz, 1H), 7.71 (s, 1H), 7.51-7.24 (m, 6H), 7.20-6.98 (m, 1H), 6.89-6.69 (m, 2H), 5.14 (br s, 1H), 4.90 (br t, J = 6.4 Hz, 1H), 4.54 (d, J = 9.4 Hz, 1H), 4.45 (t, J = 8.0 Hz, 1H), 4.33-4.20 (m, 1H), 3.99-3.86 (m, 2H), 3.69-3.47 (m, 24H), 3.05-2.81 (m, 3H), 2.71-2.58 (m, 2H), 2.46 (s, 3H), 2.12-1.95 (m, 4H), 1.82-1.70 (m, 1H), 1.48-1.32 (m, 3H), 0.93 (br d, J = 2.4 Hz, 9H). | 3 | 1135.72 |
| 221 | 1179.89 | 1181.89 | $^1$H NMR (400 MHz, MeOD) δ 8.88-8.87 (m, 1H), 8.38 (s, 1H), 7.75 (s, 1H), 7.43-7.37 (m, 4H), 7.32-7.27 (m, 1H), 6.79 (d, J = 8.4 Hz, 1H), 6.71 (t, J = 8.8, 1H), 5.00-4.97 (m, 1H), 4.67 (s, 1H), 4.61-4.57 (m, 1H), 4.43-4.37 (m, 1H), 4.03 (s, 2H), 3.83-3.72 (m, 10H), 3.66-3.52 (m, 18H), 3.15 (s, 1H), 2.95-2.94 (m, 2H), 2.86-2.83 (m, 1H), 2.78-2.75 (m, 1H), 2.47 (s, 3H), 2.23-2.13 (m, 4H), 2.02-1.92 (m, 1H), 1.55-1.49 (m, 3H), 1.04-1.02 (m, 9H). | 3 | 1179.78 |
| 222 | 1179.89 | 1181.89 | $^1$H NMR (400 MHz, MeOD) δ 8.88-8.87 (m, 1H), 7.75 (s, 1H), 7.43-7.37 (in, 4H), 7.32-7.27 (m, 1H), 6.77 (d, J = 8.0, 1H), 6.73-6.68 (m, 1H), 5.00-4.97 (m, 1H), 4.69-4.67 (m, 1H), 4.61-4.57 (m, 1H), 4.43-4.37 (m, 1H), 4.11-3.98 (m, 2H), 3.83-3.72 (m, 10H), 3.66-3.52 (m, 18H), 3.15 (s, 1H), 2.95-2.94 (m, 2H), 2.86-2.83 (m, 1H), 2.78-2.74 (m, 1H), 2.47 (s, 3H), 2.23-2.16 (m, 4H), 1.99-1.92 (m, 1H), 1.55-1.48 (m, 3H), 1.04-1.02 (m, 9H). | 3 | 1179.78 |
| 223 | 1223.93 | 1225.93 | $^1$H NMR (400 MHz, DMSO-$d_6$) δ 10.25 (br s, 1H), 8.99 (s, 1H), 8.45 (d, J = 8.0 Hz, 1H), 7.71 (s, 1H), 7.46-7.41 (m, 2H), 7.41-7.35 (m, 3H), 7.34-7.26 (m, 1H), 7.18-6.99 (m, 1H), 6.88-6.69 (m, 2H), 5.14 (br s, 1H), 4.96-4.85 (m, 1H), 4.54 (d, J = 9.2 Hz, 1H), 4.44 (t, J = 8.0 Hz, 1H), 4.34-4.24 (m, 1H), 4.00-3.90 (m, 2H), 3.69-3.43 (m, 32H), 3.08-2.79 (m, 4H), 2.64-2.56 (m, 1H), 2.46 (s, 3H), 2.09-2.01 (m, 4H), 1.81-1.72 (m, 1H), 1.37 (d, J = 6.8 Hz, 3H), 0.94 (s, 9H). | 3 | 1223.83 |
| 224 | 1223.93 | 1225.93 | $^1$H NMR (400 MHz, DMSO-$d_6$) δ 10.40 (s, 1H), 8.98 (s, 1H), 8.45 (d, J = 7.6 Hz, 1H), 7.69 (s, 1H), 7.46-7.41 (m, 2H), 7.40-7.34 (in, 3H), 7.25 (br s, 1H), 7.19-6.97 (m, 1H), 6.93-6.56 (m, 2H) 5.36-5.00 (m, 1H), 4.94-4.86 (m, 1H), 4.54 (d, J = 9.6 Hz, 1H), 4.44 (t, J = 8.0 Hz, 1H), 4.30-4.21 (m, 1H), 3.95 (s, 2H), 3.66-3.42 (m, 32H), 3.07-2.80 (m, 4H), 2.64-2.57 (m, 1H), 2.45 (s, 3H), 2.08-2.00 (m, 4H), 1.83-1.69 (m, 1H), 1.37 (d, J = 7.2 Hz, 3H), 0.93 (s, 9H). | 3 | 1223.83 |
| 225 | 1048.77 | 1050.77 | $^1$H NMR (400 MHz, DMSO-$d_6$) δ 8.97 (s, 1H), 8.41 (br s, 1H), 8.28 (s, 1H), 7.71-7.66 (m, 1H), 7.48-7.21 (m, 7H), 7.07 (br s, 1H), 6.84 (d, J = 8.0 Hz, 1H), 6.76 (t, J = 8.8 Hz, 1H), 6.06 (s, 2H), 4.94-4.84 (m, 1H), 4.57-4.41 (m, 2H), 4.31-4.23 (m, 1H), 4.01-3.86 (m, 2H), 3.57-3.27 (m, 16H), 3.07 (br s, 2H), 2.86 (s, 2H), 2.66 (d, J = 6.4 Hz, 2H), 2.46-2.42 (m, 3H), 2.11-1.97 (m, 1H), 1.83-1.72 (m, 1H), 1.48-1.32 (m, 3H), 0.91 (d, J = 5.6 Hz, 9H). | 3 | 1048.61 |
| 226 | 1048.77 | 1050.77 | $^1$H NMR (400 MHz, DMSO-$d_6$) δ 10.22 (br s, 1H), 8.98 (s, 1H), 8.83-8.36 (m, 1H), 8.19 (s, 1H), 7.69 (s, 1H), 7.45-7.24 (m, 6H), 7.17-6.90 (m, 1H), 6.83 (d, J = 8.0 Hz, 1H), 6.77 (t, J = 8.8 Hz, 1H), 6.09 (s, 2H), 5.14 (br s, 1H), 4.93-4.82 (m, 1H), 4.59-4.38 (m, 2H), 4.28 (br s, 1H), 4.03-3.87 (m, 2H), 3.61-3.48 (m, 15H), 3.08 (br s, 2H), 2.86 (s, 2H), 2.76-2.60(m, 2H), 2.46-2.41 (m, 3H), 2.11-1.96 (m, 1H), 1.84-1.71 (m, 1H), 1.49-1.29 (m, 3H), 0.90 (s, 9H). | 3 | 1048.61 |
| 227 | 1092.81 | 1094.81 | $^1$H NMR (400 MHz, DMSO-$d_6$) δ 10.21 (s, 1H), 8.98 (s, 1H), 8.43 (br d, J = 7.6 Hz, 1H), 8.21 (s, 1H), 7.70 (s, 1H), 7.45-7.29 (m, 6H), 7.22-6.99 (m, 1H), 6.89-6.73 (m, 2H), 6.07 (s, 2H), 5.13 (s, 1H), 4.90 (t, J = 7.2 Hz, 1H), 4.59-4.41 (m, 2H), 4.29 (s, 1H), 4.02-3.85 (m, 3H), 3.85-3.64 (m, 4H), 3.63-3.45 (m, 11H), 3.04 (br s, 2H), 2.93-2.59 (m, 1H), 2.93-2.59 (m, 4H), 2.45 (s, 3H), 2.45-2.39 (m, 1H), 2.35-2.32 (m, 1H), 2.14-2.00 (m, 1H), 1.83-1.71 (m, 1H), 1.36 (d, J = 7.2 Hz, 3H), 0.92 (br d, J = 5.2 Hz, 9H). | 3 | 1092.66 |
| 228 | 1136.84 | 1138.84 | $^1$H NMR (400 MHz, DMSO-$d_6$) δ 8.99 (s, 1H), 8.45 (d, J = 7.2 Hz, 1H), 8.06 (s, 2H), 7.50-7.37 (m, 7H), 6.89-6.80 (m, 2H), 6.12 (brs, 1H), 4.90-4.85 (m, 1H), 4.56-4.13 (m, 4H), 3.72-3.50 (m, 25H), 2.99, 2.88 (s, 3H), 2.70 (d, J = 24.8 Hz, 2H), 2.45 (s, 3H), 2.12-2.00 (m, 1H), 1.85-1.70 (m, 1H), 1.45-1.36 (m, 3H), 0.93 (s, 9H). | 3 | 1136.71 |
| 229 | 1136.84 | 1138.84 | $^1$H NMR (40 0MHz, DMSO-$d_6$) δ 8.99 (s, 1H), 8.45 (d, J = 7.6 Hz, 1H), 8.11-8.05 (m, 2H), 7.45-7.35 (m, 7H), 6.90-6.80 (m, 2H), 6.11 (brs, 1H), 4.95-4.85 (m, 1H), 4.68-3.95 (m, 4H), 3.73-3.45 (m, 25H), 2.99, 2.88 (s, 3H), 2.70 (d, J = 25.6 Hz, 2H), 2.45 (s, 3H), 2.09-2.03 (m, 1H), 1.81-1.70 (m, 1H), 1.37 (d, J = 6.8 Hz, 3H), 0.94 (s, 9H). | 3 | 1136.71 |
| 230 | 1180.88 | 1182.88 | $^1$H NMR (400 MHz, DMSO-$d_6$) δ 10.50 (brs, 1H), 8.99 (s, 1H), 8.44(d, J = 7.6 Hz, 1H), 8.11-7.93 (m, 2H), 7.48-7.28 (m, 6H), 6.93-6.77 (m, 2H), 6.13 (brs, 2H), 4.90 (t, J = 7.6 Hz, 1H), 4.54 (d, J = 9.2 Hz, 1H), 4.43 (t, J = 8.0 Hz, 1H), 4.31-4.21 (m, 1H), 4.20-4.01 (m, 4H), 4.00-3.87 (m, 2H), 3.78-3.65 (m, 2H), 3.64-3.36 (m, 23H), 3.01-2.84 (m, 3H), 2.77-2.62 (m, 2H), 2.45 (s, 3H), 2.10-1.99 (m, 1H), 1.83-1.70 (m, 1H), 1.51-1.32 (m, 3H), 0.93 (s, 9H). | 3 | 1180.76 |
| 231 | 1180.88 | 1182.88 | $^1$H NMR (400 MHz, DMSO-$d_6$) δ 10.49 (brs, 1H), 8.98 (s, 1H), 8.44 (d, J = 7.6 Hz, 1H), 8.05 (s, 1H), 7.95 (brs, 1H), 7.48-7.30 (m, 6H), 6.91-6.77 (m, 2H), 6.13 (brs, 2H), 4.96- | 3 | 1180.76 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| | | | 4.85 (m. 11H) 4.54 (d, J = 9.6 Hz, 1H), 4.43 (t, J = 8.4 Hz, 1H), 4.29-4.27 (m, 1H), 4.14-4.10 (m, 4H), 3.99-3.86 (m, 2H), 3.74-3.65 (m, 2H), 3.63-3.42 (m, 23H), 3.02-2.86 (m, 3H), 2.77-2.61 (m, 2H), 2.45 (s, 3H), 2.12-1.97 (m, 1H), 1.84-1.68 (m, 1H), 1.49-1.32 (m, 3H), 0.93 (s, 9H). | | |
| 232 | 1224.91 | 1226.91 | $^1$H NMR (400 MHz, METHANOL-$d_4$) δ 8.94-8.86 (m, 1H), 8.68-8.26 (m, 1H), 7.83-7.60 (m, 1H), 7.54-7.27 (m, 5H), 6.78 (d, J = 8.2 Hz, 1H), 6.72 (t, J = 8.7 Hz, 1H), 5.02 (br d, J = 7.0 Hz, 1H), 4.83-4.77 (m, 1H), 4.73-4.66 (m, 1H), 4.65-4.54 (m, 1H), 4.45 (br s, 1H), 4.15-3.49 (m, 33H), 3.26-2.92 (m, 3H), 2.92-2.68 (m, 2H), 2.57-2.44 (m, 3H), 2.41-1.93 (m, 2H), 1.61-1.48 (m, 3H), 1.14-0.96 (m, 9H). | 3 | 1224.82 |
| 233 | 1224.91 | 1226.91 | $^1$H NMR (400 MHz, METHANOL-$d_4$) δ 8.94 -8.85 (m, 1H), 8.63-8.25 (m, 1H), 7.77 (br s, 1H), 7.48-7.25 (m, 5H), 6.78 (d, J = 8.2 Hz, 1H), 6.72 (t, J = 8.7 Hz, 1H), 5.13-4.98 (m, 1H), 4.82-4.76 (m, 1H), 4.69 (s, 1H), 4.65-4.56 (m, 1H), 4.48-4.36 (m, 1H), 4.13-3.46 (m, 33H), 3.28-2.92 (m, 3H), 2.90-2.73 (m, 2H), 2.54-2.43 (m, 3H), 2.27-1.93 (m, 2H), 1.62-1.47 (m, 3H), 1.12-1.01 (m, 9H). | 3 | 1224.82 |
| 234 | 1079.79 | 1081.79 | $^1$H NMR (400 MHz, DMSO-$d_6$) δ 10.34-10.06 (m, 1H), 8.97 (s, 1H), 8.42 (br s, 1H), 7.72 (br s, 1H), 7.41 (br d, J = 7.6 Hz, 2H), 7.33 (br t, J = 8.5 Hz, 4H), 7.08 (br s, 1H), 6.86-6.71 (m, 2H), 6.33 (d, J = 7.5 Hz, 1H), 5.35 (t, J = 7.3 Hz, 1H), 5.12 (br s, 1H), 5.00-4.78 (m, 1H), 4.52 (br d, J = 9.9 Hz, 1H), 4.47-4.38 (m, 1H), 4.28 (br s, 1H), 4.01-3.88 (m, 2H), 3.79 (br s, 2H), 3.67 (br s, 6H), 3.57 (br s, 10H), 3.13-2.80 (m, 3H), 2.66-2.56 (m, 1H), 2.46-2.44 (m, 3H), 2.10-1.95 (m, 1H), 1.76 (br d, J = 6.1 Hz, 1H), 1.41-1.29 (m, 3H), 0.91 (br d, J = 5.3 Hz, 9H). | 3 | 1079.62 |
| 235 | 1079.78 | 1081.78 | $^1$H NMR (400 MHz, DMSO-$d_6$) δ 10.16 (br s, 1H), 8.98 (s, 1H), 8.79-8.25 (m, 1H), 7.73 (br s, 1H), 7.42 (br d, J = 8.1 Hz, 2H), 7.34 (br t, J = 7.8 Hz, 4H), 7.10 (br s, 1H), 6.89-6.72 (m, 2H), 6.34 (d, J = 7.5 Hz, 1H), 5.36 (t, J = 7.3 Hz, 1H), 5.13 (br s, 1H), 5.02-4.85 (m, 1H), 4.55 (br s, 1H), 4.46 (br d, J = 8.7 Hz, 1H), 4.29 (br s, 1H), 4.08-3.90 (m, 2H), 3.80 (br s, 2H), 3.68 (br s, 6H), 3.64-3.41 (m, 10H), 3.12-2.84 (m, 3H), 2.75-2.69 (m, 1H), 2.47-2.45 (m, 3H), 2.10-1.97 (m, 1H), 1.77 (br s, 1H), 1.40-1.30 (m, 3H), 0.91 (br s, 9H). | 3 | 1079.62 |
| 236 | 1123.82 | 1125.82 | $^1$H NMR (400 MHz, DMSO-$d_6$) δ 10.11 (s, 1H), 8.98-8.96 (m, 1H), 8.49-8.36 (m, 1H), 7.71 (s, 1H), 7.45-7.40 (m, 2H), 7.38-7.28 (m, 4H), 7.21-7.08 (m, 1H), 6.83-6.74 (m, 2H), 6.35 (d, J = 7.6 Hz, 1H), 5.39-5.32 (m, 1H), 5.14 (d, J = 3.6 Hz, 1H), 4.90-4.86 (m, 1H), 4.54-4.53 (m, 1H), 4.45-4.41 (m, 1H), 4.27-4.22 (m, 1H), 3.94-3.90 (m, 2H), 3.84-3.77 (m, 2H), 3.71-3.64 (m, 6H), 3.60-3.49 (m, 12H), 3.03-2.82 (m, 4H), 2.63-2.60 (m, 2H), 2.44 (s, 3H), 2.06-2.01 (m, 1H), 1.79-1.72 (m, 1H), 1.45-1.33 (m, 3H), 0.91-0.90 (m, 9H). | 3 | 1123.67 |
| 237 | 1123.82 | 1125.82 | $^1$H NMR (400 MHz, DMSO-$d_6$) δ 10.11 (s, 1H), 8.97 (s, 1H), 8.45-8.37 (m, 1H), 7.72 (s, 1H), 7.44-7.41 (m, 2H), 7.36-7.29 (m, 4H), 7.21-7.08 (m, 1H), 6.84-6.75 (m, 2H), 6.35 (d, J = 7.2 Hz, 1H), 5.37-5.33 (m, 1H), 5.14 (s, 1H), 4.91-4.87 (m, 1H), 4.54-4.52 (m, 1H), 4.46-4.42 (m, 1H), 4.28-4.21 (m, 1H), 3.95-3.91 (m, 2H), 3.85-3.77 (m, 2H), 3.76-3.63 (m, 6H), 3.62-3.50 (m, 12H), 3.03-2.83 (m, 4H), 2.62 (s, 2H), 2.45 (s, 3H), 2.07-2.02 (m, 1H), 1.80-1.74 (m, 1H), 1.36-1.34 (m, 3H), 0.92-0.91 (m, 9H). | 3 | 1123.67 |
| 238 | 1167.86 | 1169.86 | $^1$H NMR (400 MHz, DMSO-$d_6$) δ 10.36-10.02 (m, 1H), 8.98 (s, 1H), 8.43 (d, J = 7.9 Hz, 1H), 7.72 (s, 1H), 7.46-7.42 (m, 2H), 7.39-7.28 (m, 4H), 7.10 (br s, 1H), 6.85-6.73 (m, 2H), 6.34 (d, J = 7.1 Hz, 1H), 5.35 (t, J = 7.6 Hz, 1H), 5.13 (d, J = 3.3 Hz, 1H), 5.01-4.81 (m, 1H), 4.54 (d, J = 9.3 Hz, 1H), 4.44 (br t, J = 8.3 Hz, 1H), 4.28 (br s, 1H), 4.00-3.87 (m, 2H), 3.80 (br s, 2H), 3.68 (br s, 6H), 3.60-3.43 (m, 18H), 3.05-2.81 (m, 3H), 2.65-2.57 (m, 1H), 2.45 (s, 3H), 2.11-1.86 (m, 1H), 1.76 (br d, J = 4.9 Hz, 1H), 1.36 (br d, J = 5.3 Hz, 3H), 0.93 (br d, J = 2.2 Hz, 9H). | 3 | 1167.72 |
| 239 | 1167.86 | 1169.86 | $^1$H NMR (400 MHz, DMSO-$d_6$) δ 10.15 (br s, 1H), 8.97 (s, 1H), 8.42 (d, J = 7.8 Hz, 1H), 7.72 (s, 1H), 7.46-7.41 (m, 2H), 7.39-7.28 (m, 4H), 7.07 (s, 1H), 6.85-6.75 (m, 2H), 6.33 (d, J = 7.5 Hz, 1H), 5.35 (t, J = 7.2 Hz, 1H), 5.12 (d, J = 3.5 Hz, 1H), 5.00-4.84 (m, 1H), 4.53 (d, J = 9.5 Hz, 1H), 4.44 (br t, J = 7.9 Hz, 1H), 4.28 (br s, 1H), 3.96-3.88 (m, 2H), 3.79 (br s, 2H), 3.76-3.63 (m, 6H), 3.62-3.42 (m, 18H), 3.07-2.77 (m, 3H), 2.65-2.58 (m, 1H), 2.45 (s, 3H), 2.10-1.98 (m, IH), 1.83-1.71 (m, 1H), 1.36 (br d, J = 5.0 Hz, 3H), 0.92 (br d, J = 2.3 Hz, 9H). | 3 | 1167.72 |
| 240 | 1211.89 | 1213.89 | $^1$H NMR (400 MHz, METHANOL-$d_4$) δ 8.87 (s, 1H), 7.73 (s, 1H), 7.45-7.35 (m, 5H), 7.29 (q, J = 7.9 Hz, 1H), 6.77 (d, J = 8.3 Hz, 1H), 6.70 (t, J = 8.8 Hz, 1H), 5.19 (s, 1H), 5.03-4.97 (m, 1H), 4.67 (s, 1H), 4.58 (s, 10H), 4.44 (s, 1H), 4.02 (d, J = 2.0 Hz, 2H), 3.82-3.58 (m, 20H), 3.16 (s, 1H), 2.95 (s, 2H), 2.87-2.80 (m, 1H), 2.76 (s, 1H), 2.49-2.47 (m, 3H), 2.19 (d, J = 7.9 Hz, 1H), 2.01-1.93 (m, 1H), 1.54-1.48 (m, 3H), 1.06-1.02 (m, 9H). | 3 | 1211.77 |
| 241 | 1211.89 | 1213.89 | $^1$H NMR (400 MHz, DMSO-$d_6$) δ 10.19(s, 1H), 8.97 (s, 1H), 8.43 (d, J = 7.7 Hz, 1H),7.73 (s, 1H), 7.44-7.40 (m, 2H), 7.38-7.28 (m, 4H), 7.17-7.05 (m, 1H), 6.85-6.75 (m, 2H), 6.35 (d, J = 6.5 Hz, 1H), 5.35 (s, 1H), 5.13 (s, 1H), 4.89 (t, J = 7.2 Hz, 1H), 4.53 (d, J = 9.5 Hz, 1H), 4.44 (t, J = 8.2 Hz, 1H), 4.27 (s, 1H), 3.97-3.88 (m, 2H), 3.79 (s, 4H), 3.70-3.61 (m, 5H), 3.56 (dd, J = 5.3, 9.7 Hz, 7H), 3.52 (s, 5H), 3.49-3.43 (m, 10H), 3.02 (s, 1H), 2.83 (s, 1H), 2.62 (s, 1H), 2.45 (s, 3H), 2.08-2.00 (m, 1H), 1.77 (ddd, J = 4.5, 8.7, 13.1 Hz, 1H), 1.46-1.34 (m, 3H), 0.92 (s, 9H). | 3 | 1211.77 |
| 242 | 1255.91 | 1257.91 | $^1$H NMR (400 MHz, DMSO-$d_6$) δ 10.17 (br s, 1H), 9.45-8.97 (m, 1H), 8.44 (d, J = 7.8 Hz, 1H), 7.73 (s, 1H), 7.48-7.41 (m, 2H), 7.41-7.28 (m, 4H), 7.26-7.03 (m, 1H), 6.88-6.74 (m, 2H), 6.35 (d, J = 7.3 Hz, 1H), 5.36 (t, J = 7.4 Hz, 1H), 5.13 | 3 | 1255.83 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| | | | (d, J = 3.5 Hz, 1H), 5.02-4.85 (m, 1H), 4.54 (d, J = 9.4 Hz, 1H), 4.45 (t, J = 8.2 Hz, 1H), 4.28 (br s, 1H), 3.96 (s, 2H), 3.80 (br s, 2H), 3.76-3.63 (m, 6H), 3.61-3.55 (m, 6H), 3.52 (br d, J = 2.7 Hz, 6H), 3.50-3.46 (m, 8H), 3.44 (br s, 4H), 3.39 (br s, 2H), 3.08-2.81 (m, 3H), 2.63 (br s, 1H), 2.46 (s, 3H), 2.23-1.99 (m, 1H), 1.92-1.71 (m, 1H), 1.37 (d, J = 6.8 Hz, 3H), 0.94 (s, 9H). | | |
| 243 | 1255.91 | 1257.91 | $^1$H NMR (400 MHz, DMSO-$d_6$) δ 10.17 (br s, 1H), 9.51-8.95 (m, 1H), 8.82-8.40 (m, 1H), 7.73 (s, 1H), 7.46-7.41 (m, 2H), 7.41-7.29 (m, 4H), 7.27-7.00 (m, 1H), 6.91-6.71 (m, 2H), 6.35 (d, J = 7.5 Hz, 1H), 5.36 (t, J = 7.4 Hz, 1H), 5.13 (d, J = 3.2 Hz, 1H), 5.02-4.84 (m, 1H), 4.72-4.50 (m, 1H), 4.45 (t, J = 8.2 Hz, 1H), 4.29 (br s, 1H), 4.01-3.87 (m, 2H), 3.80 (br s, 2H), 3.77-3.64 (m, 6H), 3.61-3.55 (m, 6H), 3.53 (br s, 614), 3.50-3.46 (m, 8H), 3.44 (br s, 4H), 3.39 (br s, 2H), 3.07-2.80 (m, 3H), 2.62 (br s, 1H), 2.46 (s, 3H), 2.22-1.99 (m, 1H), 1.78 (ddd, J = 4.2, 8.7, 12.9 Hz, 1H), 1.49-1.36 (m, 3H), 0.97-0.92 (m, 9H). | 3 | 1255.83 |
| 244 | 1168.8 | 1170.8 | $^1$H NMR (400 MHz, DMSO-$d_6$) δ 10.03 (s, 1H), 8.99 (s, 1E1), 8.42 (br d, J = 7.6 Hz, 1H), 8.14 (s, 1H), 8.02 (s, 1H), 7.81 (br d, J = 8.0 Hz, 1H), 7.43 (br d, J = 6.4 Hz, 3H), 7.38- 7.27 (m, 4H), 7.22 (br s, 2H), 7.11-7.03 (m, 1H), 6.39 (d, J = 7.6 Hz, 1H), 5.37 (br t, J = 7.6 Hz, 1H), 5.13 (br s, 1H), 4.90 (s, 1H), 4.53 (br d, J = 9.4 Hz, 1H), 4.43 (br t, J = 8.0 Hz, 1H), 4.28 (br s, 1H), 4.00-3.83 (m, 10H), 3.72 (br s,4H), 3.55 (br d, J = 13.2 Hz, 4H), 2.45 (br s, 4H), 2.17-2.02 (m, 5H), 1.78 (br s, 3H), 1.39-1.28 (m, 8H), 0.91 (br s, 9H). | 3 | 1168.78 |
| 245 | 1212.82 | 1214.82 | $^1$H NMR (400 MHz, DMSO-$d_6$) δ 8.96 (s, 1H), 8.54-8.35 (m, 1H), 8.27 (s, 114), 8.00 (s, 1H), 7.80-7.78 (d, J = 8.0 Hz, 1H), 7.54-7.30 (m, 7H), 7.30-7.16 (m, 3H), 7.05 (s, 1H), 6.51-6.29 (m, 1H), 5.46-5.28 (m, 2H), 4.93-4.84 (m, 1H), 4.53-4.51 (d, J = 8.0 Hz, 1H), 4.47-4.37 (m, 114), 4.27 (s, 1H), 3.95-3.81 (m, 8H), 3.71 (s, 2H), 3.59-3.53 (m, 8H), 3.25-3.20 (m, 3H), 2.81-2.72 (m, 2H), 2.44 (s, 4H), 2.07 (s, 5H), 1.78-1.67 (m, 3H), 1.38-1.24 (m, 8H), 0.91 (s, 9H). | 3 | 1212.83 |
| 246 | 1256.87 | 1258.87 | $^1$H NMR (400 MHz, DMSO-$d_6$) δ 10.04 (s, 1H), 8.97 (s, 1H), 8.43-8.41 (d, J = 8.0 Hz, 114), 8.18 (s, 1H), 8.00 (s, 1H), 7.81-7.79 (d, J = 8.0 Hz, 1H), 7.58-7.26 (m, 7H), 7.24-7.14 (m, 2H), 7.09-7.01 (m, 114), 6.43-6.30 (m, 1H), 5.52-5.03 (m, 2H), 4.95-4.80 (m, 1H), 4.71-4.34 (m, 2H), 4.27 (s, 1H), 4.00-3.78 (m, 8H), 3.75-3.66 (m, 2H), 3.63-3.49 (m, 12H), 3.23-3.18 (m, 3H), 2.90-2.74 (m, 2H), 2.44 (s, 4H), 2.18-1.98 (m, 5H), 1.81-1.66 (m, 3H), 1.40-1.18 (m, 8H), 0.92 (s, 9H). | 3 | 1256.88 |
| 247 | 1300.89 | 1302.89 | $^1$H NMR (400 MHz, DMSO-$d_6$) δ 10.05 (s, 1H), 8.97 (s, 1H), 8.44-8.35 (m, 2H), 8.03-7.98 (m, 1H), 7.80 (d, J = 8.4 Hz, 1H), 7.42 (d, J = 8.4 Hz, 4H), 7.36 (d, J = 8.8 Hz, 3H), 7.28 (d, J = 2.0 Hz, 114), 7.25-7.14 (m, 2H), 7.06 (dd, J = 2.4, 4.8 Hz, 114), 6.38 (s, 1H), 5.43-5.33 (m, 2H), 5.12 (s, 1H), 4.90 (t, J = 7.2 Hz, 1H), 4.53 (d, J = 9.6 Hz, 1H), 4.46-4.41 (m, 1H), 4.37-4.15 (m, 314), 3.96-3.80 (m, 10H), 3.78-3.68 (m, 4H), 3.62-3.41 (m, 10H), 2.80 (m, 1H), 2.45 (s, 4H), 2.17-1.96 (m, 6H), 1.81-1.68 (m, 3H), 1.39-1.23 (m, 9H), 0.93 (s, 9H). | 3 | 1300.94 |
| 248 | 1344.94 | 1346.94 | $^1$H NMR (400 MHz, DMSO-$d_6$) δ 8.98 (s, 1H), 8.42 (br d, J = 7.6 Hz, 1H), 8.23 (s, 1H), 8.01 (s, 1H), 7.80 (br d, J = 8.0 Hz, 1H), 7.43-7.35 (m, 6H), 7.29 (br s, 1H), 7.19 (m, 2H), 7.07 (m, 1H), 6.39 (d, J = 7.6 Hz, 1H), 5.41-5.37 (m, 2H), 4.90 (s, 1H), 4.53 (br d, J = 9.4 Hz, 1H), 4.43 (br t, J = 8.0 Hz, 1H), 4.28 (br s, 1H), 3.95-3.85 (m, 10H), 3.71 (br s, 4H), 3.58 (m, 15H), 2.73 (br s, 4H), 2.61 (m, 2H), 2.45-2.36 (m, 4H), 1.99 (m, 5H), 1.74 (br s, 3H), 1.38-16 (m, 8H), 0.93 (br s, 9H). | 3 | 1344.99 |
| 249 | 1247.97 | 1249.98 | $^1$H NMR (400 MHz, DMSO-$d_6$) δ 9.04-8.93 (m, 1H), 8.39 (d, J = 7.6 Hz, 1H), 8.26 (brs, 1H), 8.16-7.96 (m, 2H), 7.83 (d, J = 8.4 Hz, 1H), 7.56-7.29 (m, 7H), 7.28-7.19 (m, 214), 7.08 (d, J = 2.0 Hz, 1H), 6.82 (dd, J = 10.4, 16.4 Hz, 1H), 6.20 (d, J = 16.4 Hz, 1H), 5.77 (d, J = 10.4 Hz, 1H), 4.96-4.85 (m, 1H), 4.53 (d, J = 9.6 Hz, 1H), 4.42 (t, J = 8.0 Hz, 2H), 4.29 (brs, 1H), 4.25-4.22 (m, 3H), 3.93-3.90 (m, 3H), 3.83-3.80 (m, 2H), 3.76-3.71 (m, 4H), 3.65-3.43 (m, 15H), 3.32-3.23 (m, 4H), 3.04-2.94 (m, 4H), 2.90-2.79 (m, 2H), 2.76-2.66 (m, 2H), 2.45 (s, 3H), 2.11-1.96 (m, 1H), 1.89-1.72 (m, 1H), 1.49-1.34 (m, 3H), 0.97-0.91 (m, 9H). | 3 | 3+ A83:L83 |
| 254 | 1107.86 | 1109.86 | $^1$H NMR (400 MHz, DMSO-$d_6$) δ 10.78-9.66 (s, 1H), 9.09-8.87 (s, 1H), 8.45 (d, J = 7.6 Hz, 1H), 8.38 (s, 1H), 7.80 (br d, J = 6.0 Hz, 2H), 7.43 (br d, J = 8.0 Hz, 3H), 7.38-7.31 (m, 3H), 7.27 (d, J = 2.0 Hz, 1H), 7.25-7.10 (m, 3H), 7.05 (d, J = 2.4 Hz, 1H), 5.15 (br s, 1H), 4.89 (br t, J = 7.2 Hz, 1H), 4.55 (d, J = 9.4 Hz, 1H), 4.46 (t, J = 8.0 Hz, 1H), 4.29 (br s, 1H), 3.97-3.89 (m, 2H), 3.71 (br s, 5H), 3.59 (br s, 3H), 3.52 (br s, 5H), 2.98 (s, 3H), 2.80 (br s, 3H), 2.61 (br t, J = 6.8 Hz, 2H), 2.47-2.40 (m, 6H), 2.12-2.01 (m, 1H), 1.81-1.72 (m, 1H), 1.62 (br s, 4H), 1.49-1.35 (m, 3H), 0.94 (s, 9H). | 4 | 1107.74 |
| 255 | 1087.82 | 1089.82 | $^1$H NMR (400 MHz, DMSO-$d_6$) δ 0.93-1.10 (m, 5H), 1.17-1.23 (m, 3H), 1.47-1.70 (m, 6H), 1.94-2.09 (m, 2H), 2.15-2.24 (m, 2H), 2.31 (s, 3H), 2.62-2.68 (m, 1H), 2.73-2.81 (m, 1H), 2.89 (s, 1H), 3.10 (s, 2H), 3.51-3.77 (m, 15H), 4.07-4.19 (m, 2H), 4.42-4.52 (m, 1H), 5.30-5.44 (m, 1H), 5.61-5.76 (m, 1H), 5.82-5.93 (m, 0.5H), 6.06-6.19 (m, 1H), 6.21-6.30 (m, 0.5H), 6.76-6.91 (m, 1H), 7.00-7.06 (m, 1H), 7.12-7.32 (m, 5H), 7.36-7.49 (m, 2H), 7.55-7.67 (m, 2H), 7.75-7.82 (m, 2H), 8.20-8.33 (m, 1H), 88.44-.51 (m, 1H), 9.90-10.07 (m, 1H). | 5 | 1087.71 |
| 256 | 1131.86 | 1133.86 | $^1$H NMR (400 MHz, DMSO-$d_6$) 0.86 (s, 1H), 1.04 (d, J = 11.4 Hz, 6H), 1.14-1.28 (m, 5H) 1.62 (d, J = 0.6 Hz, 6H), 2.01 (s, 2H), 2.16 (s, 1H), 2.26 (s, 3H), 2.57-2.71 (m, 2H), 2.82 (s, 1H), 3.01 (s, 1H), 3.55 (dd, J = 10.0, 9.2 Hz, 8H), 3.64-3.93 (m, 11H), 4.13 (d, J = 0.6 Hz, 2H), 4.48 (s, 1H), 5.31-5.44 (m, 1H), 5.67-5.80 (m, 1H), 6.84 (dd, J = 16.0, 10.4 Hz, 1H), 7.15-7.31 (m, 4H), 7.35-7.47 (m, 2H), 7.63 (dd, J = 11.3, 4.0 Hz, 2H), 7.78 (dd, J = 9.2, 3.7 Hz, 2H), 8.15 (d, J = 8.0 Hz, 1H), 8.46 (s, 1H), 9.93-10.12 (m, 1H). | 5 | 1131.76 |
| 257 | 1175.9 | 1177.91 | $^1$H NMR (400 MHz, DMSO-$d_6$) 0.86 (s, 1H), 1.06 (s, 6H), 1.16-1.28 (m, 5H), 1.62 (d, J = 1.2 Hz, 6H), 2.01 (s, 2H), 2.19 (s, 1H), 2.32 (s, 3H), 2.63 (d, J = 25.4 Hz, 2H), 2.80 (s, 1H), | 5 | 1175.82 |

US 11,161,841 B2

TABLE 9-continued

Data for Compounds of Table 8

| Ex. No. | MH+ (1) | MH+ (2) | NMR Transcript | Synthetic Scheme | Mol Weight |
|---|---|---|---|---|---|
| | | | 2.99 (s, 1H), 3.38-3.60 (m, 11H), 3.61-3.91 (m, 12H), 4.12 (dd, J = 1.4, 0.8 Hz, 2H), 4.47 (s, 1H), 5.32-5.43 (m, 1H), 5.73 (d, J = 10.4 Hz, 1H), 6.16 (d, J = 16.8 Hz, 1H), 6.76-6.89 (m, 1H), 7.05 (d, J = 1.9 Hz, 1H), 7.18-7.29 (m, 4H), 7.42 (s, 2H), 7.58-7.66 (m, 2H), 7.78 (s, 2H), 8.38-8.26 (m, 1H), 8.47 (s, 1H), 10.01 (s, 1H). | | |
| 258 | 1219.93 | 1221.93 | $^1$H NMR (400 MHz, DMSO-d$_6$) δ 1.02-1.17 (m, 8H), 1.30-1.35 (m, 3H), 1.53-1.68 (m, 6H), 1.98-2.06 (m, 2H), 2.20-2.24 (m, 2H), 2.33-2.44 (m, 4H), 2.59-2.68 (m, 2H), 2.80 (s, 1H), 3.00 (s, 1H), 3.44-3.55 (m, 13H), 3.72-3.81 (m, 11H), 4.12 (s, 2H), 4.45-4.49 (m, 1H), 5.37-5.40 (m, 1H), 5.71-5.75 (m, 1H), 5.86-6.28 (m, 2H), 6.80-6.87 (m, 1H), 7.05-7.27 (m, 6H), 7.40-7.45 (m, 2H), 7.61-7.68 (m, 2H), 7.78-7.80 (m, 2H), 8.48-8.49 (m, 1H), 8.60-8.62 (m, 1H), 10.00(m, 1H). | 5 | 1219.87 |
| 259 | 1263.97 | 1265.97 | $^1$H NMR (400 MHz, CD$_3$OD) δ 0.93-1.10 (m, 4H), 1.49 (d, J = 6.4 Hz, 3H)1.56-1.72 (m, 6H), 2.00-2.12 (m, 3H), 2.22-2.24 (m, 1H), 2.29-2.35 (m, 2H), 2.49 (s, 1H), 2.60 (d, J = 6.0 Hz, 3H), 2.64-2.67 (m, 1H), 2.74-2.77 (m, 2H), 2.92-2.93 (m, 1H), 3.03 (s, 1H), 3.49-3.64 (m, 15H), 3.69-3.74 (m, 3H), 3.79-3.88 (m, 12H), 4.12-4.15 (m, 2H), 4.60 (s, 1H), 5.55-5.59 (m, 1H), 5.75-5.78 (m, 1H), 6.33-6.38 (m, 1H), 6.56-6.63 (m, 3H), 7.12-7.18 (m, 3H), 7.30-7.37 (m, 4H), 7.63-7.71 (m, 4H), 8.04 (s, 1H). | 5 | 1263.92 |
| 260 | 1098.84 | 1100.84 | $^1$H NMR (400 MHz, DMSO-d$_6$) δ 0.79-1.07 (m, 5H), 1.11-1.13 (m, 3H), 1.23 (m, 2H), 1.54-1.71 (m, 7H), 2.01-2.07 (m, 2H), 2.20-2.22 (m, 3H), 2.25-2.33 (m, 1H), 2.67-2.69 (m, 1H), 2.84-2.87 (m, 1H), 2.97-3.02 (m, 2H), 3.19 (s, 1H), 3.51-3.55 (m, 4H), 3.57-3.70 (m, 6H), 3.80-3.83 (m, 3H), 3.90-3.99 (m, 3H), 4.29 (s, 214), 4.50-4.54 (m, 1H), 5.42-5.45 (m, 1H), 6.07 (m, 2H), 7.00-7.04 (m, 2H), 7.13-7.30 (m, 4H), 7.39-7.59 (m, 4H), 7.66-7.68 (m, 1H), 7.76-7.81 (m, 2H), 7.92-7.94 (m, 1H), 8.08-8.25 (m, 2H), 9.96 (s, 1H). | 5 | 1098.74 |
| 261 | 1142.88 | 1144.88 | $^1$H NMR (400 MHz, DMSO-d$_6$) 1.40-1.06 (m, 12H), 1.83-1.50 (m, 6H), 2.35-1.90 (m, 6H) 3.04-2.63 (m, 5H), 3.94-3.58 (m, 14H), 4.09 (d, J = 43.3 Hz, 3H), 4.42-4.04.26 (m, 2H), 4.50 (s, 1H), 5.44 (s, 1H), 6.26 (d, J = 70.9 Hz, 2H), 7.34-6.99 (m, 4H), 7.58-7.44 (m, 3H), 7.70 (s, 6H), 8.95-8.71 (m, 2H), 9.32 (s, 1H), 10.20 (s, 1H), 12.13-12.78 (m, 2H). | 5 | 1142.79 |
| 262 | 1186.92 | 1188.92 | $^1$H NMR (400 MHz, DMSO-d$_6$) δ 1.11 (d, J = 7.2 Hz, 3H) 1.23 (s, 4H), 1.53-1.70 (m, 8H), 2.01-2.07 (m, 3H), 2.19 (s, 3H), 2.66 (d, J = 32 Hz, 2H), 2.79 (s, 2H), 2.98 (s, 2H), 3.70-3.42 (m, 19H), 3.92-3.76 (m, 4H), 4.25 (d, J = 23.2 Hz, 2H), 4.52 (d, J = 0.6 Hz, 1H), 5.46-5.40 (m, 1H), 6.07 (s, 2H), 7.04-7.24 (m, 7H), 7.40 (s, 1H), 7.58-7.49 (m, 3H), 7.67 (d, J = 0.8 Hz, 1H), 7.76 (t, J = 7.4 Hz, 2H), 7.91 (d, J = 8.7 Hz, 1H), 8.23 (d, J = 6.4 Hz, 2H). | 5 | 1186.84 |
| 263 | 1230.95 | 1232.95 | $^1$H NMR (400 MHz, DMSO-d$_6$) δ 1.10 (s, 6H), 1.31 (d, J = 6.8 Hz, 3H), 1.54-1.78 (m, 6H), 1.99-2.12 (m, 2H), 2.19-2.28 (m, 2H), 2.44 (s, 314), 2.55-2.67 (m, 2H), 2.78 (s, 1H), 2.98 (s, 1H), 3.36-3.92 (m, 29H), 4.28 (s, 2H), 4.48-4.54 (m, 1H), 5.40-5.48 (m, 1H), 6.08 (s, 2H), 6.96-7.02 (m, 1H), 7.05 (d, J = 2.4 Hz, 1H), 7.22 (s, 2H), 7.27 (d, J = 2.0 Hz, 1H), 7.39-7.45 (m, 1H), 7.49-7.58 (m, 3H), 7.69-7.71 (m, 1H), 7.75-7.81 (m, 2H), 8.21-8.26 (m, 2H), 8.54-8.61 (m, 1H), 9.99 (s, 1H). | 5 | 1230.90 |
| 264 | 1274.99 | 1276.99 | $^1$H NMR (400 MHz, DMSO-d$_6$) δ 0.97-1.10 (m, 414), 1.17-1.19 (m, 2H), 1.34-1.36 (m, 3H), 1.51-1.72 (m, 6H), 2.50 (s, 3H), 2.55-2.60 (m, 1H), 2.66-2.69 (m, 1H), 2.77 (s, 1H), 2.94 (s, 1H), 3.25 (s, 1H), 3.34-3.67 (m, 30H), 3.83-3.87 (m, 3H), 4.18-4.20 (m, 2H), 4.48-4.50 (m, 2H), 5.39-5.42 (m, 1H), 6.77-6.80 (m, 1H), 6.92-6.93 (m, 1H), 7.05-7.09 (m, 1H), 7.14-7.15 (m, 2H), 7.27-7.39 (m, 5H), 7.62-7.64 (m, 2H), 7.97-8.00 (m, 1H), 8.19-8.22 (m, 1H). | 5 | 1274.95 |
| 265 | 1097.84 | 1099.84 | $^1$H NMR (400 MHz, MeOD) δ 8.69-8.52 (m, 1H), 7.78 (t, J = 8.4 Hz, 3H), 7.68-7.40 (m, 4H), 7.38-7.15 (m, 4H), 7.14-6.95 (m, 2H), 5.61-5.49 (m, 1H), 4.61 (br d, J = 6.0 Hz, 1H), 4.52-4.34 (m, 2H), 4.31-4.06 (m, 4H), 4.05-3.63 (m, 9H), 3.14 (s, 1H), 2.87 (br s, 1H), 2.68 (s, 3H), 2.48-2.05 (m, 6H), 1.93-1.60 (m, 6H), 1.51 (br d, J = 6.7 Hz, 3H), 1.39-1.04 (m, 6H). | 5 | 1097.75 |
| 266 | 1141.88 | 1143.88 | $^1$H NMR (400 MHz, CD$_3$OD) δ 8.39-8.20 (m, 1H), 8.06-7.91 (m, 1H), 7.89-7.73 (m, 2H), 7.65 (br d, J = 7.9 Hz, 1H), 7.60-7.37 (m, 4H), 7.35-7.29 (m, 1H), 7.23 (br s, 2H), 7.09-6.92 (m, 2H), 5.57 (br d, J = 7.5 Hz, 1H), 4.71-4.51 (m, 1H), 4.43-4.18 (m, 3H), 4.15-3.91 (m, 8H), 3.88-3.57 (m, 8H), 3.14 (br s, 1H), 3.07-2.85 (m, 3H), 2.67 (d, J = 2.2 Hz, 3H), 2.58-2.35 (m, 1H), 2.34-2.05 (m, 6H), 1.94-1.58 (m, 6H), 1.56-1.43 (m, 3H), 1.33-1.05 (m, 5H). | 5 | 1141.80 |
| 267 | 1185.91 | 1187.92 | $^1$H NMR (400 MHz, CD$_3$OD) δ 8.31 (br d, J = 7.9 Hz, 1H), 8.08-7.84 (m, 2H), 7.81-7.71 (m, 1H), 7.67 (d, J = 3.3 Hz, 1H), 7.61-7.40 (m, 4H), 7.31 (s, 1H), 7.23 (br d, J = 5.1 Hz, 2H), 7.06 (br s, 1H), 7.01-6.91 (m, 1H), 5.57 (br s, 1H), 4.61 (br d, J = 6.7 Hz, 1H), 4.34 (br s, 2H), 4.27-4.06 (m, 4H), 4.05-3.90 (m, 5H), 3.89-3.51 (m, 14H), 3.09 (br s, 1H), 2.99-2.85 (m, 3H), 2.75 (br s, 1H), 2.68 (s, 3H), 2.58-2.37 (m, 1H), 2.25 (br s, 2H), 2.20-2.11 (m, 4H), 1.93-1.62 (m, 6H), 1.50 (d, J = 6.8 Hz, 3H), 1.38-1.34 (m, 1H), 1.34-1.08 (m, 5H), 0.00-0.00 (m, 1H). | 5 | 1185.86 |
| 268 | 1229.95 | 1231.95 | $^1$H NMR (400 MHz, CD$_3$OD) δ 8.37-8.21 (m, 1H), 8.11-7.93 (m, 1H), 7.88-7.75 (m, 2H), 7.68-7.59 (m, 1H), 7.68-7.53 (m, 1H), 7.52-7.40 (m, 3H), 7.34-7.29 (m, 1H), 7.24 (br s, 2H), 7.08 (br s, 1H), 7.01-6.88 (m, 1H), 5.55 (br s, 1H), 4.62 (br d, J = 6.7 Hz, 1H), 4.34 (br s, 2H), 4.25-3.89 (m, 9H), 3.82 (br d, J = 2.9 Hz, 7H), 3.71 (br d, J = 3.8 Hz, 2H), 3.67-3.47 (m, 8H), 3.08 (br s, 1H), 3.00-2.84 (m, 3H), 2.69 (s, 3H), 2.43 (br s, 1H), 2.33-2.21 (m, 2H), 2.19-2.12 (m, 4H), 1.96-1.59 (m, 6H), 1.51 (dd, J = 1.6, 6.8 Hz, 3H), 1.43-1.03 (m, 6H). | 5 | 1229.91 |
| 269 | 1273.98 | 1275.99 | $^1$H NMR (400 MHz, CD$_3$OD) δ 8.40-8.20 (m, 1H), 8.08-7.95 (m, 1H), 7.88 (br d, J = 7.1 Hz, 1H), 7.82-7.69 (m, 2H), 7.67-7.41 (m, 4H), 7.32 (d, J = 2.2 Hz, 1H), 7.23 (d, J = 4.3 Hz, 2H), 7.08 (br s, 1H), 7.03-6.87 (m, 1H), 5.59 (br s, 1H), 4.63 (br d, J = 6.6 Hz, 1H), 4.34 (br s, 2H), 4.29-4.09 (m, 3H), 4.08-3.92 (m, 5H), 3.90-3.68 (m, 9H), 3.67-3.42 (m, 11H), 3.10 (s, 1H), 3.00-2.85 (m, 3H), 2.78 (br s, 1H), 2.69 (s, 3H), 2.59-2.41 (m, 1H), 2.27 (br s, 2H), 2.22-2.10 (m, 4H), 1.96-1.62 (m, 6H), 1.51 (d, J = 6.8 Hz, 3H), 1.41-1.06 (m, 5H). | 5 | 1273.96 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| 270 | 1109.84 | 1111.84 | $^1$H NMR (400 MHz, MeOD) δ 8.15 (m, 2H), 7.85 (m, 1H), 7.70 (t, J = 8.0 Hz, 1H), 7.43 (m, 4H), 7.29 (m, 4H), 7.06 (m, 2H), 6.71 (m, 1H), 6.29 (d, J = 16.4 Hz, 1H), 5.80 (d, J = 10.8 Hz, 1H), 5.5 (m, 1H), 4.58 (m, 1H), 4.45 (m, 2H), 4.25 (m, 2H), 4.10 (m, 21), 3.96-3.75 (m, 12H), 3.62-3.55 (m, 4H), 3.3 (m, 2H), 3.10 (m, 2H), 2.75 (m, 1H), 2.67 (s, 3H), 2.30-2.05 (m, 5H), 1.85-1.75 (m, 3H), 1.75-1.55 (m, 4H), 1.49 (m, 3H), 1.33 (m, 3H), 1.25-1.16 (m, 5H). | 5 | 1109.76 |
| 271 | 1153.87 | 1155.87 | $^1$H NMR (400 MHz, CD$_3$OD) δ 8.48 (s, 1H), 8.33-8.15 (m, 1H), 8.06 (br s, 1H), 7.74 (br d, J = 8.1 Hz, 1H), 7.50-7.34 (m, 5H), 7.25 (br s, 2H), 7.19-7.12 (m, 1H), 7.03 (br d, J = 8.7 Hz, 1H), 6.90 (d, J = 8.3 Hz, 1H), 6.81-6.68 (m, 1H), 6.25 (br d, J = 16.5 Hz, 1H), 5.78 (br d, J = 10.4 Hz, 1H), 5.54-5.48 (m, 1H), 4.35-4.14 (m, 2H), 4.03-3.51 (m, 18H), 3.10 (s, 1H), 2.96 (br s, 1H), 2.87 (br t, J = 6.9 Hz, 1H), 2.66-2.53 (m, 4H), 2.30-2.27 (m, 1H), 2.42-2.01 (m, 4H), 1.82 (br s, 3H), 1.68-1.52 (m, 3H), 1.44 (d, J = 6.8 Hz, 3H), 1.29-0.97 (m, 6H). | 5 | 1153.81 |
| 272 | 1197.91 | 1199.91 | $^1$H NMR (400 MHz, CD$_3$OD) δ 8.29 (br s, 1H), 8.11 (t, J = 7.5 Hz, 1H), 7.87 (br d, J = 15.9 Hz, 1H), 7.79 (br d, J = 8.2 Hz, 1H), 7.55-7.40 (m, 5H), 7.32 (s, 1H), 7.28-7.20 (m, 2H), 7.07 (br s, 1H), 6.95-6.86 (m, 1H), 6.84-6.70 (m, 1H), 6.32 (br d, J = 16.5 Hz, 1H), 5.84 (br d, J = 10.9 Hz, 1H), 5.53 (br s, 1H), 4.62 (br d, J = 6.2 Hz, 1H), 4.32 (br s, 2H), 4.24-3.56 (m, 25H), 3.11 (s, 1H), 2.97 (s, 2H), 2.89 (br s, 1H), 2.69 (s, 3H), 2.47-2.07 (m, 4H), 1.89-1.61 (m, 6H), 1.51 (dd, J = 1.8, 7.0 Hz, 3H), 1.39-1.03 (m, 6H). | 5 | 1197.87 |
| 273 | 1241.95 | 1243.95 | $^1$H NMR (400 MHz, CD$_3$OD) δ 8.51 (br d, J = 10.4 Hz, 1H), 8.30 (br s, 1H), 8.15-8.02 (m, 1H), 8.15-8.02 (m, 1H), 7.74 (br d, J = 8.2 Hz, 2H), 7.55-7.34 (m, 5H), 7.31-7.13 (m, 3H), 7.04 (s, 1H), 6.91-6.67 (m, 2H), 6.24 (br d, J = 17.0 Hz, 1H), 5.78 (br dd, J = 4.9, 11.5 Hz, 1H), 5.51 (br d, J = 8.7 Hz, 1H), 4.26 (br s, 2H), 4.06-3.41 (m, 28H), 3.03 (s, 1H), 2.93-2.72 (m, 3H), 2.63 (br t, J = 6.6 Hz, 1H), 2.56-2.48 (m, 3H), 2.38 (s, 1H), 2.27 (br d, J = 11.4 Hz, 2H), 2.11 (br s, 1H), 1.82 (br s, 3H), 1.71-1.55 (m, 3H), 1.39 (d, J = 6.8 Hz, 3H), 1.28-0.97 (m, 6H). | 5 | 1241.92 |
| 274 | 1285.98 | 1287.98 | $^1$H NMR (400 MHz, CD$_3$OD) δ 8.36-8.27 (m, 1H), 8.13-8.05 (m, 1H), 7.82-7.71 (m, 2H), 7.51-7.44 (m, 4H), 7.42-7.37 (m, 1H), 7.42-7.37 (m, 1H), 7.40 (t, J = 7.3 Hz, 1H), 7.26 (br d, J = 2.3 Hz, 2H), 7.21-7.16 (m, 1H), 7.04 (s, 1H), 6.94-6.86 (m, 1H), 6.77 (ddd, J = 6.6, 10.5, 17.0 Hz, 1H), 6.26 (br d, J = 16.8 Hz, 1H), 5.79 (br d, J = 10.5 Hz, 1H), 5.54-5.46 (m, 1H), 4.30 (br s, 2H), 4.04-3.42 (m, 31H), 4.04-3.42 (m, 1H), 3.05 (s, 1H), 2.88 (s, 2H), 2.79 (br t, J = 6.8 Hz, 1H), 2.72-2.61 (m, 4H), 2.43-2.03 (m, 5H), 1.90-1.57 (m, 7H), 1.49 (d, J = 7.0 Hz, 3H), 1.35-1.03 (m, 7H), 1.35-1.03 (m, 1H). | 5 | 1285.97 |
| 275 | 1077.81 | 1079.81 | $^1$H NMR (400 MHz, METHANOL-d$_4$) δ 8.30-8.01 (m, 2H), 7.94 (br d, J = 8.0 Hz, 1H), 7.86-7.58 (m, 1H), 7.54-7.33 (m, 4H), 7.24-6.91 (m, 2H), 6.84-6.66 (m, 3H), 6.29 (br d, J = 16.8 Hz, 1H), 5.81 (br d, J = 10.8 Hz, 1H), 5.54 (br d, J = 8.4 Hz, 1H), 4.62 (br d, J = 6.7 Hz, 1H), 4.48 (br s, 1H), 4.38 (br s, 1H), 4.19 (br s, 1H), 4.10-3.69 (m, 15H), 3.14 (s, 2H), 2.95 (br s, 1H), 2.84 (br s, 11-0, 2.68 (s, 3H), 2.58-2.01 (m, 5H), 1.91-1.59 (m, 7H), 1.51 (d, J = 7.2 Hz, 3H), 1.37-1.10 (m, 6H). | 5 | 1077.69 |
| 276 | 1121.84 | 1123.84 | $^1$H NMR (400 MHz, METHANOL-d$_4$) δ 8.21 (br s, 1H), 8.15-7.89 (m, 1H), 7.83-7.59 (m, 1H), 7.49-7.26 (m, 5H), 6.89-6.71 (m, 4H), 6.31 (br d, J = 14.4 Hz, 1H), 5.82 (br s, 1H), 5.51 (br s, 1H), 4.61 (br s, 1H), 4.28 (br s, 2H), 4.07-3.55 (m, 21H), 3.09-2.81 (m, 4H), 2.68 (br s, 3H), 2.59-2.02 (m, 5H), 1.92-1.58 (m, 7H), 1.50 (br s, 3H), 1.38-1.08 (m, 6H). | 5 | 1121.74 |
| 277 | 1165.88 | 1167.88 | $^1$H NMR (400 MHz, CD$_3$OD) δ 8.25 (br d, J = 7.3 Hz, 1H), 8.14-8.01 (m, 1H), 7.85-7.63 (m, 1H), 7.52-7.32 (m, 5H), 6.91-6.66 (m, 4H), 6.30 (br d, J = 16.4 Hz, 1H), 5.83 (br d, J = 10.3 Hz, 1H), 5.51 (br d, J = 7.2 Hz, 1H), 4.67-4.58 (m, 1H), 4.28 (br s, 2H), 4.16-3.51 (m, 26H), 3.16-3.03 (m, 1H), 2.97 (s, 2H), 2.86 (br s, 1H), 2.75-2.65 (m, 3H), 2.46-2.07 (m, 4H), 1.95-1.61 (m, 6H), 1.51 (d, J = 7.0 Hz, 3H), 1.31-1.06 (m, 5H). | 5 | 1165.80 |
| 278 | 1209.92 | 1211.92 | $^1$H NMR (400 MHz, CD$_3$OD) δ 8.28-8.15 (m, 1H), 8.08 (br s, 1H), 7.78-7.56 (m, 1H), 7.53-7.32 (m, 5H), 6.93-6.65 (m, 1H), 6.30 (br d, J = 16.5 Hz, 1H), 5.82 (br d, J = 11.9 Hz, 1H), 5.50 (br d, J = 4.3 Hz, 1H), 4.69-4.58 (m, 1H), 4.43-4.15 (m, 2H), 4.12-3.52 (m, 27H), 3.06 (s, 1H), 3.00-2.80 (m, 3H), 2.73-2.66 (m, 3H), 2.49-2.02 (m, 4H), 1.97-1.61 (m, 6H), 1.51 (d, J = 7.0 Hz, 3H), 1.31-1.08 (m, 3H), 1.38-1.07 (m, 1H), 1.07-1.04 (m, 1H). | 5 | 1209.85 |
| 279 | 1253.95 | 1255.95 | $^1$H NMR (400 MHz, CD$_3$OD) δ 8.23 (br s, 1H), 8.13 (br d, J = 8.2 Hz, 1H), 7.83-7.59 (m, 1H), 7.53-7.29 (m, 5H), 6.90-6.66 (m, 1H), 6.29 (br d, J = 16.6 Hz, 1H), 5.82 (br d, J = 10.1 Hz, 1H), 5.51 (br s, 1H), 4.62 (br d, J = 7.1 Hz, 1H), 4.40-4.19 (m, 2H), 4.14-3.70 (m, 19H), 3.68-3.35 (m, 12H), 3.08 (s, 1H), 2.98-2.83 (m, 3H), 2.68 (s, 3H), 2.45-2.05 (m, 4H), 1.92-1.60 (m, 6H), 1.55-1.47 (m, 3H), 1.39-1.03 (m, 5H). | 5 | 1253.90 |
| 280 | 1065.8 | 1067.8 | $^1$H NMR (400 MHz, METHANOL-d$_4$) δ 8.30-7.82 (m, 3H), 7.62-7.35 (m, 4H), 7.25-7.13 (m, 1H), 7.10-6.90 (m, 1H), 6.85-6.72 (m, 2H), 5.67-5.48 (m, 1H), 4.62 (br d, J = 6.8 Hz, 1H), 4.47 (br d, J = 4.4 Hz, 1H), 4.38 (br s, 1H), 4.17 (br s, 1H), 4.07-3.85 (m, 9H), 3.82-3.69 (m, 4H), 3.63 (br d, J = 4.8 Hz, 2H), 3.14 (s, 2H), 2.95 (br s, 1H), 2.85 (br d, J = 7.5 Hz, 1H), 2.68 (s, 3H), 2.45-2.34 (m, 1H), 2.33-2.04 (m, 7H), 1.90-1.61 (m, 7H), 1.50 (d, J = 6.8 Hz, 3H), 1.36-1.11 (m, 6H). | 5 | 1065.68 |
| 281 | 1109.84 | 1111.84 | $^1$H NMR (400 MHz, METHANOL-d$_4$) δ 8.34-8.18 (m, 1H), 8.16-7.91 (m, 1H), 7.82-7.61 (m, 1H), 7.50-7.27 (m, 5H), 6.86-6.74 (m, 3H), 5.59-5.47 (m, 1H), 4.66-4.59 (m, 1H), 4.28 (br s, 2H), 4.08-3.58 (m, 21H), 3.06 (s, 2H), 3.01-2.91 (m, 1H), 2.87 (br s, 1H), 2.68 (s, 3H), 2.50-2.06 (m, 8H), 1.92-1.61 (m, 7H), 1.50 (d, J = 6.8 Hz, 3H), 1.34-1.10 (m, 6H). | 5 | 1109.73 |
| 282 | 1153.88 | 1155.88 | $^1$H NMR (400 MHz, CD$_3$OD) δ 8.11-8.04 (m, 1H), 7.82-7.65 (m, 1H), 7.56-7.53 (m, 1H), 7.52-7.31 (m, 6H), 6.93-6.70 (m, 1H), 5.52 (br d, J = 8.1 Hz, 1H), 4.63 (d, J = 6.7 Hz, | 5 | 1153.79 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| | | | 1H), 4.29 (br s, 2H), 4.15-3.51 (m, 26H), 3.14-3.06 (m, 1H), 2.96 (s, 2H), 2.86 (br s, 1H), 2.74-2.64 (m, 4H), 2.48-2.03 (m, 8H), 1.37-1.06 (m, 6H). | | |
| 283 | 1197.91 | 1198.91 | $^1$H NMR (400 MHz, CD$_3$OD) δ 8.32-8.15 (m, 1H), 8.07 (br s, 1H), 7.78-7.56 (m, 1H), 7.52-7.28 (m, 6H), 6.91-6.67 (m, 3H), 5.51 (br d, J = 8.6 Hz, 1H), 4.68-4.55 (m, 1H), 4.38-4.16 (m, 2H), 4.12-3.52 (m, 27H), 3.05 (s, 1H), 3.00-2.82 (m, 3H), 2.67 (s, 3H), 2.46-2.05 (m, 7H), 1.94-1.59 (m, 6H), 1.50 (d, J = 7.0 Hz, 3H), 1.35-1.08 (m, 5H). | 5 | 1197.84 |
| 284 | 1241.95 | 1243.95 | $^1$H NMR (400 MHz, CD$_3$OD) δ 8.10-8.03 (m, 1H), 7.80-7.64 (m, 1H), 7.55-7.52 (m, 1H), 7.50-7.29 (m, 6H), 6.93-6.70 (m, 1H), 5.51 (br d, J = 8.1 Hz, 1H), 4.62 (d, J = 6.7 Hz, 1H), 4.28 (br s, 2H), 4.15-3.48 (m, 26H), 3.13-3.06 (m, 1H), 2.96 (s, 2H), 2.88 (br s, 1H), 2.74-2.63 (m, 4H), 2.47-2.03 (m, 8H), 1.35-1.04 (m, 6H). | 5 | 1241.89 |
| 285 | 1066.8 | 1068.8 | $^1$H NMR (400MHz, METHANOL-d$_4$) δ 8.32-8.05 (m, 1H), 8.06-7.81 (m, 2H), 7.63-7.50 (m, 1H), 7.49-7.34 (m, 3H), 7.26-7.12 (m, 1H), 7.10-6.90 (m, 1H), 6.86-6.71 (m, 2H), 5.60-5.49 (m, 1H), 4.63 (m, 1H), 4.48 (br s, 1H), 4.38 (br s, 1H), 4.22-3.45 (m, 17H), 3.14 (s, 2H), 2.94 (m, 1H), 2.84 (br s, 1H), 2.68 (s, 3H), 2.47-2.09 (m, 4H), 1.93-1.59 (m, 7H), 1.50 (d, J = 7.2 Hz, 3H), 1.38-1.12 (m, 6H). | 5 | 1066.67 |
| 286 | 1110.84 | 1112.84 | $^1$H NMR (400 MHz, METHANOL-d$_4$) δ 8.34-8.19 (m, 1H), 8.17-7.89 (m, 1H), 7.80-7.60 (m, 1H), 7.50-7.27 (m, 5H), 6.88-6.72 (m, 3H), 5.59-5.50 (m, 1H), 4.62 (br d, J = 6.8 Hz, 1H), 4.28 (br s, 2H), 4.10-3.55 (m, 21H), 3.06 (s, 2H), 3.02-2.92 (m, 1H), 2.91-2.78 (m, 1H), 2.68 (s, 3H), 2.51-2.37 (m, 1H), 2.35-2.21 (m, 2H), 2.15 (br s,H), 1.95-1.62 (m, 7H), 1.51 (d, J = 6.8 Hz, 3H), 1.39-1.05 (m, 6H). | 5 | 1110.72 |
| 287 | 1154.87 | 1156.87 | $^1$H NMR (400 MHz, METHANOL-d$_4$) δ 8.27 (br d, J = 8.0 Hz, 1H), 8.09 (d, J = 8.4 Hz, 1H), 7.81-7.67 (m, 1H), 7.50-7.37 (m, 5H), 6.88-6.76 (m, 3H), 5.55 (br d, J = 8.0 Hz, 1H), 4.65 (d, J = 6.8 Hz, 1H), 4.31 (br s, 2H), 4.06-3.58 (m, 25H), 2.99 (s, 2H), 2.89 (br s, 1H), 2.70 (s, 3H), 2.47 (br s, 1H), 2.29 (br d, J = 6.4 Hz, 2H), 2.17 (br s, 1H), 1.96-1.62 (m, 7H), 1.53 (d, J = 6.8 Hz, 3H), 1.37-1.10 (m, 6H). | 5 | 1154.77 |
| 288 | 1198.91 | 1200.91 | $^1$H NMR (400 MHz, METHANOL-d$_4$) δ 8.29-8.05 (m, 2H), 7.78-7.55 (m, 1H), 7.49-7.36 (m, 5H), 6.91-6.67 (m, 3H), 5.54 (br d, J = 6.4 Hz, 1H), 4.63 (d, J = 6.8 Hz, 1H), 4.43-4.18 (m, 1H), 4.08-3.54 (m, 28H), 3.06 (s, 1H), 2.97 (s, 2H), 2.90-2.82 (m, 1H), 2.68 (s, 3H), 2.48-2.11 (m, 4H), 1.93-1.65 (m, 6H), 1.51 (d, J = 7.2 Hz, 3H), 1.33-1.04 (m, 6H). | 5 | 1198.83 |
| 289 | 1242.95 | 1244.95 | $^1$H NMR (400 MHz, METHANOL-d$_4$) δ 8.28-8.07 (m, 2H), 7.83-7.57 (m, 1H), 7.49-7.33 (m, 5H), 6.88-6.67 (m, 3H), 5.54 (br d, J = 7.8 Hz, 1H), 4.69-4.59 (m, 1H), 4.27 (br d, J = 17.4 Hz, 2H), 4.05-3.40 (m, 32H), 3.16-3.03 (m, 1H), 3.00-2.82 (m, 4H), 2.68 (s, 3H), 2.47-2.12 (m, 4H), 1.88-1.60 (m, 6H), 1.55-1.47 (m, 3H), 1.39-1.05 (m, 6H). | 5 | 1242.88 |
| 290 | 1192.77 | 1194.77 | $^1$H NMR (400 MHz, DMSO-d$_6$) δ 0.96 (s, 9H),1.28 (s, 1H),1.62 (m, 2H), 2.64 (m, 2H) 2.85 (s, 1H), 2H), 3.03 (s, 2H), 3.74-3.37 (m, 14H), 3.96-3.84 (m, 4H),4.35 (s, 1H), 4.59 (s, 2H), 6.07 (s, 2H), 7.03 (m, 1H), 7.59-7.22 (m, 11H), 7.77 (m, 3H), 8.29 (d, J = 7.6 Hz, 1H), 8.51 (m, 2H), 9.97 (s, 1H),10.38 (s, 1H). | 6 | 1193.55 |
| 291 | 1236.8 | 1238.8 | $^1$H NMR (400 MHz, CDCl$_3$) 0.96 (s, 9H), 1.24 (s, 2H), 1.69-1.61 (m, 1H), 2.61-2.67 m, 2H), 2.81 (s, 2H), 3.00 (s, 2H), 3.70-3.40 (m, 16H), 3.89-3.97 m, 4H), 4.36 (s, 1H), 4.59 (s, 2H), 6.09 (s, 2H), 7.05 (m, 1H), 7.22-7.59 (m, 12H), 7.71-7.80 (m, 3H), 8.29 (d, J = 8.4 Hz, 2H), 8.46 (s, 1H), 9.99 (s, 1H),10.39 (s, 1H). | 6 | 1237.60 |
| 292 | 1280.84 | 1282.84 | $^1$H NMR (400 MHz, DMSO-d$_6$) δ 0.96 (s, 9H), 1.18-1.32 (m, 4H), 1.58-1.68 (m, 1H), 2.56-2.68 (m, 2H), 2.78-2.83 (m, 1H), 2.98 (s, 1H), 3.38-3.66 (m, 20H), 3.88-3.98 (m, 4H), 4.32-4.43 (m, 1H), 4.56-4.65 (m, 2H), 6.08 (s, 2H), 7.02-7.07 (m, 1H), 7.20-7.28 (m, 3H), 7.30-7.62 (m, 9H), 7.70-7.83 (m, 3H), 8.31 (d, J = 8.0 Hz, 1H), 8.40-8.51(m, 1H), 9.95-10.05 (m, 1H),10.39 (s, 1H). | 6 | 1281.65 |
| 293 | 1324.88 | 1326.88 | $^1$H NMR (400 MHz, DMSO-d$_6$) δ 0.97 (s, 9H), 1.61-1.67 (m, 1H), 2.62-2.68 (m, 2H), 2.80-2.87 (m, 2H), 2.99 (s, 1H), 3.40-3.64 (m, 27H), 3.91-3.98 (m, 4H), 4.34-4.39 (m, 1H), 4.55-4.59 (m, 2H), 6.09 (s, 2H), 7.05 (d, J = 1.6 Hz, 1H), 7.21-7.59 (m, 11H), 7.71-7.81 (m, 3H), 8.31 (d, J = 8.4 Hz, 1H), 8.44-8.48 (m, 1H), 9.98 (s, 1H), 10.40 (s, 1H). | 6 | 1325.71 |
| 294 | 1368.91 | 1370.91 | $^1$H NMR (400 MHz, DMSO-d$_6$) δ 0.97 (s, 9H), 1.37-1.40 (m, 1H), 1.62-1.68 (m, 1H), 2.52-2.53 (m, 1H), 2.60-2.68 (m, 2H), 2.81 (s, 1H), 3.00 (s, 1H), 3.37-3.64 (m, 30H), 3.92-3.98 (m, 4H), 4.34-4.39 (m, 1H), 4.57-4.60 (m, 2H), 6.09 (s, 2H), 7.05-7.05 (m, 1H), 7.22-7.24 (m, 2H), 7.27-7.28 (m, 1H), 7.33-7.60 (m, 9H), 7.72-7.81 (m, 3H), 8.31-8.33 (m, 1H), 8.46-8.49 (m. 11H 9.99 (s, 1H). 10.41 (s, 1H). | 6 | 1369.76 |
| 295 | 1191.78 | 1193.78 | $^1$H NMR (400 MHz, DMSO-d$_6$) δ 10.45-10.30 (m, 1H), 10.27-9.76 (m, 1H), 8.64-8.39 (m, 1H), 8.32-8.20 (m, 1H), 7.84-7.66 (m, 3H), 7.61-7.46 (m, 3H), 7.45-7.16 (m, 8H), 7.06-7.00 (m, 1H), 4.66-4.51 (m, 2H), 4.35 (br s, 1H), 4.00-3.59 (m, 12H), 3.58-3.41 (m, 6H), 3.07-2.81 (m, 3H), 2.65-2.55 (m, 2H), 2.10-1.98 (m, 3H), 1.72-1.57 (m, 1H), 1.29-1.22 (m, 1H), 0.96 (d, J = 2.4 Hz, 9H). | 6 | 1192.56 |
| 296 | 1235.82 | 1237.82 | $^1$H NMR (400 MHz, DMSO-d$_6$) δ 10.39 (br s, 1H), 10.02 (br s, 1H), 8.50-8.35 (m, 1H), 8.29 (br d, J = 8.6 Hz, 1H), 7.81-7.70 (m, 3H), 7.61-7.50 (m, 3H), 7.50-7.32 (m, 5H), 7.29-7.17 (m, 3H), 7.04 (s, 1H), 4.65-4.53 (m, 2H), 4.37 (br s, 1H), 3.99-3.88 (m, 4H), 3.66 (br s, 6H), 3.50 (br s, 8H), 3.44-3.39 (m, 5H), 3.01-2.79 (m, 3H), 2.60 (br s, 2H), 2.04 (d, J = 5.0 Hz, 3H), 1.69-1.58 (m, 1H), 1.26 (br d, J = 13.6 Hz, 1H), 0.96 (s, 9H). | 6 | 1236.61 |
| 297 | 1279.85 | 1281.85 | $^1$H NMR (400 MHz, DMSO-d$_6$) δ 10.37 (s, 1H), 10.04 (s, 1H), 8.45-8.42 (m, 1H), 8.29 (d, J = 8.4 Hz, 1H), 7.78-7.69 (m, 3H), 7.57-7.50 (m, 3H), 7.47-7.45 (m, 1H), 7.41-7.39 (m, 1H), 7.37-7.31 (m, 3H), 7.25-7.24 (m, 1H), 7.21-7.20 (m, 2H), 7.02 (d, J = 2.4 Hz, 1H), 4.57-4.54 (m, 2H), 4.34 (s, 1H), 3.96-3.88 (m, 4H), 3.68-3.62 (m, 6H), 3.51-3.41 (m, 17H), 2.96-2.77 (m, 3H), 2.58-2.57 (m, 2H), 2.04 (d, J = 3.2 Hz, 3H), 1.65-1.59 (m, 1H), 1.26-1.23 (m, 1H), 0.95 (s, 9H). | 6 | 1280.67 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| 298 | 1323.89 | 1325.89 | ¹H NMR (400 MHz, DMSO-d₆) δ 10.40 (s, 1H), 9.99 (br s, 1H), 8.46 (br s, 1H), 8.31 (d, J = 8.4 Hz, 1H), 7.85-7.68 (m, 3H), 7.61-7.31 (m, 8H), 7.29-7.19 (m, 3H), 7.14-7.01 (m, 1H), 4.60 (br s, 2H), 4.36 (br s, 1H), 4.03-3.88 (m, 4H), 3.68 (br s, 8H), 3.60-3.38 (m, 20H), 3.03-2.74 (m, 3H), 2.64-2.56 (m, 1H), 2.06 (s, 3H), 1.64 (br dd, J = 9.6, 13.6 Hz, 1H), 1.27 (br d, J = 13.6 Hz, 1H), 0.97 (s, 9H). | 6 | 1324.72 |
| 299 | 1367.92 | 1369.92 | ¹H NMR (400 MHz, DMSO-d₆) δ 10.41 (s, 1H), 10.29-9.94 (m, 1H), 8.49 (br s, 1H), 8.38 (br s, 1H), 7.84-7.70 (m, 3H), 7.63-7.46 (m, 4H), 7.45-7.33 (m, 4H), 7.30-7.18 (m, 3H), 7.04 (s, 1H), 4.68-4.53 (m, 2H), 4.38 (br s, 1H), 4.01-3.87 (m, 4H), 3.68 (br s, 6H), 3.55-3.39 (m, 25H), 3.01-2.80 (m, 3H), 2.61 (br s, 2H), 2.06 (s, 3H), 1.70-1.58 (m, 1H), 1.27 (br d, J = 14.2 Hz, 1H), 0.97 (s, 9H). | 6 | 1368.77 |
| 300 | 1203.78 | 1205.78 | ¹H NMR (400 MHz, DMSO-d₆) δ 10.45-10.30 (m, 1H), 9.98 (br s, 1H), 8.64-8.38 (m, 1H), 8.33-8.18 (m, 1H), 7.85-7.68 (m, 3H), 7.60-7.45 (m, 3H), 7.44-7.30 (m, 5H), 7.28-7.19 (m, 3H), 7.08-6.99 (m, 1H), 6.91-6.73 (m, 1H), 6.23-6.10 (m, 1H), 5.77-5.67 (m, 1H), 4.62-4.54 (m, 2H), 4.43-4.30 (m, 1H), 3.99-3.58 (m, 13H), 3.57-3.41 (m, 6H), 3.06-2.83 (m, 3H), 2.65-2.56 (m, 2H), 1.69-1.57 (m, 1H), 1.26 (br d, J = 14.0 Hz, 1H), 0.95 (d, J = 2.0 Hz, 9H). | 6 | 1204.57 |
| 301 | 1247.82 | 1249.82 | ¹H NMR (400 MHz, DMSO-d₆) δ 10.38 (s, 1H), 8.53-8.24 (m, 2H), 7.83-7.69 (m, 3H), 7.60-7.31 (m, 8H), 7.24 (br d, J = 17.6 Hz, 3H), 7.04 (s, 1H), 6.88-6.76 (m, 1H), 6.16 (br d, J = 16.9 Hz, 1H), 5.72 (br d, J = 10.0 Hz, 1H), 4.64-4.54 (m, 2H), 4.35 (br s, 1H), 4.01-3.64 (m, 12H), 3.50 (br d, J = 5.4 Hz, 12H), 3.06-2.78 (m, 3H), 2.60 (br s, 2H), 1.64 (br dd, J = 10.0, 13.5 Hz, 1H), 1.26 (br d, J = 14.2 Hz, 1H), 0.96 (s, 9H). | 6 | 1248.62 |
| 302 | 1291.85 | 1293.85 | ¹H NMR (400 MHz, DMSO-d₆) δ 10.39 (s, 1H), 9.99 (s, 1H), 8.45-8.42 (m, 1H), 8.30-8.29 (m, 2H), 7.79-7.77 (m, 2H), 7.74-7.71 (m, 1H), 7.58-7.48 (m, 5H), 7.41-7.34 (m, 4H), 7.26 (s, 1H), 7.25-7.21 (m, 2H), 7.04 (s, 1H), 6.86-6.80 (m, 1H), 6.18-6.14 (m, 1H), 5.73-5.71 (m, 1H), 4.59 (s, 2H), 4.27-4.41 (m, 1H), 3.97-3.90 (m, 4H), 3.80-3.71 (m, 10H), 3.52-3.45 (m, 12H), 2.98-2.79 (m, 3H), 2.62-2.60 (m, 1H), 1.66-1.60 (m, 1H), 1.28-1.24 (m, 1H), 0.96 (s, 9H). | 6 | 1292.68 |
| 303 | 1335.89 | 1337.89 | ¹H NMR (400 MHz, DMSO-d₆) δ 10.40 (s, 1H), 8.46 (br s, 1H), 8.39-8.23 (m, 2H), 7.85-7.77 (m, 2H), 7.73 (t, J = 7.2 Hz, 1H), 7.61-7.32 (m, 8H), 7.29-7.18 (m, 3H), 7.14-7.02 (m, 1H), 6.89-6.78 (m, 1H), 6.17 (br d, J = 17.6 Hz, 1H), 5.74 (br d, J = 10.4 Hz, 1H), 4.60 (br s, 2H), 4.47-4.27 (m, 1H), 3.97 (br d, J = 10.8 Hz, 1H), 3.91 (s, 3H), 3.86-3.67 (m, 8H), 3.60-3.41 (m, 20H), 3.01-2.78 (m, 3H), 2.62 (br d, J = 8.4 Hz, 1H), 1.64 (br dd, J = 10.0, 14.4 Hz, 1H), 1.27 (br d, J = 13.2 Hz, 1H), 0.97 (s, 9H). | 6 | 1336.73 |
| 304 | 1379.92 | 1381.92 | ¹H NMR (400 MHz, DMSO-d₆) δ 10.40 (s, 1H), 10.05 (br s, 1H), 8.51-8.43 (m, 1H), 8.31 (d, J = 8.4 Hz, 1H), 7.82-7.77 (m, 2H), 7.73 (br t, J = 6.7 Hz, 1H), 7.62-7.54 (m, 2H), 7.53-7.46 (m, 1H), 7.45-7.31 (m, 4H), 7.28-7.17 (m, 3H), 7.13-7.01 (m, 1H), 6.83 (dd, J = 10.5, 16.6 Hz, 1H), 6.17 (dd, J = 2.2, 16.8 Hz, 1H), 5.78-5.69 (m, 1H), 4.65-4.53 (m, 2H), 4.35 (br s, 1H), 4.02-3.87 (m, 4H), 3.85-3.67 (m, 8H), 3.56-3.38 (m, 24H), 3.03-2.77 (m, 3H), 2.62 (br d, J = 7.8 Hz, 2H), 1.64 (br dd, J = 10.0, 14.5 Hz, 1H), 1.33-1.19 (m, 1H), 0.97 (s, 9H). | 6 | 1380.78 |
| 305 | 1171.74 | 1173.74 | ¹H NMR (400 MHz, DMSO-d₆) δ 10.48-10.34 (m, 1H), 10.16 (br s, 1H), 8.63-8.43 (m, 1H), 8.34-8.24 (m, 1H), 8.20 (s, 1H), 7.79-7.69 (m, 2H), 7.61-7.26 (m, 8H), 6.93-6.68 (m, 3H), 6.22-6.09 (m, 1H), 5.77-5.65 (m, 1H), 4.64-4.53 (m, 2H), 4.36 (br s, 1H), 4.00-3.49 (m, 18H), 3.07-2.84 (m, 3H), 2.69-2.56 (m, 2H), 1.69-1.57 (m, 1H), 1.29-1.23 (m, 1H), 0.96 (d, J = 4.4 Hz, 9H). | 6 | 1172.50 |
| 306 | 1171.74 | 1173.74 | ¹H NMR (400 MHz, DMSO-d₆) δ 10.44-10.35 (m, 1H), 10.20 (br s, 1H), 8.62-8.41 (m, 1H), 8.33-8.25 (m, 1H), 8.23 (s, 1H), 7.77-7.69 (m, 2H), 7.62-7.26 (m, 8H), 6.88-6.71 (m, 3H), 6.23-6.10 (m, 1H), 5.76-5.66 (m, 1H), 4.63-4.54 (m, 2H), 4.43-4.30 (m, 1H), 3.99-3.58 (m, 14H), 3.58-3.48 (m, 4H), 3.09-2.82 (m, 3H), 2.67-2.56 (m, 2H), 1.70-1.58 (m, 1H), 1.31-1.23 (m, 1H), 0.96 (d, J = 2.4 Hz, 9H). | 6 | 1172.50 |
| 307 | 1215.78 | 1217.78 | ¹H NMR (400 MHz, DMSO-d₆) δ 10.40 (s, 1H), 10.37-10.22 (m, 1H), 8.49-8.35 (m, 1H), 8.30 (dd, J = 2.2, 8.3 Hz, 1H), 7.78-7.67 (m, 2H), 7.61-7.51 (m, 3H), 7.50-7.43 (m, 1H), 7.42-7.27 (m, 4H), 7.06 (br s, 1H), 6.88-6.72 (m, 3H), 6.15 (br d, J = 16.9 Hz, 1H), 5.76-5.67 (m, 1H), 4.63-4.52 (m, 2H), 4.36 (br s, 1H), 4.01-3.86 (m, 4H), 3.85-3.62 (m, 9H), 3.59-3.48 (m, 8H), 3.04-2.81 (m, 3H), 2.71-2.55 (m, 2H), 1.64 (br dd, J = 10.0, 13.9 Hz, 1H), 1.26 (br d, J = 13.6 Hz, 1H), 0.96 (s, 9H). | 6 | 1216.55 |
| 308 | 1215.78 | 1217.78 | ¹H NMR (400 MHz, DMSO-d₆) δ 10.40 (s, 1H), 10.37-10.16 (m, 1H), 8.51-8.39 (m, 1H), 8.37-8.27 (m, 1H), 7.77-7.69 (m, 2H), 7.61-7.44 (m, 4H), 7.43-7.28 (m, 4H), 7.26-6.98 (m, 1H), 6.87-6.74 (m, 3H), 6.16 (br d, J = 16.8 Hz, 1H), 5.72 (dd, J = 2.8, 13.0 Hz, 1H), 4.66-4.54 (m, 2H), 4.36 (br s, 1H), 4.01-3.88 (m, 4H), 3.86-3.61 (m, 9H), 3.59-3.48 (m, 8H), 3.03-2.80 (m, 3H), 2.70-2.58 (m, 2H), 1.65 (br dd, J = 9.9, 14.1 Hz, 1H), 1.31-1.21 (m, 1H), 0.97 (s, 9H). | 6 | 1216.55 |
| 309 | 1259.81 | 1261.81 | ¹H NMR (400 MHz, DMSO-d₆) δ 10.50-10.39 (m, 2H), 8.48-8.44 (m, 1H), 8.32-8.29 (m, 1H), 8.15-8.02 (m, 2H), 7.74-7.71 (m, 1H), 7.58-7.45 (m, 4H), 7.39-7.33 (m, 4H), 6.88-6.73 (m, 3H), 6.20-6.15 (m, 1H), 5.75-5.72 (m, 1H), 4.59 (s, 2H), 4.18 (s, 2H), 3.96-3.87 (m, 18H), 3.49-3.37 (m, 6H), 2.96-2.84 (m, 3H), 2.72-2.65 (m, 2H), 1.67-1.61 (m, 1H), 1.28-1.22 (m, 1H), 0.96 (s, 9H). | 6 | 1260.61 |
| 310 | 1259.81 | 1261.81 | ¹H NMR (400 MHz, DMSO-d₆) δ 10.51-10.40 (m, 2H), 8.47-8.45 (m, 1H), 8.32-8.29 (m, 1H), 8.12-8.03 (m, 2H), 7.75-7.71 (m, 1H), 7.59-7.53 (m, 4H), 7.41-7.33 (m, 4H), 6.88-6.68 (m, 3H), 6.20-6.16 (m, 1H), 5.75-5.72 (m, 1H), 4.59 (s, 2H), 4.17 (s, 314), 3.93-3.73 (m, 18H), 3.45-3.37 (m, 6H), 2.96-2.85 (m, 3H), 2.72-2.64 (m, 2H), 1.67-1.61 (m, 1H), 1.28-1.25 (m, 1H), 0.97 (s, 9H). | 6 | 1260.61 |
| 311 | 1303.85 | 1305.85 | ¹H NMR (400 MHz, DMSO-d₆) δ 10.41 (s, 1H), 10.26 (br s, 1H), 8.48 (br d, J = 3.2 Hz, 1H), 8.32 (d, J = 8.4 Hz, 1H), 7.78-7.69 (m, 2H), 7.64-7.45 (m, 4H), 7.44-7.25 (m, 4H), 7.07 (br s, 1H), 6.92-6.70 (m, 3H), 6.16 (br d, J = 16.4 Hz, 1H), 5.73 (br d, J = | 6 | 1304.66 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| | | | 10.4 Hz, 1H), 4.70-4.52 (m, 2H), 4.37 (br s, 1H), 4.03-3.87 (m, 4H), 3.84-3.66 (m, 8H), 3.54-3.43 (m, 17H), 3.03-2.78 (m, 3H), 2.72-2.57 (m, 2H), 1.76-1.55 (m, 1H), 1.27 (br d, J = 13.6 Hz, 1H), 0.98 (s, 9H). | | |
| 312 | 1303.85 | 1305.85 | $^1$H NMR (400 MHz, DMSO-$d_6$) δ 10.41 (s, 1H), 10.35 (br s, 1H), 8.47 (br d, J = 2.8 Hz, 1H), 8.32 (d, J = 8.4 Hz, 1H), 7.77-7.71 (m, 2H), 7.61-7.46 (m, 4H), 7.43-7.28 (m, 4H), 7.03 (s, 1H), 6.88-6.73 (m, 3H), 6.17 (br d, J = 16.4 Hz, 1H), 5.73 (br d, J = 10.4 Hz, 1H), 4.63-4.56 (m, 2H), 4.37 (br s, 1H), 4.01-3.89 (m, 4H), 3.84-3.63 (m, 8H), 3.54-3.41 (m, 17H), 3.05-2.75 (m, 3H), 2.72-2.57 (m, 2H), 1.65 (br dd, J = 10.4, 13.6 Hz, 1H), 1.27 (br d, J = 13.6 Hz, 114), 0.98 (s, 9H). | 6 | 1304.66 |
| 313 | 1347.88 | 1349.88 | $^1$H NMR (DMSO-$d_6$) δ 10.41 (s, 1H), 8.54-8.43 (m, 1H), 8.39-8.27 (m, 2H), 7.81-7.68 (m, 2H), 7.63-7.55 (m, 2H), 7.54-7.45 (m, 2H), 7.43-7.26 (m, 4H), 6.90-6.72 (m, 3H), 6.17 (dd, J = 2.4, 16.8 Hz, 1H), 5.73 (d, J = 12.8 Hz, 1H), 4.60 (s, 2H), 4.36 (s, 1H), 4.01-3.88 (m, 4H), 3.85-3.62 (m, 9H), 3.53-3.39 (m, 23H), 3.02 (s, 2H), 2.82 (s, 2H), 1.70-1.59 (m, 1H), 1.27 (d, J = 13.6 Hz, 1H), 0.98 (s, 9H). | 6 | 1348.71 |
| 314 | 1347.89 | 1349.89 | $^1$H NMR (DMSO-$d_6$) δ 10.40 (s, 1H), 8.47 (s, 1H), 8.31 (d, J = 8.4 Hz, 1H), 7.77-7.69 (m, 2H), 7.61-7.54 (m, 2H), 7.54-7.42 (m, 3H), 7.40-7.27 (m, 4H), 6.90-6.71 (m, 3H), 6.21-6.11 (m, 1H), 5.72 (d, J = 12.4 Hz, 1H), 4.59 (s, 2H), 4.36 (s, 1H), 4.00-3.92 (m, 1H), 3.91 (s, 3H), 3.86-3.58 (m, 16H), 3.57-3.39 (m, 15H), 3.01 (s, 2H), 2.81 (s, 2H), 2.07 (s, 1H), 1.69-1.58 (m, 1H), 1.26 (d, J = 13.6 Hz, 2H), 0.97 (s, 9H). | 6 | 1348.71 |
| 315 | 1159.75 | 1161.75 | $^1$H NMR (400 MHz, DMSO-$d_6$) δ 10.48 (br s, 1H), 10.39 (br d, J = 8.4 Hz, 114), 8.70-8.45 (m, 1H), 8.36-8.24 (m, 1H), 8.05-7.85 (m, 2H), 7.74 (br t, J = 7.2 Hz, 1H), 7.62-7.48 (m, 3H), 7.47-7.30 (m, 5H), 6.96-6.73 (m, 2H), 4.65-4.52 (m, 2H), 4.46-4.28 (m, 1H), 4.23-3.80 (m, 9H), 3.77-3.60 (m, 9H), 3.09-2.84 (m, 3H), 2.75-2.60 (m, 2H), 2.10-1.98 (m, 3H), 1.72-1.58 (m, 1H), 1.33-1.21 (m, 1H), 0.97 (d, J = 3.6 Hz, 9H). | 6 | 1160.49 |
| 316 | 1159.75 | 1161.75 | $^1$H NMR (400 MHz, DMSO-$d_6$) δ 10.49 (br s, 1H), 10.43-10.35 (m, 1H), 8.69-8.44 (m, 1H), 8.36-8.23 (m, 1H), 8.07-7.87 (m, 2H), 7.78-7.68 (m, 1H), 7.63-7.31 (m, 8H), 6.96-6.74 (m, 2H), 4.65-4.53 (m, 2H), 4.44-4.32 (m, 1H), 4.21-3.88 (m, 5H), 3.83-3.71 (m, 13H), 3.08-2.86 (m, 3H), 2.80-2.60 (m, 2H), 2.08-2.02 (m, 3H), 1.71-1.59 (m, 1H), 1.32-1.22 (m, 1H), 1.07-0.87 (m, 9H). | 6 | 1160.49 |
| 317 | 1203.78 | 1205.78 | $^1$H NMR (400 MHz, DMSO-$d_6$) δ 10.40 (s, 1H), 10.29 (br s, 1H), 8.51-8.38 (m, 1H), 8.32 (br d, J = 8.4 Hz, 1H), 7.79-7.69 (m, 2H), 7.62-7.44 (m, 4H), 7.43-7.28 (m, 4H), 7.05 (br s, 1H), 6.88-6.72 (m, 2H), 4.67-4.52 (m, 2H), 4.36 (br s, 1H), 4.01-3.87 (m, 4H), 3.58-3.46 (m, 17H), 3.06-2.80 (m, 3H), 2.72-2.57 (m, 2H), 2.09-1.97 (m, 3H), 1.65 (br dd, J = 10.2, 14.2 Hz, 1H), 1.31-1.21 (m, 1H), 0.97 (s, 9H). | 6 | 1204.54 |
| 318 | 1203.78 | 1205.78 | $^1$H NMR (400 MHz, DMSO-$d_6$) δ 10.40 (s, 1H), 10.28 (br s, 1H), 8.53-8.36 (m, 1H), 8.31 (dd, J = 2.0, 8.5 Hz, 1H), 7.79-7.67 (m, 2H), 7.61-7.43 (m, 4H), 7.43-7.28 (m, 4H), 7.06 (br s, 1H), 6.87-6.74 (m, 2H), 4.66-4.53 (m, 2H), 4.36 (br s, 1H), 4.00-3.89 (m, 4H), 3.65 (br s, 8H), 3.56-3.40 (m, 9H), 3.04-2.82 (m, 3H), 2.71-2.55 (m, 2H), 2.04 (d, J = 4.2 Hz, 3H), 1.65 (br dd, J = 10.4, 14.2 Hz, 1H), 1.27 (d, J = 13.7 Hz, 1H), 0.97 (s, 9H). | 6 | 1204.54 |
| 319 | 1247.81 | 1249.81 | $^1$H NMR (400 MHz, DMSO-$d_6$) δ 10.49-10.39 (m, 2H), 8.48-8.44 (m, 1H), 8.31 (dd, J = 2.0, 8.4 Hz, 1H), 8.02-8.01 (m, 2H), 7.74-7.71 (m, 1H), 7.58-7.45 (m, 4H), 7.38-7.33 (m, 4H), 6.88-6.79 (m, 2H), 4.58 (s, 2H), 4.16-4.12 (m, 3H), 3.96-3.90 (m, 7H), 3.55-3.37 (m, 17H), 2.96-2.84 (m, 3H), 2.71-2.65 (m, 2H), 2.04-2.03 (m, 3H), 1.67-1.61 (m, 1H), 1.28-1.24 (m, 1H), 0.96 (s, 9H). | 6 | 1248.60 |
| 320 | 1247.81 | 1249.81 | $^1$H NMR (400 MHz, DMSO-$d_6$) δ 10.50-10.39 (m, 2H), 8.47-8.45 (m, 1H), 8.31 (dd, J = 2.0, 8.4 Hz, 1H), 8.02-8.00 (m, 2H), 7.74-7.71 (m, 1H), 7.58-7.46 (m, 4H), 7.40-7.32 (m, 4H), 6.88-6.79 (m, 2H), 4.58 (s, 2H), 4.16-4.12 (m, 3H), 3.93-3.90 (m, 7H), 3.54-3.37 (m, 17H), 2.96-2.84 (m, 3H), 2.71-2.65 (m, 2H), 2.04-2.03 (m, 3H), 1.67-1.61 (m, 1H), 1.28-1.24 (m, 1H), 0.96 (s, 9H). | 6 | 1248.60 |
| 321 | 1291.84 | 1293.84 | $^1$H NMR (400 MHz, DMSO-$d_6$) δ 10.41 (s, 1H), 10.27 (br s, 1H), 8.47 (br d, J = 3.2 Hz, 1H), 8.32 (d, J = 8.4 Hz, 1H), 7.78-7.69 (m, 2H), 7.61-7.46 (m, 4H), 7.44-7.23 (m, 4H), 7.05 (br s, 1H), 6.87-6.71 (m, 2H), 4.63-4.55 (m, 2H), 4.37 (br s, 1H), 4.00-3.89 (m, 4H), 3.66 (br s, 8H), 3.52-3.41 (m, 17H), 3.03-2.80 (m, 3H), 2.70-2.56 (m, 2H), 2.05 (d, J = 1.2 Hz, 3H), 1.65 (br dd, J = 9.6, 14.2 Hz, 1H), 1.27 (br d, J = 13.6 Hz, 1H), 0.98 (s, 9H). | 6 | 1292.65 |
| 322 | 1291.85 | 1293.85 | $^1$H NMR (400 MHz, DMSO-$d_6$) δ 10.41 (s, 1H), 10.26 (br s, 1H), 8.47 (br d, J = 3.2 Hz, 1H), 8.32 (d, J = 8.4 Hz, 1H), 7.81-7.67 (m, 2H), 7.63-7.46 (m, 4H), 7.44-7.27 (m, 4H), 7.05 (br s, 1H), 6.87-6.74 (m, 2H), 4.60 (br s, 2H), 4.37 (br s, 1H), 4.03-3.89 (m, 4H), 3.66 (br s, 8H), 3.52-3.38 (m, 17H), 3.05-2.79 (m, 3H), 2.70-2.56 (m, 2H), 2.05 (d, J = 1.2 Hz, 3H), 1.65 (br dd, J = 9.6, 14.2 Hz, 1H), 1.27 (br d, J = 13.6 Hz, 1H), 0.98 (s, 9H). | 6 | 1292.65 |
| 323 | 1335.89 | 1337.89 | $^1$H NMR (DMSO-$d_6$) δ 10.41 (s, 1H), 8.49 (t, J = 5.6 Hz, 1H), 8.39-8.24 (m, 2H), 7.79-7.66 (m, 2H), 7.62-7.45 (m, 4H), 7.42-7.25 (m, 4H), 7.06 (s, 1H), 6.88-6.70 (m, 2H), 4.64-4.53 (m, 2H), 4.37 (s, 1H), 4.03-3.84 (m, 4H), 3.65 (s, 5H), 3.57-3.42 (m, 27H), 3.01 (s, 1H), 2.81 (s, 1H), 2.67-2.57 (m, 1H), 2.14-1.97 (m, 3H), 1.64 (dd, J = 9.6, 14.0 Hz, 1H), 1.26 (d, J = 14.0 Hz, 1H), 0.97 (s, 9H). | 6 | 1336.70 |
| 324 | 1335.89 | 1337.89 | $^1$H NMR (DMSO-$d_6$) δ 10.40 (s, 1H), 8.47 (t, J = 5.6 Hz, 1H), 8.38 (s, 1H), 8.31 (d, J = 8.4 Hz, 1H), 7.82-7.66 (m, 2H), 7.64-7.52 (m, 3H), 7.44-7.26 (m, 4H), 7.25-7.18 (m, 1H), 7.04 (s, 1H), 6.92-6.66 (m, 2H), 4.74-4.50 (m, 2H), 4.36 (s, 1H), 4.04-3.85 (m, 4H), 3.65 (s, 8H), 3.53-3.41 (m, 24H), 3.01 (s, 1H), 2.81 (s, 1H), 2.69-2.59 (m, 1H), 2.06 (d, J = 11.6 Hz, 3H), 1.64 (dd, J = 9.6, 14.0 Hz, 1H), 1.32-1.19 (m, 1H), 1.10-0.86 (m, 9H). | 6 | 1336.70 |

TABLE 9-continued

Data for Compounds of Table 8

| Ex. No. | MH+ (1) | MH+ (2) | NMR Transcript | Synthetic Scheme | Mol Weight |
|---|---|---|---|---|---|
| 325 | 1160.74 | 1162.74 | $^1$H NMR (400 MHz, DMSO-d$_6$) δ 10.50-10.31 (m, 1H), 10.21 (br s, 1H), 8.65-8.45 (m, 1H), 8.36-8.20 (m, 1H), 7.80-7.68 (m, 2H), 7.40 (br s, 8H), 7.28-6.87 (m, 1H), 6.85-6.75 (m, 2H), 6.09 (br s, 2H), 4.60 (br s, 2H), 4.38 (br s, 1H), 4.00-3.80 (m, 4H), 3.50 (br s, 14H), 3.07-2.85 (m, 3H), 2.62 (br s, 2H), 1.71-1.56 (m, 1H), 1.26 (br d, J = 13.8 Hz, 1H), 0.96 (d, J = 5.6 Hz, 9H). | 6 | 1161.48 |
| 326 | 1204.78 | 1206.78 | $^1$H NMR (400 MHz, DMSO-d$_6$) δ 10.40 (s, 1H), 8.54-8.39 (m, 1H), 8.30 (dd, J = 2.2, 8.4 Hz, 1H), 7.80-7.67 (m, 2H), 7.62-7.42 (m, 4H), 7.41-7.26 (m, 4H), 7.24-7.01 (m, 1H), 6.83 (d, J = 8.2 Hz, 1H), 6.76 (dt, J = 2.6, 8.7 Hz, 1H), 6.09 (s, 2H), 4.55 (br s, 2H), 4.37 (br s, 1H), 3.99-3.87 (m, 4H), 3.72-3.47 (m, 18H), 3.04-2.80 (m, 3H), 2.72-2.56 (m, 2H), 1.77-1.52 (m, 1H), 1.28-1.22 (m, 1H), 1.02-0.84 (m, 9H). | 6 | 1205.53 |
| 327 | 1248.81 | 1250.81 | $^1$H NMR (400 MHz, DMSO-d$_6$) δ 10.41 (s, 1H), 10.18 (s, 1H), 8.48-8.45 (m, 1H), 8.31-8.29 (m, 1H), 7.72-7.68 (m, 2H), 7.58-7.53 (m, 4H), 7.48-7.34 (m, 4H), 7.05 (s, 1H), 6.83-6.76 (m, 2H), 6.07 (s, 2H), 4.58 (s, 2H), 4.36 (s, 1H), 3.97-3.90 (m, 4H), 3.63.-3.44 (m, 22H), 2.99-2.79 (m, 3H), 2.59-2.52 (m, 2H), 1.66-1.60 (m, 1H), 1.27-1.23 (m, 1H), 0.96 (s, 9H). | 6 | 1249.58 |
| 328 | 1292.85 | 1294.85 | $^1$H NMR (400 MHz, DMSO-d$_6$) δ 10.41 (s, 1H), 10.19 (br s, 1H), 8.47 (br d, J = 2.8 Hz, 1H), 8.32 (d, J = 8.4 Hz, 1H), 7.82-7.67 (m, 2H), 7.64-7.45 (m, 4H), 7.43-7.25 (m, 4H), 7.21-6.96 (m, 1H), 6.89-6.73 (m, 2H), 6.07 (s, 2H), 4.60 (br s, 2H), 4.37 (br s, 1H), 4.01-3.85 (m, 4H), 3.55-3.40 (m, 26H), 3.02-2.79 (m, 3H), 2.63 (br dd, J = 18.8 Hz, 2H), 1.65 (br dd, J = 10.0,13.6 Hz, 1H), 1.27 (br d, J = 13.6 Hz, 1H), 0.98 (s, 9H). | 6 | 1293.64 |
| 329 | 1336.88 | 1338.88 | $^1$H NMR (400 MHz, DMSO-d$_6$) δ 10.41 (s, 1H), 10.16 (s, 1H), 8.48 (t, J = 5.6 Hz, 1H), 8.32 (d, J = 8.4 Hz, 1H), 8.14 (s, 1H), 7.80-7.66 (m, 2H), 7.63-7.45 (m, 4H), 7.43-7.24 (m, 4H), 7.07 (br s, 1H), 6.87-6.72 (m, 2H), 6.07 (s, 2H), 4.60 (br s, 2H), 4.37 (br s, 1H), 4.01-3.84 (m, 4H), 3.66-3.38 (m, 30H), 3.11-2.78 (m, 3H), 2.63 (br d, J = 8.8 Hz, 2H), 1.65 (dd, J = 9.6, 13.6 Hz, 1H), 1.27 (br d, J = 14.4 Hz, 1H), 0.98 (s, 9H). | 6 | 1337.69 |

TABLE 10

Compounds Prepared by Schemes 7-16

| Ex. No. | Structure | Compound Name | Synthetic Scheme |
|---|---|---|---|
| 330 | 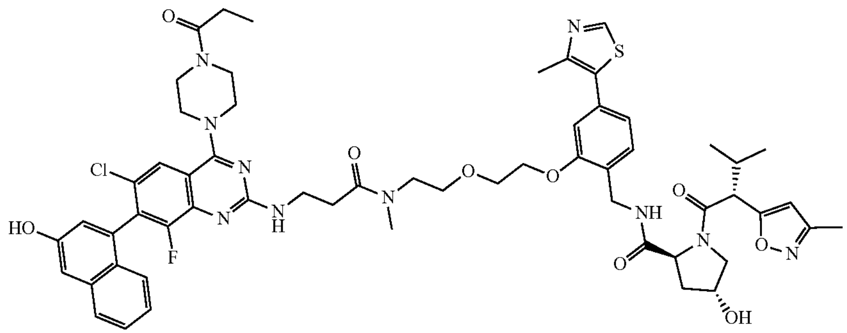 [SMILES: CCC(=O)N1CCN(c2nc(NCCC(=O)N(C)CCOCCOc3cc(-c4scnc4C)ccc3CNC(=O)[C@@H]3C[C@@H](O)CN3C(=O)[C@@H](c3cc(C)no3)C(C)C)nc3c(F)c(-c4cc(O)cc5ccccc45)c(Cl)cc23)CC1] | (2S,4R)-N-(2-(2-(2-(3-((6-chloro-8-fluoro-7-(3-hydroxynaphthalen-1-yl)-4-(4-propionylpiperazin-1-yl)quinazolin-2-yl)amino)-N-methylpropanamido)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 7 |
| 331 | 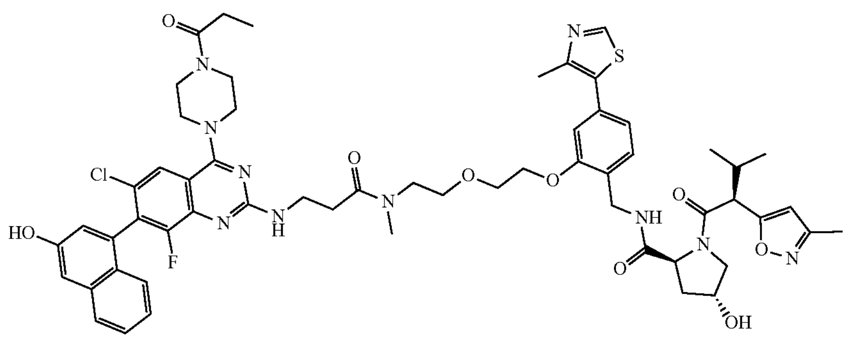 [SMILES: CCC(=O)N1CCN(c2nc(NCCC(=O)N(C)CCOCCOc3cc(-c4scnc4C)ccc3CNC(=O)[C@@H]3C[C@@H](O)CN3C(=O)[C@H](c3cc(C)no3)C(C)C)nc3c(F)c(-c4cc(O)cc5ccccc45)c(Cl)cc23)CC1] | (2S,4R)-N-(2-(2-(2-(3-((6-chloro-8-fluoro-7-(3-hydroxynaphthalen-1-yl)-4-(4-propionylpiperazin-1-yl)quinazolin-2-yl)amino)-N-methylpropanamido)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 332 | 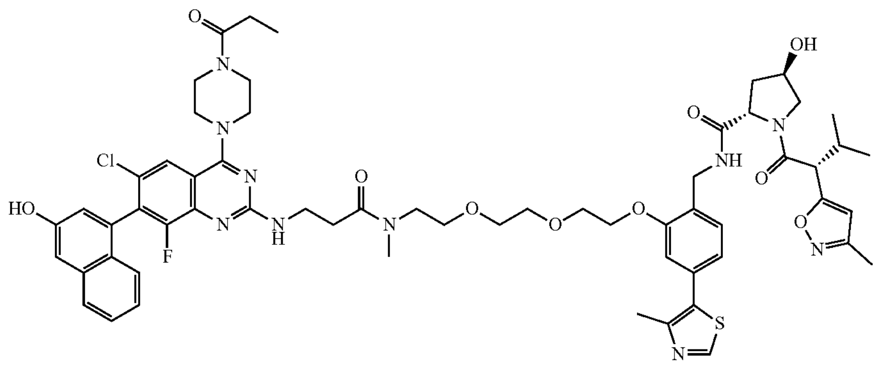 | (2S,4R)-N-(2-(2-(2-(2-(3-((6-chloro-8-fluoro-7-(3-hydroxynaphthalen-1-yl)-4-(4-propionylpiperazin-1-yl)quinazolin-2-yl)amino)-N-methylpropanamido)ethoxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 7 |
| 333 | 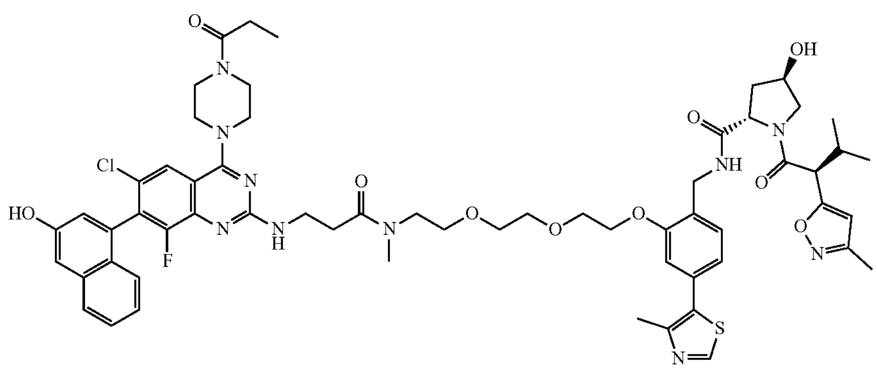 | (2S,4R)-N-(2-(2-(2-(2-(3-((6-chloro-8-fluoro-7-(3-hydroxynaphthalen-1-yl)-4-(4-propionylpiperazin-1-yl)quinazolin-2-yl)amino)-N-methylpropanamido)ethoxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 334 | 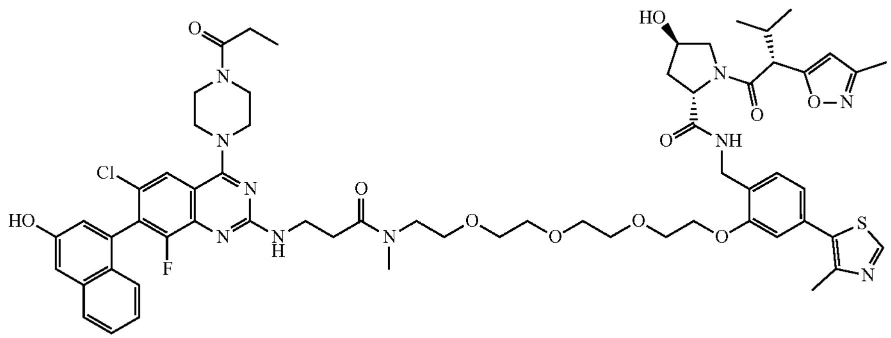 [SMILES: CCC(=O)N1CCN(c2nc(NCCC(=O)N(C)CCOCCOCCOCCOc3cc(-c4scnc4C)ccc3CNC(=O)[C@@H]3C[C@@H](O)CN3C(=O)[C@@H](c3cc(C)no3)C(C)C)nc3c(F)c(-c4cc(O)cc5ccccc45)c(Cl)cc23)CC1] | (2S,4R)-N-(2-((15-((6-chloro-8-fluoro-7-(3-hydroxynaphthalen-1-yl)-4-(4-propionylpiperazin-1-yl)quinazolin-2-yl)amino)-12-methyl-13-oxo-3,6,9-trioxa-12-azapentadecyl)oxy)-4-(4-methylthiazol-5-yl)benzyl)-4-hydroxy-1-((R)-3-methyl-2-(3-methylisoxazol-5-yl)butanoyl)pyrrolidine-2-carboxamide | 7 |
| 335 | 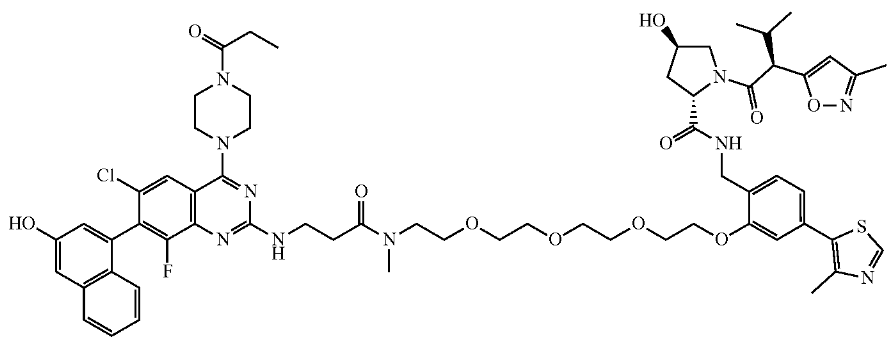 [SMILES: CCC(=O)N1CCN(c2nc(NCCC(=O)N(C)CCOCCOCCOCCOc3cc(-c4scnc4C)ccc3CNC(=O)[C@@H]3C[C@@H](O)CN3C(=O)[C@H](c3cc(C)no3)C(C)C)nc3c(F)c(-c4cc(O)cc5ccccc45)c(Cl)cc23)CC1] | (2S,4R)-N-(2-((15-((6-chloro-8-fluoro-7-(3-hydroxynaphthalen-1-yl)-4-(4-propionylpiperazin-1-yl)quinazolin-2-yl)amino)-12-methyl-13-oxo-3,6,9-trioxa-12-azapentadecyl)oxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |
| 336 | 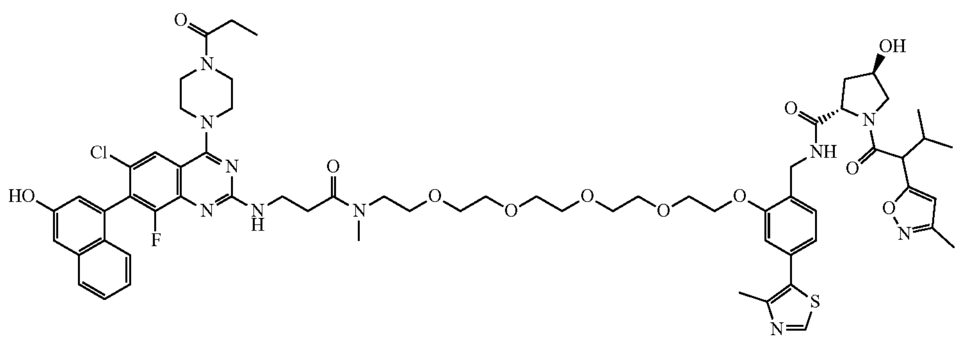 | (2S,4R)-N-(2-((18-((6-chloro-8-fluoro-7-(3-hydroxynaphthalen-1-yl)-4-(4-propionylpiperazin-1-yl)quinazolin-2-yl)amino)-15-methyl-16-oxo-3,6,9,12-tetraoxa-15-azaoctadecyl)oxy)-4-(4-methylthiazol-5-yl)benzyl)-4-hydroxy-1-(3-methyl-2-(3-methylisoxazol-5-yl)butanoyl)pyrrolidine-2-carboxamide | |

TABLE 10-continued

Compounds Prepared by Schemes 7-16

| Ex. No. | Structure | Compound Name | Synthetic Scheme |
|---|---|---|---|
| 337 | 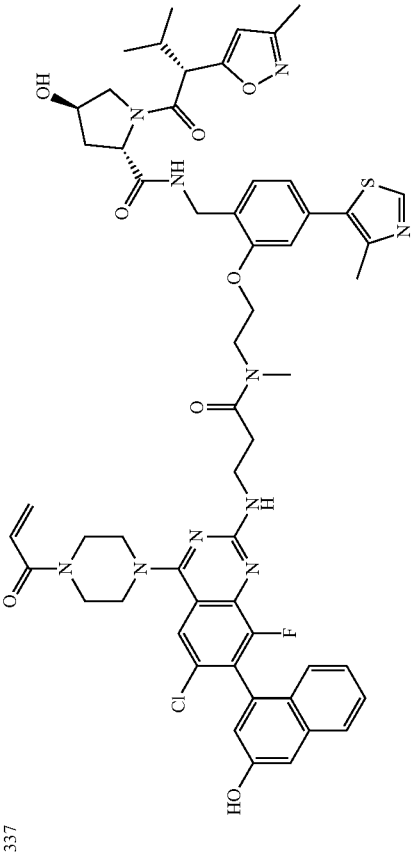 | (2S,4R)-N-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)-4-(4-hydroxy-1-((R)-3-methyl-2-(3-methylisoxazol-5-yl)butanoyl)pyrrolidine-2-carboxamide | 7 |
| 338 | 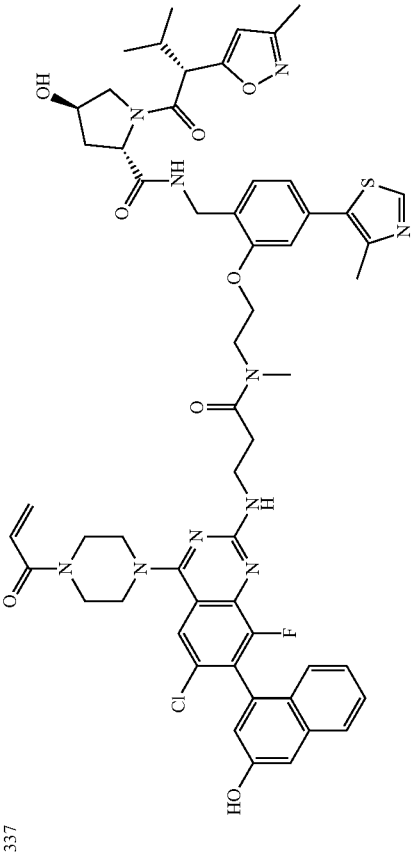 | (2S,4R)-N-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 339 | 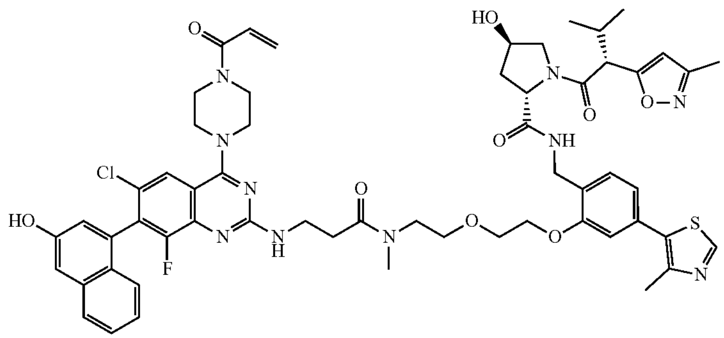 [SMILES: C=CC(=O)N1CCN(c2nc(NCCC(=O)N(C)CCOCCOc3cc(-c4scnc4C)ccc3CNC(=O)[C@@H]3C[C@@H](O)CN3C(=O)[C@@H](c3cc(C)no3)C(C)C)nc3c(F)c(-c4cc(O)cc5ccccc45)c(Cl)cc23)CC1] | (2S,4R)-N-(2-(2-(2-(3-((4-(4-acryloylpiperazin-1-yl)-6-chloro-8-fluoro-7-(3-hydroxynaphthalen-1-yl)quinazolin-2-yl)amino)ethoxy)-N-methylpropanamido)ethoxy)-4-(4-methylthiazol-5-yl)benzyl)-4-hydroxy-14(R)-3-methyl-2-(3-methylisoxazol-5-yl)butanoyl)pyrrolidine-2-carboxamide | 7 |
| 340 | 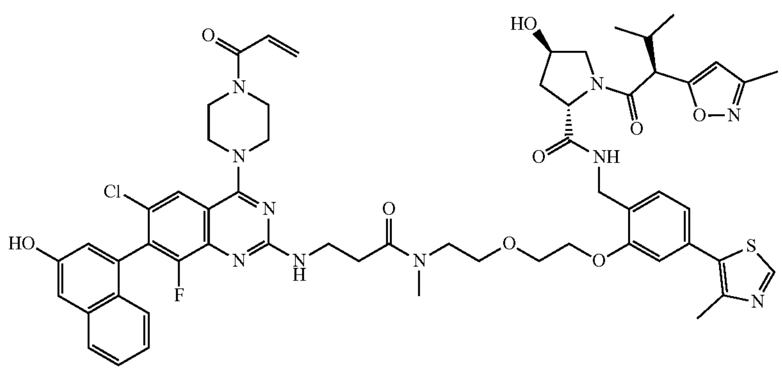 [SMILES: C=CC(=O)N1CCN(c2nc(NCCC(=O)N(C)CCOCCOc3cc(-c4scnc4C)ccc3CNC(=O)[C@@H]3C[C@@H](O)CN3C(=O)[C@H](c3cc(C)no3)C(C)C)nc3c(F)c(-c4cc(O)cc5ccccc45)c(Cl)cc23)CC1] | (2S,4R)-N-(2-(2-(2-(3-((4-(4-acryloylpiperazin-1-yl)-6-chloro-8-fluoro-7-(3-hydroxynaphthalen-1-yl)quinazolin-2-yl)amino)ethoxy)-N-methylpropanamido)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 341 | 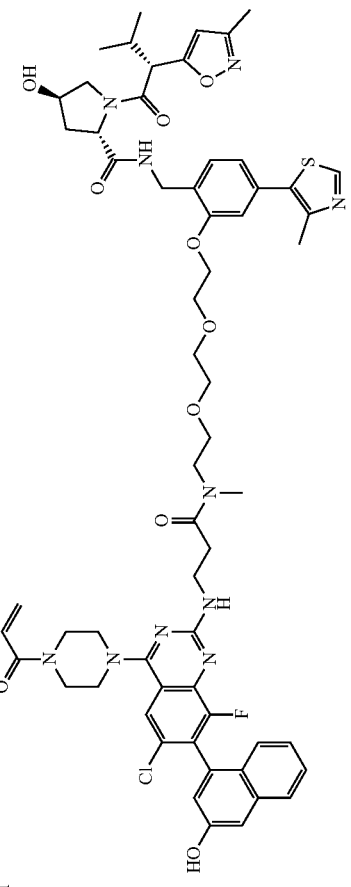 | (2S,4R)-N-(2-(2-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 7 |
| 342 | 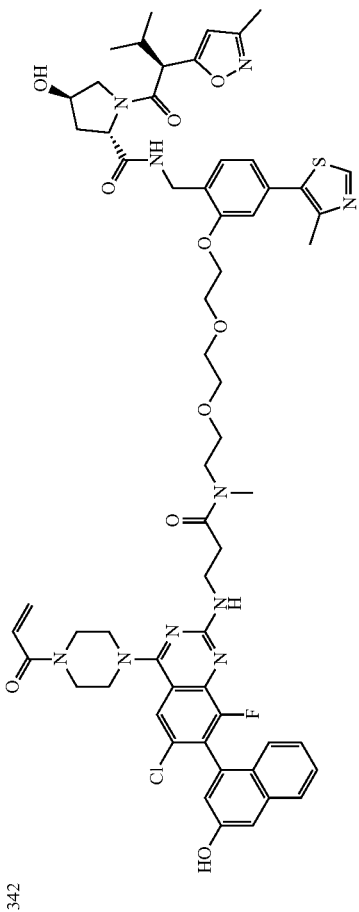 | (2S,4R)-N-(2-(2-(2-(2-(3-((4-(4-acryloylpiperazin-1-yl)-6-chloro-8-fluoro-7-(3-hydroxynaphthalen-1-yl)quinazolin-2-yl)amino)-N-methylpropanamido)ethoxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 343 | 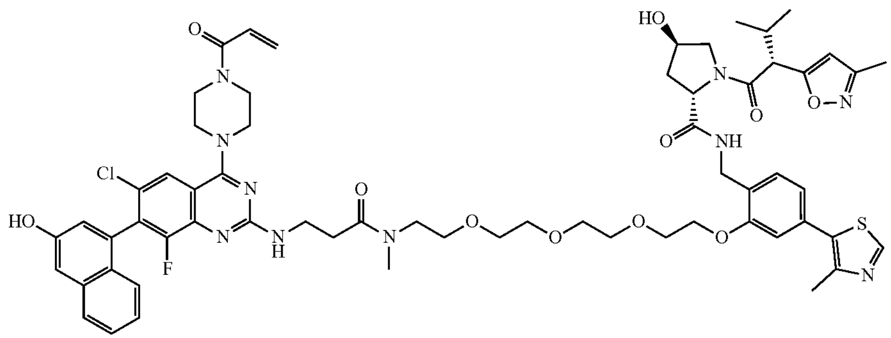 [SMILES: C=CC(=O)N1CCN(c2nc(NCCC(=O)N(C)CCOCCOCCOCCOc3cc(-c4scnc4C)ccc3CNC(=O)[C@@H]3C[C@@H](O)CN3C(=O)[C@@H](c3cc(C)no3)C(C)C)nc3c(F)c(-c4cc(O)cc5ccccc45)c(Cl)cc23)CC1] | (2S,4R)-N-(2-((15-(4-(4-acryloylpiperazin-1-yl)-6-chloro-8-fluoro-7-(3-hydroxynaphthalen-1-yl)quinazolin-2-yl)amino)-12-methyl-13-oxo-3,6,9-trioxa-12-azapentadecyl)oxy)-4-(4-methylthiazol-5-yl)benzyl)-4-hydroxy-1-((R)-3-methyl-2-(3-methylisoxazol-5-yl)butanoyl)pyrrolidine-2-carboxamide | 7 |
| 344 | 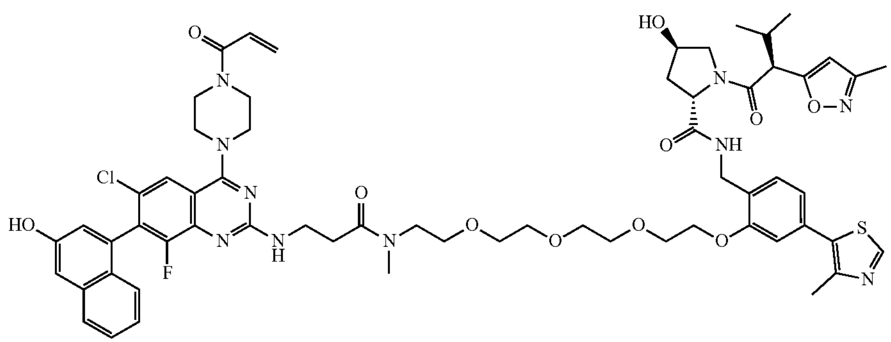 [SMILES: C=CC(=O)N1CCN(c2nc(NCCC(=O)N(C)CCOCCOCCOCCOc3cc(-c4scnc4C)ccc3CNC(=O)[C@@H]3C[C@@H](O)CN3C(=O)[C@H](c3cc(C)no3)C(C)C)nc3c(F)c(-c4cc(O)cc5ccccc45)c(Cl)cc23)CC1] | (2S,4R)-N-(2-((15-(4-(4-acryloylpiperazin-1-yl)-6-chloro-8-fluoro-7-(3-hydroxynaphthalen-1-yl)quinazolin-2-yl)amino)-12-methyl-13-oxo-3,6,9-trioxa-12-azapentadecyl)oxy)-4-(4-methylthiazol-5-yl)benzyl)-4-hydroxy-14(S)-3-methyl-2-(3-methylisoxazol-5-yl)butanoyl)pyrrolidine-2-carboxamide | 7 |
| 345 | 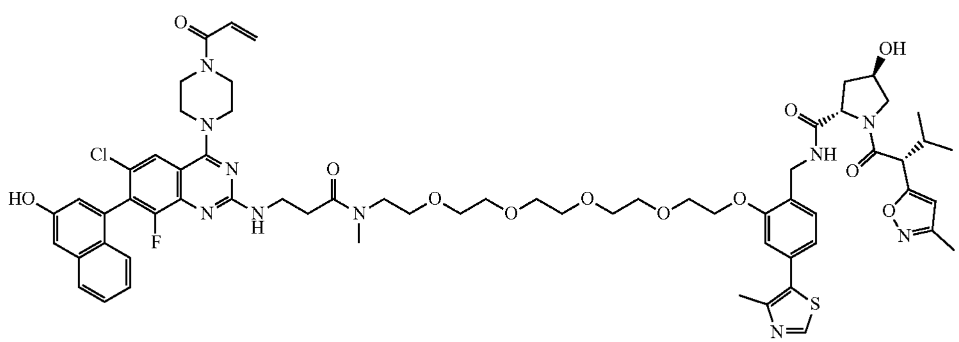 [SMILES: C=CC(=O)N1CCN(c2nc(NCCC(=O)N(C)CCOCCOCCOCCOCCOc3cc(-c4scnc4C)ccc3CNC(=O)[C@@H]3C[C@@H](O)CN3C(=O)[C@@H](c3cc(C)no3)C(C)C)nc3c(F)c(-c4cc(O)cc5ccccc45)c(Cl)cc23)CC1] | (2S,4R)-N-(2-((18-(4-(4-acryloylpiperazin-1-yl)-6-chloro-8-fluoro-7-(3-hydroxynaphthalen-1-yl)quinazolin-2-yl)amino)-15-methyl-16-oxo-3,6,9,12-tetraoxa-15-azaoctadecyl)oxy)-4-(4-methylthiazol-5-yl)benzyl)-4-hydroxy-1-((R)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 346 | 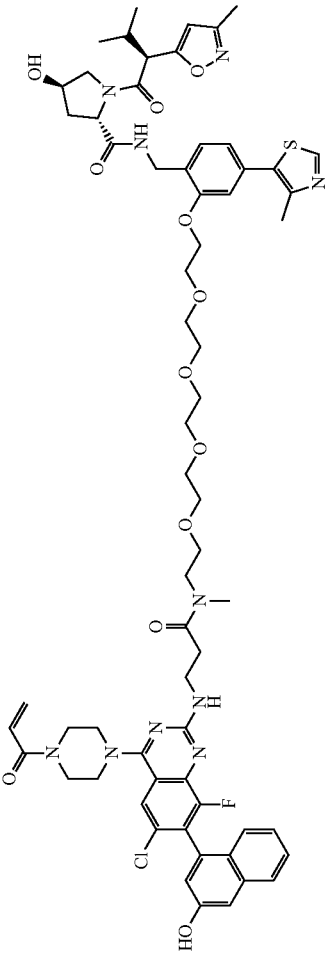 | (2S,4R)-N-(2-((18-((4-(4-acryloylpiperazin-1-yl)-6-chloro-8-fluoro-7-(3-hydroxynaphthalen-1-yl)quinazolin-2-yl)amino)-15-methyl-16-oxo-3,6,9,12-tetraoxa-15-azaoctadecyl)oxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |
| 347 | 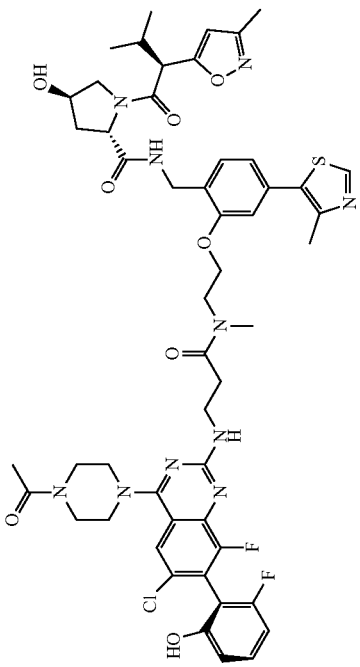 | (2S,4R)-N-(2-(2-(3-(((S)-4-(4-acetylpiperazin-1-yl)-6-chloro-8-fluoro-7-(2-fluoro-6-hydroxyphenyl)quinazolin-2-yl)amino)-N-methylpropanamido)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 348 | 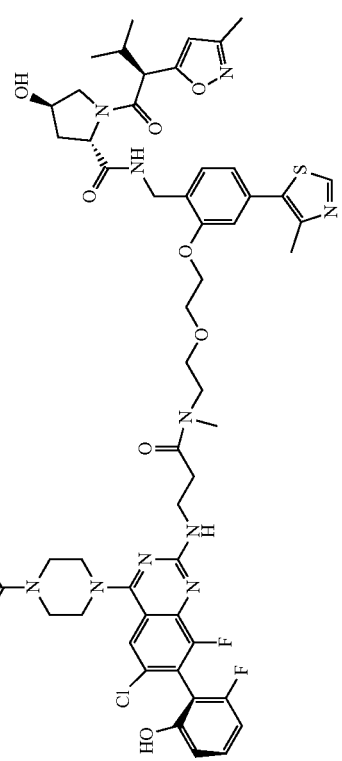 | (2S,4R)-N-(2-(2-(2-(3-(((S)-4-(4-acetylpiperazin-1-yl)-6-chloro-8-fluoro-7-(2-fluoro-6-hydroxyphenyl)quinazolin-2-yl)amino)-N-methylpropanamido)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 7 |
| 349 | 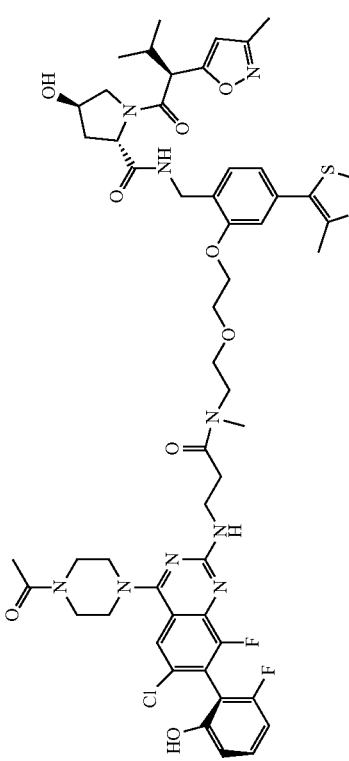 | (2S,4R)-N-(2-(2-(2-(3-(((S)-4-(4-acetylpiperazin-1-yl)-6-chloro-8-fluoro-7-(2-fluoro-6-hydroxyphenyl)quinazolin-2-yl)amino)-N-methylpropanamido)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 350 | 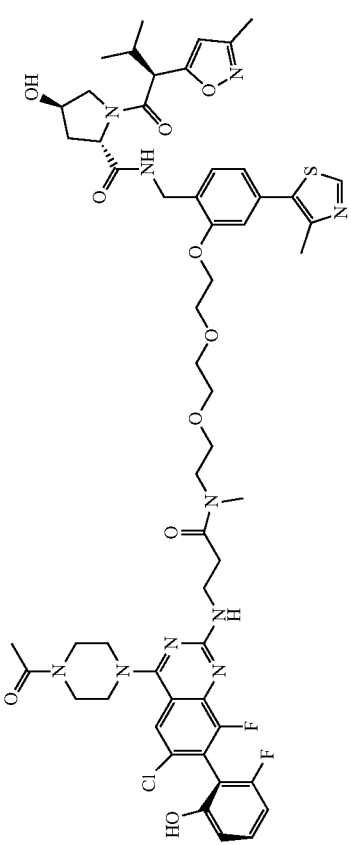 | (2S,4R)-N-(2-(2-(2-(2-(3-(((S)-4-(4-acetylpiperazin-1-yl)-6-chloro-8-fluoro-7-(2-fluoro-6-hydroxyphenyl)quinazolin-2-yl)amino)-N-methylpropanamido)ethoxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |
| 351 | 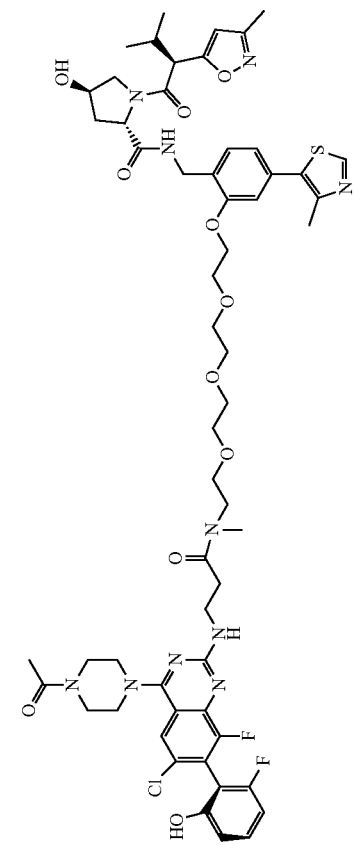 | (2S,4R)-N-(2-((1S-(((S)-4-(4-acetylpiperazin-1-yl)-6-chloro-8-fluoro-7-(2-fluoro-6-hydroxyphenyl)quinazolin-2-yl)amino)-12-methyl-13-oxo-3,6,9-trioxa-12-azapentadecyl)oxy)-4-(4-methylthiazol-5-yl)benzyl)-4-hydroxy-14(S)-3-methyl-2-(3-methylisoxazol-5-yl)butanoyl)pyrrolidine-2-carboxamide | 7 |

TABLE 10-continued

Compounds Prepared by Schemes 7-16

| Ex. No. | Structure | Compound Name | Synthetic Scheme |
|---|---|---|---|
| 352 | 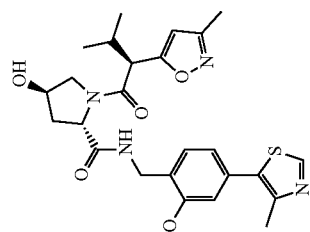 | (2S,4R)-N-(2-((1S-(((S)-4-(4-acetylpiperazin-1-yl)-6-chloro-8-fluoro-7-(2-fluoro-6-hydroxyphenyl)quinazolin-2-yl)amino)-15-methyl-16-oxo-3,6,9,12-tetraoxa-15-azaoctadecyoxy)-4-(4-methylthiazol-5-yl)benzyl)-4-hydroxy-1-((S)-3-methyl-2-(3-methylisoxazol-5-yl)butanoyl)pyrrolidine-2-carboxamide | 7 |
| 353 | 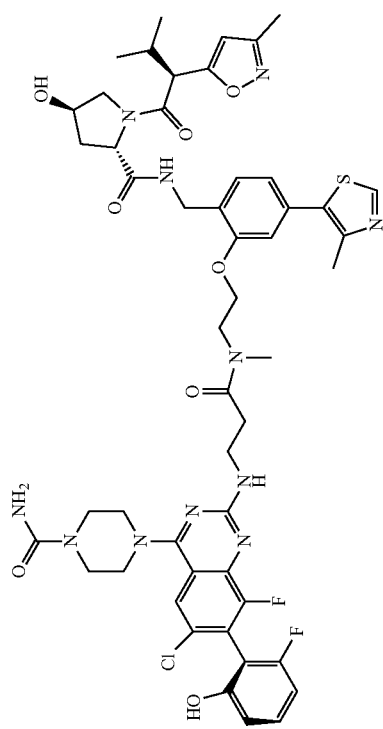 | 4-((S)-6-chloro-8-fluoro-7-(2-fluoro-6-hydroxyphenyl)-2-((3-((2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethyl)(methyl)amino)-3-oxopropyl)amino)quinazolin-4-yl)piperazine-1-carboxamide | 7 |

TABLE 10-continued

Compounds Prepared by Schemes 7-16

| Ex. No. | Structure | Compound Name | Synthetic Scheme |
|---|---|---|---|
| 354 | 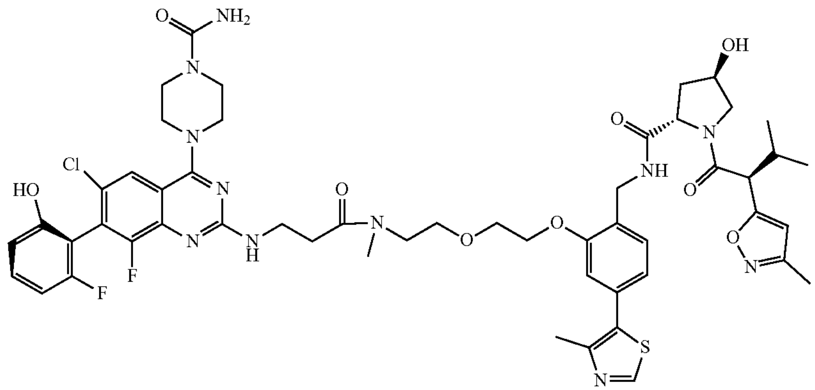 | 4-((S)-6-chloro-8-fluoro-7-(2-fluoro-6-hydroxyphenyl)-2-((3-((2-(2-(2-(4S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)amino)-3-oxopropyl)amino)quinazolin-4-yl)piperazine-1-carboxamide | 7 |
| 355 | 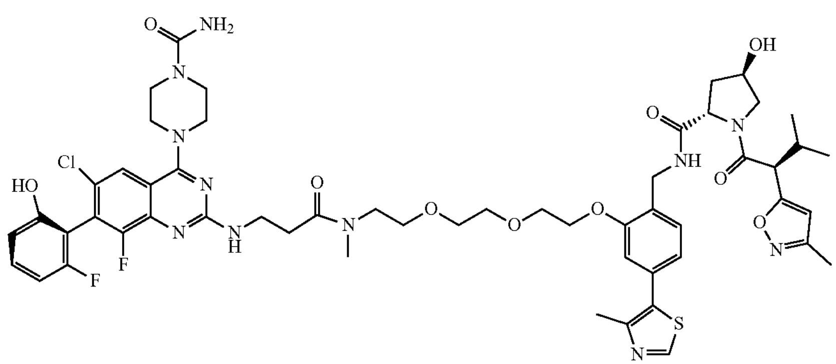 | 4-((S)-6-chloro-8-fluoro-7-(2-fluoro-6-hydroxyphenyl)-2-((3-((2-(2-(2-(4S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethyl)(methyl)amino)-3-oxopropyl)amino)quinazolin-4-yl)piperazine-1-carboxamide | 7 |

TABLE 10-continued

Compounds Prepared by Schemes 7-16

| Ex. No. | Structure | Compound Name | Synthetic Scheme |
|---|---|---|---|
| 356 | 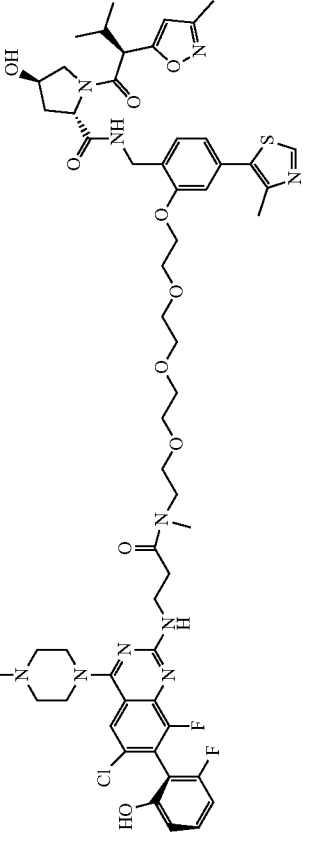 | 4-((S)-6-chloro-8-fluoro-7-(2-fluoro-6-hydroxyphenyl)-2-((1-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)-12-methyl-13-oxo-3,6,9-trioxa-12-azapentadecan-15-yl)amino)quinazolin-4-yl)piperazine-1-carboxamide | 7 |
| 357 | 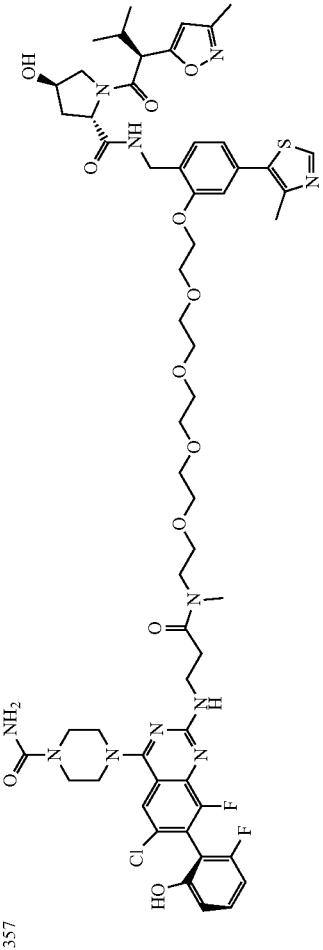 | 4-((S)-6-chloro-8-fluoro-7-(2-fluoro-6-hydroxyphenyl)-2-((1-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)-15-methyl-16-oxo-3,6,9,12-tetraoxa-15-azaoctadecan-18-yl)amino)quinazolin-4-yl)piperazine-1-carboxamide | 7 |

TABLE 10-continued

Compounds Prepared by Schemes 7-16

| Ex. No. | Structure | Compound Name | Synthetic Scheme |
|---|---|---|---|
| 358 | 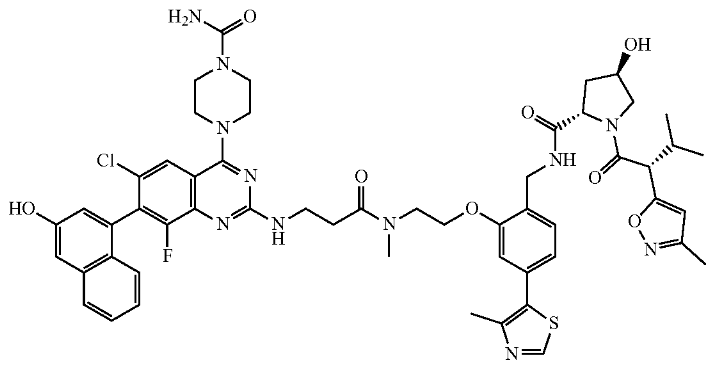 [SMILES: Cc1cc([C@H](C(=O)N2C[C@H](O)C[C@H]2C(=O)NCc2ccc(-c3scnc3C)cc2OCCN(C)C(=O)CCNc2nc(N3CCN(C(N)=O)CC3)c3cc(Cl)c(-c4cc(O)cc5ccccc45)c(F)c3n2)C(C)C)on1] | 4-(6-chloro-8-fluoro-2-((2-((2-(((2S,4R)-4-hydroxy-1-((R)-3-methyl-2-(3-methylisoxazol-5-yl)butanoyl)pyrrolidine-2-carboxamido)methyl)-5-methylthiazol-5-yl)phenoxy)ethyl)(methyl)amino)-3-oxopropyl)amino)-7-(3-hydroxynaphthalen-1-yl)quinazolin-4-yl)piperazine-1-carboxamide | 7 |
| 359 | 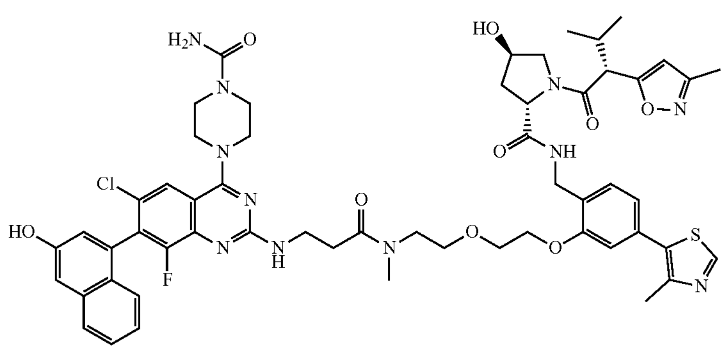 [SMILES: Cc1cc([C@H](C(=O)N2C[C@H](O)C[C@H]2C(=O)NCc2ccc(-c3scnc3C)cc2OCCOCCN(C)C(=O)CCNc2nc(N3CCN(C(N)=O)CC3)c3cc(Cl)c(-c4cc(O)cc5ccccc45)c(F)c3n2)C(C)C)on1] | 4-(6-chloro-8-fluoro-2-((3-((2-(2-(2-(((2S,4R)-4-hydroxy-1-((R)-3-methyl-2-(3-methylisoxazol-5-yl)butanoyl)pyrrolidine-2-carboxamido)methyl)-5-methylthiazol-5-yl)phenoxy)ethoxy)ethyl)(methyl)amino)-3-oxopropyl)amino)-7-(3-hydroxynaphthalen-1-yl)quinazolin-4-yl)piperazine-1-carboxamide | 7 |

TABLE 10-continued

Compounds Prepared by Schemes 7-16

| Ex. No. | Structure | Compound Name | Synthetic Scheme |
|---|---|---|---|
| 360 | 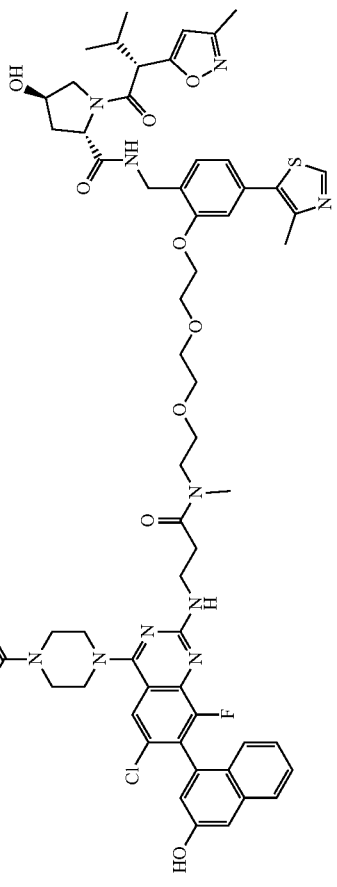 | 4-(6-chloro-8-fluoro-2-((3-((2-(2-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)ethoxy)ethyl)(methyl)amino)-3-oxopropyl)amino)-7-(3-hydroxynaphthalen-1-yl)quinazolin-4-yl)piperazine-1-carboxamide | 7 |
| 361 | 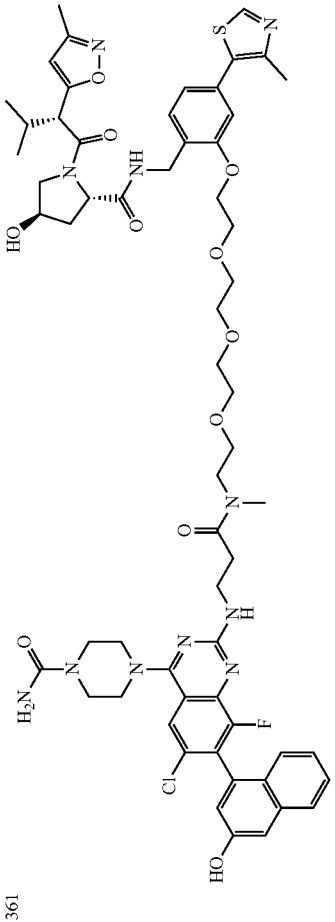 | 4-(6-chloro-8-fluoro-2-((1-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)-12-methyl-13-oxo-3,6,9-trioxa-12-azapentadecan-15-yl)amino)-7-(3-hydroxynaphthalen-1-yl)quinazolin-4-yl)piperazine-1-carboxamide | 7 |

TABLE 10-continued

Compounds Prepared by Schemes 7-16

| Ex. No. | Structure | Compound Name | Synthetic Scheme |
|---|---|---|---|
| 362 | 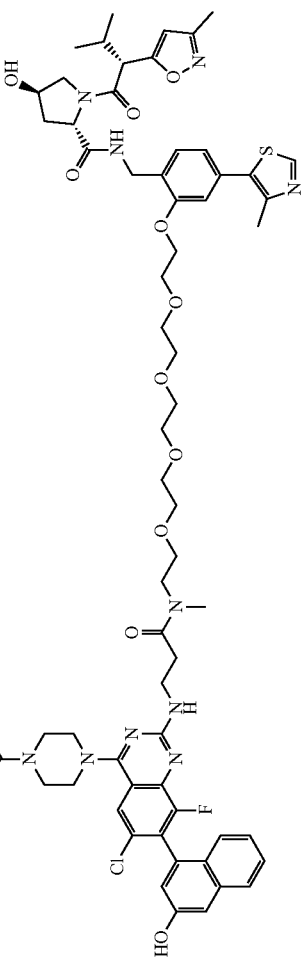 | 4-(6-chloro-8-fluoro-2-((1-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)-15-methyl-16-oxo-3,6,9,12-tetraoxa-15-azaoctadecan-18-yl)amino)-7-(3-hydroxynaphthalen-1-yl)quinazolin-4-yl)piperazine-1-carboxamide | 7 |
| 363 | 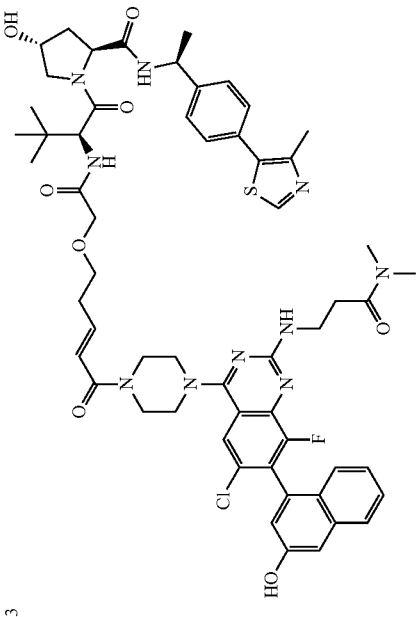 | (2S,4R)-1-((2S)-2-((E)-5-(4-(6-chloro-2-((3-(dimethylamino)-3-oxopropyl)amino)-8-fluoro-7-(3-hydroxynaphthalen-1-yl)quinazolin-4-yl)piperazin-1-yl)-5-oxopent-3-en-1-yl)oxy)acetamido)-3,3-dimethylbutanoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 364 | 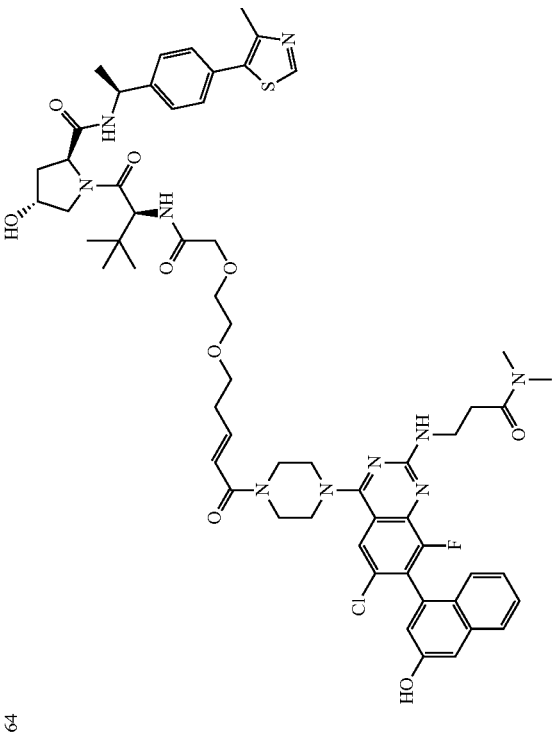 | (2S,4R)-1-((2S)-2-(2-(2-(((E)-5-(4-(6-chloro-2-((3-(dimethylamino)-3-oxopropyl)amino)-8-fluoro-7-(3-hydroxynaphthalen-1-yl)quinazolin-4-yl)piperazin-1-yl)-5-oxopent-3-en-1-yl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 8 |
| 365 | 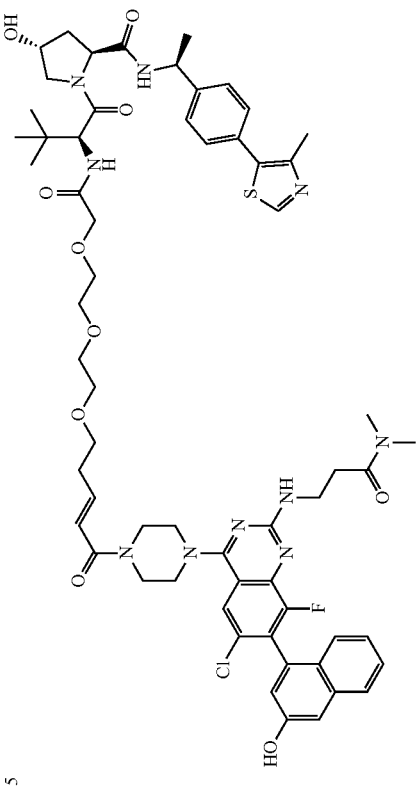 | (2S,4R)-14(2S,E)-2-(tert-butyl)-17-(4-(6-chloro-2-((3-(dimethylamino)-3-oxopropyl)amino)-8-fluoro-7-(3-hydroxynaphthalen-1-yl)quinazolin-4-yl)piperazin-1-yl)-4,17-dioxo-6,9,12-trioxa-3-azaheptadec-15-enoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 366 | 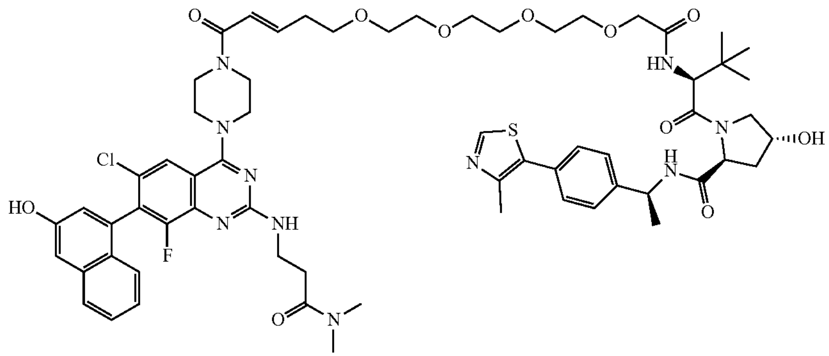 [SMILES: Cc1ncsc1-c1ccc([C@H](C)NC(=O)[C@@H]2C[C@@H](O)CN2C(=O)[C@@H](NC(=O)COCCOCCOCCOCC/C=C/C(=O)N2CCN(c3nc(NCCC(=O)N(C)C)nc4c(F)c(-c5cc(O)cc6ccccc56)c(Cl)cc34)CC2)C(C)(C)C)cc1] | (2S,4R)-1-42S,E)-2-(tert-butyl)-20-(4-(6-chloro-2-((3-(dimethyl)amino)-3-oxopropyl)amino)-8-fluoro-7-(3-hydroxynaphthalen-1-yl)quinazolin-4-yl)piperazin-1-yl)-4,20-dioxo-6,9,12,15-tetraoxa-3-azaicos-18-enoyl)-4-hydroxy-N-((S)-1-(4-(4-methylthiazol-5-yl)phenyl)ethyl)pyrrolidine-2-carboxamide | 8 |
| 367 | 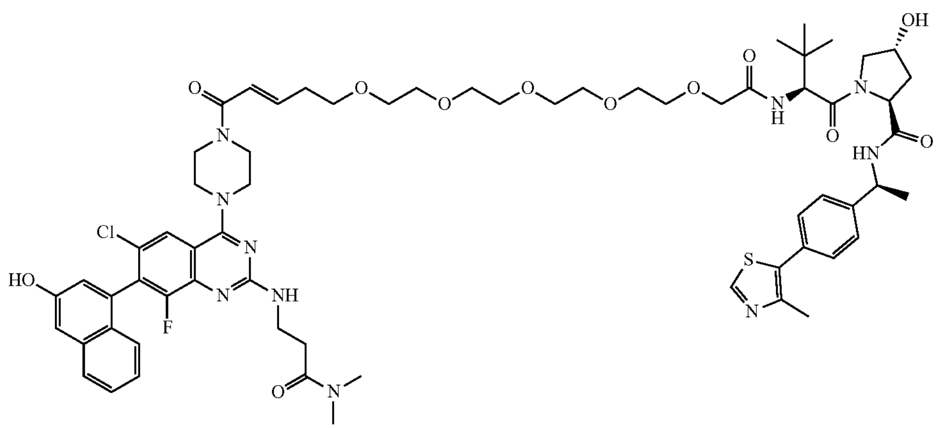 [SMILES: Cc1ncsc1-c1ccc([C@H](C)NC(=O)[C@@H]2C[C@@H](O)CN2C(=O)[C@@H](NC(=O)COCCOCCOCCOCCOCC/C=C/C(=O)N2CCN(c3nc(NCCC(=O)N(C)C)nc4c(F)c(-c5cc(O)cc6ccccc56)c(Cl)cc34)CC2)C(C)(C)C)cc1] | (2S,4R)-1-((2S,E)-2-(tert-butyl)-23-(4-(6-chloro-2-((3-(dimethyl)amino)-3-oxopropyl)amino)-8-fluoro-7-(3-hydroxynaphthalen-1-yl)quinazolin-4-yl)piperazin-1-yl)-4,23-dioxo-6,9,12,15,18-pentaoxa-3-azatricos-21-enoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 368 | 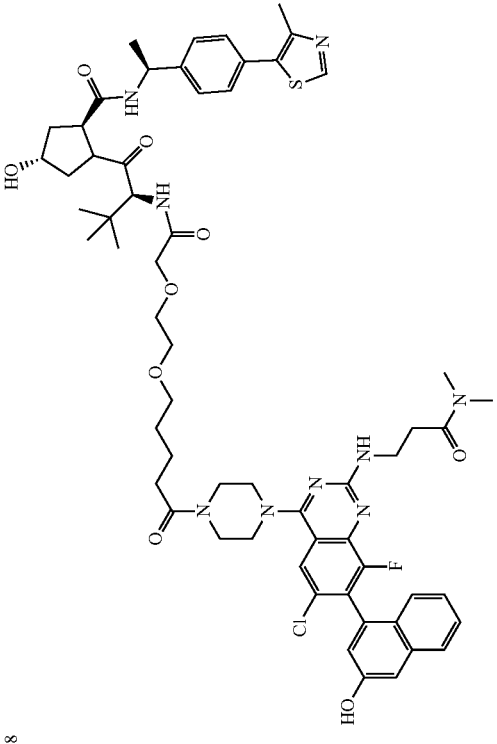 | (2S,4R)-1-((2S)-2-(2-(2-(5-(4-(6-chloro-2-((3-(dimethylamino)-3-oxopropyl)amino)-8-fluoro-7-(3-hydroxynaphthalen-1-yl)quinazolin-4-yl)piperazin-1-yl)-5-oxopentyl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 8 |
| 369 | 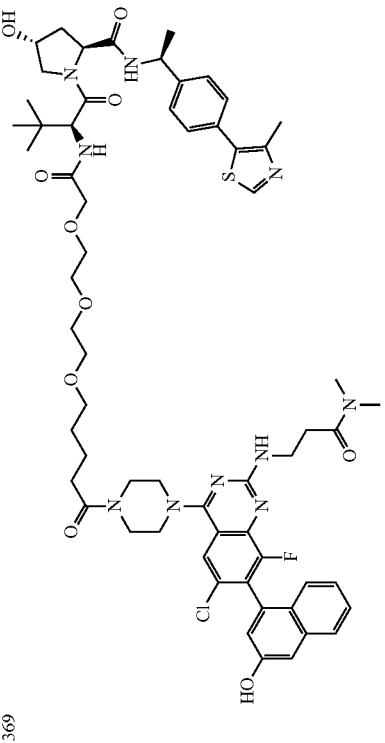 | (2S,4R)-1-((2S)-2-(tert-butyl)-17-(4-(6-chloro-2-((3-(dimethylamino)-3-oxopropyl)amino)-8-fluoro-7-(3-hydroxynaphthalen-1-yl)quinazolin-4-yl)piperazin-1-yl)-4,17-dioxo-6,9,12-trioxa-3-azaheptadecanoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 370 | 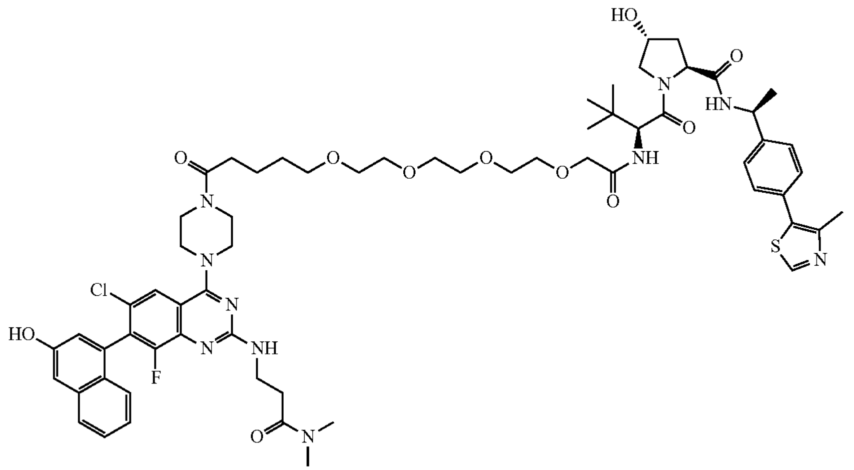 [SMILES: Cc1ncsc1-c1ccc([C@H](C)NC(=O)[C@@H]2C[C@@H](O)CN2C(=O)[C@@H](NC(=O)COCCOCCOCCOCCCCC(=O)N2CCN(c3nc(NCCC(=O)N(C)C)nc4c(F)c(-c5cc(O)cc6ccccc56)c(Cl)cc34)CC2)C(C)(C)C)cc1] | (2S,4R)-1-((2S)-2-(tert-butyl)-20-(4-(6-chloro-2-((3-(dimethylamino)-3-oxopropyl)amino)-8-fluoro-7-(3-hydroxynaphthalen-1-yl)quinazolin-4-yl)piperazin-1-yl)-4,20-dioxo-6,9,12,15-tetraoxa-3-azaicosanoyl)-4-hydroxy-N-((S)-1-(4-(4-methylthiazol-5-yl)phenyl)ethyl)pyrrolidine-2-carboxamide | 8 |
| 371 | 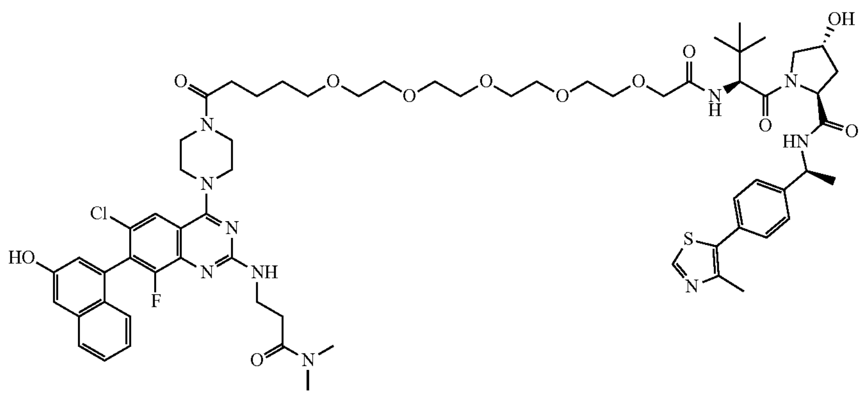 [SMILES: Cc1ncsc1-c1ccc([C@H](C)NC(=O)[C@@H]2C[C@@H](O)CN2C(=O)[C@@H](NC(=O)COCCOCCOCCOCCOCCCCC(=O)N2CCN(c3nc(NCCC(=O)N(C)C)nc4c(F)c(-c5cc(O)cc6ccccc56)c(Cl)cc34)CC2)C(C)(C)C)cc1] | (2S,4R)-1-((2S)-2-(tert-butyl)-23-(4-(6-chloro-2-((3-(dimethylamino)-3-oxopropyl)amino)-8-fluoro-7-(3-hydroxynaphthalen-1-yl)quinazolin-4-yl)piperazin-1-yl)-4,23-dioxo-6,9,12,15,18-pentaoxa-3-azatricosanoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 372 | 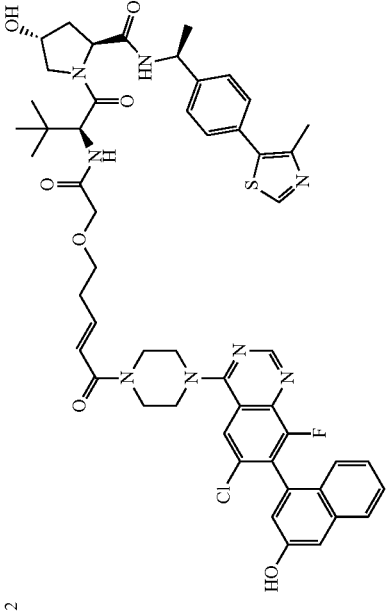 | (2S,4R)-1-((2S)-2-(2-(((E)-5-(4-(6-chloro-8-fluoro-7-(3-hydroxynaphthalen-1-yl)quinazolin-4-yl)piperazin-1-yl)-5-oxopent-3-en-1-yl)oxy)acetamido)-3,3-dimethylbutanoyl)-4-hydroxy-N-((S)-1-(4-(4-methylthiazol-5-yl)phenyl)ethyl)pyrrolidine-2-carboxamide | 8 |
| 373 | 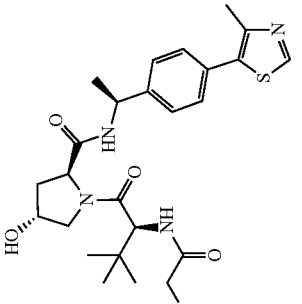 | (2S,4R)-1-((2S)-2-(2-(((E)-5-(4-(6-chloro-8-fluoro-7-(3-hydroxynaphthalen-1-yl)quinazolin-4-yl)piperazin-1-yl)-5-oxopent-3-en-1-yl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 374 | 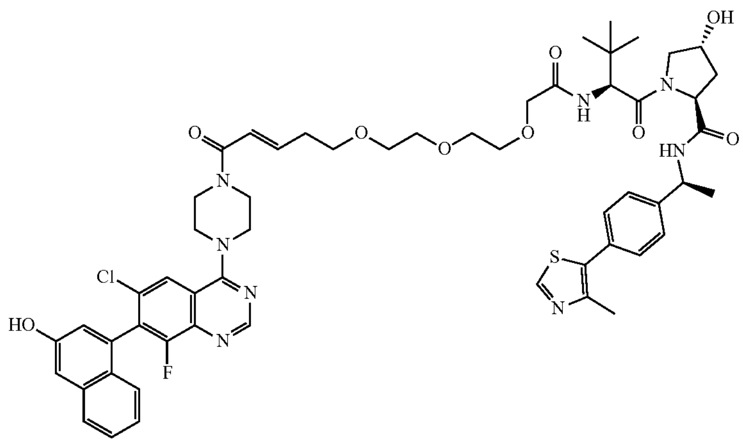 [SMILES: Cc1ncsc1-c1ccc([C@H](C)NC(=O)[C@@H]2C[C@@H](O)CN2C(=O)[C@@H](NC(=O)COCCOCCOCC/C=C/C(=O)N2CCN(c3ncnc4c(F)c(-c5cc(O)cc6ccccc56)c(Cl)cc34)CC2)C(C)(C)C)cc1] | (2S,4R)-14((2S,E)-2-(tert-butyl)-17-(4-(6-chloro-8-fluoro-7-(3-hydroxynaphthalen-1-yl)quinazolin-4-yl)piperazin-1-yl)-4,17-dioxo-6,9,12-trioxa-3-azaheptadec-15-enoyl)-4-hydroxy-N-((S)-1-(4-(4-methylthiazol-5-yl)phenyl)ethyl)pyrrolidine-2-carboxamide | 8 |
| 375 | 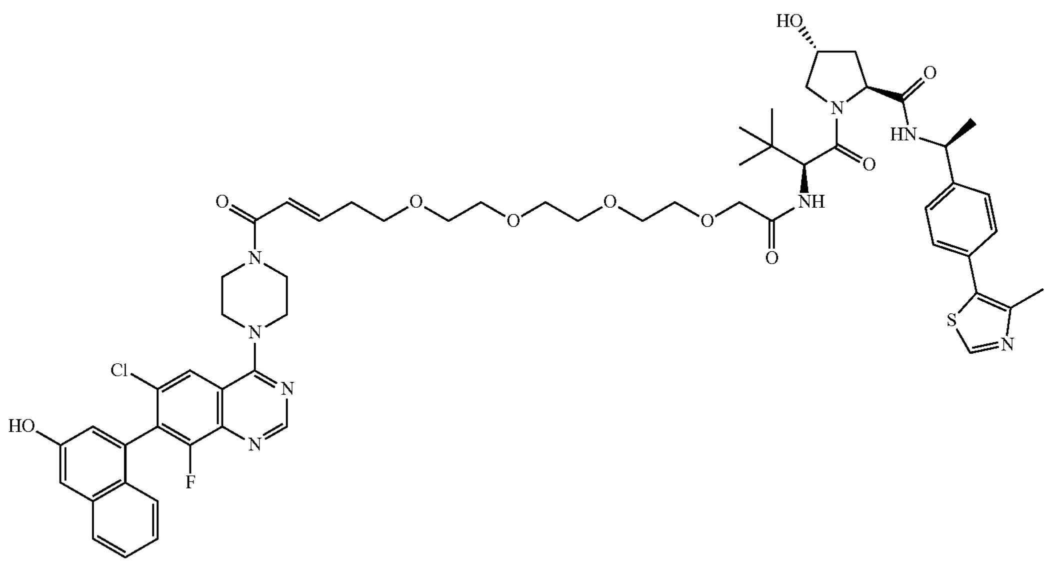 [SMILES: Cc1ncsc1-c1ccc([C@H](C)NC(=O)[C@@H]2C[C@@H](O)CN2C(=O)[C@@H](NC(=O)COCCOCCOCCOCC/C=C/C(=O)N2CCN(c3ncnc4c(F)c(-c5cc(O)cc6ccccc56)c(Cl)cc34)CC2)C(C)(C)C)cc1] | (2S,4R)-1-((2S,E)-2-(tert-butyl)-20-(4-(6-chloro-8-fluoro-7-(3-hydroxynaphthalen-1-yl)quinazolin-4-yl)piperazin-1-yl)-4,20-dioxo-6,9,12,15-tetraoxa-3-azaicos-18-enoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 376 | 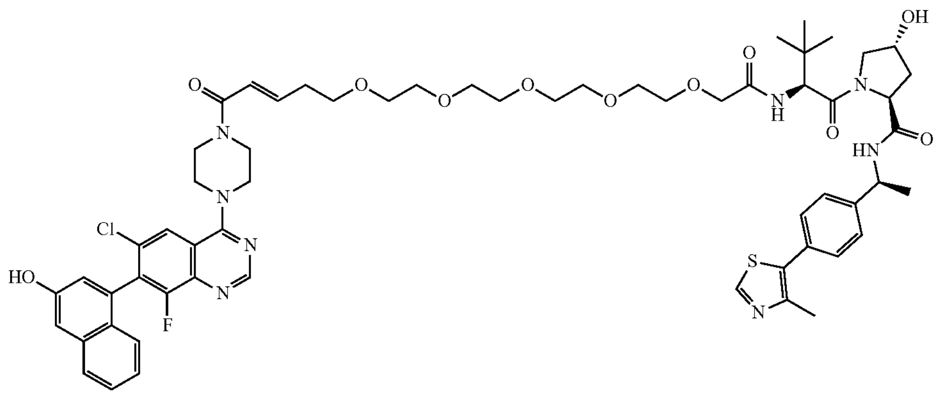 | (2S,4R)-1-((2S,E)-2-(tert-butyl)-23-(4-(6-chloro-8-fluoro-7-(3-hydroxynaphthalen-1-yl)quinazolin-4-yl)piperazin-1-yl)-4,23-dioxo-6,9,12,15,18-pentaoxa-3-azatricos-21-enoyl)-4-hydroxy-N-((S)-1-(4-(4-methylthiazol-5-yl)phenyl)ethyl)pyrrolidine-2-carboxamide | 8 |
| 377 | 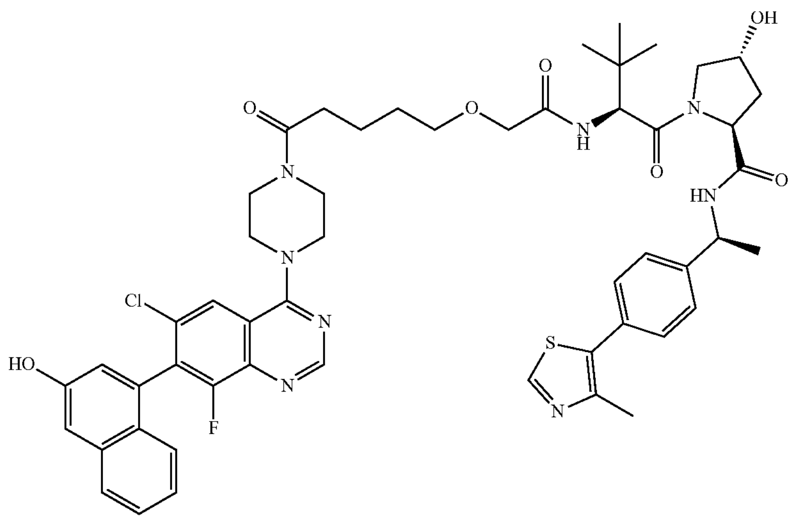 [SMILES: Cc1ncsc1-c1ccc([C@H](C)NC(=O)[C@@H]2C[C@@H](O)CN2C(=O)[C@@H](NC(=O)COCCCCC(=O)N2CCN(c3ncnc4c(F)c(-c5cc(O)cc6ccccc56)c(Cl)cc34)CC2)C(C)(C)C)cc1] | (2S,4R)-1-((2S)-2-((5-(4-(6-chloro-8-fluoro-7-(3-hydroxynaphthalen-1-yl)quinazolin-4-yl)piperazin-1-yl)-5-oxopentyl)oxy)acetamido)-3,3-dimethylbutanoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 378 | 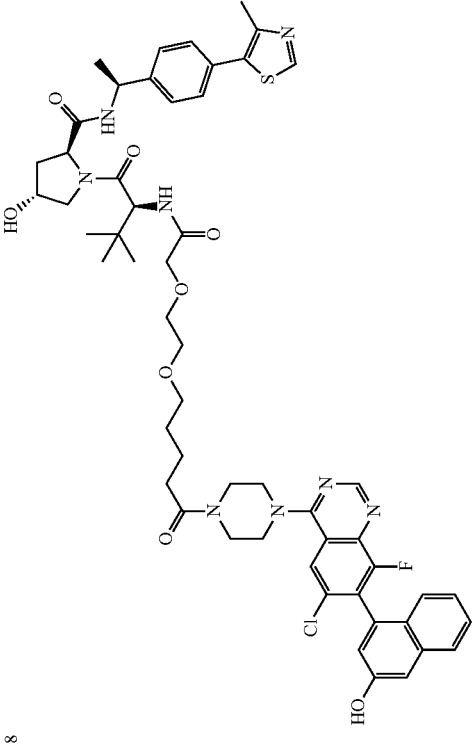 | (2S,4R)-1-((2S)-2-(2-(2-(5-(4-(6-chloro-8-fluoro-7-(3-hydroxynaphthalen-1-yl)quinazolin-4-yl)piperazin-1-yl)-5-oxopentyl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 8 |
| 379 | 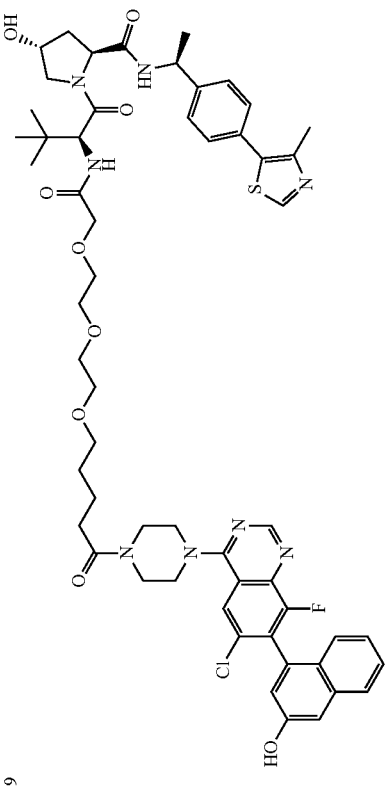 | (2S,4R)-1-((2S)-2-(tert-butyl)-17-(4-(6-chloro-8-fluoro-7-(3-hydroxynaphthalen-1-yl)quinazolin-4-yl)piperazin-1-yl)-4,17-dioxo-6,9,12-trioxa-3-azaheptadecanoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 380 | 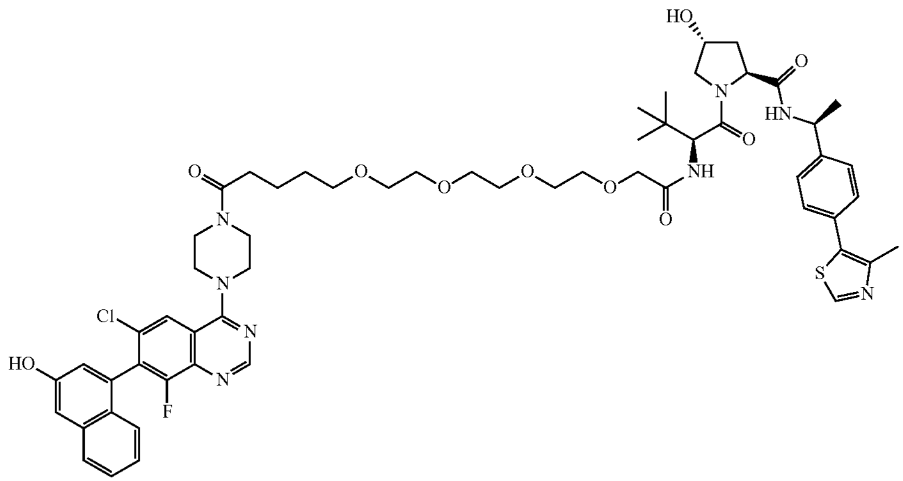 [SMILES: Cc1ncsc1-c1ccc([C@H](C)NC(=O)[C@@H]2C[C@@H](O)CN2C(=O)[C@@H](NC(=O)COCCOCCOCCOCCCCC(=O)N2CCN(c3ncnc4c(F)c(-c5cc(O)cc6ccccc56)c(Cl)cc34)CC2)C(C)(C)C)cc1] | (2S,4R)-1-((2S)-2-(tert-butyl)-20-(4-(6-chloro-8-fluoro-7-(3-hydroxynaphthalen-1-yl)quinazolin-4-yl)piperazin-1-yl)-4,20-dioxo-6,9,12,15-tetraoxa-3-azaicosanoyl)-4-hydroxy-N-((S)-1-(4-(4-methylthiazol-5-yl)phenyl)ethyl)pyrrolidine-2-carboxamide | 8 |
| 381 | 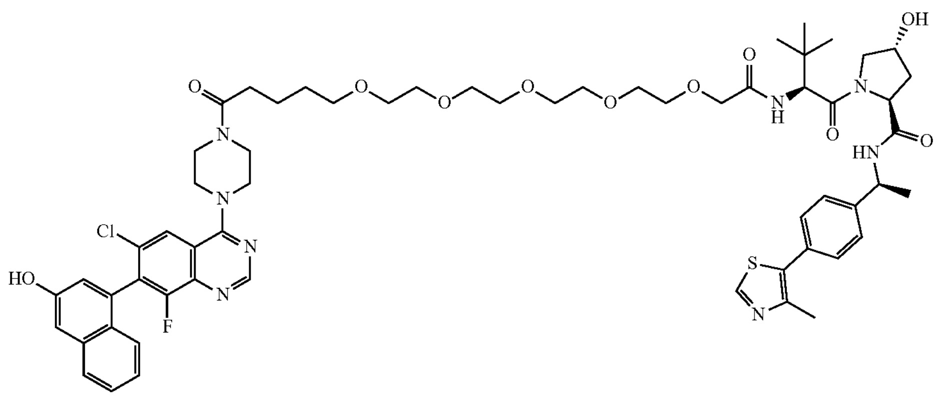 [SMILES: Cc1ncsc1-c1ccc([C@H](C)NC(=O)[C@@H]2C[C@@H](O)CN2C(=O)[C@@H](NC(=O)COCCOCCOCCOCCOCCCCC(=O)N2CCN(c3ncnc4c(F)c(-c5cc(O)cc6ccccc56)c(Cl)cc34)CC2)C(C)(C)C)cc1] | (2S,4R)-14(2S)-2-(tert-butyl)-23-(4-(6-chloro-8-fluoro-7-(3-hydroxynaphthalen-1-yl)quinazolin-4-yl)piperazin-1-yl)-4,23-dioxo-6,9,12,15,18-pentaoxa-3-azatricosanoyl)-4-hydroxy-N-((S)-1-(4-(4-methylthiazol-5-yl)phenyl)ethyl)pyrrolidine-2-carboxamide | 8 |

TABLE 10-continued

Compounds Prepared by Schemes 7-16

| Ex. No. | Structure | Compound Name | Synthetic Scheme |
|---|---|---|---|
| 382 | 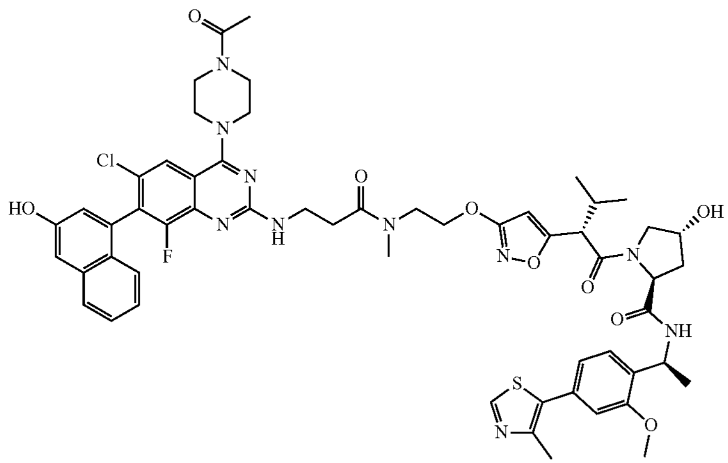 [SMILES: COc1cc(-c2scnc2C)ccc1[C@H](C)NC(=O)[C@@H]1C[C@@H](O)CN1C(=O)[C@H](c1cc(OCCN(C)C(=O)CCNc2nc(N3CCN(C(C)=O)CC3)c3cc(Cl)c(-c4cc(O)cc5ccccc45)c(F)c3n2)no1)C(C)C] | (2S,4R)-1-((2S)-2-(3-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)isoxazol-5-yl)-3-methylbutanoyl)-4-hydroxy-N-aS)-1-(2-methoxy-4-(4-methylthiazol-5-yl)phenyl)ethyl)pyrrolidine-2-carboxamide | 9 |
| 383 | 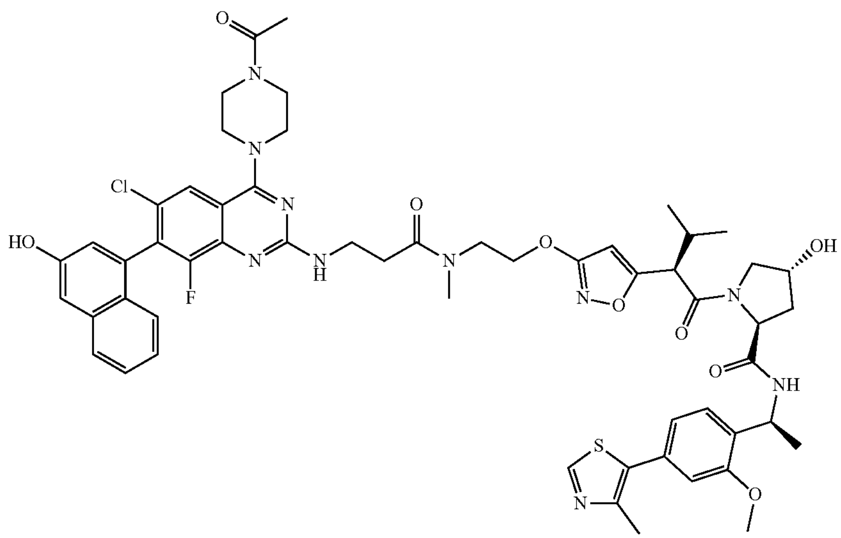 [SMILES: COc1cc(-c2scnc2C)ccc1[C@H](C)NC(=O)[C@@H]1C[C@@H](O)CN1C(=O)[C@@H](c1cc(OCCN(C)C(=O)CCNc2nc(N3CCN(C(C)=O)CC3)c3cc(Cl)c(-c4cc(O)cc5ccccc45)c(F)c3n2)no1)C(C)C] | (2S,4R)-1-((2R)-2-(3-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |

TABLE 10-continued

Compounds Prepared by Schemes 7-16

| Ex. No. | Structure | Compound Name | Synthetic Scheme |
|---|---|---|---|
| 384 | 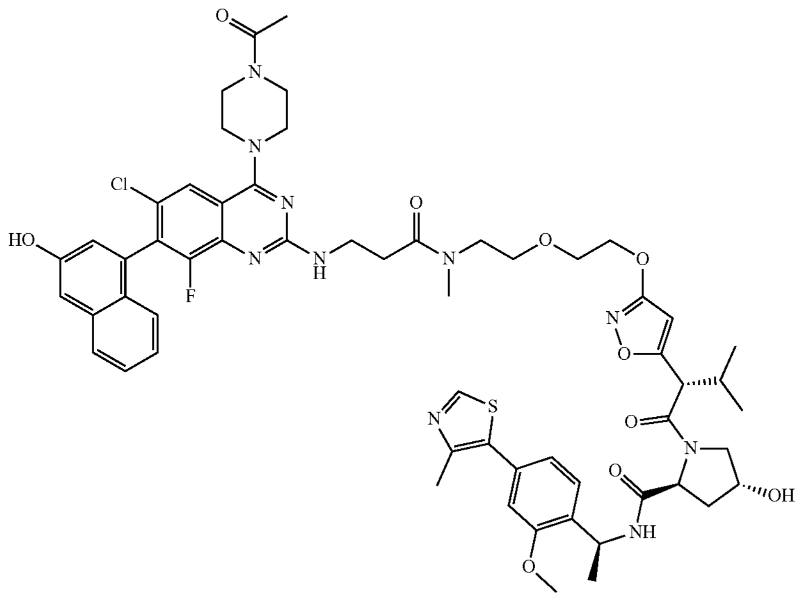 [SMILES: COc1cc(-c2scnc2C)ccc1[C@H](C)NC(=O)[C@@H]1C[C@@H](O)CN1C(=O)[C@H](c1cc(OCCOCCN(C)C(=O)CCNc2nc(N3CCN(C(C)=O)CC3)c3cc(Cl)c(-c4cc(O)cc5ccccc45)c(F)c3n2)no1)C(C)C] | (2S,4R)-1-((2S)-2-(3-(2-(3-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |

TABLE 10-continued

Compounds Prepared by Schemes 7-16

| Ex. No. | Structure | Compound Name | Synthetic Scheme |
|---|---|---|---|
| 385 | 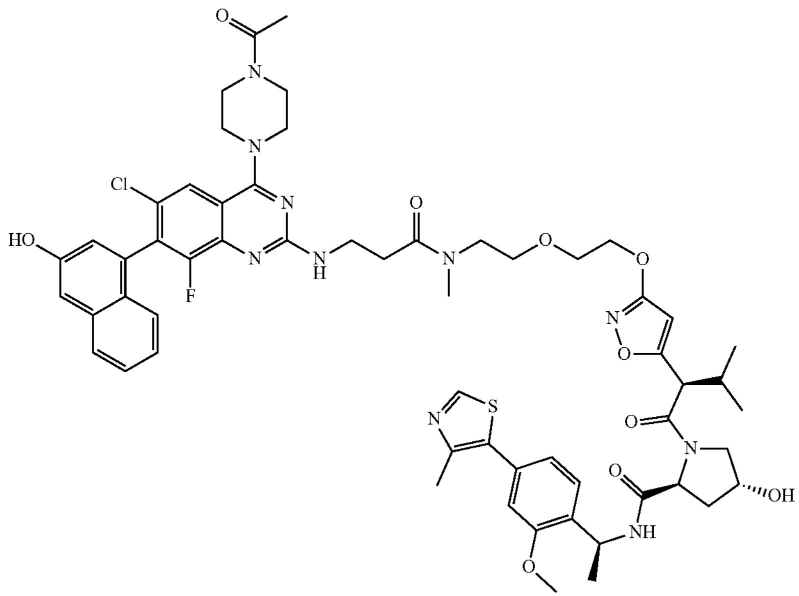 [SMILES: COc1cc(-c2scnc2C)ccc1[C@H](C)NC(=O)[C@@H]1C[C@@H](O)CN1C(=O)[C@@H](c1cc(OCCOCCN(C)C(=O)CCNc2nc(N3CCN(C(C)=O)CC3)c3cc(Cl)c(-c4cc(O)cc5ccccc45)c(F)c3n2)no1)C(C)C] | (2S,4R)-1-((2R)-2-(3-(2-(3-(2-(3-((4-(4-acetylpiperazin-1-yl)-6-chloro-8-fluoro-7-(3-hydroxynaphthlen-1-yl)quinazolin-2-yl)amino)-N-methylpropanamido)ethoxy)ethoxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |

TABLE 10-continued

Compounds Prepared by Schemes 7-16

| Ex. No. | Structure | Compound Name | Synthetic Scheme |
|---|---|---|---|
| 386 | 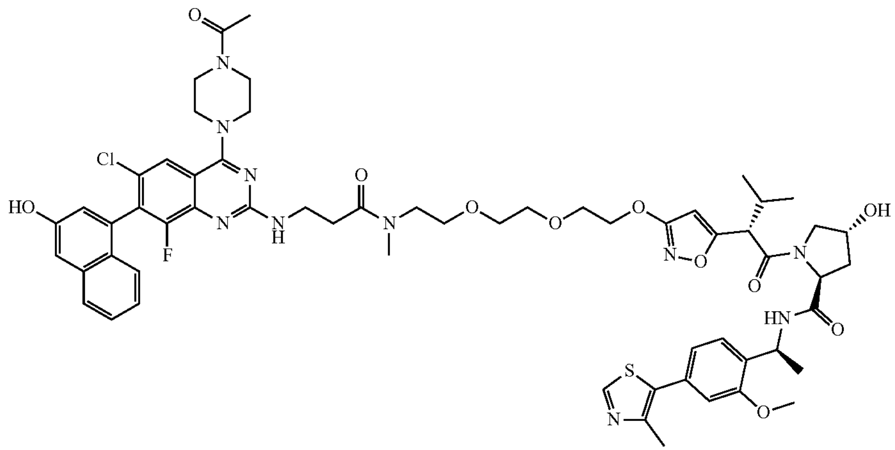 [SMILES: COc1cc(-c2scnc2C)ccc1[C@H](C)NC(=O)[C@@H]1C[C@@H](O)CN1C(=O)[C@H](c1cc(OCCOCCOCCN(C)C(=O)CCNc2nc(N3CCN(C(C)=O)CC3)c3cc(Cl)c(-c4cc(O)cc5ccccc45)c(F)c3n2)no1)C(C)C] | (2S,4R)-1-((2S)-2-(3-(2-(2-(2-(3-((4-(4-acetylpiperazin-1-yl)-6-chloro-8-fluoro-7-(3-hydroxynaphthalen-1-yl)quinazolin-2-yl)amino)-N-methyl)propanamido)ethoxy)ethoxy)ethoxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |
| 387 | 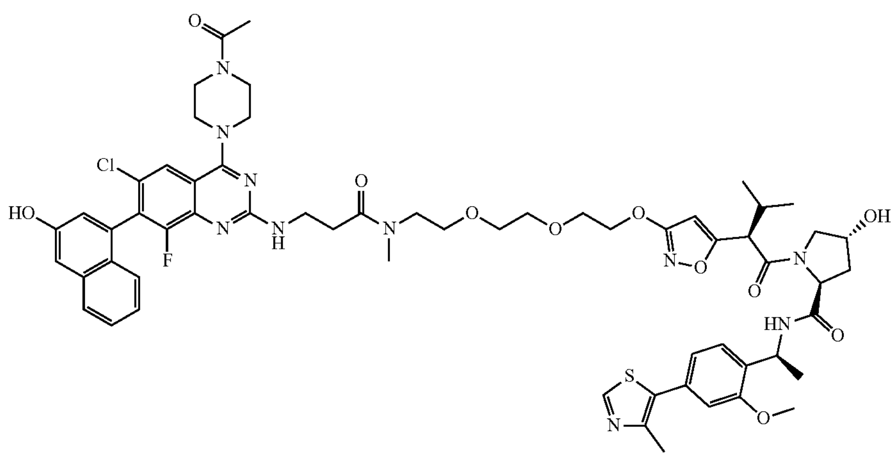 [SMILES: COc1cc(-c2scnc2C)ccc1[C@H](C)NC(=O)[C@@H]1C[C@@H](O)CN1C(=O)[C@@H](c1cc(OCCOCCOCCN(C)C(=O)CCNc2nc(N3CCN(C(C)=O)CC3)c3cc(Cl)c(-c4cc(O)cc5ccccc45)c(F)c3n2)no1)C(C)C] | (2S,4R)-1-((2R)-2-(3-(2-(2-(2-(3-((4-(4-acetylpiperazin-1-yl)-6-chloro-8-fluoro-7-(3-hydroxynaphthalen-1-yl)quinazolin-2-yl)amino)-N-methyl)propanamido)ethoxy)ethoxy)ethoxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |

TABLE 10-continued

Compounds Prepared by Schemes 7-16

| Ex. No. | Structure | Compound Name | Synthetic Scheme |
|---|---|---|---|
| 388 | 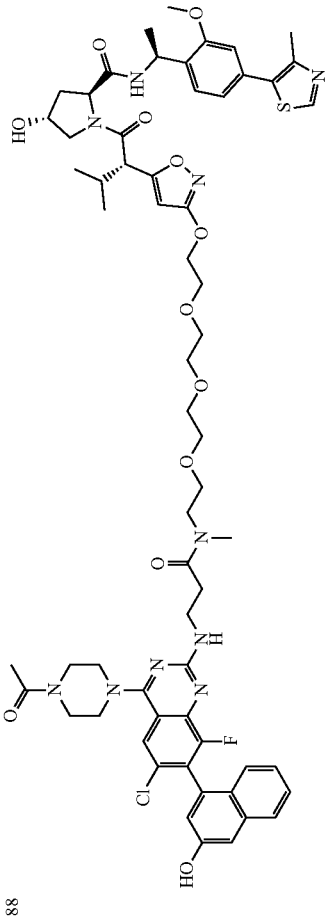 | (2S,4R)-1-((2S)-2-(3-((15-((4-(4-acetylpiperazin-1-yl)-6-chloro-8-fluoro-7-(3-hydroxynaphthalen-1-yl)quinazolin-2-yl)amino)-12-methyl-13-oxo-3,6,9-trioxa-12-azapentadecyl)oxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |
| 389 | 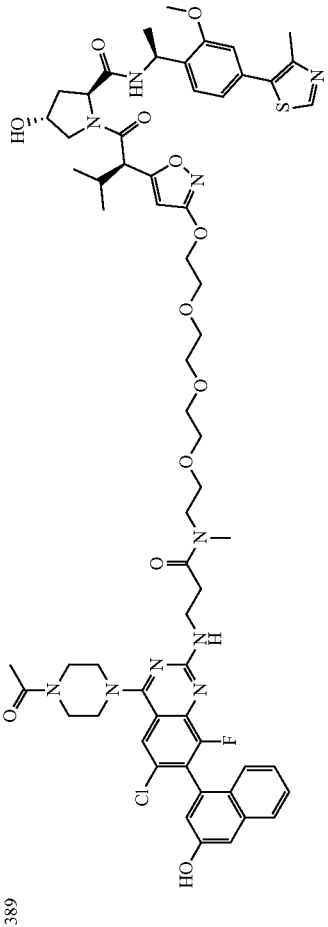 | (2S,4R)-1-((2R)-2-(3-((15-((4-(4-acetylpiperazin-1-yl)-6-chloro-8-fluoro-7-(3-hydroxynaphthalen-1-yl)quinazolin-2-yl)amino)-12-methyl-13-oxo-3,6,9-trioxa-12-azapentadecyl)oxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |

| Ex. No. | Structure | Compound Name | Synthetic Scheme |
|---|---|---|---|
| 390 | 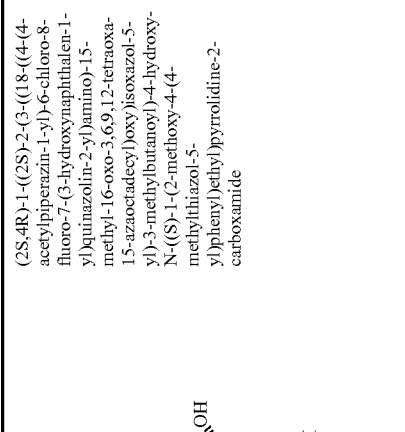 | (2S,4R)-1-((2S)-2-(3-((18-((4-(4-acetylpiperazin-1-yl)-6-chloro-8-fluoro-7-(3-hydroxynaphthalen-1-yl)quinazolin-2-yl)amino)-15-methyl-16-oxo-3,6,9,12-tetraoxa-15-azaoctadecyl)oxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |
| 391 | 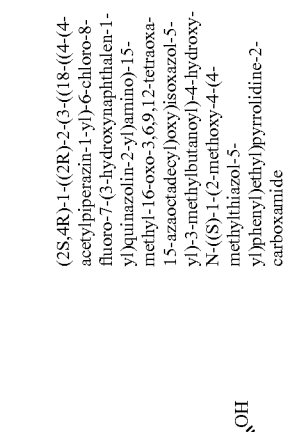 | (2S,4R)-1-((2R)-2-(3-((18-((4-(4-acetylpiperazin-1-yl)-6-chloro-8-fluoro-7-(3-hydroxynaphthalen-1-yl)quinazolin-2-yl)amino)-15-methyl-16-oxo-3,6,9,12-tetraoxa-15-azaoctadecyl)oxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |

TABLE 10-continued

Compounds Prepared by Schemes 7-16

| Ex. No. | Structure | Compound Name | Synthetic Scheme |
|---|---|---|---|
| 392 | 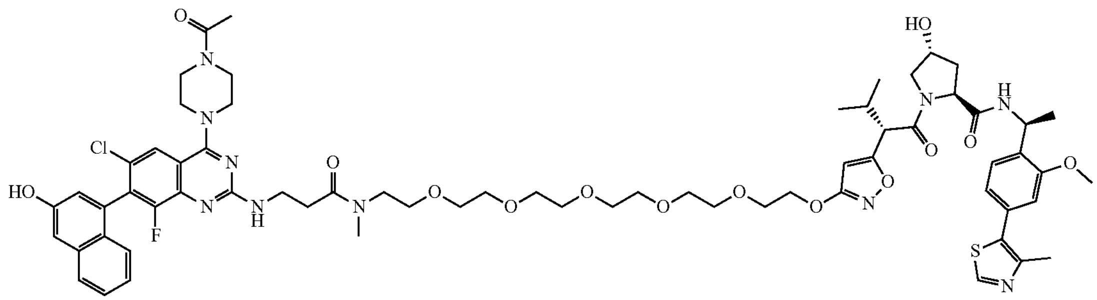 [SMILES: COc1cc(-c2scnc2C)ccc1[C@H](C)NC(=O)[C@@H]1C[C@@H](O)CN1C(=O)[C@H](c1cc(OCCOCCOCCOCCOCCOCCN(C)C(=O)CCNc2nc(N3CCN(C(C)=O)CC3)c3cc(Cl)c(-c4cc(O)cc5ccccc45)c(F)c3n2)no1)C(C)C] | (2S,4R)-1-((2S)-2-(3-(((21-((4-(4-acetylpiperazin-1-yl)-6-chloro-8-fluoro-7-(3-hydroxynaphthalen-1-yl)quinazolin-2-yl)amino)-18-methyl-19-oxo-3,6,9,12,15-pentaoxa-18-azahenicosyl)oxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |
| 393 | 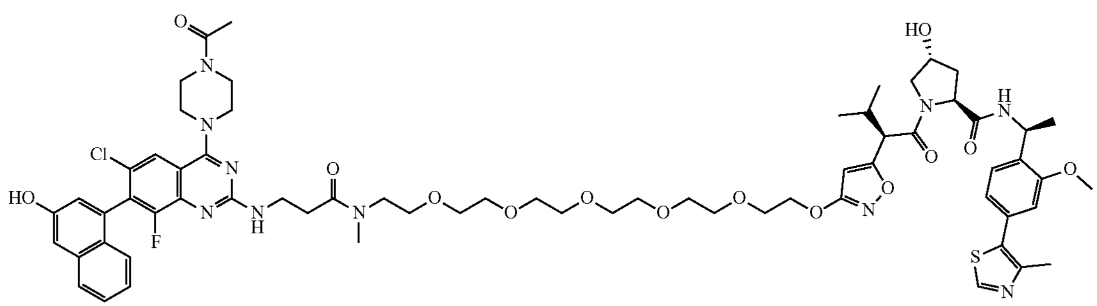 [SMILES: COc1cc(-c2scnc2C)ccc1[C@H](C)NC(=O)[C@@H]1C[C@@H](O)CN1C(=O)[C@@H](c1cc(OCCOCCOCCOCCOCCOCCN(C)C(=O)CCNc2nc(N3CCN(C(C)=O)CC3)c3cc(Cl)c(-c4cc(O)cc5ccccc45)c(F)c3n2)no1)C(C)C] | (2S,4R)-1-((2R)-2-(3-((21-((4-(4-acetylpiperazin-1-yl)-6-chloro-8-fluoro-7-(3-hydroxynaphthalen-1-yl)quinazolin-2-yl)amino)-18-methyl-19-oxo-3,6,9,12,15-pentaoxa-18-azahenicosyl)oxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |

TABLE 10-continued

Compounds Prepared by Schemes 7-16

| Ex. No. | Structure | Compound Name | Synthetic Scheme |
|---|---|---|---|
| 394 | 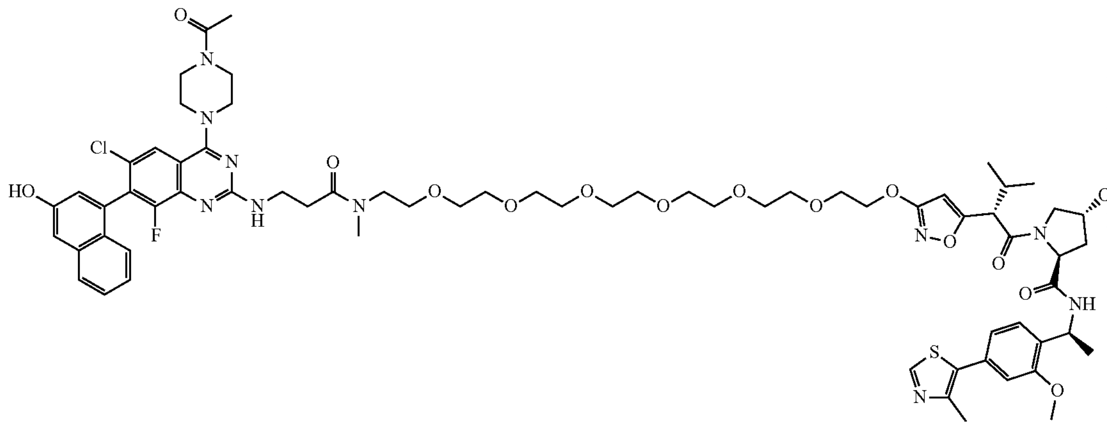 | (2S,4R)-1-((2S)-2-(3-((24-((4-(4-acetylpiperazin-1-yl)-6-chloro-8-fluoro-7-(3-hydroxynaphthalen-1-yl)quinazolin-2-yl)amino)-21-methyl-22-oxo-3,6,9,12,15,18-hexaoxa-21-azatetracosyl)oxy)isoxazol-5-yl)-3-methylbutanoyl)-4-hydroxy-N-((R)-1-(2-methoxy-4-(4-methylthiazol-5-yl)phenyl)ethyl)pyrrolidine-2-carboxamide | 9 |
| 395 | 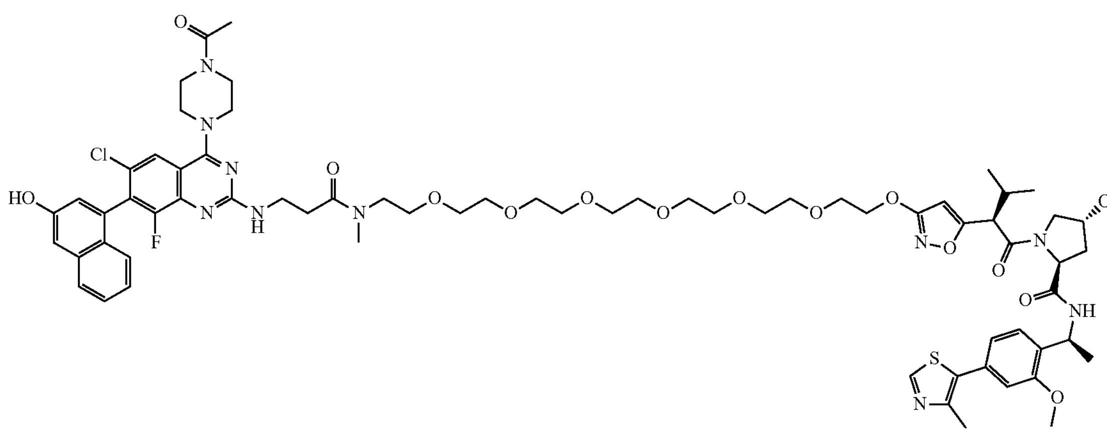 | (2S,4R)-1-((2R)-2-(3-((24-((4-(4-acetylpiperazin-1-yl)-6-chloro-8-fluoro-7-(3-hydroxynaphthalen-1-yl)quinazolin-2-yl)amino)-21-methyl-22-oxo-3,6,9,12,15,18-hexaoxa-21-azatetracosyl)oxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide | 9 |

TABLE 10-continued

Compounds Prepared by Schemes 7-16

| Ex. No. | Structure | Compound Name | Synthetic Scheme |
|---|---|---|---|
| 396 | 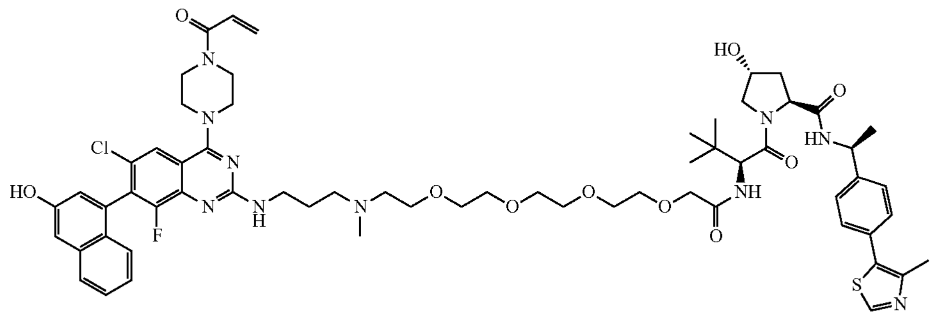 [SMILES: C=CC(=O)N1CCN(c2nc(NCCCN(C)CCOCCOCCOCCOCC(=O)N[C@H](C(=O)N3C[C@H](O)C[C@H]3C(=O)N[C@@H](C)c3ccc(-c4scnc4C)cc3)C(C)(C)C)nc3c(F)c(-c4cc(O)cc5ccccc45)c(Cl)cc23)CC1] | (2S,4R)-1-((2S)-21-((4-(4-acryloylpiperazin-1-yl)-6-chloro-8-fluoro-7-(3-hydroxynaphthalen-1-yl)quinazolin-2-yl)amino)-2-(tert-butyl)-18-methyl-4-oxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 10 |
| 397 | 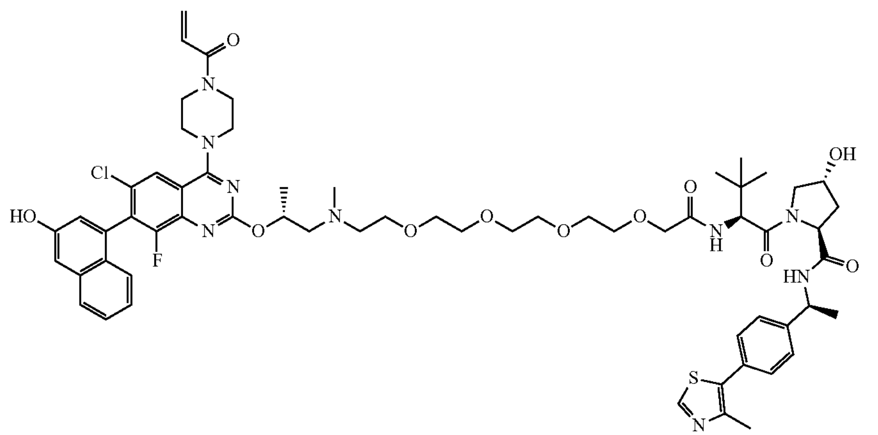 [SMILES: C=CC(=O)N1CCN(c2nc(O[C@H](C)CN(C)CCOCCOCCOCCOCC(=O)N[C@H](C(=O)N3C[C@H](O)C[C@H]3C(=O)N[C@@H](C)c3ccc(-c4scnc4C)cc3)C(C)(C)C)nc3c(F)c(-c4cc(O)cc5ccccc45)c(Cl)cc23)CC1] | (2S,4R)-1-((2S,20R)-20-((4-(4-acryloylpiperazin-1-yl)-6-chloro-8-fluoro-7-(3-hydroxynaphthalen-1-yl)quinazolin-2-yl)oxy)-2-(tert-butyl)-18-methyl-4-oxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | 11 |

TABLE 10-continued

Compounds Prepared by Schemes 7-16

| Ex. No. | Structure | Compound Name | Synthetic Scheme |
|---|---|---|---|
| 398 | 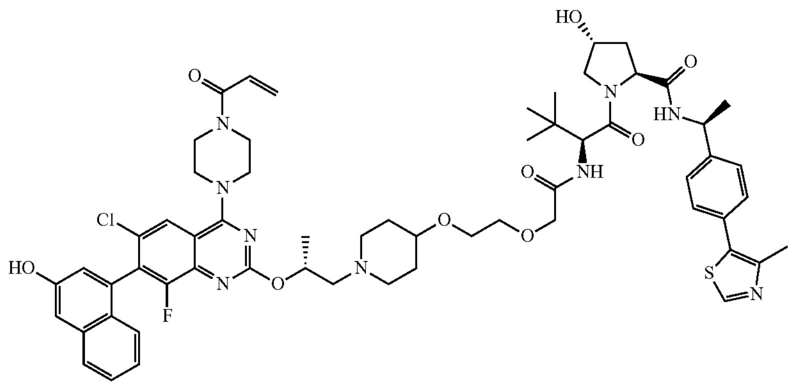 [SMILES: C=CC(=O)N1CCN(c2nc(O[C@H](C)CN3CCC(OCCOCC(=O)N[C@H](C(=O)N4C[C@H](O)C[C@H]4C(=O)N[C@@H](C)c4ccc(-c5scnc5C)cc4)C(C)(C)C)CC3)nc3c(F)c(-c4cc(O)cc5ccccc45)c(Cl)cc23)CC1] | (2S,4R)-1-((2S)-2-(2-(2-(1-((2R)-2-((4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 11 |
| 399 | 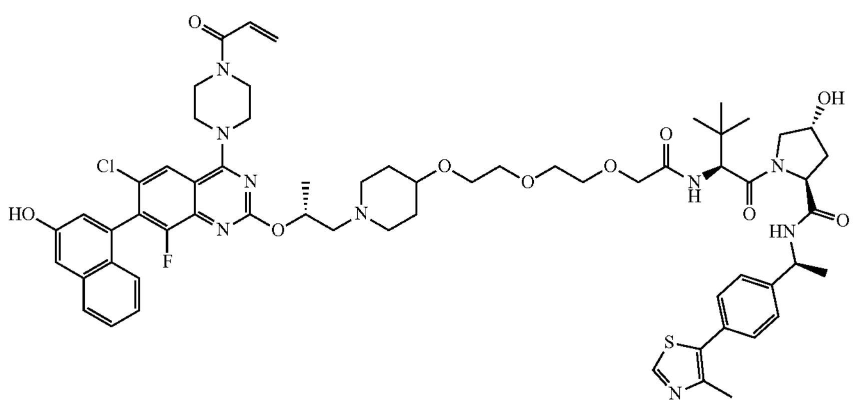 [SMILES: C=CC(=O)N1CCN(c2nc(O[C@H](C)CN3CCC(OCCOCCOCC(=O)N[C@H](C(=O)N4C[C@H](O)C[C@H]4C(=O)N[C@@H](C)c4ccc(-c5scnc5C)cc4)C(C)(C)C)CC3)nc3c(F)c(-c4cc(O)cc5ccccc45)c(Cl)cc23)CC1] | (2S,4R)-1-((2S)-2-(2-(2-(2-((1-((2R)-2-((4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 11 |

TABLE 10-continued

Compounds Prepared by Schemes 7-16

| Ex. No. | Structure | Compound Name | Synthetic Scheme |
|---|---|---|---|
| 400 | 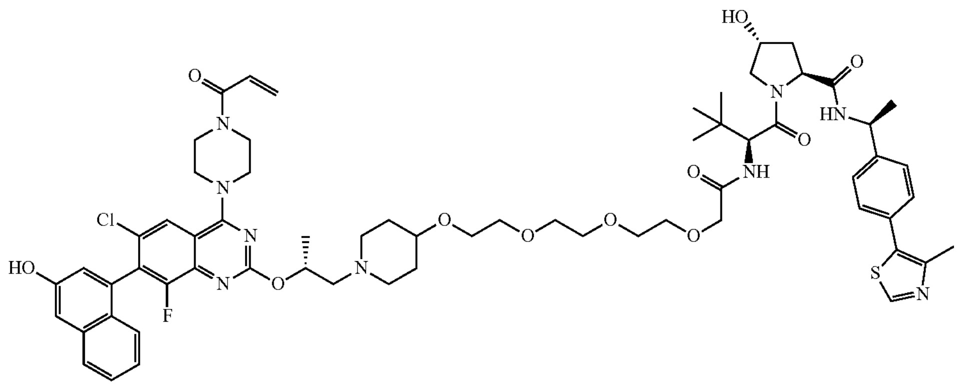 [SMILES: C=CC(=O)N1CCN(c2nc(O[C@H](C)CN3CCC(OCCOCCOCCOCC(=O)N[C@H](C(=O)N4C[C@H](O)C[C@H]4C(=O)N[C@@H](C)c4ccc(-c5scnc5C)cc4)C(C)(C)C)CC3)nc3c(F)c(-c4cc(O)cc5ccccc45)c(Cl)cc23)CC1] | (2S,4R)-1-((2S)-14-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)-2-(tert-butyl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | 11 |
| 401 | 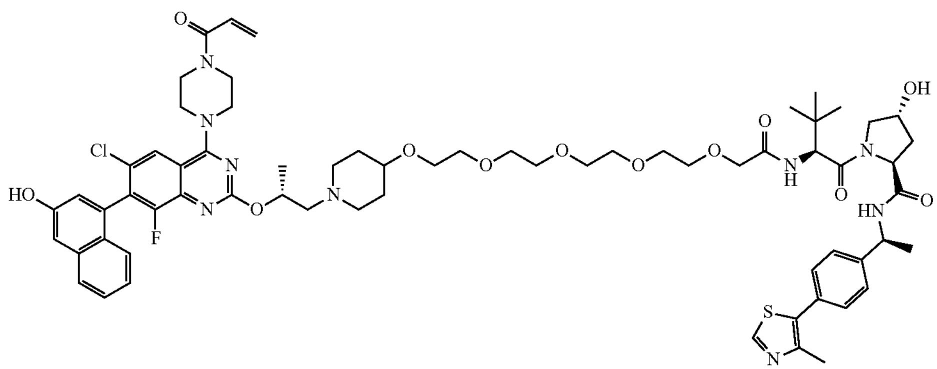 [SMILES: C=CC(=O)N1CCN(c2nc(O[C@H](C)CN3CCC(OCCOCCOCCOCCOCC(=O)N[C@H](C(=O)N4C[C@H](O)C[C@H]4C(=O)N[C@@H](C)c4ccc(-c5scnc5C)cc4)C(C)(C)C)CC3)nc3c(F)c(-c4cc(O)cc5ccccc45)c(Cl)cc23)CC1] | (2S,4R)-1-((2S)-17-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)-2-(tert-butyl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | 11 |

TABLE 10-continued

Compounds Prepared by Schemes 7-16

| Ex. No. | Structure | Compound Name | Synthetic Scheme |
|---|---|---|---|
| 402 | 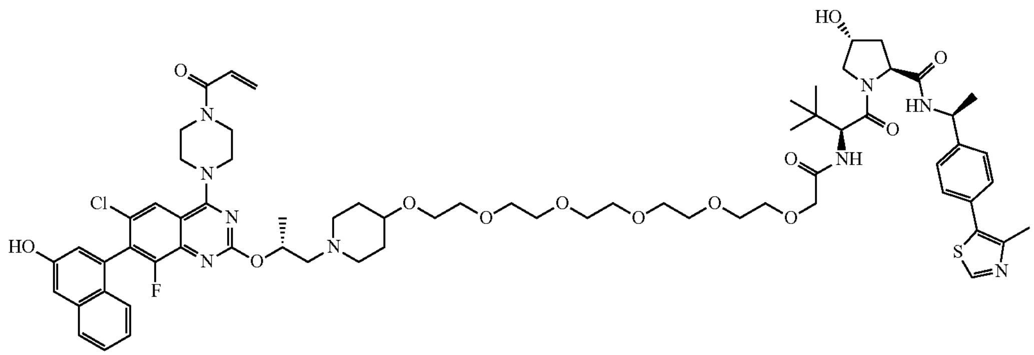 [SMILES: C=CC(=O)N1CCN(c2nc(O[C@H](C)CN3CCC(OCCOCCOCCOCCOCCOCC(=O)N[C@H](C(=O)N4C[C@H](O)C[C@H]4C(=O)N[C@@H](C)c4ccc(-c5scnc5C)cc4)C(C)(C)C)CC3)nc3c(F)c(-c4cc(O)cc5ccccc45)c(Cl)cc23)CC1] | (2S,4R)-1-((2S)-20-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)-2-(tert-butyl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | 11 |
| 403 | 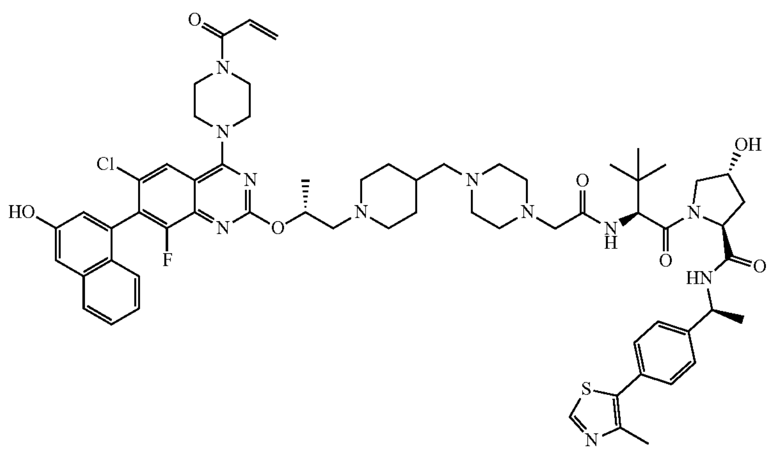 [SMILES: C=CC(=O)N1CCN(c2nc(O[C@H](C)CN3CCC(CN4CCN(CC(=O)N[C@H](C(=O)N5C[C@H](O)C[C@H]5C(=O)N[C@@H](C)c5ccc(-c6scnc6C)cc5)C(C)(C)C)CC4)CC3)nc3c(F)c(-c4cc(O)cc5ccccc45)c(Cl)cc23)CC1] | (2S,4R)-1-((2S)-2-(2-(4-((1-((2R)-2-((4-(4-acryloylpiperazin-1-yl)-6-chloro-8-fluoro-7-(3-hydroxynaphthalen-1-yl)quinazolin-1-yl)oxy)propyl)piperidin-4-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 11 |

TABLE 10-continued

Compounds Prepared by Schemes 7-16

| Ex. No. | Structure | Compound Name | Synthetic Scheme |
|---|---|---|---|
| 404 | 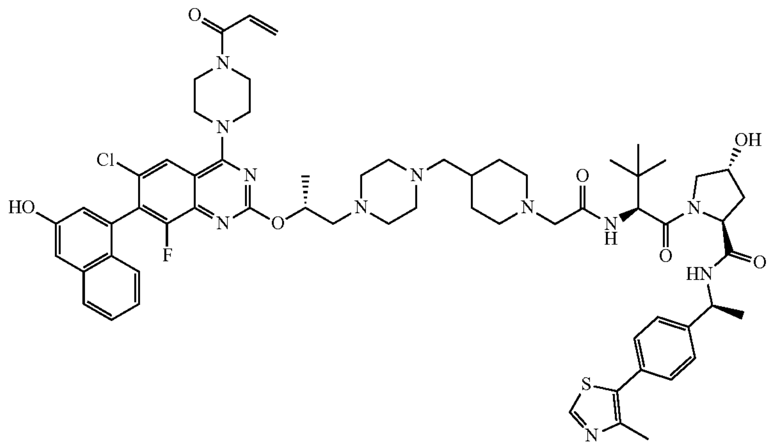 [SMILES: C=CC(=O)N1CCN(c2nc(O[C@H](C)CN3CCN(CC4CCN(CC(=O)N[C@H](C(=O)N5C[C@H](O)C[C@H]5C(=O)N[C@@H](C)c5ccc(-c6scnc6C)cc5)C(C)(C)C)CC4)CC3)nc3c(F)c(-c4cc(O)cc5ccccc45)c(Cl)cc23)CC1] | (2S,4R)-1-((2S)-2-(2-(4-(4-((2R)-2-((4-(4-acryloylpiperazin-1-yl)-6-chloro-8-fluoro-7-(3-hydroxynaphthalen-1-yl)quinazolin-2-yl)oxy)propyl)piperazin-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 11 |
| 405 | 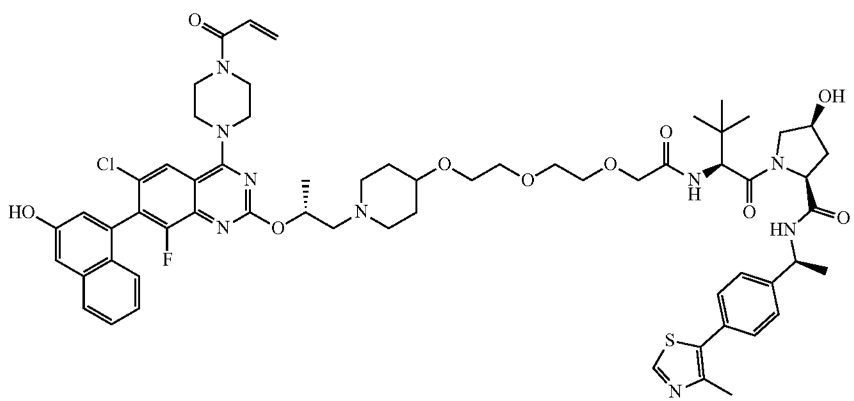 [SMILES: C=CC(=O)N1CCN(c2nc(O[C@H](C)CN3CCC(OCCOCCOCC(=O)N[C@H](C(=O)N4C[C@@H](O)C[C@H]4C(=O)N[C@@H](C)c4ccc(-c5scnc5C)cc4)C(C)(C)C)CC3)nc3c(F)c(-c4cc(O)cc5ccccc45)c(Cl)cc23)CC1] | (2S,4S)-1-((2S)-2-(2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 11 |

TABLE 10-continued

Compounds Prepared by Schemes 7-16

| Ex. No. | Structure | Compound Name | Synthetic Scheme |
|---|---|---|---|
| 406 | 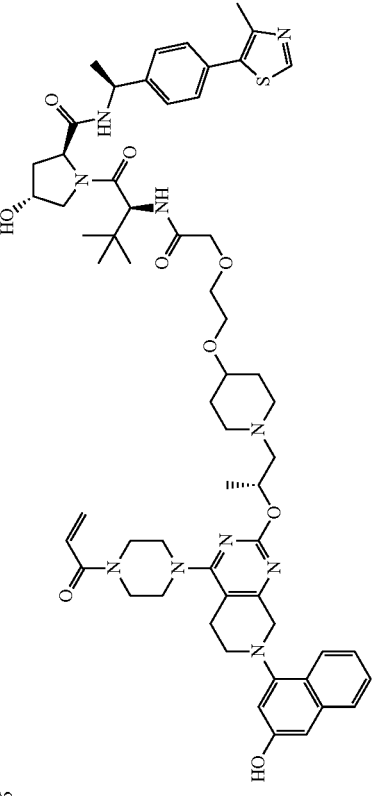 | (2S,4R)-1-((S)-2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 11 |
| 407 | 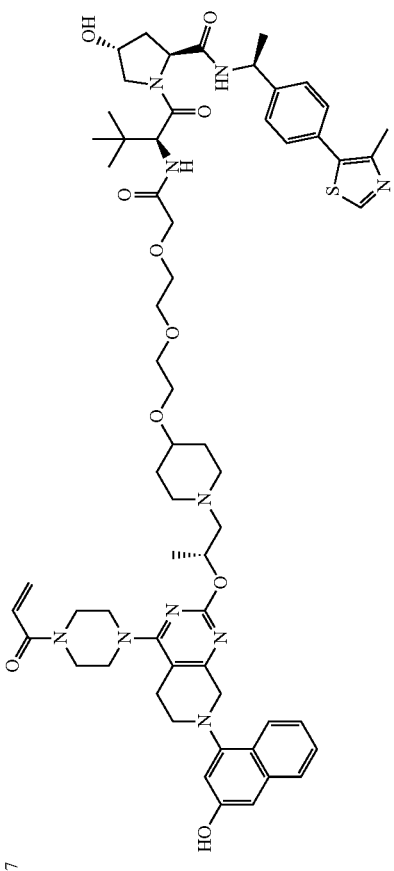 | (2S,4R)-1-((S)-2-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 11 |

TABLE 10-continued

Compounds Prepared by Schemes 7-16

| Ex. No. | Structure | Compound Name | Synthetic Scheme |
|---|---|---|---|
| 408 | 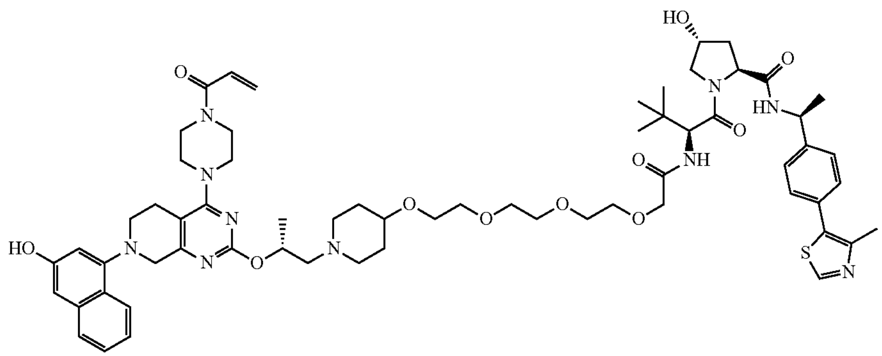 [SMILES: C=CC(=O)N1CCN(c2nc(O[C@H](C)CN3CCC(OCCOCCOCCOCC(=O)N[C@H](C(=O)N4C[C@H](O)C[C@H]4C(=O)N[C@@H](C)c4ccc(-c5scnc5C)cc4)C(C)(C)C)CC3)nc3c2CCN(c2cc(O)cc4ccccc24)C3)CC1] | (2S,4R)-14(S)-14-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-2-(tert-butyl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | 11 |
| 409 | 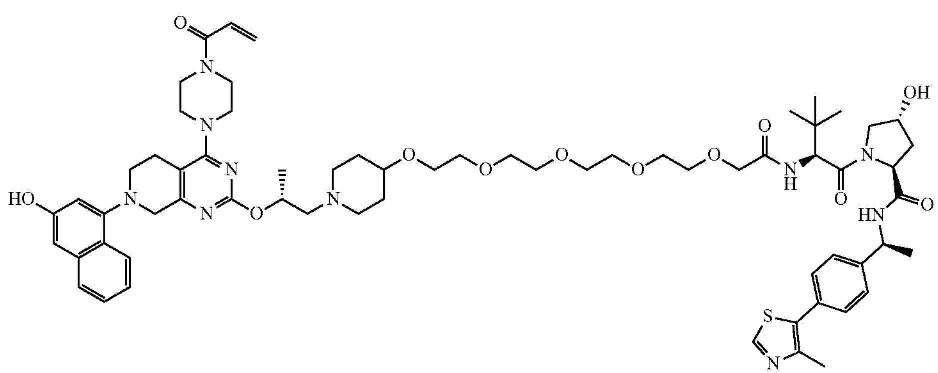 [SMILES: C=CC(=O)N1CCN(c2nc(O[C@H](C)CN3CCC(OCCOCCOCCOCCOCC(=O)N[C@H](C(=O)N4C[C@H](O)C[C@H]4C(=O)N[C@@H](C)c4ccc(-c5scnc5C)cc4)C(C)(C)C)CC3)nc3c2CCN(c2cc(O)cc4ccccc24)C3)CC1] | (2S,4R)-14(S)-17-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-2-(tert-butyl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | 11 |

TABLE 10-continued

Compounds Prepared by Schemes 7-16

| Ex. No. | Structure | Compound Name | Synthetic Scheme |
|---|---|---|---|
| 410 | 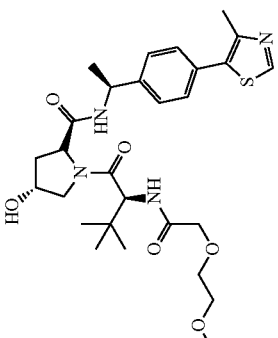 | (2S,4R)-1-((S)-20-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-2-(tert-butyl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | 11 |
| 411 | 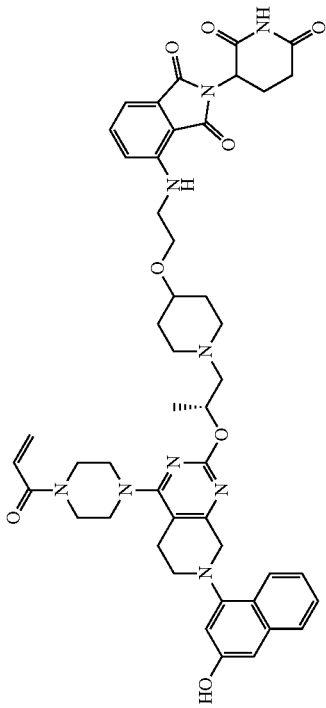 | 4-((2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethyl)amino)-2-(2,6-dioxopiperidin-3-yl)isoindoline-1,3-dione | 12 |

TABLE 10-continued

Compounds Prepared by Schemes 7-16

| Ex. No. | Structure | Compound Name | Synthetic Scheme |
|---|---|---|---|
| 412 | 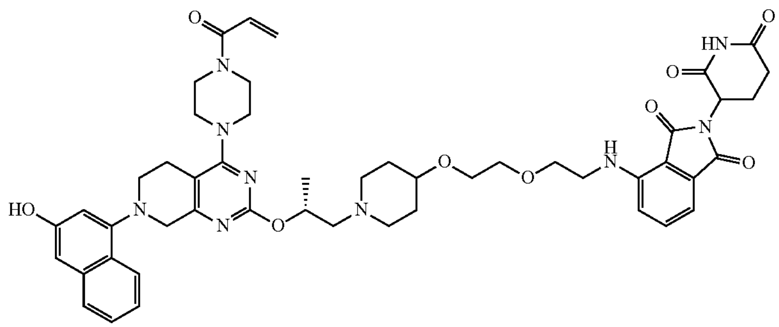 [SMILES: C=CC(=O)N1CCN(c2nc(O[C@H](C)CN3CCC(OCCOCCNc4cccc5c4C(=O)N(C4CCC(=O)NC4=O)C5=O)CC3)nc3c2CCN(c2cc(O)cc4ccccc24)C3)CC1] | 4-((2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethyl)amino)-2-(2,6-dioxopiperidin-3-yl)isoindoline-1,3-dione | 12 |
| 413 | 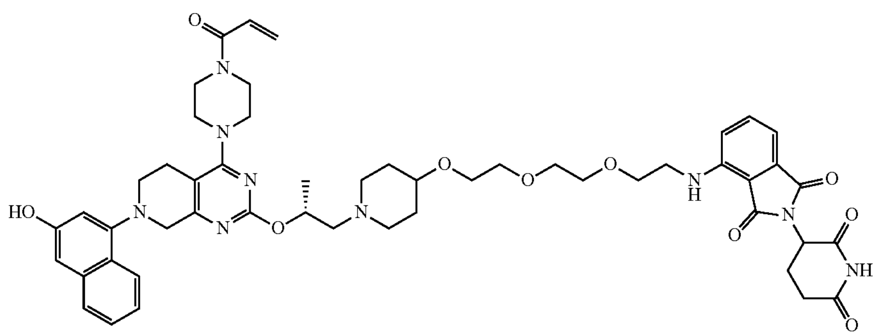 [SMILES: C=CC(=O)N1CCN(c2nc(O[C@H](C)CN3CCC(OCCOCCOCCNc4cccc5c4C(=O)N(C4CCC(=O)NC4=O)C5=O)CC3)nc3c2CCN(c2cc(O)cc4ccccc24)C3)CC1] | 4-((2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethyl)amino)-2-(2,6-dioxopiperidin-3-yl)isoindoline-1,3-dione | 12 |
| 414 | 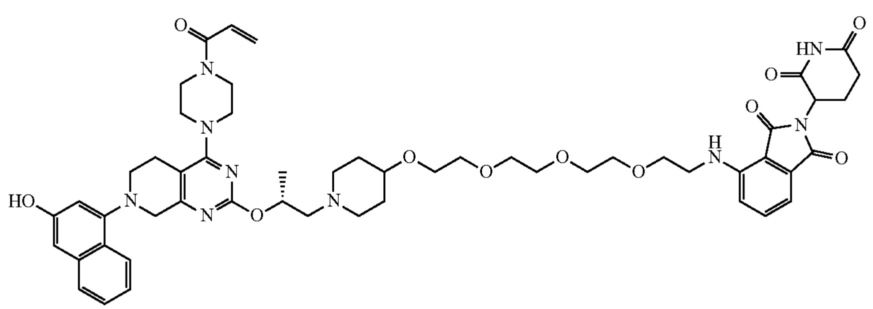 [SMILES: C=CC(=O)N1CCN(c2nc(O[C@H](C)CN3CCC(OCCOCCOCCOCCNc4cccc5c4C(=O)N(C4CCC(=O)NC4=O)C5=O)CC3)nc3c2CCN(c2cc(O)cc4ccccc24)C3)CC1] | 4-((2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)ethyl)amino)-2-(2,6-dioxopiperidin-3-yl)isoindoline-1,3-dione | 12 |

TABLE 10-continued

Compounds Prepared by Schemes 7-16

| Ex. No. | Structure | Compound Name | Synthetic Scheme |
|---|---|---|---|
| 415 | 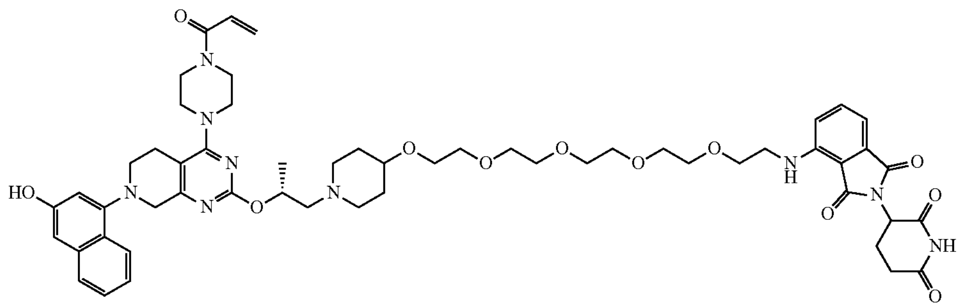 [SMILES: C=CC(=O)N1CCN(c2nc(O[C@H](C)CN3CCC(OCCOCCOCCOCCOCCNc4cccc5c4C(=O)N(C4CCC(=O)NC4=O)C5=O)CC3)nc3c2CCN(c2cc(O)cc4ccccc24)C3)CC1] | 4-((14-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-3,6,9,12-tetraoxatetradecyl)amino)-2-(2,6-dioxopiperidin-3-yl)isoindoline-1,3-dione | 12 |
| 416 | 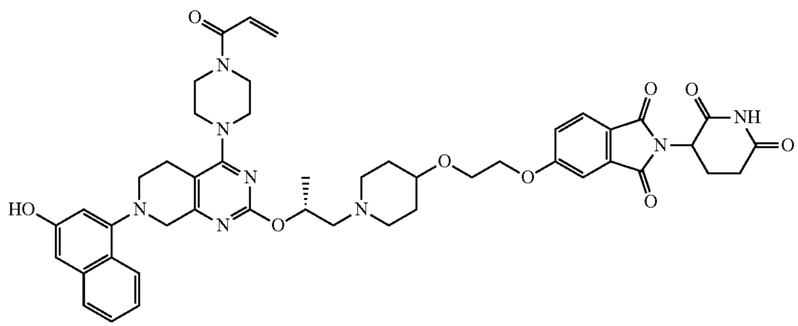 [SMILES: C=CC(=O)N1CCN(c2nc(O[C@H](C)CN3CCC(OCCOc4ccc5c(c4)C(=O)N(C4CCC(=O)NC4=O)C5=O)CC3)nc3c2CCN(c2cc(O)cc4ccccc24)C3)CC1] | 5-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)-2-(2,6-dioxopiperidin-3-yl)isoindoline-1,3-dione | 12 |
| 417 | 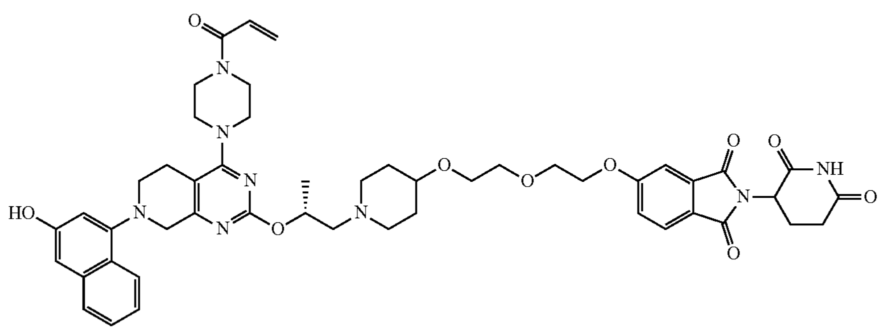 [SMILES: C=CC(=O)N1CCN(c2nc(O[C@H](C)CN3CCC(OCCOCCOc4ccc5c(c4)C(=O)N(C4CCC(=O)NC4=O)C5=O)CC3)nc3c2CCN(c2cc(O)cc4ccccc24)C3)CC1] | 5-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)-2-(2,6-dioxopiperidin-3-yl)isoindoline-1,3-dione | 12 |

TABLE 10-continued

Compounds Prepared by Schemes 7-16

| Ex. No. | Structure | Compound Name | Synthetic Scheme |
|---|---|---|---|
| 418 | 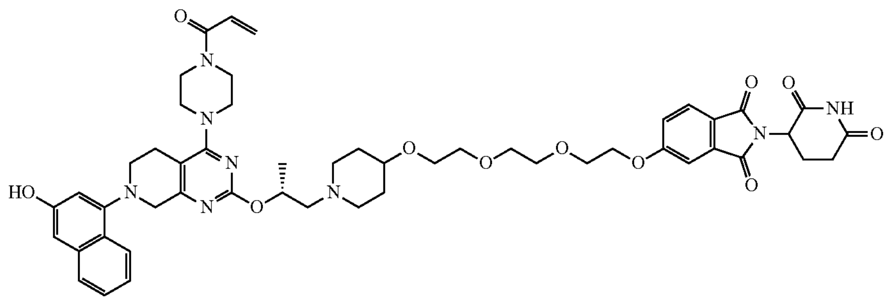 [SMILES: C=CC(=O)N1CCN(c2nc(O[C@H](C)CN3CCC(OCCOCCOCCOc4ccc5c(c4)C(=O)N(C4CCC(=O)NC4=O)C5=O)CC3)nc3c2CCN(c2cc(O)cc4ccccc24)C3)CC1] | 5-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)-2-(2,6-dioxopiperidin-3-yl)isoindoline-1,3-dione | 12 |
| 419 | 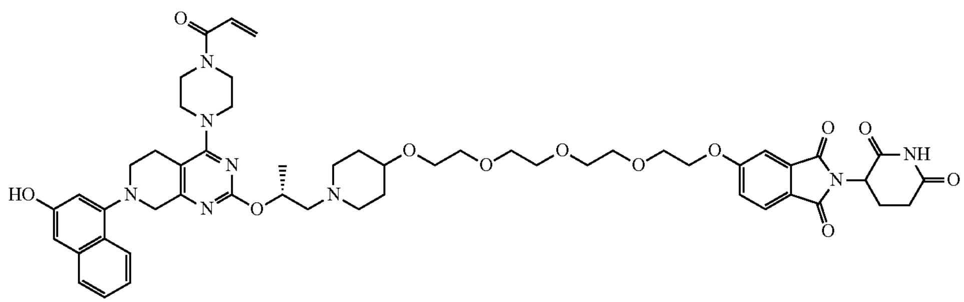 [SMILES: C=CC(=O)N1CCN(c2nc(O[C@H](C)CN3CCC(OCCOCCOCCOCCOc4ccc5c(c4)C(=O)N(C4CCC(=O)NC4=O)C5=O)CC3)nc3c2CCN(c2cc(O)cc4ccccc24)C3)CC1] | 5-(2-(2-(2-(((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)-2-(2,6-dioxopiperidin-3-yl)isoindoline-1,3-dione | 12 |
| 420 | 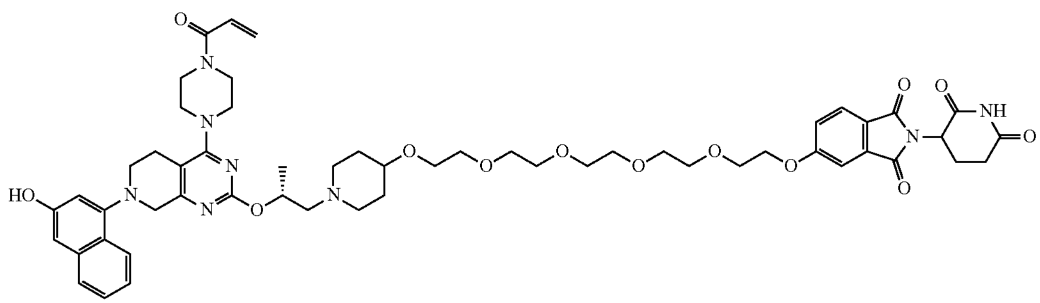 [SMILES: C=CC(=O)N1CCN(c2nc(O[C@H](C)CN3CCC(OCCOCCOCCOCCOCCOc4ccc5c(c4)C(=O)N(C4CCC(=O)NC4=O)C5=O)CC3)nc3c2CCN(c2cc(O)cc4ccccc24)C3)CC1] | 5-((14-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-3,6,9,12-tetraoxatetradecyl)oxy)-2-(2,6-dioxopiperidin-3-yl)isoindoline-1,3-dione | 12 |

TABLE 10-continued

Compounds Prepared by Schemes 7-16

| Ex. No. | Structure | Compound Name | Synthetic Scheme |
|---|---|---|---|
| 421 | 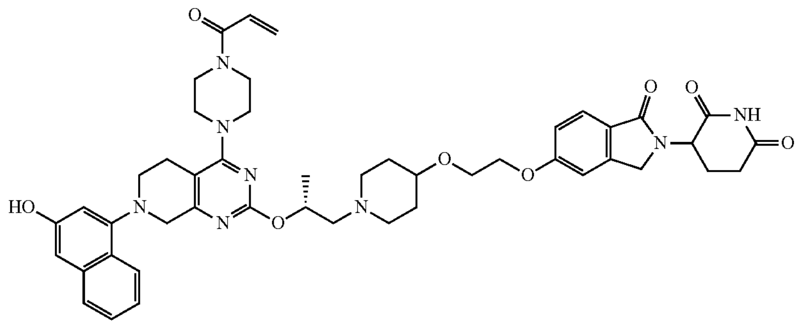 [SMILES: C=CC(=O)N1CCN(c2nc(O[C@H](C)CN3CCC(OCCOc4ccc5c(c4)CN(C4CCC(=O)NC4=O)C5=O)CC3)nc3c2CCN(c2cc(O)cc4ccccc24)C3)CC1] | 3-(5-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)-1-oxoisoindolin-2-yl)piperidine-2,6-dione | 12 |
| 422 | 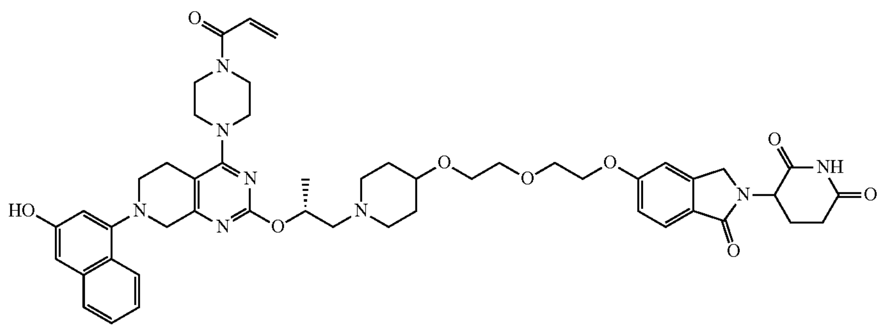 [SMILES: C=CC(=O)N1CCN(c2nc(O[C@H](C)CN3CCC(OCCOCCOc4ccc5c(c4)CN(C4CCC(=O)NC4=O)C5=O)CC3)nc3c2CCN(c2cc(O)cc4ccccc24)C3)CC1] | 3-(5-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)-1-oxoisoindolin-2-yl)piperidine-2,6-dione | 12 |
| 423 | 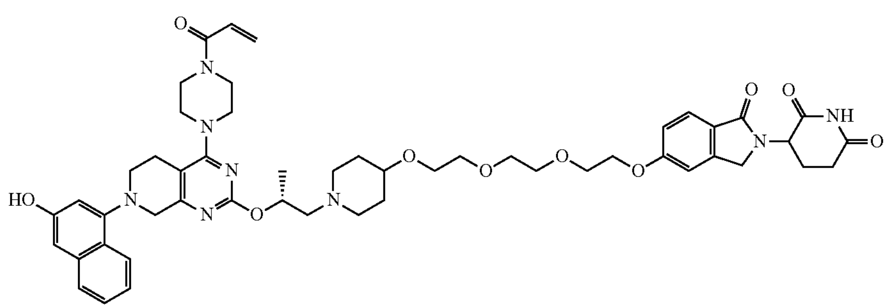 [SMILES: C=CC(=O)N1CCN(c2nc(O[C@H](C)CN3CCC(OCCOCCOCCOc4ccc5c(c4)CN(C4CCC(=O)NC4=O)C5=O)CC3)nc3c2CCN(c2cc(O)cc4ccccc24)C3)CC1] | 3-(5-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)-1-oxoisoindolin-2-yl)piperidine-2,6-dione | 12 |

TABLE 10-continued

Compounds Prepared by Schemes 7-16

| Ex. No. | Structure | Compound Name | Synthetic Scheme |
|---|---|---|---|
| 424 | 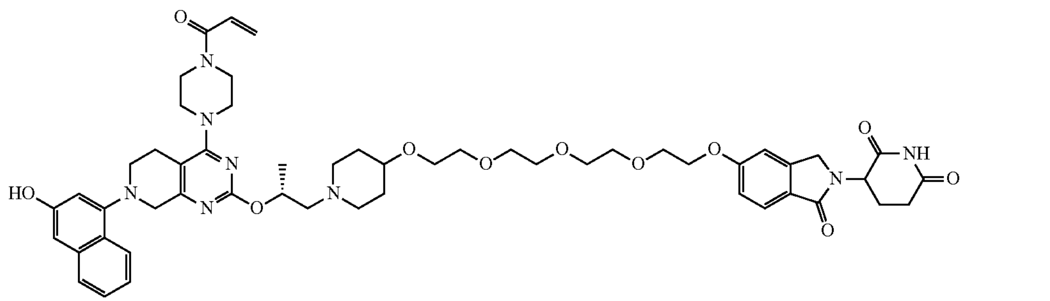 [SMILES: C=CC(=O)N1CCN(c2nc(O[C@H](C)CN3CCC(OCCOCCOCCOCCOc4ccc5c(c4)CN(C4CCC(=O)NC4=O)C5=O)CC3)nc3c2CCN(c2cc(O)cc4ccccc24)C3)CC1] | 3-(5-(2-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)-1-oxoisoindolin-2-yl)piperidine-2,6-dione | 12 |
| 425 | 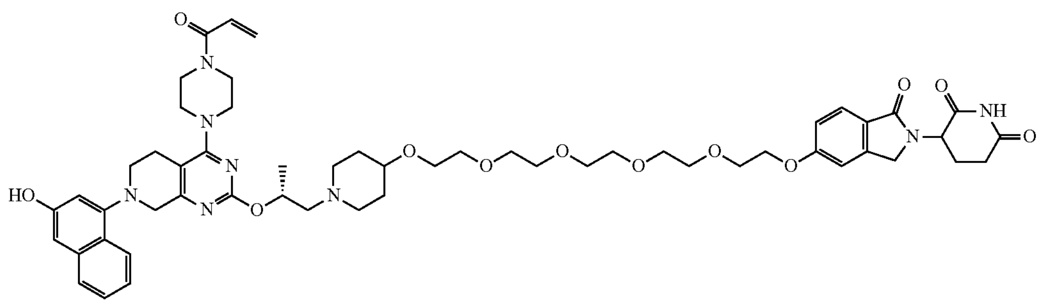 [SMILES: C=CC(=O)N1CCN(c2nc(O[C@H](C)CN3CCC(OCCOCCOCCOCCOCCOc4ccc5c(c4)CN(C4CCC(=O)NC4=O)C5=O)CC3)nc3c2CCN(c2cc(O)cc4ccccc24)C3)CC1] | 3-(5-((14-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-3,6,9,12-tetraoxatetradecyl)oxy)-1-oxoisoindolin-2-yl)piperidine-2,6-dione | 12 |
| 426 | 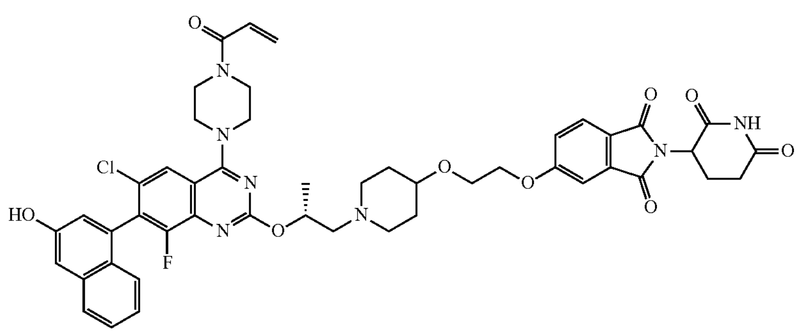 [SMILES: C=CC(=O)N1CCN(c2nc(O[C@H](C)CN3CCC(OCCOc4ccc5c(c4)C(=O)N(C4CCC(=O)NC4=O)C5=O)CC3)nc3c(F)c(-c4cc(O)cc5ccccc45)c(Cl)cc23)CC1] | 5-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)-2-(2,6-dioxopiperidin-3-yl)isoindoline-1,3-dione | 12 |

TABLE 10-continued

Compounds Prepared by Schemes 7-16

| Ex. No. | Structure | Compound Name | Synthetic Scheme |
|---|---|---|---|
| 427 | 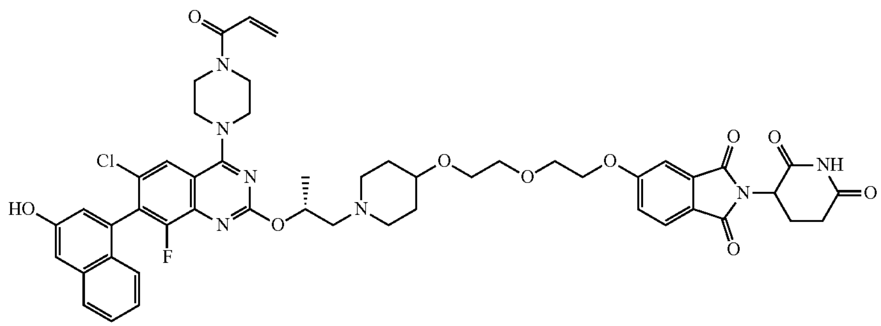 [SMILES: C=CC(=O)N1CCN(c2nc(O[C@H](C)CN3CCC(OCCOCCOc4ccc5c(c4)C(=O)N(C4CCC(=O)NC4=O)C5=O)CC3)nc3c(F)c(-c4cc(O)cc5ccccc45)c(Cl)cc23)CC1] | 5-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)-2-(2,6-dioxopiperidin-3-yl)isoindoline-1,3-dione | 12 |
| 428 | 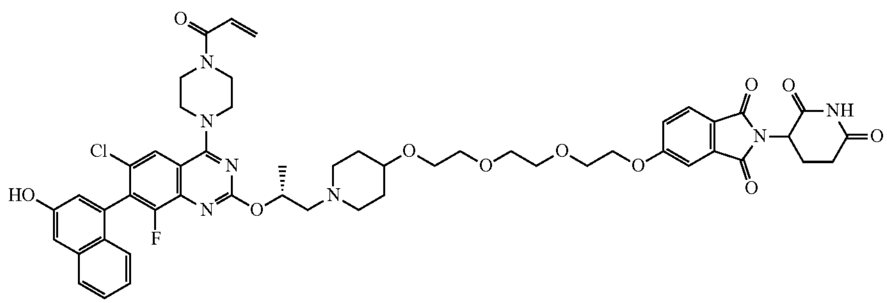 [SMILES: C=CC(=O)N1CCN(c2nc(O[C@H](C)CN3CCC(OCCOCCOCCOc4ccc5c(c4)C(=O)N(C4CCC(=O)NC4=O)C5=O)CC3)nc3c(F)c(-c4cc(O)cc5ccccc45)c(Cl)cc23)CC1] | 5-(2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)-2-(2,6-dioxopiperidin-3-yl)isoindoline-1,3-dione | 12 |
| 429 | 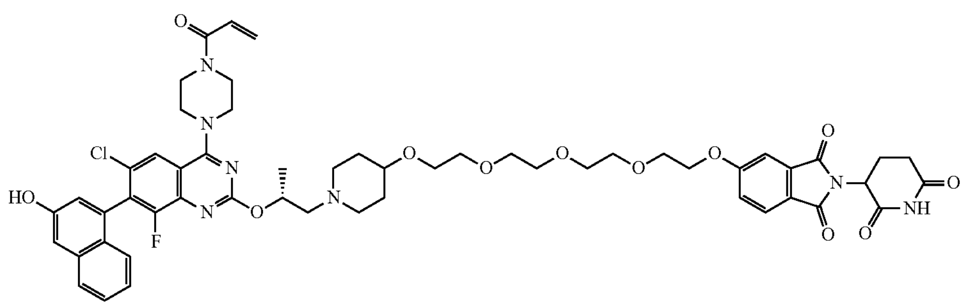 [SMILES: C=CC(=O)N1CCN(c2nc(O[C@H](C)CN3CCC(OCCOCCOCCOCCOc4ccc5c(c4)C(=O)N(C4CCC(=O)NC4=O)C5=O)CC3)nc3c(F)c(-c4cc(O)cc5ccccc45)c(Cl)cc23)CC1] | 5-(2-(2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)ethoxy)-2-(2,6-dioxopiperidin-3-yl)isoindoline-1,3-dione | 12 |

TABLE 10-continued

Compounds Prepared by Schemes 7-16

| Ex. No. | Structure | Compound Name | Synthetic Scheme |
|---|---|---|---|
| 430 | 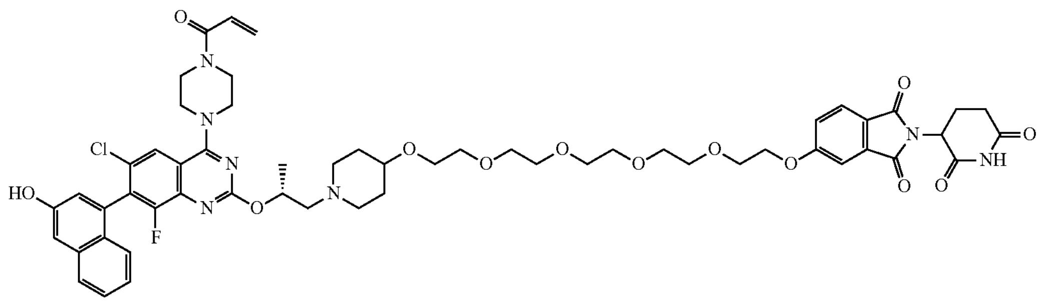 [SMILES: C=CC(=O)N1CCN(c2nc(O[C@H](C)CN3CCC(OCCOCCOCCOCCOCCOc4ccc5c(c4)C(=O)N(C4CCC(=O)NC4=O)C5=O)CC3)nc3c(F)c(-c4cc(O)cc5ccccc45)c(Cl)cc23)CC1] | 5-((14-((1-((2R)-2-(4-(4-acryloylpiperazin-1-yl)-6-chloro-8-fluoro-7-(3-hydroxynaphthalen-1-yl)quinazolin-2-yl)oxy)propyl)piperidin-4-yl)oxy)-3,6,9,12-tetraoxatetradecyl)oxy)-2-(2,6-dioxopiperidin-3-yl)isoindoline-1,3-dione | 12 |
| 431 | 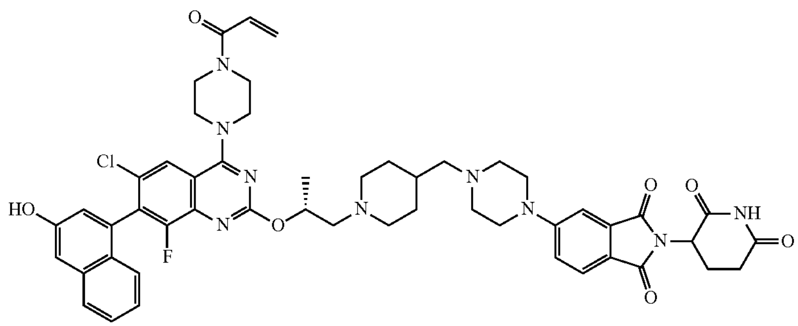 [SMILES: C=CC(=O)N1CCN(c2nc(O[C@H](C)CN3CCC(CN4CCN(c5ccc6c(c5)C(=O)N(C5CCC(=O)NC5=O)C6=O)CC4)CC3)nc3c(F)c(-c4cc(O)cc5ccccc45)c(Cl)cc23)CC1] | 5-(4-((1-((2R)-2-(4-(4-acryloylpiperazin-1-yl)-6-chloro-8-fluoro-7-(3-hydroxynaphthalen-1-yl)quinazolin-2-yl)oxy)propyl)piperidin-4-yl)methyl)piperazin-1-yl)-2-(2,6-dioxopiperidin-3-yl)isoindoline-1,3-dione | 12 |
| 432 | 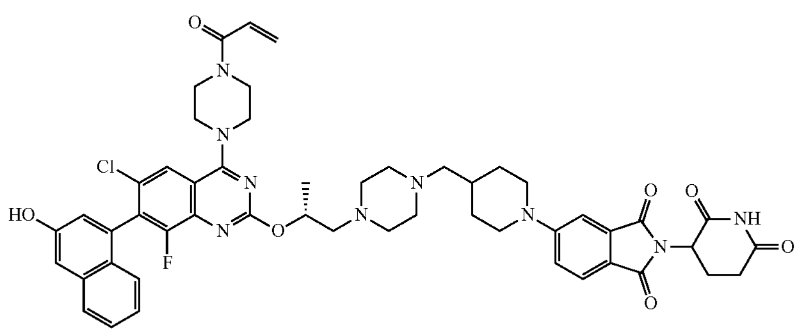 [SMILES: C=CC(=O)N1CCN(c2nc(O[C@H](C)CN3CCN(CC4CCN(c5ccc6c(c5)C(=O)N(C5CCC(=O)NC5=O)C6=O)CC4)CC3)nc3c(F)c(-c4cc(O)cc5ccccc45)c(Cl)cc23)CC1] | 5-(4-(4-((1-((2R)-2-(4-(4-acryloylpiperazin-1-yl)-6-chloro-8-fluoro-7-(3-hydroxynaphthalen-1-yl)quinazolin-2-yl)oxy)propyl)piperidin-4-yl)methyl)piperazin-1-yl)methyl)piperidin-1-yl)-2-(2,6-dioxopiperidin-3-yl)isoindoline-1,3-dione | 12 |

TABLE 10-continued

Compounds Prepared by Schemes 7-16

| Ex. No. | Structure | Compound Name | Synthetic Scheme |
|---|---|---|---|
| 433 | 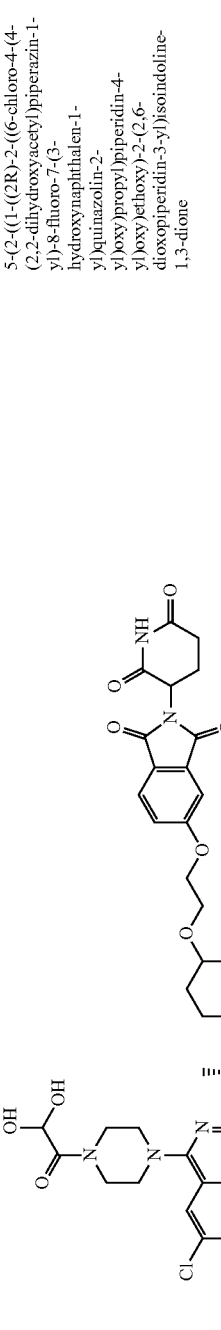 | 5-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)-2-(2,6-dioxopiperidin-3-yl)isoindoline-1,3-dione | 12 |
| 434 | 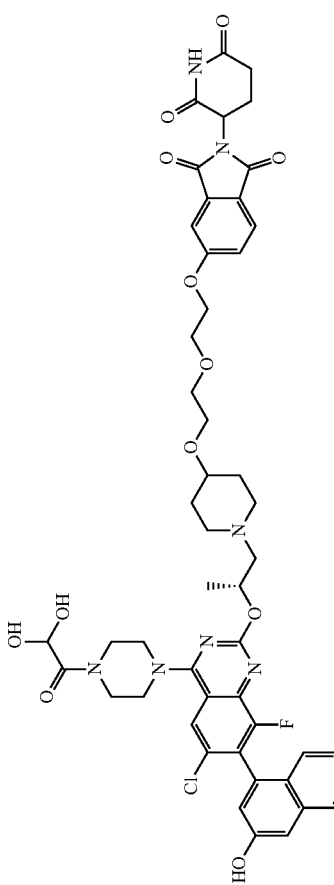 | 5-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)-2-(2,6-dioxopiperidin-3-yl)isoindoline-1,3-dione | 12 |

TABLE 10-continued

Compounds Prepared by Schemes 7-16

| Ex. No. | Structure | Compound Name | Synthetic Scheme |
|---|---|---|---|
| 435 | 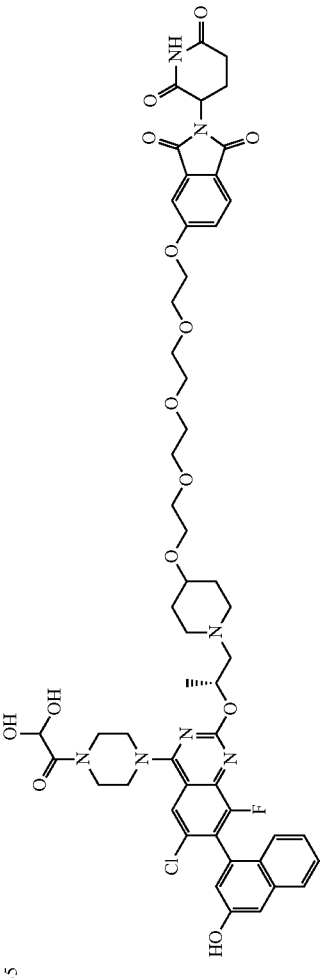 | 5-(2-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)ethoxy)-2-(2,6-dioxopiperidin-3-yl)isoindoline-1,3-dione | 12 |
| 436 | 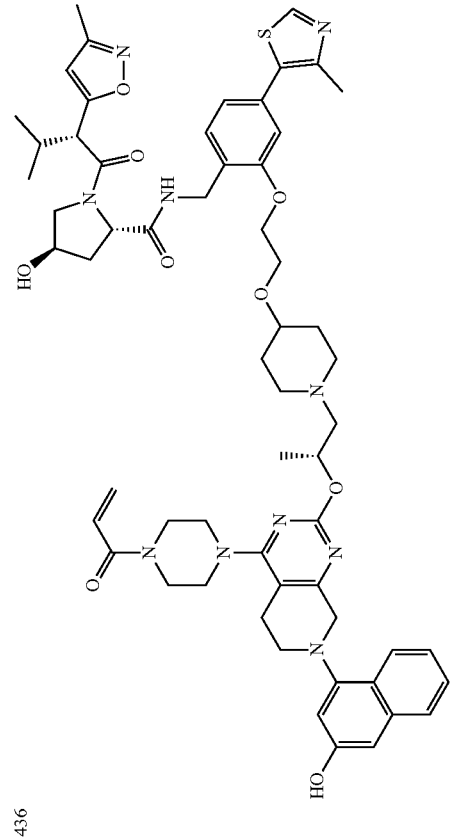 | (2S,4R)-N-(2-(2-(1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 13 |

TABLE 10-continued

Compounds Prepared by Schemes 7-16

| Ex. No. | Structure | Compound Name | Synthetic Scheme |
|---|---|---|---|
| 437 | 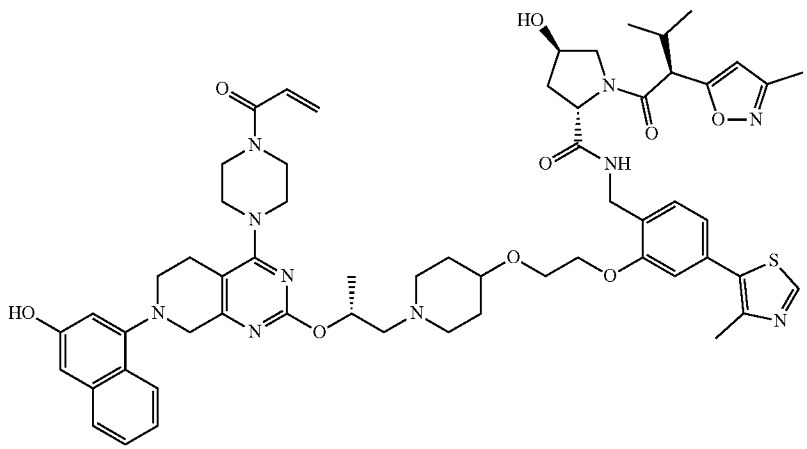 [SMILES: C=CC(=O)N1CCN(c2nc(O[C@H](C)CN3CCC(OCCOc4cc(-c5scnc5C)ccc4CNC(=O)[C@@H]4C[C@@H](O)CN4C(=O)[C@H](c4cc(C)no4)C(C)C)CC3)nc3c2CCN(c2cc(O)cc4ccccc24)C3)CC1] | (2S,4R)-N-(2-(2-((14R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 13 |
| 438 | 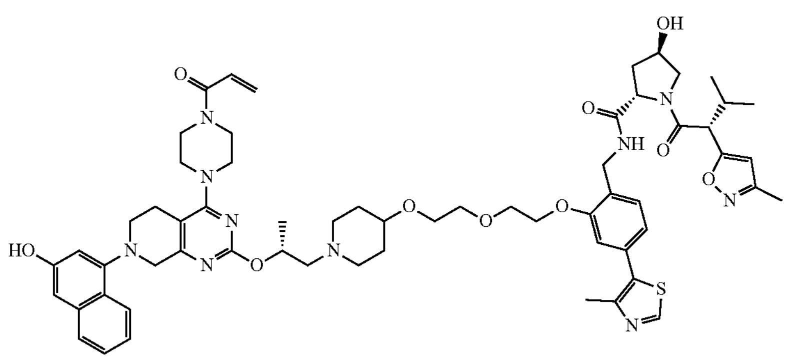 [SMILES: C=CC(=O)N1CCN(c2nc(O[C@H](C)CN3CCC(OCCOCCOc4cc(-c5scnc5C)ccc4CNC(=O)[C@@H]4C[C@@H](O)CN4C(=O)[C@@H](c4cc(C)no4)C(C)C)CC3)nc3c2CCN(c2cc(O)cc4ccccc24)C3)CC1] | (2S,4R)-N-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)-4-(4-methylthiazol-5-yl)benzyl)-4-hydroxy-14(R)-3-methyl-2-(3-methylisoxazol-5-yl)butanoyl)pyrrolidine-2-carboxamide | 13 |

TABLE 10-continued

Compounds Prepared by Schemes 7-16

| Ex. No. | Structure | Compound Name | Synthetic Scheme |
|---|---|---|---|
| 439 | 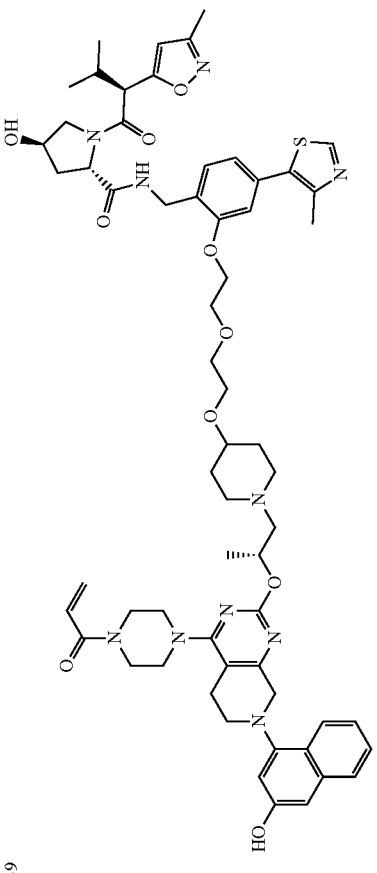 | (2S,4R)-N-(2-(2-(2-(((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 13 |
| 440 | 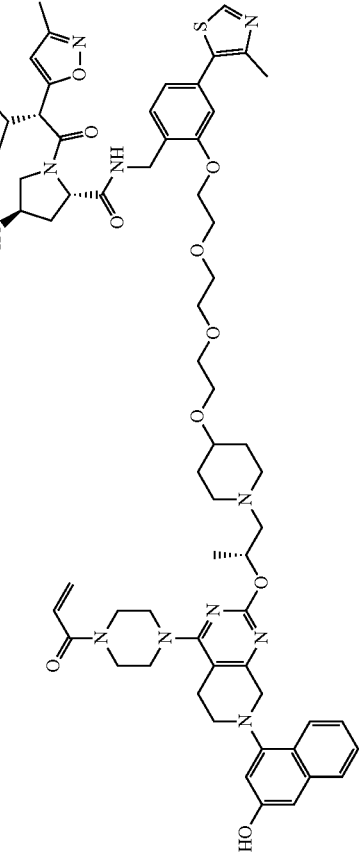 | (2S,4R)-N-(2-(2-(2-(((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 13 |

TABLE 10-continued

Compounds Prepared by Schemes 7-16

| Ex. No. | Structure | Compound Name | Synthetic Scheme |
|---|---|---|---|
| 441 | 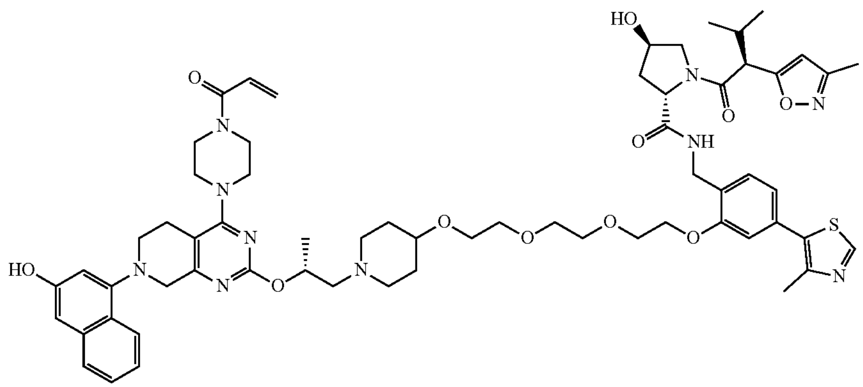 [SMILES: C=CC(=O)N1CCN(c2nc(O[C@H](C)CN3CCC(OCCOCCOCCOc4cc(-c5scnc5C)ccc4CNC(=O)[C@@H]4C[C@@H](O)CN4C(=O)[C@H](c4cc(C)no4)C(C)C)CC3)nc3c2CCN(c2cc(O)cc4ccccc24)C3)CC1] | (2S,4R)-N-(2-(2-(2-(2-((1-((R)-2-((4-(4-acryloyl)piperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)-4-(4-methylthiazol-5-yl)benzyl)-4-hydroxy-1-((S)-2-(3-methylisoxazol-5-yl)butanoyl)pyrrolidine-2-carboxamide | 13 |
| 442 | 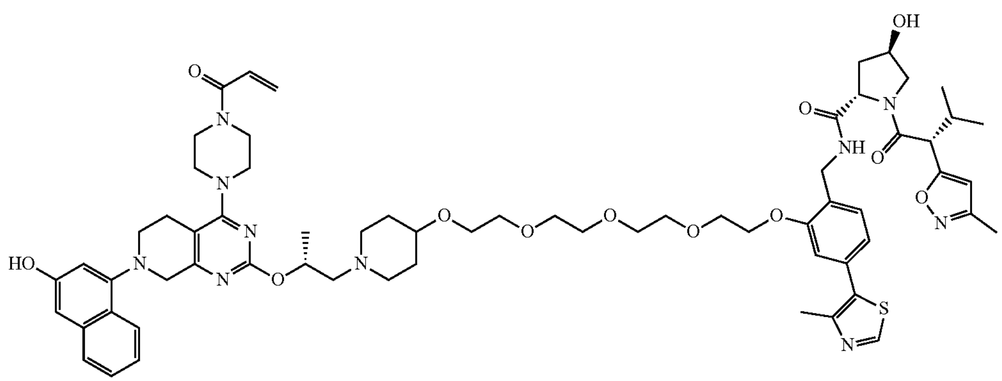 [SMILES: C=CC(=O)N1CCN(c2nc(O[C@H](C)CN3CCC(OCCOCCOCCOCCOc4cc(-c5scnc5C)ccc4CNC(=O)[C@@H]4C[C@@H](O)CN4C(=O)[C@@H](c4cc(C)no4)C(C)C)CC3)nc3c2CCN(c2cc(O)cc4ccccc24)C3)CC1] | (2S,4R)-N-(2-(2-(2-(2-((1-((R)-2-((4-(4-acryloyl)piperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 13 |

TABLE 10-continued

Compounds Prepared by Schemes 7-16

| Ex. No. | Structure | Compound Name | Synthetic Scheme |
|---|---|---|---|
| 443 | 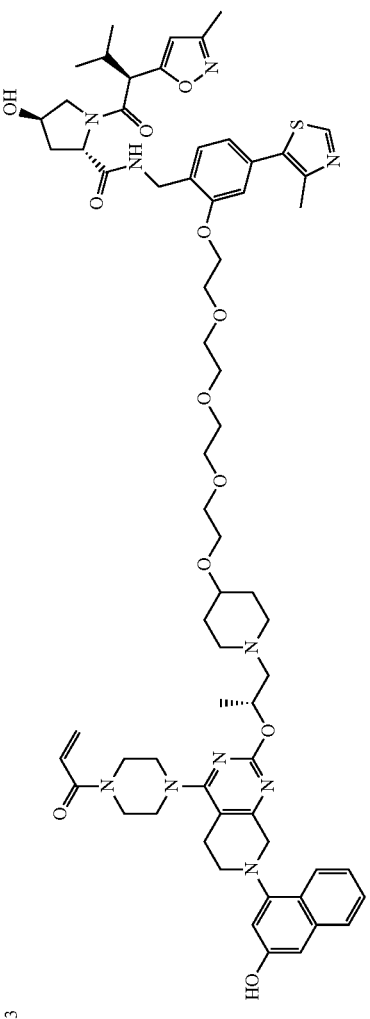 | (2S,4R)-N-(2-(2-(2-(2-(2-((1-((R)-2-((4-acryloyl)piperazin-1-yl)-7-(3-hydroxynaphthalen-1-yl)-5,6,7,8-tetrahydropyrido[3,4-d]dipyrimidin-2-yl)oxy)propyl)piperidin-4-yl)oxy)ethoxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 13 |
| 444 | 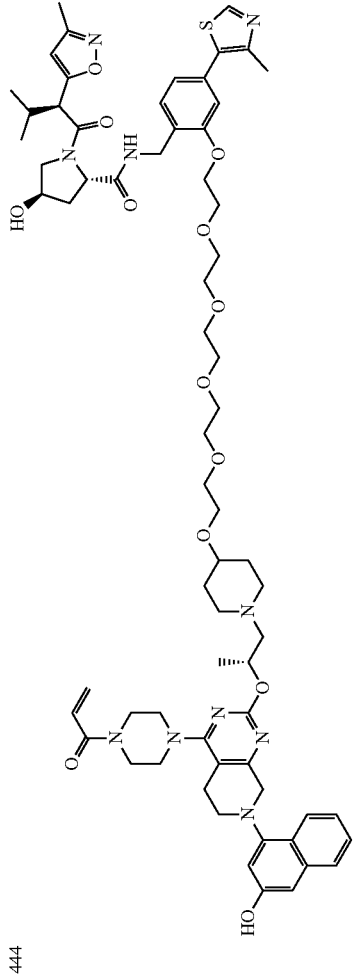 | (2S,4R)-N-(2-((14-((1-((R)-2-((4-(4-acryloyl)piperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-3,6,9,12-tetraoxatetradecyl)oxy)-4-(4-methylthiazol-5-yl)benzyl)-4-hydroxy-14(S)-3-methyl-2-(3-methylisoxazol-5-yl)butanoyl)pyrrolidine-2-carboxamide | 13 |

TABLE 10-continued

Compounds Prepared by Schemes 7-16

| Ex. No. | Structure | Compound Name | Synthetic Scheme |
|---|---|---|---|
| 445 | 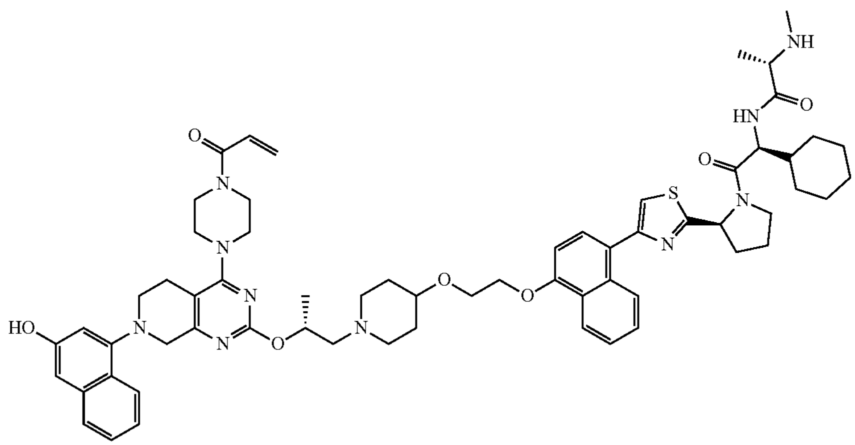 [SMILES: C=CC(=O)N1CCN(c2nc(O[C@H](C)CN3CCC(OCCOc4ccc(-c5csc([C@@H]6CCCN6C(=O)[C@@H](NC(=O)[C@H](C)NC)C6CCCCC6)n5)c5ccccc45)CC3)nc3c2CCN(c2cc(O)cc4ccccc24)C3)CC1] | (S)-N-((S)-2-((S)-2-(4-(4-(2-(4-(2-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)naphthalen-1-yl)thiazol-2-yl)pyrrolidin-1-yl)-1-cyclohexyl)-2-oxoethyl)-2-(methylamino)propanamide | 14 |
| 446 | 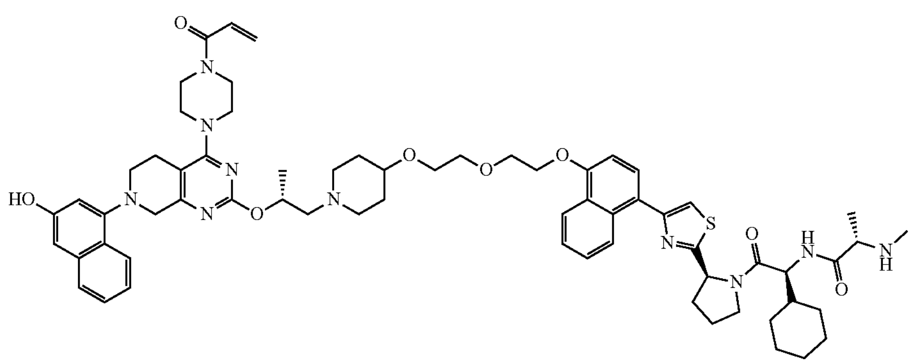 [SMILES: C=CC(=O)N1CCN(c2nc(O[C@H](C)CN3CCC(OCCOCCOc4ccc(-c5csc([C@@H]6CCCN6C(=O)[C@@H](NC(=O)[C@H](C)NC)C6CCCCC6)n5)c5ccccc45)CC3)nc3c2CCN(c2cc(O)cc4ccccc24)C3)CC1] | (S)-N-((S)-2-((S)-2-(4-(4-(2-(2-((1-(R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)naphthalen-1-yl)thiazol-2-yl)pyrrolidin-1-yl)-1-cyclohexyl)-2-oxoethyl)-2-(methylamino)propanamide | 14 |

TABLE 10-continued

Compounds Prepared by Schemes 7-16

| Ex. No. | Structure | Compound Name | Synthetic Scheme |
|---|---|---|---|
| 447 | 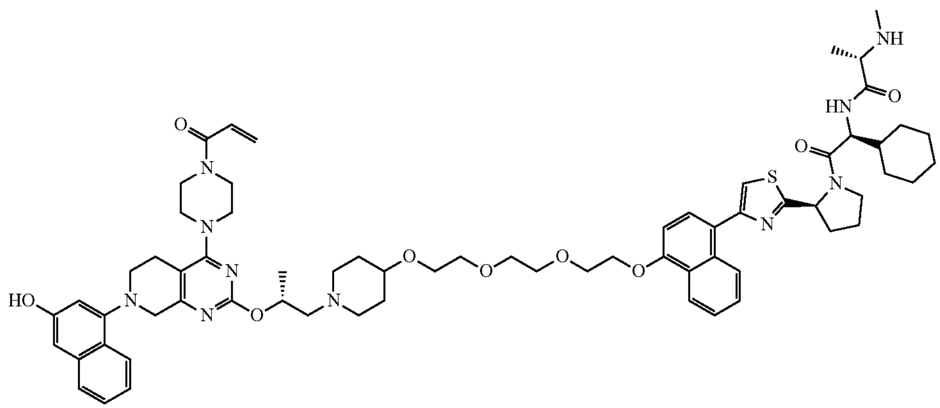 [SMILES: C=CC(=O)N1CCN(c2nc(O[C@H](C)CN3CCC(OCCOCCOCCOc4ccc(-c5csc([C@@H]6CCCN6C(=O)[C@@H](NC(=O)[C@H](C)NC)C6CCCCC6)n5)c5ccccc45)CC3)nc3c2CCN(c2cc(O)cc4ccccc24)C3)CC1] | (S)-N-((S)-2-((S)-2-(4-(4-(2-(2-(2-((1-((R)-2-((4-(4-acryloyl)piperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)naphthalen-1-yl)thiazol-2-yl)pyrrolidin-1-yl)-1-cyclohexyl-2-oxoethyl)-2-(methylamino)propanamide | 14 |
| 448 | 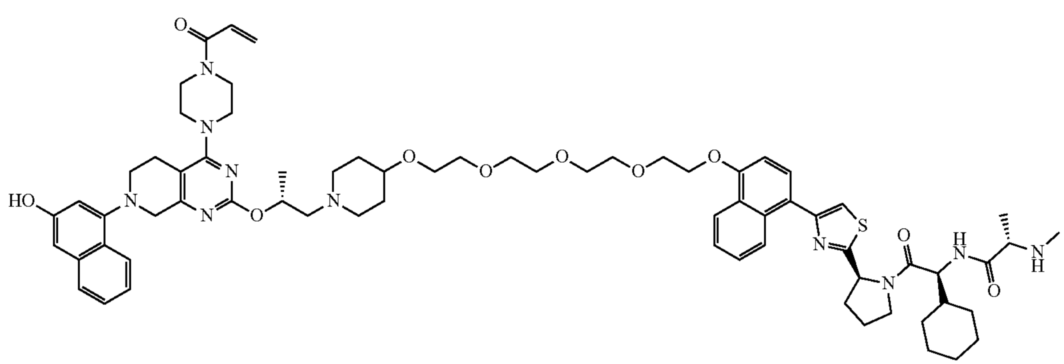 [SMILES: C=CC(=O)N1CCN(c2nc(O[C@H](C)CN3CCC(OCCOCCOCCOCCOc4ccc(-c5csc([C@@H]6CCCN6C(=O)[C@@H](NC(=O)[C@H](C)NC)C6CCCCC6)n5)c5ccccc45)CC3)nc3c2CCN(c2cc(O)cc4ccccc24)C3)CC1] | (S)-N-((S)-2-((S)-2-(4-(4-(2-(2-(2-(2-((1(R)-2-((4-(4-acryloyl)piperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethoxy)naphthalen-1-yl)thiazol-2-yl)pyrrolidin-1-yl)-1-cyclohexyl-2-oxoethyl)-2-(methylamino)propanamide | 14 |

TABLE 10-continued

Compounds Prepared by Schemes 7-16

| Ex. No. | Structure | Compound Name | Synthetic Scheme |
|---|---|---|---|
| 449 | 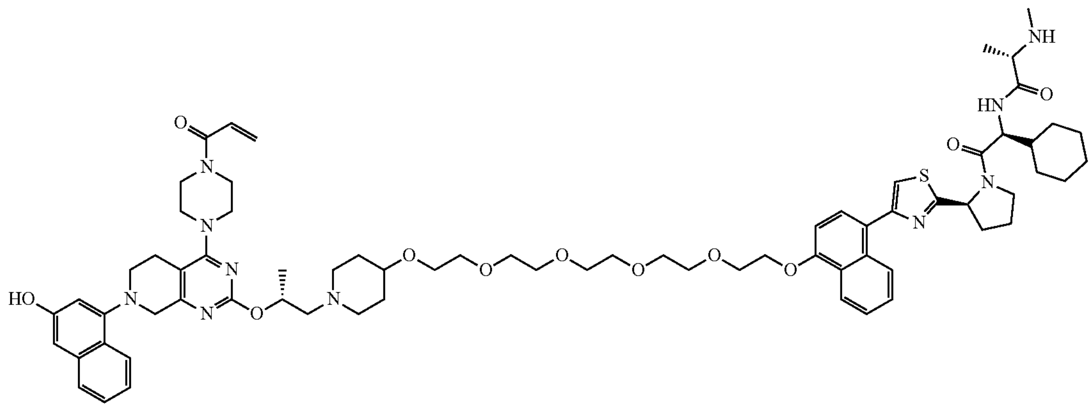 [SMILES: C=CC(=O)N1CCN(c2nc(O[C@H](C)CN3CCC(OCCOCCOCCOCCOCCOc4ccc(-c5csc([C@@H]6CCCN6C(=O)[C@@H](NC(=O)[C@H](C)NC)C6CCCCC6)n5)c5ccccc45)CC3)nc3c2CCN(c2cc(O)cc4ccccc24)C3)CC1] | (S)-N-((S)-2-((S)-2-(4-(4-(14-((1-((R)-2-(4-(4-acryloylpiperazin-1-yl)-7-(3-hydroxynaphthalen-1-yl)-5,6,7,8-tetrahydropyrido3,4-d]pyrimidin-2-yl)oxy)propyl)piperidin-4-yl)oxy)-3,6,9,12-tetraoxatetradecyl)oxy)naphthalen-1-yl)thiazol-2-yl)pyrrolidin-1-yl)-1-cyclohexyl-2-oxoethyl)-2-(methylamino)propanamide | 14 |
| 450 | 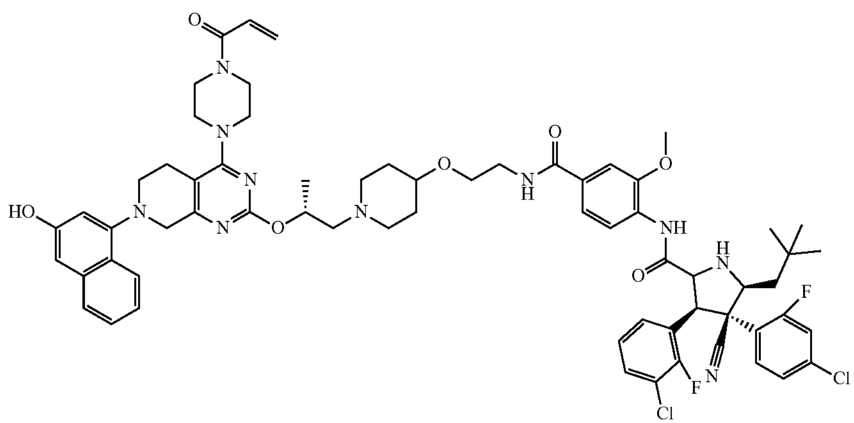 [SMILES: C=CC(=O)N1CCN(c2nc(O[C@H](C)CN3CCC(OCCNC(=O)c4ccc(NC(=O)C5N[C@@H](CC(C)(C)C)[C@](C#N)(c6ccc(Cl)cc6F)[C@H]5c5cccc(Cl)c5F)c(OC)c4)CC3)nc3c2CCN(c2cc(O)cc4ccccc24)C3)CC1] | (2R,3S,4R,5S)-N-(4-((2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 15 |

TABLE 10-continued

Compounds Prepared by Schemes 7-16

| Ex. No. | Structure | Compound Name | Synthetic Scheme |
|---|---|---|---|
| 451 | 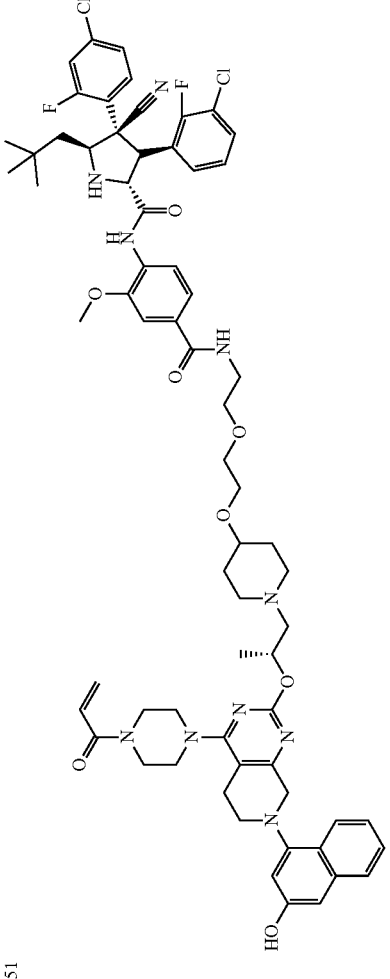 | (2R,3S,4R,5S)-N-(4-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 15 |
| 452 | 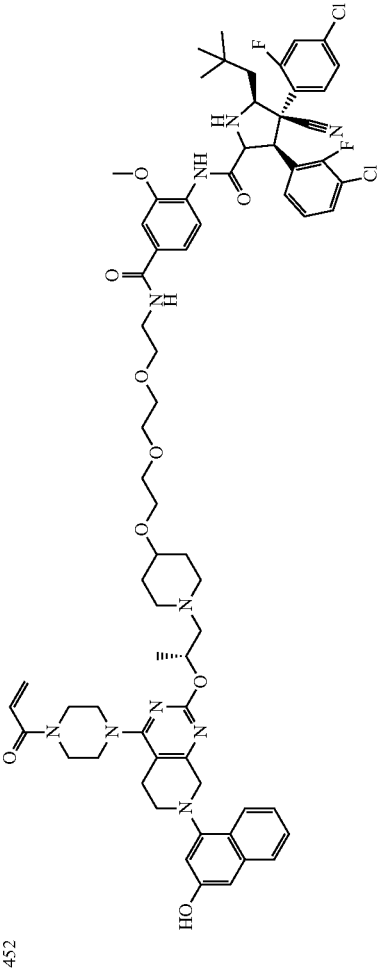 | (2R,3S,4R,5S)-N-(4-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 15 |

TABLE 10-continued

Compounds Prepared by Schemes 7-16

| Ex. No. | Structure | Compound Name | Synthetic Scheme |
|---|---|---|---|
| 453 | 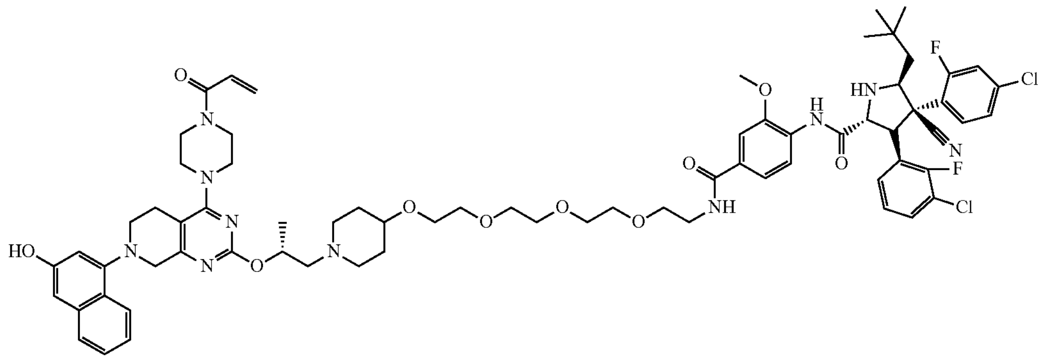 | (2R,3S,4R,5S)-N-(4-(2-(2-(2-(2-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)ethoxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 15 |
| 454 | 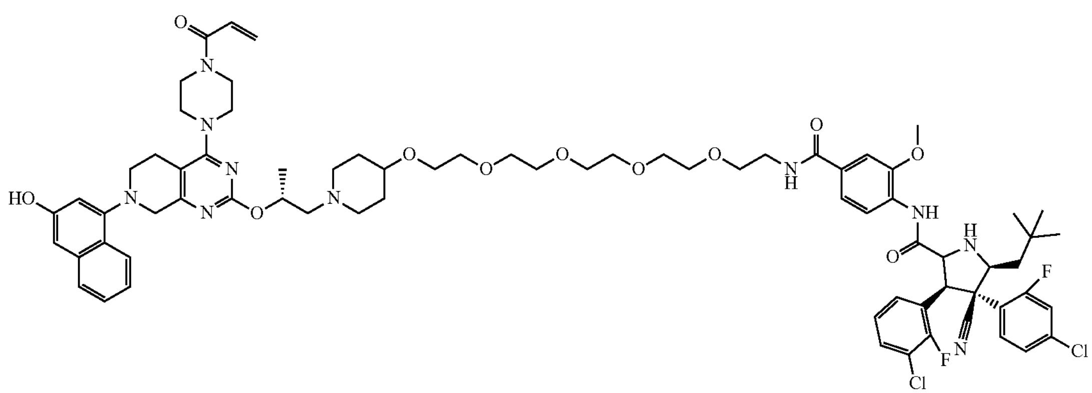 [SMILES: C=CC(=O)N1CCN(c2nc(O[C@H](C)CN3CCC(OCCOCCOCCOCCOCCNC(=O)c4ccc(NC(=O)C5N[C@@H](CC(C)(C)C)[C@](C#N)(c6ccc(Cl)cc6F)[C@H]5c5cccc(Cl)c5F)c(OC)c4)CC3)nc3c2CCN(c2cc(O)cc4ccccc24)C3)CC1] | (2R,3S,4R,5S)-N-(4-((14-((1-((R)-2-((4-(4-acryloylpiperazin-1-yl)-7-(3-hydroxynaphthalen-1-yl)-5,6,7,8-tetrahydropyrido[3,4-d]pyrimidin-2-yl)oxy)propyl)piperidin-4-yl)oxy)-3,6,9,12-tetraoxatetradecyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 15 |

TABLE 10-continued

Compounds Prepared by Schemes 7-16

| Ex. No. | Structure | Compound Name | Synthetic Scheme |
|---|---|---|---|
| 458 | 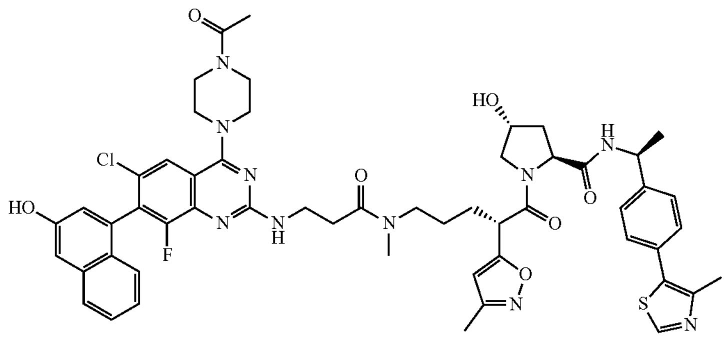 [SMILES: CC(=O)N1CCN(c2nc(NCCC(=O)N(C)CCC[C@H](C(=O)N3C[C@H](O)C[C@H]3C(=O)N[C@@H](C)c3ccc(-c4scnc4C)cc3)c3cc(C)no3)nc3c(F)c(-c4cc(O)cc5ccccc45)c(Cl)cc23)CC1] | (2S,4R)-1-((2S)-5-(3-((4-(4-acetylpiperazin-1-yl)-6-chloro-8-fluoro-7-(3-hydroxynaphthalen-1-yl)quinazolin-2-yl)amino)-N-methylpropanamido)-2-(3-methylisoxazol-5-yl)pentanoyl)-4-hydroxy-N-((S)-1-(4-(4-methylthiazol-5-yl)phenyl)ethyl)pyrrolidine-2-carboxamide | Custom |
| 459 | 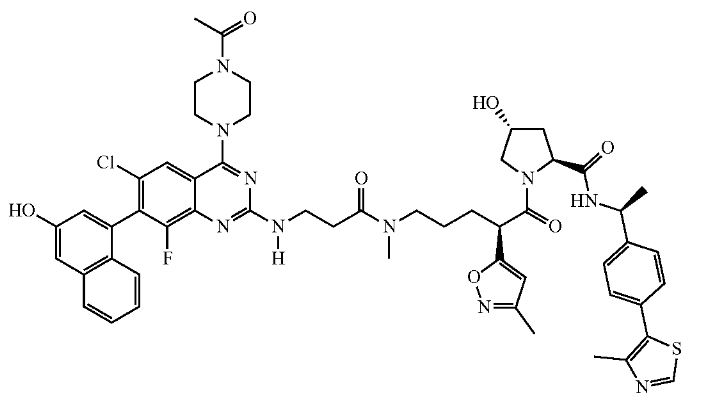 [SMILES: CC(=O)N1CCN(c2nc(NCCC(=O)N(C)CCC[C@@H](C(=O)N3C[C@H](O)C[C@H]3C(=O)N[C@@H](C)c3ccc(-c4scnc4C)cc3)c3cc(C)no3)nc3c(F)c(-c4cc(O)cc5ccccc45)c(Cl)cc23)CC1] | (2S,4R)-1-((2R)-5-(3-((4-(4-acetylpiperazin-1-yl)-6-chloro-8-fluoro-7-(3-hydroxynaphthalen-1-yl)quinazolin-2-yl)amino)-N-methylpropanamido)-2-(3-methylisoxazol-5-yl)pentanoyl)-4-hydroxy-N-((S)-1-(4-(4-methylthiazol-5-yl)phenyl)ethyl)pyrrolidine-2-carboxamide | Custom |

TABLE 10-continued

Compounds Prepared by Schemes 7-16

| Ex. No. | Structure | Compound Name | Synthetic Scheme |
|---|---|---|---|
| 460 | 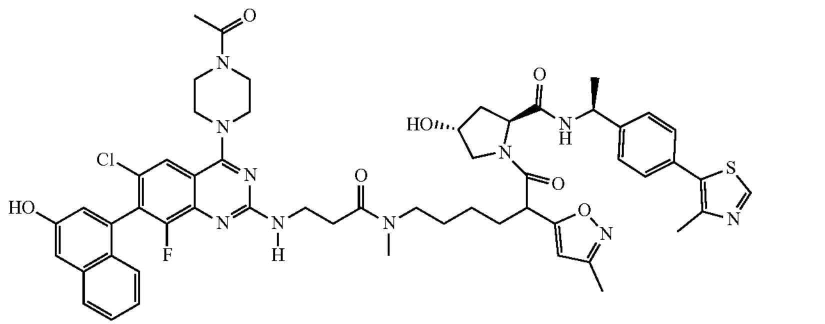 [SMILES: CC(=O)N1CCN(c2nc(NCCC(=O)N(C)CCCCC(C(=O)N3C[C@H](O)C[C@H]3C(=O)N[C@@H](C)c3ccc(-c4scnc4C)cc3)c3cc(C)no3)nc3c(F)c(-c4cc(O)cc5ccccc45)c(Cl)cc23)CC1] | (2S,4R)-1-(6-(3-((4-(4-acetylpiperazin-1-yl)-6-chloro-8-fluoro-7-(3-hydroxynaphthalen-1-yl)quinazolin-2-yl)amino)-N-methylpropanamido)-2-(3-methylisoxazol-5-yl)hexanoyl)-4-hydroxy-N-((S)-1-(4-(4-methylthiazol-5-yl)phenyl)ethyl)pyrrolidine-2-carboxamide | Custom |
| 461 | 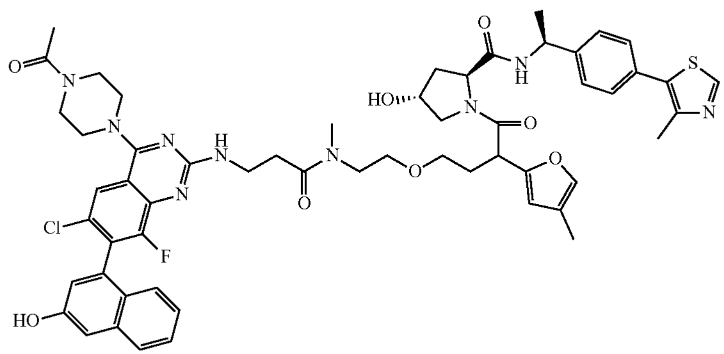 [SMILES: CC(=O)N1CCN(c2nc(NCCC(=O)N(C)CCOCCC(C(=O)N3C[C@H](O)C[C@H]3C(=O)N[C@@H](C)c3ccc(-c4scnc4C)cc3)c3cc(C)co3)nc3c(F)c(-c4cc(O)cc5ccccc45)c(Cl)cc23)CC1] | (2S,4R)-1-(4-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)-2-(3-methylisoxazol-5-yl)butanoyl)-4-hydroxy-N-((S)-1-(4-(4-methylthiazol-5-yl)phenyl)ethyl)pyrrolidine-2-carboxamide | Custom |
| 462 | 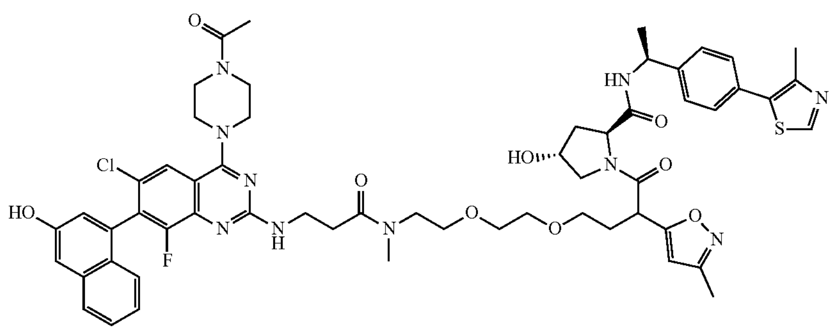 [SMILES: CC(=O)N1CCN(c2nc(NCCC(=O)N(C)CCOCCOCCC(C(=O)N3C[C@H](O)C[C@H]3C(=O)N[C@@H](C)c3ccc(-c4scnc4C)cc3)c3cc(C)no3)nc3c(F)c(-c4cc(O)cc5ccccc45)c(Cl)cc23)CC1] | (2S,4R)-1-(4-(2-(2-(3-(4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)-2-(3-methylisoxazol-5-yl)butanoyl)-4-hydroxy-N-((S)-1-(4-(4-methylthiazol-5-yl)phenyl)ethyl)pyrrolidine-2-carboxamide | Custom |

TABLE 10-continued

Compounds Prepared by Schemes 7-16

| Ex. No. | Structure | Compound Name | Synthetic Scheme |
|---|---|---|---|
| 463 | 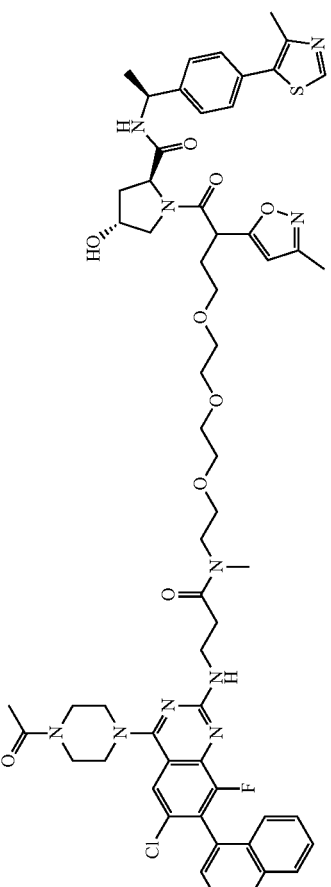 | (2S,4R)-1-(1-((4-(4-acetylpiperazin-1-yl)-6-chloro-8-fluoro-7-(3-hydroxynaphthalen-1-yl)quinazolin-2-yl)amino)-4-methyl-16-(3-methylisoxazol-5-yl)-3-oxo-7,10,13-trioxa-4-azaheptadecan-17-oyl)-4-hydroxy-N-((S)-1-(4-(4-methylthiazol-5-yl)phenyl)ethyl)pyrrolidine-2-carboxamide | Custom |
| 464 | 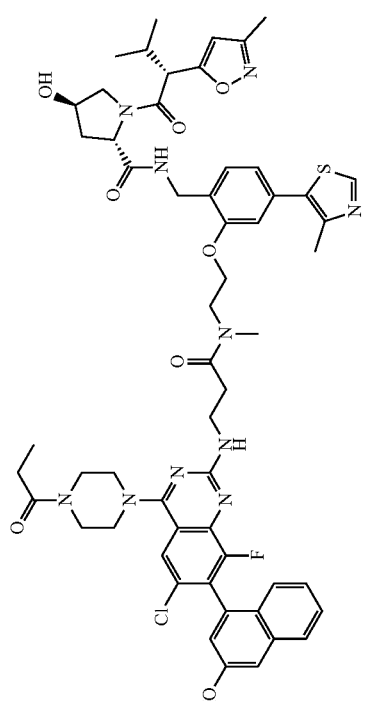 | (2S,4R)-N-(2-(2-(3-((6-chloro-8-fluoro-7-(3-hydroxynaphthalen-1-yl)-4-(4-propionylpiperazin-1-yl)quinazolin-2-yl)amino)-N-methylpropanamido)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | Custom |

TABLE 10-continued

Compounds Prepared by Schemes 7-16

| Ex. No. | Structure | Compound Name | Synthetic Scheme |
|---|---|---|---|
| 465 | 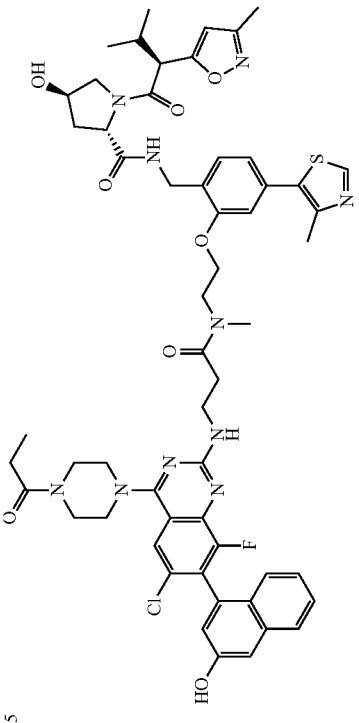 | (2S,4R)-N-(2-(2-(3-((6-chloro-8-fluoro-7-(3-hydroxynaphthalen-1-yl)-4-(4-propionylpiperazin-1-yl)quinazolin-2-yl)amino)-N-methylpropanamido)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | Custom |
| 466 | 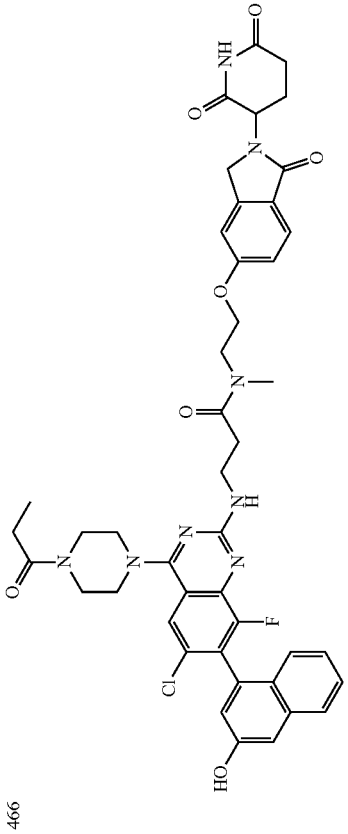 | 3-((6-chloro-8-fluoro-7-(3-hydroxynaphthalen-1-yl)-4-(4-propionylpiperazin-1-yl)quinazolin-2-yl)amino)-N-(2-((2-(2,6-dioxopiperidin-3-yl)-1-oxoisoindolin-5-yl)oxy)ethyl)-N-methylpropanamide | Custom |

TABLE 10-continued

Compounds Prepared by Schemes 7-16

| Ex. No. | Structure | Compound Name | Synthetic Scheme |
|---|---|---|---|
| 467 | 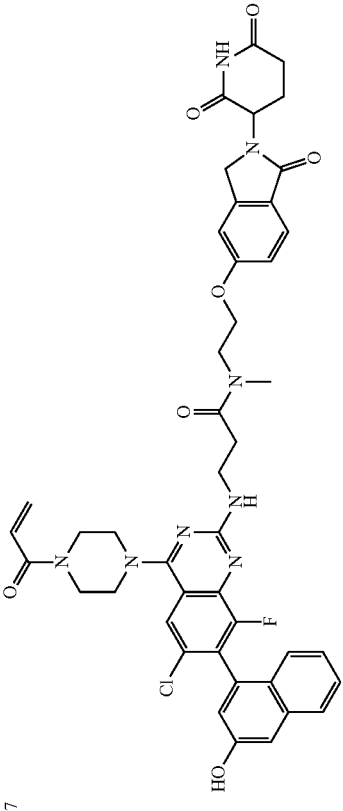 | 3-((4-(4-acryloylpiperazin-1-yl)-6-chloro-8-fluoro-7-(3-hydroxynaphthalen-1-yl)quinazolin-2-yl)amino)-N-(2-((2-(2,6-dioxopiperidin-3-yl)-1,3-dioxoisoindolin-5-yl)oxy)ethyl)-N-methylpropanamide | Custom |
| 468 | 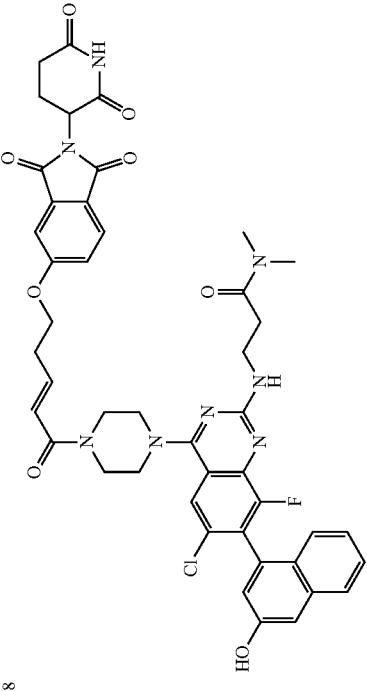 | (E)-3-((6-chloro-4-(4-(5-(2-(2,6-dioxopiperidin-3-yl)-1,3-dioxoisoindolin-5-yl)oxy)pent-2-enoyl)piperazin-1-yl)-8-fluoro-7-(3-hydroxynaphthalen-1-yl)quinazolin-2-yl)amino)-N,N-imethylpropanamide | Custom |

TABLE 10-continued

Compounds Prepared by Schemes 7-16

| Ex. No. | Structure | Compound Name | Synthetic Scheme |
|---|---|---|---|
| 469 | 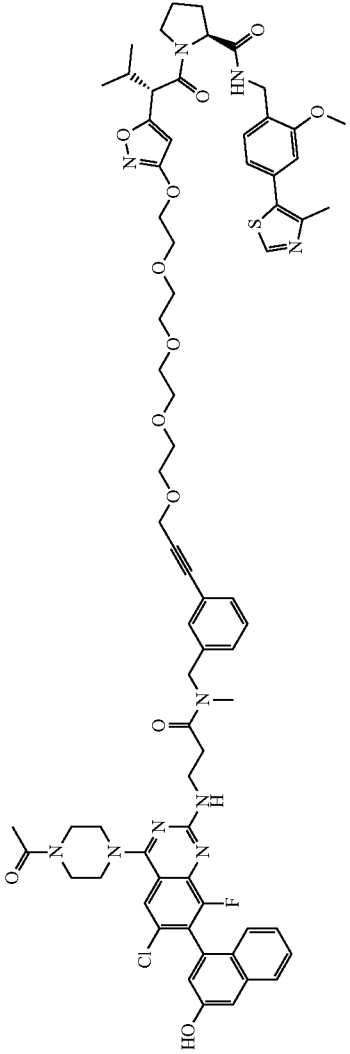 | (2S,4R)-1-((2S)-2-(3-((1S-(3-((4-(4-acetylpiperazin-1-yl)-6-chloro-8-fluoro-7-(3-hydroxynaphthalen-1-yl)quinazolin-2-yl)amino)-N-methylpropanamido)methyl)phenyl)-3,6,9,12-tetraoxapentadec-14-yn-1-yloxy)isoxazol-5-yl)-3-methylbutanoyl)-4-hydroxy-N-(2-methoxy-4-(4-methylthiazol-5-yl)benzyl)pyrrolidine-2-carboxamide | Custom |
| 470 | 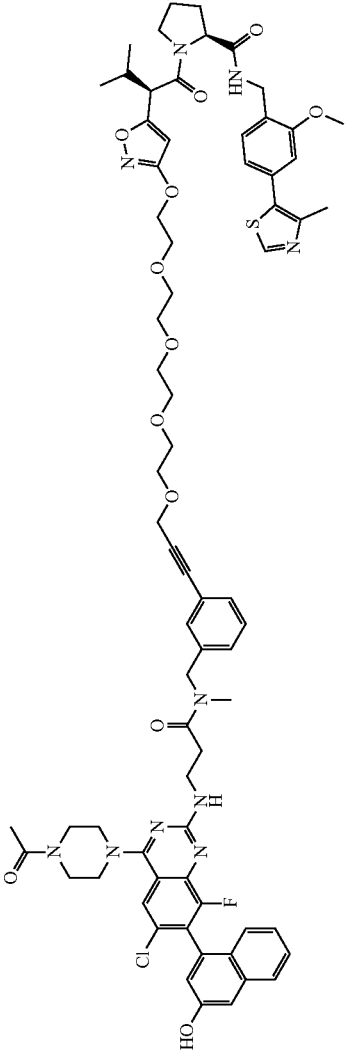 | (2S,4R)-1-((2R)-2-(3-((1S-(3-((4-(4-acetylpiperazin-1-yl)-6-chloro-8-fluoro-7-(3-hydroxynaphthalen-1-yl)quinazolin-2-yl)amino)-N-methylpropanamido)methyl)phenyl)-3,6,9,12-tetraoxapentadec-14-yn-1-yloxy)isoxazol-5-yl)-3-methylbutanoyl)-4-hydroxy-N-(2-methoxy-4-(4-methylthiazol-5-yl)benzyl)pyrrolidine-2-carboxamide | Custom |

TABLE 10-continued

Compounds Prepared by Schemes 7-16

| Ex. No. | Structure | Compound Name | Synthetic Scheme |
|---|---|---|---|
| 471 | 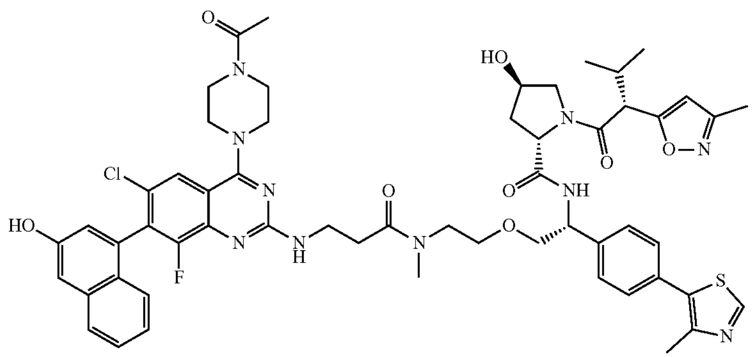 [SMILES: CC(=O)N1CCN(c2nc(NCCC(=O)N(C)CCOC[C@H](NC(=O)[C@@H]3C[C@@H](O)CN3C(=O)[C@@H](c3cc(C)no3)C(C)C)c3ccc(-c4scnc4C)cc3)nc3c(F)c(-c4cc(O)cc5ccccc45)c(Cl)cc23)CC1] | (2S,4R)-N-((1R)-2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)-1-(4-(4-methylthiazol-5-yl)phenyepethyl)-4-hydroxy-1-((R)-3-methyl-2-(3-methylisoxazol-5-yl)butanoyl)pyrrolidine-2-carboxamide | Custom |
| 472 | 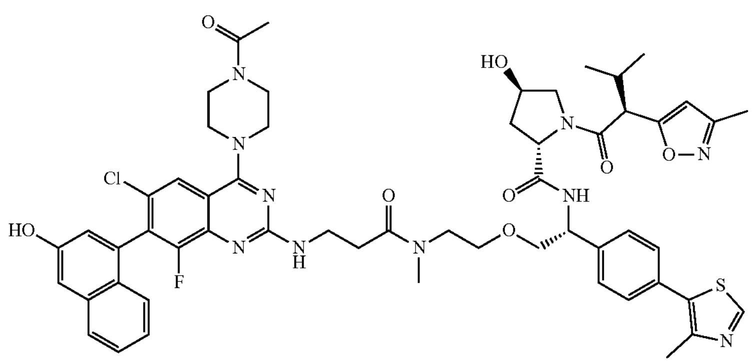 [SMILES: CC(=O)N1CCN(c2nc(NCCC(=O)N(C)CCOC[C@H](NC(=O)[C@@H]3C[C@@H](O)CN3C(=O)[C@H](c3cc(C)no3)C(C)C)c3ccc(-c4scnc4C)cc3)nc3c(F)c(-c4cc(O)cc5ccccc45)c(Cl)cc23)CC1] | (2S,4R)-N-((1R)-2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)-1-(4-(4-methylthiazol-5-yl)phenyl)ethyl)-4-hydroxy-1-((S)-3-methyl-2-(3-methylisoxazol-5-yl)butanoyl)pyrrolidine-2-carboxamide | Custom |

TABLE 10-continued

Compounds Prepared by Schemes 7-16

| Ex. No. | Structure | Compound Name | Synthetic Scheme |
|---|---|---|---|
| 473 | 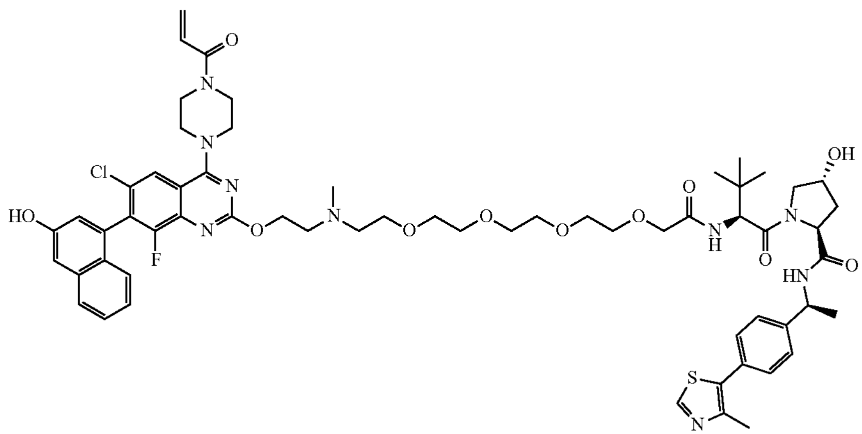 [SMILES: C=CC(=O)N1CCN(c2nc(OCCN(C)CCOCCOCCOCCOCC(=O)N[C@H](C(=O)N3C[C@H](O)C[C@H]3C(=O)N[C@@H](C)c3ccc(-c4scnc4C)cc3)C(C)(C)C)nc3c(F)c(-c4cc(O)cc5ccccc45)c(Cl)cc23)CC1] | (2S,4R)-1-((2S)-20-((4-(4-acryloylpiperazin-1-yl)-6-chloro-8-fluoro-7-(3-hydroxynaphthalen-1-yl)quinazolin-2-yl)oxy)-2-(tert-butyl)-18-methyl-4-oxo-6,9,12,15-tetraoxa-3,18-diazaicosanoyl)-4-hydroxy-N-((S)-1-(4-(4-methylthiazol-5-yl)phenyl)ethyl)pyrrolidine-2-carboxamide | Custom |
| 474 | 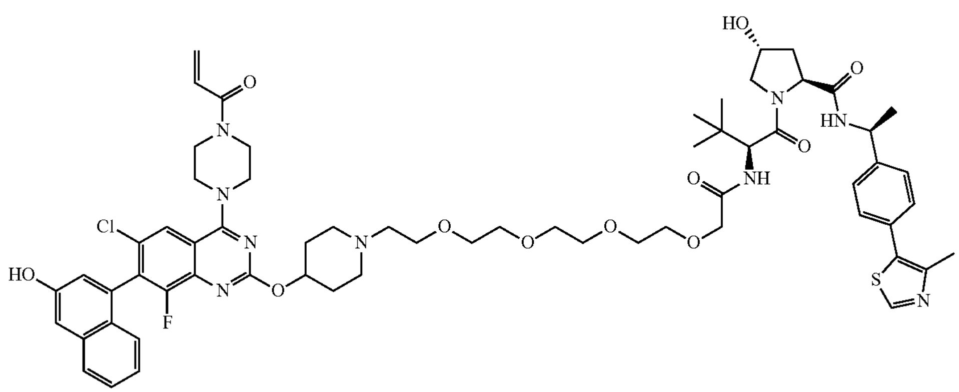 [SMILES: C=CC(=O)N1CCN(c2nc(OC3CCN(CCOCCOCCOCCOCC(=O)N[C@H](C(=O)N4C[C@H](O)C[C@H]4C(=O)N[C@@H](C)c4ccc(-c5scnc5C)cc4)C(C)(C)C)CC3)nc3c(F)c(-c4cc(O)cc5ccccc45)c(Cl)cc23)CC1] | (2S,4R)-1-((2S)-17-(4-(4-acryloylpiperazin-1-yl)-6-chloro-8-fluoro-7-(3-hydroxynaphthalen-1-yl)quinazolin-2-yl)oxy)piperidin-1-yl)-2-(tert-butyl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | Custom |

TABLE 10-continued

Compounds Prepared by Schemes 7-16

| Ex. No. | Structure | Compound Name | Synthetic Scheme |
|---|---|---|---|
| 475 | 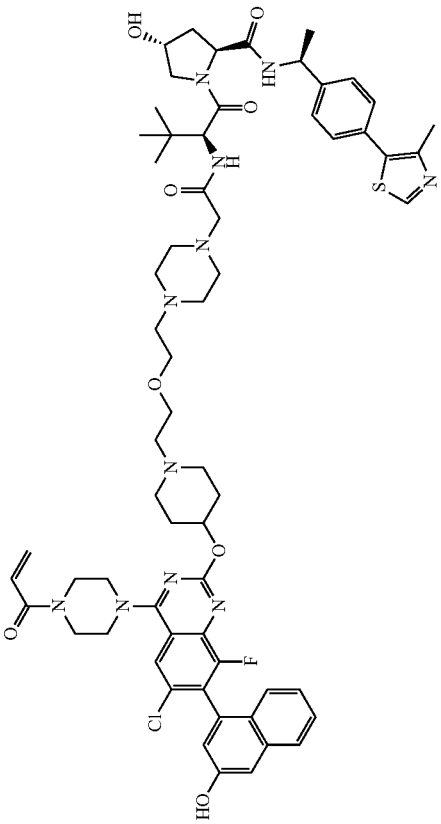 | (2S,4R)-1-((2S)-2-(2-(4-(2-(2-(4-((4-(4-acryloyl)piperazin-1-yl)-6-chloro-8-fluoro-7-(3-hydroxynaphthalen-1-yl)quinazolin-2-yl)oxy)piperidin-1-yl)ethoxy)ethyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | Custom |
| 476 | 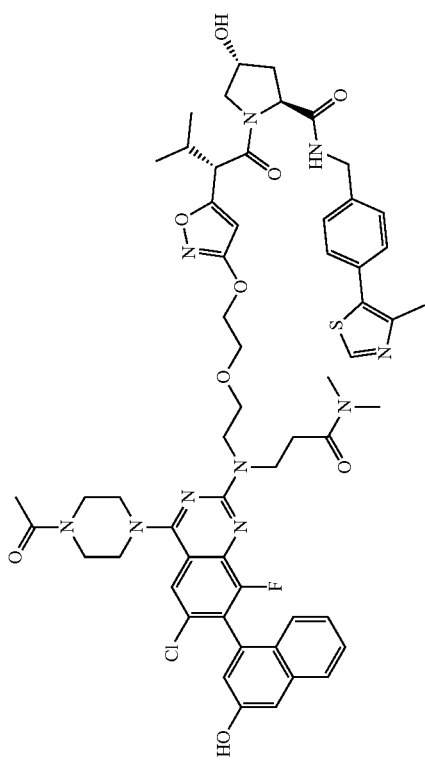 | (2S,4R)-14(2S)-2-(3-(2-((4-(4-acetylpiperazin-1-yl)-6-chloro-8-fluoro-7-(3-hydroxynaphthalen-1-yl)quinazolin-2-yl)(3-(dimethylamino)-3-oxopropyl)amino)ethoxy)ethoxy)isoxazol-5-yl)-3-methylbutanoyl)-4-hydroxy-N-(4-(4-methylthiazol-5-yl)benzyl)pyrrolidine-2-carboxamide | Custom |

TABLE 10-continued

Compounds Prepared by Schemes 7-16

| Ex. No. | Structure | Compound Name | Synthetic Scheme |
|---|---|---|---|
| 477 | 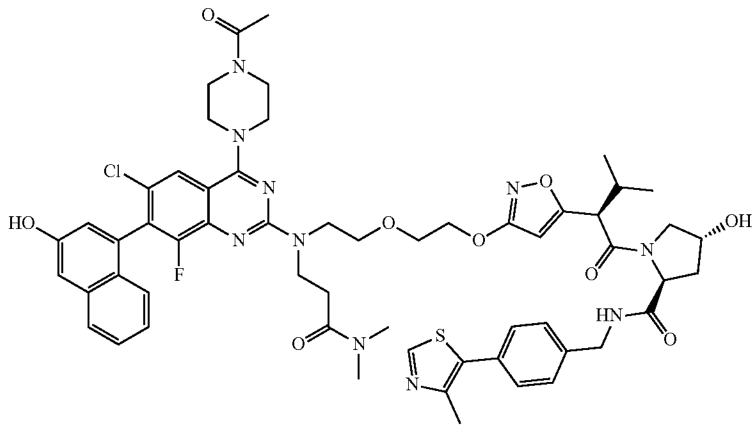 [SMILES: CC(=O)N1CCN(c2nc(N(CCOCCOc3cc([C@H](C(=O)N4C[C@H](O)C[C@H]4C(=O)NCc4ccc(-c5scnc5C)cc4)C(C)C)on3)CCC(=O)N(C)C)nc3c(F)c(-c4cc(O)cc5ccccc45)c(Cl)cc23)CC1] | (2S,4R)-1-((2R)-2-(3-(2-(2-((4-(4-acetylpiperazin-1-yl)-6-chloro-8-fluoro-7-(3-hydroxynaphthalen-1-yl)quinazolin-2-yl)(3-(dimethylamino)-3-oxopropyl)amino)ethoxy)ethoxy)isoxazol-5-yl)-3-methylbutanoyl)-4-hydroxy-N-(4-(4-methylthiazol-5-yl)benzyl)pyrrolidine-2-carboxamide | Custom |
| 478 | 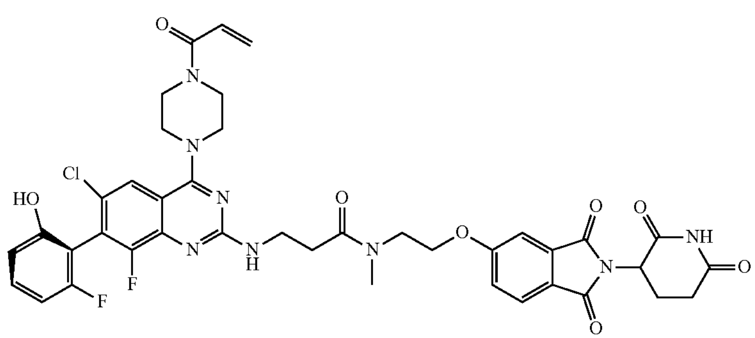 | 3-(((S)-4-(4-acryloylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-5-yl)oxy)ethyl)-N-methylpropanamide | Custom |

TABLE 10-continued

Compounds Prepared by Schemes 7-16

| Ex. No. | Structure | Compound Name | Synthetic Scheme |
|---|---|---|---|
| 479 | 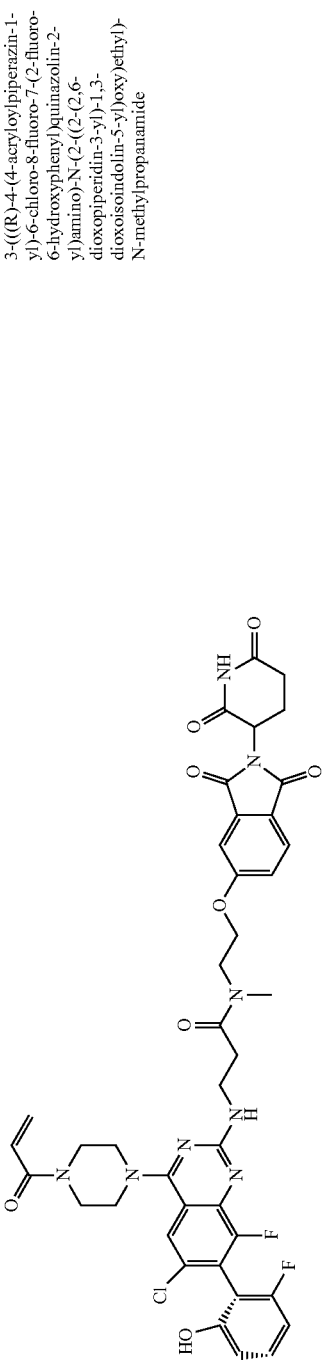 | 3-(((R)-4-(4-acryloylpiperazin-1-yl)-6-chloro-8-fluoro-7-(2-fluoro-6-hydroxyphenyl)quinazolin-2-yl)amino)-N-(2-((2-(2,6-dioxopiperidin-3-yl)-1,3-dioxoisoindolin-5-yl)oxy)ethyl)-N-methylpropanamide | Custom |
| 480 | 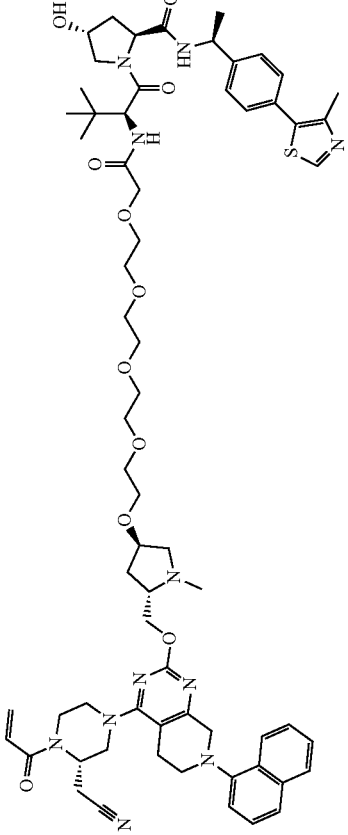 | (2S,4R)-1-((S)-17-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)-2-(tert-butyl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | Custom |

TABLE 10-continued

Compounds Prepared by Schemes 7-16

| Ex. No. | Structure | Compound Name | Synthetic Scheme |
|---|---|---|---|
| 481 | 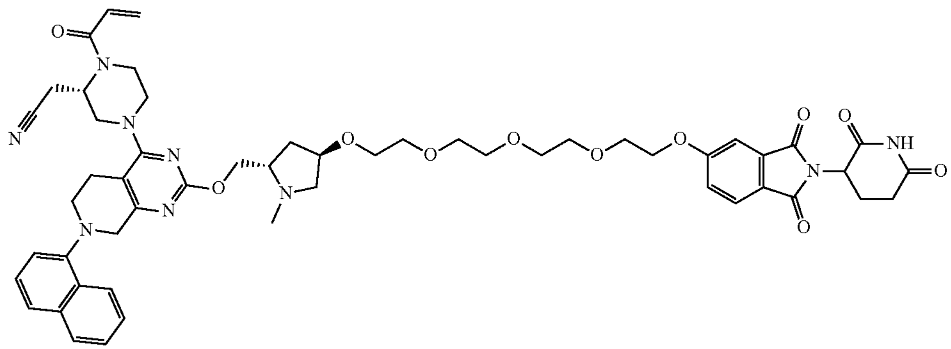 [SMILES: C=CC(=O)N1CCN(c2nc(OC[C@@H]3C[C@@H](OCCOCCOCCOCCOc4ccc5c(c4)C(=O)N(C4CCC(=O)NC4=O)C5=O)CN3C)nc3c2CCN(c2cccc4ccccc24)C3)C[C@@H]1CC#N] | 2-((2S)-1-acryloyl-4-(2-(((2S,4R)-4-(2-(2-(2-(2-((2-(2,6-dioxopiperidin-3-yl)-1,3-dioxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]dipyrimidin-4-yl)piperazin-2-yl)acetonitrile | Custom |
| 482 | 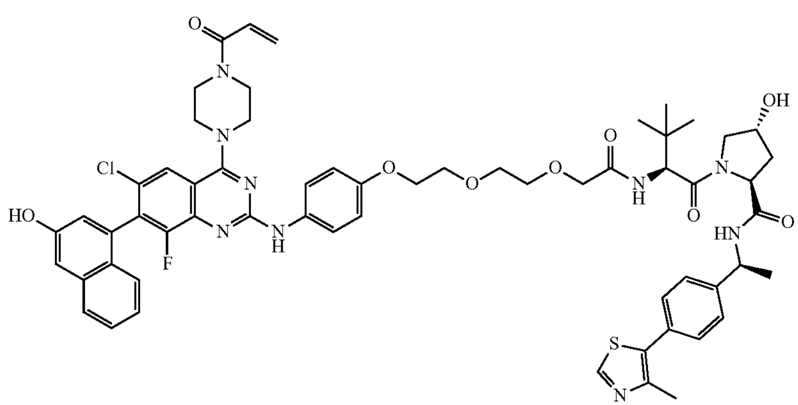 [SMILES: C=CC(=O)N1CCN(c2nc(Nc3ccc(OCCOCCOCC(=O)N[C@H](C(=O)N4C[C@H](O)C[C@H]4C(=O)N[C@@H](C)c4ccc(-c5scnc5C)cc4)C(C)(C)C)cc3)nc3c(F)c(-c4cc(O)cc5ccccc45)c(Cl)cc23)CC1] | (2S,4R)-1-42S)-2-(2-(2-(2-(4-((4-(4-acryloylpiperazin-1-yl)-6-chloro-8-fluoro-7-(3-hydroxynaphthalen-1-yl)quinazolin-2-yl)amino)phenoxy)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | Custom 1 |

TABLE 10-continued

Compounds Prepared by Schemes 7-16

| Ex. No. | Structure | Compound Name | Synthetic Scheme |
|---|---|---|---|
| 483 | 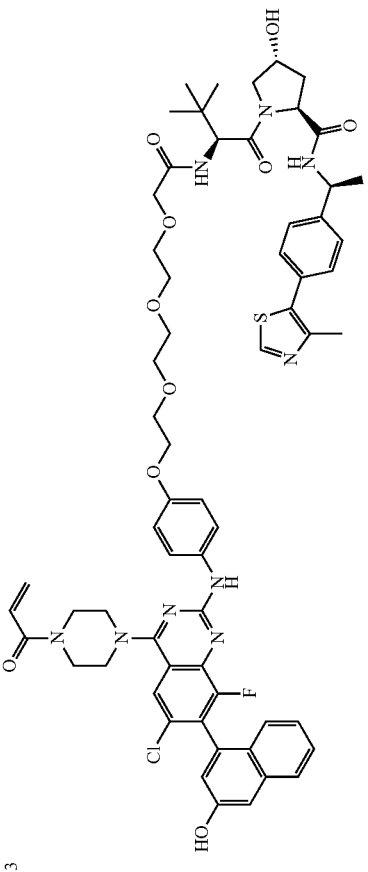 | (2S,4R)-1-((2S)-14-(4-(4-(4-acryloylpiperazin-1-yl)-6-chloro-8-fluoro-7-(3-hydroxynaphthalen-1-yl)quinazolin-2-yl)amino)phenoxy)-2-(tert-butyl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | Custom 1 |
| 484 | 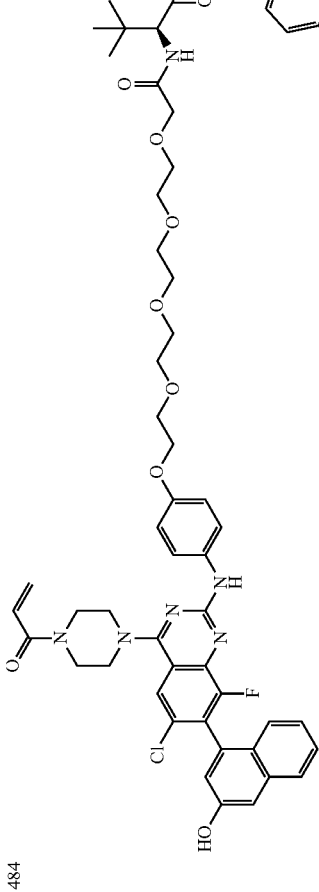 | (2S,4R)-1-((2S)-17-(4-((4-(4-acryloylpiperazin-1-yl)-6-chloro-8-fluoro-7-(3-hydroxynaphthalen-1-yl)quinazolin-2-yl)amino)phenoxy)-2-(tert-butyl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | Custom 1 |

TABLE 10-continued

Compounds Prepared by Schemes 7-16

| Ex. No. | Structure | Compound Name | Synthetic Scheme |
|---|---|---|---|
| 485 | 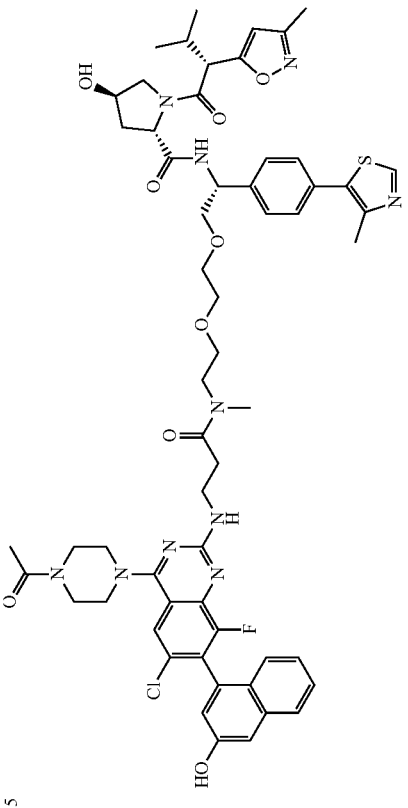 | (2S,4R)-N-((1R)-2-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)-1-(4-(4-methylthiazol-5-yl)phenyl)ethyl)-4-hydroxy-1-((R)-3-methyl-2-(3-methylisoxazol-5-yl)butanoyl)pyrrolidine-2-carboxamide | Custom 2 |
| 486 | 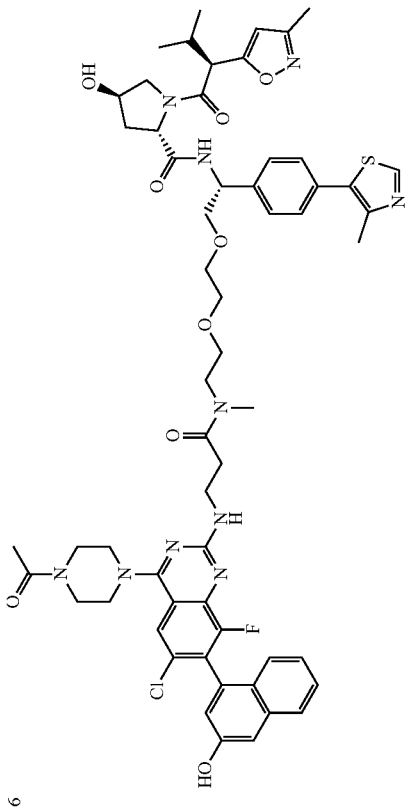 | (2S,4R)-N-((1R)-2-(2-(2-(3-((4-(4-acetylpiperazin-1-yl)-6-chloro-8-fluoro-7-(3-hydroxynaphthalen-1-yl)quinazolin-2-yl)amino)-N-methylpropanamido)ethoxy)ethoxy)-1-(4-(4-methylthiazol-5-yl)phenyl)ethyl)-4-hydroxy-1-((S)-3-methyl-2-(3-methylisoxazol-5-yl)butanoyl)pyrrolidine-2-carboxamide | Custom 2 |

TABLE 10-continued

Compounds Prepared by Schemes 7-16

| Ex. No. | Structure | Compound Name | Synthetic Scheme |
|---|---|---|---|
| 487 | 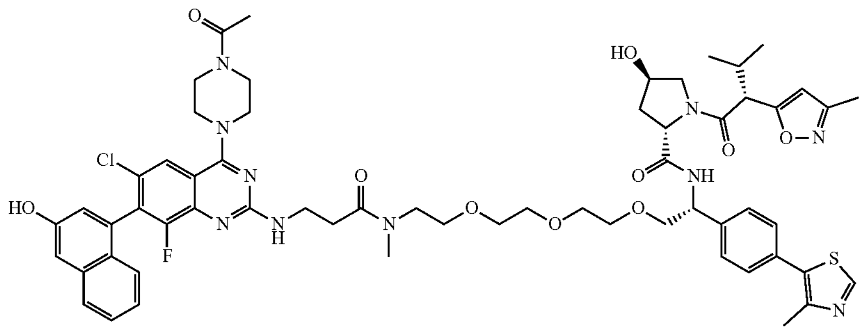 [SMILES: CC(=O)N1CCN(c2nc(NCCC(=O)N(C)CCOCCOCCOC[C@H](NC(=O)[C@@H]3C[C@@H](O)CN3C(=O)[C@@H](c3cc(C)no3)C(C)C)c3ccc(-c4scnc4C)cc3)nc3c(F)c(-c4cc(O)cc5ccccc45)c(Cl)cc23)CC1] | (2S,4R)-N-((1R)-15-((4-(4-acetylpiperazin-1-yl)-6-chloro-8-fluoro-7-(3-hydroxynaphthalen-1-yl)quinazolin-2-yl)amino)-12-methyl-1-(4-(4-methylthiazol-5-yl)phenyl)-13-oxo-3,6,9-trioxa-12-azapentadecyl)-4-hydroxy-1-((R)-3-methyl-2-(3-methylisoxazol-5-yl)butanoyl)pyrrolidine-2-carboxamide | Custom 2 |
| 488 | 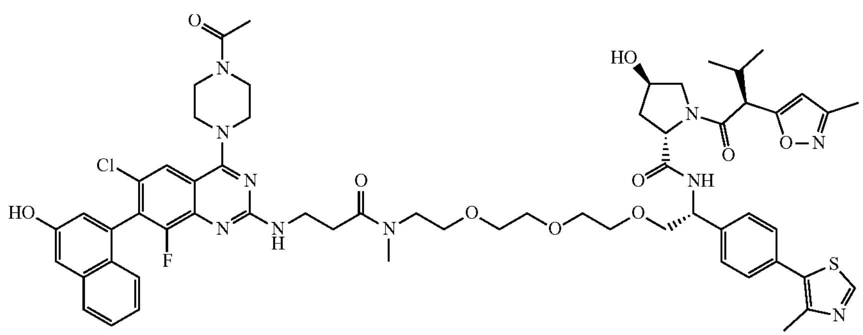 [SMILES: CC(=O)N1CCN(c2nc(NCCC(=O)N(C)CCOCCOCCOC[C@H](NC(=O)[C@@H]3C[C@@H](O)CN3C(=O)[C@H](c3cc(C)no3)C(C)C)c3ccc(-c4scnc4C)cc3)nc3c(F)c(-c4cc(O)cc5ccccc45)c(Cl)cc23)CC1] | (2S,4R)-N-((1R)-15-((4-(4-acetylpiperazin-1-yl)-6-chloro-8-fluoro-7-(3-hydroxynaphthalen-1-yl)quinazolin-2-yl)amino)-12-methyl-1-(4-(4-methylthiazol-5-yl)phenyl)-13-oxo-3,6,9-trioxa-12-azapentadecyl)-4-hydroxy-1-((S)-3-methyl-2-(3-methylisoxazol-5-yl)butanoyl)pyrrolidine-2-carboxamide | Custom 2 |

TABLE 10-continued

Compounds Prepared by Schemes 7-16

| Ex. No. | Structure | Compound Name | Synthetic Scheme |
|---|---|---|---|
| 489 | 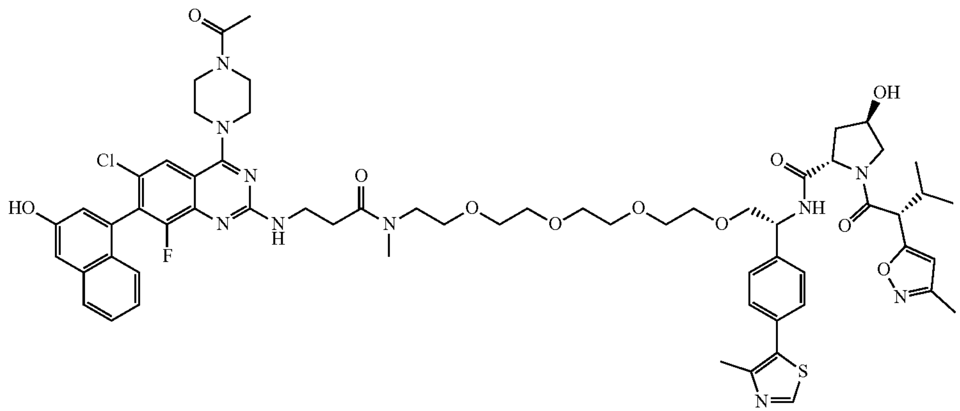 [SMILES: CC(=O)N1CCN(c2nc(NCCC(=O)N(C)CCOCCOCCOCCOC[C@H](NC(=O)[C@@H]3C[C@@H](O)CN3C(=O)[C@@H](c3cc(C)no3)C(C)C)c3ccc(-c4scnc4C)cc3)nc3c(F)c(-c4cc(O)cc5ccccc45)c(Cl)cc23)CC1] | (2S,4R)-N-((1R)-18-((4-(4-acetylpiperazin-1-yl)-6-chloro-8-fluoro-7-(3-hydroxynaphthalen-1-yl)quinazolin-2-yl)amino)-15-methyl-1-(4-(4-methylthiazol-5-yl)phenyl)-16-oxo-3,6,9,12-tetraoxa-15-azaoctadecyl)-4-hydroxy-1-((R)-3-methyl-2-(3-methylisoxazol-5-yl)butanoyl)pyrrolidine-2-carboxamide | Custom 2 |
| 490 | 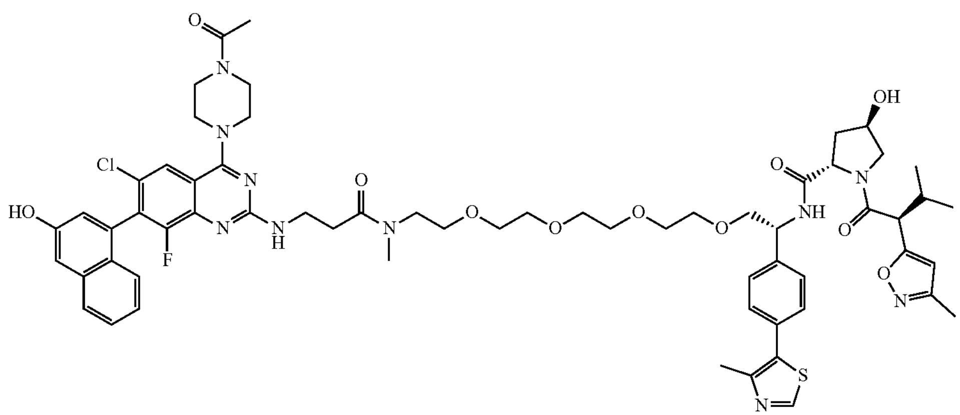 [SMILES: CC(=O)N1CCN(c2nc(NCCC(=O)N(C)CCOCCOCCOCCOC[C@H](NC(=O)[C@@H]3C[C@@H](O)CN3C(=O)[C@H](c3cc(C)no3)C(C)C)c3ccc(-c4scnc4C)cc3)nc3c(F)c(-c4cc(O)cc5ccccc45)c(Cl)cc23)CC1] | (2S,4R)-N-((1R)-18-((4-(4-acetylpiperazin-1-yl)-6-chloro-8-fluoro-7-(3-hydroxynaphthalen-1-yl)quinazolin-2-yl)amino)-15-methyl-1-(4-(4-methylthiazol-5-yl)phenyl)-16-oxo-3,6,9,12-tetraoxa-15-azaoctadecyl)-4-hydroxy-1-((S)-3-methyl-2-(3-methylisoxazol-5-yl)butanoyl)pyrrolidine-2-carboxamide | Custom 2 |

TABLE 10-continued

Compounds Prepared by Schemes 7-16

| Ex. No. | Structure | Compound Name | Synthetic Scheme |
|---|---|---|---|
| 491 | 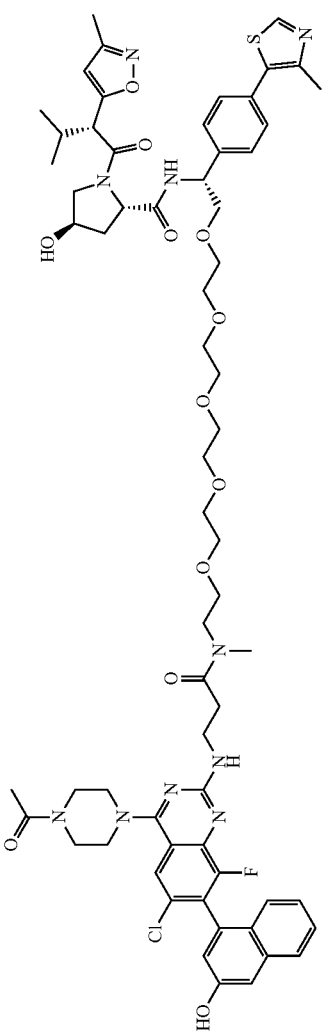 | (2S,4R)-N-((1R)-21-((4-(4-acetylpiperazin-1-yl)-6-chloro-8-fluoro-7-(3-hydroxynaphthalen-1-yl)quinazolin-2-yl)amino)-18-methyl-1-(4-(4-methylthiazol-5-yl)phenyl)-19-oxo-3,6,9,12,15-pentaoxa-18-azahenicosyl)-4-hydroxy-1-((R)-3-methyl-2-(3-methylisoxazol-5-yl)butanoyl)pyrrolidine-2-carboxamide | Custom 2 |
| 492 | 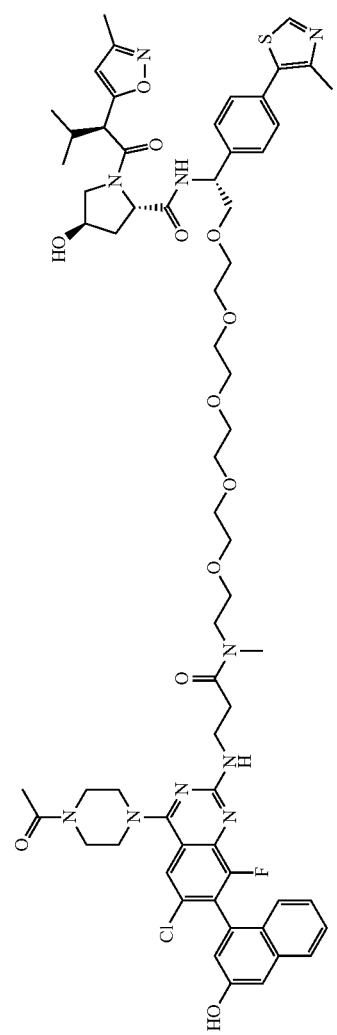 | (2S,4R)-N-((1R)-21-((4-(4-acetylpiperazin-1-yl)-6-chloro-8-fluoro-7-(3-hydroxynaphthalen-1-yl)quinazolin-2-yl)amino)-18-methyl-1-(4-(4-methylthiazol-5-yl)phenyl)-19-oxo-3,6,9,12,15-pentaoxa-18-azahenicosyl)-4-hydroxy-1-((S)-3-methyl-2-(3-methylisoxazol-5-yl)butanoyl)pyrrolidine-2-carboxamide | Custom 2 |

TABLE 10-continued
Compounds Prepared by Schemes 7-16
| Ex. No. | Structure | Compound Name | Synthetic Scheme |
|---|---|---|---|
| 493 | 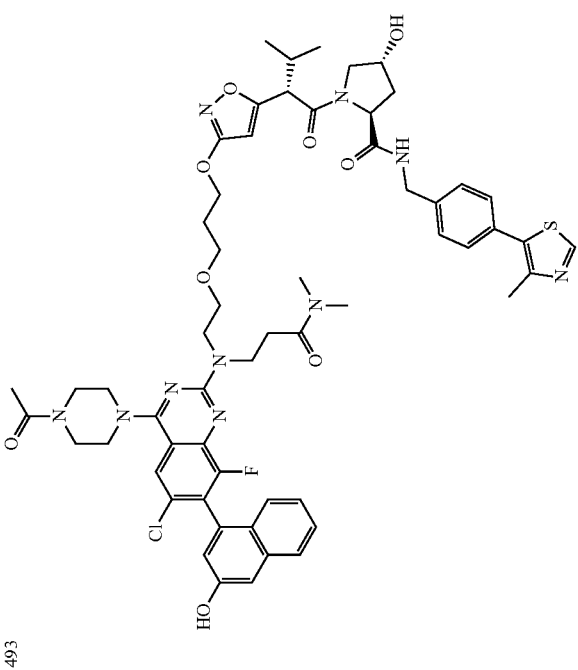 | (2S,4R)-1-((2S)-2-(3-(3-(2-((4-(4-acetylpiperazin-1-yl)-6-chloro-8-fluoro-7-(3-hydroxynaphthalen-1-yl)quinazolin-2-yl)(3-(dimethylamino)-3-oxopropyl)amino)ethoxy)propoxy)isoxazol-5-yl)-3-methylbutanoyl)-4-hydroxy-N-(4-(4-methylthiazol-5-yl)benzyl)pyrrolidine-2-carboxamide | Custom 3 |

TABLE 10-continued
Compounds Prepared by Schemes 7-16
| Ex. No. | Structure | Compound Name | Synthetic Scheme |
|---|---|---|---|
| 494 | 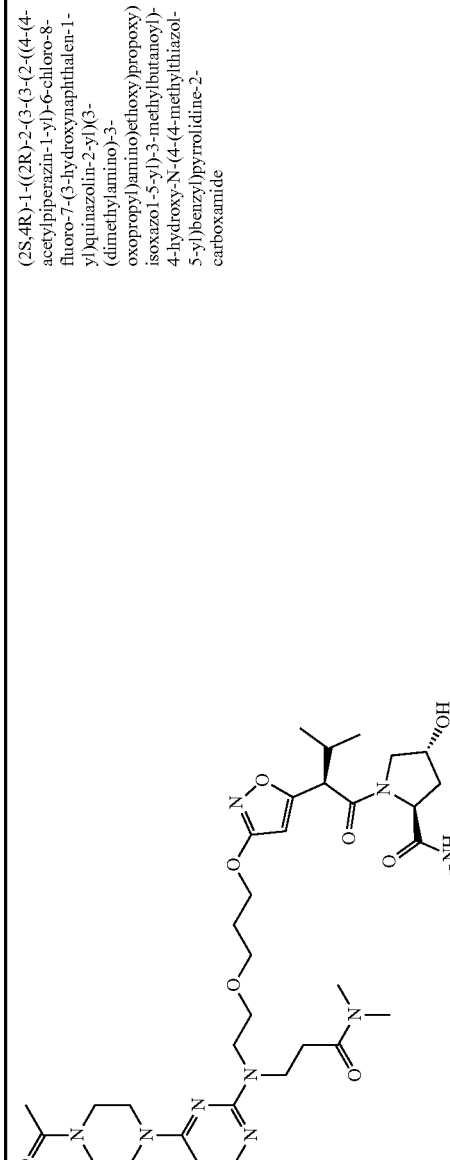 | (2S,4R)-1-((2R)-2-(3-(3-(2-((4-(4-acetylpiperazin-1-yl)-6-chloro-8-fluoro-7-(3-hydroxynaphthalen-1-yl)quinazolin-2-yl)(3-(dimethylamino)-3-oxopropyl)amino)ethoxy)propoxy)isoxazol-5-yl)-3-methylbutanoyl)-4-hydroxy-N-(4-(4-methylthiazol-5-yl)benzyl)pyrrolidine-2-carboxamide | Custom 3 |

TABLE 10-continued

Compounds Prepared by Schemes 7-16

| Ex. No. | Structure | Compound Name | Synthetic Scheme |
|---|---|---|---|
| 495 | 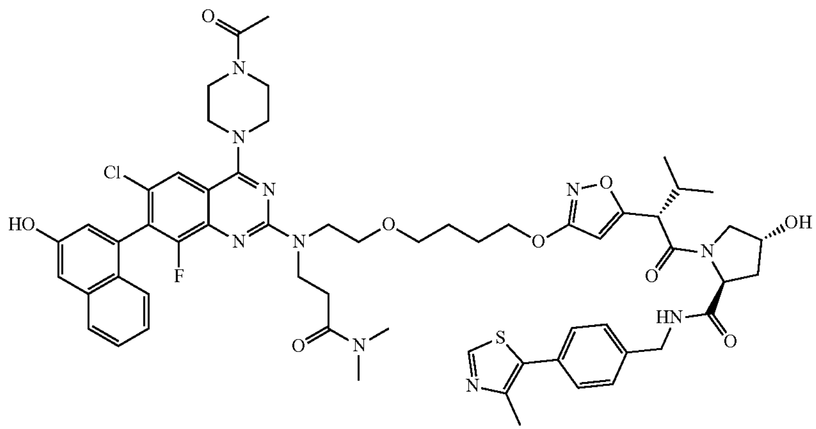 [SMILES: CC(=O)N1CCN(c2nc(N(CCOCCCCOc3cc([C@@H](C(=O)N4C[C@H](O)C[C@H]4C(=O)NCc4ccc(-c5scnc5C)cc4)C(C)C)on3)CCC(=O)N(C)C)nc3c(F)c(-c4cc(O)cc5ccccc45)c(Cl)cc23)CC1] | (2S,4R)-1-((2S)-2-(3-(4-(2-((4-(4-acetylpiperazin-1-yl)-6-chloro-8-fluoro-7-(3-hydroxynaphthalen-1-yl)quinazolin-2-yl)(3-(dimethylamino)-3-oxopropyl)amino)ethoxy)butoxy)isoxazol-5-yl)-3-methylbutanoyl)-4-hydroxy-N-(4-(4-methylthiazol-5-yl)benzyl)pyrrolidine-2-carboxamide | Custom 3 |
| 496 | 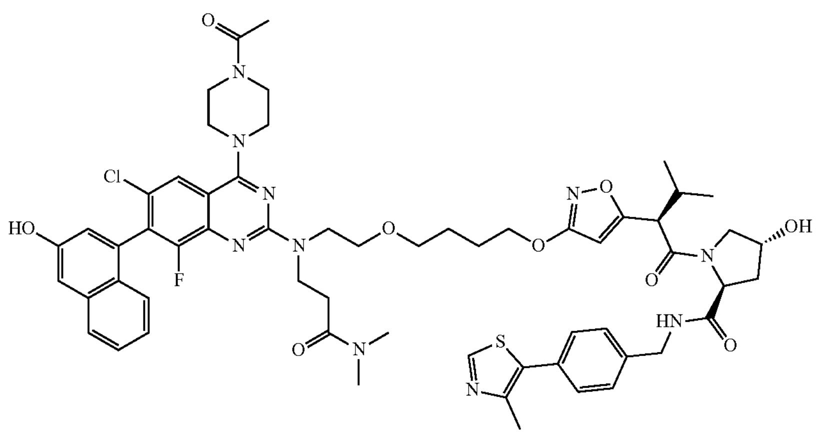 [SMILES: CC(=O)N1CCN(c2nc(N(CCOCCCCOc3cc([C@H](C(=O)N4C[C@H](O)C[C@H]4C(=O)NCc4ccc(-c5scnc5C)cc4)C(C)C)on3)CCC(=O)N(C)C)nc3c(F)c(-c4cc(O)cc5ccccc45)c(Cl)cc23)CC1] | (2S,4R)-1-((2R)-2-(3-(4-(2-((4-(4-acetylpiperazin-1-yl)-6-chloro-8-fluoro-7-(3-hydroxynaphthalen-1-yl)quinazolin-2-yl)(3-(dimethylamino)-3-oxopropyl)amino)ethoxy)butoxy)isoxazol-5-yl)-3-methylbutanoyl)-4-hydroxy-N-(4-(4-methylthiazol-5-yl)benzyl)pyrrolidine-2-carboxamide | Custom 3 |

TABLE 10-continued
Compounds Prepared by Schemes 7-16
| Ex. No. | Structure | Compound Name | Synthetic Scheme |
|---|---|---|---|
| 497 | 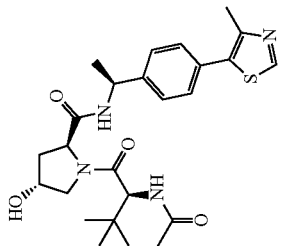 | (2S,4R)-1-((2S)-21-((4-(4-acryloylpiperazin-1-yl)-6-chloro-8-fluoro-7-(3-hydroxynaphthalen-1-yl)quinazolin-2-yl)oxy)-2-(tert-butyl)-18-methyl-4-oxo-6,9,12,15-tetraoxa-3,18-diazahenicosanoyl)-4-hydroxy-N-((S)-1-(4-(4-methylthiazol-5-yl)phenyl)ethyl)pyrrolidine-2-carboxamide | Custom |

TABLE 11

Data for Compounds of Table 10

| Ex. No. | MH+ (1) | MH+ (2) | NMR Transcript | Synthetic Scheme | Mol Weight |
|---|---|---|---|---|---|
| 330 | 1133.71 | 1135.71 | ¹H NMR (400 MHz, MeOD-d₄) δ 8.84 (br d, J = 3.7 Hz, 1H), 7.81-7.72 (m, 2H), 7.41-7.13 (m, 5H), 7.09-6.85 (m, 3H), 6.20 (d, J = 7.0 Hz, 1H), 4.62 (br d, J = 8.2 Hz, 1H), 4.42-4.34 (m, 2H), 4.24-4.09 (m, 2H), 3.98-3.49 (m, 20H), 3.15-3.10 (m, 1H), 3.01-2.70 (m, 4H), 2.51-2.36 (m, 6H), 2.24-2.15 (m, 4H), 2.13-2.02 (m, 1H), 1.21-1.13 (m, 3H), 1.08-0.98 (m, 3H), 0.88-0.82 (m, 3H). | 7 | 1133.74 |
| 331 | 1133.71 | 1135.71 | ¹H NMR (400 MHz, MeOD-d₄) δ 8.85 (br d, J = 4.4 Hz, 1H), 7.82-7.75 (m, 2H), 7.44-7.23 (m, 5H), 7.08-6.94 (m, 3H), 6.24-6.18 (m, 1H), 4.61 (br s, 1H), 4.47-4.39 (m, 2H), 4.18-4.10 (m, 2H), 3.98-3.59 (m, 20H), 3.28-3.08 (m, 3H), 2.98-2.73 (m, 4H), 2.53-2.36 (m, 6H), 2.31-2.22 (m, 4H), 2.18-2.06 (m, 1H), 1.22-1.14 (m, 1.09-0.97 (m, 3H), 0.96-0.78 (m, 3H). | 7 | 1133.74 |
| 332 | 1177.75 | 1179.75 | ¹H NMR (400 MHz, DMSO-d₆) δ 9.97 (br s, 1H), 8.97 (s, 1H), 8.49-8.21 (m, 1H), 7.84-7.72 (m, 2H), 7.45-7.38 (m, 1H), 7.36-7.27 (m, 1H), 7.26-7.18 (m, 4H), 7.05-6.94 (m, 3H), 6.23-6.18 (m, 1H), 4.49-4.05 (m, 7H), 3.80-3.42 (m, 20H), 3.03-2.75 (m, 3H), 2.65-2.56 (m, 1H), 2.45-2.43 (m, 3H), 2.39-2.35 (m, 2H), 2.30-2.22 (m, 2H), 2.20-2.14 (m, 2H), 2.13-2.10 (m, 1H), 2.06-1.97 (m, 1H), 1.94-1.87 (m, 1H), 1.75 (s, 1H), 1.04-0.98 (m, 3H), 0.97-0.90 (m, 3H), 0.81-0.73 (m, 3H), 0.68 (s, 1H). | 7 | 1177.79 |
| 333 | 1177.75 | 1179.75 | ¹H NMR (400 MHz, DMSO-d₆) δ 10.11 (br s, 1H), 8.97 (s, 1H), 8.42-8.26 (m, 1H), 7.81-7.75 (m, 2H), 7.46-7.39 (m, 1H), 7.37-7.07 (m, 5H), 7.06-6.95 (m, 3H), 6.27-5.74 (m, 1H), 4.60-3.99 (m, 7H), 3.88-3.43 (m, 18H), 3.43-3.39 (m, 1H), 3.03-2.78 (m, 3H), 2.65-2.56 (m, 2H), 2.46-2.41 (m, 4H), 2.40-2.35 (m, 2H), 2.30-2.23 (m, 1H), 2.21-2.18 (m, 2H), 2.14-2.11 (m, 1H), 2.08-1.97(m, 1H), 1.96-1.84 (m, 1H), 1.05-0.99 (m, 3H), 0.98-0.90 (m, 3H), 0.82-0.73 (m, 3H), 0.73-0.51 (m, 1H). | 7 | 1177.79 |
| 334 | 1221.76 | 1223.76 | ¹H NMR (400 MHz, METHANOL-d₄) δ 8.84 (s, 1H), 8.35 (br s, 1H), 7.80 (br s, 1H), 7.72 (d, J = 8.2 Hz, 1H), 7.43-7.30 (m, 2H), 7.28-7.22 (m, 2H), 7.20-7.13 (m, 1H), 7.06-6.93 (m, 3H), 6.21-6.04 (m, 114), 4.59 (br t, J = 7.8 Hz, 1H), 4.49-4.32 (m, 3H), 4.26-4.08 (m, 2H), 3.84-3.49 (m, 26H), 3.19-3.05 (m, 2H), 2.95-2.87 (m, 2H), 2.82 (br t, J = 6.7 Hz, 1H), 2.71 (br t, J = 6.6 Hz, 1H), 2.52-2.42 (m, 5H), 2.37 (br dd, J = 6.6, 15.5 Hz, 1H), 2.25-2.15 (m, 4H), 2.08-1.93 (m, 1H), 1.15 (dt, J = 2.9, 7.5 Hz, 3H), 1.04 (d, J = 6.6 Hz, 2.5H), 0.86 (d, J = 6.8 Hz, 2.5H), 0.69 (br d, J = 6.2 Hz, 0.5H), 0.49 (br d, J = 7.0 Hz, 0.5H). | 7 | 1221.84 |
| 335 | 1221.76 | 1223.76 | ¹H NMR (400 MHz, METHANOL-d₄) δ 8.84 (s, 1H), 7.79 (br s, 1H), 7.73 (br d, J = 7.8 Hz, 1H), 7.40 (br d, J = 7.9 Hz, 2H), 7.28-7.22 (m, 2H), 7.18 (br d, J = 8.1 Hz, 1H), 7.04-6.96 (m, 3H), 6.20 (s, 1H), 4.56-4.37 (m, 4H), 4.15 (br s, 2H), 3.91-3.71 (m, 11H), 3.64-3.43 (m, 15H), 3.11 (br s, 2H), 2.97-2.89 (m, 2H), 2.87-2.80 (m, 1H), 2.72 (br d, J = 7.0 Hz, 1H), 2.53-2.40 (m, 6H), 2.23 (s, 3H), 2.16 (s, 1H), 2.03 (br d, J = 8.9 Hz, 1H), 1.21-1.18 (m, 1H), 1.15 (dt, J = 3.1, 7.4 Hz, 2H), 1.02 (d, J = 6.5 Hz, 3H), 0.83 (d, J = 6.6 Hz, 3H). | 7 | 1221.84 |
| 336 | 1265.79 | 1267.8 | ¹H NMR (METHANOL-d₄) δ 8.86 (s, 1H), 7.83 (s, 1H), 7.75 (d, J = 8.8 Hz, 1H), 7.45-7.33 (m, 2H), 7.30-7.24 (m, 2H), 7.23-7.14 (m, 1H), 7.05-6.97 (m, 3H), 6.24-6.16 (m, 1H), 4.54-4.40 (m, 414), 4.18 (br s, 2H), 3.93-3.72 (m, 14H), 3.66-3.51 (m, 16H), 3.13-2.91 (m, 3H), 2.84 (br t, J = 6.8 Hz, 1H), 2.75 (br t, J = 6.8 Hz, 1H), 2.52-2.46 (m, 5H), 2.43-2.35 (m, 1H), 2.28-2.18 (m, 5H), 2.12-2.02 (m, 1H), 1.17 (dt, J = 1.6, 7.2 Hz, 3H), 1.07-1.02 (m, 3H), 0.87 (dd, J = 6.8, 12.0 Hz, 3H). | 7 | 1265.89 |
| 337 | 1087.79 | 1089.8 | ¹H NMR (400 MHz, METHANOL-d₄) δ 8.93-8.81 (m, 1H), 8.45 (s, 1H), 7.86-7.69 (m, 2H), 7.45-7.08 (m, 6H), 7.05-6.92 (m, 2H), 6.84 (dd, J = 10.7, 16.6 Hz, 1H), 6.29 ( d, J = 17.1 Hz, 1H), 6.18-6.06 (m, 111), 5.82 (dd, J = 2.1, 10.5 Hz, 1H), 4.17-4.09 (m, 1H), 4.69-3.97 (m, 5H), 3.95-3.61 (m, 16H), 3.17-3.00 (m, 2H), 2.90 ( s, 1H), 2.51-2.37 (m, 4H), 2.24-1.87 (m, 6H), 1.09-1.02 (m, 2.5H), 0.92-0.84 (m, 2.5H), 0.64-0.61(m, 0.5H), 0.42-0.35 (m, 0.5H). | 7 | 1087.67 |
| 338 | 1087.8 1087.79 | 189.8 1089.8 | ¹H NMR (400 MHz, METHANOL-d₄) δ 8.96-8.85 (m, 1H), 8.39 (s, 1H), 7.87-7.64 (m, 2H), 7.48-7.09 (m, 6H), 7.06-6.93 (m, 2H), 6.83 (dd, J = 10.8, 16.5 Hz, 1H), 6.36-6.18 (m, 2H), 5.88-5.78 (m, 1H), 4.67-4.05 (m, 5H), 3.99-3.70 (m, 14H), 3.66-3.48 (m, 2H), 3.43-3.35 (m, 2H), 3.07-2.84 (m, 2H), 2.54-2.35 (m, 4H), 2.25 (s, 3H), 2.21-1.92 (m, 3H), 1.08-0.96 (m, 3H), 0.92-0.78 (m, 3H). | 7 | 1087.67 |
| 339 | 1131.69 | 1133.69 | ¹H NMR (400 MHz, DMSO-d₆) δ 9.98 (br s, 1H), 8.97 (s, 1H), 8.30-8.21 (m, 1H), 7.79 (br d, J = 7.9 Hz, 2H), 7.52-7.34 (m, 1H), 7.32-6.94 (m, 8H), 6.89-6.79 (m, 1H), 6.24-6.14 (m, 2H), 5.74 (br d, J = 10.6 Hz, 1H), 5.11 (br s, 1H), 4.55-4.15 (m, 6H), 3.93-3.76 (m, 11H), 3.66-3.49 (m, 6H), 3.03-2.70 (m, 4H), 2.65-2.55 (m, 4H), 2.47-2.39 (m, 311), 2.30-2.03 (m, 1H), 2.15-2.12 (m, 2H), 2.07-2.00 (m, 1H), 1.91 (br dd, J = 5.1, 7.6 Hz, 1H), 0.97 (d, J = 6.6 Hz, 2H), 0.80 (d, J = 6.7 Hz, 2H), 0.68 (d, J = 6.5 Hz, 1H), 0.56 (br d, .1 = 6.4 Hz, 1H). | 7 | 1131.72 |
| 340 | 1131.69 | 1133.69 | ¹H NMR (400 MHz, DMSO-d₆) δ 10.01 (br s, 1H), 8.97 (s, 1H), 8.33 (br s, 1H), 7.79 (br d, J = 6.0 Hz, 2H), 7.46-7.38 (m, 1H), 7.34 (br d, J = 7.8 Hz, 1H), 7.29-7.17 (m, 4H), 7.11-6.95 (m, 3H), 6.84 (br dd, J = 10.5, 16.7 Hz, 1H), 6.24-6.14 (m, 2H), 5.74 (br d, J = 10.6 Hz, 1H), 5.08 (br s, 1H), 4.48-4.12 (m, 6H), 3.88-3.72 (m, 12H), 3.60-3.50 (m, 5H), 3.22-2.83 (m, 4H), 2.71-2.57 (m, 3H), 2.47-2.41 (m, 3H), 2.30-2.27 (m, 1H), 2.25-2.19 (m, 2H), 2.15-2.09 (m, 2H), 2.07-1.99 (m, 1H), 1.97-1.84 (m, 1H), 0.99-0.88 (m, 3H), 0.81-0.72 (m, 3H). | 7 | 1131.72 |
| 341 | 1175.7 | 1177.7 | ¹H NMR (400 MHz, DMSO-d₆) δ 10.07 (br s, 1H), 8.96 (d, J = 2.4 Hz, 1H), 8.33-8.20 (m, 1H), 8.14-7.99 (m, 1H), 7.96-7.69 (m, 2H), 7.50-7.40 (m, 1H), 7.33-7.20 (m, 4H), 7.09-6.95 (m, 3H), 6.87-6.73 (m, 1H), 6.24-6.13 (m, 2H), 5.80-5.71 (m, 1H), 5.35-4.77 (m, 1H), 4.49-4.43 (m, 1H), 4.40-4.09 (m, 10H), 3.65-3.36 (m, 16H), | 7 | 1175.77 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | 3.02-2.81 (m, 3H), 2.75-2.69 (m, 1H), 2.46-2.44 (m, 4H), 2.31-2.21 (m, 2H), 2.19 (s, 1H), 2.15-2.02 (m, 4H), 1.95-1.85 (m, 1H), 0.96 (d, J = 6.8 Hz, 2.5H), 0.80 (d, J = 6.8 Hz, 2.5H), 0.69 (d, J = 6.8 Hz, 0.5H), 0.57 (br d, J = 6.8 Hz, 0.5H). | | |
| 342 | 1175.72 | 1177.72 | $^1$H NMR (400 MHz, DMSO-d$_6$) δ 10.00 (br s, 1H), 8.96 (s, 1H), 8.37-8.28 (m, 1H), 8.24 (s, 1H), 7.83-7.75 (m, 2H), 7.45-7.38 (m, 1H), 7.37-7.31 (m, 1H), 7.28-7.25 (m, 1H), 7.23-7.18 (m, 2H), 7.13-6.96 (m, 4H), 6.89-6.76 (m, 1H), 6.25-6.11 (m, 2H), 5.78-5.69 (m, 1H), 5.20-4.98 (m, 1H), 4.43-4.30 (m, 2H), 4.28-4.22 (m, 2H), 4.19-4.06 (m, 2H), 3.87-3.42 (m, 18H), 3.41-3.38 (m, 2H), 3.02-2.76 (m, 3H), 2.63-2.57 (m, 1H), 2.46-2.40 (m, 5H), 2.29-2.22 (m, 1H), 2.19 (s, 3H), 2.14-1.99 (m, 2H), 1.96-1.87 (m, 1H), 0.98-0.90 (m, 3H), 0.79-0.72 (m, 3H). | 7 | 1175.77 |
| 343 | 1219.75 | 1221.75 | $^1$H NMR (400 MHz, DMSO-d$_6$) δ 10.19-9.90 (m, 1H), 9.00-8.71 (m, 1H), 8.41 (s, 1H), 8.26 (br s, 1H), 7.85-7.74 (m, 2H), 7.42 (br s, 1H), 7.32-7.20 (m, 4H), 7.08-6.94 (m, 3H), 6.88-6.78 (m, 1H), 6.25-6.12 (m, 2H), 5.73 (br d, J = 10.5 Hz, 1H), 5.20-4.88 (m, 1H), 4.53-4.10 (m, 8H), 3.86-3.66 (m, 10H), 3.61-3.43 (m, 17H), 3.08-2.76 (m, 3H), 2.26 (br d, J = 7.6 Hz, 2H), 2.12 (s, 3H), 2.14-2.09 (m, 1H), 1.95-1.85 (m, 1H), 1.06 (t, J = 7.0 Hz, 2H), 0.97 (br d, J = 6.7 Hz, 2.5H), 0.80 (br d, J = 6.7 Hz, 2.5H), 0.68 (br d, J = 6.8 Hz, 0.5H), 0.56 (br d, J = 6.7 Hz, 0.5H). | 7 | 1219.83 |
| 344 | 1219.75 | 1221.75 | $^1$H NMR (400 MHz, DMSO-d$_6$) δ 10.13-9.86 (m, 1H), 8.96 (s, 1H), 8.39-8.27 (m, 2H), 7.83-7.76 (m, 2H), 7.45-7.32 (m, 2H), 7.24 (br d, J = 18.1 Hz, 3H), 7.14-6.96 (m, 4H), 6.89-6.78 (m, 1H), 6.26-6.10 (m, 2H), 5.73 (br d, J = 9.8 Hz, 1H), 5.09 (br s, 1H), 4.45-4.11 (m, 7H), 3.74 (br d, J = 10.1 Hz, 10H), 3.61-3.41 (m, 17H), 3.01-2.77 (m, 3H), 2.27 (br s, 2H), 2.19 (s, 3H), 2.13-1.99 (m, 3H), 1.93 (br d, J = 8.3 Hz, 1H), 0.93 (br d, J = 6.5 Hz, 3H), 0.76 (br d, J = 6.2 Hz, 3H). | 7 | 1219.83 |
| 345 | 1263.79 | 1265.79 | $^1$H NMR (400 MHz, DMSO-d$_6$) δ 8.97 (s, 1H), 8.48-8.20 (m, 1H), 7.88-7.73 (m, 2H), 7.43 (br d, J = 4.0 Hz, 1H), 7.35-6.92 (m, 8H), 6.84 (dd, J = 10.8, 16.3 Hz, 1H), 6.30-6.04 (m, 2H), 5.74 (br d, J = 10.4 Hz, 1H), 4.54-4.11 (m, 6H), 3.90-3.66 (m, 10H), 3.62-3.44 (m, 18H), 3.02-2.75 (m, 3H), 2.71-2.56 (m, 3H), 2.48-2.43 (m, 4H), 2.36-2.22 (m, 2H), 2.20 (s, 1H), 2.13 (s, 2H), 2.10-2.02 (m, 1H), 1.98-1.87 (m, 1H), 0.97 (d, J = 6.8 Hz, 2.5H), 0.81 (d, J = 6.8 Hz, 2.5H), 0.69 (d, J = 6.8 Hz, 0.5H), 0.57 (d, J = 6.4 Hz, 0.5H). | 7 | 1263.88 |
| 346 | 1263.79 | 1265.79 | $^1$H NMR (400 MHz, DMSO-d$_6$) δ 8.97 (s, 1H), 8.47-8.23 (m, 2H), 7.87-7.71 (m, 2H), 7.47-7.39 (m, 1H), 7.35 (d, J = 7.8 Hz, 1H), 7.31-7.15 (m, 4H), 7.06-6.98 (m, 3H), 6.84 (dd, J = 10.8, 16.2 Hz, 1H), 6.32-6.06 (m, 2H), 5.74 (br d, J = 10.8 Hz, 1H), 4.43-4.15 (m, 6H), 3.88-3.69 (m, 11H), 3.63-3.45 (m, 17H), 3.01-2.79 (m, 3H), 2.72-2.57 (m, 3H), 2.47-2.42 (m, 4H), 2.36-2.23 (m, 2H), 2.20 (s, 3H), 2.15-2.01 (m, 2H), 1.98-1.88 (m, 1H), 0.98-0.89 (m, 3H), 0.77 (br d, J = 6.8 Hz, 3H). | 7 | 1263.88 |
| 347 | 1043.74 | 1045.74 | $^1$H NMR (400 MHz, METHANOL-d$_4$) δ 8.90-8.79 (m, 1H), 7.74-7.56 (m, 1H), 7.38-7.24 (m, 2H), 7.02-6.87 (m, 2H), 6.82-6.65 (m, 2H), 6.24-6.17 (m, 1H), 4.58-4.08 (m, 7H), 3.96-3.47 (m, 15H), 3.04 (s, 1H), 2.92-2.76 (m, 1H), 2.48-2.36 (m, 4H), 2.24-2.00 (m, 8H), 1.04-0.96 (m, 3H), 0.88-0.79 (m, 3H). | 7 | 1043.59 |
| 348 | 1087.78 | 1089.78 | $^1$H NMR (400 MHz, CD$_3$OD) δ 8.90-8.79 (m, 1H), 7.77-7.50 (m, 1H), 7.29 (br dd, J = 7.0, 13.3 Hz, 2H), 7.00-6.92 (m, 1H), 6.86-6.64 (m, 3H), 6.19 (d, J = 2.2 Hz, 1H), 4.50-4.28 (m, 3H), 4.18-4.00 (m, 2H), 3.89-3.83 (m, 1H), 3.80-3.62 (m, 18H), 3.12 (s, 2H), 2.97-2.92 (m, 2H), 2.88-2.65 (m, 4H), 2.48-2.33 (m, 5H), 2.21 (s, 1H), 2.19-2.12 (m, 7H), 2.19-2.12 (m, 1H), 1.04 (dd, J = 3.5, 6.7 Hz, 1H), 0.86 (d, J = 6.6 Hz, 1H). | 7 | 1087.64 |
| 349 | 1087.78 | 1089.78 | $^1$H NMR (400 MHz, CD$_3$OD) δ 8.84 (d, J = 2.6 Hz, 1H), 7.77-7.54 (m, 1H), 7.29 (br d, J = 4.5 Hz, 2H), 7.03-6.96 (m, 1H), 6.94-6.81 (m, 1H), 6.80-6.80 (m, 1H), 6.75-6.74 (m, 1H), 6.80-6.65 (m, 2H), 6.21 (s, 1H), 4.48-4.34 (m, 2H), 4.21-4.02 (m, 2H), 3.94-3.84 (m, 2H), 3.12 (s, 1H), 2.95 (s, 2H), 2.88-2.63 (m, 3H), 2.48-2.42 (m, 3H), 2.27-2.11 (m, 6H), 1.02 (dd, J = 2.5, 6.3 Hz, 1H), 0.89-0.77 (m, 1H). | 7 | 1087.64 |
| 350 | 1131.82 | 1133.82 | $^1$H NMR (400 MHz, METHANOL-d$_4$) δ 8.84 (d, J = 2.8 Hz, 1H), 7.70-7.65 (m, 1H), 7.38 (dd, J = 4.0, 7.6 Hz, 1H), 7.31-7.24 (m, 1H), 6.97 (br dd, J = 8.8, 17.6 Hz, 2H), 6.75 (d, J = 8.4 Hz, 1H), 6.69 (t, J = 8.8 Hz, 1H), 6.21 (s, 1H), 4.57-4.38 (m, 4H), 4.16 (m, 1H), 4.05 (br s, 1H), 3.94-3.44 (m, 26H), 3.10 (br s, 1H), 2.92 (s, 2H), 2.83 (m, 1H), 2.71 (m, 1H), 2.48-2.35 (m, 4H), 2.24 (s, 3H), 2.19-1.98 (m, 6H), 1.02 (d, J = 6.4 Hz, 3H), 0.84 (d, J = 6.4 Hz, 3H). | 7 | 1131.69 |
| 351 | 1175.85 | 1177.85 | $^1$H NMR (400 MHz, METHANOL-d$_4$) δ 8.84 (s, 1H), 7.70 (br s, 1H), 7.40 (d, J = 8.0 Hz, 1H), 7.32-7.24 (m, 1H), 7.03-6.97 (m, 2H), 6.76 (d, J = 8.4 Hz, 1H), 6.69 (t, J = 8.4 Hz, 1H), 6.22-5.93 (m, 1H), 4.59-4.36 (m, 5H), 4.21-4.12 (m, 2H), 3.91-3.46 (m, 30H), 3.11 (br s, 1H), 2.92 (s, 2H), 2.81 (m, 1H), 2.71 (m, 1H), 2.48-2.44 (m, 3H), 2.39 (m, 1H), 2.25-2.01 (m, 9H), 1.02 (d, J = 6.4 Hz, 3H), 0.84 (d, J = 6.8 Hz, 3H). | 7 | 1175.74 |
| 352 | 1219.88 | 1221.88 | $^1$H NMR (400 MHz, METHANOL-d$_4$) δ 8.85 (s, 1H), 7.74 (br s, 1H), 7.41 (d, J = 8.0 Hz, 1H), 7.36-7.24 (m, 1H), 7.06-6.96 (m, 2H), 6.76 (d, J = 8.4 Hz, 1H), 6.70 (t, J = 8.8 Hz, 1H), 6.21 (s, 1H), 4.57-4.40 (m, 4H), 4.19 (br s, 2H), 3.88-3.48 (m, 30H), 3.12 (br s, 1H), 2.92 (s, 2H), 2.82 (br t, J = 6.8 Hz, 1H), 2.73 (br t, J = 6.8 Hz, 1H), 2.51-2.44 (m, 3H), 2.43-2.33 (m, 1H), 2.24 (s, 3H), 2.20-1.98 (m, 6H), 1.02 (d, J = 6.4 Hz, 3H), 0.84 (d, J = 6.4 Hz, 3H). | 7 | 1219.80 |
| 353 | 1044.74 | 1046.74 | $^1$H NMR (400 MHz, METHANOL-d$_4$) δ 8.88-8.80 (m, 1H), 7.72-7.58 (m, 1H), 7.40-7.25 (m, 2H), 7.02-6.65 (m, 4H), 6.22-6.18 (m, 1H), 4.55-4.12 (m, 6H), 4.03-3.51 (m, 15H), 3.04 (s, 1H), 2.92-2.77 (m, 1H), 2.48-2.34 (m, 4H), 2.25-2.03 (m, 5H), 1.04-0.96 (m, 3H), 0.87-0.79 (m, 3H). | 7 | 1044.57 |
| 354 | 1088.78 | 1090.78 | $^1$H NMR (400 MHz, METHANOL-d$_4$) δ 8.83 (d, J = 2.8 Hz, 1H), 7.76-7.55 (m, 1H), 7.41-7.24 (m, 2H), 7.03-6.96 (m, 1H), 6.84 (br s, 1H), 6.80-6.65 (m, 2H), 6.21 (d, | 7 | 1088.63 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | J = 1.2 Hz, 1H), 4.58-4.31 (m, 4H), 4.15 (br s, 1H), 4.08 (br s, 1H), 3.92-3.54 (m, 20H), 3.12 (s, 1H), 2.95 (s, 2H), 2.89-2.66 (m, 2H), 2.47-2.36 (m, 4H), 2.25-2.03 (m, 5H), 1.03 (br d, J = 5.2 Hz, 3H), 0.84 (dd, J = 2.8, 6.8 Hz, 3H). | | |
| 355 | 1132.81 | 1134.81 | $^1$H NMR (400 MHz, METHANOL-d$_4$) δ 8.83 (d, J = 2.0 Hz, 1H), 7.66 (br d, J = 8.8 Hz, 1H), 7.37 (dd, J = 4.4, 7.6 Hz, 1H), 7.28 (q, J = 7.2 Hz, 1H), 7.03-6.91 (m, 2H), 6.75 (d, J = 8.0 Hz, 1H), 6.68 (t, J = 8.8 Hz, 1H), 6.24-5.96 (m, 1H), 4.55-4.40 (m, 4H), 4.20-4.12 (m, 1H), 4.05 (br s, 1H), 3.92-3.47 (m, 24H), 3.10 (br s, 1H), 2.92 (s, 2H), 2.82(m, 1H), 2.70 (m, 1H), 2.47-2.34 (m, 4H), 2.25-2.00 (m, 5H), 1.03 (d, J = 6.4 Hz, 3H), 0.84 (d, J = 6.8 Hz, 3H). | 7 | 1132.68 |
| 356 | 1176.85 | 1178.85 | $^1$H NMR (400 MHz, METHANOL-d$_4$) δ 8.83 (s, 1H), 7.69 (br s, 1H), 7.40 (d, J = 7.6 Hz, 1H), 7.28 (q, J = 8.0 Hz, 1H), 7.03-6.97 (m, 2H), 6.76 (d, J = 8.0 Hz, 1H), 6.68 (t, J = 8.4 Hz, 1H), 6.23-5.93 (m, 1H), 4.56-4.36 (m, 4H), 4.16 (br s, 2H), 3.90-3.48 (m, 28H), 3.10 (br s, 1H), 2.91 (s, 2H), 2.81 (m, 1H), 2.70 (m, 1H), 2.48-2.33 (m, 4H), 2.26-1.97 (m, 5H), 1.02 (d, J = 6.4 Hz, 3H), 0.84 (d, J = 6.8 Hz, 3H). | 7 | 1176.73 |
| 357 | 1220.88 | 1222.89 | $^1$H NMR (400 MHz, METHANOL-d$_4$) δ 8.85 (s, 1H), 7.73 (br s, 1H), 7.41 (d, J = 7.2 Hz, 1H), 7.35-7.23 (m, 1H), 7.05-6.95 (m, 2H), 6.76 (d, J = 8.4 Hz, 1H), 6.69 (t, J = 8.8 Hz, 1H), 6.21 (s, 1H), 4.56-4.38 (m, 4H), 4.18 (br d, J = 4.0 Hz, 2H), 3.91-3.48 (m, 31H), 3.11 (br s, 1H), 2.92 (s, 2H), 2.82 (t, J = 6.8 Hz, 1H), 2.73 (br t, J = 6.4 Hz, 1H), 2.51-2.34 (m, 4H), 2.26-2.00 (m, 5H), 1.03 (d, J = 6.8 Hz, 3H), 0.84 (d, J = 6.8 Hz, 3H). | 7 | 1220.79 |
| 358 | 1076.78 | 1078.78 | $^1$H NMR (400 MHz, DMSO-d$_6$) δ 8.96 (s, 1H), 8.28 (brs, 1H), 8.18 (s, 1H), 7.84-7.70 (m, 2H), 7.49-7.09 (m, 6H), 7.08-6.87 (m, 3H), 6.24-6.02 (m, 3H), 4.54-4.03 (m, 7H), 3.95-3.50 (m, 4H), 3.29-3.17 (m, 4H), 3.14-3.01 (m, 3H), 2.91-2.58 (m, 6H), 2.46-1.95 (m, 11H), 1.93-1.80 (m, 1H), 0.99-0.44 (m, 6H). | 7 | 1076.64 |
| 359 | 1120.81 | 1122.81 | $^1$H NMR (400 MHz, CD$_3$OD) δ 8.96-8.86 (m, 1H), 8.15-7.81 (m, 1H), 7.80-7.71 (m, 1H), 7.49-7.38 (m, 1H), 7.35-7.16 (m, 4H), 7.13-6.61 (m, 3H), 6.23-6.06 (m, 1H), 4.72-4.12 (m, 10H), 3.90-3.51 (m, 15H), 3.18-3.03 (m, 1H), 3.00-2.93 (m, 2H), 2.92-2.63 (m, 2H), 2.49-2.03 (m, 9H), 1.10-0.72 (m, 6H). | 7 | 1120.70 |
| 360 | 1164.85 | 1166.86 | $^1$H NMR (400 MHz, DMSO-d$_6$) δ 8.97 (d, J = 3.6 Hz, 1H), 8.32 (t, J = 5.6 Hz, 1H), 8.10 (s, 1H), 8.05-7.95 (m, 1H), 7.82 (d, J = 8.4 Hz, 1H), 7.47-7.45 (m, 1H), 7.34-7.24 (m, 4H), 7.09 (s, 1H), 7.03-6.96 (m, 2H), 6.22-6.10 (m, 3H), 4.51-4.10 (m, 12H), 3.86-3.60 (m, 13H), 2.97 (s, 2H), 2.85 (s, 2H), 2.78-2.65 (m, 3H), 2.46-2.44 (m, 4H), 2.31-2.25 (m, 1H), 2.20 (s, 1H), 2.15-1.98 (m, 4H), 1.93-1.87 (m, 1H), 0.96, 0.68 (d, J = 6.4 Hz, 3H), 0.79, 0.57 (d, J = 6.8 Hz, 3H). | 7 | 1164.75 |
| 361 | 1208.89 | 1210.89 | $^1$H NMR (400 MHz, DMSO-d$_6$) δ 8.97 (s, 1H), 8.32 (t, J = 5.6 Hz, 1H), 8.17-7.90 (m, 2H), 7.82 (d, J = 8.4 Hz, 1H), 7.52-7.41 (m, 1H), 7.37-7.16 (m, 4H), 7.12-6.92 (m, 3H), 6.39-5.77 (m, 3H), 4.50-4.08 (m, 11H), 3.86-3.72 (m, 8H), 3.53-3.47 (m, 13H), 3.09-2.82 (m, 4H), 2.74-2.63 (m, 2H), 2.48-2.40 (m, 4H), 2.36-2.01 (m, 5H), 1.96-1.83 (m, 1H), 1.04-0.44 (m, 6H). | 7 | 1208.80 |
| 362 | 1252.91 | 1254.91 | $^1$H NMR (400 MHz, CD$_3$OD) δ 9.02-8.79 (m, 1H), 8.18-7.99 (m, 1H), 7.76 (d, J = 8.4 Hz, 1H), 7.47-7.26 (m, 3H), 7.26-7.16 (m, 2H), 7.13-6.90 (m, 3H), 6.25-6.02 (m, 1H), 4.66-4.09 (m, 10H), 4.05-3.43 (m, 27H), 3.20-2.72 (m, 5H), 2.54-1.99 (m, 9H), 1.11-0.47 (m, 6H). | 7 | 1252.86 |
| 363 | 1105.85 | 1107.85 | $^1$H NMR (400 MHz, DMSO-d$_6$ + D$_2$O) δ 9.03-8.85 (m, 1H), 8.45 (br d, J = 7.2 Hz, 1H), 8.30 (br s, 1H), 7.89-7.72 (m, 2H), 7.46-7.15 (m, 9H), 7.02 (br s, 1H), 6.83-6.51 (m, 1H), 4.93-4.69 (m, 1H), 4.52 (br d, J = 9.6 Hz, 1H), 4.42 (br t, J = 8.0 Hz, 1H), 4.27 (br s, 1H), 3.97-3.89 (m, 2H), 3.69-3.46 (m, 8H), 3.26 (s, 1H), 2.94 (br s, 3H), 2.77 (br s, 3H), 2.59 (br t, J = 7.2 Hz, 2H), 2.44-2.37 (m, 4H), 2.13-2.00 (m, 1H), 1.76 (br d, J = 13.2 Hz, 1H), 1.49-1.22 (m, 3H), 0.84 (br s, 9H). | 8 | 1105.73 |
| 364 | 1149.87 | 1151.88 | $^1$H NMR (400 MHz, METHANOL-d$_4$) δ 9.00-8.85 (m, 1H), 8.14 (s, 1H), 7.79 (d, J = 8.4 Hz, 1H), 7.67 (br d, J = 9.4 Hz, 1H), 7.44 (s, 4H), 7.32 (d, J = 2.3 Hz, 1H), 7.25 (br s, 2H), 7.07 (d, J = 2.4 Hz, 1H), 7.00-6.91 (m, 1H), 6.65-6.54 (m, 1H), 5.06-4.95 (m, 4H), 4.74-4.68 (m, 1H), 4.62-4.52 (m, 1H), 4.45 (br s, 1H), 4.36 (br s, 3H), 4.08 (d, J = 3.3 Hz, 2H), 4.04-3.82 (m, 6H), 3.79-3.67 (m, 6H), 3.07 (s, 3H), (s, 2.97 3H), 2.81 (br s, 2H), 2.71-2.56 (m, 2H), 2.52-2.43 (m, 3H), 2.27-2.18 (m, 1H), 2.06-1.93 (m, 1H), 1.60-1.50 (m, 3H), 1.09-1.06 (m, 9H). | 8 | 1149.78 |
| 365 | 1193.91 | 1195.92 | $^1$H NMR (400 MHz, DMSO-d$_6$) δ 8.96 (s, 1H), 8.41 (d, J = 7.6 Hz, 1H), 8.32 (s, 1H), 7.79-7.78 (m, 2H), 7.43-7.41 (m, 7H), 7.37-7.35 (m, 1H), 7.26-7.22 (m, 2H), 7.20-7.15 (m, 1H), 7.04-7.03 (m, 1H), 6.75-6.71 (m, 1H), 6.59-6.53 (m, 1H), 4.92-4.88 (m, 1H), 4.56-4.54 (m, 1H), 4.44-4.40 (m, 1H), 4.25 (s, 1H), 3.96 (s, 2H), 3.79-3.59 (m, 7H), 3.58-3.54 (m, 15H), 2.97 (s, 3H), 2.79 (s, 3H), 2.60-2.58 (m, 2H), 2.46-2.44 (m, 5H), 2.04-2.02 (m, 1H), 1.77-1.75 (m, 1H), 1.38-1.36 (m, 3H), 0.94 (s, 9H). | 8 | 1193.83 |
| 366 | 1237.95 | 1239.95 | $^1$H NMR (400 MHz, DMSO-d$_6$) δ 10.03 (brs, 1H), 8.98 (s, 1H), 8.45 (d, J = 7.6 Hz, 1H), 7.81-7.76 (m, 2H), 7.45-7.33 (m, 6H), 7.30-7.10 (m, 4H), 7.05 (d, J = 1.2 Hz, 1H), 6.76-6.69 (m, 1H), 6.58 (d, J = 14.8 Hz, 1H), 5.15 (d, J = 3.2 Hz, 1H), 4.93-4.89 (m, 1H), 4.55 (d, J = 9.2 Hz, 1H), 4.45 (t, J = 8.4 Hz, 1H), 4.29 (s, 1H), 3.97 (s, 2H), 3.85-3.50 (m, 25H), 2.98 (s, 3H), 2.80 (s, 3H), 2.61 (t, J = 6.4 Hz, 2H), 2.48-2.40 (m, 5H), 2.08-2.03 (m, 1H), 1.81-1.74 (m, 1H), 1.38 (d, J = 6.8 Hz, 3H), 0.94 (s, 9H). | 8 | 1237.88 |
| 367 | 1281.98 | 1283.88 | $^1$H NMR (400 MHz, DMSO-d$_6$) δ 8.98 (s, 1H), 8.43 (d, J = 7.6 Hz, 1H), 8.34 (brs, 1H), 7.80 (d, J = 4.2 Hz, 2H), 7.47-7.35 (m, 6H), 7.27 (s, 1H), 7.23 (brs, 2H), 7.05 (s, 1H), 6.73 (td, J = 7.0, 14.4 Hz, 1H), | 8 | 1281.94 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | 6.64-6.54 (m, 1H), 4.91 (t, J = 7.2 Hz, 1H), 4.55 (d, J = 9.4 Hz, 1H), 4.45 (t, J = 8.0 Hz, 1H), 4.29 (brs, 1H), 4.00-3.91 (m, 2H), 3.85-3.53 (m, 33H), 2.98 (s, 3H), 2.80 (brs, 3H), 2.65-2.59 (m, 2H), 2.46 (s, 5H), 2.11-2.01 (m, 1H), 1.83-1.74 (m, 1H), 1.38 (d, J = 6.8 Hz, 3H), 0.95 (s, 9H). | | |
| 368 | 1151.89 | 1153.89 | $^1$H NMR (400 MHz, METHANOL-d$_4$) δ 8.96-8.81 (m, 1H), 8.15 (s, 1H), 7.79 (d, J = 8.2 Hz, 1H), 7.68 (br d, J = 8.9 Hz, 1H), 7.49-7.39 (m, 5H), 7.39-7.28 (m, 1H), 7.25 (br s, 2H), 7.07 (d, J = 2.0 Hz, 1H), 5.09-4.95 (m, 1H), 4.89 (s, 1H), 4.71 (br d, J = 9.4 Hz, 1H), 4.63-4.55 (m, 1H), 4.33 (br s, 4H), 4.13-4.01 (m, 2H), 3.98-3.82 (m, 6H), 3.78-3.72 (m, 3H), 3.70-3.65 (m, 2H), 3.60 (br t, J = 6.0 Hz, 2H), 3.37 (s, 1H), 3.07 (s, 3H), 2.98 (s, 3H), 2.81 (br s, 2H), 2.60-2.45 (m, 5H), 2.32-2.14 (m, 1H), 2.12-1.93 (m, 1H), 1.83-1.68 (m, 4H), 1.64-1.43 (m, 3H), 1.18-1.02 (m, 9H). | 8 | 1151.79 |
| 369 | 1195.93 | 1197.93 | $^1$H NMR (400 MHz, MeOD-d$_4$) δ 9.99 (s, 1H), 8.14 (s, 1H), 7.77 (d, J = 8.0 Hz, 1H), 7.57-7.55 (m, 4H), 7.53-7.51 (m, 1H), 7.30 (d, J = 2.0 Hz, 1H), 7.24 (d, J = 5.6 Hz, 1H), 7.06 (s, 1H), 5.03-5.02 (m, 1H), 4.60-4.56 (m, 1H), 4.43 (s, 1H), 4.35-4.32 (m, 4H), 4.10-4.01 (m, 2H), 3.90-3.84 (m, 7H), 3.76-3.59 (m, 10H), 3.56-3.49 (m, 2H), 3.07 (s, 3H), 2.96 (s, 3H), 2.83-2.80 (m, 1H), 2.61-2.60 (m, 3H), 2.55-2.51 (m, 2H), 2.24-2.19 (m, 1H), 1.97-1.91 (m, 1H), 1.76-1.66 (m, 4H), 1.58-1.51 (m, 3H), 1.05 (s, 9H). | 8 | 1195.85 |
| 370 | 1239.87 | 1241.87 | $^1$H NMR (400 MHz, DMSO-d$_6$) δ 8.98 (s, 1H), 8.43 (d, J = 7.6 Hz, 1H), 8.21 (s, 1H), 7.80 (d, J = 8.4 Hz, 2H), 7.46-7.33 (m, 6H), 7.27 (d, J = 2.4 Hz, 1H), 7.23 (d, J = 4.0 Hz, 2H), 7.18-7.08 (m, 1H), 7.05 (d, J = 2.4 Hz, 1H), 4.95-4.89 (m, 1H), 4.55 (d, J = 9.6 Hz, 1H), 4.46 (t, J = 8.0 Hz, 1H), 4.29 (s, 1H), 4.00 (s, 2H), 3.62-3.40 (m, 24H), 2.98 (s, 3H), 2.80 (s, 3H), 2.62 (t, J = 6.8 Hz, 2H), 2.46-2.34 (m, 7H), 2.08-1.99 (m, 1H), 1.82-1.75 (m, 1H), 1.60-1.50 (m, 4H), 1.38 (d, J = 6.8 Hz, 3H), 0.95 (s, 9H). | 8 | 1239.90 |
| 371 | 1283.9 | 1285.9 | $^1$H NMR (400 MHz, DMSO-d$_6$) δ 8.98 (s, 1H), 8.45-8.40 (m, 1H), 7.83-7.78 (m, 2H), 7.44 (d, J = 7.6 Hz, 3H), 7.38 (d, J = 8.4 Hz, 3H), 7.27 (s, 1H), 7.23 (d, J = 3.6 Hz, 2H), 7.05 (s, 1H), 5.13 (brs, 1H), 4.91 (t, J = 7.2 Hz, 1H), 4.55 (d, J = 9.2 Hz, 1H), 4.45 (t, J = 8.4 Hz, 1H), 4.29 (brs, 1H), 3.98-3.92 (m, 2H), 3.75-3.47 (m, 31H), 2.98 (s, 3H), 2.80 (brs, 3H), 2.70-2.59 (m, 2H), 2.46 (s, 3H), 2.42-2.34 (m, 3H), 2.10-2.01 (m, 1H), 1.78 (brs, 1H), 1.56 (brs, 4H), 1.38 (d, J = 6.8 Hz, 3H), 0.95 (s, 9H). | 8 | 1283.95 |
| 372 | 991.73 | 993.73 | $^1$H NMR (400 MHz, DMSO-d$_6$) δ 8.98 (s, 1H), 8.77-8.68 (m, 1H), 8.45-8.29 (m, 1H), 8.15-8.04 (m, 1H), 7.82 (d, J = 8.0 Hz, 1H), 7.42 (br d, J = 7.2 Hz, 3H), 7.40-7.28 (m, 4H), 7.21 (br s, 2H), 7.11 (s, 1H), 6.83-6.71 (m, 1H), 6.68-6.58 (m, 1H), 5.29-4.80 (m, 2H), 4.55 (br d, J = 9.4 Hz, 1H), 4.46 (br t, J = 8.0 Hz, 1H), 4.33-4.20 (m, 1H), 4.17-3.70 (m, 12H), 3.68-3.54 (m, 5H), 2.45 (s, 3H), 2.12-1.96 (m, 1H), 1.84-1.71 (m, 1H), 1.54-1.27 (m, 3H), 0.95 (s, 9H). | 8 | 991.58 |
| 373 | 1035.77 | 1037.77 | $^1$H NMR (400 MHz, METHANOL-d$_4$) δ 8.91 (s, 1H), 8.77-8.73 (m, 1H), 8.29 (s, 1H), 7.78 (d, J = 8.3 Hz, 1H), 7.66 (d, J = 9.7 Hz, 1H), 7.48-7.37 (m, 5H), 7.31 (d, J = 2.3 Hz, 1H), 7.22 (br s, 2H), 7.08 (d, J = 2.2 Hz, 1H), 6.98-6.88 (m, 1H), 6.63-6.52 (m, 1H), 4.99 (br d, J = 8.3 Hz, 1H), 4.69 (d, J = 9.7 Hz, 1H), 4.57 (t, J = 8.3 Hz, 1H), 4.45-4.31 (m, 5H), 4.10-3.81 (m, 7H), 3.79-3.63 (m, 7H), 2.64-2.55 (m, 5H), 2.26-1.86 (m, 2H), 1.58-1.45 (m, 3H), 1.08-0.95 (m, 9H). | 8 | 1035.63 |
| 374 | 1079.8 | 1081.8 | $^1$H NMR (400 MHz, MeOD-d$_4$) δ 8.84 (s, 1H), 8.66 (s, 1H), 8.08 (d, J = 1.2 Hz, 1H), 7.75 (d, J = 8.4 Hz, 1H), 7.42-7.38 (m, 5H), 7.27 (d, J = 2.4 Hz, 1H), 7.25-7.20 (m, 2H), 7.06 (s, 1H), 6.90-6.86 (m, 1H), 6.58-6.54 (m, 1H), 5.02-4.98 (m, 1H), 4.56-4.54 (m, 1H), 4.42 (s, 1H), 4.05-4.03 (m, 6H), 3.89-3.71 (m, 5H), 3.69-3.64 (m, 12H), 2.56-2.51 (m, 2H), 2.45 (s, 3H), 2.18-2.16 (m, 1H), 1.99-1.95 (m, 1H), 1.50-1.46 (m, 3H), 1.04 (s, 9H). | 8 | 1079.68 |
| 375 | 1123.75 | 1125.76 | $^1$H NMR (400 MHz, DMSO-d$_6$) δ 8.98 (s, 1H), 8.73 (s, 1H), 8.43 (d, J = 7.6 Hz, 1H), 8.10 (s, 1H), 7.82 (d, J = 8.4 Hz, 1H), 7.47-7.30 (m, 7H), 7.25-7.20 (m, 2H), 7.10 (d, J = 2.4 Hz, 1H), 6.79-6.71 (m, 1H), 6.58 (d, J = 15.2 Hz, 1H), 4.95-4.85 (m, 1H), 4.55 (d, J = 9.6 Hz, 1H), 4.46 (t, J = 8.0 Hz, 1H), 4.29 (s, 1H), 3.97-3.75 (m, 11H), 3.63-3.50 (m, 17H), 2.45 (s, 3H), 2.08-2.02 (m, 1H), 1.82-1.75 (m, 1H), 1.38 (d, J = 6.8 Hz, 3H), 0.95 (s, 9H). | 8 | 1123.74 |
| 376 | 1167.88 | 1169.88 | $^1$H NMR (400 MHz, DMSO-d$_6$) δ 10.13 (brs, 1H), 8.98 (s, 1H), 8.72 (s, 1H), 8.50-8.39 (m, 1H), 8.10 (s, 1H), 7.82 (d, J = 8.4 Hz, 1H), 7.48-7.29 (m, 8H), 7.25-7.19 (m, 2H), 7.10 (d, J = 2.0 Hz, 1H), 6.79-6.69 (m, 1H), 6.62-6.59 (m, 1H), 5.17 (brs, 1H), 4.90 (t, J = 6.8 Hz, 1H), 4.54 (d, J = 9.6 Hz, 1H), 4.44 (t, J = 8.0 Hz, 1H), 4.28 (brs, 1H), 4.02-3.71 (m, 10H), 3.67-3.49 (m, 19H), 2.45 (s, 6H), 2.11-2.00 (m, 1H), 1.82-1.71 (m, 1H), 1.37 (d, J = 6.8 Hz, 3H), 0.94 (s, 9H). | 8 | 1167.79 |
| 377 | 993.75 | 995.75 | $^1$H NMR (400 MHz, DMSO-d$_6$) δ 8.98 (s, 1H), 8.77-8.68 (m, 1H), 8.46-8.37 (m, 1H), 8.11-8.04 (m, 1H), 7.82 (d, J = 8.4 Hz, 1H), 7.48-7.40 (m, 3H), 7.38-7.30 (m, 4H), 7.22 (d, J = 3.2 Hz, 2H), 7.11 (d, J = 2.4 Hz, 1H), 5.26-4.81 (m, 2H), 4.56 (d, J = 9.6 Hz, 1H), 4.50-4.43 (m, 1H), 4.29 (br s, 1H), 4.01-3.86 (m, 6H), 3.78-3.68 (m, 4H), 3.64-3.49 (m, 5H), 2.45 (s, 5H), 2.12-1.99 (m, 1H), 1.78 (ddd, J = 4.4, 8.4, 13.2 Hz, 1H), 1.62 (br s, 4H), 1.49-1.34 (m, 3H), 0.95 (s, 9H). | 8 | 993.59 |
| 378 | 1037.78 | 1039.78 | $^1$H NMR (400 MHz, METHANOL-d$_4$) δ 8.94-8.88 (m, 1H), 8.77-8.72 (m, 1H), 8.30 (s, 1H), 7.77 (d, J = 8.4 Hz, 1H), 7.65 (d, J = 9.5 Hz, 1H), 7.48-7.38 (m, 5H), 7.35-7.28 (m, 1H), 7.22 (br s, 2H), 7.10-7.04 (m, 1H), 5.05-4.94 (m, 1H), 4.69 (d, J = 9.5 Hz, 1H), 4.55 (t, J = 8.5 Hz, 1H), 4.40 (br d, J = 14.2 Hz, 4H), 4.06 (d, J = 1.8 Hz, 2H), 3.90 (br s, 4H), 3.79-3.69 (m, 4H), 3.67-3.62 (m, 2H), 3.62-3.53 (m, 2H), 2.58-2.41 (m, 5H), 2.20-2.18 (m, 1H), 2.04-1.89 (m, 1H), 1.81-1.66 (m, 4H), 1.58-1.45 (m, 3H), 1.08-1.02 (m, 9H). | 8 | 1037.65 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| 379 | 1081.82 | 1083.82 | $^1$H NMR (400 MHz, MeOD) δ 8.84 (d, J = 3.6 Hz, 1H), 8.66 (s, 1H), 8.53 (s, 1H), 8.07 (s, 1H), 7.75 (d, J = 8.4 Hz, 1H), 7.42-7.38 (m, 5H), 7.28 (d, J = 2.4 Hz, 1H), 7.20-7.18 (m, 1H), 7.07 (d, J = 8.4 Hz, 1H), 5.04-4.98 (m, 1H), 4.68 (s, 1H), 4.58-4.55 (m, 1H), 4.43 (s, 1H), 4.05-4.04 (m, 6H), 3.81-3.75 (m, 5H), 3.71-3.66 (m, 7H), 3.63-3.62 (m, 2H), 3.53-3.49 (m, 2H), 2.51-2.48 (m, 2H), 2.45 (s, 3H), 2.25-2.15 m, 1H), 1.96-1.91 (m, 1H), 1.73-1.66 (m, 4H), 1.64-1.49 (m, 3H), 1.04-1.02 (m, 9H). | 8 | 1081.70 |
| 380 | 1125.77 | 1127.77 | $^1$H NMR (400 MHz, DMSO-d$_6$) δ 10.09 (brs, 1H), 8.98 (s, 1H), 8.72 (s, 1H), 8.45 (d, J = 8.0 Hz, 1H), 8.09 (s, 1H), 7.82 (d, J = 8.4 Hz, 1H), 7.46-7.30 (m, 7H), 7.25-7.19 (m, 2H), 7.11 (d, J = 2.0 Hz, 1H), 5.14 (d, J = 2.8 Hz, 1H), 4.95-4.86 (m, 1H), 4.55 (d, J = 9.6 Hz, 1H), 4.45 (t, J = 8.0 Hz, 1H), 4.29 (s, 1H), 4.00-3.85 (m, 6H), 3.77-3.65 (m, 4H), 3.64-3.45 (m, 14H), 3.42 (t, J = 6.0 Hz, 2H), 2.45 (s, 3H), 2.40 (t, J = 6.8 Hz, 2H), 2.09-2.02 (m, 1H), 1.81-1.74 (m, H1), 1.62-1.50 (m, 4H), 1.38 (d, J = 6.8 Hz, 3H), 0.94 (s, 9H). | 8 | 1125.75 |
| 381 | 1169.9 | 1171.9 | $^1$H NMR (400 MHz, DMSO-d$_6$) δ 8.97 (s, 1H), 8.72 (s, 1H), 8.44 (d, J = 7.6 Hz, 1H), 8.09 (s, 1H), 7.82 (d, J = 8.4 Hz, 1H), 7.47-7.35 (m, 6H), 7.31 (d, J = 2.0 Hz, 1H), 7.21 (brs, 2H), 7.11 (d, J = 2.0 Hz, 1H), 4.91 (t, J = 7.2 Hz, 1H), 4.55 (d, J = 9.6 Hz, 1H), 4.45 (t, J = 8.0 Hz, 1H), 4.29 (brs, 1H), 3.99-3.87 (m, 6H), 3.72 (brs, 4H), 3.64-3.50 (m, 22H), 2.45 (s, 5H), 2.10-2.02 (m, 1H), 1.72-1.80 (m, 1H), 1.56 (brs, 4H), 1.38 (d, J = 7.2 Hz, 3H), 0.94 (s, 9H). | 8 | 1169.81 |
| 382 | 1105.8 | 1107.8 | $^1$H NMR (DMSO-d$_6$) δ 9.02-8.93 (m, 1H), 8.32-8.23 (m, 1H), 7.83-7.72 (m, 2H), 7.46-7.38 (m, 1H), 7.36-6.94 (m, 9H), 6.18-6.02 (m, 1H), 5.26-4.93 (m, 2H), 4.56-4.40 (m, 1H), 4.25 (br s, 3H), 4.08-3.49 (m, 19H), 3.09-2.98 (m, 2H), 2.70-2.61 (m, 2H), 2.25-1.86 (m, 7H), 1.83-1.69 (m, 1H), 1.38-1.22 (m, 3H), 1.01-0.66 (m, 7H). | 9 | 1105.68 |
| 383 | 1105.8 | 1107.8 | $^1$H NMR (DMSO-d$_6$) δ 8.99 (s, 1H), 8.37 (d, J = 6.4 Hz, 1H), 7.84-7.73 (m, 2H), 7.45-6.95 (m, 10H), 6.13-5.99 (m, 1H), 5.22-5.08 (m, 1H), 4.39 (t, J = 7.6 Hz, 1H), 4.27 (s, 3H), 3.89-3.50 (m, 19H), 3.05 (s, 2H), 2.66 (d, J = 1 4.8 Hz, 2H), 2.28-1.98 (m, 7H), 1.78 (s, 1H), 1.37-1.25 (m, 3H), 0.98-0.70 (m, 7H). | 9 | 1105.68 |
| 384 | 1149.84 | 1151.84 | $^1$H NMR (400 MHz, DMSO-d$_6$) δ 10.02 (s, 1H), 9.06-8.92 (m, 1H), 8.37-8.23 (m, 1H), 7.86-7.72 (m, 2H), 7.49-6.95 (m, 10H), 6.15-6.01 (m, 1H), 5.25-5.05 (m, 2H), 4.59-4.40 (m, 1H), 4.23 (d, J = 13.6 Hz, 3H), 3.88-3.53 (m, 19H), 3.03-2.93 (m, 2H), 2.80 (s, 2H), 2.59 (s, 2H), 1.90 (s, 1H), 2.32-1.82 (m, 7H), 1.77 (d, J = 8.2 Hz, 1H), 1.26 (d, J = 6.8 Hz, 3H), 1.02-0.68 (m, 7H). | 9 | 1149.73 |
| 385 | 1149.84 | 1151.84 | $^1$H NMR (400 MHz, DMSO-d$_6$) δ 10.00 (s, 1H), 8.99 (s, 1H), 8.43-8.31 (m, 1H), 7.87-7.74 (m, 2H), 7.51-6.94 (m, 9H), 6.17-5.97 (m, 1H), 5.21-5.00 (m, 2H), 4.39 (t, J = 8.2 Hz, 1H), 4.25 (d, J = 16.4 Hz, 3H), 3.92-3.43 (m, 19H), 3.07-2.78 (m, 4H), 2.62 (s, 2H), 2.29-1.96 (m, 8H), 1.84-1.68 (m, 1H), 1.41-1.24 (m, 3H), 1.00-0.74 (m, 7H . | 9 | 1149.73 |
| 386 | 1193.87 | 1195.87 | $^1$H NMR (DMSO-d$_6$) δ 9.01-8.96 (m, 1H), 8.29 (d, J = 7.2 Hz, 1H), 7.81-7.73 (m, 2H), 7.41 (br s, 1H), 7.28-6.96 (m, 9H), 6.08 (d, J = 5.2 Hz, 1H), 5.12 (t, J = 7.2 Hz, 1H), 4.46-4.09 (m, 4H), 3.90-3.80 (m, 4H), 3.78-3.61 (m, 12H), 3.50 (d, J = 18.8 Hz, 10H), 3.04-2.96 (m, 2H), 2.80 (br s, 2H), 2.25 (d, J = 6.4 Hz, 2H), 2.10-1.96 (m, 5H), 1.78 (d = 6.8 HzM 1H), 1.38 (d, J = 6.8 Hz, 1H), 1.26 (d, J = 6.8 Hz, 3H), 1.00-0.72 (m, 8H). | 9 | 1193.79 |
| 387 | 1193.87 | 1195.87 | $^1$H NMR (DMSO-d$_6$) δ 9.01-8.96 (m, 1H), 8.29 (d, J = 7.2 Hz, 1H), 7.81-7.73 (m, 2H), 7.41 (br s, 114), 7.28-6.96 (m, 9H), 6.08 (d, J = 5.2 Hz, 1H), 5.12 (t, J = 7.2 Hz, 1H), 4.46-4.09 (m, 4H), 3.90-3.80 (m, 4H), 3.78-3.61 (m, 12H), 3.50 (d, J = 18.8 Hz, 10H), 3.04-2.96 (m, 2H), 2.80 (br s, 2H), 2.25 (d, J = 6.4 Hz, 2H), 2.10-1.96 (m, 5H), 1.78 (d, J = 6.8 Hz, 1H), 1.38 (d, J = 6.8 Hz, 1H), 1.26 (d, J = 6.8 Hz, 3H), 1.00-0.72 (m, 8H). | 9 | 1193.79 |
| 388 | 1237.91 | 1239.91 | $^1$H NMR (400 MHz, DMSO-d$_6$) δ 10.00 (s, 1H), 9.03-8.80 (m, 1H), 8.29 (d, J = 6.8 Hz, 1H), 7.85-7.70 (m, 2H), 7.49-6.93 (m, 10H), 6.22-6.04 (m, 1H), 5.30-4.92 (m, 2H), 4.59-4.38 (m, 1H), 4.22 (d, J = 18.4 Hz, 3H), 3.91-3.43 (m, 29H), 3.05-2.87 (m, 2H), 2.85-2.71 (m, 2H), 2.68-2.58 (m, 2H), 2.25 (s, 2H), 2.12-1.87 (m, 4H), 1.76 (s, 1H), 1.55-1.17 (m, 4H), 1.01-0.70 (m, 7H). | 9 | 1237.84 |
| 389 | 1237.91 | 1239.91 | $^1$H NMR (400 MHz, DMSO-d$_6$) δ 9.99 (s, 1H), 8.99 (s, 1H), 8.37 (d, J = 8.0 Hz, 1H), 7.84-7.74 (m, 2H), 7.54-6.93 (m, 10H), 6.08 (s, 1H), 5.25-4.99 (m, 2H), 4.39 (t, J = 7.8 Hz, 1H), 4.30-4.18 (m, 3H), 3.88-3.46 (m, 29H), 2.81 (s, 2H), 3.00 (s, 2H), 2.71-2.57 (m, 2H), 2.22 (s, 2H), 2.06 (s, 4H), 1.78 (d, J = 5.6 Hz, 1H), 1.43-1.12 (m, 4H), 1.00-0.69 (m, 7H). | 9 | 1237.84 |
| 390 | 1281.94 | 1283.94 | $^1$H NMR (400 MHz, DMSO-d$_6$) δ 9.05-8.94 (m, 1H), 8.29 (d, J = 8.0 Hz, 1H), 7.83-7.73 (m, 2H), 7.50-6.95 (m, 10H), 6.18-6.07 (m, 1H), 5.35-5.03 (m, 2H), 4.45 (t, J = 7.8 Hz, 1H), 4.23 (d, J = 12.6 Hz, 3H), 3.88-3.45 (m, 31H), 3.00 (s, 2H), 2.81 (s, 2H), 2.62 (d, J = 7.2 Hz, 2H), 2.47 (s, 3H), 2.32-2.20 (m, 1H), 2.13-1.73 (m, 5H), 1.41-1.24 (m, 3H), 1.00-0.74 (m, 7H). | 9 | 1281.89 |
| 391 | 1281.94 | 283.94 | $^1$H NMR (400 MHz, DMSO-d$_6$) δ 8.99 (s, 1H), 8.37 (d, J = 8.0 Hz, 1H), 7.85-7.75 (m, 2H), 7.47-7.00 (m, 10H), 6.13-5.89 (m, 1H), 5.15 (t, J = 7.2 Hz, 2H), 4.40 (t, J = 7.8 Hz, 1H), 4.30-4.21 (m, 3H), 3.93-3.47 (m, 31H), 3.01 (s, 2H), 2.82 (s, 2H), 2.63 ( d, J = 8.2 Hz, 2H), 2.48 (s, 3H), 2.29-2.18 (m, 1H), 2.11-1.73 (m, 4H), 1.41-1.27 (m, 3H), 1.01-0.76 (m, 7H). | 9 | 1281.89 |
| 392 | 1325.97 | 1327.97 | $^1$H NMR (400 MHz, DMSO-d$_6$) δ 9.03-8.92 (m, 1H), 8.26 (d, J = 8.0 Hz, 1H), 7.88-7.71 (m, 2H), 7.49-6.91 (m, 11H), 6.15-6.03 (m, 1H), 5.28-5.06 (m, 1H), 4.63-4.37 (m, 1H), 4.31-4.14 (m, 4H), 3.88-3.82 (m, 3H), 3.69-3.45 (m, 24H), 3.19- | 9 | 1325.95 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | 3.13 (m, 1H), 3.04-2.92 (m, 3H), 2.80 (s, 2H), 2.69-2.57 (m, 2H), 2.29-2.02 (m, 9H), 1.86-1.73 (m, 1H), 1.39-1.26 (m, 4H), 0.97-0.81 (m, 8H). | | |
| 393 | 1325.98 | 1327.98 | ¹H NMR (400 MHz, DMSO-d₆) δ 8.99 (s, 1H), 8.35 (d, J = 7.8 Hz, 1H), 7.88-7.74 (m, 2H), 7.48-7.00 (m, 10H), 6.10 (s, 1H), 5.21-5.12 (m, 1H), 4.41 (t, J = 7.8 Hz, 1H), 4.32-4.17 (m, 4H), 3.86 (s, 3H), 3.70-3.48 (m, 25H), 3.07-2.91 (m, 3H), 2.82 (s, 2H), 2.70-2.59 (m, 2H), 2.48 (s, 3H), 2.35-1.96 (m, 8H), 1.79 (ddd, J = 5.0, 7.6, 12.6 Hz, 1H), 1.53-1.23 (m, 4H), 1.09-0.74 (m, 5H). | 9 | 1325.95 |
| 394 | 1370.01 | 1372.02 | ¹H NMR (DMSO-d₆) δ 10.06 (br s, 1H) 8.95-9.02 (m, 1H) 8.23-8.40 (m, 1H) 7.76-7.84 (m, 2H) 7.43 (m, 1H) 6.98-7.36 (m, 8H) 6.08-6.18 (m, 1H) 4.90-5.27 (m, 2H) 4.39-4.57 (m, 1H) 4.17-4.29 (m, 3H) 3.81-3.91 (m, 4H) 3.62-3.78 (m, 11 H) 3.43-3.59 (m, 30H) 3.01 (s, 2H) 2.81 (br s, 2H) 1.87-2.30 (m, 6H) 1.70-1.85 (m, 1H) 1.23-1.41 (m, 3H) 0.96 (d, J = 6.40 Hz, 2H) 0.72-0.86 (m, 4H). | 9 | 1370.00 |
| 395 | 1370.01 | 1372.02 | ¹H NMR (DMSO-d₆) δ 8.97-9.02 (m, 1H) 8.34-8.42 (m, 1H) 7.75-7.80 (m, 2H) 7.03 (d, J = 6.8 Hz, 10H) 6.07-6.13 (m, 1H) 5.10-5.20 (m, 1H) 4.35-4.44 (m, 1H) 4.21-4.31 (m, 3H) 3.84-3.88 (m, 3H) 3.43-3.74 (m, 42H) 2.77-3.03 (m, 4H) 1.98-2.29 (m, 6H) 1.72-1.83 (m, 1H) 1.26-1.40 (m, 3H) 0.91-1.01 (m, 3H) 0.74-0.84 (m, 3H). | 9 | 1370.00 |
| 396 | 1209.95 | 1211.95 | ¹H NMR (400 MHz, DMSO-d₆) δ 9.58 (brs, 1H), 8.98 (s, 1H), 8.82-8.56 (m, 1H), 8.41 (d, J = 8.0 Hz, 1H), 8.08 (brs, 1H), 7.82 (d, J = 8.8 Hz, 1H), 7.59-7.18 (m, 9H), 7.07 (s, 1H), 6.82 (dd, J = 11.2, 16.4 Hz, 1H), 6.20 (d, J = 16.4 Hz, 1H), 5.77 (d, J = 11.2 Hz, 1H), 4.96-4.85 (m, 2H), 4.54 (d, J = 9.6 Hz, 1H), 4.43 (t, J = 8.0 Hz, 1H), 4.28 (s, 1H), 4.24-4.07 (m, 3H), 3.97-3.66 (m, 9H), 3.63-3.09 (m, 20H), 2.81 (s, 3H), 2.45 (s, 3H), 2.21-1.91 (m, 3H), 1.90-1.70 (m, 1H), 1.50-1.31 (m, 3H), 0.93 (s, 9H). | 10 | 1209.87 |
| 397 | 1210.93 | 1212.93 | ¹H NMR (400 MHz, DMSO-d₆) δ 8.97 (s, 1H), 8.42 (d, J = 7.8 Hz, 1H), 8.27 (s, 1H), 8.00 (s, 1H), 7.80 (d, J = 8.3 Hz, 1H), 7.46-7.40 (m, 4H), 7.35 (d, J = 8.1 Hz, 3H), 7.28 (d, J = 2.2 Hz, 1H), 7.21 (br d, J = 3.9 Hz, 2H), 7.07 (d, J = 2.0 Hz, 1H), 6.82 (dd, J = 10.5, 16.7 Hz, 1H), 6.18 (dd, J = 2.3, 16.7 Hz, 1H), 5.79-5.69 (m, 1H), 5.33 (q, J = 6.1 Hz, 1H), 5.14 (br s, 1H), 4.95-4.84 (m, 1H), 4.53 (d, J = 9.7 Hz, 1H), 4.43 (t, J = 8.3 Hz, 1H), 4.28 (br s, 1H), 3.96-3.72 (m, 11H), 3.62-3.47 (m, 16H), 2.74-2.66 (m, 1H), 2.60-2.55 (m, 2H), 2.44 (s, 3H), 2.26-2.25 (m, 3H), 2.02 (br d, J = 7.6 Hz, 1H), 1.77 (ddd, J = 4.7, 8.5, 12.9 Hz, 1H), 1.36 (d, J = 7.1 Hz, 3H), 1.30 (d, J = 6.1 Hz, 3H), 0.92 (s, 9H). | 11 | 1210.86 |
| 398 | 1148.88 | 1150.88 | ¹H NMR (400 MHz, DMSO-d₆) δ 10.13-9.89 (m, 1H), 8.98 (s, 1H), 8.41 (br d, J = 7.1 Hz, 1H), 8.26 (s, 1H), 8.00 (s, 1H), 7.80 (d, J = 9.2 Hz, 1H), 7.42 (br d, J = 7.0 Hz, 3H), 7.39-7.26 (m, 4H), 7.21 (br d, J = 8.3 Hz, 2H), 7.06 (br d, J = 5.4 Hz, 1H), 6.83 (dd, J = 10.6, 16.9 Hz, 1H), 6.18 (br d, J = 16.9 Hz, 1H), 5.74 (br d, J = 10.6 Hz, 1H), 5.38 (br s, 1H), 5.12 (br s, 1H), 4.88 (br d, J = 6.1 Hz, 1H), 4.52 (d, J = 9.9 Hz, 1H), 4.43 (t, J = 8.5 Hz, 1H), 4.27 (br s, 1H), 3.92 (br d, J = 8.4 Hz, 6H), 3.85 (br s, 2H), 3.78 (br s, 2H), 3.54 (br d, J = 14.1 Hz, 6H), 3.46-3.40 (m, 3H), 2.77 (br s, 2H), 2.61 (br s, 1H), 2.45 (s, 3H), 2.39 (br s, 1H), 2.15 (br s, 2H), 2.02 (br d, J = 8.6 Hz, 1H), 1.77 (br s, 3H), 1.35 (br d, J = 6.5 Hz, 3H), 1.30 (br d, J = 6.1 Hz, 3H), 0.90 (br s, 9H). | 11 | 1148.79 |
| 399 | 1192.68 1192.82 | 1194.82 | ¹H NMR (400 MHz, DMSO-d₆) δ 10.06 (br d, J = 11.9 Hz, 1H), 9.26 (br s, 1H), 8.98 (s, 1H), 8.40 (d, J = 7.7 Hz, 1H), 8.07 (s, 1H), 7.82 (d, J = 8.2 Hz, 1H), 7.48-7.33 (m, 6H), 7.30 (d, J = 2.2 Hz, 1H), 7.27-7.15 (m, 2H), 7.06 (dd, J = 2.3, 9.0 Hz, 1H), 6.83 (dd, J = 10.6, 16.6 Hz, 1H), 6.19 (dd, J = 2.2, 16.6 Hz, 1H), 5.80-5.72 (m, 1H), 5.64 (br s, 1H), 4.89 (br s, 1H), 4.54 (br d, J = 9.8 Hz, 1H), 4.42 (br t, J = 8.0 Hz, 1H), 4.28 (br s, 1H), 3.96 (br d, J = 7.3 Hz, 6H), 3.93-3.90 (m, 4H), 3.86 (br s, 5H), 3.81 (br s, 6H), 3.62-3.51 (m, 10H), 3.43-3.29 (m, 1H), 3.17 (br s, 2H), 2.45 (s, 3H), 2.12-1.86 (m, 3H), 1.77 (br s, 1H), 1.47-1.33 (m, 6H), 0.92 (s, 9H). | 11 | 1192.84 |
| 400 | 1236.95 | 1238.95 | ¹H NMR (400 MHz, DMSO-d₆) δ 10.06 (br s, 1H), 8.97 (s, 1H), 8.75-8.34 (m, 1H), 8.18 (s, 1H), 8.00 (s, 1H), 7.80 (d, J = 8.4 Hz, 1H), 7.48-7.39 (m, 3H), 7.39-7.31 (m, 3H), 7.28 (d, J = 2.3 Hz, 1H), 7.23-7.12 (m, 2H), 7.06 (dd, J = 2.4, 5.5 Hz, 1H), 6.83 (dd, J = 10.6, 16.7 Hz, 1H), 6.18 (dd, J = 2.3, 16.7 Hz, 1H), 5.79-5.68 (m, 1H), 5.39 (dt, J = 6.2, 11.9 Hz, 1H), 5.13 (br s, 1H), 4.89 (quin, J = 7.0 Hz, 1H), 4.53 (d, J = 9.6 Hz, 1H), 4.47-4.38 (m, 1H), 4.32-4.20 (m, 1H), 3.97-3.88 (m, 6H), 3.85 (br s, 2H), 3.77 (br s, 2H), 3.59-3.54 (m, 6H), 3.52 (br d, J = 2.3 Hz, 4H), 3.46 (br d, J = 3.9 Hz, 6H), 3.23 (br d, J = 4.4 Hz, 1H), 2.86-2.71 (m, 2H), 2.65-2.59 (m, 1H), 2.44 (s, 3H), 2.42-2.34 (m, 1H), 2.22-1.97 (m, 3H), 1.83-1.64 (m, 3H), 1.48-1.34 (m, 3H), 1.30 (dd, 1.8, 6.3 Hz, 3H), 0.92 (s, 9H). | 11 | 1236.90 |
| 401 | 1280.99 | 1282.99 | ¹H NMR (400 MHz, DMSO-d₆) δ 10.43-9.68 (m, 1H), 8.97 (s, 1H), 8.42 (d, J = 7.9 Hz, 1H), 8.23 (s, 1H), 8.00 (s, 1H), 7.81 (d, J = 8.2 Hz, 1H), 7.43 (br d, J = 8.2 Hz, 3H), 7.36 (d, J = 8.3 Hz, 2H), 7.29-7.15 (m, 3H), 7.06 (dd, J = 2.4, 5.0 Hz, 1H), 6.83 (dd, J = 10.1, 16.8 Hz, 1H), 6.22-6.15 (m, 1H), 5.74 (br d, J = 12.5 Hz, 1H), 5.38 (br dd, J = 5.6, 12.5 | 11 | 1280.95 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | Hz, 1H), 5.13 (s, 1H), 4.90 (br t, J = 6.9 Hz, 1H), 4.54 (d, J = 9.7 Hz, 1H), 4.47-4.39 (m, 1H), 4.28 (br s, 1H), 3.98-3.89 (m, 6H), 3.85 (br s, 2H), 3.78 (br s, 2H), 3.57 (br d, J = 9.0 Hz, 6H), 3.52 (br s, 4H), 3.49 (d, J = 2.3 Hz, 5H), 3.46 (br d, J = 3.7 Hz, 6H), 2.79 (br d, J = 16.3 Hz, 2H), 2.60 (br s, 1H), 2.45 (s, 3H), 2.37 (br d, J = 13.3 Hz, 1H), 2.13 (br s, 2H), 2.07-1.98 (m, 1H), 1.83-1.65 (m, 3H), 1.36 (d, J = 6.8 Hz, 3H), 1.30 (br d, J = 5.1 Hz, 3H), 0.93 (s, 9H). | | |
| 402 | 1325.02 | 1327.02 | $^1$H NMR (400 MHz, DMSO-d$_6$) δ 8.98 (s, 1H), 8.44 (d, J = 7.8 Hz, 1H), 8.31 (s, 1H), 8.01 (s, 1H), 7.81 (d, J = 8.4 Hz, 1H), 7.48-7.41 (m, 3H), 7.40-7.32 (m, 3H), 7.29 (d, J = 2.3 Hz, 1H), 7.27-7.14 (m, 2H), 7.07 (dd, J = 2.4, 5.1 Hz, 1H), 6.84 (dd, J = 10.4, 16.7 Hz, 1H), 6.19 (dd, J = 2.3, 16.6 Hz, 1H), 5.79-5.72 (m, 1H), 5.39 (qd, J = 6.3, 12.3 Hz, 1H), 4.90 (quin, J = 7.0 Hz, 1H), 4.54 (d, J = 9.6 Hz, 1H), 4.44 (t, J = 8.2 Hz, 1H), 4.32-4.22 (m, 1H), 4.02-3.89 (m, 6H), 3.86 (br s, 2H), 3.78 (br s, 2H), 3.64-3.59 (m, 4H), 3.56 (br d, J = 5.9 Hz, 4H), 3.54-3.5 2 (m, 6H), 3.50-3.48 (m, 10H), 3.22 (br dd, J = 4.3, 8.6 Hz, 1H), 2.88-2.70 (m, 2H), 2.66-2.58 (m, 1H), 2.45 (s, 3H), 2.42-2.35 (m, 1H), 2.19-2.00 (m, 3H), 1.84-1.64 (m, 3H), 1.37 (d, J = 7.0 Hz, 3H), 1.30 (dd, J = 1.9, 6.3 Hz, 3H), 0.99-0.89 (m, 9H). | 11 | 1325.00 |
| 403 | 1186.71 | 1188.72 | $^1$H NMR (400 MHz, DMSO-d$_6$) δ 8.96 (s, 1H), 8.44-8.42 (d, J = 8.0 Hz, 1H), 8.28 (s, 2H), 8.00 (s, 1H), 7.80-7.78 (d, J = 8.0 Hz, 1H), 7.70-7.66 (d, J = 16.0 Hz, 1H), 7.46-7.39 (m, 3H), 7.38-7.31 (m, 2H), 7.28-7.27 (d, J = 4.0 Hz, 1H), 7.26-7.15 (m, 2H), 7.10-7.03 (m, 1H), 6.88-6.77 (m, 1H), 6.22-6.13 (m, 1H), 5.78-5.71 (m, 1H), 5.45-5.36 (m, 1H), 4.92-4.81 (m, 1H), 4.50-4.32 (m, 3H), 4.26 (s, 1H), 3.99-3.69 (m, 14H), 3.11-2.79 (m, 5H), 2.44 (s, 7H), 2.11-1.85 (m, 6H), 1.79-1.69 (m, 1H), 1.59-1.49 (m, 2H), 1.41-1.26 (m, 7H), 0.90 (s, 12H). | 11 | 1186.89 |
| 404 | 1186.87 | 1188.87 | $^1$H NMR (400 MHz, DMSO-d$_6$) δ 8.98 (s, 1H), 8.45 (d, J = 7.7 Hz, 1H), 8.25 (s, 2H), 8.01 (s, 1H), 7.81 (d, J = 8.2 Hz, 1H), 7.73 (d, J = 9.7 Hz, 1H), 7.43 (d, J = 8.2 Hz, 3H), 7.36 (d, J = 8.4 Hz, 2H), 7.29 (d, J = 2.2 Hz, 1H), 7.24-7.18 (m, 2H), 7.06 (dd, J = 2.3, 8.5 Hz, 1H), 6.84 (dd, J = 10.5, 16.7 Hz, 1H), 6.18 (dd, J = 2.1, 16.6 Hz, 1H), 5.79-5.72 (m, 1H), 5.45-5.38 (m, 1H), 4.88 (t, J = 7.2 Hz, 1H), 4.51-4.39 (m, 3H), 4.27 (s, 1H), 3.95-3.73 (m, 8H), 2.99 (d, J = 14.9 Hz, 1H), 2.87-2.71 (m, 4H), 2.69-2.58 (m, 3H), 2.45 (s, 3H), 2.40 (s, 2H), 2.21 (s, 4H), 2.08-2.02 (m, 6H), 1.79-1.58 (m, 4H), 1.45-1.29 (m, 8H), 1.07 (s, 2H), 0.92 (s, 9H). | 11 | 1186.89 |
| 405 | 1192.85 | 1194.85 | $^1$H NMR (400 MHz, DMSO-d$_6$) δ 10.3-9.83 (m, 1H), 8.99-8.95 (m, 1H), 8.38 (d, J = 8.0 Hz, 1H), 8.35-8.29 (m, 1H), 8.00 (s, 1H), 7.85-7.73 (m, 1H), 7.46-7.41 (m, 3H), 7.39-7.33 (m, 3H), 7.30-7.26 (m, 1H), 7.24-7.16 (m, 2H), 7.08-7.04 (m, 1 H), 6.87-6.78 (m, 1H), 6.22-6.14 (m, 1H), 5.77-5.71 (m, 1H), 5.47-5.25 (m, 2 H), 4.95-4.85 (m, 1H), 4.53-4.44 (m, 1H), 4.42-4.29 (m, 1 H), 4.25-4.12 (m, 1 H), 3.96-3.87 (m, 6H), 3.86-3.82 (m, 2H), 3.77 (br s, 2H), 3.61-3.51 (m, 6H), 3.51-3.45 (m, 6H), 3.21 (br d, J = 4.0 Hz, 1H), 2.83-2.71 (m, 2H), 2.61 (ddd, J = 12.4, 6.8, 2.8 Hz, 1H), 2.44 (s, 3H), 2.41-2.35 (m, 1H), 2.20-2.02 (m, 2H), 1.82-1.67 (m, 2H), 1.62 (dt, J = 12.4, 6.4 Hz, 1H), 1.36 (d, J = 6.8 Hz, 3H), 1.30 (dd, J = 6.0, 1.6 Hz, 3H), 1.24 (br s, 1H), 0.96-0.88 (m, 9H). | 11 | 1192.84 |
| 406 | 1101.94 | | $^1$H NMR (400 MHz, CDCl$_3$) δ 8.60 (s, 1H), 7.94(d, J = 8.0 Hz, 1H), 7.54 (d, J = 8.4 Hz, 1H), 7.48 (d, J = 7.6 Hz, 1H), 7.32-7.20 (m, 7H), 6.82 (s, 1H), 6.69 (s, 1H), 6.49 (dd, J = 10.8, 16.8 Hz, 1H), 6.26 (d, J = 16.8 Hz, 1H), 5.68 (d, J = 10.4 Hz, 1H), 5.31-5.21 (m,1H), 5.04-4.95 (m, 1H), 4.66 (t, J = 8.0 Hz, 1H), 4.53 (d, J = 8.8 Hz, 1H), 4.43 (s, 1H), 4.14-3.92 (m, 5H), 3.70-3.30 (m, 14H), 3.27-3.12 (m, 2H), 2.90-2.75 (m, 2H), 2.72-2.60 (m, 2H), 2.43 (s, 3H), 2.40-2.30 (m, 2H), 2.28-2.10 (m, 2H), 2.06-2.00 (m, 1H), 1.60-1.42 (m, 3H), 1.40-1.33 (m, 4H), 1.25 (d, J = 6.4 Hz, 3H), 1.04 (s, 2H), 0.97 (s, 9H). | 11 | 1101.38 |
| 407 | 1145.97 | | $^1$H NMR (400 MHz, CDCl$_3$) δ 8.60 (s, 1H), 7.95 (d, J = 8.4 Hz, 1H), 7.56 (d, J = 8.0 Hz, 1H), 7.46 (d, J = 7.2 Hz, 1H), 7.34-7.21 (m, 7H), 6.83 (s, 1H), 6.70 (s, 1H), 6.50 (dd, J = 10.4, 16.8 Hz, 1H), 6.26 (dd, J = 2.0, 16.8 Hz, 1H), 5.68 (dd, J = 1.6, 10.4 Hz, 1H), 5.31-5.21 (m, 1H), 5.03-4.96 (m, 1H), 4.68 (t, J = 7.6 Hz, 1H), 4.53 (d, J = 8.8 Hz, 1H), 4.41 (s, 1H), 4.15-3.93 (m, 5H), 3.72-3.37 (m, 18H), 3.30-3.18 (m, 2H), 2.92-2.80 (m, 2H), 2.71-2.62 (m, 2H), 2.50-2.34 (m, 5H), 2.27-2.14 (m, 2H), 2.05-1.89 (m, 3H), 1.58-1.45 (m, 4H), 1.40 (d, J = 6.8 Hz, 3H), 1.26 (d, J = 6.0 Hz, 3H), 0.98 (s, 9H). | 11 | 1145.43 |
| 408 | 1190.02 | | $^1$H NMR (400 MHz, CDCl$_3$) δ 8.60 (s, 1H), 7.93 (d, J = 8.4 Hz, 1H), 7.54 (d, J = 8.0 Hz, 1H), 7.46 (d, J = 7.2 Hz, 1H), 7.33-7.20 (m, 7H), 6.81 (s, 1H), 6.69 (s, 1H), 6.49 (dd, J = 10.8, 16.8 Hz, 1H), 6.26 (d, J = 16.8 Hz, 1H), 5.68 (d, J = 10.4 Hz, 1H), 5.31-5.21 (m, 1H), 5.04-4.95 (m, 1H), 4.68 (t, J = 8.0 Hz, 1H), 4.53 (d, J = 8.8 Hz, 1H), 4.45 (s, 1H), 4.07 (s, 2H), 4.00-3.90 (m, 3H), 3.72-3.48 (m, 18H), 3.45-3.32 (m, 4H), 3.33-3.15 (m, 2H), 2.90-2.78 (m, 2H), 2.74-2.60 (m, 2H), 2.44 (s, 3H), 2.41-2.33 (m, 2H), 2.30-2.15 (m, 2H), 2.07-1.88 (m, 4H), 1.60-1.45 (m, 3H), 1.40 (d, J = 6.8 Hz, 3H), 1.26 (d, J = 6.0 Hz, 3H), 0.99 (s, 9H). | 11 | 1189.48 |
| 409 | 1234.04 | | $^1$H NMR (400 MHz, CDCl$_3$) δ 8.69 (s, 1H), 8.03 (d, J = 8.4 Hz, 1H), 7.64 (d, J = 8.4 Hz, 1H), 7.57 (d, J = 7.6Hz, 1H), 7.43-7.30 (m, 7H), 6.91 (s, 1H), 6.79 (s, 1H), 6.60 (dd, J = 10.4, 16.8 Hz, 1H), 6.36 (d, J = 18.0 Hz, 1H), 5.76 (d, J = 11.6 Hz, 1H), 5.41-5.30 (m, 1H), 5.12- | 11 | 1233.54 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | 5.07 (m, 1H), 4.76 (t, J = 7.6 Hz, 1H), 4.62 (d, J = 8.8 Hz, 1H), 4.52 (s, 1H), 4.17 (s, 2H), 4.10-3.98 (m, 3H), 3.80-3.40 (m, 26H), 3.38-3.25 (m, 2H), 2.97-2.87 (m, 2H), 2.85-2.70 (m, 2H), 2.53 (s, 3H), 2.48-2.40 (m, 1H), 2.34-2.10 (m, 7H), 1.66-1.54 (m, 2H), 1.49 (d, J = 6.8 Hz, 3H), 1.35 (d, J = 6.0 Hz, 3H), 1.07 (s, 9H). | | |
| 410 | 1278.09 | | $^1$H NMR (400 MHz, CDCl$_3$) δ 8.60 (s, 1H), 7.94 (d, J = 8.4 Hz, 1H), 7.55 (d, J = 7.6 Hz, 1H), 7.48 (d, J = 8.0 Hz, 1H), 7.34-7.21 (m, 7H), 6.82 (s, 1H), 6.71 (s, 1H), 6.51 (dd, J = 10.8, 16.8 Hz, 1H), 6.26 (d, J = 16.8 Hz, 1H), 5.68 (d, J = 10.8 Hz, 1H), 5.35-5.22 (m, 1H), 5.04-4.98 (m, 1H), 4.68 (t, J = 8.0 Hz, 1H), 4.53 (d, J = 8.8 Hz, 1H), 4.44 (s, 1H), 4.10 (s, 2H), 4.01-3.89 (m, 3H), 3.75-3.35 (m, 30H), 3.30-3.15 (m, 2H), 2.88-2.78 (m, 2H), 2.75-2.65 (m, 2H), 2.44 (s, 3H), 2.41-2.33 (m, 2H), 2.27-2.15 (m, 2H), 2.08-2.00 (m, 1H), 1.96-1.86 (m, 3H), 1.56-1.44 (m, 3H), 1.40 (d, J = 6.8 Hz, 3H), 1.26 (d, J = 6.0 Hz, 3H), 0.99 (s, 9H). | 11 | 1277.59 |
| 411 | 872.53 | | $^1$H NMR (400 MHz, CHLOROFORM-d) δ 11.08 (br s, 1H), 8.29 (s, 1H), 8.00 (d, J = 8.4 Hz, 1H), 7.66 (d, J = 8.1 Hz, 1H), 7.60-7.53 (m, 1H), 7.38 (t, J = 7.5 Hz, 1H), 7.26 (t, J = 7.1 Hz, 1H), 7.13 (d, J = 8.7 Hz, 1H), 7.02 (d, J = 7.1 Hz, 1H), 6.90-6.73 (m, 3H), 6.60 (t, J = 5.6 Hz, 1H), 6.15 (dd, J = 2.3, 16.7 Hz, 1H), 5.80-5.65 (m, 1H), 5.25-5.14 (m, 1H), 5.05 (dd, J = 5.3, 12.9 Hz, 1H), 4.05 (br s, 2H), 3.70 (br s, 2H), 3.67 (br s, 2H), 3.59 (br t, J = 5.3 Hz, 4H), 3.50 (br s, 8H), 2.93-2.82 (m, 2H), 2.72 (br s, 2H), 2.58 (br d, J = 2.7 Hz, 1H), 2.54 (br s, 2H), 2.35 (br d, J = 5.6 Hz, 1H), 2.14 (br s, 2H), 2.06-1.94 (m, 1H), 1.76 (br s, 2H), 1.40 (br d, J = 5.4 Hz, 2H), 1.24 (d, J = 6.1 Hz, 3H). | 12 | 872.00 |
| 412 | 916.75 | | $^1$H NMR (400 MHz, DMSO-d$_6$) δ 11.10 (s, 1H), 9.68-9.20 (m, 1H), 7.99 (d, J = 8.4 Hz, 1H), 7.82 (d, J = 8.2 Hz, 1H), 7.66 (d, J = 8.4 Hz, 1H), 7.44 (d, J = 2.0 Hz, 1H), 7.41-7.31 (m, 2H), 7.26 (t, J = 7.3 Hz, 1H), 6.87-6.74 (m, 3H), 6.18-6.11 (m, 1H), 5.73 (d, J = 12.8 Hz, 1H), 5.43 ( s, 1H), 5.10 (dd, J = 5.6, 13.0 Hz, 1H), 4.29 (s, 2H), 4.08 (s, 2H), 3.82-3.53 (m, 13H), 3.30-2.89 (m, 14H), 2.60 (s, 4H), 2.15-1.84 (m, 3H), 1.30 (s, 3H). | 12 | 916.05 |
| 413 | 960.81 | | $^1$H NMR (400 MHz, DMSO-d$_6$) δ 11.10(s, 1H), 9.70 (s, 1H), 8.24 (s, 1H),8.01-7.98 (d, J = 12 Hz, 1H), 7.66-7.64 (d, J = 8.0 Hz, 1H), 7.57-7.53 (m, 1H), 7.40-7.36 (m, 1H 7.28-7.24 (m, 1H). 7.12-7.10 (d, J = 8.0 Hz, 1H),7.03-7.01 (d, J = 8.0 Hz, 1H), 6.86-6.75 (m, 3H), 6.61-6.54 (m, 1H), 6.16-6.12 (m, 1H), 5.74-5.69 (m, 1H), 5.22-5.15 (m, 1H), 5.07-5.00 (m, 1H), 4.04 (s, 2H), 3.70-3.66 (d, J = 16.0 Hz, 4H), 3.62-3.57 (m, 3H), 3.54-3.49 (m, 8H), 3.45 (s, 4H), 2.93-2.82 (m, 4H), 2.71-2.65 (m, 3H), 2.63-2.55 (m, 4H), 2.33-2.32 (m, 1H), 2.11-1.95 (m, 4H), 1.75-1.72 (d, J = 12.0 Hz, 2H), 1.35-1.27 (m, 2H), 1.24-1.22 (d, J = 8.0 Hz, 3H). | 12 | 960.10 |
| 414 | 1004.84 | | $^1$H NMR (400 MHz, DMSO-d$_6$) δ 11.10 (br s, 1H), 8.22 (s, 1H), 8.01 (d, J = 8.8 Hz, 1H), 7.67 (d, J = 8.4 Hz, 1H), 7.60-7.53 (m, 1H), 7.39 (t, J = 7.6 Hz, 1H), 7.27 (t, J = 7.6 Hz, 1H), 7.13 (d, J = 8.8 Hz, 1H), 7.03 (d, J = 7.2 Hz, 1H), 6.88-6.74 (m, 3H), 6.60 (br t, J = 5.6 Hz, 1H), 6.15 (dd, J = 2.4, 16.8 Hz, 1H), 5.78-5.67 (m, 1H), 5.28-5.15 (m, 1H), 5.05 (dd, J = 5.4, 12.8 Hz, 1H), 4.06 (s, 2H), 3.75-3.64 (m, 1H), 3.68 (br s, 4H), 3.64-3.50 (m, 18H), 2.94-2.82 (m, 2H), 2.74 (br s, 2H), 2.63-2.54 (m, 2H), 2.38-2.34 (m, 1H), 2.18-1.99 (m, 9H), 1.77 (br d, J = 6.0 Hz, 2H), 1.33 (br s, 2H), 1.25 (d, J = 6.0 Hz, 3H). | 12 | 1004.16 |
| 415 | 1048.66 | | $^1$H NMR (400 MHz, DMSO-d$_6$) δ 11.09 (s, 1H), 8.31 (s, 1H), 8.00 (d, J = 8.4 Hz, 1H), 7.66 (d, J = 8.1 Hz, 1H), 7.59-7.53 (m, 1H), 7.38 (t, J = 7.3 Hz, 1H), 7.29-7.23 (m, 1H), 7.12 (d, J = 8.7 Hz, 1H), 7.03 (d, J = 7.0 Hz, 1H), 6.87-6.76 (m, 3H), 6.59 (t, J = 5.7 Hz, 1H), 6.15 (dd, J = 2.3, 16.6 Hz, 1H), 5.75-5.69 (m, 1H), 5.24-5.16 (m, 1H), 5.04 (dd, J = 5.3, 12.9 Hz, 1H), 4.05 (s, 2H), 3.69 (d, J = 13.8 Hz, 5H), 3.62-3.58 (m, 3H), 3.56-3.46 (m, 24H), 3.27-3.20 (m, 1H), 2.92-2.70 (m, 5H), 2.62-2.54 (m, 2H), 2.35 (d, J = 5.6 Hz, 1H), 2.14-2.00 (m, 3H), 1.76 (d, J = 9.8 Hz, 2H), 1.38-1.23 (m, 5H). | 12 | 1048.21 |
| 416 | 873.72 | | $^1$H NMR (400 MHz, DMSO-d$_6$) δ 11.11 (br s, 1H), 8.27 (s, 1H), 8.01 (d, J = 7.9 Hz, 1H), 7.82 (d, J = 8.3 Hz, 1H), 7.67 (d, J = 8.2 Hz, 1H), 7.45 (d, J = 2.2 Hz, 1H), 7.42-7.33 (m, 2H), 7.27 (t, J = 7.8 Hz, 1H), 7.02 (s, 1H), 6.89-6.76 (m, 3H), 6.16 (dd, J = 2.1, 16.6 Hz, 1H), 5.77-5.69 (m, 1H), 5.28-5.17 (m, 1H), 5.12 (dd, J = 5.5, 12.8 Hz, 1H), 4.29 (br s, 2H), 4.06 (s, 2H), 3.76 (br s, 2H), 3.72 (br s, 2H), 3.68 (br s, 2H), 3.51 (br s, 7H), 2.98-2.82 (m, 4H), 2.74 (br d, J = 5.5 Hz, 2H), 2.65-2.57 (m, 2H), 2.37 (br d, J = 4.5 Hz, 1H), 2.14 (br s, 2H), 2.08-2.01 (m, 1H), 1.80 (br s, 2H), 1.40 (br s, 2H), 1.26 (d, J = 6.1 Hz, 3H). | 12 | 872.98 |
| 417 | 916.57 | | $^1$H NMR (400 MHz, DMSO-d$_6$) δ 11.09 (s, 1H), 9.69 (s, 1H), 8.38 (s, 1H), 8.01 (d, J = 8.4 Hz, 1H), 7.66 (d, J = 8.2 Hz, 1H), 7.56 (t, J = 8.0 Hz, 1H), 7.38 (t, J = 7.3 Hz, 1H), 7.30-7.20 (m, 1H), 7.13 (d, J = 8.4 Hz, 1H), 7.02 (d, J = 7.2 Hz, 1H), 6.86-6.77 (m, 2H), 6.60 (s, 1H), 6.15 (d, J = 16.1 Hz, 1H), 5.72 (d, J = 12.8 Hz, 1H), 5.19 (d, J = 6.8 Hz, 1H), 5.04 (dd, J = 5.3, 13.3 Hz, 1H), 4.05 (s, 2H), 3.76-3.58 (m, 7H), 3.57-3.40 (m, 15H), 2.87 (s, 2H), 2.72 (s, 1H), 2.59 (s, 2H), 2.10 (s, 4H), 1.76 (s, 2H), 1.34 (s, 2H), 1.24 (d, J = 6.2 Hz, 3H). | 12 | 917.03 |
| 418 | 961.79 | | $^1$H NMR (400 MHz, DMSO-d$_6$) δ 11.12(s, 1H), 9.72 (s, 1H), 8.24 (s, 1H),8.01 (d, J = 4 Hz, 1H), 7.82 (d, J = 4 Hz, 1H), 7.67 (d, J = 4 Hz, 1H), 7.47-7.25 (m, 3H), 6.92-6.69 (m, 3H), 6.2-6.12 (m, 1H), 5.77-5.67 (m, 1H), 5.27-5.16 (m, 1H), 5.16-5.08 (m, 1H), 4.35-4.25 (m, 2H), 4.06 (s, 2H), 3.81-3.76 (m, 2H), 3.69 (d, J = 12 Hz, 4H), 3.60-3.57 (m, 2H), 3.57-3.46 (m, 16H), 3.28-3.21 (m, 1H), 2.97-2.87 (m, 2H), 2.83-2.70 (m, 2H), 2.64-2.54 (m, 2H), 2.33-2.24 (m, 1H), 2.18-2.01 (m, 2H), 1.77 (d, J = 12 Hz, 2H), 1.42-1.30 (m, 2H), 1.25 (d, J = 4 Hz, 3H). | 12 | 961.09 |
| 419 | 1005.83 | | $^1$H NMR (400 MHz, DMSO-d$_6$) δ 11.12 (s, 114), 8.19 (s, 2H), 8.01 (br d, J = 8.4 Hz, 1H), 7.83 (d, J = 8.4 Hz, 1H), 7.67 (d, J = 8.0 Hz, 1H), 7.54-7.33 (m, 3H), 7.31-7.23 | 12 | 1005.14 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | (m, 1H), 6.93-6.72 (m, 3H), 6.16 (dd, J = 2.4, 16.8 Hz, 1H), 5.77-5.71 (m, 1H), 5.27-5.18 (m, 1H), 5.12 (dd, J = 5.2, 13.2 Hz, 1H), 4.37-4.23 (m, 2H), 4.10-4.01 (m, 2H), 3.86-3.54 (m, 26H), 3.07-2.82 (m, 4H), 2.76 (br d, J = 13.6 Hz, 2H), 2.64-2.55 (m, 2H), 2.43-2.31 (m, 1H), 2.14 (br s, 2H), 2.09-1.98 (m, 1H), 1.78 (br d, J = 9.6 Hz, 2H), 1.35 (br s, 2H), 1.26 (d, J = 6.0 Hz, 3H). | | |
| 420 | 1049.65 | | $^1$H NMR (400 MHz, DMSO-d$_6$) δ 11.13 (s, 1H), 9.71 (s, 1H), 8.19 (s, 1H), 8.01 (d, J = 8.4 Hz, 1H), 7.82 (d, J = 8.4 Hz, 1H), 7.67 (d, J = 8.0 Hz, 1H), 7.44 (d, J = 2.4 Hz, 1H), 7.42-7.35 (m, 2H), 7.28 (d, J = 8.0 Hz, 1H), 6.88-6.81 (m, 2H), 6.77 (d, J = 2.0 Hz, 1H), 6.15 (m, 1H), 5.76-5.70 (m, 1H), 5.24-5.18 (m, 1H), 5.15-5.10 (m, 1H), 4.31-4.28 (m, 2H), 4.06 (s, 2H), 3.81-3.51 (m, 30H), 2.95-2.83 (m, 4H), 2.81-2.68 (m, 4H), 2.16-2.03 (m, 4H), 1.76 (s, 2H), 1.35 (s, 2H), 1.25 (d, J = 6.0 Hz, 3H). | 12 | 1049.19 |
| 421 | 859.54 | | $^1$H NMR (400 MHz, DMSO-d$_6$) δ 10.96 (s, 1H), 10.37-9.58 (m, 1H), 8.30 (s, 1H), 8.00 (d, J = 8.4 Hz, 1H), 7.66 (d, J = 8.0 Hz, 1H), 7.62-7.56 (m, 1H), 7.42-7.36 (m, 1H), 7.30-7.23 (m, 1H), 7.16 (d, J = 1.9 Hz, 1H), 7.08-6.99 (m, 1H), 6.88-6.79 (m, 2H), 6.76 (d, J = 2.0 Hz, 1H), 6.15 (dd, J = 2.3, 16.7 Hz, 1H), 5.84-5.61 (m, 1H), 5.25-5.17 (m, 1H), 5.06 (dd, J = 5.1, 13.3 Hz, 1H), 4.39-4.04 (m, 8H), 3.75-3.66 (m, 4H), 3.50 (br d, J = 5.9 Hz, 2H), 3.27-3.24 (m, 2H), 2.95-2.83 (m, 4H), 2.83-2.69 (m, 5H), 2.40-2.35 (m, 1H), 2.18-2.09 (m, 2H), 2.07 (s, 2H), 2.02-1.93 (m, 1H), 1.81 (br d, J = 9.8 Hz, 2H), 1.46-1.32 (m, 2H), 1.25 (br d, J = 6.1 Hz, 3H). | 12 | 859.00 |
| 422 | 903.78 | | $^1$H NMR (400 MHz, DMSO-d$_6$) δ 10.97 (s, 1H), 9.70 (br s, 1H), 8.24 (s, 1H), 8.01 (d, J = 8.5 Hz, 1H), 7.71-7.57 (m, 2H), 7.39 (t, J = 7.1 Hz, 1H), 7.27 (t, J = 7.2 Hz, 1H), 7.16 (d, J = 1.6 Hz, 1H), 7.04 (dd, J = 2.1, 8.4 Hz, 1H), 6.88-6.70 (m, 3H), 6.15 (dd, J = 2.2, 16.7 Hz, 1H), 5.80-5.64 (m, 1H), 5.29-5.16 (m, 1H), 5.06 (dd, J = 5.0, 13.3 Hz, 1H), 4.41-4.34 (m, 1H), 4.29-4.22 (m, 1H), 4.19-4.13 (m, 2H), 4.08-4.00 (m, 2H), 3.82-3.61 (m, 10H), 3.32-3.28 (m, 8H), 2.95-2.85 (m, 4H), 2.73 (br d, J = 15.5 Hz, 2H), 2.60 (br d, J = 2.1 Hz, 2H), 2.16-2.07 (m, 2H), 2.01-1.93 (m, 1H), 1.77 (br d, J = 10.0 Hz, 2H), 1.35 (br d, J = 4.0 Hz, 2H), 1.25 (br d, J = 6.3 Hz, 3H). | 12 | 903.05 |
| 423 | 947.82 | | $^1$H NMR (400 MHz, DMSO-d$_6$) δ 10.96 (s, 1H), 9.51 (s, 1H), 8.29 (s, 2H), 8.00 (d, J = 12 Hz, 1H), 7.73-7.49 (m, 2H), 7.40-7.38 (m, 1H), 7.29-7.23 (m, 1H), 7.15 (s, 1H), 7.07-6.98 (m, 1H), 6.90-6.73 (m, 3H), 6.14 (d, J = 56 Hz, 1H), 5.71 (d, J = 48 Hz, 1H), 5.27-5.14 (m, 1H), 5.07-5.01 (m, 1H), 4.31-4.15 (m, 4H), 4.11-4.01 (m, 10H), 3.16-3.10 (m, 10H), 3.03-2.84 (m, 9H), 2.17-2.06 (m, 3H), 2.02-1.90 (m, 2H), 1.82-1.68 (m, 3H), 1.34-1.31 (m, 2H), 1.24-1.22 (d, J = 8.0 Hz, 3H). | 12 | 947.10 |
| 424 | 991.65 | | $^1$H NMR (400 MHz, DMSO-d$_6$) δ 11.03 (s, 1H), 10.54-9.22 (m, 1H), 8.34 (s, 1H), 8.06 (d, J = 8.4 Hz, 1H), 7.77-7.64 (m, 2H), 7.48-7.40 (m, 1H), 7.37-7.28 (m, 1H), 7.22 (d, J = 2.0 Hz, 1H), 7.10 (dd, J = 2.0, 8.4 Hz, 1H), 6.94-6.81 (m, 3H), 6.21 (dd, J = 2.4, 16.4 Hz, 1H), 5.85-5.69 (m, 1H), 5.26 (sxt, J = 6.0 Hz, 1H), 5.13 (dd, J = 5.2, 13.2 Hz, 1H), 4.47-4.27 (m, 2H), 4.25-4.19 (m, 2H), 3.86-3.70 (m, 8H), 3.67-3.57 (m, 10H), 3.30 (br s, 1H), 3.30 (br d, J = 8.8 Hz, 4H), 3.01-2.89 (m, 3H), 2.86-2.75 (m, 2H), 2.67-2.58 (m, 3H), 2.47-2.39 (m, 2H), 2.23-2.11 (m, 2H), 2.08-1.97 (m, 1H), 1.87-1.75 (m, 2H), 1.46-1.35 (m, 2H), 1.30 (d, J = 6.4 Hz, 3H). | 12 | 991.16 |
| 425 | 1035.67 | | $^1$H NMH (400 MHz, DMSO-d$_6$) δ 10.98 (s, 1H), 8.26 (s, 1H), 8.00 (d, J = 8.4 Hz, 1H), 7.64 (m, 2H), 7.39 (m, 1H), 7.33-7.22 (m, 1H), 7.16 (s, 1H), 7.05 (m, 1H), 6.91-6.72 (m, 3H), 6.15 (m, 1H), 5.80-5.68 (m, 1H), 5.21 (d, J = 6.0 Hz, 1H), 5.07 (m, 1H), 4.43-4.23 (m, 2H), 4.20-4.13 (m, 2H), 4.06 (s, 2H), 3.79-3.55 (m, 12H), 3.53-3.48 (m, 18H), 2.94-2.65 (m, 6H), 2.41-2.31 (m, 2H), 2.18-1.92 (m, 4H), 1.77 (d, J = 11.2 Hz, 2H), 1.34 (s, 2H), 1.25 (d, J = 6.0 Hz, 3H). | 12 | 1035.21 |
| 426 | 920.45 | 922.45 | $^1$H NMR (400 MHz, DMSO-d$_6$) δ 11.11 (s, 1H), 8.29 (br s, 1H), 8.00 (s, 1H), 7.80 (br d, J = 8.4 Hz, 2H), 7.43 (br s, 2H), 7.33 (br d, J = 8.3 Hz, 1H), 7.28 (s, 1H), 7.25-7.17 (m, 2H), 7.06 (d, J = 2.6 Hz, 1H), 6.83 (dd, J = 10.5, 16.6 Hz, 1H), 6.23-6.11 (m, 1H), 5.75 (br d, J = 12.3 Hz, 1H), 5.37 (br d, J = 5.7 Hz, 1H), 5.10 (dd, J = 5.6, 12.6 Hz, 1H), 4.26 (br s, 2H), 3.92 (br s, 4H), 3.85 (br s, 2H), 3.75 (br d, J = 16.0 Hz, 6H), 2.98-2.83 (m, 1H), 2.76 (br s, 2H), 2.60 (br s, 2H), 2.38 (br s, 1H), 2.20-1.99 (m, 4H), 1.75 (br s, 2H), 1.30 (br d, J = 6.1 Hz, 3H), 1.23 (br s, 1H). | 12 | 920.39 |
| 427 | 964.48 | 966.49 | $^1$H NMR (400 MHz, DMSO-d$_6$) δ 11.12 (s, 1H), 8.34-8.31 (m, 1H), 8.01 (s, 1H), 7.81 (dd, J = 1.9, 8.3 Hz, 2H), 7.46-7.41 (m, 2H), 7.37-7.18 (m, 4H), 7.07 (dd, J = 2.3, 5.4 Hz, 1H), 6.84 (dd, J = 10.4, 16.7 Hz, 1H), 6.24-6.13 (m, 1H), 5.78-5.71 (m, 1H), 5.44-5.31 (m, 1H), 5.11 (dd, J = 5.4, 12.8 Hz, 1H), 4.29 (s, 2H), 3.97-3.69 (m, 12H), 3.57-3.48 (m, 2H), 3.22 (d, J = 8.6 Hz, 2H), 2.92-2.80 (m, 1H), 2.64-2.56 (m, 4H), 2.47-2.36 (m, 1H), 2.14-1.99 (m, 3H), 1.71 (s, 2H), 1.34-1.20 (m, 5H). | 12 | 964.45 |
| 428 | 1008.51 | 1010.52 | $^1$H NMR (400 MHz, DMSO-d$_6$) δ 11.10 (s, 1H), 8.31 (s, 2H), 7.99 (s, 1H), 7.80-7.78 (d, J = 8.0 Hz, 2H), 7.47-7.40 (m, 2H), 7.36-7.30 (m, 1H), 7.23-7.20 (m, 1H), 7.08-7.04 (m, 1H), 6.88-6.77 (m, 2H), 6.25-6.13 (m, 1H), 5.83-5.67 (m, 2H), 5.43-5.31 (m, 1H), 5.13-5.06 (m, 1H), 4.29-4.24 (m, 2H), 3.94-3.72 (m, 12H), 3.58-3.52 (m, 7H), 3.24-3.13 (m, 2H), 2.94-2.71 (m, 3H), 2.64-2.55 (m, 2H), 2.41-2.34 (m, 1H), 2.21-1.91 (m, 4H), 1.78-1.62 (m, 2H), 1.30-1.27 (m, 3H), 1.24-1.17 (m, 1H). | 12 | 1008.50 |
| 429 | 1052.55 | 1054.55 | $^1$H NMR (400 MHz, DMSO-d$_6$) δ 11.11 (br s, 1H), 10.55-9.72 (m, 1H), 8.34 (s, 1H), 8.00 (s, 1H), 7.89-7.72 (m, 2H), 7.55-7.40 (m, 2H), 7.35 (dd, J = 2.0, 8.4 Hz, 1H), 7.29 (s, 1H), 7.26-7.16 (m, 2H), 7.07 (dd, J = 2.4, 5.2 Hz, 1H), 6.83 (dd, J = 10.4, 16.8 Hz, 1H), 6.18 (dd, J = 2.0, 16.4 Hz, 1H), 5.79-5.72 (m, 1H), 5.45-5.33 (m, 1H), | 12 | 1052.55 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | 5.11 (dd, J = 5.4, 12.8 Hz, 1H), 4.33-4.25 (m, 2H), 3.95-3.76 (m, 8H), 3.59-3.51 (m, 12H), 2.61 (br s, 8H), 2.17-2.00 (m, 3H), 1.71 (br s, 3H), 1.38-1.21 (m, 6H). | | |
| 430 | 1096.73 | 1098.73 | $^1$H NMR (400 MHz, DMSO-$d_6$) δ 11.11 (s, 1H), 10.03 (br s, 1H), 8.23 (s, 1H), 8.00 (s, 1H), 7.81 (dd, J = 3.6, 8.0 Hz, 2H), 7.48-7.41 (m, 2H), 7.38-7.32 (m, 1H), 7.28 (s, 1H), 7.26-7.16 (m, 2H), 7.06 (dd, J = 2.4, 5.2 Hz, 1H), 6.83 (dd, J = 10.4, 16.8 Hz, 1H), 6.18 (dd, J = 1.6, 16.8 Hz, 1H), 5.81-5.68 (m, 1H), 5.38 (br dd, J = 5.6, 12.4 Hz, 1H), 5.11 (dd, J = 5.4, 13.6 Hz, 1H), 4.29 (br s, 2H), 3.91 (br s, 4H), 3.85 (br s, 2H), 3.77 (br d, J = 5.2 Hz, 2H), 3.51 (br d, J = 2.8 Hz, 3H), 3.47 (br t, J = 3.2 Hz, 8H), 3.44 (br d, J = 3.6 Hz, 4H), 3.21 (br s, 1H), 2.97-2.78 (m, 1H), 2.60 (br s, 4H), 2.37 (br s, 1H), 2.23-1.91 (m, 4H), 1.70 (br s, 2H), 1.30 (br d, J = 5.6 Hz, 3H), 1.14 (s, 1H). | 12 | 1096.60 |
| 431 | 958.52 | 960.52 | $^1$H NMR (400 MHz, DMSO-$d_6$) δ 11.08 (s, 1H), 10.05 (s, 1H), 8.14 (s, 1H), 8.01 (s, 1H), 7.80-7.78 (d, J = 8.0 Hz, 1H), 7.67-7.65 (d, J = 8.0 Hz, 1H), 7.46-7.38 (m, 1H), 7.29-7.28 (d, J = 8.0 Hz, 2H), 7.26-7.15 (m, 3H), 7.08-7.01 (m, 1H), 6.90-6.72 (m, 1H), 6.21-6.11 (m, 1H), 5.80-5.67 (m, 1H), 5.44 (s, 1H), 5.13-4.98 (m, 1H), 4.00-3.69 (m, 7H), 3.26-3.14 (m, 6H), 3.10-2.79 (m, 3H), 2.77-2.69 (m, 1H), 2.63-2.58 (m, 1H), 2.57-2.53 (m, 2H), 2.41 (s, 4H), 2.25-1.92 (m, 5H), 1.68-1.39 (m, 3H), 1.31-1.30 (d, J = 4.0 Hz, 3H), 1.10-0.83 (m, 2H). | 12 | 958.49 |
| 432 | 958.66 | 960.66 | $^1$H NMR (400 MHz, DMSO-$d_6$) δ 11.08 (br s, 1H), 8.18 (s, 1H), 8.02 (s, 1H), 7.81 (d, J = 8.4 Hz, 1H), 7.64 (d, J = 8.8 Hz, 1H), 7.49-7.41 (m, 1H), 7.34-7.26 (m, 2H), 7.25-7.17 (m, 3H), 7.08 (dd, J = 2.4, 6.0 Hz, 1H), 6.84 (dd, J = 10.4, 16.8 Hz, 1H), 6.19 (dd, J = 2.4, 16.8 Hz, 1H), 5.80-5.72 (m, 1H), 5.42 (td, J = 6.0, 12.4 Hz, 1H), 5.06 (dd, J = 5.4, 12.8 Hz, 1H), 4.00 (br d, J = 12.4 Hz, 9H), 3.39-3.31 (m, 1H), 3.04-2.81 (m, 4H), 2.69-2.56 (m, 2H), 2.43 (br d, J = 14.8 Hz, 4H), 2.37-2.23 (m, 4H), 2.09 (br s, 2H), 2.05-1.95 (m, 1H), 1.74 (br d, J = 14.4 Hz, 3H), 1.32 (br d, J = 5.4 Hz, 3H), 1.27-1.02 (m, 4H). | 12 | 958.49 |
| 433 | 940.58 | 942.58 | $^1$H NMR (400 MHz, DMSO-$d_6$) δ 11.11 (s, 1H), 10.03 (br s, 1H), 8.15 (s, 1H), 8.03 (s, 1H), 7.81 (d, J = 8.4 Hz, 2H), 7.49-7.38 (m, 2H), 7.37-7.27 (m, 2H), 7.26-7.16 (m, 2H), 7.10-7.05 (m, 1H), 6.38 (br s, 1H), 5.45 (dd, J = 5.2, 10.0 Hz, 1H), 5.37 (br s, 1H), 5.11 (dd, J = 5.2, 12.8 Hz, 1H), 4.28 (br s, 2H), 4.04-3.68 (m, 8H), 3.03-2.77 (m, 5H), 2.71-2.53 (m, 3H), 2.47-2.22 (m, 3H), 2.10-2.00 (m, 1H), 1.89-1.74 (m, 2H), 1.44 (br s, 2H), 1.33 (d, J = 5.6 Hz, 3H). | 12 | 940.38 |
| 434 | 984.61 | 986.61 | $^1$H NMR (400 MHz, DMSO-$d_6$) δ 11.08 (s, 1H), 10.01 (s, 1H), 8.13 (s, 1H), 8.00 (s, 1H), 7.79 (d, J = 8.3 Hz, 1H), 7.46-7.38 (m, 2H), 7.34-7.30 (m, 1H), 7.27 (s, 1H), 7.23-7.14 (m, 2H), 7.05 (dd, J = 2.4, 5.8 Hz, 1H), 6.36 (d, J = 7.3 Hz, 1H), 5.42-5.34 (m, 1H), 5.09 (dd, J = 5.4, 12.8 Hz, 1H), 4.27 (s, 2H), 3.92-3.80 (m, 5H), 3.78-3.69 (m, 4H), 3.54 (d, J = 2.6 Hz, 3H), 3.48 (dd, J = 5.1, 10.9 Hz, 4H), 2.93-2.81 (m, 3H), 2.63-2.51 (m, 5H), 2.23 (s, 2H), 2.08-1.99 (m, 1H), 1.73 (s, 2H), 1.37-1.24 (m, 5H). | 12 | 984.43 |
| 435 | 1072.68 | 1074.68 | $^1$H NMR (400 MHz, DMSO-$d_6$) δ 11.11 (s, 1H), 10.02 (s, 1H), 9.42 (s, 1H), 8.18 (s, 2H), 8.00 (s, 1H), 7.86-7.73 (m, 2H), 7.46-7.41 (m, 2H), 7.34 (d, J = 2.0, 8.1 Hz, 1H), 7.30-7.14 (m, 3H), 7.12-7.03 (m, 1H), 6.37 (d, J = 7.5 Hz, 1H), 5.43-5.30 (m, 2H), 5.11 (dd, J = 5.6, 12.9 Hz, 1H), 4.31-4.25 (m, 2H), 3.87 (d, J = 13.5 Hz, 7H), 3.73 (d, J = 19.3 Hz, 7H), 3.56 (dd, J = 2.9, 5.6 Hz, 10H), 2.93-2.79 (m, 5H), 2.18-1.96 (m, 4H), 1.70 (s, 2H), 1.34-1.23 (m, 1H), 1.32-1.23 (m, 5H). | 12 | 1072.54 |
| 436 | 1097.68 | | $^1$H NMR (400 MHz, DMSO-$d_6$) δ 9.66 (s, 1H), 8.97 (s, 1H), 8.28 (s, 1H), 8.00 (d, J = 7.7 Hz, 1H), 7.66 (d, J = 8.8 Hz, 1H), 7.37 (d, J = 6.6 Hz, 1H), 7.26 (s, 1H), 7.04-6.95 (m, 2H), 6.87-6.76 (m, 3H), 6.21-6.12 (m, 2H), 5.72 ( d, J = 12.3 Hz, 1H), 5.20(s, 1H), 4.35-4.04 (m, 8H), 3.85-3.63 (m, 8H), 3.51 (s, 14H), 2.90-2.73 (m, 2H), 2.27-2.09 (m, 9H), 2.04-1.77 (m, 5H), 1.40 ( s, 2H), 1.25 (d, J = 6.1 Hz, 3H), 0.96 (d, J = 6.6 Hz, 2H), 0.79 (d, J = 6.6 Hz, 2H), 0.69 (d, J = 6.2 Hz, 1H), 0.57 (d, J = 6.7 Hz, 1H). | 13 | 1097.35 |
| 437 | 1097.69 | | $^1$H NMR (400 MHz, DMSO-$d_6$) δ 9.68 ( s, 1H), 8.97 (s, 1H), 8.37-8.26 (m, 1H), 8.00 (d, J = 8.3 Hz, 1H), 7.66 (d, J = 8.2 Hz, 1H), 7.39-7.33 (m, 1H), 7.26 (t, J = 7.8 Hz, 1H), 7.07-6.96 (m, 2H), 6.87-6.73 (m, 3H), 6.22-6.09 (m, 2H), 5.75-5.68 (m, 1H), 5.24-5.09 (m, 1H), 4.42-3.90 (m, 8H), 3.80-3.57 (m, 8H), 3.55-3.36 (m, 14H), 2.89 (s, 1H), 2.74 (s, 1H), 2.33-2.10 (m, 8H), 2.06-1.75 (m, 5H), 1.41 (s, 2H), 1.25 ( d, J = 6.1 Hz, 3H), 0.92 (d, J = 6.6 Hz, 3H), 0.78-0.71 (m, 3H). | 13 | 1097.35 |
| 438 | 1141.71 | | $^1$H NMR (400 MHz, DMSO-$d_6$) δ 9.71 (s, 1H), 9.10-8.90 (m, 1H), 8.32-8.25 (m, 1H), 8.24 (s, 1H), 7.99 (d, J = 8.0 Hz, 1H), 7.65 (d, J = 8.0 Hz, 1H), 7.44-7.34 (m, 1H), 7.31-7.21 (m, 2H), 7.11-6.93 (m, 2H), 6.89-6.73 (m, 3H), 6.27-6.09 (m, 2H), 5.77-5.67 (m, 1H), 5.23-5.14 (m, 1H), 4.52-4.10 (m, 7H), 4.09-4.00 (m, 2H), 3.93-3.55 (m, 20H), 3.28-3.20 (m, 4H), 2.93-2.83 (m, 2H), 2.46-2.41 (m, 3H), 2.28-2.16 (m, 2H), 2.15-2.00 (m, 5H), 1.96-1.83 (m, 1H), 1.81-1.62 (m, 2H), 1.39-1.27 (m, 2H), 1.26-1.15 (m, 3H), 0.97-0.51 (m, 6H). | 13 | 1141.40 |
| 439 | 1141.71 | | $^1$H NMR (400 MHz, DMSO-$d_6$) δ 9.70 (s, 1H), 8.95 (s, 1H), 8.40-8.30 (m, 1H), 8.26 (s, 1H), 7.98 (d, J = 8.0 Hz, 1H), 7.64 (d, J = 8.0 Hz, 1H), 7.43-7.31 (m, 2H), 7.29-7.23 (m, 1H), 7.04-6.95 (m, 2H), 6.85-6.74 (m, 3H), 6.23-6.10 (m, 2H), 5.75-5.68 (m, 1H), 5.23-5.10 (m, 2H), 4.42-4.33 (m, 2H), 4.28-4.23 (m, 2H), 4.20-4.11 (m, 3H), 4.06-4.02 (m, 2H), 3.78-3.62 (m, 18H), 3.25-3.20 (m, 4H), 2.91-2.85 (m, 2H), 2.44 (s, 3H), 2.28-2.22 (m, 1H), 2.17 (s, 3H), 2.11-1.99 (m, 4H), 1.95-1.86 (m, 1H), 1.80-1.70 (m, 2H), 1.36-1.27 (m, 2H), 1.23 (d, J = 6.0 Hz, 3H), 0.91 (d, J = 6.0 Hz, 3H), 0.76-0.72 (m, 3H). | 13 | 1141.40 |
| 440 | 1185.97 | | $^1$H NMR (400 MHz, DMSO-$d_6$) δ 10.17 (s, 1H), 9.07 (s, 1H), 8.97-8.18 (m, 1H), 7.99 (d, J = 8.4 Hz, 1H), 7.65 (d, J = 8.0 Hz, 1H), 7.37-7.27 (m,1H), 7.25-7.23 (m, 2H), | 13 | 1185.45 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | 7.02-7.01 (m, 2H), 6.85-6.76 (m, 3H), 6.71-6.32 (m, 1H), 6.20-6.12 (m, 2H), 5.72 (d, J = 12.4 Hz, 1H), 5.21-5.12 (m, 1H), 4.45-4.42 (m, 1H), 4.35-4.32 (m, 1H), 4.29-4.15 (m, 4H), 4.02-4.12 (m, 2H), 3.82-3.75 (m, 4H), 3.59-3.51 (m, 6H), 3.56-3.51 (m, 12H), 3.23-3.15 (m, 1H), 2.92-2.83 (m, 2H), 2.65-2.75 (s, 2H), 2.62-2.59 (m, 1H), 2.45-2.43 (m, 3H), 2.33-2.24 (m, 1H), 2.21-2.19 (m, 1H), 2.18-1.98 (m, 7H), 1.92-1.81 (m, 1H), 1.72-1.64 (m, 2H), 1.32-1.25 (m, 2H), 1.23-1.22 (m, 3H), 0.96-0.55 (m, 6H). | | |
| 441 | 1185.97 | | $^1$H NMR (400 MHz, DMSO-d$_6$) δ 9.61 (s, 1H), 8.92-8.82 (m, 1H), 8.56-8.24 (m, 1H), 8.17 (d, J = 4.0 Hz, 1H), 7.90 (d, J = 8.0 Hz, 1H), 7.56 (d, J = 8.0 Hz, 1H), 7.33-7.23 (m, 2H), 7.19-7.15 (m, 1H), 6.97-6.87 (m, 2H), 6.77-6.65 (m, 3H), 6.12 (s, 1H), 6.08-6.02 (m, 1H), 5.67-5.58 (m, 1H), 5.17-5.05 (m, 1H), 4.34-4.23 (m, 2H), 4.22-4.13 (m, 2H), 4.11-4.04 (m, 2H), 3.95 (s, 2H), 3.72-3.64 (m, 4H), 3.64-3.53 (m, 6H), 3.52-3.47 (m, 4H), 3.47-3.41 (m, 10H), 3.17-3.11 (m, 1H), 2.79 (s, 2H), 2.69-2.61 (m, 2H), 2.37-2.35 (m, 3H), 2.23-2.13 (m, 2H), 2.10 (s, 3H), 2.05-1.87 (m, 4H), 1.85-1.78 (m, 1H), 1.70-1.57 (m, 2H), 1.27-1.18 (m, 2H), 1.14 (d, J = 4.0 Hz, 3H), 0.89-0.80 (m, 3H), 0.73-0.63 (m, 3H). | 13 | 1185.45 |
| 442 | 1229.78 | | $^1$H NMR (400 MHz, DMSO-d$_6$) δ 9.93-9.46 (m, 1H), 8.98 (s, 1H), 8.29 (t, J = 6.0 Hz, 1H), 8.01 (d, J = 8.8 Hz, 1H), 7.67 (d, J = 7.6 Hz, 1H), 7.39 (t, J = 7.2 Hz, 1H), 7.30-7.23 (m, 2H), 7.08-6.96 (m, 2H), 6.87-6.77 (m, 3H), 6.23-6.11 (m, 2H), 5.75-5.70 (m, 1H), 5.24-5.17 (m, 1H), 4.55-4.13 (m, 7H), 4.06 (s, 2H), 3.78-3.55 (m, 17H), 3.27 (br d, J = 9.7 Hz, 8H), 2.90 (br s, 2H), 2.76 (br d, J = 12.0 Hz, 2H), 2.57 (br d, J = 6.8 Hz, 5H), 2.38-2.25 (m, 3H), 2.23-2.10 (m, 6H), 1.91 (ddd, J = 5.2, 7.6, 12.6 Hz, 1H), 1.75 (br s, 2H), 1.34 (br d, J = 4.4 Hz, 2H), 1.25 (d, J = 6.0 Hz, 3H), 0.97 (d, J = 6.8 Hz, 2H), 0.80 (d, J = 6.8 Hz, 2H), 0.69 (d, J = 6.8 Hz, 1H), 0.57 (d, J = 6.8 Hz, 1H). | 13 | 1229.51 |
| 443 | 1229.78 | | $^1$H NMR (400 MHz, DMSO-d$_6$) δ 9.73 (br s, 1H), 8.98 (s, 1H), 8.36 (t, J = 5.6 Hz, 1H), 8.25 (s, 1H), 8.01 (d, J = 8.8 Hz, 1H), 7.67 (d, J = 8.4 Hz, 1H), 7.43-7.33 (m, 2H), 7.27 (t, J = 7.2 Hz, 1H), 7.08-6.97 (m, 2H), 6.88-6.75 (m, 3H), 6.23 (s, 1H), 6.15 (dd, J = 2.4, 16.8 Hz, 1H), 5.76-5.69 (m, 1H), 5.24-5.14 (m, 1H), 4.43-4.33 (m, 2H), 4.26 (br d, J = 5.4 Hz, 2H), 4.22-4.15 (m, 2H), 4.06 (s, 2H), 3.81-3.59 (m, 13H), 3.54 (br dd, J = 3.6, 6.0 Hz, 5H), 3.33-3.28 (m, 6H), 2.90 (br s, 2H), 2.74 (br s, 2H), 2.49-2.43 (m, 6H), 2.38-2.24 (m, 3H), 2.20 (s, 3H), 2.15-1.99 (m, 4H), 1.93 (ddd, J = 4.8, 8.0, 12.8 Hz, 1H), 1.75 (br s, 2H), 1.41-1.29 (m, 2H), 1.25 (d, J = 6.0 Hz, 3H), 0.97-0.89 (m, 3H), 0.81-0.73 (m, 3H). | 13 | 1229.51 |
| 444 | 1273.81 | 1275.81 | $^1$H NMR (400 MHz, DMSO-d$_6$) δ 8.97 (s, 1H), 8.36 (s, 1H), 8.00 (d, J = 8.3 Hz, 1H), 7.66 (d, J = 7.9 Hz, 1H), 7.41-7.26 (m, 3H), 7.04-6.97 (m, 2H), 6.86-6.76 (m, 3H), 6.22-6.10 (m, 2H), 5.75-5.69 (m, 1H), 5.22-5.17 (m, 1H), 4.40-4.17 (m, 7H), 4.05 (s, 2H), 3.78-3.59 (m, 13H), 3.54-3.47 (m, 19H), 3.23 (d, J = 9.2 Hz, 1H), 2.87-2.65 (m, 5H), 2.44 (s, 3H), 2.36-2.24 (m, 4H), 2.14-2.02 (m, 4H), 1.96-1.88 (m, 1H), 1.74 (s, 2H), 1.33 (m, 2H), 1.24 (d, J = 6.2 Hz, 3H), 0.93 (d, J = 6.6 Hz, 3H), 0.76 (d, J = 6.6 Hz, 3H). | 13 | 1273.56 |
| 445 | 1119.74 | | $^1$H NMR (400 MHz, DMSO-d$_6$) δ 8.32-8.18 (m, 3H), 8.00 (br d, J = 8.2 Hz, 1H), 7.95 (br d, J = 8.9 Hz, 1H), 7.69 (s, 1H), 7.66 (d, J = 8.3 Hz, 1H), 7.59 (d, J = 7.9 Hz, 1H), 7.55-7.48 (m, 2H), 7.38 (t, J = 7.3 Hz, 1H), 7.26 (t, J = 7.5 Hz, 1H), 7.03 (d, J = 8.1 Hz, 1H), 6.87-6.76 (m, 3H), 6.14 (dd, J = 2.1, 16.7 Hz, 1H), 5.76-5.68 (m, 1H), 5.43 (dd, J = 2.8, 7.9 Hz, 1H), 5.28-5.17 (m, 1H), 4.55-4.49 (m, 1H), 4.30 (br s, 2H), 4.06 (br s, 2H), 3.89 (br s, 2H), 3.81 (br t, J = 6.5 Hz, 2H), 3.67 (br s, 6H), 3.51 (br s, 2H), 3.05-2.99 (m, 2H), 2.89 (br s, 1H), 2.78 (br s, 4H), 2.60-2.55 (m, 4H), 2.38 (br d, J = 6.0 Hz, 1H), 2.26 (br d, J = 8.7 Hz, 2H), 2.20 (s, 3H), 2.17 (br s, 2H), 2.09 (s, 1H), 2.03 (br s, 2H), 1.84 (br s, 2H), 1.70 (br s, 2H), 1.56 (br s, 2H), 1.44 (br s, 2H), 1.26 (br d, J = 6.1 Hz, 3H), 1.13 (br d, J = 6.8 Hz, 3H), 1.07 (br s, 2H), 1.02 (br d, J = 6.8 Hz, 1H), 0.96 (br d, J = 12.3 Hz, 1H). | 14 | 1119.44 |
| 446 | 1163.77 | | $^1$H NMR (400 MHz, DMSO-d$_6$) δ 8.33 (s, 1H), 8.28-8.21 (m, 2H), 8.04-7.90 (m, 2H), 7.71-7.63 (m, 2H), 7.60-7.48 (m, 3H), 7.38 (t, J = 7.4 Hz, 1H), 7.26 (t, J = 7.2 Hz, 1H), 7.02 (d, J = 8.1 Hz, 1H), 6.86-6.75 (m, 3H), 6.14 (dd, J = 2.4, 16.7 Hz, 1H), 5.71 (d, J = 12.7 Hz, 1H), 5.42 (d, J = 5.6 Hz, 1H), 5.24-5.14 (m, 1H), 4.57-4.48 (m, 1H), 4.31 (s, 2H), 4.05 (s, 2H), 3.91 (s, 2H), 3.80 (t, J = 7.1 Hz, 2H), 3.71-3.63 (m, 6H), 3.56 (d, J = 5.4 Hz, 3H), 2.99 (q, J = 7.1 Hz, 3H), 2.88 (s, 2H), 2.75-2.65 (m, 3H), 2.35-2.14 (m, 10H), 2.12-2.02 (m, 4H), 1.81-1.53 (m, 10H), 1.36 (s, 2H), 1.23 (d, J = 6.1 Hz, 3H), 1.13-1.02 (m, 7H). | 14 | 1163.49 |
| 447 | 1207.96 | | $^1$H NMR (400 MHz, DMSO-d$_6$) δ 8.29-8.20 (m, 4H), 8.07-7.96 (m, 2H), 7.71-7.62 (m, 2H), 7.59-7.57 (d, J = 8.0 Hz, 1H), 7.56-7.49 (m, 2H), 7.42-7.35 (m, 1H), 7.30-7.20 (m, 1H), 7.03-7.01 (d, J = 8.0 Hz, 1H), 6.88-6.74 (m, 3H), 6.19-6.10 (m, 1H), 5.75-5.68 (m, 1H), 5.48-5.39 (m, 1H), 5.23-5.11 (m, 1H), 4.55-4.47 (m, 1H), 4.34-4.27 (m, 2H), 4.05 (s, 2H), 3.93-3.88 (m, 2H), 3.82-3.77 (m, 2H), 3.73-3.62 (m, 8H), 3.58-3.55 (m, 3H), 3.26-3.17 (m, 6H), 3.14-3.05 (m, 2H), 2.92-2.83 (m, 2H), 2.79-2.68 (m, 2H), 2.31-2.24 (m, 2H), 2.23-2.17 (m, 4H), 2.14-1.99 (m, 5H), 1.88-1.47 (m, 10H), 1.39-1.28 (m, 2H), 1.23-1.21 (d, J = 8.0 Hz, 3H), 1.16-0.94 (m, 9H). | 14 | 1207.55 |
| 448 | 1251.84 | | $^1$H NMR (400 MHz, DMSO-d$_6$) δ 10.31-9.18 (m, 1H), 8.27-8.23 (m, 2H), 8.22 (s, 3H), 8.09-7.93 (m, 2H), 7.71-7.64 (m, 2H), 7.60 (d, J = 8.0 Hz, 1H), 7.56-7.50 (m, 2H), 7.39 (t, J = 7.2 Hz, 1H), 7.30-7.23 (m, 1H), 7.03 (d, J = 8.0 Hz, 1H), 6.89-6.75 | 14 | 1251.60 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | (m, 3H), 6.15 (dd, J = 2.4, 16.8 Hz, 1H), 5.77-5.69 (m, 1H), 5.43 (dd, J = 2.8, 8.0 Hz, 1H), 5.24-5.14 (m, 1H), 4.55-4.48 (m, 1H), 4.34-4.28 (m, 2H), 4.05 (s, 2H), 3.93-3.89 (m, 2H), 3.81 (br t, J = 6.8 Hz, 2H), 3.67 (br dd, J = 3.6, 5.6 Hz, 8H), 3.54-3.49 (m, 14H), 2.90 (br s, 4H), 2.27-2.19 (m, 6H), 2.13-2.01 (m, 4H), 1.79-1.53 (m, 11H), 1.32 (br s, 3H), 1.23 (d, J = 6.0 Hz, 3H), 1.14 (d, J = 6.8 Hz, 3H), 1.10-0.94 (m, 5H). | | |
| 449 | 1295.87 | | $^1$H NMR (400 MHz, DMSO-d$_6$) δ 8.28-8.22 (m, 3H), 8.08-7.96 (m, 2H), 7.71-7.64 (m, 2H), 7.61-7.56 (m, 1H), 7.55-7.49 (m, 2H), 7.41-7.35 (m, 1H), 7.31-7.22 (m, 1H), 7.03-7.01 (d, J = 8.0 Hz, 1H), 6.90-6.73 (m, 3H), 6.20-6.10 (m, 1H), 5.76-5.69 (m, 1H), 5.46-5.39 (m, 1H), 5.25-5.15 (m, 1H), 4.56-4.48 (m, 1H), 4.35-4.27 (m, 2H), 4.04 (s, 2H), 3.93-3.87 (m, 2H), 3.84-3.77 (m, 2H), 3.74-3.60 (m, 8H), 3.60-3.51 (m, 9H), 3.29-3.16 (m, 6H), 3.14-3.05 (m, 2H), 2.94-2.83 (m, 2H), 2.78-2.63 (m, 3H), 2.37-2.29 (m, 2H), 2.27-2.17 (m, 5H), 2.14-1.99 (m, 5H), 1.87-1.47 (m, 10H), 1.38-1.28 (m, 2H), 1.23-1.22 (d, J = 4.0 Hz, 3H), 1.17-0.92 (m, 9H). | 14 | 1295.65 |
| 450 | 1213.67 | 1215.67 | $^1$H NMR (400 MHz, DMSO-d$_6$) δ 10.40 (s, 1H), 9.66 (br s, 1H), 8.47 (br t, J = 5.2 Hz, 1H), 8.31 (d, J = 8.3 Hz, 1H), 8.08-7.96 (m, 1H), 7.73 (br t, J = 6.6 Hz, 1H), 7.66 (br d, J = 8.2 Hz, 1H), 7.62-7.56 (m, 2H), 7.47 (br d, J = 9.7 Hz, 1H), 7.42-7.38 (m, 1H), 7.36 (br d, J = 3.3 Hz, 1H), 7.35-7.32 (m, 1H), 7.30-7.22 (m, 1H), 6.86-6.82 (m, 1H), 6.80-6.75 (m, 1H), 6.15 (dd, J = 2.1, 16.6 Hz, 1H), 5.75-5.69 (m, 1H), 5.25-5.15 (m, 1H), 4.61-4.55 (m, 2H), 4.37 (br s, 1H), 4.05 (br s, 2H), 3.96 (br d, J = 10.6 Hz, 2H), 3.89 (s, 3H), 3.68 (br d, J = 12.1 Hz, 3H), 3.50 (br s, 10H), 2.88 (br s, 2H), 2.76 (br s, 2H), 2.58-2.54 (m, 2H), 2.11 (br s, 2H), 1.78 (br d, J = 9.0 Hz, 2H), 1.64 (br dd, J = 9.7, 13.9 Hz, 1H), 1.45-1.26 (m, 3H), 1.24 (br d, J = 6.1 Hz, 3H), 0.97 (s, 9H). | 15 | 1214.25 |
| 451 | 1257.7 | 1259.7 | $^1$H NMR (400 MHz, DMSO-d$_6$) δ 10.40 (s, 1H), 9.66 (br s, 1H), 8.51-8.43 (m, 1H), 8.31 (d, J = 8.4 Hz, 1H), 8.00 (d, J = 8.2 Hz, 1H), 7.72 (br d, J = 7.1 Hz, 1H), 7.66 (d, J = 8.8 Hz, 1H), 7.59-7.48 (m, 4H), 7.42-7.31 (m, 4H), 7.29-7.23 (m, 1H), 6.88-6.73 (m, 3H), 6.15 (br d, J = 18.6 Hz, 1H), 5.72 (br d, J = 13.0 Hz, 1H), 5.23-5.14 (m, 1H), 4.61-4.54 (m, 2H), 4.36 (br s, 1H), 4.05 (br s, 2H), 3.98-3.87 (m, 5H), 3.66 (br s, 4H), 3.55-3.47 (m, 10H), 3.40 (br d, J = 6.2 Hz, 3H), 3.28-3.25 (m, 2H), 2.89 (br s, 2H), 2.72 (br s, 2H), 2.08 (br d, J = 9.4 Hz, 2H), 1.74 (br s, 2H), 1.69-1.57 (m, 1H), 1.40-1.26 (m, 3H), 1.23 (br d, J = 6.2 Hz, 3H), 0.97 (s, 9H). | 15 | 1258.30 |
| 452 | 1301.73 | 1303.74 | $^1$H NMR (400 MHz, DMSO-d$_6$) δ 10.40 (s, 1H), 9.67 (s, 1H), 8.56-8.42 (m, 1H), 8.31 (d, J = 8 Hz, 1H), 8.18 (s, 1H), 8.00 (d, J = 8 Hz, 1H), 7.75-7.69 (m, 1H), 7.65 (d, J = 8 Hz, 1H), 7.59-7.46 (m, 4H), 7.41-7.31 (m, 4H), 7.29-7.23 (m, 1H), 6.90-6.74 (m, 3H), 6.54 (s, 1H), 6.19-6.12 (m, 1H), 5.76-5.68 (m, 1H), 5.24-5.14 (m, 1H), 4.62-4.55 (m, 2H), 4.41-4.32 (m, 1H), 4.12-3.89 (m, 6H), 3.75-3.63 (m, 4H), 3.53-3.44 (m, 19H), 2.94-2.85 (m, 2H), 2.84-2.69 (m, 2H), 2.15-2.04 (m, 3H), 1.79-1.58 (m, 4H), 1.37-1.29 (m, 2H), 1.23 (d, J = 8.0 Hz, 3H), 0.96 (s, 9H). | 15 | 1302.36 |
| 453 | 1345.76 | 1347.77 | $^1$H NMR (400 MHz, DMSO-d$_6$) δ 10.41 (s, 1H), 9.68 (br s, 1H), 8.49 (t, J = 5.6 Hz, 1H), 8.32 (d, J = 8.4 Hz, 1H), 8.01 (d, J = 8.4 Hz, 1H), 7.73 (t, J = 6.8 Hz, 1H), 7.67 (d, J = 8.0 Hz, 1H), 7.62-7.46 (m, 4H), 7.42-7.32 (m, 4H), 7.27 (ddd, J = 1.2, 6.8, 8.4 Hz, 1H), 6.88-6.75 (m, 3H), 6.15 (dd, J = 2.4, 16.8 Hz, 1H), 5.75-5.69 (m, 1H), 5.21 (sxt, J = 6.0 Hz, 1H), 4.62-4.54 (m, 2H), 4.38 (br dd, J = 8.0, 11.6 Hz, 1H), 4.06 (s, 2H), 3.97 (br d, J = 10.8 Hz, 1H), 3.69 (br d, J = 12.4 Hz, 4H), 3.55-3.44 (m, 21H), 2.90 (br s, 2H), 2.74 (br t, J = 12.4 Hz, 2H), 2.56-2.52 (m, 8H), 2.15-2.05 (m, 2H), 1.81-1.72 (m, 2H), 1.64 (br dd, J = 10.0, 14.4 Hz, 1H), 1.40-1.29 (m, 2H), 1.25 (d, J = 6.4 Hz, 3H), 0.97 (s, 9H). | 15 | 1346.41 |
| 454 | 1389.8 | | $^1$H NMR (400 MHz, DMSO-d$_6$) δ 10.39 (s, 1H), 9.68 (s, 1H), 8.49-8.47 (m, 1H), 8.32-8.30 (m, 1H), 8.01-7.98 (m, 1H), 7.72-7.64 (m, 1H), 7.58-7.48 (m, 4H), 7.38-7.34 (m, 4H), 7.21-7.19 (m, 1H), 6.85-6.76 (m, 3H), 6.17-6.16 (m, 1H), 5.73-5.72 (m, 1H), 5.19-5.15 (m, 1H), 4.58-4.57 (m, 2H), 4.35-4.25 (m, 1H), 4.05 (s, 2H), 3.94-3.91 (m, 1H), 3.89 (s, 3H), 3.69-3.66 (m, 4H), 2.94-2.85 (m, 2H), 2.84-2.69 (m, 2H), 2.15-2.04 (m, 3H), 1.79-1.58 (m, 4H), 1.37-1.29 (m, 2H), 1.23 (d, J = 8.0 Hz, 3H), 0.96 (s, 9H). | 15 | 1390.46 |
| 458 | 1045.77 | 1047.77 | $^1$H NMR (400 MHz, DMSO-d$_6$) δ 9.00-8.93 (m, 1H), 8.48-8.32 (m, 1H), 8.26 (br s, 1H), 7.85-7.69 (m, 2H), 7.47-7.08 (m, 10H), 7.04 (br s, 1H), 6.27-6.00 (m, 1H), 5.04-4.75 (m, 1H), 4.55-4.34 (m, 1H), 4.27 (br s, 1H), 4.09 (br s, 1H), 3.66 (br s, 7H), 2.96-2.86 (m, 2H), 2.77 (s, 2H), 2.68-2.57 (m, 2H), 2.45-2.36 (m, 4H), 2.16 (br s, 3H), 2.05 (br s, 4H), 1.90-1.58 (m, 4H), 1.50 (br s, 2H), 1.32 (br d, J = 6.2 Hz, 3H). | Custom | 1045.63 |
| 459 | 1045.77 | 1047.77 | $^1$H NMR (400 MHz, METHANOL-d$_4$) δ 8.88-8.84 (m, 1H), 7.84-7.76 (m, 1H), 7.75-7.69 (m, 1H), 7.43-7.28 (m, 5H), 7.24 (br s, 1H), 7.20-7.11 (m, 1H), 7.06-6.98 (m, 1H), 6.25-6.15 (m, 1H), 5.05-4.91 (m, 1H), 4.66-4.52 (m, 1H), 4.46-4.28 (m, 1H), 4.23-3.96 (m, 1H), 3.62-3.54 (m, 1H), 3.49-3.33 (m, 4H), 3.05 (s, 2H), 2.88 (s, 1H), 2.76 (br d, J = 5.6 Hz, 2H), 2.49-2.40 (m, 3H), 2.08-1.74 (m, 4H), 1.60 (br d, J = 7.3 Hz, 3H), 1.46 (br t, J = 7.0 Hz, 3H), 1.37 (s, 1H), 1.35-1.20 (m, 6H), 0.93-0.78 (m, 3H). | Custom | 1045.63 |
| 460 | 1059.78 | 1061.78 | $^1$H NMR (400 MHz, METHANOL-d$_4$) δ 8.92 (br d, J = 5.6 Hz, 1H), 8.21-8.03 (m, 1H), 7.77 (br d, J = 8.1 Hz, 1H), 7.48-7.33 (m, 5H), 7.29 (s, 1H), 7.22 (br s, 2H), 7.05 (br s, 1H), 6.30-6.11 (m, 1H), 5.00 (br d, J = 7.1 Hz, 7H), 3.89 (br s, 7H), 3.65-3.46 (m, 2H), 3.02 (br d, J = 3.2 Hz, 2H), 2.92 (s, 1H), 2.80 (br s, 2H), 2.47 (br d, J = 3.2 Hz, 3H), 2.23-1.87 (m, 10H), 1.53-1.41 (m, 3H). | Custom | 1059.66 |
| 461 | 1075.79 | 1077.79 | $^1$H NMR (400 MHz, METHANOL-d$_4$) δ 8.91 (d, J = 3.3 Hz, 1H), 8.10 (br d, J = 8.4 Hz, 1H), 7.77 (br d, J = 7.8 Hz, 1H), 7.50-7.28 (m, 6H), 7.23 (br d, J = 4.5 Hz, 2H), 7.12-6.99 (m, 1H), 6.29-6.08 (m, 1H), 5.08-4.90 (m, 1H), 4.34 (br d, J = 16.6 | Custom | 1075.66 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | Hz, 4H), 3.93-3.76 (m, 6H), 3.71-3.38 (m, 7H), 3.11-3.05 (m, 1H), 2.98 (br d, J = 6.4 Hz, 2H), 2.88-2.65 (m, 1H), 2.47 (s, 3H), 2.32-1.88 (m, 10H), 1.54-1.37 (m, 3H). | | |
| 462 | 1119.82 | 1121.82 | $^1$H NMR (400 MHz, METHANOL-d$_4$) δ 8.90-8.75 (m, 1H), 7.82-7.65 (m, 2H), 7.45-7.29 (m, 5H), 7.23 (br s, 2H), 7.18-7.09 (m, 1H), 7.03 (br s, 1H), 6.27-6.04 (m, 1H), 5.03-4.93 (m, 1H), 4.61-4.52 (m, 1H), 4.48-4.16 (m, 2H), 3.84-3.41 (m, 21H), 3.31 (br d, J = 1.5 Hz, 2H), 3.07 (br d, J = 9.5 Hz, 1H), 2.99-2.65 (m, 4H), 2.43 (s, 3H), 2.25-1.91 (m, 10H), 1.46 (br d, J = 6.5 Hz, 3H), 1.38-1.19 (m, 2H), 0.88 (br d, J = 9.2 Hz, 1H). | Custom | 1119.71 |
| 463 | 1163.85 | 1165.85 | $^1$H NMR (400 MHz, METHANOL-d$_4$) δ 8.90-8.83 (m, 1H), 7.78-7.70 (m, 2H), 7.41-7.35 (m, 5H), 7.23 (br s, 2H), 7.20-7.11 (m, 1H), 7.03 (br s, 1H), 6.23-6.13 (m, 1H), 5.00 (td, J = 7.0, 18.7 Hz, 1H), 4.61-4.54 (m, 1H), 4.48-4.27 (m, 2H), 3.75 (br d, J = 16.5 Hz, 8H), 3.58-3.51 (m, 8H), 3.10 (br d, J = 7.6 Hz, 1H), 2.91 (br d, J = 7.0 Hz, 2H), 2.83-2.70 (m, 2H), 2.65 (s, 1H), 2.45 (d, J = 2.4 Hz, 3H), 2.24-2.10 (m, 10H), 1.47 (br dd, J = 3.1, 6.5 Hz, 3H), 1.28 (s, 1H), 0.88 (br d, J = 8.9 Hz, 1H). | Custom | 1163.76 |
| 464 | 1089.5 | 1091.5 | $^1$H NMR (400 MHz, METHANOL-d$_4$) δ 8.88-8.81 (m, 1H), 7.79-7.69 (m, 2H), 7.43-7.35 (m, 1H), 7.32-7.09 (m, 4H), 7.03-6.86 (m, 3H), 6.21-6.07 (m, 1H), 4.63-4.11 (m, 6H), 4.09-3.55 (m, 16H), 3.26-3.22 (m, 1H), 3.04-2.84 (m, 2H), 2.51-2.33 (m, 6H), 2.24-1.92 (m, 6H), 1.19-1.12 (m, 3H), 1.07-0.94 (m, 3H), 0.90-0.75 (m, 3H). | Custom | 1089.68 |
| 465 | 1089.5 | 1091.5 | $^1$H NMR (400 MHz, METHANOL-d$_4$) δ 8.91-8.81 (m, 1H), 7.80-7.60 (m, 2H), 7.45-6.72 (m, 8H), 6.24-6.05 (m, 1H), 4.61-4.04 (m, 7H), 4.01-3.52 (m, 14H), 3.29-3.19 (m, 2H), 3.06-2.85 (m, 2H), 2.52-2.35 (m, 6H), 2.27-1.92 (m, 6H), 1.21-1.10 (m, 3H), 1.09-0.93 (m, 3H), 0.92-0.77 (m, 3H). | Custom | 1089.68 |
| 466 | 851.38 | 853.38 | $^1$H NMR (400 MHz, DMSO-d$_6$) δ 10.95 (br s, 1H), 8.18 (br s, 1H), 7.84-7.74 (m, 2H), 7.65-7.48 (m, 1H), 7.47-7.36 (m, 1H), 7.33-6.86 (m, 7H), 5.06 (br dd, J = 5.1, 13.3 Hz, 1H), 4.41-4.08 (m, 4H), 3.97-3.47 (m, 12H), 3.11-2.86 (m, 4H), 2.77 (br t, J = 6.9 Hz, 1H), 2.65-2.55 (m, 2H), 2.42-2.24 (m, 3H), 1.97 (br dd, J = 4.8, 10.3 Hz, 1H), 1.10-0.93 (m, 3H). | Custom | 851.33 |
| 467 | 863.46 | | $^1$H NMR (400 MHz, DMSO-d$_6$) δ 11.11 (s, 1H), 10.04 (s, 1H), 8.06 (s, 1H), 7.81 (s, 3H), 7.45-7.22 (m, 6H), 7.06 (s, 1H), 6.82-6.78 (m, 1H), 6.18 (d, J = 16.4 Hz, 1H), 6.75 (d, J = 10.0 Hz, 1H), 5.10 (dd, J = 4.8, 13.2 Hz, 1H), 4.36-4.16 (m, 5H), 3.80-3.65 (m, 6H), 3.62-3.55 (m, 4H), 3.08 (s, 3H), 2.93-2.88 (m, 2H), 2.83 (s, 1H), 2.61-2.56 (m, 1H), 2.07-2.01 (m, 1H). | Custom | 863.30 |
| 468 | 877.62 | 879.63 | $^1$H NMR (400 MHz, DMSO-d$_6$) δ 11.11 (br s, 1H), 8.25 (s, 1H), 7.87-7.77 (m, 3H), 7.48-7.48 (m, 1H), 7.45-7.35 (m, 2H), 7.28-7.09 (m, 4H), 7.04 (s, 1H), 6.86-6.75 (m, 1H), 6.73-6.62 (m, 1H), 5.12 (dd, J = 5.1, 12.8 Hz, 1H), 4.35 (br t, J = 6.4 Hz, 2H), 3.92-3.64 (m, 7H), 3.52-3.48 (m, 3H),, 2.97 (br s, 1H), 2.89 (br s, 1H), 2.79 (br s, 3H), 2.73 (br d, J = 6.0 Hz, 2H), 2.65-2.54 (m, 4H), 2.10-1.99 (m, 1H). | Custom | 877.33 |
| 469 | 1367.97 | 1369.97 | $^1$H NMR (400 MHz, METHANOL-d$_4$) δ 0.57 (d, J = 6.72 Hz, 1H) 0.73 (d, J = 6.72 Hz, 1H) 0.90 (dd, J = 6.60, 1.83 Hz, 2H) 1.05 (d, J = 6.72 Hz, 2H) 2.02-2.37 (m, 5H) 2.50 (d, J = 1.71 Hz, 3H) 2.77-3.11 (m, 5H) 3.56-3.96 (m, 29H) 4.13-4.73 (m, 11H) 5.86-6.03 (m, 1H) 6.95-7.49 (m, 12H) 7.71-7.87 (m, 2H) 8.87 (d, J = 1.47 Hz, 1H) | Custom | 1367.99 |
| 470 | 1367.97 | 1369.97 | $^1$H NMR (400 MHz, METHANOL-d$_4$) δ 60.87 (br d, J = 6.72 Hz, 3H) 1.03 (br d, J = 6.24 Hz, 3H) 2.03-2.42 (m, 5H) 2.05-2.47 (m, 15H) 2.45-2.57 (m, 3H) 2.87 (br d, J = 15.04 Hz, 2H) 3.00-3.19 (m, 3H) 3.53-4.02 (m, 26H) 4.02-4.86 (m, 16H) 5.62-6.08 (m, 1H) 6.95-7.39 (m, 10H) 7.41-7.52 (m, 2H) 7.76-7.85 (m, 1H) 8.12-8.26 (m, 1H) 8.89-8.94 (m, 1H). | Custom | 1367.99 |
| 471 | 1089.79 | 1091.79 | $^1$H NMR (400 MHz, DMSO-d$_6$) δ 11.08 (s, 1H), 8.71 (s, 1H), 8.07 (s, 1H), 7.82 (d, J = 8.3 Hz, 2H), 7.48-7.42 (m, 2H), 7.38 (dd, J = 2.3, 8.3 Hz, 1H), 7.30 (d, J = 2.2 Hz, 1H), 7.26-7.18 (m, 2H), 7.10 (d, J = 2.3 Hz, 1H), 5.11 (dd, J = 5.3, 12.9 Hz, 1H), 4.36-4.30 (m, 2H), 3.92 (s, 4H), 3.78-3.67 (m, 6H), 3.50 (s, 2H), 2.93-2.82 (m, 1H), 2.62-2.54 (m, 2H), 2.39 (s, 2H), 2.08-1.98 (m, 1H), 1.58 (s, 4H). | Custom | 1089.68 |
| 472 | 1089.8 | 1091.8 | $^1$H NMR (400 MHz, MeOD-d$_4$) δ 8.36-8.78 (m, 1H), 7.77-7.72 (m, 2H), 7.39-7.02 (m, 9H), 6.20-6.14 (m, 1H), 5.01 (s, 1H), 4.75-4.48 (m, 2H), 4.56-4.39 (m, 1H), 3.84-3.58 (m, 18H), 3.70-2.87 (m, 314), 2.80-2.58 (m, 2H), 2.43-2.37 (m, 4H), 2.22-2.17 (m, 7H), 1.94-1.93 (m, 1H), 1.04-0.92 (m, 3H), 0.87-0.77 (m, 3H). | Custom | 1089.68 |
| 473 | 1196.9 | 1198.9 | $^1$H NMR (400 MHz, CD$_3$OD) δ 9.01-8.89 (m, 1H), 8.17-8.05 (m, 1H), 7.76 (d, J = 8.4 Hz, 1H), 7.58-7.38 (m, 5H), 7.28 (d, J = 2.4 Hz, 1H), 7.25-7.16 (m, 2H), 7.05 (d, J = 2.4 Hz, 1H), 6.89-6.73 (m, 1H), 6.36-6.23 (m, 1H), 5.86-5.75 (m, 1H), 5.04-4.94 (m, 1H), 4.82-4.75 (m, 1H), 4.69-4.63 (m, 1H), 4.58-4.51 (m, 1H), 4.46-4.31 (m, 1H), 4.16-4.06 (m, 4H), 4.05-3.99 (m, 2H), 3.98-3.89 (m, 4H), 3.88-3.80 (m, 3H), 3.80-3.39 (m, 18H), 3.11-2.99 (m, 3H), 2.51-2.42 (m, 3H), 2.40-2.13 (m, 1H), 2.03-1.90 (m, 1H), 1.60-1.43 (m, 3H), 1.07-0.96 (m, 9H). | Custom | 1196.83 |
| 474 | 1222.92 | 1224.92 | $^1$H NMR (400 MHz, DMSO-d$_6$) δ 9.56 (brs, 1H), 8.98 (s, 1H), 8.42 (d, J = 7.6 Hz, 1H), 8.04 (s, 1H), 7.81 (d, J = 8.4 Hz, 1H), 7.51-6.99 (m, 10H), 6.83 (dd, J = 10.4, 16.4 Hz, 1H), 6.25-6.10 (m, 1H), 5.83-5.69 (m, 1H), 5.44-5.13 (m, 1H), 4.97-4.80 (m, 1H), 4.53 (d, J = 9.6 Hz, 1H), 4.42 (t, J = 8.4 Hz, 1H), 4.32-4.20 (m, 1H), 4.07-3.70 (m, 10H), 3.59-3.53 (m, 16H), 3.35-3.05 (m, 6H), 3.02-2.86 (m, 2H), 2.44 (s, 3H), 2.38-2.32 (m, 1H), 2.24-2.10 (m, 2H), 2.09-1.88 (m, 2H), 1.82-1.70 (m, 1H), 1.49-1.32 (m, 3H), 0.92 (s, 9H). | Custom | 1222.87 |
| 475 | 1202.88 | 1204.88 | $^1$H NMR (400 MHz, DMSO-d$_6$) δ 8.98 (s, 1H), 8.74-8.38 (m, 1H), 8.27 (s, 2H), 8.00 (s, 1H), 7.80 (d, J = 8.3 Hz, 1H), 7.74-7.49 (m, 1H), 7.46-7.39 (m, 3H), 7.38-7.32 (m, 2H), 7.28 (d, J = 2.3 Hz, 1H), 7.25-7.16 (m, 2H), 7.06 (d, J = 2.3 Hz, 1H), 6.83 | Custom | 1202.89 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| | | | (dd, J = 10.5, 16.6 Hz, 1H), 6.18 (dd, J = 2.3, 16.7 Hz, 1H), 5.78-5.70 (m, 1H), 5.03 (td, J = 4.4, 8.3 Hz, 1H), 4.88 (quin, J = 7.0 Hz, 1H), 4.53-4.33 (m, 2H), 4.30-4.20 (m, 1H), 3.92 (br d, J = 2.5 Hz, 4H), 3.85 (br s, 2H), 3.77 (br s, 2H), 3.60-3.55 (m, 4H), 3.49 (br s, 10H), 3.02 (br d, J = 16.1 Hz, 1H), 2.91-2.83 (m, 2H), 2.78 (br s, 2H), 2.47 (br s, 4H), 2.45 (s, 3H), 2.30-2.22 (m, 2H), 2.10-1.95 (m, 3H), 1.80-1.62 (m, 1H), 1.80-1.62 (m, 2H), 1.48-1.33 (m, 3H), 0.90 (s, 8H). | | |
| 476 | 1119.81 | 1121.81 | $^1$H NMR (400 MHz, METHANOL-d$_4$) δ ppm 0.90 (br s,3H) 1.01-1.11 (m, 4H) 2.19 (s, 4H) 2.46 (d, J = 1.83 Hz, 3H) 2.88-3.08 (m, 9H) 3.69-3.97 (m, 18H) 4.27-4.65 (m, 8H) 6.00 (br s, 1H) 7.11 (br s, 1H) 7.26-7.49 (m, 10H) 7.79 (d, J = 9.29 Hz, 1H) 8.10 (s, 1H) 8.88 (d, J = 2.45 Hz, 1H). | Custom | 1119.71 |
| 477 | 1119.81 | 1121.81 | $^1$H NMR (400 MHz, METHANOL-d$_4$) δ ppm 0.86 (br d, J = 6.60 Hz, 3H) 1.03 (dd, J = 6.60, 1.96 Hz, 3H) 1.01-1.05 (m, 1H) 2.19 (s, 4H) 2.42-2.50 (m, 4H) 2.88-3.10 (m, 10H) 3.72-4.03 (m, 16H) 4.20-4.56 (m, 13H) 5.99 (br s, 1H) 7.07-7.52 (m, 12H) 7.79 (d, J = 8.44 Hz, 1H) 8.13 (s, 1H) 8.90 (s, 1H). | Custom | 1119.71 |
| 478 | 831.56 | 833.56 | $^1$H NMR (400 MHz, METHANOL-d$_4$) δ 7.83-7.54 (m, 2H), 7.39-7.04 (m, 3H), 6.83-6.64 (m, 3H), 6.35-6.17 (m, 1H), 5.86-5.72 (m, 1H), 5.08 (br dd, J = 5.2, 12.8 Hz, 1H), 4.24 (br s, 2H), 4.07-3.54 (m, 12H), 3.22 (br s, 1H), 3.05-2.64 (m, 7H), 2.16-2.04 (m, 1H). | Custom | 831.23 |
| 479 | 831.56 | 833.56 | $^1$H NMR (400 MHz, METHANOL-d$_4$) δ 7.72 (br d, J = 8.7 Hz, 2H), 7.37-7.06 (m, 3H), 6.86-6.64 (m, 3H), 6.25 (dd, J = 5.2, 15.2 Hz, 1H), 5.79 (br dd, J = 4.8, 12.0 Hz, 1H), 5.09 (br d, J = 13.2 Hz, 1H), 4.25 (br s, 2H), 4.00-3.58 (m, 12H), 3.02 (s, 2H), 2.94-2.79 (m, 3H), 2.77-2.62 (m, 3H), 2.11 (br s, 1H). | Custom | 831.23 |
| 480 | 1228.95 | | $^1$H NMR (400 MHz, DMSO-d$_6$) δ 8.97 (s, 1H), 8.41 (br d, J = 7.8 Hz, 1H), 8.23-8.14 (m, 1H), 7.97-7.88 (m, 1H), 7.64 (d, J = 8.1 Hz, 1H), 7.58-7.51 (m, 2H), 7.49-7.41 (m, 3H), 7.36 (br d, J = 8.1 Hz, 3H), 7.22 (d, J = 7.5 Hz, 1H), 6.87 (br s, 1H), 6.19 (br d, J = 16.1 Hz, 1H), 5.81-5.74 (m, 1H), 5.00-4.85 (m, 2H), 4.54 (d, J = 9.5 Hz, 1H), 4.48-4.36 (m, 2H), 4.33-4.21 (m, 3H), 4.19-4.08 (m, 4H), 4.07-3.97 (m, 3H), 3.95 (s, 2H), 3.58 (br d, J = 8.6 Hz, 6H), 3.54 (s, 4H), 3.51 (s, 3H), 3.50-3.43 (m, 4H), 3.19 (br d, J = 13.8 Hz, 3H), 3.10-2.84 (m, 4H), 2.78-2.68 (m, 2H), 2.45 (br s, 2H), 2.45-2.44 (m, 1H), 2.17 (br dd, J = 5.9, 9.4 Hz, 2H), 2.01 (br s, 2H), 1.90-1.81 (m, 2H), 1.76 (br d, J = 4.5 Hz, 1H), 1.48-1.32 (m, 3H), 0.93 (s, 9H). | Custom | 1228.52 |
| 481 | 1000.73 | | $^1$H NMR (400 MHz, DMSO-d$_6$) δ 10.71 (br s, 1H), 8.23-8.14 (m, 1H), 7.96-7.89 (m, 1H), 7.82 (d, J = 8.3 Hz, 1H), 7.64 (d, J = 8.2 Hz, 1H), 7.58-7.51 (m, 2H), 7.49-7.43 (m, 2H), 7.36 (dd, J = 2.2, 8.3 Hz, 1H), 7.27-7.20 (m, 1H), 6.87 (br s, 1H), 6.20 (br d, J = 16.5 Hz, 1H), 5.78 (br d, J = 12.2 Hz, 1H), 5.12 (dd, J = 5.4, 12.8 Hz, 1H), 5.05-4.70 (m, 1H), 4.48-4.24 (m, 3H), 4.22-3.93 (m, 7H), 3.83-3.75 (m, 2H), 3.63-3.53 (m, 5H), 3.53-3.42 (m, 8H), 3.30-3.13 (m, 4H), 3.13-2.78 (m, 6H), 2.76-2.67 (m, 1H), 2.56 (br d, J = 9.4 Hz, 214), 2.33 (s, 3H), 2.17 (dd, J = 6.1, 9.5 Hz, 2H), 2.07-1.98 (m, 1H), 1.93-1.74 (m, 2H). | Custom | 1000.12 |
| 482 | 1142.84 | 1144.84 | $^1$H NMR (400 MHz, DMSO-d$_6$) δ 9.53 (s, 1H) 8.97 (s, 1H) 8.46-8.23 (m, 2H) 7.87 (s, 1H) 7.80 (d, J = 8.4 Hz, 1H) 7.83-7.69 (m, 1H) 7.61-7.13 (m, 8H) 7.56-7.10 (m, 2H) 7.07 (d, J = 2.4 Hz, 1H) 6.95-6.78 (m, 3H) 6.18 (d, J = 16.8 Hz, 1H) 5.74 (d, J = 10.4Hz, 1H) 4.99-4.78 (m, 1H) 4.60-4.40 (m, 3H) 4.28 (s, 1H) 4.08 (s, 2H) 4.00-3.91 (m, 2H) 3.89-3.71 (m, 10H) 3.65 (s, 4H) 3.59-3.53 (m, 2H) 2.44 (s, 3H) 2.10-1.95 (m, 1H) 1.80-1.65 (m, 1H) 1.33 (d, J = 6.8 Hz, 3H) 1.24 (s, 1H) 0.93 (s, 9H). | Custom 1 | 1142.74 |
| 483 | 1186.87 | 1188.87 | $^1$H NMR (400 MHz, DMSO-d$_6$) δ 9.53 (s, 1H), 8.97 (s, 1H), 8.41 (d, J = 7.6 Hz, 1H), 8.32-8.25 (m, 1H), 7.92-7.68 (m, 4H), 7.49-7.31 (m, 6H), 7.30-7.19 (m, 3H), 7.08 (d, J = 2.1 Hz, 1H), 6.92-6.78 (m, 3H), 6.24-6.10 (m, 1H), 5.80-5.70 (m, 1H), 4.95-4.81 (m, 1H), 4.54 (d, J = 9.6 Hz, 1H), 4.44 (t, J = 8.0 Hz, 1H), 4.28 (s, 1H), 4.04 (t, J = 3.6 Hz, 2H), 3.95 (s, 2H), 3.88-3.69 (m, 9H), 3.66-3.51 (m, 11H), 2.44 (s, 3H), 2.10-1.98 (m, 1H), 1.82-1.71 (m, 1H), 1.44-1.27 (m, 3H), 0.93 (s, 9H). | Custom 1 | 1186.80 |
| 484 | 1230.91 | 1232.91 | $^1$H NMR (400 MHz, DMSO-d$_6$ + D$_2$O) δ 9.53 (br s, 1H), 8.97 (s, 1H), 8.41 (br d, J = 7.6 Hz, 1H), 7.92-7.69 (m, 4H), 7.48-7.40 (m, 3H), 7.39-7.32 (m, 3H), 7.30-7.21 (m, 3H), 7.08 (d, J = 2.4 Hz, 1H), 6.92-6.81 (m, 3H), 6.19 (dd, J = 2.0, 16.4 Hz, 1H), 5.80-5.70 (m, 1H), 5.27-4.80 (m, 2H), 4.54 (d, J = 9.6 Hz, 1H), 4.45 (t, J = 8.4 Hz, 1H), 4.28 (br s, 1H), 4.04 (br d, J = 4.4 Hz, 2H), 3.95 (s, 2H), 3.86 (br s, 8H), 3.76-3.68 (m, 3H), 3.63-3.53 (m, 14H), 2.45 (s, 3H), 2.11-1.98 (m, 1H), 1.84-1.72 (m, 1H), 1.37 (d, J = 7.2 Hz, 3H), 0.94 (s, 9H). | Custom 1 | 1230.85 |
| 485 | 1133.84 | 1135.84 | $^1$H NMR (400 MHz, DMSO-d$_6$) δ 8.92-8.82 (m, 1H), 8.33 (br s, 1H), 7.84 (br s, 1H), 7.75 (d, J = 8.2 Hz, 1H), 7.48-7.36 (m, 5H), 7.31-7.13 (m, 2H), 7.04 (d, J = 2.4 Hz, 1H), 6.27-6.19 (m, 1H), 5.16-5.06 (m, 1H), 4.60 (br t, J = 8.2 Hz, 2H), 4.44 (br s, 1H), 3.90-3.71 (m, 12H), 3.66-3.42 (m, 18H), 3.19-2.90 (m, 3H), 2.90-2.73 (m, 2H), 2.51 (s, 1H), 2.52-2.32 (m, 4H), 2.25 (d, J = 2.2 Hz, 3H), 2.19 (s, 3H), 2.02-1.92 (m, 1H), 1.11-1.03 (m, 3H), 0.90-0.83 (m, 3H). | Custom 2 | 1133.74 |
| 486 | 1133.84 | 1135.84 | $^1$H NMR (400 MHz, DMSO-d$_6$) δ 10.06 (br s, 1H), 8.96 (d, J = 3.3 Hz, 1H), 8.41 (br d, J = 8.1 Hz, 1H), 7.82-7.73 (m, 2H), 7.49-7.31 (m, 5H), 7.26 (d, J = 2.3 Hz, 1H), 7.21 (br s, 2H), 7.04 (d, J = 2.2 Hz, 2H), 6.24-6.07 (m, 1H), 5.28-4.89 (m, 2H), 4.83-4.35 (m, 1H), 4.26 (br s, 1H), 3.81-3.58 (m, 11H), 3.55-3.39 (m, 12H), 3.00-2.73 (m, 3H), 2.66-2.54 (m, 2H), 2.46-2.41 (m, 3H), 2.28-2.14 (m, 4H), 2.05 (d, J = 2.7 Hz, 4H), 1.93-1.70 (m, 1H), 0.95 (br d, J = 6.4 Hz, 3H), 0.80-0.70 (m, 3H). | Custom 2 | 1133.74 |

TABLE 11-continued

Data for Compounds of Table 10

| Ex. No. | MH+ (1) | MH+ (2) | NMR Transcript | Synthetic Scheme | Mol Weight |
|---|---|---|---|---|---|
| 487 | 1177.87 | 1179.87 | ¹H NMR (400 MHz, METHANOL-d₄) δ 8.90-8.79 (m, 1H), 7.79 (s, 1H), 7.72 (d, J = 8.3 Hz, 1H), 7.41-7.29 (m, 5H), 7.25-7.11 (m, 3H), 7.03-6.98 (m, 1H), 6.22-6.16 (m,1H), 5.06-4.97 (m, 1H), 4.71-4.55 (m, 3H), 4.45-4.29 (m, 1H), 3.81 (br dd, J = 8.7, 19.6 Hz, 12H), 3.62-3.48 (m, 12H), 3.14-3.07 (m, 2H), 2.91 (br s, 4H), 2.48-2.33 (m, 4H), 2.24-2.14 (m, 7H), 1.99-1.86 (m, 1H), 1.06-0.91 (m, 3H), 0.87-0.74 (m, 3H). | Custom 2 | 1177.79 |
| 488 | 1177.87 | 1179.87 | ¹H NMR (400 MHz, METHANOL-d₄) δ 8.84 (d, J = 1.2 Hz, 1H), 7.80 (br s, 1H), 7.73 (br d, J = 8.6 Hz, 1H), 7.42-7.33 (m, 5H), 7.25-7.13 (m, 3H), 7.03-6.98 (m, 1H), 6.21-6.18 (m, 1H), 5.06 (br s, 1H), 4.69-4.52 (m, 3H), 4.44-4.33 (m, 1H), 3.84-3.71 (m, 12H), 3.62-3.49 (m, 12H), 3.16-3.07 (m, 2H), 2.94-2.70 (m, 4H), 2.45-2.37 (m, 4H), 2.23-2.14 (m, 7H), 2.01-1.88 (m, 1H), 1.04 (d, J = 6.5 Hz, 3H), 0.84 (br d, J = 6.8 Hz, 3H). | Custom 2 | 1177.79 |
| 489 | 1221.91 | 1223.91 | ¹H NMR (400 MHz, MeOD-d₄) δ 8.89-8.83 (m, 1H), 8.43 (br s, 1H), 7.81 (br s, 1H), 7.73 (d, J = 8.2 Hz, 1H), 7.46-7.32 (m, 5H), 7.24 (d, J = 2.1 Hz, 2H), 7.18 (br t, J = 7.2 Hz, 1H), 7.02 (q, J = 2.4 Hz, 1H), 6.25-6.19 (m, 1H), 5.18-5.00 (m, 1H), 4.67-4.60 (m, 2H), 4.45-4.32 (m, 1H), 3.86-3.68 (m, 12H), 3.64-3.44 (m, 18H), 3.13-2.90 (m, 3H), 2.86-2.80 (m, 1H), 2.75 (br t, J = 6.9 Hz, 1H), 2.50-2.35 (m, 4H), 2.26-2.14 (m, 7H), 1.95 (br s, 1H), 1.06-0.91 (m, 3H), 0.89-0.75 (m, 3H). | Custom 2 | 1221.84 |
| 490 | 1221.92 | 1223.92 | ¹H NMR (400 MHz, MeOD-d₄) δ 8.92-8.82 (m, 1H), 8.33 (br s, 1H), 7.84 (br s, 1H), 7.75 (d, J = 8.2 Hz, 1H), 7.48-7.36 (m, 5H), 7.31-7.13 (m, 3H), 7.04 (d, J = 2.4 Hz, 1H), 6.27-6.19 (m, 1H), 5.16-5.06 (m, 1H), 4.60 (br t, J = 8.2 Hz, 2H), 4.44 (br s, 1H), 3.90-3.71 (m, 12H), 3.66-3.42 (m, 18H), 3.19-2.90 (m, 3H), 2.90-2.73 (m, 2H), 2.51 (s, 1H), 2.52-2.32 (m, 4H), 2.25 (d, J = 2.2 Hz, 3H), 2.19 (s, 3H), 2.02-1.92 (m, 1H), 1.11-1.03 (m, 3H), 0.90-0.83 (m, 3H). | Custom 2 | 1221.84 |
| 491 | 1265.94 | 1267.94 | ¹H NMR (400 MHz, MeOD-d₄) δ 8.92-8.82 (m, 1H), 8.33 (br s, 1H), 7.84 (br s, 1H), 7.75 (d, J = 8.2 Hz, 1H), 7.48-7.36 (m, 5H), 7.24 (br d, J = 2.3 Hz, 2H), 7.19 (br d, J = 6.0 Hz, 1H), 7.02 (s, 1H), 6.25-6.18 (m, 1H), 5.16-5.06 (m, 1H), 4.60 (br t, J = 8.2 Hz, 2H), 4.44 (br s, 1H), 3.90-3.71 (m, 12H), 3.66-3.42 (m, 22H), 3.19-2.90 (m, 3H), 2.90-2.73 (m, 1H), 2.51 (s, 1H), 2.52-2.32 (m, 4H), 2.25 (d, J = 2.2 Hz, 4H), 2.19 (s, 3H), 2.02-1.92 (m, 1H), 1.11-1.03 (m, 3H), 0.90-0.83 (m, 3H). | Custom 2 | 1265.89 |
| 492 | 1265.95 | 1267.95 | ¹H NMR (400 MHz, MeOD-d₄) δ 8.85 (s, 1H), 8.46 (br s, 1H), 7.82 (s, 1H), 7.73 (d, J = 8.4 Hz, 1H), 7.46-7.35 (m, 5H), 7.24 (br d, J = 2.3 Hz, 2H), 7.19 (br d, J = 6.0 Hz, 1H), 7.02 (s, 1H), 6.25-6.18 (m, 1H), 5.09 (s, 1H), 4.62-4.54 (m, 2H), 4.46-4.34 (m, 1H), 3.89-3.72 (m, 12H), 3.65-3.41 (m, 22H), 3.15-2.90 (m, 3H), 2.83 (br t, J = 7.0 Hz, 1H), 2.75 (br t, J = 6.8 Hz, 1H), 2.45 (s, 3H), 2.42-2.31 (m, 7H), 2.29-2.08 (m, 7H), 2.04-1.90 (m, 1H), 1.05 (d, J = 6.6 Hz, 3H), 0.89-0.81 (m, 3H). | Custom 2 | 1265.89 |
| 493 | 1133.85 | 1135.85 | ¹H NMR (400 MHz, METHANOL-d₄) δ 0.61 (dd, J = 6.6, 2.4 Hz, 1H), 0.77 (dd, J = 6.6, 2.4 Hz, 1H), 0.88 (d, J = 6.4 Hz, 2H), 1.03 (d, J = 6.4 Hz, 2H), 1.86-2.01 (m, 2H), 2.03-2.11 (m, 1H), 2.17 (s, 3H), 2.19-2.27 (m, 1H), 2.28-2.39 (m, 1H), 2.42-2.47 (m, 3H), 2.76-2.91 (m, 5H), 3.02-3.18 (m, 3H), 3.52-3.59 (m, 2H), 3.65-4.01 (m, 16H), 4.15 (br d, J = 4.8 Hz, 1H), 4.36-4.42 (m, 2H), 4.54-4.64 (m, 4H), 5.83-5.99 (m, 1H), 7.02 (d, J = 2.0 Hz, 1H), 7.14-7.21 (m, 1H), 7.22-7.28 (m, 2H), 7.32-7.50 (m, 5H), 7.71-7.82 (m, 2H), 8.81-8.87 (m, 1H). | Custom 3 | 1133.74 |
| 494 | 1133.83 | 1135.83 | ¹H NMR (400 MHz, METHANOL-d₄) δ 0.82-0.88 (m, 3H), 1.02 (dd, J = 6.0, 2.02 Hz, 3H), 1.92-2.04 (m, 2H), 2.05-2.13 (m, 1H), 2.17 (s, 3H), 2.19-2.27 (m, 1H), 2.29-2.41 (m, 1H), 2.41-2.49 (m, 3H), 2.75-2.95 (m, 5H), 3.01-3.21 (m, 3H), 3.60-3.64 (m, 2H), 3.65-4.06 (m, 16H), 4.22 (br d, J = 5.2 Hz, 1H), 4.38-4.45 (m, 1H), 4.46-4.54 (m, 2H), 4.58 (s, 4H), 5.96 (s, 1H), 6.98-7.07 (m, 1H), 7.14-7.22 (m, 1H), 7.22-7.30 (m, 2H), 7.34-7.49 (m, 5H), 7.74 (d, J = 8.0 Hz, 1H), 7.78-7.84 (m, 1H), 8.80-8.90 (m, 1H). | Custom 3 | 1133.74 |
| 495 | 1147.85 | 1149.85 | ¹H NMR (400 MHz, METHANOL-d₄) δ 0.57-0.65 (m, 1H), 0.76 (d, J = 6.4 Hz, 1H), 0.85-0.92 (m, 2H), 1.03 (d, J = 6.4 Hz, 2H), 1.54-1.79 (m, 4H), 2.01-2.10 (m, 1H), 2.14 (s, 3H), 2.19-2.27 (m, 1H), 2.27-2.38 (m, 1H), 2.40-2.47 (m, 3H), 2.76-2.93 (m, 5H), 2.99-3.16 (m, 3H), 3.42-3.49 (m, 2H), 3.63-3.81 (m, 12 H,) 3.84-4.15 (m, 6H), 4.34-4.42 (m, 2H), 4.47 (br s, 1H), 4.54-4.69 (m, 2H), 5.84-5.98 (m, 1H), 6.97-7.05 (m, 1H), 7.10-7.19 (m, 1H), 7.23 (br d, J = 2.4 Hz, 2H), 7.30-7.40 (m, 4H), 7.41-7.50 (m, 1H), 7.72 (d, J = 8.4 Hz, 1H), 7.75-7.80 (m, 1H), 8.79-8.89 (m, 1H). | Custom 3 | 1147.76 |
| 496 | 1147.86 | 1149.86 | ¹H NMR (400 MHz, METHANOL-d₄) δ 0.82-0.90 (m, 3H), 1.02 (br d, J = 6.0 Hz, 3H), 1.58-1.87 (m, 4H), 1.99-2.13 (m, 1H), 2.17 (s, 3H), 2.19-2.27 (m, 1H), 2.30-2.41 (m, 1H), 2.42 (br d, J = 1.2 Hz, 3H), 2.72-2.97 (m, 5H), 3.07-3.16 (m, 2H), 3.47-3.55 (m, 2H), 3.59-3.86 (m, 12H), 3.87-4.20 (m, 6H), 4.45-4.49 (m, 1H), 4.57-4.60 (m, 5H), 5.86-6.09 (m, 1H), 6.95-7.07 (m, 1H), 7.11-7.22 (m, 1H), 7.23-7.32 (m, 2H), 7.34-7.51 (m, 5H), 7.73 (d, J = 8.4 Hz, 1H) 7.78-7.84 (m, 1H), 8.81-8.90 (m, 1H). | Custom 3 | 1147.76 |
| 497 | 1210.9388 | 1212.9395 | ¹H NMR (400 Hz, Methanol-d₄) δ ppm 8.83 (s, 1H), 7.97 (s, 1H), 7.73 (d, J = 8 Hz, 1H), 7.38 (m, 5H), 7.24-7.14 (m, 3H), 7.02 (s, 1H), 6.78 (dd, J = 16, 12 Hz, 1H), 6.25 (d, J = 12 Hz, 1H), 5.78 (d, J = 12 Hz, 1H), 4.97 (m, 1H), 4.64 (s, 1H), 4.45-4.40 (m, 4H), 4.00-3.80 (m, 8H), 3.65-3.54 (m, 14H), 2.76-2.63 (m, 5H), 2.44 (s, 3H), 2.31 (s, 3H), 2.16 (m, 1H), 2.20-1.87 (m, 3H), 1.47 (d, J = 8 Hz, 3H), 1.00 (s, 9H). | Custom | 1210.86 |

TABLE 12

Compounds Prepared by Schemes 17-24

| Ex. No. | Structure | Compound Name | Synthetic Scheme |
|---|---|---|---|
| 498 | 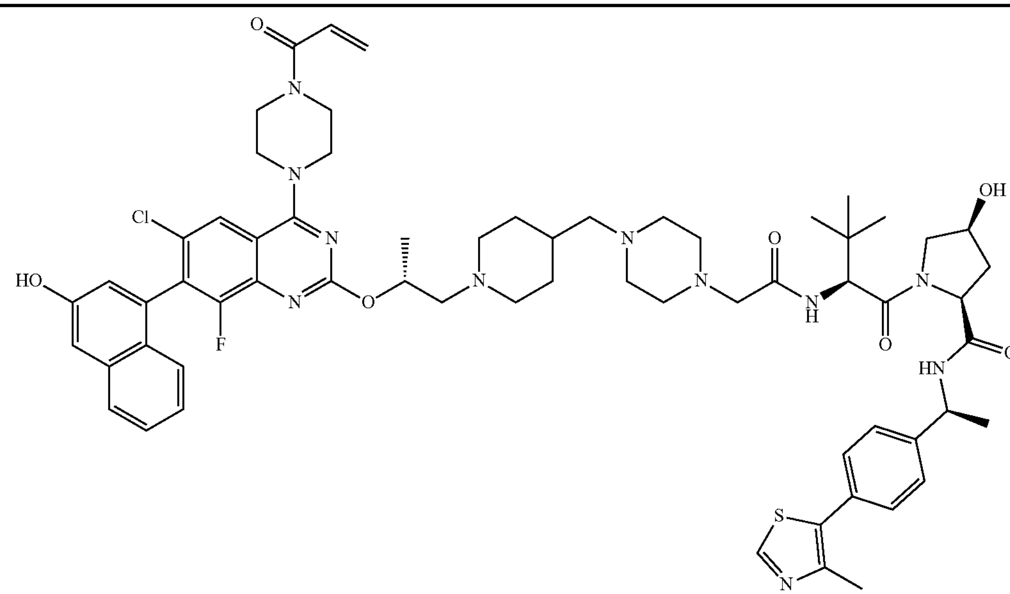 | (2S,4S)-1-((2S)-2-(2-(4-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)methyl)piperazin-1-yl)acetamido)-3,3-dimethylbutanoyl)-4-hydroxy-N-((s)-1-(4-(4-methylthiazol-5-yl)phenyl)ethyl)pyrrolidine-2-carboxamide | 11 |

TABLE 12-continued
Compounds Prepared by Schemes 17-24
| Ex. No. | Structure | Compound Name | Synthetic Scheme |
|---|---|---|---|
| 499 | 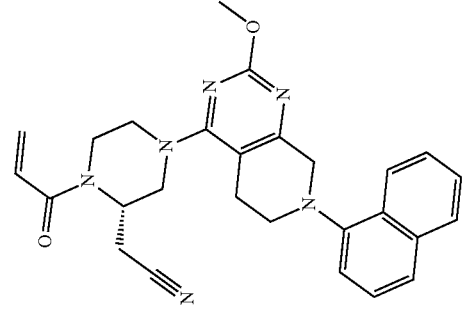 | (2S,4R)-1-((S)-2-(2-(2-(((3R,5S)-5-((((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 17 |

TABLE 12-continued
Compounds Prepared by Schemes 17-24
| Ex. No. | Structure | Compound Name | Synthetic Scheme |
|---|---|---|---|
| 500 | 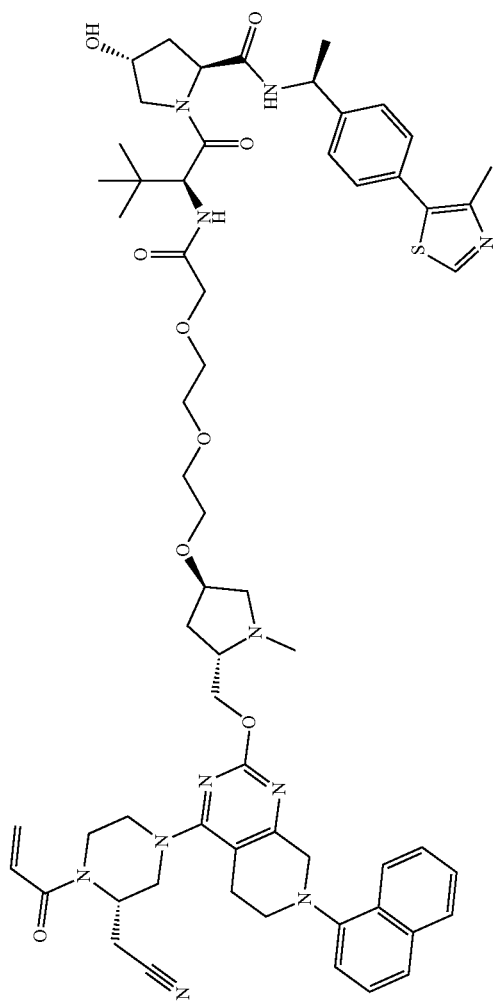 | (2S,4R)-1-((S)-2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 17 |

TABLE 12-continued
Compounds Prepared by Schemes 17-24
| Ex. No. | Structure | Compound Name | Synthetic Scheme |
|---|---|---|---|
| 501 | 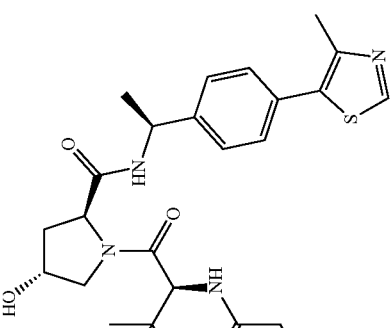 | (2S,4R)-1-((S)-14-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)-2-(tert-butyl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | 17 |

TABLE 12-continued

Compounds Prepared by Schemes 17-24

| Ex. No. | Structure | Compound Name | Synthetic Scheme |
|---|---|---|---|
| 502 | 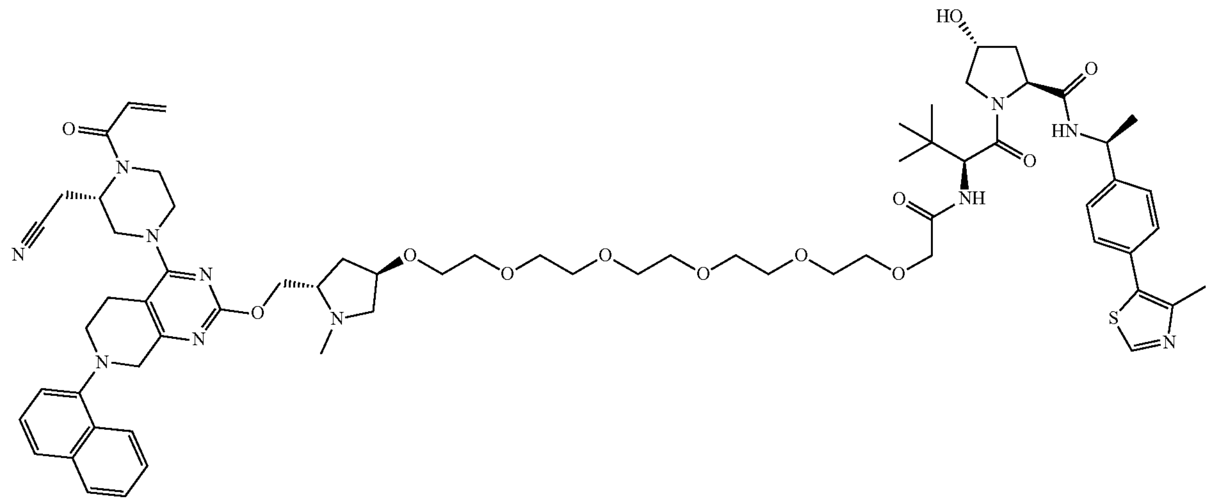 [SMILES: C=CC(=O)N1CCN(c2nc(OC[C@@H]3C[C@@H](OCCOCCOCCOCCOCCOCC(=O)N[C@H](C(=O)N4C[C@H](O)C[C@H]4C(=O)N[C@@H](C)c4ccc(-c5scnc5C)cc4)C(C)(C)C)CN3C)nc3c2CCN(c2cccc4ccccc24)C3)C[C@@H]1CC#N] | (2S,4R)-1-((S)-20-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)-2-(tert-butyl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | 17 |
| 503 | 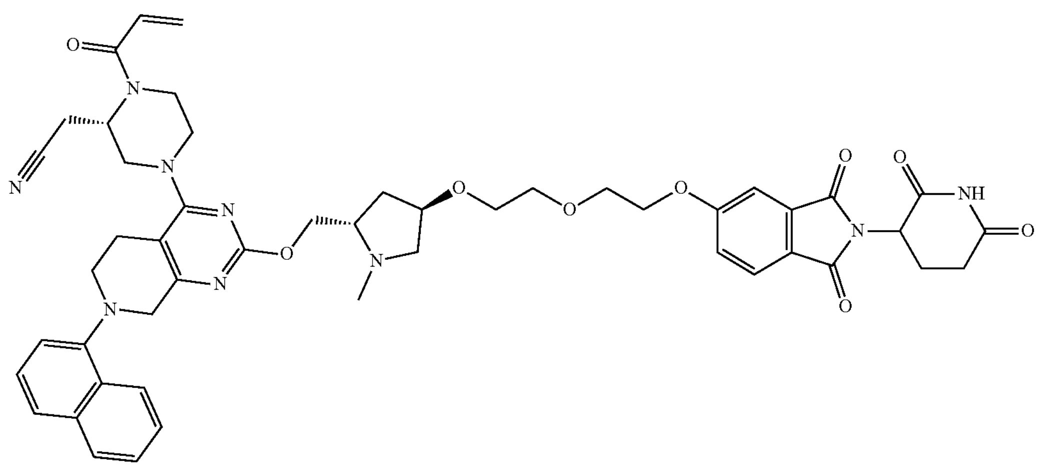 [SMILES: C=CC(=O)N1CCN(c2nc(OC[C@@H]3C[C@@H](OCCOCCOc4ccc5c(c4)C(=O)N(C4CCC(=O)NC4=O)C5=O)CN3C)nc3c2CCN(c2cccc4ccccc24)C3)C[C@@H]1CC#N] | 2-((2S)-1-acryloyl-4-(2-(((2S,4R)-4-(2-(2-(2-(2,6-dioxopiperidin-3-yl)-1,3-dioxoisoindolin-5-yl)oxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 18 |

TABLE 12-continued

Compounds Prepared by Schemes 17-24

| Ex. No. | Structure | Compound Name | Synthetic Scheme |
|---|---|---|---|
| 504 | 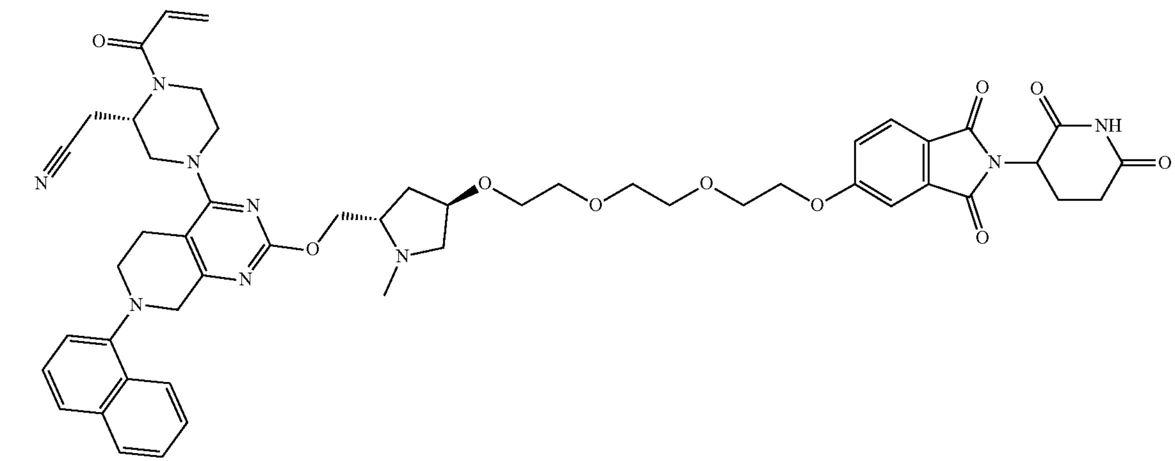 [SMILES: C=CC(=O)N1CCN(c2nc(OC[C@@H]3C[C@@H](OCCOCCOCCOc4ccc5c(c4)C(=O)N(C4CCC(=O)NC4=O)C5=O)CN3C)nc3c2CCN(c2cccc4ccccc24)C3)C[C@@H]1CC#N] | 2-((2S)-1-acryloyl-4-(2-(((2S,4R)-4-(2-(2-(2-((2-(2,6-dioxopiperidin-3-yl)-1,3-dioxoisoindolin-5-yl)oxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 18 |
| 505 | 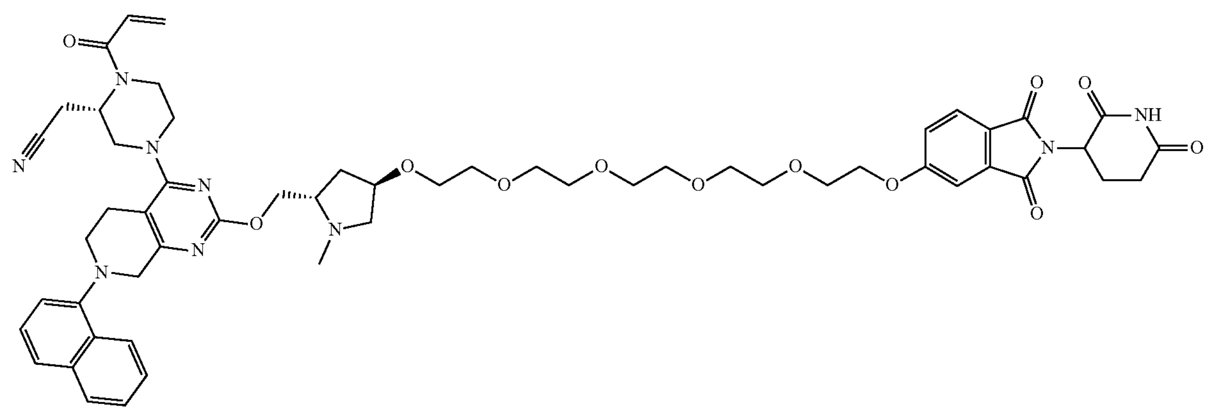 [SMILES: C=CC(=O)N1CCN(c2nc(OC[C@@H]3C[C@@H](OCCOCCOCCOCCOCCOc4ccc5c(c4)C(=O)N(C4CCC(=O)NC4=O)C5=O)CN3C)nc3c2CCN(c2cccc4ccccc24)C3)C[C@@H]1CC#N] | 2-((2S)-1-acryloyl-4-(2-(((2S,4R)-4-((14-((2-(2,6-dioxopiperidin-3-yl)-1,3-dioxoisoindolin-5-yl)oxy)-3,6,9,12-tetraoxatetradecyl)oxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 18 |

| Ex. No. | Structure | Compound Name | Synthetic Scheme |
|---|---|---|---|
| 506 | 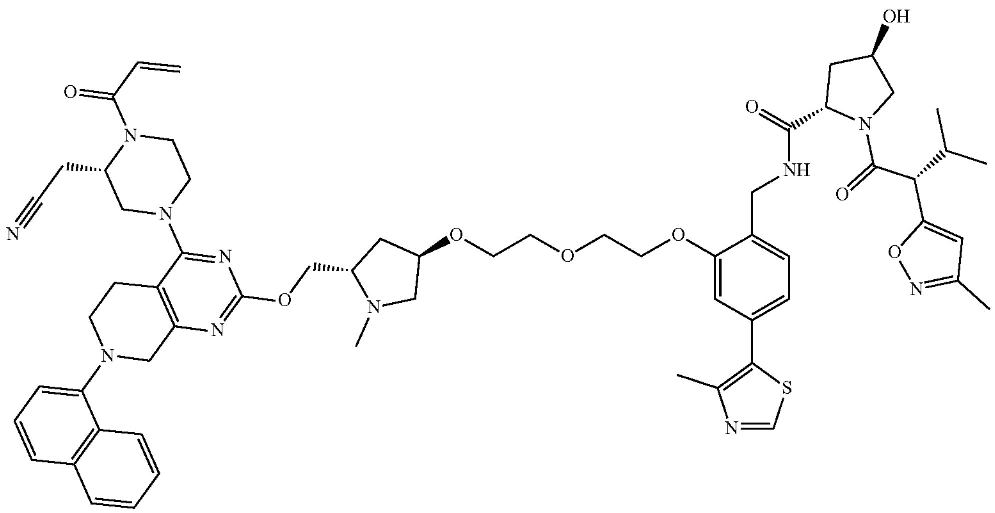 [SMILES: C=CC(=O)N1CCN(c2nc(OC[C@@H]3C[C@@H](OCCOCCOc4cc(-c5scnc5C)ccc4CNC(=O)[C@@H]4C[C@@H](O)CN4C(=O)[C@@H](c4cc(C)no4)C(C)C)CN3C)nc3c2CCN(c2cccc4ccccc24)C3)C[C@@H]1CC#N] | (2S,4R)-N-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide | 19 |
| 507 | 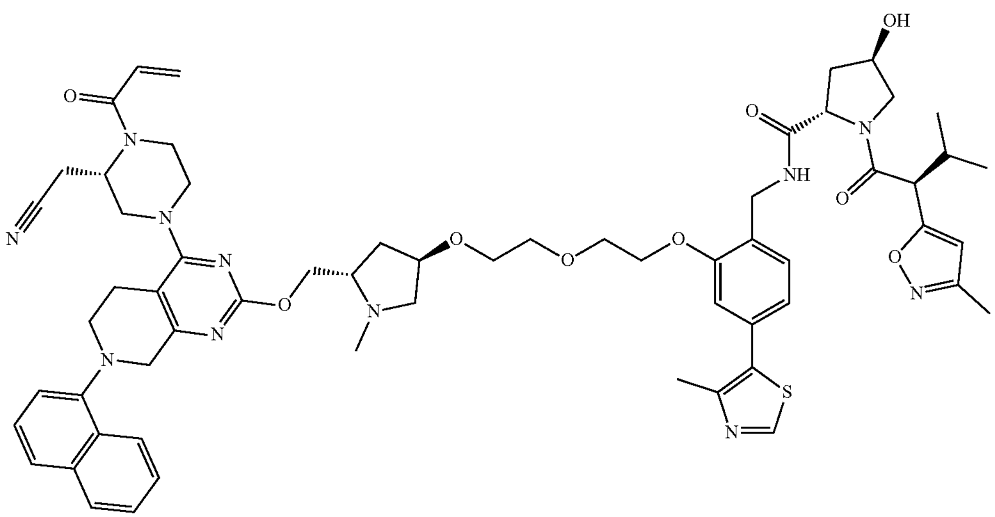 [SMILES: C=CC(=O)N1CCN(c2nc(OC[C@@H]3C[C@@H](OCCOCCOc4cc(-c5scnc5C)ccc4CNC(=O)[C@@H]4C[C@@H](O)CN4C(=O)[C@H](c4cc(C)no4)C(C)C)CN3C)nc3c2CCN(c2cccc4ccccc24)C3)C[C@@H]1CC#N] | (2S,4R)-N-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide | 19 |

TABLE 12-continued
Compounds Prepared by Schemes 17-24
| Ex. No. | Structure | Compound Name | Synthetic Scheme |
|---|---|---|---|
| 508 | 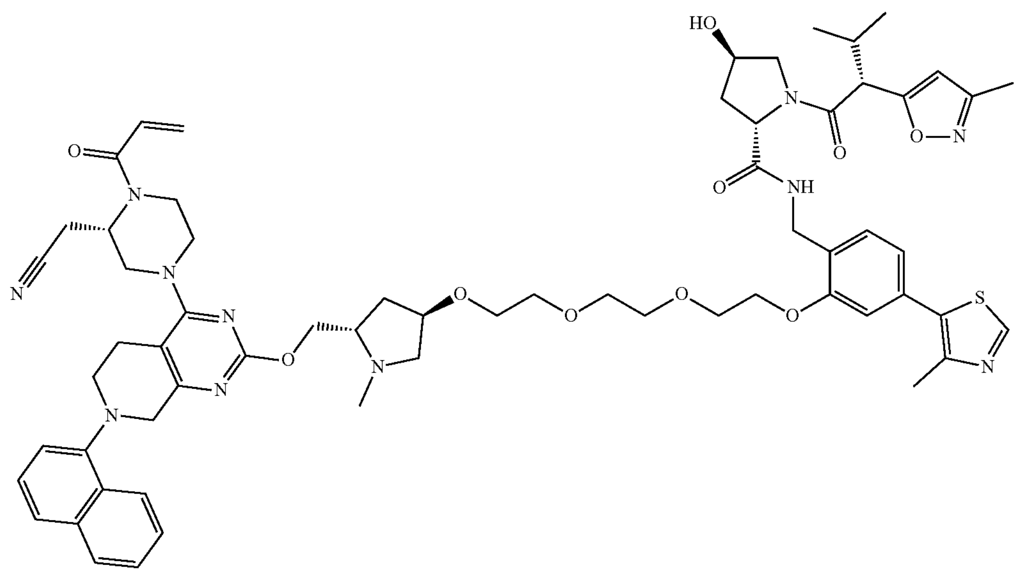 [SMILES: C=CC(=O)N1CCN(c2nc(OC[C@@H]3C[C@@H](OCCOCCOCCOc4cc(-c5scnc5C)ccc4CNC(=O)[C@@H]4C[C@@H](O)CN4C(=O)[C@@H](c4cc(C)no4)C(C)C)CN3C)nc3c2CCN(c2cccc4ccccc24)C3)C[C@@H]1CC#N] | (2S,4R)-N-(2-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-14(R)-3-methyl-2-(3-methylisoxazol-5-yl)butanoyl)pyrrolidine-2-carboxamide | 19 |

TABLE 12-continued
Compounds Prepared by Schemes 17-24
| Ex. No. | Structure | Compound Name | Synthetic Scheme |
|---|---|---|---|
| 509 | 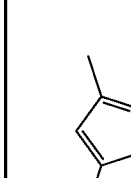 | (2S,4R)-N-(2-(2-(2-(2-(((3R,5S)-5-((((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)-4-(4-methylthiazol-5-yl)benzyl)-4-hydroxy-14(S)-3-methyl-2-(3-methylisoxazol-5-yl)butanoyppyrrolidine-2-carboxamide | 19 |

| Ex. No. | Structure | Compound Name | Synthetic Scheme |
|---|---|---|---|
| 510 | 1807 | (2S,4R)-N-(2-(2-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethoxy)-4-(4-methylthiazol-5-yl)benzyl)-4-hydroxy-1-(R)-3-methyl-2-(3-methylisoxazol-5-yl)butanoyl)pyrrolidine-2-carboxamide | 19 |
| 511 | 1808 | (2S,4R)-N-(2-(2-(2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)ethoxy)-4-(4-methylthiazol-5-yl)benzyl)-4-hydroxy-1-(S)-3-methyl-2-(3-methylisoxazol-5-yl)butanoyl)pyrrolidine-2-carboxamide | 19 |

TABLE 12-continued
Compounds Prepared by Schemes 17-24
| Ex. No. | Structure | Compound Name | Synthetic Scheme |
|---|---|---|---|
| 512 | 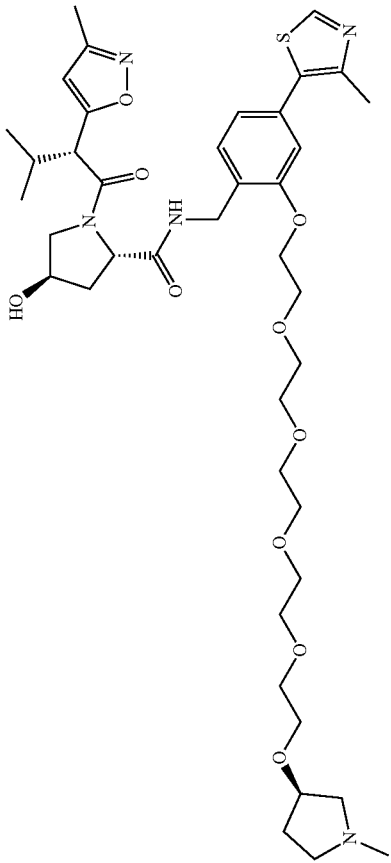 | (2S,4R)-N-(2-((14-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)-3,6,9,12-tetraoxatetradecyl)oxy)-4-(4-methylthiazol-5-yl)benzyl)-4-hydroxy-1-((R)-3-methyl-2-(3-methylisoxazol-5-yl)butanoyl)pyrrolidine-2-carboxamide | 19 |

TABLE 12-continued

Compounds Prepared by Schemes 17-24

| Ex. No. | Structure | Compound Name | Synthetic Scheme |
|---|---|---|---|
| 513 | 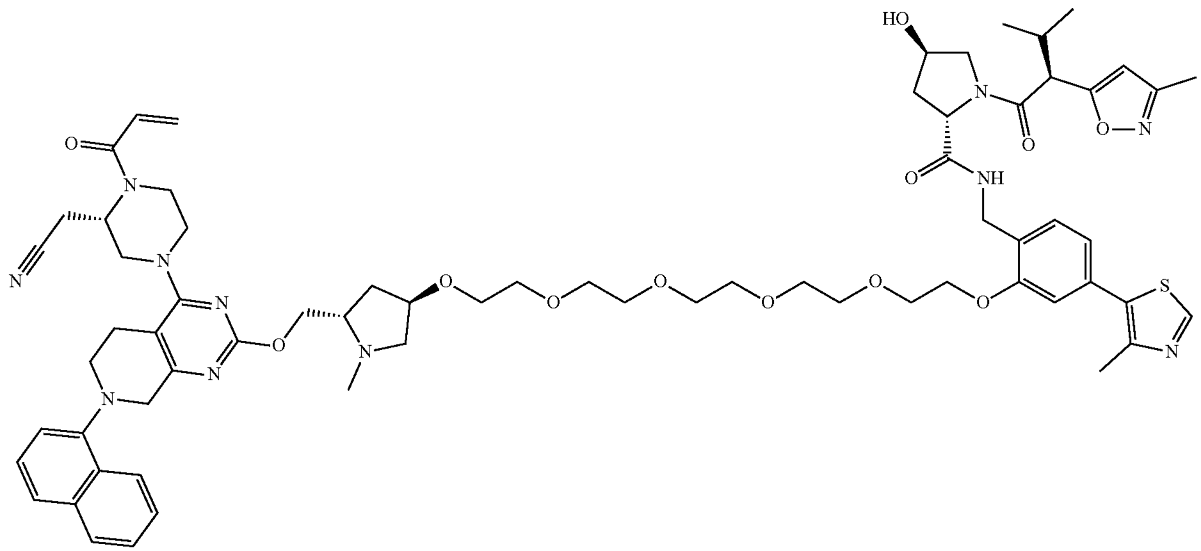 [SMILES: C=CC(=O)N1CCN(c2nc(OC[C@@H]3C[C@@H](OCCOCCOCCOCCOCCOc4cc(-c5scnc5C)ccc4CNC(=O)[C@@H]4C[C@@H](O)CN4C(=O)[C@H](c4cc(C)no4)C(C)C)CN3C)nc3c2CCN(c2cccc4ccccc24)C3)C[C@@H]1CC#N] | (2S,4R)-N-(2-((14-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)-3,6,9,12-tetraoxatetradecyl)oxy)-4-(4-methylthiazol-5-yl)benzyl)-4-hydroxy-1-((S)-3-methyl-2-(3-methylisoxazol-5-yl)butanoyl)pyrrolidine-2-carboxamide | 19 |
| 514 | 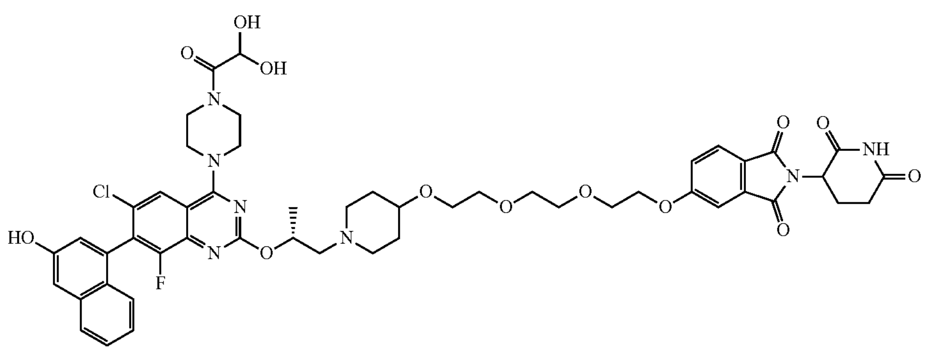 [SMILES: C[C@H](CN1CCC(OCCOCCOCCOc2ccc3c(c2)C(=O)N(C2CCC(=O)NC2=O)C3=O)CC1)Oc1nc(N2CCN(C(=O)C(O)O)CC2)c2cc(Cl)c(-c3cc(O)cc4ccccc34)c(F)c2n1] | 5-(2-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)-2-(2,6-dioxopiperidin-3-yl)isoindoline-1,3-dione | 12 |

TABLE 12-continued

Compounds Prepared by Schemes 17-24

| Ex. No. | Structure | Compound Name | Synthetic Scheme |
|---|---|---|---|
| 515 | 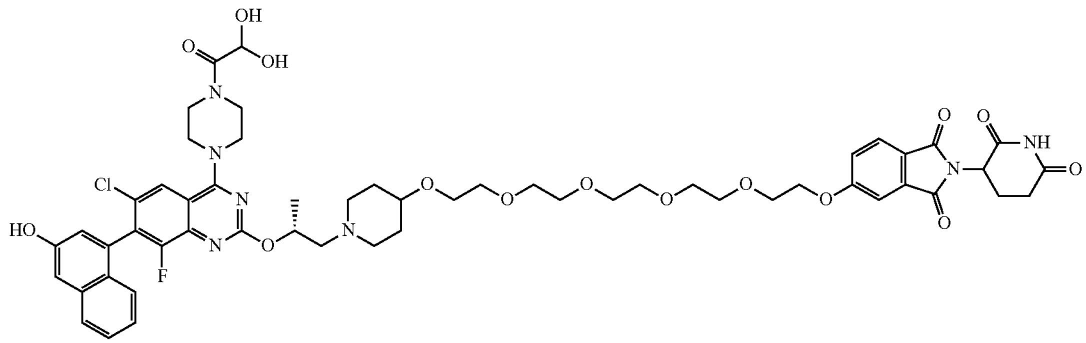 [SMILES: C[C@H](CN1CCC(OCCOCCOCCOCCOCCOc2ccc3c(c2)C(=O)N(C2CCC(=O)NC2=O)C3=O)CC1)Oc1nc(N2CCN(C(=O)C(O)O)CC2)c2cc(Cl)c(-c3cc(O)cc4ccccc34)c(F)c2n1] | 5-((14-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)-3,6,9,12-tetraoxatetradecyl)oxy)-2-(2,6-dioxopiperidin-3-yl)isoindoline-1,3-dione | 12 |
| 516 | 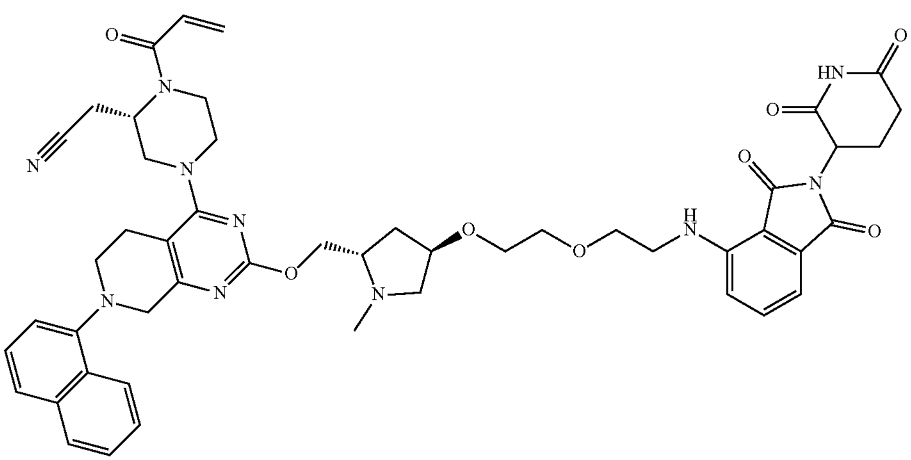 [SMILES: C=CC(=O)N1CCN(c2nc(OC[C@@H]3C[C@@H](OCCOCCNc4cccc5c4C(=O)N(C4CCC(=O)NC4=O)C5=O)CN3C)nc3c2CCN(c2cccc4ccccc24)C3)C[C@@H]1CC#N] | 2-((2S)-1-acryloyl-4-(2-4(2S,4R)-4-(2-(2-(2-(2,6-dioxopiperidin-3-yl)-1,3-dioxoisoindolin-4-yl)amino)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 20 |

TABLE 12-continued

Compounds Prepared by Schemes 17-24

| Ex. No. | Structure | Compound Name | Synthetic Scheme |
|---|---|---|---|
| 517 | 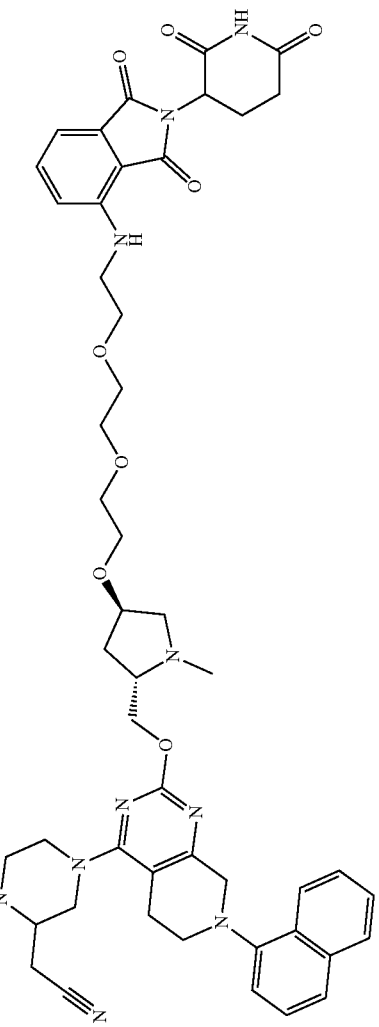 | 2-((2S)-1-acryloyl-4-(2-((2S,4R)-4-(2-(2-(2-(24-(2-(2,6-dioxopiperidin-3-yl)-1,3-dioxoisoindolin-4-yl)amino)ethoxy)ethoxy)ethoxy)1 methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 20 |
| 518 | 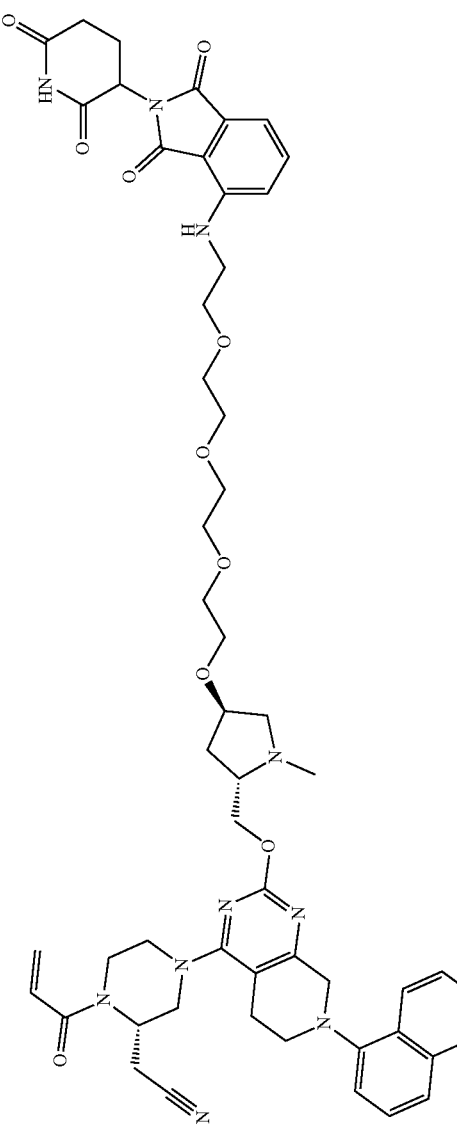 | 2-((2S)-1-acryloyl-4-(2-(((2S,4R)-4-(2-(2-(2-(2-(2,6-dioxopiperidin-3-yl)-1,3-dioxoisoindolin-4-yl)amino)ethoxy)ethoxy)ethoxy)methoxy)-1-methylpyrrolidin-2-yl)methoxy)-7-(naphthalen-1-yl)-5,6,7,8-tetrahydropyrido[3,4-d]pyrimidin-4-yppiperazin-2-yl)acetonitrile | 20 |

TABLE 12-continued

Compounds Prepared by Schemes 17-24

| Ex. No. | Structure | Compound Name | Synthetic Scheme |
|---|---|---|---|
| 519 | 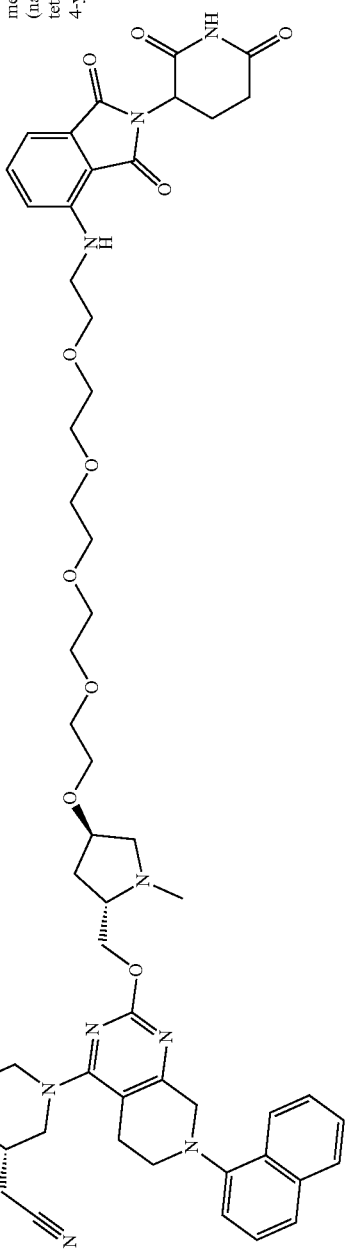 | 2-((2S)-1-acryloyl-4-(2-((2S,4R)-4-((14-(2-(2,6-dioxopiperidin-3-yl)-1,3-dioxoisoindolin-4-yl)amino)-3,6,9,12-tetraoxatetradecyl)oxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 20 |
| 520 | 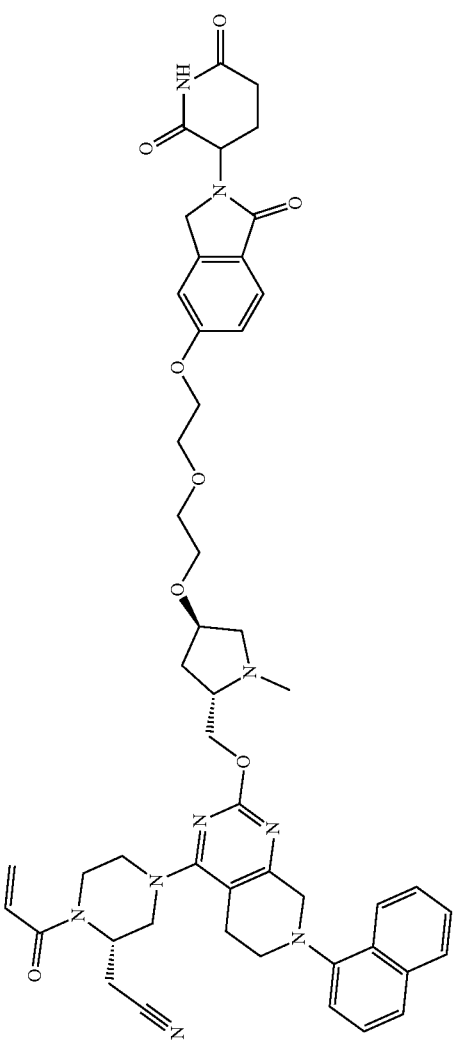 | 2-((2S)-1-acryloyl-4-(2-((2S,4R)-4-(2-(2-((2-(2,6-dioxopiperidin-3-yl)-1-oxoisoindolin-5-yl)oxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 21 |

TABLE 12-continued

Compounds Prepared by Schemes 17-24

| Ex. No. | Structure | Compound Name | Synthetic Scheme |
|---|---|---|---|
| 521 | 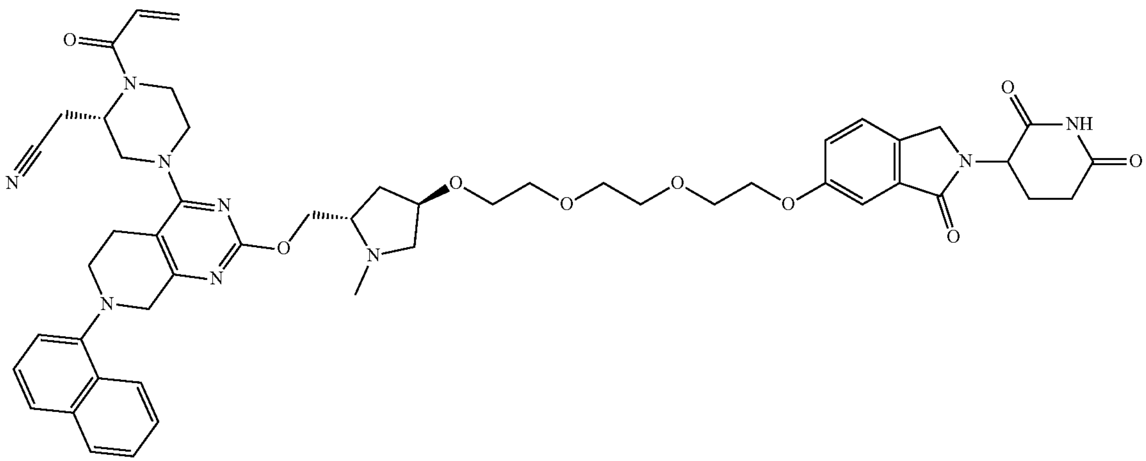 [SMILES: C=CC(=O)N1CCN(c2nc(OC[C@@H]3C[C@@H](OCCOCCOCCOc4ccc5c(c4)C(=O)N(C4CCC(=O)NC4=O)C5)CN3C)nc3c2CCN(c2cccc4ccccc24)C3)C[C@@H]1CC#N] | 2-((2S)-1-acryloyl-4-(2-(((2S,4R)-4-(2-(2-(2-(2-((2-(2,6-dioxopiperidin-3-yl)oxyisoindolin-5-yl)oxy)ethoxy)ethoxy)ethoxy)ethoxy)methyl)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 21 |
| 522 | 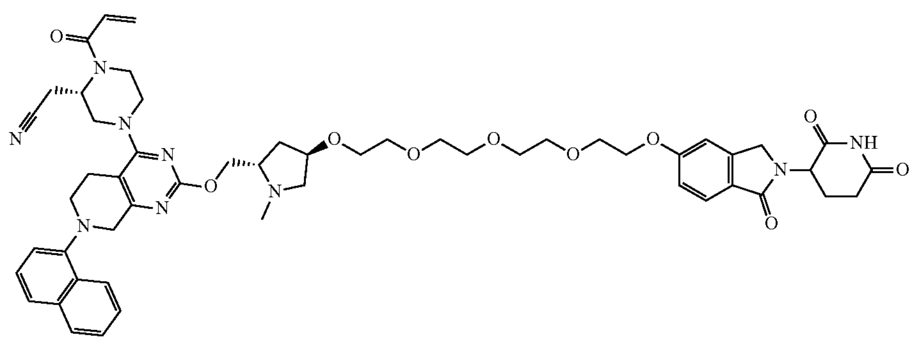 [SMILES: C=CC(=O)N1CCN(c2nc(OC[C@@H]3C[C@@H](OCCOCCOCCOCCOc4ccc5c(c4)CN(C4CCC(=O)NC4=O)C5=O)CN3C)nc3c2CCN(c2cccc4ccccc24)C3)C[C@@H]1CC#N] | 2-((2S)-1-acryloyl-4-(2-(((2S,4R)-4-(2-(2-(2-((2-(2,6-dioxopiperidin-3-yl)-1-oxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-2-yl)piperazin-4-yl)acetonitrile | 21 |

TABLE 12-continued

Compounds Prepared by Schemes 17-24

| Ex. No. | Structure | Compound Name | Synthetic Scheme |
|---|---|---|---|
| 523 | 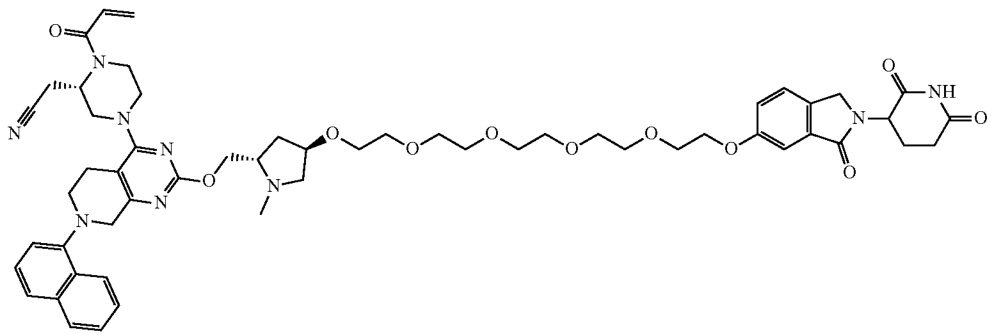 [SMILES: C=CC(=O)N1CCN(c2nc(OC[C@@H]3C[C@@H](OCCOCCOCCOCCOCCOc4ccc5c(c4)C(=O)N(C4CCC(=O)NC4=O)C5)CN3C)nc3c2CCN(c2cccc4ccccc24)C3)C[C@@H]1CC#N] | 2-((2S)-1-acryloyl-4-(2-(((2S,4R)-4-((14-((2-(2,6-dioxopiperidin-3-yl)-1-oxoisoindolin-5-yl)oxy)-3,6,9,12-tetraoxatetradecyl)oxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile | 21 |
| 524 | 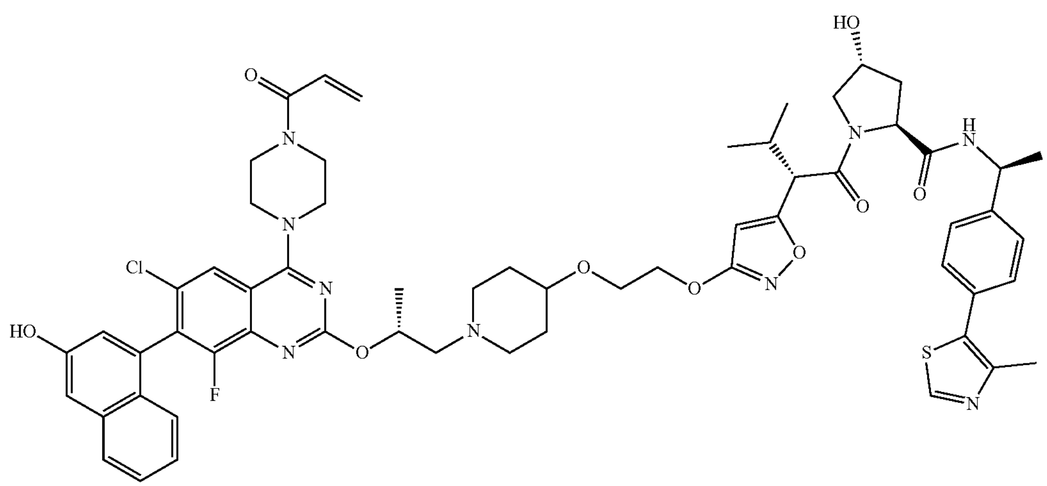 [SMILES: C=CC(=O)N1CCN(c2nc(O[C@H](C)CN3CCC(OCCOc4cc([C@@H](C(=O)N5C[C@H](O)C[C@H]5C(=O)N[C@@H](C)c5ccc(-c6scnc6C)cc5)C(C)C)on4)CC3)nc3c(F)c(-c4cc(O)cc5ccccc45)c(Cl)cc23)CC1] | (2S,4R)-1-((2S)-2-(3-(2-(1-((2R)-2-(4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)isoxazol-5-yl)-3-methylbutanoyl)-4-hydroxy-N-((s)-1-(4-(4-methylthiazol-5-yl)phenyl)ethyl)pyrrolidine-2-carboxamide | 9 |

TABLE 12-continued

Compounds Prepared by Schemes 17-24

| Ex. No. | Structure | Compound Name | Synthetic Scheme |
|---|---|---|---|
| 525 | 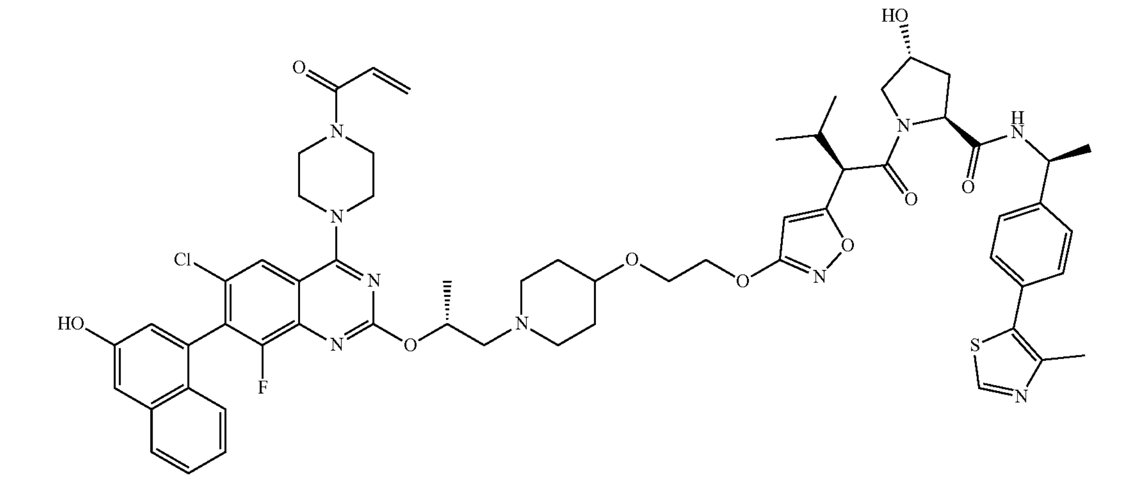 [SMILES: C=CC(=O)N1CCN(c2nc(O[C@H](C)CN3CCC(OCCOc4cc([C@H](C(=O)N5C[C@H](O)C[C@H]5C(=O)N[C@@H](C)c5ccc(-c6scnc6C)cc5)C(C)C)on4)CC3)nc3c(F)c(-c4cc(O)cc5ccccc45)c(Cl)cc23)CC1] | (2S,4R)-1-((2R)-2-(3-(2-(1-((2R)-2-((4-acryloyl)piperazin-1-yl)-6-chloro-8-fluoro-7-(3-hydroxynaphthalen-1-yl)quinazolin-2-yl)oxy)propyl)piperidin-4-yl)oxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 9 |
| 526 | 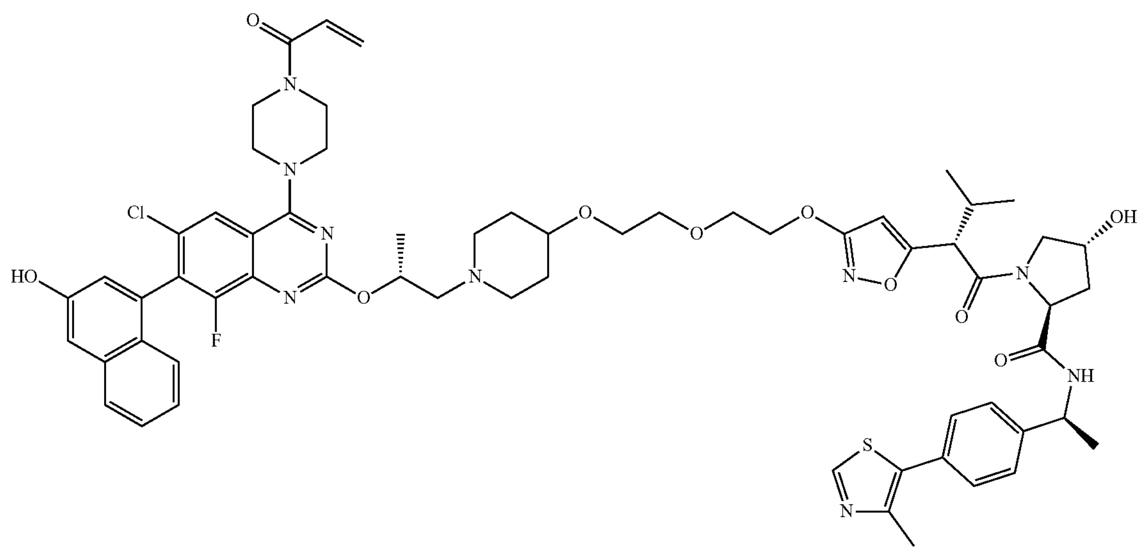 [SMILES: C=CC(=O)N1CCN(c2nc(O[C@H](C)CN3CCC(OCCOCCOc4cc([C@@H](C(=O)N5C[C@H](O)C[C@H]5C(=O)N[C@@H](C)c5ccc(-c6scnc6C)cc5)C(C)C)on4)CC3)nc3c(F)c(-c4cc(O)cc5ccccc45)c(Cl)cc23)CC1] | (2S,4R)-1-((2S)-2-(3-(2-(2-((1-((2R)-2-((4-acryloyl)piperazin-1-yl)-6-chloro-8-fluoro-7-(3-hydroxynaphthalen-1-yl)quinazolin-2-yl)oxy)propyl)piperidin-4-yl)oxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 9 |

TABLE 12-continued

Compounds Prepared by Schemes 17-24

| Ex. No. | Structure | Compound Name | Synthetic Scheme |
|---|---|---|---|
| 527 | 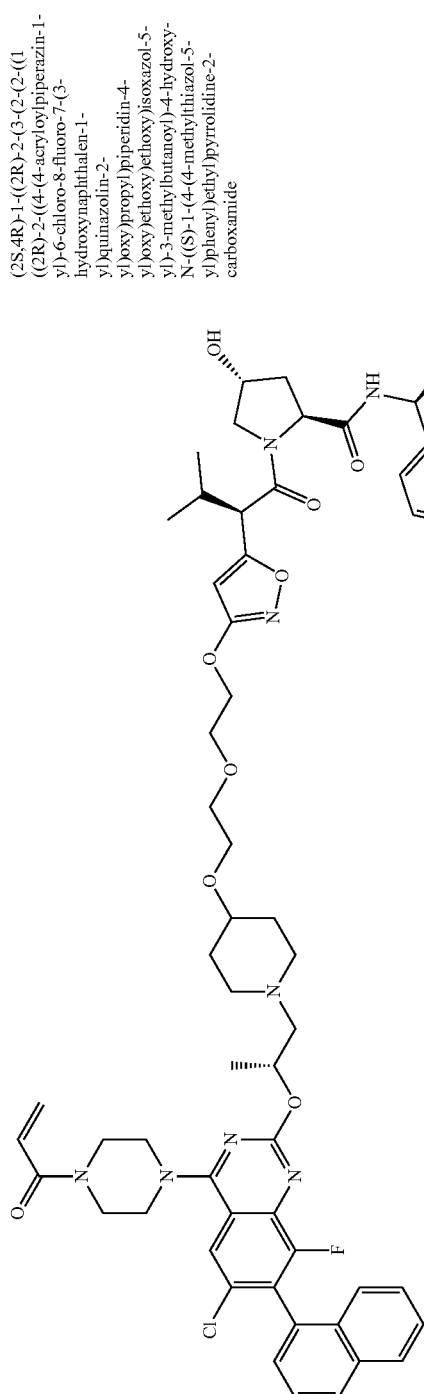 | (2S,4R)-1-((2R)-2-(3-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 9 |
| 528 | 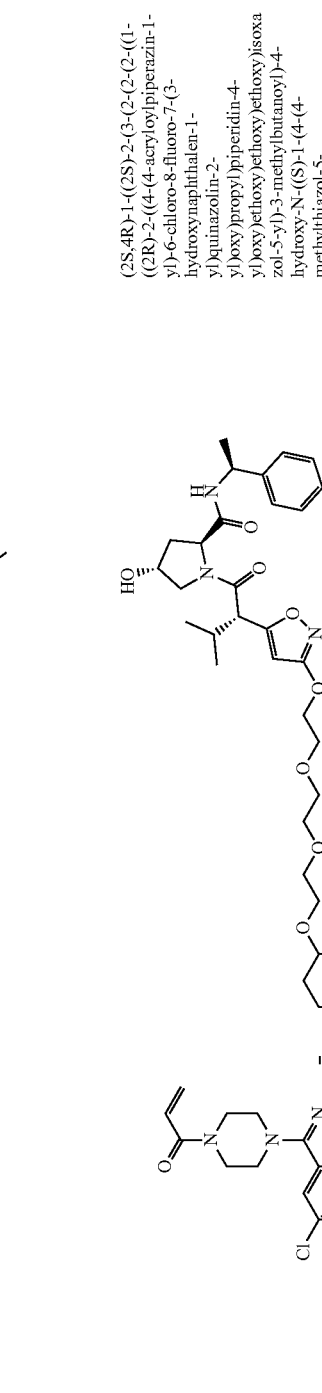 | (2S,4R)-1-((2S)-2-(3-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 9 |

TABLE 12-continued

Compounds Prepared by Schemes 17-24

| Ex. No. | Structure | Compound Name | Synthetic Scheme |
|---|---|---|---|
| 529 | 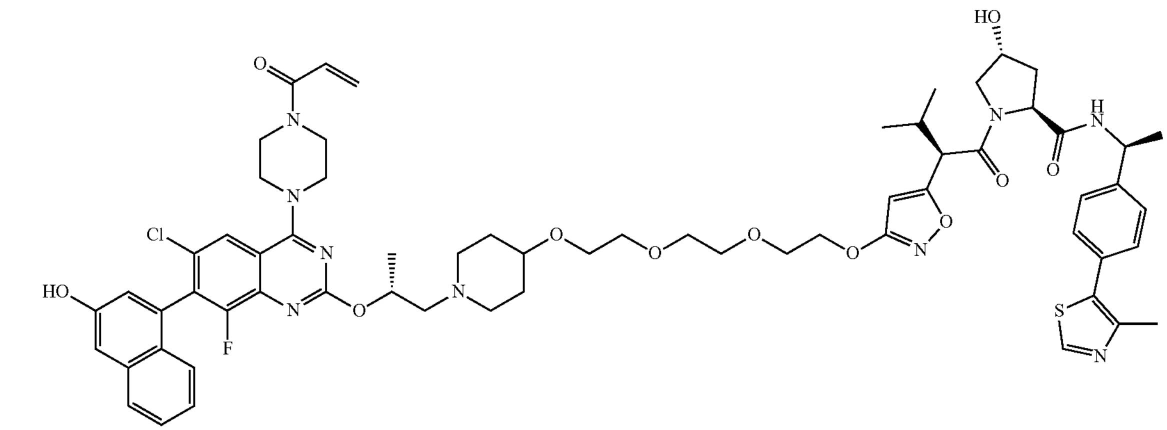 [SMILES: C=CC(=O)N1CCN(c2nc(O[C@H](C)CN3CCC(OCCOCCOCCOc4cc([C@H](C(=O)N5C[C@H](O)C[C@H]5C(=O)N[C@@H](C)c5ccc(-c6scnc6C)cc5)C(C)C)on4)CC3)nc3c(F)c(-c4cc(O)cc5ccccc45)c(Cl)cc23)CC1] | (2S,4R)-1-((2R)-2-(3-(2-(2-(2-((1-((2R)-2-((4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 9 |
| 530 | 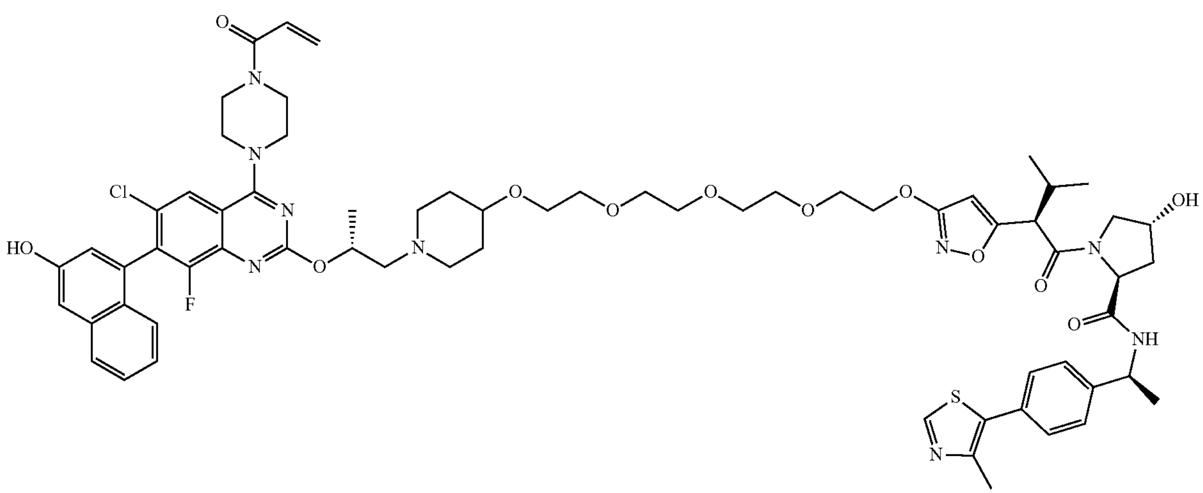 [SMILES: C=CC(=O)N1CCN(c2nc(O[C@H](C)CN3CCC(OCCOCCOCCOCCOc4cc([C@H](C(=O)N5C[C@H](O)C[C@H]5C(=O)N[C@@H](C)c5ccc(-c6scnc6C)cc5)C(C)C)on4)CC3)nc3c(F)c(-c4cc(O)cc5ccccc45)c(Cl)cc23)CC1] | (2S,4R)-1-((2R)-2-(3-(2-(2-(2-((1-((2R)-2-((4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)ethox y)isoxazol-5-yl)-3-methylbutanoyl)-4-hydroxy-N-((S)-1-(4-(4-methylthiazol-5-yl)phenyl)ethyl)pyrrolidine-2-carboxamide | 9 |

TABLE 12-continued

Compounds Prepared by Schemes 17-24

| Ex. No. | Structure | Compound Name | Synthetic Scheme |
|---|---|---|---|
| 531 | 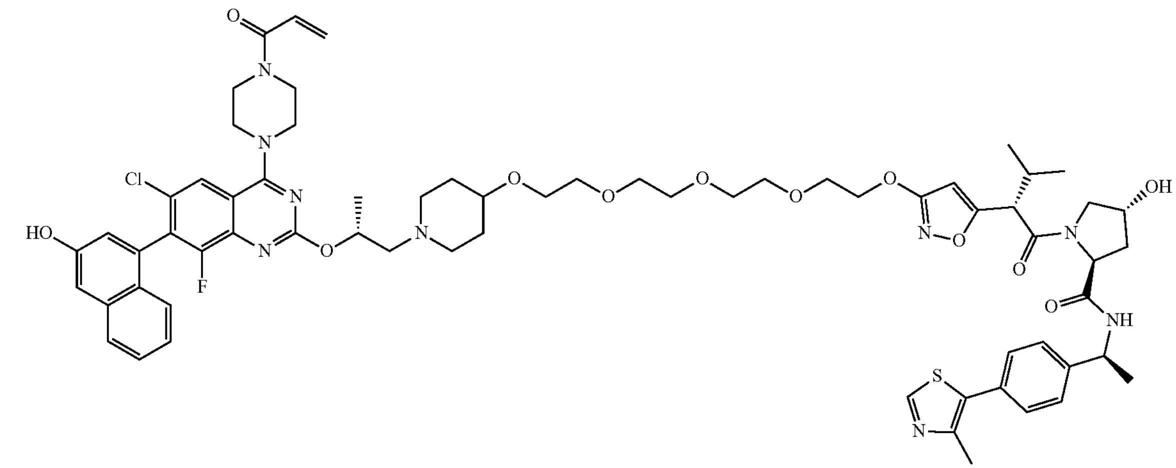 [SMILES: C=CC(=O)N1CCN(c2nc(O[C@H](C)CN3CCC(OCCOCCOCCOCCOc4cc([C@@H](C(=O)N5C[C@H](O)C[C@H]5C(=O)N[C@@H](C)c5ccc(-c6scnc6C)cc5)C(C)C)on4)CC3)nc3c(F)c(-c4cc(O)cc5ccccc45)c(Cl)cc23)CC1] | (2S,4R)-1-((2S)-2-(3-(2-(2-(2-((1-((2R)-2-((4-(4-acryloyl)piperazin-1-yl)-6-chloro-8-fluoro-7-(3-hydroxynaphthalen-1-yl)quinazolin-2-yl)oxy)propyl)piperidin-4-yl)oxy)ethoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 9 |
| 532 | 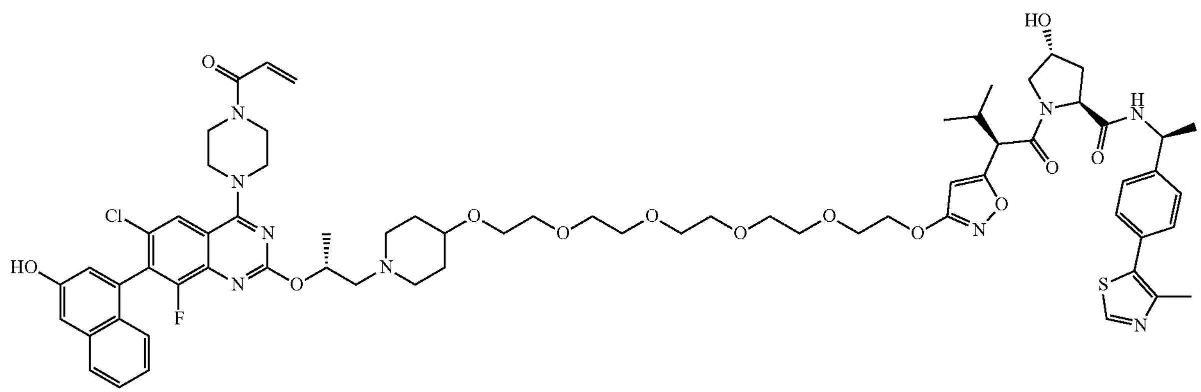 [SMILES: C=CC(=O)N1CCN(c2nc(O[C@H](C)CN3CCC(OCCOCCOCCOCCOCCOc4cc([C@H](C(=O)N5C[C@H](O)C[C@H]5C(=O)N[C@@H](C)c5ccc(-c6scnc6C)cc5)C(C)C)on4)CC3)nc3c(F)c(-c4cc(O)cc5ccccc45)c(Cl)cc23)CC1] | (2S,4R)-1-((2R)-2-(3-(14-((1-((2R)-2-((4-(4-acryloyl)piperazin-1-yl)-6-chloro-8-fluoro-7-(3-hydroxynaphthalen-1-yl)quinazolin-2-yl)oxy)propyl)piperidin-4-yl)oxy)-3,6,9,12-tetraoxatetradecyl)oxy)isoxazol-5-yl)-3-methylbutanoyl)-4-hydroxy-N-((S)-1-(4-(4-methylthiazol-5-yl)phenypethyl)pyrrolidine-2-carboxamide | 9 |

TABLE 12-continued

Compounds Prepared by Schemes 17-24

| Ex. No. | Structure | Compound Name | Synthetic Scheme |
|---|---|---|---|
| 533 | 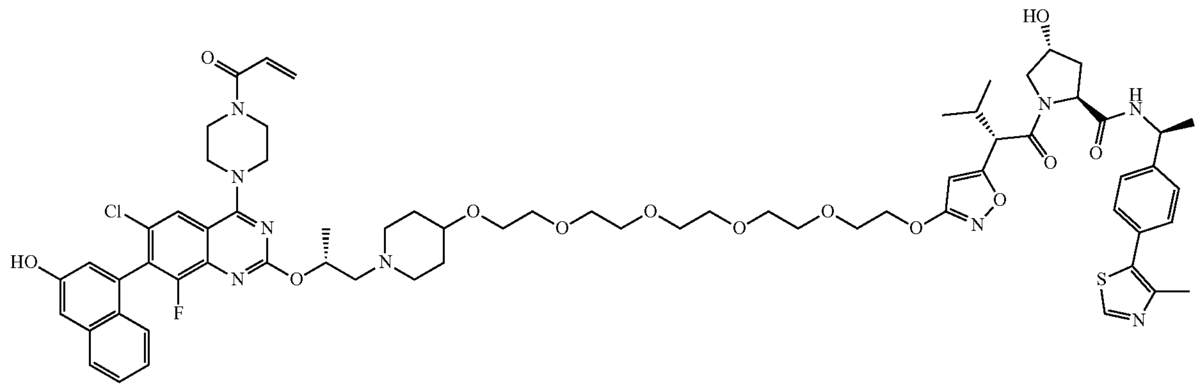 [SMILES: C=CC(=O)N1CCN(c2nc(O[C@H](C)CN3CCC(OCCOCCOCCOCCOCCOc4cc([C@@H](C(=O)N5C[C@H](O)C[C@H]5C(=O)N[C@@H](C)c5ccc(-c6scnc6C)cc5)C(C)C)on4)CC3)nc3c(F)c(-c4cc(O)cc5ccccc45)c(Cl)cc23)CC1] | (2S,4R)-1-((2S)-2-(3-((14-((1-42R)-24(4-acryloylpiperazin-1-yl)-6-chloro-8-fluoro-7-(3-hydroxynaphthalen-1-yl)quinazolin-2-yl)oxy)propyl)piperidin-4-yl)oxy)-3,6,9,12-tetraoxatetradecyl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 9 |
| 534 | 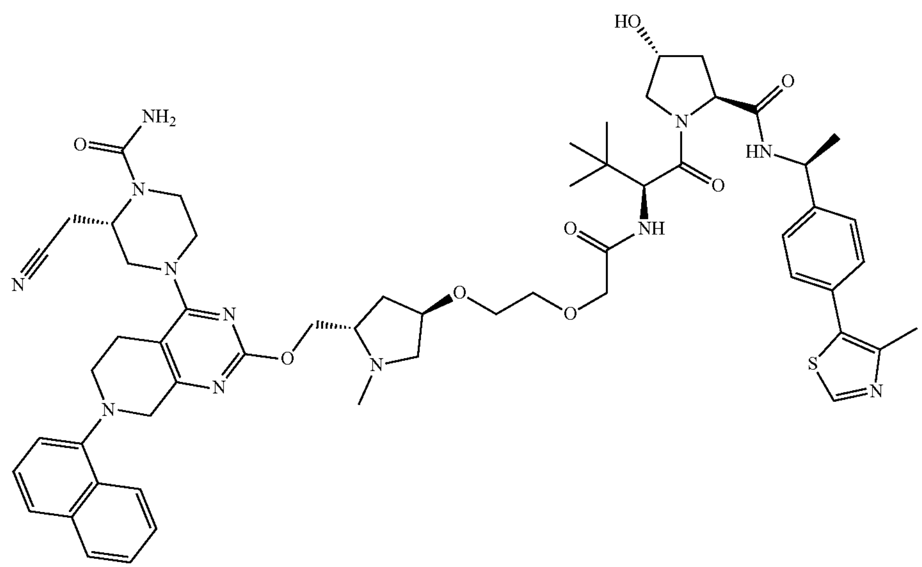 [SMILES: Cc1ncsc1-c1ccc([C@H](C)NC(=O)[C@@H]2C[C@@H](O)CN2C(=O)[C@@H](NC(=O)COCCO[C@@H]2C[C@@H](COc3nc4c(c(N5CCN(C(N)=O)[C@@H](CC#N)C5)n3)CCN(c3cccc5ccccc35)C4)N(C)C2)C(C)(C)C)cc1] | (S)-2-(cyanomethyl)-4-(2-(((2S,4R)-4-(2-(2-(((S)-1-((2S,4R)-4-hydroxy-2((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 17 |

TABLE 12-continued
Compounds Prepared by Schemes 17-24
| Ex. No. | Structure | Compound Name | Synthetic Scheme |
|---|---|---|---|
| 535 | 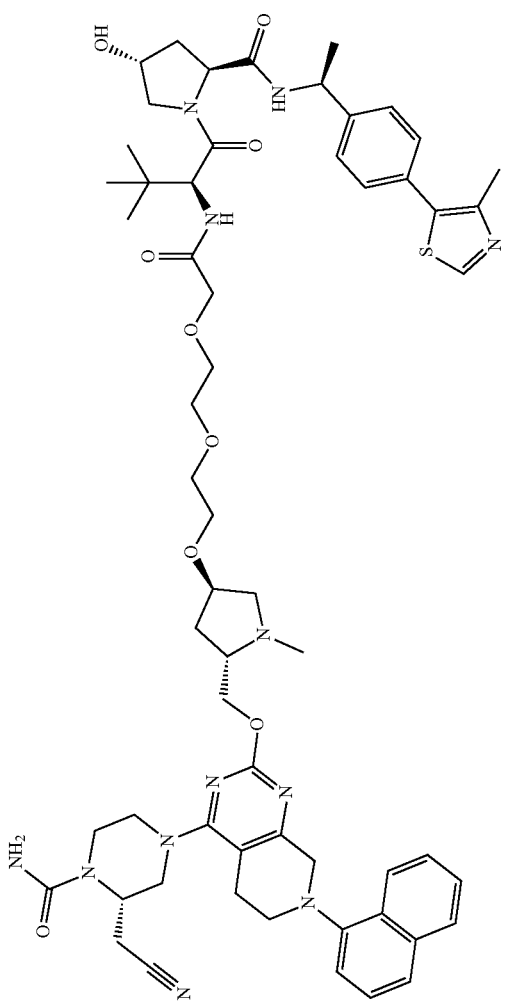 | (S)-2-(cyanomethyl)-4-(2-(((2S,4R)-4-(2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-methyl-1-oxobutan-2-yl)amino)-2-oxoethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 17 |

TABLE 12-continued
Compounds Prepared by Schemes 17-24
| Ex. No. | Structure | Compound Name | Synthetic Scheme |
|---|---|---|---|
| 536 | 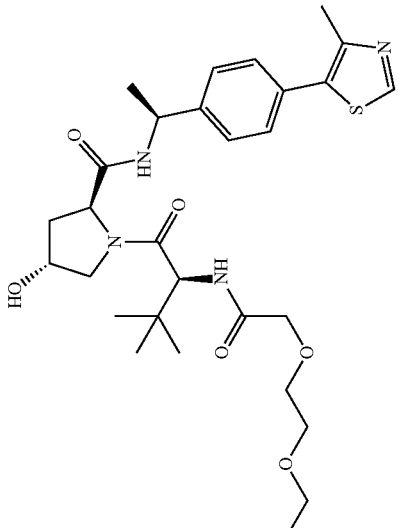 | (S)-2-(cyanomethyl)-4-(2-(((2S,4R)-4-(((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)oxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 17 |

TABLE 12-continued

Compounds Prepared by Schemes 17-24

| Ex. No. | Structure | Compound Name | Synthetic Scheme |
|---|---|---|---|
| 537 | 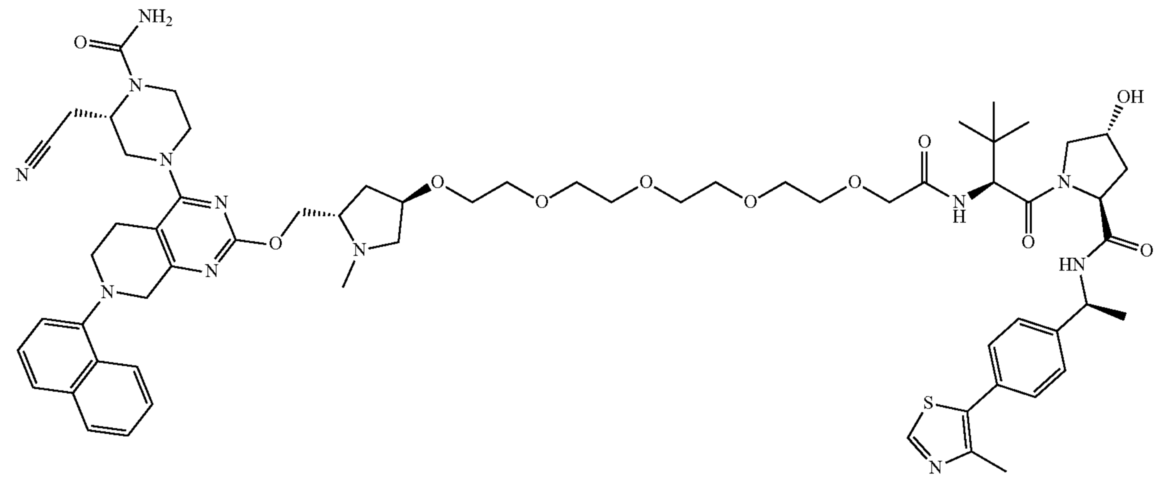 [SMILES: Cc1ncsc1-c1ccc([C@H](C)NC(=O)[C@@H]2C[C@@H](O)CN2C(=O)[C@@H](NC(=O)COCCOCCOCCOCCO[C@@H]2C[C@@H](COc3nc4c(c(N5CCN(C(N)=O)[C@@H](CC#N)C5)n3)CCN(c3cccc5ccccc35)C4)N(C)C2)C(C)(C)C)cc1] | (S)-2-(cyanomethyl)-4-(2-(((2S,4R)-4-(((S)-16-((2S,4R)-4-hydroxy-2-(((S)-1-(4-(4-methylthiazol-5-yl)phenyl)ethyl)carbamoyl)pyrrolidine-1-carbonyl)-17,17-dimethyl-14-oxo-3,6,9,12-tetraoxa-15-azaoctadecyl)oxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 17 |
| 538 | 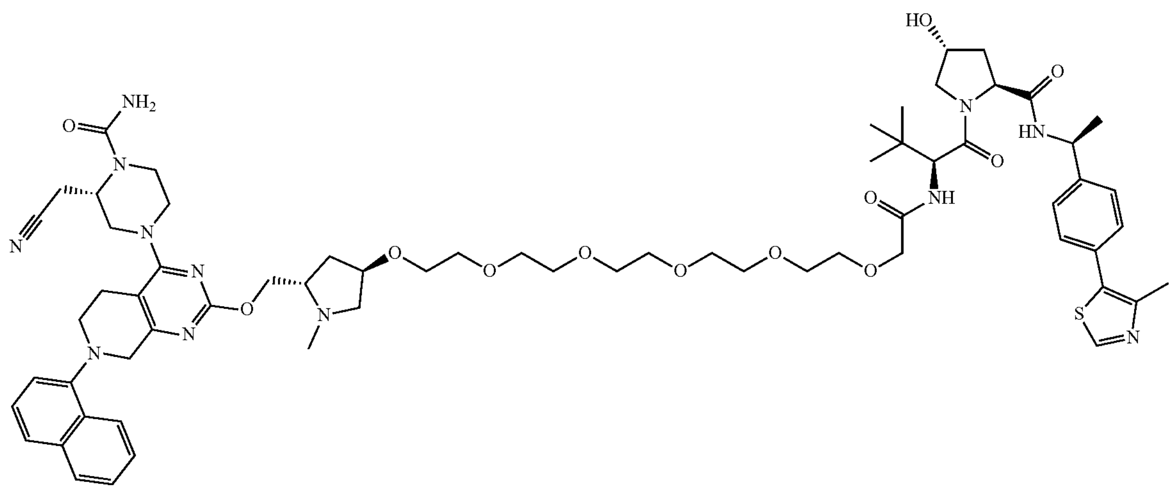 [SMILES: Cc1ncsc1-c1ccc([C@H](C)NC(=O)[C@@H]2C[C@@H](O)CN2C(=O)[C@@H](NC(=O)COCCOCCOCCOCCOCCO[C@@H]2C[C@@H](COc3nc4c(c(N5CCN(C(N)=O)[C@@H](CC#N)C5)n3)CCN(c3cccc5ccccc35)C4)N(C)C2)C(C)(C)C)cc1] | (S)-2-(cyanomethyl)-4-(2-(((2S,4R)-4-(((S)-19-((2S,4R)-4-hydroxy-2-(((S)-1-(4-(4-methylthiazol-5-yl)phenyl)ethyl)carbamoyl)pyrrolidine-1-carbonyl)-20,20-dimethyl-17-oxo-3,6,9,12,15-pentaoxa-18-azahenicosyl)oxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 17 |

TABLE 12-continued

Compounds Prepared by Schemes 17-24

| Ex. No. | Structure | Compound Name | Synthetic Scheme |
|---|---|---|---|
| 539 | 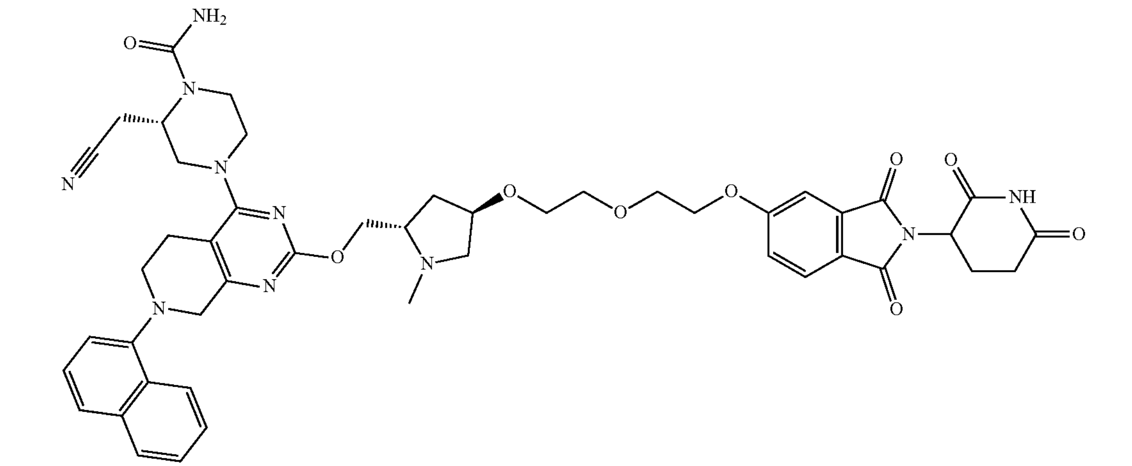 [SMILES: CN1C[C@H](OCCOCCOc2ccc3c(c2)C(=O)N(C2CCC(=O)NC2=O)C3=O)C[C@H]1COc1nc2c(c(N3CCN(C(N)=O)[C@@H](CC#N)C3)n1)CCN(c1cccc3ccccc13)C2] | (2S)-2-(cyanomethyl)-4-(2-(((2S,4R)-4-(2-(2-((2-(2,6-dioxopiperidin-3-yl)-1,3-dioxoisoindolin-5-yl)oxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 18 |
| 540 | 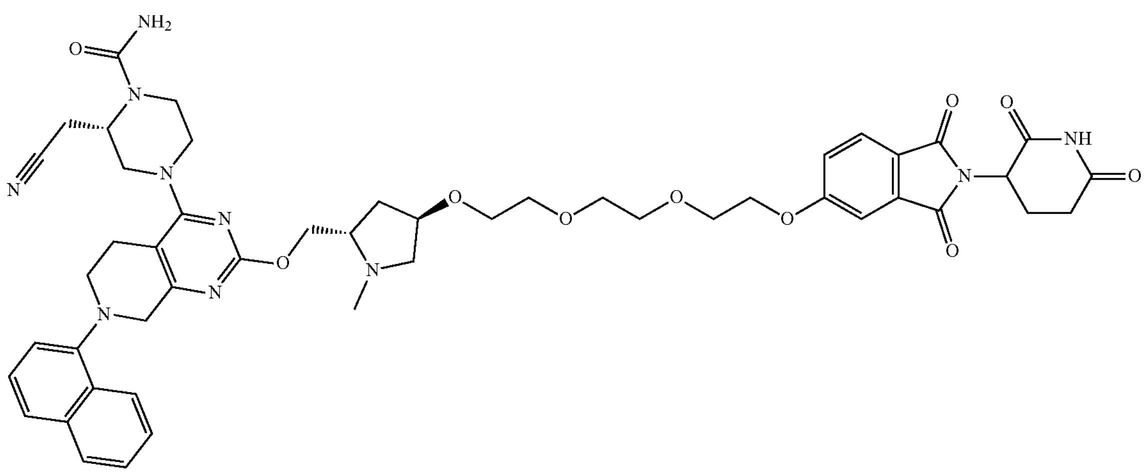 [SMILES: CN1C[C@H](OCCOCCOCCOc2ccc3c(c2)C(=O)N(C2CCC(=O)NC2=O)C3=O)C[C@H]1COc1nc2c(c(N3CCN(C(N)=O)[C@@H](CC#N)C3)n1)CCN(c1cccc3ccccc13)C2] | (2S)-2-(cyanomethyl)-4-(2-(((2S,4R)-4-(2-(2-(2-(2-(2,6-dioxopiperidin-3-yl)-1,3-dioxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 18 |

TABLE 12-continued

Compounds Prepared by Schemes 17-24

| Ex. No. | Structure | Compound Name | Synthetic Scheme |
|---|---|---|---|
| 541 | | (2S)-2-(cyanomethyl)-4-(2-(((2S,4R)-4-(2-(2-(2-(2-((2,6-dioxopiperidin-3-yl)-1,3-dioxoisoindolin-5-yl)oxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 18 |
| 541 | | (2S)-2-(cyanomethyl)-4-(2-(((2S,4R)-4-((14-((2-(2,6-dioxopiperidin-3-yl)-1,3-dioxoisoindolin-5-yl)oxy)-3,6,9,12-tetraoxatetradecyl)oxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 18 |

TABLE 12-continued

Compounds Prepared by Schemes 17-24

| Ex. No. | Structure | Compound Name | Synthetic Scheme |
|---|---|---|---|
| 543 | 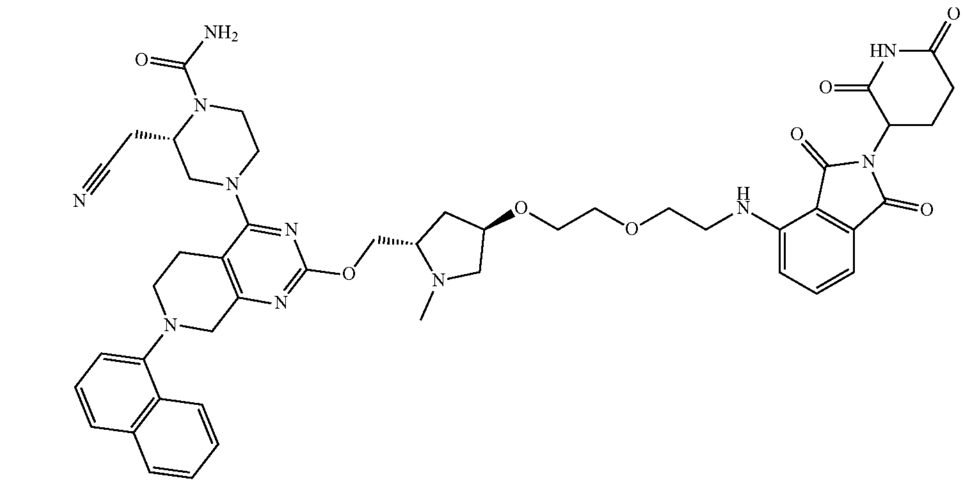 [SMILES: CN1C[C@H](OCCOCCNc2cccc3c2C(=O)N(C2CCC(=O)NC2=O)C3=O)C[C@H]1COc1nc2c(c(N3CCN(C(N)=O)[C@@H](CC#N)C3)n1)CCN(c1cccc3ccccc13)C2] | (2S)-2-(cyanomethyl)-4-(2-(((2S,4R)-4-(2-(2-(2-((2-(2,6-dioxopiperidin-3-yl)-1,3-dioxoisoindolin-4-yl)amino)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 20 |
| 544 | 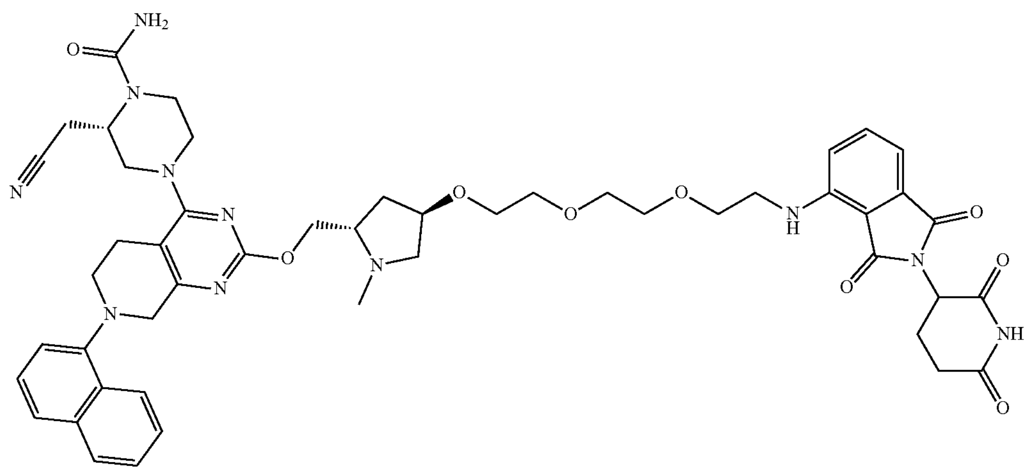 [SMILES: CN1C[C@H](OCCOCCOCCNc2cccc3c2C(=O)N(C2CCC(=O)NC2=O)C3=O)C[C@H]1COc1nc2c(c(N3CCN(C(N)=O)[C@@H](CC#N)C3)n1)CCN(c1cccc3ccccc13)C2] | (2S)-2-(cyanomethyl)-4-(2-(((2S,4R)-4-(2-(2-(2-((2-(2,6-dioxopiperidin-3-yl)-1,3-dioxoisoindolin-4-yl)amino)ethoxy)ethoxy)methoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 20 |

TABLE 12-continued

Compounds Prepared by Schemes 17-24

| Ex. No. | Structure | Compound Name | Synthetic Scheme |
|---|---|---|---|
| 545 | 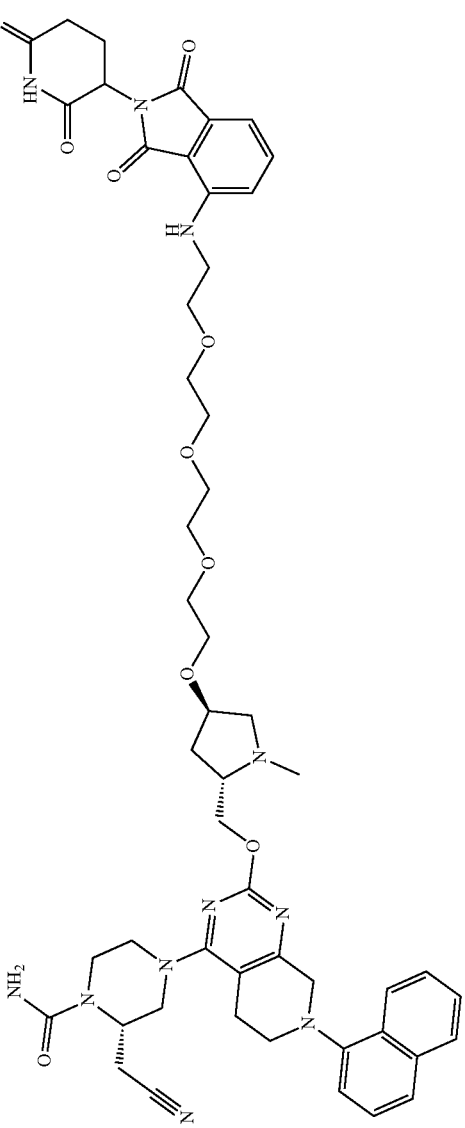 | (2S)-2-(cyanomethyl)-4-(2-(((2S,4R)-4-(2-(2-(2-(2-(2,6-dioxopiperidin-3-yl)-1,3-dioxoisoindolin-4-yl)amino)ethoxy)ethoxy)ethoxy)eth oxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 20 |
| 546 | 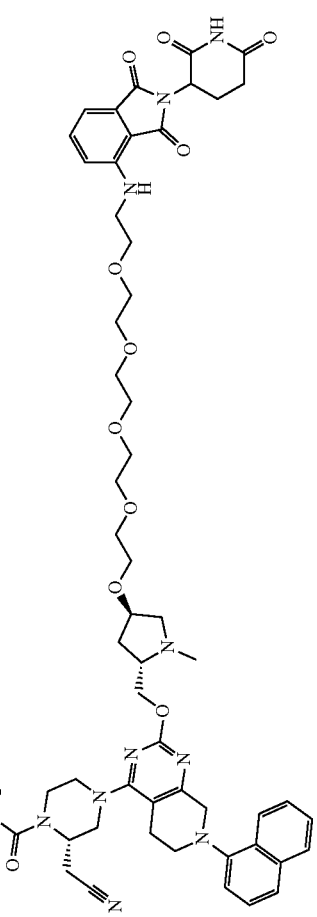 | (2S)-2-(cyanomethyl)-4-(2-(((2S,4R)-4-((14-(2-(2,6-dioxopiperidin-3-yl)-1,3-dioxoisoindolin-4-yl)amino)-3,6,9,12-tetraoxatetradecyl)oxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 20 |

TABLE 12-continued
Compounds Prepared by Schemes 17-24
| Ex. No. | Structure | Compound Name | Synthetic Scheme |
|---|---|---|---|
| 547 | 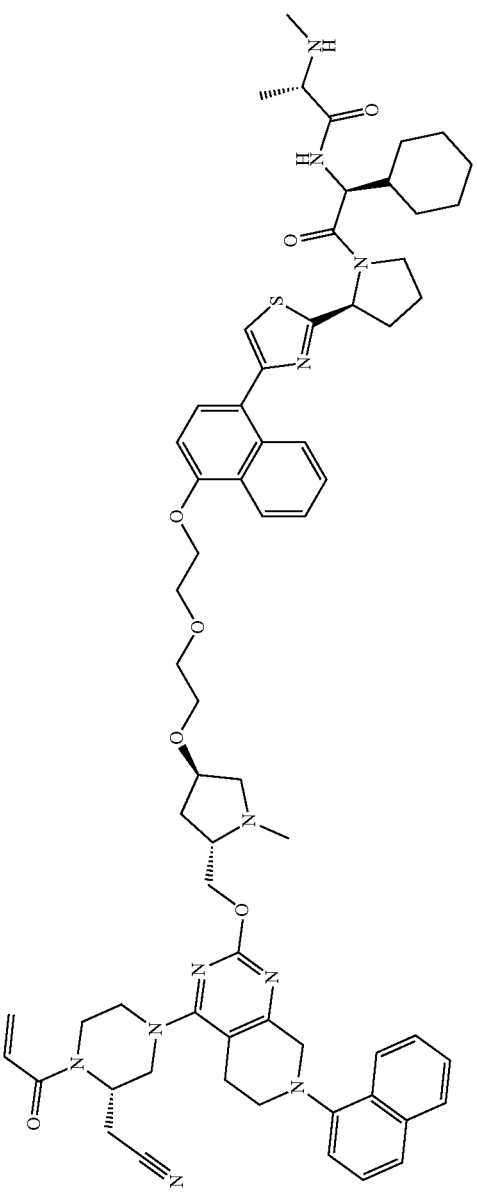 | (S)-N-((S)-2-((S)-2-(4-(4-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)naphthalen-1-yl)thiazol-2-yl)pyrrolidin-1-yl)-1-cyclohexyl-2-oxoethyl)-2-(methylamino)propanamide | 22 |

TABLE 12-continued

Compounds Prepared by Schemes 17-24

| Ex. No. | Structure | Compound Name | Synthetic Scheme |
|---|---|---|---|
| 548 | 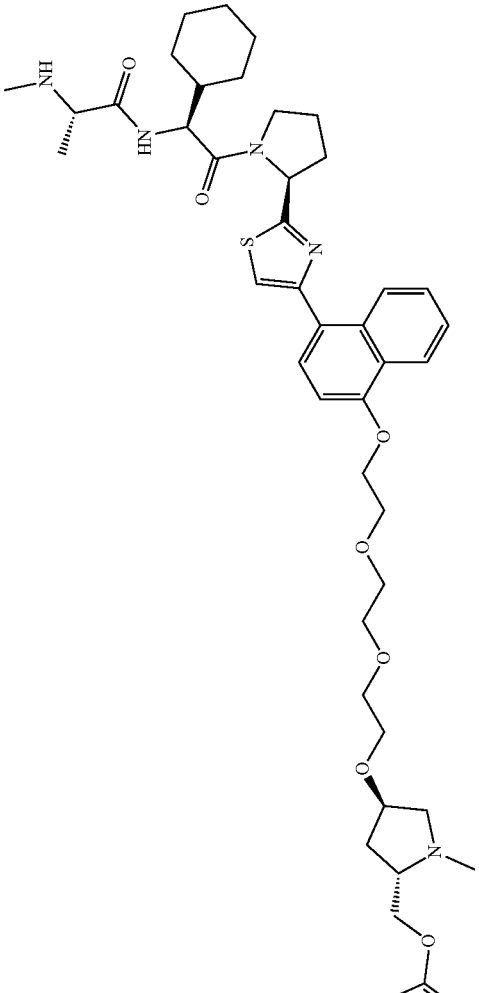 | (S)-N-((S)-2-((S)-2-(4-(4-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)naphthalen-1-yl)thiazol-2-yl)pyrrolidin-1-yl)-1-cyclohexyl-2-oxoethyl)-2-(methylamino)propanamide | 22 |
| 549 | 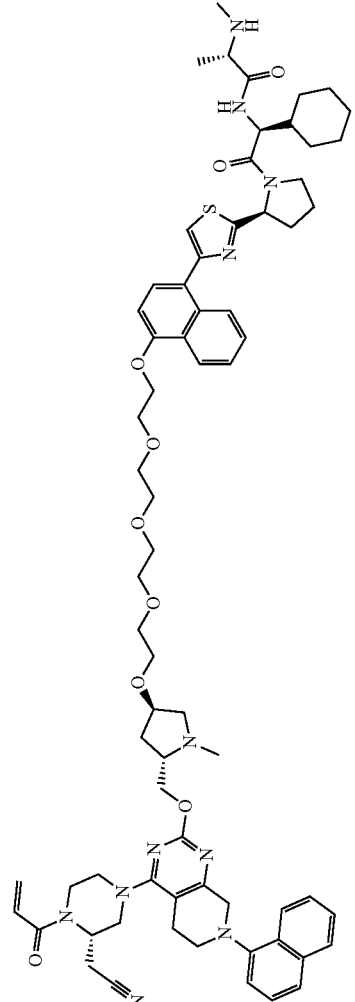 | (2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethoxy)naphthalen-1-yl)thiazol-2-yl)pyrrolidin-1-yl)-1-cyclohexyl-2-oxoethyl)-2-(methylamino)propanamide | 22 |

TABLE 12-continued
Compounds Prepared by Schemes 17-24
| Ex. No. | Structure | Compound Name | Synthetic Scheme |
|---|---|---|---|
| 550 | 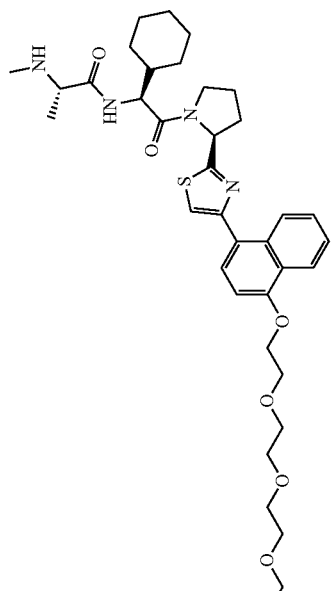 | (S)-N-((S)-2-((S)-2-(4-(4-((14-(((3R,5S)-5-((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)-3,6,9,12-tetraoxatetradecyl)oxy)naphthalen-1-yl)thiazol-2-yl)pyrrolidin-1-yl)-1-cyclohexyl-2-oxoethyl)-2-(methylamino)propanamide | 22 |

TABLE 12-continued
Compounds Prepared by Schemes 17-24
| Ex. No. | Structure | Compound Name | Synthetic Scheme |
|---|---|---|---|
| 551 | 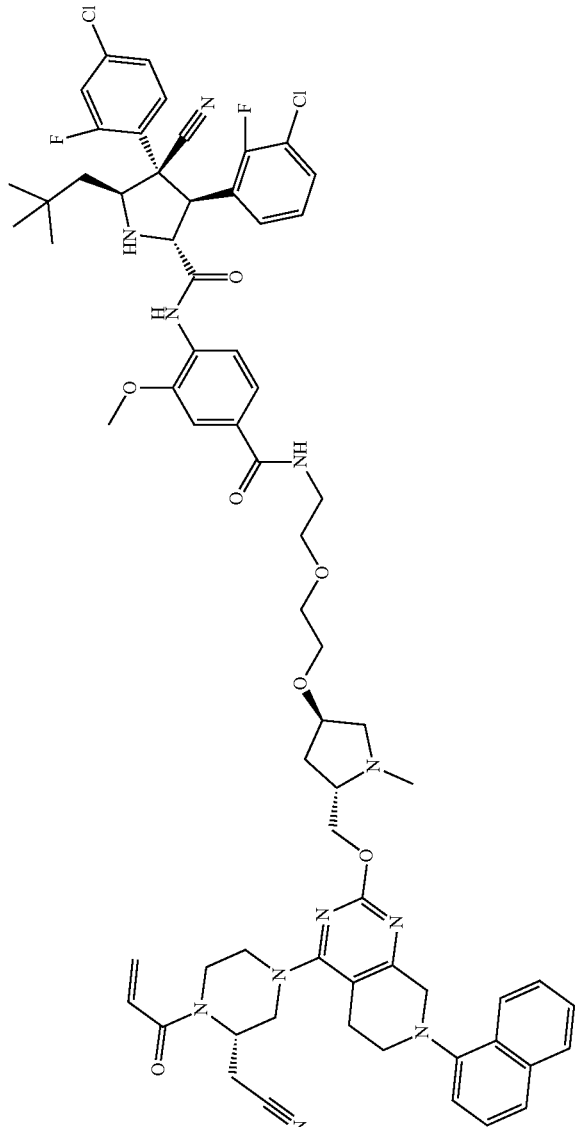 | (2R,3S,4R,5S)-N-(4-((2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 23 |

TABLE 12-continued

Compounds Prepared by Schemes 17-24

| Ex. No. | Structure | Compound Name | Synthetic Scheme |
|---|---|---|---|
| 552 | 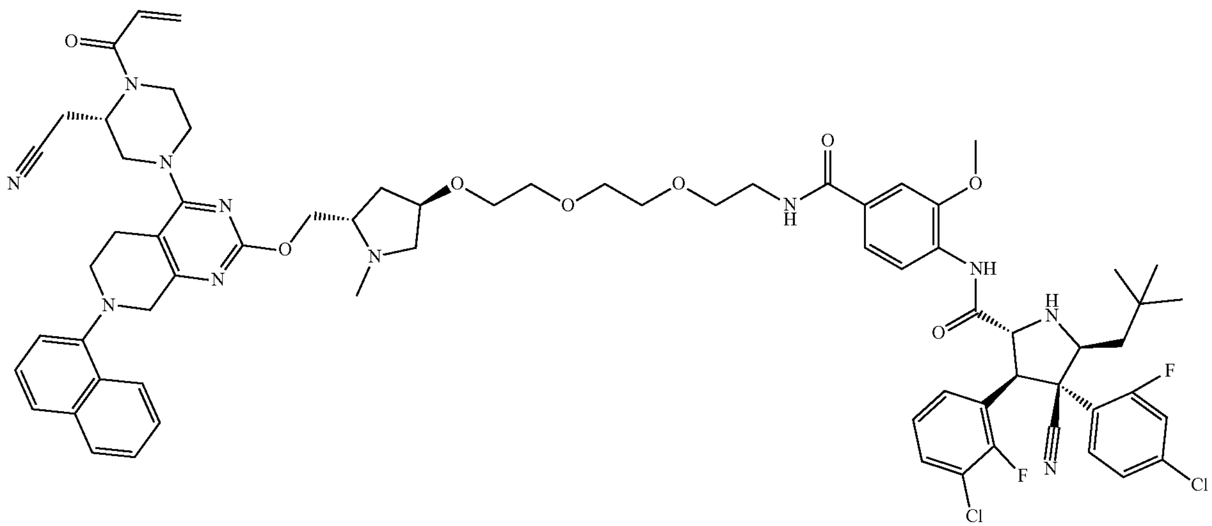 [SMILES: C=CC(=O)N1CCN(c2nc(OC[C@@H]3C[C@@H](OCCOCCOCCNC(=O)c4ccc(NC(=O)[C@@H]5N[C@@H](CC(C)(C)C)[C@](C#N)(c6ccc(Cl)cc6F)[C@H]5c5cccc(Cl)c5F)c(OC)c4)CN3C)nc3c2CCN(c2cccc4ccccc24)C3)C[C@@H]1CC#N] | (2R,3S,4R,5S)-N-(4-((2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 23 |
| 553 | 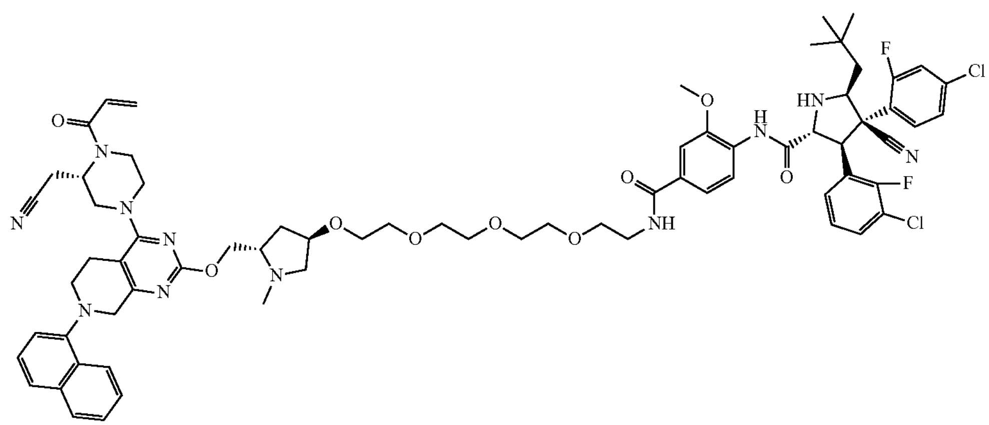 [SMILES: C=CC(=O)N1CCN(c2nc(OC[C@@H]3C[C@@H](OCCOCCOCCOCCNC(=O)c4ccc(NC(=O)[C@@H]5N[C@@H](CC(C)(C)C)[C@](C#N)(c6ccc(Cl)cc6F)[C@H]5c5cccc(Cl)c5F)c(OC)c4)CN3C)nc3c2CCN(c2cccc4ccccc24)C3)C[C@@H]1CC#N] | (2R,3S,4R,5S)-N-(4-((2-(2-(2-(((3R,5S)-5-(((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)ethoxy)ethyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 23 |

TABLE 12-continued

Compounds Prepared by Schemes 17-24

| Ex. No. | Structure | Compound Name | Synthetic Scheme |
|---|---|---|---|
| 554 | 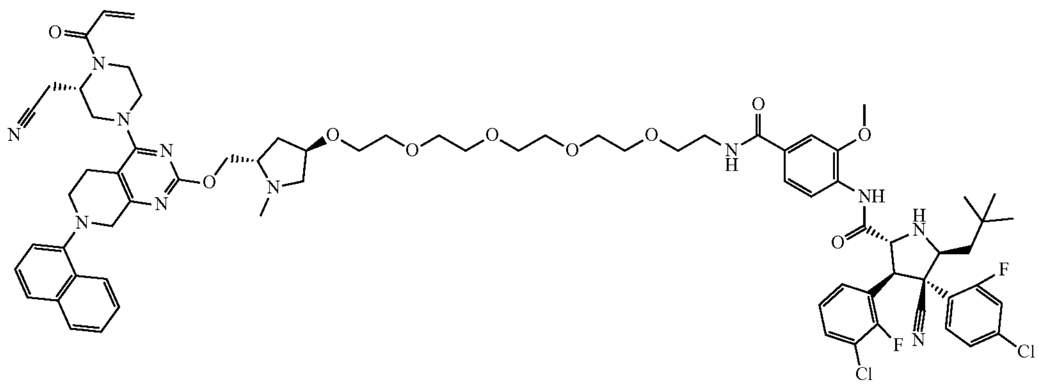 [SMILES: C=CC(=O)N1CCN(c2nc(OC[C@@H]3C[C@@H](OCCOCCOCCOCCOCCNC(=O)c4ccc(NC(=O)[C@@H]5N[C@@H](CC(C)(C)C)[C@](C#N)(c6ccc(Cl)cc6F)[C@H]5c5cccc(Cl)c5F)c(OC)c4)CN3C)nc3c2CCN(c2cccc4ccccc24)C3)C[C@@H]1CC#N] | (2R,3S,4R,5S)-N-(4-((14-(((3R,5S)-5-((4-((S)-4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-1-methylpyrrolidin-3-yl)oxy)-3,6,9,12-tetraoxatetradecyl)carbamoyl)-2-methoxyphenyl)-3-(3-chloro-2-fluorophenyl)-4-(4-chloro-2-fluorophenyl)-4-cyano-5-neopentylpyrrolidine-2-carboxamide | 23 |
| 555 | 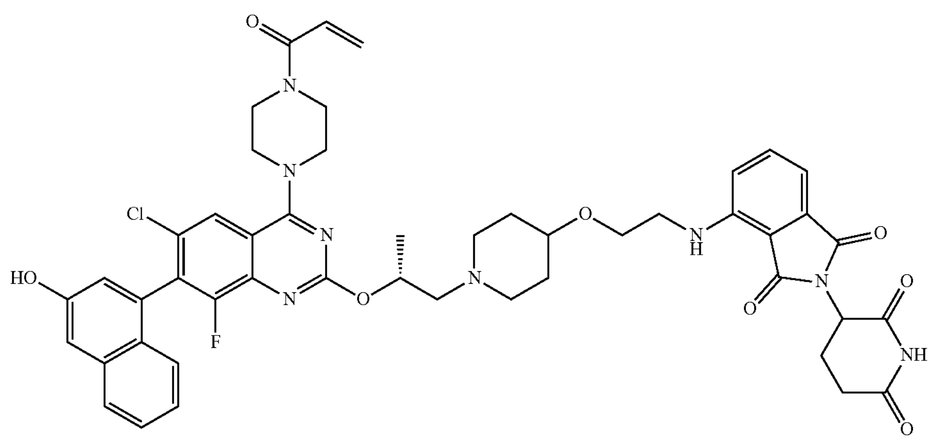 [SMILES: C=CC(=O)N1CCN(c2nc(O[C@H](C)CN3CCC(OCCNc4cccc5c4C(=O)N(C4CCC(=O)NC4=O)C5=O)CC3)nc3c(F)c(-c4cc(O)cc5ccccc45)c(Cl)cc23)CC1] | 4-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethyl)amino)-2-(2,6-dioxopiperidin-3-yl)isoindoline-1,3-dione | 12 |

TABLE 12-continued

Compounds Prepared by Schemes 17-24

| Ex. No. | Structure | Compound Name | Synthetic Scheme |
|---|---|---|---|
| 556 | 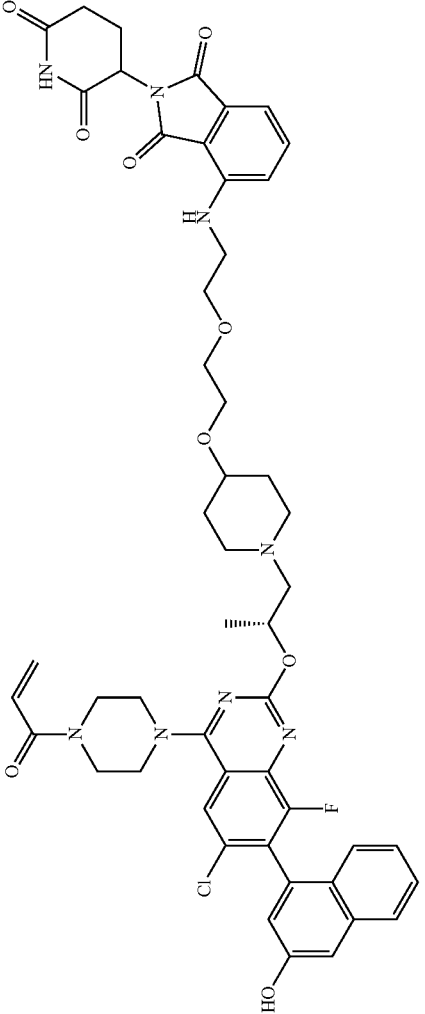 | 4-((2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethyl)amino)-2-(2,6-dioxopiperidin-3-yl)isoindoline-1,3-dione | 12 |
| 557 | 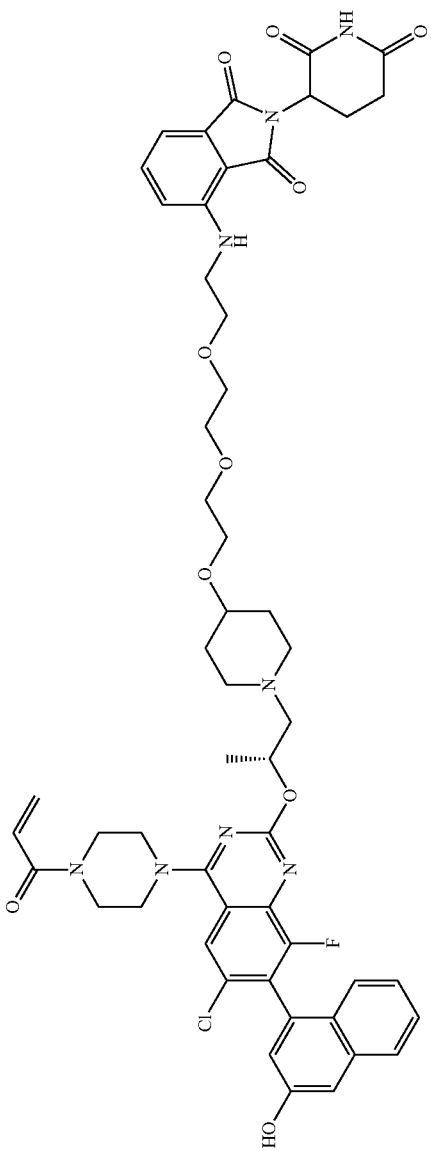 | 4-((2-(2-(2-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)ethyl)amino)-2-(2,6-dioxopiperidin-3-yl)isoindoline-1,3-dione | 12 |

TABLE 12-continued

Compounds Prepared by Schemes 17-24

| Ex. No. | Structure | Compound Name | Synthetic Scheme |
|---|---|---|---|
| 558 | 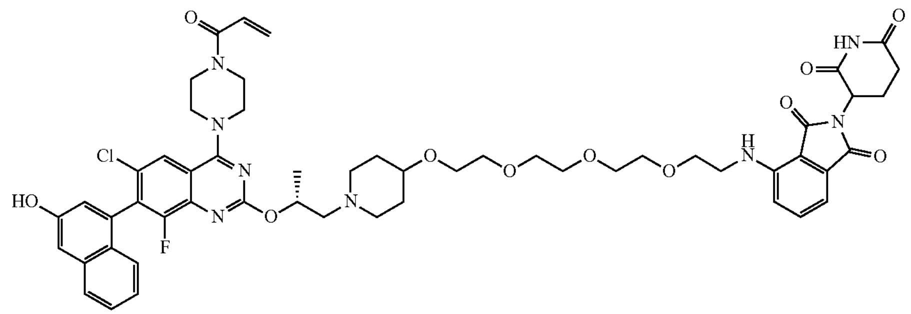 [SMILES: C=CC(=O)N1CCN(c2nc(O[C@H](C)CN3CCC(OCCOCCOCCOCCNc4cccc5c4C(=O)N(C4CCC(=O)NC4=O)C5=O)CC3)nc3c(F)c(-c4cc(O)cc5ccccc45)c(Cl)cc23)CC1] | 4-((2-(2-(2-(2-(((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)ethoxy)ethoxy)ethyl)amino)-2-(2,6-dioxopiperidin-3-yl)isoindoline-1,3-dione | 12 |
| 559 | 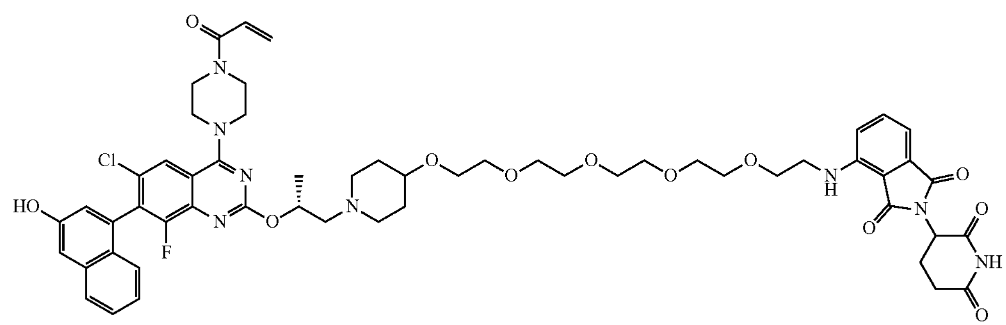 [SMILES: C=CC(=O)N1CCN(c2nc(O[C@H](C)CN3CCC(OCCOCCOCCOCCOCCNc4cccc5c4C(=O)N(C4CCC(=O)NC4=O)C5=O)CC3)nc3c(F)c(-c4cc(O)cc5ccccc45)c(Cl)cc23)CC1] | 4-((14-((1-((2R)-2-((4-(4-acryloylpiperazin-1-yl)-6-chloro-8-fluoro-7-(3-hydroxynaphthalen-1-yl)quinazolin-2-yl)oxy)propyl)piperidin-4-yl)oxy)-3,6,9,12-tetraoxatetradecyl)amino)-2-(2,6-dioxopiperidin-3-yl)isoindoline-1,3-dione | 12 |

TABLE 12-continued

Compounds Prepared by Schemes 17-24

| Ex. No. | Structure | Compound Name | Synthetic Scheme |
|---|---|---|---|
| 560 | 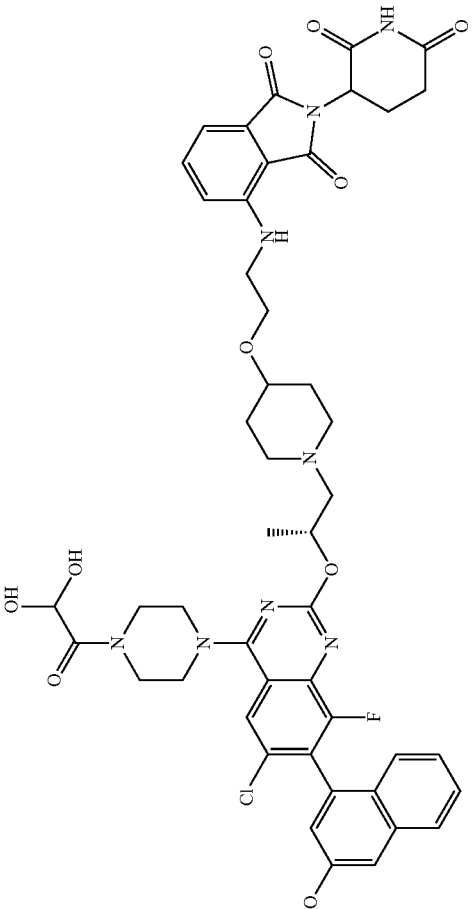 | 4-((2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethyl)amino)-2-(2,6-dioxopiperidin-3-yl)isoindoline-1,3-dione | 12 |
| 561 | 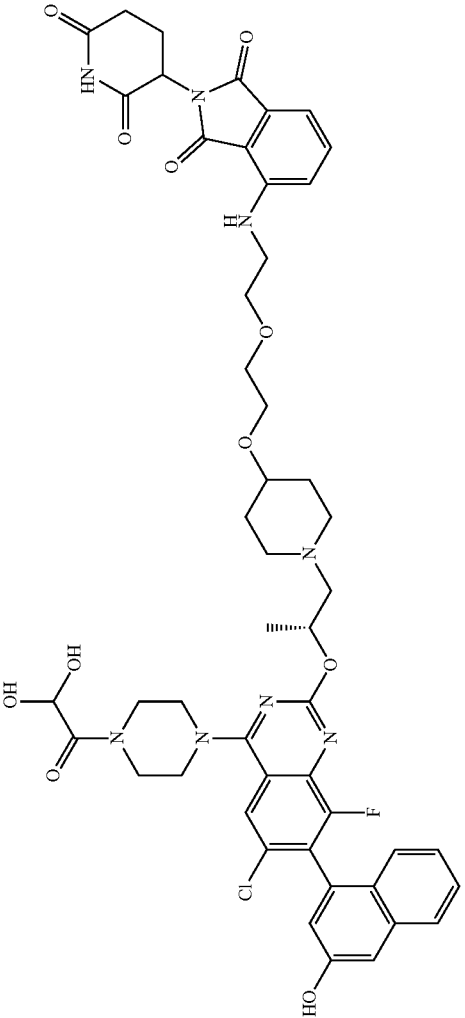 | 4-((2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethyl)amino)-2-(2,6-dioxopiperidin-3-yl)isoindoline-1,3-dione | 12 |

TABLE 12-continued

Compounds Prepared by Schemes 17-24

| Ex. No. | Structure | Compound Name | Synthetic Scheme |
|---|---|---|---|
| 562 | 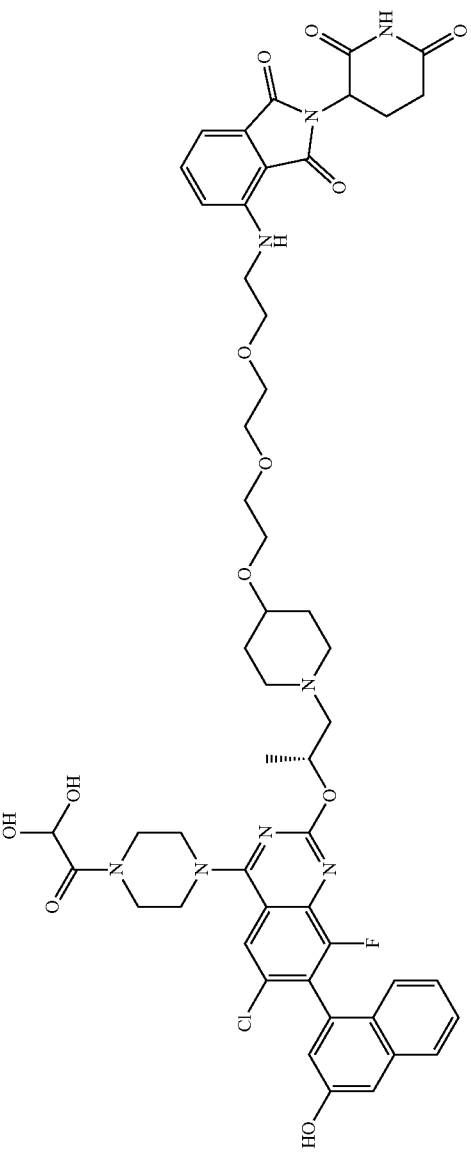 | 4-((2-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)ethyl)amino)-2-(2,6-dioxopiperidin-3-yl)isoindoline-1,3-dione | 12 |
| 563 | 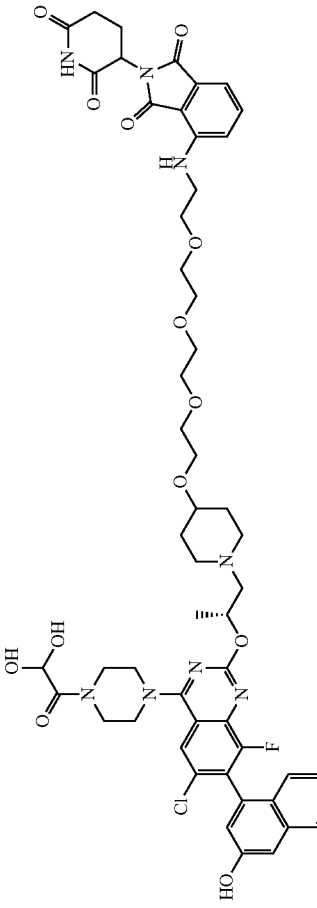 | 4-((2-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)ethyl)amino)-2-(2,6-dioxopiperidin-3-yl)isoindoline-1,3-dione | 12 |

TABLE 12-continued

Compounds Prepared by Schemes 17-24

| Ex. No. | Structure | Compound Name | Synthetic Scheme |
|---|---|---|---|
| 564 | 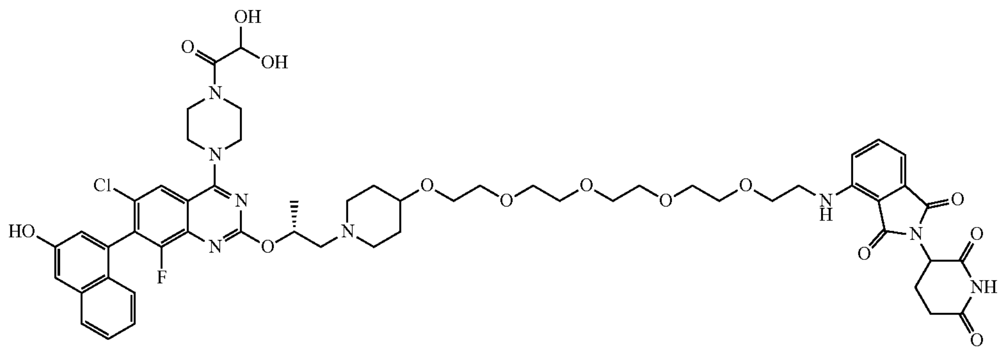 [SMILES: C[C@H](CN1CCC(OCCOCCOCCOCCOCCNc2cccc3c2C(=O)N(C2CCC(=O)NC2=O)C3=O)CC1)Oc1nc(N2CCN(C(=O)C(O)O)CC2)c2cc(Cl)c(-c3cc(O)cc4ccccc34)c(F)c2n1] | 4-((14-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)-3,6,9,12-tetraoxatetradecyl)amino)-2-(2,6-dioxopiperidin-3-yl)isoindoline-1,3-dione | 12 |
| 565 | 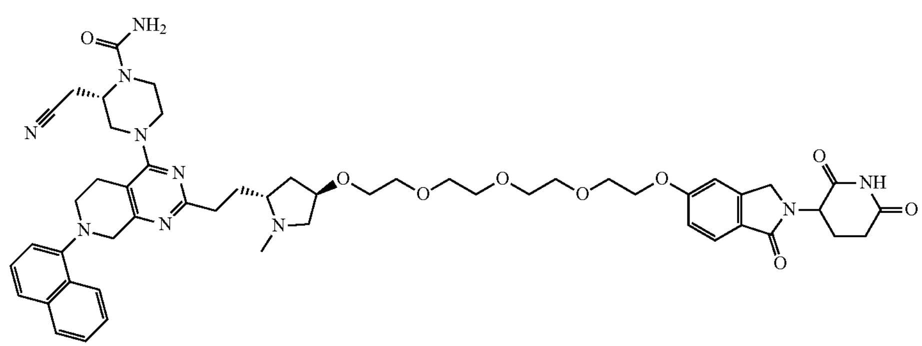 [SMILES: CN1C[C@H](OCCOCCOCCOCCOc2ccc3c(c2)CN(C2CCC(=O)NC2=O)C3=O)C[C@H]1CCc1nc2c(c(N3CCN(C(N)=O)[C@@H](CC#N)C3)n1)CCN(c1cccc3ccccc13)C2] | (2S)-2-(cyanomethyl)-4-(2-(((2S,4R)-4-(2-(2-(2-(2-((2-(2,6-dioxopiperidin-3-yl)-1-oxoisoindolin-5-yl)oxy)ethoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 21 |

TABLE 12-continued

Compounds Prepared by Schemes 17-24

| Ex. No. | Structure | Compound Name | Synthetic Scheme |
|---|---|---|---|
| 566 | 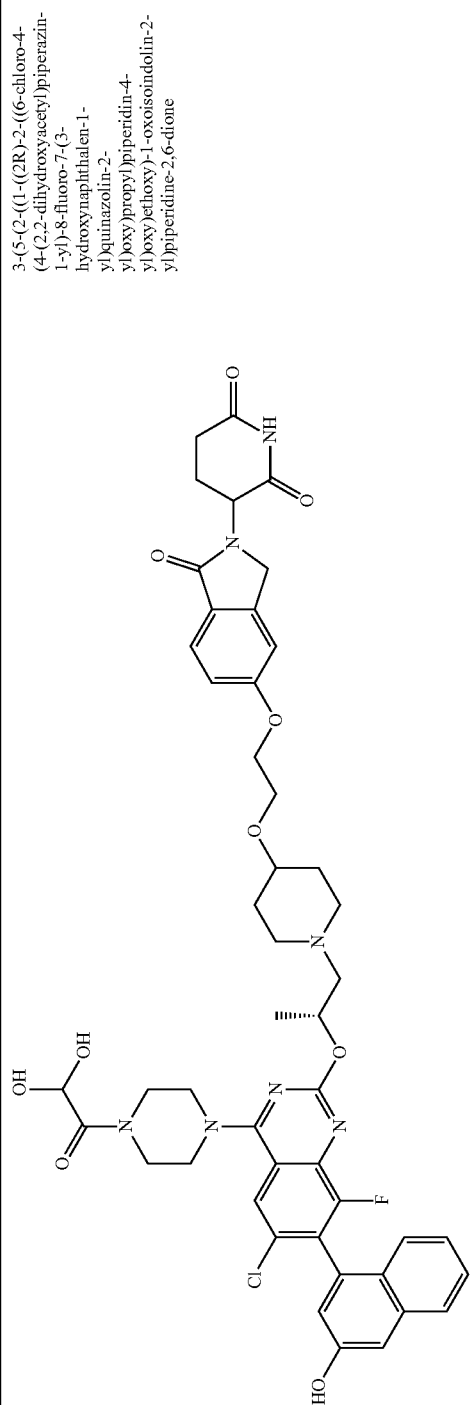 | 3-(5-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)-1-oxoisoindolin-2-yl)piperidine-2,6-dione | 12 |
| 567 | 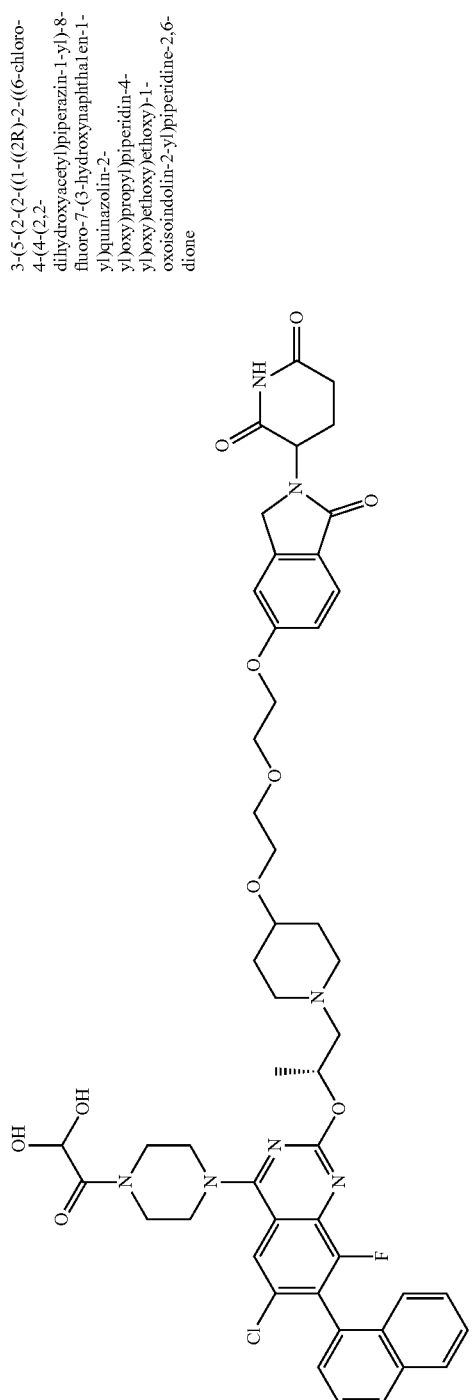 | 3-(5-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)-1-oxoisoindolin-2-yl)piperidine-2,6-dione | 12 |

TABLE 12-continued

Compounds Prepared by Schemes 17-24

| Ex. No. | Structure | Compound Name | Synthetic Scheme |
|---|---|---|---|
| 568 | 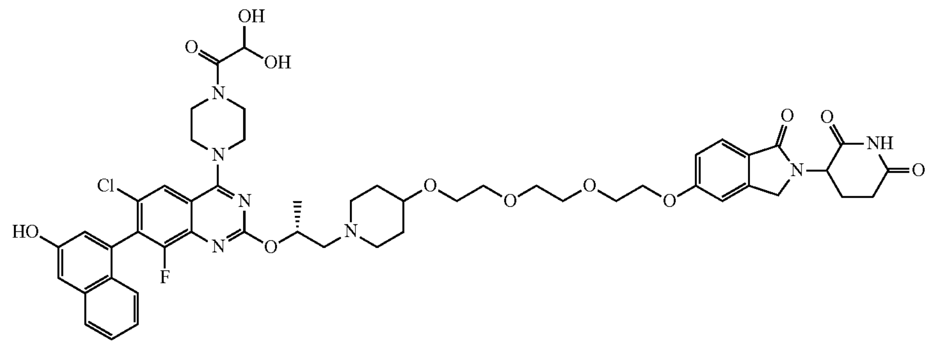 [SMILES: C[C@H](CN1CCC(OCCOCCOCCOc2ccc3c(c2)CN(C2CCC(=O)NC2=O)C3=O)CC1)Oc1nc(N2CCN(C(=O)C(O)O)CC2)c2cc(Cl)c(-c3cc(O)cc4ccccc34)c(F)c2n1] | 3-(5-(2-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)-1-oxoisoindolin-2-yl)piperidine-2,6-dione | 12 |
| 569 | 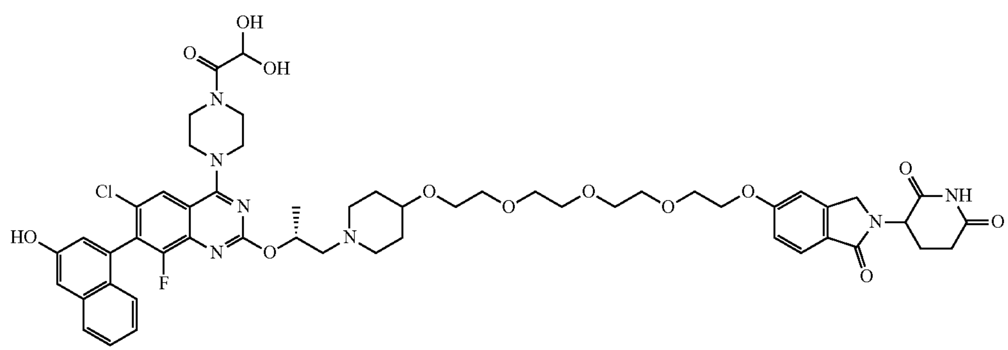 [SMILES: C[C@H](CN1CCC(OCCOCCOCCOCCOc2ccc3c(c2)CN(C2CCC(=O)NC2=O)C3=O)CC1)Oc1nc(N2CCN(C(=O)C(O)O)CC2)c2cc(Cl)c(-c3cc(O)cc4ccccc34)c(F)c2n1] | 3-(5-(2-(2-(2-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)ethoxy)ethoxy)ethoxy)-1-oxoisoindolin-2-yl)piperidine-2,6-dione | 12 |

TABLE 12-continued

Compounds Prepared by Schemes 17-24

| Ex. No. | Structure | Compound Name | Synthetic Scheme |
|---|---|---|---|
| 570 | 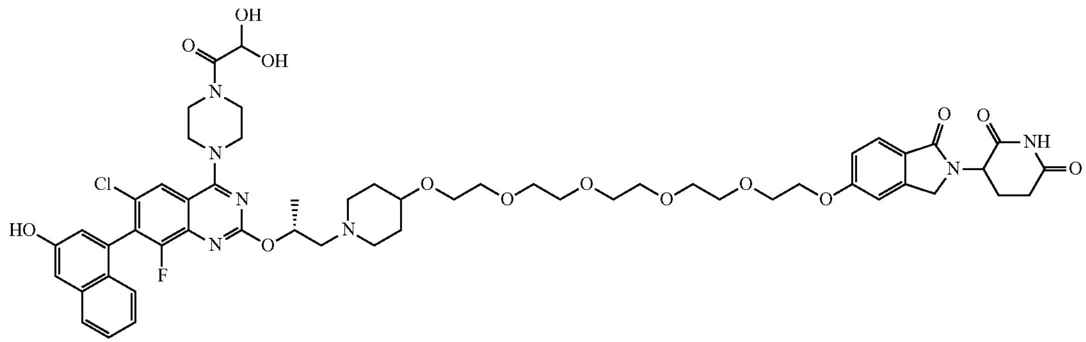 [SMILES: C[C@H](CN1CCC(OCCOCCOCCOCCOCCOc2ccc3c(c2)CN(C2CCC(=O)NC2=O)C3=O)CC1)Oc1nc(N2CCN(C(=O)C(O)O)CC2)c2cc(Cl)c(-c3cc(O)cc4ccccc34)c(F)c2n1] | 3-(5-((14-((1-((2R)-2-((6-chloro-4-(4-(2,2-dihydroxyacetyl)piperazin-1-yl)-8-fluoro-7-(3-hydroxynaphthalen-1-yl)quinazolin-2-yl)oxy)propyl)piperidin-4-yl)oxy)-3,6,9,12-tetraoxatetradecyl)oxy)-1-oxoisoindolin-2-yl)piperidine-2,6-dione | 12 |
| 571 | 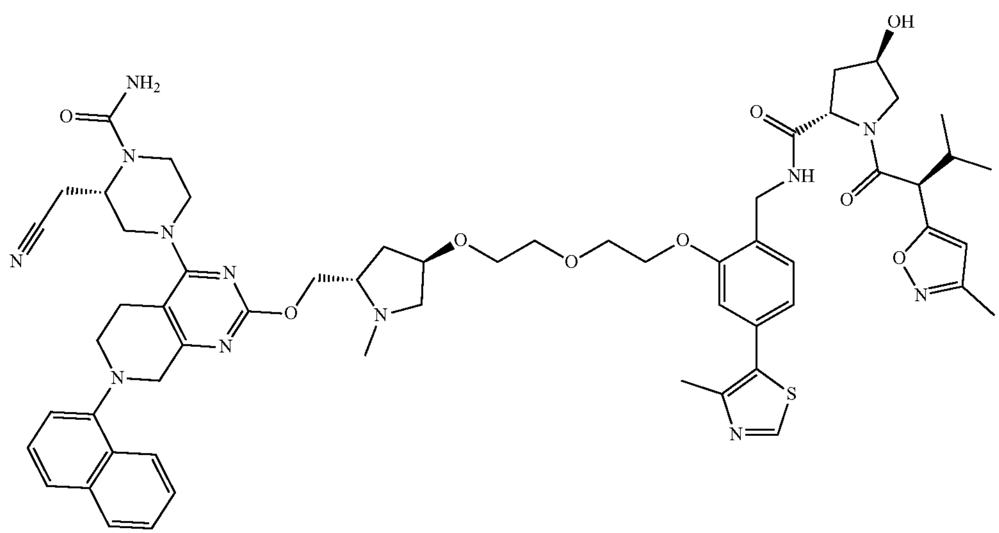 [SMILES: Cc1cc([C@@H](C(=O)N2C[C@H](O)C[C@H]2C(=O)NCc2ccc(-c3scnc3C)cc2OCCOCCO[C@@H]2C[C@@H](COc3nc4c(c(N5CCN(C(N)=O)[C@@H](CC#N)C5)n3)CCN(c3cccc5ccccc35)C4)N(C)C2)C(C)C)on1] | (S)-2-(cyanomethyl)-4-(2-(((2S,4R)-4-(2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 19 |

TABLE 12-continued

Compounds Prepared by Schemes 17-24

| Ex. No. | Structure | Compound Name | Synthetic Scheme |
|---|---|---|---|
| 572 | 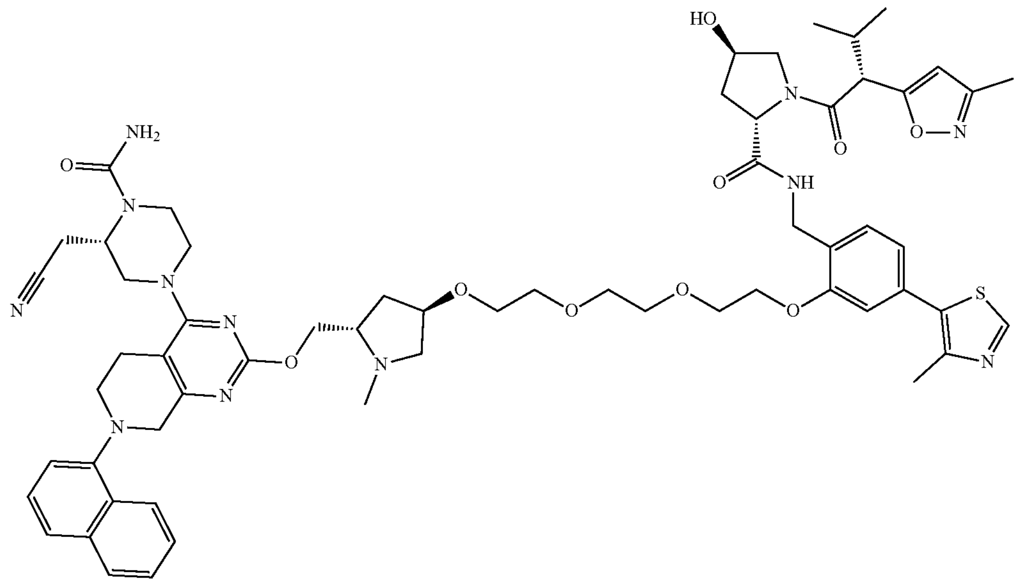 [SMILES: Cc1cc([C@H](C(=O)N2C[C@H](O)C[C@H]2C(=O)NCc2ccc(-c3scnc3C)cc2OCCOCCOCCO[C@@H]2C[C@@H](COc3nc4c(c(N5CCN(C(N)=O)[C@@H](CC#N)C5)n3)CCN(c3cccc5ccccc35)C4)N(C)C2)C(C)C)on1] | (S)-2-(cyanomethyl)-4-(2-(((2S,4R)-4-(2-(2-(2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 19 |

TABLE 12-continued
Compounds Prepared by Schemes 17-24
| Ex. No. | Structure | Compound Name | Synthetic Scheme |
|---|---|---|---|
| 573 | 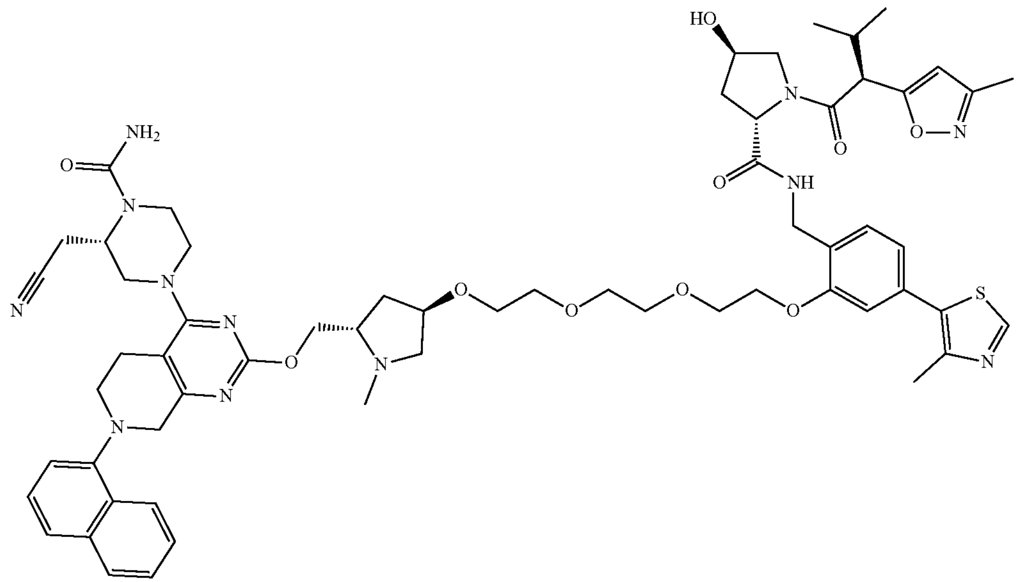 [SMILES: Cc1cc([C@@H](C(=O)N2C[C@H](O)C[C@H]2C(=O)NCc2ccc(-c3scnc3C)cc2OCCOCCOCCO[C@@H]2C[C@@H](COc3nc4c(c(N5CCN(C(N)=O)[C@@H](CC#N)C5)n3)CCN(c3cccc5ccccc35)C4)N(C)C2)C(C)C)on1] | (S)-2-(cyanomethyl)-4-(2-(((2S,4R)-4-(2-(2-(2-(((2S,4R)-4-hydroxy-1-((S)-3-methyl-2-(3-methylisoxazol-5-yl)butanoyl)pyrrolidine-2-carboxamido)methyl)-5-(4-methylthiazol-5-yl)phenoxy)ethoxy)ethoxy)-1-methylpyrrolidin-2-yl)methoxy)-7-(naphthalen-1-yl)-5,6,7,8-tetrahydropyrido[3,4-d]pyrimidin-4-yl)piperazine-1-carboxamide | 19 |

TABLE 13

Data for Compounds of Table 12

| Ex. No. | MH+ (1) | MH+ (2) | NMR Transcript | Synthetic Scheme | Mol Weight |
|---|---|---|---|---|---|
| 498 | 1186.71 | 1188.71 | ¹H NMR (400 MHz, DMSO-d₆) δ 10.17-9.95 (m, 1H), 8.98 (s, 1H), 8.39 (d, J = 7.6 Hz, 1H), 8.30 (s, 1H), 8.00 (s, 1H), 7.81 (d, J = 8.3 Hz, 1H), 7.69-7.62 (m, 1H), 7.46-7.42 (m, 3H), 7.40-7.36 (m, 2H), 7.29 (d, J = 2.1 Hz, 1H), 7.26-7.17 (m, 2H), 7.09-7.05 (m, 1H), 6.83 (dd, J = 10.4, 16.6 Hz, 1H), 6.18 (dd, J = 2.3, 16.7 Hz, 1H), 5.78-5.71 (m, 1H), 5.52-5.23 (m, 2H), 4.91 (t, J = 6.9 Hz, 1H), 4.43 (d, J = 9.3 Hz, 1H), 4.33 (dd, J = 6.8, 8.4 Hz, 1H), 4.24-4.15 (m, 1H), 4.02-3.70 (m, 12H), 3.03-2.79 (m, 5H), 2.45 (s, 7H), 2.10-1.86 (m, 5H), 1.65-1.51 (m, 3H), 1.42-1.25 (m, 8H), 0.96-0.89 (m, 12H). | 11 | 1186.87 |
| 499 | 1096.69 | | ¹H-NMR (400 MHz, DMSO-d₆) δ 8.98 (s, 1H), 8.44 (d, J = 4.0 Hz, 1H), 8.36 (s, 2H), 8.22-8.15 (m, 1H), 7.96-7.90 (m, 1H), 7.64 (d, J = 4.0 Hz, 1H), 7.56-7.51 (m, 2H), 7.48-7.41 (m, 3H), 7.38-7.33 (m, 3H), 7.23 (d, J = 8.0 Hz, 1H), 6.98-6.77 (m, 1H), 6.25-6.14 (m, 1H), 5.83-5.73 (m, 1H), 4.92-4.87 (m, 1H), 4.54 (d, J = 9.6 Hz, 1H), 4.48-4.41 (m, 2H), 4.31-4.27 (m, 2H), 4.16-4.12 (m, 3H), 4.05-4.00 (m, 3H), 3.96 (s, 2H), 3.62-3.46 (m, 6H), 3.23-3.17 (m, 2H), 3.06-3.00 (m, 2H), 2.96-2.91 (m, 3H), 2.77-2.70 (m, 2H), 2.45 (s, 3H), 2.35-2.32 (m, 3H), 2.28-2.23 (m, 2H), 2.09-2.01 (m, 2H), 1.96-1.88 (m, 2H), 1.88-1.75 (m, 3H), 1.36 (d, J = 6.8 Hz, 3H), 0.94 (s, 9H). | 17 | 1096.34 |
| 500 | 1140.72 | | ¹H NMR (400 MHz, DMSO-d₆) δ 8.98 (s, 1H), 8.44 (br d, J = 7.6 Hz, 1H), 8.30 (s, 1H), 8.22-8.14 (m, 1H), 7.97-7.88 (m, 1H), 7.64 (d, J = 8.2 Hz, 1H), 7.59-7.49(m, 2H), 7.48-7.39 (m, 3H), 7.38-7.33 (m, 2H), 7.22 (d, J = 7.2 Hz, 1H), 6.88 (br s, 1H), 6.20 (br d, J = 17.4 Hz, 1H), 5.78 (br d, J = 11.6 Hz, 1H), 5.06-4.63 (m, 2H), 4.55 (br d, J = 9.5 Hz, 1H), 4.45 (br t, J = 8.1 Hz, 1H), 4.34-4.22 (m, 2H), 4.17-4.09 (m, 3H), 4.08-3.98 (m, 3H), 3.98-3.91 (m, 2H), 3.61 (br d, J = 3.1 Hz, 2H), 3.58 (br d, J = 3.9 Hz, 4H), 3.56-3.53 (m, 1H), 3.54 (br s, 2H), 3.53-3.48 (m, 4H), 3.29 (br dd, J = 6.2, 9.5 Hz, 2H), 3.24-3.17 (m, 2H), 3.07-2.90 (m, 4H), 2.78-2.63 (m, 2H), 2.45 (s, 3H), 2.34(s, 3H), 2.19 (br dd, J = 6.0, 9.4 Hz, 1H), 2.10-2.00 (m, 1H), 1.92-1.72 (m, 3H), 1.37 (br d, J = 7.0 Hz, 3H), 0.94 (s, 9H). | 17 | 1140.40 |
| 501 | 1184.75 | | ¹H NMR (400 MHz, DMSO-d₆) δ 8.98 (s, 1H), 8.42 (br d, J = 8.4 Hz, 1H), 8.20 (s, 1H), 8.18 (br d, J = 0.6 Hz, 1H), 7.93 (br d, J = 5.3 Hz, 1H), 7.65 (d, J = 8.2 Hz, 1H), 7.54 (br d, J = 8.3 Hz, 2H), 7.50-7.41 (m, 3H), 7.37 (br d, J = 7.9 Hz, 2H), 7.23 (d, J = 7.7 Hz, 1H), 6.87 (br s, 1H), 6.20 (br d, J = I6.4 Hz, 1H), 5.78 (br d, J = 11.1 Hz, 1H), 5.16-4.98 (m, 1H), 4.91 (br t, J = 6.8 Hz, 2H), 4.55 (br d, J = 9.8 Hz, 1H), 4.45 (br t, J = 8.3 Hz, 1H), 4.30-4.23 (m, 2H), 4.16-4.10 (m, 3H), 4.03 (br d, J = 16.9 Hz, 4H), 3.98-3.91 (m, 3H), 3.60 (br d, J = 7.3 Hz, 4H), 3.55 (br s, 6H), 3.50 (br d, J = 10.3 Hz, 10H), 2.96 (br d, J = 18.8 Hz, 3H), 2.73 (br s, 1H), 2.45 (s, 3H), 2.22-2.15 (m, 2H), 2.10-1.99 (m, 2H), 1.94-1.74 (m, 4H), 1.38 (br d, J = 6.7 Hz, 3H), 0.94 (s, 9H). | 17 | 1184.45 |
| 502 | 1272.83 | | ¹H NMR (400 MHz, CD₃OD) δ 9.18 (s, 1H), 8.26-8.24 (m, 1H), 7.91-7.88 (m, 1H), 7.68 (d, J = 8.4 Hz, 1H), 7.55-7.39 (m, 7H), 7.24 (d, J = 7.2 Hz, 1H), 6.95-6.75 (m, 1H), 6.33 (d, J = 16.4 Hz, 1H), 5.87 (d, J = 10.4 Hz, 1H), 5.06-5.01 (m, 2H), 4.85-4.78 (m, 2H), 4.69 (s, 1H), 4.61-4.50 (m, 2H), 4.45-4.37 (m, 2H), 4.32 (s, 2H), 4.26-4.15 (m, 2H), 4.11-4.02 (m, 1H), 3.96-3.80 (m, 2H), 3.85-3.60 (m, 24H), 3.54-3.35 (m, 4H), 3.19 (s, 3H), 3.15-2.90 (m, 4H), 2.61-2.53 (m, 1H), 2.52, 2.51 (s, 3H), 2.25-2.15 (m, 2H), 2.00-1.92 (m, 1H), 1.58, 1.51 (d, J = 7.2 Hz, 3H), 1.06, 1.04 (s, 9H). | 17 | 1272.56 |
| 503 | 912.52 | | ¹H NMR (400 MHz, DMSO) δ 11.09(s, 1H), 8.19-8.17 (m, 1H), 7.93-7.91 (m, 1H), 7.83 (d, J = 8.0 Hz, 1H), 7.65 (d, J = 8.4 Hz, 1H), 7.55-7.52 (m, 2H), 7.48-7.44 (m, 2H), 7.38 (dd, J = 8.0 Hz, J = 2.4 Hz, 1H), 7.23 (d, J = 7.6 Hz, 1H), 6.85 (s, 1H), 6.21-6.16 (m, 1H), 5.79 (dd, J = 10.4 Hz, J = 2.4 Hz, 1H), 5.13-5.08 (m, 1H), 4.98-4.78 (m, 1H), 4.32-4.23 (m, 3H), 4.15-3.98 (m, 6H), 3.80-3.78 (m, 2H), 3.59-3.44 (m, 5H), 3.28-3.19 (m, 6H), 3.08-2.88 (m, 6H), 2.70-2.67 (m, 1H), 2.61-2.56 (m, 1H), 2.32 (s, 3H), 2.18-2.14 (m, 1H), 2.05-2.03 (m, 1H), 1.87-1.76 (m, 2H). | 18 | 912.00 |
| 504 | 956.55 | | ¹H NMR (400 MHz, DMSO-d₆) δ 11.10 (br s, 1H), 8.37-8.06 (m, 2H), 7.96-7.77 (m, 2H), 7.63 (br s, 1H), 7.58-7.42 (m, 4H), 7.36 (br s, 1H), 7.22 (m, 1H), 6.86 (br s, 1H), 6.19 (br d, J = 17.0 Hz, 1H), 5.78 (br d, J = 8.8 Hz, 1H), 5.11 (br d, J = 7.9 Hz, 1H), 5.03-4.71 (m, 1H), 4.41 (br s, 1H), 4.34-4.23 (m, 3H), 4.13 (br s, 4H), 4.02 (br d, J = 12.3 Hz, 4H), 3.78 (br s, 4H), 3.59 (br s, 2H), 3.54 (br s, 2H), 3.49 (br s, 4H), 3.30-3.16 (m, 1H), 3.06-2.86 (m, 6H), 2.67 (br s, 1H), 2.32 (br s, 3H), 2.16 (m, 1H), 2.04 (br s, 1H), 1.85 (m, 2H). | 18 | 956.05 |
| 505 | 1044.62 | | ¹H NMR (400 MHz, CDCl₃) δ 8.66 (d, J = 18.0 Hz, 1H), 8.19-8.16 (m, 1H), 7.88-7.85 (m, 1H), 7.77 (d, J = 8.0 Hz, 1H), 7.63 (d, J = 8.4 Hz, 1H), 7.55-7.48 (m, 2H), 7.44 (t, J = 8.0 Hz, 1H), 7.37 (d, J = 2.0 Hz, 1H), 7.23 (dd, J = 2.0, 8.4 Hz, 1H), 7.15 (d, J = 7.6 Hz, 1H), 6.70-6.50 (m, 1H), 6.41 (d, J = 16.4 Hz, 1H), 5.85 (d, J = 10.8 Hz, 1H), 5.10-4.87 (m, 3H), 4.80 (d, J = 10.8 Hz, 1H), 4.60 (d, J = 8.4 Hz, 1H), 4.40 (s, 2H), 4.35-4.20 (m, 4H), 4.15-3.95 (m, 3H), 3.90 (t, J = 4.8 Hz, 2H), 3.80-3.52 (m, 17H), 3.50-3.30 (m, 3H), 3.28-3.18 (m, 2H), 3.13 (s, 3H), 3.05-2.65 (m, 7H), 2.44 (dd, J = 6.8, 14.4 Hz, 1H), 2.26-2.10 (m, 2H). | 18 | 1044.16 |
| 506 | 1136.69 | | ¹H NMR (400 MHz, DMSO-d₆) δ 8.98 (s, 1H), 8.33-8.30 (m, 1H), 8.19-8.17 (m, 1H), 7.95-7.92 (m, 1H), 7.65 (d, J = 8.0 Hz, 1H), 7.55-7.53 (m, 2H), 7.47 (t, J = 7.6 Hz, 1H), 7.32-7.21 (m, 2H), 7.08-6.97 (m, 2H), 6.87 (s, 1H), 6.22-6.18 (m, 2H), 5.81-5.78 (m, 1H), 5.00-4.76 (m, 1H), 4.62-4.59 (m, 1H), 4.48-4.41 (m, 1H), 4.33-4.08 (m, 12H), 3.98-3.88 (m, 1H), 3.85 (d, J = 8.4 Hz, 1H), 3.83-3.71 (m, 3H), 3.65-3.59 (m, 6H), 3.55-3.44 (m, 1H), 3.41-3.33 (m, 1H), 3.31-3.14 (m, 4H), 3.08-3.29 (m, 7H), 2.46-2.44 (m, 3H), 2.37-2.23 (m, 2H), 2.21-2.13 (m, 3H), 2.08-1.86 (m, 2H), 1.00-0.55 (m, 6H). | 19 | 1136.37 |
| 507 | 1136.69 | | ¹H NMR (400 MHz, DMSO-d₆) δ 8.99 (s, 1H), 8.65-8.37 (m, 1H), 8.20-8.17 (m, 1H), 7.95-7.93 (m, 1H), 7.67 (d, J = 8.0 Hz, 1H), 7.56-7.54 (m, 2H), 7.47 (t, J = 7.6 Hz, 1H), 7.36 (d, J = 7.6 Hz, 1H), 7.24-7.22 (m, 1H), 7.06-7.00 (m, 2H), 6.88 (s, 1H), 6.23-6.18 (m, 2H), 5.81-5.78 (m, 1H), 4.99-4.78 (m, 1H), 4.63-4.59 (m, 1H), 4.48-4.17 (m, 12H), 4.10-4.07 (m, 3H), 3.96-3.92 (m, 1H), 3.82-3.73 (m, 5H), 3.67-3.55 (m, 5H), 3.46-3.37 (m, 2H), 3.30-3.17 (m, 4H), 3.00-2.97 (m, 7H), 2.48-2.44 (m, 3H), 2.39-2.22 (m, 2H), 2.21-2.13 (m, 3H), 2.09-1.88 (m, 2H), 0.97-0.93 (m, 3H), 0.79-0.76 (m, 3H). | 19 | 1136.37 |

TABLE 13-continued

Data for Compounds of Table 12

| Ex. No. | MH+ (1) | MH+ (2) | NMR Transcript | Synthetic Scheme | Mol Weight |
|---|---|---|---|---|---|
| 508 | 1180.72 | | $^1$H NMR (400 MHz, DMSO-d$_6$) δ 8.97 (s, 1H), 8.75 (t, J = 5.9 Hz, 1H), 8.32-8.25 (m, 1H), 8.22-8.14 (m, 1H), 7.96-7.88 (m, 1H), 7.64 (d, J = 8.3 Hz, 1H), 7.58-7.50 (m, 2H), 7.46 (t, J = 7.8 Hz, 1H), 7.32-7.19 (m, 2H), 7.09-6.94 (m, 2H), 6.87 (br s, 1H), 6.25-6.14 (m, 2H), 5.81-5.74 (m, 1H), 5.17-4.69 (m, 2H), 4.52-4.19 (m, 6H), 4.19-4.15 (m, 2H), 4.14-4.06 (m, 3H), 4.02 (br d, J = 12.8 Hz, 2H), 3.98-3.92 (m, 1H), 3.86-3.71 (m, 3H), 3.65-3.52 (m, 6H), 3.52-3.47 (m, 3H), 3.47-3.41 (m, 2H), 3.26 (br dd, J = 6.3, 9.3 Hz, 2H), 3.19 (br s, 2H), 3.08-2.97 (m, 2H), 2.94 (br s, 1H), 2.73-2.68 (m, 1H), 2.46-2.44 (m, 3H), 2.31 (s, 3H), 2.26 (br dd, J = 6.8, 15.1 Hz, 1H), 2.13 (s, 4H), 2.09-1.99 (m, 1H), 1.97-1.76 (m, 3H), 0.96 (d, J = 6.6 Hz, 2.5H), 0.79 (d, J = 6.8 Hz, 2.5H), 0.69 (d, J = 6.6 Hz, 0.5H), 0.56 (d, J = 6.8 Hz, 0.5H). | 19 | 1180.42 |
| 509 | 1180.72 | | $^1$H NMR (400 MHz, DMSO-d$_6$) δ 8.97 (s, 1H), 8.64-8.32 (m, 1H), 8.23-8.13 (m, 1H), 7.98-7.88 (m, 1H), 7.64 (d, J = 8.3 Hz, 1H), 7.59-7.50 (m, 2H), 7.46 (t, J = 7.8 Hz, 1H), 7.35 (d, J = 7.9 Hz, 1H), 7.27-7.16 (m, 1H), 7.10-6.96 (m, 2H), 6.87 (br s, 1H), 6.22-5.91 (m, 2H), 5.83-5.74 (m, 1H), 5.22-4.92 (m, 2H), 4.86-4.64 (m, 1H), 4.39 (br t, J = 7.8 Hz, 1H), 4.35 (br s, 1H), 4.29-4.21 (m, 3H), 4.20-4.16 (m, 2H), 4.13 (s, 2H), 4.09 (br dd, J = 5.8, 10.9 Hz, 1H), 4.04-3.94 (m, 3H), 3.82-3.76 (m, 3H), 3.74 (d, J = 9.6 Hz, 1H), 3.66-3.58 (m, 3H), 3.58-3.53 (m, 3H), 3.52-3.48 (m, 3H), 3.47-3.41 (m, 4H), 3.27-3.24 (m, 2H), 3.20 (br s, 2H), 3.05-2.97 (m, 2H), 2.93 (br s, 2H), 2.74-2.70 (m, 1H), 2.47-2.42 (m, 3H), 2.31 (s, 3H), 2.28-2.21 (m, 1H), 2.20-2.11 (m, 4H), 2.08-1.99 (m, 1H), 1.99-1.74 (m, 3H), 0.98-0.90 (m, 3H), 0.79-0.73 (m, 3H). | 19 | 1180.42 |
| 510 | 1224.74 | | $^1$H NMR (400 MHz, DMSO-d$_6$) δ 8.97 (s, 1H), 8.76-8.24 (m, 2H), 8.20-8.14 (m, 1H), 7.96-7.88 (m, 1H), 7.64 (d, J = 8.1 Hz, 1H), 7.58-7.50 (m, 2H), 7.46 (t, J = 7.8 Hz, 1H), 7.33-7.17 (m, 2H), 7.11-6.94 (m, 2H), 6.86 (br s, 1H), 6.25-6.15 (m, 2H), 5.78 (br d, J = 12.4 Hz, 1H), 5.13 (br s, 1H), 4.98 (br s, 1H), 4.86-4.67 (m, 1H), 4.54-4.32 (m, 4H), 4.31-4.19 (m, 4H), 4.17-4.06 (m, 5H), 4.06-3.91 (m, 4H), 3.88-3.73 (m, 4H), 3.64-3.59 (m, 3H), 3.57-3.52 (m, 4H), 3.50 (br s, 4H), 3.47 (br s, 2H), 3.26 (br d, J = 2.9 Hz, 2H), 3.17 (br s, 2H), 3.10-2.83 (m, 3H), 2.74-2.69 (m, 1H), 2.46-2.44 (m, 3H), 2.31 (s, 3H), 2.26 (br dd, J = 6.9, 15.1 Hz, 1H), 2.20-2.11 (m, 4H), 2.10-2.01 (m, 1H), 1.99-1.76 (m, 3H), 0.96 (d, J = 6.6 Hz, 2H), 0.79 (d, J = 6.8 Hz, 2H), 0.68 (d, J = 6.5 Hz, 1H), 0.56 (d, J = 6.8 Hz, 1H) | 19 | 1224.47 |
| 511 | 1224.75 | | $^1$H NMR (400 MHz, DMSO-d$_6$) δ 8.97 (s, 1H), 8.60-8.35 (m, 1H), 8.17 (br d, J = 4.9 Hz, 1H), 7.98-7.87 (m, 1H), 7.64 (d, J = 8.4 Hz, 1H), 7.57-7.50 (m, 2H), 7.46 (t, J = 7.8 Hz, 1H), 7.35 (d, J = 7.6 Hz, 1H), 7.26-7.16 (m, 1H), 7.08-6.96 (m, 2H), 6.86 (br s, 1H), 6.24-6.15 (m, 2H), 5.77 (br d, J = 11.5 Hz, 1H), 5.10 (br s, 1H), 4.99 (s, 2H), 4.86-4.61 (m, 1H), 4.45-4.32 (m, 2H), 4.29-4.21 (m, 3H), 4.18 (br d, J = 3.8 Hz, 2H), 4.13 (s, 2H), 4.10-3.91 (m, 5H), 3.82-3.72 (m, 4H), 3.65-3.58 (m, 3H), 3.57-3.52 (m, 3H), 3.50 (br s, 4H), 3.47 (br s, 2H), 3.42 (br d, J = 6.1 Hz, 2H), 3.27-3.24 (m, 2H), 3.21-3.16 (m, 3H), 2.96 (br d, J = 16.4 Hz, 3H), 2.70 (br s, 1H), 2.46 (s, 3H), 2.31 (s, 3H), 2.26 (br d, J = 10.1 Hz, 1H), 2.20-2.12 (m, 4H), 2.08-1.99 (m, 1H), 1.97-1.89 (m, 1H), 1.89-1.76 (m, 2H), 0.98-0.89 (m, 3H), 0.76 (d, J = 6.8 Hz, 3H) | 19 | 1224.47 |
| 512 | 1268.80 | | $^1$H NMR (400 MHz, CD$_3$OD) δ 8.98-8.91 (m, 1H), 8.28-8.15 (m, 1H), 7.91-7.83 (m, 1H), 7.63 (d, J = 8.4 Hz, 1H), 7.56-7.47 (m, 2H), 7.47-7.39 (m, 1H), 7.38 (t, J = 8.0 Hz, 1H), 7.24-7.17 (m, 1H), 7.13-6.97 (m, 2H), 6.94-6.71 (m, 1H), 6.31 (d, J = 16.8 Hz, 1H), 6.22-6.10 (m, 1H), 5.85 (d, J = 10.8 Hz, 1H), 5.15-4.94 (m, 1H), 4.86-4.49 (m, 4H), 4.49-4.12 (m, 11H), 3.99-3.78 (m, 4H), 3.77-3.55 (m, 21H), 3.54-3.34 (m, 4H), 3.20-2.85 (m, 6H), 2.56-2.45 (m, 4H), 2.44-2.29 (m, 1H), 2.27-2.11 (m, 5H), 2.08-1.97 (m, 1H), 1.07-0.49 (m, 6H). | 19 | 1268.52 |
| 513 | 1268.79 | | $^1$H NMR (400 MHz, CD$_3$OD) δ 8.75 (s, 1H), 8.16-8.09 (m, 1H), 7.80-7.71 (m, 1H), 7.49 (d, J = 8.4 Hz, 1H), 7.44-7.20 (m, 4H), 7.08 (d, J = 7.2 Hz, 1H), 6.99-6.88 (m, 2H), 6.87-6.58 (m, 1H), 6.19 (d, J = 16.8 Hz, 1H), 6.10 (s, 1H), 5.73 (d, J = 10.4 Hz, 1H), 5.00-4.97 (m, 1H), 4.48-3.93 (m, 14H), 3.83-3.72 (m, 3H), 3.71-3.35 (m, 20H), 3.27 (dd, J = 6.0, 10.4 Hz, 2H), 3.17-2.74 (m, 7H), 2.42-2.22 (m, 8H), 2.17-2.03 (m, 4H), 2.03-1.88 (m, 2H), 1.87-1.72 (m, 1H), 0.98-0.86 (m, 3H), 0.79-0.65 (m, 3H). | 19 | 1268.52 |
| 514 | 1028.64 | 1030.64 | $^1$H NMR (400 MHz, CDCl$_3$) δ 11.10 (s, 1H), 10.48-9.49 (m, 1H), 8.16 (s, 1H), 8.01 (s, 1H), 7.81 (d, J = 8.4 Hz, 2H), 7.48-7.39 (m, 2H), 7.37-7.14 (m, 2H), 7.07 (dd, J = 2.4, 5.2 Hz, 1H), 6.55-6.11 (m, 1H), 5.51-5.28 (m, 2H), 5.11 (dd, J = 5.2, 12.8 Hz, 1H), 4.27 (s, 2H), 3.96-3.69 (m, 12H), 3.56 (dd, J = 2.8, 5.6 Hz, 6H), 2.93-2.56 (m, 7H), 2.33-1.92 (m, 4H), 1.72 (s, 2H), 1.38-1.13 (m, 5H). | 12 | 1028.47 |
| 515 | 1116.56 | 1118.56 | $^1$H NMR (400 MHz, DMSO-d$_6$) δ 11.11 (s, 1H), 10.23-9.86 (m, 1H), 8.31 (s, 1H), 8.00 (s, 1H), 7.87-7.73 (m, 2H), 7.48-7.39 (m, 2H), 7.37-7.31 (m, 1H), 7.30-7.26 (m, 1H), 7.24-7.16 (m, 2H), 7.08-7.04 (m, 1H), 6.46-6.32 (m, 1H), 5.51-5.27 (m, 2H), 5.20-5.02 (m, 1H), 4.34-4.23 (m, 2H), 3.96-3.82 (m, 6H), 3.80-3.67 (m, 5H), 3.59-3.54 (m, 3H), 3.52-3.50 (m, 2H), 3.49-3.46 (m, 10H), 3.45-3.44 (d, J = 4.0 Hz, 6H), 2.17-2.00 (m, 4H), 1.75-1.66 (m, 2H), 1.35-1.15 (m, 6H). | 12 | 1116.58 |
| 516 | 911.54 | | $^1$H NMR (400 MHz, DMSO-d$_6$) δ 11.10 (br s, 1H), 8.29 (s, 1H), 8.19 (br s, 1H), 7.99-7.89 (m, 1H), 7.65 (d, J = 8.2 Hz, 1H), 7.59 (d, J = 8.4 Hz, 1H), 7.57-7.52 (m, 2H), 7.47 (t, J = 7.8 Hz, 1H), 7.23 (d, J = 7.3 Hz, 1H), 7.15 (d, J = 8.4 Hz, 1H), 7.04 (d, J = 7.1 Hz, 1H), 6.85 (s, 1H), 6.66-6.58 (m, 1H), 6.20 (br d, J = 16.3 Hz, 1H), 5.79 (br d, J = 10.4 Hz, 1H), 5.05 (br dd, J = 5.4, 13.0 Hz, 1H), 4.86-4.39 (m, 1H), 4.25 (br d, J = 9.9 Hz, 1H), 4.14 (s, 2H), 4.12-4.07 (m, 1H), 4.02 (br d, J = 17.9 Hz, 3H), 3.64-3.61 (m, 2H), 3.55 (br d, J = 4.5 Hz, 4H), 3.50-3.46 (m, 6H), 3.24 (br s, 1H), 3.03-2.83 (m, 6H), 2.70 (br s, 1H), 2.61-2.58 (m, 3H), 2.31 (s, 3H), 2.16 (br dd, J = 6.1, 9.3 Hz, 1H), 2.03 (br s, 1H), 1.89-1.79 (m, 2H). | 20 | 911.02 |
| 517 | 955.58 | | $^1$H NMR (400 MHz, DMSO-d$_6$) δ 11.09 (br s, 1H), 8.22-8.14 (m, 1H), 7.98-7.88 (m, 1H), 7.65 (d, J = 8.1 Hz, 1H), 7.61-7.51 (m, 3H), 7.47 (t, J = 7.8 Hz, 1H), 7.23 (d, J = 7.1 Hz, 1H), 7.14 (d, J = 8.5 Hz, 1H), 7.03 (d, J = 7.0 Hz, 1H), 6.87 (br s, 1H), 6.61 (t, J = 5.7 Hz, 1H), 6.20 (dd, J = 2.0, 16.6 Hz, 1H), 5.83-5.72 (m, 1H), 5.05 (dd, J = 5.4, 12.9 Hz, 1H), 4.85-4.34 (m, 1H), 4.25 (dd, J = 4.8, 10.9 Hz, 1H), 4.17-4.12 (m, 2H), 4.11-4.07 (m, 1H), 4.03 (br d, J = 13.0 Hz, | 20 | 955.07 |

TABLE 13-continued

Data for Compounds of Table 12

| Ex. No. | MH+ (1) | MH+ (2) | NMR Transcript | Synthetic Scheme | Mol Weight |
|---|---|---|---|---|---|
| | | | 2H), 3.99-3.92 (m, 1H), 3.66-3.60 (m, 2H), 3.59-3.51 (m, 5H), 3.51-3.49 (m, 2H), 3.48-3.40 (m, 5H), 3.27-3.24 (m, 2H), 3.21-3.14 (m, 3H), 3.04-2.82 (m, 5H), 2.75-2.69 (m, 1H), 2.63-2.56 (m, 2H), 2.32 (s, 3H), 2.16 (dd, J = 6.0, 9.5 Hz, 1H), 2.08-1.98 (m, 1H), 1.94-1.71 (m, 2H). | | |
| 518 | 999.60 | | ¹H NMR (400 MHz, DMSO-d₆) δ 11.09 (s, 1H), 8.22-8.16 (m, 1H), 7.97-7.90 (m, 1H), 7.65 (d, J = 8.3 Hz, 1H), 7.61-7.51 (m, 3H), 7.47 (t, J = 7.8 Hz, 1H), 7.23 (d, J = 7.3 Hz, (d, 1H), 7.14 J = 8.7 Hz, 1H), 7.04 (d, J = 7.0 Hz, 1H), 6.88 (br s, 1H), 6.60 (br t, J = 5.7 Hz, 1H), 6.20 (dd, J = 2.0, 16.6 Hz, 1H), 5.85-5.75 (m, 1H), 5.05 (dd, J = 5.4, 12.9 Hz, 1H), 5.02-4.73 (m, 1H), 4.26 (br dd, J = 4.6, 10.9 Hz, 1H), 4.14 (s, 2H), 4.12-4.07 (m, 1H), 4.06-3.94 (m, 3H), 3.62 (br t, J = 5.4 Hz, 2H), 3.57-3.53 (m, 4H), 3.52-3.49 (m, 4H), 3.49-3.47 (m, 2H), 3.46 (br s, 2H), 3.43 (br d, J = 6.1 Hz, 2H), 3.27 (br dd, J = 6.2, 9.5 Hz, 2H), 3.21-3.17 (m, 2H), 3.10-2.83 (m, 4H), 2.75-2.66 (m, 2H), 2.60 (br d, J = 2.7 Hz, 4H), 2.35-2.31 (m, 3H), 2.17 (br dd, J = 6.0, 9.5 Hz, 1H), 2.07-1.98 (m, 1H), 1.91-1.78 (m, 2H). | 20 | 999.12 |
| 519 | 1043.64 | | ¹H NMR (400 MHz, CD₃OD) δ 8.50 (s, HI), 8.28-8.19 (m, 1H), 7.90-7.83 (m, 1H), 7.61 (d, J = 8.0 Hz, 1H), 7.55-7.47 (m, 3H), 7.43 (t, J = 8.0 Hz, 1H), 7.20 (d, J = 7.2 Hz, 1H), 7.08-7.00 (m, 2H), 6.93-6.72 (m, 1H), 6.29 (d, J = 16.8 Hz, 1H), 5.84 (d, J = 9.6 Hz, 1H), 5.17-4.98 (m, 2H), 4.67-4.03 (m, 8H), 3.77-3.34 (m, 26H), 3.11-2.62 (m, 12H), 2.34-2.20 (m, 1H), 2.15-1.94 (m, 2H). | 20 | 1043.17 |
| 520 | 898.55 | | ¹H NMR (400 MHz, DMSO-d₆) δ 10.96 (s, 1H), 8.23-8.11 (m, 2H), 7.94-7.90 (m, 1H), 7.63-7.6 (m, 21), 7.56-7.51 (m, 2H), 7.46-7.32 (m, 1H), 7.22-7.18 (m, 1H), 7.17 (s, 1H), 7.1-7.04 (m, 1H), 6.87-6.7 (m, 1H), 6.19-6.05 (m, 1H), 5.78-5.6 (m, 1H), 5.09-4.74 (m, 2H), 4.42-4.33 (m, 2H), 4.28-3.97 (m, 12H), 3.80-3.76 (m, 2H), 3.63-3.56 (m, 2H), 3.52-3.47 (m, 2H), 3.25-3.15 (m, 2H), 3.1-2.6 (m, 5H), 2.56-2.54 (m, 1H), 2.32-2.29 (m, 5H), 2.28-2.13 (m, 2H), 2.02-1.79 (m, 4H). | 21 | 898.02 |
| 521 | 942.58 | | ¹H NMR (400 MHz, DMSO-d₆) δ 10.96 (s, 1H), 8.24 (s, 1H), 8.20-8.14 (m, 1H), 7.95-7.89 (m, 1H), 7.66-7.58 (m, 2H), 7.56-7.51 (m, 2H), 7.45-7.3 (m, 1H), 7.25-7.2 (m, 1H), 7.18-7.1 (m, 1H), 7.06-6.9 (m, 1H), 6.88-6.5 (m, 1H), 6.23-6.14 (m, 1H), 5.8-5.5 (m, 1H), 5.06-5.0 (m, 1H), 4.98-4.6 (m, 1H), 4.49-4.32 (m, 2H), 4.27-4.21 (m, 2H), 4.19-4.15 (m, 2H), 4.15-3.93 (m, 8H), 3.79-3.74 (m, 2H), 3.61-3.57 (m, 3H), 3.55-3.53 (m, 3H), 3.51-3.49 (m, 4H), 3.30-3.14 (m, 2H), 3.04-2.84 (m, 4H), 2.75-2.65 (m, 2H), 2.39-2.33 (m, 5H), 2.16-2.1 (m, 1H), 2.00-1.92 (m, 1H), 1.88-1.79 (m, 2H). | 21 | 942.07 |
| 522 | 986.62 | | ¹H NMR (400 MHz, DMSO-d₆) δ 10.98 (s, 1H), 8.22 (s, 1H), 8.20-8.14 (m, 1H), 7.97-7.89 (m, 1H), 7.62 (br dd, J = 8.4, 12.1 Hz, 2H), 7.57-7.50 (m, 2H), 7.46 (br t, J = 7.8 Hz, 1H), 7.22 (br d, J = 7.4 Hz, 1H), 7.16 (s, 1H), 7.05 (br d, J = 8.3 Hz, 1H), 6.97-6.77 (m, 1H), 6.19 (br d, J = 16.6 Hz, 1H), 5.78 (br d, J = 10.8 Hz, 1H), 5.07 (br dd, J = 4.9, 13.2 Hz, 1H), 5.01-4.75 (m, 1H), 4.50-4.30 (m, 2H), 4.29-4.21 (m, 2H), 4.17 (br s, 2H), 4.14-4.07 (m, 3H), 4.04-3.94 (m, 3H), 3.76 (br s, 2H), 3.59-3.57 (m, 2H), 3.54 (br d, J = 5.1 Hz, 2H), 3.51 (br s, 4H), 3.48 (br s, 2H), 3.43 (br d, J = 5.8 Hz, 2H), 3.27 (br dd, J = 6.3, 9.1 Hz, 2H), 3.18 (br s, 2H), 3.06-2.83 (m, 6H), 2.76-2.64 (m, 2H), 2.59 (br s, 1H), 2.39 (br dd, J = 4.4, 13.1 Hz, 1H), 2.32 (s, 3H), 2.16 (br dd, J = 6.1, 9.2 Hz, 1H), 2.01-1.77 (m, 3H). | 21 | 986.12 |
| 523 | 1030.65 | | ¹H NMR (400 MHz, CDCl₃) δ 8.49 (brs, 1H), 8.24-8.21 (m, 1H), 7.89-7.86 (m, 1H), 7.79 (d, J = 8.4 Hz, 1H), 7.62 (d, J = 8.4 Hz, 1H), 7.54-7.49 (m, 2H), 7.45 (t, J = 7.6 Hz, 1H), 7.15 (d, J = 7.2 Hz, 1H), 7.02 (dd, J = 2.0, 8.4 Hz, 1H), 6.98 (s, 1H), 6.70-6.55 (m, 1H), 6.42 (dd, J = 1.2, 16.8 Hz, 1H), 5.84 (d, J = 10.8 Hz, 1H), 5.19 (dd, J = 4.8, 13.2 Hz, 1H), 5.15 (brs , 1H), 4.80-4.40 (m, 2H), 4.33-4.10 (m, 8H), 4.07-3.95 (m, 2H), 3.90 (t, J = 4.8 Hz, 2H), 3.80-3.71 (m, 2H), 3.70-3.47 (m, 18H), 3.41-3.25 (m, 2H), 3.14-2.78 (m, 7H), 2.54 (s, 3H), 2.50-2.40 (m, 1H), 2.39-2.27 (m, 1H), 2.25-2.10 (m, 2H), 2.06-1.98 (m, 1H). | 21 | 1030.17 |
| 524 | 1144.75 | 1146.75 | ¹H NMR (400 MHz, CD₃OD) δ 9.03-8.93 (m, 1H), 8.12 (br d, J = 5.9 Hz, 1H), 7.75 (br d, J = 8.3 Hz, 1H), 7.48-7.33 (m, 5H), 7.30-7.15 (m, 3H), 7.05 (s, 1H), 6.86-6.76 (m, 1H), 6.30 (dd, J = 1.7, 16.8 Hz, 1H), 6.06-5.98 (m, 1H), 5.86-5.72 (m, 2H), 4.97 (q, J = 7.2 Hz, 2H), 4.57 (t, J = 8.1 Hz, 1H), 4.42 (br s, 1H), 4.28 (br s, 2H), 4.16 (br s, 4H), 3.95 (br s, 4H), 3.82-3.52 (m, 9H), 3.50-3.33 (m, 3H), 2.51-2.44 (m, 3H), 2.41-2.30 (m, 1H), 2.26-2.17 (m, 1H), 2.10-1.88 (m, 4H), 1.55-1.43 (m, 6H), 1.04 (d, J = 6.5 Hz, 3H), 0.95-0.85 (m, 3H). | 9 | 1144.75 |
| 525 | 1144.60 | 1146.60 | ¹H NMR (400 MHz, CD₃OD) δ 8.97-8.91 (m, 1H), 8.13-8.07 (m, 1H), 7.76 (d, J = 8.4 Hz, 1H), 7.47-7.35 (m, 5H), 7.28 (d, J = 2.4 Hz, 1H), 7.25-7.16 (m, 2H), 7.05 (dd, J = 2.4, 4.8 Hz, 1H), 6.85-6.76 (m, 1H), 6.30 (dd, J = 1.6, 16.8 Hz, 1H), 6.02-5.95 (m, 1H), 5.85-5.63 (m, 2H), 5.07-4.95 (m, 1H), 4.76 (br t, J = 7.6 Hz, 2H), 4.51 (t, J = 8.4 Hz, 1H), 4.46-4.25 (m, 3H), 4.14 (br s, 4H), 3.94 (br s, 4H), 3.86-3.76 (m, 11H), 2.50-2.44 (m, 3H), 2.42-2.29 (m, 1H), 2.18 (br dd, J = 8.6, 12.0 Hz, 1H), 2.04 (br s, 1H), 2.03-1.83 (m, 3H), 1.60-1.45 (m, 6H), 1.04 (br d, J = 6.4 Hz, 3H), 0.92-0.83 (m, 3H). | 9 | 1144.75 |
| 526 | 1188.79 | 1190.79 | ¹H NMR (400 MHz, CD₃OD) δ 8.86 (s, 1H), 8.54 (s, 1H), 8.04 (s, 1H), 7.76 (d, J = 8 Hz, 1H), 7.48-7.34 (m, 5H), 7.29-7.15 (m, 3H), 7.07-7.03 (m, 1H), 6.99-6.77 (m, 1H), 6.35-6.25 (m, 1H), 6.06-5.97 (m, 1H), 5.86-5.80 (m, 1H), 5.65 (s, 1H), 5.02-4.93 (m, 1H), 4.58 (t, J = 8 Hz, 2H), 4.43 (s, 1H), 4.32-4.22 (m, 2H), 4.04 (s, 4H), 3.94 (s, 4H), 3.80-3.48 (m, 10H), 3.27-3.07 (s, 3H), 3.00-2.64 (m, 3H), 2.52-2.45 (m, 3H), 2.42-2.30 (m, 1H), 2.27-2.16 (m, 1H), 1.97-1.66 (m, 4H), 1.61-1.40 (m, 6H), 1.05 (d, J = 6.4 Hz, 3H), 0.90 (d, J = 6.4 Hz, 3H). | 9 | 1188.80 |
| 527 | 1188.79 | 1190.79 | ¹H NMR (400 MHz, CD₃OD) δ 8.86 (s, 1H), 8.54 (s, 1H), 8.04(s, 1H), 7.76 (d, J = 8 Hz, 1H), 7.48-7.37 (m, 5H), 7.31-7.18 (m, 3H), 7.07-7.03 (m, 1H), 6.90-6.78 (m, 1H), 6.35-6.25 (m, 1H), 6.03-5.94 (m, 1H), 5.86-5.80 (m, 1H), 5.65 (s, 1H), 5.08-4.99 (m, 1H), 4.60-4.42 (m, 3H), 4.32-4.27 (m, 2H), 4.04 (s, 4H), 3.95 (s, 4H), 3.87-3.75 (m, 3H), 3.69-3.50 (m, 7H), 3.19-2.95 (s, 3H), 2.84-2.54 (m, 3H), 2.52-2.45 (m, 3H), 2.42-2.30 (m, 1H), 2.27-2.16 (m, 1H), 2.04-1.83 (m, 3H), 1.71-1.61 (m, 1H), 1.55-1.40 (m, 6H), 1.05 (d, J = 6.4 Hz, 3H), 0.90 (d, J = 6.4 Hz, 3H). | 9 | 1188.80 |

TABLE 13-continued

Data for Compounds of Table 12

| Ex. No. | MH+ (1) | MH+ (2) | NMR Transcript | Synthetic Scheme | Mol Weight |
|---|---|---|---|---|---|
| 528 | 1232.82 | 1234.82 | ¹H NMR (400 MHz, CD₃OD) δ 8.87 (s, 1H), 8.53 (s, 1H), 8.05 (s, 1H), 7.77 (d, J = 8 Hz, 1H), 7.48-7.34 (m, 5H), 7.30-7.17 (m, 3H), 7.07-7.03 (m, 1H), 6.89-6.77 (m, 1H), 6.35-6.25 (m, 1H), 6.06-5.97 (m, 1H), 5.86-5.80 (m, 1H), 5.67 (s, 1H), 5.02-4.93 (m, 1H), 4.56 (t, J = 8 Hz, 2H), 4.43 (s, 1H), 4.32-4.22 (m, 2H), 4.05 (s, 4H), 3.94 (s, 4H), 3.80-3.53 (m, 15H), 3.27-3.14 (m, 2H), 3.12-2.85 (m, 2H), 2.52-2.45 (m, 3H), 2.42-2.30 (m, 1H), 2.27-2.16 (m, 1H), 1.97-1.73 (m, 4H), 1.52-1.43 (m, 6H), 1.05 (d, J = 6.8 Hz, 3H), 0.90 (d, J = 6.4 Hz, 3H). | 9 | 1232.85 |
| 529 | 1232.82 | 1234.82 | ¹H NMR (400 MHz, CD₃OD) δ 8.89 (s, 1H), 8.55 (s, 1H), 8.05 (s, 1H), 7.77 (d, J = 8 Hz, 1H), 7.48-7.40 (m, 5H), 7.30-7.17 (m, 3H), 7.07-7.03 (m, 1H), 6.89-6.78 (m, 1H), 6.34-6.27 (m, 1H), 6.03-5.94 (m, 1H), 5.86-5.80 (m, 1H), 5.66 (s, 1H), 5.08-5.00 (m, 1H), 4.61-4.49 (m, 2H), 4.48-4.37 (m, 1H), 4.32-4.25 (m, 2H), 4.05 (s, 4H), 3.94 (s, 4H), 3.87-3.77 (m, 3H), 3.70-3.49 (m, 12H), 3.25-3.03 (m, 3H), 2.94-2.69 (m, 2H), 2.52-2.45 (m, 3H), 2.42-2.30 (m, 1H), 2.23-2.14 (m, 1H), 2.02-1.69 (m, 4H), 1.55-1.41 (m, 6H), 1.05 (d, J = 6.4 Hz, 3H), 0.90 (d, J = 6.4 Hz, 3H). | 9 | 1232.85 |
| 530 | 1276.86 | 1278.86 | ¹H NMR (400 MHz, CDCl₃) δ 8.99-8.92 (m, 1H), 8.12 (d, J = 1.6 Hz, 1H), 7.78 (d, J = 8.8 Hz, 1H), 7.49-7.38 (m, 5H), 7.30 (d, J = 2.4 Hz, 1H), 7.27-7.20 (m, 2H), 7.07 (d, J = 2.4 Hz, 1H), 6.88-6.78 (m, 1H), 6.32 (d, J = 1.6 Hz, 1H), 6.04-5.94 (m, 1H), 5.84 (d, J = 2.0 Hz, 1H), 5.77 (s, 1H), 5.04 (q, J = 7.2 Hz, 1H), 4.77 (t, J = 7.6 Hz, 1H), 4.55-4.49 (m, 1H), 4.48-4.37 (m, 1H), 4.34-4.26 (m, 2H), 4.19-4.10 (m, 4H), 3.97 (s, 4H), 3.84 (t, J = 4.0 Hz, 1H), 3.81-3.52 (m, 20H), 3.52-3.37 (m, 3H), 2.53-2.46 (m, 3H), 2.37 (q, J = 7.2 Hz, 1H), 2.24-2.15 (m, 1H), 2.13-1.79 (m, 4H), 1.62-1.48 (m, 6H), 1.09-1.00 (m, 3H), 0.93-0.84 (m, 3H). | 9 | 1276.90 |
| 531 | 1276.86 | 1278.86 | ¹H NMR (400 MHz, CDCl₃) δ 8.96-8.89 (m, 1H), 8.11 (d, J = 1.6 Hz, 1H), 7.78 (d, J = 8.0 Hz, 1H), 7.50-7.40 (m, 3H), 7.40-7.34 (m, 2H), 7.30 (d, J = 2.4 Hz, 1H), 7.27-7.18 (m, 2H), 7.09-7.01 (m, 1H), 6.83 (d, J = 10.4, 1H), 6.31 (d, J = 2.0, 1H), 6.07-5.97 (m, 1H), 5.86-5.81 (m, 1H), 5.75 (s, 1H), 5.19-4.91 (m, 2H), 4.59 (t, J = 8.0 Hz, 1H), 4.47-4.21 (m, 3H), 4.12 (d, J = 4.4 Hz, 4H), 3.96 (s, 4H), 3.81-3.37 (m, 24H), 2.52-2.43 (m, 3H), 2.42-2.32 (m, 1H), 2.28-2.18 (m, 1H), 2.15-1.83 (m, 4H), 1.61-1.46 (m, 6H), 1.24-0.99 (m, 3H), 0.97-0.84 (m, 3H). | 9 | 1276.90 |
| 532 | 1320.89 | 1322.89 | ¹H NMR (400 MHz, CDCl₃) δ 9.10-8.92 (m, 1H), 8.20-8.08 (m, 1H), 7.76 (d, J = 8.4 Hz, 1H), 7.57-7.33 (m, 5H), 7.31-7.15 (m, 3H), 7.06 (d, J = 2.0 Hz, 1H), 6.91-6.73 (m, 1H), 6.30 (dd, J = 1.6, 16.8 Hz, 1H), 6.06-5.96 (m, 1H), 5.87-5.70 (m, 2H), 4.97 (d, J = 7.2 Hz, 2H), 4.57 (t, J = 8.0 Hz, 1H), 4.46-4.33 (m, 1H), 4.31-4.10 (m, 6H), 3.95 (s, 4H), 3.77-3.53 (m, 25H), 3.47 (d, J = 13.2 Hz, 1H), 3.35 (d, J = 9.6 Hz, 1H), 3.51-3.33 (m, 1H), 2.51-2.43 (m, 3H), 2.42-2.28 (m, 1H), 2.20 (d, J = 10.0 Hz, 1H), 2.14-1.81 (m, 4H), 1.61-1.43 (m, 6H), 1.04 (d, J = 6.8 Hz, 3H), 0.96-0.85 (m, 3H). | 9 | 1320.96 |
| 533 | 1320.88 | 1322.89 | ¹H NMR (400 MHz, CDCl₃) δ 9.05-8.97 (m, 1H), 8.13 (d, J = 6.4 Hz, 1H), 7.76 (d, J = 8.4 Hz, 1H), 7.53-7.38 (m, 5H), 7.32-7.18 (m, 3H), 7.06 (s, 1H), 6.81 (dd, J = 10.8, 16.8 Hz, 1H), 6.30 (d, J = 16.8 Hz, 1H), 6.05-5.90 (m, 1H), 5.83 (d, J = 10.4 Hz, 2H), 5.08-4.99 (m, 2H), 4.82-4.70 (m, 1H), 4.56-4.34 (m, 2H), 4.32-4.13 (m, 6H), 3.95 (s, 4H), 3.77 (s, 4H), 3.65 (s, 21H), 3.48 (d, J = 12.0 Hz, 3H), 3.35 (s, 1H), 2.48 (s, 3H), 2.42-1.89 (m, 6H), 1.60-1.46 (m, 6H), 1.03 (d, J = 6.4 Hz, 3H), 0.94-0.81 (m, 3H). | 9 | 1320.96 |
| 534 | 1085.69 | | ¹H NMR (400 MHz, DMSO-d₆) δ 8.99-8.97 (s, 1H), 8.44 (d, J = 8.0 Hz, 1H), 8.32-8.25 (m, 2H), 8.22-8.17 (m, 1H), 7.95-7.91 (m, 1H), 7.66-7.63 (m, 1H), 7.56-7.52 (m, 2H), 7.49-7.46 (m, 1H), 7.44-7.41 (m, 2H), 7.37-7.34 (m, 3H), 7.23 (d, J = 8.0 Hz, 1H), 6.24 (s, 2H), 4.93-4.88 (m, 1H), 4.57-4.52 (m, 1H), 4.49-4.41 (m, 2H), 4.31-4.27 (m, 2H), 4.15-4.13 (m, 2H), 4.12-4.10 (m, 1H), 4.04-3.99 (m, 3H), 3.97-3.94 (m, 6H), 3.58-3.54 (m, 1H), 3.16-3.14 (m, 2H), 2.97-2.94 (m, 2H), 2.94-2.91 (m, 3H), 2.76-2.74 (m, 2H), 2.45 (s, 3H), 2.36-2.34 (m, 3H), 2.28-2.23 (m, 2H), 2.09-2.02 (m, 2H), 1.96-1.89 (m, 2H), 1.87-1.76 (m, 3H), 1.36 (d, J = 6.8 Hz, 3H), 0.94 (s, 9H). | 17 | 1085.32 |
| 535 | 1129.72 | | ¹H NMR (400 MHz, CD₃OD) δ 8.95-8.87 (m, 1H), 8.23 (br d, J = 5.6 Hz, 1H), 7.92-7.85 (m, 1H), 7.68-7.61 (m, 1H), 7.54-7.48 (m, 2H), 7.47-7.35 (m, 5H), 7.20 (d, J = 7.5 Hz, 1H), 5.05-4.92 (m, 2H), 4.84-4.77 (m, 2H), 4.72-4.64 (m, 2H), 4.60-4.48 (m, 2H), 4.42 (br d, J = 16.0 Hz, 2H), 4.36-4.15 (m, 4H), 4.08 (s, 2H), 3.99-3.67 (m, 12H), 3.63-3.34 (m, 6H), 3.18 (br s, 3H), 3.14-2.94 (m, 3H), 2.88-2.78 (m, 1H), 2.56 (br d, J = 7.1 Hz, 1H), 2.49-2.43 (m, 3H), 2.26-2.18 (m, 1H), 2.03-1.91 (m, 1H), 1.60-1.47 (m, 3H), 1.09-1.02 (m, 9H). | 17 | 1129.37 |
| 536 | 1173.75 | | ¹H NMR (400 MHz, DMSO-d₆) δ 9.93 (br s, 1H), 8.98 (s, 1H), 8.40 (d, J = 7.7 Hz, 1H), 8.22-8.13 (m, 1H), 7.96-7.88 (m, 1H), 7.65 (d, J = 8.3 Hz, 1H), 7.57-7.51 (m, 2H), 7.51-7.43 (m, 2H), 7.43-7.38 (m, 2H), 7.38-7.30 (m, 3H), 7.23 (d, J = 7.1 Hz, 1H), 6.26 (br s, 2H), 4.90 (quin, J = 7.0 Hz, 1H), 4.69-4.39 (m, 6H), 4.27 (br s, 2H), 4.16 (s, 2H), 4.12-3.90 (m, 7H), 3.84 (br d, J = 13.6 Hz, 8H), 3.56 (br s, 8H), 3.41-3.18 (m, 3H), 3.00 (br s, 3H), 2.97-2.80 (m, 4H), 2.52 (br s, 2H), 2.45 (s, 3H), 2.03 (br d, J = 8.8 Hz, 1H), 1.81-1.73 (m, 1H), 1.47-1.36 (m, 3H), 0.93 (s, 9H). | 17 | 1173.43 |
| 537 | 1217.93 | | ¹H NMR (400 MHz, DMSO-d₆) δ 9.20 (br s, 1H), 9.30-8.95 (m, 1H), 8.76-8.36 (m, 1H), 8.33 (s, 1H), 8.23-8.15 (m, 1H), 7.96-7.85 (m, 1H), 7.64 (d, J = 8.2 Hz, 1H), 7.59-7.51 (m, 2H), 7.50-7.30 (m, 6H), 7.27-7.14 (m, 1H), 6.23 (s, 2H), 4.97-4.85 (m, 1H), 4.71-4.40 (m, 3H), 4.33-4.21 (m, 2H), 4.19-4.06 (m, 3H), 4.04-3.93 (m, 4H), 3.85 (br d, J = 13.0 Hz, 2H), 3.66-3.57 (m, 6H), 3.57-3.53 (m, 4H), 3.53-3.46 (m, 10H), 3.23-3.13 (m, 4H), 3.00-2.81 (m, 4H), 2.76-2.70 (m, 1H), 2.45 (s, 3H), 2.34 (s, 3H), 2.18 (br dd, J = 6.1, 9.4 Hz, 1H), 2.09-1.99 (m, 1H), 1.92-1.74 (m, 3H), 1.50-1.33 (m, 3H), 0.94 (s, 9H). | 17 | 1217.48 |
| 538 | 1261.82 | | ¹H NMR (400 MHz, CD₃OD) δ 8.93 (s, 1H), 8.26-8.24 (m, 1H), 7.91-7.87 (m, 1H), 7.65 (d, J = 8.4 Hz, 1H), 7.55-7.49 (m, 2H), 7.48-7.39 (m, 5H), 7.23 (d, J = 8.0 Hz, 1H), 5.04-4.98 (m, 1H), 4.80-4.50 (m, 5H), 4.45-4.35 (m, 2H), 4.34-4.24 (m, 3H), 4.21-4.10 (m, 1H), 4.06 (d, | 17 | 1261.53 |

TABLE 13-continued

Data for Compounds of Table 12

| Ex. No. | MH+ (1) | MH+ (2) | NMR Transcript | Synthetic Scheme | Mol Weight |
|---|---|---|---|---|---|
| | | | J = 2.0 Hz, 2H), 4.55-3.80 (m, 3H), 3.78-3.61 (m, 22H), 3.55-3.36 (m, 6H), 3.18 (s, 3H), 3.16-2.96 (m, 3H), 2.87-2.81 (m, 1H), 2.55 (dd, J = 6.8, 14.0 Hz, 1H), 2.49, 2.48 (s, 3H), 2.41-2.21 (m, 2H), 2.11-1.93 (m, 1H), 1.57, 1.51 (d, J = 6.8 Hz, 3H), 1.06, 1.04 (s, 9H). | | |
| 539 | 901.52 | | ¹H NMR (400 MHz, DMSO-d₆) δ 11.10 (s, 1H), 9.97 (br s, 1H), 8.22-8.15 (m, 1H), 7.95-7.89 (m, 1H), 7.82 (d, J = 8.3 Hz, 1H), 7.65 (d, J = 8.3 Hz, 1H), 7.57-7.52 (m, 2H), 7.49-7.43 (m, 2H), 7.35 (dd, J = 2.2, 8.3 Hz, 1H), 7.22 (d, J = 7.3 Hz, 1H), 6.25 (br s, 2H), 5.10 (dd, J = 5.4, 12.8 Hz, 1H), 4.65-4.54 (m, 3H), 4.46 (dd, J = 7.0, 12.3 Hz, 1H), 4.35-4.30 (m, 2H), 4.26 (br s, 1H), 4.15 (s, 2H), 4.11-3.91 (m, 4H), 3.88-3.71 (m, 4H), 3.62 (s, 3H), 3.39-3.14 (m, 6H), 3.06-2.82 (m, 9H), 2.62-2.55 (m, 1H), 2.36 (br d, J = 6.8 Hz, 1H), 2.09-1.98 (m, 2H). | 18 | 900.98 |
| 540 | 945.56 | | ¹H NMR (400 MHz, DMSO-d₆) δ 11.13 (s, 1H), 10.04 (br s, 1H), 8.27-8.13 (m, 1H), 7.98-7.88 (m, 1H), 7.83 (d, J = 8.3 Hz, 1H), 7.66 (d, J = 8.2 Hz, 1H), 7.59-7.51 (m, 2H), 7.50-7.43 (m, 2H), 7.36 (dd, J = 2.2, 8.3 Hz, 1H), 7.23 (d, J = 7.2 Hz, 1H), 6.29 (br s, 2H), 5.12 (dd, J = 5.4, 12.8 Hz, 1H), 4.67-4.54 (m, 3H), 4.48 (br dd, J = 6.9, 12.5 Hz, 1H), 4.35-4.29 (m, 2H), 4.26 (br s, 1H), 4.16 (s, 2H), 4.11-3.91 (m, 3H), 3.85 (br d, J = 12.7 Hz, 1H), 3.81-3.70 (m, 3H), 3.65-3.52 (m, 8H), 3.43-3.13 (m, 5H), 3.10-2.96 (m, 5H), 2.94-2.80 (m, 3H), 2.64-2.53 (m, 2H), 2.40-2.33 (m, 1H), 2.09-1.98 (m, 2H). | 18 | 945.03 |
| 541 | 989.72 | | ¹H NMR (400 MHz, CDCl₃) δ 8.42-8.35 (m, 1H), 8.25-8.18 (m, 1H), 7.91-7.83 (m, 1H), 7.78 (d, J = 8.3 Hz, 1H), 7.61 (d, J = 8.2 Hz, 1H), 7.54-7.47 (m, 2H), 7.46-7.40 (m, 1H), 7.38-7.25 (s, 1H), 7.25-7.22 (m, 1H), 7.14 (d, J = 7.0 Hz, 1H), 5.12 (s, 1H), 5.0-4.9 (m, 1H), 4.89-4.71 (m, 2H), 4.38-4.3 (m, 1H), 4.29-4.23 (m, 3H), 4.20-4.15 (m, 1H), 4.05-3.92 (m, 2H), 3.92-3.87 (m, 2H), 3.84-3.75 (m, 1H), 3.75-3.70 (m, 2H), 3.70-3.60 (m, 10H), 3.59-3.49 (m, 2H), 3.47-3.35 (m, 2H), 3.32-3.20 (m, 2H), 3.1-2.98 (m, 1H), 2.94-2.85 (m, 1H), 2.84-2.78 (m, 3H), 2.76-2.71 (m, 3H), 2.75-2.68 (m, 2H), 2.23-2.2 (m, 1H), 2.18-2.1 (m, 4H). | 18 | 989.08 |
| 542 | 1033.62 | | ¹H NMR (400 MHz, DMSO-d₆) δ 11.09 (s, 1H), 8.21-8.15 (m, 1H), 7.93-7.91 (m, 1H), 7.82 (d, J = 8.4 Hz, 1H), 7.64 (d, J = 8.0 Hz, 1H), 7.58-7.50 (m, 2H), 7.48-7.44 (m, 2H), 7.36 (dd, J = 2.4, 8.4 Hz, 1H), 7.22 (d, J = 7.6 Hz, 1H), 6.25 (brs, 2H), 5.12 (dd, J = 4.8, 12.8 Hz, 1H), 4.58 (s, 1H), 4.31-4.24 (m, 3H), 4.16-4.08 (m, 3H), 4.05-3.92 (m, 3H), 3.90-3.75 (m, 3H), 3.63-3.58 (m, 2H), 3.56-3.41 (m, 15H), 3.30-3.11 (m, 5H), 3.10-2.83 (m, 6H), 2.76-2.65 (m, 2H), 2.33 (s, 3H), 2.16 (dd, J = 6.0, 9.2 Hz, 1H), 2.08-2.01 (m, 1H), 1.92-1.75 (m, 2H). | 18 | 1033.14 |
| 543 | 900.53 | | ¹H NMR (400 MHz, DMSO-d₆) δ 11.08 (s, 1H), 8.24-8.17 (m, 1H), 7.95-7.88 (m, 1H), 7.64 (d, J = 8.1 Hz, 1H), 7.60-7.51 (m, 3H), 7.47 (t, J = 7.8 Hz, 1H), 7.23 (d, J = 7.5 Hz, 1H), 7.15 (d, J = 8.7 Hz, 1H), 7.03 (d, J = 7.2 Hz, 1H), 6.61 (br t, J = 5.8 Hz, 1H), 6.23 (s, 2H), 5.05 (dd, J = 5.7, 12.9 Hz, 1H), 4.58 (br s, 1H), 4.29-4.22 (m, 1H), 4.13 (s, 3H), 4.03-3.78 (m, 4H), 3.63 (t, J = 5.2 Hz, 2H), 3.57-3.53 (m, 2H), 3.51-3.44 (m, 4H), 3.28-3.11 (m, 3H), 3.07-2.82 (m, 6H), 2.60 (br s, 2H), 2.36-2.27 (m, 4H), 2.17 (br s, 1H), 2.08-1.95 (m, 1H), 1.92-1.75 (m, 2H), 1.51 (br s, 1H). | 20 | 899.99 |
| 544 | 944.57 | | ¹H NMR (400 MHz, DMSO-d₆) δ 11.09 (s, 1H), 10.53-9.92 (m, 1H), 8.31-8.13 (m, 1H), 7.99-7.87 (m, 1H), 7.69-7.63 (m, 1H), 7.60-7.51 (m, 3H), 7.46 (t, J = 7.8 Hz, 1H), 7.27-7.19 (m, 1H), 7.12 (d, J = 8.6 Hz, 1H), 7.07-6.98 (m, 1H), 6.58 (br s, 1H), 6.26 (br s, 2H), 5.05 (br dd, J = 5.4, 12.7 Hz, 1H), 4.70-4.41 (m, 3H), 4.24 (br s, 1H), 4.15 (br s, 2H), 4.11-3.89 (m, 4H), 3.86-3.71 (m, 4H), 3.64-3.60 (m, 4H), 3.56 (br s, 10H), 3.30-3.18 (m, 2H), 3.03 (br d, J = 12.3 Hz, 2H), 2.98 (br s, 3H), 2.94-2.81 (m, 4H), 2.60 (br d, J = 2.5 Hz, 1H), 2.08-1.96 (m, 2H). | 20 | 944.05 |
| 545 | 988.61 | | ¹H NMR (400 MHz, DMSO-d₆) δ 11.11 (s, 1H), 10.42-9.85 (m, 1H), 8.25-8.12(m, 1H), 7.97-7.89 (m, 1H), 7.66 (d, J = 8.2 Hz, 1H), 7.61-7.51 (m, 3H), 7.47 (t, J = 7.8 Hz, 1H), 7.23 (d, J = 7.2 Hz, 1H), 7.16-7.10 (m, 1H), 7.04 (d, J = 7.0 Hz, 1H), 6.60 (br s, 1H), 6.28 (br s, 2H), 5.06 (dd, J = 5.4, 12.8 Hz, 1H), 4.71-4.43 (m, 3H), 4.24 (br s, 1H), 4.16 (s, 2H), 4.11-3.99 (m, 2H), 3.94 (br s, 1H), 3.85 (br d, J = 12.3 Hz, 2H), 3.73 (br s, 2H), 3.68-3.56 (m, 13H), 3.33-3.16 (m, 6H), 3.07-2.95 (m, 6H), 2.94-2.80 (m, 4H), 2.63-2.56 (m, 2H), 2.37-2.33 (m, 1H), 2.13-1.96 (m, 2H). | 20 | 988.10 |
| 546 | 1032.64 | | ¹H NMR (400 MHz, DMSO-d₆) δ 11.10 (brs, 1H), 8.33 (brs, 2H), 8.20-8.18 (m, 1H), 7.94-7.91 (m, 1H), 7.64 (d, J = 8.4 Hz, 1H), 7.60-7.52 (m, 3H), 7.46 (t, J = 7.6 Hz, 1H), 7.22 (d, J = 7.2 Hz, 1H), 7.14 (d, J = 8.4 Hz, 1H), 7.03 (d, J = 6.8 Hz, 1H), 6.60 (t, J = 6.0 Hz, 1H), 6.25 (brs, 2H), 5.05 (dd, J = 5.6, 13.2 Hz, 1H), 4.60-4.50 (m, 1H), 4.26 (dd, J = 4.4, 10.8 Hz, 1H), 4.15-4.08 (m, 3H), 4.02-3.94 (m, 4H), 3.85 (d, J = 12.0 Hz, 2H), 3.65-3.51 (m, 18H), 3.3-3.15 (m, 5H), 3.10-2.84 (m, 6H), 2.75-6.68 (m, 1H), 2.60-2.55 (m, 2H), 2.33 (s, 3H), 2.16 (dd, J = 6.0, 9.6 Hz, 1H), 2.05-1.97 (m, 1H), 1.90-1.80 (m, 2H). | 20 | 1032.15 |
| 547 | 1158.76 | | ¹H NMR (400 MHz, DMSO-d₆) δ 8.29-8.23 (m, 2H), 8.23-8.21 (m, 1H), 8.20-8.14 (m, 1H), 8.04-7.98 (m, 1H), 7.95-7.89 (m, 1H), 7.72-7.67 (m, 1H), 7.66-7.57 (m, 2H), 7.57-7.49 (m, 4H), 7.48-7.41 (m, 1H), 7.24-7.19 (m, 1H), 7.07-7.01 (m, 1H), 6.95-6.76 (m, 1H), 6.23-6.14 (m, 1H), 5.81-5.74 (m, 1H), 5.65-5.37 (m, 1H), 5.03-4.72 (m, 1H), 4.58-4.47 (m, 1H), 4.37-4.28 (m, 2H), 4.27-4.20 (m, 1H), 4.15-4.07 (m, 3H), 4.05-3.97 (m, 3H), 3.95-3.88 (m, 2H), 3.84-3.77 (m, 2H), 3.69-3.65 (m, 2H), 3.56-3.50 (m, 4H), 3.30-3.24 (m, 2H), 3.22-3.11 (m, 3H), 3.11-3.03 (m, 2H), 3.01-2.90 (m, 3H), 2.73-2.65 (m, 1H), 2.35-2.27 (m, 4H), 2.25-2.14 (m, 5H), 2.09-1.97 (m, 2H), 1.92-1.53 (m, 8H), 1.21-1.11 (m, 4H), 1.11-0.90 (m, 4H). | 22 | 1158.46 |
| 548 | 1202.79 | | ¹H NMR (400 MHz, DMSO-d₆) δ 10.13-9.85 (m, 1H), 8.83-8.70 (m, 2H), 8.28-8.22 (m, 1H), 8.20-8.13 (m, 1H), 7.97-7.90 (m, 1H), 7.73-7.63 (m, 2H), 7.61-7.50 (m, 5H), 7.49-7.43 (m, 1H), 7.21-7.19 (d, J = 7.46 Hz, 1H), 7.03-7.01 (d, J = 8.0 Hz, 1H), 6.94-6.73 (m, 1H), 6.25-6.12 (m, 1H), 5.82-5.72 (m, 1H), 5.47-5.39 (m, 1H), 5.06-4.91 (m, 1H), 4.81-4.70 (m, 1H), 4.65-4.38 (m, 5H), 4.34-4.29 (m, 2H), 4.27-4.22 (m, 1H), 4.14 (s, 2H), 4.10-4.00 (m, 3H), 3.94-3.67 (m, 12H), 3.63-3.54 (m, 9H), 3.24-3.15 (m, 2H), 3.01-2.93 (m, 5H), 2.89 (s, 1H), 2.73 (s, 1H), 2.28-2.17 (m, 2H), 2.08-1.96 (m, 3H), 1.79-1.64 (m, 4H), 1.62-1.53 (m, 2H), 1.35-1.33 (m, 2H), 1.24 (d, J = 6.85 Hz, 3H), 1.24-1.00 (m, 6H). | 22 | 1202.51 |

TABLE 13-continued

Data for Compounds of Table 12

| Ex. No. | MH+ (1) | MH+ (2) | NMR Transcript | Synthetic Scheme | Mol Weight |
|---|---|---|---|---|---|
| 549 | 1246.82 | | $^1$H NMR (400 MHz, DMSO-d$_6$) δ 8.30-8.21 (m, 3H), 8.21-8.13 (m, 1H), 8.00-7.88 (m, 2H), 7.68 (s, 1H), 7.61 (dd, J = 8.0, 18.0 Hz, 2H), 7.57-7.50 (m, 4H), 7.45 (t, J = 7.8 Hz, 1H), 7.21 (d, J = 7.5 Hz, 1H), 7.03 (d, J = 8.1 Hz, 1H), 6.86 (br s, 1H), 6.19 (br d, J = 16.8 Hz, 1H), 5.81-5.73 (m, 1H), 5.43 (dd, J = 2.8, 7.8 Hz, 1H), 5.06-4.68 (m, 1H), 4.57-4.47 (m, 1H), 4.31 (br d, J = 4.9 Hz, 2H), 4.24 (br dd, J = 4.9, 10.9 Hz, 1H), 4.15-4.07 (m, 3H), 4.05-3.94 (m, 3H), 3.94-3.89 (m, 2H), 3.80 (br t, J = 6.8 Hz, 2H), 3.70-3.65 (m, 2H), 3.60-3.56 (m, 2H), 3.56-3.46 (m, 8H), 3.45-3.40 (m, 6H), 3.27-3.22 (m, 3H), 3.19 (br s, 2H), 3.07-2.86 (m, 4H), 2.73-2.66 (m, 1H), 2.37-2.32 (m, 1H), 2.31 (s, 3H), 2.25 (br d, J = 9.5 Hz, 1H), 2.21 (s, 3H), 2.15 (br dd, J = 6.2, 9.5 Hz, 1H), 2.09-1.98 (m, 2H), 1.90-1.78 (m, 2H), 1.77-1.52 (m, 6H), 1.13 (d, J = 6.7 Hz, 3H), 1.08 (br d, J = 8.9 Hz, 2H), 1.02 (br d, J = 7.1 Hz, 1H), 0.96 (br d, J = 11.7 Hz, 1H). | 22 | 1246.56 |
| 550 | 1290.85 | | $^1$H NMR (400 MHz, CD$_3$OD) δ 8.36-8.29 (m, 1H), 8.27-8.17 (m, 1H), 8.17-8.08 (m, 1H), 7.95-7.81 (m, 1H), 7.64 (d, J = 8.4 Hz, 1H), 7.60-7.40 (m, 7H), 7.27-7.11 (m, 1H), 6.99-6.91 (m, 1H), 6.90-6.68 (m, 1H), 6.30 (d, J = 16.4 Hz, 1H), 5.84 (d, J = 11.2 Hz, 1H), 5.64-5.45 (m, 1H), 5.10-4.91 (m, 1H), 4.85-4.74 (m, 1H), 4.69-4.56 (m, 2H), 4.54-4.40 (m, 1H), 4.40-4.03 (m, 8H), 4.03-3.85 (m, 5H), 3.85-3.75 (m, 3H), 3.73-3.58 (m, 15H), 3.57-3.33 (m, 4H), 3.23-2.77 (m, 8H), 2.69-2.52 (m, 3H), 2.52-2.44 (m, 2H), 2.41-1.97 (m, 5H), 1.89-1.58 (m, 6H), 1.53-1.30 (m, 3H), 1.29-1.04 (m, 5H). | 22 | 1290.61 |
| 551 | 1252.67 | 1254.67 | $^1$H NMR (400 MHz, DMSO-d$_6$) δ 10.39 (s, 1H), 8.50-8.45 (m, 1H), 8.33-8.32 (m, 1H), 8.31-8.29 (m, 1H), 8.19-8.17 (m, 1H), 7.94-7.90 (m, 1H), 7.74-7.71 (m, 1H), 7.65 (d, J = 8.0 Hz, 1H), 7.56-7.32 (m, 11H), 7.24 (d, J = 7.6 Hz, 1H), 6.94-6.78 (m, 1H), 6.23-6.14 (m, 1H), 5.81-5.74 (m, 1H), 5.03-4.70 (m, 1H), 4.62-4.54 (m, 2H), 4.40-4.32 (m, 1H), 4.27-4.21 (m, 1H), 4.16-3.93 (m, 8H), 3.91 (s, 3H), 3.59-3.45 (m, 8H), 3.41-3.38 (m, 2H), 3.26-3.22 (m, 2H), 3.05-2.83 (m, 2H), 2.70-2.65 (m, 1H), 2.34-2.31 (m, 2H), 2.30 (s, 3H), 2.17-2.11 (m, 1H), 1.89-1.75 (m, 2H), 1.68-1.59 (m, 1H), 1.29-1.22 (m, 1H), 0.96 (s, 9H). | 23 | 1253.27 |
| 552 | 1296.72 | 1298.72 | $^1$H NMR (400 MHz, DMSO-d$_6$) δ 10.41 (s, 1H), 8.49 (br t, J = 5.5 Hz, 1H), 8.31 (d, J = 8.4 Hz, 1H), 8.22 (s, 1H), 8.20-8.14 (m, 1H), 7.96-7.89 (m, 1H), 7.72 (br t, J = 6.8 Hz, 1H), 7.64 (d, J = 8.3 Hz, 1H), 7.60-7.50 (m, 5H), 7.50-7.43 (m, 2H), 7.41-7.32 (m, 3H), 7.21 (d, J = 7.3 Hz, 1H), 6.98-6.74 (m, 1H), 6.25-6.11 (m, 1H), 5.78 (br d, J = 12.5 Hz, 1H), 5.06-4.72 (m, 1H), 4.62-4.51 (m, 2H), 4.51-4.28 (m, 2H), 4.24 (br dd, J = 4.7, 10.8 Hz, 1H), 4.15-3.93 (m, 8H), 3.91 (s, 3H), 3.55-3.51 (m, 6H), 3.50-3.47 (m, 4H), 3.45-3.43 (m, 4H), 3.25 (br d, J = 3.4 Hz, 1H), 3.16 (br s, 1H), 3.06-2.92 (m, 4H), 2.74-2.68 (m, 1H), 2.31 (s, 3H), 2.14 (dd, J = 6.1, 9.4 Hz, 1H), 1.91-1.74 (m, 2H), 1.63 (br dd, J = 9.9, 14.1 Hz, 1H), 1.31-1.10 (m, 2H), 0.96 (s, 9H). | 23 | 1297.32 |
| 553 | 1340.74 | 1342.74 | $^1$H NMR (400 MHz, DMSO-d$_6$) δ 10.41 (s, 1H), 8.49 (br t, J = 5.3 Hz, 1H), 8.32 (d, J = 8.3 Hz, 1H), 8.20 (s, 1H), 8.18 (br d, J = 6.2 Hz, 1H), 7.96-7.88 (m, 1H), 7.73 (br t, J = 6.9 Hz, 1H), 7.64 (d, J = 8.2 Hz, 1H), 7.60-7.51 (m, 5H), 7.50-7.44 (m, 2H), 7.42-7.33 (m, 3H), 7.22 (d, J = 7.5 Hz, 1H), 6.88 (br s, 1H), 6.20 (br d, J = 17.9 Hz, 1H), 5.78 (br d, J = 12.2 Hz, 1H), 5.07-4.73 (m, 1H), 4.62-4.55 (m, 2H), 4.39 (br d, J = 11.0 Hz, 2H), 4.26 (br dd, J = 4.8, 10.9 Hz, 1H), 4.18-4.07 (m, 4H), 4.07-3.94 (m, 5H), 3.92 (s, 3H), 3.56-3.52 (m, 10H), 3.48 (br d, J = 8.1 Hz, 9H), 3.27 (br dd, J = 6.1, 9.7 Hz, 1H), 3.06-2.89 (m, 2H), 2.77-2.68 (m, 1H), 2.33 (s, 3H), 2.17 (br dd, J = 5.9, 9.4 Hz, 1H), 1.89-1.60 (m, 4H), 1.27 (br d, J = 13.8 Hz, 2H), 0.97 (s, 9H). | 23 | 1341.37 |
| 554 | 1384.76 | 1386.76 | $^1$H NMR (400 MHz, CD$_3$OD) δ 8.52 (s, 1H), 8.32 (d, J = 8.4 Hz, 1H), 8.26-8.15 (m, 1H), 7.91-7.83 (m, 1H), 7.70 (t, J = 6.4 Hz, 1H), 7.61 (d, J = 8.4 Hz, 1H), 7.53 (d, J = 2.0 Hz, 1H), 7.52-7.46 (m, 2H), 7.45-7.35 (m, 3H), 7.35-7.14 (m, 5H), 6.95-6.68 (m, 1H), 6.29 (d, J = 17.2 Hz, 1H) 5.83 (d, J = 10.4 Hz, 1H), 5.17-4.92 (m, 1H), 4.73 (d, J = 8.4 Hz, 1H), 4.55 (d, J = 8.4 Hz, 1H), 4.50-4.34 (m, 2H), 4.31-4.00 (m, 7H), 3.97 (s, 3H), 3.69-3.45 (m, 22H), 3.43-3.36 (m, 1H), 3.30-3.10 (m, 4H), 3.09-2.84 (m, 4H), 2.74-2.59 (m, 4H), 2.26-2.12 (m, 1H), 2.06-1.89 (m, 1H), 1.72-1.61 (m, 1H), 1.37-1.29 (m, 1H), 1.00 (s, 9H). | 23 | 1385.43 |
| 555 | 919.47 919.46 | 921.48 921.47 | $^1$H NMR (400 MHz, DMSO-d$_6$) δ 11.06 (s, 1H), 8.23 (s, 1H), 8.00 (s, 1H), 7.80 (dd, J = 4.1, 7.9 Hz, 1H), 7.55 (dd, J = 7.8, 12.8 Hz, 1H), 7.43 (dd, J = 3.4, 11.1 Hz, 1H), 7.28 (s, 1H), 7.24-7.17 (m, 2H), 7.12 (dd, J = 2.7, 8.7 Hz, 1H), 7.08-7.04 (m, 1H), 7.01 (d, J = 7.1 Hz, 1H), 6.83 (dd, J = 10.6, 16.7 Hz, 1H), 6.59 (s, 1H), 6.18 (dd, J = 2.3, 16.6 Hz, 1H), 5.78-5.70 (m, 1H), 5.36 (d, J = 5.6 Hz, 1H), 5.09-4.98 (m, 1H), 3.95-3.77 (m, 8H), 3.61-3.53 (m, 2H), 3.41 (s, 2H), 2.90-2.71 (m, 3H), 2.65-2.56 (m, 2H), 2.52 (d, J = 1.8 Hz, 4H), 2.37 (s, 1H), 2.16 (d, J = 8.7 Hz, 2H), 2.04-1.95 (m, 1H), 1.74 (d, J = 10.9 Hz, 2H), 1.41-1.28 (m, 5H). | 12 | 919.39 |
| 556 | 963.50 963.49 | 965.51 965.49 | $^1$H NMR (400 MHz, DMSO-d$_6$) δ 11.09 (s, 1H), 8.22 (s, 2H), 8.01 (s, 1H), 7.82 (d, J = 8.3 Hz, 1H), 7.55 (br t, J = 9.1 Hz, 1H), 7.44 (d, J = 5.6 Hz, 1H), 7.29 (s, 1H), 7.22 J = 6.8 Hz, 2H), 7.12 (dd, J = 3.3, 8.3 Hz, 1H), 7.07 (dd, J = 2.3,4.5 Hz, 1H), 7.02 (d, J = 7.0 Hz, 1H), 6.84 (dd, J = 10.5, 16.8 Hz, 1H), 6.59 (s, 1H), 6.19 (dd, J = 2.2, 16.9 Hz, 1H), 5.79-5.73 (m, 1H), 5.38 (dd, J = 5.5, 11.5 Hz, 1H), 5.05 (d, J = 12.7 Hz, 1H), 3.97-3.77 (m, 9H), 3.63-3.58 (m, 3H), 3.53-3.43 (m, 2H), 3.12-2.99 (m, 1H), 2.96-2.71 (m, 4H), 2.60 (s, 2H), 2.47-2.36 (m, 2H), 2.17-1.98 (m, 3H), 1.78-1.65 (m, 2H), 1.43-1.11 (m, 6H). | 12 | 963.45 |
| 557 | 1007.53 | 1009.53 | $^1$H NMR (400 MHz, DMSO-d$_6$) δ 11.09 (s, 1H), 10.35-9.83 (m, 1H), 8.26 (s, 1H), 8.00 (s, 1H), 7.80 (dd, J = 2.5, 8.1 Hz, 1H), 7.59-7.51 (m, 1H), 7.47-7.39 (m, 1H), 7.28 (s, 1H), 7.26-7.16 (m, 2H), 7.14-7.05 (m, 2H), 7.02 (d, J = 7.0 Hz, 1H), 6.83 (dd, J = 10.5, 16.7 Hz, 1H), 6.62-6.54 (m, 1H), 6.18 (dd, J = 2.3, 16.7 Hz, 1H), 5.77-5.72 (m, 1H), 5.49-5.28 (m, 1H), 5.04 (br dd, J = 5.3, 12.7 Hz, 1H), 4.04-3.71 (m, 9H), 3.62-3.57 (m, 4H), 3.47-3.43 (m, 6H), 3.00-2.68 (m, 4H), 2.63-2.57 (m, 2H), 2.41-2.34 (m, 1H), 2.13-1.97 (m, 3H), 1.69 (br s, 2H), 1.34-1.17 (m, 5H). | 12 | 1007.50 |
| 558 | 1051.56 | 1053.57 | $^1$H NMR (400 MHz, DMSO-d$_6$) δ 11.04 (s, 1H), 10.48-9.64 (m, 1H), 8.27 (s, 1H), 7.95 (s, 1H), 7.76 (d, J = 8.1 Hz, 1H), 7.56-7.47 (m, 1H), 7.4-7.28 (m, 1H), 7.24 (s, 1H), 7.21-7.11 (m, 2H), 7.09-6.94 (m, 3H), 6.82-6.7 (m, 1H), 6.55-6.49 (m, 1H), 6.2-6.1 (m, 1H), 5.73-5.66 | 12 | 1051.55 |

TABLE 13-continued

Data for Compounds of Table 12

| Ex. No. | MH+ (1) | MH+ (2) | NMR Transcript | Synthetic Scheme | Mol Weight |
|---|---|---|---|---|---|
| | | | (m, 1H), 5.33-5.18 (m, 1H), 5.1-4.9 (m, 1H), 3.89-3.85 (m, 4H), 3.82-3.78 (m, 2H), 3.74-3.6 (m, 2H), 3.55-3.53 (m, 2H), 3.48-3.45 (m, 7.9 Hz, 8H), 3.42-3.4 (m, 4H), 2.88-2.66 (m, 4H), 2.59-2.53 (m, 2H), 2.12-1.91 (m, 4H), 1.71-1.61 (m, 2H), 1.34-1.11 (m, 6H). | | |
| 559 | 1095.59 | 1097.59 | $^1$H NMR (400 MHz, DMSO-$d_6$) δ 11.09 (s, 1H), 8.29 (s, 1H), 8.00(s, 1H), 7.81-7.92 (d, J = 8.0 Hz, 1H), 7.60-7.53 (m, 1H), 7.47-7.38 (m, 1H), 7.28 (d, J = 2.1 Hz, 1H), 7.25-7.16 (m, 2H), 7.12-7.10 (d, J = 8.6 Hz, 1H), 7.06 (dd, J = 2.4, 4.9 Hz, 1H), 7.03-7.01 (d, J = 7.1 Hz, 1H), 6.83 (dd, J = 10.4, 16.7 Hz, 1H), 6.58 (t, J = 5.8 Hz, 1H), 6.22-6.13 (m, 1H), 5.78-5.70 (m, 1H), 5.38 (br dd, J = 6.0, 12.0 Hz, 1H), 5.04 (dd, J = 5.3, 12.9 Hz, 1H), 3.98-3.72 (m, 9H), 3.60 (br t, J = 5.3 Hz, 2H), 3.54-3.50 (m, 4H), 3.45 (br dd, J = 3.1, 7.8 Hz, 14H), 2.94-2.69 (m, 4H), 2.64-2.55 (m, 2H), 2.40-2.35 (m, 1H), 2.14-2.00 (m, 3H), 1.77-1.64 (m, 2H), 1.34-1.22 (m, 5H). | 12 | 1095.61 |
| 560 | 939.46 | 941.46 | $^1$H NMR (400 MHz, DMSO-$d_6$) δ 11.08 (s, 1H), 10.06 (s, 1H), 9.42 (s, 1H), 8.35 (s, 1H), 8.01 (s, 1H), 7.80 (s, 1H), 7.59-7.52 (m, 1H), 7.47-7.40 (m, 1H), 7.28 (s, 1H), 7.24-7.16 (m, 2H), 7.13 (d, J = 8.7 Hz, 1H), 7.08-7.03 (m, 1H), 7.01 (d, J = 7.0 Hz, 1H), 6.60 (s, 1H), 6.39 (d, J = 7.0 Hz, 1H), 5.35 (s, 1H), 5.04 (dd, J = 5.6, 12.9 Hz, 1H), 3.96-3.87 (m, 4H), 3.74 (d, J =-19.4 Hz, 2H), 3.57 (d, J = 5.3 Hz, 2H), 3.41 (d, J-= 5.4 Hz, 4H), 3.01 (s, 1H), 2.90-2.73 (m, 3H), 2.65-2.58 (m, 3H), 2.23-2.10 (m, 3H), 2.09-1.91 (m, 2H), 1.74 (d, J = 12.3 Hz, 2H), 1.38-1.22 (m, 5H). | 12 | 939.38 |
| 561 | 983.49 | 985.49 | $^1$H NMR (400 MHz, DMSO-$d_6$) δ 11.09 (s, 1H), 8.14 (s, 1H), 8.01 (s, 1H), 7.81 (d, J = 4.9 Hz, 1H), 7.54 (t, J = 7.6 Hz, 1H), 7.42 (s, 1H), 7.28 (s, 1H), 7.26-6.99 (m, 5H), 6.59 (s, 1H), 6.38 (d, J = 7.3 Hz, 1H), 5.37 (d, J = 7.1 Hz, 1H), 5.04 (d, J = 13.1 Hz, 1H), 4.10 (d, J = 5.3 Hz, 1H), 3.88 (d, J = 17.9 Hz, 4H), 3.74 (d, J = 19.8 Hz, 2H), 3.59 (s, 2H), 3.54-3.39 (m, 81-1), 3.17 (s, 1H), 2.85 (d, J = 12.8 Hz, 3H), 2.58 (s, 3H), 2.44-2.35 (m, 2H), 2.29-1.95 (m, 3H), 1.72 (s, 2H), 1.37-1.18 (m, 5H). | 12 | 983.44 |
| 562 | 1027.53 | 1029.53 | $^1$H NMR (400 MHz, DMSO-$d_6$)6 11.09 (s, 1H), 10.01 (s, 1H), 8.15 (s, 1H), 8.02(s, 1H), 7.84-7.80 (m, 1H), 7.56 (t, J = 8.0 Hz, 1H), 7.49-7.40 (m, 1H), 7.29 (s, 1H), 7.27-7.17 (m, 2H), 7.14-7.06 (m, 2H), 7.03 (d, J = 7.2 Hz, 1H), 6.59 (t, J = 5.6 Hz, 1H), 6.37 (d, J = 7.2 Hz, 1H), 5.48-5.32 (m, 2H), 5.08-5.02 (m, 1H), 3.95-3.43 (m, 24H), 2.91-2.75 (m, 2H), 2.64-2.55 (m, 2H), 2.25-1.96 (m, 4H), 1.75-1.65 (m, 2H), 1.37-1.25 (m, 51-1). | 12 | 1027.49 |
| 563 | 1071.55 | 1073.56 | $^1$H NMR (400 MHz, DMSO-$d_6$) δ 11.06 (s, 1H), 10.00 (s, 1H), 8.17 (s, 1H), 7.98 (s, 1H), 7.85-7.68 (m, 1H), 7.58-7.51 (m, 1H), 7.44-7.39 (m, 1H), 7.35-7.26 (m, 1H), 7.24-7.15 (m, 3H), 7.14-7.08 (m, 1H), 7.06-6.98 (m, 2H), 6.75-6.5 (m, 1H), 6.35-5.6 (m, 1H), 5.44-5.31 (m, 2H), 5.02-4.8 (m, 1H), 3.87-3.8 (m, 6H), 3.77-3.67 (m, 2H), 3.6-3.55 (m, 2H), 3.52-3.49 (m, 4H), 3.46-3.41 (m, 10H), 2.98-2.66 (m, 4H), 2.62-2.55 (m, 2H), 2.35-2.2 (m, 1H), 2.13-1.97 (m, 3H), 1.68-1.55 (m, 2H), 1.34-1.19 (m, 6H). | 12 | 1071.54 |
| 564 | 1115.58 | 1117.58 | $^1$H NMR (400 MHz, DMSO-$d_6$) δ 11.10 (s, 1H), 8.13 (s, 1H), 8.06-7.94 (m, 1H), 7.81 (d, J = 8.3 Hz, 1H), 7.59-7.53 (m, 1H), 7.47-7.40 (m, 1H), 7.29 (d, J = 2.1 Hz, 1H), 7.26-7.15 (m, 2H), 7.12 (d, J = 8.6 Hz, 1H), 7.08-7.01 (m, 2H), 6.59 (br t, J = 5.7 Hz, 1H), 6.42-6.40 (d, J = 8.0 Hz, 1H), 5.60-5.42 (m, 1H), 5.36 (t, J = 7.3 Hz, 1H), 5.05 (dd, J = 5.4, 12.9 Hz, 1H), 4.06-3.80 (m, 6H), 3.79-3.69 (m, 2H), 3.66-3.57 (m, 3H), 3.56-3.40 (m, 22H), 3.25 (s, 1H), 2.93-2.81 (m, 2H), 2.69 (s, 1H), 2.62-2.54 (m, 2H), 2.08-1.96 (m, 2H), 1.91-1.69 (m, 2H), 1.33 (br d, J = 5.8 Hz, 4H). | 12 | 1115.59 |
| 565 | 975.61 | | $^1$H NMR (400 MHz, 400 MHz, DMSO-$d_6$) δ 10.95 (br s, 1H), 8.23 (s, 1H), 8.12-8.09 (m, 1H), 7.95-7.89 (m, 1H), 7.67-7.60 (m, 2H), 7.57-7.50 (m, 1H), 7.47 (t, J = 7.8 Hz, 1H), 7.23 (t, J = 7.5 Hz, 1H), 7.17 (d, J = 1.8 Hz, 1H), 7.06 (dd, J = 2.3, 8.4 Hz, 1H), 6.23 (s, 2H), 5.07 (dd, J = 5.1, 13.3 Hz, 1H), 4.58 (br s, 1H), 4.42-4.34 (m, 1H), 4.31-4.23 (m, 2H), 4.21-4.16 (m, 2H), 4.16-4.08 (m, 3H), 3.99 (br t, J = 14.1 Hz, 3H), 3.85 (br d, J = 12.9 Hz, 1H), 3.80-3.75 (m, 2H), 3.63-3.58 (m, 2H), 3.56-3.53 (m, 2H), 3.51 (br s, 41-1), 3.49 (br s, 1H), 3.48 (br s, 1H), 3.45 (br s, 1H), 3.20-3.14 (m, 2H), 3.15-3.11 (m, 4H), 3.10-3.01 (m, 1H), 2.95-2.88 (m, 5H), 2.59 (br s, 1H), 2.39 (br dd, J = 4.4, 13.1 Hz, 1H), 2.36 (br s, 1H), 2.32 (s, 3H), 2.16 (br dd, J = 6.1, 9.2 Hz, 1H), 2.01-1.95 (m, 2H), 1.92-1.77 (m, 2H). | 21 | 975.10 |
| 566 | 926.46 | 928.46 | $^1$H NMR (400 MHz, DMSO-$d_6$) δ 10.95 (s, 1H), 10.00 (brs, 1H), 9.36-9.42 (m, 0.4H), 8.14 (s, 1H), 8.01 (s, 1H), 7.80 (dd, J = 8.4, 4.4 Hz, 1H), 7.60 (d, J = 8.4 Hz, 1H), 7.36-7.47 (m, 1H), 7.28 (s, 1H), 7.13-7.25 (m, 3H), 7.00-7.08 (m, 2H), 6.35-6.38 (m, 1H), 5.31-5.50 (m, 1.7H), 5.06 (dd, J = 8.4, 5.2 Hz, 1H), 4.31-4.41 (m, 1H), 4.20-4.29 (m, 1H), 4.14 (s, 2H), 3.82-3.96 (m, 6H), 3.69-3.78 (m, 4H), 2.75-2.93 (m, 3H), 2.55-2.62 (m, 2H), 2.33-2.40 (m, 3H), 2.11-2.24 (m, 2H), 1.91-2.02 (m, 1H), 1.71-1.81 (m, 2H), 1.21-1.44 (m, 6H). | 12 | 926.38 |
| 567 | 970.50 | 972.50 | $^1$H NMR (400 MHz, DMSO-$d_6$) δ 10.96 (s, 1H), 10.03 (brs, 1H), 9.36-9.43 (m, 0.4H), 8.15 (s, 1H), 8.03 (s, 1H), 7.81 (d, J = 8.4 Hz, 1H), 7.61 (d, J = 8.4 Hz, 1H), 7.40-7.51 (m, 1H), 7.12-7.34 (m, 4H), 7.00-7.10 (m, 2H), 6.37-6.39 (m, 1H), 5.30-5.62 (m, 1.6H), 5.07 (dd, J = 13.2, 5.2 Hz, 1H), 4.32-4.42 (m, 1H), 4.21-4.30 (m, 1H), 4.12-4.20 (m, 2H), 3.83-4.01 (m, 6H), 3.70-3.79 (m, 4H), 3.46-3.61 (m, 5H), 2.81-3.03 (m, 4H), 2.55-2.61 (m, 3H), 2.35-2.45 (m, 2H), 1.94-2.02 (m, 1H), 1.73-1.86 (m, 2H), 1.22-1.62 (m, 6H). | 12 | 970.44 |
| 568 | 1014.52 | 1016.52 | $^1$H NMR (400 MHz, DMSO-$d_6$) δ 10.95 (s, 1H), 9.43 (s, 1H), 8.24 (s, 1H), 8.00 (s, 1H), 7.80 (d, 1 = 8.0 Hz, 1H), 7.60 (d, J = 8.4 Hz, 1H), 7.43 (dd, 1 = 5.6, 7.2 Hz, 1H), 7.28 (s, 1H), 7.25-7.12 (m, 3H), 7.09-7.00 (m, 2H), 6.65-5.99 (m, 1H), 5.45-5.31 (m, 2H), 5.06 (dd, J = 5.2, 13.2 Hz, 1H), 4.42-4.32 (m, 1H), 4.29-4.21 (m, 1H), 4.18-4.11 (m, 2H), 3.96-3.83 (m, 5H), 3.78-3.68 (m, 5H), 3.61-3.50 (m, 7H), 3.45 (s, 1H), 3.28-3.15 (m, 1H), 2.97-2.69 (m, 3H), 2.65-2.52 (m, 2H), 2.42-2.31 (m, 2H), 2.19-1.92 (m, 3H), 1.77-1.65 (m, 2H), 1.36-1.14 (m, 6H). | 12 | 1014.49 |
| 569 | 1058.56 | 1060.56 | $^1$H NMR (400 MHz, DMSO-$d_6$) δ 10.97 (s, 1H), 10.04 (br s, 1H), 9.46-9.31 (m, 1H), 8.14 (s, 1H), 8.03 (s, 1H), 7.82 (d, J = 8.0 Hz, 1H), 7.62 (d, 1 = 8.4 Hz, 1H), 7.49-7.40 (m, 1H), 7.30 (s, 1H), 7.27-7.12 (m, 3H), 7.10-7.00 (m, 2H), 6.42-6.37 (m, 1H), 5.57-5.29 (m, 2H), 5.14-5.00 (m, 1H), 4.42-4.32 (m, 1H), 4.30-4.22 (m, 1H), 4.20-4.10 (m, 2H), 4.00-3.69 (m, | 12 | 1058.54 |

TABLE 13-continued

Data for Compounds of Table 12

| Ex. No. | MH+ (1) | MH+ (2) | NMR Transcript | Synthetic Scheme | Mol Weight |
|---|---|---|---|---|---|
| | | | 10H), 3.61-3.43 (m, 10H), 3.06-2.82 (m, 4H), 2.75-2.54 (m, 3H), 2.46-2.29 (m, 5H), 2.03-1.93 (m, 1H), 1.87-1.71 (m, 2H), 1.54-1.19 (m, 6H). | | |
| 570 | 1102.59 | 1104.59 | $^1$H NMR (400 MHz, DMSO-d$_6$) δ 10.96 (s, 1H), 10.02 (s, 1H), 9.45-9.36 (m, 0.2H), 8.15 (s, 1H), 8.02 (s, 1H), 7.82 (d, J = 8.4 Hz, 1H), 7.62 (d, J = 8.4 Hz, 1H), 7.49-7.40 (m, 1H), 7.32-7.13 (m, 4H), 7.09-7.01 (m, 2H), 6.37 (d, J = 7.2 Hz, 1H), 5.48-5.33 (m, 2H), 5.11-5.02 (m, 1H), 4.43-4.23 (m, 2H), 4.21-4.12 (m, 2H), 4.00-3.82 (m, 6H), 3.79-3.68 (m, 5H), 3.62-3.42 (m, 13H), 2.99-2.77 (m, 4H), 2.74-2.59 (m, 3H), 2.42-2.15 (m, 5H), 2.03-1.93 (m, 1H), 1.81-1.68 (m, 2H), 1.43-1.08 (m, 6H). | 12 | 1102.59 |
| 571 | 1125.69 | | $^1$H NMR (400 MHz, DMSO-d$_6$) δ 10.01 (s, 1H), 8.98 (s, 1H), 8.42-8.30 (m, 1H), 8.23-8.14 (m, 1H), 7.96-7.88 (m, 1H), 7.66-7.64 (d, J = 8.0 Hz, 1H), 7.57-7.50 (m, 2H), 7.49-7.43 (m, 1H), 7.35-7.33 (d, J = 8.0 Hz, 1H), 7.25-7.18 (m, 1H), 7.08-6.96 (m, 2H), 6.42-6.13 (m, 3H), 4.64-4.54 (m, 3H), 4.49-4.13 (m, 11H), 4.10-3.98 (m, 2H), 3.96-3.53 (m, 11H), 3.49-3.11 (m, 6H), 3.10-2.79 (m, 7H), 2.47-2.44 (m, 3H), 2.34-2.21 (m, 2H), 2.21-2.12 (m, 3H), 2.09-1.97 (m, 2H), 1.95-1.86 (m, 1H), 1.01-0.88 (m, 3H), 0.82-0.71 (m, 3H). | 19 | 1125.34 |
| 572 | 1169.72 | | $^1$H NMR (400 MHz, DMSO-d$_6$) δ 10.55-9.82 (m, 1H), 8.97 (s, 1H), 8.29 (br t, J = 5.9 Hz, 1H), 8.22-8.14 (m, 1H), 7.97-7.87 (m, 1H), 7.65 (d, J = 8.1 Hz, 1H), 7.58-7.50 (m, 2H), 7.46 (t, J = 7.8 Hz, 1H), 7.32-7.19 (m, 2H), 7.10-6.94 (m, 2H), 6.39-6.05 (m, 3H), 4.66-4.54 (m, 2H), 4.52-4.44 (m, 2H), 4.42-4.32 (m, 1H), 4.30-4.20 (m, 3H), 4.18-4.13 (m, 4H), 4.10-4.00 (m, 2H), 3.93 (br s, 1H), 3.87-3.81 (m, 3H), 3.79-3.76 (m, 3H), 3.58-3.54 (m, 10H), 3.44 (br d, J = 4.9 Hz, 1H), 3.36 (br s, 1H), 3.31-3.12 (m, 5H), 3.03-2.98 (m, 5H), 2.96-2.79 (m, 3H), 2.46-2.44 (m, 3H), 2.34-2.28 (m, 1H), 2.26 (br d, J = 8.1 Hz, 1H), 2.21-2.13 (m, 3H), 2.10-1.97 (m, 2H), 1.96-1.83 (m, 1H), 0.96 (d, J = 6.6 Hz, 2.5H), 0.79 (d, J = 6.7 Hz, 2.5H), 0.70 (d, J = 6.6 Hz, 0.5H), 0.58 (d, J = 6.6 Hz, 0.5H). | 19 | 1169.40 |
| 573 | 1169.72 | | $^1$H NMR (400 MHz, DMSO-d$_6$) δ 10.43-9.83 (m, 1H), 8.97 (s, 1H), 8.62 (s, 1H), 8.36-8.19 (m, 1H), 7.99-7.89 (m, 1H), 7.65 (d, J = 8.1 Hz, 1H), 7.58-7.50 (m, 2H), 7.46 (t, J = 7.8 Hz, 1H), 7.34 (d, 1 = 7.6 Hz, 1H), 7.22 (br d, 1 = 7.3 Hz, 1H), 7.08-6.98 (m, 2H), 6.34-6.16 (m, 3H), 4.70-4.55 (m, 2H), 4.46 (br dd, J = 7.0, 12.5 Hz, 1H), 4.41-4.34 (m, 2H), 4.30-4.23 (m, 3H), 4.20-4.14 (m, 4H), 4.09-3.99 (m, 2H), 4.11-3.99 (m, 1H), 3.84 (br d, 1 = 15.3 Hz, 1H), 3.81-3.75 (m, 4H), 3.73 (s, 1H), 3.67-3.49 (m, 10H), 3.43 (br d, J = 11.3 Hz, 1H), 3.36 (br s, 1H), 3.29 (br d, J = 14.5 Hz, 1H), 3.21 (br d, J = 10.8 Hz, 3H), 3.10-2.95 (m, 6H), 2.94-2.78 (m, 3H), 2.46 (s, 3H), 2.44 (s, 1H), 2.29-2.23 (m, 1H), 2.19 (s, 3H), 2.10-1.97 (m, 2H), 1.92 (ddd, J = 4.8, 7.8, 12.6 Hz, 1H), 0.98-0.91 (m, 3H), 0.80-0.74 (m, 3H). | 19 | 1169.40 |

TABLE 14

Target Proteion Degradation via Exemplary Bifunctional Compounds from Tables 6, 8, 10, and 12.

| | SW1573 | | | | | | | | H2030 | | | | | | | |
|---|---|---|---|---|---|---|---|---|---|---|---|---|---|---|---|---|
| | | | Percent Degradation at Indicated Concentration (μM)*** | | | | | | | | Percent Degradation at Indicated Concentration (μM)*** | | | | | | |
| Ex. No. | DC$_{50}$* | D$_{Max}$** | 10 | 3 | 1 | 0.3 | 0.1 | 0.03 | 0.01 | DC$_{50}$* | D$_{Max}$** | 10 | 3 | 1 | 0.3 | 0.1 | 0.03 | 0.01 |
| 519 | nd | A | nd | nd | C | A | B | nd | nd | nd | nd | nd | nd | nd | nd | nd | nd |
| 543 | nd | nd | nd | C | C | C | nd | nd | nd | nd | nd | nd | nd | nd | nd | nd | nd |
| 539 | nd | nd | nd | C | C | C | C | C | nd | nd | nd | nd | nd | nd | nd | nd | nd |
| 525 | nd | nd | nd | nd | C | C | C | nd | nd | nd | nd | nd | nd | nd | nd | nd | nd |
| 516 | nd | B | nd | nd | B | B | C | nd | nd | nd | nd | nd | nd | nd | nd | nd | nd |
| 515 | nd | nd | nd | C | C | C | nd | nd | nd | nd | nd | nd | nd | nd | nd | nd | nd |
| 503 | nd | nd | nd | C | C | C | C | C | nd | nd | nd | nd | nd | nd | nd | nd | nd |
| 518 | nd | A | nd | nd | C | A | B | nd | nd | nd | nd | nd | nd | nd | nd | nd | nd |
| 505 | nd | nd | nd | nd | C | C | C | nd | nd | nd | nd | nd | nd | nd | nd | nd | nd |
| 504 | nd | A | nd | nd | C | A | B | nd | nd | nd | nd | nd | nd | nd | nd | nd | nd |
| 537 | nd | nd | nd | C | C | C | nd | nd | nd | nd | nd | nd | nd | nd | nd | nd | nd |
| 532 | nd | nd | nd | nd | C | C | C | nd | nd | nd | nd | nd | nd | nd | nd | nd | nd |
| 531 | nd | nd | nd | nd | C | C | C | nd | nd | nd | nd | nd | nd | nd | nd | nd | nd |
| 530 | nd | nd | nd | nd | C | C | C | nd | nd | nd | nd | nd | nd | nd | nd | nd | nd |
| 529 | nd | nd | nd | nd | C | C | C | nd | nd | nd | nd | nd | nd | nd | nd | nd | nd |
| 528 | nd | nd | nd | nd | C | C | C | nd | nd | nd | nd | nd | nd | nd | nd | nd | nd |
| 527 | nd | nd | nd | nd | C | C | C | nd | nd | nd | nd | nd | nd | nd | nd | nd | nd |
| 526 | nd | nd | nd | nd | C | C | C | nd | nd | nd | nd | nd | nd | nd | nd | nd | nd |
| 524 | nd | nd | nd | nd | C | C | C | nd | nd | nd | nd | nd | nd | nd | nd | nd | nd |
| 481 | nd | B | nd | nd | B | C | C | nd | nd | nd | nd | nd | nd | nd | nd | nd | nd |
| 247 | nd | nd | nd | C | C | C | nd | nd | nd | nd | nd | nd | nd | nd | nd | nd | nd |
| 480 | nd | nd | nd | C | C | C | nd | nd | nd | nd | nd | nd | nd | nd | nd | nd | nd |
| 245 | nd | nd | nd | C | C | C | nd | nd | nd | nd | nd | nd | nd | nd | nd | nd | nd |
| 405 | nd | nd | nd | C | C | C | nd | nd | nd | nd | nd | nd | nd | nd | nd | nd | nd |
| 475 | nd | nd | nd | C | C | C | nd | nd | nd | nd | nd | nd | nd | nd | nd | nd | nd |
| 248 | nd | nd | nd | C | C | C | nd | nd | nd | nd | nd | nd | nd | nd | nd | nd | nd |
| 246 | nd | nd | nd | C | C | C | nd | nd | nd | nd | nd | nd | nd | nd | nd | nd | nd |

TABLE 14-continued

Target Proteion Degradation via Exemplary Bifunctional Compounds from Tables 6, 8, 10, and 12.

| | | | | SW1573 | | | | | | | | | H2030 | | | | |
|---|---|---|---|---|---|---|---|---|---|---|---|---|---|---|---|---|---|
| Ex. | | | Percent Degradation at Indicated Concentration (μM)*** | | | | | | | | | Percent Degradation at Indicated Concentration (μM)*** | | | | | |
| No. | $DC_{50}$* | $D_{Max}$** | 10 | 3 | 1 | 0.3 | 0.1 | 0.03 | 0.01 | $DC_{50}$* | $D_{Max}$** | 10 | 3 | 1 | 0.3 | 0.1 | 0.03 | 0.01 |
| 244 | nd | nd | nd | C | C | C | nd | nd | nd | nd | nd | nd | nd | nd | nd | nd | nd |
| 430 | nd | nd | nd | nd | C | C | C | nd | nd | nd | nd | nd | nd | nd | nd | nd | nd |
| 404 | nd | nd | nd | nd | A | A | B | nd | nd | nd | nd | nd | nd | nd | nd | nd | nd |
| 431 | nd | nd | nd | nd | C | C | C | nd | nd | nd | nd | nd | nd | nd | nd | nd | nd |
| 403 | A | B | nd | nd | C | B | B | B | C | nd | nd | nd | nd | nd | nd | nd | nd |
| 432 | nd | nd | nd | nd | C | C | C | nd | nd | nd | nd | nd | nd | nd | nd | nd | nd |
| 427 | nd | nd | nd | nd | C | C | C | nd | nd | nd | nd | nd | nd | nd | nd | nd | nd |
| 425 | nd | nd | nd | nd | C | C | C | nd | nd | nd | nd | nd | nd | nd | nd | nd | nd |
| 429 | nd | nd | nd | nd | C | C | C | nd | nd | nd | nd | nd | nd | nd | nd | nd | nd |
| 428 | nd | nd | nd | nd | C | C | C | nd | nd | nd | nd | nd | nd | nd | nd | nd | nd |
| 426 | nd | nd | nd | nd | C | C | C | nd | nd | nd | nd | nd | nd | nd | nd | nd | nd |
| 444 | nd | nd | nd | nd | C | C | C | nd | nd | nd | nd | nd | nd | nd | nd | nd | nd |
| 424 | nd | nd | nd | nd | C | C | C | nd | nd | nd | nd | nd | nd | nd | nd | nd | nd |
| 421 | nd | nd | nd | nd | C | C | C | nd | nd | nd | nd | nd | nd | nd | nd | nd | nd |
| 420 | nd | nd | nd | nd | C | C | C | nd | nd | nd | nd | nd | nd | nd | nd | nd | nd |
| 443 | nd | nd | nd | nd | C | C | C | nd | nd | nd | nd | nd | nd | nd | nd | nd | nd |
| 442 | nd | nd | nd | nd | C | C | C | nd | nd | nd | nd | nd | nd | nd | nd | nd | nd |
| 439 | nd | nd | nd | nd | C | C | C | nd | nd | nd | nd | nd | nd | nd | nd | nd | nd |
| 438 | nd | nd | nd | nd | B | C | B | nd | nd | nd | nd | nd | nd | nd | nd | nd | nd |
| 437 | nd | nd | nd | nd | C | C | C | nd | nd | nd | nd | nd | nd | nd | nd | nd | nd |
| 436 | nd | nd | nd | nd | B | B | C | nd | nd | nd | nd | nd | nd | nd | nd | nd | nd |
| 417 | nd | nd | nd | nd | C | C | C | nd | nd | nd | nd | nd | nd | nd | nd | nd | nd |
| 415 | nd | nd | nd | nd | C | C | C | nd | nd | nd | nd | nd | nd | nd | nd | nd | nd |
| 411 | nd | nd | nd | nd | C | C | C | nd | nd | nd | nd | nd | nd | nd | nd | nd | nd |
| 441 | nd | nd | nd | nd | C | C | C | nd | nd | nd | nd | nd | nd | nd | nd | nd | nd |
| 440 | nd | nd | nd | nd | C | C | C | nd | nd | nd | nd | nd | nd | nd | nd | nd | nd |
| 419 | nd | nd | nd | nd | nd | nd | nd | nd | nd | nd | nd | nd | C | C | C | nd | nd |
| 418 | nd | nd | nd | nd | nd | nd | nd | nd | nd | nd | nd | nd | C | C | C | nd | nd |
| 416 | nd | nd | nd | nd | nd | nd | nd | nd | nd | nd | nd | nd | C | C | C | nd | nd |
| 414 | nd | nd | nd | nd | nd | nd | nd | nd | nd | nd | nd | nd | C | C | C | nd | nd |
| 409 | nd | nd | nd | nd | C | C | C | nd | nd | nd | nd | nd | nd | nd | nd | nd | nd |
| 423 | nd | nd | nd | nd | nd | nd | nd | nd | nd | nd | nd | nd | C | C | C | nd | nd |
| 413 | nd | nd | nd | nd | nd | nd | nd | nd | nd | nd | nd | nd | C | C | C | nd | nd |
| 407 | nd | nd | nd | nd | nd | nd | nd | nd | nd | nd | nd | nd | C | C | C | nd | nd |
| 152 | nd | nd | nd | nd | nd | nd | nd | nd | nd | nd | nd | nd | C | C | C | nd | nd |
| 151 | nd | nd | nd | nd | nd | nd | nd | nd | nd | nd | nd | nd | C | C | C | nd | nd |
| 150 | nd | nd | nd | nd | nd | nd | nd | nd | nd | nd | nd | nd | C | C | C | nd | nd |
| 149 | nd | nd | nd | nd | nd | nd | nd | nd | nd | nd | nd | nd | C | C | C | nd | nd |
| 240 | nd | nd | nd | nd | nd | nd | nd | nd | nd | nd | nd | nd | C | C | C | nd | nd |
| 235 | nd | nd | nd | nd | nd | nd | nd | nd | nd | nd | nd | nd | C | C | C | nd | nd |
| 422 | nd | nd | nd | nd | nd | nd | nd | nd | nd | nd | nd | nd | C | C | C | nd | nd |
| 412 | nd | nd | nd | nd | nd | nd | nd | nd | nd | nd | nd | nd | C | C | C | nd | nd |
| 410 | nd | nd | nd | nd | nd | nd | nd | nd | nd | nd | nd | nd | C | C | C | nd | nd |
| 408 | nd | nd | nd | nd | nd | nd | nd | nd | nd | nd | nd | nd | C | C | C | nd | nd |
| 406 | nd | nd | nd | nd | nd | nd | nd | nd | nd | nd | nd | nd | C | C | C | nd | nd |
| 402 | C | C | nd | nd | C | C | C | C | C | nd | C | nd | C | C | C | nd | nd |
| 401 | C | C | nd | nd | C | C | C | C | C | nd | C | nd | C | C | C | nd | nd |
| 400 | C | C | nd | nd | C | C | C | C | C | nd | C | nd | C | C | C | nd | nd |
| 398 | A | B | nd | nd | C | B | B | B | C | nd | C | nd | C | C | C | nd | nd |
| 397 | B | C | nd | nd | C | C | C | C | C | nd | nd | nd | nd | nd | nd | nd | nd |
| 239 | nd | nd | nd | nd | nd | nd | nd | nd | nd | nd | C | nd | C | C | C | nd | nd |
| 238 | nd | nd | nd | nd | nd | nd | nd | nd | nd | nd | C | nd | C | C | C | nd | nd |
| 237 | nd | nd | nd | nd | nd | nd | nd | nd | nd | nd | C | nd | C | C | C | nd | nd |
| 236 | nd | nd | nd | nd | nd | nd | nd | nd | nd | nd | C | nd | C | C | C | nd | nd |
| 234 | nd | nd | nd | nd | nd | nd | nd | nd | nd | nd | C | nd | C | C | C | nd | nd |
| 399 | A | B | C | B | B | B | B | C | nd | C | B | C | B | C | C | C | C | nd |
| 497 | nd | nd | nd | nd | nd | nd | nd | nd | nd | nd | C | nd | C | C | C | nd | nd |
| 227 | nd | nd | nd | nd | nd | nd | nd | nd | nd | nd | C | nd | C | C | C | nd | nd |
| 32 | nd | nd | nd | nd | nd | nd | nd | nd | nd | nd | C | nd | C | C | C | nd | nd |
| 146 | nd | nd | nd | nd | nd | nd | nd | nd | nd | nd | C | nd | C | C | C | nd | nd |
| 278 | nd | nd | nd | nd | nd | nd | nd | nd | nd | nd | C | nd | C | C | C | nd | nd |
| 276 | nd | nd | nd | nd | nd | nd | nd | nd | nd | nd | C | nd | C | C | C | nd | nd |
| 39 | nd | nd | nd | nd | nd | nd | nd | nd | nd | nd | C | nd | C | C | C | nd | nd |
| 37 | nd | nd | nd | nd | nd | nd | nd | nd | nd | nd | C | nd | C | C | C | nd | nd |
| 132 | nd | nd | nd | nd | nd | nd | nd | nd | nd | nd | C | nd | C | C | C | nd | nd |
| 131 | nd | nd | nd | nd | nd | nd | nd | nd | nd | nd | C | nd | C | C | C | nd | nd |
| 127 | nd | nd | nd | nd | nd | nd | nd | nd | nd | nd | C | nd | C | C | C | nd | nd |
| 34 | nd | nd | nd | nd | nd | nd | nd | nd | nd | nd | C | nd | C | C | C | nd | nd |
| 307 | nd | nd | nd | nd | nd | nd | nd | nd | nd | nd | C | nd | C | C | C | nd | nd |
| 130 | nd | nd | nd | nd | nd | nd | nd | nd | nd | nd | C | nd | C | C | C | nd | nd |
| 128 | nd | nd | nd | nd | nd | nd | nd | nd | nd | nd | C | nd | C | C | C | nd | nd |

TABLE 14-continued

Target Proteion Degradation via Exemplary Bifunctional Compounds from Tables 6, 8, 10, and 12.

| | | | SW1573 | | | | | | | | H2030 | | | | | |
|---|---|---|---|---|---|---|---|---|---|---|---|---|---|---|---|---|
| Ex. | | | Percent Degradation at Indicated Concentration (μM)*** | | | | | | | | Percent Degradation at Indicated Concentration (μM)*** | | | | | |
| No. | $DC_{50}$* | $D_{Max}$** | 10 | 3 | 1 | 0.3 | 0.1 | 0.03 | 0.01 | $DC_{50}$* | $D_{Max}$** | 10 | 3 | 1 | 0.3 | 0.1 | 0.03 | 0.01 |
| 27 | nd | nd | nd | nd | nd | nd | nd | nd | nd | nd | C | nd | C | C | C | nd | nd | nd |
| 311 | nd | nd | nd | nd | nd | nd | nd | nd | nd | nd | C | nd | C | C | C | nd | nd | nd |
| 184 | nd | nd | nd | nd | nd | nd | nd | nd | nd | nd | C | nd | C | C | C | nd | nd | nd |
| 182 | nd | nd | nd | nd | nd | nd | nd | nd | nd | nd | C | nd | C | C | C | nd | nd | nd |
| 116 | nd | nd | nd | nd | nd | nd | nd | nd | nd | nd | C | nd | C | C | C | nd | nd | nd |
| 115 | nd | nd | nd | nd | nd | nd | nd | nd | nd | nd | C | nd | C | C | C | nd | nd | nd |
| 73 | nd | nd | nd | nd | nd | nd | nd | nd | nd | nd | C | nd | C | C | C | nd | nd | nd |
| 273 | nd | nd | nd | nd | nd | nd | nd | nd | nd | nd | C | nd | C | C | C | nd | nd | nd |
| 271 | nd | nd | nd | nd | nd | nd | nd | nd | nd | nd | C | nd | C | C | C | nd | nd | nd |
| 474 | nd | nd | nd | nd | nd | nd | nd | nd | nd | nd | C | nd | C | C | C | nd | nd | nd |
| 473 | B | B | B | B | B | B | C | C | nd | B | C | C | C | C | C | C | C | nd |
| 168 | nd | nd | nd | nd | nd | nd | nd | nd | nd | nd | C | nd | C | C | C | nd | nd | nd |
| 113 | nd | nd | nd | nd | nd | nd | nd | nd | nd | nd | C | nd | C | C | C | nd | nd | nd |
| 111 | nd | nd | nd | nd | nd | nd | nd | nd | nd | nd | C | nd | C | C | C | nd | nd | nd |
| 109 | nd | nd | nd | nd | nd | nd | nd | nd | nd | nd | C | nd | C | C | C | nd | nd | nd |
| 108 | nd | nd | nd | nd | nd | nd | nd | nd | nd | nd | C | nd | C | C | C | nd | nd | nd |
| 107 | nd | nd | nd | nd | nd | nd | nd | nd | nd | nd | C | nd | C | C | C | nd | nd | nd |
| 95 | nd | nd | nd | nd | nd | nd | nd | nd | nd | nd | C | nd | C | C | C | nd | nd | nd |
| 304 | nd | nd | nd | nd | nd | nd | nd | nd | nd | nd | C | nd | C | C | C | nd | nd | nd |
| 170 | nd | nd | nd | nd | nd | nd | nd | nd | nd | nd | C | nd | C | C | C | nd | nd | nd |
| 93 | nd | nd | nd | nd | nd | nd | nd | nd | nd | nd | C | nd | C | C | C | nd | nd | nd |
| 75 | nd | nd | nd | nd | nd | nd | nd | nd | nd | nd | C | nd | C | C | C | nd | nd | nd |
| 69 | nd | nd | nd | nd | nd | nd | nd | nd | nd | nd | C | nd | C | C | C | nd | nd | nd |
| 302 | nd | nd | nd | nd | nd | nd | nd | nd | nd | nd | C | nd | C | C | C | nd | nd | nd |
| 249 | nd | nd | nd | nd | nd | nd | nd | nd | nd | nd | C | nd | C | C | C | nd | nd | nd |
| 391 | nd | nd | nd | nd | nd | nd | nd | nd | nd | nd | C | nd | C | C | C | nd | nd | nd |
| 89 | nd | nd | nd | nd | nd | nd | nd | nd | nd | nd | C | nd | C | C | C | nd | nd | nd |
| 303 | nd | nd | nd | nd | nd | nd | nd | nd | nd | nd | C | nd | C | C | C | nd | nd | nd |
| 396 | nd | nd | nd | nd | nd | nd | nd | nd | nd | nd | C | nd | C | C | C | nd | nd | nd |
| 269 | nd | nd | nd | nd | nd | nd | nd | nd | nd | nd | C | nd | C | C | C | nd | nd | nd |
| 268 | nd | nd | nd | nd | nd | nd | nd | nd | nd | nd | C | nd | C | C | C | nd | nd | nd |
| 214 | nd | nd | nd | nd | nd | nd | nd | nd | nd | nd | C | nd | C | C | C | nd | nd | nd |
| 213 | nd | nd | nd | nd | nd | nd | nd | nd | nd | nd | C | nd | C | C | C | nd | nd | nd |
| 212 | nd | nd | nd | nd | nd | nd | nd | nd | nd | nd | C | nd | C | C | C | nd | nd | nd |
| 211 | nd | nd | nd | nd | nd | nd | nd | nd | nd | nd | C | nd | C | C | C | nd | nd | nd |
| 210 | nd | nd | nd | nd | nd | nd | nd | nd | nd | nd | C | nd | C | C | C | nd | nd | nd |
| 209 | nd | nd | nd | nd | nd | nd | nd | nd | nd | nd | C | nd | C | C | C | nd | nd | nd |
| 199 | nd | nd | nd | nd | nd | nd | nd | nd | nd | nd | C | nd | C | C | C | nd | nd | nd |
| 208 | nd | nd | nd | nd | nd | nd | nd | nd | nd | nd | C | nd | C | C | C | nd | nd | nd |
| 207 | nd | nd | nd | nd | nd | nd | nd | nd | nd | nd | C | nd | C | C | C | nd | nd | nd |
| 206 | nd | nd | nd | nd | nd | nd | nd | nd | nd | nd | C | nd | C | C | C | nd | nd | nd |
| 205 | nd | nd | nd | nd | nd | nd | nd | nd | nd | nd | C | nd | C | C | C | nd | nd | nd |
| 204 | nd | nd | nd | nd | nd | nd | nd | nd | nd | nd | C | nd | C | C | C | nd | nd | nd |
| 202 | nd | nd | nd | nd | nd | nd | nd | nd | nd | nd | C | nd | C | C | C | nd | nd | nd |
| 201 | nd | nd | nd | nd | nd | nd | nd | nd | nd | nd | C | nd | C | C | C | nd | nd | nd |
| 375 | nd | nd | nd | nd | nd | nd | nd | nd | nd | nd | C | nd | C | C | C | nd | nd | nd |
| 174 | nd | nd | nd | nd | nd | nd | nd | nd | nd | nd | C | nd | C | C | C | nd | nd | nd |
| 366 | nd | nd | nd | nd | nd | nd | nd | nd | nd | nd | C | nd | C | C | C | nd | nd | nd |
| 373 | nd | nd | nd | nd | nd | nd | nd | nd | nd | nd | C | nd | C | C | C | nd | nd | nd |
| 200 | nd | nd | nd | nd | nd | nd | nd | nd | nd | nd | C | nd | C | C | C | nd | nd | nd |
| 172 | nd | nd | nd | nd | nd | nd | nd | nd | nd | nd | C | nd | C | C | C | nd | nd | nd |
| 483 | nd | nd | nd | nd | nd | nd | nd | nd | nd | nd | C | nd | C | C | C | nd | nd | nd |
| 484 | nd | nd | nd | nd | nd | nd | nd | nd | nd | nd | C | nd | C | C | C | nd | nd | nd |
| 482 | nd | nd | nd | nd | nd | nd | nd | nd | nd | nd | C | nd | C | C | C | nd | nd | nd |
| 337 | nd | nd | nd | nd | nd | nd | nd | nd | nd | nd | C | nd | C | C | C | nd | nd | nd |
| 198 | nd | nd | nd | nd | nd | nd | nd | nd | nd | nd | C | nd | C | C | C | nd | nd | nd |
| 196 | C | C | nd | C | C | C | C | C | nd | C | C | nd | C | C | C | C | C | nd |
| 195 | nd | nd | nd | nd | nd | nd | nd | nd | nd | nd | C | nd | C | C | C | nd | nd | nd |
| 468 | nd | nd | nd | nd | nd | nd | nd | nd | nd | nd | C | nd | C | C | C | nd | nd | nd |
| 363 | nd | nd | nd | nd | nd | nd | nd | nd | nd | nd | C | nd | C | C | C | nd | nd | nd |
| 338 | nd | nd | nd | nd | nd | nd | nd | nd | nd | nd | C | nd | C | C | C | nd | nd | nd |
| 341 | nd | nd | nd | nd | nd | nd | nd | nd | nd | nd | C | nd | C | C | C | nd | nd | nd |
| 467 | nd | nd | nd | nd | nd | nd | nd | nd | nd | nd | C | nd | C | C | C | nd | nd | nd |
| 68 | nd | nd | nd | nd | nd | nd | nd | nd | nd | nd | C | nd | C | C | C | nd | nd | nd |
| 344 | nd | nd | nd | nd | nd | nd | nd | nd | nd | nd | C | nd | C | C | C | nd | nd | nd |
| 343 | nd | nd | nd | nd | nd | nd | nd | nd | nd | nd | C | nd | C | C | C | nd | nd | nd |
| 342 | nd | nd | nd | nd | nd | nd | nd | nd | nd | nd | C | nd | C | C | C | nd | nd | nd |
| 346 | nd | nd | nd | nd | nd | nd | nd | nd | nd | nd | C | nd | C | C | C | nd | nd | nd |
| 345 | nd | nd | nd | nd | nd | nd | nd | nd | nd | nd | C | nd | C | C | C | nd | nd | nd |
| 193 | nd | nd | nd | nd | nd | nd | nd | nd | nd | nd | C | nd | C | C | C | nd | nd | nd |
| 67 | nd | nd | nd | nd | nd | nd | nd | nd | nd | nd | C | nd | C | C | C | nd | nd | nd |

TABLE 14-continued

Target Proteion Degradation via Exemplary Bifunctional Compounds from Tables 6, 8, 10, and 12.

| | | SW1573 | | | | | | | | | H2030 | | | | | | |
|---|---|---|---|---|---|---|---|---|---|---|---|---|---|---|---|---|---|
| | | | Percent Degradation at Indicated Concentration (µM)*** | | | | | | | | | Percent Degradation at Indicated Concentration (µM)*** | | | | | |
| Ex. No. | DC$_{50}$* | D$_{Max}$** | 10 | 3 | 1 | 0.3 | 0.1 | 0.03 | 0.01 | DC$_{50}$* | D$_{Max}$** | 10 | 3 | 1 | 0.3 | 0.1 | 0.03 | 0.01 |
| 66 | nd | nd | nd | nd | nd | nd | nd | nd | nd | nd | C | nd | C | C | C | nd | nd | nd |
| 340 | nd | nd | nd | nd | nd | nd | nd | nd | nd | nd | C | nd | C | C | C | nd | nd | nd |
| 339 | nd | nd | nd | nd | nd | nd | nd | nd | nd | nd | C | nd | C | C | C | nd | nd | nd |
| 65 | nd | nd | nd | nd | nd | nd | nd | nd | nd | nd | C | nd | C | C | C | nd | nd | nd |
| 64 | nd | nd | nd | nd | nd | nd | nd | nd | nd | nd | C | nd | C | C | C | nd | nd | nd |
| 62 | nd | nd | nd | nd | nd | nd | nd | nd | nd | nd | C | nd | C | C | C | nd | nd | nd |
| 60 | nd | nd | nd | nd | nd | nd | nd | nd | nd | nd | C | nd | C | C | C | nd | nd | nd |
| 58 | nd | nd | nd | nd | nd | nd | nd | nd | nd | nd | C | nd | C | C | C | nd | nd | nd |
| 57 | nd | nd | nd | nd | nd | nd | nd | nd | nd | nd | C | nd | C | C | C | nd | nd | nd |
| 56 | nd | nd | nd | nd | nd | nd | nd | nd | nd | nd | C | nd | C | C | C | nd | nd | nd |
| 197 | nd | nd | nd | nd | nd | nd | nd | nd | nd | nd | C | nd | C | C | C | nd | nd | nd |
| 194 | nd | nd | nd | nd | nd | nd | nd | nd | nd | nd | C | nd | C | C | C | nd | nd | nd |
| 63 | nd | nd | nd | nd | nd | nd | nd | nd | nd | nd | C | nd | nd | C | C | C | nd | nd |
| 61 | nd | nd | nd | nd | nd | nd | nd | nd | nd | nd | C | nd | nd | C | C | C | nd | nd |
| 59 | nd | nd | nd | nd | nd | nd | nd | nd | nd | nd | C | nd | nd | C | C | C | nd | nd |
| 192 | nd | nd | nd | nd | nd | nd | nd | nd | nd | nd | C | nd | nd | C | C | C | nd | nd |
| 335 | nd | nd | nd | nd | nd | nd | nd | nd | nd | nd | C | nd | C | C | C | nd | nd | nd |
| 334 | nd | nd | nd | nd | nd | nd | nd | nd | nd | nd | C | nd | C | C | C | nd | nd | nd |
| 191 | nd | nd | nd | nd | nd | nd | nd | nd | nd | nd | C | nd | nd | C | C | C | nd | nd |
| 55 | nd | nd | nd | nd | nd | nd | nd | nd | nd | nd | C | nd | nd | C | C | C | nd | nd |
| 336 | nd | nd | nd | nd | nd | nd | nd | nd | nd | nd | C | nd | C | C | C | nd | nd | nd |
| 54 | nd | nd | nd | nd | nd | nd | nd | nd | nd | nd | C | nd | C | C | C | nd | nd | nd |
| 333 | nd | nd | nd | nd | nd | nd | nd | nd | nd | nd | C | nd | C | C | C | nd | nd | nd |
| 332 | nd | nd | nd | nd | nd | nd | nd | nd | nd | nd | C | nd | C | C | C | nd | nd | nd |
| 331 | nd | nd | nd | nd | nd | nd | nd | nd | nd | nd | C | nd | C | C | C | nd | nd | nd |
| 330 | nd | nd | nd | nd | nd | nd | nd | nd | nd | nd | C | nd | C | C | C | nd | nd | nd |
| 44 | nd | nd | nd | nd | nd | nd | nd | nd | nd | nd | C | nd | C | C | C | nd | nd | nd |
| 189 | nd | nd | nd | nd | nd | nd | nd | nd | nd | nd | C | nd | C | C | C | nd | nd | nd |
| 53 | nd | nd | nd | nd | nd | nd | nd | nd | nd | nd | C | nd | C | C | C | nd | nd | nd |
| 52 | nd | nd | nd | nd | nd | nd | nd | nd | nd | nd | C | nd | C | C | C | nd | nd | nd |
| 51 | nd | nd | nd | nd | nd | nd | nd | nd | nd | nd | C | nd | C | C | C | nd | nd | nd |
| 50 | nd | nd | nd | nd | nd | nd | nd | nd | nd | nd | C | nd | C | C | C | nd | nd | nd |
| 49 | nd | nd | nd | nd | nd | nd | nd | nd | nd | nd | C | nd | C | C | C | nd | nd | nd |
| 48 | nd | nd | nd | nd | nd | nd | nd | nd | nd | nd | C | nd | C | C | C | nd | nd | nd |
| 46 | nd | nd | nd | nd | nd | nd | nd | nd | nd | nd | C | nd | C | C | C | nd | nd | nd |
| 45 | nd | nd | nd | nd | nd | nd | nd | nd | nd | nd | C | nd | C | C | C | nd | nd | nd |
| 43 | nd | nd | nd | nd | nd | nd | nd | nd | nd | nd | C | nd | C | C | C | nd | nd | nd |
| 42 | nd | nd | nd | nd | nd | nd | nd | nd | nd | nd | C | nd | C | C | C | nd | nd | nd |
| 187 | nd | nd | nd | nd | nd | nd | nd | nd | nd | nd | C | nd | C | C | C | nd | nd | nd |
| 186 | nd | nd | nd | nd | nd | nd | nd | nd | nd | nd | C | nd | C | C | C | nd | nd | nd |
| 47 | nd | nd | nd | nd | nd | nd | nd | nd | nd | nd | C | nd | C | C | C | nd | nd | nd |
| 41 | nd | nd | nd | nd | nd | nd | nd | nd | nd | nd | C | nd | C | C | C | nd | nd | nd |
| 190 | nd | nd | nd | nd | nd | nd | nd | nd | nd | nd | C | nd | C | C | C | nd | nd | nd |
| 188 | nd | nd | nd | nd | nd | nd | nd | nd | nd | nd | C | nd | C | C | C | nd | nd | nd |

*DC50 (nM) C ≥ 1000; 100 ≤ B < 1000; A < 100
**D$_{Max}$ (%): C ≤ 35; 35 < B < 70; A ≥ 70
***Percent Degradation: C ≤ 35; 35 < B < 70; A ≥ 70.
nd: not determined A novel bifunctional molecule, which contains a KRas recruiting moiety and an E3 Ligase recruiting moiety (e.g., CLM, VLM, ILM, or MLM), through PROTAC technology is described. The bifunctional molecules of the present disclosure actively degrades KRas, leading to robust cellular proliferation suppression and apoptosis induction. PROTAC mediated protein degradation provides a promising strategy in targeting the "undruggable" pathological proteins, such as KRas, by traditional approaches.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equiva-

REFERENCES

Collins M A and Pasca di Magliano M, Kras as a key oncogene and therapeutic target in pancreatic cancer. Front Physiol. 2014 Jan. 21; 4:407.

Wood K, Hensing T, Malik R, Salgia R. Prognostic and Predictive Value in KRAS in Non-Small-Cell Lung Cancer: A Review. JAMA Oncol. 2016 Jun. 1; 2(6):805-12.

Knickelbein K, Zhang L. Mutant KRAS as a critical determinant of the therapeutic response of colorectal cancer. Genes Dis. 2015 March; 2(1):4-12.

Prior I A1, Lewis P D, Mattos C. A comprehensive survey of Ras mutations in cancer. Cancer Res. 2012 May 15; 72(10):2457-67.

Ostrem J M, Shokat K M. Direct small-molecule inhibitors of KRAS: from structural insights to mechanism-based design. Nat Rev Drug Discov. 2016 November; 15(11): 771-785.

Ma Y, Gu Y, Zhang Q, Han Y, Yu S, Lu Z, Chen J. Targeted degradation of KRAS by an engineered ubiquitin ligase suppresses pancreatic cancer cell growth in vitro and in vivo. Mol Cancer Ther. 2013 March; 12(3):286-94.

Ross S J, Revenko A S, Hanson L L, Ellston R, Staniszewska A, Whalley N, Pandey S K, Revill M, Rooney C, Buckett L K, Klein S K, Hudson K, Monia B P, Zinda M, Blakey D C, Lyne P D, Macleod A R. Targeting KRAS-dependent tumors with AZD4785, a high-affinity therapeutic antisense oligonucleotide inhibitor of KRAS. Sci Transl Med. 2017 Jun. 14; 9(394).

Yuan T L, Fellmann C, Lee C S, Ritchie C D, Thapar V, Lee L C, Hsu D J, Grace D, Carver J O, Zuber J, Luo J, McCormick F, Lowe S W. Development of siRNA payloads to target KRAS-mutant cancer. Cancer Discov. 2014 October; 4(10): 1182-1197.

What is claimed is:

1. A bifunctional compound having the chemical structure:

PTM-L-ULM, or a pharmaceutically acceptable salt, enantiomer, stereoisomer, solvate, or polymorph thereof, wherein:

(a) the ULM is a Von Hippel-Lindau (VHL) ligase-binding moiety (VLM) with a chemical structure represented by:

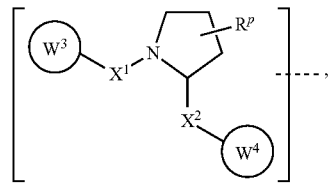

wherein:

$X^1$, and $X^2$ are each independently selected from the group of a bond, O, $NR^{Y3}$, $CR^{Y3}R^{Y4}$, C=O, C=S, SO, and $SO_2$;

$R^{Y3}$, and $R^{Y4}$ are each independently selected from the group of H, linear or branched $C_{1-6}$ alkyl, optionally substituted by 1 or more halo, and $C_{1-6}$ alkoxyl optionally substituted by 0-3 $R^P$ groups;

$R^P$ is 0, 1, 2, or 3 groups independently selected from the group H, halo, —OH, $C_{1-3}$ alkyl, and C=O;

$W^3$ is selected from the group of an optionally substituted T, an optionally substituted -T-N($R^{1a}R^{1b}$)$X^3$, an optionally substituted -T-N($R^{1a}R^{1b}$), an optionally substituted -T-Aryl, an optionally substituted -T-Heteroaryl, an optionally substituted T-biheteroaryl, an optionally substituted -T- heterocyclyl, an optionally substituted -T-bieterocyclyl, an optionally substituted —$NR^1$-T-Aryl, an optionally substituted —$NR^1$-T-Heteroaryl or an optionally substituted —$NR^1$-T- heterocyclyl;

$X^3$ is C=O, $R^1$, $R^{1a}$, or $R^{1b}$;

each of $R^1$, $R^{1a}$, and $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}$SO$_2$, N($R^{Y3}R^{Y4}$)C=O, N($R^{Y3}R^{Y4}$)C=S, N($R^{Y3}R^{Y4}$)SO, and N($R^{Y3}R^{Y4}$)SO$_2$;

T is selected from the group of an optionally substituted alkyl, —$(CH_2)_n$— group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocyclyl, or —OH groups or an amino acid side chain optionally substituted; and n is 0 to 6, $W^4$ is

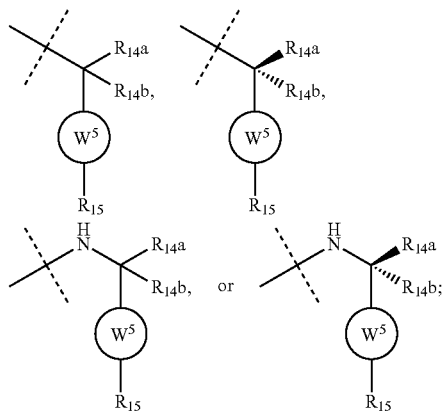

o is 0, 1, 2, 3, or 4;

$R_{14a}$, and $R_{14b}$, are each independently selected from the group of H, haloalkyl, or optionally substituted alkyl;

$W^5$ is selected from the group of an optionally substituted phenyl or an optionally substituted 5-10 membered heteroaryl;

$R_{15}$ is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl; and the dashed line indicates the site of attachment of the ULM to the linker group (L) or the PTM;

(b) the PTM is a small molecule comprising a Kirsten rat sarcoma protein (KRas) targeting moiety represented by the chemical structure:

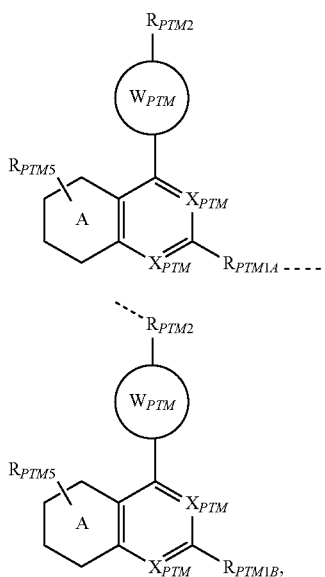

or wherein:

is an aryl, heteroaryl, cycloalkyl, or heterocycloalkyl;

$X_{PTM}$ is C or N;

$W_{PTM}$ is chosen from the group consisting of optionally substituted C3-C6 cycloalkyl, optionally substituted C3-C6 heteroalkyl, optionally substituted C3-C6 heterocycloalkyl, optionally substituted aryl, and optionally substituted heteroaryl;

$R_{PTM1A}$ is $NR_{PTM9}R_{PTM10}$, $OR_{PTM9}R_{PTM10}$, H, optionally substituted alkyl, optionally substituted alkoxy, optionally substituted C3-C6 cycloalkyl, optionally substituted O—(C3-C6 cycloalkyl), optionally substituted —O—$C_{1-4}$ alkyl-$C_{3-6}$cycloalkyl, optionally substituted C3-C6 heteroalkyl, optionally substituted O—(C3-C6 heteroalkyl), optionally substituted O—$C_{1-4}$ alkyl-$C_{3-6}$ heteroalkyl, optionally substituted O—$C_{1-4}$ alkyl-$C_{3-6}$ heterocycloalkyl, optionally substituted aryl, optionally substituted O-aryl, optionally substituted heteroaryl, optionally substituted O-heteroaryl, optionally substituted

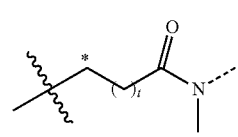

optionally substituted

PTM-I

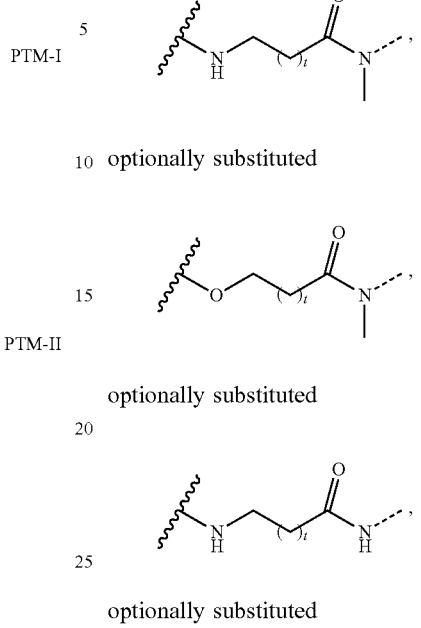

PTM-II optionally substituted

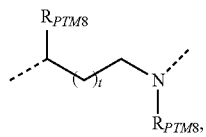

optionally substituted

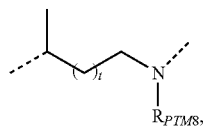

optionally substituted

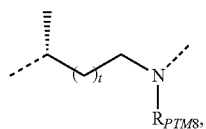

optionally substituted

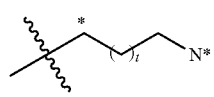

optionally substituted

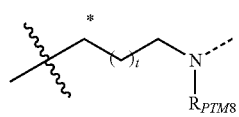

optionally substituted

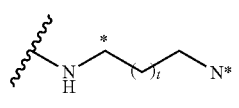

optionally substituted

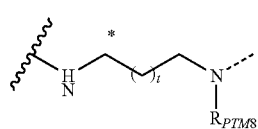

optionally substituted

or optionally substituted

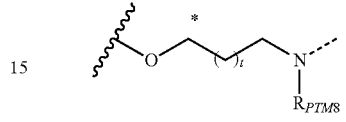

wherein N* is a N atom of a heterocycloalkyl of the linker (L);

$R_{PTM1B}$ is $NR_{PTM9}R_{PTM10}$, $OR_{PTM9}R_{PTM10}$, H, optionally substituted alkyl, optionally substituted O-alkyl, optionally substituted C3-C6 cycloalkyl, optionally substituted O—(C3-C6 cycloalkyl), optionally substituted -O-$C_{1-4}$ alkyl-$C_{3-6}$cycloalkyl, optionally substituted C3-C6 heteroalkyl, optionally substituted O—(C3-C6 heteroalkyl), optionally substituted O—$C_{1-4}$ alkyl-$C_{3-6}$ heteroalkyl, optionally substituted aryl, optionally substituted O-aryl, optionally substituted heteroaryl, optionally substituted O-heteroaryl, optionally substituted

optionally substituted

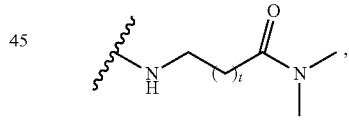

optionally substituted

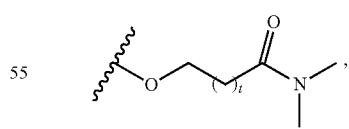

optionally substituted

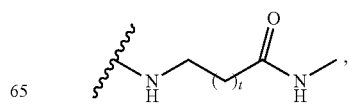

optionally substituted

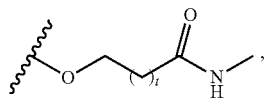

optionally substituted

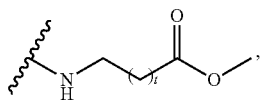

optionally substituted

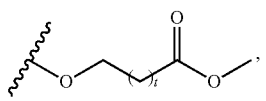

optionally substituted

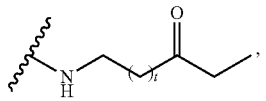

or optionally substituted

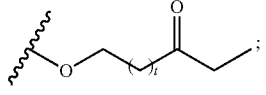

$R_{PTM9}$ and $R_{PTM10}$ are each independently H, optionally substituted C1-C6 alkyl, optionally substituted aliphatic amine, or optionally substituted aliphatic amide;

$R_{PTM2}$ is H, (C=O)$R_{PTM2'}$, or optionally substituted linear or branched alkyl;

$R_{PTM2'}$ is optionally substituted linear or branched alkyl, optionally substituted alkene, —N ($R_{PTM8}$)$_2$, or —C(OH)$_2$;

$R_{PTM3}$ is alkyl, alkoxy, phenyl, or napthalene, each independently substituted with OH, H, or halogen;

$R_{PTM4A}$ is OH, H, or halogen, optionally substituted linear or branched C1-C6 alkyl;

$R_{PTM4B}$ is OH, H, —CH$_2$CN, halogen, or optionally substituted linear or branched C1-C6 alkyl;

$R_{PTM5}$ is chosen from the group consisting of optionally substituted aryl, optionally substituted biaryl, optionally substituted heteroaryl, optionally substituted biheteroaryl, optionally substituted C3-C6 cycloalkyl, optionally substituted C3-C6 cycloheteroalkyl, halogen, H, optionally substituted linear or branched alkyl, OH, and alkoxy;

$R_{PTM8}$ is a H or an alkyl;

t is 0, 1, 2, 3, 4, 5, or 6; and the ⟋ indicates the site of attachment of at least one of the linker group (L) or the ULM; and (c) the L is a bond or a chemical linking moiety connecting the ULM and the PTM.

2. The bifunctional compound according to claim 1, wherein PTM is represented by:

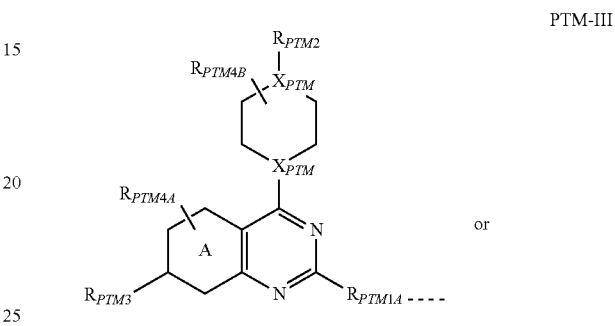

PTM-III or

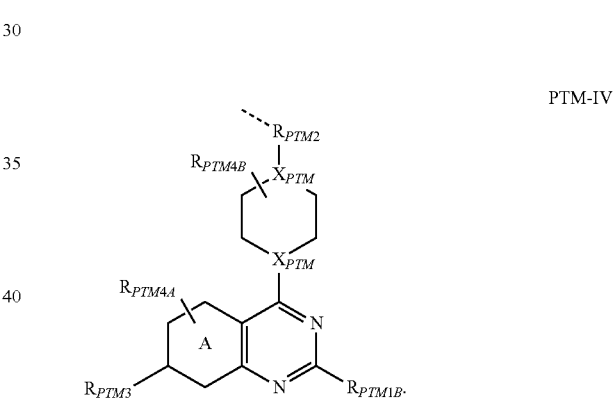

PTM-IV

3. The bifunctional compound according to claim 1, wherein the PTM is represented by:

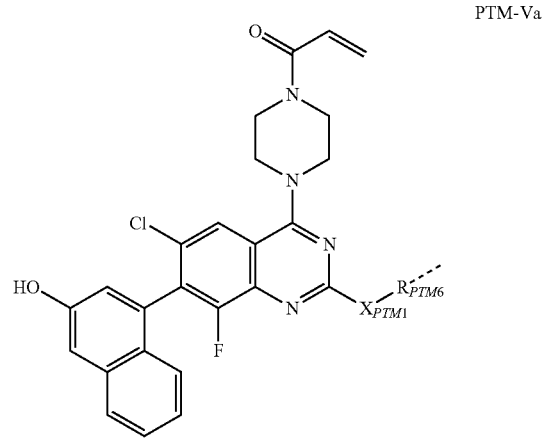

PTM-Va

-continued
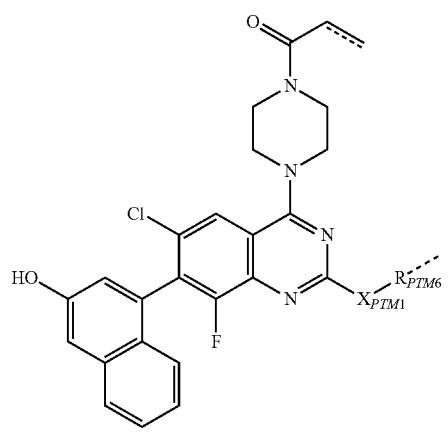
PTM-Vb
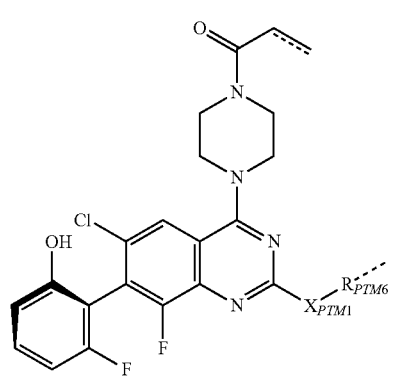
PTM-VI
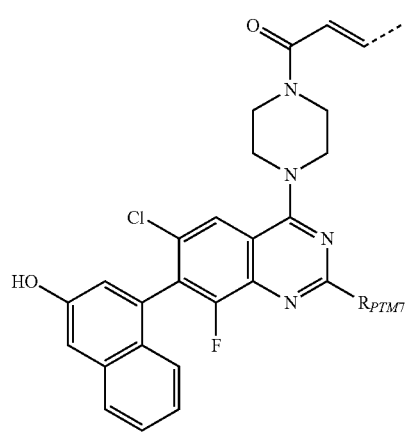
PTM-VIIa
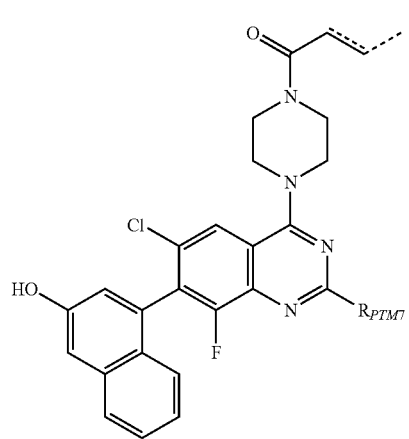
PTM-VIIb
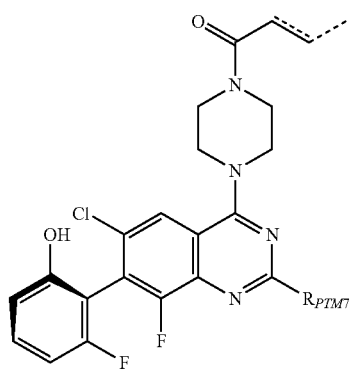
PTM-VIII
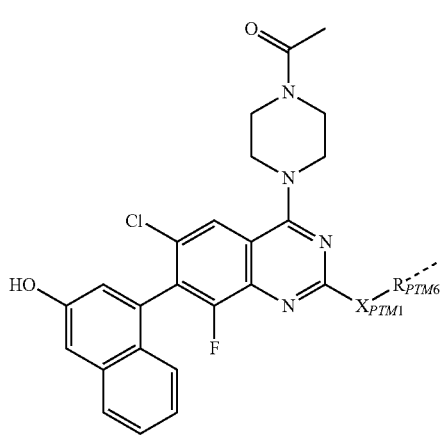
PTM-IXa
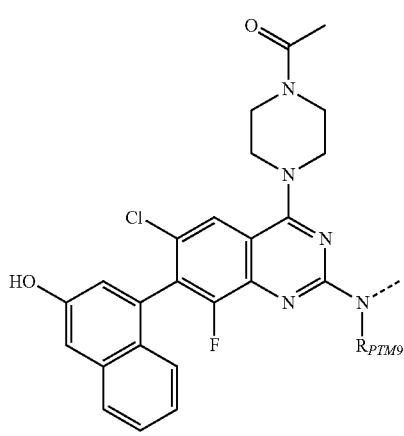
PTMI-Xb
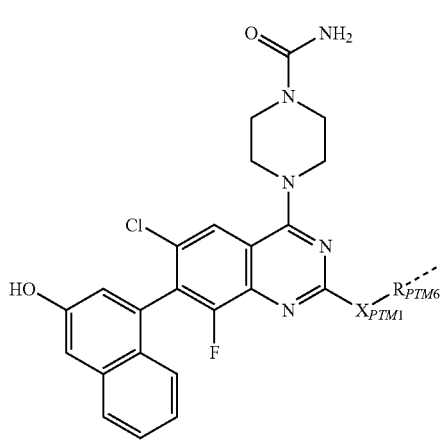
PTM-Xa -continued
PTM-Xb
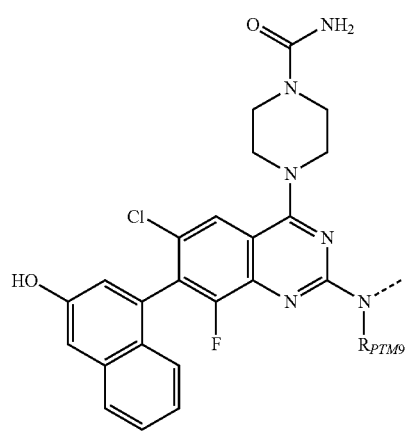
PTM-XI
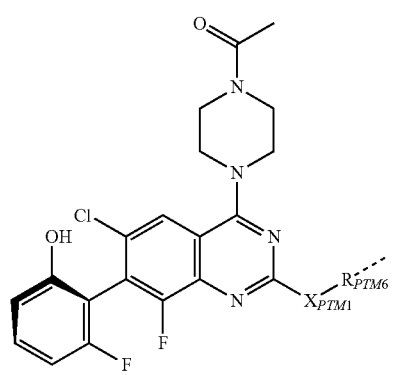
PTM-XII
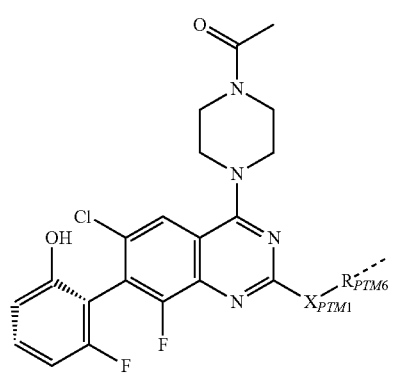
PTM-XIII
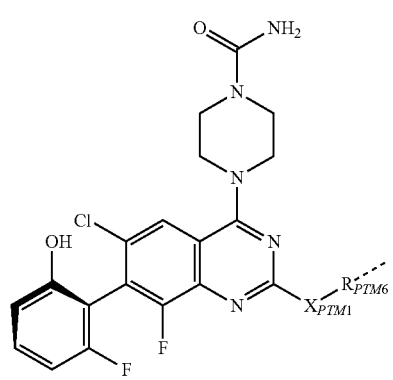
-continued
PTM-XIV
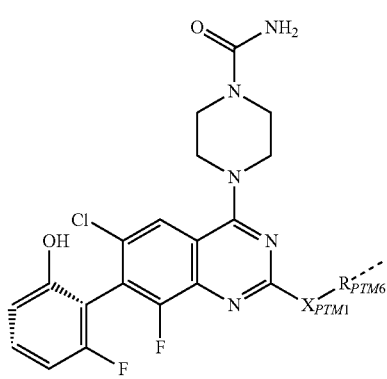
PTM-XV
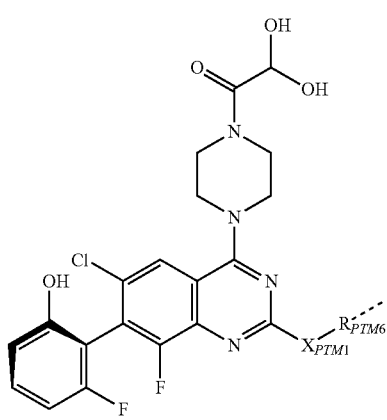
PTM-XVI
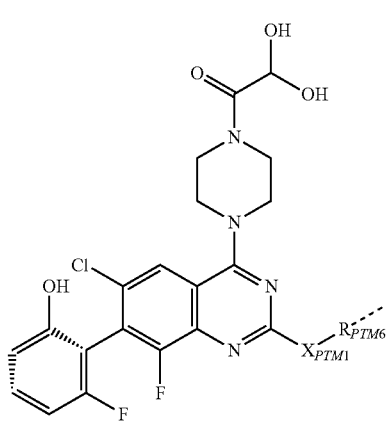
PTM-XVIIa
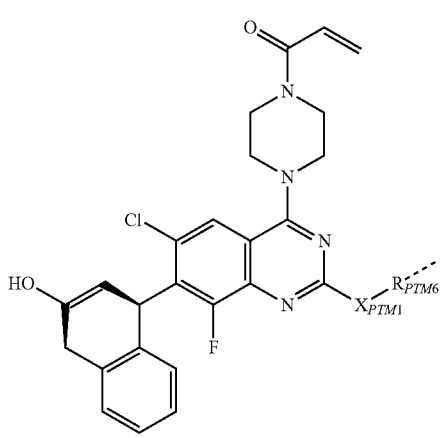

-continued
PTM-XVIIb
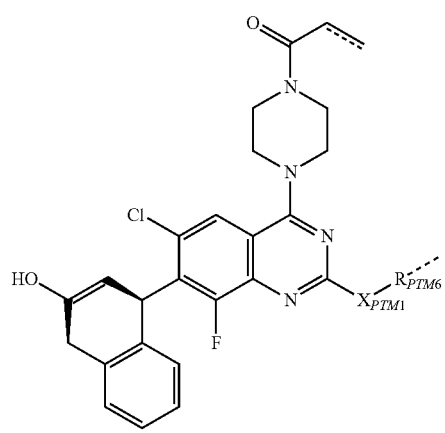
PTM-XVIII
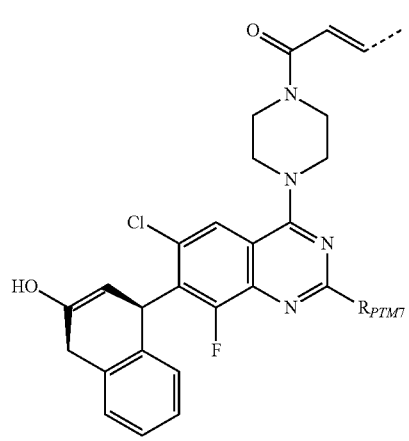
PTM-XIV
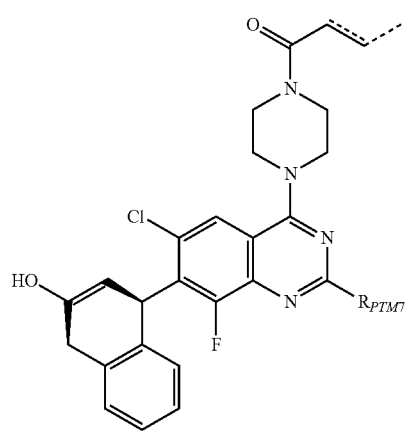
-continued
PTM-XV
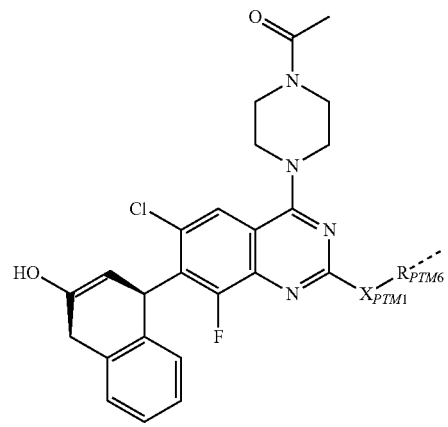
PTM-XVI
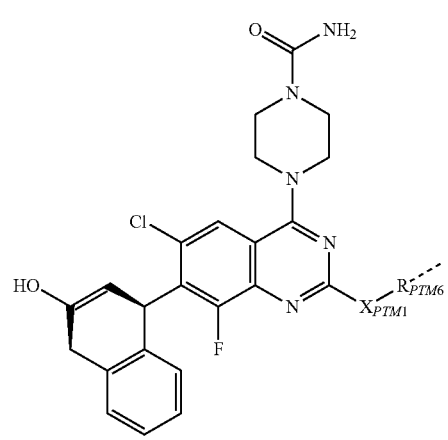
PTM-XVIIa
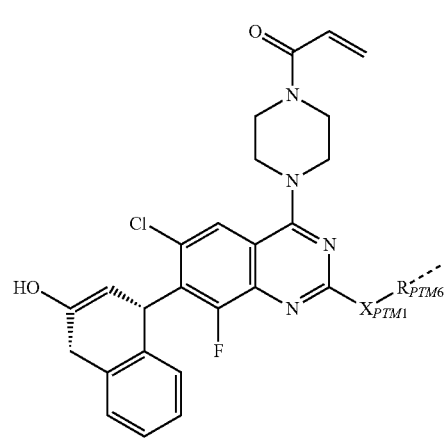

PTMXVIIb
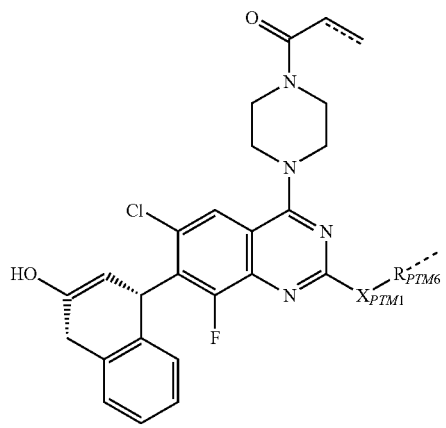
PTM-XVIII
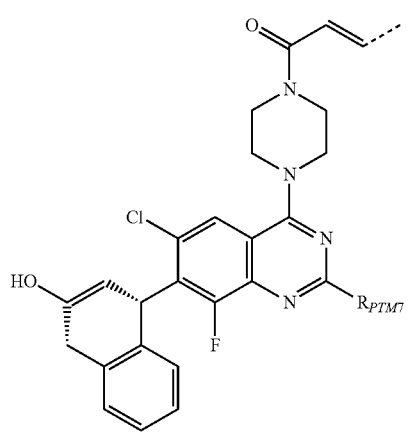
PTM-XIX
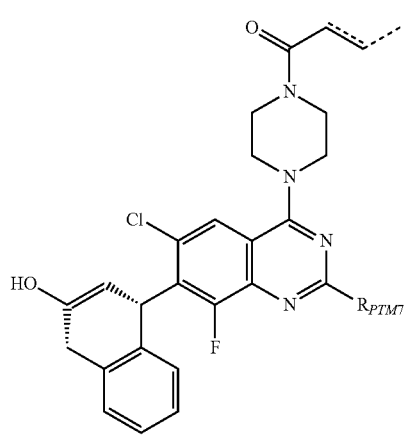
PTM-XX
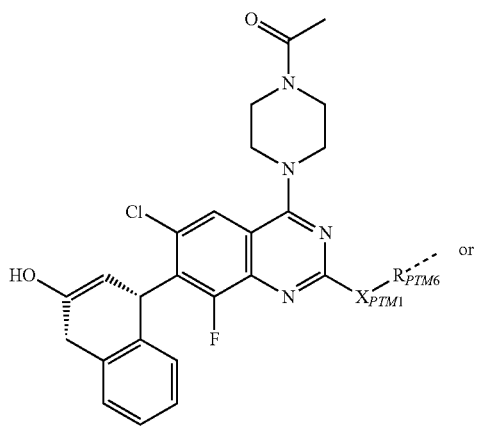
or
PTM-XXI
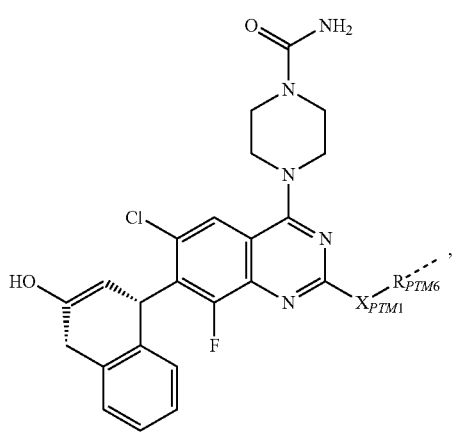
wherein:
$X_{PTM1}$ is NH or O;
$R_{PTM6}$ is aryl, heteroaryl,
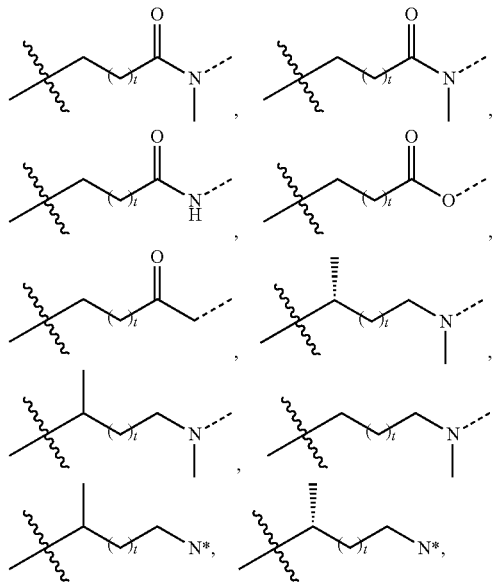

1917
-continued

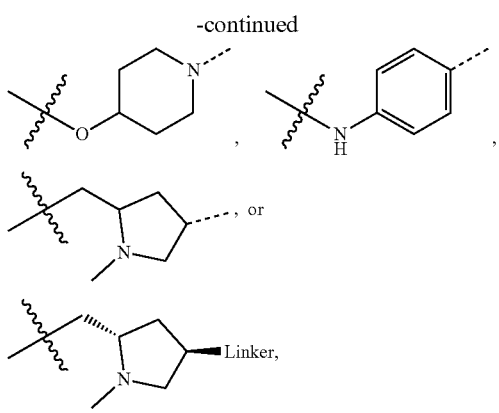

wherein N* a N atom of a heterocycloalkyl of the linker (L);
$R_{PTM7}$ is H, aryl, O-aryl, heteroaryl, O-heteroaryl,

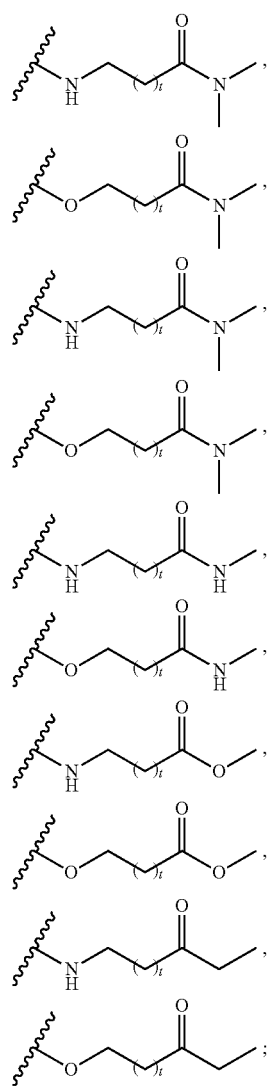

$R_{PTM9}$ is H, optionally substituted C1-C6 alkyl, optionally substituted aliphatic amine, optionally substituted aliphatic amide, optionally substituted

1918

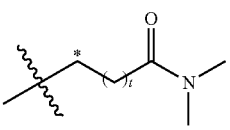

the ⫽ can be a single bond or a double bond; and the ⟋ indicates the site of attachment of at least one of the linker group (L) or the ULM.

4. The bifunctional compound according to claim 1, wherein the PTM is represented by chemical structure:

PTM-1

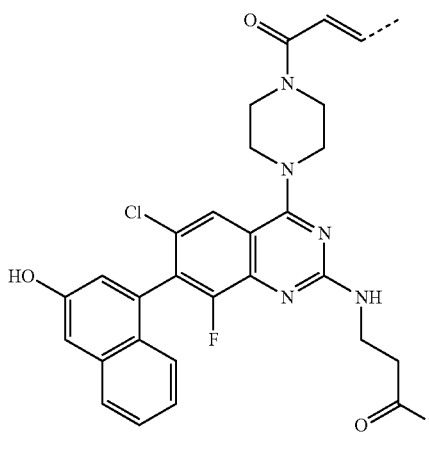

PTM-2

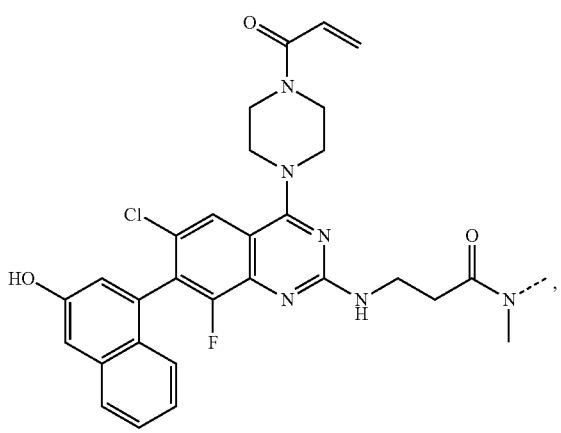

PTM-3

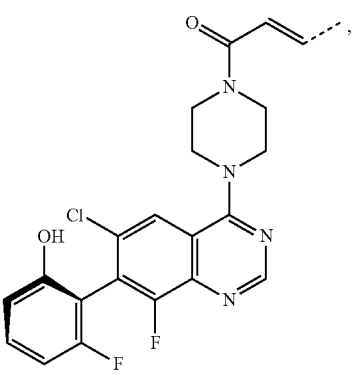

PTM-4
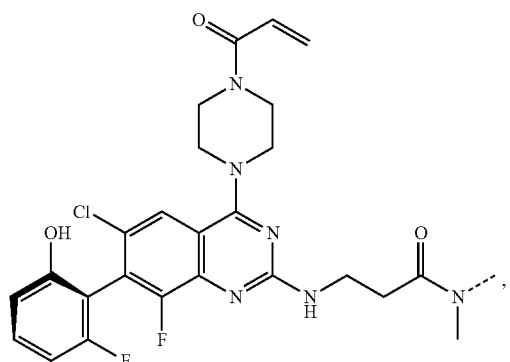
PTM-5
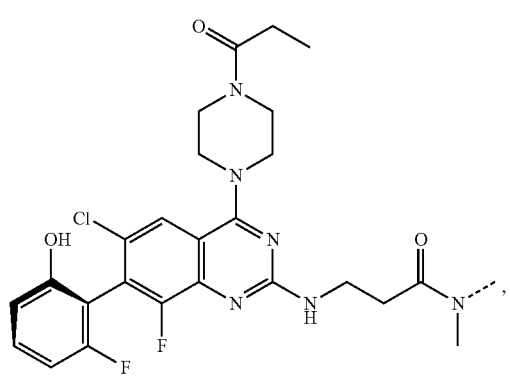
PTM-6
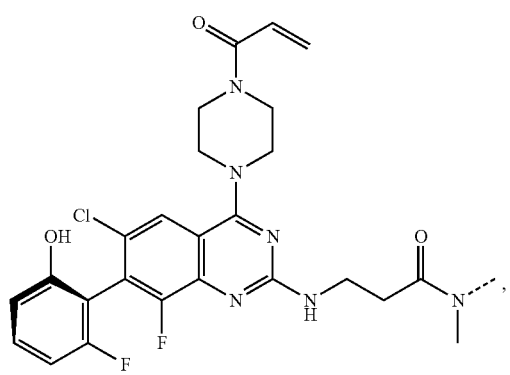
PTM-7
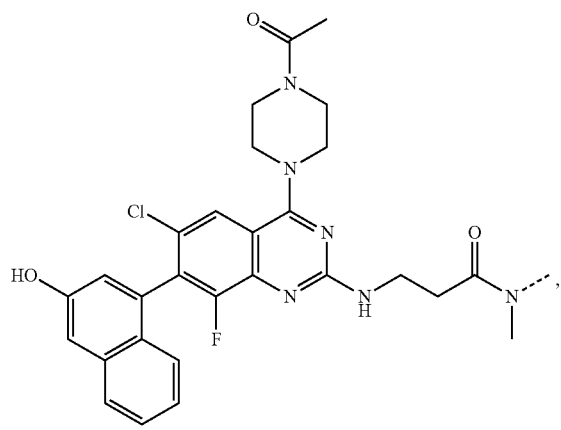
PTM-8
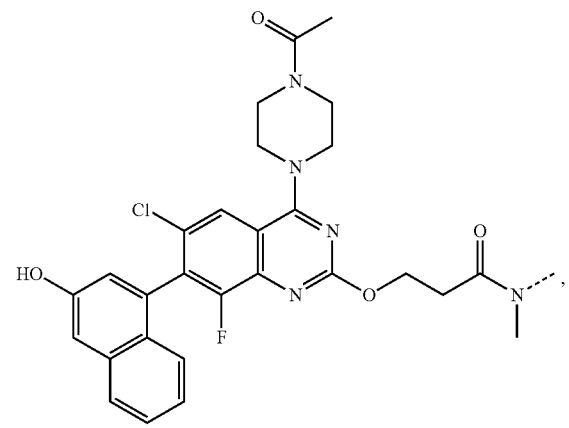
PTM-9
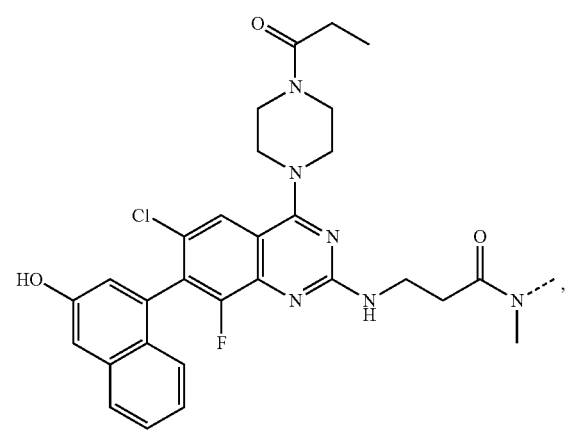
PTM-10
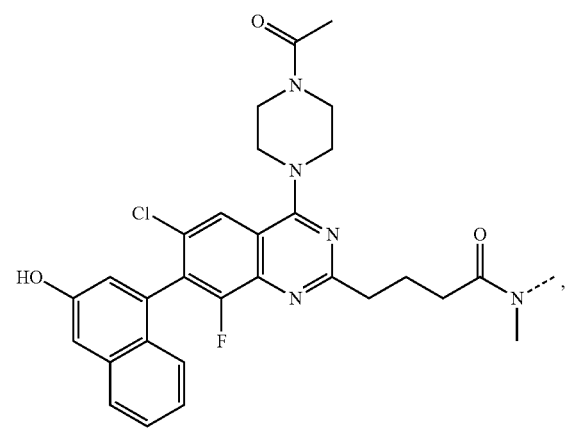

PTM-11
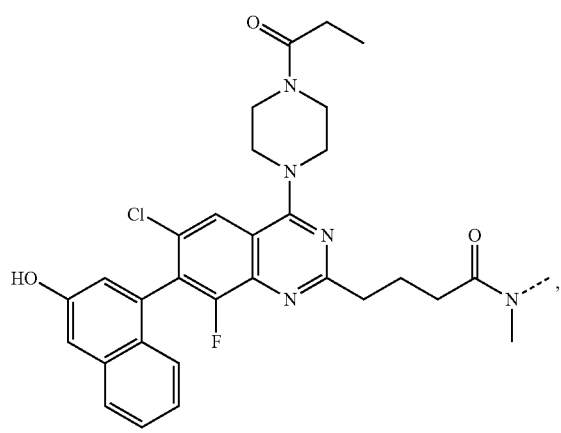
PTM-12
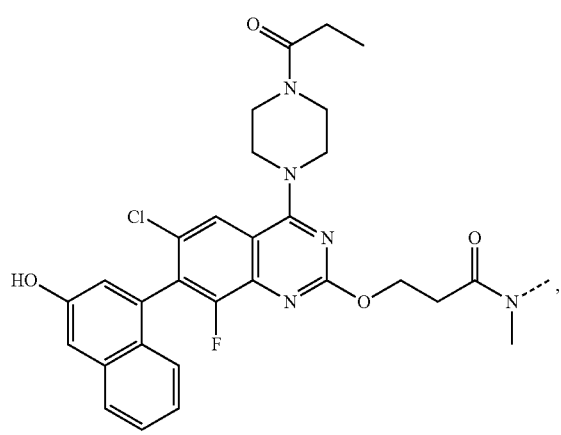
PTM-13
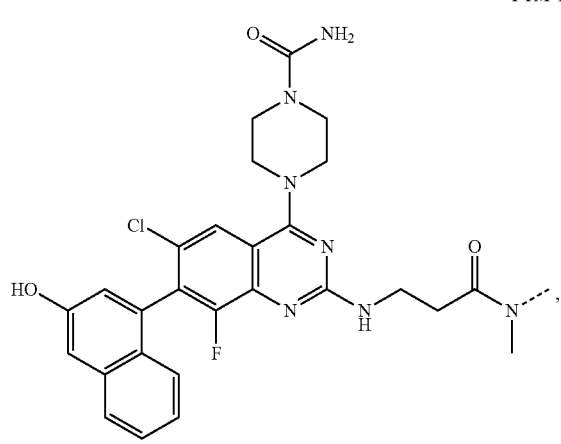
PTM-14
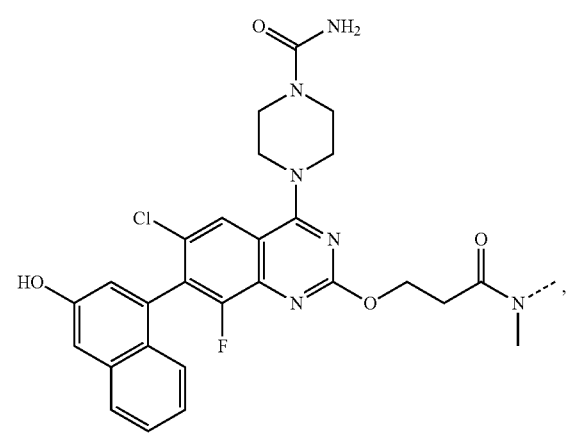
PTM-15
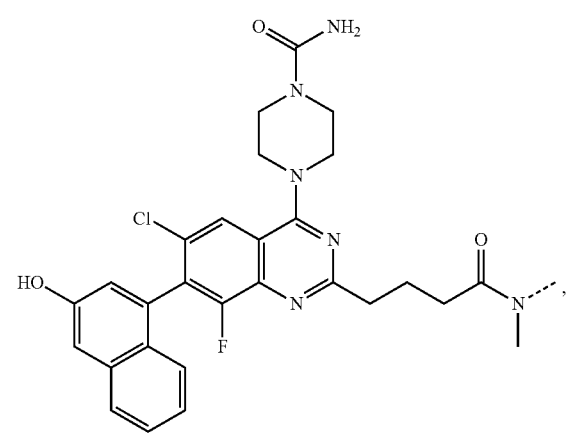
PTM-16
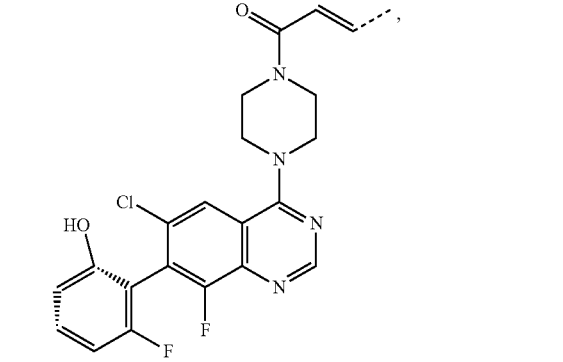
PTM-17
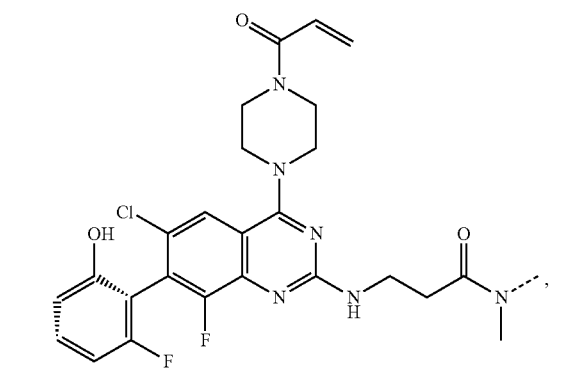

PTM-18
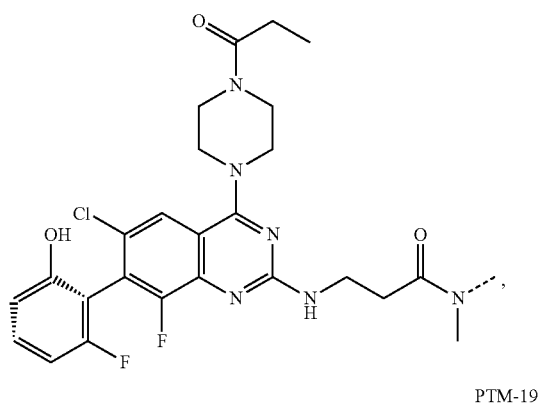
PTM-19
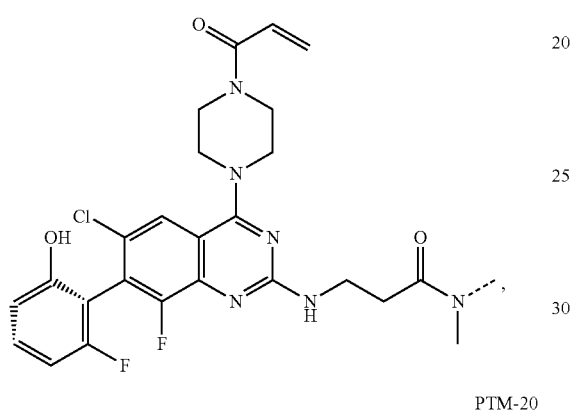
PTM-20
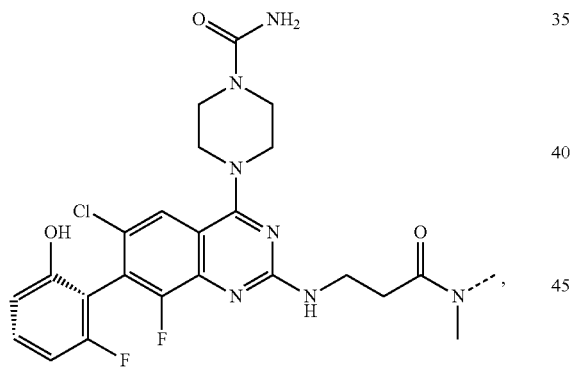
PTM-21
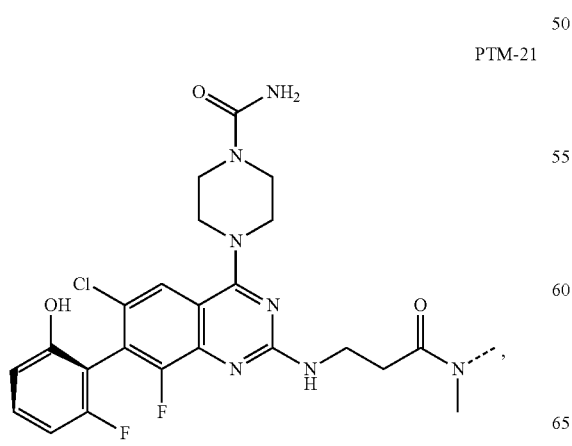
PTM-22
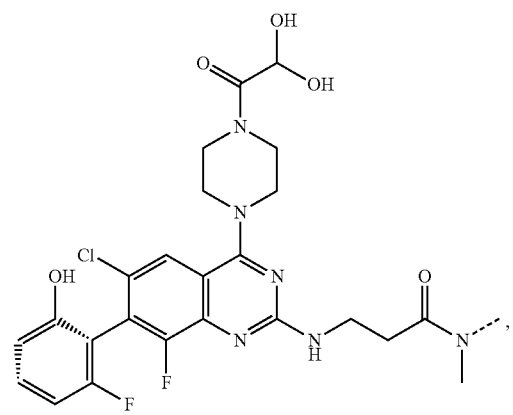
PTM-23
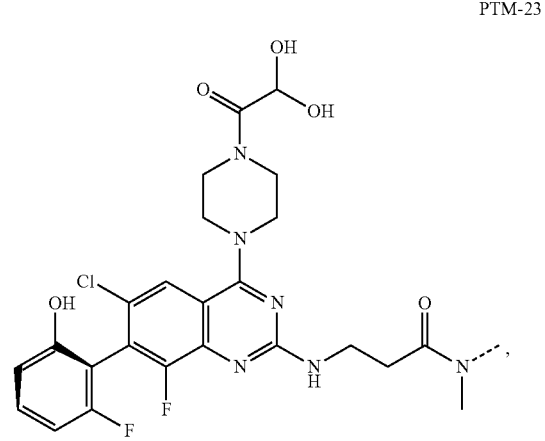
PTM-23
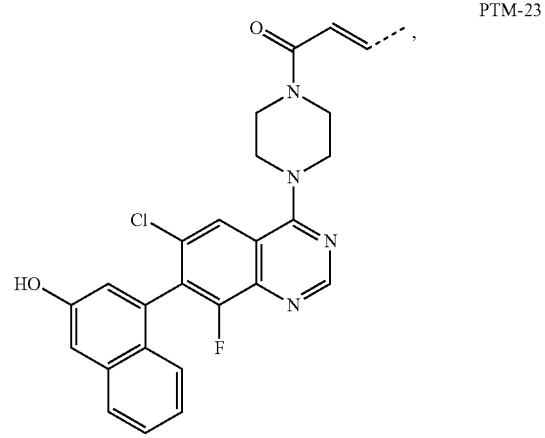

PTM-24
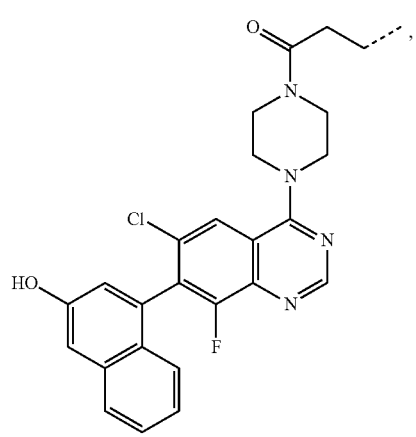
PTM-25
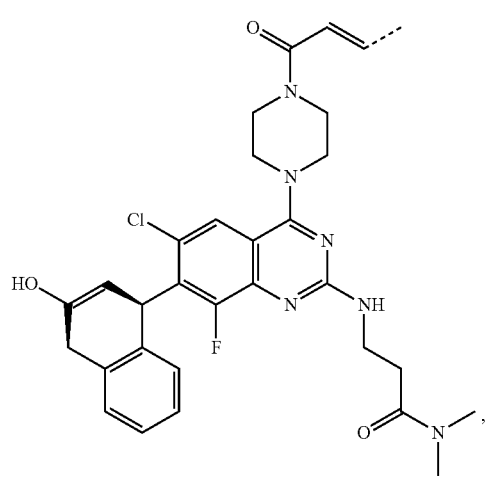
PTM-26
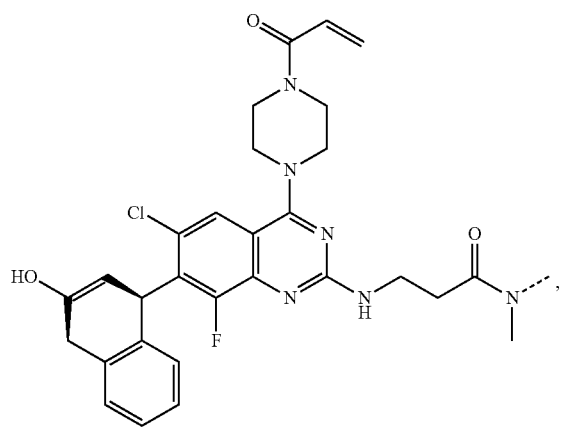
PTM-27
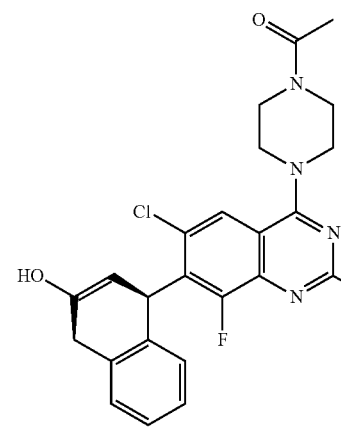
PTM-28
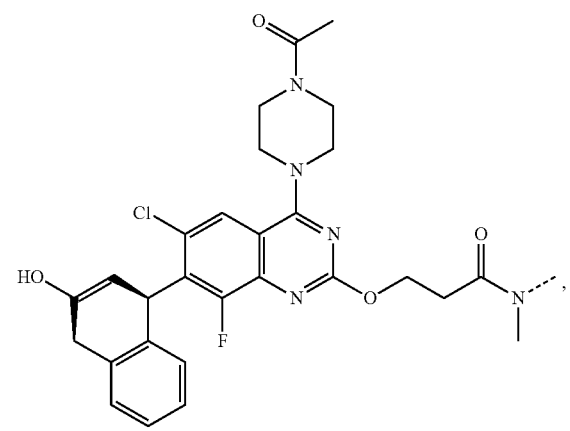
PTM-29
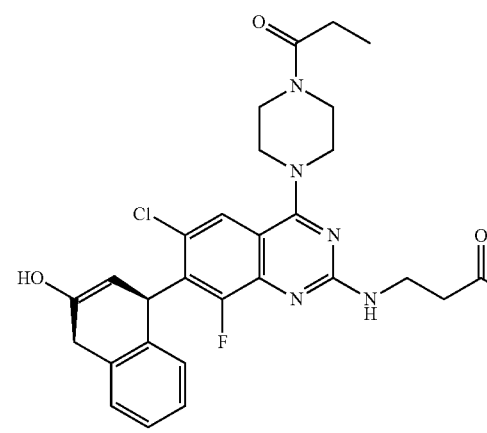

PTM-32
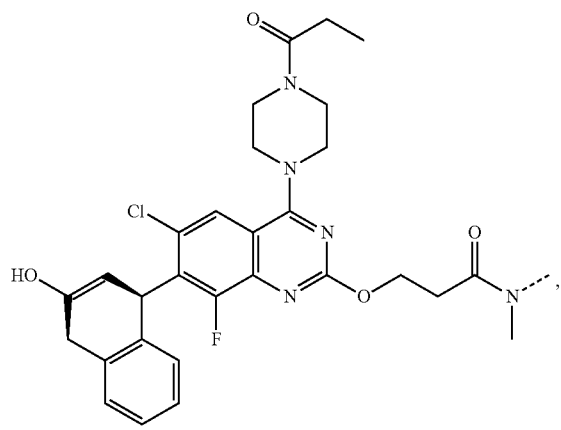
PTM-33
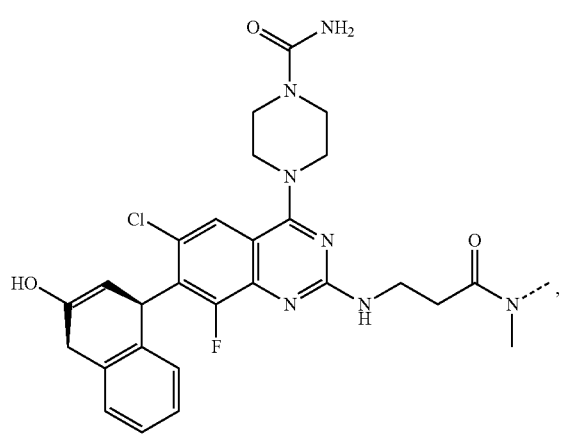
PTM-34
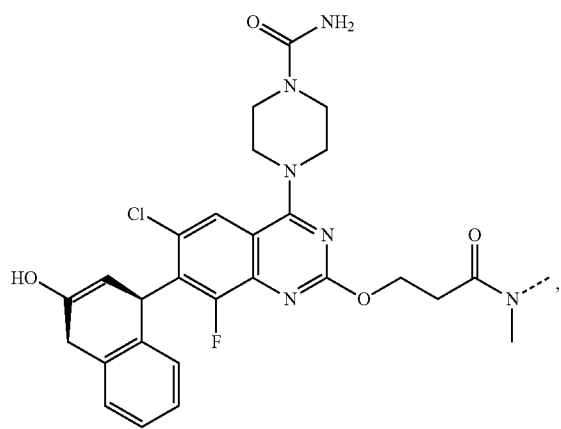
PTM-35
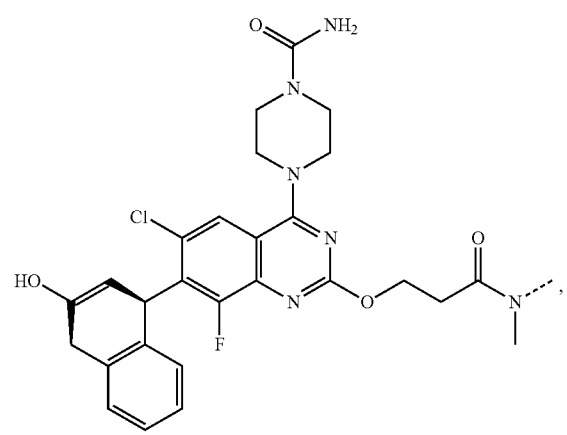
PTM-36
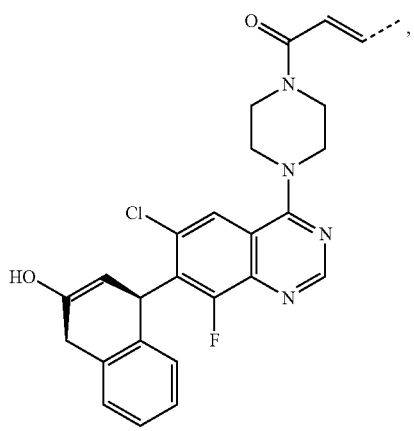
PTM-37
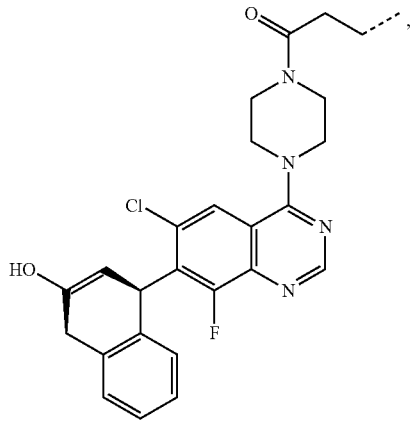

-continued
PTM-38
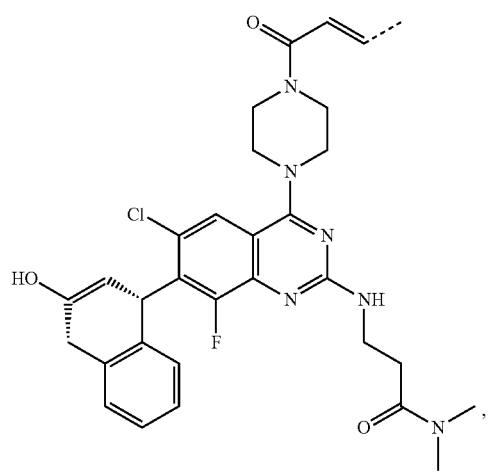
PTM-39
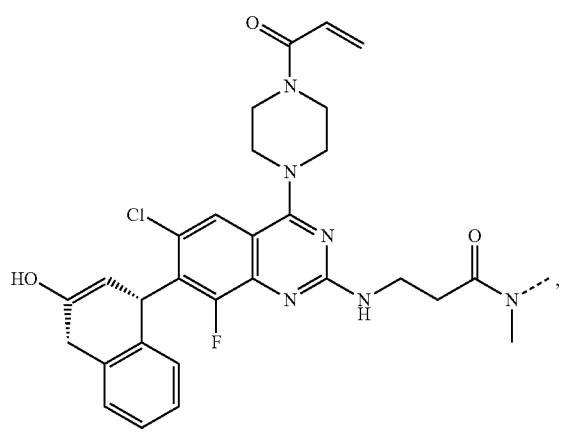
PTM-40
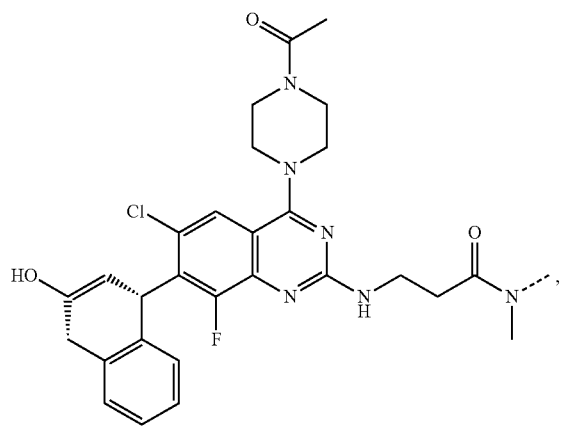
-continued
PTM-41
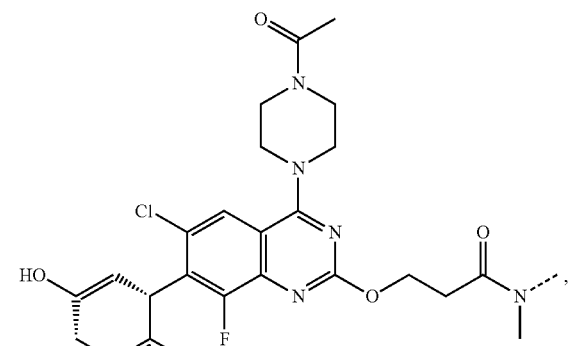
PTM-42
PTM-43
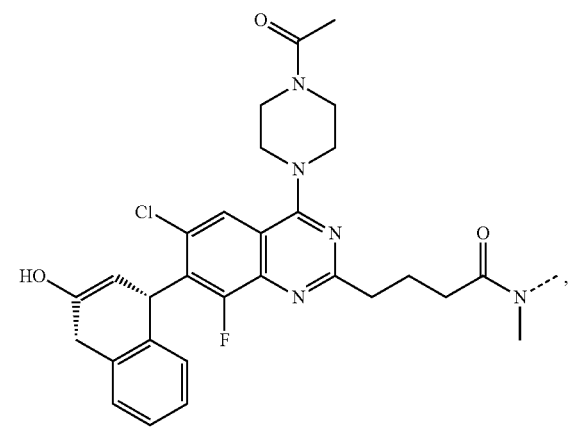

PTM-44
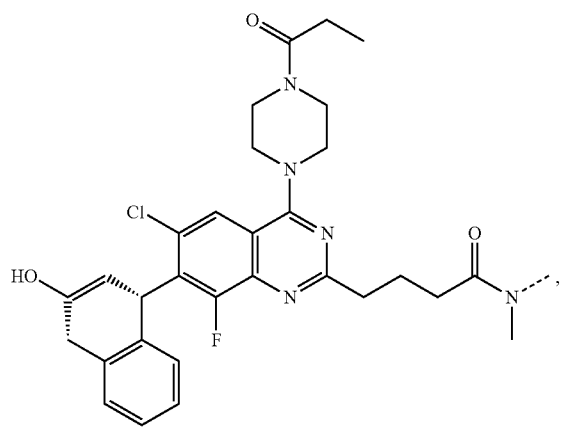
PTM-45
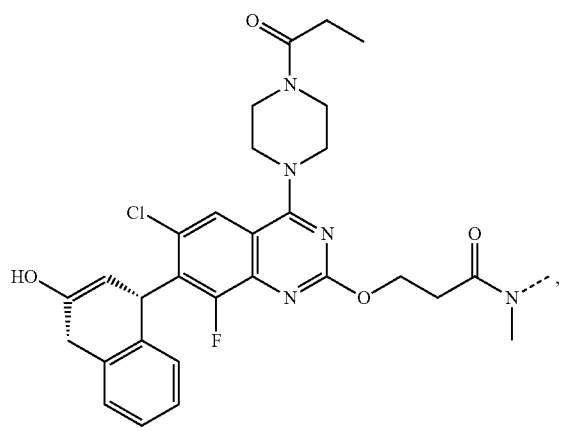
PTM-46
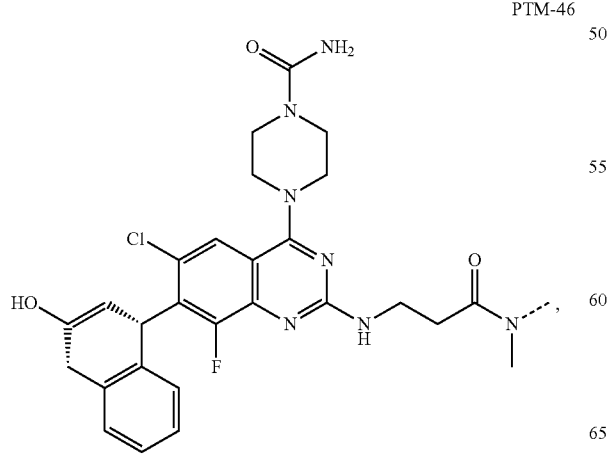
PTM-47
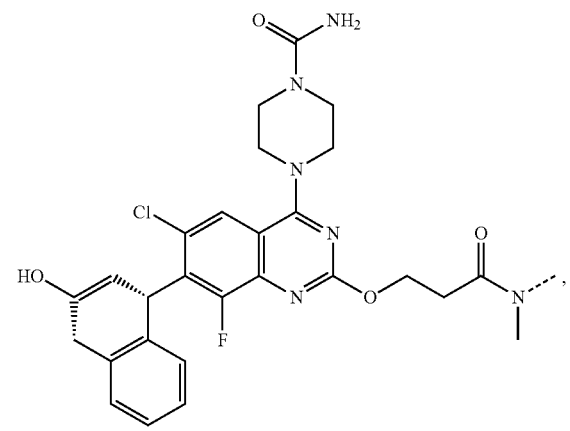
PTM-48
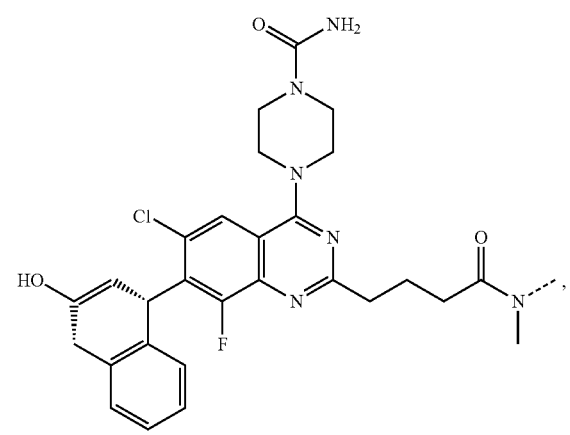
PTM-49
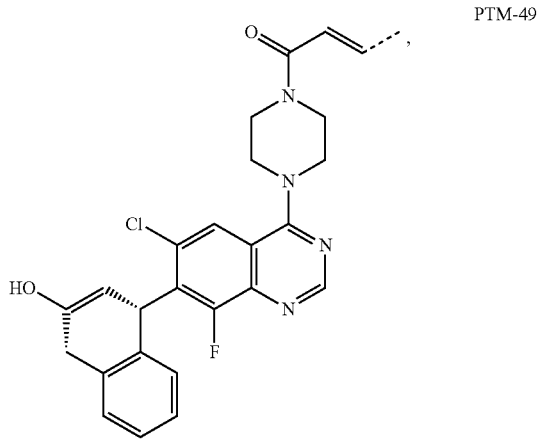

PTM-50
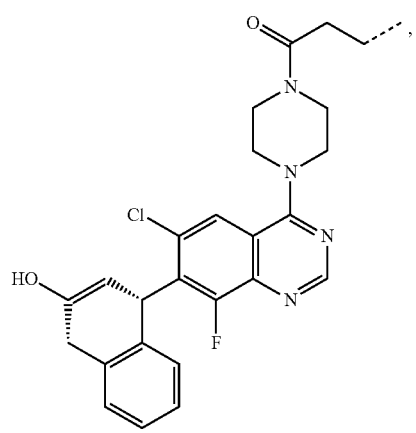
PTM-51
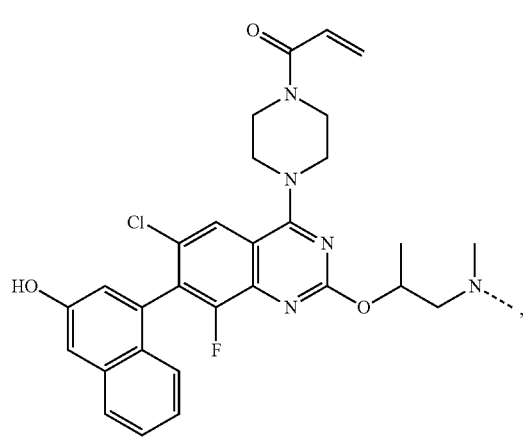
PTM-52
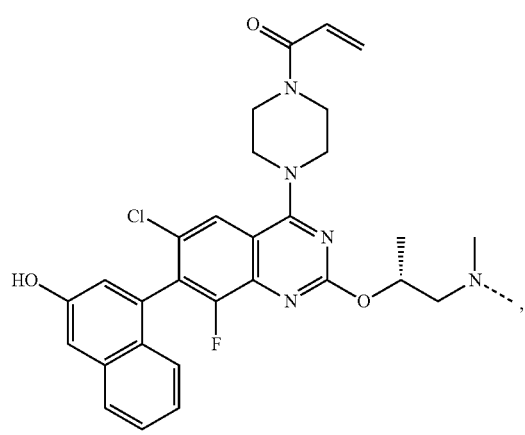
PTM-53
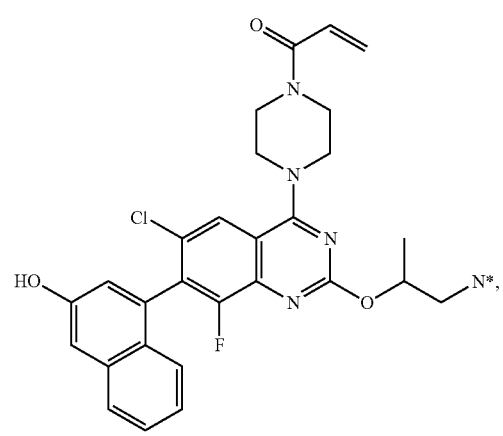
PTM-54
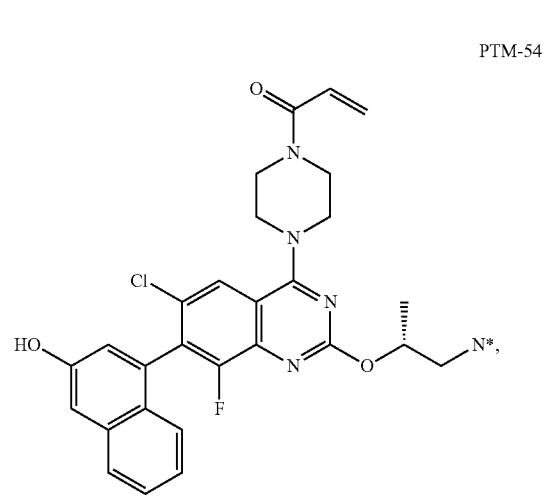
PTM-55
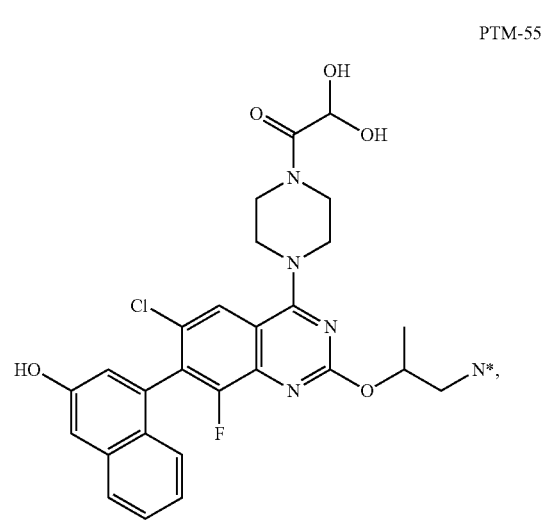

1935
-continued
PTM-56
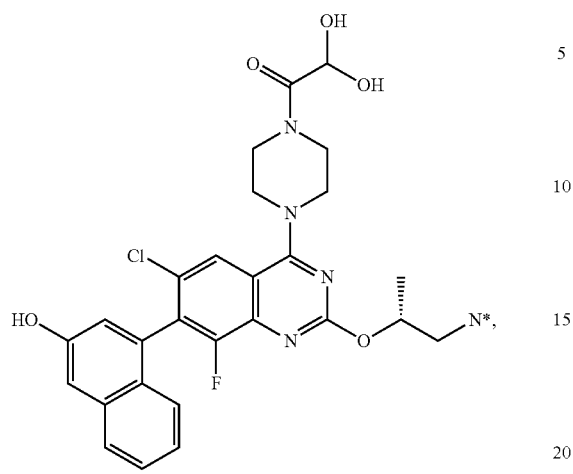
PTM-57
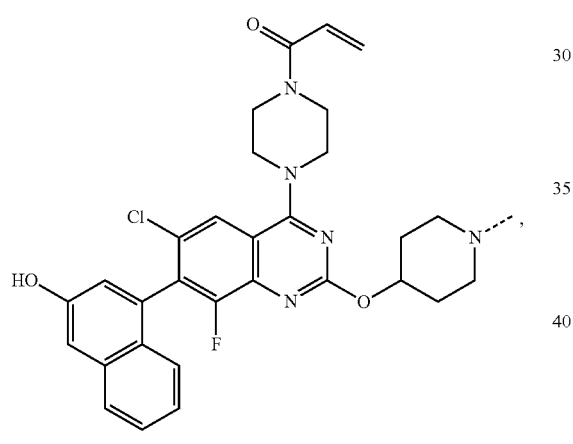
PTM-58
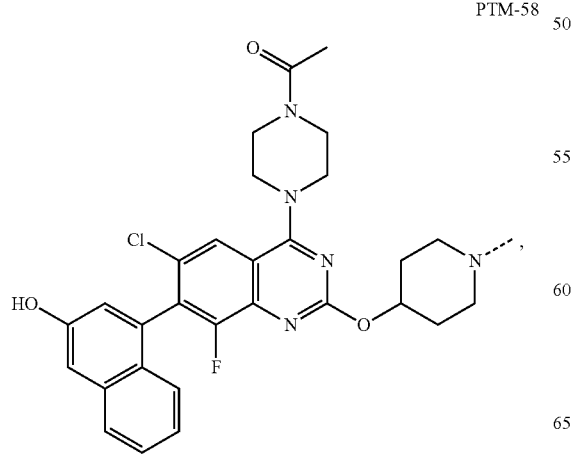
1936
-continued
PTM-59
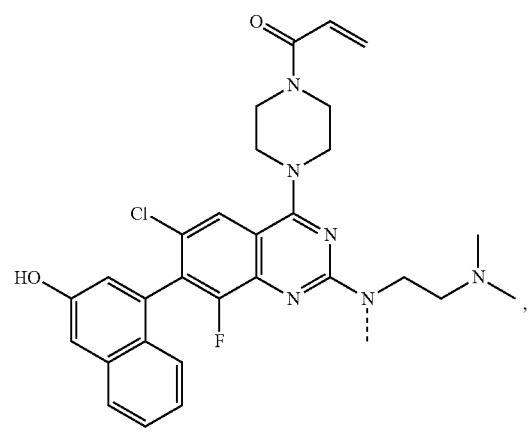
PTM-60
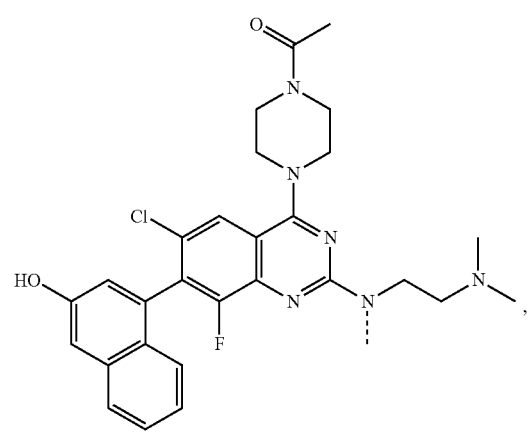
PTM-61
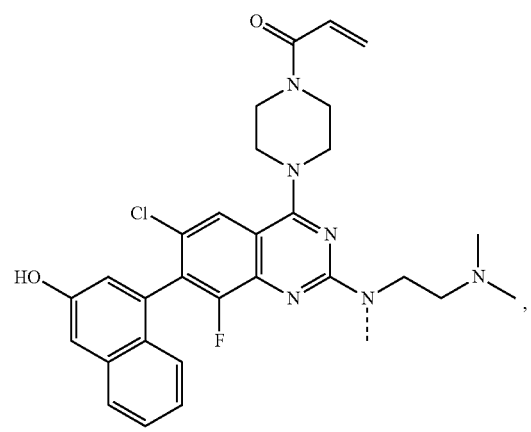

PTM-62
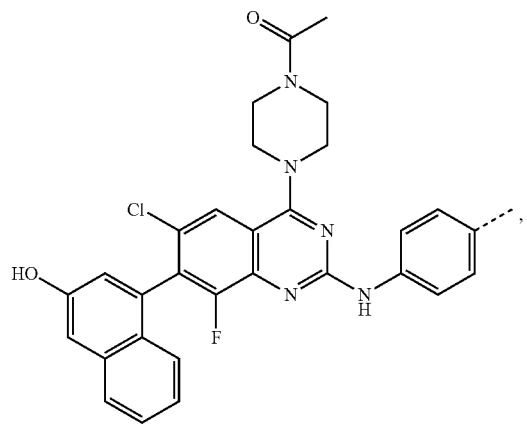
PTM-63
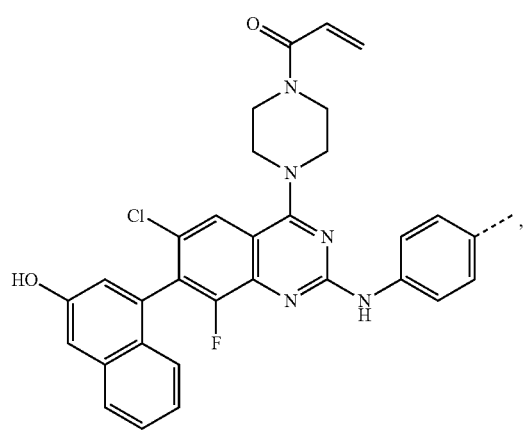
PTM-64
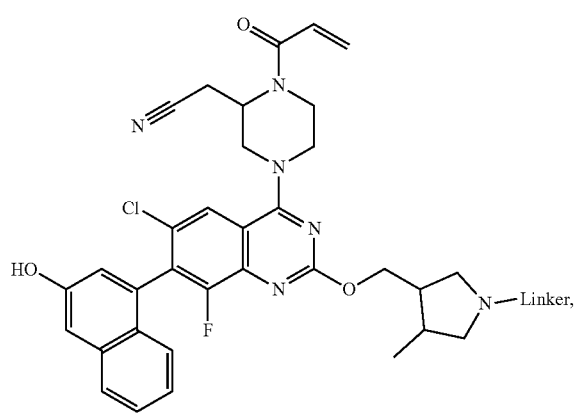
PTM-65
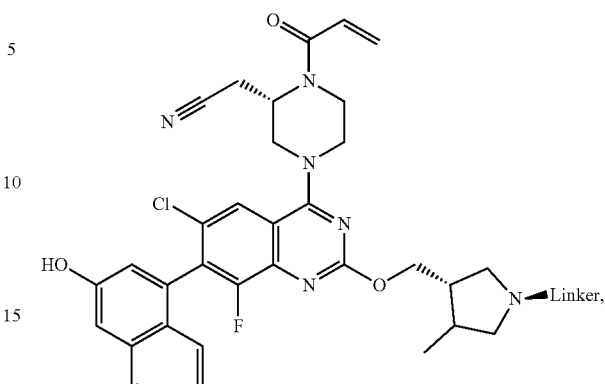
PTM-66
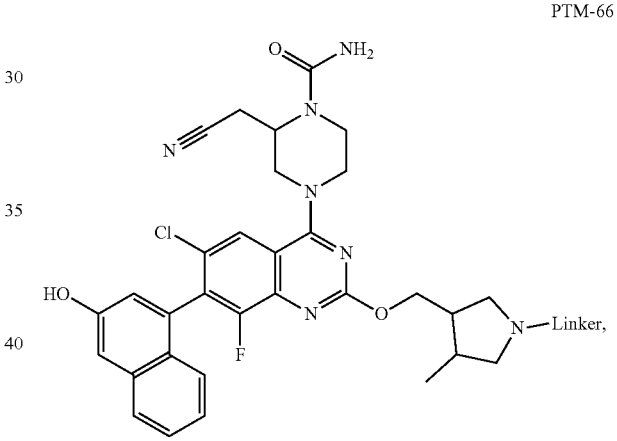
PTM-67
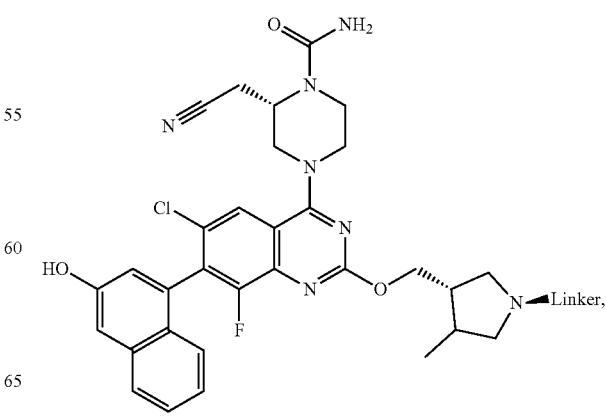

1939
-continued
PTM-68
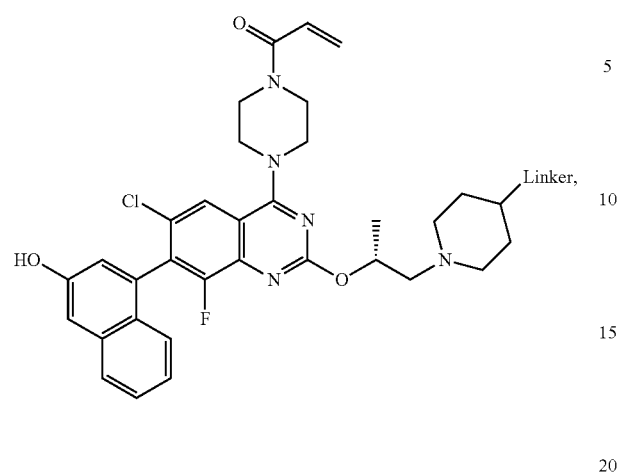
PTM-69
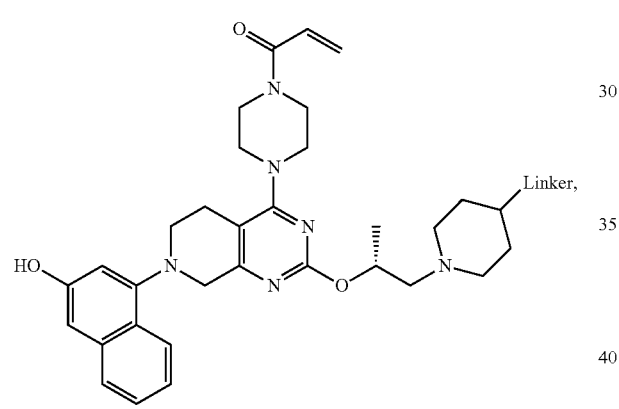
PTM-70
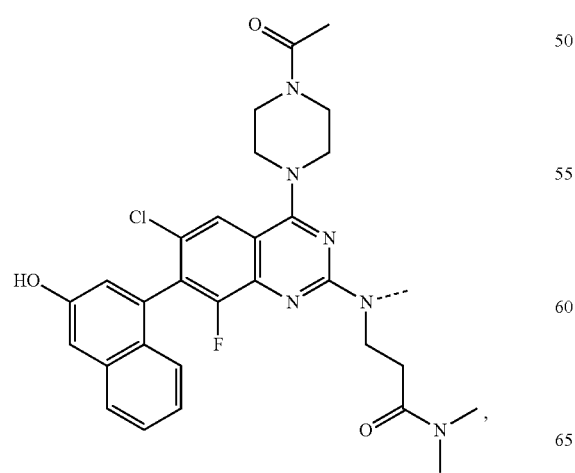
1940
-continued
PTM-71
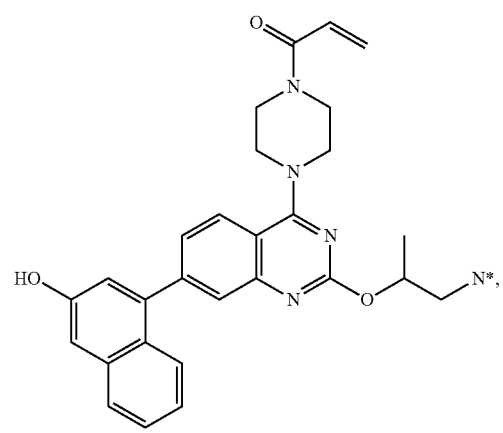
PTM-72
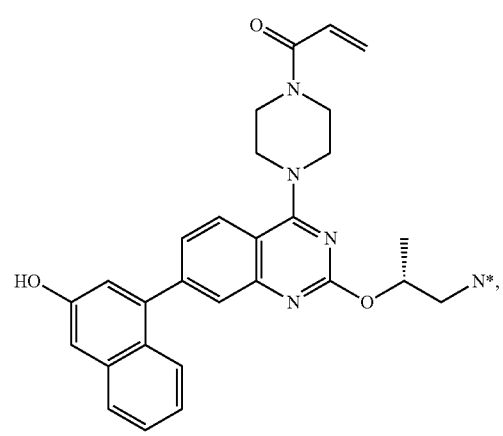
PTM-73
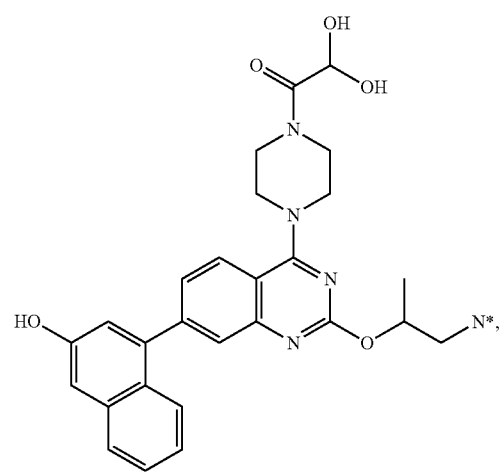

PTM-74
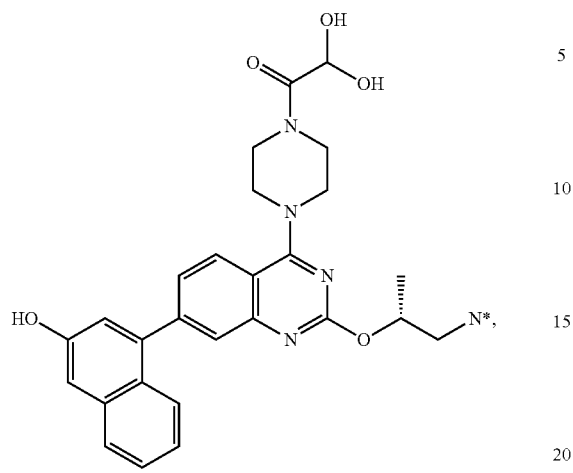
PTM-75
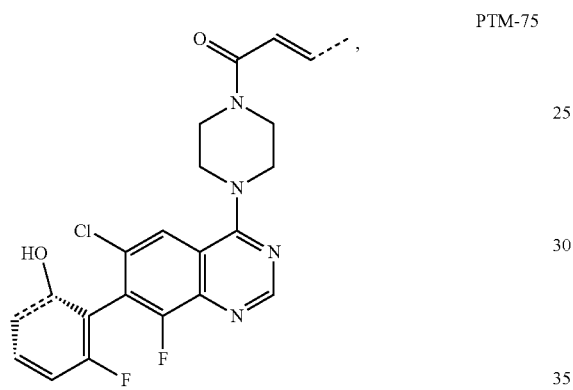
PTM-76
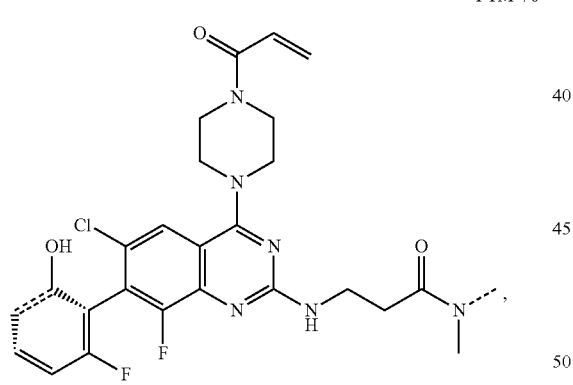
PTM-77
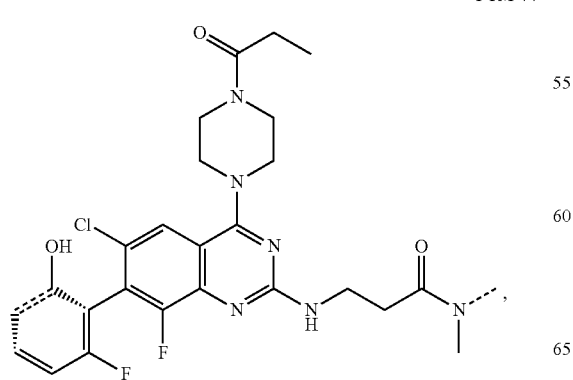
PTM-78
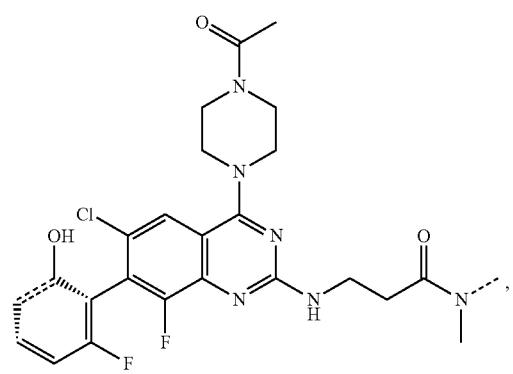
PTM-79
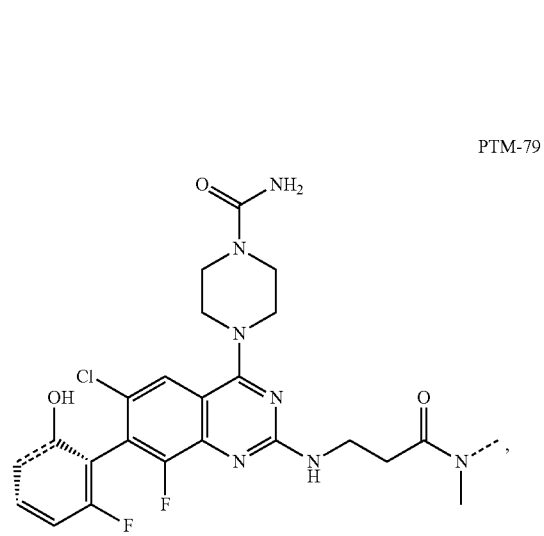
PTM-80
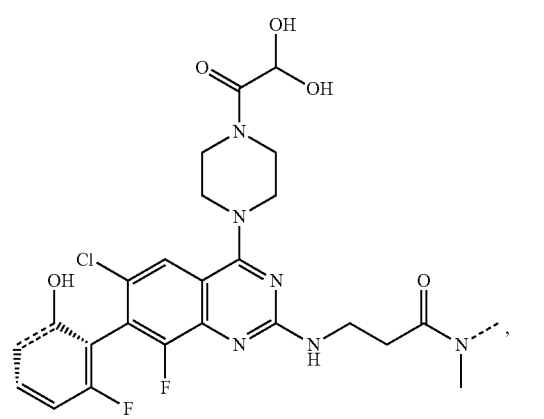

-continued
PTM-81
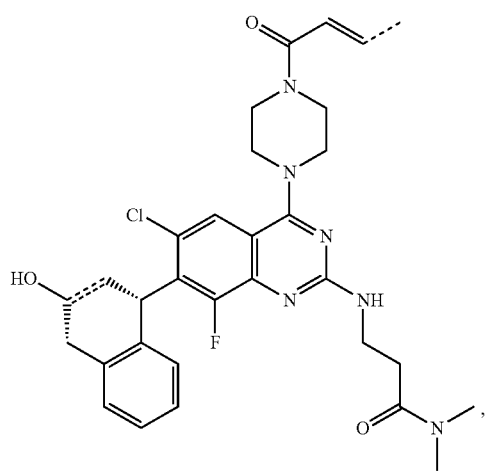
PTM-84
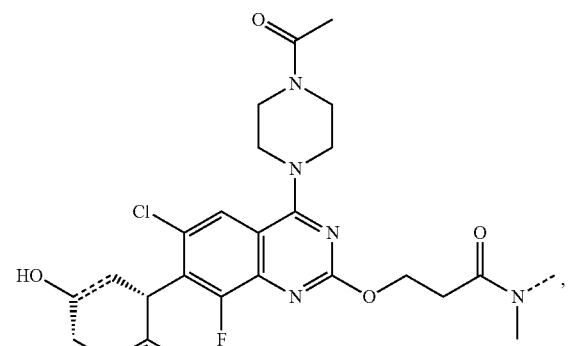
PTM-82
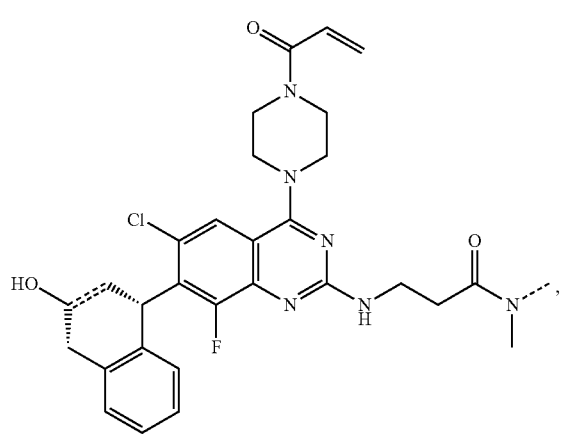
PTM-85
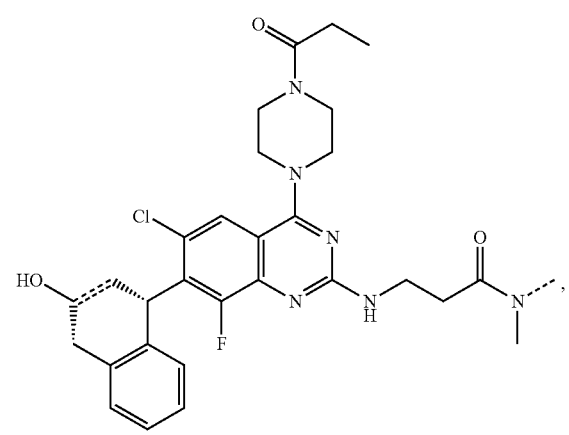
PTM-83
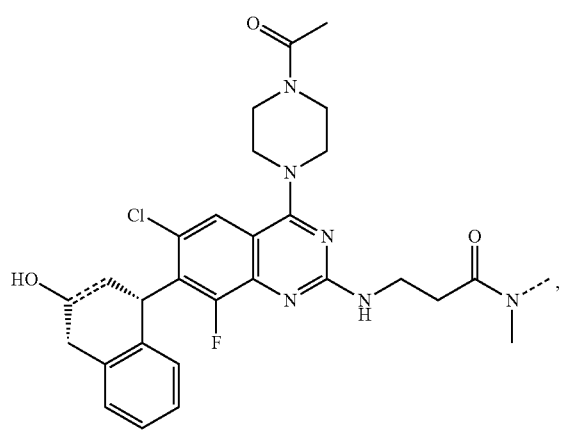
PTM-86
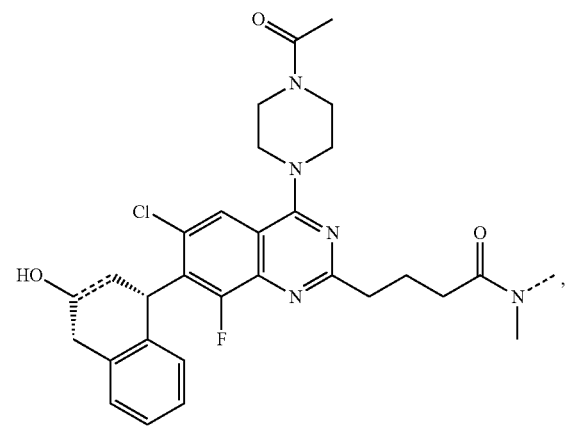

PTM-87
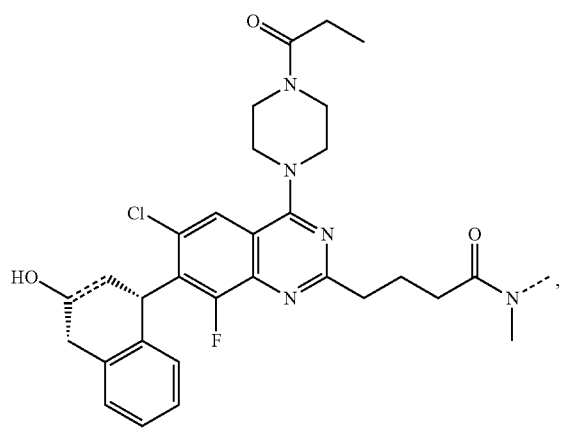
PTM-88
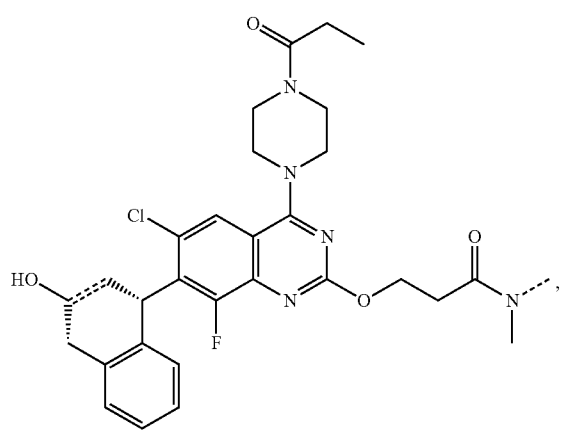
PTM-89
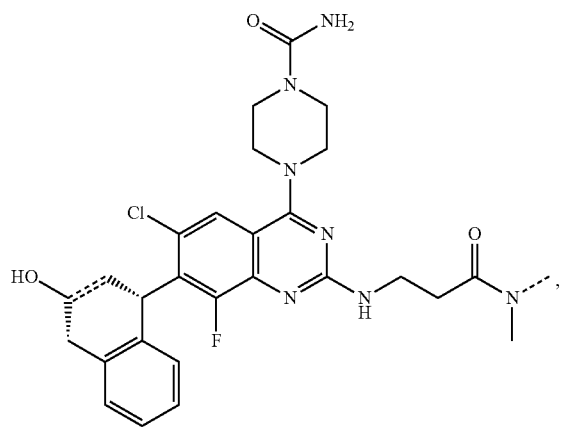
PTM-90
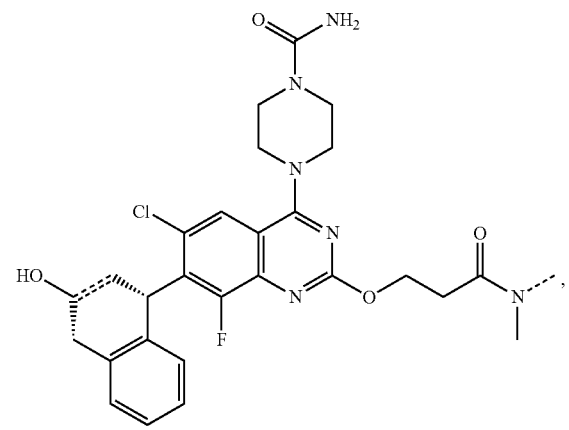
PTM-91
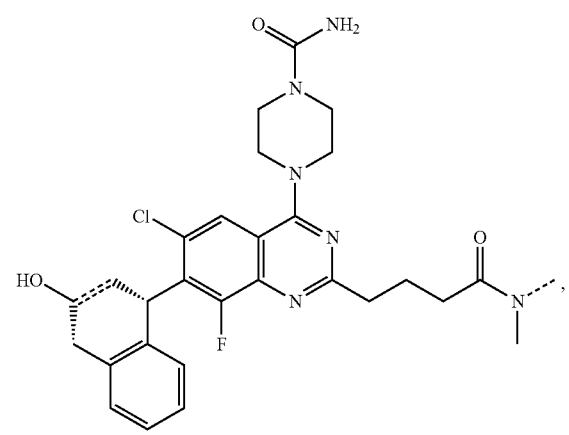
PTM-92
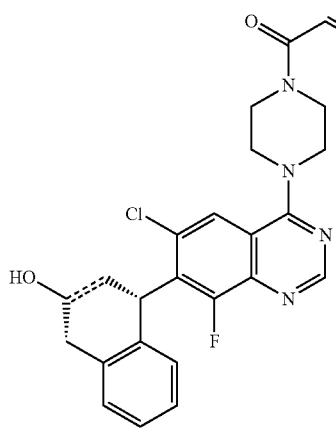

-continued

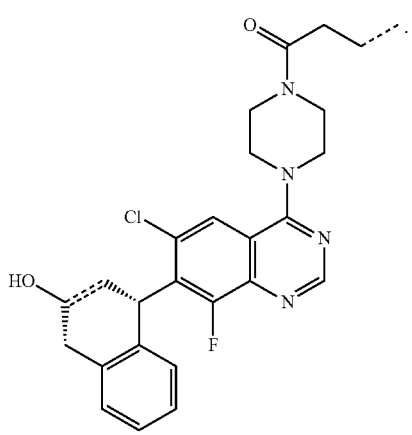

PTM-93

5. The bifunctional compound according to claim 1, wherein ULM is a Von Hippel-Lindau (VHL) ligase-binding moiety (VLM) with a chemical structure represented by:

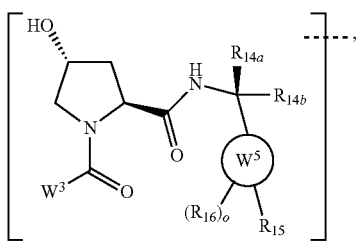

wherein:
W³ is an optionally substituted aryl, optionally substituted heteroaryl, or

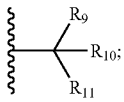

R₉ and R₁₀ are independently hydrogen, optionally substituted alkyl, optionally substituted cycloalkyl, optionally substituted hydroxyalkyl, optionally substituted heteroaryl, or haloalkyl, or R₉, R₁₀, and the carbon atom to which they are attached form an optionally substituted cycloalkyl;
R₁₁ is an optionally substituted heterocyclyl, optionally substituted alkoxy, optionally substituted heteroaryl, optionally substituted aryl,

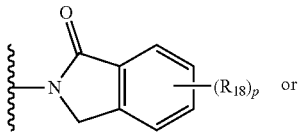 or

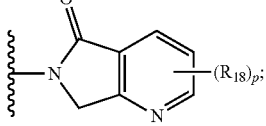

R₁₂ is H or optionally substituted alkyl;
R₁₃ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
R₁₄ₐ, and R₁₄ᵦ are each independently selected from the group of H, haloalkyl, and optionally substituted alkyl;
W⁵ is an optionally substituted phenyl or an optionally substituted 5-10 membered heteroaryl;
R₁₅ is H, halogen, CN, OH, NO₂, N R₁₄ₐR₁₄ᵦ, OR₁₄ₐ, CONR₁₄ₐR₁₄ᵦ, NR₁₄ₐCOR₁₄ᵦ, SO₂NR₁₄ₐR₁₄ᵦ, NR₁₄ₐSO₂R₁₄ᵦ, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;
each R₁₆ is independently halo, CN, optionally substituted alkyl, optionally substituted haloalkyl, optionally substituted alkoxy, hydroxy, or optionally substituted haloalkoxy;
o is 0, 1, 2, 3, or 4;
R₁₈ is halo, optionally substituted alkoxy, cyano, optionally substituted alkyl, haloalkyl, haloalkoxy or a linker; and
p is 0, 1, 2, 3, or 4, and
the dashed line indicates the site of attachment of the ULM to the linker group (L) or the PTM.

6. The bifunctional compound according to claim 1, wherein the ULM has a chemical structure selected from the group of:

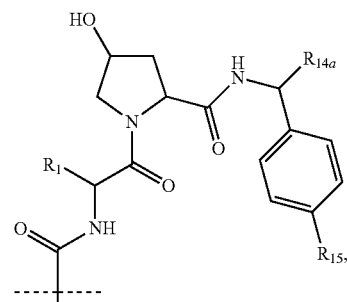

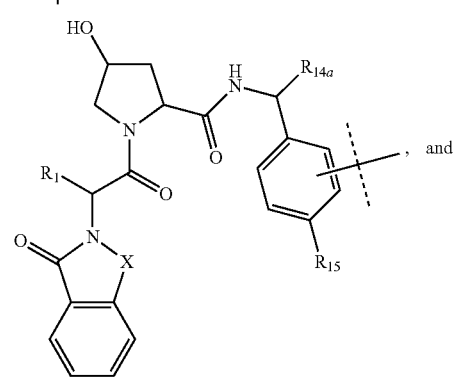

, and

-continued

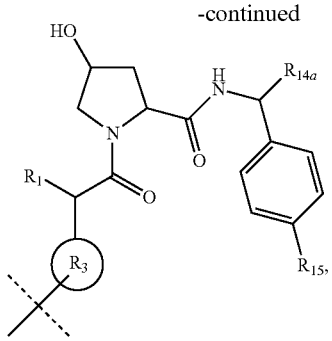

wherein:
R₁ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

R₁₄ₐ is H, haloalkyl, optionally substituted alkyl, methyl, fluoromethyl, hydroxymethyl, ethyl, isopropyl, or cyclopropyl;

R₁₅ is selected from the group consisting of H, halogen, CN, OH, NO₂, optionally substituted heteroaryl, optionally substituted aryl, optionally substituted alkyl, optionally substituted haloalkyl, optionally substituted haloalkoxy, optionally substituted cycloalkyl, or optionally substituted cycloheteroalkyl;

X is C, CH₂, or C=O

R₃ is absent or an optionally substituted 5 or 6 membered heteroaryl; and wherein the dashed line indicates the site of attachment of the ULM to the linker group (L) and the PTM.

7. The bifunctional compound according to claim 1, wherein the linker (L) comprises a chemical structural unit represented by the formula:

-(A$^L$)$_q$-, wherein:
-(A$^L$)$_q$- is a group which is connected to at least one of the ULM, the PTM, or both;

q is an integer greater than or equal to 1;

each A$^L$ is independently selected from the group consisting of, a bond, CR$^{L1}$R$^{L2}$, O, S, SO, SO₂, NR$^{L3}$, SO₂NR$^{L3}$, SONR$^{L3}$, CONR$^{L3}$, NR$^{L3}$CONR$^{L4}$, NR$^{L3}$SO₂NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO₂)NR$^{L4}$, C$_{3-11}$ cycloalkyl optionally substituted with 1-6 R$^{L1}$ and/or R$^{L2}$ groups, C$_{3-11}$ heteocyclyl optionally substituted with 1-6 R$^{L1}$ and/or R$^{L2}$ groups, aryl optionally substituted with 1-6 R$^{L1}$ and/or R$^{L2}$ groups, and heteroaryl optionally substituted with 1-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 1-4 R$^{L5}$ groups; and R$^{L1}$, R$^{L2}$, R$^{L3}$, R$^{L4}$, and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{3-8}$cycloalkyl, SC$_{3-8}$cycloalkyl, NHC$_{3-8}$cycloalkyl, N(C$_{3-8}$cycloalkyl)$_2$, N(C$_{3-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, C≡C-C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl) SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, or NH SO$_2$NH$_2$.

8. The bifunctional compound according to claim 1, wherein L is means for covalently coupling the PTM to the ULM.

9. The bifunctional compound according to claim 1, wherein the unit A$^L$ of linker (L) is selected from the group consisting of:

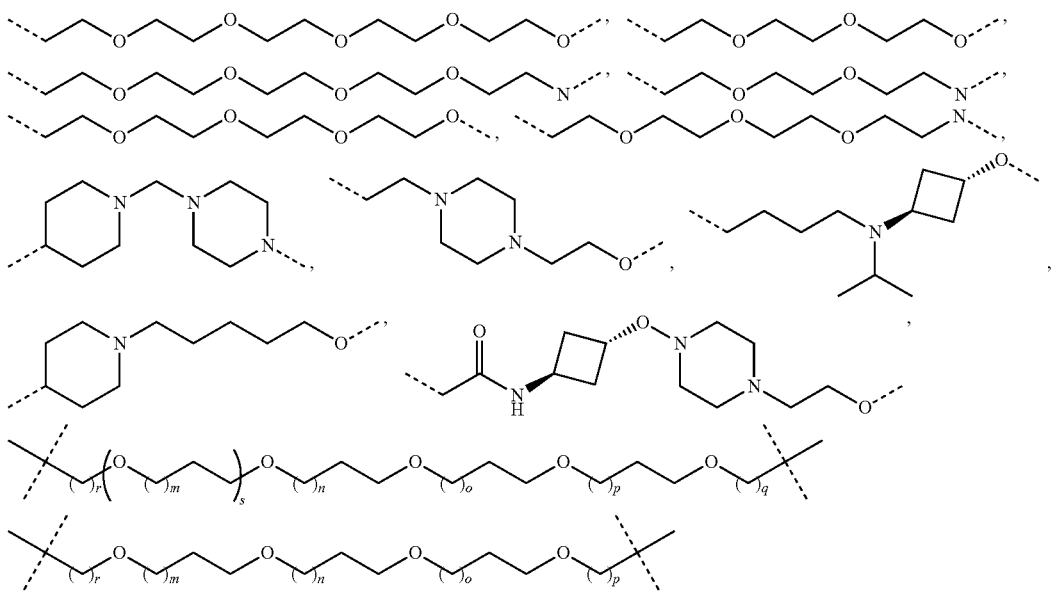

-continued
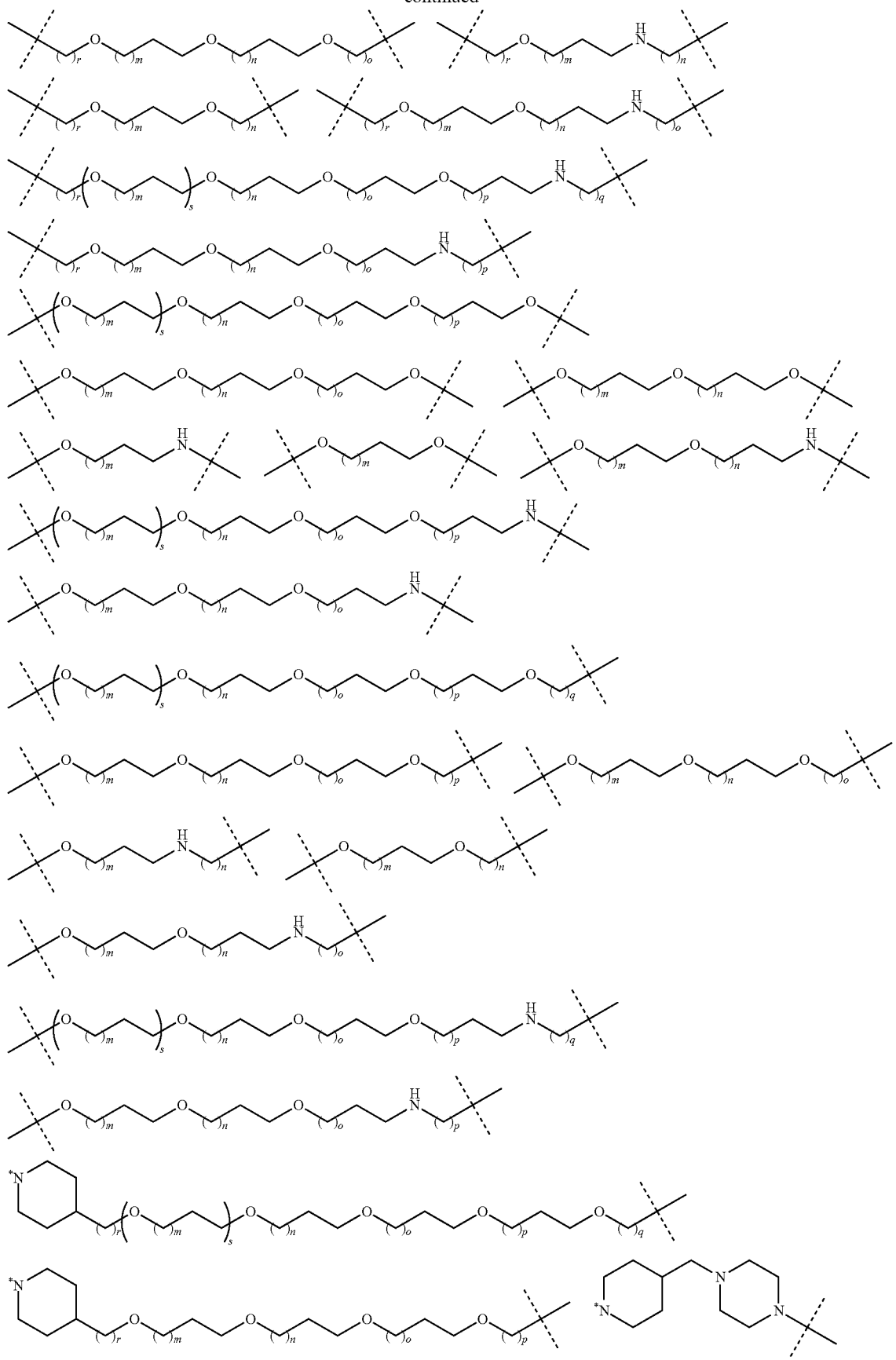

-continued
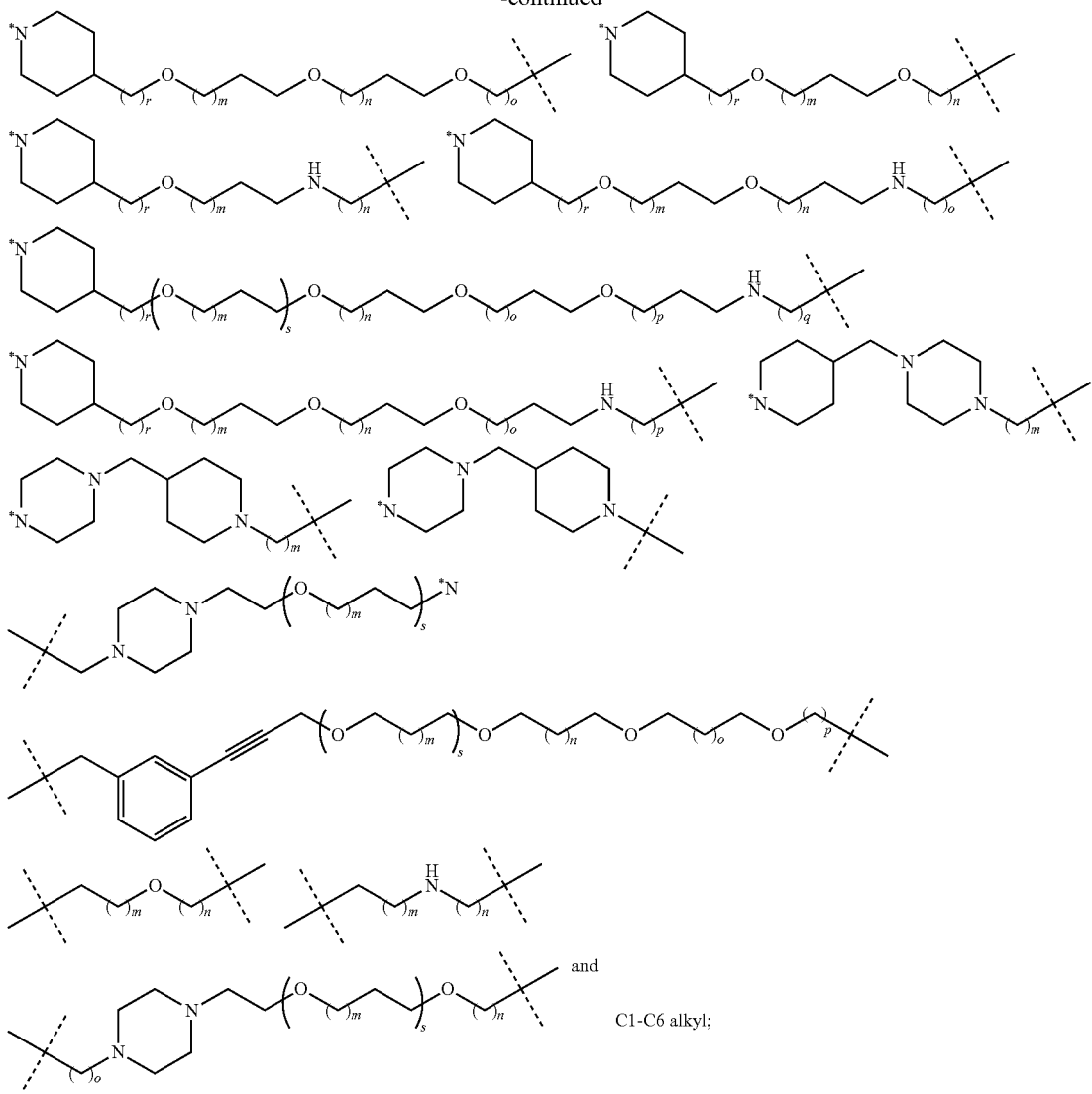
wherein:
  *N of the heterocycloalkyl is shared with the PTM; and
  each m, n, o, p, q, r, and s are independently selected from 0, 1, 2, 3, 4, 5, 6, 7, 8, 9, 10, 11, 12, 13, 14, 15, 16, 17, 18, 19, and 20.
10. The bifunctional compound according to claim 1, wherein the unit $A^L$ of linker (L) is selected from the group consisting of:
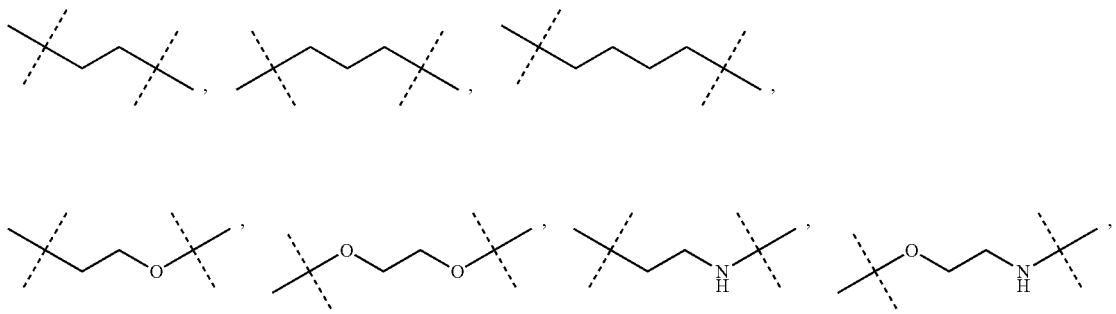

1955 1956
-continued
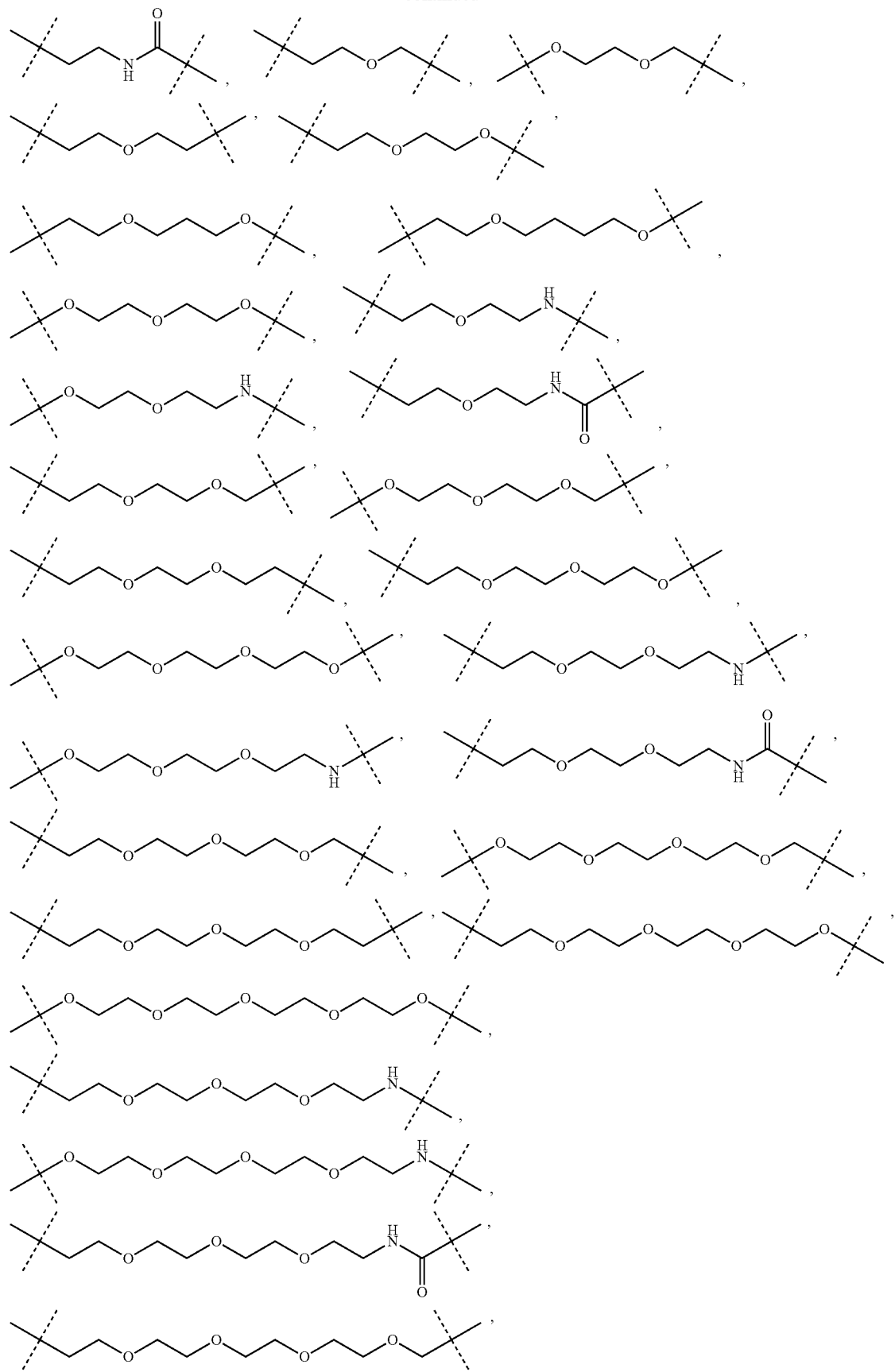

-continued
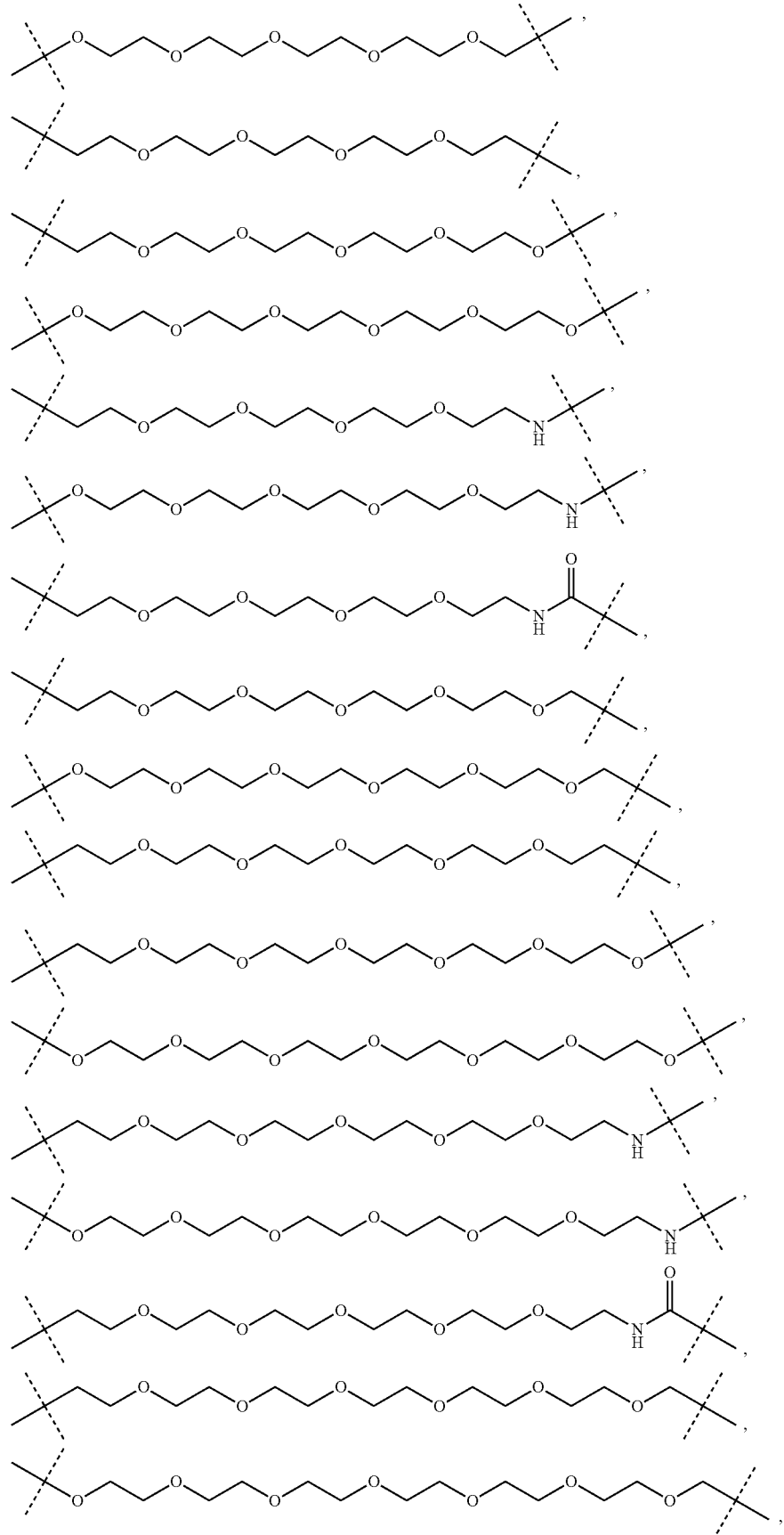

1959 1960
-continued
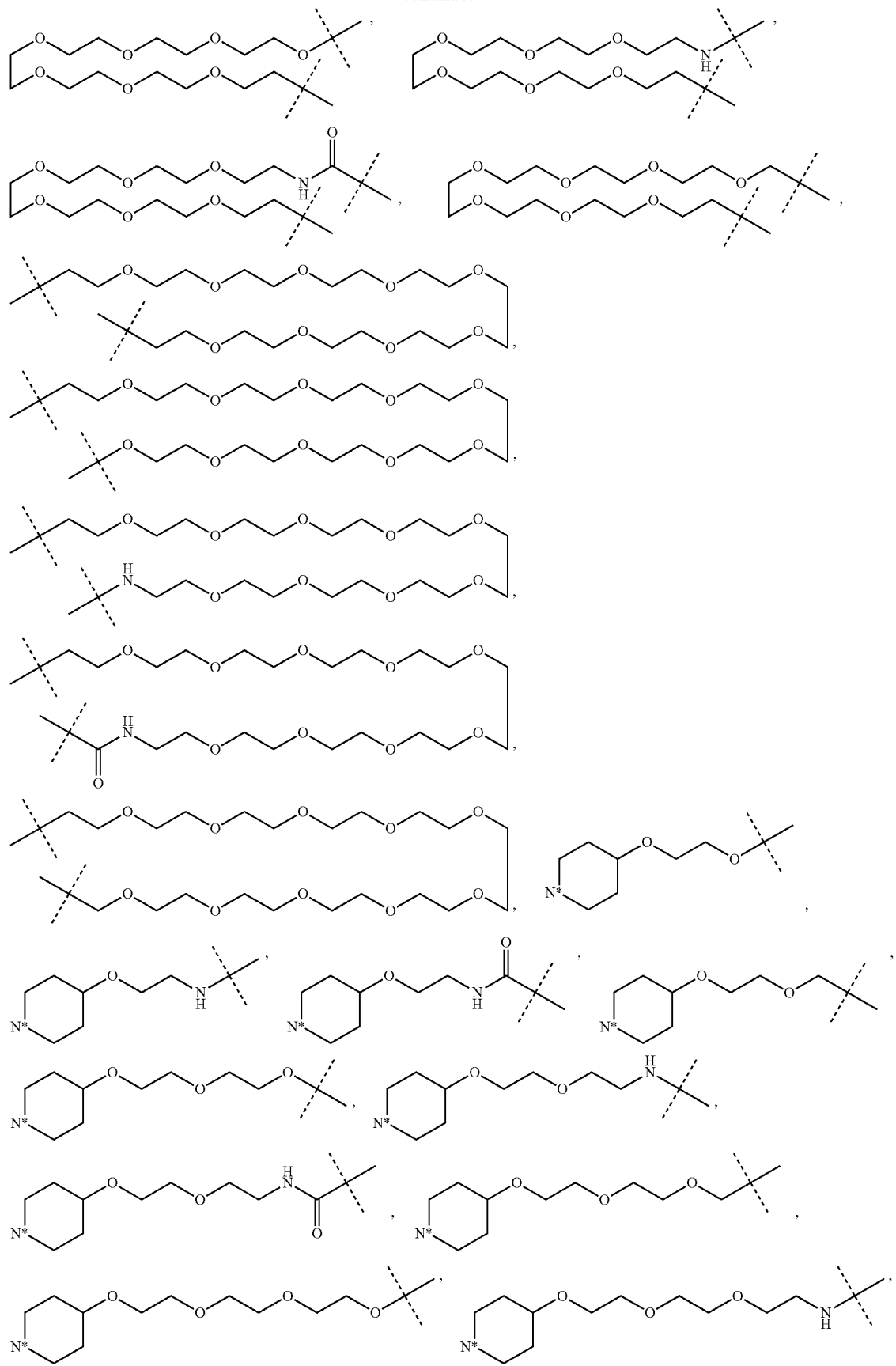

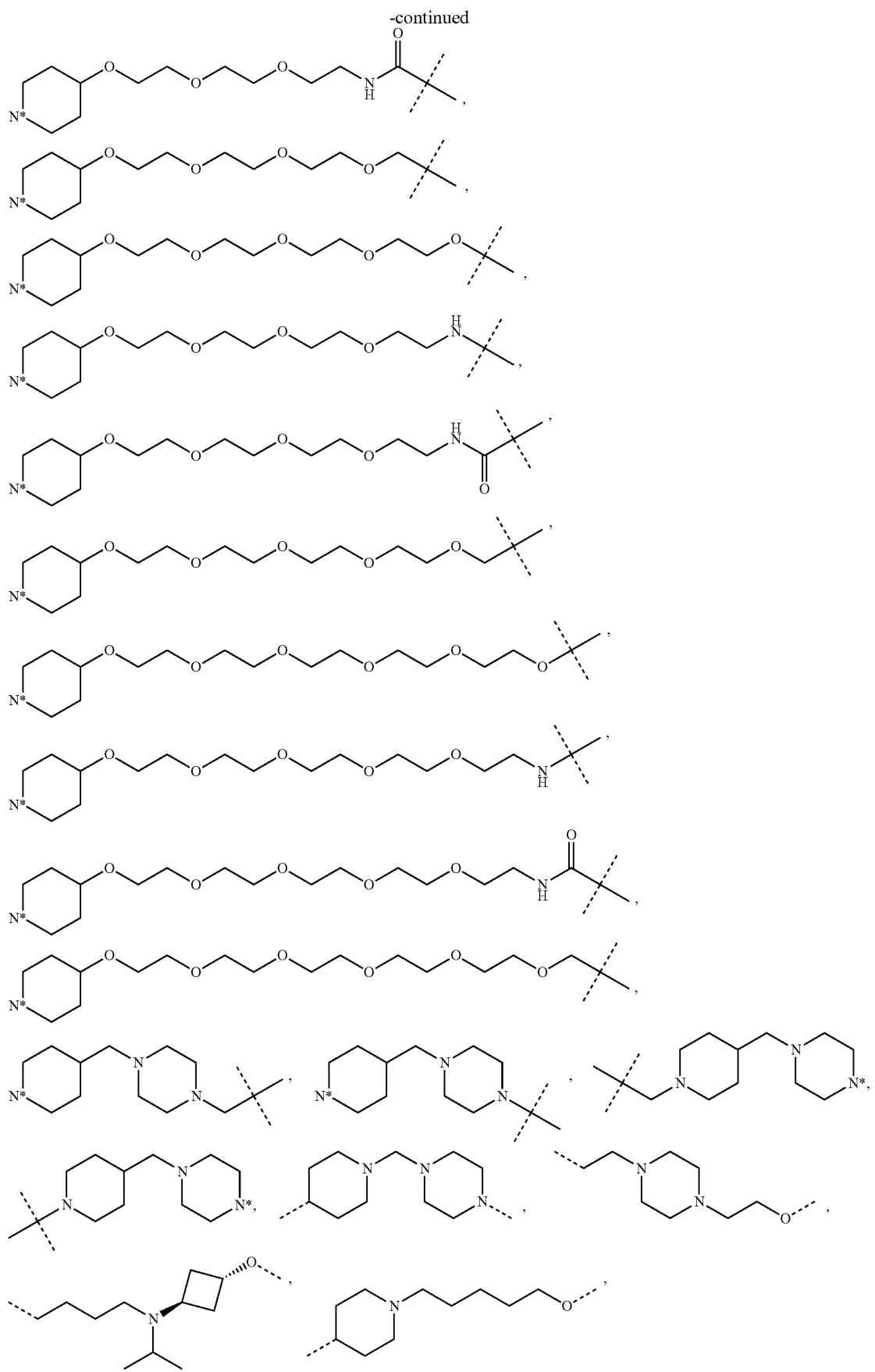

-continued

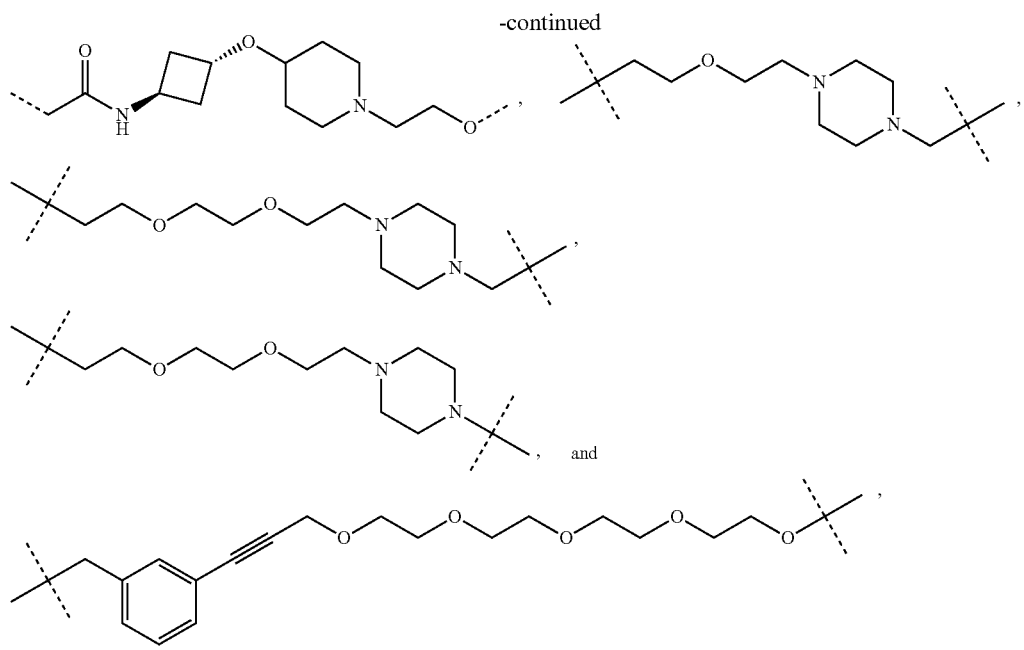

wherein N* of the heterocycloalkyl is shared with the PTM.

11. The bifunctional compound according to claim 1, wherein the linker (L) is a polyethylenoxy group optionally substituted with aryl or phenyl comprising from 1 to 10 ethylene glycol units.

12. The bifunctional compound according to claim 1, wherein the linker is an optionally substituted $C_1$-$C_{50}$ alkyl, wherein each carbon is optionally substituted with (1) a heteroatom selected from N, S, P, or Si atoms that has an appropriate number of hydrogens, substitutions, or both to complete valency, (2) an optionally substituted cycloalkyl or bicyclic cycloalkly, (3) an optionally substituted heterocyloalkyl or bicyclic heterocyloalkyl, (4) an optionally substituted aryl bicyclic aryl, or (5) optionally substituted heteroaryl or bicyclic heteroaryl, with the proviso that there is no heteroatom-heteroatom bonding.

13. The bifunctional compound according to claim 1, wherein the linker (L) comprises the following chemical structure:

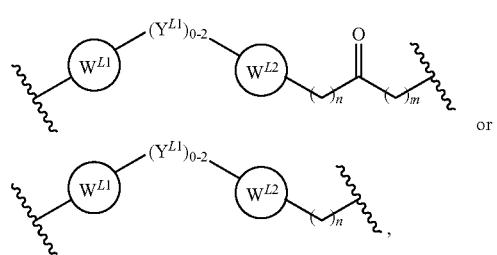

wherein:
$W^{L1}$ and $W^{L2}$ are each independently absent, or a 4-8 membered ring with 0-4 heteroatoms, optionally substituted with RQ, each RQ is independently a H, halo, OH, CN, CF3, optionally substituted linear or branched C1-C6 alkyl, optionally substituted linear or branched C1-C6 alkoxy, or 2 RQ groups taken together with the atom they are attached to, form a 4-8 membered ring system containing 0-4 heteroatoms;
$Y^{L1}$ is each independently: a bond; optionally substituted linear or branched C1-C6 alkyl and optionally one or more C atoms are replaced with O; or optionally substituted linear or branched C1-C6 alkoxy;
n is 0-10; and $\diagup\!\!\!\!\diagdown$ indicates the attachment point to the PTM or ULM moieties.

14. The bifunctional compound according to claim 1, wherein the linker (L) comprises the following chemical structure:

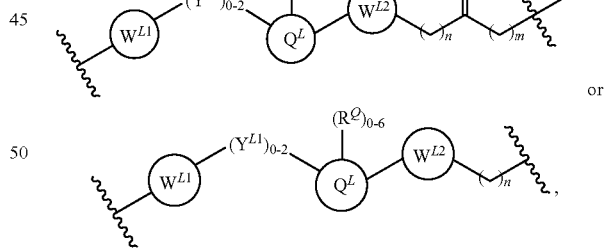

wherein:
$W^{L1}$ and $W^{L2}$ are each independently: absent; aryl; heteroaryl; cyclic; heterocyclic; $C_{1-6}$ alkyl and optionally one or more C atoms are replaced with O or N; $C_{1-6}$ alkene and optionally one or more C atoms are replaced with O; $C_{1-6}$ alkyne and optionally one or more C atoms are replaced with O; bicyclic; biaryl; biheteroaryl; or biheterocyclic, each optionally substituted with $R^Q$, each $R^Q$ is independently a H, halo, OH, CN, CF$_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl, OH, $NH_2$, $NR^{Y1}R^{Y2}$, or CN, or 2 $R^Q$ groups taken together with the atom they are attached to, form a 4-8 membered ring system containing 0-4 heteroatoms;

$Y^{L1}$ is each independently: a bond; $NR^{YL1}$; O; S; $NR^{YL2}$; $CR^{YL1}R^{YL2}$; C=O; C=S; SO; $SO_2$; optionally substituted linear or branched $C_1$-$C_6$ alkyl and optionally one or more C atoms are replaced with O; optionally substituted linear or branched $C_1$-$C_6$ alkoxy; or 3-6 membered alicyclic or aromatic ring with 0-4 heteroatoms;

$Q^L$ is a 3-6 membered alicyclic or aromatic ring with 0-4 heteroatoms, optionally bridged, optionally substituted with 0-6 $R^Q$, each $R^Q$ is independently H, linear or branched $C_{1-6}$ alkyl optionally substituted by 1 or more halo or $C_{1-6}$ alkoxyl, or 2 $R^Q$ groups taken together with the atom they are attached to, form a 3-8 membered ring system containing 0-2 heteroatoms;

$R^{YL1}$, $R^{YL2}$ are each independently H, OH, linear or branched $C_{1-6}$ alkyl optionally substituted by 1 or more halo or $C_{1-6}$ alkoxyl, or $R^1$, $R^2$ together with the atom they are attached to, form a 3-8 membered ring system containing 0-2 heteroatoms;

n is 0-10; and

 indicates the attachment point to the PTM or ULM moieties.

15. The bifunctional compound according to claim 1, wherein at least one of:
   (a) the PTM is selected from a compound of Table 4, 6, 8, 10 or 12, or a PTM of Table 1;
   (b) the ULM is selected from a compound of Tables 4, 6, 8, 10, and 12 or a ULM of Table 3;
   (c) the unit $A^L$ of linker (L) is selected from a compound of Tables 4, 6, 8, 10 and, or a L from Table 2; or
   (d) a combination thereof.

16. The bifunctional compound of claim 1, wherein the compound is selected from the group consisting of: exemplary compounds 1-249, 254-454, and 458-573.

17. A composition comprising an effective amount of a bifunctional compound of claim 1, and a pharmaceutically acceptable carrier.

18. The composition of claim 17, wherein the composition further comprises at least one of additional bioactive agent or another bifunctional compound of claim 1.

19. The composition of claim 18, wherein the additional bioactive agent is an anti-cancer agent.

20. A method for treating a disease or disorder in a subject, the method comprising administering a composition comprising a pharmaceutically acceptable carrier and an effective amount of at least one compound of claim 1 to a subject in need thereof, wherein the disease or disorder is cancer that is associated with the accumulation, aggregation, and/or overactivation of KRas, and the compound is effective in treating or ameliorating at least one symptom of the disease or disorder.

21. The method according to claim 20, wherein the disease or disorder is pancreatic cancer, colon cancer, colorectal cancer, lung cancer, non-small cell lung cancer, biliary tract malignancies, endometrial cancer, cervical cancer, bladder cancer, liver cancer, myeloid leukemia, and breast cancer.

22. The method according to claim 20, wherein the disease or disorder is pancreatic cancer, colon cancer, lung cancer, non-small cell lung cancer.

* * * * *